(12) United States Patent
Johannes et al.

(10) Patent No.: US 11,492,358 B1
(45) Date of Patent: Nov. 8, 2022

(54) MACROCYCLIC INDOLE DERIVATIVES

(71) Applicants: Bayer Aktiengesellschaft, Leverkusen (DE); Bayer Pharma Aktiengesellschaft, Berlin (DE); The Broad Institute, Inc., Cambridge, MA (US)

(72) Inventors: Sarah Anna Liesa Johannes, Leverkusen (DE); Philipp Buchgraber, Leverkusen (DE); Ulrich Klar, Leverkusen (DE); Clara Christ, Leverkusen (DE); Kai Thede, Leverkusen (DE); Joachim Kuhnke, Leverkusen (DE); Manfred Moewes, Leverkusen (DE); Knut Eis, Leverkusen (DE); Amaury Ernesto Fernandez-Montalvan, Leverkusen (DE); Nicolas Werbeck, Leverkusen (DE); Ursula Mönning, Leverkusen (DE); Philip Lienau, Leverkusen (DE); Ulrike Sack, Leverkusen (DE); Arne Scholz, Leverkusen (DE); Michael H. Serrano-Wu, Cambridge, MA (US); Christopher Lemke, Cambridge, MA (US); David McKinney, Cambridge, MA (US); Mark Fitzgerald, Cambridge, MA (US); Christopher Nasveschuk, Cambridge, MA (US); Kiel Lazarski, Cambridge, MA (US); Steven James Ferrara, Cambridge, MA (US); Laura Furst, Cambridge, MA (US); Guo Wei, Cambridge, MA (US); Patrick Ryan McCarren, Cambridge, MA (US)

(73) Assignees: The Broad Institute, Inc., Cambridge, MA (US); Bayer Aktiengesellschaft, Leverkusen (DE); Bayer Pharma Aktiengesellschaft, Berlin (DE)

( * ) Notice: Subject to any disclaimer, the term of this patent is extended or adjusted under 35 U.S.C. 154(b) by 17 days.

(21) Appl. No.: 17/186,820

(22) Filed: Feb. 26, 2021

Related U.S. Application Data

(63) Continuation of application No. 16/301,871, filed as application No. PCT/EP2017/000629 on May 17, 2017, now Pat. No. 10,981,932.

(60) Provisional application No. 62/338,942, filed on May 19, 2016.

(30) Foreign Application Priority Data

Jun. 2, 2016 (EP) .................................. 16172726

(51) Int. Cl.
*C07D 498/16* (2006.01)
*C07D 498/06* (2006.01)
*C07D 498/22* (2006.01)
*C07D 487/16* (2006.01)

(52) U.S. Cl.
CPC ......... *C07D 498/16* (2013.01); *C07D 487/16* (2013.01); *C07D 498/06* (2013.01); *C07D 498/22* (2013.01)

(58) Field of Classification Search
None
See application file for complete search history.

(56) References Cited

U.S. PATENT DOCUMENTS

| 10,981,932 B2 | 4/2021 | Johannes et al. |
| 2015/0336925 A1 | 11/2015 | Lee et al. |
| 2016/0106731 A1 | 4/2016 | Lee et al. |
| 2017/0305926 A1 | 10/2017 | Hird et al. |

(Continued)

FOREIGN PATENT DOCUMENTS

| WO | WO-2008/130970 A1 | 10/2008 |
| WO | WO-2015/031608 A1 | 3/2015 |
| WO | WO-2015/148854 A1 | 10/2015 |

(Continued)

OTHER PUBLICATIONS

Adams et al., "The Bcl-2 apoptotic switch in cancer development and therapy," Oncogene, 26:1324-1337 (2007).

(Continued)

*Primary Examiner* — Joseph R Kosack
(74) *Attorney, Agent, or Firm* — Foley Hoag LLP; David P. Halstead

(57) ABSTRACT

The present invention relates to macrocyclic indole derivatives of general formula (I)

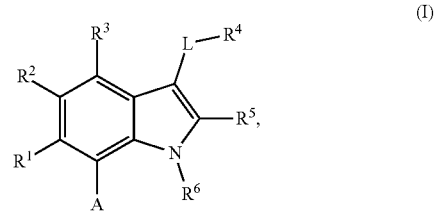

in which $R^1$, $R^2$, $R^3$, $R^4$, $R^5$, $R^6$, A and L are as defined herein, methods of preparing said compounds, intermediate compounds useful for preparing said compounds, pharmaceutical compositions and combinations comprising said compounds, and the use of said compounds for manufacturing pharmaceutical compositions for the treatment or prophylaxis of diseases, in particular of hyperproliferative disorders, as a sole agent or in combination with other active ingredients.

18 Claims, No Drawings
Specification includes a Sequence Listing.

(56) References Cited

U.S. PATENT DOCUMENTS

2020/0087322 A1     3/2020    Johannes et al.
2021/0079018 A1     3/2021    Ferrara et al.

FOREIGN PATENT DOCUMENTS

| | | |
|---|---|---|
| WO | WO-2017/152076 A1 | 9/2017 |
| WO | WO-2017/182625 A1 | 10/2017 |
| WO | WO-2017/198341 A1 | 11/2017 |
| WO | WO-2018/098534 A1 | 6/2018 |
| WO | WO-2019/096905 A1 | 5/2019 |
| WO | WO-2019/096907 A1 | 5/2019 |
| WO | WO-2019/096909 A1 | 5/2019 |
| WO | WO-2019/096911 A1 | 5/2019 |
| WO | WO-2019/096914 A1 | 5/2019 |
| WO | WO-2019/096922 A1 | 5/2019 |
| WO | WO-2020/151738 A1 | 7/2020 |
| WO | WO-2020/236556 A1 | 11/2020 |

OTHER PUBLICATIONS

Beroukhim et al., "The Landscape of Somatic Copy-Number Alteration Across Human Cancers," Nature, 463(7283):899-905 (2010).

Glaser et al., "Anti-apoptotic Mcl-1 is essential for the development and sustained growth of acute myeloid leukemia," Genes Dev, 26:120-125 (2012).

Hanahan et al., "Hallmarks of Cancer: The Next Generation," Cell 144(5):646-674 (2011).

International Preliminary Report on Patentability for International Application No. PCT/EP2017/000629 dated Nov. 20, 2018.

International Preliminary Report on Patentability for International Application No. PCT/EP2018/081370 dated May 19, 2020.

International Preliminary Report on Patentability for International Application No. PCT/EP2018/081374 dated May 19, 2020.

International Preliminary Report on Patentability for International Application No. PCT/EP2018/081378 dated May 19, 2020.

International Preliminary Report on Patentability for International Application No. PCT/EP2018/081381 dated May 19, 2020.

International Preliminary Report on Patentability for International Application No. PCT/EP2018/081388 dated May 19, 2020.

International Preliminary Report on Patentability for International Application No. PCT/EP2018/081406 dated May 19, 2020.

International Search Report and Written Opinion for International Application No. PCT/EP2017/000629 dated Sep. 6, 2019.

International Search Report and Written Opinion for International Application No. PCT/EP2018/081370 dated Feb. 13, 2019.

International Search Report and Written Opinion for International Application No. PCT/EP2018/081374 dated Feb. 13, 2019.

International Search Report and Written Opinion for International Application No. PCT/EP2018/081378 dated Jan. 9, 2019.

International Search Report and Written Opinion for International Application No. PCT/EP2018/081381 dated Jan. 15, 2019.

International Search Report and Written Opinion for International Application No. PCT/EP2018/081388 dated Feb. 14, 2019.

International Search Report and Written Opinion for International Application No. PCT/EP2018/081406 dated Feb. 11, 2019.

International Search Report and Written Opinion for International Application No. PCT/US2020/033067 dated Jul. 19, 2020.

Korsmeyer, "BCL-2 Gene Family and the Regulation of Programmed Cell Death," Cancer Res Suppl, 59(7):1693s-1700s (1999).

Pelz et al., "Discovery of 2-Indole-acylsulfonamide Myeloid Cell Leukemia 1 (Mcl-1) Inhibitors Using Fragment-Based Methods," Journal of Medicinal Chemistry, 59(5): 2054-2066 (2016).

Wertz et al., "Sensitivity to antitubulin chemotherapeutics is regulated by MCL1 and FBW7," Nature, 471:110-114 (2011).

Zhang et al., "Research progress of GSK-3 inhibitors," Progress in Chemistry, 19(4): 614-623 (2007).

Zhou et al., "MCL1 transgenic mice exhibit a high incidence of B-cell lymphoma manifested as a spectrum of histologic subtypes," Blood, 97(12):3902-3909 (2001).

SEQUENCE LISTING

<160> NUMBER OF SEQ ID NOS: 3

<210> SEQ ID NO 1
<211> LENGTH: 26
<212> TYPE: PRT
<213> ORGANISM: Artificial Sequence
<220> FEATURE:
<223> OTHER INFORMATION: Description of Artificial Sequence: Synthetic
      NoxaBH3 peptide
<220> FEATURE:
<223> OTHER INFORMATION: N-term Biotin-PEG2-PEG2
<220> FEATURE:
<221> NAME/KEY: MOD_RES
<222> LOCATION: (8)..(8)
<223> OTHER INFORMATION: Norvaline
<220> FEATURE:
<223> OTHER INFORMATION: C-term amide

<400> SEQUENCE: 1

Pro Ala Glu Leu Glu Val Glu Val Ala Thr Gln Leu Arg Arg Phe Gly
1               5                   10                  15

Asp Lys Leu Asn Phe Arg Gln Lys Leu Leu
            20                  25

<210> SEQ ID NO 2
<211> LENGTH: 25
<212> TYPE: PRT
<213> ORGANISM: Artificial Sequence
<220> FEATURE:
<223> OTHER INFORMATION: Description of Artificial Sequence: Synthetic
      Bad BH3-derived peptide
<220> FEATURE:
<223> OTHER INFORMATION: N-term Biotin-PEG2-PEG2
<220> FEATURE:
<221> NAME/KEY: MOD_RES
<222> LOCATION: (15)..(15)
<223> OTHER INFORMATION: Norleucine
<220> FEATURE:
<223> OTHER INFORMATION: C-term amide

<400> SEQUENCE: 2

Asn Leu Trp Ala Ala Gln Arg Tyr Gly Arg Glu Leu Arg Arg Leu Ser
1               5                   10                  15

Asp Glu Phe Val Asp Ser Phe Lys Lys
            20                  25

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 3

His His His His His His
1               5

MACROCYCLIC INDOLE DERIVATIVES

RELATED APPLICATIONS

This application is a continuation of U.S. patent application Ser. No. 16/301,871, filed Nov. 15, 2018, which is the U.S. national phase of International Patent Application No. PCT/EP2017/000629, filed May 17, 2017, which claims the benefit of priority to U.S. Provisional Patent Application No. 62/338,942, filed May 19, 2016.

SEQUENCE LISTING

The instant application contains a Sequence Listing which has been filed electronically in ASCII format and is hereby incorporated by reference in its entirety. Said ASCII copy, created on Nov. 7, 2019, is named BRH-00402_SL and is 1,597 byes in size.

BACKGROUND

The present invention covers macrocyclic indole derivatives of general formula (I) which inhibit the antiapoptotoic activity of MCL-1 by inhibiting its interaction with proapototic proteins.

Apoptosis, also called programmed cell death, is a natural process which allows a damaged or unwanted cell to die in a controlled manner. Deregulation of this process leads to unrestrained cell proliferation and is thus a hallmark of cancer (Hanahan and Weinberg, 2011).

Apoptosis is highly controlled by proteins of the B-cell lymphoma 2 (BCL-2) family. These proteins are characterized by their conserved regions known as BCL-2 homology (BH) domains (BH1-BH4) (Korsmeyer, 1999) through which they interact with each other. The BCL-2 family can be divided into pro-apoptotic members including BAX, BAK, BAD, BID, BIM, BMF, NOXA, and PUMA, which induce cell death, and anti-apoptotic members such as BCL-2, BCL-XL, BCL-w, Bfl1-AI, and myeloid cell leukemia-1 (MCL-1) which block apoptosis (Adams and Cory, 2007). The relative expression level of these two opponent groups of the BCL-2 family will decide if a cell will go into apoptosis or not.

MCL-1 has been identified as an important therapeutic target in cancer. MCL-1 is highly expressed in a variety of human cancers, and amplification of the MCL-1 locus is one of the most frequent somatic genetic events in human cancer, further pointing to its centrality in the pathogenesis of malignancy (Beroukhim et al., 2010). Its expression has been linked to deregulated anti-apoptotic pathways in cancer, thus leading to increased cancer cell survival, tumor development (Zhou et al., 2001) and resistance to anticancer therapies (Wertz et al., 2011). MCL-1 protein has been shown to mediate survival in models of acute myeloid leukemia (Glaser et al., 2012), lymphomas (Kelly et al., 2014) and multiple myeloma (Zhang et al., 2002). Many chemotherapeutics as well as radiation aim at inducing apoptosis in cancer cells. However, in malignant cells, apoptotic signaling is often deregulated, leading to uncontrolled growth and therapeutic resistance. One key resistance mechanism to apoptosis is to upregulate or genetically amplify MCL-1.

MCl-1 is a major inhibitor of apoptosis in cancer. MCL-1 is the largest member of the anti-apoptotic BCl-2 proteins. Its expression is tightly controlled with a half-life of only 1-4 h. With its BH-3 domain, MCL-1 tightly binds to BH-3 only containing pro-apoptotic proteins such as BAK or BAX and hinders them from inducing pores in the mitochondrial membrane, thereby blocking the intrinsic apoptotic pathway.

Thus, the specific inhibition of the interaction of MCL-1 with BH-3 only containing pro-apoptotic proteins like BAK or BAX represents a very attractive therapeutic principle to induce apoptosis in cancer cells and to address resistance against chemotherapeutics, radiation and new targeted agents. However, from WO 2015/148854, US 2016/0106731, WO 2008/130970, some indole derivatives are known as MCL-1 inhibitors. As there are no inhibitors in the clinic yet, there is still a need for further MCL-1 inhibitors to be provided.

SUMMARY

It has now been found that the compounds of the present invention effectively inhibit the activity of the anti-apoptotic BCL-2 family member Myeloid cell leukemia-1 (MCL-1) protein for which data are given in the biological experimental section and may therefore be used for the treatment or prophylaxis of hyperproliferative disorders, such as cancer disorders, for example, forms of acute leukemia, lymphoma and multiple myeloma.

In accordance with a first aspect, the present invention provides compounds of general formula (I):

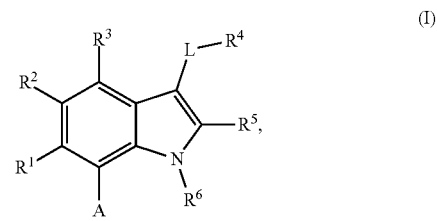

(I)

in which
A is

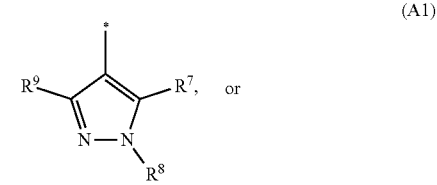

(A1)

or

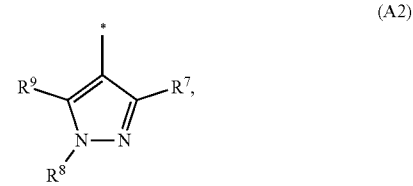

(A2)

wherein $R^6$ and $R^7$, together with two carbon atoms of the pyrazole ring, two carbon atoms of the indole moiety and the nitrogen atom to which $R^6$ is attached, form a 9- to 16-membered ring and * is the point of attachment of these moieties to the indole carbon atom bearing the A substituent or A is

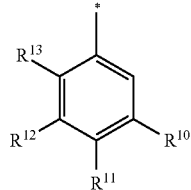

(A3)

whereby optionally one or two of the groups selected from $CR^{11}$, $CR^{12}$ or $CR^{13}$ may be replaced by a nitrogen atom,
wherein $R^6$ and $R^{10}$, together with three carbon atoms of the phenyl ring, two carbon atoms of the indole moiety and the nitrogen atom to which $R^6$ is attached, form a 9- to 16-membered ring and * is the point of attachment of these moieties to the indole carbon atom bearing the A substituent;

$R^1$ and $R^2$ are each independently selected from a hydrogen atom, a halogen atom, a cyano group, a $C_1$-$C_3$-alkyl group and a $C_1$-$C_3$-alkoxy group;

$R^3$ is selected from a hydrogen atom, a halogen atom, a cyano group, a $C_1$-$C_3$-alkyl group, a $C_1$-$C_3$-haloalkyl group, a $C_1$-$C_3$-alkoxy group, a $C_1$-$C_3$-alkylthio group, a —S(O)—($C_1$-$C_3$-alkyl) group, a —S(O)$_2$—($C_1$-$C_3$-alkyl) group, a $C_1$-$C_3$-haloalkoxy group, a $C_1$-$C_3$-haloalkylthio group and a $C_3$-$C_5$-cycloalkyl group;

$R^4$ is selected from an aryl group and a heteroaryl group, which is optionally substituted with one, two, three, four or five substituents and each substituent is independently selected from a halogen atom, a cyano group, a $C_1$-$C_3$-alkyl group, a $C_1$-$C_3$-haloalkyl group(, a $C_1$-$C_3$-alkoxy group, a $C_1$-$C_3$-thioalkyl group, a $C_1$-$C_3$-haloalkoxy group, and a ($C_1$-$C_3$)-haloalkyl-S— group and a $C_3$-$C_5$-cycloalkyl group;

L is a group —(CH$_2$)$_m$-E- wherein any CH$_2$ group is optionally substituted with one or two substituents and each substituent is independently selected from a halogen atom, a cyano group, a hydroxyl group, a $C_1$-$C_3$-alkyl group and a $C_1$-$C_3$-alkoxy group, or two substituents are optionally taken together with their intervening atoms to form a saturated or partially unsaturated 3-6-membered cycloalkyl ring, or a 3-8 membered saturated or partially unsaturated heterocyclic ring having 1-2 heteroatoms independently selected from an oxygen atom, a sulfur atom, a —S(O)— group, a —S(O)$_2$— group and a —NR$^{14}$— group;

E is a bond, an oxygen atom, a sulfur atom, a —S(O)— group, a —S(O)$_2$— group or a —NR$^{14}$— group and constitutes the connecting element to $R^4$,
where $R^{14}$ is a hydrogen atom or a $C_1$-$C_3$-alkyl group;
m is 2, 3, or 4;

$R^5$ is selected from a COOH group, or a

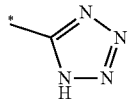

group, a —C(O)—NHS(O)$_2$($C_1$-$C_6$-alkyl) group, a —C(O)—NHS(O)$_2$($C_3$-$C_6$-cycloalkyl) group, a —C(O)—NHS(O)$_2$(aryl) group, a —C(O)—NHS(O)$_2$(CH$_2$)$_s$NHCO ($C_1$-$C_6$-alkyl) group, a —C(O)—NHS(O)$_2$(CH$_2$)$_s$NHCO ($C_3$-$C_6$-cycloalkyl) group and a —C(O)—NHS(O)$_2$ (CH$_2$)$_s$NHCO(aryl) group;

s is 0, 1, 2, or 3;

—$R^6$-$R^7$— is selected from $^\#$—(CH$_2$)$_n$—(B)$_t$(CH$_2$)$_p$—$^{\#\#}$, $^\#$—(C$_2$-C$_6$-alkenylene)-(B)$_t$—(CH$_2$)$_p$—$^{\#\#}$, $^\#$—(CH$_2$)$_n$—(B)$_t$(C$_2$-C$_6$-alkenylene)-$^{\#\#}$ and $^\#$—(CH$_2$)$_q$—(B) —(CH$_2$)$_r$—(B)—(CH$_2$)$_v$—$^{\#\#}$, wherein any CH$_2$ group is optionally substituted with one or more substituents selected from a halogen atom, a hydroxyl group, a NR$^{17}$R$^{18}$ group, a $C_1$-$C_3$-alkyl group, a $C_1$-$C_3$-haloalkyl group, a $C_1$-$C_3$-alkoxy group, a $C_1$-$C_3$-haloalkoxy group and a (heterocycloalkyl)-($C_1$-$C_3$-alkylene)- group, and where a double bond in any alkenylene can be replaced by a 1,2-cyclopropyl group, and said 1,2-cyclopropyl group is optionally substituted one or two times with a halogen atom or a $C_1$-$C_2$-alkyl group, wherein $^\#$ is the point of attachment with the indole nitrogen atom and $^{\#\#}$ is the point of attachment with the pyrazole carbon atom bearing the $R^7$ substituent;

—$R^6$-$R^{10}$— is selected from $^\#$—(CH$_2$)$_n$—(B)$_t$(CH$_2$)$_p$—$^{\#\#}$, $^\#$—(C$_2$-C$_6$-alkenylene)-(B)$_t$—(CH$_2$)$_p$, $^\#$—(CH$_2$)$_n$—(B)$_t$ (C$_2$-C$_6$-alkenylene)-$^{\#\#}$ and $^\#$—(CH$_2$)$_q$—(B)—(CH$_2$)$_r$— (B)—(CH$_2$)$_v$—$^{\#\#}$, where one or more CH$_2$ groups are optionally substituted with one or more substituents selected from a halogen atom, a hydroxyl group, a NR$^{17}$R$^{18}$ group, a $C_1$-$C_3$-alkyl group, a $C_1$-$C_3$-haloalkyl group, a $C_1$-$C_3$-alkoxy group and a $C_1$-$C_3$-haloalkoxy group, wherein $^\#$ is the point of attachment with the indole nitrogen atom and $^{\#\#}$ is the point of attachment with the carbon atom of the phenyl moiety bearing the $R^{10}$ substituent;

n is 2, 3, 4, 5, 6, 7, 8, 9, or 10;
t is 0 or 1;
p is 0, 1, 2, 3, 4, 5, or 6;
q is 2, 3, 4, 5, or 6;
r is 2, 3, 4, 5, or 6;
v is 0, 1, or 2;
where the integers selected for variables n, t, p, q, r, and v result in forming a 9- to 16-membered ring independently from the selection of variable A1, A2 or A3;

B is independently selected from a —C(O)NR$^{15}$— group, a —NR$^{15}$C(O)— group, a —N(R$^{15}$)— group, a —N(R$^{15}$)—C(=O)—N(R$^{15}$)— group, a —O—C (=O)—N(R$^{15}$)— group, a —N(R$^{15}$)—C(=O)—O— group, —O—, —S—, —S(O)—, —S(O)$_2$—, a —S(O) NR$^{15}$— group, a —NR$^{15}$S(O)— group, a —S(O)$_2$NR$^{15}$— group, a —NR$^{15}$S(O)$_2$— group,

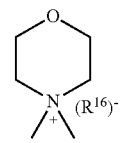

and —[N$^+$(R$^{21}$R$^{22}$)—(R$^{16}$)$^-$], $R^{15}$ is independently selected from a hydrogen atom, a $C_1$-$C_6$-alkyl group,
which is optionally substituted with one or more substituents selected from a halogen atom, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a heterocycloalkyl group, an aryl group, a (R$^{19}$)-(heterocycloalkylene)-(arylene)-O— group, a (heterocycloalkyl)-(arylene)-O— group, an aryl-O— group, an aryl-($C_1$-$C_3$-alkylene)-O— group, a ($R^{20}$)—S(O)$_2$-arylene-O— group, a ($R^{20}$)S(O)$_2$-heterocycloalkylene-arylene-O— group, an aryl-heteroarylene-O— group and an aryl-heteroarylene-O—($C_1$-$C_3$-alkylene)- group;

a phenyl group, a group

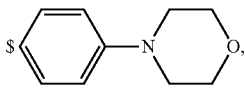

a group

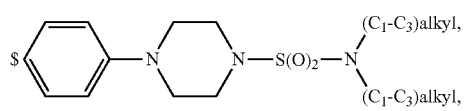

and
a group

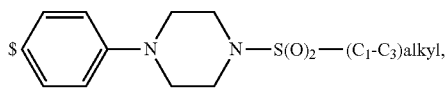

where $ is the point of attachment to the nitrogen atom, to which $R^{15}$ is attached, where $R^{16}$ is a pharmaceutically acceptable anion;

where $R^{17}$ and $R^{18}$ are each independently selected from a hydrogen atom, a $C_1$-$C_6$-alkyl group, a $C_1$-$C_6$-haloalkyl group, a $C_3$-$C_5$-cycloalkyl group, a $C_1$-$C_3$-alkyl-C(O)— group, a $C_1$-$C_3$-alkyl-S(O)$_2$— group and a $C_1$-$C_3$-alkyl-O—C(=O)— group;

where $R^{19}$ is selected from a hydrogen atom, a hydroxyl group, a cyano group, a $C_1$-$C_3$-alkyl group, a $C_1$-$C_6$-hydroxyalkyl group, a $C_1$-$C_3$-alkoxy group, a C(O)O$R^{21}$—($C_1$-$C_3$-alkylene)- group, a —C(O)O$R^{21}$ group, a —C(O)N$R^{21}R^{22}$ group, a ($C_1$-$C_3$-alkyl)-O—($C_1$-$C_3$-alkylene)-C(O)— group, a ($C_1$-$C_6$-alkyl)-C(O)-group, and a $C_3$-$C_6$-cycloalkyl-C(O)— group;

where $R^{20}$ is selected from a $C_1$-$C_3$-alkyl group, a $C_3$-$C_6$-cycloalkyl group and a $NR^{21}R^{22}$ group and where $R^{21}$ and $R^{22}$ are independently selected from a hydrogen atom or a $C_1$-$C_6$-alkyl group;

$R^8$ is selected from a hydrogen atom,
a $C_1$-$C_6$-alkyl group, which is optionally substituted with one or more substituents independently selected from a halogen atom, a hydroxyl group, a $C_1$-$C_3$-alkoxy group, a $C_1$-$C_3$-haloalkoxy group, a $C_3$-$C_6$-cycloalkyl group, a heterocycloalkyl group and a $NR^{21}R^{22}$ group;

a $C_1$-$C_3$-haloalkyl group, a $C_3$-$C_6$-cycloalkyl group and a $C_1$-$C_6$-alkyl group in which one or two not directly adjacent carbon atoms are independently replaced by a hetero atom selected from —O— or —NH—, $R^9$ is selected from a hydrogen atom,
a $C_1$-$C_4$-alkyl group,
a $C_1$-$C_3$-hydroxyalkyl group,
a $C_1$-$C_4$-haloalkyl group, a $C_1$-$C_4$-haloalkyl-NH—C(O)—O—($C_1$-$C_3$-alkylene)- group,
a $C_2$-$C_6$-haloalkenyl group,
a $C_1$-$C_6$-alkyl-O-group,
a $C_1$-$C_4$-haloalkoxy group,
a $C_1$-$C_6$-alkyl-O—($C_1$-$C_3$-alkylene)- group,
a ($C_3$-$C_7$)-cycloalkyl group,
a ($C_3$-$C_7$)-cycloalkyl-O—($C_1$-$C_3$-alkylene)- group,
a phenyl-O—($C_1$-$C_3$-alkylene)- group,
a phenyl-($C_1$-$C_3$-alkylene)-O—($C_1$-$C_3$-alkylene)- group,
a $R^{19}$-phenyl-($C_1$-$C_3$-alkylene)-O—($C_1$-$C_3$-alkylene)- group,
a $R^{19}$-phenylene-O—($C_1$-$C_3$-alkylene)- group,
a $R^{19}$-phenyl-heteroarylene-O—($C_1$-$C_3$-alkylene) group,
a ($R^{19}$)-(heterocycloalkylene)-($C_1$-$C_3$-alkylene)- group,
a ($R^{19}$)-(heterocycloalkylene)-(phenylene)-O—($C_1$-$C_3$-alkylene)- group,
a (heterocycloalkenyl)-(phenylene)-O—($C_1$-$C_3$-alkylene)- group,
a ($R^{19}$)-(heteroarylene)-($C_1$-$C_3$-alkylene)-O—($C_1$-$C_3$-alkylene)- group,
a ($R^{19}$)-(heteroarylene)-(phenylene)-O—($C_1$-$C_3$-alkylene)- group,
a ($R^{20}$)—S(O)$_2$-phenylene-O—($C_1$-$C_3$-alkylene)- group,
a ($R^{20}$)—S(O)$_2$—NH-phenylene-O—($C_1$-$C_3$-alkylene)- group,
a ($R^{20}$)—S(O)$_2$—NH-phenylene-O—($C_1$-$C_3$-alkylene)- group,
a ($R^{20}$)—S(O)$_2$—N($C_1$-$C_6$-alkyl)-phenylene-O—($C_1$-$C_3$-alkylene)- group,
a ($R^{20}$)—S(O)$_2$-heterocycloalkylene-phenylene-O—($C_1$-$C_3$-alkylene)- group,
a ($R^{19}$)-(heterocycloalkylene)-(heteroarylene)-O—($C_1$-$C_3$-alkylene)- group,
a ($R^{20}$)-heteroarylene-O—($C_1$-$C_3$-alkylene)- group,
a ($R^{19}$)-heteroarylene-O—($C_1$-$C_3$-alkylene)- group,
a ($R^{20}$)—S(O)$_2$-heteroarylene-O—($C_1$-$C_3$-alkylene)- group,
a ($R^{20}$)—S(O)$_2$-heterocycloalkylene-heteroarylene-O—($C_1$-$C_3$-alkylene)- group,
a $NR^{21}R^{22}$—($C_1$-$C_3$-alkylene)- group,
a ($C_1$-$C_3$-alkyl)-NH—($C_1$-$C_3$-alkylene)- group,
a ($C_1$-$C_3$-haloalkyl)-($C_1$-$C_3$-alkylene)-NH—($C_1$-$C_3$-alkylene)- group,
a ($C_1$-$C_3$-haloalkyl)-NH—($C_1$-$C_3$-alkylene)- group,
a ($C_1$-$C_3$-alkyl)-NH—C(O)—($C_1$-$C_3$-alkylene)- group,
a ($C_1$-$C_3$-alkyl)-N$R^{15}$—C(O)—($C_1$-$C_3$-alkylene)- group,
a ($C_1$-$C_3$-alkyl)-C(O)—NH—($C_1$-$C_3$-alkylene)- group,
a ($C_1$-$C_3$-alkyl)-C(O)—N$R^{15}$—($C_1$-$C_3$-alkylene)- group,
a group

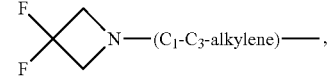

and a group

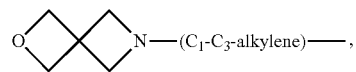

where the phenyl ring is optionally substituted with a halogen atom, a hydroxyl group, or a $C_1$-$C_3$-alkoxy group and the heterocycloalkyl group is optionally substituted with an oxo (=O) group or is optionally substituted with one or more substituents independently selected from a halogen atom, a hydroxyl group, a $C_1$-$C_3$-alkyl group, and a $C_1$-$C_3$-alkoxy group;

or $R^8$ and $R^9$ together form a 5- or 6-membered ring optionally containing one or two heteroatoms selected from —O—, and —$NR^{14}$—;

$R^{11}$ and $R^{13}$ are each independently selected from a hydrogen atom, a halogen atom, a $C_1$-$C_3$-alkyl group and a $C_1$-$C_3$-alkoxy group;

$R^{12}$ is selected from a hydrogen atom, a $C_1$-$C_3$-alkoxy group, a $C_1$-$C_3$-alkyl group, a $C_1$-$C_3$-haloalkyl group, a $C_1$-$C_3$-haloalkoxy group and a $NR^{17}R^{18}$ group;

or a tautomer, an N-oxide, or a salt thereof or a salt of a tautomer or a N-oxide or a mixture of same.

In accordance with a further aspect, the present invention provides compounds of general formula (I): in which A is

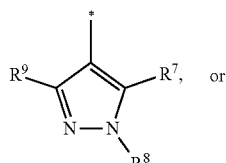

(A1)

or

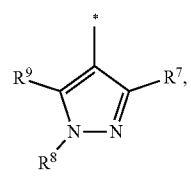

(A2)

wherein $R^6$ and $R^7$, together with two carbon atoms of the pyrazole ring, two carbon atoms of the indole moiety and the nitrogen atom to which $R^6$ is attached, form a 9- to 16-membered ring and * is the point of attachment of these moieties to the indole carbon atom bearing the A substituent or A is

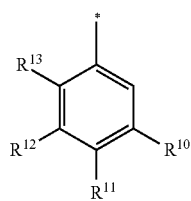

(A3)

whereby optionally one or two of the groups selected from $CR^{11}$, $CR^{12}$ or $CR^{13}$ may be replaced by a nitrogen atom, wherein $R^6$ and $R^{10}$, together with three carbon atoms of the phenyl ring, two carbon atoms of the indole moiety and the nitrogen atom to which $R^6$ is attached, form a 9- to 16-membered ring and * is the point of attachment of these moieties to the indole carbon atom bearing the A substituent;

$R^1$ and $R^2$ are each independently selected from a hydrogen atom, a halogen atom, a cyano group, a $C_1$-$C_3$-alkyl group and a $C_1$-$C_3$-alkoxy group;

$R^3$ is selected from a hydrogen atom, a halogen atom, a cyano group, a $C_1$-$C_3$-alkyl group, a $C_1$-$C_3$-haloalkyl group, a $C_1$-$C_3$-alkoxy group, a $C_1$-$C_3$-alkylthio group, a —S(O)—($C_1$-$C_3$-alkyl) group, a —S(O)$_2$—($C_1$-$C_3$-alkyl) group, a $C_1$-$C_3$-haloalkoxy group, a $C_1$-$C_3$-haloalkylthio group and a $C_3$-$C_5$-cycloalkyl group;

$R^4$ is selected from an aryl group and a heteroaryl group, which is optionally substituted with one, two, three, four or five substituents and each substituent is independently selected from a halogen atom, a cyano group, a $C_1$-$C_3$-alkyl group, a $C_1$-$C_3$-haloalkyl group(, a $C_1$-$C_3$-alkoxy group, a $C_1$-$C_3$-thioalkyl group, a $C_1$-$C_3$-haloalkoxy group, and a ($C_1$-$C_3$)-haloalkyl-S— group and a $C_3$-$C_5$-cycloalkyl group;

L is a group —$(CH_2)_m$-E- wherein any $CH_2$ group is optionally substituted with one or two substituents and each substituent is independently selected from a halogen atom, a cyano group, a hydroxyl group, a $C_1$-$C_3$-alkyl group and a $C_1$-$C_3$-alkoxy group, or two substituents are optionally taken together with their intervening atoms to form a saturated or partially unsaturated 3-6-membered cycloalkyl ring, or a 3-8 membered saturated or partially unsaturated heterocyclic ring having 1-2 heteroatoms independently selected from an oxygen atom, a sulfur atom, a —S(O)— group, a —S(O)$_2$— group and a —$NR^{14}$— group;

E is a bond, an oxygen atom, a sulfur atom, a —S(O)— group, a —S(O)$_2$— group or a —$NR^{14}$— group and constitutes the connecting element to $R^4$, where $R^{14}$ is a hydrogen atom or a $C_1$-$C_3$-alkyl group;

m is 2, 3, or 4;

$R^5$ is selected from a COOH group, or a

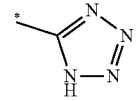

group, a —C(O)—NHS(O)$_2$($C_1$-$C_6$-alkyl) group, a —C(O)—NHS(O)$_2$($C_3$-$C_6$-cycloalkyl) group, a —C(O)—NHS(O)$_2$(aryl) group, a —C(O)—NHS(O)$_2$(CH$_2$)$_s$NHCO($C_1$-$C_6$-alkyl) group, a —C(O)—NHS(O)$_2$(CH$_2$)$_s$NHCO($C_3$-$C_6$-cycloalkyl) group and a —C(O)—NHS(O)$_2$(CH$_2$)$_s$NHCO(aryl) group;

s is 0, 1, 2, or 3;

—$R^6$-$R^7$— is selected from $^\#$—(CH$_2$)$_n$—(B)$_t$—(CH$_2$)$_p$—$^{\#\#}$, $^\#$—(C$_2$-C$_6$-alkenylene)-(B)$_t$—(CH$_2$)$_p$—$^{\#\#}$, $^\#$—(CH$_2$)$_n$—(B)$_t$(C$_2$-C$_6$-alkenylene)-$^{\#\#}$ and $^\#$—(CH$_2$)$_q$—(B)—(CH$_2$)$_t$—(B)—(CH$_2$)$_v$—$^{\#\#}$, wherein any CH$_2$ group is optionally substituted with one or more substituents selected from a halogen atom, a hydroxyl group, a NR$^{17}$R$^{18}$ group, a $C_1$-$C_3$-alkyl group, a $C_1$-$C_3$-haloalkyl group, a $C_1$-$C_3$-alkoxy group, a $C_1$-$C_3$-haloalkoxy group and a (heterocycloalkyl)-($C_1$-$C_3$-alkylene)- group, and where a double bond in any alkenylene can be replaced by a 1,2-cyclopropyl group, and said 1,2-cyclopropyl group is optionally substituted one or two times with a halogen atom or a $C_1$-$C_2$-alkyl group, wherein $^\#$ is the point of attachment with the indole nitrogen atom and $^{\#\#}$ is the point of attachment with the pyrazole carbon atom bearing the $R^7$ substituent;

—$R^6$-$R^{10}$— is selected from $^\#$—(CH$_2$)$_n$—(B)$_t$(CH$_2$)$_p$—$^{\#\#}$, $^\#$—(C$_2$-C$_6$-alkenylene)-(B)$_t$—(CH$_2$)$_p$, $^\#$—(CH$_2$)$_n$—(B)$_t$(C$_2$-C$_6$-alkenylene)-$^{\#\#}$ and $^\#$—(CH$_2$)$_q$—(B)—(CH$_2$)$_t$—(B)—(CH$_2$)$_v$—$^{\#\#}$, where one or more CH$_2$ groups are optionally substituted with one or more substituents selected from a halogen atom, a hydroxyl group, a $NR^{17}R^{18}$ group, a $C_1$-$C_3$-alkyl group, a $C_1$-$C_3$-haloalkyl group, a $C_1$-$C_3$-alkoxy group and a $C_1$-$C_3$-haloalkoxy group, wherein # is the point of attachment with the indole nitrogen atom and ## is the point of attachment with the carbon atom of the phenyl moiety bearing the $R^{10}$ substituent;

n is 2, 3, 4, 5, 6, 7, 8, 9, or 10;
t is 0 or 1;
p is 0, 1, 2, 3, 4, 5, or 6;
q is 2, 3, 4, 5, or 6;
r is 2, 3, 4, 5, or 6;
v is 0, 1, or 2;
where the integers selected for variables n, t, p, q, r, and v result in forming a 9- to 16-membered ring independently from the selection of variable A1, A2 or A3;

B is independently selected from a —C(O)$NR^{15}$— group, a —$NR^{15}$C(O)— group, a —N($R^{15}$)— group, a —N($R^{15}$)—C(=O)—N($R^{15}$)— group, a —O—C(=O)—N($R^{15}$)— group, a —N($R^{15}$)—C(=O)—O— group, —O—, —S—, —S(O)—, —S(O)$_2$—, a —S(O)$NR^{15}$— group, a —$NR^{15}$S(O)— group, a —S(O)$_2NR^{15}$— group, a —$NR^{15}$S(O)$_2$— group, $R^{15}$ is independently selected from a hydrogen atom,
  a $C_1$-$C_6$-alkyl group,
    which is optionally substituted with one or more substituents selected from a halogen atom, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a heterocycloalkyl group, an aryl group, a ($R^{19}$)-(heterocycloalkylene)-(arylene)-O— group, a (heterocycloalkyl)-(arylene)-O— group, an aryl-O— group, an aryl-($C_1$-$C_3$-alkylene)-O— group, a ($R^{20}$)—S(O)$_2$-arylene-O— group, a ($R^{20}$)S(O)$_2$-heterocycloalkylene-arylene-O— group, an aryl-heteroarylene-O— group and an aryl-heteroarylene-O—($C_1$-$C_3$-alkylene)- group;
  a phenyl group, a group

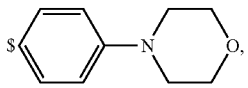

a group

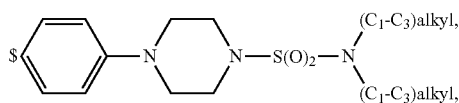

and
a group

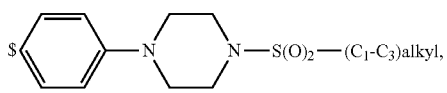

where $ is the point of attachment to the nitrogen atom, to which $R^{15}$ is attached, where $R^{16}$ is a pharmaceutically acceptable anion;
where $R^{17}$ and $R^{18}$ are each independently selected from a hydrogen atom, a $C_1$-$C_6$-alkyl group, a $C_1$-$C_6$-haloalkyl group, a $C_3$-$C_5$-cycloalkyl group, a $C_1$-$C_3$-alkyl-C(O)— group, a $C_1$-$C_3$-alkyl-S(O)$_2$— group and a $C_1$-$C_3$-alkyl-O—C(=O)— group;
where $R^{19}$ is selected from a hydrogen atom, a hydroxyl group, a cyano group, a $C_1$-$C_3$-alkyl group, a $C_1$-$C_6$-hydroxyalkyl group, a $C_1$-$C_3$-alkoxy group, a C(O)$OR^{21}$—($C_1$-$C_3$-alkylene)- group, a —C(O)$OR^{21}$ group, a —C(O)$NR^{21}R^{22}$ group, a ($C_1$-$C_3$-alkyl)-O—($C_1$-$C_3$-alkylene)-C(O)— group, a ($C_1$-$C_6$-alkyl)-C(O)-group, and a $C_3$-$C_6$-cycloalkyl-C(O)— group;
where $R^{20}$ is selected from a $C_1$-$C_3$-alkyl group, a $C_3$-$C_6$-cycloalkyl group and a $NR^{21}R^{22}$ group and where $R^{21}$ and $R^{22}$ are independently selected from a hydrogen atom or a $C_1$-$C_6$-alkyl group;

$R^8$ is selected from a hydrogen atom,
  a $C_1$-$C_6$-alkyl group, which is optionally substituted with one or more substituents independently selected from a halogen atom, a hydroxyl group, a $C_1$-$C_3$-alkoxy group, a $C_1$-$C_3$-haloalkoxy group, a $C_3$-$C_6$-cycloalkyl group, a heterocycloalkyl group and a $NR^{21}R^{22}$ group;
  a $C_1$-$C_3$-haloalkyl group, a $C_3$-$C_6$-cycloalkyl group and a $C_1$-$C_6$-alkyl group in which one or two not directly adjacent carbon atoms are independently replaced by a hetero atom selected from —O— or —NH—, $R^9$ is selected from a hydrogen atom,
  a $C_1$-$C_4$-alkyl group,
  a $C_1$-$C_3$-hydroxyalkyl group,
  a $C_1$-$C_4$-haloalkyl group,
  a $C_1$-$C_4$-haloalkyl-NH—C(O)—O—($C_1$-$C_3$-alkylene)- group,
  a $C_2$-$C_6$-haloalkenyl group,
  a $C_1$-$C_6$-alkyl-O-group,
  a $C_1$-$C_4$-haloalkoxy group,
  a $C_1$-$C_6$-alkyl-O—($C_1$-$C_3$-alkylene)- group,
  a ($C_3$-$C_7$)-cycloalkyl group,
  a ($C_3$-$C_7$)-cycloalkyl-O—($C_1$-$C_3$-alkylene)- group,
  a phenyl-O—($C_1$-$C_3$-alkylene)- group,
  a phenyl-($C_1$-$C_3$-alkylene)-O—($C_1$-$C_3$-alkylene)- group,
  a $R^{19}$-phenyl-($C_1$-$C_3$-alkylene)-O—($C_1$-$C_3$-alkylene)- group,
  a $R^{19}$-phenylene-O—($C_1$-$C_3$-alkylene)- group,
  a $R^{19}$-phenyl-heteroarylene-O—($C_1$-$C_3$-alkylene) group,
  a ($R^{19}$)-(heterocycloalkylene)-($C_1$-$C_3$-alkylene)- group,
  a ($R^{19}$)-(heterocycloalkylene)-(phenylene)-O—($C_1$-$C_3$-alkylene)- group,
  a (heterocycloalkenyl)-(phenylene)-O—($C_1$-$C_3$-alkylene)- group,
  a ($R^{19}$)-(heteroarylene)-($C_1$-$C_3$-alkylene)-O—($C_1$-$C_3$-alkylene)- group,
  a ($R^{19}$)-(heteroarylene)-(phenylene)-O—($C_1$-$C_3$-alkylene)- group,
  a ($R^{20}$)—S(O)$_2$-phenylene-O—($C_1$-$C_3$-alkylene)- group,
  a ($R^{20}$)—S(O)$_2$—NH-phenylene-O—($C_1$-$C_3$-alkylene)- group,
  a ($R^{20}$)—S(O)$_2$—NH-phenylene-O—($C_1$-$C_3$-alkylene)- group,
  a ($R^{20}$)—S(O)$_2$—N($C_1$-$C_6$-alkyl)-phenylene-O—($C_1$-$C_3$-alkylene)- group,
  a ($R^{20}$)—S(O)$_2$-heterocycloalkylene-phenylene-O—($C_1$-$C_3$-alkylene)- group,
  a ($R^{19}$)-(heterocycloalkylene)-(heteroarylene)-O—($C_1$-$C_3$-alkylene)- group,
  a ($R^{20}$)-heteroarylene-O—($C_1$-$C_3$-alkylene)- group, a ($R^{19}$)-heteroarylene-O—($C_1$-$C_3$-alkylene)- group,
a ($R^{20}$)—S(O)$_2$-heteroarylene-O—($C_1$-$C_3$-alkylene)- group,
a ($R^{20}$)—S(O)$_2$-heterocycloalkylene-heteroarylene-O—($C_1$-$C_3$-alkylene)- group,
a NR$^{21}$R$^{22}$—($C_1$-$C_3$-alkylene)- group,
a ($C_1$-$C_3$-alkyl)-NH—($C_1$-$C_3$-alkylene)- group,
a ($C_1$-$C_3$-haloalkyl)-($C_1$-$C_3$-alkylene)-NH—($C_1$-$C_3$-alkylene)- group,
a ($C_1$-$C_3$-haloalkyl)-NH—($C_1$-$C_3$-alkylene)- group,
a ($C_1$-$C_3$-alkyl)-NH—C(O)—($C_1$-$C_3$-alkylene)- group,
a ($C_1$-$C_3$-alkyl)-NR$^{15}$—C(O)—($C_1$-$C_3$-alkylene)- group,
a ($C_1$-$C_3$-alkyl)-C(O)—NH—($C_1$-$C_3$-alkylene)- group,
a ($C_1$-$C_3$-alkyl)-C(O)—NR$^{15}$—($C_1$-$C_3$-alkylene)- group,
a group

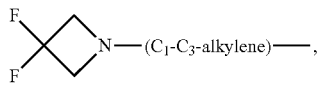

and a group

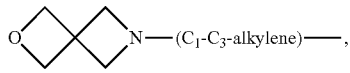

where the phenyl ring is optionally substituted with a halogen atom, a hydroxyl group, or a $C_1$-$C_3$-alkoxy group and
the heterocycloalkyl group is optionally substituted with an oxo (=O) group or is optionally substituted with one or more substituents independently selected from a halogen atom, a hydroxyl group, a $C_1$-$C_3$-alkyl group, and a $C_1$-$C_3$-alkoxy group;
or $R^8$ and $R^9$ together form a 5- or 6-membered ring optionally containing one or two heteroatoms selected from —O—, and —NR$^{14}$—;
$R^{11}$ and $R^{13}$ are each independently selected from a hydrogen atom, a halogen atom, a $C_1$-$C_3$-alkyl group and a $C_1$-$C_3$-alkoxy group;
$R^{12}$ is selected from a hydrogen atom, a $C_1$-$C_3$-alkoxy group, a $C_1$-$C_3$-alkyl group, a $C_1$-$C_3$-haloalkyl group, a $C_1$-$C_3$-haloalkoxy group and a NR$^{17}$R$^{18}$ group;
or a tautomer, an N-oxide, or a salt thereof or a salt of a tautomer or a N-oxide or a mixture of same.

In accordance with a further aspect, the present invention provides compounds of general formula (I): in which
A is

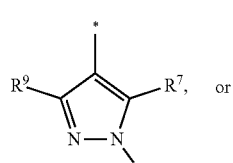

(A1)

or

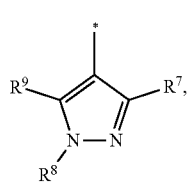

(A2)

wherein $R^6$ and $R^7$, together with two carbon atoms of the pyrazole ring, two carbon atoms of the indole moiety and the nitrogen atom to which $R^6$ is attached, form a 9- to 16-membered ring and * is the point of attachment of these moieties to the indole carbon atom bearing the A substituent
or
A is

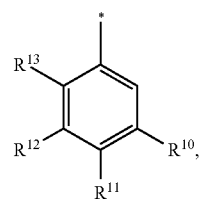

(A3)

wherein $R^6$ and $R^{10}$, together with three carbon atoms of the phenyl ring, two carbon atoms of the indole moiety and the nitrogen atom to which $R^6$ is attached, form a 9- to 16-membered ring and * is the point of attachment of these moieties to the indole carbon atom bearing the A substituent;
$R^1$ and $R^2$ are each independently selected from a hydrogen atom, a halogen atom, a cyano group, a $C_1$-$C_3$-alkyl group and a $C_1$-$C_3$-alkoxy group;
$R^3$ is selected from a hydrogen atom, a halogen atom, a cyano group, a $C_1$-$C_3$-alkyl group, a $C_1$-$C_3$-haloalkyl group, a $C_1$-$C_3$-alkoxy group, a $C_1$-$C_3$-alkylthio group, a —S(O)—($C_1$-$C_3$-alkyl) group, a —S(O)$_2$—($C_1$-$C_3$-alkyl) group, a $C_1$-$C_3$-haloalkoxy group, a $C_1$-$C_3$-haloalkylthio group and a $C_3$-$C_5$-cycloalkyl group.
$R^4$ is selected from an aryl group and a heteroaryl group, which is optionally substituted with one, two, three, four or five substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, a ($C_1$-$C_3$)-haloalkyl-S— group and a $C_3$-$C_5$-cycloalkyl group,
L is a group —(CH$_2$)$_m$-E- wherein any CH$_2$ group is optionally substituted with one or two substituents and each substituent is independently selected from a halogen atom, a cyano group, a hydroxyl group, a $C_1$-$C_3$-alkyl group and a $C_1$-$C_3$-alkoxy group, or two substituents are optionally taken together with their intervening atoms to form a saturated or partially unsaturated 3-6-membered cycloalkyl ring, or a 3-8 membered saturated or partially unsaturated heterocyclic ring having 1-2 heteroatoms independently selected from an oxygen atom, a sulfur atom, a —S(O)— group, a —S(O)$_2$— group and a —NR$^{14}$— group;
E is a bond, an oxygen atom, a sulfur atom, a —S(O)— group, a —S(O)$_2$— group or a —NR$^{14}$— group and constitutes the connecting element to $R^4$,
where $R^{14}$ is a hydrogen atom or a $C_1$-$C_3$-alkyl group;
m is 2, 3, or 4;
$R^5$ is selected from a COOH group, a

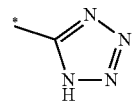 [SMILES: *c1nnn[nH]1]

group, a —C(O)—NHS(O)$_2$(C$_1$-C$_6$-alkyl) group, a —C(O)—NHS(O)$_2$(C$_3$-C$_6$-cycloalkyl) group, a —C(O)—NHS(O)$_2$(aryl) group, a —C(O)—NHS(O)$_2$(CH$_2$)$_s$NHCO(C$_1$-C$_6$-alkyl) group, a —C(O)—NHS(O)$_2$(CH$_2$)$_s$NHCO(C$_3$-C$_6$-cycloalkyl) group and a —C(O)—NHS(O)$_2$(CH$_2$)$_s$NHCO(aryl) group;

s is 0, 1, 2, or 3;

—R$^6$-R$^7$— is selected from $^\#$—(CH$_2$)$_n$—(B)$_t$—(CH$_2$)$_p$—$^{\#\#}$, $^\#$—(C$_2$-C$_6$-alkenylene)-(B)$_t$—(CH$_2$)$_p$—$^{\#\#}$, $^\#$—(CH$_2$)$_n$—(B)$_t$—(C$_2$-C$_6$-alkenylene)-$^{\#\#}$, and $^\#$—(CH$_2$)$_q$—(B)—(CH$_2$)$_r$—(B)—(CH$_2$)$_v$—$^{\#\#}$, wherein any CH$_2$ group is optionally substituted with one or more substituents selected from a halogen atom, a hydroxyl group, a NR$^{17}$R$^{18}$ group, a C$_1$-C$_3$-alkyl group, a C$_1$-C$_3$-haloalkyl group, a C$_1$-C$_3$-alkoxy group, a C$_1$-C$_3$-haloalkoxy group and a (heterocycloalkyl)-(C$_1$-C$_3$-alkylene)- group, and where a double bond in any alkenylene can be replaced by a 1,2-cyclopropyl group, and said 1,2-cyclopropyl group is optionally substituted one or two times with a halogen atom or a C$_1$-C$_2$-alkyl group, wherein $^\#$ is the point of attachment with the indole nitrogen atom and $^{\#\#}$ is the point of attachment with the pyrazole carbon atom bearing the R$^7$ substituent;

—R$^6$-R$^{10}$— is selected from $^\#$—(CH$_2$)$_n$—(B)$_t$—(CH$_2$)$_p$—$^{\#\#}$, $^\#$—(C$_2$-C$_6$-alkenylene)-(B)$_t$—(CH$_2$)$_p$—$^{\#\#}$, $^\#$—(CH$_2$)$_n$—(B)$_t$—(C$_2$-C$_6$-alkenylene)-$^{\#\#}$, and $^\#$—(CH$_2$)$_q$—(B)—(CH$_2$)$_r$—(B)—(CH$_2$)$_v$—$^{\#\#}$, where one or more CH$_2$ groups are optionally substituted with one or more substituents selected from a halogen atom, a hydroxyl group, a NR$^{17}$R$^{18}$ group, a C$_1$-C$_3$-alkyl group, a C$_1$-C$_3$-haloalkyl group, a C$_1$-C$_3$-alkoxy group and a C$_1$-C$_3$-haloalkoxy group, wherein $^\#$ is the point of attachment with the indole nitrogen atom and $^{\#\#}$ is the point of attachment with the carbon atom of the phenyl moiety bearing the R$^{10}$ substituent;

n is 2, 3, 4, 5, 6, 7, 8, 9, or 10;
t is 0 or 1;
p is 0, 1, 2, 3, 4, 5, or 6;
q is 2, 3, 4, 5, or 6;
r is 2, 3, 4, 5, or 6;
v is 0, 1, or 2;

where the integers selected for variables n, t, p, q, r, and v result in forming a 9- to 16-membered ring independently from the selection of variable A1, A2 or A3;

B is independently selected from a —C(O)NR$^{15}$— group, a —NR$^{15}$C(O)— group, a —N(R$^{15}$)— group, a —N(R$^{15}$)—C(=O)—N(R$^{15}$)— group, a —O—C(=O)—N(R$^{15}$)— group, a —N(R$^{15}$)—C(=O)—O— group, —O—, —S—, —S(O)—, —S(O)$_2$—, a —S(O)NR$^{15}$— group, a —NR$^{15}$S(O)— group, a —S(O)$_2$NR$^{15}$— group, a —NR$^{15}$S(O)$_2$— group and

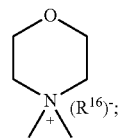

R$^{15}$ is independently selected from a hydrogen atom,
a C$_1$-C$_6$-alkyl group,
which is optionally substituted with one or more substituents selected from a halogen atom, a C$_1$-C$_3$-alkyl group, a C$_1$-C$_3$-haloalkyl group, a C$_1$-C$_3$-hydroxyalkyl group, a C$_1$-C$_3$-alkoxy group, a C$_1$-C$_3$-haloalkoxy group, a heterocycloalkyl group, an aryl group, a (R$^{19}$)-(heterocycloalkylene)-(arylene)-O— group, an aryl-O— group, a aryl-(C$_1$-C$_3$-alkylene)-O— group, a (R$^{20}$)—S(O)$_2$— arylene-O— group, a (R$^{20}$)S(O)$_2$— heterocycloalkylene-arylene-O— group and an aryl-heteroarylene-O— group;

a phenyl group, a group

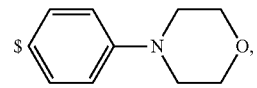

a group

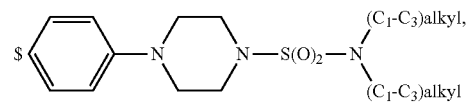

and
a group

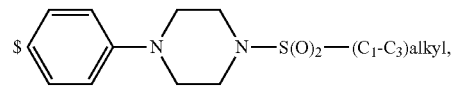

where $ is the point of attachment to the nitrogen atom, to which R$^{15}$ is attached, where R$^{16}$ is a pharmaceutically acceptable anion;
where R$^{17}$ and R$^{18}$ are each independently selected from a hydrogen atom, a C$_1$-C$_6$-alkyl group, a C$_1$-C$_6$-haloalkyl group, a C$_3$-C$_5$-cycloalkyl group, a C$_1$-C$_3$-alkyl-C(O)— group, a C$_1$-C$_3$-alkylS(O)$_2$— group and a C$_1$-C$_3$-alkyl-O—C(=O)— group;

where R$^{19}$ is selected from a hydrogen atom, a hydroxy group, a cyano group, a C$_1$-C$_3$-alkyl group, a C$_1$-C$_6$-hydroxyalkyl group, a C$_1$-C$_3$-alkoxy group, a C(O)OR$^{21}$—(C$_1$-C$_3$-alkylene)- group, a —C(O)OR$^{21}$ group, a —C(O)NR$^{21}$R$^{22}$ group, a (C$_1$-C$_3$-alkyl)-O—(C$_1$-C$_3$-alkylene)-C(O)— group, a (C$_1$-C$_6$-alkyl)-C(O)-group, group and a C$_3$-C$_6$-cycloalkyl-C(O)— group;

where R$^{20}$ is selected from a C$_1$-C$_3$-alkyl group, a C$_3$-C$_6$-cycloalkyl group, and a NR$^{21}$R$^{22}$ group; and where R$^{21}$ and R$^{22}$ is independently from each other a hydrogen or a C$_1$-C$_6$-alkyl group;

R$^8$ is a hydrogen atom,
a C$_1$-C$_6$-alkyl group, which is optionally substituted with one or more substituents independently selected from a halogen atom, a hydroxyl group, a C$_1$-C$_3$-alkoxy group, a C$_1$-C$_3$-haloalkoxy group, a C$_3$-C$_6$-cycloalkyl group, a heterocycloalkyl group and a NR$^{21}$R$^{22}$ group; or
a C$_1$-C$_3$-haloalkyl group,
a C$_3$-C$_6$-cycloalkyl group; or
a C$_1$-C$_6$-alkyl group in which one or two not directly adjacent carbon atoms are independently replaced by a hetero atom selected from —O— and —NH—;

R$^9$ is selected from a hydrogen atom,
a C$_1$-C$_4$-alkyl group,
a C$_1$-C$_3$-hydroxyalkyl group,
a C$_1$-C$_4$-haloalkyl group, C$_1$-C$_4$-haloalkyl-NH—C(O)—O—(C$_1$-C$_3$-alkylene)- group,
a C$_2$-C$_6$-haloalkenyl group, a $C_1$-$C_6$-alkyl-O-group,
a $C_1$-$C_4$-haloalkoxy group,
a $C_1$-$C_6$-alkyl-O—($C_1$-$C_3$-alkylene)- group,
a ($C_3$-$C_7$)-cycloalkyl group,
a ($C_3$-$C_7$)-cycloalkyl-O—($C_1$-$C_3$-alkylene)- group,
a phenyl-O—($C_1$-$C_3$-alkylene)- group,
a phenyl-($C_1$-$C_3$-alkylene)-O—($C_1$-$C_3$-alkylene)- group,
a ($R^{19}$)-phenylene-O—($C_1$-$C_3$-alkylene)- group,
a ($R^{19}$)-phenylene-($C_1$-$C_3$-alkylene)-O—($C_1$-$C_3$-alkylene)- group,
a ($R^{19}$)-phenylene-heteroarylene-O—($C_1$-$C_3$-alkylene) group,
a ($R^{19}$)-(heterocycloalkylene)-($C_1$-$C_6$-alkylene)- group,
a ($R^{19}$)-(heterocycloalkylene)-(phenylene)-O—($C_1$-$C_3$-alkylene)- group,
a (heterocycloalkenylene)-(phenylene)-O—($C_1$-$C_3$-alkylene)- group,
a ($R^{19}$)-(heteroarylene)-($C_1$-$C_3$-alkylene)-O—($C_1$-$C_3$-alkylene)- group,
a ($R^{19}$)-(heteroarylene)-(phenylene)-O—($C_1$-$C_3$-alkylene)- group,
a ($R^{19}$)-(phenylene)-($C_1$-$C_3$-alkylene)-O—($C_1$-$C_3$-alkylene)- group,
a ($R^{20}$)—S(O)$_2$-(phenylene)-O—($C_1$-$C_3$-alkylene)- group,
a ($R^{20}$)—S(O)$_2$—NH-phenylene-O—($C_1$-$C_3$-alkylene)- group,
a ($R^{20}$)—S(O)$_2$—N($C_1$-$C_6$-alkyl)-phenylene-O—($C_1$-$C_3$-alkylene)- group,
a ($R^{20}$)—S(O)$_2$-(heterocycloalkylene)-(phenylene)-O—($C_1$-$C_3$-alkylene)- group,
a ($R^{19}$)-(heterocycloalkylene)-(heteroarylene)-O—($C_1$-$C_3$-alkylene)- group,
a ($R^{20}$)-(heteroarylene)-O—($C_1$-$C_3$-alkylene)- group,
a ($R^{20}$)—S(O)$_2$-(heteroarylene)-O—($C_1$-$C_3$-alkylene)- group,
a ($R^{20}$)—S(O)$_2$-(heterocycloalkylene)-(heteroarylene)-O—($C_1$-$C_3$-alkylene)- group,
a $NR^{21}R^{22}$—($C_1$-$C_3$-alkylene)- group,
a ($C_1$-$C_3$-alkyl)-NH—($C_1$-$C_3$-alkylene)- group,
a ($C_1$-$C_3$-haloalkyl)-($C_1$-$C_3$-alkylene)-NH—($C_1$-$C_3$-alkylene)- group,
a ($C_1$-$C_3$-haloalkyl)-NH—($C_1$-$C_3$-alkylene)- group,
a ($C_1$-$C_3$-alkyl)-NH—C(O)—($C_1$-$C_3$-alkylene)- group,
a ($C_1$-$C_3$-alkyl)-$NR^{15}$—C(O)—($C_1$-$C_3$-alkylene)- group,
a ($C_1$-$C_3$-alkyl)-C(O)—NH—($C_1$-$C_3$-alkylene)- group,
a ($C_1$-$C_3$-alkyl)-C(O)—$NR^{15}$—($C_1$-$C_3$-alkylene)- group,
a

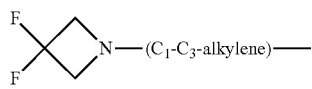

group, and a

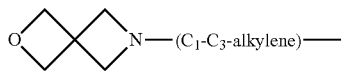

group,
where the phenyl ring is optionally substituted with a halogen atom, a hydroxyl group, or a $C_1$-$C_3$-alkoxy group and the heterocycloalkyl group is optionally substituted with an oxo (=O) group or is optionally substituted with one or more substituents independently selected from a halogen atom and a $C_1$-$C_3$-alkyl group;
or $R^8$ and $R^9$ together form a 5- or 6-membered ring optionally containing one or two heteroatoms selected from of —O— and —$NR^{14}$—;
$R^{11}$ and $R^{13}$ are each independently selected from a hydrogen atom, a halogen atom, a $C_1$-$C_3$-alkyl group and a $C_1$-$C_3$-alkoxy group;
$R^{12}$ is selected from a hydrogen atom, a $C_1$-$C_3$-alkoxy group, a $C_1$-$C_3$-alkyl group, a $C_1$-$C_3$-haloalkyl group, a $C_1$-$C_3$-haloalkoxy group and a $NR^{17}R^{18}$ group;
or a tautomer, an N-oxide, or a salt thereof or a salt of a tautomer or a N-oxide or a mixture of same.

In accordance with a further aspect, the present invention provides compounds of general formula (I): in which A is

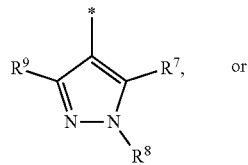

(A1)

or (A2)

wherein $R^6$ and $R^7$, together with two carbon atoms of the pyrazole ring, two carbon atoms of the indole moiety and the nitrogen atom to which $R^6$ is attached, form a 9- to 13-membered ring and * is the point of attachment of these moieties to the indole carbon atom bearing the A substituent or
A is

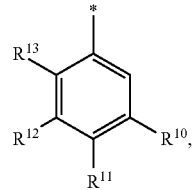

(A3)

wherein $R^6$ and $R^{10}$, together with three carbon atoms of the phenyl ring, two carbon atoms of the indole moiety and the nitrogen atom to which $R^6$ is attached, form a 9-13-membered ring and * is the point of attachment of these moieties to the indole carbon atom bearing the A substituent;
$R^1$ and $R^2$ are each independently selected from a hydrogen atom, a $C_1$-$C_3$-alkyl group, and a $C_1$-$C_3$-alkoxy group;
$R^3$ is selected from a hydrogen atom, a halogen atom, a $C_1$-$C_3$-alkyl group, and a $C_1$-$C_3$-alkoxy group;
$R^4$ is an aryl group, which is optionally substituted with one, two, three, substituents and each substituent is independently selected from a halogen atom, a $C_1$-$C_3$-alkyl group, and a $C_1$-$C_3$-haloalkyl group;

L is a group —$(CH_2)_m$-E- wherein any $CH_2$ group is optionally substituted with an $C_1$-$C_3$-alkyl group;

E is an oxygen atom;

m is 2, or 3;

$R^5$ is a COOH group;

—$R^6$-$R^7$— is selected from $^\#$—$(CH_2)_n$—$(B)_t$$(CH_2)_p$—$^{\#\#}$, $^\#$—$(C_2$-$C_6$-alkenylene)-$(B)_t$$(CH_2)_p$—$^{\#\#}$, and $^\#$—$(CH_2)_q$—$(B)$—$(CH_2)_r$—$(B)$—$(CH_2)_v$—$^{\#\#}$, wherein $^\#$ is the point of attachment with the indole nitrogen atom and $^{\#\#}$ is the point of attachment with the pyrazole carbon atom bearing the $R^7$ substituent;

—$R^6$-$R^{10}$— is $^\#$—$(CH_2)_q$—$(B)$—$(CH_2)_r$$(B)$—$(CH_2)_v$—$^{\#\#}$, wherein $^\#$ is the point of attachment with the indole nitrogen atom and $^{\#\#}$ is the point of attachment with the carbon atom of the phenyl moiety bearing the $R^{10}$ substituent;

n is 2, 3, 4, 5, or 6;

t is 0 or 1;

p is 0 or 1;

q is 2;

r is 2;

v is 0 or 1;

where the integers selected for variables n, t, p, q, r, and v result in forming a 9- to 13-membered ring independently from the selection of variable A1, A2 or A3;

B is independently selected from a —N($R^{15}$)— group, —O—, and,

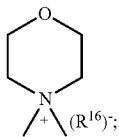

$R^{15}$ is independently selected from a hydrogen atom,
a $C_1$-$C_3$-alkyl group which is optionally substituted with a phenyl group;
a phenyl group, a group

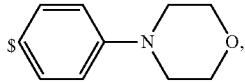

a group,

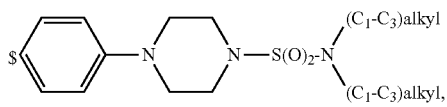

and
a group

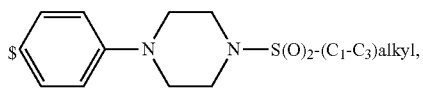

where $ is the point of attachment to the nitrogen atom, to which $R^{15}$ is attached, where $R^{16}$ is a pharmaceutically acceptable anion;

where $R^{19}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a C(O)OR$^{21}$—($C_1$-$C_3$-alkylene)- group, a —C(O)OR$^{21}$ group, a —C(O)NR$^{21}$R$^{22}$ group, a ($C_1$-$C_3$-alkyl)-O—($C_1$-$C_3$-alkylene)-C(O)— group, ($C_1$-$C_3$-alkyl)-C(O)-group, and a $C_3$-$C_6$-cycloalkyl-C(O)— group;

where $R^{20}$ is selected from a $C_1$-$C_3$-alkyl group, a $C_3$-$C_6$-cycloalkyl group, and a NR$^{21}$R$^{22}$ group; and where $R^{21}$ and $R^{22}$ are independently selected from a hydrogen atom and a $C_1$-$C_3$-alkyl group;

$R^8$ is selected from a hydrogen atom,
a $C_1$-$C_3$-alkyl group, which is optionally substituted with one or more substituents independently selected from a halogen atom, a hydroxyl group, a $C_1$-$C_3$-alkoxy group, a $C_1$-$C_3$-haloalkoxy group, a $C_3$-$C_6$-cycloalkyl group, a heterocycloalkyl group, or a NR$^{21}$R$^{22}$ group;
a $C_1$-$C_3$-haloalkyl group,
a $C_3$-$C_6$-cycloalkyl group;

$R^9$ is selected from a hydrogen atom,
a $C_1$-$C_4$-alkyl group,
a $C_1$-$C_3$-hydroxyalkyl group,
a $C_1$-$C_4$-haloalkyl group,
a $C_1$-$C_4$-haloalkyl-NH—C(O)—O—($C_1$-$C_3$-alkylene)- group,
a $C_2$-$C_6$-haloalkenyl group,
a $C_1$-$C_6$-alkyl-O— group,
a $C_1$-$C_4$-haloalkoxy group,
a $C_1$-$C_6$-alkyl-O—($C_1$-$C_3$-alkylene)- group,
a ($C_3$-$C_7$)-cycloalkyl group,
a ($C_3$-$C_7$)-cycloalkyl-O—($C_1$-$C_3$-alkylene)- group,
a phenyl-O—($C_1$-$C_3$-alkylene)- group,
a ($R^{19}$)-phenylene-($C_1$-$C_3$-alkylene)-O—($C_1$-$C_3$-alkylene)- group,
a ($R^{19}$)-phenyl-($C_1$-$C_3$-alkylene)-O—($C_1$-$C_3$-alkylene)- group,
a ($R^{19}$)-phenylene-O—($C_1$-$C_3$-alkylene)- group,
a ($R^{19}$)-phenyl-heteroarylene-O—($C_1$-$C_3$-alkylene)- group,
a ($R^{19}$)-(heterocycloalkylene)-($C_1$-$C_3$-alkylene)- group,
a ($R^{19}$)-(heterocycloalkylene)-(phenylene)-O—($C_1$-$C_3$-alkylene)- group,
a ($R^{19}$)-(heterocycloalkenylene)-(phenylene)-O—($C_1$-$C_3$-alkylene)- group,
a ($R^{19}$)-(heteroaryl-($C_1$-$C_3$-alkylene)-O—($C_1$-$C_3$-alkylene)- group,
a ($R^{19}$)-(heteroaryl)-(phenylene)-O—($C_1$-$C_3$-alkylene)- group,
a ($R^{20}$)—S(O)$_2$-phenylene-O—($C_1$-$C_3$-alkylene)- group,
a ($R^{20}$)—S(O)$_2$—NH-phenylene-O—($C_1$-$C_3$-alkylene)- group,
a ($R^{20}$)—S(O)$_2$—N—($C_1$-$C_3$-alkylene)-phenylene-O—($C_1$-$C_3$-alkylene)- group,
a ($R^{20}$)—S(O)$_2$-heterocycloalkylene-phenylene-O—($C_1$-$C_3$-alkylene)- group,
a ($R^{19}$)-(heterocycloalkylene)-(heteroarylene)-O—($C_1$-$C_3$-alkylene)- group,
a ($R^{19}$)-heteroarylene-O—($C_1$-$C_3$-alkylene)- group,
a ($R^{20}$)—S(O)$_2$-heteroarylene-O—($C_1$-$C_3$-alkylene)- group,
a ($R^{20}$)—S(O)$_2$-heterocycloalkylene-heteroarylene-O—($C_1$-$C_3$-alkylene)- group,
a NR$^{21}$R$^{22}$—($C_1$-$C_3$-alkylene)- group,
a ($C_1$-$C_3$-alkyl)-NH—($C_1$-$C_3$-alkylene)- group, a (C$_1$-C$_3$-haloalkyl)-(C$_1$-C$_3$-alkylene)-NH—(C$_1$-C$_3$-alkylene)- group, a group

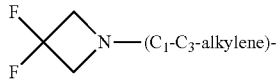

a group,

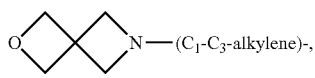

where the phenyl ring is optionally substituted with a halogen atom, a hydroxyl group, a C$_1$-C$_3$-alkoxy group and the heterocycloalkyl group is optionally substituted with an oxo (=O) group or is optionally substituted with a C$_1$-C$_3$-alkyl group;

or R$^8$ and R$^9$ together form 6-membered ring optionally containing one or two oxygen atoms, R$^{11}$ and R$^{13}$ are each independently selected from a hydrogen atom, and a C$_1$-C$_3$-alkyl group;

R$^{12}$ is selected from a hydrogen atom, and a C$_1$-C$_3$-alkoxy group;

or a tautomer, an N-oxide, or a salt thereof or a salt of a tautomer or a N-oxide or a mixture of same.

In accordance with a further aspect, the present invention provides compounds of general formula (I): in which A is

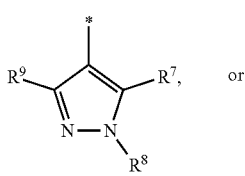 (A1)

or

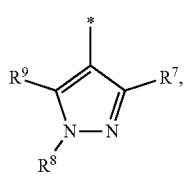 (A2)

wherein R$^6$ and R$^7$, together with two carbon atoms of the pyrazole ring, two carbon atoms of the indole moiety and the nitrogen atom to which R$^6$ is attached, form a 9- to 12-membered ring and * is the point of attachment of these moieties to the indole carbon atom bearing the A substituent or A is

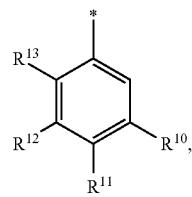 (A3)

wherein R$^6$ and R$^{10}$, together with three carbon atoms of the phenyl ring, two carbon atoms of the indole moiety and the nitrogen atom to which R$^6$ is attached, form a 9-12-membered ring and * is the point of attachment of these moieties to the indole carbon atom bearing the A substituent;

R$^1$ and R$^2$ are each independently selected from a hydrogen atom, a C$_1$-C$_3$-alkyl group, and a C$_1$-C$_3$-alkoxy group;

R$^3$ is selected from a hydrogen atom, a halogen atom, a C$_1$-C$_3$-alkyl group, and a C$_1$-C$_3$-alkoxy group;

R$^4$ is an aryl group, which is optionally substituted with one, two, three, substituents and each substituent is independently selected from a halogen atom, a C$_1$-C$_3$-alkyl group, and a C$_1$-C$_3$-haloalkyl group;

L is a group —(CH$_2$)$_m$-E- wherein any CH$_2$ group is optionally substituted with an C$_1$-C$_3$-alkyl group;

E is an oxygen atom;

m is 2, or 3;

R$^5$ is a COOH group;

—R$^6$-R$^7$— is selected from $^{\#}$—(CH$_2$)$_n$—(B)$_t$(CH$_2$)$_p$—$^{\#\#}$, $^{\#}$—(C$_2$-C$_6$-alkenylene)-(B)$_r$—(CH$_2$)$_p$—$^{\#\#}$ and $^{\#}$—(CH$_2$)$_q$—(B)—(CH$_2$)$_r$(B)—(CH$_2$)$_v$—$^{\#\#}$, wherein $^{\#}$ is the point of attachment with the indole nitrogen atom and $^{\#\#}$ is the point of attachment with the pyrazole carbon atom bearing the R$^7$ substituent;

—R$^6$-R$^{10}$— is $^{\#}$—(CH$_2$)$_q$—(B)—(CH$_2$)$_r$(B)—(CH$_2$)$_v$—$^{\#\#}$, wherein $^{\#}$ is the point of attachment with the indole nitrogen atom and $^{\#\#}$ is the point of attachment with the carbon atom of the phenyl moiety bearing the R$^{10}$ substituent;

n is 2, 3, 4, 5, or 6;

t is 0 or 1;

p is 0, or 1;

q is 2;

r is 2;

v is 0, or 1;

where the integers selected for variables n, t, p, q, r, and v result in forming a 9- to 13-membered ring independently from the selection of variable A1, A2 or A3;

B is independently selected from a —N(R$^{15}$)— group, —O—, and,

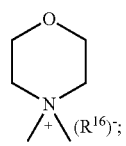

R$^{15}$ is independently selected from a hydrogen atom, a C$_1$-C$_3$-alkyl group which is optionally substituted with a phenyl group;

a phenyl group, a group

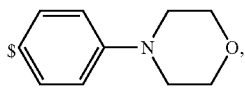

a group

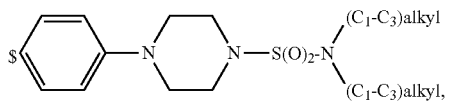

and
a group

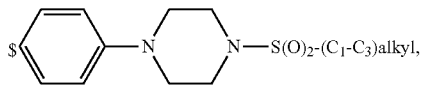

where $ is the point of attachment to the nitrogen atom, to which $R^{15}$ is attached, where $R^{16}$ is a pharmaceutically acceptable anion;

where $R^{19}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a C(O)OR$^{21}$—($C_1$-$C_3$-alkylene)- group, a —C(O)OR$^{21}$ group, a —C(O)NR$^{21}$R$^{22}$ group, a ($C_1$-$C_3$-alkyl)-O—($C_1$-$C_3$-alkylene)-C(O)— group, ($C_1$-$C_3$-alkyl)-C(O)-group, and a $C_3$-$C_6$-cycloalkyl-C(O)— group;

where $R^{20}$ is selected from a $C_1$-$C_3$-alkyl group, a $C_3$-$C_6$-cycloalkyl group, and a NR$^{21}$R$^{22}$ group; and where $R^{21}$ and $R^{22}$ are independently selected from a hydrogen atom and a $C_1$-$C_3$-alkyl group;

$R^8$ is selected from a hydrogen atom,
a $C_1$-$C_3$-alkyl group, which is optionally substituted with one or more substituents independently selected from a halogen atom, a hydroxyl group, a $C_1$-$C_3$-alkoxy group, a $C_1$-$C_3$-haloalkoxy group, a $C_3$-$C_6$-cycloalkyl group, a heterocycloalkyl group, and a NR$^{21}$R$^{22}$ group;
a $C_1$-$C_3$-haloalkyl group, and
a $C_3$-$C_6$-cycloalkyl group;

$R^9$ is selected from a hydrogen atom,
a $C_1$-$C_4$-alkyl group,
a $C_1$-$C_3$-hydroxyalkyl group,
a $C_1$-$C_4$-haloalkyl group,
a $C_1$-$C_4$-haloalkyl-NH—C(O)—O—($C_1$-$C_3$-alkylene)-group,
a $C_2$-$C_6$-haloalkenyl group,
a $C_1$-$C_6$-alkyl-O— group,
a $C_1$-$C_4$-haloalkoxy group,
a $C_1$-$C_6$-alkyl-O—($C_1$-$C_3$-alkylene)- group,
a ($C_3$-$C_7$)-cycloalkyl group,
a ($C_3$-$C_7$)-cycloalkyl-O—($C_1$-$C_3$-alkylene)- group,
a phenyl-O—($C_1$-$C_3$-alkylene)- group,
a ($R^{19}$)-(phenylene)-($C_1$-$C_3$-alkylene)-O—($C_1$-$C_3$-alkylene)- group,
a ($R^{19}$)-(phenylene)-($C_1$-$C_3$-alkylene)-O—($C_1$-$C_3$-alkylene)- group,
a ($R^{19}$)-(phenylene)-O—($C_1$-$C_3$-alkylene)- group,
a ($R^{19}$)-(phenylene)-heteroarylene)-O—($C_1$-$C_3$-alkylene)- group,
a ($R^{19}$)-(heterocycloalkylene)-($C_1$-$C_3$-alkylene)- group,
a ($R^{19}$)-(heterocycloalkylene)-(phenylene)-O—($C_1$-$C_3$-alkylene)- group,
a ($R^{19}$)-(heterocycloalkenylene)-(phenylene)-O—($C_1$-$C_3$-alkylene)- group,
a ($R^{19}$)-(heteroaryl-($C_1$-$C_3$-alkylene)-O—($C_1$-$C_3$-alkylene)- group,
a ($R^{19}$)-(heteroaryl)-(phenylene)-O—($C_1$-$C_3$-alkylene)- group,
a ($R^{20}$)—S(O)$_2$-(phenylene)-O—($C_1$-$C_3$-alkylene)- group,
a ($R^{20}$)—S(O)$_2$—NH-(phenylene)-O—($C_1$-$C_3$-alkylene)- group,
a ($R^{20}$)—S(O)$_2$—N—($C_1$-$C_3$-alkylene)-(phenylene)-O—($C_1$-$C_3$-alkylene)- group,
a ($R^{20}$)—S(O)$_2$-(heterocycloalkylene)-(phenylene)-O—($C_1$-$C_3$-alkylene)- group,
a ($R^{19}$)-(heterocycloalkylene)-(heteroarylene)-O—($C_1$-$C_3$-alkylene)- group,
a ($R^{19}$)-(heteroarylene)-O—($C_1$-$C_3$-alkylene)- group,
a ($R^{20}$)—S(O)$_2$-(heteroarylene)-O—($C_1$-$C_3$-alkylene)- group,
a ($R^{20}$)—S(O)$_2$-(heterocycloalkylene)-(heteroarylene)-O—($C_1$-$C_3$-alkylene)- group,
a NR$^{21}$R$^{22}$—($C_1$-$C_3$-alkylene)- group,
a ($C_1$-$C_3$-alkyl)-NH—($C_1$-$C_3$-alkylene)- group,
a ($C_1$-$C_3$-haloalkyl)-($C_1$-$C_3$-alkylene)-NH—($C_1$-$C_3$-alkylene)- group,
a ($C_1$-$C_3$-haloalkyl)-NH—($C_1$-$C_3$-alkylene)- group,
a ($C_1$-$C_3$-alkyl)-C(O)—NH—($C_1$-$C_3$-alkylene)- group,
a ($C_1$-$C_3$-alkyl)-C(O)—NR$^{15}$—($C_1$-$C_3$-alkylene)- group,
a group

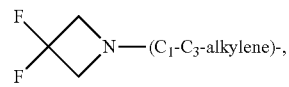

and a group

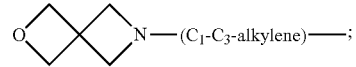

where the phenyl ring is optionally substituted with a halogen atom, a hydroxyl group or a $C_1$-$C_3$-alkoxy group and
the heterocycloalkyl group is optionally substituted with an oxo (=O) group or is optionally substituted with a $C_1$-$C_3$-alkyl group;

or $R^8$ and $R^9$ together form 6-membered ring optionally containing one or two oxygen atoms, $R^{11}$ and $R^{13}$ are each independently selected from a hydrogen atom and a $C_1$-$C_3$-alkyl group;

$R^{12}$ is selected from a hydrogen atom, and a $C_1$-$C_3$-alkoxy group;

or a tautomer, an N-oxide, or a salt thereof or a salt of a tautomer or a N-oxide or a mixture of same.

In accordance with a further aspect, the present invention provides compounds of general formula (I):
in which
A is

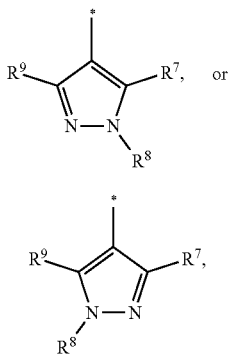

(A1)

(A2)

wherein $R^6$ and $R^7$, together with two carbon atoms of the pyrazole ring, two carbon atoms of the indole moiety and the nitrogen atom to which $R^6$ is attached, form a 9- to 13-membered ring and * is the point of attachment of these moieties to the indole carbon atom bearing the A substituent
or
A is

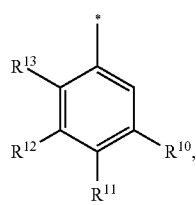

(A3)

wherein $R^6$ and $R^{10}$, together with three carbon atoms of the phenyl ring, two carbon atoms of the indole moiety and the nitrogen atom to which $R^6$ is attached, form a 9-13-membered ring and * is the point of attachment of these moieties to the indole carbon atom bearing the A substituent;
$R^1$ and $R^2$ are each independently selected from a hydrogen atom, a $C_1$-$C_3$-alkyl group and a $C_1$-$C_3$-alkoxy group;
$R^3$ is selected from a hydrogen atom, a halogen atom, a $C_1$-$C_3$-alkyl group and a $C_1$-$C_3$-alkoxy group,
$R^4$ is an aryl group, which is optionally substituted with one, two, three, substituents and each substituent is independently selected from a halogen atom, a $C_1$-$C_3$-alkyl group and a $C_1$-$C_3$-haloalkyl group,
L is a group —$(CH_2)_m$-E- wherein any $CH_2$ group is optionally substituted with an $C_1$-$C_3$-alkyl group;
E is an oxygen atom,
m is 2, or 3,
$R^5$ is a COOH group;
—$R^6$-$R^7$— is selected from $^{\#}$—$(CH_2)_n$—(B)$_t$(CH_2)_p$—$^{\#\#\#}$, $^{\#}$—$(C_2$-$C_6$-alkenylene)-(B)$_t$—$(CH_2)_p$—$^{\#\#\#}$ and $^{\#}$—$(CH_2)_q$—(B)—$(CH_2)_r$(B)—$(CH_2)_v$—$^{\#\#\#}$, wherein $^{\#}$ is the point of attachment with the indole nitrogen atom and $^{\#\#\#}$ is the point of attachment with the pyrazole carbon atom bearing the $R^7$ substituent;

—$R^6$-$R^{10}$— is $^{\#}$—$(CH_2)_q$—(B)—$(CH_2)_r$(B)—$(CH_2)_v$—$^{\#\#\#}$, wherein $^{\#}$ is the point of attachment with the indole nitrogen atom and $^{\#\#\#}$ is the point of attachment with the carbon atom of the phenyl moiety bearing the $R^{10}$ substituent;
n is 2, 3, 4, 5, or 6;
t is 0 or 1;
p is 0, or 1;
q is 2;
r is 2;
v is 0, or 1,
where the integers selected for variables n, t, p, q, r, and v result in forming a 9- to 13-membered ring independently from the selection of variable A1, A2 or A3;
B is independently selected from a a —$N(R^{15})$— group, —O— and,

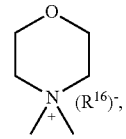

$R^{15}$ is independently selected from a hydrogen atom,
a $C_1$-$C_3$-alkyl group,
which is optionally substituted with a phenyl group;
a phenyl group, a group

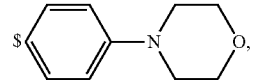

a group

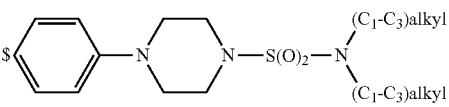

and
a group

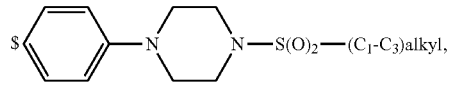

where $ is the point of attachment to the nitrogen atom, to which $R^{15}$ is attached,
where $R^{16}$ is a pharmaceutically acceptable anion;
where $R^{19}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a C(O)OR$^{21}$—($C_1$-$C_3$-alkylene)- group, a —C(O)OR$^{21}$ group, a —C(O)NR$^{21}$R$^{22}$ group, a ($C_1$-$C_3$-alkyl)-O—($C_1$-$C_3$-alkylene)-C(O)— group, a ($C_1$-$C_3$-alkyl)-C(O)— group and a $C_3$-$C_6$-cycloalkyl-C(O)— group;
where $R^{20}$ is selected from a $C_1$-$C_3$-alkyl group, a $C_3$-$C_6$-cycloalkyl group, and a NR$^{21}$R$^{22}$ group; and
where $R^{21}$ and $R^{22}$ are independently selected from a hydrogen atom and a $C_1$-$C_3$-alkyl group;

$R^8$ is selected from a hydrogen atom,
  a $C_1$-$C_3$-alkyl group, which is optionally substituted with one or more substituents independently selected from a halogen atom, a hydroxyl group, a $C_1$-$C_3$-alkoxy group, a $C_1$-$C_3$-haloalkoxy group, a $C_3$-$C_6$-cycloalkyl group, a heterocycloalkyl group and a $NR^{21}R^{22}$ group,
  a $C_1$-$C_3$-haloalkyl group and
  a $C_3$-$C_6$-cycloalkyl group,
$R^9$ is selected from a hydrogen atom,
  a $C_1$-$C_4$-alkyl group,
  a $C_1$-$C_3$-hydroxyalkyl group,
  a $C_1$-$C_4$-haloalkyl group,
  a $C_1$-$C_4$-haloalkyl-NH—C(O)—O—($C_1$-$C_3$-alkylene)- group,
  a $C_2$-$C_6$-haloalkenyl group,
  a $C_1$-$C_6$-alkyl-O— group,
  a $C_1$-$C_4$-haloalkoxy group,
  a $C_1$-$C_6$-alkyl-O—($C_1$-$C_3$-alkylene)- group,
  a ($C_3$-$C_7$)-cycloalkyl group,
  a ($C_3$-$C_7$)-cycloalkyl-O—($C_1$-$C_3$-alkylene)- group,
  a phenyl-O—($C_1$-$C_3$-alkylene)- group,
  a ($R^{19}$)-(phenylene)-($C_1$-$C_3$-alkylene)-O—($C_1$-$C_3$-alkylene)- group,
  a ($R^{19}$)-(phenylene)-($C_1$-$C_3$-alkylene)-O—($C_1$-$C_3$-alkylene)- group,
  a ($R^{19}$)-(phenylene)-O—($C_1$-$C_3$-alkylene)- group,
  a ($R^{19}$)-(phenylene)-(heteroarylene)-O—($C_1$-$C_3$-alkylene)- group,
  a ($R^{19}$)-(heterocycloalkylene)-($C_1$-$C_3$-alkylene)- group,
  a ($R^{19}$)-(heterocycloalkylene)-(phenylene)-O—($C_1$-$C_3$-alkylene)- group,
  a ($R^{19}$)-(heterocycloalkenylene)-(phenylene)-O—($C_1$-$C_3$-alkylene)- group,
  a ($R^{19}$)-(heteroarylene)-($C_1$-$C_3$-alkylene)-O—($C_1$-$C_3$-alkylene)- group,
  a ($R^{19}$)-(heteroarylene)-(phenylene)-O—($C_1$-$C_3$-alkylene)- group,
  a ($R^{19}$)-(heterocycloalkylene)-(heteroarylene)-O—($C_1$-$C_3$-alkylene)- group,
  a ($R^{19}$)-(heteroarylene)-O—($C_1$-$C_3$-alkylene)- group,
  a $NR^{21}R^{22}$—($C_1$-$C_3$-alkylene)- group,
  a ($C_1$-$C_3$-alkyl)-NH—($C_1$-$C_3$-alkylene)- group,
  a ($C_1$-$C_3$-haloalkyl)-($C_1$-$C_3$-alkylene)-NH—($C_1$-$C_3$-alkylene)- group,
  a ($C_1$-$C_3$-haloalkyl)-NH—($C_1$-$C_3$-alkylene)- group,
  a ($C_1$-$C_3$-alkyl)-C(O)—NH—($C_1$-$C_3$-alkylene)- group,
  a ($C_1$-$C_3$-alkyl)-C(O)—$NR^{15}$—($C_1$-$C_3$-alkylene)- group,
  a

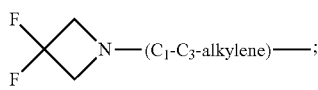

group,
  and a

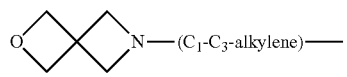

group;
where the phenyl ring is optionally substituted with a halogen atom, a hydroxyl group or a $C_1$-$C_3$-alkoxy group and the heterocycloalkyl group is optionally substituted with an oxo (=O) group or is optionally substituted with a $C_1$-$C_3$-alkyl group;
or $R^8$ and $R^9$ together form 6-membered ring optionally containing one or two oxygen atoms,
$R^{11}$ and $R^{13}$ are each independently selected from a hydrogen atom and a $C_1$-$C_3$-alkyl group;
$R^{12}$ is selected from a hydrogen atom and a $C_1$-$C_3$-alkoxy group;
or a tautomer, an N-oxide, or a salt thereof or a salt of a tautomer or a N-oxide or a mixture of same.

In accordance with a further aspect, the present invention provides compounds of general formula (I) in which:
A is

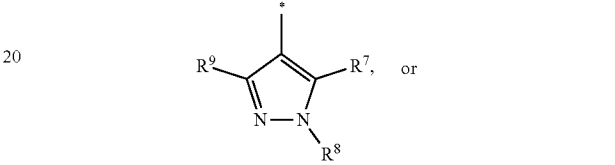

where $R^6$ and $R^7$, together with the two carbon atoms of the pyrazole ring, the two carbon atoms of the indole moiety and the nitrogen atom to which $R^6$ is attached, form a 9- or 12-membered ring and * is the point of attachment of these moieties to the indole carbon atom bearing the A substituent
or
A is

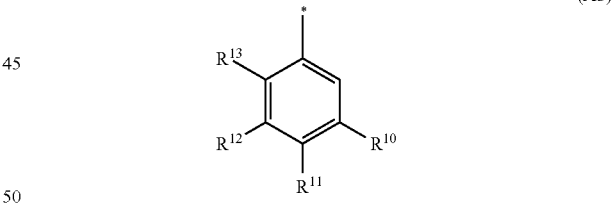

where $R^6$ and $R^{10}$, together with three carbon atoms of the phenyl ring, two carbon atoms of the indole moiety and the nitrogen atom to which $R^6$ is attached, form a 12-membered ring and * is the point of attachment of these moieties to indole carbon atom bearing the A substituent;
$R^1$, $R^2$, and $R^3$ are each hydrogen, a methyl group or a methoxy group;
$R^4$ is selected from a 1-naphthyl group,
  which is optionally substituted with one or two substituents and each substituent is independently selected from a fluorine atom, a chlorine atom, a methyl group, a trifluoromethyl group;
  a 4-chloro-3,5-dimethyl-phenyl-1-yl group, and
  a 5,6,7,8-tetrahydronaphthalen-1-yl group;
L is —$(CH_2)_3$-E- and E is —O—;
$R^5$ is —COOH;

—R$^6$-R$^7$— is selected from $^\#$—(CH$_2$)$_6$—$^{\#\#}$, $^\#$—(CH$_2$)$_3$O—CH$_2$—$^{\#\#}$, $^\#$—(CH$_2$)$_4$O—CH$_2$—$^{\#\#}$, $^\#$—(CH$_2$)$_5$O—CH$_2$—$^{\#\#}$, $^\#$—(CH$_2$)$_4$—O—(CH$_2$)$_2$—$^{\#\#}$, $^\#$—CH$_2$—CH=CH—CH$_2$—O—CH$_2$—$^{\#\#}$, $^\#$—(CH$_2$)$_2$—O—(CH$_2$)$_2$O—CH$_2$—$^{\#\#}$, $^\#$—(CH$_2$)$_2$—O—(CH$_2$)$_2$—O—$^{\#\#}$, $^\#$—(CH$_2$)$_3$—N(R$^{15}$)—$^{\#\#}$, $^\#$—(CH$_2$)$_4$—N(R$^{15}$)—$^{\#\#}$ #, —(CH$_2$)$_2$—N(R$^{15}$)—CH$_2$, $^\#$—(CH$_2$)$_3$—N(R$^{15}$)—CH$_2$—$^{\#\#}$, $^\#$—(CH$_2$)$_4$—N(R$^{15}$)—CH$_2$—$^{\#\#}$, $^\#$—(CH$_2$)$_5$—N(R$^{15}$)—CH$_2$—$^{\#\#}$, $^\#$—CH$_2$—CH=CH—CH$_2$—N(R$^{15}$)—$^{\#\#}$
and

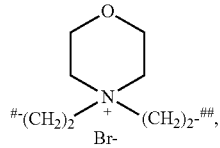

wherein $^\#$ is the point of attachment with the indole nitrogen atom and $^{\#\#}$ is the point of attachment with the pyrazole carbon atom bearing the R$^7$ substituent;
—R$^6$-R$^{10}$— is selected from $^\#$—(CH$_2$)$_2$—O—(CH$_2$)$_2$—O$^{\#\#}$ and $^\#$(CH$_2$)$_5$—O—$^\#$, wherein $^\#$ is the point of attachment with the indole nitrogen atom and $^{\#\#}$ is the point of attachment with the carbon atom of the phenyl moiety bearing the R$^{10}$ substituent;
R$^{15}$ is selected from a hydrogen atom, a methyl group, a phenyl group, a benzyl group, a group

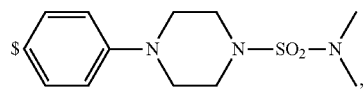

a group

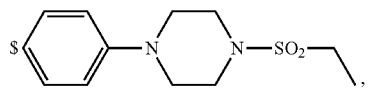

and a group

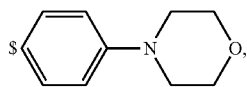

where $ is the point of attachment to the nitrogen atom, to which R$^{15}$ is attached;
R$^8$ is selected from a hydrogen atom,
 a C$_1$-C$_3$-alkyl group, which is optionally substituted with one or more substituents independently selected from a C$_1$-C$_3$-alkoxy group, a heterocycloalkyl group and a NR$^{21}$R$^{22}$ group;
 a C$_1$-C$_3$-haloalkyl group, and
 a C$_3$-C$_6$-cycloalkyl group,
R$^9$ is selected from a hydrogen atom,
 a C$_1$-C$_3$-alkyl group,
 a —CH$_2$—OH group,
 a trifluoromethyl group,
 a 2,2-difluoroethyl group,
 a 2-fluoroethenyl group,
 a methoxy group,
 a difluoromethoxy group,
 a CH$_3$—O—CH$_2$— group,
 a CH$_3$—CH$_2$—O—CH$_2$— group,
 a (CH$_3$)$_2$—CH—O—CH$_2$— group,
 a cyclopropyl group,
 a cyclopropyloxymethyl- group,
 a phenyl-O—CH$_2$— group,
 a phenyl-CH$_2$—O—CH$_2$— group,
 a methoxy-phenoxy-methyl- group,
 a [(4-cyanobenzyl)oxy]methyl group,
 a [4-(tetrahydro-2H-pyran-4-yl)phenoxy]methyl- group,
 a [4-(3,6-dihydro-2H-pyran-4-yl)phenoxy]methyl- group,
 a [4-(4-hydroxytetrahydro-2H-pyran-4-yl)phenoxy] methyl- group,
 a [4-(4-methoxytetrahydro-2H-pyran-4-yl)phenoxy] methyl- group,
 a (morpholin-4-yl)-CH$_2$— group,
 a [4-(morpholin-4-yl)phenoxy]methyl- group,
 a methyl-piperazin-methyl- group,
 a piperidin-1-ylmethyl- group,
 a (2-oxopiperidin-1-yl)methyl- group,
 a pyrrolidin-1-yl-methyl- group,
 a (2-oxopyrrolidin-1-yl)methyl- group,
 a 4-(2-oxopyridin-1(2H)-yl)phenoxy]methyl- group,
 a {4-[4-(N,N-dimethylsulfamoyl)piperazin-1-yl] phenoxy}methyl- group,
 a (methylsulfonyl)amino]phenoxy}methyl- group,
 a {4-[4-(N,N-diethylsulfamoyl)piperazin-1-yl] phenoxy}methyl- group,
 a {4-[4-(cyclopropylsulfonyl)piperazin-1-yl] phenoxy}methyl- group,
 a {4-[4-(methylsulfonyl)piperazin-1-yl]phenoxy}methyl- group,
 a 4-(methylsulfonyl)phenoxy]methyl- group,
 a [4-(piperazin-1-yl)phenoxy]methyl- group,
 a [4-(4-methylpiperazin-1-yl)phenoxy]methyl- group,
 a {4-[4-(3-hydroxy-3-methylbutyl)piperazin-1-yl] phenoxy}methyl- group,
 a {4-[4-(carboxymethyl)piperazin-1-yl]phenoxy}methyl- group,
 a [4-(4-acetylpiperazin-1-yl)phenoxy]methyl- group,
 a 4-[(cyclopropylcarbonyl)piperazin-1-yl] phenoxy}methyl- group,
 a -{4-[4-(methoxyacetyl)piperazin-1-yl] phenoxy}methyl- group,
 a {4-[4-(tert-butoxycarbonyl)piperazin-1-yl] phenoxy}methyl- group,
 a (pyrimidin-5-yloxy)methyl- group,
 a ({[2-(2-methoxyphenyl)pyrimidin-5-yl]oxy}methyl)- group,
 a [(1-methyl-1H-imidazol-2-yl)methoxy]methyl- group,
 a aminomethyl- group,
 a ethylaminomethyl- group,
 a trifluoromethyl)aminomethyl- group,
 a (2,2,-difluoroethyl)aminomethyl- group,
 a (2,2,2-trifluoroethyl)aminomethyl- group,
 a {[(2,2,2-trifluoroethyl)carbamoyl]oxy}methyl- group,
 a [(carbamoylbenzyl)oxy]methyl- group,
 a acetylamino-methyl- group,
 a acetyl(methyl)amino]methyl- group,
 a

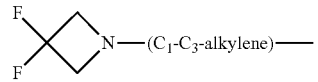

group
and a

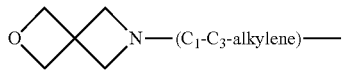

group,
or $R^8$ and $R^9$ together form a 6-membered ring optionally containing one or two oxygen atoms;
$R^{11}$ is a hydrogen atom,
$R^{12}$ is a hydrogen atom or a methoxy group,
$R^{13}$ is a hydrogen atom or a methyl group,
or a tautomer, an N-oxide, or a salt thereof or a salt of a tautomer or a N-oxide or a mixture of same.

In accordance with a further aspect, the present invention provides compounds of general formula (I):
in which
A is

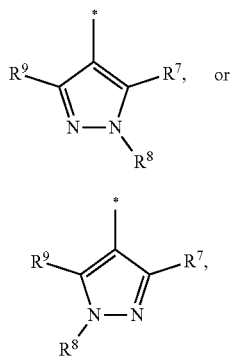

wherein $R^6$ and $R^7$, together with two carbon atoms of the pyrazole ring, two carbon atoms of the indole moiety and the nitrogen atom to which $R^6$ is attached, form a 9- to 16-membered ring and * is the point of attachment of these moieties to the indole carbon atom bearing the A substituent
or
A is

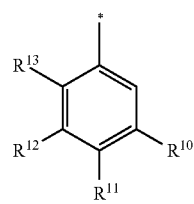

wherein $R^6$ and $R^{10}$, together with three carbon atoms of the phenyl ring, two carbon atoms of the indole moiety and the nitrogen atom to which $R^6$ is attached, form a 9- to 16-membered ring and * is the point of attachment of these moieties to the indole carbon atom bearing the A substituent;
$R^1$ and $R^2$ are each independently selected from a hydrogen atom, a halogen atom, a cyano group, and a $C_1$-$C_3$-alkyl group;

$R^3$ is selected from a hydrogen atom, a halogen atom, a cyano group, a $C_1$-$C_3$-alkyl group, a $C_1$-$C_3$-haloalkyl group, a $C_1$-$C_3$-alkoxy group, a $C_1$-$C_3$-alkylthio group, a —S(O)—($C_1$-$C_3$-alkyl) group, a —S(O)$_2$—($C_1$-$C_3$-alkyl) group, and a $C_1$-$C_3$-haloalkoxy group and a $C_1$-$C_3$-haloalkylthio group, and a $C_3$-$C_5$-cycloalkyl group;

$R^4$ is selected from an aryl group and a heteroaryl group, which is optionally substituted with one, two, three, four or five substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, a $C_1$-$C_3$-halothioalkyl group and a $C_3$-$C_5$-cycloalkyl group, L is a group —$(CH_2)_m$-E- wherein any $CH_2$ group is optionally substituted with one or two substituents and each substituent is independently selected from a halogen atom, a cyano group, a hydroxyl group, a $C_1$-$C_3$-alkyl group, and a $C_1$-$C_3$-alkoxy group, or two substituents are optionally taken together with their intervening atoms to form a saturated or partially unsaturated 3-6-membered cycloalkyl ring, or a 3-8 membered saturated or partially unsaturated heterocyclic ring having 1-2 heteroatoms independently selected from an oxygen atom, a sulfur atom, a —S(O)— group, a S(O)$_2$— group and a —NR$^{14}$— group;

E is a bond, an oxygen atom, a sulfur atom, a —S(O)— group, a S(O)$_2$ group or a —NR$^{14}$— group and constitutes the connecting element to $R^4$,
where $R^{14}$ is a hydrogen atom or a $C_1$-$C_3$-alkyl group;
m is 2, 3, or 4;
$R^5$ is selected from a COOH group, a

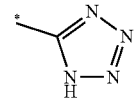 [SMILES: *c1nnn[nH]1]

group, a —C(O)—NHS(O)$_2$($C_1$-$C_6$-alkyl) group, a —C(O)—NHS(O)$_2$($C_3$-$C_6$-cycloalkyl) group, a —C(O)—NHS(O)$_2$(aryl) group, a —C(O)—NHS(O)$_2$(CH$_2$)$_s$NHCO($C_1$-$C_6$-alkyl) group, a —C(O)—NHS(O)$_2$(CH$_2$)$_s$NHCO($C_3$-$C_6$-cycloalkyl) group and a —C(O)—NHS(O)$_2$(CH$_2$)$_s$NHCO(aryl) group;
s is 0, 1, 2, or 3;
—$R^6$-$R^7$— is selected from $^\#$—(CH$_2$)$_n$—(B)$_t$—(CH$_2$)$_p$—$^{\#\#}$, $^\#$—(C$_2$-C$_6$-alkenylene)-(B)$_t$—(CH$_2$)$_p$—$^{\#\#}$, $^\#$—(CH$_2$)$_n$—(B)$_t$—(C$_2$-C$_6$-alkenylene)-$^{\#\#}$ and $^\#$—(CH$_2$)$_q$—(B)—(CH$_2$)$_t$—(B)—(CH$_2$)$_v$—$^{\#\#}$, wherein any CH$_2$ group is optionally substituted with one or more substituents selected from a halogen atom, a hydroxyl group, a NR$^{17}$R$^{18}$ group, a $C_1$-$C_3$-alkyl group, a $C_1$-$C_3$-haloalkyl group, a $C_1$-$C_3$-alkoxy group, and a $C_1$-$C_3$-haloalkoxy group, and where a double bond in any alkenylene can be replaced by a 1,2-cyclopropyl group, and said 1,2-cyclopropyl group is optionally substituted one or two times with a halogen atom or a $C_1$-$C_2$-alkyl group, wherein $^\#$ is the point of attachment with the indole nitrogen atom and $^{\#\#}$ is the point of attachment with the pyrazole carbon atom bearing the $R^7$ substituent;

—$R^6$-$R^{10}$— is selected from $^\#$—(CH$_2$)$_n$—(B)$_t$—(CH$_2$)$_p$—$^{\#\#}$, $^\#$—(C$_2$-C$_6$-alkenylene)-(B)$_t$—(CH$_2$)$_p$—$^{\#\#}$, $^\#$—(CH$_2$)$_n$—(B)$_t$—(C$_2$-C$_6$-alkenylene)-$^{\#\#}$, and $^\#$—(CH$_2$)$_q$—(B)—(CH$_2$)$_t$—(B)—(CH$_2$)$_v$—$^{\#\#}$, where one or more CH$_2$ groups are optionally substituted with one or more substituents selected from a halogen atom, a hydroxyl group, a $NR^{17}R^{18}$ group, a $C_1$-$C_3$-alkyl group, a $C_1$-$C_3$-haloalkyl group, a $C_1$-$C_3$-alkoxy group, and a $C_1$-$C_3$-haloalkoxy group, wherein # is the point of attachment with the indole nitrogen atom and ## is the point of attachment with the carbon atom of the phenyl moiety bearing the $R^{10}$ substituent;

n is 2, 3, 4, 5, 6, 7, 8, 9, or 10;

t is 0 or 1;

p is 0, 1, 2, 3, 4, 5, or 6;

q is 2, 3, 4, 5, or 6;

r is 2, 3, 4, 5, or 6;

v is 0, 1, or 2;

where the integers selected for variables n, t, p, q, r, and v result in forming a 9- to 16-membered ring independently from the selection of variable A1, A2 or A3;

B is selected from a —C(O)NR$^{15}$— group, a —NR$^{15}$C(O)— group, a —N(R$^{15}$)— group, a —N(R$^{15}$)—C(=O)—N(R$^{15}$)— group, a —O—C(=O)—N(R$^{15}$)— group, a —N(R$^{15}$)—C(=O)—O— group, —O—, —S—, —S(O)—, —S(O)$_2$—, a —S(O)NR$^{15}$— group, a —NR$^{15}$S(O)— group, a —S(O)$_2$NR$^{15}$— group, a —NR$^{15}$S(O)$_2$— group and

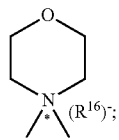

$R^{15}$ is selected from a hydrogen atom and a $C_1$-$C_6$-alkyl group which is optionally substituted with one or more substituents selected from a halogen atom, a $C_1$-$C_3$-alkyl group, a $C_1$-$C_3$-haloalkyl group and a $C_1$-$C_3$-hydroxyalkyl group, or $R^{15}$ is selected from a $C_1$-$C_3$-alkoxy-(CH$_2$)$_2$— group, a $C_1$-$C_3$-haloalkoxy-(CH$_2$)$_2$— group, a $C_1$-$C_6$-alkyl-O—(C$_2$-C$_3$-alkylene)- group, a phenyl-O—(C$_2$-C$_3$-alkylene)- group, a phenyl-(C$_1$-C$_3$-alkylene)-O—(C$_2$-C$_3$-alkylene)- group, a (heterocycloalkyl)-(C$_1$-C$_3$-alkylene)- group, a (R$^{19}$)-(heterocycloalkylene)-(phenylene)-O—(C$_2$-C$_3$-alkylene)- group, a (R$^{20}$)—S(O)$_2$-phenylene-O—(C$_2$-C$_3$-alkylene)- group, a (R$^{20}$)—S(O)$_2$-heterocycloalkylene-phenylene-O—(C$_2$-C$_3$-alkylene)- group, a phenyl-heteroaryl-O—(C$_2$-C$_3$)-alkylene- group, a phenyl group, a group

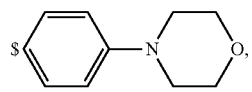

a group

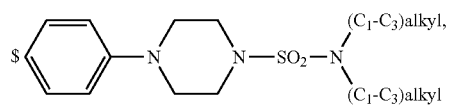

and a group

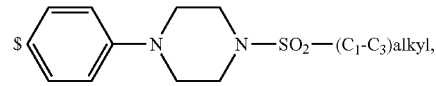

where $ is the point of attachment to the nitrogen atom, to which $R^{15}$ is attached, where $R^{16}$ is a pharmaceutically acceptable anion;

where $R^{17}$ and $R^{18}$ are each independently selected from a hydrogen atom, a $C_1$-$C_6$-alkyl group, a $C_1$-$C_6$-haloalkyl group, a $C_3$-$C_5$-cycloalkyl group, a $C_1$-$C_3$-alkyl-C(O)— group, a $C_1$-$C_3$-alkylS(O)$_2$— group and a $C_1$-$C_3$-alkyl-O—C(=O)— group;

where $R^{19}$ is selected from a hydrogen atom, a hydroxy group, a $C_1$-$C_3$-alkyl group, a $C_1$-$C_6$-hydroxyalkyl group, a $C_1$-$C_3$-alkoxy group, a —(C$_1$-C$_3$-alkylene)-C(O)OR$^{21}$ group —C(O)OR$^{21}$, a —C(O)(C$_1$-$C_3$-alkylene)-O—(C$_1$-$C_3$-alkyl) group, —C(O)(C$_1$-$C_6$-alkyl) and a —C(O)C$_3$-$C_6$-cycloalkyl group;

where $R^{20}$ is selected from a $C_1$-$C_3$-alkyl group, a $C_3$-$C_6$-cycloalkyl group, and a $NR^{21}R^{22}$ group; and where $R^{21}$ and $R^{22}$ is independently selected from a hydrogen atom and a $C_1$-$C_6$-alkyl group;

$R^8$ is a hydrogen atom, a $C_1$-$C_6$-alkyl group, which is optionally substituted with a hydroxyl group, a $C_1$-$C_3$-alkoxy group, a $C_1$-$C_3$-haloalkoxy group, a $C_3$-$C_6$-cycloalkyl group, a heterocycloalkyl group, a $NR^{21}R^{22}$ group or a $C_1$-$C_6$-alkyl group in which one or two not directly adjacent carbon atoms are independently replaced by a hetero atom selected from —O— and —NH—.

$R^9$ is a hydrogen atom, a $C_1$-$C_4$-alkyl group, a $C_1$-$C_3$-hydroxyalkyl group, a $C_1$-$C_6$-alkyl-O—(C$_1$-$C_3$-alkylene)- group, a phenyl-O—(C$_1$-$C_3$-alkylene)- group, a phenyl-(C$_1$-$C_3$-alkylene)-O—(C$_1$-$C_3$-alkylene)- group, a (heterocycloalkyl)-(C$_1$-$C_3$-alkylene)- group, a (R$^{19}$)-(heterocycloalkylene)-(phenylene)-O—(C$_1$-$C_3$-alkylene)- group, a (R$^{19}$)-(heterocycloalkenyl)-(phenylene)-O—(C$_1$-$C_3$-alkylene)- group, a (R$^{20}$)—S(O)$_2$-phenylene-O—(C$_1$-$C_3$-alkylene)- group, a (R$^{20}$)—S(O)$_2$-(heterocycloalkylene)-(phenylene)-O—(C$_1$-$C_3$-alkylene)- group, a phenyl-(heteroarylene)-O—(C$_1$-$C_3$-alkylene)- group, or a (R$^{19}$)-(heteroarylene)-(phenylene)-O—(C$_1$-$C_3$-alkylene)- group where the phenyl ring is optionally substituted with hydroxy or $C_1$-$C_3$-alkoxy, or $R^8$ and $R^9$ together form a 5- or 6-membered ring optionally containing one or two heteroatoms selected from —O— and —NR$^{14}$—, $R^{11}$ and $R^{13}$ are each independently selected from a hydrogen atom, a halogen atom, a $C_1$-$C_3$-alkyl group and a $C_1$-$C_3$-alkoxy group;

$R^{12}$ is selected from a $C_1$-$C_3$-alkoxy group, a $C_1$-$C_3$-alkyl group, a $C_1$-$C_3$-haloalkyl group, a $C_1$-$C_3$-haloalkoxy group, and a $NR^{17}R^{18}$ group;

or a tautomer, an N-oxide, or a salt thereof or a salt of a tautomer or a N-oxide or a mixture of same.

In accordance with a further aspect, the present invention provides compounds of general formula (I):
in which
A is

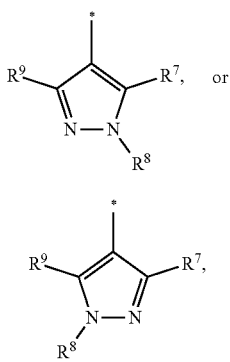

(A1)

(A2)

wherein $R^6$ and $R^7$, together with two carbon atoms of the pyrazole ring, two carbon atoms of the indole moiety and the nitrogen atom to which $R^6$ is attached, form a 9- to 16-membered ring and * is the point of attachment of these moieties to the indole carbon atom bearing the A substituent or
A is

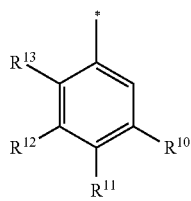

(A3)

wherein $R^6$ and $R^{10}$, together with three carbon atoms of the phenyl ring, two carbon atoms of the indole moiety and the nitrogen atom to which $R^6$ is attached, form a 9- to 16-membered ring and * is the point of attachment of these moieties to the indole carbon atom bearing the A substituent;

$R^1$ and $R^2$ are each independently selected from a hydrogen atom, a halogen atom, a cyano group and a $C_1$-$C_3$-alkyl group;

$R^3$ is selected from a hydrogen atom, a halogen atom, a cyano group, a $C_1$-$C_3$-alkyl group, a $C_1$-$C_3$-haloalkyl group, a $C_1$-$C_3$-alkoxy group, a $C_1$-$C_3$-alkylthio group, a —S(O)—($C_1$-$C_3$-alkyl) group, a —S(O)$_2$—($C_1$-$C_3$-alkyl) group, and a $C_1$-$C_3$-haloalkoxy group, a $C_1$-$C_3$-haloalkylthio group and a $C_3$-$C_5$-cycloalkyl group.

$R^4$ is selected from an aryl group and a heteroaryl group, which is optionally substituted with one, two, three, four or five substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, a $C_1$-$C_3$-halothioalkyl group and a $C_3$-$C_5$-cycloalkyl group, L is a group —(CH$_2$)$_m$-E- wherein any CH$_2$ group is optionally substituted with one or two substituents and each substituent is independently selected from a halogen atom, a cyano group, a hydroxyl group, a $C_1$-$C_3$-alkyl group, and a $C_1$-$C_3$-alkoxy group, or two substituents are optionally taken together with their intervening atoms to form a saturated or partially unsaturated 3-6-membered cycloalkyl ring, or a 3-8 membered saturated or partially unsaturated heterocyclic ring having 1-2 heteroatoms independently selected from an oxygen atom, a sulfur atom, a —S(O)— group, a S(O)$_2$— group and a —NR$^{14}$— group;

E is a bond, an oxygen atom, a sulfur atom, a —S(O)— group, a S(O)$_2$ group or a —NR$^{14}$— group and constitutes the connecting element to $R^4$,
where $R^{14}$ is a hydrogen atom or a $C_1$-$C_3$-alkyl group;
m is 2, 3, or 4;
$R^5$ is selected from a COOH group, a

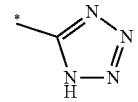

group, a —C(O)—NHS(O)$_2$(C$_1$-C$_6$-alkyl) group, a —C(O)—NHS(O)$_2$(C$_3$-C$_6$-cycloalkyl) group, a —C(O)—NHS(O)$_2$(aryl) group, a —C(O)—NHS(O)$_2$(CH$_2$)$_s$NHCO(C$_1$-C$_6$-alkyl) group, a —C(O)—NHS(O)$_2$(CH$_2$)$_s$NHCO(C$_3$-C$_6$-cycloalkyl) group and a —C(O)—NHS(O)$_2$(CH$_2$)$_s$NHCO(aryl) group;

s is 0, 1, 2, or 3;

—$R^6$-$R^7$— is selected from $^{\#}$—(CH$_2$)$_n$—(B)$_t$(CH$_2$)$_p$—$^{\#\#}$, $^{\#}$—(C$_2$-C$_6$-alkenylene)-(B)$_t$—(CH$_2$)$_p$—$^{\#\#}$, $^{\#}$—(CH$_2$)$_n$—(B)$_t$(C$_2$-C$_6$-alkenylene)-$^{\#\#}$, and $^{\#}$—(CH$_2$)$_q$—(B)—(CH$_2$)$_r$(B)—(CH$_2$)$_v$—$^{\#\#}$, wherein any CH$_2$ group is optionally substituted with one or more substituents selected from a halogen atom, a hydroxyl group, a NR$^{17}$R$^{18}$ group, a $C_1$-$C_3$-alkyl group, a $C_1$-$C_3$-haloalkyl group, a $C_1$-$C_3$-alkoxy group, and a $C_1$-$C_3$-haloalkoxy group, and where a double bond in any alkenylene can be replaced by a 1,2-cyclopropyl group, and said 1,2-cyclopropyl group is optionally substituted one or two times with a halogen atom or a $C_1$-$C_2$-alkyl group, wherein $^{\#}$ is the point of attachment with the indole nitrogen atom and $^{\#\#}$ is the point of attachment with the pyrazole carbon atom bearing the $R^7$ substituent;

—$R^6$-$R^{10}$— is selected from $^{\#}$—(CH$_2$)$_n$—(B)$_t$(CH$_2$)$_p$—$^{\#\#}$, $^{\#}$—(C$_2$-C$_6$-alkenylene)-(B)$_t$—(CH$_2$)$_p$—$^{\#\#}$, $^{\#}$—(CH$_2$)$_n$—(B)$_t$—(C$_2$-C$_6$-alkenylene)-$^{\#\#}$, and $^{\#}$—(CH$_2$)$_q$—(B)—(CH$_2$)$_r$—(B)—(CH$_2$)$_v$—$^{\#\#}$, where one or more CH$_2$ groups are optionally substituted with one or more substituents selected from a halogen atom, a hydroxyl group, a NR$^{17}$R$^{18}$ group, a $C_1$-$C_3$-alkyl group, a $C_1$-$C_3$-haloalkyl group, a $C_1$-$C_3$-alkoxy group and a $C_1$-$C_3$-haloalkoxy group, wherein $^{\#}$ is the point of attachment with the indole nitrogen atom and $^{\#\#}$ is the point of attachment with the carbon atom of the phenyl moiety bearing the $R^{10}$ substituent;

n is 2, 3, 4, 5, 6, 7, 8, 9, or 10;
t is 0 or 1;
p is 0, 1, 2, 3, 4, 5, or 6;
q is 2, 3, 4, 5, or 6;
r is 2, 3, 4, 5, or 6;
v is 0, 1, or 2;
where the integers selected for variables n, t, p, q, r, and v result in forming a 9- to 16-membered ring independently from the selection of variable A1, A2 or A3;

B is selected from a —C(O)NR$^{15}$— group, a —NR$^{15}$C(O)— group, a —N(R$^{15}$)— group, a —N(R$^{15}$)—C(=O)—N(R$^{15}$)— group, a —O—C(=O)—N(R$^{15}$)— group, a —N(R$^{15}$)—C(=O)—O— group, —O—, —S—, —S(O)—, —S(O)$_2$—, a —S(O)NR$^{15}$— group, a —NR$^{15}$S(O)— group, a —S(O)$_2$NR$^{15}$— group, a —NR$^{15}$S(O)$_2$— group, and

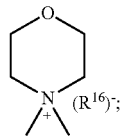

R$^{15}$ is selected from a hydrogen atom and a C$_1$-C$_6$-alkyl group which is optionally substituted with one or more substituents selected from a halogen atom, a C$_1$-C$_3$-alkyl group, a C$_1$-C$_3$-haloalkyl group and a C$_1$-C$_3$-hydroxyalkyl group, or R$^{15}$ is selected from a C$_1$-C$_3$-alkoxy-(CH$_2$)$_2$— group, a C$_1$-C$_3$-haloalkoxy-(CH$_2$)$_2$— group, a C$_1$-C$_6$-alkyl-O—(C$_2$-C$_3$-alkylene)- group, a phenyl-O—(C$_2$-C$_3$-alkylene)- group, a phenyl-(C$_1$-C$_3$-alkylene)-O—(C$_2$-C$_3$-alkylene)- group, a (heterocycloalkyl)-(C$_1$-C$_3$-alkylene)- group, a (R$^{19}$)-(heterocycloalkylene)-(phenylene)-O—(C$_2$-C$_3$-alkylene)- group, a (R$^{20}$)—S(O)$_2$-(phenylene)-O—(C$_2$-C$_3$-alkylene)- group, a (R$^{20}$)—S(O)$_2$-(heterocycloalkylene)-(phenylene)-O—(C$_2$-C$_3$-alkylene)- group, a phenyl-(heteroarylene)-O—(C$_2$-C$_3$)-(alkylene)- group, a phenyl group, a group

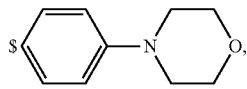

a group

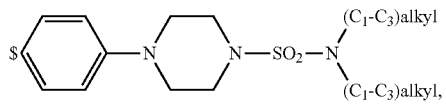

and a group

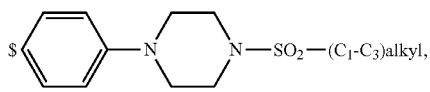

where $ is the point of attachment to the nitrogen atom, to which R$^{15}$ is attached, where R$^{16}$ is a pharmaceutically acceptable anion;

where R$^{17}$ and R$^{18}$ are each independently selected from a hydrogen atom, a C$_1$-C$_6$-alkyl group, a C$_1$-C$_6$-haloalkyl group, a C$_3$-C$_5$-cycloalkyl group, a C$_1$-C$_3$-alkyl-C(O)— group, a C$_1$-C$_3$-alkyl-S(O)$_2$— group and a C$_1$-C$_3$-alkyl-O—C(=O)— group;

where R$^{19}$ is selected from a hydrogen atom, a hydroxy group, a C$_1$-C$_3$-alkyl group, a C$_1$-C$_6$-hydroxyalkyl group, a C$_1$-C$_3$-alkoxy group, a —(C$_1$-C$_3$-alkylene)-C(O)OR$^{21}$ group —C(O)OR$^{21}$, a —C(O)(C$_1$-C$_3$-alkylene)-O—(C$_1$-C$_3$-alkyl) group, —C(O)(C$_1$-C$_6$-alkyl) and a —C(O)C$_3$-C$_6$-cycloalkyl group;

where R$^{20}$ is selected from a C$_1$-C$_3$-alkyl group, a C$_3$-C$_6$-cycloalkyl group, and a NR$^{21}$R$^{22}$ group; and where R$^{21}$ and R$^{22}$ is independently from each other a hydrogen atom or a C$_1$-C$_6$-alkyl group;

R$^8$ is a hydrogen atom, a C$_1$-C$_6$-alkyl group, which is optionally substituted with a hydroxyl group, a C$_1$-C$_3$-alkoxy group, a C$_1$-C$_3$-haloalkoxy group, a C$_3$-C$_6$-cycloalkyl group, a heterocycloalkyl group, a NR$^{21}$R$^{22}$ group, or a C$_1$-C$_6$-alkyl group in which one or two not directly adjacent carbon atoms are independently replaced by a hetero atom selected from —O— or —NH—.

R$^9$ is a hydrogen atom, a C$_1$-C$_4$-alkyl group, a C$_1$-C$_3$-hydroxyalkyl group, a C$_1$-C$_6$-alkyl-O—(C$_1$-C$_3$-alkylene)- group, a phenyl-O—(C$_1$-C$_3$-alkylene)- group, a phenyl-(C$_1$-C$_3$-alkylene)-O—(C$_1$-C$_3$-alkylene)- group, a (heterocycloalkyl)-(C$_1$-C$_3$-alkylene)- group, a (R$^{19}$)-(heterocycloalkylene)-(phenylene)-O—(C$_1$-C$_3$-alkylene)- group, a (R$^{20}$)—S(O)$_2$-(phenylene)-O—(C$_1$-C$_3$-alkylene)- group, a (R$^{20}$)—S(O)$_2$-(heterocycloalkylene)-(phenylene)-O—(C$_1$-C$_3$-alkylene)- group, or a phenyl-(heteroarylene)-O—(C$_1$-C$_3$-alkylene)- group where the phenyl ring is optionally substituted with hydroxy or C$_1$-C$_3$-alkoxy, or R$^8$ and R$^9$ together form a 5- or 6-membered ring optionally containing one or two heteroatoms selected from —O—, and —NR$^{14}$—, R$^{11}$ and R$^{13}$ are each independently selected from a hydrogen atom, a halogen atom, a C$_1$-C$_3$-alkyl group and a C$_1$-C$_3$-alkoxy group;

R$^{12}$ is selected from a C$_1$-C$_3$-alkoxy group, a C$_1$-C$_3$-alkyl group, a C$_1$-C$_3$-haloalkyl group, a C$_1$-C$_3$-haloalkoxy group and a NR$^{17}$R$^{18}$ group;

or a tautomer, an N-oxide, or a salt thereof or a salt of a tautomer or a N-oxide or a mixture of same.

In some embodiments, the present invention provides compounds of general formula (I): wherein A is

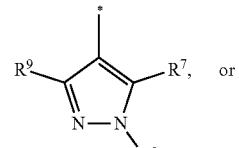

(A1)

or

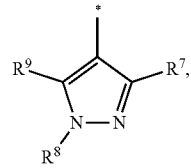

(A2)

where R$^6$ and R$^7$, together with the two carbon atoms of the pyrazole ring, the two carbon atoms of the indole moiety and the nitrogen atom to which R$^6$ is attached, form a 9 to 16-membered ring and * is the point of attachment of these moieties to indole carbon atom bearing the A substituent or

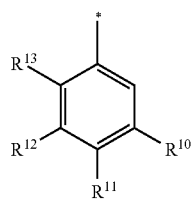
(A3)

where $R^6$ and $R^{10}$, together with three carbon atoms of the phenyl ring, two carbon atoms of the indole moiety and the nitrogen atom to which $R^6$ is attached, form a 9- to 16-membered ring and * is the point of attachment of these moieties to indole carbon atom bearing the A substituent;

$R^1$ and $R^2$ are each independently selected from a hydrogen atom, a halogen atom, a cyano group, and a $C_1$-$C_3$-alkyl group;

$R^3$ is selected from a hydrogen atom, a halogen atom, a cyano group, a $C_1$-$C_3$-alkyl group, a $C_1$-$C_3$-haloalkyl group, a $C_1$-$C_3$-alkoxy group, a $C_1$-$C_3$-alkylthio group, a $C_1$-$C_3$-haloalkoxy group, and a $C_1$-$C_3$-haloalkylthio group;

$R^4$ is an aryl group which is optionally substituted with one, two, three, four or five substituents, where each substituent is independently selected from a halogen atom, a cyano group, a $C_1$-$C_3$-alkyl group, a $C_1$-$C_3$-haloalkyl group, a $C_1$-$C_3$-alkoxy group and a $C_1$-$C_3$-haloalkoxy group;

L is a group —$(CH_2)_m$-E- which is optionally substituted with one or two substituents and each substituent is independently selected from a halogen atom, a $C_1$-$C_3$-alkyl group, and a $C_1$-$C_3$-alkoxy group, or two substituents are taken together with their intervening atoms to form a saturated or partially unsaturated 3-6-membered cycloalkyl ring, or a 3-8 membered saturated or partially unsaturated heterocyclic ring having 1-2 heteroatoms independently selected from an oxygen atom, a sulfur atom and a —$NR^{14}$— group;

E is a bond, an oxygen atom, a sulfur atom, or a —$NR^{14}$— group and constitutes the connecting element to $R^4$, where $R^{14}$ is a hydrogen atom or a $C_1$-$C_3$-alkyl group;

m is 2, 3, 4;

$R^5$ is selected from a COOH group, a

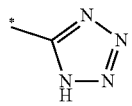

group, a —C(O)—NHS(O)$_2$($C_1$-$C_6$-alkyl) group, a —C(O)—NHS(O)$_2$($C_3$-$C_6$-cycloalkyl) group, a —C(O)—NHS(O)$_2$(aryl) group, a —C(O)—NHS(O)$_2$(CH$_2$)$_s$NHCO($C_1$-$C_6$-alkyl) group, a —C(O)—NHS(O)$_2$(CH$_2$)$_s$NHCO($C_3$-$C_6$-cycloalkyl) group and a —C(O)—NHS(O)$_2$(CH$_2$)$_s$NHCO(aryl) group;

s is 0, 1, 2, or 3;

—$R^6$-$R^7$— is selected from $^{\#}$—(CH$_2$)$_n$—(B)$_t$(CH$_2$)$_p$—$^{\#\#}$, $^{\#}$—(C$_2$-C$_6$-alkenylene)-(B)$_t$—(CH$_2$)$_p$—$^{\#\#}$, $^{\#}$—(CH$_2$)$_n$—(B)$_t$(C$_2$-C$_6$-alkenylene)-$^{\#\#}$, and $^{\#}$—(CH$_2$)$_q$—(B)—(CH$_2$)$_t$—(B)—(CH$_2$)$_v$—$^{\#\#}$, wherein any CH$_2$ group is optionally substituted with one or more substituents selected from a halogen atom, a hydroxyl group, a $NR^{17}R^{18}$ group, a $C_1$-$C_3$-alkyl group, a $C_1$-$C_3$-haloalkyl group, a $C_1$-$C_3$-alkoxy group and a $C_1$-$C_3$-haloalkoxy group, wherein $^{\#}$ is the point of attachment with the indole nitrogen atom and $^{\#\#}$ is the point of attachment with the pyrazole carbon atom bearing the $R^7$ substituent;

—$R^6$-$R^{10}$— is selected from $^{\#}$—(CH$_2$)$_n$—(B)$_t$(CH$_2$)$_p$—$^{\#\#}$, $^{\#}$—(C$_2$-C$_6$-alkenylene)-(B)$_t$—(CH$_2$)$_p$—$^{\#\#}$, $^{\#}$—(CH$_2$)$_n$—(B)$_t$(C$_2$-C$_6$-alkenylene)-$^{\#\#}$, and $^{\#}$—(CH$_2$)$_q$—(B)—(CH$_2$)$_t$—(B)—(CH$_2$)$_v$—$^{\#\#}$, where one or more CH$_2$ groups are optionally substituted with one or more substituents selected from a halogen atom, a hydroxyl group, a $NR^{17}R^{18}$ group, a $C_1$-$C_3$-alkyl group, a $C_1$-$C_3$-haloalkyl group, a $C_1$-$C_3$-alkoxy group and a $C_1$-$C_3$-haloalkoxy group, wherein $^{\#}$ is the point of attachment with the indole nitrogen atom and $^{\#\#}$ is the point of attachment with the carbon atom of the phenyl moiety bearing the $R^{10}$ substituent;

n is 2, 3, 4, 5, 6, 7, 8, 9, or 10;

t is 0 or 1;

p is 0, 1, 2, 3, 4, 5, or 6;

q is 2, 3, 4, 5, or 6;

r is 2, 3, 4, 5, or 6;

v is 0, 1, or 2;

where the integers selected for variables n, t, p, q, r, and v result in forming a 9- to 16-membered ring independently from the selection of variable A1, A2 or A3;

B is selected from a —$N(R^{15})$— group, —O—, and

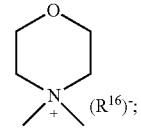

$R^{15}$ is selected from a hydrogen atom and a $C_1$-$C_6$-alkyl group which is optionally substituted with one or more substituents selected from a halogen atom, a $C_1$-$C_3$-alkyl group, a $C_1$-$C_3$-haloalkyl group, and a $C_1$-$C_3$-hydroxyalkyl group; or $R^{15}$ is selected from a $C_1$-$C_3$-alkoxy-(CH$_2$)$_2$— group, a $C_1$-$C_3$-haloalkoxy-(CH$_2$)$_2$— group, a $C_1$-$C_6$-alkyl-O—(C$_2$-C$_3$-alkylene)- group, a phenyl-O—(C$_2$-C$_3$-alkylene)- group, a phenyl-(C$_1$-C$_3$-alkylene)-O—(C$_2$-C$_3$-alkylene)- group, a (heterocycloalkyl)-(C$_1$-C$_3$-alkylene)- group, a ($R^{19}$)-(heterocycloalkylene)-(phenylene)-O—(C$_2$-C$_3$-alkylene)- group, a ($R^{20}$)—S(O)$_2$-phenylene-O—(C$_2$-C$_3$-alkylene)- group, a ($R^{20}$)—S(O)$_2$-heterocycloalkylene-phenylene-O—(C$_2$-C$_3$-alkylene)- group, a phenyl-heteroaryl-O—(C$_2$-C$_3$)-alkylene- group, a phenyl group, a group

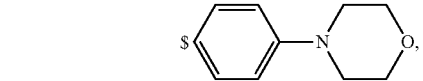

a group

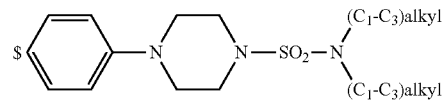

and a group

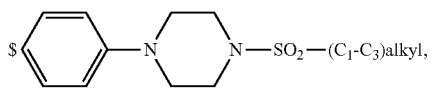

where $ is the point of attachment to the nitrogen atom, to which $R^{15}$ is attached, where $R^{16}$ is a pharmaceutically acceptable anion;

where $R^{17}$ and $R^{18}$ are each independently selected from a hydrogen atom and a $C_1$-$C_6$-alkyl group;

where $R^{19}$ is selected from a hydrogen atom, a hydroxy group, a $C_1$-$C_3$-alkyl group, a $C_1$-$C_6$-hydroxyalkyl group, a $C_1$-$C_3$-alkoxy group, a —($C_1$-$C_3$-alkylene)-C(O)$OR^{21}$ group, a —C(O)$OR^{21}$ group, a —C(O)($C_1$-$C_6$-alkyl) group, a —C(O)($C_1$-$C_3$-alkylene)-O—($C_1$-$C_3$-alkyl) group and a —C(O)$C_3$-$C_6$-cycloalkyl group;

where $R^{20}$ is selected from a $C_1$-$C_3$-alkyl group, a $C_3$-$C_6$-cycloalkyl group, and a $NR^{21}R^{22}$ group; and where $R^{21}$ and $R^{22}$ are each independently selected from a hydrogen atom and a $C_1$-$C_6$-alkyl group;

$R^8$ is a hydrogen atom, a $C_1$-$C_6$-alkyl group, which is optionally substituted with a hydroxyl group, a $C_1$-$C_3$-alkoxy group, a $C_1$-$C_3$-haloalkoxy group, a $C_3$-$C_6$-cycloalkyl group, a heterocycloalkyl group, or a $NR^{21}R^{22}$ group or a $C_1$-$C_6$-alkyl group in which one or two not directly adjacent carbon atoms are independently replaced by a hetero atom selected from —O— or —NH—.

$R^9$ is a hydrogen atom, a $C_1$-$C_4$-alkyl group, a $C_1$-$C_3$-hydroxyalkyl group, a $C_1$-$C_6$-alkyl-O—($C_1$-$C_3$-alkylene)- group, a phenyl-O—($C_1$-$C_3$-alkylene)- group, a phenyl-($C_1$-$C_3$-alkylene)-O—($C_1$-$C_3$-alkylene)- group, a (heterocycloalkyl)-($C_1$-$C_3$-alkylene)- group, a ($R^{19}$)-(heterocycloalkylene)-(phenylene)-O—($C_1$-$C_3$-alkylene)- group, a ($R^{20}$)—S(O)$_2$-(phenylene)-O—($C_1$-$C_3$-alkylene)- group, a ($R^{20}$)—S(O)$_2$-(heterocycloalkylene)-(phenylene)-O—($C_1$-$C_3$-alkylene)- group, or a phenyl-(heteroarylene)-O—($C_1$-$C_3$-alkylene)- group where the phenyl ring is optionally substituted with hydroxy or $C_1$-$C_3$-alkoxy, or $R^8$ and $R^9$ together form a 5- or 6-membered ring optionally containing one or two heteroatoms selected from —O—, and —$NR^{14}$—, $R^{11}$ and $R^{13}$ are each independently selected from a hydrogen atom, a halogen atom, a $C_1$-$C_3$-alkyl group and a $C_1$-$C_3$-alkoxy group;

$R^{12}$ is selected from a $C_1$-$C_3$-alkoxy group, a $C_1$-$C_3$-alkyl group, a $C_1$-$C_3$-haloalkyl group, a $C_1$-$C_3$-haloalkoxy group and a $NR^{17}R^{18}$ group;

or a tautomer, an N-oxide, or a salt thereof or a salt of a tautomer or a N-oxide or a mixture of same.

In some embodiments, the present invention includes compounds of general formula (I): wherein A is

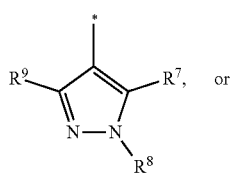

(A1) or

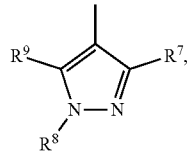

(A2)

where $R^6$ and $R^7$, together with the two carbon atoms of the pyrazole ring, the two carbon atoms of the indole moiety and the nitrogen atom to which $R^6$ is attached, form a 9 to 12-membered ring and * is the point of attachment of these moieties to indole carbon atom bearing the A substituent or

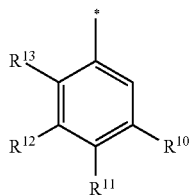

(A3)

where $R^6$ and $R^{10}$, together with three carbon atoms of the phenyl ring, two carbon atoms of the indole moiety and the nitrogen atom to which $R^6$ is attached, form a 9- to 12-membered ring and * is the point of attachment of these moieties to indole carbon atom bearing the A substituent;

$R^1$ and $R^2$ are each independently selected from a hydrogen atom, a halogen atom, a cyano group, and a $C_1$-$C_3$-alkyl group;

$R^3$ is selected from a hydrogen atom, a halogen atom, a cyano group, a $C_1$-$C_3$-alkyl group, a $C_1$-$C_3$-haloalkyl group, a $C_1$-$C_3$-alkoxy group, a $C_1$-$C_3$-alkylthio group, a $C_1$-$C_3$-haloalkoxy group and a $C_1$-$C_3$-haloalkylthio group;

$R^4$ is an aryl group which is optionally substituted with one, two, three, four or five substituents, where each substituent is independently selected from a halogen atom, a cyano group, a $C_1$-$C_3$-alkyl group, a $C_1$-$C_3$-haloalkyl group, a $C_1$-$C_3$-alkoxy group and a $C_1$-$C_3$-haloalkoxy group;

L is a group —$(CH_2)_m$-E- which is optionally substituted with one or two substituents and each substituent is independently selected from a halogen atom, a $C_1$-$C_3$-alkyl group, and a $C_1$-$C_3$-alkoxy group, or two substituents are taken together with their intervening atoms to form a saturated or partially unsaturated 3-6-membered cycloalkyl ring, or a 3-8 membered saturated or partially unsaturated heterocyclic ring having 1-2 heteroatoms independently selected from an oxygen atom, a sulfur atom and a —$NR^{14}$— group;

E is a bond, an oxygen atom, a sulfur atom, or a —$NR^{14}$— group and constitutes the connecting element to $R^4$, where $R^{14}$ is a hydrogen atom or a $C_1$-$C_3$-alkyl group;
m is 2, 3, 4;
$R^5$ is selected from a COOH group, or a

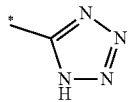

group, a —C(O)—NHS(O)$_2$($C_1$-$C_6$-alkyl) group, a —C(O)—NHS(O)$_2$($C_3$-$C_6$-cycloalkyl) group, a —C(O)—NHS(O)$_2$(aryl) group, a —C(O)—NHS(O)$_2$(CH$_2$)$_s$NHCO($C_1$-$C_6$-alkyl) group, a —C(O)—NHS(O)$_2$(CH$_2$)$_s$NHCO($C_3$-$C_6$-cycloalkyl) group and a —C(O)—NHS(O)$_2$(CH$_2$)$_s$NHCO(aryl) group;
s is 0, 1, 2, or 3;
—$R^6$-$R^7$— is selected from $^{\#}$—(CH$_2$)$_n$—(B)$_t$—(CH$_2$)$_p$—$^{\#\#}$, $^{\#}$—($C_2$-$C_6$-alkenylene)-(B)$_t$—(CH$_2$)$_p$—$^{\#\#}$, $^{\#}$—(CH$_2$)$_n$—(B)$_t$—($C_2$-$C_6$-alkenylene)-$^{\#\#}$, and $^{\#}$—(CH$_2$)$_q$—(B)—(CH$_2$)$_r$—(B)—(CH$_2$)$_v$—$^{\#\#}$, wherein any CH$_2$ group is optionally substituted with one or more substituents selected from a halogen atom, a hydroxyl group, a NR$^{17}$R$^{18}$ group, a $C_1$-$C_3$-alkyl group, a $C_1$-$C_3$-haloalkyl group, a $C_1$-$C_3$-alkoxy group and a $C_1$-$C_3$-haloalkoxy group, wherein $^{\#}$ is the point of attachment with the indole nitrogen atom and $^{\#\#}$ is the point of attachment with the pyrazole carbon atom bearing the $R^7$ substituent;
—$R^6$-$R^{10}$— is selected from $^{\#}$—(CH$_2$)$_n$—(B)$_t$—(CH$_2$)$_p$—$^{\#\#}$, $^{\#}$—($C_2$-$C_6$-alkenylene)-(B)$_t$—(CH$_2$)$_p$—$^{\#\#}$, $^{\#}$—(CH$_2$)$_n$—(B)$_t$—($C_2$-$C_6$-alkenylene)-$^{\#\#}$ and $^{\#}$—(CH$_2$)$_q$—(B)—(CH$_2$)$_r$—(B)—(CH$_2$)$_v$—$^{\#\#}$, where one or more CH$_2$ groups are optionally substituted with one or more substituents selected from a halogen atom, a hydroxyl group, a NR$^{17}$R$^{18}$ group, a $C_1$-$C_3$-alkyl group, a $C_1$-$C_3$-haloalkyl group, a $C_1$-$C_3$-alkoxy group and a $C_1$-$C_3$-haloalkoxy group, wherein $^{\#}$ is the point of attachment with the indole nitrogen atom and $^{\#\#}$ is the point of attachment with the carbon atom of the phenyl moiety bearing the $R^{10}$ substituent;
n is 2, 3, 4, 5, or 6;
t is 0 or 1;
p is 0, 1, 2, 3, 4, 5, or 6;
q is 2, 3, 4, 5, or 6;
r is 2, 3, 4, 5, or 6;
v is 0, 1, or 2;
where the integers selected for variables n, t, p, q, r, and v result in forming a 9- to 12-membered ring independently from the selection of variable A1, A2 or A3;
B is selected from a —N(R$^{15}$)— group, —O—, and

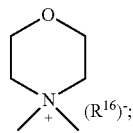

$R^{15}$ is selected from a hydrogen atom and a $C_1$-$C_6$-alkyl group which is optionally substituted with one or more substituents selected from a halogen atom, a $C_1$-$C_3$-alkyl group, a $C_1$-$C_3$-haloalkyl group and a $C_1$-$C_3$-hydroxyalkyl group; or
$R^{15}$ is selected from a $C_1$-$C_3$-alkoxy-(CH$_2$)$_2$— group, a $C_1$-$C_3$-haloalkoxy-(CH$_2$)$_2$— group, a $C_1$-$C_6$-alkyl-O—($C_2$-$C_3$-alkylene)- group, a phenyl-O—($C_2$-$C_3$-alkylene)- group, a phenyl-($C_1$-$C_3$-alkylene)-O—($C_2$-$C_3$-alkylene)- group, a (heterocycloalkyl)-($C_1$-$C_3$-alkylene)- group, a (R$^{19}$)-(heterocycloalkylene)-(phenylene)-O—($C_2$-$C_3$-alkylene)- group, a (R$^{20}$)—S(O)$_2$-(phenylene)-O—($C_2$-$C_3$-alkylene)- group, a (R$^{20}$)—S(O)$_2$-(heterocycloalkylene)-p(henylene)-O—($C_2$-$C_3$-alkylene)- group, a phenyl-(heteroarylene)-O—($C_2$-$C_3$)-(alkylene)- group, a phenyl group, a group,

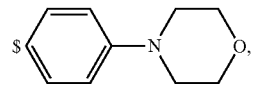

a group

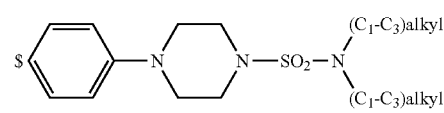

and a group

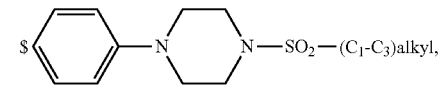

where $ is the point of attachment to the nitrogen atom, to which $R^{15}$ is attached,
where $R^{16}$ is a pharmaceutically acceptable anion;
where $R^{17}$ and $R^{18}$ are each independently selected from a hydrogen atom, and a $C_1$-$C_6$-alkyl group;
where $R^{19}$ is selected from a hydrogen atom, a hydroxy group, a $C_1$-$C_3$-alkyl group, a $C_1$-$C_6$-hydroxyalkyl group, a $C_1$-$C_3$-alkoxy group, a —($C_1$-$C_3$-alkylene)-C(O)OR$^{21}$ group, —C(O)OR$^{21}$, —C(O)($C_1$-$C_6$-alkyl), a —C(O)($C_1$-$C_3$-alkylene)-O—($C_1$-$C_3$-alkyl) group and a —C(O)$C_3$-$C_6$-cycloalkyl group;
where $R^{20}$ is selected from a $C_1$-$C_3$-alkyl group, a $C_3$-$C_6$-cycloalkyl group, and a NR$^{21}$R$^{22}$ group; and
where $R^{21}$ and $R^{22}$ are independently from each other a hydrogen atom or a $C_1$-$C_6$-alkyl group;
$R^8$ is a hydrogen atom, a $C_1$-$C_6$-alkyl group, which is optionally substituted with a hydroxyl group, a $C_1$-$C_3$-alkoxy group, a $C_1$-$C_3$-haloalkoxy group, a $C_3$-$C_6$-cycloalkyl group, a heterocycloalkyl group, or a NR$^{21}$R$^{22}$ group, or a $C_1$-$C_6$-alkyl group in which one or two not directly adjacent carbon atoms are independently replaced by a hetero atom selected from —O— or —NH—.
$R^9$ is a hydrogen atom, a $C_1$-$C_4$-alkyl group, a $C_1$-$C_3$-hydroxyalkyl group, a $C_1$-$C_6$-alkyl-O—($C_1$-$C_3$-alkylene)- group, a phenyl-O—($C_1$-$C_3$-alkylene)- group, a phenyl-($C_1$-$C_3$-alkylene)-O—($C_1$-$C_3$-alkylene)- group, a (heterocycloalkyl)-($C_1$-$C_3$-alkylene)- group, a (R$^{19}$)-(heterocycloalkylene)-(phenylene)-O—($C_1$-$C_3$-alkylene)- group, a (R$^{20}$)—S(O)$_2$-(phenylene)-O—($C_1$-$C_3$-alkylene)- group, a (R$^{20}$)—S(O)$_2$-(heterocycloalkylene)-(phenylene)-O—($C_1$-$C_3$-alkylene)- group, or a phenyl-(heteroarylene)-O—($C_1$-$C_3$-alkylene)- group where the phenyl ring is optionally substituted with hydroxy or $C_1$-$C_3$-alkoxy,
or $R^8$ and $R^9$ together form a 5- or 6-membered ring optionally containing one or two heteroatoms selected from —O—, and —NR$^{14}$—, $R^{11}$ and $R^{13}$ are each independently selected from a hydrogen atom, a halogen atom, a $C_1$-$C_3$-alkyl group and a $C_1$-$C_3$-alkoxy group;

$R^{12}$ is selected from a $C_1$-$C_3$-alkoxy group, a $C_1$-$C_3$-alkyl group, a $C_1$-$C_3$-haloalkyl group, a $C_1$-$C_3$-haloalkoxy group and a $NR^{17}R^{18}$ group;

or a tautomer, an N-oxide, or a salt thereof or a salt of a tautomer or a N-oxide or a mixture of same.

In some embodiments, the present invention includes compounds of general formula (I): wherein A is

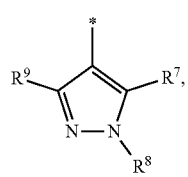

(A1)

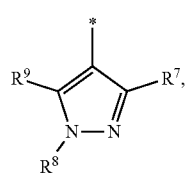

(A2)

where $R^6$ and $R^7$, together with the two carbon atoms of the pyrazole ring, the two carbon atoms of the indole moiety and the nitrogen atom to which $R^6$ is attached, form a 9- to 12-membered ring and * is the point of attachment of these moieties to indole carbon atom bearing the A substituent or

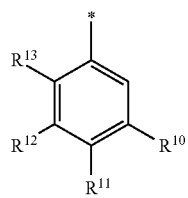

(A3)

where $R^6$ and $R^{10}$, together with three carbon atoms of the phenyl ring, two carbon atoms of the indole moiety and the nitrogen atom to which $R^6$ is attached, form a 9- to 12-membered ring and * is the point of attachment of these moieties to indole carbon atom bearing the A substituent;

$R^1$, $R^2$, and $R^3$ are each independently selected from a hydrogen atom, a halogen atom, and a $C_1$-$C_3$-alkyl group;

$R^4$ is selected from a 1-naphthyl- group, a phenyl group, and a 5,6,7,8-tetrahydronaphthalene-1-yl group, which are optionally substituted with one, two, or three substituents, where each substituent is independently selected from a halogen atom and a $C_1$-$C_3$-alkyl group;

L is —$(CH_2)_m$-E- and E is —O—;

m is 3;

$R^5$ is COOH,

—$R^6$-$R^7$— is selected from $^{\#}$—$(CH_2)_n$—$(B)_t$—$(CH_2)_p$—$^{\#\#}$, $^{\#}$—$(C_2$-$C_6$-alkenylene)-$(B)_t$—$(CH_2)_p$—$^{\#\#}$, $^{\#}$—$(CH_2)_n$—$(B)_t$—$(C_2$-$C_6$-alkenylene)-$^{\#\#}$ and $^{\#}$—$(CH_2)_q$—$(B)$—$(CH_2)_r$—$(B)$—$(CH_2)_v$—$^{\#\#}$, wherein any $CH_2$ group is optionally substituted with one or more substituents selected from a halogen atom, a hydroxyl group, a $NR^{17}R^{18}$ group, a $C_1$-$C_3$-alkyl group, a $C_1$-$C_3$-haloalkyl group, a $C_1$-$C_3$-alkoxy group and a $C_1$-$C_3$-haloalkoxy group, and wherein $^{\#}$ is the point of attachment with the indole nitrogen atom and $^{\#\#}$ is the point of attachment with the pyrazole carbon atom bearing the $R^7$ substituent;

—$R^6$-$R^{10}$— is selected from $^{\#}$—$(CH_2)_n$—$(B)_t$—$(CH_2)_p$—$^{\#\#}$ and $^{\#}$—$(CH_2)_q$—$(B)$—$(CH_2)_r$—$(B)$—$(CH_2)_v$—$^{\#\#}$ where B is O and v is 0, wherein any $CH_2$ group is optionally substituted with one or more substituents selected from a halogen atom, a hydroxyl group, a $NR^{17}R^{18}$ group, a $C_1$-$C_3$-alkyl group, a $C_1$-$C_3$-haloalkyl group, a $C_1$-$C_3$-alkoxy group and a $C_1$-$C_3$-haloalkoxy group, and wherein $^{\#}$ is the point of attachment with the indole nitrogen atom and $^{\#\#}$ is the point of attachment with the carbon atom of the phenyl moiety bearing the $R^{10}$ substituent;

n is 2, 3, 4, 5, or 6;

p is 0 or 1;

q is 2, 3, 4, 5, or 6;

t is 0 or 1, r is 2, 3, 4, 5, or 6;

v is 0, 1, or 2;

where the integers selected for variables n, t, p, q, r, and v result in variable A forming a 9- to 12-membered ring;

B is selected from a —$N(R^{15})$— group, —O— and

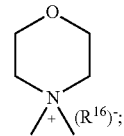

$R^{15}$ is selected from a $C_1$-$C_3$-alkyl group, a phenyl group, a group

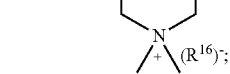

a group

and a group

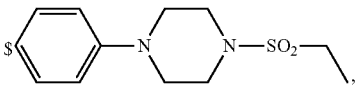

where $ is the point of attachment to the nitrogen atom, to which $R^{15}$ is attached, where $R^{16}$ is a pharmaceutically acceptable anion, where $R^{17}$ and $R^{18}$ are each independently selected from a hydrogen atom and a $C_1$-$C_6$-alkyl group;

$R^8$ is a $C_1$-$C_3$-alkyl group;

$R^9$ is selected from a hydrogen atom, a $C_1$-$C_3$-alkyl group, a $C_1$-$C_3$-hydroxyalkyl group, a $C_1$-$C_6$-alkyl-O—($C_1$-$C_3$- alkylene)- group, a phenyl-O—(C$_1$-C$_3$-alkylene)- group, a phenyl-(C$_1$-C$_3$-alkylene)-O—(C$_1$-C$_3$-alkylene)- group, a (heterocycloalkyl)-(C$_1$-C$_3$-alkylene)- group, a (R$^{19}$)-(heterocycloalkylene)-(phenylene)-O—(C$_1$-C$_3$-alkylene)- group, a (R$^{20}$)—S(O)$_2$-(phenylene)-O—(C$_1$-C$_3$-alkylene)- group, a (R$^{20}$)—S(O)$_2$-(heterocycloalkylene)-(phenylene)-O—(C$_1$-C$_3$-alkylene)- group, and a phenyl-(heteroarylene)-O—(C$_1$-C$_3$-alkylene)- group, where the phenyl ring is optionally substituted with a hydroxy group and a C$_1$-C$_3$-alkoxy group;

where R$^{19}$ is a hydrogen atom, a C$_1$-C$_3$-alkyl group, a —(C$_1$-C$_3$-alkylene)-C(O)OR$^{21}$ group, a —C(O)OR$^{21}$ group, a —C(O)(C$_1$-C$_3$-alkyl) group, a —C(O)(C$_1$-C$_3$-alkylene)-O—(C$_1$-C$_3$-alkyl) group, or a —C(O)C$_3$-C$_6$-cycloalkyl group;

where R$^{20}$ is selected from a C$_1$-C$_3$-alkyl group, a C$_3$-C$_6$-cycloalkyl group and NR$^{21}$R$^{22}$ group;

where R$^{21}$ is a C$_1$-C$_4$-alkyl group, and

R$^{11}$ and R$^{13}$ are each a hydrogen atom;

R$^{12}$ is a C$_1$-C$_3$-alkoxy group;

or a tautomer, an N-oxide, or a salt thereof or a salt of a tautomer or a N-oxide or a mixture of same.

In some embodiments, the present invention includes compounds of general formula (I): wherein A is

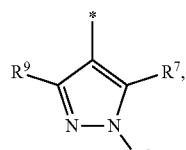

(A1)

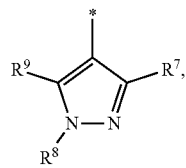

(A2)

where R$^6$ and R$^7$, together with the two carbon atoms of the pyrazole ring, the two carbon atoms of the indole moiety and the nitrogen atom to which R$^6$ is attached, form a 9- to 12-membered ring and * is the point of attachment of these moieties to indole carbon atom bearing the A substituent or

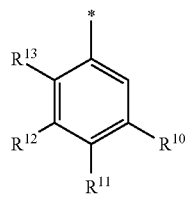

(A3)

where R$^6$ and R$^{10}$, together with three carbon atoms of the phenyl ring, two carbon atoms of the indole moiety and the nitrogen atom to which R$^6$ is attached, form a 9- to 12-membered ring and * is the point of attachment of these moieties to indole carbon atom bearing the A substituent;

R$^1$, R$^2$, and R$^3$ are each independently selected from a hydrogen atom, a halogen atom, and a C$_1$-C$_3$-alkyl group;

R$^4$ is selected from a 1-naphthyl- group, a phenyl group and a 5,6,7,8-tetrahydronaphthalene-1-yl group, which are optionally substituted with one, two, or three substituents, where each substituent is independently selected from a halogen atom and a C$_1$-C$_3$-alkyl group;

L is —(CH$_2$)$_m$-E- and E is —O—;

m is 3;

R$^5$ is COOH,

—R$^6$-R$^7$— is selected from $^{\#}$—(CH$_2$)$_n$—(B)$_t$(CH$_2$)$_p$—$^{\#\#\#}$, $^{\#}$—(C$_2$-C$_4$-alkenylene)-(B)$_t$(CH$_2$)$_p$—$^{\#\#}$, $^{\#}$—(CH$_2$)$_n$—(B)$_t$—(C$_2$-C$_4$-alkenylene)-$^{\#\#}$ and $^{\#}$—(CH$_2$)$_q$—(B)—(CH$_2$)$_r$—(B)—(CH$_2$)$_v$—$^{\#\#}$, wherein $^{\#}$ is the point of attachment with the indole nitrogen atom and $^{\#\#}$ is the point of attachment with the pyrazole carbon atom bearing the R$^7$ substituent;

—R$^6$-R$^{10}$— is selected from $^{\#}$—(CH$_2$)$_n$—(B)$_t$—(CH$_2$)$_p$—$^{\#\#}$ and $^{\#}$—(CH$_2$)$_q$—(B)—(CH$_2$)$_r$—(B)—(CH$_2$)$_v$—$^{\#\#}$ where B is O, and v is 0, wherein $^{\#}$ is the point of attachment with the indole nitrogen atom and $^{\#\#}$ is the point of attachment with the carbon atom of the phenyl moiety bearing the R$^{10}$ substituent;

n is 2, 3, 4, 5, or 6;

p is 0 or 1;

q is 2, 3, 4, 5, or 6;

t is 0 or 1, r is 2, 3, 4, 5, or 6;

v is 0, 1, or 2;

where the integers selected for variables n, t, p, q, r, and v result in forming a 9- to 12-membered ring independently from the selection of variable A1, A2 or A3;

B is selected from a —N(R$^{15}$)— group, —O—, and

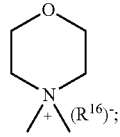

R$^{15}$ is selected from a C$_1$-C$_3$-alkyl group, a phenyl group, a group

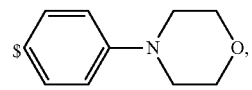

a group

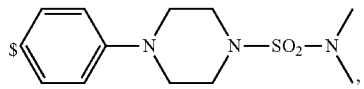

and a group

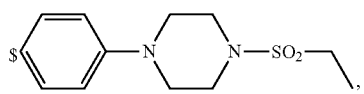

where $ is the point of attachment to the nitrogen atom, to which $R^{15}$ is attached, where $R^{16}$ is a pharmaceutically acceptable anion, where $R^{17}$ and $R^{18}$ are each independently selected from a hydrogen atom and a $C_1$-$C_6$-alkyl group;

$R^8$ is a $C_1$-$C_3$-alkyl group;

$R^9$ is selected from a hydrogen atom, a $C_1$-$C_3$-alkyl group, a $C_1$-$C_3$-hydroxyalkyl group, a $C_1$-$C_6$-alkyl-O—($C_1$-$C_3$-alkylene)- group, a phenyl-O—($C_1$-$C_3$-alkylene)- group, a phenyl-($C_1$-$C_3$-alkylene)-O—($C_1$-$C_3$-alkylene)- group, a (heterocycloalkyl)-($C_1$-$C_3$-alkylene)- group, a ($R^{19}$)-(heterocycloalkylene)-(phenylene)-O—($C_1$-$C_3$-alkylene)- group, a ($R^{20}$)—S(O)$_2$-(phenylene)-O—($C_1$-$C_3$-alkylene)- group, a ($R^{20}$)—S(O)$_2$-(heterocycloalkylene)-(phenylene)-O—($C_1$-$C_3$-alkylene)- group, and a phenyl-(heteroarylene)-O—($C_1$-$C_3$-alkylene)- group, where the phenyl ring is optionally substituted with a hydroxy group or a $C_1$-$C_3$-alkoxy group;

where $R^{19}$ is a hydrogen atom, a $C_1$-$C_3$-alkyl group, a —($C_1$-$C_3$-alkylene)-C(O)OR$^{21}$ group, a —C(O)OR$^{21}$ group, a —C(O)($C_1$-$C_3$-alkyl) group, a —C(O)($C_1$-$C_3$-alkylene)-O—($C_1$-$C_3$-alkyl) group, or a —C(O)$C_3$-$C_6$-cycloalkyl group;

where $R^{20}$ is selected from a $C_1$-$C_3$-alkyl group, a $C_3$-$C_6$-cycloalkyl group, and a NR$^{21}$R$^{22}$ group;

where $R^{21}$ is a $C_1$-$C_4$-alkyl group, and $R^{11}$ and $R^{13}$ are each a hydrogen atom;

$R^{12}$ is a $C_1$-$C_3$-alkoxy group;

or a tautomer, an N-oxide, or a salt thereof or a salt of a tautomer or a N-oxide or a mixture of same.

In some embodiments, the present invention includes compounds of general formula (I): wherein A is

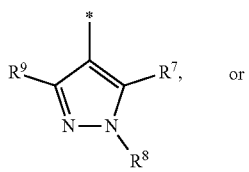

(A1)

or

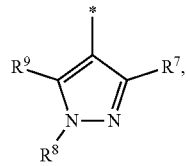

(A2)

where $R^6$ and $R^7$, together with the two carbon atoms of the pyrazole ring, the two carbon atoms of the indole moiety and the nitrogen atom to which $R^6$ is attached, form a 10- or 11-membered ring and * is the point of attachment of these moieties to the indole carbon atom bearing the A substituent or A is

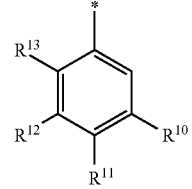

(A3)

where $R^6$ and $R^{10}$, together with three carbon atoms of the phenyl ring, two carbon atoms of the indole moiety and the nitrogen atom to which $R^6$ is attached, form a 12-membered ring and * is the point of attachment of these moieties to indole carbon atom bearing the A substituent;

$R^1$, $R^2$, and $R^3$ are a each hydrogen atom or a methyl group, $R^4$ is selected from 1-naphthyl, 4-chloro-3,5-dimethyl-phenyl-1-yl, and 5,6,7,8-tetrahydronaphthalen-1-yl;

L is —(CH$_2$)$_3$-E- and E is —O—;

$R^5$ is —COOH;

—R$^6$-R$^7$— is selected from $^{\#}$—(CH$_2$)$_6$—$^{\#\#}$, $^{\#}$—(CH$_2$)$_4$O—CH$_2$—$^{\#\#}$, $^{\#}$—CH$_2$—CH=CH—CH$_2$—O—CH$_2$—$^{\#\#}$, $^{\#}$—(CH$_2$)$_4$—NH$^{\#\#}$, $^{\#}$—(CH$_2$)$_3$—N(R$^{15}$)—CH$_2$—$^{\#\#}$, $^{\#}$—(CH$_2$)$_4$—N(R$^{15}$)—CH$_2$—$^{\#\#}$,

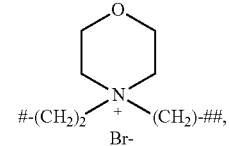

$^{\#}$—(CH$_2$)$_2$—N(phenyl)-CH$_2$—$^{\#\#}$, and $^{\#}$—(CH$_2$)$_3$—N(phenyl)-CH$_2$—$^{\#\#}$ wherein $^{\#}$ is the point of attachment with the indole nitrogen atom and $^{\#\#}$ is the point of attachment with the pyrazole carbon atom bearing the R$^7$ substituent;

—R$^6$-R$^{10}$— is selected from $^{\#}$—(CH$_2$)$_2$—O—(CH$_2$)$_2$—O$^{\#\#}$ and $^{\#}$(CH$_2$)$_5$—O—$^{\#\#}$, wherein $^{\#}$ is the point of attachment with the indole nitrogen atom and $^{\#\#}$ is the point of attachment with the carbon atom of the phenyl moiety bearing the R$^{10}$ substituent;

$R^{15}$ is selected from a methyl group, a phenyl group, a group

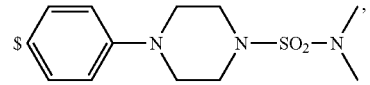

a group

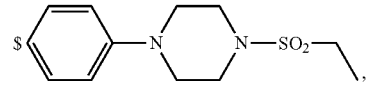

and a group

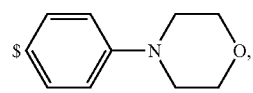

where $ is the point of attachment to the nitrogen atom, to which $R^{15}$ is attached;

$R^8$ is a methyl group;

$R^9$ is selected from a hydrogen atom, a $CH_3$ group, a —$CH_2$—OH group, a $CH_3$—O—$CH_2$— group, a $(CH_3)_2$—CH—O—$CH_2$— group, a phenyl-O—$CH_2$— group, a phenyl-$CH_2$—O—$CH_2$— group, a [4-(tetrahydro-2H-pyran-4-yl)phenoxy]methyl- group, a [4-(3,6-dihydro-2H-pyran-4-yl)phenoxy]methyl- group, a [4-(4-hydroxytetrahydro-2H-pyran-4-yl)phenoxy]methyl- group, a [4-(4-methoxytetrahydro-2H-pyran-4-yl)phenoxy]methyl- group, a (morpholin-4-yl)-$CH_2$— group, a [4-(morpholin-4-yl)phenoxy]methyl- group, a 4-(2-oxopyridin-1(2H)-yl)phenoxy]methyl- group, a {4-[4-(N,N-dimethylsulfamoyl)piperazin-1-yl]phenoxy}methyl- group, a {4-[4-(N,N-diethylsulfamoyl)piperazin-1-yl]phenoxy}methyl- group, a {4-[4-(cyclopropylsulfonyl)piperazin-1-yl]phenoxy}methyl- group, a {4-[4-(methylsulfonyl)piperazin-1-yl]phenoxy}methyl- group, a 4-(methylsulfonyl)phenoxy]methyl- group, a [4-(piperazin-1-yl)phenoxy]methyl- group, a [4-(4-methylpiperazin-1-yl)phenoxy]methyl- group, a 4-[4-(3-hydroxy-3-methylbutyl)piperazin-1-yl]phenoxy}methyl- group, a 4-[4-(carboxymethyl)piperazin-1-yl]phenoxy}methyl- group, a [4-(4-acetylpiperazin-1-yl)phenoxy]methyl- group, a 4-[4-(cyclopropylcarbonyl)piperazin-1-yl]phenoxy}methyl- group, a -{4-[4-(methoxyacetyl)piperazin-1-yl]phenoxy}methyl- group, a {4-[4-(tert-butoxycarbonyl)piperazin-1-yl]phenoxy}methyl- group, and a ({[2-(2-methoxyphenyl)pyrimidin-5-yl]oxy}methyl)- group;

$R^{12}$ is a methoxy group, $R^{10}$, $R^{11}$ and $R^{13}$ are each a hydrogen atom, or a tautomer, an N-oxide, or a salt thereof or a salt of a tautomer or a N-oxide or a mixture of same.

In some embodiments, the present invention includes compounds of general formula (I) selected from:

| Ex. No. | Name |
|---|---|
| 1-1 | (rac)-(E/Z)-3-{[4-(4-acetylpiperazin-1-yl)phenoxy]methyl}-1-methyl-7-[3-(naphthalen-1-yloxy)propyl]-1,10,13,15-tetrahydropyrazolo[4',3':9,10][1,6]oxazacycloundecino[8,7,6-hi]indole-8-carboxylic acid, |
| 1-2 | (rac)-(E/Z)-1-methyl-7-[3-(naphthalen-1-yloxy)propyl]-3-{[4-(piperazin-1-yl)phenoxy]methyl}-1,10,13,15-tetrahydropyrazolo[4',3':9,10][1,6]oxazacycloundecino[8,7,6-hi]indole-8-carboxylic acid, |
| 1-3 | (rac)-3-({4-[4-(diethylsulfamoyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 1-4 | 3-({4-[4-(diethylsulfamoyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1), |
| 1-5 | 3-({4-[4-(diethylsulfamoyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2), |
| 1-6 | (rac)-3-({4-[4-(tert-butoxycarbonyl)piperazin-1-yl]phenoxy}methyl)-1-methyl-7-[3-(naphthalen-1-yloxy)propyl]-1,10,11,12,13,15-hexahydropyrazolo[4',3':9,10][1,6]-oxazacycloundecino[8,7,6-hi]indole-8-carboxylic acid, |
| 1-7 | (rac)-1-methyl-3-{[4-(4-methylpiperazin-1-yl)phenoxy]methyl}-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 1-8 | (rac)-1-methyl-3-({4-[4-(methylsulfonyl)piperazin-1-yl]phenoxy}methyl)-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 1-9 | 1-methyl-3-({4-[4-(methylsulfonyl)piperazin-1-yl]phenoxy}methyl)-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1), |
| 1-10 | 1-methyl-3-({4-[4-(methylsulfonyl)piperazin-1-yl]phenoxy}methyl)-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2), |
| 1-11 | (rac)-3-({4-[4-(cyclopropylsulfonyl)piperazin-1-yl]phenoxy}methyl)-1-methyl-7-[3-(naphthalen-1-yloxy)propyl]-1,10,11,12,13,15-hexahydropyrazolo[4',3':9,10][1,6]-oxazacycloundecino[8,7,6-hi]indole-8-carboxylic acid, |
| 1-12 | 3-({4-[4-(cyclopropylsulfonyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1), |
| 1-13 | 3-({4-[4-(cyclopropylsulfonyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2), |
| 1-14 | (rac)-11-({4-[4-(dimethylsulfamoyl)piperazin-1-yl]phenoxy}methyl)-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid, |
| 1-15 | (+)-11-({4-[4-(dimethylsulfamoyl)piperazin-1-yl]phenoxy}methyl)-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid (enantiomer 1), |
| 1-16 | 11-({4-[4-(dimethylsulfamoyl)piperazin-1-yl]phenoxy}methyl)-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid (enantiomer 2), |

| Ex. No. | Name |
|---|---|
| 1-17 | (rac)-(E/Z)-3-({4-[4-(dimethylsulfamoyl)piperazin-1-yl]phenoxy}methyl)-1-methyl-7-[3-(naphthalen-1-yloxy)propyl]-1,10,13,15-tetrahydropyrazolo[4',3':9,10][1,6]-oxazacycloundecino[8,7,6-hi]indole-8-carboxylic acid, |
| 1-18 | (rac)-3-({4-[4-(dimethylsulfamoyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 1-19 | 3-({4-[4-(dimethylsulfamoyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1), |
| 1-20 | 3-({4-[4-(dimethylsulfamoyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2), |
| 1-21 | (rac)-3-({4-[4-(cyclopropylcarbonyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 1-22 | 3-({4-[4-(cyclopropylcarbonyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1), |
| 1-23 | 3-({4-[4-(cyclopropylcarbonyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2), |
| 1-24 | (rac)-3-{[4-(4-acetylpiperazin-1-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 1-25 | 3-{[4-(4-acetylpiperazin-1-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1), |
| 1-26 | 3-{[4-(4-acetylpiperazin-1-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2), |
| 1-27 | (rac)-3-({4-[4-(methoxyacetyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 1-28 | 3-({4-[4-(methoxyacetyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1), |
| 1-29 | 3-({4-[4-(methoxyacetyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2), |
| 1-30 | (rac)-7,9,11-trimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid, |
| 1-31 | 7,9,11-trimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid-N-ethylethanamine salt (enantiomer 1), |
| 1-32 | 7,9,11-trimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid-N-ethylethanamine salt (enantiomer 2), |
| 1-33 | (rac)-1,3-dimethyl-7-[3-(naphthalen-1-yloxy)propyl]-1,10,11,12,13,15-hexahydropyrazolo-[4',3':9,10][1,6]oxazacycloundecino[8,7,6-hi]indole-8-carboxylic acid, |
| 1-34 | 7,10,11-trimethyl-1-[3-(naphthalen-1-yloxy)propyl]-4,5,6,7,8,10-hexahydropyrazolo[3',4':7,8]-[1,5]diazecino[9,10,1-hi]indole-2-carboxylic acid-N-ethylethanamine salt (enantiomer 1), |
| 1-35 | 7,10,11-trimethyl-1-[3-(naphthalen-1-yloxy)propyl]-4,5,6,7,8,10-hexahydropyrazolo[3',4':7,8][1,5]diazecino[9,10,1-hi]indole-2-carboxylic acid-N-ethylethanamine salt (enantiomer 2), |
| 1-36 | (rac)-2,3-dimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid, |
| 1-37 | (+)-2,3-dimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (enantiomer 1), |
| 1-38 | (−)-2,3-dimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (enantiomer 2), |
| 1-39 | (rac)-3-({4-[4-(dimethylsulfamoyl)piperazin-1-yl]phenoxy}methyl)-1-methyl-7-[3-(naphthalen-1-yloxy)propyl]-10,11,12,13,14,15-hexahydro-1H-pyrazolo[4',3':4,5]azacycloundecino[3,2,1-hi]indole-8-carboxylic acid, |
| 1-40 | 3-({4-[4-(dimethylsulfamoyl)piperazin-1-yl]phenoxy}methyl)-1-methyl-7-[3-(naphthalen-1-yloxy)propyl]-10,11,12,13,14,15-hexahydro-1H-pyrazolo[4',3':4,5]azacycloundecino[3,2,1-hi]indole-8-carboxylic acid-N-ethylethanamine salt (enantiomer 1), |

-continued

| Ex. No. | Name |
|---|---|
| 1-41 | 3-({4-[4-(dimethylsulfamoyl)piperazin-1-yl]phenoxy}methyl)-1-methyl-7-[3-(naphthalen-1-yloxy)propyl]-10,11,12,13,14,15-hexahydro-1H-pyrazolo[4',3':4,5]azacycloundecino[3,2,1-hi]indole-8-carboxylic acid-N-ethylethanamine salt (enantiomer 2), |
| 1-42 | (rac)-7,9-dimethyl-11-(morpholin-4-ylmethyl)-1-[3-(naphthalen-1-yloxy)propyl]-4,5,6,7,8,9-hexahydropyrazolo[3',4':7,8][1,5]diazecino[9,10,1-hi]indole-2-carboxylic acid |
| 1-43 | (+)-7,9-dimethyl-11-(morpholin-4-ylmethyl)-1-[3-(naphthalen-1-yloxy)propyl]-4,5,6,7,8,9-hexahydropyrazolo[3',4':7,8][1,5]diazecino[9,10,1-hi]indole-2-carboxylic acid (enantiomer 1), |
| 1-44 | (−)-7,9-dimethyl-11-(morpholin-4-ylmethyl)-1-[3-(naphthalen-1-yloxy)propyl]-4,5,6,7,8,9-hexahydropyrazolo[3',4':7,8][1,5]diazecino[9,10,1-hi]indole-2-carboxylic acid (enantiomer 2), |
| 1-45 | (rac)-7,9-dimethyl-11-({4-[4-(methylsulfonyl)piperazin-1-yl]phenoxy}methyl)-1-[3-(naphthalen-1-yloxy)propyl]-4,5,6,7,8,9-hexahydropyrazolo[3',4':7,8][1,5]diazecino[9,10,1-hi]indole-2-carboxylic acid, |
| 1-46 | (+)-7,9-dimethyl-11-({4-[4-(methylsulfonyl)piperazin-1-yl]phenoxy}methyl)-1-[3-(naphthalen-1-yloxy)propyl]-4,5,6,7,8,9-hexahydropyrazolo[3',4':7,8][1,5]diazecino[9,10,1-hi]indole-2-carboxylic acid (enantiomer 1), |
| 1-47 | (−)-7,9-dimethyl-11-({4-[4-(methylsulfonyl)piperazin-1-yl]phenoxy}methyl)-1-[3-(naphthalen-1-yloxy)propyl]-4,5,6,7,8,9-hexahydropyrazolo[3',4':7,8][1,5]diazecino[9,10,1-hi]indole-2-carboxylic acid (enantiomer 2), |
| 1-48 | (rac)-7,9-dimethyl-11-{[4-(methylsulfonyl)phenoxy]methyl}-1-[3-(naphthalen-1-yloxy)propyl]-4,5,6,7,8,9-hexahydropyrazolo[3',4':7,8][1,5]diazecino[9,10,1-hi]indole-2-carboxylic acid, |
| 1-49 | (−)-7,9-dimethyl-11-{[4-(methylsulfonyl)phenoxy]methyl}-1-[3-(naphthalen-1-yloxy)propyl]-4,5,6,7,8,9-hexahydropyrazolo[3',4':7,8][1,5]diazecino[9,10,1-hi]indole-2-carboxylic acid (enantiomer 1), |
| 1-50 | (+)-7,9-dimethyl-11-{[4-(methylsulfonyl)phenoxy]methyl}-1-[3-(naphthalen-1-yloxy)propyl]-4,5,6,7,8,9-hexahydropyrazolo[3',4':7,8][1,5]diazecino[9,10,1-hi]indole-2-carboxylic acid (enantiomer 2), |
| 1-51 | (rac)-(E/Z)-1-methyl-3-{[4-(methylsulfonyl)phenoxy]methyl}-7-[3-(naphthalen-1-yloxy)propyl]-1,10,13,15-tetrahydropyrazolo[4',3':9,10][1,6]oxazacycloundecino[8,7,6-hi]indole-8-carboxylic acid, |
| 1-52 | (E/Z)-1-methyl-3-{[4-(methylsulfonyl)phenoxy]methyl}-7-[3-(naphthalen-1-yloxy)propyl]-1,10,13,15-tetrahydropyrazolo[4',3':9,10][1,6]oxazacycloundecino[8,7,6-hi]indole-8-carboxylic acid (enantiomer 1), |
| 1-53 | (E/Z)-1-methyl-3-{[4-(methylsulfonyl)phenoxy]methyl}-7-[3-(naphthalen-1-yloxy)propyl]-1,10,13,15-tetrahydropyrazolo[4',3':9,10][1,6]oxazacycloundecino[8,7,6-hi]indole-8-carboxylic acid (enantiomer 2), |
| 1-54 | (rac)-1-methyl-3-{[4-(methylsulfonyl)phenoxy]methyl}-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 1-55 | (−)-1-methyl-3-{[4-(methylsulfonyl)phenoxy]methyl}-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1), |
| 1-56 | (+)-1-methyl-3-{[4-(methylsulfonyl)phenoxy]methyl}-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2), |
| 1-57 | (rac)-7,9-dimethyl-1-[3-(naphthalen-1-yloxy)propyl]-11-{[4-(tetrahydro-2H-pyran-4-yl)phenoxy]methyl}-4,5,6,7,8,9-hexahydropyrazolo[3',4':7,8][1,5]diazecino[9,10,1-hi]indole-2-carboxylic acid, |
| 1-58 | (+)-7,9-dimethyl-1-[3-(naphthalen-1-yloxy)propyl]-11-{[4-(tetrahydro-2H-pyran-4-yl)phenoxy]methyl}-4,5,6,7,8,9-hexahydropyrazolo[3',4':7,8][1,5]diazecino[9,10,1-hi]indole-2-carboxylic acid (enantiomer 1), |
| 1-59 | (−)-7,9-dimethyl-1-[3-(naphthalen-1-yloxy)propyl]-11-{[4-(tetrahydro-2H-pyran-4-yl)phenoxy]methyl}-4,5,6,7,8,9-hexahydropyrazolo[3',4':7,8][1,5]diazecino[9,10,1-hi]indole-2-carboxylic acid (enantiomer 2), |
| 1-60 | (rac)-(E/Z)-3-{[4-(4-hydroxytetrahydro-2H-pyran-4-yl)phenoxy]methyl}-1-methyl-7-[3-(naphthalen-1-yloxy)propyl]-1,10,13,15-tetrahydropyrazolo[4',3':9,10][1,6]oxazacycloundecino[8,7,6-hi]indole-8-carboxylic acid, |
| 1-61 | (rac)-3-{[4-(4-hydroxytetrahydro-2H-pyran-4-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 1-64 | (rac)-(E/Z)-3-{[4-(4-methoxytetrahydro-2H-pyran-4-yl)phenoxy]methyl}-1-methyl-7-[3-(naphthalen-1-yloxy)propyl]-1,10,13,15-tetrahydropyrazolo[4',3':9,10][1,6]oxazacycloundecino[8,7,6-hi]indole-8-carboxylic acid, |
| 1-65 | (rac)-3-{[4-(4-methoxytetrahydro-2H-pyran-4-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 1-66 | 3-{[4-(4-methoxytetrahydro-2H-pyran-4-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1), |
| 1-67 | 3-{[4-(4-methoxytetrahydro-2H-pyran-4-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2), |

| Ex. No. | Name |
|---|---|
| 1-68 | (rac)-(11Z)-1-methyl-7-[3-(naphthalen-1-yloxy)propyl]-3-[(propan-2-yloxy)methyl]-1,10,13,15-tetrahydropyrazolo[4',3':9,10][1,6]oxazacycloundecino[8,7,6-hi]indole-8-carboxylic acid, |
| 1-69 | (rac)-1-methyl-3-[(propan-2-yloxy)methyl]-7-[3-(5,6,7,8-tetrahydronaphthalen-1-yloxy)propyl]-1,10,11,12,13,15-hexahydropyrazolo[4',3':9,10][1,6]oxazacycloundecino[8,7,6-hi]indole-8-carboxylic acid, |
| 1-70 | (rac)-7,9-dimethyl-1-[3-(naphthalen-1-yloxy)propyl]-11-[(propan-2-yloxy)methyl]-4,5,6,7,8,9-hexahydropyrazolo[3',4':7,8][1,5]diazecino[9,10,1-hi]indole-2-carboxylic acid, |
| 1-71 | 7,9-dimethyl-1-[3-(naphthalen-1-yloxy)propyl]-11-[(propan-2-yloxy)methyl]-4,5,6,7,8,9-hexahydropyrazolo[3',4':7,8][1,5]diazecino[9,10,1-hi]indole-2-carboxylic acid (enantiomer 1), |
| 1-72 | 7,9-dimethyl-1-[3-(naphthalen-1-yloxy)propyl]-11-[(propan-2-yloxy)methyl]-4,5,6,7,8,9-hexahydropyrazolo[3',4':7,8][1,5]diazecino[9,10,1-hi]indole-2-carboxylic acid (enantiomer 2), |
| 1-73 | (rac)-1,14-dimethyl-7-[3-(naphthalen-1-yloxy)propyl]-3-[(propan-2-yloxy)methyl]-10,11,12,13,14,15-hexahydro-1H-pyrazolo[3',4':8,9][1,6]diazacycloundecino[10,11,1-hi]indole-8-carboxylic acid, |
| 1-74 | 1,14-dimethyl-7-[3-(naphthalen-1-yloxy)propyl]-3-[(propan-2-yloxy)methyl]-10,11,12,13,14,15-hexahydro-1H-pyrazolo[3',4':8,9][1,6]diazacycloundecino[10,11,1-hi]indole-8-carboxylic acid (enantiomer 1), |
| 1-75 | 1,14-dimethyl-7-[3-(naphthalen-1-yloxy)propyl]-3-[(propan-2-yloxy)methyl]-10,11,12,13,14,15-hexahydro-1H-pyrazolo[3',4':8,9][1,6]diazacycloundecino[10,11,1-hi]indole-8-carboxylic acid (enantiomer 2), |
| 1-76 | (rac)-(E/Z)-1-methyl-7-[3-(naphthalen-1-yloxy)propyl]-3-(phenoxymethyl)-1,10,13,15-tetrahydropyrazolo[4',3':9,10][1,6]oxazacycloundecino[8,7,6-hi]indole-8-carboxylic acid, |
| 1-77 | (E/Z)-1-methyl-7-[3-(naphthalen-1-yloxy)propyl]-3-(phenoxymethyl)-1,10,13,15-tetrahydropyrazolo[4',3':9,10][1,6]oxazacycloundecino[8,7,6-hi]indole-8-carboxylic acid (enantiomer 1), |
| 1-78 | (E/Z)-1-methyl-7-[3-(naphthalen-1-yloxy)propyl]-3-(phenoxymethyl)-1,10,13,15-tetrahydropyrazolo[4',3':9,10][1,6]oxazacycloundecino[8,7,6-hi]indole-8-carboxylic acid (enantiomer 2), |
| 1-79 | 1-methyl-7-[3-(naphthalen-1-yloxy)propyl]-3-(phenoxymethyl)-1,10,11,12,13,15-hexahydropyrazolo[4',3':9,10][1,6]oxazacycloundecino[8,7,6-hi]indole-8-carboxylic acid (enantiomer 1), |
| 1-80 | 1-methyl-7-[3-(naphthalen-1-yloxy)propyl]-3-(phenoxymethyl)-1,10,11,12,13,15-hexahydropyrazolo[4',3':9,10][1,6]oxazacycloundecino[8,7,6-hi]indole-8-carboxylic acid (enantiomer 2), |
| 1-81 | (rac)-7,9-dimethyl-1-[3-(naphthalen-1-yloxy)propyl]-11-(phenoxymethyl)-4,5,6,7,8,9-hexahydropyrazolo[3',4':7,8][1,5]diazecino[9,10,1-hi]indole-2-carboxylic acid, |
| 1-82 | 7,9-dimethyl-1-[3-(naphthalen-1-yloxy)propyl]-11-(phenoxymethyl)-4,5,6,7,8,9-hexahydropyrazolo[3',4':7,8][1,5]diazecino[9,10,1-hi]indole-2-carboxylic acid (enantiomer 1), |
| 1-83 | 7,9-dimethyl-1-[3-(naphthalen-1-yloxy)propyl]-11-(phenoxymethyl)-4,5,6,7,8,9-hexahydropyrazolo[3',4':7,8][1,5]diazecino[9,10,1-hi]indole-2-carboxylic acid (enantiomer 2), |
| 1-84 | (rac)-1-[3-(4-chloro-3,5-dimethylphenoxy)propyl]-7,9-dimethyl-11-(phenoxymethyl)-4,5,6,7,8,9-hexahydropyrazolo[3',4':7,8][1,5]diazecino[9,10,1-hi]indole-2-carboxylic acid, |
| 1-85 | 1-[3-(4-chloro-3,5-dimethylphenoxy)propyl]-7,9-dimethyl-11-(phenoxymethyl)-4,5,6,7,8,9-hexahydropyrazolo[3',4':7,8][1,5]diazecino[9,10,1-hi]indole-2-carboxylic acid (enantiomer 1), |
| 1-86 | 1-[3-(4-chloro-3,5-dimethylphenoxy)propyl]-7,9-dimethyl-11-(phenoxymethyl)-4,5,6,7,8,9-hexahydropyrazolo[3',4':7,8][1,5]diazecino[9,10,1-hi]indole-2-carboxylic acid (enantiomer 2), |
| 1-87 | (rac)-7,9-dimethyl-11-{[4-(morpholin-4-Aphenoxy]methyl}-1-[3-(naphthalen-1-yloxy)propyl]-4,5,6,7,8,9-hexahydropyrazolo[3',4':7,8][1,5]diazecino[9,10,1-hi]indole-2-carboxylic acid, |
| 1-88 | (+)-7,9-dimethyl-11-{[4-(morpholin-4-yl)phenoxy]methyl}-1-[3-(naphthalen-1-yloxy)propyl]-4,5,6,7,8,9-hexahydropyrazolo[3',4':7,8][1,5]diazecino[9,10,1-hi]indole-2-carboxylic acid (enantiomer 1), |
| 1-89 | (−)-7,9-dimethyl-11-{[4-(morpholin-4-yl)phenoxy]methyl}-1-[3-(naphthalen-1-yloxy)propyl]-4,5,6,7,8,9-hexahydropyrazolo[3',4':7,8][1,5]diazecino[9,10,1-hi]indole-2-carboxylic acid (enantiomer 2), |
| 1-90 | (rac)-11-({[2-(2-methoxyphenyl)pyrimidin-5-yl]oxy}methyl)-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid, |
| 1-91 | 11-({[2-(2-methoxyphenyl)pyrimidin-5-yl]oxy}methyl)-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid-N-ethylethanamine salt (enantiomer 1), |
| 1-92 | 11-({[2-(2-methoxyphenyl)pyrimidin-5-yl]oxy}methyl)-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid-N-ethylethanamine salt (enantiomer 2), |
| 1-93 | (rac)-11-[(benzyloxy)methyl]-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid, |
| 1-94 | (rac)-(E/Z)-3-[(benzyloxy)methyl]-1-methyl-7-[3-(naphthalen-1-yloxy)propyl]-1,10,13,15-tetrahydropyrazolo[4',3':9,10][1,6]oxazacycloundecino[8,7,6-hi]indole-8-carboxylic acid, |

| Ex. No. | Name |
|---|---|
| 1-95 | (rac)-3-(hydroxymethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 1-96 | (rac)-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid, |
| 1-97 | (rac)-9,11-Dimethyl-1-[3-(1-naphthyloxy)propyl]-7-phenyl-4,5,6,7,8,9-hexahydropyrazolo[3',4':7,8][1,5]diazecino[9,10,1-hi]indole-2-carboxylic acid, |
| 1-98 | (rac)-9,11-Dimethyl-7-[4-(morpholin-4-Aphenyl]-1-[3-(1-naphthyloxy)propyl]-4,5,6,7,8,9-hexahydropyrazolo[3',4':7,8][1,5]diazecino[9,10,1-hi]indole-2-carboxylic acid, |
| 1-99 | 9,11-Dimethyl-7-[4-(morpholin-4-Aphenyl]-1-[3-(1-naphthyloxy)propyl]-4,5,6,7,8,9-hexahydropyrazolo[3',4':7,8][1,5]diazecino[9,10,1-hi]indole-2-carboxylic acid (enantiomer 1), |
| 1-100 | 9,11-Dimethyl-7-[4-(morpholin-4-Aphenyl]-1-[3-(1-naphthyloxy)propyl]-4,5,6,7,8,9-hexahydropyrazolo[3',4':7,8][1,5]diazecino[9,10,1-hi]indole-2-carboxylic acid (enantiomer 2), |
| 1-101 | (rac)-8,10-Dimethyl-1-[3-(1-naphthyloxy)propyl]-6-phenyl-5,6,7,8-tetrahydro-4H-pyrazolo[3',4':6,7][1,4]diazonino[8,9,1-hi]indole-2-carboxylic acid, |
| 1-102 | (rac)-11-(Methoxymethyl)-7,9-dimethyl-1-[3-(1-naphthyloxy)propyl]-4,5,6,7,8,9-hexahydropyrazolo[3',4':7,8][1,5]diazecino[9,10,1-hi]indole-2-carboxylic acid, |
| 1-103 | 11-(methoxymethyl)-7,9-dimethyl-1-[3-(1-naphthyloxy)propyl]-4,5,6,7,8,9-hexahydropyrazolo[3',4':7,8][1,5]diazecino[9,10,1-hi]indole-2-carboxylic acid (enantiomer 1), |
| 1-104 | 11-(methoxymethyl)-7,9-dimethyl-1-[3-(1-naphthyloxy)propyl]-4,5,6,7,8,9-hexahydropyrazolo[3',4':7,8][1,5]diazecino[9,10,1-hi]indole-2-carboxylic acid (enantiomer 2), |
| 1-105 | (rac)-7-{4-[4-(DimethylsulfamoyDpiperazin-1-yl]phenyl}-9,11-dimethyl-1-[3-(1-naphthyloxy) propyl]-4,5,6,7,8,9-hexahydropyrazolo[3',4':7,8][1,5]diazecino[9,10,1-hi]indole-2-carboxylic acid, |
| 1-106 | 7-{4-[4-(DimethylsulfamoyDpiperazin-1-yl]phenyl}-9,11-dimethyl-1-[3-(1-naphthyloxy) propyl]-4,5,6,7,8,9-hexahydropyrazolo[3',4':7,8][1,5]diazecino[9,10,1-hi]indole-2-carboxylic acid (enantiomer 1), |
| 1-107 | 7-{4-[4-(Dimethylsu lfamoyDpiperazin-1-yl]phenyl}-9,11-dimethyl-1-[3-(1-naphthyloxy) propyl]-4,5,6,7,8,9-hexahydropyrazolo[3',4':7,8][1,5]diazecino[9,10,1-hi]indole-2-carboxylic acid (enantiomer 2), |
| 1-108 | (rac)-7-{4-[4-(Ethylsulfonyl)piperazin-1-yl]phenyl}-9,11-dimethyl-1-[3-(1-naphthyloxy) propyl]-4,5,6,7,8,9-hexahydropyrazolo[3',4':7,8][1,5]diazecino[9,10,1-hi]indole-2-carboxylic acid, |
| 1-109 | 7-{4-[4-(Ethylsulfonyppiperazin-1-yl]phenyl}-9,11-dimethyl-1-[3-(1-naphthyloxy)propyl]-4,5,6,7,8,9-hexahydropyrazolo[3',4':7,8][1,5]diazecino[9,10,1-hi]indole-2-carboxylic acid (enantiomer 1), |
| 1-110 | 7-{4-[4-(Ethylsulfonyppiperazin-1-yl]phenyl}-9,11-dimethyl-1-[3-(1-naphthyloxy)propyl]-4,5,6,7,8,9-hexahydropyrazolo[3',4':7,8][1,5]diazecino[9,10,1-hi]indole-2-carboxylic acid (enantiomer 2), |
| 1-111 | (rac)-11-({4-[4-(Dimethylsulfamoyl)piperazin-1-yl]phenoxy}methyl)-7,10-dimethyl-1-[3-(1-naphthyloxy)propyl]-4,5,6,7,8,10-hexahydropyrazolo[3',4':7,8][1,5]diazecino[9,10,1-hi]indole-2-carboxylic acid, |
| 1-112 | 11-({4-[4-(Dimethylsulfamoyl)piperazin-1-yl]phenoxy}methyl)-7,10-dimethyl-1-[3-(1-naphthyloxy)propyl]-4,5,6,7,8,10-hexahydropyrazolo[3',4':7,8][1,5]diazecino[9,10,1-hi]indole-2-carboxylic acid (enantiomer 1), |
| 1-113 | 11-({4-[4-(Dimethylsulfamoyl)piperazin-1-yl]phenoxy}methyl)-7,10-dimethyl-1-[3-(1-naphthyloxy)propyl]-4,5,6,7,8,10-hexahydropyrazolo[3',4':7,8][1,5]diazecino[9,10,1-hi]indole-2-carboxylic acid (enantiomer 2), |
| 1-114 | (rac)-7,9-Dimethyl-1-[3-(1-naphthyloxy)propyl]-11-{[4-(2-oxopyridin-1(2H)-yl]phenoxy]methyl}-4,5,6,7,8,9-hexahydropyrazolo[3',4':7,8][1,5]diazecino[9,10,1-hi]indole-2-carboxylic acid, |
| 1-117 | (rac)-2'-Carboxy-10'-((4-(4-(N,N-dimethylsulfamoyl)piperazin-1-Aphenoxy)methyl)-8',11'-dimethyl-1'-(3-(naphthalen-1-yloxy)propyl)-4',5',7',8'-tetrahydrospiro[morpholine-4,6'-pyrazolo[3',4':6,7][1,4]diazonino[8,9,1-hi]indol]-4-ium bromide, |
| 1-118 | (rac)-12-Methoxy-1-[3-(5,6,7,8-tetrahydronaphthalen-1-yloxy)propyl]-4,5,7,8-tetrahydro-10,14-(metheno)[1,4,7]dioxazacyclotetradecino[9,8,7-hi]indole-2-carboxylic acid, |
| 1-119 | (rac)-12-Methoxy-1-[3-(1-naphthyloxy)propyl]-4,5,7,8-tetrahydro-10,14-(metheno)[1,4,7]dioxazacyclotetradecino[9,8,7-hi]indole-2-carboxylic acid, |
| 1-120 | (rac)-3-({4-[4-(CarboxymethyDpiperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 1-121 | (rac)-3-({4-[4-(3-hydroxy-3-methylbutyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid ammonium salt, |
| 1-122 | (rac)-12-Methoxy-1-[3-(naphthalen-1-yloxy)propyl]-5,6,7,8-tetrahydro-4H-10,14-(metheno)[1,7]oxazacyclotetradecino[9,8,7-hi]indole-2-carboxylic acid., |
| 003 | (rac)-9,11-dimethyl-1-[3-(1-naphthyloxy)propyl]-4,5,6,7,8,9-hexahydropyrazolo[4',3':4,5][1,6]diazecino[3,2,1-hi]indole-2-carboxylic acid, |
| 005 | (rac)-9,11-dimethyl-1-[3-(5,6,7,8-tetrahydronaphthalen-1-yloxy)propyl]-5,6,8,9-tetrahydro-4H-pyrazolo[4',3':8,9][1,5]oxazecino[7,6,5-hi]indole-2-carboxylic acid, |
| 006 | (rac)-1,3-dimethyl-7-[3-(5,6,7,8-tetrahydronaphthalen-1-yloxy)propyl]-1,10,11,12,13,15-hexahydropyrazolo[4',3':9,10][1,6]oxazacycloundecino[8,7,6-hi]indole-8-carboxylic acid, |

| Ex. No. | Name |
|---|---|
| 007 | 1,3-dimethyl-7-[3-(5,6,7,8-tetrahydronaphthalen-1-yloxy)propyl]-1,10,11,12,13,15-hexahydropyrazolo[4',3':9,10][1,6]oxazacycloundecino[8,7,6-hi]indole-8-carboxylic acid-N-ethylethanamine salt (enantiomer 1), |
| 008 | 1,3-dimethyl-7-[3-(5,6,7,8-tetrahydronaphthalen-1-yloxy)propyl]-1,10,11,12,13,15-hexahydropyrazolo[4',3':9,10][1,6]oxazacycloundecino[8,7,6-hi]indole-8-carboxylic acid-N-ethylethanamine salt (enantiomer 2), |
| 009 | (rac)-7-[3-(4-chloro-3,5-dimethylphenoxy)propyl]-1,3-dimethyl-1,10,11,12,13,15-hexahydropyrazolo[4',3':9,10][1,6]oxazacycloundecino[8,7,6-hi]indole-8-carboxylic acid, |
| 010 | 7-[3-(4-chloro-3,5-dimethylphenoxy)propyl]-1,3-dimethyl-1,10,11,12,13,15-hexahydropyrazolo[4',3':9,10][1,6]oxazacycloundecino[8,7,6-hi]indole-8-carboxylic acid-N-ethylethanamine salt (enantiomer 1), |
| 011 | 7-[3-(4-chloro-3,5-dimethylphenoxy)propyl]-1,3-dimethyl-1,10,11,12,13,15-hexahydropyrazolo[4',3':9,10][1,6]oxazacycloundecino[8,7,6-hi]indole-8-carboxylic acid-N-ethylethanamine salt (enantiomer 2), |
| 012 | (rac)-1,3-dimethyl-7-{3-[(7-methyl-1-naphthyl)oxy]propyl}-1,10,11,12,13,15-hexahydropyrazolo[4',3':9,10][1,6]oxazacycloundecino[8,7,6-hi]indole-8-carboxylic acid, |
| 013 | (rac)-1-[3-(4-chloro-3,5-dimethylphenoxy)propyl]-9,11-dimethyl-5,6,8,9-tetrahydro-4H-pyrazolo[4',3':8,9][1,5]oxazecino[7,6,5-hi]indole-2-carboxylic acid, |
| 014 | 1-[3-(4-chloro-3,5-dimethylphenoxy)propyl]-9,11-dimethyl-5,6,8,9-tetrahydro-4H-pyrazolo[4',3':8,9][1,5]oxazecino[7,6,5-hi]indole-2-carboxylic acid-N-ethylethanamine salt (enantiomer 1), |
| 015 | 1-[3-(4-chloro-3,5-dimethylphenoxy)propyl]-9,11-dimethyl-5,6,8,9-tetrahydro-4H-pyrazolo[4',3':8,9][1,5]oxazecino[7,6,5-hi]indole-2-carboxylic acid-N-ethylethanamine salt (enantiomer 2), |
| 016 | (rac)-1,3-dimethyl-7-(3-phenoxypropyl)-1,10,11,12,13,15-hexahydropyrazolo[4',3':9,10][1,6]oxazacycloundecino[8,7,6-hi]indole-8-carboxylic acid, |
| 017 | (rac)-1,3-dimethyl-7-[3-(1-naphthyloxy)propyl]-10,11,12,13,15,16-hexahydro-1H-pyrazolo[4',3':9,10][1,6]oxazacyclododecino[8,7,6-hi]indole-8-carboxylic acid, |
| 018 | (rac)-7-{3-[(6-fluoronaphthalen-1-yl)oxy]propyl}-1,3-dimethyl-1,10,11,12,13,15-hexahydropyrazolo[4',3':9,10][1,6]oxazacycloundecino[8,7,6-hi]indole-8-carboxylic acid, |
| 019 | 7-{3-[(6-fluoronaphthalen-1-yl)oxy]propyl}-1,3-dimethyl-1,10,11,12,13,15-hexahydropyrazolo[4',3':9,10][1,6]oxazacycloundecino[8,7,6-hi]indole-8-carboxylic acid-N-ethylethanamine salt (enantiomer 1), |
| 020 | 7-{3-[(6-fluoronaphthalen-1-yl)oxy]propyl}-1,3-dimethyl-1,10,11,12,13,15-hexahydropyrazolo[4',3':9,10][1,6]oxazacycloundecino[8,7,6-hi]indole-8-carboxylic acid-N-ethylethanamine salt (enantiomer 2), |
| 021 | (rac)-7-{3-[(4-fluoronaphthalen-1-yl)oxy]propyl}-1,3-dimethyl-1,10,11,12,13,15-hexahydropyrazolo[4',3':9,10][1,6]oxazacycloundecino[8,7,6-hi]indole-8-carboxylic acid, |
| 022 | 7-{3-[(4-fluoronaphthalen-1-yl)oxy]propyl}-1,3-dimethyl-1,10,11,12,13,15-hexahydropyrazolo[4',3':9,10][1,6]oxazacycloundecino[8,7,6-hi]indole-8-carboxylic acid-N-ethylethanamine salt (enantiomer 1), |
| 023 | 7-{3-[(4-fluoronaphthalen-1-yl)oxy]propyl}-1,3-dimethyl-1,10,11,12,13,15-hexahydropyrazolo[4',3':9,10][1,6]oxazacycloundecino[8,7,6-hi]indole-8-carboxylic acid-N-ethylethanamine salt (enantiomer 2) |
| 024 | (rac)-9,11,12-trimethyl-1-[3-(naphthalen-1-yloxy)propyl]-5,6,8,9-tetrahydro-4H-pyrazolo[4',3':8,9][1,5]oxazecino[7,6,5-hi]indole-2-carboxylic acid, |
| 025 | (+)-9,11,12-trimethyl-1-[3-(naphthalen-1-yloxy)propyl]-5,6,8,9-tetrahydro-4H-pyrazolo[4',3':8,9][1,5]oxazecino[7,6,5-hi]indole-2-carboxylic acid-N-ethylethanamine salt (enantiomer 1), |
| 026 | (−)-9,11,12-trimethyl-1-[3-(naphthalen-1-yloxy)propyl]-5,6,8,9-tetrahydro-4H-pyrazolo[4',3':8,9][1,5]oxazecino[7,6,5-hi]indole-2-carboxylic acid-N-ethylethanamine salt (enantiomer 2), |
| 027 | (rac)-1,3,4-trimethyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 028 | 1,3,4-trimethyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid-N-ethylethanamine salt (enantiomer 1), |
| 029 | 1,3,4-trimethyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid-N-ethylethanamine salt (enantiomer 2), |
| 038 | (rac)-(E/Z)-1,3,4-trimethyl-7-[3-(1-naphthyloxy)propyl]-1,10, 13, 15-tetrahydropyrazolo[4',3':9,10][1,6]oxazacycloundecino[8,7,6-hi]indole-8-carboxylic acid, |
| 039 | (rac)-1,3,4-trimethyl-7-[3-(5,6,7,8-tetrahydronaphthalen-1-yloxy)propyl]-1,10,11,12,13,15-hexahydropyrazolo[4',3':9,10][1,6]oxazacycloundecino[8,7,6-hi]indole-8-carboxylic acid, |
| 040 | (rac)-7-{3-[(6-chloronaphthalen-1-yl)oxy]propyl}-1,3-dimethyl-1,10,11,12,13,15-hexahydropyrazolo[4',3':9,10][1,6]oxazacycloundecino[8,7,6-hi]indole-8-carboxylic acid, |
| 041 | 7-{3-[(6-chloronaphthalen-1-yl)oxy]propyl}-1,3-dimethyl-1,10,11,12,13,15-hexahydropyrazolo[4',3':9,10][1,6]oxazacycloundecino[8,7,6-hi]indole-8-carboxylic acid-N-ethylethanamine salt (enantiomer 1), |
| 042 | 7-{3-[(6-chloronaphthalen-1-yl)oxy]propyl}-1,3-dimethyl-1,10,11,12,13,15-hexahydropyrazolo[4',3':9,10][1,6]oxazacycloundecino[8,7,6-hi]indole-8-carboxylic acid-N-ethylethanamine salt (enantiomer 2), |
| 043 | (rac)-9,11-dimethyl-1-[3-(naphthalen-1-yloxy)propyl]-5,6,8,9-tetrahydro-4H-pyrazolo[4',3':8,9][1,5]oxazecino[7,6,5-hi]indole-2-carboxylic acid, |

| Ex. No. | Name |
|---|---|
| 044 | 9,11-dimethyl-1-[3-(naphthalen-1-yloxy)propyl]-5,6,8,9-tetrahydro-4H-pyrazolo[4',3':8,9][1,5]oxazecino[7,6,5-hi]indole-2-carboxylic acid-N-ethylethanamine salt (enantiomer 1), |
| 045 | 9,11-dimethyl-1-[3-(naphthalen-1-yloxy)propyl]-5,6,8,9-tetrahydro-4H-pyrazolo[4',3':8,9][1,5]oxazecino[7,6,5-hi]indole-2-carboxylic acid-N-ethylethanamine salt (enantiomer 2) |
| 046 | (rac)-1-{3-[(6-fluoronaphthalen-1-yl)oxy]propyl}-9,11-dimethyl-5,6,8,9-tetrahydro-4H-pyrazolo[4',3':8,9][1,5]oxazecino[7,6,5-hi]indole-2-carboxylic acid |
| 047 | 1-{3-[(6-fluoronaphthalen-1-yl)oxy]propyl}-9,11-dimethyl-5,6,8,9-tetrahydro-4H-pyrazolo[4',3':8,9][1,5]oxazecino[7,6,5-hi]indole-2-carboxylic acid-N-ethylethanamine salt (enantiomer 1), |
| 048 | 1-{3-[(6-fluoronaphthalen-1-yl)oxy]propyl}-9,11-dimethyl-5,6,8,9-tetrahydro-4H-pyrazolo[4',3':8,9][1,5]oxazecino[7,6,5-hi]indole-2-carboxylic acid-N-ethylethanamine salt (enantiomer 2), |
| 049 | (rac)-7-{3-[(6-fluoro-7-methylnaphthalen-1-yl)oxy]propyl}-1,3-dimethyl-1,10,11,12,13,15-hexahydropyrazolo[4',3':9,10][1,6]oxazacycloundecino[8,7,6-hi]indole-8-carboxylic acid, |
| 050 | 7-{3-[(6-fluoro-7-methylnaphthalen-1-yl)oxy]propyl}-1,3-dimethyl-1,10,11,12,13,15-hexahydropyrazolo[4',3':9,10][1,6]oxazacycloundecino[8,7,6-hi]indole-8-carboxylic acid-N-ethylethanamine salt (enantiomer 1), |
| 051 | 7-{3-[(6-fluoro-7-methylnaphthalen-1-yl)oxy]propyl}-1,3-dimethyl-1,10,11,12,13,15-hexahydropyrazolo[4',3':9,10][1,6]oxazacycloundecino[8,7,6-hi]indole-8-carboxylic acid-N-ethylethanamine salt (enantiomer 2), |
| 052 | (rac)-10-(2-methoxyethyl)-7,11-dimethyl-1-[3-(naphthalen-1-yloxy)propyl]-4,5,6,7,8,10-hexahydropyrazolo[3',4':7,8][1,5]diazecino[9,10,1-hi]indole-2-carboxylic acid, |
| 053 | (rac)-3-methyl-2-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid, |
| 054 | 3-methyl-2-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid-N-ethylethanamine salt (enantiomer 1), |
| 055 | 3-methyl-2-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid-N-ethylethanamine salt (enantiomer 2), |
| 056 | (rac)-10-(2-methoxyethyl)-7-methyl-11-(morpholin-4-ylmethyl)-1-[3-(naphthalen-1-yloxy)propyl]-4,5,6,7,8,10-hexahydropyrazolo[3',4':7,8][1,5]diazecino[9,10,1-hi]indole-2-carboxylic acid, |
| 057 | 10-(2-methoxyethyl)-7-methyl-11-(morpholin-4-ylmethyl)-1-[3-(naphthalen-1-yloxy)propyl]-4,5,6,7,8,10-hexahydropyrazolo[3',4':7,8][1,5]diazecino[9,10,1-hi]indole-2-carboxylic acid (enantiomer 1), |
| 058 | 10-(2-methoxyethyl)-7-methyl-11-(morpholin-4-ylmethyl)-1-[3-(naphthalen-1-yloxy)propyl]-4,5,6,7,8,10-hexahydropyrazolo[3',4':7,8][1,5]diazecino[9,10,1-hi]indole-2-carboxylic acid (enantiomer 2), |
| 059 | (rac)-7,11-dimethyl-10-[2-(morpholin-4-yl)ethyl]-1-[3-(naphthalen-1-yloxy)propyl]-4,5,6,7,8,10-hexahydropyrazolo[3',4':7,8][1,5]diazecino[9,10,1-hi]indole-2-carboxylic acid, |
| 060 | 7,11-dimethyl-10-[2-(morpholin-4-yl)ethyl]-1-[3-(naphthalen-1-yloxy)propyl]-4,5,6,7,8,10-hexahydropyrazolo[3',4':7,8][1,5]diazecino[9,10,1-hi]indole-2-carboxylic acid (enantiomer 1), |
| 061 | 7,11-dimethyl-10-[2-(morpholin-4-yl)ethyl]-1-[3-(naphthalen-1-yloxy)propyl]-4,5,6,7,8,10-hexahydropyrazolo[3',4':7,8][1,5]diazecino[9,10,1-hi]indole-2-carboxylic acid (enantiomer 2), |
| 062 | (rac)-(11Z)-2,3-dimethyl-7-[3-(naphthalen-1-yloxy)propyl]-2,10,13,15-tetrahydropyrazolo[4',3':9,10][1,6]oxazacycloundecino[8,7,6-hi]indole-8-carboxylic acid, |
| 063 | (rac)-10,11-dimethyl-1-[3-(naphthalen-1-yloxy)propyl]-5,6,8,10-tetrahydro-4H-pyrazolo[4',3':8,9][1,5]oxazecino[7,6,5-hi]indole-2-carboxylic acid, |
| 064 | 10,11-dimethyl-1-[3-(naphthalen-1-yloxy)propyl]-5,6,8,10-tetrahydro-4H-pyrazolo[4',3':8,9][1,5]oxazecino[7,6,5-hi]indole-2-carboxylic acid-N-ethylethanamine salt (enantiomer 1), |
| 065 | 10,11-dimethyl-1-[3-(naphthalen-1-yloxy)propyl]-5,6,8,10-tetrahydro-4H-pyrazolo[4',3':8,9][1,5]oxazecino[7,6,5-hi]indole-2-carboxylic acid-N-ethylethanamine salt (enantiomer 2), |
| 066 | (rac)-(11Z)-2-Methyl-3-(morpholin-4-ylmethyl)-7-[3-(naphthalen-1-yloxy)propyl]-2,10,13,15-tetrahydropyrazolo[4',3':9,10][1,6]oxazacycloundecino[8,7,6-hi]indole-8-carboxylic acid, |
| 067 | (rac)-2,3,14-trimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylic acid, |
| 068 | 2,3,14-trimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylic acid (enantiomer 1), |
| 069 | 2,3,14-trimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylic acid (enantiomer 2), |
| 070 | (rac)-(11Z)-2,3,4-trimethyl-7-[3-(naphthalen-1-yloxy)propyl]-2,10,13,15-tetrahydropyrazolo[4',3':9,10][1,6]oxazacycloundecino[8,7,6-hi]indole-8-carboxylic acid, |
| 071 | (rac)-(11Z)-2-(2-methoxyethyl)-3-methyl-7-[3-(naphthalen-1-yloxy)propyl]-2,10,13,15-tetrahydropyrazolo[4',3':9,10][1,6]oxazacycloundecino[8,7,6-hi]indole-8-carboxylic acid, |
| 072 | (rac)-7,10,11,12-tetramethyl-1-[3-(naphthalen-1-yloxy)propyl]-4,5,6,7,8,10-hexahydropyrazolo[3',4':7,8][1,5]diazecino[9,10,1-hi]indole-2-carboxylic acid, |

-continued

| Ex. No. | Name |
|---|---|
| 073 | 7,10,11,12-tetramethyl-1-[3-(naphthalen-1-yloxy)propyl]-4,5,6,7,8,10-hexahydropyrazolo[3',4':7,8][1,5]diazecino[9,10,1-hi]indole-2-carboxylic acid (enantiomer 1), |
| 074 | 7,10,11,12-tetramethyl-1-[3-(naphthalen-1-yloxy)propyl]-4,5,6,7,8,10-hexahydropyrazolo[3',4':7,8][1,5]diazecino[9,10,1-hi]indole-2-carboxylic acid (enantiomer 2), |
| 075 | (rac)-2,3,4-trimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid, |
| 076 | 2,3,4-trimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (enantiomer 1), |
| 077 | 2,3,4-trimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (enantiomer 2), |
| 078 | (rac)-2-Methyl-3-(morpholin-4-ylmethyl)-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid, |
| 079 | 2-methyl-3-(morpholin-4-ylmethyl)-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid-N-ethylethanamine salt (enantiomer 1), |
| 080 | 2-methyl-3-(morpholin-4-ylmethyl)-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid-N-ethylethanamine salt (enantiomer 2), |
| 087 | (rac)-2-Methyl-3-(morpholin-4-ylmethyl)-7-[3-(naphthalen-1-yloxy)propyl]-2,10,11,13,14,16-hexahydropyrazolo[4',3':10,11][1,4,7]dioxazacyclododecino[9,8,7-hi]indole-8-carboxylic acid, |
| 096 | 3-methyl-1-[2-(morpholin-4-yl)ethyl]-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid-N-ethylethanamine salt (enantiomer 1), |
| 097 | 3-methyl-1-[2-(morpholin-4-yl)ethyl]-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid-N-ethylethanamine salt (enantiomer 2), |
| 099 | (rac)-3-(methoxymethyl)-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid, |
| 100 | 3-(methoxymethyl)-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid-N-ethylethanamine salt (enantiomer 1), |
| 101 | 3-(methoxymethyl)-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid-N-ethylethanamine salt (enantiomer 2), |
| 105 | (rac)-3-(methoxymethyl)-2-methyl-7-[3-(5,6,7,8-tetrahydronaphthalen-1-yloxy)propyl]-2,10,11,12,13,15-hexahydropyrazolo[4',3':9,10][1,6]oxazacycloundecino[8,7,6-hi]indole-8-carboxylic acid, |
| 107 | 2-(2-methoxyethyl)-3-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid-N-ethylethanamine salt (enantiomer 1), |
| 108 | 2-(2-methoxyethyl)-3-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid-N-ethylethanamine salt (enantiomer 2), |
| 113 | (rac)-7,10-dimethyl-1-[3-(naphthalen-1-yloxy)propyl]-11-(propan-2-yl)-4,5,6,7,8,10-hexahydropyrazolo[3',4':7,8][1,5]diazecino[9,10,1-hi]indole-2-carboxylic acid |
| 114 | 7,10-dimethyl-1-[3-(naphthalen-1-yloxy)propyl]-11-(propan-2-yl)-4,5,6,7,8,10-hexahydropyrazolo[3',4':7,8][1,5]diazecino[9,10,1-hi]indole-2-carboxylic acid (enantiomer 1), |
| 115 | 7,10-dimethyl-1-[3-(naphthalen-1-yloxy)propyl]-11-(propan-2-yl)-4,5,6,7,8,10-hexahydropyrazolo[3',4':7,8][1,5]diazecino[9,10,1-hi]indole-2-carboxylic acid (enantiomer 2), |
| 116 | (rac)-12-Methoxy-1-[3-(5,6,7,8-tetrahydronaphthalen-1-yloxy)propyl]-5,6,7,8-tetrahydro-4H-10,14-(metheno)[1,7]oxazacyclotetradecino[9,8,7-hi]indole-2-carboxylic acid, |
| 117 | (rac)-13-Methyl-1-[3-(naphthalen-1-yloxy)propyl]-4,5,7,8-tetrahydro-10,14-(metheno)[1,4,7]dioxazacyclotetradecino[9,8,7-hi]indole-2-carboxylic acid, |
| 118 | (rac)-(E/Z)-1-methyl-3-{[4-(morpholin-4-Aphenoxy]methyl}-7-[3-(naphthalen-1-yloxy)propyl]-1,10,13,15-tetrahydropyrazolo[4',3':9,10][1,6]oxazacycloundecino[8,7,6-hi]indole-8-carboxylic acid, |
| 119 | (+)-(E/Z)-1-methyl-3-{[4-(morpholin-4-Aphenoxy]methyl}-7-[3-(naphthalen-1-yloxy)propyl]-1,10,13,15-tetrahydropyrazolo[4',3':9,10][1,6]oxazacycloundecino[8,7,6-hi]indole-8-carboxylic acid (enantiomer 1), |
| 120 | (−)-(E/Z)-1-methyl-3-{[4-(morpholin-4-yl)phenoxy]methyl}-7-[3-(naphthalen-1-yloxy)propyl]-1,10,13,15-tetrahydropyrazolo[4',3':9,10][1,6]oxazacycloundecino[8,7,6-hi]indole-8-carboxylic acid (enantiomer 2), |
| 122 | 1-methyl-3-{[4-(morpholin-4-yl)phenoxy]methyl}-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1), |
| 123 | 1-methyl-3-{[4-(morpholin-4-yl)phenoxy]methyl}-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2), |

| Ex. No. | Name |
|---|---|
| 124 | (rac)-7,9-dimethyl-11-[2-(morpholin-4-yl)ethyl]-1-[3-(naphthalen-1-yloxy)propyl]-4,5,6,7,8,9-hexahydropyrazolo[3',4':7,8][1,5]diazecino[9,10,1-hi]indole-2-carboxylic acid, |
| 125 | 7,9-dimethyl-11-[2-(morpholin-4-yl)ethyl]-1-[3-(naphthalen-1-yloxy)propyl]-4,5,6,7,8,9-hexahydropyrazolo[3',4':7,8][1,5]diazecino[9,10,1-hi]indole-2-carboxylic acid (enantiomer 1) |
| 126 | 7,9-dimethyl-11-[2-(morpholin-4-yl)ethyl]-1-[3-(naphthalen-1-yloxy)propyl]-4,5,6,7,8,9-hexahydropyrazolo[3',4':7,8][1,5]diazecino[9,10,1-hi]indole-2-carboxylic acid (enantiomer 2), |
| 127 | (rac)-1,14-dimethyl-7-[3-(naphthalen-1-yloxy)propyl]-10,11,12,13,14,15-hexahydro-1H-pyrazolo[3',4':8,9][1,6]diazacycloundecino[10,11,1-hi]indole-8-carboxylic acid, |
| 128 | (rac)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 132 | (rac)-(E/Z)-1-methyl-3-(morpholin-4-ylmethyl)-7-[3-(naphthalen-1-yloxy)propyl]-1,10,13,15-tetrahydropyrazolo[4',3':9,10][1,6]oxazacycloundecino[8,7,6-hi]indole-8-carboxylic acid, |
| 133 | (E/Z)-1-methyl-3-(morpholin-4-ylmethyl)-7-[3-(naphthalen-1-yloxy)propyl]-1,10,13,15-tetrahydropyrazolo[4',3':9,10][1,6]oxazacycloundecino[8,7,6-hi]indole-8-carboxylic acid-N-ethylethanamine salt (enantiomer 1), |
| 134 | (E/Z)-1-methyl-3-(morpholin-4-ylmethyl)-7-[3-(naphthalen-1-yloxy)propyl]-1,10,13,15-tetrahydropyrazolo[4',3':9,10][1,6]oxazacycloundecino[8,7,6-hi]indole-8-carboxylic acid-N-ethylethanamine salt (enantiomer 2), |
| 135 | (rac)-1-methyl-3-(morpholin-4-ylmethyl)-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 136 | 1-methyl-3-(morpholin-4-ylmethyl)-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1), |
| 137 | 1-methyl-3-(morpholin-4-ylmethyl)-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2), |
| 138 | (rac)-9-methyl-11-(morpholin-4-ylmethyl)-1-[3-(naphthalen-1-yloxy)propyl]-5,6,8,9-tetrahydro-4H-pyrazolo[4',3':8,9][1,5]oxazecino[7,6,5-hi]indole-2-carboxylic acid, |
| 139 | 9-methyl-11-(morpholin-4-ylmethyl)-1-[3-(naphthalen-1-yloxy)propyl]-5,6,8,9-tetrahydro-4H-pyrazolo[4',3':8,9][1,5]oxazecino[7,6,5-hi]indole-2-carboxylic acid (enantiomer 1), |
| 140 | 9-methyl-11-(morpholin-4-ylmethyl)-1-[3-(naphthalen-1-yloxy)propyl]-5,6,8,9-tetrahydro-4H-pyrazolo[4',3':8,9][1,5]oxazecino[7,6,5-hi]indole-2-carboxylic acid (enantiomer 2), |
| 141 | (rac)-11-ethyl-7,10-dimethyl-1-[3-(1-naphthyloxy)propyl]-4,5,6,7,8,10-hexahydropyrazolo[3',4':7,8][1,5]diazecino[9,10,1-hi]indole-2-carboxylic acid, |
| 142 | 11-Ethyl-7,10-dimethyl-1-[3-(1-naphthyloxy)propyl]-4,5,6,7,8,10-hexahydropyrazolo[3',4':7,8][1,5]diazecino[9,10,1-hi]indole-2-carboxylic acid N-ethylethanamine salt (enantiomer 1), |
| 143 | 11-ethyl-7,10-dimethyl-1-[3-(1-naphthyloxy)propyl]-4,5,6,7,8,10-hexahydropyrazolo[3',4':7,8][1,5]diazecino[9,10,1-hi]indole-2-carboxylic acid N-ethylethanamine salt (enantiomer 2), |
| 144 | (rac)-11-ethyl-7,10,12-trimethyl-1-[3-(1-naphthyloxy)propyl]-4,5,6,7,8,10-hexahydropyrazolo[3',4':7,8][1,5]diazecino[9,10,1-hi]indole-2-carboxylic acid, |
| 145 | 11-Ethyl-7,10,12-trimethyl-1-[3-(1-naphthyloxy)propyl]-4,5,6,7,8,10-hexahydropyrazolo[3',4':7,8][1,5]diazecino[9,10,1-hi]indole-2-carboxylic acid N-ethylethanamine salt (enantiomer 1), |
| 146 | 11-Ethyl-7,10,12-trimethyl-1-[3-(1-naphthyloxy)propyl]-4,5,6,7,8,10-hexahydropyrazolo[3',4':7,8][1,5]diazecino[9,10,1-hi]indole-2-carboxylic acid N-ethylethanamine salt (enantiomer 2), |
| 147 | (rac)-3-Ethyl-2-methyl-7-[3-(1-naphthyloxy)propyl]-2,10,11,12,13,15-hexahydropyrazolo[4',3':9,10][1,6]oxazacycloundecino[8,7,6-hi]indole-8-carboxylic acid, |
| 148 | 3-Ethyl-2-methyl-7-[3-(1-naphthyloxy)propyl]-2,10,11,12,13,15-hexahydropyrazolo[4',3':9,10][1,6]oxazacycloundecino[8,7,6-hi]indole-8-carboxylic acid N-ethylethanamine salt (enantiomer 1), |
| 149 | 3-Ethyl-2-methyl-7-[3-(1-naphthyloxy)propyl]-2,10,11,12,13,15-hexahydropyrazolo[4',3':9,10][1,6]oxazacycloundecino[8,7,6-hi]indole-8-carboxylic acid N-ethylethanamine salt (enantiomer 2), |
| 150 | (rac)-1-methyl-3-[2-(morpholin-4-yl)ethyl]-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 151 | 1-methyl-3-[2-(morpholin-4-yl)ethyl]-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid-N-ethylethanamine salt (enantiomer 1), |
| 152 | 1-methyl-3-[2-(morpholin-4-yl)ethyl]-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid-N-ethylethanamine salt (enantiomer 2), |
| 153 | (rac)-3-Ethyl-2,4-dimethyl-7-[3-(1-naphthyloxy)propyl]-2,10,11,12,13,15-hexahydropyrazolo[4',3':9,10][1,6]oxazacycloundecino[8,7,6-hi]indole-8-carboxylic acid |
| 154 | 3-Ethyl-2,4-dimethyl-7-[3-(1-naphthyloxy)propyl]-2,10,11,12,13,15-hexahydropyrazolo[4',3':9,10][1,6]oxazacycloundecino[8,7,6-hi]indole-8-carboxylic acid N-ethylethanamine salt (enantiomer 1), |
| 155 | 3-Ethyl-2,4-dimethyl-7-[3-(1-naphthyloxy)propyl]-2,10,11,12,13,15-hexahydropyrazolo[4',3':9,10][1,6]oxazacycloundecino[8,7,6-hi]indole-8-carboxylic acid N-ethylethanamine salt (enantiomer 2), |

| Ex. No. | Name |
|---|---|
| 159 | 3-(methoxymethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid N-ethylethanamine salt (enantiomer 1), |
| 160 | 3-(methoxymethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid-N-ethylethanamine salt (enantiomer 2), |
| 169 | 3-(ethoxymethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1), |
| 170 | 3-(ethoxymethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2) |
| 171 | 3-(ethoxymethyl)-1-methyl-7-[3-(5,6,7,8-tetrahydronaphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1), |
| 172 | 3-(ethoxymethyl)-1-methyl-7-[3-(5,6,7,8-tetrahydronaphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2), |
| 177 | (rac)-3-(methoxymethyl)-1-methyl-7-[3-(naphthalen-1-yloxy)propyl]-1,11,12,13,14,16-hexahydro-10H-pyrazolo[3',4':3,4][1,7]oxazacyclododecino[5,6,7-hi]indole-8-carboxylic acid, |
| 178 | 3-(methoxymethyl)-1-methyl-7-[3-(naphthalen-1-yloxy)propyl]-1,11,12,13,14,16-hexahydro-10H-pyrazolo[3',4':3,4][1,7]oxazacyclododecino[5,6,7-hi]indole-8-carboxylic acid N-ethylethanamine salt (enantiomer 1), |
| 179 | 3-(methoxymethyl)-1-methyl-7-[3-(naphthalen-1-yloxy)propyl]-1,11,12,13,14,16-hexahydro-10H-pyrazolo[3',4':3,4][1,7]oxazacyclododecino[5,6,7-hi]indole-8-carboxylic acid N-ethylethanamine salt (enantiomer 2), |
| 183 | (rac)-3-(methoxymethyl)-1,14-dimethyl-7-[3-(naphthalen-1-yloxy)propyl]-10,11,12,13,14,15-hexahydro-1H-pyrazolo[3',4':8,9][1,6]diazacycloundecino[10,11,1-hi]indole-8-carboxylic acid, |
| 184 | 3-(methoxymethyl)-1,14-dimethyl-7-[3-(naphthalen-1-yloxy)propyl]-10,11,12,13,14,15-hexahydro-1H-pyrazolo[3',4':8,9][1,6]diazacycloundecino[10,11,1-hi]indole-8-carboxylic acid-N-ethylethanamine salt (enantiomer 1), |
| 185 | 3-(methoxymethyl)-1,14-dimethyl-7-[3-(naphthalen-1-yloxy)propyl]-10,11,12,13,14,15-hexahydro-1H-pyrazolo[3',4':8,9][1,6]diazacycloundecino[10,11,1-hi]indole-8-carboxylic acid-N-ethylethanamine salt (enantiomer 2), |
| 187 | (rac)-1,4-dimethyl-7-[3-(naphthalen-1-yloxy)propyl]-3-propyl-1,10,11,12,13,15-hexahydropyrazolo[4',3':9,10][1,6]oxazacycloundecino[8,7,6-hi]indole-8-carboxylic acid, |
| 188 | 1,4-dimethyl-7-[3-(naphthalen-1-yloxy)propyl]-3-propyl-1,10,11,12,13,15-hexahydropyrazolo[4',3':9,10][1,6]oxazacycloundecino[8,7,6-hi]indole-8-carboxylic acid-N-ethylethanamine salt (enantiomer 1), |
| 189 | 1,4-dimethyl-7-[3-(naphthalen-1-yloxy)propyl]-3-propyl-1,10,11,12,13,15-hexahydropyrazolo[4',3':9,10][1,6]oxazacycloundecino[8,7,6-hi]indole-8-carboxylic acid-N-ethylethanamine salt (enantiomer 2), |
| 190 | (rac)-2,3-dimethyl-7-[3-(1-naphthyloxy)propyl]-10,11,12,13,14,15-hexahydro-2H-pyrazolo[4',3':4,5]azacycloundecino[3,2,1-hi]indole-8-carboxylic acid, |
| 191 | 2,3-dimethyl-7-[3-(1-naphthyloxy)propyl]-10,11,12,13,14,15-hexahydro-2H-pyrazolo[4',3':4,5]azacycloundecino[3,2,1-hi]indole-8-carboxylic acid-N-ethylethanamine salt (enantiomer 1), |
| 192 | 2,3-dimethyl-7-[3-(1-naphthyloxy)propyl]-10,11,12,13,14,15-hexahydro-2H-pyrazolo[4',3':4,5]azacycloundecino[3,2,1-hi]indole-8-carboxylic acid-N-ethylethanamine salt (enantiomer 2), |
| 193 | (rac)-7,9,12-trimethyl-1-[3-(naphthalen-1-yloxy)propyl]-11-propyl-4,5,6,7,8,9-hexahydropyrazolo[3',4':7,8][1,5]diazecino[9,10,1-hi]indole-2-carboxylic acid, |
| 196 | 7,9,12-trimethyl-1-[3-(naphthalen-1-yloxy)propyl]-11-propyl-4,5,6,7,8,9-hexahydropyrazolo[3',4':7,8][1,5]diazecino[9,10,1-hi]indole-2-carboxylic acid N-ethylethanamine salt (enantiomer 1), |
| 197 | 7,9,12-trimethyl-1-[3-(naphthalen-1-yloxy)propyl]-11-propyl-4,5,6,7,8,9-hexahydropyrazolo[3',4':7,8][1,5]diazecino[9,10,1-hi]indole-2-carboxylic acid N-ethylethanamine salt (enantiomer 2), |
| 198 | (rac)-3-ethyl-1-[2-(morpholin-4-yl)ethyl]-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 199 | 3-ethyl-1-[2-(morpholin-4-yl)ethyl]-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1), |
| 200 | 3-ethyl-1-[2-(morpholin-4-yl)ethyl]-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2), |
| 201 | (rac)-3-ethyl-2-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid |
| 202 | 3-ethyl-2-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (enantiomer 1), |
| 203 | 3-ethyl-2-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (enantiomer 2), |

-continued

| Ex. No. | Name |
|---|---|
| 204 | (rac)-3-ethyl-4-methyl-2-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid, |
| 205 | 3-ethyl-4-methyl-2-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (enantiomer 1), |
| 206 | 3-ethyl-4-methyl-2-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (enantiomer 2), |
| 237 | (rac)-1,3,15-Trimethyl-7-[3-(naphthalen-1-yloxy)propyl]-1,10,11,12,13,14,15,16-octahydropyrazolo[4',3':4,5][1,7]diazacyclododecino[3,2,1-hi]indole-8-carboxylic acid, |
| 238 | (+)-1,3,15-trimethyl-7-[3-(naphthalen-1-yloxy)propyl]-1,10,11,12,13,14,15,16-octahydropyrazolo[4',3':4,5][1,7]diazacyclododecino[3,2,1-hi]indole-8-carboxylic acid (enantiomer 1), |
| 239 | (+1,3,15-trimethyl-7-[3-(naphthalen-1-yloxy)propyl]-1,10,11,12,13,14,15,16-octahydropyrazolo[4',3':4,5][1,7]diazacyclododecino[3,2,1-hi]indole-8-carboxylic acid (enantiomer 2), |
| 240 | (rac)-1,3,15-Trimethyl-7-[3-(5,6,7,8-tetrahydronaphthalen-1-yloxy)propyl]-1,10,11,12,13,14,15,16-octahydropyrazolo[4',3':4,5][1,7]diazacyclododecino[3,2,1-hi]indole-8-carboxylic acid, |
| 247 | (rac)-1-[3-(naphthalen-1-yloxy)propyl]-4,5,6,7,13,14-hexahydro-9H,12H-[1,3]oxazino[3'',2'':1',5']pyrazolo[4',3':9,10][1,6]oxazacycloundecino[8,7,6-hi]indole-2-carboxylic acid, |
| 248 | 1-[3-(naphthalen-1-yloxy)propyl]-4,5,6,7,13,14-hexahydro-9H,12H-[1,3]oxazino[3'',2'':1',5']pyrazolo[4',3':9,10][1,6]oxazacycloundecino[8,7,6-hi]indole-2-carboxylic acid (enantiomer 1), |
| 249 | 1-[3-(naphthalen-1-yloxy)propyl]-4,5,6,7,13,14-hexahydro-9H,12H-[1,3]oxazino[3'',2'':1',5']pyrazolo[4',3':9,10][1,6]oxazacycloundecino[8,7,6-hi]indole-2-carboxylic acid (enantiomer 2), |
| 250 | (rac)-1-[3-(naphthalen-1-yloxy)propyl]-4,5,6,7,12,13-hexahydro-9H,15H-[1,4]oxazino[4'',3'':1',5']pyrazolo[4',3':9,10][1,6]oxazacycloundecino[8,7,6-hi]indole-2-carboxylic acid, |
| 251 | 1-[3-(naphthalen-1-yloxy)propyl]-4,5,6,7,12,13-hexahydro-9H,15H-[1,4]oxazino[4'',3'':1',5']pyrazolo[4',3':9,10][1,6]oxazacycloundecino[8,7,6-hi]indole-2-carboxylic acid-N-ethylethanamine salt (enantiomer 1), |
| 252 | 1-[3-(naphthalen-1-yloxy)propyl]-4,5,6,7,12,13-hexahydro-9H,15H-[1,4]oxazino[4'',3'':1',5']pyrazolo[4',3':9,10][1,6]oxazacycloundecino[8,7,6-hi]indole-2-carboxylic acid-N-ethylethanamine salt (enantiomer 2), |
| 253 | (rac)-1-[3-(naphthalen-1-yloxy)propyl]-4,5,6,7,12,13,14,15-octahydro-9H-pyrido[2'':1',5']pyrazolo[4',3':9,10][1,6]oxazacycloundecino[8,7,6-hi]indole-2-carboxylic acid, |
| 254 | 1-[3-(naphthalen-1-yloxy)propyl]-4,5,6,7,12,13,14,15-octahydro-9H-pyrido[2'':1',5']pyrazolo[4',3':9,10][1,6]oxazacycloundecino[8,7,6-hi]indole-2-carboxylic acid (enantiomer 1), |
| 255 | 1-[3-(naphthalen-1-yloxy)propyl]-4,5,6,7,12,13,14,15-octahydro-9H-pyrido[2'':1',5']pyrazolo[4',3':9,10][1,6]oxazacycloundecino[8,7,6-hi]indole-2-carboxylic acid (enantiomer 2), |
| 256 | 1,3,4-trimethyl-7-[4-(naphthalen-1-yloxy)butan-2-yl]-1,10,11,12,13,15-hexahydropyrazolo[4',3':9,10][1,6]oxazacycloundecino[8,7,6-hi]indole-8-carboxylic acid (mixture of stereoisomers), |
| 257 | 1,3,4-trimethyl-7-[4-(naphthalen-1-yloxy)butan-2-yl]-1,10,11,12,13,15-hexahydropyrazolo[4',3':9,10][1,6]oxazacycloundecino[8,7,6-hi]indole-8-carboxylic acid (stereoisomer 1), |
| 258 | 1,3,4-trimethyl-7-[4-(naphthalen-1-yloxy)butan-2-yl]-1,10,11,12,13,15-hexahydropyrazolo[4',3':9,10][1,6]oxazacycloundecino[8,7,6-hi]indole-8-carboxylic acid (stereoisomer 2), |
| 259 | 1,3,4-trimethyl-7-[4-(naphthalen-1-yloxy)butan-2-yl]-1,10,11,12,13,15-hexahydropyrazolo[4',3':9,10][1,6]oxazacycloundecino[8,7,6-hi]indole-8-carboxylic acid (stereoisomer 3), |
| 260 | 1,3,4-trimethyl-7-[4-(naphthalen-1-yloxy)butan-2-yl]-1,10,11,12,13,15-hexahydropyrazolo[4',3':9,10][1,6]oxazacycloundecino[8,7,6-hi]indole-8-carboxylic acid (stereoisomer 4), |
| 261 | 3-ethyl-7-{4-[(6-fluoronaphthalen-1-yl)oxy]butan-2-yl}-1,4-dimethyl-1,10,11,12,13,15-hexahydropyrazolo[4',3':9,10][1,6]oxazacycloundecino[8,7,6-hi]indole-8-carboxylic acid (mixture of stereoisomers), |
| 262 | 3-ethyl-7-{4-[(6-fluoronaphthalen-1-yl)oxy]butan-2-yl}-1,4-dimethyl-1,10,11,12,13,15-hexahydropyrazolo[4',3':9,10][1,6]oxazacycloundecino[8,7,6-hi]indole-8-carboxylic acid (stereoisomer 1), |
| 263 | 3-ethyl-7-{4-[(6-fluoronaphthalen-1-yl)oxy]butan-2-yl}-1,4-dimethyl-1,10,11,12,13,15-hexahydropyrazolo[4',3':9,10][1,6]oxazacycloundecino[8,7,6-hi]indole-8-carboxylic acid (stereoisomer 2), |
| 264 | 3-ethyl-7-{4-[(6-fluoronaphthalen-1-yl)oxy]butan-2-yl}-1,4-dimethyl-1,10,11,12,13,15-hexahydropyrazolo[4',3':9,10][1,6]oxazacycloundecino[8,7,6-hi]indole-8-carboxylic acid (stereoisomer 3), |

| Ex. No. | Name |
|---|---|
| 265 | 3-ethyl-7-{4-[(6-fluoronaphthalen-1-yl)oxy]butan-2-yl}-1,4-dimethyl-1,10,11,12,13,15-hexahydropyrazolo[4',3':9,10][1,6]oxazacycloundecino[8,7,6-hi]indole-8-carboxylic acid (stereoisomer 4), |
| 266 | (rac)-3-ethyl-7-{3-[(6-fluoronaphthalen-1-yl)oxy]propyl}-1,4-dimethyl-1,10,11,12,13,15-hexahydropyrazolo[4',3':9,10][1,6]oxazacycloundecino[8,7,6-hi]indole-8-carboxylic acid, |
| 267 | (+)-3-ethyl-7-{3-[(6-fluoronaphthalen-1-yl)oxy]propyl}-1,4-dimethyl-1,10,11,12,13,15-hexahydropyrazolo[4',3':9,10][1,6]oxazacycloundecino[8,7,6-hi]indole-8-carboxylic acid (enantiomer 1), |
| 268 | (−)-3-ethyl-7-{3-[(6-fluoronaphthalen-1-yl)oxy]propyl}-1,4-dimethyl-1,10,11,12,13,15-hexahydropyrazolo[4',3':9,10][1,6]oxazacycloundecino[8,7,6-hi]indole-8-carboxylic acid (enantiomer 2), |
| 269 | (rac)-1-(3-(4-chloro-3,5-dimethylphenoxy)propyl)-12-ethyl-10,13-dimethyl-4,5,6,7,9,10-hexahydropyrazolo[4',3':9,10][1]oxa[6]azacycloundecino[8,7,6-hi]indole-2-carboxylic acid |
| 270 | (rac)-12-ethyl-10,13-dimethyl-1-(3-((5,6,7,8-tetrahydronaphthalen-1-yl)oxy)propyl)-4,5,6,7,9,10-hexahydropyrazolo[4',3':9,10][1]oxa[6]azacycloundecino[8,7,6-hi]indole-2-carboxylic acid, |
| 271 | 3-ethyl-1,4-dimethyl-7-[4-(naphthalen-1-yloxy)butan-2-yl]-1,10,11,12,13,15-hexahydropyrazolo[4',3':9,10][1,6]oxazacycloundecino[8,7,6-hi]indole-8-carboxylic acid (mixture of stereoisomers), |
| 272 | 3-ethyl-1,4-dimethyl-7-[4-(naphthalen-1-yloxy)butan-2-yl]-1,10,11,12,13,15-hexahydropyrazolo[4',3':9,10][1,6]oxazacycloundecino[8,7,6-hi]indole-8-carboxylic acid (stereoisomer 1), |
| 273 | 3-ethyl-1,4-dimethyl-7-[4-(naphthalen-1-yloxy)butan-2-yl]-1,10,11,12,13,15-hexahydropyrazolo[4',3':9,10][1,6]oxazacycloundecino[8,7,6-hi]indole-8-carboxylic acid (stereoisomer 2), |
| 274 | 3-ethyl-1,4-dimethyl-7-[4-(naphthalen-1-yloxy)butan-2-yl]-1,10,11,12,13,15-hexahydropyrazolo[4',3':9,10][1,6]oxazacycloundecino[8,7,6-hi]indole-8-carboxylic acid (stereoisomer 3), |
| 275 | 3-ethyl-1,4-dimethyl-7-[4-(naphthalen-1-yloxy)butan-2-yl]-1,10,11,12,13,15-hexahydropyrazolo[4',3':9,10][1,6]oxazacycloundecino[8,7,6-hi]indole-8-carboxylic acid (stereoisomer 4), |
| 276 | 7-{4-[(6-fluoronaphthalen-1-yl)oxy]butan-2-yl}-2,3,4-trimethyl-2,10,11,12,13,15-hexahydropyrazolo[4',3':9,10][1,6]oxazacycloundecino[8,7,6-hi]indole-8-carboxylic acid (mixture of stereoisomers), |
| 277 | 7-{4-[(6-fluoronaphthalen-1-yl)oxy]butan-2-yl}-2,3,4-trimethyl-2,10,11,12,13,15-hexahydropyrazolo[4',3':9,10][1,6]oxazacycloundecino[8,7,6-hi]indole-8-carboxylic acid (stereoisomer 1), |
| 278 | 7-{4-[(6-fluoronaphthalen-1-yl)oxy]butan-2-yl}-2,3,4-trimethyl-2,10,11,12,13,15-hexahydropyrazolo[4',3':9,10][1,6]oxazacycloundecino[8,7,6-hi]indole-8-carboxylic acid (stereoisomer 2), |
| 279 | 7-{4-[(6-fluoronaphthalen-1-yl)oxy]butan-2-yl}-2,3,4-trimethyl-2,10,11,12,13,15-hexahydropyrazolo[4',3':9,10][1,6]oxazacycloundecino[8,7,6-hi]indole-8-carboxylic acid (stereoisomer 3), |
| 280 | 7-{4-[(6-fluoronaphthalen-1-yl)oxy]butan-2-yl}-2,3,4-trimethyl-2,10,11,12,13,15-hexahydropyrazolo[4',3':9,10][1,6]oxazacycloundecino[8,7,6-hi]indole-8-carboxylic acid (stereoisomer 4), |
| 281 | (rac)-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid, |
| 282 | (+)-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid-N-ethylethanamine salt (enantiomer 1), |
| 283 | (−)-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid-N-ethylethanamine salt (enantiomer 2), |
| 284 | (rac)-7-{3-[(6-fluoronaphthalen-1-yl)oxy]propyl}-3-methyl-2-[2-(morpholin-4-yl)ethyl]-2,10,11,12,13,15-hexahydropyrazolo[4',3':9,10][1,6]oxazacycloundecino[8,7,6-hi]indole-8-carboxylic acid, |
| 285 | (+)-7-{3-[(6-fluoronaphthalen-1-yl)oxy]propyl}-3-methyl-2-[2-(morpholin-4-yl)ethyl]-2,10,11,12,13,15-hexahydropyrazolo[4',3':9,10][1,6]oxazacycloundecino[8,7,6-hi]indole-8-carboxylic acid-N-ethylethanamine salt (enantiomer 1) |
| 286 | (−)-7-{3-[(6-fluoronaphthalen-1-yl)oxy]propyl}-3-methyl-2-[2-(morpholin-4-yl)ethyl]-2,10,11,12,13,15-hexahydropyrazolo[4',3':9,10][1,6]oxazacycloundecino[8,7,6-hi]indole-8-carboxylic acid-N-ethylethanamine salt (enantiomer 2), |
| 287 | (rac)-3-ethyl-7-{3-[(6-fluoronaphthalen-1-yl)oxy]propyl}-1-methyl-1,10,11,12,13,15-hexahydropyrazolo[4',3':9,10][1,6]oxazacycloundecino[8,7,6-hi]indole-8-carboxylic acid, |
| 288 | (+)-3-ethyl-7-{3-[(6-fluoronaphthalen-1-yl)oxy]propyl}-1-methyl-1,10,11,12,13,15-hexahydropyrazolo[4',3':9,10][1,6]oxazacycloundecino[8,7,6-hi]indole-8-carboxylic acid (enantiomer 1), |
| 289 | (−)-3-ethyl-7-{3-[(6-fluoronaphthalen-1-yl)oxy]propyl}-1-methyl-1,10,11,12,13,15-hexahydropyrazolo[4',3':9,10][1,6]oxazacycloundecino[8,7,6-hi]indole-8-carboxylic acid (enantiomer 2), |
| 290 | (rac)-12-ethyl-11-methyl-1-(3-((5,6,7,8-tetrahydronaphthalen-1-yl)oxy)propyl)-4,5,6,7,9,11-hexahydropyrazolo[4',3':9,10][1]oxa[6]azacycloundecino[8,7,6-hi]indole-2-carboxylic acid, |
| 291 | (rac)-12-ethyl-10-methyl-1-(3-((5,6,7,8-tetrahydronaphthalen-1-yl)oxy)propyl)-4,5,6,7,9,10-hexahydropyrazolo[4',3':9,10][1]oxa[6]azacycloundecino[8,7,6-hi]indole-2-carboxylic acid, |

-continued

| Ex. No. | Name |
|---|---|
| 292 | (rac)-7-{3-[(6-fluoronaphthalen-1-yl)oxy]propyl}-3,4-dimethyl-2-[2-(morpholin-4-yl)ethyl]-2,10,11,12,13,15-hexahydropyrazolo[4',3':9,10][1,6]oxazacycloundecino[8,7,6-hi]indole-8-carboxylic acid, |
| 293 | (+)-7-{3-[(6-fluoronaphthalen-1-yl)oxy]propyl}-3,4-dimethyl-2-[2-(morpholin-4-yl)ethyl]-2,10,11,12,13,15-hexahydropyrazolo[4',3':9,10][1,6]oxazacycloundecino[8,7,6-hi]indole-8-carboxylic acid-N-ethylethanamine salt (enantiomer 1), |
| 294 | (−)-7-{3-[(6-fluoronaphthalen-1-yl)oxy]propyl}-3,4-dimethyl-2-[2-(morpholin-4-yl)ethyl]-2,10,11,12,13,15-hexahydropyrazolo[4',3':9,10][1,6]oxazacycloundecino[8,7,6-hi]indole-8-carboxylic acid-N-ethylethanamine salt (enantiomer 2), |
| 295 | (rac)-7-{3-[(6-chloronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid, |
| 296 | (+)-7-{3-[(6-chloronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid-N-ethylethanamine salt (enantiomer 1), |
| 297 | (−)-7-{3-[(6-chloronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid-N-ethylethanamine salt (enantiomer 2), |
| 298 | (rac)-3-ethyl-7-{3-[(5-fluoronaphthalen-1-yl)oxy]propyl}-1-methyl-1,10,11,12,13,15-hexahydropyrazolo[4',3':9,10][1,6]oxazacycloundecino[8,7,6-hi]indole-8-carboxylic acid, |
| 299 | 3-ethyl-7-{3-[(5-fluoronaphthalen-1-yl)oxy]propyl}-1-methyl-1,10,11,12,13,15-hexahydropyrazolo[4',3':9,10][1,6]oxazacycloundecino[8,7,6-hi]indole-8-carboxylic acid (enantiomer 2), |
| 300 | 3-ethyl-7-{3-[(5-fluoronaphthalen-1-yl)oxy]propyl}-1-methyl-1,10,11,12,13,15-hexahydropyrazolo[4',3':9,10][1,6]oxazacycloundecino[8,7,6-hi]indole-8-carboxylic acid (enantiomer 1), |
| 301 | (rac)-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid, |
| 302 | (+)-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid (enantiomer 2), |
| 303 | (−)-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid (enantiomer 1), |
| 304 | (rac)-11-(3-(6-chloronaphthalen-1-yl)oxy)propyl)-12-ethyl-10-methyl-4,5,6,7,9,10-hexahydropyrazolo[4',3':9,10][1,6]oxaazacycloundecino[8,7,6-hi]indole-2-carboxylic acid, |
| 305 | 7-{3-[(6-chloronaphthalen-1-yl)oxy]propyl}-3-ethyl-1-methyl-1,10,11,12,13,15-hexahydropyrazolo[4',3':9,10][1,6]oxazacycloundecino[8,7,6-hi]indole-8-carboxylic acid (enantiomer 1), |
| 306 | 7-{3-[(6-chloronaphthalen-1-yl)oxy]propyl}-3-ethyl-1-methyl-1,10,11,12,13,15-hexahydropyrazolo[4',3':9,10][1,6]oxazacycloundecino[8,7,6-hi]indole-8-carboxylic acid (enantiomer 2), |
| 307 | (rac)-11,12-dimethyl-1-(3-(6-methylnaphthalen-1-yl)oxy)propyl)-4,5,6,7,9,11-hexahydropyrazolo[4',3':9,10][1,6]oxaazacycloundecino[8,7,6-hi]indole-2-carboxylic acid, |
| 308 | 2,3-dimethyl-7-{3-[(6-methylnaphthalen-1-yl)oxy]propyl}-2,10,11,12,13,15-hexahydropyrazolo[4',3':9,10][1,6]oxazacycloundecino[8,7,6-hi]indole-8-carboxylic acid (enantiomer 1) |
| 309 | 2,3-dimethyl-7-{3-[(6-methylnaphthalen-1-yl)oxy]propyl}-2,10,11,12,13,15-hexahydropyrazolo[4',3':9,10][1,6]oxazacycloundecino[8,7,6-hi]indole-8-carboxylic acid (enantiomer 2), |
| 310 | (rac)-12-ethyl-10-methyl-1-(3-((6-(trifluoromethyDnaphthalen-1-yl)oxy)propyl)-4,5,6,7,9,10-hexahydropyrazolo[4',3':9,10][1]oxa[6]azacycloundecino[8,7,6-hi]indole-2-carboxylic acid, |
| 311 | 2,3-dimethyl-7-(3-{[6-(trifluoromethyl)naphthalen-1-yl]oxy}propyl)-2,10,11,12,13,15-hexahydropyrazolo[4',3':9,10][1,6]oxazacycloundecino[8,7,6-hi]indole-8-carboxylic acid (enantiomer 1), |
| 312 | 2,3-dimethyl-7-(3-{[6-(trifluoromethyl)naphthalen-1-yl]oxy}propyl)-2,10,11,12,13,15-hexahydropyrazolo[4',3':9,10][1,6]oxazacycloundecino[8,7,6-hi]indole-8-carboxylic acid (enantiomer 2), |
| 313 | (rac)-12-ethyl-10-methyl-1-(3-((6-(trifluoromethyDnaphthalen-1-yl)oxy)propyl)-4,5,6,7,9,10-hexahydropyrazolo[4',3':9,10][1,6]oxaazacycloundecino[8,7,6-hi]indole-2-carboxylic acid, |
| 314 | 3-ethyl-1-methyl-7-(3-{[6-(trifluoromethyl)naphthalen-1-yl]oxy}propyl)-1,10,11,12,13,15-hexahydropyrazolo[4',3':9,10][1,6]oxazacycloundecino[8,7,6-hi]indole-8-carboxylic acid (enantiomer 1), |
| 315 | 3-ethyl-1-methyl-7-(3-{[6-(trifluoromethyl)naphthalen-1-yl]oxy}propyl)-1,10,11,12,13,15-hexahydropyrazolo[4',3':9,10][1,6]oxazacycloundecino[8,7,6-hi]indole-8-carboxylic acid (enantiomer 2), |
| 316 | (rac)-1-(3-(5-chloronaphthalen-1-yl)oxy)propyl)-10,12-dimethyl-4,5,6,7,9,10-hexahydropyrazolo[4',3':9,10][1,6]oxaazacycloundecino[8,7,6-hi]indole-2-carboxylic acid, |
| 317 | (+)-1,3-dimethyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1), |
| 318 | (+1,3-dimethyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2), |
| 332 | (rac)-1-methyl-7-[3-(naphthalen-1-yloxy)propyl]-3-(piperidin-1-ylmethyl)-1,10,11,12,13,15-hexahydropyrazolo[4',3':9,10][1,6]oxazacycloundecino[8,7,6-hi]indole-8-carboxylic acid, |

| Ex. No. | Name |
|---|---|
| 333 | 1-methyl-7-[3-(naphthalen-1-yloxy)propyl]-3-(piperidin-1-ylmethyl)-1,10,11,12,13,15-hexahydropyrazolo[4',3':9,10][1,6]oxazacycloundecino[8,7,6-hi]indole-8-carboxylic acid (enantiomer 1), |
| 334 | 1-methyl-7-[3-(naphthalen-1-yloxy)propyl]-3-(piperidin-1-ylmethyl)-1,10,11,12,13,15-hexahydropyrazolo[4',3':9,10][1,6]oxazacycloundecino[8,7,6-hi]indole-8-carboxylic acid (enantiomer 2), |
| 335 | (rac)-1-methyl-7-[3-(naphthalen-1-yloxy)propyl]-3-(pyrrolidin-1-ylmethyl)-1,10,11,12,13,15-hexahydropyrazolo[4',3':9,10][1,6]oxazacycloundecino[8,7,6-hi]indole-8-carboxylic acid, |
| 336 | 1-methyl-7-[3-(naphthalen-1-yloxy)propyl]-3-(pyrrolidin-1-ylmethyl)-1,10,11,12,13,15-hexahydropyrazolo[4',3':9,10][1,6]oxazacycloundecino[8,7,6-hi]indole-8-carboxylic acid (enantiomer 1), |
| 337 | 1-methyl-7-[3-(naphthalen-1-yloxy)propyl]-3-(pyrrolidin-1-ylmethyl)-1,10,11,12,13,15-hexahydropyrazolo[4',3':9,10][1,6]oxazacycloundecino[8,7,6-hi]indole-8-carboxylic acid (enantiomer 2), |
| 354 | (rac)-2,3-dimethyl-7-[2-(naphthalen-1-yl)ethyl]-2,10,11,12,13,15-hexahydropyrazolo[4',3':9,10][1,6]oxazacycloundecino[8,7,6-hi]indole-8-carboxylic acid, |
| 355 | (rac)-2,3-dimethyl-7-{2-[4-(trifluoromethyl)phenyl]ethyl}-2,10,11,12,13,15-hexahydropyrazolo[4',3':9,10][1,6]oxazacycloundecino[8,7,6-hi]indole-8-carboxylic acid, |
| 356 | (rac)-2,3-dimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylic acid, |
| 357 | (rac)-2,3-dimethyl-7-[2-(naphthalen-2-yloxy)ethyl]-2,10,11,12,13,15-hexahydropyrazolo[4',3':9,10][1,6]oxazacycloundecino[8,7,6-hi]indole-8-carboxylic acid, |
| 360 | (rac)-7-methyl-1-[3-(naphthalen-1-yloxy)propyl]-5,6,7,8,12,13-hexahydro-4H,11H-[1,3]oxazino[3'',2'':1',5']pyrazolo[3',4':7,8][1,5]diazecino[9,10,1-hi]indole-2-carboxylic acid, |
| 361 | (rac)-7-methyl-1-[3-(naphthalen-1-yloxy)propyl]-5,6,7,8,11,12,13,14-octahydro-4H-pyrido[1,2'':1',5']pyrazolo[3',4':7,8][1,5]diazecino[9,10,1-hi]indole-2-carboxylic acid, |
| 362 | 11,12,13-trimethyl-1-(4-(naphthalen-1-yloxy)butan-2-yl)-4,5,6,7,9,11-hexahydropyrazolo[4',3':9,10][1,6]oxaazacycloundecino[8,7,6-hi]indole-2-carboxylic acid (mixture of stereoisomers), |
| 363 | 11,12,13-trimethyl-1-(4-((5,6,7,8-tetrahydronaphthalen-1-yl)oxy)butan-2-yl)-4,5,6,7,9,11-hexahydropyrazolo[4',3':9,10][1,6]oxaazacycloundecino[8,7,6-hi]indole-2-carboxylic acid (mixture of stereoisomers) and |
| 364 | (rac)-10,12-dimethyl-1-(3-(6-(trifluoromethyl)naphthalen-1-yl)oxy)propyl)-4,5,6,7,9,10-hexahydropyrazolo[4',3':9,10][1,6]oxaazacycloundecino[8,7,6-hi]indole-2-carboxylic acid. | or a tautomer, an N-oxide, or a salt thereof or a salt of a tautomer or a N-oxide or a mixture of same.

In some embodiments, the present invention includes compounds of general formula (I) selected from:

| Ex.No. | Name |
|---|---|
| 001 | (rac)-(E/Z)-8-benzyl-9,11-dimethyl-1-[3-(1-naphthyloxy)propyl]-4,7,8,9-tetrahydropyrazolo[4',3':4,5][1,6]diazecino[3,2,1-hi]indole-2-carboxylic acid, |
| 002 | (rac)-8-benzyl-9,11-dimethyl-1-[3-(1-naphthyloxy)propyl]-4,5,6,7,8,9-hexahydropyrazolo[4',3':4,5][1,6]diazecino[3,2,1-hi]indole-2-carboxylic acid (Example 002), |
| 004 | (rac)-(7-benzyl-11-({54-[4-(dimethylsulfamoyl)piperazin-1-yl]phenoxy}methyl)-9-methyl-1-[3-(1-naphthyloxy)propyl]-4,5,6,7,8,9-hexahydropyrazolo[3',4':7,8][1,5]diazecino[9,10,1-hi]indole-2-carboxylic acid, |
| 081 | (rac)-3-Cyclopropyl-2-ethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid, |
| 082 | 3-cyclopropyl-2-ethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid - N-ethylethanamine salt (enantiomer 1), |
| 083 | 3-cyclopropyl-2-ethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid - N-ethylethanamine salt (enantiomer 2), |
| 084 | (rac)-3-Cyclopropyl-2-(2-methoxyethyl)-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid, |
| 085 | 3-Cyclopropyl-2-(2-methoxyethyl)-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid - N-ethylethanamine salt (enantiomer 1), |
| 086 | 3-Cyclopropyl-2-(2-methoxyethyl)-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid - N-ethylethanamine salt (enantiomer 2), |
| 088 | (rac)-3-Cyclopropyl-1-ethyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 089 | 3-cyclopropyl-1-ethyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid - N-ethylethanamine salt (enantiomer 1), |
| 090 | 3-cyclopropyl-1-ethyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid - N-ethylethanamine salt (enantiomer 2), |
| 091 | (rac)-(11Z)-3-methyl-7-[3-(naphthalen-1-yloxy)propyl]-2-(2,2,2-trifluoroethyl)-2,10,13,15-tetrahydropyrazolo[4',3':9,10][1,6]oxazacycloundecino[8,7,6-hi]indole-8-carboxylic acid, |

-continued

| Ex.No. | Name |
|---|---|
| 092 | (rac)-2-cyclopropyl-3-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid, |
| 093 | 2-cyclopropyl-3-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid - N-ethylethanamine salt (enantiomer 1), |
| 094 | 2-cyclopropyl-3-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid - N-ethylethanamine salt (enantiomer 2), |
| 098 | (rac)-(11Z)-3-methyl-7-[3-(naphthalen-1-yloxy)propyl]-1-(2,2,2-trifluoroethyl)-1,10,13,15-tetrahydropyrazolo[4',3':9,10][1,6]oxazacycloundecino[8,7,6-hi]indole-8-carboxylic acid, |
| 102 | (rac)-3-Cyclopropyl-1-(2-methoxyethyl)-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 103 | 3-cyclopropyl-1-(2-methoxyethyl)-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid - N-ethylethanamine salt (enantiomer 1), |
| 104 | 3-cyclopropyl-1-(2-methoxyethyl)-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid - N-ethylethanamine salt (enantiomer 2), |
| 109 | (rac)-3-methyl-7-[3-(naphthalen-1-yloxy)propyl]-1-(2,2,2-trifluoroethyl)-1,10,11,12,13,15-hexahydropyrazolo[4',3':9,10][1,6]oxazacycloundecino[8,7,6-hi]indole-8-carboxylic acid, |
| 110 | 3-methyl-7-[3-(naphthalen-1-yloxy)propyl]-1-(2,2,2-trifluoroethyl)-1,10,11,12,13,15-hexahydropyrazolo[4',3':9,10][1,6]oxazacycloundecino[8,7,6-hi]indole-8-carboxylic acid - N-ethylethanamine salt (enantiomer 1), |
| 111 | 3-methyl-7-[3-(naphthalen-1-yloxy)propyl]-1-(2,2,2-trifluoroethyl)-1,10,11,12,13,15-hexahydropyrazolo[4',3':9,10][1,6]oxazacycloundecino[8,7,6-hi]indole-8-carboxylic acid - N-ethylethanamine salt (enantiomer 2), |
| 129 | (rac)-7,9-dimethyl-1-[3-(naphthalen-1-yloxy)propyl]-11-{[(2,2,2-trifluoroethyl)amino]methyl}-4,5,6,7,8,9-hexahydropyrazolo[3',4':7,8][1,5]diazecino[9,10,1-hi]indole-2-carboxylic acid (racemate), |
| 130 | 7,9-dimethyl-1-[3-(naphthalen-1-yloxy)propyl]-11-{[(2,2,2-trifluoroethyl)amino]methyl}-4,5,6,7,8,9-hexahydropyrazolo[3',4':7,8][1,5]diazecino[9,10,1-hi]indole-2-carboxylic acid-N-ethylethanamine salt (enantiomer 1), |
| 131 | 7,9-dimethyl-1-[3-(naphthalen-1-yloxy)propyl]-11-{[(2,2,2-trifluoroethyl)amino]methyl}-4,5,6,7,8,9-hexahydropyrazolo[3',4':7,8][1,5]diazecino[9,10,1-hi]indole-2-carboxylic acid-N-ethylethanamine salt (enantiomer 2), |
| 156 | (rac)-3-[(ethylamino)methyl]-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 157 | (rac)-7,9-dimethyl-1-[3-(naphthalen-1-yloxy)propyl]-11-[(3-oxomorpholin-4-yl)methyl]-4,5,6,7,8,9-hexahydropyrazolo[3',4':7,8][1,5]diazecino[9,10,1-hi]indole-2-carboxylic acid, |
| 161 | (rac)-3-methyl-7-[3-(5,6,7,8-tetrahydronaphthalen-1-yloxy)propyl]-1-(2,2,2-trifluoroethyl)-1,10,11,12,13,15-hexahydropyrazolo[4',3':9,10][1,6]oxazacycloundecino[8,7,6-hi]indole-8-carboxylic acid, |
| 162 | 3-methyl-7-[3-(5,6,7,8-tetrahydronaphthalen-1-yloxy)propyl]-1-(2,2,2-trifluoroethyl)-1,10,11,12,13,15-hexahydropyrazolo[4',3':9,10][1,6]oxazacycloundecino[8,7,6-hi]indole-8-carboxylic acid - N-ethylethanamine salt (enantiomer 1), |
| 163 | 3-methyl-7-[3-(5,6,7,8-tetrahydronaphthalen-1-yloxy)propyl]-1-(2,2,2-trifluoroethyl)-1,10,11,12,13,15-hexahydropyrazolo[4',3':9,10][1,6]oxazacycloundecino[8,7,6-hi]indole-8-carboxylic acid - N-ethylethanamine salt (enantiomer 2), |
| 164 | (rac)-3-Cyclopropyl-1-(2-methoxyethyl)-7-[3-(5,6,7,8-tetrahydronaphthalen-1-yloxy)propyl]-1,10,11,12,13,15-hexahydropyrazolo[4',3':9,10][1,6]oxazacycloundecino[8,7,6-hi]indole-8-carboxylic acid, |
| 165 | 3-Cyclopropyl-1-(2-methoxyethyl)-7-[3-(5,6,7,8-tetrahydronaphthalen-1-yloxy)propyl]-1,10,11,12,13,15-hexahydropyrazolo[4',3':9,10][1,6]oxazacycloundecino[8,7,6-hi]indole-8-carboxylic acid - N-ethylethanamine salt (enantiomer 1), |
| 166 | 3-Cyclopropyl-1-(2-methoxyethyl)-7-[3-(5,6,7,8-tetrahydronaphthalen-1-yloxy)propyl]-1,10,11,12,13,15-hexahydropyrazolo[4',3':9,10][1,6]oxazacycloundecino[8,7,6-hi]indole-8-carboxylic acid - N-ethylethanamine salt (enantiomer 2), |
| 180 | (rac)-3-[(3,3-difluoroazetidin-1-yl)methyl]-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 181 | 3-[(3,3-difluoroazetidin-1-yl)methyl]-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid - N- ethylethanamine salt (enantiomer 1), |
| 182 | 3-[(3,3-difluoroazetidin-1-yl)methyl]-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid - N- ethylethanamine salt (enantiomer 2), |
| 186 | (rac)-2-methyl-7-[3-(naphthalen-1-yloxy)propyl]-3-(trifluoromethyl)-2,10,11,12,13,15-hexahydropyrazolo[4',3':9,10][1,6]oxazacycloundecino[8,7,6-hi]indole-8-carboxylic acid, |
| 194 | 2-methyl-7-[3-(naphthalen-1-yloxy)propyl]-3-(trifluoromethyl)-2,10,11,12,13,15-hexahydropyrazolo[4',3':9,10][1,6]oxazacycloundecino[8,7,6-hi]indole-8-carboxylic acid (enantiomer 1), |
| 195 | 2-methyl-7-[3-(naphthalen-1-yloxy)propyl]-3-(trifluoromethyl)-2,10,11,12,13,15-hexahydropyrazolo[4',3':9,10][1,6]oxazacycloundecino[8,7,6-hi]indole-8-carboxylic acid (enantiomer 2), |
| 207 | (rac)-3-methoxy-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylate, |

| Ex.No. | Name |
|---|---|
| 208 | 3-methoxy-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylate (enantiomer 1), |
| 209 | 3-methoxy-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylate (enantiomer 2), |
| 210 | (rac)-1-methyl-7-[3-(naphthalen-1-yloxy)propyl]-3-[(pyrimidin-5-yloxy)methyl]-1,10,11,12,13,15-hexahydropyrazolo[4',3':9,10][1,6]oxazacycloundecino[8,7,6-hi]indole-8-carboxylic acid, |
| 211 | 1-methyl-7-[3-(naphthalen-1-yloxy)propyl]-3-[(pyrimidin-5-yloxy)methyl]-1,10,11,12,13,15-hexahydropyrazolo[4',3':9,10][1,6]oxazacycloundecino[8,7,6-hi]indole-8-carboxylic acid (enantiomer 1), |
| 212 | 1-methyl-7-[3-(naphthalen-1-yloxy)propyl]-3-[(pyrimidin-5-yloxy)methyl]-1,10,11,12,13,15-hexahydropyrazolo[4',3':9,10][1,6]oxazacycloundecino[8,7,6-hi]indole-8-carboxylic acid (enantiomer 2), |
| 213 | (rac)-3-[(cyclopropyloxy)methyl]-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 214 | 3-[(cyclopropyloxy)methyl]-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1) |
| 215 | 3-[(cyclopropyloxy)methyl]-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2), |
| 216 | (rac)-1-methyl-7-[3-(naphthalen-1-yloxy)propyl]-3-(trifluoromethyl)-1,10,11,12,13,15-hexahydropyrazolo[4',3':9,10][1,6]oxazacycloundecino[8,7,6-hi]indole-8-carboxylic acid, |
| 217 | 1-methyl-7-[3-(naphthalen-1-yloxy)propyl]-3-(trifluoromethyl)-1,10,11,12,13,15-hexahydropyrazolo[4',3':9,10][1,6]oxazacycloundecino[8,7,6-hi]indole-8-carboxylic acid (enantiomer 1), |
| 218 | 1-methyl-7-[3-(naphthalen-1-yloxy)propyl]-3-(trifluoromethyl)-1,10,11,12,13,15-hexahydropyrazolo[4',3':9,10][1,6]oxazacycloundecino[8,7,6-hi]indole-8-carboxylic acid (enantiomer 2), |
| 219 | (rac)-1-methyl-7-[3-(naphthalen-1-yloxy)propyl]-3-(2,2,2-trifluoroethyl)-1,10,11,12,13,15-hexahydropyrazolo[4',3':9,10][1,6]oxazacycloundecino[8,7,6-hi]indole-8-carboxylic acid, |
| 220 | 1-methyl-7-[3-(naphthalen-1-yloxy)propyl]-3-(2,2,2-trifluoroethyl)-1,10,11,12,13,15-hexahydropyrazolo[4',3':9,10][1,6]oxazacycloundecino[8,7,6-hi]indole-8-carboxylic acid - N-ethylethanamine salt (enantiomer 1), |
| 221 | 1-methyl-7-[3-(naphthalen-1-yloxy)propyl]-3-(2,2,2-trifluoroethyl)-1,10,11,12,13,15-hexahydropyrazolo[4',3':9,10][1,6]oxazacycloundecino[8,7,6-hi]indole-8-carboxylic acid - N-ethylethanamine salt (enantiomer 2), |
| 222 | (rac)-1,14-dimethyl-7-[3-(naphthalen-1-yloxy)propyl]-3-(2,2,2-trifluoroethyl)-10,11,12,13,14,15-hexahydro-1H-pyrazolo[3',4':8,9][1,6]diazacycloundecino[10,11,1-hi]indole-8-carboxylic acid, |
| 223 | 1,14-dimethyl-7-[3-(naphthalen-1-yloxy)propyl]-3-(2,2,2-trifluoroethyl)-10,11,12,13,14,15-hexahydro-1H-pyrazolo[3',4':8,9][1,6]diazacycloundecino[10,11,1-hi]indole-8-carboxylic acid (enantiomer 1), |
| 224 | 1,14-dimethyl-7-[3-(naphthalen-1-yloxy)propyl]-3-(2,2,2-trifluoroethyl)-10,11,12,13,14,15-hexahydro-1H-pyrazolo[3',4':8,9][1,6]diazacycloundecino[10,11,1-hi]indole-8-carboxylic acid (enantiomer 2), |
| 225 | (rac)-3-[(E)-2-fluoroethenyl]-1,14-dimethyl-7-[3-(naphthalen-1-yloxy)propyl]-10,11,12,13,14,15-hexahydro-1H-pyrazolo[3',4':8,9][1,6]diazacycloundecino[10,11,1-hi]indole-8-carboxylic acid, |
| 226 | 3-[(E)-2-fluoroethenyl]-1,14-dimethyl-7-[3-(naphthalen-1-yloxy)propyl]-10,11,12,13,14,15-hexahydro-1H-pyrazolo[3',4':8,9][1,6]diazacycloundecino[10,11,1-hi]indole-8-carboxylic acid (enantiomer 1), |
| 227 | 3-[(E)-2-fluoroethenyl]-1,14-dimethyl-7-[3-(naphthalen-1-yloxy)propyl]-10,11,12,13,14,15-hexahydro-1H-pyrazolo[3',4':8,9][1,6]diazacycloundecino[10,11,1-hi]indole-8-carboxylic acid (enantiomer 2), |
| 228 | 3-(2,2-difluoroethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 229 | 3-(2,2-difluoroethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1), |
| 230 | 3-(2,2-difluoroethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2), |
| 231 | (rac)-1-methyl-3-{[(1-methyl-1H-imidazol-2-yl)methoxy]methyl}-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 232 | (+)-1-methyl-3-{[(1-methyl-1H-imidazol-2-yl)methoxy]methyl}-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1), |
| 233 | (−)-1-methyl-3-{[(1-methyl-1H-imidazol-2-yl)methoxy]methyl}-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2), |

-continued

| Ex.No. | Name |
| --- | --- |
| 234 | (rac)-3-(difluoromethoxy)-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid |
| 235 | (−)-3-(difluoromethoxy)-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (enantiomer 1), |
| 236 | (−)-1,3,15-trimethyl-7-[3-(naphthalen-1-yloxy)propyl]-1,10,11,12,13,14,15,16-octahydropyrazolo[4',3':4,5][1,7]diazacyclododecino[3,2,1-hi]indole-8-carboxylic acid (enantiomer 2), |
| 241 | 3-methyl-7-[3-(naphthalen-1-yloxy)propyl]-2-(2,2,2-trifluoroethyl)-2,10,11,12,13,15-hexahydropyrazolo[4',3':9,10][1,6]oxazacycloundecino[8,7,6-hi]indole-8-carboxylic acid (enantiomer 1), |
| 242 | 3-methyl-7-[3-(naphthalen-1-yloxy)propyl]-2-(2,2,2-trifluoroethyl)-2,10,11,12,13,15-hexahydropyrazolo[4',3':9,10][1,6]oxazacycloundecino[8,7,6-hi]indole-8-carboxylic acid (enantiomer 2), |
| 243 | (rac)-2-[2-(dimethylamino)ethyl]-3-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid trifluoroacetic acid salt, |
| 244 | (rac)-1-[2-(dimethylamino)ethyl]-3-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid trifluoroacetic acid salt, |
| 319 | (rac)-3-[(4-methoxyphenoxy)methyl]-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 320 | 3-[(4-methoxyphenoxy)methyl]-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid - N- ethylethanamine salt (enantiomer 1), |
| 321 | 3-[(4-methoxyphenoxy)methyl]-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid - N- ethylethanamine salt (enantiomer 2), |
| 322 | 1-methyl-3-({4-[(methylsulfonyl)amino]phenoxy}methyl)-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid - N- ethylethanamine salt (enantiomer 1), |
| 323 | 1-methyl-3-({4-[(methylsulfonyl)amino]phenoxy}methyl)-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid - N- ethylethanamine salt (enantiomer 2), |
| 324 | (rac)-7,10-dimethyl-1-[3-(naphthalen-1-yloxy)propyl]-11-(trifluoromethyl)-4,5,6,7,8,10-hexahydropyrazolo[3',4':7,8][1,5]diazecino[9,10,1-hi]indole-2-carboxylic acid, |
| 325 | (rac)-1-methyl-7-[3-(naphthalen-1-yloxy)propyl]-3-[(2-oxopiperidin-1-yl)methyl]-1,10,11,12,13,15-hexahydropyrazolo[4',3':9,10][1,6]oxazacycloundecino[8,7,6-hi]indole-8-carboxylic acid, |
| 326 | 1-methyl-7-[3-(naphthalen-1-yloxy)propyl]-3-[(2-oxopiperidin-1-yl)methyl]-1,10,11,12,13,15-hexahydropyrazolo[4',3':9,10][1,6]oxazacycloundecino[8,7,6-hi]indole-8-carboxylic acid (enantiomer 1), |
| 327 | 1-methyl-7-[3-(naphthalen-1-yloxy)propyl]-3-[(2-oxopiperidin-1-yl)methyl]-1,10,11,12,13,15-hexahydropyrazolo[4',3':9,10][1,6]oxazacycloundecino[8,7,6-hi]indole-8-carboxylic acid (enantiomer 2), |
| 328 | (rac)-1-methyl-7-[3-(naphthalen-1-yloxy)propyl]-3-[(2-oxopyrrolidin-1-yl)methyl]-1,10,11,12,13,15-hexahydropyrazolo[4',3':9,10][1,6]oxazacycloundecino[8,7,6-hi]indole-8-carboxylic acid, |
| 329 | 1-methyl-7-[3-(naphthalen-1-yloxy)propyl]-3-[(2-oxopyrrolidin-1-yl)methyl]-1,10,11,12,13,15-hexahydropyrazolo[4',3':9,10][1,6]oxazacycloundecino[8,7,6-hi]indole-8-carboxylic acid (enantiomer 2), |
| 330 | 1-methyl-7-[3-(naphthalen-1-yloxy)propyl]-3-[(2-oxopyrrolidin-1-yl)methyl]-1,10,11,12,13,15-hexahydropyrazolo[4',3':9,10][1,6]oxazacycloundecino[8,7,6-hi]indole-8-carboxylic acid (enantiomer 1), |
| 331 | (rac)-3-[(dimethylamino)methyl]-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 338 | (rac)-3-(aminomethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 339 | (rac)-3-[(acetylamino)methyl]-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 340 | 3-[(acetylamino)methyl]-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1), |
| 341 | 3-[(acetylamino)methyl]-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2), |
| 342 | (rac)-3-{[acetyl(methyl)amino]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 343 | 1-methyl-7-[3-(naphthalen-1-yloxy)propyl]-3-({[(2,2,2-trifluoroethyl)carbamoyl]oxy}methyl)-1,10,11,12,13,15-hexahydropyrazolo[4',3':9,10][1,6]oxazacycloundecino[8,7,6-hi]indole-8-carboxylic acid (enantiomer 1), |
| 344 | 1-methyl-7-[3-(naphthalen-1-yloxy)propyl]-3-(2-oxa-6-azaspiro[3.3]hept-6-ylmethyl)-1,10,11,12,13,15-hexahydropyrazolo[4',3':9,10][1,6]oxazacycloundecino[8,7,6-hi]indole-8-carboxylic acid - N- ethylethanamine salt (enantiomer 1), |

| Ex.No. | Name |
|---|---|
| 345 | 1-methyl-7-[3-(naphthalen-1-yloxy)propyl]-3-(2-oxa-6-azaspiro[3.3]hept-6-ylmethyl)-1,10,11,12,13,15-hexahydropyrazolo[4',3':9,10][1,6]oxazacycloundecino[8,7,6-hi]indole-8-carboxylic acid - N- ethylethanamine salt (enantiomer 2), |
| 346 | (rac)-3-{[(4-carbamoylbenzyhoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 347 | 3-{[(4-cyanobenzyl)oxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid - N- ethylethanamine salt (enantiomer 1), |
| 348 | 3-{[(4-cyanobenzyl)oxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid - N- ethylethanamine salt (enantiomer 2), |
| 349 | (rac)-4-methoxy-2,3-dimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid, |
| 350 | 4-methoxy-2,3-dimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid - N-ethylethanamine salt (enantiomer 1), |
| 351 | 4-methoxy-2,3-dimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid - N-ethylethanamine salt (enantiomer 2), |
| 352 | 4-methoxy-1,3-dimethyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid ammonium salt (enantiomer 1), |
| 353 | 4-methoxy-1,3-dimethyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid ammonium salt (enantiomer 2), |
| 358 | (rac)-(11Z)-2-methyl-3-[(4-methylpiperazin-1-yl)methyl]-7-[3-(naphthalen-1-yloxy)propyl]-2,10,13,15-tetrahydropyrazolo[4',3':9,10][1,6]oxazacycloundecino[8,7,6-hi]indole-8-carboxylic acid and |
| 359 | (rac)-2-methyl-3-[(4-methylpiperazin-1-yl)methyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid. | or a tautomer, an N-oxide, or a salt thereof or a salt of a tautomer or a N-oxide or a mixture of same.

In some embodiments, the present invention includes compounds of general formula (I) selected from:

| Ex.No. | Name |
|---|---|
| 1-1 | (rac)-(E/Z)-3-{[4-(4-acetylpiperazin-1-yl)phenoxy]methyly}-methyl-7-[3-(naphthalen-1-yloxy)propyl]-1,10,13,15-tetrahydropyrazolo[4',3':9,10][1,6]oxazacycloundecino[8,7,6-hi]indole-8-carboxylic acid, |
| 1-2 | (rac)-(E/Z)-1-methyl-7-[3-(naphthalen-1-yloxy)propyl]-3-{[4-(piperazin-1-yl)phenoxy]methyl}-1,10,13,15-tetrahydropyrazolo[4',3':9,10][1,6]oxazacycloundecino[8,7,6-hi]indole-8-carboxylic acid, |
| 1-3 | (rac)-3-({4-[4-(diethylsulfamoyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 1-4 | 3-({4-[4-(diethylsulfamoyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1), |
| 1-5 | 3-({4-[4-(diethylsulfamoyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2), |
| 1-6 | (rac)-3-({4-[4-(tert-butoxycarbonyl)piperazin-1-yl]phenoxy}methyl)-1-methyl-7-[3-(naphthalen-1-yloxy)propyl]-1,10,11,12,13,15-hexahydropyrazolo[4',3':9,10][1,6]-oxazacycloundecino[8,7,6-hi]indole-8-carboxylic acid, |
| 1-7 | (rac)-1-methyl-3-{[4-(4-methylpiperazin-1-yl)phenoxy]methyl}-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 1-8 | (rac)-1-methyl-3-({4-[4-(methylsulfonyl)piperazin-1-yl]phenoxy}methyl)-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 1-9 | 1-methyl-3-({4-[4-(methylsulfonyl)piperazin-1-yl]phenoxy}methyl)-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1), |
| 1-10 | 1-methyl-3-({4-[4-(methylsulfonyl)piperazin-1-yl]phenoxy}methyl)-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2), |

-continued

| Ex.No. | Name |
|---|---|
| 1-11 | (rac)-3-({4-[4-(cyclopropylsulfonyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 1-12 | 3-({4-[4-(cyclopropylsulfonyl)piperazin-1-yl]phenoxy}methyl)-1-methyl-7-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1), |
| 1-13 | 3-({4-[4-(cyclopropylsulfonyl)piperazin-1-yl]phenoxy}methyl)-1-methyl-7-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2), |
| 1-14 | (rac)-11-({4-[4-(dimethylsulfamoyl)piperazin-1-yl]phenoxy}methyl)-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid, |
| 1-15 | (+)-11-({4-[4-(dimethylsulfamoyl)piperazin-1-yl]phenoxy}methyl)-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid (enantiomer 1), |
| 1-16 | 11-({4-[4-(dimethylsulfamoyl)piperazin-1-yl]phenoxy}methyl)-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid (enantiomer 2), |
| 1-17 | (rac)-(E/Z)-3-({4-[4-(dimethylsulfamoyl)piperazin-1-yl]phenoxy}methyl)-1-methyl-7-[3-(naphthalen-1-yloxy)propyl]-1,10,13,15-tetrahydropyrazolo[4',3':9,10][1,6]oxazacycloundecino[8,7,6-hi]indole-8-carboxylic acid, |
| 1-18 | (rac)-3-({4-[4-(dimethylsulfamoyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 1-19 | 3-({4-[4-(dimethylsulfamoyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1), |
| 1-20 | 3-({4-[4-(dimethylsulfamoyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2), |
| 1-21 | (rac)-3-({4-[4-(cyclopropylcarbonyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 1-22 | 3-({4-[4-(cyclopropylcarbonyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1), |
| 1-23 | 3-({4-[4-(cyclopropylcarbonyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2), |
| 1-24 | (rac)-3-{[4-(4-acetylpiperazin-1-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 1-25 | 3-{[4-(4-acetylpiperazin-1-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1), |
| 1-26 | 3-{[4-(4-acetylpiperazin-1-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2), |
| 1-27 | (rac)-3-({4-[4-(methoxyacetyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 1-28 | 3-({4-[4-(methoxyacetyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1), |
| 1-29 | 3-({4-[4-(methoxyacetyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2), |
| 1-30 | (rac)-7,9,11-trimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid, |
| 1-31 | 7,9,11-trimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid- N-ethylethanamine salt (enantiomer 1), |
| 1-32 | 7,9,11-trimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid- N-ethylethanamine salt (enantiomer 2), |
| 1-33 | (rac)-1,3-dimethyl-7-[3-(naphthalen-1-yloxy)propyl]-1,10,11,12,13,15-hexahydropyrazolo-[4',3':9,10][1,6]oxazacycloundecino[8,7,6-hi]indole-8-carboxylic acid, |

| Ex.No. | Name |
|---|---|
| 1-34 | 7,10,11-trimethyl-1-[3-(naphthalen-1-yloxy)propyl]-4,5,6,7,8,10-hexahydropyrazolo[3',4':7,8]-[1,5]diazecino[9,10,1-hi]indole-2-carboxylic acid - N-ethylethanamine salt (enantiomer 1), |
| 1-35 | 7,10,11-trimethyl-1-[3-(naphthalen-1-yloxy)propyl]-4,5,6,7,8,10-hexahydropyrazolo[3',4':7,8][1,5]diazecino[9,10,1-hi]indole-2-carboxylic acid - N-ethylethanamine salt (enantiomer 2), |
| 1-36 | (rac)-2,3-dimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid, |
| 1-37 | (+)-2,3-dimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (enantiomer 1), |
| 1-38 | (−)-2,3-dimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (enantiomer 2), |
| 1-39 | (rac)-3-({4-[4-(dimethylsulfamoyl)piperazin-1-yl]phenoxy}methyl)-1-methyl-7-[3-(naphthalen-1-yloxy)propyl]-10,11,12,13,14,15-hexahydro-1H-pyrazolo[4',3':4,5]azacycloundecino[3,2,1-hi]indole-8-carboxylic acid, |
| 1-40 | 3-({4-[4-(dimethylsulfamoyl)piperazin-1-yl]phenoxy}methyl)-1-methyl-7-[3-(naphthalen-1-yloxy)propyl]-10,11,12,13,14,15-hexahydro-1H-pyrazolo[4',3':4,5]azacycloundecino[3,2,1-hi]indole-8-carboxylic acid - N-ethylethanamine salt (enantiomer 1), |
| 1-41 | 3-({4-[4-(dimethylsulfamoyl)piperazin-1-yl]phenoxy}methyl)-1-methyl-7-[3-(naphthalen-1-yloxy)propyl]-10,11,12,13,14,15-hexahydro-1H-pyrazolo[4',3':4,5]azacycloundecino[3,2,1-hi]indole-8-carboxylic acid - N-ethylethanamine salt (enantiomer 2), |
| 1-42 | (rac)-7,9-dimethyl-11-(morpholin-4-ylmethyl)-1-[3-(naphthalen-1-yloxy)propyl]-4,5,6,7,8,9-hexahydropyrazolo[3',4':7,8][1,5]diazecino[9,10,1-hi]indole-2-carboxylic acid |
| 1-43 | (+)-7,9-dimethyl-11-(morpholin-4-ylmethyl)-1-[3-(naphthalen-1-yloxy)propyl]-4,5,6,7,8,9-hexahydropyrazolo[3',4':7,8][1,5]diazecino[9,10,1-hi]indole-2-carboxylic acid (enantiomer 1), |
| 1-44 | (−)-7,9-dimethyl-11-(morpholin-4-ylmethyl)-1-[3-(naphthalen-1-yloxy)propyl]-4,5,6,7,8,9-hexahydropyrazolo[3',4':7,8][1,5]diazecino[9,10,1-hi]indole-2-carboxylic acid (enantiomer 2), |
| 1-45 | (rac)-7,9-dimethyl-11-({4-[4-(methylsulfonyl)piperazin-1-yl]phenoxy}methyl)-1-[3-(naphthalen-1-yloxy)propyl]-4,5,6,7,8,9-hexahydropyrazolo[3',4':7,8][1,5]diazecino[9,10,1-hi]indole-2-carboxylic acid, |
| 1-46 | (+)-7,9-dimethyl-11-({4-[4-(methylsulfonyl)piperazin-1-yl]phenoxy}methyl)-1-[3-(naphthalen-1-yloxy)propyl]-4,5,6,7,8,9-hexahydropyrazolo[3',4':7,8][1,5]diazecino[9,10,1-hi]indole-2-carboxylic acid (enantiomer 1), |
| 1-47 | (−)-7,9-dimethyl-11-({4-[4-(methylsulfonyl)piperazin-1-yl]phenoxy}methyl)-1-[3-(naphthalen-1-yloxy)propyl]-4,5,6,7,8,9-hexahydropyrazolo[3',4':7,8][1,5]diazecino[9,10,1-hi]indole-2-carboxylic acid (enantiomer 2), |
| 1-48 | (rac)-7,9-dimethyl-11-{[4-(methylsulfonyl)phenoxy]methyl}-1-[3-(naphthalen-1-yloxy)propyl]-4,5,6,7,8,9-hexahydropyrazolo[3',4':7,8][1,5]diazecino[9,10,1-hi]indole-2-carboxylic acid, |
| 1-49 | (−)-7,9-dimethyl-11-{[4-(methylsulfonyl)phenoxy]methyl}-1-[3-(naphthalen-1-yloxy)propyl]-4,5,6,7,8,9-hexahydropyrazolo[3',4':7,8][1,5]diazecino[9,10,1-hi]indole-2-carboxylic acid (enantiomer 1), |
| 1-50 | (+)-7,9-dimethyl-11-{[4-(methylsulfonyl)phenoxy]methyl}-1-[3-(naphthalen-1-yloxy)propyl]-4,5,6,7,8,9-hexahydropyrazolo[3',4':7,8][1,5]diazecino[9,10,1-hi]indole-2-carboxylic acid (enantiomer 2), |
| 1-51 | (rac)-(E/Z)-1-methyl-3-{[4-(methylsulfonyl)phenoxy]methyl}-7-[3-(naphthalen-1-yloxy)propyl]-1,10,13,15-tetrahydropyrazolo[4',3':9,10][1,6]oxazacycloundecino[8,7,6-hi]indole-8-carboxylic acid, |
| 1-52 | (E/Z)-1-methyl-3-{[4-(methylsulfonyl)phenoxy]methyl}-7-[3-(naphthalen-1-yloxy)propyl]-1,10,13,15-tetrahydropyrazolo[4',3':9,10][1,6]oxazacycloundecino[8,7,6-hi]indole-8-carboxylic acid (enantiomer 1), |
| 1-53 | (E/Z)-1-methyl-3-{[4-(methylsulfonyl)phenoxy]methyl}-7-[3-(naphthalen-1-yloxy)propyl]-1,10,13,15-tetrahydropyrazolo[4',3':9,10][1,6]oxazacycloundecino[8,7,6-hi]indole-8-carboxylic acid (enantiomer 2), |
| 1-54 | (rac)-1-methyl-3-{[4-(methylsulfonyl)phenoxy]methyl}-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 1-55 | (−)-1-methyl-3-{[4-(methylsulfonyl)phenoxy]methyl}-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1), |
| 1-56 | (+)-1-methyl-3-{[4-(methylsulfonyl)phenoxy]methyl}-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2), |
| 1-57 | (rac)-7,9-dimethyl-1-[3-(naphthalen-1-yloxy)propyl]-11-{[4-(tetrahydro-2H-pyran-4-yl)phenoxy]methyl}-4,5,6,7,8,9-hexahydropyrazolo[3',4':7,8][1,5]diazecino[9,10,1-hi]indole-2-carboxylic acid, |
| 1-58 | (+)-7,9-dimethyl-1-[3-(naphthalen-1-yloxy)propyl]-11-{[4-(tetrahydro-2H-pyran-4-yl)phenoxy]methyl}-4,5,6,7,8,9-hexahydropyrazolo[3',4':7,8][1,5]diazecino[9,10,1-hi]indole-2-carboxylic acid (enantiomer 1), |
| 1-59 | (−)-7,9-dimethyl-1-[3-(naphthalen-1-yloxy)propyl]-11-{[4-(tetrahydro-2H-pyran-4-yl)phenoxy]methyl}-4,5,6,7,8,9-hexahydropyrazolo[3',4':7,8][1,5]diazecino[9,10,1-hi]indole-2-carboxylic acid (enantiomer 2), |

| Ex.No. | Name |
|---|---|
| 1-60 | (rac)-(E/Z)-3-{[4-(4-hydroxytetrahydro-2H-pyran-4-yl)phenoxy]methyl}-1-methyl-7-[3-(naphthalen-1-yloxy)propyl]-1,10,13,15-tetrahydropyrazolo[4',3':9,10][1,6]oxazacycloundecino[8,7,6-hi]indole-8-carboxylic acid, |
| 1-61 | (rac)-3-{[4-(4-hydroxytetrahydro-2H-pyran-4-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 1-62 | 3-{[4-(3,6-dihydro-2H-pyran-4-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1), |
| 1-63 | 3-{[4-(3,6-dihydro-2H-pyran-4-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2), |
| 1-64 | (rac)-(E/Z)-3-{[4-(4-methoxytetrahydro-2H-pyran-4-yl)phenoxy]methyl}-1-methyl-7-[3-(naphthalen-1-yloxy)propyl]-1,10,13,15-tetrahydropyrazolo[4',3':9,10][1,6]oxazacycloundecino[8,7,6-hi]indole-8-carboxylic acid, |
| 1-65 | (rac)-3-{[4-(4-methoxytetrahydro-2H-pyran-4-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 1-66 | 3-{[4-(4-methoxytetrahydro-2H-pyran-4-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1), |
| 1-67 | 3-{[4-(4-methoxytetrahydro-2H-pyran-4-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2), |
| 1-68 | (rac)-(11Z)-1-methyl-7-[3-(naphthalen-1-yloxy)propyl]-3-[(propan-2-yloxy)methyl]-1,10,13,15-tetrahydropyrazolo[4',3':9,10][1,6]oxazacycloundecino[8,7,6-hi]indole-8-carboxylic acid, |
| 1-69 | (rac)-1-methyl-3-[(propan-2-yloxy)methyl]-7-[3-(5,6,7,8-tetrahydronaphthalen-1-yloxy)propyl]-1,10,11,12,13,15-hexahydropyrazolo[4',3':9,10][1,6]oxazacycloundecino[8,7,6-hi]indole-8-carboxylic acid, |
| 1-70 | (rac)-7,9-dimethyl-1-[3-(naphthalen-1-yloxy)propyl]-11-[(propan-2-yloxy)methyl]-4,5,6,7,8,9-hexahydropyrazolo[3',4':7,8][1,5]diazecino[9,10,1-hi]indole-2-carboxylic acid, |
| 1-71 | 7,9-dimethyl-1-[3-(naphthalen-1-yloxy)propyl]-11-[(propan-2-yloxy)methyl]-4,5,6,7,8,9-hexahydropyrazolo[3',4':7,8][1,5]diazecino[9,10,1-hi]indole-2-carboxylic acid (enantiomer 1), |
| 1-72 | 7,9-dimethyl-1-[3-(naphthalen-1-yloxy)propyl]-11-[(propan-2-yloxy)methyl]-4,5,6,7,8,9-hexahydropyrazolo[3',4':7,8][1,5]diazecino[9,10,1-hi]indole-2-carboxylic acid (enantiomer 2), |
| 1-73 | (rac)-1,14-dimethyl-7-[3-(naphthalen-1-yloxy)propyl]-3-[(propan-2-yloxy)methyl]-10,11,12,13,14,15-hexahydro-1H-pyrazolo[3',4':8,9][1,6]diazacycloundecino[10,11,1-hi]indole-8-carboxylic acid, |
| 1-74 | 1,14-dimethyl-7-[3-(naphthalen-1-yloxy)propyl]-3-[(propan-2-yloxy)methyl]-10,11,12,13,14,15-hexahydro-1H-pyrazolo[3',4':8,9][1,6]diazacycloundecino[10,11,1-hi]indole-8-carboxylic acid (enantiomer 1), |
| 1-75 | 1,14-dimethyl-7-[3-(naphthalen-1-yloxy)propyl]-3-[(propan-2-yloxy)methyl]-10,11,12,13,14,15-hexahydro-1H-pyrazolo[3',4':8,9][1,6]diazacycloundecino[10,11,1-hi]indole-8-carboxylic acid (enantiomer 2), |
| 1-76 | (rac)-(E/Z)-1-methyl-7-[3-(naphthalen-1-yloxy)propyl]-3-(phenoxymethyl)-1,10,13,15-tetrahydropyrazolo[4',3':9,10][1,6]oxazacycloundecino[8,7,6-hi]indole-8-carboxylic acid, |
| 1-77 | (E/Z)-1-methyl-7-[3-(naphthalen-1-yloxy)propyl]-3-(phenoxymethyl)-1,10,13,15-tetrahydropyrazolo[4',3':9,10][1,6]oxazacycloundecino[8,7,6-hi]indole-8-carboxylic acid (enantiomer 1), |
| 1-78 | (E/Z)-1-methyl-7-[3-(naphthalen-1-yloxy)propyl]-3-(phenoxymethyl)-1,10,13,15-tetrahydropyrazolo[4',3':9,10][1,6]oxazacycloundecino[8,7,6-hi]indole-8-carboxylic acid (enantiomer 2), |
| 1-79 | 1-methyl-7-[3-(naphthalen-1-yloxy)propyl]-3-(phenoxymethyl)-1,10,11,12,13,15-hexahydropyrazolo[4',3':9,10][1,6]oxazacycloundecino[8,7,6-hi]indole-8-carboxylic acid (enantiomer 1), |
| 1-80 | 1-methyl-7-[3-(naphthalen-1-yloxy)propyl]-3-(phenoxymethyl)-1,10,11,12,13,15-hexahydropyrazolo[4',3':9,10][1,6]oxazacycloundecino[8,7,6-hi]indole-8-carboxylic acid (enantiomer 2), |
| 1-81 | (rac)-7,9-dimethyl-1-[3-(naphthalen-1-yloxy)propyl]-11-(phenoxymethyl)-4,5,6,7,8,9-hexahydropyrazolo[3',4':7,8][1,5]diazecino[9,10,1-hi]indole-2-carboxylic acid, |
| 1-82 | 7,9-dimethyl-1-[3-(naphthalen-1-yloxy)propyl]-11-(phenoxymethyl)-4,5,6,7,8,9-hexahydropyrazolo[3',4':7,8][1,5]diazecino[9,10,1-hi]indole-2-carboxylic acid (enantiomer 1), |
| 1-83 | 7,9-dimethyl-1-[3-(naphthalen-1-yloxy)propyl]-11-(phenoxymethyl)-4,5,6,7,8,9-hexahydropyrazolo[3',4':7,8][1,5]diazecino[9,10,1-hi]indole-2-carboxylic acid (enantiomer 2), |
| 1-84 | (rac)-1-[3-(4-chloro-3,5-dimethylphenoxy)propyl]-7,9-dimethyl-11-(phenoxymethyl)-4,5,6,7,8,9-hexahydropyrazolo[3',4':7,8][1,5]diazecino[9,10,1-hi]indole-2-carboxylic acid, |

| Ex.No. | Name |
|---|---|
| 1-85 | 1-[3-(4-chloro-3,5-dimethylphenoxy)propyl]-7,9-dimethyl-11-(phenoxymethyl)-4,5,6,7,8,9-hexahydropyrazolo[3',4':7,8][1,5]diazecino[9,10,1-hi]indole-2-carboxylic acid (enantiomer 1), |
| 1-86 | 1-[3-(4-chloro-3,5-dimethylphenoxy)propyl]-7,9-dimethyl-11-(phenoxymethyl)-4,5,6,7,8,9-hexahydropyrazolo[3',4':7,8][1,5]diazecino[9,10,1-hi]indole-2-carboxylic acid (enantiomer 2), |
| 1-87 | (rac)-7,9-dimethyl-11-{[4-(morpholin-4-yl)phenoxy]methyl}-1-[3-(naphthalen-1-yloxy)propyl]-4,5,6,7,8,9-hexahydropyrazolo[3',4':7,8][1,5]diazecino[9,10,1-hi]indole-2-carboxylic acid, |
| 1-88 | (+)-7,9-dimethyl-11-{[4-(morpholin-4-yl)phenoxy]methyl}-1-[3-(naphthalen-1-yloxy)propyl]-4,5,6,7,8,9-hexahydropyrazolo[3',4':7,8][1,5]diazecino[9,10,1-hi]indole-2-carboxylic acid (enantiomer 1), |
| 1-89 | (−)-7,9-dimethyl-11-{[4-(morpholin-4-yl)phenoxy]methyl}-1-[3-(naphthalen-1-yloxy)propyl]-4,5,6,7,8,9-hexahydropyrazolo[3',4':7,8][1,5]diazecino[9,10,1-hi]indole-2-carboxylic acid (enantiomer 2), |
| 1-90 | (rac)-11-({[2-(2-methoxyphenyl)pyrimidin-5-yl]oxy}methyl)-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid, |
| 1-91 | 11-({[2-(2-methoxyphenyl)pyrimidin-5-yl]oxy}methyl)-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid - N-ethylethanamine salt (enantiomer 1), |
| 1-92 | 11-({[2-(2-methoxyphenyl)pyrimidin-5-yl]oxy}methyl)-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid - N-ethylethanamine salt (enantiomer 2), |
| 1-93 | (rac)-11-[(benzyloxy)methyl]-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid, |
| 1-94 | (rac)-(E/Z)-3-[(benzyloxy)methyl]-1-methyl-7-[3-(naphthalen-1-yloxy)propyl]-1,10,13,15-tetrahydropyrazolo[4',3':9,10][1,6]oxazacycloundecino[8,7,6-hi]indole-8-carboxylic acid, |
| 1-95 | (rac)-3-(hydroxymethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 1-96 | (rac)-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid, |
| 1-97 | (rac)-9,11-Dimethyl-1-[3-(1-naphthyloxy)propyl]-7-phenyl-4,5,6,7,8,9-hexahydropyrazolo[3',4':7,8][1,5]diazecino[9,10,1-hi]indole-2-carboxylic acid, |
| 1-98 | (rac)-9,11-Dimethyl-7-[4-(morpholin-4-yl)phenyl]-1-[3-(1-naphthyloxy)propyl]-4,5,6,7,8,9-hexahydropyrazolo[3',4':7,8][1,5]diazecino[9,10,1-hi]indole-2-carboxylic acid, |
| 1-99 | 9,11-Dimethyl-7-[4-(morpholin-4-yl)phenyl]-1-[3-(1-naphthyloxy)propyl]-4,5,6,7,8,9-hexahydropyrazolo[3',4':7,8][1,5]diazecino[9,10,1-hi]indole-2-carboxylic acid (enantiomer 1), |
| 1-100 | 9,11-Dimethyl-7-[4-(morpholin-4-yl)phenyl]-1-[3-(1-naphthyloxy)propyl]-4,5,6,7,8,9-hexahydropyrazolo[3',4':7,8][1,5]diazecino[9,10,1-hi]indole-2-carboxylic acid (enantiomer 2), |
| 1-101 | (rac)-8,10-Dimethyl-1-[3-(1-naphthyloxy)propyl]-6-phenyl-5,6,7,8-tetrahydro-4H-pyrazolo[3',4':6,7][1,4]diazonino[8,9,1-hi]indole-2-carboxylic acid, |
| 1-102 | (rac)-11-(Methoxymethyl)-7,9-dimethyl-1-[3-(1-naphthyloxy)propyl]-4,5,6,7,8,9-hexahydropyrazolo[3',4':7,8][1,5]diazecino[9,10,1-hi]indole-2-carboxylic acid, |
| 1-103 | 11-(methoxymethyl)-7,9-dimethyl-1-[3-(1-naphthyloxy)propyl]-4,5,6,7,8,9-hexahydropyrazolo[3',4':7,8][1,5]diazecino[9,10,1-hi]indole-2-carboxylic acid (enantiomer 1), |
| 1-104 | 11-(methoxymethyl)-7,9-dimethyl-1-[3-(1-naphthyloxy)propyl]-4,5,6,7,8,9-hexahydropyrazolo[3',4':7,8][1,5]diazecino[9,10,1-hi]indole-2-carboxylic acid (enantiomer 2), |
| 1-105 | (rac)-7-{4-[4-(Dimethylsulfamoyl)piperazin-1-yl]phenyl}-9,11-dimethyl-1-[3-(1-naphthyloxy)propyl]-4,5,6,7,8,9-hexahydropyrazolo[3',4':7,8][1,5]diazecino[9,10,1-hi]indole-2-carboxylic acid, |
| 1-106 | 7-{4-[4-(Dimethylsulfamoyl)piperazin-1-yl]phenyl}-9,11-dimethyl-1-[3-(1-naphthyloxy)propyl]-4,5,6,7,8,9-hexahydropyrazolo[3',4':7,8][1,5]diazecino[9,10,1-hi]indole-2-carboxylic acid (enantiomer 1), |
| 1-107 | 7-{4-[4-(Dimethylsulfamoyl)piperazin-1-yl]phenyl}-9,11-dimethyl-1-[3-(1-naphthyloxy)propyl]-4,5,6,7,8,9-hexahydropyrazolo[3',4':7,8][1,5]diazecino[9,10,1-hi]indole-2-carboxylic acid (enantiomer 2), |
| 1-108 | (rac)-7-{4-[4-(Ethylsulfonyl)piperazin-1-yl]phenyl}-9,11-dimethyl-1-[3-(1-naphthyloxy)propyl]-4,5,6,7,8,9-hexahydropyrazolo[3',4':7,8][1,5]diazecino[9,10,1-hi]indole-2-carboxylic acid, |
| 1-109 | 7-{4-[4-(Ethylsulfonyl)piperazin-1-yl]phenyl}-9,11-dimethyl-1-[3-(1-naphthyloxy)propyl]-4,5,6,7,8,9-hexahydropyrazolo[3',4':7,8][1,5]diazecino[9,10,1-hi]indole-2-carboxylic acid (enantiomer 1), |
| 1-110 | 7-{4-[4-(Ethylsulfonyl)piperazin-1-yl]phenyl}-9,11-dimethyl-1-[3-(1-naphthyloxy)propyl]-4,5,6,7,8,9-hexahydropyrazolo[3',4':7,8][1,5]diazecino[9,10,1-hi]indole-2-carboxylic acid (enantiomer 2), |
| 1-111 | (rac)-11-({4-[4-(Dimethylsulfamoyl)piperazin-1-yl]phenoxy}methyl)-7,10-dimethyl-1-[3-(1-naphthyloxy)propyl]-4,5,6,7,8,10-hexahydropyrazolo[3',4':7,8][1,5]diazecino[9,10,1-hi]indole-2-carboxylic acid, |
| 1-112 | 11-({4-[4-(Dimethylsulfamoyl)piperazin-1-yl]phenoxy}methyl)-7,10-dimethyl-1-[3-(1-naphthyloxy)propyl]-4,5,6,7,8,10-hexahydropyrazolo[3',4':7,8][1,5]diazecino[9,10,1-hi]indole-2-carboxylic acid (enantiomer 1), |

| Ex.No. | Name |
|---|---|
| 1-113 | 11-({4-[4-(Dimethylsulfamoyl)piperazin-1-yl]phenoxy}methyl)-7,10-dimethyl-1-[3-(1-naphthyloxy)propyl]-4,5,6,7,8,10-hexahydropyrazolo[3',4':7,8][1,5]diazecino[9,10,1-hi]indole-2-carboxylic acid (enantiomer 2), |
| 1-114 | (rac)-7,9-Dimethyl-1-[3-(1-naphthyloxy)propyl]-11-{[4-(2-oxopyridin-1(2H)-yl)phenoxy]methyl}-4,5,6,7,8,9-hexahydropyrazolo[3',4':7,8][1,5]diazecino[9,10,1-hi]indole-2-carboxylic acid, |
| 1-115 | 7,9-Dimethyl-1-[3-(1-naphthyloxy)propyl]-11-{[4-(2-oxopyridin-1(2H)-yl)phenoxy]methyl}-4,5,6,7,8,9-hexahydropyrazolo[3',4':7,8][1,5]diazecino[9,10,1-hi]indole-2-carboxylic acid (enantiomer 1), |
| 1-116 | 7,9-Dimethyl-1-[3-(1-naphthyloxy)propyl]-11-{[4-(2-oxopyridin-1(2H)-yl)phenoxy]methyl}-4,5,6,7,8,9-hexahydropyrazolo[3',4':7,8][1,5]diazecino[9,10,1-hi]indole-2-carboxylic acid (enantiomer 2), |
| 1-117 | (rac)-2'-Carboxy-10'4(4-(4-(N,N-dimethylsulfamoyl)piperazin-1-yl)phenoxy)methyl)-8',11'-dimethyl-1'-(3-(naphthalen-1-yloxy)propyl)-4',5',7',8'-tetrahydrospiro[morpholine-4,6'-pyrazolo[3',4':6,7][1,4]diazonino[8,9,1-hi]indol]-4-ium bromide, |
| 1-118 | (rac)-12-Methoxy-1-[3-(5,6,7,8-tetrahydronaphthalen-1-yloxy)propyl]-4,5,7,8-tetrahydro-10,14-(metheno)[1,4,7]dioxazacyclotetradecino[9,8,7-hi]indole-2-carboxylic acid, |
| 1-119 | (rac)-12-Methoxy-1-[3-(1-naphthyloxy)propyl]-4,5,7,8-tetrahydro-10,14-(metheno)[1,4,7]dioxazacyclotetradecino[9,8,7-hi]indole-2-carboxylic acid, |
| 1-120 | (rac)-3-({4-[4-(Carboxymethyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 1-121 | (rac)-3-({4-[4-(3-hydroxy-3-methylbutyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid ammonium salt, |
| 1-122 | (rac)-12-Methoxy-1-[3-(naphthalen-1-yloxy)propyl]-5,6,7,8-tetrahydro-4H-10,14-(metheno)[1,7]oxazacyclotetradecino[9,8,7-hi]indole-2-carboxylic acid. | or a tautomer, an N-oxide, or a salt thereof or a salt of a tautomer or a N-oxide or a mixture of same.

In some embodiments, the present invention includes compounds of general formula (I) selected from:

| Ex.No. | Name |
|---|---|
| 1-1 | (rac)-(E/Z)-3-{[4-(4-acetylpiperazin-1-yl)phenoxy]methyl}-1-methyl-7-[3-(naphthalen-1-yloxy)propyl]-1,10,13,15-tetrahydropyrazolo[4',3':9,10][1,6]oxazacycloundecino[8,7,6-hi]indole-8-carboxylic acid, |
| 1-2 | (rac)-(E/Z)-1-methyl-7-[3-(naphthalen-1-yloxy)propyl]-3-{[4-(piperazin-1-yl)phenoxy]methyl}-1,10,13,15-tetrahydropyrazolo[4',3':9,10][1,6]oxazacycloundecino[8,7,6-hi]indole-8-carboxylic acid, |
| 1-3 | (rac)-3-({4-[4-(diethylsulfamoyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 1-4 | 3-({4-[4-(diethylsulfamoyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1), |
| 1-5 | 3-({4-[4-(diethylsulfamoyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2), |
| 1-6 | (rac)-3-({4-[4-(tert-butoxycarbonyl)piperazin-1-yl]phenoxy}methyl)-1-methyl-7-[3-(naphthalen-1-yloxy)propyl]-1,10,11,12,13,15-hexahydropyrazolo[4',3':9,10][1,6]-oxazacycloundecino[8,7,6-hi]indole-8-carboxylic acid, |
| 1-7 | (rac)-1-methyl-3-{[4-(4-methylpiperazin-1-yl)phenoxy]methyl}-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 1-8 | (rac)-1-methyl-3-({4-[4-(methylsulfonyl)piperazin-1-yl]phenoxy}methyl)-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 1-9 | 1-methyl-3-({4-[4-(methylsulfonyl)piperazin-1-yl]phenoxy}methyl)-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1), |
| 1-10 | 1-methyl-3-({4-[4-(methylsulfonyl)piperazin-1-yl]phenoxy}methyl)-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2), |
| 1-11 | (rac)-3-({4-[4-(cyclopropylsulfonyl)piperazin-1-yl]phenoxy}methyl)-1-methyl-7-[3-(naphthalen-1-yloxy)propyl]-1,10,11,12,13,15-hexahydropyrazolo[4',3':9,10][1,6]-oxazacycloundecino[8,7,6-hi]indole-8-carboxylic acid, |

| Ex.No. | Name |
|---|---|
| 1-12 | 3-({4-[4-(cyclopropylsulfonyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1), |
| 1-13 | 3-({4-[4-(cyclopropylsulfonyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2), |
| 1-14 | (rac)-11-({4-[4-(dimethylsulfamoyl)piperazin-1-yl]phenoxy}methyl)-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid, |
| 1-15 | (+)-11-({4-[4-(dimethylsulfamoyl)piperazin-1-yl]phenoxy}methyl)-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid (enantiomer 1), |
| 1-16 | 11-({4-[4-(dimethylsulfamoyl)piperazin-1-yl]phenoxy}methyl)-7,9-dimethyl-1-[3-(naphthalen-1-yloxy)propy]-4,5,6,7,8,9-hexahydropyrazolo[3',4':7,8][1,5]diazecino[9,10,1-hi]indole-2-carboxylic acid (enantiomer 2), |
| 1-17 | (rac)-(E/Z)-3-({4-[4-(dimethylsulfamoyl)piperazin-1-yl]phenoxy}methyl)-1-methyl-7-[3-(naphthalen-1-yloxy)propyl]-1,10,13,15-tetrahydropyrazolo[4',3':9,10][1,6]-oxazacycloundecino[8,7,6-hi]indole-8-carboxylic acid, |
| 1-18 | (rac)-3-({4-[4-(dimethylsulfamoyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 1-19 | 3-({4-[4-(dimethylsulfamoyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1), |
| 1-20 | 3-({4-[4-(dimethylsulfamoyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2), |
| 1-21 | (rac)-3-({4-[4-(cyclopropylcarbonyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 1-22 | 3-({4-[4-(cyclopropylcarbonyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1), |
| 1-23 | 3-({4-[4-(cyclopropylcarbonyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2), |
| 1-24 | (rac)-3-{[4-(4-acetylpiperazin-1-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 1-25 | 3-{[4-(4-acetylpiperazin-1-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1), |
| 1-26 | 3-{[4-(4-acetylpiperazin-1-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2), |
| 1-27 | (rac)-3-({4-[4-(methoxyacetyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 1-28 | 3-({4-[4-(methoxyacetyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1), |
| 1-29 | 3-({4-[4-(methoxyacetyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2), |
| 1-30 | (rac)-7,9,11-trimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid, |
| 1-31 | 7,9,11-trimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid - N-ethylethanamine salt (enantiomer 1), |
| 1-32 | 7,9,11-trimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid - N-ethylethanamine salt (enantiomer 2), |
| 1-33 | (rac)-1,3-dimethyl-7-[3-(naphthalen-1-yloxy)propyl]-1,10,11,12,13,15-hexahydropyrazolo-[4',3':9,10][1,6]oxazacycloundecino[8,7,6-hi]indole-8-carboxylic acid, |
| 1-34 | 7,10,11-trimethyl-1-[3-(naphthalen-1-yloxy)propyl]-4,5,6,7,8,10-hexahydropyrazolo[3',4':7,8][1,5]diazecino[9,10,1-hi]indole-2-carboxylic acid - N-ethylethanamine salt (enantiomer 1), |

| Ex.No. | Name |
|---|---|
| 1-35 | 7,10,11-trimethyl-1-[3-(naphthalen-1-yloxy)propyl]-4,5,6,7,8,10-hexahydropyrazolo[3',4':7,8][1,5]diazecino[9,10,1-hi]indole-2-carboxylic acid - N-ethylethanamine salt (enantiomer 2), |
| 1-36 | (rac)-2,3-dimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid, |
| 1-37 | (+)-2,3-dimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (enantiomer 1), |
| 1-38 | (−)-2,3-dimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (enantiomer 2), |
| 1-39 | (rac)-3-({4-[4-(dimethylsulfamoyl)piperazin-1-yl]phenoxy}methyl)-1-methyl-7-[3-(naphthalen-1-yloxy)propyl]-10,11,12,13,14,15-hexahydro-1H-pyrazolo[4',3':4,5]azacycloundecino[3,2,1-hi]indole-8-carboxylic acid, |
| 1-40 | 3-({4-[4-(dimethylsulfamoyl)piperazin-1-yl]phenoxy}methyl)-1-methyl-7-[3-(naphthalen-1-yloxy)propyl]-10,11,12,13,14,15-hexahydro-1H-pyrazolo[4',3':4,5]azacycloundecino[3,2,1-hi]indole-8-carboxylic acid - N-ethylethanamine salt (enantiomer 1), |
| 1-41 | 3-({4-[4-(dimethylsulfamoyl)piperazin-1-yl]phenoxy}methyl)-1-methyl-7-[3-(naphthalen-1-yloxy)propyl]-10,11,12,13,14,15-hexahydro-1H-pyrazolo[4',3':4,5]azacycloundecino[3,2,1-hi]indole-8-carboxylic acid - N-ethylethanamine salt (enantiomer 2), |
| 1-42 | (rac)-7,9-dimethyl-11-(morpholin-4-ylmethyl)-1-[3-(naphthalen-1-yloxy)propyl]-4,5,6,7,8,9-hexahydropyrazolo[3',4':7,8][1,5]diazecino[9,10,1-hi]indole-2-carboxylic acid |
| 1-43 | (+)-7,9-dimethyl-11-(morpholin-4-ylmethyl)-1-[3-(naphthalen-1-yloxy)propyl]-4,5,6,7,8,9-hexahydropyrazolo[3',4':7,8][1,5]diazecino[9,10,1-hi]indole-2-carboxylic acid (enantiomer 1), |
| 1-44 | (−)-7,9-dimethyl-11-(morpholin-4-ylmethyl)-1-[3-(naphthalen-1-yloxy)propyl]-4,5,6,7,8,9-hexahydropyrazolo[3',4':7,8][1,5]diazecino[9,10,1-hi]indole-2-carboxylic acid (enantiomer 2), |
| 1-45 | (rac)-7,9-dimethyl-11-({4-[4-(methylsulfonyl)piperazin-1-yl]phenoxy}methyl)-1-[3-(naphthalen-1-yloxy)propyl]-4,5,6,7,8,9-hexahydropyrazolo[3',4':7,8][1,5]diazecino[9,10,1-hi]indole-2-carboxylic acid, |
| 1-46 | (+)-7,9-dimethyl-11-({4-[4-(methylsulfonyl)piperazin-1-yl]phenoxy}methyl)-1-[3-(naphthalen-1-yloxy)propyl]-4,5,6,7,8,9-hexahydropyrazolo[3',4':7,8][1,5]diazecino[9,10,1-hi]indole-2-carboxylic acid (enantiomer 1), |
| 1-47 | (−)-7,9-dimethyl-11-({4-[4-(methylsulfonyl)piperazin-1-yl]phenoxy}methyl)-1-[3-(naphthalen-1-yloxy)propyl]-4,5,6,7,8,9-hexahydropyrazolo[3',4':7,8][1,5]diazecino[9,10,1-hi]indole-2-carboxylic acid (enantiomer 2), |
| 1-48 | (rac)-7,9-dimethyl-11-{[4-(methylsulfonyl)phenoxy]methyl}-1-[3-(naphthalen-1-yloxy)propyl]-4,5,6,7,8,9-hexahydropyrazolo[3',4':7,8][1,5]diazecino[9,10,1-hi]indole-2-carboxylic acid, |
| 1-49 | (−)-7,9-dimethyl-11-{[4-(methylsulfonyl)phenoxy]methyl}-1-[3-(naphthalen-1-yloxy)propyl]-4,5,6,7,8,9-hexahydropyrazolo[3',4':7,8][1,5]diazecino[9,10,1-hi]indole-2-carboxylic acid (enantiomer 1), |
| 1-50 | (+)-7,9-dimethyl-11-{[4-(methylsulfonyl)phenoxy]methyl}-1-[3-(naphthalen-1-yloxy)propyl]-4,5,6,7,8,9-hexahydropyrazolo[3',4':7,8][1,5]diazecino[9,10,1-hi]indole-2-carboxylic acid (enantiomer 2), |
| 1-51 | (rac)-(E/Z)-1-methyl-3-{[4-(methylsulfonyl)phenoxy]methyl}-7-[3-(naphthalen-1-yloxy)propyl]-1,10,13,15-tetrahydropyrazolo[4',3':9,10][1,6]oxazacycloundecino[8,7,6-hi]indole-8-carboxylic acid, |
| 1-52 | (E/Z)-1-methyl-3-{[4-(methylsulfonyl)phenoxy]methyl}-7-[3-(naphthalen-1-yloxy)propyl]-1,10,13,15-tetrahydropyrazolo[4',3':9,10][1,6]oxazacycloundecino[8,7,6-hi]indole-8-carboxylic acid (enantiomer 1), |
| 1-53 | (E/Z)-1-methyl-3-{[4-(methylsulfonyl)phenoxy]methyl}-7-[3-(naphthalen-1-yloxy)propyl]-1,10,13,15-tetrahydropyrazolo[4',3':9,10][1,6]oxazacycloundecino[8,7,6-hi]indole-8-carboxylic acid (enantiomer 2), |
| 1-54 | (rac)-1-methyl-3-{[4-(methylsulfonyl)phenoxy]methyl}-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 1-55 | (−)-1-methyl-3-{[4-(methylsulfonyl)phenoxy]methyl}-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1), |
| 1-56 | (+)-1-methyl-3-{[4-(methylsulfonyl)phenoxy]methyl}-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2), |
| 1-57 | (rac)-7,9-dimethyl-1-[3-(naphthalen-1-yloxy)propyl]-11-{[4-(tetrahydro-2H-pyran-4-yl)phenoxy]methyl}-4,5,6,7,8,9-hexahydropyrazolo[3',4':7,8][1,5]diazecino[9,10,1-hi]indole-2-carboxylic acid, |
| 1-58 | (+)-7,9-dimethyl-1-[3-(naphthalen-1-yloxy)propyl]-11-{[4-(tetrahydro-2H-pyran-4-yl)phenoxy]methyl}-4,5,6,7,8,9-hexahydropyrazolo[3',4':7,8][1,5]diazecino[9,10,1-hi]indole-2-carboxylic acid (enantiomer 1), |
| 1-59 | (+)-7,9-dimethyl-1-[3-(naphthalen-1-yloxy)propyl]-11-{[4-(tetrahydro-2H-pyran-4-yl)phenoxy]methyl}-4,5,6,7,8,9-hexahydropyrazolo[3',4':7,8][1,5]diazecino[9,10,1-hi]indole-2-carboxylic acid (enantiomer 2), |
| 1-60 | (rac)-(E/Z)-3-{[4-(4-hydroxytetrahydro-2H-pyran-4-yl)phenoxy]methyl}-1-methyl-7-[3-(naphthalen-1-yloxy)propyl]-1,10,13,15-tetrahydropyrazolo[4',3':9,10][1,6]oxazacycloundecino[8,7,6-hi]indole-8-carboxylic acid, |
| 1-61 | (rac)-3-{[4-(4-hydroxytetrahydro-2H-pyran-4-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |

| Ex.No. | Name |
| --- | --- |
| 1-64 | (rac)-(E/Z)-3-{[4-(4-methoxytetrahydro-2H-pyran-4-yl)phenoxy]methyl}-1-methyl-7-[3-(naphthalen-1-yloxy)propyl]-1,10,13,15-tetrahydropyrazolo[4',3':9,10][1,6]oxazacycloundecino[8,7,6-hi]indole-8-carboxylic acid, |
| 1-65 | (rac)-3-{[4-(4-methoxytetrahydro-2H-pyran-4-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 1-66 | 3-{[4-(4-methoxytetrahydro-2H-pyran-4-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1), |
| 1-67 | 3-{[4-(4-methoxytetrahydro-2H-pyran-4-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2), |
| 1-68 | (rac)-(11Z)-1-methyl-7-[3-(naphthalen-1-yloxy)propyl]-3-[(propan-2-yloxy)methyl]-1,10,13,15-tetrahydropyrazolo[4',3':9,10][1,6]oxazacycloundecino[8,7,6-hi]indole-8-carboxylic acid, |
| 1-69 | (rac)-1-methyl-3-[(propan-2-yloxy)methyl]-7-[3-(5,6,7,8-tetrahydronaphthalen-1-yloxy)propyl]-1,10,11,12,13,15-hexahydropyrazolo[4',3':9,10][1,6]oxazacycloundecino[8,7,6-hi]indole-8-carboxylic acid, |
| 1-70 | (rac)-7,9-dimethyl-1-[3-(naphthalen-1-yloxy)propyl]-11-[(propan-2-yloxy)methyl]-4,5,6,7,8,9-hexahydropyrazolo[3',4':7,8][1,5]diazecino[9,10,1-hi]indole-2-carboxylic acid, |
| 1-71 | 7,9-dimethyl-1-[3-(naphthalen-1-yloxy)propyl]-11-[(propan-2-yloxy)methyl]-4,5,6,7,8,9-hexahydropyrazolo[3',4':7,8][1,5]diazecino[9,10,1-hi]indole-2-carboxylic acid (enantiomer 1), |
| 1-72 | 7,9-dimethyl-1-[3-(naphthalen-1-yloxy)propyl]-11-[(propan-2-yloxy)methyl]-4,5,6,7,8,9-hexahydropyrazolo[3',4':7,8][1,5]diazecino[9,10,1-hi]indole-2-carboxylic acid (enantiomer 2), |
| 1-73 | (rac)-1,14-dimethyl-7-[3-(naphthalen-1-yloxy)propyl]-3-](propan-2-yloxy)methyl]-10,11,12,13,14,15-hexahydro-1H-pyrazolo[3',4':8,9][1,6]diazacycloundecino[10,11,1-hi]indole-8-carboxylic acid, |
| 1-74 | 1,14-dimethyl-7-[3-(naphthalen-1-yloxy)propyl]-3-[(propan-2-yloxy)methyl]-10,11,12,13,14,15-hexahydro-1H-pyrazolo[3',4':8,9][1,6]diazacycloundecino[10,11,1-hi]indole-8-carboxylic acid (enantiomer 1), |
| 1-75 | 1,14-dimethyl-7-[3-(naphthalen-1-yloxy)propyl]-3-[(propan-2-yloxy)methyl]-10,11,12,13,14,15-hexahydro-1H-pyrazolo[3',4':8,9][1,6]diazacycloundecino[10,11,1-hi]indole-8-carboxylic acid (enantiomer 2), |
| 1-76 | (rac)-(E/Z)-1-methyl-7-[3-(naphthalen-1-yloxy)propyl]-3-(phenoxymethyl)-1,10,13,15-tetrahydropyrazolo[4',3':9,10][1,6]oxazacycloundecino[8,7,6-hi]indole-8-carboxylic acid, |
| 1-77 | (E/Z)-1-methyl-7-[3-(naphthalen-1-yloxy)propyl]-3-(phenoxymethyl)-1,10,13,15-tetrahydropyrazolo[4',3':9,10][1,6]oxazacycloundecino[8,7,6-hi]indole-8-carboxylic acid (enantiomer 1), |
| 1-78 | (E/Z)-1-methyl-7-[3-(naphthalen-1-yloxy)propyl]-3-(phenoxymethyl)-1,10,13,15-tetrahydropyrazolo[4',3':9,10][1,6]oxazacycloundecino[8,7,6-hi]indole-8-carboxylic acid (enantiomer 2), |
| 1-79 | 1-methyl-7-[3-(naphthalen-1-yloxy)propyl]-3-(phenoxymethyl)-1,10,11,12,13,15-hexahydropyrazolo[4',3':9,10][1,6]oxazacycloundecino[8,7,6-hi]indole-8-carboxylic acid (enantiomer 1), |
| 1-80 | 1-methyl-7-[3-(naphthalen-1-yloxy)propyl]-3-(phenoxymethyl)-1,10,11,12,13,15-hexahydropyrazolo[4',3':9,10][1,6]oxazacycloundecino[8,7,6-hi]indole-8-carboxylic acid (enantiomer 2), |
| 1-81 | (rac)-7,9-dimethyl-1-[3-(naphthalen-1-yloxy)propyl]-11-(phenoxymethyl)-4,5,6,7,8,9-hexahydropyrazolo[3',4':7,8][1,5]diazecino[9,10,1-hi]indole-2-carboxylic acid, |
| 1-82 | 7,9-dimethyl-1-[3-(naphthalen-1-yloxy)propyl]-11-(phenoxymethyl)-4,5,6,7,8,9-hexahydropyrazolo[3',4':7,8][1,5]diazecino[9,10,1-hi]indole-2-carboxylic acid (enantiomer 1), |
| 1-83 | 7,9-dimethyl-1-[3-(naphthalen-1-yloxy)propyl]-11-(phenoxymethyl)-4,5,6,7,8,9-hexahydropyrazolo[3',4':7,8][1,5]diazecino[9,10,1-hi]indole-2-carboxylic acid (enantiomer 2), |
| 1-84 | (rac)-1-[3-(4-chloro-3,5-dimethylphenoxy)propyl]-7,9-dimethyl-11-(phenoxymethyl)-4,5,6,7,8,9-hexahydropyrazolo[3',4':7,8][1,5]diazecino[9,10,1-hi]indole-2-carboxylic acid, |
| 1-85 | 1-[3-(4-chloro-3,5-dimethylphenoxy)propyl]-7,9-dimethyl-11-(phenoxymethyl)-4,5,6,7,8,9-hexahydropyrazolo[3',4':7,8][1,5]diazecino[9,10,1-hi]indole-2-carboxylic acid (enantiomer 1), |
| 1-86 | 1-[3-(4-chloro-3,5-dimethylphenoxy)propyl]-7,9-dimethyl-11-(phenoxymethyl)-4,5,6,7,8,9-hexahydropyrazolo[3',4':7,8][1,5]diazecino[9,10,1-hi]indole-2-carboxylic acid (enantiomer 2), |
| 1-87 | (rac)-7,9-dimethyl-11-{[4-(morpholin-4-yl)phenoxy]methyl}-1-[3-(naphthalen-1-yloxy)propyl]-4,5,6,7,8,9-hexahydropyrazolo[3',4':7,8][1,5]diazecino[9,10,1-hi]indole-2-carboxylic acid, |
| 1-88 | (+)-7,9-dimethyl-11-{[4-(morpholin-4-yl)phenoxy]methyl}-1-[3-(naphthalen-1-yloxy)propyl]-4,5,6,7,8,9-hexahydropyrazolo[3',4':7,8][1,5]diazecino[9,10,1-hi]indole-2-carboxylic acid (enantiomer 1), |
| 1-89 | (−)-7,9-dimethyl-11-{[4-(morpholin-4-yl)phenoxy]methyl}-1-[3-(naphthalen-1-yloxy)propyl]-4,5,6,7,8,9-hexahydropyrazolo[3',4':7,8][1,5]diazecino[9,10,1-hi]indole-2-carboxylic acid (enantiomer 2), |
| 1-90 | (rac)-11-({[2-(2-methoxyphenyl)pyrimidin-5-yl]oxy}methyl)-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid, |
| 1-91 | 11-({[2-(2-methoxyphenyl)pyrimidin-5-yl]oxy}methyl)-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid - N-ethylethanamine salt (enantiomer 1), |

-continued

| Ex.No. | Name |
|---|---|
| 1-92 | 11-({[2-(2-methoxyphenyl)pyrimidin-5-yl]oxy}methyl)-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid - N-ethylethanamine salt (enantiomer 2), |
| 1-93 | (rac)-11-[(benzyloxy)methyl]-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid, |
| 1-94 | (rac)-(E/Z)-3-[(benzyloxy)methyl]-1-methyl-7-[3-(naphthalen-1-yloxy)propyl]-1,10,13,15-tetrahydropyrazolo[4',3':9,10][1,6]oxazacycloundecino[8,7,6-hi]indole-8-carboxylic acid, |
| 1-95 | (rac)-3-(hydroxymethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 1-96 | (rac)-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid, |
| 1-97 | (rac)-9,11-Dimethyl-1-[3-(1-naphthyloxy)propyl]-7-phenyl-4,5,6,7,8,9-hexahydropyrazolo[3',4':7,8][1,5]diazecino[9,10,1-hi]indole-2-carboxylic acid, |
| 1-98 | (rac)-9,11-Dimethyl-7-[4-(morpholin-4-yl)phenyl]-1-[3-(1-naphthyloxy)propyl]-4,5,6,7,8,9-hexahydropyrazolo[3',4':7,8][1,5]diazecino[9,10,1-hi]indole-2-carboxylic acid, |
| 1-99 | 9,11-Dimethyl-7-[4-(morpholin-4-yl)phenyl]-1-[3-(1-naphthyloxy)propyl]-4,5,6,7,8,9-hexahydropyrazolo[3',4':7,8][1,5]diazecino[9,10,1-hi]indole-2-carboxylic acid (enantiomer 1), |
| 1-100 | 9,11-Dimethyl-7-[4-(morpholin-4-yl)phenyl]-1-[3-(1-naphthyloxy)propyl]-4,5,6,7,8,9-hexahydropyrazolo[3',4':7,8][1,5]diazecino[9,10,1-hi]indole-2-carboxylic acid (enantiomer 2), |
| 1-101 | (rac)-8,10-Dimethyl-1-[3-(1-naphthyloxy)propyl]-6-phenyl-5,6,7,8-tetrahydro-4H-pyrazolo[3',4':6,7][1,4]diazonino[8,9,1-hi]indole-2-carboxylic acid, |
| 1-102 | (rac)-11-(Methoxymethyl)-7,9-dimethyl-1-[3-(1-naphthyloxy)propyl]-4,5,6,7,8,9-hexahydropyrazolo[3',4':7,8][1,5]diazecino[9,10,1-hi]indole-2-carboxylic acid, |
| 1-103 | 11-(methoxymethyl)-7,9-dimethyl-1-[3-(1-naphthyloxy)propyl]-4,5,6,7,8,9-hexahydropyrazolo[3',4':7,8][1,5]diazecino[9,10,1-hi]indole-2-carboxylic acid (enantiomer 1), |
| 1-104 | 11-(methoxymethyl)-7,9-dimethyl-1-[3-(1-naphthyloxy)propyl]-4,5,6,7,8,9-hexahydropyrazolo[3',4':7,8][1,5]diazecino[9,10,1-hi]indole-2-carboxylic acid (enantiomer 2), |
| 1-105 | (rac)-7-{4-[4-(Dimethylsulfamoyl)piperazin-1-yl]phenyl}-9,11-dimethyl-1-[3-(1-naphthyloxy)propyl]-4,5,6,7,8,9-hexahydropyrazolo[3',4':7,8][1,5]diazecino[9,10,1-hi]indole-2-carboxylic acid, |
| 1-106 | 7-{4-[4-(Dimethylsulfamoyl)piperazin-1-yl]phenyl}-9,11-dimethyl-1-[3-(1-naphthyloxy)propyl]-4,5,6,7,8,9-hexahydropyrazolo[3',4':7,8][1,5]diazecino[9,10,1-hi]indole-2-carboxylic acid (enantiomer 1), |
| 1-107 | 7-{4-[4-(Dimethylsulfamoyl)piperazin-1-yl]phenyl}-9,11-dimethyl-1-[3-(1-naphthyloxy)propyl]-4,5,6,7,8,9-hexahydropyrazolo[3',4':7,8][1,5]diazecino[9,10,1-hi]indole-2-carboxylic acid (enantiomer 2), |
| 1-108 | (rac)-7-{4-[4-(Ethylsulfonyl)piperazin-1-yl]phenyl}-9,11-dimethyl-1-[3-(1-naphthyloxy)propyl[-4,5,6,7,8,9-hexahydropyrazolo[3',4':7,8][1,5]diazecino[9,10,1-hi]indole-2-carboxylic acid, |
| 1-109 | 7-{4-[4-(Ethylsulfonyl)piperazin-1-yl]phenyl}-9,11-dimethyl-1-[3-(1-naphthyloxy)propyl]-4,5,6,7,8,9-hexahydropyrazolo[3',4':7,8][1,5]diazecino[9,10,1-hi]indole-2-carboxylic acid (enantiomer 1), |
| 1-110 | 7-{4-[4-(Ethylsulfonyl)piperazin-1-yl]phenyl}-9,11-dimethyl-1-[3-(1-naphthyloxy)propyl]-4,5,6,7,8,9-hexahydropyrazolo[3',4':7,8][1,5]diazecino[9,10,1-hi]indole-2-carboxylic acid (enantiomer 2), |
| 1-111 | (rac)-11-({4-[4-(Dimethylsulfamoyl)piperazin-1-yl]phenoxy}methyl)-7,10-dimethyl-1-[3-(1-naphthyloxy)propyl]-4,5,6,7,8,10-hexahydropyrazolo[3',4':7,8][1,5]diazecino[9,10,1-hi]indole-2-carboxylic acid, |
| 1-112 | 11-({4-[4-(Dimethylsulfamoyl)piperazin-1-yl]phenoxy}methyl)-7,10-dimethyl-1-[3-(1-naphthyloxy)propyl]-4,5,6,7,8,10-hexahydropyrazolo[3',4':7,8][1,5]diazecino[9,10,1-hi]indole-2-carboxylic acid (enantiomer 1), |
| 1-113 | 11-({4-[4-(Dimethylsulfamoyl)piperazin-1-yl]phenoxy}methyl)-7,10-dimethyl-1-[3-(1-naphthyloxy)propyl]-4,5,6,7,8,10-hexahydropyrazolo[3',4':7,8][1,5]diazecino[9,10,1-hi]indole-2-carboxylic acid (enantiomer 2), |
| 1-114 | (rac)-7,9-Dimethyl-1-[3-(1-naphthyloxy)propyl]-11-{[4-(2-oxopyridin-1(2H)-yl]phenoxy]methyl}-4,5,6,7,8,9-hexahydropyrazolo[3',4':7,8][1,5]diazecino[9,10,1-hi]indole-2-carboxylic acid, |
| 1-117 | (rac)-2'-Carboxy-10'-((4-(4-(N,N-dimethylsulfamoyl)piperazin-1-yl)phenoxy)methyl)-8',11'-dimethyl-1'-(3-(naphthalen-1-yloxy)propyl)-4',5',7',8'-tetrahydrospiro[morpholine-4,6'-pyrazolo[3',4':6,7][1,4]diazonino[8,9,1-hi]indol]-4-ium bromide, |
| 1-118 | (rac)-12-Methoxy-1-[3-(5,6,7,8-tetrahydronaphthalen-1-yloxy)propyl]-4,5,7,8-tetrahydro-10,14-(metheno)[1,4,7]dioxazacyclotetradecino[9,8,7-hi]indole-2-carboxylic acid, |
| 1-119 | (rac)-12-Methoxy-1-[3-(1-naphthyloxy)propyl]-4,5,7,8-tetrahydro-10,14-(metheno)[1,4,7]dioxazacyclotetradecino[9,8,7-hi]indole-2-carboxylic acid, |
| 1-120 | (rac)-3-({4-[4-(Carboxymethyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, |
| 1-121 | (rac)-3-({4-[4-(3-hydroxy-3-methylbutyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid ammonium salt, |
| 1-122 | (rac)-12-Methoxy-1-[3-(naphthalen-1-yloxy)propyl]-5,6,7,8-tetrahydro-4H-10,14-(metheno)[1,7]oxazacyclotetradecino[9,8,7-hi]indole-2-carboxylic acid. | or a tautomer, an N-oxide, or a salt thereof or a salt of a tautomer or a N-oxide or a mixture of same.

In some embodiments, the present invention includes compounds of general formula (I) selected from example 001-example 364, or a tautomer, an N-oxide, or a salt thereof or a salt of a tautomer or a N-oxide or a mixture of same.

In some embodiments, the present invention includes all compounds of general formula (I) as disclosed in the example section, starting from example 1-1 and ending up with example 364, or a tautomer, an N-oxide, or a salt thereof or a salt of a tautomer or a N-oxide or a mixture of same.

DETAILED DESCRIPTION

Definitions

The term "substituted" means that one or more hydrogen atoms on the designated atom or group are replaced with a selection from the indicated group, provided that the designated atom's normal valency under the existing circumstances is not exceeded. Combinations of substituents and/or variables are permissible.

The term "optionally substituted" means that the number of substituents can be equal to or different from zero. Unless otherwise indicated, it is possible that optionally substituted groups are substituted with as many optional substituents as can be accommodated by replacing a hydrogen atom with a non-hydrogen substituent on any available carbon or nitrogen atom. Commonly, it is possible for the number of optional substituents, when present, to be 1, 2, 3, 4 or 5, in particular 1, 2 or 3.

When groups in the compounds according to the invention are substituted, it is possible for said groups to be mono-substituted or poly-substituted with substituent(s), unless otherwise specified. Within the scope of the present invention, the meanings of all groups which occur repeatedly are independent from one another. It is possible that groups in the compounds according to the invention are substituted with one, two, three, four or five identical or different substituents, particularly with one, two or three substituents.

Oxo, an oxo group or an oxo substituent means a doubly attached oxygen atom =O. Oxo may be attached to atoms of suitable valency, for example to a saturated carbon atom or to a sulfur atom. For example, but without limitation, one oxo group is can be attached to a carbon atom, resulting in the formation of a carbonyl group C(=O), or two oxo groups are can be attached to one sulfur atom, resulting in the formation of a sulfonyl group —S(=O)$_2$. The term "ring substituent" means a substituent attached to an aromatic or nonaromatic ring which replaces an available hydrogen atom on the ring.

Should a composite substituent be composed of more than one parts, e.g., ($C_1$-$C_4$-alkoxy)-($C_1$-$C_4$-alkyl)-, it is possible for the position of a given part to be at any suitable position of said composite substituent, i.e. the $C_1$-$C_4$-alkoxy part can be attached to any carbon atom of the $C_1$-$C_4$-alkyl part of said ($C_1$-$C_4$-alkoxy)-($C_1$-$C_4$-alkyl)- group. A hyphen at the beginning or at the end of such a composite substituent indicates the point of attachment of said composite substituent to the rest of the molecule. Should a ring, comprising carbon atoms and optionally one or more heteroatoms, such as nitrogen, oxygen or sulfur atoms for example, be substituted with a substituent, it is possible for said substituent to be bound at any suitable position of said ring, be it bound to a suitable carbon atom and/or to a suitable heteroatom.

The term "comprising" when used in the specification includes "consisting of" but does not have to be the scope indicated by "consisting of."

If within the present text any item is referred to as "as mentioned herein", it means that it may be mentioned anywhere in the present text.

If within the present text any item is referred to as "supra" within the description it indicates any of the respective disclosures made within the specification in any of the preceding pages, or above on the same page.

If within the present text any item is referred to as "infra" within the description it indicates any of the respective disclosures made within the specification in any of the subsequent pages, or below on the same page.

The terms as mentioned in the present text have the following meanings:

The term "halogen atom" means a fluorine, chlorine, bromine or iodine atom, particularly a fluorine, chlorine or bromine atom.

The term "$C_1$-$C_6$-alkyl-" means a linear or branched, saturated hydrocarbon group having 1, 2, 3, 4, 5, 6, 7 or 8 carbon atoms, e.g., a methyl-, ethyl-, propyl-, iso-propyl-, n-butyl-, iso-butyl-, sec-butyl-, tert-butyl-, n-pentyl-, iso-pentyl-, 2-methylbutyl-, 1-methylbutyl-, 1-ethylpropyl-, 1,2-dimethylpropyl-, neo-pentyl-, 1,1-dimethylpropyl-, n-hexyl-, 4-methylpentyl-, 3-methylpentyl-, 2-methylpentyl-, 1-methylpentyl-, 2-ethylbutyl-, 1-ethylbutyl-, 3,3-dimethylbutyl-, 2,2-dimethylbutyl-, 1,1-dimethylbutyl-, 2,3-dimethylbutyl-, 1,3-dimethylbutyl-, 1,2-dimethylbutyl-, n-heptyl-, 5-methylhexyl-, 4-methylhexyl-, 2-methylhexyl-, 1-methylhexyl-, 2-ethylpentyl-, 1-ethylpentyl-, 3,3-dimethylpentyl-, 2,2-dimethylpentyl-, 1,1-dimethylpentyl-, 2,3-dimethylpentyl-1,3-dimethylpentyl-, 1,2-dimethylpentyl-, n-octyl-, 6-methylheptyl-, 4-methylheptyl-, 2-methylheptyl-, 1-methylheptyl-, 2-ethylhexyl-, 1-ethylhexyl-, 3,3-dimethylhexyl-, 2,2-dimethylhexyl-, 1,1-dimethylhexyl-, 2,3-dimethylhexyl-, 1,3-dimethylhexyl-, 1,2-dimethylhexyl-group, or an isomer thereof. Preferably, said group has 1, 2, 3, 4, 5 or 6 carbon atoms ("$C_1$-$C_6$-alkyl-"), e.g., a methyl-, ethyl-, n-propyl-, iso-propyl-, n-butyl-, iso-butyl-, sec-butyl-, tert-butyl-, n-pentyl-, iso-pentyl-, 2-methylbutyl-, 1-methylbutyl-, 1-ethylpropyl-, 1,2-dimethylpropyl-, neo-pentyl-, 1,1-dimethylpropyl-, n-hexyl-, 4-methylpentyl-, 3-methylpentyl-, 2-methylpentyl-, 1-methylpentyl-, 2-ethylbutyl-, 1-ethylbutyl-, 3,3-dimethylbutyl-, 2,2-dimethylbutyl-, 1,1-dimethylbutyl-, 2,3-dimethylbutyl-, 1,3-dimethylbutyl- or 1,2-dimethylbutyl- group, or an isomer thereof. More preferably, said group has 1, 2, 3 or 4 carbon atoms ("$C_1$-$C_4$-alkyl-"), e.g., a methyl-, ethyl-, n-propyl-, iso-propyl-, n-butyl-, iso-butyl-, sec-butyl- or tert-butyl- group, 1, 2 or 3 carbon atoms ("$C_1$-$C_3$-alkyl-"), e.g., a methyl-, ethyl-, n-propyl- or iso-propyl- group, or 1 or 2 carbon atoms ("$C_1$-$C_2$-alkyl-"), e.g., a methyl-, ethyl-group.

The same definitions can be applied should the alkyl group be placed within a chain as a bivalent "$C_1$-$C_6$-alkylene" moiety. All names as mentioned above then will bear an "ene" added to the end, thus e.g., a "pentyl" becomes a bivalent "pentylene" group. In addition, the term "$C_1$-$C_6$-heteroalkyl" refers to a $C_1$-$C_6$-alkyl group in which one or more of the carbon atoms have been replaced with an atom selected from N, O, S, or P, which are substituted as mentioned herein to satisfy atom valency requirements.

The term "$C_2$-$C_6$-alkylene" means a linear or branched, saturated, divalent hydrocarbon chain (or "tether") having 2, 3, 4, 5 or 6 carbon atoms, e.g., —$CH_2$—$CH_2$— ("ethylene" or "$C_2$-alkylene"), —$CH_2$—$CH_2$—$CH_2$—, —C(H)($CH_3$)—$CH_2$— or —C($CH_3$)$_2$—) ("propylene" or "$C_3$-alkylene"), or, for example —CH$_2$—C(H)(CH$_3$)—CH$_2$—, —CH$_2$—C(CH$_3$)$_2$—), —CH$_2$—CH$_2$—CH$_2$—CH$_2$— ("butylene" or "C$_4$-alkylene"), "C$_5$-alkylene", e.g., —CH$_2$—CH$_2$—CH$_2$—CH$_2$—CH$_2$— ("n-pentylene"), or "—C$_6$-alkylene-", e.g., —CH$_2$—CH$_2$—CH$_2$—CH$_2$—CH$_2$—CH$_2$— ("n-hexylene") or —C(CH$_3$)$_2$—C(CH$_3$)$_2$— group.

The term "hydroxy-(C$_1$-C$_6$-alkyl)-" means a linear or branched, saturated, hydrocarbon group in which one or more hydrogen atoms of a "C$_1$-C$_6$-alkyl-" as defined supra are each replaced by a hydroxy group, e.g., a hydroxymethyl-, 1-hydroxyethyl-, 2-hydroxyethyl-, 1,2-dihydroxyethyl-, 3-hydroxypropyl-, 2-hydroxypropyl-, 2,3-dihydroxypropyl-, 1,3-dihydroxypropan-2-yl-, 3-hydroxy-2-methylpropyl-, 2-hydroxy-2-methyl-propyl-, or 1-hydroxy-2-methyl-propyl- group. Particularly the hydroxyalkyl group means a linear or branched, saturated, monovalent hydrocarbon group has 1, 2 or 3 carbon atoms in which 1hydrogen atom is replaced with a hydroxy group e.g. a hydroxymethyl, 1-hydroxyethyl, 2-hydroxyethyl, 3-hydroxypropyl, 2-hydroxypropyl, 1-hydroxypropyl, 2-hydroxy-2-methyl-ethyl.

The term "C$_1$-C$_6$-haloalkyl" means a linear or branched, saturated, monovalent hydrocarbon group in which the term "C$_1$-C$_6$-alkyl" is as defined supra, and in which one or more of the hydrogen atoms are replaced, identically or differently, with a halogen atom. Preferably, said halogen atom is a fluorine atom. Said C$_1$-C$_6$-haloalkyl, particularly a C$_1$-C$_3$-haloalkyl group is, for example, fluoromethyl, difluoromethyl, trifluoromethyl, 2-fluoroethyl, 2,2-difluoroethyl, 2,2,2-trifluoroethyl, pentafluoroethyl, 3,3,3-trifluoropropyl or 1,3-difluoropropan-2-yl.

The term "C$_1$-C$_6$-alkoxy" means a linear or branched, saturated, monovalent group of formula (C$_1$-C$_6$-alkyl)-O—, in which the term "C$_1$-C$_6$-alkyl" is as defined supra, e.g. a methoxy, ethoxy, n-propoxy, isopropoxy, n-butoxy, sec-butoxy, isobutoxy, tert-butoxy, pentyloxy, isopentyloxy or n-hexyloxy group, or an isomer thereof.

The term "C$_1$-C$_6$-alkylthio" or "C$_1$-C$_6$-thioalkyl" means a linear or branched, saturated, monovalent group of formula (C$_1$-C$_6$-alkyl)-S—, in which the term "C$_1$-C$_6$-alkyl" is as defined supra, e.g. a methylthio, ethylthio, n-propylthio, isopropylthio, n-butylthio, sec-butylthio, isobutylthio, tert-butylthio, pentylthio, isopentylthio or n-hexylthio group, or an isomer thereof.

The term "C$_1$-C$_6$-haloalkoxy" means a linear or branched, saturated, monovalent C$_1$-C$_6$-alkoxy group, as defined supra, in which one or more of the hydrogen atoms is replaced, identically or differently, with a halogen atom. Preferably, said halogen atom in "C$_1$-C$_6$-haloalkoxy-" is fluorine, resulting in a group referred herein as "C$_1$-C$_6$-fluoroalkoxy-". Representative C$_1$-C$_6$-fluoroalkoxy- groups include, for example, —OCF$_3$, —OCHF$_2$, —OCH$_2$F, —OCF$_2$CF$_3$ and —OCH$_2$CF$_3$.

The term "C$_1$-C$_6$-haloalkylthio" or "C$_1$-C$_6$-halothioalkyl" or "C$_1$-C$_6$-haloalkyl-S—" means a linear or branched, saturated, monovalent C$_1$-C$_6$-alkylthio group, as defined supra, in which one or more of the hydrogen atoms is replaced, identically or differently, with a halogen atom. Preferably, said halogen atom in "C$_1$-C$_6$-haloalkylthio-" is fluorine.

The term "C$_2$-C$_6$-alkenyl-" means a linear or branched, monovalent hydrocarbon group, which contains one or more double bonds, and which has 2, 3, 4, 5 or 6 carbon atoms, preferably 2, 3 or 4 carbon atoms ("C$_2$-C$_4$-alkenyl-") or 2 or 3 carbon atoms ("C$_2$-C$_3$-alkenyl-"), it being understood that in the case in which said alkenyl- group contains more than one double bond, then said double bonds may be isolated from, or conjugated with, each other. Representative alkenyl- groups include, for example, an ethenyl-, prop-2-enyl-, (E)-prop-1-enyl-, (Z)-prop-1-enyl-, iso-propenyl-, but-3-enyl-, (E)-but-2-enyl-, (Z)-but-2-enyl-, (E)-but-1-enyl-, (Z)-but-1-enyl-, 2-methylprop-2-enyl-, 1-methylprop-2-enyl-, 2-methylprop-1-enyl-, (E)-1-methylprop-1-enyl-, (Z)-1-methylprop-1-enyl-, buta-1,3-dienyl-, pent-4-enyl-, (E)-pent-3-enyl-, (Z)-pent-3-enyl-, (E)-pent-2-enyl-, (Z)-pent-2-enyl-, (E)-pent-1-enyl-, (Z)-pent-1-enyl-, 3-methylbut-3-enyl-, 2-methylbut-3-enyl-, 1-methylbut-3-enyl-, 3-methylbut-2-enyl-, (E)-2-methylbut-2-enyl-, (Z)-2-methylbut-2-enyl-, (E)-1-methylbut-2-enyl-, (Z)-1-methylbut-2-enyl-, (E)-3-methylbut-1-enyl-, (Z)-3-methylbut-1-enyl-, (E)-2-methylbut-1-enyl-, (Z)-2-methylbut-1-enyl-, (E)-1-methylbut-1-enyl-, (Z)-1-methylbut-1-enyl-, 1,1-dimethylprop-2-enyl-, 1-ethylprop-1-enyl-, 1-propylvinyl-, 1-isopropylvinyl-, (E)-3,3-dimethylprop-1-enyl-, (Z)-3,3-dimethylprop-1-enyl-, penta-1,4-dienyl-, hex-5-enyl-, (E)-hex-4-enyl-, (Z)-hex-4-enyl-, (E)-hex-3-enyl-, (Z)-hex-3-enyl-, (E)-hex-2-enyl-, (Z)-hex-2-enyl-, (E)-hex-1-enyl-, (Z)-hex-1-enyl-, 4-methylpent-4-enyl-, 3-methylpent-4-enyl-, 2-methylpent-4-enyl-, 1-methylpent-4-enyl-, 4-methylpent-3-enyl-, (E)-3-methylpent-3-enyl-, (Z)-3-methylpent-3-enyl-, (E)-2-methylpent-3-enyl-, (Z)-2-methylpent-3-enyl-, (E)-1-methylpent-3-enyl-, (Z)-1-methylpent-3-enyl-, (E)-4-methylpent-2-enyl-, (Z)-4-methylpent-2-enyl-, (E)-3-methylpent-2-enyl-, (Z)-3-methylpent-2-enyl-, (E)-2-methylpent-2-enyl-, (Z)-2-methylpent-2-enyl-, (E)-1-methylpent-2-enyl-, (Z)-1-methylpent-2-enyl-, (E)-4-methylpent-1-enyl-, (Z)-4-methylpent-1-enyl-, (E)-3-methylpent-1-enyl-, (Z)-3-methylpent-1-enyl-, (E)-2-methylpent-1-enyl-, (Z)-2-methylpent-1-enyl-, (E)-1-methylpent-1-enyl-, (Z)-1-methylpent-1-enyl-, 3-ethylbut-3-enyl-, 2-ethylbut-3-enyl-, 1-ethylbut-3-enyl-, (E)-3-ethylbut-2-enyl-, (Z)-3-ethylbut-2-enyl-, (E)-2-ethylbut-2-enyl-, (Z)-2-ethylbut-2-enyl-, (E)-1-ethylbut-2-enyl-, (Z)-1-ethylbut-2-enyl-, (E)-3-ethylbut-1-enyl-, (Z)-3-ethylbut-1-enyl-, 2-ethylbut-1-enyl-, (E)-1-ethylbut-1-enyl-, (Z)-1-ethylbut-1-enyl-, 2-propylprop-2-enyl-, 1-propylprop-2-enyl-, 2-isopropylprop-2-enyl-, 1-isopropylprop-2-enyl-, (E)-2-propylprop-1-enyl-, (Z)-2-propylprop-1-enyl-, (E)-1-propylprop-1-enyl-, (Z)-1-propylprop-1-enyl-, (E)-2-isopropylprop-1-enyl-, (Z)-2-isopropylprop-1-enyl-, (E)-1-isopropylprop-1-enyl-, (Z)-1-isopropylprop-1-enyl-, hexa-1,5-dienyl- and 1-(1,1-dimethylethyl-)ethenyl- group. Particularly, said group is ethenyl- or prop-2-enyl-.

The same definitions can be applied should the alkenyl group be placed within a chain as a bivalent "C$_1$-C$_6$-alkenylene" moiety. All names as mentioned above then will bear a "ene" added to their end, thus e.g., a "pentenyl" becomes a bivalent "pentenylene" group.

The term "C$_2$-C$_6$-haloalkenyl-" means a linear or branched hydrocarbon group in which one or more of the hydrogen atoms of a "C$_2$-C$_6$-alkenyl-" as defined supra are each replaced, identically or differently, by a halogen atom. Preferably, said halogen atom is fluorine, resulting in a group referred herein as "C$_2$-C$_6$-fluoroalkenyl-". Representative C$_2$-C$_6$-fluoroalkenyl- groups include, for example, —CH=CF$_2$, —CF=CH$_2$, —CF=CF$_2$, —C(CH$_3$)=CF$_2$, —CH=C(F)—CH$_3$, —CH$_2$—CF=CF$_2$ and —CF$_2$—CH=CH$_2$.

The term "C$_2$-C$_6$-alkynyl-" means a linear or branched, monovalent hydrocarbon group which contains one or more triple bonds, and which contains 2, 3, 4, 5 or 6 carbon atoms, preferably 2, 3 or 4 carbon atoms ("C$_2$-C$_4$-alkynyl-") or 2 or 3 carbon atoms ("C$_2$-C$_3$-alkynyl-"). Representative C$_2$-C$_6$-alkynyl- groups include, for example, ethynyl-, prop-1-ynyl-, prop-2-ynyl-, but-1-ynyl-, but-2-ynyl-, but-3-ynyl-, pent-1-ynyl-, pent-2-ynyl, pent-3-ynyl-, pent-4-ynyl-, hex- 1-ynyl-, hex-2-ynyl-, hex-3-ynyl-, hex-4-ynyl-, hex-5-ynyl-, 1-methylprop-2-ynyl-, 2-methylbut-3-ynyl-, 1-methylbut-3-ynyl-, 1-methylbut-2-ynyl-, 3-methylbut-1-ynyl-, 1-ethylprop-2-ynyl-, 3-methylpent-4-ynyl-, 2-methylpent-4-ynyl-, 1-methylpent-4-ynyl-, 2-methylpent-3-ynyl-, 1-methylpent-3-ynyl-, 4-methylpent-2-ynyl-, 1-methylpent-2-ynyl-, 4-methylpent-1-ynyl-, 3-methylpent-1-ynyl-, 2-ethylbut-3-ynyl-, 1-ethylbut-3-ynyl-, 1-ethylbut-2-ynyl-, 1-propylprop-2-ynyl-, 1-isopropylprop-2-ynyl-, 2,2-dimethylbut-3-ynyl-, 1,1-dimethylbut-3-ynyl-, 1,1-dimethylbut-2-ynyl- and 3,3-dimethylbut-1-ynyl- group. Particularly, said alkynyl- group is ethynyl-, prop-1-ynyl- or prop-2-ynyl-.

The term "$C_3$-$C_{10}$-cycloalkyl-" means a saturated mono- or bicyclic hydrocarbon ring which contains 3, 4, 5, 6, 7, 8, 9 or 10 carbon atoms ("$C_3$-$C_{10}$-cycloalkyl-"). Said $C_3$-$C_{10}$-cycloalkyl- group may be, for example, a monocyclic hydrocarbon ring, e.g., a cyclopropyl-, cyclobutyl-, cyclopentyl-, cyclohexyl- or cycloheptyl- group, or a bicyclic hydrocarbon ring, such as decalinyl-. Preferably, said hydrocarbon ring is monocyclic and contains 3, 4, 5, 6 or 7 carbon atoms ("$C_3$-$C_7$-cycloalkyl-"), e.g., a cyclopropyl-, cyclobutyl-, cyclopentyl-, cyclohexyl- or cycloheptyl- group, or 3, 4, 5 or 6 carbon atoms ("$C_3$-$C_6$-cycloalkyl-"), e.g., a cyclopropyl-, cyclobutyl-, cyclopentyl- or cyclohexyl- group. A cycloalkyl group may be optionally substituted as defined at the respective part wherein such term is used.

The term "$C_4$-$C_8$-cycloalkenyl" means a monovalent, mono- or bicyclic hydrocarbon ring which contains 4, 5, 6, 7 or 8 carbon atoms and one double bond. Particularly, said ring contains 4, 5 or 6 carbon atoms ("$C_4$-$C_6$-cycloalkenyl"). Said $C_4$-$C_8$-cycloalkenyl group is for example, a monocyclic hydrocarbon ring, e.g., a cyclobutenyl, cyclopentenyl, cyclohexenyl, cycloheptenyl or cyclooctenyl group, or a bicyclic hydrocarbon ring, e.g., a bicyclo[2.2.1]hept-2-enyl or bicyclo[2.2.2]oct-2-enyl.

The term "4- to 10-membered heterocycloalkyl-" means a saturated mono- or bicyclic hydrocarbon ring which contains 3, 4, 5, 6, 7, 8 or 9 carbon atoms, and which contains 1, 2, 3 or 4 heteroatoms which may be identical or different, said heteroatoms preferably selected from oxygen, nitrogen or sulfur, and wherein carbon atoms and heteroatoms add up to 4, 5, 6, 7, 8, 9 or 10 ring atoms in total, it being possible for said heterocycloalkyl- group to be attached to the rest of the molecule via any one of the carbon atoms or, if present, a nitrogen atom. "Heterospirocycloalkyl-", "heterobicycloalkyl-" and "bridged heterocycloalkyl-", as defined infra, are also included within the scope of this definition.

Preferably, said "4- to 10-membered heterocycloalkyl-" is monocyclic and contains 3, 4, 5 or 6 carbon atoms, and one or two of the above-mentioned heteroatoms, adding up to 4, 5, 6 or 7 ring atoms in total (a "4- to 7-membered monocyclic heterocycloalkyl-"), or contains 3, 4 or 5 carbon atoms, and one or two of the above-mentioned heteroatoms, adding up to 4, 5 or 6 ring atoms in total (a "4- to 6-membered monocyclic heterocycloalkyl-"), or contains 3, 4 or 5 carbon atoms, and one or two of the above-mentioned heteroatoms, adding up to 5 or 6 ring atoms in total (a "5- to 6-membered monocyclic heterocycloalkyl-"); it being possible for said heterocycloalkyl- group to be attached to the rest of the molecule via any one of the carbon atoms or the nitrogen atoms, if present.

Exemplarily, without being limited thereto, said "4- to 7-membered monocyclic heterocycloalkyl-", can be a 4-membered ring, a "4-membered heterocycloalkyl-", such as azetidinyl- or oxetanyl-; or a 5-membered ring, a "5-membered heterocycloalkyl-", such as tetrahydrofuranyl-, dioxolinyl-, pyrrolidinyl-, imidazolidinyl-, pyrazolidinyl- or pyrrolinyl-; or a 6-membered ring, a "6-membered heterocycloalkyl-", such as tetrahydropyranyl-, piperidinyl-, morpholinyl-, 3-oxomorpholin-4-yl, dithianyl-, thiomorpholinyl- or piperazinyl-; or a 7-membered ring, a "7-membered heterocycloalkyl-", such as azepanyl-, diazepanyl- or oxazepanyl-, for example. Were suitable those heterocycloalkyl groups may be one or more times substituted with $C_1$-$C_3$-alkyl, $C_1$-$C_3$-alkoxy, hydroxy, halogen or a carbonyl group.

The term "5- to 7-membered heterocycloalkenyl" means a monocyclic, unsaturated, nonaromatic heterocycle with 5, 6, or 7 ring atoms in total, which contains one or two double bonds and one or two identical or different ring heteroatoms from the series: N, O, S; it being possible for said heterocycloalkenyl group to be attached to the rest of the molecule via any one of the carbon atoms or, if present, a nitrogen atom.

Said heterocycloalkenyl group is, for example, 4H-pyranyl, 3,6-dihydro-2H-pyran-4-yl 2H-pyranyl, dihydropyridinyl, tetrahydropyridinyl, 2-oxopyridin-1(2H)-yl, 2,5-dihydro-1H-pyrrolyl, [1,3]dioxolyl, 4H-[1,3,4]thiadiazinyl, 2,5-dihydrofuranyl, 2,3-dihydrofuranyl, 2,5-dihydrothiophenyl, 2,3-dihydrothiophenyl, 4,5-dihydrooxazolyl or 4H-[1,4]thiazinyl. Those heterocycloalkenyl groups may be substituted with hydroxy or methoxy.

The term "fused heterocycloalkyl" or "heterobicycloalkyl-" means a bicyclic, saturated heterocycle with 6, 7, 8, 9 or 10 ring atoms in total, in which the two rings share two adjacent ring atoms, which "fused heterocycloalkyl" contains one or two identical or different ring heteroatoms from the series: N, O, S; it being possible for said fused heterocycloalkyl group to be attached to the rest of the molecule via any one of the carbon atoms or, if present, a nitrogen atom.

Said fused heterocycloalkyl or "heterobicycloalkyl-" group is, for example, azabicyclo[3.3.0]octyl, azabicyclo[4.3.0]nonyl, diazabicyclo[4.3.0]nonyl, oxazabicyclo[4.3.0]nonyl, thiazabicyclo[4.3.0]-nonyl or azabicyclo[4.4.0]decyl.

The term "aryl" means phenyl, naphthyl, 5,6-dihydronaphthyl, 7,8-dihydronaphthyl, 5,6,7,8-tetrahydronaphthyl, which are optionally substituted with one, two, three, four or five substituents, each substituent independently selected from halogen, cyano, $C_1$-$C_3$-alkyl, $C_1$-$C_3$-haloalkyl, $C_1$-$C_3$-alkoxy, $C_1$-$C_3$-thioalkyl, $C_1$-$C_3$-haloalkoxy, $C_1$-$C_3$-halothioalkyl, $C_3$-$C_5$-cycloalkyl, particularly halogen, $C_1$-$C_3$-alkyl, $C_1$-$C_3$-haloalkyl, $C_1$-$C_3$-alkoxy, $C_1$-$C_3$-haloalkoxy.

The term "heteroaryl-" means a monocyclic, bicyclic or tricyclic aromatic ring system having 5, 6, 7, 8, 9, 10, 11, 12, 13 or 14 ring atoms (a "5- to 14-membered heteroaryl-" group), preferably 5, 6, 9 or 10 ring atoms, and which contains 1, 2, 3 or 4 heteroatoms which may be identical or different, said heteroatoms selected from oxygen, nitrogen and sulfur. Said heteroaryl- group can be a 5-membered heteroaryl- group, such as, for example, thienyl-, furanyl-, pyrrolyl-, oxazolyl-, thiazolyl-, imidazolyl-, pyrazolyl-, isoxazolyl-, isothiazolyl-, oxadiazolyl-, triazolyl-, thiadiazolyl- or tetrazolyl-; or a 6-membered heteroaryl- group, such as, for example, pyridyl-, pyridazinyl-, pyrimidyl-, pyrazinyl- or triazinyl-; or a benzo-fused 5-membered heteroaryl- group, such as, for example, benzofuranyl-, benzothienyl-, benzoxazolyl-, benzisoxazolyl-, benzimidazolyl-, benzothiazolyl-, benzotriazolyl-, indazolyl-, indolyl- or isoindolyl-; or a benzo-fused 6-membered heteroaryl- group, such as, for example, quinolinyl-, quinazolinyl-, isoquinolinyl-, cinnolinyl-, phthalazinyl- or quinoxalinyl-; or another bicyclic group, such as, for example, indolizinyl-, purinyl- or pteridinyl-; or a tricyclic heteroaryl- group, such as, for example, carbazolyl-, acridinyl- or phenazinyl-.

Preferably, "heteroaryl-" is a monocyclic aromatic ring system having 5 or 6 ring atoms and which contains at least one heteroatom, if more than one, they may be identical or different, said heteroatom being selected from oxygen, nitrogen and sulfur ("5- to 6-membered monocyclic heteroaryl-"), such as, for example, thienyl-, furanyl-, pyrrolyl-, oxazolyl-, thiazolyl-, imidazolyl-, pyrazolyl-, isoxazolyl-, isothiazolyl-, oxadiazolyl-, triazolyl-, thiadiazolyl-, tetrazolyl-, pyridyl-, pyridazinyl-, pyrimidyl-, pyrazinyl- or triazinyl-.

In general, and unless otherwise mentioned, said heteroaryl- groups include all the possible isomeric forms thereof, e.g., the positional isomers thereof. Thus, for some illustrative non-restricting example, the term pyridyl- includes pyridin-2-yl-, pyridin-3-yl- and pyridin-4-yl-; the term thienyl- includes thien-2-yl- and thien-3-yl-. Furthermore, said heteroaryl- groups can be attached to the rest of the molecule via any one of the carbon atoms, or, if applicable, a nitrogen atom, e.g., pyrrol-1-yl-, pyrazol-1-yl- or imidazol-1-yl-.

In general, and unless otherwise mentioned, the heteroaryl or heteroarylene groups include all possible isomeric forms thereof, e.g., tautomers and positional isomers with respect to the point of linkage to the rest of the molecule. Thus, for some illustrative non-restricting examples, the term pyridinyl includes pyridin-2-yl, pyridin-3-yl and pyridin-4-yl; or the term thienyl includes thien-2-yl and thien-3-yl.

Particularly, the heteroaryl group is a pyridyl- or pyrimidyl group or a imidazolyl group. including a hydroxy substitution of the pyridyl group leading e.g. to a 2-hydroxypyridine which is the tautomeric form to a 2-oxo-2(1H)-pyridine.

The term "$C_1$-$C_6$", as used throughout this text, e.g., in the context of the definition of "$C_1$-$C_6$-alkyl-", "$C_1$-$C_6$-haloalkyl-", "$C_1$-$C_6$-alkoxy-" or "$C_1$-$C_6$-haloalkoxy-" is to be understood as meaning an alkyl group having a whole number of carbon atoms from 1 to 6, i.e., 1, 2, 3, 4, 5 or 6 carbon atoms. It is to be understood further that said term "$C_1$-$C_6$" is to be interpreted as disclosing any sub-range comprised therein, e.g. $C_1$-$C_6$, $C_2$-$C_5$, $C_3$-$C_4$, $C_1$-$C_2$, $C_1$-$C_3$, $C_1$-$C_4$, $C_1$-$C_5$, $C_1$-$C_6$; preferably $C_1$-$C_2$, $C_1$-$C_3$, $C_1$-$C_4$, $C_1$-$C_5$, $C_1$-$C_6$; more preferably $C_1$-$C_4$; in the case of "$C_1$-$C_6$-haloalkyl-" or "$C_1$-$C_6$-haloalkoxy-" even more preferably $C_1$-$C_2$.

Similarly, as used herein, the term "$C_2$-$C_6$", as used throughout this text, e.g., in the context of the definitions of "$C_2$-$C_6$-alkenyl-" and "$C_2$-$C_6$-alkynyl-", is to be understood as meaning an alkenyl- group or an alkynyl group having a whole number of carbon atoms from 2 to 6, i.e., 2, 3, 4, 5 or 6 carbon atoms. It is to be understood further that said term "$C_2$-$C_6$" is to be interpreted as disclosing any sub-range comprised therein, e.g., $C_2$-$C_6$, $C_3$-$C_5$, $C_3$-$C_4$, $C_2$-$C_3$, $C_2$-$C_4$, $C_2$-$C_5$; preferably $C_2$-$C_3$.

Further, as used herein, the term "$C_3$-$C_7$", as used throughout this text, e.g., in the context of the definition of "$C_3$-$C_7$-cycloalkyl-", is to be understood as meaning a cycloalkyl- group having a whole number of carbon atoms of 3 to 7, i.e., 3, 4, 5, 6 or 7 carbon atoms. It is to be understood further that said term "$C_3$-$C_7$" is to be interpreted as disclosing any sub-range comprised therein, e.g., $C_3$-$C_6$, $C_4$-$C_5$, $C_3$-$C_5$, $C_3$-$C_4$, $C_4$-$C_6$, $C_5$-$C_7$; preferably $C_3$-$C_6$.

As used herein, the term "leaving group" refers to an atom or a group of atoms that is displaced in a chemical reaction as stable species taking with it the bonding electrons, e.g., typically forming an anion. Preferably, a leaving group is selected from the group comprising: halo, in particular chloro, bromo or iodo, (methylsulfonyl)oxy-, [(4-methylphenyl)sulfonyl]oxy-, [(trifluoromethyl)sulfonyl]oxy-, [(nonafluorobutyl)sulfonyl]oxy-, [(4-bromophenyl)sulfonyl]oxy-, [(4-nitrophenyl)sulfonyl]oxy-, [(2-nitrophenyl) sulfonyl]oxy-, [(4-isopropylphenyl)sulfonyl]oxy-, [(2,4,6-triisopropylphenyl)sulfonyl]oxy-, [(2,4,6-trimethylphenyl) sulfonyl]oxy-, [(4-tert-butylphenyl)sulfonyl]oxy-, (phenylsulfonyl)oxy- and [(4-methoxyphenyl)sulfonyl] oxy-.

As used herein, the term "protective group" is a protective group attached to an oxygen or nitrogen atom in intermediates used for the preparation of compounds of the general formula (I). Such groups are introduced e.g., by chemical modification of the respective hydroxy or amino group in order to obtain chemoselectivity in a subsequent chemical reaction. Protective groups for hydroxy and amino groups are described for example in T.W. Greene and P.G.M. Wuts in *Protective Groups in Organic Synthesis*, 4$^{th}$ edition, Wiley 2006; more specifically, protective groups for amino groups can be selected from substituted sulfonyl groups, such as mesyl-, tosyl- or phenylsulfonyl-, acyl groups such as benzoyl, acetyl or tetrahydropyranoyl, or carbamate based groups, such as tert.-butoxycarbonyl (Boc). Protective groups for hydroxy groups can be selected from acyl groups such as benzoyl, acetyl, pivaloyl or tetrahydropyranoyl, or can include silicon, as in e.g., tert-butyldimethylsilyl, tert-butyldiphenylsilyl, triethylsilyl or triisopropylsilyl.

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulphur, fluorine, chlorine, bromine and iodine, such as $^2$H (deuterium), $^3$H (tritium), $^{11}$C, $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I, respectively. Accordingly, recitation of "hydrogen" or "H" should be understood to encompass $^1$H (protium), $^2$H (deuterium), and $^3$H (tritium) unless otherwise specified. Certain isotopic variations of a compound of the invention, for example, those in which one or more radioactive isotopes such as $^3$H or $^{14}$C are incorporated, are useful in drug and/or substrate tissue distribution studies. Tritiated and carbon-14, i.e., $^{14}$C, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

With respect to the treatment and/or prophylaxis of the disorders specified herein, the isotopic variant(s) of the compounds of general formula (I) preferably contain deuterium ("deuterium-containing compounds of general formula (I)"). Isotopic variants of the compounds of general formula (I) in which one or more radioactive isotopes, such as $^3$H or $^{14}$C, are incorporated are useful, e.g., in drug and/or substrate tissue distribution studies. These isotopes are particularly preferred for the ease of their incorporation and detectability. Positron-emitting isotopes such as $^{18}F$ or $^{11}C$ may be incorporated into a compound of general formula (I). These isotopic variants of the compounds of general formula (I) are useful for in vivo imaging applications. Deuterium-containing and $^{13}C$-containing compounds of general formula (I) can be used in mass spectrometry analyses in the context of preclinical or clinical studies.

Isotopic variants of the compounds of general formula (I) can generally be prepared by methods known to a person skilled in the art, such as those described in the schemes and/or examples herein, by substituting a reagent for an isotopic variant of said reagent, preferably for a deuterium-containing reagent. Depending on the desired sites of deuteration, in some cases deuterium from $D_2O$ can be incorporated either directly into the compounds or into reagents that are useful for synthesizing such compounds. Deuterium gas is also a useful reagent for incorporating deuterium into molecules. Catalytic deuteration of olefinic bonds and acetylenic bonds is a rapid route for incorporation of deuterium. Metal catalysts (i.e. Pd, Pt, and Rh) in the presence of deuterium gas can be used to directly exchange deuterium for hydrogen in functional groups containing hydrocarbons. A variety of deuterated reagents and synthetic building blocks are commercially available from companies such as for example C/D/N Isotopes, Quebec, Canada; Cambridge Isotope Laboratories Inc., Andover, Mass., USA; and CombiPhos Catalysts, Inc., Princeton, N.J., USA.

The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [C. L. Perrin, et al., J. Am. Chem. Soc., 2007, 129, 4490], basicity [C. L. Perrin et al., J. Am. Chem. Soc., 2005, 127, 9641], lipophilicity [B. Testa et al., Int. J. Pharm., 1984, 19(3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and enhances the formation of a desired metabolite (e.g., Nevirapine: A. M. Sharma et al., Chem. Res. Toxicol., 2013, 26, 410; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. ML-337 (C. J. Wenthur et al., J. Med. Chem., 2013, 56, 5208) and Odanacatib (K. Kassahun et al., WO2012/112363) are examples for this deuterium effect. Still other cases have been reported in which reduced rates of metabolism result in an increase in exposure of the drug without changing the rate of systemic clearance (e.g., Rofecoxib: F. Schneider et al., Arzneim. Forsch./Drug. Res., 2006, 56, 295; Telaprevir: F. Maltais et al., J. Med. Chem., 2009, 52, 7993). Deuterated drugs showing this effect may have reduced dosing requirements (e.g., lower number of doses or lower dosage to achieve the desired effect) and/or may produce lower metabolite loads.

A compound of general formula (I) may have multiple potential sites of vulnerability to metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g., cytochrome $P_{450}$.

For example, in some embodiments, the present invention concerns a deuterium-containing compound of general formula (I), e.g.:

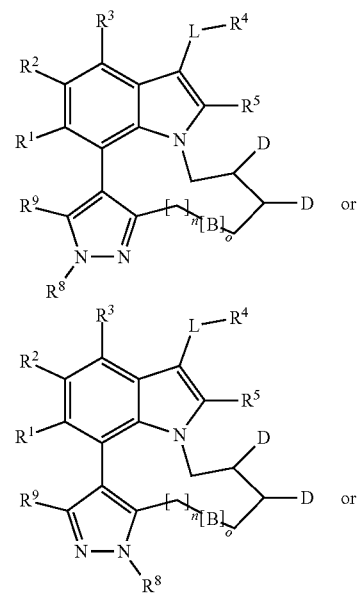

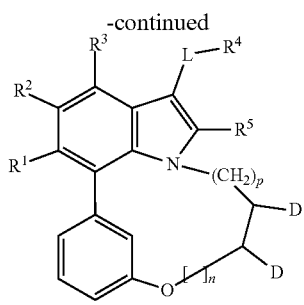

Such deuterium-containing compounds can be prepared by methods well-known to the person skilled in the art. Particularly, such deuterium-containing compounds can be prepared from the corresponding olefins, which are available by methods known to the person skilled in the art, such as ring closing metathesis reactions, as discussed e.g., in the general description of the synthesis of compounds of general formula (I), infra, in the context of Schemes 2c and 2j, respectively.

Where the plural form of the word compounds, salts, polymorphs, hydrates, solvates and the like, is used herein, this is taken to mean also a single compound, salt, polymorph, isomer, hydrate, solvate or the like.

By "stable compound' or "stable structure" is meant a compound that is sufficiently robust to survive isolation to a useful degree of purity from a reaction mixture, and formulation into an efficacious therapeutic agent.

Compounds of the present invention, as well as the corresponding macrocyclic intermediates of formula (II), are typically chiral merely as a result of restricted rotation around at least one single bond, which is due to limited comformational flexibility of their macrocyclic core as a whole. Hence, compounds of the present invention as well as the corresponding macrocyclic intermediates of formula (II), can exist as atropisomers. Atropisomers represent a subclass of conformers which arise from restricted rotation around a single bond. The conformers (called atropisomers) can be isolated as separated species (IUPAC Gold book, http://goldbook.iupac.org/A00511.html; *Pure and Appl. Chem.*, 2009, 68, 2193-2222). This induced chirality belongs to the axial type of chirality. The compounds of the present invention as well as the corresponding macrocyclic intermediates of formula (II), furthermore optionally contain one or more asymmetric centrers, depending upon the location and nature of the various substituents desired. It is possible that one or more asymmetric carbon atoms are present in the (R) or (S) configuration, which can result in racemic mixtures in the case of a single asymmetric center, and in diastereomeric mixtures in the case of multiple asymmetric centers. Hence, compounds of the present invention, as well as the corresponding macrocyclic intermediates of formula (II), featuring the abovementioned atropisomerism and an additional asymmetric centre can also exist as diasteromeric mixtures as described supra.

Preferred compounds are those which produce the more desirable biological activity. Separated, pure or partially purified isomers and stereoisomers or racemic or diastereomeric mixtures of the compounds of the present invention are also included within the scope of the present invention. The purification and the separation of such materials can be accomplished by standard techniques known in the art.

If only one isomer (enantiomer) displays the desired biological activity, and the second isomer (enantiomer) is inactive, the preferred isomer is the one which produces the more desirable biological activity. These separated, pure or partially purified isomers or racemic mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers. Suitable HPLC columns using a chiral phase are commercially available, such as those manufactured by Daicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials, enantioselective catalytic reactions, and other suitable methods.

In order to distinguish different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, in any ratio. Isolation of a single stereoisomer, e.g., a single enantiomer or a single diastereomer, of a compound of the present invention may be achieved by any suitable method, such as chromatography, especially chiral chromatography, for example.

Further, it is possible for the compounds of the present invention to exist as tautomers. For example, any compound of the present invention which contains an pyrazol moiety as a heteroaryl group for example can exist as a 1H tautomer, or a 2H tautomer, or even a mixture in any amount of the two tautomers, namely:

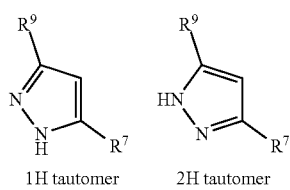

1H tautomer     2H tautomer

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also includes useful forms of the compounds of the present invention, such as metabolites, hydrates, solvates, prodrugs, salts, in particular pharmaceutically acceptable salts, and/or co-precipitates.

The compounds of the present invention can exist as a hydrate, or as a solvate, wherein the compounds of the present invention form a crystal that contains molecules of polar solvents, in particular water, methanol or ethanol, for example, as structural element of the crystal lattice of the compounds. The molecules of polar solvents, in particular water, may be present in a stoichiometric or non-stoichiometric ratio with the molecules of the compound. In the case of stoichiometric solvates, e.g., a hydrate, hemi-, (semi-), mono-, sesqui-, di-, tri-, tetra-, penta- etc. solvates or hydrates, respectively, are possible. The present invention includes all such hydrates or solvates.

Further, it is possible for the compounds of the present invention to exist in free form, e.g., as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "pharmaceutically acceptable salt" refers to an inorganic or organic acid addition salt of a compound of the present invention. For example, see S. M. Berge, et al. "Pharmaceutical Salts," J. Pharm. Sci. 1977, 66, 1-19. It includes any physiologically acceptable salt as referred to below.

Physiologically acceptable salts of the compounds according to the invention encompass acid addition salts of mineral acids, carboxylic acids and sulfonic acids, for example salts of hydrochloric acid, hydrobromic acid, hydroiodic acid, sulfuric acid, bisulfuric acid, phosphoric acid, nitric acid or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalenedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

A "pharmaceutically acceptable anion" refers to the deprotonated form of a conventional acid, such as, for example, a hydroxide, a carboxylate, a sulfate, a halide, a phosphate, or a nitrate.

Physiologically acceptable salts of the compounds according to the invention also comprise salts of conventional bases, such as, by way of example and by preference, alkali metal salts (for example lithium, sodium and potassium salts), alkaline earth metal salts (for example calcium, strontium and magnesium salts) and ammonium salts derived from ammonia or organic amines with 1 to 16 C atoms, such as, by way of example and by preference, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine, N-methylglucamine, dimethylglucamine, ethylglucamine, 1,6-hexadiamine, glucosamine, sarcosine, serinol, tris(hydroxymethyl)aminomethane, aminopropanediol, Sovak base, and 1-amino-2,3,4-butanetriol.

Additionally, the compounds according to the invention may form salts with a quaternary ammonium ion obtainable, e.g., by quaternization of a basic nitrogen-containing group with agents such as lower alkylhalides such as methyl-, ethyl-, propyl-, and butylchlorides, -bromides and -iodides; dialkylsulfates such as dimethyl-, diethyl-, dibutyl- and diamylsulfates, long chain halides such as decyl-, lauryl-, myristyl- and stearylchlorides, -bromides and -iodides, aralkylhalides such as benzyl- and phenethylbromides and others. Examples of suitable quaternary ammonium ions are tetramethylammonium, tetraethylammonium, tetra(n-propyl)ammonium, tetra (n-butyl)ammonium, or N-benzyl-N,N,N-trimethylammonium.

The present invention includes all possible salts of the compounds of the present invention as single salts, or as any mixture of said salts, in any ratio.

Unless specified otherwise, suffixes to chemical names or structural formulae relating to salts, such as "hydrochloride", "trifluoroacetate", "sodium salt", or "x HCl", "x $CF_3COOH$", "x $Na^+$", for example, mean a salt form, the stoichiometry of which salt form not being specified.

Solvates and hydrates of disclosed intermediates or example compounds, or salts thereof, which have been obtained, by the preparation and/or purification processes described herein, may be formed in any ratio.

Furthermore, the present invention includes all possible crystalline forms, or polymorphs, of the compounds of the present invention, either as a single polymorph, or as a mixture of more than one polymorph, in any ratio.

Moreover, the present invention also includes prodrugs of the compounds according to the invention. The term "prodrugs" designates compounds which themselves can be biologically active or inactive, but are converted (for example metabolically or hydrolytically) into compounds according to the invention during their residence time in the body. Derivatives of the compounds of formula (I) and the salts thereof which are converted into a compound of formula (I) or a salt thereof in a biological system (bioprecursors or pro-drugs) are covered by the invention. Said biological system may be, for example, a mammalian organism, particularly a human subject. The bioprecursor is, for example, converted into the compound of formula (I) or a salt thereof by metabolic processes.

DESCRIPTION

In accordance with a first aspect, the present invention provides compounds of formula (I)

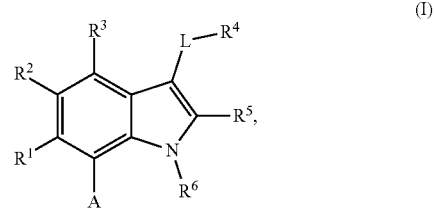

(I)

in which

A is

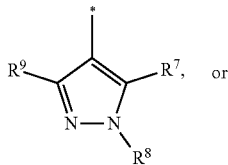

(A1)

or

A is

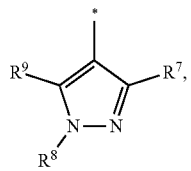

(A2)

wherein $R^6$ and $R^7$, together with two carbon atoms of the pyrazole ring, two carbon atoms of the indole moiety and the nitrogen atom to which $R^6$ is attached, form a 9- to 16-membered ring and * is the point of attachment of these moieties to the indole carbon atom bearing the A substituent or A is

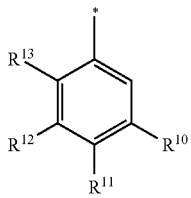

(A3)

whereby optionally one or two of the groups selected from $CR^{11}$, $CR^{12}$ or $CR^{13}$ may be replaced by a nitrogen atom, wherein $R^6$ and $R^{10}$, together with three carbon atoms of the phenyl ring, two carbon atoms of the indole moiety and the nitrogen atom to which $R^6$ is attached, form a 9- to 16-membered ring and * is the point of attachment of these moieties to the indole carbon atom bearing the A substituent;

$R^1$ and $R^2$ are each independently selected from a hydrogen atom, a halogen atom, a cyano group, a $C_1$-$C_3$-alkyl group and a $C_1$-$C_3$-alkoxy group;

$R^3$ is selected from a hydrogen atom, a halogen atom, a cyano group, a $C_1$-$C_3$-alkyl group, a $C_1$-$C_3$-haloalkyl group, a $C_1$-$C_3$-alkoxy group, a $C_1$-$C_3$-alkylthio group, a —S(O)—($C_1$-$C_3$-alkyl) group, a —S(O)$_2$—($C_1$-$C_3$-alkyl) group, and a $C_1$-$C_3$-haloalkoxy group, a $C_1$-$C_3$-haloalkylthio group and a $C_3$-$C_5$-cycloalkyl group.

$R^4$ is selected from an aryl group and a heteroaryl group, which is optionally substituted with one, two, three, four or five substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, a $(C_1$-$C_3)$-haloalkyl-S— group and a $C_3$-$C_5$-cycloalkyl group, L is a group —(CH$_2$)$_m$-E- wherein any CH$_2$ group is optionally substituted with one or two substituents and each substituent is independently selected from a halogen atom, a cyano group, a hydroxyl group, a $C_1$-$C_3$-alkyl group, and a $C_1$-$C_3$-alkoxy group, or two substituents are optionally taken together with their intervening atoms to form a saturated or partially unsaturated 3-6-membered cycloalkyl ring, or a 3-8 membered saturated or partially unsaturated heterocyclic ring having 1-2 heteroatoms independently selected from an oxygen atom, a sulfur atom, a —S(O)— group, a —S(O)$_2$— group and a —NR$^{14}$— group;

E is a bond, an oxygen atom, a sulfur atom, a —S(O)— group, a —S(O)$_2$— group or a —NR$^{14}$— group and constitutes the connecting element to $R^4$, where $R^{14}$ is a hydrogen atom or a $C_1$-$C_3$-alkyl group;

m is 2, 3, or 4;

$R^5$ is selected from a COOH group, or a

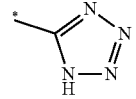 [SMILES: *c1nnn[nH]1]

group, a —C(O)—NHS(O)$_2$($C_1$-$C_6$-alkyl) group, a —C(O)—NHS(O)$_2$($C_3$-$C_6$-cycloalkyl) group, a —C(O)—NHS(O)$_2$(aryl) group, a —C(O)—NHS(O)$_2$(CH$_2$)$_s$NHCO ($C_1$-$C_6$-alkyl) group, a —C(O)—NHS(O)$_2$(CH$_2$)$_s$NHCO ($C_3$-$C_6$-cycloalkyl) group and a —C(O)—NHS(O)$_2$(CH$_2$)$_s$NHCO(aryl) group;

s is 0, 1, 2, or 3;

—$R^6$-$R^7$— is selected from $^{\#}$—(CH$_2$)$_n$—(B)$_t$—(CH$_2$)$_p$—$^{\#\#}$, $^{\#}$—(C$_2$-$C_6$-alkenylene)-(B)$_t$—(CH$_2$)$_p$—$^{\#\#}$, $^{\#}$—(CH$_2$)$_n$—(B)$_t$(C$_2$-$C_6$-alkenylene)-$^{\#\#}$ and $^{\#}$—(CH$_2$)$_q$—(B)—(CH$_2$)$_r$(B)—(CH$_2$)$_v$—$^{\#\#}$, wherein any CH$_2$ group is optionally substituted with one or more substituents selected from a halogen atom, a hydroxyl group, a NR$^{17}$R$^{18}$ group, a $C_1$-$C_3$-alkyl group, a $C_1$-$C_3$-haloalkyl group, a $C_1$-$C_3$-alkoxy group, a $C_1$-$C_3$-haloalkoxy group and a (heterocycloalkyl)-($C_1$-$C_3$-alkylene)- group, and where a double bond in any alkenylene can be replaced by a 1,2-cyclopropyl group, and said 1,2-cyclopropyl group is optionally substituted one or two times with a halogen atom or a $C_1$-$C_2$-alkyl group, wherein $^{\#}$ is the point of attachment with the indole nitrogen atom and $^{\#\#}$ is the point of attachment with the pyrazole carbon atom bearing the $R^7$ substituent;

—$R^6$-$R^{10}$— is selected from $^{\#}$—(CH$_2$)$_n$—(B)$_t$(CH$_2$)$_p$—$^{\#\#}$ $^{\#}$—(C$_2$-$C_6$-alkenylene)-(B)$_t$—(CH$_2$)$_p$, $^{\#}$—(CH$_2$)$_n$—(B)$_t$(C$_2$-$C_6$-alkenylene)-$^{\#\#}$ and $^{\#}$—(CH$_2$)$_q$—(B)—(CH$_2$)$_t$—(B)—(CH$_2$)$_v$—$^{\#\#}$, where one or more CH$_2$ groups are optionally substituted with one or more substituents selected from a halogen atom, a hydroxyl group, a NR$^{17}$R$^{18}$ group, a $C_1$-$C_3$-alkyl group, a $C_1$-$C_3$-haloalkyl group, a $C_1$-$C_3$-alkoxy group and a $C_1$-$C_3$-haloalkoxy group, wherein $^{\#}$ is the point of attachment with the indole nitrogen atom and $^{\#\#}$ is the point of attachment with the carbon atom of the phenyl moiety bearing the $R^{10}$ substituent;

atoms, n is 2, 3, 4, 5, 6, 7, 8, 9, or 10;

t is 0 or 1;

p is 0, 1, 2, 3, 4, 5, or 6;

q is 2, 3, 4, 5, or 6;

r is 2, 3, 4, 5, or 6;

v is 0, 1, or 2;

where the integers selected for variables n, t, p, q, r, and v result in forming a 9- to 16-membered ring independently from the selection of variable A1, A2 or A3;

B is independently selected from a —C(O)NR$^{15}$— group, a —NR$^{15}$C(O)— group, a —N(R$^{15}$)— group, a —N(R$^{15}$)—C(=O)—N(R$^{15}$)— group, a —O—C(=O)—N(R$^{15}$)— group, a —N(R$^{15}$)—C(=O)—O— group, —O—, —S—, —S(O)—, —S(O)$_2$—, a —S(O)NR$^{15}$— group, a —NR$^{15}$S(O)— group, a —S(O)$_2$NR$^{15}$— group, a —NR$^{15}$S(O)$_2$— group,

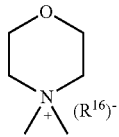

and —[N$^+$(R$^{21}$R$^{22}$)—(R$^{16}$)$^-$],

R$^{15}$ is independently selected from a hydrogen atom,
a C$_1$-C$_6$-alkyl group
which is optionally substituted with one or more substituents selected from a halogen atom, a C$_1$-C$_3$-alkyl group, a C$_1$-C$_3$-haloalkyl group, a C$_1$-C$_3$-hydroxyalkyl group, a C$_1$-C$_3$-alkoxy group, a C$_1$-C$_3$-haloalkoxy group, a heterocycloalkyl group, a aryl group, a (R$^{19}$)-(heterocycloalkylene)-(arylene)-O— group, a (heterocycloalkyl)-(arylene)-O— group, an aryl-O— group, an aryl-(C$_1$-C$_3$-alkylene)-O— group, a (R$^{20}$)—S(O)$_2$-arylene-O— group, a (R$^{20}$)S(O)$_2$-heterocycloalkylene-arylene-O— group, an aryl-heteroarylene-O— group, a aryl-heteroarylene-O—(C$_1$-C$_3$-alkylene)- group,
a phenyl group, a group

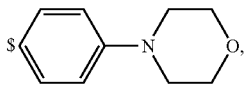

a group

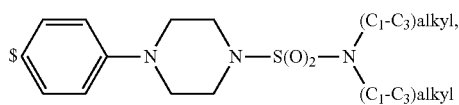

and
a group,

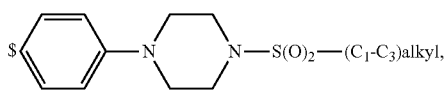

where $ is the point of attachment to the nitrogen atom, to which R$^{15}$ is attached,
where R$^{16}$ is a pharmaceutically acceptable anion;
where R$^{17}$ and R$^{18}$ are each independently selected from a hydrogen atom, a C$_1$-C$_6$-alkyl group, a C$_1$-C$_6$-haloalkyl group, a C$_3$-C$_5$-cycloalkyl group, a C$_1$-C$_3$-alkyl-C(O)— group, a C$_1$-C$_3$-alkyl-S(O)$_2$— group and a C$_1$-C$_3$-alkyl-O—C(=O)— group;

where R$^{19}$ is selected from a hydrogen atom, a hydroxy group, a cyano group, a C$_1$-C$_3$-alkyl group, a C$_1$-C$_6$-hydroxyalkyl group, a C$_1$-C$_3$-alkoxy group, a C(O)OR$^{21}$—(C$_1$-C$_3$-alkylene)- group, a —C(O)OR$^{21}$ group, a —C(O)NR$^{21}$R$^{22}$ group, a (C$_1$-C$_3$-alkyl)-O—(C$_1$-C$_3$-alkylene)-C(O)— group, (C$_1$-C$_6$-alkyl)-C(O)-group and a C$_3$-C$_6$-cycloalkyl-C(O)— group;
where R$^{20}$ is selected from a C$_1$-C$_3$-alkyl group, a C$_3$-C$_6$-cycloalkyl group, and a NR$^{21}$R$^{22}$ group; and
where R$^{21}$ and R$^{22}$ are independently selected from a hydrogen atom and a C$_1$-C$_6$-alkyl group;

R$^8$ is selected from a hydrogen atom,
a C$_1$-C$_6$-alkyl group, which is optionally substituted with one or more substituents independently selected from a halogen atom, a hydroxyl group, a C$_1$-C$_3$-alkoxy group, a C$_1$-C$_3$-haloalkoxy group, a C$_3$-C$_6$-cycloalkyl group, a heterocycloalkyl group and a NR$^{21}$R$^{22}$ group, or
a C$_1$-C$_3$-haloalkyl group,
a C$_3$-C$_6$-cycloalkyl group and
a C$_1$-C$_6$-alkyl group in which one or two not directly adjacent carbon atoms are independently replaced by a hetero atom selected from —O— and —NH—, R$^9$ is selected from a hydrogen atom,
a C$_1$-C$_4$-alkyl group,
a C$_1$-C$_3$-hydroxyalkyl group,
a C$_1$-C$_4$-haloalkyl group,
a C$_1$-C$_4$-haloalkyl-NH—C(O)—O—(C$_1$-C$_3$-alkylene)- group,
a C$_2$-C$_6$-haloalkenyl group,
a C$_1$-C$_6$-alkyl-O-group,
a C$_1$-C$_4$-haloalkoxy group,
a C$_1$-C$_6$-alkyl-O—(C$_1$-C$_3$-alkylene)- group,
a (C$_3$-C$_7$)-cycloalkyl group,
a (C$_3$-C$_7$)-cycloalkyl-O—(C$_1$-C$_3$-alkylene)- group,
a phenyl-O—(C$_1$-C$_3$-alkylene)- group,
a phenyl-(C$_1$-C$_3$-alkylene)-O—(C$_1$-C$_3$-alkylene)- group,
a R$^{19}$-phenyl-(C$_1$-C$_3$-alkylene)-O—(C$_1$-C$_3$-alkylene)- group,
a R$^{19}$-phenylene-O—(C$_1$-C$_3$-alkylene)- group,
a R$^{19}$-phenyl-heteroaryl-O—(C$_1$-C$_3$-alkylene)- group,
a (R$^{19}$)-(heterocycloalkyl)-(C$_1$-C$_3$-alkylene)- group,
a (R$^{19}$)-(heterocycloalkylene)-(phenylene)-O—(C$_1$-C$_3$-alkylene)- group,
a (heterocycloalkenylene)-(phenylene)-O—(C$_1$-C$_3$-alkylene)- group,
a (R$^{19}$)-(heteroaryl-(C$_1$-C$_3$-alkylene)-O—(C$_1$-C$_3$-alkylene)- group,
a (R$^{19}$)-(heteroaryl)-(phenylene)-O—(C$_1$-C$_3$-alkylene)- group,
a (R$^{20}$)—S(O)$_2$-phenylene-O—(C$_1$-C$_3$-alkylene)- group,
a (R$^{20}$)—S(O)$_2$—NH-phenylene-O—(C$_1$-C$_3$-alkylene)- group,
a (R$^{20}$)—S(O)$_2$—NH-phenylene-O—(C$_1$-C$_3$-alkylene)- group,
a (R$^{20}$)—S(O)$_2$—N(C$_1$-C$_6$-alkyl)-phenylene-O—(C$_1$-C$_3$-alkylene)- group,
a (R$^{20}$)—S(O)$_2$-heterocycloalkylene-phenylene-O—(C$_1$-C$_3$-alkylene)- group,
a (R$^{19}$)-(heterocycloalkylene)-(heteroarylene)-O—(C$_1$-C$_3$-alkylene)- group,
a (R$^{20}$)-heteroarylene-O—(C$_1$-C$_3$-alkylene)- group,
a (R$^{19}$)-heteroarylene-O—(C$_1$-C$_3$-alkylene)- group,
a (R$^{20}$)—S(O)$_2$-heteroarylene-O—(C$_1$-C$_3$-alkylene)- group,
a (R$^{20}$)—S(O)$_2$-heterocycloalkylene-heteroarylene-O—(C$_1$-C$_3$-alkylene)- group, a NR$^{21}$R$^{22}$—(C$_1$-C$_3$-alkylene)- group,
a (C$_1$-C$_3$-alkyl)-NH—(C$_1$-C$_3$-alkylene)- group,
a (C$_1$-C$_3$-haloalkyl)-(C$_1$-C$_3$-alkylene)-NH—(C$_1$-C$_3$-alkylene)- group,
a (C$_1$-C$_3$-haloalkyl)-NH—(C$_1$-C$_3$-alkylene)- group,
a (C$_1$-C$_3$-alkyl)-NH—C(O)—(C$_1$-C$_3$-alkylene)- group,
a (C$_1$-C$_3$-alkyl)-NR$^{15}$—C(O)—(C$_1$-C$_3$-alkylene)- group,
a (C$_1$-C$_3$-alkyl)-C(O)—NH—(C$_1$-C$_3$-alkylene)- group,
a (C$_1$-C$_3$-alkyl)-C(O)—NR$^{15}$—(C$_1$-C$_3$-alkylene)- group,
a

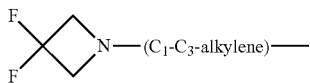

group and a

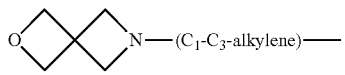

group,
where the phenyl ring is optionally substituted with a halogen atom, a hydroxyl group, or a C$_1$-C$_3$-alkoxy group and
the heterocycloalkyl group is optionally substituted with an oxo (=O) group or is optionally substituted with one or more substituents independently selected from a halogen atom, a hydroxyl group, a C$_1$-C$_3$-alkyl group and a C$_1$-C$_3$-alkoxy group,
or R$^8$ and R$^9$ together form a 5- or 6-membered ring optionally containing one or two heteroatoms selected from —O— and —NR$^{14}$—,
R$^{11}$ and R$^{13}$ are each independently selected from a hydrogen atom, a halogen atom, a C$_1$-C$_3$-alkyl group and a C$_1$-C$_3$-alkoxy group;
R$^{12}$ is selected from a hydrogen atom, a C$_1$-C$_3$-alkoxy group, a C$_1$-C$_3$-alkyl group, a C$_1$-C$_3$-haloalkyl group, a C$_1$-C$_3$-haloalkoxy group and a NR$^{17}$R$^{18}$ group;
or a tautomer, an N-oxide, or a salt thereof or a salt of a tautomer or a N-oxide or a mixture of same.

FURTHER EMBODIMENTS OF THE FIRST ASPECT OF THE PRESENT INVENTION

In some embodiments, the present invention includes compounds of formula (I), supra, in which R$^1$, R$^2$, and R$^3$ are each selected from a hydrogen atom, a halogen atom, and a C$_1$-C$_3$-alkyl group, or stereoisomers, tautomers, N-oxides, and salts thereof, and mixtures of same.

In some embodiments, the present invention includes compounds of formula (I), supra, in which R$^1$, R$^2$, and R$^3$ are each selected from a hydrogen atom, a halogen atom, a C$_1$-C$_3$-alkyl group and a C$_1$-C$_3$-alkoxy group, or stereoisomers, tautomers, N-oxides, and salts thereof, and mixtures of same.

In some embodiments, the present invention includes compounds of formula (I), supra, in which R$^1$, R$^2$, and R$^3$ are each selected from a hydrogen atom, a halogen atom and a C$_1$-C$_3$-alkyl group, or stereoisomers, tautomers, N-oxides, and salts thereof, and mixtures of same.

In some embodiments, the present invention includes compounds of formula (I), supra, in which R$^1$ and R$^2$ are each independently selected from a hydrogen atom, a halogen atom, a cyano group, and a C$_1$-C$_3$-alkyl group.

In some embodiments, the present invention includes compounds of formula (I), supra, in which R$^1$ and R$^2$ are each independently selected from a hydrogen atom, a halogen atom and a C$_1$-C$_3$-alkyl group.

In some embodiments, the present invention includes compounds of formula (I), supra, in which R$^1$ and R$^2$ are each independently selected from a hydrogen atom and a C$_1$-C$_3$-alkyl group.

In some embodiments, the present invention includes compounds of formula (I), supra, in which R$^1$ and R$^2$ are a hydrogen atom.

In some embodiments, the present invention includes compounds of formula (I), supra, in which R$^1$ is a hydrogen atom.

In some embodiments, the present invention includes compounds of formula (I), supra, in which R$^2$ is a hydrogen atom.

In some embodiments, the present invention includes compounds of formula (I), supra, in which R$^3$ is selected from a hydrogen atom, a halogen atom, a cyano group, a C$_1$-C$_3$-alkyl group, a C$_1$-C$_3$-haloalkyl group, a C$_1$-C$_3$-alkoxy group, a C$_1$-C$_3$-alkylthio group, a —S(O)—(C$_1$-C$_3$-alkyl) group, a —S(O)$_2$—(C$_1$-C$_3$-alkyl) group, a C$_1$-C$_3$-haloalkoxy group, a C$_1$-C$_3$-haloalkylthio group, and a C$_3$-C$_5$-cycloalkyl group.

In some embodiments, the present invention includes compounds of formula (I), supra, in which R$^3$ is selected from a hydrogen atom, a halogen atom, a cyano group, a C$_1$-C$_3$-alkyl group, a C$_1$-C$_3$-haloalkyl group, a C$_1$-C$_3$-alkoxy group, a C$_1$-C$_3$-alkylthio group, a C$_1$-C$_3$-haloalkoxy group, a C$_1$-C$_3$-haloalkylthio group, and a C$_3$-C$_5$-cycloalkyl group.

In some embodiments, the present invention includes compounds of formula (I), supra, in which R$^3$ is a hydrogen atom.

In some embodiments, the present invention includes compounds of formula (I), supra, in which R$^4$ is selected from an aryl group and a heteroaryl group, which is optionally substituted with one, two, three, four or five substituents and each substituent is independently selected from a halogen atom, a cyano group, a C$_1$-C$_3$-alkyl group, a C$_1$-C$_3$-haloalkyl group, a C$_1$-C$_3$-alkoxy group, a C$_1$-C$_3$-thioalkyl group, a C$_1$-C$_3$-haloalkoxy group, a (C$_1$-C$_3$)-haloalkyl-S— group, and a C$_3$-C$_5$-cycloalkyl group, or a, a tautomer, an N-oxide, or a salt thereof or a salt of a tautomer or a N-oxide or a mixture of same.

In some embodiments, the present invention includes compounds of formula (I), supra, in which R$^4$ is an aryl group, which is optionally substituted with one, two, or three substituents and each substituent is independently selected from a halogen atom, a C$_1$-C$_3$-alkyl group, and a C$_1$-C$_3$-haloalkyl group, or a, a tautomer, an N-oxide, or a salt thereof or a salt of a tautomer or a N-oxide or a mixture of same.

In other embodiments, the present invention includes compounds of formula (I), supra, in which R$^4$ is selected from an aryl group and a heteroaryl group, which is optionally substituted with one, two, three, four or five substituents and each substituent is independently selected from a halogen atom, a cyano group, a C$_1$-C$_3$-alkyl group, a C$_1$-C$_3$-haloalkyl group, a C$_1$-C$_3$-alkoxy group, a C$_1$-C$_3$-thioalkyl group, a C$_1$-C$_3$-haloalkoxy group, and a C$_1$-C$_3$-halothioalkyl group, or a, a tautomer, an N-oxide, or a salt thereof or a salt of a tautomer or a N-oxide or a mixture of same.

In other embodiments, the present invention includes compounds of formula (I), supra, in which $R^4$ is an aryl group or a heteroaryl group, which is optionally substituted with one, two, three, four or five substituents and each substituent is independently selected from a halogen atom, a cyano group, a $C_1$-$C_3$-alkyl group, a $C_1$-$C_3$-haloalkyl group, a $C_1$-$C_3$-alkoxy group, and a $C_1$-$C_3$-haloalkoxy group, or a, a tautomer, an N-oxide, or a salt thereof or a salt of a tautomer or a N-oxide or a mixture of same.

In other embodiments, the present invention provides compounds of formula (I), supra, in which $R^4$ is an aryl group, which is optionally substituted with one, two, three, four or five substituents and each substituent independently is selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, and a $C_1$-$C_3$-halothioalkyl group, or a tautomer, an N-oxide, or a salt thereof or a salt of a tautomer or a N-oxide or a mixture of same.

In other embodiments, the present invention includes compounds of formula (I), supra, in which $R^4$ is an aryl group, which is optionally substituted with one, two, or three substituents and each substituent is independently selected from a halogen atom, a cyano group, a $C_1$-$C_3$-alkyl group, a $C_1$-$C_3$-haloalkyl group, a $C_1$-$C_3$-alkoxy group, and a $C_1$-$C_3$-haloalkoxy group or a tautomer, an N-oxide, or a salt thereof or a salt of a tautomer or a N-oxide or a mixture of same.

In other embodiments, the present invention includes compounds of formula (I), supra, in which $R^4$ is a group, which is optionally substituted with one, two or three substituents and each substituent is independently selected from a halogen atom, a $C_1$-$C_3$-alkyl group and a $C_1$-$C_3$-haloalkyl group, or a tautomer, an N-oxide, or a salt thereof or a salt of a tautomer or a N-oxide or a mixture of same.

In other embodiments, the present invention includes compounds of formula (I), supra, in which $R^4$ is a heteroaryl group, which is optionally substituted with one, two, three, four or five substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, and a $C_1$-$C_3$-halothioalkyl group, or a tautomer, an N-oxide, or a salt thereof or a salt of a tautomer or a N-oxide or a mixture of same.

In other embodiments, the present invention includes compounds of formula (I), supra, in which $R^4$ is a heteroaryl group, which is optionally substituted with one, two, three, four or five substituents and each substituent is independently selected from a halogen atom, a cyano group, a $C_1$-$C_3$-alkyl group, a $C_1$-$C_3$-haloalkyl group, and a $C_1$-$C_3$-alkoxy group, or a tautomer, an N-oxide, or a salt thereof or a salt of a tautomer or a N-oxide or a mixture of same.

In further embodiments the present invention includes compounds of formula (I), supra, in which $R^4$ is selected from a 1-naphthyl group, a 4-chloro-3,5-dimethyl-phenyl-1-yl group, and a 5,6,7,8-tetrahydronaphthalene-1-yl group, or a tautomer, an N-oxide, or a salt thereof or a salt of a tautomer or a N-oxide or a mixture of same.

In further embodiments the present invention includes compounds of formula (I), supra, in which $R^4$ is selected from
a 1-naphthyl group, which is optionally substituted one or two times with a group selected from a fluorine atom, a chlorine atom, a methyl group or a trifluoromethyl group,
a 4-chloro-3,5-dimethyl-phenyl-1-yl group, and
a 5,6,7,8-tetrahydronaphthalene-1-yl group, or a tautomer, an N-oxide, or a salt thereof or a salt of a tautomer or a N-oxide or a mixture of same.

In other embodiments, the present invention includes compounds of formula (I), supra, in which $R^4$ is selected from a phenyl group, a naphthyl group, a 5,6-dihydronaphthyl group, a 7,8-dihydronaphthyl group, and a 5,6,7,8-tetrahydronaphthyl group, each of which are optionally substituted with one, two, three, four or five substituents, particularly one, two or three substituents, and each substituent is independently selected from a halogen atom, a $C_1$-$C_3$-alkyl group, a $C_1$-$C_3$-haloalkyl group, a $C_1$-$C_3$-alkoxy group, and a $C_1$-$C_3$-haloalkoxy group, or a tautomer, an N-oxide, or a salt thereof or a salt of a tautomer or a N-oxide or a mixture of same.

In other embodiments, the present invention includes compounds of formula (I), supra, in which $R^4$ is selected from a phenyl group, a naphthyl group, and a 5,6,7,8-tetrahydronaphthyl group, each of which are optionally substituted with one, two or three substituents, and each substituent is independently selected from a halogen atom, a $C_1$-$C_3$-alkyl group, a $C_1$-$C_3$-haloalkyl group, a $C_1$-$C_3$-alkoxy group, and a $C_1$-$C_3$-haloalkoxy group, or a tautomer, an N-oxide, or a salt thereof or a salt of a tautomer or a N-oxide or a mixture of same.

In other embodiments, the present invention includes compounds of formula (I), supra, in which $R^4$ is selected from a phenyl group, a naphthyl group, and a 5,6,7,8-tetrahydronaphthyl group, each of which are optionally substituted with one, two or three substituents, and each substituent is independently selected from a halogen atom and a $C_1$-$C_3$-alkyl group, or a tautomer, an N-oxide, or a salt thereof or a salt of a tautomer or a N-oxide or a mixture of same.

In other embodiments, the present invention includes compounds of formula (I), supra, in which $R^4$ is a 4-chloro-3,5-dimethyl-phenyl-1-yl group, or a, a tautomer, an N-oxide, or a salt thereof or a salt of a tautomer or a N-oxide or a mixture of same.

In further embodiments, the present invention includes compounds of formula (I), supra, in which $R^4$ is a 5,6,7,8-tetrahydronaphthalene-1-yl group, or a, a tautomer, an N-oxide, or a salt thereof or a salt of a tautomer or a N-oxide or a mixture of same.

In further embodiments, the present invention includes compounds of formula (I), supra, in which $R^4$ is a 1-naphthyl group, or a, a tautomer, an N-oxide, or a salt thereof or a salt of a tautomer or a N-oxide or a mixture of same.

In further embodiments, the present invention includes compounds of formula (I), supra, in which $R^4$ is a 1-naphthyl group, which is optionally substituted one or two times with a group selected from a fluorine atom, a chlorine atom, a methyl group and a trifluoromethyl group, or a tautomer, an N-oxide, or a salt thereof or a salt of a tautomer or a N-oxide or a mixture of same.

In further embodiments, the present invention includes compounds of formula (I), supra, in which $R^4$ is a halo-naphthyl group, particularly 6-halo-naphthyl group, more particularly a 6-chloro-naphthyl group or a 6-fluoro-naphthyl group.

In further embodiments, the present invention includes compounds of formula (I), supra, in which $R^4$ is selected from a 4-chloro-3,5-dimethyl-phenyl-1-yl group and a 5,6,7,8-tetrahydronaphthalene-1-yl group, or a tautomer, an N-oxide, or a salt thereof or a salt of a tautomer or a N-oxide or a mixture of same.

In other embodiments, the present invention includes compounds of formula (I), supra, in which $R^4$ has one, two or three optional substituents.

In other embodiments, the present invention includes compounds of formula (I), supra, in which L is a group —$(CH_2)_m$-E- which is optionally substituted with one or two substituents and each substituent is independently selected from a halogen atom, a hydroxyl group, a $C_1$-$C_3$-alkyl group, and a $C_1$-$C_3$-alkoxy group, or two substituents are taken together with their intervening atoms to form a saturated or partially unsaturated 3-6-membered cycloalkyl ring, or a 3-8 membered saturated or partially unsaturated heterocyclic ring having 1-2 heteroatoms independently selected from an oxygen atom, a sulfur atom, a —S(O)— group, a —S(O)$_2$— group, and a —NR$^{14}$— group, or a tautomer, an N-oxide, or a salt thereof or a salt of a tautomer or a N-oxide or a mixture of same.

In other embodiments, the present invention includes compounds of formula (I), supra, in which L is a group —$(CH_2)_m$-E- which is optionally substituted with one or two substituents and each substituent is independently selected from a halogen atom, a hydroxyl group, a $C_1$-$C_3$-alkyl group, and a $C_1$-$C_3$-alkoxy group, or two substituents are taken together with their intervening atoms to form a saturated or partially unsaturated 3-6-membered ring, or a 3-8 membered saturated or partially unsaturated heterocyclic ring having 1-2 heteroatoms independently selected from an oxygen atom, a sulfur atom, a —S(O)— group, a —S(O)$_2$— group, and a —NR$^{14}$— group, or a tautomer, an N-oxide, or a salt thereof or a salt of a tautomer or a N-oxide or a mixture of same.

In other embodiments, the present invention includes compounds of formula (I), supra, in which L is a —$(CH_2)_m$-E- group which is optionally substituted with a $C_1$-$C_3$-alkyl group, particularly with a methyl group.

In other embodiments, the present invention includes compounds of formula (I), supra, in which L is an unsubstituted group —$(CH_2)_m$-E-.

In further embodiments, the present invention includes compounds of formula (I), supra, in which E is an oxygen atom, or a tautomer, an N-oxide, or a salt thereof or a salt of a tautomer or a N-oxide or a mixture of same.

In other embodiments, the present invention includes compounds of formula (I), supra, in which L is a —$(CH_2)_m$-E- group which is optionally substituted with a $C_1$-$C_3$-alkyl group, particularly with a methyl group, and E is a oxygen atom.

In other embodiments, the present invention includes compounds of formula (I), supra, in which L is an unsubstituted group —$(CH_2)_m$-E- and E is an oxygen atom.

In yet further embodiments, the present invention includes compounds of formula (I), supra, in which $R^5$ is a COOH group, a

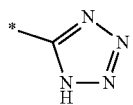

group, a —C(O)—NHS(O)$_2$($C_1$-$C_6$-alkyl) group, a —C(O)—NHS(O)$_2$($C_3$-$C_6$-cycloalkyl) group, a —C(O)—NHS(O)$_2$(aryl) group, a —C(O)—NHS(O)$_2$(CH$_2$)$_2$NHCO($C_1$-$C_6$-alkyl) group, a —C(O)—NHS(O)$_2$(CH$_2$)$_2$NHCO($C_3$-$C_6$-cycloalkyl) group, or a —C(O)—NHS(O)$_2$(CH$_2$)$_2$NHCO(aryl) group, or a tautomer, an N-oxide, or a salt thereof or a salt of a tautomer or a N-oxide or a mixture of same.

In further embodiments, the present invention includes compounds of formula (I), supra, in $R^5$ is a COOH group, or a

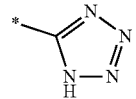

group, or a tautomer, an N-oxide, or a salt thereof or a salt of a tautomer or a N-oxide or a mixture of same.

In further embodiments, the present invention includes compounds of formula (I), supra, in $R^5$ is a COOH group, or a tautomer, an N-oxide, or a salt thereof or a salt of a tautomer or a N-oxide or a mixture of same.

In other embodiments, the present invention includes compounds of formula (I), supra, in which —$R^6$-$R^7$— is selected from $^{\#}$—$(CH_2)_n$—(B)$_t$—$(CH_2)_p$—$^{\#\#}$, $^{\#}$—($C_2$-$C_6$-alkenylene)-(B)$_t$—$(CH_2)_p$—$^{\#\#}$, $^{\#}$—$(CH_2)_n$—(B)$_t$—($C_2$-$C_6$-alkenylene)-$^{\#\#}$, and $^{\#}$—$(CH_2)_q$—(B)—$(CH_2)_t$—(B)—$(CH_2)_v$—$^{\#\#}$, wherein any $CH_2$ group is optionally substituted with one or more substituents selected from a halogen atom, a hydroxyl group, a NR$^{17}$R$^{18}$ group, a $C_1$-$C_3$-alkyl group, a $C_1$-$C_3$-haloalkyl group, a $C_1$-$C_3$-alkoxy group, a $C_1$-$C_3$-haloalkoxy group, and a (heterocycloalkyl)-($C_1$-$C_3$-alkylene)- group, and where the alkenylene can be replaced by a 1,2-cyclopropyl group, wherein $^{\#}$ is the point of attachment with the indole nitrogen atom and $^{\#\#}$ is the point of attachment with the pyrazole carbon atom bearing the $R^7$ substituent, or a tautomer, an N-oxide, or a salt thereof or a salt of a tautomer or a N-oxide or a mixture of same.

In further embodiments, the present invention includes compounds of formula (I), supra, in which —$R^6$-$R^7$— is selected from $^{\#}$—$(CH_2)_n$—(B)$_t$—$(CH_2)_p$—$^{\#\#}$, $^{\#}$—($C_2$-$C_6$-alkenylene)-(B)$_t$—$(CH_2)_p$—$^{\#\#}$, $^{\#}$—$(CH_2)_n$—(B)$_t$—($C_2$-$C_6$-alkenylene)-$^{\#\#}$, and $^{\#}$—$(CH_2)_n$—(O)—$(CH_2)_t$—(O)—$(CH_2)_v$—$^{\#\#}$, where t and v are each 1, wherein any $CH_2$ group is optionally substituted with one or more substituents selected from a halogen atom, a hydroxyl group, a NR$^{17}$R$^{18}$ group, a $C_1$-$C_3$-alkyl group, a $C_1$-$C_3$-haloalkyl group, a $C_1$-$C_3$-alkoxy group, and a $C_1$-$C_3$-haloalkoxy group, and where the alkenylene can be replaced by a 1,2-cyclopropyl group, wherein $^{\#}$ is the point of attachment with the indole nitrogen atom and $^{\#\#}$ is the point of attachment with the pyrazole carbon atom bearing the $R^7$ substituent, or a tautomer, an N-oxide, or a salt thereof or a salt of a tautomer or a N-oxide or a mixture of same.

In other embodiments, the present invention includes compounds of formula (I), supra, in which —$R^6$-$R^7$— is selected from $^{\#}$—$(CH_2)_n$—(B)$_t$—$(CH_2)_p$—$^{\#\#}$, $^{\#}$—($C_2$-$C_6$-alkenylene)-(B)$_t$—$(CH_2)_p$—$^{\#\#}$, $^{\#}$—$(CH_2)_n$—(B)$_t$—($C_2$-$C_6$-alkenylene)-$^{\#\#}$, and $^{\#}$—$(CH_2)_q$—(B)—$(CH_2)_t$(B)—$(CH_2)_v$—$^{\#\#}$, or a tautomer, an N-oxide, or a salt thereof or a salt of a tautomer or a N-oxide or a mixture of same.

In other embodiments, the present invention includes compounds of formula (I), supra, in which —$R^6$-$R^7$— is selected from $^{\#}$—$(CH_2)_n$—(B)$_t$—$(CH_2)_p$—$^{\#\#}$, and $^{\#}$—($C_2$-$C_6$-alkenylene)-(B)$_t$—$(CH_2)_p$—$^{\#\#}$, wherein $^{\#}$ is the point of attachment with the indole nitrogen atom and $^{\#\#}$ is the point of attachment with the pyrazole carbon atom bearing the $R^7$ substituent, or a tautomer, an N-oxide, or a salt thereof or a salt of a tautomer or a N-oxide or a mixture of same.

In other embodiments, the present invention includes compounds of formula (I), supra, in which —R$^6$-R$^7$— is selected from $^\#$—(CH$_2$)$_n$—(B)$_t$—(CH$_2$)$_p$—$^{\#\#}$, and $^\#$—(C$_2$-C$_6$-alkenylene)-(B)$_t$—(CH$_2$)$_p$—$^{\#\#}$, wherein $^\#$ is the point of attachment with the indole nitrogen atom and $^{\#\#}$ is the point of attachment with the pyrazole carbon atom bearing the R$^7$ substituent, and A is A1 or A2, or a tautomer, an N-oxide, or a salt thereof or a salt of a tautomer or a N-oxide or a mixture of same.

In other embodiments, the present invention includes compounds of formula (I), supra, in which —R$^6$-R$^7$— is selected from —(CH$_2$)$_3$—N(CH$_3$)—CH$_2$—, —(CH$_2$)$_2$-(morpholinylium]$^+$-CH$_2$—, —(CH$_2$)$_2$—N(R$^{15}$)—CH$_2$—, —CH$_2$—CH=CH—CH$_2$—O—CH$_2$, —(CH$_2$—)$_6$, and —(CH$_2$)$_2$—O—(CH$_2$)$_2$—O—, or a tautomer, an N-oxide, or a salt thereof or a salt of a tautomer or a N-oxide or a mixture of same.

In other embodiments, the present invention includes compounds of formula (I), supra, in which —R$^6$-R$^7$— is selected from —(CH$_2$)$_3$—N(CH$_3$)—CH$_2$—, —(CH$_2$)$_4$—N(CH$_3$)—CH$_2$—, —(CH$_2$)$_2$-(morpholinylium]$^+$-CH$_2$—, —(CH$_2$)$_2$—N(R$^{15}$)—CH$_2$—, —CH$_2$—CH=CH—CH$_2$—O—CH$_2$—, —CH$_2$—CH=CH—CH$_2$—N(CH$_2$-phenyl)-, —(CH$_2$)$_3$O—CH$_2$—, —(CH$_2$)$_4$O—CH$_2$—, —(CH$_2$)$_5$—O—CH$_2$, —(CH$_2$—)$_6$, —(CH$_2$)$_5$—O—, —(CH$_2$)$_2$—O—CH$_2$—, —(CH$_2$)$_2$—O—(CH$_2$)$_2$—O—, —(CH$_2$)$_4$—N(CH$_2$-phenyl)-, and —(CH$_2$)$_3$—N(CH$_2$-phenyl)-, or a tautomer, an N-oxide, or a salt thereof or a salt of a tautomer or a N-oxide or a mixture of same.

In other embodiments, the present invention includes compounds of formula (I), supra, in which —R$^6$-R$^7$— is selected from —(CH$_2$)$_3$—N(CH$_3$)—CH$_2$—, —(CH$_2$)$_4$—N(CH$_3$)—CH$_2$—, —(CH$_2$)$_3$O—CH$_2$—, —(CH$_2$)$_4$O—CH$_2$—, and —(CH$_2$—)$_6$—, or a tautomer, an N-oxide, or a salt thereof or a salt of a tautomer or a N-oxide or a mixture of same.

In other embodiments, the present invention includes compounds of formula (I), supra, in which —R$^6$-R$^7$— is selected from —(CH$_2$)$_3$—N(CH$_3$)—CH$_2$—, and —(CH$_2$)$_4$—N(CH$_3$)—CH$_2$ or a tautomer, an N-oxide, or a salt thereof or a salt of a tautomer or a N-oxide or a mixture of same.

In other embodiments, the present invention includes compounds of formula (I), supra, in which —R$^6$-R$^7$— is selected from —(CH$_2$)$_3$O—CH$_2$—, —(CH$_2$)$_4$O—CH$_2$—, and —(CH$_2$—)$_6$—, or a tautomer, an N-oxide, or a salt thereof or a salt of a tautomer or a N-oxide or a mixture of same.

In other embodiments, the present invention includes compounds of formula (I), supra, in which —R$^6$-R$^7$— is *—(CH$_2$)$_n$—(B)$_t$—(CH$_2$)$_p$—$^\#$, or a tautomer, an N-oxide, or a salt thereof or a salt of a tautomer or a N-oxide or a mixture of same.

In further embodiments, the present invention includes compounds of formula (I), supra, in which —R$^6$-R$^7$— is $^\#$—(CH$_2$)$_n$—O—(CH$_2$)$_t$—O—CH$_2$—$^{\#\#}$, wherein * is the point of attachment with the indole nitrogen atom and $^\#$ is the point of attachment with the pyrazole carbon atom bearing the R$^7$ substituent, or a tautomer, an N-oxide, or a salt thereof or a salt of a tautomer or a N-oxide or a mixture of same.

In other embodiments, the present invention includes compounds of formula (I), supra, in which —R$^6$-R$^{10}$— is selected from $^\#$—(CH$_2$)$_n$—(B)$_t$(CH$_2$)$_p$—$^{\#\#}$, $^\#$—(C$_2$-C$_6$-alkenylen)$_q$-(B)$_t$—(CH$_2$)$_p$, and $^\#$—(CH$_2$)$_n$—O—(CH$_2$)$_t$O—$^{\#\#}$, where one or more CH$_2$ groups are optionally substituted with one or more substituents selected from a halogen atom, a hydroxyl group, a C$_1$-C$_3$-alkyl group, a C$_1$-C$_3$-haloalkyl group, a C$_1$-C$_3$-alkoxy group, and a C$_1$-C$_3$-haloalkoxy group, wherein $^\#$ is the point of attachment with the indole nitrogen atom and $^{\#\#}$ is the point of attachment with the carbon atom of the phenyl moiety bearing the R$^{10}$ substituent, or a tautomer, an N-oxide, or a salt thereof or a salt of a tautomer or a N-oxide or a mixture of same.

In other embodiments, the present invention includes compounds of formula (I), supra, in which —R$^6$-R$^{10}$— is $^\#$—(CH$_2$)$_q$—(B)—(CH$_2$)$_t$(B)—(CH$_2$)$_v$—$^{\#\#}$, where one or more CH$_2$ groups are optionally substituted with one or more substituents selected from a halogen atom, a hydroxyl group, a C$_1$-C$_3$-alkyl group, a C$_1$-C$_3$-haloalkyl group, a C$_1$-C$_3$-alkoxy group, and a C$_1$-C$_3$-haloalkoxy group, wherein $^\#$ is the point of attachment with the indole nitrogen atom and $^{\#\#}$ is the point of attachment with the carbon atom of the phenyl moiety bearing the R$^{10}$ substituent, or a tautomer, an N-oxide, or a salt thereof or a salt of a tautomer or a N-oxide or a mixture of same.

In further embodiments, the present invention includes compounds of formula (I), supra, in which —R$^6$-R$^{10}$— is $^\#$—(CH$_2$)$_n$—(B)$_t$—(CH$_2$)$_p$—$^{\#\#}$, wherein $^\#$ is the point of attachment with the indole nitrogen atom and $^{\#\#}$ is the point of attachment with the carbon atom of the phenyl moiety bearing the R$^{10}$ substituent, or a tautomer, an N-oxide, or a salt thereof or a salt of a tautomer or a N-oxide or a mixture of same.

In other embodiments, the present invention includes compounds of formula (I), supra, in which —R$^6$-R$^{10}$— is $^\#$—(CH$_2$)$_n$—O—(CH$_2$)$_t$O—$^{\#\#}$, wherein $^\#$ is the point of attachment with the indole nitrogen atom and $^{\#\#}$ is the point of attachment with the carbon atom of the phenyl moiety bearing the R$^{10}$ substituent, or a tautomer, an N-oxide, or a salt thereof or a salt of a tautomer or a N-oxide or a mixture of same.

In other embodiments, the present invention includes compounds of formula (I), supra, in which —R$^6$-R$^{10}$— is $^\#$—(CH$_2$)$_n$—O—(CH$_2$)$_t$O—$^{\#\#}$, or $^\#$—(CH$_2$)$_n$—(B)$_t$(CH$_2$)$_p$—$^{\#\#}$ and A is A3 or a tautomer, an N-oxide, or a salt thereof or a salt of a tautomer or a N-oxide or a mixture of same.

In other embodiments, the present invention includes compounds of formula (I), supra, in which —R$^6$-R$^{10}$— is —(CH$_2$)$_2$—O—(CH$_2$)$_2$—O— or —(CH$_2$)$_5$—O— or a tautomer, an N-oxide, or a salt thereof or a salt of a tautomer or a N-oxide or a mixture of same.

For —R$^6$-R$^7$— and —R$^6$-R$^{10}$— moieties in which B occurs more than once such as e.g. $^\#$—(CH$_2$)$_q$—(B)—(CH$_2$)$_t$(B)—(CH$_2$)$_v$—$^{\#\#}$ it is understood that if one B is a nitrogen atom and the other B is an oxygen atom following, both, the nitrogen atom and the oxygen atom, have to be separated by at least two carbon atoms or a tautomer, an N-oxide, or a salt thereof or a salt of a tautomer or a N-oxide or a mixture of same.

In further embodiments, the present invention includes compounds of formula (I), supra, in which B is independently selected from a —C(O)NR$^{15}$— group, a —NR$^{15}$C(O)— group, a —N(R$^{15}$)— group, a —N(R$^{15}$)—C(=O)—N(R$^{15}$)— group, a —O—C(=O)—N(R$^{15}$)— group, a —N(R$^{15}$)—C(=O)—O— group, —O—, —S—, —S(O)—, —S(O)$_2$—, a —S(O)NR$^{15}$— group, a —NR$^{15}$S(O)— group, a —S(O)$_2$NR$^{15}$— group, a —NR$^{15}$S(O)$_2$— group, or a tautomer, an N-oxide, or a salt thereof or a salt of a tautomer or a N-oxide or a mixture of same.

In further embodiments, the present invention includes compounds of formula (I), supra, in which B is independently selected from a —C(O)NR$^{15}$— group, a —NR$^{15}$C(O)— group, a —N(R$^{15}$)— group, —O—, —S—, —S(O)— and —S(O)$_2$—, or a tautomer, an N-oxide, or a salt thereof or a salt of a tautomer or a N-oxide or a mixture of same.

In further embodiments, the present invention includes compounds of formula (I), supra, in which B is independently selected from a —N(R$^{15}$)— group, —O—, —S—, —S(O)— and —S(O)$_2$—, or a tautomer, an N-oxide, or a salt thereof or a salt of a tautomer or a N-oxide or a mixture of same.

In further embodiments, the present invention includes compounds of formula (I), supra, in which B is independently selected from a —C(O)NR$^{15}$— group, a —NR$^{15}$C(O)— group, a —N(R$^{15}$)— group, —O— and —S— or a tautomer, an N-oxide, or a salt thereof or a salt of a tautomer or a N-oxide or a mixture of same.

In further embodiments, the present invention includes compounds of formula (I), supra, in which B is independently selected from In further embodiments, the present invention includes compounds of formula (I), supra, in which B is independently selected from —O—, —S— and a —N(R$^{15}$)— group or a tautomer, an N-oxide, or a salt thereof or a salt of a tautomer or a N-oxide or a mixture of same.

In further embodiments, the present invention includes compounds of formula (I), supra, in which B is independently selected from a —C(O)NR$^{15}$— group, a —NR$^{15}$C(O)— group and a —N(R$^{15}$)— group or a tautomer, an N-oxide, or a salt thereof or a salt of a tautomer or a N-oxide or a mixture of same.

In further embodiments, the present invention includes compounds of formula (I), supra, in which B is independently selected from a —O—, —S—, —S(O)— and —S(O)$_2$—, or a tautomer, an N-oxide, or a salt thereof or a salt of a tautomer or a N-oxide or a mixture of same.

In further embodiments, the present invention includes compounds of formula (I), supra, in which B is independently selected from a —N(R$^{15}$)—C(=O)—N(R$^{15}$)— group, a —O—C(=O)—N(R$^{15}$)— group, a —N(R$^{15}$)—C(=O)—O— group, a —NR$^{15}$S(O)— group, a —S(O)$_2$NR$^{15}$— group, a —NR$^{15}$S(O)$_2$— group, or a tautomer, an N-oxide, or a salt thereof or a salt of a tautomer or a N-oxide or a mixture of same.

In further embodiments, the present invention includes compounds of formula (I), supra, in which B is independently selected from a a —NR$^{15}$S(O)— group, a —S(O)$_2$NR$^{15}$— group and a —NR$^{15}$S(O)$_2$— group, or a tautomer, an N-oxide, or a salt thereof or a salt of a tautomer or a N-oxide or a mixture of same.

In further embodiments, the present invention includes compounds of formula (I), supra, in which B is an oxygen atom or —NR$^{15}$— or a tautomer, an N-oxide, or a salt thereof or a salt of a tautomer or a N-oxide or a mixture of same.

In further embodiments, the present invention includes compounds of formula (I), supra, in which B is an oxygen atom or a tautomer, an N-oxide, or a salt thereof or a salt of a tautomer or a N-oxide or a mixture of same.

In further embodiments, the present invention includes compounds of formula (I), supra, in which B is —NR$^{15}$—, particularly —NH— or —N(C$_1$-C$_3$-alkyl)-, more particularly —NH— or —N(CH$_3$)— or a tautomer, an N-oxide, or a salt thereof or a salt of a tautomer or a N-oxide or a mixture of same.

In further embodiments, the present invention includes compounds of formula (I), supra, in which B is a cation with R$^{16}$ as the respective anion, particularly

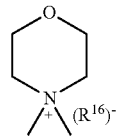

or —N$^+$(R$^{21}$R$^{22}$)(R$^{16}$)$^-$, more particularly

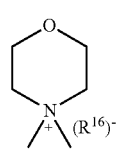

or —N$^+$(CH$_3$)$_2$(R$^{16}$)$^-$ or a tautomer, an N-oxide, or a salt thereof or a salt of a tautomer or a N-oxide or a mixture of same.

In other embodiments, the present invention includes compounds of formula (I), supra, in which A is A1, or a tautomer, an N-oxide, or a salt thereof or a salt of a tautomer or a N-oxide or a mixture of same.

In further embodiments, the present invention includes compounds of formula (I), supra, in which A is A2, or a tautomer, an N-oxide, or a salt thereof or a salt of a tautomer or a N-oxide or a mixture of same.

In yet other embodiments, the present invention includes compounds of formula (I), supra, in which A is A3, or a tautomer, an N-oxide, or a salt thereof or a salt of a tautomer or a N-oxide or a mixture of same.

In yet other embodiments, the present invention includes compounds of formula (I), supra, in which A is A3 and the macrocyclic ring is a 9- membered-, a 10-membered-, a 11-membered-, a 12-membered-, a 13-membered-, a 14-membered-, a 15-membered- or a 16-membered ring, particularly a 9- membered-, a 10-membered-, a 11-membered-, or a 12-membered ring, more particularly a 12-membered ring or a tautomer, an N-oxide, or a salt thereof or a salt of a tautomer or a N-oxide or a mixture of same.

In yet other embodiments, the present invention includes compounds of formula (I), supra, in which A is A3 whereby optionally one or two of the groups selected from CR$^{11}$, CR$^{12}$ or CR$^{13}$ may be replaced by a nitrogen atom, wherein R$^6$ and R$^{10}$, together with three carbon atoms of the phenyl ring, two carbon atoms of the indole moiety and the nitrogen atom to which R$^6$ is attached, form a 9- to 16-membered ring and * is the point of attachment of these moieties to the indole carbon atom bearing the A substituent;

In yet other embodiments, the present invention includes compounds of formula (I), supra, in which A is A3 wherein R$^6$ and R$^{10}$, together with three carbon atoms of the phenyl ring, two carbon atoms of the indole moiety and the nitrogen atom to which R$^6$ is attached, form a 9- to 16-membered ring and * is the point of attachment of these moieties to the indole carbon atom bearing the A substituent;

In yet other embodiments, the present invention includes compounds of formula (I), supra, in which A is A3 wherein R$^6$ and R$^{10}$, together with three carbon atoms of the phenyl ring, two carbon atoms of the indole moiety and the nitrogen atom to which R$^6$ is attached, form a 11- to 16-membered ring and * is the point of attachment of these moieties to the indole carbon atom bearing the A substituent;

In yet other embodiments, the present invention includes compounds of formula (I), supra, in which A is A3 wherein $R^6$ and $R^{10}$, together with three carbon atoms of the phenyl ring, two carbon atoms of the indole moiety and the nitrogen atom to which $R^6$ is attached, form a 12-membered ring and * is the point of attachment of these moieties to the indole carbon atom bearing the A substituent;

In further embodiments, the present invention includes compounds of formula (I), supra, in which A is A1 or A2, or a tautomer, an N-oxide, or a salt thereof or a salt of a tautomer or a N-oxide or a mixture of same.

In other embodiments, the present invention includes compounds of formula (I), supra, in which A is A1 or A2 and the macrocyclic ring is a 9- membered-, a 10-membered-, a 11-membered-, a 12-membered-, a 13-membered-, a 14-membered-, a 15-membered- or a 16-membered ring, particularly a 9- to 12-membered ring or a 12- or a 13-membered ring, more particularly a 10- to 11-membered ring, or a tautomer, an N-oxide, or a salt thereof or a salt of a tautomer or a N-oxide or a mixture of same.

In other embodiments, the present invention includes compounds of formula (I), supra, in which A is A1 or A2, which together with the indole moiety and the $R^6$-$R^7$ form a 9- membered-, a 10-membered-, a 11-membered- or a 12-membered macrocyclic ring or a tautomer, an N-oxide, or a salt thereof or a salt of a tautomer or a N-oxide or a mixture of same.

In yet other embodiments, the present invention includes compounds of formula (I), supra, in which A is A1, which together with the indole moiety and the $R^6$-$R^7$ form a 9- membered-, a 10-membered-, a 11-membered- or a 12-membered macrocyclic ring or a tautomer, an N-oxide, or a salt thereof or a salt of a tautomer or a N-oxide or a mixture of same.

In yet other embodiments, the present invention includes compounds of formula (I), supra, in which A is A2, which together with the indole moiety and the $R^6$-$R^7$ form a 9- membered-, a 10-membered-, a 11-membered- or a 12-membered macrocyclic ring or a tautomer, an N-oxide, or a salt thereof or a salt of a tautomer or a N-oxide or a mixture of same.

In yet other embodiments, the present invention includes compounds of formula (I), supra, in which A is A1 or A2, which together with the indole moiety and the $R^6$-$R^7$ form a 10-membered- or a 11-membered macrocyclic ring or a tautomer, an N-oxide, or a salt thereof or a salt of a tautomer or a N-oxide or a mixture of same.

In yet other embodiments, the present invention includes compounds of formula (I), supra, in which A is A1 or A2, which together with the indole moiety and the $R^6$-$R^7$ form a 11-membered macrocyclic ring or a tautomer, an N-oxide, or a salt thereof or a salt of a tautomer or a N-oxide or a mixture of same.

In yet other embodiments, the present invention includes compounds of formula (I), supra, in which A is A1 and $R^8$ and $R^9$ are $C_1$-$C_3$-alkyl, particularly methyl.

In still other embodiments, the present invention includes compounds of formula (I), supra, in which A is A2 and $R^8$ and $R^9$ are independently selected from $C_1$-$C_3$-alkyl, particularly from methyl or ethyl.

In further embodiments, the present invention includes compounds of formula (I), supra, in which A is A1 or A2 and $R^8$ and $R^9$ are independently selected from $C_1$-$C_3$-alkyl or a —($C_1$-$C_3$-alkyl)-heterocyclyl.

The integers selected for variables n, t, p, q, r, and v may result in different ring sizes but still the rings obtained have to fulfill the rule that only rings of a ring size of 9 members up to a ring size of 16 members are encompassed.

In further embodiments, the present invention includes compounds of formula (I), supra, in which n is 2, 3, 4, 5, 6;
t is 0 or 1;
p is 0, 1, or 2;
q is 2;
r is 2;
v is 0 or 1.

In further embodiments, the present invention includes compounds of formula (I), supra, in which n is 2, 3, 4, 5, 6;
t is 1;
p is 1;
q is 2;
r is 2;
v is 0 or 1.

The limitations relating to A1 and A2 are independent from the limitations relating to A3.

In further embodiments, the present invention includes compounds of formula (I), supra, in which $R^8$ is selected from a $C_1$-$C_6$-alkyl group, which is optionally substituted with one or more substituents independently selected from
  a halogen atom, a hydroxyl group, a $C_1$-$C_3$-alkoxy group, a $C_1$-$C_3$-haloalkoxy group, a $C_3$-$C_6$-cycloalkyl group, a heterocycloalkyl group, and a $NR^{21}R^{22}$ group; or
a $C_1$-$C_3$-haloalkyl group,
a $C_3$-$C_6$-cycloalkyl group and
a $C_1$-$C_6$-alkyl group in which one or two not directly adjacent carbon atoms are independently replaced by a hetero atom selected from —O— and —NH—, or a tautomer, an N-oxide, or a salt thereof or a salt of a tautomer or a N-oxide or a mixture of same.

In further embodiments, the present invention includes compounds of formula (I), supra, in which $R^8$ is selected from a $C_1$-$C_3$-alkyl group, which is optionally substituted with one or more substituents independently selected from
  a halogen atom, a hydroxyl group, a $C_1$-$C_3$-alkoxy group, a $C_1$-$C_3$-haloalkoxy group, a $C_3$-$C_6$-cycloalkyl group, a heterocycloalkyl group, and a $NR^{21}R^{22}$ group; or
a $C_1$-$C_3$-haloalkyl group,
a $C_3$-$C_6$-cycloalkyl group and
a $C_1$-$C_6$-alkyl group in which one or two not directly adjacent carbon atoms are independently replaced by a hetero atom selected from —O— or —NH—, or a tautomer, an N-oxide, or a salt thereof or a salt of a tautomer or a N-oxide or a mixture of same.

In further embodiments, the present invention includes compounds of formula (I), supra, in which $R^8$ is a $C_1$-$C_6$-alkyl group which is optionally substituted with one or more heterocycloalkyl groups or a tautomer, an N-oxide, or a salt thereof or a salt of a tautomer or a N-oxide or a mixture of same.

In further embodiments, the present invention includes compounds of formula (I), supra, in which $R^8$ is a $C_1$-$C_6$-alkyl group which is optionally substituted with a heterocycloalkyl group or a tautomer, an N-oxide, or a salt thereof or a salt of a tautomer or a N-oxide or a mixture of same.

In further embodiments, the present invention includes compounds of formula (I), supra, in which $R^8$ is selected from
a hydrogen atom,
a $C_1$-$C_3$-alkyl group, which is optionally substituted with one or more substituents independently selected from a halogen atom, a hydroxyl group, a $C_1$-$C_3$-alkoxy group, a $C_1$-$C_3$-haloalkoxy group, a $C_3$-$C_6$-cycloalkyl group, a heterocycloalkyl group, and a $NR^{21}R^{22}$ group;
a $C_1$-$C_3$-haloalkyl group,
a $C_3$-$C_6$-cycloalkyl group and
a $C_1$-$C_3$-alkyl group in which one or two not directly adjacent carbon atoms are independently replaced by a hetero atom selected from —O— and —NH—, or a tautomer, an N-oxide, or a salt thereof or a salt of a tautomer or a N-oxide or a mixture of same.

In further embodiments, the present invention includes compounds of formula (I), supra, in which $R^8$ is selected from
a hydrogen atom,
a $C_1$-$C_3$-alkyl group, which is substituted with one or more substituents independently selected from a halogen atom, a $C_1$-$C_3$-alkoxy group, a heterocycloalkyl group, and a $NR^{21}R^{22}$ group;
a $C_1$-$C_3$-haloalkyl group, and
a $C_3$-$C_6$-cycloalkyl group; or a tautomer, an N-oxide, or a salt thereof or a salt of a tautomer or a N-oxide or a mixture of same.

In further embodiments, the present invention includes compounds of formula (I), supra, in which $R^8$ is selected from
a $C_1$-$C_3$-alkyl group, which is optionally substituted with one or more substituents independently selected from
a halogen atom, a hydroxyl group, a $C_1$-$C_3$-alkoxy group, a heterocycloalkyl group, and a $NR^{21}R^{22}$ group;
a $C_1$-$C_3$-haloalkyl group,
a $C_3$-$C_6$-cycloalkyl group; and
a $C_1$-$C_3$-alkyl group in which one or two not directly adjacent carbon atoms are independently replaced by a hetero atom which is —O— or a tautomer, an N-oxide, or a salt thereof or a salt of a tautomer or a N-oxide or a mixture of same.

In further embodiments, the present invention includes compounds of formula (I), supra, in which $R^8$ is selected from methyl, ethyl, 1,1,1-trifluoroethyl, methoxyethyl, morpholino-ethyl, cyclopropyl, and N,N-dimethylaminoethyl or a tautomer, an N-oxide, or a tautomer, an N-oxide, or a salt thereof or a salt of a tautomer or a N-oxide or a mixture of same.

In further embodiments, the present invention includes compounds of formula (I), supra, in which $R^8$ is selected from a hydrogen atom, and a $C_1$-$C_6$-alkyl group, which is optionally substituted with hydroxy, $C_1$-$C_3$-alkoxy, $C_1$-$C_3$-haloalkoxy, $C_3$-$C_6$-cycloalkyl, heterocycloalkyl, $NR^{17}R^{18}$, or a $C_1$-$C_6$-alkyl group in which one or two not directly adjacent carbon atoms are independently replaced by a hetero atom selected from —O— or —NH— or a tautomer, an N-oxide, or a salt thereof or a salt of a tautomer or a N-oxide or a mixture of same.

In further embodiments, the present invention includes compounds of formula (I), supra, in which $R^8$ is selected from a hydrogen atom and a $C_1$-$C_6$-alkyl group, which is optionally substituted with one or more substituents selected from a hydroxyl group, a $C_1$-$C_3$-alkoxy group, and a heterocycloalkyl group, or a tautomer, an N-oxide, or a salt thereof or a salt of a tautomer or a N-oxide or a mixture of same.

In other embodiments, the present invention includes compounds of formula (I), supra, in which $R^8$ is a $C_1$-$C_3$-alkyl group, more particularly a methyl group, or a tautomer, an N-oxide, or a salt thereof or a salt of a tautomer or a N-oxide or a mixture of same.

In further embodiments, the present invention includes compounds of formula (I), supra, in which $R^8$ is an unsubstituted $C_1$-$C_6$-alkyl group, more specifically an unsubstituted $C_1$-$C_3$-alkyl group or a tautomer, an N-oxide, or a salt thereof or a salt of a tautomer or a N-oxide or a mixture of same.

In further embodiments, the present invention includes compounds of formula (I), supra, in which $R^8$ is a $C_1$-$C_3$-alkyl group substituted with one or more halogen atoms or stereoisomers, tautomers, N-oxides, and salts thereof, and mixtures of same.

In further embodiments, the present invention includes compounds of formula (I), supra, in which $R^8$ is a $C_1$-$C_3$-alkyl group substituted with one or more $C_1$-$C_3$-alkoxy groups or a tautomer, an N-oxide, or a salt thereof or a salt of a tautomer or a N-oxide or a mixture of same.

In further embodiments, the present invention includes compounds of formula (I), supra, in which $R^8$ is a $C_1$-$C_3$-alkyl group substituted with one or more heterocycloalkyl groups or a tautomer, an N-oxide, or a salt thereof or a salt of a tautomer or a N-oxide or a mixture of same.

In further embodiments, the present invention includes compounds of formula (I), supra, in which $R^8$ is a $C_1$-$C_3$-alkyl group substituted with a heterocycloalkyl group or a tautomer, an N-oxide, or a salt thereof or a salt of a tautomer or a N-oxide or a mixture of same.

In further embodiments, the present invention includes compounds of formula (I), supra, in which $R^8$ is a $C_1$-$C_3$-alkyl group substituted with a heterocycloalkyl group or a tautomer, an N-oxide, or a salt thereof or a salt of a tautomer or a N-oxide or a mixture of same.

In further embodiments, the present invention includes compounds of formula (I), supra, in which $R^8$ is a $C_1$-$C_3$-haloalkyl group or a tautomer, an N-oxide, or a salt thereof or a salt of a tautomer or a N-oxide or a mixture of same.

In further embodiments, the present invention includes compounds of formula (I), supra, in which $R^8$ is a $C_3$-$C_6$-cycloalkyl group or a tautomer, an N-oxide, or a salt thereof or a salt of a tautomer or a N-oxide or a mixture of same.

In further embodiments, the present invention includes compounds of formula (I), supra, in which $R^8$ is a $C_1$-$C_3$-alkyl group which is substituted with $NR^{21}R^{22}$ particularly —N(CH$_3$)$_2$ or a tautomer, an N-oxide, or a salt thereof or a salt of a tautomer or a N-oxide or a mixture of same.

In further embodiments, the present invention includes compounds of formula (I), supra, in which $R^9$ is a hydrogen atom,
a $C_1$-$C_4$-alkyl group,
a $C_1$-$C_3$-hydroxyalkyl group,
a $C_1$-$C_4$-haloalkyl group,
a $C_1$-$C_4$-haloalkyl-NH—C(O)—O—($C_1$-$C_3$-alkylene)- group,
a $C_2$-$C_6$-haloalkenyl group,
a $C_1$-$C_6$-alkyl-O-group,
a $C_1$-$C_4$-haloalkoxy group,
a $C_1$-$C_6$-alkyl-O—($C_1$-$C_3$-alkylene)- group,
a ($C_3$-$C_7$)-cycloalkyl group,
a ($C_3$-$C_7$)-cycloalkyl-O—($C_1$-$C_3$-alkylene)- group,
a phenyl-O—($C_1$-$C_3$-alkylene)- group,
a phenyl-($C_1$-$C_3$-alkylene)-O—($C_1$-$C_3$-alkylene)- group,
a $R^{19}$-phenyl-($C_1$-$C_3$-alkylene)-O—($C_1$-$C_3$-alkylene)- group, a R$^{19}$-phenylene-O—(C$_1$-C$_3$-alkylene)- group,
a R$^{19}$-phenyl-heteroaryl-O—(C$_1$-C$_3$-alkylene) group,
a (R$^{19}$)-(heterocycloalkyl)-(C$_1$-C$_3$-alkylene)- group,
a (R$^{19}$)-(heterocycloalkylene)-(phenylene)-O—(C$_1$-C$_3$-alkylene)- group,
a (heterocycloalkenylene)-(phenylene)-O—(C$_1$-C$_3$-alkylene)- group,
a (R$^{19}$)-(heteroaryl-(C$_1$-C$_3$-alkylene)-O—(C$_1$-C$_3$-alkylene)- group,
a (R$^{19}$)-(heteroaryl)-(phenylene)-O—(C$_1$-C$_3$-alkylene)- group,
a (R$^{20}$)—S(O)$_2$-(phenylene)-O—(C$_1$-C$_3$-alkylene)- group,
a (R$^{20}$)—S(O)$_2$—NH-(phenylene)-O—(C$_1$-C$_3$-alkylene)- group,
a (R$^{20}$)—S(O)$_2$—NH-(phenylene)-O—(C$_1$-C$_3$-alkylene)- group,
a (R$^{20}$)—S(O)$_2$—N(C$_1$-C$_6$-alkyl)-(phenylene)-O—(C$_1$-C$_3$-alkylene)- group,
a (R$^{20}$)—S(O)$_2$-(heterocycloalkylene)-(phenylene)-O—(C$_1$-C$_3$-alkylene)- group,
a (R$^{19}$)-(heterocycloalkylene)-(heteroarylene)-O—(C$_1$-C$_3$-alkylen)- group,
a (R$^{20}$)-(heteroarylene)-O—(C$_1$-C$_3$-alkylene)- group,
a (R$^{19}$)-(heteroarylene)-O—(C$_1$-C$_3$-alkylene)- group,
a (R$^{20}$)—S(O)$_2$-(heteroarylene)-O—(C$_1$-C$_3$-alkylene)- group,
a (R$^{20}$)—S(O)$_2$-(heterocycloalkylene)-(heteroarylene)-O—(C$_1$-C$_3$-alkylene)- group,
a NR$^{21}$R$^{22}$—(C$_1$-C$_3$-alkylene)- group,
a (C$_1$-C$_3$-alkyl)-NH—(C$_1$-C$_3$-alkylene)- group,
a (C$_1$-C$_3$-haloalkyl)-(C$_1$-C$_3$-alkylene)-NH—(C$_1$-C$_3$-alkylene)- group,
a (C$_1$-C$_3$-haloalkyl)-NH—(C$_1$-C$_3$-alkylene)- group,
a (C$_1$-C$_3$-alkyl)-NH—C(O)—(C$_1$-C$_3$-alkylene)- group,
a (C$_1$-C$_3$-alkyl)-NR$^{15}$—C(O)—(C$_1$-C$_3$-alkylene)- group,
a (C$_1$-C$_3$-alkyl)-C(O)—NH—(C$_1$-C$_3$-alkylene)- group,
a (C$_1$-C$_3$-alkyl)-C(O)—NR$^{15}$—(C$_1$-C$_3$-alkylene)- group,
a

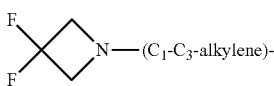

group or a

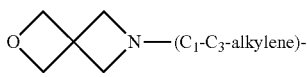

group, where the phenyl ring is optionally substituted with a halogen atom, a hydroxyl group, or a C$_1$-C$_3$-alkoxy group and
the heterocycloalkyl group is optionally substituted with an oxo (=O) group or is optionally substituted with one or more substituents independently selected from a halogen atom, and a C$_1$-C$_3$-alkyl group, or a tautomer, an N-oxide, or a salt thereof or a salt of a tautomer or a N-oxide or a mixture of same.

In further embodiments, the present invention includes compounds of formula (I), supra, in which R$^9$ is selected from a hydrogen atom,
a C$_1$-C$_4$-alkyl group,
a C$_1$-C$_3$-hydroxyalkyl group,
a C$_1$-C$_4$-haloalkyl group,
a C$_1$-C$_4$-haloalkyl-NH—C(O)—O—(C$_1$-C$_3$-alkylene)- group,
a C$_2$-C$_6$-haloalkenyl group,
a C$_1$-C$_6$-alkyl-O-group,
a C$_1$-C$_4$-haloalkoxy group,
a C$_1$-C$_6$-alkyl-O—(C$_1$-C$_3$-alkylene)- group,
a (C$_3$-C$_7$)-cycloalkyl group,
a (C$_3$-C$_7$-cycloalkyl)-O—(C$_1$-C$_3$-alkylene)- group,
a phenyl-O—(C$_1$-C$_3$-alkylene)- group,
a phenyl-(C$_1$-C$_3$-alkylene)-O—(C$_1$-C$_3$-alkylene)- group,
a (R$^{19}$)-(phenylene)-O—(C$_1$-C$_3$-alkylene)- group,
a (R$^{19}$)-(phenylene)-(C$_1$-C$_3$-alkylene)-O—(C$_1$-C$_3$-alkylene)- group,
a (R$^{19}$)-(phenylene)-(heteroarylene)-O—(C$_1$-C$_3$-alkylene) group,
a (R$^{19}$)-(heterocycloalkylene)-(C$_1$-C$_6$-alkylene)- group,
a (R$^{19}$)-(heterocycloalkylene)-(phenylene)-O—(C$_1$-C$_3$-alkylene)- group,
a (heterocycloalkenyl)-(phenylene)-O—(C$_1$-C$_3$-alkylene)- group,
a (R$^{19}$)-(heteroarylene)-(C$_1$-C$_3$-alkylene)-O—(C$_1$-C$_3$-alkylene)- group,
a (R$^{19}$)-(heteroarylene)-(phenylene)-O—(C$_1$-C$_3$-alkylene)- group,
a (R$^{19}$)-(phenylene)-(C$_1$-C$_3$-alkylene)-O—(C$_1$-C$_3$-alkylene)- group,
a (R$^{20}$)—S(O)$_2$-(phenylene)-O—(C$_1$-C$_3$-alkylene)- group,
a (R$^{20}$)—S(O)$_2$—NH-(phenylene)-O—(C$_1$-C$_3$-alkylene)- group,
a (R$^{20}$)—S(O)$_2$—N(C$_1$-C$_6$-alkyl)-(phenylene)-O—(C$_1$-C$_3$-alkylene)- group,
a (R$^{20}$)—S(O)$_2$-(heterocycloalkylene)-(phenylene)-O—(C$_1$-C$_3$-alkylene)- group,
a (R$^{19}$)-(heterocycloalkylene)-(heteroarylene)-O—(C$_1$-C$_3$-alkylene)- group,
a (R$^{20}$)-(heteroarylene)-O—(C$_1$-C$_3$-alkylene)- group,
a (R$^{20}$)—S(O)$_2$-(heteroarylene)-O—(C$_1$-C$_3$-alkylene)- group,
a (R$^{20}$)—S(O)$_2$-(heterocycloalkylene)-(heteroarylene)-O—(C$_1$-C$_3$-alkylene)- group,
a NR$^{21}$R$^{22}$—(C$_1$-C$_3$-alkylene)- group,
a (C$_1$-C$_3$-alkyl)-NH—(C$_1$-C$_3$-alkylene)- group,
a (C$_1$-C$_3$-haloalkyl)-(C$_1$-C$_3$-alkylene)-NH—(C$_1$-C$_3$-alkylene)- group,
a (C$_1$-C$_3$-haloalkyl)-NH—(C$_1$-C$_3$-alkylene)- group,
a (C$_1$-C$_3$-alkyl)-NH—C(O)—(C$_1$-C$_3$-alkylene)- group
a (C$_1$-C$_3$-alkyl)-NR$^{15}$—C(O)—(C$_1$-C$_3$-alkylene)- group
a (C$_1$-C$_3$-alkyl)-C(O)—NH—(C$_1$-C$_3$-alkylene)- group
a (C$_1$-C$_3$-alkyl)-C(O)—NR$^{15}$—(C$_1$-C$_3$-alkylene)- group,
a

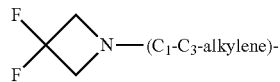

group, and a

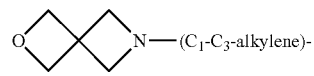

group,
   where the phenyl ring is optionally substituted with a halogen atom, a hydroxyl group, or a $C_1$-$C_3$-alkoxy group and
   the heterocycloalkyl group is optionally substituted with an oxo (=O) group or is optionally substituted with one or more substituents independently selected from a halogen atom, and a $C_1$-$C_3$-alkyl group;
or $R^8$ and $R^9$ together form a 5- or 6-membered ring optionally containing one or two heteroatoms selected from of —O—, and —$NR^{14}$—;
and where
$R^{19}$ is selected from a hydrogen atom, a hydroxyl group, a cyano group, a $C_1$-$C_3$-alkyl group, a $C_1$-$C_6$-hydroxyalkyl group, a $C_1$-$C_3$-alkoxy group, a $C(O)OR^{21}$—($C_1$-$C_3$-alkylene)- group, a —$C(O)OR^{21}$ group, a —$C(O)NR^{21}R^{22}$ group, a ($C_1$-$C_3$-alkyl)-O—($C_1$-$C_3$-alkylene)-C(O)— group, a ($C_1$-$C_6$-alkyl)-C(O)-group, and a $C_3$-$C_6$-cycloalkyl-C(O)— group and where $R^{19}$ is located at any position chemically possible;
where $R^{20}$ is selected from a $C_1$-$C_3$-alkyl group, a $C_3$-$C_6$-cycloalkyl group, and a $NR^{21}R^{22}$ group and where $R^{20}$ is located at any position chemically possible; and
where $R^{21}$, $R^{22}$ are independently selected from a hydrogen atom or a $C_1$-$C_6$-alkyl group;
or a tautomer, an N-oxide, or a salt thereof or a salt of a tautomer or a N-oxide or a mixture of same.

In further embodiments, the present invention includes compounds of formula (I), supra, in which $R^9$ is
a hydrogen atom,
a $C_1$-$C_4$-alkyl group,
a $C_1$-$C_3$-hydroxyalkyl group,
a $C_1$-$C_4$-haloalkyl group,
a $C_1$-$C_4$-haloalkyl-NH—C(O)—O—($C_1$-$C_3$-alkylene)- group,
a $C_2$-$C_6$-haloalkenyl group,
a $C_1$-$C_6$-alkyl-O— group,
a $C_1$-$C_4$-haloalkoxy group,
a $C_1$-$C_6$-alkyl-O—($C_1$-$C_3$-alkylene)- group,
a ($C_3$-$C_7$)-cycloalkyl group,
a ($C_3$-$C_7$)-cycloalkyl-O—($C_1$-$C_3$-alkylene)- group,
a phenyl-O—($C_1$-$C_3$-alkylene)- group,
a ($R^{19}$)-(phenylene)-($C_1$-$C_3$-alkylene)-O—($C_1$-$C_3$-alkylene)- group,
a ($R^{19}$)-(phenylene)-($C_1$-$C_3$-alkylene)-O—($C_1$-$C_3$-alkylene)- group,
a ($R^{19}$)-(phenylene)-O—($C_1$-$C_3$-alkylene)- group,
a ($R^{19}$)-(phenylene)-(heteroarylene)-O—($C_1$-$C_3$-alkylene)-group,
a ($R^{19}$)-(heterocycloalkylene)-($C_1$-$C_3$-alkylene)- group,
a ($R^{19}$)-(heterocycloalkylene)-(phenylene)-O—($C_1$-$C_3$-alkylene)- group,
a ($R^{19}$)-(heterocycloalkenylene)-(phenylene)-O—($C_1$-$C_3$-alkylene)- group,
a ($R^{19}$)-(heteroarylene)-($C_1$-$C_3$-alkylene)-O—($C_1$-$C_3$-alkylene)- group,
a ($R^{19}$)-(heteroarylene)-(phenylene)-O—($C_1$-$C_3$-alkylene)- group,
a ($R^{20}$)—$S(O)_2$-(phenylene)-O—($C_1$-$C_3$-alkylene)- group,
a ($R^{20}$)—$S(O)_2$—NH-(phenylene)-O—($C_1$-$C_3$-alkylene)-group,
a ($R^{20}$)—$S(O)_2$-(heterocycloalkylene)-(phenylene)-O—($C_1$-$C_3$-alkylene)- group,
a ($R^{19}$)-(heteroarylene)-O—($C_1$-$C_3$-alkylene)- group,
a $NR^{21}R^{22}$—($C_1$-$C_3$-alkylene)- group,
a ($C_1$-$C_3$-alkyl)-NH—($C_1$-$C_3$-alkylene)- group,
a ($C_1$-$C_3$-haloalkyl)-($C_1$-$C_3$-alkylene)-NH—($C_1$-$C_3$-alkylene)- group,
a ($C_1$-$C_3$-haloalkyl)-NH—($C_1$-$C_3$-alkylene)- group,
a ($C_1$-$C_3$-alkyl)-C(O)—NH—($C_1$-$C_3$-alkylene)- group,
a ($C_1$-$C_3$-alkyl)-C(O)—$NR^{15}$—($C_1$-$C_3$-alkylene)- group,
a group, or a group, where the phenyl ring is optionally substituted with a halogen atom, a hydroxyl group, or a $C_1$-$C_3$-alkoxy group and
the heterocycloalkyl group is optionally substituted with an oxo (=O) group or is optionally substituted with one or more substituents independently selected from a halogen atom, and a $C_1$-$C_3$-alkyl group, or a tautomer, an N-oxide, or a salt thereof or a salt of a tautomer or a N-oxide or a mixture of same.

In further embodiments, the present invention includes compounds of formula (I), supra, in which $R^9$ is
a hydrogen atom,
a $C_1$-$C_4$-alkyl group,
a $C_1$-$C_3$-hydroxyalkyl group,
a $C_1$-$C_4$-haloalkyl group,
a $C_2$-$C_6$-haloalkenyl group,
a ($C_3$-$C_7$)-cycloalkyl group
a ($C_3$-$C_7$)-cycloalkyl-O—($C_1$-$C_3$-alkylene)- group,
a (heterocycloalkyl)-($C_1$-$C_3$-alkylene)- group, or
a $NR^{21}R^{22}$—($C_1$-$C_3$-alkylene)- group,
the heterocycloalkyl group is optionally substituted with an oxo (=O) group or is optionally substituted with one or more substituents independently selected from a halogen atom, a $C_1$-$C_3$-alkyl group, or a tautomer, an N-oxide, or a salt thereof or a salt of a tautomer or a N-oxide or a mixture of same.

In further embodiments, the present invention includes compounds of formula (I), supra, in which $R^9$ is
a $C_1$-$C_6$-alkyl-O-group,
a $C_1$-$C_4$-haloalkoxy group,
a $C_1$-$C_6$-alkyl-O—($C_1$-$C_3$-alkylene)- group,
a ($C_3$-$C_7$)-cycloalkyl-O—($C_1$-$C_3$-alkylene)- group,
a phenyl-O—($C_1$-$C_3$-alkylene)- group,
a phenyl-($C_1$-$C_3$-alkylene)-O—($C_1$-$C_3$-alkylene)- group,
a $R^{19}$-phenyl-($C_1$-$C_3$-alkylene)-O—($C_1$-$C_3$-alkylene)-group,
a phenyl-(heteroarylene)-O—($C_1$-$C_3$-alkylene),
a ($R^{19}$)-(phenylene)-(heteroarylene)-O—($C_1$-$C_3$-alkylene),
a (heterocycloalkylene)-(phenylene)-O—($C_1$-$C_3$-alkylene)- group,
a (heterocycloalkenylene)-(phenylene)-O—($C_1$-$C_3$-alkylene)- group,
a ($R^{19}$)-(heterocycloalkylene)-(phenylene)-O—($C_1$-$C_3$-alkylene)- group,
a ($R^{19}$)-(heteroarylene)-($C_1$-$C_3$-alkylene)-O—($C_1$-$C_3$-alkylene)- group, a (R$^{19}$)-(heteroarylene)-(phenylene)-O—(C$_1$-C$_3$-alkylene)- group,
a (R$^{20}$)—S(O)$_2$-(phenylene)-O—(C$_1$-C$_3$-alkylene)- group,
a (R$^{20}$)—S(O)$_2$—NH-(phenylene)-O—(C$_1$-C$_3$-alkylene)- group,
a (R$^{20}$)—S(O)$_2$-(heterocycloalkylene)-(phenylene)-O—(C$_1$-C$_3$-alkylene)- group, or
a (R$^{20}$)-(heteroarylene)-O—(C$_1$-C$_3$-alkylene)- group,
where the phenyl ring is optionally substituted with halogen, hydroxy, or C$_1$-C$_3$-alkoxy and
the heterocycloalkyl group is optionally substituted with an oxo (=O) group or is optionally substituted with one or more substituents independently selected from a halogen atom, and a C$_1$-C$_3$-alkyl group, or a tautomer, an N-oxide, or a salt thereof or a salt of a tautomer or a N-oxide or a mixture of same.

In further embodiments, the present invention includes compounds of formula (I), supra, in which R$^9$ is
C$_1$-C$_4$-haloalkyl-NH—C(O)—O—(C$_1$-C$_3$-alkylene)- group,
a (C$_1$-C$_3$-haloalkyl)-NH—(C$_1$-C$_3$-alkylene)- group,
a (C$_1$-C$_3$-alkyl)-NH—C(O)—(C$_1$-C$_3$-alkylene)- group,
a (C$_1$-C$_3$-alkyl)-NR$^{15}$—C(O)—(C$_1$-C$_3$-alkylene)- group,
a (C$_1$-C$_3$-alkyl)-C(O)—NH—(C$_1$-C$_3$-alkylene)- group,
a (C$_1$-C$_3$-alkyl)-C(O)—NR$^{15}$—(C$_1$-C$_3$-alkylene)- group,
a (R$^{20}$)—S(O)$_2$—NH-(phenylene)-O—(C$_1$-C$_3$-alkylene)- group,
a NR$^{21}$R$^{22}$—(C$_1$-C$_3$-alkylene)- group,
a (C$_1$-C$_3$-alkyl)-NH—(C$_1$-C$_3$-alkylene)- group,
a (C$_1$-C$_3$-haloalkyl)-(C$_1$-C$_3$-alkylene)-NH—(C$_1$-C$_3$-alkylene)- group
a

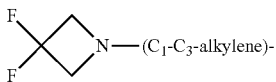

group, or a

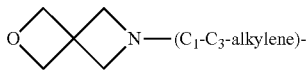

group, where the phenyl ring is optionally substituted with a halogen atom, a hydroxyl group, or a C$_1$-C$_3$-alkoxy group and
the heterocycloalkyl group is optionally substituted with an oxo (=O) group or is optionally substituted with one or more substituents independently selected from a halogen atom, and a C$_1$-C$_3$-alkyl group, or a tautomer, an N-oxide, or a salt thereof or a salt of a tautomer or a N-oxide or a mixture of same.

In further embodiments, the present invention includes compounds of formula (I), supra, in which R$^9$ is
a (heterocycloalkyl)-(C$_1$-C$_3$-alkylene)- group,
a (heterocycloalkylene)-(phenylene)-O—(C$_1$-C$_3$-alkylene)- group,
a (heterocycloalkenylene)-(phenylene)-O—(C$_1$-C$_3$-alkylene)- group,
a (R$^{19}$)-(heterocycloalkylene)-(phenylene)-O—(C$_1$-C$_3$-alkylene)- group,
a (R$^{19}$)-(heteroaryl-(C$_1$-C$_3$-alkylene)-O—(C$_1$-C$_3$-alkylene)- group,
a (R$^{19}$)-(heteroaryl)-(phenylene)-O—(C$_1$-C$_3$-alkylene)- group,
a (R$^{20}$)—S(O)$_2$-(heterocycloalkylene)-(phenylene)-O—(C$_1$-C$_3$-alkylene)- group, or
a (R$^{20}$)-(heteroarylene)-O—(C$_1$-C$_3$-alkylene)- group,
where the phenyl ring is optionally substituted with a halogen atom, a hydroxyl group, or a C$_1$-C$_3$-alkoxy group and
the heterocycloalkyl group is optionally substituted with an oxo (=O) group or is optionally substituted with one or more substituents independently selected from a halogen atom, and a C$_1$-C$_3$-alkyl group, or a tautomer, an N-oxide, or a salt thereof or a salt of a tautomer or a N-oxide or a mixture of same.

In further embodiments, the present invention includes compounds of formula (I), supra, in which R$^9$ is
a (heterocycloalkyl)-(C$_1$-C$_3$-alkylene)- group,
a (heterocycloalkyl)-(phenylene)-O—(C$_1$-C$_3$-alkylene)- group,
a (heterocycloalkenyl)-(phenylene)-O—(C$_1$-C$_3$-alkylene)- group,
a (R$^{19}$)-(heterocycloalkylene)-(phenylene)-O—(C$_1$-C$_3$-alkylene)- group, or
a (R$^{20}$)—S(O)$_2$-(heterocycloalkylene)-(phenylene)-O—(C$_1$-C$_3$-alkylene)- group,
where the phenyl ring is optionally substituted with a halogen atom, a hydroxyl group, or a C$_1$-C$_3$-alkoxy group and
the heterocycloalkyl group is optionally substituted with an oxo (=O) group or is optionally substituted with one or more substituents independently selected from a halogen atom, and a C$_1$-C$_3$-alkyl group, or a tautomer, an N-oxide, or a salt thereof or a salt of a tautomer or a N-oxide or a mixture of same.

In further embodiments, the present invention includes compounds of formula (I), supra, in which R$^9$ is
a (R$^{19}$)-(heteroaryl-(C$_1$-C$_3$-alkylene)-O—(C$_1$-C$_3$-alkylene)- group,
a (R$^{19}$)-(heteroaryl)-(phenylene)-O—(C$_1$-C$_3$-alkylene)- group, or
a (R$^{20}$)-(heteroarylene)-O—(C$_1$-C$_3$-alkylene)- group,
where the phenyl ring is optionally substituted with a halogen atom, a hydroxyl group, or a C$_1$-C$_3$-alkoxy group and
the heterocycloalkyl group is optionally substituted with an oxo (=O) group or is optionally substituted with one or more substituents independently selected from a halogen atom, and a C$_1$-C$_3$-alkyl group, or a tautomer, an N-oxide, or a salt thereof or a salt of a tautomer or a N-oxide or a mixture of same.

In further embodiments, the present invention includes compounds of formula (I), supra, in which R$^9$ is
a phenyl-O—(C$_1$-C$_3$-alkylene)- group,
a phenyl-(C$_1$-C$_3$-alkylene)-O—(C$_1$-C$_3$-alkylene)- group,
a R$^{19}$-(phenylene)-(C$_1$-C$_3$-alkylene)-O—(C$_1$-C$_3$-alkylene)- group,
a phenyl-(heteroarylene)-O—(C$_1$-C$_3$-alkylene),
a (R$^{19}$)-(phenylene)-(heteroarylene)-O—(C$_1$-C$_3$-alkylene),
a (heterocycloalkylene)-(phenylene)-O—(C$_1$-C$_3$-alkylene)- group,
a (heterocycloalkenylene)-(phenylene)-O—(C$_1$-C$_3$-alkylene)- group,
a (R$^{19}$)-(heterocycloalkylene)-(phenylene)-O—(C$_1$-C$_3$-alkylene)- group,
a (R$^{19}$)-(heteroarylene)-(phenylene)-O—(C$_1$-C$_3$-alkylene)- group,
a (R$^{20}$)—S(O)$_2$-(phenylene)-O—(C$_1$-C$_3$-alkylene)- group,
a (R$^{20}$)—S(O)$_2$—NH-(phenylene)-O—(C$_1$-C$_3$-alkylene)- group, or a (R$^{20}$)—S(O)$_2$-(heterocycloalkylene)-(phenylene)-O—(C$_1$-C$_3$-alkylene)- group,
where the phenyl ring is optionally substituted with a halogen atom, a hydroxyl group, or a C$_1$-C$_3$-alkoxy group and
the heterocycloalkyl group is optionally substituted with an oxo (=O) group or is optionally substituted with one or more substituents independently selected from a halogen atom, and a C$_1$-C$_3$-alkyl group, or a tautomer, an N-oxide, or a salt thereof or a salt of a tautomer or a N-oxide or a mixture of same.

In further embodiments, the present invention includes compounds of formula (I), supra, in which R$^9$ is
a C$_1$-C$_4$-alkyl group,
a C$_1$-C$_4$-haloalkyl group,
a C$_1$-C$_6$-alkyl-O-group,
a C$_1$-C$_6$-alkyl-O—(C$_1$-C$_3$-alkylene)- group,
a (C$_3$-C$_7$)-cycloalkyl group,
a phenyl-O—(C$_1$-C$_3$-alkylene)- group,
a R$^{19}$-(phenylene)-(C$_1$-C$_3$-alkylene)-O—(C$_1$-C$_3$-alkylene)- group,
a (heterocycloalkyl)-(C$_1$-C$_3$-alkylene)- group, or
a (R$^{19}$)-(heterocycloalkylene)-(phenylene)-O—(C$_1$-C$_3$-alkylene)- group,
or a tautomer, an N-oxide, or a salt thereof or a salt of a tautomer or a N-oxide or a mixture of same.

In further embodiments, the present invention includes compounds of formula (I), supra, in which R$^9$ is selected from a hydrogen atom, a C$_1$-C$_3$-alkyl group, a C$_1$-C$_3$-hydroxyalkyl group, a C$_1$-C$_6$-alkyl-O—(C$_1$-C$_3$-alkylene)- group, a phenyl-O—(C$_1$-C$_3$-alkylene)- group, a phenyl-(C$_1$-C$_3$-alkylene)-O—(C$_1$-C$_3$-alkylene)- group, a (heterocycloalkyl)-(C$_1$-C$_3$-alkylene)- group, a (R$^{19}$)-(heterocycloalkylene)-(phenylene)-O—(C$_1$-C$_3$-alkylene)- group, a (R$^{20}$)—S(O)$_2$-phenylene-O—(C$_1$-C$_3$-alkylene)- group, a (R$^{20}$)—S(O)$_2$-(heterocycloalkylene)-(phenylene)-O—(C$_1$-C$_3$-alkylene)- group, and a phenyl-(heteroarylene)-O—(C$_1$-C$_3$-alkylene)- group, where the phenyl ring is optionally substituted with a hydroxyl group or a C$_1$-C$_3$-alkoxy group, or a tautomer, an N-oxide, or a salt thereof or a salt of a tautomer or a N-oxide or a mixture of same.

In further embodiments, the present invention includes compounds of formula (I), supra, in which R$^9$ is selected from a C$_1$-C$_3$-alkyl group, a C$_1$-C$_6$-alkyl-O—(C$_1$-C$_3$-alkylene)- group, a phenyl-O—(C$_1$-C$_3$-alkylene)- group, a phenyl-(C$_1$-C$_3$-alkylene)-O—(C$_1$-C$_3$-alkylene)- group, a (R$^{19}$)-(heterocycloalkylene)-(phenylene)-O—(C$_1$-C$_3$-alkylen)- group, a (R$^{20}$)—S(O)$_2$-phenylene-O—(C$_1$-C$_3$-alkylene)- group and a (R$^{20}$)—S(O)$_2$-(heterocycloalkylene)-(phenylene)-O—(C$_1$-C$_3$-alkylene)- group, where the phenyl ring is optionally substituted with a hydroxyl group or a C$_1$-C$_3$-alkoxy group, or a tautomer, an N-oxide, or a salt thereof or a salt of a tautomer or a N-oxide or a mixture of same.

In further embodiments, the present invention includes compounds of formula (I), supra, in which R$^9$ is selected from a heterocycloalkenyl-(phenylene)-O—(C$_1$-C$_3$-alkylene) group, a (R$^{19}$)-(heteroarylene)-(phenylene)-O—(C$_1$-C$_3$-alkylene)- group, In other embodiments, the present invention includes compounds of formula (I), supra, in which R$^9$ is selected from a (R$^{20}$)—S(O)$_2$-(phenylene)-O—(C$_1$-C$_3$-alkylene)- group and a (R$^{20}$)—S(O)$_2$— (heterocycloalkylene)-(phenylene)-O—(C$_1$-C$_3$-alkylene)- group, where the phenyl ring is optionally substituted with a hydroxyl group or a C$_1$-C$_3$-alkoxy group, or a tautomer, an N-oxide, or a salt thereof or a salt of a tautomer or a N-oxide or a mixture of same.

In further embodiments, the present invention includes compounds of formula (I), supra, in which R$^9$ is selected from a hydrogen atom, a C$_1$-C$_3$-alkyl group, a C$_1$-C$_3$-hydroxyalkyl group, a C$_1$-C$_6$-alkyl-O—(C$_1$-C$_3$-alkylene)- group, a phenyl-O—(C$_1$-C$_3$-alkylene)- group, a phenyl-(C$_1$-C$_3$-alkylene)-O—(C$_1$-C$_3$-alkylene)- group, a (heterocycloalkyl)-(C$_1$-C$_3$-alkylene)- group, a (R$^{19}$)-(heterocycloalkylene)-(phenylene)-O—(C$_1$-C$_3$-alkylene)- group, a (R$^{20}$)—S(O)$_2$-(phenylene)-O—(C$_1$-C$_3$-alkylene)- group, a (R$^{20}$)—S(O)$_2$-(heterocycloalkylene)-(phenylene)-O—(C$_1$-C$_3$-alkylene)- group, and a phenyl-(heteroarylene)-O—(C$_1$-C$_3$-alkylene)- group, wherein the phenyl ring is optionally substituted with a hydroxyl group or a C$_1$-C$_3$-alkoxy group, or a tautomer, an N-oxide, or a salt thereof or a salt of a tautomer or a N-oxide or a mixture of same.

In further embodiments, the present invention includes compounds of formula (I), supra, in which R$^9$ is selected from a hydrogen atom, a C$_1$-C$_3$-alkyl group, a C$_1$-C$_3$-hydroxyalkyl group, a C$_1$-C$_6$-alkyl-O—(C$_1$-C$_3$-alkylene)- group, a phenyl-O—(C$_1$-C$_3$-alkylene)- group, a phenyl-(C$_1$-C$_3$-alkylene)-O—(C$_1$-C$_3$-alkylene)- group, a (heterocycloalkyl)-(C$_1$-C$_3$-alkylene)- group, a (R$^{19}$)-(heterocycloalkylene)-(phenylene)-O—(C$_1$-C$_3$-alkylene)- group, a heteroarylene-phenylene-O—(C$_1$-C$_3$-alkylene) group, a (R$^{20}$)—S(O)$_2$-(phenylene)-O—(C$_1$-C$_3$-alkylene)- group, a (R$^{20}$)—S(O)$_2$— (heterocycloalkylene)-(phenylene)-O—(C$_1$-C$_3$-alkylene)- group, a (heterocycloalkenyl)-(phenylene)-O—(C$_1$-C$_3$-alkylene)- group, and a phenyl-(heteroarylene)-O—(C$_1$-C$_3$-alkylene)- group, wherein the phenyl ring is optionally substituted with a hydroxyl group or a C$_1$-C$_3$-alkoxy group, or a tautomer, an N-oxide, or a salt thereof or a salt of a tautomer or a N-oxide or a mixture of same.

In further embodiments, the present invention includes compounds of formula (I), supra, in which R$^9$ is selected from a C$_1$-C$_3$-alkyl group, a C$_1$-C$_3$-hydroxyalkyl group, a C$_1$-C$_6$-alkyl-O—(C$_1$-C$_3$-alkylene)- group, a phenyl-O—(C$_1$-C$_3$-alkylene)- group, a phenyl-(C$_1$-C$_3$-alkylene)-O—(C$_1$-C$_3$-alkylene)- group, a (heterocycloalkyl)-(C$_1$-C$_3$-alkylene)- group, a (R$^{19}$)-(heterocycloalkylene)-(phenylene)-O—(C$_1$-C$_3$-alkylene)- group, and a phenyl-(heteroarylene)-O—(C$_1$-C$_3$-alkylene)- group, where the phenyl ring is optionally substituted with a hydroxyl group or a C$_1$-C$_3$-alkoxy group, or a tautomer, an N-oxide, or a salt thereof or a salt of a tautomer or a N-oxide or a mixture of same.

In further embodiments, the present invention includes compounds of formula (I), supra, in which R$^9$ is selected from a hydrogen atom, a C$_1$-C$_3$-alkyl group, a C$_1$-C$_3$-hydroxyalkyl group, a C$_1$-C$_6$-alkyl-O—(C$_1$-C$_3$-alkylene)- group, a phenyl-O—(C$_1$-C$_3$-alkylene)- group, a phenyl-(C$_1$-C$_3$-alkylene)-O—(C$_1$-C$_3$-alkylene)- group, a (heterocycloalkyl)-(C$_1$-C$_3$-alkylene)- group, a (R$^{19}$)-(heterocycloalkylene)-(phenylene)-O—(C$_1$-C$_3$-alkylene)- group, a (R$^{20}$)—S(O)$_2$— (phenylene)-O—(C$_1$-C$_3$-alkylene)- group, and a phenyl-(heteroarylene)-O—(C$_1$-C$_3$-alkylene)- group, where the phenyl ring is optionally substituted with a hydroxyl group or a C$_1$-C$_3$-alkoxy group, or a tautomer, an N-oxide, or a salt thereof or a salt of a tautomer or a N-oxide or a mixture of same.

In further embodiments, the present invention includes compounds of formula (I), supra, in which R$^9$ is a (R$^{19}$)-(heterocycloalkylene)-(phenylene)-O—(C$_1$-C$_3$-alkylene)- group, where the phenyl ring is optionally substituted with a hydroxyl group or a C$_1$-C$_3$-alkoxy group, or a tautomer, an N-oxide, or a salt thereof or a salt of a tautomer or a N-oxide or a mixture of same.

In further embodiments, the present invention includes compounds of formula (I), supra, in which $R^9$ is any $R^9$ residue as exemplified in the example section, selected from a hydrogen atom, a $CH_3$ group, a ethyl group, a n-propyl group, a isopropyl group(, a trifluormethyl group, a —$OCH_3$ group, a difluormethoxy- group, a —$CH_2$—OH group, a (piperidin-1-yl)methylene group, a (2-oxopiperidin-1-yl)methyl- group, a (2-oxopyrrolidin-1-yl)methyl- group, a (pyrrolidin-1-yl)methyl-group, a pyrimidin-5-yloxy)methyl- group, a 1-methyl-1H-imidazol-2-yl)methoxy]methyl- group, a $CH_3$—O—$CH_2$— group, a $CH_3$—$CH_2$—O—$CH_2$— group, a $(CH_3)_2$—CH—O—$CH_2$— group, a cyclopropyloxymethyl- group, a phenyl-O—$CH_2$— group, a phenyl-$CH_2$—O—$CH_2$— group, a 2,2,2-trifluoroethyl) carbamoyl]oxy}methyl- group, a 4-carbamoylbenzyl)oxy] methyl- group, a 4-cyoano-benzyloxymethyl- group, a methoxy-phenyl-$CH_2$—O—$CH_2$— group, a methoxyphenoxymethyl- group, a [4-(tetrahydro-2H-pyran-4-yl)phenoxy]methyl- group, a methylpiperazin-methyl- group, a 3-(3,3-difluoroazetidin-1-yl)methylene- group, a 3-oxomorpholin-4-yl)methyl- group, 7, a [4-(3,6-dihydro-2H-pyran-4-yl)phenoxy]methyl- group, a [4-(4-hydroxytetrahydro-2H-pyran-4-yl)phenoxy]methyl- group, a [4-(4-methoxytetrahydro-2H-pyran-4-yl)phenoxy]methyl- group, a (morpholin-4-yl)-$CH_2$— group,

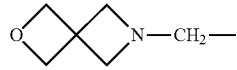

group, a a [4-(morpholin-4-yl)phenoxy]methyl- group, a [4-(2-oxopyridin-1(2H)-yl)phenoxy]methyl- group, a {4-[4-(N,N-dimethylsulfamoyl)piperazin-1-yl]phenoxy}methyl- group, a methylsulfonamido-phenoxymethyl- group, a {4-[4-(N,N-diethylsulfamoyl)piperazin-1-yl]phenoxy}methyl- group, a {4-[4-(cyclopropylsulfonyl)piperazin-1-yl] phenoxy}methyl- group, a {4-[4-(methylsulfonyl)piperazin-1-yl]phenoxy}methyl- group, a 4-(methylsulfonyl)phenoxy] methyl-group, a [4-(piperazin-1-yl)phenoxy]methyl- group, a [4-(4-methylpiperazin-1-yl)phenoxy]methyl-group, a 4-[4-(3-hydroxy-3-methylbutyl)piperazin-1-yl] phenoxy}methyl- group, a 4-[4-(carboxymethyl)piperazin-1-yl]phenoxy}methyl- group, a [4-(4-acetylpiperazin-1-yl) phenoxy]methyl- group, a 4-[4-(cyclopropylcarbonyl) piperazin-1-yl]phenoxy}methyl- group, a -{4-[4-(methoxyacetyl)piperazin-1-yl]phenoxy}methyl- group, a {4-[4-(tert-butoxycarbonyl)piperazin-1-yl] phenoxy}methyl- group, and a ({[2-(2-methoxyphenyl)pyrimidin-5-yl]oxy}methyl)- group, or stereoisomers, tautomers, N-oxides, and salts thereof, and mixtures of same.

In further embodiments, the present invention includes compounds of formula (I), supra, in which $R^9$ is selected from a hydrogen atom, a $C_1$-$C_3$-alkyl group, a $CH_3$—$CH_2$— group, a $CH_3$—$CH_2$—$CH_2$— group, a $(CH_3)_2$—$CH_2$— group, a —$CH_2$—OH group, a trifluoromethyl group, a 2,2-difluoroethyl group, a 2-fluoroethenyl group, a methoxy group, a difluoromethoxy group, a $CH_3$—O—$CH_2$— group, a $CH_3$—$CH_2$—O—$CH_2$— group, a $(CH_3)_2$—CH—O—$CH_2$— group, a cyclopropyl group, a cyclopropyloxymethyl- group, a phenyl-O—$CH_2$— group, a phenyl-$CH_2$—O—$CH_2$— group, a methoxy-phenoxy-methyl- group, a [(4-cyanobenzyl)oxy]methyl group, a [4-(tetrahydro-2H-pyran-4-yl)phenoxy]methyl- group, a [4-(3,6-dihydro-2H-pyran-4-yl)phenoxy]methyl- group, a [4-(4-hydroxytetrahydro-2H-pyran-4-yl)phenoxy]methyl- group, a [4-(4-methoxytetrahydro-2H-pyran-4-yl)phenoxy]methyl- group, a (morpholin-4-yl)-$CH_2$— group, a [4-(morpholin-4-yl)phenoxy]methyl- group, a methyl-piperazin-methyl- group, a piperidin-1-ylmethyl- group, a (2-oxopiperidin-1-yl)methyl- group, a pyrrolidin-1-yl-methyl- group, a (2-oxopyrrolidin-1-yl)methyl-group, a 4-(2-oxopyridin-1(2H)-yl)phenoxy] methyl- group, a {4-[4-(N,N-dimethylsulfamoyl)piperazin-1-yl]phenoxy}methyl- group, a (methylsulfonyl)amino] phenoxy}methyl- group, a {4-[4-(N,N-diethylsulfamoyl) piperazin-1-yl]phenoxy}methyl- group, a {4-[4-(cyclopropylsulfonyl)piperazin-1-yl]phenoxy}methyl- group, a {4-[4-(methylsulfonyl)piperazin-1-yl] phenoxy}methyl- group, a 4-(methylsulfonyl)phenoxy] methyl- group, a [4-(piperazin-1-yl)phenoxy]methyl- group, a [4-(4-methylpiperazin-1-yl)phenoxy]methyl- group, a 4-[4-(3-hydroxy-3-methylbutyl)piperazin-1-yl] phenoxy}methyl- group, a 4-[4-(carboxymethyl)piperazin-1-yl]phenoxy}methyl- group, a [4-(4-acetylpiperazin-1-yl) phenoxy]methyl- group, a 4-[4-(cyclopropylcarbonyl) piperazin-1-yl]phenoxy}methyl- group, a -{4-[4-(methoxyacetyl)piperazin-1-yl]phenoxy}methyl- group, a {4-[4-(tert-butoxycarbonyl)piperazin-1-yl] phenoxy}methyl- group, a (pyrimidin-5-yloxy)methyl- group, a ({[2-(2-methoxyphenyl)pyrimidin-5-yl] oxy}methyl)- group, a [(1-methyl-1H-imidazol-2-yl) methoxy]methyl- group, an aminomethyl- group, a ethylaminomethyl- group, a trifluoromethyl)aminomethyl-group, a (2,2, -difluoroethyl)aminomethyl- group, a (2,2,2-trifluoroethyl)aminomethyl- group, a {[(2,2,2-trifluoroethyl) carbamoyl]oxy}methyl- group, a [(carbamoylbenzyl)oxy] methyl- group, a acetylamino-methyl- group, a acetyl (methyl)amino]methyl- group, a

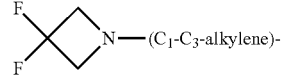

group, and
a

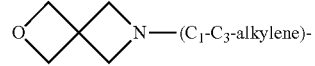

group,
or $R^8$ and $R^9$ together form a 6-membered ring optionally containing one or two oxygen atoms; or stereoisomers, tautomers, N-oxides, and salts thereof, and mixtures of same.

In further embodiments, the present invention includes compounds of formula (I), supra, in which $R^9$ is selected from a hydrogen atom, a $CH_3$ group, a ethyl group, a n-propyl group, a isopropyl group, a trifluormethyl group, a —$OCH_3$ group, a difluormethoxy- group, a —$CH_2$—OH group, a (piperidin-1-yl)methyl- group, a (2-oxopiperidin-1-yl)methyl- group, a (2-oxopyrrolidin-1-yl)methyl- group, a (pyrrolidin-1-yl)methyl- group, a pyrimidin-5-yloxy) methyl- group, a 1-methyl-1H-imidazol-2-yl)methoxy] methyl- group, a $CH_3$—O—$CH_2$— group, a $CH_3$—$CH_2$—O—$CH_2$— group, a cyclopropyloxymethyl- group, a 2,2,2-trifluoroethyl)carbamoyl]oxy}methyl- group, a 4-carbamoylbenzyl)oxy]methyl- group, a 4-cyoano-benzyloxymethyl- group, a methoxy-phenyl-$CH_2$—O—$CH_2$— group, a methoxyphenoxymethyl- group, a [4-(tetrahydro-2H-pyran-4-yl)phenoxy]methyl- group, a methylpiperazinmethyl- group, a 3-(3,3-difluoroazetidin-1-yl)methylene-group, a 3-oxomorpholin-4-yl)methyl- group, 7, a [4-(3,6-dihydro-2H-pyran-4-yl)phenoxy]methyl- group, a [4-(4-hydroxytetrahydro-2H-pyran-4-yl)phenoxy]methyl- group, a [4-(4-methoxytetrahydro-2H-pyran-4-yl)phenoxy]methyl-group, a (morpholin-4-yl)-$CH_2$— group,

group, a [4-(morpholin-4-yl)phenoxy]methyl- group, a methylsulfonamido-phenoxymethyl- group, and a pyrimidin-5-yl]oxy}methyl)- group, or a tautomer, an N-oxide, or a salt thereof or a salt of a tautomer or a N-oxide or a mixture of same.

In further embodiments, the present invention includes compounds of formula (I), supra, in which $R^9$ is selected from a hydrogen atom, a $CH_3$ group, a —$CH_2$—OH group, a $CH_3$—O—$CH_2$— group, a $(CH_3)_2$—CH—O—$CH_2$— group, a phenyl-O—$CH_2$— group, a phenyl-$CH_2$—O—$CH_2$— group, a [4-(tetrahydro-2H-pyran-4-yl)phenoxy]methyl- group, a [4-(3,6-dihydro-2H-pyran-4-yl)phenoxy]methyl- group, a [4-(4-hydroxytetrahydro-2H-pyran-4-yl)phenoxy]methyl- group, a [4-(4-methoxytetrahydro-2H-pyran-4-yl)phenoxy]methyl- group, a (morpholin-4-yl)-$CH_2$— group, a [4-(morpholin-4-yl)phenoxy]methyl-group, a [4-(2-oxopyridin-1(2H)-yl)phenoxy]methyl- group, a {4-[4-(N,N-dimethylsulfamoyl)piperazin-1-yl]phenoxy}methyl- group, a {4-[4-(N,N-diethylsulfamoyl)piperazin-1-yl]phenoxy}methyl- group, a {4-[4-(cyclopropylsulfonyl)piperazin-1-yl]phenoxy}methyl- group, a {4-[4-(methylsulfonyl)piperazin-1-yl]phenoxy}methyl- group, a 4-(methylsulfonyl)phenoxy]methyl- group, a [4-(piperazin-1-yl)phenoxy]methyl- group, a [4-(4-methylpiperazin-1-yl)phenoxy]methyl- group, a 4-[4-(3-hydroxy-3-methylbutyl)piperazin-1-yl]phenoxy}methyl- group, a 4-[4-(carboxymethyl)piperazin-1-yl]phenoxy}methyl- group, a [4-(4-acetylpiperazin-1-yl)phenoxy]methyl- group, a 4-[4-(cyclopropylcarbonyl)piperazin-1-yl]phenoxy}methyl-group, a -{4-[4-(methoxyacetyl)piperazin-1-yl]phenoxy}methyl- group, a {4-[4-(tert-butoxycarbonyl)piperazin-1-yl]phenoxy}methyl- group, and a ({[2-(2-methoxyphenyl)pyrimidin-5-yl]oxy}methyl)- group, or a tautomer, an N-oxide, or a salt thereof or a salt of a tautomer or a N-oxide or a mixture of same.

In further embodiments, the present invention includes compounds of formula (I), supra, in which $R^9$ is selected from $R^9$ is selected from a hydrogen atom, a $C_1$-$C_3$-alkyl group, a —$CH_2$—OH group, a trifluoromethyl group, a 2,2-difluoroethyl group, a 2-fluoroethenyl group, a methoxy group, a difluoromethoxy group, a $CH_3$—O—$CH_2$— group, a $CH_3$—$CH_2$—O—$CH_2$— group, a $(CH_3)_2$—CH—O—$CH_2$— group, a cyclopropyl group, a cyclopropyloxymethyl- group, a phenyl-O—$CH_2$— group, a phenyl-$CH_2$—O—$CH_2$— group, a methoxy-phenoxy-methyl- group, a [(4-cyanobenzyl)oxy]methyl group, a [4-(tetrahydro-2H-pyran-4-yl)phenoxy]methyl- group, a [4-(3,6-dihydro-2H-pyran-4-yl)phenoxy]methyl- group, a [4-(4-hydroxytetrahydro-2H-pyran-4-yl)phenoxy]methyl- group, a [4-(4-methoxytetrahydro-2H-pyran-4-yl)phenoxy]methyl- group, a (morpholin-4-yl)-$CH_2$— group, a [4-(morpholin-4-yl)phenoxy]methyl- group, a piperidin-1-ylmethyl- group, a (2-oxopiperidin-1-yl)methyl- group, a pyrrolidin-1-yl-methyl- group, a (2-oxopyrrolidin-1-yl)methyl- group, a 4-(2-oxopyridin-1(2H)-yl)phenoxy]methyl- group, a (methylsulfonyl)amino]phenoxy}methyl- group, a 4-(methylsulfonyl)phenoxy]methyl- group, a (pyrimidin-5-yloxy) methyl- group, a ({[2-(2-methoxyphenyl)pyrimidin-5-yl]oxy}methyl)- group, a [(1-methyl-1H-imidazol-2-yl) methoxy]methyl- group, a aminomethyl- group, a ethylaminomethyl- group, a trifluoromethyl)aminomethyl-group, a (2,2,-difluoroethyl)aminomethyl- group, a (2,2,2-trifluoroethyl)aminomethyl- group, a {[(2,2,2-trifluoroethyl) carbamoyl]oxy}methyl- group, a [(carbamoylbenzyl)oxy] methyl- group, a acetylamino-methyl- group, a acetyl (methyl)amino]methyl- group, or a tautomer, an N-oxide, or a salt thereof or a salt of a tautomer or a N-oxide or a mixture of same.

In further embodiments, the present invention includes compounds of formula (I), supra, in which $R^9$ is selected from a hydrogen atom,
a $C_1$-$C_4$-alkyl group,
a $C_1$-$C_3$-hydroxyalkyl group,
a $C_1$-$C_4$-haloalkyl group, $C_1$-$C_4$-haloalkyl-NH—C(O)—O—($C_1$-$C_3$-alkylen)- group,
a $C_2$-$C_6$-haloalkenyl group,
a $C_1$-$C_6$-alkyl-O-group,
a $C_1$-$C_4$-haloalkoxy group,
a $C_1$-$C_6$-alkyl-O—($C_1$-$C_3$-alkylen)- group,
a ($C_3$-$C_7$)-cycloalkyl group
a ($C_3$-$C_7$)-cycloalkyl-O—($C_1$-$C_3$-alkylene)- group,
a phenyl-O—($C_1$-$C_3$-alkylene)- group,
a phenyl-($C_1$-$C_3$-alkylene)-O—($C_1$-$C_3$-alkylene)- group,
a $R^{19}$-phenyl-($C_1$-$C_3$-alkylene)-O—($C_1$-$C_3$-alkylene)- group,
a $R^{19}$-phenylene-O—($C_1$-$C_3$-alkylene)- group,
a $R^{19}$-phenyl-heteroaryl-O—($C_1$-$C_3$-alkylen),
a ($R^{19}$)-(heterocycloalkyl)-($C_1$-$C_3$-alkylene)- group,
a ($R^{19}$)-(heterocycloalkylene)-(phenylene)-O—($C_1$-$C_3$-alkylene)- group,
a (heterocycloalkenylene)-(phenylene)-O—($C_1$-$C_3$-alkylene)- group,
a ($R^{19}$)-(heteroaryl-($C_1$-$C_3$-alkylene)-O—($C_1$-$C_3$-alkylene)- group,
a ($R^{19}$)-(heteroaryl)-(phenylene)-O—($C_1$-$C_3$-alkylene)- group,
a ($R^{20}$)—S(O)$_2$-phenylene-O—($C_1$-$C_3$-alkylene)- group,
a ($R^{20}$)—S(O)$_2$—NH-phenylene-O—($C_1$-$C_3$-alkylene)- group,
a ($R^{20}$)—S(O)$_2$-heterocycloalkylene-phenylene-O—($C_1$-$C_3$-alkylene)- group,
a ($R^{19}$)-(heterocycloalkylene)-(heteroarylene)-O—($C_1$-$C_3$-alkylen)- group,
a ($R^{20}$)-heteroarylene-O—($C_1$-$C_3$-alkylene)- group, $NR^{21}R^{22}$—($C_1$-$C_3$-alkylene)- group,
a ($C_1$-$C_3$-alkyl)-NH—($C_1$-$C_3$-alkylene)- group,
a ($C_1$-$C_3$-haloalkyl)-($C_1$-$C_3$-alkylene)-NH—($C_1$-$C_3$-alkylene)- group,
a ($C_1$-$C_3$-haloalkyl)-NH—($C_1$-$C_3$-alkylene)- group,
a ($C_1$-$C_3$-alkyl)-C(O)—NH—($C_1$-$C_3$-alkylene)- group
a ($C_1$-$C_3$-alkyl)-C(O)—$NR^{15}$—($C_1$-$C_3$-alkylene)- group,
a group F
⟨⟩N—($C_1$-$C_3$-alkylene)
F a group

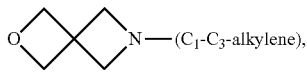

the heterocycloalkyl group is optionally substituted with an oxo (=O) group or is optionally substituted with a $C_1$-$C_3$-alkyl group,
or $R^8$ and $R^9$ together form a 5- or 6-membered ring optionally containing a oxygen atom, or a tautomer, an N-oxide, or a salt thereof or a salt of a tautomer or a N-oxide or a mixture of same.

In further embodiments, the present invention includes compounds of formula (I), supra, in which $R^9$ is selected from a hydrogen atom,
a $C_1$-$C_4$-alkyl group,
a $C_1$-$C_3$-hydroxyalkyl group,
a $C_1$-$C_6$-alkyl-O—($C_1$-$C_3$-alkylen)- group,
a phenyl-O—($C_1$-$C_3$-alkylene)- group,
a phenyl-($C_1$-$C_3$-alkylene)-O—($C_1$-$C_3$-alkylene)- group,
a $R^{19}$-phenyl-heteroaryl-O—($C_1$-$C_3$-alkylen),
a ($R^{19}$)-(heterocycloalkylene)-(phenylene)-O—($C_1$-$C_3$-alkylene)- group a (heterocycloalkenylene)-(phenylene)-O—($C_1$-$C_3$-alkylene)- group,
a ($R^{19}$)-(heteroaryl)-(phenylene)-O—($C_1$-$C_3$-alkylene)- group,
a ($R^{20}$)—S(O)$_2$-phenylene-O—($C_1$-$C_3$-alkylene)- group,
a ($R^{20}$)—S(O)$_2$-heterocycloalkylene-phenylene-O—($C_1$-$C_3$-alkylene)- group,
or a tautomer, an N-oxide, or a salt thereof or a salt of a tautomer or a N-oxide or a mixture of same.

In further embodiments, the present invention includes compounds of formula (I), supra, in which $R^8$ and $R^9$ together form a 5- or 6-membered ring optionally containing one or two heteroatoms selected from —O—, and —NR$^{14}$—, or a tautomer, an N-oxide, or a salt thereof or a salt of a tautomer or a N-oxide or a mixture of same.

In further embodiments, the present invention includes compounds of formula (I), supra, in which $R^8$ and $R^9$ together form a 5- or 6-membered ring optionally containing one or two oxygen atoms, or a tautomer, an N-oxide, or a salt thereof or a salt of a tautomer or a N-oxide or a mixture of same.

In further embodiments, the present invention includes compounds of formula (I), supra, in which $R^8$ and $R^9$ together form a 6-membered ring optionally containing one or two oxygen atoms, or a tautomer, an N-oxide, or a salt thereof or a salt of a tautomer or a N-oxide or a mixture of same.

In further embodiments, the present invention includes compounds of formula (I), supra, in which $R^8$ and $R^9$ together form a 6-membered ring optionally containing one oxygen atoms, or a tautomer, an N-oxide, or a salt thereof or a salt of a tautomer or a N-oxide or a mixture of same.

In further embodiments, the present invention includes compounds of formula (I), supra, in which $R^8$ and $R^9$ together are *—(CH$_2$)$_3$—O—**, *—(CH$_2$)$_2$O—CH$_2$—**, —(CH$_2$)$_4$—, where * means the point of attachment at the pyrazol nitrogen atom ($R^8$ site) whereas ** means the point of attachment to the carbon atom ($R^9$ site) of the pyrazol.

In further embodiments, the present invention includes compounds of formula (I), supra, in which $R^{12}$ is a methoxy group, or a tautomer, an N-oxide, or a salt thereof or a salt of a tautomer or a N-oxide or a mixture of same.

In further embodiments, the present invention includes compounds of formula (I), supra, in which $R^{12}$ is hydrogen or a methoxy group, or a tautomer, an N-oxide, or a salt thereof or a salt of a tautomer or a N-oxide or a mixture of same.

In further embodiments, the present invention includes compounds of formula (I), supra, in which $R^{13}$ is hydrogen or a methyl group, or a tautomer, an N-oxide, or a salt thereof or a salt of a tautomer or a N-oxide or a mixture of same.

In further embodiments, the present invention includes compounds of formula (I), supra, in which $R^{15}$ is selected from
a hydrogen atom,
a $C_1$-$C_6$-alkyl group
which is optionally substituted with one or more substituents selected from a halogen atom, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a heterocycloalkyl group, an aryl group, a ($R^{19}$)-(heterocycloalkylene)-(arylene)-O— group, an aryl-O— group, an aryl-($C_1$-$C_3$-alkylene)-O— group, a ($R^{20}$)—S(O)$_2$-arylene-O— group, a ($R^{20}$)S(O)$_2$-heterocycloalkylene-arylene-O— group, and an aryl-heteroarylene-O— group;
a phenyl group,
a group

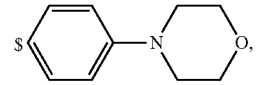

a group

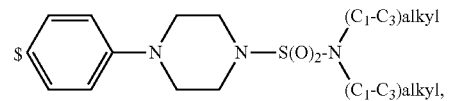

and
a group

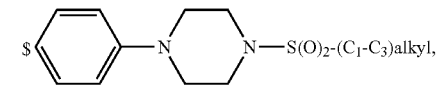

where $ is the point of attachment to the nitrogen atom, to which $R^{15}$ is attached, or stereoisomers, tautomers, N-oxides, and salts thereof, and mixtures of same.

In further embodiments, the present invention includes compounds of formula (I), supra, in which $R^{15}$ is selected from
a hydrogen atom,
a $C_1$-$C_6$-alkyl group
which is optionally substituted with one or more substituents selected from a halogen atom, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a heterocycloalkyl group, a phenyl group, a ($R^{19}$)-(heterocycloalkylene)-(phenylene)-O— group, a phenyl-O— group, a phenyl-($C_1$-$C_3$-alkylene)-O— group, a ($R^{20}$)—S(O)$_2$-(phenylene)-O— group, a ($R^{20}$)

S(O)$_2$—(heterocycloalkylene)-(phenylene)-O— group, and a phenyl-(heteroarylene)-O— group;
a phenyl group,
a group

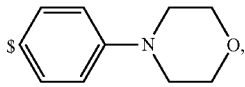

a group

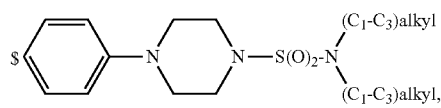

and
a group

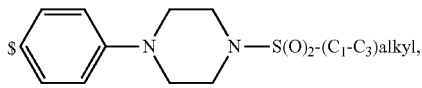

where $ is the point of attachment to the nitrogen atom, to which R$^{15}$ is attached, or a tautomer, an N-oxide, or a salt thereof or a salt of a tautomer or a N-oxide or a mixture of same.

In further embodiments, the present invention includes compounds of formula (I), supra, in which R$^{15}$ is selected from
a hydrogen atom,
a C$_1$-C$_6$-alkyl group
which is optionally substituted with a phenyl group
a phenyl group,
a group,

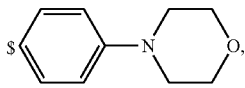

a group

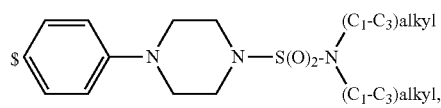

and
a group

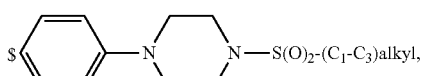

where $ is the point of attachment to the nitrogen atom, to which R$^{15}$ is attached, or stereoisomers, tautomers, N-oxides, and salts thereof, and mixtures of same.

In further embodiments, the present invention includes compounds of formula (I), supra, in which R$^{15}$ is selected from
a hydrogen atom,
a C$_1$-C$_3$-alkyl group
which is optionally substituted with a phenyl group
a phenyl group,
a group

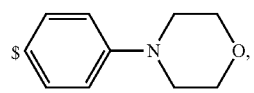

a group

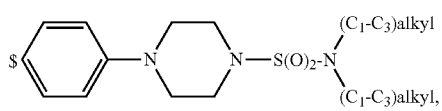

and
a group

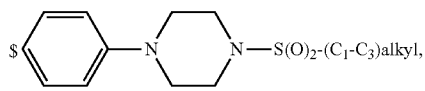

where $ is the point of attachment to the nitrogen atom, to which R$^{15}$ is attached, or a tautomer, an N-oxide, or a salt thereof or a salt of a tautomer or a N-oxide or a mixture of same.

In further embodiments, the present invention includes compounds of formula (I), supra, in which R$^{15}$ is selected from a hydrogen atom and a C$_1$-C$_6$-alkyl group which is optionally substituted with one or more substituents selected from a halogen atom, a C$_1$-C$_3$-alkyl group, a C$_1$-C$_3$-haloalkyl group, and a C$_1$-C$_3$-hydroxyalkyl group, or
R$^{15}$ is selected from a C$_1$-C$_3$-alkoxy-(CH$_2$)$_2$— group, a C$_1$-C$_3$-haloalkoxy-(CH$_2$)$_2$— group, a C$_1$-C$_6$-alkyl-O—(C$_2$-C$_3$-alkylene)- group, a phenyl-O—(C$_2$-C$_3$-alkylene)- group, a phenyl-(C$_1$-C$_3$-alkylene)-O—(C$_2$-C$_3$-alkylene)- group, a (heterocycloalkyl)-(C$_1$-C$_3$-alkylene)- group, a (R$^{19}$)-(heterocycloalkylene)-(phenylene)-O—(C$_2$-C$_3$-alkylene)- group, a (R$^{20}$)—S(O)$_2$-(phenylene)-O—(C$_2$-C$_3$-alkylene)- group, a (R$^{20}$)—S(O)$_2$-(heterocycloalkylene)-(phenylene)-O—(C$_2$-C$_3$-alkylene)- group, a phenyl-(heteroarylene)-O—(C$_2$-C$_3$)-alkylene- group, a phenyl group, a group

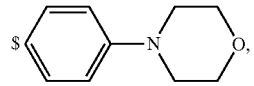

a group

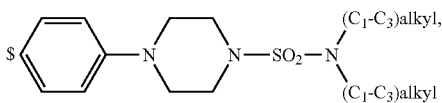

and
and a group

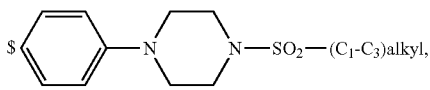

where $ is the point of attachment to the nitrogen atom, to which $R^{15}$ is attached or stereoisomers, tautomers, N-oxides, and salts thereof, and mixtures of same.

In further embodiments, the present invention includes compounds of formula (I), supra, in which $R^{15}$ is selected from a hydrogen atom and a $C_1$-$C_6$-alkyl group which is optionally substituted with one or more substituents selected from a halogen atom, a $C_1$-$C_3$-alkyl group, a $C_1$-$C_3$-haloalkyl group, and a $C_1$-$C_3$-hydroxyalkyl group; or $R^{15}$ is selected from a $C_1$-$C_3$-alkoxy-$(CH_2)_2$— group, a $C_1$-$C_3$-haloalkoxy-$(CH_2)_2$— group, a $C_1$-$C_6$-alkyl-O—($C_2$-$C_3$-alkylene)- group, a phenyl-O—($C_2$-$C_3$-alkylene)- group, a phenyl-($C_1$-$C_3$-alkylene)-O—($C_2$-$C_3$-alkylene)- group, a (heterocycloalkyl)-($C_1$-$C_3$-alkylene)- group, a ($R^{19}$)-(heterocycloalkylene)-(phenylene)-O—($C_2$-$C_3$-alkylene)- group, a ($R^{20}$)—S(O)$_2$-(phenylene)-O—($C_2$-$C_3$-alkylene)- group, a ($R^{20}$)—S(O)$_2$-(heterocycloalkylene)-(phenylene)-O—($C_2$-$C_3$-alkylene)- group, a phenyl-(heteroarylene)-O—($C_2$-$C_3$-alkylene)- group, a phenyl group, a group

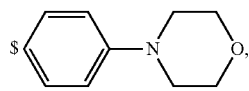

a group

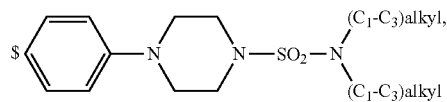

and
a group

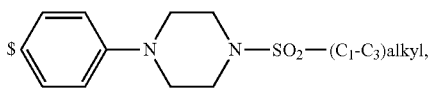

where $ is the point of attachment to the nitrogen atom, to which $R^{15}$ is attached, stereoisomers, tautomers, N-oxides, and salts thereof, and mixtures of same.

In further embodiments, the present invention includes compounds of formula (I), supra, in which $R^{15}$ is selected from a hydrogen atom, a $C_1$-$C_3$-alkyl group, a $C_1$-$C_3$-alkyl group which is substituted with a phenyl group, a phenyl group, a group

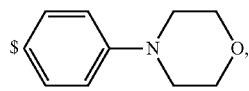

a group

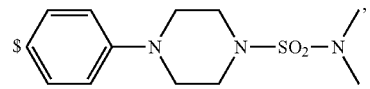

and a group

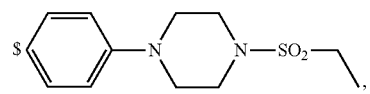

where $ is the point of attachment to the nitrogen atom, to which $R^{15}$ is attached, stereoisomers, tautomers, N-oxides, and salts thereof, and mixtures of same.

In further embodiments, the present invention includes compounds of formula (I), supra, in which $R^{15}$ is selected from a $C_1$-$C_3$-alkyl group, a $C_1$-$C_3$-alkyl group which is substituted with a phenyl group;

a phenyl group, a group

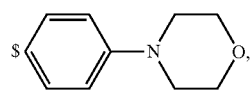

a group

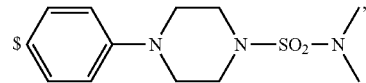

and a group

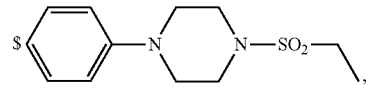

where $ is the point of attachment to the nitrogen atom, to which $R^{15}$ is attached, or a tautomer, an N-oxide, or a salt thereof or a salt of a tautomer or a N-oxide or a mixture of same.

In further embodiments, the present invention includes compounds of formula (I), supra, in which $R^{15}$ is selected from a $C_1$-$C_3$-alkyl group, a phenyl group, a group

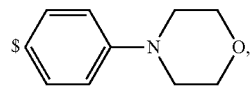

a group

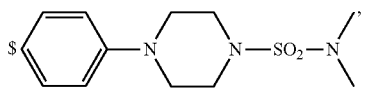

a group

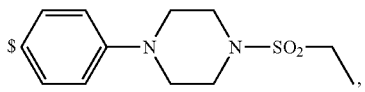

where $ is the point of attachment to the nitrogen atom, to which $R^{15}$ is attached, or a tautomer, an N-oxide, or a salt thereof or a salt of a tautomer or a N-oxide or a mixture of same.

In further embodiments, the present invention includes compounds of formula (I), supra, in which $R^{15}$ is an unsubstituted $C_1$-$C_6$-alkyl group, preferably a $C_1$-$C_3$-alkyl group, more preferably a methyl group and salts thereof, and mixtures of same.

In further embodiments, the present invention includes compounds of formula (I), supra, in which $R^{15}$ is a $C_1$-$C_6$-alkyl group which is optionally substituted with phenyl and salts thereof, and mixtures of same.

In further embodiments, the present invention includes compounds of formula (I), supra, in which $R^{15}$ is a $C_1$-$C_6$-alkyl group which is substituted with phenyl and salts thereof, and mixtures of same.

In further embodiments, the present invention includes compounds of formula (I), supra, in which $R^{16}$ is selected from pharmaceutically acceptable anions, preferably selected from Cl⁻, Br⁻, Acetate ($CH_3CO_2$)⁻, trifluoroacetate ($CF_3CO_2$)⁻, and formate ($HCO_2$)⁻ or an inner salt of the anion of another portion of the same molecule, or where two molecule zwitter ions form two salt pairs.

$R^{19}$ and $R^{20}$ are substitutents which may be located at any position of the residue bearing such substituent which can be adressed by chemically suitable methods irrespective at which position such residue may bear further substitutents, e.g. a morpholine ring bearing a $R^{19}$ substituent can be 2-methyl-morpholine or 3-methyl-morpholine or a tetrahydropyrane bearing a $R^{19}$ substituent can be 3-hydroxy-tetrahydropyrane or 4-hydroxy-tetrahydropyrane leading to e.g. $R^9$ is a [4-(4-hydroxytetrahydro-2H-pyran-4-yl)phenoxy]methyl- group.

In yet further embodiments, the present invention includes compounds of formula (I), supra, in which $R^{19}$ is a $C_1$-$C_3$-alkyl group, or stereoisomers, tautomers, N-oxides, and salts thereof, and mixtures of same.

In further embodiments, the present invention includes compounds of formula (I), supra, wherein $R^{20}$ is selected from a $C_1$-C-alkyl group, a $C_3$-$C_6$-cycloalkyl group, particularly a cyclopropyl group, and a $NR^{21}R^{22}$ group, and $R^{17}$ and $R^{18}$ are each independently selected from a hydrogen atom and a $C_1$-$C_3$-alkyl group, or a tautomer, an N-oxide, or a salt thereof or a salt of a tautomer or a N-oxide or a mixture of same.

In further embodiments, the present invention includes compounds of formula (I), supra, wherein $R^{19}$ is selected from a hydrogen atom, a $C_1$-$C_3$-alkyl group, a $C_1$-$C_6$-hydroxyalkyl group, a $C_1$-$C_3$-alkoxy group, a —($C_1$-$C_3$-alkylene)-C(O)OR$^{21}$ group, a —C(O)OR$^{21}$ group, a —C(O)—($C_1$-$C_6$-alkyl) group, a —C(O)($C_1$-$C_3$-alkylene)-O—($C_1$-$C_3$-alkyl) group, and a —C(O)$C_3$-$C_6$-cycloalkyl group, and $R^{21}$ is a hydrogen atom or a $C_1$-$C_6$-alkyl group, or a tautomer, an N-oxide, or a salt thereof or a salt of a tautomer or a N-oxide or a mixture of same.

In further embodiments, the present invention includes compounds of formula (I), supra, in which $R^{19}$ is a hydroxyl group or a $C_1$-$C_3$-alkoxy group, or a tautomer, an N-oxide, or a salt thereof or a salt of a tautomer or a N-oxide or a mixture of same.

In yet further embodiments, the present invention includes compounds of formula (I), supra, wherein B is selected from a —N(R$^{15}$)— group, —O—, and

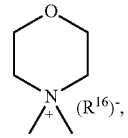

$R^{15}$ is selected from a hydrogen atom and a $C_1$-$C_6$-alkyl group which is optionally substituted with one or more substituents selected from a halogen atom, a $C_1$-$C_3$-alkyl group, a $C_1$-$C_3$-haloalkyl group, and a $C_1$-$C_3$-hydroxyalkyl group, or $R^{15}$ is selected from a $C_1$-$C_3$-alkoxy-(CH$_2$)$_2$— group, a $C_1$-$C_3$-haloalkoxy-(CH$_2$)$_2$— group, a $C_1$-$C_6$-alkyl-O—(C$_2$-$C_3$-alkylene)- group, a phenyl-O—(C$_2$-$C_3$-alkylene)- group, a phenyl-(C$_1$-$C_3$-alkylene)-O—(C$_2$-$C_3$-alkylene)- group, a (heterocycloalkyl)-(C$_1$-$C_3$-alkylene)- group, a (R$^{19}$)-(heterocycloalkylene)-(phenylene)-O—(C$_2$-$C_3$-alkylene)- group, a (R$^{20}$)—S(O)$_2$-(phenylene)-O—(C$_2$-$C_3$-alkylene)- group, a (R$^{20}$)—S(O)$_2$-(heterocycloalkylene)-(phenylene)-O—(C$_2$-$C_3$-alkylene)- group, a phenyl-(heteroarylene)-O—(C$_2$-$C_3$-alkylene)- group, a phenyl group, a group

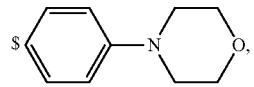

a group

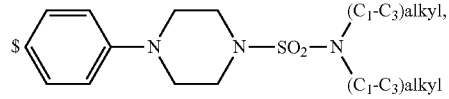

and a group

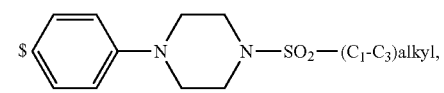

where $ is the point of attachment to the nitrogen atom, to which $R^{15}$ is attached, where $R^{16}$ is a pharmaceutically acceptable anion, where $R^{17}$ and $R^{18}$ are each independently selected from a hydrogen atom and a $C_1$-$C_6$-alkyl group, where $R^{19}$ is selected from a hydrogen atom, a hydroxy group, a $C_1$-$C_3$-alkyl group, a $C_1$-$C_6$-hydroxyalkyl group, a $C_1$-$C_3$-alkoxy group, a —($C_1$-$C_3$-alkylene)-C(O)$OR^{21}$ group, a —C(O)($C_1$-$C_6$-alkyl) group, a —C(O)$OR^{21}$ group, a —C(O)($C_1$-$C_3$-alkylene)-O—($C_1$-$C_3$-alkyl) group, and a —C(O)$C_3$-$C_6$-cycloalkyl group, where $R^{20}$ is selected from a $C_1$-$C_3$-alkyl group, a $C_3$-$C_6$-cycloalkyl group, and a $NR^{21}R^{22}$ group, and $R^{21}$ is a hydrogen atom or a $C_1$-$C_6$-alkyl group;

or a tautomer, an N-oxide, or a salt thereof or a salt of a tautomer or a N-oxide or a mixture of same.

In yet further embodiments, the present invention includes compounds of formula (I), supra, in which B is selected from a —C(O)$NR_{15}$— group, a —$NR_{15}$C(O)— group, a —N($R^{15}$)— group, —O—, —S—, —S(O)—, —S(O)$_2$—, and

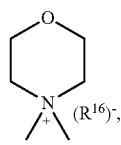

$R^{15}$ is selected from a hydrogen atom, and a $C_1$-$C_6$-alkyl group which is optionally substituted with one or more substituents selected from a halogen atom, a $C_1$-$C_3$-alkyl group, a $C_1$-$C_3$-haloalkyl group, and a $C_1$-$C_3$-hydroxyalkyl group, or $R^{15}$ is selected from a $C_1$-$C_3$-alkoxy-(CH$_2$)$_2$— group, a $C_1$-$C_3$-haloalkoxy-(CH$_2$)$_2$— group, a $C_1$-$C_6$-alkyl-O—(C$_2$-$C_3$-alkylene)- group, a phenyl-O—(C$_2$-$C_3$-alkylene)- group, a phenyl-($C_1$-$C_3$-alkylene)-O—(C$_2$-$C_3$-alkylene)- group, a (heterocycloalkyl)-($C_1$-$C_3$-alkylene)- group, a ($R^{19}$)-(heterocycloalkylene)-(phenylene)-O—(C$_2$-$C_3$-alkylene)- group, a ($R^{20}$)—S(O)$_2$-phenylene-O—(C$_2$-$C_3$-alkylene)- group, a ($R^{20}$)—S(O)$_2$-heterocycloalkylene-phenylene-O—(C$_2$-$C_3$-alkylene)- group, a phenyl-heteroaryl-O—(C$_2$-$C_3$)-alkylene- group, a phenyl group, a group

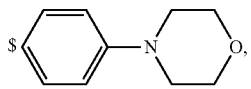

a group

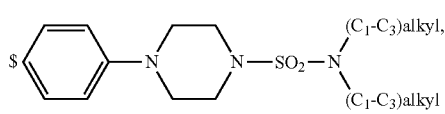

and a group

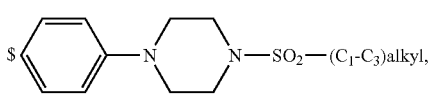

where $ is the point of attachment to the nitrogen atom, to which $R^{15}$ is attached,
where $R^{16}$ is a pharmaceutically acceptable anion,
or a tautomer, an N-oxide, or a salt thereof or a salt of a tautomer or a N-oxide or a mixture of same.

In further embodiments, the present invention includes compounds of formula (I), supra, in which B is selected from a —N($R^{15}$)— group and —O—,
$R^{15}$ is a $C_1$-$C_3$-alkyl group, a phenyl group, a group

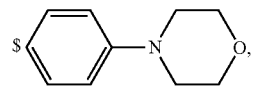

a group

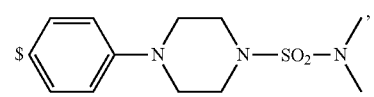

and a group

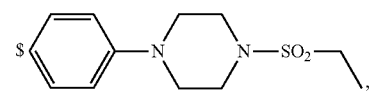

where $ is the point of attachment to the nitrogen atom, to which $R^{15}$ is attached,
where $R^{16}$ is a pharmaceutically acceptable anion,
or stereoisomers, tautomers, N-oxides, and salts thereof, and mixtures of same.

In further embodiments, the present invention includes compounds of formula (I), supra, in which $R^{15}$ is selected from a methyl group, a phenyl group, a group

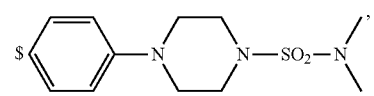 [SMILES: CN(C)S(=O)(=O)N1CCN(c2ccccc2)CC1]

a group

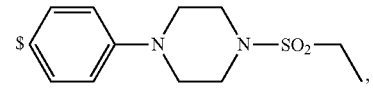

and a group

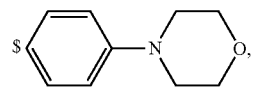

or stereoisomers, tautomers, N-oxides, and salts thereof, and mixtures of same.

In further embodiments, the present invention includes compounds of formula (I), supra, in which B is selected from a —N($R^{15}$)— group and —O—, or stereoisomers, tautomers, N-oxides, and salts thereof, and mixtures of same.

In other embodiments, the present invention includes compounds of formula (I), supra, in which B is a —N($R^{15}$)— group, or a tautomer, an N-oxide, or a salt thereof or a salt of a tautomer or a N-oxide or a mixture of same.

In further embodiments, the present invention includes compounds of formula (I), supra, in which B is —O—, or a tautomer, an N-oxide, or a salt thereof or a salt of a tautomer or a N-oxide or a mixture of same.

In further embodiments, the present invention includes compounds of formula (I), supra, in which $R^{15}$ is a $C_1$-$C_6$-alkyl group which is optionally substituted with one or more substituents selected from a halogen atom, a $C_1$-$C_3$-alkyl group, a $C_1$-$C_3$-haloalkyl group, and a $C_1$-$C_3$-hydroxyalkyl group, more particularly methyl, or a tautomer, an N-oxide, or a salt thereof or a salt of a tautomer or an N-oxide or a mixture of same.

In further embodiments, the present invention includes compounds of formula (I), which are salts.

In further embodiments, the present invention includes compounds of formula (I), which are a tautomer, or a salt thereof or a salt of a tautomer or a mixture of same In further embodiments, the present invention includes compounds of formula (I), which are a an N-oxide, or a salt thereof or a salt of an N-oxide or a mixture of same In a particular further embodiment of the first aspect, the present invention provides combinations of two or more of the above mentioned embodiments under the heading "further embodiments of the first aspect of the present invention".

Furthermore it is understood that the invention includes any subcombination of the disclosed single embodiments herein for certain residues or subcombination of residues of formula (I).

The present invention includes any sub-combination within any embodiments or aspects of the present invention of compounds of general formula (I), supra.

The present invention includes any sub-combination within any embodiments or aspects of the present invention of compounds or intermediate compounds of general formula (I or II). The present invention includes the compounds of general formula (I) which are disclosed in the Example Section of this text, infra.

GENERAL SYNTHESIS OF COMPOUNDS OF GENERAL FORMULA (I) OF THE PRESENT INVENTION

A. General Synthesis Route

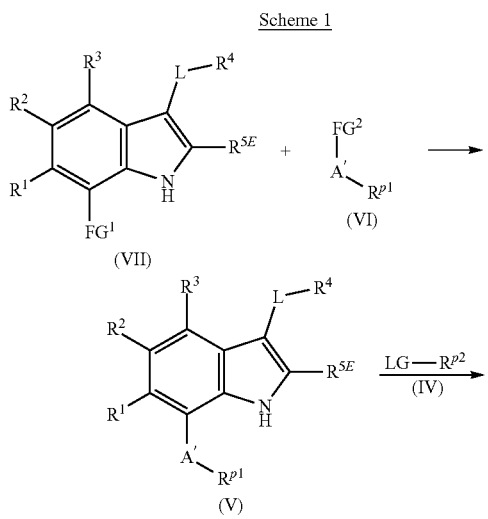

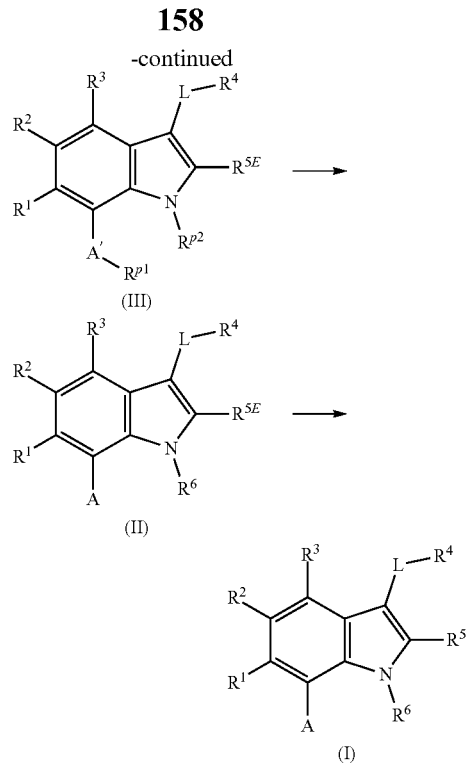

Compounds of general formula (I) can be synthesized according to the general synthesis route depicted in Scheme 1, encompassing a Suzuki coupling of starting materials of formulae (VII) and (VI) to give intermediates of formula (V), elaboration of the macrocylic core by attachment of a group $R^{p2}$ to the indole nitrogen present in compounds of formula (V), followed by macrocyclisation of the resulting intermediates of formula (III), e.g. by ring closing metathesis or intramolecular nucleophilic substitution, to give macrocyclic intermediates of formula (II). Dependent inter alia on the nature of $R^{p1}$ and $R^{p2}$, the conversion of compounds of formula (V) into said macrocyclic intermediates of formula (II) may proceed with or without the intermediacy of intermediates of formula (III); for details see e.g. the Schemes 2a-2o, infra. Finally, conversion of $R^{5E}$ into $R^5$, e.g. by ester saponification, optionally followed by conversion of the resulting carboxylic acid into an acylsulfonamide according to methods known to the person skilled in the art (see for example: *Bioorg. Med Chem. Lett.* 2006, 16, 3639-3641; *Bioorg. Med Chem. Lett.* 2012, 22, 713-717; *Org. Lett.* 2012, 14(2), 556-559), yields the compounds of formula (I).

Said general synthesis route commences with a well-known Suzuki coupling of compounds of formula (VII), in which $R^1$, $R^2$, $R^3$, $R^4$ and L are as defined for the compounds of general formula (I), and in which $R^{5E}$ represents a group suitable to act as a precursor of a —C(=O)OH or a tetrazol-5-yl group, preferably a group —C(=O)O—$C_{1-4}$-alkyl, with compounds of formula (VI), in which A', together with the group $R^{p1}$ attached to it, represents a group suitable to act as precursor of a group A as defined for the compounds of general formula (I), to give compounds of formula (V). The group -L-$R^4$, attached to C-3 of the indole core in formula (VII), can alternatively be established, partially or completely, on later stage (see e.g. Schemes 4d, 4e and 4f and their discussion for details). Examples of groups A' are exemplified further below in this chapter. In formulae (VI) and (VII), $FG^1$ in combination with $FG^2$ represents a pair of functional groups together enabling a Suzuki coupling; either FG¹ represents chloro, bromo, iodo or a trifluoromethanesulfonyl- group and FG² represents a group —B(OR$^B$)$_2$, or vice versa. Said group —B(OR$^B$)$_2$ may be a boronic acid moiety (R$^B$=—H) or an alkyl ester of the boronic acid, e.g. its isopropyl ester (R$^B$=C$_1$-C$_4$-alkyl, e.g. —CH(CH$_3$)$_2$), or an ester derived from a diol such as pinacol in which the boronic acid intermediate forms a cyclic boronic ester, preferably a 4,4,5,5-tetramethyl-1,3,2-dioxaborolane (R$^B$-R$^B$=C$_2$-C$_6$-alkylene, preferably —C(CH$_3$)$_2$—C(CH$_3$)$_2$—). Many boronic acids and their esters are commercially available and their synthesis is well-known to the person skilled in the art; see e.g. D. G. Hall, Boronic Acids, 2005 WILEY-VCH Verlag GmbH & Co. KGaA, Weinheim, ISBN 3-527-30991-8 and references cited therein, and Journal of Medicinal Chemistry, 2015, 58, 2180-2194. Alternatively to boronic acid derivatives, also tetrafluoroborates, in which —BF$_4^-$ replaces the —B(OR$^B$)$_2$ moiety, can also be employed.

Said Suzuki coupling reaction can be catalysed by palladium catalysts, exemplified by but not limited to by Pd(0) catalysts such as tetrakis(triphenylphosphine)palladium(0) [Pd(PPh$_3$)$_4$], tris(dibenzylideneacetone)di-palladium(0) [Pd$_2$(dba)$_3$] in combination with a ligand, e.g. a phosphine such as triphenylphosphine, or by Pd(II) catalysts such as dichlorobis(triphenylphosphine)-palladium(II) [Pd(PPh$_3$)$_2$Cl$_2$], dichloropalladium-tricyclohexylphosphine (1:2), palladium(II) acetate in combination with a ligand, e.g. a phosphine such as triphenylphosphine, chloro(2-dicyclohexylphosphino-2',4',6'-triisopropyl-1,1'-biphenyl)[2-(2'-amino-1,1'-biphenyl)]palladium(II), (2-Dicyclohexylphosphino-2',4',6'-triisopropyl-1,1'-biphenyl)[2-(2'-amino-1,1'-biphenyl)]palladium(II) methanesulfonate, or by [1,1'-bis(diphenylphosphino)ferrocene]-palladium dichloride, in free form [Pd(dppf)Cl$_2$] or as dichloromethane adduct [Pd(dppf)Cl$_2$×CH$_2$Cl$_2$].

The reaction is preferably carried out in solvents such as 1,2-dimethoxyethane, 1,4-dioxane, DMF, THF, or n-propanol, or mixtures thereof, optionally also in mixture with water, and in the presence of a base such as aqueous potassium carbonate, aqueous sodium carbonate or aqueous potassium phosphate. In certain cases, also certain alkali halides, such as lithium chloride or potassium fluoride, can be added as advantageous additives to the reaction mixture.

The reaction is performed at temperatures ranging from room temperature (i.e. 20° C.) to the boiling point of the solvent. Additionally, the reaction can be performed at temperatures above the boiling point using pressure tubes and a microwave oven. (for a review on Suzuki couplings see: D. G. Hall, Boronic Acids, 2005 WILEY-VCH Verlag GmbH & Co. KGaA, Weinheim, ISBN 3-527-30991-8 and references cited therein).

The reaction is preferably completed after 1 to 36 hours of reaction time.

Synthetic approaches to starting materials of formulae (VI) and (VII) are discussed in context of Schemes 4a-4f and paragraphs subsequent to these, infra.

Compounds of formula (II) can be obtained using various methods described in more detail below, e.g. by reacting compounds of formula (V) with compounds of formula (IV) in which LG represents a leaving group, preferably bromo or iodo, and in which R$^{P2}$ represents a group suitable to act as a precursor for the group R$^6$ as defined for the compounds of general formula (I). The following paragraphs outline more specific examples of said conversion of compounds of formulae (Va), (Vc), (Vg), (Vh), (Vj) and (Vk), all constituting sub-compartments of formula (V), into compounds of (IIa), (IIb), (IIc), (IIe), (IIf), (IIg), (IIh), (IIi), (IIj), (IIk), (IIm), (IIn) and (IIo), all of them constituting sub-compartments of formula (II), some of which with the intermediacy of compounds of formulae (IIIa), (IIIb), (IIIc), (IIIf), (IIIg), (IIIh), (IIIi), and (IIIo), all of them constituting sub-compartments of formula (III), as discussed in the context of Scheme 1.

Certain compounds of the present invention, as well as the corresponding macrocyclic intermediates of formula (II), may feature an olefinic double bond of unknown configuration as a part of their macrocyclic core, cf. those intermediates of formulae (IIc), (IIg), (IIi) and (IIo) shown and discussed in context of Schemes 2c, 2d, 2e, 2g, 2i and 2o. Said olefinic double bond is therefore displayed as

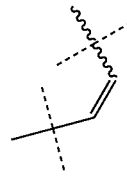

therein. This visualization means that the respective olefinic double bond may be present in either (E) or (Z) configuration, or as a mixture of (E) and (Z) isomers.

However, in compounds featuring an olefinic double bond which is not part of said macrocyclic core, e.g. those of formulae (Vh) and (IIIi), said visualization

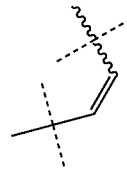

indicates a mixture of (E) and (Z) isomers, according to the usual practice of the person skilled in the art.

Said macrocyclic intermediates of formula (II) can finally be converted into the compounds of general formula (I) as described in further detail in context with Scheme 3, infra.

B. More Specific Synthesis Routes for Establishing the Macrocyclic Core, Schemes 2a-2o Examples for R$^{P1}$ and R$^{P2}$ groups, as referred to in the general Synthesis Route of Scheme 1 above, are listed below and are put into their synthetic context in the more specific synthesis routes for establishing the macrocyclic core as present in advanced macrocyclic intermediates of formula (II), from compounds of formula (V), described further below. R$^{P1}$ groups are exemplified by but not limited to groups such as —CH$_2$—OH, —(CH$_2$)$_b$—OH, —(CH$_2$)$_b$-LG$^2$, —(CH$_2$)$_b$-LG$^3$, (CH$_2$)$_c$—OH, —(CH$_2$)$_c$—O—(CH$_2$)$_d$—CH=CH$_2$, —CH=CH—(CH$_2$)$_g$—OH, —CH=CH—(CH$_2$)$_g$-LG$^{11}$, —(CH$_2$)$_{g+2}$-LG$^{10}$, —NH(PG$^2$), —N(PG$^2$)-(CH$_2$)$_d$—CH=CH$_2$, —OH, —O—(CH$_2$)$_d$—CH=CH$_2$, —(CH$_2$)$_c$—NR$^{15}$(PG$^2$), in which LG$^2$, LG$^3$, LG$^{10}$ and LG$^{11}$, independently from each other, represent a leaving group as defined supra, preferably chloro, bromo or iodo, in which R$^{15}$ is as defined for the compounds of general formula (I), in which PG$^2$ represents a protective group, and in which indices "b", "c", "d" and "g" are as defined infra, and $R^{p2}$ groups are exemplified by but not limited to groups such as —$(CH_2)_a$—$N(R^{15})$—$PG^1$,

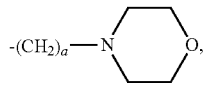

—$(CH_2)_e$—$CH$=$CH_2$, —$(CH_2)_f$-$LG^9$ or a hydrogen atom, in which $R^{15}$ is as defined for the compounds of general formula (I), $PG^1$ represents a hydrogen atom or a protective group, $LG^9$ represents a leaving group as defined supra, preferably chloro, bromo or iodo, and indices "a", "e" and "f" are as defined infra.

The reader is referred to the fact that the indices "a", "b", "c", "d", "e", "f", "g", "h", "i" and "j" used within and in the context of the following Schemes 2a-2o have been introduced independently from the corresponding indices "n", "p", "q", "r", "t" and "v" used in the claims, in order to reflect diversity of chemotypes encompassed within the general formula (I), and of the various synthesis routes useful for their preparation. Said diversity encompasses inter alia

- the fact that whilst A contributes two carbon atoms to the macrocyclic core if being derived from pyrazole, A contributes three carbon atoms to the macrocyclic core if being derived from benzene, pyridine, pyrimidine or pyridazine;
- the fact that inherently unstable formaldehyde aminals or hemiaminals result when "t" represents an integer 1 and a nitrogen or oxygen atom (but not a carbon atom), which is encoded for by $(B)_t$, is separated from the core indole nitrogen only by one carbon atom,
- the fact that certain parts of precursor groups of —$R^6$-$R^7$ and —$R^6R^{10}$, such as olefinic double bonds, have been drawn explicitly in some the Schemes for the sake of chemical clarity, mandating independent indices for the remaining parts of said precursor groups.

Scheme 2a

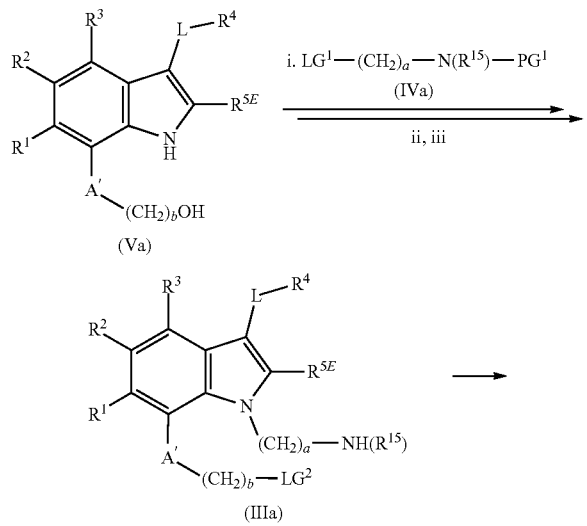

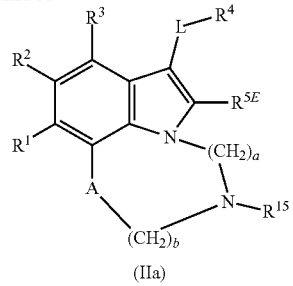

According to Scheme 2a, compounds of formula (IIa), in which $R^7$ (which is a feature of group A as defined for the compounds of general formula (I)) and $R^6$ together form a ##—$(CH_2)_b$—$N(R^{15})$—$(CH_2)_a$—# group, in which # represents the point of attachment to the indole nitrogen atom and ## represents the point of attachment to the pyrazole carbon atom bearing the $R^7$ substituent, can be obtained from compounds of formula (Va), in which $R^1$, $R^2$, $R^3$, $R^4$ and L are as defined for the compounds of general formula (I), in which $R^{5E}$ represents a group suitable to act as a precursor of a —$C$(=O)OH or a tetrazol-5-yl group, preferably a group —$C$(=O)O—$C_{1-4}$-alkyl, and in which $R^{p2}$ represents a hydrogen atom and $R^{p1}$ (see General Synthesis Route, Scheme 1) represents a —$(CH_2)_b$—OH group (in which the index "b" represents an integer selected from 0, 1, 2, 3, 4, 5, 6, 7 and 8), by (i) reacting with compounds of formula (IVa), in which $R^{15}$ is as defined for the compounds of general formula (I), the index "a" represents an integer selected from 2, 3, 4, 5, 6, 7, 8, 9 and 10, with the proviso that the sum of the integers representing indices "a" and "b" is at least 3 and does not exceed 10, $LG^1$ represents a leaving group and $PG^1$ represents a hydrogen atom or a protective group, followed by (ii) conversion of said —$(CH_2)_b$—OH group into a —$(CH_2)_b$-$LG^2$ group, and (iii), if $PG^1$ represents a protective group, cleavage of said protective group, to give compounds of formula (IIIa), in which $R^{p1}$ represents a —$(CH_2)_b$-$LG^2$ group (in which in turn $LG^2$ represents a leaving group, preferably bromo), and in which $R^{p2}$ represents a —$(CH_2)_a$—$NH(R^{15})$ group. Dependent on the reaction and/or work-up conditions, compounds of the formula (IIIa) can be isolated as free bases or as salts, e.g. salts with hydrochloric acid. Subsequently, said compounds of formula (IIIa) can be subjected to an intramolecular nucleophilic substitution, giving rise to the corresponding macrocyclic intermediates of formula (IIa).

The abovementioned sequence of transformations can be advantageously accomplished by (step i) deprotonating a compound of formula (Va) with a suitable base, such as caesium carbonate, potassium tert-butoxide, or sodium hydride, in a suitable solvent, such as DMF, acetonitrile or THF, followed by addition of a compound of formula (IVa); subsequently (step ii) by halogenation of said —$(CH_2)_b$—OH group, e.g. by treatment with tetrabromomethane and triphenylphosphine in a halogenated hydrocarbon, such as dichloromethane, as a solvent, and (step iii), if $PG^1$ represents a protective group, by an appropriate deprotection method (see e.g. T.W. Greene and P.G.M. Wuts in Protective Groups in Organic Synthesis, 4$^{th}$ edition, Wiley 2006), such as the cleavage of a tert-butoxycarbonyl group by hydrogen chloride in dioxane or by trifluoroacetic acid. The subsequent macrocyclization is favorably accomplished by reacting a compound of formula (IIIa) in the presence of a base such as an alkali carbonate or an alkali phosphate, preferably cesium carbonate, in a dipolar aprotic solvent such as dimethylformamide (DMF), dimethylacetamide or N-methyl pyrrolidin-2-one, preferably DMF, at a temperature between 20° C. and 120° C., preferably between 50° C. and 80° C.

Scheme 2b

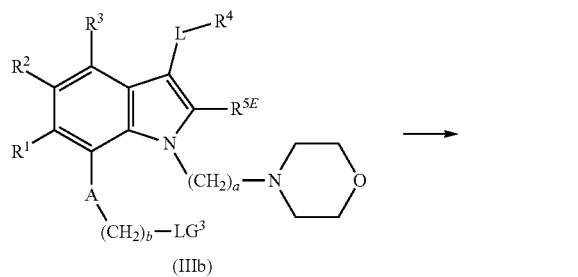

(IIIb)

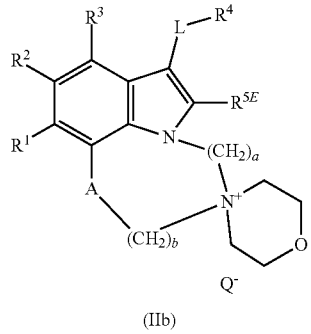

(IIb)

In an analogous fashion, and as outlined in Scheme 2b, compounds of formula (IIb), in which $R^7$ (which is a feature of group A as defined for the compounds of general formula (I)) and $R^6$ together form a

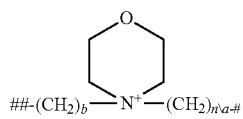

group, in which $^\#$ represents the point of attachment to the indole nitrogen atom and $^{\#\#}$ represents the point of attachment to the pyrazole carbon atom bearing the $R^7$ substituent, and in which $Q^-$ represents an anion corresponding to a leaving group, preferably a halide ion such as a bromide ion, can be obtained from compounds of formula (IIIb), in which $R^1$, $R^2$, $R^3$, $R^4$ and L are as defined for the compounds of general formula (I), in which $R^{5E}$ represents a group suitable to act as a precursor of a —C(=O)OH or a tetrazol-5-yl group, preferably a group —C(=O)O—$C_{1-4}$-alkyl, in which $R^{P1}$ (see General Synthesis Route, Scheme 1) represents a —(CH$_2$)$_b$-LG$^3$ group (in which the index "b" represents an integer selected from 0, 1, 2, 3, 4, 5, 6, 7 and 8, and LG represents a leaving group, preferably bromo), and in which $R^{P2}$ (see General Synthesis Route, Scheme 1) represents a

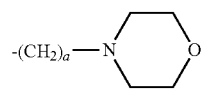

group (in which the index "a" represents an integer selected from 2, 3, 4, 5, 6, 7, 8, 9 and 10), by subjection to an intramolecular nucleophilic substitution, with the proviso that the sum of the integers representing indices "a" and "b" is at least 3 and does not exceed 10. Compounds of formula (IIIb) can be prepared in analogy to the approach outlined in Scheme 2a, supra.

Said intramolecular nucleophilic substitution can be favorably accomplished by reacting a compound of formula (IIIb) in the presence of a base such as an alkali carbonate or an alkali phosphate, preferably potassium carbonate, in a dipolar aprotic solvent such as dimethylformamide (DMF), dimethylacetamide (DMA) or N-methyl pyrrolidin-2-one, preferably DMA, at a temperature between 20° C. and 120° C., preferably between 40° C. and 70° C.

Scheme 2c

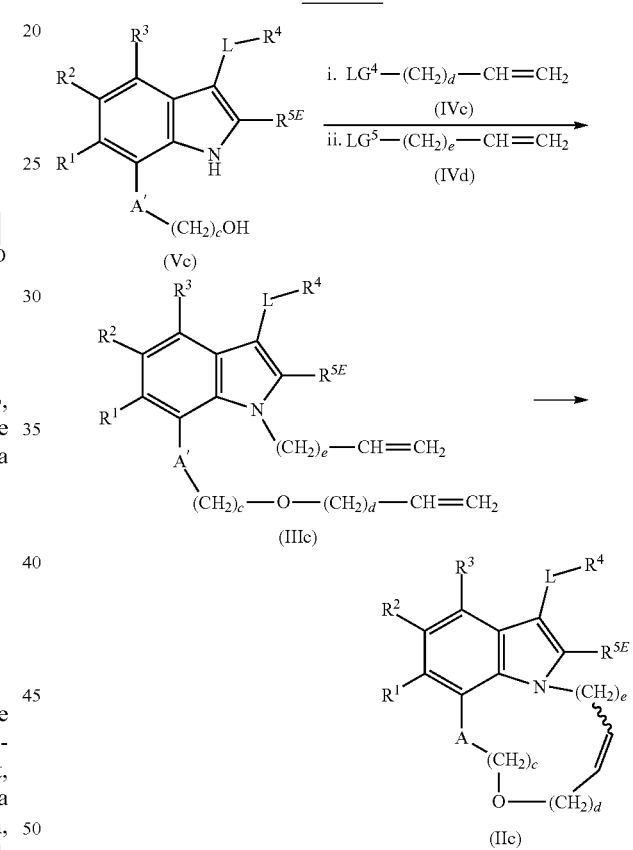

According to Scheme 2c, compounds of formula (IIc), in which $R^7$ (which is a feature of group A as defined for the compounds of general formula (I)) and $R^6$ together form a $^{\#\#}$—(CH$_2$)$_c$—O—(CH$_2$)$_d$—CH=CH—(CH$_2$)$_e$—$^\#$ group, in which $^\#$ represents the point of attachment to the indole nitrogen atom and $^{\#\#}$ represents the point of attachment to the pyrazole carbon atom bearing the $R^7$ substituent, can be obtained from compounds of formula (Vc), in which $R^1$, $R^2$, $R^3$, $R^4$ and L are as defined for the compounds of general formula (I), in which $R^{5E}$ represents a group suitable to act as a precursor of a —C(=O)OH or a tetrazol-5-yl group, preferably a group —C(=O)O—$C_{1-4}$-alkyl, in which $R^{P2}$ represents a hydrogen atom and $R^{P1}$ (see General Synthesis Route, Scheme 1) represents a —(CH$_2$)$_c$—OH group, in which index "c" represents an integer selected from 0, 1, 2 and 3, by reacting with compounds of formula (IVc), followed by compounds of formula (IVd), in which indices "d" and "e", independently from each other, represent an integer selected from 1, 2, 3, 4, 5 and 6, with the proviso that the sum of the integers representing indices "c", "d" and "e" does not exceed 8, and $LG^4$ and $LG^5$, independently from each other, represent a leaving group, to give compounds of formula (IIIc), in which $R^{p1}$ represents a —$(CH_2)_c$—O—$(CH_2)_d$—CH=$CH_2$ group, and in which $R^{p2}$ represents a —$(CH_2)_e$—CH=$CH_2$ group. Subsequently, said compounds of formula (IIIc) can be subjected to a ring closing metathesis (RCM) reaction (see e.g. *Chem. Rev.*, 2009, 109 (8), pp 3783-3816), giving rise to the corresponding macrocyclic intermediates of formula (IIc).

The abovementioned sequence of transformations can be advantageously accomplished by deprotonating a compound of formula (Vc) with one equivalent of a suitable base, such as sodium hydride or cesium carbonate, in a suitable solvent, such as THF, dimethylformamide (DMF) or dimethylacetamide (DMA), followed by addition of a compound of formula (IVc), followed by the addition of one further equivalent of a suitable base, such as sodium hydride or cesium carbonate, followed by addition of a compound of formula (IVd). Whenever indices "d" and "e" are identical, said base can be added in one portion, followed by one reagent of formula (IVc) or (IVd). The subsequent macrocyclization is favorably accomplished by reacting a compound of formula (IIIc) in the presence of a catalyst suitable for the performance of a ring closing metathesis exemplified by but not limited to (1,3-bis(2,4,6-trimethylphenyl)-2-imidazolidinylidene)dichloro(phenylmethylene) (tricyclohexylphosphine)ruthenium or (1,3-bis-(2,4,6-trimethylphenyl)-2-imidazolidinylidene)dichloro(o-isopropoxyphenylmethylene)ruthenium, in a halogenated hydrocarbon such as dichloromethane, chloroform, or 1,2-dichloroethane, preferably dichloromethane, at a temperature between 0° C. and 50° C., preferably between 20° C. and 30° C., using pressure tubes and a microwave oven if needed.

In an alternative approach outlined in Scheme 2d, compounds of the formula (IIc), as defined above in context of Scheme 2c, can be prepared in one synthetic step from compounds of formula (Vc), in which $R^1$, $R^2$, $R^3$, $R^4$ and L are as defined for the compounds of general formula (I), in which $R^{5E}$ represents a group suitable to act as a precursor of a —C(=O)OH or a tetrazol-5-yl group, preferably a group —C(=O)O—$C_{1-4}$-alkyl, in which $R^{p2}$ represents a hydrogen atom and $R^{p1}$ (see General Synthesis Route, Scheme 1) represents a —$(CH_2)_c$—OH group, in which in turn index "c" represents an integer selected from 0, 1, 2 or 3, by reacting with compounds of formula (IVe), in which indices "d" and "e", independently from each other, represent an integer selected from 1, 2, 3, 4, 5 and 6, with the proviso that the sum of the integers representing indices "c", "d" and "e" does not exceed 8, and $LG^6$ and $LG^7$ represent, independently from each other, a leaving group, preferably chloro, bromo or iodo, giving rise to the corresponding macrocyclic intermediates of formula (IIc). If compounds of formula (IVe) are being employed as (Z)-alkenes, macrocyclic compounds of formulas (IIc) can be obtained as single (Z) double bond isomers.

Said reaction can be advantageously accomplished by reacting a compound of formula (Vc) with a compound of formula (IVe) in the presence of a base such as an alkali carbonate or an alkali phosphate, preferably cesium carbonate, preferably in the presence of an alkali iodide, preferably sodium iodide (to convert $LG^6$ and/or $LG^7$ into iodo in situ), in a solvent such as dimethylformamide (DMF), 1,2-dimethoxyethane, bis-(2-methoxymethyl) ether or acetonitrile, at a temperature between 0° C. and 100° C., preferably between 15° C. and 75° C.

In a preferred embodiment of the invention, said reaction is performed in the presence of one to three equivalents (relative to the compound of formula (IVe) of sodium iodide, in a solvent selected from acetonitrile and bis-(2-methoxymethyl) ether, initially at a temperature between 15° C. and 40° C. for a period of 2 to 30 hours, followed by a temperature between 50° C. and 80° C., for a period of 2 to 8 hours.

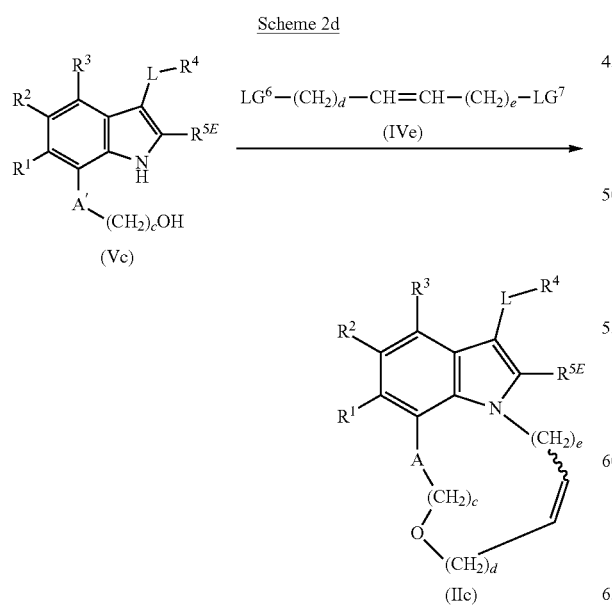

Scheme 2d

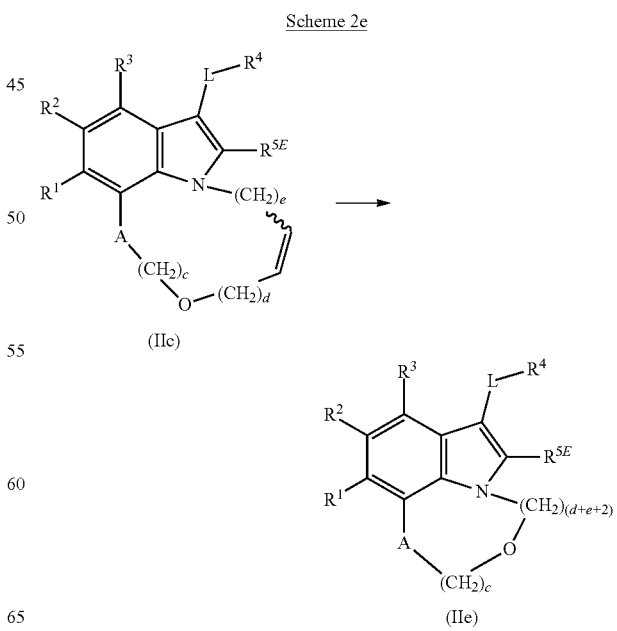

Scheme 2e

According to Scheme 2e, Compounds of formula (IIe), in which $R^7$ (which is a feature of group A as defined for the compounds of general formula (I)) and $R^6$ together form a $^{\#\#}$—$(CH_2)_c$—O—$(CH_2)_{(d+e+2)}$—$^\#$ group, in which $^\#$ represents the point of attachment to the indole nitrogen atom and $^{\#\#}$ represents the point of attachment to the pyrazole carbon atom bearing the $R^7$ substituent, can be obtained from compounds of formula (IIc), in which $R^1$, $R^2$, $R^3$, $R^4$ and L are as defined for the compounds of general formula (I), in which $R^{5E}$ represents a group suitable to act as a precursor of a —C(=O)OH or a tetrazol-5-yl group, preferably a group —C(=O)O—$C_{1-4}$-alkyl, and in which $R^7$ and $R^6$ together form a —$(CH_2)_c$—O—$(CH_2)_d$—CH=CH—$(CH_2)_e$— group as defined in context of Schemes 2c and 2d, by hydrogenation of the olefinic double bond.

Said hydrogenation of the olefinic double bond can be advantageously accomplished by catalytic hydrogenation which is well known to the person skilled in the art, e.g. by reacting a solution of a compound of formula (IIc) in a solvent such as methanol, ethanol, THF or ethyl acetate, with an atmosphere of hydrogen under ambient or elevated pressure, in the presence of a hydrogenation catalyst such as palladium on carbon.

atom bearing the $R^7$ substituent, can be obtained from compounds of formula (Vc), in which $R^1$, $R^2$, $R^3$, $R^4$ and L are as defined for the compounds of general formula (I), in which $R^{5E}$ represents a group suitable to act as a precursor of a —C(=O)OH or a tetrazol-5-yl group, preferably a group —C(=O)O—$C_{1-4}$-alkyl, in which $R^{P2}$ represents a hydrogen atom and $R^{P1}$ (see General Synthesis Route, Scheme 1) represents a —$(CH_2)_c$—OH group, in which in turn index "c" represents an integer selected from 0, 1, 2 or 3, by reacting with compounds of formula (IVf), in which index "f" represents an integer selected from 2, 3, 4, 5, 6, 7, 8 and 9, with the proviso that the sum of the integers representing indices "c" and "f" is at least 3 and does not exceed 10, and in which $LG^s$ and $LG^9$ represent, independently from each other, a leaving group, preferably bromo or iodo, giving rise to the corresponding macrocyclic intermediates of formula (IIf). Dependent on the reaction conditions and the choice of leaving groups $LG^s$ and $LG^9$, intermediate compounds of formula (IIIf) can be isolated and subsequently cyclised to the corresponding macrocyclic intermediates of formula (IIf).

Said reaction can be advantageously accomplished in one step by reacting a compound of formula (Vc) with a compound of formula (IVf), in which both $LG^8$ and $LG^9$ represent iodo, in the presence of a base such as an alkali carbonate or an alkali phosphate, preferably cesium carbonate, in a solvent such as dimethylformamide (DMF) or dimethylsulfoxide (DMSO), at a temperature between 0° C. and 100° C., preferably between 15° C. and 50° C.

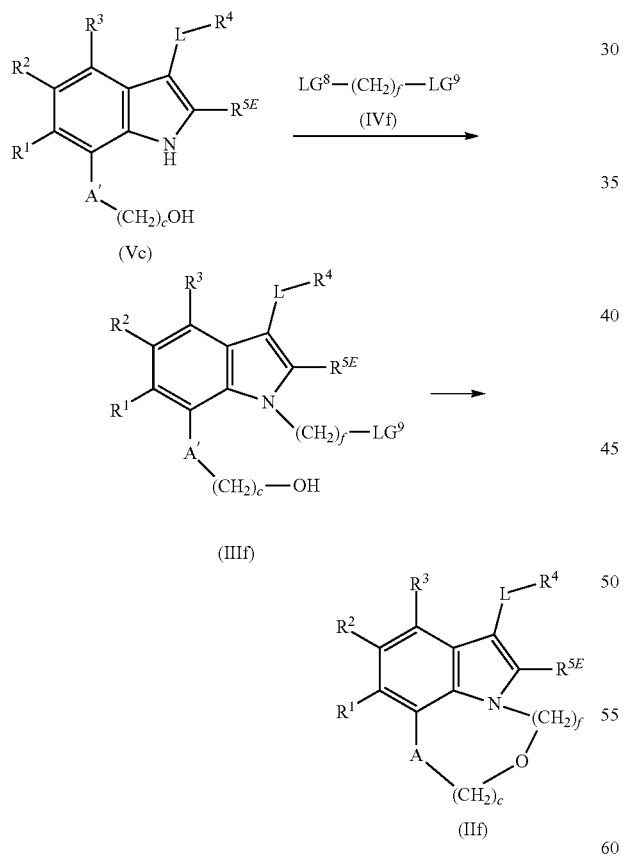

Scheme 2f

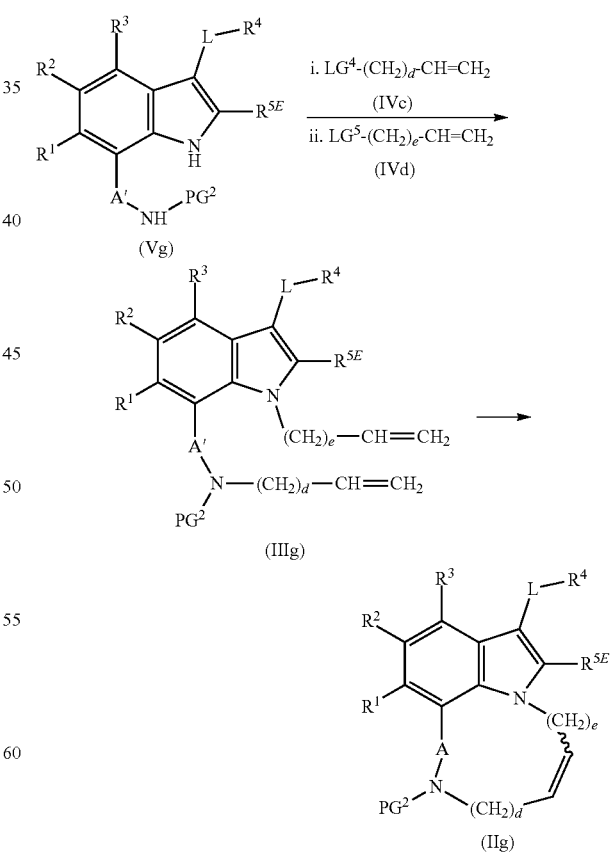

Scheme 2g

According to Scheme 2f, compounds of the formula (IIf), in which $R^7$ (which is a feature of group A as defined for the compounds of general formula (I)) and $R^6$ together form a $^{\#\#}$—$(CH_2)_c$—O—$(CH_2)_f$—$^\#$ group, in which $^\#$ represents the point of attachment to the indole nitrogen atom and $^{\#\#}$ represents the point of attachment to the pyrazole carbon According to Scheme 2g, compounds of formula (IIg), in which $R^7$ (which is a feature of group A as defined for the compounds of general formula (I)) and R⁶ together form a ##—N(PG²)-(CH₂)_d—CH=CH—(CH₂)_e—# group, in which # represents the point of attachment to the indole nitrogen atom and ## represents the point of attachment to the pyrazole carbon atom bearing the R⁷ substituent, can be obtained from compounds of formula (Vg), in which R¹, R², R³, R⁴ and L are as defined for the compounds of general formula (I), in which R^{5E} represents a group suitable to act as a precursor of a —C(=O)OH or a tetrazol-5-yl group, preferably a group —C(=O)O—C_{1-4}-alkyl, in which R^{P2} represents a hydrogen atom and R^{P1} (see General Synthesis Route, Scheme 1) represents a —NH-PG² group, in which PG² in turn represents a protective group for a nitrogen atom, such as benzyl, by reacting with compounds of formula (IVc), followed by compounds of formula (IVd), in which indices "d" and "e", independently from each other, represent an integer selected from 1, 2, 3, 4, 5 and 6, with the proviso that the sum of the integers representing indices "d" and "e" does not exceed 8, and LG⁴ and LG⁵, independently from each other, represent a leaving group, to give compounds of formula (IIIg), in which R^{P1} represents a —N(PG²)-(CH₂)_d—CH=CH₂ group, and in which R^{P2} represents a —(CH₂)_e—CH=CH₂ group. Subsequently, said compounds of formula (IIIg) can be subjected to a ring closing metathesis (RCM) reaction (see e.g. *Chem. Rev.*, 2009, 109 (8), pp 3783-3816), giving rise to the corresponding macrocyclic intermediates of formula (IIg). Optionally, the olefinic double bond present in formula (IIg) can be hydrogenated as discussed in context of Scheme 2e subsequently or on later stage.

The abovementioned sequence of transformations can be advantageously accomplished by deprotonating a compound of formula (Vg) with one equivalent of a suitable base, such as sodium hydride or cesium carbonate, in a suitable solvent, such as THF, dimethylformamide (DMF) or dimethylacetamide (DMA), followed by addition of a compound of formula (IVc), followed by the addition of one further equivalent of a suitable base, such as sodium hydride or cesium carbonate, followed by addition of a compound of formula (IVd). Whenever indices "d" and "e" are identical, said base can be added in one portion, followed by one reagent of formula (IVc) or (IVd). The subsequent macrocyclization is favorably accomplished by reacting a compound of formula (IIIg) in the presence of a catalyst suitable for the performance of a ring closing metathesis exemplified by but not limited to (1,3-bis(2,4,6-trimethylphenyl)-2-imidazolidinylidene)dichloro(phenylmethylene) (tricyclohexylphosphine)ruthenium or (1,3-bis-(2,4,6-trimethylphenyl)-2-imidazolidinylidene)dichloro(o-isopropoxyphenylmethylene)ruthenium, in a hydrocarbon such as benzene, toluene or xylene, preferably toluene, at a temperature between 50° C. and 120° C., preferably between 80° C. and 100° C., adding multiple portions of said catalyst over the reaction time, using pressure tubes and a microwave oven if needed.

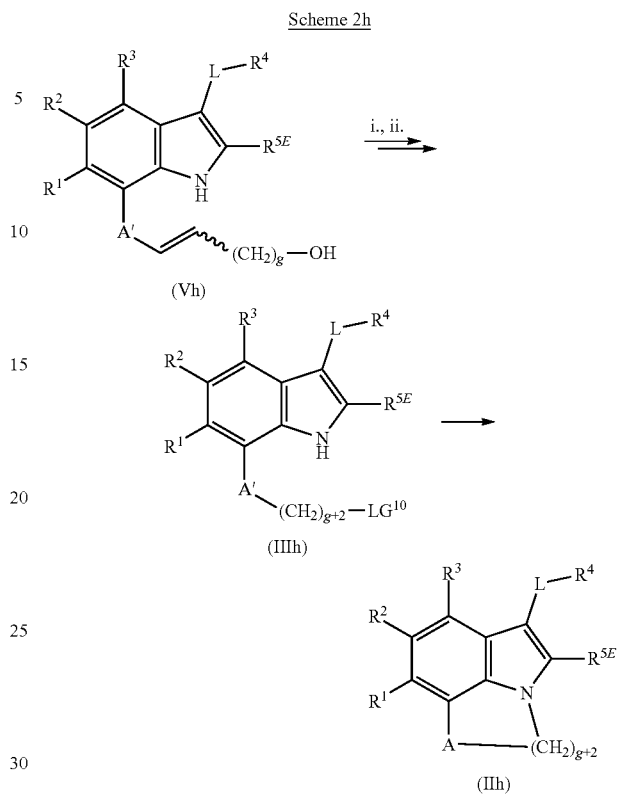

Scheme 2h

As outlined in Scheme 2h, compounds of formula (IIh), in which R⁷ (which is a feature of group A as defined for the compounds of general formula (I)) and R⁶ together form a —(CH₂)_{g+2}— group, can be obtained from compounds of formula (Vh), in which R¹, R², R³, R⁴ and L are as defined for the compounds of general formula (I), in which R^{5E} represents a group suitable to act as a precursor of a —C(=O)OH or a tetrazol-5-yl group, preferably a group —C(=O)O—C_{1-4}-alkyl, and in which R^{P2} represents a hydrogen atom and R^{P1} (see General Synthesis Route, Scheme 1) represents a —CH=CH—(CH₂)_g—OH group (in which the index "g" represents an integer selected from 2, 3, 4, 5, 6, 7, 8 and 9), by (i) conversion of said —CH=CH—(CH₂)_g—OH group into a —(CH₂)_{g+2}—OH group by means of catalytic hydrogenation, and (ii) conversion of said —(CH₂)_{g+2}—OH group into a —(CH₂)_{g+2}-LG¹⁰ group, to give compounds of formula (IIIh), in which R^{P1} represents a —(CH₂)_{g+2}-LG¹⁰ group (in which in turn LG¹⁰ represents a leaving group, preferably bromo), and in which R^{P2} represents a hydrogen atom. Subsequently, said compounds of formula (IIIh) can be subjected to an intramolecular nucleophilic substitution, giving rise to the corresponding macrocyclic intermediates of formula (IIh).

The abovementioned sequence of transformations can be advantageously accomplished by (step i) hydrogenating a compound of formula (Vh) in an atmosphere of hydrogen at a pressure between 1 and 20 bar, in ethanol as a solvent and in the presence of a palladium on charcoal hydrogenation catalyst, followed (step ii) by halogenation of the resulting —(CH₂)_{g+2}—OH group, e.g. by treatment with tetrabromomethane and triphenylphosphine in a halogenated hydrocarbon, such as dichloromethane, as a solvent. The subsequent macrocyclization can be favorably accomplished by reacting a compound of formula (IIIh) in the presence of a base such as potassium tert-butoxide, in an ethereal solvent such as 1,4-dioxane, THF or 1,2-dimethoxyethane, preferably 1,4-dioxane, at a temperature between 20° C. and 120° C., preferably between 60° C. and 100° C., using pressure tubes and a microwave oven if needed.

Starting materials of the formula (Vh) are available in analogy to Scheme 1, e.g. by employing a compound of formula (VI), in which $FG^2$ represents a halogen atom such as bromine, and in which $R^{p1}$ represents a —$(CH_2)$—OH group, which can be (a) oxidized by methods well known to the person skilled in the art, such as a Swern oxidation, to the corresponding aldehyde (in which $R^{p1}$ represents a —C(=O)H group), followed by (b) reacting said aldehyde in a well known Wittig or Wadsworth-Horner-Emmons olefination reaction with a suitable phosphonium salt, and (c) subsequently establishing the terminal hydroxy group from a precursor group present in said phosphonium salt, e.g. by removal of a protective group or reduction of a corresponding carboxylic acid ester to give the corresponding hydroxyalkenyl compound of formula (VI) in which $R^{p1}$ represents a —CH=CH—$(CH_2)_g$—OH group, and finally (d) a Suzuki coupling with a compound of formula (VII) as outlined in Scheme 1.

$(CH_2)_g$-$LG^{11}$ group, to give compounds of formula (IIIi), in which $R^{p1}$ represents a —CH=CH—$(CH_2)_g$-$LG^{11}$ group (in which in turn $LG^{11}$ represents a leaving group, preferably bromo), and in which $R^{p2}$ (see General Synthesis Route, Scheme 1) represents a hydrogen atom. Subsequently, said compounds of formula (IIIi) can be subjected to an intramolecular nucleophilic substitution, giving rise to the corresponding macrocyclic intermediates of formula (IIi).

The abovementioned conversion of the hydroxy group present in said —CH=CH—$(CH_2)_g$—OH group into a leaving group can be advantageously accomplished e.g. by halogenation, such as treatment with tetrabromomethane and triphenylphosphine in a halogenated hydrocarbon, such as dichloromethane, as a solvent. The subsequent macrocyclization can be favorably accomplished by reacting a compound of formula (IIIi) in the presence of a base such as cesium carbonate or potassium tert-butoxide, in an ethereal solvent such as 1,4-dioxane, THF or 1,2-dimethoxyethane, or a dipolar aprotic solvent such as dimethylformamide (DMF), dimethylacetamide (DMA) or N-methyl pyrrolidin-2-one, at a temperature between 20° C. and 120° C.

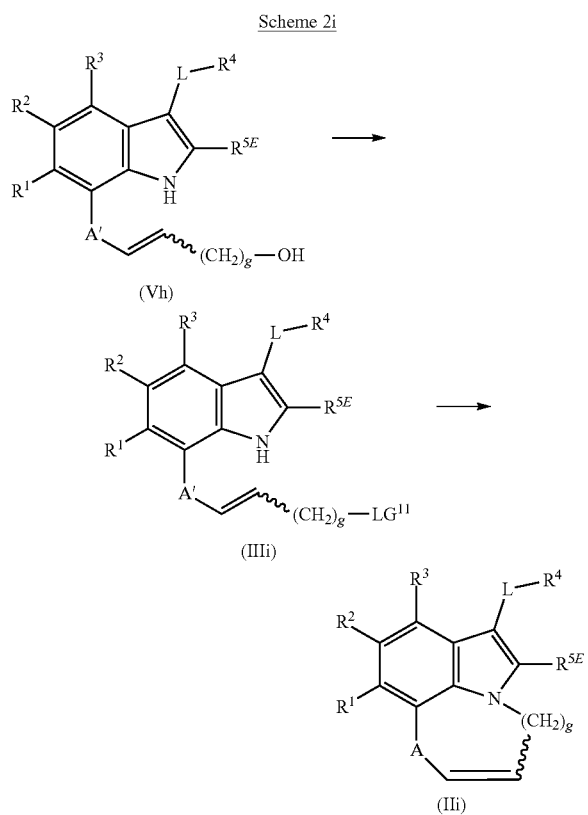

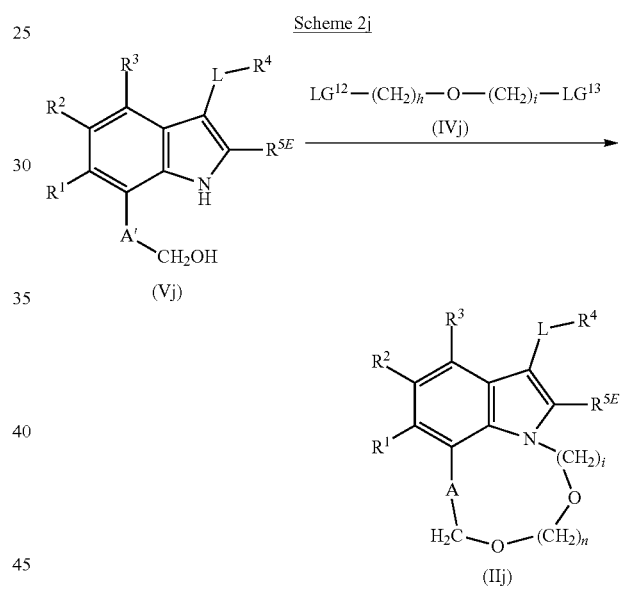

In an analogous fashion, and as shown in Scheme 2i, compounds of formula (IIi), in which $R^7$ (which is a feature of group A as defined for the compounds of general formula (I)) and $R^6$ together form a $^{\#\#}$—CH=CH—$(CH_2)_g$—$^\#$ group, in which $^\#$ represents the point of attachment to the indole nitrogen atom and $^{\#\#}$ represents the point of attachment to the pyrazole carbon atom bearing the $R^7$ substituent, can be obtained from compounds of formula (Vh), as defined in context of Scheme 2h, by conversion of its —CH=CH—$(CH_2)_g$—OH group into a —CH=CH—

As outlined in Scheme 2j, compounds of formula (IIj), in which $R^7$ (which is a feature of group A as defined for the compounds of general formula (I)) and $R^6$ together form an $^{\#\#}$—$CH_2$—O—$(CH_2)_h$—O—$(CH_2)_i$—$^\#$ group, in which $^\#$ represents the point of attachment to the indole nitrogen atom and $^{\#\#}$ represents the point of attachment to the pyrazole carbon atom bearing the $R^7$ substituent, can be obtained from compounds of formula (Vj), in which $R^1$, $R^2$, $R^3$, $R^4$ and L are as defined for the compounds of general formula (I), in which $R^{5E}$ represents a group suitable to act as a precursor of a —C(=O)OH or a tetrazol-5-yl group, preferably a group —C(=O)O—$C_{1-4}$-alkyl, in which $R^{p2}$ represents a hydrogen atom and $R^{p1}$ (see general Synthesis Route, Scheme 1) represents a hydroxymethyl group, by reaction with compounds of formula (IVj), in which the indices "h" and "i", independently from each other, represent an integer selected from 2, 3, 4, 5 and 6, with the proviso that the sum of the integers representing indices "h" and "i" does not exceed 8, and in which $LG^{12}$ and $LG^{13}$, independently from each other, represent a leaving group, preferably iodo), to directly give the corresponding macrocyclic intermediates of formula (IIj). If said indices "h" and "i" are different from each other, regioisomeric mixtures (inverse arrangement of "h" and "i" in the reaction product) may result which may be separated by methods known to the person skilled in the art, such as preparative HPLC.

Said reaction can be favorably accomplished by reacting a compound of formula (Vj) with a compound of formula (IVj) in the presence of a base such as an alkali carbonate or an alkali phosphate, preferably cesium carbonate, in a solvent such bis-(2-methoxyethyl) ether, at a temperature between 15° C. and 100° C., preferably between 15° C. and 80° C.

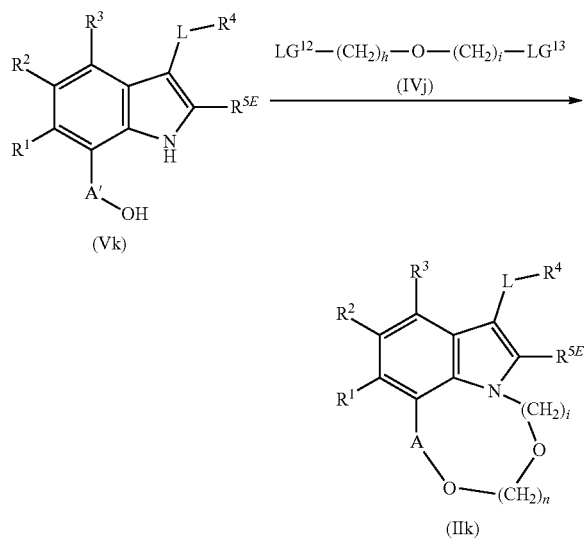

As outlined in Scheme 2k, compounds of formula (IIk), in which $R^{10}$ (which is a feature of group A as defined for the compounds of general formula (I)) and $R^6$ together form an $^{\#\#}$—O—$(CH_2)_h$—O—$(CH_2)_i$—$^{\#}$ group, in which $^{\#}$ represents the point of attachment to the indole nitrogen atom and $^{\#\#}$ represents the point of attachment to the phenyl, pyridinyl, pyrimidinyl or pyridazinyl carbon atom bearing the $R^{10}$ substituent, can be obtained from compounds of formula (Vk), in which $R^1$, $R^2$, $R^3$, $R^4$ and L are as defined for the compounds of general formula (I), in which $R^{5E}$ represents a group suitable to act as a precursor of a —C(=O)OH or a tetrazol-5-yl group, preferably a group —C(=O)O—$C_{1-4}$-alkyl, in which $R^{P2}$ represents a hydrogen atom and in which $R^{P1}$ (see General Synthesis Route, Scheme 1) represents a hydroxy group, by reaction with compounds of formula (IVj), in which the indices "h" and "i", independently from each other, represent an integer selected from 2, 3, 4, 5 and 6, with the proviso that the sum of the integers representing indices "h" and "i" does not exceed 8, and in which $LG^{12}$ and $LG^{13}$ independently from each other represent a leaving group, preferably bromo), to directly give the corresponding macrocyclic intermediates of formula (IIk). If said indices "h" and "i" are different from each other, regioisomeric mixtures (inverse arrangement of "h" and "i" in the reaction product) may result which may be separated by methods known to the person skilled in the art, such as preparative HPLC.

Said reaction can be favorably accomplished by reacting a compound of formula (Vk) with a compound of formula (IVj) in the presence of a base such as an alkali carbonate or an alkali phosphate, preferably cesium carbonate, in a dipolar aprotic solvent such as dimethylformamide (DMF), dimethylacetamide (DMA) or N-methyl pyrrolidin-2-one, preferably DMA, at a temperature between 20° C. and 150° C., preferably between 60° C. and 100° C.

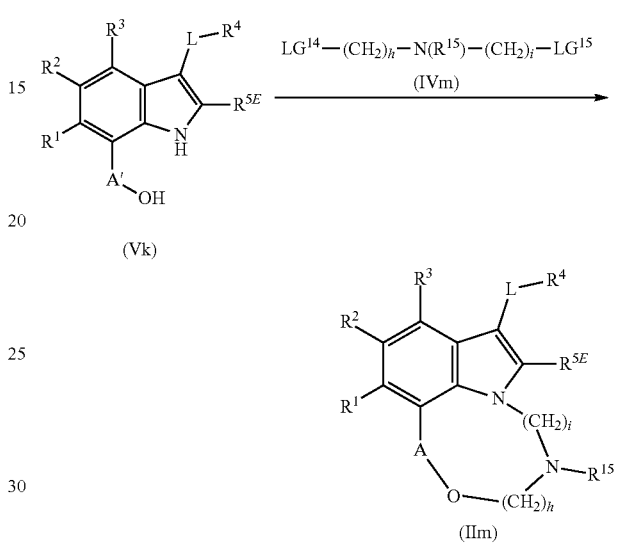

In an analogous fashion, and as outlined in Scheme 2m, compounds of formula (IIm), in which $R^{10}$ (which is a feature of group A as defined for the compounds of general formula (I)) and $R^6$ together form an $^{\#\#}$—O—$(CH_2)_h$—N$(R^{15})$—$(CH_2)_i$—$^{\#}$ group, in which $^{\#}$ represents the point of attachment to the indole nitrogen atom and $^{\#\#}$ represents the point of attachment to the phenyl, pyridinyl, pyrimidinyl or pyridazinyl carbon atom bearing the $R^{10}$ substituent, can be obtained from compounds of formula (Vk), as defined in context of Scheme 2k, by reaction with compounds of formula (IVm), in which the indices "h" and "i", independently from each other, represent an integer selected from 2, 3, 4, 5 and 6, with the proviso that the sum of the integers representing indices "h" and "i" does not exceed 8, and in which $LG^{14}$ and $LG^{15}$, independently from each other represent a leaving group, preferably bromo), and in which $R^{15}$ is as defined for the compounds of the general formula (I), to directly give the corresponding macrocyclic intermediates of formula (IIm). If said indices "h" and "i" are different from each other, regioisomeric mixtures (inverse arrangement of "h" and "i" in the reaction product) may result which may be separated by methods known to the person skilled in the art, such as preparative HPLC.

Said reaction can be favorably accomplished by reacting a compound of formula (Vk) with a compound of formula (IVm) in the presence of a base such as an alkali carbonate or an alkali phosphate, preferably cesium carbonate, in a dipolar aprotic solvent such as dimethylformamide (DMF), dimethylacetamide (DMA) or N-methyl pyrrolidin-2-one, at a temperature between 20° C. and 150° C.

Scheme 2n

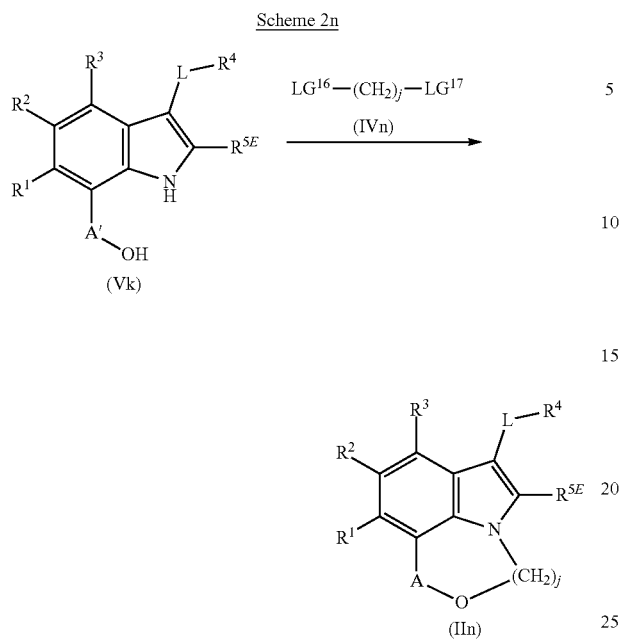

As outlined in Scheme 2n, compounds of formula (IIn), in which $R^{10}$ (which is a feature of group A as defined for the compounds of general formula (I)) and $R^6$ together form an $^{\#\#}$—O—$(CH_2)_j$—$^{\#}$ group, in which $^{\#}$ represents the point of attachment to the indole nitrogen atom and * represents the point of attachment to the phenyl, pyridinyl, pyrimidinyl or pyridazinyl carbon atom bearing the $R^{10}$ substituent, can be obtained from compounds of formula (Vk), as defined in context of Scheme 2k, by reaction with compounds of formula (IVn), in which $LG^{16}$ and $LG^{17}$, independently from each other, represent a leaving group, preferably bromo), and in which index "j" represents an integer selected from 2, 3, 4, 5, 6, 7, 8 and 9, to directly give the corresponding macrocyclic intermediates of formula (IIn).

Said reaction can be favorably accomplished by reacting a compound of formula (Vk) with a compound of formula (IVn) in the presence of a base such as an alkali alkoxide, preferably potassium 2-methylpropan-2-olate (herein also referred to as potassium tert.-butylate or potassium tert.-butoxide), in an ethereal solvent such as 1,4-dioxane, THF or 1,2-dimethoxyethane, preferably THF, at a temperature between 20° C. and 120° C., preferably between 60° C. and 100° C., using pressure tubes and a microwave oven if needed.

Scheme 2o

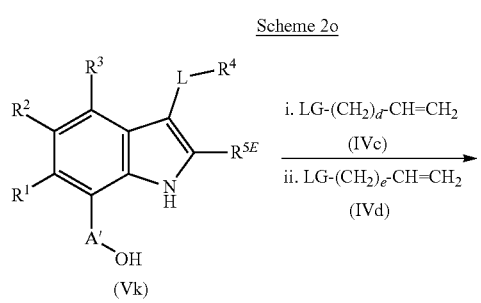

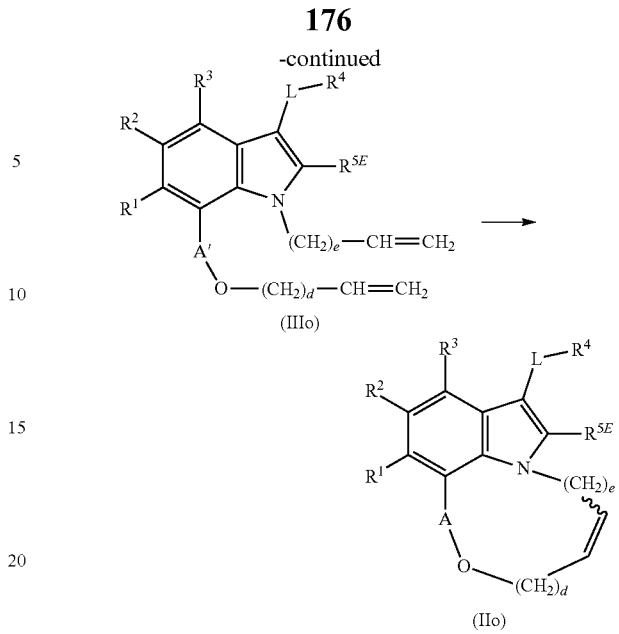

According to Scheme 2o, and in some analogy to Scheme 2c, compounds of formula (IIo), in which $R^{10}$ (which is a feature of group A as defined for the compounds of general formula (I)) and $R^6$ together form a $^{\#\#}$—O—$(CH_2)_d$—CH=CH—$(CH_2)_e$—$^{\#}$ group, in which $^{\#}$ represents the point of attachment to the indole nitrogen atom and $^{\#\#}$ represents the point of attachment to the phenyl, pyridinyl, pyrimidinyl or pyridazinyl carbon atom bearing the $R^{10}$ substituent, can be obtained from compounds of formula (Vk), as defined in context of Scheme 2k, by reacting with compounds of formula (IVc), followed by compounds of formula (IVd), in which indices "d" and "e", independently from each other, represent an integer selected from 1, 2, 3, 4, 5 and 6, with the proviso that the sum of the integers representing indices "d" and "e" does not exceed 7, and in which $LG^4$ and $LG^5$, independently from each other, represent a leaving group, to give compounds of formula (IIIo), in which $R^{p1}$ represents a —O—$(CH_2)_d$—CH=CH$_2$ group, and in which $R^{p2}$ represents a —$(CH_2)_e$—CH=CH$_2$ group. Subsequently, said compounds of formula (IIIo) can be subjected to a ring closing metathesis (RCM) reaction (see e.g. *Chem. Rev.*, 2009, 109 (8), pp 3783-3816), giving rise to the corresponding macrocyclic intermediates of formula (IIo).

The abovementioned sequence of transformations can be advantageously accomplished by deprotonating a compound of formula (Vk) with on equivalent of a suitable base, such as sodium hydride or cesium carbonate, in a suitable solvent, such as THF, dimethylformamide (DMF) or dimethylacetamide (DMA), followed by addition of a compound of formula (IVc), followed by the addition of one further equivalent of a suitable base, such as sodium hydride or cesium carbonate, followed by addition of a compound of formula (IVd). Whenever indices "d" and "e" are identical, said base can be added in one portion, followed by one reagent of formula (IVc) or (IVd). The subsequent macrocyclization is favorably accomplished by reacting a compound of formula (IIIo) in the presence of a catalyst suitable for the performance of a ring closing metathesis exemplified by but not limited to (1,3-bis(2,4,6-trimethylphenyl)-2-imidazolidinylidene)dichloro(phenylmethylene)(tricyclohexylphosphine)ruthenium
or
(1,3-bis-(2,4,6-trimethylphenyl)-2-imidazolidinylidene)dichloro(o-isopropoxyphenylmethylene)ruthenium,
in a halogenated hydrocarbon such as dichloromethane, chloroform, or 1,2-dichloroethane, at a temperature between 0° C. and 50° C., using pressure tubes and a microwave oven if needed.

C. Conversion into Compounds of Formula (I), Scheme 3

Scheme 3

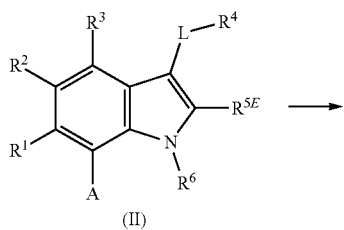

(II)

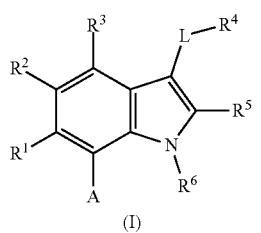

(I)

According to Scheme 3, compounds of formula (II), such as the compounds of the formulae (IIa), (IIb), (IIc), (IIe), (IIf), (IIg), (IIh), (IIi), (IIj), (IIk), (IIm), (IIn) and (IIo), in which $R^1$, $R^2$, $R^3$, $R^4$, $R^6$, A and L are as defined for the compounds of general formula (I), and in which $R^{5E}$ represents a group suitable to act as a precursor of a —C(=O)OH or a tetrazol-5-yl group, preferably a carboxylic ester group, such as e.g. a —C(=O)O—$C_{1-4}$-alkyl group or a benzyl ester, can be readily converted into compounds of formula (I) by transforming group $R^{5E}$ into group $R^5$ as defined for the compounds of general formula (I), preferably by reacting with an alkali hydroxide, such as potassium hydroxide, sodium hydroxide, lithium hydroxide, preferably lithium hydroxide, in a mixture of water with THF and/or an aliphatic alcohol of the formula $C_1$-$C_3$-alkyl-OH, preferably methanol or ethanol, at a temperature between 0° C. and 100° C., preferably between 20° C. and 60° C. and subsequent usual workup as known by the person skilled in the art and as for example disclosed in the experimental section.

Said compounds of general formula (I) may be obtained as free acids or converted into pharmaceutically acceptable salts thereof, such as alkali salts, e.g. sodium or potassium salts, earth alkali salts, e.g. magnesium or calcium salts, and ammonium salts, e.g. ammonium ($NH_4^+$), diethylammonium (herein also referred to as N-ethylethanamine salts) or triethylammonium salts, by methods known to the person skilled in the art. Compounds of the invention featuring a quarternary nitrogen atom, such as those obtainable from macrocyclic intermediates of formula (IIb), are typically isolated as inner carboxylate salts or as salts with a counteranion of the quarternary nitrogen, such as chloride, bromide, methylsulfonate, and the like. Further, compounds of formula (I) in which $R^5$ represents a free carboxylic acid group can be optionally converted into an acylsulfonamide according to methods known to the person skilled in the art (see for example: *Bioorg. Med Chem. Lett.* 2006, 16, 3639-3641; *Bioorg. Med Chem. Lett.* 2012, 22, 713-717; *Org. Lett.* 2012, 14(2), 556-559).

Further, single enantiomers of said compounds of general formula (I) may be obtained by methods known to the person skilled in the art, such as preparative HPLC on a chiral stationary phase, as described supra, and as exemplified in the Experimental Section, infra.

D. Synthesis Routes to Starting Materials of Formulae (VI) and (VII); Alternative Synthesis Routes to Compounds of Formula (I), Schemes 4a-4f As outlined in Schemes 4a, 4b and 4c below, various approaches, which are intended to illustrate but not to limit the synthetic routes available to the person skilled in the art for this purpose, can be followed in order to prepare starting materials of the formula (VI), as defined in the context of Scheme 1, supra, i.e. in which A', together with the group $R^{P1}$ attached to it, represents a group suitable to act as precursor of a group A as defined for the compounds of general formula (I), and in which $FG^2$, in combination with the group $FG^1$ present in formula (VII), represents a pair of functional groups together enabling a Suzuki coupling; either $FG^1$ represents chloro, bromo, iodo or a trifluoromethanesulfonyl- group and $FG^2$ represents a group —B(OR$^B$)$_2$ as defined supra, or vice versa. Preferably, $FG^2$ represents bromo. Conversion of compounds, in which $FG^2$ represents bromo, into compounds in which $FG^2$ represents a group —B(OR$^B$)$_2$, is possible on various steps of the outlined synthesis routes using methods well known to the person skilled in the art.

Scheme 4a

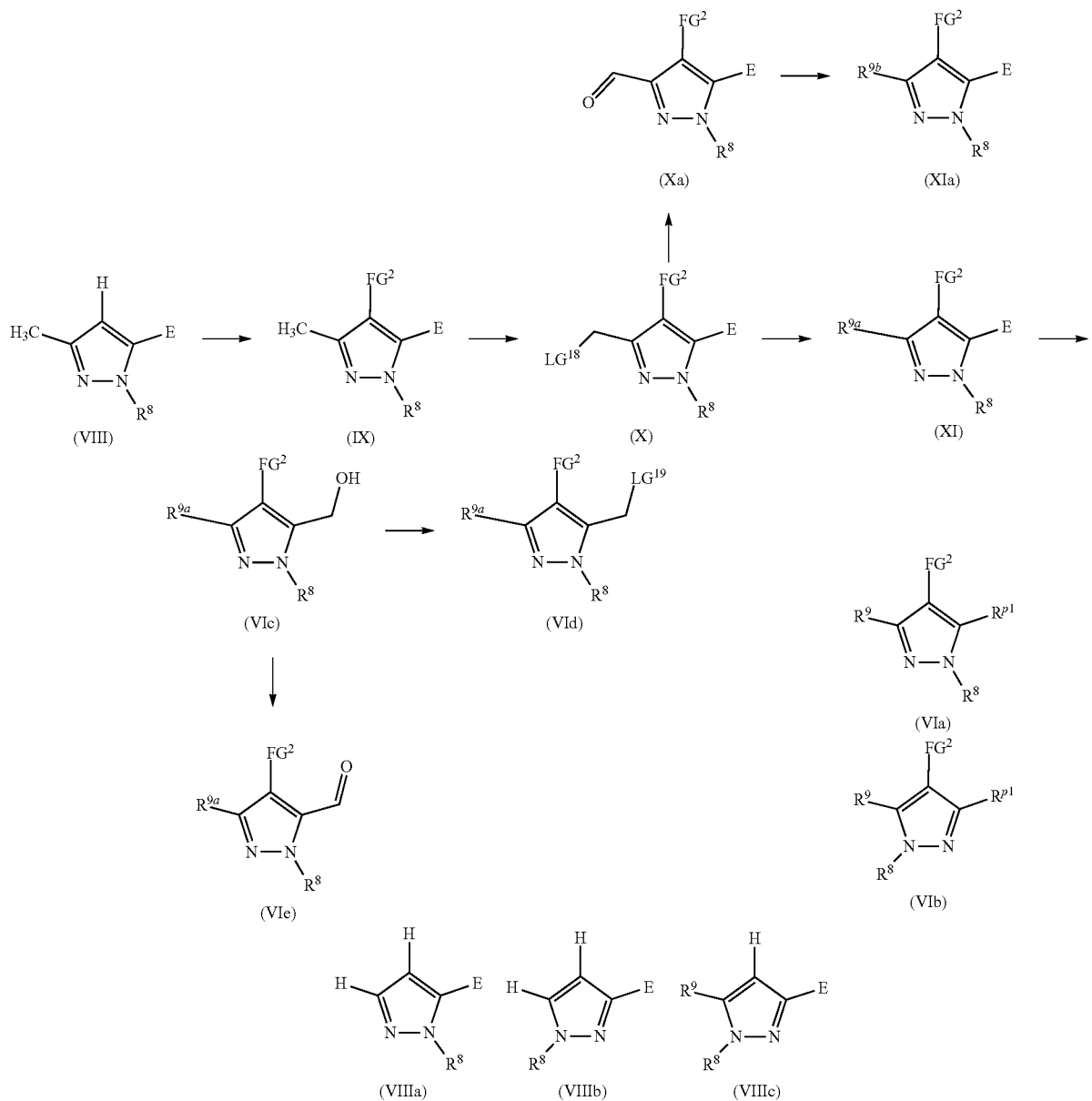

Scheme 4a illustrates synthesis routes enabling the preparation of compounds of formula (VI), in which A' is derived from pyrazole, namely compounds of formulae (VIa), (VIb), (VIc), (VId) and (VIe), all constituting sub-compartments for formula (VI), wherein (VIc), (VId) and (VIe), in turn, constitute sub-compartments of formula (VIa).

Starting from well-known pyrazole carboxylates of formula (VIII), in which E represents a group —C(=O)O—$C_1$-$C_6$-alkyl, and in which $R^8$ is defined as for the compounds of general formula (I), treatment of said compounds of formula (VIII) with an N-halo succinimide, preferably N-bromo succinimide, or with an elemental halogen such as bromine ($Br_2$) e.g. in glacial acetic acid, can be used to prepare compounds of formula (IX), in which $FG^2$ represents chloro, bromo, iodo, preferably bromo. Said compounds of formula (IX) can be reacted again with an N-halo succinimide, preferably N-bromo succinimide, but in the presence of a radical starter such as benzoyl peroxide at this time, to form compounds of formula (X), in which $LG^{18}$ represents chloro, bromo, iodo, preferably bromo. Reaction of said compounds of formula (X) e.g. with suitable alcohols or phenols, preferably in the presence of a suitable base, can be used for further elaboration of compounds of formula (XI), in which $R^{9a}$ represents a group such as an alkoxymethyl, heterocycloxymethyl, arylmethoxymethyl or aryloxymethyl group, thus constituting a subset of the group $R^9$ as defined for the compounds of general formula (I). The —C(=O)O—$C_1$-$C_6$-alkyl group present in compounds of formula (XI) can then be reduced to the corresponding primary alcohols of formula (VIc), e.g. using lithium aluminium hydride or diisobutyl aluminium hydride. Said primary alcohols of formula (VIc) can be further elaborated to compounds of formula (VId), in which LG$^{19}$ represents a leaving group, preferably bromo, e.g. by treatment with tetrabromomethane and triphenylphosphine, or to aldehydes of formula (VIe), e.g. by the well-known Swern oxidation. Hence, said processing of the —C(=O)O—C$_1$-C$_6$-alkyl group present in compounds of formula (XI) results in the formation of suitable R$^{p1}$ groups. Further R$^{p1}$ groups and their precursors can be elaborated from commercially available starting materials and/or using methods well known to the person skilled in the art; for specific instructive examples, see e.g. the protocols relating to Intermediates 20, 21, 22, 78 and 79 in the Experimental Section, infra.

Further, pyrazole-based intermediates of formula (XIa), in which R$^{9b}$ represents a group selected from a C$_1$-C$_4$-haloalkyl or C$_2$-C$_4$-haloalkenyl group, R$^{9b}$ thus constituting yet another subset of the group R$^9$ as defined for the compounds of general formula (I), can be prepared from abovementioned compounds of formula (X), by conversion of the group —CH$_2$LG$^{18}$ into a formyl group by well-known methods, such as (i.) nucleophilic substitution of the group LG$^{18}$ with an alkali acetate, such as potassium acetate, followed by (ii.) cleavage of the resulting actoxymethyl group e.g. with potassium carbonate in ethanol reduction and (iii.) oxidation with an agent such as manganese dioxide, to give formylpyrazole derivatives of formula (Xa). Said formylpyrazole derivatives of formula (Xa) can subsequently converted into intermediates of formula (XIa) as defined supra e.g. using known methods, e.g. by reacting with difluoro(triphenylphosphonio)acetate (see e.g. *J. Org. Chem.* 2014, 79, 7122-7131 or *Chem. Commun.* 2013, 49, 7513-7515).

Compounds of formula (VIII) are well known to the person skilled in the art and are commercially available in many cases, or, alternatively, can be prepared according to known methods (see e.g. *Chem. Rev.* 2011, 111, 6984-7034; JP 2001335564 A; *Org. Lett.*, 2011, 13 (6), pp 1436-1439; *J. Org. Chem.* 2003, 68(15), 5977-5982) from readily available precursor compounds; for specific examples see e.g. the protocols relating to Intermediates 92, 96 and 122).

In an analogous fashion, pyrazole carboxylates of formula (VIIIa), in which E represents a group —C(=O)O—C$_1$-C$_6$-alkyl, and in which R$^8$ is defined as for the compounds of general formula (I), can be elaborated into compounds of formula (VIa), in which R$^9$ represents a hydrogen atom. Likewise, compounds of formula (VIa), in which R$^9$ represents a methyl group can be prepared by directly subjecting compounds of formula (IX) to a reduction e.g. using lithium aluminium hydride or diisobutyl aluminium hydride.

Furthermore, regioisomeric pyrazole carboxylates of formula (VIIIb) and (VIIIc) can be elaborated into pyrazole derivatives of formula (VIb), in analogy to the conversion of compounds of formula (VIII) into compounds of formulae (VIc), (VId) and (VIe), supra.

Scheme 4b

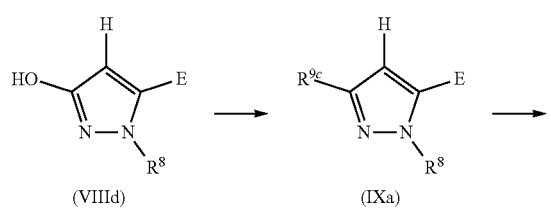

(VIIId) → (IXa) →

-continued

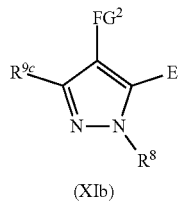

(XIb)

As outlined in Scheme 4b, pyrazole intermediates of formula (XIb), in which R$^{9c}$ represents a C$_1$-C$_6$-alkyl-O— group or a C$_1$-C$_4$-haloalkoxy group, R$^{9c}$ thus constituting yet another subset of the group R$^9$ as defined for the compounds of general formula (I), can be prepared from hydroxy pyrazoles of formula (VIIId), in which E represents a group —C(=O)O—C$_1$-C$_6$-alkyl, and R$^8$ is defined as for the compounds of general formula (I), by reacting with a compound suitable for the introduction of R$^{9c}$, such as a compound of the formula C$_1$-C$_6$-alkyl-Br, C$_1$-C$_6$-alkyl-I or C$_1$-C$_4$-haloalkyl-I, or with sodium chloro(difluoro)acetate, in the presence of an alkali carbonate, preferably potassium carbonate or caesium carbonate, in a solvent such as N,N-dimethylformamide, to give compounds of formula (IXa). Subsequent treatment of said compounds of formula (IXa) with an N-halo succinimide, preferably N-bromo succinimide, e.g. in acetonitrile, or with an elemental halogen such as bromine (Br$_2$) e.g. in glacial acetic acid, can be used to prepare compounds of formula (XIb), in which FG$^2$ represents chloro, bromo, iodo, preferably bromo.

Scheme 4c

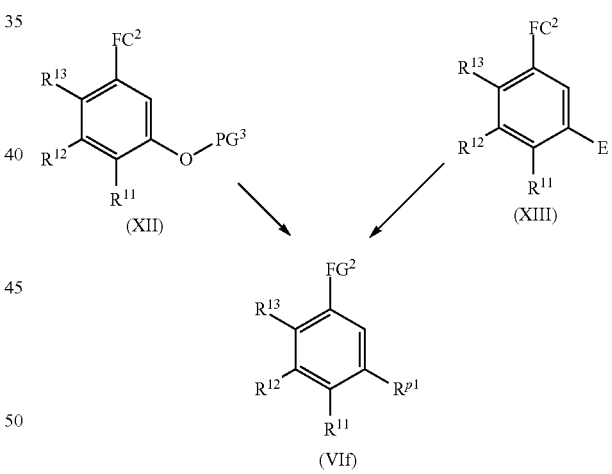

Scheme 4c illustrates synthesis routes enabling the preparation of compounds of formula (VI), in which A' is derived from phenyl, pyridinyl, pyrimidinyl or pyridazinyl, namely compounds of formula (VIf), constituting yet another subcompartment of formula (VI).

Starting from compounds of formula (XII), in which R$^{11}$, R$^{12}$, and R$^{13}$ are as defined for the compounds of general formula (I), and wherein one or two of the groups selected from CR$^{11}$, CR$^{12}$ or CR$^{13}$ may be replaced by a nitrogen atom, and in which FG$^2$, in combination with the group FG$^1$ present in formula (VII), represents a pair of functional groups together enabling a Suzuki coupling; either FG$^1$ represents chloro, bromo, iodo or a trifluoromethanesulfonyl- group and FG$^2$ represents a group —B(OR$^B$)$_2$ as defined supra, or vice versa, and in which PG³ represents a protective group, compounds of formula (VIf), in which R^{p1} represents a hydroxy group, can be readily obtained. Likewise, compounds of formula (XIII), in which R¹¹, R¹² and R¹³ are as defined for the compounds of general formula (I), and wherein one or two of the groups selected from CR¹¹, CR¹² or CR¹³ may be replaced by a nitrogen atom, and in which FG², in combination with the group FG¹ present in formula (VII), represents a pair of functional groups together enabling a Suzuki coupling; either FG¹ represents chloro, bromo, iodo or a trifluoromethanesulfonyl- group and FG² represents a group —B(OR^B)₂ as defined supra, or vice versa, and E represents a group —C(=O)O—C₁-C₆-alkyl, can be converted into compounds of formula (VIf), in which R^{p1} represents a —CH₂—OH group, a —C(=O)H group, or a —CH₂-LG²⁰ group, in which LG²⁰ represents a leaving group, preferably bromo, in analogy to the methods discussed in the context of the preceding Schemes, in particular Scheme 4a.

Compounds of formulae (XII) and (XIII) are commercially available, and known to the person skilled in the art, in considerable variety. Using known methods, groups R¹¹, R¹² and R¹³ can be broadly modified using known methods at various stages of the synthesis. Protective groups as present in compounds of formula (XII), and methods of their removal, are well known to the person skilled in the art, see e.g. T.W. Greene and P.G.M. Wuts in Protective Groups in Organic Synthesis, 4$^{th}$ edition, Wiley 2006.

Indole based starting materials of formula (VII), in which R¹, R², R³, R⁴ and L are as defined for the compounds of general formula (I), in which R^{5E} represents a group suitable to act as a precursor of a —C(=O)OH or a tetrazol-5-yl group, preferably a group —C(=O)O—C₁₋₄-alkyl, and in which FG¹ represents chloro, bromo, iodo, a trifluoromethanesulfonyl- group or a group —B(OR^B)₂, preferably a group —B(OR^B)₂, can be prepared using methods well known to the person skilled in the art, see e.g. Journal of Medicinal Chemistry, 2015, 58, 2180-2194. Said approach is illustrated in detail by the protocols describing the synthesis of Intermediates 13 to 19 in the experimental section, infra. Said group —B(OR^B)₂ may be a boronic acid moiety (R^B=H) or an alkyl ester of the boronic acid, e.g. its isopropyl ester (R^B=C₁-C₄-alkyl, e.g. —CH(CH₃)₂), or an ester derived from a diol such as pinacol in which the boronic acid intermediate forms a cyclic boronic ester, preferably a 4,4,5,5-tetramethyl-1,3,2-dioxaborolane (R^B-R^B=C₂-C₆-alkylene, preferably —C(CH₃)₂—C(CH₃)₂—). Alternatively to boronic acid derivatives, also tetrafluoroborates, in which —BF₄⁻ replaces the —B(OR^B)₂ moiety, can also be employed.

Scheme 4d

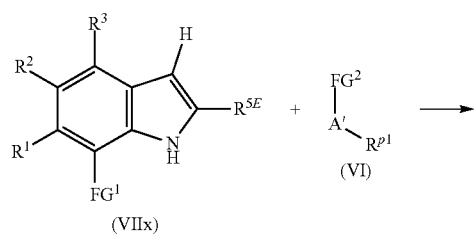

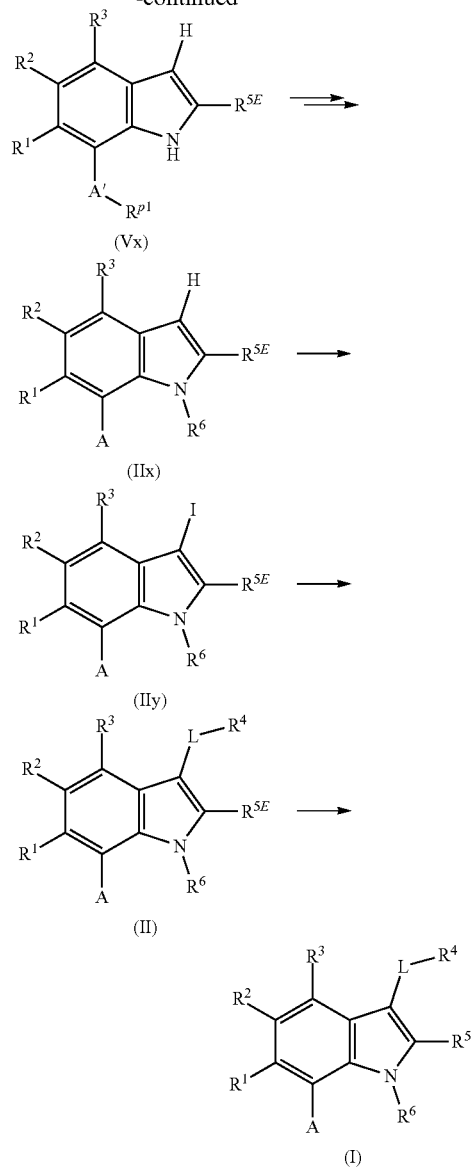

Scheme 4d outlines a modified general synthesis route for compounds of general formula (I) which employs indole starting materials of formula (VIIx) which differ from aforementioned indole starting materials of formula (VII) in that the C-3 carbon atom of the indole moiety is not substituted by -L-R⁴ but completely void of substitution.

In a general sense, and in analogy to the discussion regarding Scheme 1, indole starting materials of formula (VIIx), in which R¹, R² and R³ are as defined for the compounds of general formula (I), in which R^{5E} represents a group suitable to act as a precursor of a —C(=O)OH or a tetrazol-5-yl group, preferably a group —C(=O)O—C₁₋₄-alkyl, and in which FG¹ represents chloro, bromo, iodo, a trifluoromethanesulfonyl- group or a group —B(OR^B)₂, preferably a group —B(OR^B)₂, can be reacted in a well-known Suzuki coupling with compounds of formula (VI), in which A', together with the group R^{p1} attached to it, represents a group suitable to act as precursor of a group A as defined for the compounds of general formula (I), to give compounds of formula (Vx). Said indole starting materials of formula (VIIx) are well known to the person skilled in the art and are commercially available in certain cases. In a subsequent step (or series of steps), the macrocyclic core can be elaborated using approaches such as those outlined and discussed in the context of Schemes 2a to 20, or analogous methods, to furnish macrocyclic intermediate compounds of formula (IIx). Said intermediate compounds of formula (IIx) can be subsequently subjected to a halogenation reaction, e.g. with a N-halosuccinimide, such as N-iodosuccinimide, in a solvent such as tetrahydrofurane, at a temperature between 0° C. and 80° C., to give intermediate compounds of formula (IIy), in which the hitherto unsubstituted C-3 carbon of the indole is halogenated, preferably iodinated, allowing to subject said compounds of formula (IIy) to various transition metal catalysed, preferably palladium catalysed coupling reactions suitable for the introduction of a group -L-$R^4$, in which $R^4$ and L are as described for the compounds of general formula (I), or a suitable precursor group. Such reagents may be alkynes (to be employed in the well-known Sonogashira coupling), or vinylboronic acid derivatives (to be employed in the well-known Suzuki coupling). Conversion of the thus introduced alkenyl or alkynyl substituents attached to C-3 of the indole can be converted into L-$R^4$ groups by well-known methods such as catalytic hydrogenolysis or hydroboration, followed by a Mitsunobu coupling (see for example: K. C. K. Swamy et al, Chem. Rev. 2009, 109, 2551), to give compounds of formula (II), which can be converted into compounds of general formula (I) as described in the context of Scheme 3, supra.

Said vinylboronic acid derivative may be void of further substitution, rendering further elaboration of the -L-$R^4$ group e.g. via hydroboration and Mitsunobu etherification mandatory, or may already feature e.g. an allylic ether to a group $R^4$ as defined for the compounds of general formula (I) and as shown in Scheme 4e, limiting further elaboration to a hydrogenation of the olefinic double bond present in the resulting intermediates of formula (IIz-1) to give advanced intermediates of formula (IIz-2).

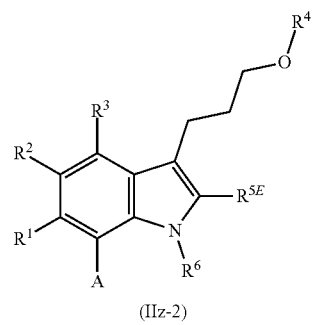

(IIz-2)

Scheme 4e

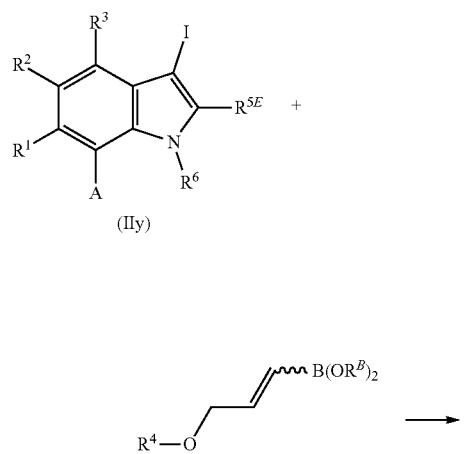

Scheme 4f

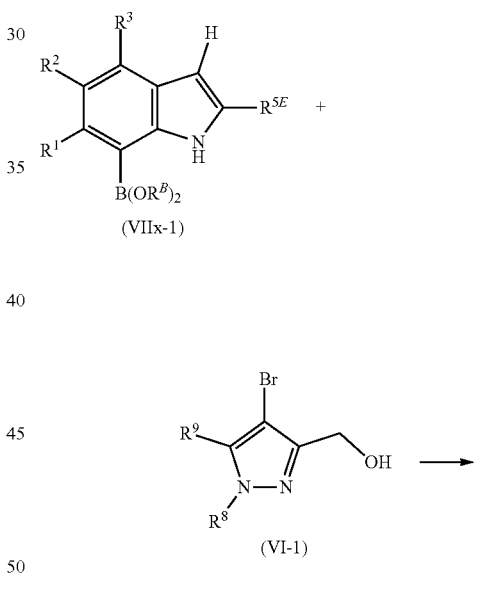

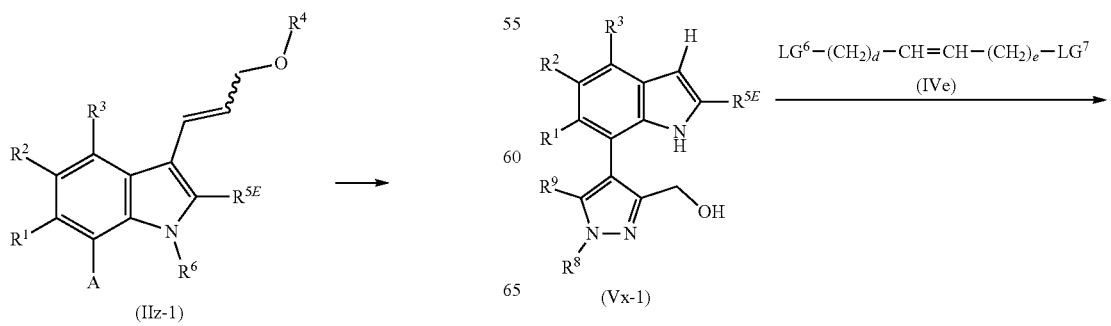

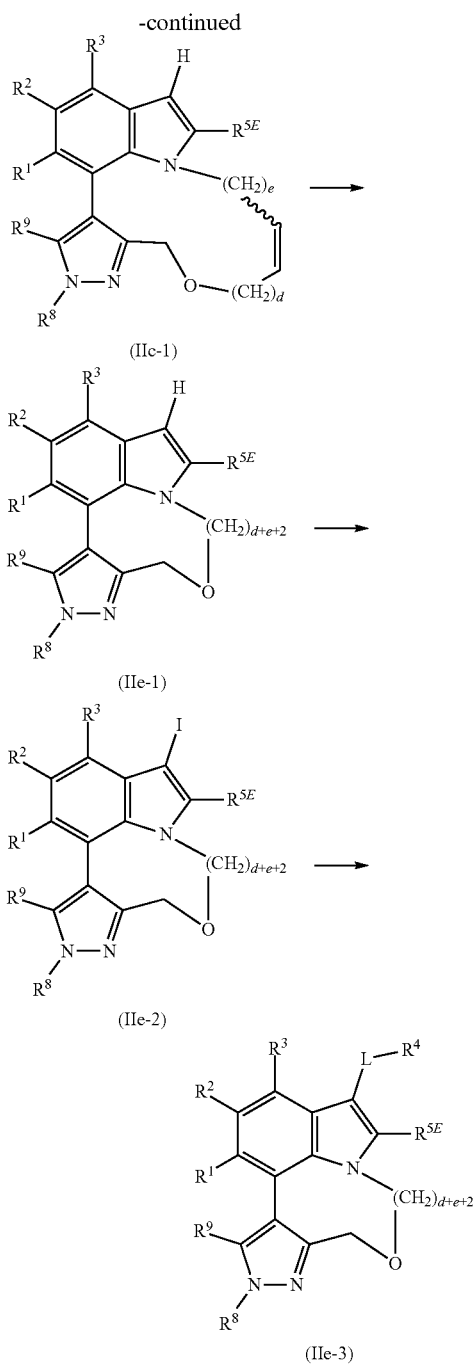

Scheme 4f summarises a more specific synthetic route exemplifying but not limiting the general approach outlined in Scheme 4d, starting from indolylboronic acid derivatives of formula (VIIx-1), in which $R^1$, $R^2$ and $R^3$ are as defined for the compounds of general formula (I), in which $R^{5E}$ represents a group suitable to act as a precursor of a —C(=O)OH or a tetrazol-5-yl group, preferably a group —C(=O)O—$C_{1-4}$-alkyl, and in which $FG^1$ represents a group —B(OR$^B$)$_2$. Said group —B(OR$^B$)$_2$ may be a boronic acid moiety ($R^B$=—H) or an alkyl ester of the boronic acid, e.g. its isopropyl ester ($R^B$=$C_1$-$C_4$-alkyl, e.g. —CH(CH$_3$)$_2$), or an ester derived from a diol such as pinacol in which the boronic acid intermediate forms a cyclic boronic ester, preferably a 4,4,5,5-tetramethyl-1,3,2-dioxaborolane ($R^B$-

$R^B$=$C_2$-$C_6$-alkylene, preferably —C(CH$_3$)$_2$—C(CH$_3$)$_2$—). Said indolylboronic acid derivative of formula (VIIx-1) can be reacted with a pyrazole derivative of the formula (VI-1), in which $R^8$ and $R^9$ are as defined for the compounds of general formula (I), in a well-known Suzuki coupling, to give a compound of formula (Vx-1).

Said Suzuki coupling reaction can be catalysed by palladium catalysts as listed in the discussion of Scheme 1, preferably chloro(2-dicyclohexylphosphino-2',4',6'-triisopropyl-1,1'-biphenyl)[2-(2'-amino-1,1'-biphenyl)]palladium (II) (also referred to herein as XPhos Pd G2).

The reaction is preferably carried out in solvents such as 1,2-dimethoxyethane, 1,4-dioxane, DMF, THF, or n-propanol, or mixtures thereof, optionally also in mixture with water, preferably in a mixture of THF and water, and in the presence of a base such as aqueous potassium carbonate, aqueous sodium carbonate or potassium phosphate, preferably potassium phosphate.

The reaction is performed at temperatures ranging from room temperature (i.e. 20° C.) to the boiling point of the solvent. Further on, the reaction can be performed at temperatures above the boiling point using pressure tubes and a microwave oven. (for a review on Suzuki couplings see: D. G. Hall, Boronic Acids, 2005 WILEY-VCH Verlag GmbH & Co. KGaA, Weinheim, ISBN 3-527-30991-8 and references cited therein).

Indolylboronic acid derivatives of formula (VIIx-1) are readily available e.g. from the corresponding 7-bromo- or 7-iodoindoles, which are known to the person skilled in the art and which are also commercially available in certain cases, via Suzuki coupling with a suitable diboron reagent such as 4,4,4',4',5,5,5',5'-octamethyl-2,2'-bi-1,3,2-dioxaborolane.

The resulting intermediate compound of the formula (Vx-1) can subsequently be reacted with a compound of the formula (IVe), in which indices "d" and "e", independently from each other, represent an integer selected from 1, 2, 3, 4, 5 and 6, with the proviso that the sum of the integers representing indices "d" and "e" does not exceed 7, and $LG^6$ and $LG^7$ represent, independently from each other, a leaving group, preferably chloro, bromo or iodo, according to the methods discussed in context of Scheme 2d, supra, and subsequent hydrogenolysis of the olefinic double bond being present in the resulting macrocyclic compound of formula (IIc-1), according to the methods discussed in context of Scheme 2e, supra, to give a macrocyclic intermediate compound of formula (IIe-1).

Said macrocyclic intermediate compound of formula (IIe-1) can be further iodinated, to give an intermediate compound of formula (IIe-2), which can be subjected to a Suzuki or Sonogashira coupling to give intermediate compounds of formula (IIe-3) and can be eventually converted into a corresponding compound of formula (I), according to the methods outlined in the context of Schemes 4d, 4e, and 3.

Modification of any of the substituents, such as $R^1$, $R^2$, $R^3$, $R^4$, $R^5$, $R^{5E}$, $R^6$, $R^1$, $R^8$, $R^9$, $R^{10}$, $R^{11}$, $R^{12}$, $R^{13}$, $R^{p1}$ and $R^{p2}$ can be achieved before and/or after the exemplified transformation. However, also other routes may be used to synthesise the target compounds, in accordance with common general knowledge of a person skilled in the art of organic synthesis. Also, suitable and optionally protected precursor groups of said substituents can be carried through the synthesis routes described in context of the Schemes above, to be elaborated into the actual substituents as defined for the general formula (I), as exemplified e.g. for $R^4$ in Intermediates 47 to 59 in the Experimental Section below.

Said modifications can be such as the introduction of protective groups, cleavage of protective groups, reduction or oxidation of functional groups, formation or cleavage of esters or carboxamides, halogenation, metallation, substitution or other reactions known to a person skilled in the art. These transformations include those which introduce a functionality which allows for further interconversion of substituents. Appropriate protective groups and their introduction and cleavage are well-known to a person skilled in the art (see for example T.W. Greene and P.G.M. Wuts in Protective Groups in Organic Synthesis, 4$^{th}$ edition, Wiley 2006). Further, it is possible that two or more successive steps may be performed without work-up being performed between said steps, e.g. a "one-pot" reaction, as it is well-known to a person skilled in the art.

In accordance with a further aspect, the present invention provides a method of preparing a compound of general formula (I) according to any one of claims 1 to 5, said method comprising the step of allowing an intermediate compound of general formula (II):

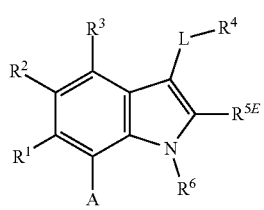

(II)

in which $R^1$, $R^2$, $R^3$, $R^4$, $R^6$, A and L are as defined for the compound of general formula (I) according to any one of claims 1 to 5, and $R^{5E}$ represents a carboxylic ester group or a benzyl ester to react with an alkali hydroxide in a mixture of water with THF and/or an aliphatic alcohol of formula $C_1$-$C_3$-alkyl-OH, at a temperature between 0° C. and 100° C. including 0° C. and 100° C., to transform the group $R^{5E}$ into a group $R^5$ as defined for the compounds of general formula (I), and subsequently optionally to convert the free acid group $R^5$ into a pharmaceutically acceptable salts thereof to obtain a compound of general formula (I)

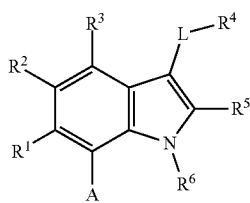

(I)

in which $R^1$, $R^2$, $R^3$, $R^4$, $R^5$, $R^6$, A and L are as defined for the compound of general formula (I) according to any one of claims 1 to 6 or a stereoisomer, a tautomer, an N-oxide, a hydrate, a solvate, or a salt thereof, or a mixture of same and subsequently optionally separating enantiomers by means of preparative HPLC on a chiral stationary phase.

In accordance with a further aspect, the present invention covers a method of preparing compounds of general formula (I) according to any one of claims 1 to 5, said method comprising the step of allowing an intermediate compound of general formula (II)

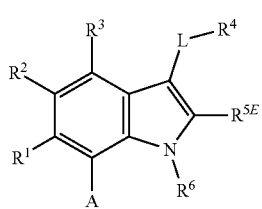

(II)

in which $R^1$, $R^2$, $R^3$, $R^4$, $R^6$, A and L are as defined for the compound of general formula (I) according to any one of claims 1 to 5, and $R^{5E}$ represents a carboxylic ester group or a benzyl ester to react with an alkali hydroxide such as potassium hydroxide, sodium hydroxide, lithium hydroxide, preferably lithium hydroxide, in a mixture of water with THF and/or an aliphatic alcohol of the formula $C_1$-$C_3$-alkyl-OH, preferably methanol or ethanol, at a temperature between 0° C. and 100° C., preferably between 20° C. and 60° C., to transform the group $R^{5E}$ into a group $R^5$ as defined for the compounds of general formula (I), and subsequently optionally to convert the free acid group $R^5$ into a pharmaceutically acceptable salts thereof to obtain a compound of general formula (I)

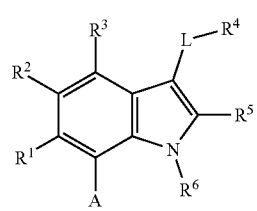

(I)

in which $R^1$, $R^2$, $R^3$, $R^4$, $R^5$, $R^6$, A and L are as defined for the compound of general formula (I) according to any one of claims 1 to 5 or a stereoisomer, a tautomer, an N-oxide, a hydrate, a solvate, or a salt thereof, or a mixture of same and subsequently optionally separating enantiomers by means of preparative HPLC on a chiral stationary phase.

The present invention provides methods of preparing compounds of the present invention of general formula (I), said methods comprising the steps as described in the Experimental Section herein.

In accordance with a further aspect, the present invention provides intermediate compounds which are useful for the preparation of the compounds of general formula (I), supra.

Particularly, the invention provides the intermediate compounds of general formula (II)

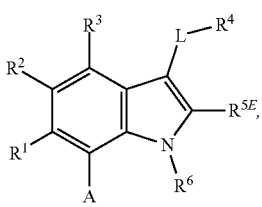

(II)

in which $R^1$, $R^2$, $R^3$, $R^4$, $R^6$, A and L are as defined for the compound of general formula (I) according to any one of claims 1 to 5, and $R^{5E}$ represents a carboxylic ester group or a benzyl group.

In accordance with another aspect, the present invention provides the use of said intermediate compounds for the preparation of a compound of general formula (I) as defined supra.

In accordance with another aspect, the present invention provides a method of using the intermediate compound of general formula (II) for the preparation of a compound of general formula (I).

The present invention provides the intermediate compounds which are disclosed in the Example Section of this text, infra.

The present invention provides any sub-combination within any embodiment or aspect of the present invention of intermediate compounds of general formula (II), supra.

The compounds of general formula (I) of the present invention can be converted to any salt, preferably pharmaceutically acceptable salts, as described herein, by any method which is known to the person skilled in the art. Similarly, any salt of a compound of general formula (I) of the present invention can be converted into the free compound, by any method which is known to the person skilled in the art.

Methods and Administration

Compounds of general formula (I) of the present invention demonstrate a valuable pharmacological spectrum of action and pharmacokinetic profile, both of which could not have been predicted. Compounds of the present invention have surprisingly been found to effectively inhibit MCL-1 activity, and it is possible therefore that said compounds can be used for the treatment or prophylaxis of diseases, preferably hyperproliferative disorders in humans and animals.

As used herein, "prophylaxis" includes a use of the compound that, in a statistical sample, reduces the occurrence of the disorder or condition in the treated sample relative to an untreated control sample, or delays the onset or reduces the severity of one or more symptoms of the disorder or condition relative to the untreated control sample, when administered to prior to the onset of the disorder or condition.

Compounds of the present invention can be utilized to inhibit, block, reduce, and/or decrease cell proliferation and/or cell division, and/or induce apoptosis. Disclosed methods include administering to a mammal in need thereof, including a human, an amount of a compound of general formula (I) of the present invention, or a pharmaceutically acceptable salt, isomer, polymorph, metabolite, hydrate, solvate or ester thereof, which is effective to treat the disorder.

Hyperproliferative disorders include, but are not limited to, for example: psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancers include, but are not limited to, invasive ductal carcinoma, invasive lobular carcinoma, ductal carcinoma in situ, and lobular carcinoma in situ.

Examples of cancers of the respiratory tract include, but are not limited to, small-cell and non-small-cell lung carcinoma, as well as bronchial adenoma and pleuropulmonary blastoma.

Examples of brain cancers include, but are not limited to, brain stem and hypophtalmic glioma, cerebellar and cerebral astrocytoma, medulloblastoma, ependymoma, as well as neuroectodermal and pineal tumours.

Tumours of the male reproductive organs include, but are not limited to, prostate and testicular cancer.

Tumours of the female reproductive organs include, but are not limited to, endometrial, cervical, ovarian, vaginal, and vulvar cancer, as well as sarcoma of the uterus.

Tumours of the digestive tract include, but are not limited to, anal, colon, colorectal, oesophageal, gallbladder, gastric, pancreatic, rectal, small-intestine, and salivary gland cancers.

Tumours of the urinary tract include, but are not limited to, bladder, penile, kidney, renal pelvis, ureter, urethral and human papillary renal cancers.

Eye cancers include, but are not limited to, intraocular melanoma and retinoblastoma.

Examples of liver cancers include, but are not limited to, hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to, basal cell carcinoma, squamous cell carcinoma, Kaposi's sarcoma, malignant melanoma, Merkel cell skin cancer, and non-melanoma skin cancer.

Head-and-neck cancers include, but are not limited to, laryngeal, hypopharyngeal, nasopharyngeal, oropharyngeal cancer, lip and oral cavity cancer and squamous cell.

Lymphomas include, but are not limited to, AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to, sarcoma of the soft tissue, osteosarcoma, malignant fibrous histiocytoma, lymphosarcoma, and rhabdomyosarcoma.

Leukemias include, but are not limited to, acute myeloid leukemia, acute lymphoblastic leukemia, chronic lymphocytic leukemia, chronic myelogenous leukemia, and hairy cell leukemia.

The present invention also provides methods of treating angiogenic disorders including diseases associated with excessive and/or abnormal angiogenesis.

Inappropriate and ectopic expression of angiogenesis can be deleterious to an organism. A number of pathological conditions are associated with the growth of extraneous blood vessels. These include, for example, diabetic retinopathy, ischemic retinal-vein occlusion, and retinopathy of prematurity [Aiello et al., New Engl. J. Med., 1994, 331, 1480, Peer et al., Lab. Invest., 1995, 72, 638], age-related macular degeneration (AMD) [Lopez et al., Invest. Opthtalmol. Vis. Sci., 1996, 37, 855], neovascular glaucoma, psoriasis, retrolental fibroplasias, angiofibroma, inflammation, rheumatoid arthritis (RA), restenosis, in-stent restenosis, and vascular graft restenosis. In addition, the increased blood supply associated with cancerous and neoplastic tissue encourages growth, leading to rapid tumour enlargement and metastasis. Moreover, the growth of new blood and lymph vessels in a tumour provides an escape route for rapidly dividing cells, encouraging metastasis and the consequence spread of the cancer. Thus, compounds of general formula (I) of the present invention can be utilized to treat and/or prevent any of the aforementioned angiogenesis disorders, for example by inhibiting and/or reducing blood vessel formation; by inhibiting, blocking, reducing, and/or decreasing endothelial cell proliferation, or other pathways involved in angiogenesis, as well as causing cell death or apoptosis of such cell types.

These disorders have been well characterized in humans, but also exist with a similar etiology in other mammals, and can be treated by administering pharmaceutical compositions of the present invention.

By "subject" is meant a mammal, including, but not limited to, a human or non-human mammal, such as a bovine, equine, canine, ovine, or feline.

The term "treating" or "treatment" as stated throughout this document is used conventionally, for example the management or care of a subject for the purpose of combating, alleviating, reducing, relieving, and/or improving the condition of a disease or disorder, such as a carcinoma.

The compounds of the present invention can be used in particular in therapy and prevention, i.e., prophylaxis, of tumour growth and metastases, especially in solid tumours of all indications and stages with or without pre-treatment of the tumour growth.

Generally, the use of chemotherapeutic agents and/or anti-cancer agents in combination with a compound or pharmaceutical composition of the present invention will serve to:
1. yield better efficacy in reducing the growth of a tumour or even eliminate the tumour as compared to administration of either agent alone,
2. provide for the administration of lesser amounts of the administered chemotherapeutic agents,
3. provide for a chemotherapeutic treatment that is well tolerated in the patient with fewer deleterious pharmacological complications than observed with single agent chemotherapies and certain other combined therapies,
4. provide for treating a broader spectrum of different cancer types in mammals, especially humans,
5. provide for a higher response rate among treated patients,
6. provide for a longer survival time among treated patients compared to standard chemotherapy treatments,
7. provide a longer time for tumour progression, and/or
8. yield efficacy and tolerability results at least as good as those of the agents used alone, compared to known instances where other cancer agent combinations produce antagonistic effects.

In addition, the compounds of general formula (I) of the present invention can also be used in combination with radiotherapy and/or surgical intervention.

In some embodiments of the present invention, the compounds of general formula (I) of the present invention may be used to sensitize a cell to radiation, i.e., treatment of a cell with a compound of the present invention prior to radiation treatment of the cell renders the cell more susceptible to DNA damage and cell death than the cell would be in the absence of any treatment with a compound of the present invention. In some embodiments, the cell is treated with at least one compound of general formula (I) of the present invention.

Thus, the present invention also provides a method of killing a cell, wherein a cell is administered one or more compounds of the present invention in combination with conventional radiation therapy.

The present invention also provides a method of rendering a cell more susceptible to cell death, wherein the cell is treated with one or more compounds of general formula (I) of the present invention prior to the treatment of the cell to cause or induce cell death. In some embodiments, after the cell is treated with one or more compounds of general formula (I) of the present invention, the cell is treated with at least one compound, or at least one method, or a combination thereof, in order to cause DNA damage for the purpose of inhibiting the function of the normal cell or killing the cell.

In other embodiments of the present invention, a cell is killed by treating the cell with at least one DNA damaging agent, i.e., after treating a cell with one or more compounds of general formula (I) of the present invention to sensitize the cell to cell death, the cell is treated with at least one DNA damaging agent to kill the cell. DNA damaging agents useful in the present invention include, but are not limited to, chemotherapeutic agents (e.g., cis platin), ionizing radiation (X-rays, ultraviolet radiation), carcinogenic agents, and mutagenic agents.

In other embodiments, a cell is killed by treating the cell with at least one method to cause or induce DNA damage. Such methods include, but are not limited to, activation of a cell signalling pathway that results in DNA damage when the pathway is activated, inhibiting of a cell signalling pathway that results in DNA damage when the pathway is inhibited, and inducing a biochemical change in a cell, wherein the change results in DNA damage. By way of a non-limiting example, a DNA repair pathway in a cell can be inhibited, thereby preventing the repair of DNA damage and resulting in an abnormal accumulation of DNA damage in a cell.

In some embodiments, a compound of general formula (I) of the present invention is administered to a cell prior to the radiation or other induction of DNA damage in the cell. In some embodiments, a compound of general formula (I) of the present invention is administered to a cell concomitantly with the radiation or other induction of DNA damage in the cell. In some embodiments, a compound of general formula (I) of the present invention is administered to a cell immediately after radiation or other induction of DNA damage in the cell has begun.

In some embodiments, the cell is in vitro. In some embodiments, the cell is in vivo.

Thus in some embodiments, the present invention includes a method of inhibiting proliferation of a cell and/or the induction of apoptosis in a cell, comprising contacting the cell with a compound of formula (I) according to any one of claims 1-6.

Furthermore in some embodiments, the present invention includes a method of using a compound of general formula (I) for the treatment of diseases.

Particularly in some embodiments, the present invention includes a method of treating a hyperproliferative disease, more particularly cancer, comprising administering an effective amount of at lest one compound of general formula (I) according to any one of claims 1-6.

Furthermore in some embodiments, the present invention includes a method of treating cancer, particularly lymphoma, non-Hodgkin-lymphoma type, diffuse large B-cell lymphoma subtype, acute leukemia, acute myeloid leukemia type, multiple myeloma, ovarian cancer, comprising administering an effective amount of at least one compound of formula (I) according to any one of claims 1-6.

Furthermore in some embodiments, the present invention includes a method of treating cancer, particularly multiple myeloma, ovarian carcinoma, acute monocytic leukemia, melanoma and lung cancer. comprising administering an effective amount of at least one compound of formula (I) according to any one of claims 1-6.

In some embodiments the present invention provides for compounds of general formula (I) for use in a method of treating cancer, particularly where the cancer disease is multiple myeloma, ovarian carcinoma, acute monocytic leukemia, melanoma and lung cancer.

Furthermore in some embodiments, the present invention includes a method of treating cancer, particularly breast cancer; lung cancer; lymphoma including non-Hodgkin-lymphoma type, diffuse large B-cell lymphoma subtype including GC-DLBCL* and ABC-DLBCL subtypes, and mantle cell lymphoma; acute leukemia, acute myeloid leukemia type, acute monocytic leukemia; melanoma; multiple myeloma; ovarian cancer; pancreas cancer comprising administering an effective amount of at least one compound of formula (I) according to any one of claims 1-6. GC-DLBCL means Germinal B-cell Diffuse Large B-Cell Lymphoma and  ABC-DLBCL means Activated B-cell Diffuse Large B-Cell Lymphoma Furthermore in some embodiments, the present invention includes a method of treating cancer, particularly breast cancer, lung cancer, diffuse large B-cell lymphoma subtype including GC-DLBCL* and ABC-DLBCL subtypes, mantle cell lymphoma, acute monocytic leukemia, melanoma, ovarian cancer, pancreas cancer comprising administering an effective amount of at least one compound of formula (I) according to any one of claims 1-6**. Furthermore in accordance with another aspect, the present invention provides a compound of formula (I) for use of treating diseases.

In some embodiments, the present invention includes a compound of general formula (I) for use in a method of inhibiting proliferation of a cell and/or the induction of apoptosis in a cell, comprising contacting the cell with a compound of formula (I) according to any one of claims 1-6. Particularly in some embodiments, the present invention includes compounds of general formula (I) for use in a method of treating a hyperproliferative disease, more particularly wherein the hyperproliferative disease is cancer, and yet even more particularly wherein the cancer disease is lymphoma, non-Hodgkin-lymphoma type, diffuse large B-cell lymphoma subtype, ovarian cancer, multiple myeloma, acute leukemia, and acute myeloid leukemia. Particularly in some embodiments, the present invention includes compounds of general formula (I) for use in a method of treating a hyperproliferative disease, more particularly wherein the hyperproliferative disease is cancer, and yet even more particularly wherein the cancer disease breast cancer; lung cancer; lymphoma including non-Hodgkin-lymphoma type, diffuse large B-cell lymphoma subtype including GC-DLBCL* and ABC-DLBCL** subtypes, and mantle cell lymphoma; acute leukemia, acute myeloid leukemia type, acute monocytic leukemia; melanoma; multiple myeloma; ovarian cancer; pancreas cancer.

In some embodiments, the present invention includes use of the compounds of general formula (I) for the manufacture of a medicament for the treatment of a hyperproliferative disease, particularly cancer and more particularly lymphoma, non-Hodgkin-lymphoma type, diffuse large B-cell lymphoma subtype, ovarian cancer, multiple myeloma, acute leukemia, and acute myeloid leukemia type.

It is possible for the compounds according to the invention to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, or otic route or as an implant or stent.

For these administration routes, it is possible for the compounds according to the invention to be administered in suitable administration forms.

For oral administration, it is possible to formulate the compounds according to the invention into dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatin capsules), sugar-coated tablets, granules, pellets, powders, emulsions, suspensions, aerosols or solutions. It is possible to incorporate the compounds according to the invention in crystalline and/or amorphous and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation (inter alia powder inhalers, nebulizers), nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixturae agitandae), lipophilic suspensions, emulsions, ointments, creams, transdermal therapeutic systems (such as, for example, patches), milk, pastes, foams, dusting powders, implants or stents.

The compounds according to the invention can be incorporated into the stated administration forms. This can be effected in a manner known per se by mixing with pharmaceutically suitable excipients. Pharmaceutically suitable excipients include, inter alia, fillers and carriers (for example, cellulose, microcrystalline cellulose (such as, for example, Avicel®), lactose, mannitol, starch, calcium phosphate (such as, for example, Di-Cafos®)), ointment bases (for example petroleum jelly, paraffins, triglycerides, waxes, wool wax, wool wax alcohols, lanolin, hydrophilic ointment, polyethylene glycols), bases for suppositories (for example, polyethylene glycols, cacao butter, hard fat), solvents (for example, water, ethanol, isopropanol, glycerol, propylene glycol, medium chain-length triglycerides, fatty oils, liquid polyethylene glycols, paraffins), surfactants, emulsifiers, dispersants or wetters (for example, sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxyethylene fatty acid esters, polyoxyethylene fatty alcohol ethers, glycerol fatty acid esters, poloxamers (such as, for example, Pluronic®), buffers, acids and bases (for example, phosphates, carbonates, citric acid, acetic acid, hydrochloric acid, sodium hydroxide solution, ammonium carbonate, trometamol, triethanolamine), isotonicity agents (for example, glucose, sodium chloride), adsorbents (for example, highly-disperse silicas), viscosity-increasing agents, gel formers, thickeners and/or binders (for example, polyvinylpyrrolidone, methylcellulose, hydroxypropylmethylcellulose, hydroxypropylcellulose, carboxymethylcellulose-sodium, starch, carbomers, polyacrylic acids (such as, for example, Carbopol®); alginates, gelatin), disintegrants (for example, modified starch, carboxymethylcellulose-sodium, sodium starch glycolate (such as, for example, Explotab®), cross- linked polyvinylpyrrolidone, croscarmellose-sodium (such as, for example, AcDiSol®)), flow regulators, lubricants, glidants and mould release agents (for example, magnesium stearate, stearic acid, talc, highly-disperse silicas (such as, for example, Aerosil®)), coating materials (for example, sugar, shellac) and film formers for films or diffusion membranes which dissolve rapidly or in a modified manner (for example, polyvinylpyrrolidones (such as, for example, Kollidon®), polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®)), capsule materials (for example, gelatin, hydroxypropylmethylcellulose), synthetic polymers (for example, polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and blockcopolymers), plasticizers (for example, polyethylene glycols, propylene glycol, glycerol, triacetine, triacetyl citrate, dibutyl phthalate), penetration enhancers, stabilisers (for example, antioxidants such as, for example, ascorbic acid, ascorbyl palmitate, sodium ascorbate, butylhydroxyanisole, butylhydroxytoluene, propyl gallate), preservatives (for example, parabens, sorbic acid, thiomersal, benzalkonium chloride, chlorhexidine acetate, sodium benzoate), colourants (for example, inorganic pigments such as, for example, iron oxides, titanium dioxide), and flavourings, sweeteners, flavour- and/or odour-masking agents.

The present invention furthermore relates to a pharmaceutical composition which comprise at least one compound according to the invention, conventionally together with one or more pharmaceutically suitable excipient(s), and to their use according to the present invention.

In some embodiments, the present invention includes pharmaceutical combinations, in particular medicaments, comprising at least one compound of general formula (I) of the present invention and at least one or more further active ingredients, in particular for the treatment and/or prophylaxis of a hyperproliferative disorder, particularly cancer.

Particularly, the present invention includes a pharmaceutical combination, which comprises:

one or more first active ingredients, in particular compounds of general formula (I) as defined supra, and one or more further active ingredients, in particular for the treatment and/or prophylaxis of hyperproliferative disorder, particularly cancer.

The term "combination" in the present invention is used as known to persons skilled in the art, it being possible for said combination to be a fixed combination, a non-fixed combination or a kit-of-parts.

A "fixed combination" in the present invention is used as known to persons skilled in the art and is defined as a combination wherein, for example, a first active ingredient, such as one or more compounds of general formula (I) of the present invention, and a further active ingredient are present together in one unit dosage or in one single entity. One example of a "fixed combination" is a pharmaceutical composition wherein a first active ingredient and a further active ingredient are present in admixture for simultaneous administration, such as in a formulation. Another example of a "fixed combination" is a pharmaceutical combination wherein a first active ingredient and a further active ingredient are present in one unit without being in admixture.

A non-fixed combination or "kit-of-parts" in the present invention is used as known to persons skilled in the art and is defined as a combination wherein a first active ingredient and a further active ingredient are present in more than one unit. One example of a non-fixed combination or kit-of-parts is a combination wherein the first active ingredient and the further active ingredient are present separately. It is possible for the components of the non-fixed combination or kit-of-parts to be administered separately, sequentially, simultaneously, concurrently or chronologically staggered.

The compounds of the present invention can be administered as the sole pharmaceutical agent, or in combination with one or more other pharmaceutically active ingredients where the combination causes no unacceptable adverse effects. The present invention also includes such pharmaceutical combinations. For example, the compounds of the present invention can be combined with known anti-cancer agents.

Examples of anti-cancer agents include:

131I-chTNT, abarelix, abiraterone, aclarubicin, ado-trastuzumab emtansine, afatinib, aflibercept, aldesleukin, alemtuzumab, Alendronic acid, alitretinoin, altretamine, amifostine, aminoglutethimide, Hexyl aminolevulinate, amrubicin, amsacrine, anastrozole, ancestim, anethole dithiolethione, angiotensin II, antithrombin III, aprepitant, arcitumomab, arglabin, arsenic trioxide, asparaginase, axitinib, azacitidine, basiliximab, belotecan, bendamustine, belinostat, bevacizumab, bexarotene, bicalutamide, bisantrene, bleomycin, bortezomib, buserelin, bosutinib, brentuximab vedotin, busulfan, cabazitaxel, cabozantinib, calcium folinate, calcium levofolinate, capecitabine, capromab, carboplatin, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, copanlisib, crisantaspase, cyclophosphamide, cyproterone, cytarabine, dacarbazine, dactinomycin, darbepoetin alfa, dabrafenib, dasatinib, daunorubicin, decitabine, degarelix, denileukin diftitox, denosumab, depreotide, deslorelin, dexrazoxane, dibrospidium chloride, dianhydrogalactitol, diclofenac, docetaxel, dolasetron, doxifluridine, doxorubicin, doxorubicin+ estrone, dronabinol, eculizumab, edrecolomab, elliptinium acetate, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, Iansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, Ianreotide, lapatinib, lasocholine, lenalidomide, lenograstim, lentinan, letrozole, leuprorelin, levamisole, levonorgestrel, levothyroxine sodium, lisuride, lobaplatin, lomustine, Ionidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, nedaplatin, nelarabine, neridronic acid, nivolumabpentetreotide, nilotinib, nilutamide, nimorazole, nimotuzumab, nimustine, nitracrine, nivolumab, obinutuzumab, octreotide, ofatumumab, omacetaxine mepesuccinate, omeprazole, ondansetron, oprelvekin, orgotein, orilotimod, oxaliplatin, oxycodone, oxymetholone, ozogamicine, p53 gene therapy, paclitaxel, palifermin, palladium-103 seed, palonosetron, pamidronic acid, panitumumab, pantoprazole, pazopanib, pegaspargase, PEG-epoetin beta (methoxy PEG-epoetin beta), pembrolizumab, pegfilgrastim, peginterferon alfa-2b, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, romidepsin, romiplostim, romurtide, roniciclib, samarium (153Sm) lexidronam, sargramostim, satumomab, secretin, sipuleucel-T, sizofiran, sobuzoxane, sodium glycididazole, sorafenib, stanozolol, streptozocin, sunitinib, talaporfin, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

Based upon standard laboratory techniques known to evaluate compounds useful for the treatment of hyperproliferative diseases, by standard toxicity tests and by standard pharmacological assays for the determination of treatment of the conditions identified above in mammals, and by comparison of these results with the results of known active ingredients or medicaments that are used to treat these conditions, the effective dosage of the compounds of the present invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 40 mg/kg body weight per day. Clinically useful dosing schedules will range from one to three times a day dosing to once every four weeks dosing. In addition, it is possible for "drug holidays", in which a patient is not dosed with a drug for a certain period of time, to be beneficial to the overall balance between pharmacological effect and tolerability. It is possible for a unit dosage to contain from about 0.5 mg to about 3000 mg of active ingredient, and can be administered one or more times per day or less than once a day. The average daily dosage for administration by injection, including intravenous, intramuscular, subcutaneous and parenteral injections, and use of infusion techniques will preferably be from about 0.01 to about 200 mg/kg of total body weight. The average daily rectal dosage regimen will preferably be from about 0.01 to about 200 mg/kg of total body weight. The average daily vaginal dosage regimen will preferably be from about 0.01 to about 200 mg/kg of total body weight. The average daily topical dosage regimen will preferably be from about 0.1 to about 200 mg administered between one to four times daily. The transdermal concentration will preferably be that required to maintain a daily dose of from about 0.01 to about 200 mg/kg. The average daily inhalation dosage regimen will preferably be from about 0.01 to about 100 mg/kg of total body weight.

In one embodiment the average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from abut 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt

EXPERIMENTAL SECTION

Experimental Section

NMR Spectra

To the extent NMR peak forms and multiplicities are specified, they are stated as they appear in the spectra, possible higher order effects have not been considered.

The $^1$H-NMR data of selected examples are listed in the form of $^1$H-NMR peaklists. For each signal peak the δ value in ppm is given, followed by the signal intensity, reported in round brackets. The δ value-signal intensity pairs from different peaks are separated by commas. Therefore, a peaklist is described by the general form: $\delta_1$ (intensity$_1$), $\delta_2$ (intensity$_2$), . . . , $\delta_i$ (intensity$_i$), . . . , $\delta_n$ (intensity$_n$).

The intensity of a sharp signal correlates with the height (in cm) of the signal in a printed NMR spectrum. When compared with other signals, this data can be correlated to the real ratios of the signal intensities. In the case of broad signals, more than one peak, or the center of the signal along with their relative intensity, compared to the most intense signal displayed in the spectrum, are shown. A $^1$H-NMR peaklist is similar to a classical $^1$H-NMR readout, and thus usually contains all the peaks listed in a classical NMR interpretation. Moreover, similar to classical $^1$H-NMR printouts, peaklists can show solvent signals, signals derived from stereoisomers of target compounds (also the subject of the invention), and/or peaks of impurities. The peaks of stereoisomers, and/or peaks of impurities are typically displayed with a lower intensity compared to the peaks of the target compounds (e.g., with a purity of >90%). Such stereoisomers and/or impurities may be typical for the particular manufacturing process, and therefore their peaks may help to identify the reproduction of our manufacturing process on the basis of "by-product fingerprints". An expert who calculates the peaks of the target compounds by known methods (MestReC, ACD simulation, or by use of empirically evaluated expectation values), can isolate the peaks of target compounds as required, optionally using additional intensity filters. Such an operation would be similar to peak-picking in classical $^1$H-NMR interpretation. A detailed description of the reporting of NMR data in the form of peaklists can be found in the publication "Citation of NMR Peaklist Data within Patent Applications" (cf. Research Disclosure Database Number 605005, 2014, 1 Aug. 2014, or http://www.researchdisclosure.com/searching-disclosures). In the peak picking routine, as described in the Research Disclosure Database Number 605005, the parameter "MinimumHeight" can be adjusted between 1% and 4%. Depending on the chemical structure and/or depending on the concentration of the measured compound it may be reasonable to set the parameter "MinimumHeight"<1%.

Experimental Section

Abbreviations

The following table lists the abbreviations used in this paragraph and in the Intermediates and Examples section as far as they are not explained within the text body. Other abbreviations have their meanings customary per se to the skilled person. A comprehensive list of the abbreviations utilized by organic chemists of ordinary skill in the art appears presented in the first issue of each volume of the Journal of Organic Chemistry; this list is typically presented in a table entitled Standard List of Abbreviations. The abbreviations contained therein, and all abbreviations utilized by organic chemists of ordinary skill in the art are hereby incorporated by reference. In case of doubt, the abbreviations and/or their meaning according to the following table shall prevail.

TABLE 1

Abbreviations

| Abbreviation | Meaning |
|---|---|
| BPR | Back Pressure Regulator |
| BOC | tert-butoxycarbonyl- |
| br. | broad signal (NMR) |
| CyJohnPhos | Biphenyl-2-yl(dicyclohexyl)phosphine |
| DABAL | (mu-1,4-diazabicyclo[2.2.2]octane-kappaN1:kappaN4)(hexamethyl)dialuminium [CAS No. 137203-34-0] |
| d | doublet (NMR) |
| DAD | Diode array detector |
| dd | doublet of doublet (NMR) |
| dt | doublet of triplet (NMR) |
| DMF | N,N-dimethylformamide |
| DMSO | dimethylsulfoxide |
| EDTA | ethylenediaminetetraacetic acid |
| ee | enantiomeric excess |
| ESI | electrospray (ES) ionisation |
| Grubbs 2$^{nd}$ Generation Catalyst | (1,3-Bis(2,4,6-trimethylphenyl)-2-imidazolidinylidene)dichloro(phenylmethylene)(tricyclohexylphosphine) ruthenium (CAS No 246047-72-3) |
| h, hr (hrs) | hour(s) |
| HATU | 1-[bis(dimethylamino)methylene]-1H-1,2,3-triazolo[4,5-b]-pyridinium 3-oxid hexafluorophosphate |
| HCl | hydrogen chloride, hydrochloric acid |
| HPLC | high performance liquid chromatography |
| HRP | horseradish peroxidase |
| LC-MS | liquid chromatography-mass spectrometry |
| m | multiplet (NMR) |
| Min | minute(s) |
| MS | mass spectrometry |
| MTP | microtiter plate |
| MWD | Multiple wavelength detector |
| Na-K-tartrate | Sodium potassium tartrate |
| NMR | nuclear magnetic resonance spectroscopy: chemical shifts (δ) are given in ppm. The chemical shifts were corrected by setting the DMSO signal to 2.50 ppm using unless otherwise stated. |
| NAD$^+$ | nicotinamide adenine dinucleotide |
| PBS | phosphate buffered saline |
| Pd/C | Palladium on carbon |
| Pd(dppf)Cl$_2$x CH$_2$Cl$_2$ | [1,1'-Bis-(diphenylphosphino)-ferrocen]-dichloropalladium(II), complex with dichloromethanen |
| PG | protecting group |
| Ph | phenyl |
| PyBOP | benzotriazol-1-yl-oxytripyrrolidinophosphonium hexafluorophosphate |
| q | quartet (NMR) |
| quin | quintet (NMR) |
| RF | reflux |
| rt | room temperature |
| R$_t$, Rt | retention time |
| s | singulet (NMR) |
| SFC | Supercritical Fluid Chromatography |
| SPA | Scintillation proximity assay |
| T3P | 1-propanephosphonic anhydride |
| TBAF | tetrabutylammonium fluoride |
| t | triplet (NMR) |
| td | triplet of doublet (NMR) |
| TFA | trifluoroacetic acid |
| THF | tetrahydrofuran |
| TLC | thin layer chromatography |
| wt- % | percent of weight |
| [$^3$H]- | tritium |
| δ | chemical shift |

TABLE 1-continued

Abbreviations

| Abbreviation | Meaning |
| --- | --- |
| XPhos Pd G2 | Chloro(2-dicyclohexylphosphino-2',4',6'-triisopropyl-1,1'-biphenyl)[2-(2'-amino-1,1'-biphenyl)]palladium(II) (Cas No: 1310584-14-5) |
| XPhos Pd G3 | (2-Dicyclohexylphosphino-2',4',6'-triisopropyl-1,1'-biphenyl)[2-(2'-amino-1,1'-biphenyl)]palladium(II) methanesulfonate (Cas No: 1445085-55-1) |

Other abbreviations have their meanings customary per se to the skilled person.

The various aspects of the invention described in this application are illustrated by the following examples which are not meant to limit the invention in any way.

The example testing experiments described herein serve to illustrate the present invention and the invention is not limited to the examples given.

Experimental Section

Chemical Naming & Display of Double Bond Isomery

Chemical names were generated using the ACD/Name software from ACD/Labs. In some cases generally accepted names of commercially available reagents were used in place of ACD/Name generated names.

Certain compounds of the present invention, as well as the corresponding macrocyclic intermediates, feature an olefinic double bond as a part of their macrocyclic core, e.g. Examples 1-1, 1-2, 1-17, 1-51, 1-64, 1-76, 1-94, 001, 038, 118 and 132, as well as Intermediates 1-10, 1-13, 1-32, 1-55, 1-88, 1-132, 1-168, 25, 49, 75, 141, 214, 273 and 292, the (E)/(Z) configuration of which being unknown. Said olefinic double bond is therefore displayed as

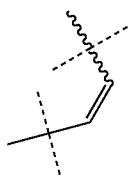

herein. This visualization means that the respective olefinic double bond in said macrocyclic compounds may be present in either (E) or (Z) configuration, or as a mixture of (E) and (Z) isomers.

In other cases, in particular when a stereochemically homogeneous (Z)-alkene has been employed as an immediate precursor in macrocycle formation, configuration of the resulting macrocycle is assumed to be (Z) and displayed accordingly, e.g. in Intermediates 143, 171, 190, 200, 256, 332, 378, 423 and 446, as well as in Examples 062, 070, 098 and 358.

However, in compounds featuring an olefinic double bond which is not part of said macrocyclic core, e.g. in Intermediates 1-58, 1-59, 1-60, 321, 322 and 323, said visualization

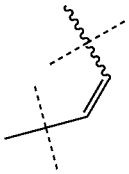

indicates a mixture of (E) and (Z) isomers, according to the usual practice of the person skilled in the art.

For Example 1-68, it has been shown by NMR (C-NMR-BB, C-NMR-DEPT, COLOC, COSY, H-NMR, HETCOR, LC-ES+, NOESY) that the olefinic double bond in its macrocyclic core features (Z) configuration. It is assumed that this also applies to its precursor, i.e. Intermediate 1-118. For these two compounds, the (Z) configuration is therefore shown explicitly in their structural formulae.

Experimental Section

General Part

All reagents, for which the synthesis is not described in the experimental part, are either commercially available, or are known compounds or may be formed from known compounds by known methods by a person skilled in the art.

"Silicone filter" refers to filter papers which are made hydrophobic (impermeable to water) by impregnation with a silicone. With the aid of these filters, water can be separated from water-immiscible organic solvents by means of a filtration (i.e. filter paper type MN 617 WA, Macherey-Nagel).

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be removed by trituration using a suitable solvent or solvent mixture. In some cases, the compounds may be purified by chromatography, particularly flash column chromatography, using for example prepacked silica gel cartridges, e.g. Biotage SNAP cartridges KP-Sil® or KP-NH® in combination with a Biotage autopurifier system (SP4® or Isolera Four®) and eluents such as gradients of hexane/ethyl acetate or DCM/methanol. In flash column chromatography, unmodified ("regular") silica gel may be used as well as aminophase functionalized silica gel. As used herein, "Biotage SNAP cartridge silica" refers to the use of regular silica gel; "Biotage SNAP cartridge NH$_2$ silica" refers to the use of aminophase functionalized silica gel. If reference is made to flash column chromatography or to flash chromatography in the experimental section without specification of a stationary phase, regular silica gel was used.

In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid, diethylamine or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

UPLC-MS Standard Procedures

Analytical UPLC-MS was performed as described below. The masses (m/z) are reported from the positive mode electrospray ionisation unless the negative mode is indicated (ESI–). In most of the cases method 1 is used. If not, it is indicated.

Analytical UPLC Methods:

Method 1:
Instrument: Waters Acquity UPLCMS SingleQuad; Column: Acquity UPLC BEH C18 1.7 µm, 50×2.1 mm; eluent A: water+0.1 vol % formic acid (99%), eluent B: acetonitrile; gradient: 0-1.6 min 1-99% B, 1.6-2.0 min 99% B; flow 0.8 ml/min; temperature: 60° C.; DAD scan: 210-400 nm.

Method 2:
Instrument: Waters Acquity UPLCMS SingleQuad; Column: Acquity UPLC BEH C18 1.7 µm, 50×2.1 mm; eluent A: water+0.2 vol % aqueous ammonia (32%), eluent B: acetonitrile; gradient: 0-1.6 min 1-99% B, 1.6-2.0 min 99% B; flow 0.8 ml/min; temperature: 60° C.; DAD scan: 210-400 nm.

Method 3:
Instrument: Waters Acquity UPLCMS SingleQuad; Column: Acquity UPLC BEH C18 1.7 50×2.1 mm; eluent A: water+0.1 vol % formic acid (99%), eluent B: acetonitrile; gradient: 0-1.6 min 1-99% B, 1.6-2.0 min 99% B; flow 0.8 ml/min; temperature: 60° C.; DAD scan: 210-400 nm.

Method 4:
Instrument: Waters Acquity UPLCMS SingleQuad; Column: Acquity UPLC BEH C18 1.7 µm, 50×2.1 mm; eluent A: water+0.2 vol % aqueous ammonia (32%), eluent B: acetonitrile; gradient: 0-1.6 min 1-99% B, 1.6-2.0 min 99% B; flow 0.8 ml/min; temperature: 60° C.; DAD scan: 210-400 nm Preparative HPLC Methods:

Method P1:
Instrument: Waters Autopurification MS SingleQuad; Column: Waters XBrigde C18 5µ 100×30 mm; eluent A: water+0.1 vol % formic acid (99%), eluent B: acetonitrile; gradient: 0-5.5 min 5-100% B; flow 70 ml/min; temperature: 25° C.; DAD scan: 210-400 nm.

Method P2:
Instrument: Waters Autopurification MS SingleQuad; Column: Waters XBrigde C18 5µ 100×30 mm; eluent A: water+0.2 vol % aqueous ammonia (32%), eluent B: acetonitrile; gradient: 0-5.5 min 5-100% B; flow 70 ml/min; temperature: 25° C.; DAD scan: 210-400 nm.

Method P3:
Instrument: Pump: Labomatic HD-5000 or HD-3000, Head HDK 280, low pressure gradient module ND-B1000; Manual injection valve: Rheodyne 3725i038; Detector: Knauer Azura UVD 2.15; Collector: Labomatic Labocol Vario-4000; Column: Chromatorex RP C-18 10 µm, 125×30 mm; solvent A: water+0.1 vol-% formic acid, solvent B: acetonitrile; gradient: 0.00-0.50 min 40% B (150 ml/min), 0.50-6.00 min 40-80% B (150 ml/min), 6.00-6.10 min 80-100% B (150 ml/min), 6.10-8.00 min 100% B (150 ml/min), UV-Detection.

Method P4:
Instrument: Pump: Labomatic HD-5000 or HD-3000, Head HDK 280, low pressure gradient module ND-B1000; Manual injection valve: Rheodyne 3725i038; Detector: Knauer Azura UVD 2.15; Collector: Labomatic Labocol Vario-4000; Column: Chromatorex RP C-18 10 µm, 125×30 mm; Solvent A: water+0.1 Vol-% formic acid (32%), Solvent B: acetonitrile, Gradient: 0.00-0.50 min 30% B (150 ml/min), 0.50-6.00 min 30-70% B (150 mL/min), 6.00-6.10 min 70-100% B (150 mL/min), 6.10-8.00 min 100% B (150 mL/min), UV-Detection.

Method P5:
Instrument: Pump: Labomatic HD-5000 or HD-3000, Head HDK 280, low pressure gradient module ND-B1000; Manual injection valve: Rheodyne 3725i038; Detector: Knauer Azura UVD 2.15; Collector: Labomatic Labocol Vario-4000; Column: Chromatorex RP C-18 10 µm, 125×30 mm; Solvent A: water+0.1 Vol-% formic acid (32%), Solvent B: acetonitrile, Gradient: 0.00-0.50 min 35% B (150 ml/min), 0.50-6.00 min 35-100% B (150 mL/min), 6.00-8.00 min 100% B (150 mL/min), UV-Detection.

Method P6:
Instrument: Pump: Labomatic HD-5000 or HD-3000, Head HDK 280, low pressure gradient module ND-B1000; Manual injection valve: Rheodyne 3725i038; Detector: Knauer Azura UVD 2.15; Collector: Labomatic Labocol Vario-4000; Column: Chromatorex RP C-18 10 µm, 125×30 mm; Solvent A: water+0.1 Vol-% formic acid (32%), Solvent B: acetonitrile, Gradient: 0.00-0.50 min 20% B (150 ml/min), 0.50-6.00 min 20-90% B (150 mL/min), 6.00-6.10 min 90-100% B (150 mL/min), 6.10-8.00 min 100% B (150 mL/min), UV-Detection.

Method P7:
Instrument: Pump: Labomatic HD-5000 or HD-3000, Head HDK 280, low pressure gradient module ND-B1000; Manual injection valve: Rheodyne 3725i038; Detector: Knauer Azura UVD 2.15; Collector: Labomatic Labocol Vario-4000; Column: Chromatorex RP C-18 10 µm, 125×30 mm; Solvent A: water+0.1 Vol-% formic acid (32%), Solvent B: acetonitrile, gradient: 0.00-0.50 min 10% B (150 ml/min), 0.50-6.00 min 10-50% B (150 ml/min), 6.00-6.10 min 50-100% B (150 ml/min), 6.10-8.00 min 100% B (150 ml/min), UV-Detection.

Method P8:
Instrument: Pump: Labomatic HD-5000 or HD-3000, Head HDK 280, low pressure gradient module ND-B1000; Manual injection valve: Rheodyne 3725i038; Detector: Knauer Azura UVD 2.15; Collector: Labomatic Labocol Vario-4000; Column: XBridge, RP C18 5 µm, 100×30 mm; Solvent A: water+0.2 Vol-% ammonia (32%), Solvent B: acetonitrile, gradient: 0.00-2.00 min 10% B (60 ml/min), 2.00-14.00 min 10-50% B (60 ml/min), 14.00-14.10 min 50-100% B (60 ml/min), 14.10-17.00 min 100% B (60 ml/min), UV-Detection.

Method P9:
Instrument: Pump: Labomatic HD-5000 or HD-3000, Head HDK 280, low pressure gradient module ND-B1000; Manual injection valve: Rheodyne 3725i038; Detector: Knauer Azura UVD 2.15; Collector: Labomatic Labocol Vario-4000; Column: Chromatorex RP C-18 10 µm, 125×30 mm; Solvent A: water+0.1 vol-% formic acid (32%), Solvent B: acetonitrile, gradient: 0.00-0.50 min 35% B (150 ml/min), 0.50-6.00 min 35-65% B (150 ml/min), 6.00-6.10 min 65-100% B (150 ml/min), 6.10-8.00 min 100% B (150 ml/min), UV-Detection.
Method P10:
Instrument: Pump: Labomatic HD-5000 or HD-3000, Head HDK 280, low pressure gradient module ND-B1000; Manual injection valve: Rheodyne 3725i038; Detector: Knauer Azura UVD 2.15; Collector: Labomatic Labocol Vario-4000; Column: Chromatorex RP C-18 10 μm, 125×30 mm; Solvent A: water+0.2 Vol-% ammonia (32%), Solvent B: acetonitrile; Gradient: 0.00-0.50 min 65% B (150 ml/min), 0.50-6.00 min 65-100% B (150 mL/min), 6.00-8.00 min 100% B (150 mL/min), UV-Detection.
Method P11:
Instrument: Pump: Labomatic HD-5000 or HD-3000, Head HDK 280, low pressure gradient module ND-B1000; Manual injection valve: Rheodyne 3725i038; Detector: Knauer Azura UVD 2.15; Collector: Labomatic Labocol Vario-4000; Column: Chromatorex RP C-18 10 μm, 125×30 mm; Solvent A: water+0.2 Vol-% ammonia (32%), Solvent B: acetonitrile; Gradient: 0.00-0.50 min 15% B (150 ml/min), 0.50-6.00 min 15-55% B (150 mL/min), 6.00-6.10 min 55-100% B (150 mL/min), 6.10-8.00 min 100% B (150 mL/min), UV-Detection.
Method P12:
Instrument: Pump: Labomatic HD-5000 or HD-3000, Head HDK 280, low pressure gradient module ND-B1000; Manual injection valve: Rheodyne 3725i038; Detector: Knauer Azura UVD 2.15; Collector: Labomatic Labocol Vario-4000; Column: Chromatorex RP C-18 10 μm, 125×30 mm; Solvent A: water+0.2 Vol-% ammonia (32%), Solvent B: acetonitrile, Gradient: 0.00-0.50 min 30% B (150 ml/min), 0.50-6.00 min 30-70% B (150 mL/min), 6.00-6.10 min 70-100% B (150 mL/min), 6.10-8.00 min 100% B (150 mL/min), UV-Detection.
Specific Optial Rotation Methods:
Method O1:
Instrument: JASCO P2000 Polarimeter; wavelength 589 nm; temperature: 20° C.; integration time 10 s; path length 100 mm.

Experimental Section

Intermediates

Intermediate 1-1 tert-Butyl (3-bromopropyl)methylcarbamate

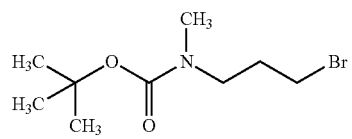

To a solution of tert-butyl (3-hydroxypropyl)methylcarbamate (5.25 g, 27.2 mmol, CAS 98642-44-5) and triphenylphosphane (9.36 g, 99% purity, 35.3 mmol) in dichloromethane (110 ml) was added tetrabromomethane (11.8 g, 99% purity, 35.3 mmol) over a period of 30 minutes at 0° C. and the mixture was stirred at 0° C. for 14 hours. The reaction was diluted with dichloromethane and the mixture was washed with sodium bicarbonate solution, sodium thiosulfate solution and brine. The organic phase was dried over sodium sulfate. The mixture was filtered and the filtrate was concentrated under reduced pressure. The crude product was purified by flash chromatography (Biotage SNAP cartridge $NH_2$ silica, hexanes/ethyl acetate gradient, 7%→60% ethyl acetate) to give the title compound (5.9 g).
$^1$H-NMR (400 MHz, CHLOROFORM-d) δ [ppm]: 0.009 (1.77), 1.402 (16.00), 1.536 (1.37), 2.022 (0.46), 2.815 (5.06), 3.275 (1.19), 3.292 (1.89), 3.308 (1.16), 3.326 (1.19), 3.343 (2.23), 3.360 (1.04).

Intermediate 1-2

Ethyl 7-bromo-3-(3-bromopropyl)-1H-indole-2-carboxylate

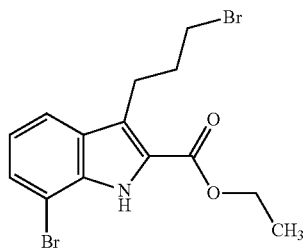 [SMILES: CCOC(=O)c1[nH]c2c(Br)cccc2c1CCCBr]

A mixture comprising ethyl 7-bromo-3-(3-hydroxypropyl)-1H-indole-2-carboxylate (20.0 g, 61.3 mmol, prepared as described in Journal of Medicinal Chemistry, 2015, 58, 2180-2194), tetrabromomethane (50.8 g, 153 mmol), pyridine (12 mL), dichloromethane (150 mL) and acetonitrile (350 mL) was cooled to 0° C. Triphenylphosphane (62.3 g, 237 mmol) was added and the reaction was stirred at rt overnight. Dichloromethane was removed, the precipitate filtered off and the filtrate concentrated. The residue was purified by repeated flash chromatography (Biotage SNAP cartridge silica 750 g, ethyl acetate: dichloromethane) to give the title compound (18.6 g).
MS: m/z=388 [M+H]$^+$.

Intermediate 1-3

Ethyl 7-bromo-3-[3-(naphthalen-1-yloxy)propyl]-1H-indole-2-carboxylate

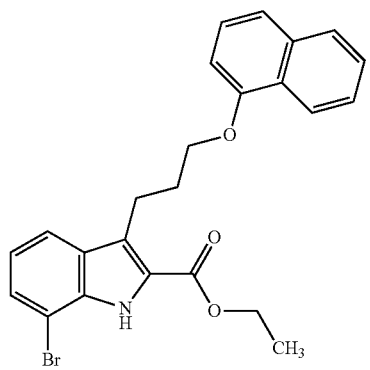 [SMILES: CCOC(=O)c1[nH]c2c(Br)cccc2c1CCCOc1cccc2ccccc12]

To a solution of naphthalen-1-ol (6.87 g, 47.7 mmol) in N,N-dimethylacetamide (180 mL) were added potassium carbonate (6.59 g, 47.7 mmol) followed by the solution of ethyl 7-bromo-3-(3-bromopropyl)-1H-indole-2-carboxylate (18.6 g, 47.7 mmol) in N,N-dimethylacetamide (85 mL). The mixture was stirred at 50° C. for 30 hours, poured into water and extracted with ethyl acetate. The organic layer was washed with water and brine and dried over sodium sulfate. After filtration and removal of the solvent the residue was purified by flash chromatography (Biotage SNAP cartridge silica 340 g, ethyl acetate: n-hexane) to give the title compound (13.5 g, 62% yield).

MS: m/z=452 [M+H]$^+$.

Intermediate 1-4

Ethyl 3-[3-(naphthalen-1-yloxy)propyl]-7-(4,4,5,5-tetramethyl-1,3,2-dioxaborolan-2-yl)-1H-indole-2-carboxylate

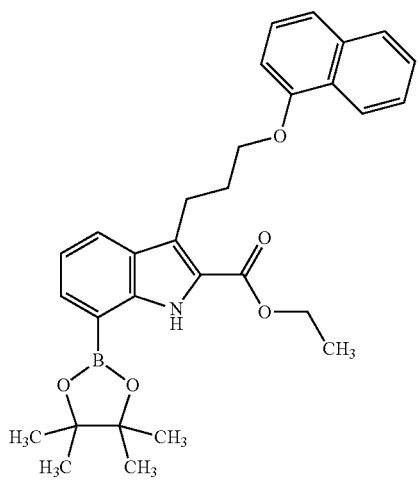 [SMILES: CCOC(=O)c1[nH]c2c(B3OC(C)(C)C(C)(C)O3)cccc2c1CCCOc1cccc2ccccc12]

Ethyl 3-[3-(naphthalen-1-yloxy)propyl]-7-(4,4,5,5-tetramethyl-1,3,2-dioxaborolan-2-yl)-1H-indole-2-carboxylate was prepared as described in the literature (Journal of Medicinal Chemistry, 2015, 58, 2180-2194).

Intermediate 1-5

Ethyl 4-bromo-3-(bromomethyl)-1-methyl-1H-pyrazole-5-carboxylate

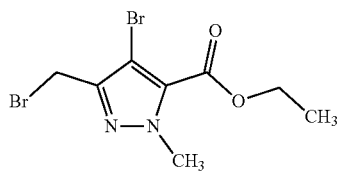

4-Bromo-3-bromomethyl-1-methyl-1H-pyrazole-5-carboxylic acid ethyl ester was prepared as described in the literature (Journal of Medicinal Chemistry, 2014, 57, 4720-4744) starting from ethyl 1,3-dimethyl-1H-pyrazole-5-carboxylate (CAS 5744-40-1).

LC-MS (Method 1): Rt=1.23 min; MS (ESIpos): m/z=324 [M+H]$^+$

Intermediate 1-6 tert-butyl 4-(4-{[4-bromo-5-(ethoxycarbonyl)-1-methyl-1H-pyrazol-3-yl]methoxy}phenyl)piperazine-1-carboxylate

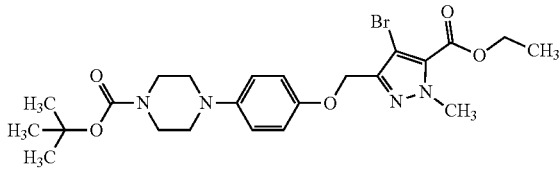 [SMILES: CCOC(=O)c1c(Br)c(COc2ccc(N3CCN(C(=O)OC(C)(C)C)CC3)cc2)nn1C]

A mixture of ethyl 4-bromo-3-(bromomethyl)-1-methyl-1H-pyrazole-5-carboxylate (10.9 g, 33.3 mmol), tert-butyl 4-(4-hydroxyphenyl)piperazine-1-carboxylate (10.0 g, 34.9 mmol, CAS 158985-2-2) and potassium carbonate (13.8 g, 99.8 mmol) in DMF (100 ml) was stirred for 12 h at room temperature. For work-up, water was added and the mixture was extracted with ethyl acetate, the organic phase was washed with water, filtrated through a silicone filter and concentrated. The residue was purified by flash chromatography (hexanes/ethyl acetate gradient, 20%→30% ethyl acetate) to give the title compound (11.9 g, 68% yield).

LC-MS (Method 2): R$_t$=1.50 min; MS (ESIpos): m/z=523 [M+H]$^+$ $^1$H-NMR (400 MHz, DMSO-d6) δ [ppm]: 1.155 (1.12), 1.173 (2.34), 1.190 (1.18), 1.318 (1.52), 1.335 (3.30), 1.353 (1.55), 1.413 (16.00), 1.988 (4.49), 2.941 (0.94), 2.954 (1.31), 2.966 (1.04), 3.427 (0.87), 3.439 (1.14), 3.450 (0.78), 4.017 (1.04), 4.035 (1.03), 4.081 (5.74), 4.324 (0.45), 4.342 (1.45), 4.359 (1.44), 4.377 (0.43), 4.924 (2.68), 6.911 (4.03).

Intermediate 1-7 tert-butyl 4-(4-{[4-bromo-5-(hydroxymethyl)-1-methyl-1H-pyrazol-3-yl]methoxy}phenyl)piperazine-1-carboxylate

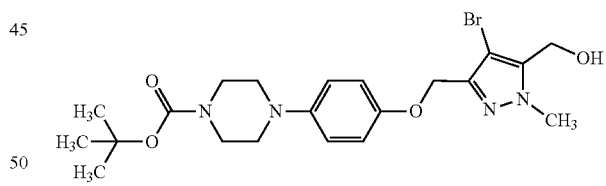

Lithium borohydride (603 mg, 27.7 mmol) was added in portions under ice cooling to a solution of tert-butyl 4-(4-{[4-bromo-5-(ethoxycarbonyl)-1-methyl-1H-pyrazol-3-yl]methoxy}phenyl)piperazine-1-carboxylate (14.5 g, 27.7 mmol) in THF (540 ml). After complete conversion of the starting material, the reaction mixture was quenched by addition of saturated aqueous ammonium chloride and the mixture was extracted three times with ethyl acetate. The combined organic phases were filtrated through a silicone filter, concentrated under reduced pressure and the residue was purified by flash chromatography (hexanes/ethyl acetate gradient, 50%→100% ethyl acetate) to give the title compound (8.55 g, 64% yield).

LC-MS (Method 2): R$_t$=1.22 min; MS (ESIpos): m/z=481 [M+H]$^+$

¹H-NMR (400 MHz, DMSO-d6) δ [ppm]: 1.413 (16.00), 2.522 (1.93), 2.935 (1.01), 2.948 (1.42), 2.961 (1.16), 3.427 (0.93), 3.439 (1.24), 3.450 (0.91), 3.856 (5.85), 4.471 (0.88), 4.482 (0.92), 4.851 (2.76), 5.411 (0.48), 6.905 (4.28).

Intermediate 1-8 ethyl 7-[3-({4-[4-(tert-butoxycarbonyl)piperazin-1-yl]phenoxy}methyl)-5-(hydroxymethyl)-1-methyl-1H-pyrazol-4-yl]-3-[3-(naphthalen-1-yloxy)propyl]-1H-indole-2-carboxylate

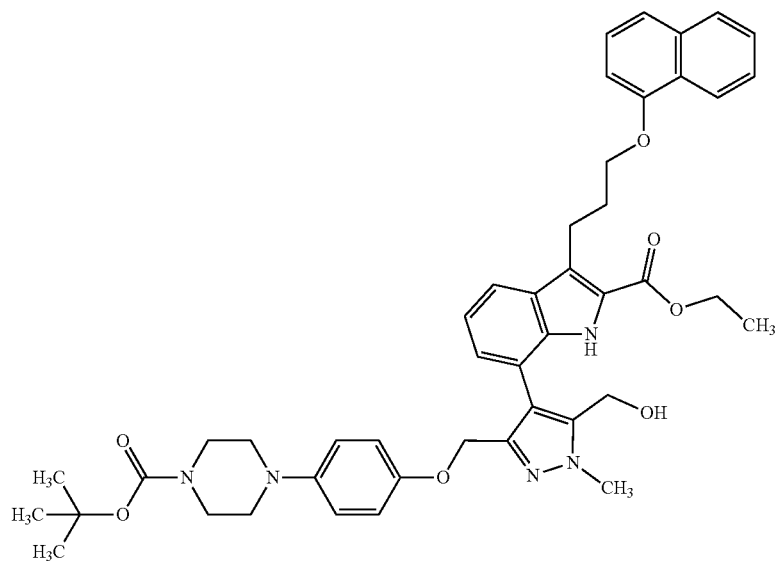

XPhos Pd G2 (see abbreviation list; 317 mg, 403 μmol) was added to a degassed mixture of ethyl 3-[3-(naphthalen-1-yloxy)propyl]-7-(4,4,5,5-tetramethyl-1,3,2-dioxaborolan-2-yl)-1H-indole-2-carboxylate (6.57 g, 13.2 mmol), tert-butyl 4-(4-{[4-bromo-5-(hydroxymethyl)-1-methyl-1H-pyrazol-3-yl]methoxy}phenyl)piperazine-1-carboxylate (5.76 g, 12.0 mmol), aqueous potassium phosphate solution (48 ml, 0.50 M, 24 mmol) and THF (150 ml). The mixture was stirred for 2 h at 45° C. For work-up, ethyl acetate was added, the mixture was filtrated through a pad of celite, eluted with ethyl acetate and the organic phase was washed with brine, filtrated through a silicone filter and concentrated. The residue was purified by flash chromatography (hexanes/ethyl acetate gradient) to give the title compound (8.07 g, 79% yield).

LC-MS (Method 2): $R_t$=1.71 min; MS (ESIpos): m/z=775 [M+H]⁺

¹H-NMR (400 MHz, DMSO-d6): δ [ppm]=10.77 (br s, 1H), 8.21-8.17 (m, 1H), 7.86-7.82 (m, 1H), 7.67 (dd, 1H), 7.53-7.44 (m, 2H), 7.44-7.41 (m, 1H), 7.39-7.34 (m, 1H), 7.21 (dd, 1H), 7.03 (t, 1H), 6.87 (d, 1H), 6.78-6.72 (m, 4H), 5.71 (br s, 1H), 4.85-4.63 (m, 2H), 4.45-4.30 (m, 2H), 4.26-4.15 (m, 4H), 3.93 (s, 3H), 3.42-3.36 (m, 4H), 2.91-2.83 (m, 4H), 2.65 (t, 1H), 2.30 (t, 1H), 2.24-2.16 (m, 2H), 1.38 (s, 9H), 1.24 (t, 3H)

Intermediate 1-9 ethyl 7-{3-({4-[4-(tert-butoxycarbonyl)piperazin-1-yl]phenoxy}methyl)-1-methyl-5-[(prop-2-en-1-yloxy)methyl]-1H-pyrazol-4-yl}-3-[3-(naphthalen-1-yloxy) propyl]-1-(prop-2-en-1-yl)-1H-indole-2-carboxylate

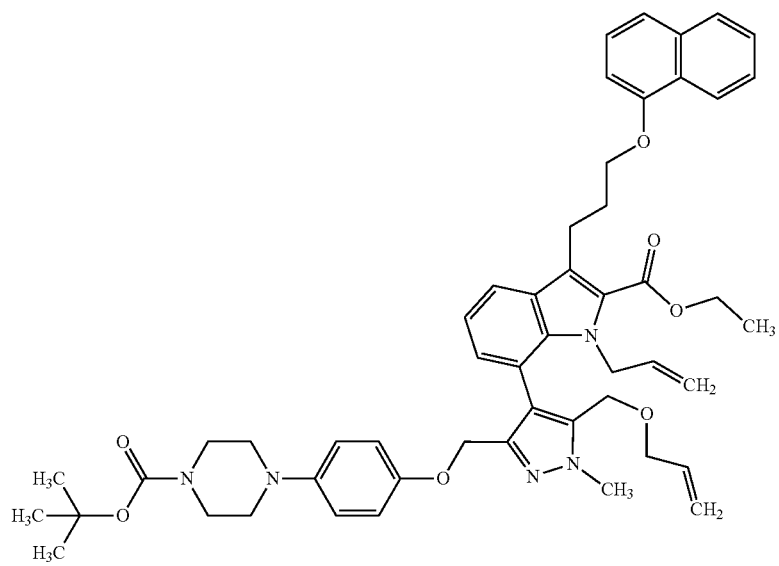 [SMILES: C=CCOCc1c(-c2cccc3c(CCCOc4cccc5ccccc45)c(C(=O)OCC)n(CC=C)c23)c(COc2ccc(N3CCN(C(=O)OC(C)(C)C)CC3)cc2)nn1C]

Sodium hydride (929 mg, 60% suspension in mineral oil, 23.2 mmol) was added to a solution of ethyl 7-[3-({4-[4-(tert-butoxycarbonyl)piperazin-1-yl]phenoxy}methyl)-5-(hydroxymethyl)-1-methyl-1H-pyrazol-4-yl]-3-[3-(naphthalen-1-yloxy)propyl]-1H-indole-2-carboxylate (5.99 g, 7.74 mmol) in THF (100 ml) at 0° C. and the mixture was stirred for 30 min. Allyl bromide (2.0 ml, 23 mmol) was added at 0° C. and the mixture was stirred at room temperature for 2 days. Additional portions of sodium hydride (309 mg, 60% suspension in mineral oil, 7.73 mmol) and allyl bromide (0.67 ml, 7.7 mmol) were added and the mixture was stirred for further 3 days at room temperature. For work-up, brine was added and the mixture was extracted with ethyl acetate. The organic phase was washed with brine, filtrated through a silicone filter and concentrated. The residue was purified by flash chromatography (Biotage SNAP cartridge silica 100 g, hexanes/ethyl acetate gradient, 0%→60% ethyl acetate) to give the title compound (5.77 g, 81% yield).

LC-MS ( ): Rt=1.85 min; MS (ESIpos): m/z=855 [M+H]$^+$ $^1$H-NMR (400 MHz, DMSO-d6) δ [ppm]: 1.132 (2.13), 1.149 (4.24), 1.167 (2.05), 1.211 (0.20), 1.224 (1.41), 1.241 (3.00), 1.259 (1.41), 1.371 (16.00), 1.390 (0.34), 1.956 (0.14), 1.965 (8.21), 2.158 (0.29), 2.176 (0.41), 2.194 (0.31), 2.209 (0.11), 2.296 (0.25), 2.300 (0.56), 2.304 (0.76), 2.309 (0.55), 2.313 (0.25), 2.638 (0.27), 2.642 (0.56), 2.646 (0.79), 2.651 (0.55), 2.655 (0.25), 2.803 (0.79), 2.815 (1.12), 2.827 (0.85), 3.252 (0.34), 3.271 (0.57), 3.291 (0.53), 3.331 (0.99), 3.344 (1.20), 3.357 (0.84), 3.737 (0.18), 3.740 (0.11), 3.747 (0.11), 3.751 (0.18), 3.754 (0.11), 3.766 (0.22), 3.770 (0.37), 3.773 (0.23), 3.780 (0.23), 3.783 (0.37), 3.787 (0.23), 3.816 (0.23), 3.819 (0.38), 3.823 (0.25), 3.829 (0.25), 3.832 (0.38), 3.836 (0.23), 3.848 (0.13), 3.852 (0.19), 3.856 (0.13), 3.861 (0.15), 3.865 (0.22), 3.869 (0.17), 3.886 (4.49), 3.977 (0.60), 3.995 (1.78), 4.013 (1.78), 4.030 (0.59), 4.052 (0.56), 4.082 (0.66), 4.115 (0.45), 4.139 (0.41), 4.154 (1.16), 4.169 (0.41), 4.189 (0.38), 4.207 (1.21), 4.224 (1.18), 4.242 (0.36), 4.271 (0.66), 4.301 (0.56), 4.648 (1.78), 4.672 (0.13), 4.677 (0.11), 4.684 (0.13), 4.714 (0.74), 4.728 (0.28), 4.732 (0.32), 4.736 (0.46), 4.740 (0.42), 4.762 (0.24), 4.768 (0.24), 4.772 (0.25), 4.816 (0.11), 4.978 (0.36), 4.983 (0.42), 4.986 (0.22), 5.005 (0.79), 5.009 (0.70), 5.045 (0.22), 5.049 (0.48), 5.054 (0.43), 5.057 (0.15), 5.428 (0.17), 5.441 (0.13), 5.455 (0.20), 5.460 (0.13), 5.467 (0.11), 5.472 (0.17), 5.484 (0.14), 5.498 (0.18), 5.666 (0.15), 5.679 (0.29), 5.692 (0.24), 5.706 (0.29), 5.709 (0.17), 5.719 (0.17), 5.723 (0.27), 5.736 (0.20), 5.749 (0.24), 6.583 (0.99), 6.589 (0.36), 6.601 (0.43), 6.606 (1.36), 6.614 (0.15), 6.692 (0.17), 6.701 (1.37), 6.724 (0.93), 6.827 (0.52), 6.845 (0.57), 6.978 (0.39), 6.981 (0.45), 6.996 (0.69), 6.999 (0.66), 7.032 (0.61), 7.052 (0.69), 7.070 (0.34), 7.332 (0.39), 7.353 (0.74), 7.372 (0.55), 7.422 (0.75), 7.443 (0.45), 7.469 (0.15), 7.481 (0.50), 7.486 (0.78), 7.497 (0.97), 7.505 (0.85), 7.511 (0.51), 7.523 (0.17), 7.728 (0.51), 7.731 (0.53), 7.747 (0.48), 7.750 (0.47), 7.835 (0.43), 7.838 (0.33), 7.845 (0.23), 7.852 (0.31), 7.858 (0.37), 8.200 (0.37), 8.207 (0.31), 8.215 (0.18), 8.224 (0.36).

Intermediate 1-10

(rac)-(E/Z)-ethyl 3-({4-[4-(tert-butoxycarbonyl)piperazin-1-yl]phenoxy}methyl)-1-methyl-7-[3-(naphthalen-1-yloxy)propyl]-1,10,13,15-tetrahydropyrazolo[4',3':9,10][1,6]oxazacycloundecino[8,7,6-hi]indole-8-carboxylate

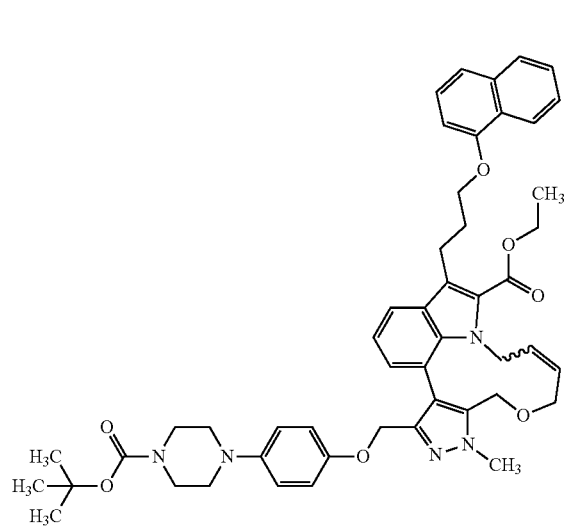 [SMILES: CCOC(=O)c1c(CCCOc2cccc3ccccc23)c2cccc3c2n1CC=CCOCc1c-3c(COc2ccc(N3CCN(C(=O)OC(C)(C)C)CC3)cc2)nn1C]

(1,3-Bis(2,4,6-trimethylphenyl)-2-imidazolidinylidene)dichloro(phenylmethylene)(tricyclohexylphosphine)ruthenium (Grubbs 2nd generation catalyst; CAS No 246047-72-3; 573 mg, 674 µmol) was added to a solution of ethyl 7-{3-({4-[4-(tert-butoxycarbonyl)piperazin-1-yl]phenoxy}methyl)-1-methyl-5-[(prop-2-en-1-yloxy)methyl]-1H-pyrazol-4-yl}-3-[3-(naphthalen-1-yloxy)propyl]-1-(prop-2-en-1-yl)-1H-indole-2-carboxylate (5.76 g, 6.74 mmol) in dichloromethane (87 ml) and the mixture was stirred at room temperature overnight. For work-up, the reaction mixture was concentrated and the residue was purified by flash chromatography (Biotage SNAP cartridge silica 50 g, hexanes/ethyl acetate gradient, 0%→40% ethyl acetate) to give the title compound (2.51 g) together with unidentified impurities.

LC-MS (Method 2): $R_t$=1.81 min; MS (ESIpos): m/z=826 [M+H]$^+$

Intermediate 1-11

(rac)-ethyl 3-({4-[4-(tert-butoxycarbonyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate

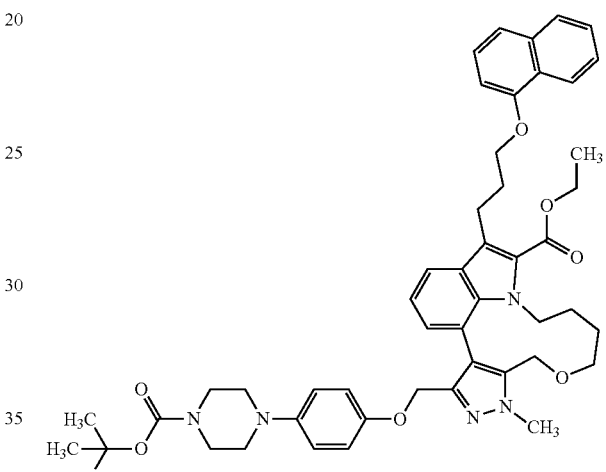

An autoclave was charged with (rac)-(E/Z)-ethyl 3-({4-[4-(tert-butoxycarbonyl)piperazin-1-yl]phenoxy}methyl)-1-methyl-7-[3-(naphthalen-1-yloxy)propyl]-1,10,13,15-tetrahydropyrazolo[4',3':9,10][1,6]oxazacycloundecino[8,7,6-hi]indole-8-carboxylate (2.50 g, 3.03 mmol), ethanol (15 ml), THF (10 ml) and palladium 10% on charcoal (322 mg, 303 µmol) and the mixture was stirred under 15.6 bar hydrogen atmosphere at room temperature for 26 h. For work-up, the mixture was filtrated through a pad of celite, eluted with ethyl acetate and the combined filtrates were concentrated under reduced pressure to give the title compound (2.45 g, 88% yield), which was directly used in the next step.

LC-MS (Method 2): $R_t$=1.83 min; MS (ESIpos): m/z=828.5 [M+H]$^+$

Intermediate 1-12

(rac)-ethyl 1-methyl-7-[3-(naphthalen-1-yloxy)propyl]-3-{[4-(piperazin-1-yl)phenoxy]methyl}-1,10,11,12,13,15-hexahydropyrazolo[4',3':9,10][1,6]oxazacycloundecino[8,7,6-hi]indole-8-carboxylate hydrochloric acid salt

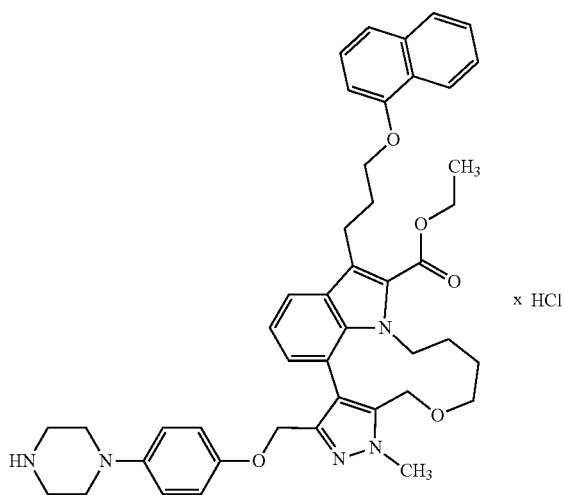 [SMILES: CCOC(=O)c1c(CCCOc2cccc3ccccc23)c2cccc3c2n1CCCCOCc1c-3c(COc2ccc(N3CCNCC3)cc2)nn1C ; Cl]

Hydrochloric acid (7.4 ml, 4.0 M in dioxane, 30 mmol) was added to a solution of (rac)-ethyl 3-({4-[4-(tert-butoxycarbonyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (2.45 g, 2.96 mmol) in ethanol (47 ml) and the mixture was stirred for 16 h at room temperature. For work-up, the reaction mixture was concentrated to give the title compound (2.53 g) which was used in the next step without further purification.

LC-MS (Method 1): $R_t$=1.28 min; MS (ESIpos): m/z=728 $[M+H]^+$ $^1$H-NMR (400 MHz, DMSO-d6) δ [ppm]: 0.334 (0.45), 0.353 (1.03), 0.370 (0.53), 1.035 (7.43), 1.052 (15.17), 1.070 (7.18), 1.232 (1.00), 1.249 (1.13), 1.267 (1.80), 1.281 (5.58), 1.285 (3.40), 1.299 (11.02), 1.317 (5.19), 1.352 (1.43), 1.907 (0.45), 2.163 (1.22), 2.179 (1.99), 2.194 (1.37), 2.323 (0.81), 2.327 (1.15), 2.331 (0.81), 2.518 (4.51), 2.523 (3.01), 2.665 (0.81), 2.669 (1.11), 2.674 (0.77), 2.808 (0.71), 2.820 (0.58), 2.837 (0.71), 3.129 (13.88), 3.155 (3.40), 3.204 (0.41), 3.223 (0.71), 3.238 (0.71), 3.257 (1.24), 3.276 (0.83), 3.315 (0.51), 3.332 (0.94), 3.351 (0.66), 3.366 (0.66), 3.410 (2.12), 3.428 (7.01), 3.445 (6.75), 3.462 (2.65), 3.470 (0.98), 3.487 (1.03), 3.499 (0.53), 3.564 (11.26), 3.923 (16.00), 3.945 (2.59), 4.066 (0.60), 4.090 (1.02), 4.125 (2.16), 4.134 (1.82), 4.186 (0.68), 4.211 (0.45), 4.219 (0.43), 4.237 (1.03), 4.246 (0.92), 4.255 (1.17), 4.266 (3.22), 4.282 (2.76), 4.299 (4.25), 4.317 (1.94), 4.327 (1.09), 4.335 (1.00), 4.344 (1.07), 4.366 (0.58), 4.408 (1.28), 4.419 (1.03), 4.445 (1.62), 4.458 (3.18), 4.487 (4.14), 4.533 (3.84), 4.673 (2.46), 4.686 (2.90), 4.707 (2.56), 4.714 (2.69), 4.738 (0.45), 6.557 (3.63), 6.580 (4.34), 6.663 (0.60), 6.685 (0.81), 6.748 (3.70), 6.771 (2.99), 6.796 (2.11), 6.805 (0.98), 6.814 (2.24), 6.828 (0.60), 6.856 (1.90), 6.858 (1.97), 6.874 (2.46), 6.876 (2.31), 6.978 (1.99), 6.997 (2.35), 7.015 (1.49), 7.036 (0.94), 7.049 (0.68), 7.347 (1.45), 7.367 (2.61), 7.387 (1.99), 7.445 (2.84), 7.466 (1.84), 7.500 (0.66), 7.512 (2.03), 7.517 (3.20), 7.526 (3.65), 7.536 (3.44), 7.541 (2.01), 7.553 (0.66), 7.716 (1.97), 7.719 (2.11), 7.736 (1.86), 7.739 (1.80), 7.863 (1.88), 7.873 (1.02), 7.880 (1.28), 7.886 (1.58), 8.225 (1.49), 8.233 (1.24), 8.250 (1.43), 9.012 (1.37).

Intermediate 1-13

(rac)-(E/Z)-ethyl 1-methyl-7-[3-(naphthalen-1-yloxy)propyl]-3-{[4-(piperazin-1-yl)phenoxy]methyl}-1,10,13,15-tetrahydropyrazolo[4',3':9,10][1,6]oxazacycloundecino[8,7,6-hi]indole-8-carboxylate hydrochloric acid salt

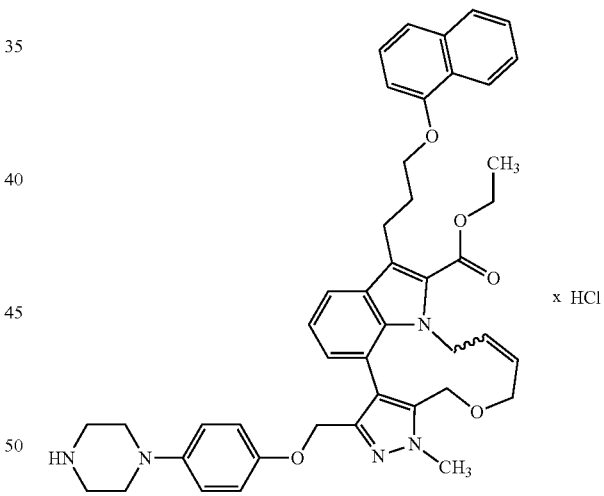

Hydrochloric acid (3.9 ml, 4.0 M in dioxane, 16 mmol) was added to a solution of (rac)-(E/Z)-ethyl 3-({4-[4-(tert-butoxycarbonyl)piperazin-1-yl]phenoxy}methyl)-1-methyl-7-[3-(naphthalen-1-yloxy)propyl]-1,10,13,15-tetrahydropyrazolo[4',3':9,10][1,6]oxazacycloundecino[8,7,6-hi]indole-8-carboxylate (see Intermediate 1-10; 175 mg, 212 μmol) in methanol (2.4 ml) and the mixture was stirred for 1 h at room temperature. For work-up, the reaction mixture was concentrated to give the title compound (178 mg) which was used in the next step without further purification.

Intermediate 1-14

(rac)-(E/Z)-ethyl 3-{[4-(4-acetylpiperazin-1-yl)phenoxy]methyl}-1-methyl-7-[3-(naphthalen-1-yloxy)propyl]-1,10,13,15-tetrahydropyrazolo[4',3':9,10][1,6]oxazacycloundecino[8,7,6-hi]indole-8-carboxylate

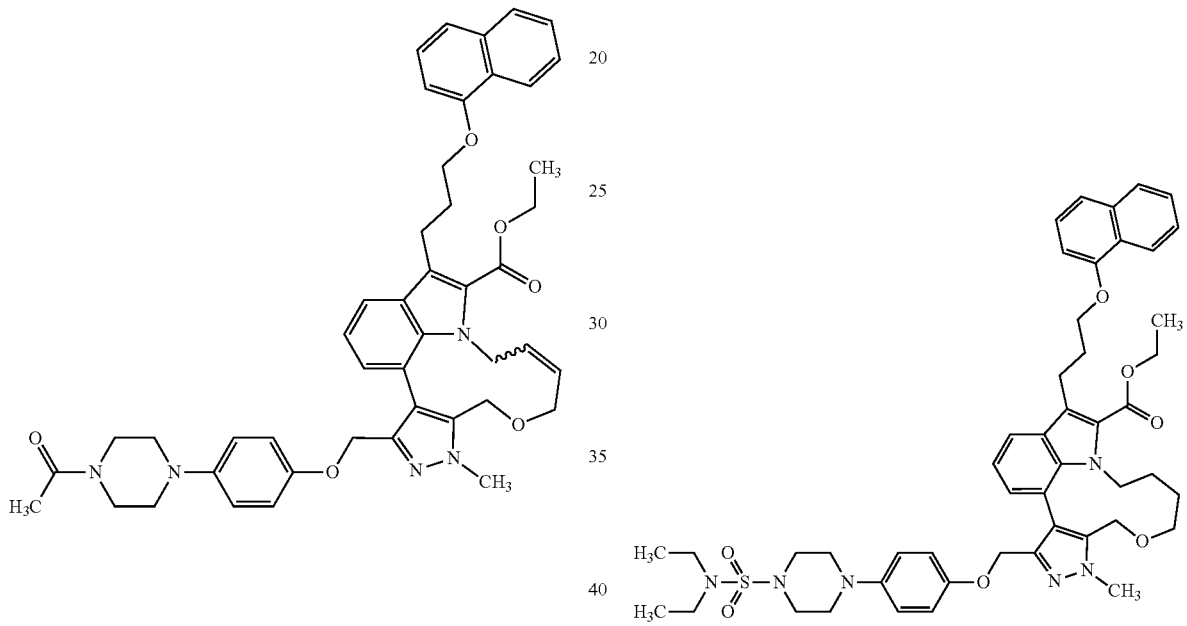

Pyridine (120 µl, 1.5 mmol) and acetyl chloride (41 µl, 580 µmol) were added to a solution of (rac)-ethyl 1-methyl-7-[3-(naphthalen-1-yloxy)propyl]-3-{[4-(piperazin-1-yl)phenoxy]methyl}-1,10,13,15-tetrahydropyrazolo[4',3':9,10][1,6]oxazacycloundecino[8,7,6-hi]indole-8-carboxylate hydrochloric acid salt (222 mg) in dichloromethane (2.8 ml) at 0° C. and the mixture was stirred at 0° C. for 1 h. For work-up, water was added and the mixture was extracted three times with a mixture of dichloromethane/2-propanol (4:1). The combined organic phase were washed with brine, filtrated through a silicone filter and concentrated. The residue was purified by flash chromatography (Biotage SNAP cartridge silica 10 g, ethyl acetate/methanol gradient 0%→20% methanol) to give the title compound (159 mg, 95% purity, 68% yield).

LC-MS (Method 2): $R_t$=1.61 min; MS (ESIpos): m/z=769 [M+H]$^+$ $^1$H-NMR (400 MHz, DMSO-d6): δ [ppm]=8.25-8.19 (m, 1H), 7.91-7.85 (m, 1H), 7.73 (dd, 1H), 7.55-7.35 (m, 4H), 7.01 (dd, 1H), 6.85-6.77 (m, 2H), 6.70-6.61 (m, 2H), 6.49-6.45 (m, 2H), 5.20 (td, 1H), 5.06-4.92 (m, 2H), 4.82-4.59 (m, 3H), 4.38-4.22 (m, 4H), 4.18-4.05 (m, 2H), 3.94 (s, 3H), 3.81 (dd, 1H), 3.55-3.39 (m, 5H), 3.29-3.20 (m, 1H), 2.90-2.77 (m, 4H), 2.26-2.11 (m, 2H), 1.96 (s, 3H), 1.33-1.28 (m, 3H)

Intermediate 1-15

(rac)-ethyl 3-({4-[4-(diethylsulfamoyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate Diethylsulfamyl chloride (64.3 mg, 375 µmol) was added dropwise to a solution of (rac)-ethyl 1-methyl-7-[3-(naphthalen-1-yloxy)propyl]-3-{[4-(piperazin-1-yl)phenoxy]methyl}-1,10,11,12,13,15-hexahydropyrazolo[4',3':9,10][1,6]oxazacycloundecino[8,7,6-hi]indole-8-carboxylate hydrochloric acid salt (see Intermediate 1-12, 250 mg, 312 µmol) and N,N-diisopropylethylamine (270 µl, 1.6 mmol) in dichloromethane (5.6 ml, 87 mmol) at 0° C. and the mixture was stirred for 24 h at room temperature. For work-up, the mixture was diluted with dichloromethane, washed with water and brine and the organic phase was filtered through a silicone filter and concentrated. The residue was purified by flash chromatography (Biotage SNAP cartridge silica, hexanes/ethyl acetate gradient, 0%→100% ethyl acetate) to give the title compound (169 mg, 86% purity, 54% yield).

LC-MS (Method 2): $R_t$=1.77 min; MS (ESIpos): m/z=863 [M+H]$^+$

221

Intermediate 1-16

(rac)-ethyl 1-methyl-3-{[4-(4-methylpiperazin-1-yl)phenoxy]methyl}-7-[3-(naphthalen-1-yloxy)propyl]-1,10,11,12,13,15-hexahydropyrazolo[4',3':9,10][1,6]oxazacycloundecino[8,7,6-hi]indole-8-carboxylate

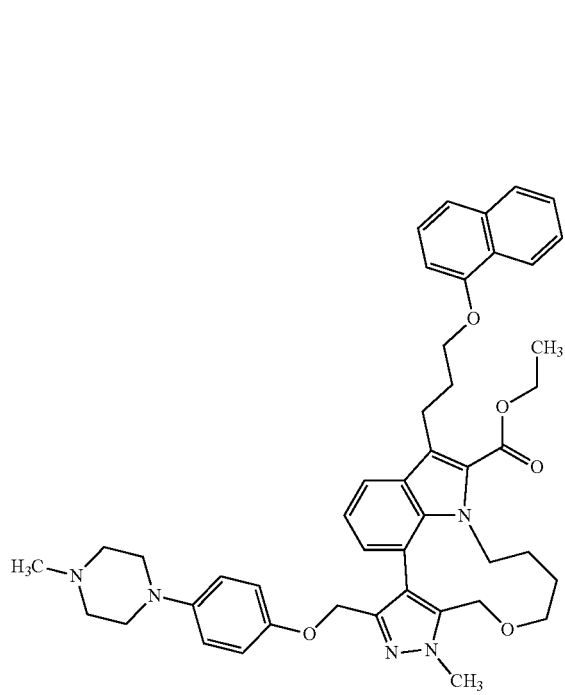 [SMILES: CCOC(=O)c1c(CCCOc2cccc3ccccc23)c2cccc3c2n1CCCCOCc1c-3c(COc2ccc(N3CCN(C)CC3)cc2)nn1C]

Acetic acid (16 μl, 270 μmol) was added to a solution of (rac)-ethyl 1-methyl-7-[3-(naphthalen-1-yloxy)propyl]-3-{[4-(piperazin-1-yl)phenoxy]methyl}-1,10,11,12,13,15-hexahydropyrazolo[4',3':9,10][1,6]oxazacycloundecino[8,7,6-hi]indole-8-carboxylate (see Intermediate 1-12, 100 mg, 137 μmol) in methanol (2.2 ml) and the mixture was stirred for 5 min. Sodium cyanoborohydride (17.3 mg, 275 μmol) was added and the mixture was stirred for 5 min, aqueous formaldehyde (22 μl, 35% purity, 270 μmol) was added and the mixture was stirred at 60° C. for 6 h and overnight at room temperature. For work-up, the reaction mixture was concentrated under reduced pressure, ethyl acetate was added and the organic phase was washed with saturated sodium bicarbonate solution. The aqueous phase was extracted with ethyl acetate and the combined organic phases were filtrated through a silicone filter and concentrated under reduced pressure to give the title compound (77.0 mg) which was used in the next step without further purification.

LC-MS (Method 1): $R_t$=1.65 min; MS (ESIpos): m/z=742 [M+H]$^+$

222

Intermediate 1-17

(rac)-ethyl 1-methyl-3-({4-[4-(methylsulfonyl)piperazin-1-yl]phenoxy}methyl)-7-[3-(naphthalen-1-yloxy)propyl]-1,10,11,12,13,15-hexahydropyrazolo[4',3':9,10][1,6]oxazacycloundecino[8,7,6-hi]indole-8-carboxylate

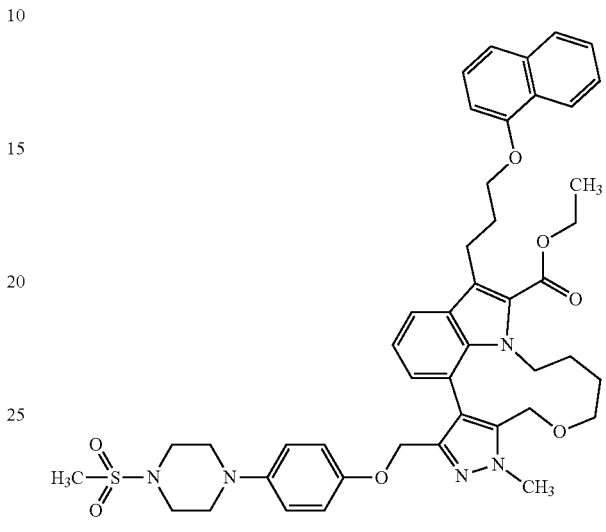

Methanesulfonyl chloride (29 μl, 370 μmol) was added to a solution of (rac)-ethyl 1-methyl-7-[3-(naphthalen-1-yloxy)propyl]-3-{[4-(piperazin-1-yl)phenoxy]methyl}-1,10,11,12,13,15-hexahydropyrazolo[4',3':9,10][1,6]oxazacycloundecino[8,7,6-hi]indole-8-carboxylate hydrochloric acid salt (see Intermediate 1-12, 250 mg, 312 μmol) and N,N-diisopropylethylamine (270 μl, 1.6 mmol) in dichloromethane (5.6 ml) at 0° C. and the mixture was stirred for 24 at room temperature. For work-up, the mixture was concentrated and the residue was purified by flash chromatography (Biotage SNAP cartridge silica 25 g, hexanes/ethyl acetate gradient, 0%→100% ethyl acetate) to give the title compound (187 mg).

LC-MS (Method 2): $R_t$=1.64 min; MS (ESIpos): m/z=806 [M+H]$^+$ $^1$H-NMR (400 MHz, DMSO-d6) δ [ppm]: 0.355 (0.51), 1.041 (0.96), 1.056 (0.77), 1.154 (0.80), 1.172 (1.67), 1.190 (0.90), 1.235 (0.67), 1.250 (0.71), 1.269 (1.03), 1.282 (4.08), 1.286 (1.70), 1.300 (8.39), 1.317 (3.95), 1.987 (2.89), 2.163 (0.80), 2.180 (1.25), 2.195 (0.87), 2.318 (0.64), 2.322 (1.41), 2.326 (1.93), 2.331 (1.32), 2.336 (0.61), 2.518 (7.10), 2.522 (4.82), 2.659 (0.67), 2.664 (1.41), 2.668 (1.93), 2.673 (1.35), 2.678 (0.61), 2.810 (0.51), 2.823 (0.42), 2.840 (0.58), 2.863 (16.00), 2.880 (2.12), 2.944 (2.15), 2.956 (3.05), 2.969 (2.89), 2.993 (0.42), 3.110 (3.02), 3.123 (3.18), 3.134 (2.25), 3.159 (0.45), 3.220 (0.48), 3.235 (0.45), 3.254 (0.74), 3.273 (0.42), 3.358 (0.55), 3.374 (0.51), 3.459 (0.55), 3.473 (0.45), 3.489 (0.51), 3.922 (11.79), 3.944 (1.32), 4.017 (0.67), 4.035 (0.67), 4.096 (0.67), 4.110 (1.06), 4.127 (1.70), 4.141 (0.84), 4.236 (0.71), 4.246 (0.48), 4.254 (0.77), 4.264 (1.41), 4.271 (1.51), 4.281 (1.48), 4.284 (0.96), 4.303 (2.28), 4.320 (1.25), 4.329 (0.74), 4.347 (0.67), 4.414 (0.61), 4.444 (1.70), 4.472 (1.77), 4.674 (1.64), 4.681 (2.12), 4.709 (2.38), 6.511 (2.89), 6.534 (3.57), 6.638 (0.42), 6.687 (3.50), 6.692 (1.03), 6.709 (2.70), 6.747 (0.39), 6.799 (1.35), 6.816 (1.48), 6.857 (1.38), 6.860 (1.45), 6.875 (1.70), 6.877 (1.67), 6.986 (1.41), 7.004 (1.45), 7.006 (1.70), 7.024 (1.16), 7.039 (0.48), 7.348 (1.06),

Intermediate 1-18

(rac)-ethyl 3-({4-[4-(cyclopropylsulfonyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate

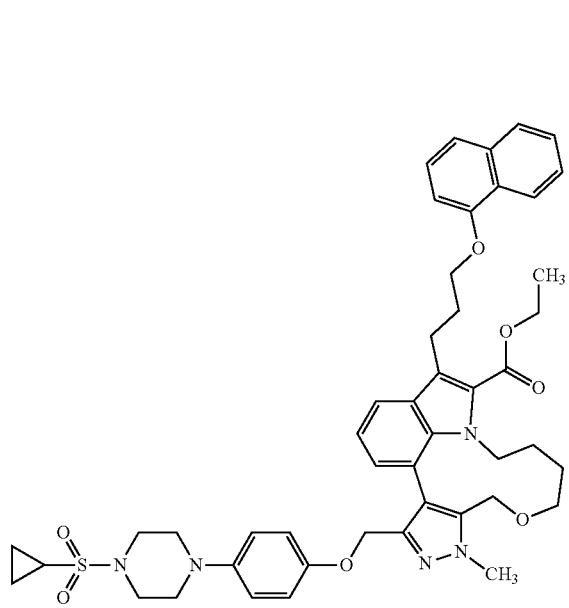 [SMILES: CCOC(=O)c1c(CCCOc2cccc3ccccc23)c2cccc3c2n1CCCCOCc1c-3c(COc2ccc(N3CCN(S(=O)(=O)C4CC4)CC3)cc2)nn1C]

The title compound was prepared in analogy to the synthesis of (rac)-ethyl 1-methyl-3-({4-[4-(methylsulfonyl)piperazin-1-yl]phenoxy}methyl)-7-[3-(naphthalen-1-yloxy)propyl]-1,10,11,12,13,15-hexahydropyrazolo[4',3':9,10][1,6]oxazacycloundecino[8,7,6-hi]indole-8-carboxylate using cyclopropanesulfonyl chloride (38 µl, 370 µmol) as reactant to give the title compound (206 mg, 79% yield).

LC-MS (Method 2): $R_t$=1.70 min; MS (ESIpos): m/z=832 [M+H]$^+$ $^1$H-NMR (400 MHz, DMSO-d6) δ [ppm]: 0.893 (0.52), 0.898 (0.63), 0.906 (0.75), 0.910 (0.85), 0.950 (0.61), 0.970 (0.72), 1.154 (4.14), 1.172 (8.23), 1.190 (3.99), 1.270 (0.44), 1.284 (1.61), 1.302 (3.22), 1.320 (1.54), 1.988 (16.00), 2.074 (3.18), 2.178 (0.52), 2.323 (0.57), 2.327 (0.81), 2.331 (0.59), 2.518 (3.17), 2.523 (2.17), 2.565 (0.42), 2.665 (0.59), 2.669 (0.82), 2.673 (0.59), 2.926 (0.89), 2.939 (1.22), 2.951 (1.09), 3.185 (1.11), 3.198 (1.30), 3.209 (0.96), 3.924 (4.74), 3.945 (0.61), 4.000 (1.16), 4.018 (3.50), 4.035 (3.53), 4.053 (1.19), 4.109 (0.46), 4.123 (0.79), 4.266 (0.56), 4.274 (0.61), 4.284 (0.61), 4.305 (0.87), 4.323 (0.49), 4.442 (0.71), 4.470 (0.72), 4.675 (0.64), 4.683 (0.87), 4.710 (0.87), 6.505 (1.11), 6.528 (1.37), 6.680 (1.37), 6.702 (1.05), 6.797 (0.56), 6.815 (0.59), 6.858 (0.55), 6.861 (0.61), 6.875 (0.68), 6.879 (0.67), 6.989 (0.56), 7.008 (0.68), 7.026 (0.44), 7.348 (0.42), 7.369 (0.77), 7.388 (0.57), 7.444 (0.79), 7.465 (0.51), 7.509 (0.56), 7.514 (0.96), 7.523 (1.08), 7.533 (0.96), 7.537 (0.64), 7.724 (0.60), 7.726 (0.61), 7.744 (0.52), 7.747 (0.52), 7.859 (0.48), 7.882 (0.41).

Intermediate 1-19

4-(4-Hydroxyphenyl)-N,N-dimethylpiperazine-1-sulfonamide

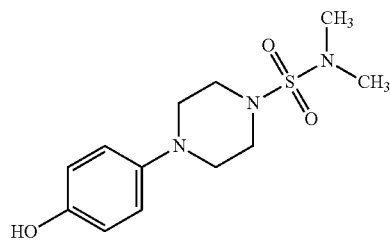 [SMILES: CN(C)S(=O)(=O)N1CCN(c2ccc(O)cc2)CC1]

To a mixture comprising 4-(piperazin-1-yl)phenol (2.50 g, 14.0 mmol; CAS-No: 56621-48-8), THF (50 mL), N,N-diisopropylethylamine (12 mL, 70 mmol) was added dimethylsulfamyl chloride (1.8 mL, 17 mmol) and the reaction was stirred at rt overnight. Methanol was added and the solvents removed. The residue was purified by flash chromatography (Biotage SNAP cartridge 340 g, ethyl acetate: n-hexane) to give the title compound (3.58 g, 89% yield). MS: m/z=286 [M+H]$^+$.

Intermediate 1-20 ethyl 4-bromo-1-methyl-3-{[4-(piperazin-1-yl)phenoxy]methyl}-1H-pyrazole-5-carboxylate hydrochloric acid salt

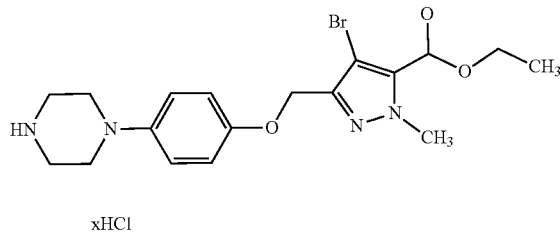 [SMILES: CCOC(O)c1c(Br)c(COc2ccc(N3CCNCC3)cc2)nn1C]

xHCl

To a solution of tert-butyl 4-(4-{[4-bromo-5-(ethoxycarbonyl)-1-methyl-1H-pyrazol-3-yl]methoxy}phenyl)piperazine-1-carboxylate (see Intermediate 1-6; 8.42 g, 16.1 mmol) in 1,4-dioxane (30 ml) was added a solution of HCl in dioxan (40 ml, 4.0 M, 160 mmol) at 0° C. and the mixture was stirred for 3 hours at room temperature. For work-up the mixture was concentrated under reduced pressure and the crude product was used in the subsequent steps without further purification.

Intermediate 1-21

Ethyl 4-bromo-3-({4-[4-(dimethylsulfamoyl)piperazin-1-yl]phenoxy}methyl)-1-methyl-1H-pyrazole-5-carboxylate

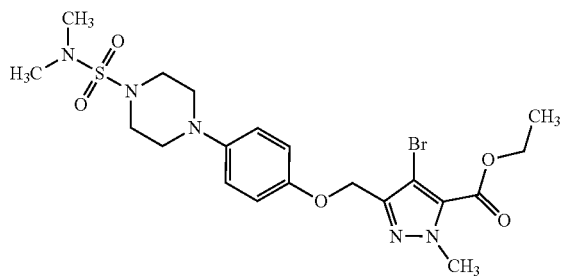 [SMILES: CCOC(=O)c1c(Br)c(COc2ccc(N3CCN(S(=O)(=O)N(C)C)CC3)cc2)nn1C]

To a solution of ethyl 4-bromo-1-methyl-3-{[4-(piperazin-1-yl)phenoxy]methyl}-1H-pyrazole-5-carboxylate hydrochloric acid salt (220 mg) in dichloromethane (9.0 mL) were added at 0° C. N,N-diisopropylethylamine (390 µL, 2.2 mmol) and dimethylsulfamyl chloride (57 µL, 530 µmol). The mixture was stirred at rt overnight. Dichloromethane, water and brine were added, the organic layer was washed with brine and dried over sodium sulfate. After filtration and removal of the solvents the residue was purified by flash chromatography (Biotage SNAP cartridge silica 25 g, EtOH:dichloromethane) to give the title compound (219 mg).
MS: m/z=530 [M+H]$^+$.

Intermediate 1-22

4-(4-{[4-Bromo-5-(hydroxymethyl)-1-methyl-1H-pyrazol-3-yl]methoxy}phenyl)-N,N-dimethylpiperazine-1-sulfonamide

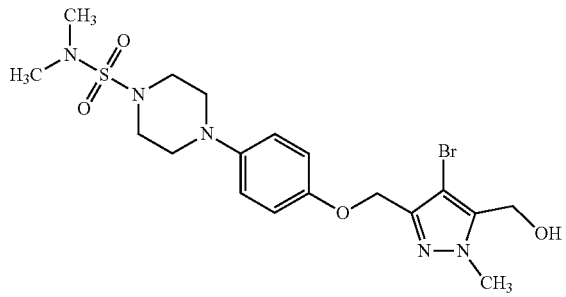 [SMILES: CN(C)S(=O)(=O)N1CCN(c2ccc(OCc3nn(C)c(CO)c3Br)cc2)CC1]

To a solution of ethyl 4-bromo-3-({4-[4-(dimethylsulfamoyl)piperazin-1-yl]phenoxy}methyl)-1-methyl-1H-pyrazole-5-carboxylate (6.92 g, 13.0 mmol) in THF (110 mL) at 0° C. was added a solution of lithium aluminium hydride (6.5 mL, 2.0 M in THF, 13 mmol) and the mixture was stirred at 0° C. for 1 h. Ice was carefully added, water was added and the mixture was extracted with ethyl acetate. The organic layer was washed with brine and dried over sodium sulfate. Filtration and removal of the solvents the residue yielded the title compound (6.21 g, 97% yield) which was used without further purification.
MS: m/z=488 [M+H]$^+$.

Intermediate 1-23 ethyl 7-[3-({4-[4-(dimethylsulfamoyl)piperazin-1-yl]phenoxy}methyl)-5-(hydroxymethyl)-1-methyl-1H-pyrazol-4-yl]-3-[3-(naphthalen-1-yloxy)propyl]-1H-indole-2-carboxylate

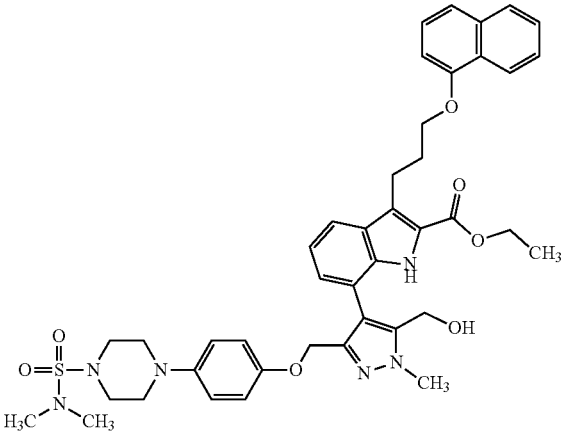

XPhos Pd G2 (see abbreviation list; 32.1 mg, 40.8 µmol) was added to a degassed mixture of ethyl 3-[3-(naphthalen-1-yloxy)propyl]-7-(4,4,5,5-tetramethyl-1,3,2-dioxaborolan-2-yl)-1H-indole-2-carboxylate (see Intermediate 1-4; 677 mg, 1.36 mmol), 4-(4-{[4-bromo-5-(hydroxymethyl)-1-methyl-1H-pyrazol-3-yl]methoxy}phenyl)-N,N-dimethylpiperazine-1-sulfonamide (602 mg, 1.23 mmol), aqueous potassium phosphate solution (4.9 ml, 0.50 M, 2.5 mmol) and THF (15 ml). The mixture was stirred for 2 h at 45° C. For work-up, ethyl acetate was added, the mixture was filtrated through a pad of celite, eluted with ethyl acetate and the organic phase was washed with brine, filtrated through a silicone filter and concentrated. The residue was purified by flash chromatography (dichloromethane/ethyl acetate gradient) to give the title compound (468 mg, 42% yield)

LC-MS (Method 2): R$_t$=1.55 min; MS (ESIpos): m/z=781 [M+H]$^+$ $^1$H-NMR (400 MHz, DMSO-d6) δ [ppm]: 1.066 (2.01), 1.156 (0.45), 1.172 (0.47), 1.242 (1.50), 1.259 (3.31), 1.277 (1.54), 1.987 (0.74), 2.074 (0.79), 2.221 (0.40), 2.322 (0.49), 2.326 (0.69), 2.331 (0.47), 2.518 (2.70), 2.522 (1.85), 2.664 (0.49), 2.668 (0.66), 2.673 (0.47), 2.782 (16.00), 2.797 (2.52), 2.987 (0.91), 3.000 (1.23), 3.012 (1.11), 3.235 (1.19), 3.248 (1.26), 3.259 (0.99), 3.857 (0.78), 3.956 (4.52), 4.188 (0.42), 4.203 (0.85), 4.221 (0.49), 4.240 (0.92), 4.258 (0.89), 6.787 (2.17), 6.796 (2.20), 6.889 (0.57), 6.906 (0.61), 6.913 (0.52), 6.916 (0.51), 7.047 (0.50), 7.221 (0.59), 7.237 (0.48), 7.364 (0.41), 7.384 (0.76), 7.403 (0.62), 7.443 (0.78), 7.464 (0.43), 7.490 (0.47), 7.494 (0.40), 7.505 (0.51), 7.511 (0.73), 7.514 (0.50), 7.525 (0.42), 7.529 (0.45), 7.682 (0.52), 7.702 (0.48), 7.854 (0.47), 7.873 (0.51), 8.202 (0.41), 8.206 (0.42).

Intermediate 1-24 ethyl 1-{3-[(tert-butoxycarbonyl)(methyl)amino]
propyl}-7-[3-({4-[4-(dimethylsulfamoyl)piperazin-
1-yl]phenoxy}methyl)-5-(hydroxymethyl)-1-methyl-
1H-pyrazol-4-yl]-3-[3-(naphthalen-1-yloxy)propyl]-
1H-indole-2-carboxylate

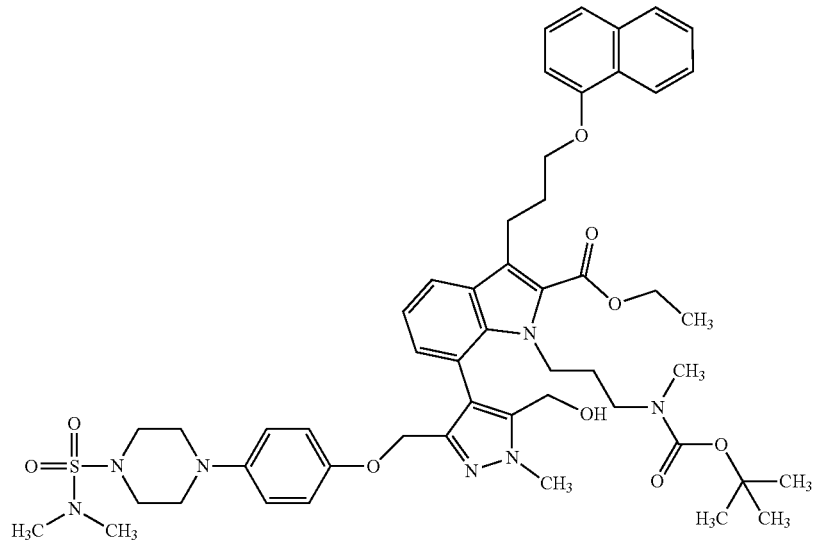 [SMILES: CCOC(=O)c1c(CCCOc2cccc3ccccc23)c2cccc(-c3c(COc4ccc(N5CCN(S(=O)(=O)N(C)C)CC5)cc4)nn(C)c3CBr)c2n1CCCN(C)C(=O)OC(C)(C)C]

To a solution of ethyl 7-[3-({4-[4-(dimethylsulfamoyl)piperazin-1-yl]phenoxy}methyl)-5-(hydroxymethyl)-1-methyl-1H-pyrazol-4-yl]-3-[3-(naphthalen-1-yloxy)propyl]-1H-indole-2-carboxylate (3.60 g, 4.61 mmol) in DMF (60 ml, 780 mmol) was added caesium carbonate (7.51 g, 23.0 mmol) and the mixture was stirred for 10 min at room temperature. Tert-butyl (3-bromopropyl)methylcarbamate (see Intermediate 1-1; 1.39 g, 5.53 mmol) was added and the reaction was stirred for 24 hours at room temperature and for 7 hours at 50° C. For work-up, the reaction mixture was poured into water. The mixture was extracted with ethyl acetate. The combined organic phases washed with brine and dried over sodium sulfate. After filtration and removal of the solvent the crude product was purified twice by flash chromatography (dichloromethane/ethyl acetate gradient, 0%→100% ethyl acetate, followed by Biotage SNAP cartridge $NH_2$ silica hexane/ethyl acetate gradient, 60%→100% ethyl acetate) to give the title compound (2.1 g).

LC-MS (Method 1): Rt=1.66 min; MS (ESIpos): m/z=953 $[M+H]^+$

Intermediate 1-25 ethyl 7-[5-(bromomethyl)-3-({4-[4-(dimethylsulfamoyl)piperazin-1-yl]phenoxy}methyl)-1-methyl-1H-pyrazol-4-yl]-1-{3-[(tert-butoxycarbonyl)(methyl)amino]propyl}-3-[3-(naphthalen-1-yloxy)propyl]-1H-indole-2-carboxylate

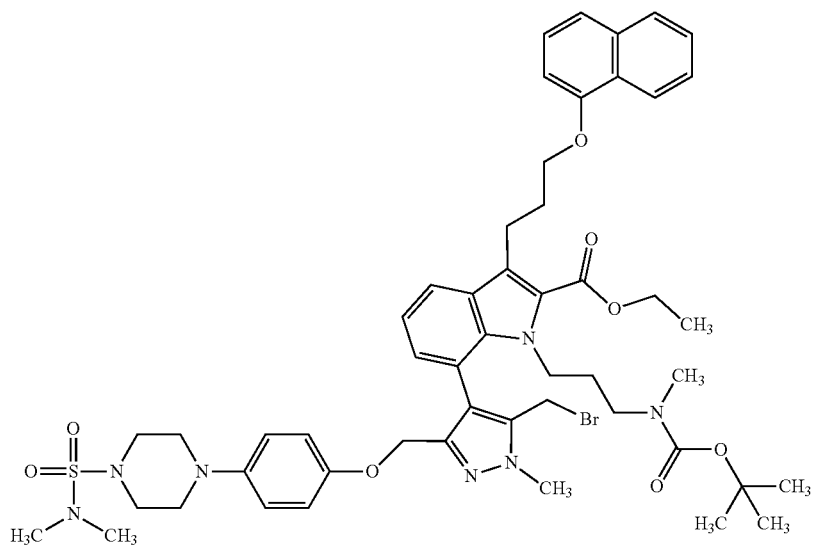

229

To a solution of ethyl 1-{3-[(tert-butoxycarbonyl)(methyl)amino]propyl}-7-[3-({4-[4-(dimethylsulfamoyl)piperazin-1-yl]phenoxy}methyl)-5-(hydroxymethyl)-1-methyl-1H-pyrazol-4-yl]-3-[3-(naphthalen-1-yloxy)propyl]-1H-indole-2-carboxylate (2.10 g, 2.21 mmol) in dichloromethane (40 ml, 630 mmol), triphenylphosphine (1.39 g, 5.29 mmol) was added at 0° C. and the mixture was stirred at 0° C. for 10 min. Tetrabromomethane (1.61 g, 4.85 mmol) was added and the reaction was stirred for 90 minutes at room temperature. For work-up, the reaction mixture was concentrated under reduced pressure and the crude product was used in the subsequent steps without further purification.

LC-MS (Method 1): Rt=1.81 min; MS (ESIpos): m/z=1014 [M+H]$^+$

Intermediate 1-26 ethyl 7-[5-(bromomethyl)-3-({4-[4-(dimethylsulfamoyl)piperazin-1-yl]phenoxy}methyl)-1-methyl-1H-pyrazol-4-yl]-1-[3-(methylamino)propyl]-3-[3-(naphthalen-1-yloxy)propyl]-1H-indole-2-carboxylate hydrochloric acid salt

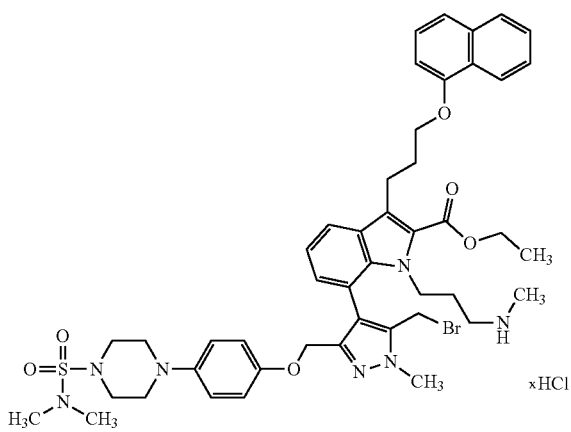

To a solution of ethyl 7-[5-(bromomethyl)-3-({4-[4-(dimethylsulfamoyl)piperazin-1-yl]phenoxy}methyl)-1-methyl-1H-pyrazol-4-yl]-1-{3-[(tert-butoxycarbonyl)(methyl)amino]propyl}-3-[3-(naphthalen-1-yloxy)propyl]-1H-indole-2-carboxylate (2.24 g, 2.21 mmol) in methanol (40 ml) was added a 4 M solution of HCl in dioxan (41 ml, 4.0 M, 160 mmol) at 0° C. and the mixture was stirred for 2 h at room temperature. For work-up the mixture was concentrated under reduced pressure and the crude product was used in the subsequent steps without further purification.

230

Intermediate 1-27

(rac)-ethyl 11-({4-[4-(dimethylsulfamoyl)piperazin-1-yl]phenoxy}methyl)-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylate To a solution of ethyl 7-[5-(bromomethyl)-3-({4-[4-(dimethylsulfamoyl)piperazin-1-yl]phenoxy}methyl)-1-methyl-1H-pyrazol-4-yl]-1-[3-(methylamino)propyl]-3-[3-(naphthalen-1-yloxy)propyl]-1H-indole-2-carboxylate hydrochloric acid salt (2.10 g) in DMF (220 ml, 2.9 mol) was added caesium carbonate (3.60 g, 11.0 mmol) and the reaction was stirred at 65° C. for 20 hours. For work-up the mixture was concentrated under reduced pressure and the residue was purified by flash chromatography (Biotage SNAP cartridge NH$_2$ silica, dichloromethane/ethyl acetate gradient, 0%→100% ethyl acetate) to give the title compound (1.54 g).

LC-MS (Method 2): Rt=1.77 min; MS (ESIpos): m/z=834 [M+H]$^+$ $^1$H-NMR (400 MHz, CHLOROFORM-d) δ [ppm]: 0.000 (1.01), 1.190 (0.44), 1.292 (1.39), 1.310 (3.07), 1.328 (1.42), 1.498 (0.54), 1.978 (0.85), 2.181 (1.78), 2.252 (0.51), 2.763 (16.00), 2.921 (1.03), 2.933 (1.24), 2.938 (0.91), 2.946 (1.21), 3.246 (1.24), 3.253 (0.98), 3.258 (1.28), 3.271 (1.12), 3.909 (2.73), 4.108 (0.46), 4.124 (0.98), 4.139 (0.44), 4.247 (0.46), 4.258 (0.60), 4.265 (0.50), 4.275 (0.56), 4.739 (0.91), 4.753 (0.89), 6.576 (0.41), 6.599 (0.97), 6.628 (1.49), 6.650 (0.58), 6.669 (0.49), 6.686 (0.51), 6.945 (0.53), 6.950 (0.67), 6.959 (1.19), 7.268 (0.74), 7.287 (0.61), 7.334 (0.72), 7.355 (0.42), 7.413 (0.71), 7.423 (0.80), 7.432 (0.69), 7.437 (0.55), 7.726 (0.41).

Intermediate 1-28

(rac)-methyl 11-({4-[4-(dimethylsulfamoyl)piperazin-1-yl]phenoxy}methyl)-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylate

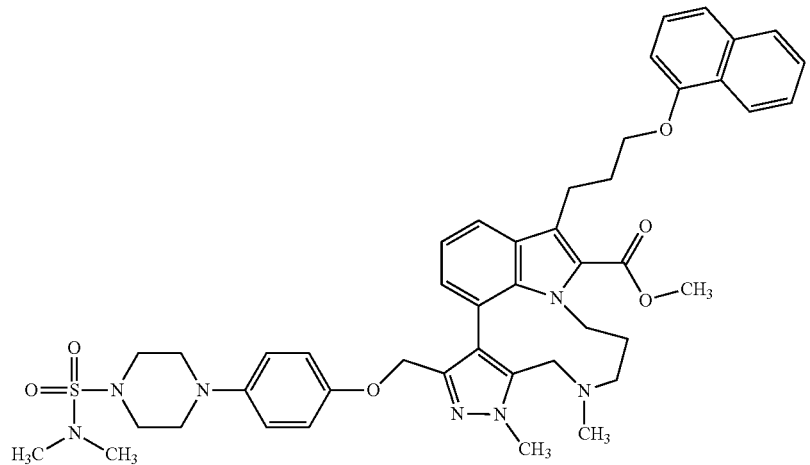 [SMILES: COC(=O)c1c(CCCOc2cccc3ccccc23)c2cccc3c2n1CCCN(C)Cc1c-3c(COc2ccc(N3CCN(S(=O)(=O)N(C)C)CC3)cc2)nn1C]

The title compound (110 mg) was isolated as a side product of Example 1-14.

LC-MS (Method 2): Rt=1.70 min; MS (ESIpos): m/z=820 [M+H]$^+$

The title compound (110 mg) was separated into enantiomers by chiral HPLC to give enantiomer 1 and enantiomer 2.

Preparative chiral HPLC method: Instrument: Labomatic HD5000, Labocord-5000; Gilson GX-241, Labcol Vario 4000, column: Chiralpak IB 5μ 250×30 mm; eluent A: tert.-butylmethylether+0.1 Vol-% diethylamine (99%); eluent B: ethanol; isocratic: 90% A+10% B; flow 50.0 ml/min; UV 280 nm Analytical chiral HPLC method: Instrument: Agilent HPLC 1260; column: Chiralpak IB 3μ 100×4.6 mm; eluent A: tert.-butylmethylether+0.1 Vol-% diethylamine (99%); eluent B: ethanol; isocratik: 90% A+10% B; flow 1.4 ml/min; temperature: 25° C.; DAD 280 nm

Intermediate 1-29 methyl 11-({4-[4-(dimethylsulfamoyl) piperazin-1-yl]phenoxy}methyl)-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylate (Enantiomer 1)

After chiral separation (method see Intermediate 1-28) the obtained product was further purified by flash chromatography (dichloromethane/methanol gradient, 0%→10% methanol) to give after lyophilization the title compound (23 mg).

Analytical Chiral HPLC (method see Intermediate 1-28): R$_t$=1.84 min.

$^1$H-NMR (400 MHz, DMSO-d6) δ [ppm]: 2.168 (3.77), 2.185 (0.68), 2.201 (0.43), 2.756 (16.00), 2.895 (1.09), 2.908 (1.48), 2.920 (1.30), 2.993 (0.50), 3.029 (0.53), 3.177 (1.39), 3.190 (1.54), 3.202 (1.14), 3.621 (0.55), 3.657 (0.60), 3.757 (5.22), 3.879 (4.80), 4.146 (0.46), 4.162 (0.93), 4.177 (0.49), 4.698 (1.78), 6.477 (1.19), 6.499 (1.47), 6.642 (1.51), 6.665 (1.14), 6.836 (0.64), 6.854 (0.69), 6.952 (0.43), 6.966 (0.86), 6.969 (0.77), 6.987 (0.70), 7.006 (0.77), 7.353 (0.43), 7.374 (0.83), 7.393 (0.61), 7.441 (0.91), 7.462 (0.54), 7.511 (0.68), 7.513 (0.76), 7.524 (0.88), 7.535 (0.79), 7.708 (0.57), 7.711 (0.59), 7.728 (0.55), 7.731 (0.52), 7.857 (0.51), 7.870 (0.41), 7.880 (0.43), 8.218 (0.45), 8.242 (0.41).

Intermediate 1-30 methyl 11-({4-[4-(dimethylsulfamoyl) piperazin-1-yl]phenoxy}methyl)-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylate (Enantiomer 2)

After chiral separation (method see Intermediate 1-28) the obtained product was further purified by flash chromatography (dichloromethane/methanol gradient, 0%→10% methanol) to give after lyophilization the title compound (26 mg).

Analytical Chiral HPLC (method see Intermediate 1-28): R$_t$=2.56 min.

$^1$H-NMR (400 MHz, DMSO-d6): δ [ppm]=8.27-8.12 (m, 1H), 7.93-7.78 (m, 1H), 7.70 (dd, 1H), 7.55-7.47 (m, 2H), 7.46-7.39 (m, 1H), 7.38-7.30 (m, 1H), 7.05-6.90 (m, 2H), 6.82 (d, 1H), 6.69-6.58 (m, 2H), 6.52-6.34 (m, 2H), 4.74-4.61 (m, 2H), 4.26-4.10 (m, 3H), 3.86 (s, 3H), 3.68-3.55 (m, 2H), 3.39-3.29 (m, 4H), 3.28-3.21 (m, 1H), 3.20-3.10 (m, 4H), 2.99 (d, 1H), 2.93-2.83 (m, 4H), 2.73 (s, 6H), 2.33-2.23 (m, 1H), 2.20-2.11 (m, 5H), 1.83 (br dd, 1H), 1.59-1.36 (m, 2H), 1.07 (t, 1H).

Intermediate 1-31 ethyl 7-{3-({4-[4-(dimethylsulfamoyl) piperazin-1-yl]phenoxy}methyl)-1-methyl-5-[(prop-2-en-1-yloxy)methyl]-1H-pyrazol-4-yl}-3-[3-(naphthalen-1-yloxy)propyl]-1-(prop-2-en-1-yl)-1H-indole-2-carboxylate

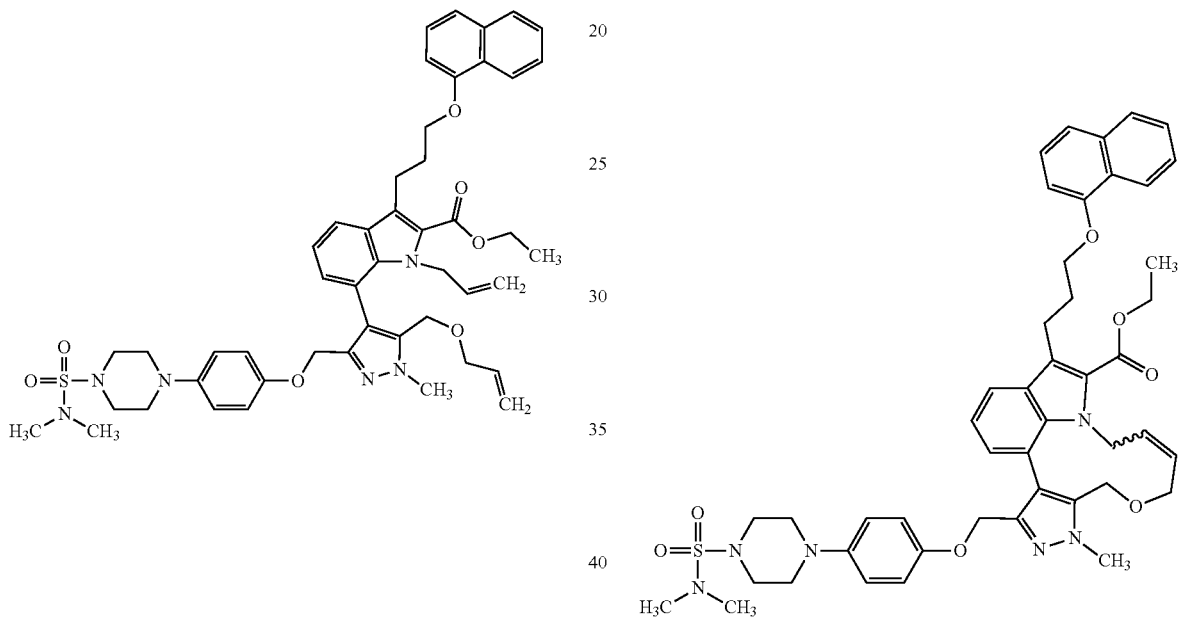

Sodium hydride (71.4 mg, 60% suspension in mineral oil, 1.79 mmol) was added at 0° C. to a solution of ethyl 7-[3-({4-[4-(dimethylsulfamoyl)piperazin-1-yl]phenoxy}methyl)-5-(hydroxymethyl)-1-methyl-1H-pyrazol-4-yl]-3-[3-(naphthalen-1-yloxy)propyl]-1H-indole-2-carboxylate (see Intermediate 1-23; 465 mg, 595 µmol) in THF (7.8 ml) and the mixture was stirred for 30 min at that temperature. Allyl bromide (150 µl, 1.8 mmol) in THF (0.5 ml) was added and the mixture was stirred for 24 h at room temperature. For work-up, water was added and the mixture was extracted three times with ethyl acetate, the combined organic phases were washed with brine, filtrated through a silicone filter and concentrated. The residue was purified by flash chromatography (Biotage SNAP cartridge silica 25 g, hexanes/ethyl acetate gradient, 12%→60% ethyl acetate) to give the title compound (277 mg, 54% yield).

LC-MS (Method 2): $R_f$=1.86 min; MS (ESIpos): m/z=861 [M+H]$^+$ $^1$H-NMR (400 MHz, DMSO-d6): δ [ppm]=8.25-8.22 (m, 1H), 7.88-7.85 (m, 1H), 7.76 (dd, 1H), 7.55-7.49 (m, 2H), 7.46 (d, 1H), 7.38 (t, 1H), 7.10-7.05 (m, 1H), 7.01 (dd, 1H), 6.86 (d, 1H), 6.76-6.72 (m, 2H), 6.65-6.61 (m, 2H), 5.78- 5.69 (m, 1H), 5.55-5.42 (m, 1H), 5.10-4.98 (m, 2H), 4.86-4.73 (m, 3H), 4.68 (s, 2H), 4.34-4.06 (m, 7H), 3.91 (s, 3H), 3.89-3.74 (m, 2H), 3.31-3.26 (m, 2H), 3.22-3.18 (m, 4H), 2.96-2.92 (m, 4H), 2.76 (s, 6H), 2.25-2.13 (m, 2H), 1.27 (t, 3H)

Intermediate 1-32

(rac)-(E/Z)-ethyl-3-({4-[4-(dimethylsulfamoyl)piperazin-1-yl]phenoxy}methyl)-1-methyl-7-[3-(naphthalen-1-yloxy)propyl]-1,10,13,15-tetrahydropyrazolo[4',3':9,10][1,6]oxazacycloundecino[8,7,6-hi]indole-8-carboxylate (1,3-Bis(2,4,6-trimethylphenyl)-2-imidazolidinylidene)dichloro(phenylmethylene)(tricyclohexylphosphine)ruthenium (CAS No 246047-72-3; Grubbs 2nd generation catalyst; 27.1 mg, 31.9 µmol) was added to a solution of ethyl 7-{3-({4-[4-(dimethylsulfamoyl)piperazin-1-yl]phenoxy}methyl)-1-methyl-5-[(prop-2-en-1-yloxy)methyl]-1H-pyrazol-4-yl}-3-[3-(naphthalen-1-yloxy)propyl]-1-(prop-2-en-1-yl)-1H-indole-2-carboxylate (275 mg, 319 µmol) in dichloromethane (4.1 ml) and the mixture was stirred at room temperature overnight. For work-up, the reaction mixture was concentrated and the residue was purified by flash chromatography (Biotage SNAP cartridge silica 25 g, hexanes/ethyl acetate gradient, 0%→60% ethyl acetate) to give the title compound (117 mg), together with impurities and was used in the next step without further purification.

LC-MS (Method 2): $R_f$=1.69 min; MS (ESIpos): m/z=833 [M+H]$^+$

Intermediate 1-33

(rac)-ethyl 3-({4-[4-(dimethylsulfamoyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate

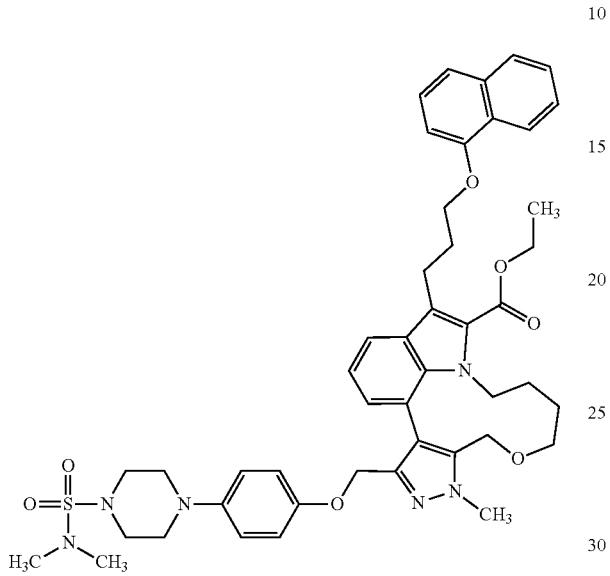

An autoclave was charged with (rac)-(E/Z)-ethyl 3-({4-[4-(dimethylsulfamoyl)piperazin-1-yl]phenoxy}methyl)-1-methyl-7-[3-(naphthalen-1-yloxy)propyl]-1,10,13,15-tetrahydropyrazolo[4',3':9,10][1,6]oxazacycloundecino[8,7,6-hi]indole-8-carboxylate (128 mg, 154 µmol), ethanol (4.0 ml), THF (1.5 ml) and palladium 10% on charcoal (16.3 mg, 15.4 µmol) and the mixture was stirred under 15 bar hydrogen atmosphere at room temperature for 18.5 h. For work-up, the mixture was filtrated through a pad of celite, eluted with ethyl acetate and the combined filtrates were concentrated under reduced pressure to give the title compound (128 mg), which was directly used in the next step.

LC-MS (Method 2): $R_t$=1.69 min; MS (ESIpos): m/z=836 [M+H]$^+$ $^1$H-NMR (400 MHz, DMSO-d6) δ [ppm]: 1.035 (0.53), 1.043 (0.42), 1.053 (0.78), 1.268 (0.41), 1.282 (1.60), 1.299 (3.11), 1.318 (1.50), 2.176 (0.53), 2.326 (0.47), 2.518 (2.02), 2.522 (1.32), 2.668 (0.48), 2.743 (16.00), 2.760 (1.45), 2.796 (0.45), 2.885 (0.90), 2.898 (1.22), 2.910 (1.12), 3.147 (1.16), 3.160 (1.28), 3.172 (0.98), 3.922 (4.63), 4.108 (0.49), 4.124 (0.82), 4.264 (0.55), 4.273 (0.63), 4.282 (0.62), 4.302 (0.78), 4.306 (0.67), 4.320 (0.51), 4.441 (0.69), 4.469 (0.70), 4.674 (0.64), 4.682 (0.77), 4.710 (0.83), 6.498 (1.08), 6.521 (1.35), 6.668 (1.16), 6.691 (0.89), 6.796 (0.57), 6.815 (0.60), 6.856 (0.58), 6.859 (0.58), 6.874 (0.74), 6.876 (0.66), 6.987 (0.59), 7.007 (0.71), 7.025 (0.45), 7.347 (0.42), 7.366 (0.77), 7.386 (0.59), 7.442 (0.85), 7.463 (0.53), 7.507 (0.58), 7.512 (0.89), 7.522 (1.02), 7.531 (0.97), 7.536 (0.56), 7.722 (0.56), 7.725 (0.59), 7.742 (0.57), 7.745 (0.55), 7.857 (0.50), 7.880 (0.41), 8.219 (0.43), 8.243 (0.40).

Intermediate 1-34

(rac)-ethyl 3-({4-[4-(cyclopropylcarbonyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate

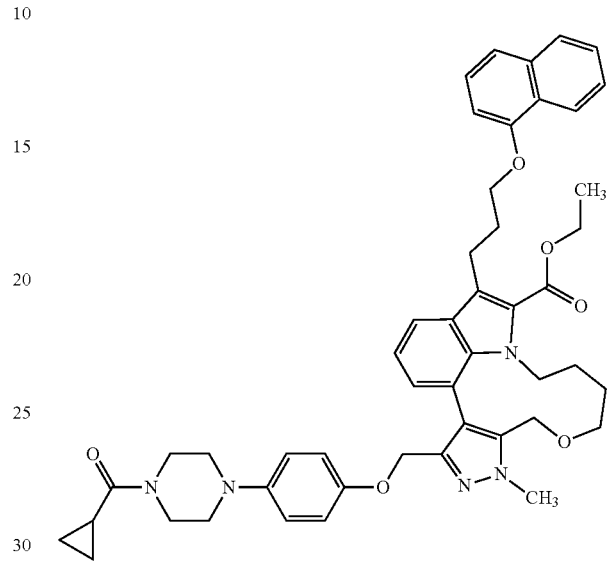

A mixture of (rac)-ethyl 1-methyl-7-[3-(naphthalen-1-yloxy)propyl]-3-{[4-(piperazin-1-yl)phenoxy]methyl}-1,10,11,12,13,15-hexahydropyrazolo[4',3':9,10][1,6]oxazacycloundecino[8,7,6-hi]indole-8-carboxylate hydrochloric acid salt (see Intermediate 1-12; 250 mg, 312 µmol) and N,N-diisopropylethylamine (270 µl, 1.6 mmol) in dichloromethane (5.6 ml) was stirred for 10 min. Cyclopropanecarbonyl chloride (39.2 mg, 375 µmol) was then added and the mixture was stirred for 24 h at room temperature. For work-up, the reaction mixture was concentrated and the residue was purified by flash chromatography (Biotage SNAP cartridge silica 25 g, hexanes/ethyl acetate gradient, 0%→100% ethyl acetate) to give the title compound (190 mg, 76% yield).

LC-MS (Method 2): $R_t$=1.70 min; MS (ESIpos): m/z=796 [M+H]$^+$ $^1$H-NMR (400 MHz, DMSO-d6) δ [ppm]: 0.665 (0.84), 0.672 (2.16), 0.678 (1.26), 0.685 (1.14), 0.692 (3.06), 0.697 (2.94), 0.705 (2.22), 0.710 (2.58), 0.717 (1.20), 1.044 (0.90), 1.154 (3.30), 1.173 (6.59), 1.191 (3.42), 1.269 (0.96), 1.283 (3.54), 1.287 (1.62), 1.301 (6.71), 1.319 (3.24), 1.920 (0.84), 1.988 (13.18), 2.074 (4.91), 2.178 (1.26), 2.327 (3.54), 2.331 (2.58), 2.337 (1.20), 2.518 (16.00), 2.523 (10.55), 2.669 (3.60), 2.673 (2.58), 2.678 (1.20), 2.813 (1.44), 2.842 (1.14), 2.860 (1.14), 3.491 (1.38), 3.659 (0.84), 3.924 (10.13), 3.944 (1.08), 4.000 (1.02), 4.018 (3.00), 4.035 (3.00), 4.053 (1.08), 4.110 (1.14), 4.123 (1.86), 4.237 (0.60), 4.255 (0.66), 4.264 (1.20), 4.274 (1.38), 4.282 (1.38), 4.303 (1.62), 4.307 (1.50), 4.320 (1.08), 4.330 (0.60), 4.439 (1.56), 4.467 (1.62), 4.675 (1.56), 4.682 (1.98), 4.709 (2.40), 6.495 (2.46), 6.501 (0.96), 6.518 (2.94), 6.671 (3.00), 6.689 (0.96), 6.694 (2.34), 6.797 (1.26), 6.815 (1.38), 6.857 (1.20), 6.860 (1.32), 6.875 (1.56), 6.878 (1.50), 6.987 (1.20), 7.008 (1.44), 7.025 (0.96), 7.347 (0.90), 7.367 (1.68), 7.386 (1.26), 7.443 (1.80), 7.464 (1.14), 7.506 (1.20), 7.511 (1.98), 7.521 (2.28), 7.530 (2.10), 7.535 (1.32), 7.723 (1.38), 7.726 (1.38), 7.743 (1.20), 7.747 (1.14), 7.857 (1.08), 7.875 (0.78), 7.880 (0.90), 8.221 (0.96), 8.227 (0.78), 8.246 (0.90).

Intermediate 1-35

(rac)-ethyl 3-{[4-(4-acetylpiperazin-1-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate

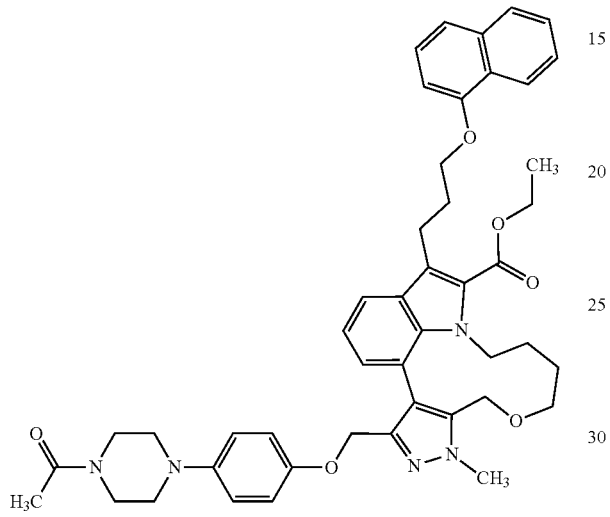

A mixture of (rac)-ethyl 1-methyl-7-[3-(naphthalen-1-yloxy)propyl]-3-{[4-(piperazin-1-yl)phenoxy]methyl}-1,10,11,12,13,15-hexahydropyrazolo[4',3':9,10][1,6]oxazacycloundecino[8,7,6-hi]indole-8-carboxylate hydrochloric acid salt (see Intermediate 1-12; 285 mg, 356 µmol) and pyridine (140 µl, 1.8 mmol) in dichloromethane (6.4 ml) was stirred for 10 min. Acetic anhydride (40 µl, 430 µmol) was then added and the mixture was stirred for 24 h at room temperature. For work-up, the reaction mixture was concentrated and the residue was purified by flash chromatography (Biotage SNAP cartridge silica 25 g, hexanes/ethyl acetate gradient, 0%→100% ethyl acetate) to give the title compound (190 mg, 86% purity, 69% yield).

LC-MS (Method 2): $R_t$=1.64 min; MS (ESIpos): m/z=770 [M+H]$^+$ $^1$H-NMR (400 MHz, DMSO-d6) δ [ppm]: 1.043 (0.67), 1.154 (3.99), 1.172 (8.00), 1.190 (4.07), 1.236 (0.51), 1.268 (0.74), 1.282 (2.27), 1.300 (4.08), 1.317 (1.97), 1.966 (7.56), 1.988 (16.00), 2.160 (0.58), 2.176 (0.86), 2.194 (0.63), 2.323 (0.67), 2.327 (0.87), 2.331 (0.67), 2.522 (2.93), 2.665 (0.64), 2.669 (0.87), 2.673 (0.66), 2.785 (0.79), 2.798 (1.21), 2.810 (1.19), 2.829 (1.14), 2.841 (1.43), 2.855 (0.95), 3.252 (0.52), 3.376 (0.45), 3.405 (0.89), 3.419 (1.11), 3.430 (0.86), 3.447 (1.11), 3.461 (1.57), 3.473 (1.19), 3.490 (0.60), 3.922 (6.19), 3.944 (0.87), 3.999 (1.22), 4.018 (3.54), 4.035 (3.54), 4.053 (1.25), 4.106 (0.76), 4.120 (1.27), 4.134 (0.70), 4.253 (0.45), 4.263 (0.80), 4.272 (0.95), 4.281 (0.92), 4.302 (1.09), 4.320 (0.70), 4.329 (0.41), 4.416 (0.41), 4.437 (0.96), 4.452 (0.41), 4.465 (1.09), 4.677 (1.52), 4.707 (1.50), 6.497 (1.54), 6.520 (1.92), 6.664 (1.89), 6.687 (1.46), 6.792 (0.85), 6.811 (0.92), 6.858 (0.87), 6.874 (1.01), 6.985 (0.71), 7.004 (0.96), 7.022 (0.58), 7.345 (0.54), 7.365 (1.06), 7.384 (0.77), 7.443 (1.18), 7.464 (0.76), 7.507 (0.77), 7.512 (1.21), 7.522 (1.50), 7.531 (1.31), 7.536 (0.85), 7.724 (0.92), 7.742 (0.79), 7.859 (0.76), 7.875 (0.57), 7.882 (0.63), 8.220 (0.60), 8.227 (0.58), 8.244 (0.60).

Intermediate 1-36

(rac)-ethyl 3-({4-[4-(methoxyacetyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate

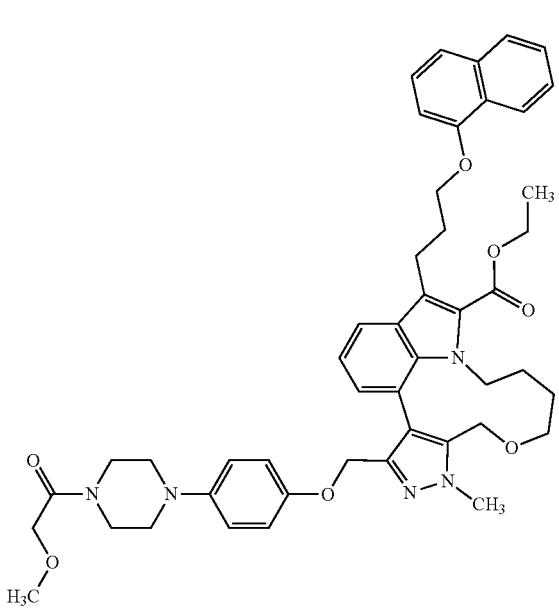 [SMILES: CCOC(=O)c1c(CCCOc2cccc3ccccc23)c2cccc3c2n1CCCCOCc1c-3c(COc2ccc(N3CCN(C(=O)COC)CC3)cc2)nn1C]

A mixture of (rac)-ethyl 1-methyl-7-[3-(naphthalen-1-yloxy)propyl]-3-{[4-(piperazin-1-yl)phenoxy]methyl}-1,10,11,12,13,15-hexahydropyrazolo[4',3':9,10][1,6]oxazacycloundecino[8,7,6-hi]indole-8-carboxylate hydrochloric acid salt (see Intermediate 1-12; 250 mg, 312 µmol) and N,N-diisopropylethylamine (270 µl, 1.6 mmol) in dichloromethane (5.6 ml) was stirred for 10 min. Methoxyacetyl chloride (34 µl, 370 µmol) was then added and the mixture was stirred for 24 h at room temperature. For work-up, the reaction mixture was concentrated and the residue was purified by flash chromatography (Biotage SNAP cartridge silica 25 g, hexanes/ethyl acetate gradient, 0%→100% ethyl acetate) to give the title compound (166 mg, 90% purity, 66% yield).

LC-MS (Method 2): $R_t$=1.64 min; MS (ESIpos): m/z=800 [M+H]$^+$ $^1$H-NMR (400 MHz, DMSO-d6) δ [ppm]: 0.354 (0.45), 1.042 (0.79), 1.056 (0.63), 1.234 (0.50), 1.248 (0.59), 1.267 (0.91), 1.281 (3.10), 1.285 (1.51), 1.298 (6.04), 1.316 (2.92), 1.988 (0.61), 2.160 (0.66), 2.176 (1.04), 2.194 (0.73), 2.323 (0.79), 2.327 (1.08), 2.331 (0.77), 2.518 (4.48), 2.523 (2.99), 2.665 (0.81), 2.669 (1.09), 2.673 (0.77), 2.840 (2.08), 3.218 (0.41), 3.224 (0.41), 3.234 (0.43), 3.257 (16.00), 3.266 (2.76), 3.360 (0.56), 3.393 (1.16), 3.431 (0.41), 3.442 (0.50), 3.461 (1.18), 3.474 (1.36), 3.488 (1.09), 3.922 (8.80), 3.944 (1.13), 4.054 (7.02), 4.074 (1.24), 4.095 (0.72), 4.108 (0.91), 4.120 (1.49), 4.234 (0.52), 4.251 (0.61), 4.261 (1.04), 4.271 (1.18), 4.279 (1.18), 4.299 (1.34), 4.305 (1.24), 4.317 (0.97), 4.327 (0.54), 4.344 (0.52), 4.413 (0.50), 4.439 (1.36), 4.450

(0.48), 4.467 (1.40), 4.676 (1.97), 4.705 (1.90), 6.500 (2.15), 6.523 (2.65), 6.668 (2.62), 6.690 (2.01), 6.792 (1.09), 6.811 (1.16), 6.855 (1.06), 6.858 (1.16), 6.873 (1.33), 6.875 (1.33), 6.984 (1.04), 7.003 (1.29), 7.021 (0.84), 7.037 (0.41), 7.344 (0.81), 7.365 (1.49), 7.384 (1.11), 7.443 (1.56), 7.463 (0.99), 7.507 (1.02), 7.514 (1.59), 7.523 (2.13), 7.532 (1.79), 7.538 (1.15), 7.550 (0.39), 7.720 (1.13), 7.723 (1.22), 7.740 (1.06), 7.743 (1.02), 7.859 (0.97), 7.869 (0.50), 7.877 (0.70), 7.882 (0.82), 8.220 (0.81), 8.227 (0.73), 8.236 (0.45), 8.244 (0.77).

Intermediate 1-37 ethyl 4-bromo-1,3-dimethyl-1H-pyrazole-5-carboxylate

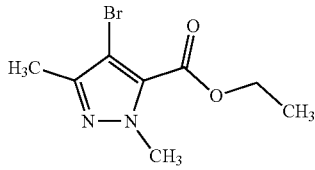

N-Bromosuccinimide (11.2 g, 62.4 mmol) was added to a solution of ethyl 1,3-dimethyl-1H-pyrazole-5-carboxylate (5.00 g, 29.7 mmol, CAS No: 5744-40-1) in 1,2-dichloroethane (100 ml) and the mixture was stirred for 15 h at 65-80° C. followed by 3 d at room temperature. For work-up, the mixture was diluted with ethyl acetate, washed with water and the organic phase was filtrated through a silicone filter and concentrated. The residue was purified by flash chromatography (Biotage SNAP cartridge silica, hexanes/dichloromethane gradient, 0%→100% dichloromethane) to give the title compound (6.69 g, 89% yield).

LC-MS (Method 2): $R_t$=1.15 min; MS (ESIpos): m/z=247 [M+H]$^+$ $^1$H-NMR (400 MHz, DMSO-d6) δ [ppm]: 1.308 (4.21), 1.325 (8.89), 1.343 (4.18), 2.155 (14.47), 3.862 (1.45), 4.008 (16.00), 4.302 (1.34), 4.320 (4.19), 4.337 (4.07), 4.355 (1.24).

Intermediate 1-38

(4-bromo-1,3-dimethyl-1H-pyrazol-5-yl)methanol

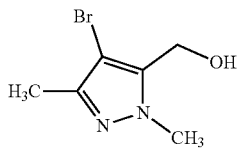

Lithium aluminium hydride (27 ml, 1.0 M in THF, 27 mmol) was added dropwise at 0° C. to a solution of ethyl 4-bromo-1,3-dimethyl-1H-pyrazole-5-carboxylate (6.69 g, 27.1 mmol) in THF (220 ml) and the mixture was stirred at 0° C. for 1.5 h. The reaction was quenched by dropwise addition of water (5.4 ml) followed by aqueous sodium hydroxide (5.4 ml, 2 M, 11 mmol) and again water (5.4 ml). The mixture was then filtrated through a pad of celite, eluted with THF and the filtrate was concentrated. The residue was purified by flash chromatography (Biotage SNAP cartridge silica 100 g, hexanes/ethyl acetate gradient, 20%→80% ethyl acetate) to give the title compound (3.77 g, 67% yield).

$^1$H-NMR (400 MHz, DMSO-d6) δ [ppm]: 2.083 (14.56), 3.334 (16.00), 4.422 (2.80), 4.435 (2.81), 5.311 (0.59), 5.325 (1.50), 5.337 (0.56).

Intermediate 1-39

Ethyl 7-[5-(hydroxymethyl)-1,3-dimethyl-1H-pyrazol-4-yl]-3-[3-(1-naphthyloxy)propyl]-1H-indole-2-carboxylate

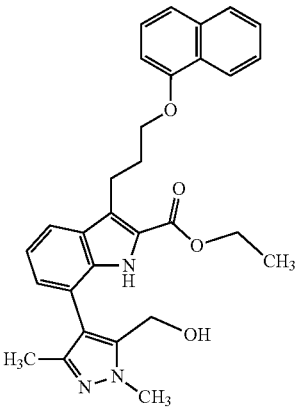

XPhos Pd G2 (see abbreviations; 109 mg, 138 μmol) was added to a degassed mixture of ethyl 3-[3-(naphthalen-1-yloxy)propyl]-7-(4,4,5,5-tetramethyl-1,3,2-dioxaborolan-2-yl)-1H-indole-2-carboxylate (see Intermediate 1-4; 2.50 g, 5.01 mmol), (4-bromo-1,3-dimethyl-1H-pyrazol-5-yl)methanol (933 mg, 4.55 mmol) aqueous potassium phosphate solution (18 ml, 0.50 M, 9.1 mmol) and THF (55 ml). The mixture was stirred for 2 h at 45° C. For work-up, ethyl acetate was added, the mixture was filtrated through a pad of celite, eluted with ethyl acetate and the organic phase was washed with brine, filtrated through a silicone filter and concentrated. The residue was purified by flash chromatography (Biotage SNAP cartridge silica 50 g, hexanes/ethyl acetate gradient, 50%→100% ethyl acetate) to give the title compound (1.45 g, 57% yield).

LC-MS (Method 2): $R_t$=1.52 min; MS (ESIpos): m/z=498 [M+H]$^+$ $^1$H-NMR (400 MHz, DMSO-d6) δ [ppm]: 1.260 (5.06), 1.278 (11.54), 1.296 (5.20), 2.067 (16.00), 2.214 (1.01), 2.230 (1.35), 2.249 (1.04), 2.518 (2.38), 2.523 (1.64), 3.160 (0.97), 3.173 (0.93), 3.350 (2.33), 3.354 (2.31), 3.372 (1.26), 3.864 (15.21), 4.200 (1.44), 4.215 (2.97), 4.230 (1.53), 4.236 (1.75), 4.254 (4.67), 4.272 (4.59), 4.290 (1.49), 4.329 (1.12), 5.711 (1.56), 5.759 (1.07), 6.905 (1.64), 6.908 (1.72), 6.924 (1.87), 6.927 (1.75), 7.068 (1.22), 7.086 (2.45), 7.106 (2.54), 7.120 (2.64), 7.123 (2.89), 7.138 (1.35), 7.141 (0.98), 7.373 (1.32), 7.394 (2.57), 7.413 (2.10), 7.450 (2.58), 7.471 (1.42), 7.491 (0.60), 7.504 (1.58), 7.508 (1.42), 7.514 (1.71), 7.521 (3.41), 7.528 (1.75), 7.533 (1.50), 7.538 (1.67), 7.550 (0.63), 7.664 (1.56), 7.668 (1.60), 7.684 (1.54), 7.688 (1.40), 7.860 (1.49), 7.863 (1.22), 7.868 (0.83), 7.878 (1.42), 7.883 (1.28), 8.225 (1.33), 8.230 (1.25), 8.247 (1.16), 8.249 (1.25), 10.911 (2.23).

Intermediate 1-40 ethyl 1-{3-[(tert-butoxycarbonyl)(methyl)amino]propyl}-7-[5-(hydroxymethyl)-1,3-dimethyl-1H-pyrazol-4-yl]-3-[3-(naphthalen-1-yloxy)propyl]-1H-indole-2-carboxylate

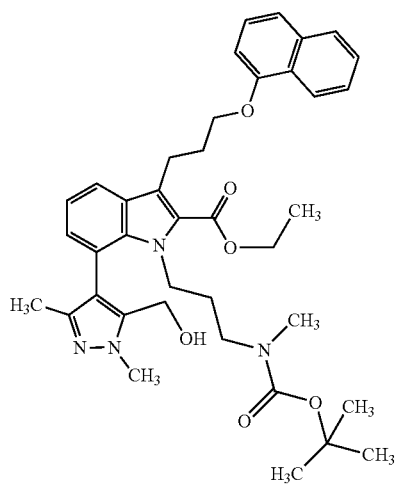 [SMILES: CCOC(=O)c1c(CCCOc2cccc3ccccc23)c2cccc(-c3c(C)nn(C)c3CO)c2n1CCCN(C)C(=O)OC(C)(C)C]

A mixture of ethyl 7-[5-(hydroxymethyl)-1,3-dimethyl-1H-pyrazol-4-yl]-3-[3-(naphthalen-1-yloxy)propyl]-1H-indole-2-carboxylate (1.28 g, 2.57 mmol) and caesium carbonate (4.19 g, 12.9 mmol) in DMF (32 ml) was stirred for 10 min at room temperature. tert-butyl (3-bromopropyl)methylcarbamate (see Intermediate 1-1; 714 mg, 2.83 mmol) was then added and the mixture was stirred for 48 h at room temperature. For work-up, the reaction mixture was combined with a second batch which was prepared similarly. Water was added, and the mixture was extracted with a mixture of dichloromethane/2-propanol (4:1). The combined organic phases were filtrated through a silicone filter and concentrated. The residue was purified by preparative HPLC (Method P10) to give the title compound (1.40 g).

LC-MS (Method 2): $R_t$=1.67 min; MS (ESIneg): m/z=667 [M–H]⁻

¹H-NMR (400 MHz, DMSO-d6) δ [ppm]: 1.270 (12.41), 1.288 (16.00), 1.306 (8.26), 1.363 (3.19), 1.907 (13.15), 2.197 (1.54), 2.214 (2.22), 2.232 (1.54), 2.247 (0.57), 2.318 (0.51), 2.322 (1.02), 2.326 (1.31), 2.331 (0.97), 2.336 (0.46), 2.518 (5.35), 2.523 (4.10), 2.535 (12.01), 2.659 (0.91), 2.664 (1.42), 2.669 (1.77), 2.673 (1.37), 2.678 (0.85), 3.159 (1.25), 3.172 (1.31), 3.280 (1.88), 3.302 (3.30), 3.859 (6.66), 4.030 (0.57), 4.215 (2.62), 4.231 (4.78), 4.245 (3.76), 4.262 (3.99), 4.267 (3.76), 4.280 (3.76), 4.286 (3.19), 4.298 (1.71), 4.303 (1.42), 4.313 (1.20), 5.190 (0.91), 6.908 (2.62), 6.927 (2.90), 7.013 (2.33), 7.016 (2.45), 7.030 (3.64), 7.034 (3.30), 7.080 (1.42), 7.099 (1.99), 7.117 (0.91), 7.373 (2.11), 7.393 (3.87), 7.412 (3.19), 7.452 (3.99), 7.473 (2.22), 7.490 (0.57), 7.495 (0.91), 7.507 (2.68), 7.514 (3.30), 7.523 (5.18), 7.531 (3.76), 7.538 (2.68), 7.550 (0.91), 7.555 (0.51), 7.734 (2.62), 7.737 (2.62), 7.754 (2.39), 7.757 (2.28), 7.861 (2.33), 7.864 (1.71), 7.871 (1.20), 7.879 (1.65), 7.885 (1.94), 8.215 (2.05), 8.222 (1.71), 8.230 (0.97), 8.239 (1.82).

Intermediate 1-41 ethyl 7-[5-(bromomethyl)-1,3-dimethyl-1H-pyrazol-4-yl]-1-{3-[(tert-butoxycarbonyl)(methyl)amino]propyl}-3-[3-(naphthalen-1-yloxy)propyl]-1H-indole-2-carboxylate

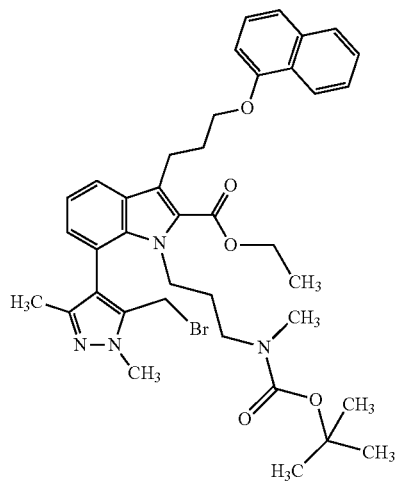 [SMILES: CCOC(=O)c1c(CCCOc2cccc3ccccc23)c2cccc(-c3c(C)nn(C)c3CBr)c2n1CCCN(C)C(=O)OC(C)(C)C]

A mixture of ethyl 1-{3-[(tert-butoxycarbonyl)(methyl)amino]propyl}-7-[5-(hydroxymethyl)-1,3-dimethyl-1H-pyrazol-4-yl]-3-[3-(naphthalen-1-yloxy)propyl]-1H-indole-2-carboxylate (1.30 g, 1.94 mmol) and triphenylphosphine (1.22 g, 4.66 mmol) in dichloromethane (36 ml) was stirred for 10 min at 0° C. Tetrabromomethane (1.42 g, 4.28 mmol) was then added and the mixture was stirred for 2 h at room temperature. For work-up, the reaction mixture was concentrated and the crude product was used in the subsequent step without further purification.

LC-MS (Method 2): $R_t$=1.84 min; MS (ESIpos): m/z=731 [M+H]⁺

Intermediate 1-42 ethyl 7-[5-(bromomethyl)-1,3-dimethyl-1H-pyrazol-4-yl]-1-[3-(methylamino)propyl]-3-[3-(naphthalen-1-yloxy)propyl]-1H-indole-2-carboxylate hydrochloric acid salt

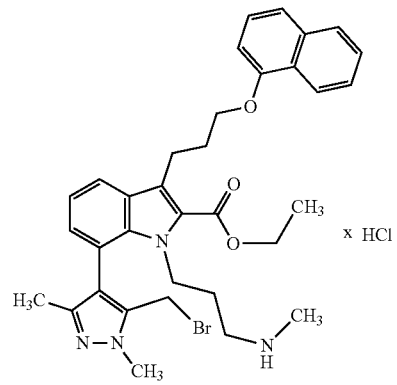

Hydrochloric acid (36 ml, 4.0 M in dioxane, 140 mmol) was added at 0° C. to a solution of ethyl 7-[5-(bromomethyl)-1,3-dimethyl-1H-pyrazol-4-yl]-1-{3-[(tert-butoxycarbonyl)(methyl)amino]propyl}-3-[3-(naphthalen-1-yloxy)propyl]-1H-indole-2-carboxylate (1.42 g, 1.94 mmol) in methanol (22 ml) and the mixture was stirred for 2 h at room temperature. For work-up, the reaction mixture was concentrated to give the title compound (3.83 g) which was used in the next step without further purification.

Intermediate 1-43

(rac)-ethyl 7,9,11-trimethyl-1-[3-(naphthalen-1-yloxy)propyl]-4,5,6,7,8,9-hexahydropyrazolo[3',4':7,8][1,5]diazecino[9,10,1-hi]indole-2-carboxylate

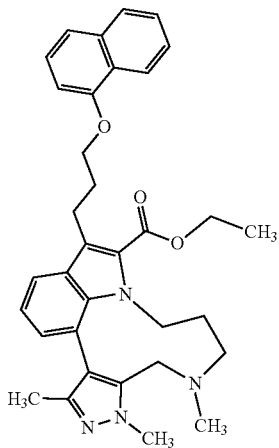 [SMILES: CCOC(=O)c1c(CCCOc2cccc3ccccc23)c2cccc3c2n1CCCN(C)Cc1c-3c(C)nn1C]

A mixture of ethyl 7-[5-(bromomethyl)-1,3-dimethyl-1H-pyrazol-4-yl]-1-[3-(methylamino)propyl]-3-[3-(naphthalen-1-yloxy)propyl]-1H-indole-2-carboxylate hydrochloric acid salt (1.30 g) and caesium carbonate (3.17 g, 9.73 mmol) in DMF (190 ml) was stirred for 20 h at 65° C. For work-up, water was added and the mixture was extracted with a mixture of dichloromethane/2-propanol (4:1). The combined organic phases were filtrated through a silicone filter and the residue was purified by flash chromatography (Biotage SNAP cartridge silica 50 g, hexanes/ethyl acetate gradient, 20%→100% ethyl acetate) to give the title compound (522 mg).

LC-MS (Method 2): $R_t$=1.75 min; MS (ESIpos): m/z=551 [M+H]$^+$ $^1$H-NMR (400 MHz, DMSO-d$_6$): δ [ppm]=8.24-8.19 (m, 1H), 7.90-7.85 (m, 1H), 7.73 (dd, 1H), 7.56-7.48 (m, 2H), 7.48-7.42 (m, 1H), 7.42-7.37 (m, 1H), 7.05 (dd, 1H), 6.94-6.88 (m, 2H), 4.42 (dt, 1H), 4.31-4.18 (m, 4H), 3.85-3.75 (m, 4H), 3.59 (d, 1H), 3.41-3.35 (m, 1H), 3.31-3.22 (m, 1H), 2.96 (d, 1H), 2.35-2.29 (m, 1H), 2.23-2.15 (m, 5H), 1.91-1.82 (m, 4H), 1.60-1.46 (m, 2H), 1.27 (t, 3H)

Intermediate 1-44 ethyl 7-{1,3-dimethyl-5-[(prop-2-en-1-yloxy)methyl]-1H-pyrazol-4-yl}-3-[3-(naphthalen-1-yloxy)propyl]-1-(prop-2-en-1-yl)-1H-indole-2-carboxylate

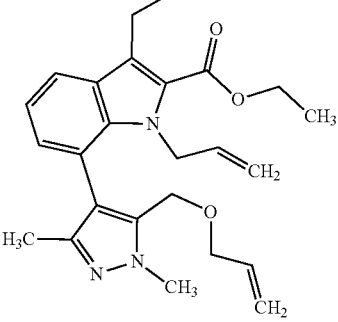

Sodium hydride (338 mg, 60% suspension in mineral oil, 8.44 mmol) was added at 0° C. to a solution of ethyl 7-[5-(hydroxymethyl)-1,3-dimethyl-1H-pyrazol-4-yl]-3-[3-(naphthalen-1-yloxy)propyl]-1H-indole-2-carboxylate (see Intermediate 1-39; 1.20 g, 2.41 mmol) in THF (33 ml), and the mixture was stirred for 30 min at that temperature. Allyl bromide (730 μl, 8.4 mmol) in THF (0.5 ml) was added and the mixture was stirred for 3 days at room temperature. Additional portions of sodium hydride (105 mg, 55% suspension in mineral oil, 2.41 mmol) and allyl bromide (310 μl, 3.6 mmol) were added and the mixture was stirred for 3 more days. For work-up, brine was added and the mixture was extracted three times with ethyl acetate, the combined organic phases were washed with brine, filtrated through a silicone filter and concentrated. The residue was purified by flash chromatography (Biotage SNAP cartridge silica 25 g, hexanes/ethyl acetate gradient 50%→100% ethyl acetate) to give the title (895 mg, 64% yield).

LC-MS (Method 2): $R_t$=1.77 min; MS (ESIpos): m/z=578 [M+H]$^+$ $^1$H-NMR (400 MHz, DMSO-d6) δ [ppm]: 1.154 (4.94), 1.171 (10.07), 1.189 (4.78), 1.246 (4.66), 1.264 (10.52), 1.282 (4.76), 1.913 (14.41), 1.987 (16.00), 2.083 (0.46), 2.202 (0.87), 2.218 (1.16), 2.238 (0.91), 2.322 (0.41), 2.326 (0.56), 2.518 (2.26), 2.522 (1.58), 2.664 (0.41), 2.668 (0.55), 3.295 (1.14), 3.316 (1.69), 3.755 (0.54), 3.769 (0.54), 3.784 (0.76), 3.788 (1.28), 3.791 (0.79), 3.798 (0.79), 3.802 (1.31), 3.805 (0.83), 3.825 (15.02), 3.838 (1.01), 3.841 (1.43), 3.845 (0.84), 3.861 (0.57), 3.874 (0.56), 3.999 (1.29), 4.017 (3.77), 4.034 (3.70), 4.052 (1.18), 4.088 (1.98), 4.106 (1.17), 4.110 (1.25), 4.119 (2.58), 4.149 (1.18), 4.152 (1.21), 4.212 (2.08), 4.224 (2.89), 4.230 (4.80), 4.239 (1.42), 4.248 (4.02), 4.266 (3.64), 4.296 (2.02), 4.667 (0.44), 4.679 (0.46), 4.709 (0.72), 4.720 (1.85), 4.724 (1.60), 4.746 (1.32), 4.749 (1.23), 4.829 (0.65), 4.841 (0.73), 4.871 (0.47), 4.883 (0.49), 4.993 (0.50), 4.997 (1.10), 5.002 (1.38), 5.005 (0.61), 5.023 (1.68), 5.026 (2.41), 5.031 (1.86), 5.035 (0.49), 5.065 (0.70), 5.069 (1.56), 5.074 (1.45), 5.078 (0.51), 5.406 (0.69), 5.419 (0.46), 5.432 (0.75), 5.449 (0.76), 5.461 (0.42), 5.475 (0.63), 5.687 (0.50), 5.701 (0.99), 5.714 (0.81), 5.727 (1.04), 5.730 (0.55), 5.741 (0.56), 5.744 (0.97), 5.758 (0.71), 5.770 (0.88), 5.784 (0.40), 6.901 (1.57), 6.918 (1.71), 6.969 (1.67), 6.972 (1.79), 6.987 (2.14), 6.990 (2.05), 7.097 (1.95), 7.114 (1.76), 7.117 (2.10), 7.135 (1.51), 7.373 (1.31), 7.393 (2.38), 7.412 (2.00), 7.454 (2.36), 7.474 (1.34), 7.497 (0.52), 7.510 (1.58), 7.516 (2.33), 7.525 (3.29), 7.534 (2.62), 7.540 (1.75), 7.552 (0.58), 7.767 (1.75), 7.770 (1.77), 7.787 (1.63), 7.790 (1.59), 7.862 (1.36), 7.865 (0.99), 7.872 (0.67), 7.880 (0.97), 7.886 (1.15), 8.226 (1.20), 8.233 (0.95), 8.239 (0.51), 8.241 (0.55), 8.250 (1.11).

Intermediate 1-45

(rac)-(E/Z)-ethyl-1,3-dimethyl-7-[3-(naphthalen-1-yloxy)propyl]-1,10,13,15-tetrahydropyrazolo[4',3':9,10][1,6]oxazacycloundecino[8,7,6-hi]indole-8-carboxylate

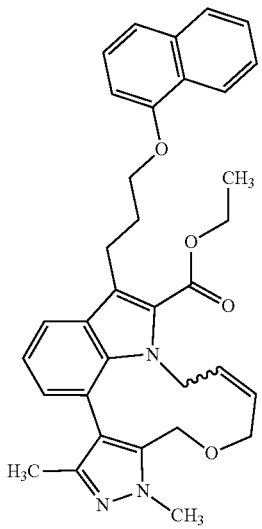 [SMILES: CCOC(=O)c1c(CCCOc2cccc3ccccc23)c2cccc3c2n1CC=CCOCc1c-3c(C)nn1C]

(1,3-Bis(2,4,6-trimethylphenyl)-2-imidazolidinylidene)dichloro(phenylmethylene)(tricyclohexylphosphine)ruthenium (CAS No 246047-72-3; Grubbs 2nd generation catalyst; 131 mg, 154 µmol) was added to a degassed solution of ethyl 7-{1,3-dimethyl-5-[(prop-2-en-1-yloxy)methyl]-1H-pyrazol-4-yl}-3-[3-(naphthalen-1-yloxy)propyl]-1-(prop-2-en-1-yl)-1H-indole-2-carboxylate (890 mg, 1.54 mmol) in dichloromethane (20 ml), and the mixture was stirred at room temperature overnight. For work-up, the reaction mixture was concentrated and the residue was purified by flash chromatography (Biotage SNAP cartridge silica 25 g, hexanes/ethyl acetate gradient, 0%→100% ethyl acetate) to give the title compound (479 mg, 57% yield), together impurities and was used in the next step without further purification.

LC-MS (Method 1): $R_t$=1.71 min; MS (ESIpos): m/z=550 [M+H]$^+$

Intermediate 1-46

(rac)-ethyl 1,3-dimethyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate

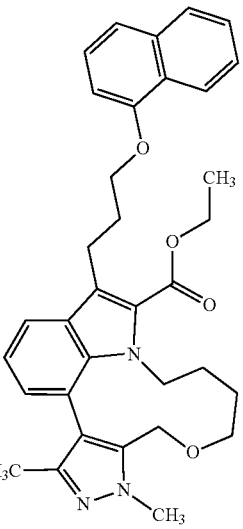

The title compound was prepared in analogy to the synthesis of (rac)-ethyl 3-({4-[4-(tert-butoxycarbonyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (see Intermediate 1-11) using (rac)-(E/Z)- ethyl 1,3-dimethyl-7-[3-(naphthalen-1-yloxy)propyl]-1,10,13,15-tetrahydropyrazolo[4',3':9,10][1,6]oxazacycloundecino[8,7,6-hi]indole-8-carboxylate (475 mg, 864 µmol) as starting material to give the title compound (453 mg, 95% yield) which was used in the next step without further purification.

LC-MS (Method 2): $R_t$=1.70 min; MS (ESIpos): m/z=552 [M+H]$^+$

Intermediate 1-47 ethyl 4-bromo-1,5-dimethyl-1H-pyrazole-3-carboxylate

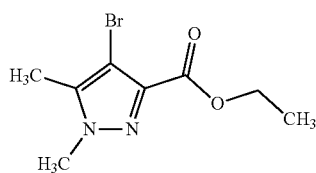

N-Bromosuccinimide (16.3 g, 90.5 mmol) was added to a solution of ethyl 1,5-dimethyl-1H-pyrazole-3-carboxylate (7.25 g, 43.1 mmol, CAS No 5744-51-4) in 1,2-dichloroethane (150 ml) and the mixture was stirred for 15 h at 80° C. For work-up, the mixture was diluted with dichloromethane, washed with water and the organic phase was filtrated through a silicone filter and concentrated. The residue was purified by flash chromatography (Biotage SNAP cartridge silica 340 g, hexanes/dichloromethane gradient, 0→100% dichloromethane) to give the title compound (6.49 g, 61% yield).

1H-NMR (400 MHz, DMSO-d6) δ [ppm]: 1.261 (4.14), 1.278 (8.78), 1.296 (4.21), 2.268 (14.94), 2.518 (0.74), 2.523 (0.49), 3.857 (16.00), 4.229 (1.31), 4.247 (4.03), 4.264 (3.94), 4.282 (1.24).

Intermediate 1-48

(4-bromo-1,5-dimethyl-1H-pyrazol-3-yl)methanol

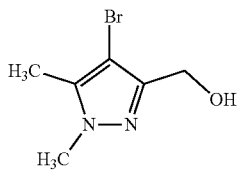

Lithium borohydride (711 mg, 32.6 mmol) was added to a solution of ethyl 4-bromo-1,5-dimethyl-1H-pyrazole-3-carboxylate (6.45 g, 26.1 mmol) in THF (150 ml) and the mixture was stirred for 1 h at room temperature and 7 h at 60° C. The reaction was quenched by addition of saturated aqueous ammonium chloride solution and the mixture was extracted with ethyl acetate. The organic phase was filtrated through a silicone filter and concentrated. The residue was purified by flash chromatography (hexanes/ethyl acetate gradient, 50%→100% ethyl acetate) to give the title compound (4.07 g, 76% yield).

1H-NMR (400 MHz, DMSO-d6) δ [ppm]: 2.205 (16.00), 2.518 (0.43), 3.330 (10.35), 4.285 (3.97), 4.299 (4.13), 4.933 (1.00), 4.946 (2.22), 4.960 (0.93).

Intermediate 1-49 ethyl 7-[3-(hydroxymethyl)-1,5-dimethyl-1H-pyrazol-4-yl]-3-[3-(naphthalen-1-yloxy)propyl]-1H-indole-2-carboxylate

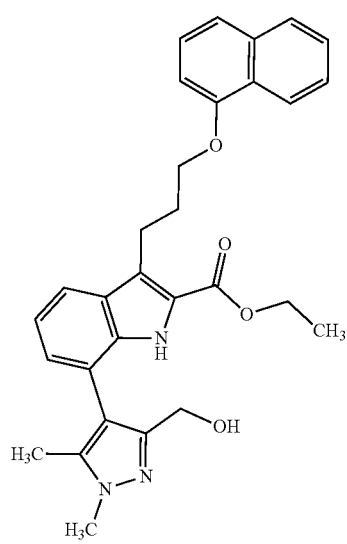

XPhos Pd G2 (see abbreviations; 483 mg, 613 µmol) was added to a degassed mixture of ethyl 3-[3-(naphthalen-1-yloxy)propyl]-7-(4,4,5,5-tetramethyl-1,3,2-dioxaborolan-2-yl)-1H-indole-2-carboxylate (see Intermediate 1-4; 10.0 g, 20.0 mmol), (4-bromo-1,5-dimethyl-1H-pyrazol-3-yl)methanol (3.73 g, 18.2 mmol), aqueous potassium phosphate solution (73 ml, 0.50 M, 36 mmol) and THF (220 ml). The mixture was stirred for 2 h at 45° C. For work-up, ethyl acetate was added, the mixture was filtrated through a pad of celite, eluted with ethyl acetate and the organic phase was washed with brine, filtrated through a silicone filter and concentrated. The residue was purified by flash chromatography (Biotage SNAP cartridge silica 340 g, hexanes/ethyl acetate gradient, 50%→100% ethyl acetate) to give the title compound (6.26 g, 63% yield).

LC-MS (Method 1): $R_t$=1.53 min; MS (ESIpos): m/z=498 [M+H]+

1H-NMR (400 MHz, DMSO-d6) δ [ppm]: 1.155 (0.41), 1.173 (0.87), 1.190 (0.43), 1.256 (4.82), 1.273 (10.89), 1.291 (4.91), 1.988 (1.61), 2.164 (15.76), 2.205 (5.25), 2.213 (1.06), 2.231 (1.35), 2.250 (1.03), 2.518 (4.03), 2.523 (2.82), 3.355 (2.05), 3.373 (1.25), 3.726 (4.77), 3.802 (16.00), 4.199 (1.49), 4.214 (3.13), 4.222 (2.24), 4.229 (1.83), 4.240 (5.74), 4.249 (2.82), 4.258 (5.54), 4.275 (1.50), 4.286 (1.45), 4.300 (1.40), 4.947 (0.67), 5.705 (1.59), 6.907 (1.76), 6.925 (1.90), 7.060 (0.72), 7.077 (2.44), 7.090 (2.89), 7.096 (5.04), 7.108 (0.79), 7.373 (1.28), 7.394 (2.46), 7.413 (2.02), 7.450 (2.56), 7.471 (1.40), 7.492 (0.58), 7.505 (1.56), 7.509 (1.42), 7.514 (1.62), 7.521 (3.30), 7.529 (1.74), 7.533 (1.54), 7.538 (1.62), 7.551 (0.63), 7.656 (1.49), 7.662 (1.33), 7.674 (1.37), 7.679 (1.33), 7.861 (1.49), 7.868 (0.80), 7.879 (1.35), 7.884 (1.25), 8.230 (1.30), 8.236 (1.23), 8.254 (1.25), 11.324 (1.73).

Intermediate 1-50 ethyl 1-{3-[(tert-butoxycarbonyl)(methyl)amino]propyl}-7-[3-(hydroxymethyl)-1,5-dimethyl-1H-pyrazol-4-yl]-3-[3-(naphthalen-1-yloxy)propyl]-1H-indole-2-carboxylate

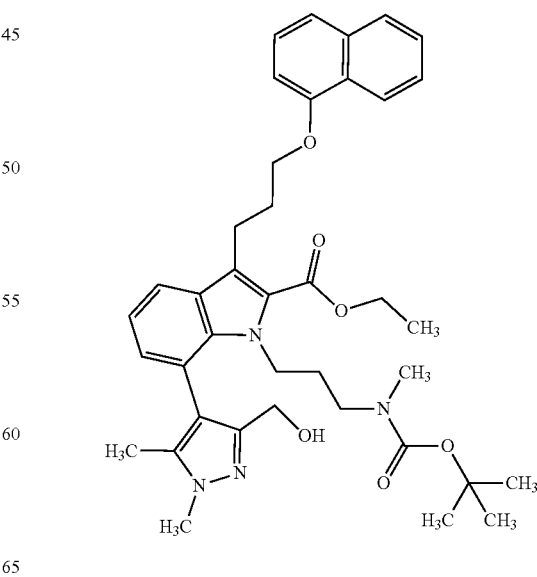

A mixture of ethyl 7-[3-(hydroxymethyl)-1,5-dimethyl-1H-pyrazol-4-yl]-3-[3-(naphthalen-1-yloxy)propyl]-1H-indole-2-carboxylate (1.50 g, 3.01 mmol) and caesium carbonate (4.91 g, 15.1 mmol) in DMF (37 ml) was stirred for 10 min at room temperature. tert-butyl (3-bromopropyl)methylcarbamate (see Intermediate 1-1; 836 mg, 3.32 mmol) was then added and the mixture was stirred for 48 h at room temperature. For work-up, water was added, and the mixture was extracted with a mixture of dichloromethane/2-propanol (4:1). The combined organic phases were filtrated through a silicone filter and concentrated. The residue was purified by flash chromatography (Biotage SNAP cartridge silica 50 g, hexanes/ethyl acetate gradient, 20%→100% ethyl acetate) to give the title compound (1.02 g, 50% yield).

LC-MS (Method 2): $R_t$=1.70 min; MS (ESIpos): m/z=669 [M+H]$^+$ $^1$H-NMR (400 MHz, DMSO-d6) δ [ppm]: 1.271 (9.34), 1.289 (12.93), 1.306 (6.30), 1.363 (2.95), 2.023 (16.00), 2.196 (1.08), 2.212 (1.42), 2.233 (1.10), 2.322 (0.78), 2.327 (1.16), 2.332 (0.84), 2.518 (5.09), 2.523 (4.61), 2.536 (1.76), 2.540 (1.60), 2.560 (1.32), 2.665 (1.16), 2.669 (1.52), 2.673 (1.18), 3.279 (1.34), 3.301 (1.96), 3.316 (1.68), 3.800 (3.35), 4.152 (1.10), 4.166 (1.12), 4.221 (1.78), 4.236 (3.65), 4.247 (3.15), 4.265 (5.07), 4.283 (4.75), 4.301 (1.48), 5.759 (3.61), 6.914 (1.86), 6.916 (1.92), 6.933 (2.09), 6.935 (1.98), 7.034 (1.18), 7.070 (0.94), 7.089 (1.28), 7.376 (1.70), 7.396 (3.01), 7.415 (2.53), 7.454 (3.03), 7.475 (1.66), 7.498 (0.62), 7.511 (1.98), 7.515 (3.57), 7.525 (4.03), 7.534 (3.67), 7.539 (2.25), 7.551 (0.72), 7.719 (1.94), 7.722 (2.01), 7.739 (1.86), 7.742 (1.80), 7.863 (1.70), 7.867 (1.24), 7.874 (0.86), 7.878 (1.06), 7.881 (1.12), 7.886 (1.46), 8.224 (1.50), 8.231 (1.04), 8.243 (0.82), 8.245 (1.08), 8.248 (1.40).

Intermediate 1-51 ethyl 7-[3-(bromomethyl)-1,5-dimethyl-1H-pyrazol-4-yl]-1-{3-[(tert-butoxycarbonyl)(methyl)amino]propyl}-3-[3-(naphthalen-1-yloxy)propyl]-1H-indole-2-carboxylate

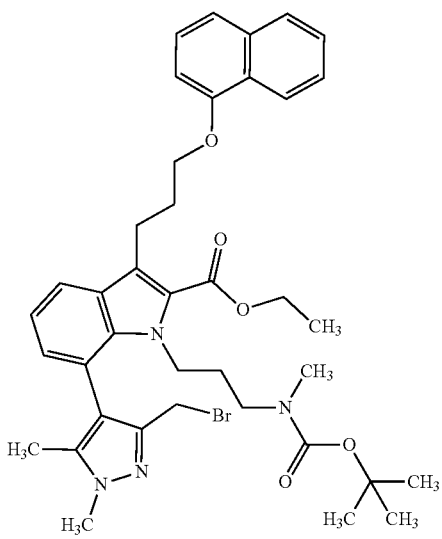 [SMILES: CCOC(=O)c1c(CCCOc2cccc3ccccc23)c2cccc(-c3c(CBr)nn(C)c3C)c2n1CCCN(C)C(=O)OC(C)(C)C]

A mixture of ethyl 1-{3-[(tert-butoxycarbonyl)(methyl)amino]propyl}-7-[3-(hydroxymethyl)-1,5-dimethyl-1H-pyrazol-4-yl]-3-[3-(naphthalen-1-yloxy)propyl]-1H-indole-2-carboxylate (1.02 g, 1.53 mmol) and triphenylphosphine (960 mg, 3.66 mmol) in dichloromethane (28 ml) was stirred for 10 min at 0° C. Tetrabromomethane (1.11 g, 3.36 mmol) was then added and the mixture was stirred for 2 h at room temperature. For work-up the reaction mixture was concentrated and the crude product (3.5 g) was used in the subsequent step without further purification.

LC-MS (Method 1): $R_t$=1.84 min; MS (ESIpos): m/z=731 [M+H]$^+$

Intermediate 1-52 ethyl 7-[3-(bromomethyl)-1,5-dimethyl-1H-pyrazol-4-yl]-1-[3-(methylamino)propyl]-3-[3-(naphthalen-1-yloxy)propyl]-1H-indole-2-carboxylate hydrochloric acid salt

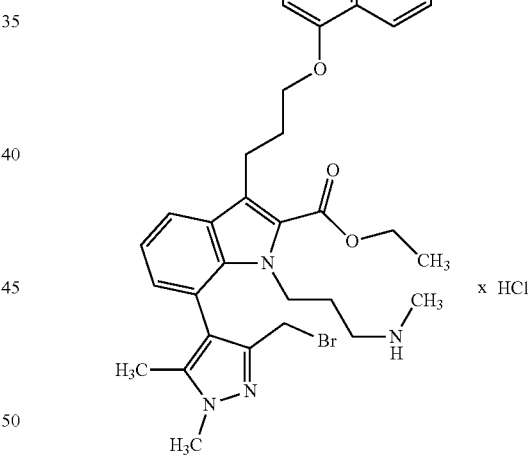

Hydrochloric acid (28 ml, 4.0 M in dioxane, 110 mmol) was added to a solution of ethyl 7-[3-(bromomethyl)-1,5-dimethyl-1H-pyrazol-4-yl]-1-{3-[(tert-butoxycarbonyl)(methyl)amino]propyl}-3-[3-(naphthalen-1-yloxy)propyl]-1H-indole-2-carboxylate (1.12 g, 1.53 mmol) in methanol (18 ml) and the mixture was stirred for 2 h at room temperature. For work-up, the reaction mixture was concentrated to give the title compound (3.7 g) which was used in the next step without further purification.

Intermediate 1-53

(rac)-ethyl 7,10,11-trimethyl-1-[3-(naphthalen-1-yloxy)propyl]-4,5,6,7,8,10-hexahydropyrazolo[3',4':7,8][1,5]diazecino[9,10,1-hi]indole-2-carboxylate

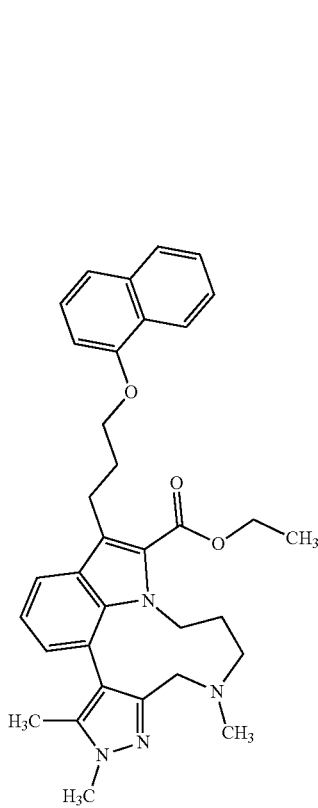 [SMILES: CCOC(=O)c1c(CCCOc2cccc3ccccc23)c2cccc3c2n1CCCN(C)Cc1nn(C)c(C)c1-3]

A mixture of ethyl 7-[3-(bromomethyl)-1,5-dimethyl-1H-pyrazol-4-yl]-1-[3-(methylamino)propyl]-3-[3-(naphthalen-1-yloxy)propyl]-1H-indole-2-carboxylate hydrochloric acid salt (1.02 g) and caesium carbonate (2.48 g, 7.63 mmol) in DMF (150 ml) was stirred for 20 h at 65° C. For work-up, water was added and the mixture was extracted with a mixture of dichloromethane/2-propanol (4:1). The combined organic phases were filtrated through a silicone filter and the residue was purified by flash chromatography (Biotage SNAP cartridge silica 50 g, hexanes/ethyl acetate gradient, 20%→100% ethyl acetate followed by an ethyl acetate/ethanol gradient, 0%→20% ethanol) to give the title compound (515 mg).

LC-MS (Method 1): $R_t$=1.46 min; MS (ESIpos): m/z=551 [M+H]$^+$

Intermediate 1-54 ethyl 7-{1,5-dimethyl-3-[(prop-2-en-1-yloxy)methyl]-1H-pyrazol-4-yl}-3-[3-(naphthalen-1-yloxy)propyl]-1-(prop-2-en-1-yl)-1H-indole-2-carboxylate

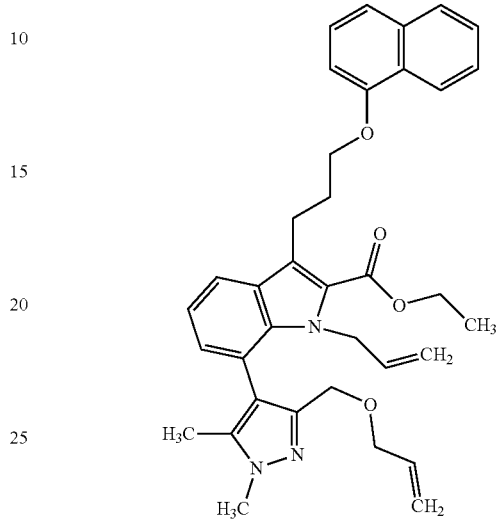

Sodium hydride (1.62 g, 60% suspension in mineral oil, 40.4 mmol) was added at 0° C. to a solution of ethyl 7-[3-(hydroxymethyl)-1,5-dimethyl-1H-pyrazol-4-yl]-3-[3-(naphthalen-1-yloxy)propyl]-1H-indole-2-carboxylate (see Intermediate 1-49; 5.75 g, 11.6 mmol) in THF (160 ml) and the mixture was stirred for 30 min at that temperature. Allyl bromide (3.5 ml, 40 mmol) in THF was added and the mixture was stirred for 24 h at room temperature. For work-up, brine was added and the mixture was extracted three times with ethyl acetate, the combined organic phases were washed with brine, filtrated through a silicone filter and concentrated. The residue was purified by flash chromatography (Biotage SNAP cartridge silica 340 g, hexanes/ethyl acetate gradient 50%→100% ethyl acetate) to give the title compound (5.39 g, 81% yield).

LC-MS (Method 1): $R_t$=1.73 min; MS (ESIpos): m/z=578 [M+H]$^+$ $^1$H-NMR (400 MHz, DMSO-d6) δ [ppm]: 1.154 (4.21), 1.172 (8.94), 1.189 (4.42), 1.246 (2.03), 1.263 (4.58), 1.281 (2.07), 1.984 (7.95), 1.987 (16.00), 2.199 (0.42), 2.218 (0.58), 2.235 (0.42), 2.518 (0.87), 2.522 (0.57), 3.294 (0.54), 3.315 (0.83), 3.725 (0.68), 3.728 (0.42), 3.733 (0.43), 3.737 (0.68), 3.742 (0.44), 3.745 (0.46), 3.749 (0.69), 3.753 (0.41), 3.758 (0.46), 3.762 (0.70), 3.766 (0.43), 3.782 (0.43), 3.792 (6.66), 3.999 (1.08), 4.017 (3.27), 4.035 (3.30), 4.053 (1.09), 4.083 (0.78), 4.111 (1.43), 4.127 (0.56), 4.131 (0.54), 4.157 (1.47), 4.170 (0.60), 4.174 (0.59), 4.186 (0.84), 4.205 (0.67), 4.210 (0.89), 4.220 (1.34), 4.228 (2.16), 4.235 (0.71), 4.246 (1.88), 4.264 (0.55), 4.726 (0.58), 4.730 (0.58), 4.752 (0.62), 4.756 (0.71), 4.769 (0.83), 4.781 (0.86), 4.927 (0.52), 4.932 (0.67), 4.949 (0.85), 4.953 (1.08), 4.958 (0.88), 4.992 (0.77), 4.997 (0.64), 5.581 (0.52), 5.594 (0.47), 5.607 (0.48), 5.623 (0.45), 5.650 (0.41), 6.897 (0.73), 6.915 (0.81), 6.980 (0.73), 6.983 (0.75), 6.998 (1.02), 7.001 (0.92), 7.074 (0.89), 7.094 (0.99), 7.112 (0.61), 7.373 (0.56), 7.393 (1.06), 7.412 (0.88), 7.453 (1.08), 7.474 (0.60), 7.513 (0.75), 7.517 (1.20), 7.527 (1.35), 7.536 (1.17), 7.541 (0.81), 7.749 (0.81), 7.752 (0.83), 7.769 (0.77), 7.772 (0.70), 7.863 (0.62), 7.866 (0.43), 7.880 (0.41), 7.886 (0.52), 8.234 (0.56), 8.259 (0.49).

Intermediate 1-55

(rac)-(E/Z)-ethyl-2,3-dimethyl-7-[3-(naphthalen-1-yloxy)propyl]-2,10,13,15-tetrahydropyrazolo[4',3':9,10][1,6]oxazacycloundecino[8,7,6-hi]indole-8-carboxylate

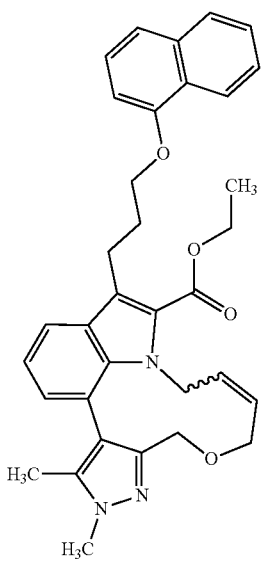 [SMILES: CCOC(=O)c1c(CCCOc2cccc3ccccc23)c2cccc3c2n1CC=CCOCc1nn(C)c(C)c1-3]

1,3-Bis(2,4,6-trimethylphenyl)-2-imidazolidinylidene)dichloro(phenylmethylene)(tricyclohexylphosphine)ruthenium (CAS No 246047-72-3; Grubbs 2nd generation catalyst; 792 mg, 933 μmol) was added to a solution of ethyl 7-{1,5-dimethyl-3-[(prop-2-en-1-yloxy)methyl]-1H-pyrazol-4-yl}-3-[3-(naphthalen-1-yloxy)propyl]-1-(prop-2-en-1-yl)-1H-indole-2-carboxylate (5.39 g, 9.33 mmol) in dichloromethane (120 ml) and the mixture was stirred at room temperature overnight. For work-up, the reaction mixture was concentrated and the residue was purified by flash chromatography (Biotage SNAP cartridge silica 100 g, hexanes/ethyl acetate gradient, 50%→100% ethyl acetate) to give the title compound (789 mg, 15% yield).

$^1$H-NMR (400 MHz, DMSO-$d_6$): δ [ppm]=8.24-8.17 (m, 1H), 7.90-7.80 (m, 1H), 7.74 (dd, 1H), 7.54-7.35 (m, 4H), 7.07 (dd, 1H), 6.94-6.83 (m, 2H), 5.27 (td, 1H), 5.11 (td, 1H), 4.92-4.70 (m, 2H), 4.37-4.17 (m, 6H), 3.82 (s, 3H), 3.73 (t, 1H), 3.57 (dd, 1H), 3.39-3.32 (m, 1H), 3.29-3.22 (m, 1H), 2.22 (br dd, 2H), 1.82 (s, 3H), 1.26 (t, 3H)

Intermediate 1-56

(rac)-ethyl 2,3-dimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylate

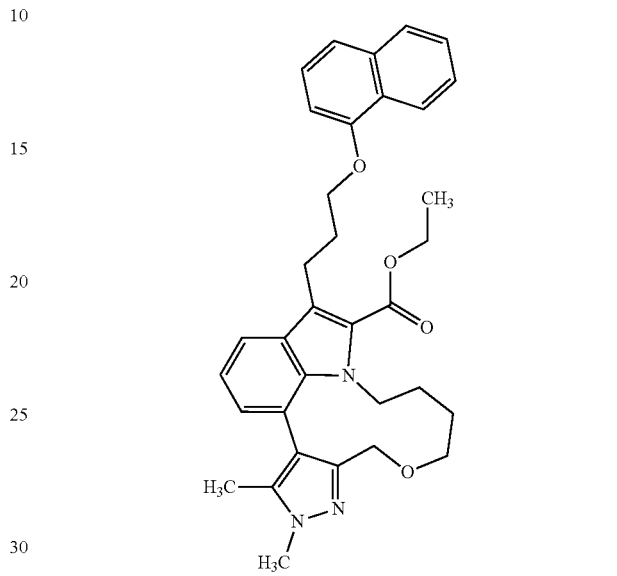

The title compound was prepared in analogy to the synthesis of (rac)-ethyl 3-({4-[4-(tert-butoxycarbonyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (see Intermediate 1-11) using (rac)-(E/Z)-ethyl 2,3-dimethyl-7-[3-(naphthalen-1-yloxy)propyl]-2,10,13,15-tetrahydropyrazolo[4',3':9,10][1,6]oxazacycloundecino[8,7,6-hi]indole-8-carboxylate (785 mg, 1.43 mmol) as starting material to give the title compound (758 mg, 96% yield) which was used in the next step without further purification.

LC-MS (Method 2): R$_t$=1.68 min; MS (ESIpos): m/z=552 [M+H]$^+$

Intermediate 1-57 tert-butyl 4-{4-[(4-bromo-5-formyl-1-methyl-1H-pyrazol-3-yl)methoxy]phenyl}piperazine-1-carboxylate

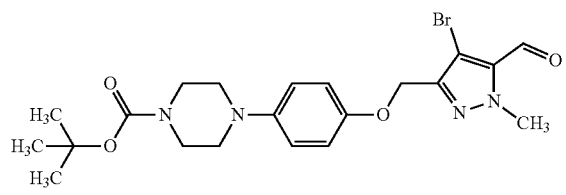 [SMILES: Cn1nc(COc2ccc(N3CCN(C(=O)OC(C)(C)C)CC3)cc2)c(Br)c1C=O]

A solution of DMSO (1.6 ml, 22 mmol) in dichloromethane (1 ml) was added dropwise at −78° C. to a solution of oxalyl chloride (5.6 ml, 2.0 M in dichloromethane, 11 mmol) in dichloromethane (58 ml) and the mixture was stirred for 20 min. A solution of tert-butyl 4-(4-{[4-bromo-5-(hydroxymethyl)-1-methyl-1H-pyrazol-3-yl]methoxy}phenyl)piperazine-1-carboxylate (see Intermediate 1-7; 3.60 g, 7.48 mmol) in dichloromethane (1 ml) was added and the mixture was stirred for 1 h at −78° C. Triethylamine (6.3 ml, 45 mmol) was then added dropwise and the mixture was allowed to warm to 0° C. over 1 h. The mixture was then poured onto ice-water and the phases were separated. The aqueous phase was extracted with ethyl acetate and the combined organic phases were washed with brine, filtrated through a silicone filter and concentrated. The residue was purified by flash chromatography (hexanes/ethyl acetate gradient, 0%→50% then 100% ethyl acetate) to give the title compound (3.54 g, 96% yield).

LC-MS (Method 2): $R_t$=1.41 min; MS (ESIpos): m/z=479 [M+H]$^+$ $^1$H-NMR (400 MHz, DMSO-d6) δ [ppm]: 1.172 (0.91), 1.413 (16.00), 1.988 (1.73), 2.956 (1.15), 2.969 (0.93), 3.441 (0.99), 4.095 (6.48), 4.953 (2.82), 6.916 (2.21), 6.924 (2.37), 9.839 (2.73).

Intermediate 1-58 tert-butyl 4-[4-({4-bromo-5-[6-ethoxy-6-oxohex-1-en-1-yl]-1-methyl-1H-pyrazol-3-yl}methoxy)phenyl]piperazine-1-carboxylate; mixture of E/Z isomers

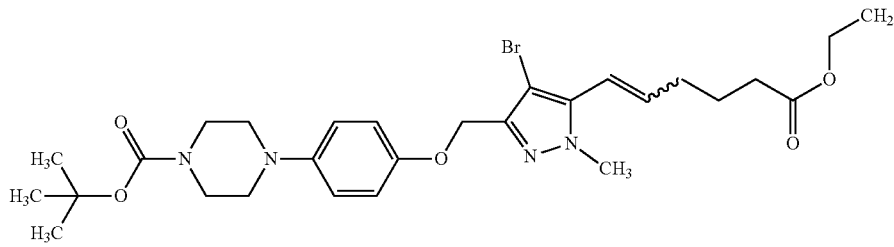 [SMILES: CCOC(=O)CCCC=Cc1c(Br)c(COc2ccc(N3CCN(C(=O)OC(C)(C)C)CC3)cc2)nn1C]

n-Butyl lithium (1.8 ml, 2.5 M in hexanes, 4.4 mmol) was added dropwise at −78° C. to a suspension of (5-ethoxy-5-oxopentyl)(triphenyl)phosphonium bromide (2.21 g, 4.69 mmol, CAS No 54110-96-2) in THF (30 ml) and the mixture was stirred for 1 h at 0° C. Upon cooling to −78° C., a solution of tert-butyl 4-{4-[(4-bromo-5-formyl-1-methyl-1H-pyrazol-3-yl)methoxy]phenyl}piperazine-1-carboxylate (1.50 g, 3.13 mmol) in THF (3 ml) was added dropwise and the mixture was allowed to warm to room temperature overnight. For work-up, saturated aqueous ammonium chloride was added and the mixture was extracted with ethyl acetate, the organic phase was washed with brine, filtrated through a silicone filter and concentrated. The residue was purified by flash chromatography (Biotage SNAP cartridge silica, hexanes/ethyl acetate gradient 20%→100% ethyl acetate) to give the title compound (931 mg, 50% yield) as a mixture of E/Z isomers.

LC-MS (Method 2): $R_t$=1.53 and 1.56 min; MS (ESIpos): m/z=591 [M+H]$^+$ $^1$H-NMR (400 MHz, DMSO-d$_6$, mixture of E/Z isomers): δ [ppm]=6.96-6.85 (m, 4H), 6.54-6.45 (m, 0.5H), 6.41-6.34 (m, 0.5H), 6.20 (d, 0.4H), 6.06-5.99 (m, 0.4H), 4.90-4.83 (m, 2H), 4.08-3.95 (m, 2H), 3.83 (s, 1.8H), 3.70 (s, 1.2H), 3.49-3.39 (m, 4H), 3.00-2.90 (m, 4H), 2.43-2.23 (m, 3H), 2.05-2.00 (m, 1H), 1.76-1.57 (m, 2H), 1.41 (s, 9H), 1.17 (t, 2H), 1.12 (t, 1H)

Intermediate 1-59 tert-butyl 4-[4-({4-bromo-5-[6-hydroxyhex-1-en-1-yl]-1-methyl-1H-pyrazol-3-yl}methoxy)phenyl]piperazine-1-carboxylate mixture of E/Z isomers

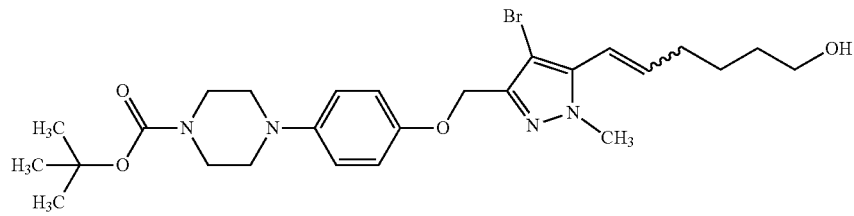 [SMILES: Cn1nc(COc2ccc(N3CCN(C(=O)OC(C)(C)C)CC3)cc2)c(Br)c1C=CCCCCO]

Lithium borohydride (34.2 mg, 1.57 mmol) was added under ice cooling to a solution of tert-butyl 4-[4-({4-bromo-5-[6-ethoxy-6-oxohex-1-en-1-yl]-1-methyl-1H-pyrazol-3-yl}methoxy)phenyl]piperazine-1-carboxylate (mixture of E/Z isomers; 931 mg, 1.57 mmol) in THF (31 ml), and the mixture was allowed to warm to room temperature. Another portion of lithium borohydride (34.2 mg, 1.57 mmol) was added and the mixture was stirred for 4 h at 50° C. For work-up, the reaction mixture was combined with a second batch which was prepared similarly. Saturated aqueous ammonium chloride was added and the mixture was extracted with ethyl acetate. The combined organic phases were filtrated through a silicone filter, concentrated under reduced pressure and the residue was purified by flash chromatography (Biotage SNAP cartridge silica 25 g, hexanes/ethyl acetate gradient, 50%→100% ethyl acetate) to give the title compound (1.12 g) as mixture of E/Z-isomers.

LC-MS (Method 2): $R_t$=1.38 min; MS (ESIpos): m/z=549 [M+H]$^+$ $^1$H-NMR (400 MHz, DMSO-d$_6$, mixture of E/Z isomers): δ [ppm]=6.92-6.86 (m, 4H), 6.51 (dt, 0.5H), 6.35 (dt, 0.5H), 6.17-6.12 (m, 0.5H), 6.05-5.98 (m, 0.5H), 4.86-4.79 (m, 2H), 4.39-4.30 (m, 1H), 3.80 (s, 1.5H), 3.70-3.67 (m, 1.5H), 3.44-3.38 (m, 4H), 2.95-2.89 (m, 4H), 2.27-2.20 (m, 1H), 2.01-1.93 (m, 1H), 1.50-1.42 (m, 2H), 1.42-1.33 (m, 11H)

Intermediate 1-60 ethyl 7-{3-({4-[4-(tert-butoxycarbonyl)piperazin-1-yl]phenoxy}methyl)-5-[6-hydroxyhex-1-en-1-yl]-1-methyl-1H-pyrazol-4-yl}-3-[3-(naphthalen-1-yloxy)propyl]-1H-indole-2-carboxylate mixture of E/Z-isomers

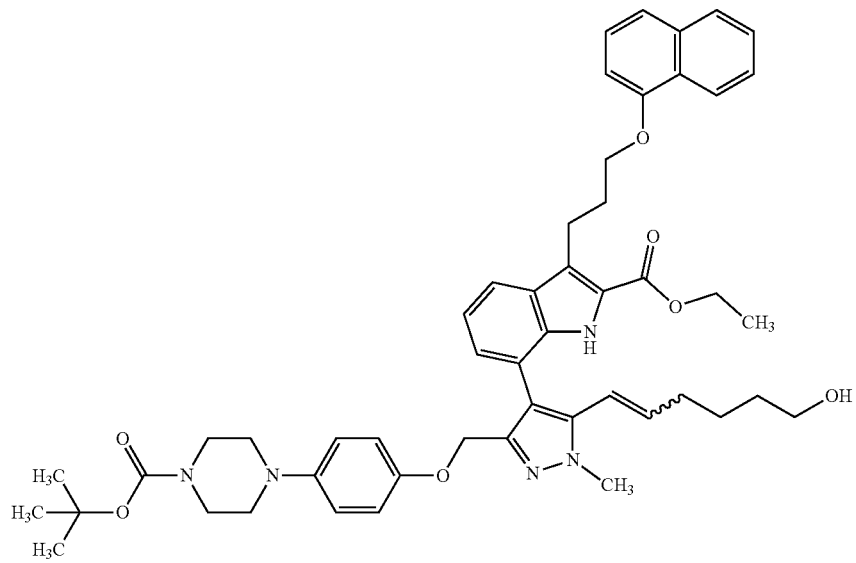

XPhos Pd G2 (see abbreviations, 54.0 mg, 68.7 μmol) was added to a degassed mixture of ethyl 3-[3-(naphthalen-1-yloxy)propyl]-7-(4,4,5,5-tetramethyl-1,3,2-dioxaborolan-2-yl)-1H-indole-2-carboxylate (see Intermediate 1-4; 1.12 g, 2.24 mmol), tert-butyl 4-[4-({4-bromo-5-[6-hydroxyhex-1-en-1-yl]-1-methyl-1H-pyrazol-3-yl}methoxy)phenyl]piperazine-1-carboxylate mixture of E/Z-isomers (1.12 g, 2.04 mmol), aqueous potassium phosphate solution (8.2 ml, 0.50 M, 4.1 mmol) and THF (25 ml) and the mixture was stirred for 2 h at 45° C. For work-up, ethyl acetate was added, the mixture was filtrated through a pad of celite, eluted with ethyl acetate and the organic phase was washed with brine, filtrated through a silicone filter and concentrated. The residue was purified by flash chromatography (Biotage SNAP cartridge silica 50 g, hexanes/ethyl acetate gradient, 0%→100% ethyl acetate) to give the title compound (1.21 g, 64% yield) as a mixture of E/Z-isomers.

LC-MS (Method 2): $R_t$=1.72 min; MS (ESIneg): m/z=840 [M−H]$^−$

Intermediate 1-61 ethyl 7-[3-({4-[4-(tert-butoxycarbonyl) piperazin-1-yl]phenoxy}methyl)-5-(6-hydroxyhexyl)-1-methyl-1H-pyrazol-4-yl]-3-[3-(naphthalen-1-yloxy)propyl]-1H-indole-2-carboxylate

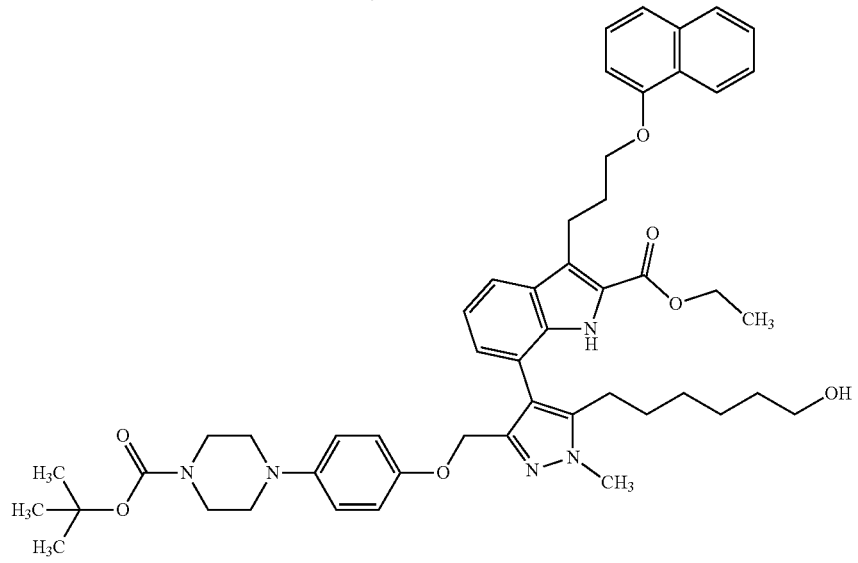

An autoclave was charged with ethyl 7-{3-({4-[4-(tert-butoxycarbonyl)piperazin-1-yl]phenoxy}methyl)-5-[6-hydroxyhex-1-en-1-yl]-1-methyl-1H-pyrazol-4-yl}-3-[3-(naphthalen-1-yloxy)propyl]-1H-indole-2-carboxylate mixture of E/Z-isomers (1.20 g, 1.43 mmol), ethanol (30 ml, 520 mmol) and palladium 10% on charcoal (100 mg, 10 wt-% Pd) and the mixture was stirred at room temperature under 1 atmosphere hydrogen for 1 h, followed by 4 h at 15 bar hydrogen atmosphere, followed by 20.5 h at 19 bar hydrogen atmosphere. For work-up, the mixture was filtrated through a pad of celite, eluted with tetrahydrofuran and methanol and the combined filtrates were concentrated under reduced pressure to give the title compound (1.15 g, 90% purity, 86% yield), which was directly used in the next step.

LC-MS (Method 2): $R_t$=1.74 min; MS (ESIpos): m/z=844 [M+H]$^+$

Intermediate 1-62 ethyl 7-[5-(6-bromohexyl)-3-({4-[4-(tert-butoxycarbonyl) piperazin-1-yl]phenoxy}methyl)-1-methyl-1H-pyrazol-4-yl]-3-[3-(naphthalen-1-yloxy)propyl]-1H-indole-2-carboxylate

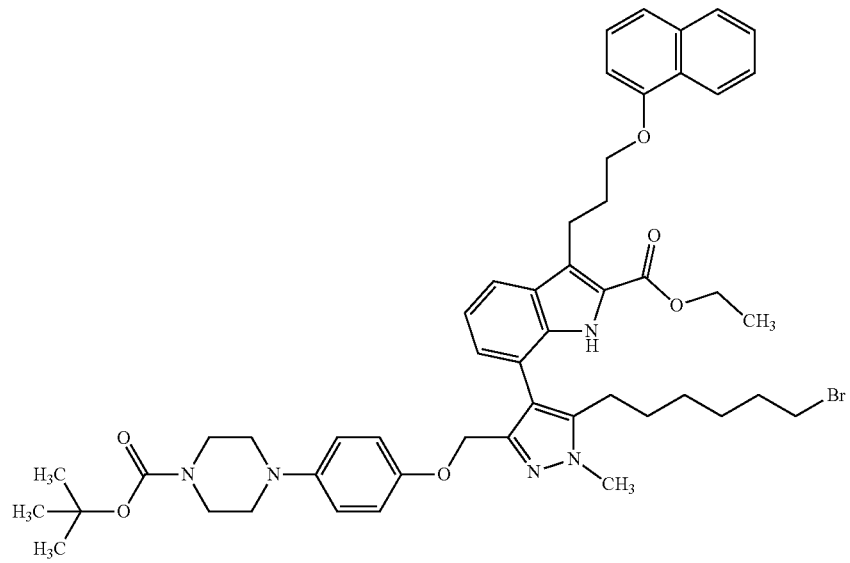

A mixture of ethyl 7-[3-({4-[4-(tert-butoxycarbonyl)piperazin-1-yl]phenoxy}methyl)-5-(6-hydroxyhexyl)-1-methyl-1H-pyrazol-4-yl]-3-[3-(naphthalen-1-yloxy)propyl]-1H-indole-2-carboxylate (1.02 g, 1.20 mmol) and triphenylphosphine (758 mg, 2.89 mmol) in dichloromethane (22 ml) was stirred for 10 min at 0° C. Tetrabromomethane (878 mg, 2.65 mmol) was then added and the mixture was stirred for 2 h at room temperature. For work-up the reaction mixture was concentrated and the residue was purified by flash chromatography (Biotage SNAP cartridge silica, hexanes/ethyl acetate gradient) to give the title compound (1.07 g) as a mixture with triphenylphosphine oxide which was used in the next step without further purification.

LC-MS (Method 1): $R_t$=1.89 min; MS (ESIpos): m/z=806 [M+H]$^+$

Intermediate 1-63

(rac)-ethyl 3-({4-[4-(tert-butoxycarbonyl)piperazin-1-yl]phenoxy}methyl)-1-methyl-7-[3-(naphthalen-1-yloxy)propyl]-10,11,12,13,14,15-hexahydro-1H-pyrazolo[4',3':4,5]azacycloundecino[3,2,1-hi]indole-8-carboxylate A mixture of ethyl 7-[5-(6-bromohexyl)-3-({4-[4-(tert-butoxycarbonyl)piperazin-1-yl]phenoxy}methyl)-1-methyl-1H-pyrazol-4-yl]-3-[3-(naphthalen-1-yloxy)propyl]-1H-indole-2-carboxylate (705 mg, crude product) and potassium tert-butoxide (620 μl, 1.0 M in THF, 620 μmol) in 1,4-dioxane (35 ml) was stirred for 6 h at 80° C. For work-up, the mixture was poured into ice-water, extracted with ethyl acetate and the combined organic phases were filtrated through a silicone filter and concentrated. The residue was purified by flash chromatography (Biotage SNAP cartridge silica, hexanes/ethyl acetate gradient, 50%→100% ethyl acetate) to give the title compound (112 mg), which contains impurities and was used in the next step without further purification.

LC-MS (Method 1): Rt=1.89 min, MS (ESIpos): m/z=826 [M+H]$^+$

Intermediate 1-64

(rac)-ethyl 1-methyl-7-[3-(naphthalen-1-yloxy)propyl]-3-{[4-(piperazin-1-yl)phenoxy]methyl}-10,11,12,13,14,15-hexahydro-1H-pyrazolo[4',3':4,5]azacycloundecino[3,2,1-hi]indole-8-carboxylate hydrochloric acid salt

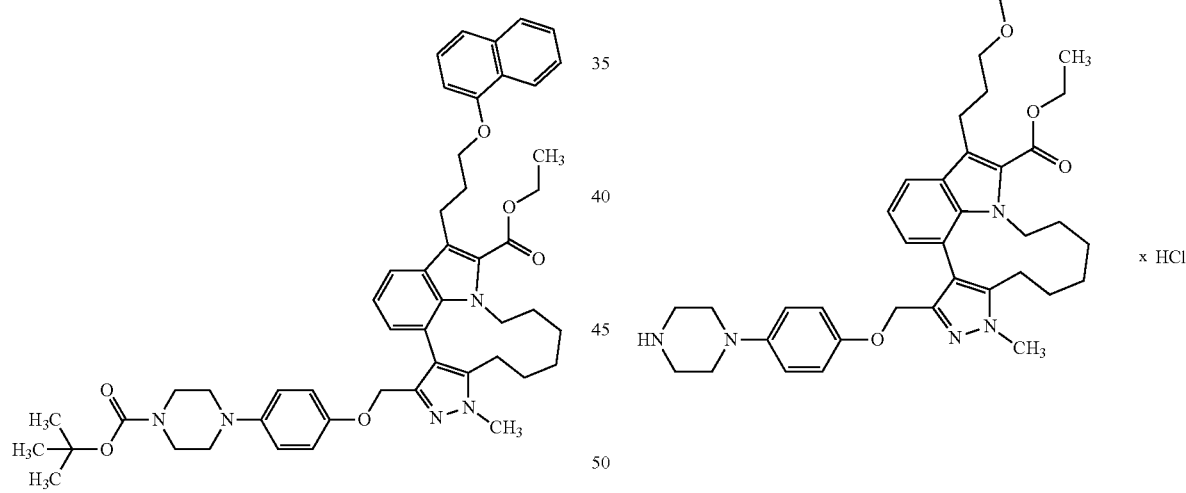

Hydrochloric acid (1.1 ml, 4.0 M in dioxane, 4.5 mmol) was added to a solution of (rac)-ethyl 3-({4-[4-(tert-butoxycarbonyl)piperazin-1-yl]phenoxy}methyl)-1-methyl-7-[3-(naphthalen-1-yloxy)propyl]-10,11,12,13,14,15-hexahydro-1H-pyrazolo[4',3':4,5]azacycloundecino[3,2,1-hi]indole-8-carboxylate (185 mg) in ethanol (3.6 ml) and the mixture was stirred for 16 h at room temperature. For work-up, the reaction mixture was concentrated to give the title compound (200 mg) which was used in the next step without further purification.

Intermediate 1-65

(rac)-ethyl 3-({4-[4-(dimethylsulfamoyl)piperazin-1-yl]phenoxy}methyl)-1-methyl-7-[3-(naphthalen-1-yloxy)propyl]-10,11,12,13,14,15-hexahydro-1H-pyrazolo[4',3':4,5]azacycloundecino[3,2,1-hi]indole-8-carboxylate

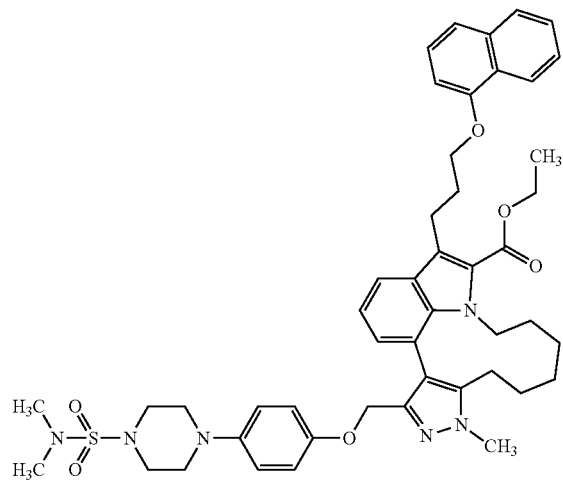 [SMILES: CCOC(=O)c1c(CCCOc2cccc3ccccc23)c2cccc3c2n1CCCCCCc1c-3c(COc2ccc(N3CCN(S(=O)(=O)N(C)C)CC3)cc2)nn1C]

A mixture of (rac)-ethyl 1-methyl-7-[3-(naphthalen-1-yloxy)propyl]-3-{[4-(piperazin-1-yl)phenoxy]methyl}-10,11,12,13,14,15-hexahydro-1H-pyrazolo[4',3':4,5]azacycloundecino[3,2,1-hi]indole-8-carboxylate hydrochloric acid salt (176 mg) and N,N-diisopropylethylamine (190 µl, 1.1 mmol) in dichloromethane (4.0 ml) was stirred for 10 min. Dimethylsulfamyl chloride (35 µl, 330 µmol) was added and the mixture was stirred for 24 h at room temperature. For work-up, the reaction mixture was diluted with dichloromethane and then washed with water and brine. The organic phase was filtrated through a silicone filter and concentrated. The residue was purified by flash chromatography (hexanes/ethyl acetate gradient) to give the title compound (147 mg) together with impurities, which was used in the next step without further purification.

LC-MS (Method 1): R$_t$=1.79 min; MS (ESIpos): m/z=833 [M+H]$^+$

Intermediate 1-66 ethyl 4-bromo-1-methyl-3-(morpholin-4-ylmethyl)-1H-pyrazole-5-carboxylate

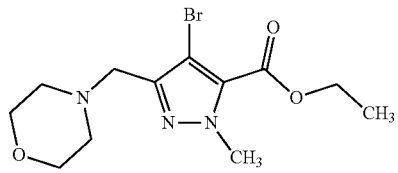 [SMILES: CCOC(=O)c1c(Br)c(CN2CCOCC2)nn1C]

To a solution of morpholine (3.4 ml, 39 mmol) in acetonitrile (77 ml) was added potassium carbonate (5.34 g, 38.7 mmol) and the mixture was stirred for 10 min at room temperature. Ethyl 4-bromo-3-(bromomethyl)-1-methyl-1H-pyrazole-5-carboxylate (see Intermediate 1-5; 6.00 g, 18.4 mmol) was added and the reaction was stirred for 3 hours at room temperature. For work-up, the reaction mixture was poured into sodium chloride solution. The precipitate formed was collected by filtration, washed with water and dried to give the title compound (5.20 g).

LC-MS (Method 2): R$_t$=1.04 min; MS (ESIpos): m/z=332 [M+H]$^+$

Intermediate 1-67

[4-bromo-1-methyl-3-(morpholin-4-ylmethyl)-1H-pyrazol-5-yl]methanol

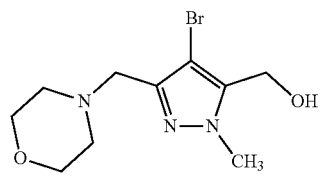 [SMILES: Cn1nc(CN2CCOCC2)c(Br)c1CO]

To a solution of ethyl 4-bromo-1-methyl-3-(morpholin-4-ylmethyl)-1H-pyrazole-5-carboxylate (5.20 g, 15.7 mmol) in THF (120 ml) was added a solution of lithium aluminium hydride in THF (7.8 ml, 2.0 M, 16 mmol) at −10° C. The reaction was stirred at −10° C. for one hour. For work-up, water (0.8 ml) was added dropwise followed by the addition of an aqueous 2 M sodium hydroxide solution (0.8 ml) and water (0.8 ml). The mixture was filtrated through a pad of celite. The residue was washed with ethyl acetate and the filtrate was concentrated under reduced pressure. The resulting precipitate was filtrated and washed with ethyl acetate to give the title compound (4.1 g).

LC-MS (Method 2): Rt=0.66 min; MS (ESIpos): m/z=290 [M+H]$^+$

Intermediate 1-68 ethyl 7-[5-(hydroxymethyl)-1-methyl-3-(morpholin-4-ylmethyl)-1H-pyrazol-4-yl]-3-[3-(naphthalen-1-yloxy)propyl]-1H-indole-2-carboxylate

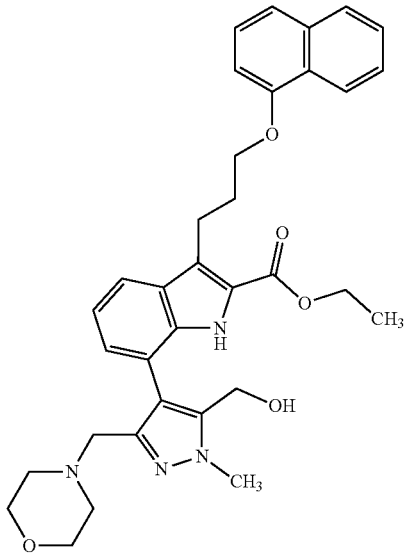

To a solution of ethyl 3-[3-(naphthalen-1-yloxy)propyl]-7-(4,4,5,5-tetramethyl-1,3,2-dioxaborolan-2-yl)-1H-indole-2-carboxylate (see Intermediate 1-4; 4.82 g, 9.65 mmol) and [4-bromo-1-methyl-3-(morpholin-4-ylmethyl)-1H-pyrazol-5-yl]methanol (2.80 g, 9.65 mmol) in 1,4-dioxane (120 ml) were added a 2M solution of potassium carbonate (14 ml, 2.0 M, 29 mmol). The mixture was degassed and purged with argon several times. Pd(dppf)Cl$_2$×CH$_2$Cl$_2$ (1.58 g, 1.93 mmol) was added and the mixture was purged with argon for 10 minutes. The reaction was stirred at 80° C. for 3.5 h. After cooling the reaction was filtrated and the residue was washed with dichloromethane. The filtrate was concentrated under reduced pressure and the residue was purified by flash chromatography (dichloromethane/ethyl acetate gradient, 0%→100% ethyl acetate) to give the title compound (2.84 g).

$^1$H-NMR (400 MHz, DMSO-d6) δ [ppm]: 1.066 (8.09), 1.154 (3.97), 1.171 (7.72), 1.189 (3.62), 1.260 (5.07), 1.278 (11.28), 1.295 (5.18), 1.987 (14.71), 2.235 (1.38), 2.254 (1.08), 2.518 (1.87), 2.522 (1.27), 3.136 (2.94), 3.356 (1.77), 3.375 (1.12), 3.565 (0.87), 3.591 (2.36), 3.602 (3.91), 3.613 (2.30), 3.914 (16.00), 3.938 (1.47), 3.999 (1.06), 4.017 (3.16), 4.034 (3.06), 4.052 (0.97), 4.197 (1.39), 4.212 (2.82), 4.226 (1.42), 4.271 (1.35), 4.289 (1.33), 4.350 (1.64), 4.357 (1.69), 4.361 (1.65), 4.369 (1.04), 5.416 (0.91), 5.428 (2.24), 6.882 (1.65), 6.885 (1.72), 6.901 (1.89), 6.904 (1.77), 7.105 (1.54), 7.123 (2.21), 7.125 (2.00), 7.143 (1.90), 7.244 (2.12), 7.247 (2.30), 7.263 (1.80), 7.265 (1.68), 7.363 (1.37), 7.383 (2.58), 7.402 (2.19), 7.440 (2.58), 7.454 (0.90), 7.461 (1.50), 7.468 (1.49), 7.471 (1.67), 7.488 (1.55), 7.492 (1.39), 7.497 (1.41), 7.501 (1.58), 7.514 (0.82), 7.517 (1.59), 7.521 (1.59), 7.534 (0.86), 7.538 (0.72), 7.719 (1.77), 7.737 (1.66), 7.851 (1.53), 7.853 (1.67), 7.871 (1.61), 7.874 (1.40), 8.147 (1.47), 8.149 (1.54), 8.151 (1.48), 8.168 (1.35), 8.169 (1.44), 8.171 (1.36), 11.340 (2.54).

Intermediate 1-69 ethyl 1-{3-[(tert-butoxycarbonyl)(methyl)amino]propyl}-7-[5-(hydroxymethyl)-1-methyl-3-(morpholin-4-ylmethyl)-1H-pyrazol-4-yl]-3-[3-(naphthalen-1-yloxy)propyl]-1H-indole-2-carboxylate

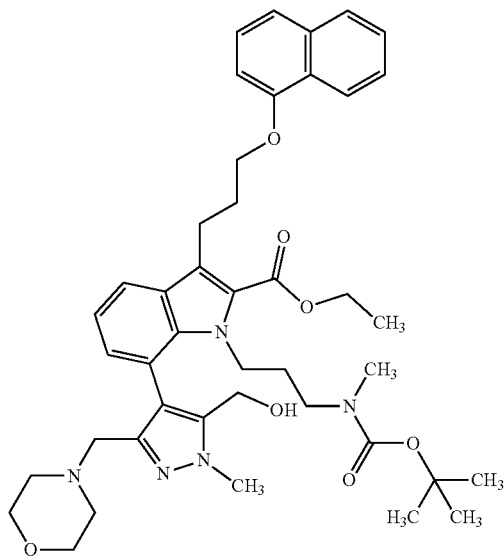 [SMILES: CCOC(=O)c1c(CCCOc2cccc3ccccc23)c2cccc(-c3c(CN4CCOCC4)nn(C)c3CO)c2n1CCCN(C)C(=O)OC(C)(C)C]

To a solution of ethyl 7-[5-(hydroxymethyl)-1-methyl-3-(morpholin-4-ylmethyl)-1H-pyrazol-4-yl]-3-[3-(naphthalen-1-yloxy)propyl]-1H-indole-2-carboxylate (2.00 g, 3.43 mmol) in DMF (45 ml) was added caesium carbonate (5.59 g, 17.2 mmol) and the mixture was stirred for 10 min at room temperature. Tert-butyl (3-bromopropyl)methylcarbamate (see Intermediate 1-1; 1.04 g, 4.12 mmol) was added and the reaction was stirred for 3 days at room temperature. For work-up, the reaction mixture was filtrated and the filtrate was concentrated under reduced pressure. The residue was purified by flash chromatography (dichloromethane/methanol gradient, 0%→5% methanol) to give the title compound (1.6 g).

Intermediate 1-70 ethyl 7-[5-(bromomethyl)-1-methyl-3-(morpholin-4-ylmethyl)-1H-pyrazol-4-yl]-1-{3-[(tert-butoxycarbonyl)(methyl)amino]propyl}-3-[3-(naphthalen-1-yloxy)propyl]-1H-indole-2-carboxylate

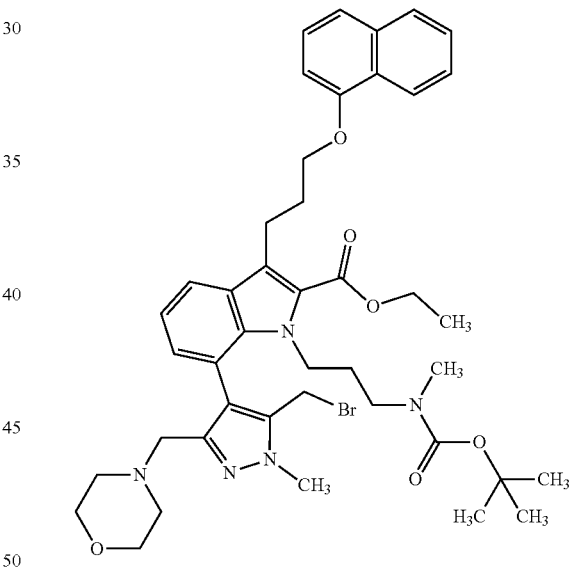

To a solution of ethyl 1-{3-[(tert-butoxycarbonyl)(methyl)amino]propyl}-7-[5-(hydroxymethyl)-1-methyl-3-(morpholin-4-ylmethyl)-1H-pyrazol-4-yl]-3-[3-(naphthalen-1-yloxy)propyl]-1H-indole-2-carboxylate (1.60 g, 2.12 mmol) in dichloromethane (41 ml), triphenylphosphine (835 mg, 3.18 mmol) was added at 0° C. and the mixture was stirred at 0° C. for 10 min. Tetrabromomethane (1.06 g, 3.18 mmol) was added and the reaction was stirred at 0° C. for 2 hours. For work-up, the reaction mixture was concentrated under reduced pressure and the crude product was purified by flash chromatography (dichloromethane/methanol gradient, 2%→5% methanol) to give the title compound (1.44 g).

Intermediate 1-71 ethyl 7-[5-(bromomethyl)-1-methyl-3-(morpholin-4-ylmethyl)-1H-pyrazol-4-yl]-1-[3-(methylamino)propyl]-3-[3-(naphthalen-1-yloxy)propyl]-1H-indole-2-carboxylate hydrochloric acid salt

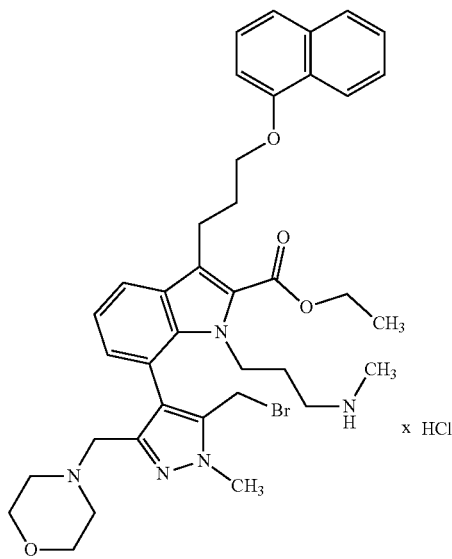

To a solution of ethyl 7-[5-(bromomethyl)-1-methyl-3-(morpholin-4-ylmethyl)-1H-pyrazol-4-yl]-1-{3-[(tert-butoxycarbonyl)(methyl)amino]propyl}-3-[3-(naphthalen-1-yloxy)propyl]-1H-indole-2-carboxylate (1.44 g, 1.76 mmol) in methanol (33 ml) was added a 4 M solution of HCl in dioxan (33 ml, 4.0 M, 130 mmol) at 0° C. and the mixture was stirred for 3 h at room temperature. For work-up the mixture was concentrated under reduced pressure and the crude product was used for the subsequent steps without further purification.

Intermediate 1-72

(rac)-ethyl 7,9-dimethyl-11-(morpholin-4-ylmethyl)-1-[3-(naphthalen-1-yloxy)propyl]-4,5,6,7,8,9-hexahydropyrazolo[3',4':7,8][1,5]diazecino[9,10,1-hi]indole-2-carboxylate

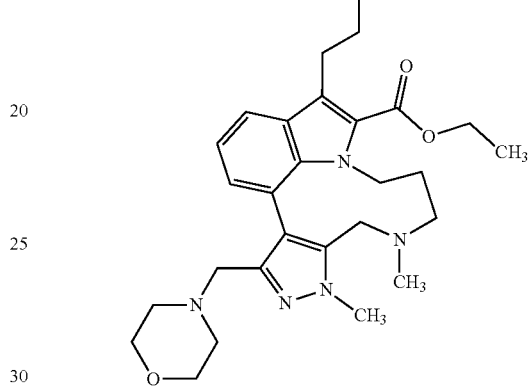

To a solution of ethyl 7-[5-(bromomethyl)-1-methyl-3-(morpholin-4-ylmethyl)-1H-pyrazol-4-yl]-1-[3-(methylamino)propyl]-3-[3-(naphthalen-1-yloxy)propyl]-1H-indole-2-carboxylate hydrochloric acid salt (849 mg) in DMF (99 ml) was added caesium carbonate (1.84 g, 5.64 mmol) and the reaction was stirred at 65° C. for 2 hours. For work-up, the mixture was concentrated under reduced pressure, water and ethyl acetate were added to the residue and the aqueous phase was extracted with ethyl acetate. The combined organic phases were filtrated through a silicone filter and concentrated. The residue was purified by flash chromatography (dichloromethane/methanol gradient, 0%→10% methanol) to give the title compound (447 mg).
LC-MS (Method 2): Rt=1.74 min; MS (ESIpos): m/z=636.5 [M+H]$^+$ $^1$H-NMR (400 MHz, DMSO-d6) δ [ppm]: 1.252 (5.00), 1.270 (10.90), 1.288 (5.22), 1.484 (1.47), 2.006 (0.98), 2.024 (1.34), 2.040 (1.30), 2.047 (1.14), 2.159 (1.54), 2.177 (2.06), 2.195 (2.15), 2.224 (13.20), 2.322 (1.21), 2.327 (1.31), 2.331 (0.89), 2.523 (3.80), 2.669 (0.80), 3.013 (1.72), 3.030 (2.02), 3.049 (1.94), 3.062 (2.85), 3.172 (3.60), 3.205 (3.64), 3.211 (2.04), 3.227 (1.89), 3.243 (1.31), 3.257 (1.05), 3.277 (1.16), 3.349 (1.31), 3.382 (0.75), 3.610 (1.85), 3.646 (1.66), 3.739 (0.78), 3.836 (16.00), 4.148 (1.25), 4.162 (2.47), 4.179 (1.34), 4.190 (1.04), 4.200 (0.71), 4.208 (0.86), 4.217 (2.00), 4.221 (0.99), 4.235 (2.20), 4.239 (2.16), 4.253 (0.94), 4.257 (1.97), 4.266 (0.78), 4.284 (0.71), 4.406 (0.93), 4.442 (0.86), 5.759 (0.64), 6.837 (1.97), 6.856 (2.18), 6.929 (1.53), 6.932 (1.64), 6.947 (2.61), 6.950 (2.36), 6.990 (2.20), 7.010 (2.40), 7.027 (1.38), 7.351 (1.44), 7.372 (2.67), 7.391 (2.11), 7.442 (2.80), 7.463 (1.72), 7.497 (0.59), 7.509 (1.76), 7.514 (2.90), 7.524 (3.64), 7.533 (3.20), 7.538 (1.97), 7.550 (0.69), 7.701 (1.93), 7.704 (2.02), 7.721 (1.90), 7.724 (1.77), 7.857 (1.68), 7.861 (1.23), 7.867 (0.87), 7.875 (1.12), 7.880 (1.44), 8.223 (1.40), 8.230 (1.13), 8.247 (1.34).

Intermediate 1-73 ethyl 4-bromo-1-methyl-3-({4-[4-(methylsulfonyl)piperazin-1-yl]phenoxy}methyl)-1H-pyrazole-5-carboxylate

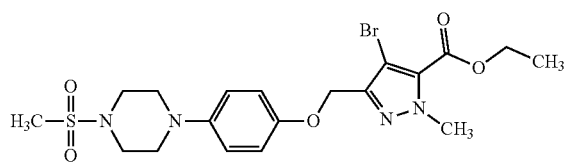 [SMILES: CCOC(=O)c1c(Br)c(COc2ccc(N3CCN(S(C)(=O)=O)CC3)cc2)nn1C]

To a solution of ethyl 4-bromo-1-methyl-3-{[4-(piperazin-1-yl)phenoxy]methyl}-1H-pyrazole-5-carboxylate hydrochloric acid salt (see Intermediate 1-20; 7.10 g) in dichloromethane (300 ml) was added N,N-diisopropylethylamine (15 ml, 100% purity, 84 mmol) at 0° C. and the mixture was stirred for 10 min. Methanesulfonyl chloride (1.6 ml, 20 mmol) was added and the reaction was stirred for 3 hours at 0° C. For work-up dichloromethane was added and the organic phase was washed with water and brine. The organic phase was dried over sodium sulfate. After filtration the solvents were removed under reduced pressure and the crude product (7.76 g) was used for subsequent steps without further purification.

LC-MS (Method 2): Rt=1.23 min; MS (ESIpos): m/z=501 [M+H]$^+$

Intermediate 1-74

[4-bromo-1-methyl-3-({4-[4-(methylsulfonyl)piperazin-1-yl]phenoxy}methyl)-1H-pyrazol-5-yl]methanol

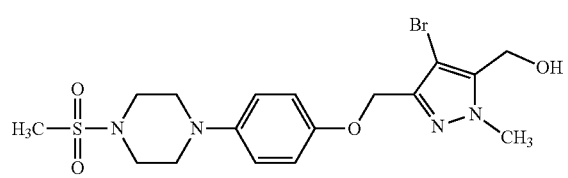 [SMILES: Cn1nc(COc2ccc(N3CCN(S(C)(=O)=O)CC3)cc2)c(Br)c1CO]

To a solution of ethyl 4-bromo-1-methyl-3-({4-[4-(methylsulfonyl)piperazin-1-yl]phenoxy}methyl)-1H-pyrazole-5-carboxylate (7.76 g, 15.5 mmol) in THF (200 ml) at 0° C. was added the solution of lithium aluminium hydride (7.7 ml, 2.0 M, 15 mmol) and the mixture was stirred at 0° C. for 2 hours. Ice was carefully added and the mixture was stirred for 30 minutes. A solution of sodium potassium tartrate was added and the mixture was poured into water. The mixture was extracted with dichloromethane/methanol (9:1), and the combined organic layers were washed with brine and dried over sodium sulfate. After filtration and removal of the solvents the crude product (6.74 g) was used without further purification in the subsequent steps.

LC-MS (Method 2): Rt=0.80 min; MS (ESIpos): m/z=459 [M+H]$^+$

Intermediate 1-75 ethyl 7-[5-(hydroxymethyl)-1-methyl-3-({4-[4-(methylsulfonyl)piperazin-1-yl]phenoxy}methyl)-1H-pyrazol-4-yl]-3-[3-(naphthalen-1-yloxy)propyl]-1H-indole-2-carboxylate

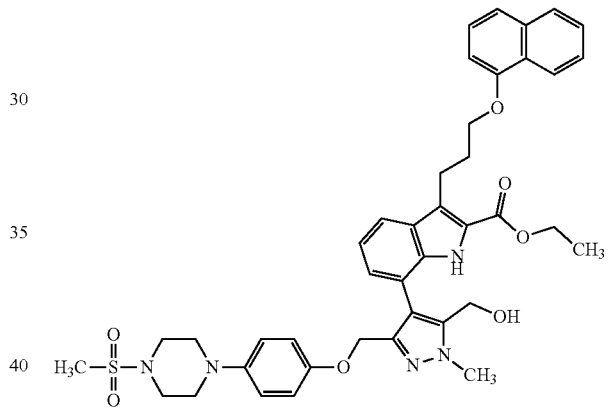

To a solution of ethyl 3-[3-(naphthalen-1-yloxy)propyl]-7-(4,4,5,5-tetramethyl-1,3,2-dioxaborolan-2-yl)-1H-indole-2-carboxylate (see Intermediate 1-4; 7.33 g, 14.7 mmol) and [4-bromo-1-methyl-3-({4-[4-(methylsulfonyl)piperazin-1-yl]phenoxy}methyl)-1H-pyrazol-5-yl]methanol (6.74 g, 14.7 mmol) in 1,4-dioxane (190 ml) were added a 2M solution of potassium carbonate (22 ml, 2.0 M, 44 mmol). The mixture was degassed and purged with argon several times. Pd(dppf)Cl$_2$×CH$_2$Cl$_2$ (2.40 g, 2.93 mmol) was added and the mixture was purged with argon for 10 minutes. The reaction was stirred at 80° C. for 6 h. For work-up the mixture was concentrated under reduced pressure and the residue was purified by flash chromatography (dichloromethane/methanol gradient, 0%→100% methanol) to give the title compound (8.92 g).

LC-MS (Method 2): Rt=1.50 min; MS (ESIpos): m/z=752 [M+H]$^+$

Intermediate 1-76 ethyl 1-{3-[(tert-butoxycarbonyl)(methyl)amino]propyl}-7-[5-(hydroxymethyl)-1-methyl-3-({4-[4-(methylsulfonyl)piperazin-1-yl]phenoxy}methyl)-1H-pyrazol-4-yl]-3-[3-(naphthalen-1-yloxy)propyl]-1H-indole-2-carboxylate

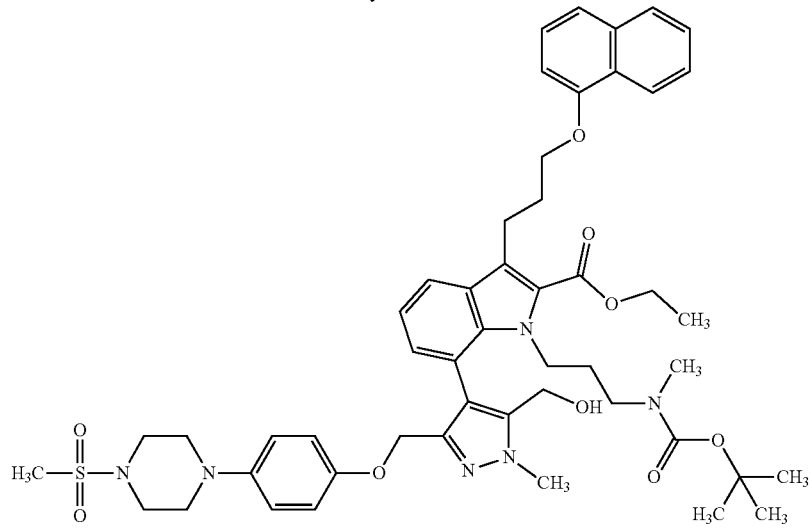

To a solution of ethyl 7-[5-(hydroxymethyl)-1-methyl-3-({4-[4-(methylsulfonyl)piperazin-1-yl]phenoxy}methyl)-1H-pyrazol-4-yl]-3-[3-(naphthalen-1-yloxy)propyl]-1H-indole-2-carboxylate (3.00 g, 3.99 mmol) in DMF (52 ml) was added caesium carbonate (6.50 g, 19.9 mmol) and the mixture was stirred for 10 min at room temperature. Tert-butyl (3-bromopropyl)methylcarbamate (see Intermediate 1-1; 1.21 g, 4.79 mmol) was added and the reaction was stirred for 3 days at room temperature. For work-up, the reaction mixture was concentrated under reduced pressure. The residue was purified by flash chromatography (dichloromethane/methanol gradient, 0%→10% methanol) to give the title compound (1.65 g).

LC-MS (Method 2): Rt=1.59 min; MS (ESIpos): m/z=923 [M+H]$^+$

Intermediate 1-77 ethyl 7-[5-(bromomethyl)-1-methyl-3-({4-[4-(methylsulfonyl)piperazin-1-yl]phenoxy}methyl)-1H-pyrazol-4-yl]-1-{3-[(tert-butoxycarbonyl)(methyl)amino]propyl}-3-[3-(naphthalen-1-yloxy)propyl]-1H-indole-2-carboxylate

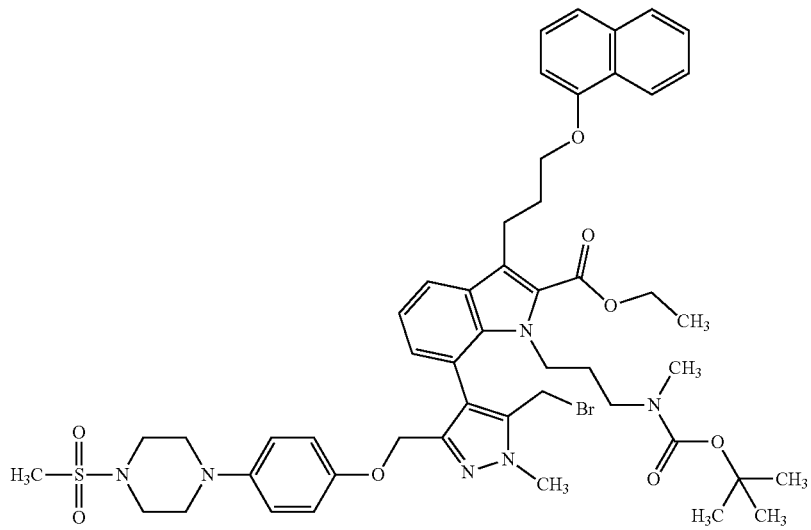 [SMILES: CCOC(=O)c1c(CCCOc2cccc3ccccc23)c2cccc(-c3c(COc4ccc(N5CCN(S(C)(=O)=O)CC5)cc4)nn(C)c3CBr)c2n1CCCN(C)C(=O)OC(C)(C)C]

To a solution of ethyl 1-{3-[(tert-butoxycarbonyl)(methyl)amino]propyl}-7-[5-(hydroxymethyl)-1-methyl-3-({4-[4-(methylsulfonyl)piperazin-1-yl]phenoxy}methyl)-1H-pyrazol-4-yl]-3-[3-(naphthalen-1-yloxy)propyl]-1H-indole-2-carboxylate (1.60 g, 1.73 mmol) in dichloromethane (32 ml) triphenylphosphine (682 mg, 2.60 mmol) was added at 0° C. and the mixture was stirred at 0° C. for 10 min. Tetrabromomethane (862 mg, 2.60 mmol) was added and the reaction was stirred at 0° C. for 2 hours. For work-up, the reaction mixture was concentrated under reduced pressure and the crude product was purified by flash chromatography (dichloromethane/methanol gradient, 2%→5% methanol) to give the title compound (1.5 g).

LC-MS (Method 1): Rt=1.78 min; MS (ESIpos): m/z=986 [M+H]$^+$

Intermediate 1-78 ethyl 7-[5-(bromomethyl)-1-methyl-3-({4-[4-(methylsulfonyl)piperazin-1-yl]phenoxy}methyl)-1H-pyrazol-4-yl]-1-[3-(methylamino)propyl]-3-[3-(naphthalen-1-yloxy)propyl]-1H-indole-2-carboxylate hydrochloric acid salt

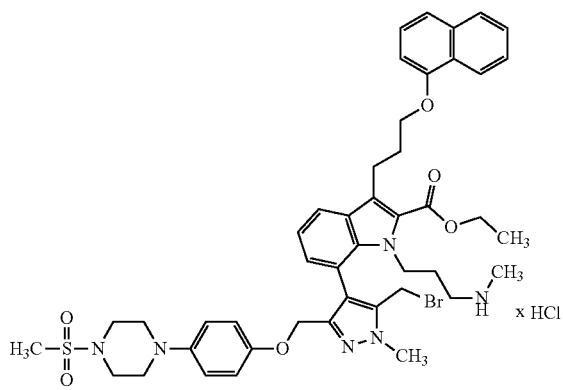

To a solution of ethyl 7-[5-(bromomethyl)-1-methyl-3-({4-[4-(methylsulfonyl)piperazin-1-yl]phenoxy}methyl)-1H-pyrazol-4-yl]-1-{3-[(tert-butoxycarbonyl)(methyl)amino]propyl}-3-[3-(naphthalen-1-yloxy)propyl]-1H-indole-2-carboxylate (1.50 g, 1.52 mmol) in methanol (28 ml) was added a 4 M solution of HCl in dioxan (29 ml, 4.0 M, 110 mmol) at 0° C., and the mixture was stirred for 5 hours at room temperature. For work-up, the mixture was concentrated under reduced pressure and the crude product was used for the subsequent steps without further purification.

Intermediate 1-79

(rac)-ethyl 7,9-dimethyl-11-({4-[4-(methylsulfonyl)piperazin-1-yl]phenoxy}methyl)-1-[3-(naphthalen-1-yloxy)propyl]-4,5,6,7,8,9-hexahydropyrazolo[3',4':7,8][1,5]diazecino[9,10,1-hi]indole-2-carboxylate

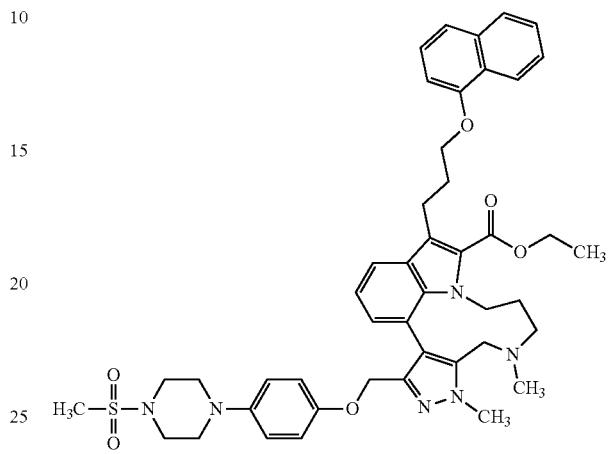

To a solution of ethyl 7-[5-(bromomethyl)-1-methyl-3-({4-[4-(methylsulfonyl)piperazin-1-yl]phenoxy}methyl)-1H-pyrazol-4-yl]-1-[3-(methylamino)propyl]-3-[3-(naphthalen-1-yloxy)propyl]-1H-indole-2-carboxylate hydrochloric acid salt (1.60 g) in DMF (160 ml) was added caesium carbonate (2.83 g, 8.67 mmol) and the reaction was stirred at 65° C. for 4 hours and for 16 hours at room temperature. For work-up, the mixture was poured into water and sodium chloride was added. The mixture was stirred for 10 minutes. The resulting precipitate was collected via filtration and the residue was washed with water. The residue was purified by flash chromatography (dichloromethane/methanol gradient, 0%→10% methanol) to give the title compound (990 mg).

LC-MS (Method 2): Rt=1.69 min; MS (ESIpos): m/z=805 [M+H]$^+$

Intermediate 1-80 ethyl 4-bromo-1-methyl-3-{[4-(methylsulfonyl)phenoxy]methyl}-1H-pyrazole-5-carboxylate

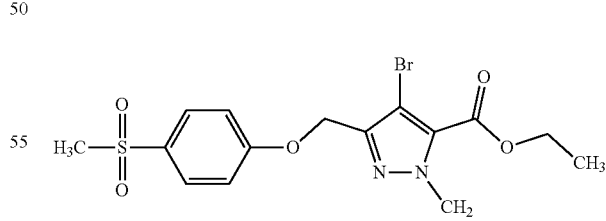

To a solution of 4-(methylsulfonyl)phenol (2.03 g, 11.8 mmol) in DMF (35 ml) was added potassium carbonate (4.65 g, 33.7 mmol) and the mixture was stirred for 10 min at room temperature. Ethyl 4-bromo-3-(bromomethyl)-1-methyl-1H-pyrazole-5-carboxylate (see Intermediate 1-5; 3.66 g, 11.2 mmol) was added and the reaction was stirred for 2 hours at room temperature. For work-up, the reaction mixture was poured into an aqueous sodium chloride solution. The resulting precipitate was collected via filtration and the filtrate was washed with water to give the title compound (4.8 g), which was used in the subsequent steps without further purification.

LC-MS (Method 1): Rt=1.10 min; MS (ESIpos): m/z=417 [M+H]$^+$

Intermediate 1-81

(4-bromo-1-methyl-3-{[4-(methylsulfonyl)phenoxy]methyl}-1H-pyrazol-5-yl)methanol Intermediate 1-82 ethyl 7-[5-(hydroxymethyl)-1-methyl-3-{[4-(methylsulfonyl)phenoxy]methyl}-1H-pyrazol-4-yl]-3-[3-(naphthalen-1-yloxy)propyl]-1H-indole-2-carboxylate

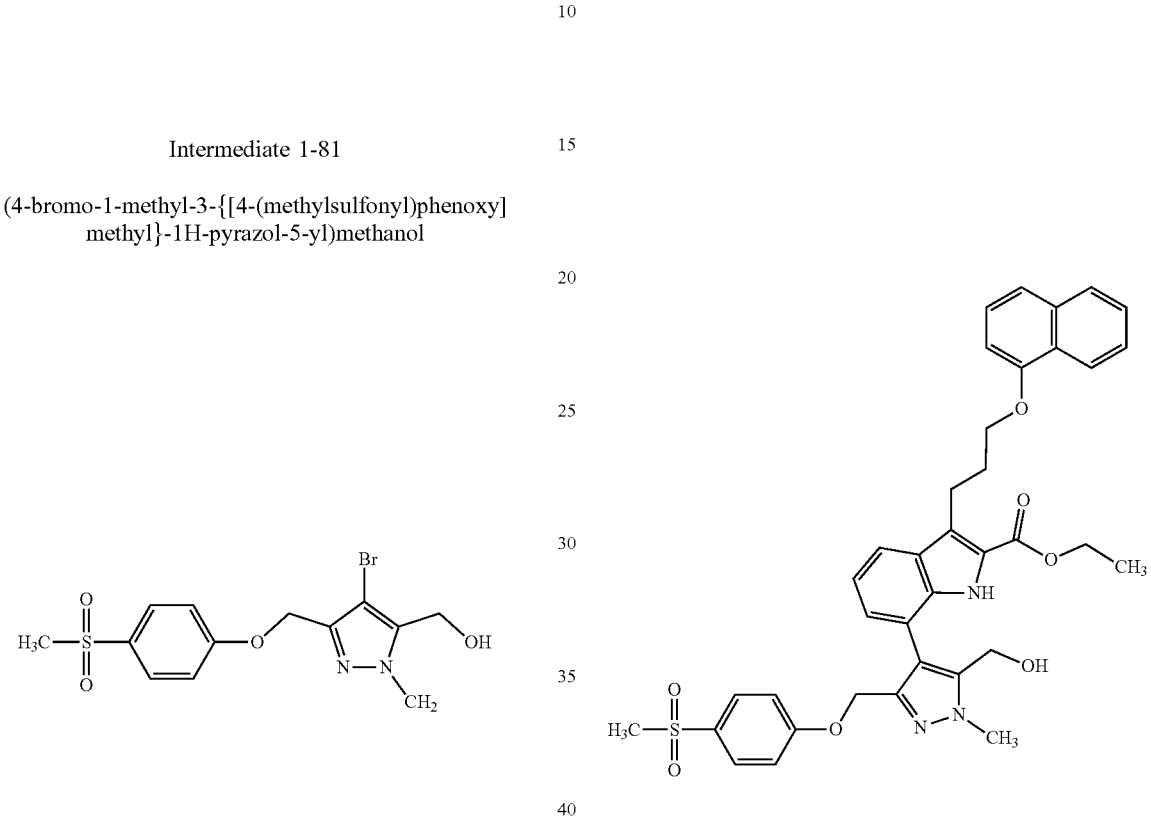

To a solution of ethyl 4-bromo-1-methyl-3-{[4-(methylsulfonyl)phenoxy]methyl}-1H-pyrazole-5-carboxylate (4.75 g, 11.4 mmol) in THF (84 ml) at 0° C. was added the solution of lithium aluminium hydride (5.7 ml, 2.0 M, 11 mmol) and the mixture was stirred at 0° C. for 30 min. For work-up, water (1.0 ml) was added dropwise, followed by the addition of an aqueous 2 M sodium hydroxide solution (1.0 ml), and again water (1.0 ml). The mixture was filtrated through a pad of celite. The residue was washed with ethyl acetate and the filtrate was concentrated under reduced pressure. The resulting precipitate was filtrated and washed with ethyl acetate to give the title compound (3.3 g, contains 9% of a debrominated side product).

LC-MS (Method 1): Rt=0.78 min; MS (ESIpos): m/z=375 [M+H]$^+$ $^1$H-NMR (400 MHz, DMSO-d6) δ [ppm]: 1.988 (0.60), 3.154 (1.77), 3.164 (16.00), 3.333 (8.88), 3.772 (1.82), 4.480 (4.29), 4.494 (4.36), 5.074 (7.63), 5.082 (0.94), 5.416 (1.34), 5.430 (3.28), 5.444 (1.19), 7.246 (3.95), 7.252 (1.15), 7.263 (1.14), 7.269 (4.39), 7.835 (4.74), 7.840 (1.37), 7.852 (1.16), 7.858 (4.07).

To a solution of ethyl 3-[3-(naphthalen-1-yloxy)propyl]-7-(4,4,5,5-tetramethyl-1,3,2-dioxaborolan-2-yl)-1H-indole-2-carboxylate (see Intermediate 1-4; 4.43 g, 100% purity, 8.87 mmol) and (4-bromo-1-methyl-3-{[4-(methylsulfonyl)phenoxy]methyl}-1H-pyrazol-5-yl)methanol (3.33 g, 8.87 mmol) in 1,4-dioxane (110 ml) were added an aqueous 2 M solution of potassium carbonate (13 ml, 2.0 M, 27 mmol). The mixture was degassed and purged with argon several times. Pd(dppf)Cl$_2$×CH$_2$Cl$_2$ (1.45 g, 1.77 mmol) was added and the mixture was purged with argon for 10 minutes. The reaction was stirred at 80° C. for 3.5 h. For work-up, the reaction mixture was concentrated under reduced pressure and the residue was purified by flash chromatography (dichloromethane/ethyl acetate gradient, 0%→100% ethyl acetate) to give the title compound (4.2 g).

LC-MS (Method 2): Rt=1.47 min; MS (ESIpos): m/z=668 [M+H]$^+$

Intermediate 1-83 ethyl 1-{3-[(tert-butoxycarbonyl)(methyl)amino]propyl}-7-[5-(hydroxymethyl)-1-methyl-3-{[4-(methylsulfonyl)phenoxy]methyl}-1H-pyrazol-4-yl]-3-[3-(naphthalen-1-yloxy)propyl]-1H-indole-2-carboxylate

Intermediate 1-84 ethyl 7-[5-(bromomethyl)-1-methyl-3-{[4-(methylsulfonyl)phenoxy]methyl}-1H-pyrazol-4-yl]-1-{3-[(tert-butoxycarbonyl)(methyl)amino]propyl}-3-[3-(naphthalen-1-yloxy)propyl]-1H-indole-2-carboxylate

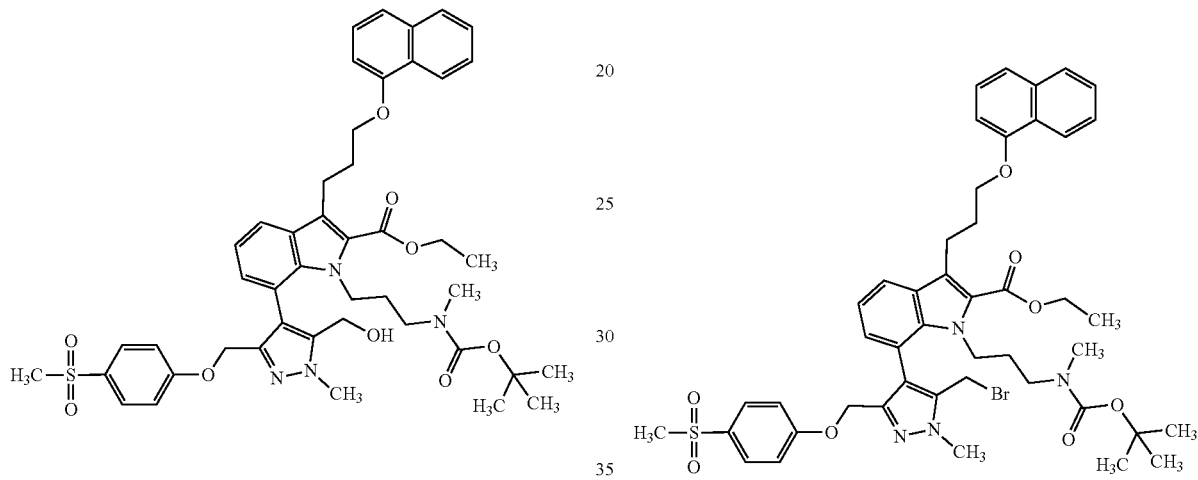

To a solution of ethyl 7-[5-(hydroxymethyl)-1-methyl-3-{[4-(methylsulfonyl)phenoxy]methyl}-1H-pyrazol-4-yl]-3-[3-(naphthalen-1-yloxy)propyl]-1H-indole-2-carboxylate (1.30 g, 1.95 mmol) in DMF (25 ml) was added caesium carbonate (3.17 g, 9.73 mmol) and the mixture was stirred for 10 min at room temperature. Tert-butyl (3-bromopropyl)methylcarbamate (see Intermediate 1-1, 589 mg, 2.34 mmol) was added and the reaction was stirred for 3 days at room temperature and 4 hours at 50° C. For work-up, the reaction mixture was filtrated and the filtrate was concentrated under reduced pressure. The residue was purified twice by flash chromatography (dichloromethane/methanol gradient, 0%→5% methanol followed by dichloromethane/ethyl acetate gradient 0→100% ethyl acetate) to give the title compound (1.0 g).

To a solution of ethyl 1-{3-[(tert-butoxycarbonyl)(methyl)amino]propyl}-7-[5-(hydroxymethyl)-1-methyl-3-{[4-(methylsulfonyl)phenoxy]methyl}-1H-pyrazol-4-yl]-3-[3-(naphthalen-1-yloxy)propyl]-1H-indole-2-carboxylate (1.00 g, 1.19 mmol) in dichloromethane (22 ml) was added triphenylphosphine (750 mg, 2.86 mmol) at 0° C., and the mixture was stirred at 0° C. for 10 min. Tetrabromomethane (870 mg, 2.62 mmol) was added, and the reaction was stirred at 0° C. for 90 minutes. For work-up, the reaction mixture was concentrated under reduced pressure and the crude product was purified by flash chromatography (dichloromethane/methanol gradient, 0%→10% methanol) to give the title compound (1.44 g).

Intermediate 1-85 ethyl 7-[5-(bromomethyl)-1-methyl-3-{[4-(methyl-sulfonyl)phenoxy]methyl}-1H-pyrazol-4-yl]-1-[3-(methylamino)propyl]-3-[3-(naphthalen-1-yloxy)propyl]-1H-indole-2-carboxylate hydrochloric acid salt

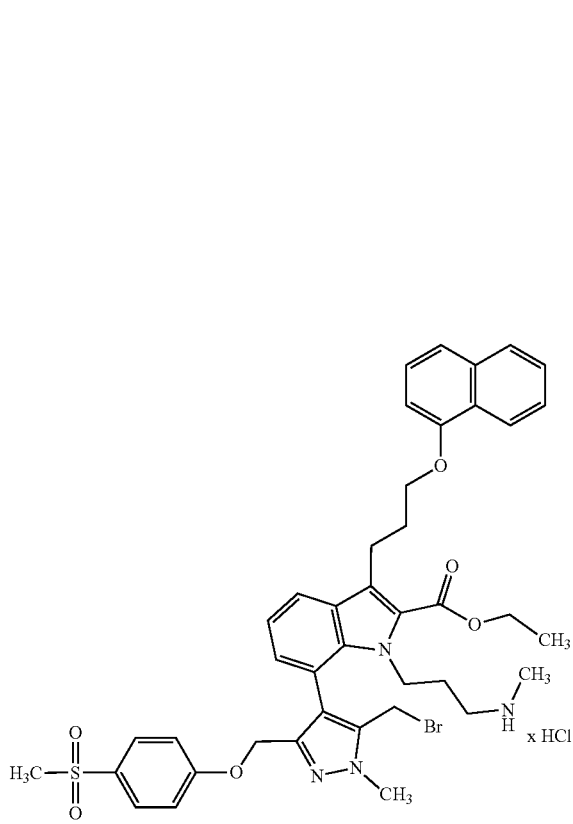 [SMILES: CCOC(=O)c1c(CCCOc2cccc3ccccc23)c2cccc(-c3c(COc4ccc(S(C)(=O)=O)cc4)nn(C)c3CBr)c2n1CCCNC]

To a solution of ethyl 7-[5-(bromomethyl)-1-methyl-3-{[4-(methylsulfonyl)phenoxy]methyl}-1H-pyrazol-4-yl]-1-{3-[(tert-butoxycarbonyl)(methyl)amino]propyl}-3-[3-(naphthalen-1-yloxy)propyl]-1H-indole-2-carboxylate (1.08 g, 1.19 mmol) in methanol (22 ml) was added a 4 M solution of HCl in dioxan (22 ml, 4.0 M, 86 mmol) at 0° C. and the mixture was stirred for 1 h at room temperature. For work-up the mixture was concentrated under reduced pressure and the crude product was used for the subsequent steps without further purification.

Intermediate 1-86

(rac)-ethyl 7,9-dimethyl-11-{[4-(methylsulfonyl)phenoxy]methyl}-1-[3-(naphthalen-1-yloxy)propyl]-4,5,6,7,8,9-hexahydropyrazolo[3',4':7,8][1,5]diazecino[9,10,1-hi]indole-2-carboxylate

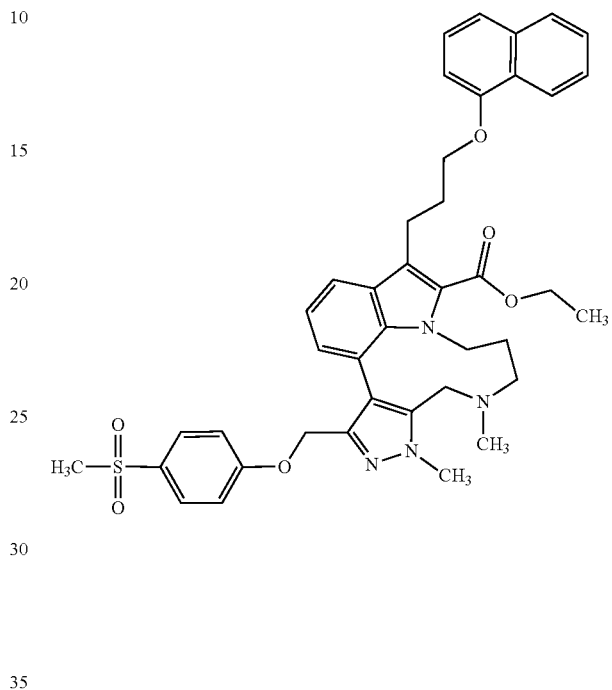

To a solution of ethyl 7-[5-(bromomethyl)-1-methyl-3-{[4-(methylsulfonyl)phenoxy]methyl}-1H-pyrazol-4-yl]-1-[3-(methylamino)propyl]-3-[3-(naphthalen-1-yloxy)propyl]-1H-indole-2-carboxylate hydrochloric acid salt (999 mg) in DMF (100 ml) was added caesium carbonate (1.94 g, 5.96 mmol) and the reaction was stirred at 65° C. for 16 hours. For work-up the mixture was concentrated under reduced pressure and the crude product was purified by flash chromatography (dichloromethane/ethyl acetate gradient, 0%→100% ethyl acetate) to give the title compound (353 mg).

LC-MS (Method 2): Rt=1.70 min; MS (ESIpos): m/z=721 [M+H]$^+$ $^1$H-NMR (400 MHz, DMSO-d6) δ [ppm]: 1.154 (1.70), 1.171 (3.40), 1.189 (1.58), 1.266 (4.05), 1.284 (9.21), 1.301 (4.14), 1.987 (6.00), 2.180 (9.69), 2.518 (2.07), 2.522 (1.44), 3.017 (1.19), 3.053 (1.28), 3.086 (16.00), 3.639 (1.60), 3.675 (1.17), 3.895 (13.32), 4.017 (1.28), 4.034 (1.24), 4.171 (1.83), 4.183 (1.52), 4.202 (0.90), 4.219 (1.26), 4.229 (1.68), 4.247 (1.55), 4.259 (1.65), 4.277 (1.43), 4.287 (0.67), 4.304 (0.67), 4.901 (4.87), 6.842 (4.59), 6.847 (2.47), 6.859 (1.42), 6.865 (5.63), 6.960 (0.89), 6.973 (2.65), 6.978 (4.69), 6.996 (2.28), 7.013 (0.78), 7.350 (1.19), 7.371 (2.11), 7.390 (1.72), 7.440 (2.09), 7.461 (1.26), 7.503 (1.35), 7.508 (1.31), 7.511 (1.66), 7.519 (3.04), 7.527 (1.86), 7.530 (1.47), 7.535 (1.47), 7.547 (0.76), 7.637 (4.83), 7.642 (1.40), 7.654 (1.16), 7.660 (4.20), 7.694 (1.44), 7.699 (1.51), 7.712 (1.30), 7.717 (1.28), 7.856 (1.24), 7.859 (0.93), 7.873 (0.95), 7.879 (1.03), 8.217 (1.09), 8.224 (0.96), 8.239 (0.88), 8.241 (0.98).

Intermediate 1-87 ethyl 7-(1-methyl-3-{[4-(methylsulfonyl)phenoxy]methyl}-5-[(prop-2-en-1-yloxy)methyl]-1H-pyrazol-4-yl)-3-[3-(naphthalen-1-yloxy)propyl]-1-(prop-2-en-1-yl)-1H-indole-2-carboxylate

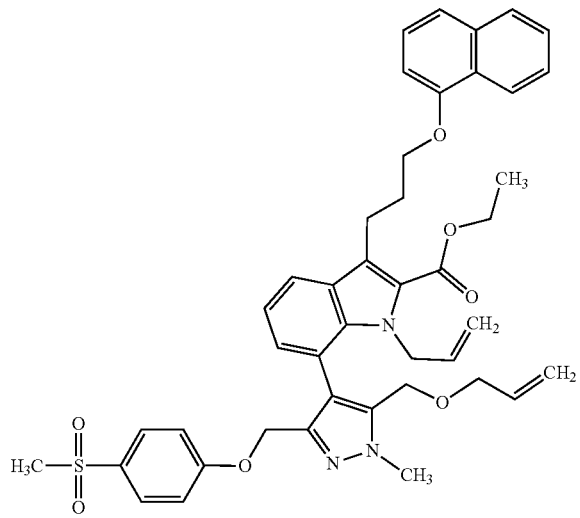 [SMILES: C=CCOCc1c(-c2cccc3c(CCCOc4cccc5ccccc45)c(C(=O)OCC)n(CC=C)c23)c(COc2ccc(S(C)(=O)=O)cc2)nn1C]

To a solution of ethyl 7-[5-(hydroxymethyl)-1-methyl-3-{[4-(methylsulfonyl)phenoxy]methyl}-1H-pyrazol-4-yl]-3-[3-(naphthalen-1-yloxy)propyl]-1H-indole-2-carboxylate (see Intermediate 1-82, 1.30 g, 1.95 mmol) in THF (26 ml) was added sodium hydride (179 mg, 60%, 4.48 mmol) at 0° C. and the mixture was stirred for 2 hours at room temperature. The reaction was cooled down to 0° C. and a solution of allyl bromide (390 µl, 4.5 mmol) in THF (2 ml) was added. The mixture was stirred for 3 days at room temperature and for one day at 40° C. For work-up, an aqueous sodium chloride solution was added and the mixture was extracted with ethyl acetate. The combined organic phases were filtrated through a silicone filter and concentrated under reduced pressure. The residue was purified by flash chromatography (dichloromethane/ethyl acetate gradient, 0%→100% ethyl acetate) to give the title compound (722 mg).

$^1$H-NMR (400 MHz, DMSO-d6) δ [ppm]: 1.154 (1.15), 1.172 (2.51), 1.190 (1.25), 1.243 (4.07), 1.261 (8.92), 1.279 (4.03), 1.988 (4.27), 2.185 (1.01), 2.518 (4.85), 2.523 (3.48), 3.096 (16.00), 3.117 (0.79), 3.164 (7.10), 3.268 (0.97), 3.288 (1.44), 3.797 (1.03), 3.811 (1.07), 3.847 (2.55), 3.860 (1.25), 3.866 (6.21), 3.927 (14.08), 3.983 (0.67), 3.987 (1.13), 3.990 (0.75), 3.997 (0.71), 4.000 (1.31), 4.004 (0.65), 4.017 (0.93), 4.035 (0.89), 4.094 (1.62), 4.119 (1.21), 4.124 (2.69), 4.162 (1.72), 4.166 (1.86), 4.176 (1.44), 4.181 (1.42), 4.209 (1.15), 4.227 (3.40), 4.245 (3.30), 4.262 (1.03), 4.301 (2.04), 4.331 (1.64), 4.522 (2.89), 4.738 (1.74), 4.741 (1.62), 4.764 (1.21), 4.767 (1.40), 4.876 (2.57), 4.887 (2.55), 4.916 (0.63), 5.000 (1.05), 5.005 (1.34), 5.023 (1.07), 5.026 (2.25), 5.031 (2.29), 5.070 (1.52), 5.075 (1.52), 5.089 (2.53), 5.701 (0.87), 5.714 (0.67), 5.727 (0.87), 5.744 (0.83), 5.770 (0.69), 6.856 (1.31), 6.859 (1.36), 6.875 (1.48), 6.878 (1.42), 6.987 (3.84), 6.992 (1.13), 7.004 (1.27), 7.010 (4.37), 7.015 (1.50), 7.029 (2.00), 7.033 (1.90), 7.057 (1.92), 7.077 (2.02), 7.094 (1.09), 7.250 (1.58), 7.272 (1.68), 7.357 (1.19), 7.377 (2.12), 7.396 (1.72), 7.443 (2.14), 7.464 (1.27), 7.504 (1.40), 7.510 (2.39), 7.519 (2.83), 7.529 (2.47), 7.534 (1.54), 7.707 (4.63), 7.712 (1.25), 7.724 (1.27), 7.729 (4.29), 7.750 (1.54), 7.754 (1.46), 7.769 (1.31), 7.773 (1.27), 7.838 (1.80), 7.856 (1.50), 7.860 (2.51), 7.872 (0.87), 7.875 (0.89), 7.880 (1.03), 8.225 (1.03), 8.232 (0.81), 8.249 (0.97).

Intermediate 1-88

(rac)-(E/Z)-ethyl-1-methyl-3-{[4-(methylsulfonyl)phenoxy]methyl}-7-[3-(naphthalen-1-yloxy)propyl]-1,10,13,15-tetrahydropyrazolo[4',3':9,10][1,6]oxaza-cycloundecino[8,7,6-hi]indole-8-carboxylate

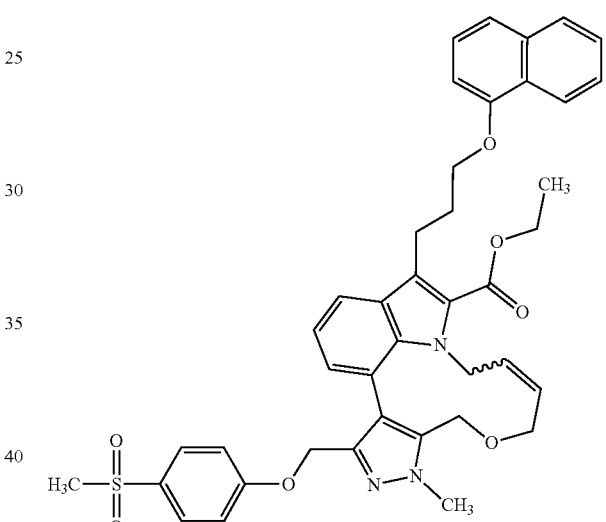

A solution of ethyl 7-(1-methyl-3-{[4-(methylsulfonyl)phenoxy]methyl}-5-[(prop-2-en-1-yloxy)methyl]-1H-pyrazol-4-yl)-3-[3-(naphthalen-1-yloxy)propyl]-1-(prop-2-en-1-yl)-1H-indole-2-carboxylate (720 mg, 963 µmol) in dichloromethane (12 ml) was purged with argon several times. (1,3-Bis(2,4,6-trimethylphenyl)-2-imidazolidinylidene)dichloro(phenylmethylene) (tricyclohexylphosphine)ruthenium (81.7 mg, 96.3 µmol) (Grubbs $2^{nd}$ generation catalyst) was added and the reaction was stirred for 2 days at room temperature. For work-up, the reaction mixture was concentrated under reduced pressure and the residue was purified by flash chromatography (dichloromethane/methanol gradient, 0%→10% methanol) to give the title compound (710 mg).

LC-MS (Method 2): Rt=1.64 min; MS (ESIpos): m/z=720 [M+H]$^+$

Intermediate 1-89

(rac)-ethyl 1-methyl-3-{[4-(methylsulfonyl)phenoxy]methyl}-7-[3-(naphthalen-1-yloxy)propyl]-1,10,11,12,13,15-hexahydropyrazolo[4',3':9,10][1,6]oxazacycloundecino[8,7,6-hi]indole-8-carboxylate

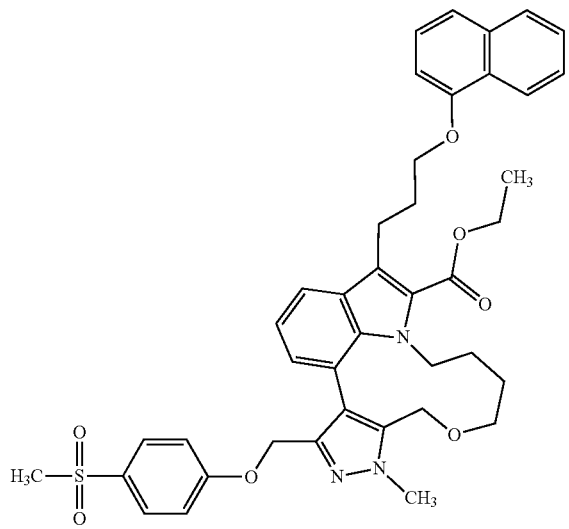 [SMILES: CCOC(=O)c1c(CCCOc2cccc3ccccc23)c2cccc3c2n1CCCCOCc1c-3c(COc2ccc(S(C)(=O)=O)cc2)nn1C]

To a solution of (rac)-(E/Z)-ethyl-1-methyl-3-{[4-(methylsulfonyl)phenoxy]methyl}-7-[3-(naphthalen-1-yloxy)propyl]-1,10,13,15-tetrahydropyrazolo[4',3':9,10][1,6]oxazacycloundecino[8,7,6-hi]indole-8-carboxylate (600 mg, 833 µmol) in THF (15 ml) was added Pd/C (100 mg, 10%) and the reaction was stirred under an atmosphere of hydrogen (25.1 bar) at room temperature for 8 hours. An additional portion of Pd/C (100 mg, 10%) was added and the reaction was stirred under an atmosphere of hydrogen (25.1 bar) at room temperature for 6 hours. For work-up, the mixture was filtered through a pad of celite. The residue was washed with water and the filtrate was concentrated under reduced pressure. The residue was purified by flash chromatography (hexane/ethyl acetate gradient, 10%→75% ethyl acetate) to give the title compound (247 mg).

$^1$H-NMR (400 MHz, DMSO-d6) δ [ppm]: 0.585 (0.51), 1.034 (0.94), 1.048 (0.87), 1.154 (3.39), 1.172 (7.47), 1.190 (3.89), 1.243 (1.07), 1.263 (1.05), 1.275 (4.41), 1.280 (1.39), 1.293 (9.30), 1.311 (4.29), 1.987 (13.91), 2.147 (0.94), 2.322 (0.62), 2.326 (0.86), 2.332 (0.58), 2.518 (3.01), 2.522 (2.09), 2.664 (0.65), 2.668 (0.89), 2.673 (0.64), 2.827 (0.55), 2.839 (0.40), 2.857 (0.57), 3.077 (16.00), 3.090 (1.62), 3.154 (2.04), 3.211 (0.42), 3.224 (0.48), 3.244 (0.68), 3.349 (0.42), 3.459 (0.60), 3.473 (0.48), 3.488 (0.57), 3.830 (1.98), 3.939 (14.19), 3.999 (1.21), 4.017 (3.30), 4.034 (3.26), 4.053 (1.36), 4.067 (0.42), 4.079 (0.50), 4.088 (0.57), 4.104 (0.94), 4.117 (0.69), 4.129 (0.94), 4.144 (0.57), 4.154 (0.47), 4.223 (0.86), 4.232 (0.43), 4.240 (0.85), 4.249 (1.33), 4.262 (0.48), 4.267 (1.54), 4.280 (2.06), 4.298 (1.63), 4.316 (2.16), 4.325 (0.87), 4.333 (0.64), 4.343 (1.07), 4.349 (0.75), 4.360 (0.61), 4.384 (0.64), 4.667 (1.72), 4.675 (1.77), 4.696 (1.98), 4.709 (1.55), 4.875 (1.98), 4.905 (1.76), 5.114 (0.90), 6.806 (1.50), 6.824 (1.63), 6.843 (0.50), 6.850 (4.13), 6.855 (1.18), 6.867 (1.50), 6.872 (4.63), 6.878 (1.91), 6.892 (1.97), 6.895 (1.91), 6.979 (1.90), 6.996 (1.94), 6.998 (2.04), 7.017 (1.26), 7.036 (0.42), 7.221 (0.48), 7.244 (0.54), 7.348 (1.22), 7.368 (2.19), 7.387 (1.72), 7.439 (2.20), 7.460 (1.34), 7.496 (0.46), 7.508 (1.52), 7.513 (2.56), 7.523 (2.95), 7.532 (2.62), 7.537 (1.62), 7.549 (0.53), 7.638 (0.47), 7.646 (4.70), 7.651 (1.25), 7.663 (1.25), 7.668 (4.35), 7.698 (0.48), 7.707 (1.62), 7.710 (1.77), 7.720 (0.65), 7.727 (1.57), 7.731 (1.44), 7.818 (0.55), 7.841 (0.54), 7.856 (1.39), 7.859 (0.97), 7.867 (0.68), 7.870 (0.82), 7.874 (0.90), 7.879 (1.15), 8.229 (1.16), 8.237 (0.83), 8.241 (0.57), 8.244 (0.57), 8.253 (1.00).

Intermediate 1-90

4-[4-(benzyloxy)phenyl]tetrahydro-2H-pyran-4-ol

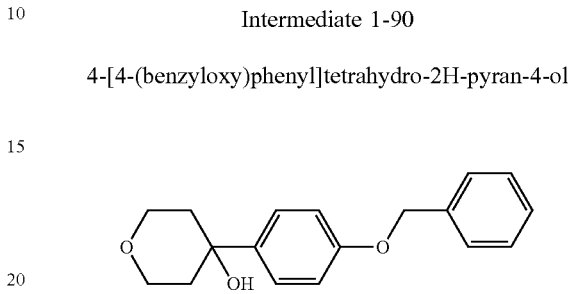

To a solution of benzyl 4-bromophenyl ether (14.7 g, 96% purity, 53.6 mmol) in THF (130 ml) was added a 2.5 M solution of n-butyl lithium in hexane (24 ml, 2.5 M, 59 mmol) at −78° C. and the mixture was stirred for 30 min. A solution tetrahydro-4H-pyran-4-one (5.5 ml, 99% purity, 59 mmol) in THF (25 ml) was added at −78° C. and the reaction was stirred for 2 hours at room temperature. For work-up, ethyl acetate was added to the reaction and the organic phase was washed with saturated aqueous ammonium chloride solution and brine. The organic phase was dried over sodium sulfate. After filtration and removal of the solvents the residue was recrystallized (diethyl ether) to give the title compound (10.3 g).

Intermediate 1-91

4-(tetrahydro-2H-pyran-4-yl)phenol

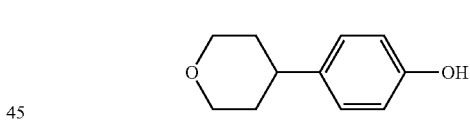

A mixture of 4-[4-(benzyloxy)phenyl]tetrahydro-2H-pyran-4-ol (5.35 g, 18.8 mmol) and Pd/C (535 mg) in ethanol (250 ml) was stirred under an atmosphere of hydrogen at room temperature for 7 hours. For work-up, the mixture was filtered through a pad of celite. The residue was washed with ethyl acetate and the filtrate was concentrated under reduced pressure. The residue was triturated with ethyl acetate to give the title compound (1.7 g).

LC-MS (Method 1): Rt=0.82 min; MS (ESIpos): m/z=179 [M+H]$^+$ $^1$H-NMR (400 MHz, CHLOROFORM-d) δ [ppm]: 0.000 (1.95), 1.183 (0.54), 1.576 (0.56), 1.653 (1.05), 1.657 (1.22), 1.661 (1.33), 1.668 (6.67), 1.677 (6.70), 1.682 (5.42), 1.685 (5.83), 1.693 (9.04), 1.703 (5.97), 1.721 (2.75), 1.727 (1.55), 1.732 (3.03), 1.736 (1.47), 1.755 (0.86), 1.765 (0.89), 2.585 (0.81), 2.597 (1.08), 2.612 (1.75), 2.625 (2.26), 2.638 (1.37), 2.650 (1.21), 2.664 (0.67), 3.429 (3.56), 3.436 (2.29), 3.439 (1.93), 3.457 (6.16), 3.465 (5.17), 3.483 (2.60), 3.493 (3.68), 3.996 (3.55), 3.999 (3.53), 4.004 (3.78), 4.006 (3.63), 4.009 (3.37), 4.023 (3.19), 4.032 (4.48), 4.038 (2.84), 5.033 (4.83), 6.698 (1.29), 6.705 (13.60), 6.711 (4.20), 6.722 (4.58), 6.727

(16.00), 6.735 (1.64), 7.006 (1.35), 7.013 (12.99), 7.017 (3.93), 7.029 (3.62), 7.033 (11.47), 7.041 (1.10).

Intermediate 1-92 ethyl 4-bromo-1-methyl-3-{[4-(tetrahydro-2H-pyran-4-yl)phenoxy]methyl}-1H-pyrazole-5-carboxylate

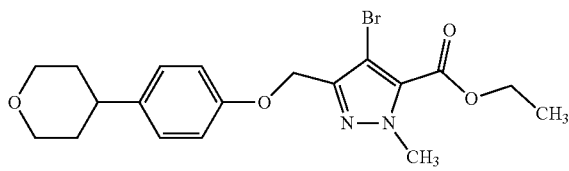 [SMILES: CCOC(=O)c1c(Br)c(COc2ccc(C3CCOCC3)cc2)nn1C]

To a solution of 4-(tetrahydro-2H-pyran-4-yl)phenol (800 mg, 4.35 mmol) in DMF (13 ml) was added caesium carbonate (4.05 g, 12.4 mmol) and the mixture was stirred for 10 min at room temperature. A solution of ethyl 4-bromo-3-(bromomethyl)-1-methyl-1H-pyrazole-5-carboxylate (see Intermediate 1-5; 1.35 g, 4.15 mmol) in DMF (10 ml) was added and the reaction was stirred for 2 hours at room temperature. For work-up, the reaction mixture was poured into an aqueous sodium chloride solution. The resulting precipitate was collected via filtration and the filtrate was washed with water to give the title compound (1.7 g), which was used in the subsequent steps without further purification.

LC-MS (Method 1): Rt=1.37 min; MS (ESIpos): m/z=423 [M+H]$^+$ $^1$H-NMR (400 MHz, DMSO-d6) δ [ppm]: 1.319 (4.09), 1.337 (9.13), 1.354 (4.23), 1.593 (0.68), 1.599 (0.48), 1.604 (0.58), 1.622 (1.39), 1.633 (1.97), 1.640 (1.51), 1.648 (1.84), 1.656 (1.55), 2.518 (0.59), 2.523 (0.40), 2.668 (0.48), 2.679 (0.43), 2.694 (0.58), 2.706 (0.41), 2.729 (0.44), 2.888 (0.45), 3.375 (0.69), 3.385 (0.73), 3.404 (1.33), 3.411 (1.55), 3.432 (0.67), 3.439 (0.75), 3.884 (0.66), 3.911 (1.27), 3.920 (0.98), 3.939 (0.95), 3.944 (0.87), 4.087 (16.00), 4.325 (1.23), 4.343 (4.01), 4.361 (3.94), 4.379 (1.16), 4.970 (7.14), 6.944 (3.13), 6.949 (0.98), 6.960 (1.09), 6.965 (3.70), 7.160 (3.41), 7.165 (1.01), 7.177 (0.93), 7.182 (2.75).

Intermediate 1-93

(4-bromo-1-methyl-3-{[4-(tetrahydro-2H-pyran-4-yl)phenoxy]methyl}-1H-pyrazol-5-yl)methanol

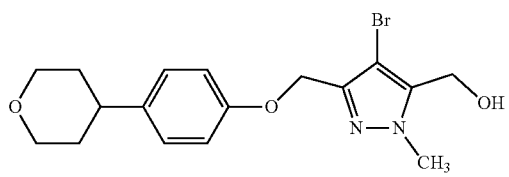 [SMILES: Cn1nc(COc2ccc(C3CCOCC3)cc2)c(Br)c1CO]

To a solution of ethyl 4-bromo-1-methyl-3-{[4-(tetrahydro-2H-pyran-4-yl)phenoxy]methyl}-1H-pyrazole-5-carboxylate (1.72 g, 4.06 mmol) in THF (30 ml) at 0° C. was added a solution of lithium aluminium hydride in THF (2.0 ml, 2.0 M, 4.1 mmol) and the mixture was stirred at 0° C. for 20 min. For work-up, water (0.4 ml) was added dropwise, followed by the addition of aqueous 2 M sodium hydroxide solution (0.4 ml), and again water (0.4 ml). The mixture was filtrated through a pad of celite. The residue was washed with THF and the filtrate was concentrated under reduced pressure to give the title compound (1.45 g).

LC-MS (Method 1): Rt=1.04 min; MS (ESIpos): m/z=381 [M+H]$^+$

Intermediate 1-94 ethyl 7-[5-(hydroxymethyl)-1-methyl-3-{[4-(tetrahydro-2H-pyran-4-yl)phenoxy]methyl}-1H-pyrazol-4-yl]-3-[3-(naphthalen-1-yloxy)propyl]-1H-indole-2-carboxylate

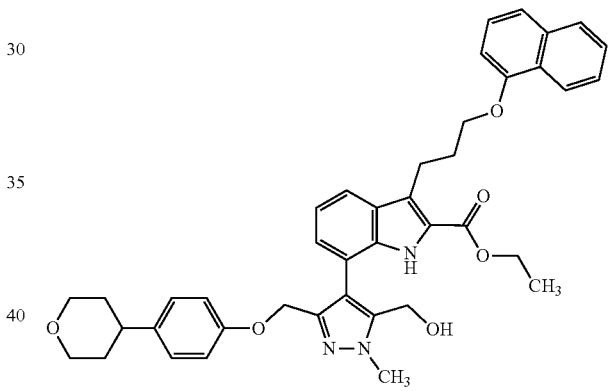

To a solution of ethyl 3-[3-(naphthalen-1-yloxy)propyl]-7-(4,4,5,5-tetramethyl-1,3,2-dioxaborolan-2-yl)-1H-indole-2-carboxylate (see Intermediate 1-4; 846 mg, 1.69 mmol) and (4-bromo-1-methyl-3-{[4-(tetrahydro-2H-pyran-4-yl)phenoxy]methyl}-1H-pyrazol-5-yl)methanol (615 mg, 1.61 mmol) in 1,2-dimethoxyethane (25 ml) were added an aqueous 2 M solution of potassium carbonate (2.4 ml, 2.0 M, 4.8 mmol) and potassium fluoride (187 mg, 3.23 mmol). The mixture was degassed and purged with argon several times. XPhosPd G2 (127 mg, 161 µmol) was added and the mixture was purged with argon for 10 minutes. The reaction was stirred at 80° C. for 3.5 h. For work-up, the reaction mixture was filtrated through a pad of celite. The residue was washed with dichloromethane and the filtrate was concentrated under reduced pressure. The residue was purified by flash chromatography (hexane/ethyl acetate gradient, 0%→100% ethyl acetate) to give the title compound (330 mg).

LC-MS (Method 1): Rt=1.61 min; MS (ESIpos): m/z=675 [M+H]$^+$

287

Intermediate 1-95 ethyl 1-{3-[(tert-butoxycarbonyl)(methyl)amino]
propyl}-7-[5-(hydroxymethyl)-1-methyl-3-{[4-(tet-
rahydro-2H-pyran-4-yl)phenoxy]methyl}-1H-pyra-
zol-4-yl]-3-[3-(naphthalen-1-yloxy)propyl]-1H-
indole-2-carboxylate

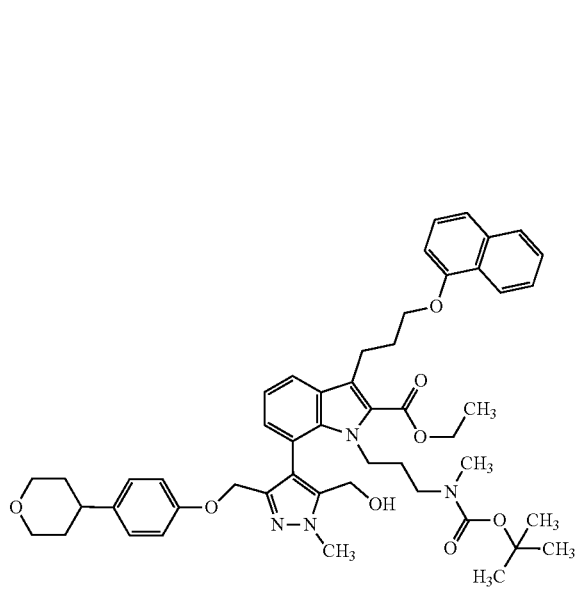

To a solution of ethyl 7-[5-(hydroxymethyl)-1-methyl-3-
{[4-(tetrahydro-2H-pyran-4-yl)phenoxy]methyl}-1H-pyra-
zol-4-yl]-3-[3-(naphthalen-1-yloxy)propyl]-1H-indole-2-
carboxylate (330 mg, 490 µmol) in DMF (6.1 ml, 79 mmol)
were added caesium carbonate (798 mg, 2.45 mmol) and
tert-butyl (3-bromopropyl)methylcarbamate (see Intermedi-
ate 1-1; 148 mg, 588 µmol) and the reaction was stirred for
2.5 hours at 60° C. An additional portion of tert-butyl
(3-bromopropyl)methylcarbamate (98 mg, 392 µmol) was
added and the mixture was stirred for another 3.5 hours at
50° C. For work-up, the reaction mixture was poured into an
aqueous sodium chloride solution. The resulting precipitate
was collected by filtration. The residue was washed with
water and was purified by flash chromatography (dichlo-
romethane/ethyl acetate gradient, 0%→100% ethyl acetate)
to give the title compound (300 mg).

LC-MS (Method 1): Rt=1.72 min; MS (ESIpos): m/z=845
[M+H]$^+$

288

Intermediate 1-96 ethyl 7-[5-(bromomethyl)-1-methyl-3-{[4-(tetra-
hydro-2H-pyran-4-yl)phenoxy]methyl}-1H-pyrazol-
4-yl]-1-{3-[(tert-butoxycarbonyl)(methyl)amino]
propyl}-3-[3-(naphthalen-1-yloxy)propyl]-1H-
indole-2-carboxylate

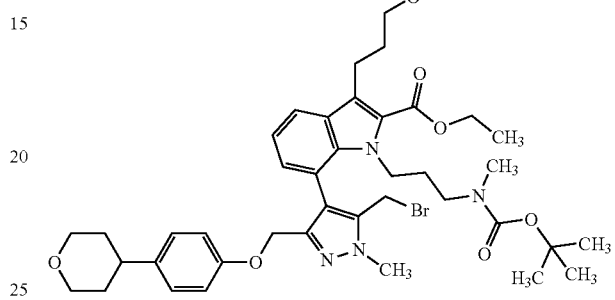

To a solution of ethyl 1-{3-[(tert-butoxycarbonyl)
(methyl)amino]propyl}-7-[5-(hydroxymethyl)-1-methyl-3-
{[4-(tetrahydro-2H-pyran-4-yl)phenoxy]methyl}-1H-pyra-
zol-4-yl]-3-[3-(naphthalen-1-yloxy)propyl]-1H-indole-2-
carboxylate (298 mg, 353 µmol) in dichloromethane (6.4 ml)
was added triphenylphosphine (222 mg, 846 µmol) at 0° C.
and the mixture was stirred at 0° C. for 10 min. Tetrabro-
momethane (257 mg, 776 µmol) was added and the reaction
was stirred at for 90 minutes at room temperature. For
work-up, the reaction mixture was concentrated under
reduced pressure to give the title compound which was used
in the subsequent steps without further purification.

Intermediate 1-97 ethyl 7-[5-(bromomethyl)-1-methyl-3-{[4-(tetra-
hydro-2H-pyran-4-yl)phenoxy]methyl}-1H-pyrazol-
4-yl]-1-[3-(methylamino)propyl]-3-[3-(naphthalen-
1-yloxy)propyl]-1H-indole-2-carboxylate
hydrochloric acid salt To a solution of ethyl 7-[5-(bromomethyl)-1-methyl-3-{[4-(tetrahydro-2H-pyran-4-yl)phenoxy]methyl}-1H-pyrazol-4-yl]-1-{3-[(tert-butoxycarbonyl)(methyl)amino]propyl}-3-[3-(naphthalen-1-yloxy)propyl]-1H-indole-2-carboxylate (321 mg, 353 µmol) in methanol (6.4 ml) was added a 4 M solution of HCl in dioxan (6.4 ml, 4.0 M, 26 mmol) at 0° C. and the mixture was stirred for 16 hours at room temperature. For work-up, the mixture was concentrated under reduced pressure and the crude product was used for the subsequent steps without further purification.

Intermediate 1-98

(rac)-ethyl 7,9-dimethyl-1-[3-(naphthalen-1-yloxy)propyl]-11-{[4-(tetrahydro-2H-pyran-4-yl)phenoxy]methyl}-4,5,6,7,8,9-hexahydropyrazolo[3',4':7,8][1,5]diazecino[9,10,1-hi]indole-2-carboxylate

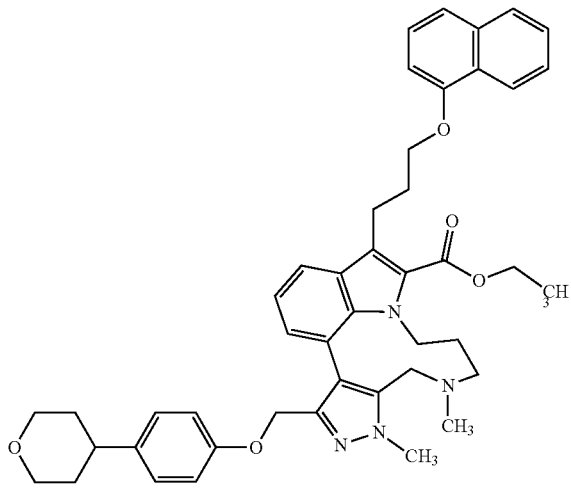

To a solution of ethyl 7-[5-(bromomethyl)-1-methyl-3-{[4-(tetrahydro-2H-pyran-4-yl)phenoxy]methyl}-1H-pyrazol-4-yl]-1-[3-(methylamino)propyl]-3-[3-(naphthalen-1-yloxy)propyl]-1H-indole-2-carboxylate hydrochloric acid salt (298 mg) in DMF (31 ml) was added caesium carbonate (575 mg, 1.77 mmol) and the reaction was stirred at 65° C. for 2 hours. For work-up, the mixture was concentrated under reduced pressure and the residue was purified by flash chromatography (Biotage SNAP cartridge NH$_2$ silica, hexane/ethyl acetate gradient, 0%→100% ethyl acetate) to give the title compound (107 mg).

LC-MS (Method 2): Rt=1.78 min; MS (ESIpos): m/z=727 [M+H]$^+$

Intermediate 1-99

4-(4-hydroxyphenyl)tetrahydro-2H-pyran-4-ol

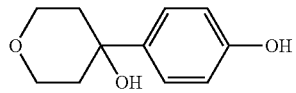 [SMILES: Oc1ccc(C2(O)CCOCC2)cc1]

To a suspension of Pd/C (758 mg, 10% wt-% Pd, 712 µmol) in ethanol (310 ml) and pyridine (10 ml) was added 4-[4-(benzyloxy)phenyl]tetrahydro-2H-pyran-4-ol (see Intermediate 1-90; 7.50 g, 26.4 mmol) and the mixture was stirred under an atmosphere of hydrogen for 8 hours at room temperature. For work-up, the mixture was filtered through a pad of celite. The residue was washed with THF and the filtrate was concentrated under reduced pressure to give after trituration with ethyl acetate the title compound (4.7 g).

$^1$H-NMR (400 MHz, DMSO-d6) δ [ppm]: 1.481 (5.55), 1.511 (6.54), 1.846 (2.40), 1.858 (2.64), 1.877 (4.00), 1.889 (3.95), 1.909 (2.38), 1.922 (2.12), 1.988 (0.70), 2.518 (1.40), 2.523 (0.92), 3.338 (8.10), 3.645 (2.63), 3.655 (3.01), 3.672 (5.38), 3.682 (5.13), 3.716 (4.57), 3.721 (5.45), 3.746 (6.71), 3.749 (6.47), 3.774 (2.84), 3.778 (2.34), 4.801 (13.52), 6.679 (1.60), 6.686 (15.19), 6.691 (4.67), 6.703 (4.91), 6.708 (16.00), 6.715 (1.69), 7.240 (1.75), 7.247 (15.65), 7.252 (4.73), 7.264 (4.65), 7.270 (14.22), 7.276 (1.49), 9.209 (14.05).

Intermediate 1-100 ethyl 4-bromo-3-{[4-(4-hydroxytetrahydro-2H-pyran-4-yl)phenoxy]methyl}-1-methyl-1H-pyrazole-5-carboxylate

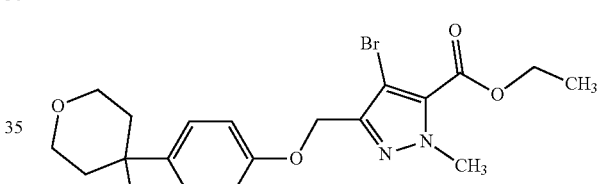

To a solution of 4-(4-hydroxyphenyl)tetrahydro-2H-pyran-4-ol (2.35 g, 12.1 mmol) in DMF (40 ml) was added caesium carbonate (11.8 g, 36.3 mmol) and the mixture was stirred for 10 min at room temperature. Ethyl 4-bromo-3-(bromomethyl)-1-methyl-1H-pyrazole-5-carboxylate (see Intermediate 1-5; 3.94 g, 12.1 mmol) was added and the reaction was stirred for 4 hours at room temperature. For work-up, the reaction mixture was poured into an aqueous sodium chloride solution. The mixture was extracted with ethyl acetate and the combined organic phases were dried over sodium sulfate. After filtration and removal of the solvents the residue was purified by flash chromatography (hexane/ethyl acetate gradient, 12%→100% ethyl acetate) to give the title compound (5.05 g).

$^1$H-NMR (400 MHz, DMSO-d6) δ [ppm]: 1.320 (4.17), 1.337 (9.68), 1.355 (4.26), 1.493 (1.15), 1.523 (1.28), 1.883 (0.44), 1.895 (0.52), 1.914 (0.78), 1.926 (0.76), 1.946 (0.47), 2.518 (0.55), 3.663 (0.51), 3.673 (0.60), 3.691 (1.07), 3.700 (1.03), 3.735 (1.10), 3.759 (1.29), 3.763 (1.30), 3.787 (0.56), 4.089 (16.00), 4.326 (1.10), 4.344 (3.65), 4.362 (3.65), 4.380 (1.07), 4.925 (2.93), 4.987 (6.21), 6.963 (3.05), 6.968 (0.90), 6.979 (0.93), 6.985 (3.39), 7.383 (3.40), 7.389 (0.95), 7.400 (0.90), 7.405 (2.89).

Intermediate 1-101

4-(4-{[4-bromo-5-(hydroxymethyl)-1-methyl-1H-pyrazol-3-yl]methoxy}phenyl)tetrahydro-2H-pyran-4-ol

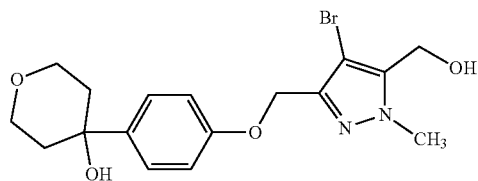 [SMILES: Cn1nc(COc2ccc(C3(O)CCOCC3)cc2)c(Br)c1CO]

To a solution of ethyl 4-bromo-3-{[4-(4-hydroxytetrahydro-2H-pyran-4-yl)phenoxy]methyl}-1-methyl-1H-pyrazole-5-carboxylate (5.00 g, 11.4 mmol) in THF (110 ml) at 0° C. was added a solution of lithium aluminium hydride in THF (5.7 ml, 2.0 M, 11 mmol) and the mixture was stirred at 0° C. for 2 hours. Ice was carefully added and the mixture was stirred for 30 minutes. The mixture was poured into water and was extracted with ethyl acetate/THF. The combined organic layers were washed with brine and dried over sodium sulfate. After filtration and removal of the solvents the crude product (3.80 g) was used without further purification in the subsequent steps.

$^1$H-NMR (400 MHz, DMSO-d6) δ [ppm]: 1.173 (0.43), 1.493 (1.63), 1.523 (1.87), 1.881 (0.63), 1.894 (0.73), 1.913 (1.14), 1.924 (1.09), 1.945 (0.68), 1.957 (0.57), 1.988 (0.75), 3.332 (16.00), 3.662 (0.74), 3.672 (0.89), 3.686 (1.60), 3.699 (1.50), 3.734 (1.54), 3.762 (2.96), 3.771 (0.46), 3.787 (0.78), 4.475 (3.53), 4.489 (3.56), 4.915 (9.87), 4.929 (0.62), 5.400 (0.89), 5.414 (2.17), 5.427 (0.85), 6.948 (0.62), 6.955 (3.69), 6.960 (1.27), 6.972 (1.27), 6.977 (4.00), 6.984 (0.46), 7.366 (0.49), 7.373 (4.25), 7.378 (1.45), 7.390 (1.22), 7.395 (3.69).

Intermediate 1-102 ethyl 7-[5-(hydroxymethyl)-3-{[4-(4-hydroxytetrahydro-2H-pyran-4-yl)phenoxy]methyl}-1-methyl-1H-pyrazol-4-yl]-3-[3-(naphthalen-1-yloxy)propyl]-1H-indole-2-carboxylate To a solution of ethyl 3-[3-(naphthalen-1-yloxy)propyl]-7-(4,4,5,5-tetramethyl-1,3,2-dioxaborolan-2-yl)-1H-indole-2-carboxylate (see Intermediate 1-4; 3.46 g, 6.92 mmol) and 4-(4-{[4-bromo-5-(hydroxymethyl)-1-methyl-1H-pyrazol-3-yl]methoxy}phenyl)tetrahydro-2H-pyran-4-ol (2.50 g, 6.29 mmol) in 1,4-dioxane (81 ml) were added an aqueous 2 M solution of potassium carbonate (9.4 ml, 2.0 M, 19 mmol). The mixture was degassed and purged with argon several times. Pd(dppf)Cl$_2$×CH$_2$Cl$_2$ (921 mg, 1.26 mmol) was added and the mixture was purged with argon for 10 minutes. The reaction was stirred at 80° C. for 6 h. For work-up, the reaction mixture was concentrated under reduced pressure and the residue was purified by flash chromatography (dichloromethane/acetone gradient, 5%→40% acetone) to give the title compound (2.87 g).

LC-MS (Method 2): Rt=1.46 min; MS (ESIpos): m/z=690 [M+H]$^+$ $^1$H-NMR (400 MHz, DMSO-d6) δ [ppm]: 1.067 (10.64), 1.138 (0.55), 1.247 (4.80), 1.265 (10.83), 1.282 (4.96), 1.457 (1.80), 1.488 (2.12), 1.834 (0.66), 1.846 (0.80), 1.865 (1.22), 1.877 (1.22), 1.897 (0.79), 1.910 (0.70), 2.084 (14.06), 2.204 (0.97), 2.223 (1.33), 2.240 (1.04), 2.327 (0.54), 2.518 (2.22), 2.523 (1.56), 2.669 (0.54), 3.347 (1.98), 3.365 (1.12), 3.639 (0.82), 3.650 (1.00), 3.663 (1.72), 3.675 (1.67), 3.713 (1.66), 3.741 (2.07), 3.765 (1.05), 3.865 (2.13), 3.939 (1.84), 3.963 (16.00), 4.190 (1.40), 4.206 (2.84), 4.221 (1.47), 4.228 (1.30), 4.247 (3.21), 4.264 (3.10), 4.282 (1.00), 4.383 (0.70), 4.476 (0.60), 4.490 (0.59), 4.813 (0.65), 4.875 (4.65), 4.916 (1.21), 5.413 (0.42), 5.730 (1.11), 5.742 (2.64), 5.753 (1.16), 5.759 (8.54), 6.825 (4.14), 6.847 (4.46), 6.892 (1.80), 6.909 (1.91), 6.955 (0.48), 6.977 (0.52), 7.031 (1.59), 7.049 (2.07), 7.051 (2.01), 7.069 (1.75), 7.227 (2.17), 7.229 (2.27), 7.245 (1.86), 7.247 (1.82), 7.280 (4.75), 7.302 (4.15), 7.362 (1.42), 7.373 (0.66), 7.383 (2.61), 7.395 (0.61), 7.402 (2.13), 7.442 (2.67), 7.463 (1.52), 7.473 (0.58), 7.477 (0.74), 7.490 (1.53), 7.494 (1.41), 7.504 (1.72), 7.510 (2.57), 7.514 (1.74), 7.524 (1.53), 7.528 (1.73), 7.541 (0.78), 7.545 (0.55), 7.685 (1.88), 7.705 (1.74), 7.853 (1.56), 7.860 (0.98), 7.872 (1.67), 7.877 (1.36), 8.207 (1.34), 8.210 (1.39), 8.229 (1.28), 8.231 (1.33), 10.830 (2.89).

Intermediate 1-103 ethyl 7-(3-{[4-(4-hydroxytetrahydro-2H-pyran-4-yl)phenoxy]methyl}-1-methyl-5-[(prop-2-en-1-yloxy)methyl]-1H-pyrazol-4-yl)-3-[3-(naphthalen-1-yloxy)propyl]-1-(prop-2-en-1-yl)-1H-indole-2-carboxylate

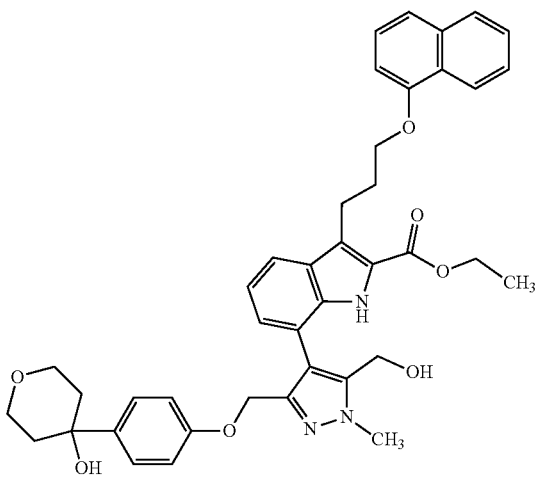 [SMILES: CCOC(=O)c1[nH]c2c(-c3c(COc4ccc(C5(O)CCOCC5)cc4)nn(C)c3CO)cccc2c1CCCOc1cccc2ccccc12]
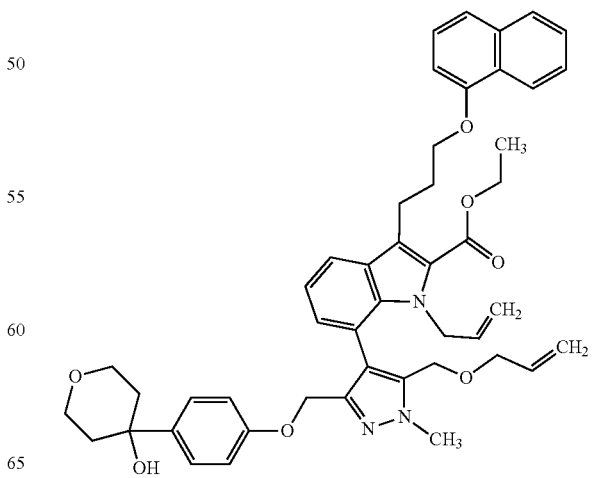

To a solution of ethyl 7-[5-(hydroxymethyl)-3-{[4-(4-hydroxytetrahydro-2H-pyran-4-yl)phenoxy]methyl}-1-methyl-1H-pyrazol-4-yl]-3-[3-(naphthalen-1-yloxy)propyl]-1H-indole-2-carboxylate (1.40 g, 2.03 mmol) in THF (27 ml) was added sodium hydride (203 mg, 60% purity, 5.07 mmol) at 0° C. and the mixture was stirred for 2 hours at room temperature. The reaction was cooled down to 0° C. and a solution of allyl bromide (440 µl, 5.1 mmol) in THF (1 ml) was added. The mixture was stirred for 5 days at room temperature. For work-up, an aqueous sodium chloride solution was added and the mixture was extracted with ethyl acetate. The combined organic phases were washed with brine and the organic phase was dried over sodium sulfate and concentrated under reduced pressure. The residue was purified by flash chromatography (hexane/ethyl acetate gradient, 50%→100% ethyl acetate) to give the title compound (802 mg).

LC-MS (Method 1): Rt=1.67 min; MS (ESIpos): m/z=771 [M+H]$^+$

Intermediate 1-104

(rac)-(E/Z)-ethyl-3-{[4-(4-hydroxytetrahydro-2H-pyran-4-yl)phenoxy]methyl}-1-methyl-7-[3-(naphthalen-1-yloxy)propyl]-1,10,13,15-tetrahydropyrazolo[4',3':9,10][1,6]oxazacycloundecino[8,7,6-hi]indole-8-carboxylate

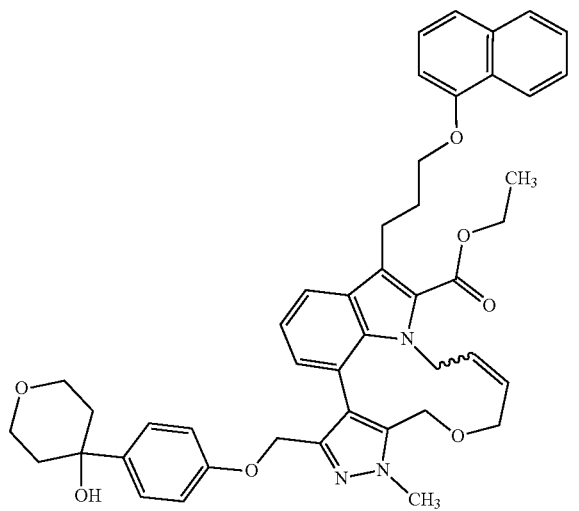 [SMILES: CCOC(=O)c1c(CCCOc2cccc3ccccc23)c2cccc3c2n1CC=CCOCc1c-3c(COc2ccc(C3(O)CCOCC3)cc2)nn1C]

A solution of ethyl 7-(3-{[4-(4-hydroxytetrahydro-2H-pyran-4-yl)phenoxy]methyl}-1-methyl-5-[(prop-2-en-1-yloxy)methyl]-1H-pyrazol-4-yl)-3-[3-(naphthalen-1-yloxy)propyl]-1-(prop-2-en-1-yl)-1H-indole-2-carboxylate (802 mg, 1.04 mmol) in dichloromethane (13 ml) was purged with argon several times. (1,3-Bis(2,4,6-trimethylphenyl)-2-imidazolidinylidene)dichloro(phenylmethylene)(tricyclohexylphosphine)ruthenium (88.5 mg, 104 µmol) (Grubbs 2$^{nd}$ generation catalyst) was added and the reaction was stirred for 3 days at room temperature. For work-up, the reaction mixture was concentrated under reduced pressure and the residue was purified by flash chromatography (dichloromethane/acetone gradient, 0%→20% acetone) to give the title compound (510 mg).

$^1$H-NMR (400 MHz, DMSO-d6) δ [ppm]: 1.236 (0.41), 1.254 (0.68), 1.283 (0.61), 1.293 (4.70), 1.301 (1.08), 1.311 (10.50), 1.328 (4.81), 1.394 (1.89), 1.425 (2.18), 1.769 (0.69), 1.780 (0.82), 1.800 (1.31), 1.811 (1.28), 1.832 (0.84), 1.844 (0.68), 2.084 (0.41), 2.154 (0.68), 2.172 (1.09), 2.185 (1.12), 2.202 (0.81), 2.323 (0.54), 2.327 (0.78), 2.331 (0.54), 2.518 (3.36), 2.523 (2.39), 2.665 (0.61), 2.669 (0.81), 2.673 (0.57), 2.728 (1.49), 2.888 (1.82), 3.251 (0.49), 3.264 (0.64), 3.285 (0.92), 3.302 (0.62), 3.348 (0.88), 3.363 (0.46), 3.488 (0.62), 3.519 (1.07), 3.551 (0.73), 3.581 (0.92), 3.592 (1.11), 3.608 (1.80), 3.619 (1.62), 3.664 (1.82), 3.693 (2.27), 3.718 (1.01), 3.788 (0.73), 3.799 (0.78), 3.820 (0.70), 3.832 (0.57), 3.856 (0.45), 3.896 (0.58), 3.917 (0.51), 3.925 (1.34), 3.948 (16.00), 4.077 (0.58), 4.085 (0.68), 4.101 (1.01), 4.122 (0.69), 4.137 (1.12), 4.152 (0.74), 4.162 (0.69), 4.223 (1.88), 4.241 (0.46), 4.258 (2.38), 4.269 (0.82), 4.277 (0.97), 4.286 (1.81), 4.295 (0.45), 4.304 (2.36), 4.322 (2.19), 4.340 (1.68), 4.349 (0.85), 4.358 (0.51), 4.367 (0.85), 4.400 (1.92), 4.428 (2.27), 4.652 (2.23), 4.681 (2.01), 4.707 (0.51), 4.743 (2.38), 4.778 (2.45), 4.809 (4.58), 4.819 (0.57), 4.959 (0.95), 5.000 (1.80), 5.024 (1.14), 5.051 (0.62), 5.181 (0.41), 5.197 (0.61), 5.206 (0.64), 5.759 (3.26), 6.546 (4.15), 6.568 (4.35), 6.787 (1.81), 6.796 (0.46), 6.805 (1.95), 6.822 (2.11), 6.825 (2.14), 6.840 (2.41), 6.842 (2.30), 6.981 (2.11), 7.001 (2.24), 7.019 (1.50), 7.174 (4.66), 7.179 (1.53), 7.191 (1.65), 7.196 (4.32), 7.343 (1.43), 7.363 (2.54), 7.377 (0.76), 7.382 (2.04), 7.396 (0.41), 7.438 (2.72), 7.459 (1.69), 7.482 (0.49), 7.486 (0.69), 7.499 (1.73), 7.504 (1.72), 7.509 (1.89), 7.516 (3.65), 7.523 (1.91), 7.528 (1.76), 7.533 (1.81), 7.545 (0.69), 7.550 (0.43), 7.705 (1.93), 7.707 (2.01), 7.725 (1.91), 7.728 (1.89), 7.855 (1.73), 7.863 (0.89), 7.873 (1.62), 7.878 (1.39), 8.209 (1.32), 8.215 (1.35), 8.226 (0.76), 8.234 (1.31).

Intermediate 1-105

(rac)-ethyl 3-{[4-(4-hydroxytetrahydro-2H-pyran-4-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate

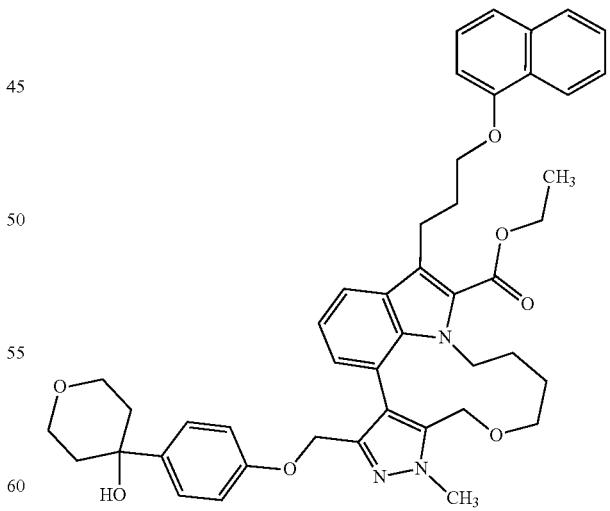

To a suspension of Pd/C (123 mg, 10 wt-% Pd, 116 µmol) in ethanol (10 ml) and pyridine (470 µl) was added (rac)-(E/Z)-ethyl-3-{[4-(4-hydroxytetrahydro-2H-pyran-4-yl)phenoxy]methyl}-1-methyl-7-[3-(naphthalen-1-yloxy)propyl]-1,10,13,15-tetrahydropyrazolo[4',3':9,10][1,6]

oxazacycloundecino[8,7,6-hi]indole-8-carboxylate (430 mg, 580 µmol) and the reaction was stirred under an atmosphere of hydrogen at room temperature for 24 hours. For work-up, the mixture was filtered through a pad of celite. The residue was washed with THF and the filtrate was concentrated under reduced pressure to give the title compound (420 mg), which was used in the subsequent steps without further purification.

LC-MS (Method 1): Rt=1.64 min; MS (ESIpos): m/z=744 [M+H]$^+$

Intermediate 1-106

4-[4-(benzyloxy)phenyl]-4-methoxytetrahydro-2H-pyran

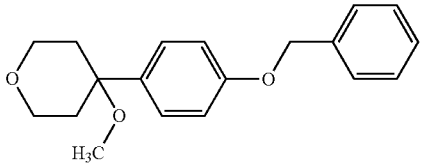 [SMILES: COC1(c2ccc(OCc3ccccc3)cc2)CCOCC1]

To a solution of 4-[4-(benzyloxy)phenyl]tetrahydro-2H-pyran-4-ol (see Intermediate 1-90; 2.70 g, 9.50 mmol) in DMF (20 ml) was added sodium hydride (380 mg, 60% purity, 9.50 mmol) at 0° C. and the mixture was stirred for 1 hour at room temperature. Iodomethane (540 µl, 8.6 mmol) was added dropwise and the reaction was stirred for 24 hours at room temperature. For work-up, the mixture was poured into water. The mixture was extracted with ethyl acetate and the combined organic phases were washed with brine. The organic phase was dried over sodium sulfate. After filtration and removal of the solvent the crude product was purified by flash chromatography (hexane/ethyl acetate gradient, 12%→60% ethyl acetate) to give the title compound (2.2 g).

$^1$H-NMR (400 MHz, DMSO-d6) δ [ppm]: 1.855 (0.87), 1.873 (1.92), 1.888 (2.31), 2.518 (0.89), 2.523 (0.61), 2.830 (16.00), 3.653 (2.41), 3.661 (3.01), 3.671 (2.24), 3.679 (2.03), 5.097 (5.79), 6.997 (2.97), 7.002 (0.90), 7.014 (1.00), 7.019 (3.44), 7.294 (3.39), 7.299 (0.99), 7.311 (1.22), 7.316 (3.01), 7.323 (0.53), 7.329 (1.22), 7.347 (1.03), 7.351 (0.59), 7.377 (1.38), 7.392 (1.13), 7.396 (2.88), 7.408 (0.45), 7.413 (1.57), 7.416 (1.06), 7.443 (2.55), 7.461 (1.40), 7.465 (1.01).

Intermediate 1-107

4-(4-methoxytetrahydro-2H-pyran-4-yl)phenol

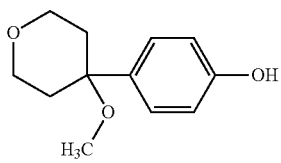

To a suspension of Pd/C (212 mg, 10 wt-% Pd, 199 µmol) in ethanol (86 ml) and pyridine (2.8 ml) was added 4-[4-(benzyloxy)phenyl]-4-methoxytetrahydro-2H-pyran (2.20 g, 7.37 mmol) and the reaction was stirred under an atmosphere of hydrogen at room temperature for 24 hours. For work-up, the mixture was filtered through a pad of celite. The residue was washed with THF and the filtrate was concentrated under reduced pressure to give after trituration with hexane/diethyl ether the title compound (1.51 g).

$^1$H-NMR (400 MHz, DMSO-d6) δ [ppm]: 1.826 (0.83), 1.846 (1.22), 1.867 (2.19), 1.900 (0.44), 2.810 (16.00), 3.641 (2.47), 3.648 (2.98), 3.662 (1.99), 3.668 (1.48), 6.736 (3.12), 6.741 (0.93), 6.752 (1.00), 6.757 (3.52), 7.164 (3.32), 7.169 (0.98), 7.180 (0.95), 7.185 (3.01), 9.389 (0.83).

Intermediate 1-108 ethyl 4-bromo-3-{[4-(4-methoxytetrahydro-2H-pyran-4-yl)phenoxy]methyl}-1-methyl-1H-pyrazole-5-carboxylate

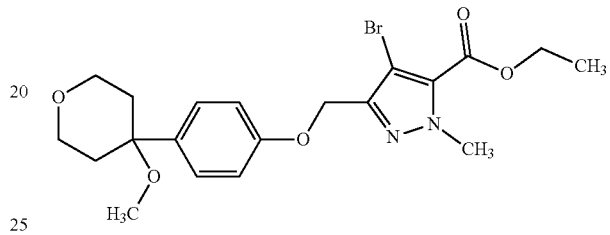

To a solution of 4-(4-methoxytetrahydro-2H-pyran-4-yl)phenol (1.51 g, 7.25 mmol) in DMF (24 ml) was added caesium carbonate (7.09 g, 21.8 mmol) and the mixture was stirred for 10 min at room temperature. ethyl 4-bromo-3-(bromomethyl)-1-methyl-1H-pyrazole-5-carboxylate (see Intermediate 1-5; 2.36 g, 7.25 mmol) was added and the reaction was stirred for 3 hours at room temperature. For work-up, the reaction mixture was poured into a sodium chloride solution and the mixture was extracted with ethyl acetate. The combined organic layers were washed with brine and dried over sodium sulfate. After filtration and removal of the solvents the crude product was purified by flash chromatography (hexane/ethyl acetate gradient, 12%→100% ethyl acetate) to give the title compound (3.11 g).

$^1$H-NMR (400 MHz, DMSO-d6) δ [ppm]: 1.321 (3.74), 1.326 (0.46), 1.339 (8.34), 1.357 (3.88), 1.862 (0.86), 1.880 (1.94), 1.892 (1.97), 1.898 (1.97), 2.518 (1.23), 2.523 (0.92), 2.810 (0.62), 2.838 (16.00), 3.658 (2.06), 3.666 (2.71), 3.675 (2.03), 3.684 (2.04), 4.095 (15.27), 4.330 (1.14), 4.347 (3.76), 4.365 (3.74), 4.383 (1.09), 5.005 (6.33), 7.019 (2.86), 7.024 (0.83), 7.036 (0.92), 7.041 (3.33), 7.304 (3.29), 7.309 (0.90), 7.321 (0.84), 7.326 (2.76).

Intermediate 1-109

(4-bromo-3-{[4-(4-methoxytetrahydro-2H-pyran-4-yl)phenoxy]methyl}-1-methyl-1H-pyrazol-5-yl)methanol

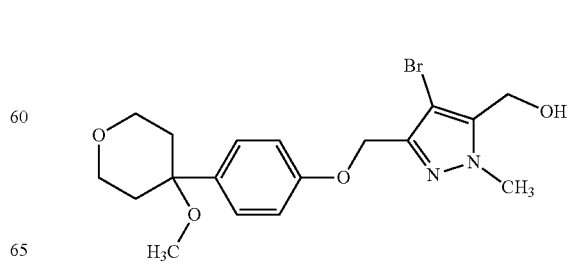

To a solution of ethyl 4-bromo-3-{[4-(4-methoxytetrahydro-2H-pyran-4-yl)phenoxy]methyl}-1-methyl-1H-pyrazole-5-carboxylate (3.11 g, 6.86 mmol) in THF (67 ml) at 0° C. was added a solution of lithium aluminium hydride in THF (3.4 ml, 2.0 M, 6.9 mmol) and the mixture was stirred at 0° C. for 3 hours. Ice was carefully added and the mixture was stirred for 30 minutes. A solution of sodium potassium tartrate was added and the mixture was extracted with ethyl acetate. The combined organic layers were washed with brine and dried over sodium sulfate. After filtration and removal of the solvents the crude product was triturated with diethyl ether/ethyl acetate to give the title compound (2.4 g).

$^1$H-NMR (400 MHz, DMSO-d6) δ [ppm]: 1.861 (0.84), 1.879 (2.06), 1.892 (2.19), 1.897 (2.00), 1.988 (0.47), 2.518 (0.77), 2.523 (0.52), 2.828 (2.85), 2.838 (16.00), 3.331 (7.95), 3.657 (2.22), 3.666 (2.79), 3.675 (2.24), 3.683 (2.06), 3.769 (2.77), 4.462 (0.63), 4.476 (0.94), 4.481 (3.49), 4.495 (3.57), 4.933 (6.16), 4.944 (1.16), 5.260 (0.52), 5.404 (1.15), 5.418 (2.67), 5.431 (1.02), 6.228 (0.66), 6.981 (0.47), 7.003 (0.76), 7.011 (2.79), 7.016 (0.80), 7.029 (0.91), 7.034 (3.13), 7.279 (0.58), 7.294 (3.12), 7.299 (1.13), 7.311 (0.84), 7.317 (2.52).

To a solution of ethyl 3-[3-(naphthalen-1-yloxy)propyl]-7-(4,4,5,5-tetramethyl-1,3,2-dioxaborolan-2-yl)-1H-indole-2-carboxylate (see Intermediate 1-4; 3.21 g, 6.42 mmol) and (4-bromo-3-{[4-(4-methoxytetrahydro-2H-pyran-4-yl)phenoxy]methyl}-1-methyl-1H-pyrazol-5-yl)methanol (2.40 g, 5.84 mmol) in 1,4-dioxane (75 ml) was added an aqueous 2 M solution of potassium carbonate (8.8 ml, 2.0 M, 18 mmol). The mixture was degassed and purged with argon several times. Pd(dppf)Cl$_2$×CH$_2$Cl$_2$ (854 mg, 1.17 mmol) was added and the mixture was purged with argon for 10 minutes. The reaction was stirred at 80° C. for 6 h. For work-up, the reaction mixture was concentrated under reduced pressure and the residue was purified by flash chromatography (dichloromethane/acetone gradient, 0%→40% acetone) to give the title compound (3.1 g).

LC-MS (Method 1): Rt=1.58 min; MS (ESIneg): m/z=702 [M–H]$^-$

Intermediate 1-111 ethyl 7-(3-{[4-(4-methoxytetrahydro-2H-pyran-4-yl)phenoxy]methyl}-1-methyl-5-[(prop-2-en-1-yloxy)methyl]-1H-pyrazol-4-yl)-3-[3-(naphthalen-1-yloxy)propyl]-1-(prop-2-en-1-yl)-1H-indole-2-carboxylate Intermediate 1-110 ethyl 7-[5-(hydroxymethyl)-3-{[4-(4-methoxytetrahydro-2H-pyran-4-yl)phenoxy]methyl}-1-methyl-1H-pyrazol-4-yl]-3-[3-(naphthalen-1-yloxy)propyl]-1H-indole-2-carboxylate

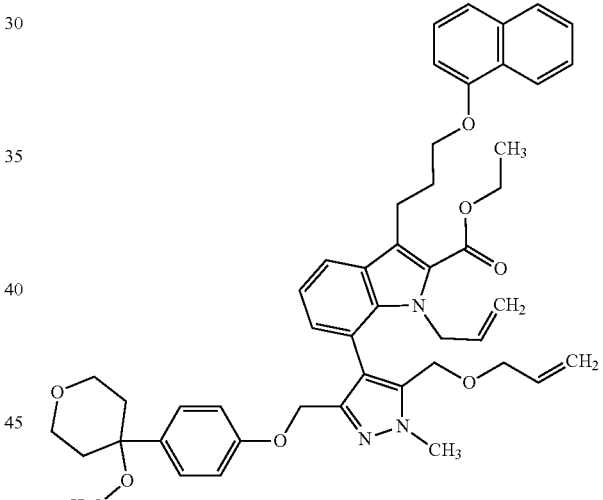

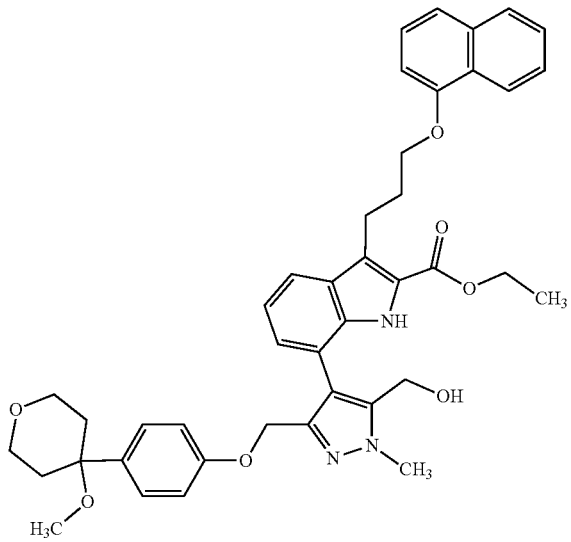 [SMILES: CCOC(=O)c1[nH]c2c(-c3c(COc4ccc(C5(OC)CCOCC5)cc4)nn(C)c3CO)cccc2c1CCCOc1cccc2ccccc12]

To a solution of ethyl 7-[5-(hydroxymethyl)-3-{[4-(4-methoxytetrahydro-2H-pyran-4-yl)phenoxy]methyl}-1-methyl-1H-pyrazol-4-yl]-3-[3-(naphthalen-1-yloxy)propyl]-1H-indole-2-carboxylate (1.55 g, 2.20 mmol) in THF (30 ml) was added sodium hydride (220 mg, 60% purity, 5.51 mmol) at 0° C. and the mixture was stirred for 2 hours at room temperature. The reaction was cooled down to 0° C. and a solution of allyl bromide (480 µl, 5.5 mmol) in THF (1 ml) was added. The mixture was stirred for 5 days at room temperature. For work-up, aqueous sodium chloride solution was added and the mixture was extracted with ethyl acetate. The combined organic phases were washed with brine dried over sodium sulfate, filtrated and the filtrate was concentrated under reduced pressure. The residue was purified by flash chromatography (hexane/ethyl acetate gradient, 30%→100% ethyl acetate) to give the title compound (1.17 g).

Intermediate 1-112

(rac)-(E/Z)-ethyl-3-{[4-(4-methoxytetrahydro-2H-pyran-4-yl)phenoxy]methyl}-1-methyl-7-[3-(1-naphthyloxy)propyl]-1,10,13,15-tetrahydropyrazolo[4',3':9,10][1,6]oxazacycloundecino[8,7,6-hi]indole-8-carboxylate

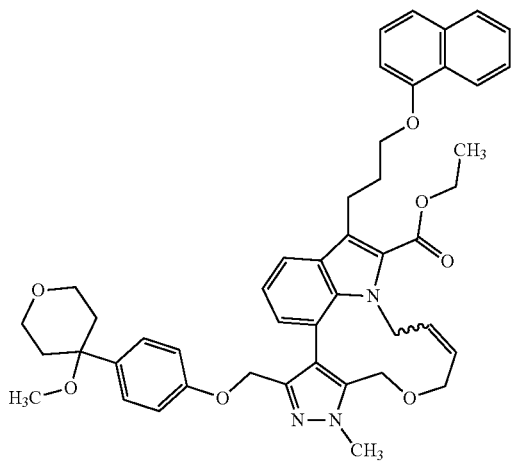 [SMILES: CCOC(=O)c1c(CCCOc2cccc3ccccc23)c2cccc3c2n1CC=CCOCc1c-3c(COc2ccc(C3(OC)CCOCC3)cc2)nn1C]

A solution of ethyl 7-(3-{[4-(4-methoxytetrahydro-2H-pyran-4-yl)phenoxy]methyl}-1-methyl-5-[(prop-2-en-1-yloxy)methyl]-1H-pyrazol-4-yl)-3-[3-(naphthalen-1-yloxy)propyl]-1-(prop-2-en-1-yl)-1H-indole-2-carboxylate (1.17 g, 1.49 mmol) in dichloromethane (19 ml) was purged with argon several times. (1,3-Bis(2,4,6-trimethylphenyl)-2-imidazolidinylidene)dichloro(phenylmethylene)(tricyclohexylphosphine)ruthenium (127 mg, 149 µmol) (Grubbs 2$^{nd}$ generation catalyst) was added and the reaction was stirred for 3 days at room temperature under an argon atmosphere. For work-up, the reaction mixture was concentrated under reduced pressure and the residue was purified by flash chromatography (hexane/ethyl acetate gradient, 12%→100% ethyl acetate) to give the title compound (440 mg).

$^1$H-NMR (400 MHz, DMSO-d6) δ [ppm]: 1.279 (0.50), 1.290 (3.66), 1.296 (1.11), 1.308 (8.06), 1.325 (3.70), 1.722 (0.92), 1.742 (2.11), 1.755 (2.36), 1.987 (0.50), 2.150 (0.64), 2.166 (0.92), 2.184 (0.68), 2.323 (0.45), 2.327 (0.61), 2.331 (0.43), 2.518 (2.51), 2.523 (1.75), 2.665 (0.47), 2.669 (0.62), 2.673 (0.43), 2.712 (16.00), 2.760 (0.47), 3.252 (0.43), 3.271 (0.61), 3.485 (0.45), 3.516 (0.80), 3.559 (2.30), 3.567 (2.77), 3.578 (2.23), 3.789 (0.45), 3.800 (0.54), 3.821 (0.46), 3.934 (0.55), 3.944 (0.80), 3.953 (11.73), 4.117 (0.58), 4.132 (1.18), 4.140 (1.16), 4.155 (0.66), 4.226 (1.32), 4.255 (0.96), 4.260 (1.51), 4.273 (0.71), 4.283 (1.28), 4.300 (1.63), 4.318 (1.64), 4.336 (1.25), 4.346 (0.64), 4.363 (0.62), 4.439 (1.41), 4.468 (1.67), 4.684 (1.71), 4.693 (0.47), 4.713 (1.56), 4.734 (0.59), 4.748 (1.56), 4.760 (0.67), 4.782 (1.40), 4.933 (0.68), 4.972 (0.49), 4.998 (0.40), 5.026 (0.71), 5.052 (0.41), 5.197 (0.45), 5.209 (0.43), 5.759 (1.03), 6.568 (2.93), 6.590 (3.12), 6.801 (1.37), 6.818 (1.51), 6.832 (1.49), 6.834 (1.58), 6.849 (1.73), 6.852 (1.65), 6.999 (1.47), 7.016 (1.45), 7.018 (1.64), 7.037 (1.18), 7.056 (3.19), 7.072 (1.15), 7.078 (2.90), 7.343 (1.08), 7.363 (1.83), 7.382 (1.44), 7.440 (1.97), 7.461 (1.26), 7.483 (0.49), 7.497 (1.17), 7.500 (1.12), 7.509 (1.34), 7.515 (2.30), 7.521 (1.27), 7.529 (1.16), 7.533 (1.26), 7.546 (0.52), 7.714 (1.40), 7.717 (1.41), 7.734 (1.41), 7.736 (1.27), 7.856 (1.23), 7.863 (0.68), 7.874 (1.29), 7.879 (1.04), 8.198 (0.98), 8.204 (1.04), 8.222 (0.96).

Intermediate 1-113

(rac)-ethyl 3-{[4-(4-methoxytetrahydro-2H-pyran-4-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate

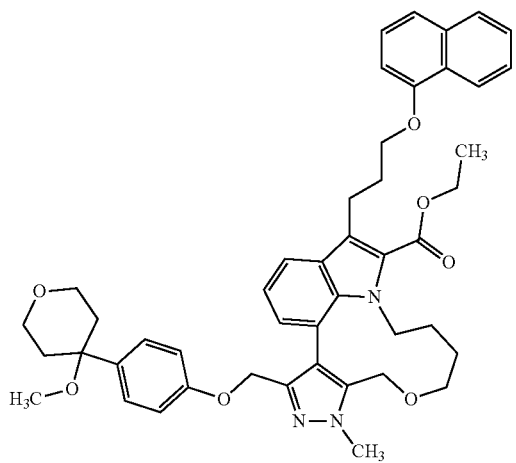 [SMILES: CCOC(=O)c1c(CCCOc2cccc3ccccc23)c2cccc3c2n1CCCCOCc1c-3c(COc2ccc(C3(OC)CCOCC3)cc2)nn1C]

To a suspension of Pd/C (101 mg, 10 wt-% Pd, 95.2 µmol) in ethanol (8.3 ml) and pyridine (390 µl) was added (rac)-(E/Z)-ethyl-3-{[4-(4-methoxytetrahydro-2H-pyran-4-yl)phenoxy]methyl}-1-methyl-7-[3-(naphthalen-1-yloxy)propyl]-1,10,13,15-tetrahydropyrazolo[4',3':9,10][1,6]oxazacycloundecino[8,7,6-hi]indole-8-carboxylate (360 mg, 476 µmol) and the reaction was stirred under an atmosphere of hydrogen at room temperature for 24 hours. For work-up, the mixture was filtered through a pad of celite. The residue was washed with THF and the filtrate was concentrated under reduced pressure to give the title compound (350 mg), which was used in the subsequent steps without further purification.

LC-MS (Method 1): Rt=1.75 min; MS (ESIpos): m/z=758 [M+H]$^+$ $^1$H-NMR (400 MHz, DMSO-d6) δ [ppm]: 1.044 (1.10), 1.059 (0.89), 1.234 (0.94), 1.251 (1.00), 1.261 (0.94), 1.275 (4.18), 1.293 (8.19), 1.311 (3.89), 1.750 (2.71), 1.784 (0.51), 1.885 (0.41), 2.142 (0.90), 2.159 (1.39), 2.176 (0.98), 2.327 (0.51), 2.518 (2.31), 2.523 (1.54), 2.665 (0.40), 2.669 (0.55), 2.674 (0.47), 2.712 (16.00), 2.744 (0.73), 2.768 (0.65), 2.815 (0.56), 2.826 (0.50), 2.844 (0.57), 3.209 (0.49), 3.224 (0.51), 3.242 (0.78), 3.368 (0.57), 3.464 (0.62), 3.476 (0.48), 3.493 (0.59), 3.564 (2.67), 3.570 (2.72), 3.578 (2.48), 3.586 (2.05), 3.613 (0.40), 3.934 (12.32), 3.955 (0.65), 4.097 (0.65), 4.115 (1.41), 4.130 (2.61), 4.146 (1.15), 4.227 (0.74), 4.237 (0.45), 4.245 (0.88), 4.255 (1.32), 4.263 (0.57), 4.272 (1.50), 4.279 (1.83), 4.290 (0.71), 4.296 (1.57), 4.313 (2.75), 4.323 (0.80), 4.331 (0.44), 4.341 (0.68), 4.408 (0.67), 4.419 (0.41), 4.445 (0.58), 4.529 (1.54), 4.558 (1.84), 4.680 (1.60), 4.714 (1.44), 4.758 (1.90), 4.786 (1.63), 6.611 (3.26), 6.633 (3.44), 6.796 (1.54), 6.815 (1.67), 6.868 (1.47), 6.871 (1.51), 6.886 (1.91), 6.888 (1.79), 6.989 (1.51), 7.008 (1.80), 7.026 (1.15), 7.070 (3.53), 7.092 (3.10), 7.340 (1.09), 7.360 (2.07), 7.380 (1.77), 7.439 (2.19), 7.460 (1.42), 7.488 (0.52), 7.501 (1.34), 7.505 (1.27), 7.510 (1.48), 7.517 (2.83), 7.525 (1.52), 7.530 (1.34), 7.534 (1.40), 7.547 (0.51), 7.720 (1.52), 7.723 (1.59), 7.740 (1.44), 7.743 (1.36), 7.855 (1.35), 7.863 (0.69), 7.873 (1.24), 7.878 (1.10), 8.213 (1.10), 8.218 (1.05), 8.237 (1.04).

Intermediate 1-114 ethyl 4-bromo-1-methyl-3-[(propan-2-yloxy) methyl]-1H-pyrazole-5-carboxylate

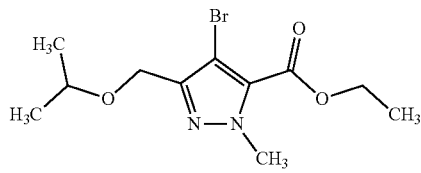 [SMILES: CCOC(=O)c1c(Br)c(COC(C)C)nn1C]

To a solution of propan-2-ol (850 µl, 11 mmol) in dry DMF (35 ml) was slowly added sodium hydride (442 mg, 60% purity, 11.0 mmol) at 0° C. and the mixture was stirred for 1 hour at room temperature. A solution of ethyl 4-bromo-3-(bromomethyl)-1-methyl-1H-pyrazole-5-carboxylate (see Intermediate 1-5; 3.00 g, 9.20 mmol) in dry DMF (25 ml) was added dropwise and the mixture was stirred for 24 hours at room temperature. For work-up, the reaction mixture was poured into water and the mixture was extracted with ethyl acetate. The combined organic phases were washed with brine and were dried over sodium sulfate. After filtration the filtrate was concentrated under reduced pressure and the residue was purified by flash chromatography (hexane/ethyl acetate gradient, 5%→30% ethyl acetate) to give the title compound (1.7 g).

LC-MS (Method 1): Rt=1.25 min; MS (ESIpos): m/z=305 [M+H]$^+$

Intermediate 1-115

{4-bromo-1-methyl-3-[(propan-2-yloxy)methyl]-1H-pyrazol-5-yl}methanol

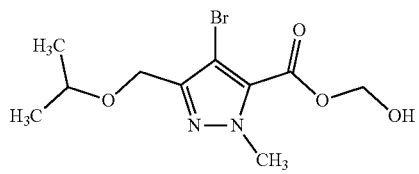 [SMILES: CC(C)OCc1nn(C)c(C(=O)OCO)c1Br]

To a solution of ethyl 4-bromo-1-methyl-3-[(propan-2-yloxy)methyl]-1H-pyrazole-5-carboxylate (4.70 g, 15.4 mmol) in THF (150 ml) at 0° C. was added a solution of lithium aluminium hydride in THF (7.7 ml, 15.4 mmol) and the mixture was stirred at 0° C. for 2 hours. Ice was carefully added and the mixture was stirred for 30 minutes. The mixture was poured into water and the mixture was extracted with ethyl acetate. The combined organic layers were washed with brine and dried over sodium sulfate. After filtration and removal of the solvents the crude product was used without further purification in the subsequent steps (contains [4-bromo-3-(ethoxymethyl)-1-methyl-1H-pyrazol-5-yl]methanol as a impurity).

Intermediate 1-116 ethyl 7-{5-(hydroxymethyl)-1-methyl-3-[(propan-2-yloxy)methyl]-1H-pyrazol-4-yl}-3-[3-(naphthalen-1-yloxy)propyl]-1H-indole-2-carboxylate

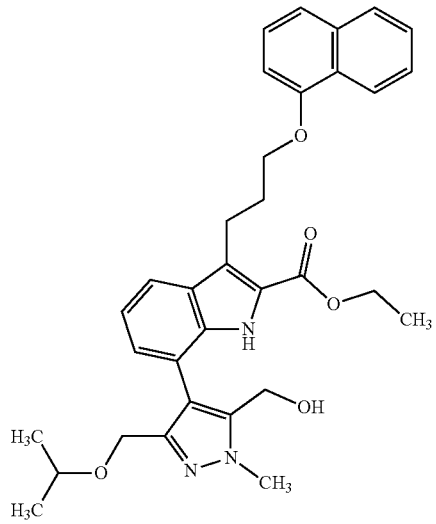 [SMILES: CCOC(=O)c1[nH]c2c(-c3c(COC(C)C)nn(C)c3CO)cccc2c1CCCOc1cccc2ccccc12]

To a solution of ethyl 3-[3-(naphthalen-1-yloxy)propyl]-7-(4,4,5,5-tetramethyl-1,3,2-dioxaborolan-2-yl)-1H-indole-2-carboxylate (6.79 g, 13.6 mmol) and {4-bromo-1-methyl-3-[(propan-2-yloxy)methyl]-1H-pyrazol-5-yl}methanol (see Intermediate 1-4; 3.25 g, 12.4 mmol) in 1,4-dioxane (160 ml) was added a 2 M aqueous solution of potassium carbonate (19 ml, 2.0 M, 37 mmol). The mixture was degassed and purged with argon several times. Pd(dppf)Cl$_2$×CH$_2$Cl$_2$ (1.81 g, 2.47 mmol) was added and the mixture was purged with argon for 10 minutes. The reaction was stirred at 80° C. for 20 hours. For work-up, the reaction mixture was concentrated under reduced pressure and the residue was purified twice by flash chromatography (hexane/ethyl acetate gradient, 20%→100% ethyl acetate, followed by hexane/ethyl acetate gradient, 50%→100% ethyl acetate) to give the title compound (4.4 g). (contains ethyl 7-[3-(ethoxymethyl)-5-(hydroxymethyl)-1-methyl-1H-pyrazol-4-yl]-3-[3-(1-naphthyloxy)propyl]-1H-indole-2-carboxylate as an impurity)

Intermediate 1-117

Ethyl 7-{1-methyl-3-[(propan-2-yloxy)methyl]-5-[(prop-2-en-1-yloxy)methyl]-1H-pyrazol-4-yl}-3-[3-(naphthalen-1-yloxy)propyl]-1-(prop-2-en-1-yl)-1H-indole-2-carboxylate

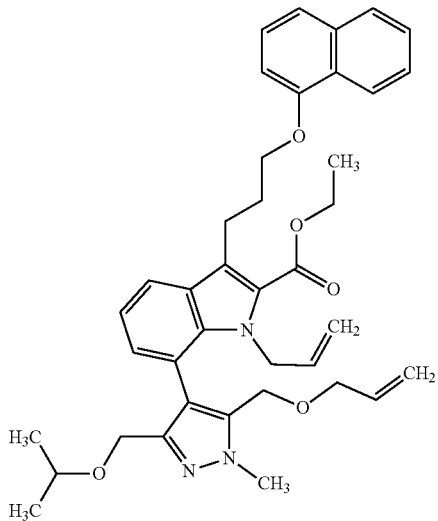 [SMILES: C=CCOCc1c(-c2cccc3c(CCCOc4cccc5ccccc45)c(C(=O)OCC)n(CC=C)c23)c(COC(C)C)nn1C]

To a solution of ethyl 7-{5-(hydroxymethyl)-1-methyl-3-[(propan-2-yloxy)methyl]-1H-pyrazol-4-yl}-3-[3-(naphthalen-1-yloxy)propyl]-1H-indole-2-carboxylate (1.37 g, 2.47 mmol) in THF (33 ml) was added sodium hydride (296 mg, 60% purity, 7.40 mmol) at 0° C. and the mixture was stirred for 2 hours at room temperature. The reaction was cooled down to 0° C. and a solution of allyl bromide (640 µl, 7.4 mmol) in THF (1 ml) was added. The mixture was stirred for 3 days at room temperature. For work-up, aqueous sodium chloride solution was added and the mixture was extracted with ethyl acetate. The combined organic phases were washed with brine and were dried over sodium sulfate and filtrated. The filtrate was concentrated under reduced pressure and the residue was purified by flash chromatography (hexane/ethyl acetate gradient, 12%→100% ethyl acetate) to give the title compound (440 mg).

LC-MS (Method 1): Rt=1.77 min; MS (ESIpos): m/z=637 [M+H]+

$^1$H-NMR (400 MHz, DMSO-d6) δ [ppm]: 0.682 (8.23), 0.697 (8.35), 0.829 (8.36), 0.845 (8.38), 0.853 (0.53), 0.870 (0.91), 0.888 (0.42), 1.093 (0.60), 1.237 (4.70), 1.255 (10.79), 1.273 (4.79), 2.191 (0.88), 2.207 (1.39), 2.224 (0.94), 2.327 (0.46), 2.518 (1.49), 2.523 (1.13), 2.669 (0.45), 3.244 (0.59), 3.259 (1.58), 3.274 (2.07), 3.289 (1.78), 3.304 (1.27), 3.311 (1.43), 3.322 (1.62), 3.769 (0.53), 3.783 (0.58), 3.798 (0.84), 3.802 (2.14), 3.806 (0.77), 3.812 (0.75), 3.816 (1.25), 3.820 (0.71), 3.838 (0.79), 3.842 (1.35), 3.846 (1.00), 3.852 (0.98), 3.855 (1.41), 3.859 (1.03), 3.871 (16.00), 3.878 (2.08), 3.884 (0.53), 3.888 (0.62), 4.078 (1.95), 4.100 (6.11), 4.109 (2.74), 4.129 (1.31), 4.133 (1.26), 4.173 (2.23), 4.176 (2.13), 4.189 (2.62), 4.199 (1.85), 4.204 (1.43), 4.217 (3.96), 4.235 (3.53), 4.252 (1.05), 4.290 (2.32), 4.306 (0.68), 4.320 (1.91), 4.655 (0.40), 4.667 (0.46), 4.698 (0.71), 4.701 (0.63), 4.713 (1.73), 4.717 (1.41), 4.739 (1.30), 4.742 (1.25), 4.810 (0.63), 4.815 (0.60), 4.820 (0.71), 4.852 (0.44), 4.863 (0.43), 5.006 (0.55), 5.009 (1.14), 5.014 (1.36), 5.017 (0.60), 5.032 (0.63), 5.036 (1.21), 5.040 (1.83), 5.045 (1.55), 5.050 (1.25), 5.054 (0.45), 5.084 (0.64), 5.088 (1.59), 5.093 (1.38), 5.097 (0.52), 5.435 (0.65), 5.447 (0.50), 5.460 (0.69), 5.465 (0.41), 5.477 (0.69), 5.490 (0.45), 5.503 (0.59), 5.701 (0.54), 5.715 (1.01), 5.727 (0.82), 5.741 (1.07), 5.744 (0.56), 5.759 (14.41), 5.771 (0.70), 5.784 (0.86), 6.864 (1.52), 6.881 (1.78), 6.984 (1.43), 6.987 (1.61), 7.002 (2.11), 7.005 (2.01), 7.070 (1.96), 7.090 (2.04), 7.108 (1.36), 7.362 (1.31), 7.383 (2.24), 7.402 (1.85), 7.449 (2.38), 7.470 (1.39), 7.501 (0.50), 7.513 (1.67), 7.517 (2.47), 7.527 (2.96), 7.537 (2.32), 7.540 (1.84), 7.553 (0.55), 7.763 (1.67), 7.766 (1.70), 7.783 (1.58), 7.786 (1.52), 7.861 (1.35), 7.865 (0.93), 7.875 (0.85), 7.878 (0.87), 7.884 (1.14), 8.235 (1.20), 8.246 (0.83), 8.259 (1.08).

Intermediate 1-118

(rac)-ethyl (11Z)-1-methyl-7-[3-(naphthalen-1-yloxy)propyl]-3-[(propan-2-yloxy)methyl]-1,10,13,15-tetrahydropyrazolo[4',3':9,10][1,6]oxazacycloundecino[8,7,6-hi]indole-8-carboxylate

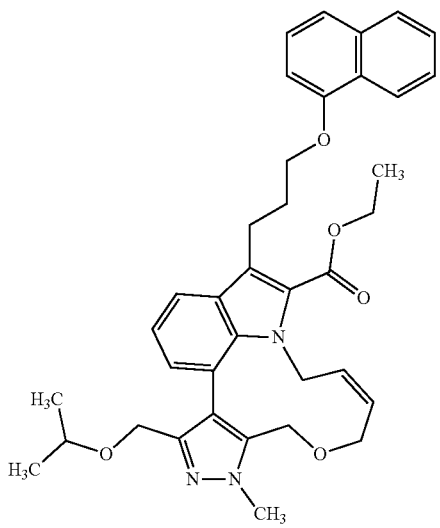 [SMILES: CCOC(=O)c1c(CCCOc2cccc3ccccc23)c2cccc3c2n1C/C=C\COCc1c-3c(COC(C)C)nn1C]

A solution of ethyl 7-{1-methyl-3-[(propan-2-yloxy)methyl]-5-[(prop-2-en-1-yloxy)methyl]-1H-pyrazol-4-yl}-3-[3-(naphthalen-1-yloxy)propyl]-1-(prop-2-en-1-yl)-1H-indole-2-carboxylate (340 mg, 535 µmol) in dichloromethane (6.9 ml) was purged with argon several times. (1,3-Bis(2,4,6-trimethylphenyl)-2-imidazolidinylidene)dichloro(phenylmethylene)(tricyclohexylphosphine)ruthenium (45.4 mg, 53.5 µmol) (Grubbs 2$^{nd}$ generation catalyst) was added and the reaction was stirred for 1 day at room temperature. For work-up, the reaction mixture was concentrated under reduced pressure and the residue was purified by flash chromatography (hexane/ethyl acetate gradient, 12%→100% ethyl acetate) to give the title compound (290 mg).

LC-MS (Method 1): Rt=1.69 min; MS (ESIpos): m/z=608 [M+H]+

$^1$H-NMR (400 MHz, DMSO-d6) δ [ppm]: 0.532 (8.89), 0.547 (8.90), 0.698 (8.56), 0.713 (8.56), 0.740 (0.71), 1.259 (5.50), 1.277 (12.26), 1.294 (5.58), 2.204 (1.04), 2.220 (1.66), 2.236 (1.13), 2.254 (0.40), 2.323 (0.43), 2.327 (0.62), 2.332 (0.42), 2.518 (2.15), 2.523 (1.59), 2.665 (0.44), 2.669 (0.63), 2.674 (0.41), 3.038 (0.56), 3.053 (1.51), 3.068 (2.03), 3.083 (1.46), 3.098 (0.57), 3.278 (0.61), 3.292 (0.57), 3.311 (1.00), 3.369 (0.45), 3.388 (0.90), 3.406 (0.53), 3.422 (0.60), 3.468 (0.61), 3.499 (1.08), 3.530 (0.73), 3.767 (0.65), 3.778 (0.79), 3.798 (2.71), 3.810 (0.64), 3.826 (2.81), 3.884 (0.52), 3.905 (16.00), 3.912 (1.81), 3.970 (2.76), 3.998 (2.32), 4.182 (1.40), 4.197 (2.98), 4.206 (1.12), 4.213 (1.56), 4.220 (2.23), 4.224 (1.43), 4.233 (0.76), 4.242 (0.97), 4.251 (2.48), 4.255 (2.53), 4.269 (2.16), 4.275 (2.12), 4.287 (0.80), 4.292 (1.91), 4.302 (0.72), 4.310 (0.54), 4.319 (0.67), 4.689 (0.49), 4.720 (2.40), 4.754 (2.62), 4.957 (0.93), 4.971 (0.59), 4.995 (2.19), 5.020 (0.54), 5.186 (0.56), 5.198 (0.57), 5.759 (3.72), 6.810 (1.88), 6.814 (2.04), 6.828 (2.20), 6.831 (2.13), 6.872 (1.80), 6.889 (2.01), 7.045 (1.82), 7.063 (1.93), 7.065 (2.26), 7.083 (1.76), 7.367 (1.40), 7.387 (2.67), 7.406 (2.15), 7.449 (2.75), 7.470 (1.58), 7.494 (0.59), 7.506 (1.56), 7.511 (1.60), 7.513 (2.04), 7.522 (3.60), 7.527 (0.89), 7.530 (2.12), 7.533 (1.82), 7.537 (1.89), 7.550 (0.68), 7.765 (1.92), 7.767 (2.01), 7.785 (1.83), 7.787 (1.79), 7.860 (1.56), 7.868 (0.79), 7.877 (1.23), 7.883 (1.36), 8.214 (1.33), 8.221 (1.13), 8.231 (0.70), 8.236 (1.08), 8.239 (1.19).

Intermediate 1-119

(rac)-ethyl 1-methyl-3-[(propan-2-yloxy)methyl]-7-[3-(5,6,7,8-tetrahydronaphthalen-1-yloxy)propyl]-1,10,11,12,13,15-hexahydropyrazolo[4',3':9,10][1,6]oxazacycloundecino[8,7,6-hi]indole-8-carboxylate

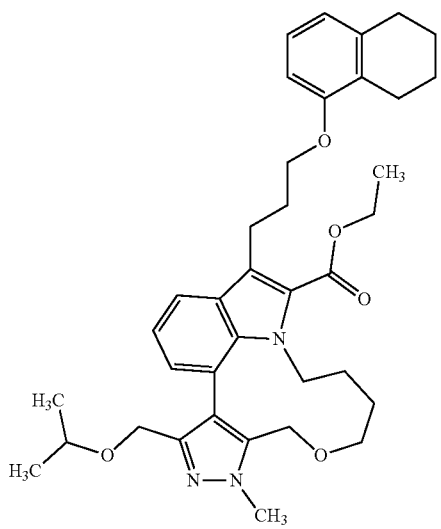 [SMILES: CCOC(=O)c1c(CCCOc2cccc3c2CCCC3)c2cccc3c2n1CCCCOCc1c-3c(COC(C)C)nn1C]

To a suspension of Pd/C (84.0 mg, 10 wt-% Pd, 79.0 μmol) in ethanol (6.9 ml) was added (rac)-ethyl (11Z)-1-methyl-7-[3-(naphthalen-1-yloxy)propyl]-3-[(propan-2-yloxy)methyl]-1,10,13,15-tetrahydropyrazolo[4',3':9,10][1,6]oxazacycloundecino[8,7,6-hi]indole-8-carboxylate (240 mg, 395 μmol) and the reaction was stirred under an atmosphere of hydrogen at room temperature for 4 days. For work-up, the mixture was filtered through a pad of celite. The residue was washed with THF and the filtrate was concentrated under reduced pressure to give the title compound (220 mg), which was used in the subsequent steps without further purification.

LC-MS (Method 1): Rt=1.83 min; MS (ESIpos): m/z=615 [M+H]$^+$

Intermediate 1-120 ethyl 1-{3-[(tert-butoxycarbonyl)(methyl)amino]propyl}-7-{5-(hydroxymethyl)-1-methyl-3-[(propan-2-yloxy)methyl]-1H-pyrazol-4-yl}-3-[3-(naphthalen-1-yloxy)propyl]-1H-indole-2-carboxylate

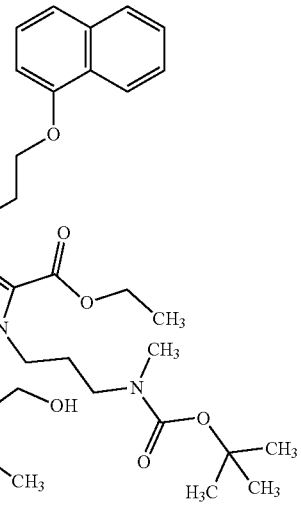

To a solution of ethyl 7-{5-(hydroxymethyl)-1-methyl-3-[(propan-2-yloxy)methyl]-1H-pyrazol-4-yl}-3-[3-(naphthalen-1-yloxy)propyl]-1H-indole-2-carboxylate (see Intermediate 1-116; 1.37 g, 2.47 mmol) in DMF (32 ml) was added caesium carbonate (4.02 g, 12.3 mmol) and the mixture was stirred for 10 min at room temperature. Tert-butyl (3-bromopropyl)methylcarbamate (see Intermediate 1-1; 746 mg, 2.96 mmol) was added and the reaction was stirred for 2 days at room temperature. For work-up, the reaction mixture was poured into water. The mixture was extracted with ethyl acetate. The combined organic phases were washed with brine and dried over sodium sulfate. After filtration and removal of the solvent the crude product was purified by flash chromatography (dichloromethane/methanol gradient, 15%→50% methanol) to give the title compound (1.1 g). (contains ethyl 1-{3-[(tert-butoxycarbonyl)(methyl)amino]propyl}-7-[3-(ethoxymethyl)-5-(hydroxymethyl)-1-methyl-1H-pyrazol-4-yl]-3-[3-(1-naphthyloxy)propyl]-1H-indole-2-carboxylate as an impurity)

Intermediate 1-121 ethyl 7-{5-(bromomethyl)-1-methyl-3-[(propan-2-yloxy)methyl]-1H-pyrazol-4-yl}-1-{3-[(tert-butoxycarbonyl)(methyl)amino]propyl}-3-[3-(naphthalen-1-yloxy)propyl]-1H-indole-2-carboxylate

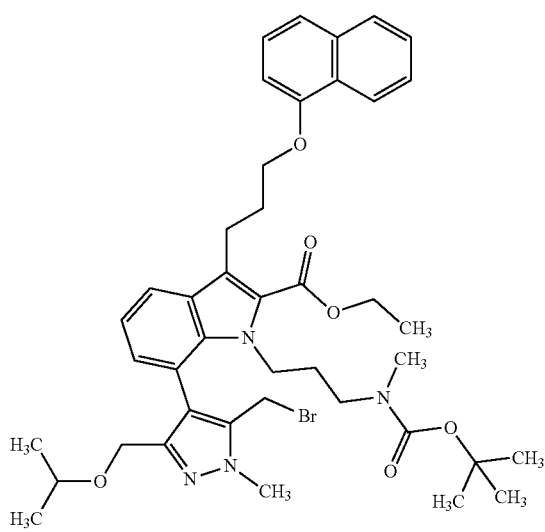 [SMILES: CCOC(=O)c1c(CCCOc2cccc3ccccc23)c2cccc(-c3c(COC(C)C)nn(C)c3CBr)c2n1CCCN(C)C(=O)OC(C)(C)C]

To a solution of ethyl 1-{3-[(tert-butoxycarbonyl)(methyl)amino]propyl}-7-{5-(hydroxymethyl)-1-methyl-3-[(propan-2-yloxy)methyl]-1H-pyrazol-4-yl}-3-[3-(naphthalen-1-yloxy)propyl]-1H-indole-2-carboxylate (1.10 g, 1.51 mmol) in dichloromethane (28 ml) was added triphenylphosphine (953 mg, 3.63 mmol) at 0° C. and the mixture was stirred at 0° C. for 10 min. Tetrabromomethane (1.10 g, 3.33 mmol) was added and the reaction was stirred at 0° C. for 4 hours. For work-up, the reaction mixture was concentrated under reduced pressure and the crude product was purified by flash chromatography (hexane/ethyl acetate gradient, 12%→50% ethyl acetate) to give the title compound (350 mg).

Intermediate 1-122 ethyl 7-{5-(bromomethyl)-1-methyl-3-[(propan-2-yloxy)methyl]-1H-pyrazol-4-yl}-1-[3-(methylamino)propyl]-3-[3-(naphthalen-1-yloxy)propyl]-1H-indole-2-carboxylate hydrochloric acid salt

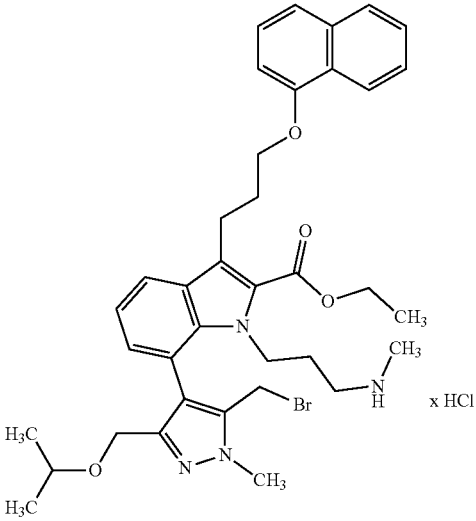 [SMILES: CCOC(=O)c1c(CCCOc2cccc3ccccc23)c2cccc(-c3c(COC(C)C)nn(C)c3CBr)c2n1CCCNC ; "x HCl"]
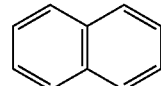

To a solution of ethyl 7-{5-(bromomethyl)-1-methyl-3-[(propan-2-yloxy)methyl]-1H-pyrazol-4-yl}-1-{3-[(tert-butoxycarbonyl)(methyl)amino]propyl}-3-[3-(naphthalen-1-yloxy)propyl]-1H-indole-2-carboxylate (350 mg, 443 μmol) in methanol (8.0 ml) was added a 4 M solution of HCl in dioxan (7.8 ml, 4.0 M, 31 mmol) at 0° C. and the mixture was stirred for 2 h at room temperature. For work-up, the mixture was concentrated under reduced pressure and the crude product was used for the subsequent steps without further purification.

Intermediate 1-123

(rac)-ethyl 7,9-dimethyl-1-[3-(naphthalen-1-yloxy)propyl]-11-[(propan-2-yloxy)methyl]-4,5,6,7,8,9-hexahydropyrazolo[3',4':7,8][1,5]diazecino[9,10,1-hi]indole-2-carboxylate

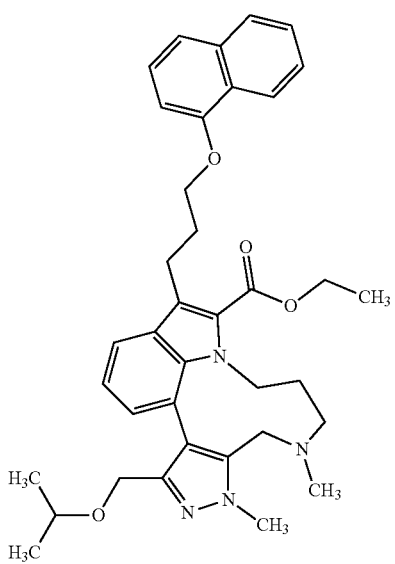 [SMILES: CCOC(=O)c1c(CCCOc2cccc3ccccc23)c2cccc3c2n1CCCN(C)Cc1c-3c(COC(C)C)nn1C]

To a solution of ethyl 7-{5-(bromomethyl)-1-methyl-3-[(propan-2-yloxy)methyl]-1H-pyrazol-4-yl}-1-[3-(methylamino)propyl]-3-[3-(naphthalen-1-yloxy)propyl]-1H-indole-2-carboxylate hydrochloric acid salt (325 mg) in DMF (45 ml) was added caesium carbonate (729 mg, 2.24 mmol) and the reaction was stirred at 65° C. for 4 days. For work-up the mixture was concentrated under reduced pressure and the residue was purified by flash chromatography (dichloromethane/methanol gradient, 0%→6% methanol) to give the title compound (200 mg).

LC-MS (Method 2): Rt=1.78 min; MS (ESIpos): m/z=609 [M+H]$^+$

Intermediate 1-124 ethyl 1-{4-[(tert-butoxycarbonyl)(methyl)amino]butyl}-7-{5-(hydroxymethyl)-1-methyl-3-[(propan-2-yloxy)methyl]-1H-pyrazol-4-yl}-3-[3-(naphthalen-1-yloxy)propyl]-1H-indole-2-carboxylate

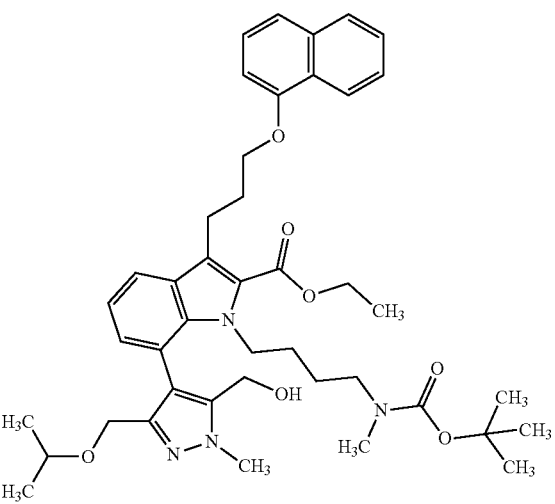 [SMILES: CCOC(=O)c1c(CCCOc2cccc3ccccc23)c2cccc(-c3c(COC(C)C)nn(C)c3CO)c2n1CCCCN(C)C(=O)OC(C)(C)C]

To a solution of ethyl 7-{5-(hydroxymethyl)-1-methyl-3-[(propan-2-yloxy)methyl]-1H-pyrazol-4-yl}-3-[3-(naphthalen-1-yloxy)propyl]-1H-indole-2-carboxylate (1.37 g, 2.47 mmol) in DMF (32 ml) was added caesium carbonate (4.02 g, 12.3 mmol) and the mixture was stirred for 10 min at room temperature. tert-Butyl (4-bromobutyl)methylcarbamate (788 mg, 2.96 mmol, prepared in analogy to Intermediate 1-1 with tert-butyl (4-hydroxybutyl)methylcarbamate as starting material) was added and the reaction was stirred for 2 days at room temperature. For work-up, the reaction mixture was poured into water. The mixture was extracted with ethyl acetate. The combined organic phases washed with brine and dried over sodium sulfate. After filtration and removal of the solvent, the crude product was purified twice by flash chromatography (dichloromethane/methanol gradient, 0%→10% methanol followed by dichloromethane/methanol gradient, 1.5%→5% methanol) to give the title compound (1.1 g) (contains ethyl 1-{4-[(tert-butoxycarbonyl)(methyl)amino]butyl}-7-[3-(ethoxymethyl)-5-(hydroxymethyl)-1-methyl-1H-pyrazol-4-yl]-3-[3-(1-naphthyloxy)propyl]-1H-indole-2-carboxylate as an impurity).

311

Intermediate 1-125 ethyl 7-{5-(bromomethyl)-1-methyl-3-[(propan-2-yloxy)methyl]-1H-pyrazol-4-yl}-1-{4-[(tert-butoxycarbonyl)(methyl)amino]butyl}-3-[3-(naphthalen-1-yloxy)propyl]-1H-indole-2-carboxylate

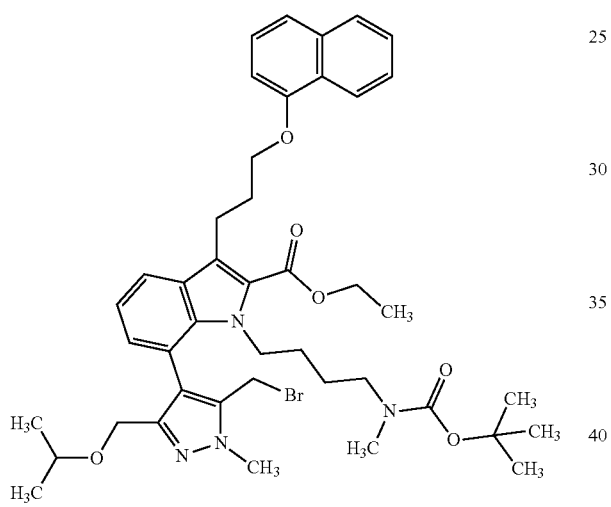

To a solution of ethyl 1-{4-[(tert-butoxycarbonyl)(methyl)amino]butyl}-7-{5-(hydroxymethyl)-1-methyl-3-[(propan-2-yloxy)methyl]-1H-pyrazol-4-yl}-3-[3-(naphthalen-1-yloxy)propyl]-1H-indole-2-carboxylate (1.15 g, 1.55 mmol) in dichloromethane (28 ml), triphenylphosphine (977 mg, 3.72 mmol) was added at 0° C. and the mixture was stirred at 0° C. for 10 min. Tetrabromomethane (1.13 g, 3.41 mmol) was added and the reaction was stirred at 0° C. for 4 hours. For work-up, the reaction mixture was concentrated under reduced pressure and the crude product was purified by flash chromatography (hexane/ethyl acetate gradient, 12%→50% ethyl acetate) to give the title compound (590 mg) (contains ethyl 7-[5-(bromomethyl)-3-(ethoxymethyl)-1-methyl-1H-pyrazol-4-yl]-1-{4-[(tert-butoxycarbonyl)(methyl)amino]butyl}-3-[3-(1-naphthyloxy)propyl]-1H-indole-2-carboxylate as an impurity).

312

Intermediate 1-126 ethyl 7-{5-(bromomethyl)-1-methyl-3-[(propan-2-yloxy)methyl]-1H-pyrazol-4-yl}-1-[4-(methylamino)butyl]-3-[3-(naphthalen-1-yloxy)propyl]-1H-indole-2-carboxylate hydrochloric acid salt

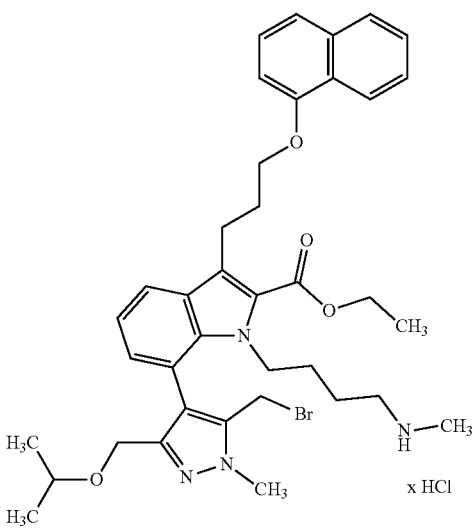 [SMILES: CCOC(=O)c1c(CCCOc2cccc3ccccc23)c2cccc(-c3c(COC(C)C)nn(C)c3CBr)c2n1CCCCNC]

To a solution of ethyl 7-{5-(bromomethyl)-1-methyl-3-[(propan-2-yloxy)methyl]-1H-pyrazol-4-yl}-1-{4-[(tert-butoxycarbonyl)(methyl)amino]butyl}-3-[3-(naphthalen-1-yloxy)propyl]-1H-indole-2-carboxylate (560 mg, 697 μmol) in methanol (13 ml) was added a 4 M solution of HCl in dioxan (12 ml, 4.0 M, 49 mmol) at 0° C., and the mixture was stirred for 3 h at room temperature. For work-up, the mixture was concentrated under reduced pressure and the crude product was used for the subsequent steps without further purification (contains ethyl 7-[5-(bromomethyl)-3-(ethoxymethyl)-1-methyl-1H-pyrazol-4-yl]-1-[4-(methylamino)butyl]-3-[3-(1-naphthyloxy)propyl]-1H-indole-2-carboxylate hydrochloric acid salt as an impurity).

Intermediate 1-127

(rac)-ethyl 1,14-dimethyl-7-[3-(naphthalen-1-yloxy)
propyl]-3-[(propan-2-yloxy)methyl]-10,11,12,13,14,
15-hexahydro-1H-pyrazolo[3',4':8,9][1,6]diazacy-
cloundecino[10,11,1-hi]indole-8-carboxylate

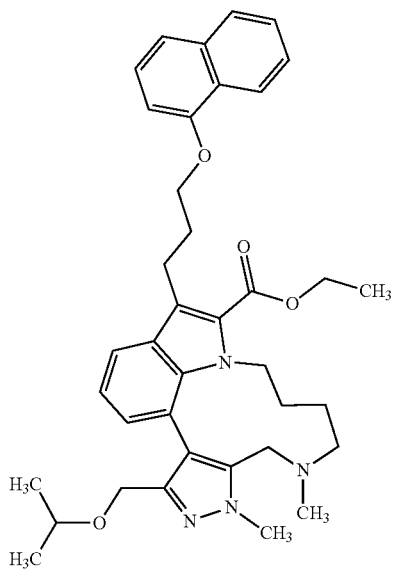 [SMILES: CCOC(=O)c1c(CCCOc2cccc3ccccc23)c2cccc3c2n1CCCCN(C)Cc1c-3c(COC(C)C)nn1C]

To a solution of ethyl 7-{5-(bromomethyl)-1-methyl-3-[(propan-2-yloxy)methyl]-1H-pyrazol-4-yl}-1-[4-(methylamino)butyl]-3-[3-(naphthalen-1-yloxy)propyl]-1H-indole-2-carboxylate hydrochloric acid salt (530 mg) in DMF (72 ml) was added caesium carbonate (1.17 g, 3.58 mmol) and the reaction was stirred at 65° C. for 4 days. For work-up the mixture was concentrated under reduced pressure and the residue was purified by flash chromatography (dichloromethane/methanol gradient, 0%→6% methanol) to give the title compound (420 mg) (contains (rac)-ethyl 3-(ethoxymethyl)-1,14-dimethyl-7-[3-(1-naphthyloxy)propyl]-10,11,12,13,14,15-hexahydro-1H-pyrazolo[3',4':8,9][1,6]diazacycloundecino[10,11,1-hi]indole-8-carboxylate as an impurity).

Intermediate 1-128 ethyl 4-bromo-1-methyl-3-(phenoxymethyl)-1H-
pyrazole-5-carboxylate

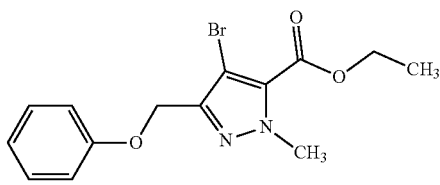 [SMILES: CCOC(=O)c1c(Br)c(COc2ccccc2)nn1C]

To a solution of phenol (919 mg, 99% purity, 9.66 mmol) in DMF (29 ml) was added potassium carbonate (3.82 g, 27.6 mmol) and the mixture was stirred for 10 min at room temperature. Ethyl 4-bromo-3-(bromomethyl)-1-methyl-1H-pyrazole-5-carboxylate (see Intermediate 1-5; 3.00 g, 9.20 mmol) was added and the reaction was stirred for 20 hours at room temperature. For work-up, the reaction mixture was poured into water. The mixture was extracted with ethyl acetate. The combined organic phases washed with brine and dried over sodium sulfate. After filtration and removal of the solvent the crude product was purified by flash chromatography (hexane/ethyl acetate gradient, 0%→50% ethyl acetate) to give the title compound (2.95 g).

LC-MS (Method 1): Rt=1.36 min; MS (ESIpos): m/z=339 [M+H]$^+$ $^1$H-NMR (400 MHz, CHLOROFORM-d) δ [ppm]: 0.015 (0.59), 0.033 (0.63), 1.365 (3.83), 1.382 (7.71), 1.401 (3.83), 1.512 (4.75), 3.914 (0.59), 4.130 (16.00), 4.160 (0.62), 4.342 (1.23), 4.360 (3.89), 4.378 (3.88), 4.396 (1.20), 5.011 (9.31), 6.912 (0.68), 6.915 (0.44), 6.931 (1.47), 6.947 (0.48), 6.949 (0.86), 6.952 (0.60), 6.974 (1.75), 6.976 (2.09), 6.979 (1.18), 6.991 (0.70), 6.996 (2.63), 6.999 (2.00), 7.234 (1.84), 7.239 (0.69), 7.252 (2.11), 7.256 (2.10), 7.269 (0.56), 7.274 (1.48).

Intermediate 1-129

[4-bromo-1-methyl-3-(phenoxymethyl)-1H-pyrazol-
5-yl]methanol

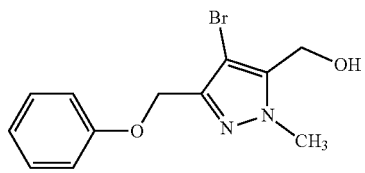 [SMILES: Cn1nc(COc2ccccc2)c(Br)c1CO]

To a solution of ethyl 4-bromo-1-methyl-3-(phenoxymethyl)-1H-pyrazole-5-carboxylate (2.95 g, 8.70 mmol) in THF (71 ml) at 0° C. was added a solution of lithium aluminium hydride in THF (4.3 ml, 2.0 M, 8.7 mmol) and the mixture was stirred at 0° C. for 1 hour. Ice was added and the mixture was stirred for 30 minutes. The reaction was poured into water and the mixture was extracted with ethyl acetate. The combined organic layers were washed with brine and dried over sodium sulfate. After filtration and removal of the solvents the crude product (2.5 g) was used without further purification in the subsequent steps.

315

Intermediate 1-130 ethyl 7-[5-(hydroxymethyl)-1-methyl-3-(phenoxymethyl)-1H-pyrazol-4-yl]-3-[3-(naphthalen-1-yloxy)propyl]-1H-indole-2-carboxylate

316

Intermediate 1-131 ethyl 7-{1-methyl-3-(phenoxymethyl)-5-[(prop-2-en-1-yloxy)methyl]-1H-pyrazol-4-yl}-3-[3-(naphthalen-1-yloxy)propyl]-1-(prop-2-en-1-yl)-1H-indole-2-carboxylate

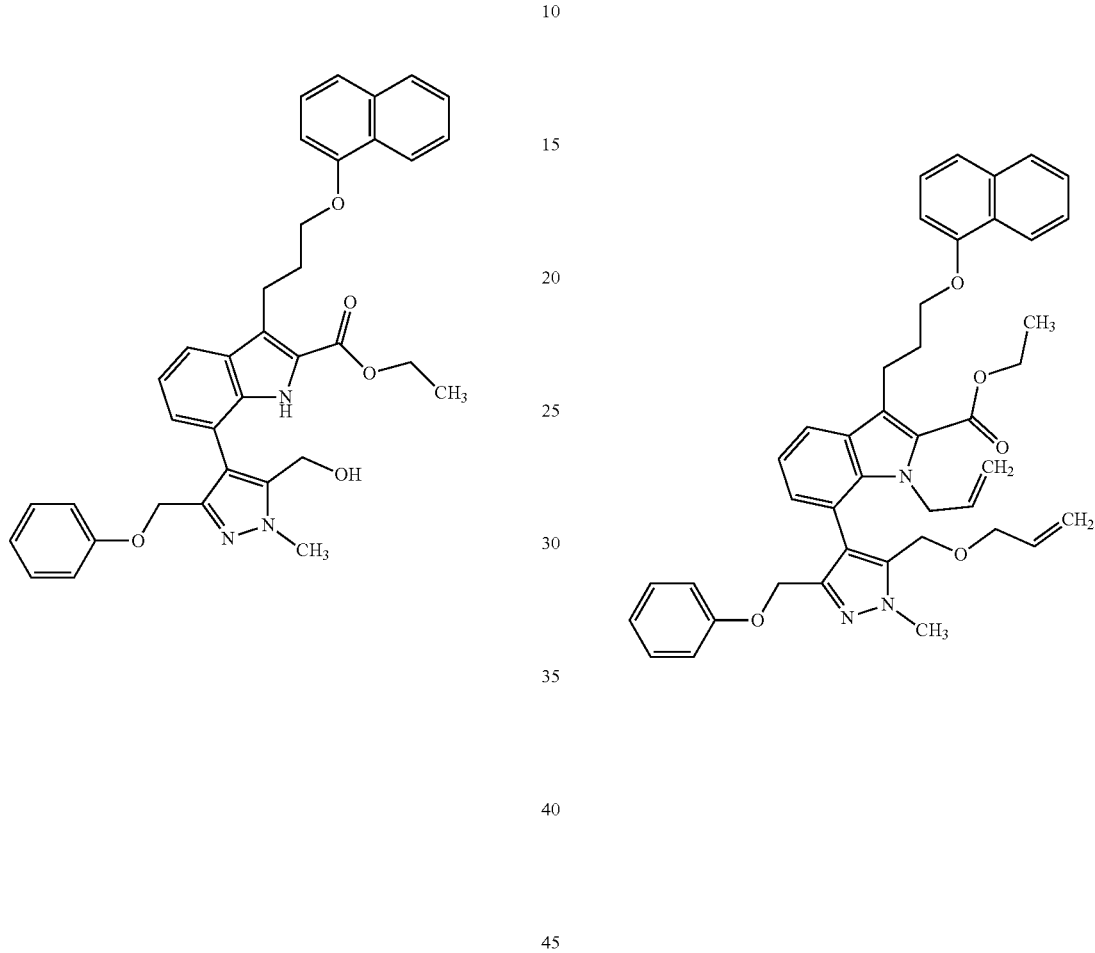

To a solution of ethyl 3-[3-(naphthalen-1-yloxy)propyl]-7-(4,4,5,5-tetramethyl-1,3,2-dioxaborolan-2-yl)-1H-indole-2-carboxylate (see Intermediate 1-4; 2.52 g, 5.05 mmol) and [4-bromo-1-methyl-3-(phenoxymethyl)-1H-pyrazol-5-yl]methanol (1.50 g, 5.05 mmol) in 1,4-dioxane (65 ml) were added aqueous 2 M solution of potassium carbonate (7.6 ml, 2.0 M, 15 mmol). The mixture was degassed and purged with argon several times. Pd(dppf)Cl$_2$×CH$_2$Cl$_2$ (824 mg, 1.01 mmol) was added and the mixture was purged with argon for 10 minutes. The reaction was stirred at 80° C. for 5 h. For work-up, the reaction mixture was concentrated under reduced pressure and the residue was purified by flash chromatography (hexane/ethyl acetate gradient, 50%→100% ethyl acetate) to give the title compound (2.1 g).

LC-MS (Method 2): Rt=1.66 min; MS (ESIpos): m/z=590 [M+H]$^+$

To a solution of ethyl 7-[5-(hydroxymethyl)-1-methyl-3-(phenoxymethyl)-1H-pyrazol-4-yl]-3-[3-(naphthalen-1-yloxy)propyl]-1H-indole-2-carboxylate (700 mg, 1.19 mmol) in THF (16 ml) was added sodium hydride (104 mg, 60% purity, 2.61 mmol) at 0° C. and the mixture was stirred for 2 hours at room temperature. The reaction was cooled down to 0° C. and a solution of allyl bromide (230 µl, 2.6 mmol) in THF (1 ml) was added. The mixture was stirred for 5 days at room temperature. For work-up, a sodium chloride solution was added and the mixture was extracted with ethyl acetate. The combined organic phases were washed with brine and were dried over sodium sulfate. After filtration and removal of the solvent, the crude product was purified by flash chromatography (hexane/ethyl acetate gradient, 12%→60% ethyl acetate) to give the title compound (330 mg).

317

Intermediate 1-132

(rac)- (E/Z)-ethyl-1-methyl-7-[3-(naphthalen-1-yloxy)propyl]-3-(phenoxymethyl)-1,10,13,15-tetrahydropyrazolo[4',3':9,10][1,6]oxazacycloundecino[8,7,6-hi]indole-8-carboxylate

318

Intermediate 1-133

(rac)-ethyl 1-methyl-7-[3-(naphthalen-1-yloxy)propyl]-3-(phenoxymethyl)-1,10,11,12,13,15-hexahydropyrazolo[4',3':9,10][1,6]oxazacycloundecino[8,7,6-hi]indole-8-carboxylate

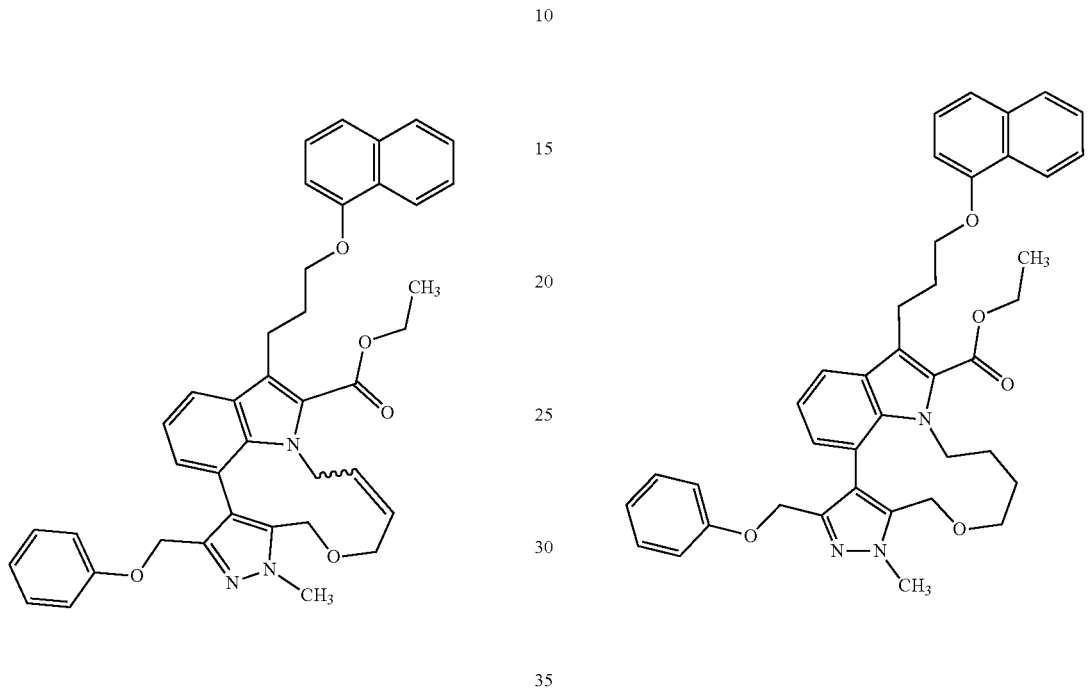

A solution of ethyl 7-{1-methyl-3-(phenoxymethyl)-5-[(prop-2-en-1-yloxy)methyl]-1H-pyrazol-4-yl}-3-[3-(naphthalen-1-yloxy)propyl]-1-(prop-2-en-1-yl)-1H-indole-2-carboxylate (330 mg, 493 µmol) in dichloromethane (6.3 ml) was purged with argon several times. (1,3-Bis(2,4,6-trimethylphenyl)-2-imidazolidinylidene)dichloro(phenylmethylene)(tricyclohexylphosphine)ruthenium (41.8 mg, 49.3 µmol) (Grubbs $2^{nd}$ generation catalyst) was added and the reaction was stirred for 24 hours at room temperature. For work-up, the reaction mixture was concentrated under reduced pressure and the residue was purified by flash chromatography (hexane/ethyl acetate gradient, 12%→100% ethyl acetate) to give the title compound (180 mg).

A suspension of (rac)-(E/Z)-ethyl 1-methyl-7-[3-(naphthalen-1-yloxy)propyl]-3-(phenoxymethyl)-1,10,13,15-tetrahydropyrazolo[4',3':9,10][1,6]oxazacycloundecino[8,7,6-hi]indole-8-carboxylate (180 mg, 280 µmol) and Pd/C (29.8 mg, 10 wt-% Pd, 28.0 µmol) in ethanol (4.9 ml, 84 mmol) was stirred under an atmosphere of hydrogen at room temperature for 24 hours. For work-up the mixture was filtered through a pad of celite. The residue was washed with ethyl acetate and the filtrate was concentrated under reduced pressure. The residue was purified by flash chromatography (dichloromethane/methanol gradient, 0%→10% methanol) to give the title compound (125 mg).

LC-MS (Method 2): Rt=1.77 min; MS (ESIpos): m/z=644 [M+H]$^+$

The title compound (125 mg) was separated into enantiomers by chiral HPLC to give enantiomer 1 and enantiomer 2.

Preparative chiral HPLC method: Instrument: Labomatic HD5000, Labocord-5000; Gilson GX-241, Labcol Vario 4000, column: Chiralpak IA 5µ 250×30 mm; eluent A: hexane+0.1 Vol-% diethyl amine (99%); eluent B: ethanol; gradient: 5-50% B in 20 min; flow 40.0 ml/min; UV 254 nm Analytical chiral HPLC method: Instrument: Agilent HPLC 1260; column: Chiralpak IA 3µ 100×4.6 mm; eluent A: hexane+0.1 Vol-% diethyl amine (99%); eluent B: 2-propanol; gradient: 5-50% B in 7 min; flow 1.4 ml/min; temperature: 25° C.; DAD 254 nm

Intermediate 1-134 ethyl 1-methyl-7-[3-(naphthalen-1-yloxy)propyl]-3-(phenoxymethyl)-1,10,11,12,13,15-hexahydropyrazolo[4',3':9,10][1,6]oxazacycloundecino[8,7,6-hi]indole-8-carboxylate (Enantiomer 1)

Chiral separation (method see Intermediate 1-133) gave the title compound (20 mg).
Analytical Chiral HPLC (method see intermediate 133): $R_t$=3.95 min.

Intermediate 1-135 ethyl 1-methyl-7-[3-(naphthalen-1-yloxy)propyl]-3-(phenoxymethyl)-1,10,11,12,13,15-hexahydropyrazolo[4',3':9,10][1,6]oxazacycloundecino[8,7,6-hi]indole-8-carboxylate (Enantiomer 2)

Chiral separation (method see Intermediate 1-133) gave the title compound (25 mg).
Analytical Chiral HPLC (method see Intermediate 1-133): $R_t$=5.78 min.

Intermediate 1-136 ethyl 1-{3-[(tert-butoxycarbonyl)(methyl)amino]propyl}-7-[5-(hydroxymethyl)-1-methyl-3-(phenoxymethyl)-1H-pyrazol-4-yl]-3-[3-(naphthalen-1-yloxy)propyl]-1H-indole-2-carboxylate

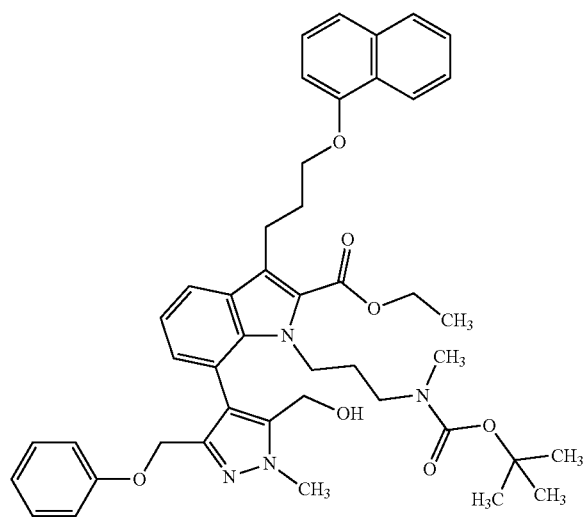 [SMILES: CCOC(=O)c1c(CCCOc2cccc3ccccc23)c2cccc(-c3c(COc4ccccc4)nn(C)c3CO)c2n1CCCN(C)C(=O)OC(C)(C)C]

To a solution of ethyl 7-[5-(hydroxymethyl)-1-methyl-3-(phenoxymethyl)-1H-pyrazol-4-yl]-3-[3-(naphthalen-1-yloxy)propyl]-1H-indole-2-carboxylate (see Intermediate 1-130; 700 mg, 1.19 mmol) in DMF (16 ml) was added caesium carbonate (1.93 g, 5.94 mmol) and the mixture was stirred for 10 min at room temperature. Tert-butyl (3-bromopropyl)methylcarbamate (see Intermediate 1-1; 359 mg, 1.42 mmol) was added and the reaction was stirred for 24 hours at room temperature and for 7 hours at 70° C. For work-up, the reaction mixture was poured into water. The mixture was extracted with ethyl acetate. The combined organic phases were washed with brine and dried over sodium sulfate. After filtration and removal of the solvent, the crude product was purified by flash chromatography (Biotage SNAP cartridge NH$_2$ silica, dichloromethane/ethyl acetate gradient, 0%→100% ethyl acetate) to give the title compound (280 mg).

Intermediate 1-137 ethyl 7-[5-(bromomethyl)-1-methyl-3-(phenoxymethyl)-1H-pyrazol-4-yl]-1-{3-[(tert-butoxycarbonyl)(methyl)amino]propyl}-3-[3-(naphthalen-1-yloxy)propyl]-1H-indole-2-carboxylate

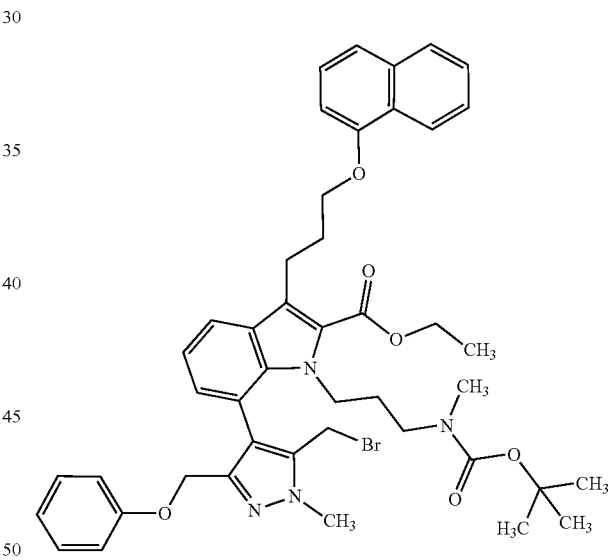

To a solution of ethyl 1-{3-[(tert-butoxycarbonyl)(methyl)amino]propyl}-7-[5-(hydroxymethyl)-1-methyl-3-(phenoxymethyl)-1H-pyrazol-4-yl]-3-[3-(naphthalen-1-yloxy)propyl]-1H-indole-2-carboxylate (280 mg, 368 µmol) in dichloromethane (6.7 ml), triphenylphosphine (232 mg, 883 µmol) was added at 0° C. and the mixture was stirred at 0° C. for 10 min. Tetrabromomethane (268 mg, 810 µmol) was added and the reaction was stirred for 2 hours at room temperature. For work-up, the reaction mixture was concentrated under reduced pressure and the crude product (303 mg) was used in the subsequent steps without further purification.

321

Intermediate 1-138 ethyl 7-[5-(bromomethyl)-1-methyl-3-(phenoxymethyl)-1H-pyrazol-4-yl]-1-[3-(methylamino)propyl]-3-[3-(naphthalen-1-yloxy)propyl]-1H-indole-2-carboxylate hydrochloric acid salt

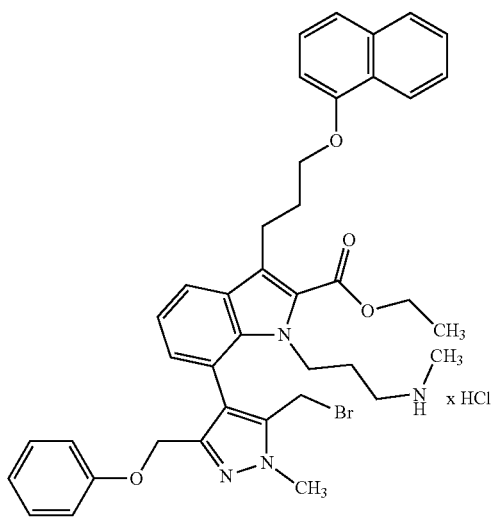 [SMILES: CCOC(=O)c1c(CCCOc2cccc3ccccc23)c2cccc(-c3c(COc4ccccc4)nn(C)c3CBr)c2n1CCCNC]

To a solution of ethyl 7-[5-(bromomethyl)-1-methyl-3-(phenoxymethyl)-1H-pyrazol-4-yl]-1-{3-[(tert-butoxycarbonyl)(methyl)amino]propyl}-3-[3-(naphthalen-1-yloxy)propyl]-1H-indole-2-carboxylate (303 mg, 368 µmol) in methanol (6.7 ml) was added a 4 M solution of HCl in dioxan (6.8 ml, 4.0 M, 27 mmol) at 0° C., and the mixture was stirred for 2 hours at room temperature. For work-up, the mixture was concentrated under reduced pressure and the crude product (280 mg) was used for the subsequent steps without further purification.

322

Intermediate 1-139

(rac)-ethyl 7,9-dimethyl-1-[3-(naphthalen-1-yloxy)propyl]-11-(phenoxymethyl)-4,5,6,7,8,9-hexahydropyrazolo[3',4':7,8][1,5]diazecino[9,10,1-hi]indole-2-carboxylate

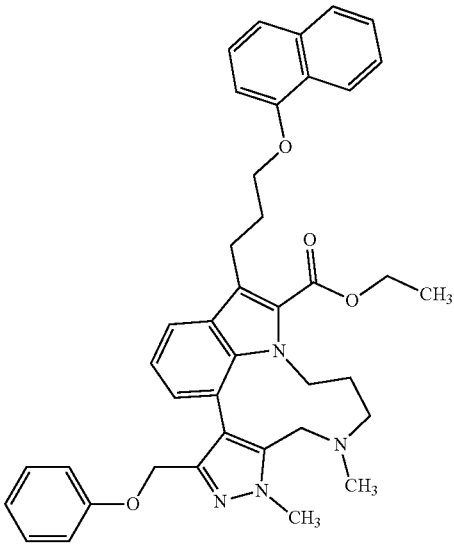 [SMILES: CCOC(=O)c1c(CCCOc2cccc3ccccc23)c2cccc3c2n1CCCN(C)Cc1c-3c(COc2ccccc2)nn1C]

To a solution of ethyl 7-[5-(bromomethyl)-1-methyl-3-(phenoxymethyl)-1H-pyrazol-4-yl]-1-[3-(methylamino)propyl]-3-[3-(naphthalen-1-yloxy)propyl]-1H-indole-2-carboxylate hydrochloric acid salt (280 mg) in DMF (37 ml) was added caesium carbonate (600 mg, 1.84 mmol) and the reaction was stirred at 65° C. for 20 hours. For work-up the mixture was concentrated under reduced pressure and the residue was purified twice by flash chromatography (dichloromethane/ethyl acetate gradient, 0%→100% ethyl acetate followed by additional flash chromatography (Biotage SNAP cartridge NH$_2$ silica dichloromethane/ethyl acetate gradient, 0%→10% ethyl acetate) to give the title compound (145 mg).

LC-MS (Method 2): Rt=1.82 min; MS (ESIpos): m/z=643 [M+H]$^+$ $^1$H-NMR (400 MHz, CHLOROFORM-d) δ [ppm]: 0.000 (0.52), 0.009 (16.00), 0.018 (0.56), 1.131 (0.50), 1.149 (1.03), 1.167 (0.57), 1.194 (1.10), 1.294 (5.09), 1.312 (10.78), 1.330 (5.02), 1.513 (2.57), 2.195 (3.84), 2.219 (0.71), 2.237 (1.30), 2.254 (1.97), 2.271 (1.29), 2.288 (0.51), 3.137 (0.52), 3.172 (0.65), 3.259 (0.56), 3.274 (0.64), 3.293 (1.06), 3.311 (0.51), 3.329 (0.60), 3.348 (1.11), 3.367 (0.74), 3.381 (0.69), 3.410 (0.67), 3.427 (0.89), 3.458 (0.51), 3.750 (0.58), 3.761 (0.41), 3.924 (5.51), 4.112 (1.71), 4.127 (3.61), 4.142 (1.62), 4.223 (0.46), 4.232 (0.54), 4.241 (0.52), 4.249 (2.07), 4.267 (3.25), 4.285 (2.33), 4.294 (0.66), 4.302 (0.82), 4.311 (0.81), 4.318 (0.88), 4.330 (0.59), 4.343 (0.41), 4.356 (0.76), 4.767 (1.06), 4.795 (3.67), 4.814 (3.43), 4.841 (1.00), 4.953 (1.37), 6.665 (1.72), 6.674 (2.41), 6.684 (1.94), 6.692 (2.35), 6.746 (1.03), 6.764 (2.21), 6.780 (0.80), 6.783 (1.24), 6.935 (0.42), 6.949 (1.22), 6.964 (2.87), 6.968 (3.29), 6.981 (0.83), 6.991 (0.47), 7.038 (2.76), 7.043 (0.94), 7.056 (3.09), 7.059 (3.05), 7.073 (0.78), 7.078 (2.10), 7.212 (0.43), 7.255 (1.44), 7.276 (2.64), 7.295 (2.16), 7.342 (2.52), 7.362 (1.49), 7.404 (0.47), 7.416 (1.58), 7.419 (2.30), 7.429 (2.76), 7.438 (2.09), 7.443 (1.98), 7.455 (0.57), 7.617 (0.87), 7.634 (0.91), 7.733 (1.46), 7.736 (0.96), 7.746 (1.02), 7.750 (0.86), 7.756 (1.22), 8.293 (0.72), 8.302 (0.70), 8.316 (0.69).

Intermediate 1-140 ethyl 3-[3-(4-chloro-3,5-dimethylphenoxy)propyl]-7-[5-(hydroxymethyl)-1-methyl-3-(phenoxymethyl)-1H-pyrazol-4-yl]-1H-indole-2-carboxylate

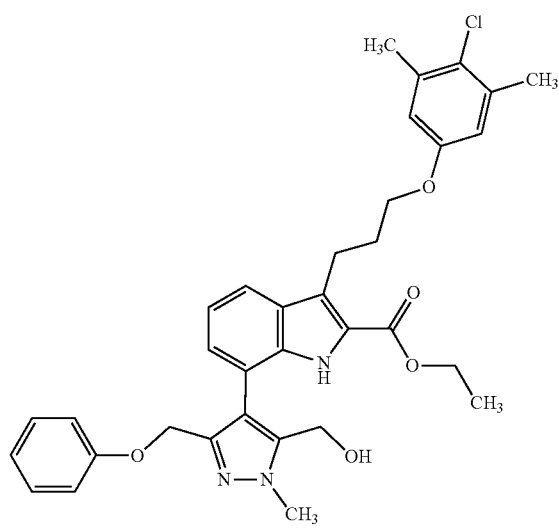

To a solution of ethyl 3-[3-(4-chloro-3,5-dimethylphenoxy)propyl]-7-(4,4,5,5-tetramethyl-1,3,2-dioxaborolan-2-yl)-1H-indole-2-carboxylate (1.81 g, 3.53 mmol, prepared as described in WO 2015031608) and [4-bromo-1-methyl-3-(phenoxymethyl)-1H-pyrazol-5-yl]methanol (see Intermediate 1-129; 1.00 g, 3.37 mmol) in 1,4-dioxane (44 ml) were added aqueous 2 M solution of potassium carbonate (5.0 ml, 2.0 M, 10 mmol). The mixture was degassed and purged with argon several times. Pd(dppf)Cl$_2$×CH$_2$Cl$_2$ (550 mg, 673 µmol) was added and the mixture was purged with argon for 10 minutes. The reaction was stirred at 80° C. for 18 h. For work-up, the reaction mixture was diluted with ethyl acetate and washed with water. The organic phase was washed with brine and was filtrated through a silicone filter. The organic phase was concentrated and the residue was purified by flash chromatography (hexane/dichloromethane gradient, 0%→100% dichloromethane, then dichloromethane/ethyl acetate gradient, 0%→50% ethyl acetate) to give the title compound (427 mg).

LC-MS (Method 1): Rt=1.68 min; MS (ESIpos): m/z=602 [M+H]$^+$

Intermediate 1-141 ethyl 1-{3-[(tert-butoxycarbonyl)(methyl)amino]propyl}-3-[3-(4-chloro-3,5-dimethylphenoxy)propyl]-7-[5-(hydroxymethyl)-1-methyl-3-(phenoxymethyl)-1H-pyrazol-4-yl]-1H-indole-2-carboxylate

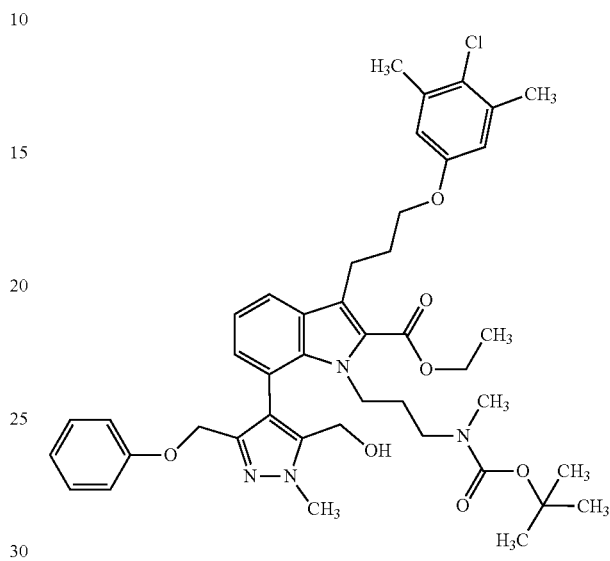

To a solution of ethyl 3-[3-(4-chloro-3,5-dimethylphenoxy)propyl]-7-[5-(hydroxymethyl)-1-methyl-3-(phenoxymethyl)-1H-pyrazol-4-yl]-1H-indole-2-carboxylate (425 mg, 706 µmol) in DMF (8.7 ml, 110 mmol) were added caesium carbonate (1.15 g, 3.53 mmol) and tert-butyl (3-bromopropyl)methylcarbamate (see Intermediate 1-1; 214 mg, 847 µmol), and the reaction was stirred for 3 hours at 60° C. An additional portion of tert-butyl (3-bromopropyl)methylcarbamate (89 mg, 353 µmol) was added and the mixture was stirred for another 2 hours at 60° C. For work-up, the reaction mixture was poured into aqueous sodium chloride solution. The resulting precipitate was collected via filtration and the residue was washed with water. The residue was purified by flash chromatography (dichloromethane/ethyl acetate gradient, 0%→100% ethyl acetate) to give the title compound (207 mg).

LC-MS (Method 1): Rt=1.90 min; MS (ESIpos): m/z=773 [M+H]$^+$ $^1$H-NMR (400 MHz, DMSO-d6) δ [ppm]: 1.066 (0.67), 1.154 (2.41), 1.172 (4.85), 1.190 (2.43), 1.232 (0.62), 1.266 (2.61), 1.308 (2.94), 1.325 (5.64), 1.343 (3.29), 1.370 (1.93), 1.380 (2.05), 1.988 (9.23), 2.013 (0.59), 2.262 (16.00), 2.327 (0.42), 2.518 (1.50), 2.523 (1.05), 2.550 (1.86), 2.665 (0.49), 2.669 (0.59), 2.673 (0.45), 2.729 (1.13), 2.888 (1.20), 3.117 (0.63), 3.136 (0.97), 3.154 (0.60), 3.939 (1.07), 3.955 (3.05), 3.999 (0.71), 4.018 (1.93), 4.035 (1.93), 4.053 (0.65), 4.272 (0.90), 4.290 (2.39), 4.307 (2.18), 4.325 (0.70), 4.750 (1.17), 6.712 (1.33), 6.738 (4.96), 6.799 (0.47), 6.817 (1.01), 6.836 (0.57), 7.053 (0.44), 7.067 (1.31), 7.074 (1.87), 7.093 (1.42), 7.106 (1.25), 7.110 (1.04), 7.125 (1.56), 7.146 (0.91), 7.675 (0.95), 7.679 (0.86), 7.693 (0.82), 7.698 (0.86).

325

Intermediate 1-142 ethyl 7-[5-(bromomethyl)-1-methyl-3-(phenoxymethyl)-1H-pyrazol-4-yl]-1-{3-[(tert-butoxycarbonyl)(methyl)amino]propyl}-3-[3-(4-chloro-3,5-dimethylphenoxy)propyl]-1H-indole-2-carboxylate

326

Intermediate 1-143 ethyl 7-[5-(bromomethyl)-1-methyl-3-(phenoxymethyl)-1H-pyrazol-4-yl]-3-[3-(4-chloro-3,5-dimethylphenoxy)propyl]-1-[3-(methylamino)propyl]-1H-indole-2-carboxylate hydrochloric acid salt

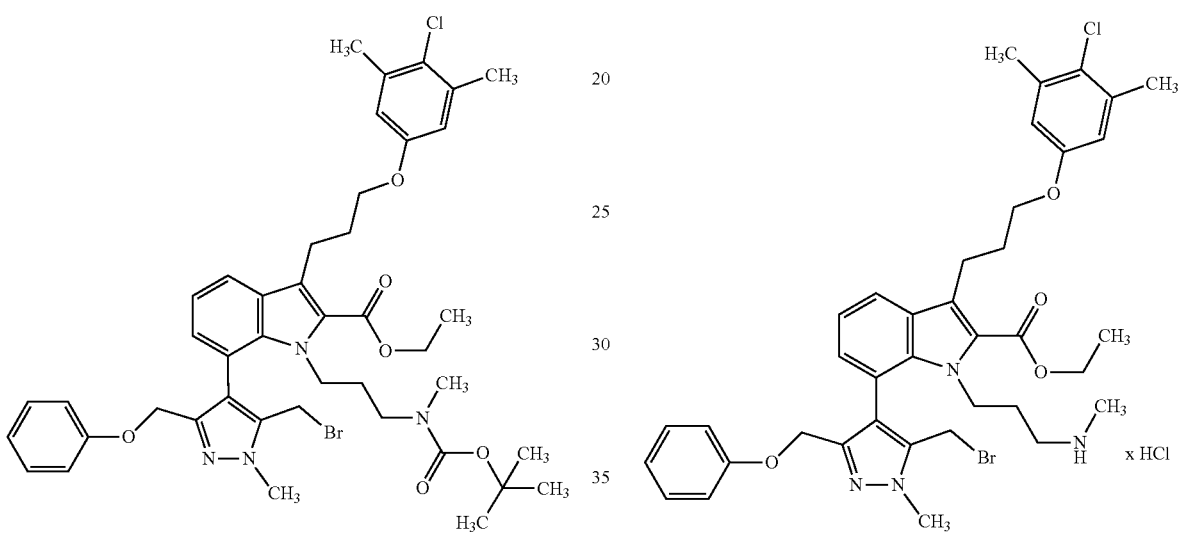

To a solution of ethyl 1-{3-[(tert-butoxycarbonyl)(methyl)amino]propyl}-3-[3-(4-chloro-3,5-dimethylphenoxy)propyl]-7-[5-(hydroxymethyl)-1-methyl-3-(phenoxymethyl)-1H-pyrazol-4-yl]-1H-indole-2-carboxylate (205 mg, 265 µmol) in dichloromethane (4.8 ml), triphenylphosphine (167 mg, 636 µmol) was added at 0° C. and the mixture was stirred at 0° C. for 10 min. Tetrabromomethane (193 mg, 583 µmol) was added and the reaction was stirred for 90 minutes at room temperature. For work-up, the reaction mixture was concentrated under reduced pressure and the crude product was used in the subsequent steps without further purification.

To a solution of ethyl 7-[5-(bromomethyl)-1-methyl-3-(phenoxymethyl)-1H-pyrazol-4-yl]-1-{3-[(tert-butoxycarbonyl)(methyl)amino]propyl}-3-[3-(4-chloro-3,5-dimethylphenoxy)propyl]-1H-indole-2-carboxylate (222 mg, 265 µmol) in methanol (4.8 ml) was added a 4 M solution of HCl in dioxan (4.8 ml, 4.0 M, 19 mmol) at 0° C., and the mixture was stirred for 2 hours at room temperature. For work-up, the mixture was concentrated under reduced pressure and the crude product was used for the subsequent steps without further purification.

Intermediate 1-144

(rac)-ethyl 1-[3-(4-chloro-3,5-dimethylphenoxy)propyl]-7,9-dimethyl-11-(phenoxymethyl)-4,5,6,7,8,9-hexahydropyrazolo[3',4':7,8][1,5]diazecino[9,10,1-hi]indole-2-carboxylate

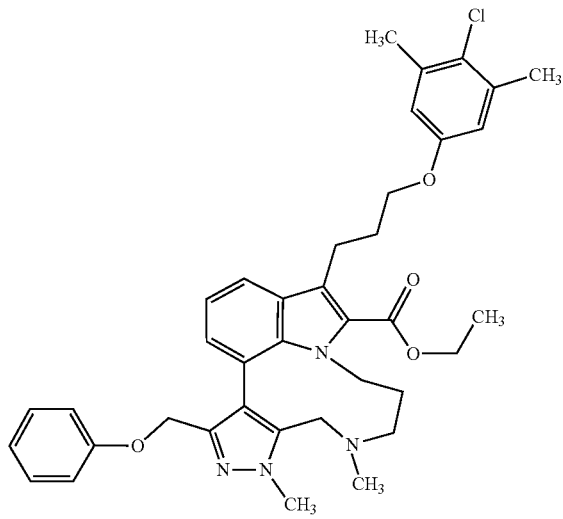

To a solution of ethyl 7-[5-(bromomethyl)-1-methyl-3-(phenoxymethyl)-1H-pyrazol-4-yl]-3-[3-(4-chloro-3,5-dimethylphenoxy)propyl]-1-[3-(methylamino)propyl]-1H-indole-2-carboxylate hydrochloric acid salt (252 mg) in DMF (33 ml) was added caesium carbonate (532 mg, 1.63 mmol) and the reaction was stirred at 65° C. for 16 hours. For work-up the mixture was poured into water and sodium chloride was added. The mixture was stirred for 10 minutes. The resulting precipitate was collected via filtration and the residue was washed with water. The residue was purified by flash chromatography (hexane/dichloromethane gradient, 10%→100% dichloromethane) to give the title compound (120 mg).

LC-MS (Method 2): Rt=1.86 min; MS (ESIpos): m/z=655 [M+H]+

$^1$H-NMR (400 MHz, DMSO-d6) δ [ppm]: 0.814 (0.41), 0.831 (0.95), 0.837 (0.43), 0.841 (0.46), 0.850 (0.55), 0.853 (0.58), 0.858 (1.06), 0.937 (0.81), 0.953 (0.87), 1.238 (0.76), 1.302 (2.78), 1.320 (6.07), 1.337 (2.82), 1.395 (2.19), 1.479 (0.48), 1.983 (0.64), 2.000 (0.96), 2.016 (0.65), 2.184 (6.23), 2.262 (16.00), 2.323 (0.58), 2.327 (0.74), 2.331 (0.58), 2.518 (1.74), 2.523 (1.15), 2.669 (0.52), 3.013 (0.87), 3.050 (0.93), 3.127 (0.57), 3.190 (0.56), 3.643 (1.13), 3.679 (1.23), 3.889 (9.03), 3.922 (0.79), 3.937 (1.60), 3.953 (0.75), 4.231 (0.61), 4.240 (0.70), 4.249 (0.70), 4.258 (1.09), 4.267 (0.64), 4.276 (1.48), 4.285 (1.27), 4.294 (0.48), 4.303 (0.99), 4.312 (0.42), 4.330 (0.42), 4.758 (3.86), 6.624 (1.59), 6.627 (1.91), 6.647 (2.04), 6.649 (1.60), 6.733 (4.39), 6.768 (0.59), 6.786 (1.26), 6.804 (0.72), 6.961 (0.79), 6.965 (0.88), 6.979 (1.43), 6.982 (1.33), 7.012 (1.29), 7.032 (1.38), 7.049 (0.83), 7.059 (1.59), 7.063 (0.56), 7.077 (1.82), 7.080 (1.77), 7.094 (0.46), 7.099 (1.25), 7.650 (1.02), 7.653 (1.06), 7.670 (0.98), 7.673 (0.93).

Intermediate 1-145 ethyl 4-bromo-1-methyl-3-{[4-(morpholin-4-yl)phenoxy]methyl}-1H-pyrazole-5-carboxylate

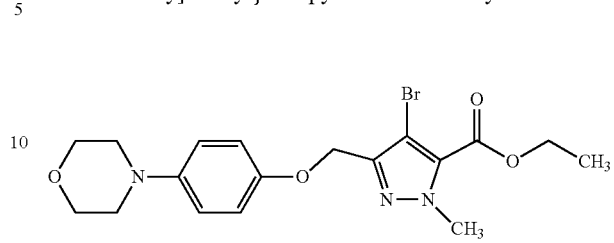

To a solution of 4-(morpholin-4-yl)phenol (2.00 g, 11.2 mmol, CAS 6291-23-2) in (4.41 g, 31.9 mmol) was added potassium carbonate DMF (35 ml) and the mixture was stirred for 10 min at room temperature. ethyl 4-bromo-3-(bromomethyl)-1-methyl-1H-pyrazole-5-carboxylate (see Intermediate 1-5; 3.46 g, 10.6 mmol) was added and the reaction was stirred for 4 hours at room temperature. For work-up, the reaction mixture was concentrated under reduced pressure. The residue was partitioned between water and ethyl acetate and the aqueous phase was then extracted with ethyl acetate. The combined organic phases were washed with aqueous 2 M sodium hydroxide solution and brine and dried over sodium sulfate. After filtration and removal of the solvent, the crude product was triturated with methanol to give the title compound (4 g).

LC-MS (Method 1): Rt=424.00 min; MS (ESIpos): m/z=1 [M+H]+

$^1$H-NMR (400 MHz, CHLOROFORM-d) δ [ppm]: 1.416 (4.00), 1.433 (8.05), 1.452 (3.90), 3.064 (1.27), 3.076 (1.70), 3.087 (1.31), 3.855 (1.39), 3.867 (1.87), 3.877 (1.40), 4.176 (16.00), 4.392 (1.27), 4.410 (3.97), 4.428 (3.68), 4.446 (1.16), 5.016 (5.93), 6.979 (1.81), 7.002 (1.19).

Intermediate 1-146

(4-bromo-1-methyl-3-{[4-(morpholin-4-yl)phenoxy]methyl}-1H-pyrazol-5-yl)methanol

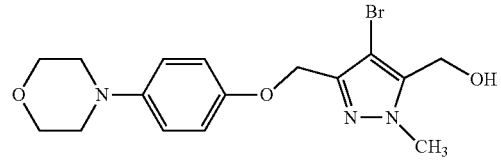 [SMILES: Cn1nc(COc2ccc(N3CCOCC3)cc2)c(Br)c1CO]

To a solution of ethyl 4-bromo-1-methyl-3-{[4-(morpholin-4-yl)phenoxy]methyl}-1H-pyrazole-5-carboxylate (4.03 g, 9.50 mmol) in THF (95 mL) at 0° C. was added a solution of lithium aluminium hydride in THF (4.7 ml, 2.0 M, 9.5 mmol), and the mixture was stirred at 0° C. for 1 hour. For work-up, aqueous 2 M sodium hydroxide solution (4 ml) was added and the mixture was stirred for 10 min. Sodium sulfate was added and the mixture was stirred for 10 min. The mixture was filtrated and the filtrate was concentrated under reduced pressure to give the crude title compound (3.54 g) which was used without further purification.

LC-MS (Method 2): Rt=0.93 min; MS (ESIpos): m/z=382 [M+H]+

Intermediate 1-147 ethyl 7-[5-(hydroxymethyl)-1-methyl-3-{[4-(morpholin-4-yl)phenoxy]methyl}-1H-pyrazol-4-yl]-3-[3-(naphthalen-1-yloxy)propyl]-1H-indole-2-carboxylate

Intermediate 1-148 ethyl 1-{3-[(tert-butoxycarbonyl)(methyl)amino]propyl}-7-[5-(hydroxymethyl)-1-methyl-3-{[4-(morpholin-4-yl)phenoxy]methyl}-1H-pyrazol-4-yl]-3-[3-(naphthalen-1-yloxy)propyl]-1H-indole-2-carboxylate

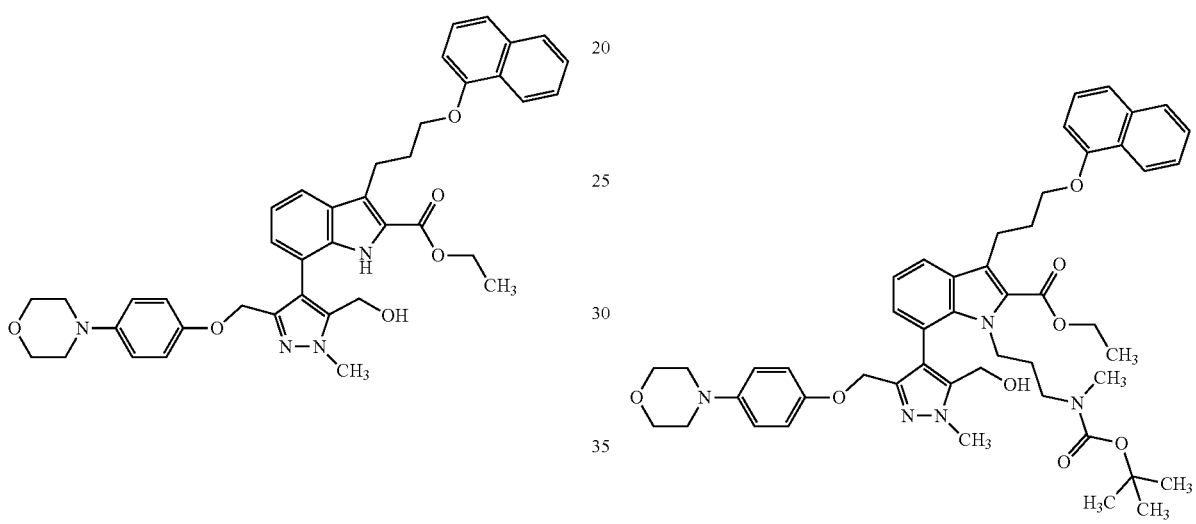

To a solution of ethyl 3-[3-(naphthalen-1-yloxy)propyl]-7-(4,4,5,5-tetramethyl-1,3,2-dioxaborolan-2-yl)-1H-indole-2-carboxylate (see Intermediate 1-4; 3.85 g, 7.72 mmol) and (4-bromo-1-methyl-3-{[4-(morpholin-4-yl)phenoxy]methyl}-1H-pyrazol-5-yl)methanol (3.35 g, 80% purity, 7.01 mmol) in 1,4-dioxane (90 ml) were added aqueous 2 M solution of potassium carbonate (11 ml, 2.0 M, 21 mmol). The mixture was degassed and purged with argon several times. Pd(dppf)Cl$_2$×CH$_2$Cl$_2$ (1.15 g, 1.40 mmol) was added and the mixture was purged with argon for 10 minutes. The reaction was stirred at 80° C. for 16 h. For work-up, the reaction mixture was diluted with ethyl acetate and was filtered through a pad of celite. The filtrate was concentrated under reduced pressure and the residue was dissolved in ethyl acetate. The organic phase was washed with water and brine and the organic phase was dried over sodium sulfate. The mixture was filtrated and the filtrate was concentrated under reduced pressure. The residue was purified by flash chromatography (dichloromethane/ethyl acetate gradient, 17%→100% ethyl acetate) to give the title compound (3.9 g).

LC-MS (Method 2): Rt=1.58 min; MS (ESIpos): m/z=675 [M+H]$^+$

To a solution of ethyl 7-[5-(hydroxymethyl)-1-methyl-3-{[4-(morpholin-4-yl)phenoxy]methyl}-1H-pyrazol-4-yl]-3-[3-(naphthalen-1-yloxy)propyl]-1H-indole-2-carboxylate (1.00 g, 1.48 mmol) in DMF (15 ml) was added caesium carbonate (2.41 g, 7.41 mmol) and the mixture was stirred for 10 min at room temperature. Tert-butyl (3-bromopropyl)methylcarbamate (see Intermediate 1-1, 448 mg, 1.78 mmol) was added and the reaction was stirred for 4 days at room temperature. For work-up, the reaction mixture was concentrated under reduced pressure. The residue was dissolved in ethyl acetate and the organic phase was washed with water and brine and dried over sodium sulfate. After filtration and removal of the solvent the crude product was purified by flash chromatography (dichloromethane/acetone gradient, 5%→40% acetone) to give the title compound (1.0 g).

Intermediate 1-149 ethyl 7-[5-(bromomethyl)-1-methyl-3-{[4-(morpholin-4-yl)phenoxy]methyl}-1H-pyrazol-4-yl]-1-{3-[(tert-butoxycarbonyl)(methyl)amino]propyl}-3-[3-(naphthalen-1-yloxy)propyl]-1H-indole-2-carboxylate

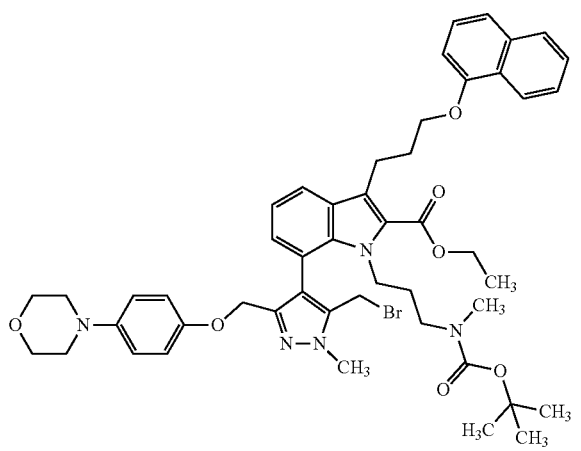 [SMILES: CCOC(=O)c1c(CCCOc2cccc3ccccc23)c2cccc(-c3c(COc4ccc(N5CCOCC5)cc4)nn(C)c3CBr)c2n1CCCN(C)C(=O)OC(C)(C)C]

To a solution of ethyl 1-{3-[(tert-butoxycarbonyl)(methyl)amino]propyl}-7-[5-(hydroxymethyl)-1-methyl-3-{[4-(morpholin-4-yl)phenoxy]methyl}-1H-pyrazol-4-yl]-3-[3-(naphthalen-1-yloxy)propyl]-1H-indole-2-carboxylate (870 mg, 1.03 mmol) in dichloromethane (15 ml), triphenylphosphine (647 mg, 2.47 mmol) was added at 0° C. and the mixture was stirred at 0° C. for 10 min. Tetrabromomethane (750 mg, 2.26 mmol) was added and the reaction was stirred at room temperature for 120 minutes. For work-up, the reaction mixture was concentrated under reduced pressure and the crude product was used in the subsequent steps without further purification.

Intermediate 1-150 ethyl 7-[5-(bromomethyl)-1-methyl-3-{[4-(morpholin-4-yl)phenoxy]methyl}-1H-pyrazol-4-yl]-1-[3-(methylamino)propyl]-3-[3-(naphthalen-1-yloxy)propyl]-1H-indole-2-carboxylate hydrochloric acid salt

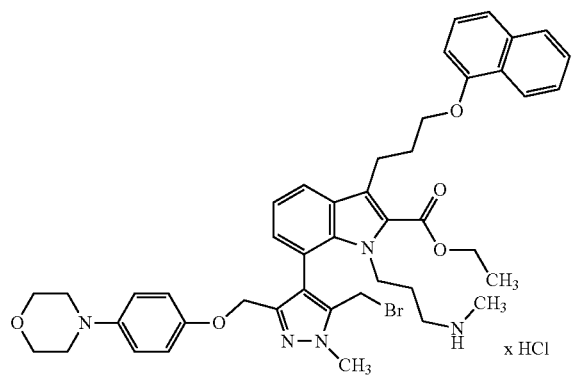 [SMILES: CCOC(=O)c1c(CCCOc2cccc3ccccc23)c2cccc(-c3c(COc4ccc(N5CCOCC5)cc4)nn(C)c3CBr)c2n1CCCNC]

To a solution of ethyl 7-[5-(bromomethyl)-1-methyl-3-{[4-(morpholin-4-yl)phenoxy]methyl}-1H-pyrazol-4-yl]-1-{3-[(tert-butoxycarbonyl)(methyl)amino]propyl}-3-[3-(naphthalen-1-yloxy)propyl]-1H-indole-2-carboxylate (930 µg, 1.0 µmol) in methanol (10 ml) was added a 4 M solution of HCl in dioxan (10 ml, 4.0 M, 40 mmol) at 0° C. and the mixture was stirred for 90 minutes at room temperature. For work-up, the mixture was concentrated under reduced pressure and the crude product was used for the subsequent steps without further purification.

Intermediate 1-151

(rac)-ethyl 7,9-dimethyl-11-{[4-(morpholin-4-yl)phenoxy]methyl}-1-[3-(naphthalen-1-yloxy)propyl]-4,5,6,7,8,9-hexahydropyrazolo[3',4':7,8][1,5]diazecino[9,10,1-hi]indole-2-carboxylate

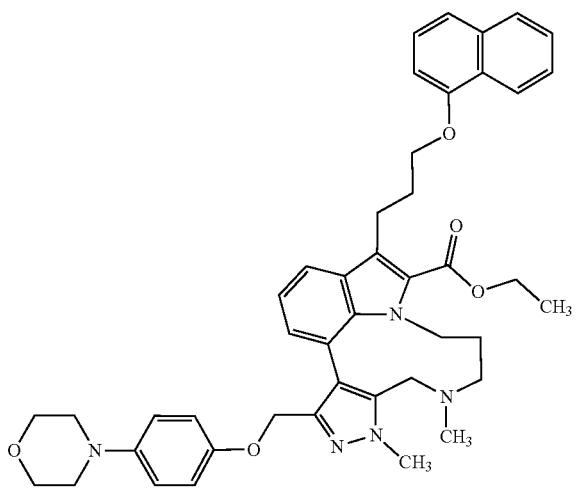 [SMILES: CCOC(=O)c1c(CCCOc2cccc3ccccc23)c2cccc3c2n1CCCN(C)Cc1c-3c(COc2ccc(N3CCOCC3)cc2)nn1C]

To a solution of ethyl 7-[5-(bromomethyl)-1-methyl-3-{[4-(morpholin-4-yl)phenoxy]methyl}-1H-pyrazol-4-yl]-1-[3-(methylamino)propyl]-3-[3-(naphthalen-1-yloxy)propyl]-1H-indole-2-carboxylate hydrochloric acid salt (869 mg) in DMF (25 ml) was added caesium carbonate (1.67 g, 5.14 mmol) and the reaction was stirred at 65° C. for 120 minutes and for 16 hours at room temperature. For work-up, the mixture was concentrated under reduced pressure and the residue was purified twice by flash chromatography (dichloromethane/methanol gradient, 0%→10% methanol followed by dichloromethane/methanol gradient, 1.5%→5% methanol) to give the title compound (512 mg).

LC-MS (Method 2): Rt=1.78 min; MS (ESIpos): m/z=728 [M+H]$^+$ $^1$H-NMR (400 MHz, DMSO-d6) δ [ppm]: 1.268 (1.65), 1.286 (3.74), 1.304 (1.68), 2.085 (1.64), 2.177 (3.78), 2.200 (0.55), 2.327 (0.43), 2.518 (1.27), 2.523 (0.94), 2.825 (1.19), 2.837 (1.43), 2.848 (1.32), 2.997 (0.48), 3.032 (0.51), 3.615 (1.41), 3.627 (1.91), 3.639 (1.39), 3.661 (0.56), 3.880 (5.34), 4.154 (0.43), 4.169 (0.91), 4.185 (0.44), 4.234 (0.71), 4.239 (0.41), 4.252 (0.75), 4.256 (0.80), 4.275 (0.69), 4.686 (1.61), 5.759 (16.00), 6.476 (1.27), 6.493 (0.44), 6.499 (1.70), 6.616 (1.66), 6.622 (0.43), 6.639 (1.21), 6.839 (0.59), 6.857 (0.63), 6.947 (0.45), 6.961 (0.89), 6.964 (0.81), 6.979 (0.85), 6.998 (0.85), 7.016 (0.42), 7.350 (0.49), 7.370 (0.87), 7.389 (0.67), 7.442 (0.84), 7.463 (0.52), 7.502 (0.53), 7.507 (0.47), 7.511 (0.59), 7.519 (1.20), 7.527 (0.59), 7.531 (0.53), 7.535

(0.59), 7.699 (0.60), 7.703 (0.64), 7.719 (0.56), 7.722 (0.55), 7.858 (0.49), 7.875 (0.46), 7.881 (0.41), 8.210 (0.44), 8.216 (0.41).

Intermediate 1-152

2-(2-methoxyphenyl)pyrimidin-5-ol

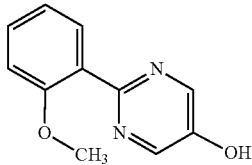

To a solution of (2-methoxyphenyl)boronic acid (500 mg, 3.29 mmol, CAS 5720-06-9) and 2-chloropyrimidin-5-ol (286 mg, 2.19 mmol, CAS 4983-28-2) in 1,4-dioxane (173 mg) and water (5 ml) was added potassium carbonate (1.21 g, 8.77 mmol). The mixture was degassed and purged with argon several times. XPhosPd G2 (173 mg, 219 μmol) was added and the mixture was purged with argon for 10 minutes. The reaction was stirred at 80° C. for 21 hours. For work-up, the reaction mixture was diluted with ethyl acetate and was filtered through a pad of celite. The residue was washed with ethyl acetate and the filtrate was washed with aqueous ammonium chloride solution. The organic phase was dried over sodium sulfate and the mixture was filtrated. The filtrate was concentrated under reduced pressure. The residue was purified by flash chromatography hexane/ethyl acetate gradient, 5%→100% ethyl acetate) to give the title compound (370 mg).

LC-MS (Method 1): Rt=0.71 min; MS (ESIpos): m/z=203 [M+H]$^+$

Intermediate 1-153 ethyl 4-bromo-3-({[2-(2-methoxyphenyl)pyrimidin-5-yl]oxy}methyl)-1-methyl-1H-pyrazole-5-carboxylate

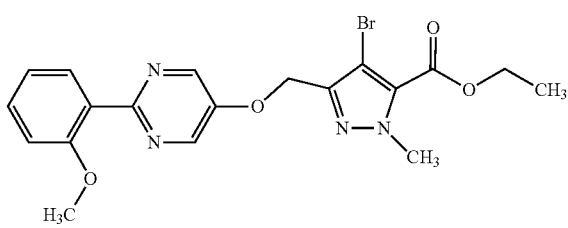 [SMILES: CCOC(=O)c1c(Br)c(COc2cnc(-c3ccccc3OC)nc2)nn1C]

To a solution of 2-(2-methoxyphenyl)pyrimidin-5-ol (797 mg, 3.94 mmol) in DMF (13 ml) was added potassium carbonate (1.56 g, 11.3 mmol) and the mixture was stirred for 10 min at room temperature. Ethyl 4-bromo-3-(bromomethyl)-1-methyl-1H-pyrazole-5-carboxylate (see Intermediate 1-5; 1.22 g, 3.75 mmol) was added and the reaction was stirred for 4 hours at room temperature. For work-up, the reaction mixture was diluted with ethyl acetate. The mixture was washed with aqueous 2 M sodium hydroxide solution and brine. The organic phase was dried over sodium sulfate and the mixture was filtrated. The filtrate was concentrated under reduced pressure and the residue was purified by flash chromatography dichloromethane/ethyl acetate gradient, 3%→20% ethyl acetate) to give the title compound (1.5 g).

LC-MS (Method 1): Rt=1.22 min; MS (ESIpos): m/z=447 [M+H]$^+$ $^1$H-NMR (400 MHz, CHLOROFORM-d) δ [ppm]: 1.251 (1.14), 1.268 (2.43), 1.286 (1.16), 1.425 (4.02), 1.443 (9.27), 1.461 (4.52), 2.055 (3.75), 3.903 (6.16), 4.121 (0.81), 4.139 (0.82), 4.192 (16.00), 4.406 (1.29), 4.423 (4.27), 4.441 (4.27), 4.459 (1.27), 5.229 (6.82), 5.309 (1.53), 7.029 (1.12), 7.048 (1.61), 7.064 (1.34), 7.066 (1.14), 7.083 (0.73), 7.085 (0.67), 7.399 (0.47), 7.404 (0.52), 7.419 (0.73), 7.421 (0.74), 7.424 (0.72), 7.443 (0.41), 7.701 (0.62), 7.720 (0.58), 8.699 (2.54).

Intermediate 1-154

[4-bromo-3-({[2-(2-methoxyphenyl)pyrimidin-5-yl]oxy}methyl)-1-methyl-1H-pyrazol-5-yl]methanol

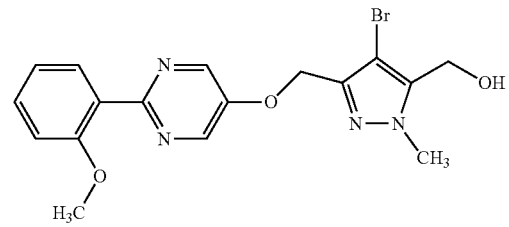 [SMILES: COc1ccccc1-c1ncc(OCc2nn(C)c(CO)c2Br)cn1]

To a solution of ethyl 4-bromo-3-({[2-(2-methoxyphenyl)pyrimidin-5-yl]oxy}methyl)-1-methyl-1H-pyrazole-5-carboxylate (1.52 g, 3.39 mmol) in THF (35 ml) at 0° C. was added a solution of lithium aluminium hydride in THF (1.7 ml, 2.0 M, 3.4 mmol) and the mixture was stirred at 0° C. for 1 hour. For work-up, aqueous 2 M sodium hydroxide solution (2 ml) was added at 0° C. and the mixture was stirred for 10 minutes at room temperature. Sodium sulfate was added and the mixture was stirred for 10 min. The mixture was filtered and the filtrate was concentrated under reduced pressure. The crude product (1.21 g) was used in the subsequent steps without further purification.

Intermediate 1-155 ethyl 7-[5-(hydroxymethyl)-3-({[2-(2-methoxyphenyl)pyrimidin-5-yl]oxy}methyl)-1-methyl-1H-pyrazol-4-yl]-3-[3-(naphthalen-1-yloxy)propyl]-1H-indole-2-carboxylate

Intermediate 1-156 ethyl 1-{3-[(tert-butoxycarbonyl)(methyl)amino]propyl}-7-[5-(hydroxymethyl)-3-({[2-(2-methoxyphenyl)pyrimidin-5-yl]oxy}methyl)-1-methyl-1H-pyrazol-4-yl]-3-[3-(naphthalen-1-yloxy)propyl]-1H-indole-2-carboxylate

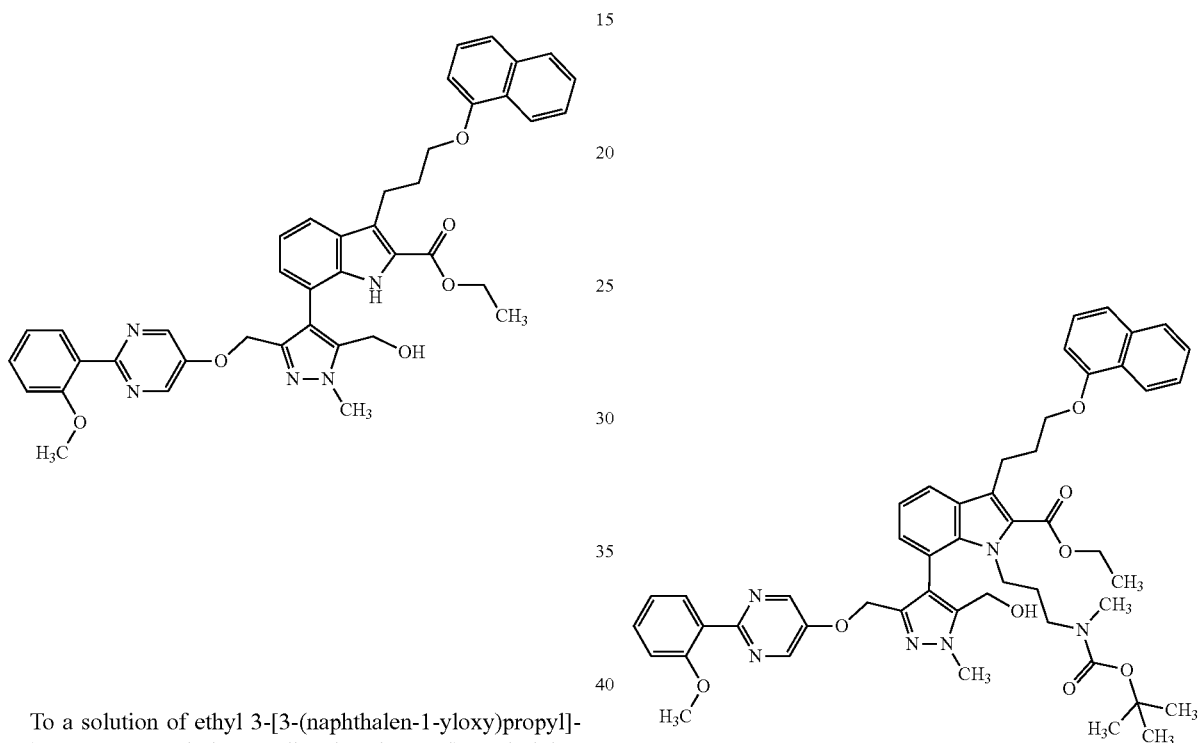

To a solution of ethyl 3-[3-(naphthalen-1-yloxy)propyl]-7-(4,4,5,5-tetramethyl-1,3,2-dioxaborolan-2-yl)-1H-indole-2-carboxylate (see Intermediate 1-4; 1.63 g, 3.26 mmol) and [4-bromo-3-({[2-(2-methoxyphenyl)pyrimidin-5-yl]oxy}methyl)-1-methyl-1H-pyrazol-5-yl]methanol (1.20 g, 2.96 mmol) in 1,4-dioxane (37 ml) was added aqueous 2 M solution of potassium carbonate (4.4 ml, 2.0 M, 8.9 mmol). The mixture was degassed and purged with argon several times. Pd(dppf)Cl$_2$×CH$_2$Cl$_2$ (484 mg, 592 µmol) was added and the mixture was purged with argon for 10 minutes. The reaction was stirred at 80° C. for 16 h. For work-up, the reaction mixture was diluted with ethyl acetate and was filtered through a pad of celite. The filtrate was concentrated under reduced pressure and the residue was dissolved in ethyl acetate. The organic phase was washed with water and brine and the organic phase was dried over sodium sulfate. The mixture was filtrated and the filtrate was concentrated under reduced pressure. The residue was purified by flash chromatography (dichloromethane/ethyl acetate gradient, 20%→90% ethyl acetate) to give the title compound (240 mg).

LC-MS (Method 1): Rt=1.54 min; MS (ESIpos): m/z=698 [M+H]$^+$

To a solution of ethyl 7-[5-(hydroxymethyl)-3-({[2-(2-methoxyphenyl)pyrimidin-5-yl]oxy}methyl)-1-methyl-1H-pyrazol-4-yl]-3-[3-(naphthalen-1-yloxy)propyl]-1H-indole-2-carboxylate (240 mg, 344 µmol) in DMF (3.5 ml) was added caesium carbonate (560 mg, 1.72 mmol) and the mixture was stirred for 10 min at room temperature. Tert-butyl (3-bromopropyl)methylcarbamate (see Intermediate 1-1; 104 mg, 413 µmol) was added and the reaction was stirred for 1 day at 40° C. For work-up, the reaction mixture was concentrated under reduced pressure and the residue was dissolved in ethyl acetate. The mixture was washed with water and brine and dried over sodium sulfate. After filtration and removal of the solvents the crude product was purified by flash chromatography (dichloromethane/acetone gradient, 5%→40% acetone) to give the title compound (207 mg).

337

Intermediate 1-157 ethyl 7-[5-(bromomethyl)-3-({[2-(2-methoxyphenyl)pyrimidin-5-yl]oxy}methyl)-1-methyl-1H-pyrazol-4-yl]-1-{3-[(tert-butoxycarbonyl)(methyl)amino]propyl}-3-[3-(naphthalen-1-yloxy)propyl]-1H-indole-2-carboxylate

338

Intermediate 1-158 ethyl 7-[5-(bromomethyl)-3-({[2-(2-methoxyphenyl)pyrimidin-5-yl]oxy}methyl)-1-methyl-1H-pyrazol-4-yl]-1-[3-(methylamino)propyl]-3-[3-(naphthalen-1-yloxy)propyl]-1H-indole-2-carboxylate hydrochloric acid salt

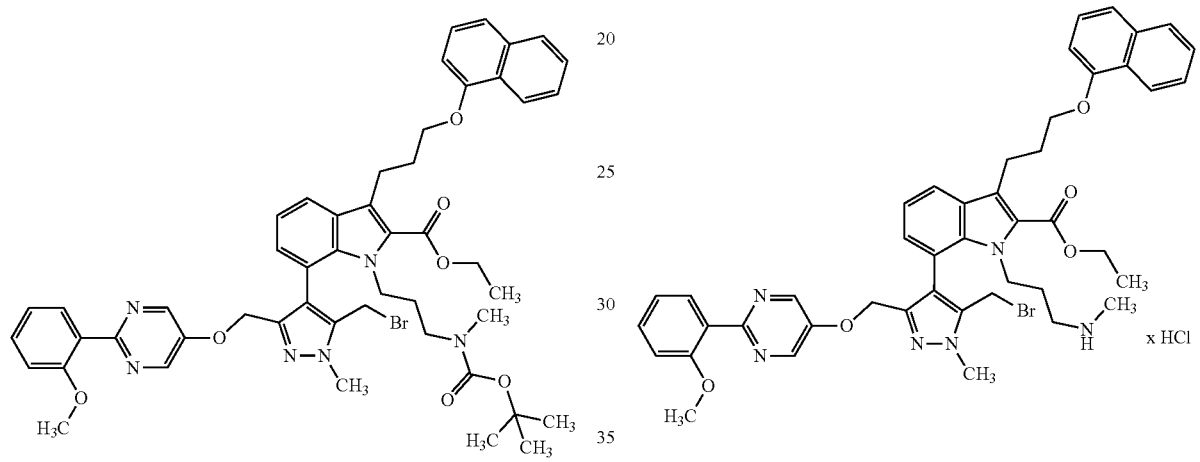

To a solution of ethyl 1-{3-[(tert-butoxycarbonyl)(methyl)amino]propyl}-7-[5-(hydroxymethyl)-3-({[2-(2-methoxyphenyl)pyrimidin-5-yl]oxy}methyl)-1-methyl-1H-pyrazol-4-yl]-3-[3-(naphthalen-1-yloxy)propyl]-1H-indole-2-carboxylate (90.0 mg, 104 μmol) in dichloromethane (1.0 ml), triphenylphosphine (65.2 mg, 249 μmol) was added at 0° C. and the mixture was stirred at 0° C. for 10 min. Tetrabromomethane (65.2 mg, 249 μmol) was added and the reaction was stirred at room temperature for 120 minutes. For work-up, the reaction mixture was concentrated under reduced pressure and the crude product was used in the subsequent steps without further purification.

To a solution of ethyl 7-[5-(bromomethyl)-3-({[2-(2-methoxyphenyl)pyrimidin-5-yl]oxy}methyl)-1-methyl-1H-pyrazol-4-yl]-1-{3-[(tert-butoxycarbonyl)(methyl)amino]propyl}-3-[3-(naphthalen-1-yloxy)propyl]-1H-indole-2-carboxylate (96.9 mg, 104 μmol) in methanol (1.0 ml) was added a 4 M solution of HCl in dioxan (1.0 ml, 4.0 M, 4.0 mmol) at 0° C. and the mixture was stirred for 90 minutes at room temperature. For work-up, the mixture was concentrated under reduced pressure and the crude product was used for the subsequent steps without further purification.

Intermediate 1-159

(rac)-ethyl 11-({[2-(2-methoxyphenyl)pyrimidin-5-yl]oxy}methyl)-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylate

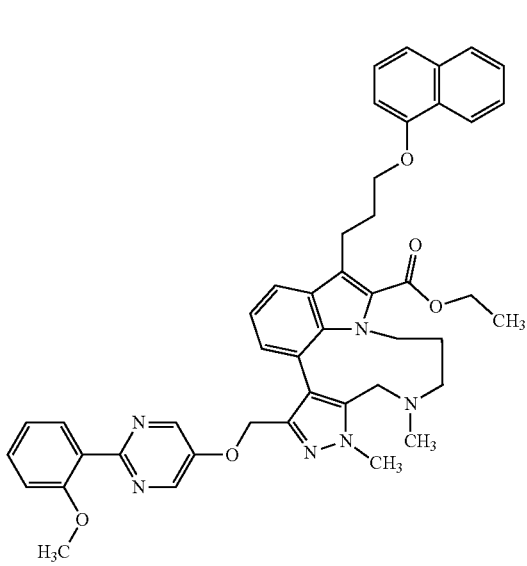 [SMILES: CCOC(=O)c1c(CCCOc2cccc3ccccc23)c2cccc3c2n1CCCN(C)Cc1c-3c(COc2cnc(-c3ccccc3OC)nc2)nn1C]

To a solution of ethyl 7-[5-(bromomethyl)-3-({[2-(2-methoxyphenyl)pyrimidin-5-yl]oxy}methyl)-1-methyl-1H-pyrazol-4-yl]-1-[3-(methylamino)propyl]-3-[3-(naphthalen-1-yloxy)propyl]-1H-indole-2-carboxylate hydrochloric acid salt (90.3 mg) in DMF (3.0 ml) was added caesium carbonate (169 mg, 520 µmol) and the reaction was stirred at 65° C. for 120 minutes and subsequently at room temperature for 16 hours. For work-up, the mixture was concentrated under reduced pressure and the residue was purified by flash chromatography (dichloromethane/methanol gradient, 0%→10% methanol) to give the title compound (47 mg).

$^1$H-NMR (400 MHz, CHLOROFORM-d) δ [ppm]: 1.183 (0.43), 1.269 (3.64), 1.286 (7.88), 1.304 (3.79), 1.519 (0.98), 2.013 (0.47), 2.032 (0.42), 2.190 (9.03), 2.222 (1.04), 2.239 (1.68), 2.256 (1.12), 2.295 (0.45), 2.310 (0.45), 3.153 (1.27), 3.189 (1.57), 3.255 (0.46), 3.270 (0.59), 3.289 (1.07), 3.308 (0.88), 3.328 (1.06), 3.347 (0.56), 3.362 (0.48), 3.426 (1.57), 3.462 (1.24), 3.707 (0.45), 3.718 (0.62), 3.729 (0.45), 3.744 (0.74), 3.759 (16.00), 3.919 (12.65), 4.107 (1.41), 4.122 (2.98), 4.137 (1.36), 4.196 (0.44), 4.205 (0.47), 4.213 (0.49), 4.223 (1.79), 4.241 (2.71), 4.260 (1.76), 4.269 (0.49), 4.277 (0.47), 4.286 (0.44), 4.389 (0.76), 4.426 (0.70), 4.874 (1.46), 4.902 (2.67), 4.958 (2.56), 4.986 (1.45), 6.678 (1.50), 6.696 (1.57), 6.906 (1.64), 6.926 (2.67), 6.944 (2.23), 6.947 (1.99), 6.955 (4.25), 6.960 (2.55), 6.973 (2.09), 6.990 (0.57), 7.243 (1.01), 7.263 (2.04), 7.274 (0.97), 7.278 (1.11), 7.282 (1.74), 7.294 (1.18), 7.296 (1.16), 7.299 (1.08), 7.313 (0.77), 7.317 (0.84), 7.327 (2.08), 7.347 (1.17), 7.392 (0.41), 7.404 (1.46), 7.407 (1.83), 7.418 (2.26), 7.427 (1.84), 7.430 (1.60), 7.443 (0.43), 7.537 (1.49), 7.541 (1.48), 7.555 (1.43), 7.560 (1.33), 7.636 (1.22), 7.642 (1.28), 7.654 (1.08), 7.659 (1.15), 7.720 (1.16), 7.723 (0.82), 7.733 (0.89), 7.737 (0.75), 7.743 (0.96), 8.279 (0.98), 8.290 (0.83), 8.303 (1.02), 8.324 (11.16).

Intermediate 1-160 ethyl 3-[(benzyloxy)methyl]-4-bromo-1-methyl-1H-pyrazole-5-carboxylate

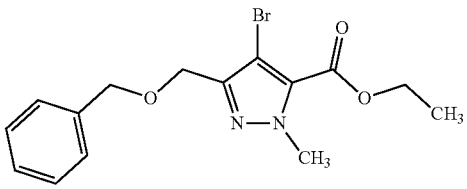 [SMILES: CCOC(=O)c1c(Br)c(COCc2ccccc2)nn1C]

To a solution of phenylmethanol (1.0 ml, 9.7 mmol) in DMF (19 ml) was added sodium hydride (386 mg, 60% purity, 9.66 mmol) and the mixture was stirred for 1 hour at room temperature. A solution of ethyl 4-bromo-3-(bromomethyl)-1-methyl-1H-pyrazole-5-carboxylate (see Intermediate 1-5; 2.86 g, 8.78 mmol) in DMF (15 ml) was added and the reaction was stirred for 24 hours at room temperature. For work-up, the reaction mixture was poured into water. The mixture was extracted with ethyl acetate. The combined organic phases were washed with brine and dried over sodium sulfate. After filtration and removal of the solvent the crude product was purified by flash chromatography (hexane/ethyl acetate gradient, 5%→30% ethyl acetate) to give the title compound (2.1 g).

$^1$H-NMR (400 MHz, CHLOROFORM-d) δ [ppm]: 1.184 (0.57), 1.348 (3.71), 1.367 (8.26), 1.384 (4.12), 1.501 (1.84), 4.091 (4.32), 4.099 (16.00), 4.322 (1.25), 4.339 (3.71), 4.358 (3.80), 4.375 (1.22), 4.447 (0.68), 4.479 (2.38), 4.487 (9.88), 4.529 (1.63), 4.536 (6.24), 5.334 (1.47), 7.221 (0.99), 7.234 (0.54), 7.238 (0.92), 7.243 (0.53), 7.263 (1.08), 7.268 (0.63), 7.279 (1.32), 7.282 (2.67), 7.294 (0.71), 7.300 (1.71), 7.303 (1.29), 7.310 (1.10), 7.318 (2.59), 7.335 (1.55), 7.408 (0.44).

Intermediate 1-161

{3-[(benzyloxy)methyl]-4-bromo-1-methyl-1H-pyrazol-5-yl}methanol

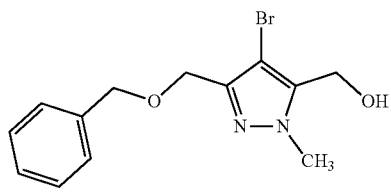 [SMILES: Cn1nc(COCc2ccccc2)c(Br)c1CO]

To a solution of ethyl 3-[(benzyloxy)methyl]-4-bromo-1-methyl-1H-pyrazole-5-carboxylate (2.00 g, 5.66 mmol) in THF (55 ml) at 0° C. was added a solution of lithium aluminium hydride in THF (2.8 ml, 2.0 M, 5.7 mmol) and the mixture was stirred at 0° C. for 2 hours. Ice was carefully added and the reaction mixture was stirred for 30 minutes. The reaction mixture was poured into water and the mixture was extracted with ethyl acetate. The combined organic layers were washed with brine and dried over sodium sulfate. After filtration and removal of the solvents the crude product (1.81 g) was used without further purification in the subsequent steps.

LC-MS (Method 2): Rt=1.00 min; MS (ESIpos): m/z=311 [M+H]+

¹H-NMR (400 MHz, DMSO-d6) δ [ppm]: 1.073 (0.50), 1.090 (1.16), 1.108 (0.51), 1.354 (1.12), 2.518 (0.49), 3.333 (16.00), 3.427 (0.52), 3.444 (0.55), 3.747 (3.38), 3.832 (2.07), 4.301 (1.15), 4.383 (2.25), 4.390 (15.44), 4.458 (1.00), 4.467 (5.95), 4.474 (2.58), 4.480 (7.04), 4.487 (12.64), 4.496 (1.40), 5.167 (0.77), 5.378 (1.50), 5.391 (3.12), 5.405 (1.24), 6.164 (0.75), 7.264 (0.57), 7.271 (0.68), 7.280 (1.35), 7.285 (0.73), 7.287 (1.16), 7.294 (1.04), 7.297 (1.28), 7.302 (1.38), 7.308 (4.01), 7.317 (2.45), 7.321 (2.55), 7.333 (11.80), 7.338 (4.09), 7.347 (3.39), 7.350 (3.63), 7.355 (1.23), 7.364 (0.42), 7.368 (0.90), 7.371 (0.58).

Intermediate 1-162 ethyl 7-{3-[(benzyloxy)methyl]-5-(hydroxymethyl)-1-methyl-1H-pyrazol-4-yl}-3-[3-(naphthalen-1-yloxy)propyl]-1H-indole-2-carboxylate

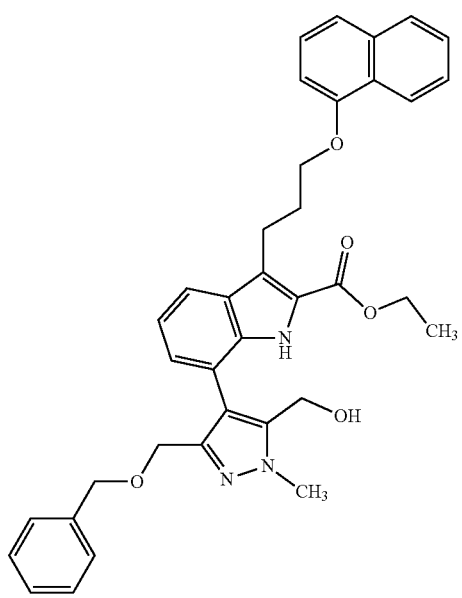 [SMILES: CCOC(=O)c1[nH]c2c(-c3c(COCc4ccccc4)nn(C)c3CO)cccc2c1CCCOc1cccc2ccccc12]

To a solution of ethyl 3-[3-(naphthalen-1-yloxy)propyl]-7-(4,4,5,5-tetramethyl-1,3,2-dioxaborolan-2-yl)-1H-indole-2-carboxylate (see Intermediate 1-4; 3.76 g, 7.52 mmol) and {3-[(benzyloxy)methyl]-4-bromo-1-methyl-1H-pyrazol-5-yl}methanol (1.80 g, 5.78 mmol) in 1,4-dioxane (74 ml) was added aqueous 2 M solution of potassium carbonate (8.7 ml, 2.0 M, 17 mmol). The mixture was degassed and purged with argon several times. Pd(dppf)Cl₂×CH₂Cl₂ (846 mg, 1.16 mmol) was added and the mixture was purged with argon for 10 minutes. The reaction was stirred at 80° C. for 4 h. For work-up, the reaction mixture was concentrated under reduced pressure and the residue was purified by flash chromatography (hexane/ethyl acetate gradient, 50%→100% ethyl acetate) to give the title compound (2.7 g).

LC-MS (Method 1): Rt=1.62 min; MS (ESIpos): m/z=604 [M+H]+

¹H-NMR (400 MHz, DMSO-d6) δ [ppm]: 1.154 (0.85), 1.172 (1.68), 1.190 (0.89), 1.232 (4.91), 1.250 (10.40), 1.267 (4.86), 1.988 (3.26), 2.225 (0.94), 2.243 (1.30), 2.261 (0.97), 2.327 (0.48), 2.469 (0.43), 2.518 (2.11), 2.523 (1.47), 2.669 (0.48), 3.350 (1.44), 3.369 (1.93), 3.387 (1.13), 3.942 (16.00), 4.017 (0.77), 4.035 (0.74), 4.200 (1.49), 4.208 (1.74), 4.215 (3.06), 4.226 (3.77), 4.244 (3.17), 4.262 (1.67), 4.272 (3.07), 4.378 (1.46), 4.423 (3.23), 5.661 (1.18), 5.673 (2.87), 5.685 (1.15), 5.760 (2.67), 6.898 (1.69), 6.915 (1.84), 7.065 (1.54), 7.082 (2.08), 7.084 (1.93), 7.103 (1.84), 7.133 (2.37), 7.149 (3.09), 7.153 (2.79), 7.210 (1.55), 7.217 (0.51), 7.222 (1.37), 7.227 (2.17), 7.231 (1.42), 7.236 (3.76), 7.240 (1.80), 7.244 (2.47), 7.247 (2.69), 7.254 (3.32), 7.262 (2.11), 7.264 (1.94), 7.271 (1.03), 7.275 (0.72), 7.370 (1.36), 7.391 (2.53), 7.410 (2.09), 7.451 (2.51), 7.472 (1.44), 7.483 (0.47), 7.487 (0.66), 7.500 (1.51), 7.504 (1.39), 7.512 (1.63), 7.518 (3.25), 7.524 (1.63), 7.531 (1.49), 7.535 (1.62), 7.549 (0.68), 7.552 (0.47), 7.704 (1.83), 7.724 (1.69), 7.861 (1.46), 7.868 (0.85), 7.879 (1.54), 7.884 (1.25), 8.219 (1.29), 8.224 (1.26), 8.241 (1.17), 8.244 (1.22), 10.880 (2.67).

Intermediate 1-163 ethyl 7-{3-[(benzyloxy)methyl]-5-(hydroxymethyl)-1-methyl-1H-pyrazol-4-yl}-1-{3-[(tert-butoxycarbonyl)(methyl)amino]propyl}-3-[3-(naphthalen-1-yloxy)propyl]-1H-indole-2-carboxylate

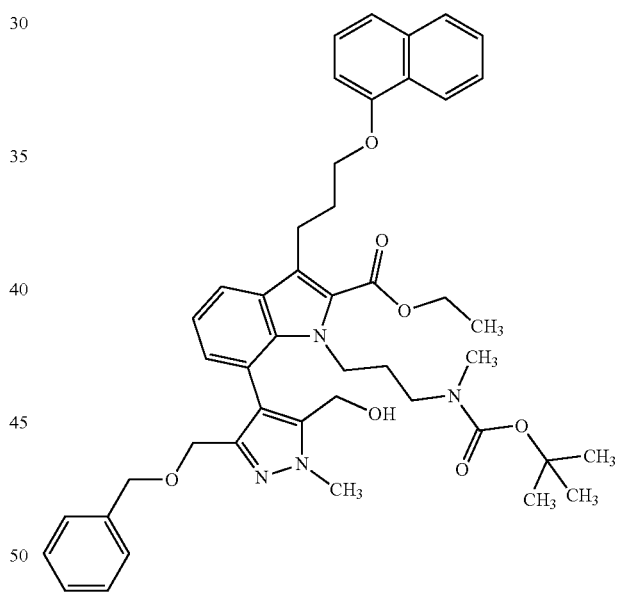

To a solution of ethyl 7-{3-[(benzyloxy)methyl]-5-(hydroxymethyl)-1-methyl-1H-pyrazol-4-yl}-3-[3-(naphthalen-1-yloxy)propyl]-1H-indole-2-carboxylate (1.35 g, 2.24 mmol) in DMF (29 ml) was added caesium carbonate (3.64 g, 11.2 mmol), and the mixture was stirred for 10 min at room temperature. Tert-butyl (3-bromopropyl)methylcarbamate (see Intermediate 1-1; 677 mg, 2.68 mmol) was added and the reaction was stirred for 1 day at room temperature and subsequently for 8 hours at 40° C. For work-up, the reaction mixture was poured into water. The mixture was extracted with ethyl acetate. The combined organic phases were washed with brine and dried over sodium sulfate. After filtration and removal of the solvent, the crude product was purified by flash chromatography (dichloromethane/methanol gradient, 0%→10% methanol) to give the title compound (1.2 g).

Intermediate 1-164 ethyl 7-{3-[(benzyloxy)methyl]-5-(bromomethyl)-1-methyl-1H-pyrazol-4-yl}-1-{3-[(tert-butoxycarbonyl)(methyl)amino]propyl}-3-[3-(naphthalen-1-yloxy)propyl]-1H-indole-2-carboxylate

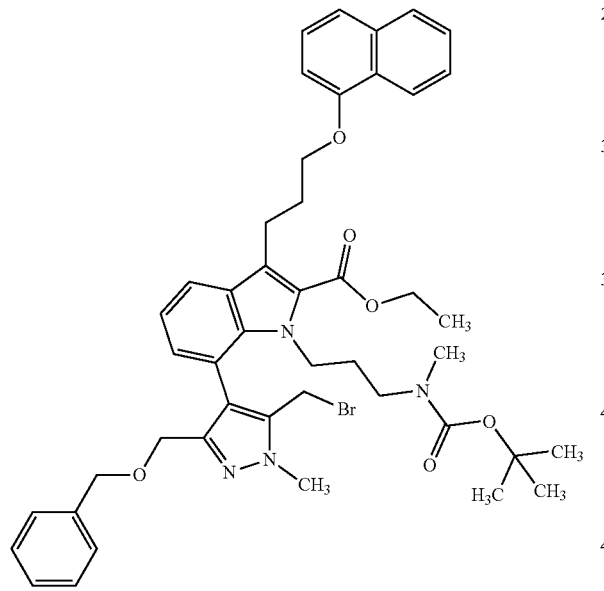

To a solution of ethyl 7-{3-[(benzyloxy)methyl]-5-(hydroxymethyl)-1-methyl-1H-pyrazol-4-yl}-1-{3-[(tert-butoxycarbonyl)(methyl)amino]propyl}-3-[3-(naphthalen-1-yloxy)propyl]-1H-indole-2-carboxylate (1.22 g, 1.57 mmol) in dichloromethane (29 ml), triphenylphosphine (991 mg, 3.78 mmol) was added at 0° C. and the mixture was stirred at 0° C. for 10 min. Tetrabromomethane (1.15 g, 3.46 mmol) was added and the reaction was stirred for 2 hours at room temperature. For work-up, the reaction mixture was concentrated under reduced pressure and the crude product was purified by flash chromatography (hexane/ethyl acetate gradient, 12%→55% ethyl acetate) to give the title compound (410 mg).

Intermediate 1-165 ethyl 7-{3-[(benzyloxy)methyl]-5-(bromomethyl)-1-methyl-1H-pyrazol-4-yl}-1-[3-(methylamino)propyl]-3-[3-(naphthalen-1-yloxy)propyl]-1H-indole-2-carboxylate hydrochloric acid salt To a solution of ethyl 7-{3-[(benzyloxy)methyl]-5-(bromomethyl)-1-methyl-1H-pyrazol-4-yl}-1-{3-[(tert-butoxycarbonyl)(methyl)amino]propyl}-3-[3-(naphthalen-1-yloxy)propyl]-1H-indole-2-carboxylate (410 mg, 489 μmol) in methanol (9.0 ml) was added a 4 M solution of HCl in dioxan (9.1 ml, 4.0 M, 36 mmol) at 0° C., and the mixture was stirred for 24 hours at room temperature. For work-up, the mixture was concentrated under reduced pressure and the crude product was used for the subsequent steps without further purification.

Intermediate 1-166

(rac)-ethyl 11-[(benzyloxy)methyl]-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylate

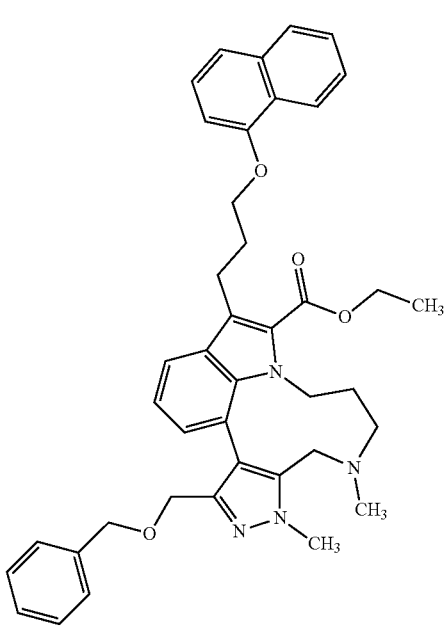 [SMILES: CCOC(=O)c1c(CCCOc2cccc3ccccc23)c2cccc3c2n1CCCN(C)Cc1c-3c(COCc2ccccc2)nn1C]

To a solution of ethyl 7-{3-[(benzyloxy)methyl]-5-(bromomethyl)-1-methyl-1H-pyrazol-4-yl}-1-[3-(methylamino)propyl]-3-[3-(naphthalen-1-yloxy)propyl]-1H-indole-2-carboxylate hydrochloric acid salt (380 mg) in DMF (49 ml) was added caesium carbonate (800 mg, 2.45 mmol) and the reaction was stirred at 65° C. for 24 hours. For work-up, the reaction mixture was concentrated under reduced pressure and the residue was purified by flash chromatography (dichloromethane/ethyl acetate gradient, 0%→100% ethyl acetate) to give the title compound (270 mg).

Intermediate 1-167 ethyl 7-{3-[(benzyloxy)methyl]-1-methyl-5-[(prop-2-en-1-yloxy)methyl]-1H-pyrazol-4-yl}-3-[3-(naphthalen-1-yloxy)propyl]-1-(prop-2-en-1-yl)-1H-indole-2-carboxylate

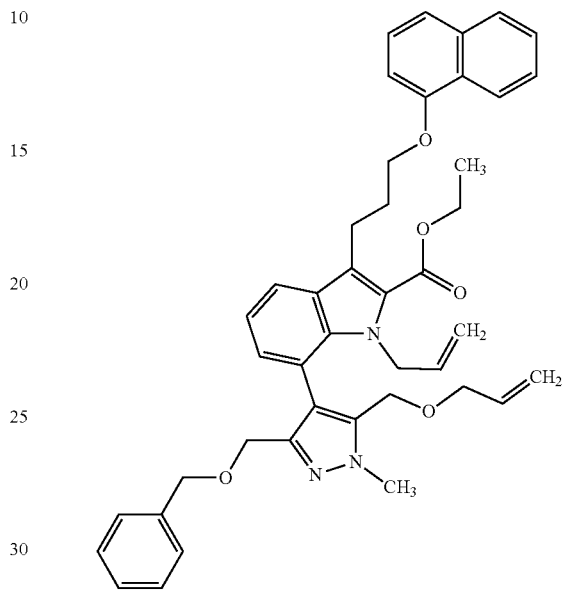

To a solution of ethyl 7-{3-[(benzyloxy)methyl]-5-(hydroxymethyl)-1-methyl-1H-pyrazol-4-yl}-3-[3-(naphthalen-1-yloxy)propyl]-1H-indole-2-carboxylate (see Intermediate 1-162; 1.35 g, 2.24 mmol) in THF (30 ml) was added sodium hydride (224 mg, 60% purity, 5.59 mmol) at 0° C. and the mixture was stirred for 2 hours at room temperature. The reaction was cooled down to 0° C. and a solution of allyl bromide (480 µl, 5.6 mmol) in THF (1 ml) was added. The mixture was stirred for 4 days at room temperature. For work-up, aqueous sodium chloride solution was added and the mixture was extracted with ethyl acetate. The combined organic phases were washed with brine, dried over sodium sulfate and the mixture was filtered. The filtrate was concentrated under reduced pressure and the residue was purified by flash chromatography (hexane/ethyl acetate gradient, 12%→100% ethyl acetate) to give the title compound (995 mg).

$^1$H-NMR (400 MHz, DMSO-d6) δ [ppm]: 1.234 (4.69), 1.252 (10.46), 1.270 (4.71), 2.209 (0.87), 2.226 (1.19), 2.245 (0.93), 2.323 (0.43), 2.327 (0.60), 2.332 (0.41), 2.518 (2.59), 2.523 (1.82), 2.665 (0.43), 2.669 (0.60), 2.674 (0.43), 3.307 (1.15), 3.752 (1.55), 3.757 (0.59), 3.771 (0.57), 3.786 (0.73), 3.790 (1.24), 3.794 (0.74), 3.800 (0.79), 3.804 (1.28), 3.807 (0.74), 3.832 (0.75), 3.836 (1.27), 3.840 (0.78), 3.845 (0.80), 3.849 (1.26), 3.853 (0.75), 3.865 (0.57), 3.868 (0.63), 3.872 (0.46), 3.882 (0.94), 3.892 (16.00), 3.905 (0.52), 4.071 (1.95), 4.101 (2.80), 4.108 (1.27), 4.147 (1.16), 4.151 (1.22), 4.170 (1.58), 4.198 (4.40), 4.213 (3.41), 4.216 (4.40), 4.230 (5.86), 4.233 (4.31), 4.248 (1.03), 4.251 (0.87), 4.258 (1.72), 4.269 (3.39), 4.292 (2.93), 4.296 (3.82), 4.323 (2.13), 4.326 (1.52), 4.395 (0.74), 4.478 (0.58), 4.490 (0.69), 4.674 (1.32), 4.677 (1.31), 4.700 (1.64), 4.703 (1.99), 4.716 (0.82), 4.754 (0.72), 4.764 (0.80), 4.997 (0.52), 5.000 (1.17), 5.005 (1.39), 5.009 (0.64), 5.026 (1.83), 5.031 (2.54), 5.035 (1.92), 5.039 (0.52), 5.069 (0.68), 5.073 (1.62), 5.078 (1.47), 5.082 (0.52), 5.409 (0.60), 5.423 (0.45), 5.435 (0.61), 5.440 (0.42), 5.453 (0.60), 5.465 (0.43), 5.478 (0.54), 5.691 (0.48), 5.704 (1.01), 5.716 (0.78), 5.730 (1.04), 5.734 (0.52), 5.744 (0.56), 5.747 (0.98), 5.760 (0.70), 5.773 (0.85), 5.787 (0.41), 6.886 (1.68), 6.904 (1.79), 6.941 (1.62), 6.947 (1.92), 6.956 (2.18), 6.965 (2.02), 7.020 (1.50), 7.024 (1.57), 7.038 (2.29), 7.041 (2.10), 7.095 (2.05), 7.115 (2.16), 7.133 (1.43), 7.137 (0.73), 7.147 (7.13), 7.153 (5.13), 7.161 (2.89), 7.163 (3.15), 7.169 (0.69), 7.172 (0.64), 7.328 (0.41), 7.366 (1.37), 7.386 (2.46), 7.405 (1.98), 7.454 (2.38), 7.474 (1.42), 7.504 (0.49), 7.515 (1.71), 7.519 (2.13), 7.529 (2.63), 7.537 (1.89), 7.539 (2.11), 7.542 (1.90), 7.554 (0.51), 7.796 (1.73), 7.799 (1.77), 7.815 (1.62), 7.818 (1.57), 7.865 (1.37), 7.868 (0.93), 7.878 (1.03), 7.882 (0.89), 7.888 (1.16), 8.242 (1.22), 8.253 (0.97), 8.266 (1.09).

Intermediate 1-168

(rac)-(E/Z)-ethyl-3-[(benzyloxy)methyl]-1-methyl-7-[3-(naphthalen-1-yloxy)propyl]-1,10,13,15-tetrahydropyrazolo[4',3':9,10][1,6]oxazacycloundecino[8,7,6-hi]indole-8-carboxylate

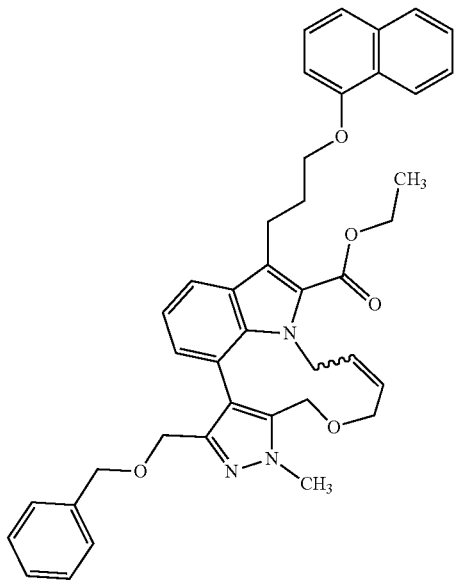 [SMILES: CCOC(=O)c1c(CCCOc2cccc3ccccc23)c2cccc3c2n1CC=CCOCc1c-3c(COCc2ccccc2)nn1C]

A solution of ethyl 7-{3-[(benzyloxy)methyl]-1-methyl-5-[(prop-2-en-1-yloxy)methyl]-1H-pyrazol-4-yl}-3-[3-(naphthalen-1-yloxy)propyl]-1-(prop-2-en-1-yl)-1H-indole-2-carboxylate (996 mg, 1.46 mmol) in dichloromethane (19 ml) was purged with argon several times. (1,3-Bis(2,4,6-trimethylphenyl)-2-imidazolidinylidene)dichloro(phenylmethylene)(tricyclohexylphosphine)ruthenium (124 mg, 146 µmol) (Grubbs 2$^{nd}$ generation catalyst) was added and the reaction was stirred for 3 days at room temperature. For work-up, the reaction mixture was concentrated under reduced pressure and the residue was purified twice by flash chromatography (hexane/ethyl acetate gradient, 12%→100% ethyl acetate) to give the title compound (710 mg).

Intermediate 1-169

(rac)-ethyl 3-(hydroxymethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate

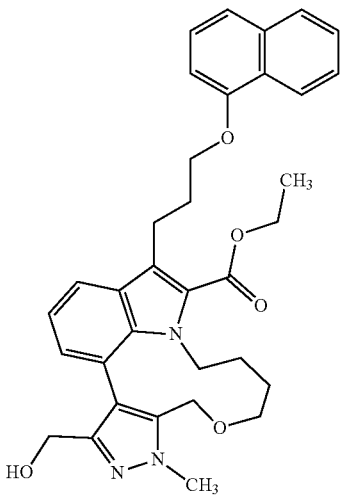 [SMILES: CCOC(=O)c1c(CCCOc2cccc3ccccc23)c2cccc3c2n1CCCCOCc1c-3c(CO)nn1C]

A suspension of (rac)-(E/Z)-ethyl 3-[(benzyloxy)methyl]-1-methyl-7-[3-(naphthalen-1-yloxy)propyl]-1,10,13,15-tetrahydropyrazolo[4',3':9,10][1,6]oxazacycloundecino[8,7,6-hi]indole-8-carboxylate (200 mg, 305 µmol) and Pd/C (32.4 mg, 10 wt-% Pd, 30.5 µmol) in ethanol (5.3 ml) was stirred under an atmosphere of hydrogen at room temperature for 4 days. For work-up, the mixture was filtered through a pad of celite. The residue was washed with ethanol and ethyl acetate, and the filtrate was concentrated under reduced pressure. The residue was purified by flash chromatography (dichloromethane/acetone gradient, 0%→40% acetone) to give the title compound (160 mg).

Intermediate 1-170

(4-bromo-1-methyl-1H-pyrazol-5-yl)methanol

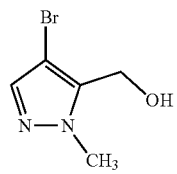

To a solution of methyl 4-bromo-1-methyl-1H-pyrazole-5-carboxylate (5.00 g, 22.8 mmol, CAS 1328640-39-6) in THF (170 ml) at 0° C. was added a solution of lithium aluminium hydride in THF (11 ml, 2.0 M, 23 mmol) and the mixture was stirred at 0° C. for 60 min. For work-up, water (1 ml) was added dropwise, followed by the addition of 2 M sodium hydroxide solution (1 ml) and again water (1 ml).

349

The mixture was filtrated through a pad of celite. The residue was washed with dichloromethane and the filtrate was concentrated under reduced pressure. The residue was triturated with dichloromethane to give the title compound (3.85 g).

LC-MS (Method 2): Rt=0.61 min; MS (ESIpos): m/z=191 [M+H]$^+$

Intermediate 1-171 ethyl 7-[5-(hydroxymethyl)-1-methyl-1H-pyrazol-4-yl]-3-[3-(naphthalen-1-yloxy)propyl]-1H-indole-2-carboxylate

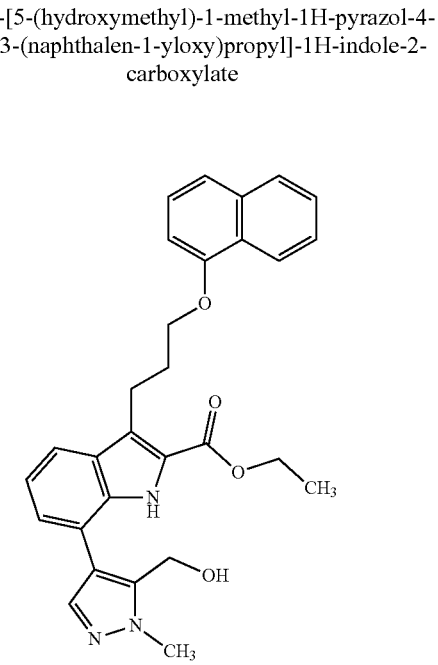

To a solution of ethyl 3-[3-(naphthalen-1-yloxy)propyl]-7-(4,4,5,5-tetramethyl-1,3,2-dioxaborolan-2-yl)-1H-indole-2-carboxylate (see Intermediate 1-4; 9.93 g, 19.9 mmol) and (4-bromo-1-methyl-1H-pyrazol-5-yl)methanol (3.80 g, 19.9 mmol) in 1,4-dioxane (260 ml) was added aqueous 2 M solution of potassium carbonate (30 ml, 2.0 M, 60 mmol). The mixture was degassed and purged with argon several times. Pd(dppf)Cl$_2$×CH$_2$Cl$_2$ (3.25 g, 3.98 mmol) was added and the mixture was purged with argon for 10 minutes. The reaction was stirred at 80° C. for 24 hours. For work-up, the reaction mixture was filtered and the residue was washed with dichloromethane. The filtrate was concentrated under reduced pressure and the residue was purified by flash chromatography (dichloromethane/ethyl acetate gradient, 0%→100% ethyl acetate) to give the title compound (8.1 g).

LC-MS (Method 2): Rt=1.54 min; MS (ESIpos): m/z=484 [M+H]$^+$ $^1$H-NMR (400 MHz, DMSO-d6) δ [ppm]: 1.066 (16.00), 1.270 (0.72), 1.288 (1.61), 1.306 (0.73), 3.160 (1.60), 3.173 (1.64), 3.939 (2.89), 3.951 (2.36), 4.194 (0.49), 4.262 (0.66), 4.279 (0.65), 4.474 (0.46), 4.485 (0.44), 7.517 (0.48), 7.584 (0.98).

350

Intermediate 1-172 ethyl 1-{3-[(tert-butoxycarbonyl)(methyl)amino]propyl}-7-[5-(hydroxymethyl)-1-methyl-1H-pyrazol-4-yl]-3-[3-(naphthalen-1-yloxy)propyl]-1H-indole-2-carboxylate

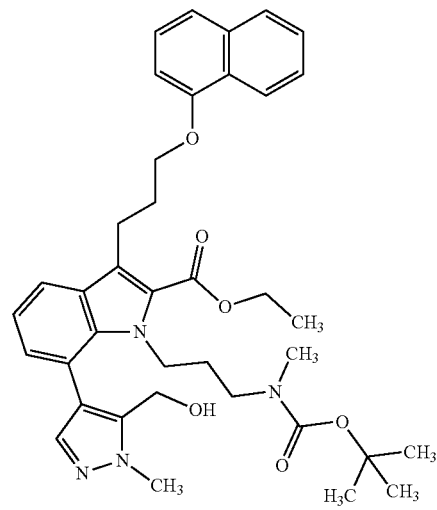 [SMILES: CCOC(=O)c1c(CCCOc2cccc3ccccc23)c2cccc(-c3cnn(C)c3CBr)c2n1CCCN(C)C(=O)OC(C)(C)C]

To a solution of ethyl 7-[5-(hydroxymethyl)-1-methyl-1H-pyrazol-4-yl]-3-[3-(naphthalen-1-yloxy)propyl]-1H-indole-2-carboxylate (1.20 g, 2.48 mmol) in DMF (32 ml) was added caesium carbonate (4.04 g, 12.4 mmol), and the mixture was stirred for 10 min at room temperature. Tert-butyl (3-bromopropyl)methylcarbamate (see Intermediate 1-1; 626 mg, 2.48 mmol) was added and the reaction was stirred for 5 days at room temperature. For work-up, the reaction mixture was filtered and the residue was concentrated under reduced pressure. The crude product was purified twice by flash chromatography (dichloromethane/methanol gradient, 0%→5% methanol, followed by dichloromethane/methanol gradient, 2%→5% methanol) to give the title compound (1.0 g).

LC-MS (Method 1): Rt=1.68 min; MS (ESIpos): m/z=655 [M+H]$^+$

351

Intermediate 1-173 ethyl 7-[5-(bromomethyl)-1-methyl-1H-pyrazol-4-yl]-1-{3-[(tert-butoxycarbonyl)(methyl)amino]propyl}-3-[3-(naphthalen-1-yloxy)propyl]-1H-indole-2-carboxylate

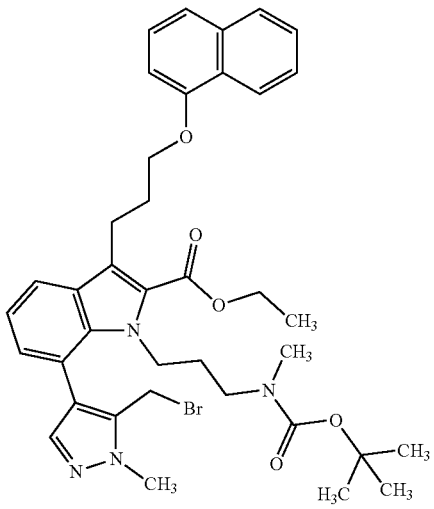

To a solution of ethyl 1-{3-[(tert-butoxycarbonyl)(methyl)amino]propyl}-7-[5-(hydroxymethyl)-1-methyl-1H-pyrazol-4-yl]-3-[3-(naphthalen-1-yloxy)propyl]-1H-indole-2-carboxylate (1.00 g, 1.53 mmol) in dichloromethane (28 ml), triphenylphosphine (961 mg, 3.67 mmol) was added at 0° C. and the mixture was stirred at 0° C. for 10 min. Tetrabromomethane (1.11 g, 3.36 mmol) was added and the reaction was stirred at 0° C. for 5 hours. For work-up, the reaction mixture was concentrated under reduced pressure and the crude product (1.1 g) was used in the subsequent steps without further purification.

352

Intermediate 1-174 ethyl 7-[5-(bromomethyl)-1-methyl-1H-pyrazol-4-yl]-1-[3-(methylamino)propyl]-3-[3-(naphthalen-1-yloxy)propyl]-1H-indole-2-carboxylate hydrochloric acid salt

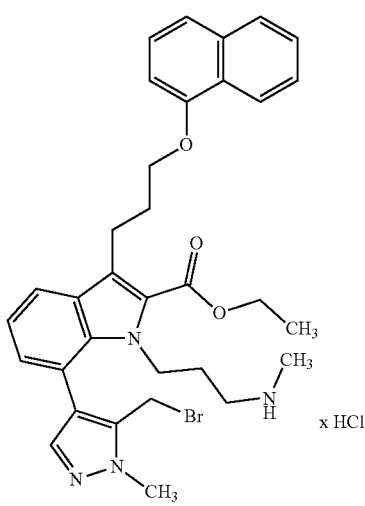 [SMILES: CCOC(=O)c1c(CCCOc2cccc3ccccc23)c2cccc(-c3cnn(C)c3CBr)c2n1CCCNC ; "x HCl"]

To a solution of ethyl 7-[5-(bromomethyl)-1-methyl-1H-pyrazol-4-yl]-1-{3-[(tert-butoxycarbonyl)(methyl)amino]propyl}-3-[3-(naphthalen-1-yloxy)propyl]-1H-indole-2-carboxylate (1.00 g, 1.39 mmol) in methanol (25 ml) was added a 4 M solution of HCl in dioxan (24 ml, 4.0 M, 98 mmol) at 0° C. and the mixture was stirred for 2 hours at room temperature. For work-up, the mixture was concentrated under reduced pressure and the crude product (950 mg) was used for the subsequent steps without further purification.

Intermediate 1-175

(rac)-ethyl 7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylate

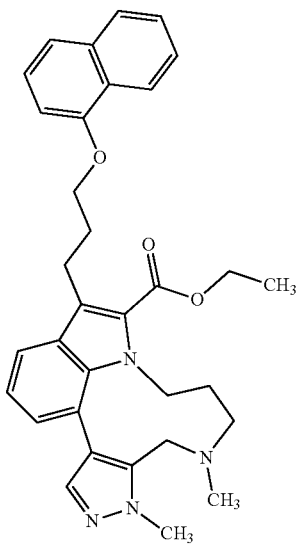 [SMILES: CCOC(=O)c1c(CCCOc2cccc3ccccc23)c2cccc3c2n1CCCN(C)Cc1c-3cnn1C]

To a solution of ethyl 7-[5-(bromomethyl)-1-methyl-1H-pyrazol-4-yl]-1-[3-(methylamino)propyl]-3-[3-(naphthalen-1-yloxy)propyl]-1H-indole-2-carboxylate hydrochloric acid salt (950 mg) in DMF (100 ml) was added caesium carbonate (2.37 g, 7.26 mmol) and the reaction was stirred at 65° C. for 17 hours. For work-up, the mixture was concentrated under reduced pressure and the residue was purified twice by flash chromatography (Biotage SNAP cartridge $NH_2$ silica, dichloromethane/methanol gradient, 0%→5% methanol followed by hexane/ethyl acetate gradient, 7%→100% ethyl acetate) to give the title compound (430 mg).

LC-MS (Method 2): Rt=1.73 min; MS (ESIpos): m/z=537 [M+H]$^+$ $^1$H-NMR (400 MHz, DMSO-d6) δ [ppm]: 1.253 (4.59), 1.270 (10.02), 1.288 (4.67), 1.541 (1.32), 1.880 (0.45), 1.899 (0.43), 1.907 (0.49), 1.919 (0.51), 2.178 (13.23), 2.203 (1.23), 2.220 (0.41), 2.304 (0.42), 2.318 (0.80), 2.327 (0.84), 2.338 (0.49), 2.355 (0.51), 2.518 (1.48), 2.523 (0.99), 2.888 (0.40), 3.046 (1.69), 3.082 (1.83), 3.239 (0.65), 3.254 (0.65), 3.273 (1.06), 3.291 (0.46), 3.350 (1.07), 3.369 (0.62), 3.383 (0.65), 3.640 (1.76), 3.676 (1.58), 3.789 (0.46), 3.804 (0.73), 3.825 (0.54), 3.839 (0.42), 3.877 (16.00), 4.165 (1.50), 4.180 (3.14), 4.193 (1.78), 4.201 (0.85), 4.210 (0.71), 4.220 (2.20), 4.238 (3.11), 4.257 (2.11), 4.266 (0.61), 4.274 (0.54), 4.284 (0.56), 4.376 (0.43), 4.387 (0.93), 4.398 (0.50), 4.412 (0.47), 4.424 (0.86), 5.759 (1.46), 6.873 (1.89), 6.891 (2.02), 6.936 (1.30), 6.939 (1.52), 6.953 (2.53), 6.956 (2.42), 6.987 (2.15), 7.006 (2.41), 7.024 (1.27), 7.365 (7.19), 7.382 (2.55), 7.402 (1.98), 7.444 (2.69), 7.465 (1.52), 7.483 (0.42), 7.487 (0.59), 7.500 (1.46), 7.504 (1.35), 7.512 (1.55), 7.518 (3.16), 7.524 (1.61), 7.531 (1.45), 7.535 (1.59), 7.549 (0.62), 7.552 (0.42), 7.714 (1.78), 7.717 (1.91), 7.734 (1.69), 7.737 (1.67), 7.856 (1.58), 7.863 (0.87), 7.875 (1.52), 7.880 (1.32), 8.182 (1.33), 8.187 (1.34), 8.206 (1.29).

Intermediate 1-176

N-(3-Bromopropyl)aniline

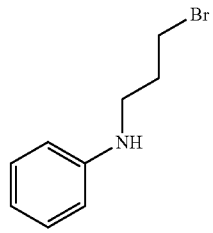 [SMILES: BrCCCNc1ccccc1]

To a solution of aniline (2.0 g, 21.4 mmol, 1.0 eq) in DMF (12.0 mL) was added potassium carbonate (5.9 g, 42.8 mmol, 2.0 eq) and 1,2-dibromopropane (4.3 g, 21.4 mmol, 1.0 eq). The mixture was stirred at 70° C. for 2 hours, cooled to rt, diluted with ethyl acetate (80 ml). The organic layer was washed with water (2×20 mL), brine (20 mL), dried over sodium sulfate, filtered and concentrated. The crude product was purified by flash chromatography (ethyl acetate/hexanes=1/5) to give the title compound (1.7 g) as a colorless oil.

MS: m/z=214 [M+H]$^+$.

Intermediate 1-177

Ethyl 1-(3-anilinopropyl)-7-[5-(hydroxymethyl)-1,3-dimethyl-1H-pyrazol-4-yl]-3-[3-(1-naphthyloxy)propyl]-1H-indole-2-carboxylate

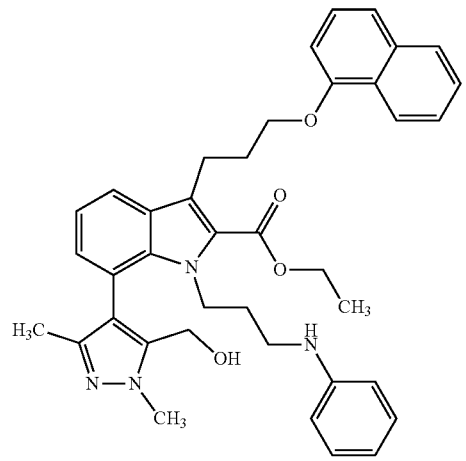

To a solution of ethyl 7-[5-(hydroxymethyl)-1,3-dimethyl-1H-pyrazol-4-yl]-3-[3-(1-naphthyloxy)propyl]-1H-indole-2-carboxylate (see Intermediate 1-39; 0.1 g, 0.2 mmol, 1.0 eq) in DMF (3.0 mL) was added caesium carbonate (0.2 g, 0.6 mmol, 3.0 eq). The mixture was stirred at rt for 10 min. N-(3-bromopropyl)aniline (66.0 mg, 0.3 mmol, 1.5 eq) was added and the mixture was stirred at 25° C. for 17 hrs, cooled to rt, diluted with ethyl acetate (30 mL), washed with water, dried over sodium sulfate, filtered and concentrated.

The residue was purified by flash chromatography (ethyl acetate/dichloromethane=1/1 with 3% methanol) to give the title compound (60.0 mg) as white solid.

MS: m/z=631 [M+H]⁺.

Intermediate 1-178

Ethyl 1-(3-anilinopropyl)-7-[5-(bromomethyl)-1,3-dimethyl-1H-pyrazol-4-yl]-3-[3-(1-naphthyloxy)propyl]-1H-indole-2-carboxylate

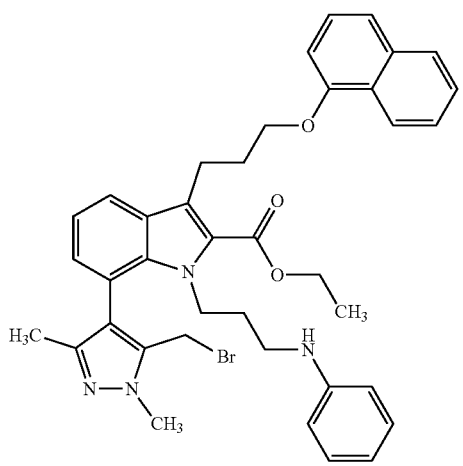 [SMILES: CCOC(=O)c1c(CCCOc2cccc3ccccc23)c2cccc(-c3c(C)nn(C)c3CBr)c2n1CCCNc1ccccc1]

To a solution of ethyl 1-(3-anilinopropyl)-7-[5-(hydroxymethyl)-1,3-dimethyl-1H-pyrazol-4-yl]-3-[3-(1-naphthyloxy)propyl]-1H-indole-2-carboxylate (60.0 mg, 0.095 mmol, 1.0 eq) in dichloromethane (2.0 mL) at 0° C. was added triphenylphosphine (60.0 mg, 0.23 mmol, 2.4 eq). The mixture was stirred at 0° C. for 10 min before a solution of tetrabromomethane (69.4 mg, 0.21 mmol, 2.2 eq) in dichloromethane (0.5 ml) was added. The resulting mixture was stirred at rt for 18 hrs, concentrated to afford the crude title compound, which was used directly in the next step.

MS: m/z=693 [M+H]⁺.

Intermediate 1-179

(rac)-Ethyl 9,11-dimethyl-1-[3-(1-naphthyloxy)propyl]-7-phenyl-4,5,6,7,8,9-hexahydropyrazolo[3',4':7,8][1,5]diazecino[9,10,1-hi]indole-2-carboxylate

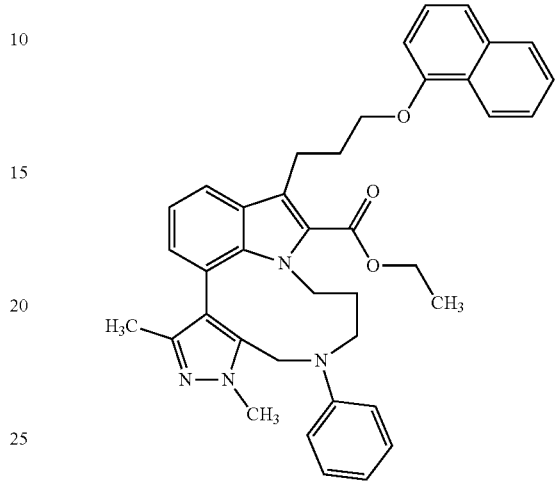

To a solution of crude ethyl 1-(3-anilinopropyl)-7-[5-(bromomethyl)-1,3-dimethyl-1H-pyrazol-4-yl]-3-[3-(1-naphthyloxy)propyl]-1H-indole-2-carboxylate (~0.095 mmol, 1.0 eq) in DMF (11.0 mL) was added caesium carbonate (155 mg, 0.47 mmol, 5.0 eq). The resulting mixture was stirred at 65° C. for 16 hrs, cooled to rt, and concentrated under reduced pressure. The residue was then partitioned between a mixture of ethyl acetate and hexanes (1/1, 25 mL) and water (10 mL). The organic layer was separated, dried over sodium sulfate, filtered and concentrated. The residue was purified by flash chromatography (ethyl acetate/dichloromethane=1/2) to give the title compound (34.0 mg) as white solid.

MS: m/z=613 [M+H]⁺.

Intermediate 1-180

N-(3-Bromopropyl)-4-(morpholin-4-yl)aniline

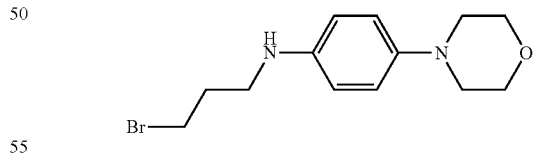

To a solution of 4-(morpholin-4-yl)aniline (2.0 g, 21.4 mmol, 1.0 eq) in DMF (12.0 mL) was added was added potassium carbonate (5.9 g, 42.8 mmol, 2.0 eq) and 1,3-dibromopropane (4.3 g, 21.4 mmol, 1.0 eq). The mixture was stirred at 70° C. for 2 hrs, cooled to rt, diluted with ethyl acetate (80 mL), washed with water (2×20 mL), brine (20 mL), dried over sodium sulfate, filtered and concentrated. The crude product was purified by flash chromatography (ethyl acetate/hexanes=1:5) to give the title compound (1.7 g) as a colorless oil.

MS: m/z=299 [M+H]⁺.

357

Intermediate 1-181

Ethyl 7-[5-(hydroxymethyl)-1,3-dimethyl-1H-pyrazol-4-yl]-1-(3-{[4-(morpholin-4-yl)phenyl]amino}propyl)-3-[3-(1-naphthyloxy)propyl]-1H-indole-2-carboxylate

358

Intermediate 1-182

Ethyl 7-[5-(bromomethyl)-1,3-dimethyl-1H-pyrazol-4-yl]-1-(3-{[4-(morpholin-4-yl)phenyl]amino}propyl)-3-[3-(1-naphthyloxy)propyl]-1H-indole-2-carboxylate

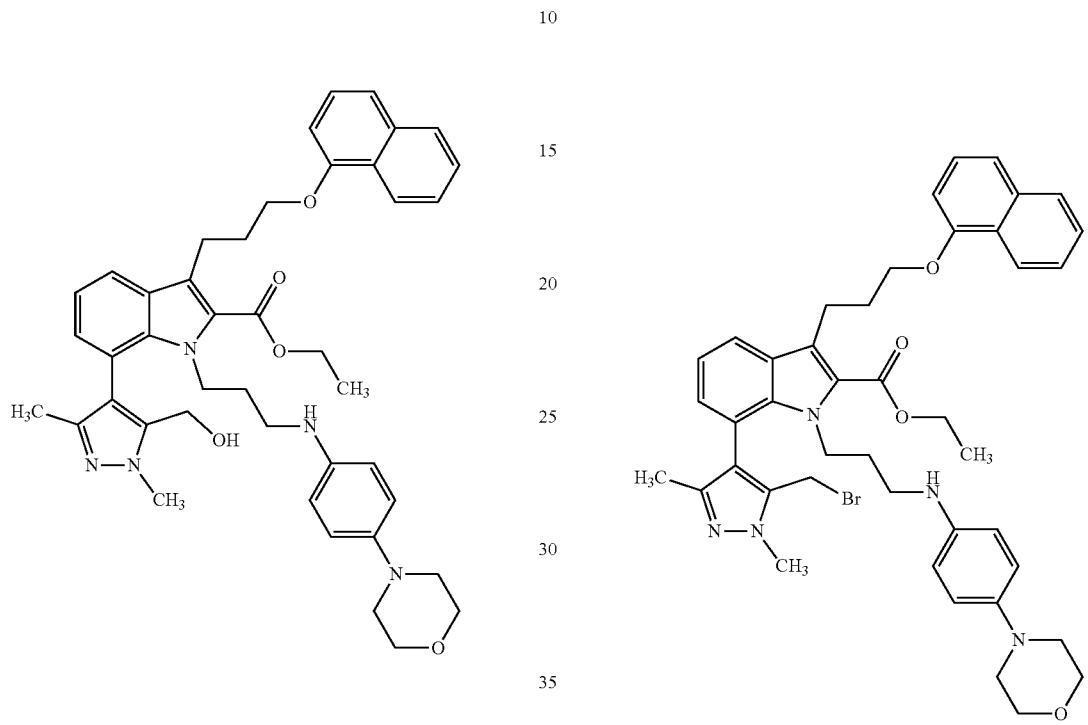

To a solution of ethyl 7-[5-(hydroxymethyl)-1,3-dimethyl-1H-pyrazol-4-yl]-3-[3-(1-naphthyloxy)propyl]-1H-indole-2-carboxylate (see Intermediate 1-39; 0.1 g, 0.2 mmol, 1.0 eq) in DMF (3.0 mL) was added caesium carbonate (200 mg, 0.6 mmol, 3.0 eq). The mixture was stirred at rt for 10 min. N-(3-bromopropyl)-4-(morpholin-4-yl)aniline (66.0 mg, 0.3 mmol, 1.5 eq) was added and the mixture was stirred at 25° C. for 17 hrs, cooled to rt, diluted with ethyl acetate (30 mL), washed with water, dried over sodium sulfate, filtered and concentrated. The residue was purified by flash chromatography (ethyl acetate/dichloromethane=1/1 with 3% methanol) to give the title compound (60.0 mg) as a white solid.

MS: m/z=716 [M+H]$^+$.

To a solution of ethyl 7-[5-(hydroxymethyl)-1,3-dimethyl-1H-pyrazol-4-yl]-1-(3-{[4-(morpholin-4-yl)phenyl]amino}propyl)-3-[3-(1-naphthyloxy)propyl]-1H-indole-2-carboxylate (60.0 mg, 0.084 mmol, 1.0 eq) in dichloromethane (2.0 mL) at 0° C. was added triphenylphosphine (60.0 mg, 0.23 mmol, 2.4 eq). The mixture was stirred at 0° C. for 10 min before a solution of tetrabromomethane (69.4 mg, 0.21 mmol, 2.5 eq) in dichloromethane (0.5 ml) was added. The resulting mixture was stirred at rt for 18 hrs, concentrated to afford the crude title compound, which was used directly in the next step.

MS: m/z=778 [M+H]$^+$.

Intermediate 1-183

(rac)-Ethyl 9,11-dimethyl-7-[4-(morpholin-4-yl)
phenyl]-1-[3-(1-naphthyloxy)propyl]-4,5,6,7,8,9-
hexahydropyrazolo[3',4':7,8][1,5]diazecino[9,10,1-
hi]indole-2-carboxylate

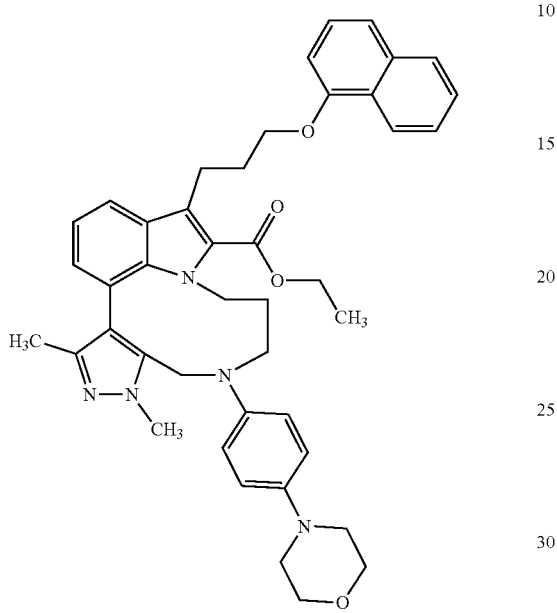

To a solution of the crude ethyl 7-[5-(bromomethyl)-1,3-dimethyl-1H-pyrazol-4-yl]-1-(3-{[4-(morpholin-4-yl)phenyl]amino}propyl)-3-[3-(1-naphthyloxy)propyl]-1H-indole-2-carboxylate (0.084 mmol, 1.0 eq) in DMF (11.0 mL) was added caesium carbonate (0.155 g, 0.47 mmol, 5.0 eq). The resulting mixture was stirred at 65° C. for 16 hrs, cooled to rt and concentrated under reduced pressure. The residue was then partitioned between a mixture of ethyl acetate and hexanes (1/1, 25 mL) and water (10 mL). The organic layer was separated, dried over sodium sulfate, filtered and concentrated. The residue was purified by flash chromatography (1:2 of ethyl acetate/dichloromethane) to give the title compound (40 mg, 68%) as white solid.

MS: m/z=698 [M+H]$^+$.

Intermediate 1-184

N-(2-Bromoethyl)aniline

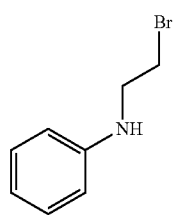

To a solution of aniline (2.0 g, 21.4 mmol, 1.0 eq) in DMF (12.0 mL) was added potassium carbonate (5.9 g, 42.8 mmol, 2.0 eq) and 1,2-dibromoethane (4.3 g, 21.4 mmol, 1.0 eq). The mixture was stirred at 70° C. for 2 hrs, cooled to rt, diluted with ethyl acetate (80 mL), washed with water (2×20 mL), brine (20 mL), dried over sodium sulfate, filtered and concentrated. The crude product was purified by flash chromatography (ethyl acetate/hexanes=1/5) to give the title compound (0.40 g, 9%) as a colorless oil.

MS: m/z=200 [M+H]$^+$.

Intermediate 1-185

Ethyl 1-(2-anilinoethyl)-7-[5-(hydroxymethyl)-1,3-
dimethyl-1H-pyrazol-4-yl]-3-[3-(1-naphthyloxy)
propyl]-1H-indole-2-carboxylate

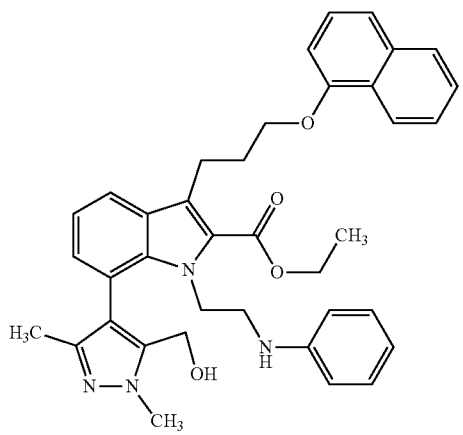

To a solution of ethyl 7-[5-(hydroxymethyl)-1,3-dimethyl-1H-pyrazol-4-yl]-3-[3-(1-naphthyloxy)propyl]-1H-indole-2-carboxylate (see Intermediate 1-39; 0.11 g, 0.22 mmol, 1.0 eq) in DMF (3 mL) was added caesium carbonate (0.22 g, 0.66 mmol, 3.0 eq). The mixture was stirred at rt for 10 min. N-(2-bromoethyl)aniline (66.4 mg, 0.33 mmol, 1.5 eq) was added and the mixture was stirred at 35° C. for 17 hrs, cooled to rt, diluted with ethyl acetate (30 mL), washed with water, dried over sodium sulfate, filtered and concentrated. The residue was purified by flash chromatography (ethyl acetate/dichloromethane=1/1 with 2% methanol) to give the title compound (25.0 mg, 18%) as white solid.

MS: m/z=617 [M+H]$^+$.

Intermediate 1-186

Ethyl 1-(2-anilinoethyl)-7-[5-(bromomethyl)-1,3-dimethyl-1H-pyrazol-4-yl]-3-[3-(1-naphthyloxy)propyl]-1H-indole-2-carboxylate

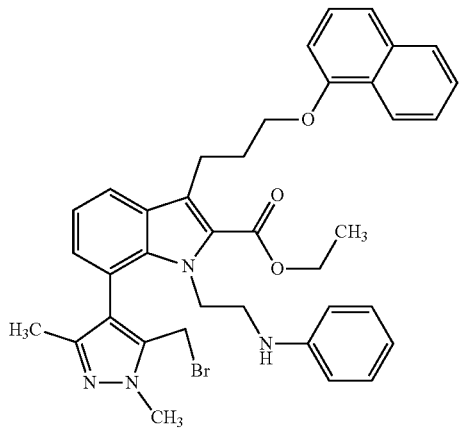 [SMILES: CCOC(=O)c1c(CCCOc2cccc3ccccc23)c2cccc(-c3c(C)nn(C)c3CBr)c2n1CCNc1ccccc1]

To a solution of ethyl 1-(2-anilinoethyl)-7-[5-(hydroxymethyl)-1,3-dimethyl-1H-pyrazol-4-yl]-3-[3-(1-naphthyloxy)propyl]-1H-indole-2-carboxylate (25.0 mg, 0.04 mmol, 1.0 eq) in dichloromethane (2.0 mL) at 0° C. was added triphenylphosphine (25.5 mg, 0.97 mmol, 2.4 eq). The mixture was stirred at 0° C. for 10 min before a solution of tetrabromomethane (29.4 mg, 0.89 mmol, 2.2 eq) in dichloromethane (0.5 ml) was added. The resulting mixture was stirred at rt for 18 hrs, concentrated to afford the crude title compound, which was used directly in the next step.

MS: m/z=679 [M+H]$^+$.

Intermediate 1-187

(rac)-Ethyl 8,10-dimethyl-1-[3-(1-naphthyloxy)propyl]-6-phenyl-5,6,7,8-tetrahydro-4H-pyrazolo[3',4':6,7][1,4]diazonino[8,9,1-hi]indole-2-carboxylate

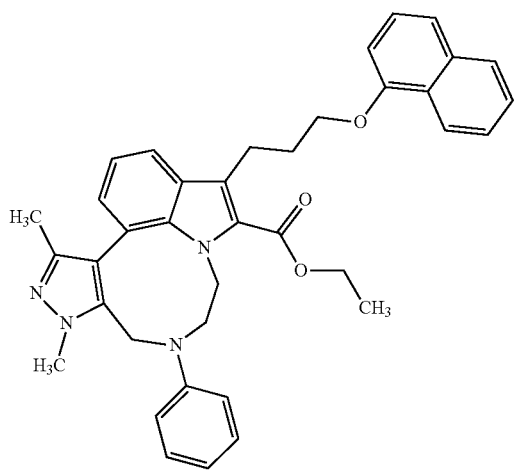 [SMILES: CCOC(=O)c1c(CCCOc2cccc3ccccc23)c2cccc3c2n1CCN(c1ccccc1)Cc1c-3c(C)nn1C]

To a solution of ethyl 1-(2-anilinoethyl)-7-[5-(bromomethyl)-1,3-dimethyl-1H-pyrazol-4-yl]-3-[3-(1-naphthyloxy)propyl]-1H-indole-2-carboxylate (~0.04 mmol, 1.0 eq) in DMF (11 mL) was added caesium carbonate (65.0 mg, 0.2 mmol, 5.0 eq). The resulting mixture was stirred at 65° C. for 16 hrs, cooled to rt and concentrated under reduced pressure. The residue was then partitioned between a mixture of ethyl acetate and hexanes (1/1, 25.0 mL) and water (10.0 mL). The organic layer was separated, dried over sodium sulfate, filtered and concentrated. The residue was purified by prep. HPLC (Instrument: Varian SD-200; Column: Phenomenex Luna 10μ 250×21.6 mm; eluent A: water+0.1% trifluoracetic acid, Eluent B: acetonitrile+0.1% trifluoracetic acid; gradient: 0.0 min 95% A→30.0 min 0% A→32.0 min 0% A→35 min 95% A→36.0 min 95% A (stop); flow 20 ml/min; temperature: rt ° C.; detector Varian Variable wavelength UV detector) to give the title compound (3.5 mg) as white solid.

MS: m/z=599 [M+H]$^+$.

Intermediate 1-188

Ethyl 4-bromo-3-(methoxymethyl)-1-methyl-1H-pyrazole-5-carboxylate

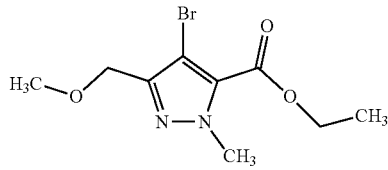

To methanol (5.0 mL) was added sodium (0.18 g, 7.66 mmol, 5.0 eq). The mixture was stirred at rt until all sodium had reacted. ethyl 4-bromo-3-(bromomethyl)-1-methyl-1H-pyrazole-5-carboxylate (see Intermediate 1-5; 0.50 g, 1.53 mmol, 1.0 eq) was added. The mixture was stirred at rt for 2.0 hrs, diluted with ethyl acetate (30 mL), washed with water (2×10 mL), brine (10 mL), dried over sodium sulfate, filtered and concentrated. The crude product was purified by flash chromatography (ethyl acetate/hexanes=1/5) to give the title compound (0.21 g, 49.5%) as light yellow solid.

MS: m/z=277 [M+H]$^+$.

Intermediate 1-189

[4-Bromo-3-(methoxymethyl)-1-methyl-1H-pyrazol-5-yl]methanol

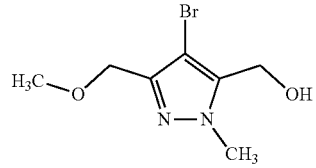

To a solution of ethyl 4-bromo-3-(methoxymethyl)-1-methyl-1H-pyrazole-5-carboxylate (0.20 g, 0.72 mmol, 1.0 eq) in THF (5.0 mL) was added lithium aluminium hydride (2 N in THF, 0.36 mL, 0.72 mmol, 1.0 eq) dropwise at 0° C. The resulting mixture was stirred at 0° C. for 20 min. Water (0.1 mL) was added dropwise, followed by a 10% solution of sodium hydroxide in water (0.1 mL) and again water (0.1 mL). The resulting mixture was stirred at rt for 30 min and then passed through a pad of Celite. The filtrate was concentrated to give the title compound (0.17 g, 100%) as a white solid which was used directly in the next step.

MS: m/z=235 [M+H]$^+$.

Intermediate 1-190

Ethyl 7-[5-(hydroxymethyl)-3-(methoxymethyl)-1-methyl-1H-pyrazol-4-yl]-3-[3-(1-naphthyloxy)propyl]-1H-indole-2-carboxylate

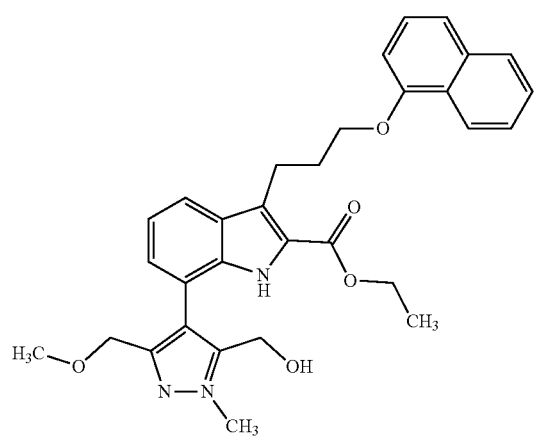

Sodium carbonate (0.30 g, 2.8 mmol, 4.0 eq), water (1.5 mL) and [4-bromo-3-(methoxymethyl)-1-methyl-1H-pyrazol-5-yl]methanol (0.17 g, 0.72 mmol, 1.0 eq) was added to a solution of ethyl 3-[3-(1-naphthyloxy)propyl]-7-(4,4,5,5-tetramethyl-1,3,2-dioxaborolan-2-yl)-1H-indole-2-carboxylate (see Intermediate 1-4; 0.36 g, 0.72 mmol, 1.0 eq) in dioxane (4 mL). The mixture was de-gassed three times. Tetrakis(triphenylphosphine)palladium(0) (Pd(PPh$_3$)$_4$; 65.0 mg, 0.056 mmol, 8.0 mol %) was added. The mixture was de-gassed another three times, stirred at 80° C. for 12 hrs and cooled to rt The reaction mixture was diluted with ethyl acetate (50 mL), washed with water, dried over sodium sulfate, filtered and concentrated. The residue was purified by flash chromatography (ethyl acetate/dichloromethane=1/1 to 2/1) to give the title compound (0.15 g, 39.5%) as a light yellow solid.

MS: m/z=528 [M+H]$^+$.

Intermediate 1-191

Ethyl 1-{3-[(tert-butoxycarbonyl)(methyl)amino]propyl}-7-[5-(hydroxymethyl)-3-(methoxymethyl)-1-methyl-1H-pyrazol-4-yl]-3-[3-(1-naphthyloxy)propyl]-1H-indole-2-carboxylate To a solution of ethyl 7-[5-(hydroxymethyl)-3-(methoxymethyl)-1-methyl-1H-pyrazol-4-yl]-3-[3-(1-naphthyloxy)propyl]-1H-indole-2-carboxylate (0.15 g, 0.27 mmol, 1.0 eq) in DMF (3.0 mL) was added caesium carbonate (0.36 g, 1.10 mmol, 4.0 eq). The mixture was stirred at rt for 10 min. tert-butyl (3-bromopropyl)methylcarbamate (see Intermediate 1-1; 83.2 mg, 0.33 mmol, 1.2 eq) was added. The mixture was stirred at 35° C. for 8.0 hrs, cooled to rt, diluted with ethyl acetate (30 mL), washed with water, dried over sodium sulfate, and was filtered and concentrated. The residue was purified by flash chromatography (ethyl acetate/hexanes=1/1 to 2/1) to give the title compound (0.10 g, 52.1%) as white solid.

MS: m/z=699 [M+H]$^+$.

Intermediate 1-192

Ethyl 7-[5-(bromomethyl)-3-(methoxymethyl)-1-methyl-1H-pyrazol-4-yl]-1-{3-[(tert-butoxycarbonyl)(methyl)amino]propyl}-3-[3-(1-naphthyloxy)propyl]-1H-indole-2-carboxylate

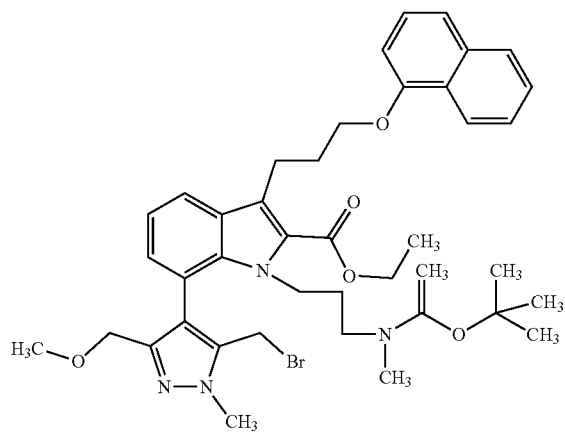 [SMILES: C=C(OC(C)(C)C)N(C)CCCn1c(C(=O)OCC)c(CCCOc2cccc3ccccc23)c2cccc(-c3c(COC)nn(C)c3CBr)c21]

To a solution of ethyl 1-{3-[(tert-butoxycarbonyl)(methyl)amino]propyl}-7-[5-(hydroxymethyl)-3-(methoxymethyl)-1-methyl-1H-pyrazol-4-yl]-3-[3-(1-naphthyloxy)propyl]-1H-indole-2-carboxylate (0.10 g, 0.14 mmol, 1.0 eq) in dichloromethane (2.0 mL) at 0° C. was added triphenylphosphine (0.18 g, 0.68 mmol, 4.8 eq). The mixture was stirred at 0° C. for 10 min. before a solution of tetrabromomethane (0.21 g, 0.63 mmol, 4.4 eq) in dichloromethane (1 ml) was added. The resulting mixture was stirred at rt for 18 hrs, concentrated, and the crude title compound was used directly in the next step.

MS: m/z=761 [M+H]⁺.

Intermediate 1-193

Ethyl 7-[5-(bromomethyl)-3-(methoxymethyl)-1-methyl-1H-pyrazol-4-yl]-1-[3-(methylamino)propyl]-3-[3-(1-naphthyloxy)propyl]-1H-indole-2-carboxylate hydrochloric acid salt

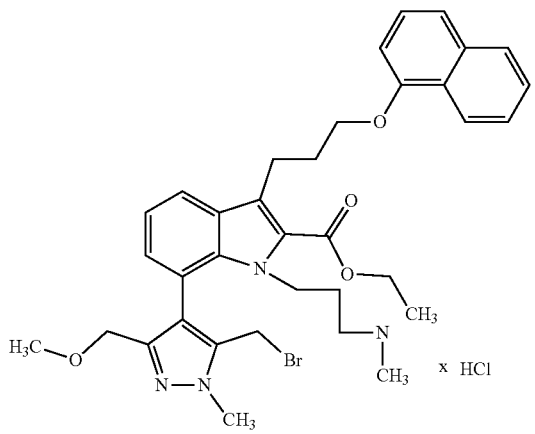 [SMILES: CCOC(=O)c1c(CCCOc2cccc3ccccc23)c2cccc(-c3c(COC)nn(C)c3CBr)c2n1CCCNC ; Cl]

To a solution of crude ethyl 7-[5-(bromomethyl)-3-(methoxymethyl)-1-methyl-1H-pyrazol-4-yl]-1-{3-[(tert-butoxycarbonyl)(methyl)amino]propyl}-3-[3-(1-naphthyloxy)propyl]-1H-indole-2-carboxylate (0.14 mmol) in methanol (2.0 mL) was added HCl in dioxane (4 N, 2.0 mL) at 0° C. The mixture was stirred at room temperature for 2 hrs and then concentrated to give the crude title compound which was used directly in the next step.

MS: m/z=661 [M+H]⁺.

Intermediate 1-194

(rac)-Ethyl 11-(methoxymethyl)-7,9-dimethyl-1-[3-(1-naphthyloxy)propyl]-4,5,6,7,8,9-hexahydropyrazolo[3',4':7,8][1,5]diazecino[9,10,1-hi]indole-2-carboxylate

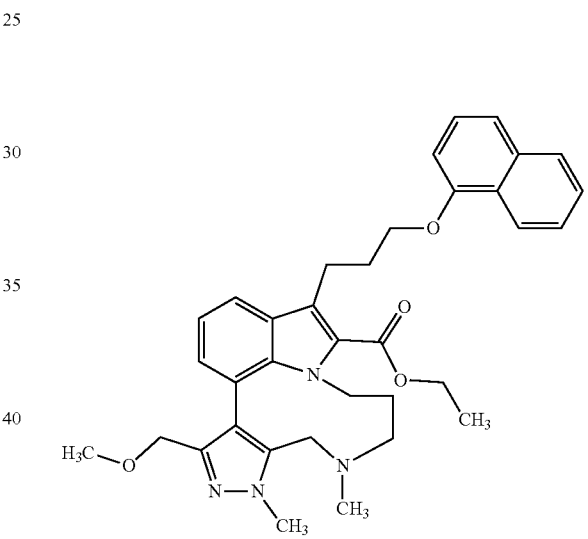

To a solution of crude ethyl 7-[5-(bromomethyl)-3-(methoxymethyl)-1-methyl-1H-pyrazol-4-yl]-1-[3-(methylamino)propyl]-3-[3-(1-naphthyloxy)propyl]-1H-indole-2-carboxylate hydrochloric acid salt (0.14 mmol, 1.0 eq) in DMF (11.0 mL) was added caesium carbonate (0.23 g, 0.71 mmol, 5.0 eq). The resulting mixture was stirred at 30° C. for 16 hrs, cooled to rt and concentrated under reduced pressure. The residue was then partitioned between a mixture of ethyl acetate and hexanes (1/1, 25.0 mL) and water (10.0 mL). The organic layer was separated, dried over sodium sulfate, filtered and concentrated. The residue was purified by flash chromatography (ethyl acetate/dichloromethane=1/1) to to give the title compound (35.0 mg, 42.2% over the last three steps) as a light brown oil (~90% purity).

MS: m/z=581 [M+H]⁺.

Intermediate 1-195

N-(3-Bromopropyl)-4-iodoaniline

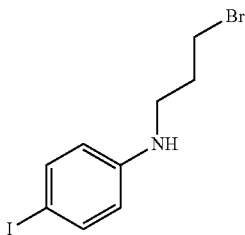 [SMILES: BrCCCNc1ccc(I)cc1]

To a solution of 4-iodoaniline (1.0 g, 4.6 mmol, 1.0 eq) in DMF (6.0 mL) was added was added caesium carbonate (3.0 g, 9.1 mmol, 2.0 eq) and 1,3-dibromopropane (0.9 g, 4.6 mmol, 1.0 eq). The mixture was stirred at 70° C. for 12.0 hrs, cooled to rt, diluted with ethyl acetate (60 mL), washed with water (2×20 mL), brine (20 mL), dried over sodium sulfate, and was filtered and concentrated. The crude product was purified by flash chromatography (ethyl acetate/hexanes=1/5) to give the title compound (0.5 g, 32.0%) as a light brown oil.

MS: m/z=340 [M+H]$^+$.

Intermediate 1-196

Ethyl 7-[5-(hydroxymethyl)-1,3-dimethyl-1H-pyrazol-4-yl]-1-{3-[(4-iodophenyl)amino]propyl}-3-[3-(1-naphthyloxy)propyl]-1H-indole-2-carboxylate

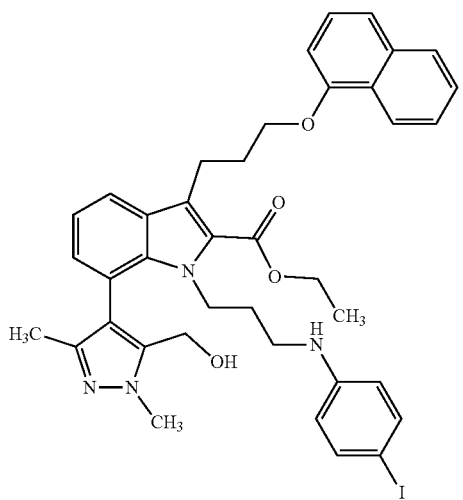

To a solution of ethyl 7-[5-(hydroxymethyl)-1,3-dimethyl-1H-pyrazol-4-yl]-3-[3-(1-naphthyloxy)propyl]-1H-indole-2-carboxylate (see Intermediate 1-39; 0.41 g, 0.82 mmol, 1.0 eq) in DMF (8.0 mL) was added caesium carbonate (1.1 g, 3.3 mmol, 4.0 eq). The mixture was stirred at rt for 10 min. N-(3-bromopropyl)-4-iodoaniline (0.42 g, 1.2 mmol, 1.5 eq) was added and the mixture was stirred at room temperature for 17 hrs, and was then diluted with ethyl acetate (40 mL), washed with water, dried over sodium sulfate, filtered and concentrated. The residue was purified by flash chromatography (ethyl acetate/dichloromethane=1/1 with 2% methanol) to give the title compound (0.30 g, 48.2%) as a white solid.

MS: m/z=757 [M+H]$^+$.

Intermediate 1-197

Ethyl 7-[5-(bromomethyl)-1,3-dimethyl-1H-pyrazol-4-yl]-1-{3-[(4-iodophenyl)amino]propyl}-3-[3-(1-naphthyloxy)propyl]-1H-indole-2-carboxylate

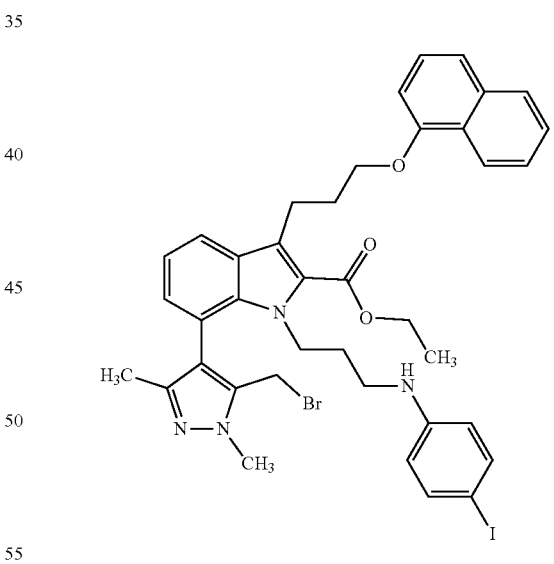

To a solution of ethyl 7-[5-(hydroxymethyl)-1,3-dimethyl-1H-pyrazol-4-yl]-1-{3-[(4-iodophenyl)amino]propyl}-3-[3-(1-naphthyloxy)propyl]-1H-indole-2-carboxylate (0.3 g, 0.4 mmol, 1.0 eq) in DCM (6.0 mL) at 0° C. was added PPh$_3$ (0.25 g, 0.95 mmol, 2.4 eq). The mixture was stirred at 0° C. for 10 min. before a solution of tetrabromomethane (0.29 g, 0.87 mmol, 2.2 eq) was added. The resulting mixture was stirred at rt for 18 hrs, concentrated to afford the crude title compound which was used directly in the next step.

MS: m/z=819 [M+H]$^+$.

369

Intermediate 1-198

(rac)-Ethyl 7-(4-iodophenyl)-9,11-dimethyl-1-[3-(1-naphthyloxy)propyl]-4,5,6,7,8,9-hexahydropyrazolo[3',4':7,8][1,5]diazecino[9,10,1-hi]indole-2-carboxylate

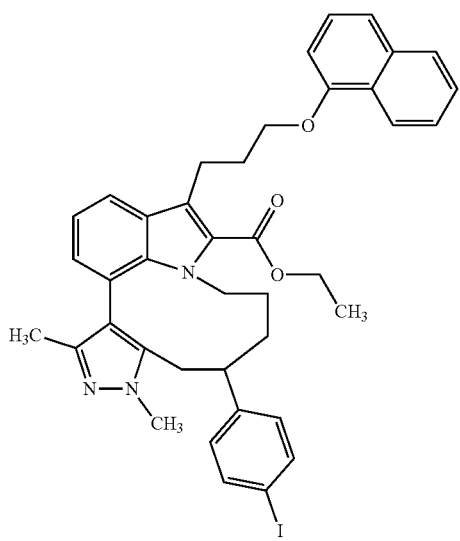 [SMILES: CCOC(=O)c1c(CCCOc2cccc3ccccc23)c2cccc3c2n1CCCC(c1ccc(I)cc1)Cc1c-3c(C)nn1C]

To a solution of ethyl 7-[5-(bromomethyl)-1,3-dimethyl-1H-pyrazol-4-yl]-1-{3-[(4-iodophenyl)amino]propyl}-3-[3-(1-naphthyloxy)propyl]-1H-indole-2-carboxylate (−0.4 mmol, 1.0 eq) in DMF (40.0 mL) was added caesium carbonate (0.65 g, 1.98 mmol, 5.0 eq). The resulting mixture was stirred at 60° C. for 16 hrs, cooled to rt and concentrated under reduced pressure. The residue was then partitioned between a mixture of ethyl acetate (35.0 mL) and water (10.0 mL). The organic layer was separated, dried over sodium sulfate, filtered and concentrated. The residue was purified by flash chromatography (ethyl acetate/dichloromethane=1/1) to give the title compound (150 mg, 50.4% over the last two steps) as a yellow solid.

MS: m/z=739 [M+H]$^+$.

370

Intermediate 1-199

(rac)-Ethyl 7-{4-[4-(tert-butoxycarbonyl) piperazin-1-yl]phenyl}-9,11-dimethyl-1-[3-(1-naphthyloxy)propyl]-4,5,6,7,8,9-hexahydropyrazolo[3',4':7,8][1,5]diazecino[9,10,1-hi]indole-2-carboxylate

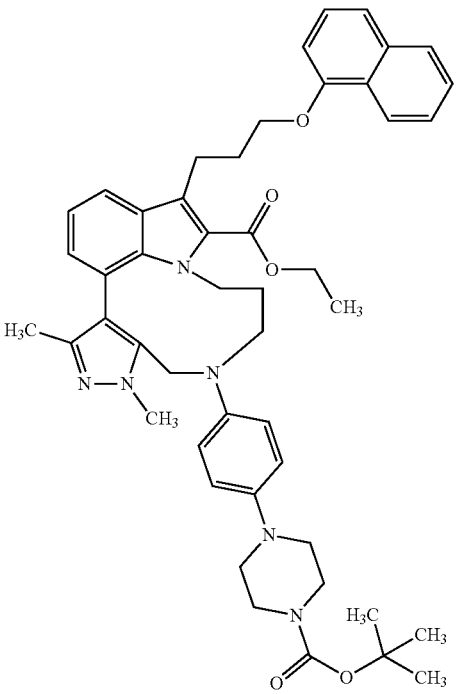 [SMILES: CCOC(=O)c1c(CCCOc2cccc3ccccc23)c2cccc3c2n1CCCN(c1ccc(N2CCN(C(=O)OC(C)(C)C)CC2)cc1)Cc1c-3c(C)nn1C]

A suspension of (rac)-ethyl 7-(4-iodophenyl)-9,11-dimethyl-1-[3-(1-naphthyloxy)propyl]-4,5,6,7,8,9-hexahydropyrazolo[3',4':7,8][1,5]diazecino[9,10,1-hi]indole-2-carboxylate (0.15 g, 0.2 mmol, 1.0 eq), Piperazine-1-carboxylic acid tert-butyl ester (45.4 mg, 0.24 mmol, 1.2 eq) and sodium 2-methylpropan-2-olate (28.8 mg, 0.3 mmol, 1.5 eq) in dioxane was degassed three times. CyJohnPhos ((Biphenyl-2-yl(dicyclohexyl)phosphine) (7.0 mg, 0.02 mmol, 0.1 eq) and palladium(II)acetate (2.2 mg, 0.01 mmol, 5 mol %) were added. The mixture was degassed three times, stirred at 80° C. for 16 hrs, and then cooled to rt. The reaction mixture was diluted with ethyl acetate (30 mL), washed with water, dried over sodium sulfate, and then filtered and concentrated. The residue was purified by flash chromatography (ethyl acetate/dichloromethane=1/1) to give the title compound (51 mg, 32.1%) as a yellow solid.

MS: m/z=797 [M+H]$^+$.

371

Intermediate 1-200

(rac)-Ethyl 7-{4-[4-(dimethylsulfamoyl)piperazin-1-yl]phenyl}-9,11-dimethyl-1-[3-(1-naphthyloxy) propyl]-4,5,6,7,8,9-hexahydropyrazolo[3',4':7,8][1,5]diazecino[9,10,1-hi]indole-2-carboxylate

372

Intermediate 1-201

(rac)-Ethyl 7-{4-[4-(ethylsulfonyl) piperazin-1-yl]phenyl}-9,11-dimethyl-1-[3-(1-naphthyloxy)propyl]-4,5,6,7,8,9-hexahydropyrazolo[3',4':7,8][1,5]diazecino[9,10,1-hi]indole-2-carboxylate

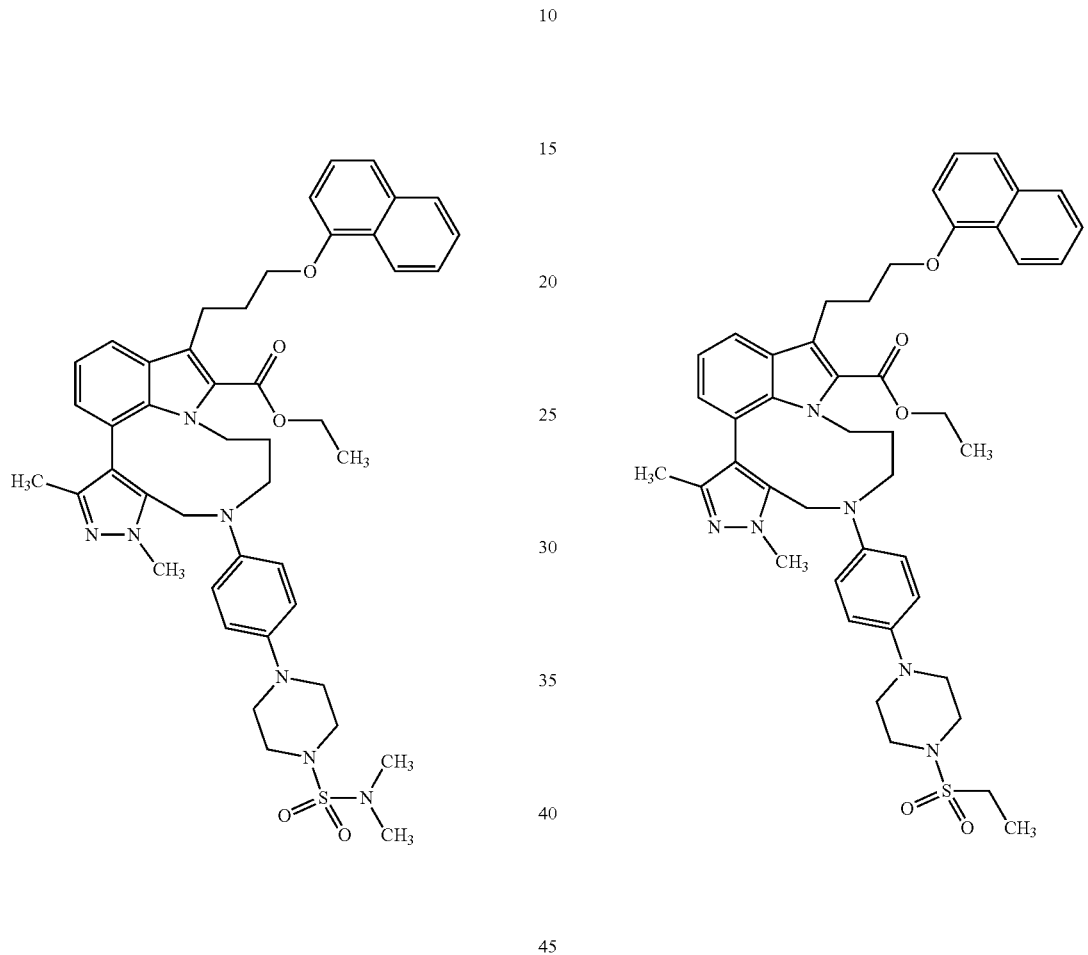

To a solution of (rac)-ethyl 7-{4-[4-(tert-butoxycarbonyl)piperazin-1-yl]phenyl}-9,11-dimethyl-1-[3-(1-naphthyloxy)propyl]-4,5,6,7,8,9-hexahydropyrazolo[3',4':7,8][1,5]diazecino[9,10,1-hi]indole-2-carboxylate (50 mg, 0.06 mmol, 1.0 eq) in methanol (1 mL) was added 4 N HCl in dioxane (1 mL). The mixture was stirred at rt for 2 hrs, concentrated and dried on high vacuum. To the residue (0.06 mmol) in dichloromethane (2.0 mL) was added diisopropylethylamine (41 mg, 0.3 mmol, 5.0 eq). The mixture was stirred at 0° C. for 10 min. A solution of N,N-dimethylsulfamoyl chloride (11 mg, 0.075 mmol, 1.2 eq) in dichloromethane (0.5 mL) was added. The mixture was stirred at rt for 15 hrs, concentrated. The residue was purified by flash chromatography (ethyl acetate/dichloromethane=1/1) to give the title compound (41 mg, 81%) as a colorless oil.

MS: m/z=804 [M+H]$^+$.

To a solution of (rac)-ethyl 7-{4-[4-(tert-butoxycarbonyl)piperazin-1-yl]phenyl}-9,11-dimethyl-1-[3-(1-naphthyloxy)propyl]-4,5,6,7,8,9-hexahydropyrazolo[3',4':7,8][1,5]diazecino[9,10,1-hi]indole-2-carboxylate (see Intermediate 1-199; 49 mg, 0.06 mmol, 1.0 eq) in methanol (1 mL) was added 4 N HCl in dioxane (1 mL). The mixture was stirred at rt for 2 hrs, concentrated and dried on high vacuum. To a solution of the residue in dichloromethane (2.0 mL) was added diisopropylethylamine (41 mg, 0.3 mmol, 5.0 eq). The mixture was stirred at 0° C. for 10 min. A solution of ethanesulfonyl chloride (11 mg, 0.086 mmol, 1.4 eq) in dichloromethane (0.5 mL) was added. The mixture was stirred at rt for 15 hrs and was then concentrated. The residue was purified by flash chromatography (ethyl acetate/dichloromethane=1/1) to give the title compound (35 mg, 72.8%) as a colorless oil.

MS: m/z=789 [M+H]$^+$.

Intermediate 1-202

Ethyl 4-bromo-5-(bromomethyl)-1-methyl-1H-pyrazole-3-carboxylate

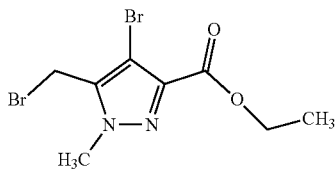

To a solution of ethyl 1,5-dimethyl-1H-pyrazole-3-carboxylate (0.3 g, 1.78 mmol, 1.0 eq, CAS 5744-51-4) in 1,2-dichloroethane (5.5 mL) was added N-Bromo succinimide (0.67 g, 3.75 mmol, 2.1 eq), followed by benzoyl peroxide (0.056 g, 0.23 mmol, 13 mol %). The mixture was stirred at reflux for 16 hrs, concentrated and then partitioned between ethyl acetate (30 mL) and water (10 mL). The organic layer was separated, washed with brine (10 mL), dried over sodium sulfate, filtered and concentrated. The crude product was purified by flash chromatography (ethyl acetate/hexanes=1/5) to give the title compound (0.32 g, 55.6%) as a white solid.

MS: m/z=325 [M+H]$^+$.

Intermediate 1-203 tert-Butyl 4-(4-{[4-bromo-3-(ethoxycarbonyl)-1-methyl-1H-pyrazol-5-yl]methoxy}phenyl)piperazine-1-carboxylate

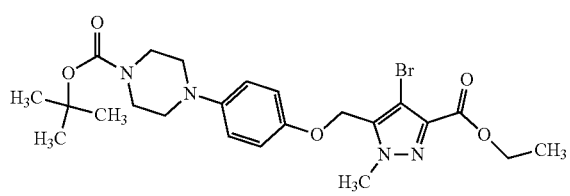 [SMILES: CCOC(=O)c1nn(C)c(COc2ccc(N3CCN(C(=O)OC(C)(C)C)CC3)cc2)c1Br]

To a solution of tert-butyl 4-(4-hydroxyphenyl)piperazine-1-carboxylate (0.29 g, 1.0 mmol, 1.05 eq, CAS 158985-25-2) in DMF (3.0 mL) was added potassium carbonate (0.41 g, 3.0 mmol, 3.0 eq). The mixture was stirred at rt for 10 min. A mixture of ethyl 4-bromo-5-(bromomethyl)-1-methyl-1H-pyrazole-3-carboxylate (0.32 g, 0.98 mmol, 1.0 eq) was added. The mixture was stirred at rt for 2.0 hrs, diluted with ethyl acetate (30 mL), washed with water (2×10 mL), brine (10 mL), dried over sodium sulfate, filtered and concentrated. The crude product was purified by flash chromatography (ethyl acetate/hexanes=1/5 to 1/1) to give the title compound (0.29 g, 55.9%) of as a colorless oil.

MS: m/z=523 [M+H]$^+$.

Intermediate 1-204

Ethyl 4-bromo-5-({4-[4-(dimethylsulfamoyl)piperazin-1-yl]phenoxy}methyl)-1-methyl-1H-pyrazole-3-carboxylate

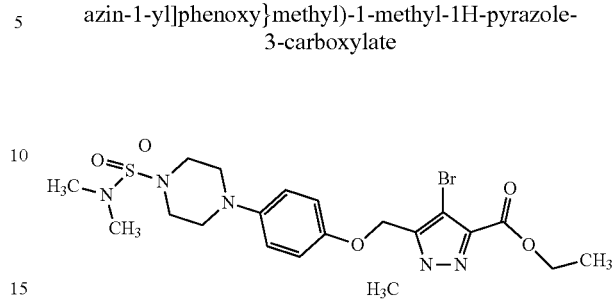

tert-Butyl 4-(4-{[4-bromo-3-(ethoxycarbonyl)-1-methyl-1H-pyrazol-5-yl]methoxy}phenyl) piperazine-1-carboxylate (0.29 g, 0.56 mmol, 1.0 eq) was treated with 2 N HCl in methanol (3.0 mL, 10 eq) at 0° C. for 2.0 hrs. The mixture was concentrated and dried on high vacuum to give 0.26 g of a yellow, solid residue. Diisopropylethylamine (0.36 g, 2.8 mmol, 5.0 eq) was added to a suspension of the residue in dichloromethane (10 mL) at 0° C. The mixture was stirred for 10 min. To the mixture was added N,N-dimethylsulfamoyl chloride (0.10 g, 0.67 mmol, 1.2 eq). The mixture was then stirred at rt for 16 hrs. Water (10 mL) was added and the organic layer was separated, dried over sodium sulfate, filtered and concentrated. The residue was purified by flash chromatography (ethyl acetate/dichloromethane=1/5) to give the title compound (0.25 g, 84.2%) as a white solid.

MS: m/z=531 [M+H]$^+$.

Intermediate 1-205

4-(4-{[4-Bromo-3-(hydroxymethyl)-1-methyl-1H-pyrazol-5-yl]methoxy}phenyl)-N,N-dimethylpiperazine-1-sulfonamide

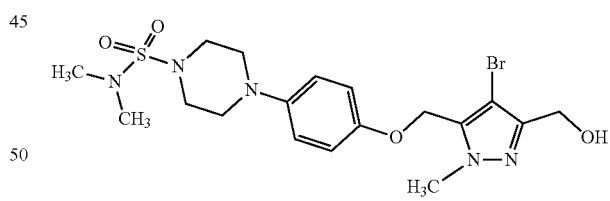

To a solution of ethyl 4-bromo-5-({4-[4-(dimethylsulfamoyl)piperazin-1-yl]phenoxy}methyl)-1-methyl-1H-pyrazole-3-carboxylate (0.25 g, 0.48 mmol, 1.0 eq) in THF (3.0 mL) was added lithium aluminium hydride (2 N in THF, 0.24 mL, 0.48 mmol, 1.0 eq) dropwise at 0° C. The resulting mixture was stirred at 0° C. for 20.0 min. Water (0.1 mL) was added dropwise, followed by 10% NaOH in water (0.1 mL) and water (0.1 mL). The resulting mixture was stirred at rt for 30 min, passed through a pad of Celite. The filtrate was concentrated to give the title compound (0.23 g, 100%) as a white solid which was used directly in the next step.

MS: m/z=488 [M+H]$^+$.

Intermediate 1-206

Ethyl 7-[5-({4-[4-(dimethylsulfamoyl)piperazin-1-yl]phenoxy}methyl)-3-(hydroxymethyl)-1-methyl-1H-pyrazol-4-yl]-3-[3-(1-naphthyloxy)propyl]-1H-indole-2-carboxylate

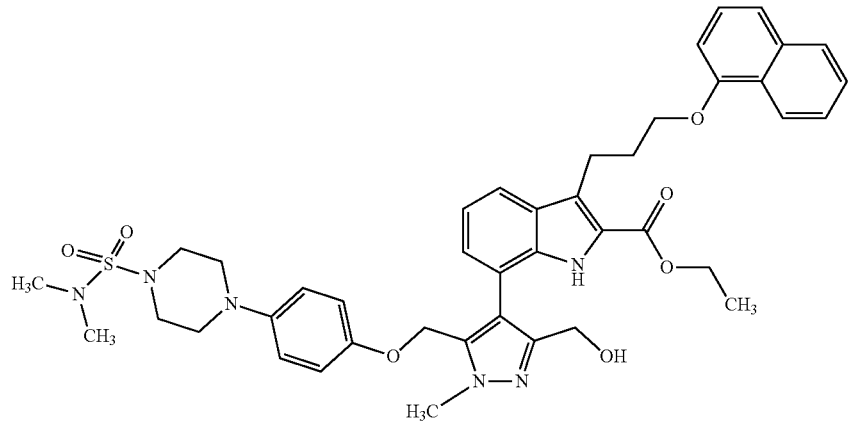 [SMILES: CCOC(=O)c1[nH]c2c(-c3c(CO)nn(C)c3COc3ccc(N4CCN(S(=O)(=O)N(C)C)CC4)cc3)cccc2c1CCCOc1cccc2ccccc12]

Sodium carbonate (0.20 g, 1.92 mmol, 4.0 eq), water (1.2 mL) and 4-(4-{[4-bromo-3-(hydroxymethyl)-1-methyl-1H-pyrazol-5-yl]methoxy}phenyl)-N,N-dimethylpiperazine-1-sulfonamide (0.23 g, 0.48 mmol, 1.0 eq) was added to a solution of ethyl 3-[3-(naphthalen-1-yloxy)propyl]-7-(4,4,5,5-tetramethyl-1,3,2-dioxaborolan-2-yl)-1H-indole-2-carboxylate (see Intermediate 1-4; 240.0 mg, 0.48 mmol, 1.0 eq) in dioxane (4 mL). The mixture was de-gassed three times. Tetrakis(triphenylphosphine)palladium(0) (Pd(PPh$_3$)$_4$; 44.0 mg, 0.038 mmol, 8.0 mol %) was added. The mixture was de-gassed another three times, stirred at 80° C. for 12 hrs and cooled to rt. The reaction mixture was diluted with ethyl acetate (50 mL), washed with water, dried over sodium sulfate, filtered and concentrated. The residue was purified by flash chromatography (ethyl acetate/dichloromethane=1/1 to 2/1) to give the title compound (0.17 g, 45.3%) as a white solid.

MS: m/z=781 [M+H]$^+$.

Intermediate 1-207

Ethyl 1-{3-[(tert-butoxycarbonyl)(methyl)amino]propyl}-7-[5-({4-[4-(dimethylsulfamoyl)piperazin-1-yl]phenoxy}methyl)-3-(hydroxymethyl)-1-methyl-1H-pyrazol-4-yl]-3-[3-(1-naphthyloxy)propyl]-1H-indole-2-carboxylate

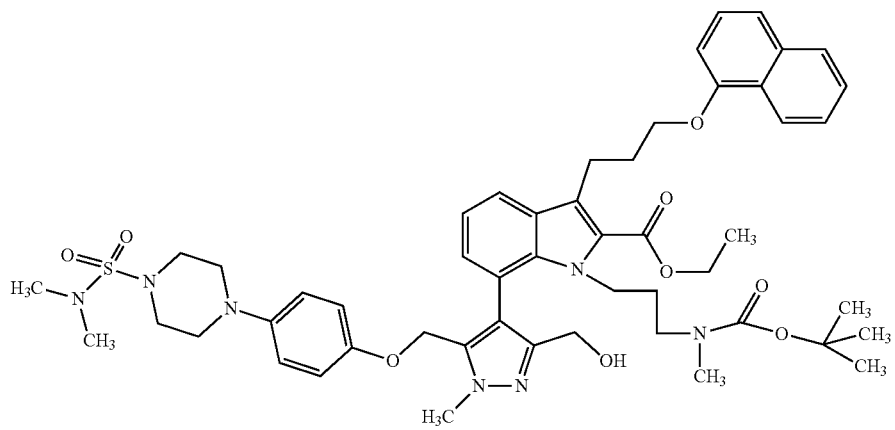 [SMILES: CCOC(=O)c1c(CCCOc2cccc3ccccc23)c2cccc(-c3c(CO)nn(C)c3COc3ccc(N4CCN(S(=O)(=O)N(C)C)CC4)cc3)c2n1CCCN(C)C(=O)OC(C)(C)C]

To a solution of ethyl 7-[5-({4-[4-(dimethylsulfamoyl)piperazin-1-yl]phenoxy}methyl)-3-(hydroxymethyl)-1-methyl-1H-pyrazol-4-yl]-3-[3-(1-naphthyloxy)propyl]-1H-indole-2-carboxylate (0.17 g, 0.22 mmol, 1.0 eq) in DMF (3.0 mL) was added caesium carbonate (0.35 g, 1.09 mmol, 5.0 eq). The mixture was stirred at rt for 10 min. tert-butyl (3-bromopropyl)methylcarbamate (see Intermediate 1-1; 55.0 mg, 0.22 mmol, 1.0 eq) was added. The mixture was stirred at 35° C. for 8.0 hrs, cooled to rt, diluted with ethyl acetate (30 mL), washed with water, dried over sodium sulfate, filtered and concentrated. The residue was purified by flash chromatography (ethyl acetate/hexanes=1/1) to give the title compound (0.106 g, 51.1%) of as a white solid.

MS: m/z=952 [M+H]$^+$.

Intermediate 1-208

Ethyl 7-[3-(bromomethyl)-5-({4-[4-(dimethylsulfamoyl) piperazin-1-yl]phenoxy}methyl)-1-methyl-1H-pyrazol-4-yl]-1-{3-[(tert-butoxycarbonyl)(methyl)amino]propyl}-3-[3-(1-naphthyloxy)propyl]-1H-indole-2-carboxylate

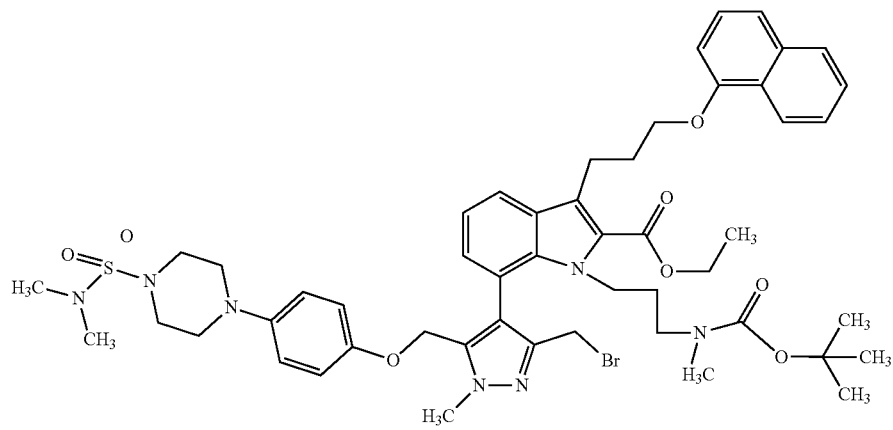

To a solution of ethyl 1-{3-[(tert-butoxycarbonyl)(methyl)amino]propyl}-7-[5-({4-[4-(dimethylsulfamoyl)piperazin-1-yl]phenoxy}methyl)-3-(hydroxymethyl)-1-methyl-1H-pyrazol-4-yl]-3-[3-(1-naphthyloxy)propyl]-1H-indole-2-carboxylate (0.17 g, 0.17 mmol, 1.0 eq) in dichloromethane (4.0 mL) at 0° C. was added triphenylphosphine (0.17 g, 0.63 mmol, 3.6 eq). The mixture was stirred at 0° C. for 10 min. before a solution of tetrabromomethane (0.19 g, 0.57 mmol, 3.3 eq) in dichloromethane (1 ml) was added. The resulting mixture was stirred at rt for 18 hrs, concentrated and the crude title compound was used directly in the next step.

MS: m/z=1014 [M+H]$^+$.

Intermediate 1-209

Ethyl 7-[3-(bromomethyl)-5-({4-[4-(dimethylsulfamoyl) piperazin-1-yl]phenoxy}methyl)-1-methyl-1H-pyrazol-4-yl]-1-[3-(methylamino)propyl]-3-[3-(1-naphthyloxy)propyl]-1H-indole-2-carboxylate hydrochloric acid salt

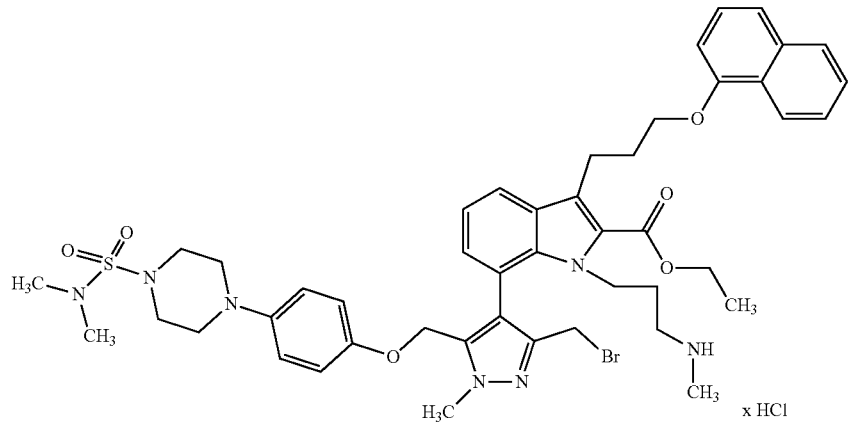 [SMILES: CCOC(=O)c1c(CCCOc2cccc3ccccc23)c2cccc(-c3c(CBr)nn(C)c3COc3ccc(N4CCN(S(=O)(=O)N(C)C)CC4)cc3)c2n1CCCNC]

To a crude ethyl 7-[3-(bromomethyl)-5-({4-[4-(dimethylsulfamoyl)piperazin-1-yl]phenoxy}methyl)-1-methyl-1H-pyrazol-4-yl]-1-{3-[(tert-butoxycarbonyl)(methyl)amino]propyl}-3-[3-(1-naphthyloxy)propyl]-1H-indole-2-carboxylate (0.17 mmol) in methanol (2.0 mL) was added HCl in dioxane (4 N, 2.0 mL) at 0° C. The mixture was stirred at room temperature for 2 hrs and then concentrated to give the crude title compound which was used directly in the next step.

MS: m/z=914 [M+H]$^+$.

Intermediate 1-210

(rac)-Ethyl 11-({4-[4-(dimethylsulfamoyl)piperazin-1-yl]phenoxy}methyl)-7,10-dimethyl-1-[3-(1-naphthyloxy)propyl]-4,5,6,7,8,10-hexahydropyrazolo[3',4':7,8][1,5]diazecino[9,10,1-hi]indole-2-carboxylate

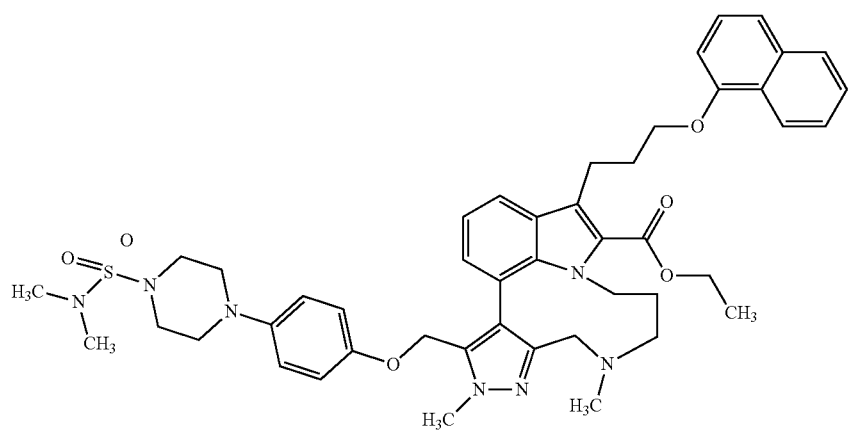

To a solution of the crude ethyl 7-[3-(bromomethyl)-5-({4-[4-(dimethylsulfamoyl)piperazin-1-yl]phenoxy}methyl)-1-methyl-1H-pyrazol-4-yl]-1-[3-(methylamino)propyl]-3-[3-(1-naphthyloxy)propyl]-1H-indole-2-carboxylate hydrochloric acid salt (155 mg, 0.17 mmol, 1.0 eq) in DMF (18.0 mL) was added caesium carbonate (0.28 g, 0.85 mmol, 5.0 eq). The resulting mixture was stirred at 65° C. for 16 hrs, cooled to rt and concentrated under reduced pressure. The residue was then partitioned between a mixture of ethyl acetate and hexanes (1/1, 25.0 mL) and water (10.0 mL). The organic layer was separated, dried over sodium sulfate, filtered and concentrated. The residue was purified by preparative HPLC (Instrument: Varian SD-200; Column: Phenomenex Luna 10μ 250×21.6 mm; eluent A: water+0.1% trifluoracetic acid, Eluent B: acetonitrile+0.1% trifluoracetic acid; gradient: 0.0 min 95% A→30.0 min 0% A→32.0 min 0% A→35 min 95% A→36.0 min 95% A (stop); flow 20 ml/min; temperature: rt ° C.; detector Varian Variable wavelength UV detector) to give the title compound (60.6 mg, 41.7% over the last three steps) as a colorless oil.

MS: m/z=834 [M+H]$^+$.

Intermediate 1-211

Ethyl 3-(acetoxymethyl)-4-bromo-1-methyl-1H-pyrazole-5-carboxylate

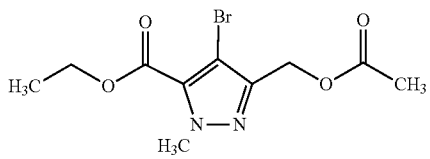

To a solution of ethyl 4-bromo-5-(bromomethyl)-1-methyl-1H-pyrazole-3-carboxylate (see Intermediate 1-202; 1.20 g, 3.70 mmol, 1.00 eq) in DMF (10 mL) was added sodium acetate (3.03 g, 37.0 mmol, 10.0 eq). The suspension was heated to 80° C. overnight. The reaction mixture was cooled to room temperature, diluted with ethyl acetate and washed with water. The organic phase was separated, dried with sodium sulfate, and concentrated to dryness. The residue was purified by flash column chromatography (silica, hexanes/ethyl acetate=3:2) to give the title compound (810 mg).

Intermediate 1-212

4-Bromo-3-(hydroxymethyl)-1-methyl-1H-pyrazole-5-carboxylic acid

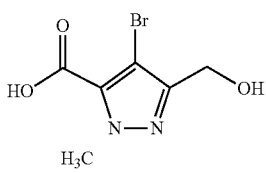

A solution of ethyl 3-(acetoxymethyl)-4-bromo-1-methyl-1H-pyrazole-5-carboxylate (810 mg, 2.66 mmol, 1.0 eq) in methanol (3 mL) was treated with sodium methoxide (288 mg, 5.33 mmol, 2.0 eq) at room temperature overnight. The reaction mixture was concentrated, diluted with ethyl acetate, and acidified to pH 5 with aqueous 2N HCl. The organic phase was separated, dried with sodium sulfate, and concentrated to afford the title compound (520 mg) as a white solid.

Intermediate 1-213

4-Bromo-3-({[tert-butyl(dimethyl)silyl]oxy}methyl)-1-methyl-1H-pyrazole-5-carboxylic acid

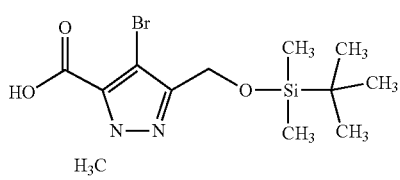

A solution of 4-bromo-3-(hydroxymethyl)-1-methyl-1H-pyrazole-5-carboxylic acid (520 mg, 2.41 mmol, 1.0 eq) in DMF (5 mL) was added tert-butyl(chloro)dimethylsilane (726 mg, 4.81 mmol, 2.0 eq) and diisopropylethylamine (1.99 mL, 12.1 mmol, 5.0 eq). The mixture was stirred at room temperature overnight. The reaction mixture was concentrated, diluted with ethyl acetate, and washed with brine. The organic phase was separated, dried with sodium sulfate, and concentrated to afford the title compound (820 mg).

Intermediate 1-214

[4-Bromo-3-({[tert-butyl(dimethyl)silyl]oxy}methyl)-1-methyl-1H-pyrazol-5-yl]methanol

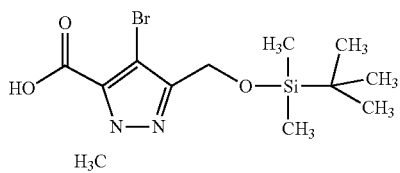

A solution of 4-bromo-3-({[tert-butyl(dimethyl)silyl]oxy}methyl)-1-methyl-1H-pyrazole-5-carboxylic acid (820 mg, 2.36 mmol, 1.0 eq) in THF (5 mL) was treated with borane (2.0 M in THF, 4.71 mL, 9.42 mmol, 4.0 eq) at 0° C. The reaction was warmed to room temperature and heated to reflux 2 h. The reaction mixture was cooled to 0° C. and methanol was added to stop the reaction. After concentration, the residue was purified by flash column chromatography (silica, hexanes/ethyl acetate=1:1) to give the title compound (430 mg).

Intermediate 1-215

Ethyl 7-[3-({[tert-butyl(dimethyl)silyl]oxy}methyl)-5-(hydroxymethyl)-1-methyl-1H-pyrazol-4-yl]-3-[3-(1-naphthyloxy)propyl]-1H-indole-2-carboxylate

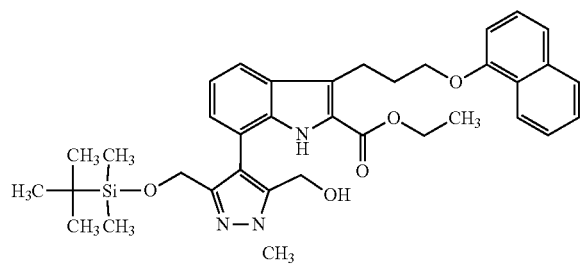

A mixture of ethyl 3-[3-(naphthalen-1-yloxy)propyl]-7-(4,4,5,5-tetramethyl-1,3,2-dioxaborolan-2-yl)-1H-indole-2-carboxylate (see Intermediate 1-4; 660 mg, 1.32 mmol, 1.00 eq), [4-bromo-3-({[tert-butyl(dimethyl)silyl]oxy}methyl)-1-methyl-1H-pyrazol-5-yl]methanol (442 mg, 1.32 mmol, 1.00 eq), Tetrakis(triphenylphosphine)palladium(0) (Pd(PPh$_3$)$_4$; 153 mg, 0.132 mmol, 0.100 eq), and sodium carbonate (700 mg, 6.60 mmol, 5.00 eq) in dioxane/water (15/3 mL) was degassed 3 times and refilled with nitrogen. The reaction mixture was heated to 90° C. overnight. The reaction mixture was cooled to room temperature. The reaction mixture was diluted with ethyl acetate and washed with a saturated aqueous solution of sodium bicarbonate. The organic phase was separated, dried with sodium sulfate, and concentrated to dryness. The residue was purified by flash column chromatography (silica, dichloromethane/ethyl acetate=1:1) to give the title compound (365 mg).

Intermediate 1-216

Ethyl 1-{3-[(tert-butoxycarbonyl)(methyl)amino]propyl}-7-[3-({[tert-butyl(dimethyl)silyl]oxy}methyl)-5-(hydroxymethyl)-1-methyl-1H-pyrazol-4-yl]-3-[3-(1-naphthyloxy)propyl]-1H-indole-2-carboxylate

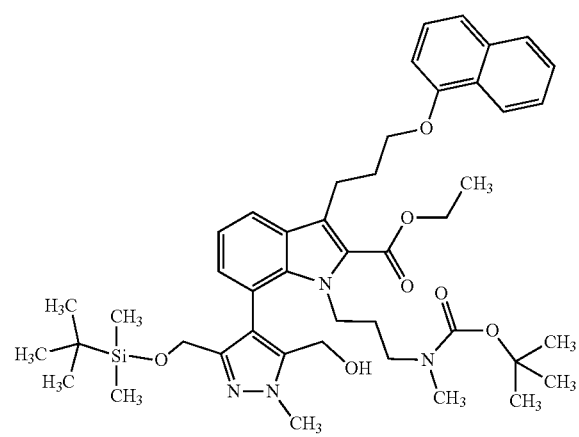 [SMILES: CCOC(=O)c1c(CCCOc2cccc3ccccc23)c2cccc(-c3c(CO[Si](C)(C)C(C)(C)C)nn(C)c3CO)c2n1CCCN(C)C(=O)OC(C)(C)C]

To a solution of ethyl 7-[3-({[tert-butyl(dimethyl)silyl]oxy}methyl)-5-(hydroxymethyl)-1-methyl-1H-pyrazol-4-yl]-3-[3-(1-naphthyloxy)propyl]-1H-indole-2-carboxylate (365 mg, 0.582 mmol, 1.0 eq) in DMF (10 mL) was added (3-bromo-propyl)-methyl-carbamic acid tert-butyl ester (see Intermediate 1-1; 292 mg, 1.16 mmol, 2.0 eq) and caesium carbonate (759 mg, 2.33 mmol, 4.0 eq). The reaction was stirred at room temperature overnight. The mixture was concentrated, diluted with ethyl acetate, and washed with water. The organic phase was separated, dried with sodium sulfate, and concentrated. The residue was purified by preparative TLC (silica, DCMdichloromethane/ethyl acetate=1:1+1% methanol) to give the title compound (298 mg).

MS: m/z=799 (M+H).

Intermediate 1-217

Ethyl 1-{3-[(tert-butoxycarbonyl)(methyl)amino]propyl}-7-[3-({[tert-butyl(dimethyl)silyl]oxy}methyl)-1-methyl-5-{[(methylsulfonyl)oxy]methyl}-1H-pyrazol-4-yl]-3-[3-(1-naphthyloxy)propyl]-1H-indole-2-carboxylate

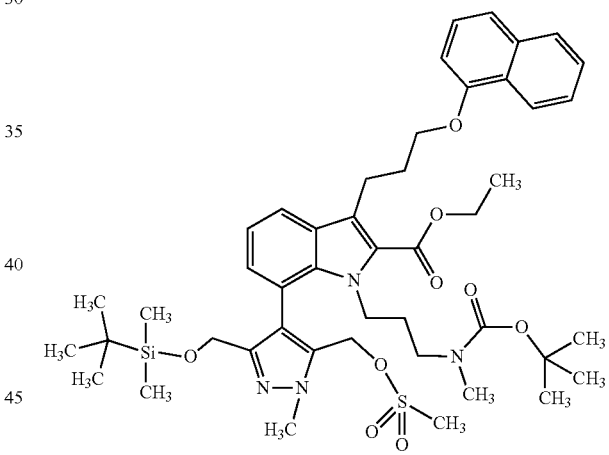

To a solution of ethyl 1-{3-[(tert-butoxycarbonyl)(methyl)amino]propyl}-7-[3-({[tert-butyl(dimethyl)silyl]oxy}methyl)-5-(hydroxymethyl)-1-methyl-1H-pyrazol-4-yl]-3-[3-(1-naphthyloxy)propyl]-1H-indole-2-carboxylate (298 mg, 0.373 mmol, 1.0 eq) in dichloromethane (20 mL) was added diisopropylethylamine (185 μL, 1.12 mmol, 3.0 eq) and methylsulfonyl chloride (64 mg, 0.561 mmol, 1.5 eq) at 0° C. The reaction was warmed to room temperature and stirred for 2 h. The mixture was concentrated and the residue was purified by flash column chromatography (silica, dichloromethane/ethyl acetate=2:1) to give the title compound (240 mg).

MS: m/z=877 (M+H).

Intermediate 1-218

Ethyl 7-[5-(chloromethyl)-3-(hydroxymethyl)-1-methyl-1H-pyrazol-4-yl]-1-[3-(methylamino)propyl]-3-[3-(1-naphthyloxy)propyl]-1H-indole-2-carboxylate hydrochloric acid salt

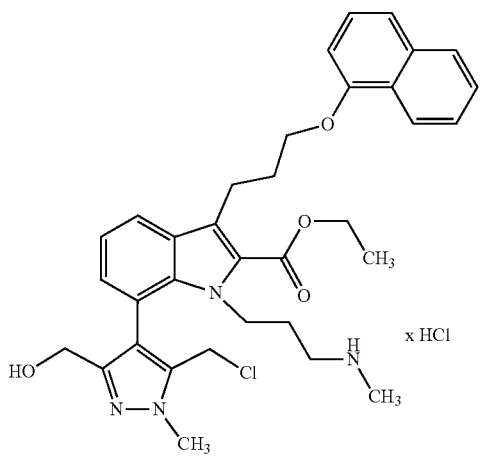 [SMILES: CCOC(=O)c1c(CCCOc2cccc3ccccc23)c2cccc(-c3c(CO)nn(C)c3CCl)c2n1CCCNC]

A solution of ethyl 1-{3-[(tert-butoxycarbonyl)(methyl)amino]propyl}-7-[3-({[tert-butyl(dimethyl)silyl]oxy}methyl)-1-methyl-5-{[(methylsulfonyl)oxy]methyl}-1H-pyrazol-4-yl]-3-[3-(1-naphthyloxy)propyl]-1H-indole-2-carboxylate (240 mg) was treated with HCl/dioxane (4.0 M, 10 mL) at room temperature 1 h. The reaction was concentrated to dryness. The residue was used for next step without further purification.

Intermediate 1-219

(rac)-Ethyl 11-(hydroxymethyl)-7,9-dimethyl-1-[3-(1-naphthyloxy)propyl]-4,5,6,7,8,9-hexahydropyrazolo[3',4':7,8][1,5]diazecino[9,10,1-hi]indole-2-carboxylate

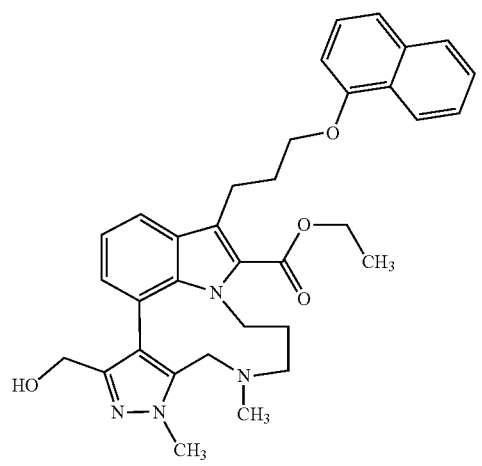 [SMILES: CCOC(=O)c1c(CCCOc2cccc3ccccc23)c2cccc3c2n1CCCN(C)Cc1c-3c(CO)nn1C]

To a solution of ethyl 7-[5-(chloromethyl)-3-(hydroxymethyl)-1-methyl-1H-pyrazol-4-yl]-1-[3-(methylamino)propyl]-3-[3-(1-naphthyloxy)propyl]-1H-indole-2-carboxylate hydrochloric acid salt (165 mg, 0.274 mmol, 1.0 eq) in DMF (10 mL) was added caesium carbonate (357 mg, 1.10 mmol, 4.0 eq). The reaction was stirred at room temperature overnight. The mixture was filtered and filtrate was concentrated to dryness. The residue was purified by preparative HPLC (Instrument: Varian SD-200; Column: Phenomenex Luna 10μ 250×21.6 mm; eluent A: water+0.1% trifluoroacetic acid, Eluent B: acetonitrile+0.1% trifluoroacetic acid; gradient: 0.0 min 95% A→30.0 min 0% A→32.0 min 0% A→35 min 95% A→36.0 min 95% A (stop); flow 20 ml/min; temperature: rt °C.; detector Varian Variable wavelength UV detector) to give the title compound (51 mg).

Intermediate 1-220

(rac)-Ethyl 11-(chloromethyl)-7,9-dimethyl-1-[3-(1-naphthyloxy) propyl]-4,5,6,7,8,9-hexahydropyrazolo[3',4':7,8][1,5]diazecino[9,10,1-hi]indole-2-carboxylate To a solution of (rac)-ethyl 11-(hydroxymethyl)-7,9-dimethyl-1-[3-(1-naphthyloxy)propyl]-4,5,6,7,8,9-hexahydropyrazolo[3',4':7,8][1,5]diazecino[9,10,1-hi]indole-2-carboxylate (42 mg, 0.074 mmol, 1.0 eq) in dichloromethane (2 mL) was added diisopropylethylamine (61 μL, 0.37 mmol, 5.0 eq) and methylsulfonyl chloride (17 mg, 0.15 mmol, 2.0 eq) at 0° C. The reaction mixture was warmed to room temperature and stirred for 2 h. The mixture was concentrated and the residue was purified by preparative TLC (silica, dichloromethane/ethyl acetate=1:1) to give the title compound (39 mg).

MS: m/z=585 (M+H).

Intermediate 1-221

(rac)-Ethyl 7,9-dimethyl-1-[3-(1-naphthyloxy)propyl]-11-{[4-(2-oxopyridin-1(2H)-yl)phenoxy]methyl}-4,5,6,7,8,9-hexahydropyrazolo[3',4':7,8][1,5]diazecino[9,10,1-hi]indole-2-carboxylate

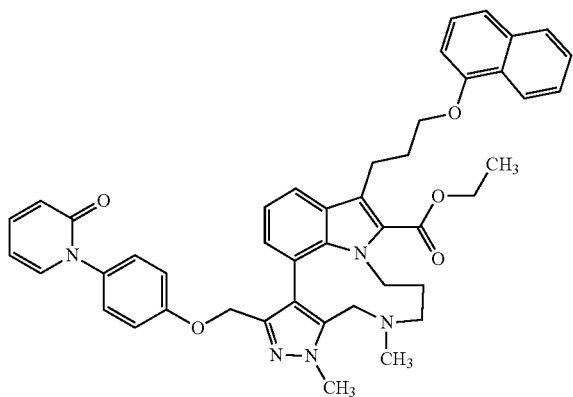 [SMILES: CCOC(=O)c1c(CCCOc2cccc3ccccc23)c2cccc3c2n1CCCN(C)Cc1c-3c(COc2ccc(-n3ccccc3=O)cc2)nn1C]

To a solution of (rac)-ethyl 11-(chloromethyl)-7,9-dimethyl-1-[3-(1-naphthyloxy)propyl]-4,5,6,7,8,9-hexahydropyrazolo[3',4':7,8][1,5]diazecino[9,10,1-hi]indole-2-carboxylate (39 mg, 0.067 mmol, 1.0 eq) and 1-(4-hydroxyphenyl)-1H-pyridin-2-one (25 mg, 0.13 mmol, 2.0 eq; CAS-No: 859538-51-5) in DMF (1 mL) was added caesium carbonate (109 mg, 0.341 mmol, 5.0 eq). The reaction was stirred at 40° C. 2 h. The mixture was diluted with ethyl acetate and washed with water. The organic phase was separated and concentrated to dryness. The residue was used for next step without further purification.

Intermediate 1-222

2-[2-(2-Bromo-3-methylphenyl)hydrazinylidene]hexanedioic acid

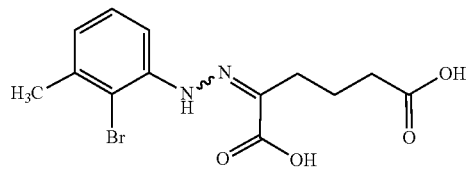

To a mixture comprising 2-bromo-3-methylaniline (25.4 g, 137 mmol; CAS-No: 54879-20-8), water (61 mL) and concentrated hydrochloric acid (110 mL, 37% in water) was slowly added at −5° C. a solution of sodium nitrite (9.71 g, 141 mmol) in water (36 mL), keeping the temperature at 0° C. This mixture was slowly added to a solution of ethyl 2-oxocyclopentanecarboxylate (19 mL, 130 mmol; CAS-No: 611-10-9) in potassium hydroxide (190 mL, 4.0 M in water, 780 mmol) at 0° C. The reaction was stirred at rt overnight, concentrated hydrochloric acid (105 mL, 37% in water) was added and stirring continued for 1 h. The precipitate was filtered, washed with water, re-dissolved in saturated aqueous sodium hydrogen carbonate and undissolved components were filtered off. To the filtrate was added concentrated hydrochloric acid until pH 2 was reached. The precipitate was isolated by filtration, washed with water and dried to give the title compound (28.3 g, 60% yield).

MS: m/z=343 [M+H]$^+$.

Intermediate 1-223

Ethyl 7-bromo-3-(3-ethoxy-3-oxopropyl)-6-methyl-1H-indole-2-carboxylate

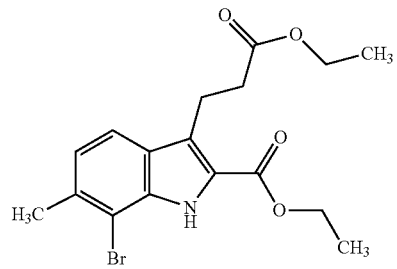 [SMILES: CCOC(=O)CCc1c(C(=O)OCC)[nH]c2c(Br)c(C)ccc12]

To a solution of 2-[2-(2-bromo-3-methylphenyl)hydrazinylidene]hexanedioic acid (28.2 g, 82.3 mmol) in ethanol (720 mL) was added concentrated sulfuric acid (180 mL) and the mixture was stirred at 90° C. overnight. After concentration, dichloromethane was added, the organic layer washed with water and dried over sodium sulfate. After filtration and removal of the solvent the residue was purified by flash chromatography (Biotage SNAP cartridge silica 750 g, ethyl acetate: n-hexane) to give the title compound together with ethyl 3-(7-bromo-6-methyl-1H-indol-3-yl)propanoate as a 7:3-mixture (18.9 g, 64% yield).

MS: m/z=382 [M+H]$^+$.

Intermediate 1-224

3-[7-Bromo-2-(ethoxycarbonyl)-6-methyl-1H-indol-3-yl]propanoic acid

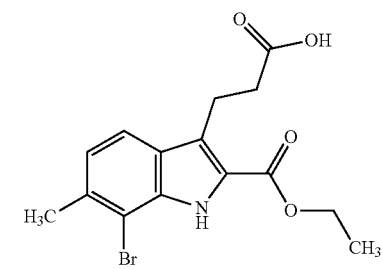 [SMILES: CCOC(=O)c1[nH]c2c(Br)c(C)ccc2c1CCC(=O)O]

A 7:3-mixture of ethyl 7-bromo-3-(3-ethoxy-3-oxopropyl)-6-methyl-1H-indole-2-carboxylate and ethyl 3-(7-bromo-6-methyl-1H-indol-3-yl)propanoate (18.9 g, 52.4 mmol) was solved in glacial acetic acid (170 mL) at 80° C. Hydrochloric acid (23 mL, 37% in water, 270 mmol) was added and the mixture was heated at 80° C. for 3 hrs. After cooling to rt, water (230 mL) was added, the precipitate collected, washed with water and dried to give the title compound together with 3-(7-bromo-6-methyl-1H-indol-3-yl)propanoic acid as a 7:3-mixture (15.5 g, 89% yield).

MS: m/z=354 [M+H]$^+$.

Intermediate 1-225

Ethyl 7-bromo-3-(3-hydroxypropyl)-6-methyl-1H-indole-2-carboxylate

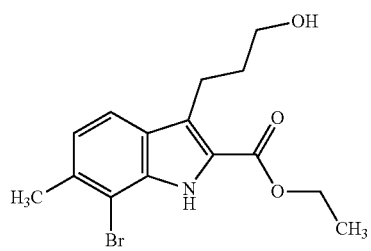 [SMILES: CCOC(=O)c1[nH]c2c(Br)c(C)ccc2c1CCCO]

A solution of a 7:3-mixture of 3-[7-bromo-2-(ethoxycarbonyl)-6-methyl-1H-indol-3-yl]propanoic acid and 3-(7-bromo-6-methyl-1H-indol-3-yl)propanoic acid (15.5 g, 46.6 mmol) in THF (110 mL) was cooled to −25° C. Borane (61 mL, 1.0 M in THF, 61 mmol) was added over 1 h, the mixture warmed to RT and stirring was continued for 1.5 hr. Methanol (50 mL) was added, the mixture concentrated and purified by repeated Biotage (Biotage SNAP cartridge silica 750 g, ethyl acetate: n-hexane) to give the title compound 8.49 g (57% yield).

MS: m/z=340 [M+H]$^+$.

Intermediate 1-226

Ethyl 7-bromo-3-(3-bromopropyl)-6-methyl-1H-indole-2-carboxylate

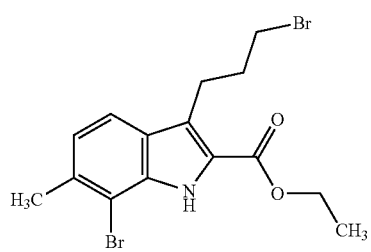 [SMILES: CCOC(=O)c1[nH]c2c(Br)c(C)ccc2c1CCCBr]

A mixture comprising ethyl 7-bromo-3-(3-hydroxypropyl)-6-methyl-1H-indole-2-carboxylate (20.2 g, 59.4 mmol), tetrabromomethane (78.8 g, 237 mmol), pyridine (19 mL), dichloromethane (140 mL) and acetonitrile (340 mL) was cooled to 0° C. Triphenylphosphane (62.3 g, 237 mmol) was added and the reaction was stirred at rt overnight. Dichloromethane was removed, the precipitate was filtered off and the filtrate concentrated. The residue was purified by repeated flash chromatography (Biotage SNAP cartridge silica 750 g, ethyl acetate: dichloromethane) to give the title compound (7.76 g, 87% yield).

MS: m/z=402 [M+H]$^+$.

Intermediate 1-227

Ethyl 7-bromo-6-methyl-3-[3-(naphthalen-1-yloxy)propyl]-1H-indole-2-carboxylate

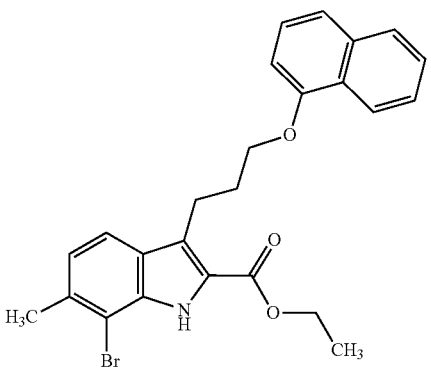 [SMILES: CCOC(=O)c1[nH]c2c(Br)c(C)ccc2c1CCCOc1cccc2ccccc12]

To a solution of naphthalen-1-ol (3.32 g, 23.0 mmol) in N,N-dimethylacetamide (35 mL) was added potassium carbonate (3.18 g, 23.0 mmol), followed by a solution of ethyl 7-bromo-3-(3-bromopropyl)-6-methyl-1H-indole-2-carboxylate (7.74 g, 19.2 mmol) in N,N-dimethylacetamide (70 mL). The mixture was stirred at 50° C. for 2.5 days, poured into water and extracted with ethyl acetate. The organic layer was washed with water and brine and dried over sodium sulfate. After filtration and removal of the solvent the residue was purified by flash chromatography (Biotage SNAP cartridge silica 750 g, ethyl acetate: n-hexane) to give the title compound (7.76 g, 87% yield)

MS: m/z=466 [M+H]$^+$.

Intermediate 1-228

Ethyl 6-methyl-3-[3-(naphthalen-1-yloxy)propyl]-7-(4,4,5,5-tetramethyl-1,3,2-dioxaborolan-2-yl)-1H-indole-2-carboxylate

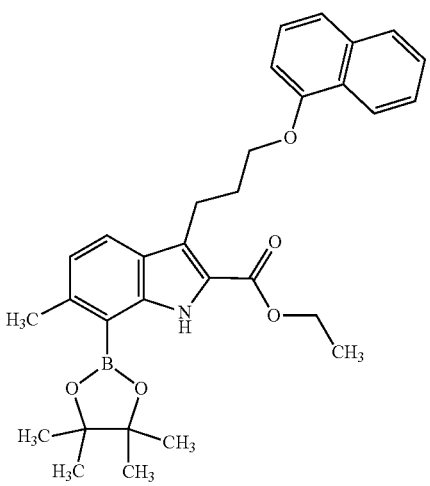 [SMILES: CCOC(=O)c1[nH]c2c(B3OC(C)(C)C(C)(C)O3)c(C)ccc2c1CCCOc1cccc2ccccc12]

To a solution of ethyl 7-bromo-6-methyl-3-[3-(naphthalen-1-yloxy)propyl]-1H-indole-2-carboxylate (2.50 g, 5.36 mmol) in 1,4-dioxane (35 mL) were added 4,4,4',4',5,5,5', 5'-octamethyl-2,2'-bi-1,3,2-dioxaborolane (2.72 g, 10.7 mmol) and potassium acetate (2.10 g, 21.4 mmol). The mixture was degassed and purged with argon several times. [1,1'-Bis(diphenylphosphino)ferrocene]dichloropalladium (II) (876 mg, 1.07 mmol; complex with dichloromethane) was added and the mixture stirred at 85° C. overnight. After cooling the mixture was poured into water and extracted with ethyl acetate. The organic layer was washed with water and brine and dried over sodium sulfate. After filtration and removal of the solvent the residue was purified by flash chromatography (Biotage SNAP cartridge silica 340 g, ethyl acetate: n-hexane) to give the title compound (1.65 g, 60% yield).

MS: m/z=514 [M+H]$^+$.

Intermediate 1-229

Ethyl 7-[3-({4-[4-(dimethylsulfamoyl)piperazin-1-yl]phenoxy}methyl)-5-(hydroxymethyl)-1-methyl-1H-pyrazol-4-yl]-6-methyl-3-[3-(naphthalen-1-yloxy)propyl]-1H-indole-2-carboxylate

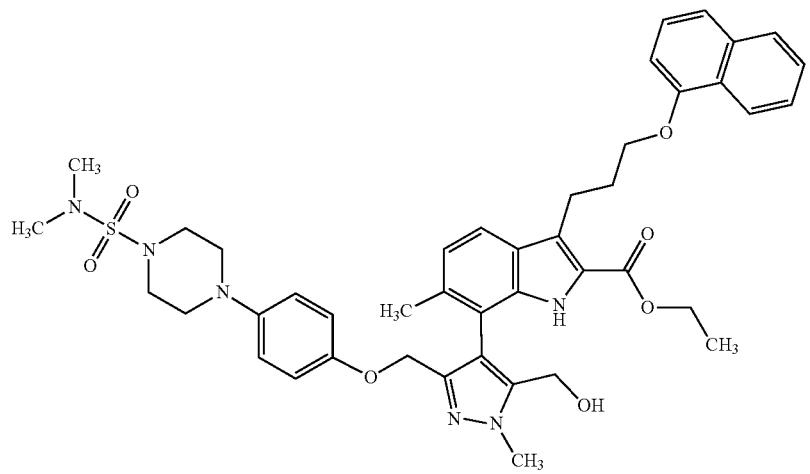

To a solution of 4-(4-{[4-bromo-5-(hydroxymethyl)-1-methyl-1H-pyrazol-3-yl]methoxy}phenyl)-N,N-dimethylpiperazine-1-sulfonamide (see Intermediate 1-22; 1.42 g, 90% purity, 2.62 mmol) in 1,4-dioxane (28 mL) were added ethyl 6-methyl-3-[3-(naphthalen-1-yloxy)propyl]-7-(4,4,5,5-tetramethyl-1,3,2-dioxaborolan-2-yl)-1H-indole-2-carboxylate (1.57 g, 90% purity, 2.75 mmol), lithium chloride (222 mg, 5.23 mmol) and sodium carbonate (1.11 g, 10.5 mmol) in water (7.0 mL). The mixture was degassed and purged with argon several times. Tetrakis(triphenylphosphine)palladium(0) (605 mg, 523 μmol) was added and the mixture stirred at 120° C. under microwave irradiation for 11 h. After cooling dichloromethane and methanol were added, the organic layer was washed with brine and dried over sodium sulfate. After filtration and removal of the solvents the residue was purified by flash chromatography (Biotage SNAP cartridge silica 340 g, ethanol:dichloromethane) to give the title compound (655 mg, 31% yield).

MS: m/z=795 [M+H]$^+$.

Intermediate 1-230

Ethyl 7-[3-({4-[4-(dimethylsulfamoyl)piperazin-1-yl]phenoxy}methyl)-5-(hydroxymethyl)-1-methyl-1H-pyrazol-4-yl]-6-methyl-1-[2-(morpholin-4-yl)ethyl]-3-[3-(naphthalen-1-yloxy)propyl]-1H-indole-2-carboxylate

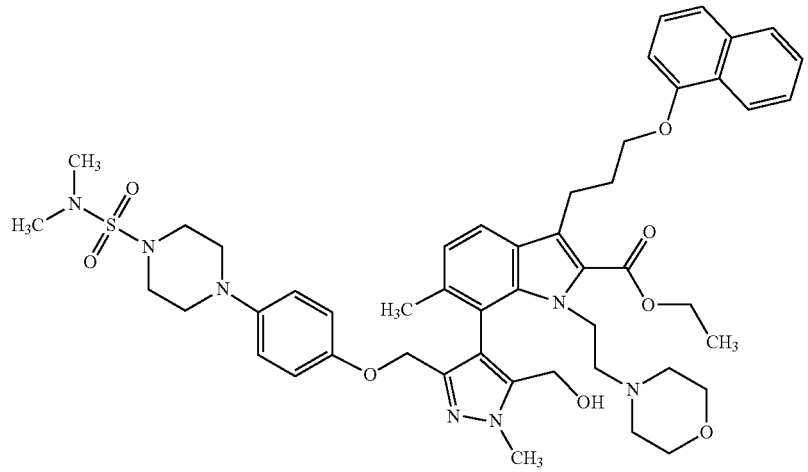 [SMILES: CCOC(=O)c1c(CCCOc2cccc3ccccc23)c2ccc(C)c(-c3c(COc4ccc(N5CCN(S(=O)(=O)N(C)C)CC5)cc4)nn(C)c3CBr)c2n1CCN1CCOCC1]

To a solution of ethyl 7-[3-({4-[4-(dimethylsulfamoyl)piperazin-1-yl]phenoxy}methyl)-5-(hydroxymethyl)-1-methyl-1H-pyrazol-4-yl]-6-methyl-3-[3-(naphthalen-1-yloxy)propyl]-1H-indole-2-carboxylate (50.0 mg, 62.9 μmol) in N,N-dimethylacetamide (1.3 mL) were added caesium carbonate (77.9 mg, 239 μmol), tetrabutylammonium iodide (5.11 mg, 13.8 μmol) and 4-(2-chloroethyl)morpholine hydrochloride (30.4 mg, 164 μmol). The mixture was stirred at 120° C. under microwave irradiation for 1 hr. After cooling dichloromethane, water and brine were added, the organic layer was washed with brine and dried over sodium sulfate. After filtration and removal of the solvents the residue was purified by preparative TLC (ethyl acetate) to give the title compound (32.1 mg, 56% yield).

MS: m/z=908 [M+H]$^+$.

Intermediate 1-231

Ethyl 7-[5-(bromomethyl)-3-({4-[4-(dimethylsulfamoyl)piperazin-1-yl]phenoxy}methyl)-1-methyl-1H-pyrazol-4-yl]-6-methyl-1-[2-(morpholin-4-yl)ethyl]-3-[3-(naphthalen-1-yloxy)propyl]-1H-indole-2-carboxylate

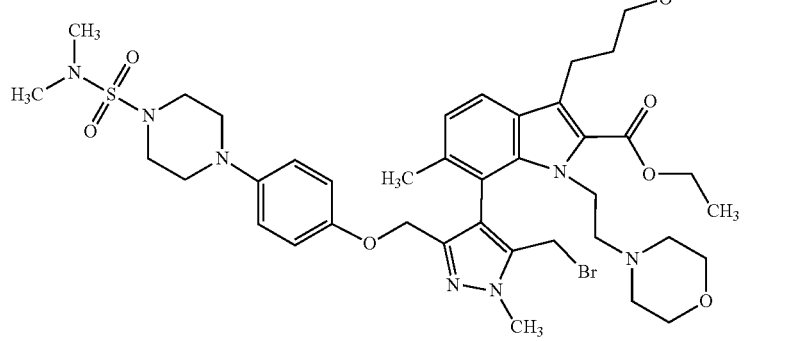

To a solution of ethyl 7-[3-({4-[4-(dimethylsulfamoyl)piperazin-1-yl]phenoxy}methyl)-5-(hydroxymethyl)-1-methyl-1H-pyrazol-4-yl]-6-methyl-1-[2-(morpholin-4-yl)ethyl]-3-[3-(naphthalen-1-yloxy)propyl]-1H-indole-2-carboxylate (44.2 mg, 48.7 µmol) in dichloromethane (810 µL) were added at 0° C. triphenylphosphine (30.6 mg, 117 µmol) a solution of tetrabromomethane (35.5 mg, 107 µmol) in dichloromethane (400 µL) and the mixture was stirred at rt overnight. Another portion of triphenylphosphine (30.6 mg, 117 µmol) and tetrabromomethane (35.5 mg, 107 µmol) were added and stirring continued for 1 day. The reaction mixture was directly purified by chromatography by flash chromatography (Biotage SNAP cartridge silica 10 g, methanol:dichloromethane) to give the title compound (25.3 mg, 51% yield).

MS: m/z=970 [M+H]$^+$.

Intermediate 1-232

(rac)-2'-Ethoxycarbonyl-10'-((4-(4-(N,N-dimethylsulfamoyl)piperazin-1-yl)phenoxy)methyl)-8',11'-dimethyl-1'-(3-(naphthalen-1-yloxy)propyl)-4',5',7',8'-tetrahydrospiro[morpholine-4,6'-pyrazolo[3',4':6,7][1,4]diazonino[8,9,1-hi]indol]-4-ium bromide

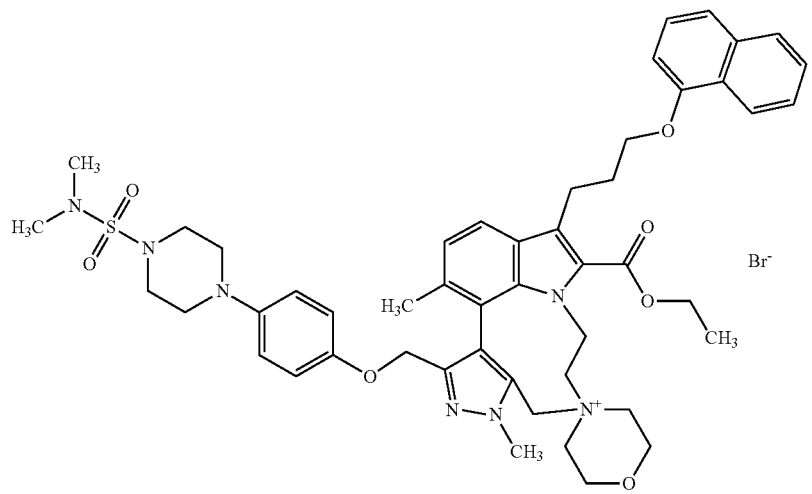 [SMILES: CCOC(=O)c1c(CCCOc2cccc3ccccc23)c2ccc(C)c3c2n1CC[N+]1(CCOCC1)Cc1c-3c(COc2ccc(N3CCN(S(=O)(=O)N(C)C)CC3)cc2)nn1C ; [Br-]]

To a solution of 4-(4-hydroxyphenyl)-N,N-dimethylpiperazine-1-sulfonamide (8.11 mg, 28.4 µmol) in N,N-dimethylacetamide (150 µl) was added potassium carbonate (9.82 mg, 71.1 µmol). After 10 minutes of stirring at RT the solution of ethyl 7-[5-(bromomethyl)-3-({4-[4-(dimethylsulfamoyl)piperazin-1-yl]phenoxy}methyl)-1-methyl-1H-pyrazol-4-yl]-6-methyl-1-[2-(morpholin-4-yl)ethyl]-3-[3-(naphthalen-1-yloxy)propyl]-1H-indole-2-carboxylate (23.0 mg, 23.7 µmol) in N,N-dimethylacetamide (150 µl) was added and the mixture stirred at 50° C. overnight. The solvent was removed and the residue purified by preparative TLC (methanol: dichloromethane) to give the title compound (4.5 mg, 20% yield).

MS: m/z=890.5 [M+H]$^+$.

397

Intermediate 1-233

Ethyl 7-[3-(benzyloxy)-5-methoxyphenyl]-3-[3-(naphthalen-1-yloxy)propyl]-1H-indole-2-carboxylate

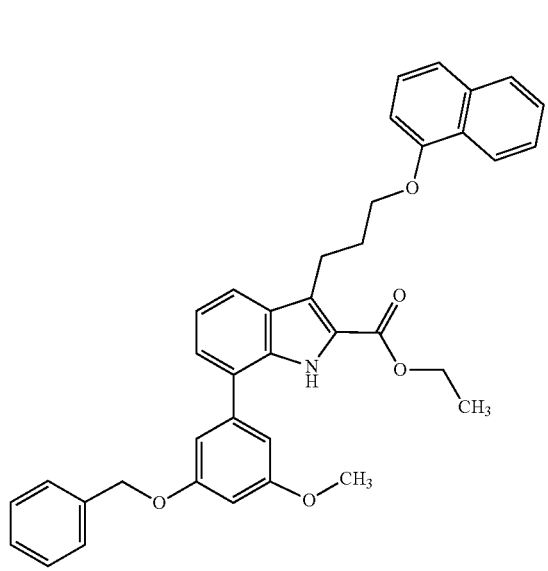 [SMILES: CCOC(=O)c1[nH]c2c(-c3cc(OC)cc(OCc4ccccc4)c3)cccc2c1CCCOc1cccc2ccccc12]

To a solution of ethyl 7-bromo-3-[3-(naphthalen-1-yloxy)propyl]-1H-indole-2-carboxylate (see Intermediate 1-3; 2.50 g, 5.53 mmol) in 1,4-dioxane (50 mL) were added [3-(benzyloxy)-5-methoxyphenyl]boronic acid (2.14 g, 8.29 mmol), lithium chloride (469 mg, 11.1 mmol) and sodium carbonate (11 ml, 2.0 M in water, 22 mmol). The mixture was degassed and purged with argon several times. [1,1'-Bis(diphenylphosphino)ferrocene]dichloropalladium(II) (903 mg, 1.11 mmol; complex with dichloromethane) was added and the mixture stirred at 100° C. overnight. After cooling, acetonitrile was added, the mixture was filtered, concentrated and the residue was purified by flash chromatography (Biotage SNAP cartridge silica 340 g, ethyl acetate: n-hexane) to give the title compound (3.03 g, 94% yield).

MS: m/z=586.3 [M+H]$^+$.

398

Intermediate 1-234

Ethyl 7-(3-hydroxy-5-methoxyphenyl)-3-[3-(5,6,7,8-tetrahydronaphthalen-1-yloxy)propyl]-1H-indole-2-carboxylate

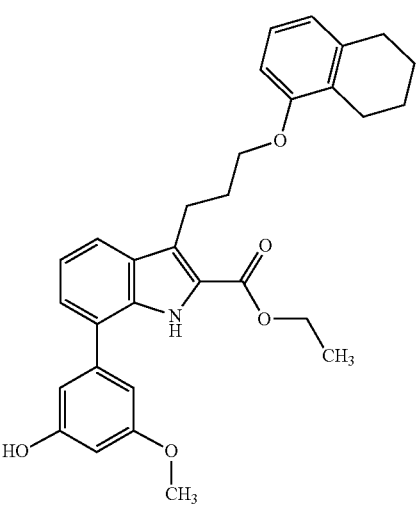 [SMILES: CCOC(=O)c1[nH]c2c(-c3cc(O)cc(OC)c3)cccc2c1CCCOc1cccc2c1CCCC2]

To a solution of ethyl 7-[3-(benzyloxy)-5-methoxyphenyl]-3-[3-(naphthalen-1-yloxy)propyl]-1H-indole-2-carboxylate (1.00 g, 1.71 mmol) in THF (35 ml) and ethanol (35 ml) was added palladium on charcoal (363 mg, 10%, 341 μmol) and the mixture was vigorously stirred under an atmosphere of hydrogen at rt for 2 days. Dichloromethane was added, the catalyst was filtered off, the filtrate was concentrated and the residue was purified by flash chromatography (Biotage SNAP cartridge silica 100 g, ethyl acetate: n-hexane) to give the title compound (501 mg, 59% yield).

MS: m/z=500 [M+H]$^+$.

Intermediate 1-235

(rac)-Ethyl 12-methoxy-1-[3-(5,6,7,8-tetrahydronaphthalen-1-yloxy)propyl]-4,5,7,8-tetrahydro-10,14-(metheno)[1,4,7]dioxazacyclotetradecino[9,8,7-hi]indole-2-carboxylate

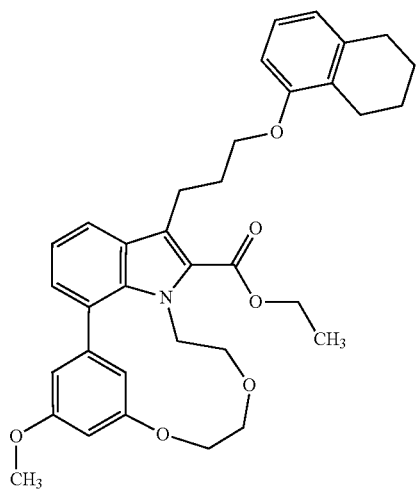 [SMILES: CCOC(=O)c1c(CCCOc2cccc3c2CCCC3)c2cccc3c2n1CCOCCOc1cc(OC)cc-3c1]

A mixture comprising ethyl 7-(3-hydroxy-5-methoxyphenyl)-3-[3-(5,6,7,8-tetrahydronaphthalen-1-yloxy)propyl]-1H-indole-2-carboxylate (50.0 mg, 100 µmol), bis(2-bromoethyl) ether (31 µl, 250 µmol), caesium carbonate (163 mg, 500 µmol) and N,N-dimethylacetamide (4.0 ml) was stirred at 80° C. overnight. The mixture was filtered, concentrated and purified by preparative TLC (ethyl acetate: n-hexane) to give the title compound (21.6 mg, 38% yield).

MS: m/z=570.3 [M+H]$^+$.

Intermediate 1-236

Ethyl 7-(3-hydroxy-5-methoxyphenyl)-3-[3-(naphthalen-1-yloxy)propyl]-1H-indole-2-carboxylate

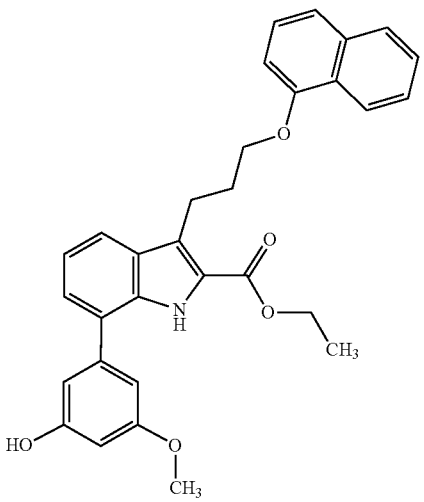 [SMILES: CCOC(=O)c1[nH]c2c(-c3cc(O)cc(OC)c3)cccc2c1CCCOc1cccc2ccccc12]

To a solution of ethyl 7-[3-(benzyloxy)-5-methoxyphenyl]-3-[3-(naphthalen-1-yloxy)propyl]-1H-indole-2-carboxylate (see Intermediate 1-233; 880 mg, 1.50 mmol) in THF (30 ml) and ethanol (30 ml) was added palladium on charcoal (320 mg, 10%, 300 µmol) and the mixture was vigorously stirred under an atmosphere of hydrogen at rt for 2.5 hrs. Dichloromethane was added, the catalyst was filtered off, the filtrate was concentrated and the residue was purified by flash chromatography (Biotage SNAP cartridge silica 100 g, ethyl acetate: n-hexane) to give the title compound (665 mg, 89% yield).

MS: m/z=496.2 [M+H]$^+$.

Intermediate 1-237

(rac)-Ethyl 12-methoxy-1-[3-(naphthalen-1-yloxy)propyl]-4,5,7,8-tetrahydro-10,14-(metheno)[1,4,7]dioxazacyclotetradecino[9,8,7-hi]indole-2-carboxylate

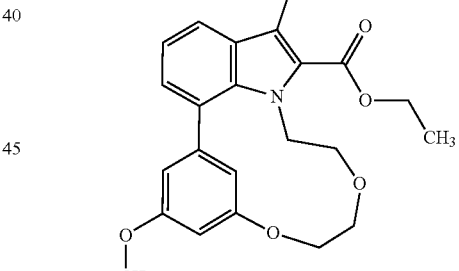

A mixture comprising ethyl 7-(3-hydroxy-5-methoxyphenyl)-3-[3-(naphthalen-1-yloxy)propyl]-1H-indole-2-carboxylate (79.0 mg, 159 µmol), bis(2-bromoethyl) ether (50 µl, 400 µmol), caesium carbonate (260 mg, 797 µmol) and N,N-dimethylacetamide (5.0 ml) was stirred at 80° C. overnight. The mixture was filtered, concentrated and purified by preparative TLC (ethyl acetate: n-hexane) to give the title compound (23.5 mg, 26% yield).

MS: m/z=566 [M+H]$^+$.

401

Intermediate 1-238

(rac)-Ethyl 3-({4-[4-(2-methoxy-2-oxoethyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate

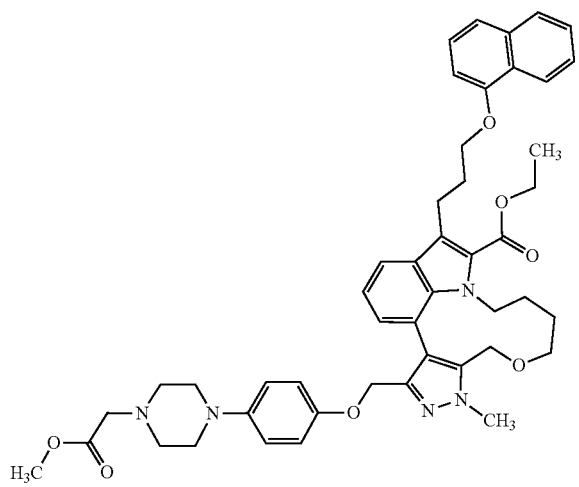 [SMILES: CCOC(=O)c1c(CCCOc2cccc3ccccc23)c2cccc3c2n1CCCCOCc1c-3c(COc2ccc(N3CCN(CC(=O)OC)CC3)cc2)nn1C]

To a solution of (rac)-ethyl 1-methyl-7-[3-(naphthalen-1-yloxy)propyl]-3-{[4-(piperazin-1-yl)phenoxy]methyl}-1,10,11,12,13,15-hexahydropyrazolo[4',3':9,10][1,6]oxazacycloundecino[8,7,6-hi]indole-8-carboxylate hydrochloric acid salt (see Intermediate 1-12; 250 mg) in DMF (2.6 ml) were added N,N-diisopropylethylamine (163 µl, 937 µmol) and after 10 min. of stirring methyl chloroacetate (33.9 mg, 312 µmol). The mixture was stirred at rt for 24 hrs, poured into water and extracted with ethyl acetate. The organic layer was washed with brine, dried and concentrated. The crude product was purified by flash chromatography (Biotage SNAP cartridge silica 10 g, ethyl acetate:n-hexane) to give the title compound (152 mg, 61% yield).

MS: m/z=801.6 [M+H]$^+$

402

Intermediate 1-239

(rac)-Ethyl 3-({4-[4-(3-hydroxy-3-methylbutyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate To a solution of (rac)-ethyl 1-methyl-7-[3-(naphthalen-1-yloxy)propyl]-3-{[4-(piperazin-1-yl)phenoxy]methyl}-1,10,11,12,13,15-hexahydropyrazolo[4',3':9,10][1,6]oxazacycloundecino[8,7,6-hi]indole-8-carboxylate hydrochloric acid salt (see Intermediate 1-12; 109 mg) in DMF (1.2 ml) were added N,N-diisopropylethylamine (71 µl, 410 µmol) and after 10 min of stirring 4-bromo-2-methylbutan-2-ol (22.7 mg, 136 µmol). The mixture was stirred at rt for 24 hrs, another portion 4-bromo-2-methylbutan-2-ol (22.7 mg, 136 µmol) was added and stirring continued for 2.5 days. The mixture was poured into water and extracted with ethyl acetate. The organic layer was washed with brine, dried and concentrated. The crude product was purified by HPLC (Method P2) to give the title compound (44 mg, 33% yield).

MS: m/z=814 [M+H]$^+$

Intermediate 1-240

(rac)-Ethyl 12-methoxy-1-[3-(naphthalen-1-yloxy)propyl]-5,6,7,8-tetrahydro-4H-10,14-(metheno)[1,7]oxazacyclotetradecino[9,8,7-hi]indole-2-carboxylate

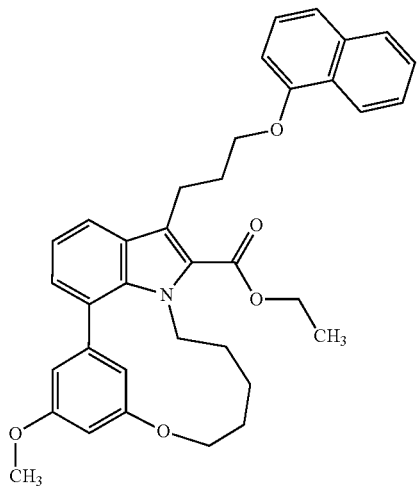 [SMILES: CCOC(=O)c1c(CCCOc2cccc3ccccc23)c2cccc3c2n1CCCCCOc1cc(OC)cc-3c1]

To a solution of ethyl 7-(3-hydroxy-5-methoxyphenyl)-3-[3-(naphthalen-1-yloxy)propyl]-1H-indole-2-carboxylate (see Intermediate 1-236; 150 mg, 303 µmol) in THF (15 mL) were added potassium 2-methylpropan-2-olate (84.9 mg, 757 µmol), 1,5-dibromopentane (100 µl, 760 µmol) and the mixture was stirred at 80° C. overnight. After filtration and concentration the residue was purified by preparative TLC (ethyl acetate:n-hexane) to give the title compound 42.0 mg (25% yield).

MS: m/z=564.3 [M+H]+.

Intermediate 1 tert-Butyl (3-bromopropyl)methylcarbamate

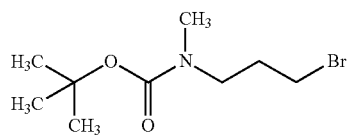

To a solution of tert-butyl (3-hydroxypropyl)methylcarbamate (5.25 g, 27.2 mmol, CAS 98642-44-5) and triphenylphosphine (9.36 g, 99% purity, 35.3 mmol) in dichloromethane (110 ml) was added tetrabromomethane (11.8 g, 99% purity, 35.3 mmol) over a period of 30 minutes at 0° C. and the mixture was stirred at 0° C. for 14 hours. The reaction was diluted with dichloromethane and the mixture was washed with sodium bicarbonate solution, sodium thiosulfate solution and brine. The organic phase was dried over sodium sulfate. The mixture was filtered and the filtrate was concentrated under reduced pressure. The crude product was purified by flash chromatography (Biotage SNAP cartridge NH2 silica, hexanes/ethyl acetate gradient, 7%→60% ethyl acetate) to give the title compound (5.9 g).

1H-NMR (400 MHz, CHLOROFORM-d) δ [ppm]: 0.009 (1.77), 1.402 (16.00), 1.536 (1.37), 2.022 (0.46), 2.815 (5.06), 3.275 (1.19), 3.292 (1.89), 3.308 (1.16), 3.326 (1.19), 3.343 (2.23), 3.360 (1.04).

Intermediate 2 tert-butyl (4-bromobutyl)methylcarbamate

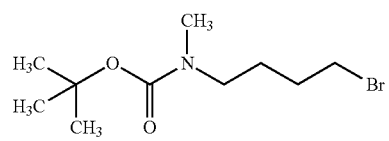

The title compound was prepared in analogy to intermediate 1 with tert-butyl (4-hydroxybutyl)methylcarbamate as starting material.

Intermediate 3

Ethyl 7-bromo-3-(3-bromopropyl)-1H-indole-2-carboxylate

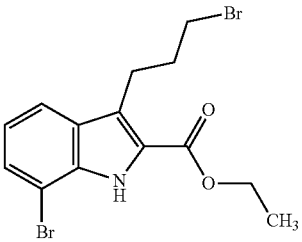 [SMILES: CCOC(=O)c1[nH]c2c(Br)cccc2c1CCCBr]

A mixture of ethyl 7-bromo-3-(3-hydroxypropyl)-1H-indole-2-carboxylate (20.0 g, 61.3 mmol, prepared as described in Journal of Medicinal Chemistry, 2015, 58, 2180-2194), tetrabromomethane (50.8 g, 153 mmol), pyridine (12 mL), dichloromethane (150 mL) and acetonitrile (350 mL) was cooled to 0° C. Triphenylphosphine (62.3 g, 237 mmol) was added and the reaction was stirred at rt overnight. Dichloromethane was removed, the precipitate filtered off and the filtrate concentrated. The residue was purified by repeated flash chromatography (Biotage SNAP cartridge silica 750 g, ethyl acetate: dichloromethane) to give the title compound (18.6 g).

MS: m/z=388 [M+H]+.

Intermediate 4

Ethyl 7-bromo-3-[3-(naphthalen-1-yloxy)propyl]-1H-indole-2-carboxylate

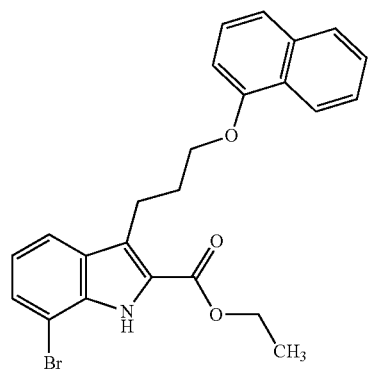 [SMILES: CCOC(=O)c1[nH]c2c(Br)cccc2c1CCCOc1cccc2ccccc12]

To a solution of naphthalen-1-ol (6.87 g, 47.7 mmol) in N,N-dimethylacetamide (180 mL) were added potassium carbonate (6.59 g, 47.7 mmol) followed by the solution of ethyl 7-bromo-3-(3-bromopropyl)-1H-indole-2-carboxylate (18.6 g, 47.7 mmol) in N,N-dimethylacetamide (85 mL). The mixture was stirred at 50° C. for 30 hours, poured into water and extracted with ethyl acetate. The organic layer was washed with water and brine and dried over sodium sulfate. After filtration and removal of the solvent the residue was purified by flash chromatography (Biotage SNAP cartridge silica 340 g, ethyl acetate: n-hexane) to give the title compound (13.5 g, 62% yield).
MS: m/z=452 [M+H]$^+$.

Intermediate 5

Ethyl 3-[3-(naphthalen-1-yloxy)propyl]-7-(4,4,5,5-tetramethyl-1,3,2-dioxaborolan-2-yl)-1H-indole-2-carboxylate

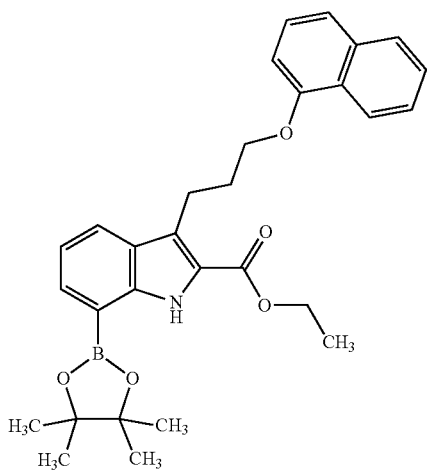 [SMILES: CCOC(=O)c1[nH]c2c(B3OC(C)(C)C(C)(C)O3)cccc2c1CCCOc1cccc2ccccc12]

Ethyl 3-[3-(naphthalen-1-yloxy)propyl]-7-(4,4,5,5-tetramethyl-1,3,2-dioxaborolan-2-yl)-1H-indole-2-carboxylate was prepared as described in the literature (Journal of Medicinal Chemistry, 2015, 58, 2180-2194).

Intermediate 6

Ethyl 4-bromo-3-(bromomethyl)-1-methyl-1H-pyrazole-5-carboxylate

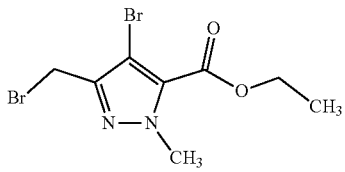

4-Bromo-3-bromomethyl-1-methyl-1H-pyrazole-5-carboxylic acid ethyl ester was prepared as described in the literature (Journal of Medicinal Chemistry, 2014, 57, 4720-4744) starting from ethyl 1,3-dimethyl-1H-pyrazole-5-carboxylate (CAS 5744-40-1).
LC-MS (Method 1): Rt=1.23 min; MS (ESIpos): m/z=324 [M+H]$^+$

Intermediate 7 ethyl 4-bromo-1,3-dimethyl-1H-pyrazole-5-carboxylate

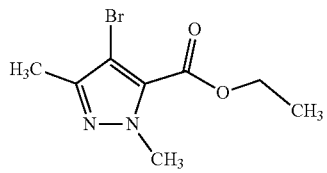

N-Bromosuccinimide (11.2 g, 62.4 mmol) was added to a solution of ethyl 1,3-dimethyl-1H-pyrazole-5-carboxylate (5.00 g, 29.7 mmol, CAS No: 5744-40-1) in 1,2-dichloroethane (100 ml) and the mixture was stirred for 15 h at 65-80° C. followed by 3 d at room temperature. For work-up, the mixture was diluted with ethyl acetate, washed with water and the organic phase was filtered through a silicone filter and concentrated. The residue was purified by flash chromatography (Biotage SNAP cartridge silica, hexanes/dichloromethane gradient, 0%→100% dichloromethane) to give the title compound (6.69 g, 89% yield).
LC-MS (Method 2): R$_t$=1.15 min; MS (ESIpos): m/z=247 [M+H]$^+$
$^1$H-NMR (400 MHz, DMSO-d6) δ [ppm]: 1.308 (4.21), 1.325 (8.89), 1.343 (4.18), 2.155 (14.47), 3.862 (1.45), 4.008 (16.00), 4.302 (1.34), 4.320 (4.19), 4.337 (4.07), 4.355 (1.24).

Intermediate 8

(4-bromo-1,3-dimethyl-1H-pyrazol-5-yl)methanol

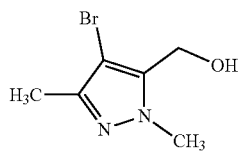

Lithium aluminium hydride (27 ml, 1.0 M in THF, 27 mmol) was added dropwise at 0° C. to a solution of ethyl 4-bromo-1,3-dimethyl-1H-pyrazole-5-carboxylate (6.69 g, 27.1 mmol) in THF (220 ml) and the mixture was stirred at 0° C. for 1.5 h. The reaction was quenched by dropwise addition of water (5.4 ml) followed by aqueous sodium hydroxide (5.4 ml, 2 M, 11 mmol) and again water (5.4 ml). The mixture was then filtered through a pad of celite, eluted with THF and the filtrate was concentrated. The residue was purified by flash chromatography (Biotage SNAP cartridge silica 100 g, hexanes/ethyl acetate gradient, 20%→80% ethyl acetate) to give the title compound (3.77 g, 67% yield).

¹H-NMR (400 MHz, DMSO-d6) δ [ppm]: 2.083 (14.56), 3.334 (16.00), 4.422 (2.80), 4.435 (2.81), 5.311 (0.59), 5.325 (1.50), 5.337 (0.56).

Intermediate 9

Ethyl 7-[5-(hydroxymethyl)-1,3-dimethyl-1H-pyrazol-4-yl]-3-[3-(1-naphthyloxy)propyl]-1H-indole-2-carboxylate

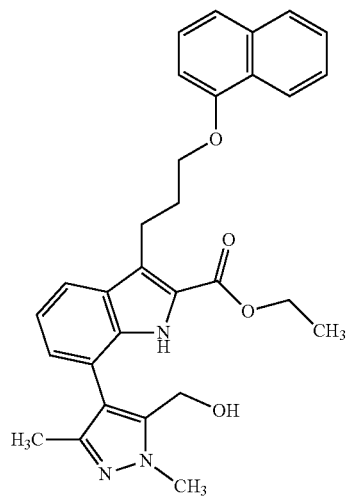

XPhos Pd G2 (see abbreviations; 109 mg, 138 µmol) was added to a degassed mixture of ethyl 3-[3-(naphthalen-1-yloxy)propyl]-7-(4,4,5,5-tetramethyl-1,3,2-dioxaborolan-2-yl)-1H-indole-2-carboxylate (see Intermediate 5; 2.50 g, 5.01 mmol), (4-bromo-1,3-dimethyl-1H-pyrazol-5-yl)methanol (933 mg, 4.55 mmol) aqueous potassium phosphate solution (18 ml, 0.50 M, 9.1 mmol) and THF (55 ml). The mixture was stirred for 2 h at 45° C. For work-up, ethyl acetate was added, the mixture was filtered through a pad of celite, eluted with ethyl acetate and the organic phase was washed with brine, filtrated through a silicone filter and concentrated. The residue was purified by flash chromatography (Biotage SNAP cartridge silica 50 g, hexanes/ethyl acetate gradient, 50%→100% ethyl acetate) to give the title compound (1.45 g, 57% yield).

LC-MS (Method 2): $R_t$=1.52 min; MS (ESIpos): m/z=498 [M+H]⁺

¹H-NMR (400 MHz, DMSO-d6) δ [ppm]: 1.260 (5.06), 1.278 (11.54), 1.296 (5.20), 2.067 (16.00), 2.214 (1.01), 2.230 (1.35), 2.249 (1.04), 2.518 (2.38), 2.523 (1.64), 3.160 (0.97), 3.173 (0.93), 3.350 (2.33), 3.354 (2.31), 3.372 (1.26), 3.864 (15.21), 4.200 (1.44), 4.215 (2.97), 4.230 (1.53), 4.236 (1.75), 4.254 (4.67), 4.272 (4.59), 4.290 (1.49), 4.329 (1.12), 5.711 (1.56), 5.759 (1.07), 6.905 (1.64), 6.908 (1.72), 6.924 (1.87), 6.927 (1.75), 7.068 (1.22), 7.086 (2.45), 7.106 (2.54), 7.120 (2.64), 7.123 (2.89), 7.138 (1.35), 7.141 (0.98), 7.373 (1.32), 7.394 (2.57), 7.413 (2.10), 7.450 (2.58), 7.471 (1.42), 7.491 (0.60), 7.504 (1.58), 7.508 (1.42), 7.514 (1.71), 7.521 (3.41), 7.528 (1.75), 7.533 (1.50), 7.538 (1.67), 7.550 (0.63), 7.664 (1.56), 7.668 (1.60), 7.684 (1.54), 7.688 (1.40), 7.860 (1.49), 7.863 (1.22), 7.868 (0.83), 7.878 (1.42), 7.883 (1.28), 8.225 (1.33), 8.230 (1.25), 8.247 (1.16), 8.249 (1.25), 10.911 (2.23).

Intermediate 10 ethyl 4-bromo-1,5-dimethyl-1H-pyrazole-3-carboxylate

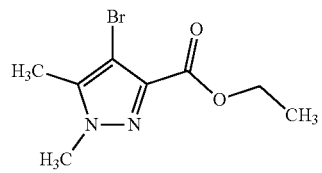

N-Bromosuccinimide (16.3 g, 90.5 mmol) was added to a solution of ethyl 1,5-dimethyl-1H-pyrazole-3-carboxylate (7.25 g, 43.1 mmol, CAS No 5744-51-4) in 1,2-dichloroethane (150 ml) and the mixture was stirred for 15 h at 80° C. For work-up, the mixture was diluted with dichloromethane, washed with water and the organic phase was filtered through a silicone filter and concentrated. The residue was purified by flash chromatography (Biotage SNAP cartridge silica 340 g, hexanes/dichloromethane gradient, 0→100% dichloromethane) to give the title compound (6.49 g, 61% yield).

¹H-NMR (400 MHz, DMSO-d6) δ [ppm]: 1.261 (4.14), 1.278 (8.78), 1.296 (4.21), 2.268 (14.94), 2.518 (0.74), 2.523 (0.49), 3.857 (16.00), 4.229 (1.31), 4.247 (4.03), 4.264 (3.94), 4.282 (1.24).

Intermediate 11

(4-bromo-1,5-dimethyl-1H-pyrazol-3-yl)methanol

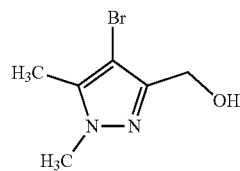

Lithium borohydride (711 mg, 32.6 mmol) was added to a solution of ethyl 4-bromo-1,5-dimethyl-1H-pyrazole-3-carboxylate (6.45 g, 26.1 mmol) in THF (150 ml) and the mixture was stirred for 1 h at room temperature and 7 h at 60° C. The reaction was quenched by addition of saturated aqueous ammonium chloride solution and the mixture was extracted with ethyl acetate. The organic phase was filtered through a silicone filter and concentrated. The residue was purified by flash chromatography (hexanes/ethyl acetate gradient, 50%→100% ethyl acetate) to give the title compound (4.07 g, 76% yield).

¹H-NMR (400 MHz, DMSO-d6) δ [ppm]: 2.205 (16.00), 2.518 (0.43), 3.330 (10.35), 4.285 (3.97), 4.299 (4.13), 4.933 (1.00), 4.946 (2.22), 4.960 (0.93).

Intermediate 12 ethyl 7-[3-(hydroxymethyl)-1,5-dimethyl-1H-pyrazol-4-yl]-3-[3-(naphthalen-1-yloxy)propyl]-1H-indole-2-carboxylate

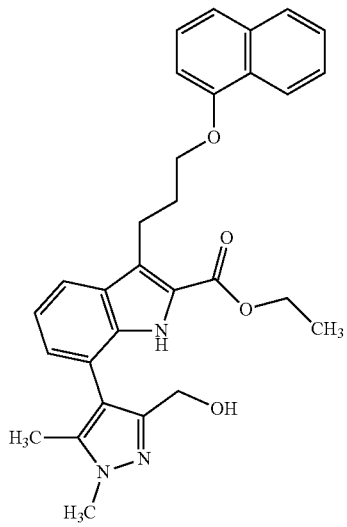

XPhos Pd G2 (see abbreviations; 483 mg, 613 µmol) was added to a degassed mixture of ethyl 3-[3-(naphthalen-1-yloxy)propyl]-7-(4,4,5,5-tetramethyl-1,3,2-dioxaborolan-2-yl)-1H-indole-2-carboxylate (see Intermediate 5; 10.0 g, 20.0 mmol), (4-bromo-1,5-dimethyl-1H-pyrazol-3-yl)methanol (3.73 g, 18.2 mmol), aqueous potassium phosphate solution (73 ml, 0.50 M, 36 mmol) and THF (220 ml). The mixture was stirred for 2 h at 45° C. For work-up, ethyl acetate was added, the mixture was filtered through a pad of celite, eluted with ethyl acetate and the organic phase was washed with brine, filtered through a silicone filter and concentrated. The residue was purified by flash chromatography (Biotage SNAP cartridge silica 340 g, hexanes/ethyl acetate gradient, 50%→100% ethyl acetate) to give the title compound (6.26 g, 63% yield).

LC-MS (Method 1): $R_t$=1.53 min; MS (ESIpos): m/z=498 [M+H]⁺

¹H-NMR (400 MHz, DMSO-d6) δ [ppm]: 1.155 (0.41), 1.173 (0.87), 1.190 (0.43), 1.256 (4.82), 1.273 (10.89), 1.291 (4.91), 1.988 (1.61), 2.164 (15.76), 2.205 (5.25), 2.213 (1.06), 2.231 (1.35), 2.250 (1.03), 2.518 (4.03), 2.523 (2.82), 3.355 (2.05), 3.373 (1.25), 3.726 (4.77), 3.802 (16.00), 4.199 (1.49), 4.214 (3.13), 4.222 (2.24), 4.229 (1.83), 4.240 (5.74), 4.249 (2.82), 4.258 (5.54), 4.275 (1.50), 4.286 (1.45), 4.300 (1.40), 4.947 (0.67), 5.705 (1.59), 6.907 (1.76), 6.925 (1.90), 7.060 (0.72), 7.077 (2.44), 7.090 (2.89), 7.096 (5.04), 7.108 (0.79), 7.373 (1.28), 7.394 (2.46), 7.413 (2.02), 7.450 (2.56), 7.471 (1.40), 7.492 (0.58), 7.505 (1.56), 7.509 (1.42), 7.514 (1.62), 7.521 (3.30), 7.529 (1.74), 7.533 (1.54), 7.538 (1.62), 7.551 (0.63), 7.656 (1.49), 7.662 (1.33), 7.674 (1.37), 7.679 (1.33), 7.861 (1.49), 7.868 (0.80), 7.879 (1.35), 7.884 (1.25), 8.230 (1.30), 8.236 (1.23), 8.254 (1.25), 11.324 (1.73).

Intermediate 13

2-[2-(2-Bromo-3-methylphenyl)hydrazinylidene]hexanedioic acid

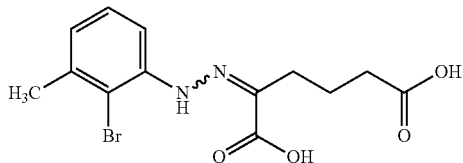 [SMILES: Cc1cccc(NN=C(CCCC(=O)O)C(=O)O)c1Br]

To a mixture of 2-bromo-3-methylaniline (25.4 g, 137 mmol; CAS-No: 54879-20-8), water (61 mL) and concentrated hydrochloric acid (110 mL, 37% in water) was slowly added at −5° C. a solution of sodium nitrite (9.71 g, 141 mmol) in water (36 mL), keeping the temperature at 0° C. This mixture was slowly added to a solution of ethyl 2-oxocyclopentanecarboxylate (19 mL, 130 mmol; CAS-No: 611-10-9) in potassium hydroxide (190 mL, 4.0 M in water, 780 mmol) at 0° C. The reaction was stirred at rt overnight, concentrated hydrochloric acid (105 mL, 37% in water) was added and stirring continued for 1 h. The precipitate was filtered, washed with water, re-dissolved in saturated aqueous sodium hydrogen carbonate and undissolved components were filtered off. To the filtrate was added concentrated hydrochloric acid until pH 2 was reached. The precipitate was isolated by filtration, washed with water and dried to give the title compound (28.3 g, 60% yield).

MS: m/z=343 [M+H]⁺.

Intermediate 14

Ethyl 7-bromo-3-(3-ethoxy-3-oxopropyl)-6-methyl-1H-indole-2-carboxylate

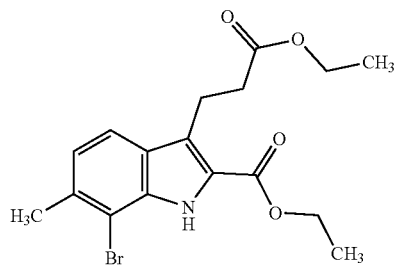

To a solution of 2-[2-(2-bromo-3-methylphenyl)hydrazinylidene]hexanedioic acid (28.2 g, 82.3 mmol) in ethanol (720 mL) was added concentrated sulfuric acid (180 mL) and the mixture was stirred at 90° C. overnight. After concentration, dichloromethane was added, the organic layer washed with water and dried over sodium sulfate. After filtration and removal of the solvent the residue was purified by flash chromatography (Biotage SNAP cartridge silica 750 g, ethyl acetate: n-hexane) to give the title compound together with ethyl 3-(7-bromo-6-methyl-1H-indol-3-yl)propanoate as a 7:3-mixture (18.9 g, 64% yield).

MS: m/z=382 [M+H]⁺.

Intermediate 15

3-[7-Bromo-2-(ethoxycarbonyl)-6-methyl-1H-indol-3-yl]propanoic acid

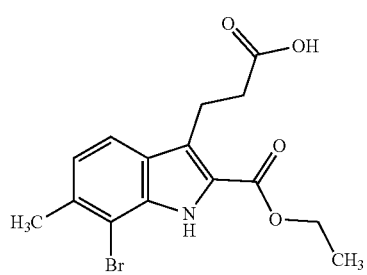

A 7:3-mixture of ethyl 7-bromo-3-(3-ethoxy-3-oxopropyl)-6-methyl-1H-indole-2-carboxylate and ethyl 3-(7-bromo-6-methyl-1H-indol-3-yl)propanoate (18.9 g, 52.4 mmol) was solved in glacial acetic acid (170 mL) at 80° C. Hydrochloric acid (23 mL, 37% in water, 270 mmol) was added and the mixture was heated at 80° C. for 3 hrs. After cooling to rt, water (230 mL) was added, the precipitate collected, washed with water and dried to give the title compound together with 3-(7-bromo-6-methyl-1H-indol-3-yl)propanoic acid as a 7:3-mixture (15.5 g, 89% yield).

MS: m/z=354 [M+H]$^+$.

Intermediate 16

Ethyl 7-bromo-3-(3-hydroxypropyl)-6-methyl-1H-indole-2-carboxylate

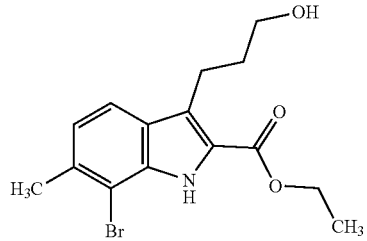

A solution of a 7:3-mixture of 3-[7-bromo-2-(ethoxycarbonyl)-6-methyl-1H-indol-3-yl]propanoic acid and 3-(7-bromo-6-methyl-1H-indol-3-yl)propanoic acid (15.5 g, 46.6 mmol) in THF (110 mL) was cooled to −25° C. Borane (61 mL, 1.0 M in THF, 61 mmol) was added over 1 h, the mixture warmed to RT and stirring was continued for 1.5 hr. Methanol (50 mL) was added, the mixture concentrated and purified by repeated Biotage (Biotage SNAP cartridge silica 750 g, ethyl acetate: n-hexane) to give the title compound (8.49 g, 57% yield).

MS: m/z=340 [M+H]$^+$.

Intermediate 17

Ethyl 7-bromo-3-(3-bromopropyl)-6-methyl-1H-indole-2-carboxylate

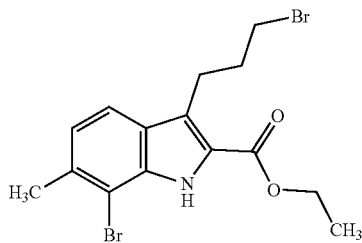

A mixture of ethyl 7-bromo-3-(3-hydroxypropyl)-6-methyl-1H-indole-2-carboxylate (20.2 g, 59.4 mmol), tetrabromomethane (78.8 g, 237 mmol), pyridine (19 mL), dichloromethane (140 mL) and acetonitrile (340 mL) was cooled to 0° C. Triphenylphosphine (62.3 g, 237 mmol) was added and the reaction was stirred at rt overnight. Dichloromethane was removed, the precipitate was filtered off and the filtrate concentrated. The residue was purified by repeated flash chromatography (Biotage SNAP cartridge silica 750 g, ethyl acetate: dichloromethane) to give the title compound (19.7 g, 82% yield).

MS: m/z=402 [M+H]$^+$.

Intermediate 18

Ethyl 7-bromo-6-methyl-3-[3-(naphthalen-1-yloxy)propyl]-1H-indole-2-carboxylate

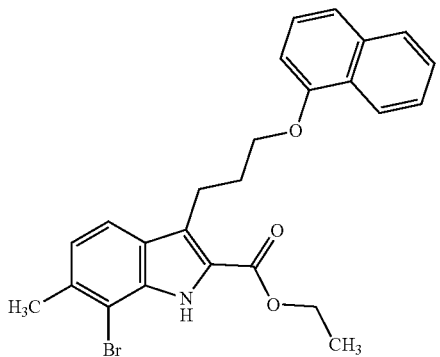

To a solution of naphthalen-1-ol (3.32 g, 23.0 mmol) in N,N-dimethylacetamide (35 mL) was added potassium carbonate (3.18 g, 23.0 mmol), followed by a solution of ethyl 7-bromo-3-(3-bromopropyl)-6-methyl-1H-indole-2-carboxylate (7.74 g, 19.2 mmol) in N,N-dimethylacetamide (70 mL). The mixture was stirred at 50° C. for 2.5 days, poured into water and extracted with ethyl acetate. The organic layer was washed with water and brine and dried over sodium sulfate. After filtration and removal of the solvent the residue was purified by flash chromatography (Biotage SNAP cartridge silica 750 g, ethyl acetate: n-hexane) to give the title compound (7.76 g, 87% yield)

MS: m/z=466 [M+H]+.

Intermediate 19

Ethyl 6-methyl-3-[3-(naphthalen-1-yloxy)propyl]-7-(4,4,5,5-tetramethyl-1,3,2-dioxaborolan-2-yl)-1H-indole-2-carboxylate

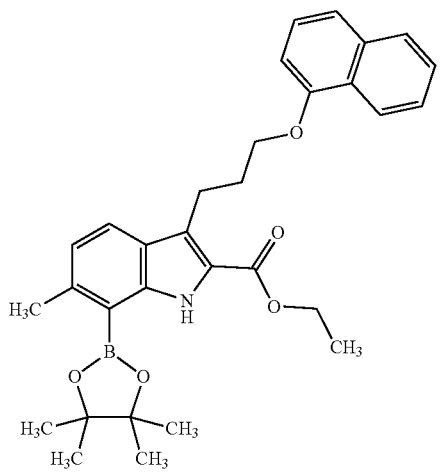

To a solution of ethyl 7-bromo-6-methyl-3-[3-(naphthalen-1-yloxy)propyl]-1H-indole-2-carboxylate (2.50 g, 5.36 mmol) in 1,4-dioxane (35 mL) were added 4,4,4',4',5,5,5',5'-octamethyl-2,2'-bi-1,3,2-dioxaborolane (2.72 g, 10.7 mmol) and potassium acetate (2.10 g, 21.4 mmol). The mixture was degassed and purged with argon several times. [1,1'-Bis(diphenylphosphino)ferrocene]dichloropalladium (II) (876 mg, 1.07 mmol; complex with dichloromethane) was added and the mixture stirred at 85° C. overnight. After cooling the mixture was poured into water and extracted with ethyl acetate. The organic layer was washed with water and brine and dried over sodium sulfate. After filtration and removal of the solvent the residue was purified by flash chromatography (Biotage SNAP cartridge silica 340 g, ethyl acetate: n-hexane) to give the title compound (1.65 g, 60% yield).

MS: m/z=514 [M+H]+.

Intermediate 20

N-(4-iodo-1,3-dimethyl-1H-pyrazol-5-yl)benzamide

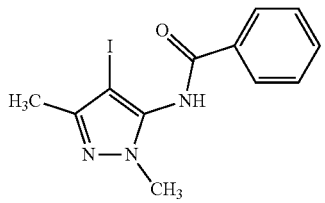 [SMILES: Cc1nn(C)c(NC(=O)c2ccccc2)c1I]

To a solution of N-(1,3-dimethyl-1H-pyrazol-5-yl)benzamide (CAS 54384-73-5, 100 mg, 0.465 mmol) in dichloromethane (1 mL) at 23° C. was added N-iodosuccinimide (110 mg, 0.488 mmol), and the mixture was stirred for 1 h. Upon completion of the reaction, the reaction mixture was concentrated and adsorbed onto silica gel. The crude product was purified by flash chromatography on silica gel (0-100% ethyl acetate/hexanes) to afford the title compound (149 mg, 0.436 mmol).

$^1$H NMR (500 MHz, CDCl3) δ [ppm]: 7.94 (d, J=7.3 Hz, 2H), 7.63 (t, J=7.4 Hz, 1H), 7.54 (t, J=7.5 Hz, 2H), 7.47 (s, 1H), 3.80 (s, 3H), 2.25 (s, 3H).

MS: m/z=342.0 [M+H]+

Intermediate 21

N-benzyl-1,3-dimethyl-1H-pyrazol-5-amine

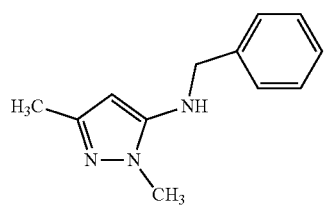

To a solution of N-(4-iodo-1,3-dimethyl-1H-pyrazol-5-yl)benzamide (751 mg, 2.20 mmol) in tetrahydrofuran (4.4 mL) at 0° C. was added lithium aluminium hydride (334 mg, 8.81 mmol) and the mixture was stirred for 16 h at 80° C. Upon completion, the reaction was stopped by adding 350 µL of water, 700 µL of 15% aqueous sodium hydroxide solution, 1.05 mL of water, and magnesium sulfate was added. The mixture was allowed to stir at room temperature for 15 min and then filtered through Celite. The filter cake was rinsed with tetrahydrofuran and the filtrate was concentrated. The crude product was purified by reverse phase flash chromatography on C18 silica gel (0-60% acetonitrile/water with 10 mM ammonium formate buffer) to afford, after lyophilization, the title compound (330 mg, 1.64 mmol).

MS: m/z=202.2 [M+H]+

Intermediate 22

N-benzyl-4-iodo-1,3-dimethyl-1H-pyrazol-5-amine

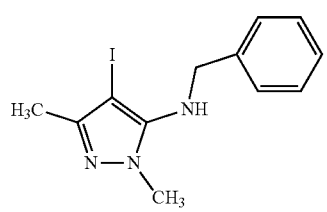 [SMILES: Cc1nn(C)c(NCc2ccccc2)c1I]

To a solution of N-benzyl-1,3-dimethyl-1H-pyrazol-5-amine (325 mg, 1.62 mmol) in dichloromethane (20 mL) at 23° C. was added N-iodosuccinimide (381 mg, 1.70 mmol), and the mixture was stirred for 1 h. Upon completion of the reaction, the reaction mixture was concentrated, dissolved in dimethylsulfoxide, and purified by reverse phase flash chromatography on C18 silica gel (0-100% acetonitrile in water with 10 mM ammonium formate buffer) to afford the title compound (490 mg, 1.50 mmol).

MS: m/z=328.24 [M+H]+

415

Intermediate 23 ethyl 7-[5-(benzylamino)-1,3-dimethyl-1H-pyrazol-4-yl]-3-[3-(1-naphthyloxy)propyl]-1H-indole-2-carboxylate

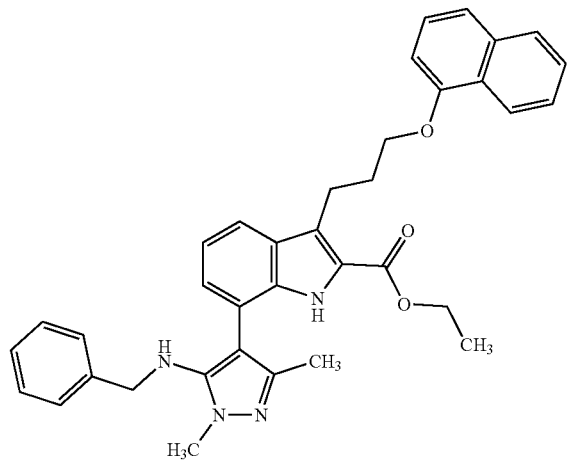

A vial was charged with ethyl 3-[3-(naphthalen-1-yloxy)propyl]-7-(4,4,5,5-tetramethyl-1,3,2-dioxaborolan-2-yl)-1H-indole-2-carboxylate (see Intermediate 5, 580 mg, 0.941 mmol), N-benzyl-4-iodo-1,3-dimethyl-1H-pyrazol-5-amine (462 mg, 1.411 mmol) and sodium carbonate (598 mg, 5.64 mmol) under inert atmosphere and dissolved in a 4:1 mixture of degassed 1,4-dioxane (15 mL)/water (3.8 mL). To this, was added tetrakis(triphenylphosphine)palladium (0) (163 mg, 0.141 mmol) and the reaction mixture was heated to 85° C. After stirring for 90 min, the reaction was stopped by adding water, and the reaction mixture was diluted with ethyl acetate, and the organic phase was washed with brine, dried over magnesium sulfate and concentrated. The crude residue was purified by flash chromatography on silica gel (0-100% ethyl acetate/hexanes) to afford the title compound (190.8 mg, 0.326 mmol).

$^1$H NMR (500 MHz, CDCl$_3$) δ [ppm]: 8.99 (s, 1H), 8.41-8.34 (m, 1H), 7.84-7.78 (m, 1H), 7.67 (d, J=7.6 Hz, 1H), 7.52-7.46 (m, 2H), 7.41 (d, J=8.3 Hz, 1H), 7.37-7.32 (m, 1H), 7.17-7.10 (m, 5H), 6.97-6.90 (m, 2H), 6.77 (d, J=7.2 Hz, 1H), 4.38 (q, J=7.1 Hz, 2H), 4.23 (t, J=6.2 Hz, 2H), 3.83 (s, 2H), 3.70 (s, 3H), 3.64 (s, 1H), 3.47-3.40 (m, 2H), 2.42-2.34 (m, 2H), 2.16 (s, 3H), 1.38 (t, J=7.1 Hz, 3H). Rt=2.22 min;

MS: m/z=573.4 [M+H]$^+$

416

Intermediate 24 ethyl 1-allyl-7-{5-[allyl(benzyl)amino]-1,3-dimethyl-1H-pyrazol-4-yl}-3-[3-(1-naphthyloxy)propyl]-1H-indole-2-carboxylate

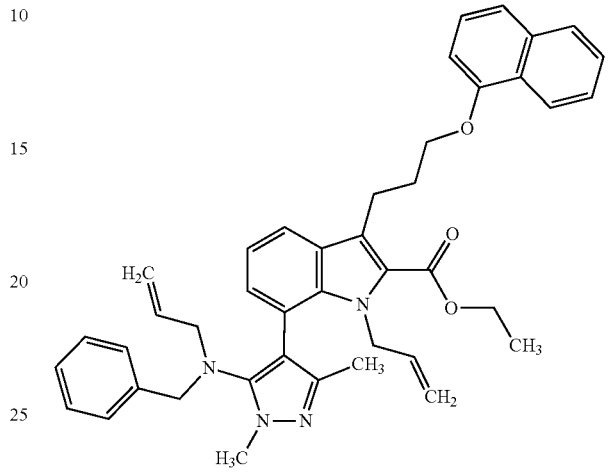

A screw-cap vial was charged with ethyl 7-[5-(benzylamino)-1,3-dimethyl-1H-pyrazol-4-yl]-3-[3-(1-naphthyloxy)propyl]-1H-indole-2-carboxylate (190 mg, 0.332 mmol), 3-bromoprop-1-ene (172 μl, 1.99 mmol), sodium hydride (53.1 mg, 1.33 mmol) and anhydrous dimethylformamide (11 mL). After stirring at 25° C. for 18 h, additional sodium hydride (20 mg) and 3-bromoprop-1-ene (172 μl, 1.99 mmol) were added and the mixture was heated to reflux for 12 h. The reaction was stopped by adding water, and the mixture was extracted with ethyl acetate. The organic layer was washed with water and dried over magnesium sulfate. The solvent was removed in vacuo and the resulting crude residue was purified by flash chromatography on silica gel (0-40% ethyl acetate/hexanes) to afford the title compound (155.6 mg, 0.238 mmol).

$^1$H NMR (500 MHz, CDCl$_3$) δ [ppm]: 8.42-8.37 (m, 1H), 7.83-7.79 (m, 1H), 7.74 (dd, J=8.0, 1.2 Hz, 1H), 7.53-7.48 (m, 2H), 7.42 (d, J=8.3 Hz, 1H), 7.36-7.32 (m, 1H), 7.25-7.18 (m, 3H), 7.09-7.02 (m, 3H), 6.91 (dd, J=7.1, 1.1 Hz, 1H), 6.77 (d, J=7.1 Hz, 1H), 5.76-5.67 (m, 1H), 5.60-5.51 (m, 1H), 5.06 (s, 1H), 5.05-5.01 (m, 1H), 4.94-4.87 (m, 1H), 4.82-4.76 (m, 2H), 4.35-4.28 (m, 3H), 4.23 (t, J=6.3 Hz, 2H), 3.83 (d, J=14.5 Hz, 1H), 3.76 (s, 3H), 3.72 (d, J=14.5 Hz, 1H), 3.44-3.25 (m, 4H), 2.37 (p, J=7.3 Hz, 2H), 1.98 (s, 3H), 1.35 (t, J=7.1 Hz, 3H).

MS: m/z=635.5 [M+H]$^+$

Intermediate 25

(rac)-ethyl (5E/Z)-8-benzyl-9,11-dimethyl-1-[3-(1-naphthyloxy)propyl]-4,7,8,9-tetrahydropyrazolo[4′,3′:4,5][1,6]diazecino[3,2,1-hi]indole-2-carboxylate

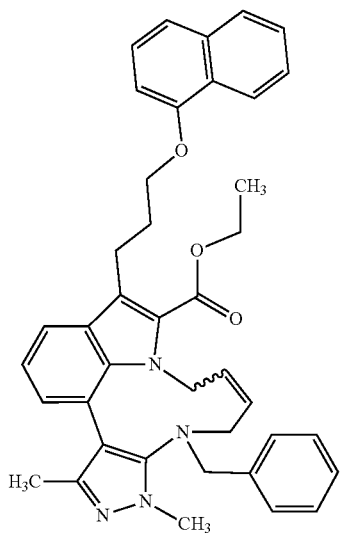 [SMILES: CCOC(=O)c1c(CCCOc2cccc3ccccc23)c2cccc3c2n1CC=CCN(Cc1ccccc1)c1c-3c(C)nn1C]

To a solution of ethyl 1-allyl-7-{5-[allyl(benzyl)amino]-1,3-dimethyl-1H-pyrazol-4-yl}-3-[3-(1-naphthyloxy)propyl]-1H-indole-2-carboxylate (140 mg, 0.214 mmol) in dry toluene (35 mL), was added Grubbs 2nd generation catalyst (see abbreviation list; 18.2 mg, 0.021 mmol) in 3 portions at equal time intervals every 2 h at 90° C. under nitrogen atmosphere. After stirring for an additional 90 min, the reaction mixture was cooled to room temperature, concentrated, and the crude product was purified by flash chromatography on silica gel (0-50% ethyl acetate/hexanes) to afford the title compound (130 mg, 0.207 mmol).

$^{1}$H NMR (500 MHz, CDCl$_3$) δ [ppm]: 8.42-8.36 (m, 1H), 7.85-7.79 (m, 1H), 7.76 (dd, J=7.7, 1.2 Hz, 1H), 7.54-7.48 (m, 2H), 7.43 (d, J=8.3 Hz, 1H), 7.35 (t, J=7.9 Hz, 1H), 7.25-7.14 (m, 5H), 7.10 (d, J=6.5 Hz, 2H), 6.79 (d, J=7.5 Hz, 1H), 5.77-5.64 (m, 2H), 4.81 (dd, J=17.0, 5.3 Hz, 1H), 4.67 (d, J=17.0 Hz, 1H), 4.35 (q, J=7.1 Hz, 2H), 4.25 (t, J=6.1 Hz, 2H), 3.68 (d, J=13.1 Hz, 1H), 3.58-3.50 (m, 4H), 3.50-3.38 (m, 3H), 3.03 (dd, J=11.6, 6.7 Hz, 1H), 2.43-2.32 (m, 2H), 2.10 (s, 3H), 1.38 (t, J=7.1 Hz, 3H).

MS: m/z=625.5 [M+H]$^{+}$

Intermediate 26 tert-butyl 4-(4-{[4-bromo-5-(ethoxycarbonyl)-1-methyl-1H-pyrazol-3-yl]methoxy}phenyl)piperazine-1-carboxylate

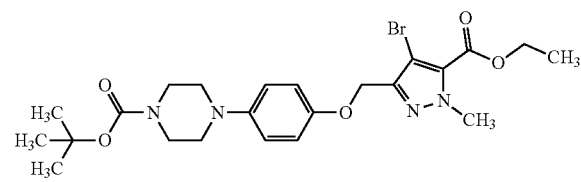

A mixture of ethyl 4-bromo-3-(bromomethyl)-1-methyl-1H-pyrazole-5-carboxylate (see Intermediate 6; 10.9 g, 33.3 mmol), tert-butyl 4-(4-hydroxyphenyl)piperazine-1-carboxylate (10.0 g, 34.9 mmol, CAS 158985-25-2) and potassium carbonate (13.8 g, 99.8 mmol) in DMF (100 ml) was stirred for 12 h at room temperature. For work-up, water was added and the mixture was extracted with ethyl acetate, the organic phase was washed with water, filtered through a silicone filter and concentrated. The residue was purified by flash chromatography (hexanes/ethyl acetate gradient, 20%→30% ethyl acetate) to give the title compound (11.9 g, 68% yield).

LC-MS (Method 2): R$_t$=1.50 min; MS (ESIpos): m/z=523 [M+H]$^{+}$ $^{1}$H-NMR (400 MHz, DMSO-d6) δ [ppm]: 1.155 (1.12), 1.173 (2.34), 1.190 (1.18), 1.318 (1.52), 1.335 (3.30), 1.353 (1.55), 1.413 (16.00), 1.988 (4.49), 2.941 (0.94), 2.954 (1.31), 2.966 (1.04), 3.427 (0.87), 3.439 (1.14), 3.450 (0.78), 4.017 (1.04), 4.035 (1.03), 4.081 (5.74), 4.324 (0.45), 4.342 (1.45), 4.359 (1.44), 4.377 (0.43), 4.924 (2.68), 6.911 (4.03).

Intermediate 27 ethyl 4-bromo-1-methyl-3-{[4-(piperazin-1-yl)phenoxy]methyl}-1H-pyrazole-5-carboxylate hydrochloric acid salt

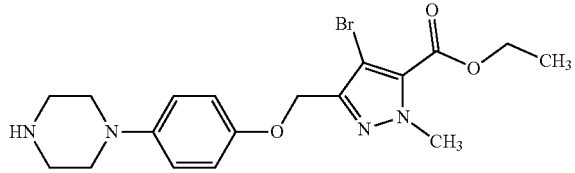 [SMILES: CCOC(=O)c1c(Br)c(COc2ccc(N3CCNCC3)cc2)nn1C]

To a solution of tert-butyl 4-(4-{[4-bromo-5-(ethoxycarbonyl)-1-methyl-1H-pyrazol-3-yl]methoxy}phenyl)piperazine-1-carboxylate (see intermediate 26 8.42 g, 16.1 mmol) in 1,4-dioxane (30 ml) was added a solution of HCl in dioxan (40 ml, 4.0 M, 160 mmol) at 0° C. and the mixture was stirred for 3 hours at room temperature. For work-up the mixture was concentrated under reduced pressure and the crude product was used in the subsequent steps without further purification.

Intermediate 28

Ethyl 4-bromo-3-({4-[4-(dimethylsulfamoyl)piperazin-1-yl]phenoxy}methyl)-1-methyl-1H-pyrazole-5-carboxylate

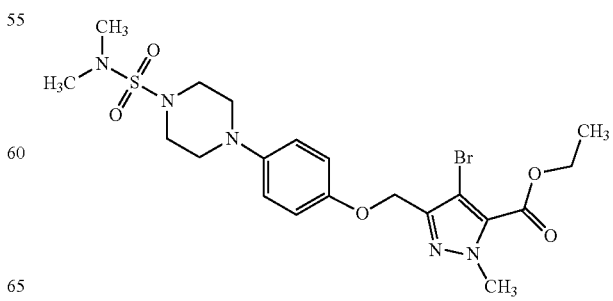

419

To a solution of ethyl 4-bromo-1-methyl-3-{[4-(piperazin-1-yl)phenoxy]methyl}-1H-pyrazole-5-carboxylate hydrochloric acid salt (see intermediate 27, 220 mg) in dichloromethane (9.0 mL) were added at 0° C. N,N-diisopropylethylamine (390 µL, 2.2 mmol) and dimethylsulfamyl chloride (57 µL, 530 µmol). The mixture was stirred at rt overnight. Dichloromethane, water and brine were added, the organic layer was washed with brine and dried over sodium sulfate. After filtration and removal of the solvents the residue was purified by flash chromatography (Biotage SNAP cartridge silica 25 g, EtOH:dichloromethane) to give the title compound (219 mg).

MS: m/z=530 [M+H]$^+$.

Intermediate 29

4-(4-{[4-Bromo-5-(hydroxymethyl)-1-methyl-1H-pyrazol-3-yl]methoxy}phenyl)-N,N-dimethylpiperazine-1-sulfonamide

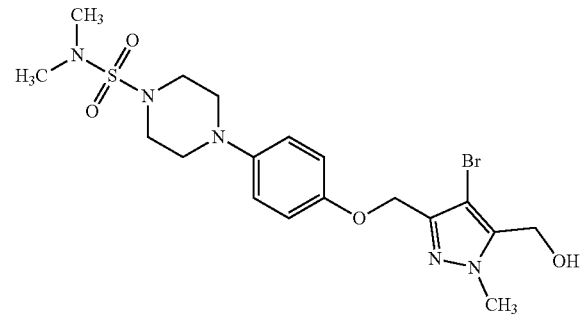 [SMILES: CN(C)S(=O)(=O)N1CCN(c2ccc(OCc3nn(C)c(CO)c3Br)cc2)CC1]

To a solution of ethyl 4-bromo-3-({4-[4-(dimethylsulfamoyl)piperazin-1-yl]phenoxy}methyl)-1-methyl-1H-pyrazole-5-carboxylate (see intermediate 28, 6.92 g, 13.0 mmol) in THF (110 mL) at 0° C. was added a solution of lithium aluminium hydride (6.5 mL, 2.0 M in THF, 13 mmol) and the mixture was stirred at 0° C. for 1 h. Ice was carefully added, water was added and the mixture was extracted with ethyl acetate. The organic layer was washed with brine and dried over sodium sulfate. Filtration and removal of the solvents the residue yielded the title compound (6.21 g, 97% yield) which was used without further purification.

MS: m/z=488 [M+H]$^+$.

420

Intermediate 30 ethyl 7-[3-({4-[4-(dimethylsulfamoyl)piperazin-1-yl]phenoxy}methyl)-5-(hydroxymethyl)-1-methyl-1H-pyrazol-4-yl]-3-[3-(naphthalen-1-yloxy)propyl]-1H-indole-2-carboxylate XPhos Pd G2 (see abbreviation list; 32.1 mg, 40.8 µmol) was added to a degassed mixture of ethyl 3-[3-(naphthalen-1-yloxy)propyl]-7-(4,4,5,5-tetramethyl-1,3,2-dioxaborolan-2-yl)-1H-indole-2-carboxylate (see Intermediate 5; 677 mg, 1.36 mmol), 4-(4-{[4-bromo-5-(hydroxymethyl)-1-methyl-1H-pyrazol-3-yl]methoxy}phenyl)-N,N-dimethylpiperazine-1-sulfonamide (602 mg, 1.23 mmol), aqueous potassium phosphate solution (4.9 ml, 0.50 M, 2.5 mmol) and THF (15 ml). The mixture was stirred for 2 h at 45° C. For work-up, ethyl acetate was added, the mixture was filtered through a pad of celite, eluted with ethyl acetate and the organic phase was washed with brine, filtered through a silicone filter and concentrated. The residue was purified by flash chromatography (dichloromethane/ethyl acetate gradient) to give the title compound (468 mg, 42% yield).

LC-MS (Method 2): R$_t$=1.55 min; MS (ESIpos): m/z=781 [M+H]$^+$ $^1$H-NMR (400 MHz, DMSO-d6) δ [ppm]: 1.066 (2.01), 1.156 (0.45), 1.172 (0.47), 1.242 (1.50), 1.259 (3.31), 1.277 (1.54), 1.987 (0.74), 2.074 (0.79), 2.221 (0.40), 2.322 (0.49), 2.326 (0.69), 2.331 (0.47), 2.518 (2.70), 2.522 (1.85), 2.664 (0.49), 2.668 (0.66), 2.673 (0.47), 2.782 (16.00), 2.797 (2.52), 2.987 (0.91), 3.000 (1.23), 3.012 (1.11), 3.235 (1.19), 3.248 (1.26), 3.259 (0.99), 3.857 (0.78), 3.956 (4.52), 4.188 (0.42), 4.203 (0.85), 4.221 (0.49), 4.240 (0.92), 4.258 (0.89), 6.787 (2.17), 6.796 (2.20), 6.889 (0.57), 6.906 (0.61), 6.913 (0.52), 6.916 (0.51), 7.047 (0.50), 7.221 (0.59), 7.237 (0.48), 7.364 (0.41), 7.384 (0.76), 7.403 (0.62), 7.443 (0.78), 7.464 (0.43), 7.490 (0.47), 7.494 (0.40), 7.505 (0.51), 7.511 (0.73), 7.514 (0.50), 7.525 (0.42), 7.529 (0.45), 7.682 (0.52), 7.702 (0.48), 7.854 (0.47), 7.873 (0.51), 8.202 (0.41), 8.206 (0.42).

Intermediate 31

3-(benzylamino)propan-1-ol

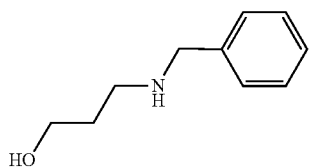 [SMILES: OCCCNCc1ccccc1]

To a solution of 3-amino-propan-1-ol (3.0 g, 39.9 mmol) in N,N-dimethylformamide (30 mL) was added caesium carbonate (26 g, 79.9 mmol) and the mixture was stirred at room temperature for 10 min. Benzyl bromide (3.4 g, 19.9 mmol) was then added portionwise and the mixture was stirred at 25° C. for 15 h, diluted with dichloromethane (200 mL), washed with water, dried over sodium sulfate, filtered and concentrated. The crude residue (3.5 g) was used directly in the next step without further purification.

MS: m/z=166 [M+H]$^+$

Intermediate 32 tert-butyl benzyl(3-hydroxypropyl)carbamate

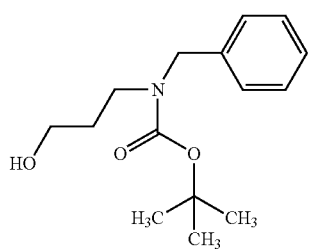 [SMILES: CC(C)(C)OC(=O)N(CCCO)Cc1ccccc1]

To a solution of 3-(benzylamino)propan-1-ol (3.5 g, 39.9 mmol) in tetrahydrofuran (35 mL) at 0° C. was added triethylamine (12.0 g, 120 mmol) and di-tert-butyl dicarbonate (8.7 g, 39.9 mmol). The mixture was stirred at 25° C. for 15 h and concentrated. The residue was partitioned between ethyl acetate (100 mL) and water (40 mL). The organic layer was separated, dried over sodium sulfate, filtered and concentrated. The residue was purified by flash chromatography (25% ethyl acetate/dichloromethane with 2% methanol) to give the title compound (2.0 g).

MS: m/z=288 [M+Na]$^+$ $^1$H NMR (300 MHz, CDCl$_3$) δ [ppm]: 7.36-7.21 (m, 5H), 4.39 (m, 2H), 3.80-3.70 (m, 1H), 3.60-3.50 (m, 2H), 3.42-3.32 (m, 2H), 1.47 (bs, 9H).

Intermediate 33 tert-butyl benzyl(3-bromopropyl)carbamate

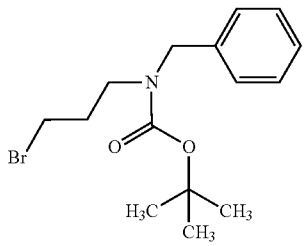 [SMILES: CC(C)(C)OC(=O)N(CCCBr)Cc1ccccc1]

To a solution of tert-butyl benzyl(3-hydroxypropyl)carbamate (1.0 g, 3.92 mmol) in dichloromethane (6 mL) at 0° C. was added triphenylphosphine (1.13 g, 4.31 mmol). The mixture was stirred at 0° C. for 20 min. Tetrabromomethane (1.43 g, 4.31 mmol) in dichloromethane (3 mL) was added, and the mixture was stirred at room temperature for 16 h and concentrated. The residue was purified by flash chromatography (20% ethyl acetate/hexanes) to give the title compound (1.0 g).

$^1$H NMR (300 MHz, CDCl$_3$) δ [ppm]: 7.36-7.21 (m, 5H), 4.50-4.43 (bs, 2H), 3.42-3.25 (m, 4H), 2.15-1.95 (m, 2H), 1.47 (bs, 9H).

Intermediate 34 ethyl 1-{3-[benzyl(tert-butoxycarbonyl)amino]propyl}-7-[3-({4-[4-(dimethylsulfamoyl)piperazin-1-yl]phenoxy}methyl)-5-(hydroxymethyl)-1-methyl-1H-pyrazol-4-yl]-3-[3-(1-naphthyloxy)propyl]-1H-indole-2-carboxylate

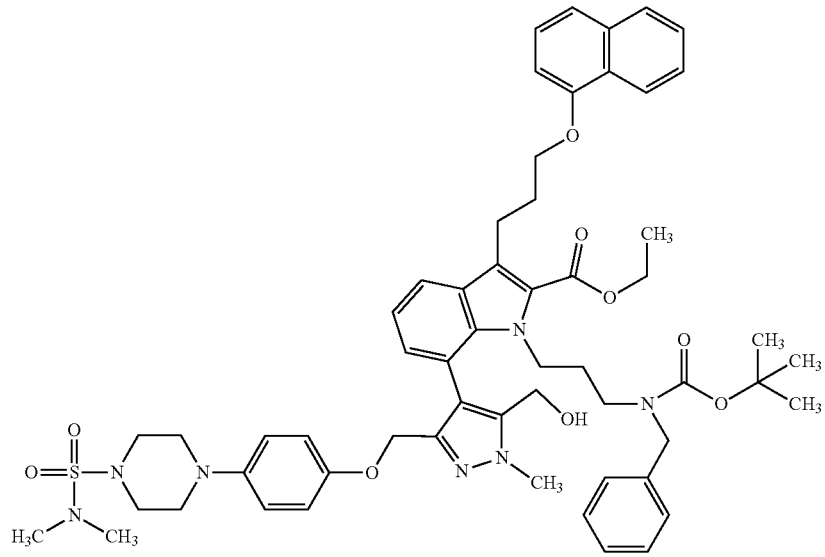 [SMILES: CCOC(=O)c1c(CCCOc2cccc3ccccc23)c2cccc(-c3c(COc4ccc(N5CCN(S(=O)(=O)N(C)C)CC5)cc4)nn(C)c3CO)c2n1CCCN(Cc1ccccc1)C(=O)OC(C)(C)C]

To a solution of ethyl 7-[3-({4-[4-(dimethylsulfamoyl)piperazin-1-yl]phenoxy}methyl)-5-(hydroxymethyl)-1-methyl-1H-pyrazol-4-yl]-3-[3-(naphthalen-1-yloxy)propyl]-1H-indole-2-carboxylate (see Intermediate 30, 0.22 g, 0.28 mmol) in N,N-dimethylformamide (3 mL) was added caesium carbonate (0.28 g, 0.85 mmol) and the mixture was stirred at room temperature for 10 min. tert-Butyl benzyl(3-bromopropyl)carbamate (0.11 g, 0.34 mmol) was added and the mixture was stirred at 25° C. for 18 h, diluted with ethyl acetate (35 mL), washed with water, dried over sodium sulfate, filtered and concentrated. The residue was purified by flash chromatography (1:2 ethyl acetate/dichloromethane with 1% methanol) to give the title compound (0.10 g).
MS: m/z=1028 [M+H]$^+$.

Intermediate 35 ethyl 1-{3-[benzyl(tert-butoxycarbonyl)amino]propyl}-7-[5-(bromomethyl)-3-({4-[4-(dimethylsulfamoyl)piperazin-1-yl]phenoxy}methyl)-1-methyl-1H-pyrazol-4-yl]-3-[3-(1-naphthyloxy)propyl]-1H-indole-2-carboxylate

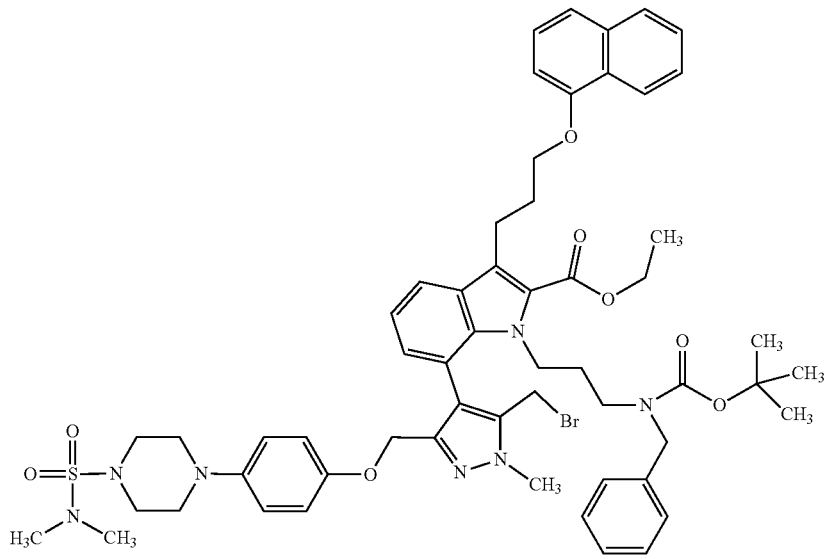 [SMILES: CCOC(=O)c1c(CCCOc2cccc3ccccc23)c2cccc(-c3c(COc4ccc(N5CCN(S(=O)(=O)N(C)C)CC5)cc4)nn(C)c3CBr)c2n1CCCN(Cc1ccccc1)C(=O)OC(C)(C)C]

To a solution of ethyl 1-{3-[benzyl(tert-butoxycarbonyl)amino]propyl}-7-[3-({4-[4-(dimethylsulfamoyl)piperazin-1-yl]phenoxy}methyl)-5-(hydroxymethyl)-1-methyl-1H-pyrazol-4-yl]-3-[3-(1-naphthyloxy)propyl]-1H-indole-2-carboxylate (see intermediate 34, 0.10 g, 0.10 mmol) in dichloromethane (2 mL) at 0° C. was added triphenylphosphine (63.0 mg, 0.24 mmol) and the mixture was stirred at 0° C. for 10 min before adding a solution of tetrabromomethane (0.5 mL, 0.22 mmol) in dichloromethane. The resulting mixture was stirred at room temperature for 18 h, concentrated and the crude title compound was used directly in the next step.

MS: m/z=1090 [M+H]$^+$

Intermediate 36 ethyl 1-[3-(benzylamino)propyl]-7-[5-(bromomethyl)-3-({4-[4-(dimethylsulfamoyl)piperazin-1-yl]phenoxy}methyl)-1-methyl-1H-pyrazol-4-yl]-3-[3-(1-naphthyloxy)propyl]-1H-indole-2-carboxylate hydrochloric acid salt

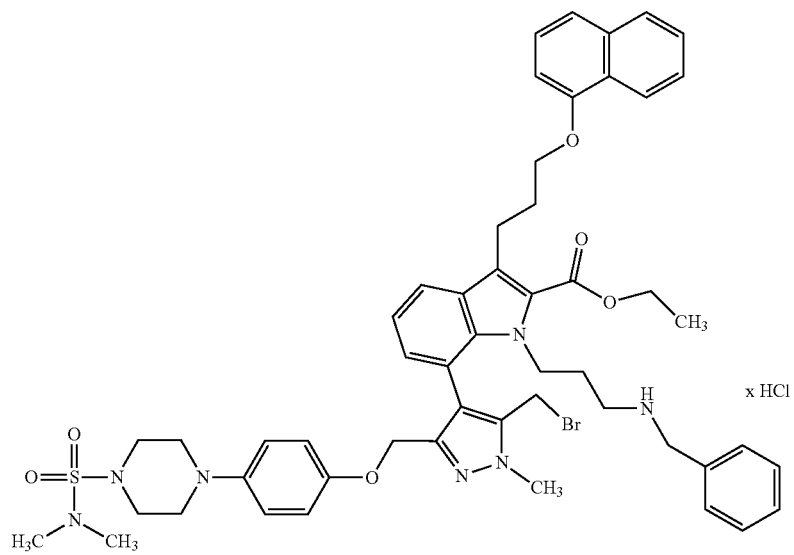 [SMILES: CCOC(=O)c1c(CCCOc2cccc3ccccc23)c2cccc(-c3c(COc4ccc(N5CCN(S(=O)(=O)N(C)C)CC5)cc4)nn(C)c3CBr)c2n1CCCNCc1ccccc1]

To a solution of crude ethyl 1-{3-[benzyl(tert-butoxycarbonyl)amino]propyl}-7-[5-(bromomethyl)-3-({4-[4-(dimethylsulfamoyl)piperazin-1-yl]phenoxy}methyl)-1-methyl-1H-pyrazol-4-yl]-3-[3-(1-naphthyloxy)propyl]-1H-indole-2-carboxylate (see intermediate 35, 0.10 mmol) in methanol (2 mL) was added HCl in dioxane (4 N, 2 mL) at 0° C. The mixture was stirred at room temperature for 2 h and concentrated to give the crude title compound which was used directly in the next step.

MS: m/z=990 [M+H]$^+$

Intermediate 37

(rac)-ethyl 7-benzyl-11-({4-[4-(dimethylsulfamoyl)piperazin-1-yl]phenoxy}methyl)-9-methyl-1-[3-(1-naphthyloxy)propyl]-4,5,6,7,8,9-hexahydropyrazolo[3',4':7,8][1,5]diazecino[9,10,1-hi]indole-2-carboxylate

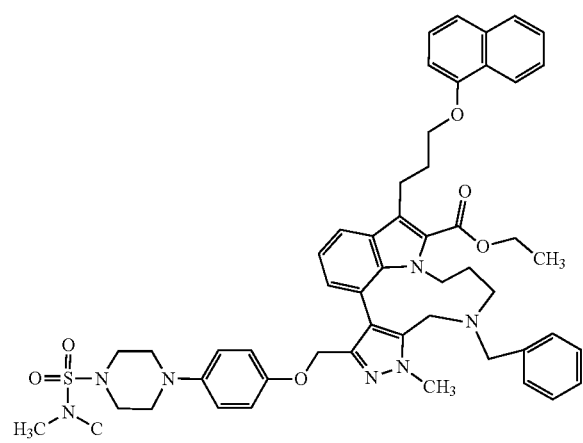

To a solution of crude ethyl 1-[3-(benzylamino)propyl]-7-[5-(bromomethyl)-3-({4-[4-(dimethylsulfamoyl)piperazin-1-yl]phenoxy}methyl)-1-methyl-1H-pyrazol-4-yl]-3-[3-(1-naphthyloxy)propyl]-1H-indole-2-carboxylate hydrochloric acid salt (see intermediate 36, 0.10 mmol) in N,N-dimethylformamide (11 mL) was added caesium carbonate (0.16 g, 0.50 mmol). The resulting mixture was stirred at room temperature for 16 h and concentrated under reduced pressure. The residue was then diluted with ethyl acetate (60 mL) and washed twice with water. The organic layer was separated, dried over sodium sulfate, filtered and concentrated. The residue was purified by flash chromatography (1:2 ethyl acetate/dichloromethane) to give the title compound (53 mg).

MS: m/z=910 [M+H]$^+$ $^1$H NMR (300 MHz, CDCl$_3$) δ [ppm]: 8.39-8.36 (m, 1H), 7.83-7.60 (m, 2H), 7.51-7.48 (m, 2H), 7.43-7.35 (m, 2H), 7.10-6.91 (m, 5H), 6.75-6.61 (m, 7H), 4.80 (s, 2H), 4.49-4.43 (m, 1H), 4.33-4.28 (m, 2H), 4.22-4.18 (m, 2H), 3.92-3.85 (m, 4H), 3.58-3.43 (d, 1H), 3.47-3.30 (m, 12H), 3.01-2.97 (m, 4H), 2.86 (s, 6H), 2.36-2.31 (m, 4H), 1.39-1.34 (t, 3H).

Intermediate 38 ethyl 3-(3-hydroxypropyl)-7-(4,4,5,5-tetramethyl-1,3,2-dioxaborolan-2-yl)-1H-indole-2-carboxylate

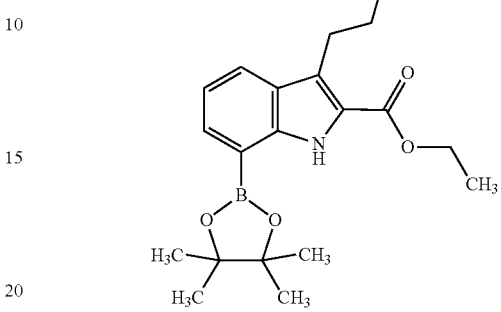

A solution of ethyl 7-bromo-3-(3-hydroxypropyl)-1H-indole-2-carboxylate (6.8 g, 20.8 mmol, prepared as described in Journal of Medicinal Chemistry, 2015, 58, 2180-2194) in dioxane (225 ml) was treated with 4,4,4',4',5,5,5',5'-octamethyl-2,2'-bi-1,3,2-dioxaborolane (8.00 g, 31.5 mmol), potassium acetate (4 g, 40.7 mmol), degassed and heated to 80° C. and treated with [1,1'-bis(diphenylphosphino)ferrocene]dichloropalladium(II) (750 mg, 0.92 mmol). The resulting mixture was stirred at that temperature for 4 h, cooled to room temperature, volatiles were removed under reduced pressure, the residue was suspended in a mixture of ethyl acetate and hexanes, filtered through a pad of silica gel, washed with a mixture of ethyl acetate and hexanes (1:1), and the filtrate was concentrated to give the title compound which was used without further manipulation.

MS (ESI): m/z=374 [M+H]$^+$

Intermediate 39 ethyl 3-(3-{[tert-butyl(dimethyl)silyl]oxy}propyl)-7-(4,4,5,5-tetramethyl-1,3,2-dioxaborolan-2-yl)-1H-indole-2-carboxylate

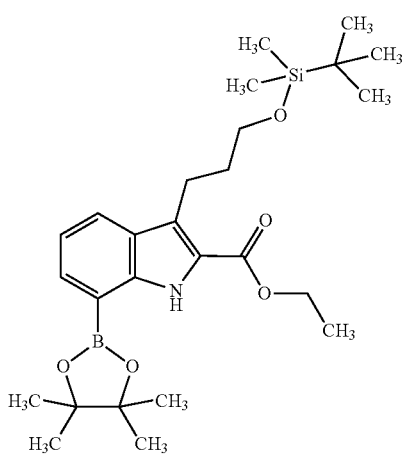 [SMILES: CCOC(=O)c1[nH]c2c(B3OC(C)(C)C(C)(C)O3)cccc2c1CCCO[Si](C)(C)C(C)(C)C]

A solution of crude ethyl 3-(3-hydroxypropyl)-7-(4,4,5,5-tetramethyl-1,3,2-dioxaborolan-2-yl)-1H-indole-2-carboxylate (see intermediate 28, 20.8 mmol) in dichloromethane (200 ml) was treated with imidazole (3 g, 44 mmol) and tert-butyldimethylsilyl chloride (5 g, 33 mmol), and stirred at room temperature for 16 hours. The resulting suspension was filtered through a pad of silica gel, diluted with hexanes, the organic phase was washed with water, saturated aqueous sodium bicarbonate solution, and saturated aqueous sodium chloride solution, the combined aqueous phases were extracted with a mixture of ethyl acetate and hexanes, the combined organic layers were dried over magnesium sulfate, solids were removed by filtration, volatiles were removed under reduced pressure, and the residue was purified by normal phase chromatography on silica gel (40 g) eluting with a gradient of ethyl acetate in hexanes (0-5%) to give the title compound as a solid (15 g).

MS (ESI): m/z=488 [M+H]$^+$

A solution of ethyl 3-(3-{[tert-butyl(dimethyl) silyl]oxy}propyl)-7-(4,4,5,5-tetramethyl-1,3,2-dioxaborolan-2-yl)-1H-indole-2-carboxylate (see intermediate 39, 3.2 g, 4.9 mmol) and (4-bromo-1,3-dimethyl-1H-pyrazol-5-yl) methanol (see Intermediate 8, 1 g, 4.9 mmol) in tetrahydrofuran (60 ml), and aqueous potassium phosphate (0.5 M, 20 ml) was degassed, treated with Palladium XPhos G2 precatalyst (see abbreviation list, 188 mg, 0.24 mmol), degassed, and heated to 45° C. for 16 hours, cooled to room temperature, volatiles removed under reduced pressure, and the residue was purified by normal phase chromatography on silica gel (40 g), eluting with a gradient of ethyl acetate in hexanes (0-100%) to give the title compound as a colorless oil (576 mg).

MS (ESI): m/z=486 [M+H]$^+$

H NMR (400 MHz, Chloroform-d) δ [ppm]: 9.20 (s, 1H), 7.71 (dd, J=7.9, 1.2 Hz, 1H), 7.19 (t, J=7.5 Hz, 1H), 7.14 (dd, J=7.1, 1.3 Hz, 1H), 4.57 (s, 2H), 4.38 (q, J=7.1 Hz, 2H), 4.02 (d, J=4.2 Hz, 3H), 3.72 (t, J=6.4 Hz, 2H), 3.21-3.12 (m, 2H), 2.22 (s, 3H), 1.98-1.86 (m, 2H), 1.39 (t, J=7.1 Hz, 3H), 0.93 (s, 9H), 0.07 (s, 6H).

Intermediate 41 ethyl 3-(3-{[tert-butyl(dimethyl)silyl]oxy}propyl)-7-[5-(hydroxymethyl)-1,3-dimethyl-1H-pyrazol-4-yl]-1-(3-bromopropyl)-1H-indole-2-carboxylate Intermediate 40 ethyl 3-(3-{[tert-butyl(dimethyl)silyl]oxy}propyl)-7-[5-(hydroxymethyl)-1,3-dimethyl-1H-pyrazol-4-yl]-1H-indole-2-carboxylate

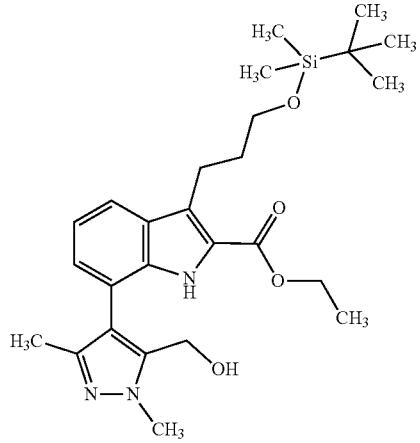 [SMILES: CCOC(=O)c1[nH]c2c(-c3c(C)nn(C)c3CO)cccc2c1CCCO[Si](C)(C)C(C)(C)C]

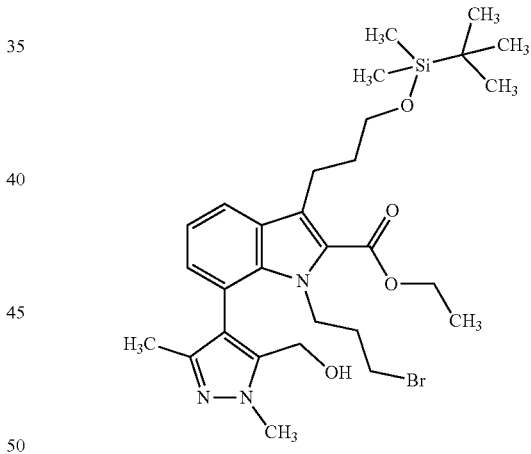

To a solution of ethyl 3-(3-{[tert-butyl(dimethyl)silyl]oxy}propyl)-7-[5-(hydroxymethyl)-1,3-dimethyl-1H-pyrazol-4-yl]-1H-indole-2-carboxylate (2 g, 4.1 mmol) in acetonitrile (20 ml) was added 1,3-dibromopropane (1 ml, 9.8 mmol) and caesium carbonate (2 g, 6.13 mmol) and the resulting mixture was stirred at room temperature for 2 hours, warmed to 40° C. for 2 hours, then stirred at room temperature for 16 hours. The reaction mixture was then diluted with ethyl acetate, filtered through a pad of silica gel, volatiles were removed under reduced pressure, and the residue was purified by normal phase chromatography on silica gel eluting with a gradient of ethyl acetate in hexanes (10-50%) to give the title compound as a colorless oil (870 mg).

MS (ESIpos): m/z=606 [M+H]$^+$

431

Intermediate 42

(rac)-ethyl 1-(3-{[tert-butyl(dimethyl)silyl]oxy}propyl)-9,11-dimethyl-5,6,8,9-tetrahydro-4H-pyrazolo[4',3':8,9][1,5]oxazecino[7,6,5-hi]indole-2-carboxylate

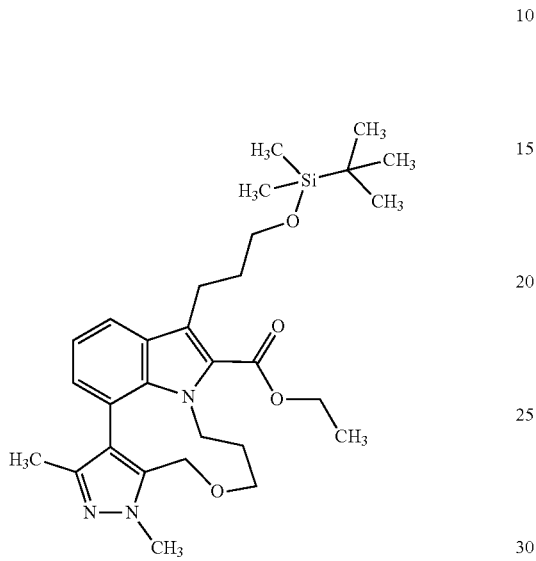

A solution of ethyl 3-(3-{[tert-butyl(dimethyl)silyl]oxy}propyl)-7-[5-(hydroxymethyl)-1,3-dimethyl-1H-pyrazol-4-yl]-1-(3-bromopropyl)-1H-indole-2-carboxylate (1.6 g, 2.4 mmol) in dimethyl formamide (20 ml) in an ice water bath was treated with sodium hydride (100 mg, 60% in oil, 2.5 mmol), after 20 minutes, the reaction was diluted with acetic acid (2 ml), followed by ethyl acetate, hexanes, and water, and the layers were separated. The organic phase was successively washed with water, saturated aqueous ammonium chloride solution, and saturated aqueous sodium chloride solution, dried over magnesium sulfate, solids were removed by filtration, volatiles were removed under reduced pressure and the residue was purified by normal phase chromatography on silica gel (40 g) eluted with a gradient of ethyl acetate in hexanes (0-50%) to give the title compound with other materials as a pale yellow oil (752 mg).

$^1$H NMR (400 MHz, Chloroform-d) δ [ppm]: 7.73 (dd, J=8.0, 1.3 Hz, 1H), 7.12 (dd, J=8.1, 7.0 Hz, 1H), 7.00 (dd, J=7.1, 1.3 Hz, 1H), 4.73 (d, J=14.3 Hz, 1H), 4.59 (dt, J=14.7, 3.9 Hz, 1H), 4.46-4.30 (m, 2H), 3.99 (ddd, J=14.9, 12.3, 2.9 Hz, 1H), 3.92 (s, 3H), 3.88 (dd, J=13.4, 9.6 Hz, 1H), 3.82 (d, J=14.3 Hz, 1H), 3.71 (td, J=6.4, 2.3 Hz, 2H), 3.25-3.01 (m, 2H), 2.77-2.66 (m, 1H), 2.06 (s, 3H), 1.93-1.83 (m, 2H), 1.82-1.58 (m, 2H), 1.41 (t, J=7.1 Hz, 3H), 0.93 (s, 9H), 0.07 (s, 6H).

MS (ESI): m/z=526 [M+H]$^+$

432

Intermediate 43

(rac)-ethyl 1-(3-hydroxypropyl)-9,11-dimethyl-5,6,8,9-tetrahydro-4H-pyrazolo[4',3':8,9][1,5]oxazecino[7,6,5-hi]indole-2-carboxylate

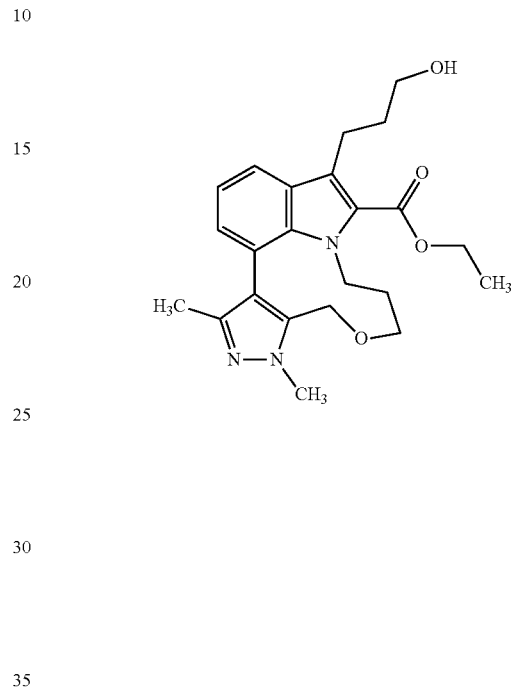

To a solution of (rac)-ethyl 1-(3-{[tert-butyl(dimethyl)silyl]oxy}propyl)-9,11-dimethyl-5,6,8,9-tetrahydro-4H-pyrazolo[4',3':8,9][1,5]oxazecino[7,6,5-hi]indole-2-carboxylate (752 mg, 1.43 mmol) in ethanol (50 ml) and acetic acid (3 ml) was added potassium fluoride (235 mg, 4 mmol) and the suspension was stirred at room temperature for 1 hour and then heated to 60° C. for 21 hours. The reaction mixture was cooled to room temperature, volatiles were removed under reduced pressure, the residue was then purified by normal phase chromatography on silica gel (24 g), eluting with a gradient of ethyl acetate in hexanes (0-100%) to give the title compound as a colorless oil (100 mg).

$^1$H NMR (400 MHz, Chloroform-d) δ [ppm]: 7.70 (dd, J=8.1, 1.3 Hz, 1H), 7.12 (dd, J=8.1, 7.0 Hz, 1H), 7.01 (dd, J=7.1, 1.3 Hz, 1H), 4.73 (d, J=14.3 Hz, 1H), 4.55 (dt, J=14.9, 4.0 Hz, 1H), 4.47-4.28 (m, 2H), 4.01 (ddd, J=14.9, 11.5, 3.5 Hz, 1H), 3.92 (s, 3H), 3.90-3.84 (m, 1H), 3.81 (d, J=14.3 Hz, 1H), 3.61 (dp, J=10.8, 5.3 Hz, 2H), 3.28-3.08 (m, 2H), 2.69 (ddd, J=12.6, 10.4, 1.9 Hz, 1H), 2.07 (s, 3H), 2.02-1.89 (m, 3H), 1.79-1.58 (m, 2H), 1.39 (t, J=7.1 Hz, 3H).

MS (ESI): m/z=412 [M+H]$^+$

433

Intermediate 44

(rac)-ethyl 9,11-dimethyl-1-[3-(5,6,7,8-tetrahydronaphthalen-1-yloxy)propyl]-5,6,8,9-tetrahydro-4H-pyrazolo[4',3':8,9][1,5]oxazecino[7,6,5-hi]indole-2-carboxylate To a solution of (rac)-ethyl 1-(3-hydroxypropyl)-9,11-dimethyl-5,6,8,9-tetrahydro-4H-pyrazolo[4',3':8,9][1,5]oxazecino[7,6,5-hi]indole-2-carboxylate (see intermediate 43, 105 mg, 0.25 mmol) and 5,6,7,8-tetrahydronaphthalen-1-ol (62 mg, 0.42 mmol) in tetrahydrofuran (4 ml) cooled to 0° C. using an ice water bath was added a solution of triphenylphosphine (133 mg, 0.38 mmol) and diisopropyl azodicarboxylate (80 mg, 0.38 mmol) in tetrahydrofuran (5 ml) which had been stirred in an ice water bath for ten minutes. The reaction mixture was allowed to warm to room temperature over 16 hours, volatiles were removed under reduced pressure, and the residue was purified by normal phase chromatography on silica gel (4 g) eluting with a gradient of ethyl acetate in hexanes (10-60%) to give the title compound as a colorless solid (35 mg).

MS (ESI): m/z=542 [M+H]$^+$

434

Intermediate 45

(rac)-ethyl 1-[3-(4-chloro-3,5-dimethylphenoxy)propyl]-9,11-dimethyl-5,6,8,9-tetrahydro-4H-pyrazolo[4',3':8,9][1,5]oxazecino[7,6,5-hi]indole-2-carboxylate To a solution of (rac)-ethyl 1-(3-hydroxypropyl)-9,11-dimethyl-5,6,8,9-tetrahydro-4H-pyrazolo[4',3':8,9][1,5]oxazecino[7,6,5-hi]indole-2-carboxylate (see Intermediate 43, 180 mg, 0.44 mmol) and 4-chloro-3,5-dimethylphenol (181 mg, 1.15 mmol) and triphenylphosphine (250 mg, 0.95 mmol) in tetrahydrofuran (20 ml) cooled to 0° C. using an ice water bath was added diisopropyl azodicarboxylate (142 mg, 0.71 mmol). The reaction mixture was allowed to warm to room temperature over 16 hours, volatiles were removed under reduced pressure, and the residue was purified by normal phase chromatography on silica gel (12 g) eluting with a gradient of ethyl acetate in hexanes (0-50%) to give the title compound together with unidentified impurities as a colorless solid (200 mg).

MS (ESI): m/z=550 [M+H]$^+$

Intermediate 46

(rac)-ethyl 1-{3-[(6-fluoro-1-naphthyl)oxy]propyl}-9,11-dimethyl-5,6,8,9-tetrahydro-4H-pyrazolo[4',3':8,9][1,5]oxazecino[7,6,5-hi]indole-2-carboxylate

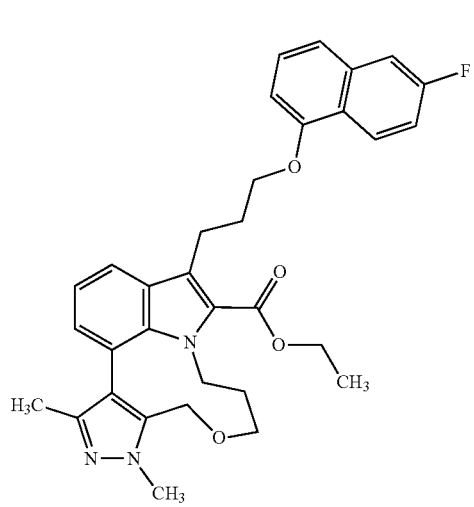 [SMILES: CCOC(=O)c1c(CCCOc2cccc3cc(F)ccc23)c2cccc3c2n1CCCOCc1c-3c(C)nn1C]

To a solution of (rac)-ethyl 1-(3-hydroxypropyl)-9,11-dimethyl-5,6,8,9-tetrahydro-4H-pyrazolo[4',3':8,9][1,5]oxazecino[7,6,5-hi]indole-2-carboxylate (see Intermediate 43, 75 mg, 0.18 mmol) and 6-fluoronaphthalen-1-ol (65 mg, 0.36 mmol) in tetrahydrofuran (4 ml) cooled to 0° C. using an ice water bath was added a solution of triphenylphosphine (96 mg, 0.36 mmol) and diisopropyl azodicarboxylate (55 mg, 0.27 mmol) in tetrahydrofuran (2 ml) which had been stirred in an ice water bath for ten minutes. The reaction mixture was allowed to warm to room temperature over 16 hours, volatiles were removed under reduced pressure, and the residue was purified by normal phase chromatography on silica gel (12 g) eluting with a gradient of ethyl acetate in hexanes (25-75%) to give the title compound as a colorless solid (48 mg).

MS (ESI): m/z=556 [M+H]$^+$

Intermediate 47 ethyl 1-allyl-3-(3-{[tert-butyl(dimethyl)silyl]oxy}propyl)-7-[5-(hydroxymethyl)-1,3-dimethyl-1H-pyrazol-4-yl]-1H-indole-2-carboxylate

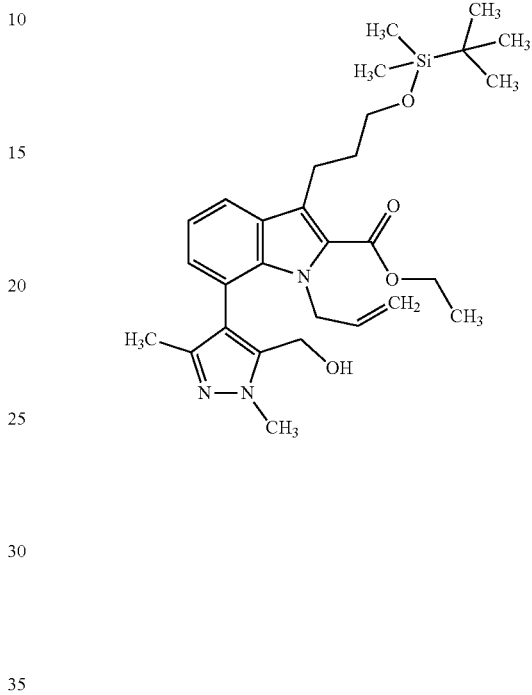

To a solution of ethyl 3-(3-{[tert-butyl(dimethyl)silyl]oxy}propyl)-7-[5-(hydroxymethyl)-1,3-dimethyl-1H-pyrazol-4-yl]-1H-indole-2-carboxylate (see Intermediate 40, 5.3 g, 10.9 mmol) in acetonitrile (20 ml) and allyl bromide (1.39 g, 11.4) was added caesium carbonate (3.8 g, 11.6 mmol) and the mixture was heated to 25° C. for 16 hours. The reaction mixture was diluted with ethyl acetate, solids were removed by filtration, the filtrate was concentrated under reduced pressure, and the residue was purified by normal phase chromatography on silica gel (120 g) eluting with a gradient of ethyl acetate in hexanes (0-50%) to provide the title compound as an oil (4.35 g).

$^1$H NMR (400 MHz, Chloroform-d) δ [ppm]: 7.73 (dd, J=8.1, 1.3 Hz, 1H), 7.14 (dd, J=8.0, 7.1 Hz, 1H), 6.96 (dd, J=7.1, 1.2 Hz, 1H), 5.56 (ddt, J=17.2, 10.4, 4.2 Hz, 1H), 5.08 (ddt, J=17.7, 4.1, 2.0 Hz, 1H), 4.78 (dt, J=10.6, 1.6 Hz, 1H), 4.67 (ddt, J=17.5, 4.2, 1.9 Hz, 1H), 4.49-4.29 (m, 5H), 4.14 (dt, J=17.1, 1.6 Hz, 1H), 3.96 (s, 3H), 3.71 (t, J=6.4 Hz, 2H), 3.19-3.06 (m, 2H), 2.14 (p, J=5.8 Hz, 1H), 1.97-1.83 (m, 3H), 1.39 (t, J=7.1 Hz, 3H), 0.93 (d, J=5.7 Hz, 1H), 0.93 (s, 9H), 0.07 (s, 6H).

MS (ESI): m/z=526 [M+H]$^+$

Intermediate 48 ethyl 1-allyl-7-{5-[(allyloxy)methyl]-1,3-dimethyl-1H-pyrazol-4-yl}-3-(3-{[tert-butyl(dimethyl)silyl]oxy}propyl)-1H-indole-2-carboxylate

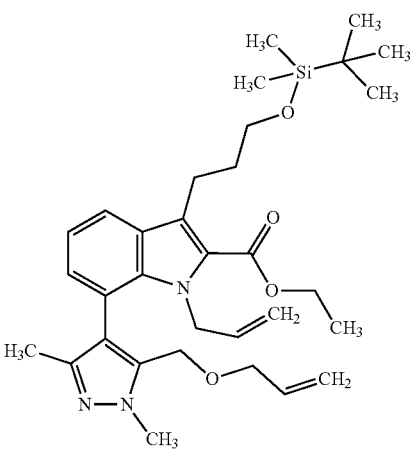 [SMILES: C=CCOCc1c(-c2cccc3c(CCCO[Si](C)(C)C(C)(C)C)c(C(=O)OCC)n(CC=C)c23)c(C)nn1C]

To a solution of ethyl 1-allyl-3-(3-{[tert-butyl(dimethyl)silyl]oxy}propyl)-7-[5-(hydroxymethyl)-1,3-dimethyl-1H-pyrazol-4-yl]-1H-indole-2-carboxylate (see intermediate 47, 5.0 g, 9.5 mmol) in dimethyl formamide (40 ml) cooled to 0° C. using an ice water bath was added allyl bromide (2.8 g, 23 mmol) and sodium hydride (60% in oil, 450 mg, 11.7 mmol). After stirring for 1 hour at that temperature, the reaction mixture was treated with acetic acid (2 ml), ethyl acetate, and water, layers were separated and the organic phase was washed successively with saturated aqueous ammonium chloride solution, saturated aqueous sodium chloride solution, the combined aqueous phases were extracted with ethyl acetate, the combined organic layers were dried over magnesium sulfate, insoluble materials were removed by filtration, the filtrate was concentrated under reduced pressure and the residue was purified by normal phase chromatography on silica gel (120 g) eluting with a gradient of ethyl acetate in hexanes (10-50%) to give the title compound as a pale amber oil (2.7 g).

$^1$H NMR (400 MHz, DMSO-d$_6$) δ [ppm]: 7.72 (dd, J=8.0, 1.2 Hz, 1H), 7.16 (dd, J=8.0, 7.1 Hz, 1H), 6.98 (dd, J=7.1, 1.2 Hz, 1H), 5.74 (ddt, J=17.4, 10.6, 5.4 Hz, 1H), 5.43 (ddt, J=17.2, 9.9, 4.7 Hz, 1H), 5.10-4.96 (m, 2H), 4.84 (ddt, J=17.0, 4.6, 1.8 Hz, 1H), 4.73 (dt, J=11.0, 1.9 Hz, 1H), 4.70-4.63 (m, 1H), 4.34-4.24 (m, 3H), 4.17-4.08 (m, 2H), 3.89-3.76 (m, 5H), 3.64 (t, J=6.5 Hz, 2H), 3.12-2.96 (m, 2H), 1.91 (s, 3H), 1.80 (dq, J=8.6, 6.6 Hz, 2H), 1.32 (t, J=7.1 Hz, 3H), 0.87 (s, 9H), 0.02 (s, 6H).

MS (ESI): m/z=566 [M+H]$^+$

Intermediate 49

(rac)-ethyl (E/Z)-7-(3-{[tert-butyl(dimethyl)silyl]oxy}propyl)-1,3-dimethyl-1,10,13,15-tetrahydropyrazolo[4',3':9,10][1,6]oxazacycloundecino[8,7,6-hi]indole-8-carboxylate

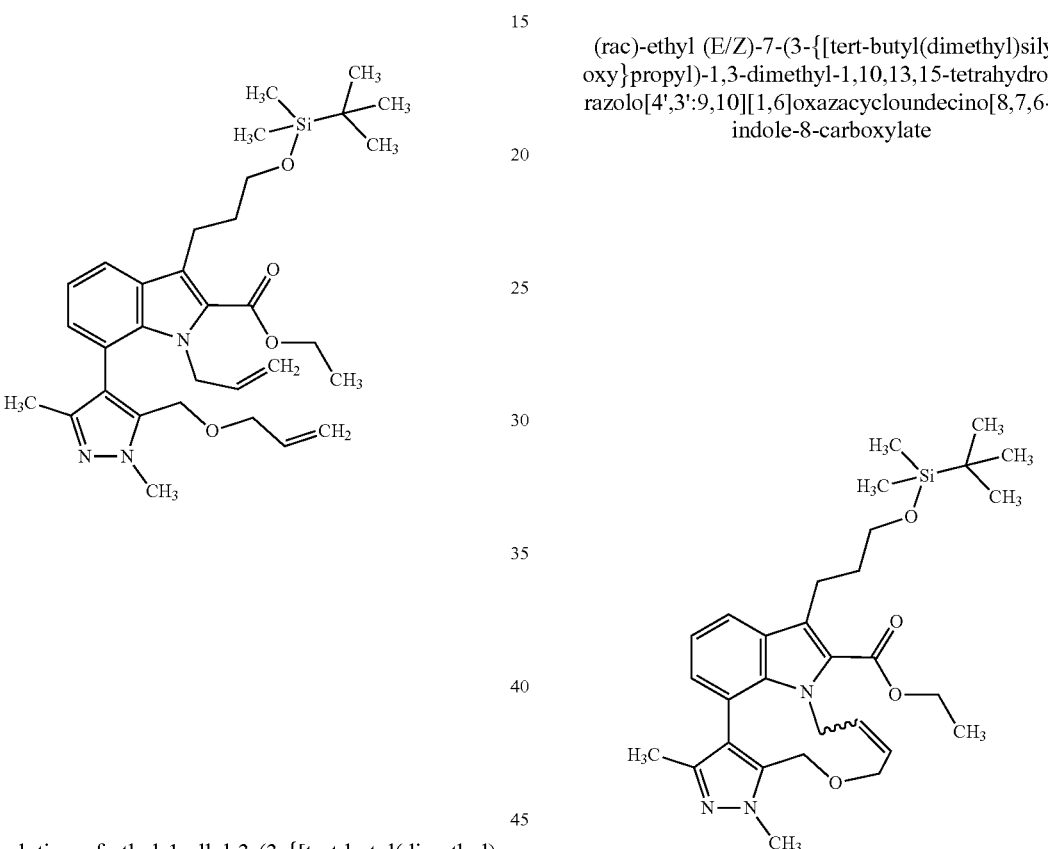

To a solution of ethyl 1-allyl-7-{5-[(allyloxy)methyl]-1,3-dimethyl-1H-pyrazol-4-yl}-3-(3-{[tert-butyl(dimethyl)silyl]oxy}propyl)-1H-indole-2-carboxylate (see intermediate 48, 2.7 g, 4.8 mmol) and (1,3-bis(2,4,6-trimethylphenyl)-2-imidazolidinylidene) dichloro (phenylmethylene) (tricyclohexylphosphine)ruthenium (Grubbs 2$^{nd}$ Generation catalyst, 205 mg, 0.24 mmol) in dichloromethane (100 ml) was stirred at room temperature for 16 hours, volatiles were removed and the residue was purified by normal phase chromatography on silica gel (24 g) eluting with a gradient of ethyl acetate in hexanes (20-40%) to obtain the title compound as a pale yellow gum (1.36 g).

MS (ESI): m/z=538 [M+H]$^+$

Intermediate 50 and Intermediate 51

(rac)-ethyl 7-(3-{[tert-butyl(dimethyl)silyl]oxy}propyl)-1,3-dimethyl-1,10,11,12,13,15-hexahydropyrazolo[4',3':9,10][1,6]oxazacycloundecino[8,7,6-hi]indole-8-carboxylate (Intermediate 50) and (rac)-ethyl 7-(3-hydroxypropyl)-1,3-dimethyl-1,10,11,12,13,15-hexahydropyrazolo[4',3':9,10][1,6]oxazacycloundecino[8,7,6-hi]indole-8-carboxylate (Intermediate 51)

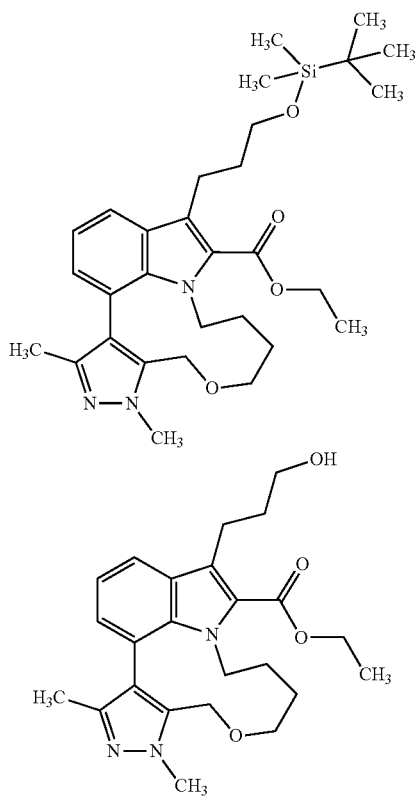

To a degassed solution of (rac)-ethyl (E/Z)-7-(3-{[tert-butyl(dimethyl)silyl]oxy}propyl)-1,3-dimethyl-1,10,13,15-tetrahydropyrazolo[4',3':9,10][1,6]oxazacycloundecino[8,7,6-hi]indole-8-carboxylate (1.36 g, 2.5 mmol) in ethanol (30 ml) was added palladium black (10% on carbon, 250 mg, 0.23 mmol), the suspension was degassed and then placed under one atmosphere of hydrogen for 16 hours, the suspension was degassed, and then filtered through a pad of celite, volatiles were removed under reduced pressure and the residue was purified by normal phase chromatography on silica gel (24 g) eluting with a gradient of ethyl acetate in hexanes (10-100%) to give the title compounds (rac)-ethyl 7-(3-{[tert-butyl(dimethyl)silyl]oxy}propyl)-1,3-dimethyl-1,10,11,12,13,15-hexahydropyrazolo[4',3':9,10][1,6]oxazacycloundecino[8,7,6-hi]indole-8-carboxylate (320 mg) and (rac)-ethyl 7-(3-hydroxypropyl)-1,3-dimethyl-1,10,11,12,13,15-hexahydropyrazolo[4',3':9,10][1,6]oxazacycloundecino[8,7,6-hi]indole-8-carboxylate (550 mg) as colorless gums.

Intermediate 50

$^1$H NMR (400 MHz, Chloroform-d) δ [ppm]: 7.76 (dd, J=8.1, 1.3 Hz, 1H), 7.12 (dd, J=8.1, 7.1 Hz, 1H), 6.87 (dd, J=7.1, 1.2 Hz, 1H), 4.66 (dt, J=14.3, 4.0 Hz, 1H), 4.59 (d, J=13.4 Hz, 1H), 4.47 (d, J=13.5 Hz, 1H), 4.45-4.30 (m, 2H), 4.12 (q, J=7.1 Hz, 1H), 4.07 (s, 3H), 4.02 (dd, J=14.4, 3.5 Hz, 0H), 3.70 (t, J=6.4 Hz, 2H), 3.59-3.45 (m, 1H), 3.20 (dt, J=13.2, 7.7 Hz, 1H), 3.09 (dt, J=13.3, 7.7 Hz, 1H), 3.01-2.87 (m, 1H), 2.05 (d, J=8.7 Hz, 4H), 1.89 (p, J=7.0 Hz, 2H), 1.68 (d, J=35.4 Hz, 1H), 1.51 (dd, J=12.2, 6.7 Hz, 1H), 1.42 (t, J=7.1 Hz, 3H), 1.32-1.22 (m, 3H), 1.15 (tt, J=16.2, 9.1 Hz, 2H), 0.93 (s, 11H), 0.07 (s, 7H).

LRMS(ESI) M+H+ 540.

Intermediate 51

(rac)-ethyl 7-(3-hydroxypropyl)-1,3-dimethyl-1,10,11,12,13,15-hexahydropyrazolo[4',3':9,10][1,6]oxazacycloundecino[8,7,6-hi]indole-8-carboxylate

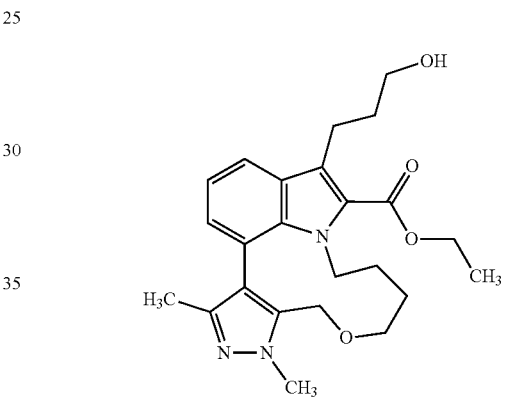

To a solution of (rac)-ethyl 7-(3-{[tert-butyl(dimethyl)silyl]oxy}propyl)-1,3-dimethyl-1,10,11,12,13,15-hexahydropyrazolo[4',3':9,10][1,6]oxazacycloundecino[8,7,6-hi]indole-8-carboxylate (see Intermediate 50, 320 mg, 0.6 mmol) in ethanol (40 ml) and acetic acid (2 ml) was added potassium fluoride (750 mg, 12.9 mmol), and the mixture was heated to 50° C. for 60 hours. Volatiles were removed under reduced pressure, and the residue was purified by normal phase chromatography on silica gel (12 g) eluting with a gradient of ethyl acetate in hexanes (0-100%) to give the title compound as a colorless solid (228 mg).

$^1$H NMR (400 MHz, Chloroform-d) δ [ppm]: 7.71 (dd, J=8.1, 1.3 Hz, 1H), 7.12 (dd, J=8.0, 7.1 Hz, 1H), 6.90 (dd, J=7.1, 1.2 Hz, 1H), 4.62-4.52 (m, 2H), 4.51-4.39 (m, 2H), 4.35 (dt, J=10.9, 7.1 Hz, 1H), 4.22-4.15 (m, 1H), 4.12 (q, J=7.2 Hz, 1H), 3.98 (s, 3H), 3.70-3.56 (m, 2H), 3.55-3.44 (m, 1H), 3.22 (t, J=7.1 Hz, 2H), 2.94 (ddd, J=12.1, 8.2, 5.5 Hz, 1H), 2.08-1.90 (m, 7H), 1.83-1.45 (m, 9H), 1.41 (t, J=7.1 Hz, 3H), 1.26 (t, J=7.2 Hz, 2H), 1.14 (tt, J=14.2, 7.2 Hz, 2H).

MS (ESI): m/z=426 [M+H]$^+$

441

Intermediate 53

(rac)-ethyl 1,3-dimethyl-7-[3-(5,6,7,8-tetrahydronaphthalen-1-yloxy)propyl]-1,10,11,12,13,15-hexahydropyrazolo[4',3':9,10][1,6]oxazacycloundecino[8,7,6-hi]indole-8-carboxylate

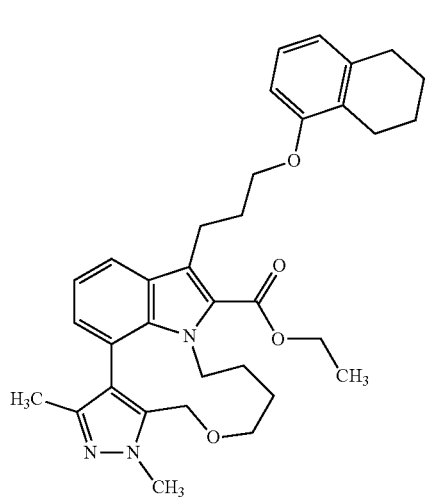 [SMILES: CCOC(=O)c1c(CCCOc2cccc3c2CCCC3)c2cccc3c2n1CCCCOCc1c-3c(C)nn1C]

A solution of triphenylphosphine (204 mg, 0.78 mmol) in tetrahydrofuran (5 ml) cooled to 0° C. using an ice water bath was treated with di-isopropylazodicarboxylate (120 mg, 0.59 mmol), after ten minutes this was added to a solution of (rac)-ethyl 7-(3-hydroxypropyl)-1,3-dimethyl-1,10,11,12,13,15-hexahydropyrazolo[4',3':9,10][1,6]oxazacycloundecino[8,7,6-hi]indole-8-carboxylate (see intermediate 51, 165 mg, 0.39 mmol) and 5,6,7,8-tetrahydronapth-1-ol (170 mg, 1.14 mmol) in tetrahydrofuran (10 ml) cooled to 0° C. using an ice water bath. The mixture was then allowed to warm to room temperature over 16 hours, volatiles were removed under reduced pressure and the residue was purified by normal phase chromatography on silica gel (12 g) eluting with a gradient of ethyl acetate in hexanes (0-100%) to give the title compound as a colorless oil (160 mg).

MS (ESI): m/z=556 [M+H]$^+$

442

Intermediate 54

(rac)-ethyl 7-[3-(4-chloro-3,5-dimethylphenoxy)propyl]-1,3-dimethyl-1,10,11,12,13,15-hexahydropyrazolo[4',3':9,10][1,6]oxazacycloundecino[8,7,6-hi]indole-8-carboxylate

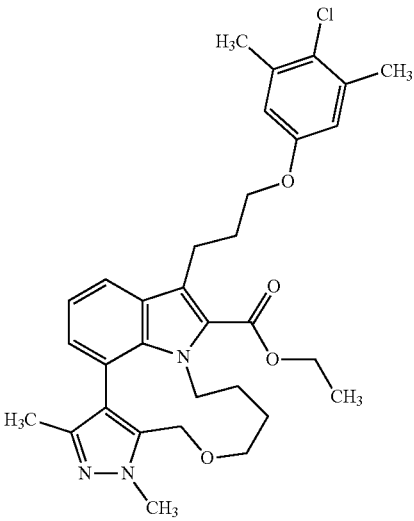

A solution of triphenylphosphine (204 mg, 0.78 mmol) in tetrahydrofuran (5 ml) cooled to 0° C. using an ice water bath was treated with di-isopropylazodicarboxylate (120 mg, 0.59 mmol), after ten minutes this was added to a solution of (rac)-ethyl 7-(3-hydroxypropyl)-1,3-dimethyl-1,10,11,12,13,15-hexahydropyrazolo[4',3':9,10][1,6]oxazacycloundecino[8,7,6-hi]indole-8-carboxylate (see Intermediate 51, 165 mg, 0.39 mmol) and 4-chloro-3,5-dimethyl phenol (180 mg, 1.14 mmol) in tetrahydrofuran (4 ml) cooled to 0° C. using an ice water bath. The mixture was then allowed to warm to room temperature over 16 hours, volatiles were removed under reduced pressure and the residue was purified by normal phase chromatography on silica gel (12 g) eluting with a gradient of ethyl acetate in hexanes (10-80%) to give the title compound as a colorless oil (190 mg).

MS (ESI): m/z=564 [M+H]$^+$

443

Intermediate 55

(rac)-ethyl 1,3-dimethyl-7-{3-[(7-methyl-1-naphthyl)oxy]propyl}-1,10,11,12,13,15-hexahydropyrazolo[4',3':9,10][1,6]oxazacycloundecino[8,7,6-hi]indole-8-carboxylate

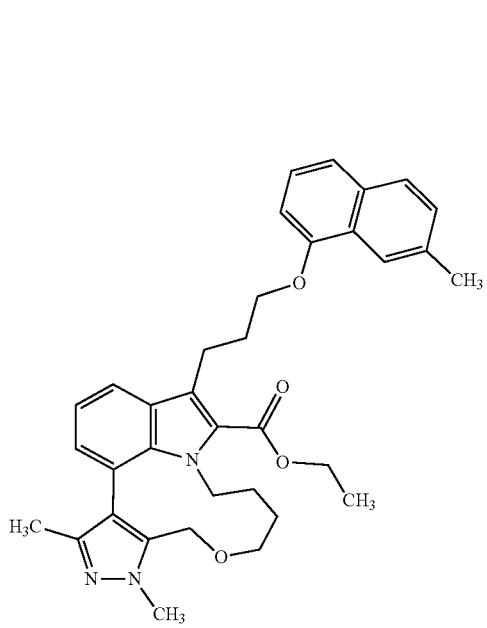

A solution of triphenylphosphine (150 mg, 0.57 mmol) in tetrahydrofuran (10 ml) cooled to 0° C. using an ice water bath was treated with di-tertbutylazodicarboxylate (103 mg, 0.45 mmol), after ten minutes this was added to a solution of (rac)-ethyl 7-(3-hydroxypropyl)-1,3-dimethyl-1,10,11,12,13,15-hexahydropyrazolo[4',3':9,10][1,6]oxazacycloundecino[8,7,6-hi]indole-8-carboxylate (see Intermediate 51,165 mg, 0.39 mmol) and 7-methyl-naphthalen-1-ol (180 mg, 1.14 mmol) in tetrahydrofuran (5 ml) cooled to 0° C. using an ice water bath. The mixture was then allowed to warm to room temperature over 16 hours, volatiles were removed under reduced pressure and the residue was purified by normal phase chromatography on silica gel (12 g) eluting with a gradient of ethyl acetate in hexanes (10-80%) to give the title compound as a colorless oil (85 mg).

MS (ESI): m/z=566 [M+H]$^+$

444

Intermediate 56

(rac)-ethyl 1,3-dimethyl-7-(3-phenoxypropyl)-1,10,11,12,13,15-hexahydropyrazolo[4',3':9,10][1,6]oxazacycloundecino[8,7,6-hi]indole-8-carboxylate

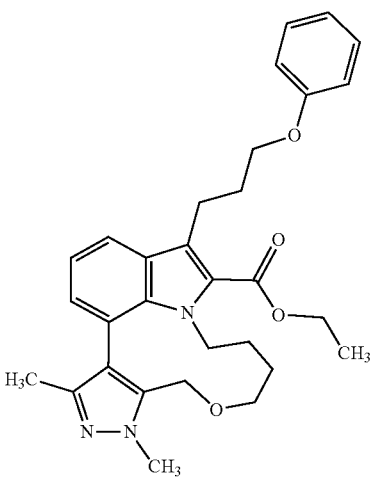

A solution of triphenylphosphine (68 mg, 0.26 mmol) in tetrahydrofuran (10 ml) cooled to 0° C. using an ice water bath was treated with di-isopropyl azodicarboxylate (41 mg, 0.2 mmol), after fifteen minutes this was added to a solution of (rac)-ethyl 7-(3-hydroxypropyl)-1,3-dimethyl-1, 10, 11, 12,13,15-hexahydropyrazolo[4',3':9,10][1,6]oxazacycloundecino[8,7,6-hi]indole-8-carboxylate (see Intermediate 51, 55 mg, 0.13 mmol) and phenol (140 mg, 1.5 mmol) in tetrahydrofuran (10 ml) cooled to 0° C. using an ice water bath. The mixture was then allowed to warm to room temperature over 16 hours, volatiles were removed under reduced pressure and the residue was purified by normal phase chromatography on silica gel (24 g) eluting with a gradient of ethyl acetate in hexanes (30-70%) to give the title compound as a colorless oil (54 mg).

MS (ESI): m/z=502 [M+H]$^+$

445

Intermediate 57

(rac)-ethyl 7-{3-[(6-fluoro-1-naphthyl)oxy]propyl}-1,3-dimethyl-1,10,11,12,13,15-hexahydropyrazolo[4',3':9,10][1,6]oxazacycloundecino[8,7,6-hi]indole-8-carboxylate

446

Intermediate 58

(rac)-ethyl 1,3-dimethyl-7-(3-{[(4-methylphenyl)sulfonyl]oxy}propyl)-1,10,11,12,13,15-hexahydropyrazolo[4',3':9,10][1,6]oxazacycloundecino[8,7,6-hi]indole-8-carboxylate

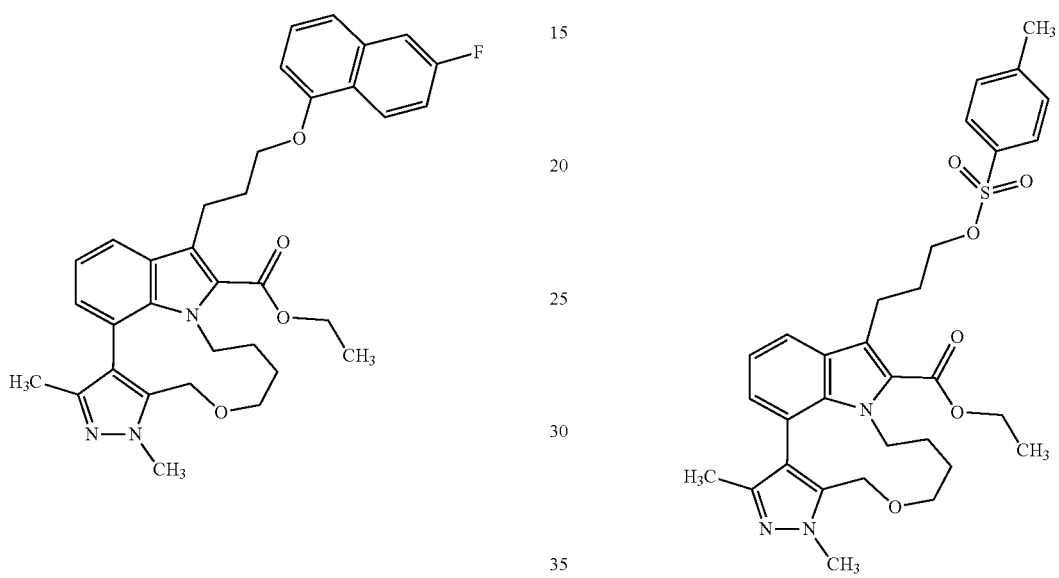

A solution of triphenylphosphine (129 mg, 0.49 mmol) in tetrahydrofuran (5 ml) cooled to 0° C. using an ice water bath was treated with di-isopropyl azodicarboxylate (75 mg, 0.37 mmol), after ten minutes this was added to a solution of (rac)-ethyl 7-(3-hydroxypropyl)-1,3-dimethyl-1,10,11,12,13,15-hexahydropyrazolo[4',3':9,10][1,6]oxazacycloundecino[8,7,6-hi]indole-8-carboxylate (see Intermediate 51, 55 mg, 0.13 mmol) and 6-fluoronaphylen-1-ol (60 mg, 0.37 mmol) in tetrahydrofuran (10 ml) cooled to 0° C. using an ice water bath. The mixture was then allowed to warm to room temperature over 4 hours, volatiles were removed under reduced pressure and the residue was purified by normal phase chromatography on silica gel (24 g) eluting with a gradient of ethyl acetate in hexanes (0-100%) to give the title compound as a colorless film (50 mg).

MS (ESI): m/z=570 [M+H]$^+$

To a solution of (rac)-ethyl 7-(3-hydroxypropyl)-1,3-dimethyl-1,10,11,12,13,15-hexahydropyrazolo[4',3':9,10][1,6]oxazacycloundecino[8,7,6-hi]indole-8-carboxylate (see Intermediate 51, 100 mg, 0.24 mmol) and triethylamine (726 mg, 7.2 mmol) in dichloromethane (20 ml) was added p-toluene sulfonyl chloride (100 mg, 0.52 mmol) and stirred at room temperature for 4 hours, volatiles were removed and the residue purified by normal phase chromatography on silica gel (12 g), eluting with a gradient of ethyl acetate in hexanes (25-75%) to yield the title compound as a solid (75 mg).

MS (ESI): m/z=580 [M+H]$^+$

Intermediate 59

(rac)-ethyl 7-{3-[(4-fluoro-1-naphthyl)oxy]propyl}-1,3-dimethyl-1,10,11,12,13,15-hexahydropyrazolo[4',3':9,10][1,6]oxazacycloundecino[8,7,6-hi]indole-8-carboxylate

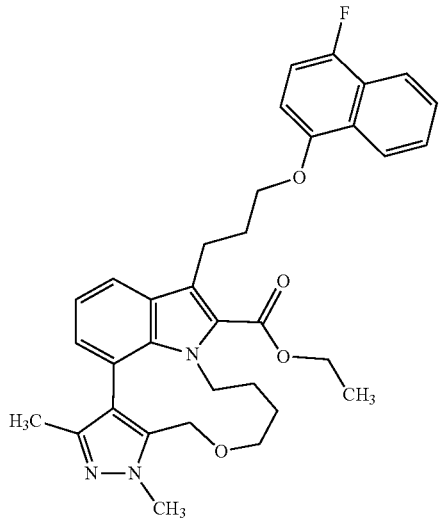

To a solution of (rac)-ethyl 1,3-dimethyl-7-(3-{[(4-methylphenyl)sulfonyl]oxy}propyl)-1,10,11,12,13,15-hexahydropyrazolo[4',3':9,10][1,6]oxazacycloundecino[8,7,6-hi]indole-8-carboxylate (see intermediate 58, 75 mg, 0.13 mmol) and 4-fluoro-1-naphthol (162 mg, 1 mmol) in dimethyl formamide (5 ml) was added sodium hydride (60% in oil, 40 mg, 1 mmol) at room temperature, the solution was then warmed to 50° C. for 16 hours, cooled to room temperature, diluted with ethyl acetate, washed with water, saturated aqueous sodium bicarbonate solution, saturated aqueous sodium chloride solution, and dried over magnesium sulfate. Insoluble materials were removed by filtration and volatiles were removed under reduced pressure. The residue was purified by normal phase chromatography on silica gel (12 g) eluting with a gradient of ethyl acetate in hexanes (25-75%) to afford the title compound as a red film (46 mg).

MS (ESI): m/z=570 [M+H]$^+$

Intermediate 60

2-bromo-1-(4-chlorophenyl)ethanone

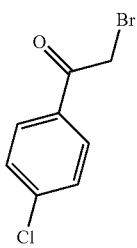 [SMILES: O=C(CBr)c1ccc(Cl)cc1]

To a solution of 4'chloroacetophenone (3 g, 19.4 mmol) in dichloromethane (100 ml) and acetic acid (2 ml) was treated with bromine (1.2 ml, 21 mmol) and stirred at room temperature for 16 hours, volatiles were removed under reduced pressure to give the title compound with unidentified impurities as a cream colored solid (4.66 g).

MS (ESI): m/z=233/235 [M+H]$^+$

Intermediate 61

S-[2-(4-chlorophenyl)-2-oxoethyl] O-ethyl carbonodithioate

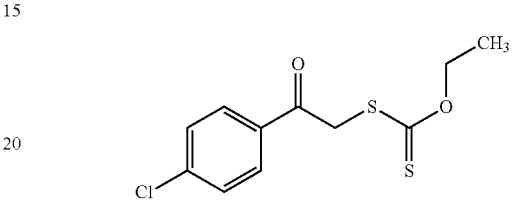

To a solution of 2-bromo-1-(4-chlorophenyl)ethanone (4.66 g, 20 mmol) in acetone (100 ml) was added potassium ethyl xanthate (4 g, 24.95 mmol), after 3 hours, the reaction was filtered to remove insoluble materials, the filtrate was concentrated under reduced pressure and the residue was purified by normal phase chromatography on silica gel (120 g) eluting with a gradient of ethyl acetate in hexanes (0-20%) to give the title compound as a white solid (3.3 g).

$^1$H NMR (400 MHz, Chloroform-d) δ [ppm]: 7.97 (dd, J=8.5, 1.5 Hz, 2H), 7.48 (dd, J=8.5, 1.5 Hz, 2H), 4.69-4.59 (m, 4H), 1.53 (d, J=1.3 Hz, 3H), 1.40 (td, J=7.2, 1.3 Hz, 3H).

MS (ESI): m/z=275 [M+H]$^+$

Intermediate 62

(rac)-4-(4-chlorophenyl)-1-[(ethoxycarbonothioyl)sulfanyl]-4-oxobutyl pivalate

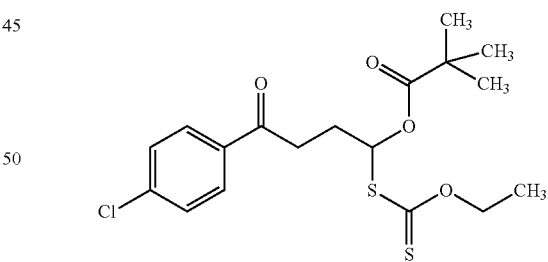

A solution of S-[2-(4-chlorophenyl)-2-oxoethyl] O-ethyl carbonodithioate (3.3 g, 12 mmol) and vinyl pivalate (3.1 g, 24 mmol) in ethyl acetate (100 ml) was heated to reflux and Di(dodecanoyl) peroxide was added in aliquots of (500 mg, 1.25 mmol) with 1 hour reflux between additions until all S-[2-(4-chlorophenyl)-2-oxoethyl] O-ethyl carbonodithioate was consumed. Volatiles were removed under reduced pressure and the residue was dissolved in hexanes and adsorbed onto basic alumina (10 g) and purified by normal phase chromatography on silica gel (40 g) eluting with a gradient of ethyl acetate in hexanes (0-10%) to give the title compound as a yellow oil (2.5 g).

¹H NMR (400 MHz, Chloroform-d) δ [ppm]: 7.93-7.83 (m, 2H), 7.49-7.39 (m, 2H), 6.71 (t, J=6.5 Hz, 1H), 4.63 (qd, J=7.1, 2.1 Hz, 2H), 4.12 (q, J=7.2 Hz, 1H), 3.10 (td, J=7.0, 2.6 Hz, 2H), 2.59 (s, 0H), 2.48-2.28 (m, 2H), 2.04 (s, 1H), 1.54 (s, 2H), 1.41 (t, J=7.1 Hz, 3H), 1.26 (t, J=7.1 Hz, 1H), 1.19 (s, 9H).

Intermediate 63

(rac)-7-chloro-4-oxo-1,2,3,4-tetrahydronaphthalen-1-yl pivalate

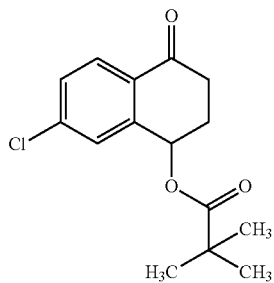 [SMILES: CC(C)(C)C(=O)OC1CCC(=O)c2ccc(Cl)cc21]

A solution of (rac)-4-(4-chlorophenyl)-1-[(ethoxycarbonothioyl)sulfanyl]-4-oxobutyl pivalate (2.5 g, 6.2 mmol) in ethyl acetate (100 ml) was heated to reflux and four times successively treated with Di(dodecanoyl) peroxide (700 mg, 1.75 mmol) and heated at reflux for 2 hours; after consumption of (rac)-4-(4-chlorophenyl)-1-[(ethoxycarbonothioyl)sulfanyl]-4-oxobutyl pivalate, volatiles were removed under reduced pressure, and the residue was purified by normal phase chromatography eluting through a pad of basic alumina and a column of silica gel (40 g) with a gradient of ethyl acetate in hexanes (0-15%) to give the title compound (1.7 g).

¹H NMR (400 MHz, Chloroform-d) δ [ppm]: 8.00 (d, J=8.2 Hz, 1H), 7.47-7.35 (m, 2H), 6.05 (dd, J=7.1, 3.8 Hz, 1H), 2.89 (ddd, J=17.5, 8.6, 4.7 Hz, 1H), 2.68 (ddd, J=17.5, 8.3, 4.7 Hz, 1H), 2.40 (ddt, J=13.1, 8.7, 4.3 Hz, 1H), 2.25 (dddd, J=13.4, 8.3, 7.2, 4.7 Hz, 1H), 1.24 (s, 9H).

Intermediate 64

6-chloro-1-naphthol

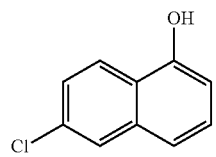 [SMILES: Oc1cccc2cc(Cl)ccc12]

To a solution of 7-chloro-4-oxo-1,2,3,4-tetrahydronaphthalen-1-yl pivalate (1.7 g, 6.07 mmol) in toluene (150 ml) was added toluene sulfonic acid (1.3 g, 6.8 mmol), affixed with a dean stark trap and heated to reflux for 3 hours, cooled to room temperature, volatiles were removed under reduced pressure and the residue purified by normal phase chromatography on silica gel (40 g) eluting with a gradient of ethyl acetate in hexanes (0-20%) to give the title compound with unidentified impurities as a brown gum, this material was dissolved in refluxing hexanes (40 ml) and cooled to room temperature. The resulting solid was isolated by filtration to give the title compound (170 mg).

¹H NMR (400 MHz, Chloroform-d) δ [ppm]: 8.14 (d, J=9.0 Hz, 1H), 7.79 (d, J=2.1 Hz, 1H), 7.42 (dd, J=8.9, 2.1 Hz, 1H), 7.37-7.29 (m, 2H), 6.80 (dd, J=6.5, 2.0 Hz, 1H), 5.21 (s, 1H).

LRMS (ESI) M+H+ 179.

Intermediate 65

(rac)-ethyl 7-{3-[(6-chloro-1-naphthyl)oxy]propyl}-1,3-dimethyl-1,10,11,12,13,15-hexahydropyrazolo[4',3':9,10][1,6]oxazacycloundecino[8,7,6-hi]indole-8-carboxylate

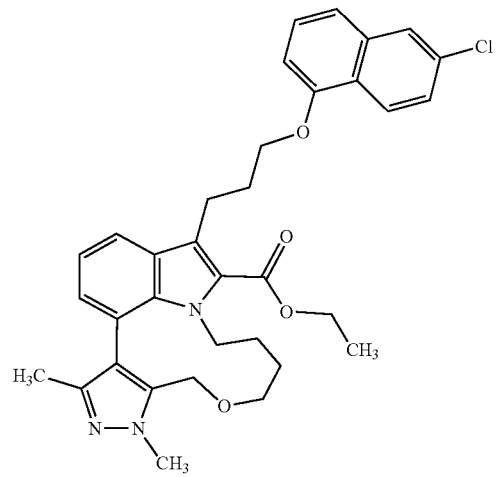

A solution of triphenyl phosphine (204 mg, 0.78 mmol) in tetrahydrofuran (5 ml) in an ice water bath was treated with di-isopropylazodicarboxylate (120 mg, 0.59 mmol), after ten minutes this was added to a solution of (rac)-ethyl 7-(3-hydroxypropyl)-1,3-dimethyl-1,10,11,12,13,15-hexahydropyrazolo[4',3':9,10][1,6]oxazacycloundecino[8,7,6-hi]indole-8-carboxylate (see Intermediate 51, 90 mg, 0.22 mmol) and 6-chloro-1-naphthol (170 mg, 1.14 mmol) in tetrahydrofuran (4 ml) in an ice water bath, this mixture was allowed to warm to room temperature over 16 hours, volatiles were removed under reduced pressure and the residue was purified by normal phase chromatography on silica gel (12 g) eluting with a gradient of ethyl acetate in hexanes (25-75%) to give the title compound as a colorless oil (89 mg).

¹H NMR (400 MHz, Chloroform-d) b 8.28 (d, J=9.0 Hz, 1H), 7.78 (d, J=2.1 Hz, 1H), 7.71 (dd, J=8.1, 1.3 Hz, 1H), 7.41 (dd, J=9.0, 2.1 Hz, 1H), 7.36 (d, J=7.7 Hz, 1H), 7.32 (d, J=8.2 Hz, 1H), 7.06 (dd, J=8.0, 7.0 Hz, 1H), 6.88 (dd, J=7.1, 1.3 Hz, 1H), 6.76 (dd, J=7.5, 1.2 Hz, 1H), 4.65 (dt, J=14.4, 3.9 Hz, 1H), 4.58 (d, J=13.4 Hz, 1H), 4.45 (d, J=13.4 Hz, 1H), 4.41-4.26 (m, 2H), 4.21 (t, J=6.2 Hz, 2H), 4.19-4.07 (m, 1H), 3.94 (s, 3H), 3.55-3.39 (m, 2H), 3.34 (dt, J=13.5, 7.5 Hz, 1H), 2.88 (ddd, J=11.5, 9.0, 4.3 Hz, 1H), 2.34 (p, J=7.0 Hz, 2H), 1.98 (s, 3H), 1.47 (ttd, J=11.0, 6.9, 3.3 Hz, 1H), 1.37 (t, J=7.1 Hz, 3H), 1.30-1.17 (m, 2H), 1.16-1.01 (m, 1H).

MS (ESI): m/z=587 [M+H]$^+$

Intermediate 66

2-bromo-1-(4-fluoro-3-methylphenyl)ethanone

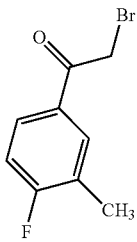

To a solution of 4-fluoro-3-methyl-acetophenone (Ark pharm, CAS-369-32-4 AK-48194, 5 g, 32.85 mmol) in dichloromethane (100 ml) and acetic acid (3 ml) was added bromine (5.24 g, 32.85 mmol) and stirred at room temperature for 1 hour, volatiles were removed under reduced pressure to give the title compound (7.57 g).

Intermediate 67

O-ethyl S-[2-(4-fluoro-3-methylphenyl)-2-oxoethyl] carbonodithioate

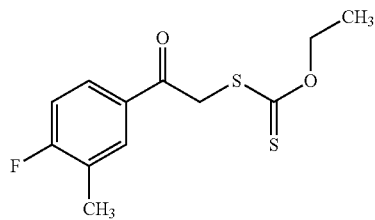 [SMILES: CCOC(=S)SCC(=O)c1ccc(F)c(C)c1]

To a solution of 2-bromo-1-(4-fluoro-3-methylphenyl) ethanone (7.57 g theory 32.7 mmol) in acetone (50 ml) was added potassium ethyl xanthate (5.3 g, 33 mmol) and stirred at room temperature for 16 hours, insoluble materials were removed by filtration, volatiles were removed under reduced pressure and the residue was purified by normal phase chromatography on silica gel (40 g) eluting with a gradient of dichloromethane in hexanes (0-50%) to give the title compound as a tacky solid (7.86 g).

LRMS (ESI) M+H+ 273 M−H− 271.

Intermediate 68

(rac)-7-fluoro-6-methyl-4-oxo-1,2,3,4-tetrahydronaphthalen-1-yl pivalate

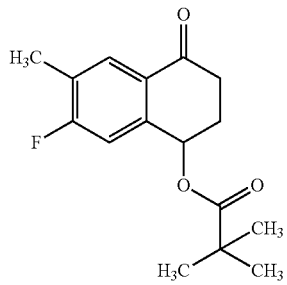 [SMILES: Cc1cc2c(cc1F)C(OC(=O)C(C)(C)C)CCC2=O]

To a refluxing solution of O-ethyl S-[2-(4-fluoro-3-methylphenyl)-2-oxoethyl] carbonodithioate (7.87 g, 28.9 mmol) and vinyl pivalate (8.66 g, 67.5 mmol) in ethyl acetate (100 ml) was added Di(dodecanoyl) peroxide (600 mg, 1.5 mmol) every 90 minutes until complete consumption of O-ethyl S-[2-(4-fluoro-3-methylphenyl)-2-oxoethyl] carbonodithioate was apparent. Volatiles were removed under reduced pressure and the residue was dissolved in ethyl acetate (100 ml), heated to reflux, and treated with Di(dodecanoyl) peroxide (1 g, 2.5 mmol) every 60 minutes until the formation of the title compound was complete. The reaction mixture was cooled to room temperature and the volatiles were removed under reduced pressure, the residue was purified by normal phase chromatography on silica gel (80 g) after eluting through basic aluminum oxide (10 g), eluting with a gradient of ethyl acetate in hexanes (0-20%) to give crude title compound which was further purified by normal phase chromatography on silica gel (40 g) eluting with a gradient of ethyl acetate in hexanes (5-15%) to give the title compound along with the 8-methyl isomer and other unidentified impurities (2.5 g).

Intermediate 69

6-fluoro-7-methyl-1-naphthol

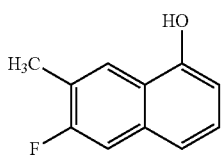

To a solution of (rac)-7-fluoro-6-methyl-4-oxo-1,2,3,4-tetrahydronaphthalen-1-yl pivalate (2.5 g, 9.0 mmol) in toluene (75 ml) was added toluene sulfonic acid (750 mg, 4.5 mmol) and heated to reflux for 9 hours. The reaction mixture was cooled to room temperature, volatiles were removed under reduced pressure, and the residue was purified by normal phase chromatography on silica gel (80 g) eluting with a gradient of ethyl acetate in hexanes (0-30%) to afford the title compound along with impurities. This material was further purified by normal phase chromatography on silica gel (80 g) eluting with a gradient of ethyl acetate in hexanes (5-10%) to afford an off white solid which was dissolved in refluxing hexanes, cooled to room temperature, and the resulting solid was isolated by filtration to give the title compound as a white solid (74 mg).

$^1$H NMR (400 MHz, Chloroform-d) δ [ppm]: 8.03 (d, J=7.9 Hz, 1H), 7.39 (d, J=10.8 Hz, 1H), 7.35 (d, J=8.3 Hz, 1H), 7.26 (d, J=8.6 Hz, 1H), 6.77-6.72 (m, 1H), 5.13 (s, 1H), 2.49 (t, J=1.4 Hz, 3H).

Intermediate 70

(rac)-ethyl 7-{3-[(6-fluoro-7-methyl-1-naphthyl)oxy]propyl}-1,3-dimethyl-1,10,11,12,13,15-hexahydropyrazolo[4',3':9,10][1,6]oxazacycloundecino[8,7,6-hi]indole-8-carboxylate

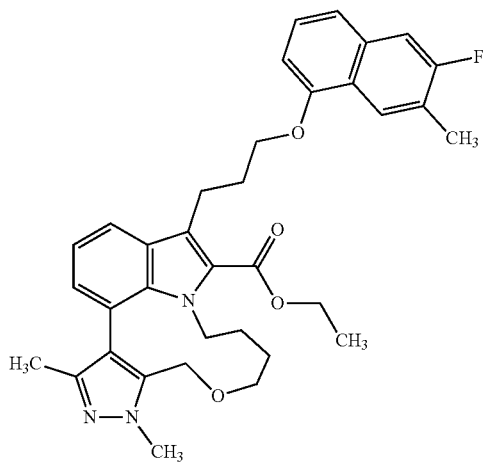 [SMILES: CCOC(=O)c1c(CCCOc2cccc3cc(F)c(C)cc23)c2cccc3c2n1CCCCOCc1c-3c(C)nn1C]

A solution of triphenylphosphine (240 mg, 0.92 mmol) in tetrahydrofuran (10 ml) cooled to 0° C. using an ice water bath was treated with di-isopropyl azodicarboxylate (124 mg, 0.61 mmol), after fifteen minutes this was added to a solution of (rac)-ethyl 7-(3-hydroxypropyl)-1,3-dimethyl-1,10,11,12,13,15-hexahydropyrazolo[4',3':9,10][1,6]oxazacycloundecino[8,7,6-hi]indole-8-carboxylate (see Intermediate 51, 165 mg, 0.39 mmol) and 6-fluoro-7-methyl-1-naphthol (70 mg, 0.4 mmol) in tetrahydrofuran (10 ml) cooled to 0° C. using an ice water bath. This mixture was allowed to warm to room temperature over 16 hours, volatiles were removed under reduced pressure and the residue was purified by normal phase chromatography on silica gel (24 g) eluting with a gradient of ethyl acetate in hexanes (30-70%) to give the title compound as a colorless oil (100 mg).

MS (ESI): m/z=585 [M+H]$^+$

Intermediate 71 ethyl 3-(3-hydroxypropyl)-6-methyl-7-(4,4,5,5-tetramethyl-1,3,2-dioxaborolan-2-yl)-1H-indole-2-carboxylate

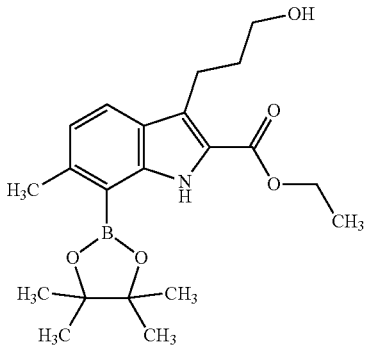 [SMILES: CCOC(=O)c1[nH]c2c(B3OC(C)(C)C(C)(C)O3)c(C)ccc2c1CCCO]

To a solution of ethyl 7-bromo-3-(3-hydroxypropyl)-6-methyl-1H-indole-2-carboxylate (see Intermediate 16, 4.5 g, 12.5 mmol) and 4,4,4',4',5,5,5',5'-octamethyl-2,2'-bi-1,3,2-dioxaborolane (6.7 g, 26.3 mmol) in dioxane (30 ml) was added potassium acetate (2.6 g, 27 mmol) and [1,1'-bis(diphenylphosphino)ferrocene]dichloropalladium(II) (200 mg, 0.27 mmol). The resulting solution was degassed, and then heated to 80° C. for 3 hours. The reaction mixture was cooled to room temperature, volatiles were removed and the residue was partitioned between ethyl acetate and water, the organic layer was washed successively with water, brine, and then dried over magnesium sulfate, filtered to remove insoluble material, and volatiles were removed under reduced pressure. The resulting residue was purified by normal phase chromatography on silica gel (120 g), eluting with a gradient of ethyl acetate in hexanes (20-30%) to give the title compound as a pale brown solid (2.23 g).

1H NMR (400 MHz, Chloroform-d) δ [ppm]: 9.88 (s, 1H), 7.67 (d, J=8.2 Hz, 1H), 7.01 (d, J=8.3 Hz, 1H), 4.44 (q, J=7.1 Hz, 2H), 3.56 (t, J=5.8 Hz, 2H), 3.26 (t, J=6.8 Hz, 2H), 2.70 (s, 3H), 2.00-1.91 (m, 2H), 1.46 (t, J=7.2 Hz, 3H), 1.43 (s, 12H).

MS (ESI): m/z=388 [M+H]$^+$

Intermediate 72 ethyl 7-[5-(hydroxymethyl)-1,3-dimethyl-1H-pyrazol-4-yl]-6-methyl-3-[3-(1-naphthyloxy)propyl]-1H-indole-2-carboxylate

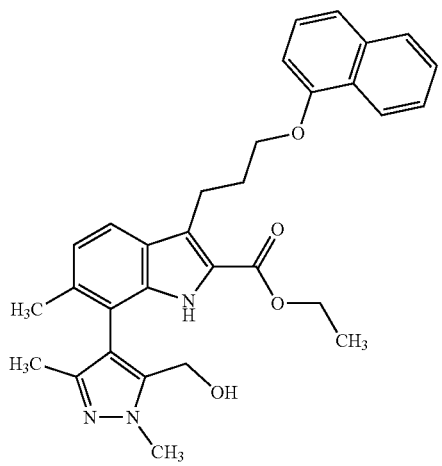 [SMILES: CCOC(=O)c1[nH]c2c(-c3c(C)nn(C)c3CO)c(C)ccc2c1CCCOc1cccc2ccccc12]

A solution of ethyl 6-methyl-3-[3-(naphthalen-1-yloxy)propyl]-7-(4,4,5,5-tetramethyl-1,3,2-dioxaborolan-2-yl)-1H-indole-2-carboxylate (see Intermediate 19, 1.3 g, 2.55 mmol) and (4-bromo-1,3-dimethyl-1H-pyrazol-5-yl)methanol (see Intermediate 8, 672 mg, 3.3 mmol) in a mixture of tetrahydrofuran (40 ml) and aqueous potassium phosphate (0.5M, 20 ml, 10 mmol), was degassed, treated with Palladium XPhos G2 precatalyst (see abbreviation list, 100 mg, 0.13 mmol), degassed again, and heated to 45° C. for 90 minutes. The reaction mixture was cooled to room temperature, volatiles were removed under reduced pressure, and the residue was partitioned between ethyl acetate and water. The organic phase was subsequently washed with saturated aqueous sodium chloride solution, dried over magnesium sulfate, solids were removed by filtration, volatiles were removed under reduced pressure, and the residue was purified by normal phase chromatography on silica gel (40 g) eluting with a gradient of ethyl acetate in hexanes (0-100%), to obtain the title compound as a pale grey solid (970 mg).

$^1$H NMR (400 MHz, DMSO-$d_6$) δ [ppm]: 10.15 (s, 1H), 8.38-8.16 (m, 1H), 7.95-7.80 (m, 1H), 7.58 (d, J=8.2 Hz, 1H), 7.52 (qd, J=7.1, 3.4 Hz, 2H), 7.46 (d, J=8.2 Hz, 1H), 7.40 (t, J=7.9 Hz, 1H), 6.99 (d, J=8.3 Hz, 1H), 6.92 (d, J=7.5 Hz, 1H), 5.17 (t, J=4.7 Hz, 1H), 4.31-4.17 (m, 5H), 4.09 (dd, J=12.7, 4.4 Hz, 1H), 3.87 (s, 3H), 3.39-3.23 (m, 2H), 2.27-2.17 (m, 2H), 2.12 (s, 3H), 1.86 (s, 3H), 1.26 (t, J=7.1 Hz, 3H).

MS (ESI): m/z=512 [M+H]$^+$

Intermediate 73 and Intermediate 74 ethyl 1-allyl-7-{5-[(allyloxy)methyl]-1,3-dimethyl-1H-pyrazol-4-yl}-6-methyl-3-[3-(1-naphthyloxy)propyl]-1H-indole-2-carboxylate and (Intermediate 73)

(rac)-ethyl 9,11,12-trimethyl-1-[3-(1-naphthyloxy)propyl]-5,6,8,9-tetrahydro-4H-pyrazolo[4',3':8,9][1,5]oxazecino[7,6,5-hi]indole-2-carboxylate (Intermediate 74)

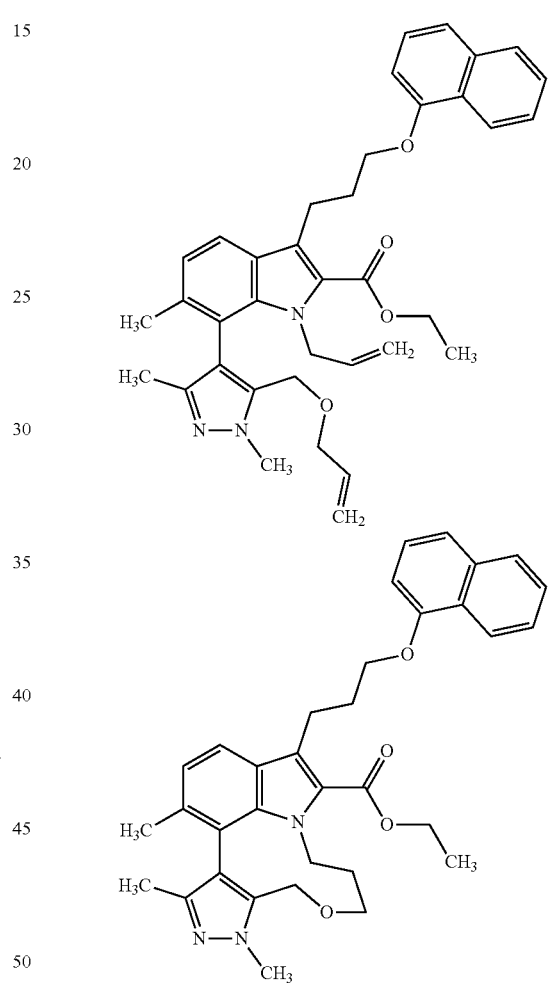

Step 1)

To a solution of ethyl 7-[5-(hydroxymethyl)-1,3-dimethyl-1H-pyrazol-4-yl]-6-methyl-3-[3-(1-naphthyloxy)propyl]-1H-indole-2-carboxylate (1080 mg, 2.1 mmol) in acetonitrile (40 ml) was added 1,3-dibromopropane (6 g, 30 mmol), and caesium carbonate (1.09 g, 3.3 mmol). The mixture was stirred at room temperature for 16 hours, then heated to 40° C. for 8 hours, and then warmed to 45° C. for 16 hours. Additional caesium carbonate (400 mg, 1.3 mmol), and 1,3-dibromopropane (4 g, 20 mmol) were added, and the suspension was heated to 50° C. for 8 hours, cooled to room temperature and stirred at that temperature for 60 hours. Allyl bromide (280 mg, 2.3 mmol) and caesium carbonate (300 mg, 0.92 mmol) were added and the suspension heated to 50° C. for 5 hours, at which time volatiles were removed, the residue was suspended in a mixture of ethyl acetate and hexanes, and purified by normal phase chromatography on silica gel (80 g), eluting with a gradient of ethyl acetate in hexanes (20-60%) to give a mixture of compounds (950 mg) which was subjected to further reaction (see below)

Step 2)

A solution of the above mixture (950 mg) in tetrahydrofuran (40 ml) cooled to 0° C. using an ice water bath was treated with sodium hydride (60% in oil, 60 mg, 1.5 mmol). After 90 minutes, this mixture was treated with dimethyl formamide (5 ml), and sodium hydride (20 mg, 0.5 mmol). After further 10 minutes, allyl bromide (200 mg, 1.5 mmol) was added, after additional 2 hours sodium hydride (20 mg, 0.5 mmol) was added, after further 10 minutes, allyl bromide (200 mg, 1.5 mmol) was added, and the reaction allowed to warm to room temperature over 16 hours. The reaction mixture was diluted with aqueous hydrochloric acid (1M, 100 ml), and extracted three times with ethyl acetate. Organic phases were washed with saturated aqueous sodium chloride solution and were dried over magnesium sulfate. The solids were removed by filtration, and the volatiles were removed under reduced pressure, the residue was purified by normal phase chromatography on silica gel (40 g) eluting with a gradient of ethyl acetate in hexanes (20-75%) to give the first title compound ethyl 1-allyl-7-{5-[(allyloxy)methyl]-1,3-dimethyl-1H-pyrazol-4-yl}-6-methyl-3-[3-(1-naphthyloxy)propyl]-1H-indole-2-carboxylate (380 mg) and the second title compound (rac)-ethyl 9,11,12-trimethyl-1-[3-(1-naphthyloxy)propyl]-5,6,8,9-tetrahydro-4H-pyrazolo[4',3':8,9][1,5]oxazecino[7,6,5-hi]indole-2-carboxylate (260 mg) as colorless oils.

Intermediate 73

MS (ESI): m/z=593 [M+H]$^+$ $^1$H NMR (400 MHz, Chloroform-d) δ [ppm]: 8.54-8.31 (m, 1H), 7.93-7.76 (m, 1H), 7.66 (d, J=8.1 Hz, 1H), 7.60-7.49 (m, 2H), 7.45 (d, J=8.2 Hz, 1H), 7.38 (t, J=7.9 Hz, 1H), 7.07 (d, J=8.2 Hz, 1H), 6.81 (d, J=7.5 Hz, 1H), 5.78 (ddt, J=16.2, 10.9, 5.6 Hz, 1H), 5.55 (ddt, J=17.6, 9.5, 4.4 Hz, 1H), 5.23-5.03 (m, 2H), 4.90-4.66 (m, 3H), 4.33 (q, J=7.3 Hz, 2H), 4.25 (m, 3H), 4.18 (d, J=12.1 Hz, 1H), 4.06 (d, J=12.0 Hz, 1H), 3.96 (s, 3H), 3.91-3.73 (m, 2H), 3.38 (t, J=7.5 Hz, 2H), 2.36 (p, J=6.6 Hz, 2H), 2.13 (s, 3H), 2.02 (s, 3H), 1.37 (t, J=7.1 Hz, 3H).

Intermediate 74

MS (ESI): m/z=552 [M+H]$^+$ $^1$H NMR (400 MHz, Chloroform-d) δ [ppm]: 8.41-8.29 (m, 1H), 7.86-7.77 (m, 1H), 7.65 (d, J=8.2 Hz, 1H), 7.56-7.45 (m, 2H), 7.42 (d, J=8.2 Hz, 1H), 7.35 (t, J=7.9 Hz, 1H), 7.04 (d, J=8.2 Hz, 1H), 6.78 (dd, J=7.5, 1.0 Hz, 1H), 4.72 (d, J=14.2 Hz, 1H), 4.62 (dt, J=14.7, 3.6 Hz, 1H), 4.32 (dddd, J=18.0, 10.8, 7.1, 3.7 Hz, 2H), 4.21 (t, J=6.1 Hz, 2H), 3.95 (s, 3H), 3.81 (dt, J=12.4, 3.2 Hz, 2H), 3.77-3.69 (m, 1H), 3.42 (dt, J=13.4, 7.5 Hz, 1H), 3.32 (dt, J=13.4, 7.5 Hz, 1H), 2.70-2.54 (m, 1H), 2.33 (h, J=7.3 Hz, 2H), 2.10 (s, 3H), 2.00 (s, 3H), 1.71 (tt, J=12.2, 4.2 Hz, 1H), 1.60 (ddq, J=15.8, 13.3, 2.6 Hz, 1H), 1.36 (t, J=7.1 Hz, 3H).

Intermediate 75

(rac)-ethyl (E/Z)-1,3,4-trimethyl-7-[3-(1-naphthyloxy)propyl]-1,10,13,15-tetrahydropyrazolo[4',3':9,10][1,6]oxazacycloundecino[8,7,6-hi]indole-8-carboxylate

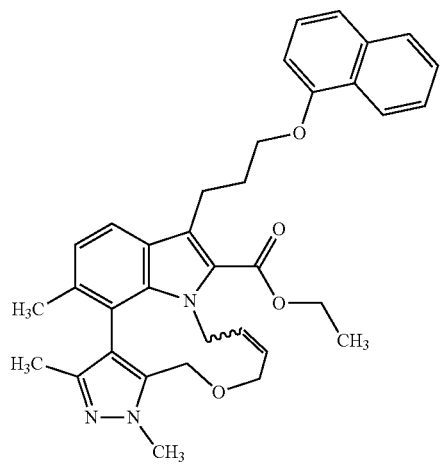 [SMILES: CCOC(=O)c1c(CCCOc2cccc3ccccc23)c2ccc(C)c3c2n1CC=CCOCc1c-3c(C)nn1C]

A solution of ethyl 1-allyl-7-{5-[(allyloxy)methyl]-1,3-dimethyl-1H-pyrazol-4-yl}-6-methyl-3-[3-(1-naphthyloxy)propyl]-1H-indole-2-carboxylate (see Intermediate 73, 380 mg, 0.64 mmol) and (1,3-bis(2,4,6-trimethylphenyl)-2-imidazolidinylidene)dichloro(phenylmethylene)(tricyclohexylphosphine)ruthenium (70 mg, 0.08 mmol) in dichloromethane (40 ml) was stirred at room temperature for 16 hours. Volatiles were removed under reduced pressure and the residue was purified by normal phase chromatography on silica gel (24 g) eluting with a gradient of ethyl acetate in hexanes (0-80%) to give the title compound as a pale black film (280 mg).

$^1$H NMR (400 MHz, Chloroform-d) δ [ppm]: 8.39-8.30 (m, 1H), 7.85-7.76 (m, 1H), 7.61 (d, J=8.1 Hz, 1H), 7.49 (td, J=7.3, 6.4, 4.2 Hz, 2H), 7.42 (d, J=8.2 Hz, 1H), 7.35 (t, J=7.9 Hz, 1H), 7.04 (d, J=8.2 Hz, 1H), 6.78 (d, J=7.5 Hz, 1H), 5.20 (t, J=9.4 Hz, 1H), 5.08 (d, J=16.2 Hz, 1H), 4.99 (t, J=10.8 Hz, 1H), 4.69 (dd, J=16.2, 10.2 Hz, 1H), 4.59 (d, J=13.6 Hz, 1H), 4.39 (s, 1H), 4.36 (dd, J=6.7, 4.2 Hz, 1H), 4.31 (dd, J=10.8, 7.1 Hz, 1H), 4.23 (t, J=6.1 Hz, 2H), 3.99 (s, 3H), 3.82 (dd, J=12.9, 4.9 Hz, 1H), 3.68 (t, J=12.2 Hz, 1H), 3.38 (qt, J=13.5, 7.4 Hz, 2H), 2.35 (p, J=7.0 Hz, 2H), 1.93 (s, 3H), 1.82 (s, 3H), 1.37 (t, J=7.1 Hz, 3H).

MS (ESI): m/z=564 [M+H]$^+$

Intermediate 76

(rac)-ethyl 1,3,4-trimethyl-7-[3-(1-naphthyloxy) propyl]-1,10,11,12,13,15-hexahydropyrazolo[4',3':9,10][1,6]oxazacycloundecino[8,7,6-hi]indole-8-carboxylate

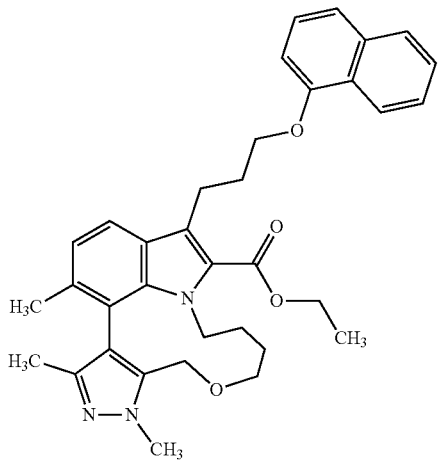 [SMILES: CCOC(=O)c1c(CCCOc2cccc3ccccc23)c2ccc(C)c3c2n1CCCCOCc1c-3c(C)nn1C]

To a degassed solution of (rac)-ethyl (E/Z)-1,3,4-trimethyl-7-[3-(1-naphthyloxy)propyl]-1,10,13,15-tetrahydropyrazolo[4',3':9,10][1,6]oxazacycloundecino[8,7,6-hi]indole-8-carboxylate (280 mg, 0.5 mmol) in ethanol (40 ml) was added palladium on carbon (10%, 100 mg, 0.09 mmol), stirred under one atmosphere of hydrogen for 16 hours. The reaction mixture was degassed, filtered through a pad of Celite, volatiles were removed under reduced pressure, and the residue was purified by normal phase chromatography on silica gel (24 g), eluting with a gradient of ethyl acetate in hexanes (25-75%) to give the title compound (160 mg).

MS (ESI): m/z=566 [M+H]$^+$

Intermediate 77

(rac)-ethyl 1,3,4-trimethyl-7-[3-(5,6,7,8-tetrahydronaphthalen-1-yloxy)propyl]-1,10,11,12,13,15-hexahydropyrazolo[4',3':9,10][1,6]oxazacycloundecino[8,7,6-hi]indole-8-carboxylate

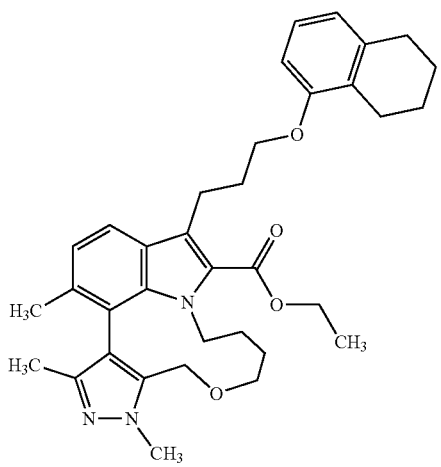 [SMILES: CCOC(=O)c1c(CCCOc2cccc3c2CCCC3)c2ccc(C)c3c2n1CCCCOCc1c-3c(C)nn1C]

A solution of (rac)-ethyl 1,3,4-trimethyl-7-[3-(1-naphthyloxy)propyl]-1,10,11,12,13,15-hexahydropyrazolo[4',3':9,10][1,6]oxazacycloundecino[8,7,6-hi]indole-8-carboxylate (60 mg, 0.11 mmol) in ethanol (40 ml) was degassed, treated with palladium on carbon (10%, 210 mg, 2 mmol) and placed under 1 atmosphere of hydrogen gas for 16 hours. The reaction mixture was filtered through a pad of Celite, and volatiles were removed, to give the title compound as a dark gum (60 mg).

MS (ESI): m/z=570 [M+H]$^+$

Intermediate 78

2-(1,3-dimethyl-1H-pyrazol-5-yl)ethanol

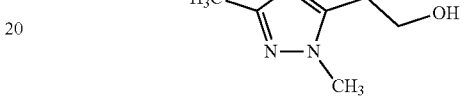

A solution of 2-(1,3-dimethyl-1H-pyrazol-5-yl)acetic acid (3.0 g, 19.4 mmol, CAS 196717-12-1) in tetrahydrofuran (78 mL) at 0° C. was treated with borane (1.0 M in tetrahydrofuran, 58.2 mL, 58.2 mmol) drop-wise via addition funnel. The cooling bath was removed and the reaction mixture was stirred at room temperature overnight. The mixture was cooled to 0° C. and the reaction was stopped by carefully adding methanol. The mixture was concentrated and the crude residue was re-dissolved in methanol and heated at reflux for 30 min to liberate the free alcohol. The mixture was then cooled to room temperature and concentrated to obtain the title compound (2.75 g).

MS: m/z=141 [M+H]$^+$ $^1$H NMR (300 MHz, Chloroform-d) δ [ppm]: 5.87 (s, 1H), 3.85 (q, J=6.1 Hz, 2H), 3.72 (s, 3H), 2.89-2.61 (m, 3H), 2.20 (s, 3H).

Intermediate 79

2-(4-bromo-1,3-dimethyl-1H-pyrazol-5-yl)ethanol

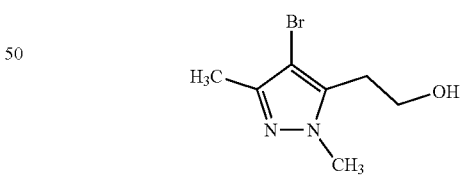

To a solution of 2-(1,3-dimethyl-1H-pyrazol-5-yl)ethanol (2.7 g, 19.2 mmol) in methanol (53 mL) at 0° C. was added pyridinium tribromide (6.14 g, 19.2 mmol). The mixture was stirred at 0° C. for 30 min, then at room temperature overnight. The reaction mixture was diluted with 10% aqueous potassium carbonate solution and extracted three times with dichloromethane. The combined organic layers were dried over sodium sulfate, filtered, and concentrated. The crude residue was purified by flash chromatography on silica gel (0-10% methanol/dichloromethane) to obtain 2-(4-bromo-1,3-dimethyl-1H-pyrazol-5-yl)ethanol (3.59 g).

¹H NMR (300 MHz, Chloroform-d) δ [ppm]: 3.93-3.78 (m, 4H), 2.91 (t, J=6.4 Hz, 2H), 2.22 (s, 3H), 1.73-1.57 (m, 1H).

Intermediate 80 ethyl 7-[5-(2-hydroxyethyl)-1,3-dimethyl-1H-pyrazol-4-yl]-3-[3-(1-naphthyloxy)propyl]-1H-indole-2-carboxylate

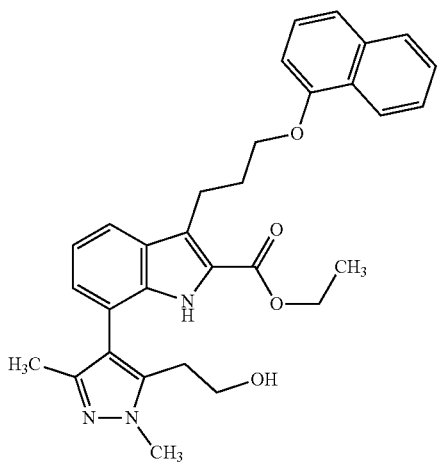 [SMILES: CCOC(=O)c1[nH]c2c(-c3c(C)nn(C)c3CCO)cccc2c1CCCOc1cccc2ccccc12]

Intermediate 81 ethyl 1-allyl-7-{5-[2-(allyloxy)ethyl]-1,3-dimethyl-1H-pyrazol-4-yl}-3-[3-(1-naphthyloxy)propyl]-1H-indole-2-carboxylate

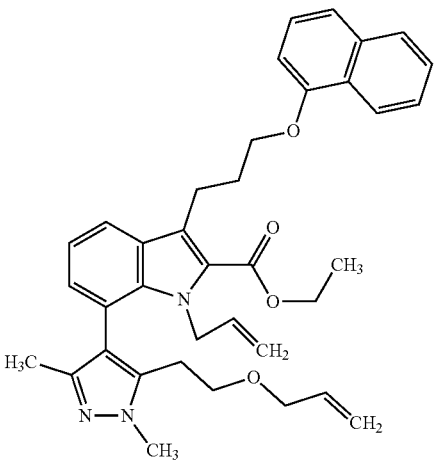 [SMILES: C=CCOCCc1c(-c2cccc3c(CCCOc4cccc5ccccc45)c(C(=O)OCC)n(CC=C)c23)c(C)nn1C]

A flask equipped with a stirrer bar was charged with ethyl 3-(3-(naphthalen-1-yloxy)propyl)-7-(4,4,5,5-tetramethyl-1,3,2-dioxaborolan-2-yl)-1H-indole-2-carboxylate (see Intermediate 5, 1.99 g, 3.98 mmol), 2-(4-bromo-1,3-dimethyl-1H-pyrazol-5-yl)ethanol (871 mg, 3.98 mmol), tetrahydrofuran (40 mL), and potassium phosphate (0.5 M in water, 15.9 mL, 7.96 mmol) and the mixture was degassed via argon sparging for 15 min. Xphos Pd G3 (84.2 mg, 99.5 µmol) was then added and the mixture was stirred at 50° C. for 2 h. Upon cooling to room temperature, the mixture was diluted with water and extracted three times with ethyl acetate. The combined organic phases were washed with brine, dried over sodium sulfate, filtered, and concentrated. The crude residue was purified by flash chromatography on silica gel (20% methanol/dichloromethane) to obtain the title compound (1.96 g).

MS: m/z=512 [M+H]⁺

¹H NMR (300 MHz, Chloroform-d) δ [ppm]: 9.32 (s, 1H), 8.43-8.33 (m, 1H), 7.87-7.77 (m, 1H), 7.76-7.66 (m, 1H), 7.57-7.31 (m, 4H), 7.28 (s, 2H), 7.21-7.09 (m, 2H), 6.80 (dd, J=7.4, 1.1 Hz, 1H), 4.37 (q, J=7.1 Hz, 2H), 4.25 (t, J=6.1 Hz, 2H), 3.91 (s, 3H), 3.81 (q, J=6.6, 6.0 Hz, 4H), 3.44 (t, J=7.5 Hz, 2H), 2.75 (s, 2H), 2.37 (q, J=7.0 Hz, 2H), 2.22 (s, 1H), 2.14 (s, 4H), 1.95 (s, 2H), 1.38 (t, J=7.1 Hz, 3H), 1.26 (s, 13H).

To a solution of ethyl 7-[5-(2-hydroxyethyl)-1,3-dimethyl-1H-pyrazol-4-yl]-3-[3-(1-naphthyloxy)propyl]-1H-indole-2-carboxylate (0.130 g, 0.254 mmol) in anhydrous tetrahydrofuran (4 mL) at 0° C. was added 95% sodium hydride (22.4 mg, 0.889 mmol). The mixture was stirred for 30 min at 0° C. before adding 3-bromoprop-1-ene (76.4 µL, 0.889 mmol). The mixture was stirred overnight at rt, diluted with brine, and extracted three times with ethyl acetate. The combined organic phases were dried over sodium sulfate, filtered, and concentrated. The crude residue was purified by flash chromatography on silica gel (20-70% ethyl acetate/hexanes) to obtain the title compound (66.7 mg).

MS: m/z=594 [M+H]⁺

¹H NMR (300 MHz, Chloroform-d) δ [ppm]: 8.47-8.35 (m, 1H), 7.83 (dd, J=6.5, 3.0 Hz, 1H), 7.74 (dd, J=8.0, 1.3 Hz, 1H), 7.56-7.47 (m, 1H), 7.40 (dt, J=15.7, 8.2 Hz, 1H), 7.17-7.06 (m, 1H), 7.02 (dd, J=7.1, 1.3 Hz, 1H), 6.80 (d, J=7.4 Hz, 1H), 5.80 (ddt, J=17.2, 10.6, 5.3 Hz, 1H), 5.54 (ddt, J=17.2, 10.3, 4.4 Hz, 1H), 5.23-5.08 (m, 2H), 4.98-4.74 (m, 2H), 4.41-4.17 (m, 4H), 3.89 (s, 2H), 3.83 (dt, J=5.6, 1.5 Hz, 2H), 3.40 (td, J=6.9, 3.4 Hz, 4H), 2.83-2.63 (m, 1H), 2.36 (t, J=7.4 Hz, 2H), 2.05 (s, 2H), 1.37 (t, J=7.1 Hz, 2H).

463

Intermediate 82

(rac)-ethyl (E/Z)-1,3-dimethyl-7-[3-(1-naphthyloxy)propyl]-10,13,15,16-tetrahydro-1H-pyrazolo[4',3':9,10][1,6]oxazacyclododecino[8,7,6-hi]indole-8-carboxylate

464

Intermediate 83

(rac)-ethyl 1,3-dimethyl-7-[3-(1-naphthyloxy)propyl]-10,11,12,13,15,16-hexahydro-1H-pyrazolo[4',3':9,10][1,6]oxazacyclododecino[8,7,6-hi]indole-8-carboxylate

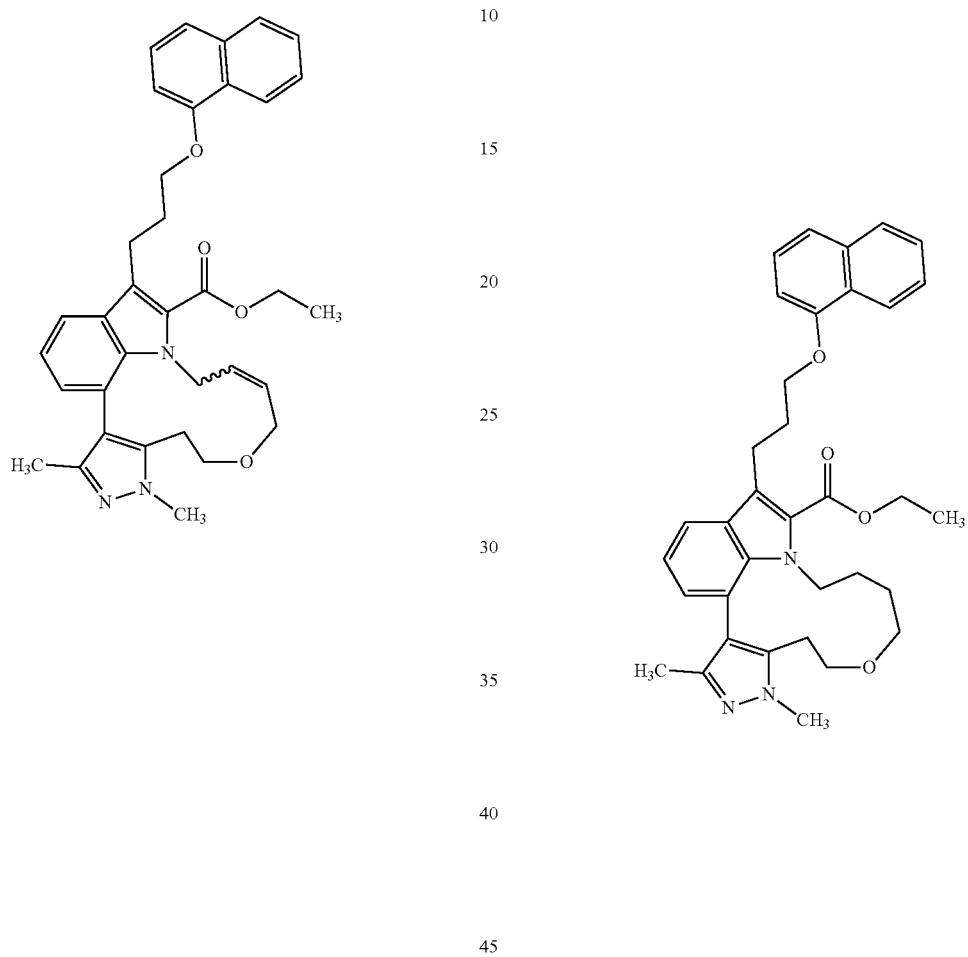

To a solution of ethyl 1-allyl-7-{5-[2-(allyloxy)ethyl]-1,3-dimethyl-1H-pyrazol-4-yl}-3-[3-(1-naphthyloxy)propyl]-1H-indole-2-carboxylate (66.7 mg, 0.112 mmol) in dry dichloromethane (2.2 mL) was added Grubbs 2nd generation catalyst (see abbreviation list; 9.5 mg, 11.2 μmol). The mixture was stirred for 2 days at room temperature, during which time more catalyst was added to drive conversion. The mixture was concentrated and purified by flash chromatography on silica gel (0-100% ethyl acetate/hexanes) to obtain the title compound (30 mg) as well as recovered starting material (18 mg).

MS: m/z=564 [M+H]$^+$ $^1$H NMR (300 MHz, Chloroform-d) δ [ppm]: 8.46-8.34 (m, 1H), 7.89-7.67 (m, 2H), 7.58-7.23 (m, 5H), 7.19-6.99 (m, 2H), 6.81 (ddd, J=7.5, 3.2, 1.3 Hz, 1H), 5.70-5.50 (m, 1H), 5.25 (ddd, J=16.0, 10.1, 5.9 Hz, 1H), 5.06 (d, J=9.3 Hz, 1H), 4.51-3.88 (m, 9H), 3.77-3.55 (m, 1H), 3.53-3.15 (m, 4H), 3.11-2.78 (m, 2H), 2.45-2.29 (m, 2H), 2.14-1.95 (m, 5H), 1.47-1.20 (m, 5H).

To a solution of (rac)-ethyl (E/Z)-1,3-dimethyl-7-[3-(1-naphthyloxy)propyl]-10,13,15,16-tetrahydro-1H-pyrazolo[4',3':9,10][1,6]oxazacyclododecino[8,7,6-hi]indole-8-carboxylate (33 mg, 58.5 μmol) in ethanol (1 mL) was purged with nitrogen before adding 10% palladium (6.21 mg, 5.85 μmol) on carbon. The reaction mixture was purged with hydrogen and was then stirred under a hydrogen balloon for 3 h. The mixture was subsequently filtered trough a pad of Celite and concentrated to obtain the title compound which was used in the next step without purification.

MS: m/z=566 [M+H]$^+$

465

Intermediate 84 ethyl 7-[5-({[tert-butyl(dimethyl)silyl]oxy}methyl)-1,3-dimethyl-1H-pyrazol-4-yl]-3-[3-(1-naphthyloxy)propyl]-1H-indole-2-carboxylate

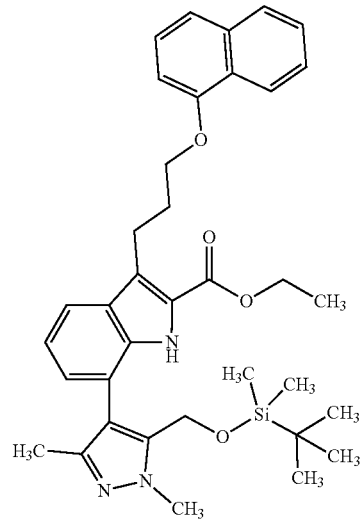 [SMILES: CCOC(=O)c1[nH]c2c(-c3c(C)nn(C)c3CO[Si](C)(C)C(C)(C)C)cccc2c1CCCOc1cccc2ccccc12]

To a solution of ethyl 7-[5-(hydroxymethyl)-1,3-dimethyl-1H-pyrazol-4-yl]-3-[3-(1-naphthyloxy)propyl]-1H-indole-2-carboxylate (see Intermediate 9, 0.5 g, 1.0 mmol) and tert-butylchlorodimethylsilane (226 mg, 1.50 mmol) in dichloromethane (10 mL) at 0° C. was added 1H-imidazole (136 mg, 2.0 mmol). The mixture was stirred at room temperature overnight, diluted with water, and extracted three times with dichloromethane. The combined organic phases were washed with saturated aqueous sodium bicarbonate solution, dried over sodium sulfate, filtered, and concentrated. The crude residue was purified by flash chromatography on silica gel (0-30% ethyl acetate/hexanes) to obtain the title compound (0.525 g).

MS: m/z=612 [M+H]$^+$ $^1$H NMR (300 MHz, Chloroform-d) δ [ppm]: 8.58 (s, 1H), 8.43-8.33 (m, 1H), 7.88-7.77 (m, 1H), 7.77-7.66 (m, 1H), 7.57-7.23 (m, 5H), 7.21-7.08 (m, 2H), 6.82-6.73 (m, 1H), 4.50-4.30 (m, 4H), 4.23 (t, J=6.2 Hz, 2H), 3.97 (s, 3H), 3.45 (t, J=7.5 Hz, 2H), 2.38 (p, J=6.6 Hz, 2H), 2.18 (s, 3H), 1.37 (t, J=7.1 Hz, 3H), 0.82 (s, 9H), −0.09 (s, 6H).

466

Intermediate 85 ethyl 1-{3-[(tert-butoxycarbonyl)amino]propyl}-7-[5-({[tert-butyl(dimethyl)silyl]oxy}methyl)-1,3-dimethyl-1H-pyrazol-4-yl]-3-[3-(1-naphthyloxy)propyl]-1H-indole-2-carboxylate

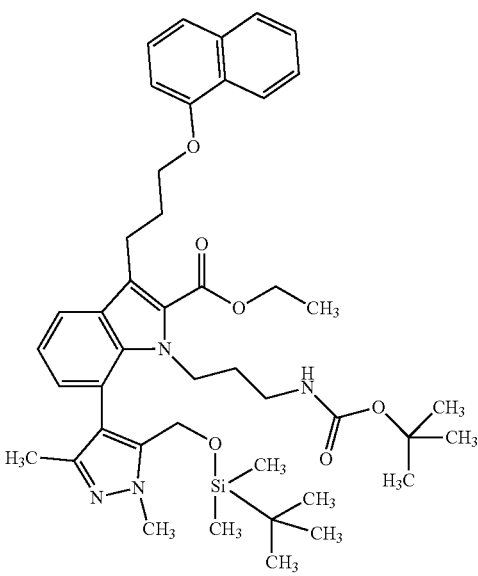 [SMILES: CCOC(=O)c1c(CCCOc2cccc3ccccc23)c2cccc(-c3c(C)nn(C)c3CO[Si](C)(C)C(C)(C)C)c2n1CCCNC(=O)OC(C)(C)C]

To a solution of ethyl 7-[5-({[tert-butyl(dimethyl)silyl]oxy}methyl)-1,3-dimethyl-1H-pyrazol-4-yl]-3-[3-(1-naphthyloxy)propyl]-1H-indole-2-carboxylate (0.52 g, 0.849 mmol) in dimethylformamide (12 mL) was added caesium carbonate (1.10 g, 3.39 mmol). The mixture was stirred at room temperature for 10 min before adding tert-butyl (3-bromopropyl)carbamate (222 mg, 0.933 mmol). The mixture was stirred at room temperature for 24 h, at which point more tert-butyl (3-bromopropyl)carbamate (22 mg. 0.1 eq) was added and the mixture was stirred overnight. The reaction mixture was concentrated and diluted with water, extracted three times with ethyl acetate and the combined organic phases were washed with water and brine, dried over sodium sulfate, filtered and concentrated. The residue was purified by flash chromatography on silica gel (30% ethyl acetate/hexanes) to give the title compound (582 mg).

MS: m/z=770 [M+H]$^+$ $^1$H NMR (300 MHz, Chloroform-d) δ [ppm]: 7.88-7.69 (m, 1H), 7.58-7.25 (m, 2H), 7.16-6.96 (m, 1H), 4.60-4.30 (m, 3H), 4.23 (t, J=6.1 Hz, 2H), 3.98 (s, 2H), 3.40 (t, J=7.5 Hz, 1H), 2.79-2.69 (m, 1H), 2.34 (t, J=7.2 Hz, 1H), 2.10 (s, 2H), 1.58 (d, J=1.9 Hz, 1H), 1.41 (d, J=8.6 Hz, 7H), 0.84 (s, 6H), −0.08 (d, J=6.0 Hz, 2H).

Intermediate 86 ethyl 1-{3-[(tert-butoxycarbonyl)amino]propyl}-7-[5-(hydroxymethyl)-1,3-dimethyl-1H-pyrazol-4-yl]-3-[3-(1-naphthyloxy)propyl]-1H-indole-2-carboxylate

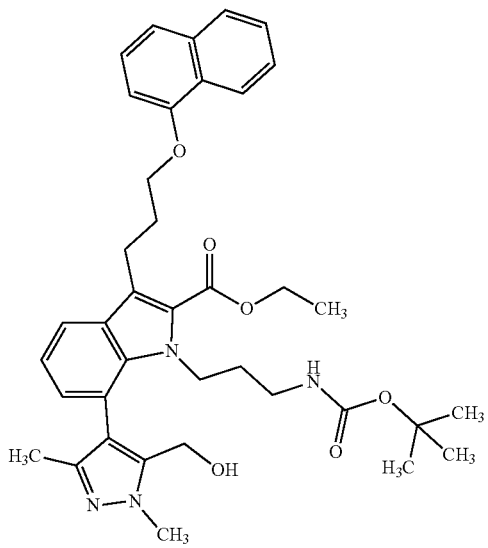 [SMILES: CCOC(=O)c1c(CCCOc2cccc3ccccc23)c2cccc(-c3c(C)nn(C)c3CO)c2n1CCCNC(=O)OC(C)(C)C]

To a solution of ethyl 1-{3-[(tert-butoxycarbonyl)amino]propyl}-7-[5-({[tert-butyl(dimethyl)silyl]oxy}methyl)-1,3-dimethyl-1H-pyrazol-4-yl]-3-[3-(1-naphthyloxy)propyl]-1H-indole-2-carboxylate (see intermediate 85, 0.564 g, 0.732 mmol) in tetrahydrofuran (7 mL) at room temperature was added tetrabutylammonium fluoride (1 M in tetrahydrofuran, 1.09 mL, 1.09 mmol). The reaction mixture was stirred at room temperature 1 h and then the reaction was stopped by adding saturated aqueous ammonium chloride solution. The mixture was extracted three times with ethyl acetate and the combined organic phases were dried over sodium sulfate, filtered, and concentrated. The residue was purified by flash chromatography on silica gel (0-10% methanol/dichloromethane) to obtain the title compound (0.475 g).

MS: m/z=655 [M+H]$^+$ $^1$H NMR (300 MHz, Chloroform-d) δ [ppm]: 8.40 (dt, J=7.2, 3.6 Hz, 1H), 7.89-7.69 (m, 2H), 7.59-7.31 (m, 4H), 7.21-7.04 (m, 1H), 6.93 (d, J=7.1 Hz, 1H), 6.85-6.75 (m, 1H), 5.28 (d, J=0.9 Hz, 1H), 4.61 (ddd, J=19.6, 14.3, 9.2 Hz, 4H), 4.46-4.01 (m, 8H), 3.41 (td, J=7.1, 3.2 Hz, 2H), 2.63 (dtd, J=28.8, 14.0, 13.5, 6.6 Hz, 2H), 2.35 (p, J=6.9 Hz, 2H), 2.05 (s, 3H), 1.51 (q, J=7.7, 6.1 Hz, 1H), 1.39 (d, J=7.9 Hz, 12H).

Intermediate 87 ethyl 7-[5-(bromomethyl)-1,3-dimethyl-1H-pyrazol-4-yl]-1-{3-[(tert-butoxycarbonyl)amino]propyl}-3-[3-(1-naphthyloxy)propyl]-1H-indole-2-carboxylate

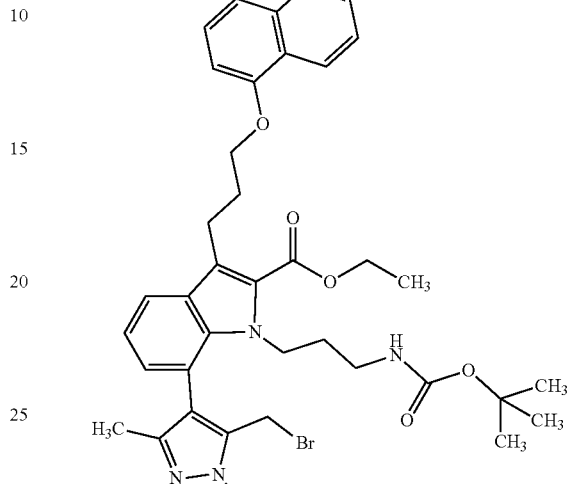

To a solution of ethyl 1-{3-[(tert-butoxycarbonyl)amino]propyl}-7-[5-(hydroxymethyl)-1,3-dimethyl-1H-pyrazol-4-yl]-3-[3-(1-naphthyloxy)propyl]-1H-indole-2-carboxylate (0.475 g, 0.723 mmol) in dichloromethane (13 mL) at 0° C. was added triphenylphosphine (264 mg, 1.01 mmol) and the mixture was stirred at 0° C. for 10 min. A 0.5 M solution of tetrabromomethane (1.73 mL, 0.867 mmol) in dichloromethane was added and the resulting mixture was stirred at room temperature for 1 h and concentrated onto Celite. The Celite-supported material was purified by flash chromatography on silica gel (0-100% ethyl acetate/hexanes) to obtain the title compound (361 mg).

MS: m/z=719 [M+H]$^+$ $^1$H NMR (300 MHz, Chloroform-d) δ [ppm]: 8.41-8.31 (m, 1H), 7.88-7.72 (m, 2H), 7.58-7.32 (m, 3H), 7.28 (d, J=3.1 Hz, 5H), 7.22-7.06 (m, 2H), 6.81 (dd, J=7.5, 1.3 Hz, 1H), 4.52 (d, J=11.4 Hz, 1H), 4.45-4.19 (m, 6H), 4.00 (s, 3H), 3.40 (t, J=7.5 Hz, 2H), 2.69 (q, J=6.6 Hz, 2H), 2.35 (t, J=7.2 Hz, 2H), 2.07 (s, 3H), 1.61-1.54 (m, 4H), 1.41 (t, J=7.2 Hz, 4H).

469

Intermediate 88

(rac)-ethyl 9,11-dimethyl-1-[3-(1-naphthyloxy)propyl]-4,5,6,7,8,9-hexahydropyrazolo[3',4':7,8][1,5]diazecino[9,10,1-hi]indole-2-carboxylate

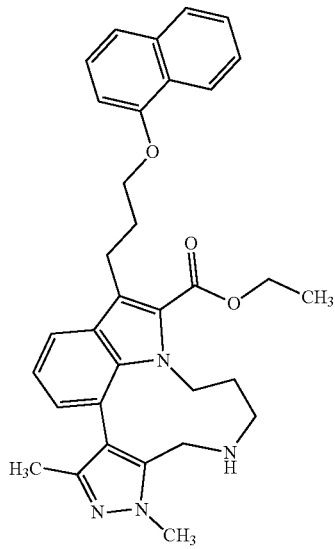 [SMILES: CCOC(=O)c1c(CCCOc2cccc3ccccc23)c2cccc3c2n1CCCNCc1c-3c(C)nn1C]

To a solution of ethyl 7-[5-(bromomethyl)-1,3-dimethyl-1H-pyrazol-4-yl]-1-{3-[(tert-butoxycarbonyl)amino]propyl}-3-[3-(1-naphthyloxy)propyl]-1H-indole-2-carboxylate (0.351 g, 0.487 mmol) in methanol (5 mL) at 0° C. was added hydrogen chloride (4 M in 1,4-dioxane, 4.85 mL, 19.4 mmol). The mixture was stirred at room temperature 2 h and was then concentrated three times from toluene. The resulting ammonium salt was dissolved in dimethylformamide (50 mL) and to this was added caesium carbonate (795 mg, 2.44 mmol) and the mixture was stirred at 30° C. for 24 h. The mixture was concentrated and diluted with water, extracted three times with ethyl acetate and the combined organic phases were washed with water and brine, dried over sodium sulfate, filtered and concentrated. The residue was purified by flash chromatography on silica gel (50% ethyl acetate/hexanes) to give the title compound (78.9 mg).

MS: m/z=537 [M+H]$^+$ $^1$H NMR (400 MHz, Chloroform-d) δ [ppm]: 8.42-8.33 (m, 1H), 7.88-7.69 (m, 2H), 7.60-7.29 (m, 4H), 7.18-7.01 (m, 2H), 6.80 (d, J=7.3 Hz, 1H), 4.58 (dt, J=14.6, 3.7 Hz, 1H), 4.45-4.16 (m, 4H), 4.09-3.84 (m, 5H), 3.42 (ddt, J=44.5, 13.5, 7.5 Hz, 2H), 3.23 (d, J=15.0 Hz, 1H), 2.88 (ddd, J=15.1, 5.9, 2.3 Hz, 1H), 2.36 (p, J=7.0 Hz, 2H), 2.09 (s, 3H), 1.92-1.74 (m, 3H), 1.52-1.32 (m, 4H).

470

Intermediate 91 ethyl 1-(2-methoxyethyl)-5-methyl-1H-pyrazole-3-carboxylate

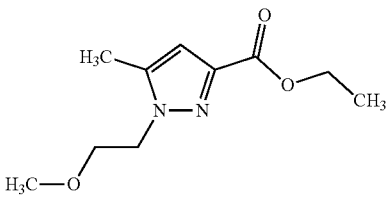

A mixture of (2-methoxyethyl)hydrazine ethanedioate (4.50 g, 25.0 mmol) and ethyl 2,4-dioxopentanoate (3.95 g, 25.0 mmol) in acetic acid (36 ml, 620 mmol) was stirred at 100° C. for 3 h. Upon cooling, the mixture was concentrated. Saturated sodium bicarbonate solution was added and the mixture was extracted with a mixture of dichloromethane and 2-propanol (4:1). The combined organic phases were filtered through a silicone filter and concentrated. The residue was purified by flash chromatography (100 g Biotage SNAP cartridge silica, hexanes/ethyl acetate gradient, 0%→50% ethyl acetate) to give the title compound 4.63 g (87% yield) together with ethyl 1-(2-methoxyethyl)-3-methyl-1H-pyrazole-5-carboxylate (0.59 g, 11% yield).

LC-MS (Method 1): R$_t$=0.87 min; MS (ESIpos): m/z=213 [M+H]$^+$ $^1$H-NMR (400 MHz, DMSO-d6) δ [ppm]: 1.247 (6.92), 1.265 (16.00), 1.283 (7.20), 2.276 (15.10), 2.278 (15.64), 2.518 (0.43), 3.329 (8.39), 3.641 (2.80), 3.653 (4.93), 3.667 (3.08), 4.204 (1.93), 4.222 (6.27), 4.233 (3.14), 4.240 (6.58), 4.247 (5.00), 4.258 (2.69), 4.260 (2.91), 6.494 (4.04), 6.495 (4.05).

Intermediate 92 ethyl 1-(2-methoxyethyl)-3-methyl-1H-pyrazole-5-carboxylate

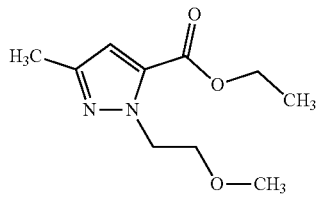

The title compound was isolated as a side product in the synthesis of ethyl 1-(2-methoxyethyl)-5-methyl-1H-pyrazole-3-carboxylate.

LC-MS (Method 1): Rt=1.01 min; MS (ESIpos): m/z=213 [M+H]$^+$ $^1$H-NMR (400 MHz, DMSO-d$_6$): δ [ppm]=6.63 (s, 1H), 4.57 (t, 2H), 4.27 (q, 2H), 3.63 (t, 2H), 3.18 (s, 3H), 2.17 (s, 3H), 1.28 (t, 3H)

Intermediate 93 ethyl 4-bromo-1-(2-methoxyethyl)-5-methyl-1H-pyrazole-3-carboxylate

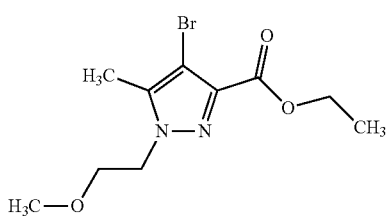 [SMILES: CCOC(=O)c1nn(CCOC)c(C)c1Br]

N-Bromosuccinimide (4.08 g, 22.9 mmol) was added to a solution of ethyl 1-(2-methoxyethyl)-5-methyl-1H-pyrazole-3-carboxylate (see Intermediate 91; 4.63 g, 21.8 mmol) in acetonitrile (60 ml) and the mixture was stirred for 2 h at 50° C.: For work-up, the mixture was diluted with ethyl acetate, washed with water and the organic phase was filtered through a silicone filter and concentrated to give the title compound (7.23 g) which was used in the next step without further purification.

LC-MS (Method 1): Rt=1.05 min; MS (ESIpos): m/z=291 [M+H]$^+$

Intermediate 94

[4-bromo-1-(2-methoxyethyl)-5-methyl-1H-pyrazol-3-yl]methanol

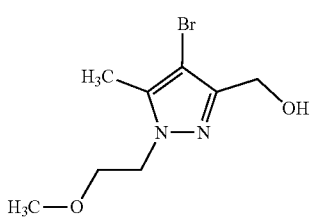

Lithium borohydride (811 mg, 37.2 mmol) was added to a solution of ethyl 4-bromo-1-(2-methoxyethyl)-5-methyl-1H-pyrazole-3-carboxylate (7.23 g, 24.8 mmol) in THF (150 ml) and the mixture was stirred for 4 h 60° C. Sodium sulfate was added and the mixture was stirred for 1 h at room temperature. Solids were filtered off, washed with THF and the filtrate was concentrated. The residue was purified by flash chromatography (110 g Biotage SNAP cartridge NH$_2$ silica, hexanes/ethyl acetate gradient, 0%→60% ethyl acetate) to give the title compound (4.55 g, 74% yield).

LC-MS (Method 2): R$_t$=0.75 min; MS (ESIpos): m/z=249 [M+H]$^+$ $^1$H-NMR (400 MHz, DMSO-d6) δ [ppm]: 2.213 (16.00), 3.200 (0.85), 3.331 (4.72), 3.596 (1.81), 3.610 (3.32), 3.623 (1.98), 4.171 (1.87), 4.185 (3.26), 4.198 (1.71), 4.305 (4.71), 4.319 (4.76), 4.966 (1.44), 4.980 (3.34), 4.994 (1.39).

Intermediate 95 ethyl 5-methyl-1-[2-(morpholin-4-yl)ethyl]-1H-pyrazole-3-carboxylate

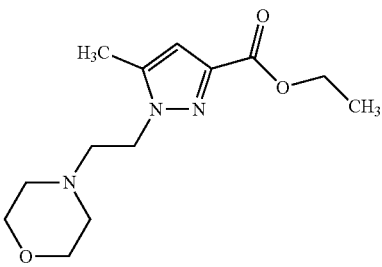 [SMILES: CCOC(=O)c1cc(C)n(CCN2CCOCC2)n1]

A mixture of 4-(2-hydrazinylethyl)morpholine (2.90 g, 20.0 mmol) and ethyl 2,4-dioxopentanoate (3.16 g, 20.0 mmol) in acetic acid (29 ml) was stirred at 100° C. für 3 h. Upon cooling, the mixture was concentrated. The residue was dissolved in ethyl acetate and the mixture was washed with saturated aqueous sodium bicarbonate solution and brine. The organic phase was filtered through a silicone filter and concentrated. The residue was purified by flash chromatography (Biotage SNAP cartridge silica, hexanes/ethyl acetate gradient, 0%→100% ethyl acetate) to give the title compound 3.00 g (56% yield) together with the regioisomer ethyl 3-methyl-1-[2-(morpholin-4-yl)ethyl]-1H-pyrazole-5-carboxylate (0.81 g, 15% yield).

LC-MS (Method 2): R$_t$=0.85 min; MS (ESIpos): m/z=268 [M+H]$^+$ $^1$H-NMR (400 MHz, DMSO-d6) δ [ppm]: 1.244 (6.85), 1.262 (15.35), 1.279 (6.90), 2.303 (16.00), 2.305 (15.43), 2.387 (2.98), 2.398 (4.03), 2.409 (3.05), 2.518 (0.89), 2.522 (0.59), 2.634 (2.44), 2.651 (5.37), 2.667 (2.68), 3.522 (4.23), 3.533 (5.25), 3.545 (4.03), 4.175 (2.47), 4.192 (5.21), 4.200 (2.48), 4.208 (2.56), 4.217 (6.82), 4.235 (6.61), 4.253 (1.97), 6.497 (4.52), 6.499 (4.34).

Intermediate 96 ethyl 3-methyl-1-[2-(morpholin-4-yl)ethyl]-1H-pyrazole-5-carboxylate

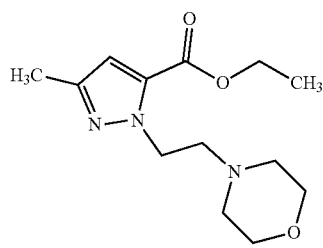 [SMILES: CCOC(=O)c1cc(C)nn1CCN1CCOCC1]

The title compound was isolated as a side product in the synthesis of ethyl 5-methyl-1-[2-(morpholin-4-yl)ethyl]-1H-pyrazole-3-carboxylate intermediate 97 0.87 g (15% yield).

LC-MS (Method 2): Rt=0.99 min; MS (ESIpos): m/z=268 [M+H]$^+$

¹H-NMR (400 MHz, DMSO-d₆): δ [ppm]=6.62 (s, 1H), 4.51 (t, 2H), 4.27 (q, 2H), 3.53-3.48 (m, 4H), 2.60 (t, 2H), 2.39-2.35 (m, 4H), 2.17 (s, 3H), 1.29 (t, 3H)

Intermediate 98 ethyl 4-bromo-5-methyl-1-[2-(morpholin-4-yl)ethyl]-1H-pyrazole-3-carboxylate

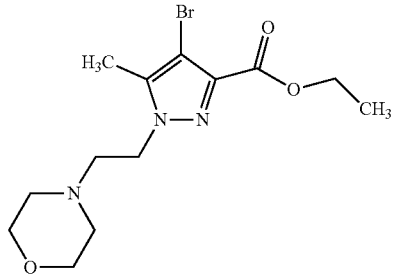 [SMILES: CCOC(=O)c1nn(CCN2CCOCC2)c(C)c1Br]

A solution of bromine in acetic acid (22 ml, 1.0 M, 22 mmol) was added to a solution of ethyl 5-methyl-1-[2-(morpholin-4-yl)ethyl]-1H-pyrazole-3-carboxylate (2.90 g, 10.8 mmol) in acetic acid (62 ml) at 0° C., and the mixture was stirred for 12 h at room temperature. For work-up, ice water was added followed by saturated aqueous sodium thiosulfate solution, and basified with saturated sodium bicarbonate solution. The mixture was extracted with ethyl acetate and the combined organic phases were filtered through a silicone filter and concentrated. The residue was purified by flash chromatography (Biotage SNAP cartridge silica, hexanes/ethyl acetate gradient, 50%→100% ethyl acetate) to give the title compound (3.3 g, 84% yield).

LC-MS (Method 2): Rt=1.10 min; MS (ESIpos): m/z=346.1 [M+H]⁺

¹H-NMR (400 MHz, DMSO-d₆): δ [ppm]=4.30-4.23 (m, 4H), 3.57-3.48 (m, 4H), 2.65 (t, 2H), 2.47-2.38 (m, 4H), 2.34-2.28 (m, 3H), 1.28 (t, 3H)

Intermediate 99

{4-bromo-5-methyl-1-[2-(morpholin-4-yl)ethyl]-1H-pyrazol-3-yl}methanol

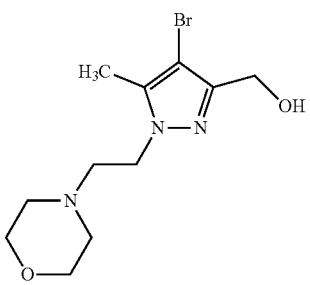 [SMILES: Cc1c(Br)c(CO)nn1CCN1CCOCC1]

Lithium borohydride (209 mg, 9.59 mmol) was added to a solution of ethyl 4-bromo-5-methyl-1-[2-(morpholin-4-yl)ethyl]-1H-pyrazole-3-carboxylate (3.32 g, 9.59 mmol) in THF (85 ml) and the mixture was stirred for 2 h room temperature and 8 h at 60° C. For work-up, saturated aqueous ammonium chloride solution was added and the mixture was extracted with ethyl acetate, the organic phase was filtered through a silicone filter and concentrated. The residue was purified by flash chromatography (Biotage SNAP cartridge silica, dichloromethane/methanol gradient 0%→20% methanol) to give the title compound 2.47 g (84% yield).

LC-MS (Method 1): $R_t$=0.49 min; MS (ESIpos): m/z=304 [M+H]⁺

¹H-NMR (400 MHz, DMSO-d₆): δ [ppm]=4.97 (t, 1H), 4.30 (d, 2H), 4.13 (t, 2H), 3.61-3.48 (m, 4H), 2.61 (t, 2H), 2.42-2.37 (m, 4H)

Intermediate 100 ethyl 4-bromo-3-methyl-1-[2-(morpholin-4-yl)ethyl]-1H-pyrazole-5-carboxylate

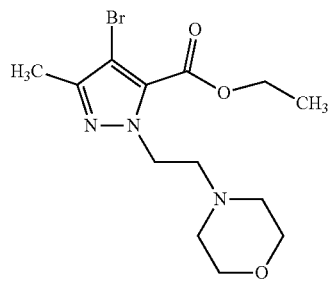 [SMILES: CCOC(=O)c1c(Br)c(C)nn1CCN1CCOCC1]

A solution of bromine in acetic acid (6.4 ml, 1.0 M, 6.4 mmol) was added to a solution of ethyl 3-methyl-1-[2-(morpholin-4-yl)ethyl]-1H-pyrazole-5-carboxylate (850 mg, 3.18 mmol) in acetic acid (18 ml) at 0° C., and the mixture was stirred for 12 h at room temperature. For work-up, ice water was added followed by saturated aqueous sodium thiosulfate solution, and basified with saturated aqueous sodium bicarbonate solution. The mixture was extracted with ethyl acetate and the combined organic phases were filtered through a silicone filter and concentrated. The residue was purified by flash chromatography (Biotage SNAP cartridge silica, hexanes/ethyl acetate gradient, 0%→100% ethyl acetate) to give the title compound 672 mg (58% yield).

LC-MS (Method 1): $R_t$=0.80 min; MS (ESIpos): m/z=346 [M+H]⁺

¹H-NMR (400 MHz, DMSO-d6) δ [ppm]: 1.154 (1.59), 1.172 (3.31), 1.190 (1.69), 1.312 (4.07), 1.322 (0.49), 1.330 (8.74), 1.347 (4.10), 1.987 (6.55), 2.165 (16.00), 2.327 (0.42), 2.340 (2.19), 2.351 (3.08), 2.363 (2.44), 2.522 (0.77), 2.574 (1.62), 2.591 (3.60), 2.607 (1.71), 3.486 (2.72), 3.497 (3.62), 3.509 (2.82), 3.999 (0.49), 4.017 (1.48), 4.035 (1.47), 4.053 (0.48), 4.310 (1.31), 4.328 (4.08), 4.346 (4.05), 4.363 (1.26), 4.486 (1.66), 4.503 (3.48), 4.519 (1.64).

Intermediate 101

{4-bromo-3-methyl-1-[2-(morpholin-4-yl)ethyl]-1H-pyrazol-5-yl}methanol

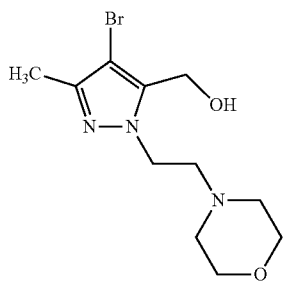 [SMILES: Cc1nn(CCN2CCOCC2)c(CO)c1Br]

Lithium borohydride (52.7 mg, 2.42 mmol) was added to a solution of ethyl 4-bromo-3-methyl-1-[2-(morpholin-4-yl)ethyl]-1H-pyrazole-5-carboxylate (670 mg, 1.94 mmol) in THF (11 ml) and the mixture was stirred for 30 min at room temperature and 6 h at 60° C. Additional lithium borohydride (21.1 mg, 968 µmol) was added and the mixture was stirred for 6 h at 60° C. For work-up, saturated aqueous ammonium chloride solution was added and the mixture was extracted with ethyl acetate, the organic phase was filtered through a silicone filter and concentrated. The residue was purified by flash chromatography (Biotage SNAP cartridge silica, hexanes to ethyl acetate to ethyl acetate/ethanol 4:1 gradient) to give the title compound 409 mg (68% yield).

LC-MS (Method 2): $R_t$=0.78 min; MS (ESIpos): m/z=304 [M+H]$^+$ $^1$H-NMR (400 MHz, DMSO-d6) δ [ppm]: 1.988 (0.51), 2.095 (16.00), 2.392 (2.00), 2.522 (1.19), 2.628 (1.69), 2.644 (3.61), 2.661 (1.85), 2.668 (0.45), 3.159 (0.55), 3.172 (0.58), 3.532 (2.91), 3.543 (3.89), 3.554 (3.00), 4.187 (1.71), 4.204 (3.51), 4.220 (1.66), 4.445 (2.07), 4.455 (2.17), 5.489 (0.85).

Intermediate 102 ethyl 4-bromo-5-(bromomethyl)-1-(2-methoxyethyl)-1H-pyrazole-3-carboxylate

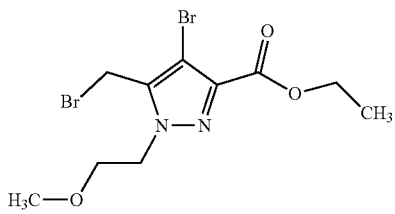

N-Bromosuccinimide (3.13 g, 17.6 mmol) was added to a solution of ethyl 1-(2-methoxyethyl)-5-methyl-1H-pyrazole-3-carboxylate (see Intermediate 91; 1.78 g, 8.39 mmol) in 1,2-dichloroethane (28 ml) and the mixture was stirred for 6 h at 80° C. For work-up, the mixture was diluted with dichloromethane, washed with water and the organic phase was filtered through a silicone filter and concentrated. The residue was purified by flash chromatography (100 g Biotage SNAP cartridge silica, hexanes/ethyl acetate gradient, 20%→100% ethyl acetate) to give ethyl 4-bromo-1-(2-methoxyethyl)-5-methyl-1H-pyrazole-3-carboxylate (2.22 g, 91% yield) and the title compound ethyl 4-bromo-5-(bromomethyl)-1-(2-methoxyethyl)-1H-pyrazole-3-carboxylate (0.65 g, 21%).

LC-MS (Method 2): Rt=1.18 min; MS (ESIpos): m/z=370 [M+H]$^+$ $^1$H-NMR (400 MHz, DMSO-d$_6$): δ [ppm]=4.77 (s, 2H), 4.47 (t, 2H), 4.29 (q, 2H), 3.71 (t, 2H), 3.23 (s, 3H), 1.29 (t, 4H)

Intermediate 103 ethyl 4-bromo-1-(2-methoxyethyl)-5-(morpholin-4-ylmethyl)-1H-pyrazole-3-carboxylate

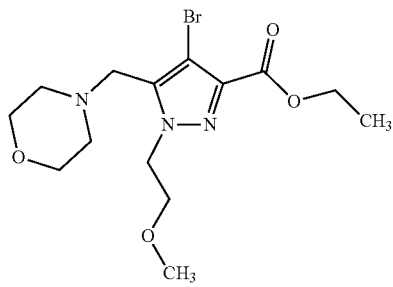 [SMILES: CCOC(=O)c1nn(CCOC)c(CN2CCOCC2)c1Br]

A mixture of ethyl 4-bromo-5-(bromomethyl)-1-(2-methoxyethyl)-1H-pyrazole-3-carboxylate (645 mg, 1.74 mmol), morpholine (320 µl, 3.7 mmol) and potassium carbonate (506 mg, 3.66 mmol) in acetonitrile (7.3 ml) was stirred at room temperature for 12 h. For work-up, water and brine were added and the mixture was extracted with ethyl acetate, filtered through a silicone filter and concentrated to give the title compound (660 mg, 101% yield) which was used in the next step without further purification.

LC-MS (Method 2): $R_t$=1.09 min; MS (ESIpos): m/z=376 [M+H]$^+$ $^1$H-NMR (400 MHz, DMSO-d6) δ [ppm]: 1.172 (0.74), 1.270 (3.47), 1.288 (7.63), 1.305 (3.48), 1.987 (1.42), 2.210 (0.74), 2.326 (0.43), 2.361 (2.19), 2.372 (1.61), 2.518 (1.21), 2.522 (0.81), 3.231 (16.00), 3.527 (1.71), 3.538 (2.41), 3.549 (1.73), 3.586 (5.13), 3.713 (1.27), 3.727 (2.76), 3.741 (1.32), 4.250 (1.00), 4.267 (3.16), 4.285 (3.10), 4.303 (0.95), 4.450 (1.29), 4.464 (2.50), 4.477 (1.16).

Intermediate 104

[4-bromo-1-(2-methoxyethyl)-5-(morpholin-4-ylmethyl)-1H-pyrazol-3-yl]methanol

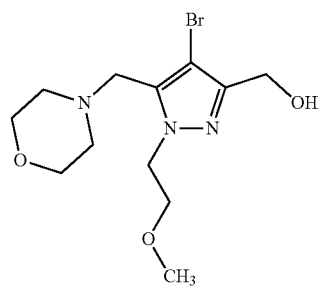 [SMILES: COCCn1nc(CO)c(Br)c1CN1CCOCC1]

Lithium borohydride (38.2 mg, 1.75 mmol) was added to a solution of ethyl 4-bromo-1-(2-methoxyethyl)-5-(morpholin-4-ylmethyl)-1H-pyrazole-3-carboxylate (660 mg, 1.75 mmol) in THF (16 ml) and the mixture was stirred for 2 h room temperature and 8 h at 60° C. For work-up, saturated aqueous ammonium chloride solution was added and the mixture was extracted with ethyl acetate, the organic phase was filtered through a silicone filter and concentrated. The residue was purified by flash chromatography (Biotage SNAP cartridge silica, hexanes/ethyl acetate gradient 50%→100% ethyl acetate) to give the title compound 383 mg (90% purity, 59% yield).

LC-MS (Method 1): $R_t$=0.49 min; MS (ESIpos): m/z=335 [M+H]$^+$ $^1$H-NMR (400 MHz, DMSO-d$_6$): δ [ppm]=5.05-4.99 (m, 1H), 4.35-4.27 (m, 4H), 3.68 (t, 2H), 3.59-3.47 (m, 6H), 3.23 (s, 3H), 2.37-2.28 (m, 4H)

Intermediate 105 ethyl 4-bromo-1-methyl-5-(morpholin-4-ylmethyl)-1H-pyrazole-3-carboxylate

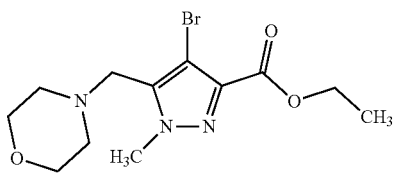 [SMILES: CCOC(=O)c1nn(C)c(CN2CCOCC2)c1Br]

The title compound (3.29 g, 99% yield) was prepared in analogy to the synthesis of ethyl 4-bromo-1-(2-methoxyethyl)-5-(morpholin-4-ylmethyl)-1H-pyrazole-3-carboxylate (see intermediate 103) using ethyl 4-bromo-5-(bromomethyl)-1-methyl-1H-pyrazole-3-carboxylate (see intermediate 300, 3.26 g, 10.0 mmol) as starting material.

LC-MS (Method 1): $R_t$=0.75 min; MS (ESIpos): m/z=332 [M+H]$^+$ $^1$H-NMR (400 MHz, DMSO-d6) δ [ppm]: 1.172 (0.42), 1.263 (4.12), 1.281 (9.01), 1.288 (0.40), 1.298 (4.21), 1.987 (0.82), 2.353 (2.19), 2.364 (3.08), 2.375 (2.27), 2.518 (0.75), 2.522 (0.50), 3.527 (2.53), 3.538 (3.43), 3.549 (2.52), 3.568 (7.74), 3.948 (16.00), 4.238 (1.28), 4.256 (4.01), 4.274 (3.94), 4.291 (1.21).

Intermediate 106

[4-bromo-1-methyl-5-(morpholin-4-ylmethyl)-1H-pyrazol-3-yl]methanol

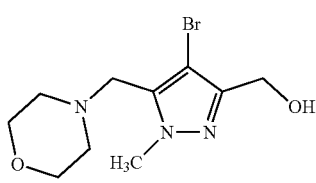 [SMILES: Cn1nc(CO)c(Br)c1CN1CCOCC1]

The title compound (2.15 g, 71% yield) was prepared in analogy to the synthesis of [4-bromo-1-(2-methoxyethyl)-5-(morpholin-4-ylmethyl)-1H-pyrazol-3-yl]methanol using ethyl 4-bromo-1-methyl-5-(morpholin-4-ylmethyl)-1H-pyrazole-3-carboxylate (3.29 g, 9.90 mmol,) as starting material.

LC-MS (Method 2): $R_t$=0.69 min; MS (ESIpos): m/z=290 [M+H]$^+$ $^1$H-NMR (400 MHz, DMSO-d$_6$): δ [ppm]=4.99 (t, 1H), 4.32 (d, 2H), 3.82 (s, 3H), 3.58-3.51 (m, 4H), 3.50 (s, 2H), 2.41-2.29 (m, 4H)

Intermediate 107

4-bromo-5-(methoxymethyl)-1-methyl-1H-pyrazole-3-carboxylic acid

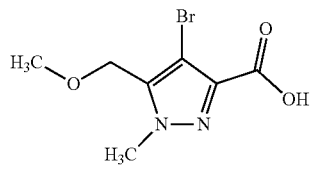

A mixture of ethyl 4-bromo-5-(bromomethyl)-1-methyl-1H-pyrazole-3-carboxylate (see intermediate 300, 3.70 g, 11.3 mmol) and potassium carbonate (7.84 g, 56.7 mmol) in methanol (100 ml) was stirred at 40° C. for 16 h. For work-up, the mixture was concentrated, water and citric acid were added and the mixture was extracted with a mixture of dichloromethane and 2-propanol (4:1) to give the title compound (2.94 g) which was used in the next step without further purification.

LC-MS (Method 1): Rt=0.67 min; MS (ESIpos): m/z=249 [M+H]$^+$

Intermediate 108 ethyl 4-bromo-5-(methoxymethyl)-1-methyl-1H-pyrazole-3-carboxylate

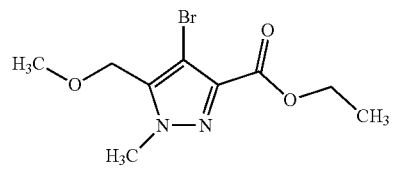

A mixture of 4-bromo-5-(methoxymethyl)-1-methyl-1H-pyrazole-3-carboxylic acid (2.65 g, 10.6 mmol), iodoethane (860 µl, 11 mmol) and caesium carbonate (10.4 g, 31.9 mmol) in DMF (60 ml) was stirred at room temperature for 3 h. For work-up, water was added and the mixture was extracted with ethyl acetate, the organic phase was washed with water, filtered through a silicone filter and concentrated to give the title compound (3.10 g), which was used in the next step without further purification.

LC-MS (Method 1): Rt=0.98 min; MS (ESIpos): m/z=277 [M+H]$^+$

Intermediate 109

[4-bromo-5-(methoxymethyl)-1-methyl-1H-pyrazol-3-yl]methanol

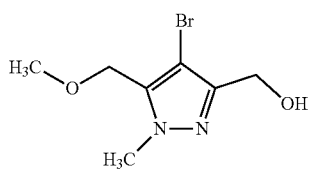

Lithium borohydride (366 mg, 16.8 mmol) was added to a solution of ethyl 4-bromo-5-(methoxymethyl)-1-methyl-1H-pyrazole-3-carboxylate (3.10 g, 11.2 mmol) in THF (91 ml) and the mixture was stirred for 16 h at 60° C. For work-up, ammonium sulfate was added and the mixture was stirred for 1 h, solids were filtered off, and the filtrate was concentrated. The residue was purified by flash chromatography (55 g Biotage SNAP cartridge NH$_2$ silica, hexanes/ethyl acetate gradient 0%→20% ethyl acetate) to give the title compound 1.06 g (40% yield).

LC-MS (Method 1): R$_t$=0.67 min; MS (ESIpos): m/z=217 [M–H$_2$O+H]$^+$ $^1$H-NMR (500 MHz, DMSO-d6) δ [ppm]: 2.514 (0.89), 2.518 (0.85), 2.522 (0.70), 3.253 (16.00), 3.328 (13.71), 4.327 (4.12), 4.338 (3.92), 4.433 (7.81), 5.018 (1.11), 5.029 (2.55), 5.040 (1.07).

Intermediate 110 ethyl 5-cyclopropyl-1-ethyl-1H-pyrazole-3-carboxylate

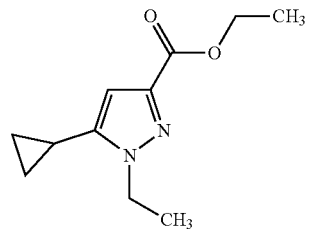

A mixture of 5-cyclopropyl-1H-pyrazole-3-carboxylic acid (CAS No 133261-6-0, Combi-Blocks; or Bioorg. Med. Chem. Lett, 2007, 17, 5620-5623, 2.50 g, 16.4 mmol), iodoethane (3.2 ml, 39 mmol) and potassium carbonate (6.81 g, 49.3 mmol) in DMF (37 ml) was stirred at 50° C. for 4 h. For work-up, water was added and the mixture was extracted with ethyl acetate, the combined organic phases were washed with brine, filtered through a silicone filter and concentrated. The residue was purified by flash chromatography (Biotage SNAP cartridge silica, hexanes/ethyl acetate gradient 20%→50% ethyl acetate) to give the title compound 1.49 g (43% yield) and the regioisomer ethyl 3-cyclopropyl-1-ethyl-1H-pyrazole-5-carboxylate (1.53 g, 44% yield)

LC-MS (Method 2): R$_t$=1.06 min; MS (ESIpos): m/z=209 [M+H]$^+$ $^1$H-NMR (400 MHz, DMSO-d6) δ [ppm]: 0.657 (1.09), 0.667 (3.58), 0.672 (3.40), 0.679 (3.56), 0.683 (2.53), 0.685 (3.49), 0.695 (1.39), 0.934 (1.32), 0.944 (3.26), 0.950 (3.26), 0.955 (1.64), 0.961 (1.55), 0.965 (3.35), 0.971 (3.20), 0.982 (1.09), 1.237 (7.38), 1.255 (16.00), 1.272 (7.54), 1.341 (6.48), 1.359 (14.32), 1.377 (6.65), 1.891 (0.42), 1.904 (0.85), 1.912 (0.91), 1.916 (0.61), 1.925 (1.60), 1.934 (0.59), 1.937 (0.84), 1.945 (0.77), 3.330 (6.48), 4.191 (2.32), 4.209 (7.22), 4.227 (8.94), 4.245 (8.29), 4.264 (6.09), 4.281 (1.86), 6.356 (7.05).

Intermediate 111 ethyl 3-cyclopropyl-1-ethyl-1H-pyrazole-5-carboxylate

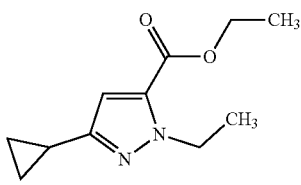

The title compound was isolated as side product in the synthesis of ethyl 5-cyclopropyl-1-ethyl-1H-pyrazole-3-carboxylate (1.53 g, 44% yield).

LC-MS (Method 2): R$_t$=1.24 min; MS (ESIpos): m/z=209 [M+H]$^+$ $^1$H-NMR (400 MHz, DMSO-d6) δ [ppm]: 0.632 (0.77), 0.642 (2.60), 0.648 (2.62), 0.655 (2.68), 0.661 (2.62), 0.670 (1.00), 0.837 (0.97), 0.846 (2.37), 0.852 (2.32), 0.858 (1.27), 0.863 (1.18), 0.867 (2.51), 0.873 (2.29), 0.884 (0.78), 1.263 (7.78), 1.281 (16.00), 1.298 (7.68), 1.861 (0.75), 1.869 (0.80), 1.881 (1.40), 1.890 (0.53), 1.893 (0.76), 1.902 (0.69), 4.237 (1.50), 4.255 (4.53), 4.272 (4.48), 4.290 (1.43), 4.367 (1.27), 4.385 (3.86), 4.403 (3.85), 4.420 (1.23), 6.534 (5.97).

Intermediate 112 ethyl 4-bromo-5-cyclopropyl-1-ethyl-1H-pyrazole-3-carboxylate

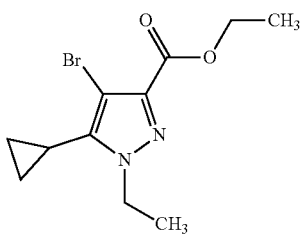 [SMILES: CCOC(=O)c1nn(CC)c(C2CC2)c1Br]

N-Bromosuccinimide (2.43 g, 13.6 mmol) was added to a solution of ethyl 5-cyclopropyl-1-ethyl-1H-pyrazole-3-carboxylate (1.35 g, 6.49 mmol) in acetonitrile (27 ml) and the mixture was stirred for 4.5 h at 60° C. For work-up, the mixture was diluted with ethyl acetate, washed with water and the organic phase was filtered through a silicone filter and concentrated. The residue was purified by flash chromatography (Biotage SNAP cartridge silica, hexanes/ethyl acetate gradient, 20→50% ethyl acetate) to give the title compound 1.31 g (69% yield).

LC-MS (Method 2): R$_t$=1.20 min; MS (ESIpos): m/z=287 [M+H]$^+$

Intermediate 113

(4-bromo-5-cyclopropyl-1-ethyl-1H-pyrazol-3-yl)methanol

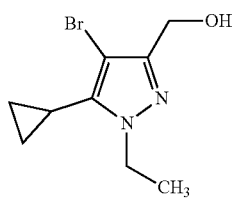

The title compound (982 mg, 86% yield) was prepared in analogy to the synthesis of [4-bromo-1-(2-methoxyethyl)-5-(morpholin-4-ylmethyl)-1H-pyrazol-3-yl]methanol using ethyl 4-bromo-5-cyclopropyl-1-ethyl-1H-pyrazole-3-carboxylate (1.31 g, 4.56 mmol) as starting material.

LC-MS (Method 1): $R_t$=0.91 min; MS (ESIpos): m/z=245 [M+H]$^+$ $^1$H-NMR (400 MHz, DMSO-d6) δ [ppm]: 0.774 (1.09), 0.785 (3.78), 0.790 (3.63), 0.799 (4.01), 0.804 (3.70), 0.814 (1.57), 0.973 (1.48), 0.984 (3.39), 0.989 (3.51), 0.994 (1.75), 1.000 (1.57), 1.004 (3.61), 1.010 (3.44), 1.021 (1.16), 1.155 (0.44), 1.173 (0.93), 1.191 (0.48), 1.300 (0.41), 1.312 (7.16), 1.329 (16.00), 1.347 (7.35), 1.719 (0.62), 1.732 (1.27), 1.739 (1.26), 1.745 (0.71), 1.753 (2.41), 1.760 (0.73), 1.766 (1.17), 1.774 (1.16), 1.787 (0.53), 1.988 (1.75), 2.518 (0.78), 2.523 (0.50), 3.159 (1.17), 3.172 (1.22), 4.018 (0.40), 4.035 (0.41), 4.131 (2.24), 4.149 (7.09), 4.167 (6.94), 4.185 (2.13), 4.283 (6.88), 4.297 (7.03), 4.926 (1.57), 4.940 (3.54), 4.954 (1.47).

Intermediate 114

(4-bromo-3-cyclopropyl-1-ethyl-1H-pyrazol-5-yl)methanol

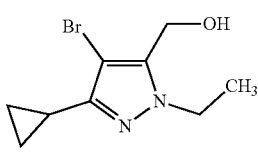

The title compound (565 mg, 80% purity, 40% yield) was prepared in 2 steps in analogy to the synthesis of (4-bromo-5-cyclopropyl-1-ethyl-1H-pyrazol-3-yl)methanol using ethyl 3-cyclopropyl-1-ethyl-1H-pyrazole-5-carboxylate (1.52 g, 7.27 mmol) as starting material.

LC-MS (Method 2): $R_t$=0.94 min; MS (ESIpos): m/z=245 [M+H]$^+$

Intermediate 115

2-methoxyethyl 5-cyclopropyl-1-(2-methoxyethyl)-1H-pyrazole-3-carboxylate

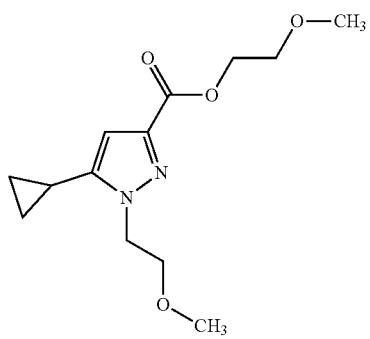 [SMILES: COCCOC(=O)c1cc(C2CC2)n(CCOC)n1]

The title compound was prepared in analogy to the synthesis of ethyl 5-cyclopropyl-1-ethyl-1H-pyrazole-3-carboxylate using 5-cyclopropyl-1H-pyrazole-3-carboxylic acid (CAS No 133261-6-0, Combi-Blocks; or Bioorg. Med. Chem. Lett, 2007, 17, 5620-5623, 2.40 g, 15.8 mmol) and 2-bromoethyl methyl ether (3.6 ml, 38 mmol) as starting materials to give the title compound (1.28 g, 30% yield) and the regioisomer 2-methoxyethyl 3-cyclopropyl-1-(2-methoxyethyl)-1H-pyrazole-5-carboxylate (2.01 g, 46% yield).

LC-MS (Method 2): $R_t$=0.92 min; MS (ESIpos): m/z=268 [M+H]$^+$ $^1$H-NMR (400 MHz, DMSO-d$_6$): δ [ppm]=6.36 (s, 1H), 4.39 (t, 2H), 4.33-4.28 (m, 2H), 3.72 (t, 2H), 3.61-3.56 (m, 2H), 3.27 (s, 3H), 3.22 (s, 3H), 1.98-1.90 (m, 1H), 0.99-0.92 (m, 2H), 0.70-0.65 (m, 2H)

Intermediate 116

2-methoxyethyl 3-cyclopropyl-1-(2-methoxyethyl)-1H-pyrazole-5-carboxylate

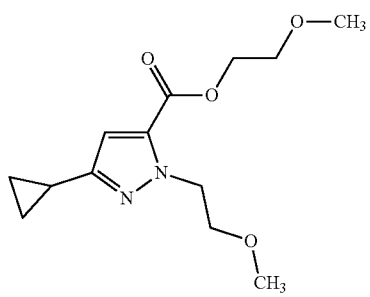 [SMILES: COCCOC(=O)c1cc(C2CC2)nn1CCOC]

The title compound was isolated as side product in the synthesis 2-methoxyethyl 5-cyclopropyl-1-(2-methoxyethyl)-1H-pyrazole-3-carboxylate (2.01 g, 46% yield).

LC-MS (Method 2): $R_t$=1.02 min; MS (ESIpos): m/z=268 [M+H]$^+$ $^1$H-NMR (400 MHz, DMSO-d$_6$): δ [ppm]=6.54 (s, 1H), 4.55 (t, 2H), 4.36-4.32 (m, 2H), 3.64-3.59 (m, 4H), 3.33 (s, 3H), 3.18 (s, 3H), 1.94-1.86 (m, 1H), 0.90-0.84 (m, 2H), 0.68-0.63 (m, 2H)

Intermediate 117

2-methoxyethyl 4-bromo-5-cyclopropyl-1-(2-methoxyethyl)-1H-pyrazole-3-carboxylate

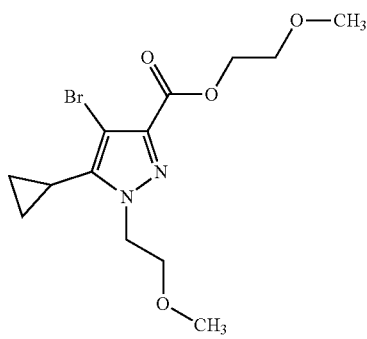 [SMILES: COCCOC(=O)c1nn(CCOC)c(C2CC2)c1Br]

N-Bromosuccinimide (1.02 g, 5.72 mmol) was added to a solution of 2-methoxyethyl 5-cyclopropyl-1-(2-methoxyethyl)-1H-pyrazole-3-carboxylate (1.28 g, 4.77 mmol) in acetonitrile (30 ml) and the mixture was stirred for 16 h at 50° C. For work-up, the mixture was diluted with ethyl acetate, washed with water and the organic phase was filtered through a silicone filter and concentrated to give the title compound (1.78 g) which was used in the next step without further purification.

LC-MS (Method 1): Rt=1.09 min; MS (ESIpos): m/z=346 [M+H]$^+$ $^1$H-NMR (400 MHz, DMSO-d6) δ [ppm]: 0.833 (1.11), 0.838 (1.02), 0.846 (1.15), 0.852 (1.05), 0.862 (0.50), 1.024 (0.43), 1.035 (0.98), 1.040 (1.07), 1.045 (0.54), 1.052 (0.51), 1.056 (1.08), 1.062 (1.00), 1.757 (0.76), 1.988 (0.81), 2.518 (0.98), 2.523 (0.73), 2.562 (8.31), 3.277 (16.00), 3.554 (1.23), 3.594 (1.48), 3.603 (0.98), 3.606 (1.56), 3.610 (0.97), 3.618 (1.50), 3.719 (1.08), 3.732 (2.03), 3.745 (1.17), 4.331 (1.52), 4.340 (0.91), 4.343 (1.48), 4.347 (0.93), 4.355 (1.44), 4.413 (1.09), 4.426 (1.94), 4.439 (1.04).

Intermediate 118

[4-bromo-5-cyclopropyl-1-(2-methoxyethyl)-1H-pyrazol-3-yl]methanol

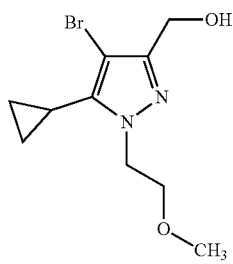

Lithium borohydride (201 mg, 9.22 mmol) was added to a solution of 2-methoxyethyl 4-bromo-5-cyclopropyl-1-(2-methoxyethyl)-1H-pyrazole-3-carboxylate (1.60 g, 4.61 mmol,) in THF (37 ml) and the mixture was stirred for 16 h at 60° C. For work-up, solid sodium sulfate was added and the mixture was stirred for 1 h, solids were filtered off and the filtrate was concentrated. The residue was purified by flash chromatography (55 g Biotage SNAP cartridge NH$_2$ silica, hexanes/ethyl acetate gradient 0%→100% ethyl acetate) to give the title compound (930 mg, 73% yield).

LC-MS (Method 1): R$_t$=0.87 min; MS (ESIpos): m/z=275 [M+H]$^+$ $^1$H-NMR (400 MHz, DMSO-d6) δ [ppm]: 0.778 (0.48), 0.788 (1.56), 0.794 (1.42), 0.802 (1.60), 0.807 (1.42), 0.817 (0.62), 0.970 (0.62), 0.980 (1.39), 0.986 (1.44), 0.991 (0.71), 0.997 (0.70), 1.001 (1.45), 1.007 (1.30), 1.018 (0.46), 1.705 (0.52), 1.712 (0.52), 1.726 (0.98), 1.739 (0.47), 1.746 (0.46), 2.518 (1.05), 2.522 (0.66), 3.200 (0.42), 3.216 (16.00), 3.675 (1.56), 3.688 (3.11), 3.702 (1.65), 4.267 (1.68), 4.281 (3.24), 4.288 (4.06), 4.294 (1.77), 4.301 (4.08), 4.947 (1.06), 4.960 (2.37), 4.974 (1.04).

Intermediate 119

2-methoxyethyl 4-bromo-3-cyclopropyl-1-(2-methoxyethyl)-1H-pyrazole-5-carboxylate

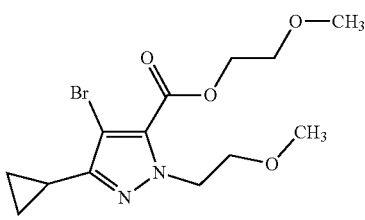 [SMILES: COCCOC(=O)c1c(Br)c(C2CC2)nn1CCOC]

N-Bromosuccinimide (2.77 g, 15.6 mmol) was added to a solution of 2-methoxyethyl 3-cyclopropyl-1-(2-methoxyethyl)-1H-pyrazole-5-carboxylate (1.99 g, 7.41 mmol) in acetonitrile (31 ml) and the mixture was stirred for 5 h at 60° C. For work-up, the mixture was diluted with ethyl acetate, washed with water and the organic phase was filtered through a silicone filter and concentrated. The residue was purified by flash chromatography (Biotage SNAP cartridge silica, hexanes/ethyl acetate gradient, 20→50% ethyl acetate) to give the title compound (2.28 g, 88% yield).

LC-MS (Method 2): R$_t$=1.24 min; MS (ESIpos): m/z=347 [M+H]$^+$

Intermediate 120

[4-bromo-3-cyclopropyl-1-(2-methoxyethyl)-1H-pyrazol-5-yl]methanol

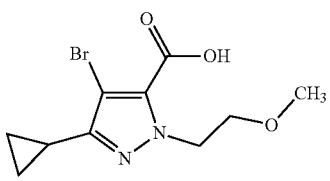 [SMILES: COCCn1nc(C2CC2)c(Br)c1C(=O)O]

The title compound (1.20 g, 67% yield) was prepared in analogy to the synthesis of {4-bromo-3-methyl-1-[2-(morpholin-4-yl)ethyl]-1H-pyrazol-5-yl}methanol using 2-methoxyethyl 4-bromo-3-cyclopropyl-1-(2-methoxyethyl)-1H-pyrazole-5-carboxylate (2.28 g, 6.57 mmol) as starting material.

LC-MS (Method 2): R$_t$=0.93 min; MS (ESIpos): m/z=275 [M+H]$^+$

¹H-NMR (400 MHz, DMSO-d₆): δ [ppm]=5.31-5.27 (m, 1H), 4.46-4.42 (m, 2H), 4.22 (t, 2H), 3.60 (t, 2H), 3.20 (s, 3H), 1.81-1.73 (m, 1H), 0.88-0.83 (m, 2H), 0.76-0.70 (m, 2H)

Intermediate 121 ethyl 5-methyl-1-(2,2,2-trifluoroethyl)-1H-pyrazole-3-carboxylate

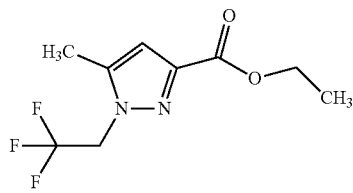 [SMILES: CCOC(=O)c1cc(C)n(CC(F)(F)F)n1]

The title compound was prepared in analogy to the synthesis of ethyl 1-(2-methoxyethyl)-5-methyl-1H-pyrazole-3-carboxylate using (2,2,2-trifluoroethyl)hydrazine (2.8 ml, 32 mmol) and ethyl 2,4-dioxopentanoate (5.00 g, 31.6 mmol) as starting materials to give the title compound (1.12 g, 15% yield) and the regioisomer ethyl 3-methyl-1-(2,2,2-trifluoroethyl)-1H-pyrazole-5-carboxylate (3.19 g, 42% yield).

LC-MS (Method 1): R$_t$=1.02 min; MS (ESIpos): m/z=237 [M+H]⁺

¹H-NMR (400 MHz, DMSO-de): δ [ppm]=6.62 (s, 1H), 5.236 (q, 2H), 4.26 (q, 2H), 2.33 (s, 3H), 1.27 (t, 2H), 1.23 (t, 3H)

Intermediate 122 ethyl 3-methyl-1-(2,2,2-trifluoroethyl)-1H-pyrazole-5-carboxylate

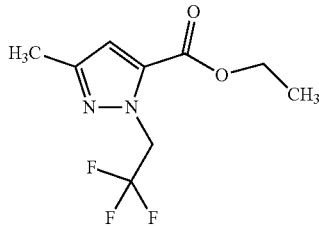 [SMILES: CCOC(=O)c1cc(C)nn1CC(F)(F)F]

The title compound was isolated as a side product in the synthesis of ethyl 5-methyl-1-(2,2,2-trifluoroethyl)-1H-pyrazole-3-carboxylate (3.19 g, 42% yield).

LC-MS (Method 1): R$_t$=1.19 min; MS (ESIpos): m/z=237 [M+H]⁺

¹H-NMR (400 MHz, DMSO-d₆): δ [ppm]=6.82 (s, 1H), 5.35 (q, 2H), 4.30 (q, 2H), 2.22 (s, 3H), 1.29 (t, 3H)

Intermediate 123

[4-bromo-5-methyl-1-(2,2,2-trifluoroethyl)-1H-pyrazol-3-yl]methanol

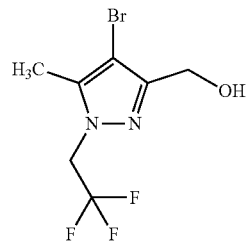

The title compound (1.10 g, 91% yield) was prepared in 2 steps in analogy to the synthesis of {4-bromo-5-methyl-1-[2-(morpholin-4-yl)ethyl]-1H-pyrazol-3-yl}methanol using ethyl 5-methyl-1-(2,2,2-trifluoroethyl)-1H-pyrazole-3-carboxylate (1.12 g, 4.74 mmol) as starting material.

LC-MS (Method 2): R$_t$=0.85 min; MS (ESIpos): m/z=273 [M+H]⁺

¹H-NMR (400 MHz, DMSO-d6) δ [ppm]: 2.271 (16.00), 2.518 (1.47), 2.523 (0.98), 4.332 (4.11), 4.346 (4.31), 5.081 (1.30), 5.095 (1.03), 5.105 (4.35), 5.108 (3.16), 5.128 (3.72), 5.151 (1.12).

Intermediate 124

[4-bromo-3-methyl-1-(2,2,2-trifluoroethyl)-1H-pyrazol-5-yl]methanol

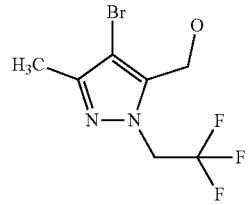

The title compound (2.82 g, 83% yield) was prepared in 2 steps in analogy to the synthesis of {4-bromo-5-methyl-1-[2-(morpholin-4-yl)ethyl]-1H-pyrazol-3-yl}methanol using ethyl 3-methyl-1-(2,2,2-trifluoroethyl)-1H-pyrazole-5-carboxylate (2.98 g, 12.6 mmol) as starting material.

LC-MS (Method 2): R$_t$=0.92 min; MS (ESIpos): m/z=273 [M+H]⁺

¹H-NMR (400 MHz, DMSO-d6) δ [ppm]: 2.133 (16.00), 2.523 (0.89), 4.490 (2.55), 4.503 (2.63), 5.052 (0.99), 5.075 (2.92), 5.097 (2.85), 5.120 (0.89), 5.546 (0.55), 5.559 (1.48), 5.572 (0.56).

Intermediate 125 ethyl 1-cyclopropyl-5-methyl-1H-pyrazole-3-carboxylate

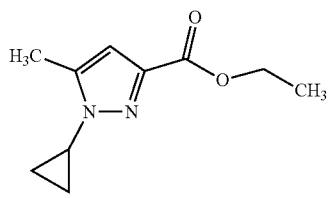

The title compound was prepared in analogy to the synthesis of ethyl 1-(2-methoxyethyl)-5-methyl-1H-pyrazole-3-carboxylate using cyclopropylhydrazine dihydrochloride (3.63 g, 25.0 mmol) and ethyl 2,4-dioxopentanoate (3.95 g, 25.0 mmol) as starting materials to give the title compound (2.31 g, 47% yield) and the regioisomer ethyl 1-cyclopropyl-3-methyl-1H-pyrazole-5-carboxylate (1.26 g, 26% yield).

LC-MS (Method 2): $R_t$=0.95 min; MS (ESIpos): m/z=195 [M+H]$^+$ $^1$H-NMR (400 MHz, DMSO-d6) δ [ppm]: 1.009 (1.44), 1.010 (1.57), 1.012 (1.59), 1.017 (2.32), 1.022 (1.82), 1.028 (1.57), 1.030 (1.75), 1.035 (4.04), 1.040 (3.10), 1.043 (2.36), 1.048 (3.31), 1.051 (3.66), 1.056 (1.65), 1.058 (1.45), 1.237 (7.16), 1.254 (15.85), 1.272 (7.33), 2.351 (16.00), 2.518 (0.74), 2.523 (0.49), 3.565 (0.51), 3.576 (0.83), 3.584 (0.98), 3.593 (1.87), 3.600 (0.72), 3.603 (0.92), 3.610 (0.80), 3.620 (0.47), 4.194 (2.16), 4.212 (6.85), 4.230 (6.71), 4.247 (2.05), 6.518 (4.60), 6.519 (4.52).

Intermediate 126 ethyl 1-cyclopropyl-3-methyl-1H-pyrazole-5-carboxylate

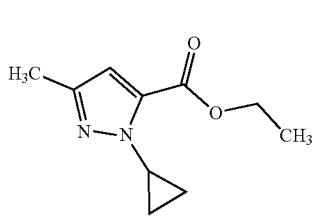

The title compound was isolated as side product in the synthesis of ethyl 1-cyclopropyl-5-methyl-1H-pyrazole-3-carboxylate (1.26 g, 26% yield).

LC-MS (Method 2): $R_t$=1.12 min; MS (ESIpos): m/z=195 [M+H]$^+$ $^1$H-NMR (400 MHz, DMSO-d6) δ [ppm]: 0.938 (0.51), 0.950 (1.23), 0.953 (1.42), 0.958 (2.19), 0.969 (1.86), 0.977 (1.74), 0.979 (1.34), 0.987 (0.87), 1.060 (0.78), 1.062 (0.90), 1.073 (2.48), 1.081 (2.45), 1.088 (1.30), 1.091 (1.44), 1.102 (0.53), 1.277 (6.45), 1.295 (14.10), 1.312 (6.52), 2.140 (16.00), 4.181 (0.41), 4.190 (0.84), 4.199 (1.07), 4.209 (1.67), 4.219 (0.99), 4.228 (0.82), 4.261 (1.99), 4.278 (6.40), 4.296 (6.33), 4.314 (1.91), 6.641 (4.46).

Intermediate 127

(4-bromo-1-cyclopropyl-5-methyl-1H-pyrazol-3-yl)methanol

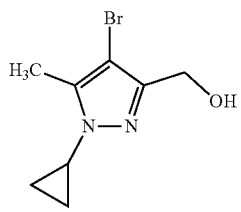

The title compound (1.77 g, 69% yield) was prepared in 2 steps in analogy to the synthesis of [4-bromo-3-cyclopropyl-1-(2-methoxyethyl)-1H-pyrazol-5-yl]methanol using ethyl 1-cyclopropyl-5-methyl-1H-pyrazole-3-carboxylate (2.31 g, 11.9 mmol) as starting material.

LC-MS (Method 2): $R_t$=0.80 min; MS (ESIpos): m/z=231 [M+H]$^+$ $^1$H-NMR (400 MHz, DMSO-d6) δ [ppm]: 0.965 (0.84), 0.967 (0.80), 0.972 (1.87), 0.976 (0.99), 0.981 (0.66), 0.983 (0.85), 0.988 (2.26), 0.991 (2.50), 0.993 (2.43), 0.998 (2.06), 1.002 (1.91), 1.005 (0.86), 1.007 (0.72), 2.286 (16.00), 2.518 (0.74), 2.523 (0.55), 3.489 (0.50), 3.498 (1.01), 3.508 (0.44), 4.273 (3.35), 4.287 (3.54), 4.940 (0.80), 4.954 (1.88), 4.968 (0.74).

Intermediate 128 ethyl 1-methyl-5-(propan-2-yl)-1H-pyrazole-3-carboxylate

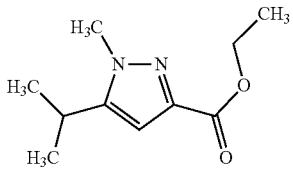

The title compound was prepared in analogy to the synthesis of ethyl 1-(2-methoxyethyl)-5-methyl-1H-pyrazole-3-carboxylate using ethyl 5-methyl-2,4-dioxohexanoate (5.00 g, 26.9 mmol) and methylhydrazine (1.4 ml, 27 mmol) as starting materials to give the title compound 2.98 g (57% yield) and the regioisomer ethyl 3-isopropyl-1-methyl-1H-pyrazole-5-carboxylate (0.46 g, 9% yield LC-MS (Method 1): $R_t$=1.03 min; MS (ESIpos): m/z=197 [M+H]$^+$ $^1$H-NMR (400 MHz, DMSO-d6) δ [ppm]: 1.185 (14.12), 1.202 (14.32), 1.244 (3.84), 1.263 (8.12), 1.280 (3.88), 2.523 (1.29), 3.019 (0.80), 3.036 (1.04), 3.053 (0.76), 3.833 (16.00), 4.200 (1.24), 4.218 (3.85), 4.236 (3.79), 4.254 (1.19), 6.525 (4.09).

Intermediate 129 ethyl 3-isopropyl-1-methyl-1H-pyrazole-5-carboxylate

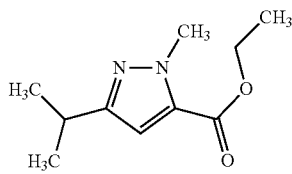

The title compound was isolated as a side product in the synthesis of ethyl 1-methyl-5-(propan-2-yl)-1H-pyrazole-3-carboxylate (0.46 g, 9% yield).

LC-MS (Method 1): $R_t$=1.22 min; MS (ESIpos): m/z=197 [M+H]$^+$ $^1$H-NMR (400 MHz, DMSO-d6) δ [ppm]: 1.175 (15.82), 1.192 (16.00), 1.273 (3.90), 1.291 (8.81), 1.309 (4.04), 2.859 (0.70), 2.876 (0.91), 2.893 (0.66), 4.008 (15.25), 4.245 (1.16), 4.263 (3.74), 4.281 (3.73), 4.299 (1.14), 6.678 (3.66).

Intermediate 130 ethyl 4-bromo-1-methyl-5-(propan-2-yl)-1H-pyrazole-3-carboxylate

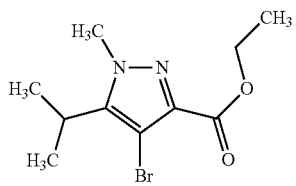

N-Bromosuccinimide (2.70 g, 15.2 mmol) was added to a solution of ethyl 1-methyl-5-(propan-2-yl)-1H-pyrazole-3-carboxylate (2.98 g, 15.2 mmol) in 1,2-dichloroethane (50 ml, 630 mmol) and the mixture was stirred for 2 h at 80° C. For work-up, saturated aqueous sodium thiosulfate solution was added and the mixture was extracted with dichloromethane and the combined organic phases were filtered through a silicone filter and concentrated to give the title compound (4.91 g, 118% calculated yield) which was used in the next step without further purification.

LC-MS (Method 1): $R_t$=1.18 min; MS (ESIpos): m/z=275 [M+H]$^+$

Intermediate 131

[4-bromo-1-methyl-5-(propan-2-yl)-1H-pyrazol-3-yl]methanol

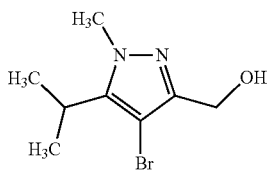

The title compound (2.62 g, 63% yield) was prepared in analogy to the synthesis of [4-bromo-5-cyclopropyl-1-(2-methoxyethyl)-1H-pyrazol-3-yl]methanol using ethyl 4-bromo-1-methyl-5-(propan-2-yl)-1H-pyrazole-3-carboxylate (4.91 g, 17.8 mmol) as starting material.

LC-MS (Method 1): $R_t$=0.89 min; MS (ESIpos): m/z=233 [M+H]$^+$ $^1$H-NMR (400 MHz, DMSO-d6) δ [ppm]: 1.286 (13.15), 1.304 (13.14), 2.518 (1.06), 2.523 (0.77), 3.182 (0.81), 3.200 (1.06), 3.218 (0.74), 3.776 (16.00), 4.272 (4.29), 4.286 (4.50), 4.917 (1.23), 4.931 (2.82), 4.945 (1.18).

Intermediate 134

(rac)-ethyl 9,11-dimethyl-1-[3-(naphthalen-1-yloxy)propyl]-5,6,8,9-tetrahydro-4H-pyrazolo[4',3':8,9][1,5]oxazecino[7,6,5-hi]indole-2-carboxylate

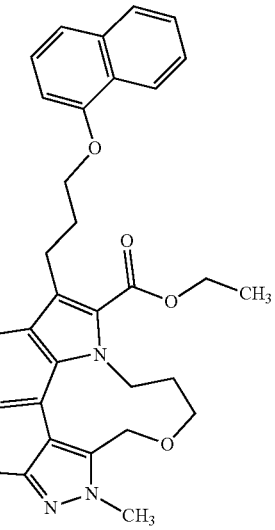

A mixture of ethyl 7-[5-(hydroxymethyl)-1,3-dimethyl-1H-pyrazol-4-yl]-3-[3-(naphthalen-1-yloxy)propyl]-1H-indole-2-carboxylate (see Intermediate 9, 600 mg, 1.21 mmol), caesium carbonate (1.96 g, 6.03 mmol) and 1,3-diiodopropane (140 μl, 1.2 mmol) in acetonitrile (15 ml, 280 mmol) was stirred for 4 days at room temperature followed by 16 h at 60° C. For work-up, the mixture was concentrated, water was added and the mixture was extracted with a mixture of dichloromethane and 2-propanol (4:1). The combined organic phases were filtered through a silicone filter and concentrated. The residue was purified by flash chromatography (50 g Biotage SNAP cartridge silica, hexanes/ethyl acetate gradient, 0%→100% ethyl acetate) to give the title compound (230 mg, 35% yield).

LC-MS (Method 1): $R_t$=1.70 min; MS (ESIpos): m/z=538.3 [MH]$^+$ $^1$H-NMR (400 MHz, DMSO-d6) δ [ppm]: 1.562 (0.55), 1.588 (0.50), 1.628 (0.46), 1.657 (0.53), 1.921 (16.00), 2.074 (4.25), 2.182 (0.99), 2.199 (1.41), 2.216 (1.05), 2.323 (0.71), 2.327 (0.97), 2.331 (0.70), 2.518 (3.40), 2.523 (2.26), 2.555 (0.49), 2.582 (0.84), 2.611 (0.52), 2.665 (0.65), 2.669 (0.90), 2.674 (0.62), 3.254 (0.50), 3.269 (0.62), 3.287 (0.93), 3.307 (0.59), 3.362 (0.97), 3.380 (0.59), 3.396 (0.52), 3.622 (1.84), 3.658 (1.88), 3.701 (0.71), 3.733 (0.65), 3.816 (15.64), 3.853 (0.44), 3.882 (0.87), 3.911 (0.50), 3.918

(0.41), 4.186 (1.47), 4.201 (3.07), 4.215 (1.40), 4.514 (0.82), 4.549 (0.76), 4.746 (2.02), 4.781 (1.93), 6.887 (1.87), 6.905 (2.02), 6.932 (1.78), 6.935 (1.82), 6.949 (2.37), 6.952 (2.14), 7.046 (2.07), 7.065 (2.26), 7.084 (1.52), 7.368 (1.38), 7.388 (2.64), 7.407 (2.20), 7.443 (2.74), 7.464 (1.49), 7.478 (0.52), 7.482 (0.67), 7.495 (1.55), 7.499 (1.37), 7.510 (1.75), 7.514 (2.36), 7.519 (1.72), 7.530 (1.47), 7.533 (1.69), 7.547 (0.71), 7.550 (0.52), 7.750 (1.87), 7.753 (1.93), 7.770 (1.78), 7.773 (1.69), 7.853 (1.64), 7.859 (0.99), 7.872 (1.76), 7.877 (1.37), 8.198 (1.44), 8.201 (1.46), 8.220 (1.37), 13.214 (1.09).

Intermediate 135 ethyl 7-[3-(hydroxymethyl)-1-(2-methoxyethyl)-5-methyl-1H-pyrazol-4-yl]-3-[3-(naphthalen-1-yloxy)propyl]-1H-indole-2-carboxylate

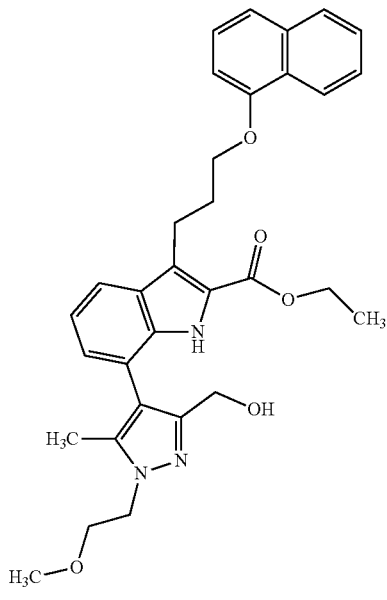 [SMILES: CCOC(=O)c1[nH]c2c(-c3c(CO)nn(CCOC)c3C)cccc2c1CCCOc1cccc2ccccc12]

XPhos Pd G2 (see abbreviation list, 125 mg, 159 µmol) was added to a degassed mixture of ethyl 3-[3-(naphthalen-1-yloxy)propyl]-7-(4,4,5,5-tetramethyl-1,3,2-dioxaborolan-2-yl)-1H-indole-2-carboxylate (see Intermediate 5, 2.59 g, 5.19 mmol [4-bromo-1-(2-methoxyethyl)-5-methyl-1H-pyrazol-3-yl]methanol (see Intermediate 94, 1.18 g, 4.72 mmol) aqueous potassium phosphate solution (19 ml, 0.50 M, 9.4 mmol) and THF (57 ml) and the mixture was stirred for 2 h at 45° C. For work-up, ethyl acetate was added, the mixture was filtered through a pad of celite, eluted with ethyl acetate and the organic phase was washed with brine, filtered through a silicone filter and concentrated. The residue was purified by flash chromatography (50 g Biotage SNAP cartridge silica, hexanes/ethyl acetate gradient, 50%→100% ethyl acetate) to give the title compound (2.04 g, 95% purity, 69% yield).

LC-MS (Method 2): R$_t$=1.57 min; MS (ESIpos): m/z=542 [M+H]$^+$ $^1$H-NMR (400 MHz, DMSO-d6) δ [ppm]: 1.155 (0.81), 1.173 (1.63), 1.190 (0.85), 1.258 (2.78), 1.275 (6.49), 1.293 (2.86), 1.988 (2.92), 2.166 (0.56), 2.182 (8.51), 2.213 (1.92), 2.233 (0.70), 2.250 (0.52), 2.327 (0.45), 2.518 (1.58), 2.523 (1.09), 2.669 (0.45), 3.205 (1.77), 3.266 (1.08), 3.273 (16.00), 3.358 (0.98), 3.375 (0.60), 3.725 (1.01), 3.739 (2.26), 3.753 (1.10), 4.017 (0.60), 4.035 (0.58), 4.200 (0.85), 4.216 (1.74), 4.225 (1.21), 4.230 (1.01), 4.242 (3.70), 4.256 (2.44), 4.260 (3.71), 4.269 (1.86), 4.278 (1.28), 4.305 (0.41), 5.777 (0.74), 6.908 (0.91), 6.925 (1.00), 7.080 (1.65), 7.084 (1.78), 7.094 (3.19), 7.373 (0.73), 7.394 (1.38), 7.413 (1.23), 7.450 (1.39), 7.471 (0.85), 7.491 (0.41), 7.504 (0.91), 7.508 (0.78), 7.513 (0.97), 7.521 (1.96), 7.528 (0.96), 7.533 (0.85), 7.537 (0.96), 7.660 (0.78), 7.670 (0.68), 7.674 (0.77), 7.684 (0.67), 7.860 (0.80), 7.868 (0.43), 7.878 (0.77), 7.884 (0.68), 8.228 (0.72), 8.234 (0.66), 8.250 (0.61), 8.252 (0.66), 11.346 (0.87).

Intermediate 136 ethyl 1-{3-[(tert-butoxycarbonyl)(methyl)amino]propyl}-7-[3-(hydroxymethyl)-1-(2-methoxyethyl)-5-methyl-1H-pyrazol-4-yl]-3-[3-(naphthalen-1-yloxy)propyl]-1H-indole-2-carboxylate

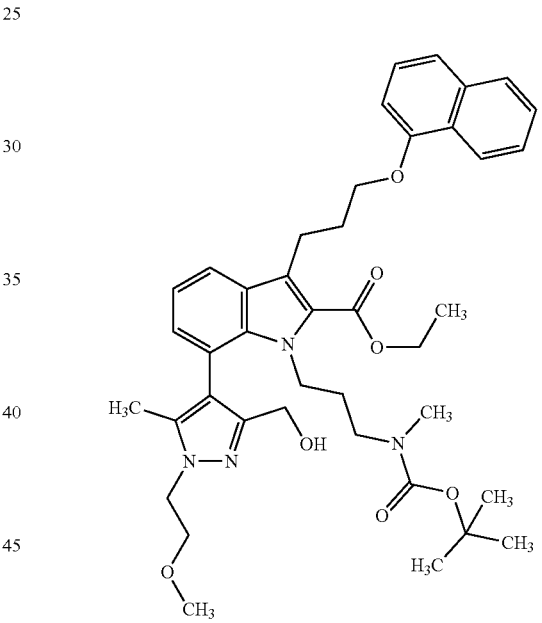

A mixture of ethyl 7-[3-(hydroxymethyl)-1-(2-methoxyethyl)-5-methyl-1H-pyrazol-4-yl]-3-[3-(naphthalen-1-yloxy)propyl]-1H-indole-2-carboxylate (1.02 g, 1.88 mmol, caesium carbonate (3.07 g, 9.42 mmol) and tert-butyl (3-bromopropyl)methylcarbamate (see Intermediate 1, 522 mg, 2.07 mmol) in DMF (23 ml) was stirred for 2 days at room temperature. For work-up, water was added and the mixture was extracted with a mixture of dichloromethane and 2-propanol (4:1). The combined organic phases were filtered through a silicone filter and concentrated. The residue was purified by flash chromatography (Biotage SNAP cartridge silica, hexanes to ethyl acetate to ethyl acetate/ethanol 4:1 gradient) to give the title compound (740 mg, 73% purity, 40% yield).

LC-MS (Method 2): R$_t$=1.71 min; MS (ESIpos): m/z=713 [M+H]$^+$

493

Intermediate 137 ethyl 7-[3-(bromomethyl)-1-(2-methoxyethyl)-5-methyl-1H-pyrazol-4-yl]-1-{3-[(tert-butoxycarbonyl)(methyl)amino]propyl}-3-[3-(naphthalen-1-yloxy)propyl]-1H-indole-2-carboxylate

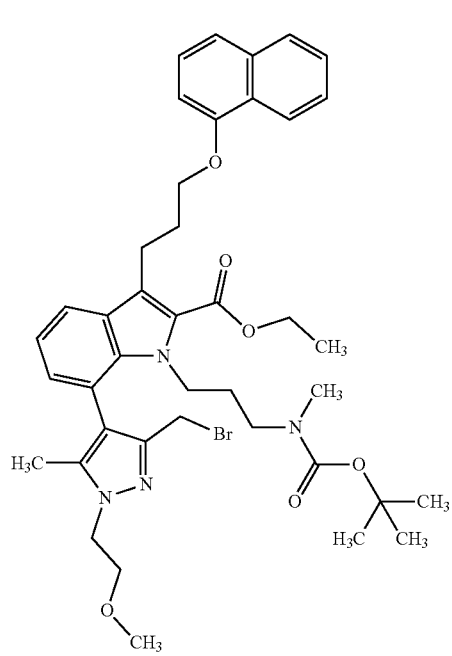 [SMILES: CCOC(=O)c1c(CCCOc2cccc3ccccc23)c2cccc(-c3c(CBr)nn(CCOC)c3C)c2n1CCCN(C)C(=O)OC(C)(C)C]

Tetrabromomethane (757 mg, 2.28 mmol) was added to a solution of ethyl 1-{3-[(tert-butoxycarbonyl)(methyl)amino]propyl}-7-[3-(hydroxymethyl)-1-(2-methoxyethyl)-5-methyl-1H-pyrazol-4-yl]-3-[3-(naphthalen-1-yloxy)propyl]-1H-indole-2-carboxylate (740 mg, 1.04 mmol) and triphenylphosphine (653 mg, 2.49 mmol) in dichloromethane (19 ml) at 0° C. and the mixture was stirred for 2 h at room temperature. For work-up, the mixture was concentrated and used in the next step without further purification.

LC-MS (Method 2): $R_t$=1.81 min; MS (ESIpos): m/z=775 [M+H]$^+$

494

Intermediate 138 ethyl 7-[3-(bromomethyl)-1-(2-methoxyethyl)-5-methyl-1H-pyrazol-4-yl]-1-[3-(methylamino)propyl]-3-[3-(naphthalen-1-yloxy)propyl]-1H-indole-2-carboxylate hydrochloric acid salt Hydrogen chloride (19 ml, 4.0 M in dioxane, 77 mmol) was added to a solution of ethyl 7-[3-(bromomethyl)-1-(2-methoxyethyl)-5-methyl-1H-pyrazol-4-yl]-1-{3-[(tert-butoxycarbonyl)(methyl)amino]propyl}-3-[3-(naphthalen-1-yloxy)propyl]-1H-indole-2-carboxylate (1.50 g, 54% purity, 1.04 mmol) in ethanol (17 ml) and the mixture was stirred for 2 h at room temperature. For work-up, the reaction mixture was concentrated to give the title compound (1.50 g) which was used in the next step without further purification.

Intermediate 139

(rac)-ethyl 10-(2-methoxyethyl)-7,11-dimethyl-1-[3-(naphthalen-1-yloxy)propyl]-4,5,6,7,8,10-hexahydropyrazolo[3',4':7,8][1,5]diazecino[9,10,1-hi]indole-2-carboxylate

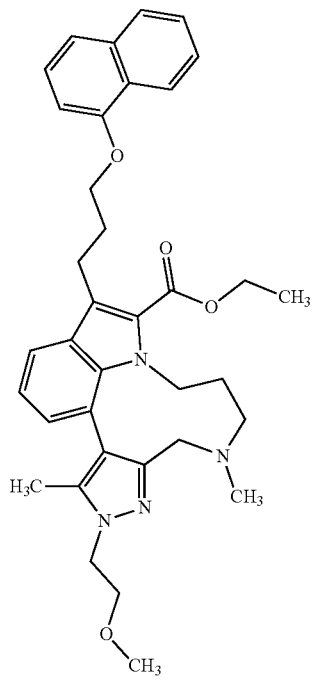 [SMILES: CCOC(=O)c1c(CCCOc2cccc3ccccc23)c2cccc3c2n1CCCN(C)Cc1nn(CCOC)c(C)c1-3]

A mixture of ethyl 7-[3-(bromomethyl)-1-(2-methoxyethyl)-5-methyl-1H-pyrazol-4-yl]-1-[3-(methylamino)propyl]-3-[3-(naphthalen-1-yloxy)propyl]-1H-indole-2-carboxylate hydrochloric acid salt (1.50 g, crude product) and caesium carbonate (1.70 g, 5.21 mmol) in DMF (100 ml) was stirred at 65° C. for 20 h. For work-up, water was added and the mixture was extracted with a mixture of dichloromethane and 2-propanol (4:1). The combined organic phases were filtered through a silicone filter and concentrated. The residue was purified by flash chromatography (50 g Biotage SNAP cartridge silica, hexanes/ethyl acetate 1:1 gradient to ethyl acetate/ethanol 4:1) followed by preparative HPLC [Instrument: Waters Autopurification system; column: Waters XBrigde C18 5μ 100×30 mm; eluent A: water+0.1 vol-% TFA (99%), eluent B: acetonitrile; gradient: 0.00-0.50 min 35% B (25→70 mL/min), 0.51-5.50 min 70-90% B (70 mL/min), DAD scan: 210-400 nm] to give the title compound (79.0 mg, 13% yield).

LC-MS (Method 2): $R_t$=1.75 min; MS (ESIpos): m/z=595 [M+H]$^+$ $^1$H-NMR (400 MHz, DMSO-d6) δ [ppm]: 1.155 (0.74), 1.173 (1.60), 1.190 (0.84), 1.259 (2.81), 1.277 (6.36), 1.295 (2.88), 1.852 (7.08), 1.988 (3.02), 2.013 (9.29), 2.075 (1.51), 2.176 (0.56), 2.193 (0.84), 2.209 (0.56), 2.318 (0.42), 2.323 (0.95), 2.327 (1.37), 2.332 (0.95), 2.337 (0.39), 2.443 (0.53), 2.518 (5.09), 2.523 (3.69), 2.660 (0.44), 2.665 (1.00), 2.669 (1.39), 2.673 (0.95), 2.679 (0.42), 3.151 (0.70), 3.184 (1.23), 3.238 (1.79), 3.245 (16.00), 3.270 (1.02), 3.347 (0.95), 3.656 (0.39), 3.668 (0.53), 3.682 (1.04), 3.695 (0.56), 3.705 (1.07), 3.718 (0.63), 4.017 (0.63), 4.035 (0.60), 4.178 (0.70), 4.189 (1.07), 4.196 (1.28), 4.203 (1.60), 4.217 (2.16), 4.223 (1.49), 4.232 (1.28), 4.241 (1.18), 4.249 (1.16), 4.259 (0.49), 4.267 (1.02), 4.277 (0.44), 4.294 (0.44), 6.805 (1.04), 6.808 (1.04), 6.822 (1.25), 6.826 (1.18), 6.874 (0.98), 6.891 (1.07), 6.969 (1.04), 6.986 (1.07), 6.988 (1.23), 7.006 (0.93), 7.364 (0.79), 7.385 (1.39), 7.404 (1.16), 7.447 (1.39), 7.468 (0.84), 7.509 (0.91), 7.516 (1.23), 7.525 (2.02), 7.533 (1.42), 7.540 (0.98), 7.680 (1.07), 7.682 (1.04), 7.700 (1.00), 7.703 (0.93), 7.860 (0.84), 7.869 (0.44), 7.878 (0.58), 7.883 (0.70), 8.216 (0.72), 8.223 (0.58), 8.240 (0.67).

Intermediate 140 ethyl 7-{3-(hydroxymethyl)-5-methyl-1-[2-(morpholin-4-yl)ethyl]-1H-pyrazol-4-yl}-3-[3-(naphthalen-1-yloxy)propyl]-1H-indole-2-carboxylate

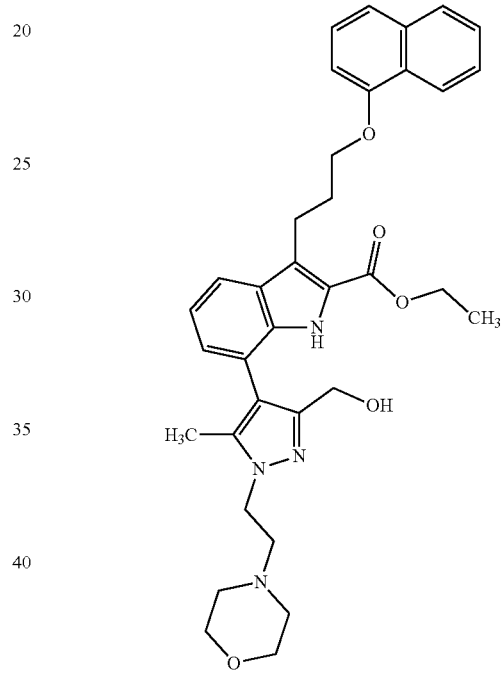

XPhos Pd G2 (see abbreviation list, 128 mg, 163 μmol) was added to a degassed mixture of ethyl 3-[3-(naphthalen-1-yloxy)propyl]-7-(4,4,5,5-tetramethyl-1,3,2-dioxaborolan-2-yl)-1H-indole-2-carboxylate (see Intermediate 5, 2.65 g, 5.32 mmol), {4-bromo-5-methyl-1-[2-(morpholin-4-yl)ethyl]-1H-pyrazol-3-yl}methanol (see Intermediate 99, 1.47 g, 4.83 mmol) aqueous potassium phosphate solution (19 ml, 0.50 M, 9.7 mmol) and THF (59 ml) and the mixture was stirred for 2 h at 45° C. For work-up, ethyl acetate was added, the mixture was filtered through a pad of celite, eluted with ethyl acetate and the organic phase was washed with brine, filtered through a silicone filter and concentrated. The residue was purified by flash chromatography (100 g Biotage SNAP cartridge silica, dichloromethane/methanol 9:1) to give the title compound (2.86 g, 95% purity, 86% yield).

LC-MS (Method 1): $R_t$=1.40 min; MS (ESIpos): m/z=597 [M+H]$^+$ $^1$H-NMR (400 MHz, DMSO-d$_6$): δ [ppm]=11.34 (s, 1H), 8.27-8.21 (m, 1H), 7.91-7.83 (m, 1H), 7.71-7.64 (m, 1H), 7.56-7.37 (m, 4H), 7.14-7.04 (m, 2H), 6.92 (d, 1H), 5.76 (t, 1H), 4.30-4.16 (m, 8H), 3.62-3.54 (m, 4H), 3.39-3.35 (m, 2H), 2.73 (t, 2H), 2.48-2.43 (m, 4H), 2.27-2.15 (m, 5H), 1.27 (t, 3H).

Intermediate 141

(rac)-ethyl (11E/Z)-3-methyl-2-[2-(morpholin-4-yl)ethyl]-7-[3-(naphthalen-1-yloxy)propyl]-2,10,13,15-tetrahydropyrazolo[4',3':9,10][1,6]oxazacycloundecino[8,7,6-hi]indole-8-carboxylate

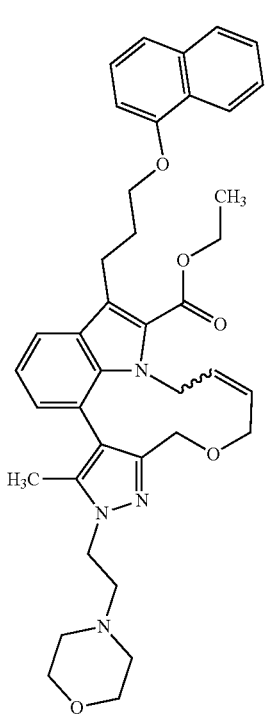 [SMILES: CCOC(=O)c1c(CCCOc2cccc3ccccc23)c2cccc3c2n1CC=CCOCc1nn(CCN2CCOCC2)c(C)c1-3]

A mixture of ethyl 7-{3-(hydroxymethyl)-5-methyl-1-[2-(morpholin-4-yl)ethyl]-1H-pyrazol-4-yl}-3-[3-(naphthalen-1-yloxy)propyl]-1H-indole-2-carboxylate (1.27 g, 2.13 mmol), caesium carbonate (3.47 g, 10.6 mmol) and (E)-1,4-dibromobut-2-ene (455 mg, 2.13 mmol) in DMF (40 ml) was stirred for 20 h at room temperature. For work-up, the mixture was concentrated, water was added and the mixture was extracted with a mixture of dichloromethane and 2-propanol (4:1). The combined organic phases were filtered through a silicone filter and concentrated. The residue was purified by flash chromatography (25 g Biotage SNAP cartridge silica, hexanes to ethyl acetate to ethyl acetate/ethanol 9:1 gradient) to give the title compound (827 mg, 60% yield).

LC-MS (Method 2): $R_t$=1.65 min; MS (ESIpos): m/z=649 [M+H]$^+$

Intermediate 142

(rac)-ethyl 3-methyl-2-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylate

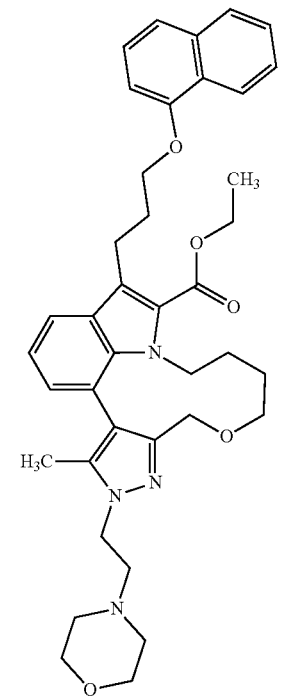 [SMILES: CCOC(=O)c1c(CCCOc2cccc3ccccc23)c2cccc3c2n1CCCCOCc1nn(CCN2CCOCC2)c(C)c1-3]

An autoclave was charged with (rac)-ethyl (11E/Z)-3-methyl-2-[2-(morpholin-4-yl)ethyl]-7-[3-(naphthalen-1-yloxy)propyl]-2,10,13,15-tetrahydropyrazolo[4',3':9,10][1,6]oxazacycloundecino[8,7,6-hi]indole-8-carboxylate (827 mg, 1.27 mmol), ethanol (22 ml), THF (4.5 ml) and palladium 10% on charcoal (136 mg, 127 μmol) and the mixture was stirred under 21 bar hydrogen atmosphere at room temperature over night. For work-up, the mixture was filtered through a pad of celite, eluted with ethyl acetate and the combined filtrates were concentrated under reduced pressure to give the title compound (757 mg, 90% purity, 82% yield), which was directly used in the next step.

LC-MS (Method 1): $R_t$=1.57 min; MS (ESIpos): m/z=651 [M+H]$^+$

499

Intermediate 143

(rac)-ethyl (11Z)-2-(2-methoxyethyl)-3-methyl-7-[3-(naphthalen-1-yloxy)propyl]-2,10,13,15-tetrahydropyrazolo[4',3':9,10][1,6]oxazacycloundecino[8,7,6-hi]indole-8-carboxylate

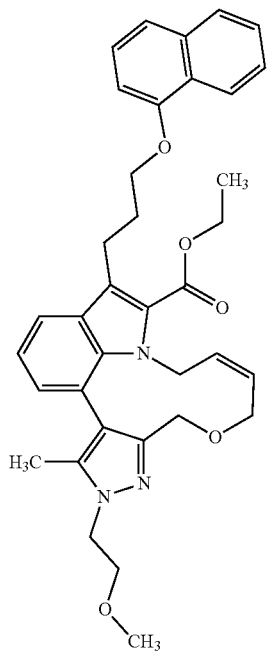 [SMILES: CCOC(=O)c1c(CCCOc2cccc3ccccc23)c2cccc3c2n1C/C=C\COCc1nn(CCOC)c(C)c1-3]

A mixture of ethyl 7-[3-(hydroxymethyl)-1-(2-methoxyethyl)-5-methyl-1H-pyrazol-4-yl]-3-[3-(naphthalen-1-yloxy)propyl]-1H-indole-2-carboxylate (see Intermediate 135, 900 mg, 1.66 mmol), (2Z)-1,4-dichlorobut-2-ene (170 µl, 1.7 mmol), caesium carbonate (2.71 g, 8.31 mmol) and sodium iodide (498 mg, 3.32 mmol) in 1,2-dimethoxyethane (56 ml) was stirred for 20 h at room temperature followed by 5 h at 60° C. For work-up, the mixture was concentrated, water was added and the mixture was extracted with a mixture of dichloromethane and 2-propanol (4:1). The combined organic phases were filtered through a silicone filter and concentrated. The residue was purified by flash chromatography (25 g Biotage SNAP cartridge silica, hexanes/ethyl acetate gradient, 0%→100% ethyl acetate) to give the title compound (490 mg, 92% purity, 46% yield).

LC-MS (Method 2): $R_t$=1.67 min; MS (ESIpos): m/z=594 [M+H]$^+$ $^1$H-NMR (400 MHz, DMSO-d$_6$): δ [ppm]=8.26-8.19 (m, 1H), 7.90-7.84 (m, 1H), 7.77 (dd, 1H), 7.56-7.36 (m, 4H), 7.13-7.06 (m, 1H), 6.94-6.88 (m, 2H), 5.29 (td, 1H), 5.11 (td, 1H), 4.90-4.81 (m, 1H), 4.76-4.65 (m, 1H), 4.41-4.21 (m, 8H), 3.78-3.67 (m, 3H), 3.63-3.55 (m, 1H), 3.43-3.34 (m, 1H), 3.32-3.27 (m, 1H), 3.26 (s, 3H), 2.29-2.18 (m, 2H), 1.88-1.81 (m, 3H), 1.28 (t, 3H)

500

Intermediate 144

(rac)-ethyl 2-(2-methoxyethyl)-3-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylate

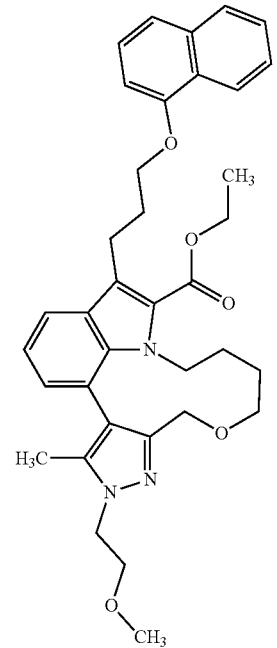 [SMILES: CCOC(=O)c1c(CCCOc2cccc3ccccc23)c2cccc3c2n1CCCCOCc1nn(CCOC)c(C)c1-3]

An autoclave was charged with (rac)-ethyl (11Z)-2-(2-methoxyethyl)-3-methyl-7-[3-(naphthalen-1-yloxy)propyl]-2,10,13,15-tetrahydropyrazolo[4',3':9,10][1,6]oxazacycloundecino[8,7,6-hi]indole-8-carboxylate (400 mg, 674 µmol), ethanol (12 ml), THF (2.4 ml) and palladium 10% on charcoal (71.7 mg, 10% purity, 67.4 µmol) and the mixture was stirred under 21 bar hydrogen atmosphere at room temperature for 22 h. For work-up, the mixture was filtered through a pad of celite, eluted with ethyl acetate and the combined filtrates were concentrated under reduced pressure to give the title compound (400 mg, 90% yield), which was directly used in the next step.

LC-MS (Method 2): $R_t$=1.68 min; MS (ESIpos): m/z=596 [M+H]$^+$

501
Intermediate 145 ethyl 1-{3-[(tert-butoxycarbonyl)(methyl)amino]propyl}-7-{3-(hydroxymethyl)-5-methyl-1-[2-(morpholin-4-yl)ethyl]-1H-pyrazol-4-yl}-3-[3-(naphthalen-1-yloxy)propyl]-1H-indole-2-carboxylate

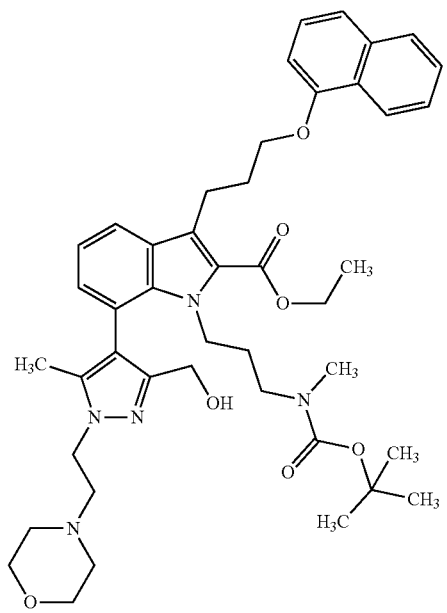 [SMILES: CCOC(=O)c1c(CCCOc2cccc3ccccc23)c2cccc(-c3c(CO)nn(CCN4CCOCC4)c3C)c2n1CCCN(C)C(=O)OC(C)(C)C]

A mixture of ethyl 7-{3-(hydroxymethyl)-5-methyl-1-[2-(morpholin-4-yl)ethyl]-1H-pyrazol-4-yl}-3-[3-(naphthalen-1-yloxy)propyl]-1H-indole-2-carboxylate (see Intermediate 140, 1.43 g, 2.40 mmol), caesium carbonate (3.90 g, 12.0 mmol) and tert-butyl (3-bromopropyl)methylcarbamate (see Intermediate 1, 665 mg, 2.64 mmol) in DMF (30 ml) was stirred for 2 days at room temperature. For work-up, water was added, and the mixture was extracted with a mixture of dichloromethane and 2-propanol (4:1). The combined organic phases were filtered through a silicone filter and concentrated. The residue was purified by flash chromatography (Biotage SNAP cartridge silica, hexanes/ethyl acetate gradient, 50%→100% ethyl acetate) to give the title compound (1.38 g, 82% purity, 61% yield).

LC-MS (Method 2): $R_t$=1.68 min; MS (ESIpos): m/z=768 [M+H]$^+$

502
Intermediate 146 ethyl 7-{3-(bromomethyl)-5-methyl-1-[2-(morpholin-4-yl)ethyl]-1H-pyrazol-4-yl}-1-{3-[(tert-butoxycarbonyl)(methyl)amino]propyl}-3-[3-(naphthalen-1-yloxy)propyl]-1H-indole-2-carboxylate

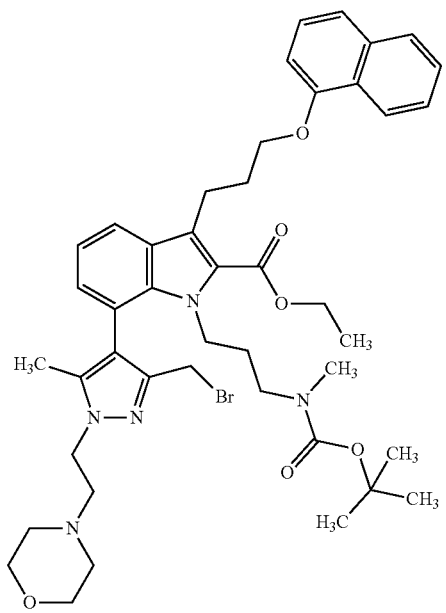 [SMILES: CCOC(=O)c1c(CCCOc2cccc3ccccc23)c2cccc(-c3c(CBr)nn(CCN4CCOCC4)c3C)c2n1CCCN(C)C(=O)OC(C)(C)C]

Tetrabromomethane (1.31 g, 3.95 mmol) was added to a solution of ethyl 1-{3-[(tert-butoxycarbonyl)(methyl)amino]propyl}-7-{3-(hydroxymethyl)-5-methyl-1-[2-(morpholin-4-yl)ethyl]-1H-pyrazol-4-yl}-3-[3-(naphthalen-1-yloxy)propyl]-1H-indole-2-carboxylate (1.38 g, 1.80 mmol) and triphenylphosphine (1.13 g, 4.31 mmol) in dichloromethane (33 ml) at 0° C. and the mixture was stirred for 2 h at room temperature. For work-up, the mixture was concentrated and used in the next step without further purification.

LC-MS (Method 2): $R_t$=1.81 min; MS (ESIpos): m/z=830 [M+H]$^+$

503

Intermediate 147 ethyl 7-{3-(bromomethyl)-5-methyl-1-[2-(morpholin-4-yl)ethyl]-1H-pyrazol-4-yl}-1-[3-(methylamino)propyl]-3-[3-(naphthalen-1-yloxy)propyl]-1H-indole-2-carboxylate hydrochloric acid salt

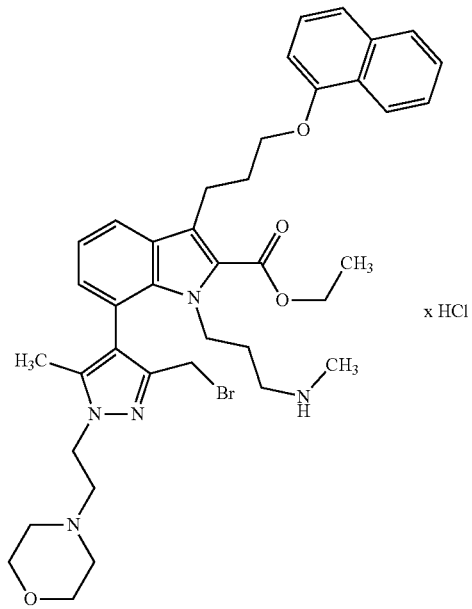 [SMILES: CCOC(=O)c1c(CCCOc2cccc3ccccc23)c2cccc(-c3c(CBr)nn(CCN4CCOCC4)c3C)c2n1CCCNC ; "x HCl"]

x HCl

Hydrogen chloride (33 ml, 4.0 M in dioxane, 130 mmol) was added to a solution of ethyl 7-{3-(bromomethyl)-5-methyl-1-[2-(morpholin-4-yl)ethyl]-1H-pyrazol-4-yl}-1-{3-[(tert-butoxycarbonyl)(methyl)amino]propyl}-3-[3-(naphthalen-1-yloxy)propyl]-1H-indole-2-carboxylate (3.87 g) in ethanol (30 ml) and the mixture was stirred for 2 h at room temperature. For work-up, the reaction mixture was concentrated to give the title compound (3.90 g) which was used in the next step without further purification.

504

Intermediate 148

(rac)-ethyl 7,11-dimethyl-10-[2-(morpholin-4-yl)ethyl]-1-[3-(naphthalen-1-yloxy)propyl]-4,5,6,7,8,10-hexahydropyrazolo[3',4':7,8][1,5]diazecino[9,10,1-hi]indole-2-carboxylate

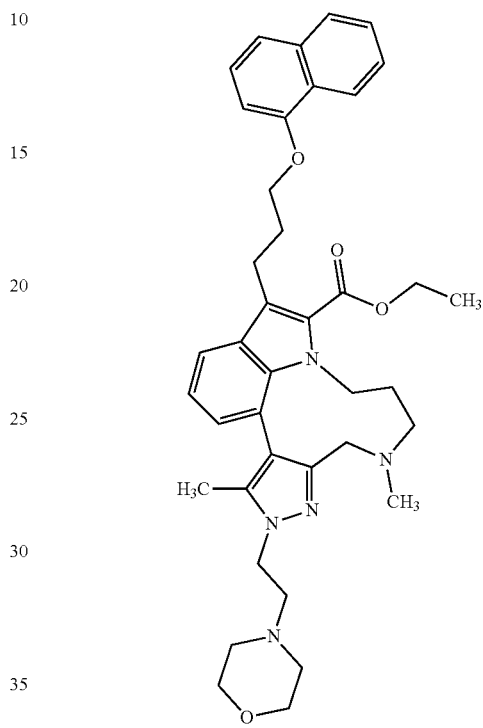

A mixture of ethyl 7-{3-(bromomethyl)-5-methyl-1-[2-(morpholin-4-yl)ethyl]-1H-pyrazol-4-yl}-1-[3-(methylamino)propyl]-3-[3-(naphthalen-1-yloxy)propyl]-1H-indole-2-carboxylate hydrochloric acid salt (3.90 g) and caesium carbonate (2.93 g, 8.98 mmol) in DMF (180 ml) was stirred for 20 h at 65° C. For work-up, water was added and the mixture was extracted with a mixture of dichloromethane and 2-propanol (4:1). The combined organic phases were filtered through a silicone filter and concentrated. The residue was purified by flash chromatography (50 g Biotage SNAP cartridge silica, hexanes/ethyl acetate 1:1 to ethyl acetate to ethyl acetate/ethanol 4:1 gradient) followed by preparative HPLC [Instrument: Labomatic HD5000, Labocord-5000; Gilson GX-241, Labcol Vario 4000, column: XBrigde C18 5µ 150×30 mm; eluent B: water+0.2 vol-% ammonia (32%); eluent C: acetonitrile; gradient: 3-10 min 75-95% C, 10.1-12 min 100% C; flow 50.0 ml/min; UV 254 nm] to give the title compound (330 mg, 93% purity, 26% yield).

LC-MS (Method 4): $R_t$=1.72 min; MS (ESIpos): m/z=650 [M+H]$^+$ $^1$H-NMR (400 MHz, DMSO-d$_6$): δ [ppm]=8.25-8.21 (m, 1H), 7.89-7.84 (m, 1H), 7.69 (dd, 1H), 7.56-7.36 (m, 4H), 6.99 (dd, 1H), 6.88 (d, 1H), 6.81 (dd, 1H), 4.50-4.42 (m, 1H), 4.32-4.10 (m, 6H), 3.86 (br dd, 1H), 3.53 (t, 4H), 3.27-3.19 (m, 3H), 3.19-3.12 (m, 1H), 2.77-2.61 (m, 2H), 2.45-2.35 (m, 4H), 2.24-2.15 (m, 2H), 2.08-1.99 (m, 4H), 1.85 (s, 3H), 1.64-1.40 (m, 2H), 1.28 (t, 3H)

Intermediate 149 ethyl 7-{5-(hydroxymethyl)-3-methyl-1-[2-(morpholin-4-yl)ethyl]-1H-pyrazol-4-yl}-3-[3-(naphthalen-1-yloxy)propyl]-1H-indole-2-carboxylate

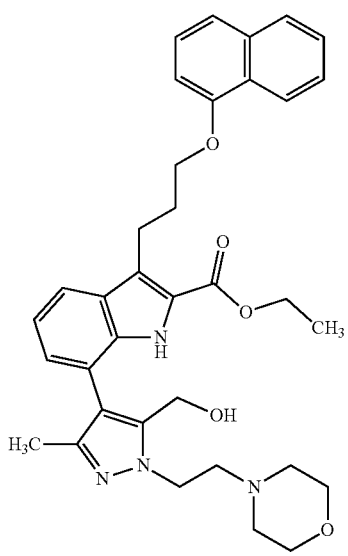 [SMILES: CCOC(=O)c1[nH]c2c(-c3c(C)nn(CCN4CCOCC4)c3CO)cccc2c1CCCOc1cccc2ccccc12]

XPhos Pd G2 (see abbreviation list, 34.9 mg, 44.3 µmol) was added to a degassed mixture of ethyl 3-[3-(naphthalen-1-yloxy)propyl]-7-(4,4,5,5-tetramethyl-1,3,2-dioxaborolan-2-yl)-1H-indole-2-carboxylate (see Intermediate 5, 722 mg, 1.45 mmol), {4-bromo-3-methyl-1-[2-(morpholin-4-yl)ethyl]-1H-pyrazol-5-yl}methanol (see Intermediate 101, 400 mg, 1.31 mmol), aqueous potassium phosphate solution (5.3 ml, 0.50 M, 2.6 mmol) and THF (16 ml) and the mixture was stirred for 2 h at 45° C. For work-up, ethyl acetate was added, the mixture was filtered through a pad of celite, eluted with ethyl acetate and the organic phase was washed with brine, filtered through a silicone filter and concentrated. The residue was purified by flash chromatography (Biotage SNAP cartridge silica, hexanes to ethyl acetate to ethyl acetate/ethanol 1:1 gradient) to give the title compound (709 mg, 79% yield).

LC-MS (Method 1): Rt=1.37 min; MS (ESIneg): m/z=565 [M−H]−

$^1$H-NMR (400 MHz, DMSO-d6) δ [ppm]: 1.066 (0.44), 1.255 (4.90), 1.263 (0.52), 1.273 (10.97), 1.290 (4.99), 2.099 (16.00), 2.217 (0.92), 2.235 (1.26), 2.253 (0.96), 2.322 (0.76), 2.327 (1.05), 2.332 (0.78), 2.518 (4.25), 2.523 (2.92), 2.660 (0.42), 2.664 (0.78), 2.669 (1.07), 2.673 (0.76), 2.749 (1.35), 2.766 (2.99), 2.782 (1.42), 3.361 (1.88), 3.378 (1.11), 3.597 (3.05), 3.608 (4.53), 3.620 (3.01), 4.200 (1.44), 4.216 (2.83), 4.230 (1.44), 4.239 (1.63), 4.256 (4.62), 4.274 (4.88), 4.292 (2.55), 4.296 (2.55), 4.312 (1.31), 5.759 (0.52), 6.246 (0.74), 6.906 (1.70), 6.923 (1.83), 7.077 (1.27), 7.095 (2.20), 7.115 (2.01), 7.145 (2.27), 7.148 (2.49), 7.163 (1.37), 7.166 (1.22), 7.373 (1.39), 7.393 (2.49), 7.412 (2.14), 7.449 (2.51), 7.470 (1.39), 7.481 (0.52), 7.485 (0.63), 7.498 (1.57), 7.502 (1.35), 7.511 (1.68), 7.516 (2.92), 7.522 (1.68), 7.530 (1.46), 7.535 (1.63), 7.547 (0.70), 7.551 (0.48), 7.674 (1.70), 7.676 (1.74), 7.693 (1.66), 7.696 (1.53), 7.859 (1.46), 7.865 (0.87), 7.877 (1.63), 7.882 (1.24), 8.212 (1.31), 8.217 (1.31), 8.234 (1.22), 8.236 (1.27), 10.943 (1.22).

Intermediate 150

(rac)-ethyl (11Z)-3-methyl-1-[2-(morpholin-4-yl)ethyl]-7-[3-(naphthalen-1-yloxy)propyl]-1,10,13,15-tetrahydropyrazolo[4',3':9,10][1,6]oxazacycloundecino[8,7,6-hi]indole-8-carboxylate

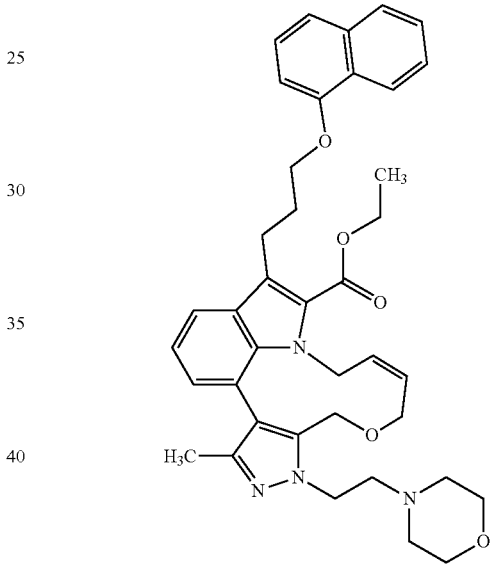

The title compound was prepared in analogy to the synthesis of (rac)-ethyl (11Z)-2-(2-methoxyethyl)-3-methyl-7-[3-(naphthalen-1-yloxy)propyl]-2,10,13,15-tetrahydropyrazolo[4',3':9,10][1,6]oxazacycloundecino[8,7,6-hi]indole-8-carboxylate using ethyl 7-{5-(hydroxymethyl)-3-methyl-1-[2-(morpholin-4-yl)ethyl]-1H-pyrazol-4-yl}-3-[3-(naphthalen-1-yloxy)propyl]-1H-indole-2-carboxylate (602 mg, 1.01 mmol), as starting material. The crude product was purified by flash chromatography (Biotage SNAP cartridge silica, hexanes to ethyl acetate to ethyl acetate/ethanol 4:1 gradient) to give the title compound (307 mg, 70% purity, 47% yield).

LC-MS (Method 2): R$_t$=1.69 min; MS (ESIpos): m/z=649 [M+H]+

507

Intermediate 151

(rac)-ethyl 3-methyl-1-[2-(morpholin-4-yl)ethyl]-7-[3-(naphthalen-1-yloxy)propyl]-1,10,11,12,13,15-hexahydropyrazolo[4',3':9,10][1,6]oxazacycloundecino[8,7,6-hi]indole-8-carboxylate

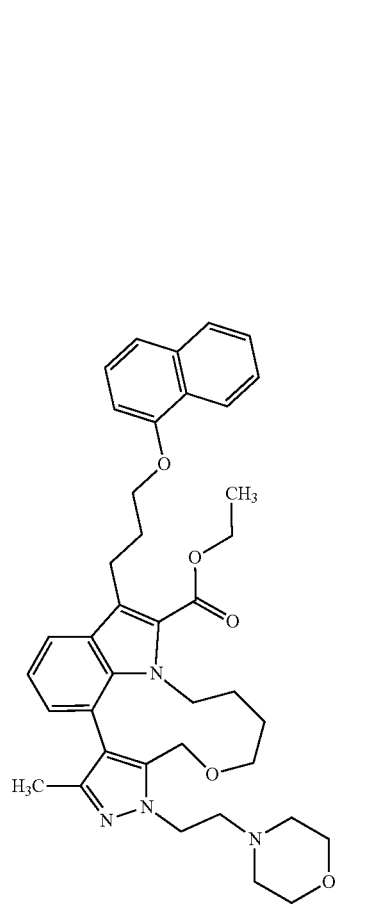 [SMILES: CCOC(=O)c1c(CCCOc2cccc3ccccc23)c2cccc3c2n1CCCCOCc1c-3c(C)nn1CCN1CCOCC1]

An autoclave was charged with (rac)-ethyl (11Z)-3-methyl-1-[2-(morpholin-4-yl)ethyl]-7-[3-(naphthalen-1-yloxy)propyl]-1,10,13,15-tetrahydropyrazolo[4',3':9,10][1,6]oxazacycloundecino[8,7,6-hi]indole-8-carboxylate (307 mg, 473 µmol), ethanol (8.3 ml), THF (1.7 ml) and palladium 10% on charcoal (50.3 mg, 10% purity, 47.3 µmol) and the mixture was stirred under 21 bar hydrogen atmosphere at room temperature for 22 h. For work-up, the mixture was filtered through a pad of celite, eluted with ethyl acetate and the combined filtrates were concentrated under reduced pressure to give the title compound (287 mg), which was directly used in the next step.

LC-MS (Method 2): $R_t$=1.69 min; MS (ESIpos): m/z=651 [M+H]$^+$

508

Intermediate 152 ethyl 7-[3-(hydroxymethyl)-1-(2-methoxyethyl)-5-(morpholin-4-ylmethyl)-1H-pyrazol-4-yl]-3-[3-(naphthalen-1-yloxy)propyl]-1H-indole-2-carboxylate

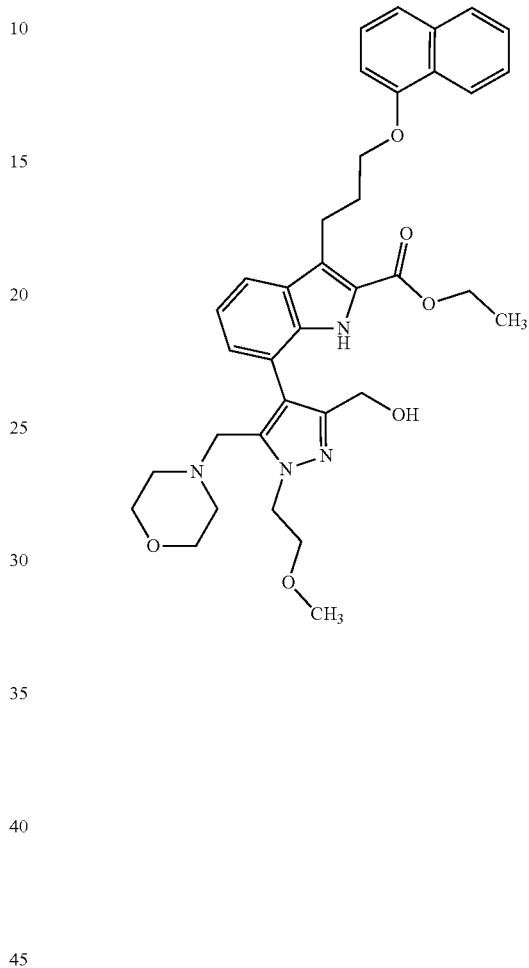

XPhos Pd G2 (see abbreviation list, 30.1 mg, 38.3 µmol) was added to a degassed mixture of ethyl 3-[3-(naphthalen-1-yloxy)propyl]-7-(4,4,5,5-tetramethyl-1,3,2-dioxaborolan-2-yl)-1H-indole-2-carboxylate (see Intermediate 5, 625 mg, 1.25 mmol), [4-bromo-1-(2-methoxyethyl)-5-(morpholin-4-ylmethyl)-1H-pyrazol-3-yl]methanol (see Intermediate 104, 380 mg, 1.14 mmol), aqueous potassium phosphate solution (4.5 ml, 0.50 M, 2.3 mmol) and THF (14 ml) and the mixture was stirred for 2 h at 45° C. For work-up, ethyl acetate was added, the mixture was filtered through a pad of celite, eluted with ethyl acetate and the organic phase was washed with brine, filtered through a silicone filter and concentrated. The residue was purified by flash chromatography (25 g Biotage SNAP cartridge silica, dichloromethane/methanol 9:1) to give the title compound (693 mg, 83% yield).

LC-MS (Method 2): $R_t$=1.56 min; MS (ESIpos): m/z=627 [M+H]$^+$

509

Intermediate 153 ethyl 1-{3-[(tert-butoxycarbonyl)(methyl)amino]
propyl}-7-[3-(hydroxymethyl)-1-(2-methoxyethyl)-
5-(morpholin-4-ylmethyl)-1H-pyrazol-4-yl]-3-[3-
(naphthalen-1-yloxy)propyl]-1H-indole-2-
carboxylate

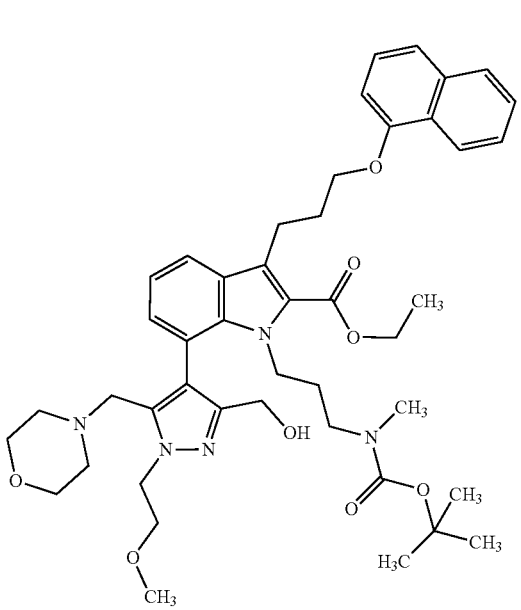 [SMILES: CCOC(=O)c1c(CCCOc2cccc3ccccc23)c2cccc(-c3c(CO)nn(CCOC)c3CN3CCOCC3)c2n1CCCN(C)C(=O)OC(C)(C)C]

510

Intermediate 154 ethyl 7-[3-(bromomethyl)-1-(2-methoxyethyl)-5-
(morpholin-4-ylmethyl)-1H-pyrazol-4-yl]-1-{3-
[(tert-butoxycarbonyl)(methyl)amino]propyl}-3-[3-
(naphthalen-1-yloxy)propyl]-1H-indole-2-
carboxylate

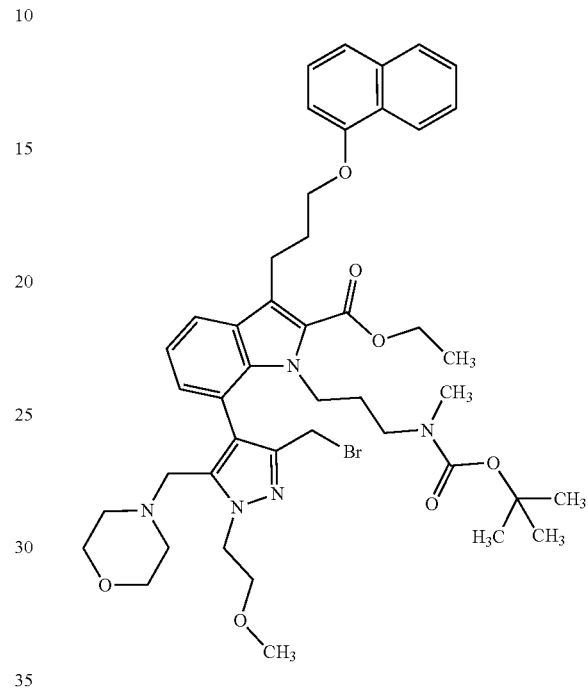

A mixture of ethyl 7-[3-(hydroxymethyl)-1-(2-methoxyethyl)-5-(morpholin-4-ylmethyl)-1H-pyrazol-4-yl]-3-[3-(naphthalen-1-yloxy)propyl]-1H-indole-2-carboxylate (690 mg, 1.10 mmol), caesium carbonate (1.79 g, 5.50 mmol) and tert-butyl (3-bromopropyl)methylcarbamate (see Intermediate 1, 305 mg, 1.21 mmol) in DMF (14 ml) was stirred for 2 d at room temperature. For work-up, water was added, and the mixture was extracted with a mixture of dichloromethane and 2-propanol (4:1). The combined organic phases were filtered through a silicone filter and concentrated. The residue was purified by flash chromatography (Biotage SNAP cartridge silica, hexanes/ethyl acetate gradient, 50%→100% ethyl acetate) to give the title compound (650 mg, 90% purity, 67% yield).

LC-MS (Method 2): $R_t$=1.67 min; MS (ESIneg$s$): m/z=796.5 [M−H]⁻

Tetrabromomethane (535 mg, 1.61 mmol) was added to a solution of ethyl 1-{3-[(tert-butoxycarbonyl)(methyl)amino]propyl}-7-[3-(hydroxymethyl)-1-(2-methoxyethyl)-5-(morpholin-4-ylmethyl)-1H-pyrazol-4-yl]-3-[3-(naphthalen-1-yloxy)propyl]-1H-indole-2-carboxylate (650 mg, 90% purity, 733 µmol) and triphenylphosphine (461 mg, 1.76 mmol) in dichloromethane (13 ml) at 0° C., and the mixture was stirred for 2 h at room temperature. For work-up, the mixture was concentrated to give the title compound (1.15 g) which was used in the next step without further purification.

LC-MS (Method 2): $R_t$=1.83 min; MS (ESIpos): m/z=860 [M+H]⁺

Intermediate 155 ethyl 7-[3-(bromomethyl)-1-(2-methoxyethyl)-5-(morpholin-4-ylmethyl)-1H-pyrazol-4-yl]-1-[3-(methylamino)propyl]-3-[3-(naphthalen-1-yloxy)propyl]-1H-indole-2-carboxylate hydrochloric acid salt

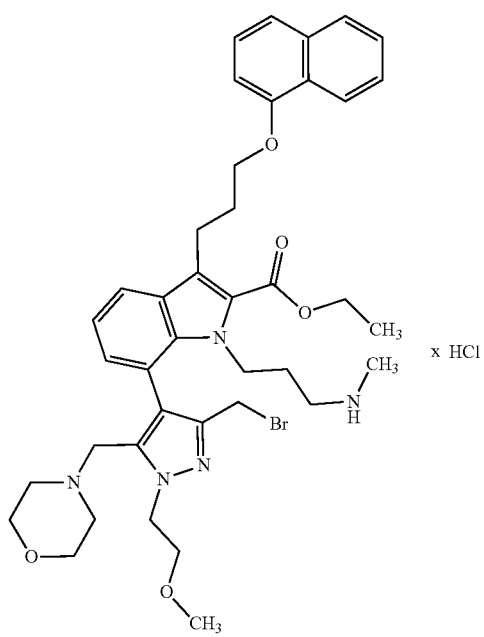

Hydrogen chloride (14 ml, 4.0 M in dioxane, 54 mmol) was added to a solution of ethyl 7-[3-(bromomethyl)-1-(2-methoxyethyl)-5-(morpholin-4-ylmethyl)-1H-pyrazol-4-yl]-1-{3-[(tert-butoxycarbonyl)(methyl)amino]propyl}-3-[3-(naphthalen-1-yloxy)propyl]-1H-indole-2-carboxylate (1.15 g) in ethanol (12 ml) and the mixture was stirred for 2 h at room temperature. For work-up, the reaction mixture was concentrated to give the title compound (1.62 g) which was used in the next step without further purification.

Intermediate 156

(rac)-ethyl 10-(2-methoxyethyl)-7-methyl-11-(morpholin-4-ylmethyl)-1-[3-(naphthalen-1-yloxy)propyl]-4,5,6,7,8,10-hexahydropyrazolo[3',4':7,8][1,5]diazecino[9,10,1-hi]indole-2-carboxylate

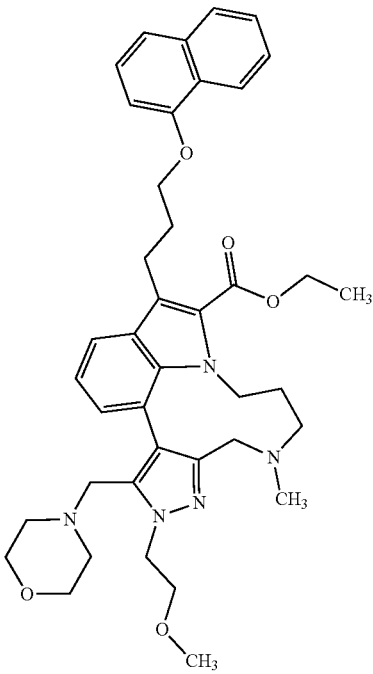 [SMILES: CCOC(=O)c1c(CCCOc2cccc3ccccc23)c2cccc3c2n1CCCN(C)Cc1nn(CCOC)c(CN2CCOCC2)c1-3]

A mixture of ethyl 7-[3-(bromomethyl)-1-(2-methoxyethyl)-5-(morpholin-4-ylmethyl)-1H-pyrazol-4-yl]-1-[3-(methylamino)propyl]-3-[3-(naphthalen-1-yloxy)propyl]-1H-indole-2-carboxylate hydrochloric acid salt (1.62 g) and caesium carbonate (1.21 g, 3.71 mmol) in DMF (74 ml) was stirred for 20 h at 65° C. For work-up, water was added and the mixture was extracted with a mixture of dichloromethane and 2-propanol (4:1). The combined organic phases were filtered through a silicone filter and concentrated. The residue was purified by flash chromatography (50 g Biotage SNAP cartridge silica, hexanes/ethyl acetate 1:1 to ethyl acetate to ethyl acetate/ethanol 4:1 gradient) followed by preparative HPLC [Instrument: Labomatic HD5000, Labocord-5000; Gilson GX-241, Labcol Vario 4000, column: XBrigde C18 5μ 150×30 mm; eluent A: water+0.1 vol-% formic acid (99%); eluent C: acetonitrile; gradient: 3-10 min 59-79% C, 10.1-12 min 100% C; flow 50.0 ml/min; UV 254 nm] to give the title compound (68.0 mg, 13% yield).

LC-MS (Method 2): $R_t$=1.76 min; MS (ESIpos): m/z=680 [M+H]$^+$ $^1$H-NMR (400 MHz, DMSO-d6) δ [ppm]: 1.260 (2.77), 1.277 (5.99), 1.295 (2.82), 1.854 (7.37), 2.031 (0.44), 2.198 (2.31), 2.331 (0.48), 2.416 (0.53), 2.452 (0.51), 2.518 (2.69), 2.522 (1.81), 2.673 (0.47), 3.166 (0.88), 3.183 (0.91), 3.199 (1.34), 3.216 (1.33), 3.245 (0.41), 3.274 (16.00), 3.300 (1.77), 3.309 (1.43), 3.357 (0.53), 3.464 (1.96), 3.474 (1.91), 3.723 (0.57), 3.738 (1.44), 3.754 (1.73), 3.768 (0.84), 3.779 (0.60), 4.164 (0.56), 4.179 (1.13), 4.186 (1.11), 4.194 (1.10), 4.203 (0.78), 4.212 (0.68), 4.221 (1.08), 4.232 (0.50), 4.239 (1.10), 4.251 (1.09), 4.257 (0.43), 4.269 (1.01), 4.277 (0.46), 4.295 (0.43), 4.387 (1.03), 4.402 (1.96), 4.417 (0.92), 6.815

(1.05), 6.818 (1.05), 6.833 (1.29), 6.836 (1.22), 6.857 (1.14), 6.875 (1.22), 6.968 (1.05), 6.988 (1.26), 7.006 (0.84), 7.358 (0.80), 7.379 (1.52), 7.398 (1.13), 7.445 (1.59), 7.466 (0.93), 7.513 (1.08), 7.517 (1.72), 7.527 (1.88), 7.536 (1.68), 7.541 (1.09), 7.695 (1.11), 7.697 (1.13), 7.714 (1.06), 7.717 (1.00), 7.860 (0.92), 7.871 (0.52), 7.875 (0.58), 7.877 (0.59), 7.883 (0.76), 8.234 (0.80), 8.242 (0.57), 8.258 (0.74).

Intermediate 157

(rac)-ethyl 10,11-dimethyl-1-[3-(naphthalen-1-yloxy) propyl]-5,6,8,10-tetrahydro-4H-pyrazolo[4',3':8,9][1,5]oxazecino[7,6,5-hi]indole-2-carboxylate

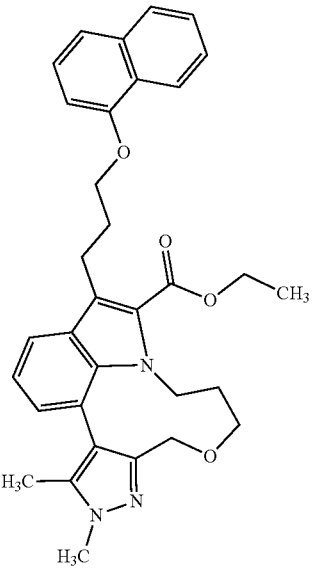 [SMILES: CCOC(=O)c1c(CCCOc2cccc3ccccc23)c2cccc3c2n1CCCOCc1nn(C)c(C)c1-3]

A mixture of ethyl 7-[3-(hydroxymethyl)-1,5-dimethyl-1H-pyrazol-4-yl]-3-[3-(naphthalen-1-yloxy)propyl]-1H-indole-2-carboxylate (see Intermediate 12, 700 mg, 1.41 mmol), 1,3-diiodopropane (160 µl, 1.4 mmol) and caesium carbonate (2.29 g, 7.03 mmol) in DMF (22 ml) was stirred for 20 h at room temperature. For work-up, water was added and the mixture was extracted with ethyl acetate. The combined organic phases were filtered through a silicone filter and concentrated. The residue was purified by flash chromatography (50 g Biotage SNAP cartridge silica, hexanes/ethyl acetate gradient, 0%→100% ethyl acetate) to give the title compound (120 mg, 16% yield).

LC-MS (Method 1): $R_t$=1.68 min; MS (ESIpos): m/z=538 [M+H]$^+$ $^1$H-NMR (400 MHz, DMSO-d$_6$): δ [ppm]=8.26-8.20 (m, 1H), 7.90-7.86 (m, 1H), 7.75 (d, 1H), 7.55-7.45 (m, 3H), 7.42-7.38 (m, 1H), 7.08-7.03 (m, 1H), 6.94-6.88 (m, 2H), 4.55-4.46 (m, 1H), 4.30-4.19 (m, 5H), 4.05-3.93 (m, 2H), 3.81 (s, 3H), 3.50-3.42 (m, 1H), 3.31-3.22 (m, 1H), 3.08-3.03 (m, 1H), 2.26-2.16 (m, 2H), 2.01 (s, 3H), 1.76-1.40 (m, 2H), 1.27 (t, 3H)

Intermediate 158

(rac)-ethyl (11Z)-2,3-dimethyl-7-[3-(naphthalen-1-yloxy)propyl]-2,10,13,15-tetrahydropyrazolo[4',3':9,10][1,6]oxazacycloundecino[8,7,6-hi]indole-8-carboxylate

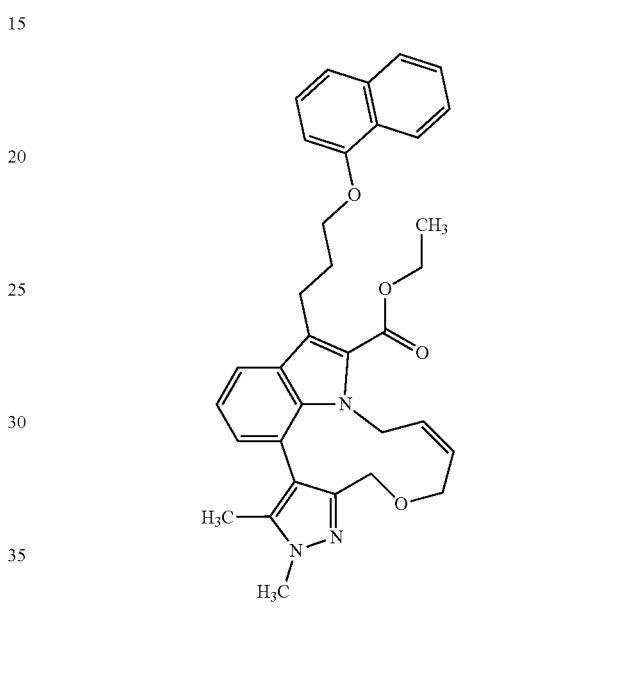

A mixture of ethyl 7-[3-(hydroxymethyl)-1,5-dimethyl-1H-pyrazol-4-yl]-3-[3-(naphthalen-1-yloxy)propyl]-1H-indole-2-carboxylate (see Intermediate 12, 661 mg, 1.33 mmol), (2Z)-1,4-dichlorobut-2-ene (140 µl, 1.3 mmol), caesium carbonate (2.16 g, 6.64 mmol) and sodium iodide (398 mg, 2.66 mmol) in bis(2-methoxyethyl) ether (46 ml) was stirred for 20 h at room temperature followed by 6 h 70° C. For work-up, water was added and the mixture was extracted with a mixture of dichloromethane and 2-propanol (4:1). The combined organic phases were filtered through a silicone filter and concentrated. The residue was purified by flash chromatography (Biotage SNAP cartridge silica, hexanes/ethyl acetate gradient) to give the title compound (281 mg, 37% yield).

LC-MS (Method 2): $R_t$=1.65 min; MS (ESIpos): m/z=550 [M+H]$^+$ $^1$H-NMR (600 MHz, DMSO-d$_6$): δ [ppm]=8.26-8.22 (m, 1H), 7.89-7.85 (m, 1H), 7.77 (dd, 1H), 7.55-7.37 (m, 4H), 7.11-7.07 (m, 1H), 6.93 (d, 1H), 6.88 (dd, 1H), 5.30 (td, 1H), 5.14 (td, 1H), 4.89 (br d, 1H), 4.79 (dd, 1H), 4.37 (d, 1H), 4.35-4.23 (m, 5H), 3.84 (s, 3H), 3.76 (t, 1H), 3.62-3.57 (m, 1H), 3.40-3.36 (m, 1H), 3.33-3.27 (m, 1H), 2.55-2.52 (m, 1H), 2.29-2.22 (m, 2H), 1.85 (s, 3H), 1.29 (t, 3H)

515
Intermediate 159 ethyl 1-{4-[(tert-butoxycarbonyl)(methyl)amino]butyl}-7-[3-(hydroxymethyl)-1,5-dimethyl-1H-pyrazol-4-yl]-3-[3-(naphthalen-1-yloxy)propyl]-1H-indole-2-carboxylate

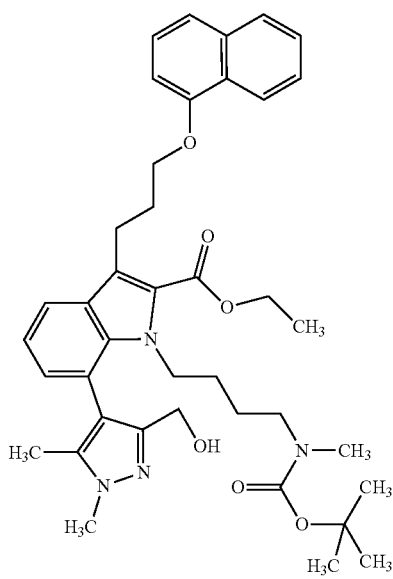 [SMILES: CCOC(=O)c1c(CCCOc2cccc3ccccc23)c2cccc(-c3c(CO)nn(C)c3C)c2n1CCCCN(C)C(=O)OC(C)(C)C]

The title compound (1.88 g, 91% yield) was prepared in analogy to the synthesis of ethyl 1-{3-[(tert-butoxycarbonyl)(methyl)amino]propyl}-7-[3-(hydroxymethyl)-1-(2-methoxyethyl)-5-(morpholin-4-ylmethyl)-1H-pyrazol-4-yl]-3-[3-(naphthalen-1-yloxy)propyl]-1H-indole-2-carboxylate, using ethyl 7-[3-(hydroxymethyl)-1,5-dimethyl-1H-pyrazol-4-yl]-3-[3-(naphthalen-1-yloxy)propyl]-1H-indole-2-carboxylate (see Intermediate 12, 1.50 g, 3.01 mmol) as starting material.

LC-MS (Method 1): $R_t$=1.69 min; MS (ESIpos): m/z=683 [M+H]$^+$

516
Intermediate 160 ethyl 7-[3-(bromomethyl)-1,5-dimethyl-1H-pyrazol-4-yl]-1-{4-[(tert-butoxycarbonyl)(methyl)amino]butyl}-3-[3-(naphthalen-1-yloxy)propyl]-1H-indole-2-carboxylate

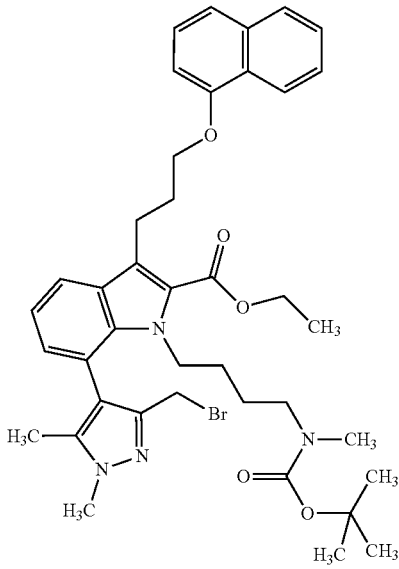 [SMILES: CCOC(=O)c1c(CCCOc2cccc3ccccc23)c2cccc(-c3c(CBr)nn(C)c3C)c2n1CCCCN(C)C(=O)OC(C)(C)C]

Tetrabromomethane (2.01 g, 6.06 mmol) was added to a solution of ethyl 1-{4-[(tert-butoxycarbonyl)(methyl)amino]butyl}-7-[3-(hydroxymethyl)-1,5-dimethyl-1H-pyrazol-4-yl]-3-[3-(naphthalen-1-yloxy)propyl]-1H-indole-2-carboxylate (1.88 g, 2.75 mmol) and triphenylphosphine (1.73 g, 6.61 mmol) in dichloromethane (40 ml) at 0° C. and the mixture was stirred for 16 h at room temperature. For work-up, the mixture was concentrated and the residue was purified by flash chromatography (100 g Biotage SNAP cartridge silica, hexanes/ethyl acetate gradient, 0%→100% ethyl acetate) to give the title compound (0.55 g, 27% yield).

LC-MS (Method 1): Rt=1.82 min; MS (ESIpos): m/z=745 [M+H]$^+$

517

Intermediate 161 ethyl 7-[3-(bromomethyl)-1,5-dimethyl-1H-pyrazol-4-yl]-1-[4-(methylamino)butyl]-3-[3-(naphthalen-1-yloxy)propyl]-1H-indole-2-carboxylate hydrochloric acid salt

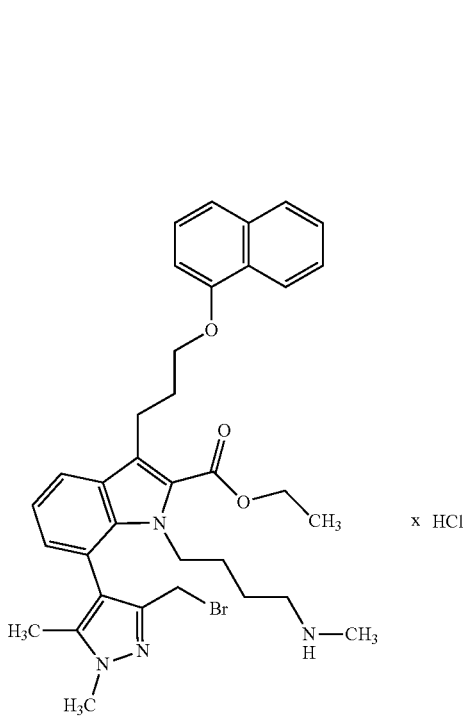

Hydrogen chloride (6.8 ml, 4.0 M in dioxane, 27 mmol) was added to a solution of ethyl 7-[3-(bromomethyl)-1,5-dimethyl-1H-pyrazol-4-yl]-1-{4-[(tert-butoxycarbonyl)(methyl)amino]butyl}-3-[3-(naphthalen-1-yloxy)propyl]-1H-indole-2-carboxylate (550 mg, 737 µmol) in ethanol (12 ml) and the mixture was stirred for 16 h at room temperature. Additional hydrogen chloride (3.4 ml, 4.0 M in dioxane, 14 mmol) was added and the mixture was stirred for additional 2 h. For work-up, the reaction mixture was concentrated to give the title compound (700 mg) which was used in the next step without further purification.

518

Intermediate 162

(rac)-ethyl 2,3,14-trimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylate

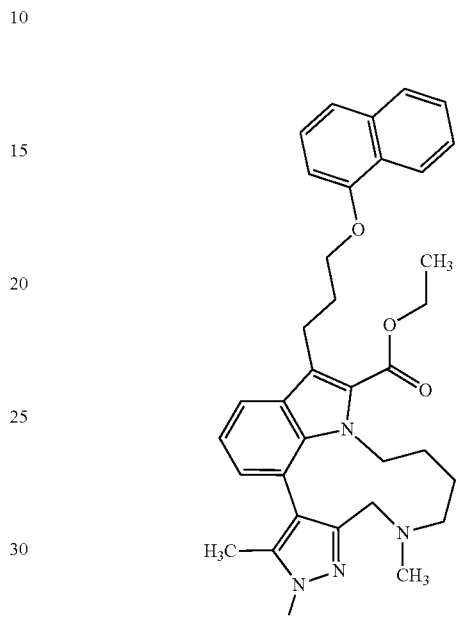

A mixture of ethyl 7-[3-(bromomethyl)-1,5-dimethyl-1H-pyrazol-4-yl]-1-[4-(methylamino)butyl]-3-[3-(naphthalen-1-yloxy)propyl]-1H-indole-2-carboxylate hydrochloric acid salt (700 mg) and caesium carbonate (836 mg, 2.57 mmol) in DMF (16 ml) was stirred for 16 h at 65° C. For work-up, water was added and the mixture was extracted with a mixture of dichloromethane and 2-propanol (4:1). The combined organic phases were filtered through a silicone filter and concentrated. The residue was purified by flash chromatography (28 g Biotage SNAP cartridge NH$_2$ silica, hexanes/ethyl acetate 0%→60% ethyl acetate) to give the title compound (290 mg, 100% yield).

LC-MS (Method 1): R$_t$=1.47 min; MS (ESIpos): m/z=565 [M+H]$^+$

Intermediate 163 ethyl 7-[3-(hydroxymethyl)-1,5-dimethyl-1H-pyrazol-4-yl]-6-methyl-3-[3-(naphthalen-1-yloxy)propyl]-1H-indole-2-carboxylate

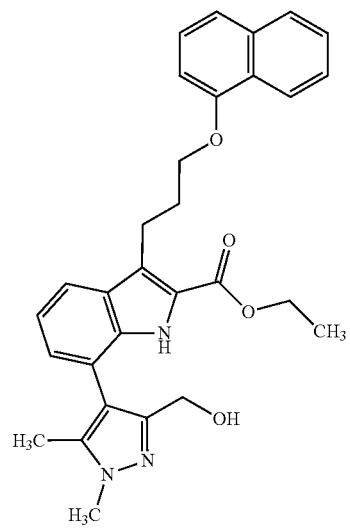

XPhos Pd G2 (see abbreviation list, 136 mg, 173 μmol) was added to a degassed mixture of ethyl 6-methyl-3-[3-(naphthalen-1-yloxy)propyl]-7-(4,4,5,5-tetramethyl-1,3,2-dioxaborolan-2-yl)-1H-indole-2-carboxylate (see Intermediate 19, 2.63 g, 5.12 mmol), (4-bromo-1,5-dimethyl-1H-pyrazol-3-yl)methanol (see Intermediate 11, 1.10 g, 5.38 mmol) aqueous potassium phosphate solution (20 ml, 0.50 M, 10 mmol) and THF (62 ml), and the mixture was stirred for 2 h at 45° C. For work-up, ethyl acetate was added, the mixture was filtered through a pad of celite, eluted with ethyl acetate and the organic phase was filtered through a silicone filter and was finally concentrated. The residue was purified by flash chromatography (50 g Biotage SNAP cartridge silica, hexanes/ethyl acetate gradient, 20→100% ethyl acetate) to give the title compound (1.95 g, 71% yield).

LC-MS (Method 2): $R_t$=1.55 min; MS (ESIpos): m/z=512 [M+H]$^+$ $^1$H-NMR (400 MHz, DMSO-d$_6$): δ [ppm]=10.32 (s, 1H), 8.28-8.23 (m, 1H), 7.90-7.85 (m, 1H), 7.58-7.38 (m, 5H), 6.99 (d, 1H), 6.92 (d, 1H), 5.06 (s, 1H), 4.30-4.18 (m, 5H), 4.06-3.97 (m, 1H), 3.80 (s, 3H), 3.32-3.27 (m, 2H), 2.26-2.16 (m, 2H), 2.12 (s, 3H), 1.94 (s, 3H), 1.25 (t, 3H).

Intermediate 164

(rac)-ethyl (11Z)-2,3,4-trimethyl-7-[3-(naphthalen-1-yloxy)propyl]-2,10,13,15-tetrahydropyrazolo[4',3': 9,10][1,6]oxazacycloundecino[8,7,6-hi]indole-8-carboxylate

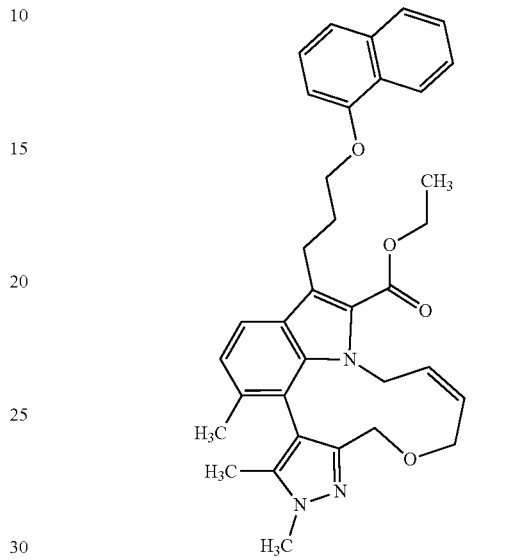

A mixture of ethyl 7-[3-(hydroxymethyl)-1,5-dimethyl-1H-pyrazol-4-yl]-6-methyl-3-[3-(naphthalen-1-yloxy)propyl]-1H-indole-2-carboxylate (1.07 g, 2.09 mmol), (2Z)-1,4-dichlorobut-2-ene (220 μl, 2.1 mmol), caesium carbonate (3.41 g, 10.5 mmol) and sodium iodide (313 mg, 2.09 mmol) in 1,2-dimethoxyethane (70 ml) was stirred for 20 h at room temperature followed by 5 h at 65° C. For work-up, water was added and the mixture was extracted with a mixture of dichloromethane and 2-propanol (4:1). The combined organic phases were filtered through a silicone filter and concentrated. The residue was purified by flash chromatography (Biotage SNAP cartridge silica, hexanes/ethyl acetate gradient, 0%→100% ethyl acetate) to give the title compound (693 mg, 56% yield).

LC-MS (Method 2): $R_t$=1.68 min; MS (ESIpos): m/z=564 [M+H]$^+$ $^1$H-NMR (400 MHz, DMSO-d6) δ [ppm]: 1.154 (0.81), 1.172 (1.68), 1.190 (0.86), 1.259 (4.91), 1.277 (10.96), 1.295 (5.01), 1.768 (16.00), 1.900 (12.77), 1.987 (3.08), 2.074 (1.32), 2.205 (2.35), 2.224 (1.23), 2.242 (0.86), 2.332 (0.58), 2.518 (3.14), 2.522 (2.15), 2.673 (0.59), 3.234 (0.98), 3.242 (0.45), 3.257 (0.62), 3.275 (0.95), 3.296 (0.92), 3.316 (1.41), 3.349 (0.57), 3.568 (0.57), 3.582 (0.69), 3.599 (0.86), 3.612 (0.76), 3.725 (1.54), 3.759 (0.88), 3.788 (1.26), 3.818 (0.65), 3.860 (15.50), 4.017 (0.69), 4.034 (0.69), 4.100 (1.94), 4.133 (2.21), 4.207 (1.15), 4.219 (1.51), 4.225 (1.73), 4.235 (4.23), 4.252 (2.74), 4.261 (0.79), 4.270 (0.62), 4.278 (1.85), 4.285 (0.55), 4.296 (1.73), 4.305 (0.92), 4.314 (0.48), 4.323 (0.91), 4.392 (2.26), 4.424 (1.92), 4.602 (0.52), 4.629 (0.65), 4.641 (0.78), 4.668 (0.85), 4.826 (0.95), 4.865 (0.69), 4.952 (0.51), 4.959 (0.54), 4.979 (0.96), 4.986 (0.91), 5.006 (0.55), 5.012 (0.48), 5.229 (0.64), 5.241 (0.61), 6.917 (1.71), 6.934 (1.87), 7.046 (2.38), 7.067 (2.62), 7.379 (1.34), 7.399 (2.52), 7.418 (2.12), 7.456 (2.62), 7.476 (1.41), 7.487 (0.47), 7.492 (0.62), 7.504 (1.56), 7.509 (1.37), 7.515 (1.60), 7.522

(3.41), 7.528 (1.67), 7.535 (1.51), 7.539 (1.71), 7.552 (0.66), 7.556 (0.44), 7.644 (2.79), 7.664 (2.50), 7.864 (1.50), 7.871 (0.85), 7.882 (1.56), 7.887 (1.27), 8.212 (1.33), 8.217 (1.24), 8.230 (0.72), 8.234 (1.20), 8.236 (1.26).

Intermediate 165

(rac)-ethyl 2,3,4-trimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylate

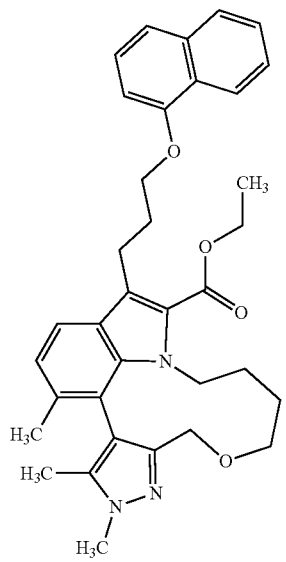 [SMILES: CCOC(=O)c1c(CCCOc2cccc3ccccc23)c2ccc(C)c3c2n1CCCCOCc1nn(C)c(C)c1-3]

An autoclave was charged with (rac)-ethyl (11Z)-2,3,4-trimethyl-7-[3-(naphthalen-1-yloxy)propyl]-2,10,13,15-tetrahydropyrazolo[4',3':9,10][1,6]oxazacycloundecino[8,7,6-hi]indole-8-carboxylate (570 mg, 1.01 mmol), ethanol (18 ml), THF (3.6 ml) and palladium 10% on charcoal (108 mg, 10% purity, 101 µmol) and the mixture was stirred under 21 bar hydrogen atmosphere at room temperature for 22 h. For work-up, the mixture was filtered through a pad of celite, eluted with ethyl acetate and the combined filtrates were concentrated under reduced pressure to give the title compound (550 mg, 87% yield), which was directly used in the next step.

LC-MS (Method 2): Rt=1.70 min, MS (ESIpos): m/z=566 [M+H]$^+$

Intermediate 166 ethyl 1-{3-[(tert-butoxycarbonyl)(methyl)amino]propyl}-7-[3-(hydroxymethyl)-1,5-dimethyl-1H-pyrazol-4-yl]-6-methyl-3-[3-(naphthalen-1-yloxy)propyl]-1H-indole-2-carboxylate

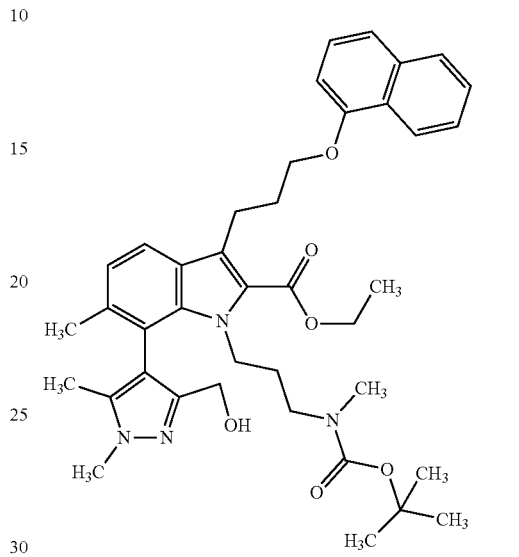

A mixture of ethyl 7-[3-(hydroxymethyl)-1,5-dimethyl-1H-pyrazol-4-yl]-6-methyl-3-[3-(naphthalen-1-yloxy)propyl]-1H-indole-2-carboxylate (see Intermediate 163, 850 mg, 1.66 mmol caesium carbonate (2.71 g, 8.31 mmol) and tert-butyl (3-bromopropyl)methylcarbamate (see Intermediate 1, 461 mg, 1.83 mmol) in DMF (21 ml) was stirred for 24 h at room temperature. For work-up, water was added, and the mixture was extracted with a mixture of dichloromethane and 2-propanol (4:1). The combined organic phases were filtered through a silicone filter and concentrated. The residue was purified by flash chromatography (50 g Biotage SNAP cartridge silica, hexanes/ethyl acetate/ gradient, 50%→100% ethyl acetate) to give the title compound (1.01 g, 84% yield).

LC-MS (Method 2): R$_t$=1.72 min; MS (ESIpos): m/z=683 [M+H]$^+$ $^1$H-NMR (400 MHz, DMSO-d6) δ [ppm]: 1.144 (0.55), 1.256 (3.84), 1.274 (8.32), 1.292 (5.83), 1.305 (3.99), 1.367 (2.64), 1.470 (0.45), 1.962 (8.52), 1.988 (0.50), 2.012 (7.88), 2.175 (0.95), 2.196 (1.30), 2.206 (6.83), 2.518 (16.00), 2.523 (10.92), 2.605 (1.89), 3.159 (0.65), 3.172 (0.65), 3.235 (3.94), 3.261 (1.69), 3.278 (1.15), 3.419 (0.55), 3.432 (0.65), 3.487 (0.65), 3.500 (0.50), 3.726 (6.08), 3.821 (2.34), 4.040 (1.40), 4.054 (1.20), 4.070 (1.64), 4.084 (1.60), 4.110 (0.75), 4.215 (1.40), 4.229 (2.89), 4.241 (3.54), 4.258 (2.74), 4.276 (0.90), 4.285 (1.69), 4.299 (1.64), 4.669 (0.90), 4.947 (0.75), 6.919 (1.64), 6.938 (1.79), 7.013 (1.50), 7.034 (1.60), 7.379 (1.15), 7.400 (2.34), 7.419 (1.84), 7.457 (2.49), 7.478 (1.35), 7.501 (0.45), 7.513 (1.50), 7.517 (2.49), 7.528 (2.89), 7.536 (2.64), 7.542 (1.69), 7.554 (0.50), 7.610 (2.19), 7.631 (1.99), 7.865 (1.40), 7.883 (0.90), 7.889 (1.20), 8.227 (1.20), 8.235 (0.85), 8.251 (1.15).

523

Intermediate 167 ethyl 7-[3-(bromomethyl)-1,5-dimethyl-1H-pyrazol-4-yl]-1-{3-[(tert-butoxycarbonyl)(methyl)amino]propyl}-6-methyl-3-[3-(naphthalen-1-yloxy)propyl]-1H-indole-2-carboxylate

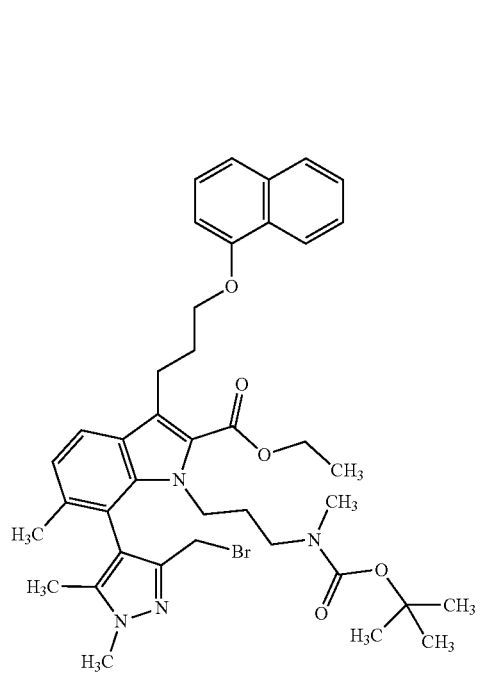 [SMILES: CCOC(=O)c1c(CCCOc2cccc3ccccc23)c2ccc(C)c(-c3c(CBr)nn(C)c3C)c2n1CCCN(C)C(=O)OC(C)(C)C]

Tetrabromomethane (1.02 g, 3.08 mmol) was added to a solution of ethyl 1-{3-[(tert-butoxycarbonyl)(methyl)amino]propyl}-7-[3-(hydroxymethyl)-1,5-dimethyl-1H-pyrazol-4-yl]-6-methyl-3-[3-(naphthalen-1-yloxy)propyl]-1H-indole-2-carboxylate (957 mg, 1.40 mmol) and triphenylphosphine (882 mg, 3.36 mmol) in dichloromethane (26 ml) at 0° C. and the mixture was stirred for 2 h at room temperature. For work-up, the mixture was concentrated (2.87 g) and used in the next step without further purification.

LC-MS (Method 2): $R_t$=1.84 min; MS (ESIpos): m/z=745 [M+H]$^+$

524

Intermediate 168 ethyl 7-[3-(bromomethyl)-1,5-dimethyl-1H-pyrazol-4-yl]-6-methyl-1-[3-(methylamino)propyl]-3-[3-(naphthalen-1-yloxy)propyl]-1H-indole-2-carboxylate hydrochloric acid salt Hydrogen chloride (26 ml, 4.0 M in dioxane, 100 mmol) was added to a solution of ethyl 7-[3-(bromomethyl)-1,5-dimethyl-1H-pyrazol-4-yl]-1-{3-[(tert-butoxycarbonyl)(methyl)amino]propyl}-6-methyl-3-[3-(naphthalen-1-yloxy)propyl]-1H-indole-2-carboxylate (2.86 g) in ethanol (23 ml) and the mixture was stirred for 2 h at room temperature. For work-up, the reaction mixture was concentrated to give the title compound (2.70 g) which was used in the next step without further purification.

Intermediate 169

(rac)-ethyl 7,10,11,12-tetramethyl-1-[3-(naphthalen-1-yloxy)propyl]-4,5,6,7,8,10-hexahydropyrazolo[3',4':7,8][1,5]diazecino[9,10,1-hi]indole-2-carboxylate formic acid salt

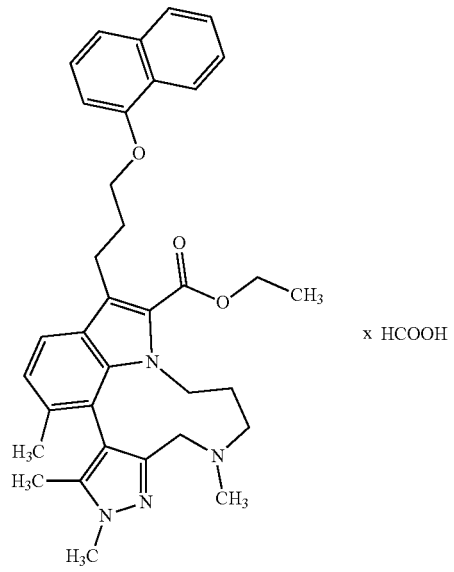 [SMILES: CCOC(=O)c1c(CCCOc2cccc3ccccc23)c2ccc(C)c3c2n1CCCN(C)Cc1nn(C)c(C)c1-3 ; "HCOOH"]

x HCOOH

A mixture of ethyl 7-[3-(bromomethyl)-1,5-dimethyl-1H-pyrazol-4-yl]-6-methyl-1-[3-(methylamino)propyl]-3-[3-(naphthalen-1-yloxy)propyl]-1H-indole-2-carboxylate hydrochloric acid salt (1.93 g) and caesium carbonate (2.28 g, 7.00 mmol) in DMF (110 ml) was stirred for 8 h at 65° C. For work-up, water was added and the mixture was extracted with a mixture of dichloromethane and 2-propanol (4:1). The combined organic phases were filtered through a silicone filter and concentrated. The residue was purified by flash chromatography (50 g Biotage SNAP cartridge silica, hexanes/ethyl acetate 1:1 to ethyl acetate to ethyl acetate/ethanol 4:1 gradient) followed by preparative HPLC to give the title compound (155 mg, 18% yield).

LC-MS (Method 2): $R_t$=1.75 min; MS (ESIpos): m/z=565 [M+H]$^+$ $^1$H-NMR (400 MHz, DMSO-d$_6$): δ [ppm]=8.26-8.21 (m, 1H), 8.16 (s, 1H), 7.88 (s, 1H), 7.87-7.86 (m, 1H), 7.60-7.36 (m, 5H), 6.97 (d, 1H), 6.89 (d, 1H), 4.47 (br dd, 1H), 4.30-4.14 (m, 4H), 3.79 (s, 3H), 3.78-3.71 (m, 1H), 3.29-3.15 (m, 2H), 3.07 (d, 1H), 2.47-2.35 (m, 2H), 2.18 (quin, 2H), 2.00-1.88 (m, 10H), 1.60-1.49 (m, 1H), 1.36-1.30 (m, 1H), 1.27 (t, 3H)

Intermediate 170 ethyl 7-[3-(hydroxymethyl)-5-methyl-1-(2,2,2-trifluoroethyl)-1H-pyrazol-4-yl]-3-[3-(naphthalen-1-yloxy)propyl]-1H-indole-2-carboxylate

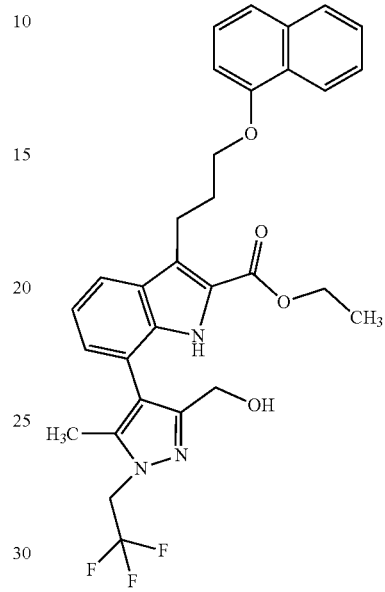

XPhos Pd G2 (see abbreviation list, 93.4 mg, 119 μmol) was added to a degassed mixture of ethyl 3-[3-(naphthalen-1-yloxy)propyl]-7-(4,4,5,5-tetramethyl-1,3,2-dioxaborolan-2-yl)-1H-indole-2-carboxylate (Intermediate 5, 1.76 g, 3.52 mmol), [4-bromo-5-methyl-1-(2,2,2-trifluoroethyl)-1H-pyrazol-3-yl]methanol (see Intermediate 123, 1.01 g, 3.70 mmol), aqueous potassium phosphate solution (14 ml, 0.50 M, 7.0 mmol) and THF (43 ml) and the mixture was stirred for 2 h at 45° C. For work-up, ethyl acetate was added, the mixture was filtered through a pad of celite, eluted with ethyl acetate and the organic phase was washed with brine, filtered through a silicone filter and concentrated. The residue was purified by flash chromatography (100 g Biotage SNAP cartridge silica, hexanes/ethyl acetate gradient, 0%→50% ethyl acetate) to give the title compound (2.08 g, 103% calculated yield).

LC-MS (Method 2): $R_t$=1.59 min; MS (ESIpos): m/z=566 [M+H]$^+$ $^1$H-NMR (400 MHz, DMSO-d6) δ [ppm]: 1.066 (7.77), 1.257 (5.28), 1.275 (11.70), 1.293 (5.43), 2.205 (15.02), 2.232 (1.66), 2.251 (1.21), 2.272 (1.51), 2.331 (3.17), 2.518 (16.00), 2.523 (10.72), 2.673 (3.09), 3.358 (2.42), 3.376 (1.43), 3.938 (1.21), 4.205 (1.74), 4.219 (3.55), 4.229 (2.34), 4.246 (4.98), 4.265 (5.28), 4.282 (3.70), 4.332 (0.53), 4.346 (0.53), 5.107 (1.06), 5.131 (2.11), 5.154 (1.96), 5.177 (0.60), 5.732 (1.58), 6.911 (2.11), 6.929 (2.26), 7.072 (0.68), 7.091 (1.74), 7.109 (1.58), 7.124 (2.04), 7.141 (0.83), 7.375 (1.36), 7.396 (2.87), 7.415 (2.26), 7.452 (3.09), 7.472 (1.66), 7.490 (0.68), 7.502 (1.66), 7.507 (1.58), 7.512 (1.74), 7.520 (3.70), 7.526 (1.89), 7.532 (1.66), 7.536 (1.81), 7.549 (0.68), 7.690 (1.66), 7.708 (1.51), 7.861 (1.74), 7.869 (0.98), 7.879 (1.66), 7.885 (1.43), 8.224 (1.51), 8.229 (1.51), 8.248 (1.43), 11.294 (1.06).

Intermediate 171

(rac)-ethyl (11Z)-3-methyl-7-[3-(naphthalen-1-yloxy)propyl]-2-(2,2,2-trifluoroethyl)-2,10,13,15-tetrahydropyrazolo[4',3':9,10][1,6]oxazacycloundecino[8,7,6-hi]indole-8-carboxylate

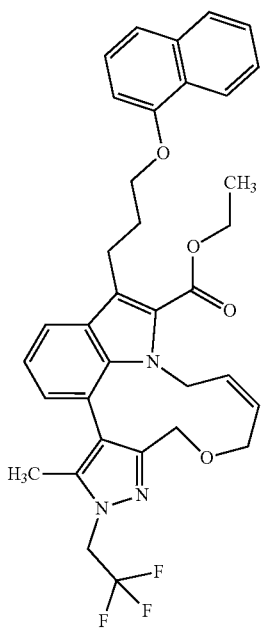 [SMILES: CCOC(=O)c1c(CCCOc2cccc3ccccc23)c2cccc3c2n1C/C=C\COCc1nn(CC(F)(F)F)c(C)c1-3]

A mixture of ethyl 7-[3-(hydroxymethyl)-5-methyl-1-(2,2,2-trifluoroethyl)-1H-pyrazol-4-yl]-3-[3-(naphthalen-1-yloxy)propyl]-1H-indole-2-carboxylate (1.02 g, 1.81 mmol), (2Z)-1,4-dichlorobut-2-ene (228 µl, 2.2 mmol), sodium iodide (543 mg, 3.62 mmol) and caesium carbonate (2.95 g, 9.05 mmol) in acetonitrile (31 ml) was stirred for 18 h at room temperature, followed by 7 h at 60° C. For work-up, water was added and the mixture was extracted with a mixture of dichloromethane and 2-propanol (4:1). The combined organic phases were filtered through a silicone filter and concentrated. The residue was purified by flash chromatography (50 g Biotage SNAP cartridge silica, hexanes/ethyl acetate gradient, 0%→100% ethyl acetate.) to give the title compound (759 mg, 64% yield).

LC-MS (Method 1): $R_t$=1.71 min; MS (ESIpos): m/z=618 [M+H]$^+$ $^1$H-NMR (400 MHz, DMSO-d$_6$): δ [ppm]=8.24-8.20 (m, 1H), 7.90-7.85 (m, 1H), 7.79 (dd, 1H), 7.56-7.38 (m, 4H), 7.14-7.09 (m, 1H), 6.95-6.91 (m, 2H), 5.35-5.12 (m, 4H), 4.88 (br d, 1H), 4.64 (dd, 1H), 4.43-4.21 (m, 6H), 3.72 (t, 1H), 3.61 (dd, 1H), 3.41-3.35 (m, 1H), 3.32-3.26 (m, 1H), 2.29-2.18 (m, 2H), 1.90 (s, 3H), 1.28 (t, 3H)

Intermediate 172 ethyl 7-[5-(hydroxymethyl)-3-methyl-1-(2,2,2-trifluoroethyl)-1H-pyrazol-4-yl]-3-[3-(naphthalen-1-yloxy)propyl]-1H-indole-2-carboxylate

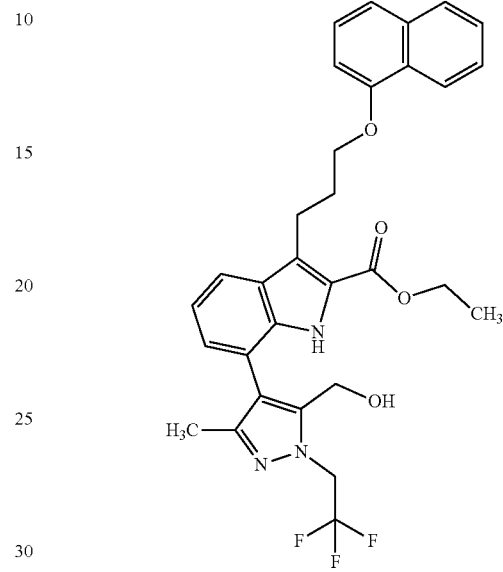

XPhos Pd G2 (see abbreviation list, 121 mg, 154 µmol) was added to a degassed mixture of ethyl 3-[3-(naphthalen-1-yloxy)propyl]-7-(4,4,5,5-tetramethyl-1,3,2-dioxaborolan-2-yl)-1H-indole-2-carboxylate (see Intermediate 5, 2.28 g, 4.57 mmol), [4-bromo-3-methyl-1-(2,2,2-trifluoroethyl)-1H-pyrazol-5-yl]methanol (see Intermediate 124, 1.31 g, 4.79 mmol) aqueous potassium phosphate solution (18 ml, 0.50 M, 9.1 mmol) and THF (56 ml) and the mixture was stirred for 2 h at 45° C. For work-up, ethyl acetate was added, the mixture was filtered through a pad of celite, eluted with ethyl acetate and the organic phase was washed with brine, filtered through a silicone filter and concentrated. The residue was purified by flash chromatography (100 g Biotage SNAP cartridge silica, hexanes/ethyl acetate gradient, 20%→100% ethyl acetate) to give the title compound (2.10 g, 77% yield).

LC-MS (Method 1): $R_t$=1.63 min; MS (ESIpos): m/z=566 [M+H]$^+$ $^1$H-NMR (400 MHz, DMSO-d6) δ [ppm]: 1.066 (8.26), 1.154 (0.47), 1.172 (0.90), 1.190 (0.45), 1.258 (4.76), 1.276 (10.47), 1.294 (4.83), 1.988 (1.60), 2.081 (16.00), 2.216 (0.97), 2.232 (1.29), 2.251 (0.99), 2.518 (3.54), 2.523 (2.37), 3.357 (2.01), 3.374 (1.17), 3.939 (1.29), 4.204 (1.38), 4.219 (2.84), 4.234 (1.49), 4.239 (1.78), 4.257 (4.20), 4.274 (4.11), 4.292 (1.29), 4.364 (1.11), 5.100 (0.70), 5.123 (1.94), 5.145 (1.83), 5.168 (0.56), 5.788 (0.88), 6.910 (1.69), 6.927 (1.90), 7.081 (1.22), 7.099 (2.14), 7.119 (1.92), 7.156 (2.23), 7.158 (2.39), 7.174 (1.42), 7.176 (1.24), 7.375 (1.29), 7.395 (2.46), 7.414 (2.03), 7.452 (2.55), 7.472 (1.38), 7.491 (0.54), 7.504 (1.47), 7.507 (1.31), 7.513 (1.56), 7.521 (3.29), 7.528 (1.62), 7.533 (1.44), 7.537 (1.60), 7.550 (0.63), 7.703 (1.74), 7.705 (1.74), 7.723 (1.67), 7.726 (1.58), 7.861 (1.44), 7.869 (0.79), 7.879 (1.40), 7.884 (1.22), 8.221 (1.26), 8.227 (1.22), 8.246 (1.20), 10.950 (0.99).

Intermediate 173

(rac)-ethyl (11Z)-3-methyl-7-[3-(naphthalen-1-yloxy)propyl]-1-(2,2,2-trifluoroethyl)-1,10,13,15-tetrahydropyrazolo[4',3':9,10][1,6]oxazacycloundecino[8,7,6-hi]indole-8-carboxylate

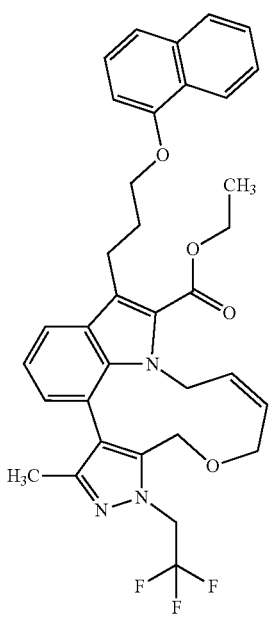 [SMILES: CCOC(=O)c1c(CCCOc2cccc3ccccc23)c2cccc3c2n1C/C=C\COCc1c-3c(C)nn1CC(F)(F)F]

A mixture of ethyl 7-[5-(hydroxymethyl)-3-methyl-1-(2,2,2-trifluoroethyl)-1H-pyrazol-4-yl]-3-[3-(naphthalen-1-yloxy)propyl]-1H-indole-2-carboxylate (980 mg, 1.73 mmol), (2Z)-1,4-dichlorobut-2-ene (220 µl, 2.1 mmol), sodium iodide (519 mg, 3.47 mmol) and caesium carbonate (2.82 g, 8.66 mmol) in acetonitrile (29 ml) was stirred for 17 h at room temperature followed by 6.5 h at 65° C. For work-up, water was added and the mixture was extracted with a mixture of dichloromethane and 2-propanol (4:1). The combined organic phases were filtered through a silicone filter and concentrated. The residue was purified by flash chromatography (50 g Biotage SNAP cartridge silica, hexanes/ethyl acetate gradient, 0%→50% ethyl acetate) to give the title compound (678 mg, 63% yield).

LC-MS (Method 1): $R_t$=1.78 min; MS (ESIpos): m/z=618 [M+H]$^+$ $^1$H-NMR (400 MHz, DMSO-d$_6$): δ [ppm]=8.20 (dd, 1H), 7.89-7.80 (m, 2H), 7.55-7.38 (m, 4H), 7.15-7.10 (m, 1H), 6.93 (d, 1H), 6.87 (dd, 1H), 5.22-4.91 (m, 5H), 4.70 (d, 1H), 4.61 (dd, 1H), 4.36-4.21 (m, 5H), 3.78 (dd, 1H), 3.55 (t, 1H), 3.42-3.35 (m, 1H), 3.31-3.26 (m, 1H), 2.30-2.21 (m, 2H), 1.76 (s, 3H), 1.29 (t, 3H)

Intermediate 174

(rac)-ethyl 3-methyl-7-[3-(naphthalen-1-yloxy)propyl]-1-(2,2,2-trifluoroethyl)-1,10,11,12,13,15-hexahydropyrazolo[4',3':9,10][1,6]oxazacycloundecino[8,7,6-hi]indole-8-carboxylate

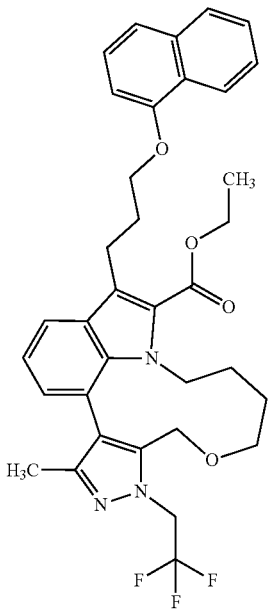 [SMILES: CCOC(=O)c1c(CCCOc2cccc3ccccc23)c2cccc3c2n1CCCCOCc1c-3c(C)nn1CC(F)(F)F]

An autoclave was charged with (rac)-ethyl (11Z)-3-methyl-7-[3-(naphthalen-1-yloxy)propyl]-1-(2,2,2-trifluoroethyl)-1,10,13,15-tetrahydropyrazolo[4',3':9,10][1,6]oxazacycloundecino[8,7,6-hi]indole-8-carboxylate (580 mg, 939 µmol), ethanol (19 ml), THF (3.8 ml) and palladium 10% on charcoal (99.9 mg, 10% purity, 93.9 µmol) and the mixture was stirred under 25 bar hydrogen atmosphere at room temperature for 22 h. For work-up, the mixture was filtered through a pad of celite, eluted with ethyl acetate and the combined filtrates were concentrated under reduced pressure to give the title compound 560 mg (96% yield), which was directly used in the next step.

LC-MS (Method 1): $R_t$=1.77 min; MS (ESIpos): m/z=620 [M+H]$^+$

Intermediate 175 ethyl 7-[1-cyclopropyl-3-(hydroxymethyl)-5-methyl-1H-pyrazol-4-yl]-3-[3-(naphthalen-1-yloxy)propyl]-1H-indole-2-carboxylate

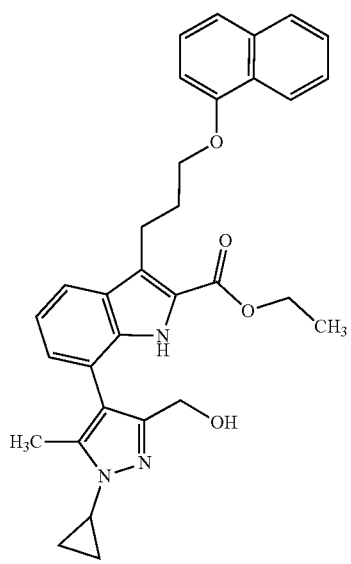

XPhos Pd G2 (see abbreviation list, 201 mg, 255 µmol) was added to a degassed mixture of ethyl 3-[3-(naphthalen-1-yloxy)propyl]-7-(4,4,5,5-tetramethyl-1,3,2-dioxaborolan-2-yl)-1H-indole-2-carboxylate (see Intermediate 5, 3.64 g, 7.29 mmol), (4-bromo-1-cyclopropyl-5-methyl-1H-pyrazol-3-yl)methanol (see Intermediate 127, 1.77 g, 7.66 mmol) aqueous potassium phosphate solution (29 ml, 0.50 M, 15 mmol) and THF (89 ml) and the mixture was stirred for 2 h at 45° C. For work-up, ethyl acetate was added, the mixture was filtered through a pad of celite, eluted with ethyl acetate and the organic phase was washed with brine, filtered through a silicone filter and concentrated. The residue was purified by flash chromatography (100 g Biotage SNAP cartridge silica, hexanes/ethyl acetate gradient, 50%→100% ethyl acetate) to give the title compound (3.26 g, 84% yield).

LC-MS (Method 2): $R_t$=1.59 min; MS (ESIpos): m/z=524 [M+H]$^+$ $^1$H-NMR (400 MHz, DMSO-d6) δ [ppm]: 0.987 (0.48), 0.991 (0.50), 1.001 (0.40), 1.007 (0.61), 1.021 (1.59), 1.026 (2.03), 1.039 (2.01), 1.044 (1.81), 1.056 (0.84), 1.117 (0.88), 1.127 (2.60), 1.135 (2.46), 1.142 (1.45), 1.146 (1.21), 1.154 (2.35), 1.172 (4.20), 1.190 (2.15), 1.255 (4.65), 1.273 (10.40), 1.291 (4.77), 1.988 (7.79), 2.213 (1.01), 2.233 (1.51), 2.247 (16.00), 2.285 (2.35), 2.518 (1.06), 2.523 (0.72), 3.355 (1.87), 3.372 (1.16), 3.530 (0.76), 3.539 (1.04), 3.549 (1.43), 3.557 (0.93), 3.566 (0.70), 3.999 (0.61), 4.017 (1.78), 4.035 (1.73), 4.053 (0.59), 4.198 (1.47), 4.213 (3.11), 4.224 (2.49), 4.228 (2.26), 4.241 (6.92), 4.259 (4.65), 4.276 (1.97), 4.290 (0.78), 5.682 (1.54), 6.906 (1.77), 6.924 (1.90), 7.060 (1.06), 7.079 (2.52), 7.098 (2.46), 7.107 (2.53), 7.111 (2.79), 7.125 (1.15), 7.129 (0.80), 7.372 (1.28), 7.393 (2.49), 7.412 (2.03), 7.450 (2.58), 7.471 (1.41), 7.491 (0.56), 7.504 (1.50), 7.509 (1.36), 7.513 (1.61), 7.521 (3.27), 7.528 (1.69), 7.533 (1.47), 7.537 (1.60), 7.550 (0.60), 7.659 (1.64), 7.662 (1.59), 7.678 (1.56), 7.682 (1.41), 7.860 (1.48), 7.868 (0.78), 7.878 (1.36), 7.883 (1.24), 8.230 (1.27), 8.237 (1.22), 8.248 (0.64), 8.255 (1.20), 11.329 (1.78).

Intermediate 176

(rac)-ethyl (11Z)-2-cyclopropyl-3-methyl-7-[3-(naphthalen-1-yloxy)propyl]-2,10,13,15-tetrahydropyrazolo[4',3':9,10][1,6]oxazacycloundecino[8,7,6-hi]indole-8-carboxylate

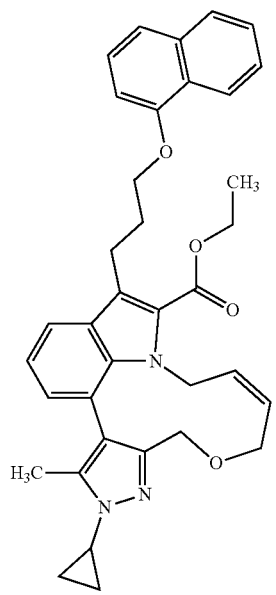 [SMILES: CCOC(=O)c1c(CCCOc2cccc3ccccc23)c2cccc3c2n1C/C=C\COCc1nn(C2CC2)c(C)c1-3]

A mixture of ethyl 7-[1-cyclopropyl-3-(hydroxymethyl)-5-methyl-1H-pyrazol-4-yl]-3-[3-(naphthalen-1-yloxy)propyl]-1H-indole-2-carboxylate (524 mg, 1.00 mmol), (2Z)-1,4-dichlorobut-2-ene (132 µl, 1.3 mmol), sodium iodide (300 mg, 2.00 mmol) and caesium carbonate (1.63 g, 5.00 mmol) in acetonitrile (12 ml) was stirred for 20 h at room temperature followed by 6 h at 60° C. For work-up, water was added and the mixture was extracted with a mixture of dichloromethane and 2-propanol (4:1). The combined organic phases were filtered through a silicone filter and concentrated. The residue was purified by flash chromatography (Biotage SNAP cartridge silica, hexanes/ethyl acetate gradient) to give the title compound (373 mg, 64% yield).

LC-MS (Method 2): $R_t$=1.72 min; MS (ESIpos): m/z=576 [M+H]$^+$ $^1$H-NMR (400 MHz, DMSO-d$_6$): δ [ppm]=8.26-8.20 (m, 1H), 7.90-7.85 (m, 1H), 7.77 (dd, 1H), 7.56-7.38 (m, 4H), 7.09 (t, 1H), 6.95-6.87 (m, 2H), 5.30 (td, 1H), 5.14 (td, 1H), 4.93-4.85 (m, 1H), 4.79-4.67 (m, 1H), 4.37-4.17 (m, 6H), 3.74-3.55 (m, 3H), 3.42-3.35 (m, 1H), 3.31-3.25 (m, 1H), 2.28-2.19 (m, 2H), 1.93 (s, 3H), 1.29 (t, 3H), 1.24-1.19 (m, 1H), 1.11-0.94 (m, 4H)

Intermediate 177

(rac)-ethyl 2-cyclopropyl-3-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylate

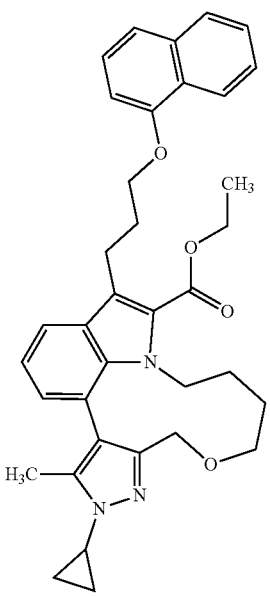 [SMILES: CCOC(=O)c1c(CCCOc2cccc3ccccc23)c2cccc3c2n1CCCCOCc1nn(C2CC2)c(C)c1-3]

An autoclave was charged with (rac)-ethyl (11Z)-2-cyclopropyl-3-methyl-7-[3-(naphthalen-1-yloxy)propyl]-2,10,13,15-tetrahydropyrazolo[4',3':9,10][1,6]oxazacycloundecino[8,7,6-hi]indole-8-carboxylate (370 mg, 643 µmol), ethanol (11 ml), THF (2.3 ml) and palladium 10% on charcoal (68.4 mg, 10% purity, 64.3 µmol) and the mixture was stirred under 22 bar hydrogen atmosphere at room temperature for 24 h. For work-up, the mixture was filtered through a pad of celite, eluted with ethyl acetate and the combined filtrates were concentrated under reduced pressure to give the title compound (349 mg), which was directly used in the next step.

LC-MS (Method 2): Rt=1.74 min; MS (ESIpos): m/z=578 [M+H]$^+$

Intermediate 178 ethyl 7-[3-(hydroxymethyl)-5-(methoxymethyl)-1-methyl-1H-pyrazol-4-yl]-3-[3-(naphthalen-1-yloxy)propyl]-1H-indole-2-carboxylate

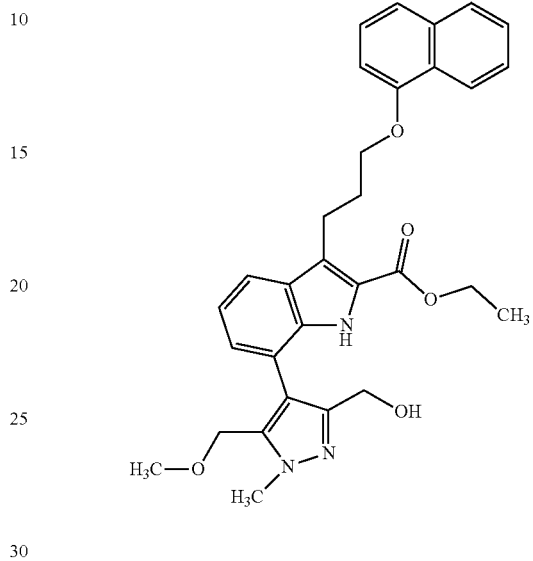

XPhos Pd G2 (see abbreviation list, 114 mg, 145 µmol) was added to a degassed mixture of ethyl 3-[3-(naphthalen-1-yloxy)propyl]-7-(4,4,5,5-tetramethyl-1,3,2-dioxaborolan-2-yl)-1H-indole-2-carboxylate (see Intermediate 5, 2.14 g, 4.29 mmol), [4-bromo-5-(methoxymethyl)-1-methyl-1H-pyrazol-3-yl]methanol (see Intermediate 109, 1.06 g, 4.51 mmol), aqueous potassium phosphate solution (17 ml, 0.50 M, 8.6 mmol) and THF (52 ml) and the mixture was stirred for 2 h at 45° C. For work-up, ethyl acetate was added, the mixture was filtered through a pad of celite, eluted with ethyl acetate and the organic phase was washed with brine, filtered through a silicone filter and concentrated. The residue was purified by flash chromatography (55 g Biotage SNAP cartridge NH$_2$ silica, hexanes/ethyl acetate gradient, 0%→15% ethyl acetate) to give the title compound (1.60 g, 71% yield).

LC-MS (Method 2): R$_t$=1.55 min; MS (ESIpos): m/z=528 [M+H]$^+$ $^1$H-NMR (400 MHz, DMSO-d6) δ [ppm]: 1.153 (1.43), 1.171 (3.05), 1.189 (1.55), 1.256 (4.77), 1.274 (10.78), 1.291 (4.92), 1.987 (5.03), 2.220 (0.96), 2.237 (1.28), 2.256 (0.98), 2.518 (0.52), 3.244 (1.73), 3.338 (11.72), 3.346 (1.38), 3.366 (1.81), 3.383 (1.13), 3.708 (0.90), 3.894 (16.00), 3.999 (0.41), 4.016 (1.23), 4.034 (1.20), 4.200 (1.38), 4.215 (2.86), 4.231 (1.41), 4.239 (1.44), 4.257 (4.17), 4.276 (6.66), 4.278 (7.41), 4.293 (3.21), 4.406 (0.48), 5.568 (0.66), 5.579 (1.64), 5.590 (0.64), 5.759 (0.46), 6.900 (1.71), 6.917 (1.85), 7.094 (1.40), 7.112 (2.18), 7.132 (1.89), 7.199 (2.18), 7.202 (2.33), 7.217 (1.61), 7.220 (1.49), 7.368 (1.26), 7.389 (2.47), 7.408 (2.02), 7.446 (2.52), 7.467 (1.40), 7.473 (0.57), 7.477 (0.66), 7.490 (1.44), 7.494 (1.28), 7.506 (1.68), 7.509 (1.99), 7.512 (2.16), 7.514 (1.76), 7.526 (1.35), 7.530 (1.54), 7.543 (0.68), 7.547 (0.49), 7.705 (1.79), 7.724 (1.65), 7.856 (1.49), 7.861 (0.94), 7.875 (1.63), 7.879 (1.26), 8.204 (1.29), 8.208 (1.36), 8.224 (0.98), 8.226 (1.25), 8.228 (1.24), 11.065 (2.39).

535

Intermediate 179

(rac)-ethyl (11Z)-3-(methoxymethyl)-2-methyl-7-[3-(naphthalen-1-yloxy)propyl]-2,10,13,15-tetrahydropyrazolo[4',3':9,10][1,6]oxazacycloundecino[8,7,6-hi]indole-8-carboxylate

536

Intermediate 180

(rac)-ethyl 3-(methoxymethyl)-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylate

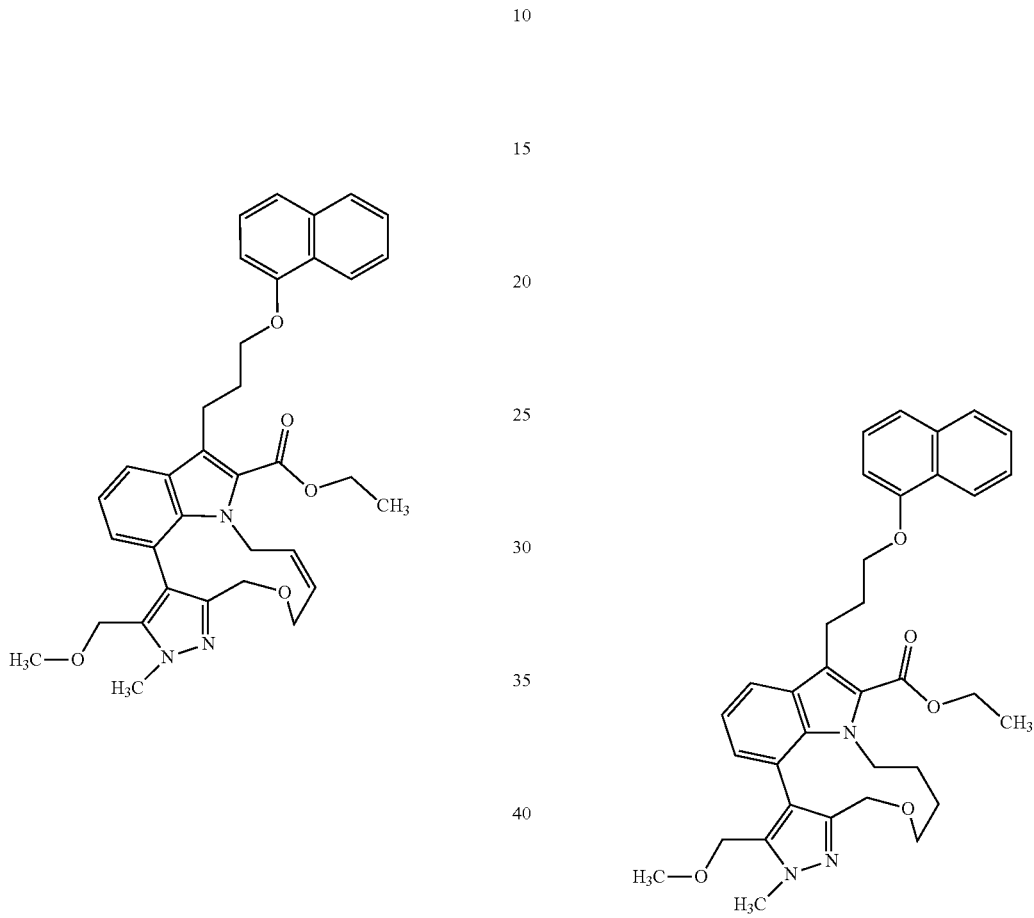

A mixture of ethyl 7-[3-(hydroxymethyl)-5-(methoxymethyl)-1-methyl-1H-pyrazol-4-yl]-3-[3-(naphthalen-1-yloxy)propyl]-1H-indole-2-carboxylate (800 mg, 1.52 mmol), (2Z)-1,4-dichlorobut-2-ene (190 µl, 1.8 mmol), sodium iodide (455 mg, 3.03 mmol) and caesium carbonate (2.47 g, 7.58 mmol) in acetonitrile (23 ml) was stirred 4 h at room temperature followed by 16 h at 60° C. For work-up, water was added and the mixture was extracted with a mixture of dichloromethane and 2-propanol (4:1). The combined organic phases were filtered through a silicone filter and concentrated. The residue was purified by flash chromatography (28 g Biotage SNAP cartridge NH$_2$ silica, hexanes/ethyl acetate gradient 0%→50% ethyl acetate) to give the title compound (380 mg, 43% yield).

LC-MS (Method 1): Rt=1.66 min, MS (ESIpos): m/z=580 [M+H]$^+$ $^1$H-NMR (400 MHz, DMSO-d$_6$): δ [ppm]=8.25-8.20 (m, 1H), 7.90-7.85 (m, 1H), 7.79 (dd, 1H), 7.56-7.37 (m, 4H), 7.11-7.06 (m, 1H), 6.94-6.88 (m, 2H), 5.30 (td, 1H), 5.16 (td, 1H), 4.86 (br d, 1H), 4.74 (dd, 1H), 4.41 (d, 1H), 4.35-4.20 (m, 5H), 4.07-3.99 (m, 1H), 3.97-3.87 (m, 4H), 3.79-3.72 (m, 1H), 3.66-3.60 (m, 1H), 3.40-3.34 (m, 1H), 3.31-3.26 (m, 1H), 3.00 (s, 3H), 2.28-2.20 (m, 2H), 1.28 (t, 3H)

An autoclave was charged with (rac)-ethyl (11Z)-3-(methoxymethyl)-2-methyl-7-[3-(naphthalen-1-yloxy)propyl]-2,10,13,15-tetrahydropyrazolo[4',3':9,10][1,6]oxazacycloundecino[8,7,6-hi]indole-8-carboxylate (380 mg, 656 µmol), ethanol (11 ml), THF (2.3 ml) and palladium 10% on charcoal (69.7 mg, 10% purity, 65.6 µmol) and the mixture was stirred under 26 bar hydrogen atmosphere at room temperature for 22 h. For work-up, the mixture was filtered through a pad of celite, eluted with ethyl acetate and the combined filtrates were concentrated under reduced pressure to give the title compound (370 mg), which was directly used in the next step.

LC-MS (Method 1): Rt=1.69 min; MS (ESIpos): m/z=582 [M+H]$^+$

Intermediate 184 ethyl 7-[3-(hydroxymethyl)-1-methyl-5-(propan-2-yl)-1H-pyrazol-4-yl]-3-[3-(naphthalen-1-yloxy)propyl]-1H-indole-2-carboxylate

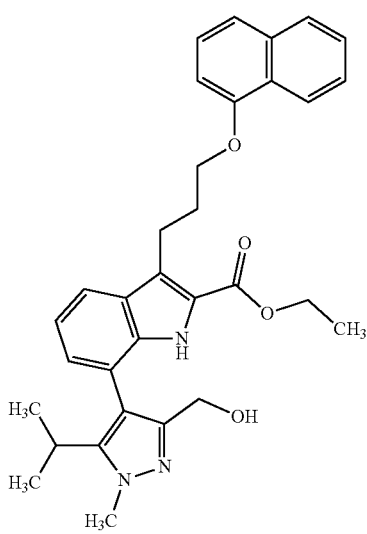 [SMILES: CCOC(=O)c1[nH]c2c(-c3c(CO)nn(C)c3C(C)C)cccc2c1CCCOc1cccc2ccccc12]

XPhos Pd G2 (203 mg, 257 µmol) was added to a degassed mixture of ethyl 3-[3-(naphthalen-1-yloxy)propyl]-7-(4,4,5,5-tetramethyl-1,3,2-dioxaborolan-2-yl)-1H-indole-2-carboxylate (see Intermediate 5, 2.83 g, 5.66 mmol), [4-bromo-1-methyl-5-(propan-2-yl)-1H-pyrazol-3-yl]methanol (see Intermediate 131, 1.20 g, 5.15 mmol), aqueous potassium phosphate solution (21 ml, 0.50 M, 10 mmol) and THF (63 ml) and the mixture was stirred for 2 h at 50° C. For work-up, ethyl acetate was added, the mixture was filtered through a pad of celite, eluted with ethyl acetate and the organic phase was washed with brine, filtered through a silicone filter and concentrated. The residue was purified by flash chromatography (100 g Biotage SNAP cartridge silica, hexanes/ethyl acetate gradient, 0%→100% ethyl acetate) to give the title compound (1.45 g, 49% yield).

LC-MS (Method 1): $R_t$=1.63 min; MS (ESIneg): m/z=524 [M–H]$^-$ $^1$H-NMR (400 MHz, DMSO-d6) δ [ppm]: 1.042 (3.13), 1.059 (3.21), 1.128 (3.37), 1.146 (3.28), 1.154 (1.20), 1.160 (4.39), 1.172 (1.24), 1.177 (4.33), 1.250 (3.97), 1.268 (8.47), 1.286 (4.06), 1.987 (1.56), 2.214 (0.84), 2.230 (1.09), 2.250 (0.84), 2.518 (0.90), 2.729 (0.88), 2.887 (1.10), 3.012 (0.84), 3.030 (1.11), 3.048 (0.76), 3.334 (16.00), 3.346 (1.61), 3.364 (0.96), 3.677 (4.47), 3.869 (0.81), 4.017 (0.80), 4.044 (0.76), 4.058 (0.72), 4.195 (1.02), 4.204 (1.84), 4.219 (2.68), 4.225 (2.27), 4.234 (1.76), 4.243 (3.80), 4.261 (3.53), 4.279 (1.06), 4.292 (1.19), 4.306 (1.22), 4.871 (0.74), 5.199 (1.06), 5.211 (1.89), 5.223 (1.02), 5.759 (1.74), 5.958 (0.99), 6.906 (1.44), 6.923 (1.54), 7.036 (0.89), 7.049 (2.32), 7.054 (2.43), 7.056 (2.68), 7.075 (2.15), 7.093 (0.85), 7.373 (1.05), 7.393 (2.03), 7.412 (1.75), 7.453 (2.11), 7.474 (1.19), 7.512 (1.34), 7.517 (2.28), 7.527 (2.62), 7.536 (2.38), 7.541 (1.46), 7.670 (1.17), 7.674 (1.22), 7.688 (1.08), 7.692 (1.11), 7.863 (1.18), 7.866 (0.88), 7.878 (0.73), 7.880 (0.79), 7.886 (1.00), 8.253 (1.05), 8.260 (0.77), 8.276 (0.97), 10.841 (2.18).

Intermediate 185 ethyl 1-{3-[(tert-butoxycarbonyl)(methyl)amino]propyl}-7-[3-(hydroxymethyl)-1-methyl-5-(propan-2-yl)-1H-pyrazol-4-yl]-3-[3-(naphthalen-1-yloxy)propyl]-1H-indole-2-carboxylate

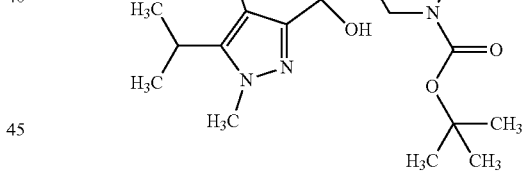

A mixture of ethyl 7-[3-(hydroxymethyl)-1-methyl-5-(propan-2-yl)-1H-pyrazol-4-yl]-3-[3-(naphthalen-1-yloxy)propyl]-1H-indole-2-carboxylate (1.40 g, 2.66 mmol), caesium carbonate (4.34 g, 13.3 mmol), potassium iodide (88.4 mg, 533 µmol) and tert-butyl (3-chloropropyl)methylcarbamate (see Intermediate 1, 830 mg, 4.00 mmol) in DMF (35 ml) was stirred for 19 h at 80° C. For work-up, water was added, and the mixture was extracted with ethyl acetate. The combined organic phases were filtered through a silicone filter and concentrated. The residue was purified by flash chromatography (50 g Biotage SNAP cartridge silica, hexanes/ethyl acetate gradient 0%→100% ethyl acetate) to give the title compound (1.26 g, 68% yield).

LC-MS (Method 1): $R_t$=1.76 min; MS (ESIpos): m/z=697 [M+H]$^+$

Intermediate 186 ethyl 7-[3-(bromomethyl)-1-methyl-5-(propan-2-yl)-1H-pyrazol-4-yl]-1-{3-[(tert-butoxycarbonyl)(methyl)amino]propyl}-3-[3-(naphthalen-1-yloxy)propyl]-1H-indole-2-carboxylate

Intermediate 187 ethyl 7-[3-(bromomethyl)-1-methyl-5-(propan-2-yl)-1H-pyrazol-4-yl]-1-[3-(methylamino) propyl]-3-[3-(naphthalen-1-yloxy)propyl]-1H-indole-2-carboxylate hydrochloric acid salt

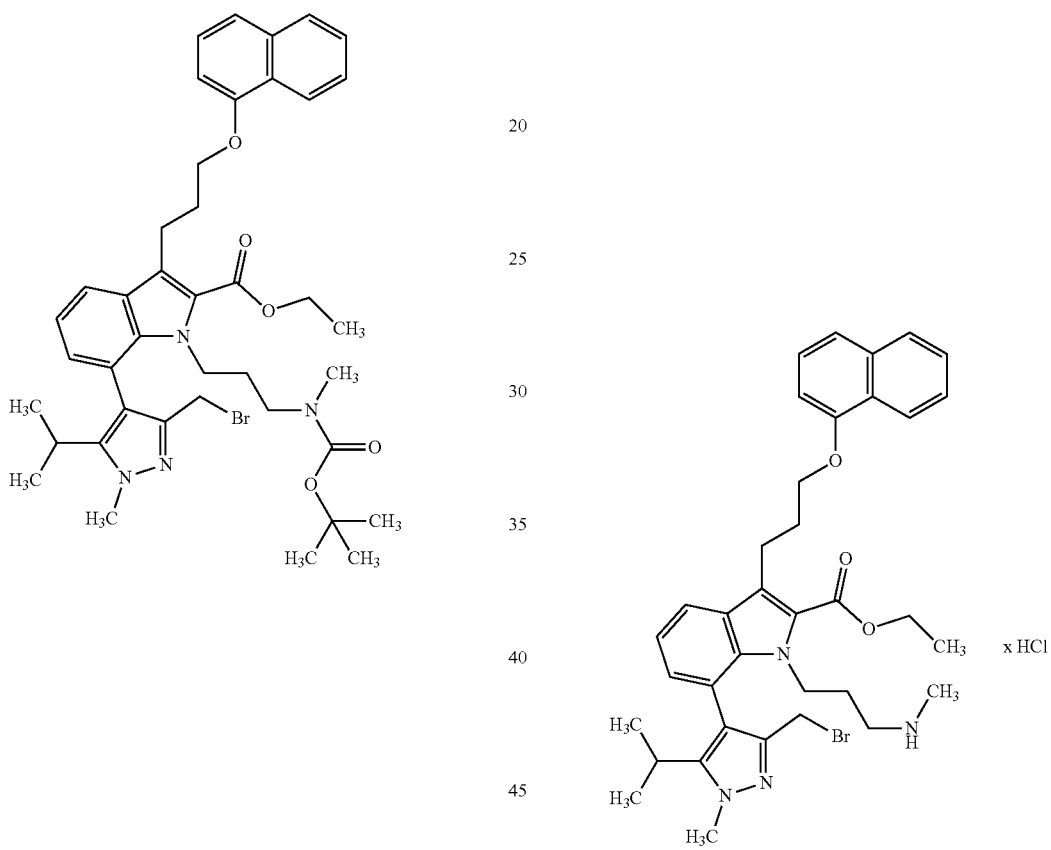

Tetrabromomethane (1.32 g, 3.98 mmol) was added to a solution of ethyl 1-{3-[(tert-butoxycarbonyl)(methyl)amino]propyl}-7-[3-(hydroxymethyl)-1-methyl-5-(propan-2-yl)-1H-pyrazol-4-yl]-3-[3-(naphthalen-1-yloxy)propyl]-1H-indole-2-carboxylate (1.26 g, 1.81 mmol) and triphenylphosphine (1.14 g, 4.34 mmol) in dichloromethane (33 ml) at 0° C. and the mixture was stirred for 2 h at room temperature. For work-up, the mixture was concentrated and used in the next step without further purification.

LC-MS (Method 1): Rt=1.88 min; MS (ESIpos): m/z=759 [M+H]$^+$

Hydrogen chloride (52 ml, 4.0 M in dioxane, 210 mmol) was added to a solution of ethyl 7-[3-(bromomethyl)-1-methyl-5-(propan-2-yl)-1H-pyrazol-4-yl]-1-{3-[(tert-butoxycarbonyl)(methyl)amino]propyl}-3-[3-(naphthalen-1-yloxy)propyl]-1H-indole-2-carboxylate (4.26 g) in ethanol (47 ml) and the mixture was stirred for 2 h at room temperature. For work-up, the reaction mixture was concentrated to give the title compound (3.84 g) which was used in the next step without further purification.

Intermediate 188

(rac)-ethyl 7,10-dimethyl-1-[3-(naphthalen-1-yloxy)propyl]-11-(propan-2-yl)-4,5,6,7,8,10-hexahydropyrazolo[3',4':7,8][1,5]diazecino[9,10,1-hi]indole-2-carboxylate

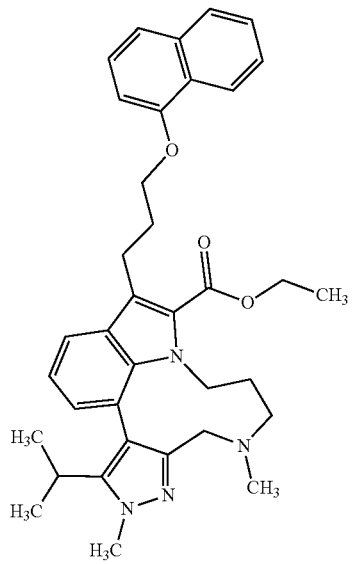 [SMILES: CCOC(=O)c1c(CCCOc2cccc3ccccc23)c2cccc3c2n1CCCN(C)Cc1nn(C)c(C(C)C)c1-3]

A mixture of ethyl 7-[3-(bromomethyl)-1-methyl-5-(propan-2-yl)-1H-pyrazol-4-yl]-1-[3-(methylamino)propyl]-3-[3-(naphthalen-1-yloxy)propyl]-1H-indole-2-carboxylate hydrochloric acid salt (3.84 g) and caesium carbonate (4.45 g, 13.7 mmol) in DMF (84 ml) was stirred for 2 h at 65° C. For work-up, water was added and the mixture was extracted with a mixture of dichloromethane and 2-propanol (4:1). The combined organic phases were filtered through a silicone filter and concentrated. The residue was purified by flash chromatography (100 g Biotage SNAP cartridge silica, hexanes/ethyl acetate gradient, 0%→100% ethyl acetate) followed by flash chromatography (28 g Biotage SNAP cartridge $NH_2$ silica, hexanes/ethyl acetate gradient, 0%→25% ethyl acetate) to give the title compound (140 mg, 9% yield).

LC-MS (Method 1): $R_t$=1.41 min; MS (ESIpos): m/z=579 [M+H]$^+$ $^1$H-NMR (400 MHz, DMSO-d6) δ [ppm]: 0.864 (6.20), 0.882 (6.28), 1.039 (6.53), 1.057 (6.55), 1.155 (1.75), 1.173 (3.66), 1.190 (1.91), 1.236 (0.41), 1.259 (0.60), 1.275 (4.94), 1.284 (0.93), 1.292 (10.76), 1.310 (5.05), 1.361 (0.44), 1.393 (0.49), 1.544 (0.55), 1.761 (12.59), 1.953 (0.71), 1.988 (7.43), 2.160 (0.44), 2.183 (1.06), 2.200 (1.64), 2.216 (1.12), 2.323 (1.20), 2.327 (1.69), 2.332 (1.20), 2.337 (0.52), 2.359 (0.44), 2.387 (0.74), 2.518 (6.44), 2.523 (4.40), 2.660 (0.55), 2.665 (1.23), 2.669 (1.69), 2.674 (1.17), 2.679 (0.55), 2.687 (1.34), 2.728 (1.34), 2.888 (1.67), 3.013 (0.90), 3.030 (1.26), 3.048 (0.90), 3.100 (1.17), 3.133 (2.35), 3.172 (2.57), 3.204 (1.20), 3.249 (0.52), 3.264 (0.66), 3.282 (1.09), 3.307 (1.04), 3.359 (0.63), 3.819 (16.00), 3.846 (0.66), 3.868 (0.63), 3.879 (0.68), 3.902 (0.66), 4.000 (0.49), 4.017 (1.42), 4.035 (1.37), 4.053 (0.44), 4.164 (1.04), 4.174 (1.86), 4.179 (1.88), 4.188 (1.23), 4.206 (1.15), 4.214 (0.63), 4.223 (0.98), 4.232 (1.75), 4.250 (1.91), 4.272 (1.91), 4.281 (0.41), 4.290 (1.80), 4.299 (0.90), 4.307 (0.57), 4.316 (0.85), 4.519 (0.60), 4.534 (0.63), 4.553 (0.57), 4.568 (0.57), 5.759 (2.48), 6.845 (1.97), 6.852 (1.86), 6.855 (1.97), 6.862 (2.21), 6.869 (2.54), 6.872 (2.29), 6.939 (2.13), 6.957 (1.86), 6.959 (2.24), 6.977 (1.50), 7.354 (1.42), 7.374 (2.62), 7.393 (2.08), 7.445 (2.57), 7.466 (1.56), 7.506 (0.49), 7.520 (2.29), 7.523 (1.77), 7.531 (2.27), 7.538 (1.83), 7.541 (2.29), 7.544 (2.32), 7.554 (0.60), 7.667 (1.91), 7.670 (2.02), 7.687 (1.80), 7.689 (1.69), 7.861 (1.45), 7.865 (0.98), 7.874 (1.39), 7.878 (0.93), 7.884 (1.26), 8.253 (1.31), 8.263 (1.09), 8.277 (1.20).

Intermediate 189

Ethyl 7-[3-(hydroxymethyl)-1-methyl-5-(morpholin-4-ylmethyl)-1H-pyrazol-4-yl]-3-[3-(naphthalen-1-yloxy)propyl]-1H-indole-2-carboxylate

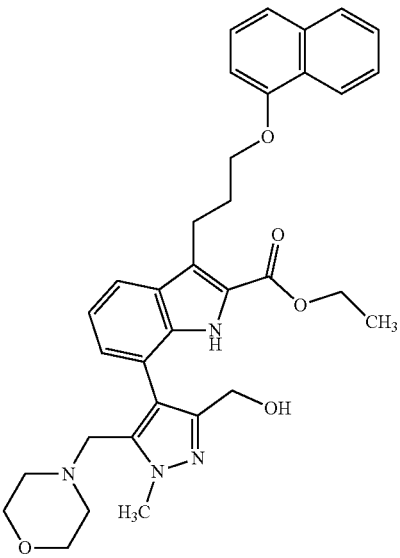 [SMILES: CCOC(=O)c1[nH]c2c(-c3c(CO)nn(C)c3CN3CCOCC3)cccc2c1CCCOc1cccc2ccccc12]

XPhos Pd G2 (see abbreviation list, 187 mg, 238 μmol) was added to a degassed mixture of ethyl 3-[3-(naphthalen-1-yloxy)propyl]-7-(4,4,5,5-tetramethyl-1,3,2-dioxaborolan-2-yl)-1H-indole-2-carboxylate (see Intermediate 5, 3.52 g, 7.06 mmol; prepared according to Journal of Medicinal Chemistry 2015, 58, 2180-2194), [4-bromo-1-methyl-5-(morpholin-4-ylmethyl)-1H-pyrazol-3-yl]methanol (see Intermediate 106, 2.15 g, 7.41 mmol), aqueous potassium phosphate solution (28 mL, 0.50 M) and THF (86 mL). The mixture was stirred at 50° C. for 2 hrs. The mixture was poured into water and extracted with ethyl acetate. The organic layer was dried using a silica filter and after removal of the solvent the residue was purified by flash chromatography to give the title compound 4.17 g (100% yield).

LC-MS: m/z=583.3 [M+H]$^+$

543

Intermediate 190

(rac)-Ethyl (11Z)-2-methyl-3-(morpholin-4-ylmethyl)-7-[3-(naphthalen-1-yloxy)propyl]-2,10,13,15-tetrahydropyrazolo[4',3':9,10][1,6]oxazacycloundecino[8,7,6-hi]indole-8-carboxylate

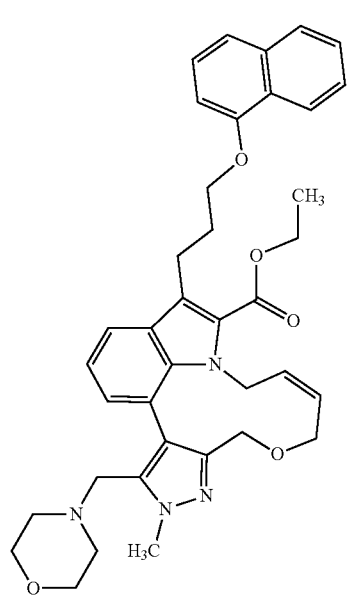 [SMILES: CCOC(=O)c1c(CCCOc2cccc3ccccc23)c2cccc3c2n1C/C=C\COCc1nn(C)c(CN2CCOCC2)c1-3]

A mixture of ethyl 7-[3-(hydroxymethyl)-1-methyl-5-(morpholin-4-ylmethyl)-1H-pyrazol-4-yl]-3-[3-(naphthalen-1-yloxy)propyl]-1H-indole-2-carboxylate (200 mg, 343 µmol), caesium carbonate (559 mg, 1.72 mmol), acetonitrile (19.7 mL), (2Z)-1,4-dichlorobut-2-ene (36 µL, 340 µmol) and sodium iodide (51.4 mg, 343 µmol) was stirred at RT for 20 hrs and at 60° C. for 6.5 hrs. The mixture was poured into ice-water and was extracted with dichloromethane/2-propanol. The organic layer was dried using a silicone filter and purified by flash chromatography (ethyl acetate:n-hexane) to give the title compound (95.0 mg, 41% yield).

LC-MS: m/z=635.3 [M+H]$^+$

544

Intermediate 191

(rac)-Ethyl 2-methyl-3-(morpholin-4-ylmethyl)-7-[3-(naphthalen-1-yloxy)propyl]-2,10,11,12,13,15-hexahydropyrazolo[4',3':9,10][1,6]oxazacycloundecino[8,7,6-hi]indole-8-carboxylate

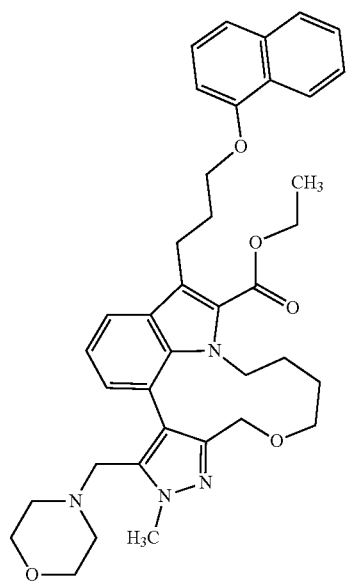 [SMILES: CCOC(=O)c1c(CCCOc2cccc3ccccc23)c2cccc3c2n1CCCCOCc1nn(C)c(CN2CCOCC2)c1-3]

To a solution of (rac)-ethyl (11Z)-2-methyl-3-(morpholin-4-ylmethyl)-7-[3-(naphthalen-1-yloxy)propyl]-2,10,13,15-tetrahydropyrazolo[4',3':9,10][1,6]oxazacycloundecino[8,7,6-hi]indole-8-carboxylate (324 mg, 510 µmol) in THF (1.8 mL) and ethanol (8.9 mL) was added palladium on charcoal (54.3 mg, 10%, 51.0 µmol) and the mixture was vigorously stirred under an atmosphere of hydrogen at 21 bar at RT for 22 hrs. The catalyst was filtered off, and the filtrate was concentrated to give the title compound (325 mg, 97% yield).

LC-MS: m/z=637.3 [M+H]$^+$

545

Intermediate 192

(rac)-Ethyl 2-methyl-3-(morpholin-4-ylmethyl)-7-[3-(naphthalen-1-yloxy)propyl]-2,10,11,13,14,16-hexahydropyrazolo[4',3':10,11][1,4,7]dioxazacyclododecino[9,8,7-hi]indole-8-carboxylate

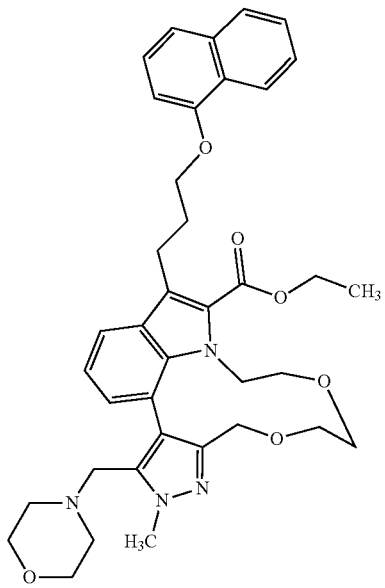 [SMILES: CCOC(=O)c1c(CCCOc2cccc3ccccc23)c2cccc3c2n1CCOCCOCc1nn(C)c(CN2CCOCC2)c1-3]

A mixture of ethyl 7-[3-(hydroxymethyl)-1-methyl-5-(morpholin-4-ylmethyl)-1H-pyrazol-4-yl]-3-[3-(naphthalen-1-yloxy)propyl]-1H-indole-2-carboxylate (see Intermediate 189, 750 mg, 1.29 mmol), caesium carbonate (2.10 g, 6.44 mmol), bis(2-methoxyethyl) ether (59 mL), bis(2-iodoethyl) ether (180 μL, 1.3 mmol) and sodium iodide (193 mg, 1.29 mmol) was stirred at RT for 20 hrs and at 70° C. for 6 hrs. The mixture was poured into ice-water and was extracted with dichloromethane/2-propanol. The organic layer was dried using a silicone filter and purified by flash chromatography (SNAP silica 25 g, ethyl acetate:n-hexane) and preparative HPLC (method P1) to give the title compound (30.8 mg, 4% yield).

LC-MS: m/z=653.4 [M+H]$^+$

546

Intermediate 193

Ethyl 7-[5-cyclopropyl-1-ethyl-3-(hydroxymethyl)-1H-pyrazol-4-yl]-3-[3-(naphthalen-1-yloxy)propyl]-1H-indole-2-carboxylate

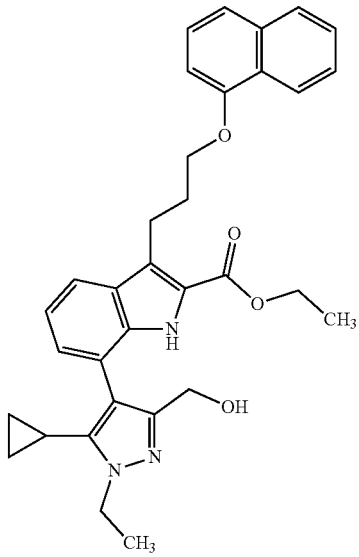 [SMILES: CCOC(=O)c1[nH]c2c(-c3c(CO)nn(CC)c3C3CC3)cccc2c1CCCOc1cccc2ccccc12]

XPhos Pd G2 (see abbreviation list, 106 mg, 135 μmol) was added to a degassed mixture of ethyl 3-[3-(naphthalen-1-yloxy)propyl]-7-(4,4,5,5-tetramethyl-1,3,2-dioxaborolan-2-yl)-1H-indole-2-carboxylate (2.20 g, 4.40 mmol; prepared according to Journal of Medicinal Chemistry 2015, 58, 2180-2194), (4-bromo-5-cyclopropyl-1-ethyl-1H-pyrazol-3-yl)methanol (see Intermediate 113, 980 mg, 4.00 mmol), aqueous potassium phosphate solution (16 mL, 0.50 M) and THF (49 mL). The mixture was stirred at 45° C. for 2 hrs. Ethyl acetate was added and the organic layer was washed with brine and dried using a silicone filter. After removal of the solvent the residue was purified by flash chromatography (Biotage, SNAP silica 50 g, ethyl acetate:n-hexane) to give the title compound (351 mg, 14% yield).

LC-MS: m/z=538.2 [M+H]$^+$.

547

Intermediate 194

(rac)-Ethyl (11Z)-3-cyclopropyl-2-ethyl-7-[3-(naphthalen-1-yloxy)propyl]-2,10,13,15-tetrahydropyrazolo[4',3':9,10][1,6]oxazacycloundecino[8,7,6-hi]indole-8-carboxylate

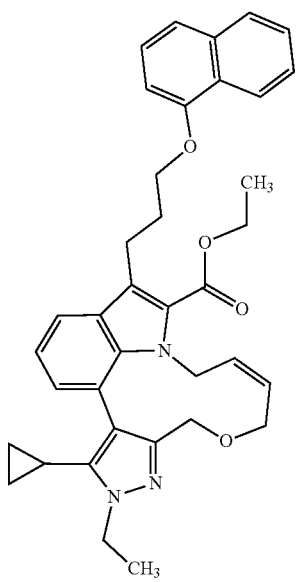 [SMILES: CCOC(=O)c1c(CCCOc2cccc3ccccc23)c2cccc3c2n1C/C=C\COCc1nn(CC)c(C2CC2)c1-3]

A mixture of ethyl 7-[5-cyclopropyl-1-ethyl-3-(hydroxymethyl)-1H-pyrazol-4-yl]-3-[3-(naphthalen-1-yloxy)propyl]-1H-indole-2-carboxylate (350 mg, 651 µmol), caesium carbonate (1.06 g, 3.25 mmol), 1,2-dimethoxyethane (25 mL), (2Z)-1,4-dichlorobut-2-ene (68 µL, 650 µmol) and sodium iodide (97.6 mg, 651 µmol) was stirred at RT for 4 days and at 50° C. for 5 hrs. The mixture was poured into ice-water and was extracted with dichloromethane/2-propanol. The organic layer was dried using a silica filter and purified by flash chromatography (SNAP silica 25 g, ethyl acetate:n-hexane) to give the title compound (155 mg, 39% yield).

LC-MS: m/z=590.3 [M+H]$^+$

548

Intermediate 195

(rac)-Ethyl 3-cyclopropyl-2-ethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylate

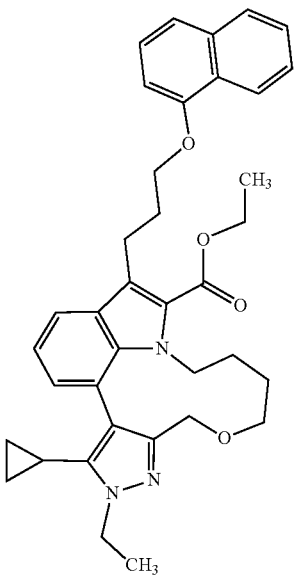 [SMILES: CCOC(=O)c1c(CCCOc2cccc3ccccc23)c2cccc3c2n1CCCCOCc1nn(CC)c(C2CC2)c1-3]

To a solution of (rac)-ethyl (11Z)-3-cyclopropyl-2-ethyl-7-[3-(naphthalen-1-yloxy)propyl]-2,10,13,15-tetrahydropyrazolo[4',3':9,10][1,6]oxazacycloundecino[8,7,6-hi]indole-8-carboxylate (155 mg, 263 µmol) in THF (940 µL) and ethanol (4.6 mL) was added palladium on charcoal (28.0 mg, 10%, 26.3 µmol) and the mixture was vigorously stirred under an atmosphere of hydrogen at 20 bar at RT for 22 hrs. The catalyst was filtered off, and the filtrate was concentrated to give the title compound (138 mg, 89% yield).

LC-MS: m/z=592.3 [M+H]$^+$

Intermediate 196

Ethyl 7-[3-cyclopropyl-1-ethyl-5-(hydroxymethyl)-1H-pyrazol-4-yl]-3-[3-(naphthalen-1-yloxy)propyl]-1H-indole-2-carboxylate

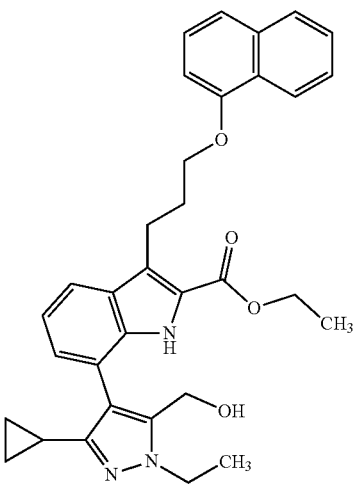 [SMILES: CCOC(=O)c1[nH]c2c(-c3c(C4CC4)nn(CC)c3CO)cccc2c1CCCOc1cccc2ccccc12]

XPhos Pd G2 (see abbreviation list, 57.7 mg, 73.3 µmol;) was added to a degassed mixture of ethyl 3-[3-(naphthalen-1-yloxy)propyl]-7-(4,4,5,5-tetramethyl-1,3,2-dioxaborolan-2-yl)-1H-indole-2-carboxylate (1.09 g, 2.18 mmol; prepared according to Journal of Medicinal Chemistry 2015, 58, 2180-2194), (4-bromo-3-cyclopropyl-1-ethyl-1H-pyrazol-5-yl)methanol (see Intermediate 114; 560 mg, 2.28 mmol), aqueous potassium phosphate solution (8.7 mL, 0.50 M) and THF (26 mL). The mixture was stirred at 45° C. for 2.25 hrs. Ethyl acetate was added and the organic layer was washed with brine and dried using a silicone filter. After removal of the solvent the residue was purified by flash chromatography (Biotage, SNAP silica 50 g, ethyl acetate:n-hexane) to give the title compound (988 mg, 84% yield).

LC-MS: m/z=538.3 [M+H]$^+$.

Intermediate 197

(rac)-Ethyl (11Z)-3-cyclopropyl-1-ethyl-7-[3-(naphthalen-1-yloxy)propyl]-1,10,13,15-tetrahydropyrazolo[4′,3′:9,10][1,6]oxazacycloundecino[8,7,6-hi]indole-8-carboxylate

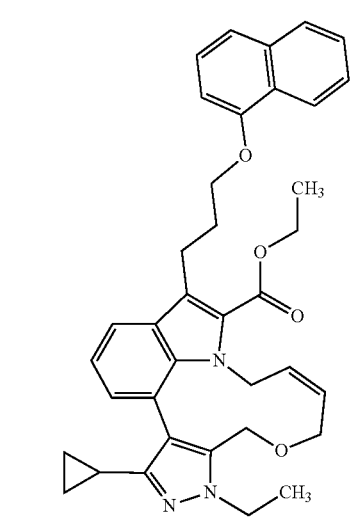 [SMILES: CCOC(=O)c1c(CCCOc2cccc3ccccc23)c2cccc3c2n1C/C=C\COCc1c-3c(C2CC2)nn1CC]

A mixture of ethyl 7-[3-cyclopropyl-1-ethyl-5-(hydroxymethyl)-1H-pyrazol-4-yl]-3-[3-(naphthalen-1-yloxy)propyl]-1H-indole-2-carboxylate (980 mg, 1.82 mmol), caesium carbonate (2.97 g, 9.11 mmol), bis(2-methoxyethyl) ether (70 mL), (2Z)-1,4-dichlorobut-2-ene (190 µL, 1.8 mmol) and sodium iodide (273 mg, 1.82 mmol) was stirred at RT for 20 hrs and at 70° C. for 23 hrs. The mixture was poured into ice-water and was extracted with dichloromethane/2-propanol. The organic layer was dried using a silicone filter and purified by flash chromatography (SNAP silica 50 g, ethyl acetate:n-hexane) to give the title compound (427 mg, 39% yield).

LC-MS: m/z=590.3 [M+H]$^+$

Intermediate 198

(rac)-Ethyl 3-cyclopropyl-1-ethyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate

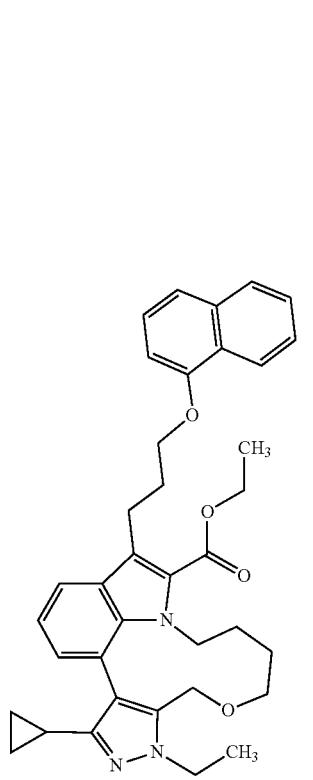 [SMILES: CCOC(=O)c1c(CCCOc2cccc3ccccc23)c2cccc3c2n1CCCCOCc1c-3c(C2CC2)nn1CC]

To a solution of (rac)-ethyl (11Z)-3-cyclopropyl-1-ethyl-7-[3-(naphthalen-1-yloxy)propyl]-1,10,13,15-tetrahydropyrazolo[4',3':9,10][1,6]oxazacycloundecino[8,7,6-hi]indole-8-carboxylate (427 mg, 724 μmol) in THF (2.9 mL) and ethanol (15 mL) was added palladium on charcoal (77.0 mg, 10%, 72.4 μmol) and the mixture was vigorously stirred under an atmosphere of hydrogen at 21 bar at RT for 22 hrs. The catalyst was filtered off, and the filtrate was concentrated to give the title compound (401 mg, 94% yield).

LC-MS: m/z=592.3 [M+H]$^+$

Intermediate 199

Ethyl 7-[5-cyclopropyl-3-(hydroxymethyl)-1-(2-methoxyethyl)-1H-pyrazol-4-yl]-3-[3-(naphthalen-1-yloxy)propyl]-1H-indole-2-carboxylate

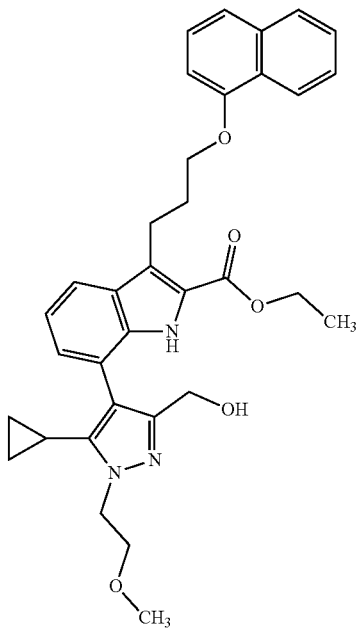 [SMILES: CCOC(=O)c1[nH]c2c(-c3c(CO)nn(CCOC)c3C3CC3)cccc2c1CCCOc1cccc2ccccc12]

XPhos Pd G2 (see abbreviation list, 133 mg, 169 μmol) was added to a degassed mixture of ethyl 3-[3-(naphthalen-1-yloxy)propyl]-7-(4,4,5,5-tetramethyl-1,3,2-dioxaborolan-2-yl)-1H-indole-2-carboxylate (1.69 g, 3.38 mmol; prepared according to Journal of Medicinal Chemistry 2015, 58, 2180-2194), [4-bromo-5-cyclopropyl-1-(2-methoxyethyl)-1H-pyrazol-3-yl]methanol (see Intermediate 118, 930 mg, 3.38 mmol), aqueous potassium phosphate solution (14 mL, 0.50 M) and THF (41 mL). The mixture was stirred at 50° C. for 2 hrs. Ethyl acetate and water were added and the organic layer was washed with brine and dried using a silicone filter. After removal of the solvent the residue was purified by flash chromatography (Biotage, SNAP NH$_2$ 55 g, ethyl acetate:n-hexane) to give the title compound (1.33 g, 69% yield).

LC-MS: m/z=568.3 [M+H]$^+$.

553

Intermediate 200

(rac)-Ethyl (11Z)-3-cyclopropyl-2-(2-methoxy-ethyl)-7-[3-(naphthalen-1-yloxy)propyl]-2,10,13,15-tetrahydropyrazolo[4',3':9,10][1,6]oxazacycloundecino[8,7,6-hi]indole-8-carboxylate

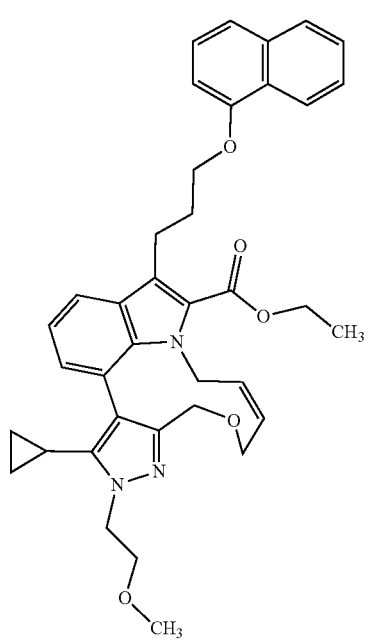 [SMILES: CCOC(=O)c1c(CCCOc2cccc3ccccc23)c2cccc3c2n1C/C=C\COCc1nn(CCOC)c(C2CC2)c1-3]

A mixture of ethyl 7-[5-cyclopropyl-3-(hydroxymethyl)-1-(2-methoxyethyl)-1H-pyrazol-4-yl]-3-[3-(naphthalen-1-yloxy)propyl]-1H-indole-2-carboxylate (600 mg, 1.06 mmol), caesium carbonate (1.72 g, 5.29 mmol), bis(2-methoxyethyl) ether (48 mL), (2Z)-1,4-dichlorobut-2-ene (111 μL, 1.06 mmol) and sodium iodide (317 mg, 2.11 mmol) was stirred at RT overnight and at 60° C. for 2 hrs. The mixture was poured into water and was extracted with dichloromethane/2-propanol. The organic layer was dried using a silicone filter and purified by flash chromatography (SNAP NH₂ 55 g, ethyl acetate:n-hexane) to give the title compound (250 mg, 38% yield).
LC-MS: m/z=620.2 [M+H]⁺

554

Intermediate 201

(rac)-Ethyl 3-cyclopropyl-2-(2-methoxyethyl)-7-[3-(naphthalen-1-yloxy)propyl]-2,10,11,12,13,15-hexahydropyrazolo[4',3':9,10][1,6]oxazacycloundecino[8,7,6-hi]indole-8-carboxylate

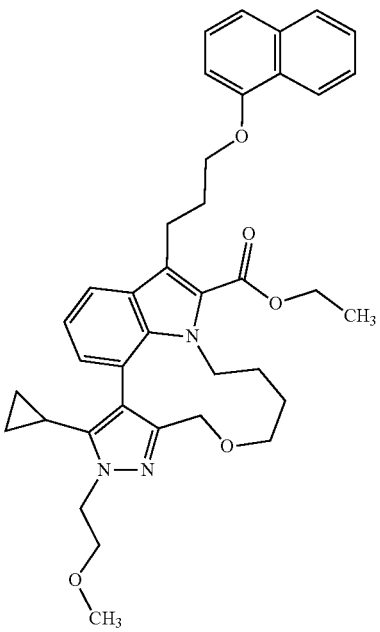 [SMILES: CCOC(=O)c1c(CCCOc2cccc3ccccc23)c2cccc3c2n1CCCCOCc1nn(CCOC)c(C2CC2)c1-3]

To a solution of (rac)-ethyl (11Z)-3-cyclopropyl-2-(2-methoxyethyl)-7-[3-(naphthalen-1-yloxy)propyl]-2,10,13,15-tetrahydropyrazolo[4',3':9,10][1,6]oxazacycloundecino[8,7,6-hi]indole-8-carboxylate (250 mg, 403 μmol) in THF (1.4 mL) and ethanol (7 mL) was added palladium on charcoal (42.9 mg, 10%, 40.3 μmol) and the mixture was vigorously stirred under an atmosphere of hydrogen at RT at 21 bar for 22 hrs. The catalyst was filtered off and the filtrate was concentrated to give the title compound (250 mg, 100% yield).
LC-MS: m/z=622.3 [M+H]⁺.

555

Intermediate 202

Ethyl 7-[3-cyclopropyl-5-(hydroxymethyl)-1-(2-methoxyethyl)-1H-pyrazol-4-yl]-3-[3-(naphthalen-1-yloxy)propyl]-1H-indole-2-carboxylate

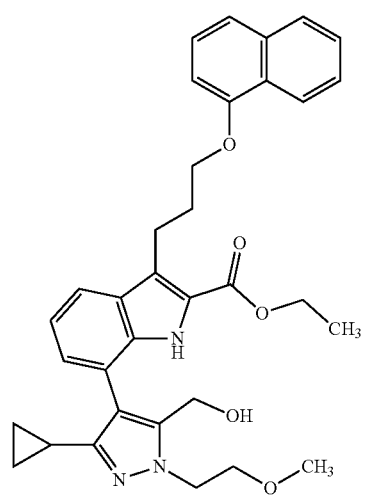 [SMILES: CCOC(=O)c1[nH]c2c(-c3c(C4CC4)nn(CCOC)c3CO)cccc2c1CCCOc1cccc2ccccc12]

XPhos Pd G2 (see abbreviation list, 110 mg, 140 µmol) was added to a degassed mixture of ethyl 3-[3-(naphthalen-1-yloxy)propyl]-7-(4,4,5,5-tetramethyl-1,3,2-dioxaborolan-2-yl)-1H-indole-2-carboxylate (2.07 g, 4.15 mmol; prepared according to Journal of Medicinal Chemistry 2015, 58, 2180-2194), [4-bromo-3-cyclopropyl-1-(2-methoxyethyl)-1H-pyrazol-5-yl]methanol (see Intermediate 120, 1.20 g, 4.36 mmol), aqueous potassium phosphate solution (17 mL, 0.50 M) and THF (51 mL). The mixture was stirred at 45° C. for 3 hrs. Ethyl acetate was added and the organic layer was washed with brine and dried using a silicone filter. After removal of the solvent the residue was purified by flash chromatography (Biotage, SNAP silica 100 g, ethyl acetate: n-hexane) to give the title compound (1.98 g, 82% yield).

LC-MS: m/z=568.3 [M+H]$^+$.

556

Intermediate 203

(rac)-Ethyl (11Z)-3-cyclopropyl-1-(2-methoxyethyl)-7-[3-(naphthalen-1-yloxy)propyl]-1,10,13,15-tetrahydropyrazolo[4',3':9,10][1,6]oxazacycloundecino[8,7,6-hi]indole-8-carboxylate

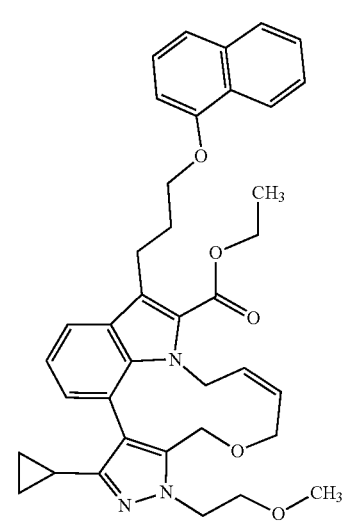 [SMILES: CCOC(=O)c1c(CCCOc2cccc3ccccc23)c2cccc3c2n1C/C=C\COCc1c-3c(C2CC2)nn1CCOC]

A mixture of ethyl 7-[3-cyclopropyl-5-(hydroxymethyl)-1-(2-methoxyethyl)-1H-pyrazol-4-yl]-3-[3-(naphthalen-1-yloxy)propyl]-1H-indole-2-carboxylate (900 mg, 1.59 mmol), caesium carbonate (2.58 g, 7.93 mmol bis(2-methoxyethyl) ether (61 mL), (2Z)-1,4-dichlorobut-2-ene (170 µL, 1.6 mmol) and sodium iodide (238 mg, 1.59 mmol) was stirred at RT for 20 hrs and at 70° C. for 28 hrs. The mixture was poured into ice-water and was extracted with dichloromethane/2-propanol. The organic layer was dried using a silicone filter and purified by flash chromatography (SNAP silica 50 g, ethyl acetate:n-hexane) to give the title compound (263 mg, 26% yield).

LC-MS: m/z=620.3 [M+H]$^+$

Intermediate 204

(rac)-Ethyl 3-cyclopropyl-1-(2-methoxyethyl)-7-[3-(naphthalen-1-yloxy)propyl]-1,10,11,12,13,15-hexahydropyrazolo[4',3':9,10][1,6]oxazacycloundecino[8,7,6-hi]indole-8-carboxylate and (rac)-ethyl 3-cyclopropyl-1-(2-methoxyethyl)-7-[3-(5,6,7,8-tetrahydronaphthalen-1-yloxy)propyl]-1,10,11,12,13,15-hexahydropyrazolo[4',3':9,10][1,6]oxazacycloundecino[8,7,6-hi]indole-8-carboxylate

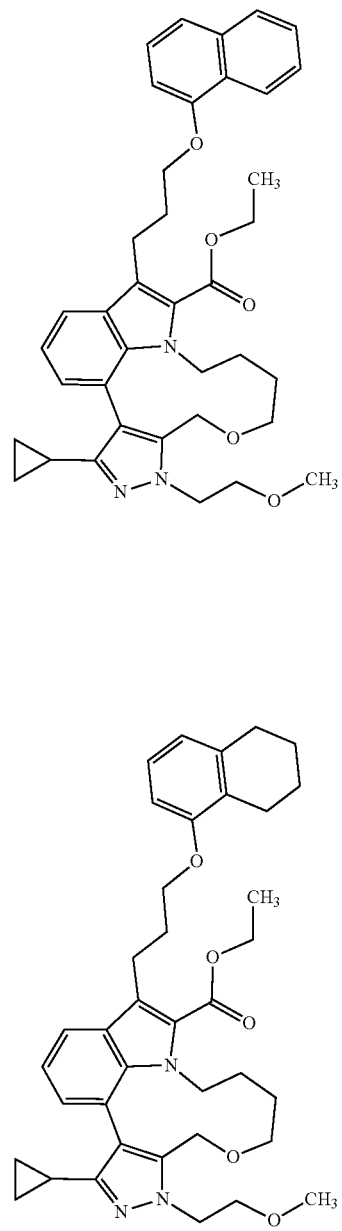

To a solution of (rac)-ethyl (11Z)-3-cyclopropyl-1-(2-methoxyethyl)-7-[3-(naphthalen-1-yloxy)propyl]-1,10,13,15-tetrahydropyrazolo[4',3':9,10][1,6]oxazacycloundecino[8,7,6-hi]indole-8-carboxylate (263 mg, 424 μmol) in THF (1.5 mL) and ethanol (7.4 mL) was added palladium on charcoal (45.2 mg, 10%, 42.4 μmol) and the mixture was vigorously stirred under an atmosphere of hydrogen at RT at 21 bar for 22 hrs. The catalyst was filtered off, the filtrate was concentrated and the residue (230 mg) containing a mixture of the title compounds each as mixture of atropisomers was used without further purification.

LC-MS: m/z=622.3, 626.4 [M+H]+.

Intermediate 205

Ethyl 7-[3-(benzyloxy)-5-methoxyphenyl]-3-[3-(naphthalen-1-yloxy)propyl]-1H-indole-2-carboxylate

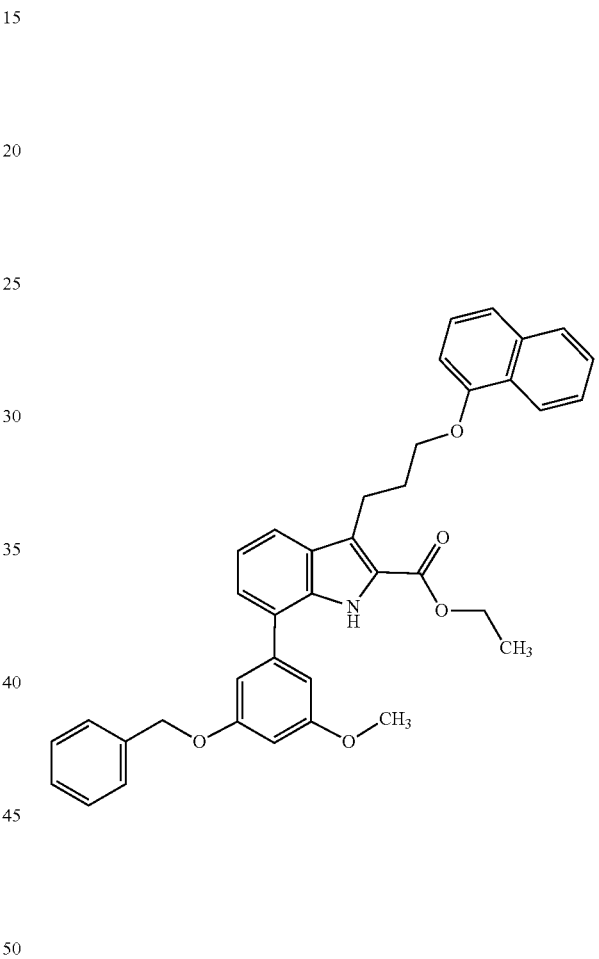

To a solution of ethyl 7-bromo-3-[3-(naphthalen-1-yloxy)propyl]-1H-indole-2-carboxylate (see Intermediate 4, 2.50 g, 5.53 mmol) in 1,4-dioxane (50 mL) were added [3-(benzyloxy)-5-methoxyphenyl]boronic acid (2.14 g, 8.29 mmol), lithium chloride (469 mg, 11.1 mmol) and sodium carbonate (11 mL, 2.0 M in water, 22 mmol). The mixture was degassed and purged with argon several times. [1,1'-Bis(diphenylphosphino)ferrocene]dichloropalladium(II) (903 mg, 1.11 mmol; complex with dichloromethane) was added and the mixture was stirred at 100° C. overnight. After cooling acetonitrile was added, the mixture was filtered, concentrated and purified by Biotage (SNAP silica 340 g, ethyl acetate:n-hexane) to give the title compound (3.03 g, 94% yield).

LC-MS: m/z=586.3 [M+H]+.

Intermediate 206

Ethyl 7-(3-hydroxy-5-methoxyphenyl)-3-[3-(5,6,7,8-tetrahydronaphthalen-1-yloxy)propyl]-1H-indole-2-carboxylate

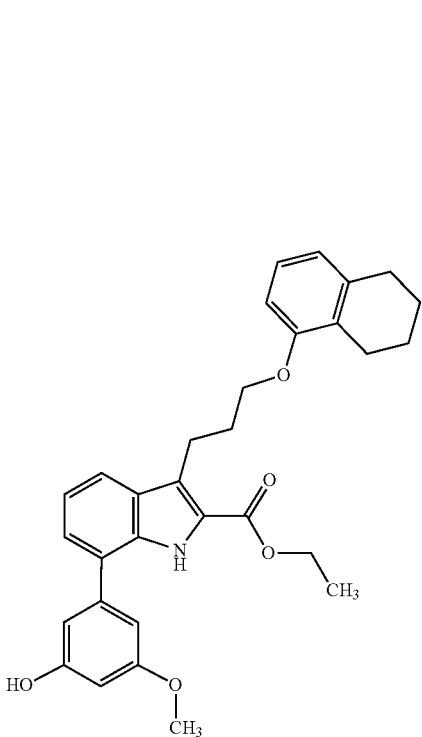 [SMILES: CCOC(=O)c1[nH]c2c(-c3cc(O)cc(OC)c3)cccc2c1CCCOc1cccc2c1CCCC2]

To a solution of ethyl 7-[3-(benzyloxy)-5-methoxyphenyl]-3-[3-(naphthalen-1-yloxy)propyl]-1H-indole-2-carboxylate (1.00 g, 1.71 mmol) in THF (35 mL) and ethanol (35 mL) was added palladium on charcoal (363 mg, 10%, 341 µmol) and the mixture was vigorously stirred under an atmosphere of hydrogen at RT for 2 days. Dichloromethane was added, the catalyst was filtered off, the filtrate was concentrated and the residue was purified by Biotage (SNAP silica 100 g, ethyl acetate:n-hexane) to give the title compound (501 mg, 59% yield).

LC-MS: m/z=500 [M+H]$^+$.

Intermediate 207

(rac)-Ethyl 12-methoxy-1-[3-(5,6,7,8-tetrahydronaphthalen-1-yloxy)propyl]-5,6,7,8-tetrahydro-4H-10,14-(metheno)[1,7]oxazacyclotetradecino[9,8,7-hi]indole-2-carboxylate

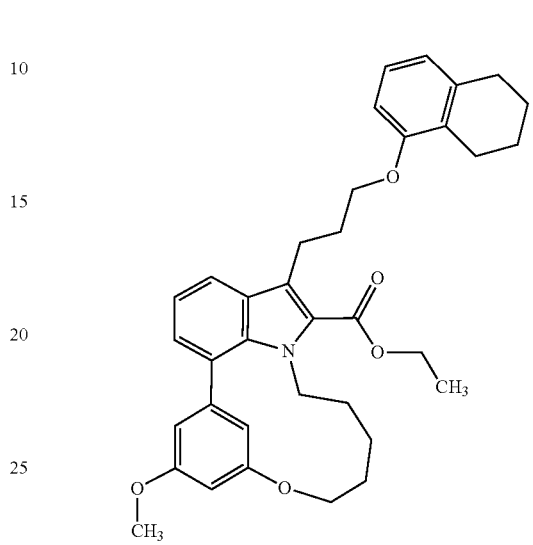

A mixture of ethyl 7-(3-hydroxy-5-methoxyphenyl)-3-[3-(5,6,7,8-tetrahydronaphthalen-1-yloxy)propyl]-1H-indole-2-carboxylate (50.0 mg, 100 µmol), 1,5-dibromopentane (34 µL, 250 µmol), potassium tert.-butylate (28 mg, 250 µmol) and THF (5.0 mL) was stirred at 80° C. overnight. The mixture was filtered, concentrated and purified by preparative TLC (ethyl acetate:n-hexane) to give the title compound (11.3 mg, 20% yield).

LC-MS: m/z=568.3 [M+H]$^+$.

Intermediate 208

Ethyl 7-(5-hydroxy-2-methylphenyl)-3-[3-(naphthalen-1-yloxy)propyl]-1H-indole-2-carboxylate

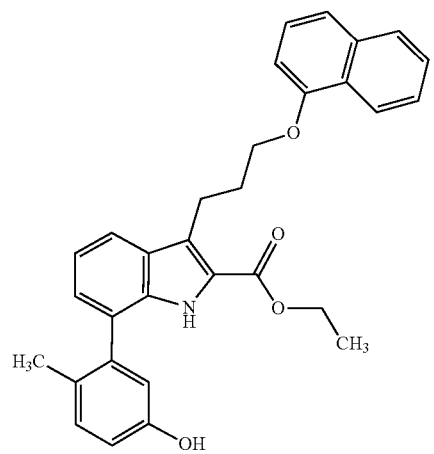 [SMILES: CCOC(=O)c1[nH]c2c(-c3cc(O)ccc3C)cccc2c1CCCOc1cccc2ccccc12]

To a solution of ethyl 7-bromo-3-[3-(naphthalen-1-yloxy)propyl]-1H-indole-2-carboxylate (see Intermediate 4, 2.00 g, 4.42 mmol) in 1,4-dioxane (40 mL) were added (5-hydroxy-2-methylphenyl)boronic acid (1.01 g, 6.63 mmol), lithium chloride (375 mg, 8.84 mmol) and sodium carbonate (8.8 mL, 2.0 M in water, 17.6 mmol). The mixture was degassed and purged with argon several times. [1,1'-Bis(diphenylphosphino)ferrocene]dichloropalladium(II) (722 mg, 884 µmol; complex with dichloromethane) was added and the mixture was stirred at 100° C. overnight. After cooling dichloromethane was added, the mixture was filtered, concentrated and purified by Biotage (SNAP silica 100 g, ethyl acetate:n-hexane) to give the title compound (1.7 g, 80% yield).

LC-MS: m/z=480.2 [M+H]$^+$.

Intermediate 209

(rac)-Ethyl 13-methyl-1-[3-(naphthalen-1-yloxy)propyl]-4,5,7,8-tetrahydro-10,14-(metheno)[1,4,7]dioxazacyclotetradecino[9,8,7-hi]indole-2-carboxylate

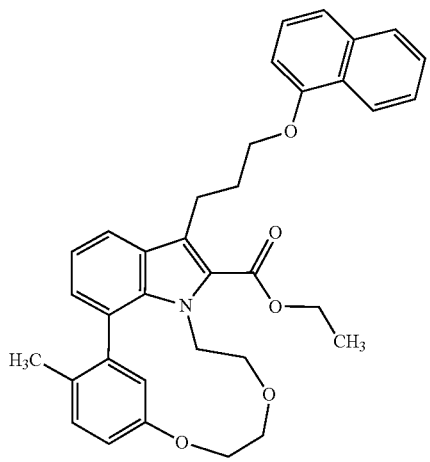 [SMILES: CCOC(=O)c1c(CCCOc2cccc3ccccc23)c2cccc3c2n1CCOCCOc1ccc(C)c-3c1]

A mixture of ethyl 7-(5-hydroxy-2-methylphenyl)-3-[3-(naphthalen-1-yloxy)propyl]-1H-indole-2-carboxylate (100 mg, 209 µmol), bis(2-bromoethyl) ether (66 µL, 250 µmol), caesium carbonate (340 mg, 1.0 mmol) and N,N-dimethylacetamide (7.0 mL) was stirred at 80° C. overnight. The mixture was filtered, concentrated and purified by preparative TLC (ethyl acetate:n-hexane) to give the title compound (40.1 mg, 35% yield).

LC-MS: m/z=550.2 [M+H]$^+$.

Intermediate 210 ethyl 4-bromo-1-methyl-3-{[4-(morpholin-4-yl)phenoxy]methyl}-1H-pyrazole-5-carboxylate

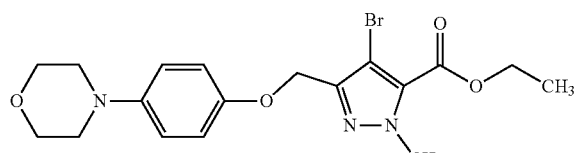

To a solution of 4-(morpholin-4-yl)phenol (2.00 g, 11.2 mmol, CAS 6291-23-2) in DMF (35 ml) was added potassium carbonate (4.41 g, 31.9 mmol) and the mixture was stirred for 10 min at room temperature. Ethyl 4-bromo-3-(bromomethyl)-1-methyl-1H-pyrazole-5-carboxylate (see Intermediate 6; 3.46 g, 10.6 mmol) was added and the reaction was stirred for 4 hours at room temperature. For work-up, the reaction mixture was concentrated under reduced pressure. The residue was partitioned between water and ethyl acetate and the aqueous phase was then extracted with ethyl acetate. The combined organic phases were washed with aqueous 2 M sodium hydroxide solution and brine and dried over sodium sulfate. After filtration and removal of the solvent, the crude product was triturated with methanol to give the title compound (4 g).

LC-MS (Method 1): Rt=424.00 min; MS (ESIpos): m/z=1 [M+H]$^+$ $^1$H-NMR (400 MHz, CHLOROFORM-d) δ [ppm]: 1.416 (4.00), 1.433 (8.05), 1.452 (3.90), 3.064 (1.27), 3.076 (1.70), 3.087 (1.31), 3.855 (1.39), 3.867 (1.87), 3.877 (1.40), 4.176 (16.00), 4.392 (1.27), 4.410 (3.97), 4.428 (3.68), 4.446 (1.16), 5.016 (5.93), 6.979 (1.81), 7.002 (1.19).

Intermediate 211

(4-bromo-1-methyl-3-{[4-(morpholin-4-yl)phenoxy]methyl}-1H-pyrazol-5-yl)methanol

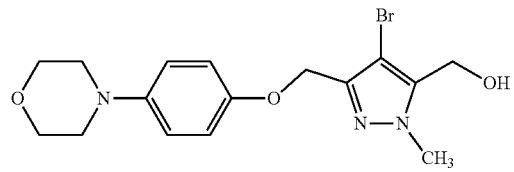 [SMILES: Cn1nc(COc2ccc(N3CCOCC3)cc2)c(Br)c1CO]

To a solution of ethyl 4-bromo-1-methyl-3-{[4-(morpholin-4-yl)phenoxy]methyl}-1H-pyrazole-5-carboxylate (4.03 g, 9.50 mmol) in THF (95 mL) at 0° C. was added a solution of lithium aluminium hydride in THF (4.7 ml, 2.0 M, 9.5 mmol), and the mixture was stirred at 0° C. for 1 hour. For work-up, aqueous 2 M sodium hydroxide solution (4 ml) was added and the mixture was stirred for 10 min. Sodium sulfate was added and the mixture was stirred for 10 min. The mixture was filtered and the filtrate was concentrated under reduced pressure to give the crude title compound (3.54 g) which was used without further purification.

LC-MS (Method 2): Rt=0.93 min; MS (ESIpos): m/z=382 [M+H]$^+$

Intermediate 212 ethyl 7-[5-(hydroxymethyl)-1-methyl-3-{[4-(morpholin-4-yl)phenoxy]methyl}-1H-pyrazol-4-yl]-3-[3-(naphthalen-1-yloxy)propyl]-1H-indole-2-carboxylate

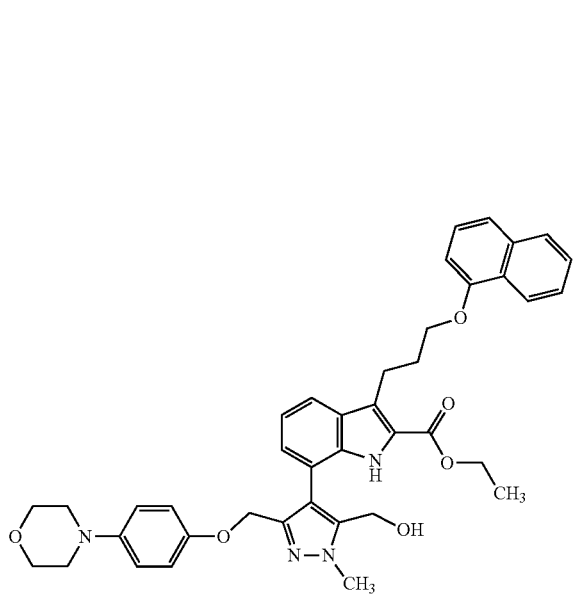

To a solution of ethyl 3-[3-(naphthalen-1-yloxy)propyl]-7-(4,4,5,5-tetramethyl-1,3,2-dioxaborolan-2-yl)-1H-indole-2-carboxylate (see Intermediate 5; 3.85 g, 7.72 mmol) and (4-bromo-1-methyl-3-{[4-(morpholin-4-yl)phenoxy]methyl}-1H-pyrazol-5-yl)methanol (3.35 g, 80% purity, 7.01 mmol) in 1,4-dioxane (90 ml) were added aqueous 2 M solution of potassium carbonate (11 ml, 2.0 M, 21 mmol). The mixture was degassed and purged with argon several times. Pd(dppf)Cl$_2$×CH$_2$Cl$_2$ (1.15 g, 1.40 mmol) was added and the mixture was purged with argon for 10 minutes. The reaction was stirred at 80° C. for 16 h. For work-up, the reaction mixture was diluted with ethyl acetate and was filtered through a pad of celite. The filtrate was concentrated under reduced pressure and the residue was dissolved in ethyl acetate. The organic phase was washed with water and brine and the organic phase was dried over sodium sulfate. The mixture was filtered and the filtrate was concentrated under reduced pressure. The residue was purified by flash chromatography (dichloromethane/ethyl acetate gradient, 17%→100% ethyl acetate) to give the title compound (3.9 g).

LC-MS (Method 2): Rt=1.58 min; MS (ESIpos): m/z=675 [M+H]$^+$

Intermediate 213 ethyl 7-(1-methyl-3-{[4-(morpholin-4-yl)phenoxy]methyl}-5-[(prop-2-en-1-yloxy)methyl]-1H-pyrazol-4-yl)-3-[3-(naphthalen-1-yloxy)propyl]-1-(prop-2-en-1-yl)-1H-indole-2-carboxylate

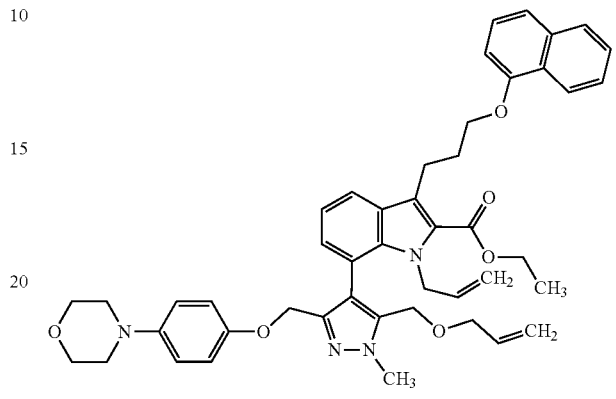

To a solution of ethyl 7-[5-(hydroxymethyl)-1-methyl-3-{[4-(morpholin-4-yl)phenoxy]methyl}-1H-pyrazol-4-yl]-3-[3-(naphthalen-1-yloxy)propyl]-1H-indole-2-carboxylate (675 mg, 1.00 mmol) in THF (10 ml) was added sodium hydride (100 mg, 60% purity, 2.50 mmol) at 0° C. and the mixture was stirred for 2 hours at room temperature. The reaction was cooled down to 0° C. and a solution of allyl bromide (220 µl, 2.5 mmol) in THF (1 ml) was added. The mixture was stirred for 6 days at room temperature. For work-up, the reaction was poured into an aqueous sodium chloride solution and the mixture was extracted with ethyl acetate. The combined organic phases were dried over sodium sulfate. After filtration and removal of the solvent, the crude product was purified by flash chromatography (dichloromethane/ethyl acetate gradient, 7%→60% ethyl acetate) to give the title compound (649 mg).

LC-MS (Method 1): Rt=1.75 min; MS (ESIpos): m/z=755 [M+H]$^+$ $^1$H-NMR (400 MHz, CHLOROFORM-d) δ [ppm]: 1.252 (4.04), 1.270 (8.21), 1.288 (4.42), 1.348 (3.79), 1.366 (8.76), 1.383 (4.06), 2.057 (16.00), 2.344 (1.20), 2.977 (2.23), 3.386 (1.46), 3.391 (1.53), 3.785 (1.63), 3.788 (2.03), 3.798 (2.84), 3.801 (3.34), 3.805 (2.78), 3.813 (2.35), 3.816 (2.18), 3.819 (1.31), 3.862 (1.27), 3.865 (1.69), 3.869 (1.46), 3.875 (1.23), 3.879 (1.58), 3.882 (1.09), 3.900 (0.79), 3.933 (5.84), 3.988 (0.98), 4.002 (1.15), 4.014 (15.43), 4.105 (1.09), 4.123 (3.65), 4.126 (2.14), 4.141 (3.41), 4.157 (2.86), 4.195 (1.32), 4.211 (2.86), 4.226 (1.66), 4.233 (1.03), 4.272 (0.92), 4.276 (0.94), 4.303 (1.32), 4.310 (2.62), 4.321 (3.94), 4.338 (4.16), 4.342 (2.49), 4.356 (1.14), 4.539 (3.59), 4.760 (1.04), 4.764 (1.10), 4.786 (1.38), 4.790 (1.84), 4.794 (3.56), 4.798 (3.46), 4.981 (2.35), 5.082 (0.96), 5.086 (1.24), 5.101 (1.35), 5.105 (1.51), 5.109 (1.40), 5.112 (1.36), 5.144 (1.45), 5.148 (1.26), 5.748 (0.80), 5.774 (0.81), 5.791 (0.75), 5.817 (0.65), 6.734 (3.67), 6.755 (1.75), 6.758 (1.83), 6.774 (1.63), 6.777 (1.58), 7.070 (4.97), 7.079 (2.47), 7.084 (2.60), 7.331 (1.10), 7.351 (2.07), 7.370 (1.78), 7.416 (2.00), 7.437 (1.15), 7.491 (1.61), 7.494 (1.77), 7.497 (1.42), 7.504 (1.76), 7.506 (1.77), 7.511 (1.44), 7.515 (1.81), 7.518 (1.82), 7.725 (1.32), 7.734 (1.32), 7.738 (0.97), 7.747 (1.19), 7.806 (1.14), 7.818 (1.10), 7.829 (0.96), 8.368 (0.98), 8.393 (0.89).

Intermediate 214

(rac)-ethyl (E/Z)-1-methyl-3-{[4-(morpholin-4-yl)phenoxy]methyl}-7-[3-(naphthalen-1-yloxy)propyl]-1,10,13,15-tetrahydropyrazolo[4',3':9,10][1,6]oxazacycloundecino[8,7,6-hi]indole-8-carboxylate

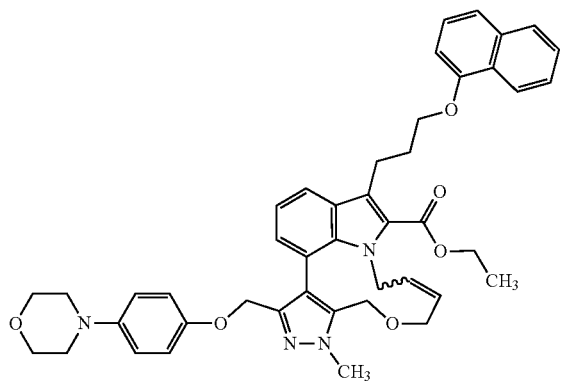

A solution of ethyl 7-(1-methyl-3-{[4-(morpholin-4-yl)phenoxy]methyl}-5-[(prop-2-en-1-yloxy)methyl]-1H-pyrazol-4-yl)-3-[3-(naphthalen-1-yloxy)propyl]-1-(prop-2-en-1-yl)-1H-indole-2-carboxylate (590 mg, 782 μmol) in dichloromethane (20 ml, 310 mmol) was purged with argon several times. (1,3-Bis(2,4,6-trimethylphenyl)-2-imidazolidinylidene)dichloro(phenylmethylene)(tricyclohexylphosphine)ruthenium (66.4 mg, 78.2 μmol) (Grubbs 2$^{nd}$ generation catalyst) was added and the reaction was stirred for 44 hours at room temperature. For work-up, the reaction mixture was concentrated under reduced pressure and the residue was purified by flash chromatography (dichloromethane/ethyl acetate gradient, 7%→60% ethyl acetate) to give the title compound (303 mg).

LC-MS (Method 1): Rt=1.70 min; MS (ESIpos): m/z=727 [M+H]$^+$

Intermediate 215

(rac)-ethyl 1-methyl-3-{[4-(morpholin-4-yl)phenoxy]methyl}-7-[3-(naphthalen-1-yloxy)propyl]-1,10,11,12,13,15-hexahydropyrazolo[4',3':9,10][1,6]oxazacycloundecino[8,7,6-hi]indole-8-carboxylate

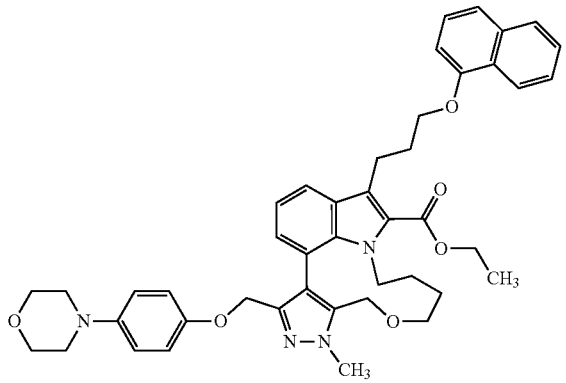 [SMILES: CCOC(=O)c1c(CCCOc2cccc3ccccc23)c2cccc3c2n1CC=CCOCc1c-3c(COc2ccc(N3CCOCC3)cc2)nn1C]

A suspension of (rac)-ethyl (E/Z)-1-methyl-3-{[4-(morpholin-4-yl)phenoxy]methyl}-7-[3-(naphthalen-1-yloxy)propyl]-1,10,13,15-tetrahydropyrazolo[4',3':9,10][1,6]oxazacycloundecino[8,7,6-hi]indole-8-carboxylate (200 mg, 275 μmol) and Pd/C (29.3 mg, 10% purity, 27.5 μmol) in ethanol (4.8 ml, 83 mmol) was stirred under an atmosphere of hydrogen at room temperature for 20 hours. For work-up the mixture was filtered through a pad of celite. The residue was washed with ethanol and the filtrate was concentrated under reduced pressure. The residue was purified by flash chromatography (dichloromethane/ethylacetate gradient, 6%→60% ethylacetate) to give a mixture of the title compound and (rac)-ethyl (E/Z)-1-methyl-3-{[4-(morpholin-4-yl)phenoxy]methyl}-7-[3-(naphthalen-1-yloxy)propyl]-1,10,13,15-tetrahydropyrazolo[4',3':9,10][1,6]oxazacycloundecino[8,7,6-hi]indole-8-carboxylate (161 mg).

Intermediate 216 ethyl 4-bromo-3-(cyanomethyl)-1-methyl-1H-pyrazole-5-carboxylate

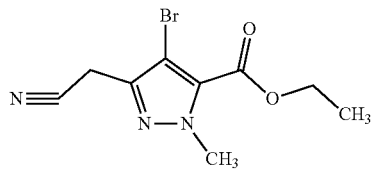

To a solution of ethyl 4-bromo-3-(bromomethyl)-1-methyl-1H-pyrazole-5-carboxylate (see Intermediate 6, 10.0 g, 30.7 mmol) in DMF (110 ml) and water (5.5 ml, 310 mmol) was added sodium cyanide (1.70 g, 97% purity, 33.7 mmol) and the mixture was stirred for 3 hours at room temperature. For work-up, the reaction was poured into water and the mixture was extracted three times with ethyl acetate. The combined organic phases were washed with brine and the organic phase was dried over sodium sulfate. After filtration and removal of the solvent, the crude product was triturated with hexane to give the title compound (12.1 g).

Intermediate 217

[4-bromo-5-(ethoxycarbonyl)-1-methyl-1H-pyrazol-3-yl]acetic acid

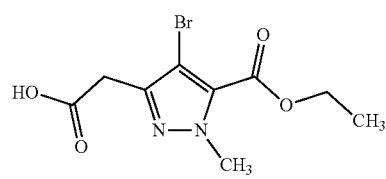

A mixture of ethyl 4-bromo-3-(cyanomethyl)-1-methyl-1H-pyrazole-5-carboxylate (12.1 g, 44.5 mmol) in a 4 M solution of HCl in dioxane (170 ml, 670 mmol) and hydrochloric acid (130 ml, 37%, 1.6 mol) was heated to 80° C. and the reaction was stirred at 80° C. for 8 hours. For work-up, the reaction was poured into water and the mixture was extracted with dichloromethane (3 times). The combined organic phases were washed with brine and the organic phase was dried over sodium sulfate. After filtration and removal of the solvent, the crude product (13.2 g) was used in the subsequent steps without further purification.

LC-MS (Method 2): Rt=0.50 min; MS (ESIpos): m/z=3 [M+H]$^+$

Intermediate 218 ethyl 4-bromo-3-(2-hydroxyethyl)-1-methyl-1H-pyrazole-5-carboxylate

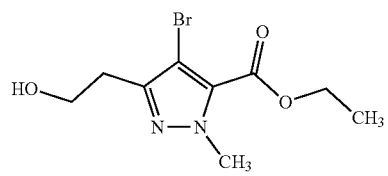

To a solution of [4-bromo-5-(ethoxycarbonyl)-1-methyl-1H-pyrazol-3-yl]acetic acid (13.2 g, 45.3 mmol) in THF (140 ml, 1.7 mol) at −25° C. was added a solution of boran-THF-complex in THF (57 ml, 1.0 M, 57 mmol) dropwise and the mixture was allowed to warm to room temperature. The reaction was stirred for 22 hours at room temperature. For work-up, methanol (50 ml) was added dropwise and the reaction was then poured into water. The mixture was extracted three times with ethyl acetate and the combined organic phases were washed with brine. The organic phase was dried over sodium sulfate. After filtration and removal of the solvent, the crude product (14.8 g) was used in the subsequent steps without further purification.

LC-MS (Method 2): Rt=0.90 min; MS (ESIpos): m/z=277 [M+H]$^+$

Intermediate 219 ethyl 4-bromo-3-(2-bromoethyl)-1-methyl-1H-pyrazole-5-carboxylate

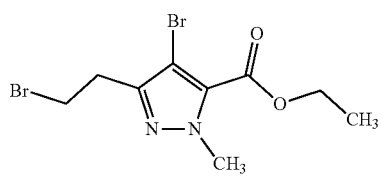

To a solution of ethyl 4-bromo-3-(2-hydroxyethyl)-1-methyl-1H-pyrazole-5-carboxylate (650 mg, 2.35 mmol) in dichloromethane (43 ml, 670 mmol), triphenylphosphine (738 mg, 2.81 mmol) was added at 0° C. and the mixture was stirred at 0° C. for 10 min. Tetrabromomethane (933 mg, 2.81 mmol) was added and the reaction was stirred at 0° C. for 2 hours and for 2 hours at room temperature. For work-up the reaction was diluted with dichloromethane and the mixture was washed with aqueous sodium bicarbonate solution and brine. The organic phase was dried over sodium sulfate. After filtration and removal of the solvent, the crude product was purified by flash chromatography (hexane/ethyl acetate gradient, 0%→30% ethyl acetate) to give the title compound (497 mg).

$^1$H-NMR (400 MHz, CHLOROFORM-d) δ [ppm]: 0.000 (0.65), 1.338 (3.86), 1.356 (8.15), 1.374 (3.89), 1.484 (4.00), 3.118 (1.78), 3.137 (3.62), 3.156 (2.17), 3.538 (2.28), 3.557 (3.97), 3.575 (1.89), 4.059 (16.00), 4.307 (1.20), 4.325 (3.61), 4.343 (3.52), 4.361 (1.15).

Intermediate 220 ethyl 4-bromo-1-methyl-3-[2-(morpholin-4-yl)ethyl]-1H-pyrazole-5-carboxylate

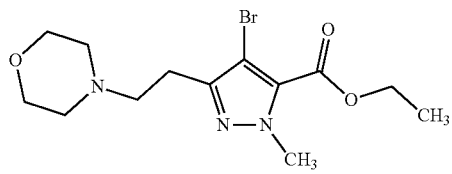 [SMILES: CCOC(=O)c1c(Br)c(CCN2CCOCC2)nn1C]

To a solution of morpholine (530 μl, 6.1 mmol) in acetonitrile (25 ml, 480 mmol) was added potassium carbonate (845 mg, 6.11 mmol) and the mixture was stirred for 10 min at room temperature. Ethyl 4-bromo-3-(2-bromoethyl)-1-methyl-1H-pyrazole-5-carboxylate (495 mg, 1.46 mmol) was added and the reaction was stirred for 3 hours at room temperature and for 30 hours at 50° C. For work-up the reaction mixture was poured into an aqueous solution of sodium chloride. The resulting precipitate collected by filtration, washed with water and dried in vacuo at 50° C. to give the crude product (420 mg) which was used in the subsequent steps without further purification.

LC-MS (Method 2): Rt=1.21 min; MS (ESIpos): m/z=346 [M+H]$^+$ $^1$H-NMR (400 MHz, CHLOROFORM-d) δ [ppm]: 0.000 (0.69), 1.184 (0.44), 1.336 (3.92), 1.354 (7.96), 1.371 (3.84), 2.491 (1.53), 2.615 (0.69), 2.761 (0.77), 2.780 (0.88), 3.681 (2.29), 4.042 (16.00), 4.089 (0.42), 4.303 (1.27), 4.321 (3.82), 4.339 (3.68), 4.357 (1.19).

Intermediate 221

{4-bromo-1-methyl-3-[2-(morpholin-4-yl)ethyl]-1H-pyrazol-5-yl}methanol

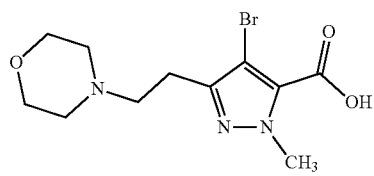 [SMILES: Cn1nc(CCN2CCOCC2)c(Br)c1C(=O)O]

To a solution of ethyl 4-bromo-1-methyl-3-[2-(morpholin-4-yl)ethyl]-1H-pyrazole-5-carboxylate (420 mg, 1.21 mmol) in THF (12 ml, 150 mmol) at 0° C. was added a solution of lithium aluminium hydride (610 μl, 2.0 M in THF, 1.2 mmol) and the mixture was stirred at 0° C. for 3 hours. Ice was carefully added and the mixture was stirred for 30 minutes. The reaction was poured into a solution of Na—K tartrate and the mixture was extracted three times with ethyl acetate. The combined organic layers were washed with brine and dried over sodium sulfate. After filtration and removal of the solvents the crude product was triturated with diethyl ether to give the title compound (250 mg).

¹H-NMR (400 MHz, CHLOROFORM-d) δ [ppm]: 0.000 (1.44), 1.140 (0.65), 2.490 (1.87), 2.603 (0.84), 2.620 (0.81), 2.709 (1.16), 2.730 (1.12), 2.748 (0.67), 3.677 (3.01), 3.776 (0.98), 3.832 (16.00), 4.563 (0.53), 4.596 (9.18).

Intermediate 222 ethyl 7-{5-(hydroxymethyl)-1-methyl-3-[2-(morpholin-4-yl)ethyl]-1H-pyrazol-4-yl}-3-[3-(naphthalen-1-yloxy)propyl]-1H-indole-2-carboxylate

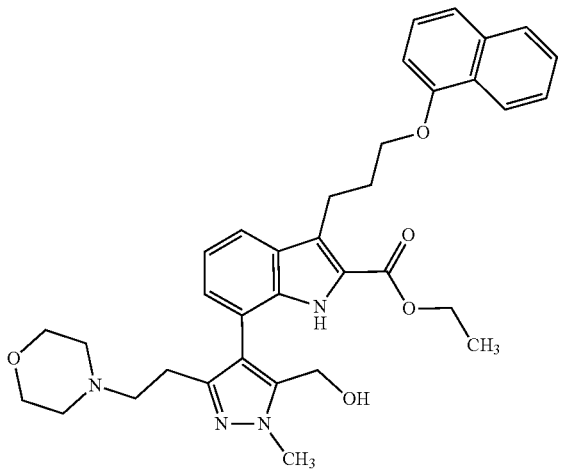

To a solution of ethyl 3-[3-(naphthalen-1-yloxy)propyl]-7-(4,4,5,5-tetramethyl-1,3,2-dioxaborolan-2-yl)-1H-indole-2-carboxylate (see Intermediate 5, 386 mg, 100% purity, 773 µmol) and {4-bromo-1-methyl-3-[2-(morpholin-4-yl)ethyl]-1H-pyrazol-5-yl}methanol (235 mg, 773 µmol) in 1,4-dioxane (9.9 ml, 120 mmol) were added an aqueous 2 M solution of potassium carbonate (1.2 ml, 2.0 M, 2.3 mmol). The mixture was degassed and purged with argon several times. Pd(dppf)Cl₂×CH₂Cl₂ (126 mg, 155 µmol) was added and the mixture was purged with argon for 10 minutes. The reaction mixture was stirred at 80° C. for 8 hours. For work-up, the reaction mixture was poured into water and the mixture was extracted four times with ethyl acetate. The combined organic phases were dried over sodium sulfate. After filtration and removal of the solvent, the crude product was purified by flash chromatography (dichloromethane/acetone gradient, 0%→50% acetone) to give the title compound (220 mg).

¹H-NMR (400 MHz, DMSO-d6) δ [ppm]: 1.066 (0.63), 1.071 (0.56), 1.088 (1.05), 1.105 (0.52), 1.233 (0.98), 1.258 (5.03), 1.276 (10.68), 1.293 (5.01), 2.153 (3.47), 2.211 (1.22), 2.229 (1.61), 2.247 (1.18), 2.322 (0.67), 2.327 (0.87), 2.332 (0.69), 2.399 (1.14), 2.522 (1.75), 2.599 (1.09), 2.664 (0.64), 2.669 (0.78), 2.673 (0.56), 3.356 (2.95), 3.371 (4.64), 3.377 (5.04), 3.388 (3.54), 3.554 (0.47), 3.565 (0.67), 3.784 (1.82), 3.877 (16.00), 4.188 (1.73), 4.204 (3.35), 4.218 (1.82), 4.237 (1.79), 4.254 (4.67), 4.272 (4.48), 4.290 (1.45), 4.429 (0.67), 4.442 (0.64), 5.627 (1.28), 5.639 (2.89), 5.649 (1.19), 6.891 (1.96), 6.909 (2.11), 7.062 (1.24), 7.079 (2.48), 7.099 (2.26), 7.120 (2.65), 7.123 (2.72), 7.138 (1.43), 7.141 (1.18), 7.367 (1.37), 7.388 (2.61), 7.407 (2.08), 7.449 (2.85), 7.469 (1.61), 7.490 (0.45), 7.495 (0.65), 7.508 (1.74), 7.512 (1.82), 7.515 (2.17), 7.523 (3.65), 7.532 (2.31), 7.539 (1.87), 7.551 (0.69), 7.675 (1.87), 7.694 (1.75), 7.860 (1.66), 7.869 (0.90), 7.878 (1.37), 7.884 (1.38), 8.233 (1.43), 8.239 (1.28), 8.248 (0.74), 8.257 (1.36), 10.823 (3.04).

Intermediate 223 ethyl 1-{3-[(tert-butoxycarbonyl)(methyl)amino]propyl}-7-{5-(hydroxymethyl)-1-methyl-3-[2-(morpholin-4-yl)ethyl]-1H-pyrazol-4-yl}-3-[3-(naphthalen-1-yloxy)propyl]-1H-indole-2-carboxylate

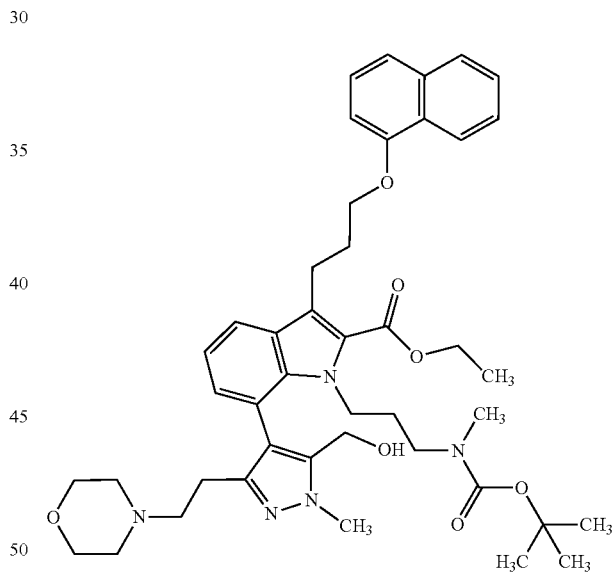

To a solution of ethyl 7-{5-(hydroxymethyl)-1-methyl-3-[2-(morpholin-4-yl)ethyl]-1H-pyrazol-4-yl}-3-[3-(naphthalen-1-yloxy)propyl]-1H-indole-2-carboxylate (220 mg, 369 µmol) in DMF (4.8 ml, 63 mmol) was added caesium carbonate (601 mg, 1.84 mmol) and the mixture was stirred for 10 min at room temperature. tert-butyl (3-bromopropyl)methylcarbamate (see Intermediate 1, 112 mg, 442 µmol) was added and the reaction mixture was stirred for 4 days at room temperature. For work-up the reaction mixture was filtered and the filtrate was concentrated under reduced pressure. The crude product was purified by flash chromatography (dichloromethane/methanol gradient, 0%→10% methanol) to give the title compound (140 mg).

LC-MS (Method 2): R$_t$=1.63 min; MS (ESIpos): m/z=768 [M+H]⁺

571
Intermediate 224 ethyl 7-{5-(bromomethyl)-1-methyl-3-[2-(morpholin-4-yl)ethyl]-1H-pyrazol-4-yl}-1-{3-[(tert-butoxycarbonyl)(methyl)amino]propyl}-3-[3-(naphthalen-1-yloxy)propyl]-1H-indole-2-carboxylate

572
Intermediate 225 ethyl 7-{5-(bromomethyl)-1-methyl-3-[2-(morpholin-4-yl)ethyl]-1H-pyrazol-4-yl}-1-[3-(methylamino)propyl]-3-[3-(naphthalen-1-yloxy)propyl]-1H-indole-2-carboxylate hydrochloric acid salt

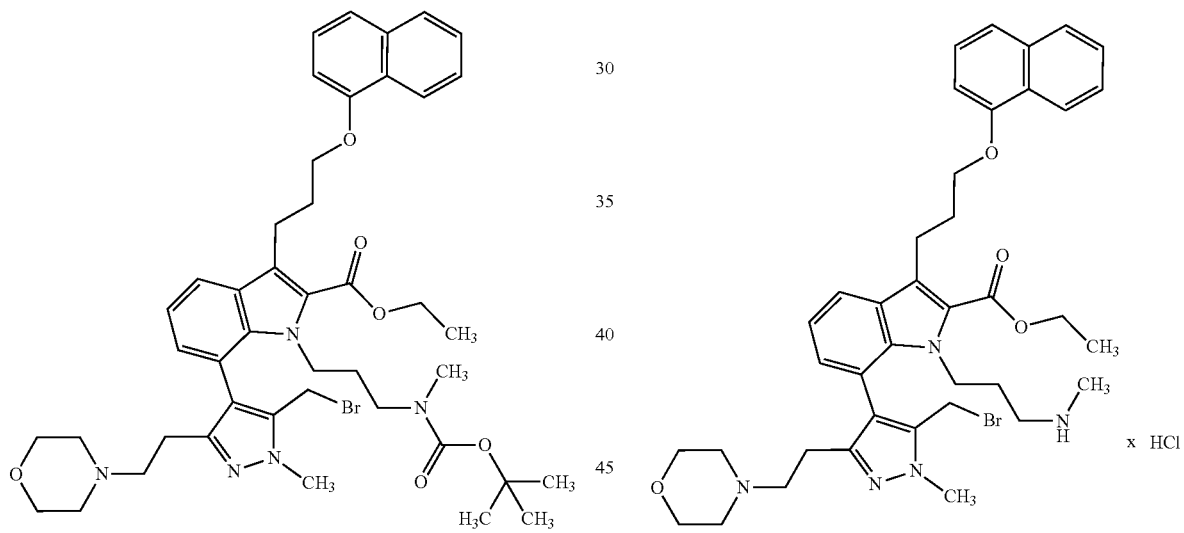

To a solution of ethyl 1-{3-[(tert-butoxycarbonyl)(methyl)amino]propyl}-7-{5-(hydroxymethyl)-1-methyl-3-[2-(morpholin-4-yl)ethyl]-1H-pyrazol-4-yl}-3-[3-(naphthalen-1-yloxy)propyl]-1H-indole-2-carboxylate (140 mg, 182 µmol) in dichloromethane (3.3 ml, 52 mmol), triphenylphosphine (115 mg, 438 µmol) was added at 0° C. and the mixture was stirred at 0° C. for 10 min. Tetrabromomethane (145 mg, 438 µmol) was added and the reaction mixture was stirred at 0° C. for 4 hours. For work-up the reaction mixture was concentrated under reduced pressure and the crude product was used in the subsequent steps without further purification.

To a solution of ethyl 7-{5-(bromomethyl)-1-methyl-3-[2-(morpholin-4-yl)ethyl]-1H-pyrazol-4-yl}-1-{3-[(tert-butoxycarbonyl)(methyl)amino]propyl}-3-[3-(naphthalen-1-yloxy)propyl]-1H-indole-2-carboxylate (150 mg) in methanol (3.3 ml, 51 mmol) was added a 4 M solution of hydrogen chloride in dioxan (3.2 ml, 4.0 M, 13 mmol) at 0° C. and the mixture was stirred for 3 hours at room temperature. For work-up the mixture was concentrated under reduced pressure and the crude product was used for the subsequent steps without further purification.

Intermediate 226

(rac)-ethyl 7,9-dimethyl-11-[2-(morpholin-4-yl) ethyl]-1-[3-(naphthalen-1-yloxy)propyl]-4,5,6,7,8,9-hexahydropyrazolo[3',4':7,8][1,5]diazecino[9,10,1-hi]indole-2-carboxylate

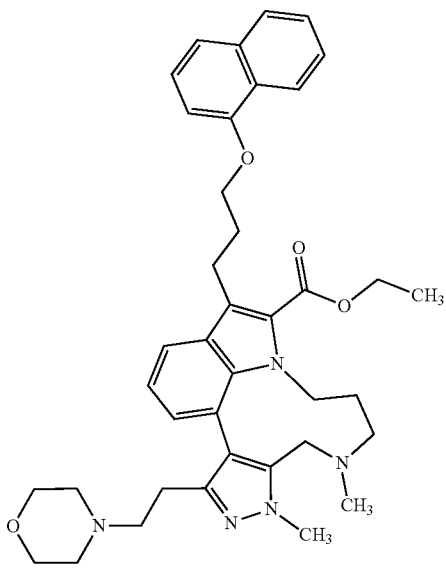 [SMILES: CCOC(=O)c1c(CCCOc2cccc3ccccc23)c2cccc3c2n1CCCN(C)Cc1c-3c(CCN2CCOCC2)nn1C]

To a solution of ethyl 7-{5-(bromomethyl)-1-methyl-3-[2-(morpholin-4-yl)ethyl]-1H-pyrazol-4-yl}-1-[3-(methylamino)propyl]-3-[3-(naphthalen-1-yloxy)propyl]-1H-indole-2-carboxylate hydrochloric acid salt (150 mg) in DMF (15 ml, 200 mmol) was added caesium carbonate (319 mg, 978 µmol) and the reaction was stirred at 65° C. for 5 hours. For work-up the mixture was concentrated under reduced pressure and the residue was purified by flash chromatography (dichloromethane/methanol gradient, 0%→6% methanol) to give the title compound (92 mg).

LC-MS (Method 2): $R_t$=1.72 min; MS (ESIpos): m/z=650 [M+H]$^+$

Intermediate 227

(rac)-ethyl 4-bromo-1-methyl-3-[2-(tetrahydro-2H-pyran-2-yloxy)ethyl]-1H-pyrazole-5-carboxylate

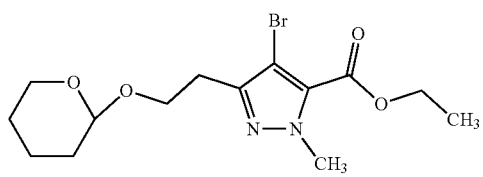 [SMILES: CCOC(=O)c1c(Br)c(CCOC2CCCCO2)nn1C]

To a mixture of ethyl 4-bromo-3-(2-hydroxyethyl)-1-methyl-1H-pyrazole-5-carboxylate (14.8 g, 53.4 mmol) (see Intermediate 218) and 3,4-dihydro-2H-pyran (20 ml, 97% purity, 210 mmol) in THF (370 ml, 4.5 mol) was added pyridinium p-toluenesulfonate (2.74 g, 98% purity, 10.7 mmol) and the mixture was stirred for 5 days at 50° C. For work-up, the reaction was diluted with ethyl acetate and the mixture was washed with aqueous sodium bicarbonate solution and brine. The organic phase was dried over sodium sulfate. After filtration and removal of the solvent, the crude product was purified by flash chromatography (hexane/ethyl acetate gradient, 7%→60% ethyl acetate) to give the title compound (10.5 g).

$^1$H-NMR (400 MHz, CHLOROFORM-d) δ [ppm]: 0.000 (1.04), 1.333 (3.95), 1.351 (8.45), 1.369 (4.04), 1.427 (0.62), 1.442 (0.89), 1.459 (1.02), 1.474 (0.68), 1.486 (0.63), 1.491 (0.65), 1.502 (6.55), 1.512 (0.76), 1.522 (0.67), 1.529 (0.65), 1.540 (0.54), 1.545 (0.53), 1.606 (0.40), 1.622 (0.43), 1.631 (0.70), 1.639 (0.60), 1.743 (0.44), 1.767 (0.42), 2.861 (0.98), 2.867 (0.97), 2.878 (1.21), 2.881 (1.44), 2.884 (1.52), 2.886 (1.32), 2.898 (1.08), 2.903 (1.08), 3.410 (0.44), 3.424 (0.45), 3.438 (0.57), 3.600 (0.55), 3.618 (0.68), 3.619 (0.79), 3.625 (0.89), 3.636 (0.61), 3.641 (0.94), 3.644 (0.91), 3.661 (0.59), 3.734 (0.46), 3.755 (0.42), 3.762 (0.75), 3.783 (0.42), 3.877 (0.64), 3.894 (0.83), 3.897 (0.71), 3.902 (0.61), 3.914 (0.64), 3.919 (0.77), 3.921 (0.62), 3.939 (0.52), 4.040 (16.00), 4.073 (0.65), 4.300 (1.17), 4.318 (3.77), 4.335 (3.81), 4.353 (1.20), 4.570 (0.83), 4.579 (1.21), 4.588 (0.84).

Intermediate 228

(rac)-{4-bromo-1-methyl-3-[2-(tetrahydro-2H-pyran-2-yloxy)ethyl]-1H-pyrazol-5-yl}methanol

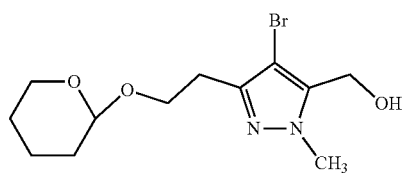 [SMILES: Cn1nc(CCOC2CCCCO2)c(Br)c1CO]

To a solution of (rac)-ethyl 4-bromo-1-methyl-3-[2-(tetrahydro-2H-pyran-2-yloxy)ethyl]-1H-pyrazole-5-carboxylate (10.5 g, 29.1 mmol) in THF (280 ml) at 0° C. was added the solution of lithium aluminium hydride (15 ml, 2.0 M, 29 mmol) and the mixture was stirred at 0° C. for 3 hours. Ice was carefully added and the mixture was stirred for 30 minutes. The reaction was poured into a solution of Na—K tartrate and the mixture was extracted three times with ethyl acetate. The combined organic layers were washed with brine and dried over sodium sulfate. After filtration and removal of the solvents the crude product (9 g) was used without further purification in the subsequent steps.

Intermediate 229

(rac)-ethyl 7-{5-(hydroxymethyl)-1-methyl-3-[2-(tetrahydro-2H-pyran-2-yloxy)ethyl]-1H-pyrazol-4-yl}-3-[3-(naphthalen-1-yloxy)propyl]-1H-indole-2-carboxylate

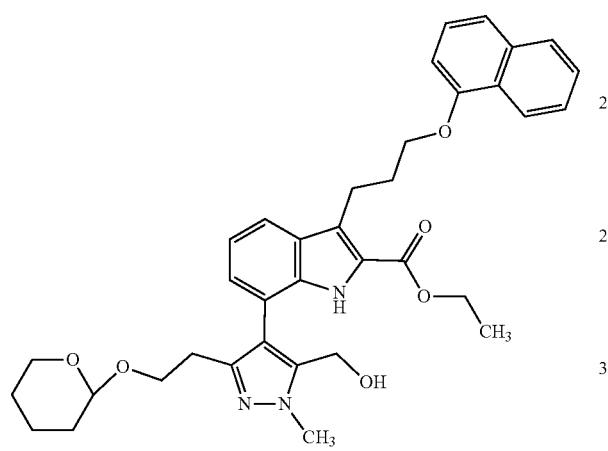

To a solution of ethyl 3-[3-(naphthalen-1-yloxy)propyl]-7-(4,4,5,5-tetramethyl-1,3,2-dioxaborolan-2-yl)-1H-indole-2-carboxylate (see Intermediate 5, 12.5 g, 100% purity, 25.1 mmol) and {4-bromo-1-methyl-3-[2-(tetrahydro-2H-pyran-2-yloxy)ethyl]-1H-pyrazol-5-yl}methanol (8.00 g, 25.1 mmol) in 1,4-dioxane (320 ml) were added an aqueous 2 M solution of potassium carbonate (38 ml, 2.0 M, 75 mmol). The mixture was degassed and purged with argon several times. Pd(dppf)Cl$_2$×CH$_2$CL$_2$ (4.09 g, 5.01 mmol) was added and the mixture was purged with argon for 10 minutes. The reaction mixture was stirred at 80° C. for 18 hours. For work-up, the reaction mixture was poured into water and the mixture was extracted four times with ethyl acetate. The combined organic layers were washed with brine and dried over sodium sulfate. After filtration and removal of the solvents the crude product was purified twice by flash chromatography (dichloromethane/acetone gradient, 20%→60% acetone) to give the title compound (9.2 g).

$^1$H-NMR (400 MHz, DMSO-d6) δ [ppm]: 1.067 (16.00), 1.259 (4.40), 1.277 (9.41), 1.295 (4.83), 1.310 (0.79), 1.343 (0.55), 1.370 (0.42), 1.379 (0.46), 1.433 (0.83), 1.444 (1.06), 1.454 (0.86), 1.517 (0.41), 2.084 (2.80), 2.213 (0.71), 2.230 (1.02), 2.248 (0.75), 2.327 (0.49), 2.518 (1.83), 2.523 (1.34), 2.669 (0.57), 2.674 (0.42), 2.688 (0.90), 2.706 (1.97), 2.720 (1.05), 2.725 (1.44), 2.737 (0.91), 3.226 (0.40), 3.254 (0.47), 3.355 (1.46), 3.372 (0.81), 3.494 (0.46), 3.508 (0.61), 3.526 (0.77), 3.532 (0.54), 3.544 (0.50), 3.550 (0.72), 3.691 (8.28), 3.703 (0.57), 3.716 (0.51), 3.723 (0.57), 3.781 (0.72), 3.786 (0.55), 3.791 (2.23), 3.805 (0.56), 3.884 (12.81), 3.939 (2.57), 4.089 (0.43), 4.198 (1.13), 4.213 (2.29), 4.228 (1.21), 4.238 (1.23), 4.256 (3.16), 4.273 (3.06), 4.291 (0.99), 4.369 (0.61), 4.413 (1.97), 4.426 (1.97), 4.433 (0.71), 4.447 (0.64), 4.576 (0.62), 4.587 (0.43), 5.167 (0.59), 5.181 (1.37), 5.195 (0.58), 5.669 (1.02), 5.759 (1.31), 5.988 (1.71), 6.901 (1.33), 6.918 (1.45), 7.070 (1.13), 7.088 (1.74), 7.090 (1.45), 7.108 (1.61), 7.166 (1.38), 7.182 (0.92), 7.373 (1.12), 7.393 (2.04), 7.412 (1.75), 7.450 (2.03), 7.471 (1.11), 7.494 (0.49), 7.506 (1.34), 7.511 (1.23), 7.514 (1.61), 7.522 (2.84), 7.530 (1.65), 7.533 (1.33), 7.538 (1.45), 7.551 (0.51), 7.679 (1.36), 7.698 (1.26), 7.860 (1.16), 7.863 (0.90), 7.869 (0.60), 7.878 (0.95), 7.884 (0.99), 8.230 (1.04), 8.236 (0.93), 8.244 (0.46), 8.246 (0.50), 8.254 (0.95), 10.847 (1.58).

Intermediate 230 ethyl (11Z)-1-methyl-7-[3-(naphthalen-1-yloxy)propyl]-3-[2-(tetrahydro-2H-pyran-2-yloxy)ethyl]-1,10,13,15-tetrahydropyrazolo[4',3':9,10][1,6]oxazacycloundecino[8,7,6-hi]indole-8-carboxylate (Mixture of Stereoisomers)

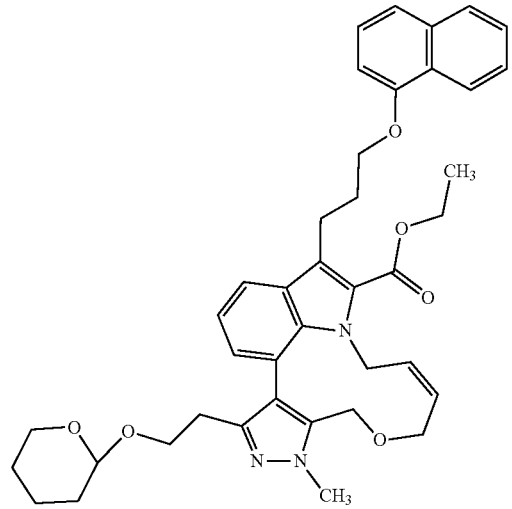

To a solution of ethyl 7-{5-(hydroxymethyl)-1-methyl-3-[2-(tetrahydro-2H-pyran-2-yloxy)ethyl]-1H-pyrazol-4-yl}-3-[3-(naphthalen-1-yloxy)propyl]-1H-indole-2-carboxylate (7.00 g, 11.4 mmol) in acetonitrile (130 ml) was added caesium carbonate (18.8 g, 57.2 mmol) and the mixture was stirred for 10 min at room temperature. (2Z)-1,4-dichlorobut-2-ene (1.3 ml, 13 mmol) and sodium iodide (3.46 g, 22.9 mmol) was added and the reaction mixture was stirred for 5 hours at 40° C. For work-up, the reaction mixture was filtered and the residue was washed with ethyl acetate. The filtrate was concentrated under reduced pressure and the crude product was purified by flash chromatography (dichloromethane/acetone gradient, 5%→40% acetone) to give the title compound (6.3 g).

Intermediate 231 ethyl 1-methyl-7-[3-(naphthalen-1-yloxy)propyl]-3-[2-(tetrahydro-2H-pyran-2-yloxy)ethyl]-1,10,11,12,13,15-hexahydropyrazolo[4',3':9,10][1,6]oxazacycloundecino[8,7,6-hi]indole-8-carboxylate (Mixture of Stereoisomers)

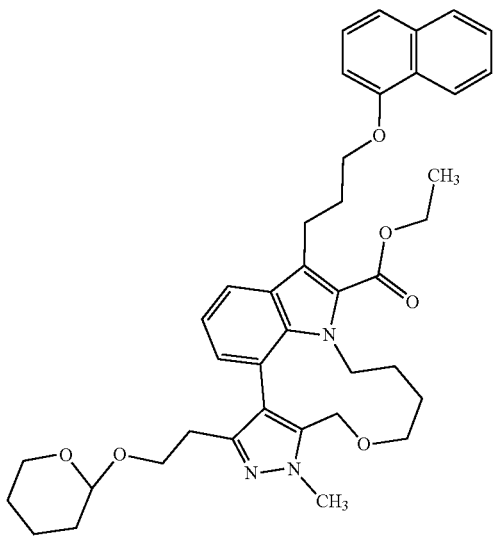

A suspension of ethyl (11Z)-1-methyl-7-[3-(naphthalen-1-yloxy)propyl]-3-[2-(tetrahydro-2H-pyran-2-yloxy)ethyl]-1,10,13,15-tetrahydropyrazolo[4',3':9,10][1,6]oxazacycloundecino[8,7,6-hi]indole-8-carboxylate (mixture of stereoisomers; 6.30 g, 9.49 mmol) and Pd/C (636 mg, 10%, 598 µmol) in ethanol (170 ml) was stirred under an atmosphere of hydrogen at room temperature for 18 hours. For work-up the mixture was filtered through a pad of celite, washed with THF and the filtrate was concentrated under reduced pressure. The residue was purified by flash chromatography (hexane/ethyl acetate gradient, 12%→100% ethyl acetate) to give the title compound (4.8 g, contains (rac)-ethyl 3-(2-hydroxyethyl)-1-methyl-7-[3-(1-naphthyloxy)propyl]-1,10,11,12,13,15-hexahydropyrazolo[4',3':9,10][1,6]oxazacycloundecino[8,7,6-hi]indole-8-carboxylate as a side product).

LC-MS (Method 1): Rt=1.75 min; MS (ESIpos): m/z=666 [M+H]$^+$

Side product: LC-MS (Method 1): Rt=1.56 min; MS (ESIpos): m/z=582 [M+H]$^+$

Intermediate 232

(rac)-ethyl 3-(2-hydroxyethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate

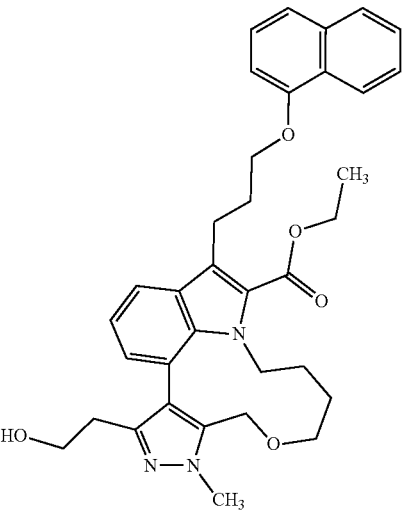

To a solution of ethyl 1-methyl-7-[3-(naphthalen-1-yloxy)propyl]-3-[2-(tetrahydro-2H-pyran-2-yloxy)ethyl]-1,10,11,12,13,15-hexahydropyrazolo[4',3':9,10][1,6]oxazacycloundecino[8,7,6-hi]indole-8-carboxylate (mixture of stereoisomers; 4.80 g, 7.21 mmol) in ethanol (150 ml) at 0° C. was added p-touluensulfonic acide (1.24 g, 7.21 mmol) and the mixture was stirred at room temperature for 5 hours. For work-up, the reaction was poured into a solution of sodium bicarbonate in water and the mixture was extracted three times with ethyl acetate. The combined organic layers were washed with brine and dried over sodium sulfate. After filtration and removal of the solvents the crude product was purified by flash chromatography (dichloromethane/acetone gradient, 6%→40% acetone) to give the title compound (3.3 g)

LC-MS (Method 2): Rt=1.56 min; MS (ESIpos): m/z=582 [M+H]$^+$ $^1$H-NMR (400 MHz, DMSO-d6) δ [ppm]: 1.014 (1.07), 1.026 (1.04), 1.233 (1.12), 1.244 (0.99), 1.265 (5.19), 1.283 (11.21), 1.300 (5.09), 1.308 (0.64), 2.084 (15.61), 2.225 (0.92), 2.238 (0.73), 2.295 (0.43), 2.308 (0.81), 2.313 (0.46), 2.325 (1.09), 2.331 (1.33), 2.338 (0.92), 2.347 (0.96), 2.356 (1.11), 2.361 (0.89), 2.373 (0.46), 2.378 (0.83), 2.390 (0.43), 2.518 (1.63), 2.523 (1.07), 2.669 (0.48), 2.770 (0.70), 2.782 (0.49), 2.788 (0.46), 2.800 (0.72), 3.254 (0.40), 3.271 (0.56), 3.288 (0.75), 3.309 (0.60), 3.320 (0.94), 3.342 (1.92), 3.348 (1.78), 3.356 (1.72), 3.373 (0.90), 3.378 (0.95), 3.394 (0.43), 3.410 (0.77), 3.423 (0.56), 3.439 (0.72), 3.851 (16.00), 4.017 (0.50), 4.033 (0.68), 4.053 (0.49), 4.206 (1.13), 4.226 (2.72), 4.233 (3.22), 4.239 (2.00), 4.251 (2.76), 4.260 (2.23), 4.268 (1.29), 4.285 (1.81), 4.304 (1.66), 4.312 (0.98), 4.321 (0.53), 4.330 (1.02), 4.422 (0.95), 4.427 (1.97), 4.441 (4.08), 4.455 (2.03), 4.613 (2.02), 4.646 (1.79), 5.759 (0.62), 6.872 (1.91), 6.875 (2.00), 6.889 (2.26), 6.892 (2.14), 6.914 (1.69), 6.931 (1.84), 7.062 (1.89), 7.080 (1.92), 7.082 (2.21), 7.100 (1.64), 7.378 (1.33), 7.399 (2.51), 7.418 (2.09), 7.456 (2.53), 7.477 (1.38), 7.501 (0.52), 7.513 (1.64), 7.518 (2.85), 7.528

(3.42), 7.537 (3.01), 7.542 (1.81), 7.554 (0.59), 7.772 (1.86), 7.775 (1.92), 7.792 (1.78), 7.796 (1.65), 7.865 (1.42), 7.868 (1.01), 7.875 (0.71), 7.880 (0.85), 7.882 (0.96), 7.888 (1.22), 8.233 (1.28), 8.240 (0.90), 8.245 (0.58), 8.247 (0.56), 8.257 (1.18).

Intermediate 233

(rac)-ethyl 3-(2-bromoethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate

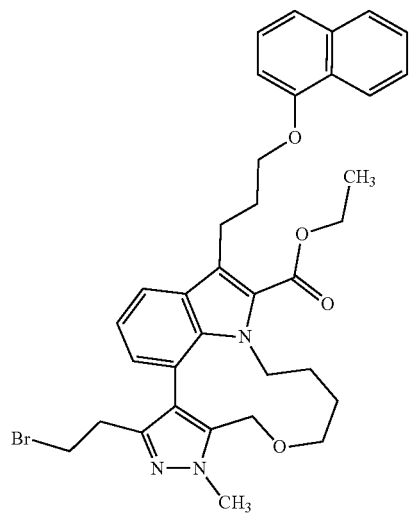

To a solution of (rac)-ethyl 3-(2-hydroxyethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (850 mg, 1.46 mmol) in dichloromethane (27 ml), triphenylphosphine (575 mg, 2.19 mmol) was added at 0° C. and the mixture was stirred at 0° C. for 10 min. Tetrabromomethane (727 mg, 2.19 mmol) was added and the reaction was stirred at room temperature for 6 hours. For work-up, the reaction was concentrated under reduced pressure and the crude product was purified by flash chromatography (dichloromethane/acetone gradient, 7%→50% acetone) to give the title compound (640 mg).

¹H-NMR (400 MHz, DMSO-d6) δ [ppm]: 1.035 (1.11), 1.231 (1.52), 1.263 (5.35), 1.281 (10.57), 1.299 (4.87), 1.987 (0.44), 2.208 (0.86), 2.225 (1.24), 2.242 (0.93), 2.323 (0.43), 2.327 (0.59), 2.331 (0.42), 2.518 (2.51), 2.523 (1.80), 2.633 (0.48), 2.651 (0.88), 2.670 (1.51), 2.689 (1.66), 2.707 (0.77), 2.730 (0.70), 2.748 (1.57), 2.767 (0.89), 2.786 (0.84), 2.803 (0.55), 2.817 (0.75), 2.827 (0.52), 2.846 (0.78), 3.256 (0.46), 3.271 (0.58), 3.290 (0.86), 3.309 (0.50), 3.350 (0.99), 3.367 (0.66), 3.381 (2.57), 3.398 (4.86), 3.416 (2.24), 3.423 (1.06), 3.438 (0.70), 3.452 (0.74), 3.883 (16.00), 3.901 (0.42), 4.006 (0.65), 4.023 (0.68), 4.042 (0.72), 4.187 (0.43), 4.204 (1.80), 4.214 (2.48), 4.222 (1.81), 4.231 (2.68), 4.239 (0.70), 4.249 (2.60), 4.266 (1.07), 4.283 (2.97), 4.301 (1.79), 4.310 (0.95), 4.318 (0.52), 4.328 (0.89), 4.436 (0.84), 4.448 (0.48), 4.459 (0.43), 4.471 (0.75), 4.634 (2.04), 4.667 (1.81), 5.759 (2.64), 6.889 (1.72), 6.908 (3.74), 6.922 (2.18), 6.925 (2.19), 7.065 (1.80), 7.085 (2.23), 7.103 (1.66), 7.368 (1.27), 7.388 (2.48), 7.407 (2.01), 7.450 (2.58), 7.471 (1.48), 7.497 (0.51), 7.509 (1.53), 7.516 (2.10), 7.524 (3.42), 7.533 (2.18), 7.540 (1.75), 7.552 (0.60), 7.788 (1.79), 7.791 (1.89), 7.808 (1.73), 7.811 (1.68), 7.861 (1.47), 7.871 (0.74), 7.879 (1.15), 7.885 (1.28), 8.222 (1.28), 8.229 (1.13), 8.237 (0.60), 8.246 (1.18).

Intermediate 234

(rac)-ethyl 1-methyl-3-[2-(morpholin-4-yl)ethyl]-7-[3-(naphthalen-1-yloxy)propyl]-1,10,11,12,13,15-hexahydropyrazolo[4',3':9,10][1,6]oxazacycloundecino[8,7,6-hi]indole-8-carboxylate

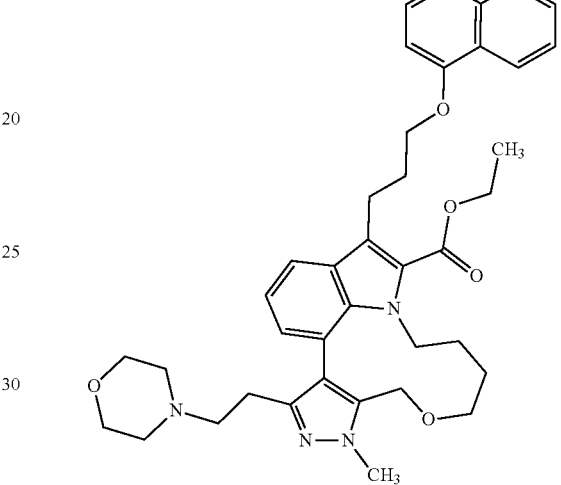

To a solution of morpholine (87 μl, 990 μmol) in acetonitrile (4.3 ml) was added potassium carbonate (144 mg, 1.04 mmol) and the mixture was stirred for 10 min at room temperature. (rac)-Ethyl 3-(2-bromoethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (160 mg, 248 μmol) was added and the reaction mixture was stirred for 17 hours at 50° C. For work-up, the reaction mixture was poured into an aqueous sodium chloride solution. The resulting precipitate was collected by filtration, washed with water and dried to give the title compound (160 mg), which was used in the subsequent steps without further purification.

LC-MS (Method 2): Rt=1.64 min; MS (ESIpos): m/z=651 [M+H]⁺

Intermediate 235

(4-bromo-1-methyl-1H-pyrazol-5-yl)methanol

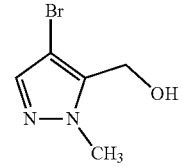

To a solution of methyl 4-bromo-1-methyl-1H-pyrazole-5-carboxylate (5.00 g, 22.8 mmol, CAS 1328640-39-6) in THF (170 ml) at 0° C. was added a solution of lithium aluminium hydride in THF (11 ml, 2.0 M, 23 mmol) and the mixture was stirred at 0° C. for 60 min. For work-up, water (1 ml) was added dropwise, followed by the addition of aqueous 2 M sodium hydroxide solution (1 ml) and again water (1 ml). The mixture was filtered through a pad of celite. The residue was washed with dichloromethane and the filtrate was concentrated under reduced pressure. The residue was triturated with dichloromethane to give the title compound (3.85 g).

LC-MS (Method 2): Rt=0.61 min; MS (ESIpos): m/z=191 [M+H]$^+$ $^1$H-NMR (400 MHz, DMSO-d6) δ [ppm]: 1.088 (0.41), 1.231 (1.15), 1.246 (5.06), 1.264 (10.69), 1.282 (5.09), 1.512 (1.15), 1.809 (0.47), 1.829 (0.45), 1.838 (0.49), 1.847 (0.47), 1.857 (0.43), 1.960 (1.28), 1.975 (1.28), 2.055 (1.06), 2.187 (13.16), 2.206 (1.33), 2.223 (0.53), 2.259 (1.17), 2.277 (2.82), 2.295 (2.44), 2.317 (0.69), 2.322 (0.93), 2.326 (1.30), 2.331 (1.01), 2.342 (0.52), 2.413 (1.89), 2.432 (2.63), 2.450 (1.37), 2.518 (2.77), 2.522 (1.88), 2.664 (0.62), 2.668 (0.81), 2.673 (0.58), 2.945 (1.63), 2.980 (1.73), 3.223 (1.37), 3.239 (1.75), 3.255 (1.07), 3.276 (2.13), 3.285 (1.70), 3.293 (2.04), 3.306 (0.97), 3.313 (1.18), 3.351 (1.21), 3.371 (0.80), 3.385 (0.70), 3.579 (1.74), 3.615 (1.58), 3.810 (16.00), 3.830 (0.86), 3.844 (0.45), 3.853 (0.52), 3.915 (0.43), 4.156 (1.28), 4.172 (2.56), 4.182 (1.60), 4.187 (1.40), 4.200 (0.93), 4.209 (1.93), 4.214 (0.92), 4.227 (2.02), 4.232 (2.10), 4.245 (0.78), 4.250 (1.81), 4.259 (0.75), 4.267 (0.56), 4.277 (0.70), 4.399 (0.41), 4.410 (0.88), 4.420 (0.48), 4.434 (0.45), 4.446 (0.81), 6.855 (1.97), 6.874 (2.10), 6.917 (1.67), 6.920 (1.77), 6.935 (2.34), 6.938 (2.18), 7.014 (2.00), 7.034 (2.25), 7.052 (1.43), 7.357 (1.41), 7.377 (2.67), 7.396 (2.03), 7.445 (2.71), 7.466 (1.60), 7.495 (0.58), 7.507 (1.60), 7.514 (2.19), 7.523 (3.47), 7.531 (2.37), 7.538 (1.78), 7.550 (0.62), 7.718 (1.86), 7.721 (1.97), 7.738 (1.81), 7.742 (1.70), 7.858 (1.59), 7.867 (0.81), 7.875 (1.23), 7.882 (1.33), 8.217 (1.37), 8.223 (1.19), 8.232 (0.66), 8.241 (1.30).

Intermediate 236 ethyl 7-[5-(hydroxymethyl)-1-methyl-1H-pyrazol-4-yl]-3-[3-(naphthalen-1-yloxy)propyl]-1H-indole-2-carboxylate

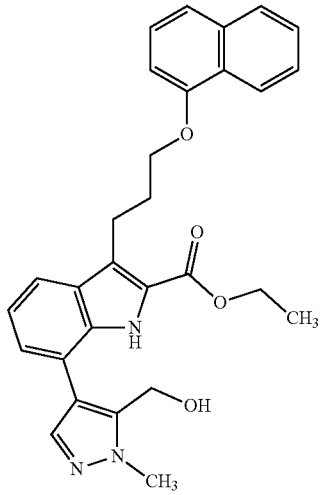 [SMILES: CCOC(=O)c1[nH]c2c(-c3cnn(C)c3CO)cccc2c1CCCOc1cccc2ccccc12]

To a solution of ethyl 3-[3-(naphthalen-1-yloxy)propyl]-7-(4,4,5,5-tetramethyl-1,3,2-dioxaborolan-2-yl)-1H-indole-2-carboxylate (see Intermediate 5; 9.93 g, 19.9 mmol) and (4-bromo-1-methyl-1H-pyrazol-5-yl)methanol (3.80 g, 19.9 mmol) in 1,4-dioxane (260 ml) was added aqueous 2 M solution of potassium carbonate (30 ml, 2.0 M, 60 mmol). The mixture was degassed and purged with argon several times. Pd(dppf)Cl$_2$×CH$_2$Cl$_2$ (3.25 g, 3.98 mmol) was added and the mixture was purged with argon for 10 minutes. The reaction mixture was stirred at 80° C. for 24 hours. For work-up, the reaction mixture was filtered and the residue was washed with dichloromethane. The filtrate was concentrated under reduced pressure and the residue was purified by flash chromatography (dichloromethane/ethyl acetate gradient, 0%→100% ethyl acetate) to give the title compound (8.1 g).

LC-MS (Method 2): Rt=1.54 min; MS (ESIpos): m/z=484 [M+H]$^+$ $^1$H-NMR (400 MHz, DMSO-d6) δ [ppm]: 1.066 (16.00), 1.270 (0.72), 1.288 (1.61), 1.306 (0.73), 3.160 (1.60), 3.173 (1.64), 3.939 (2.89), 3.951 (2.36), 4.194 (0.49), 4.262 (0.66), 4.279 (0.65), 4.474 (0.46), 4.485 (0.44), 7.517 (0.48), 7.584 (0.98).

Intermediate 237 ethyl 1-{4-[(tert-butoxycarbonyl)(methyl)amino]butyl}-7-[5-(hydroxymethyl)-1-methyl-1H-pyrazol-4-yl]-3-[3-(naphthalen-1-yloxy)propyl]-1H-indole-2-carboxylate

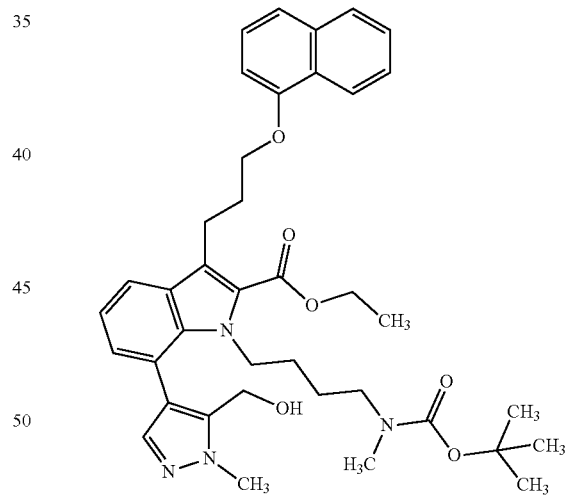

To a solution of ethyl 7-[5-(hydroxymethyl)-1-methyl-1H-pyrazol-4-yl]-3-[3-(naphthalen-1-yloxy)propyl]-1H-indole-2-carboxylate (1.20 g, 2.48 mmol) in DMF (32 ml, 420 mmol) was added caesium carbonate (4.04 g, 12.4 mmol) and the mixture was stirred for 10 min at room temperature. Tert-butyl (4-bromobutyl)methylcarbamate (see Intermediate 2, 793 mg, 2.98 mmol) was added and the reaction mixture was stirred for 4 days at room temperature. For work-up the reaction mixture was poured into water. The mixture was extracted with ethyl acetate. The combined organic phases washed with brine and dried over sodium sulfate. After filtration and removal of the solvent the crude product was purified by flash chromatography (Biotage

Intermediate 238 ethyl 7-[5-(bromomethyl)-1-methyl-1H-pyrazol-4-yl]-1-{4-[(tert-butoxycarbonyl)(methyl)amino]butyl}-3-[3-(naphthalen-1-yloxy)propyl]-1H-indole-2-carboxylate

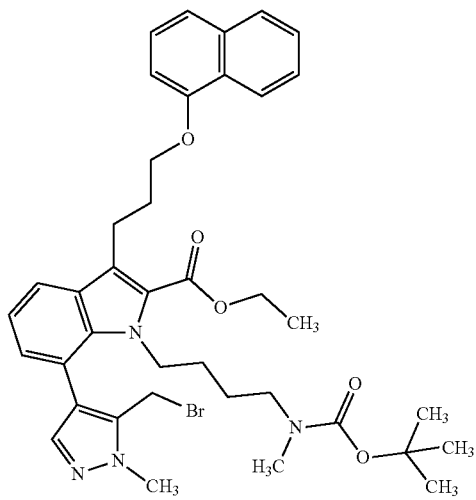 [SMILES: CCOC(=O)c1c(CCCOc2cccc3ccccc23)c2cccc(-c3cnn(C)c3CO)c2n1CCCCN(C)C(=O)OC(C)(C)C]

To a solution of ethyl 1-{4-[(tert-butoxycarbonyl)(methyl)amino]butyl}-7-[5-(hydroxymethyl)-1-methyl-1H-pyrazol-4-yl]-3-[3-(naphthalen-1-yloxy)propyl]-1H-indole-2-carboxylate (700 mg, 1.05 mmol) in dichloromethane (19 ml, 300 mmol), triphenylphosphine (412 mg, 1.57 mmol) was added at 0° C. and the mixture was stirred at 0° C. for 10 min. Tetrabromomethane (521 mg, 1.57 mmol) was added and the reaction mixture was stirred at 0° C. for 6 hours. For work-up the reaction mixture was concentrated under reduced pressure and the crude product was purified by flash chromatography (Biotage SNAP cartridge silica 25 g, hexane/ethylacetate gradient, 7%→10% ethyl acetate) to give the title compound (410 mg).

Intermediate 239 ethyl 7-[5-(bromomethyl)-1-methyl-1H-pyrazol-4-yl]-1-[4-(methylamino)butyl]-3-[3-(naphthalen-1-yloxy)propyl]-1H-indole-2-carboxylate hydrochloric acid salt

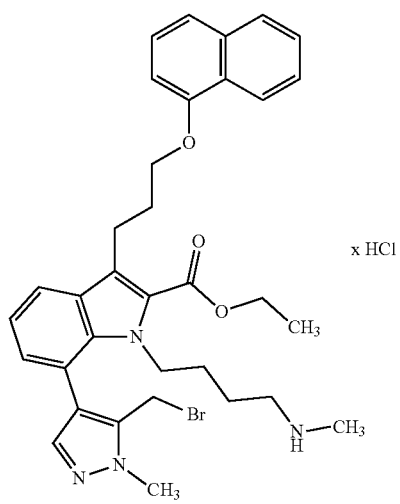 [SMILES: CCOC(=O)c1c(CCCOc2cccc3ccccc23)c2cccc(-c3cnn(C)c3CBr)c2n1CCCCNC]

To a solution of ethyl 7-[5-(bromomethyl)-1-methyl-1H-pyrazol-4-yl]-1-{4-[(tert-butoxycarbonyl)(methyl)amino]butyl}-3-[3-(naphthalen-1-yloxy)propyl]-1H-indole-2-carboxylate (420 mg, 574 µmol) in methanol (10 ml, 160 mmol) was added a 4 M solution of hydrogen chloride in dioxan (10 ml, 4.0 M, 40 mmol) at 0° C. and the mixture was stirred for 1 h at room temperature. For work-up the mixture was concentrated under reduced pressure and the crude product was used for the subsequent steps without further purification.

(SNAP cartridge silica, dichloromethane/methanol gradient, 2%→10% methanol) to give the title compound (700 mg).

Intermediate 240

(rac)-ethyl 1,14-dimethyl-7-[3-(naphthalen-1-yloxy)propyl]-10,11,12,13,14,15-hexahydro-1H-pyrazolo[3',4':8,9][1,6]diazacycloundecino[10,11,1-hi]indole-8-carboxylate

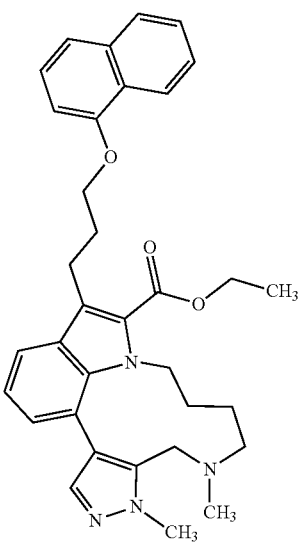 [SMILES: CCOC(=O)c1c(CCCOc2cccc3ccccc23)c2cccc3c2n1CCCCN(C)Cc1c-3cnn1C]

To a solution of ethyl 7-[5-(bromomethyl)-1-methyl-1H-pyrazol-4-yl]-1-[4-(methylamino)butyl]-3-[3-(naphthalen-1-yloxy)propyl]-1H-indole-2-carboxylate hydrochloric acid salt (385 mg) in DMF (51 ml, 660 mmol) was added caesium carbonate (939 mg, 2.88 mmol) and the reaction was stirred at 65° C. for 8 hours. For work-up, the mixture was concentrated under reduced pressure. The residue was purified by flash chromatography (Biotage SNAP cartridge silica 25 g, dichloromethane/methanol gradient, 0%→6% methanol) to give the title compound (280 mg).

LC-MS (Method 2): $R_t$=1.78 min; MS (ESIpos): m/z=551 [M+H]$^+$ $^1$H-NMR (400 MHz, DMSO-d6) δ [ppm]: 0.737 (0.45), 0.764 (0.52), 0.968 (0.45), 1.070 (0.82), 1.088 (0.91), 1.105 (0.68), 1.229 (0.94), 1.250 (5.16), 1.268 (10.87), 1.286 (5.15), 1.332 (0.44), 1.872 (0.67), 1.900 (0.43), 2.157 (10.78), 2.170 (1.33), 2.188 (1.78), 2.205 (1.20), 2.221 (0.49), 2.322 (0.44), 2.326 (0.56), 2.386 (0.49), 2.404 (0.49), 2.428 (0.47), 2.446 (0.51), 2.518 (2.59), 2.522 (1.88), 2.530 (0.86), 2.535 (0.69), 2.664 (0.44), 2.669 (0.58), 2.673 (0.43), 2.729 (0.84), 2.888 (1.02), 3.230 (0.67), 3.245 (0.61), 3.264 (1.01), 3.282 (0.53), 3.299 (1.60), 3.317 (0.60), 3.365 (0.64), 3.370 (0.53), 3.384 (0.97), 3.402 (0.60), 3.417 (0.71), 3.683 (1.74), 3.715 (1.57), 3.840 (0.67), 3.911 (16.00), 3.975 (0.69), 3.996 (0.71), 4.024 (0.49), 4.187 (2.31), 4.202 (3.25), 4.215 (2.83), 4.232 (1.90), 4.239 (0.76), 4.250 (0.69), 4.257 (1.86), 4.274 (1.73), 4.284 (0.91), 4.292 (0.56), 4.301 (0.89), 4.457 (0.72), 4.479 (0.62), 4.493 (0.63), 6.866 (1.74), 6.868 (1.95), 6.883 (2.27), 6.886 (2.22), 6.898 (1.87), 6.915 (1.93), 7.025 (1.95), 7.045 (2.21), 7.063 (1.59), 7.372 (1.29), 7.392 (2.63), 7.398 (0.56), 7.408 (7.81), 7.452 (2.63), 7.472 (1.53), 7.502 (0.57), 7.514 (1.84), 7.519 (2.87), 7.529 (3.28), 7.538 (2.98), 7.543 (1.93), 7.554 (0.68), 7.742 (1.91), 7.745 (1.93), 7.762 (1.82), 7.765 (1.73), 7.862 (1.53), 7.866 (1.09), 7.873 (0.86), 7.877 (0.98), 7.880 (1.04), 7.885 (1.29), 8.218 (1.29), 8.225 (0.95), 8.242 (1.21).

Intermediate 241 ethyl 7-{1-methyl-5-[(prop-2-en-1-yloxy)methyl]-1H-pyrazol-4-yl}-3-[3-(naphthalen-1-yloxy)propyl]-1-(prop-2-en-1-yl)-1H-indole-2-carboxylate

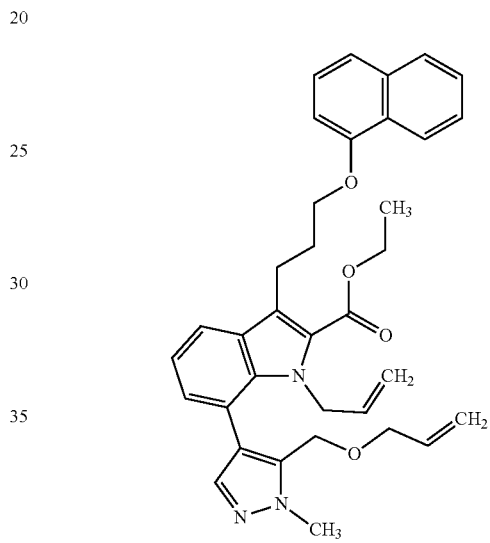

To a solution of ethyl 7-[5-(hydroxymethyl)-1-methyl-1H-pyrazol-4-yl]-3-[3-(naphthalen-1-yloxy)propyl]-1H-indole-2-carboxylate (see Intermediate 236, 1.00 g, 2.07 mmol) in THF (28 ml, 350 mmol) was added sodium hydride (248 mg, 60% purity, 6.20 mmol) at 0° C. and the mixture was stirred for 2 hours at room temperature. The reaction was cooled down to 0° C. and a solution of allyl bromide (herein also referred to as 3-bromoprop-1-ene, 540 μl, 6.2 mmol) in THF (1 ml) was added. The mixture was stirred for 5 days at room temperature. For work-up, the mixture was poured into an aqueous solution of sodium chloride and the mixture was extracted with ethyl acetate. The combined organic phases were washed with brine and were dried over sodium sulfate. After filtration and removal of the solvent, the crude product was purified by flash chromatography (hexane/ethyl acetate gradient, 12%→100% ethyl acetate) to give the title compound (300 mg).

LC-MS (Method 2): Rt=1.77 min; MS (ESIpos): m/z=564 [M+H]$^+$

Intermediate 242

(rac)-ethyl (E/Z)-1-methyl-7-[3-(naphthalen-1-yloxy)propyl]-1,10,13,15-tetrahydropyrazolo[4',3':9,10][1,6]oxazacycloundecino[8,7,6-hi]indole-8-carboxylate

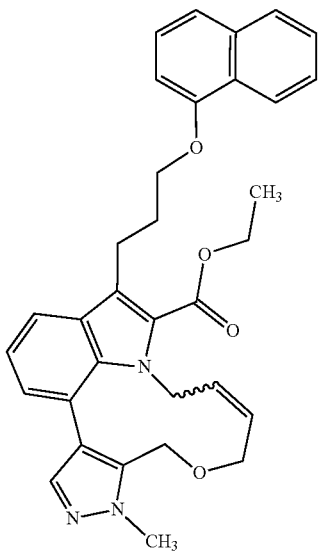 [SMILES: CCOC(=O)c1c(CCCOc2cccc3ccccc23)c2cccc3c2n1CC=CCOCc1c-3cnn1C]

A solution of ethyl 7-{1-methyl-5-[(prop-2-en-1-yloxy)methyl]-1H-pyrazol-4-yl}-3-[3-(naphthalen-1-yloxy)propyl]-1-(prop-2-en-1-yl)-1H-indole-2-carboxylate (300 mg, 532 μmol) in dichloromethane (6.8 ml, 110 mmol) was purged with argon several times. (1,3-Bis(2,4,6-trimethylphenyl)-2-imidazolidinylidene)dichloro(phenylmethylene)(tricyclohexylphosphine)ruthenium (45.2 mg, 53.2 μmol) (Grubbs $2^{nd}$ generation catalyst) was added and the reaction mixture was stirred for 24 hours at room temperature. For work-up, the reaction mixture was concentrated under reduced pressure and the residue was purified by flash chromatography (dichloromethane/acetone gradient, 0%→40% acetone) to give the title compound (120 mg).

LC-MS (Method 2): $R_t$=1.68 min; MS (ESIpos): m/z=536 [M+H]$^+$ $^1$H-NMR (400 MHz, DMSO-d6) δ [ppm]: 1.088 (0.51), 1.260 (3.90), 1.265 (0.74), 1.278 (8.49), 1.283 (1.14), 1.295 (3.93), 1.300 (0.54), 2.210 (0.99), 2.226 (1.24), 2.243 (0.84), 2.323 (0.46), 2.327 (0.64), 2.332 (0.46), 2.518 (2.12), 2.523 (1.56), 2.665 (0.44), 2.669 (0.62), 2.673 (0.44), 3.269 (0.49), 3.285 (0.55), 3.304 (0.84), 3.365 (0.43), 3.371 (0.45), 3.384 (0.80), 3.389 (0.53), 3.398 (0.47), 3.418 (0.46), 3.474 (0.51), 3.504 (0.93), 3.536 (0.63), 3.769 (3.68), 3.776 (0.75), 3.801 (0.58), 3.812 (0.58), 3.918 (0.53), 3.938 (16.00), 4.202 (0.59), 4.213 (1.48), 4.219 (1.63), 4.228 (2.98), 4.237 (1.38), 4.246 (3.59), 4.258 (0.82), 4.264 (1.64), 4.276 (1.96), 4.281 (2.29), 4.294 (1.54), 4.302 (0.64), 4.311 (0.44), 4.320 (0.61), 4.645 (0.45), 4.673 (0.55), 4.686 (0.62), 4.714 (0.64), 4.735 (1.87), 4.769 (1.71), 4.928 (1.13), 4.950 (0.91), 4.955 (0.90), 4.964 (0.71), 4.976 (0.61), 5.181 (0.54), 5.192 (0.50), 6.861 (1.57), 6.864 (1.72), 6.869 (0.54), 6.879 (1.89), 6.881 (1.81), 6.887 (0.49), 6.914 (1.55), 6.933 (1.66), 7.068 (1.50), 7.077 (0.45), 7.086 (1.58), 7.088 (1.85), 7.095 (0.47), 7.097 (0.50), 7.106 (1.41), 7.379 (1.23), 7.390 (7.43), 7.399 (3.05), 7.418 (1.89), 7.453 (2.60), 7.474 (1.41), 7.482 (0.44), 7.487 (0.53), 7.499 (1.25), 7.504 (1.07), 7.507 (0.73), 7.513 (1.61), 7.518 (2.26), 7.523 (1.91), 7.532 (1.60), 7.537 (1.57), 7.549 (0.60), 7.554 (0.48), 7.774 (1.54), 7.777 (1.60), 7.783 (0.47), 7.785 (0.49), 7.794 (1.45), 7.797 (1.42), 7.861 (1.50), 7.867 (0.82), 7.880 (1.54), 7.884 (1.23), 8.182 (1.07), 8.186 (1.03), 8.200 (0.79), 8.206 (1.14).

Intermediate 243

(rac)-ethyl 1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate

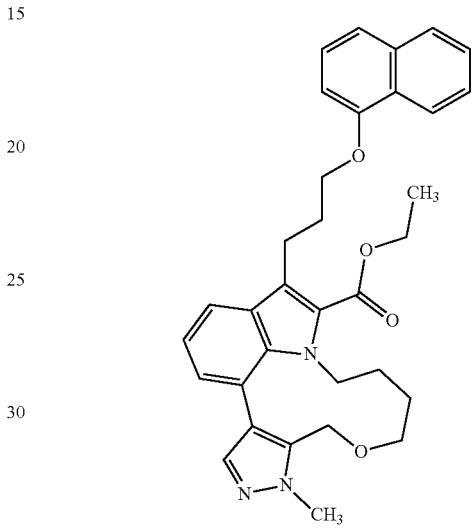

A suspension of (rac)-ethyl (E/Z)-1-methyl-7-[3-(naphthalen-1-yloxy)propyl]-1,10,13,15-tetrahydropyrazolo[4',3':9,10][1,6]oxazacycloundecino[8,7,6-hi]indole-8-carboxylate (120 mg, 224 μmol) and Pd/C (35.8 mg, 10% purity, 33.6 μmol) in ethanol (3.9 ml, 67 mmol) was stirred under an atmosphere of hydrogen at room temperature for 2 days. For work-up the mixture was filtered through a pad of celite. The residue was washed with THF and the filtrate was concentrated under reduced pressure to give the crude compound (120 mg) which was used in subsequent steps without further purification.

Intermediate 244 ethyl 3-[(acetyloxy)methyl]-4-bromo-1-methyl-1H-pyrazole-5-carboxylate

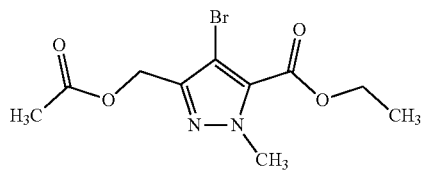 [SMILES: CCOC(=O)c1c(Br)c(COC(C)=O)nn1C]

To a solution of ethyl 4-bromo-3-(bromomethyl)-1-methyl-1H-pyrazole-5-carboxylate (see Intermediate 6, 20.0 g, 61.3 mmol) in DMF (400 ml) was added potassium acetate (7.30 g, 73.6 mmol) and the mixture was stirred for 3 hours at room temperature. For work-up, the mixture was

Intermediate 245 ethyl 4-bromo-3-(hydroxymethyl)-1-methyl-1H-pyrazole-5-carboxylate

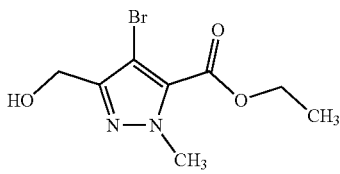

To a solution of ethyl 3-[(acetyloxy)methyl]-4-bromo-1-methyl-1H-pyrazole-5-carboxylate (18.5 g, 60.6 mmol) in ethanol (320 ml) was added potassium carbonate (8.38 g, 60.6 mmol) and the mixture was stirred for 4 hours at room temperature. For work-up, the mixture was poured into water and the mixture was extracted three times with ethyl acetate. The combined organic phases were washed with brine and were dried over sodium sulfate. After filtration and removal of the solvent, the crude product (15.8 g) was used in the subsequent steps without further purification.

Intermediate 246

(rac)-ethyl 4-bromo-1-methyl-3-[(tetrahydro-2H-pyran-2-yloxy)methyl]-1H-pyrazole-5-carboxylate

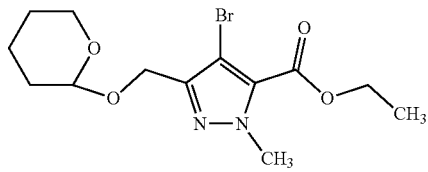 [SMILES: CCOC(=O)c1c(Br)c(COC2CCCCO2)nn1C]

To a mixture of ethyl 4-bromo-3-(hydroxymethyl)-1-methyl-1H-pyrazole-5-carboxylate (15.8 g, 60.1 mmol) and 3,4-dihydro-2H-pyran (23 ml, 97% purity, 240 mmol) in THF (410 ml) was added pyridinium p-toluenesulfonate (3.08 g, 12.0 mmol) and the mixture was stirred for 3 hours at 50° C. For work-up, the reaction was diluted with ethyl acetate and the mixture was washed with aqueous sodium bicarbonate solution and brine. The organic phase was dried over sodium sulfate. After filtration and removal of the solvent, the crude product (21 g) was used in the subsequent steps without further purification.

Intermediate 247

(rac)-{4-bromo-1-methyl-3-[(tetrahydro-2H-pyran-2-yloxy)methyl]-1H-pyrazol-5-yl}methanol

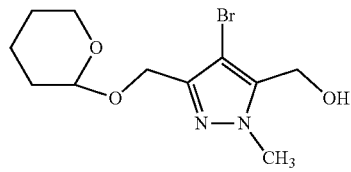 [SMILES: Cn1nc(COC2CCCCO2)c(Br)c1CO]

To a solution of (rac)-ethyl 4-bromo-1-methyl-3-[(tetrahydro-2H-pyran-2-yloxy)methyl]-1H-pyrazole-5-carboxylate (21.0 g, 60.5 mmol) in THF (590 ml) at 0° C. was added a solution of lithium aluminium hydride (30 ml, 2.0 M in THF, 60 mmol) and the mixture was stirred at 0° C. for 3 hours. Ice was carefully added and the mixture was stirred for 30 minutes. A solution of Na—K tartrate was added and the mixture was poured into water. The mixture was extracted three times with ethyl acetate. The combined organic layers were washed with brine and dried over sodium sulfate. After filtration and removal of the solvents the crude product (18.5 g) was used without further purification in the subsequent steps.

Intermediate 248

(rac)-ethyl 7-{5-(hydroxymethyl)-1-methyl-3-[(tetrahydro-2H-pyran-2-yloxy)methyl]-1H-pyrazol-4-yl}-3-[3-(naphthalen-1-yloxy)propyl]-1H-indole-2-carboxylate

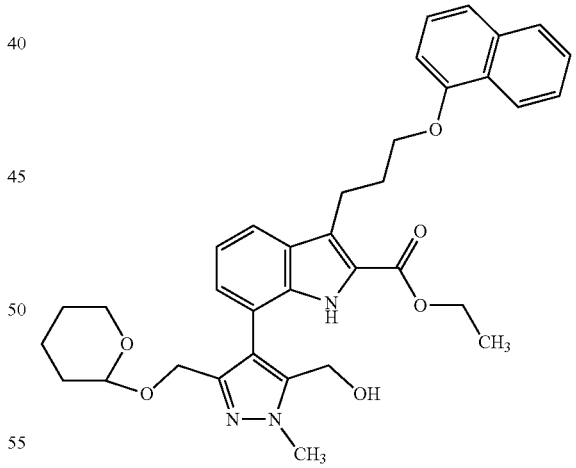

To a solution of (rac)-ethyl 3-[3-(naphthalen-1-yloxy)propyl]-7-(4,4,5,5-tetramethyl-1,3,2-dioxaborolan-2-yl)-1H-indole-2-carboxylate (see Intermediate 5, 30.3 g, 60.6 mmol) and {4-bromo-1-methyl-3-[(tetrahydro-2H-pyran-2-yloxy)methyl]-1H-pyrazol-5-yl}methanol (18.5 g, 60.6 mmol) in dioxane (780 ml) was added an aqueous 2 M solution of potassium carbonate (91 ml, 2.0 M, 180 mmol). The mixture was degassed and purged with argon several times. Pd(dppf)Cl$_2$×CH$_2$Cl$_2$ (9.90 g, 12.1 mmol) was added and the mixture was purged with argon for 10 minutes. The reaction mixture was stirred at 80° C. for 5 hours. For work-up, the reaction mixture was poured into water and the mixture was extracted four times with ethyl acetate. The combined organic phases were washed with brine and dried over sodium sulfate. After filtration and removal of the solvents the crude product was purified by flash chromatography (dichloromethane/acetone gradient, 10%→55% acetone) to give the title compound (27.7 g).

LC-MS (Method 1): Rt=1.57 min; MS (ESIpos): m/z=598 [M+H]$^+$

Intermediate 249

(rac)-ethyl 1-{3-[(tert-butoxycarbonyl)(methyl)amino]propyl}-7-{5-(hydroxymethyl)-1-methyl-3-[(tetrahydro-2H-pyran-2-yloxy)methyl]-1H-pyrazol-4-yl}-3-[3-(naphthalen-1-yloxy)propyl]-1H-indole-2-carboxylate

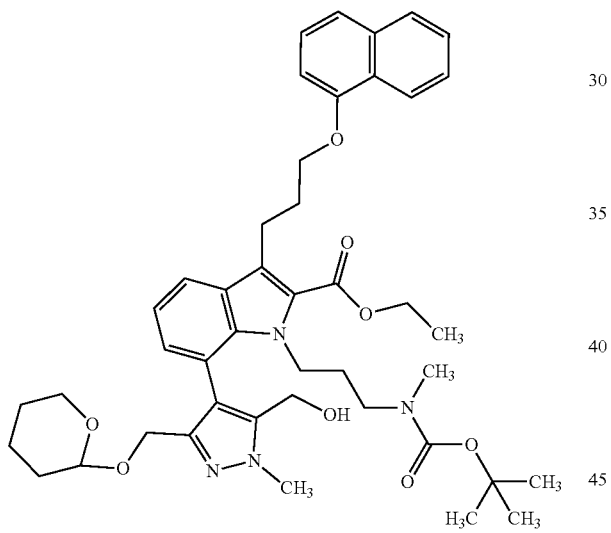

To a solution of (rac)-ethyl 7-{5-(hydroxymethyl)-1-methyl-3-[(tetrahydro-2H-pyran-2-yloxy)methyl]-1H-pyrazol-4-yl}-3-[3-(naphthalen-1-yloxy)propyl]-1H-indole-2-carboxylate (5.00 g, 8.37 mmol) in DMF (110 ml) was added caesium carbonate (13.6 g, 41.8 mmol) and the mixture was stirred for 10 min at room temperature. tert-Butyl (3-bromopropyl)methylcarbamate (see Intermediate 1, 2.53 g, 10.0 mmol) was added and the reaction mixture was stirred for 4 days at room temperature. For work-up, the reaction was poured into water. The mixture was extracted with ethyl acetate. The combined organic phases were washed with brine and dried over sodium sulfate. After filtration and removal of the solvent the crude product was purified by flash chromatography (dichloromethane/methanol gradient, 0%→10% methanol) to give the title compound (4.4 g).

Intermediate 250 ethyl 7-[5-(bromomethyl)-3-(hydroxymethyl)-1-methyl-1H-pyrazol-4-yl]-1-[3-(methylamino)propyl]-3-[3-(naphthalen-1-yloxy)propyl]-1H-indole-2-carboxylate hydrochloric acid salt

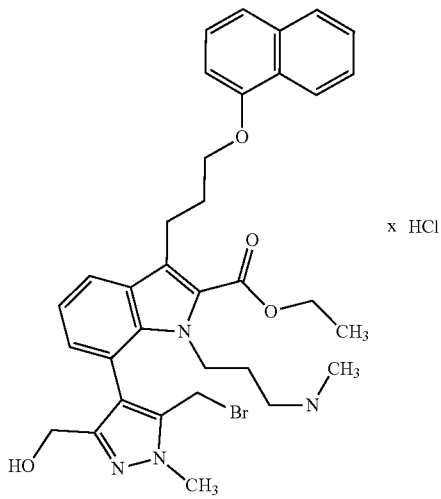 [SMILES: CCOC(=O)c1c(CCCOc2cccc3ccccc23)c2cccc(-c3c(CO)nn(C)c3CBr)c2n1CCCNC ; Cl]

Step 1: To a solution of (rac)-ethyl 1-{3-[(tert-butoxycarbonyl)(methyl)amino]propyl}-7-{5-(hydroxymethyl)-1-methyl-3-[(tetrahydro-2H-pyran-2-yloxy)methyl]-1H-pyrazol-4-yl}-3-[3-(naphthalen-1-yloxy)propyl]-1H-indole-2-carboxylate (4.36 g, 5.67 mmol) in dichloromethane (100 ml), triphenylphosphine (3.57 g, 13.6 mmol) was added at 0° C. and the mixture was stirred at 0° C. for 10 min. Tetrabromomethane (4.14 g, 12.5 mmol) was added and the reaction was stirred at 0° C. for 3 hours.

Step 2: To the solution obtained from Step 1 was added a 4 M solution of hydrogen chloride in dioxane (99 ml, 4.0 M, 400 mmol) at 0° C. and the mixture was stirred for 1 h at room temperature. For work-up the mixture was concentrated under reduced pressure and the crude product was used for the subsequent steps without further purification.

Intermediate 251

(rac)-ethyl 11-(hydroxymethyl)-7,9-dimethyl-1-[3-(naphthalen-1-yloxy)propyl]-4,5,6,7,8,9-hexahydro-pyrazolo[3',4':7,8][1,5]diazecino[9,10,1-hi]indole-2-carboxylate

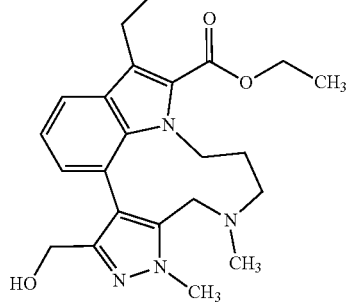

To a solution of ethyl 7-[5-(bromomethyl)-3-(hydroxymethyl)-1-methyl-1H-pyrazol-4-yl]-1-[3-(methylamino)propyl]-3-[3-(naphthalen-1-yloxy)propyl]-1H-indole-2-carboxylate hydrochloric acid salt (3.88 g) in DMF (350 ml) was added caesium carbonate (9.24 g, 28.4 mmol) and the reaction was stirred at 65° C. for 17 hours. For work-up the mixture was concentrated under reduced pressure and the residue was purified by flash chromatography (dichloromethane/methanol gradient, 2%→10% methanol) to give the title compound (600 mg).

LC-MS (Method 2): Rt=1.59 min; MS (ESIpos): m/z=567 [M+H]$^+$ $^1$H-NMR (400 MHz, DMSO-d6) δ [ppm]: 1.132 (1.15), 1.150 (2.41), 1.168 (1.31), 1.209 (0.57), 1.218 (0.87), 1.230 (5.08), 1.236 (1.65), 1.247 (10.92), 1.253 (1.26), 1.265 (5.17), 1.468 (0.51), 1.571 (0.46), 1.799 (0.48), 1.819 (0.48), 1.832 (0.53), 1.853 (0.44), 1.965 (4.19), 2.142 (10.32), 2.157 (1.38), 2.174 (1.70), 2.191 (1.19), 2.295 (0.71), 2.300 (1.10), 2.304 (1.59), 2.309 (1.24), 2.321 (0.50), 2.342 (0.41), 2.568 (0.51), 2.637 (0.42), 2.642 (0.81), 2.646 (1.10), 2.651 (0.80), 2.705 (2.02), 2.865 (2.42), 2.898 (1.40), 2.935 (1.43), 3.221 (0.58), 3.237 (0.73), 3.255 (1.04), 3.274 (0.57), 3.320 (1.29), 3.338 (0.67), 3.353 (0.64), 3.565 (1.47), 3.600 (1.35), 3.795 (0.48), 3.804 (0.60), 3.824 (16.00), 3.840 (0.88), 3.855 (0.65), 3.865 (0.51), 3.995 (0.99), 4.013 (0.94), 4.031 (0.41), 4.081 (0.92), 4.093 (1.03), 4.110 (1.86), 4.123 (1.86), 4.147 (1.93), 4.161 (2.25), 4.169 (1.65), 4.176 (2.42), 4.188 (3.49), 4.195 (3.13), 4.201 (2.11), 4.204 (2.11), 4.213 (2.57), 4.219 (2.42), 4.231 (1.06), 4.237 (2.12), 4.245 (0.96), 4.254 (0.74), 4.263 (0.88), 4.315 (0.50), 4.326 (0.90), 4.338 (0.55), 4.351 (0.57), 4.363 (0.83), 4.645 (1.66), 4.659 (2.39), 4.672 (1.49), 6.868 (0.44), 6.876 (1.73), 6.893 (1.89), 6.929 (1.58), 6.932 (1.70), 6.947 (2.64), 6.950 (2.41), 6.989 (2.25), 7.009 (2.34), 7.027 (1.38), 7.351 (1.43), 7.371 (2.62), 7.390 (2.18), 7.430 (2.69), 7.450 (1.54), 7.470 (0.44), 7.475 (0.71), 7.487 (1.86), 7.493 (2.80), 7.502 (3.79), 7.511 (3.20), 7.517 (2.21), 7.524 (0.80), 7.529 (1.10), 7.532 (0.76), 7.542 (0.67), 7.550 (0.64), 7.569 (0.42), 7.573 (0.74), 7.590 (0.73), 7.599 (0.81), 7.603 (0.85), 7.607 (0.58), 7.610 (0.57), 7.615 (0.44), 7.619 (0.57), 7.623 (0.58), 7.679 (0.42), 7.684 (1.79), 7.688 (1.93), 7.696 (0.55), 7.705 (1.81), 7.708 (1.77), 7.718 (0.50), 7.839 (1.63), 7.842 (1.24), 7.849 (0.88), 7.855 (1.10), 7.857 (1.13), 7.863 (1.35), 8.194 (1.31), 8.201 (1.10), 8.208 (0.71), 8.218 (1.31).

Intermediate 252

(rac)-ethyl 11-(bromomethyl)-7,9-dimethyl-1-[3-(naphthalen-1-yloxy)propyl]-4,5,6,7,8,9-hexahydro-pyrazolo[3',4':7,8][1,5]diazecino[9,10,1-hi]indole-2-carboxylate

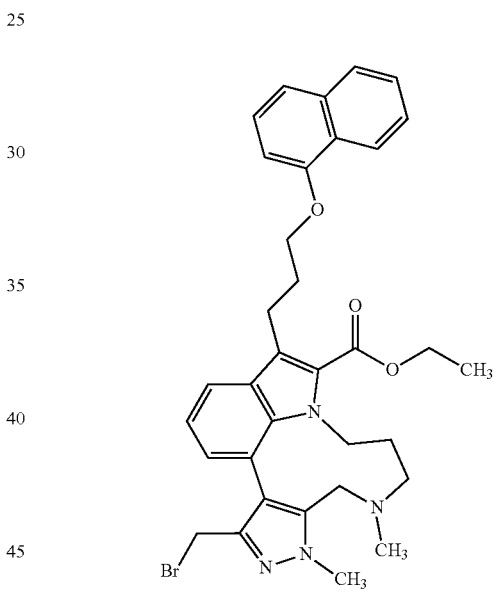

To a solution of (rac)-ethyl 11-(hydroxymethyl)-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylate (250 mg, 441 μmol) in dichloromethane (8.1 ml), triphenylphosphine (278 mg, 1.06 mmol) was added at 0° C. and the mixture was stirred at 0° C. for 10 min. Tetrabromomethane (351 mg, 1.06 mmol) was added and the reaction was stirred for 4 hours. For work-up, the reaction was concentrated under reduced pressure and the crude product was purified by flash chromatography (dichloromethane/acetone gradient, 10%→50% acetone) to give the title compound (122 mg).

LC-MS (Method 2): Rt=1.83 min; MS (ESIpos): m/z=629 [M+H]$^+$

Intermediate 253

(rac)-ethyl 7,9-dimethyl-1-[3-(naphthalen-1-yloxy)propyl]-11-{[(2,2,2-trifluoroethyl)amino]methyl}-4,5,6,7,8,9-hexahydropyrazolo[3',4':7,8][1,5]diazecino[9,10,1-hi]indole-2-carboxylate

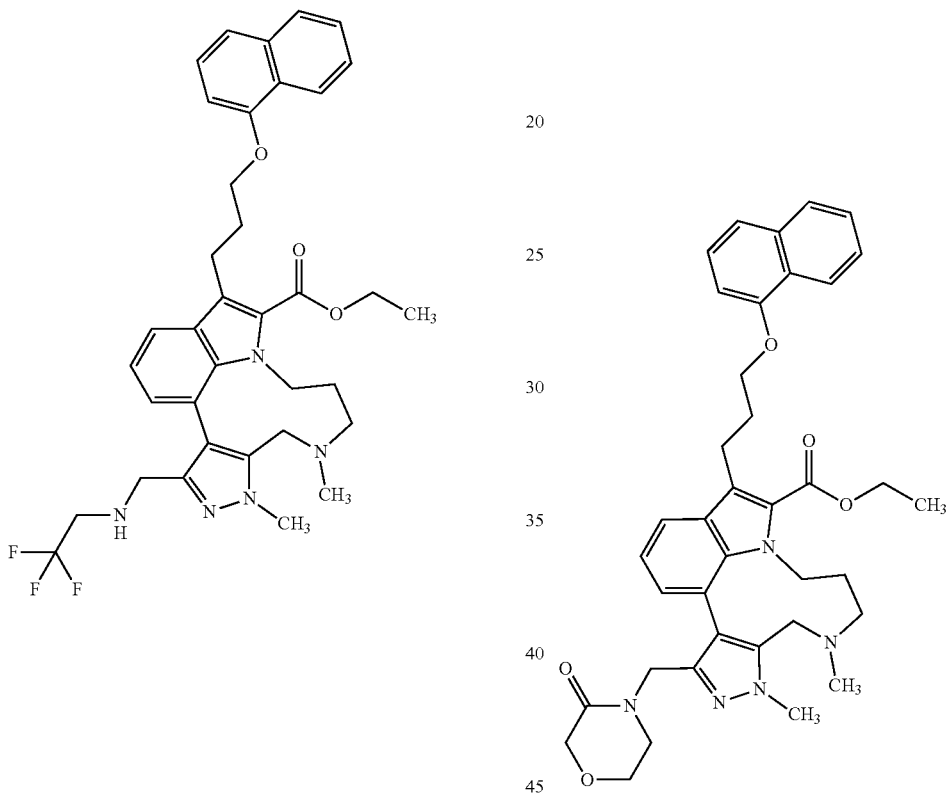

A mixture of (rac)-ethyl 11-(bromomethyl)-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylate (231 mg, 366 µmol) and 2,2,2-trifluoroethanamine (120 µl, 98% purity, 1.5 mmol) in THF (2.1 ml) was stirred at 45° C. for 3 hours. For work-up, the mixture was concentrated and the residue was purified by flash chromatography (dichloromethane/acetone gradient, 0%→50% acetone) to give the title compound (160 mg).

LC-MS (Method 2): $R_t$=1.75 min; MS (ESIpos): m/z=648 [M+H]$^+$ $^1$H-NMR (400 MHz, DMSO-d6) δ [ppm]: 0.833 (0.58), 0.851 (1.02), 1.137 (3.01), 1.232 (6.29), 1.269 (8.33), 1.286 (16.00), 1.304 (7.80), 1.907 (1.99), 1.926 (2.04), 2.115 (1.46), 2.187 (2.70), 2.203 (3.63), 2.220 (2.57), 2.322 (2.13), 2.327 (2.75), 2.331 (1.99), 2.518 (11.48), 2.522 (7.53), 2.665 (2.13), 2.669 (2.66), 2.673 (1.95), 2.953 (6.56), 2.964 (6.29), 3.087 (2.26), 3.110 (2.17), 3.430 (4.03), 3.770 (1.33), 3.794 (1.02), 3.808 (0.84), 4.013 (15.73), 4.049 (1.42), 4.072 (1.15), 4.220 (3.63), 4.234 (6.03), 4.251 (4.96), 4.264 (4.57), 4.281 (3.55), 4.299 (1.15), 4.308 (0.93), 4.533 (1.37), 4.563 (2.75), 4.600 (1.73), 5.759 (1.51), 6.911 (3.10), 6.929 (3.01), 7.040 (2.48), 7.056 (3.19), 7.133 (2.04), 7.152 (2.79), 7.171 (1.42), 7.384 (1.91), 7.405 (3.77), 7.424 (2.70), 7.463 (5.01), 7.484 (2.84), 7.505 (1.33), 7.517 (3.50), 7.523 (4.83), 7.533 (6.16), 7.542 (5.10), 7.547 (3.37), 7.560 (1.15), 7.852 (2.88), 7.872 (5.50), 7.890 (2.57), 7.896 (2.48), 8.225 (2.88), 8.232 (2.53), 8.249 (2.66), 9.500 (1.02).

Intermediate 254

(rac)-ethyl 7,9-dimethyl-1-[3-(naphthalen-1-yloxy)propyl]-11-[(3-oxomorpholin-4-yl)methyl]-4,5,6,7,8,9-hexahydropyrazolo[3',4':7,8][1,5]diazecino[9,10,1-hi]indole-2-carboxylate To a solution of morpholin-3-one (19.5 mg, 193 µmol) in THF (1.1 ml) was added sodium hydride (7.75 mg, 60% purity, 194 µmol) and the mixture was stirred for 90 min at room temperature. A cooled solution of (rac)-ethyl 11-(bromomethyl)-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylate (122 mg, 194 µmol) in THF (1.1 ml) was added and the reaction mixture was stirred for 3 days at room temperature. For work-up, water was added to the reaction mixture. The mixture was concentrated under reduced pressure and the crude product was purified by flash chromatography (dichloromethane/methanol gradient, 0%→10% methanol) to give the title compound (120 mg).

LC-MS (Method 2): Rt=1.73 min; MS (ESIpos): m/z=650 [M+H]$^+$

Intermediate 255 ethyl (11Z)-1-methyl-7-[3-(naphthalen-1-yloxy)propyl]-3-[(tetrahydro-2H-pyran-2-yloxy)methyl]-1,10,13,15-tetrahydropyrazolo[4',3':9,10][1,6]oxazacycloundecino[8,7,6-hi]indole-8-carboxylate (Mixture of Stereoisomers)

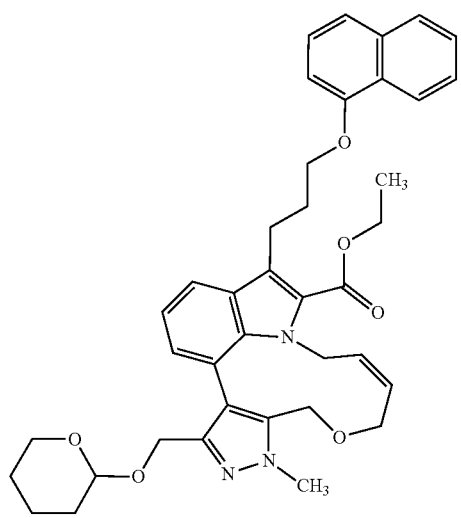 [SMILES: CCOC(=O)c1c(CCCOc2cccc3ccccc23)c2cccc3c2n1C/C=C\COCc1c-3c(COC2CCCCO2)nn1C]

To a solution of (rac)-ethyl 7-{5-(hydroxymethyl)-1-methyl-3-[(tetrahydro-2H-pyran-2-yloxy)methyl]-1H-pyrazol-4-yl}-3-[3-(naphthalen-1-yloxy)propyl]-1H-indole-2-carboxylate (see Intermediate 248, 23.0 g, 38.5 mmol) in acetonitrile (300 ml) was added caesium carbonate (62.7 g, 192 mmol) and the mixture was stirred for 10 min at room temperature. (2Z)-1,4-dichlorobut-2-ene (4.0 ml, 38 mmol) and sodium iodide (11.5 g, 77.0 mmol) were added and the reaction mixture was stirred for 18 hours at 35° C. and for 2 hours at 50° C. For work-up the reaction mixture was cooled down to room temperature and water (20 ml) was added. The precipitate was filtered off and the residue was washed with dichloromethane. The filtrate was concentrated under reduced pressure and the crude product was purified by flash chromatography (dichloromethane/acetone gradient, 0%→20% acetone) to give the title compound (13.4 g).

$^1$H-NMR (400 MHz, DMSO-d6) δ [ppm]: 0.934 (0.41), 0.956 (0.48), 0.993 (0.44), 1.002 (0.41), 1.025 (0.51), 1.066 (0.80), 1.132 (1.38), 1.145 (1.33), 1.154 (1.72), 1.177 (1.31), 1.185 (1.26), 1.204 (0.87), 1.216 (0.92), 1.255 (5.70), 1.258 (6.04), 1.273 (12.32), 1.276 (12.48), 1.290 (6.79), 1.293 (6.67), 1.316 (0.70), 1.345 (0.58), 1.357 (0.53), 1.373 (0.44), 1.723 (0.65), 2.084 (11.05), 2.172 (0.99), 2.188 (1.94), 2.204 (2.06), 2.221 (1.16), 2.336 (0.44), 2.456 (0.73), 2.518 (5.87), 2.522 (3.76), 2.678 (0.46), 2.765 (0.65), 2.791 (0.53), 2.888 (0.53), 2.898 (0.95), 2.910 (0.92), 2.933 (0.68), 2.940 (0.65), 3.252 (0.61), 3.265 (0.99), 3.285 (1.02), 3.298 (1.02), 3.361 (0.41), 3.370 (0.61), 3.378 (1.02), 3.383 (0.95), 3.396 (1.24), 3.411 (0.99), 3.429 (0.75), 3.492 (0.61), 3.522 (1.21), 3.551 (1.21), 3.580 (0.65), 3.773 (0.63), 3.785 (0.80), 3.806 (1.19), 3.824 (2.72), 3.838 (0.58), 3.852 (2.52), 3.857 (0.92), 3.916 (16.00), 3.922 (15.01), 3.944 (1.04), 3.950 (2.38), 3.960 (1.02), 3.977 (2.96), 3.990 (2.86), 4.017 (0.90), 4.180 (2.55), 4.194 (1.36), 4.200 (1.33), 4.208 (4.46), 4.218 (4.24), 4.228 (4.32), 4.236 (2.72), 4.245 (4.02), 4.254 (2.50), 4.263 (4.02), 4.276 (0.82), 4.283 (2.06), 4.294 (1.89), 4.301 (1.75), 4.311 (1.96), 4.321 (1.07), 4.328 (1.16), 4.333 (0.53), 4.338 (1.67), 4.346 (2.30), 4.359 (0.41), 4.689 (0.51), 4.717 (0.65), 4.729 (2.79), 4.733 (2.67), 4.763 (2.16), 4.767 (2.16), 4.787 (0.48), 4.814 (0.53), 4.827 (0.63), 4.854 (0.63), 4.977 (0.92), 4.990 (1.04), 5.017 (1.16), 5.031 (0.85), 5.052 (0.51), 5.074 (1.45), 5.101 (0.48), 5.204 (0.80), 5.220 (0.68), 5.228 (0.68), 5.759 (1.48), 6.834 (1.60), 6.837 (1.79), 6.852 (1.94), 6.855 (2.18), 6.857 (2.21), 6.860 (1.96), 6.874 (2.04), 6.878 (2.01), 6.892 (1.60), 6.911 (3.05), 6.928 (1.58), 7.064 (1.92), 7.069 (1.84), 7.082 (1.96), 7.084 (2.38), 7.086 (2.18), 7.088 (2.08), 7.102 (1.62), 7.107 (1.58), 7.374 (1.33), 7.384 (1.28), 7.394 (2.40), 7.404 (2.21), 7.413 (2.06), 7.423 (1.92), 7.456 (2.72), 7.474 (1.53), 7.489 (0.44), 7.493 (0.85), 7.498 (0.63), 7.506 (1.60), 7.510 (2.81), 7.514 (2.67), 7.521 (3.76), 7.525 (3.56), 7.530 (2.25), 7.534 (3.08), 7.537 (2.40), 7.540 (1.89), 7.550 (0.75), 7.553 (0.73), 7.765 (1.70), 7.768 (1.92), 7.776 (1.77), 7.778 (1.87), 7.785 (1.77), 7.788 (1.70), 7.796 (1.65), 7.799 (1.58), 7.865 (2.28), 7.868 (1.48), 7.875 (0.85), 7.880 (1.67), 7.884 (1.72), 8.211 (1.33), 8.218 (1.99), 8.226 (1.41), 8.235 (1.48), 8.243 (1.16).

Intermediate 256

(rac)-ethyl (11Z)-3-(hydroxymethyl)-1-methyl-7-[3-(naphthalen-1-yloxy)propyl]-1,10,13,15-tetrahydropyrazolo[4',3':9,10][1,6]oxazacycloundecino[8,7,6-hi]indole-8-carboxylate

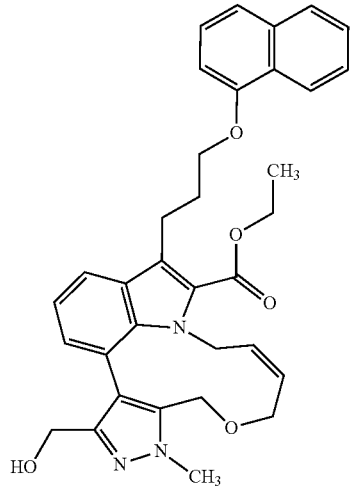 [SMILES: CCOC(=O)c1c(CCCOc2cccc3ccccc23)c2cccc3c2n1C/C=C\COCc1c-3c(CO)nn1C]

A mixture of ethyl (11Z)-1-methyl-7-[3-(naphthalen-1-yloxy)propyl]-3-[(tetrahydro-2H-pyran-2-yloxy)methyl]-1,10,13,15-tetrahydropyrazolo[4',3':9,10][1,6]oxazacycloundecino[8,7,6-hi]indole-8-carboxylate (mixture of stereoisomers; 13.7 g, 21.1 mmol) and p-toluenesulfonic acid (3.64 g, 21.1 mmol) in ethanol (430 ml) was stirred for 19 hours at room temperature. For work-up, the mixture was concentrated under reduced pressure and the residue was purified by flash chromatography (Biotage SNAP cartridge NH$_2$ silica, dichloromethane/ethanol gradient, 0%→10% ethanol) to give the title compound (12.4 g).

LC-MS (Method 2): Rt=1.55 min; MS (ESIpos): m/z=566 [M+H]$^+$ $^1$H-NMR (400 MHz, DMSO-d6) δ [ppm]: 1.101 (2.10), 1.118 (4.35), 1.136 (2.23), 1.265 (4.86), 1.272 (0.73), 1.282 (10.74), 1.300 (4.97), 1.434 (0.70), 1.443 (0.82), 1.453 (0.52), 1.462 (0.42), 1.723 (0.45), 2.227 (0.84), 2.245 (1.18), 2.261 (0.88), 2.518 (1.43), 2.522 (0.97), 3.304 (0.68), 3.354 (1.30), 3.361 (0.53), 3.372 (1.03), 3.379 (0.84), 3.385 (0.54), 3.390 (0.47), 3.396 (0.80), 3.473 (0.66), 3.503 (1.14), 3.533 (0.78), 3.639 (0.60), 3.657 (0.60), 3.664 (0.53), 3.681 (0.52), 3.767 (0.72), 3.778 (0.80), 3.799 (0.68), 3.811 (0.60), 3.904 (16.00), 3.916 (0.67), 3.923 (0.52), 3.971 (2.66), 3.975 (2.70), 3.984 (2.69), 3.988 (2.65), 4.168 (1.85), 4.203 (2.27), 4.220 (1.05), 4.230 (0.74), 4.238 (1.30), 4.247 (2.69), 4.259 (3.06), 4.265 (2.81), 4.274 (1.49), 4.286 (2.07), 4.303 (1.74), 4.313 (0.90), 4.321 (0.54), 4.330 (0.87), 4.536 (0.58), 4.548 (0.40), 4.593 (1.76), 4.605 (3.87), 4.619 (1.62), 4.702 (2.08), 4.736 (2.38), 4.762 (0.68), 4.775 (0.76), 4.801 (0.90), 4.939 (1.00), 4.983 (1.37), 5.011 (1.00), 5.037 (0.57), 5.170 (0.42), 5.186 (0.65), 5.197 (0.62), 5.758 (1.14), 6.834 (1.93), 6.837 (1.97), 6.852 (2.23), 6.855 (2.11), 6.934 (1.75), 6.951 (1.86), 7.070 (1.86), 7.088 (2.09), 7.090 (2.25), 7.108 (1.67), 7.386 (1.27), 7.407 (2.52), 7.426 (2.10), 7.459 (2.69), 7.479 (1.41), 7.488 (0.42), 7.493 (0.61), 7.505 (1.57), 7.510 (1.51), 7.514 (1.79), 7.523 (3.42), 7.530 (1.82), 7.534 (1.65), 7.538 (1.74), 7.551 (0.66), 7.764 (1.92), 7.767 (1.98), 7.785 (1.85), 7.787 (1.77), 7.864 (1.57), 7.873 (0.82), 7.882 (1.41), 7.888 (1.31), 8.213 (1.34), 8.219 (1.29), 8.230 (0.68), 8.237 (1.27).

Intermediate 257

(rac)-ethyl 3-(hydroxymethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate

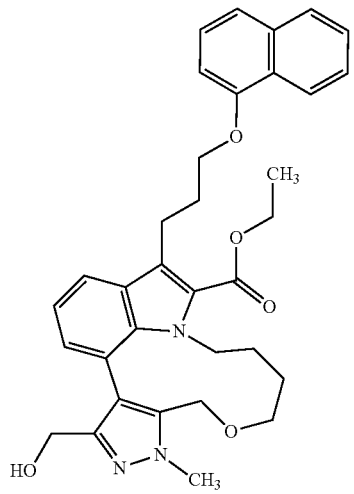 [SMILES: CCOC(=O)c1c(CCCOc2cccc3ccccc23)c2cccc3c2n1CCCCOCc1c-3c(CO)nn1C]

A suspension of (rac)-ethyl (11Z)-3-(hydroxymethyl)-1-methyl-7-[3-(naphthalen-1-yloxy)propyl]-1,10,13,15-tetrahydropyrazolo[4',3':9,10][1,6]oxazacycloundecino[8,7,6-hi]indole-8-carboxylate (1.18 g, 2.09 mmol) and Pd/C (118 mg) in ethanol (36 ml) was stirred under an atmosphere of hydrogen at room temperature for 16 hours. For work-up the mixture was filtered through a pad of celite. The residue was washed with ethyl acetate and the filtrate was concentrated under reduced pressure. The residue was purified by flash chromatography (dichloromethane/acetone gradient, 0%→30% acetone) to give the title compound (1 g).

LC-MS (Method 1): R$_t$=1.58 min; MS (ESIpos): m/z=568 [M+H]$^+$ $^1$H-NMR (400 MHz, DMSO-d6) δ [ppm]: 1.014 (0.89), 1.030 (0.79), 1.229 (0.53), 1.258 (3.29), 1.275 (7.14), 1.284 (0.94), 1.293 (3.49), 1.302 (0.94), 1.320 (0.44), 2.084 (16.00), 2.214 (0.70), 2.327 (0.40), 2.518 (2.86), 2.522 (1.88), 2.669 (0.46), 2.771 (0.48), 2.800 (0.51), 3.261 (0.42), 3.278 (0.52), 3.355 (0.59), 3.416 (0.55), 3.428 (0.41), 3.446 (0.52), 3.880 (11.52), 4.059 (1.67), 4.066 (1.75), 4.073 (1.96), 4.078 (1.86), 4.096 (0.48), 4.108 (0.49), 4.119 (0.52), 4.197 (0.70), 4.212 (1.54), 4.214 (1.55), 4.224 (1.89), 4.241 (2.37), 4.246 (2.04), 4.255 (1.19), 4.259 (0.91), 4.272 (1.22), 4.290 (1.09), 4.299 (0.63), 4.317 (0.62), 4.399 (0.62), 4.435 (0.51), 4.640 (1.37), 4.672 (1.94), 4.684 (2.20), 4.698 (1.10), 5.759 (0.68), 6.860 (1.24), 6.863 (1.41), 6.877 (1.53), 6.880 (1.53), 6.919 (1.18), 6.936 (1.23), 7.041 (1.21), 7.058 (1.25), 7.060 (1.52), 7.078 (1.06), 7.381 (0.86), 7.401 (1.64), 7.420 (1.32), 7.457 (1.74), 7.478 (0.96), 7.514 (1.07), 7.519 (1.94), 7.528 (2.15), 7.538 (1.97), 7.542 (1.23), 7.554 (0.40), 7.758 (1.20), 7.761 (1.30), 7.778 (1.15), 7.781 (1.18), 7.865 (0.96), 7.869 (0.72), 7.876 (0.51), 7.880 (0.59), 7.883 (0.66), 7.889 (0.84), 8.232 (0.84), 8.240 (0.61), 8.256 (0.81).

Intermediate 258

(rac)-ethyl 3-(bromomethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate

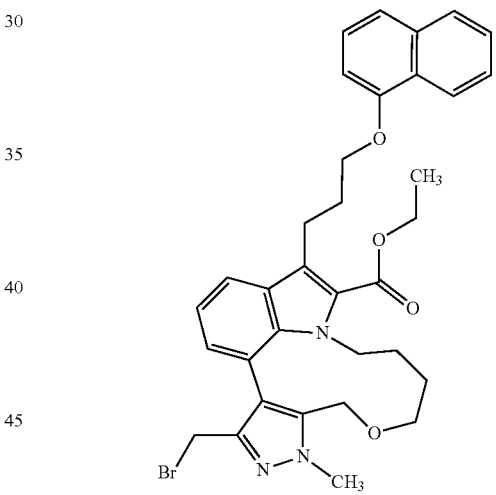

To a solution of (rac)-ethyl 3-(hydroxymethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (1.01 g, 1.78 mmol) in dichloromethane (33 ml), triphenylphosphine (700 mg, 2.67 mmol) was added at 0° C. and the mixture was stirred at 0° C. for 10 min. Tetrabromomethane (885 mg, 2.67 mmol) was added and the reaction mixture was stirred for 3 hours at room temperature. Additional portions of triphenylphosphine (140 mg, 0.53 mmol) and tetrabromomethane (177 mg, 0.53 mmol) were added and the mixture was stirred for 1.5 hours at room temperature. For work-up the reaction mixture was concentrated under reduced pressure and the crude product was purified by flash chromatography (hexane/ethyl acetate gradient, 0%→75% ethyl acetate) to give the title compound (755 mg).

LC-MS (Method 1): Rt=1.71 min; MS (ESIpos): m/z=630 [M+H]$^+$

¹H-NMR (400 MHz, DMSO-d6) δ [ppm]: 1.035 (1.37), 1.047 (1.24), 1.154 (2.01), 1.172 (4.15), 1.190 (2.11), 1.231 (0.68), 1.262 (5.23), 1.271 (1.89), 1.279 (11.13), 1.289 (2.57), 1.297 (5.80), 1.307 (1.28), 1.988 (7.26), 2.221 (1.08), 2.235 (1.07), 2.518 (2.60), 2.523 (1.74), 2.860 (0.81), 2.872 (0.54), 2.889 (0.79), 3.260 (0.44), 3.276 (0.64), 3.294 (0.83), 3.314 (0.57), 3.353 (1.00), 3.371 (0.63), 3.387 (0.47), 3.449 (0.82), 3.464 (0.75), 3.478 (0.82), 3.918 (16.00), 3.948 (0.47), 3.962 (2.13), 3.982 (0.73), 3.999 (1.13), 4.017 (2.06), 4.035 (1.67), 4.053 (0.57), 4.187 (7.58), 4.204 (1.45), 4.213 (1.54), 4.222 (2.24), 4.228 (4.01), 4.248 (2.66), 4.262 (2.44), 4.274 (0.50), 4.282 (1.82), 4.292 (0.60), 4.299 (1.64), 4.309 (0.95), 4.317 (0.56), 4.327 (1.08), 4.420 (0.48), 4.431 (0.90), 4.443 (0.50), 4.456 (0.43), 4.467 (0.79), 4.643 (2.08), 4.676 (1.84), 6.900 (1.96), 6.908 (1.96), 6.911 (2.19), 6.919 (2.16), 6.926 (2.34), 6.929 (2.26), 7.081 (1.78), 7.101 (2.26), 7.119 (1.55), 7.372 (1.25), 7.393 (2.47), 7.403 (0.42), 7.412 (1.98), 7.452 (2.63), 7.464 (0.42), 7.473 (1.48), 7.495 (0.57), 7.508 (1.49), 7.512 (1.53), 7.516 (2.03), 7.524 (3.49), 7.532 (2.28), 7.540 (1.86), 7.552 (0.60), 7.811 (1.81), 7.814 (1.93), 7.832 (1.78), 7.835 (1.73), 7.863 (1.61), 7.871 (0.94), 7.880 (1.33), 7.886 (1.31), 8.222 (1.39), 8.228 (1.28), 8.237 (0.68), 8.246 (1.35).

Intermediate 259

(rac)-ethyl 3-[(ethylamino)methyl]-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate

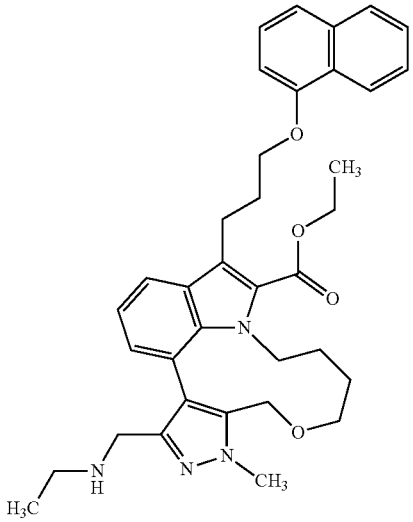

To a solution of ethanamine (790 μl, 2.0 M, 1.6 mmol) in THF (1.3 ml) was added (rac)-ethyl 3-(bromomethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (250 mg, 396 μmol) and the reaction mixture was stirred for 3 hours at room temperature. For work-up the reaction mixture was concentrated under reduced pressure and the crude product was purified by flash chromatography (dichlormethane/methanol gradient, 0%→10% methanol) to give the title compound (233 mg).

LC-MS (Method 2): $R_t$=1.67 min; MS (ESIpos): m/z=595 [M+H]⁺

¹H-NMR (400 MHz, DMSO-d6) δ [ppm]: 0.809 (3.03), 0.827 (6.16), 0.845 (3.10), 0.963 (0.52), 1.041 (1.24), 1.154 (0.72), 1.172 (1.34), 1.190 (0.79), 1.232 (4.06), 1.241 (3.03), 1.244 (2.75), 1.260 (6.92), 1.277 (12.25), 1.295 (5.54), 1.758 (0.93), 1.988 (2.17), 2.178 (0.52), 2.199 (1.03), 2.214 (1.41), 2.233 (1.00), 2.336 (0.65), 2.438 (0.96), 2.456 (1.55), 2.518 (6.85), 2.523 (4.71), 2.678 (0.69), 2.834 (0.83), 2.846 (0.55), 2.863 (0.79), 3.251 (0.58), 3.268 (0.69), 3.285 (1.03), 3.346 (1.93), 3.381 (2.34), 3.429 (2.24), 3.443 (0.93), 3.459 (1.17), 3.599 (0.79), 3.779 (1.24), 3.905 (16.00), 4.007 (0.69), 4.018 (0.72), 4.025 (0.72), 4.035 (0.69), 4.042 (0.76), 4.198 (1.31), 4.205 (2.24), 4.213 (2.41), 4.222 (2.06), 4.231 (2.34), 4.239 (0.72), 4.249 (2.06), 4.260 (2.34), 4.267 (1.03), 4.277 (2.13), 4.295 (3.89), 4.304 (1.17), 4.312 (0.72), 4.322 (1.03), 4.403 (0.89), 4.416 (0.48), 4.427 (0.45), 4.439 (0.79), 4.647 (2.13), 4.681 (1.89), 5.760 (0.52), 6.885 (2.00), 6.904 (3.92), 6.921 (2.34), 6.924 (2.41), 7.070 (2.00), 7.089 (2.34), 7.108 (1.65), 7.369 (1.48), 7.389 (2.75), 7.408 (2.20), 7.453 (2.99), 7.474 (1.69), 7.493 (0.48), 7.498 (0.72), 7.511 (1.86), 7.517 (2.44), 7.526 (3.85), 7.535 (2.41), 7.542 (2.00), 7.554 (0.65), 7.789 (1.89), 7.792 (2.06), 7.809 (1.86), 7.812 (1.79), 7.864 (1.69), 7.873 (1.00), 7.881 (1.27), 7.887 (1.38), 8.220 (1.51), 8.227 (1.31), 8.236 (0.76), 8.244 (1.34).

Intermediate 260 ethyl 4-bromo-1-methyl-3-(morpholin-4-ylmethyl)-1H-pyrazole-5-carboxylate

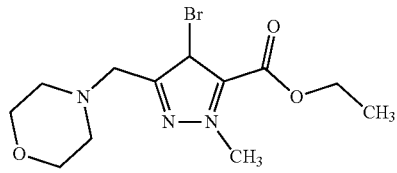

To a solution of morpholine (3.4 ml, 39 mmol) in acetonitrile (77 ml) was added potassium carbonate (5.34 g, 38.7 mmol) and the mixture was stirred for 10 min at room temperature. Ethyl 4-bromo-3-(bromomethyl)-1-methyl-1H-pyrazole-5-carboxylate (see Intermediate 6; 6.00 g, 18.4 mmol) was added and the reaction mixture was stirred for 3 hours at room temperature. For work-up, the reaction mixture was poured into aqueous sodium chloride solution. The precipitate formed was collected by filtration, washed with water and dried to give the title compound (5.20 g).

LC-MS (Method 2): $R_t$=1.04 min; MS (ESIpos): m/z=332 [M+H]⁺

Intermediate 261

[4-bromo-1-methyl-3-(morpholin-4-ylmethyl)-1H-pyrazol-5-yl]methanol

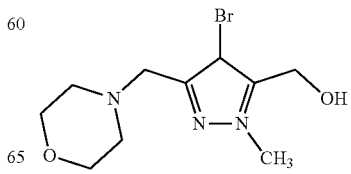

To a solution of ethyl 4-bromo-1-methyl-3-(morpholin-4-ylmethyl)-1H-pyrazole-5-carboxylate (5.20 g, 15.7 mmol) in THF (120 ml) was added a solution of lithium aluminium hydride in THF (7.8 ml, 2.0 M, 16 mmol) at −10° C. The reaction mixture was stirred at −10° C. for one hour. For work-up, water (0.8 ml) was added dropwise, followed by the addition of an aqueous 2 M sodium hydroxide solution (0.8 ml) and water (0.8 ml). The mixture was filtered through a pad of celite. The residue was washed with ethyl acetate and the filtrate was concentrated under reduced pressure. The resulting precipitate was filtered and washed with ethyl acetate to give the title compound (4.1 g).

LC-MS (Method 2): Rt=0.66 min; MS (ESIpos): m/z=290 [M+H]$^+$

Intermediate 262 ethyl 7-[5-(hydroxymethyl)-1-methyl-3-(morpholin-4-ylmethyl)-1H-pyrazol-4-yl]-3-[3-(naphthalen-1-yloxy)propyl]-1H-indole-2-carboxylate

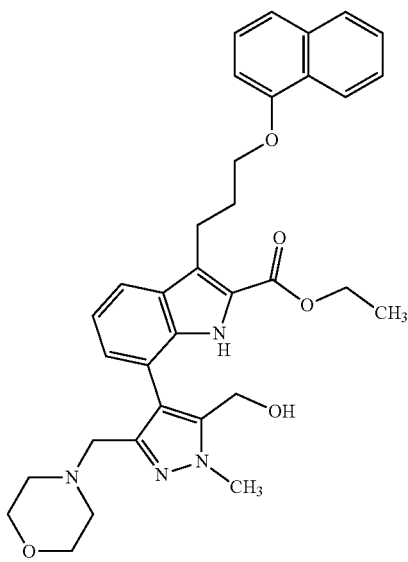

To a solution of ethyl 3-[3-(naphthalen-1-yloxy)propyl]-7-(4,4,5,5-tetramethyl-1,3,2-dioxaborolan-2-yl)-1H-indole-2-carboxylate (see Intermediate 5; 4.82 g, 9.65 mmol) and [4-bromo-1-methyl-3-(morpholin-4-ylmethyl)-1H-pyrazol-5-yl]methanol (2.80 g, 9.65 mmol) in 1,4-dioxane (120 ml) were added an aqueous 2M solution of potassium carbonate (14 ml, 2.0 M, 29 mmol). The mixture was degassed and purged with argon several times. Pd(dppf)Cl$_2$×CH$_2$Cl$_2$ (1.58 g, 1.93 mmol) was added and the mixture was purged with argon for 10 minutes. The reaction mixture was stirred at 80° C. for 3.5 h. After cooling the reaction mixture was filtered and the residue was washed with dichloromethane. The filtrate was concentrated under reduced pressure and the residue was purified by flash chromatography (dichloromethane/ethyl acetate gradient, 0%→100% ethyl acetate) to give the title compound (2.84 g).

$^1$H-NMR (400 MHz, DMSO-d6) δ [ppm]: 1.066 (8.09), 1.154 (3.97), 1.171 (7.72), 1.189 (3.62), 1.260 (5.07), 1.278 (11.28), 1.295 (5.18), 1.987 (14.71), 2.235 (1.38), 2.254 (1.08), 2.518 (1.87), 2.522 (1.27), 3.136 (2.94), 3.356 (1.77), 3.375 (1.12), 3.565 (0.87), 3.591 (2.36), 3.602 (3.91), 3.613 (2.30), 3.914 (16.00), 3.938 (1.47), 3.999 (1.06), 4.017 (3.16), 4.034 (3.06), 4.052 (0.97), 4.197 (1.39), 4.212 (2.82), 4.226 (1.42), 4.271 (1.35), 4.289 (1.33), 4.350 (1.64), 4.357 (1.69), 4.361 (1.65), 4.369 (1.04), 5.416 (0.91), 5.428 (2.24), 6.882 (1.65), 6.885 (1.72), 6.901 (1.89), 6.904 (1.77), 7.105 (1.54), 7.123 (2.21), 7.125 (2.00), 7.143 (1.90), 7.244 (2.12), 7.247 (2.30), 7.263 (1.80), 7.265 (1.68), 7.363 (1.37), 7.383 (2.58), 7.402 (2.19), 7.440 (2.58), 7.454 (0.90), 7.461 (1.50), 7.468 (1.49), 7.471 (1.67), 7.488 (1.55), 7.492 (1.39), 7.497 (1.41), 7.501 (1.58), 7.514 (0.82), 7.517 (1.59), 7.521 (1.59), 7.534 (0.86), 7.538 (0.72), 7.719 (1.77), 7.737 (1.66), 7.851 (1.53), 7.853 (1.67), 7.871 (1.61), 7.874 (1.40), 8.147 (1.47), 8.149 (1.54), 8.151 (1.48), 8.168 (1.35), 8.169 (1.44), 8.171 (1.36), 11.340 (2.54).

Intermediate 263 ethyl 7-{1-methyl-3-(morpholin-4-ylmethyl)-5-[(prop-2-en-1-yloxy)methyl]-1H-pyrazol-4-yl}-3-[3-(naphthalen-1-yloxy)propyl]-1-(prop-2-en-1-yl)-1H-indole-2-carboxylate

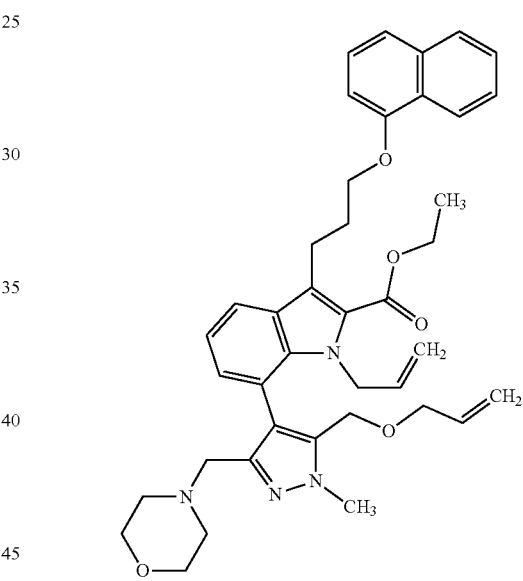

To a solution of ethyl 7-[5-(hydroxymethyl)-1-methyl-3-(morpholin-4-ylmethyl)-1H-pyrazol-4-yl]-3-[3-(naphthalen-1-yloxy)propyl]-1H-indole-2-carboxylate (950 mg, 1.63 mmol) in THF (22 ml) was added sodium hydride (156 mg, 60% purity, 3.91 mmol) at 0° C. and the mixture was stirred for 2 hours at room temperature. The reaction mixture was cooled down to 0° C. and a solution of allyl bromide (340 μl, 3.9 mmol) in THF (2 ml) was added. The mixture was stirred for 3 days at room temperature and for 1 day at 40° C. For work-up, an aqueous sodium chloride solution was added and the mixture was extracted with ethyl acetate. The combined organic phases were filtered through a silicone filter and concentrated. The residue was purified by flash chromatography (dichloromethane/methanol gradient, 0%→7% methanol) to give the title compound (588 mg).

LC-MS (Method 2): Rt=1.73 min; MS (ESIpos): m/z=663 [M+H]$^+$ $^1$H-NMR (400 MHz, DMSO-d6) δ [ppm]: 1.066 (8.71), 1.240 (5.06), 1.258 (11.18), 1.275 (5.03), 1.986 (0.58), 2.063 (0.53), 2.074 (0.97), 2.090 (1.10), 2.102 (1.49), 2.114 (0.91), 2.169 (1.31), 2.179 (1.32), 2.197 (1.75), 2.213 (1.82), 2.230 (1.10), 2.518 (1.55), 2.522 (1.03), 3.082 (1.73), 3.115 (2.48), 3.216 (2.53), 3.249 (1.88), 3.298 (4.62), 3.310 (3.58), 3.320 (2.53), 3.768 (0.53), 3.782 (0.55), 3.797 (0.86), 3.801 (1.41), 3.805 (0.87), 3.811 (0.93), 3.815 (1.45), 3.819 (0.86), 3.831 (0.95), 3.835 (1.53), 3.839 (1.04), 3.845 (1.09), 3.848 (1.67), 3.852 (1.30), 3.864 (16.00), 3.877 (0.56), 3.881 (0.68), 3.884 (0.42), 3.939 (1.41), 4.101 (1.98), 4.131 (2.99), 4.138 (1.37), 4.177 (2.63), 4.181 (2.15), 4.192 (2.97), 4.201 (1.96), 4.208 (1.55), 4.219 (3.71), 4.236 (3.35), 4.254 (1.07), 4.281 (2.49), 4.311 (1.98), 4.619 (0.51), 4.632 (0.55), 4.662 (0.76), 4.674 (0.71), 4.718 (1.29), 4.722 (1.24), 4.744 (1.33), 4.748 (1.28), 4.852 (0.68), 4.863 (0.72), 4.894 (0.56), 4.906 (0.53), 5.003 (0.61), 5.007 (1.24), 5.011 (1.47), 5.014 (0.67), 5.030 (0.71), 5.033 (1.49), 5.037 (2.15), 5.041 (2.20), 5.045 (1.32), 5.050 (0.53), 5.080 (0.76), 5.084 (1.73), 5.089 (1.47), 5.093 (0.54), 5.427 (0.71), 5.440 (0.50), 5.453 (0.74), 5.457 (0.42), 5.469 (0.72), 5.482 (0.45), 5.495 (0.61), 5.698 (0.51), 5.711 (1.11), 5.724 (0.81), 5.737 (1.13), 5.741 (0.57), 5.751 (0.63), 5.755 (1.09), 5.758 (1.27), 5.768 (0.72), 5.781 (0.86), 5.795 (0.42), 6.868 (1.73), 6.886 (1.89), 6.992 (1.63), 6.996 (1.62), 7.010 (2.35), 7.013 (2.09), 7.074 (2.03), 7.093 (2.21), 7.112 (1.38), 7.362 (1.41), 7.382 (2.51), 7.402 (2.02), 7.449 (2.56), 7.470 (1.49), 7.500 (0.55), 7.512 (1.80), 7.516 (2.79), 7.526 (3.23), 7.536 (2.71), 7.540 (1.92), 7.552 (0.58), 7.755 (1.86), 7.758 (1.89), 7.775 (1.74), 7.778 (1.61), 7.861 (1.48), 7.864 (1.05), 7.872 (0.80), 7.875 (0.92), 7.878 (0.96), 7.884 (1.24), 8.234 (1.32), 8.242 (0.88), 8.248 (0.64), 8.258 (1.18).

Intermediate 264

(rac)-ethyl (E/Z)-1-methyl-3-(morpholin-4-ylmethyl)-7-[3-(naphthalen-1-yloxy)propyl]-1,10,13,15-tetrahydropyrazolo[4',3':9,10][1,6]oxazacycloundecino[8,7,6-hi]indole-8-carboxylate

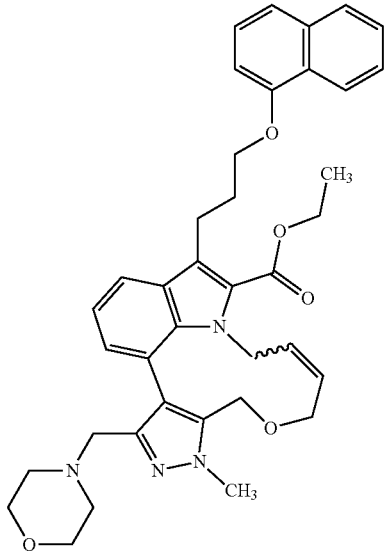 [SMILES: CCOC(=O)c1c(CCCOc2cccc3ccccc23)c2cccc3c2n1CC=CCOCc1c-3c(CN2CCOCC2)nn1C]

A solution of ethyl 7-{1-methyl-3-(morpholin-4-ylmethyl)-5-[(prop-2-en-1-yloxy)methyl]-1H-pyrazol-4-yl}-3-[3-(naphthalen-1-yloxy)propyl]-1-(prop-2-en-1-yl)-1H-indole-2-carboxylate (580 mg, 875 μmol) in dichloromethane (11 ml) was purged with argon several times. (1,3-Bis(2,4,6-trimethylphenyl)-2-imidazolidinylidene)dichloro(phenylmethylene)(tricyclohexylphosphine)ruthenium (74.3 mg, 87.5 μmol) (Grubbs 2$^{nd}$ generation catalyst) was added and the reaction mixture was stirred for 2 days at room temperature. For work-up, the reaction mixture was concentrated under reduced pressure and the residue was purified by flash chromatography (dichloromethane/methanol gradient, 0%→5% methanol) to give the title compound (79 mg).

LC-MS (Method 2): Rt=1.70 min; MS (ESIpos): m/z=635 [M+H]$^+$ $^1$H-NMR (400 MHz, DMSO-d6) δ [ppm]: 1.232 (1.20), 1.241 (1.42), 1.259 (2.25), 1.265 (4.66), 1.282 (9.63), 1.300 (4.46), 1.837 (0.83), 1.843 (0.83), 1.855 (1.10), 1.864 (0.97), 1.873 (0.99), 1.879 (0.85), 2.084 (5.88), 2.104 (1.24), 2.197 (0.77), 2.213 (1.40), 2.229 (1.62), 2.246 (1.07), 2.323 (0.89), 2.327 (1.22), 2.331 (0.87), 2.337 (0.43), 2.518 (5.46), 2.523 (3.69), 2.660 (0.43), 2.665 (0.89), 2.669 (1.22), 2.673 (0.87), 2.900 (0.45), 2.933 (3.37), 2.939 (3.29), 2.972 (0.45), 3.116 (0.55), 3.172 (0.95), 3.216 (1.80), 3.225 (1.40), 3.232 (1.40), 3.244 (0.77), 3.252 (0.97), 3.286 (1.22), 3.300 (1.80), 3.373 (0.51), 3.390 (0.85), 3.409 (0.61), 3.423 (0.57), 3.492 (0.63), 3.523 (1.07), 3.554 (0.73), 3.566 (0.63), 3.770 (0.71), 3.780 (0.85), 3.802 (0.77), 3.813 (0.71), 3.851 (0.51), 3.864 (2.41), 3.891 (14.05), 4.132 (0.55), 4.164 (1.40), 4.179 (3.18), 4.194 (1.91), 4.211 (0.75), 4.224 (2.11), 4.229 (1.16), 4.238 (1.20), 4.246 (0.89), 4.257 (3.22), 4.274 (1.91), 4.279 (2.03), 4.291 (0.75), 4.296 (1.66), 4.306 (0.71), 4.314 (0.59), 4.323 (0.63), 4.686 (0.55), 4.709 (2.25), 4.726 (0.87), 4.743 (2.05), 4.970 (0.91), 5.007 (2.29), 5.038 (0.77), 5.190 (0.59), 5.201 (0.59), 5.759 (16.00), 6.791 (1.70), 6.794 (1.78), 6.809 (1.99), 6.811 (1.91), 6.856 (1.66), 6.874 (1.95), 7.013 (0.41), 7.025 (1.72), 7.046 (1.97), 7.063 (1.46), 7.093 (0.45), 7.360 (1.24), 7.381 (2.39), 7.400 (1.85), 7.447 (2.51), 7.467 (1.48), 7.495 (0.55), 7.508 (1.56), 7.514 (2.35), 7.524 (3.16), 7.532 (2.37), 7.538 (2.07), 7.551 (0.61), 7.752 (1.78), 7.755 (1.99), 7.772 (1.74), 7.774 (1.85), 7.859 (1.52), 7.868 (0.85), 7.877 (1.24), 7.883 (1.32), 8.218 (1.20), 8.225 (1.07), 8.234 (0.83), 8.243 (1.30).

Intermediate 265

(rac)-ethyl 1-methyl-3-(morpholin-4-ylmethyl)-7-[3-(naphthalen-1-yloxy)propyl]-1,10,11,12,13,15-hexahydropyrazolo[4',3':9,10][1,6]oxazacycloundecino[8,7,6-hi]indole-8-carboxylate

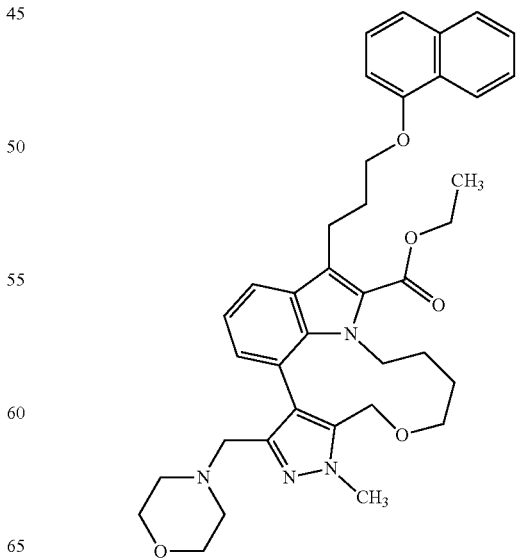

A mixture of ethyl 7-[5-(hydroxymethyl)-1-methyl-3-(morpholin-4-ylmethyl)-1H-pyrazol-4-yl]-3-[3-(naphthalen-1-yloxy)propyl]-1H-indole-2-carboxylate (100 mg, 172 µmol), 1,4-diiodobutane (24 µl, 180 µmol) and caesium carbonate (168 mg, 515 µmol) in DMF (6.8 ml) was stirred at 50° C. for 3 hours and for 17 hours at room temperature. For work-up, the mixture was concentrated and the residue was purified by flash chromatography (dichloromethane/acetone gradient, 0%→75% acetone) to give the title compound (34 mg).

$^1$H-NMR (400 MHz, DMSO-d6) δ [ppm]: 0.852 (0.68), 1.137 (1.58), 1.232 (2.89), 1.268 (5.58), 1.275 (1.37), 1.286 (11.84), 1.292 (2.05), 1.304 (5.37), 1.310 (0.95), 1.894 (0.74), 2.069 (0.95), 2.084 (4.00), 2.097 (1.53), 2.115 (1.16), 2.168 (1.47), 2.188 (1.74), 2.205 (2.11), 2.223 (1.16), 2.318 (1.00), 2.322 (2.32), 2.326 (3.21), 2.332 (2.26), 2.336 (1.00), 2.456 (0.79), 2.460 (0.79), 2.518 (11.32), 2.522 (7.84), 2.660 (1.00), 2.664 (2.37), 2.668 (3.21), 2.673 (2.26), 2.678 (1.00), 3.057 (1.74), 3.090 (2.32), 3.242 (2.53), 3.275 (4.89), 3.285 (5.89), 3.297 (4.26), 3.883 (16.00), 3.903 (2.16), 3.913 (0.42), 4.045 (0.47), 4.066 (0.68), 4.080 (0.47), 4.089 (0.58), 4.180 (1.37), 4.196 (2.95), 4.211 (1.47), 4.232 (0.89), 4.242 (1.05), 4.249 (1.32), 4.264 (3.74), 4.267 (3.79), 4.274 (2.11), 4.282 (3.26), 4.285 (3.32), 4.300 (1.26), 4.326 (1.53), 4.340 (1.42), 4.359 (0.95), 4.373 (0.84), 4.640 (1.00), 4.645 (1.05), 4.683 (1.16), 4.688 (1.26), 4.756 (1.11), 4.761 (1.11), 4.782 (1.26), 4.787 (1.16), 5.196 (1.26), 5.207 (1.95), 5.210 (1.89), 5.221 (1.47), 5.233 (0.63), 5.250 (0.95), 5.267 (0.89), 5.293 (0.58), 6.882 (1.95), 6.901 (2.00), 7.023 (0.89), 7.027 (1.32), 7.041 (2.95), 7.045 (2.74), 7.052 (2.95), 7.071 (2.89), 7.089 (1.16), 7.370 (1.58), 7.390 (2.79), 7.409 (2.26), 7.452 (2.89), 7.473 (1.68), 7.506 (0.63), 7.518 (2.21), 7.521 (2.53), 7.523 (2.05), 7.532 (2.84), 7.539 (2.16), 7.542 (2.47), 7.545 (2.32), 7.556 (0.63), 7.721 (1.74), 7.725 (1.95), 7.740 (1.63), 7.744 (1.74), 7.863 (1.63), 7.868 (1.11), 7.877 (1.47), 7.881 (1.05), 7.887 (1.37), 8.238 (1.42), 8.249 (1.16), 8.262 (1.26).

Intermediate 266

(rac)-ethyl 9-methyl-11-(morpholin-4-ylmethyl)-1-[3-(naphthalen-1-yloxy)propyl]-5,6,8,9-tetrahydro-4H-pyrazolo[4',3':8,9][1,5]oxazecino[7,6,5-hi]indole-2-carboxylate

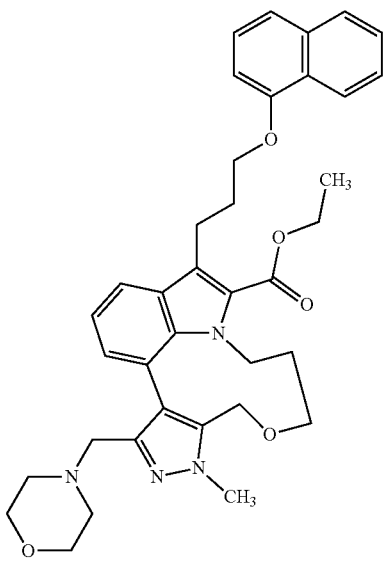 [SMILES: CCOC(=O)c1c(CCCOc2cccc3ccccc23)c2cccc3c2n1CCCOCc1c-3c(CN2CCOCC2)nn1C]

To a solution of ethyl 7-[5-(hydroxymethyl)-1-methyl-3-(morpholin-4-ylmethyl)-1H-pyrazol-4-yl]-3-[3-(naphthalen-1-yloxy)propyl]-1H-indole-2-carboxylate (see Intermediate 262, 400 mg, 686 µmol) in DMF (27 ml) was added caesium carbonate (671 mg, 2.06 mmol) and 1,3-diiodopropane (83 µl, 720 µmol), and the reaction mixture was stirred for 20 hours at room temperature. For work-up, the mixture was concentrated under reduced pressure and the crude product was purified by flash chromatography (dichloromethane/methanol gradient, 0%→10% methanol) to give the title compound (90 mg).

LC-MS (Method 2): Rt=1.53 min; MS (ESIpos): m/z=623 [M+H]$^+$

Intermediate 267

Ethyl 7-[5-ethyl-3-(hydroxymethyl)-1-methyl-1H-pyrazol-4-yl]-3-[3-(1-naphthyloxy)propyl]-1H-indole-2-carboxylate

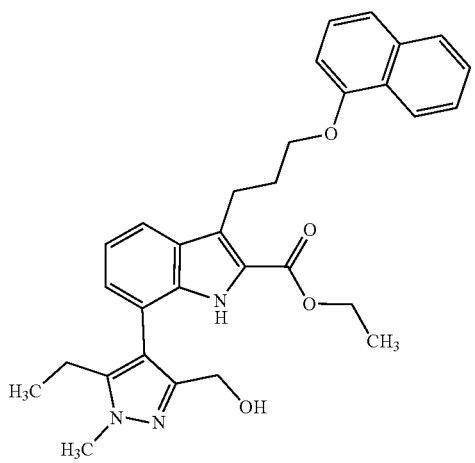

A degassed solution of ethyl 3-[3-(naphthalen-1-yloxy)propyl]-7-(4,4,5,5-tetramethyl-1,3,2-dioxaborolan-2-yl)-1H-indole-2-carboxylate (see Intermediate 5, 3.13 g, 6.27 mmol; prepared according to a procedure described in Journal of Medicinal Chemistry, 2015, 58, 2180-2194) and (4-bromo-5-ethyl-1-methyl-1H-pyrazol-3-yl)methanol (1.37 g, 6.27 mmol, Intermediate 400) in 1,4-dioxane (80 mL) was purged with argon. [1,1'-Bis(diphenylphosphino)ferrocene]dichloropalladium(II) (1.02 g, 1.25 mmol; complex with dichloromethane) was added and the mixture was stirred at 85° C. for 24 hrs. After cooling the mixture was poured into water and extracted with ethyl acetate. The organic layer was washed with water and brine and dried over sodium sulfate. After filtration and removal of the solvent the residue was purified by flash chromatography (Biotage SNAP cartridge silica 80 g, acetonitrile:dichloromethane) to give the title compound (2.00 g, 62% yield).

MS: m/z=512.3 [M+H]$^+$.

609

Intermediate 268

Ethyl 1-{3-[(tert-butoxycarbonyl)(methyl)amino]propyl}-7-[5-ethyl-3-(hydroxymethyl)-1-methyl-1H-pyrazol-4-yl]-3-[3-(1-naphthyloxy)propyl]-1H-indole-2-carboxylate

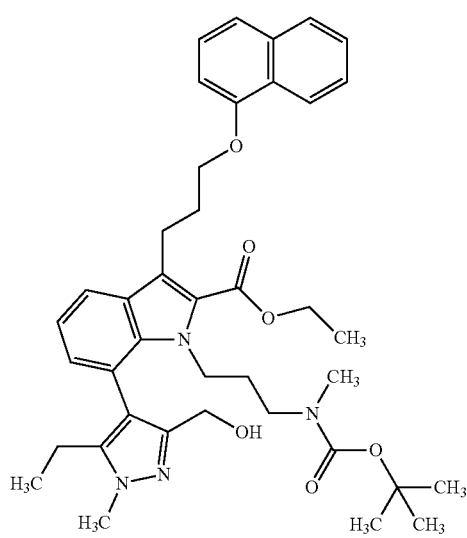 [SMILES: CCOC(=O)c1c(CCCOc2cccc3ccccc23)c2cccc(-c3c(CO)nn(C)c3CC)c2n1CCCN(C)C(=O)OC(C)(C)C]

A mixture of ethyl 7-[5-ethyl-3-(hydroxymethyl)-1-methyl-1H-pyrazol-4-yl]-3-[3-(1-naphthyloxy)propyl]-1H-indole-2-carboxylate (1.00 g, 1.95 mmol), tert-butyl (3-bromopropyl)methylcarbamate (see Intermediate 1, 591 mg, 2.35 mmol; CAS-No.: 828272-19-1), DMF (26 mL) and caesium carbonate (3.18 g, 9.77 mmol) was stirred at room temperature for 5 days. Water was added, the mixture was extracted with ethyl acetate, the organic layer was washed with brine and dried over sodium sulfate. After filtration and concentration the residue was purified by flash chromatography (Biotage SNAP cartridge silica 50 g, methanol:dichloromethane) to give the title compound (770 mg, 58% yield).

LC-MS: m/z=683.0 [M+H]$^+$.

610

Intermediate 269

Ethyl 7-[3-(bromomethyl)-5-ethyl-1-methyl-1H-pyrazol-4-yl]-1-{3-[(tert-butoxycarbonyl)(methyl)amino]propyl}-3-[3-(1-naphthyloxy)propyl]-1H-indole-2-carboxylate

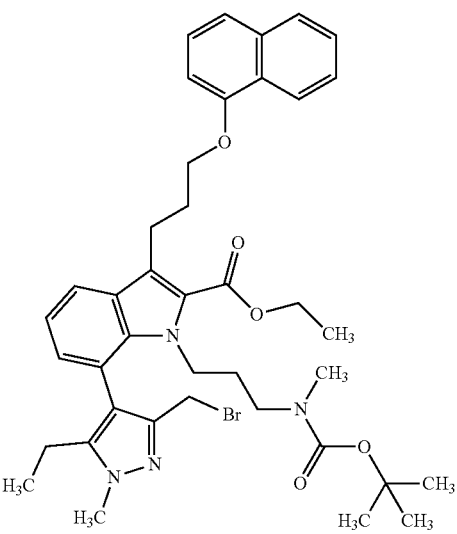 [SMILES: CCOC(=O)c1c(CCCOc2cccc3ccccc23)c2cccc(-c3c(CBr)nn(C)c3CC)c2n1CCCN(C)C(=O)OC(C)(C)C]

To a solution of ethyl 1-{3-[(tert-butoxycarbonyl)(methyl)amino]propyl}-7-[5-ethyl-3-(hydroxymethyl)-1-methyl-1H-pyrazol-4-yl]-3-[3-(1-naphthyloxy)propyl]-1H-indole-2-carboxylate (770 mg, 1.13 mmol) and triphenylphosphine (710 mg, 2.71 mmol) in dichloromethane (21 mL) was added tetrabromomethane (897 mg, 2.71 mmol) at 0° C. and the mixture was stirred at 0° C. for 5 hrs. The mixture was concentrated to give the crude title compound (900 mg) that was used without further purification.

LC-MS: m/z=745.6 [M+H]$^+$.

611

Intermediate 270

Ethyl 7-[3-(bromomethyl)-5-ethyl-1-methyl-1H-pyrazol-4-yl]-1-[3-(methylamino)propyl]-3-[3-(1-naphthyloxy)propyl]-1H-indole-2-carboxylate hydrochloric acid salt

612

Intermediate 271

(rac)-Ethyl 11-ethyl-7,10-dimethyl-1-[3-(1-naphthyloxy)propyl]-4,5,6,7,8,10-hexahydropyrazolo[3',4':7,8][1,5]diazecino[9,10,1-hi]indole-2-carboxylate

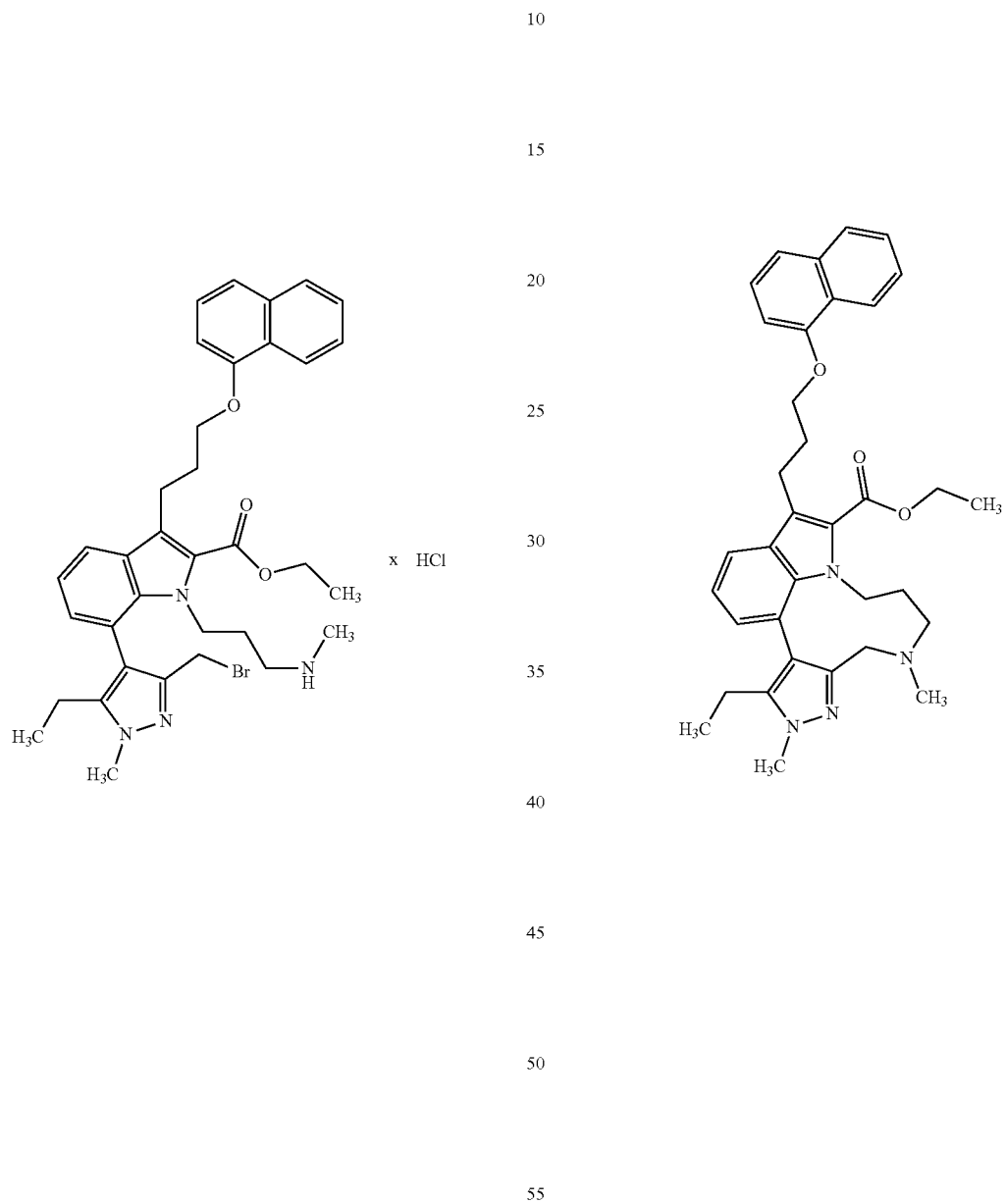

A mixture of ethyl 7-[3-(bromomethyl)-5-ethyl-1-methyl-1H-pyrazol-4-yl]-1-{3-[(tert-butoxycarbonyl)(methyl)amino]propyl}-3-[3-(1-naphthyloxy)propyl]-1H-indole-2-carboxylate (900 mg, 1.21 mmol), hydrogen chloride (21 mL, 4.0 M in dioxane) and methanol (22 mL) was stirred at RT for 3 hrs. The mixture was concentrated to give the title compound (823 mg, 100% yield) that was used without further purification.

A mixture of ethyl 7-[3-(bromomethyl)-5-ethyl-1-methyl-1H-pyrazol-4-yl]-1-[3-(methylamino)propyl]-3-[3-(1-naphthyloxy)propyl]-1H-indole-2-carboxylate hydrochloric acid salt (835 mg), DMF (94 mL) and caesium carbonate (1.99 g, 6.12 mmol) was stirred at 65° C. for 24 hrs. The mixture was concentrated and purified by flash chromatography (Biotage SNAP cartridge silica 40 g, methanol:dichloromethane) to give the title compound (160 mg, 23% yield).

LC-MS: m/z=565.0 [M+H]$^+$.

613

Intermediate 272

Ethyl 1-allyl-7-{3-[(allyloxy)methyl]-5-ethyl-1-methyl-1H-pyrazol-4-yl}-3-[3-(1-naphthyloxy)propyl]-1H-indole-2-carboxylate

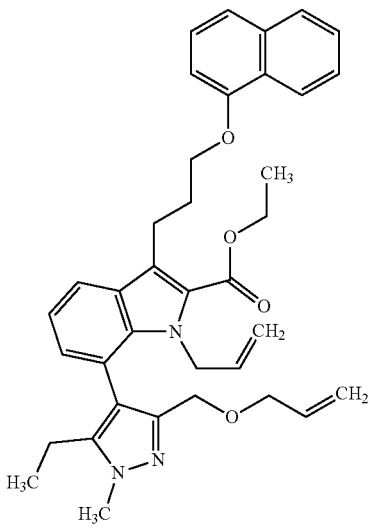 [SMILES: C=CCOCc1nn(C)c(CC)c1-c1cccc2c(CCCOc3cccc4ccccc34)c(C(=O)OCC)n(CC=C)c12]

Sodium hydride (313 mg, 60% suspension in mineral oil, 7.82 mmol) was added to a solution of Ethyl 7-[5-ethyl-3-(hydroxymethyl)-1-methyl-1H-pyrazol-4-yl]-3-[3-(1-naphthyloxy)propyl]-1H-indole-2-carboxylate (see Intermediate 267, 1.00 g, 1.95 mmol) in THF (26 mL) at 0° C. and the mixture was stirred at room temperature for 2 hrs. 3-Bromoprop-1-ene (680 µL, 7.8 mmol) was added at 0° C. and the mixture was stirred at room temperature for 5 days. The mixture was poured in brine and extracted with ethyl acetate. The organic phase was washed with brine and dried over sodium sulfate. After filtration and removal of the solvent the residue was purified by flash chromatography (Biotage SNAP cartridge silica 80 g, acetonitrile:dichloromethane) to give the title compound (450 mg, 39% yield).

LC-MS: m/z=592.2 [M+H]$^+$.

614

Intermediate 273

(rac)-Ethyl (11Z/Z)-3-ethyl-2-methyl-7-[3-(1-naphthyloxy)propyl]-2,10,13,15-tetrahydropyrazolo[4',3':9,10][1,6]oxazacycloundecino[8,7,6-hi]indole-8-carboxylate

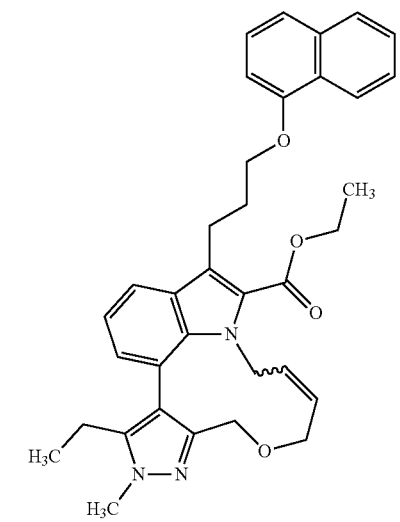 [SMILES: CCOC(=O)c1c(CCCOc2cccc3ccccc23)c2cccc3c2n1CC=CCOCc1nn(C)c(CC)c1-3]

Benzylidene[1,3-bis(2,4,6-trimethylphenyl)imidazolidin-2-ylidene]dichlororuthenium-tricyclohexylphosphane (64.6 mg, 76.0 µmol) was added to a solution of ethyl 1-allyl-7-{3-[(allyloxy)methyl]-5-ethyl-1-methyl-1H-pyrazol-4-yl}-3-[3-(1-naphthyloxy)propyl]-1H-indole-2-carboxylate (450 mg, 760 µmol) in dichloromethane (9.8 mL) and the mixture was stirred at RT for 2 days. The mixture was concentrated and the residue was purified by flash chromatography (Biotage SNAP cartridge silica 25 g, acetonitrile:dichloromethane) to give the title compound (150 mg, 35% yield).

LC-MS: m/z=564.4 [M+H]$^+$.

615

Intermediate 274

(rac)-Ethyl 3-ethyl-2-methyl-7-[3-(1-naphthyloxy)propyl]-2,10,11,12,13,15-hexahydropyrazolo[4',3':9,10][1,6]oxazacycloundecino[8,7,6-hi]indole-8-carboxylate

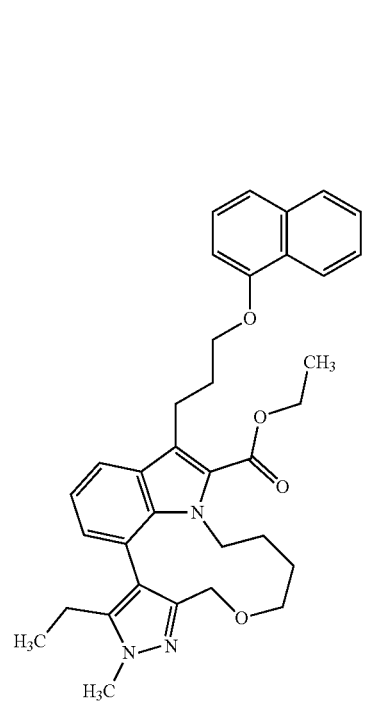 [SMILES: CCOC(=O)c1c(CCCOc2cccc3ccccc23)c2cccc3c2n1CCCCOCc1nn(C)c(CC)c1-3]

To a suspension of Pd/C (42.5 mg, 10% purity, 39.9 μmol) in ethanol (4.6 mL) was added (rac)-ethyl (11Z/Z)-3-ethyl-2-methyl-7-[3-(1-naphthyloxy)propyl]-2,10,13,15-tetrahydropyrazolo[4',3':9,10][1,6]oxazacycloundecino[8,7,6-hi]indole-8-carboxylate (150 mg, 266 μmol) and the mixture was stirred under an atmosphere of hydrogen for 24 hrs at room temperature. The mixture was filtered through a pad of celite, the residue was washed with THF and the filtrate was concentrated to give the title compound (120 mg, 80% yield).

LC-MS: m/z=566.4 [M+H]$^+$.

616

Intermediate 275

Ethyl 7-[5-ethyl-3-(hydroxymethyl)-1-methyl-1H-pyrazol-4-yl]-6-methyl-3-[3-(1-naphthyloxy)propyl]-1H-indole-2-carboxylate

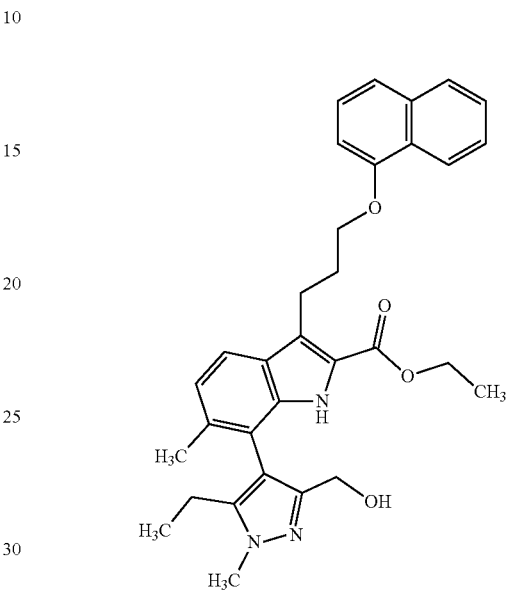

XPhos Pd G2 (see abbreviation list, 168 mg, 214 μmol) was added to a degassed mixture of ethyl 6-methyl-3-[3-(naphthalen-1-yloxy)propyl]-7-(4,4,5,5-tetramethyl-1,3,2-dioxaborolan-2-yl)-1H-indole-2-carboxylate (see Intermediate 19, 3.94 g, 7.67 mmol), (4-bromo-5-ethyl-1-methyl-1H-pyrazol-3-yl)methanol (1.40 g, 6.39 mmol, Intermediate 400), aqueous potassium phosphate solution (26 mL, 0.50 M) and THF (78 mL). The mixture was stirred at 60° C. for 2 hrs. The mixture was poured into water and extracted with ethyl acetate. The organic layer was washed with water and brine and dried over sodium sulfate. After filtration and removal of the solvent the residue was purified by flash chromatography (Biotage, SNAP silica 80 g, acetonitrile:dichloromethane) to give the title compound (1.20 g, 30% yield).

LC-MS: m/z=526.4 [M+H]$^+$.

617

Intermediate 276

Ethyl 1-{3-[(tert-butoxycarbonyl)(methyl)amino]
propyl}-7-[5-ethyl-3-(hydroxymethyl)-1-methyl-1H-
pyrazol-4-yl]-6-methyl-3-[3-(1-naphthyloxy)propyl]-
1H-indole-2-carboxylate

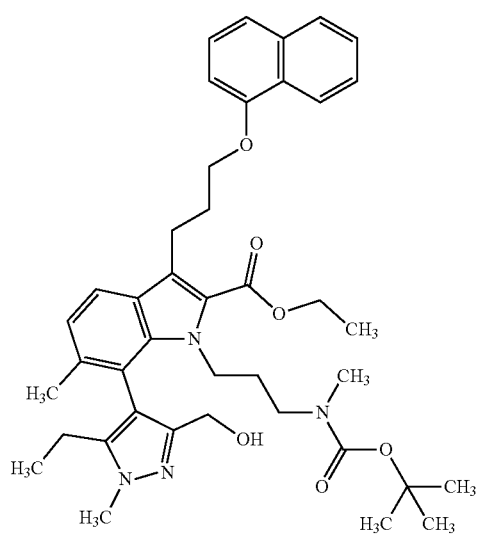 [SMILES: CCOC(=O)c1c(CCCOc2cccc3ccccc23)c2ccc(C)c(-c3c(CO)nn(C)c3CC)c2n1CCCN(C)C(=O)OC(C)(C)C]

A mixture of ethyl 7-[5-ethyl-3-(hydroxymethyl)-1-methyl-1H-pyrazol-4-yl]-6-methyl-3-[3-(1-naphthyloxy)propyl]-1H-indole-2-carboxylate (800 mg, 1.52 mmol), tert-butyl (3-bromopropyl)methylcarbamate (see Intermediate 1, 461 mg, 1.83 mmol; CAS-No.: 828272-19-1), DMF (20 mL) and caesium carbonate (2.48 g, 7.61 mmol) was stirred at RT for 3 days. Water was added, the mixture extracted with ethyl acetate, the organic layer washed with brine and dried over sodium sulfate. After filtration and concentration the residue was purified by flash chromatography (Biotage SNAP cartridge silica 50 g, methanol:dichloromethane) to give the title compound (690 mg, 65% yield).

LC-MS: m/z=697.6 [M+H]+.

618

Intermediate 277

Ethyl 7-[3-(bromomethyl)-5-ethyl-1-methyl-1H-
pyrazol-4-yl]-1-{3-[(tert-butoxycarbonyl)(methyl)
amino]propyl}-6-methyl-3-[3-(1-naphthyloxy)pro-
pyl]-1H-indole-2-carboxylate

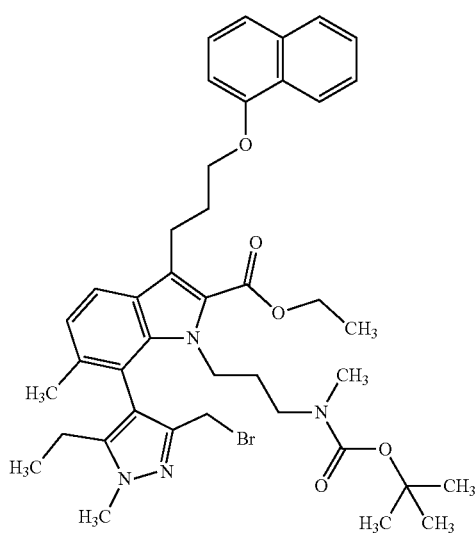

To a solution of ethyl 1-{3-[(tert-butoxycarbonyl)(methyl)amino]propyl}-7-[5-ethyl-3-(hydroxymethyl)-1-methyl-1H-pyrazol-4-yl]-6-methyl-3-[3-(1-naphthyloxy)propyl]-1H-indole-2-carboxylate (690 mg, 990 µmol) and triphenylphosphine (623 mg, 2.38 mmol) in dichloromethane (18 mL) was added tetrabromomethane (788 mg, 2.38 mmol) at 0° C. and the mixture was stirred at 0° C. for 3 hrs. The mixture was concentrated to give the crude title compound (752 mg) that was used without further purification.

Intermediate 278

Ethyl 7-[3-(bromomethyl)-5-ethyl-1-methyl-1H-pyrazol-4-yl]-6-methyl-1-[3-(methylamino)propyl]-3-[3-(1-naphthyloxy)propyl]-1H-indole-2-carboxylate hydrochloric acid salt

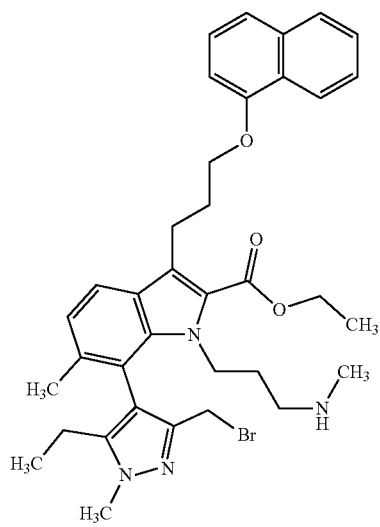

A mixture of ethyl 7-[3-(bromomethyl)-5-ethyl-1-methyl-1H-pyrazol-4-yl]-1-{3-[(tert-butoxycarbonyl)(methyl)amino]propyl}-6-methyl-3-[3-(1-naphthyloxy)propyl]-1H-indole-2-carboxylate (753 mg, 991 µmol), hydrogen chloride (17 mL, 4.0 M in 1,4-dioxane) and methanol (22 mL) was stirred at RT for 3 hrs. The mixture was concentrated to give the title compound (689 mg) that was used without further purification.

Intermediate 279

(rac)-Ethyl 11-ethyl-7,10,12-trimethyl-1-[3-(1-naphthyloxy)propyl]-4,5,6,7,8,10-hexahydropyrazolo[3',4':7,8][1,5]diazecino[9,10,1-hi]indole-2-carboxylate

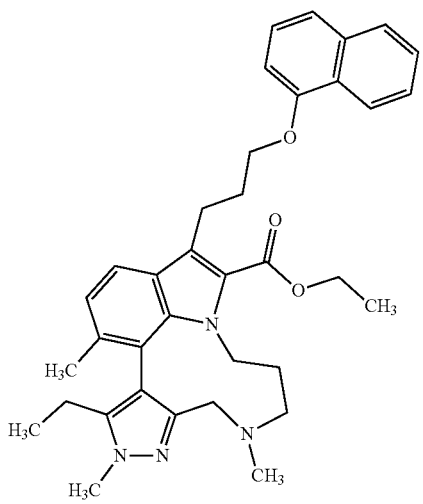 [SMILES: CCOC(=O)c1c(CCCOc2cccc3ccccc23)c2ccc(C)c3c2n1CCCN(C)Cc1nn(C)c(CC)c1-3]

A mixture of ethyl 7-[3-(bromomethyl)-5-ethyl-1-methyl-1H-pyrazol-4-yl]-6-methyl-1-[3-(methylamino)propyl]-3-[3-(1-naphthyloxy)propyl]-1H-indole-2-carboxylate hydrochloric acid salt (690 mg), DMF (61 mL) and caesium carbonate (1.61 g, 4.96 mmol) was stirred at 65° C. for 17 hrs. The mixture was concentrated and purified by flash chromatography (Biotage SNAP cartridge silica 40 g, methanol:dichloromethane) to give the title compound (350 mg, 61% yield).

LC-MS: m/z=579.5 [M+H]$^+$.

Intermediate 280

Ethyl 1-allyl-7-{3-[(allyloxy)methyl]-5-ethyl-1-methyl-1H-pyrazol-4-yl}-6-methyl-3-[3-(1-naphthyloxy)propyl]-1H-indole-2-carboxylate

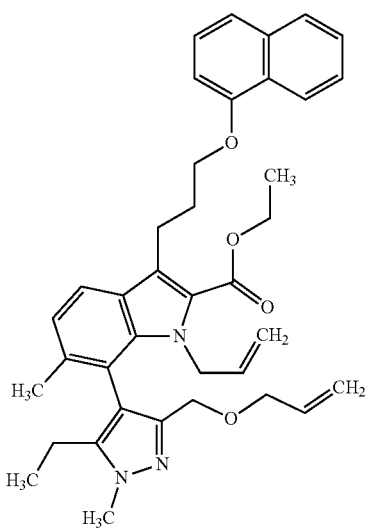 [SMILES: C=CCOCc1nn(C)c(CC)c1-c1c(C)ccc2c(CCCOc3cccc4ccccc34)c(C(=O)OCC)n(CC=C)c12]

Sodium hydride (183 mg, 60% suspension in mineral oil, 4.57 mmol) was added to a solution of ethyl 7-[5-ethyl-3-(hydroxymethyl)-1-methyl-1H-pyrazol-4-yl]-6-methyl-3-[3-(1-naphthyloxy)propyl]-1H-indole-2-carboxylate (see Intermediate 275, 600 mg, 1.14 mmol) in THF (15 mL) at 0° C. and the mixture was stirred at RT for 2 hrs. 3-Bromoprop-1-ene (400 µL, 4.6 mmol) was added at 0° C. and the mixture was stirred at room temperature for 6 days. The mixture was poured into brine and extracted with ethyl acetate. The organic phase was washed with brine and dried over sodium sulfate. After filtration and removal of the solvent the residue was purified by flash chromatography (Biotage SNAP cartridge silica 40 g, ethyl acetate:n-Hexane) to give the title compound (421 mg, 61% yield).

LC-MS: m/z=606.5 [M+H]$^+$.

621

Intermediate 281

(rac)-Ethyl (11E/Z)-3-ethyl-2,4-dimethyl-7-[3-(1-naphthyloxy)propyl]-2,10,13,15-tetrahydropyrazolo[4',3':9,10][1,6]oxazacycloundecino[8,7,6-hi]indole-8-carboxylate

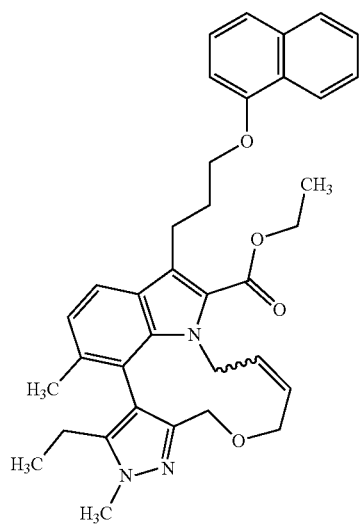 [SMILES: CCOC(=O)c1c(CCCOc2cccc3ccccc23)c2ccc(C)c3c2n1CC=CCOCc1nn(C)c(CC)c1-3]

[1,3-Bis(2,4,6-trimethylphenyl)-2-imidazolidinylidene] dichloro(2-isopropoxyphenylmethylene) ruthenium (89.7 mg, 97% purity, 139 μmol) was added to a degassed solution of ethyl 1-allyl-7-{3-[(allyloxy)methyl]-5-ethyl-1-methyl-1H-pyrazol-4-yl}-6-methyl-3-[3-(1-naphthyloxy)propyl]-1H-indole-2-carboxylate (421 mg, 694 μmol) in dichloromethane (100 mL) and the mixture was stirred at RT for 24 hrs. The mixture was concentrated and the residue was purified by flash chromatography (Biotage SNAP cartridge silica 25 g, acetonitrile:dichloromethane) to give the title compound (280 mg, 70% yield).

LC-MS: m/z=578.4 [M+H]⁺.

622

Intermediate 282

(rac)-Ethyl 3-ethyl-2,4-dimethyl-7-[3-(1-naphthyloxy)propyl]-2,10,11,12,13,15-hexahydropyrazolo[4',3':9,10][1,6]oxazacycloundecino[8,7,6-hi]indole-8-carboxylate

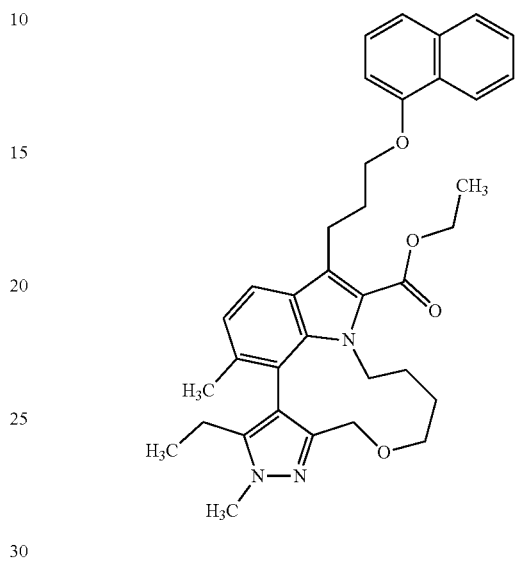

To a suspension of Pd/C (77.4 mg, 10% purity, 72.7 μmol) in ethanol (8.5 mL) was added (rac)-ethyl (11E/Z)-3-ethyl-2,4-dimethyl-7-[3-(1-naphthyloxy)propyl]-2,10,13,15-tetrahydropyrazolo[4',3':9,10][1,6]oxazacycloundecino[8,7,6-hi]indole-8-carboxylate (280 mg, 485 μmol) and the mixture was stirred under an atmosphere of hydrogen for 24 hrs at room temperature. The mixture was filtered through a pad of celite, the residue was washed with THF and the filtrate was concentrated to give the title compound (260 mg, 93% yield).

LC-MS: m/z=580.3 [M+H]⁺.

Intermediate 283 methyl 4-bromo-3-(methoxymethyl)-1-methyl-1H-pyrazole-5-carboxylate

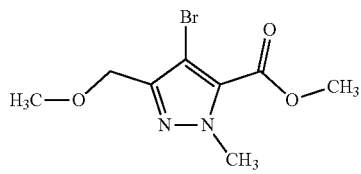

To a mixture of methanol (6.0 ml, 150 mmol) in DMF (150 ml) was added potassium carbonate (20.3 g, 147 mmol) and the mixture was stirred for 10 min at room temperature. Ethyl 4-bromo-3-(bromomethyl)-1-methyl-1H-pyrazole-5-carboxylate (see Intermediate 6, 16.0 g, 49.1 mmol) was added and the reaction mixture was stirred for 20 hours at room temperature and for 4 hours at 40° C. For work-up the reaction mixture was poured into water. The mixture was extracted with ethyl acetate. The combined organic phases washed with brine and were filtered trough a silicone filter.

After removal of the solvent the crude product was purified by flash chromatography (hexane/ethyl acetate gradient, 20%→100% ethyl acetate) to give the title compound (3.3 g).

Intermediate 284

[4-bromo-3-(methoxymethyl)-1-methyl-1H-pyrazol-5-yl]methanol

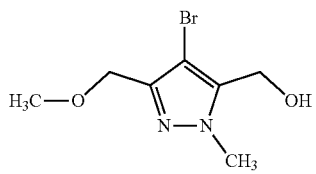

To a solution of methyl 4-bromo-3-(methoxymethyl)-1-methyl-1H-pyrazole-5-carboxylate (3.30 g, 12.5 mmol) in THF (93 ml) at 0° C. was added a solution of lithium aluminium hydride in THF (6.3 ml, 2.0 M, 13 mmol) and the mixture was stirred at 0° C. for 90 min. For work-up water (0.4 ml) were added dropwise, followed by the addition of aqueous 2 M sodium hydroxide solution (0.4 ml) and water (0.4 ml). The mixture was filtered through a pad of celite. The residue was washed with ethyl acetate and the filtrate was concentrated under reduced pressure. The residue was triturated with dichloromethane. The crude product was purified by flash chromatography (dichloromethane/methanol gradient, 3%→10% methanol) to give the title compound (2.1 g).

$^1$H-NMR (400 MHz, DMSO-d6) δ [ppm]: 1.090 (0.54), 3.331 (4.60), 3.831 (1.44), 3.837 (16.00), 4.264 (9.77), 4.299 (0.58), 4.458 (4.62), 4.472 (4.85), 5.369 (1.36), 5.382 (2.79), 5.396 (1.25).

Intermediate 285 ethyl 7-[5-(hydroxymethyl)-3-(methoxymethyl)-1-methyl-1H-pyrazol-4-yl]-3-[3-(naphthalen-1-yloxy)propyl]-1H-indole-2-carboxylate

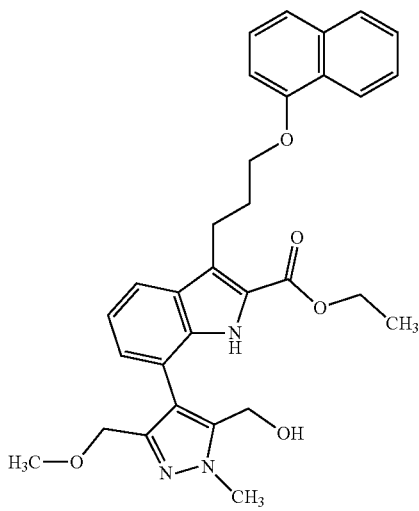

To a solution of ethyl 3-[3-(naphthalen-1-yloxy)propyl]-7-(4,4,5,5-tetramethyl-1,3,2-dioxaborolan-2-yl)-1H-indole-2-carboxylate (see Intermediate 5, 4.46 g, 100% purity, 8.93 mmol) and [4-bromo-3-(methoxymethyl)-1-methyl-1H-pyrazol-5-yl]methanol (2.10 g, 8.93 mmol) in 1,4-dioxane (110 ml) was added a 2 M aqueous solution of potassium carbonate (13 ml, 2.0 M, 27 mmol). The mixture was degassed and purged with argon several times. Pd(dppf)Cl$_2$× CH$_2$Cl$_2$ (1.46 g, 1.79 mmol) was added and the mixture was purged with argon for 10 minutes. The reaction mixture was stirred at 80° C. for 5 hours. For work-up the reaction mixture was concentrated under reduced pressure and the residue was purified by flash chromatography (dichloromethane/methanol gradient, 0%→10% methanol) to give the title compound (2.3 g).

$^1$H-NMR (400 MHz, DMSO-d6) δ [ppm]: 1.066 (16.00), 1.262 (0.77), 1.279 (1.74), 1.297 (0.79), 3.236 (3.60), 3.565 (0.74), 3.936 (2.57), 3.939 (3.63), 4.172 (0.95), 4.216 (0.45), 4.269 (0.60), 4.287 (0.58), 4.374 (0.46), 4.385 (0.45), 5.595 (0.46), 7.447 (0.41), 7.507 (0.40), 7.512 (0.43).

Intermediate 286

(rac)-ethyl 3-(methoxymethyl)-1-methyl-7-[3-(naphthalen-1-yloxy)propyl]-1,10,11,12,13,15-hexahydropyrazolo[4′,3′:9,10][1,6]oxazacycloundecino[8,7,6-hi]indole-8-carboxylate

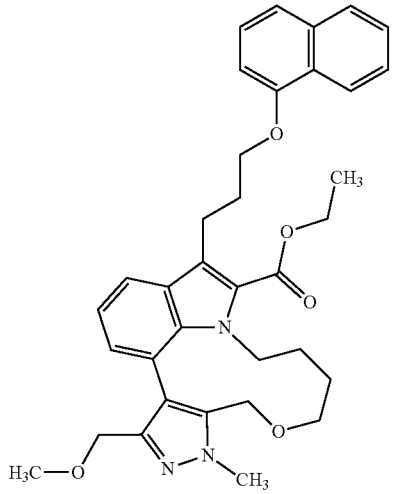 [SMILES: CCOC(=O)c1c(CCCOc2cccc3ccccc23)c2cccc3c2n1CCCCOCc1c-3c(COC)nn1C]

To a solution of ethyl 7-[5-(hydroxymethyl)-3-(methoxymethyl)-1-methyl-1H-pyrazol-4-yl]-3-[3-(naphthalen-1-yloxy)propyl]-1H-indole-2-carboxylate (304 mg, 576 µmol) in DMSO (30 ml) was added caesium carbonate (563 mg, 1.73 mmol) and 1,4-diiodobutane (80 µl, 600 µmol) and the reaction was stirred for 4.5 hours at 50° C. An additional portion of 1,4-diiodobutane (76 µl, 576 µmol) was added and the mixture was stirred for 17 hours at 50° C. For work-up, the reaction mixture was concentrated under reduced pressure and the crude product was purified by flash chromatography (dichloromethane/ethanol gradient, 5%→60% ethanol) to give the title compound (57 mg).

LC-MS (Method 2): Rt=1.58 min; MS (ESIpos): m/z=582 [M+H]$^+$

Intermediate 287

Mixture of ethyl 4-bromo-1-methyl-3-[(propan-2-yloxy)methyl]-1H-pyrazole-5-carboxylate and ethyl 4-bromo-3-(ethoxymethyl)-1-methyl-1H-pyrazole-5-carboxylate

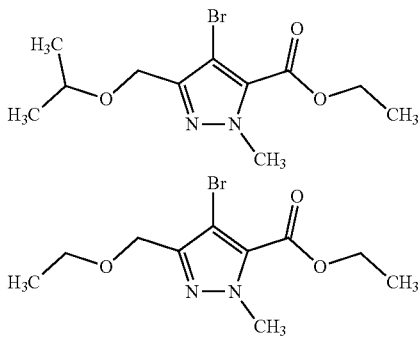

To a solution of propan-2-ol (850 µl, 11 mmol) in dry DMF (35 ml) was slowly added sodium hydride (442 mg, 60% purity, 11.0 mmol) at 0° C. and the mixture was stirred for 1 hour at room temperature. A solution of ethyl 4-bromo-3-(bromomethyl)-1-methyl-1H-pyrazole-5-carboxylate (see Intermediate 6; 3.00 g, 9.20 mmol) in dry DMF (25 ml) was added dropwise and the mixture was stirred for 24 hours at room temperature. For work-up, the reaction mixture was poured into water and the mixture was extracted with ethyl acetate. The combined organic phases were washed with brine and were dried over sodium sulfate. After filtration the filtrate was concentrated under reduced pressure and the residue was purified by flash chromatography (hexane/ethyl acetate gradient, 7%→30% ethyl acetate) to give the title compounds (3 g). (Ethyl 4-bromo-3-(ethoxymethyl)-1-methyl-1H-pyrazole-5-carboxylate was formed as a side product probably due to ethanol impurities in the reaction mixture).

Intermediate 288

Mixture of {4-bromo-1-methyl-3-[(propan-2-yloxy)methyl]-1H-pyrazol-5-yl}methanol and [4-bromo-3-(ethoxymethyl)-1-methyl-1H-pyrazol-5-yl]methanol

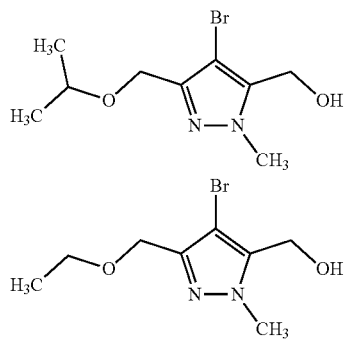

To a solution of a mixture of ethyl 4-bromo-1-methyl-3-[(propan-2-yloxy)methyl]-1H-pyrazole-5-carboxylate and ethyl 4-bromo-3-(ethoxymethyl)-1-methyl-1H-pyrazole-5-carboxylate (4.70 g) in THF (150 ml) at 0° C. was added a solution of lithium aluminium hydride in THF (7.7 ml, 15.4 mmol) and the mixture was stirred at 0° C. for 2 hours. Ice was carefully added and the mixture was stirred for 30 minutes. The mixture was poured into water and the mixture was extracted with ethyl acetate. The combined organic layers were washed with brine and dried over sodium sulfate. After filtration and removal of the solvents the crude product was used without further purification in the subsequent steps.

Intermediate 289

Mixture of ethyl 7-{5-(hydroxymethyl)-1-methyl-3-[(propan-2-yloxy)methyl]-1H-pyrazol-4-yl}-3-[3-(naphthalen-1-yloxy)propyl]-1H-indole-2-carboxylate and ethyl 7-[3-(ethoxymethyl)-5-(hydroxymethyl)-1-methyl-1H-pyrazol-4-yl]-3-[3-(1-naphthyloxy)propyl]-1H-indole-2-carboxylate

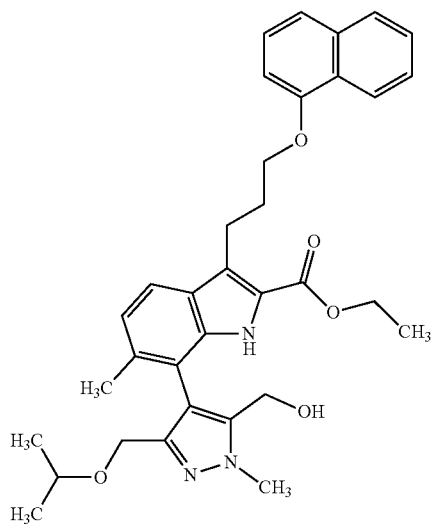

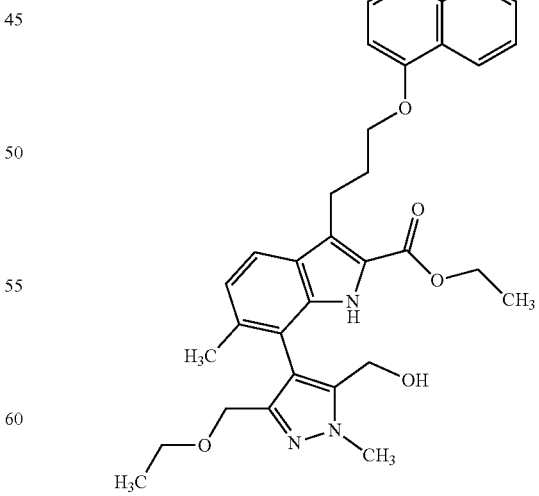

To a solution of a ethyl 3-[3-(naphthalen-1-yloxy)propyl]-7-(4,4,5,5-tetramethyl-1,3,2-dioxaborolan-2-yl)-1H-indole-2-carboxylate (see Intermediate 5, 6.79 g, 13.6 mmol) and a mixture of {4-bromo-1-methyl-3-[(propan-2-yloxy)methyl]-1H-pyrazol-5-yl}methanol and [4-bromo-3-(ethoxymethyl)-1-methyl-1H-pyrazol-5-yl]methanol (3.25 g, 12.4 mmol) in 1,4-dioxane (160 ml) was added a 2 M aqueous solution of potassium carbonate (19 ml, 2.0 M, 37 mmol). The mixture was degassed and purged with argon several times. Pd(dppf)Cl$_2$×CH$_2$Cl$_2$ (1.81 g, 2.47 mmol) was added and the mixture was purged with argon for 10 minutes. The reaction mixture was stirred at 80° C. for 20 hours. For work-up, the reaction mixture was concentrated under reduced pressure and the residue was purified twice by flash chromatography (hexane/ethyl acetate gradient, 20%→100% ethyl acetate, followed by hexane/ethyl acetate gradient, 50%→100% ethyl acetate) to give the title compounds (4.4 g).

Intermediate 290 and Intermediate 291

Ethyl 7-{1-methyl-3-[(propan-2-yloxy)methyl]-5-[(prop-2-en-1-yloxy)methyl]-1H-pyrazol-4-yl}-3-[3-(naphthalen-1-yloxy)propyl]-1-(prop-2-en-1-yl)-1H-indole-2-carboxylate (Intermediate 290) and ethyl 1-allyl-7-{5-[(allyloxy)methyl]-3-(ethoxymethyl)-1-methyl-1H-pyrazol-4-yl}-3-[3-(1-naphthyloxy)propyl]-1H-indole-2-carboxylate (Intermediate 291)

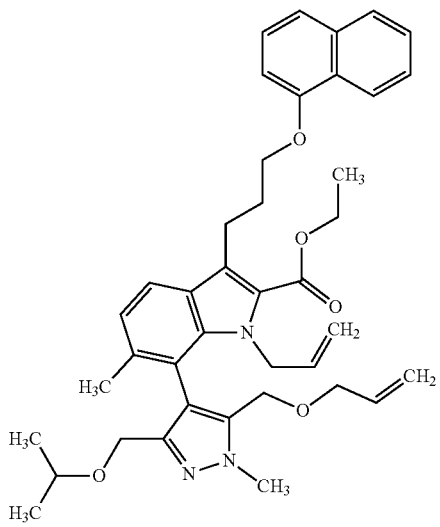

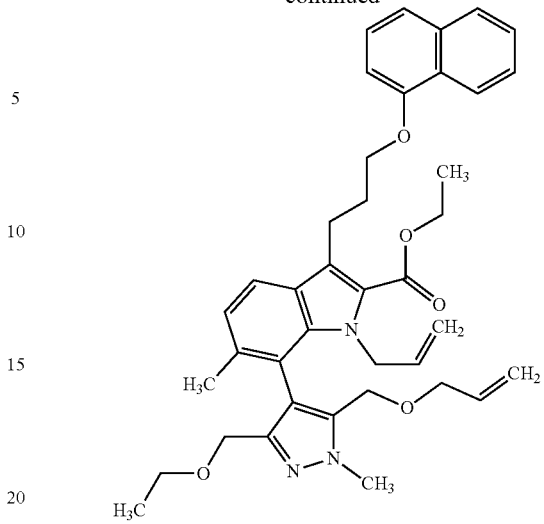

To a solution of a mixture of ethyl 7-{5-(hydroxymethyl)-1-methyl-3-[(propan-2-yloxy)methyl]-1H-pyrazol-4-yl}-3-[3-(naphthalen-1-yloxy)propyl]-1H-indole-2-carboxylate and ethyl 7-[3-(ethoxymethyl)-5-(hydroxymethyl)-1-methyl-1H-pyrazol-4-yl]-3-[3-(1-naphthyloxy)propyl]-1H-indole-2-carboxylate (1.37 g, 2.47 mmol) in THF (33 ml) was added sodium hydride (296 mg, 60% purity, 7.40 mmol) at 0° C. and the mixture was stirred for 2 hours at room temperature. The reaction was cooled down to 0° C. and a solution of allyl bromide (640 µl, 7.4 mmol) in THF (1 ml) was added. The mixture was stirred for 3 days at room temperature. For work-up, aqueous sodium chloride solution was added and the mixture was extracted with ethyl acetate. The combined organic phases were washed with brine and were dried over sodium sulfate and filtered. The filtrate was concentrated under reduced pressure and the residue was purified by flash chromatography (hexane/ethyl acetate gradient, 12%→100% ethyl acetate) to give ethyl 7-{1-methyl-3-[(propan-2-yloxy)methyl]-5-[(prop-2-en-1-yloxy)methyl]-1H-pyrazol-4-yl}-3-[3-(naphthalen-1-yloxy)propyl]-1-(prop-2-en-1-yl)-1H-indole-2-carboxylate (Intermediate 290, 440 mg) and ethyl 1-allyl-7-{5-[(allyloxy)methyl]-3-(ethoxymethyl)-1-methyl-1H-pyrazol-4-yl}-3-[3-(1-naphthyloxy)propyl]-1H-indole-2-carboxylate (Intermediate 291, 710 mg).

Intermediate 290

LC-MS (Method 1): Rt=1.77 min; MS (ESIpos): m/z=637 [M+H]$^+$ $^1$H-NMR (400 MHz, DMSO-d6) δ [ppm]: 0.682 (8.23), 0.697 (8.35), 0.829 (8.36), 0.845 (8.38), 0.853 (0.53), 0.870 (0.91), 0.888 (0.42), 1.093 (0.60), 1.237 (4.70), 1.255 (10.79), 1.273 (4.79), 2.191 (0.88), 2.207 (1.39), 2.224 (0.94), 2.327 (0.46), 2.518 (1.49), 2.523 (1.13), 2.669 (0.45), 3.244 (0.59), 3.259 (1.58), 3.274 (2.07), 3.289 (1.78), 3.304 (1.27), 3.311 (1.43), 3.322 (1.62), 3.769 (0.53), 3.783 (0.58), 3.798 (0.84), 3.802 (2.14), 3.806 (0.77), 3.812 (0.75), 3.816 (1.25), 3.820 (0.71), 3.838 (0.79), 3.842 (1.35), 3.846 (1.00), 3.852 (0.98), 3.855 (1.41), 3.859 (1.03), 3.871 (16.00), 3.878 (2.08), 3.884 (0.53), 3.888 (0.62), 4.078 (1.95), 4.100 (6.11), 4.109 (2.74), 4.129 (1.31), 4.133 (1.26), 4.173 (2.23), 4.176 (2.13), 4.189 (2.62), 4.199 (1.85), 4.204 (1.43), 4.217 (3.96), 4.235 (3.53), 4.252 (1.05), 4.290 (2.32), 4.306 (0.68), 4.320 (1.91), 4.655 (0.40), 4.667 (0.46), 4.698 (0.71), 4.701

(0.63), 4.713 (1.73), 4.717 (1.41), 4.739 (1.30), 4.742 (1.25), 4.810 (0.63), 4.815 (0.60), 4.820 (0.71), 4.852 (0.44), 4.863 (0.43), 5.006 (0.55), 5.009 (1.14), 5.014 (1.36), 5.017 (0.60), 5.032 (0.63), 5.036 (1.21), 5.040 (1.83), 5.045 (1.55), 5.050 (1.25), 5.054 (0.45), 5.084 (0.64), 5.088 (1.59), 5.093 (1.38), 5.097 (0.52), 5.435 (0.65), 5.447 (0.50), 5.460 (0.69), 5.465 (0.41), 5.477 (0.69), 5.490 (0.45), 5.503 (0.59), 5.701 (0.54), 5.715 (1.01), 5.727 (0.82), 5.741 (1.07), 5.744 (0.56), 5.759 (14.41), 5.771 (0.70), 5.784 (0.86), 6.864 (1.52), 6.881 (1.78), 6.984 (1.43), 6.987 (1.61), 7.002 (2.11), 7.005 (2.01), 7.070 (1.96), 7.090 (2.04), 7.108 (1.36), 7.362 (1.31), 7.383 (2.24), 7.402 (1.85), 7.449 (2.38), 7.470 (1.39), 7.501 (0.50), 7.513 (1.67), 7.517 (2.47), 7.527 (2.96), 7.537 (2.32), 7.540 (1.84), 7.553 (0.55), 7.763 (1.67), 7.766 (1.70), 7.783 (1.58), 7.786 (1.52), 7.861 (1.35), 7.865 (0.93), 7.875 (0.85), 7.878 (0.87), 7.884 (1.14), 8.235 (1.20), 8.246 (0.83), 8.259 (1.08).

Intermediate 291

LC-MS (Method 2): Rt=1.77 min; MS (ESIpos): m/z=622 [M+H]$^+$ $^1$H-NMR (400 MHz, DMSO-d6) δ [ppm]: 0.682 (0.69), 0.697 (0.71), 0.829 (0.73), 0.845 (0.86), 0.854 (5.23), 0.870 (11.81), 0.888 (5.50), 1.239 (4.98), 1.257 (11.03), 1.263 (1.12), 1.275 (5.07), 2.198 (1.02), 2.216 (1.39), 2.235 (1.08), 2.327 (0.48), 2.518 (1.86), 2.523 (1.31), 2.669 (0.50), 3.154 (0.97), 3.160 (0.62), 3.172 (1.10), 3.178 (1.98), 3.195 (1.89), 3.205 (0.59), 3.212 (0.55), 3.223 (1.89), 3.229 (0.43), 3.240 (1.96), 3.246 (1.11), 3.258 (0.73), 3.264 (1.08), 3.282 (0.43), 3.294 (1.25), 3.315 (1.96), 3.752 (0.57), 3.766 (0.61), 3.781 (0.78), 3.785 (1.38), 3.788 (0.87), 3.795 (0.82), 3.799 (1.37), 3.802 (0.88), 3.827 (0.78), 3.830 (1.30), 3.834 (0.84), 3.840 (0.86), 3.843 (1.40), 3.847 (0.88), 3.859 (0.56), 3.863 (0.85), 3.871 (2.09), 3.879 (16.00), 3.893 (0.95), 3.899 (0.62), 4.073 (2.13), 4.083 (1.60), 4.104 (2.94), 4.112 (3.76), 4.136 (4.76), 4.166 (1.65), 4.176 (1.57), 4.180 (1.54), 4.193 (1.66), 4.202 (2.49), 4.209 (3.32), 4.220 (5.29), 4.238 (4.38), 4.256 (1.32), 4.266 (0.46), 4.275 (2.54), 4.306 (2.13), 4.664 (0.41), 4.676 (0.43), 4.715 (2.03), 4.718 (2.03), 4.740 (1.46), 4.744 (1.42), 4.772 (0.75), 4.778 (0.75), 4.782 (0.84), 4.813 (0.46), 4.825 (0.47), 4.994 (0.53), 4.997 (1.18), 5.002 (1.47), 5.005 (0.72), 5.025 (2.58), 5.028 (2.29), 5.064 (0.74), 5.069 (1.71), 5.073 (1.57), 5.078 (0.56), 5.422 (0.64), 5.435 (0.59), 5.447 (0.74), 5.453 (0.44), 5.460 (0.43), 5.465 (0.73), 5.477 (0.54), 5.491 (0.65), 5.686 (0.49), 5.700 (1.05), 5.713 (0.84), 5.726 (1.09), 5.729 (0.57), 5.740 (0.66), 5.743 (1.07), 5.759 (11.36), 5.769 (0.93), 5.783 (0.49), 6.884 (1.89), 6.901 (1.89), 6.992 (1.64), 6.994 (1.69), 7.010 (2.32), 7.013 (2.14), 7.084 (2.02), 7.105 (2.34), 7.122 (1.52), 7.367 (1.37), 7.388 (2.49), 7.407 (1.98), 7.452 (2.66), 7.472 (1.54), 7.500 (0.56), 7.512 (1.81), 7.517 (3.06), 7.527 (3.52), 7.536 (3.05), 7.540 (2.04), 7.553 (0.61), 7.770 (1.85), 7.773 (1.89), 7.791 (1.73), 7.793 (1.68), 7.861 (1.55), 7.865 (1.10), 7.873 (0.89), 7.877 (1.00), 7.879 (1.03), 7.885 (1.30), 8.233 (1.33), 8.240 (0.92), 8.257 (1.23).

Intermediate 292

(rac)-ethyl (E/Z)-3-(ethoxymethyl)-1-methyl-7-[3-(naphthalen-1-yloxy)propyl]-1,10,13,15-tetrahydro-pyrazolo[4',3':9,10][1,6]oxazacycloundecino[8,7,6-hi]indole-8-carboxylate

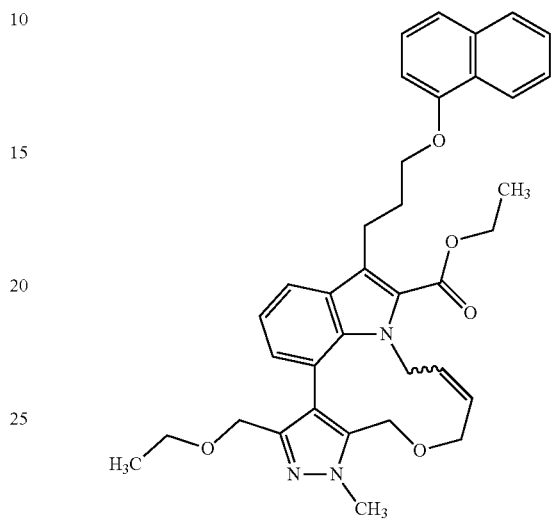

A solution of ethyl 7-{3-(ethoxymethyl)-1-methyl-5-[(prop-2-en-1-yloxy)methyl]-1H-pyrazol-4-yl}-3-[3-(naphthalen-1-yloxy)propyl]-1-(prop-2-en-1-yl)-1H-indole-2-carboxylate (710 mg, 1.14 mmol) in dichloromethane (15 ml, 230 mmol) was purged with argon several times. (1,3-Bis(2,4,6-trimethylphenyl)-2-imidazolidinylidene)dichloro(phenylmethylene)(tricyclohexylphosphine)ruthenium benzylidene[1,3-bis(2,4,6-trimethylphenyl)imidazolidin-2-ylidene]dichlororuthenium-tricyclohexylphosphane (1:1) (97.0 mg, 114 μmol) (Grubbs 2$^{nd}$ generation catalyst) was added and the reaction mixture was stirred for 24 hours at room temperature. For work-up, the reaction mixture was concentrated under reduced pressure and the residue was purified by flash chromatography (hexane/ethyl acetate gradient, 12%→100% ethyl acetate) to give the title compound (320 mg).

$^1$H-NMR (400 MHz, DMSO-d6) δ [ppm]: 0.723 (5.17), 0.740 (11.35), 0.758 (5.59), 0.777 (1.04), 0.795 (0.46), 1.259 (5.02), 1.277 (11.13), 1.295 (5.10), 2.221 (0.99), 2.238 (1.43), 2.255 (0.99), 2.518 (1.98), 2.523 (1.44), 2.938 (1.23), 2.943 (0.54), 2.955 (1.29), 2.961 (1.66), 2.973 (0.44), 2.978 (1.65), 2.996 (0.46), 3.059 (0.45), 3.076 (1.58), 3.082 (0.46), 3.094 (1.74), 3.100 (1.31), 3.112 (0.51), 3.117 (1.16), 3.287 (0.47), 3.302 (0.59), 3.320 (1.18), 3.347 (0.62), 3.367 (0.95), 3.385 (0.54), 3.401 (0.48), 3.471 (0.59), 3.502 (1.04), 3.533 (0.72), 3.767 (0.62), 3.777 (0.72), 3.799 (0.64), 3.811 (0.53), 3.872 (2.04), 3.901 (3.80), 3.912 (16.00), 3.956 (3.20), 3.984 (1.91), 4.206 (2.74), 4.219 (2.98), 4.234 (1.63), 4.240 (2.58), 4.249 (1.94), 4.257 (0.54), 4.260 (0.74), 4.266 (1.87), 4.278 (1.86), 4.284 (0.68), 4.296 (1.76), 4.305 (0.78), 4.314 (0.51), 4.323 (0.77), 4.671 (0.44), 4.699 (0.61), 4.713 (0.83), 4.720 (2.16), 4.739 (0.79), 4.754 (1.94), 4.952 (1.23), 4.983 (1.44), 5.005 (0.57), 5.181 (0.56), 5.192 (0.57), 5.759 (0.78), 6.821 (1.91), 6.824 (2.01), 6.839 (2.20), 6.841 (2.07), 6.890 (1.68), 6.907 (1.76), 7.057 (1.87), 7.076 (1.87), 7.077 (2.24), 7.095 (1.77), 7.369 (1.33), 7.390 (2.46), 7.409 (1.98), 7.450 (2.56), 7.471 (1.47), 7.490 (0.59), 7.502 (1.43), 7.507 (1.38), 7.510 (0.91), 7.513 (1.71), 7.520 (3.27), 7.527 (1.71), 7.532 (1.55), 7.537 (1.74), 7.549 (0.65), 7.554 (0.42), 7.771 (1.88), 7.773 (1.97), 7.791 (1.77), 7.794 (1.73), 7.860 (1.49), 7.868 (0.81), 7.878 (1.46), 7.884 (1.26), 8.208 (1.25), 8.214 (1.18), 8.226 (0.69), 8.231 (1.11), 8.233 (1.19).

Intermediate 293

(rac)-ethyl 3-(ethoxymethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate and (rac)-ethyl 3-(ethoxymethyl)-1-methyl-7-[3-(5,6,7,8-tetrahydronaphthalen-1-yloxy)propyl]-1,10,11,12,13,15-hexahydropyrazolo[4',3':9,10][1,6]oxazacycloundecino[8,7,6-hi]indole-8-carboxylate

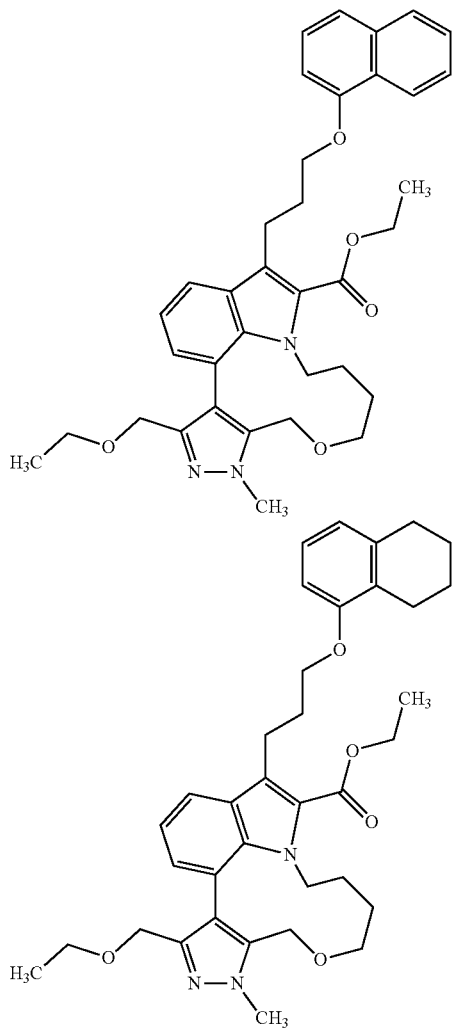

A suspension of (rac)-ethyl (11Z)-3-(ethoxymethyl)-1-methyl-7-[3-(naphthalen-1-yloxy)propyl]-1,10,13,15-tetrahydropyrazolo[4',3':9,10][1,6]oxazacycloundecino[8,7,6-hi]indole-8-carboxylate (320 mg, 539 µmol) and Pd/C (115 mg, 10% purity, 108 µmol) in ethanol (9.4 ml) was stirred under an atmosphere of hydrogen at room temperature for 28 hours. For work-up the mixture was filtered through a pad of celite. The residue was washed with THF and the filtrate was concentrated under reduced pressure to give a mixture of the title compounds (280 mg).

Intermediate 300 ethyl 4-bromo-5-(bromomethyl)-1-methyl-1H-pyrazole-3-carboxylate

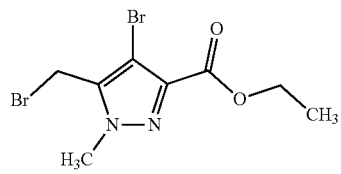

N-Bromosuccinimide (112 g, 624 mmol) was added to a solution of ethyl 1,5-dimethyl-1H-pyrazole-3-carboxylate (50.0 g, 297 mmol, CAS No 5744-51-4) in 1,2-dichloroethane (1.0 l) and the mixture was stirred for 15 h at 80° C. Upon cooling, dichloromethane (1 l) was added and the mixture was washed twice with water (2.5 l), dried and concentrated. The residue was purified by flash chromatography (750 g Biotage SNAP cartridge, hexane/dichloromethane gradient) to give the title compound (82.1 g, 85% yield).

$^1$H-NMR (400 MHz, DMSO-$d_6$): δ [ppm]=4.78 (s, 2H), 4.28 (q, 2H), 3.97 (s, 3H), 1.29 (t, 3H)

Intermediate 301

(rac)-ethyl 3-(methoxymethyl)-1-methyl-7-[3-(naphthalen-1-yloxy)propyl]-1,11,12,13,14,16-hexahydro-10H-pyrazolo[3',4':3,4][1,7]oxazacyclododecino[5,6,7-hi]indole-8-carboxylate

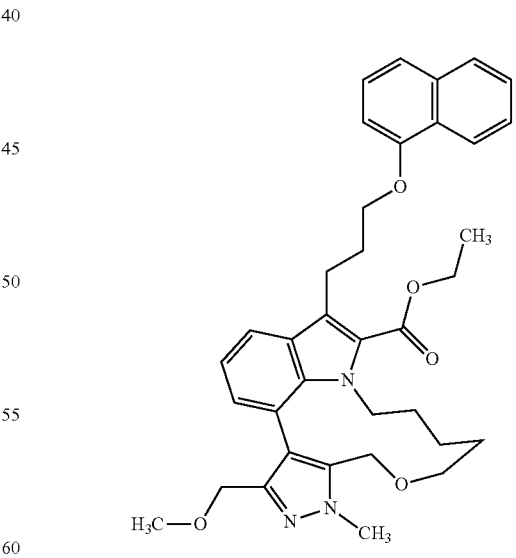

A mixture of ethyl 7-[5-(hydroxymethyl)-3-(methoxymethyl)-1-methyl-1H-pyrazol-4-yl]-3-[3-(naphthalen-1-yloxy)propyl]-1H-indole-2-carboxylate (377 mg, 715 µmol; see Intermediate 285), 1,5-diiodopentane (110 µl, 710 µmol) and caesium carbonate (698 mg, 2.14 mmol) in diethylenglycoldimethylether (41 ml, 290 mmol) was stirred for 5 days at room temperature. For work-up, the reaction mixture was concentrated under reduced pressure. The residue was combined with another batch which had been prepared accordingly, and the mixture was purified twice by flash chromatography (dichloromethane/methanol gradient, 0%→10% methanol followed by dichloromethane/acetone gradient 0→25% acetone) to give the title compound (86 mg) as a racemic mixture.

¹H-NMR (400 MHz, DMSO-d6) δ [ppm]: 0.848 (0.40), 1.233 (0.71), 1.264 (3.17), 1.271 (0.77), 1.282 (6.77), 1.288 (1.13), 1.299 (3.07), 1.305 (0.51), 1.466 (0.61), 1.484 (0.75), 1.503 (0.50), 2.191 (0.61), 2.210 (0.85), 2.228 (0.65), 2.326 (0.45), 2.518 (1.86), 2.522 (1.19), 2.669 (0.46), 3.045 (0.83), 3.052 (16.00), 3.073 (0.42), 3.279 (0.79), 3.298 (1.20), 3.317 (0.89), 3.917 (9.24), 3.933 (0.96), 4.024 (1.45), 4.053 (2.11), 4.107 (0.40), 4.132 (0.41), 4.152 (2.08), 4.181 (1.47), 4.187 (0.81), 4.197 (0.79), 4.210 (1.06), 4.219 (1.50), 4.225 (2.19), 4.242 (1.65), 4.259 (2.62), 4.277 (2.38), 4.294 (1.42), 4.308 (0.87), 4.326 (0.61), 4.340 (0.52), 4.796 (0.57), 4.801 (0.81), 4.810 (0.85), 4.838 (1.71), 4.840 (1.73), 5.207 (0.79), 5.218 (1.04), 5.221 (1.20), 5.232 (0.85), 5.438 (0.49), 6.908 (1.15), 6.925 (1.20), 7.022 (0.77), 7.026 (0.89), 7.040 (1.59), 7.043 (1.42), 7.067 (1.36), 7.087 (1.48), 7.105 (0.74), 7.376 (0.89), 7.396 (1.66), 7.415 (1.40), 7.455 (1.75), 7.476 (0.97), 7.514 (1.11), 7.519 (1.76), 7.529 (2.03), 7.539 (1.70), 7.542 (1.27), 7.554 (0.40), 7.740 (1.12), 7.744 (1.15), 7.760 (1.04), 7.763 (1.01), 7.864 (1.00), 7.868 (0.70), 7.879 (0.63), 7.882 (0.65), 7.887 (0.86), 8.231 (0.82), 8.239 (0.56), 8.255 (0.73).

Intermediate 302

(rac)-ethyl 3-[(3,3-difluoroazetidin-1-yl)methyl]-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate

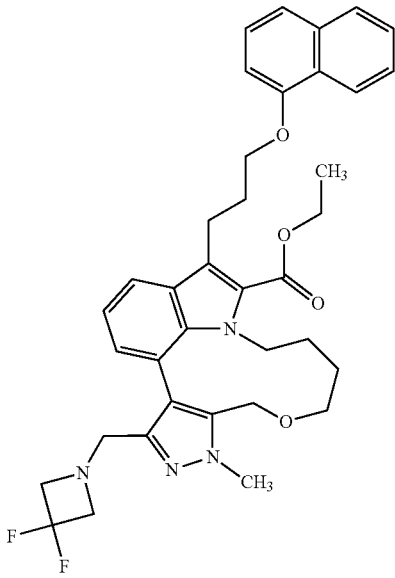 [SMILES: CCOC(=O)c1c(CCCOc2cccc3ccccc23)c2cccc3c2n1CCCCOCc1c-3c(CN2CC(F)(F)C2)nn1C]

To a solution of 3,3-difluoroazetidine hydrochloride salt (82.2 mg, 634 μmol) in DMF (2.0 ml) was added caesium carbonate (413 mg, 1.27 mmol) and the mixture was stirred for 10 minutes. (rac)-ethyl 3-(bromomethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (200 mg, 317 μmol; see Intermediate 258) was added and the reaction mixture was stirred for 16 hours at 40° C. For work-up the reaction mixture was concentrated under reduced pressure and the crude product was purified by flash chromatography (dichlormethane/acetone gradient, 0%→30% acetone) to give the title compound (124 mg).

LC-MS (Method 1): Rt=1.65 min; MS (ESIpos): m/z=644 [M+H]⁺

¹H-NMR (400 MHz, DMSO-d6) δ [ppm]: 1.018 (1.05), 1.236 (1.75), 1.259 (5.63), 1.277 (11.14), 1.295 (5.13), 2.085 (1.27), 2.204 (0.86), 2.221 (1.25), 2.239 (0.93), 2.318 (0.46), 2.323 (1.03), 2.327 (1.49), 2.331 (1.03), 2.336 (0.46), 2.518 (5.27), 2.523 (3.66), 2.660 (0.50), 2.665 (1.10), 2.669 (1.53), 2.673 (1.08), 2.678 (0.50), 2.728 (5.22), 2.789 (0.72), 2.799 (0.50), 2.818 (0.74), 2.889 (6.66), 3.197 (1.10), 3.230 (1.77), 3.253 (0.48), 3.269 (0.60), 3.288 (0.96), 3.307 (0.69), 3.318 (2.44), 3.349 (4.10), 3.359 (2.40), 3.363 (2.42), 3.368 (3.69), 3.381 (2.04), 3.394 (1.49), 3.399 (1.96), 3.408 (0.91), 3.424 (0.91), 3.438 (0.77), 3.888 (16.00), 3.906 (0.67), 3.971 (0.55), 3.988 (0.67), 4.006 (0.67), 4.183 (0.55), 4.201 (1.80), 4.210 (2.49), 4.219 (1.84), 4.228 (3.11), 4.231 (2.51), 4.245 (1.96), 4.258 (0.84), 4.265 (2.18), 4.276 (1.92), 4.285 (0.41), 4.293 (1.70), 4.303 (0.98), 4.311 (0.53), 4.320 (0.96), 4.408 (0.84), 4.420 (0.46), 4.432 (0.41), 4.444 (0.74), 4.636 (2.04), 4.669 (1.82), 6.881 (3.40), 6.884 (3.69), 6.901 (3.98), 7.053 (1.92), 7.071 (1.84), 7.074 (2.20), 7.091 (1.63), 7.363 (1.44), 7.384 (2.59), 7.403 (1.99), 7.451 (2.59), 7.472 (1.53), 7.498 (0.55), 7.511 (1.56), 7.517 (2.25), 7.526 (3.59), 7.535 (2.42), 7.541 (1.80), 7.553 (0.62), 7.778 (1.77), 7.781 (1.96), 7.798 (1.75), 7.801 (1.72), 7.863 (1.46), 7.871 (0.77), 7.880 (1.10), 7.886 (1.27), 7.951 (0.79), 8.222 (1.32), 8.229 (1.13), 8.237 (0.60), 8.246 (1.20).

Intermediate 303 ethyl 1-{4-[(tert-butoxycarbonyl)(methyl)amino]butyl}-7-[5-(hydroxymethyl)-3-(methoxymethyl)-1-methyl-1H-pyrazol-4-yl]-3-[3-(naphthalen-1-yloxy)propyl]-1H-indole-2-carboxylate

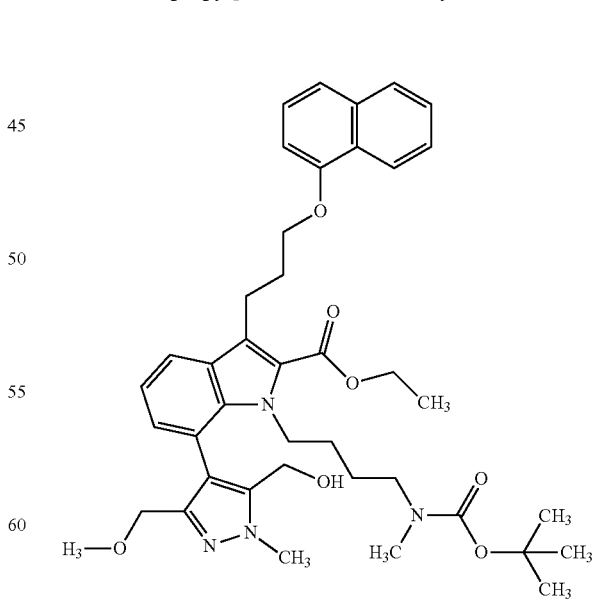

A mixture of ethyl 7-[5-(hydroxymethyl)-3-(methoxymethyl)-1-methyl-1H-pyrazol-4-yl]-3-[3-(naphthalen-1-yloxy)propyl]-1H-indole-2-carboxylate (420 mg, 796 μmol;

Intermediate 304 ethyl 7-[5-(bromomethyl)-3-(methoxymethyl)-1-methyl-1H-pyrazol-4-yl]-1-{4-[(tert-butoxycarbonyl)(methyl)amino]butyl}-3-[3-(naphthalen-1-yloxy)propyl]-1H-indole-2-carboxylate see Intermediate 285), tert-butyl (4-bromobutyl)methylcarbamate (233 mg, 876 μmol; see Intermediate 2) and caesium carbonate (778 mg, 2.39 mmol) in DMF (10 ml) was stirred for 3 days at room temperature. Tert-butyl (4-bromobutyl)methylcarbamate (0.3 eq, see Intermediate 2) was added and the reaction was stirred for additional 7 days at room temperature. For work-up the reaction mixture was concentrated under reduced pressure and the crude product was purified by flash chromatography (dichlormethane/acetone gradient, 0%→50% acetone) to give the title compound (280 mg).

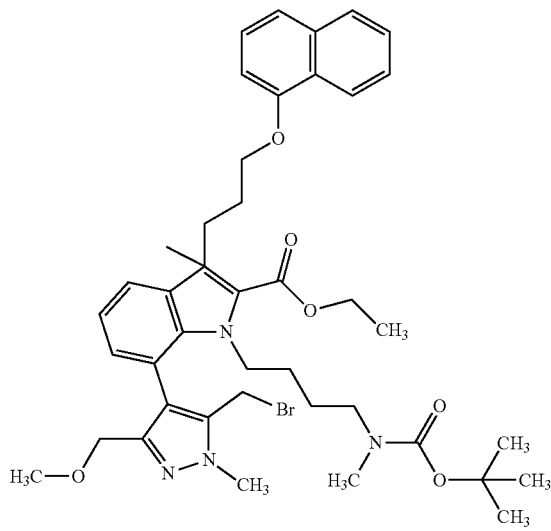

To a solution of ethyl 1-{4-[(tert-butoxycarbonyl)(methyl)amino]butyl}-7-[5-(hydroxymethyl)-3-(methoxymethyl)-1-methyl-1H-pyrazol-4-yl]-3-[3-(naphthalen-1-yloxy)propyl]-1H-indole-2-carboxylate (275 mg, 386 μmol; see Intermediate 303) in dichloromethane (10 ml) triphenylphosphine (243 mg, 926 μmol) was added at 0° C. and the mixture was stirred at 0° C. for 10 min. Tetrabromomethane (281 mg, 849 μmol) was added and the reaction mixture was stirred at room temperature for 90 minutes. For work-up the reaction mixture was concentrated under reduced pressure and the crude title (299 mg) compound thus obtained was used in the following steps without further purification.

Intermediate 305 ethyl 7-[5-(bromomethyl)-3-(methoxymethyl)-1-methyl-1H-pyrazol-4-yl]-1-[4-(methylamino)butyl]-3-[3-(naphthalen-1-yloxy)propyl]-1H-indole-2-carboxylate hydrochloric acid salt

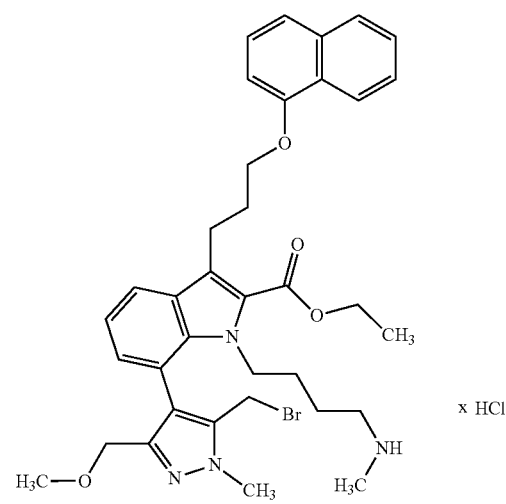 [SMILES: CCOC(=O)c1c(CCCOc2cccc3ccccc23)c2cccc(-c3c(COC)nn(C)c3CBr)c2n1CCCCNC ; Cl]

To a solution of crude ethyl 7-[5-(bromomethyl)-3-(methoxymethyl)-1-methyl-1H-pyrazol-4-yl]-1-{4-[(tert-butoxycarbonyl)(methyl)amino]butyl}-3-[3-(naphthalen-1-yloxy)propyl]-1H-indole-2-carboxylate (299 mg; see Intermediate 304) in methanol (7.0 ml) was added a 4 M solution of HCL in dioxan (7.0 ml, 28 mmol) at 0° C. and the mixture was stirred for 90 minutes at room temperature. For work-up the mixture was concentrated under reduced pressure and the crude title compound (269 mg) was used for the subsequent steps without further purification.

Intermediate 306

(rac)-ethyl 3-(methoxymethyl)-1,14-dimethyl-7-[3-(naphthalen-1-yloxy)propyl]-10,11,12,13,14,15-hexahydro-1H-pyrazolo[3',4':8,9][1,6]diazacycloundecino[10,11,1-hi]indole-8-carboxylate

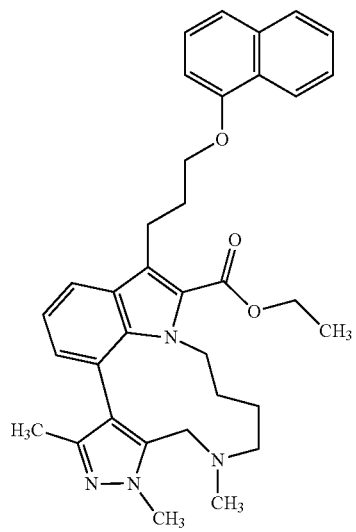 [SMILES: CCOC(=O)c1c(CCCOc2cccc3ccccc23)c2cccc3c2n1CCCCN(C)Cc1c-3c(C)nn1C]

To a solution of ethyl 7-[5-(bromomethyl)-3-(methoxymethyl)-1-methyl-1H-pyrazol-4-yl]-1-[4-(methylamino)butyl]-3-[3-(naphthalen-1-yloxy)propyl]-1H-indole-2-carboxylate hydrochloric acid salt (269 mg; see Intermediate 305) in DMF (35 ml) was added caesium carbonate (650 mg, 1.99 mmol) and the reaction mixture was stirred at room temperature for 2 days. For work-up the reaction mixture was concentrated under reduced pressure and the crude product was purified by flash chromatography (hexane/ethyl acetate gradient, 25%→100% ethyl acetate) to give the title compound (191 mg).

LC-MS (Method 2): Rt=1.74 min; MS (ESIpos): m/z=596 [M+H]$^+$ $^1$H-NMR (400 MHz, DMSO-d6) δ [ppm]: 1.154 (0.66), 1.172 (1.35), 1.190 (0.66), 1.261 (2.71), 1.268 (0.67), 1.279 (5.99), 1.297 (2.82), 1.987 (2.11), 2.157 (5.17), 2.195 (0.49), 2.212 (0.72), 2.230 (0.51), 2.518 (1.71), 2.523 (1.13), 2.955 (16.00), 3.238 (0.79), 3.271 (0.93), 3.279 (0.59), 3.356 (0.48), 3.677 (0.86), 3.710 (0.76), 3.885 (0.68), 3.896 (8.26), 3.936 (0.65), 3.965 (2.16), 3.980 (2.16), 4.009 (0.61), 4.017 (0.53), 4.035 (0.51), 4.198 (0.67), 4.208 (0.84), 4.216 (0.92), 4.225 (2.15), 4.233 (0.57), 4.243 (1.33), 4.260 (0.48), 4.277 (0.91), 4.295 (0.87), 4.304 (0.49), 4.321 (0.48), 6.836 (0.93), 6.839 (1.09), 6.853 (1.13), 6.857 (1.08), 6.898 (0.90), 6.915 (0.93), 7.029 (0.93), 7.047 (0.96), 7.049 (1.14), 7.067 (0.85), 7.371 (0.69), 7.392 (1.28), 7.411 (1.07), 7.455 (1.30), 7.475 (0.74), 7.518 (1.03), 7.520 (1.16), 7.523 (0.97), 7.532 (1.33), 7.539 (1.02), 7.542 (1.19), 7.544 (1.21), 7.747 (0.96), 7.751 (1.00), 7.768 (0.93), 7.771 (0.86), 7.865 (0.75), 7.868 (0.49), 7.877 (0.67), 7.882 (0.49), 7.888 (0.64), 8.248 (0.69), 8.255 (0.40), 8.259 (0.55), 8.272 (0.61).

Intermediate 307

[4-bromo-1-methyl-5-(trifluoromethyl)-1H-pyrazol-3-yl]methanol

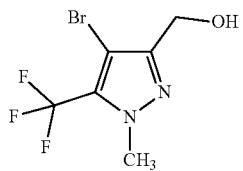

To a solution of 4-bromo-1-methyl-5-(trifluoromethyl)-1H-pyrazole-3-carboxylic acid (1.50 g, 5.49 mmol, CAS 497833-03-1) in THF (14 ml) was added 1,1-carbonyldiimidazole (1.34 g, 8.24 mmol) and the suspension was stirred for 1 hour at room temperature. The mixture was cooled down to 0° C. and a solution of sodium borohydride (624 mg, 16.5 mmol) in water (14 ml) was added and the reaction mixture was stirred for 5 hours at room temperature. For work-up the reaction mixture was poured into an aqueous solution of citric acid (10%) and the mixture was extracted with ethyl acetate. The combined organic phases were washed with brine and dried over sodium sulfate. After filtration and removal of the solvents the crude product was used without further purification in the subsequent steps.

LC-MS (Method 2): Rt=0.89 min; MS (ESIpos): m/z=259 [M+H]$^+$

Intermediate 308 ethyl 7-[3-(hydroxymethyl)-1-methyl-5-(trifluoromethyl)-1H-pyrazol-4-yl]-3-[3-(naphthalen-1-yloxy)propyl]-1H-indole-2-carboxylate

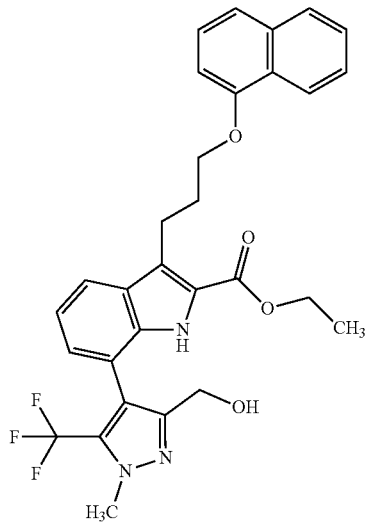

A solution of ethyl 3-[3-(naphthalen-1-yloxy)propyl]-7-(4,4,5,5-tetramethyl-1,3,2-dioxaborolan-2-yl)-1H-indole-2-carboxylate (1.85 g, 3.71 mmol; see Intermediate 5) and [4-bromo-1-methyl-5-(trifluoromethyl)-1H-pyrazol-3-yl]methanol (800 mg, 3.09 mmol; see Intermediate 307) in THF (34 ml) was degassed and purged with argon several times. An aqueous solution of potassium carbonate (3.7 ml, 2.0 M, 7.4 mmol) and Tetrakis(triphenylphosphine)palladium(0) (Pd(PPh$_3$)$_4$ (428 mg, 371 μmol) were added and the mixture was purged with argon for 3 minutes. The reaction was stirred at 110° C. for 3 h in a microwave. For work-up the reaction was concentrated under reduced pressure and the residue was purified by flash chromatography (hexane/ethyl acetate gradient, 12%→100% ethyl acetate) to give the title compound (1.2 g).

LC-MS (Method 2): Rt=1.56 min; MS (ESIneg): m/z=550 [M−H]$^−$ $^1$H-NMR (400 MHz, DMSO-d6) δ [ppm]: 0.967 (1.07), 0.991 (0.72), 1.095 (1.13), 1.107 (4.32), 1.133 (7.39), 1.152 (16.00), 1.169 (7.20), 1.233 (0.66), 1.414 (0.58), 1.903 (1.47), 2.047 (4.64), 2.116 (0.43), 2.172 (1.53), 2.190 (2.39), 2.207 (1.75), 2.239 (0.85), 2.248 (0.72), 2.262 (1.51), 2.268 (1.60), 2.283 (3.56), 2.308 (2.71), 2.312 (2.75), 2.323 (1.90), 2.327 (2.28), 2.332 (2.02), 2.359 (0.83), 2.518 (5.69), 2.523 (4.05), 2.540 (2.28), 2.660 (0.47), 2.665 (0.98), 2.669 (1.34), 2.674 (0.94), 2.679 (0.51), 2.744 (0.83), 2.820 (1.73), 2.839 (5.43), 2.857 (5.18), 2.875 (1.64), 3.120 (0.49), 3.138 (0.87), 3.152 (0.92), 3.171 (1.19), 3.189 (0.72), 3.316 (4.58), 3.336 (9.33), 3.348 (11.31), 3.359 (8.07), 3.399 (2.09), 3.807 (0.60), 3.859 (1.04), 4.139 (1.81), 4.155 (3.71), 4.172 (1.83), 4.245 (2.15), 4.279 (2.39), 4.615 (2.60), 4.648 (2.39), 4.689 (0.81), 4.722 (0.70), 6.654 (1.70), 6.672 (1.92), 6.834 (2.22), 6.852 (2.41), 6.904 (1.77), 6.923 (2.49), 6.941 (1.58), 7.333 (1.60), 7.354 (3.00), 7.373 (2.28), 7.424 (3.39), 7.445 (2.07), 7.476 (0.49), 7.480 (0.75), 7.493 (2.00), 7.497 (2.02), 7.501 (2.56), 7.509 (4.37), 7.517 (2.54), 7.520 (2.26), 7.525 (2.22), 7.538 (0.83), 7.542 (0.51), 7.585 (1.94), 7.603 (1.79), 7.843 (2.05), 7.851 (1.04), 7.861 (1.75), 7.867 (1.73), 8.226 (1.73), 8.232 (1.62), 8.250 (1.60).

Intermediate 309

(rac)-ethyl (11Z)-2-methyl-7-[3-(naphthalen-1-yloxy)propyl]-3-(trifluoromethyl)-2,10,13,15-tetrahydropyrazolo[4',3':9,10][1,6]oxazacycloundecino[8,7,6-hi]indole-8-carboxylate

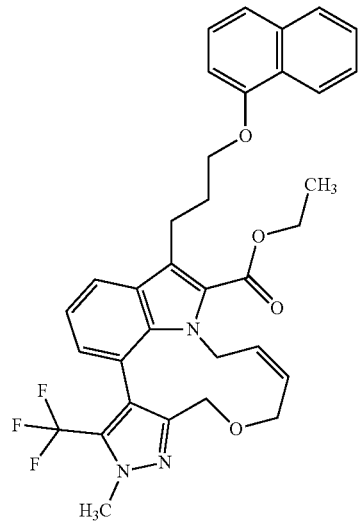 [SMILES: CCOC(=O)c1c(CCCOc2cccc3ccccc23)c2cccc3c2n1C/C=C\COCc1nn(C)c(C(F)(F)F)c1-3]

To a solution of ethyl 7-[3-(hydroxymethyl)-1-methyl-5-(trifluoromethyl)-1H-pyrazol-4-yl]-3-[3-(naphthalen-1-yloxy)propyl]-1H-indole-2-carboxylate (600 mg, 1.09 mmol; see Intermediate 308) in acetonitrile (12 ml) was added caesium carbonate (1.79 g, 5.44 mmol) and the mixture was stirred for 10 min at room temperature. (2Z)-1,4-dichlorobut-2-ene (130 μl, 1.2 mmol) and sodium iodide (329 mg, 2.18 mmol) were added and the reaction mixture was stirred for 20 hours at 40° C. For work-up the reaction mixture was poured into water. The mixture was extracted with ethyl acetate. The combined organic phases washed with brine and dried over sodium sulfate. After filtration and removal of the solvent the crude product was purified by flash chromatography (dichloromethane/acetone gradient, 0%→40% acetone) to give the title compound (346 mg).

$^1$H-NMR (400 MHz, DMSO-d6) δ [ppm]: 1.233 (0.53), 1.269 (7.18), 1.287 (16.00), 1.304 (7.32), 1.987 (0.61), 2.197 (0.49), 2.215 (1.34), 2.231 (1.99), 2.249 (1.35), 2.266 (0.47), 2.323 (0.53), 2.327 (0.78), 2.332 (0.55), 2.518 (3.36), 2.523 (2.37), 2.665 (0.53), 2.669 (0.75), 2.673 (0.53), 3.278 (0.60), 3.294 (0.91), 3.312 (1.61), 3.342 (1.80), 3.361 (0.82), 3.376 (0.61), 3.638 (0.65), 3.652 (0.83), 3.668 (1.53), 3.682 (1.32), 3.711 (1.35), 3.737 (1.52), 3.767 (0.75), 4.099 (10.77), 4.102 (11.24), 4.211 (0.80), 4.221 (2.04), 4.229 (2.52), 4.239 (5.02), 4.247 (2.65), 4.251 (2.24), 4.256 (3.18), 4.273 (0.78), 4.273 (5.98), 4.285 (1.01), 4.291 (0.91), 4.303 (2.52), 4.312 (0.48), 4.321 (2.43), 4.330 (1.35), 4.338 (0.70), 4.347 (1.35), 4.365 (0.40), 4.436 (3.46), 4.470 (2.75), 4.561 (0.86), 4.588 (0.96), 4.600 (1.13), 4.627 (1.18), 4.926 (1.25), 4.963 (1.00), 5.171 (0.61), 5.178 (0.61), 5.198 (1.31), 5.205 (1.31), 5.225 (0.86), 5.231 (0.83), 5.288 (0.61), 5.302 (0.64), 5.316 (0.93), 5.328 (0.87), 5.341 (0.44), 5.759 (1.40), 6.910 (2.43), 6.927 (2.60), 6.956 (2.58), 6.960 (2.73), 6.974 (3.33), 6.977 (3.27), 7.084 (2.89), 7.102 (2.78), 7.104 (3.41), 7.122 (2.22), 7.376 (2.04), 7.396 (3.57), 7.415 (2.95), 7.456 (3.65), 7.476 (2.08), 7.487 (0.70), 7.491 (0.92), 7.504 (2.30), 7.508 (1.99), 7.514 (2.39), 7.521 (5.00), 7.528 (2.49), 7.533 (2.26), 7.538 (2.57), 7.551 (1.01), 7.555 (0.65), 7.810 (2.67), 7.812 (2.85), 7.830 (2.50), 7.832 (2.58), 7.863 (2.12), 7.870 (1.25), 7.880 (2.10), 7.886 (1.84), 8.215 (1.83), 8.221 (1.76), 8.232 (1.00), 8.237 (1.69), 8.239 (1.84).

Intermediate 310

(rac)-ethyl 2-methyl-7-[3-(naphthalen-1-yloxy)propyl]-3-(trifluoromethyl)-2,10,11,12,13,15-hexahydropyrazolo[4',3':9,10][1,6]oxazacycloundecino[8,7,6-hi]indole-8-carboxylate

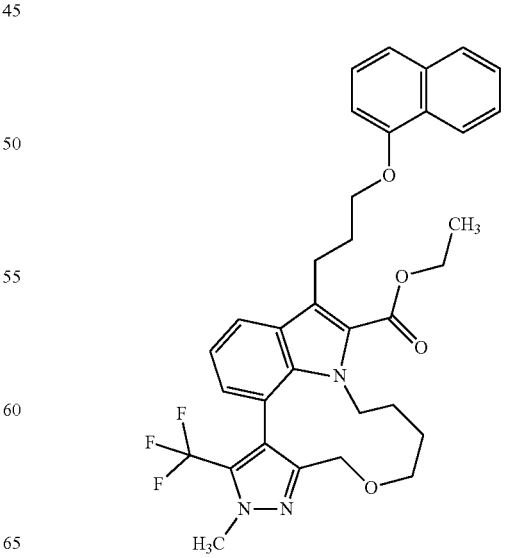

A suspension of (rac)-ethyl (11Z)-2-methyl-7-[3-(naphthalen-1-yloxy)propyl]-3-(trifluoromethyl)-2,10,13,15-tetrahydropyrazolo[4',3':9,10][1,6]oxazacycloundecino[8,7,6-hi]indole-8-carboxylate (346 mg, 574 µmol; see Intermediate 309) and Pd/C (61.0 mg, 57.4 µmol, 10%) in ethanol (15 ml) was stirred under an atmosphere of hydrogen at room temperature for 2 days. For work-up the mixture was filtered through a pad of celite. The residue was washed with ethyl acetate and the filtrate was concentrated under reduced pressure. The residue was purified by flash chromatography (hexane/acetone gradient, 6%→40% acetone) to give the title compound (130 mg).

LC-MS (Method 2): Rt=1.72 min; MS (ESIpos): m/z=606 [M+H]$^+$ $^1$H-NMR (400 MHz, DMSO-d6) δ [ppm]: 1.006 (0.60), 1.039 (0.75), 1.070 (1.09), 1.083 (0.79), 1.088 (1.80), 1.106 (1.35), 1.118 (0.86), 1.128 (0.81), 1.144 (1.01), 1.183 (0.81), 1.210 (0.94), 1.233 (1.14), 1.261 (7.39), 1.279 (16.00), 1.296 (7.54), 1.379 (0.77), 2.194 (1.56), 2.211 (2.36), 2.228 (1.76), 2.246 (0.66), 2.322 (0.88), 2.326 (1.26), 2.331 (0.99), 2.522 (8.72), 2.664 (0.88), 2.668 (1.26), 2.673 (1.01), 3.013 (0.49), 3.025 (0.69), 3.039 (1.18), 3.051 (1.26), 3.064 (0.73), 3.076 (0.58), 3.240 (0.73), 3.255 (0.96), 3.274 (1.56), 3.293 (0.86), 3.306 (0.96), 3.353 (1.93), 3.359 (2.08), 3.371 (1.93), 3.378 (1.31), 3.388 (1.33), 3.718 (0.49), 3.732 (0.66), 3.738 (0.71), 3.753 (1.14), 3.767 (0.75), 3.774 (0.84), 3.788 (0.58), 4.064 (13.47), 4.175 (0.69), 4.184 (1.56), 4.201 (3.92), 4.213 (3.21), 4.219 (2.91), 4.229 (3.68), 4.237 (1.52), 4.246 (2.87), 4.264 (4.28), 4.275 (1.69), 4.295 (5.03), 4.302 (1.88), 4.310 (3.08), 4.320 (2.03), 4.328 (1.05), 4.337 (1.61), 4.355 (0.49), 4.509 (3.58), 4.541 (2.93), 6.886 (2.89), 6.905 (3.06), 7.012 (1.95), 7.015 (2.46), 7.030 (3.77), 7.032 (3.92), 7.065 (3.49), 7.084 (4.01), 7.102 (2.14), 7.367 (2.08), 7.387 (3.98), 7.406 (3.08), 7.453 (4.01), 7.474 (2.40), 7.503 (0.77), 7.515 (2.51), 7.519 (4.16), 7.529 (4.90), 7.538 (4.22), 7.543 (3.36), 7.554 (1.01), 7.559 (0.47), 7.778 (2.70), 7.781 (3.15), 7.799 (2.63), 7.802 (2.83), 7.863 (2.23), 7.867 (1.80), 7.877 (1.50), 7.881 (1.59), 7.887 (2.06), 8.243 (1.99), 8.253 (1.46), 8.266 (2.01).

Intermediate 311 ethyl 4-bromo-1-methyl-3-propyl-1H-pyrazole-5-carboxylate

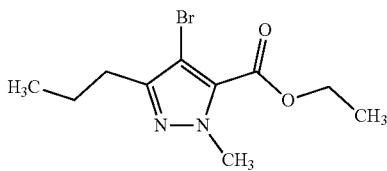

To a solution of ethyl 1-methyl-3-propyl-1H-pyrazole-5-carboxylate (4.85 g, 24.7 mmol, CAS 133261-7-1) in acetonitrile (65 ml), N-Bromosuccinimide (4.67 g, 99% purity, 25.9 mmol) was added and the mixture was stirred at 50° C. for 6 hours. For work-up, the mixture was concentrated and the residue was poured into water. The mixture was extracted with ethyl acetate and the combined organic phases were washed with brine and dried over sodium sulfate. After filtration and removal of the solvent the crude product was purified by flash chromatography (hexane/ethyl acetate gradient, 12%→60% ethyl acetate) to give the title compound (6.2 g).

LC-MS (Method 2): Rt=1.35 min; MS (ESIpos): m/z=277 [M+H]$^+$ $^1$H-NMR (400 MHz, CHLOROFORM-d) δ [ppm]: 0.009 (2.23), 0.887 (3.25), 0.905 (7.10), 0.924 (3.55), 1.345 (3.97), 1.363 (8.40), 1.381 (4.14), 1.509 (4.44), 1.586 (1.12), 1.605 (1.82), 1.624 (1.76), 1.643 (1.07), 2.517 (2.29), 2.537 (2.48), 2.555 (2.07), 2.718 (1.12), 2.908 (0.60), 4.050 (16.00), 4.310 (1.28), 4.328 (3.99), 4.346 (3.96), 4.363 (1.25).

Intermediate 312

(4-bromo-1-methyl-3-propyl-1H-pyrazol-5-yl)methanol

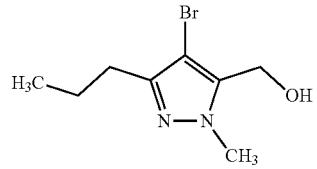

To a solution of ethyl 4-bromo-1-methyl-3-propyl-1H-pyrazole-5-carboxylate (6.20 g, 22.5 mmol; see Intermediate 311) in THF (91 ml) was added a solution of lithium borohydride in THF (14 ml, 2.0 M in THF, 27 mmol) and the mixture was stirred at 60° C. for 20 hours. Sodium sulfate hydrate was added and the mixture was stirred for 1 hour at room temperature. After filtration and removal of the solvents the crude product was purified by flash chromatography (hexane/ethyl acetate gradient, 25%→100% ethyl acetate) to give the title compound (4.8 g).

LC-MS (Method 2): Rt=0.90 min; MS (ESIpos): m/z=233 [M+H]$^+$ $^1$H-NMR (400 MHz, CHLOROFORM-d) δ [ppm]: 0.009 (0.98), 0.883 (3.27), 0.902 (7.26), 0.920 (3.56), 1.571 (1.09), 1.578 (2.83), 1.590 (1.62), 1.609 (1.52), 1.627 (0.98), 1.840 (0.95), 1.856 (2.04), 1.871 (0.95), 2.467 (2.15), 2.484 (1.01), 2.487 (2.17), 2.506 (1.94), 3.828 (16.00), 4.595 (4.77), 4.610 (4.72).

Intermediate 313 ethyl 7-[5-(hydroxymethyl)-1-methyl-3-propyl-1H-pyrazol-4-yl]-6-methyl-3-[3-(naphthalen-1-yloxy)propyl]-1H-indole-2-carboxylate

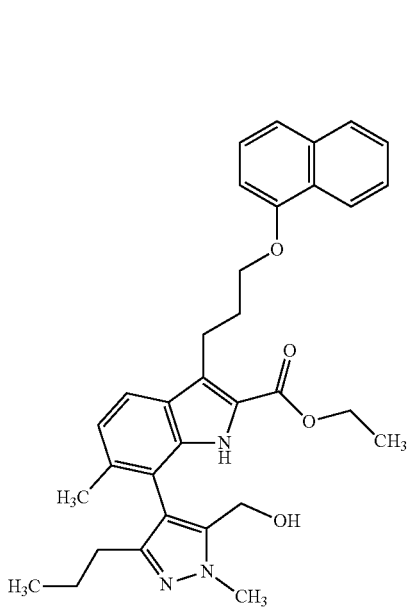

A solution of ethyl 6-methyl-3-[3-(naphthalen-1-yloxy)propyl]-7-(4,4,5,5-tetramethyl-1,3,2-dioxaborolan-2-yl)-1H-indole-2-carboxylate (2.25 g, 4.38 mmol; see Intermediate 19) and (4-bromo-1-methyl-3-propyl-1H-pyrazol-5-yl)methanol (929 mg, 3.98 mmol; see Intermediate 312) in THF (48 ml) was degassed and purged with argon several times. An aqueous 0.5 M solution of potassium carbonate (16 ml, 0.50 M, 8.0 mmol) and XPhos Pd G2 (109 mg, 0.14 mmol) were added and the mixture was purged with argon several times. The reaction was stirred at 50° C. for 3 hours. For work-up the reaction was poured into water and the mixture was extracted with ethyl acetate. The combined organic phases were washed with brine and dried over sodium sulfate. After filtration and removal of the solvent the crude product was purified by flash chromatography (hexane/ethyl acetate gradient, 50%→100% ethyl acetate) to give the title compound (1.4 g).

Intermediate 314

(rac)-ethyl (11Z)-1,4-dimethyl-7-[3-(naphthalen-1-yloxy)propyl]-3-propyl-1,10,13,15-tetrahydropyrazolo[4',3':9,10][1,6]oxazacycloundecino[8,7,6-hi]indole-8-carboxylate

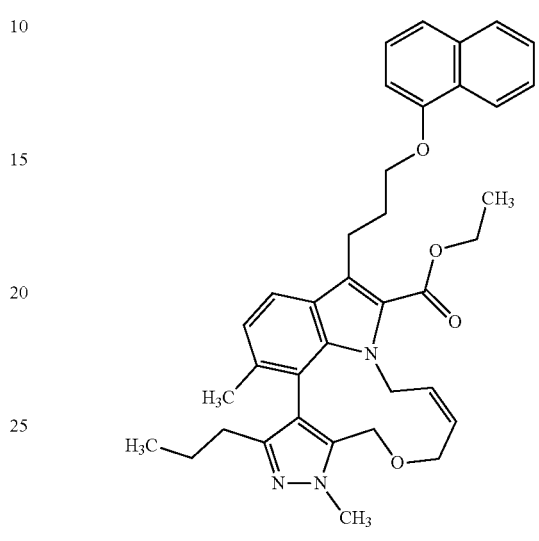

To a solution of ethyl 7-[5-(hydroxymethyl)-1-methyl-3-propyl-1H-pyrazol-4-yl]-6-methyl-3-[3-(naphthalen-1-yloxy)propyl]-1H-indole-2-carboxylate (710 mg, 1.32 mmol; see Intermediate 313) in acetonitrile (15 ml) was added caesium carbonate (2.16 g, 6.58 mmol) and the mixture was stirred for 10 min at room temperature. (2Z)-1,4-dichlorobut-2-ene (160 µl, 95% purity, 1.4 mmol) and sodium iodide (398 mg, 2.63 mmol) were added and the reaction mixture was stirred for 22 hours at 40° C. For work-up the reaction mixture was poured into water. The mixture was extracted with ethyl acetate. The combined organic phases were washed with brine and dried over sodium sulfate. After filtration and removal of the solvent the crude product was purified by flash chromatography (dichloromethane/acetone gradient, 0%→40% acetone) to give the title compound (600 mg).

LC-MS (Method 1): Rt=1.79 min; MS (ESIpos): m/z=593 [M+H]$^+$ $^1$H-NMR (400 MHz, DMSO-d6) δ [ppm]: 0.625 (4.12), 0.644 (10.13), 0.662 (4.60), 1.171 (0.78), 1.180 (0.77), 1.189 (1.40), 1.199 (1.51), 1.208 (1.38), 1.217 (1.67), 1.226 (0.93), 1.235 (1.10), 1.243 (0.48), 1.249 (0.54), 1.258 (5.09), 1.276 (11.21), 1.293 (5.11), 1.873 (12.64), 1.954 (1.46), 1.971 (2.59), 1.988 (1.31), 1.992 (1.14), 2.225 (0.88), 2.243 (1.26), 2.259 (0.92), 2.327 (0.57), 2.518 (2.33), 2.523 (1.60), 2.669 (0.55), 3.275 (0.67), 3.294 (1.48), 3.313 (1.53), 3.347 (0.44), 3.489 (0.60), 3.520 (1.15), 3.551 (0.76), 3.741 (0.63), 3.753 (0.73), 3.774 (0.58), 3.785 (0.56), 3.887 (16.00), 4.093 (1.79), 4.128 (1.89), 4.201 (2.02), 4.219 (2.60), 4.228 (2.68), 4.246 (1.87), 4.255 (0.65), 4.263 (0.61), 4.273 (1.84), 4.290 (1.71), 4.299 (0.88), 4.308 (0.49), 4.317 (0.87), 4.535 (0.51), 4.561 (0.64), 4.575 (0.67), 4.601 (0.78), 4.709 (2.00), 4.742 (1.86), 4.781 (0.53), 4.807 (0.94), 4.834 (0.52), 4.896 (0.87), 4.933 (0.73), 5.133 (0.59), 5.144 (0.58), 6.889 (1.70), 6.906 (1.85), 7.044 (2.33), 7.065 (2.56), 7.367 (1.36), 7.387 (2.52), 7.406 (2.07), 7.450 (2.51), 7.471 (1.48), 7.479 (0.59), 7.483 (0.72), 7.496 (1.52), 7.500 (1.37), 7.503 (0.74), 7.511

(1.66), 7.514 (2.02), 7.517 (2.26), 7.520 (1.76), 7.531 (1.46), 7.535 (1.67), 7.548 (0.73), 7.553 (0.54), 7.653 (2.85), 7.673 (2.52), 7.860 (1.49), 7.865 (0.95), 7.879 (1.65), 7.883 (1.29), 8.198 (1.28), 8.202 (1.36), 8.221 (1.25), 8.222 (1.25).

Intermediate 315

(rac)-ethyl 1,4-dimethyl-7-[3-(naphthalen-1-yloxy)propyl]-3-propyl-1,10,11,12,13,15-hexahydropyrazolo[4',3':9,10][1,6]oxazacycloundecino[8,7,6-hi]indole-8-carboxylate

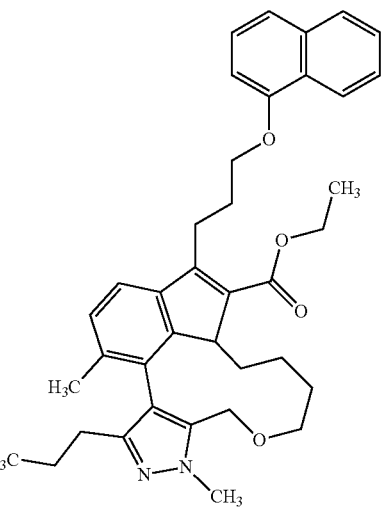

A suspension of (rac)-ethyl (11Z)-1,4-dimethyl-7-[3-(naphthalen-1-yloxy)propyl]-3-propyl-1,10,13,15-tetrahydropyrazolo[4',3':9,10][1,6]oxazacycloundecino[8,7,6-hi]indole-8-carboxylate (600 mg, 1.01 mmol; see Intermediate 314) and Pd/C (108 mg, 10% purity, 101 µmol) in ethanol (27 ml) was stirred under an atmosphere of hydrogen at room temperature for 24 hours. For work-up the mixture was filtered through a pad of celite. The residue was washed with ethyl acetate and the filtrate was concentrated under reduced pressure to give the title compound (575 mg) which was used in the following steps without further purification.

LC-MS (Method 2): Rt=1.80 min; MS (ESIpos): m/z=594 [M+H]$^+$

Intermediate 316 ethyl 1-{3-[(tert-butoxycarbonyl)(methyl)amino]propyl}-7-[5-(hydroxymethyl)-1-methyl-3-propyl-1H-pyrazol-4-yl]-6-methyl-3-[3-(naphthalen-1-yloxy)propyl]-1H-indole-2-carboxylate

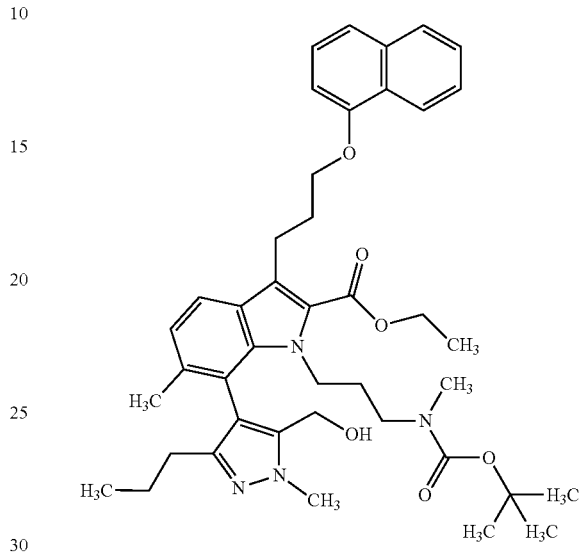

To a solution of ethyl 7-[5-(hydroxymethyl)-1-methyl-3-propyl-1H-pyrazol-4-yl]-6-methyl-3-[3-(naphthalen-1-yloxy)propyl]-1H-indole-2-carboxylate (710 mg, 1.32 mmol; see Intermediate 313) in DMF (17 ml) was added caesium carbonate (2.14 g, 6.58 mmol) and the mixture was stirred for 10 min at room temperature. Tert-butyl (3-bromopropyl)methylcarbamate (423 mg, 94% purity, 1.58 mmol, Intermediate 1) was added and the reaction was stirred for 5 days at room temperature. For work-up the reaction was poured into water. The mixture was extracted with ethyl acetate. The combined organic phases were washed with brine and dried over sodium sulfate. After filtration and removal of the solvent the crude product was purified by flash chromatography (hexane/ethyl acetate gradient, 12%→100% ethyl acetate) to give the title compound (860 mg).

LC-MS (Method 2): Rt=1.80 min; MS (ESIpos): m/z=712 [M+H]$^+$ $^1$H-NMR (400 MHz, DMSO-d6) δ [ppm]: 0.730 (3.84), 0.748 (8.76), 0.767 (4.29), 0.886 (0.67), 1.066 (0.78), 1.232 (1.12), 1.254 (5.57), 1.272 (11.86), 1.290 (7.08), 1.308 (6.06), 1.361 (5.16), 1.380 (6.92), 1.394 (2.65), 1.413 (1.24), 2.028 (16.00), 2.061 (0.65), 2.080 (1.02), 2.097 (1.10), 2.117 (0.71), 2.159 (1.31), 2.178 (2.80), 2.196 (2.80), 2.215 (2.04), 2.233 (0.84), 2.323 (0.84), 2.327 (1.18), 2.332 (0.84), 2.518 (5.39), 2.523 (3.82), 2.603 (4.31), 2.665 (1.24), 2.669 (1.61), 2.673 (1.29), 2.783 (0.59), 3.237 (1.39), 3.257 (2.20), 3.275 (1.41), 3.683 (1.45), 3.809 (0.63), 3.827 (0.67), 3.847 (0.86), 3.891 (4.53), 4.204 (3.08), 4.219 (5.04), 4.236 (3.84), 4.240 (3.41), 4.254 (2.57), 4.258 (2.63), 4.271 (1.00), 4.422 (0.41), 5.178 (0.67), 6.902 (2.14), 6.920 (2.31), 7.017 (2.12), 7.038 (2.33), 7.371 (1.80), 7.392 (3.31), 7.411 (2.78), 7.453 (3.39), 7.474 (1.98), 7.493 (0.43), 7.498 (0.78), 7.510 (2.06), 7.516 (3.29), 7.525 (4.41), 7.535 (3.71), 7.540 (2.35), 7.553 (0.82), 7.557 (0.41), 7.620 (3.06), 7.641 (2.73), 7.863 (1.92), 7.873 (0.98), 7.881 (1.35), 7.887 (1.65), 8.223 (1.65), 8.230 (1.35), 8.238 (0.82), 8.247 (1.55).

Intermediate 317 ethyl 7-[5-(bromomethyl)-1-methyl-3-propyl-1H-pyrazol-4-yl]-1-{3-[(tert-butoxycarbonyl)(methyl)amino]propyl}-6-methyl-3-[3-(naphthalen-1-yloxy)propyl]-1H-indole-2-carboxylate

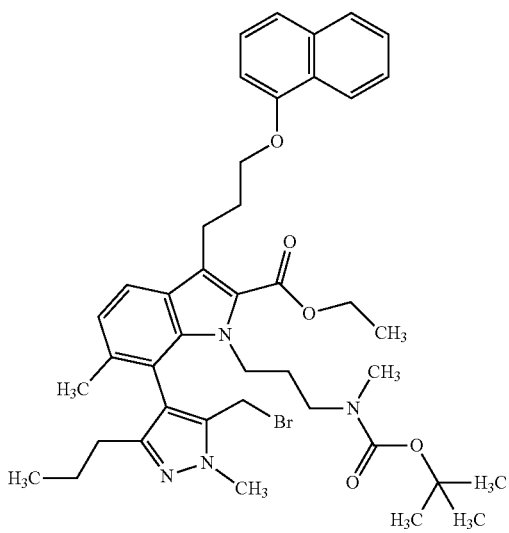 [SMILES: CCCc1nn(C)c(CBr)c1-c1c(C)ccc2c(CCCOc3cccc4ccccc34)c(C(=O)OCC)n(CCCN(C)C(=O)OC(C)(C)C)c12]

To a solution of ethyl 1-{3-[(tert-butoxycarbonyl)(methyl)amino]propyl}-7-[5-(hydroxymethyl)-1-methyl-3-propyl-1H-pyrazol-4-yl]-6-methyl-3-[3-(naphthalen-1-yloxy)propyl]-1H-indole-2-carboxylate (860 mg, 1.21 mmol; see Intermediate 316) in dichloromethane (22 ml) triphenylphosphine (769 mg, 2.90 mmol) was added at 0° C. and the mixture was stirred at 0° C. for 10 min. Tetrabromomethane (963 mg, 2.90 mmol) was added and the reaction was stirred at 0° C. for 2 hours. For work-up the reaction was concentrated under reduced pressure and the thus obtained crude title compound (939 mg) was used in the following steps without further purification.

LC-MS (Method 2): Rt=1.96 min; MS (ESIpos): m/z=773 [M+H]+

Intermediate 318 ethyl 7-[5-(bromomethyl)-1-methyl-3-propyl-1H-pyrazol-4-yl]-6-methyl-1-[3-(methylamino)propyl]-3-[3-(naphthalen-1-yloxy)propyl]-1H-indole-2-carboxylate hydrochloric acid salt

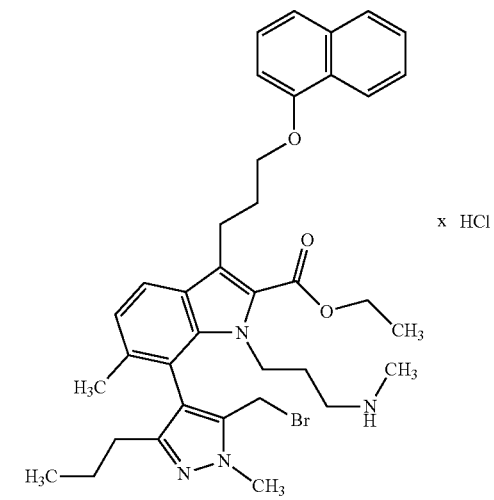

To a solution of ethyl 7-[5-(bromomethyl)-1-methyl-3-propyl-1H-pyrazol-4-yl]-1-{3-[(tert-butoxycarbonyl)(methyl)amino]propyl}-6-methyl-3-[3-(naphthalen-1-yloxy)propyl]-1H-indole-2-carboxylate (935 mg; see Intermediate 317) in methanol (22 ml) was added a 4 M solution of HCl in dioxane (21 ml, 4.0 M, 85 mmol) at 0° C. and the mixture was stirred for 3 h at room temperature. For work-up the mixture was concentrated under reduced pressure and the crude title compound (858 mg) thus obtained was used for the subsequent steps without further purification.

Intermediate 319

(rac)-ethyl 7,9,12-trimethyl-1-[3-(naphthalen-1-yloxy)propyl]-11-propyl-4,5,6,7,8,9-hexahydropyrazolo[3',4':7,8][1,5]diazecino[9,10,1-hi]indole-2-carboxylate

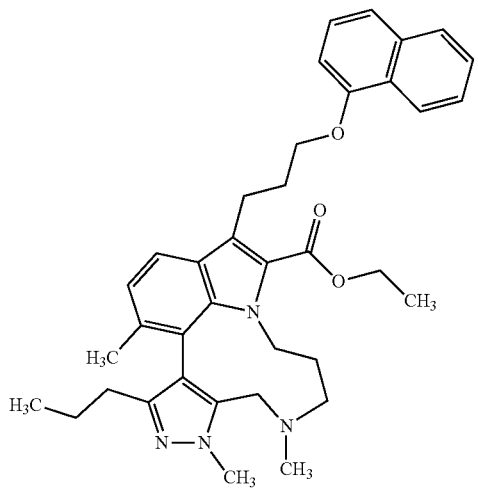 [SMILES: CCCc1nn(C)c2c1-c1c(C)ccc3c(CCCOc4cccc5ccccc45)c(C(=O)OCC)n(c13)CCCN(C)C2]

To a solution of ethyl 7-[5-(bromomethyl)-1-methyl-3-propyl-1H-pyrazol-4-yl]-6-methyl-1-[3-(methylamino)propyl]-3-[3-(naphthalen-1-yloxy)propyl]-1H-indole-2-carboxylate hydrochloric acid salt (858 mg; see Intermediate 318) in DMF (74 ml) was added caesium carbonate (1.97 g, 6.04 mmol) and the reaction mixture was stirred at 65° C. for 18 hours. For work-up the mixture was concentrated under reduced pressure and the crude product was purified by flash chromatography (dichloromethane/acetone gradient, 0%→10% acetone) to give the title compound (480 mg, 81% purity).

Intermediate 320

4-bromo-1,5-dimethyl-1H-pyrazole-3-carbaldehyde

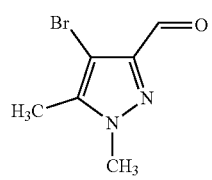

DMSO (17 ml) was added dropwise at −78° C. to a solution of oxalyl chloride (60 ml, 2.0 M, 120 mmol) in dichloromethane and the mixture was stirred for 15 min. A solution of (4-bromo-1,5-dimethyl-1H-pyrazol-3-yl)methanol (16.5 g, 80.5 mmol; see Intermediate 11) in dichloromethane (80 ml) was added, followed by the addition of triethylamine (68 ml, 480 mmol), and the mixture was stirred for 24 h at room temperature. For work-up, water was added to the reaction mixture and the phases were separated. The aqueous phase was extracted with dichloromethane/isopropanol (4:1) and the combined organic phases were washed with brine and were dried over sodium sulfate. After filtration and removal of the solvent the title compound (10.3 g) was used in the following steps without further purification.

$^1$H-NMR (400 MHz, CHLOROFORM-d) δ [ppm]: 1.517 (0.92), 2.223 (0.63), 2.258 (16.00), 3.804 (0.55), 3.866 (15.20), 9.854 (5.90).

Intermediate 321 ethyl (5E/Z)-6-(4-bromo-1,5-dimethyl-1H-pyrazol-3-yl)hex-5-enoate

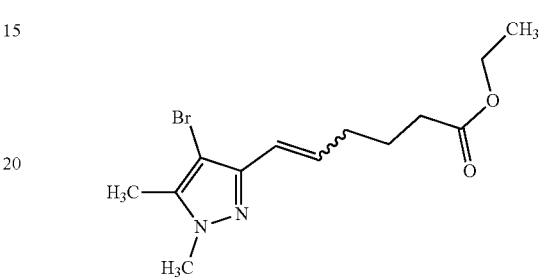

n-Butyl lithium (29 ml, 2.5 M in hexane, 71 mmol) was added dropwise at −78° C. to a suspension of (5-ethoxy-5-oxopentyl)(triphenyl)phosphonium bromide (37.9 g, 95% purity, 76.4 mmol, CAS 118026-77-0) in THF (550 ml) and the mixture was stirred for 1 h at 0° C. Upon cooling to −78° C., a solution of 4-bromo-1,5-dimethyl-1H-pyrazole-3-carbaldehyde (10.3 g, 50.9 mmol; see Intermediate 320) in THF (100 ml) was added dropwise and the mixture was allowed to warm to 0° C. The reaction mixture was stirred for 4 hours at 0° C., for 24 hours at room temperature and for 4 hours at 40° C. For work-up, saturated aqueous ammonium chloride solution was added and the mixture was poured into water. The mixture was extracted with ethyl acetate, the combined organic phases were washed with brine and were dried over sodium sulfate. After filtration and removal of the solvent the residue was purified by flash chromatography (hexane/ethyl acetate gradient 12%→50% ethyl acetate) to give the title compound (3.1 g) as a mixture of E/Z isomers.

Intermediate 322

(5E/Z)-6-(4-bromo-1,5-dimethyl-1H-pyrazol-3-yl)hex-5-en-1-ol

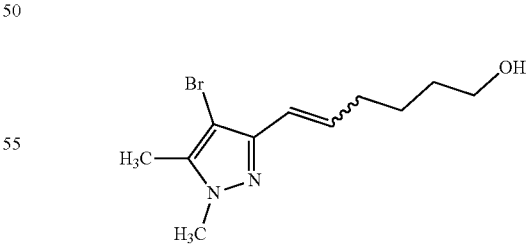

To a solution of ethyl (5E/Z)-6-(4-bromo-1,5-dimethyl-1H-pyrazol-3-yl)hex-5-enoate (2.85 g, 9.04 mmol; see Intermediate 321) in THF (40 ml) was added a solution of lithium borohydride in THF (9.9 ml, 2.0 M, 20 mmol) and the mixture was stirred at 50° C. for 8 hours. For work-up, sodium sulphate hydrate was added and the mixture was stirred for 1 hour at room temperature. The mixture was filtrated and the filtrate was concentrated under reduced pressure to give the title compound (2.15 g) which was used in the subsequent steps without further purification.

$^1$H-NMR (400 MHz, CHLOROFORM-d) δ [ppm]: 1.514 (0.72), 1.529 (1.64), 1.533 (1.64), 1.538 (1.00), 1.547 (1.15), 1.550 (1.17), 1.554 (1.14), 1.557 (1.29), 1.562 (1.67), 1.576 (1.55), 1.591 (0.79), 2.184 (0.80), 2.187 (0.73), 2.193 (16.00), 2.460 (0.45), 2.478 (0.99), 2.480 (0.99), 2.497 (1.06), 2.516 (0.48), 2.519 (0.44), 3.657 (0.90), 3.668 (0.92), 3.681 (0.47), 3.716 (0.50), 3.740 (0.52), 3.754 (14.99), 5.746 (0.48), 5.766 (1.01), 5.775 (0.59), 5.785 (0.50), 5.795 (1.22), 5.814 (0.58), 6.135 (0.71), 6.139 (1.35), 6.142 (0.71), 6.165 (0.59), 6.168 (1.11), 6.171 (0.58).

Intermediate 323 ethyl 7-{3-[(1E/Z)-6-hydroxyhex-1-en-1-yl]-1,5-dimethyl-1H-pyrazol-4-yl}-3-[3-(1-naphthyloxy)propyl]-1H-indole-2-carboxylate

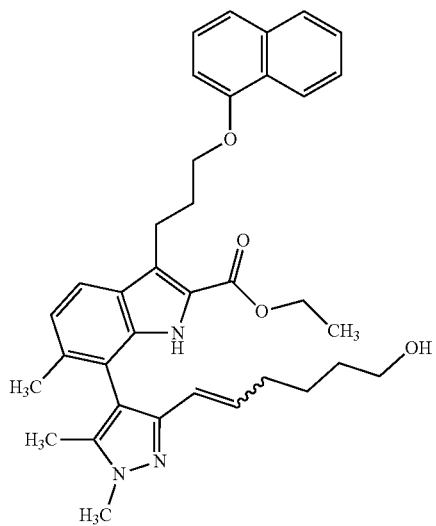

To a solution of ethyl 3-[3-(naphthalen-1-yloxy)propyl]-7-(4,4,5,5-tetramethyl-1,3,2-dioxaborolan-2-yl)-1H-indole-2-carboxylate (2.01 g, 4.03 mmol; see Intermediate 5) and (5E/Z)-6-(4-bromo-1,5-dimethyl-1H-pyrazol-3-yl)hex-5-en-1-ol (3.66 mmol; see Intermediate 322) in THF (45 ml) were added an aqueous solution of potassium phosphate (15 ml, 0.50 M, 7.3 mmol). The mixture was degassed and purged with argon several times. XPhos Pd G2 (see abbreviation list, 101 mg, 128 µmol) was added and the mixture was purged with argon for 10 minutes. The reaction mixture was stirred at 50° C. for 2 h. For work-up, water was added and the mixture was extracted with ethyl acetate. The combined organic phases were filtered through a silicone filter and concentrated. The residue was purified by flash chromatography (hexane/ethyl acetate gradient, 25%→100% ethyl acetate) to give the title compound (1.53 g).

$^1$H-NMR (400 MHz, DMSO-d6) δ [ppm]: 1.067 (7.55), 1.172 (0.66), 1.215 (0.41), 1.233 (1.00), 1.253 (5.37), 1.271 (12.18), 1.289 (5.50), 1.326 (0.67), 1.333 (0.65), 1.344 (1.18), 1.353 (1.00), 1.362 (1.39), 1.379 (1.43), 1.394 (1.64), 1.410 (1.34), 1.427 (0.79), 1.988 (1.03), 2.043 (16.00), 2.210 (0.98), 2.226 (1.33), 2.246 (1.05), 2.261 (0.42), 2.327 (0.53), 2.518 (2.85), 2.523 (1.95), 2.535 (1.72), 2.551 (1.66), 2.569 (0.63), 2.669 (0.55), 3.351 (1.97), 3.366 (3.22), 3.380 (3.21), 3.396 (1.22), 3.673 (0.44), 3.809 (15.95), 3.939 (1.08), 4.199 (1.38), 4.214 (2.91), 4.230 (1.49), 4.238 (1.77), 4.256 (4.73), 4.273 (4.54), 4.291 (1.36), 4.309 (2.04), 4.322 (4.62), 4.335 (1.90), 5.428 (0.65), 5.447 (1.36), 5.458 (0.67), 5.465 (0.59), 5.476 (1.51), 5.494 (0.71), 5.759 (0.60), 5.827 (0.91), 5.831 (1.89), 5.834 (0.94), 5.855 (0.77), 5.859 (1.51), 6.904 (1.75), 6.921 (1.95), 6.975 (1.65), 6.979 (1.71), 6.993 (2.61), 6.996 (2.33), 7.046 (2.27), 7.064 (1.82), 7.066 (2.32), 7.084 (1.44), 7.371 (1.43), 7.391 (2.55), 7.410 (2.16), 7.449 (2.60), 7.469 (1.45), 7.492 (0.59), 7.504 (1.62), 7.509 (1.50), 7.512 (2.00), 7.520 (3.85), 7.528 (2.21), 7.531 (1.82), 7.536 (1.91), 7.548 (0.66), 7.662 (1.81), 7.682 (1.64), 7.859 (1.52), 7.867 (0.84), 7.876 (1.28), 7.882 (1.35), 8.221 (1.30), 8.227 (1.20), 8.237 (0.63), 8.245 (1.28), 10.640 (2.81).

Intermediate 324 ethyl 7-[3-(6-hydroxyhexyl)-1,5-dimethyl-1H-pyrazol-4-yl]-3-[3-(1-naphthyloxy)propyl]-1H-indole-2-carboxylate

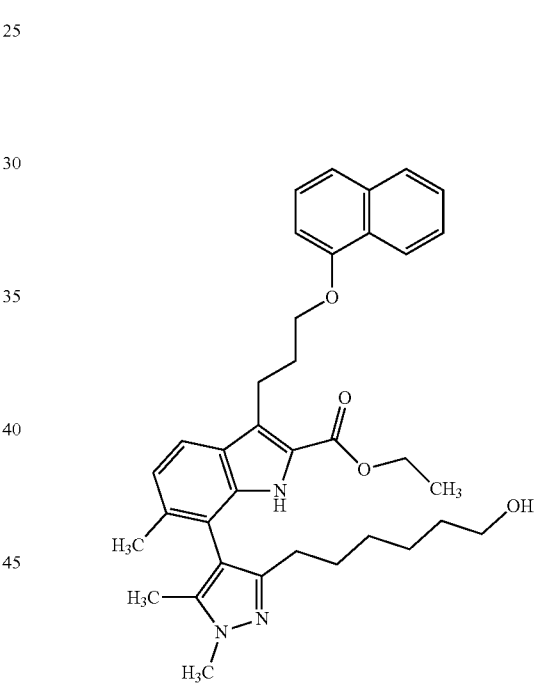

An autoclave was charged with ethyl 7-{3-[(1E/Z)-6-hydroxyhex-1-en-1-yl]-1,5-dimethyl-1H-pyrazol-4-yl}-3-[3-(1-naphthyloxy)propyl]-1H-indole-2-carboxylate (1.53 g, 2.70 mmol; see Intermediate 323), ethanol (50 ml), THF (5 ml) and palladium 10% on charcoal (288 mg, 270 µmol) and the mixture was stirred under 20 bar hydrogen atmosphere at room temperature for 22 hours. For work-up, the mixture was filtered through a pad of celite, eluted with ethanol and THF and the combined filtrates were concentrated under reduced pressure to give the title compound (1.51 g), which was directly used in the next step.

LC-MS (Method 2): Rt=1.58 min; MS (ESIpos): m/z=568 [M+H]$^+$

Intermediate 325 ethyl 7-[3-(6-bromohexyl)-1,5-dimethyl-1H-pyrazol-4-yl]-3-[3-(1-naphthyloxy)propyl]-1H-indole-2-carboxylate

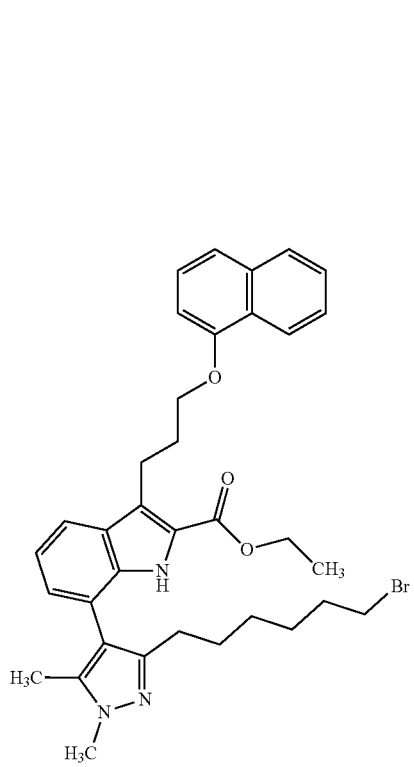

To a solution of ethyl 7-[3-(6-hydroxyhexyl)-1,5-dimethyl-1H-pyrazol-4-yl]-3-[3-(1-naphthyloxy)propyl]-1H-indole-2-carboxylate (2.66 mmol; see Intermediate 324) in dichloromethane (49 ml), triphenylphosphine (1.69 g, 6.38 mmol) was added at 0° C. and the mixture was stirred at 0° C. for 10 min. Tetrabromomethane (1.94 g, 5.85 mmol) was added and the reaction mixture was stirred at 0° C. for 3 hours. For work-up, the reaction mixture was concentrated under reduced pressure and the crude title compound (1.65 g) was used in the subsequent steps without further purification.

Intermediate 326

(rac)-ethyl 2,3-dimethyl-7-[3-(1-naphthyloxy)propyl]-10,11,12,13,14,15-hexahydro-2H-pyrazolo[4',3':4,5]azacycloundecino[3,2,1-hi]indole-8-carboxylate

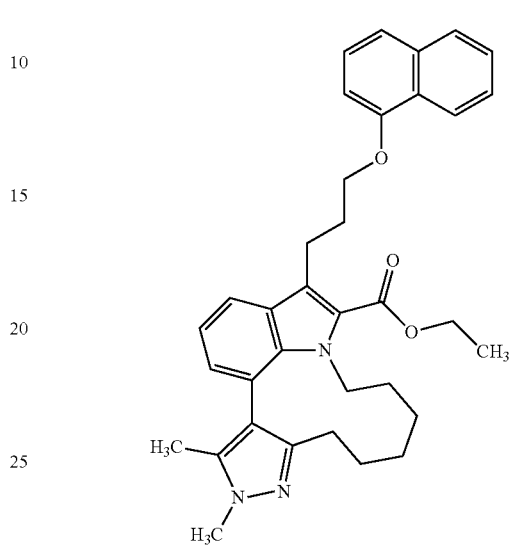

To a solution of ethyl 7-[3-(6-bromohexyl)-1,5-dimethyl-1H-pyrazol-4-yl]-3-[3-(1-naphthyloxy)propyl]-1H-indole-2-carboxylate (2.68 mmol; see Intermediate 325) in 1,4-dioxane (140 ml) was added a solution of potassium-tert-butylat in THF (13 ml, 1.0 M, 13 mmol) and the mixture was stirred at 80° C. for 1 day. For work-up, the reaction mixture was concentrated under reduced pressure and the residue was purified by flash chromatography (hexane/ethyl acetate gradient, 12%→100% ethyl acetate) to give the title compound (260 mg) as a racemic mixture.

LC-MS (Method 2): Rt=1.78 min; MS (ESIpos): m/z=550 [M+H]$^+$

Intermediate 327 ethyl 5-ethyl-1-[2-(morpholin-4-yl)ethyl]-1H-pyrazole-3-carboxylate

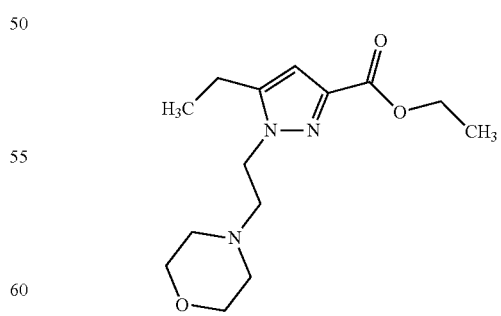

To a mixture of ethyl 2,4-dioxohexanoate (3.00 g, 17.1 mmol) in acetic acid (24 ml) was added 4-(2-hydrazinylethyl)morpholine (2.53 g, 17.1 mmol) at 0° C. and the reaction mixture was stirred at 100° C. for 3 h. Upon cooling, the mixture was concentrated. The residue was diluted with ethyl acetate and the organic phase was washed with saturated aqueous sodium bicarbonate solution and brine. The organic phase was dried over sodium sulfate. After filtration and removal of the solvents the crude product was purified by flash chromatography (hexane/ethyl acetate gradient, 50%→100% ethyl acetate) to give the title compound (1.96 g).

¹H-NMR (400 MHz, DMSO-d6) δ [ppm]: 1.192 (5.34), 1.211 (12.80), 1.230 (6.02), 1.249 (7.04), 1.267 (16.00), 1.285 (7.15), 2.385 (2.88), 2.396 (3.98), 2.408 (3.12), 2.518 (1.26), 2.523 (0.85), 2.642 (3.19), 2.658 (5.49), 2.661 (5.21), 2.663 (4.60), 2.669 (1.00), 2.675 (2.92), 2.680 (3.82), 2.682 (3.66), 2.700 (1.08), 3.519 (4.16), 3.530 (5.19), 3.542 (4.09), 4.175 (2.39), 4.192 (4.57), 4.207 (3.68), 4.225 (6.71), 4.242 (6.56), 4.260 (1.95), 6.511 (5.60).

Intermediate 328 ethyl 3-ethyl-1-[2-(morpholin-4-yl)ethyl]-1H-pyrazole-5-carboxylate

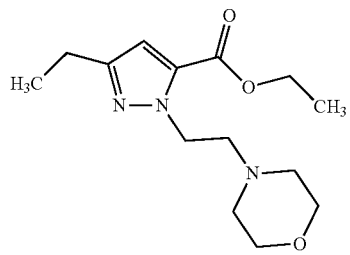 [SMILES: CCOC(=O)c1cc(CC)nn1CCN1CCOCC1]

The title compound was isolated as a side product in the synthesis of ethyl 5-ethyl-1-[2-(morpholin-4-yl)ethyl]-1H-pyrazole-3-carboxylate.

¹H-NMR (500 MHz, DMSO-d6) δ [ppm]: 0.000 (5.34), 1.145 (7.12), 1.155 (0.41), 1.160 (16.00), 1.175 (7.30), 1.283 (6.71), 1.298 (14.69), 1.312 (7.24), 1.906 (0.75), 2.367 (2.57), 2.376 (3.50), 2.384 (2.63), 2.529 (1.62), 2.544 (4.72), 2.559 (4.59), 2.574 (1.47), 2.602 (2.50), 2.615 (4.09), 2.629 (2.56), 3.329 (3.25), 3.501 (3.51), 3.510 (4.71), 3.519 (3.52), 4.255 (2.16), 4.269 (6.47), 4.284 (6.75), 4.298 (2.08), 4.507 (2.42), 4.520 (4.07), 4.534 (2.37), 6.653 (7.25).

Intermediate 329 ethyl 4-bromo-3-ethyl-1-[2-(morpholin-4-yl)ethyl]-1H-pyrazole-5-carboxylate

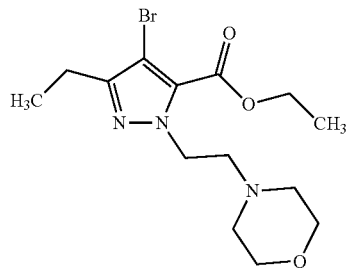 [SMILES: CCOC(=O)c1c(Br)c(CC)nn1CCN1CCOCC1]

A solution of bromine in acetic acid (8.2 ml, 1.0 M, 8.2 mmol) was added to a solution of ethyl 3-ethyl-1-[2-(morpholin-4-yl)ethyl]-1H-pyrazole-5-carboxylate (770 mg, 2.74 mmol; see Intermediate 328) in acetic acid (16 ml) at 0° C., and the mixture was stirred for 4 h at room temperature. For work-up, the reaction was poured into ice water followed by the addition of a saturated aqueous sodium thiosulfate solution and the pH of the mixture was adjusted to pH>7 by the addition of saturated aqueous sodium bicarbonate solution. The mixture was extracted with ethyl acetate and the combined organic phases were dried over sodium sulfate. After filtration and removal of the solvents the crude product was purified by flash chromatography (hexane/ethyl acetate gradient, 0%→100% ethyl acetate) to give the title compound (810 mg).

LC-MS (Method 2): Rt=1.28 min; MS (ESIpos): m/z=360 [M+H]⁺

¹H-NMR (400 MHz, CDCl₃): δ [ppm]=4.61 (t, 2H), 4.39 (q, 2H), 3.75-3.53 (m, 4H), 2.71 (t, 2H), 2.64 (q, 2H), 2.51-2.36 (m, 4H), 1.59 (s, 2H), 1.43 (t, 3H), 1.23 (t, 3H)

Intermediate 330

{4-bromo-3-ethyl-1-[2-(morpholin-4-yl)ethyl]-1H-pyrazol-5-yl}methanol

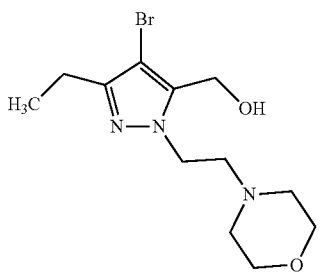 [SMILES: CCc1nn(CCN2CCOCC2)c(CO)c1Br]

To a solution of ethyl 4-bromo-3-ethyl-1-[2-(morpholin-4-yl)ethyl]-1H-pyrazole-5-carboxylate (810 mg, 2.25 mmol; see Intermediate 329) in THF (9 ml) was added a solution of lithium borohydride in THF (1.3 ml, 2.0 M, 2.7 mmol) and the mixture was stirred at 60° C. for 24 hours. For work-up, sodium sulfate hydrate was added and the mixture was stirred for 1 hour at room temperature. The mixture was filtrated and the filtrate was concentrated under reduced pressure and the crude product was purified by flash chromatography (dichloromethane/acetone gradient, 0%→40% acetone) to give the title compound (650 mg).

Intermediate 331 ethyl 7-{3-ethyl-5-(hydroxymethyl)-1-[2-(morpholin-4-yl)ethyl]-1H-pyrazol-4-yl}-3-[3-(naphthalen-1-yloxy)propyl]-1H-indole-2-carboxylate

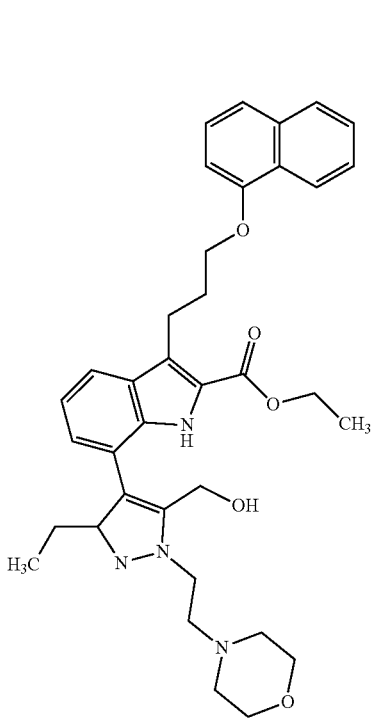

To a solution of ethyl 3-[3-(naphthalen-1-yloxy)propyl]-7-(4,4,5,5-tetramethyl-1,3,2-dioxaborolan-2-yl)-1H-indole-2-carboxylate (1.12 g, 2.25 mmol; see Intermediate 5) and {4-bromo-3-ethyl-1-[2-(morpholin-4-yl)ethyl]-1H-pyrazol-5-yl}methanol (650 mg, 2.04 mmol; see Intermediate 330) in THF (25 ml) was added an aqueous solution of potassium phosphate (8.2 ml, 0.50 M, 4.1 mmol). The mixture was degassed and purged with argon several times. XPhos Pd G2 (see abbreviation list, 56.3 mg, 71.5 µmol) was added and the mixture was purged with argon several times. The reaction mixture was stirred at 50° C. for 3 h. For work-up, water was added and the mixture was extracted with ethyl acetate. The combined organic phases were dried over sodium sulfate. After filtration and removal of the solvents the crude product was purified by flash chromatography (dichloromethane/acetone gradient, 0%→40% acetone) to give the title compound (1.08 g).

LC-MS (Method 2): Rt=1.63 min; MS (ESIpos): m/z=611 [M+H]+

Intermediate 332

(rac)-ethyl (11Z)-3-ethyl-1-[2-(morpholin-4-yl)ethyl]-7-[3-(naphthalen-1-yloxy)propyl]-1,10,13,15-tetrahydropyrazolo[4',3':9,10][1,6]oxazacycloundecino[8,7,6-hi]indole-8-carboxylate

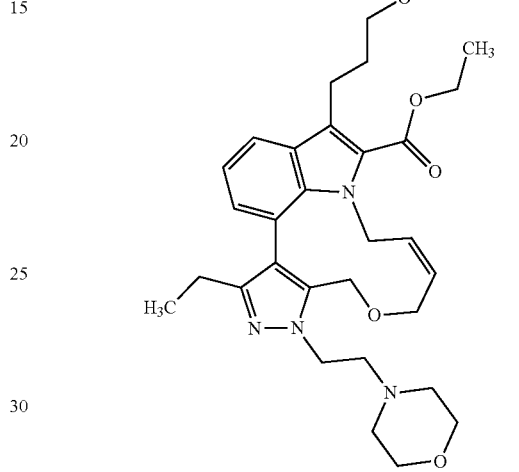

To a solution of ethyl 7-{3-ethyl-5-(hydroxymethyl)-1-[2-(morpholin-4-yl)ethyl]-1H-pyrazol-4-yl}-3-[3-(naphthalen-1-yloxy)propyl]-1H-indole-2-carboxylate (1.08 g, 1.75 mmol; see Intermediate 331) in acetonitrile (19 ml) was added caesium carbonate (2.85 g, 8.75 mmol) and the mixture was stirred for 10 min at room temperature. (2Z)-1,4-dichlorobut-2-ene (210 µl, 95% purity, 1.9 mmol) and sodium iodide (530 mg, 3.50 mmol) were added and the reaction mixture was stirred for 18 hours at 40° C. For work-up the reaction mixture was poured into water. The mixture was extracted with ethyl acetate. The combined organic phases were washed with brine and dried over sodium sulfate. After filtration and removal of the solvent the crude product was purified by flash chromatography (dichloromethane/acetone gradient, 20%→60% acetone) to give the title compound (550 mg).

$^1$H-NMR (400 MHz, DMSO-d6) δ [ppm]: 0.816 (6.75), 0.835 (16.00), 0.854 (6.95), 1.112 (0.91), 1.131 (2.20), 1.138 (1.27), 1.150 (1.01), 1.230 (0.48), 1.270 (7.09), 1.287 (15.84), 1.305 (7.17), 2.047 (1.41), 2.067 (3.59), 2.084 (3.39), 2.103 (1.11), 2.116 (0.58), 2.235 (1.31), 2.253 (1.85), 2.269 (1.35), 2.323 (0.87), 2.327 (1.21), 2.332 (0.83), 2.403 (1.95), 2.415 (1.73), 2.432 (2.42), 2.442 (1.29), 2.454 (0.60), 2.460 (0.79), 2.464 (0.69), 2.480 (2.42), 2.518 (6.07), 2.523 (4.37), 2.534 (1.61), 2.544 (0.81), 2.649 (0.77), 2.665 (1.19), 2.669 (1.27), 2.674 (0.83), 2.720 (0.46), 2.738 (1.01), 2.751 (1.05), 2.769 (1.29), 2.785 (0.71), 2.838 (0.71), 2.856 (1.57), 2.869 (0.66), 2.876 (0.89), 2.887 (1.15), 2.906 (0.50), 3.290 (0.54), 3.307 (1.07), 3.347 (1.99), 3.368 (0.87), 3.382 (0.52), 3.530 (0.71), 3.544 (1.47), 3.554 (0.93), 3.577 (6.77), 3.588 (9.63), 3.599 (5.26), 3.744 (0.95), 3.755 (1.25), 3.776 (0.85), 3.788 (0.83), 4.209 (2.70), 4.217 (1.29), 4.224 (2.34), 4.228 (2.36), 4.233 (2.48), 4.243 (7.17), 4.251 (3.99), 4.259 (2.68), 4.268 (4.90), 4.278 (1.83), 4.287 (4.29), 4.296 (3.49), 4.304 (2.08), 4.313 (2.74), 4.323 (1.47), 4.331 (0.77), 4.340 (1.41), 4.358 (0.40), 4.449 (0.46), 4.461 (0.46), 4.671 (0.62), 4.696 (0.91), 4.708 (0.99), 4.736 (1.23), 4.745 (2.72), 4.779 (2.46), 4.896 (0.75), 4.923 (1.43), 4.948 (2.48), 4.991 (1.05), 5.131 (0.54), 5.141 (0.60), 5.159 (0.85), 5.167 (0.85), 5.196 (0.42), 5.759 (3.79), 6.811 (2.76), 6.814 (2.98), 6.829 (3.16), 6.831 (3.04), 6.911 (2.52), 6.928 (2.76), 7.084 (2.76), 7.102 (2.90), 7.103 (3.16), 7.122 (2.36), 7.374 (2.06), 7.395 (3.65), 7.414 (3.06), 7.453 (3.81), 7.474 (2.14), 7.481 (0.85), 7.485 (0.97), 7.498 (2.16), 7.502 (1.95), 7.512 (2.38), 7.518 (3.63), 7.521 (2.42), 7.532 (2.12), 7.535 (2.52), 7.549 (1.03), 7.553 (0.75), 7.773 (2.76), 7.777 (2.84), 7.794 (2.66), 7.796 (2.46), 7.861 (2.20), 7.867 (1.39), 7.880 (2.48), 7.884 (1.91), 8.197 (1.93), 8.202 (1.97), 8.221 (1.83).

Intermediate 333

(rac)-ethyl 3-ethyl-1-[2-(morpholin-4-yl)ethyl]-7-[3-(naphthalen-1-yloxy) propyl]-1,10,11,12,13,15-hexahydropyrazolo[4',3':9,10][1,6]oxazacycloundecino[8,7,6-hi]indole-8-carboxylate

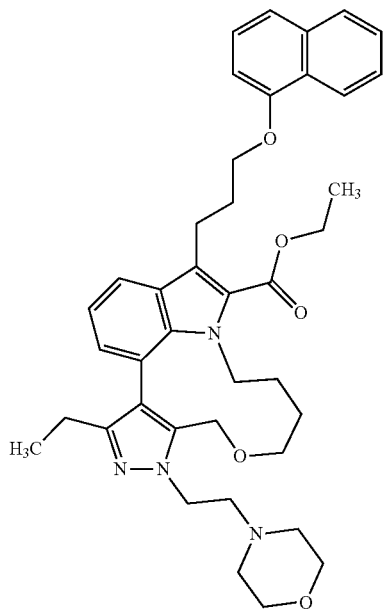 [SMILES: CCOC(=O)c1c(CCCOc2cccc3ccccc23)c2cccc3c2n1CCCCOCc1c-3c(CC)nn1CCN1CCOCC1]

A suspension of (rac)-ethyl (11Z)-3-ethyl-1-[2-(morpholin-4-yl)ethyl]-7-[3-(naphthalen-1-yloxy)propyl]-1,10,13,15-tetrahydropyrazolo[4',3':9,10][1,6]oxazacycloundecino[8,7,6-hi]indole-8-carboxylate (550 mg, 830 µmol; see Intermediate 332) and Pd/C (56.9 mg, 53.5 µmol) in ethanol (22 ml) was stirred under an atmosphere of hydrogen at room temperature for 18 hours. For work-up, the mixture was filtered through a pad of celite. The residue was washed with ethyl acetate and the filtrate was concentrated under reduced pressure and the crude title compound was used in the subsequent steps without further purification.

$^1$H-NMR (400 MHz, DMSO-d6) δ [ppm]: 0.835 (0.46), 0.867 (6.87), 0.886 (15.90), 0.905 (7.04), 0.971 (0.56), 0.989 (1.38), 1.005 (1.73), 1.019 (1.52), 1.112 (0.94), 1.120 (0.40), 1.131 (2.11), 1.150 (1.00), 1.231 (2.59), 1.263 (7.87), 1.281 (16.00), 1.299 (7.52), 2.139 (1.69), 2.158 (5.22), 2.177 (5.08), 2.196 (2.24), 2.220 (1.90), 2.237 (1.46), 2.323 (0.86), 2.327 (1.17), 2.332 (0.86), 2.337 (0.46), 2.369 (0.86), 2.380 (1.73), 2.396 (2.13), 2.408 (2.94), 2.461 (0.67), 2.480 (3.41), 2.518 (7.16), 2.523 (4.91), 2.649 (0.73), 2.665 (1.13), 2.669 (1.23), 2.673 (0.84), 2.729 (0.69), 2.746 (1.23), 2.760 (1.59), 2.777 (1.67), 2.796 (1.94), 2.813 (1.11), 2.827 (1.13), 2.843 (1.19), 2.853 (0.81), 2.871 (1.00), 2.888 (0.48), 3.252 (0.69), 3.268 (0.94), 3.285 (1.38), 3.306 (1.00), 3.366 (1.09), 3.383 (1.27), 3.399 (1.46), 3.412 (0.94), 3.429 (1.02), 3.445 (0.48), 3.530 (0.77), 3.542 (1.23), 3.559 (5.33), 3.570 (9.65), 3.582 (5.43), 4.024 (0.48), 4.041 (0.65), 4.060 (1.02), 4.078 (0.75), 4.094 (0.54), 4.185 (0.71), 4.204 (3.05), 4.221 (5.41), 4.230 (5.16), 4.234 (4.87), 4.248 (5.35), 4.266 (2.26), 4.283 (5.14), 4.301 (2.61), 4.310 (1.48), 4.319 (0.81), 4.328 (1.40), 4.346 (0.44), 4.430 (1.25), 4.442 (0.82), 4.454 (1.07), 4.466 (1.23), 4.660 (2.59), 4.693 (2.36), 5.759 (1.80), 6.851 (2.69), 6.854 (2.84), 6.869 (3.24), 6.872 (3.03), 6.894 (2.65), 6.912 (2.94), 7.054 (2.65), 7.072 (2.86), 7.074 (3.18), 7.092 (2.32), 7.369 (2.01), 7.390 (3.76), 7.409 (3.05), 7.452 (4.03), 7.472 (2.28), 7.490 (0.58), 7.495 (0.90), 7.508 (2.42), 7.512 (2.40), 7.515 (3.07), 7.523 (5.20), 7.532 (3.15), 7.535 (2.65), 7.539 (2.67), 7.552 (0.94), 7.556 (0.54), 7.763 (2.71), 7.766 (2.88), 7.784 (2.61), 7.787 (2.51), 7.861 (2.36), 7.870 (1.21), 7.879 (1.96), 7.885 (2.00), 8.221 (2.05), 8.227 (1.82), 8.238 (0.98), 8.245 (1.86).

Intermediate 334 ethyl 4-bromo-5-ethyl-1-[2-(morpholin-4-yl)ethyl]-1H-pyrazole-3-carboxylate

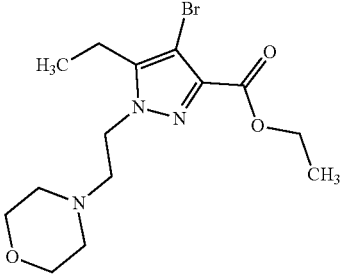 [SMILES: CCOC(=O)c1nn(CCN2CCOCC2)c(CC)c1Br]

A solution of bromine in acetic acid (35 ml, 1.0 M, 35 mmol) was added to a solution of ethyl 5-ethyl-1-[2-(morpholin-4-yl)ethyl]-1H-pyrazole-3-carboxylate (3.30 g, 11.7 mmol; see Intermediate 327) in acetic acid (12 ml) at 0° C., and the mixture was stirred for 4 h at room temperature. For work-up, the reaction mixture was poured into ice water followed by the addition of a saturated aqueous sodium thiosulfate solution, and the pH of the mixture was adjusted to pH>7 by the addition of saturated aqueous sodium bicarbonate solution. The mixture was extracted with ethyl acetate and the combined organic phases were washed with brine and were dried over sodium sulfate. After filtration and removal of the solvents the crude product was purified by flash chromatography (hexane/ethyl acetate gradient, 0%→100% ethyl acetate) to give the title compound (3.54 g)

LC-MS (Method 2): Rt=1.09 min; MS (ESIpos): m/z=360 [M+H]$^+$ $^1$H-NMR (400 MHz, CHLOROFORM-d) δ [ppm]: 0.000 (1.04), 0.018 (1.17), 1.133 (5.55), 1.152 (12.67), 1.171 (5.77), 1.332 (7.44), 1.350 (16.00), 1.368 (7.71), 1.520 (6.74), 2.407 (4.64), 2.418 (5.82), 2.430 (5.13), 2.667 (1.68), 2.686 (5.35), 2.705 (5.25), 2.724 (1.70), 2.732 (3.47), 2.749 (5.00), 2.766 (3.51), 3.604 (5.50), 3.616 (5.96), 3.627 (5.50), 4.172 (3.57), 4.190 (4.95), 4.206 (3.34), 4.340 (2.39), 4.358 (7.39), 4.375 (7.21), 4.393 (2.23).

Intermediate 335

{4-bromo-5-ethyl-1-[2-(morpholin-4-yl)ethyl]-1H-pyrazol-3-yl}methanol

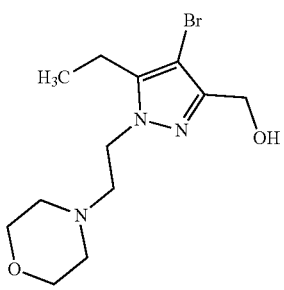 [SMILES: CCc1c(Br)c(CO)nn1CCN1CCOCC1]

To a solution of ethyl 4-bromo-5-ethyl-1-[2-(morpholin-4-yl)ethyl]-1H-pyrazole-3-carboxylate (3.54 g, 9.83 mmol; see Intermediate 334) in THF (40 ml) was added a solution of lithium borohydride in THF (5.9 ml, 2.0 M, 12 mmol) and the mixture was stirred at 60° C. for 24 hours. For work-up, sodium sulfate hydrate was added and the mixture was stirred for 1 hour at room temperature. The mixture was filtrated and the filtrate was concentrated under reduced pressure and the crude product was purified by flash chromatography (dichloromethane/acetone gradient, 0%→40% acetone) to give the title compound (2.9 g).

$^1$H-NMR (400 MHz, CHLOROFORM-d) δ [ppm]: 0.000 (0.71), 0.018 (0.73), 1.122 (6.19), 1.141 (13.77), 1.160 (6.38), 1.372 (0.61), 1.581 (0.51), 2.414 (5.08), 2.426 (6.45), 2.437 (5.45), 2.600 (2.03), 2.619 (6.23), 2.638 (6.10), 2.657 (1.86), 2.690 (3.85), 2.708 (5.10), 2.726 (4.07), 3.619 (6.39), 3.631 (6.95), 3.642 (6.38), 4.066 (3.98), 4.084 (5.06), 4.101 (3.89), 4.573 (16.00).

Intermediate 336 ethyl 7-{5-ethyl-3-(hydroxymethyl)-1-[2-(morpholin-4-yl)ethyl]-1H-pyrazol-4-yl}-3-[3-(naphthalen-1-yloxy)propyl]-1H-indole-2-carboxylate To a solution of ethyl 3-[3-(naphthalen-1-yloxy)propyl]-7-(4,4,5,5-tetramethyl-1,3,2-dioxaborolan-2-yl)-1H-indole-2-carboxylate (2.25 g, 4.51 mmol; see Intermediate 5) and {4-bromo-5-ethyl-1-[2-(morpholin-4-yl)ethyl]-1H-pyrazol-3-yl}methanol (1.30 g, 4.10 mmol; see Intermediate 335) in THF (50 ml) was added an aqueous solution of potassium phosphate (16 ml, 0.50 M, 8.2 mmol). The mixture was degassed and purged with argon several times. XPhos Pd G2 (see abbreviation list, 56.3 mg, 71.5 μmol) was added and the mixture was purged with argon several times. The reaction was stirred at 50° C. for 4 h. For work-up, water was added and the mixture was extracted with ethyl acetate. The combined organic phases were washed with brine and were dried over sodium sulfate. After filtration and removal of the solvents, the crude product was purified by flash chromatography (dichloromethane/ethanol gradient, 0%→10% ethanol) to give the title compound (2.1 g).

LC-MS (Method 2): Rt=1.57 min; MS (ESIpos): m/z=611 [M+H]$^+$

Intermediate 337

(rac)-ethyl (11Z)-3-ethyl-2-[2-(morpholin-4-yl)ethyl]-7-[3-(naphthalen-1-yloxy)propyl]-2,10,13,15-tetrahydropyrazolo[4',3':9,10][1,6]oxazacycloundecino[8,7,6-hi]indole-8-carboxylate

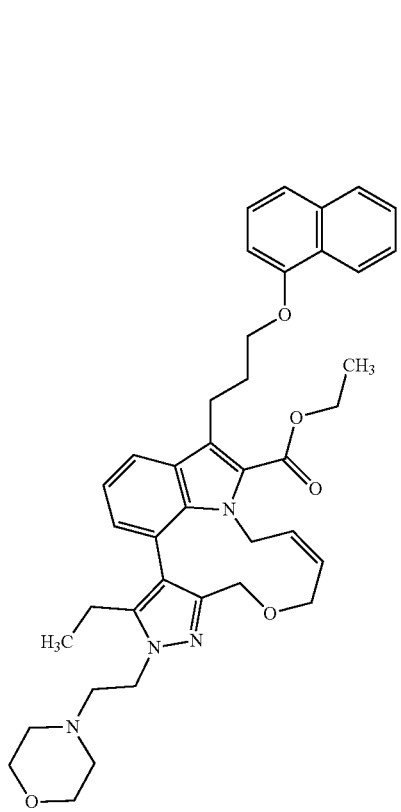 [SMILES: CCOC(=O)c1c(CCCOc2cccc3ccccc23)c2cccc3c2n1C/C=C\COCc1nn(CCN2CCOCC2)c(CC)c1-3]

To a solution of ethyl 7-{5-ethyl-3-(hydroxymethyl)-1-[2-(morpholin-4-yl)ethyl]-1H-pyrazol-4-yl}-3-[3-(naphthalen-1-yloxy)propyl]-1H-indole-2-carboxylate (2.13 g, 3.45 mmol; see Intermediate 336) in acetonitrile (38 ml) was added caesium carbonate (5.62 g, 17.3 mmol) and the mixture was stirred for 10 min at room temperature. (2Z)-1,4-dichlorobut-2-ene (420 µl, 3.8 mmol) and sodium iodide (1.05 g, 6.91 mmol) were added and the reaction mixture was stirred for 18 hours at 40° C. For work-up, the reaction mixture was poured into water. The mixture was extracted with ethyl acetate. The combined organic phases were washed with brine and dried over sodium sulfate. After filtration and removal of the solvent the crude product was purified by flash chromatography (dichloromethane/acetone gradient, 15%→60% acetone) to give the title compound (1.36 g).

LC-MS (Method 2): Rt=1.69 min; MS (ESIpos): m/z=663 [M+H]+

Intermediate 338

(rac)-ethyl 3-ethyl-2-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylate

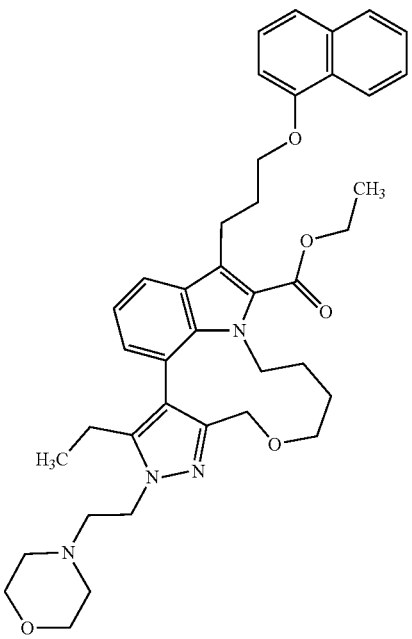 [SMILES: CCOC(=O)c1c(CCCOc2cccc3ccccc23)c2cccc3c2n1CCCCOCc1nn(CCN2CCOCC2)c(CC)c1-3]

A suspension of Pd/C (141 mg, 10% purity, 132 µmol) and (rac)-ethyl (11Z)-3-ethyl-2-[2-(morpholin-4-yl)ethyl]-7-[3-(naphthalen-1-yloxy)propyl]-2,10,13,15-tetrahydropyrazolo[4',3':9,10][1,6]oxazacycloundecino[8,7,6-hi]indole-8-carboxylate (1.36 g, 2.05 mmol; see Intermediate 337) in ethanol (54 ml, 920 mmol) was stirred under an atmosphere of hydrogen at room temperature for 18 hours. For work-up, the mixture was filtered through a pad of celite. The residue was washed with ethyl acetate and the filtrate was concentrated under reduced pressure to give the title compound (1.28 g), which was used in the subsequent steps without further purification.

1H-NMR (400 MHz, DMSO-d6) δ[ppm]: 0.784 (4.24), 0.804 (10.10), 0.822 (4.58), 0.923 (0.55), 0.932 (0.59), 0.953 (0.64), 0.961 (0.62), 1.066 (0.51), 1.117 (0.41), 1.138 (0.96), 1.163 (0.48), 1.233 (0.99), 1.259 (7.51), 1.277 (16.00), 1.295 (7.71), 2.207 (1.95), 2.226 (4.08), 2.245 (3.60), 2.263 (1.24), 2.323 (0.78), 2.327 (1.08), 2.332 (0.78), 2.389 (1.03), 2.405 (1.63), 2.416 (2.63), 2.429 (1.83), 2.447 (2.59), 2.459 (1.79), 2.518 (5.06), 2.523 (3.37), 2.665 (0.78), 2.669 (1.05), 2.673 (0.76), 2.692 (0.41), 2.708 (0.83), 2.724 (1.19), 2.740 (1.53), 2.755 (0.75), 2.784 (0.71), 2.801 (1.67), 2.817 (1.15), 2.833 (0.92), 2.850 (0.41), 3.083 (0.51), 3.095 (0.89), 3.108 (0.96), 3.121 (0.59), 3.134 (0.50), 3.243 (0.57), 3.276 (1.88), 3.297 (1.54), 3.304 (1.46), 3.358 (0.75), 3.375 (0.43), 3.530 (4.44), 3.542 (8.17), 3.553 (4.48), 3.895 (0.41), 3.906 (0.46), 3.919 (0.55), 3.929 (0.98), 3.939 (0.62), 3.953 (0.69), 4.102 (0.43), 4.117 (0.82), 4.137 (0.94), 4.153 (1.63), 4.169 (4.03), 4.183 (1.83), 4.200 (6.23), 4.210 (4.12), 4.219 (4.21), 4.228 (4.30), 4.245 (3.53), 4.263 (1.24), 4.271 (0.91), 4.289 (2.50), 4.298 (0.53), 4.306 (2.31), 4.316 (1.42), 4.324 (0.67), 4.333 (1.44), 4.351 (0.43), 4.513 (3.09), 4.544 (2.73), 6.890 (2.54), 6.907 (2.77), 6.948 (2.47), 6.951 (2.70), 6.966 (3.32), 6.969 (3.16), 7.059 (2.77), 7.077 (2.77), 7.079 (3.30), 7.097 (2.22), 7.367 (2.06), 7.387 (3.66), 7.406 (2.91), 7.453 (3.71), 7.474 (2.18), 7.504 (0.75), 7.516 (2.65), 7.520 (3.32), 7.530 (4.01), 7.538 (2.93), 7.540 (3.25), 7.544 (2.93), 7.555 (0.82), 7.729 (2.70), 7.731 (2.84), 7.748 (2.56), 7.751 (2.52), 7.864 (2.11), 7.868 (1.47), 7.877 (1.58), 7.881 (1.39), 7.887 (1.83), 8.245 (1.83), 8.255 (1.51), 8.269 (1.74).

Intermediate 339 ethyl 7-{5-ethyl-3-(hydroxymethyl)-1-[2-(morpholin-4-yl)ethyl]-1H-pyrazol-4-yl}-6-methyl-3-[3-(naphthalen-1-yloxy)propyl]-1H-indole-2-carboxylate

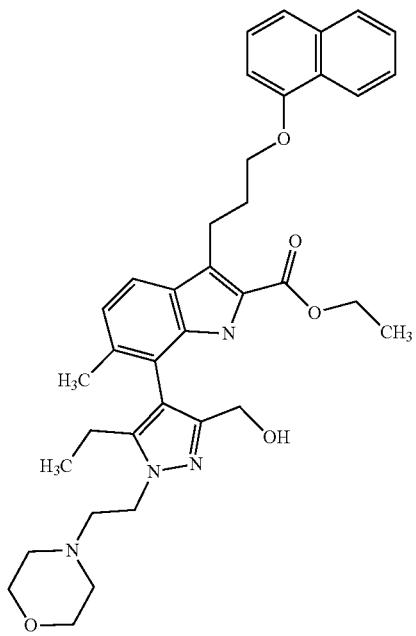 [SMILES: CCOC(=O)c1[nH]c2c(-c3c(CO)nn(CCN4CCOCC4)c3CC)c(C)ccc2c1CCCOc1cccc2ccccc12]

To a solution of ethyl 6-methyl-3-[3-(naphthalen-1-yloxy)propyl]-7-(4,4,5,5-tetramethyl-1,3,2-dioxaborolan-2-yl)-1H-indole-2-carboxylate (2.25 g, 4.38 mmol; see Intermediate 19) and {4-bromo-5-ethyl-1-[2-(morpholin-4-yl)ethyl]-1H-pyrazol-3-yl}methanol (1.27 g, 3.98 mmol; see Intermediate 335) in THF (48 ml) was added an aqueous solution of potassium phosphate (16 ml, 0.50 M, 8.0 mmol). The mixture was degassed and purged with argon several times. XPhos Pd G2 (see abbreviation list, 109 mg, 0.14 mmol) was added and the mixture was purged with argon several times. The reaction mixture was stirred at 50° C. for 6 h. For work-up, water was added and the mixture was extracted with ethyl acetate. The combined organic phases were washed with brine and were dried over sodium sulfate. After filtration and removal of the solvents the crude product was purified by flash chromatography (dichloromethane/ethanol gradient, 0%→10% ethanol) to give the title compound (1.95 g).

Intermediate 340

(rac)-ethyl (11Z)-3-ethyl-4-methyl-2-[2-(morpholin-4-yl)ethyl]-7-[3-(naphthalen-1-yloxy)propyl]-2,10,13,15-tetrahydropyrazolo[4',3':9,10][1,6]oxazacycloundecino[8,7,6-hi]indole-8-carboxylate

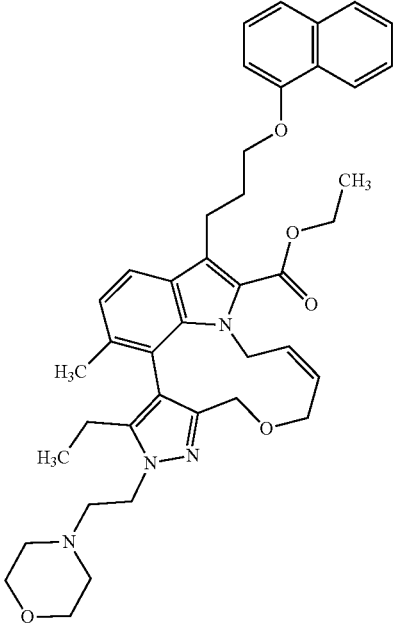 [SMILES: CCOC(=O)c1c(CCCOc2cccc3ccccc23)c2ccc(C)c3c2n1C/C=C\COCc1nn(CCN2CCOCC2)c(CC)c1-3]

To a solution of ethyl 7-{5-ethyl-3-(hydroxymethyl)-1-[2-(morpholin-4-yl)ethyl]-1H-pyrazol-4-yl}-6-methyl-3-[3-(naphthalen-1-yloxy)propyl]-1H-indole-2-carboxylate (1.95 g, 83% purity, 2.59 mmol; see Intermediate 339) in acetonitrile (29 ml) was added caesium carbonate (4.22 g, 13.0 mmol) and the mixture was stirred for 10 min at room temperature. (2Z)-1,4-dichlorobut-2-ene (320 µl, 2.8 mmol) and sodium iodide (784 mg, 5.18 mmol) were added and the reaction mixture was stirred for 18 hours at 40° C. For work-up, the reaction mixture was poured into water. The mixture was extracted with ethyl acetate. The combined organic phases washed with brine and dried over sodium sulfate. After filtration and removal of the solvent the crude product was purified by flash chromatography (dichloromethane/acetone gradient, 10%→60% acetone) to give the title compound (700 mg).

$^1$H-NMR (400 MHz, DMSO-d6) δ[ppm]: 0.713 (4.00), 0.732 (9.22), 0.751 (4.05), 1.066 (1.58), 1.138 (1.20), 1.230 (0.48), 1.257 (6.05), 1.275 (13.14), 1.293 (6.15), 1.930 (16.00), 2.116 (0.52), 2.169 (0.96), 2.188 (2.91), 2.208 (3.27), 2.227 (1.97), 2.323 (0.61), 2.327 (0.85), 2.331 (0.62), 2.398 (0.96), 2.414 (1.36), 2.427 (2.02), 2.437 (1.30), 2.461 (2.14), 2.478 (1.87), 2.518 (3.24), 2.523 (2.19), 2.665 (0.68), 2.669 (0.92), 2.673 (0.68), 2.721 (0.88), 2.737 (0.95), 2.753 (1.46), 2.767 (0.65), 2.809 (0.61), 2.825 (1.24), 2.841 (1.08), 2.858 (0.71), 3.243 (0.44), 3.259 (0.79), 3.277 (1.23), 3.297 (0.95), 3.306 (1.29), 3.517 (3.72), 3.528 (6.66), 3.540 (3.76), 3.559 (0.99), 3.573 (1.09), 3.590 (1.17), 3.602 (1.00), 3.761 (0.98), 3.790 (1.57), 3.820 (0.79), 3.970 (0.45), 4.118 (2.46), 4.151 (2.97), 4.176 (0.91), 4.189 (0.91), 4.196 (0.95), 4.207 (2.08), 4.212 (2.56), 4.224 (2.83), 4.233 (4.39), 4.251 (2.84), 4.265 (1.22), 4.269 (1.13), 4.277 (1.39), 4.283 (2.60), 4.293 (1.22), 4.301 (2.33), 4.310 (1.63), 4.318 (0.79), 4.328 (1.43), 4.400 (2.96), 4.432 (2.52), 4.583 (0.66), 4.609 (0.79), 4.621 (1.03), 4.636 (0.41), 4.648 (1.17), 4.804 (1.23), 4.842 (0.86), 4.935 (0.65), 4.941 (0.62), 4.962 (1.22), 4.968 (1.17), 4.989 (0.66), 5.206 (0.48), 5.219 (0.51), 5.234 (0.85), 5.246 (0.79), 5.261 (0.42), 5.759 (1.12), 6.906 (2.26), 6.924 (2.42), 7.047 (3.08), 7.068 (3.41), 7.374 (1.67), 7.395 (3.21), 7.414 (2.65), 7.455 (3.32), 7.476 (1.88), 7.487 (0.62), 7.491 (0.81), 7.504 (1.97), 7.508 (1.77), 7.516 (2.02), 7.522 (4.29), 7.528 (2.14), 7.535 (1.85), 7.539 (2.14), 7.552 (0.85), 7.556 (0.58), 7.643 (3.58), 7.664 (3.18), 7.864 (1.92), 7.871 (1.08), 7.882 (1.98), 7.887 (1.66), 8.217 (1.67), 8.223 (1.64), 8.242 (1.58).

Intermediate 341

(rac)-ethyl 3-ethyl-4-methyl-2-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylate

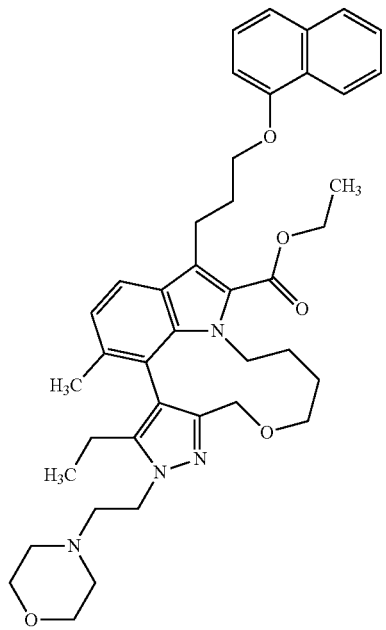 [SMILES: CCOC(=O)c1c(CCCOc2cccc3ccccc23)c2ccc(C)c3c2n1CCCCOCc1nn(CCN2CCOCC2)c(CC)c1-3]

A suspension of (rac)-ethyl (11Z)-3-ethyl-4-methyl-2-[2-(morpholin-4-yl)ethyl]-7-[3-(naphthalen-1-yloxy)propyl]-2,10,13,15-tetrahydropyrazolo[4',3':9,10][1,6]oxazacycloundecino[8,7,6-hi]indole-8-carboxylate (700 mg, 1.03 mmol; see Intermediate 340) and Pd/C (71.0 mg, 10%, 66.7 µmol) in ethanol (27 ml) was stirred under an atmosphere of hydrogen at room temperature for 18 hours. For work-up, the mixture was filtered through a pad of celite. The residue was washed with ethyl acetate and the filtrate was concentrated under reduced pressure to give the title compound (700 mg), which was used in the subsequent steps without further purification.

Intermediate 342 ethyl 5-methoxy-1-methyl-1H-pyrazole-3-carboxylate

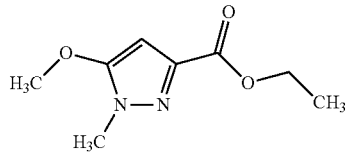

To a mixture of ethyl 5-hydroxy-1H-pyrazole-3-carboxylate (10.0 g, 64.0 mmol, CAS 51986-17-5) in DMF (300 ml) was added caesium carbonate (45.9 g, 141 mmol) and the mixture was stirred at room temperature for 10 min. The reaction was cooled down to 0° C. and iodomethane (8.2 ml, 130 mmol) was added and the mixture was stirred at room temperature overnight. For work-up, the reaction was concentrated under reduced pressure and the crude product was purified by flash chromatography (hexane/acetone gradient, 0%→100% acetone) to give the title compound (1.46 g).

Intermediate 343 ethyl 4-bromo-5-methoxy-1-methyl-1H-pyrazole-3-carboxylate

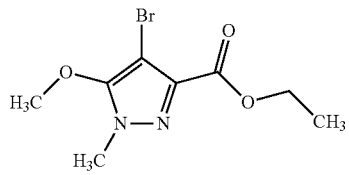

To a solution of ethyl 5-methoxy-1-methyl-1H-pyrazole-3-carboxylate (1.90 g, 10.3 mmol; see Intermediate 342) in acetonitrile (27 ml) was added N-Bromosuccinimide (2.02 g, 11.3 mmol) and the mixture was stirred at 60° C. for 3 hours. For work-up, the reaction mixture was concentrated under reduced pressure. Hexane (30 ml) and a few drops of dichloromethane were added, the resulting precipitate was filtrated off and the filtrate was concentrated under reduced pressure to give the crude product which was purified by flash chromatography (hexane/ethyl acetate gradient, 0%→75% ethyl acetate) to give the title compound (2.2 g).

LC-MS (Method 2): Rt=0.98 min; MS (ESIpos): m/z=261 [M+H]$^+$ $^1$H-NMR (400 MHz, DMSO-d6) δ[ppm]: 1.259 (2.79), 1.277 (5.90), 1.295 (2.77), 3.329 (4.08), 4.012 (16.00), 4.232 (0.89), 4.250 (2.83), 4.268 (2.74), 4.285 (0.83).

Intermediate 344

(4-bromo-5-methoxy-1-methyl-1H-pyrazol-3-yl)methanol

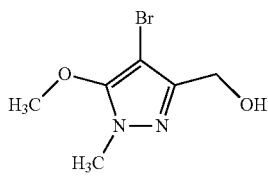

To a solution of ethyl 4-bromo-5-methoxy-1-methyl-1H-pyrazole-3-carboxylate (2.20 g, 8.36 mmol; see Intermediate 343) in THF (34 ml) was added a solution of lithium borohydride in THF (5.0 ml, 2.0 M, 10 mmol) and the mixture was stirred at 60° C. for 17 h. For work-up, sodium sulfate and water were added and the reaction mixture was stirred for 1 hour at room temperature. The mixture was filtrated and the residue was washed with a mixture of dichloromethane and methanol. The filtrate was concentrated under reduced pressure and the crude product was purified by flash chromatography (dichloromethane/methanol 9:1) to give the title compound (755 mg).

$^1$H-NMR (400 MHz, DMSO-d$_6$): δ [ppm]=5.05-4.92 (m, 1H), 4.25 (d, 2H), 3.97 (s, 3H), 3.64-3.57 (m, 3H), 3.33 (s, 2H)

Intermediate 345 ethyl 7-[3-(hydroxymethyl)-5-methoxy-1-methyl-1H-pyrazol-4-yl]-3-[3-(naphthalen-1-yloxy)propyl]-1H-indole-2-carboxylate

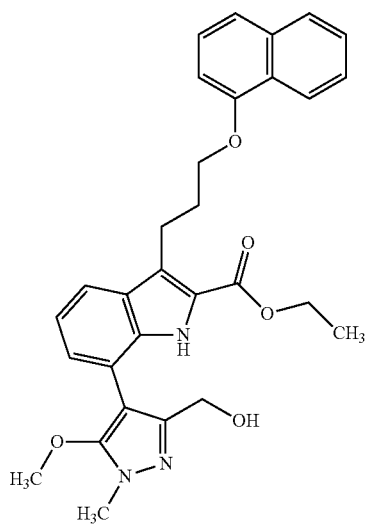 [SMILES: CCOC(=O)c1[nH]c2c(-c3c(CO)nn(C)c3OC)cccc2c1CCCOc1cccc2ccccc12]

To a solution of ethyl 3-[3-(naphthalen-1-yloxy)propyl]-7-(4,4,5,5-tetramethyl-1,3,2-dioxaborolan-2-yl)-1H-indole-2-carboxylate (1.86 g, 3.73 mmol; see Intermediate 5) and (4-bromo-5-methoxy-1-methyl-1H-pyrazol-3-yl)methanol (750 mg, 3.39 mmol; see Intermediate 344) in THF (41 ml) was added an aqueous solution of potassium phosphate (14 ml, 0.50 M, 6.8 mmol). The mixture was degassed and purged with argon several times. XPhos Pd G2 (see abbreviation list, 93.4 mg, 119 µmol) was added and the mixture was purged with argon several times. The reaction mixture was stirred at 50° C. for 2 h. For work-up, the reaction was filtrated and the residue was washed with dichloromethane. The filtrate was concentrated and the crude product was purified by flash chromatography (dichloromethane/acetone gradient, 0%→40% acetone) to give the title compound (1.09 g).

LC-MS (Method 2): Rt=1.49 min; MS (ESIpos): m/z=514 [M+H]$^+$ $^1$H-NMR (400 MHz, DMSO-d6) δ[ppm]: 1.066 (16.00), 1.267 (1.79), 1.284 (4.03), 1.302 (1.84), 2.234 (0.46), 2.518 (0.88), 2.523 (0.62), 3.356 (0.65), 3.373 (0.42), 3.510 (8.55), 3.604 (2.64), 3.695 (6.22), 3.939 (2.57), 3.971 (3.34), 4.201 (1.55), 4.215 (1.77), 4.231 (0.53), 4.242 (1.32), 4.256 (1.00), 4.260 (1.69), 4.278 (1.62), 4.295 (0.47), 4.995 (0.48), 5.642 (0.86), 6.904 (0.62), 6.921 (0.67), 7.065 (0.58), 7.083 (0.81), 7.085 (0.75), 7.103 (0.69), 7.274 (0.80), 7.277 (0.85), 7.293 (0.72), 7.295 (0.65), 7.371 (0.49), 7.392 (0.90), 7.411 (0.74), 7.450 (0.91), 7.471 (0.51), 7.507 (0.57), 7.511 (0.54), 7.514 (0.69), 7.523 (1.28), 7.531 (0.75), 7.533 (0.60), 7.538 (0.62), 7.671 (0.67), 7.690 (0.62), 7.861 (0.52), 7.878 (0.43), 7.884 (0.44), 8.234 (0.46), 8.241 (0.41), 8.258 (0.43), 11.247 (0.88).

Intermediate 346

(rac)-ethyl (11Z)-3-methoxy-2-methyl-7-[3-(naphthalen-1-yloxy)propyl]-2,10,13,15-tetrahydropyrazolo[4',3':9,10][1,6]oxazacycloundecino[8,7,6-hi]indole-8-carboxylate

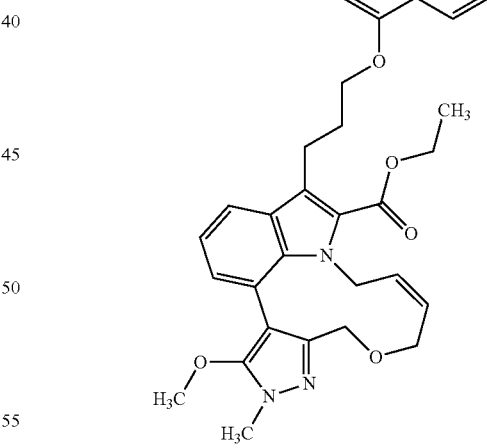

To a solution of ethyl 7-[3-(hydroxymethyl)-5-methoxy-1-methyl-1H-pyrazol-4-yl]-3-[3-(naphthalen-1-yloxy)propyl]-1H-indole-2-carboxylate (1.09 g, 2.12 mmol; see Intermediate 345) in acetonitrile (23 ml) was added caesium carbonate (3.46 g, 10.6 mmol) and the mixture was stirred for 10 min at room temperature. (2Z)-1,4-dichlorobut-2-ene (260 µl, 2.3 mmol) and sodium iodide (643 mg, 4.24 mmol) were added and the reaction mixture was stirred for 23 hours at 40° C. For work-up, the reaction mixture was concentrated under reduced pressure, and the crude product was purified by flash chromatography (dichloromethane/acetone gradient, 0%→25% acetone) to give the title compound (529 mg).

LC-MS (Method 2): $R_t$=1.65 min; MS (ESIpos): m/z=566 [M+H]$^+$ $^1$H-NMR (400 MHz, DMSO-d6) δ[ppm]: 1.275 (1.76), 1.293 (3.96), 1.311 (1.80), 2.085 (0.46), 2.228 (0.48), 2.518 (1.27), 2.523 (0.89), 3.306 (0.41), 3.321 (10.42), 3.329 (16.00), 4.187 (0.41), 4.207 (0.50), 4.220 (1.68), 4.235 (0.77), 4.244 (1.31), 4.263 (0.64), 4.277 (0.48), 4.280 (0.71), 4.305 (0.66), 4.323 (0.60), 5.759 (0.41), 6.899 (0.59), 6.917 (0.63), 6.982 (0.55), 6.985 (0.62), 7.000 (0.85), 7.003 (0.81), 7.055 (0.76), 7.073 (0.66), 7.075 (0.87), 7.093 (0.53), 7.372 (0.47), 7.393 (0.87), 7.412 (0.72), 7.453 (0.87), 7.474 (0.49), 7.509 (0.57), 7.514 (0.58), 7.516 (0.75), 7.525 (1.23), 7.533 (0.79), 7.540 (0.63), 7.767 (0.65), 7.770 (0.69), 7.787 (0.63), 7.791 (0.59), 7.863 (0.49), 7.886 (0.43), 8.221 (0.45), 8.246 (0.41).

Intermediate 347

(rac)-ethyl 3-methoxy-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylate

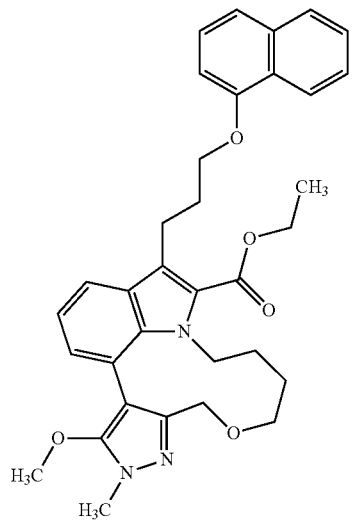 [SMILES: CCOC(=O)c1c(CCCOc2cccc3ccccc23)c2cccc3c2n1CCCCOCc1nn(C)c(OC)c1-3]

A suspension of Pd/C (55.0 mg, 517 μmol) and (rac)-ethyl (11Z)-3-methoxy-2-methyl-7-[3-(naphthalen-1-yloxy)propyl]-2,10,13,15-tetrahydropyrazolo[4',3':9,10][1,6]oxazacycloundecino[8,7,6-hi]indole-8-carboxylate (525 mg, 928 μmol; see Intermediate 346) in ethanol (22 ml) was stirred under an atmosphere of hydrogen at room temperature for 4 h. For work-up, the mixture was filtered through a pad of celite. The residue was washed with ethanol and the filtrate was concentrated under reduced pressure and the residue was purified by flash chromatography (dichloromethane/acetone gradient, 0%→30% acetone) to give the title compound (460 mg).

LC-MS (Method 2): Rt=1.68 min; MS (ESIpos): m/z=568 [M+H]$^+$ $^1$H-NMR (400 MHz, DMSO-d6) δ[ppm]: 1.268 (1.29), 1.285 (2.91), 1.303 (1.32), 2.085 (2.50), 2.518 (1.57), 2.523 (1.06), 3.316 (7.67), 3.329 (16.00), 4.041 (0.56), 4.072 (0.60), 4.190 (0.50), 4.196 (0.42), 4.209 (0.43), 4.235 (0.47), 4.253 (0.52), 4.294 (0.51), 4.311 (0.45), 4.463 (0.57), 4.494 (0.51), 6.876 (0.44), 6.892 (0.49), 7.048 (1.44), 7.053 (0.79), 7.065 (0.74), 7.383 (0.66), 7.402 (0.54), 7.450 (0.64), 7.517 (0.49), 7.520 (0.54), 7.523 (0.45), 7.531 (0.60), 7.538 (0.47), 7.541 (0.57), 7.544 (0.56), 7.742 (0.45), 7.749 (0.47), 7.765 (0.40).

Intermediate 348

(rac)-ethyl 1-methyl-7-[3-(naphthalen-1-yloxy)propyl]-3-[(pyrimidin-5-yloxy)methyl]-1,10,11,12,13,15-hexahydropyrazolo[4',3':9,10][1,6]oxazacycloundecino[8,7,6-hi]indole-8-carboxylate

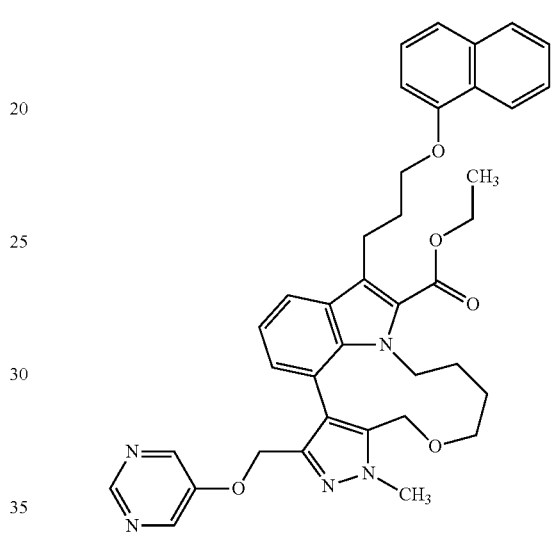

To a solution of pyrimidin-5-ol (45.7 mg, 476 μmol) in DMF (2.0 ml) caesium carbonate (310 mg, 951 μmol) was added. After stirring for 10 minutes (rac)-ethyl 3-(bromomethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (see Intermediate 258; 200 mg, 317 μmol) was added and stirring continued for 2 hours. After concentration to dryness the residue was purified by flash chromatography (Biotage SNAP cartridge silica 25 g, dichloromethane/methanol gradient, 0%-10% methanol) to give the title compound (151 mg).

LC-MS (Method 2): Rt=1.63 min; MS (ESIpos): m/z=647 [M+H]$^+$ $^1$H-NMR (400 MHz, DMSO-d6) δ[ppm]: 0.852 (0.54), 1.044 (0.91), 1.145 (0.54), 1.233 (2.99), 1.262 (1.12), 1.271 (4.20), 1.280 (0.83), 1.289 (8.81), 1.306 (4.16), 1.321 (0.54), 2.126 (0.79), 2.142 (1.25), 2.159 (0.83), 2.332 (1.75), 2.337 (0.75), 2.518 (9.64), 2.523 (6.73), 2.673 (1.79), 2.679 (0.79), 2.728 (12.80), 2.821 (0.54), 2.850 (0.54), 2.889 (15.54), 3.189 (0.46), 3.204 (0.42), 3.223 (0.75), 3.296 (0.42), 3.347 (0.71), 3.460 (0.58), 3.473 (0.50), 3.489 (0.58), 3.914 (0.42), 3.921 (0.42), 3.944 (12.76), 3.961 (1.66), 3.986 (0.50), 4.004 (0.54), 4.022 (0.58), 4.100 (0.58), 4.116 (1.29), 4.130 (1.29), 4.144 (0.62), 4.212 (0.75), 4.221 (0.54), 4.230 (0.83), 4.239 (1.41), 4.257 (1.95), 4.275 (1.87), 4.292 (2.58), 4.301 (0.87), 4.310 (0.54), 4.319 (0.96), 4.325 (1.50), 4.336 (0.42), 4.353 (0.62), 4.389 (0.54), 4.677 (1.66), 4.711 (1.37), 4.743 (1.70), 4.772 (2.04), 4.960 (2.16), 4.989 (1.83), 6.839 (1.37), 6.857 (1.45), 6.877 (1.45), 6.880 (1.54), 6.894 (1.87), 6.898 (1.79), 6.994 (1.58), 7.012 (1.45), 7.014 (1.70), 7.032 (1.21), 7.357 (1.04), 7.377 (1.95), 7.396 (1.58), 7.444 (2.08), 7.465 (1.25), 7.500 (0.46), 7.512 (1.54), 7.516 (2.08), 7.526 (2.49), 7.535 (2.04), 7.540 (1.62), 7.551 (0.50), 7.705 (1.45), 7.708 (1.50), 7.725 (1.37), 7.727 (1.29), 7.860 (1.25), 7.863 (0.96), 7.874 (0.75), 7.877 (0.83), 7.883 (1.08), 7.951 (1.83), 8.177 (1.91), 8.203 (16.00), 8.227 (1.08), 8.233 (0.75), 8.252 (0.96), 8.636 (1.00), 8.644 (7.94).

Intermediate 349

(rac)-ethyl 3-[(cyclopropyloxy)methyl]-1-methyl-7-[3-(naphthalen-1-yloxy) propyl]-1,10,11,12,13,15-hexahydropyrazolo[4',3':9,10][1,6]oxazacycloundecino[8,7,6-hi]indole-8-carboxylate

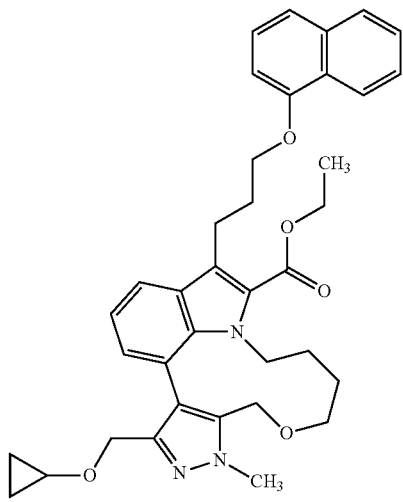 [SMILES: CCOC(=O)c1c(CCCOc2cccc3ccccc23)c2cccc3c2n1CCCCOCc1c-3c(COC2CC2)nn1C]

To a solution of cyclopropanol (32 µl, 630 µmol) in DMF (2.0 ml), caesium carbonate (413 mg, 1.27 mmol) was added. After stirring for 10 minutes, (rac)-ethyl 3-(bromomethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (see Intermediate 258; 200 mg, 317 µmol) was added and stirring was continued at 40° C. for 16 hours. After concentration to dryness the residue was purified by flash chromatography (Biotage SNAP cartridge silica 25 g, dichloromethane/acetone gradient, 0%-30% acetone) to give the title compound (33 mg).

LC-MS (Method 2): Rt=1.72 min; MS (ESIpos): m/z=608 [M+H]+

Intermediate 350

[4-bromo-1-methyl-3-(trifluoromethyl)-1H-pyrazol-5-yl]methanol

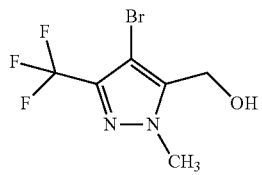

To a solution of 4-bromo-1-methyl-3-(trifluoromethyl)-1H-pyrazole-5-carboxylic acid (4.87 g, 17.8 mmol; purchased from Enamine Ltd., for a preparation procedure see also: *Eur. J. Org. Chem.* 2002, 17, 2913-2920) in THF (100 ml), a borane-tetrahydrofurane complex in THF (110 ml, 1.0 M, 110 mmol) was added via a dropping funnel, and the resulting mixture was stirred at room temperature for 4 days. After addition of a 10% solution of citric acid in water (32 ml) the mixture was extracted with ethyl acetate. After washing of the organic phase with a saturated aqueous solution of sodium chloride the organic phase was dried over sodium sulphate and evaporated after filtration. The residue was purified by flash chromatography (Biotage SNAP cartridge silica, dichloromethane/acetone gradient, 0%-20% acetone) to give the title compound (4.0 g).

$^1$H-NMR (400 MHz, CHLOROFORM-d) δ [ppm]: 0.015 (1.10), 0.033 (1.16), 1.514 (6.82), 1.686 (2.19), 1.701 (4.76), 1.716 (2.33), 3.973 (16.00), 4.685 (9.41), 4.700 (9.51).

Intermediate 351 ethyl 7-[5-(hydroxymethyl)-1-methyl-3-(trifluoromethyl)-1H-pyrazol-4-yl]-3-[3-(naphthalen-1-yloxy) propyl]-1H-indole-2-carboxylate

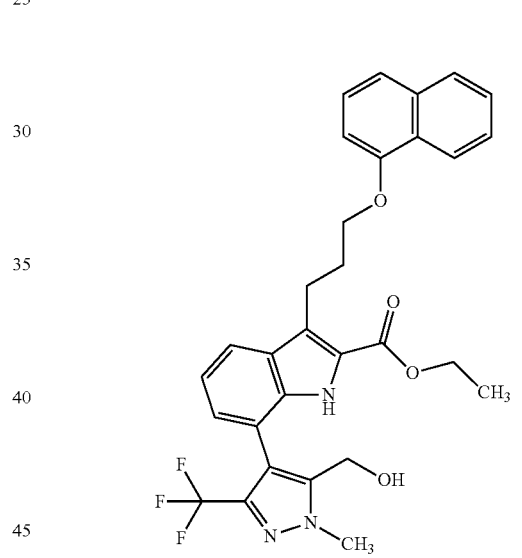

Ethyl 3-[3-(naphthalen-1-yloxy)propyl]-7-(4,4,5,5-tetramethyl-1,3,2-dioxaborolan-2-yl)-1H-indole-2-carboxylate (see Intermediate 5, 925 mg, 1.85 mmol) and [4-bromo-1-methyl-3-(trifluoromethyl)-1H-pyrazol-5-yl]methanol (see Intermediate 350; 400 mg, 1.54 mmol) were dissolved in THF (17 ml). After purging 3 minutes with argon palladium:triphenylphosphane (1:4) (214 mg, 185 µmol) and an aqueous solution of potassium carbonate (1.9 ml, 2.0 M, 3.7 mmol) were added. The reaction vessel was closed and heated to 110° C. for 3 hours in a microwave reactor. 2 identical reactions were combined and evaporated. The residue was purified by flash chromatography (Biotage SNAP cartridge silica, dichloromethane/acetone gradient, 5%-20% acetone) to give the title compound (1.28 g).

LC-MS (Method 2): Rt=1.58 min; MS (ESIpos): m/z=553 [M+H]+

$^1$H-NMR (400 MHz, DMSO-d6) δ[ppm]: 1.254 (5.92), 1.272 (13.93), 1.289 (6.09), 2.084 (16.00), 2.211 (0.92), 2.227 (1.27), 2.247 (0.98), 2.518 (1.90), 2.523 (1.35), 3.349 (1.94), 3.367 (1.16), 3.949 (2.11), 4.010 (11.60), 4.209

(1.58), 4.225 (3.54), 4.240 (1.76), 4.245 (2.16), 4.263 (5.79), 4.281 (5.85), 4.299 (1.73), 4.515 (1.17), 4.529 (1.20), 5.395 (0.74), 5.408 (1.80), 5.419 (0.69), 5.560 (0.67), 6.914 (1.84), 6.931 (1.99), 7.072 (1.12), 7.091 (3.15), 7.109 (5.00), 7.114 (2.70), 7.128 (0.75), 7.376 (1.58), 7.397 (2.73), 7.416 (2.35), 7.455 (2.75), 7.476 (1.50), 7.501 (0.64), 7.513 (1.93), 7.518 (3.04), 7.528 (3.85), 7.537 (3.42), 7.542 (2.01), 7.554 (0.68), 7.742 (1.58), 7.746 (1.49), 7.761 (1.52), 7.765 (1.40), 7.864 (1.55), 7.868 (1.10), 7.874 (0.77), 7.879 (0.96), 7.882 (1.04), 7.887 (1.33), 8.242 (1.43), 8.250 (1.04), 8.255 (0.62), 8.257 (0.61), 8.266 (1.28), 11.004 (2.43).

Intermediate 352

(rac)-ethyl (11Z)-1-methyl-7-[3-(naphthalen-1-yloxy)propyl]-3-(trifluoromethyl)-1,10,13,15-tetrahydropyrazolo[4',3':9,10][1,6]oxazacycloundecino[8,7,6-hi]indole-8-carboxylate

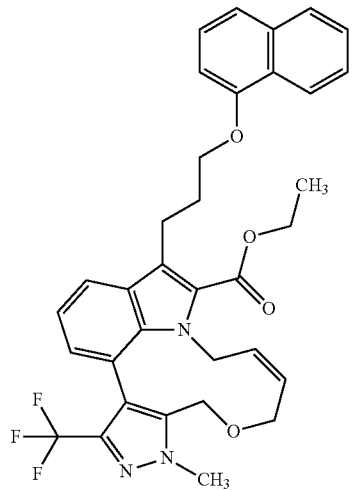 [SMILES: CCOC(=O)c1c(CCCOc2cccc3ccccc23)c2cccc3c2n1C/C=C\COCc1c-3c(C(F)(F)F)nn1C]

Ethyl 7-[5-(hydroxymethyl)-1-methyl-3-(trifluoromethyl)-1H-pyrazol-4-yl]-3-[3-(naphthalen-1-yloxy)propyl]-1H-indole-2-carboxylate (see Intermediate 351; 1.28 g, 2.30 mmol) and caesium carbonate (3.74 g, 11.5 mmol) were mixed in acetonitrile (25 ml) and stirred for ten minutes at ambient temperature. After addition of (2Z)-1,4-dichlorobut-2-ene (280 µl, 95% purity, 2.5 mmol) and sodium iodide (696 mg, 4.59 mmol), the mixture was stirred 24 hours at 40° C. After addition of water, the mixture was extracted three times with ethyl acetate. The combined organic phases were washed with a saturated aqueous solution of sodium chloride, dried over sodium sulphate and evaporated after filtration. The residue was purified by flash chromatography (Biotage SNAP cartridge silica, hexane/ethyl acetate gradient, 12%-100% ethyl acetate) to give the title compound (0.9 g).

LC-MS (Method 2): Rt=1.73 min; MS (ESIpos): m/z=605 [M+H]+

$^1$H-NMR (400 MHz, DMSO-d6) δ[ppm]: 1.154 (0.44), 1.172 (0.92), 1.190 (0.49), 1.259 (0.40), 1.268 (7.20), 1.286 (16.00), 1.304 (7.39), 1.987 (1.73), 2.067 (0.44), 2.212 (0.43), 2.231 (1.32), 2.248 (1.96), 2.264 (1.38), 2.283 (0.47), 2.518 (2.50), 2.523 (1.77), 3.296 (0.45), 3.311 (1.00), 3.346 (2.01), 3.364 (0.88), 3.379 (0.43), 3.539 (0.90), 3.570 (1.53), 3.600 (1.12), 3.800 (0.94), 3.812 (1.11), 3.832 (0.89), 3.844 (0.79), 4.017 (0.64), 4.033 (15.56), 4.202 (2.72), 4.208 (0.83), 4.226 (2.73), 4.237 (4.23), 4.244 (5.76), 4.253 (3.48), 4.259 (2.16), 4.270 (2.75), 4.277 (0.99), 4.288 (0.90), 4.295 (2.84), 4.304 (0.47), 4.312 (2.61), 4.322 (1.30), 4.330 (0.74), 4.340 (1.28), 4.544 (0.61), 4.572 (0.92), 4.587 (1.01), 4.613 (1.23), 4.779 (2.91), 4.815 (2.75), 4.987 (0.62), 4.992 (0.71), 5.019 (1.79), 5.028 (1.65), 5.041 (1.10), 5.067 (1.07), 5.160 (0.66), 5.172 (0.54), 5.190 (0.80), 5.200 (0.76), 6.909 (5.24), 6.911 (5.33), 6.927 (5.40), 6.930 (5.55), 7.100 (2.82), 7.117 (3.05), 7.119 (3.42), 7.137 (2.36), 7.376 (2.02), 7.396 (3.71), 7.415 (3.16), 7.454 (3.66), 7.475 (2.12), 7.481 (1.05), 7.494 (2.21), 7.498 (1.94), 7.501 (1.01), 7.510 (2.52), 7.513 (3.01), 7.516 (3.26), 7.518 (2.55), 7.530 (2.05), 7.534 (2.40), 7.547 (1.06), 7.551 (0.75), 7.833 (2.87), 7.836 (2.87), 7.853 (2.85), 7.856 (2.78), 7.861 (2.35), 7.867 (1.44), 7.880 (2.43), 7.884 (1.86), 8.192 (1.97), 8.196 (1.98), 8.214 (1.85), 8.216 (1.81).

Intermediate 353

(rac)-ethyl 1-methyl-7-[3-(naphthalen-1-yloxy)propyl]-3-(trifluoromethyl)-1,10,11,12,13,15-hexahydropyrazolo[4',3':9,10][1,6]oxazacycloundecino[8,7,6-hi]indole-8-carboxylate

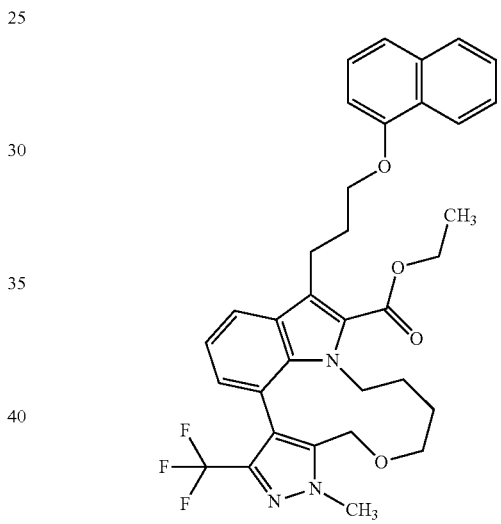

Pd/C (10%. 102 mg, 96.2 µmol) and (rac)-ethyl (11Z)-1-methyl-7-[3-(naphthalen-1-yloxy)propyl]-3-(trifluoromethyl)-1,10,13,15-tetrahydropyrazolo[4',3':9,10][1,6]oxazacycloundecino[8,7,6-hi]indole-8-carboxylate (see Intermediate 352; 900 mg, 1.49 mmol) in ethanol (39 ml) were reacted under an atmosphere of hydrogen at ambient pressure for 8 hours. Filtration and evaporation of the filtrate gave the title compound (890 mg).

LC-MS (Method 2): Rt=1.66 min; MS (ESIpos): m/z=607 [M+H]+

$^1$H-NMR (400 MHz, CHLOROFORM-d) δ [ppm]: 0.000 (1.05), 0.018 (0.98), 0.605 (0.66), 0.624 (1.81), 0.642 (0.96), 0.825 (0.49), 0.843 (0.43), 1.040 (0.50), 1.059 (0.93), 1.073 (1.14), 1.100 (0.87), 1.121 (0.58), 1.193 (1.08), 1.221 (0.83), 1.250 (0.59), 1.294 (6.27), 1.298 (2.08), 1.311 (12.80), 1.316 (3.75), 1.329 (6.11), 1.333 (1.81), 1.371 (0.58), 1.493 (5.30), 1.514 (0.61), 2.245 (0.57), 2.261 (1.73), 2.279 (2.61), 2.296 (1.80), 2.313 (0.64), 2.843 (0.54), 2.856 (0.67), 2.865 (0.60), 2.874 (0.79), 2.887 (0.72), 2.894 (0.64), 2.908 (0.53), 3.257 (0.43), 3.275 (0.79), 3.290 (1.01), 3.308 (1.72), 3.317 (0.81), 3.327 (0.88), 3.349 (0.90), 3.368 (1.70), 3.386 (0.89), 3.401 (0.81), 3.437 (0.58), 3.455 (1.02), 3.467 (0.71), 3.473 (0.72), 3.486 (0.90), 3.504 (0.49), 3.919 (0.75), 3.945 (0.79), 3.952 (1.22), 3.960 (0.86), 3.981 (0.87), 3.988 (1.07), 3.999 (16.00), 4.023 (0.66), 4.034 (3.69), 4.141 (2.57), 4.156 (5.38), 4.172 (2.58), 4.218 (0.99), 4.227 (0.68), 4.235 (1.04), 4.245 (2.11), 4.254 (0.52), 4.263 (2.45), 4.268 (0.98), 4.281 (1.87), 4.286 (2.36), 4.299 (1.28), 4.304 (2.20), 4.313 (1.14), 4.321 (0.74), 4.331 (1.05), 4.355 (2.76), 4.389 (3.25), 4.519 (3.52), 4.553 (2.45), 4.581 (0.58), 4.589 (1.21), 4.599 (0.61), 4.617 (0.57), 4.626 (1.12), 4.634 (0.53), 5.238 (0.76), 6.699 (2.38), 6.706 (0.75), 6.717 (2.53), 6.725 (0.72), 6.835 (2.01), 6.838 (2.24), 6.853 (2.64), 6.856 (2.63), 6.966 (2.30), 6.986 (2.84), 7.004 (1.98), 7.014 (0.77), 7.020 (1.16), 7.039 (0.79), 7.270 (1.59), 7.290 (3.25), 7.309 (2.60), 7.349 (3.52), 7.370 (1.93), 7.408 (0.62), 7.420 (2.22), 7.424 (3.51), 7.434 (3.92), 7.443 (3.42), 7.447 (2.97), 7.458 (0.75), 7.684 (0.47), 7.688 (0.50), 7.708 (2.58), 7.710 (2.55), 7.728 (2.40), 7.731 (2.56), 7.737 (2.22), 7.751 (1.44), 7.754 (1.36), 7.760 (1.75), 8.287 (1.65), 8.297 (1.37), 8.311 (1.69).

Intermediate 354 ethyl 4-bromo-3-formyl-1-methyl-1H-pyrazole-5-carboxylate

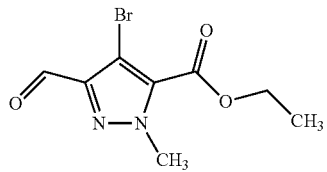

Ethyl 4-bromo-3-(hydroxymethyl)-1-methyl-1H-pyrazole-5-carboxylate (see Intermediate 245; 1.00 g, 3.80 mmol) was dissolved in dichloromethane (17 ml). Then manganese dioxide (2.64 g, 30.4 mmol) was added in portions and the resulting mixture was stirred at 50° C. for 4 hours. After filtration over celite and washing of the filter cake with dichloromethane, the filtrate was evaporated to give the title compound (900 mg).

LC-MS (Method 2): Rt=1.00 min; MS (ESIpos): m/z=261 [M+H]+

$^1$H-NMR (400 MHz, CHLOROFORM-d) δ [ppm]: 0.009 (1.97), 1.374 (4.07), 1.391 (9.17), 1.409 (4.43), 1.502 (2.61), 2.192 (0.43), 4.042 (0.43), 4.211 (16.00), 4.362 (1.38), 4.380 (4.28), 4.398 (4.04), 4.415 (1.16), 9.929 (7.26).

Intermediate 355 ethyl 4-bromo-1-methyl-3-(2,2,2-trifluoroethyl)-1H-pyrazole-5-carboxylate

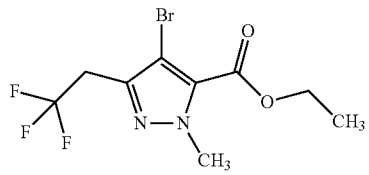 [SMILES: CCOC(=O)c1c(Br)c(CC(F)(F)F)nn1C]

A suspension of ethyl 4-bromo-3-formyl-1H-pyrazole-5-carboxylate (see Intermediate 354, 900 mg, 3.45 mmol) and difluoro(triphenylphosphonio)acetate (2.46 g, 6.89 mmol; for a preparation see: *Chem. Comm.* 2013, 49, 7513-7515) in DMF (15 ml) was heated to 60° C. for one hour. Then N,N,N-tributylbutan-1-aminium fluoride (10 ml, 1.0 M in THF, 10 mmol) was added and the stirring was continued at 60° C. for three hours. After cooling to room temperature, a saturated aqueous ammonium chloride solution was added and the resulting mixture was extracted with ethyl acetate. The organic phase was washed with a saturated aqueous solution of sodium chloride, dried over sodium sulphate and evaporated after filtration. The residue was purified by flash chromatography (Biotage SNAP cartridge silica, hexane/ethyl acetate gradient, 6%-30% ethyl acetate) to give the title compound (0.45 g).

$^1$H-NMR (400 MHz, CHLOROFORM-d) δ [ppm]: 0.018 (0.45), 1.353 (3.67), 1.370 (8.13), 1.388 (4.03), 1.496 (3.47), 3.389 (0.97), 3.414 (2.80), 3.440 (2.85), 3.466 (0.93), 4.110 (16.00), 4.328 (1.19), 4.346 (3.50), 4.364 (3.58), 4.382 (1.20).

Intermediate 356

[4-bromo-1-methyl-3-(2,2,2-trifluoroethyl)-1H-pyrazol-5-yl]methanol

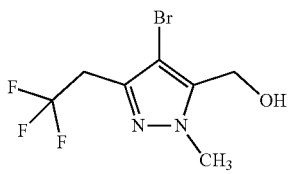

To a solution of ethyl 4-bromo-1-methyl-3-(2,2,2-trifluoroethyl)-1H-pyrazole-5-carboxylate (see Intermediate 355; 1.45 g, 4.60 mmol) in THF (19 ml) was added carefully a solution of lithium borohydride in THF (2.8 ml, 2.0 M, 5.5 mmol) via a syringe at room temperature. Then the reaction mixture was stirred at 60° C. for 19 hours. After cooling to room temperature, sodium sulphate decahydrate was added in small portions and stirring was continued for one hour. After filtration the filtrate was evaporated. The residue was purified by flash chromatography (Biotage SNAP cartridge silica, hexane/ethyl acetate gradient, 12%-100% ethyl acetate) to give the title compound (1.12 g).

$^1$H-NMR (400 MHz, CHLOROFORM-d) δ [ppm]: 1.514 (1.09), 1.672 (0.50), 1.686 (1.05), 1.701 (0.52), 3.330 (1.13), 3.356 (3.29), 3.382 (3.29), 3.408 (1.08), 3.898 (16.00), 4.634 (2.86), 4.649 (2.86).

Intermediate 357 ethyl 7-[5-(hydroxymethyl)-1-methyl-3-(2,2,2-trifluoroethyl)-1H-pyrazol-4-yl]-3-[3-(naphthalen-1-yloxy)propyl]-1H-indole-2-carboxylate

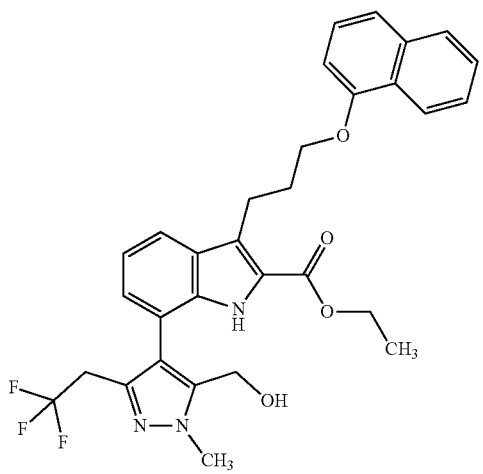

Ethyl 3-[3-(naphthalen-1-yloxy)propyl]-7-(4,4,5,5-tetramethyl-1,3,2-dioxaborolan-2-yl)-1H-indole-2-carboxylate (see intermediate 5; 2.01 g, 4.03 mmol) and [4-bromo-1-methyl-3-(2,2,2-trifluoroethyl)-1H-pyrazol-5-yl]methanol (see Intermediate 356; 1.00 g, 3.66 mmol) were reacted under ultrasound in THF (45 ml) for five minutes under an argon atmosphere. Then an aqueous solution of potassium phosphate (15 ml, 0.50 M, 7.3 mmol) was added and the mixture was purged with argon. Afterwards XPhos Pd G2 (144 mg, 183 µmol) was added. The mixture then was evaporated and purged with argon twice. After stirring the reaction mixture for 4 hours at 40° C., it was poured into water and extracted three times with ethyl acetate. The combined organic phases were washed with a saturated aqueous solution of sodium chloride, dried over sodium sulphate and evaporated after filtration. The residue was purified by flash chromatography (Biotage SNAP cartridge silica, hexane/ethyl acetate gradient, 12%-100% ethyl acetate) to give the title compound (2.1 g).

LC-MS (Method 2): Rt=1.58 min; MS (ESIpos): m/z=567 [M+H]$^+$ $^1$H-NMR (400 MHz, DMSO-d6) δ[ppm]: 1.067 (3.21), 1.154 (1.43), 1.172 (2.88), 1.190 (1.47), 1.260 (5.21), 1.278 (11.61), 1.295 (5.26), 1.987 (4.59), 2.214 (0.81), 2.232 (1.14), 2.249 (0.85), 2.518 (1.45), 2.523 (1.12), 3.350 (1.68), 3.371 (1.00), 3.539 (0.42), 3.747 (1.29), 3.939 (16.00), 4.017 (1.04), 4.035 (1.04), 4.204 (1.24), 4.219 (2.61), 4.235 (1.55), 4.260 (2.11), 4.275 (1.84), 4.292 (0.67), 4.367 (0.49), 5.600 (1.02), 6.906 (1.61), 6.923 (1.76), 7.084 (0.74), 7.102 (2.49), 7.114 (2.79), 7.120 (5.45), 7.131 (0.76), 7.373 (1.36), 7.393 (2.38), 7.412 (1.98), 7.452 (2.38), 7.473 (1.33), 7.494 (0.59), 7.507 (1.57), 7.511 (1.42), 7.515 (1.83), 7.523 (3.54), 7.531 (1.81), 7.535 (1.50), 7.539 (1.73), 7.551 (0.59), 7.709 (1.54), 7.715 (1.33), 7.725 (1.40), 7.732 (1.30), 7.861 (1.36), 7.865 (1.07), 7.870 (0.71), 7.879 (1.17), 7.885 (1.16), 8.232 (1.26), 8.238 (1.13), 8.247 (0.52), 8.248 (0.59), 8.254 (1.03), 8.257 (1.11), 10.916 (1.16).

Intermediate 358

(rac)-ethyl (11Z)-1-methyl-7-[3-(naphthalen-1-yloxy)propyl]-3-(2,2,2-trifluoroethyl)-1,10,13,15-tetrahydropyrazolo[4',3':9,10][1,6]oxazacycloundecino[8,7,6-hi]indole-8-carboxylate

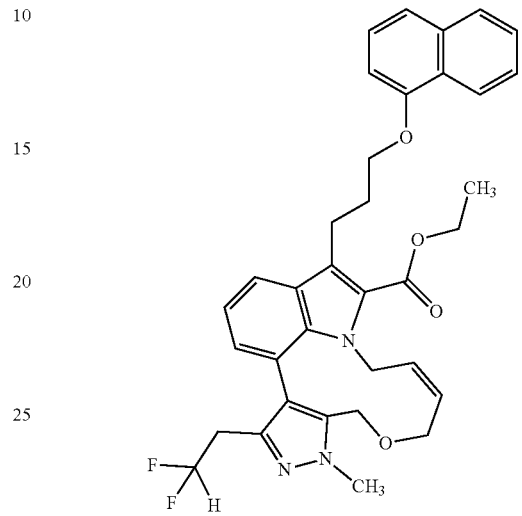

Ethyl 7-[5-(hydroxymethyl)-1-methyl-3-(2,2,2-trifluoroethyl)-1H-pyrazol-4-yl]-3-[3-(naphthalen-1-yloxy)propyl]-1H-indole-2-carboxylate (see Intermediate 357; 1.05 g, 1.86 mmol) and caesium carbonate (3.02 g, 9.28 mmol) were mixed in acetonitrile (21 ml) and stirred for ten minutes at ambient temperature. After addition of (2Z)-1,4-dichlorobut-2-ene (230 µl, 95% purity, 2.0 mmol) and sodium iodide (562 mg, 3.71 mmol), the mixture was stirred 24 hours at 40° C. After addition of water the mixture was extracted three times with ethyl acetate. The combined organic phases were washed with a saturated aqueous solution of sodium chloride, dried over sodium sulphate and evaporated after filtration. The residue was purified by flash chromatography (Biotage SNAP cartridge silica, hexane/ethyl acetate gradient, 12%-100% ethyl acetate) to give the title compound (0.73 g).

LC-MS (Method 2): Rt=1.73 min; MS (ESIpos): m/z=619 [M+H]$^+$ $^1$H-NMR (400 MHz, DMSO-d6) δ[ppm]: 1.272 (4.91), 1.289 (11.16), 1.307 (5.05), 1.987 (0.57), 2.235 (0.81), 2.253 (1.17), 2.269 (0.86), 2.518 (2.08), 2.523 (1.46), 2.990 (0.43), 3.018 (0.45), 3.028 (0.89), 3.056 (0.96), 3.083 (1.00), 3.111 (0.82), 3.121 (0.50), 3.315 (0.68), 3.349 (1.23), 3.367 (0.57), 3.478 (0.59), 3.509 (1.04), 3.540 (0.72), 3.788 (0.60), 3.800 (0.78), 3.821 (0.58), 3.833 (0.54), 3.945 (16.00), 4.195 (1.76), 4.229 (3.75), 4.243 (2.85), 4.247 (2.08), 4.256 (2.78), 4.274 (1.85), 4.280 (0.64), 4.292 (0.58), 4.297 (1.76), 4.316 (1.66), 4.324 (0.89), 4.333 (0.48), 4.342 (0.91), 4.615 (0.50), 4.641 (0.58), 4.655 (0.66), 4.683 (0.64), 4.737 (1.95), 4.772 (1.81), 4.969 (0.84), 4.983 (0.57), 5.006 (2.20), 5.031 (0.55), 5.188 (0.52), 5.200 (0.54), 5.759 (0.67), 6.831 (1.62), 6.834 (1.68), 6.849 (1.86), 6.852 (1.78), 6.906 (1.65), 6.923 (1.78), 7.091 (1.94), 7.109 (1.88), 7.111 (2.19), 7.129 (1.68), 7.371 (1.34), 7.392 (2.45), 7.411 (2.06), 7.452 (2.39), 7.473 (1.36), 7.482 (0.49), 7.485 (0.65), 7.499 (1.43), 7.502 (1.32), 7.506 (0.66), 7.511 (1.57), 7.517 (2.62), 7.523 (1.57), 7.531 (1.43), 7.535 (1.66), 7.548 (0.69), 7.553 (0.47), 7.813 (1.84), 7.815

(1.92), 7.833 (1.73), 7.836 (1.71), 7.861 (1.41), 7.867 (0.86), 7.879 (1.59), 7.884 (1.21), 8.200 (1.28), 8.205 (1.27), 8.222 (1.16), 8.224 (1.19).

Intermediate 359

(rac)-ethyl 1-methyl-7-[3-(naphthalen-1-yloxy)propyl]-3-(2,2,2-trifluoroethyl)-1,10,11,12,13,15-hexahydropyrazolo[4',3':9,10][1,6]oxazacycloundecino[8,7,6-hi]indole-8-carboxylate

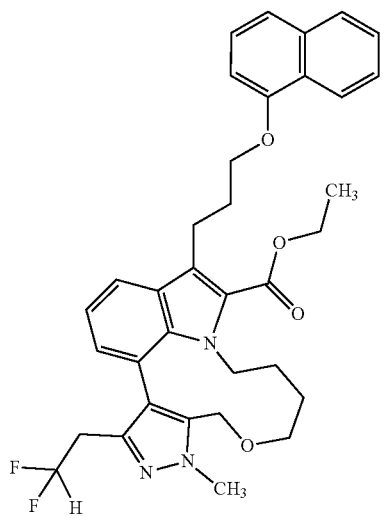 [SMILES: CCOC(=O)c1c(CCCOc2cccc3ccccc23)c2cccc3c2n1CCCCOCc1c-3c(CC(F)F)nn1C]

(rac)-Ethyl (11Z)-1-methyl-7-[3-(naphthalen-1-yloxy)propyl]-3-(2,2,2-trifluoroethyl)-1,10,13,15-tetrahydropyrazolo[4',3':9,10][1,6]oxazacycloundecino[8,7,6-hi]indole-8-carboxylate (see Intermediate 358; 730 mg, 1.18 mmol) and Pd/C (10%, 62.9 mg, 59.1 µmol) were reacted under an atmosphere of hydrogen in ethanol (31 ml) at ambient pressure for 8 hours. Filtration, evaporation of the filtrate, and flash chromatography of the residue (Biotage SNAP cartridge silica, hexane/ethyl acetate gradient, 12%-100% ethyl acetate) gave the title compound (0.70 g).

LC-MS (Method 2): Rt=1.66 min; MS (ESIpos): m/z=621 [M+H]$^+$

Intermediate 360 ethyl 1-{4-[(tert-butoxycarbonyl)(methyl)amino]butyl}-7-[5-(hydroxymethyl)-1-methyl-3-(2,2,2-trifluoroethyl)-1H-pyrazol-4-yl]-3-[3-(naphthalen-1-yloxy)propyl]-1H-indole-2-carboxylate

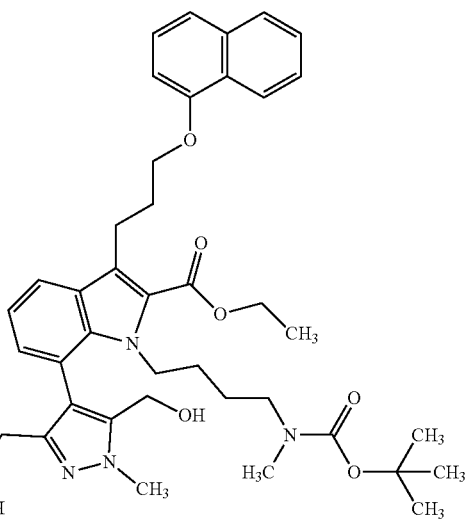

Caesium carbonate (2.04 g, 6.26 mmol) was added to a solution of ethyl 7-[5-(hydroxymethyl)-1-methyl-3-(2,2,2-trifluoroethyl)-1H-pyrazol-4-yl]-3-[3-(naphthalen-1-yloxy)propyl]-1H-indole-2-carboxylate (see intermediate 357; 708 mg, 1.25 mmol) in DMF (16 ml). After stirring for ten minutes, tert-butyl 4-bromobutyl)methylcarbamate (see Intermediate 2; 400 mg, 1.50 mmol) was added and stirring continued for seven days. After addition of water the mixture was extracted three times with ethyl acetate. The combined organic phases were washed with a saturated aqueous solution of sodium chloride, dried over sodium sulphate and evaporated after filtration. The residue was purified by flash chromatography (Biotage SNAP cartridge silica, hexane/ethyl acetate gradient, 12%-100% ethyl acetate) to give the title compound (0.50 g).

LC-MS (Method 02): Rt=1.73 min; MS (ESIpos): m/z=752 [M+H]$^+$

Intermediate 361 ethyl 7-[5-(bromomethyl)-1-methyl-3-(2,2,2-trifluoroethyl)-1H-pyrazol-4-yl]-1-{4-[(tert-butoxycarbonyl)(methyl)amino]butyl}-3-[3-(naphthalen-1-yloxy)propyl]-1H-indole-2-carboxylate

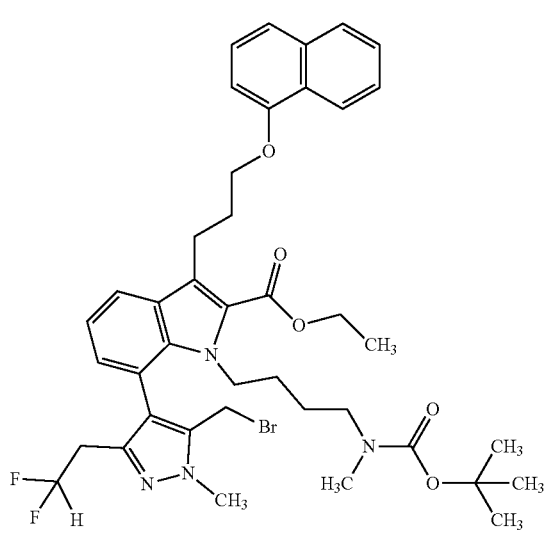 [SMILES: CCOC(=O)c1c(CCCOc2cccc3ccccc23)c2cccc(-c3c(CC(F)F)nn(C)c3CBr)c2n1CCCCN(C)C(=O)OC(C)(C)C]

At 0° C., to a solution of ethyl 1-{4-[(tert-butoxycarbonyl)(methyl)amino]butyl}-7-[5-(hydroxymethyl)-1-methyl-3-(2,2,2-trifluoroethyl)-1H-pyrazol-4-yl]-3-[3-(naphthalen-1-yloxy)propyl]-1H-indole-2-carboxylate (see Intermediate 360; 500 mg, 666 µmol) in dichloromethane (12 ml) was added triphenylphosphine (262 mg, 999 µmol) and the resulting mixture was stirred for 10 minutes. After addition of carbon tetrabromide (331 mg, 999 µmol), the mixture was stirred at room temperature for 28 hours. Then the mixture was evaporated and the residue was purified by flash chromatography (Biotage SNAP cartridge silica, hexane/ethyl acetate gradient, 7%→60% ethyl acetate) to give the title compound (0.54 g).

LC-MS (Method 1): Rt=1.82 min; MS (ESIpos): m/z=815 [M+H]$^+$

Intermediate 362 ethyl 7-[5-(bromomethyl)-1-methyl-3-(2,2,2-trifluoroethyl)-1H-pyrazol-4-yl]-1-[4-(methylamino)butyl]-3-[3-(naphthalen-1-yloxy)propyl]-1H-indole-2-carboxylate hydrochloric acid salt

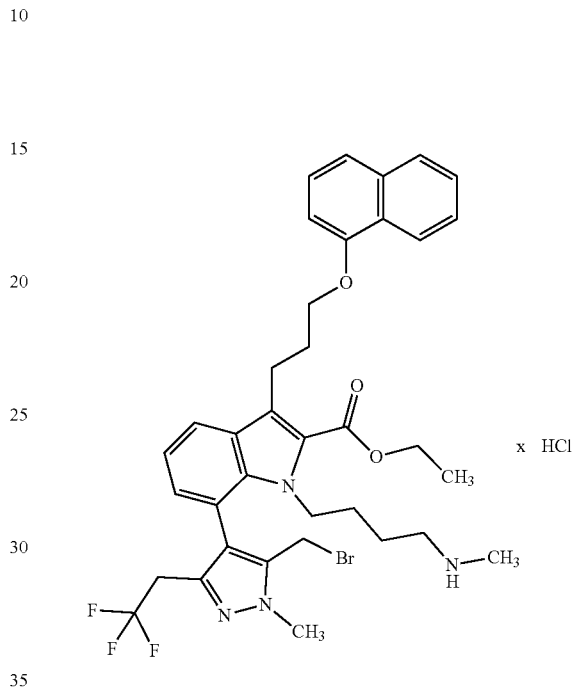

At 0° C. a solution of hydrochloric acid in 1,4-dioxane (12 ml, 4.0 M, 46 mmol) was added to a solution of ethyl 7-[5-(bromomethyl)-1-methyl-3-(2,2,2-trifluoroethyl)-1H-pyrazol-4-yl]-1-{4-[(tert-butoxycarbonyl)(methyl)amino]butyl}-3-[3-(naphthalen-1-yloxy)propyl]-1H-indole-2-carboxylate (see Intermediate 361; 540 mg, 664 µmol) in methanol (12 ml). Then the reaction mixture was stirred at room temperature for two hours and evaporated to dryness. The crude title compound thus obtained (500 mg) was used in the next step without purification.

685

Intermediate 363

(rac)-ethyl 1,14-dimethyl-7-[3-(naphthalen-1-yloxy)
propyl]-3-(2,2,2-trifluoroethyl)-10,11,12,13,14,15-
hexahydro-1H-pyrazolo[3',4':8,9][1,6]diazacycloun-
decino[10,11,1-hi]indole-8-carboxylate

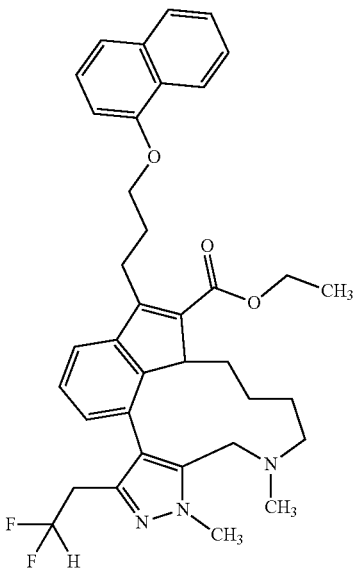 [SMILES: CCOC(=O)C1=C(CCCOc2cccc3ccccc23)c2cccc3c2C1CCCCN(C)Cc1c-3c(CC(F)F)nn1C]

Crude ethyl 7-[5-(bromomethyl)-1-methyl-3-(2,2,2-trifluoroethyl)-1H-pyrazol-4-yl]-1-[4-(methylamino)butyl]-3-[3-(naphthalen-1-yloxy)propyl]-1H-indole-2-carboxylate hydrochloric acid salt (see Intermediate 362; 500 mg) was dissolved in DMF (59 ml) and caesium carbonate (1.09 g, 3.33 mmol) was added. The mixture was then stirred at 60° C. for 20 hours. After cooling and removing the volatiles under reduced pressure, the residue was purified by flash chromatography (Biotage SNAP cartridge silica, dichloromethane/methanol gradient, 0%-60% methanol) to give the title compound (0.21 g).

LC-MS (Method 2): Rt=1.81 min; MS (ESIpos): m/z=634 [M+H]+

$^1$H-NMR (400 MHz, DMSO-d6) δ[ppm]: 0.726 (0.46), 0.753 (0.53), 0.984 (0.44), 1.088 (0.75), 1.264 (5.12), 1.282 (10.93), 1.300 (5.34), 1.878 (0.41), 1.906 (0.70), 1.935 (0.43), 2.150 (10.62), 2.199 (0.94), 2.215 (1.33), 2.232 (0.99), 2.423 (0.51), 2.442 (0.52), 2.466 (0.50), 2.518 (2.24), 2.523 (1.52), 3.015 (0.60), 3.043 (0.62), 3.054 (0.89), 3.082 (0.77), 3.217 (0.84), 3.229 (0.43), 3.247 (2.55), 3.256 (1.12), 3.266 (0.78), 3.281 (2.42), 3.304 (0.53), 3.350 (0.97), 3.370 (0.66), 3.385 (0.50), 3.681 (1.81), 3.714 (1.61), 3.843 (0.41), 3.872 (0.71), 3.919 (16.00), 4.204 (1.02), 4.222 (2.00), 4.231 (3.24), 4.248 (2.84), 4.267 (0.90), 4.286 (1.75), 4.303 (1.63), 4.313 (0.95), 4.321 (0.47), 4.330 (0.92), 4.482 (0.71), 4.518 (0.65), 6.849 (1.74), 6.851 (1.83), 6.867 (2.08), 6.869 (2.03), 6.900 (1.90), 6.919 (2.06), 7.057 (1.89), 7.077 (2.24), 7.095 (1.60), 7.370 (1.40), 7.390 (2.67), 7.409 (2.09), 7.455 (2.73), 7.475 (1.57), 7.504 (0.50), 7.516 (1.74), 7.519 (2.47), 7.529 (2.99), 7.539 (2.46), 7.543 (2.04), 7.554 (0.58), 7.780 (1.90), 7.783 (1.99), 7.800 (1.82), 7.803 (1.79), 7.864 (1.54), 7.868 (1.05), 7.877 (1.02), 7.882 (0.97), 7.887 (1.30), 8.246 (1.33), 8.256 (1.01), 8.270 (1.25).

686

Intermediate 364 ethyl 4-bromo-3-(2,2-difluoroethenyl)-1-methyl-1H-pyrazole-5-carboxylate

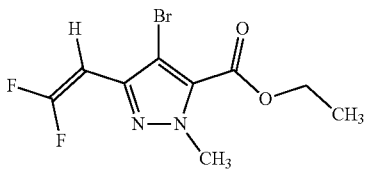 [SMILES: CCOC(=O)c1c(Br)c(C=C(F)F)nn1C]

A mixture of ethyl 4-bromo-3-formyl-1-methyl-1H-pyrazole-5-carboxylate (see Intermediate 354; 3.00 g, 11.5 mmol) and difluoro(triphenylphosphonio)acetate (8.19 g, 23.0 mmol; for a preparation see: Chem. Comm. 2013, 49, 7513-7515) in DMF (49 ml) was stirred at 60° C. for 3 hours. After cooling to room temperature, a saturated aqueous ammonium chloride solution was added and the resulting mixture was extracted with ethyl acetate. The organic phase was washed with a saturated aqueous solution of sodium chloride, dried over sodium sulphate and evaporated after filtration. The residue was purified twice by flash chromatography (Biotage SNAP cartridge silica, hexane/ethyl acetate gradient, gradient for first chromatography 5%→30% ethyl acetate, gradient for second chromatography 6%-30% ethyl acetate) to give the title compound (2.32 g).

$^1$H-NMR (400 MHz, CHLOROFORM-d) δ [ppm]: 1.351 (3.96), 1.369 (8.21), 1.387 (4.01), 1.491 (3.60), 4.116 (16.00), 4.325 (1.28), 4.342 (3.87), 4.360 (3.75), 4.378 (1.21), 5.249 (1.28), 5.254 (1.29), 5.312 (1.31), 5.318 (1.31).

Intermediate 365

[4-bromo-3-(2,2-difluoroethenyl)-1-methyl-1H-pyrazol-5-yl]methanol

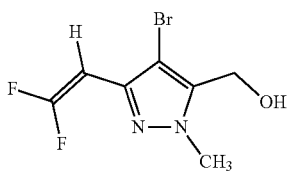

To a solution of ethyl 4-bromo-3-(2,2-difluoroethenyl)-1-methyl-1H-pyrazole-5-carboxylate (see Intermediate 364; 1.16 g, 3.93 mmol) in THF (16 ml) was added carefully a solution of lithium borohydride solution in THF (2.4 ml, 2.0 M, 4.7 mmol) via a syringe at room temperature and the reaction mixture was stirred at room temperature for 48 hours. Then sodium sulphate decahydrate was added in small portions and stirring was continued for one hour. After filtration the filtrate was evaporated. The residue was purified by flash chromatography (Biotage SNAP cartridge silica, hexane/ethyl acetate gradient, 12%-60% ethyl acetate) to give the title compound (0.81 g).

$^1$H-NMR (500 MHz, DMSO-d6) δ [ppm]: 0.000 (3.46), 2.517 (0.75), 2.521 (0.75), 2.525 (0.59), 3.331 (16.00), 4.469 (6.20), 4.480 (6.29), 5.403 (1.23), 5.414 (2.46), 5.426 (1.16), 5.506 (2.07), 5.511 (2.10), 5.559 (1.94), 5.565 (1.97).

Intermediate 366

{4-bromo-3-[(E)-2-fluorovinyl]-1-methyl-1H-pyrazol-5-yl}methanol

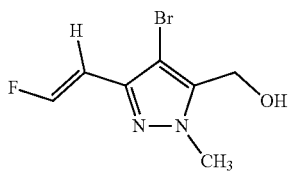

To a solution of ethyl 4-bromo-3-(2,2-difluoroethenyl)-1-methyl-1H-pyrazole-5-carboxylate (see Intermediate 364; 1.16 g, 3.93 mmol) in THF (16 ml) was added carefully a lithium borohydride solution in THF (2.4 ml, 2.0 M, 4.7 mmol) via a syringe at room temperature and the reaction mixture then was stirred at 60° C. for 24 hours. After cooling to room temperature sodium sulphate decahydrate was added in small portions and stirring was continued for one hour. After filtration the filtrate was evaporated. The residue was purified by flash chromatography (Biotage SNAP cartridge silica, hexane/ethyl acetate gradient, 12%-60% ethyl acetate) to give the title compound (0.30 g).

$^1$H-NMR (500 MHz, DMSO-d6) δ[ppm]: 0.000 (3.42), 2.517 (0.63), 2.521 (0.64), 2.525 (0.50), 3.330 (16.00), 3.851 (1.73), 3.859 (0.90), 3.868 (1.21), 4.461 (8.43), 4.469 (0.98), 4.473 (7.82), 4.480 (0.62), 4.485 (0.57), 5.390 (2.32), 5.401 (5.24), 5.412 (2.01), 6.256 (1.97), 6.278 (2.35), 6.295 (2.26), 6.318 (2.36), 7.516 (2.31), 7.538 (2.31), 7.683 (2.51), 7.706 (2.42).

Intermediate 367 ethyl 7-{3-[(E)-2-fluoroethenyl]-5-(hydroxymethyl)-1-methyl-1H-pyrazol-4-yl}-3-[3-(naphthalen-1-yloxy)propyl]-1H-indole-2-carboxylate

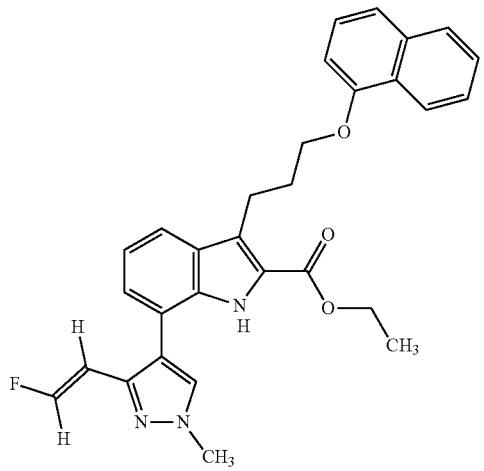

Ethyl 3-[3-(naphthalen-1-yloxy)propyl]-7-(4,4,5,5-tetramethyl-1,3,2-dioxaborolan-2-yl)-1H-indole-2-carboxylate (see Intermediate 5, 771 mg, 1.54 mmol) and {4-bromo-3-[(E)-2-fluoroethenyl]-1-methyl-1H-pyrazol-5-yl}methanol (see Intermediate 366; 330 mg, 1.40 mmol) were reacted under ultrasound in THF (17 ml) for five minutes under an argon atmosphere. Then an aqueous solution of potassium phosphate (5.6 ml, 0.50 M, 2.8 mmol) was added and the mixture was purged with argon. Afterwards XPhos Pd G2 (55.2 mg, 70.2 µmol) was added. The mixture then was evaporated and purged with argon twice. After stirring the reaction mixture for 5 hours at 35° C., it was poured into water and was extracted three times with ethyl acetate. The combined organic phases were washed with a saturated aqueous solution of sodium chloride, dried over sodium sulphate and evaporated after filtration. The residue was purified by flash chromatography (Biotage SNAP cartridge silica, hexane/ethyl acetate gradient, 12%-100% ethyl acetate) to give the title compound (0.51 g).

LC-MS (Method 2): Rt=1.57 min; MS (ESIpos): m/z=529 [M+H]$^+$ $^1$H-NMR (400 MHz, DMSO-d6) δ[ppm]: 1.258 (5.16), 1.275 (11.08), 1.293 (5.20), 2.217 (1.16), 2.233 (1.61), 2.252 (1.21), 2.518 (2.46), 2.522 (1.56), 3.358 (2.29), 3.376 (1.37), 3.921 (16.00), 3.937 (0.96), 3.953 (0.69), 4.201 (1.68), 4.216 (3.43), 4.231 (1.74), 4.240 (1.83), 4.258 (4.97), 4.275 (5.00), 4.293 (1.87), 4.321 (0.83), 5.623 (1.51), 6.043 (1.57), 6.071 (1.82), 6.092 (1.60), 6.121 (1.67), 6.903 (2.05), 6.921 (2.16), 7.079 (1.14), 7.084 (0.71), 7.092 (3.96), 7.095 (4.56), 7.105 (2.06), 7.112 (2.88), 7.133 (1.89), 7.317 (1.68), 7.345 (1.72), 7.371 (1.40), 7.392 (2.81), 7.411 (2.23), 7.449 (2.96), 7.470 (1.63), 7.484 (0.46), 7.489 (0.66), 7.501 (1.63), 7.506 (1.60), 7.511 (1.83), 7.518 (3.61), 7.525 (1.87), 7.530 (1.71), 7.535 (1.78), 7.547 (0.68), 7.552 (0.45), 7.714 (1.61), 7.719 (1.67), 7.732 (1.41), 7.737 (1.44), 7.859 (1.71), 7.867 (0.94), 7.877 (1.59), 7.882 (1.45), 8.214 (1.39), 8.221 (1.45), 8.238 (1.37), 10.905 (2.21).

Intermediate 368 ethyl 1-{4-[(tert-butoxycarbonyl)(methyl)amino]butyl}-7-{3-[(E)-2-fluoroethenyl]-5-(hydroxymethyl)-1-methyl-1H-pyrazol-4-yl}-3-[3-(naphthalen-1-yloxy)propyl]-1H-indole-2-carboxylate

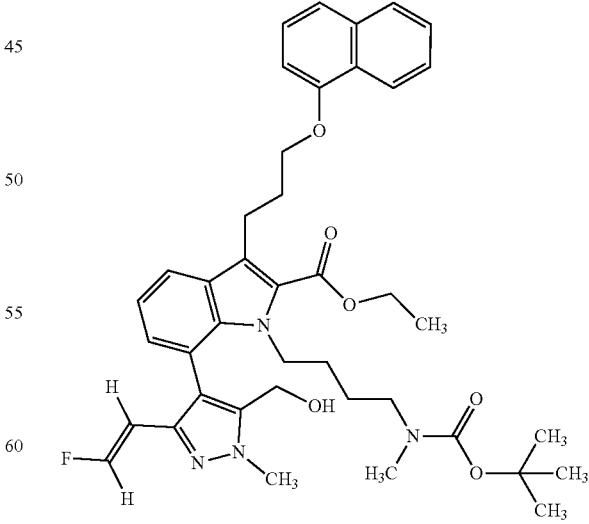

Caesium carbonate (772 mg, 2.37 mmol) was added to a solution of ethyl 7-{3-[(E)-2-fluoroethenyl]-5-(hydroxymethyl)-1-methyl-1H-pyrazol-4-yl}-3-[3-(naphthalen-1- yloxy)propyl]-1H-indole-2-carboxylate (see Intermediate 367; 250 mg, 474 μmol) in DMF (6.2 ml). After stirring for ten minutes, tert-butyl (4-bromobutyl)methylcarbamate (see Intermediate 2; 158 mg, 592 μmol) was added and stirring was continued for four days. After addition of water, the mixture was extracted three times with ethyl acetate. The combined organic phases were washed with a saturated aqueous solution of sodium chloride, dried over sodium sulphate and evaporated after filtration. The residue was purified by flash chromatography (Biotage SNAP cartridge silica, hexane/ethyl acetate gradient, 12%-100% ethyl acetate) to give the title compound (0.20 g).

LC-MS (Method 2): Rt=1.73 min; MS (ESIpos): m/z=715 [M+H]$^+$ $^1$H-NMR (400 MHz, DMSO-d6) δ[ppm]: 0.894 (0.91), 1.071 (0.43), 1.089 (0.82), 1.127 (1.02), 1.144 (0.95), 1.239 (5.25), 1.262 (5.57), 1.279 (8.98), 1.297 (4.86), 1.339 (3.48), 1.380 (1.94), 2.191 (1.21), 2.210 (1.60), 2.227 (1.23), 2.518 (4.53), 2.523 (3.07), 2.621 (4.10), 2.834 (1.30), 3.282 (1.47), 3.302 (2.18), 3.912 (16.00), 3.945 (1.21), 4.206 (2.22), 4.221 (4.32), 4.238 (2.59), 4.248 (2.03), 4.257 (3.86), 4.274 (2.83), 4.293 (1.15), 5.275 (1.14), 5.288 (1.88), 5.299 (1.02), 5.966 (1.53), 5.994 (1.81), 6.017 (1.56), 6.045 (1.68), 6.754 (0.41), 6.783 (0.41), 6.904 (2.16), 6.922 (2.33), 6.965 (0.41), 6.992 (0.41), 7.029 (1.15), 7.045 (1.69), 7.093 (2.64), 7.112 (2.92), 7.130 (1.68), 7.376 (1.68), 7.396 (3.15), 7.415 (2.53), 7.456 (3.39), 7.477 (1.90), 7.501 (0.71), 7.513 (2.12), 7.519 (3.69), 7.528 (4.43), 7.537 (3.93), 7.543 (2.35), 7.554 (0.78), 7.786 (2.24), 7.789 (2.35), 7.806 (2.05), 7.809 (1.99), 7.865 (1.92), 7.876 (0.99), 7.883 (1.32), 7.889 (1.68), 8.225 (1.60), 8.232 (1.25), 8.237 (0.82), 8.249 (1.56).

Intermediate 369 ethyl 7-{5-(bromomethyl)-3-[(E)-2-fluoroethenyl]-1-methyl-1H-pyrazol-4-yl}-1-{4-[(tert-butoxycarbonyl)(methyl)amino]butyl}-3-[3-(naphthalen-1-yloxy)propyl]-1H-indole-2-carboxylate

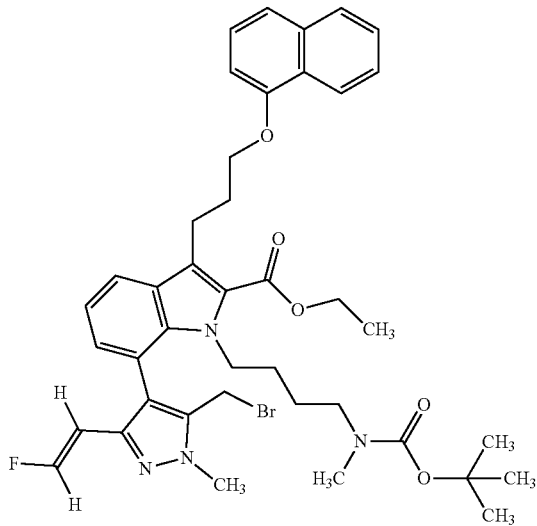 [SMILES: CCOC(=O)c1c(CCCOc2cccc3ccccc23)c2cccc(-c3c(/C=C/F)nn(C)c3CBr)c2n1CCCCN(C)C(=O)OC(C)(C)C]

To a mixture of ethyl 1-{4-[(tert-butoxycarbonyl)(methyl)amino]butyl}-7-{3-[(E)-2-fluoroethenyl]-5-(hydroxymethyl)-1-methyl-1H-pyrazol-4-yl}-3-[3-(naphthalen-1-yloxy)propyl]-1H-indole-2-carboxylate (see Intermediate 368; 200 mg, 281 μmol) and 3 mmol/g triphenylphosphane polymer (99.3 mg, 379 μmol) in dichloromethane (2.3 ml), carbon tetrabromide (122 mg, 365 μmol) was added at 0° C. in portions during 30 minutes. After stirring of the mixture for 24 hours at room temperature it was filtered and the filtrate evaporated to dryness. The crude title compound (220 mg) was further used without purification.

Intermediate 370 ethyl 7-{5-(bromomethyl)-3-[(E)-2-fluoroethenyl]-1-methyl-1H-pyrazol-4-yl}-1-[4-(methylamino)butyl]-3-[3-(naphthalen-1-yloxy)propyl]-1H-indole-2-carboxylate hydrochloric acid salt

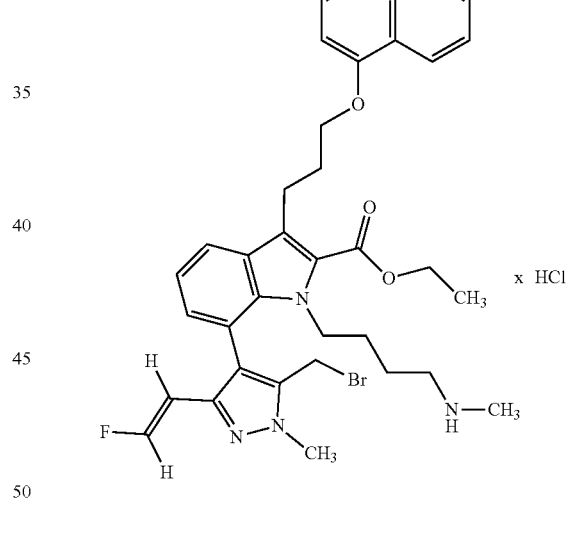

At 0° C. a solution of hydrochloric acid in 1,4-dioxane (5.0 ml, 4.0 M, 20 mmol) was added to a solution of ethyl 7-{5-(bromomethyl)-3-[(E)-2-fluoroethenyl]-1-methyl-1H-pyrazol-4-yl}-1-{4-[(tert-butoxycarbonyl)(methyl)amino]butyl}-3-[3-(naphthalen-1-yloxy)propyl]-1H-indole-2-carboxylate (see Intermediate 369; 220 mg, 284 μmol) in methanol (5.1 ml). Then the reaction mixture was stirred at room temperature for two hours, evaporated to dryness and the crude title compound (200 mg) was further used without purification.

Intermediate 371

(rac)-ethyl 3-[(E)-2-fluoroethenyl]-1,14-dimethyl-7-[3-(naphthalen-1-yloxy)propyl]-10,11,12,13,14,15-hexahydro-1H-pyrazolo[3',4':8,9][1,6]diazacycloundecino[10,11,1-hi]indole-8-carboxylate

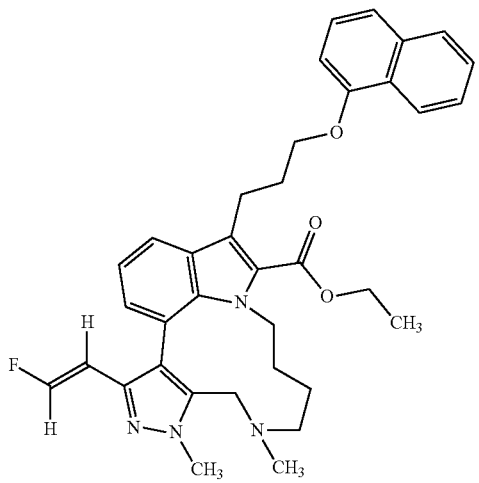 [SMILES: CCOC(=O)c1c(CCCOc2cccc3ccccc23)c2cccc3c2n1CCCCN(C)Cc1c-3c(/C=C/F)nn1C]

Crude ethyl 7-{5-(bromomethyl)-3-[(E)-2-fluoroethenyl]-1-methyl-1H-pyrazol-4-yl}-1-[4-(methylamino)butyl]-3-[3-(naphthalen-1-yloxy)propyl]-1H-indole-2-carboxylate hydrochloric acid salt (see Intermediate 370; 200 mg, 281 µmol) was dissolved in DMF (25 ml), and caesium carbonate (458 mg, 1.40 mmol) was added. The mixture was then stirred at 50° C. for 4 hours. After cooling and removing the volatiles under reduced pressure, the residue was purified by flash chromatography (Biotage SNAP cartridge silica, hexane/ethyl acetate gradient, 50%-100% ethyl acetate) to give the title compound (104 mg).

LC-MS (Method 2): Rt=1.70 min; MS (ESIpos): m/z=596 [M+H]$^+$ $^1$H-NMR (400 MHz, DMSO-d6) δ[ppm]: 0.707 (0.40), 0.734 (0.47), 0.976 (0.40), 1.090 (0.48), 1.230 (0.43), 1.261 (5.28), 1.278 (11.84), 1.296 (5.56), 1.882 (0.62), 2.152 (9.82), 2.204 (0.98), 2.221 (1.52), 2.237 (0.98), 2.401 (0.40), 2.418 (0.42), 2.425 (0.42), 2.518 (3.40), 2.523 (2.44), 2.686 (0.43), 2.888 (0.42), 3.251 (1.52), 3.264 (0.65), 3.283 (1.93), 3.297 (1.04), 3.316 (0.61), 3.347 (0.53), 3.366 (0.90), 3.384 (0.53), 3.399 (0.59), 3.677 (1.66), 3.710 (1.48), 3.866 (0.40), 3.896 (16.00), 3.927 (0.68), 4.194 (1.43), 4.200 (1.49), 4.214 (2.97), 4.221 (2.50), 4.230 (1.65), 4.239 (1.96), 4.256 (0.57), 4.262 (0.59), 4.280 (1.77), 4.297 (1.60), 4.307 (1.03), 4.316 (0.47), 4.324 (1.03), 4.514 (0.64), 4.549 (0.57), 5.759 (0.61), 5.883 (1.57), 5.912 (2.02), 5.934 (1.66), 5.963 (1.74), 6.495 (1.74), 6.524 (1.77), 6.707 (1.62), 6.736 (1.63), 6.881 (1.97), 6.883 (2.84), 6.898 (2.35), 6.901 (2.56), 6.903 (2.11), 7.061 (1.99), 7.079 (1.91), 7.081 (2.10), 7.099 (1.55), 7.364 (1.43), 7.385 (2.42), 7.404 (1.99), 7.452 (2.50), 7.473 (1.49), 7.502 (0.53), 7.514 (1.83), 7.519 (2.80), 7.529 (3.26), 7.539 (2.63), 7.542 (2.02), 7.554 (0.67), 7.797 (1.91), 7.800 (1.90), 7.817 (1.77), 7.820 (1.63), 7.863 (1.48), 7.867 (1.03), 7.875 (0.81), 7.877 (0.95), 7.880 (0.98), 7.886 (1.26), 8.236 (1.27), 8.247 (0.82), 8.250 (0.62), 8.261 (1.21).

Intermediate 372 ethyl 7-[3-(2,2-difluoroethenyl)-5-(hydroxymethyl)-1-methyl-1H-pyrazol-4-yl]-3-[3-(naphthalen-1-yloxy)propyl]-1H-indole-2-carboxylate

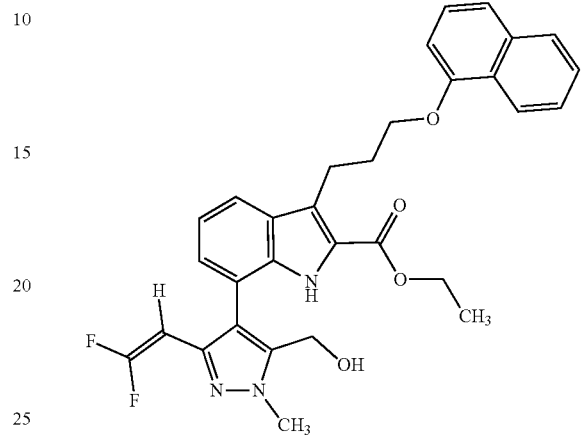

Ethyl 3-[3-(naphthalen-1-yloxy)propyl]-7-(4,4,5,5-tetramethyl-1,3,2-dioxaborolan-2-yl)-1H-indole-2-carboxylate (see Intermediate 5, 2.17 g, 4.35 mmol) and [4-bromo-3-(2,2-difluoroethenyl)-1-methyl-1H-pyrazol-5-yl]methanol (see Intermediate 365; 1.00 g, 3.95 mmol) were reacted under ultrasound in THF (48 ml) for five minutes under an argon atmosphere. Then an aqueous solution of potassium phosphate (16 ml, 0.50 M, 7.9 mmol) was added and the mixture was purged with argon. Afterwards, XPhos Pd G2 (155 mg, 198 µmol) was added. The mixture then was evaporated and purged with argon twice. After stirring the reaction mixture for 5 hours at room temperature, it was poured into water and was extracted three times with ethyl acetate. The combined organic phases were washed with a saturated aqueous solution of sodium chloride, dried over sodium sulphate and evaporated after filtration. The residue was purified by flash chromatography (Biotage SNAP cartridge silica, hexane/ethyl acetate gradient, 12%→100% ethyl acetate) to give the title compound (1.86 g).

LC-MS (Method 2): Rt=1.60 min; MS (ESIpos): m/z=547 [M+H]$^+$ $^1$H-NMR (400 MHz, DMSO-d6) δ[ppm]: 1.067 (16.00), 1.154 (1.03), 1.171 (1.85), 1.189 (0.87), 1.259 (4.44), 1.277 (9.85), 1.295 (4.48), 1.987 (3.52), 2.214 (0.80), 2.231 (1.09), 2.250 (0.84), 2.518 (1.59), 2.522 (0.98), 3.356 (1.59), 3.374 (0.98), 3.939 (2.95), 3.949 (13.94), 4.017 (0.76), 4.034 (0.73), 4.200 (1.16), 4.215 (2.44), 4.230 (1.18), 4.240 (1.34), 4.258 (3.98), 4.276 (3.95), 4.293 (1.27), 4.342 (0.59), 5.207 (1.56), 5.215 (1.57), 5.275 (1.45), 5.283 (1.44), 5.678 (1.07), 6.903 (1.48), 6.920 (1.59), 6.922 (1.52), 7.086 (0.50), 7.095 (5.63), 7.103 (2.58), 7.110 (2.71), 7.128 (0.46), 7.371 (1.21), 7.392 (2.16), 7.411 (1.84), 7.449 (2.16), 7.469 (1.20), 7.487 (0.54), 7.499 (1.35), 7.504 (1.20), 7.506 (0.63), 7.510 (1.37), 7.517 (3.02), 7.523 (1.46), 7.530 (1.31), 7.534 (1.51), 7.547 (0.60), 7.708 (1.25), 7.717 (1.20), 7.722 (1.03), 7.731 (1.14), 7.858 (1.24), 7.866 (0.71), 7.877 (1.32), 7.882 (1.10), 8.212 (1.10), 8.219 (1.06), 8.228 (0.49), 8.230 (0.60), 8.234 (0.98), 8.237 (1.08), 10.933 (1.54).

Intermediate 373 ethyl 7-[3-(2,2-difluoroethyl)-5-(hydroxymethyl)-1-methyl-1H-pyrazol-4-yl]-3-[3-(naphthalen-1-yloxy)propyl]-1H-indole-2-carboxylate

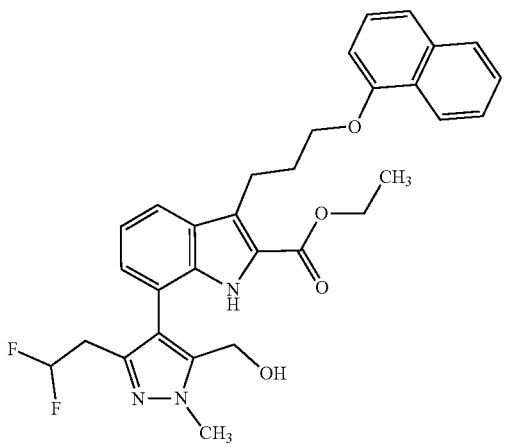 [SMILES: CCOC(=O)c1[nH]c2c(-c3c(CC(F)F)nn(C)c3CO)cccc2c1CCCOc1cccc2ccccc12]

Ethyl 7-[3-(2,2-difluoroethenyl)-5-(hydroxymethyl)-1-methyl-1H-pyrazol-4-yl]-3-[3-(naphthalen-1-yloxy)propyl]-1H-indole-2-carboxylate (see Intermediate 372; 500 mg, 916 µmol) was reacted under an atmosphere of hydrogen in ethanol (69 ml) at ambient pressure for 48 hours using Pd/C (10%, 49.8 mg, 47.7 µmol) as catalyst. Filtration over Celite and evaporation of the filtrate gave the crude title compound (470 mg), which was further used without purification.

Intermediate 374

(rac)-ethyl (11Z)-3-(2,2-difluoroethyl)-1-methyl-7-[3-(naphthalen-1-yloxy)propyl]-1,10,13,15-tetrahydropyrazolo[4',3':9,10][1,6]oxazacycloundecino[8,7,6-hi]indole-8-carboxylate

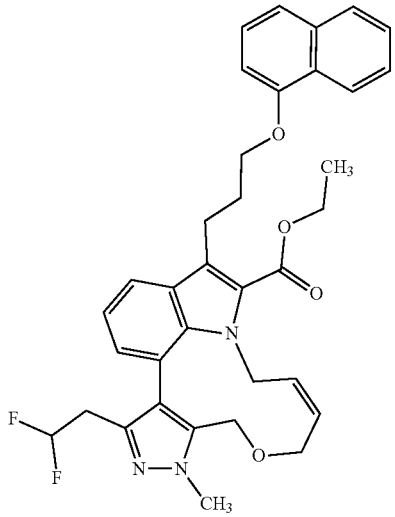 [SMILES: CCOC(=O)c1c(CCCOc2cccc3ccccc23)c2cccc3c2n1C/C=C\COCc1c-3c(CC(F)F)nn1C]

Ethyl 7-[3-(2,2-difluoroethyl)-5-(hydroxymethyl)-1-methyl-1H-pyrazol-4-yl]-3-[3-(naphthalen-1-yloxy)propyl]-1H-indole-2-carboxylate (see Intermediate 373; 470 mg, 858 µmol) and caesium carbonate (1.40 g, 4.29 mmol) were mixed in acetonitrile (9.5 ml) and stirred for ten minutes at ambient temperature. After addition of (2Z)-1,4-dichlorobut-2-ene (100 µl, 940 µmol) and sodium iodide (260 mg, 1.72 mmol), the mixture was stirred 18 hours at 40° C. After addition of water, the mixture was extracted three times with ethyl acetate. The combined organic phases were washed with a saturated aqueous solution of sodium chloride, dried over sodium sulphate and evaporated after filtration. The residue was purified by flash chromatography (Biotage SNAP cartridge silica, hexane/ethyl acetate gradient, 6%→60% ethyl acetate) to give the title compound (0.28 g).

LC-MS (Method 2): Rt=1.71 min; MS (ESIpos): m/z=601 [M+H]$^+$ $^1$H-NMR (400 MHz, DMSO-d6) δ[ppm]: 1.066 (3.41), 1.270 (4.93), 1.288 (10.92), 1.306 (5.06), 2.237 (0.92), 2.254 (1.34), 2.270 (0.98), 2.323 (0.49), 2.327 (0.69), 2.331 (0.51), 2.518 (2.87), 2.523 (1.97), 2.591 (0.41), 2.603 (0.52), 2.610 (0.55), 2.622 (0.49), 2.635 (0.77), 2.647 (0.90), 2.652 (0.87), 2.665 (1.25), 2.669 (1.03), 2.673 (0.70), 2.678 (0.64), 2.689 (0.56), 2.697 (0.52), 2.708 (0.42), 3.314 (0.71), 3.351 (1.58), 3.369 (0.62), 3.471 (0.66), 3.502 (1.18), 3.533 (0.79), 3.775 (0.68), 3.785 (0.79), 3.807 (0.64), 3.818 (0.58), 3.921 (16.00), 3.939 (0.62), 4.199 (1.88), 4.227 (1.98), 4.233 (3.06), 4.245 (3.91), 4.253 (2.38), 4.260 (1.58), 4.271 (1.92), 4.278 (0.69), 4.289 (0.62), 4.296 (1.84), 4.313 (1.71), 4.323 (0.89), 4.331 (0.50), 4.341 (0.89), 4.619 (0.54), 4.647 (0.66), 4.660 (0.72), 4.688 (0.71), 4.726 (2.14), 4.760 (1.94), 4.958 (1.06), 4.972 (1.14), 4.998 (1.27), 5.162 (0.42), 5.180 (0.63), 5.190 (0.62), 5.759 (1.30), 5.791 (0.70), 5.920 (0.61), 5.931 (1.37), 5.943 (0.63), 6.072 (0.60), 6.841 (1.83), 6.843 (1.94), 6.858 (2.15), 6.861 (2.08), 6.912 (1.80), 6.929 (1.93), 7.094 (1.89), 7.114 (2.26), 7.132 (1.65), 7.375 (1.31), 7.395 (2.58), 7.414 (2.10), 7.453 (2.62), 7.474 (1.48), 7.483 (0.52), 7.486 (0.62), 7.500 (1.53), 7.504 (1.36), 7.512 (1.59), 7.518 (2.95), 7.524 (1.67), 7.532 (1.48), 7.536 (1.67), 7.549 (0.69), 7.554 (0.47), 7.806 (1.88), 7.808 (1.99), 7.826 (1.81), 7.828 (1.77), 7.862 (1.53), 7.869 (0.92), 7.880 (1.62), 7.885 (1.33), 8.201 (1.32), 8.205 (1.33), 8.225 (1.29).

Intermediate 375

(rac)-ethyl 3-(2,2-difluoroethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate

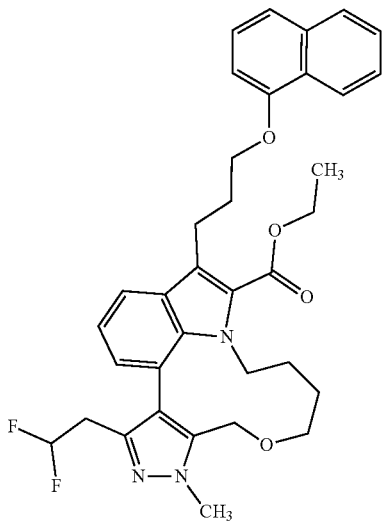 [SMILES: CCOC(=O)c1c(CCCOc2cccc3ccccc23)c2cccc3c2n1CCCCOCc1c-3c(CC(F)F)nn1C]

(rac)-Ethyl (11Z)-3-(2,2-difluoroethyl)-1-methyl-7-[3-(naphthalen-1-yloxy)propyl]-1,10,13,15-tetrahydropyrazolo[4',3':9,10][1,6]oxazacycloundecino[8,7,6-hi]indole-8-carboxylate (see intermediate 374, 280 mg, 467 μmol) and Pd/C (10%, 29.8 mg, 28.0 μmol) were reacted under an atmosphere of hydrogen in ethanol (12 ml) at ambient pressure for 5 hours. Filtration and evaporation of the filtrate and flash chromatography of the residue (Biotage SNAP cartridge silica, hexane/ethyl acetate gradient, 12%→100% ethyl acetate) to give the title compound (0.25 g).

LC-MS (Method 2): Rt=1.70 min; MS (ESIpos): m/z=603 [M+H]$^+$ $^1$H-NMR (400 MHz, DMSO-d6) δ[ppm]: 0.587 (1.14), 0.605 (0.56), 1.035 (0.99), 1.066 (1.67), 1.071 (0.62), 1.088 (0.97), 1.105 (0.59), 1.263 (5.51), 1.280 (10.70), 1.298 (4.86), 2.222 (1.05), 2.239 (0.74), 2.322 (0.46), 2.327 (0.65), 2.332 (0.47), 2.518 (3.10), 2.523 (2.04), 2.665 (0.62), 2.669 (0.97), 2.673 (0.74), 2.679 (0.66), 2.703 (0.42), 2.713 (0.71), 2.724 (0.60), 2.746 (0.65), 2.757 (0.81), 2.789 (0.47), 2.829 (0.75), 2.839 (0.54), 2.858 (0.68), 3.269 (0.54), 3.287 (0.79), 3.308 (0.50), 3.347 (0.82), 3.365 (0.52), 3.371 (0.60), 3.382 (0.42), 3.388 (0.50), 3.431 (0.71), 3.445 (0.57), 3.460 (0.65), 3.901 (16.00), 3.972 (0.52), 3.989 (0.61), 4.008 (0.64), 4.204 (1.51), 4.213 (1.49), 4.221 (2.70), 4.231 (2.49), 4.245 (2.50), 4.249 (2.50), 4.266 (1.48), 4.279 (2.14), 4.284 (2.22), 4.294 (0.44), 4.302 (1.59), 4.311 (0.98), 4.319 (0.57), 4.329 (1.00), 4.401 (0.73), 4.413 (0.41), 4.437 (0.64), 4.641 (1.81), 4.675 (1.61), 5.848 (0.57), 5.978 (0.54), 5.990 (1.24), 6.001 (0.57), 6.130 (0.54), 6.882 (1.61), 6.885 (1.76), 6.895 (1.70), 6.900 (2.14), 6.903 (2.00), 6.912 (1.76), 7.067 (1.72), 7.085 (2.08), 7.087 (2.12), 7.105 (1.82), 7.369 (1.22), 7.390 (2.27), 7.397 (0.50), 7.409 (1.89), 7.451 (2.40), 7.472 (1.37), 7.495 (0.53), 7.508 (1.46), 7.512 (1.49), 7.515 (2.06), 7.523 (3.33), 7.532 (1.93), 7.534 (1.85), 7.539 (1.78), 7.551 (0.63), 7.794 (1.68), 7.797 (1.70), 7.814 (1.61), 7.816 (1.52), 7.861 (1.44), 7.870 (0.72), 7.879 (1.16), 7.885 (1.25), 8.220 (1.34), 8.227 (1.15), 8.236 (0.60), 8.245 (1.25).

Intermediate 376 ethyl 7-(4,4,5,5-tetramethyl-1,3,2-dioxaborolan-2-yl)-1H-indole-2-carboxylate

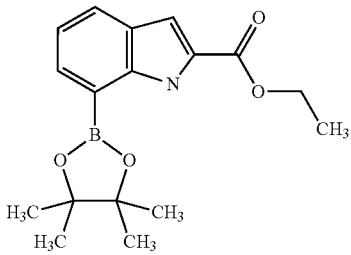 [SMILES: CCOC(=O)c1cc2cccc(B3OC(C)(C)C(C)(C)O3)c2[nH]1]

A solution of ethyl 7-bromo-1H-indole-2-carboxylate (12.4 g, 45.0 mmol) in 1,4-dioxane (600 ml) was purged 10 minutes with argon. Then 4,4,4',4',5,5,5',5'-octamethyl-2,2'-bi-1,3,2-dioxaborolane (23.1 g, 90.0 mmol) and potassium acetate (13.4 g, 135 mmol) were added and the mixture was again purged for 10 minutes with argon. After addition of dichloro[bis(triphenyl-λ$^5$-phosphanyl)]palladium (1.94 g, 98% purity, 2.70 mmol), the mixture then was repeatedly evaporated and purged with argon. Subsequently, the reaction mixture was stirred at 110° C. for three hours, followed by stirring at 80° C. for 18 hours. After cooling to room temperature, the mixture was evaporated to dryness. The residue was triturated in a 500 ml portion of hexane and filtered. The filtrate was concentrated and subjected to flash chromatography (Biotage SNAP cartridge silica, hexane/ethyl acetate gradient, 0%→30% ethyl acetate, with a constant amount of 10% dichloromethane). The fractions containing the desired compound were evaporated and the residue was triturated in 100 ml hexane at 0° C. After filtration the title compound was obtained as the filter cake (6.75 g) LC-MS (Method 2): Rt=1.45 min; MS (ESIpos): m/z=316 [M+H]$^+$ $^1$H-NMR (400 MHz, DMSO-d6) δ[ppm]: 1.329 (1.72), 1.347 (3.87), 1.365 (2.16), 1.375 (16.00), 4.332 (0.51), 4.350 (1.69), 4.368 (1.67), 4.385 (0.49), 7.151 (0.68), 7.168 (0.73), 7.171 (0.69), 7.188 (0.75), 7.238 (1.23), 7.244 (1.25), 7.628 (0.66), 7.631 (0.73), 7.646 (0.63), 7.648 (0.59), 7.853 (0.56), 7.873 (0.52).

Intermediate 377 ethyl 7-[3-(hydroxymethyl)-1,5-dimethyl-1H-pyrazol-4-yl]-1H-indole-2-carboxylate

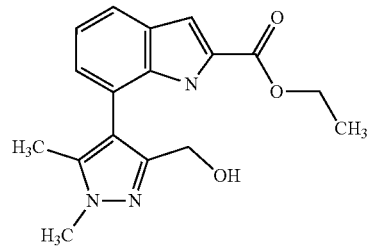 [SMILES: CCOC(=O)c1cc2cccc(-c3c(CO)nn(C)c3C)c2[nH]1]

Ethyl 7-(4,4,5,5-tetramethyl-1,3,2-dioxaborolan-2-yl)-1H-indole-2-carboxylate (see Intermediate 376; 15.6 g, 39.6 mmol) and (4-bromo-1,5-dimethyl-1H-pyrazol-3-yl)methanol (see Intermediate 11; 12.2 g, 59.4 mmol) were dissolved in THF (500 ml) under a constant stream of argon. After 10 minutes, an aqueous solution of potassium phosphate (160 ml, 0.50 M, 79 mmol), and XPhos Pd G2 (1.56 g, 1.98 mmol) were added maintaining the argon stream. Then the reaction mixture was stirred at 45° C. for 15 hours in an argon atmosphere. After cooling to room temperature, the THF was distilled off under reduced pressure, and the remaining water phase was decanted. The residue was purified by flash chromatography (Biotage SNAP cartridge silica, dichloromethane/ethanol gradient, 0%→20% ethanol). The fractions containing the desired compound were again subjected to flash chromatography under the same conditions as before to give the title compound (11.1 g).

LC-MS (Method 2): Rt=1.06 min; MS (ESIneg): m/z=313 [M−H]⁻

¹H-NMR (400 MHz, DMSO-d6) δ[ppm]: 1.289 (5.04), 1.307 (11.72), 1.324 (5.15), 2.153 (16.00), 2.205 (0.86), 2.518 (0.51), 3.332 (8.65), 3.725 (0.83), 4.260 (3.66), 4.278 (5.01), 4.287 (0.46), 4.296 (4.84), 4.301 (0.51), 4.313 (1.40), 5.635 (1.11), 5.759 (1.08), 7.106 (0.89), 7.109 (1.27), 7.124 (2.93), 7.128 (2.46), 7.139 (2.73), 7.158 (2.90), 7.176 (1.30), 7.225 (3.15), 7.622 (1.64), 7.625 (1.78), 7.641 (1.57), 7.644 (1.47), 11.590 (0.81).

Intermediate 378

(rac)-ethyl (11Z)-2,3-dimethyl-2,10,13,15-tetrahydropyrazolo[4',3':9,10][1,6]oxazacycloundecino[8,7,6-hi]indole-8-carboxylate

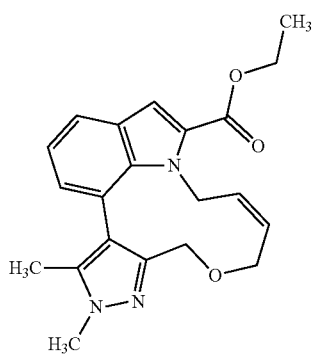 [SMILES: CCOC(=O)c1cc2cccc3c2n1C/C=C\COCc1nn(C)c(C)c1-3]

Ethyl 7-[3-(hydroxymethyl)-1,5-dimethyl-1H-pyrazol-4-yl]-1H-indole-2-carboxylate (see Intermediate 377; 11.1 g, 35.5 mmol) and caesium carbonate (34.7 g, 106 mmol) were mixed in acetonitrile (390 ml) and the resulting mixture was stirred for ten minutes at ambient temperature. After addition of (2Z)-1,4-dichlorobut-2-ene (3.9 ml, 35 mmol) and sodium iodide (10.7 g, 71.0 mmol), the mixture was stirred 75 hours at 60° C. After evaporation of the reaction mixture, The residue was purified by flash chromatography (Biotage SNAP cartridge silica, dichloromethane/acetone gradient, 0%→100% acetone) to give the title compound (5.1 g).

LC-MS (Method 2): Rt=1.27 min; MS (ESIpos): m/z=367 [M+H]⁺

¹H-NMR (400 MHz, DMSO-d6) δ[ppm]: 1.308 (4.44), 1.326 (9.95), 1.343 (4.56), 1.368 (0.46), 1.385 (1.04), 1.403 (0.47), 1.837 (14.53), 1.853 (1.49), 2.084 (6.08), 2.518 (0.77), 2.523 (0.55), 3.330 (16.00), 3.599 (0.52), 3.612 (0.61), 3.629 (0.78), 3.642 (0.73), 3.766 (0.80), 3.793 (0.99), 3.822 (0.71), 4.254 (1.51), 4.271 (0.58), 4.280 (0.70), 4.287 (2.53), 4.294 (0.85), 4.298 (2.01), 4.312 (2.01), 4.316 (2.14), 4.330 (1.92), 4.333 (0.76), 4.338 (0.56), 4.347 (0.73), 4.356 (0.65), 4.366 (2.43), 4.399 (1.49), 4.796 (0.49), 4.822 (0.58), 4.834 (0.72), 4.860 (0.86), 5.000 (0.75), 5.038 (0.51), 5.271 (0.78), 5.278 (0.79), 5.297 (0.60), 5.304 (0.57), 5.354 (0.51), 5.367 (0.50), 5.759 (1.53), 6.872 (1.69), 6.875 (1.74), 6.889 (2.03), 6.892 (1.84), 7.124 (1.94), 7.141 (1.91), 7.143 (2.17), 7.161 (1.67), 7.476 (5.56), 7.702 (1.79), 7.705 (1.83), 7.722 (1.71), 7.725 (1.63).

Intermediate 379

(rac)-ethyl 2,3-dimethyl-2,10,11,12,13,15-hexahydropyrazolo[4',3':9,10][1,6]oxazacycloundecino[8,7,6-hi]indole-8-carboxylate

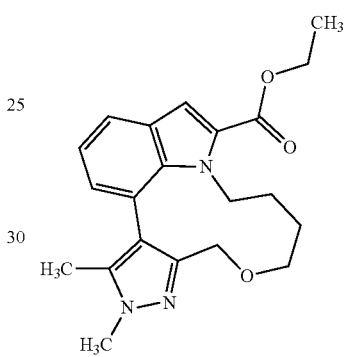

In an 600 ml autoclave, to a solution (rac)-ethyl (11Z)-2,3-dimethyl-2,10,13,15-tetrahydropyrazolo[4',3':9,10][1,6]oxazacycloundecino[8,7,6-hi]indole-8-carboxylate (see Intermediate 378; 4.87 g, 13.3 mmol) in a mixture of ethanol/THF (5:1), Pd/C (10%, 0.7 g) was added. The autoclave then was pressurized with hydrogen to 25 bar and the reaction mixture was stirred at room temperature for 23 hours. After changing the gas in the reactor from hydrogen to nitrogen, the reaction mixture was kept at room temperature for 72 hours. After filtration, the filtrate was evaporated and the residue was purified by flash chromatography (Biotage SNAP cartridge silica, dichloromethane/acetone gradient, 0%-50% acetone) to give the title compound (3.12 g).

LC-MS (Method 2): Rt=1.30 min; MS (ESIpos): m/z=369 [M+H]⁺

¹H-NMR (400 MHz, DMSO-d6) δ[ppm]: 1.045 (0.42), 1.056 (0.40), 1.172 (0.77), 1.186 (0.81), 1.196 (0.74), 1.208 (0.47), 1.298 (4.75), 1.315 (10.72), 1.333 (5.13), 1.353 (0.41), 1.805 (16.00), 2.084 (1.66), 2.518 (1.25), 2.523 (0.87), 3.088 (0.71), 3.102 (0.62), 3.112 (0.49), 3.271 (0.41), 3.280 (0.54), 3.285 (0.62), 3.295 (0.67), 3.309 (0.51), 3.331 (13.44), 3.930 (0.67), 3.943 (0.42), 3.953 (0.45), 4.194 (2.21), 4.226 (2.57), 4.248 (0.52), 4.258 (0.57), 4.266 (0.54), 4.275 (2.05), 4.291 (2.46), 4.293 (2.60), 4.308 (2.12), 4.318 (0.55), 4.326 (0.62), 4.336 (0.84), 4.353 (0.69), 4.370 (0.64), 4.389 (0.49), 4.510 (2.32), 4.541 (1.97), 5.760 (1.24), 6.940 (1.64), 6.942 (1.88), 6.958 (2.03), 6.960 (2.05), 7.129 (1.87), 7.147 (1.95), 7.149 (2.40), 7.167 (1.72), 7.414 (5.92), 7.689 (1.89), 7.692 (2.04), 7.709 (1.79), 7.712 (1.78).

Intermediate 380

(rac)-ethyl 7-iodo-2,3-dimethyl-2,10,11,12,13,15-hexahydropyrazolo[4',3':9,10][1,6]oxazacycloundecino[8,7,6-hi]indole-8-carboxylate

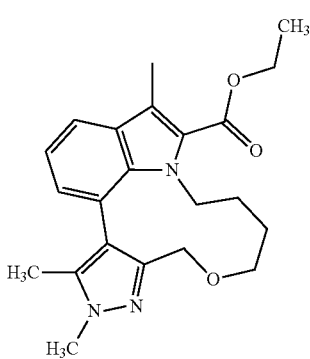 [SMILES: CCOC(=O)c1c(C)c2cccc3c2n1CCCCOCc1nn(C)c(C)c1-3]

A mixture of (rac)-ethyl 2,3-dimethyl-2,10,11,12,13,15-hexahydropyrazolo[4',3':9,10][1,6]oxazacycloundecino[8,7,6-hi]indole-8-carboxylate (see Intermediate 379; 1.50 g, 4.08 mmol) and 1-iodopyrrolidine-2,5-dione (also referred to as N-iodosuccinimide herein); 1.38 g, 6.12 mmol) in THF (30 ml) were stirred for five days at 50° C. Then a second portion of 1-iodopyrrolidine-2,5-dione (0.8 g, 3.5 mmol) was added and stirring continued for five hours at 70° C., followed by stirring at room temperature for 14 days. After evaporation to dryness, the residue was subjected to flash chromatography (Biotage SNAP cartridge silica, dichloromethane/ethyl acetate gradient, 0%-100% ethyl acetate) to give the title compound (1.8 g).

$^1$H-NMR (400 MHz, DMSO-d6) δ[ppm]: 1.154 (1.40), 1.164 (0.82), 1.171 (2.89), 1.183 (1.03), 1.189 (1.84), 1.321 (0.53), 1.335 (0.46), 1.338 (0.49), 1.347 (0.49), 1.352 (0.71), 1.359 (5.23), 1.376 (11.30), 1.394 (5.16), 1.826 (16.00), 1.987 (3.89), 2.518 (1.10), 2.522 (0.78), 2.562 (4.56), 3.067 (0.51), 3.072 (0.53), 3.088 (0.57), 3.292 (0.82), 3.304 (0.60), 3.316 (0.66), 3.329 (14.90), 3.999 (0.57), 4.009 (0.67), 4.017 (1.08), 4.022 (0.46), 4.034 (1.12), 4.162 (2.21), 4.194 (2.52), 4.202 (0.45), 4.218 (0.57), 4.223 (0.51), 4.238 (0.64), 4.253 (0.43), 4.258 (0.43), 4.298 (1.03), 4.307 (0.48), 4.316 (0.98), 4.325 (1.60), 4.343 (1.67), 4.361 (0.50), 4.381 (0.52), 4.399 (1.70), 4.416 (1.56), 4.426 (1.03), 4.435 (0.46), 4.444 (1.04), 4.486 (2.21), 4.517 (1.92), 7.028 (1.90), 7.031 (2.02), 7.046 (2.31), 7.049 (2.14), 7.237 (1.94), 7.256 (1.80), 7.257 (2.44), 7.275 (1.86), 7.491 (2.18), 7.494 (2.22), 7.511 (1.79), 7.514 (1.75).

Intermediate 381

(rac)-ethyl 2,3-dimethyl-7-(naphthalen-1-ylethynyl)-2,10,11,12,13,15-hexahydropyrazolo[4',3':9,10][1,6]oxazacycloundecino[8,7,6-hi]indole-8-carboxylate

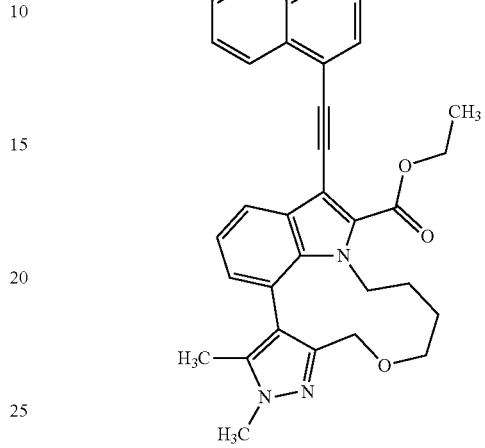

To a mixture of (rac)-ethyl 7-iodo-2,3-dimethyl-2,10,11,12,13,15-hexahydropyrazolo[4',3':9,10][1,6]oxazacycloundecino[8,7,6-hi]indole-8-carboxylate (see intermediate 380, 200 mg, 405 μmol), dichloro[bis(triphenyl-λ$^5$-phosphanyl)]palladium (5.71 mg, 8.11 μmol) and copper(I)iodide (770 μg, 4.1 μmol) in triethylamine (5.0 ml), 1-ethynylnaphthalene (69 μl, 490 μmol) was added dropwise. The reaction mixture was then stirred 17 hours at room temperature, followed by stirring for 6 hours at 60° C. Then, acetonitrile (10 ml) was added and stirring was continued at 100° C. for 72 hours. After cooling to room temperature, the reaction mixture was evaporated to dryness and the residue was subjected to flash chromatography (Biotage SNAP cartridge silica, dichloromethane/ethyl acetate gradient, 0%→100% ethyl acetate, followed by ethyl acetate/ethanol gradient, 0%-20% ethanol) to give the title compound (196 mg).

LC-MS (Method 2): $R_t$=1.64 min; MS (ESIpos): m/z=519 [M+H]$^+$ $^1$H-NMR (400 MHz, DMSO-d6) δ[ppm]: 1.009 (0.40), 1.088 (0.50), 1.145 (0.62), 1.154 (3.01), 1.172 (6.36), 1.190 (3.42), 1.239 (1.50), 1.316 (0.57), 1.345 (4.96), 1.352 (0.64), 1.363 (11.44), 1.381 (5.10), 1.469 (0.45), 1.805 (0.78), 1.824 (0.43), 1.832 (0.47), 1.855 (16.00), 1.987 (10.59), 2.518 (5.34), 2.522 (3.63), 2.562 (4.32), 3.112 (0.59), 3.136 (0.62), 3.357 (0.66), 3.802 (1.21), 3.822 (14.93), 3.999 (0.78), 4.017 (2.23), 4.034 (2.37), 4.053 (0.90), 4.068 (0.64), 4.082 (0.40), 4.091 (0.43), 4.208 (2.02), 4.240 (2.28), 4.393 (0.66), 4.411 (0.69), 4.424 (1.12), 4.433 (0.71), 4.442 (0.90), 4.451 (1.88), 4.464 (0.74), 4.469 (1.95), 4.482 (1.99), 4.487 (0.71), 4.500 (1.85), 4.509 (0.90), 4.518 (0.52), 4.527 (0.85), 4.543 (2.18), 4.575 (1.85), 7.095 (1.99), 7.098 (2.21), 7.113 (2.28), 7.116 (2.18), 7.339 (2.18), 7.357 (2.14), 7.359 (2.40), 7.377 (1.78), 7.592 (1.73), 7.611 (1.90), 7.613 (1.99), 7.627 (0.88), 7.631 (2.30), 7.644 (1.19), 7.647 (1.69), 7.650 (1.00), 7.664 (1.23), 7.667 (1.16), 7.715 (1.09), 7.718 (1.21), 7.732 (0.90), 7.736 (1.61), 7.739 (1.31), 7.752 (0.83), 7.756 (0.78), 7.903 (1.95), 7.906 (2.28), 7.921 (1.92), 7.924 (1.76), 7.942 (2.28), 7.945 (2.49), 7.962 (2.11), 7.965 (1.97), 8.017 (1.85), 8.035 (2.37), 8.053 (1.52), 8.520 (1.54), 8.541 (1.47).

Intermediate 382

(rac)-2,3-dimethyl-7-(naphthalen-1-ylethynyl)-2,10,11,12,13,15-hexahydropyrazolo[4',3':9,10][1,6]oxazacycloundecino[8,7,6-hi]indole-8-carboxylic acid

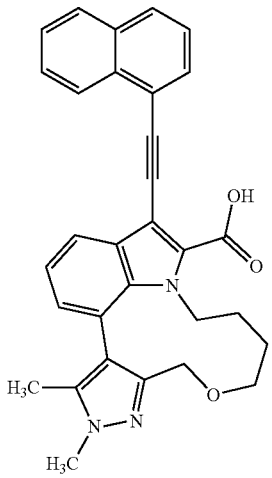 [SMILES: Cc1c2c(nn1C)COCCCCn1c(C(=O)O)c(C#Cc3cccc4ccccc34)c3cccc-2c31]

A solution of (rac)-ethyl 2,3-dimethyl-7-(naphthalen-1-ylethynyl)-2,10,11,12,13,15-hexahydropyrazolo[4',3':9,10][1,6]oxazacycloundecino[8,7,6-hi]indole-8-carboxylate (see Intermediate 381; 190 mg, 367 µmol) in a mixture of THF (10 ml), ethanol (5.0 ml) and an aqueous lithium hydroxide solution (5.0 ml, 1.0 M, 5.0 mmol) was stirred 17 hours at room temperature, followed by 24 hours at 40° C. Then the reaction mixture was partitioned between water and ethyl acetate. After washing of the organic phase with a saturated aqueous sodium chloride solution, the organic phase was filtered through a hydrophobic filter. Evaporation of the filtrate yielded the crude title compound (180 mg).

LC-MS (Method 2): $R_f$=0.78 min; MS (ESIpos): m/z=490 [M+H]$^+$ $^1$H-NMR (400 MHz, DMSO-d6) δ[ppm]: 0.882 (0.71), 1.070 (0.50), 1.092 (0.78), 1.108 (0.71), 1.124 (1.16), 1.147 (0.84), 1.166 (2.30), 1.178 (2.25), 1.233 (6.51), 1.286 (1.54), 1.322 (2.56), 1.329 (2.87), 1.364 (9.41), 1.408 (2.66), 1.480 (0.97), 1.855 (15.75), 2.083 (8.92), 2.327 (0.97), 2.668 (0.97), 3.112 (1.07), 3.131 (1.01), 3.819 (16.00), 3.991 (0.69), 4.012 (0.92), 4.209 (2.33), 4.240 (2.67), 4.447 (0.86), 4.463 (0.84), 4.478 (0.81), 4.532 (2.58), 4.563 (2.15), 6.784 (0.48), 7.043 (2.03), 7.060 (2.25), 7.117 (1.24), 7.299 (1.52), 7.317 (2.49), 7.336 (1.39), 7.565 (1.49), 7.584 (2.61), 7.603 (2.61), 7.618 (2.16), 7.637 (1.82), 7.655 (1.63), 7.675 (2.13), 7.692 (0.99), 7.878 (2.56), 7.895 (2.31), 7.920 (2.33), 7.939 (2.16), 7.977 (2.59), 7.998 (4.59), 8.019 (2.30), 8.625 (1.95), 8.645 (1.90).

Intermediate 383

(rac)-ethyl 2,3-dimethyl-7-{[4-(trifluoromethyl)phenyl]ethynyl}-2,10,11,12,13,15-hexahydropyrazolo[4',3':9,10][1,6]oxazacycloundecino[8,7,6-hi]indole-8-carboxylate

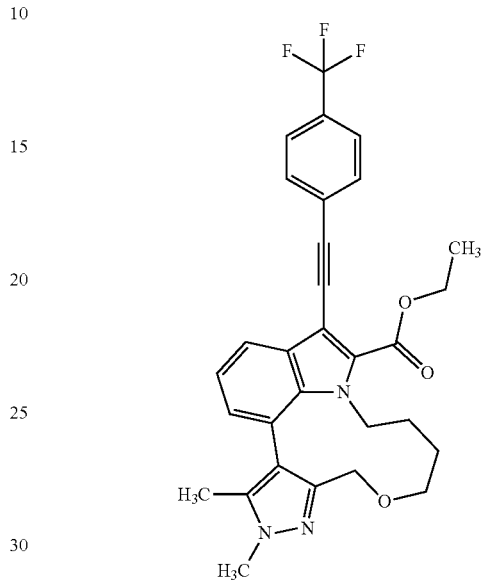

To a mixture of (rac)-ethyl 7-iodo-2,3-dimethyl-2,10,11,12,13,15-hexahydropyrazolo[4',3':9,10][1,6]oxazacycloundecino[8,7,6-hi]indole-8-carboxylate (see Intermediate 380; 200 mg, 405 µmol), dichloro[bis(triphenyl-λ$^5$-phosphanyl)]palladium (5.71 mg, 8.11 µmol) and copper(I) iodide (770 µg, 4.1 µmol) in a mixture of triethylamine (1.0 ml) and acetonitrile (10 ml), 1-ethynyl-4-(trifluoromethyl)benzene (82 µl, 490 µmol) was added dropwise. The reaction mixture was then stirred 17 hours at room temperature, followed by stirring for 6 hours at 60° C. Then stirring was continued at 100° C. for 72 hours. After cooling to room temperature, the reaction mixture was evaporated to dryness and the residue was subjected to flash chromatography (Biotage SNAP cartridge silica, dichloromethane/acetone gradient, 0%-100% acetone) to give the title compound (112 mg).

LC-MS (Method 2): Rt=1.53 min; MS (ESIpos): m/z=536 [M+H]$^+$ $^1$H-NMR (400 MHz, DMSO-d6) δ[ppm]: 1.204 (0.84), 1.213 (1.01), 1.232 (1.26), 1.353 (0.58), 1.361 (2.91), 1.379 (6.31), 1.397 (3.04), 1.829 (9.73), 2.084 (2.43), 2.322 (0.76), 2.327 (1.04), 2.331 (0.79), 2.518 (8.00), 2.522 (4.89), 2.562 (1.47), 2.665 (0.76), 2.669 (1.04), 2.673 (0.79), 3.092 (0.47), 3.112 (0.47), 3.307 (0.67), 3.801 (2.28), 3.811 (8.95), 4.038 (0.49), 4.195 (1.46), 4.227 (1.44), 4.342 (0.70), 4.351 (0.52), 4.360 (0.76), 4.369 (1.40), 4.387 (1.40), 4.405 (0.68), 4.414 (0.49), 4.432 (1.04), 4.450 (0.95), 4.459 (0.61), 4.477 (0.59), 4.526 (1.35), 4.557 (1.13), 7.075 (1.15), 7.078 (1.22), 7.093 (1.35), 7.096 (1.26), 7.301 (1.17), 7.322 (1.42), 7.339 (1.01), 7.834 (16.00), 7.875 (1.31), 7.878 (1.44), 7.896 (1.26), 7.899 (1.20).

Intermediate 384

(rac)-ethyl 2,3-dimethyl-7-{2-[4-(trifluoromethyl)phenyl]ethyl}-2,10,11,12,13,15-hexahydropyrazolo[4',3':9,10][1,6]oxazacycloundecino[8,7,6-hi]indole-8-carboxylate

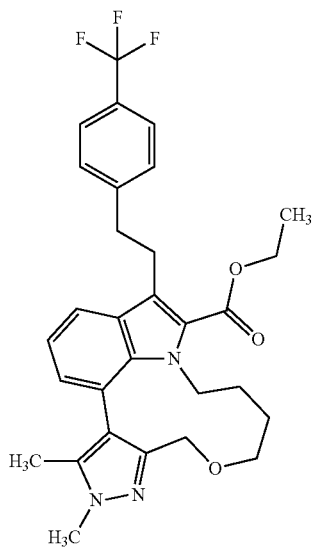 [SMILES: CCOC(=O)c1c(CCc2ccc(C(F)(F)F)cc2)c2cccc3c2n1CCCCOCc1nn(C)c(C)c1-3]

A mixture of (rac)-ethyl 2,3-dimethyl-7-{[4-(trifluoromethyl)phenyl]ethynyl}-2,10,11,12,13,15-hexahydropyrazolo[4',3':9,10][1,6]oxazacycloundecino[8,7,6-hi]indole-8-carboxylate (see Intermediate 383; 60.0 mg, 112 µmol) and a commercially available heterogeneous catalyst kit (Strem/Evonik, 10% Palladium on activated carbon, Pearlman (50-70% wetted powder) Evonik E 101 NE/W 10% Pd; 20.0 mg, 188 µmol) in ethanol (20 ml) was stirred under a hydrogen atmosphere for 29 hours. After filtration, a fresh portion of the above mentioned Pd-catalyst (20 mg) was added to the filtrate and stirring under an atmosphere of hydrogen was continued for 24 hours. After filtration and evaporation of the filtrate, the residue was subjected to flash chromatography (Biotage SNAP cartridge silica, dichloromethane/acetone gradient, 0%→30% acetone) to give the title compound (35 mg).

LC-MS (Method 2): $R_t$=1.59 min; MS (ESIpos): m/z=540 [M+H]$^+$ $^1$H-NMR (400 MHz, DMSO-d6) δ[ppm]: 1.153 (0.47), 1.176 (0.58), 1.188 (0.57), 1.202 (0.51), 1.232 (0.92), 1.277 (5.03), 1.294 (10.76), 1.312 (4.99), 1.352 (0.82), 1.817 (16.00), 2.518 (4.52), 2.522 (3.12), 2.961 (0.68), 2.979 (1.48), 2.999 (0.97), 3.081 (0.60), 3.094 (0.62), 3.269 (0.66), 3.276 (0.60), 3.285 (0.88), 3.301 (1.05), 3.346 (1.21), 3.358 (0.41), 3.365 (0.53), 3.802 (15.77), 3.905 (0.60), 3.928 (0.45), 4.176 (2.49), 4.195 (1.46), 4.207 (2.75), 4.213 (1.68), 4.221 (1.79), 4.230 (0.66), 4.239 (1.77), 4.257 (0.57), 4.261 (0.58), 4.278 (1.71), 4.297 (1.56), 4.305 (0.95), 4.314 (0.47), 4.323 (0.97), 4.513 (2.10), 4.544 (1.79), 6.949 (1.83), 6.952 (1.83), 6.967 (2.24), 6.969 (2.01), 7.121 (1.93), 7.138 (1.89), 7.140 (2.24), 7.158 (1.62), 7.384 (2.38), 7.404 (2.79), 7.587 (3.02), 7.607 (2.49), 7.727 (1.81), 7.729 (1.95), 7.746 (1.73), 7.749 (1.70).

Intermediate 385

(rac)-ethyl 7-ethenyl-2,3-dimethyl-2,10,11,12,13,15-hexahydropyrazolo[4',3':9,10][1,6]oxazacycloundecino[8,7,6-hi]indole-8-carboxylate

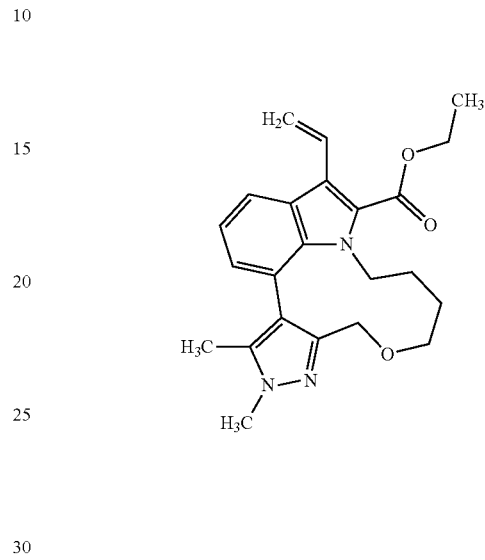

To (rac)-ethyl 7-iodo-2,3-dimethyl-2,10,11,12,13,15-hexahydropyrazolo[4',3':9,10][1,6]oxazacycloundecino[8,7,6-hi]indole-8-carboxylate (see Intermediate 380; 500 mg, 1.01 mmol) in a mixture of DMF (10 ml) and water (1.9 ml), 2-ethenyl-4,4,5,5-tetramethyl-1,3,2-dioxaborolane (600 µl, 3.5 mmol) and sodium carbonate (645 mg, 6.08 mmol) were added. The mixture then was stirred at 80° C. for four hours, followed by stirring at room temperature for 24 hours. Subsequently the reaction mixture was evaporated to dryness. The residue was pooled with the residue from an identical reaction on a 100 mg scale and was then subjected to flash chromatography (Biotage SNAP cartridge silica, dichloromethane/acetone gradient, 0%-25% acetone) to give the title compound (385 mg).

LC-MS (Method 2): $R_t$=1.36 min; MS (ESIpos): m/z=395 [M+H]$^+$ $^1$H-NMR (400 MHz, DMSO-d6) δ[ppm]: 1.167 (0.59), 1.172 (0.68), 1.180 (0.87), 1.193 (0.88), 1.205 (0.84), 1.216 (0.59), 1.230 (0.52), 1.309 (5.09), 1.315 (0.74), 1.327 (11.03), 1.340 (0.85), 1.345 (5.09), 1.352 (0.49), 1.825 (16.00), 1.832 (0.87), 2.518 (2.23), 2.522 (1.58), 3.082 (0.66), 3.096 (0.59), 3.106 (0.43), 3.280 (0.40), 3.288 (0.53), 3.293 (0.61), 3.302 (0.57), 3.318 (0.68), 3.803 (15.91), 3.975 (0.71), 3.986 (0.43), 3.998 (0.48), 4.174 (2.56), 4.192 (0.65), 4.205 (2.78), 4.284 (0.91), 4.294 (0.49), 4.302 (0.91), 4.311 (1.64), 4.329 (1.73), 4.347 (0.59), 4.350 (0.58), 4.369 (1.65), 4.387 (1.61), 4.395 (0.95), 4.404 (0.49), 4.413 (0.95), 4.515 (2.16), 4.547 (1.82), 5.461 (1.68), 5.465 (1.47), 5.491 (1.48), 5.494 (1.80), 5.835 (1.38), 5.839 (1.42), 5.881 (1.46), 5.884 (1.56), 6.993 (1.72), 6.996 (1.82), 7.011 (2.17), 7.014 (2.01), 7.197 (1.94), 7.214 (1.80), 7.217 (2.30), 7.220 (1.81), 7.235 (1.62), 7.249 (1.61), 7.266 (1.58), 7.295 (1.33), 7.969 (1.65), 7.972 (1.84), 7.989 (1.67), 7.992 (1.62).

Intermediate 386

(rac)-ethyl 7-(2-hydroxyethyl)-2,3-dimethyl-2,10,11,12,13,15-hexahydropyrazolo[4',3':9,10][1,6]oxazacycloundecino[8,7,6-hi]indole-8-carboxylate

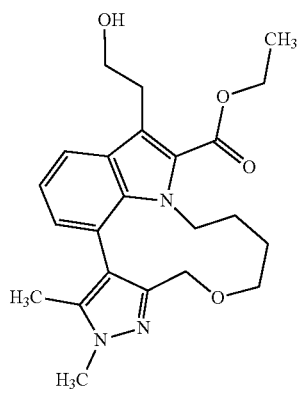 [SMILES: CCOC(=O)c1c(CCO)c2cccc3c2n1CCCCOCc1nn(C)c(C)c1-3]

Under an argon atmosphere, 9-borabicyclo[3.3.1]nonane (0.5 M in THF 16 ml, 8.2 mmol) was added dropwise to a solution of (rac)-ethyl 7-ethenyl-2,3-dimethyl-2,10,11,12,13,15-hexahydropyrazolo[4',3':9,10][1,6]oxazacycloundecino[8,7,6-hi]indole-8-carboxylate (see intermediate 385, 270 mg, 686 µmol) in THF (47 ml). After stirring the mixture for two hours at room temperature, it was cooled to 0° C., and an aqueous sodium hydroxide solution (5%, 4.2 ml, 5.5 mmol) was added dropwise. Five minutes later, an aqueous hydrogen peroxide solution (30%, 1.1 ml, 10 mmol) was added dropwise at the same temperature. This was followed by stirring at room temperature for 24 hours. The reaction mixture then was partitioned between water and ethyl acetate. The organic phase then was washed with a saturated aqueous disodium sulfurothioate (also referred herein as sodium thiosulfate) solution followed by a wash with a saturated aqueous sodium chloride solution. The organic phase then was filtered through a hydrophobic filter and the filtrate was evaporated to dryness. The residue was pooled with the residue from an identical reaction on a 50 mg scale and was then subjected to flash chromatography (Biotage SNAP cartridge silica, dichloromethane/acetone gradient, 0%-30% acetone) to give the title compound (107 mg).

LC-MS (Method 2): Rt=1.04 min; MS (ESIpos): m/z=413 [M+H]$^+$ $^1$H-NMR (400 MHz, DMSO-d6) δ[ppm]: 1.145 (0.77), 1.163 (0.69), 1.176 (0.77), 1.188 (0.63), 1.200 (0.49), 1.214 (0.40), 1.234 (0.75), 1.270 (0.54), 1.285 (0.54), 1.313 (5.19), 1.331 (11.56), 1.349 (5.19), 1.817 (0.80), 1.827 (16.00), 2.084 (6.51), 2.332 (1.20), 2.336 (0.52), 2.518 (5.94), 2.523 (4.19), 2.673 (1.20), 2.678 (0.49), 3.073 (0.66), 3.086 (0.60), 3.097 (0.63), 3.112 (0.69), 3.128 (0.54), 3.143 (0.60), 3.149 (0.57), 3.164 (0.46), 3.224 (0.57), 3.230 (0.60), 3.245 (0.60), 3.256 (0.69), 3.261 (0.86), 3.269 (0.60), 3.277 (0.89), 3.294 (0.46), 3.553 (0.40), 3.569 (0.60), 3.574 (0.46), 3.589 (0.80), 3.603 (0.77), 3.610 (0.52), 3.616 (0.46), 3.623 (0.63), 3.798 (15.51), 3.917 (0.63), 3.939 (0.43), 4.163 (2.15), 4.194 (2.47), 4.203 (0.72), 4.218 (0.43), 4.223 (0.43), 4.231 (0.40), 4.248 (0.97), 4.258 (0.49), 4.266 (0.97), 4.275 (1.69), 4.293 (1.75), 4.310 (0.52), 4.319 (0.54), 4.337 (1.84), 4.355 (1.66), 4.364 (0.97), 4.373 (0.46), 4.382 (0.97), 4.482 (2.09), 4.513 (1.81), 4.682 (1.18), 4.696 (3.13), 4.710 (1.18), 6.925 (1.78), 6.929 (1.86), 6.943 (2.18), 6.946 (1.95), 7.121 (1.81), 7.138 (1.75), 7.140 (2.24), 7.158 (1.72), 7.704 (1.69), 7.706 (1.89), 7.724 (1.75), 7.727 (1.69).

Intermediate 387

(rac)-ethyl 2,3-dimethyl-7-[2-(naphthalen-2-yloxy)ethyl]-2,10,11,12,13,15-hexahydropyrazolo[4',3':9,10][1,6]oxazacycloundecino[8,7,6-hi]indole-8-carboxylate

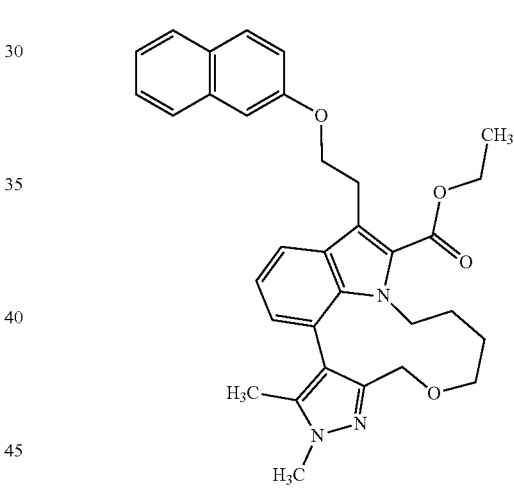

To a mixture of (rac)-ethyl 7-(2-hydroxyethyl)-2,3-dimethyl-2,10,11,12,13,15-hexahydropyrazolo[4',3':9,10][1,6]oxazacycloundecino[8,7,6-hi]indole-8-carboxylate (see Intermediate 386; 138 mg, 65% purity, 218 µmol), naphthalen-2-ol (95.2 mg, 654 µmol) and triphenylphosphane (173 mg, 654 µmol) in THF (1.8 ml), dipropan-2-yl (E)-diazene-1,2-dicarboxylate (also referred to herein as diisopropyl azodicarboxylate; 130 µl, 650 µmol) was added dropwise at 0° C. After stirring the reaction mixture for four days at room temperature, it was evaporated to dryness and the residue was subjected to flash chromatography (Biotage SNAP cartridge silica, dichloromethane/acetone gradient, 0%-40% acetone) to give the title compound (107 mg).

LC-MS (Method 2): Rt=1.56 min; MS (ESIpos): m/z=539 [M+H]$^+$

Intermediate 388 ethyl 1-{4-[bis(tert-butoxycarbonyl)amino]butyl}-7-[3-(hydroxymethyl)-1,5-dimethyl-1H-pyrazol-4-yl]-3-[3-(naphthalen-1-yloxy)propyl]-1H-indole-2-carboxylate

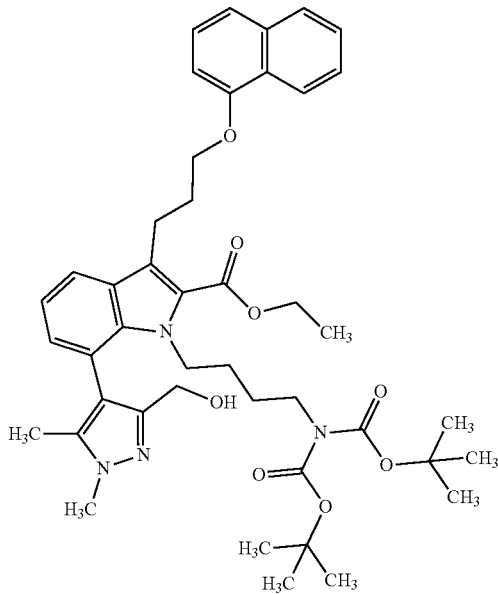 [SMILES: CCOC(=O)c1c(CCCOc2cccc3ccccc23)c2cccc(-c3c(CO)nn(C)c3C)c2n1CCCCN(C(=O)OC(C)(C)C)C(=O)OC(C)(C)C]

A mixture of ethyl 7-[3-(hydroxymethyl)-1,5-dimethyl-1H-pyrazol-4-yl]-3-[3-(naphthalen-1-yloxy)propyl]-1H-indole-2-carboxylate (see Intermediate 12; 5.00 g, 10.0 mmol) and caesium carbonate (16.4 g, 50.2 mmol) in DMF (130 ml) was stirred for 30 minutes at room temperature. Then di-tert-butyl (4-bromobutyl)imidodicarbonate (4.25 g, 12.1 mmol; for a preparation see: *Helv. Chim. Acta* 1991, 74, 800-806) was added, and the mixture was stirred at room temperature for 5 days. After the addition of water, the mixture was extracted three times with ethyl acetate. The combined organic phases were washed with an aqueous saturated sodium chloride solution, dried with sodium sulphate and filtered. After evaporation of the filtrate to dryness, the residue was subjected to flash chromatography (Biotage SNAP cartridge silica, dichloromethane/acetone gradient, 0%-40% acetone) to give the title compound (5.18 g).

LC-MS (Method 2): Rt=1.75 min; MS (ESIpos): m/z=770 [M+H]$^+$ $^1$H-NMR (400 MHz, CHLOROFORM-d) δ [ppm]: 0.018 (0.16), 1.299 (0.78), 1.317 (1.70), 1.335 (0.78), 1.387 (16.00), 1.445 (0.64), 1.535 (2.81), 2.055 (0.19), 2.071 (0.47), 2.077 (2.60), 2.083 (0.30), 2.113 (0.16), 2.241 (0.17), 2.257 (0.21), 2.278 (0.18), 2.824 (1.72), 2.897 (2.06), 3.191 (0.18), 3.209 (0.36), 3.228 (0.20), 3.288 (0.22), 3.307 (0.30), 3.326 (0.21), 3.811 (2.56), 4.147 (0.34), 4.162 (0.64), 4.177 (0.35), 4.257 (0.22), 4.274 (0.66), 4.292 (0.62), 4.310 (0.19), 4.426 (0.35), 4.440 (0.62), 4.455 (0.34), 6.721 (0.26), 6.723 (0.26), 6.740 (0.28), 6.742 (0.27), 6.947 (0.22), 6.950 (0.25), 6.965 (0.40), 6.968 (0.36), 7.011 (0.34), 7.028 (0.28), 7.030 (0.39), 7.048 (0.23), 7.281 (0.20), 7.301 (0.39), 7.320 (0.34), 7.353 (0.39), 7.374 (0.20), 7.427 (0.41), 7.432 (0.27), 7.437 (0.31), 7.441 (0.31), 7.445 (0.29), 7.451 (0.44), 7.634 (0.28), 7.637 (0.31), 7.654 (0.29), 7.657 (0.28), 7.740 (0.22), 7.752 (0.18), 7.763 (0.19), 7.959 (0.22), 8.304 (0.19), 8.316 (0.16), 8.329 (0.18).

Intermediate 389 ethyl 1-{4-[bis(tert-butoxycarbonyl)amino]butyl}-7-[3-(bromomethyl)-1,5-dimethyl-1H-pyrazol-4-yl]-3-[3-(naphthalen-1-yloxy)propyl]-1H-indole-2-carboxylate

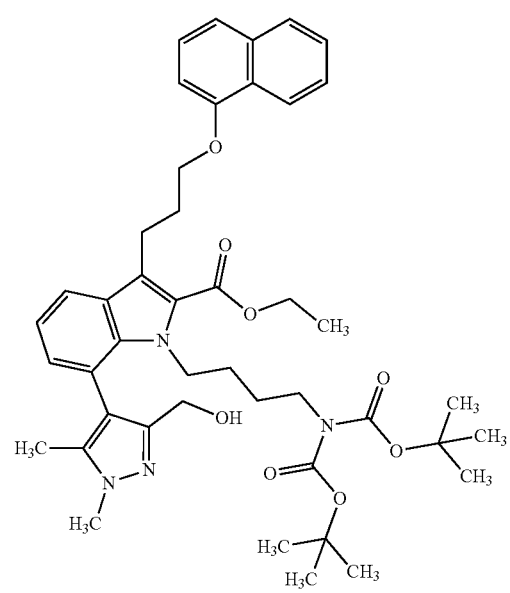 [SMILES: CCOC(=O)c1c(CCCOc2cccc3ccccc23)c2cccc(-c3c(CO)nn(C)c3C)c2n1CCCCN(C(=O)OC(C)(C)C)C(=O)OC(C)(C)C]

At 0° C., triphenylphosphane (2.65 g, 10.1 mmol) was added to a solution of ethyl 1-{4-[bis(tert-butoxycarbonyl)amino]butyl}-7-[3-(hydroxymethyl)-1,5-dimethyl-1H-pyrazol-4-yl]-3-[3-(naphthalen-1-yloxy)propyl]-1H-indole-2-carboxylate (see Intermediate 388; 5.18 g, 6.74 mmol) in dichloromethane (120 ml), and the mixture was stirred for 10 minutes at 0° C. Then carbon tetrabromide (3.35 g, 10.1 mmol) was added and stirring was continued for 24 hours at room temperature. After evaporation of the reaction mixture to dryness, the residue was subjected to flash chromatography (Biotage SNAP cartridge silica, hexane/ethyl acetate gradient, 7%→60% acetone) to give the title compound (4.06 g).

$^1$H-NMR (400 MHz, CHLOROFORM-d) δ [ppm]: 0.009 (3.37), 1.094 (0.17), 1.303 (0.80), 1.320 (1.80), 1.338 (0.85), 1.382 (16.00), 1.506 (1.51), 2.079 (2.03), 2.084 (1.02), 2.251 (0.18), 2.268 (0.24), 2.287 (0.19), 3.213 (0.18), 3.232 (0.27), 3.248 (0.16), 3.296 (0.25), 3.315 (0.34), 3.333 (0.23), 3.833 (2.11), 3.837 (1.09), 4.153 (0.29), 4.167 (0.81), 4.183 (0.34), 4.193 (0.48), 4.260 (0.23), 4.277 (0.69), 4.295 (0.74), 4.313 (0.21), 4.325 (0.47), 4.351 (0.28), 4.412 (0.18), 5.239 (0.29), 6.724 (0.29), 6.742 (0.32), 7.033 (0.18), 7.038 (0.36), 7.042 (0.40), 7.044 (0.43), 7.052 (0.16), 7.063 (0.34), 7.281 (0.22), 7.302 (0.41), 7.320 (0.37), 7.354 (0.43), 7.375 (0.22), 7.427 (0.41), 7.432 (0.28), 7.438 (0.32), 7.441 (0.34), 7.446 (0.30), 7.451 (0.44), 7.662 (0.28), 7.667 (0.22), 7.681 (0.27), 7.686 (0.20), 7.740 (0.23), 7.752 (0.20), 7.764 (0.20), 8.304 (0.20), 8.316 (0.17), 8.329 (0.19).

Intermediate 390 ethyl 1-(4-aminobutyl)-7-[3-(bromomethyl)-1,5-dimethyl-1H-pyrazol-4-yl]-3-[3-(naphthalen-1-yloxy)propyl]-1H-indole-2-carboxylate hydrochloric acid salt

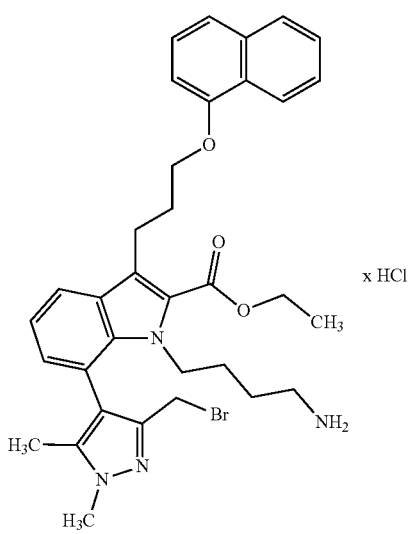 [SMILES: CCOC(=O)c1c(CCCOc2cccc3ccccc23)c2cccc(-c3c(CBr)nn(C)c3C)c2n1CCCCN]

At 0° C., hydrochloric acid in 1,4-dioxane (85 ml, 4.0 M, 340 mmol) was added to a stirred solution of ethyl 1-{4-[bis(tert-butoxycarbonyl)amino]butyl}-7-[3-(bromomethyl)-1,5-dimethyl-1H-pyrazol-4-yl]-3-[3-(naphthalen-1-yloxy)propyl]-1H-indole-2-carboxylate (see Intermediate 389; 4.06 g, 4.88 mmol) in methanol (55 ml). Then stirring was continued at room temperature for two hours. After evaporation to dryness the crude title compound (3.5 g) was further used as obtained.

Intermediate 391

(rac)-ethyl 2,3-dimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylate

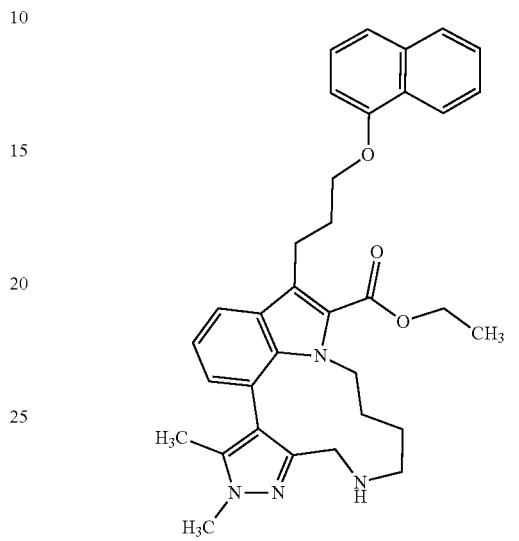

To a solution of ethyl 1-(4-aminobutyl)-7-[3-(bromomethyl)-1,5-dimethyl-1H-pyrazol-4-yl]-3-[3-(naphthalen-1-yloxy)propyl]-1H-indole-2-carboxylate hydrochloric acid salt (see Intermediate 390; 3.50 g) in DMF (410 ml) was added caesium carbonate (8.09 g, 24.8 mmol). Then the reaction mixture was stirred at 65° C. for 28 hours. After cooling to room temperature and addition of water, the mixture was extracted three times with ethyl acetate. The combined organic phases then were washed with an aqueous saturated sodium chloride solution, dried with sodium sulphate and filtered. Evaporation of the filtrate to dryness yielded the crude title compound (2.75 g).

LC-MS (Method 1): Rt=1.36 min; MS (ESIpos): m/z=552 [M+H]$^+$ $^1$H-NMR (400 MHz, DMSO-d6) δ[ppm]: 0.869 (0.45), 0.983 (0.48), 1.144 (0.41), 1.179 (0.95), 1.196 (0.90), 1.226 (0.55), 1.234 (0.51), 1.261 (4.80), 1.278 (10.45), 1.296 (4.89), 1.844 (16.00), 1.927 (0.43), 2.045 (0.64), 2.058 (0.57), 2.076 (0.69), 2.194 (1.02), 2.211 (1.45), 2.228 (1.07), 2.419 (0.46), 2.436 (0.59), 2.455 (0.45), 2.470 (0.40), 2.518 (1.83), 2.523 (1.30), 2.727 (10.22), 2.729 (9.77), 2.888 (12.42), 3.238 (0.56), 3.254 (0.68), 3.272 (1.00), 3.291 (0.60), 3.332 (6.45), 3.365 (0.75), 3.380 (0.61), 3.542 (0.63), 3.576 (2.64), 3.588 (2.57), 3.622 (0.58), 3.800 (1.42), 3.836 (0.49), 4.021 (0.57), 4.039 (0.65), 4.055 (0.68), 4.180 (0.45), 4.198 (1.63), 4.207 (1.66), 4.216 (2.92), 4.220 (2.37), 4.225 (2.81), 4.230 (1.42), 4.233 (1.45), 4.242 (2.10), 4.262 (0.82), 4.280 (1.82), 4.298 (1.77), 4.307 (1.00), 4.316 (0.63), 4.324 (1.32), 4.341 (0.89), 4.354 (0.50), 4.359 (0.48), 4.374 (0.68), 5.759 (0.97), 6.855 (1.87), 6.858 (1.93), 6.872 (2.27), 6.876 (2.07), 6.899 (1.83), 6.916 (2.01), 7.031 (1.88), 7.049 (1.91), 7.051 (2.23), 7.069 (1.62), 7.371 (1.43), 7.392 (2.71), 7.411 (2.23), 7.452 (2.84), 7.473 (1.62), 7.501 (0.65), 7.513 (1.91), 7.518 (2.90), 7.528 (3.29), 7.537 (2.70), 7.541 (2.03), 7.553 (0.61), 7.713 (1.94), 7.717 (1.99), 7.734 (1.84), 7.736 (1.80), 7.862 (1.63), 7.866 (1.15), 7.874 (0.89), 7.877 (1.04), 7.880 (1.07), 7.886 (1.34), 7.951 (1.51), 8.236 (1.31), 8.247 (0.91), 8.260 (1.26).

Intermediate 392 methyl 5-(difluoromethoxy)-1-methyl-1H-pyrazole-3-carboxylate

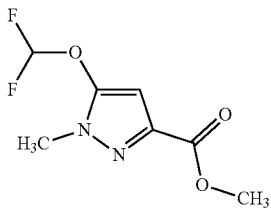

Methyl 5-hydroxy-1-methyl-1H-pyrazole-3-carboxylate (1.00 g, 6.40 mmol) and sodium chloro(difluoro)acetate (1.95 g, 12.8 mmol) were provided in DMF (20 mL) and potassium carbonate (1.77 g, 12.8 mmol) was added. The reaction mixture was stirred for 20 minutes at 130° C. After cooling to room temperature, the reaction mixture was diluted with water and extracted with ethyl acetate. The combined organic phases were washed with brine, filtered through a silicone filter and concentrated. Purification by flash chromatography on silica gel (ethyl acetate/hexanes) yielded 973 mg (98% purity, 72% yield) of the title compound.

LC-MS (Method 1): $R_t$=0.80 min; MS (ESIpos): m/z=207 [M+H]$^+$ $^1$H-NMR (400 MHz, DMSO-d6) δ[ppm]: 3.332 (12.31), 3.791 (16.00), 6.499 (3.17), 7.152 (1.42), 7.332 (2.94), 7.512 (1.36).

Intermediate 393 methyl 4-bromo-5-(difluoromethoxy)-1-methyl-1H-pyrazole-3-carboxylate

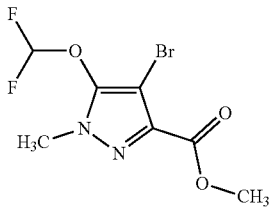

A solution of bromine in glacial acetic acid (9.4 ml, 1.0 M, 9.4 mmol) was added to a solution of methyl 5-(difluoromethoxy)-1-methyl-1H-pyrazole-3-carboxylate (see Intermediate 392; 973 mg, 4.72 mmol) in glacial acetic acid (7 ml). The reaction mixture was stirred for 96 h at room temperature and was poured into ice water. An aqueous sodium thiosulfate solution (10%) was added, the mixture was extracted with ethyl acetate and the combined organic phases were washed with brine, filtered through a silicone filter and concentrated to give 1.26 g (96% purity, 90% yield) of the title compound.

LC-MS (Method 1): $R_t$=0.94 min; MS (ESIpos): m/z=285 [M+H]$^+$ $^1$H-NMR (400 MHz, DMSO-d6) δ[ppm]: 1.907 (1.29), 3.332 (16.00), 7.133 (1.36), 7.311 (2.76), 7.488 (1.23).

Intermediate 394

[4-bromo-5-(difluoromethoxy)-1-methyl-1H-pyrazol-3-yl]methanol

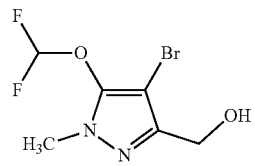

Lithium borohydride (120 mg, 5.53 mmol) was added to a solution of methyl 4-bromo-5-(difluoromethoxy)-1-methyl-1H-pyrazole-3-carboxylate (see Intermediate 393; 1.26 g, 4.42 mmol) in THF (20 ml), and the reaction mixture was stirred for 20 h at room temperature and for 2 h at 60° C. Saturated aqueous ammonium chloride solution was added and the mixture was extracted with ethyl acetate, the organic phase was washed with brine, filtered through a silicone filter and concentrated to give 1.02 g (90% purity, 81% yield) of the title compound.

LC-MS (Method 1): $R_t$=0.79 min; MS (ESIpos): m/z=239 [M+H]$^+$ $^1$H-NMR (400 MHz, DMSO-d6) δ[ppm]: 2.518 (0.43), 3.332 (16.00), 3.598 (0.67), 4.302 (8.99), 4.316 (9.10), 5.123 (2.52), 5.137 (5.54), 5.150 (2.25), 7.086 (2.92), 7.264 (5.18), 7.442 (2.64).

Intermediate 395 ethyl 7-[5-(difluoromethoxy)-3-(hydroxymethyl)-1-methyl-1H-pyrazol-4-yl]-3-[3-(naphthalen-1-yloxy)propyl]-1H-indole-2-carboxylate

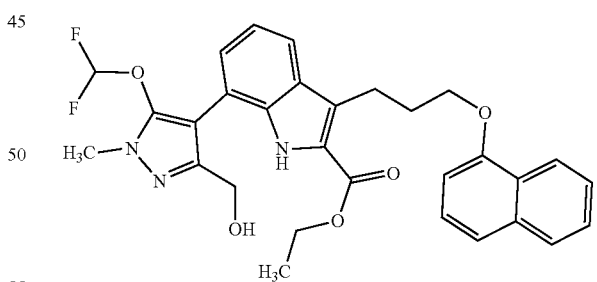

XPhos Pd G2 (see abbreviation list, 61.2 mg, 77.8 µmol) was added to a degassed mixture of ethyl 3-[3-(naphthalen-1-yloxy)propyl]-7-(4,4,5,5-tetramethyl-1,3,2-dioxaborolan-2-yl)-1H-indole-2-carboxylate (see Intermediate 5, 777 mg, 1.56 mmol), [4-bromo-5-(difluoromethoxy)-1-methyl-1H-pyrazol-3-yl]methanol (see Intermediate 394; 400 mg, 1.56 mmol) and an aqueous potassium phosphate solution (6.2 ml, 0.50 M, 3.1 mmol) in THF (8.0 ml), and the mixture was stirred for 2 h at 45° C. Ethyl acetate and brine were added, the mixture was extracted with ethyl acetate, the combined organic phases were filtered through a silicone filter and concentrated. Purification by flash chromatography on silica gel (ethyl acetate/hexanes) yielded 880 mg (98% purity, 100% yield) of the title compound.

LC-MS (Method 1): $R_t$=1.53 min; MS (ESIpos): m/z=550 [M+H]$^+$ $^1$H-NMR (400 MHz, DMSO-d6) δ[ppm]: 1.067 (0.82), 1.154 (1.26), 1.172 (2.41), 1.190 (1.18), 1.266 (3.71), 1.284 (8.54), 1.301 (3.82), 1.988 (4.21), 2.084 (0.68), 2.210 (0.68), 2.229 (0.90), 2.246 (0.71), 2.518 (1.57), 2.523 (1.04), 3.348 (1.45), 3.369 (0.85), 3.772 (10.36), 4.017 (0.96), 4.035 (0.96), 4.203 (0.99), 4.218 (2.09), 4.233 (1.07), 4.245 (1.53), 4.254 (3.22), 4.263 (3.90), 4.280 (3.31), 4.298 (0.95), 5.675 (0.87), 5.759 (16.00), 6.697 (1.11), 6.876 (2.17), 6.906 (1.23), 6.923 (1.36), 7.056 (1.03), 7.060 (1.25), 7.078 (1.64), 7.080 (1.48), 7.098 (1.43), 7.224 (1.67), 7.226 (1.73), 7.242 (1.41), 7.244 (1.29), 7.374 (1.01), 7.394 (1.83), 7.413 (1.57), 7.452 (1.83), 7.473 (0.99), 7.498 (0.41), 7.510 (1.22), 7.516 (1.80), 7.525 (2.56), 7.535 (2.04), 7.540 (1.26), 7.552 (0.41), 7.691 (1.33), 7.693 (1.34), 7.711 (1.25), 7.713 (1.19), 7.862 (1.03), 7.865 (0.75), 7.872 (0.51), 7.878 (0.68), 7.880 (0.71), 7.886 (0.88), 8.242 (0.92), 8.250 (0.73), 8.255 (0.40), 8.257 (0.41), 8.267 (0.86), 11.314 (1.01).

Intermediate 396

(rac)-ethyl (11Z)-3-(difluoromethoxy)-2-methyl-7-[3-(naphthalen-1-yloxy)propyl]-2,10,13,15-tetrahydropyrazolo[4',3':9,10][1,6]oxazacycloundecino[8,7,6-hi]indole-8-carboxylate

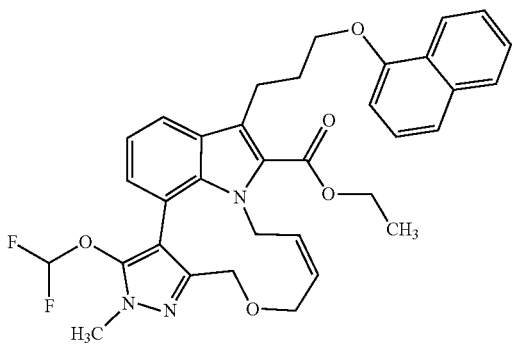 [SMILES: CCOC(=O)c1c(CCCOc2cccc3ccccc23)c2cccc3c2n1C/C=C\COCc1nn(C)c(OC(F)F)c1-3]

A mixture of ethyl 7-[5-(difluoromethoxy)-3-(hydroxymethyl)-1-methyl-1H-pyrazol-4-yl]-3-[3-(naphthalen-1-yloxy)propyl]-1H-indole-2-carboxylate (see Intermediate 395; 1.06 g, 1.93 mmol), (2Z)-1,4-dichlorobut-2-ene (300 μl, 2.9 mmol), caesium carbonate (3.14 g, 9.64 mmol) and sodium iodide (578 mg, 3.86 mmol) in acetonitrile (15 ml) was stirred for 20 h at room temperature and for 4 h at 65° C. Water was added, the mixture was extracted with ethyl acetate, the combined organic phases were washed with brine, filtered through a silicone filter and concentrated. Purification by flash chromatography on silica gel (ethyl acetate/hexanes) yielded 653 mg (98% purity, 55% yield) of the title compound.

LC-MS (Method 1): $R_t$=1.65 min; MS (ESIpos): m/z=603 [M+H]$^+$ $^1$H-NMR (400 MHz, DMSO-d6) δ[ppm]: 1.154 (2.40), 1.172 (4.95), 1.190 (2.50), 1.272 (5.08), 1.290 (11.09), 1.308 (5.18), 1.987 (8.79), 2.207 (1.07), 2.225 (1.52), 2.242 (1.13), 2.518 (2.54), 2.523 (1.68), 3.271 (0.47), 3.287 (0.76), 3.304 (1.29), 3.372 (0.54), 3.635 (0.76), 3.648 (0.90), 3.665 (1.15), 3.678 (1.01), 3.693 (0.45), 3.809 (16.00), 3.833 (1.43), 3.862 (0.80), 3.999 (0.72), 4.018 (2.07), 4.035 (2.08), 4.053 (0.70), 4.214 (3.48), 4.230 (3.33), 4.247 (4.30), 4.260 (1.94), 4.269 (0.49), 4.278 (1.90), 4.296 (0.79), 4.301 (1.99), 4.310 (0.44), 4.318 (1.97), 4.329 (3.45), 4.346 (0.93), 4.363 (2.11), 4.813 (0.50), 4.838 (0.60), 4.851 (1.09), 4.877 (1.25), 4.914 (1.28), 4.949 (0.55), 5.223 (0.49), 5.231 (0.52), 5.250 (1.03), 5.258 (1.07), 5.276 (0.72), 5.284 (0.73), 5.318 (0.57), 5.332 (0.60), 5.345 (0.80), 5.359 (0.76), 6.664 (1.69), 6.842 (2.66), 6.907 (2.05), 6.925 (2.25), 6.956 (1.80), 6.958 (1.86), 6.973 (2.50), 6.975 (2.36), 7.022 (1.48), 7.061 (2.11), 7.081 (2.58), 7.099 (1.60), 7.376 (1.41), 7.396 (2.80), 7.415 (2.17), 7.456 (3.00), 7.477 (1.68), 7.497 (0.62), 7.509 (1.74), 7.516 (2.40), 7.525 (3.71), 7.534 (2.62), 7.540 (1.91), 7.552 (0.64), 7.783 (2.09), 7.785 (2.14), 7.802 (2.01), 7.805 (1.89), 7.864 (1.71), 7.873 (0.91), 7.882 (1.31), 7.887 (1.42), 8.225 (1.46), 8.231 (1.28), 8.240 (0.74), 8.249 (1.40).

Intermediate 397

(rac)-ethyl 3-(difluoromethoxy)-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylate

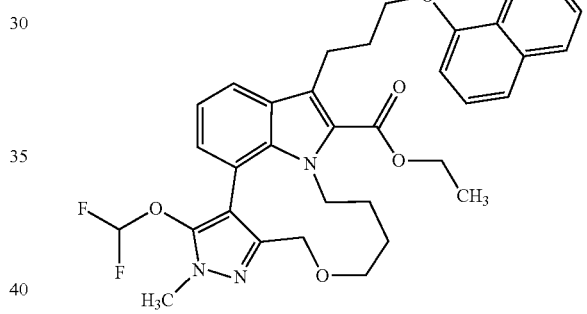

Palladium on charcoal (114 mg, 10%, 107 μmol) was added to a solution of ethyl (11Z)-3-(difluoromethoxy)-2-methyl-7-[3-(naphthalen-1-yloxy)propyl]-2,10,13,15-tetrahydropyrazolo[4',3':9,10][1,6]oxazacycloundecino[8,7,6-hi]indole-8-carboxylate (see Intermediate 396; 645 mg, 1.07 mmol) in THF (4.0 mL) and ethanol (20 mL), and the mixture was vigorously stirred under an atmosphere of hydrogen at room temperature and 20 bar for 25 h. The catalyst was filtered off and the filtrate was concentrated. Purification by flash chromatography on silica gel (ethyl acetate/hexanes) yielded 435 mg (95% purity, 64% yield) of the title compound.

LC-MS (Method 1): $R_t$=1.67 min; MS (ESIpos): m/z=605 [M+H]$^+$ $^1$H-NMR (400 MHz, DMSO-d6) δ[ppm]: 1.154 (4.89), 1.172 (9.79), 1.190 (4.92), 1.207 (0.64), 1.231 (0.51), 1.264 (3.07), 1.282 (6.87), 1.299 (3.14), 1.988 (16.00), 2.191 (0.47), 2.207 (0.69), 2.224 (0.51), 2.518 (1.00), 2.523 (0.72), 3.266 (0.51), 3.358 (0.68), 3.773 (8.61), 3.970 (0.41), 4.000 (1.38), 4.017 (3.78), 4.035 (3.68), 4.053 (1.16), 4.128 (1.32), 4.160 (1.47), 4.176 (0.43), 4.192 (1.07), 4.206 (1.59), 4.215 (0.60), 4.223 (0.96), 4.233 (1.28), 4.251 (1.35), 4.268 (0.62), 4.271 (0.73), 4.289 (1.30), 4.307 (1.13), 4.316 (0.63), 4.334 (0.62), 4.501 (1.34), 4.532 (1.17), 5.759 (12.80), 6.618 (1.05), 6.797 (1.95), 6.881 (1.05), 6.898 (1.15), 6.976 (0.87), 7.010 (0.68), 7.013 (0.78), 7.028 (1.59), 7.032 (1.37), 7.050 (1.58), 7.069 (1.62), 7.087 (0.81), 7.365 (0.88), 7.385 (1.52), 7.405 (1.24), 7.452 (1.53), 7.473 (0.90), 7.517 (1.18), 7.520 (1.33), 7.523 (1.06), 7.531 (1.37), 7.538 (1.11), 7.541 (1.33), 7.544 (1.33), 7.756 (1.13), 7.759 (1.17), 7.775 (1.07), 7.778 (0.98), 7.863 (0.86), 7.867 (0.58), 7.876 (0.80), 7.880 (0.53), 7.886 (0.73), 8.245 (0.78), 8.255 (0.64), 8.269 (0.72).

Intermediate 398 ethyl 5-ethyl-1-methyl-1H-pyrazole-3-carboxylate

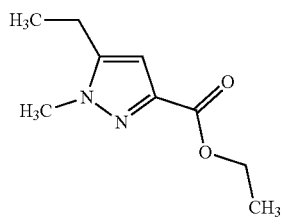

Ethyl 2,4-dioxohexanoate (5.00 g, 29.0 mmol) was provided in glacial acetic acid (20 ml), methylhydrazine (1.5 ml, 29 mmol) was added at 0° C. and the reaction mixture was stirred at room temperature for 23 h. Methylhydrazine (0.5 ml, 8.7 mmol) was added, the reaction mixture was stirred at room temperature for 24 h, was poured into ice water and was extracted with ethyl acetate. The combined organic phases were washed with brine, filtered through a silicone filter and concentrated. Purification by flash chromatography on silica gel (ethyl acetate/hexanes) yielded 2.13 g (99% purity, 40% yield) of the title compound.

LC-MS (Method 1): $R_t$=0.92 min; MS (ESIpos): m/z=183 [M+H]$^+$ $^1$H-NMR (400 MHz, DMSO-d6) δ[ppm]: 1.170 (6.09), 1.188 (12.55), 1.208 (6.57), 1.245 (7.14), 1.263 (16.00), 1.280 (7.23), 2.601 (1.10), 2.602 (1.08), 2.619 (3.24), 2.621 (3.35), 2.638 (3.29), 2.640 (3.34), 2.657 (1.02), 2.659 (1.03), 3.331 (8.78), 4.200 (1.95), 4.218 (6.25), 4.236 (6.29), 4.254 (1.95), 5.759 (0.98), 6.518 (4.92).

Intermediate 399 ethyl 4-bromo-5-ethyl-1-methyl-1H-pyrazole-3-carboxylate

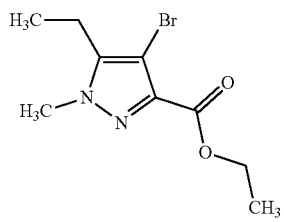

A solution of bromine in glacial acetic acid (23 ml, 1.0 M, 23 mmol) was added to a solution of ethyl 5-ethyl-1-methyl-1H-pyrazole-3-carboxylate (see intermediate 398; 2.10 g, 11.5 mmol) in glacial acetic acid (15 ml). The reaction mixture was stirred for 18 h at room temperature and was poured into ice water. An aqueous sodium thiosulfate solution (10%) was added, the mixture was extracted with ethyl acetate and the combined organic phases were washed with brine, filtered through a silicone filter and concentrated to give 2.97 g (91% purity, 90% yield) of the title compound.

LC-MS (Method 1): $R_t$=1.08 min; MS (ESIpos): m/z=261 [M+H]$^+$ $^1$H-NMR (400 MHz, DMSO-d6) δ[ppm]: 1.077 (2.69), 1.096 (6.29), 1.115 (2.81), 1.260 (3.48), 1.278 (7.87), 1.295 (3.68), 1.907 (1.63), 2.518 (0.62), 2.523 (0.41), 2.673 (0.89), 2.692 (2.71), 2.711 (2.65), 2.730 (0.75), 3.894 (16.00), 4.231 (1.11), 4.249 (3.60), 4.266 (3.59), 4.284 (1.10).

Intermediate 400

(4-bromo-5-ethyl-1-methyl-1H-pyrazol-3-yl)methanol

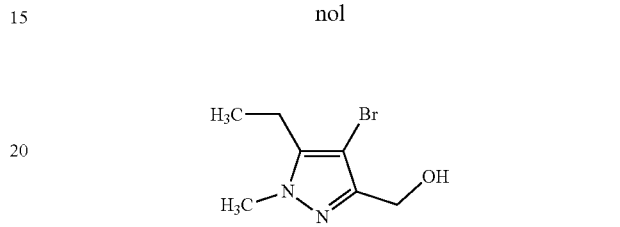

Lithium borohydride (310 mg, 14.2 mmol) was added to a solution of ethyl 4-bromo-5-ethyl-1-methyl-1H-pyrazole-3-carboxylate (see Intermediate 399; 2.97 g, 11.4 mmol) in THF (45 ml) and the reaction mixture was stirred for 20 h at room temperature and then for 22 h at 60° C. Lithium borohydride (62 mg, 2.8 mmol) was added and the reaction mixture was stirred for 24 h at room temperature and 3 h at 60° C. Saturated aqueous ammonium chloride solution was added and the mixture was extracted with ethyl acetate, the combined organic phases were washed with brine, filtered through a silicone filter and concentrated to give 2.18 g (90% purity, 79% yield) of the title compound.

LC-MS (Method 1): $R_t$=0.79 min; MS (ESIpos): m/z=219 [M+H]$^+$ $^1$H-NMR (400 MHz, DMSO-d6) δ[ppm]: 1.068 (3.21), 1.087 (7.19), 1.105 (3.37), 2.518 (0.44), 2.609 (1.02), 2.628 (3.36), 2.647 (3.29), 2.666 (1.04), 3.761 (16.00), 4.287 (4.77), 4.301 (4.91), 4.941 (1.34), 4.955 (2.69), 4.969 (1.21).

Intermediate 401 ethyl 7-[5-ethyl-3-(hydroxymethyl)-1-methyl-1H-pyrazol-4-yl]-3-[3-(naphthalen-1-yloxy) propyl]-1H-indole-2-carboxylate

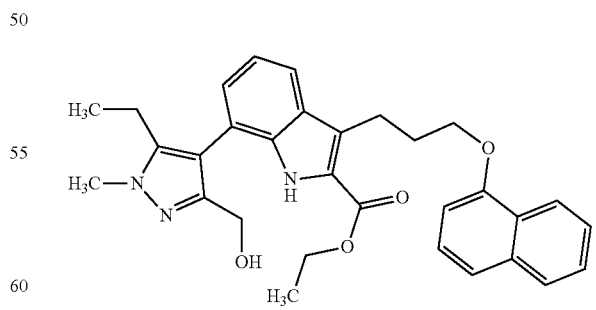

XPhos Pd G2 (see abbreviation list, 89.8 mg, 114 μmol) was added to a degassed mixture of ethyl 3-[3-(naphthalen-1-yloxy)propyl]-7-(4,4,5,5-tetramethyl-1,3,2-dioxaborolan-2-yl)-1H-indole-2-carboxylate (see Intermediate 5; 1.14 g, 2.28 mmol), (4-bromo-5-ethyl-1-methyl-1H-pyrazol-3-yl)

methanol (see Intermediate 400; 500 mg, 2.28 mmol) and an aqueous potassium phosphate solution (9.1 ml, 0.50 M, 4.6 mmol) in THF (10 ml), and the mixture was stirred for 2 h at 45° C. Water and brine were added, the mixture was extracted with ethyl acetate, the combined organic phases were filtered through a silicone filter and concentrated. Purification by flash chromatography on silica gel (ethyl acetate/hexanes) yielded 965 mg (100% purity, 83% yield) of the title compound.

LC-MS (Method 1): $R_t$=1.59 min; MS (ESIpos): m/z=513 [M+H]$^+$ $^1$H-NMR (400 MHz, DMSO-d6) δ[ppm]: 1.008 (2.80), 1.026 (6.39), 1.045 (2.92), 1.154 (1.88), 1.172 (3.96), 1.189 (1.99), 1.252 (4.63), 1.270 (10.37), 1.288 (4.75), 1.987 (7.01), 2.215 (0.99), 2.232 (1.33), 2.251 (1.02), 2.518 (1.78), 2.523 (1.29), 2.553 (0.93), 2.572 (0.86), 3.370 (1.29), 3.642 (0.52), 3.840 (16.00), 3.999 (0.52), 4.017 (1.58), 4.035 (1.58), 4.053 (0.54), 4.202 (1.97), 4.217 (4.20), 4.232 (2.33), 4.239 (5.11), 4.257 (4.48), 4.274 (1.35), 5.616 (0.77), 5.627 (1.92), 5.638 (0.75), 5.758 (1.60), 6.908 (1.78), 6.925 (1.88), 7.082 (2.91), 7.087 (2.98), 7.096 (5.65), 7.104 (0.59), 7.373 (1.31), 7.393 (2.48), 7.412 (2.01), 7.451 (2.57), 7.472 (1.43), 7.494 (0.56), 7.507 (1.51), 7.511 (1.47), 7.514 (1.87), 7.523 (3.30), 7.531 (1.96), 7.533 (1.63), 7.538 (1.69), 7.551 (0.57), 7.666 (1.31), 7.679 (1.35), 7.690 (1.17), 7.861 (1.45), 7.870 (0.77), 7.878 (1.22), 7.884 (1.26), 8.237 (1.27), 8.243 (1.17), 8.253 (0.61), 8.261 (1.22), 11.208 (2.51).

Intermediate 402

(rac)-ethyl (11Z)-3-ethyl-2-methyl-7-[3-(naphthalen-1-yloxy)propyl]-2,10,13,15-tetrahydropyrazolo[4',3':9,10][1,6]oxazacycloundecino[8,7,6-hi]indole-8-carboxylate

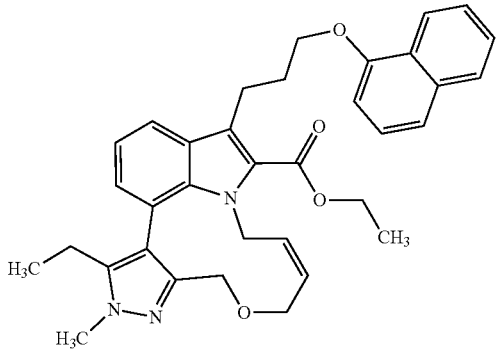 [SMILES: CCOC(=O)c1c(CCCOc2cccc3ccccc23)c2cccc3c2n1C/C=C\COCc1nn(C)c(CC)c1-3]

A mixture of ethyl 7-[5-ethyl-3-(hydroxymethyl)-1-methyl-1H-pyrazol-4-yl]-3-[3-(naphthalen-1-yloxy)propyl]-1H-indole-2-carboxylate (see Intermediate 401; 955 mg, 1.87 mmol), (2Z)-1,4-dichlorobut-2-ene (290 μl, 2.8 mmol), caesium carbonate (3.04 g, 9.33 mmol) and sodium iodide (560 mg, 3.73 mmol) in acetonitrile (10 ml) was stirred for 21 h at room temperature and for 5 h at 65° C. Water was added, the mixture was extracted with ethyl acetate, the combined organic phases were washed with brine, filtered through a silicone filter and concentrated. Purification by flash chromatography on silica gel (ethyl acetate/hexanes) yielded 675 mg (99% purity, 64% yield) of the title compound.

LC-MS (Method 1): $R_t$=1.66 min; MS (ESIpos): m/z=565 [M+H]$^+$ $^1$H-NMR (400 MHz, DMSO-d6) δ[ppm]: 0.820 (3.19), 0.839 (7.40), 0.858 (3.36), 1.154 (0.56), 1.172 (1.08), 1.189 (0.56), 1.266 (4.77), 1.284 (10.52), 1.301 (4.89), 1.987 (1.98), 2.161 (0.43), 2.180 (0.80), 2.198 (1.51), 2.217 (1.86), 2.228 (1.94), 2.236 (1.53), 2.246 (2.18), 2.264 (1.27), 2.284 (0.54), 2.518 (2.33), 2.523 (1.59), 3.292 (0.69), 3.308 (1.23), 3.371 (0.54), 3.571 (0.63), 3.583 (0.76), 3.601 (1.01), 3.615 (0.88), 3.737 (0.88), 3.765 (1.32), 3.794 (0.80), 3.870 (16.00), 4.017 (0.47), 4.035 (0.47), 4.227 (3.38), 4.244 (3.71), 4.253 (2.67), 4.260 (4.29), 4.271 (2.01), 4.276 (0.76), 4.288 (0.69), 4.295 (1.77), 4.312 (1.68), 4.321 (0.86), 4.330 (0.52), 4.339 (0.88), 4.354 (2.85), 4.386 (1.85), 4.747 (0.43), 4.773 (0.50), 4.785 (0.97), 4.811 (1.12), 4.848 (1.14), 4.884 (0.48), 5.106 (0.48), 5.113 (0.52), 5.133 (0.93), 5.140 (0.99), 5.159 (0.56), 5.166 (0.54), 5.270 (0.41), 5.285 (0.45), 5.298 (0.71), 5.311 (0.71), 5.758 (0.63), 6.879 (1.85), 6.882 (1.96), 6.897 (2.26), 6.900 (2.14), 6.917 (1.86), 6.934 (1.98), 7.072 (1.85), 7.093 (2.29), 7.110 (1.62), 7.377 (1.34), 7.398 (2.55), 7.417 (2.05), 7.456 (2.74), 7.477 (1.51), 7.494 (0.60), 7.507 (1.55), 7.511 (1.49), 7.516 (1.85), 7.523 (3.43), 7.531 (1.90), 7.535 (1.66), 7.540 (1.73), 7.552 (0.65), 7.754 (1.90), 7.757 (2.00), 7.774 (1.86), 7.777 (1.79), 7.864 (1.57), 7.872 (0.84), 7.882 (1.34), 7.887 (1.34), 8.222 (1.32), 8.229 (1.29), 8.239 (0.69), 8.246 (1.29).

Intermediate 403

(rac)-ethyl 3-ethyl-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylate

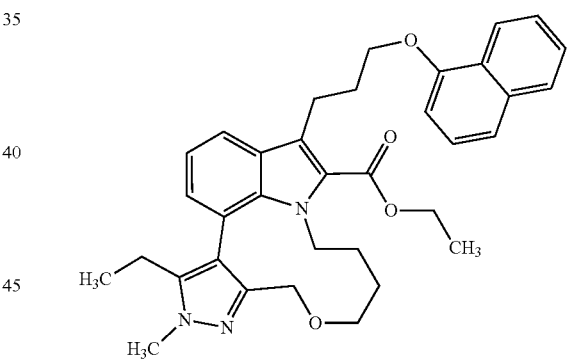

Palladium on charcoal (125 mg, 10% purity, 117 μmol) was added to a solution of ethyl (11Z)-3-ethyl-2-methyl-7-[3-(naphthalen-1-yloxy)propyl]-2,10,13,15-tetrahydropyrazolo[4',3':9,10][1,6]oxazacycloundecino[8,7,6-hi]indole-8-carboxylate (see Intermediate 402; 660 mg, 1.17 mmol) in THF (4.4 mL) and ethanol (22 mL) and the mixture was vigorously stirred under an atmosphere of hydrogen at room temperature and 20 bar for 22 h. The catalyst was filtered off and the filtrate was concentrated. Purification by by flash chromatography on silica gel (ethyl acetate/hexanes) yielded 470 mg (97% purity, 69% yield) of the title compound.

LC-MS (Method 1): $R_t$=1.74 min; MS (ESIpos): m/z=567 [M+H]$^+$ $^1$H-NMR (400 MHz, DMSO-d6) δ[ppm]: 0.815 (3.13), 0.834 (7.19), 0.853 (3.20), 0.934 (0.41), 0.953 (0.45), 1.153 (2.06), 1.172 (3.95), 1.189 (2.28), 1.197 (0.70), 1.211 (0.59), 1.224 (0.58), 1.236 (0.53), 1.260 (4.99), 1.277 (10.55), 1.295 (5.13), 1.880 (1.25), 1.986 (6.70), 2.116 (0.53), 2.135

(0.82), 2.153 (1.20), 2.172 (1.03), 2.192 (0.89), 2.211 (1.88), 2.230 (2.14), 2.247 (1.36), 2.266 (0.64), 2.518 (1.53), 2.522 (1.00), 3.102 (0.75), 3.115 (0.71), 3.128 (0.51), 3.242 (0.44), 3.263 (0.97), 3.278 (1.53), 3.297 (1.53), 3.828 (16.00), 3.947 (0.75), 3.958 (0.46), 3.971 (0.51), 3.999 (0.61), 4.016 (1.61), 4.034 (1.57), 4.052 (0.51), 4.160 (2.40), 4.191 (3.27), 4.201 (2.29), 4.209 (2.25), 4.220 (2.92), 4.229 (2.40), 4.236 (1.30), 4.246 (2.00), 4.264 (0.67), 4.267 (0.63), 4.286 (1.66), 4.303 (1.60), 4.312 (0.91), 4.321 (0.48), 4.330 (0.88), 4.495 (2.29), 4.526 (1.98), 6.891 (1.87), 6.909 (2.03), 6.937 (1.80), 6.939 (1.81), 6.954 (2.37), 6.957 (2.18), 7.055 (1.85), 7.075 (2.27), 7.093 (1.50), 7.367 (1.31), 7.387 (2.52), 7.407 (1.97), 7.453 (2.64), 7.473 (1.54), 7.504 (0.50), 7.516 (1.88), 7.519 (2.30), 7.529 (2.78), 7.539 (2.25), 7.542 (2.00), 7.554 (0.51), 7.727 (1.93), 7.730 (1.95), 7.747 (1.85), 7.750 (1.74), 7.863 (1.48), 7.867 (1.01), 7.876 (1.15), 7.880 (0.93), 7.887 (1.25), 8.244 (1.33), 8.255 (1.06), 8.269 (1.20).

Intermediate 404 tert-Butyl (5-hydroxypentyl)methylcarbamate

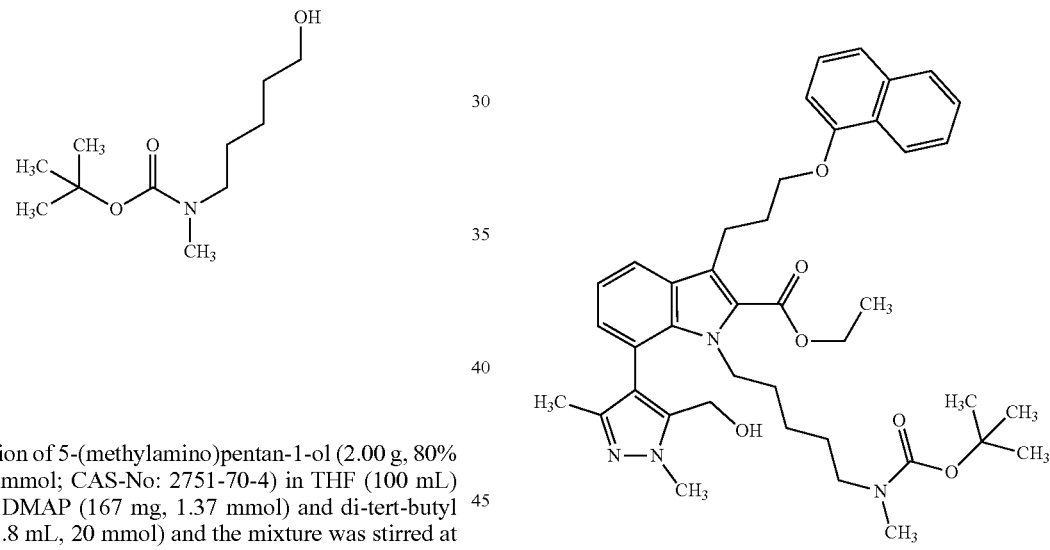

To a solution of 5-(methylamino)pentan-1-ol (2.00 g, 80% purity, 13.7 mmol; CAS-No: 2751-70-4) in THF (100 mL) were added DMAP (167 mg, 1.37 mmol) and di-tert-butyl carbonate (4.8 mL, 20 mmol) and the mixture was stirred at RT overnight. After concentration, the residue was purified by chromatography (Biotage SNAP cartridge silica 100 g, ethyl acetate:n-hexane) to give 2.01 g (68% yield) of the title compound.

MS: m/z=218.4 [M+H]$^+$.

Intermediate 405 tert-Butyl (5-bromopentyl)methylcarbamate

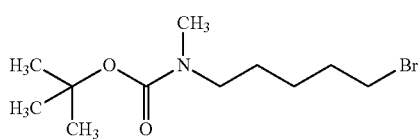

To a mixture of tert-butyl (5-hydroxypentyl)methylcarbamate (4.37 g, 20.1 mmol) and triphenylphosphane (7.91 g, 30.2 mmol; see Intermediate 404) in dichloromethane (90 mL) was added at 0° C. tetrabromomethane (10.0 g, 30.2 mmol) over 30 minutes. The mixture was stirred at RT for 4 hours, concentrated and the residue was purified by chromatography (Biotage SNAP cartridge silica 340 g, ethyl acetate:n-hexane) to give 5.31 g (94% yield) of the title compound.

MS: m/z=280.2 [M+H]$^+$.

Intermediate 406

Ethyl 1-{5-[(tert-butoxycarbonyl)(methyl)amino] pentyl}-7-[5-(hydroxymethyl)-1,3-dimethyl-1H-pyrazol-4-yl]-3-[3-(naphthalen-1-yloxy)propyl]-1H-indole-2-carboxylate

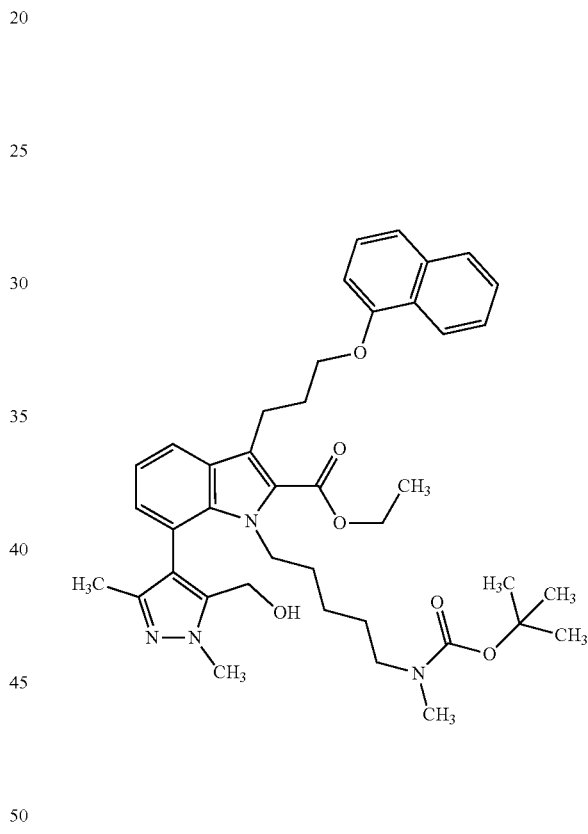

To a solution of ethyl 7-[5-(hydroxymethyl)-1,3-dimethyl-1H-pyrazol-4-yl]-3-[3-(naphthalen-1-yloxy)propyl]-1H-indole-2-carboxylate (750 mg, 1.51 mmol; see Intermediate 1-39) in DMA (16 mL) were added caesium carbonate (2.46 g, 7.54 mmol) and after 10 minutes of stirring a solution of tert-butyl (5-bromopentyl)methylcarbamate (1.27 g, 4.52 mmol; see Intermediate 405) in DMA (4.0 mL). The mixture was stirred at RT for 2.5 days, poured into water, extracted with ethyl acetate, the organic layer was washed with water and brine and dried over sodium sulfate. After filtration and concentration, the residue was purified by chromatography (Biotage SNAP cartridge silica 100 g, ethyl acetate:n-hexane) to give 824 mg (78% yield) of the title compound.

MS: m/z=697.6 [M+H]$^+$.

721

Intermediate 407

Ethyl 1-{5-[(tert-butoxycarbonyl)(methyl)amino]pentyl}-7-[5-(chloromethyl)-1,3-dimethyl-1H-pyrazol-4-yl]-3-[3-(naphthalen-1-yloxy)propyl]-1H-indole-2-carboxylate

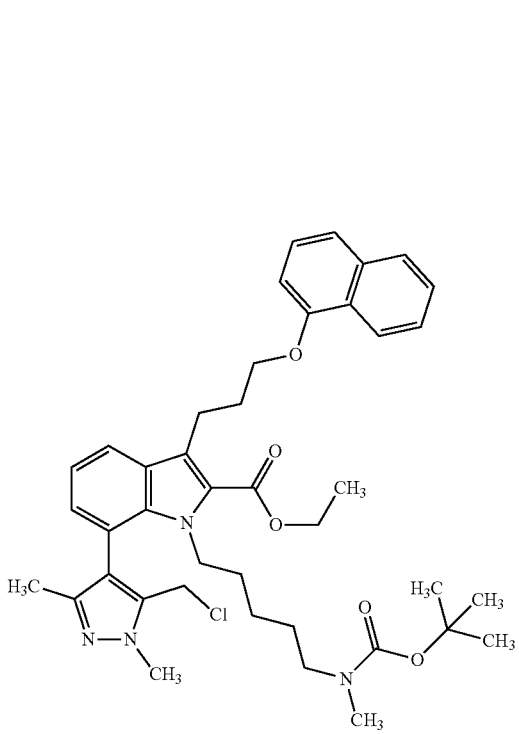 [SMILES: CCOC(=O)c1c(CCCOc2cccc3ccccc23)c2cccc(-c3c(C)nn(C)c3CCl)c2n1CCCCCN(C)C(=O)OC(C)(C)C]

A mixture of ethyl 1-{5-[(tert-butoxycarbonyl)(methyl)amino]pentyl}-7-[5-(hydroxymethyl)-1,3-dimethyl-1H-pyrazol-4-yl]-3-[3-(naphthalen-1-yloxy)propyl]-1H-indole-2-carboxylate (821 mg, 1.18 mmol; see Intermediate 406), tetrachloromethane (450 µL, 4.7 mmol), pyridine (380 µL, 4.7 mmol) and acetonitrile (11 mL) was cooled to 0° C. Triphenylphosphine (1.24 g, 4.71 mmol) was added and the reaction mixture was stirred at RT overnight. After concentration, the residue was purified by chromatography (Biotage SNAP cartridge silica 100 g, ethyl acetate:n-hexane) to give 714 mg (85% yield) of the title compound.
MS: m/z=715.5 [M+H]$^+$.

722

Intermediate 408

Ethyl 7-[5-(chloromethyl)-1,3-dimethyl-1H-pyrazol-4-yl]-1-[5-(methylamino)pentyl]-3-[3-(naphthalen-1-yloxy)propyl]-1H-indole-2-carboxylate hydrochloric acid salt

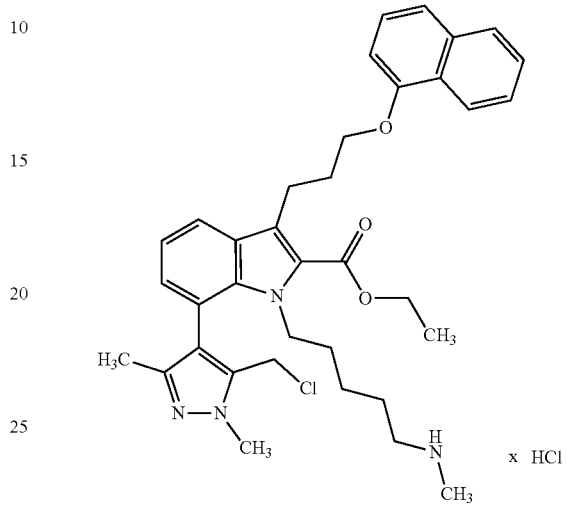

To a solution of ethyl 1-{5-[(tert-butoxycarbonyl)(methyl)amino]pentyl}-7-[5-(chloromethyl)-1,3-dimethyl-1H-pyrazol-4-yl]-3-[3-(naphthalen-1-yloxy)propyl]-1H-indole-2-carboxylate (714 mg, 998 µmol; see Intermediate 407) in ethanol (18 mL) was added hydrogen chloride (8.7 mL, 4.0 M solution in dioxane, 35 mmol) and the mixture was stirred at RT overnight. The mixture was concentrated to give 672 mg of the title compound that was used without further purification.
MS: m/z=615.4 [M+H]$^+$.

Intermediate 409

(rac)-Ethyl 1,3,15-trimethyl-7-[3-(naphthalen-1-yloxy)propyl]-1,10,11,12,13,14,15,16-octahydropyrazolo[4',3':4,5][1,7]diazacyclododecino[3,2,1-hi]indole-8-carboxylate

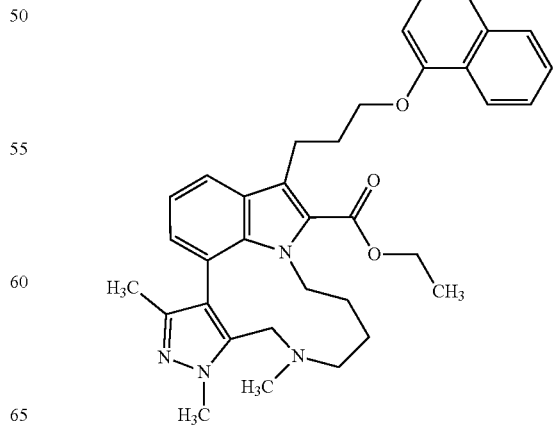

To a solution of ethyl 7-[5-(chloromethyl)-1,3-dimethyl-1H-pyrazol-4-yl]-1-[5-(methylamino)pentyl]-3-[3-(naphthalen-1-yloxy)propyl]-1H-indole-2-carboxylate hydrochloric acid salt (670 mg; see Intermediate 408) in DMA (35 mL) were added sodium iodide (224 mg, 1.50 mmol) and caesium carbonate (1.62 g, 4.99 mmol), and the mixture was stirred at 65° C. for 2.5 days. The mixture was poured into water, extracted with ethyl acetate and the organic layer was dried over sodium sulfate. After filtration and concentration the residue was purified by chromatography (Biotage SNAP cartridge silica 100 g, ethanol:dichloromethane) to give the title compound (613 mg).

MS: m/z=579.5 [M+H]$^+$.

Intermediate 410 ethyl 1-[2-(dimethylamino)ethyl]-5-methyl-1H-pyrazole-3-carboxylate

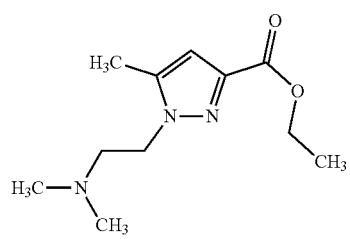 [SMILES: CCOC(=O)c1cc(C)n(CCN(C)C)n1]

A mixture of ethyl 2,4-dioxopentanoate (3.83 g, 24.2 mmol) and 2-hydrazinyl-N,N-dimethylethanamine (2.50 g, 24.2 mmol, CAS No 1754-57-0) in acetic acid (35 ml) was stirred at 100° C. for 3 h. Upon cooling, the mixture was concentrated. Saturated aqueous sodium bicarbonate solution was added and the mixture was extracted with a mixture of dichloromethane and 2-propanol (4:1). The combined organic phases were filtered through a silicone filter and concentrated. The residue was purified by flash chromatography (110 g Biotage SNAP cartridge NH$_2$ silica, hexanes/ethyl acetate gradient, 0%→60% ethyl acetate) to give the title compound 3.35 g (61% yield) together with the regioisomer ethyl 1-[2-(dimethylamino)ethyl]-3-methyl-1H-pyrazole-5-carboxylate 1.27 g, (23% yield, see Intermediate 411).

LC-MS (Method 1): R$_t$=0.56 min; MS (ESIpos): m/z=226 [M+H]$^+$ $^1$H-NMR (400 MHz, DMSO-d6) δ[ppm]: 1.246 (2.29), 1.263 (5.03), 1.281 (2.33), 2.163 (16.00), 2.292 (5.65), 2.518 (0.53), 2.523 (0.37), 2.571 (0.91), 2.587 (1.97), 2.605 (0.95), 4.141 (0.99), 4.158 (2.01), 4.174 (0.97), 4.201 (0.69), 4.219 (2.22), 4.237 (2.21), 4.255 (0.68), 6.492 (1.57).

Intermediate 411 ethyl 1-[2-(dimethylamino)ethyl]-3-methyl-1H-pyrazole-5-carboxylate

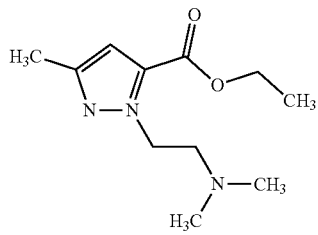

The title compound was isolated as a side product in the synthesis of ethyl 1-[2-(dimethylamino)ethyl]-5-methyl-1H-pyrazole-3-carboxylate (see Intermediate 410).

LC-MS (Method 1): R$_t$=0.63 min; MS (ESIpos): m/z=226 [M+H]$^+$ $^1$H-NMR (400 MHz, DMSO-d6) δ[ppm]: 1.265 (2.19), 1.283 (4.61), 1.301 (2.21), 2.144 (16.00), 2.163 (0.48), 2.169 (6.53), 2.518 (0.39), 2.523 (0.27), 2.548 (0.92), 2.565 (1.63), 2.583 (0.95), 4.245 (0.70), 4.263 (2.24), 4.281 (2.23), 4.298 (0.70), 4.460 (0.95), 4.477 (1.60), 4.495 (0.95), 6.621 (1.92).

Intermediate 412 ethyl 4-bromo-1-[2-(dimethylamino)ethyl]-5-methyl-1H-pyrazole-3-carboxylate

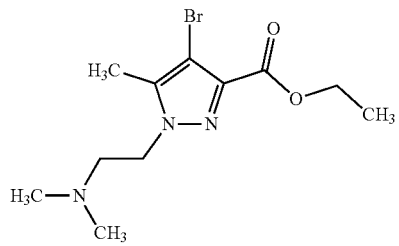 [SMILES: CCOC(=O)c1nn(CCN(C)C)c(C)c1Br]

A solution of bromine in acetic acid (30 ml, 1.0 M, 30 mmol) was added to a solution of ethyl 1-[2-(dimethylamino)ethyl]-5-methyl-1H-pyrazole-3-carboxylate (see Intermediate 410; 3.35 g, 14.9 mmol) in acetic acid (85 ml) at 0° C., and the mixture was stirred for 4 h at room temperature. The precipitate was collected by filtration and washed with hexanes and then dissolved in ethyl acetate. The ethyl acetate phase was washed with saturated aqueous sodium bicarbonate solution, filtered through a silicone filter and concentrated to give the title compound 3.74 g (83% yield).

LC-MS (Method 1): R$_t$=0.70 min; MS (ESIpos): m/z=304 [M+H]$^+$

1H-NMR (400 MHz, DMSO-d6): d [ppm]=4.31-4.21 (m, 4H), 2.72-2.59 (m, 2H), 2.30 (s, 3H), 2.20 (br s, 6H), 1.28 (t, 3H)

Intermediate 413

{4-bromo-1-[2-(dimethylamino)ethyl]-5-methyl-1H-pyrazol-3-yl}methanol

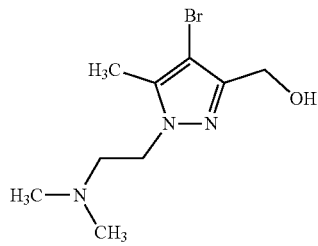

The title compound (2.29 g, 71% yield) was prepared in analogy to the synthesis of Intermediate 94 using ethyl 4-bromo-1-[2-(dimethylamino)ethyl]-5-methyl-1H-pyrazole-3-carboxylate (3.74 g, 12.3 mmol; see Intermediate 412) as starting material.

LC-MS (Method 1): $R_t$=0.86 min; MS (ESIpos): m/z=262 [M+H]$^+$ $^1$H-NMR (400 MHz, DMSO-d$_6$): δ [ppm]=5.00 (t, 1H), 4.47-4.39 (m, 2H), 4.32 (d, 2H), 3.08-3.01 (m, 2H), 2.56 (s, 6H), 2.27 (s, 3H)

Intermediate 414 ethyl 4-bromo-1-[2-(dimethylamino)ethyl]-3-methyl-1H-pyrazole-5-carboxylate

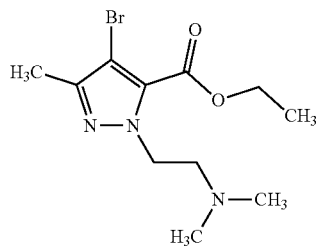

A solution of bromine in acetic acid (10 ml, 1.0 M, 10 mmol) was added to a solution of ethyl 1-[2-(dimethylamino)ethyl]-3-methyl-1H-pyrazole-5-carboxylate (1.14 g, 5.06 mmol; see Intermediate 411) in acetic acid (29 ml) at 0° C., and the mixture was stirred for 4 h at room temperature. For work-up, ice water was added, followed by aqueous saturated sodium thiosulfate solution, and pH was adjusted at pH>7 by the addition of saturated aqueous sodium bicarbonate solution. The mixture was extracted with ethyl acetate and the combined organic phases were filtered through a silicone filter and concentrated to give the title compound (1.79 g).

LC-MS (Method 1): $R_t$=0.74 min; MS (ESIpos): m/z=304 [M+H]$^+$ $^1$H-NMR (400 MHz, DMSO-d$_6$): δ [ppm]=4.47 (t, 2H), 4.33 (q, 2H), 2.57-2.52 (m, 2H), 2.16 (s, 3H), 2.13 (s, 6H), 1.33 (t, 3H)

Intermediate 415

{4-bromo-1-[2-(dimethylamino)ethyl]-3-methyl-1H-pyrazol-5-yl}methanol

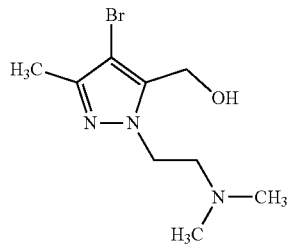

Lithium aluminum hydride (5.9 ml, 1.0 M solution in THF, 5.9 mmol) was added to a solution of ethyl 4-bromo-1-[2-(dimethylamino)ethyl]-3-methyl-1H-pyrazole-5-carboxylate (1.79 g, 5.88 mmol; see Intermediate 414) in THF (48 ml) and the mixture was stirred for 1 h at 0° C. For work-up, sodium sulfate was added and the mixture was stirred for 1 h. Solids were filtered off and the filtrate was concentrated. The residue was purified by flash chromatography (50 g Biotage SNAP cartridge silica, dichloromethane/ethanol gradient, 0%→15% ethanol) to give the title compound 1.03 g (67% yield).

LC-MS (Method 1): $R_t$=0.54 min; MS (ESIpos): m/z=262 [M+H]$^+$ $^1$H-NMR (400 MHz, DMSO-d$_6$): δ [ppm]=5.62 (br s, 1H), 4.42 (s, 2H), 4.17 (t, 2H), 2.58 (t, 2H), 2.16 (s, 6H), 2.10 (s, 3H)

Intermediate 416

(3-bromo-6,7-dihydro-5H-pyrazolo[5,1-b][1,3]oxazin-2-yl)methanol

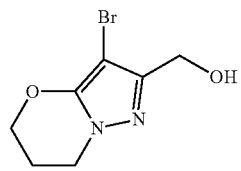 [SMILES: OCc1nn2c(c1Br)OCCC2]

The title compound 740 mg (92% yield) was prepared in analogy to the synthesis of Intermediate 94 using ethyl 3-bromo-6,7-dihydro-5H-pyrazolo[5,1-b][1,3]oxazine-2-carboxylate (950 mg, 3.45 mmol, CAS No 1779121-90-2) as starting material.

$^1$H-NMR (400 MHz, DMSO-d6) δ[ppm]: 2.144 (1.37), 2.159 (3.89), 2.169 (4.08), 2.174 (4.00), 2.185 (4.01), 2.201 (1.41), 2.518 (1.25), 2.523 (0.85), 4.020 (5.67), 4.035 (11.76), 4.051 (5.33), 4.236 (15.30), 4.250 (16.00), 4.316 (6.18), 4.327 (4.58), 4.329 (6.32), 4.342 (6.13), 4.949 (4.44), 4.962 (9.52), 4.976 (4.12).

Intermediate 417 ethyl 3-bromo-6,7-dihydro-4H-pyrazolo[5,1-c][1,4]oxazine-2-carboxylate

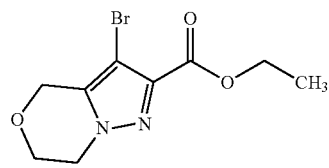

N-Bromosuccinimide (1.81 g, 10.2 mmol) was added to a solution of ethyl 6,7-dihydro-4H-pyrazolo[5,1-c][1,4]oxazine-2-carboxylate (1.90 g, 9.68 mmol, CAS No 623565-57-1) in acetonitrile (90 ml) and the mixture was stirred for 4 h at 50° C. For work-up, the mixture was concentrated, water was added and the mixture was extracted with a mixture of dichloromethane and 2-propanol (4:1). The organic phase was filtered through a silicone filter and concentrated to give the title compound (3.10 g), which was used in the next step without further purification.

LC-MS (Method 1): $R_t$=0.93 min; MS (ESIpos): m/z=275 [M+H]$^+$ $^1$H-NMR (400 MHz, DMSO-d6) δ[ppm]: 1.026 (3.17), 1.041 (3.12), 1.271 (6.96), 1.289 (16.00), 1.306 (7.36), 2.518 (0.82), 2.562 (10.25), 4.082 (1.55), 4.095 (3.90), 4.098 (2.24), 4.108 (3.15), 4.179 (2.70), 4.192 (3.22), 4.205 (1.42), 4.252 (2.13), 4.270 (7.00), 4.288 (6.92), 4.305 (2.07), 4.731 (10.44).

Intermediate 418

(3-bromo-6,7-dihydro-4H-pyrazolo[5,1-c][1,4]oxazin-2-yl)methanol

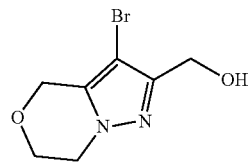 [SMILES: OCc1nn2c(c1Br)COCC2]

The title compound (1.17 g) was prepared in analogy to the synthesis of Intermediate 94 using ethyl 3-bromo-6,7-dihydro-4H-pyrazolo[5,1-c][1,4]oxazine-2-carboxylate (3.24 g, 11.8 mmol; see Intermediate 417) as starting material.

$^1$H-NMR (400 MHz, DMSO-de): δ [ppm]=5.05 (t, 1H), 4.68 (s, 2H), 4.34 (d, 2H), 4.05 (s, 4H)

Intermediate 419 ethyl 3-bromo-4,5,6,7-tetrahydropyrazolo[1,5-a]pyridine-2-carboxylate

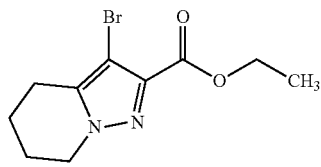

N-Bromosuccinimide (962 mg, 5.41 mmol) was added to a solution of ethyl 4,5,6,7-tetrahydropyrazolo[1,5-a]pyridine-2-carboxylate (1.00 g, 5.15 mmol, CAS No 307307-84-2) in acetonitrile (48 ml) and the mixture was stirred for 4 h at 50° C. For work-up, the mixture was concentrated, water was added and the mixture was extracted with a mixture of dichloromethane and 2-propanol (4:1). The organic phase was filtered through a silicone filter and concentrated to give the title compound (1.53 g) which was used in the next step without further purification.

LC-MS (Method 1): $R_t$=1.09 min; MS (ESIpos): m/z=273 [M+H]$^+$ $^1$H-NMR (400 MHz, DMSO-d$_6$): δ [ppm]=4.26 (q, 2H), 4.12 (t, 2H), 2.64 (t, 2H), 2.01-1.94 (m, 2H), 1.86-1.78 (m, 2H), 1.28 (t, 3H)

Intermediate 420

(3-bromo-4,5,6,7-tetrahydropyrazolo[1,5-a]pyridin-2-yl)methanol

The title compound (980 mg) was prepared in analogy to the synthesis of Intermediate 94 using ethyl 3-bromo-4,5,6,7-tetrahydropyrazolo[1,5-a]pyridine-2-carboxylate (1.53 g, 5.60 mmol; see intermediate 419) as starting material.

$^1$H-NMR (400 MHz, DMSO-d$_6$): δ [ppm]=4.96 (t, 1H), 4.31 (d, 2H), 3.99 (t, 2H), 2.59 (t, 2H), 1.97-1.89 (m, 2H), 1.85-1.73 (m, 2H)

Intermediate 421

(rac)-ethyl 3-methyl-7-[3-(naphthalen-1-yloxy)propyl]-2-(2,2,2-trifluoroethyl)-2,10,11,12,13,15-hexahydropyrazolo[4',3':9,10][1,6]oxazacycloundecino[8,7,6-hi]indole-8-carboxylate

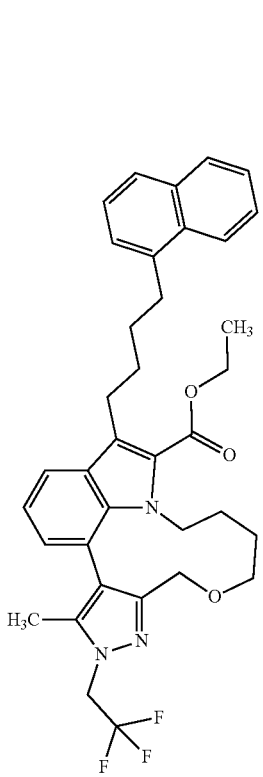 [SMILES: CCOC(=O)c1c(CCCCc2cccc3ccccc23)c2cccc3c2n1CCCCOCc1nn(CC(F)(F)F)c(C)c1-3]

The title compound (410 mg) was prepared in analogy to the synthesis of Intermediate 174 using (rac)-ethyl (11Z)-3-methyl-7-[3-(naphthalen-1-yloxy)propyl]-2-(2,2,2-trifluoroethyl)-2,10,13,15-tetrahydropyrazolo[4',3':9,10][1,6]oxazacycloundecino[8,7,6-hi]indole-8-carboxylate (280 mg, 453 μmol; see intermediate 171) as starting material.

LC-MS (Method 1): $R_t$=1.74 min; MS (ESIpos): m/z=620 [M+H]$^+$

Intermediate 422 ethyl 7-{1-[2-(dimethylamino)ethyl]-3-(hydroxymethyl)-5-methyl-1H-pyrazol-4-yl}-3-[3-(naphthalen-1-yloxy)propyl]-1H-indole-2-carboxylate

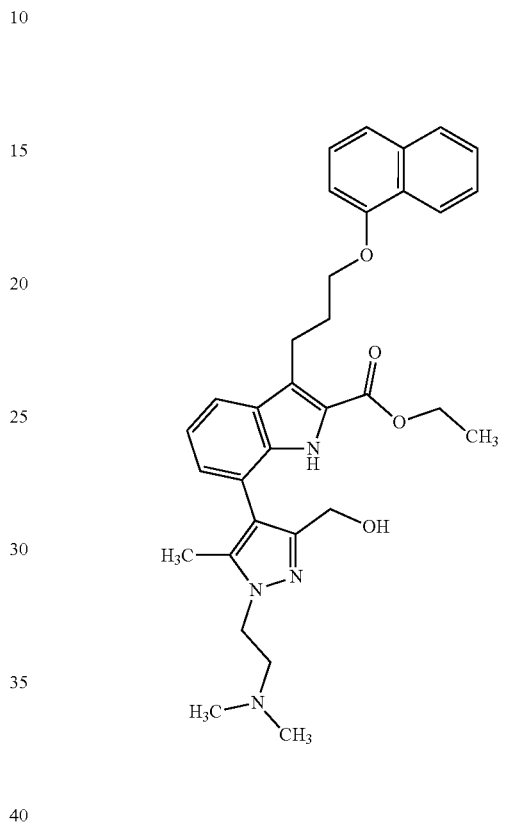

The title compound (1.51 g, 63% yield) was prepared in analogy to the synthesis of Intermediate 199 using ethyl 3-[3-(naphthalen-1-yloxy)propyl]-7-(4,4,5,5-tetramethyl-1,3,2-dioxaborolan-2-yl)-1H-indole-2-carboxylate (2.15 g, 4.31 mmol; see intermediate 5) and {4-bromo-1-[2-(dimethylamino)ethyl]-5-methyl-1H-pyrazol-3-yl}methanol (1.13 g, 4.31 mmol; see intermediate 413) as starting materials.

$^1$H-NMR (400 MHz, DMSO-d6) δ[ppm]: 1.066 (3.83), 1.154 (1.04), 1.172 (1.98), 1.190 (0.98), 1.256 (2.00), 1.274 (4.62), 1.292 (2.07), 1.988 (4.04), 2.154 (1.27), 2.191 (6.34), 2.224 (16.00), 2.250 (0.42), 2.518 (1.20), 2.523 (0.89), 2.658 (0.71), 2.669 (0.55), 2.675 (1.31), 2.693 (0.72), 3.358 (0.74), 3.374 (0.45), 3.939 (0.61), 4.017 (0.88), 4.035 (0.86), 4.150 (0.59), 4.167 (1.00), 4.185 (0.59), 4.200 (0.58), 4.215 (1.18), 4.224 (0.85), 4.230 (0.65), 4.242 (2.02), 4.259 (2.39), 4.277 (0.77), 5.760 (0.55), 5.763 (0.70), 6.908 (0.70), 6.925 (0.74), 7.080 (1.14), 7.084 (1.23), 7.094 (2.38), 7.373 (0.56), 7.394 (1.00), 7.412 (0.84), 7.450 (1.03), 7.471 (0.56), 7.504 (0.64), 7.508 (0.57), 7.513 (0.67), 7.521 (1.44), 7.528 (0.71), 7.533 (0.62), 7.537 (0.71), 7.660 (0.53), 7.669 (0.47), 7.673 (0.53), 7.682 (0.48), 7.860 (0.59), 7.878 (0.56), 7.884 (0.51), 8.229 (0.53), 8.234 (0.49), 8.253 (0.49), 11.353 (0.92).

731
Intermediate 423

(rac)-ethyl (11Z)-2-[2-(dimethylamino)ethyl]-3-methyl-7-[3-(naphthalen-1-yloxy)propyl]-2,10,13,15-tetrahydropyrazolo[4',3':9,10][1,6]oxazacycloundecino[8,7,6-hi]indole-8-carboxylate

732
Intermediate 424

(rac)-ethyl 2-[2-(dimethylamino)ethyl]-3-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylate

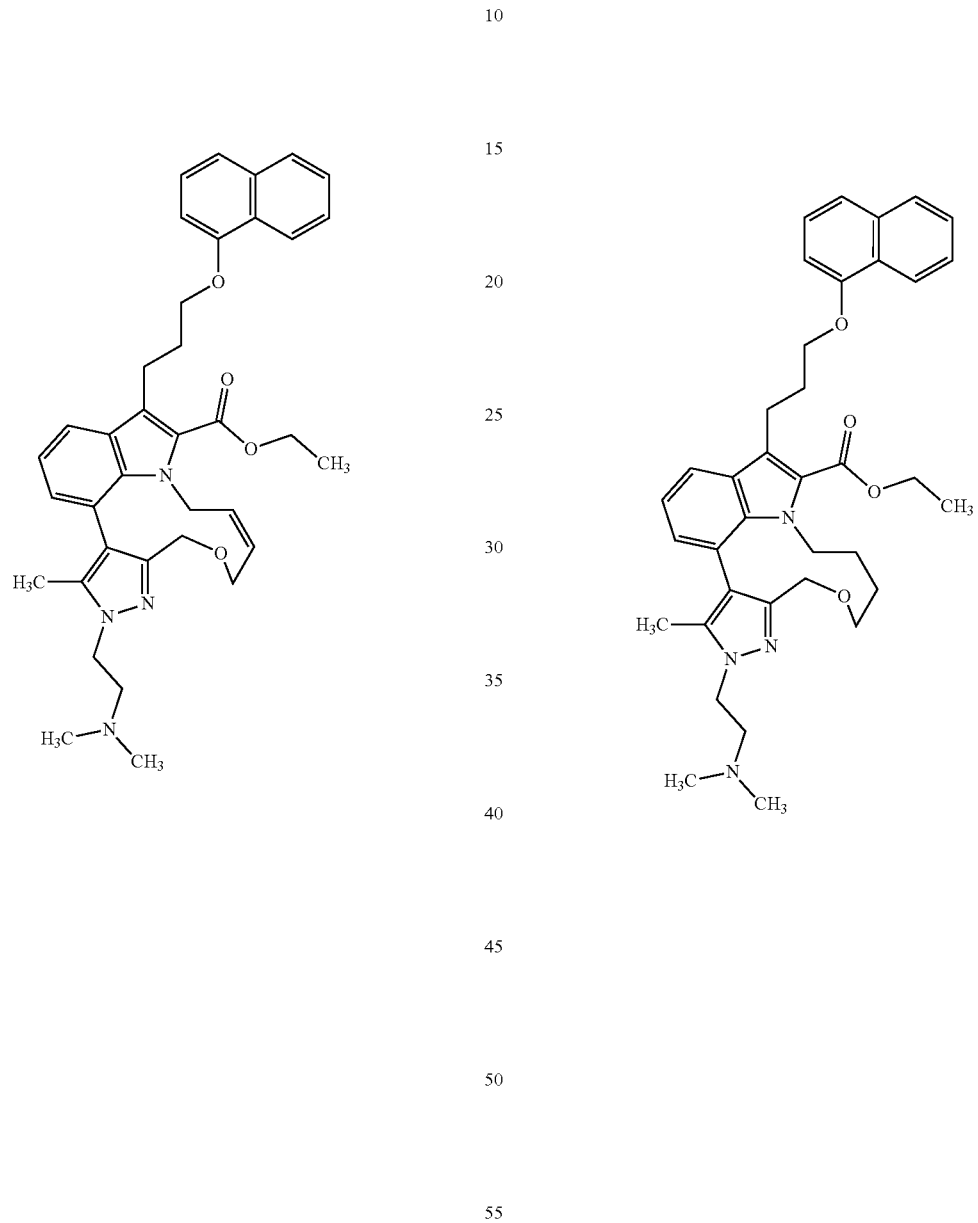

The title compound (70.0 mg, 9% yield) was prepared in analogy to the synthesis of Intermediate 200 using ethyl 7-{1-[2-(dimethylamino)ethyl]-3-(hydroxymethyl)-5-methyl-1H-pyrazol-4-yl}-3-[3-(naphthalen-1-yloxy)propyl]-1H-indole-2-carboxylate (750 mg, 1.35 mmol) as starting material. The crude product was purified by flash chromatography (25 g Biotage SNAP cartridge silica, dichloromethane/ethanol gradient, 0%→15% ethanol).

LC-MS (Method 1): Rt=1.50 min; MS (ESIpos): m/z=607 [M+H]$^+$

The title compound (90 mg) was prepared in analogy to the synthesis of Intermediate 174 using (rac)-ethyl (11Z)-2-[2-(dimethylamino)ethyl]-3-methyl-7-[3-(naphthalen-1-yloxy)propyl]-2,10,13,15-tetrahydropyrazolo[4',3':9,10][1,6]oxazacycloundecino[8,7,6-hi]indole-8-carboxylate (70.0 mg, 115 µmol) as starting material.

LC-MS (Method 2): R$_t$=1.71 min; MS (ESIpos): m/z=609 [M+H]$^+$

Intermediate 425 ethyl 7-{1-[2-(dimethylamino)ethyl]-5-(hydroxymethyl)-3-methyl-1H-pyrazol-4-yl}-3-[3-(naphthalen-1-yloxy)propyl]-1H-indole-2-carboxylate

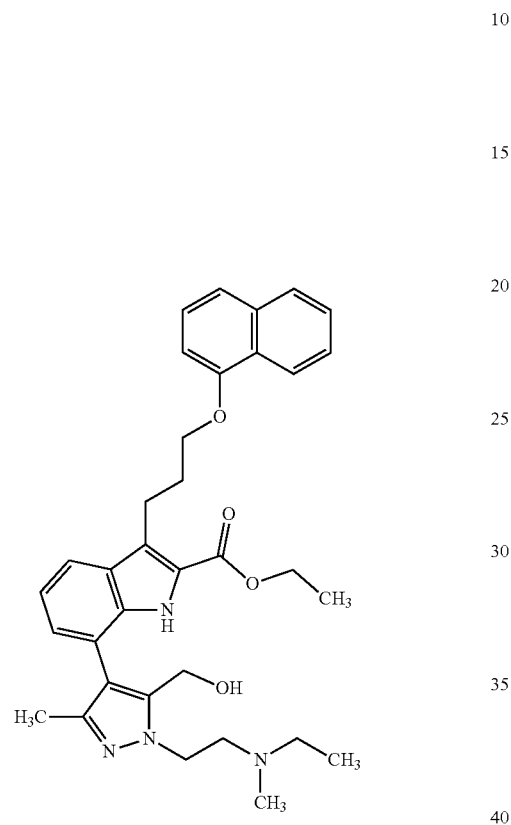

The title compound (2.28 g) was prepared in analogy to the synthesis of Intermediate 199 using ethyl 3-[3-(naphthalen-1-yloxy)propyl]-7-(4,4,5,5-tetramethyl-1,3,2-dioxaborolan-2-yl)-1H-indole-2-carboxylate (1.96 g, 3.93 mmol; see Intermediate 5) and {4-bromo-1-[2-(dimethylamino)ethyl]-3-methyl-1H-pyrazol-5-yl}methanol (1.03 g, 3.93 mmol; see Intermediate 415) as starting materials. The crude product was purified by flash chromatography (110 g Biotage SNAP cartridge $NH_2$ silica, ethyl acetate/ethanol gradient, 0%→10% ethanol).

LC-MS (Method 1): Rt=1.46 min; MS (ESIpos): m/z=555 [M+H]$^+$ $^1$H-NMR (400 MHz, DMSO-d$_6$): δ [ppm]=11.04 (s, 1H), 8.26-8.20 (m, 1H), 7.90-7.84 (m, 1H), 7.68 (d, 1H), 7.55-7.35 (m, 4H), 7.18-7.08 (m, 2H), 6.91 (d, 1H), 6.70 (br s, 1H), 4.35-4.16 (m, 7H), 3.41-3.34 (m, 2H), 2.72-2.66 (m, 2H), 2.27-2.21 (m, 7H), 2.10 (s, 3H), 1.27 (t, 3H)

Intermediate 426

(rac)-ethyl (11Z)-1-[2-(dimethylamino)ethyl]-3-methyl-7-[3-(naphthalen-1-yloxy)propyl]-1,10,13,15-tetrahydropyrazolo[4',3':9,10][1,6]oxazacycloundecino[8,7,6-hi]indole-8-carboxylate

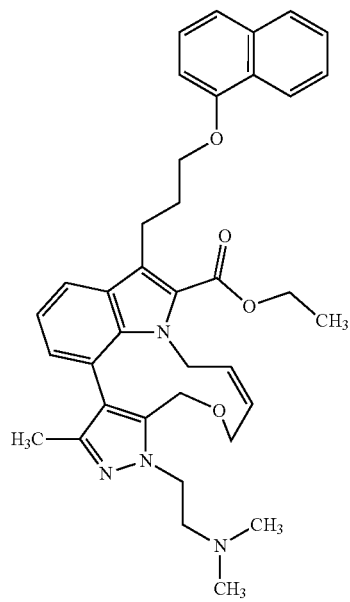 [SMILES: CCOC(=O)c1c(CCCOc2cccc3ccccc23)c2cccc3c2n1C/C=C\COCc1c-3c(C)nn1CCN(C)C]

The title compound (100 mg, 15% yield) was prepared in analogy to the synthesis of Intermediate 200 using ethyl 7-{1-[2-(dimethylamino)ethyl]-5-(hydroxymethyl)-3-methyl-1H-pyrazol-4-yl}-3-[3-(naphthalen-1-yloxy)propyl]-1H-indole-2-carboxylate (630 mg, 1.14 mmol) as starting material. The crude product was purified by flash chromatography (25 g Biotage SNAP cartridge silica, dichloromethane/ethanol gradient, 0%→20% ethanol).

LC-MS (Method 1): R$_t$=1.56 min; MS (ESIpos): m/z=607 [M+H]$^+$

Intermediate 427

(rac)-ethyl 1-[2-(dimethylamino)ethyl]-3-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate

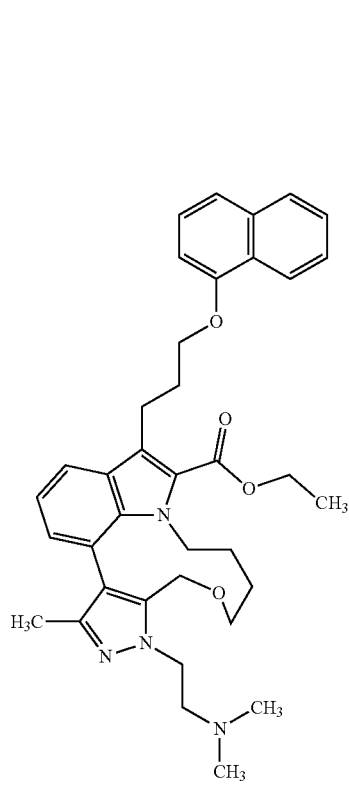

The title compound (110 mg) was prepared in analogy to the synthesis of Intermediate 174 using (rac)-ethyl (11Z)-1-[2-(dimethylamino)ethyl]-3-methyl-7-[3-(naphthalen-1-yloxy)propyl]-1,10,13,15-tetrahydropyrazolo[4',3':9,10][1,6]oxazacycloundecino[8,7,6-hi]indole-8-carboxylate (100 mg, 165 μmol) as starting material.

LC-MS (Method 2): $R_t$=1.74 min; MS (ESIpos): m/z=609 [M+H]$^+$

Intermediate 428 ethyl 7-[2-(hydroxymethyl)-6,7-dihydro-5H-pyrazolo[5,1-b][1,3]oxazin-3-yl]-3-[3-(naphthalen-1-yloxy)propyl]-1H-indole-2-carboxylate

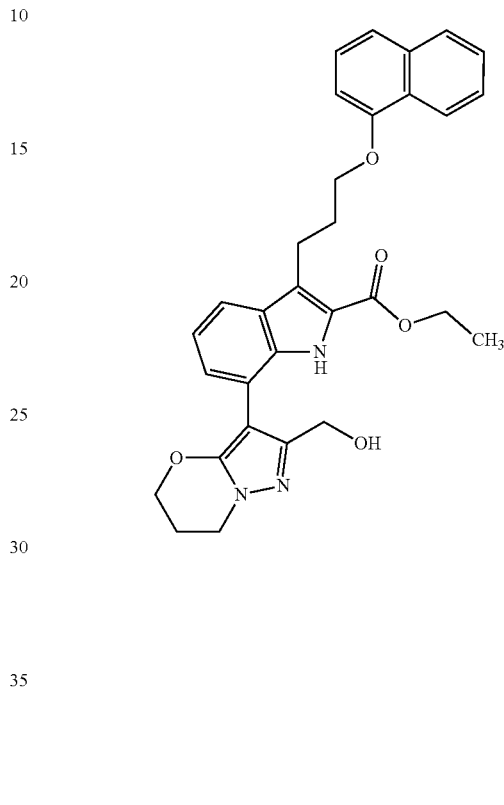

The title compound (1.60 g, 92% yield). was prepared in analogy to the synthesis of Intermediate 199 using ethyl 3-[3-(naphthalen-1-yloxy)propyl]-7-(4,4,5,5-tetramethyl-1,3,2-dioxaborolan-2-yl)-1H-indole-2-carboxylate (1.65 g, 3.31 mmol; see Intermediate 5) and (3-bromo-6,7-dihydro-5H-pyrazolo[5,1-b][1,3]oxazin-2-yl)methanol (810 mg, 3.48 mmol; see intermediate 416) as starting materials. The crude product was purified by flash chromatography (100 g Biotage SNAP cartridge silica, dichloromethane/ethanol gradient, 0%→5% ethanol).

LC-MS (Method 1): $R_t$=1.51 min; MS (ESIpos): m/z=526 [M+H]$^+$ $^1$H-NMR (400 MHz, DMSO-d$_6$): δ [ppm]=11.28 (s, 1H), 8.26-8.22 (m, 1H), 7.89-7.85 (m, 1H), 7.60 (d, 1H), 7.55-7.36 (m, 4H), 7.27 (dd, 1H), 7.02 (dd, 1H), 6.90 (d, 1H), 5.76 (s, 1H), 4.38-4.31 (m, 2H), 4.29-4.11 (m, 8H), 3.45-3.34 (m, 2H), 2.29-2.16 (m, 4H), 1.29 (t, 3H), 1.07 (s, 6H)

Intermediate 429

(rac)-ethyl (5Z)-1-[3-(naphthalen-1-yloxy)propyl]-4,7,13,14-tetrahydro-9H,12H-[1,3]oxazino[3",2":1',5']pyrazolo[4',3':9,10][1,6]oxazacycloundecino[8,7,6-hi]indole-2-carboxylate

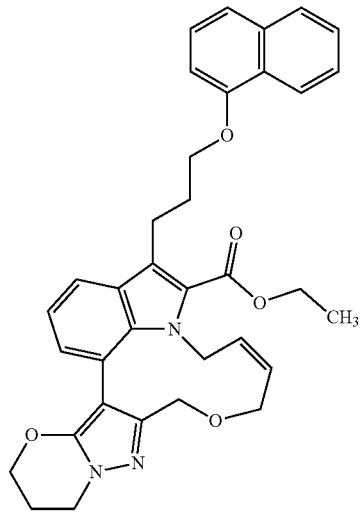 [SMILES: CCOC(=O)c1c(CCCOc2cccc3ccccc23)c2cccc3c2n1C/C=C\COCc1nn2c(c1-3)OCCC2]

A mixture of ethyl 7-[2-(hydroxymethyl)-6,7-dihydro-5H-pyrazolo[5,1-b][1,3]oxazin-3-yl]-3-[3-(naphthalen-1-yloxy)propyl]-1H-indole-2-carboxylate (500 mg, 951 µmol), (2Z)-1,4-dichlorobut-2-ene (120 µl, 1.1 mmol), caesium carbonate (1.55 g, 4.76 mmol) and sodium iodide (285 mg, 1.90 mmol) in acetonitrile (20 ml) was stirred for 16 h at room temperature, followed by 4 h at 60° C. For work-up, the mixture was concentrated, water was added and the mixture was extracted with a mixture of dichloromethane and 2-propanol (4:1). The combined organic phases were filtered through a silicone filter and concentrated. The residue was purified by flash chromatography (28 g Biotage SNAP cartridge NH₂ silica, hexanes/ethyl acetate gradient, 0%→100% ethyl acetate) to give the title compound (180 mg, 33% yield).

LC-MS (Method 1): $R_t$=1.60 min; MS (ESIpos): m/z=578 [M+H]⁺

¹H-NMR (400 MHz, DMSO-d6) δ[ppm]: 0.852 (0.46), 1.154 (3.87), 1.173 (8.11), 1.190 (4.27), 1.237 (0.82), 1.265 (3.73), 1.282 (8.34), 1.300 (3.81), 1.391 (0.84), 1.988 (16.00), 2.174 (0.58), 2.190 (1.05), 2.207 (1.26), 2.224 (1.02), 2.518 (2.49), 2.523 (1.74), 3.266 (0.44), 3.285 (0.62), 3.346 (0.55), 3.365 (0.66), 3.384 (0.40), 3.577 (0.47), 3.591 (0.58), 3.607 (0.67), 3.621 (0.58), 3.829 (0.58), 3.857 (0.87), 3.886 (0.49), 4.000 (1.14), 4.017 (3.39), 4.035 (3.29), 4.053 (1.05), 4.136 (0.59), 4.152 (0.87), 4.169 (0.89), 4.178 (0.51), 4.189 (0.58), 4.197 (0.49), 4.211 (1.40), 4.226 (3.20), 4.233 (1.62), 4.242 (2.52), 4.251 (2.12), 4.260 (3.41), 4.266 (3.62), 4.286 (1.78), 4.299 (0.57), 4.304 (1.35), 4.312 (0.69), 4.321 (0.40), 4.330 (0.68), 4.895 (0.41), 4.932 (0.70), 5.009 (0.55), 5.035 (0.70), 5.073 (0.54), 5.196 (0.70), 5.203 (0.66), 5.222 (0.41), 5.331 (0.49), 5.344 (0.46), 5.759 (1.17), 6.905 (1.41), 6.907 (1.44), 6.922 (3.06), 6.925 (2.14), 6.939 (1.39), 7.036 (1.54), 7.054 (1.49), 7.056 (1.76), 7.074 (1.20), 7.381 (1.02), 7.402 (1.84), 7.421 (1.55), 7.458 (1.88), 7.479 (1.03), 7.501 (0.41), 7.514 (1.24), 7.519 (2.23), 7.528 (2.63), 7.538 (2.33), 7.543 (1.42), 7.555 (0.43), 7.726 (1.42), 7.729 (1.49), 7.746 (1.36), 7.749 (1.26), 7.865 (1.07), 7.868 (0.76), 7.875 (0.58), 7.880 (0.70), 7.883 (0.74), 7.889 (0.92), 8.222 (0.97), 8.229 (0.73), 8.234 (0.44), 8.247 (0.90).

Intermediate 430

(rac)-ethyl 1-[3-(naphthalen-1-yloxy)propyl]-4,5,6,7,13,14-hexahydro-9H,12H-[1,3]oxazino[3",2":1',5']pyrazolo[4',3':9,10][1,6]oxazacycloundecino[8,7,6-hi]indole-2-carboxylate

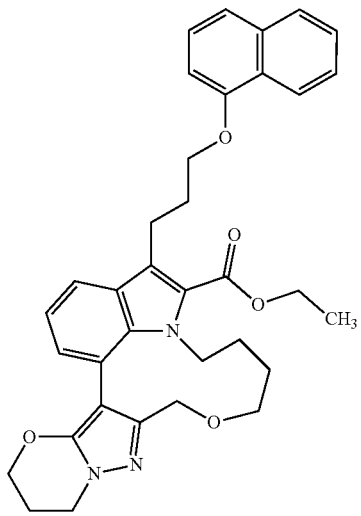 [SMILES: CCOC(=O)c1c(CCCOc2cccc3ccccc23)c2cccc3c2n1CCCCOCc1nn2c(c1-3)OCCC2]

The title compound (220 mg) was prepared in analogy to the synthesis of Intermediate 174 using (rac)-ethyl (5Z)-1-[3-(naphthalen-1-yloxy)propyl]-4,7,13,14-tetrahydro-9H,12H-[1,3]oxazino[3",2":1',5']pyrazolo[4',3':9,10][1,6]oxazacycloundecino[8,7,6-hi]indole-2-carboxylate (180 mg, 312 µmol) as starting material.

LC-MS (Method 1): $R_t$=1.63 min; MS (ESIpos): m/z=580 [M+H]⁺

¹H-NMR (400 MHz, DMSO-d6) δ[ppm]: 0.655 (0.81), 0.853 (0.66), 1.035 (6.59), 1.053 (16.00), 1.066 (13.91), 1.071 (7.69), 1.145 (0.66), 1.201 (1.35), 1.237 (1.54), 1.258 (6.70), 1.275 (14.50), 1.286 (1.90), 1.293 (6.85), 1.303 (1.21), 1.320 (0.92), 1.353 (6.19), 1.392 (1.54), 1.758 (1.65), 2.182 (2.86), 2.204 (1.94), 2.323 (1.57), 2.327 (2.27), 2.331 (1.57), 2.518 (9.08), 2.523 (6.37), 2.665 (1.61), 2.669 (2.23), 2.673 (1.54), 3.165 (0.92), 3.181 (0.81), 3.204 (0.73), 3.219 (0.70), 3.235 (0.77), 3.252 (1.03), 3.273 (1.21), 3.285 (1.17), 3.297 (1.06), 3.310 (1.06), 3.354 (1.35), 3.369 (0.77), 3.387 (0.77), 3.405 (1.35), 3.417 (1.14), 3.423 (3.22), 3.435 (3.33), 3.440 (2.93), 3.453 (3.00), 3.457 (1.03), 3.470 (1.03), 3.599 (1.32), 3.939 (2.27), 4.067 (3.26), 4.083 (0.77), 4.098 (4.10), 4.115 (1.65), 4.130 (1.24), 4.143 (1.65), 4.162 (1.39), 4.170 (1.46), 4.181 (2.75), 4.198 (5.31), 4.205 (4.36), 4.216 (4.10), 4.226 (4.06), 4.243 (3.88), 4.255 (1.32), 4.262 (2.05), 4.273 (2.89), 4.280 (1.43), 4.291 (2.56), 4.300 (1.79), 4.308 (0.92), 4.318 (1.65), 4.343 (2.20), 4.356 (4.17), 4.368 (2.09), 4.502 (2.89), 4.534 (2.64), 6.903 (2.34), 6.920 (2.56), 6.955 (2.16), 6.958 (2.38), 6.973 (3.41), 6.976 (3.08), 7.026 (3.04), 7.046 (3.41), 7.064 (2.01), 7.374 (1.87), 7.394 (3.41), 7.413 (2.71), 7.456 (3.73), 7.477 (2.05), 7.509 (0.66), 7.522 (3.37), 7.526 (2.42), 7.535 (3.00), 7.540 (2.64), 7.546 (3.41), 7.557 (0.73), 7.704 (2.49), 7.707 (2.60), 7.724 (2.38), 7.728 (2.27), 7.865

(2.12), 7.870 (1.35), 7.878 (2.01), 7.882 (1.32), 7.889 (1.79), 8.240 (1.76), 8.252 (1.43), 8.264 (1.54).

Intermediate 431 ethyl 7-[2-(hydroxymethyl)-6,7-dihydro-4H-pyrazolo[5,1-c][1,4]oxazin-3-yl]-3-[3-(naphthalen-1-yloxy)propyl]-1H-indole-2-carboxylate

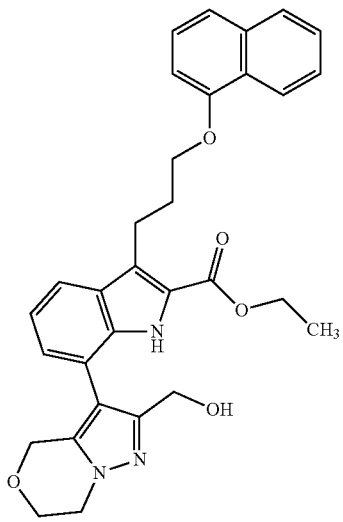 [SMILES: CCOC(=O)c1[nH]c2c(-c3c(CO)nn4c3COCC4)cccc2c1CCCOc1cccc2ccccc12]

XPhos Pd G2 (see abbreviation list, 127 mg, 161 µmol) was added to a degassed mixture of ethyl 3-[3-(naphthalen-1-yloxy)propyl]-7-(4,4,5,5-tetramethyl-1,3,2-dioxaborolan-2-yl)-1H-indole-2-carboxylate (2.39 g, 4.78 mmol; see Intermediate 5), (3-bromo-6,7-dihydro-4H-pyrazolo[5,1-c][1,4]oxazin-2-yl)methanol (1.17 g, 5.02 mmol; see Intermediate 418), aqueous potassium phosphate solution (19 ml, 0.50 M, 9.6 mmol) and THF (58 ml), and the mixture was stirred for 3 h at 50° C. For work-up, the mixture was concentrated, water and a mixture of dichloromethane and 2-propanol (4:1) was added and the phases were separated. The combined organic phases were filtered through a silicone filter and concentrated. The residue was purified by flash chromatography (100 g Snap Cartridge, hexanes/ethyl acetate gradient 0%→100% ethyl acetate) to give the title compound 2.09 g (83% yield).

LC-MS (Method 1): $R_t$=1.52 min; MS (ESIpos): m/z=526 [M+H]$^+$ $^1$H-NMR (400 MHz, DMSO-d6) δ[ppm]: 1.154 (1.71), 1.172 (3.67), 1.190 (1.86), 1.263 (7.03), 1.281 (16.00), 1.299 (7.27), 1.988 (6.21), 2.192 (0.46), 2.209 (1.40), 2.226 (1.88), 2.245 (1.44), 2.260 (0.50), 2.518 (3.11), 2.523 (2.19), 3.352 (2.69), 3.370 (1.67), 3.999 (0.49), 4.017 (1.44), 4.035 (1.41), 4.053 (7.73), 4.103 (1.17), 4.114 (3.07), 4.127 (2.77), 4.163 (2.76), 4.177 (3.03), 4.193 (2.54), 4.209 (4.24), 4.224 (2.16), 4.229 (2.62), 4.247 (6.66), 4.265 (6.54), 4.283 (1.93), 4.334 (5.19), 4.338 (5.95), 4.352 (3.05), 4.683 (3.86), 4.741 (6.58), 5.036 (0.73), 5.050 (1.58), 5.064 (0.67), 5.937 (2.15), 6.904 (2.51), 6.921 (2.69), 7.032 (1.66), 7.049 (3.49), 7.069 (3.34), 7.084 (3.38), 7.087 (3.86), 7.101 (1.74), 7.105 (1.36), 7.372 (1.94), 7.392 (3.64), 7.411 (3.03), 7.448 (3.71), 7.469 (2.03), 7.483 (0.63), 7.486 (0.86), 7.500 (2.15), 7.504 (1.96), 7.511 (2.30), 7.517 (4.65), 7.524 (2.30), 7.530 (2.08), 7.535 (2.38), 7.547 (0.94), 7.552 (0.58), 7.657 (2.35), 7.660 (2.35), 7.677 (2.27), 7.679 (2.11), 7.858 (2.15), 7.865 (1.17), 7.877 (2.15), 7.882 (1.82), 8.217 (1.90), 8.222 (1.82), 8.241 (1.81), 11.610 (2.69).

Intermediate 432

(rac)-ethyl (5Z)-1-[3-(naphthalen-1-yloxy)propyl]-4,7,12,13-tetrahydro-9H,15H-[1,4]oxazino[4",3":1',5']pyrazolo[4',3':9,10][1,6]oxazacycloundecino[8,7,6-hi]indole-2-carboxylate

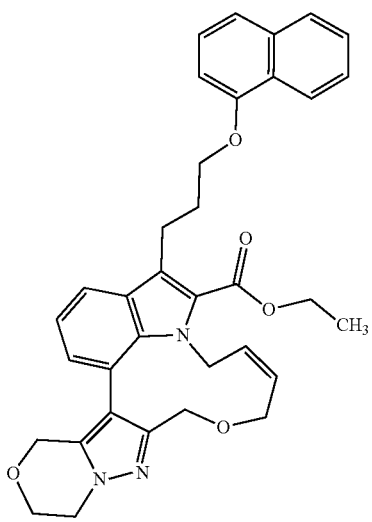 [SMILES: CCOC(=O)c1c(CCCOc2cccc3ccccc23)c2cccc3c2n1C/C=C\COCc1nn2c(c1-3)COCC2]

The title compound (280 mg, 51% yield). was prepared in analogy to the synthesis of Intermediate 429 using ethyl 7-[2-(hydroxymethyl)-6,7-dihydro-4H-pyrazolo[5,1-c][1,4]oxazin-3-yl]-3-[3-(naphthalen-1-yloxy)propyl]-1H-indole-2-carboxylate (500 mg, 951 µmol) starting material.

LC-MS (Method 1): $R_t$=1.64 min; MS (ESIpos): m/z=578 [M+H]$^+$ $^1$H-NMR (400 MHz, DMSO-d6) δ[ppm]: 1.154 (1.05), 1.172 (2.30), 1.190 (1.18), 1.268 (7.19), 1.285 (16.00), 1.304 (7.33), 1.987 (3.86), 2.221 (1.33), 2.233 (1.35), 2.518 (2.33), 2.523 (1.63), 3.283 (0.84), 3.301 (1.18), 3.323 (1.62), 3.342 (1.38), 3.360 (0.80), 3.606 (0.80), 3.620 (0.98), 3.637 (1.36), 3.650 (1.16), 3.748 (1.20), 3.776 (1.67), 3.805 (0.89), 4.017 (0.86), 4.035 (0.90), 4.053 (0.73), 4.070 (0.96), 4.085 (1.40), 4.093 (0.98), 4.109 (1.41), 4.123 (1.35), 4.146 (1.46), 4.173 (1.03), 4.187 (1.18), 4.230 (2.94), 4.242 (4.45), 4.247 (3.06), 4.257 (5.13), 4.275 (5.37), 4.292 (1.60), 4.296 (3.66), 4.305 (4.86), 4.314 (6.79), 4.323 (2.52), 4.328 (4.62), 4.340 (1.53), 4.365 (0.88), 4.403 (3.79), 4.435 (2.61), 4.757 (0.69), 4.784 (0.81), 4.796 (1.20), 4.822 (1.35), 4.907 (1.42), 4.945 (0.84), 5.126 (0.68), 5.133 (0.69), 5.153 (1.34), 5.160 (1.35), 5.179 (0.80), 5.186 (0.77), 5.300 (0.93), 5.313 (0.88), 6.917 (3.31), 6.920 (5.40), 6.935 (3.76), 6.938 (5.10), 7.072 (3.13), 7.090 (2.92), 7.092 (3.29), 7.110 (2.48), 7.380 (2.07), 7.400 (3.69), 7.419 (3.19), 7.456 (3.70), 7.476 (1.99), 7.491 (0.90), 7.504 (2.33), 7.508 (2.02), 7.513 (2.49), 7.521 (5.29), 7.528 (2.57), 7.533 (2.26), 7.537 (2.59), 7.550 (0.98), 7.759 (2.80), 7.762 (2.94), 7.779 (2.61), 7.782 (2.59), 7.862 (2.13), 7.870 (1.17), 7.880 (2.10), 7.886 (1.85), 8.206 (1.92), 8.212 (1.79), 8.223 (0.96), 8.228 (1.64), 8.231 (1.80).

Intermediate 433

(rac)-ethyl 1-[3-(naphthalen-1-yloxy)propyl]-4,5,6,7,12,13-hexahydro-9H,15H-[1,4]oxazino[4",3":1',5']pyrazolo[4',3':9,10][1,6]oxazacycloundecino[8,7,6-hi]indole-2-carboxylate

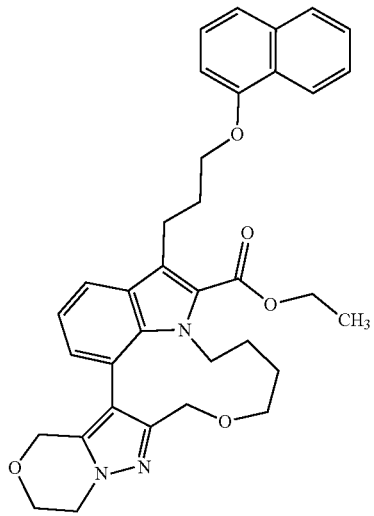 [SMILES: CCOC(=O)c1c(CCCOc2cccc3ccccc23)c2cccc3c2n1CCCCOCc1nn2c(c1-3)COCC2]

The title compound (310 mg) was prepared in analogy to the synthesis of Intermediate 174 using (rac)-ethyl (5Z)-1-[3-(naphthalen-1-yloxy)propyl]-4,7,12,13-tetrahydro-9H,15H-[1,4]oxazino[4",3":1',5']pyrazolo[4',3':9,10][1,6]oxazacycloundecino[8,7,6-hi]indole-2-carboxylate (280 mg, 485 µmol) as starting material.

LC-MS (Method 1): R$_t$=1.67 min; MS (ESIpos): m/z=580 [M+H]$^+$

Intermediate 434 ethyl 7-[2-(hydroxymethyl)-4,5,6,7-tetrahydropyrazolo[1,5-a]pyridin-3-yl]-3-[3-(naphthalen-1-yloxy)propyl]-1H-indole-2-carboxylate

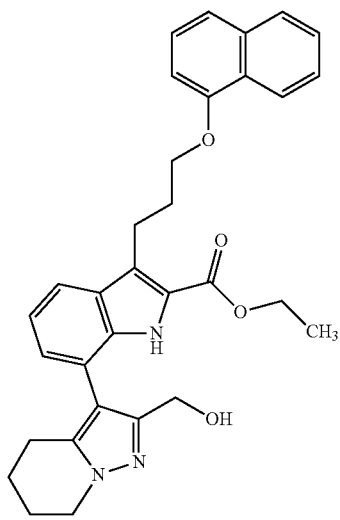 [SMILES: CCOC(=O)c1[nH]c2c(-c3c(CO)nn4c3CCCC4)cccc2c1CCCOc1cccc2ccccc12]

The title compound (1.05 g, 50% yield) was prepared in analogy to the synthesis of Intermediate 199 using ethyl 3-[3-(naphthalen-1-yloxy)propyl]-7-(4,4,5,5-tetramethyl-1,3,2-dioxaborolan-2-yl)-1H-indole-2-carboxylate (2.02 g, 4.04 mmol; see Intermediate 5) and (3-bromo-4,5,6,7-tetrahydropyrazolo[1,5-a]pyridin-2-yl)methanol (980 mg, 4.24 mmol; see Intermediate 420) as starting materials.

LC-MS (Method 1): R$_t$=1.61 min; MS (ESIneg): m/z=522 [M−H]$^-$ $^1$H-NMR (400 MHz, DMSO-d6) δ[ppm]: 1.067 (0.67), 1.154 (1.20), 1.172 (2.37), 1.190 (1.13), 1.259 (6.91), 1.277 (16.00), 1.294 (7.15), 1.754 (1.65), 1.769 (1.39), 1.988 (5.01), 1.996 (1.40), 2.009 (1.66), 2.211 (1.29), 2.229 (1.72), 2.247 (1.30), 2.327 (0.65), 2.518 (2.29), 2.523 (1.62), 2.647 (1.88), 2.660 (1.25), 2.665 (1.36), 2.669 (1.19), 2.673 (0.77), 3.352 (2.45), 3.370 (1.51), 4.017 (0.96), 4.035 (0.95), 4.103 (1.61), 4.118 (3.09), 4.133 (1.59), 4.194 (1.83), 4.209 (3.89), 4.222 (3.38), 4.240 (6.36), 4.258 (6.33), 4.275 (2.51), 4.288 (3.36), 4.305 (1.03), 4.320 (0.80), 5.760 (0.82), 5.829 (2.01), 6.903 (2.30), 6.920 (2.53), 7.038 (2.06), 7.055 (3.01), 7.057 (2.57), 7.076 (2.80), 7.138 (3.07), 7.141 (3.24), 7.156 (2.22), 7.159 (2.01), 7.371 (1.87), 7.392 (3.51), 7.411 (2.98), 7.449 (3.45), 7.469 (1.86), 7.488 (0.80), 7.501 (2.16), 7.505 (1.84), 7.511 (2.15), 7.518 (4.70), 7.525 (2.29), 7.531 (2.02), 7.535 (2.35), 7.548 (0.92), 7.639 (2.37), 7.658 (2.25), 7.858 (1.99), 7.866 (1.09), 7.877 (2.03), 7.882 (1.69), 8.222 (1.78), 8.228 (1.66), 8.240 (0.92), 8.245 (1.54), 8.247 (1.66), 11.492 (2.87).

Intermediate 435

(rac)-ethyl (5Z)-1-[3-(naphthalen-1-yloxy)propyl]-4,7,12,13,14,15-hexahydro-9H-pyrido[1",2":1',5']pyrazolo[4',3':9,10][1,6]oxazacycloundecino[8,7,6-hi]indole-2-carboxylate

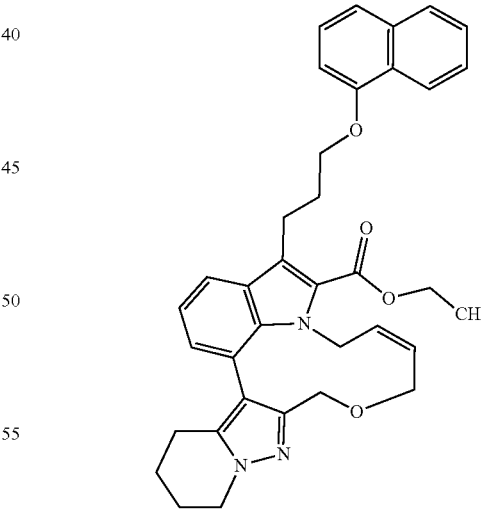

A mixture of ethyl 7-[2-(hydroxymethyl)-4,5,6,7-tetrahydropyrazolo[1,5-a]pyridin-3-yl]-3-[3-(naphthalen-1-yloxy)propyl]-1H-indole-2-carboxylate (400 mg, 764 µmol), (2Z)-1,4-dichlorobut-2-ene (96 µl, 920 µmol), caesium carbonate (1.24 g, 3.82 mmol) and sodium iodide (229 mg, 1.53 mmol) in acetonitrile (16 ml, 310 mmol) was stirred for 16 h at room temperature followed by 4 h at 60° C. For work-up, water was added and the mixture was extracted three times with ethyl acetate. The combined organic phases were filtered through a silicone filter and concentrated. The residue was purified by flash chromatography (25 g Biotage SNAP cartridge silica, hexanes/ethyl acetate gradient, 0%→100% ethyl acetate) to give the title compound (260 mg, 59% yield).

LC-MS (Method 1): $R_t$=1.72 min; MS (ESIpos): m/z=576 [M+H]$^+$ $^1$H-NMR (400 MHz, DMSO-d6) δ[ppm]: 1.155 (3.57), 1.173 (7.82), 1.190 (4.02), 1.269 (5.42), 1.287 (12.32), 1.304 (5.57), 1.681 (0.52), 1.741 (0.57), 1.988 (16.00), 2.169 (0.82), 2.185 (1.90), 2.198 (1.87), 2.214 (1.45), 2.224 (1.27), 2.518 (6.15), 2.523 (4.27), 3.268 (0.45), 3.284 (0.70), 3.302 (1.07), 3.351 (1.20), 3.368 (0.72), 3.385 (0.47), 3.568 (0.65), 3.581 (0.77), 3.598 (1.02), 3.611 (0.90), 3.729 (0.90), 3.757 (1.32), 3.786 (0.72), 4.000 (1.10), 4.017 (3.25), 4.035 (3.12), 4.053 (1.07), 4.075 (0.55), 4.090 (0.82), 4.107 (0.82), 4.121 (0.47), 4.190 (0.52), 4.205 (1.07), 4.226 (2.77), 4.241 (3.55), 4.254 (3.20), 4.271 (2.48), 4.275 (2.22), 4.289 (0.70), 4.296 (2.22), 4.307 (3.32), 4.314 (2.25), 4.323 (1.02), 4.331 (0.55), 4.340 (0.97), 4.368 (3.12), 4.400 (1.82), 4.762 (0.50), 4.789 (0.60), 4.801 (0.97), 4.827 (1.07), 4.887 (1.10), 4.924 (0.57), 5.101 (0.50), 5.108 (0.55), 5.128 (0.97), 5.135 (1.05), 5.154 (0.57), 5.161 (0.57), 5.267 (0.42), 5.280 (0.45), 5.294 (0.72), 5.307 (0.72), 5.759 (4.45), 6.887 (2.12), 6.889 (2.32), 6.905 (2.57), 6.907 (2.50), 6.920 (1.92), 6.936 (2.05), 7.068 (2.15), 7.086 (2.25), 7.088 (2.60), 7.105 (1.87), 7.379 (1.50), 7.400 (2.82), 7.419 (2.37), 7.456 (2.85), 7.476 (1.50), 7.488 (0.50), 7.492 (0.67), 7.505 (1.77), 7.509 (1.52), 7.515 (1.87), 7.522 (3.97), 7.529 (1.92), 7.535 (1.67), 7.539 (1.95), 7.552 (0.75), 7.556 (0.45), 7.741 (2.15), 7.744 (2.25), 7.761 (2.07), 7.765 (1.95), 7.863 (1.65), 7.870 (0.90), 7.881 (1.67), 7.886 (1.37), 8.209 (1.47), 8.215 (1.37), 8.234 (1.37).

Intermediate 436

(rac)-ethyl 1-[3-(naphthalen-1-yloxy) propyl]-4,5,6,7,12,13,14,15-octahydro-9H-pyrido[1'',2'':1',5']pyrazolo[4',3':9,10][1,6]oxazacycloundecino[8,7,6-hi]indole-2-carboxylate

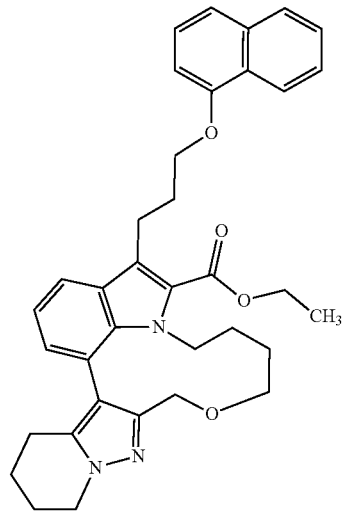 [SMILES: CCOC(=O)c1c(CCCOc2cccc3ccccc23)c2cccc3c2n1CCCCOCc1nn2c(c1-3)CCCC2]

The title compound (280 mg) was prepared in analogy to the synthesis of Intermediate 174 using (rac)-ethyl (5Z)-1-[3-(naphthalen-1-yloxy)propyl]-4,7,12,13,14,15-hexahydro-9H-pyrido[1'',2'':1',5']pyrazolo[4',3':9,10][1,6]oxazacycloundecino[8,7,6-hi]indole-2-carboxylate (260 mg, 452 µmol) as starting material.

LC-MS (Method 1): $R_t$=1.74 min; MS (ESIpos): m/z=578 [M+H]$^+$ $^1$H-NMR (400 MHz, DMSO-d6) δ[ppm]: 0.579 (0.39), 0.598 (1.30), 0.616 (0.64), 1.035 (7.56), 1.053 (16.00), 1.070 (7.17), 1.146 (0.82), 1.177 (0.85), 1.232 (0.42), 1.263 (4.45), 1.267 (1.91), 1.281 (9.77), 1.285 (3.66), 1.299 (4.81), 1.303 (2.00), 1.353 (4.48), 1.636 (0.48), 1.652 (0.54), 1.713 (0.76), 1.725 (0.73), 1.741 (0.76), 1.757 (1.24), 1.774 (0.48), 1.945 (1.09), 1.960 (1.57), 1.975 (1.24), 2.138 (0.64), 2.154 (1.63), 2.169 (1.60), 2.187 (1.48), 2.209 (1.33), 2.518 (6.41), 2.523 (4.39), 3.077 (0.64), 3.092 (0.60), 3.236 (0.45), 3.269 (1.42), 3.290 (1.33), 3.369 (0.67), 3.385 (0.39), 3.405 (1.18), 3.417 (1.21), 3.423 (3.45), 3.435 (3.57), 3.440 (3.05), 3.453 (3.12), 3.457 (1.15), 3.470 (1.12), 3.599 (0.85), 3.946 (0.60), 4.023 (0.60), 4.040 (0.73), 4.056 (0.91), 4.072 (0.60), 4.168 (0.76), 4.184 (2.90), 4.193 (1.39), 4.203 (2.12), 4.215 (3.81), 4.220 (2.51), 4.230 (2.78), 4.248 (2.54), 4.265 (1.84), 4.282 (1.42), 4.287 (1.97), 4.296 (0.76), 4.304 (1.84), 4.313 (1.12), 4.322 (0.51), 4.331 (0.88), 4.344 (2.39), 4.357 (4.51), 4.370 (2.33), 4.534 (1.94), 4.566 (1.69), 4.749 (0.70), 6.896 (1.51), 6.913 (1.97), 6.932 (0.42), 6.949 (1.48), 6.951 (1.57), 6.966 (1.97), 6.969 (1.88), 7.054 (2.51), 7.074 (2.45), 7.091 (1.45), 7.370 (1.15), 7.379 (0.51), 7.390 (2.21), 7.400 (0.91), 7.409 (1.78), 7.419 (0.70), 7.453 (2.60), 7.474 (1.48), 7.501 (0.54), 7.513 (1.78), 7.518 (3.12), 7.528 (3.54), 7.537 (3.24), 7.542 (1.88), 7.554 (0.60), 7.718 (1.84), 7.721 (1.75), 7.738 (1.57), 7.741 (1.69), 7.863 (1.66), 7.873 (0.82), 7.880 (1.12), 7.886 (1.39), 8.230 (1.36), 8.239 (0.91), 8.255 (1.06).

Intermediate 437

(rac)-diethyl 3-methylhexanedioate

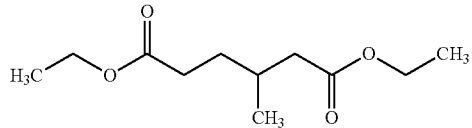

A solution of (rac)-3-methyl adipic acid (13.1 g) in ethanol (100 ml) and hexanes (50 ml) was treated with sulfuric acid (2 ml), affixed with a Dean Stark trap, and heated to reflux, removing 80 ml of the more dense fraction from the Dean Stark trap. The reaction was cooled to room temperature, volatiles were removed under reduced pressure, the residue was partitioned between ethyl acetate and water, the organic layer was washed with water, then saturated aqueous sodium bicarbonate solution, saturated aqueous sodium chloride solution, and was then dried over magnesium sulfate. Insoluble materials were removed by filtration, and volatiles were removed under reduced pressure to give the title compound as a colorless oil (17.5 g).

$^1$H NMR (400 MHz, Chloroform-d) δ 4.13 (qd, J=7.1, 2.1 Hz, 4H), 2.41-2.22 (m, 3H), 2.14 (dd, J=14.8, 8.0 Hz, 1H), 2.03-1.91 (m, 1H), 1.76-1.62 (m, 1H), 1.53 (dddd, J=13.9, 9.3, 7.9, 6.4 Hz, 1H), 1.25 (td, J=7.2, 0.8 Hz, 6H), 0.96 (d, J=6.7 Hz, 3H).

Intermediate 438 ethyl 4-methyl-2-oxocyclopentane-1-carboxylate
(Mixture of Stereoisomers)

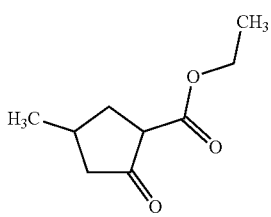

To a solution of (rac)-diethyl-3-methyl-hexanedioate (25 g, 115 mmol; see Intermediate 437) in toluene (250 ml) was added potassium tert-butoxide (13.4 g, 119 mmol), and the resulting thick yellow suspension was heated to reflux for 7 hours. Volatiles were removed under reduced pressure and the resulting orange paste was diluted with hexanes (200 ml), ethyl acetate (50 ml) and aqueous hydrochloric acid (3M, 100 ml). The layers were separated and the organic phase was washed with saturated aqueous sodium chloride solution, the combined aqueous phases were back extracted with a mixture of ethyl acetate in hexanes (1:1), and the combined organic layers were dried over magnesium sulfate. Insoluble materials were removed by filtration and volatiles were removed under reduced pressure to give the title compound in moderate purity as a pale yellow syrup (20.8 g), which was used without further manipulation.

Intermediate 439

(rac)-ethyl 7-bromo-3-(4-ethoxy-4-oxobutan-2-yl)-6-methyl-1H-indole-2-carboxylate

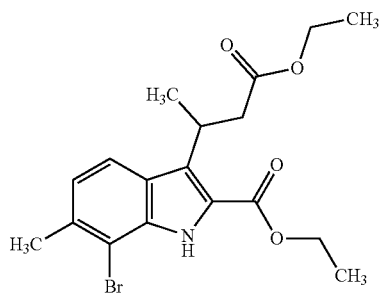 [SMILES: CCOC(=O)CC(C)c1c(C(=O)OCC)[nH]c2c(Br)c(C)ccc12]

To a mixture of 2-bromo-3-methyl-aniline (10 g, 53.7 mmol) in water (70 ml) and aqueous hydrogen chloride (3 M, 50 ml, 150 mmol) in an ice water bath was added an ice cold solution of sodium nitrite (3.7 g, 53.7 mmol) in water (50 ml) over twenty minutes. The mixture was stirred an additional 10 minutes at that temperature, at which point a solution of potassium acetate (31.9 g, 326 mmol) in water (20 ml) was added. To this mixture was added a solution of ethyl 4-methyl-2-oxocyclopentanecarboxylate (mixture of stereoisomers, 13 g, 57.2 mmol; see Intermediate 438) in ethanol (20 ml) and the mixture was stirred at 0° C. for one hour. The mixture was then diluted with ethyl acetate (150 ml), layers were separated, and the organic phase was washed with saturated aqueous sodium chloride solution. The combined aqueous phases were back extracted with ethyl acetate, the combined organic layers were washed with saturated aqueous sodium chloride solution, and the combined organic phases were dried over magnesium sulfate. Insoluble materials were removed by filtration, and the filtrate was concentrated under reduced pressure to yield a red syrup. This material was dissolved in ethanol (150 ml), treated with sulfuric acid (7.6 ml, 143 mmol), and heated to reflux for 20 hours. The reaction was then treated with sulfuric acid (2 ml), and toluene (20 ml), and heating to reflux was continued for an additional 24 hours, at which time sulfuric acid (4 ml) and triethyl ortho formate (4 ml) were added, and the mixture was heated to reflux for an additional 6 hours, then cooled to room temperature, and diluted with ethyl acetate (100 ml). The organic phase was washed three times with water (50 ml each), saturated aqueous sodium bicarbonate solution (50 ml), and saturated aqueous sodium chloride solution (50 ml), and the combined aqueous phases were back extracted with ethyl acetate. The combined organic layers were dried over magnesium sulfate, insoluble materials were removed by filtration, and the filtrate was concentrated under reduced pressure. The resulting residue was treated with toluene sulfonic acid monohydrate (12 g), and suspended in toluene (200 ml), heated to reflux for 2 hours, diluted with ethanol (5 ml) and heated for 16 hours at reflux. The mixture was cooled to room temperature, volatiles were removed under reduced pressure, and the residue was suspended in a mixture of ethyl acetate (200 ml), hexanes (100 ml), methanol (100 ml), and water (100 ml). The layers were separated and the organic layer was washed with water (100 ml), twice with saturated aqueous sodium bicarbonate solution (50 ml each), and the combined organic layers were passed thorough a short pad of silica gel. The filtrate was concentrated under reduced pressure, the residue was dissolved in dichloromethane (20 ml) and hexanes (100 ml), and purified by normal phase flash chromatography on silica gel eluting with ethyl acetate in hexanes (10%), to give the title compound as an amber oil (5.3 g) in moderate purity.

LRMS (ESIpos):m/z=398 [M+H]$^+$

Intermediate 440

(rac)-ethyl 7-bromo-3-(4-hydroxybutan-2-yl)-6-methyl-1H-indole-2-carboxylate

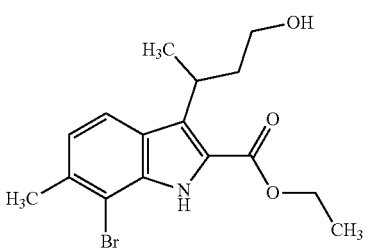 [SMILES: CCOC(=O)c1[nH]c2c(Br)c(C)ccc2c1C(C)CCO]

To a solution of impure (rac)-ethyl 7-bromo-3-(4-ethoxy-4-oxobutan-2-yl)-6-methyl-1H-indole-2-carboxylate (7.3 g; see Intermediate 439) in tetrahydrofuran (100 ml) at 35° C. was added borane dimethyl sulfide (4 ml), and stirred for 48 hours, additional borane dimethyl sulfide (2 ml) was added and heated continued for an additional 24 hours, followed by additional borane dimethyl sulfide (1 ml) and heated for an additional 16 hours. The reaction mixture was cooled to room temperature, the reaction was stopped by the slow addition of methanol (16 ml), the mixture was then stirred at room temperature for 60 hours, volatiles were removed under reduced pressure and the residue was purified by flash chromatography on silica gel eluting with a gradient of ethyl acetate in hexanes (25-75%) to give the title compound as an amber gum (3.1 g).

LRMS (ESIpos) m/z=356 [M+H]$^+$ $^1$H NMR (400 MHz, Chloroform-d) δ 8.64 (s, 1H), 7.65 (d, J=8.3 Hz, 1H), 7.05-6.95 (m, 1H), 4.45 (p, J=7.1 Hz, 2H), 4.20-4.00 (m, 1H), 3.52 (ddd, J=16.1, 9.2, 4.7 Hz, 1H), 3.41-3.27 (m, 1H), 2.52 (s, 3H), 2.48-2.42 (m, 1H), 2.13-1.98 (m, 2H), 1.51 (d, J=7.1 Hz, 3H), 1.45 (t, J=7.2 Hz, 3H).

Intermediate 441

(rac)-ethyl 3-(4-hydroxybutan-2-yl)-6-methyl-7-(4,4,5,5-tetramethyl-1,3,2-dioxaborolan-2-yl)-1H-indole-2-carboxylate

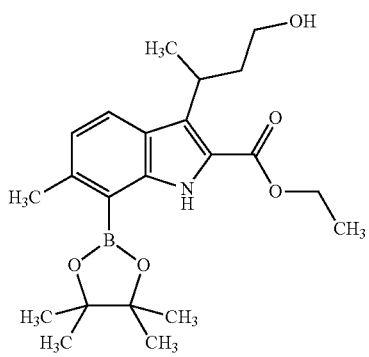 [SMILES: CCOC(=O)c1[nH]c2c(B3OC(C)(C)C(C)(C)O3)c(C)ccc2c1C(C)CCO]

A degassed mixture of (rac)-ethyl 7-bromo-3-(4-hydroxybutan-2-yl)-6-methyl-1H-indole-2-carboxylate (3.1 g, 8.75 mmol; see Intermediate 440), bispinocolatodiboron (4.44 g, 17.5 mmol), potassium acetate (2.25 g, 22.9 mmol), and Pd(dppf)Cl$_2$×CH$_2$Cl$_2$, 335 mg. 0.41 mol) in dioxane (60 ml) was heated to 80° C. for 19 hours. The mixture was cooled to room temperature, diluted with ethyl acetate (50 ml), filtered through a pad of silica gel, which was washed three times with ethyl acetate (50 ml each), and the combined filtrate was adsorbed onto celite (8 g), and purified by flash chromatography on silica gel eluting with a gradient of ethyl acetate in hexanes (10-50%) to give the title compound as a yellow gum. This material was triturated from hot hexanes to afford the title compound as a white powder (1.61 g).

LRMS (ESIpos) m/z=402 [M+H]$^+$ $^1$H NMR (400 MHz, DMSO-d6) δ 9.85 (s, 1H), 7.83 (d, J=8.3 Hz, 1H), 6.94 (d, J=8.4 Hz, 1H), 4.31 (qt, J=7.2, 3.7 Hz, 2H), 4.24 (t, J=5.1 Hz, 1H), 3.89 (dt, J=8.7, 6.7 Hz, 1H), 3.35-3.26 (m, 1H), 3.21 (ddt, J=10.6, 8.2, 5.6 Hz, 1H), 2.58 (s, 3H), 2.06-1.85 (m, 2H), 1.41-1.33 (m, 18H).

Intermediate 442

(rac)-ethyl 3-(4-((tert-butyldimethylsilyl)oxy)butan-2-yl)-6-methyl-7-(4,4,5,5-tetramethyl-1,3,2-dioxaborolan-2-yl)-1H-indole-2-carboxylate

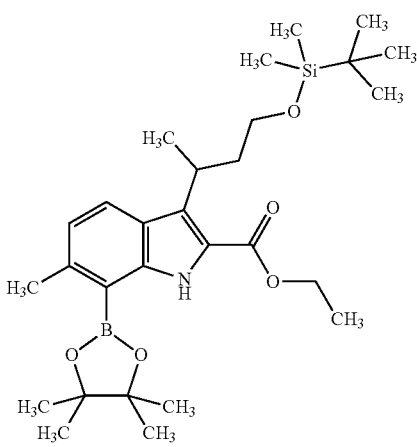 [SMILES: CCOC(=O)c1[nH]c2c(B3OC(C)(C)C(C)(C)O3)c(C)ccc2c1C(C)CCO[Si](C)(C)C(C)(C)C]

A solution of (rac)-ethyl 3-(4-hydroxybutan-2-yl)-6-methyl-7-(4,4,5,5-tetramethyl-1,3,2-dioxaborolan-2-yl)-1H-indole-2-carboxylate (1.61 g, 4.01 mmol; see Intermediate 441) in dichloromethane (50 ml) was treated with a mixture of imidazole (1.4 g, 20.6 mmol) and tert-butyldimethylsilyl chloride (1.1 g, 7.29 mmol) in dichloromethane (25 ml) and the resulting white suspension was stirred at room temperature for 210 minutes. The reaction was then stopped by the addition of ethanol (3 ml), the mixture was diluted with ethyl acetate (100 ml), and concentrated under reduced pressure to half volume. The resulting suspension was washed twice with water (50 ml each), and saturated aqueous sodium chloride solution. The combined aqueous phases were back extracted with ethyl acetate, and combined organic layers were dried over sodium sulfate. Insoluble materials were removed by filtration, and the filtrate was concentrated under reduced pressure. The resulting residue was purified by flash chromatography on silica gel eluting with a gradient of dichloromethane in hexanes (0-100%) to give the title compound as a colorless gum (2.01 g).

LRMS (ESIpos) m/z=516 [M+H]$^+$ $^1$H NMR (400 MHz, Chloroform-d) δ 9.90 (s, 1H), 7.78 (d, J=8.3 Hz, 1H), 6.92 (d, J=8.3 Hz, 1H), 4.38 (q, J=7.1 Hz, 2H), 3.96 (q, J=7.3 Hz, 1H), 3.61-3.43 (m, 2H), 2.66 (s, 3H), 2.25-2.12 (m, 1H), 2.02 (dq, J=13.7, 6.6 Hz, 1H), 1.43 (dd, J=7.1, 4.1 Hz, 6H), 1.40 (s, 12H), 0.85 (s, 9H), −0.04 (s, 6H).

Intermediate 443

(rac)-ethyl 7-bromo-6-methyl-3-(4-(naphthalen-1-yloxy)butan-2-yl)-1H-indole-2-carboxylate

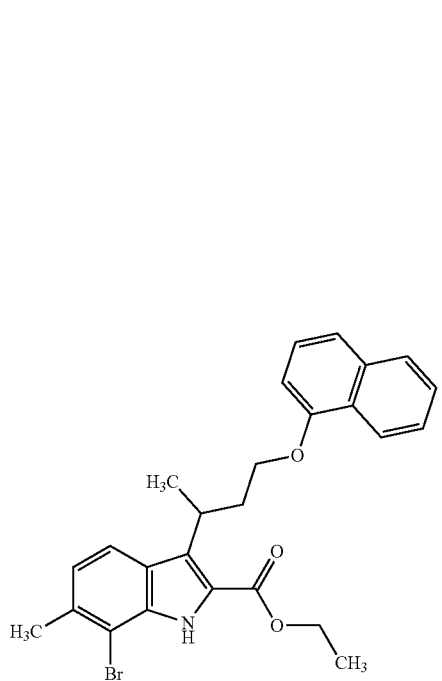 [SMILES: CCOC(=O)c1[nH]c2c(Br)c(C)ccc2c1C(C)CCOc1cccc2ccccc12]

A solution of triphenylphosphine (2.04 g, 7.78 mmol) in tetrahydrofuran (50 ml) at 0° C. was treated with diisopropylazodicarboxylate (1.22 g, 6.03 mmol) and stirred for 10 minutes, this solution was then added to a pre-mixed solution of ethyl 7-bromo-3-(4-hydroxybutan-2-yl)-6-methyl-1H-indole-2-carboxylate (1.38 g, 3.9 mmol; see Intermediate 440) and naphthalen-1-ol (840 mg, 5.83 mmol) in tetrahydrofuran (20 ml) at 0° C., and stirred for 16 hours, allowing the mixture to slowly warm to room temperature. Volatiles were removed and the residue was purified by flash chromatography on silica gel eluting with a gradient of ethyl acetate in hexanes (0-50%) to give the title compound as an amber gum (960 mg).

MS (ESIpos) m/z=480 [M+H]+

$^1$H NMR (400 MHz, Chloroform-d) δ 8.71 (s, 1H), 8.15-8.05 (m, 1H), 7.77 (d, J=8.0 Hz, 1H), 7.72 (d, J=8.3 Hz, 1H), 7.48 (ddd, J=8.1, 6.7, 1.4 Hz, 1H), 7.42 (ddd, J=8.2, 6.8, 1.4 Hz, 1H), 7.37 (d, J=8.3 Hz, 1H), 7.32-7.29 (m, 1H), 7.00 (d, J=8.2 Hz, 1H), 6.69-6.61 (m, 1H), 4.31 (pd, J=7.2, 4.5 Hz, 3H), 4.09 (t, J=6.4 Hz, 2H), 2.67-2.56 (m, 1H), 2.54 (s, 3H), 2.45 (dt, J=13.4, 6.5 Hz, 1H), 1.58 (d, J=7.2 Hz, 3H), 1.33 (t, J=7.1 Hz, 3H).

Intermediate 444

(rac)-ethyl 6-methyl-3-(4-(naphthalen-1-yloxy)butan-2-yl)-7-(4,4,5,5-tetramethyl-1,3,2-dioxaborolan-2-yl)-1H-indole-2-carboxylate

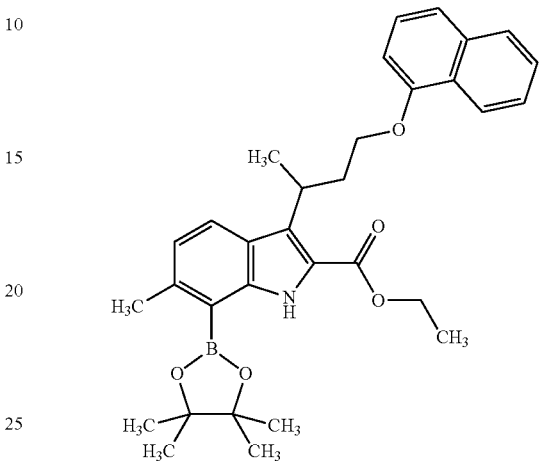

A degassed mixture of (rac)-ethyl 7-bromo-6-methyl-3-(4-(naphthalen-1-yloxy)butan-2-yl)-1H-indole-2-carboxylate (940 mg, 1.95 mmol; see Intermediate 443), bispinocolatodiboron (1.03 g, 4.05 mmol), potassium acetate (2.1 g, 21.3 mmol), and Pd(dppf)Cl$_2$×CH$_2$Cl$_2$, (100 mg. 0.063 mol) in dioxane (20 ml) was heated to 80° C. for 16 hours. The mixture was cooled to room temperature, diluted with ethyl acetate (20 ml), filtered through a pad of silica gel, and the silica gel was washed ethyl acetate (150 ml). The filtrate was adsorbed onto celite, and purified by flash chromatography on silica gel eluting with a gradient of dichloromethane in hexanes (0-50%) to give the title compound as a colorless film (600 mg).

LRMS (ESIpos) m/z=528 [M+H]+

$^1$H NMR (400 MHz, Chloroform-d) δ 9.93 (s, 1H), 8.23-8.12 (m, 1H), 7.83 (d, J=8.3 Hz, 1H), 7.77-7.72 (m, 1H), 7.48-7.38 (m, 2H), 7.34 (d, J=8.2 Hz, 1H), 7.29-7.22 (m, 1H), 6.93 (d, J=8.3 Hz, 1H), 6.62 (d, J=7.5 Hz, 1H), 4.28 (qt, J=6.7, 3.4 Hz, 3H), 4.11-3.99 (m, 2H), 2.66 (s, 3H), 2.59 (ddt, J=12.6, 9.8, 6.2 Hz, 1H), 2.42 (dq, J=13.1, 6.6 Hz, 1H), 1.56 (d, J=7.1 Hz, 3H), 1.40 (s, 12H), 1.32 (t, J=7.1 Hz, 3H).

Intermediate 445

(rac)-ethyl 7-(5-(hydroxymethyl)-1,3-dimethyl-1H-pyrazol-4-yl)-6-methyl-3-(4-(naphthalen-1-yloxy)butan-2-yl)-1H-indole-2-carboxylate

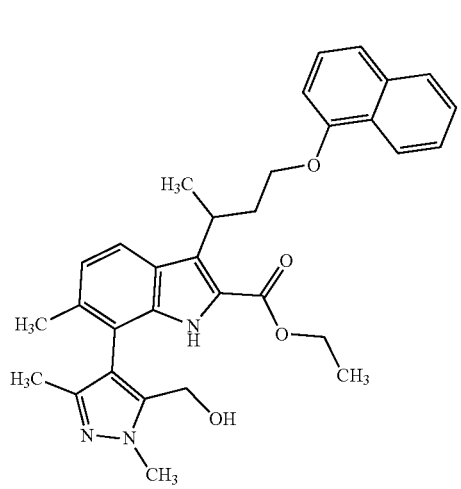 [SMILES: CCOC(=O)c1[nH]c2c(-c3c(C)nn(C)c3CO)c(C)ccc2c1C(C)CCOc1cccc2ccccc12]

A degassed mixture of (rac)-ethyl 6-methyl-3-(4-(naphthalen-1-yloxy)butan-2-yl)-7-(4,4,5,5-tetramethyl-1,3,2-dioxaborolan-2-yl)-1H-indole-2-carboxylate (600 mg, 1.13 mmol; see Intermediate 444), (4-bromo-1,3-dimethyl-1H-pyrazol-5-yl)methanol (323 mg, 1.57 mmol; see Intermediate 8), Xphos Pd G2 (90 mg, 0.114 mmol), dioxane (24 ml) and aqueous potassium phosphate tribasic solution (1M, 5 ml) was heated to 40° C. for 90 minutes. The reaction mixture was cooled to room temperature, diluted with ethyl acetate, and the organic phase was sequentially washed with water, and saturated aqueous sodium chloride solution. The combined aqueous washes were back extracted with ethyl acetate, and the combined organic layers were dried over magnesium sulfate. Insoluble materials were removed by filtration, volatiles were removed under reduced pressure, and the residue was purified by flash chromatography on silica gel eluting with a gradient of ethyl acetate in hexanes (0-100%) to give the title compound (524 mg) as a pale yellow oil.

LRMS (ESIpos) m/z=526 [M+H]$^+$

Intermediate 446 ethyl (Z)-10,12,13-trimethyl-1-(4-(naphthalen-1-yloxy)butan-2-yl)-4,7,9,10-tetrahydropyrazolo[4',3':9,10][1]oxa[6]azacycloundecino[8,7,6-hi]indole-2-carboxylate (Mixture of Stereoisomers)

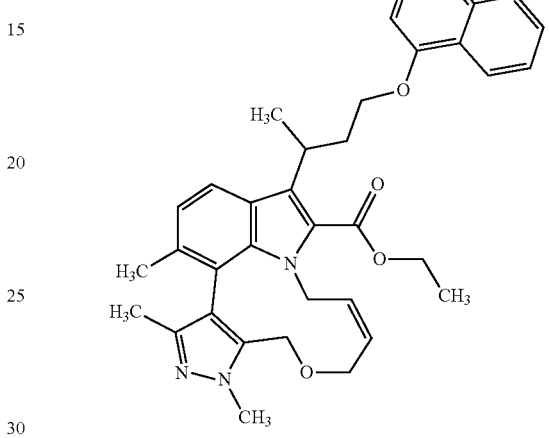

A mixture of (rac)-ethyl 7-(5-(hydroxymethyl)-1,3-dimethyl-1H-pyrazol-4-yl)-6-methyl-3-(4-(naphthalen-1-yloxy)butan-2-yl)-1H-indole-2-carboxylate (520 mg; see Intermediate 445), caesium carbonate (700 mg), and (2Z)-1,4-dichlorobut-2-ene (0.16 ml) in acetonitrile (25 ml) was treated with potassium iodide (800 mg) and stirred at room temperature for 16 hours. The mixture was then warmed to 25° C., and treated with sodium sulfite (3.3 g), and stirred at that temperature for 48 hours; the reaction mixture was then treated with (2Z)-1,4-dichlorobut-2-ene (0.2 ml), and stirred at that temperature for 24 hours. The reaction mixture was then diluted with ethyl acetate (100 ml), insoluble materials were removed by filtration, and the filtrate was concentrated under reduced pressure. The residue was purified by flash chromatography on silica gel eluting with a gradient of ethyl acetate in hexanes (0-100%) to give the title compound as a white foam (180 mg).

LRMS (ESIpos) m/z=578 [M+H]$^+$

Intermediate 447 ethyl 10,12,13-trimethyl-1-(4-(naphthalen-1-yloxy)butan-2-yl)-4,5,6,7,9,10-hexahydropyrazolo[4',3':9,10][1]oxa[6]azacycloundecino[8,7,6-hi]indole-2-carboxylate (Mixture of Stereoisomers)

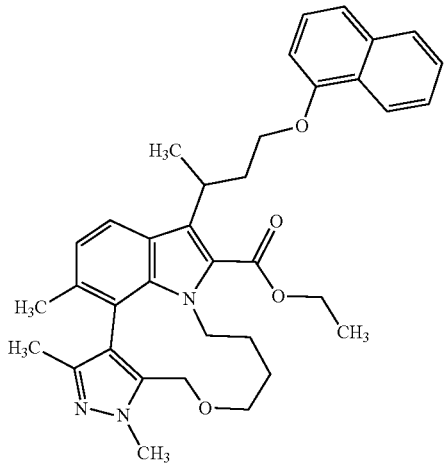 [SMILES: CCOC(=O)c1c(C(C)CCOc2cccc3ccccc23)c2ccc(C)c3c2n1CCCCOCc1c-3c(C)nn1C]

A degassed mixture of ethyl (Z)-10,12,13-trimethyl-1-(4-(naphthalen-1-yloxy)butan-2-yl)-4,7,9,10-tetrahydropyrazolo[4',3':9,10][1]oxa[6]azacycloundecino[8,7,6-hi]indole-2-carboxylate (mixture of stereoisomers, 180 mg; see Intermediate 446) and palladium on carbon (10%, 150 mg) in ethanol (20 ml) was placed under an atmosphere of hydrogen for 90 minutes, the mixture was then degassed, filtered through celite, volatiles were removed under reduced pressure and the residue was purified by flash chromatography on silica gel eluting with a gradient of ethyl acetate in hexanes (10-50%) to give the title compound as a colorless oil (108 mg).

LRMS (ESIpos) m/z=580 [M+H]$^+$

Intermediate 448

(rac)-ethyl 3-(4-((tert-butyldimethylsilyl)oxy)butan-2-yl)-7-(3-ethyl-5-(hydroxymethyl)-1-methyl-1H-pyrazol-4-yl)-6-methyl-1H-indole-2-carboxylate

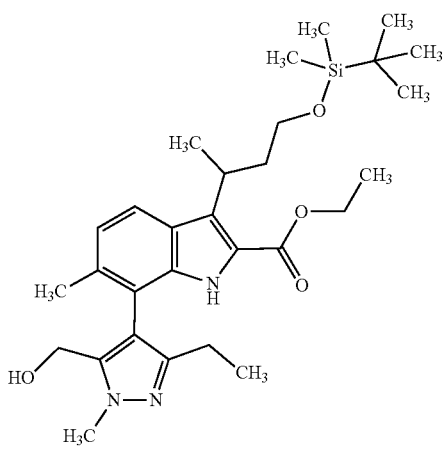 [SMILES: CCOC(=O)c1[nH]c2c(-c3c(CC)nn(C)c3CO)c(C)ccc2c1C(C)CCO[Si](C)(C)C(C)(C)C]

A degassed mixture of (rac)-ethyl 3-(4-((tert-butyldimethylsilyl)oxy)butan-2-yl)-6-methyl-7-(4,4,5,5-tetramethyl-1,3,2-dioxaborolan-2-yl)-1H-indole-2-carboxylate (825 mg, 1.6 mmol; see Intermediate 442), 1-methyl-3-ethyl-4-bromo-5-hydroxymethylpyrazole (400 mg, 1.8 mmol; see Intermediate 509), XPhos Pd G2 (100 mg) in dioxane (20 ml) and aqueous solution of potassium phosphate tribasic (1M, 4 ml) was heated to 45° C. for 16 hours. The reaction mixture was cooled to room temperature, volatiles were removed and the residue was partitioned between ethyl acetate and water. The layers were separated and the organic phase was washed with water, saturated aqueous sodium hydrogen carbonate solution, saturated aqueous sodium chloride solution; the combined aqueous washes were back extracted with ethyl acetate, and the combined organic layers were dried over magnesium sulfate. Insoluble materials were removed by filtration, volatiles were removed under reduced pressure, and the residue was purified by flash chromatography on silica gel eluting with a gradient of ethyl acetate in hexanes (0-100%) to give the title compound as a brown foam (415 mg).

LRMS (ESIpos) m/z=528 [M+H]$^+$ $^1$H NMR (400 MHz, Chloroform-d) δ 8.31 (s, 1H), 7.70 (d, J=8.4 Hz, 1H), 7.03 (d, J=8.3 Hz, 1H), 4.50-4.26 (m, 4H), 4.02 (s, 3H), 4.00-3.90 (m, 1H), 3.55 (ddd, J=15.3, 11.7, 7.3 Hz, 2H), 2.39 (q, J=7.6 Hz, 2H), 2.21 (s, 3H), 2.17 (d, J=7.7 Hz, 0H), 2.06 (dt, J=13.2, 6.6 Hz, 1H), 1.49-1.43 (m, 4H), 1.37 (t, J=7.1 Hz, 3H), 1.04 (q, J=7.5 Hz, 3H), 0.84 (d, J=5.0 Hz, 9H), −0.05 (s, 3H), −0.06 (d, J=1.8 Hz, 3H).

Intermediate 449 ethyl (Z)-1-(4-((tert-butyldimethylsilyl)oxy)butan-2-yl)-12-ethyl-10,13-dimethyl-4,7,9,10-tetrahydropyrazolo[4',3':9,10][1]oxa[6]azacycloundecino[8,7,6-hi]indole-2-carboxylate (Mixture of Stereoisomers)

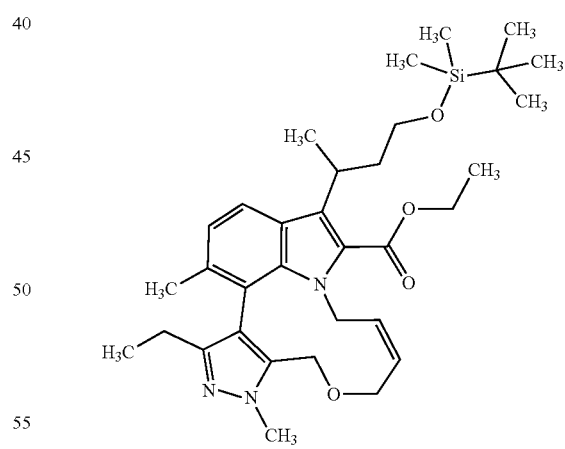

To a solution of (rac)-ethyl 3-(4-((tert-butyldimethylsilyl)oxy)butan-2-yl)-7-(3-ethyl-5-(hydroxymethyl)-1-methyl-1H-pyrazol-4-yl)-6-methyl-1H-indole-2-carboxylate (427 mg, 0.8 mmol; see Intermediate 448) and (2Z)-1,4-dichlorobut-2-ene (0.2 ml, 1.9 mmol) in N,N-dimethylformamide (15 ml) at 0° C. was added sodium hydride (60% in oil, 100 mg, 2.5 mmol), after stirring for 2 hours, additional sodium hydride (60% in oil, 10 mg) was added, after additional 2 hours, sodium hydride (60% in oil, 100 mg) was added, and the mixture was allowed to warm to room temperature over 16 hours. The reaction was stopped by the addition of acetic acid (2 ml), volatiles were removed under reduced pressure, and the residue was partitioned between ethyl acetate and water. The layers were separated and the organic phase was washed with saturated aqueous sodium hydrogen carbonate solution, and saturated aqueous sodium chloride solution. The combined aqueous washes were back extracted with ethyl acetate, the combined organic phases were dried over magnesium sulfate, insoluble materials were removed by filtration, volatiles were removed under reduced pressure and the residue was purified by flash chromatography on silica gel eluting with a gradient of ethyl acetate in hexanes (0-100%) to give the title compound as a colorless gum (407 mg).

LRMS (ESIpos) m/z=580 [M+H]$^+$ $^1$H NMR (400 MHz, Chloroform-d) δ 7.72 (d, J=8.2 Hz, 1H), 7.03 (d, J=8.2 Hz, 1H), 5.21 (s, 1H), 4.91 (s, 1H), 4.76 (d, J=17.1 Hz, 1H), 4.69-4.54 (m, 2H), 4.46-4.28 (m, 3H), 4.00 (d, J=0.8 Hz, 3H), 3.88-3.77 (m, 2H), 3.67 (t, J=11.9 Hz, 2H), 3.44 (t, J=6.9 Hz, 1H), 2.27-2.12 (m, 3H), 2.10-1.98 (m, 1H), 1.94 (s, 3H), 1.48 (dd, J=20.0, 7.2 Hz, 3H), 1.38 (td, J=7.1, 1.8 Hz, 3H), 0.91 (dt, J=11.6, 7.6 Hz, 3H), 0.84 (d, J=9.4 Hz, 9H), −0.03 (d, J=4.0 Hz, 3H), −0.08 (d, J=2.8 Hz, 3H).

Intermediate 450 ethyl 12-ethyl-1-(4-hydroxybutan-2-yl)-10,13-dimethyl-4,5,6,7,9,10-hexahydropyrazolo[4',3':9,10][1]oxa[6]azacycloundecino[8,7,6-hi]indole-2-carboxylate (Mixture of Stereoisomers)

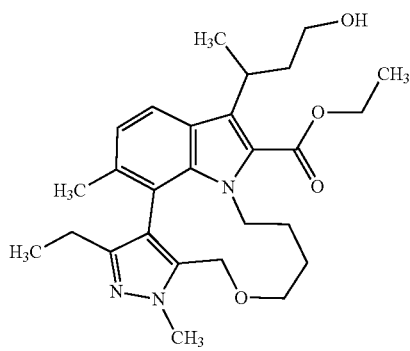 [SMILES: CCOC(=O)c1c(C(C)CCO)c2ccc(C)c3c2n1CCCCOCc1c-3c(CC)nn1C]

To a degassed mixture of ethyl (Z)-1-(4-((tert-butyldimethylsilyl)oxy)butan-2-yl)-12-ethyl-10,13-dimethyl-4,7,9,10-tetrahydropyrazolo[4',3':9,10][1]oxa[6]azacycloundecino[8,7,6-hi]indole-2-carboxylate (mixture of stereoisomers, 407 mg; see Intermediate 449) in ethanol (40 ml) was added palladium on carbon (10%, 160 mg). The mixture was degassed and then exposed to a hydrogen atmosphere for 1 hour, degassed, treated with concentrated aqueous hydrochloric acid (0.2 ml), filtered through a pad of celite, and stirred at room temperature for 2 hours. Volatiles were removed under reduced pressure and the residue was purified by flash chromatography on silica gel eluting with a gradient of ethyl acetate in hexanes (0-100%) to give the title compound as a colorless film (220 mg).

LRMS (ESIpos) m/z=468 [M+H]$^+$ $^1$H NMR (400 MHz, Chloroform-d) δ 7.72 (dd, J=8.3, 6.6 Hz, 1H), 7.02 (dd, J=8.3, 2.0 Hz, 1H), 4.58 (dd, J=13.3, 8.8 Hz, 1H), 4.51-4.19 (m, 4H), 4.18-4.04 (m, 1H), 3.97 (s, 3H), 3.91 (ddd, J=10.4, 7.2, 5.5 Hz, 0H), 3.85-3.75 (m, 1H), 3.60-3.43 (m, 3H), 3.42-3.25 (m, 1H), 3.11-2.94 (m, 1H), 2.37-2.21 (m, 2H), 2.21-2.01 (m, 2H), 1.98 (d, J=7.5 Hz, 3H), 1.78 (t, J=5.9 Hz, 0H), 1.52 (t, J=6.9 Hz, 3H), 1.38 (td, J=7.1, 4.2 Hz, 3H), 1.34-1.05 (m, 4H), 0.98 (dt, J=17.6, 7.6 Hz, 3H).

Intermediate 451 ethyl 12-ethyl-1-(4-((6-fluoronaphthalen-1-yl)oxy)butan-2-yl)-10,13-dimethyl-4,5,6,7,9,10-hexahydropyrazolo[4',3':9,10][1]oxa[6]azacycloundecino[8,7,6-hi]indole-2-carboxylate (Mixture of Stereoisomers)

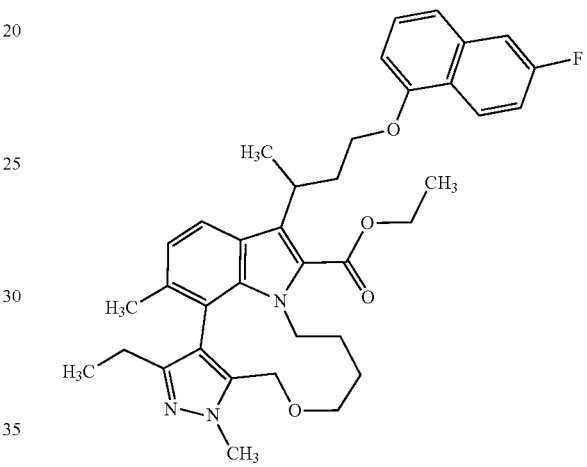

A solution of triphenyl phosphine (246 mg, 0.94 mmol) and di-tert-butyl azodicarboxylate (162 mg) in tetrahydrofuran (10 ml) at 0° C. was stirred for 15 minutes, then added to a solution of ethyl 12-ethyl-1-(4-hydroxybutan-2-yl)-10,13-dimethyl-4,5,6,7,9,10-hexahydropyrazolo[4',3':9,10][1]oxa[6]azacycloundecino[8,7,6-hi]indole-2-carboxylate (mixture of stereoisomers, 220 mg; see Intermediate 450) and 6-fluoronaphthalen-1-ol (100 mg) in tetrahydrofuran (10 ml) at 0° C., and the was mixture stirred at that temperature for 2 hours, at which time additional triphenylphosphine (250 mg) and di-tert-butyl azodicarboxylate (160 mg) were added. After stirring at that temperature for further 2 hours, the mixture was adsorbed onto celite, and purified by flash chromatography on silica gel eluting with a gradient of ethyl acetate in hexanes (0-100%) to give the title compound (158 mg) in as a colorless film.

LRMS (ESIpos) m/z=612 [M+H]$^+$ $^1$H NMR (400 MHz, Chloroform-d) δ 8.18 (ddd, J=81.8, 9.2, 5.8 Hz, 1H), 7.82 (dd, J=23.3, 8.3 Hz, 1H), 7.38 (td, J=10.3, 2.6 Hz, 1H), 7.33-7.26 (m, 2H), 7.26-7.10 (m, 1H), 7.07 (dd, J=18.3, 8.3 Hz, 1H), 6.58 (q, J=4.8 Hz, 1H), 4.56 (dd, J=29.0, 13.3 Hz, 1H), 4.40-4.23 (m, 3H), 4.23-4.00 (m, 4H), 3.98 (d, J=9.6 Hz, 4H), 3.61-3.24 (m, 1H), 2.97 (dddd, J=32.8, 11.8, 7.8, 5.5 Hz, 1H), 2.76-2.37 (m, 2H), 2.35-2.23 (m, 2H), 2.01 (d, J=7.0 Hz, 3H), 1.63 (dd, J=16.4, 7.2 Hz, 3H), 1.55-1.34 (m, 1H), 1.29 (q, J=6.9 Hz, 2H), 1.23 (t, J=7.1 Hz, 2H), 1.17-1.06 (m, 1H), 1.00 (q, J=7.4 Hz, 4H);

$^{19}$F NMR (376 MHz, Chloroform-d) δ −115.13, −115.23.

Intermediate 452 ethyl 3-(3-((tert-butyldimethylsilyl)oxy)propyl)-7-(3-ethyl-5-(hydroxymethyl)-1-methyl-1H-pyrazol-4-yl)-1H-indole-2-carboxylate

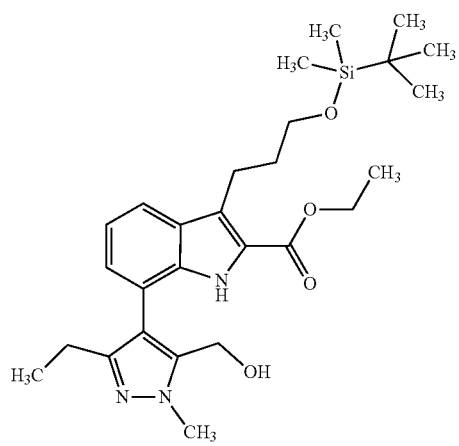

A degassed mixture of ethyl 3-(3-((tert-butyldimethylsilyl)oxy)propyl)-7-(4,4,5,5-tetramethyl-1,3,2-dioxaborolan-2-yl)-1H-indole-2-carboxylate (4.45 g, 9.14 mmol; see Intermediate 39), (4-bromo-3-ethyl-1-methyl-1H-pyrazol-5-yl)methanol (1.67 g, 7.62 mmol; see Intermediate 509), XPhos Pd G2 (299 mg, 381 μmol), aqueous solution of potassium phosphate tribasic (1M, 15.2 mL) and 1,4-dioxane (169 mL) and water (30 mL) was heated to 40° C. for 90 minutes. The mixture was cooled to room temperature, diluted with ethyl acetate and water, filtered through a pad of celite, and diluted further with ethyl acetate and water. Layers were separated and the organic phase was washed with saturated aqueous sodium chloride solution and dried over magnesium sulfate. Insoluble materials were removed by filtration, and the filtrate was concentrated under reduced pressure. The residue was purified by flash chromatography on silica gel eluting with a gradient of ethyl acetate in hexanes (0-50%) to give the title compound as an off white solid (1.98 g).

LRMS (ESIpos) m/z=500 [M+H]+

$^1$H NMR (400 MHz, Chloroform-d) δ 9.08 (s, 1H), 7.75-7.62 (m, 1H), 7.22-7.10 (m, 2H), 4.54 (s, 2H), 4.37 (q, J=7.1 Hz, 2H), 4.12 (q, J=7.1 Hz, 1H), 3.99 (s, 3H), 3.72 (t, J=6.4 Hz, 2H), 3.21-3.12 (m, 2H), 2.57 (d, J=8.0 Hz, 2H), 2.04 (s, 2H), 1.92 (dt, J=15.3, 6.6 Hz, 1H), 1.92 (s, 1H), 1.39 (t, J=7.1 Hz, 3H), 1.30-1.20 (m, 2H), 1.11 (t, J=7.5 Hz, 3H), 0.93 (s, 9H), 0.07 (s, 6H).

Intermediate 453

(rac)-ethyl (Z)-1-(3-((tert-butyldimethylsilyl)oxy)propyl)-12-ethyl-10-methyl-4,7,9,10-tetrahydropyrazolo[4',3':9,10][1]oxa[6]azacycloundecino[8,7,6-hi]indole-2-carboxylate

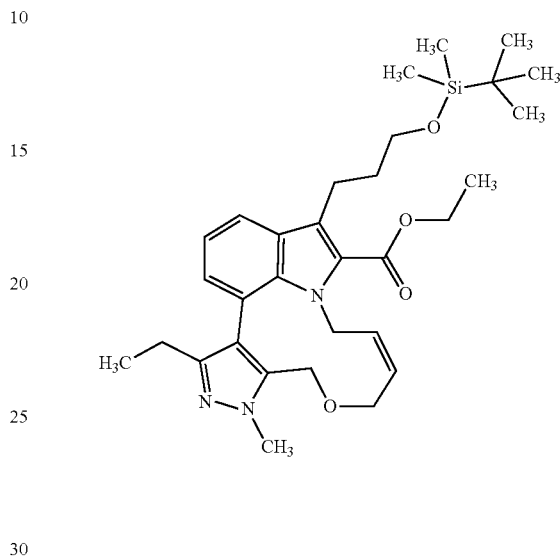

To a stirred solution of ethyl 3-(3-((tert-butyldimethylsilyl)oxy)propyl)-7-(3-ethyl-5-(hydroxymethyl)-1-methyl-1H-pyrazol-4-yl)-1H-indole-2-carboxylate (2.23 g, 4.46 mmol; see Intermediate 452) and (2Z)-1,4-dichlorobut-2-ene (0.6 ml, 5.69 mmol) in N,N-dimethylformamide (20 ml) at 0° C. was added sodium hydride (60% in oil, 220 mg, 5.5 mmol) and the mixture was allowed to warm to room temperature over 15 hours, at which time additional sodium hydride (60% in oil, 220 mg) was added. After stirring at room temperature for 4 hours, (Z)-1,4-dichlorobut-2-ene (0.2 ml) was added, and after 1 additional hour glacial acetic acid (2 ml) was added. Volatiles were removed under reduced pressure, the residue was partitioned between ethyl acetate and aqueous sodium bicarbonate solution, the organic phase was washed with saturated aqueous sodium chloride solution, combined aqueous washes were back extracted with ethyl acetate, and the combined organic phases were dried over sodium sulfate. Insoluble materials were removed by filtration, the filtrate was concentrated under reduced pressure, and the residue was purified by flash chromatography on silica gel, eluting with a gradient of ethyl acetate in hexanes (0-100%) to give the title compound and a faintly yellow oil (1.16 g).

LRMS (ESIpos) m/z=552 [M+H]+

$^1$H NMR (300 MHz, Chloroform-d) δ 7.71 (dd, J=8.0, 1.2 Hz, 1H), 7.15-7.08 (m, 1H), 6.86 (dd, J=7.1, 1.2 Hz, 1H), 5.23 (s, 1H), 5.16-5.01 (m, 2H), 4.81 (dd, J=15.9, 10.7 Hz, 1H), 4.61 (d, J=13.8 Hz, 1H), 4.48 (d, J=13.9 Hz, 1H), 4.44-4.30 (m, 2H), 3.99 (s, 3H), 3.83 (dd, J=13.4, 4.7 Hz, 1H), 3.76-3.60 (m, 3H), 3.28-2.99 (m, 2H), 2.24 (q, J=7.5 Hz, 2H), 1.93 (q, J=6.9 Hz, 2H), 1.42 (t, J=7.1 Hz, 3H), 0.95 (t, J=7.5 Hz, 3H), 0.93 (s, 9H), 0.07 (s, 6H).

Intermediate 454

(rac)-ethyl 12-ethyl-1-(3-hydroxypropyl)-10-methyl-4,5,6,7,9,10-hexahydropyrazolo[4',3':9,10][1,6]oxaazacycloundecino[8,7,6-hi]indole-2-carboxylate

Intermediate 455

(rac)-ethyl 1-(3-bromopropyl)-12-ethyl-10-methyl-4,5,6,7,9,10-hexahydropyrazolo[4',3':9,10][1,6]oxaazacycloundecino[8,7,6-hi]indole-2-carboxylate

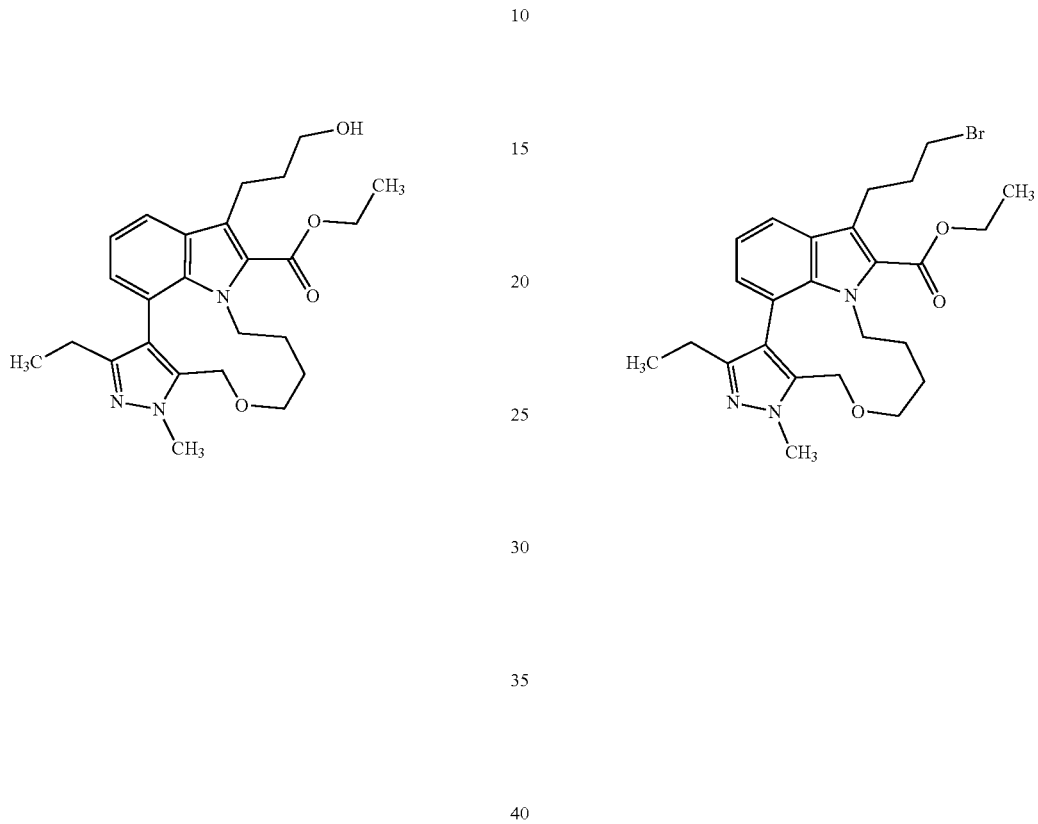

A solution of (rac)-(Z)-ethyl 1-(3-((tert-butyldimethylsilyl)oxy)propyl)-12-ethyl-10-methyl-4,7,9,10-tetrahydropyrazolo[4',3':9,10][1,6]oxaazacycloundecino[8,7,6-hi]indole-2-carboxylate (1.16 g, 2.1 mmol; see Intermediate 453) in ethanol (50 ml) was degassed and treated with palladium on carbon (10%, 223 mg), and was then degassed again and placed under an atmosphere of hydrogen for 3 hours. The suspension was degassed, filtered through a pad of celite, and the filter cake was washed three times with ethanol (20 ml each), and the combined filtrate and washes were treated with concentrated aqueous hydrochloric acid (0.2 ml, 12M), and allowed to stand for 5 minutes. Volatiles were removed under reduced pressure and the residue was purified by flash chromatography on silica gel eluting with a gradient of ethyl acetate in hexanes (50-100%) to give the title compound as a white solid (497 mg).

LRMS (ESIpos) m/z=440 [M+H]$^+$ $^1$H NMR (300 MHz, Chloroform-d) δ 7.69 (dd, J=8.1, 1.3 Hz, 1H), 7.09 (dd, J=8.0, 7.1 Hz, 1H), 6.90 (dd, J=7.1, 1.2 Hz, 1H), 4.56 (d, J=13.2 Hz, 1H), 4.52-4.27 (m, 4H), 4.19 (ddd, J=13.8, 10.2, 2.9 Hz, 1H), 3.94 (s, 3H), 3.73-3.43 (m, 3H), 3.20 (t, J=7.1 Hz, 2H), 2.93 (ddd, J=11.7, 8.3, 5.2 Hz, 1H), 2.68 (s, 1H), 2.33 (qd, J=7.5, 2.3 Hz, 2H), 2.11-1.86 (m, 2H), 1.39 (t, J=7.1 Hz, 5H), 1.32-1.04 (m, 2H), 1.00 (t, J=7.6 Hz, 3H).

To a solution of (rac)-ethyl 12-ethyl-1-(3-hydroxypropyl)-10-methyl-4,5,6,7,9,10-hexahydropyrazolo[4',3':9,10][1,6]oxaazacycloundecino[8,7,6-hi]indole-2-carboxylate (497 mg, 1.13 mmol; see Intermediate 454) and triphenyl phosphine (400 mg, 1.5 mmol) in dichloromethane (20 ml) at 0° C. was treated perbromomethane (also referred to as tetrabromomethane herein, 525 mg, 1.58 mmol). After stirring for 30 minutes, volatiles were removed under reduced pressure and the residue was purified by normal phase chromatography on silica gel eluting with a gradient of ethyl acetate in hexanes (0-100%) to give the title compound as a pale yellow film (430 mg, 1.13 mmol).

LRMS (ESIpos) m/z 504 [M+H]$^+$ $^1$H NMR (400 MHz, Chloroform-d) δ 7.70 (d, J=8.0 Hz, 1H), 7.08 (t, J=7.5 Hz, 1H), 6.88 (d, J=7.0 Hz, 1H), 4.58 (dd, J=17.5, 13.8 Hz, 2H), 4.49-4.28 (m, 3H), 4.16 (ddd, J=14.0, 10.5, 2.8 Hz, 1H), 3.92 (s, 3H), 3.47 (ddt, J=10.3, 6.6, 4.1 Hz, 3H), 3.23 (ddt, J=38.4, 13.8, 7.3 Hz, 2H), 2.88 (ddd, J=12.8, 9.1, 4.2 Hz, 1H), 2.30 (dtt, J=35.1, 14.1, 7.4 Hz, 4H), 1.55-1.31 (m, 4H), 1.31-1.03 (m, 3H), 0.98 (t, J=7.6 Hz, 3H).

761

Intermediate 456 ethyl 3-(3-((tert-butyldimethylsilyl)oxy)propyl)-7-(3-(hydroxymethyl)-1,5-dimethyl-1H-pyrazol-4-yl)-1H-indole-2-carboxylate

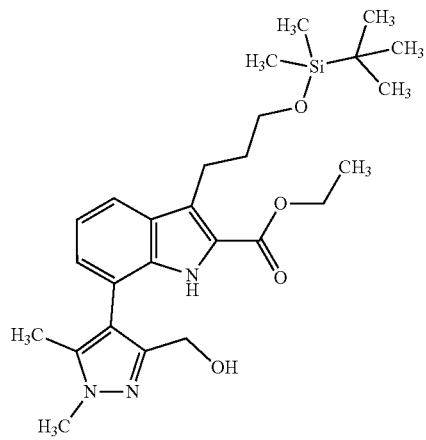 [SMILES: CCOC(=O)c1[nH]c2c(-c3c(CO)nn(C)c3C)cccc2c1CCCO[Si](C)(C)C(C)(C)C]

A degassed mixture of ethyl 3-(3-((tert-butyldimethylsilyl)oxy)propyl)-7-(4,4,5,5-tetramethyl-1,3,2-dioxaborolan-2-yl)-1H-indole-2-carboxylate (8.6 g, 17.6 mmol; see Intermediate 39), (4-bromo-1,5-dimethyl-1H-pyrazol-3-yl)methanol (3.77 g, 18.4 mmol; see Intermediate 11), tetrahydrofuran (176 mL), XPhos Pd G3 (595 mg, 0.7 mmol), tetrahydrofuran (176 ml) and aqueous solution of potassium phosphate tribasic (0.5M, 70.4 mL, 35.2 mmol) was stirred at 50° C. for 16 hours. The mixture was cooled to room temperature and diluted with ethyl acetate and water. The layers were separated and the aqueous phase was extracted twice more with ethyl acetate. The combined organic phases were washed with saturated aqueous sodium chloride solution, dried over sodium sulfate, insoluble materials were removed by filtration and volatiles were removed under reduced pressure. The residue was purified by flash chromatography on silica gel eluting with a gradient of ethyl acetate in hexanes (0-100%) to give the title compound (6.9 g) as a beige solid.

LRMS (ESIpos) m/z=486 [M+H]+

762

Intermediate 457

(rac)-(Z)-ethyl 1-(3-((tert-butyldimethylsilyl)oxy)propyl)-11,12-dimethyl-4,7,9,11-tetrahydropyrazolo[4',3':9,10][1,6]oxaazacycloundecino[8,7,6-hi]indole-2-carboxylate

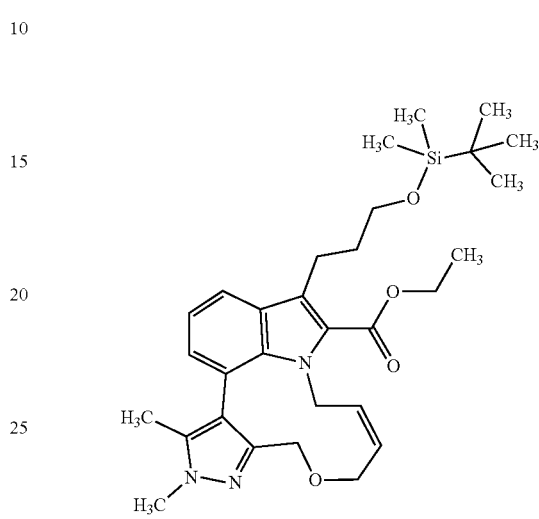

A stirred solution of ethyl 3-(3-((tert-butyldimethylsilyl)oxy)propyl)-7-(3-(hydroxymethyl)-1,5-dimethyl-1H-pyrazol-4-yl)-1H-indole-2-carboxylate (1.8 g, 3.7 mmol; see Intermediate 456) in N,N-dimethyl formamide (20 ml) was cooled in an ice water bath and treated with (2Z)-1,4-dichlorobut-2-ene (0.5 ml), followed by sodium hydride (60% in oil, 350 mg). After 210 minutes additional sodium hydride (60%, 150 mg) was added, and the mixture was allowed to warm to room temperature over 16 hours. The mixture was then treated with (2Z)-1,4-dichlorobut-2-ene (0.5 ml) and stirred at room temperature for 3 hours, at which time sodium hydride (60%, 180 mg) was added, and the mixture was stirred for 5 hours, glacial acetic acid (6 ml) was added, and then volatiles were removed under reduced pressure. The residue was partitioned between ethyl acetate (100 ml) and water (50 ml), the organic phase was washed with aqueous hydrogen chloride (3M, 50 ml), saturated aqueous sodium chloride solution, and the combined aqueous washes were back extracted with ethyl acetate (100 ml). The combined organic phases were dried over magnesium sulfate, insoluble materials were removed by filtration, and the filtrate was concentrated under reduced pressure. The residue was purified by flash chromatography on silica gel eluting with a gradient of ethyl acetate in hexanes (0-100%) to give the title compound, as an amber gum (1.8 g).

LRMS (ESIpos) m/z=538 [M+H]+

Intermediate 458

(rac)-ethyl 1-(3-hydroxypropyl)-11,12-dimethyl-4,5,6,7,9,11-hexahydropyrazolo[4',3':9,10][1,6]oxaazacycloundecino[8,7,6-hi]indole-2-carboxylate

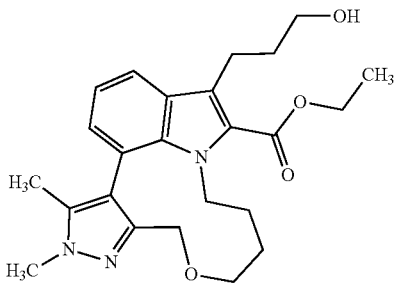 [SMILES: CCOC(=O)c1c(CCCO)c2cccc3c2n1CCCCOCc1nn(C)c(C)c1-3]

To a degassed solution of (rac)-(Z)-ethyl 1-(3-((tert-butyldimethylsilyl)oxy)propyl)-11,12-dimethyl-4,7,9,11-tetrahydropyrazolo[4',3':9,10][1,6]oxaazacycloundecino[8,7,6-hi]indole-2-carboxylate (1.8 g, 3.34 mmol; see Intermediate 457) in ethanol (40 ml) was added palladium on carbon (10%, 380 mg), the mixture was further degassed, and placed under an atmosphere of hydrogen for 1 hour, at which time concentrated aqueous hydrochloric acid (0.1 ml) was added. After stirring for an additional 1 hour, the mixture was degassed, filtered through a pad of celite, the filter cake was rinsed three times with ethyl acetate (20 ml each), and the combined filtrate and washes were concentrated under reduced pressure. The residue was purified by normal phase chromatography on silica gel eluting with a gradient of ethyl acetate in hexanes (50-100%) to give the title compound as a white foam (520 mg).

LRMS (ESIpos) m/z=426 [M+H]$^+$ $^1$H NMR (300 MHz, Chloroform-d) δ 7.69-7.63 (m, 1H), 7.18-7.09 (m, 1H), 7.02-6.96 (m, 1H), 4.65 (d, J=12.5 Hz, 1H), 4.52-4.32 (m, 3H), 4.22 (s, 1H), 4.16-3.98 (m, 1H), 3.87 (s, 3H), 3.58 (s, 3H), 3.47-3.39 (m, 1H), 3.36-3.11 (m, 2H), 2.61 (s, 1H), 2.14-1.93 (m, 2H), 1.91 (s, 3H), 1.41 (t, J=7.1 Hz, 4H), 1.31-1.11 (m, 3H).

Intermediate 459

(rac)-ethyl 1-(3-bromopropyl)-11,12-dimethyl-4,5,6,7,9,11-hexahydropyrazolo[4',3':9,10][1,6]oxaazacycloundecino[8,7,6-hi]indole-2-carboxylate

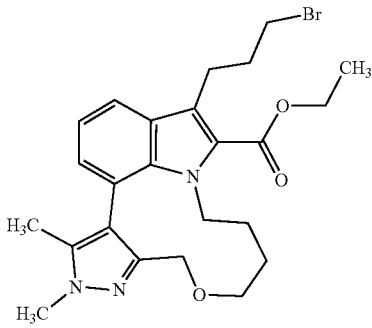 [SMILES: CCOC(=O)c1c(CCCBr)c2cccc3c2n1CCCCOCc1nn(C)c(C)c1-3]

A solution of (rac)-ethyl 1-(3-hydroxypropyl)-11,12-dimethyl-4,5,6,7,9,11-hexahydropyrazolo[4',3':9,10][1,6]oxaazacycloundecino[8,7,6-hi]indole-2-carboxylate (550 mg, 1.29 mmol; see Intermediate 458) and triphenylphosphine (460 mg, 1.75 mmol) in dichloromethane (20 ml) was placed in an ice water bath, and treated with perbromomethane (also referred to herein as tetrabromomethane; 660 mg, 1.99 mmol). After stirring for 30 minutes at that temperature, volatiles were removed under reduced pressure and the residue was purified by normal phase chromatography on silica gel eluting with a gradient of ethyl acetate in hexanes (0-100%) to give the title compound as a colorless film (410 mg).

LRMS (ESIpos) m/z=488 [M+H]$^+$.

Intermediate 460

(rac)-ethyl 1-(3-((6-fluoronaphthalen-1-yl)oxy)propyl)-11,12-dimethyl-4,5,6,7,9,11-hexahydropyrazolo[4',3':9,10][1,6]oxaazacycloundecino[8,7,6-hi]indole-2-carboxylate

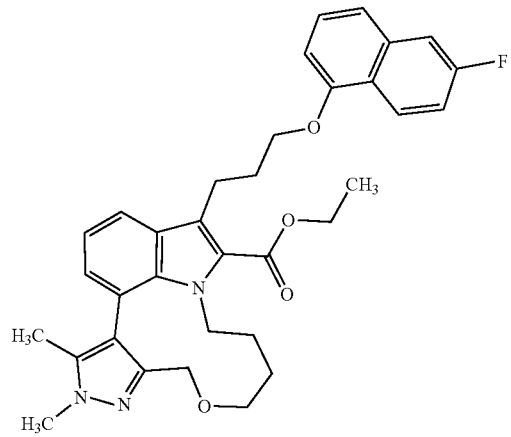 [SMILES: CCOC(=O)c1c(CCCOc2cccc3cc(F)ccc23)c2cccc3c2n1CCCCOCc1nn(C)c(C)c1-3]

To a solution of (rac)-ethyl 1-(3-bromopropyl)-11,12-dimethyl-4,5,6,7,9,11-hexahydropyrazolo[4',3':9,10][1,6]oxaazacycloundecino[8,7,6-hi]indole-2-carboxylate (100 mg, 0.2 mmol; see Intermediate 459), in tetrahydrofuran (10 ml) was added caesium carbonate (400 mg, 1.2 mmol) and 6-fluoronaphthalene-1-ol (80 mg, 0.38 mmol) and the mixture was heated to 55° C. for 64 hours. The mixture was diluted with ethyl acetate (10 ml) and cooled to room temperature, insoluble materials were removed by filtration, and the filter cake was washed with a small amount of ethyl acetate, combined filtrate and washes were concentrated under reduced pressure. The residue was dissolved in dichloromethane, and purified by normal phase flash chromatography on silica gel eluting with a gradient of ethyl acetate in hexanes (25-75%) to give the title compound in moderate purity (130 mg), which was carried forward without further manipulation.

LRMS (ESIpos) m/z=570 [M+H]$^+$.

Intermediate 461 ethyl 12-ethyl-10,13-dimethyl-1-(4-(naphthalen-1-yloxy) butan-2-yl)-4,5,6,7,9,10-hexahydropyrazolo[4',3':9,10][1,6]oxaazacycloundecino[8,7,6-hi]indole-2-carboxylate (Mixture of Stereoisomers)

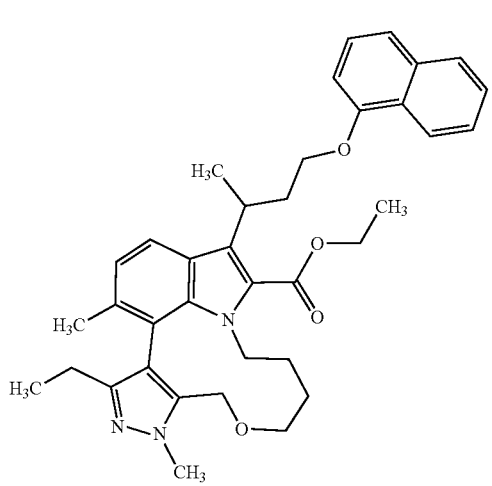 [SMILES: CCOC(=O)c1c(C(C)CCOc2cccc3ccccc23)c2ccc(C)c3c2n1CCCCOCc1c-3c(CC)nn1C]

A mixture of ethyl 12-ethyl-1-(4-hydroxybutan-2-yl)-10,13-dimethyl-4,5,6,7,9,10-hexahydropyrazolo[4',3':9,10][1]oxa[6]azacycloundecino[8,7,6-hi]indole-2-carboxylate (mixture of stereoisomers, 114 mg; see Intermediate 450), 1-naphthol (80 mg), and triphenyl phosphine (250 mg) in tetrahydrofuran (20 ml) at 0° C. was treated with di-tert-butyl azodicarboxylate (168 mg) and was allowed to warm to room temperature over 17 hours. The mixture was adsorbed onto celite and purified by flash chromatography on silica gel eluting with a gradient of ethyl acetate in hexanes (25-50%) to give the title compound (60 mg) in moderate purity as a colorless film.

LRMS (ESIpos) m/z=594 [M+H]$^+$

1H NMR (400 MHz, Chloroform-d) δ 8.18 (ddd, J=70.9, 7.5, 1.4 Hz, 1H), 7.81 (dd, J=21.2, 8.3 Hz, 1H), 7.74 (d, J=8.3 Hz, 1H), 7.50-7.40 (m, 1H), 7.40-7.31 (m, 2H), 7.26 (s, 1H), 7.04 (dd, J=17.2, 8.3 Hz, 1H), 6.61 (dt, J=7.6, 1.4 Hz, 1H), 4.54 (dd, J=32.4, 13.3 Hz, 1H), 4.40-4.19 (m, 2H), 4.18-4.00 (m, 4H), 3.96 (d, J=9.3 Hz, 3H), 3.59-3.23 (m, 1H), 3.06-2.83 (m, 1H), 2.75-2.51 (m, 1H), 2.45 (dp, J=14.2, 7.6, 7.1 Hz, 1H), 2.35-2.16 (m, 2H), 2.04 (s, 1H), 1.99 (d, J=6.1 Hz, 3H), 1.61 (dd, J=15.1, 7.2 Hz, 3H), 1.34-1.16 (m, 6H), 1.11 (dddt, J=12.7, 7.4, 4.4, 2.7 Hz, 1H), 1.04-0.92 (m, 3H), 0.80 (dq, J=14.4, 7.0 Hz, 1H).

Intermediate 462

(rac)-ethyl 3-(4-((tert-butyldimethylsilyl)oxy)butan-2-yl)-7-(3-(hydroxymethyl)-1,5-dimethyl-1H-pyrazol-4-yl)-6-methyl-1H-indole-2-carboxylate

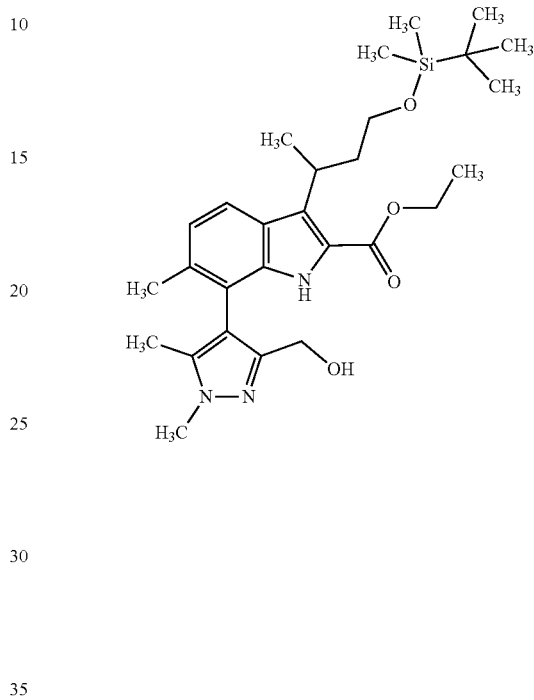

A degassed mixture of (rac)-ethyl 3-(4-((tert-butyldimethylsilyl)oxy)butan-2-yl)-6-methyl-7-(4,4,5,5-tetramethyl-1,3,2-dioxaborolan-2-yl)-1H-indole-2-carboxylate (2.0 g, 3.87 mmol; see Intermediate 442), (4-bromo-1,5-dimethyl-1H-pyrazol-3-yl)methanol (972 mg, 4.74 mmol; see Intermediate 11) and Xphos Pd G2 (208 mg, 0.25 mmol) in aqueous solution of potassium phosphate tribasic (1M, 10 ml) and dioxane (50 ml) was heated to 40° C. for 19 hours. The mixture was cooled to room temperature, volatiles were removed under reduced pressure, and the residue was partitioned between ethyl acetate and water. The layers were separated and the organic phase was washed with saturated aqueous sodium chloride solution, and the combined aqueous phases were back extracted with ethyl acetate. The combined organic layers were dried over magnesium sulfate, insoluble materials were removed by filtration, volatiles were removed under reduced pressure, and the residue was purified by flash chromatography on silica gel eluting with a gradient of ethyl acetate in hexanes (0-100%) to give the title compound as a mixture with other components as an amber oil (1.52 g), which was used without further manipulation.

LRMS (ESI)pos m/z=514 [M+H]$^+$ $^1$H NMR (400 MHz, Chloroform-d) δ 8.94 (d, J=11.9 Hz, 1H), 7.72 (d, J=8.4 Hz, 1H), 7.03 (dd, J=8.5, 1.7 Hz, 1H), 4.52 (dd, J=12.7, 4.7 Hz, 1H), 4.41-4.27 (m, 3H), 4.05-3.92 (m, 1H), 3.86 (s, 3H), 3.69-3.49 (m, 2H), 2.22 (s, 3H), 2.19-2.06 (m, 2H), 2.04 (d, J=2.8 Hz, 3H), 1.47 (dd, J=7.1, 4.1 Hz, 3H), 1.36 (td, J=7.1, 1.2 Hz, 3H), 0.86 (d, J=6.2 Hz, 9H), −0.03 (d, J=7.0 Hz, 6H).

Intermediate 463 ethyl (Z)-1-(4-((tert-butyldimethylsilyl)oxy)butan-2-yl)-11,12,13-trimethyl-4,7,9,11-tetrahydropyrazolo[4',3':9,10][1]oxa[6]azacycloundecino[8,7,6-hi]indole-2-carboxylate (Mixture of Stereoisomers)

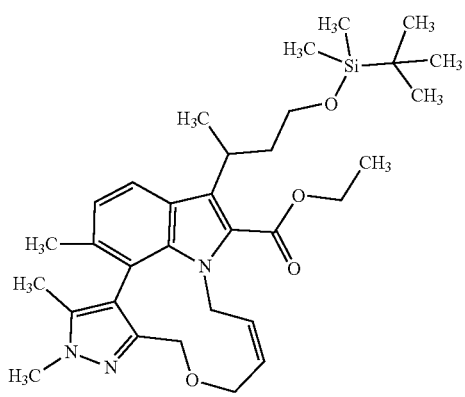 [SMILES: CCOC(=O)c1c(C(C)CCO[Si](C)(C)C(C)(C)C)c2ccc(C)c3c2n1C/C=C\COCc1nn(C)c(C)c1-3]

A mixture of crude (rac)-ethyl 3-(4-((tert-butyldimethylsilyl)oxy)butan-2-yl)-7-(3-(hydroxymethyl)-1,5-dimethyl-1H-pyrazol-4-yl)-6-methyl-1H-indole-2-carboxylate (1.52 g, 2.95 mmol; see Intermediate 462) and (2Z)-1,4-dichlorobut-2-ene (0.4 ml, 475 mg) in N,N-dimethylformamide (40 ml) at ° C. was treated with sodium hydride (60% in oil, 220 mg, 5.5 mmol) and stirred at that temperature for 1 hour, at which time additional sodium hydride (60% in oil, 300 mg) was added and the mixture was allowed to warm to room temperature over 18 hours. (2Z)-1,4-dichlorobut-2-ene (0.4 ml) was added, and the mixture was stirred for 5 hours, additional sodium hydride (60% in oil, 200 mg) was added and the mixture was stirred at room temperature for an additional 18 hours. The reaction was stopped by the addition of acetic acid (2 ml), volatiles were removed under reduced pressure, and the residue was partitioned between water and ethyl acetate. The layers were separated and the organic phase was washed with water, saturated aqueous sodium hydrogen carbonate solution, saturated aqueous sodium chloride solution, the combined aqueous washes were back extracted with ethyl acetate, and the combined organic layers were dried over magnesium sulfate. Insoluble materials were removed by filtration and the filtrate was concentrated under reduced pressure. The residue was purified by flash chromatography on silica gel eluting with a gradient of ethyl acetate in hexanes (0-100%) to give the title compound as a mixture of diastereomers, as an amber gum (720 mg).

LRMS (ESIpos) m/z=566 [M+H]$^+$ $^1$H NMR (400 MHz, Chloroform-d) δ 7.74 (d, J=8.3 Hz, 1H), 7.05 (d, J=8.3 Hz, 1H), 5.29 (s, 1H), 4.98 (s, 1H), 4.77 (d, J=16.2 Hz, 1H), 4.66 (d, J=13.3 Hz, 1H), 4.56 (s, 1H), 4.38 (dd, J=13.9, 8.0 Hz, 3H), 4.05 (s, 3H), 3.92 (d, J=12.9 Hz, 1H), 3.88-3.77 (m, 2H), 3.69 (d, J=17.9 Hz, 1H), 3.58-3.50 (m, 2H), 3.47 (t, J=7.0 Hz, 1H), 1.96 (d, J=2.0 Hz, 3H), 1.89 (d, J=7.9 Hz, 3H), 1.47 (dd, J=21.2, 7.1 Hz, 3H), 1.40 (td, J=7.1, 1.1 Hz, 3H), 0.85 (d, J=6.4 Hz, 9H), −0.04 (dd, J=16.3, 3.5 Hz, 6H).

Intermediate 464 ethyl 1-(4-hydroxybutan-2-yl)-11,12,13-trimethyl-4,5,6,7,9,11-hexahydropyrazolo[4',3':9,10][1]oxa[6]azacycloundecino[8,7,6-hi]indole-2-carboxylate (Mixture of Stereoisomers)

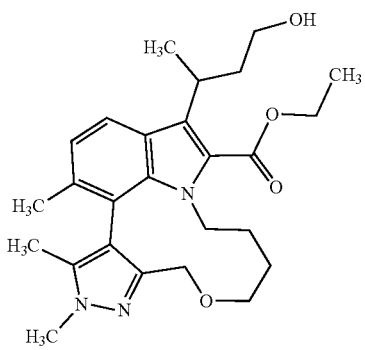 [SMILES: CCOC(=O)c1c(C(C)CCO)c2ccc(C)c3c2n1CCCCOCc1nn(C)c(C)c1-3]

To a degassed mixture of ethyl (Z)-1-(4-((tert-butyldimethylsilyl)oxy)butan-2-yl)-11,12,13-trimethyl-4,7,9,11-tetrahydropyrazolo[4',3':9,10][1]oxa[6]azacycloundecino[8,7,6-hi]indole-2-carboxylate (mixture of stereoisomers; 715 mg, 1.26 mmol; see Intermediate 463) in ethanol (100 ml) was added palladium on carbon (10%, 500 mg), the mixture was degassed, and then subjected to an atmosphere of hydrogen for 15 hours. The mixture was degassed, filtered through a pad of celite, and volatiles were removed; the residue was purified by flash chromatography on silica gel eluting with a gradient of ethyl acetate in hexanes (50-100%) to give the title compound as a mixture of isomers, as a white foam (460 mg).

LRMS (ESIpos) m/z=454 [M+H]$^+$ $^1$H NMR (400 MHz, Chloroform-d) δ 7.70 (dd, J=8.3, 6.7 Hz, 1H), 7.04 (d, J=8.3 Hz, 1H), 4.61-4.28 (m, 4H), 4.08 (d, J=10.4 Hz, 1H), 3.95 (t, J=7.6 Hz, 1H), 3.91 (d, J=2.1 Hz, 3H), 3.84 (dd, J=15.4, 8.1 Hz, 1H), 3.58-3.49 (m, 1H), 3.46 (dd, J=10.9, 5.4 Hz, 1H), 3.42-3.31 (m, 1H), 3.27 (t, J=10.4 Hz, 1H), 2.25-2.11 (m, 1H), 2.11-2.00 (m, 4H), 1.86 (d, J=23.4 Hz, 3H), 1.51 (t, J=7.4 Hz, 3H), 1.44-1.36 (m, 4H), 1.30 (d, J=20.7 Hz, 1H), 1.16 (d, J=10.5 Hz, 2H).

Intermediate 465 ethyl 1-(4-((6-fluoronaphthalen-1-yl)oxy)butan-2-yl)-11,12,13-trimethyl-4,5,6,7,9,11-hexahydropyrazolo[4',3':9,10][1]oxa[6]azacycloundecino[8,7,6-hi]indole-2-carboxylate (Mixture of Stereoisomers)

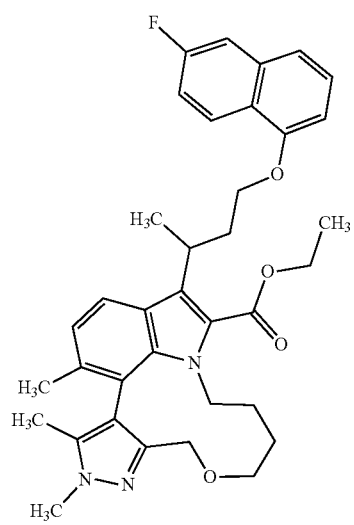 [SMILES: CCOC(=O)c1c(C(C)CCOc2cccc3cc(F)ccc23)c2ccc(C)c3c2n1CCCCOCc1nn(C)c(C)c1-3]

To a solution of triphenylphosphine (780 mg, 3 mmol) in tetrahydrofuran (30 ml) at 0° C. was added diisopropyl azodicarboxylate (0.6 ml, 3 mmol) and the mixture was stirred at that temperature for 15 minutes. A portion of the above white suspension (10 ml, 1 mmol) was added to an ice cold mixture of ethyl 1-(4-hydroxybutan-2-yl)-11,12,13-trimethyl-4,5,6,7,9,11-hexahydropyrazolo[4',3':9,10][1]oxa[6]azacycloundecino[8,7,6-hi]indole-2-carboxylate (mixture of stereoisomers; 230 mg, 0.5 mmol; see Intermediate 464) and 6-fluoronaphthol (also referred to herein as 6-fluoronaphthalene-1-ol; 123 mg, 0.76 mmol) in tetrahydrofuran (10 ml), and the mixture was allowed to warm to room temperature over 20 hours. Volatiles were removed and the residue was purified by flash chromatography on silica gel eluting with a gradient of ethyl acetate in hexanes (25-50%) to give the title compound as a colorless film (110 mg).

LRMS (ESIpos) m/z=598 [M+H]$^+$ $^1$H NMR (400 MHz, Chloroform-d) δ 8.22 (ddd, J=9.2, 7.3, 5.8 Hz, 1H), 7.75 (dd, J=13.6, 8.2 Hz, 1H), 7.36 (ddd, J=10.1, 5.9, 2.6 Hz, 1H), 7.31-7.24 (m, 2H), 7.18 (dddd, J=11.0, 9.3, 8.4, 2.6 Hz, 1H), 7.05 (dd, J=9.5, 8.3 Hz, 1H), 6.57 (dd, J=5.1, 3.5 Hz, 1H), 4.51 (dd, J=22.0, 12.5 Hz, 1H), 4.38 (d, J=12.5, 5.6 Hz, 1H), 4.31-4.15 (m, 2H), 4.17-4.09 (m, 2H), 4.09-4.01 (m, 1H), 4.01-3.90 (m, 1H), 3.88 (s, 3H), 3.50-3.33 (m, 1H), 3.25 (qd, J=11.1, 5.5 Hz, 1H), 2.58 (tdt, J=21.6, 9.5, 5.9 Hz, 1H), 2.49-2.34 (m, 1H), 2.11-2.01 (m, 4H), 1.83 (d, J=11.0 Hz, 3H), 1.58 (dd, J=16.0, 7.2 Hz, 3H), 1.46-0.98 (m, 7H); $^{19}$F NMR (376 MHz, Chloroform-d) δ −115.13, −115.28.

Intermediate 466

(rac)-ethyl 1-(3-((6-chloronaphthalen-1-yl)oxy)propyl)-11,12-dimethyl-4,5,6,7,9,11-hexahydropyrazolo[4',3':9,10][1,6]oxaazacycloundecino[8,7,6-hi]indole-2-carboxylate

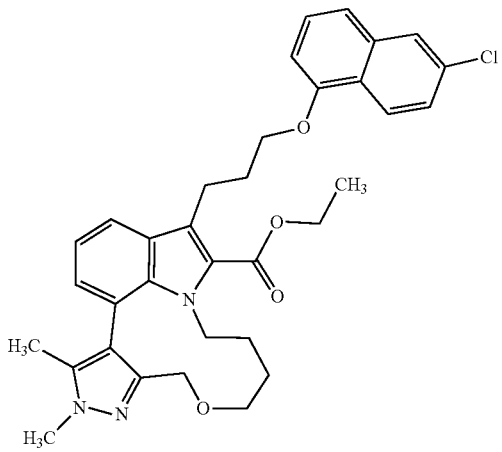 [SMILES: CCOC(=O)c1c(CCCOc2cccc3cc(Cl)ccc23)c2cccc3c2n1CCCCOCc1nn(C)c(C)c1-3]

A solution of (rac)-ethyl 1-(3-bromopropyl)-11,12-dimethyl-4,5,6,7,9,11-hexahydropyrazolo[4',3':9,10][1,6]oxaazacycloundecino[8,7,6-hi]indole-2-carboxylate (100 mg, 0.2 mmol; see Intermediate 459), in tetrahydrofuran (10 ml) was treated with caesium carbonate (400 mg, 1.2 mmol), 6-chloronaphthalene-1-ol (80 mg, 0.38 mmol), and heated to 55° C. for 64 hours. The mixture was diluted with ethyl acetate (10 ml), cooled to room temperature, the resulting solids were removed by filtration, and were washed with a small amount of ethyl acetate. The combined filtrates and washes were concentrated under reduced pressure, and the residue was dissolved in dichloromethane, and purified by normal phase flash chromatography on silica gel eluting with a gradient of ethyl acetate in hexanes (25-75%) to afford the title compound (125 mg) in moderate purity, which was used without further manipulation.

LRMS (ESIpos) m/z=586 [M+H]$^+$

Intermediate 467 ethyl 3-(3-((tert-butyldimethylsilyl)oxy)propyl)-6-methyl-7-(4,4,5,5-tetramethyl-1,3,2-dioxaborolan-2-yl)-1H-indole-2-carboxylate

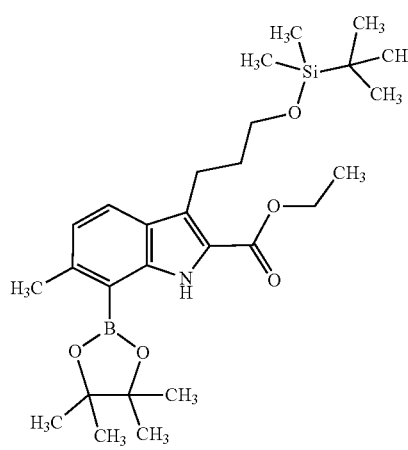

A solution of ethyl 3-(3-hydroxypropyl)-6-methyl-7-(4,4,5,5-tetramethyl-1,3,2-dioxaborolan-2-yl)-1H-indole-2-carboxylate (3.48 g, 8.98 mmol; see Intermediate 71) in dichloromethane (88 mL) was treated with 1H-imidazole (1.21 g, 17.9 mmol, 2 eq), and tert-butyldimethylsilyl chloride (2.01 g, 13.4 mmol, 1.5 eq), to afford a white suspension, which was stirred at room temperature for 5 hours. The reaction mixture was diluted with water (200 ml), and the aqueous phase was extracted three times with dichloromethane (100 ml each), the combined organic layers were washed with saturated aqueous sodium chloride solution and dried over magnesium sulfate. Insoluble materials were removed by filtration, volatiles were removed under reduced pressure, and the residue was purified by flash chromatography on silica gel eluting with a gradient of dichloromethane in hexanes (0-60%) to afford the title compound as a colorless oil (2.99 g).

LRMS (ESIpos) m/z=502 [M+H]$^+$ $^1$H NMR (400 MHz, Chloroform-d) δ 9.83 (s, 1H), 7.67 (d, J=8.1 Hz, 1H), 6.96 (d, J=8.1 Hz, 1H), 4.45-4.34 (m, 2H), 3.67 (t, J=6.4 Hz, 2H), 3.12 (t, J=7.7 Hz, 2H), 2.67 (s, 3H), 1.87 (p, J=6.8 Hz, 2H), 1.47-1.35 (m, 18H), 0.92 (s, 12H), 0.08 (dd, J=18.3, 1.5 Hz, 9H).

Intermediate 468 ethyl 3-(3-((tert-butyldimethylsilyl)oxy) propyl)-7-(3-ethyl-5-(hydroxymethyl)-1-methyl-1H-pyrazol-4-yl)-6-methyl-1H-indole-2-carboxylate

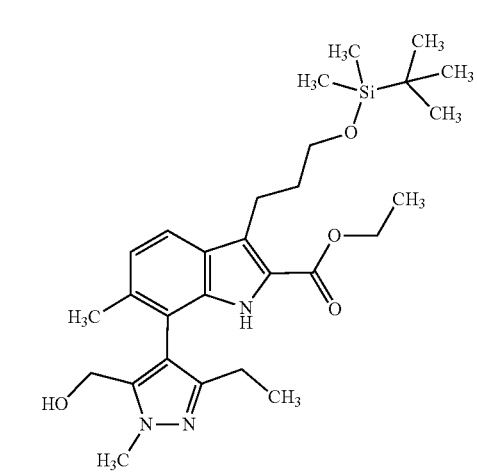 [SMILES: CCOC(=O)c1[nH]c2c(-c3c(CC)nn(C)c3CO)c(C)ccc2c1CCCO[Si](C)(C)C(C)(C)C]

A degassed mixture of ethyl 3-(3-((tert-butyldimethylsilyl)oxy)propyl)-6-methyl-7-(4,4,5,5-tetramethyl-1,3,2-dioxaborolan-2-yl)-1H-indole-2-carboxylate (2.80 g, 5.58 mmol; see Intermediate 467), (4-bromo-3-ethyl-1-methyl-1H-pyrazol-5-yl)methanol (1.46 g, 6.69 mmol; see Intermediate 509), XPhos Pd G2 (219 mg, 279 µmol), aqueous solution of potassium phosphate tribasic (1M, 11.1 mL, 11.1 mmol) in water (25 mL) and 1,4-dioxane (121 mL) was heated to 40° C. for 1 hour. The reaction mixture was cooled to room temperature, diluted with ethyl acetate and water, and the layers were separated. The organic layer was washed with saturated aqueous sodium chloride solution and dried over magnesium sulfate. Solids were removed by filtration and volatiles were removed under reduced pressure. The residue was purified by flash chromatography on silica gel eluting with a gradient of ethyl acetate in hexanes (0-100%) to give the title compound (1.73 g, 3.36 mmol).

LRMS (ESIpos): m/z=514.4 [M+H]$^+$ $^1$H NMR (400 MHz, Chloroform-d) δ 8.35 (s, 1H), 7.59 (d, J=8.2 Hz, 1H), 7.26 (s, 2H), 7.07 (d, J=8.2 Hz, 1H), 4.48-4.25 (m, 4H), 4.12 (q, J=7.1 Hz, 3H), 4.06-3.93 (m, 3H), 3.71 (t, J=6.4 Hz, 2H), 3.19-3.02 (m, 2H), 2.39 (qd, J=7.6, 1.3 Hz, 2H), 2.22 (s, 3H), 2.04 (s, 4H), 1.90 (dt, J=12.9, 6.4 Hz, 2H), 1.70-1.46 (m, 1H), 1.38 (t, J=7.1 Hz, 3H), 1.26 (t, J=7.1 Hz, 4H), 1.03 (dd, J=8.1, 7.0 Hz, 3H), 0.92 (s, 11H).

Intermediate 469

(rac)-ethyl (Z)-1-(3-((tert-butyldimethylsilyl)oxy)propyl)-12-ethyl-10,13-dimethyl-4,7,9,10-tetrahydropyrazolo[4',3':9,10][1]oxa[6]azacycloundecino[8,7,6-hi]indole-2-carboxylate

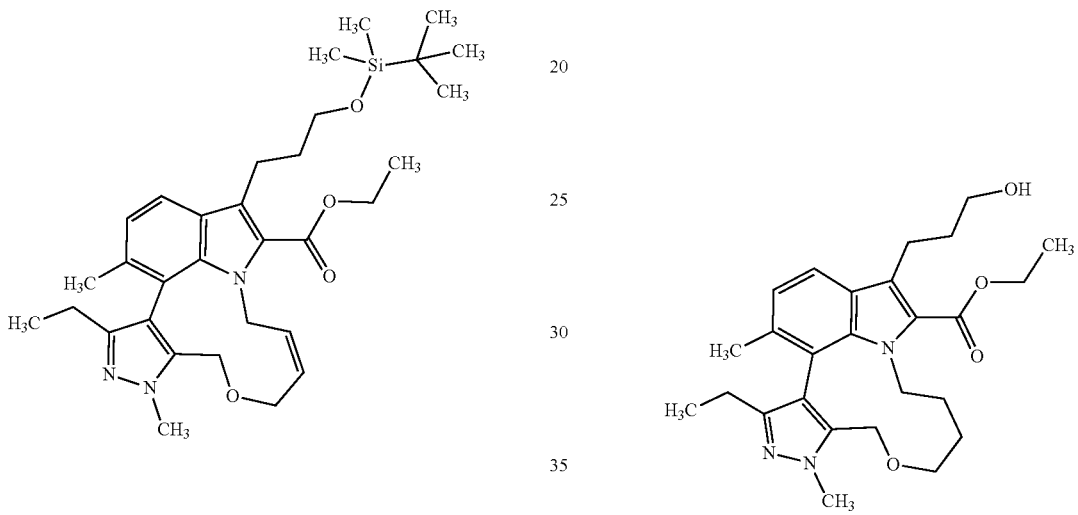

To a solution of ethyl 3-(3-((tert-butyldimethylsilyl)oxy)propyl)-7-(3-ethyl-5-(hydroxymethyl)-1-methyl-1H-pyrazol-4-yl)-6-methyl-1H-indole-2-carboxylate (1.24 g, 2.41 mmol; see Intermediate 468) in N,N-dimethylformamide (37 mL) at 0° C. were added (2Z)-1,4-dichlorobut-2-ene (278 μL, 2.65 mmol) and sodium hydride (60% in oil, 63.5 mg, 2.65 mmol) and the mixture was stirred for 2 hours. Additional sodium hydride (60% in oil, 63.5 mg, 2.65 mmol) was added and the mixture was stirred for 2 hours; additional sodium hydride (60% in oil, 63.5 mg, 2.65 mmol) was added and the mixture was allowed to warm to room temperature over 19 hours, at which time additional sodium hydride (60% in oil, 63.5 mg, 2.65 mmol) was added and the reaction stirred at room temperature for 5 hours. The reaction was then stopped by the addition of acetic acid (0.5 mL), volatiles were removed under reduced pressure, and the residue was diluted with water and ethyl acetate. The layers were separated and the organic layer was washed twice with saturated aqueous sodium chloride. The combined aqueous washes were back extracted twice with ethyl acetate. The combined organic layers were dried over magnesium sulfate, solids were removed by filtration and volatiles were removed under reduced pressure. The residue was purified by flash chromatography on silica gel eluting with a gradient of ethyl acetate in hexanes (10-30%) to give the title compound (940 mg, 1.66 mmol).

LRMS (ESIpos): m/z=566.6 [M+H]$^+$ $^1$H NMR (400 MHz, Chloroform-d) δ 7.60 (d, J=8.1 Hz, 1H), 5.21 (td, J=11.3, 4.7 Hz, 1H), 5.12-4.94 (m, 2H), 4.75-4.55 (m, 2H), 4.44-4.29 (m, 3H), 4.00 (s, 3H), 3.83 (dd, J=12.9, 4.8 Hz, 1H), 3.75-3.63 (m, 3H), 3.22-3.02 (m, 2H), 2.22-2.08 (m, 2H), 1.97-1.85 (m, 5H), 1.41 (t, J=7.1 Hz, 3H), 0.93 (s, 8H), 0.90 (t, J=7.5 Hz, 4H), 0.07 (s, 6H).

Intermediate 470

(rac)-ethyl 12-ethyl-1-(3-hydroxypropyl)-10,13-dimethyl-4,5,6,7,9,10-hexahydropyrazolo[4',3':9,10][1]oxa[6]azacycloundecino[8,7,6-hi]indole-2-carboxylate To a degassed solution of (rac)-(Z)-ethyl 1-(3-((tert-butyldimethylsilyl)oxy)propyl)-12-ethyl-10,13-dimethyl-4,7,9,10-tetrahydropyrazolo[4',3':9,10][1,6]oxaazacycloundecino[8,7,6-hi]indole-2-carboxylate (940 mg, 1.66 mmol; see Intermediate 469) in ethanol (150 mL) was added palladium on carbon (10% by mass, 883 mg, 830 μmol) and the mixture was placed under an atmosphere of hydrogen for 18 hours. The reaction mixture was degassed, filtered through celite and volatiles were removed under reduced pressure to give title compound (830 mg) which was used without further manipulation.

LRMS (ESIpos): m/z=454.4 [M+H]$^+$ $^1$H NMR (400 MHz, Chloroform-d) δ 7.59 (d, J=8.1 Hz, 1H), 7.07 (d, J=8.1 Hz, 1H), 4.58 (d, J=12.9 Hz, 1H), 4.49-4.36 (m, 1H), 4.38-4.27 (m, 1H), 4.12 (t, J=11.9 Hz, 1H), 3.99 (s, 3H), 3.72 (q, J=7.0 Hz, 1H), 3.61 (t, J=6.2 Hz, 2H), 3.52 (s, 1H), 3.24-3.12 (m, 2H), 3.02 (s, 1H), 2.28 (d, J=7.4 Hz, 2H), 1.39 (t, J=7.0 Hz, 3H), 1.24 (t, J=6.9 Hz, 2H), 1.22 (s, 3H), 1.10 (d, J=16.1 Hz, 1H), 1.02-0.89 (m, 4H), 0.93-0.83 (m, 1H), 0.08 (d, J=15.9 Hz, 1H).

Intermediate 471

(rac)-ethyl 12-ethyl-1-(3-((6-fluoronaphthalen-1-yl)oxy)propyl)-10,13-dimethyl-4,5,6,7,9,10-hexahydropyrazolo[4',3':9,10][1]oxa[6]azacycloundecino[8,7,6-hi]indole-2-carboxylate

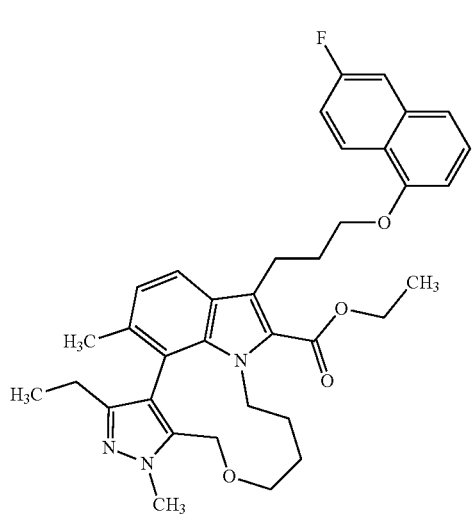 [SMILES: CCOC(=O)c1c(CCCOc2cccc3cc(F)ccc23)c2ccc(C)c3c2n1CCCCOCc1c-3c(CC)nn1C]

To a stirred solution of crude (rac)-ethyl 12-ethyl-1-(3-hydroxypropyl)-10,13-dimethyl-4,5,6,7,9,10-hexahydropyrazolo[4',3':9,10][1]oxa[6]azacycloundecino[8,7,6-hi]indole-2-carboxylate (200 mg; see Intermediate 470) at 0° C. were added 6-fluoronaphthalen-1-ol (107 mg, 660 µmol), tetrahydrofuran (15 mL), triphenylphosphine (230 mg, 880 µmol) and (E)-di-tert-butyl diazene-1,2-dicarboxylate (also referred to herein as di-tert-butyl azodicarboxylate; 157 mg, 682 µmol). 20 hours later, triphenylphosphine (230 mg, 880 µmol) and (E)-di-tert-butyl diazene-1,2-dicarboxylate (157 mg, 682 µmol) were added again. After stirring at room temperature for 150 minutes, water (0.5 ml) was added. The volatiles were removed under reduced pressure and the residue was purified by flash chromatography on silica gel eluting with a gradient of ethyl acetate in hexanes (0-50%) to give the title compound (130 mg, 250 µmol).

LRMS (ESIpos): m/z=598.4 [M+H]$^+$ $^1$H NMR (400 MHz, Chloroform-d) δ 8.35 (dd, J=9.2, 5.8 Hz, 1H), 7.61 (d, J=8.2 Hz, 1H), 7.44-7.29 (m, 3H), 7.28-7.19 (m, 1H), 7.01 (d, J=8.2 Hz, 1H), 6.71 (dd, J=7.0, 1.7 Hz, 1H), 4.58 (d, J=13.5 Hz, 2H), 4.43-4.23 (m, 3H), 4.24-4.06 (m, 3H), 3.97 (s, 3H), 3.57-3.23 (m, 3H), 3.03-2.92 (m, 1H), 2.41-2.19 (m, 4H), 1.98 (s, 3H), 1.36 (t, J=7.1 Hz, 3H), 1.30-1.17 (m, 2H), 1.24 (s, 1H), 1.16-1.02 (m, 1H), 0.98 (t, J=7.6 Hz, 3H).

Intermediate 472

(rac)-ethyl 12-ethyl-10,13-dimethyl-1-(3-((5,6,7,8-tetrahydronaphthalen-1-yl)oxy)propyl)-4,5,6,7,9,10-hexahydropyrazolo[4',3':9,10][1]oxa[6]azacycloundecino[8,7,6-hi]indole-2-carboxylate

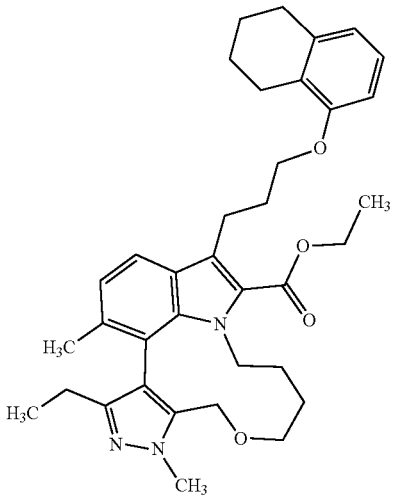 [SMILES: CCOC(=O)c1c(CCCOc2cccc3c2CCCC3)c2ccc(C)c3c2n1CCCCOCc1c-3c(CC)nn1C]

A mixture of triphenylphosphine (230 mg, 880 µmol) and (E)-di-tert-butyl diazene-1,2-dicarboxylate (157 mg, 682 µmol) in tetrahydrofuran (5 mL) at 0° C. was stirred for 10 minutes, and was then added to a solution of crude (rac)-ethyl 12-ethyl-1-(3-hydroxypropyl)-10,13-dimethyl-4,5,6,7,9,10-hexahydropyrazolo[4',3':9,10][1]oxa[6]azacycloundecino[8,7,6-hi]indole-2-carboxylate (200 mg; see Intermediate 470) and 5,6,7,8-tetrahydronaphthalen-1-ol (97.8 mg, 660 µmol). in tetrahydrofuran (10 ml) at 0° C. The mixture was allowed to warm to room temperature over 20 hours, then to the mixture were added triphenylphosphine (230 mg, 880 µmol) and (E)-di-tert-butyl diazene-1,2-dicarboxylate (157 mg, 682 µmol), and the mixture was stirred at that temperature for 6 hours, the solution was then heated to 40° C. for 2 hours. 5,6,7,8-Tetrahydronaphthalen-1-ol (97.8 mg, 660 µmol), triphenylphosphine (230 mg, 880 µmol) and (E)-di-tert-butyl diazene-1,2-dicarboxylate (157 mg, 682 µmol) were then added and the mixture was stirred at that temperature for 18 hours, at which time further 5,6,7,8-tetrahydronaphthalen-1-ol (97.8 mg, 660 µmol), triphenylphosphine (230 mg, 880 µmol) and (E)-di-tert-butyl diazene-1,2-dicarboxylate (157 mg, 682 µmol) were added. After stirring at that temperature for 7 hours, the mixture was treated with water (0.5 ml), the volatiles were removed under reduced pressure and the residue was purified by flash chromatography on silica gel eluting with a gradient of ethyl acetate in hexanes (0-50%) to give the title compound (200 mg, 342 µmol).

LRMS (ESIpos): m/z=584.5 [M+H]$^+$ $^1$H NMR (400 MHz, Chloroform-d) δ 7.61 (d, J=8.2 Hz, 1H), 7.09-6.99 (m, 2H), 6.69 (d, J=7.6 Hz, 1H), 6.62 (d, J=8.0 Hz, 1H), 4.59 (d, J=13.4 Hz, 2H), 4.47-4.26 (m, 3H), 4.12 (tt, J=10.2, 2.6 Hz, 1H), 4.05 (t, J=6.2 Hz, 2H), 3.98 (s, 3H), 3.54 (dt, J=11.8, 7.1 Hz, 1H), 3.27 (dddd, J=38.4, 13.5, 8.7, 6.7 Hz, 2H), 2.98 (ddt, J=11.8, 8.8, 4.4 Hz, 1H), 2.77 (t, J=6.2 Hz, 4H), 2.29 (qd, J=7.5, 1.6 Hz, 2H), 2.25-2.14 (m, 2H), 1.99 (s, 3H), 1.80 (tqd, J=12.2, 5.7, 3.6, 2.9 Hz, 4H), 1.48 (d, J=5.7 Hz, 2H), 1.40 (t, J=7.2 Hz, 4H), 1.30-1.05 (m, 4H), 0.98 (t, J=7.6 Hz, 3H).

Intermediate 473

(rac)-ethyl 1-(3-(4-chloro-3,5-dimethylphenoxy)propyl)-12-ethyl-10,13-dimethyl-4,5,6,7,9,10-hexahydropyrazolo[4',3':9,10][1]oxa[6]azacycloundecino[8,7,6-hi]indole-2-carboxylate

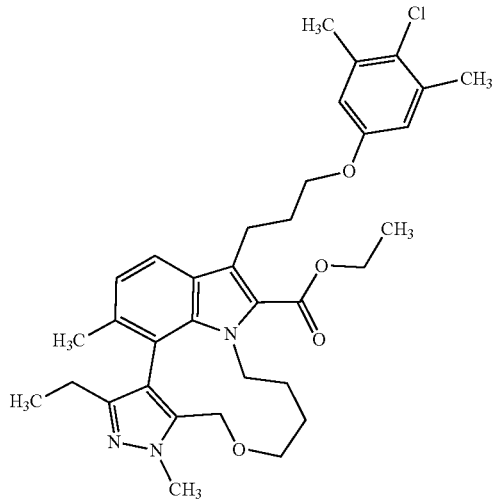 [SMILES: CCOC(=O)c1c(CCCOc2cc(C)c(Cl)c(C)c2)c2ccc(C)c3c2n1CCCCOCc1c-3c(CC)nn1C]

A mixture of triphenylphosphine (230 mg, 880 µmol) and (E)-di-tert-butyl diazene-1,2-dicarboxylate (157 mg, 682 µmol) in tetrahydrofuran (5 mL) at 0° C. was stirred for 10 minutes, and was then added to a solution of crude (rac)-ethyl 12-ethyl-1-(3-hydroxypropyl)-10,13-dimethyl-4,5,6,7,9,10-hexahydropyrazolo[4',3':9,10][1]oxa[6]azacycloundecino[8,7,6-hi]indole-2-carboxylate (200 mg; see Intermediate 470) and 4-chloro-3,5-dimethylphenol (97.8 mg, 660 µmol) in tetrahydrofuran (10 ml) at 0° C. The mixture was allowed to warm to room temperature over 20 hours, then to the mixture were added triphenylphosphine (230 mg, 880 µmol) and (E)-di-tert-butyl diazene-1,2-dicarboxylate (157 mg, 682 µmol) and the mixture was stirred at that temperature for 6 hours, and the solution was then heated to 40° C. for 2 hours. 4-Chloro-3,5-dimethylphenol (97.8 mg, 660 µmol), triphenylphosphine (230 mg, 880 µmol) and (E)-di-tert-butyl diazene-1,2-dicarboxylate (157 mg, 682 µmol) were then added and the mixture was stirred at that temperature for 18 hours, at which time further 4-chloro-3,5-dimethylphenol (97.8 mg, 660 µmol), triphenylphosphine (230 mg, 880 µmol) and (E)-di-tert-butyl diazene-1,2-dicarboxylate (157 mg, 682 µmol) were added. After stirring at that temperature for 7 hours, the mixture was treated with water (0.5 ml), the volatiles were removed under reduced pressure and the residue was purified by flash chromatography on silica gel eluting with a gradient of ethyl acetate in hexanes (0-50%) to give the title compound (260 mg, 439 µmol).

LRMS (ESIpos): m/z=592.4 [M+H]$^+$ $^1$H NMR (400 MHz, Chloroform-d) δ 7.58 (d, J=8.2 Hz, 1H), 7.03 (d, J=8.2 Hz, 1H), 6.62 (s, 2H), 4.58 (dd, J=13.7, 2.8 Hz, 2H), 4.43-4.26 (m, 3H), 4.16-4.02 (m, 2H), 4.01-3.91 (m, 5H), 3.52 (dt, J=11.8, 7.0 Hz, 1H), 3.34-3.13 (m, 2H), 2.97 (ddt, J=11.6, 8.7, 4.5 Hz, 1H), 2.32 (s, 6H), 2.27 (qd, J=7.6, 1.5 Hz, 2H), 2.14 (h, J=6.8 Hz, 2H), 1.98 (s, 3H), 1.53-1.34 (m, 4H), 1.32-1.03 (m, 5H), 0.97 (t, J=7.6 Hz, 3H).

Intermediate 474 ethyl 3-(3-((tert-butyldimethylsilyl)oxy)propyl)-7-(5-ethyl-3-(hydroxymethyl)-1-methyl-1H-pyrazol-4-yl)-1H-indole-2-carboxylate

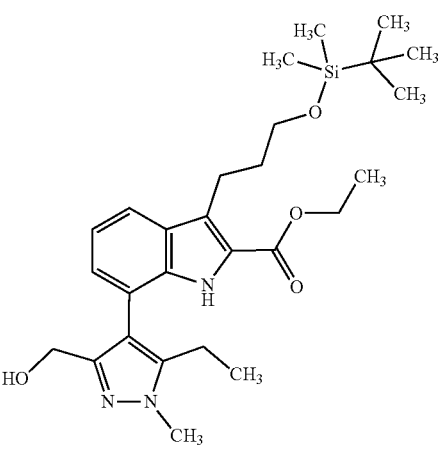 [SMILES: CCOC(=O)c1[nH]c2c(-c3c(CO)nn(C)c3CC)cccc2c1CCCO[Si](C)(C)C(C)(C)C]

A degassed mixture of ethyl 3-(3-((tert-butyldimethylsilyl)oxy)propyl)-7-(4,4,5,5-tetramethyl-1,3,2-dioxaborolan-2-yl)-1H-indole-2-carboxylate (770 mg, 1.58 mmol; see Intermediate 39), (4-bromo-5-ethyl-1-methyl-1H-pyrazol-3-yl)methanol (290 mg, 1.32 mmol; see Intermediate 400), XPhos Pd G2 (51.9 mg, 66 µmol), aqueous solution of potassium phosphate tribasic (1 M, 2.64 mL, 2.64 mmol) and water (7 mL) in 1,4-dioxane (29.3 mL) was heated to 40° C. for 150 minutes. The reaction mixture was cooled to room temperature, diluted with ethyl acetate and water, layers were separated, the organic layer was washed with saturated aqueous sodium chloride solution and dried over magnesium sulfate. Solids were removed by filtration and volatiles were removed under reduced pressure. The residue was purified by flash chromatography on silica gel eluting with a gradient of ethyl acetate in hexanes (0-50%) to give the title compound (620 m g, 1.24 mmol).

LRMS (ESIpos): m/z=501.4 [M+H]$^+$ $^1$H NMR (400 MHz, Chloroform-d) δ 9.66 (s, 1H), 7.70 (d, J=7.9 Hz, 1H), 7.21-7.14 (m, 1H), 7.12 (dd, J=7.2, 1.3 Hz, 1H), 4.52 (s, 2H), 4.37 (q, J=7.1 Hz, 2H), 4.12 (q, J=7.2 Hz, 1H), 3.92 (s, 3H), 3.72 (t, J=6.4 Hz, 2H), 3.22-3.13 (m, 2H), 2.61 (d, J=7.8 Hz, 2H), 2.04 (s, 1H), 1.99-1.87 (m, 2H), 1.38 (t, J=7.1 Hz, 3H), 1.25 (d, J=6.8 Hz, 1H), 1.13 (t, J=7.6 Hz, 3H), 0.93 (s, 7H), 0.92 (s, 1H), 0.07 (s, 5H).

Intermediate 475

(rac)-ethyl (Z)-1-(3-((tert-butyldimethylsilyl)oxy)propyl)-12-ethyl-10,13-dimethyl-4,7,9,10-tetrahydropyrazolo[4',3':9,10][1]oxa[6]azacycloundecino[8,7,6-hi]indole-2-carboxylate

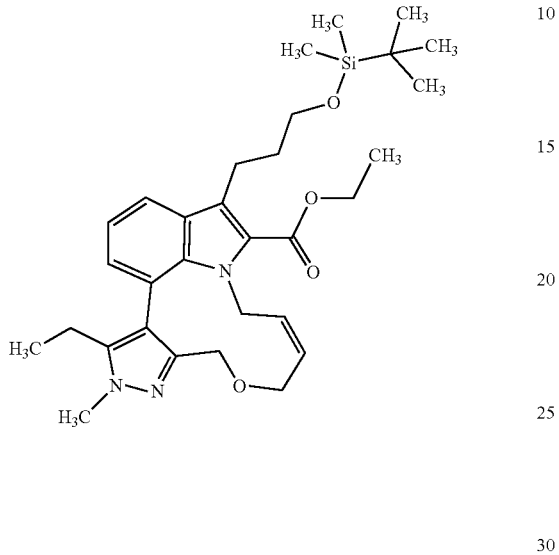

A mixture of ethyl 3-(3-((tert-butyldimethylsilyl)oxy)propyl)-7-(5-ethyl-3-(hydroxymethyl)-1-methyl-1H-pyrazol-4-yl)-1H-indole-2-carboxylate (590 mg, 1.18 mmol; see Intermediate 474) and (2Z)-1,4-dichlorobut-2-ene (148 μL, 1.41 mmol) in N,N-dimethylformamide (18 mL) at 0° C. was treated with sodium hydride (60% in oil, 30.9 mg, 1.29 mmol). After 2 hours, sodium hydride (60% in oil, 30.9 mg, 1.29 mmol) was added and the mixture was allowed to warm to room temperature over 17 hours, Additional sodium hydride (60% in oil, 30.9 mg, 1.29 mmol) was added, and the mixture was stirred for 5 hours, at which time additional sodium hydride (60% in oil, 30.9 mg, 1.29 mmol) was added and the mixture stirred at room temperature for 23 hours. The reaction was then stopped by the addition of acetic acid (0.5 mL), volatiles were removed under reduced pressure, and the residue was diluted with water and ethyl acetate. The layers were separated and the organic layers were washed twice with saturated aqueous sodium chloride solution. The combined aqueous layers were back extracted twice with ethyl acetate, and the combined organic layers were dried over magnesium sulfate. Solids were removed by filtration and volatiles were removed under reduced pressure. The residue was purified by flash chromatography on silica gel eluting with a gradient of ethyl acetate in hexanes (0-50%) to give the title compound (490 mg, 888 μmol).

LRMS (ESIpos): m/z=553.5 [M+H]$^+$ $^1$H NMR (400 MHz, Chloroform-d) δ 7.67 (dd, J=8.0, 1.3 Hz, 1H), 7.07 (dd, J=8.0, 7.1 Hz, 1H), 6.86 (dd, J=7.1, 1.2 Hz, 1H), 5.36-5.14 (m, 2H), 5.06-4.96 (m, 1H), 4.84 (dd, J=15.6, 10.4 Hz, 1H), 4.54 (d, J=13.2 Hz, 1H), 4.46-4.26 (m, 3H), 3.94 (d, J=11.9 Hz, 1H), 3.90 (s, 3H), 3.79-3.64 (m, 3H), 3.22-3.01 (m, 2H), 2.31-2.20 (m, 2H), 1.96-1.83 (m, 1H), 1.38 (t, J=7.1 Hz, 3H), 0.89 (s, 9H), 0.95-0.85 (m, 3H), 0.04 (s, 6H).

Intermediate 476

(rac)-ethyl 12-ethyl-1-(3-hydroxypropyl)-11-methyl-4,5,6,7,9,11-hexahydropyrazolo[4',3':9,10][1]oxa[6]azacycloundecino[8,7,6-hi]indole-2-carboxylate

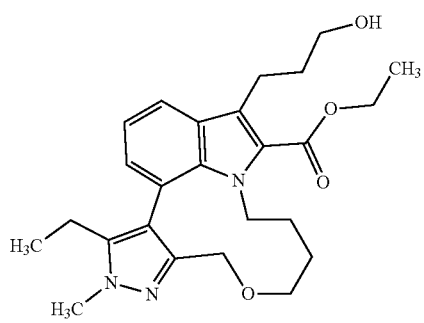 [SMILES: CCOC(=O)c1c(CCCO)c2cccc3c2n1CCCCOCc1nn(C)c(CC)c1-3]

A degassed mixture of (rac)-ethyl (Z)-12-ethyl-1-(3-hydroxypropyl)-11-methyl-4,7,9,11-tetrahydropyrazolo[4',3':9,10][1]oxa[6]azacycloundecino[8,7,6-hi]indole-2-carboxylate (490 mg, 888 μmol; see Intermediate 475) in ethanol (110 mL) was treated with palladium on carbon (10% by mass, 472 mg, 444 μmol) and placed under an atmosphere of hydrogen for 3 hours. Subsequently, the reaction mixture was degassed, filtered through celite and volatiles were removed under reduced pressure. The residue was purified by flash chromatography on silica gel eluting with a gradient of ethyl acetate in hexanes (0-50%) to give the title compound (320 mg, 728 μmol).

LRMS (ESIpos): m/z=440.4[M+H]$^+$ $^1$H NMR (400 MHz, Chloroform-d) δ 7.62 (dd, J=7.8, 2.2 Hz, 1H), 7.06 (q, J=6.9 Hz, 1H), 6.94 (dd, J=7.2, 3.6 Hz, 1H), 4.60 (dd, J=12.5, 3.1 Hz, 1H), 4.38 (td, J=7.2, 3.7 Hz, 1H), 4.30 (ddd, J=11.0, 8.2, 3.5 Hz, 2H), 4.19 (dt, J=14.3, 7.1 Hz, 1H), 4.04 (ddt, J=14.0, 10.1, 4.4 Hz, 1H), 3.83 (d, J=4.2 Hz, 3H), 3.55 (q, J=6.4, 5.9 Hz, 2H), 3.38 (dt, J=9.8, 4.4 Hz, 1H), 3.27-3.05 (m, 4H), 2.99 (s, 1H), 2.23 (dqq, J=11.5, 7.9, 3.9 Hz, 2H), 1.98 (td, J=11.8, 10.5, 5.3 Hz, 1H), 1.34 (pt, J=10.6, 5.9 Hz, 5H), 1.14 (d, J=10.2 Hz, 2H), 0.89 (td, J=7.5, 3.6 Hz, 3H).

Intermediate 477

(rac)-ethyl 12-ethyl-1-(3-((5-fluoronaphthalen-1-yl)oxy)propyl)-11-methyl-4,5,6,7,9,11-hexahydropyrazolo[4',3':9,10][1]oxa[6]azacycloundecino[8,7,6-hi]indole-2-carboxylate

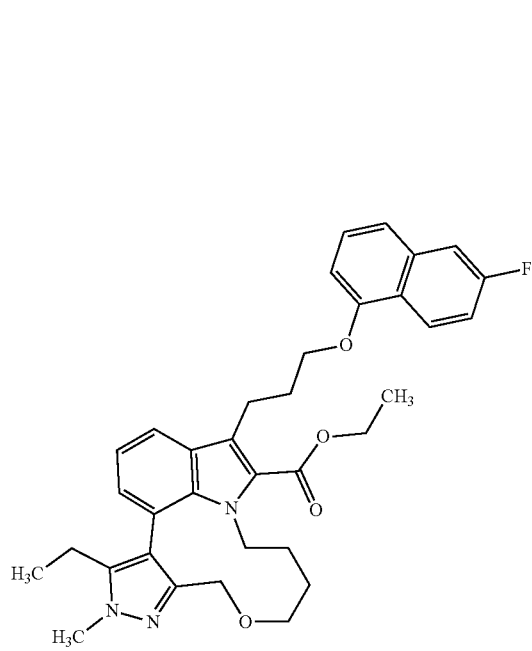 [SMILES: CCOC(=O)c1c(CCCOc2cccc3cc(F)ccc23)c2cccc3c2n1CCCCOCc1nn(C)c(CC)c1-3]

To a solution of (rac)-ethyl 12-ethyl-1-(3-hydroxypropyl)-11-methyl-4,5,6,7,9,11-hexahydropyrazolo[4',3':9,10][1]oxa[6]azacycloundecino[8,7,6-hi]indole-2-carboxylate (220 mg, 500 μmol; see Intermediate 476), 6-fluoronaphthalen-1-ol (121 mg, 750 μmol), and triphenylphosphine (262 mg, 1 mmol) in tetrahydrofuran (17 mL) at 0° C. was added (E)-di-tert-butyl diazene-1,2-dicarboxylate (178 mg, 775 μmol), and the mixture was allowed to warm to room temperature over 19 hours. Water (0.5 ml) was then added, volatiles were removed under reduced pressure and the residue was purified by flash chromatography on silica gel eluting with a gradient of ethyl acetate in hexanes (0-50%) to give the title compound (160 mg, 274 μmol).

LRMS (ESIpos): m/z=584.4 [M+H]$^+$ $^1$H NMR (400 MHz, Chloroform-d) δ 8.39 (dd, J=9.3, 5.8 Hz, 1H), 7.70 (d, J=8.0 Hz, 1H), 7.47-7.32 (m, 3H), 7.27 (td, J=8.8, 3.4 Hz, 1H), 7.09 (t, J=7.5 Hz, 1H), 7.00 (d, J=7.0 Hz, 1H), 6.77-6.70 (m, 1H), 4.70 (d, J=12.5 Hz, 1H), 4.47-4.27 (m, 4H), 4.23 (t, J=6.4 Hz, 2H), 4.11 (ddd, J=13.6, 9.5, 3.7 Hz, 1H), 3.91 (s, 3H), 3.51-3.25 (m, 3H), 2.37 (td, J=7.0, 3.4 Hz, 2H), 2.28 (td, J=7.5, 4.4 Hz, 2H), 1.49 (ddt, J=21.1, 17.3, 6.2 Hz, 1H), 1.39 (t, J=7.1 Hz, 4H), 1.31-1.19 (m, 2H), 0.95 (t, J=7.5 Hz, 3H).

Intermediate 478 ethyl 3-(3-((tert-butyldimethylsilyl)oxy)propyl)-7-(3-(hydroxymethyl)-5-methyl-1-(2-morpholinoethyl)-1H-pyrazol-4-yl)-1H-indole-2-carboxylate

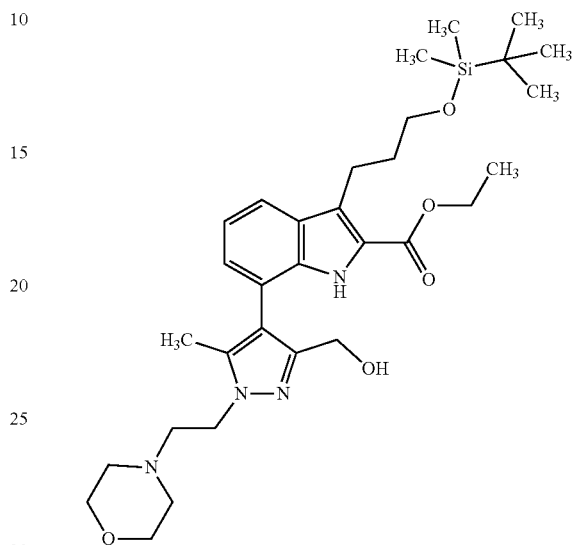

A degassed mixture of ethyl 3-(3-((tert-butyldimethylsilyl)oxy)propyl)-7-(4,4,5,5-tetramethyl-1,3,2-dioxaborolan-2-yl)-1H-indole-2-carboxylate (687 mg, 1.41 mmol; see intermediate 39), {4-bromo-5-methyl-1-[2-(morpholin-4-yl)ethyl]-1H-pyrazol-3-yl}methanol (520 mg, 1.70 mmol; see Intermediate 99), XPhos Pd G2 (55.7 mg, 70.8 μmol), and an aqueous solution of potassium phosphate tribasic (1M, 2.8 mL, 2.8 mmol) in 1.4-dioxane (31.3 mL) and water (7 mL) was heated to 40° C. for 210 minutes. The reaction mixture was cooled to room temperature, diluted with ethyl acetate and water, the layers were separated, the organic layer was washed with saturated aqueous sodium chloride solution and dried over magnesium sulfate. Solids were removed by filtration and volatiles were removed under reduced pressure. The residue was purified by flash chromatography on silica gel eluting with a gradient of methanol in dichloromethane (5-15%) to give the crude title compound. This material was purified by flash chromatography on silica gel eluting with a gradient of methanol in dichloromethane (0-5%) to give the crude title compound (650 mg, 67% yield).

LRMS: m/z=585 [M+H]$^+$ $^1$H NMR (400 MHz, Chloroform-d) δ 9.96 (s, 0H), 7.70 (d, J=8.0 Hz, 1H), 7.17 (t, J=7.6 Hz, 1H), 7.10 (d, J=7.0 Hz, 1H), 4.63 (s, 1H), 4.55 (s, 2H), 4.37 (q, J=7.1 Hz, 2H), 4.25 (t, J=6.9 Hz, 2H), 4.14 (t, J=6.8 Hz, 1H), 3.70 (dq, J=9.9, 5.4, 4.0 Hz, 8H), 3.17 (t, J=7.7 Hz, 2H), 2.85 (s, 2H), 2.73 (t, J=6.8 Hz, 1H), 2.53 (s, 4H), 2.47 (s, 2H), 2.28 (s, 1H), 2.26 (s, 3H), 1.99-1.85 (m, 2H), 1.67 (s, 2H), 1.38 (t, J=7.1 Hz, 3H), 1.25 (d, J=6.5 Hz, 0H), 0.93 (s, 9H), 0.07 (s, 6H).

Intermediate 479

(rac)-ethyl (Z)-1-(3-((tert-butyldimethylsilyl)oxy)propyl)-12-methyl-11-(2-morpholinoethyl)-4,7,9,11-tetrahydropyrazolo[4',3':9,10][1]oxa[6]azacycloundecino[8,7,6-hi]indole-2-carboxylate

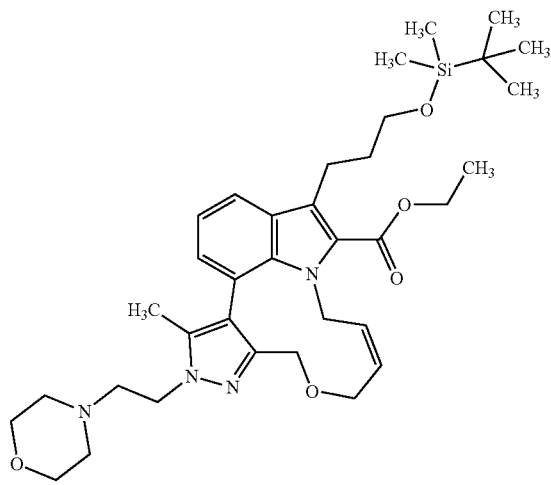 [SMILES: CCOC(=O)c1c(CCCO[Si](C)(C)C(C)(C)C)c2cccc3c2n1C/C=C\COCc1nn(CCN2CCOCC2)c(C)c1-3]

To a stirred solution of (rac)-ethyl 3-(3-((tert-butyldimethylsilyl)oxy)propyl)-7-(3-(hydroxymethyl)-5-methyl-1-(2-morpholinoethyl)-1H-pyrazol-4-yl)-1H-indole-2-carboxylate (555 mg; see Intermediate 478) in N,N-dimethylformamide (14.5 mL) at 0° C. was added (2Z)-1,4-dichlorobut-2-ene (108 µL, 1.04 mmol) and sodium hydride (60% in oil, 24.9 mg, 1.04 mmol) and the mixture was stirred for 4 hours. Then, additional sodium hydride (60% in oil, 24.9 mg, 1.04 mmol) was added, and the mixture was stirred for 2 hours; then, sodium hydride (60% in oil, 24.9 mg, 1.04 mmol) was added and the mixture was stirred again for 18 hours. Finally, sodium hydride (60% in oil, 24.9 mg, 1.04 mmol) was added and the mixture was stirred for an additional 24 hours, the reaction was then stopped by the addition of acetic acid (0.5 mL). Volatiles were removed under reduced pressure, and the residue was diluted with water and ethyl acetate. The layers were separated and the organic layer was washed twice with saturated aqueous sodium chloride solution. The combined aqueous washes were back extracted three times with ethyl acetate. The combined organic layers were dried over magnesium sulfate, solids were removed by filtration and volatiles were removed under reduced pressure. The residue was purified by flash chromatography on silica gel eluting with a gradient of methanol in dichloromethane (0-5%) to give the title compound (380 mg, 596 µmol).

MS (ESIpos): m/z=637.5 [M+H]+

$^1$H NMR (400 MHz, Chloroform-d) δ 7.66 (d, J=7.9 Hz, 1H), 7.07 (t, J=7.6 Hz, 1H), 6.84 (d, J=7.1 Hz, 1H), 5.27 (td, J=11.2, 5.0 Hz, 1H), 5.14 (t, J=10.8 Hz, 1H), 4.99 (d, J=15.5 Hz, 1H), 4.75 (dd, J=15.6, 10.5 Hz, 1H), 4.54 (d, J=13.3 Hz, 1H), 4.46-4.26 (m, 3H), 4.22 (t, J=6.6 Hz, 2H), 3.88 (t, J=11.8 Hz, 1H), 3.70 (dt, J=22.5, 5.6 Hz, 3H), 3.62 (d, J=4.8 Hz, 4H), 3.10 (ddt, J=40.2, 14.0, 7.4 Hz, 2H), 2.82 (dh, J=26.9, 6.4 Hz, 2H), 2.51-2.44 (m, 4H), 1.88 (t, J=7.6 Hz, 5H), 1.37 (t, J=7.2 Hz, 3H), 0.88 (s, 9H), 0.02 (s, 6H).

Intermediate 480

(rac)-ethyl 1-(3-hydroxypropyl)-12-methyl-11-(2-morpholinoethyl)-4,5,6,7,9,11-hexahydropyrazolo[4',3':9,10][1]oxa[6]azacycloundecino[8,7,6-hi]indole-2-carboxylate

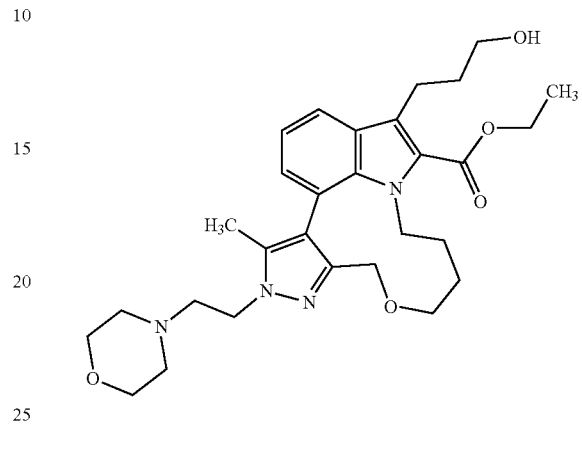

A degassed solution of (rac)-ethyl (Z)-1-(3-((tert-butyldimethylsilyl)oxy)propyl)-12-methyl-11-(2-morpholinoethyl)-4,7,9,11-tetrahydropyrazolo[4',3':9,10][1]oxa[6]azacycloundecino[8,7,6-hi]indole-2-carboxylate (380 mg, 596 µmol; see Intermediate 479) in ethanol (70 mL) was treated with palladium on carbon (10% by mass, 316 mg, 298 µmol), and was then stirred under a hydrogen atmosphere for 66 hours. The reaction mixture was degassed, filtered through celite, and treated with aqueous hydrochloric acid (3 M, 1 ml) and stirred at room temperature for 2 hours. Volatiles were removed under reduced pressure and the mixture was diluted with water and ethyl acetate. Aqueous sodium hydroxide solution (3 mL, 1 N) was added, layers were separated, the organic layer was washed once with saturated aqueous sodium chloride and the combined aqueous phases were extracted once with ethyl acetate. The combined organic layers were dried over sodium sulfate, solids were removed by filtration, and volatiles were removed under reduced pressure. The residue was purified by flash chromatography on silica gel eluting with a gradient of methanol in dichloromethane (0-10%) to give title compound (240 mg, 457 µmol).

LRMS (ESIpos): m/z=525.5 [M+H]+

$^1$H NMR (400 MHz, Chloroform-d) δ 7.62 (dd, J=7.8, 2.2 Hz, 1H), 7.06 (q, J=6.9 Hz, 1H), 6.94 (dd, J=7.2, 3.6 Hz, 1H), 4.60 (dd, J=12.5, 3.1 Hz, 1H), 4.38 (td, J=7.2, 3.7 Hz, 1H), 4.30 (ddd, J=11.0, 8.2, 3.5 Hz, 2H), 4.19 (dt, J=14.3, 7.1 Hz, 1H), 4.04 (ddt, J=14.0, 10.1, 4.4 Hz, 1H), 3.83 (d, J=4.2 Hz, 3H), 3.55 (q, J=6.4, 5.9 Hz, 2H), 3.38 (dt, J=9.8, 4.4 Hz, 1H), 3.27-3.05 (m, 4H), 2.99 (s, 1H), 2.23 (dqq, J=11.5, 7.9, 3.9 Hz, 2H), 1.98 (td, J=11.8, 10.5, 5.3 Hz, 1H), 1.34 (pt, J=10.6, 5.9 Hz, 5H), 1.14 (d, J=10.2 Hz, 2H), 0.89 (td, J=7.5, 3.6 Hz, 3H).

Intermediate 481

(rac)-ethyl 1-(3-((6-fluoronaphthalen-1-yl)oxy)propyl)-12-methyl-11-(2-morpholinoethyl)-4,5,6,7,9,11-hexahydropyrazolo[4',3':9,10][1]oxa[6]azacycloundecino[8,7,6-hi]indole-2-carboxylate

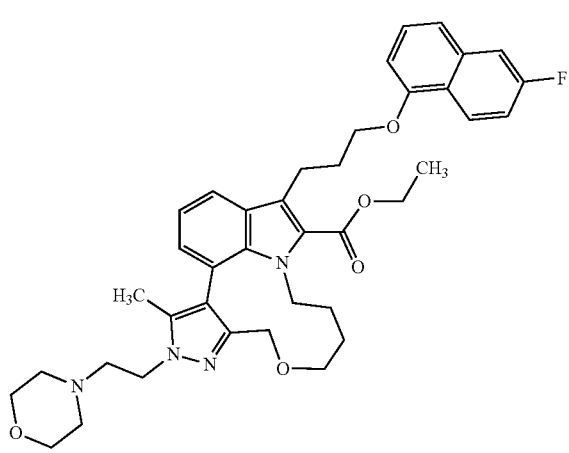 [SMILES: CCOC(=O)c1c(CCCOc2cccc3cc(F)ccc23)c2cccc3c2n1CCCCOCc1nn(CCN2CCOCC2)c(C)c1-3]

To a stirred solution of (rac)-ethyl 1-(3-hydroxypropyl)-12-methyl-11-(2-morpholinoethyl)-4,5,6,7,9,11-hexahydropyrazolo[4',3':9,10][1]oxa[6]azacycloundecino[8,7,6-hi]indole-2-carboxylate (240 mg, 457 µmol) and 6-fluoronaphthalen-1-ol (111 mg, 685 µmol) in tetrahydrofuran (15 mL) at 0° C. was added triphenylphosphine (239 mg, 914 µmol) and (E)-di-tert-butyl diazene-1,2-dicarboxylate (163 mg, 708 µmol), and the mixture allowed to warm to room temperature over 24 hours. Additional triphenylphosphine (272 mg, 1.04 mmol) and (E)-di-tert-butyl diazene-1,2-dicarboxylate (186 mg, 810 µmol) were added and the mixture was stirred for 23 hours at room temperature, at which time further triphenylphosphine (272 mg, 1.04 mmol) and (E)-di-tert-butyl diazene-1,2-dicarboxylate (186 mg, 810 µmol) were added. After stirring for 5 hours, the reaction was stopped by the addition of water (0.5 ml), the volatiles were removed under reduced pressure, and the residue was purified by flash chromatography on silica gel eluting with a gradient of ethyl acetate in hexanes (0-100%) followed by a gradient of methanol in dichloromethane (0-3%) to give the title compound (300 mg, 448 µmol).

LRMS (ESIpos): m/z=669.5 [M+H]$^+$ $^1$H NMR (300 MHz, Chloroform-d) δ 8.35 (d, J=3.4 Hz, 0H), 7.75-7.60 (m, 2H), 7.61-7.18 (m, 4H), 7.08 (dd, J=8.0, 7.1 Hz, 1H), 6.97 (dd, J=7.1, 1.3 Hz, 1H), 6.72 (dd, J=6.6, 2.0 Hz, 1H), 4.69 (d, J=12.5 Hz, 1H), 4.46-4.26 (m, 4H), 4.21 (q, J=6.7 Hz, 4H), 4.08-3.87 (m, 0H), 3.74-3.65 (m, 5H), 3.52-3.14 (m, 2H), 2.99-2.73 (m, 2H), 2.57-2.47 (m, 5H), 2.33 (p, J=6.8 Hz, 2H), 1.92 (s, 3H), 1.46 (d, J=17.8 Hz, 1H), 1.37 (t, J=7.1 Hz, 3H), 1.17 (d, J=10.0 Hz, 3H).

Intermediate 482

(rac)-ethyl 12-ethyl-1-(3-((6-fluoronaphthalen-1-yl)oxy)propyl)-10-methyl-4,5,6,7,9,10-hexahydropyrazolo[4',3':9,10][1]oxa[6]azacycloundecino[8,7,6-hi]indole-2-carboxylate

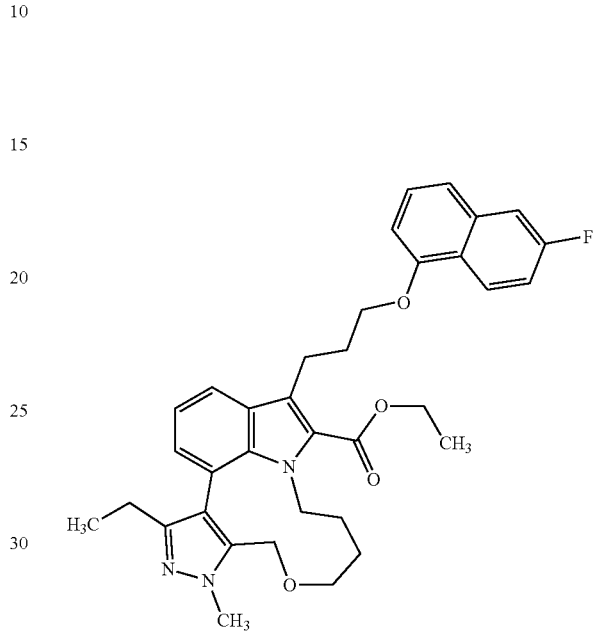

To a stirred solution of (rac)-ethyl 12-ethyl-1-(3-hydroxypropyl)-10-methyl-4,5,6,7,9,10-hexahydropyrazolo[4',3':9,10][1]oxa[6]azacycloundecino[8,7,6-hi]indole-2-carboxylate (300 mg, 682 µmol; see Intermediate 454) and 6-fluoronaphthalen-1-ol (165 mg, 1.02 mmol) in tetrahydrofuran (22 mL) at 0° C. was added triphenylphosphine (356 mg, 1.36 mmol) and (E)-di-tert-butyl diazene-1,2-dicarboxylate (241 mg, 1.05 mmol), and the mixture was allowed to warm to room temperature over 19 hours. The reaction was stopped by the addition of water (0.5 ml) and the volatiles were removed under reduced pressure. The residue was purified by flash chromatography on silica gel eluting with a gradient of ethyl acetate in hexanes (0-50%) to give the title compound (390 mg, 668 µmol).

LRMS (ESIpos): m/z=584.4 [M+H]$^+$ $^1$H NMR (400 MHz, Chloroform-d) δ 8.36 (dd, J=9.3, 5.7 Hz, 1H), 7.73 (dd, J=8.1, 1.3 Hz, 1H), 7.40 (dd, J=10.0, 2.6 Hz, 1H), 7.37-7.30 (m, 2H), 7.24 (d, J=2.6 Hz, 0H), 7.06 (t, J=7.6 Hz, 1H), 6.90 (dd, J=7.1, 1.3 Hz, 1H), 6.71 (dd, J=7.0, 1.7 Hz, 1H), 4.64 (dt, J=14.3, 3.9 Hz, 1H), 4.58 (d, J=13.4 Hz, 1H), 4.45 (d, J=13.4 Hz, 1H), 4.34 (dd, J=14.5, 7.2 Hz, 1H), 4.22 (q, J=5.9 Hz, 3H), 4.13 (s, 0H), 3.96 (s, 3H), 3.56-3.29 (m, 3H), 2.98-2.87 (m, 1H), 2.46-2.27 (m, 4H), 1.61-1.42 (m, 1H), 1.37 (t, J=7.1 Hz, 3H), 1.33-1.17 (m, 1H), 1.24 (s, 1H), 1.11 (s, 0H), 1.03 (t, J=7.6 Hz, 3H).

Intermediate 483

(rac)-ethyl 12-ethyl-10-methyl-1-(3-((5,6,7,8-tetra-hydronaphthalen-1-yl)oxy)propyl)-4,5,6,7,9,10-hexahydropyrazolo[4',3':9,10][1]oxa[6]azacycloun-decino[8,7,6-hi]indole-2-carboxylate

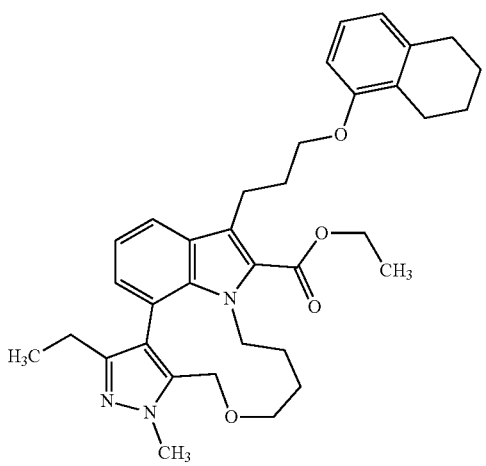 [SMILES: CCOC(=O)c1c(CCCOc2cccc3c2CCCC3)c2cccc3c2n1CCCCOCc1c-3c(CC)nn1C]

To a stirred solution of (rac)-ethyl 12-ethyl-1-(3-hydroxy-propyl)-10-methyl-4,5,6,7,9,10-hexahydropyrazolo[4',3':9,10][1]oxa[6]azacycloundecino[8,7,6-hi]indole-2-carboxylate (230 mg, 523 µmol; see Intermediate 454) and 5,6,7,8-tetrahydronaphthalen-1-ol (116 mg, 784 µmol), in tetrahydrofuran (17 mL) at 0° C. was added triphenylphosphine (272 mg, 1.04 mmol) and (E)-di-tert-butyl diazene-1,2-dicarboxylate (186 mg, 810 µmol). The mixture was allowed to warm to room temperature over 16 hours, and was then treated with additional 5,6,7,8-tetrahydronaphthalen-1-ol (116 mg, 784 µmol), triphenylphosphine (272 mg, 1.04 mmol) and (E)-di-tert-butyl diazene-1,2-dicarboxylate (186 mg, 810 µmol), and was then stirred for. 6 hours. with the reaction was stopped by the addition of water (0.5 ml), volatiles were removed under reduced pressure and the residue was purified by flash chromatography on silica gel eluting with a gradient of ethyl acetate in hexanes (0-40%) to give the title compound (291 mg, 510 µmol).

MS (ESIpos): m/z=570.5 [M+H]$^+$ $^1$H NMR (400 MHz, Chloroform-d) δ 7.73 (dd, J=8.1, 1.3 Hz, 1H), 7.15-7.00 (m, 2H), 6.91 (dd, J=7.1, 1.2 Hz, 1H), 6.70 (d, J=7.6 Hz, 1H), 6.63 (d, J=8.1 Hz, 1H), 4.65 (dd, J=14.3, 4.1 Hz, 1H), 4.60 (d, J=13.4 Hz, 1H), 4.48 (d, J=13.4 Hz, 1H), 4.44-4.28 (m, 2H), 4.26-4.08 (m, 1H), 4.07 (t, J=6.2 Hz, 2H), 3.97 (s, 3H), 3.53 (dt, J=11.8, 7.1 Hz, 1H), 3.32 (dddd, J=40.2, 13.3, 8.7, 6.7 Hz, 2H), 2.93 (ddt, J=11.4, 8.7, 4.2 Hz, 1H), 2.78 (q, J=5.5 Hz, 4H), 2.37 (qd, J=7.4, 5.5 Hz, 2H), 2.28-2.17 (m, 2H), 1.89-1.73 (m, 4H), 1.52 (s, 1H), 1.41 (t, J=7.1 Hz, 3H), 1.32-1.19 (m, 2H), 1.14 (s, 1H), 1.04 (t, J=7.6 Hz, 3H).

Intermediate 484

(rac)-ethyl 12-ethyl-11-methyl-1-(3-((5,6,7,8-tetra-hydronaphthalen-1-yl)oxy) propyl)-4,5,6,7,9,11-hexahydropyrazolo[4',3':9,10][1]oxa[6]azacycloun-decino[8,7,6-hi]indole-2-carboxylate

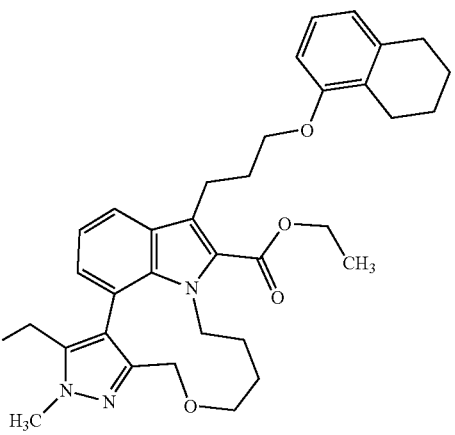

To a stirred solution of (rac)-ethyl 12-ethyl-1-(3-hydroxy-propyl)-11-methyl-4,5,6,7,9,11-hexahydropyrazolo[4',3':9,10][1]oxa[6]azacycloundecino[8,7,6-hi]indole-2-carboxylate (140 mg, 310 µmol; see Intermediate 476) in tetrahydrofuran (9 ml) at 0° C. was added 5,6,7,8-tetrahydronaphthalen-1-ol (60.6 mg, 409 µmol), triphenylphosphine (143 mg, 546 µmol) and (E)-di-tert-butyl diazene-1,2-dicarboxylate (97.4 mg, 423 µmol) and the mixture was allowed to warm to room temperature over 27 hours. The reaction was stopped by the addition of water (0.5 ml), the volatiles were removed under reduced pressure and the residue was purified by flash chromatography on silica gel eluting with a gradient of ethyl acetate in hexanes (0-50%) to give the title compound (170 mg, 298 µmol).

LRMS (ESIpos): m/z=570.4 [M+H]$^+$ $^1$H NMR (300 MHz, Chloroform-d) δ 7.69 (dd, J=8.0, 1.3 Hz, 1H), 7.18-6.95 (m, 3H), 6.75-6.58 (m, 2H), 4.69 (d, J=12.4 Hz, 1H), 4.48-4.22 (m, 3H), 4.20-4.00 (m, 2H), 3.90 (s, 3H), 3.46 (ddd, J=10.3, 5.7, 1.8 Hz, 1H), 3.29 (ddd, J=14.5, 9.1, 6.8 Hz, 3H), 2.78 (td, J=5.7, 3.2 Hz, 4H), 2.43-2.00 (m, 3H), 1.88-1.72 (m, 4H), 1.41 (t, J=7.1 Hz, 3H), 1.31-1.17 (m, 2H), 0.94 (t, J=7.6 Hz, 3H).

Intermediate 485 ethyl 3-(3-((tert-butyldimethylsilyl)oxy)propyl)-7-(3-(hydroxymethyl)-5-methyl-1-(2-morpholinoethyl)-1H-pyrazol-4-yl)-6-methyl-1H-indole-2-carboxylate

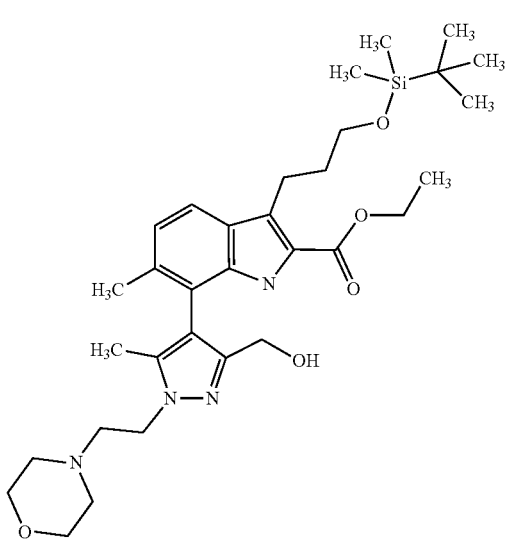 [SMILES: CCOC(=O)c1[nH]c2c(-c3c(CO)nn(CCN4CCOCC4)c3C)c(C)ccc2c1CCCO[Si](C)(C)C(C)(C)C]

A degassed mixture of ethyl 3-(3-((tert-butyldimethylsilyl)oxy)propyl)-6-methyl-7-(4,4,5,5-tetramethyl-1,3,2-dioxaborolan-2-yl)-1H-indole-2-carboxylate (1.81 g, 3.62 mmol; see Intermediate 467), {4-bromo-5-methyl-1-[2-(morpholin-4-yl)ethyl]-1H-pyrazol-3-yl}methanol (920 mg, 3.02 mmol; see Intermediate 99), XPhos Pd G2 (118 mg, 151 μmol), an aqueous solution of potassium phosphate tribasic (1M, 6 mL, 6 mmol) and water (12 mL) in 1,4-dioxane (67 mL) was heated to 40° C. for 21 hours. The reaction mixture was cooled to room temperature, diluted with ethyl acetate and water. The layers were separated, the organic layer was washed with saturated aqueous sodium chloride solution and dried over magnesium sulfate. Solids were removed by filtration and volatiles were removed under reduced pressure. The residue was purified by flash chromatography on silica gel eluting with a gradient of methanol in dichloromethane (0-5%) to give the title compound (590 mg, 32.7% yield).

LRMS: m/z=599.4 [M+H]$^+$ $^1$H NMR (300 MHz, Chloroform-d) δ 8.74 (s, 1H), 7.59 (d, J=8.1 Hz, 1H), 7.07 (d, J=8.3 Hz, 1H), 5.30 (s, 2H), 4.63 (s, 2H), 4.48 (d, J=12.9 Hz, 1H), 4.36 (dd, J=8.1, 6.1 Hz, 2H), 4.25 (d, J=6.9 Hz, 2H), 4.13 (t, J=6.9 Hz, 2H), 3.76-3.63 (m, 10H), 3.18-3.07 (m, 2H), 2.87 (t, J=6.8 Hz, 2H), 2.72 (t, J=7.0 Hz, 2H), 2.55 (dq, J=10.3, 4.7 Hz, 4H), 2.49-2.41 (m, 4H), 2.28 (d, J=0.4 Hz, 3H), 2.20 (s, 3H), 2.06 (s, 3H), 1.90 (s, 2H), 1.70 (s, 2H), 1.37 (t, J=7.1 Hz, 3H), 0.92 (s, 9H), 0.91 (s, 1H), 0.07 (s, 6H).

Intermediate 486

(rac)-ethyl (Z)-1-(3-((tert-butyldimethylsilyl)oxy)propyl)-12,13-dimethyl-11-(2-morpholinoethyl)-4,7,9,11-tetrahydropyrazolo[4',3':9,10][1]oxa[6]azacycloundecino[8,7,6-hi]indole-2-carboxylate

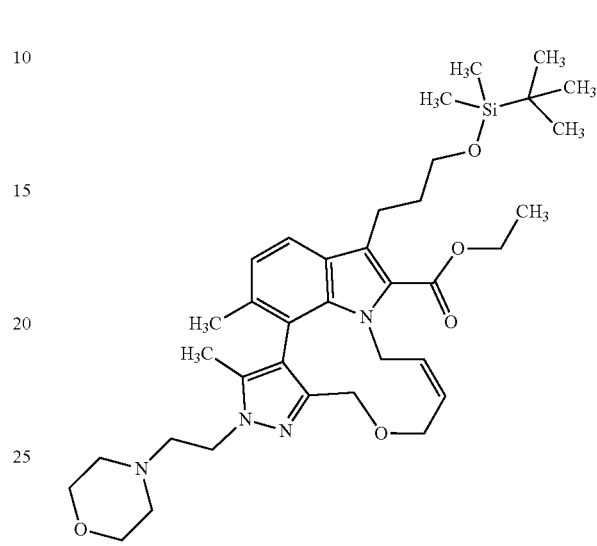

To a stirred solution of ethyl 3-(3-((tert-butyldimethylsilyl)oxy)propyl)-7-(3-(hydroxymethyl)-5-methyl-1-(2-morpholinoethyl)-1H-pyrazol-4-yl)-6-methyl-1H-indole-2-carboxylate (590 mg, 985 μmol; see Intermediate 485) in dimethylformamide (15 mL) at 0° C. was added (2Z)-1,4-dichlorobut-2-ene (147 μL, 1.18 mmol) and sodium hydride (60% in oil, 25.9 mg, 1.08 mmol) and the mixture was allowed to warm to room temperature over 19 hours. Sodium hydride (60% in oil, 25.9 mg, 1.08 mmol) was added and the mixture was stirred for 24 hours; sodium hydride (60% in oil, 25.9 mg, 1.08 mmol) was added and the mixture was stirred for further 6 hours; additional sodium hydride (60% in oil, 25.9 mg, 1.08 mmol) was added and the mixture was stirred for 17 hours; further sodium hydride (60% in oil, 25.9 mg, 1.08 mmol) was added, and after 7 hours, additional sodium hydride (60% in oil, 25.9 mg, 1.08 mmol) was added and the mixture was stirred for another 24 hours. At this point, the reaction was stopped by the addition of acetic acid (0.5 ml) and volatiles were removed under reduced pressure. The residue was diluted with water and ethyl acetate, the layers were separated and the organic layer was washed twice with saturated aqueous sodium chloride. Combined aqueous washes were back extracted twice with ethyl acetate. Organic layers were combined, dried over magnesium sulfate, solids were removed by filtration and volatiles were removed under reduced pressure. The residue was purified by flash chromatography on silica gel eluting with a gradient of methanol in dichloromethane (0-5%) to give the title compound (310 mg, 48.3% yield).

LRMS: m/z=652.4 [M+H]$^+$ $^1$H NMR (300 MHz, Chloroform-d) δ 7.57 (d, J=8.1 Hz, 1H), 7.05 (d, J=8.2 Hz, 1H), 5.23 (ddd, J=12.0, 7.9, 3.2 Hz, 1H), 5.08-4.92 (m, 2H), 4.61 (dd, J=18.3, 12.2 Hz, 2H), 4.46-4.20 (m, 4H), 3.93 (t, J=12.0 Hz, 1H), 3.81-3.59 (m, 8H), 3.22-2.95 (m, 2H), 2.84 (td, J=6.4, 3.8 Hz, 2H), 2.49 (dd, J=5.6, 3.7 Hz, 4H), 1.90 (d, J=20.9 Hz, 5H), 1.37 (t, J=7.1 Hz, 3H), 0.89 (s, 8H), 0.04 (s, 6H).

Intermediate 487

(rac)-ethyl 1-(3-hydroxypropyl)-12,13-dimethyl-11-(2-morpholinoethyl)-4,5,6,7,9,11-hexahydropyrazolo[4',3':9,10][1]oxa[6]azacycloundecino[8,7,6-hi]indole-2-carboxylate

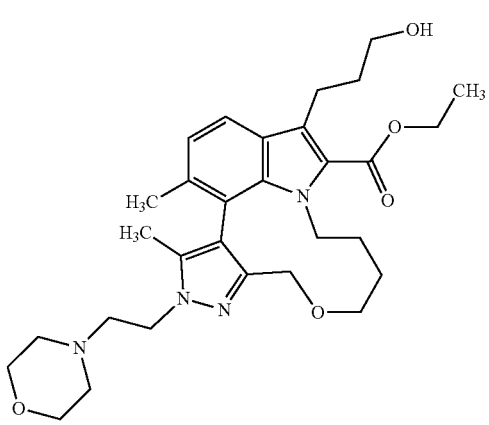 [SMILES: CCOC(=O)c1c(CCCO)c2ccc(C)c3c2n1CCCCOCc1nn(CCN2CCOCC2)c(C)c1-3]

A stirred solution of (rac)-ethyl (Z)-1-(3-(((tert-butyldimethylsilyl)oxy)propyl)-12,13-dimethyl-11-(2-morpholinoethyl)-4,7,9,11-tetrahydropyrazolo[4',3':9,10][1]oxa[6]azacycloundecino[8,7,6-hi]indole-2-carboxylate (300 mg, 460 µmol; see Intermediate 486) in ethanol (57.4 mL) was treated with palladium on carbon (10% by mass, 243 mg, 230 µmol) and placed under a hydrogen atmosphere for 23 hours. The reaction mixture was degassed and filtered through celite, the filtrate was treated with aqueous hydrochloric acid (3M, 1 ml) and stirred at room temperature for 30 minutes, volatiles were removed under reduced pressure and the mixture was diluted with water and ethyl acetate, and aqueous sodium hydroxide solution (3 mL, 1 N) was added. Then, layers were separated, the organic layer was washed once with saturated aqueous sodium chloride solution, and the combined aqueous layers were extracted once with ethyl acetate. The combined organic layers were dried over sodium sulfate, and volatiles were removed under reduced pressure. The residue was purified by flash chromatography on silica gel eluting with a gradient of methanol in dichloromethane (0-3%) to give the title compound (240 mg, 457 µmol).

LRMS (ESIpos): m/z=539.3 [M+H]$^+$ $^1$H NMR (400 MHz, Chloroform-d) δ 7.53 (d, J=8.1 Hz, 1H), 7.06 (d, J=8.2 Hz, 1H), 4.51 (d, J=12.6 Hz, 1H), 4.45-4.25 (m, 3H), 4.20 (q, J=5.8, 5.1 Hz, 2H), 4.17-4.08 (m, 1H), 3.91 (ddd, J=13.2, 9.2, 3.6 Hz, 1H), 3.65 (t, J=4.6 Hz, 4H), 3.65-3.47 (m, 2H), 3.49-3.34 (m, 1H), 3.29-3.17 (m, 1H), 3.17-3.05 (m, 1H), 2.82 (td, J=6.4, 2.3 Hz, 2H), 2.54-2.44 (m, 4H), 2.04 (s, 3H), 2.06-1.79 (m, 1H), 1.84 (s, 3H), 1.37 (t, J=7.1 Hz, 5H), 1.26-1.08 (m, 3H).

Intermediate 488

(rac)-ethyl 1-(3-((6-fluoronaphthalen-1-yl)oxy)propyl)-12,13-dimethyl-11-(2-morpholinoethyl)-4,5,6,7,9,11-hexahydropyrazolo[4',3':9,10][1]oxa[6]azacycloundecino[8,7,6-hi]indole-2-carboxylate

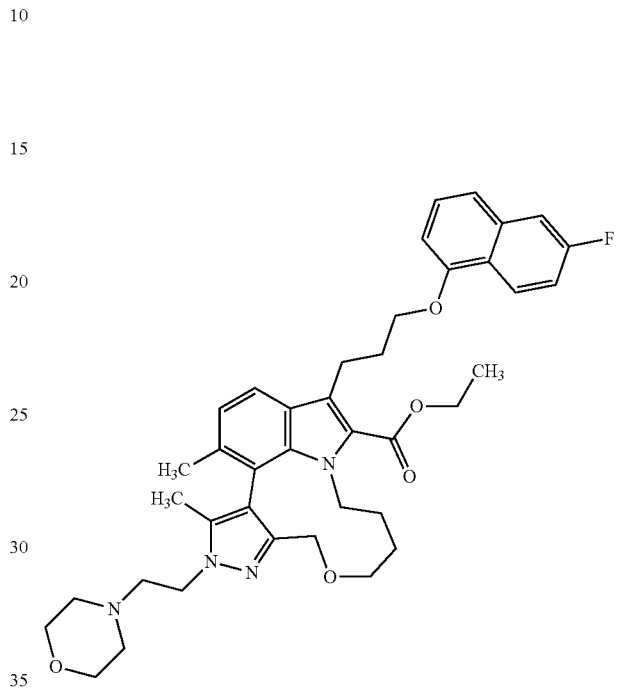

To a stirred solution of (rac)-ethyl 1-(3-hydroxypropyl)-12,13-dimethyl-11-(2-morpholinoethyl)-4,5,6,7,9,11-hexahydropyrazolo[4',3':9,10][1]oxa[6]azacycloundecino[8,7,6-hi]indole-2-carboxylate (240 mg, 445 µmol; see Intermediate 487) and 6-fluoronaphthalen-1-ol (108 mg, 667 µmol) in tetrahydrofuran (15 mL) at 0° C. was added triphenylphosphine (233 mg, 890 µmol) and (E)-di-tert-butyl diazene-1,2-dicarboxylate (158 mg, 689 µmol), and the mixture allowed to warm to room temperature over 18 hours. The reaction was stopped by the addition of water (0.5 ml), volatiles were removed under reduced pressure and the residue was purified by flash chromatography on silica gel eluting with a gradient of methanol in dichloromethane (0-3%) to give the title compound (200 mg, 292 µmol).

LRMS (ESIpos): m/z=683.3 [M+H]$^+$ $^1$H NMR (300 MHz, Chloroform-d) δ 8.28 (dd, J=9.3, 5.8 Hz, 1H), 7.49 (d, J=8.2 Hz, 1H), 7.37-7.09 (m, 3H), 6.94 (d, J=8.2 Hz, 1H), 6.63 (dd, J=6.8, 1.9 Hz, 1H), 4.48 (d, J=12.5 Hz, 1H), 4.41-4.30 (m, 1H), 4.25 (dd, J=11.6, 7.1 Hz, 1H), 4.13 (dt, J=12.9, 6.3 Hz, 4H), 3.86 (ddd, J=13.3, 9.5, 3.0 Hz, 1H), 3.60 (t, J=4.6 Hz, 4H), 3.43-3.12 (m, 4H), 2.75 (t, J=6.4 Hz, 2H), 2.43 (dt, J=7.2, 2.7 Hz, 4H), 2.32-2.16 (m, 2H), 1.98 (s, 3H), 1.77 (s, 3H), 1.27 (d, J=7.1 Hz, 2H), 1.21-1.02 (m, 2H).

Intermediate 489

(rac)-ethyl 12-ethyl-10-methyl-1-(3-((6-chloronaphthalen-1-yl)oxy)propyl)-4,5,6,7,9,10-hexahydropyrazolo[4',3':9,10][1,6]oxaazacycloundecino[8,7,6-hi]indole-2-carboxylate

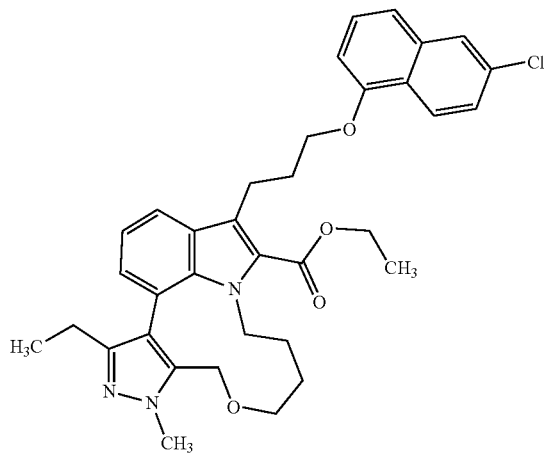 [SMILES: CCOC(=O)c1c(CCCOc2cccc3cc(Cl)ccc23)c2cccc3c2n1CCCCOCc1c-3c(CC)nn1C]

A mixture of caesium carbonate (200 mg, 0.61 mmol), 6-chloronaphthalen-1-ol (53 mg; see Intermediate 64) and (rac)-ethyl 1-(3-bromopropyl)-12-ethyl-10-methyl-4,5,6,7,9,10-hexahydropyrazolo[4',3':9,10][1,6]oxaazacycloundecino[8,7,6-hi]indole-2-carboxylate (107 mg, 0.21 mmol; see Intermediate 455) in tetrahydrofuran (7 ml) was heated to 35° C. for 17 hours, and was then warmed to 45° C. for 96 hours, cooled to room temperature, then heated to 55° C. for 22 hours. The crude reaction mixture was used in the next step without further manipulation.

LRMS (ESIpos) m/z=600 [M+H]+

Intermediate 490

(rac)-ethyl 11,12-dimethyl-1-(3-((6-methylnaphthalen-1-yl)oxy)propyl)-4,5,6,7,9,11-hexahydropyrazolo[4',3':9,10][1,6]oxaazacycloundecino[8,7,6-hi]indole-2-carboxylate

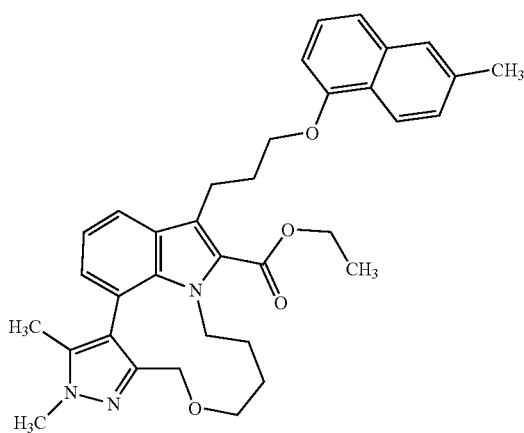

To a solution of (rac)-ethyl 1-(3-bromopropyl)-11,12-dimethyl-4,5,6,7,9,11-hexahydropyrazolo[4',3':9,10][1,6]oxaazacycloundecino[8,7,6-hi]indole-2-carboxylate (100 mg, 0.2 mmol; see Intermediate 459) in tetrahydrofuran (10 ml) was added caesium carbonate (400 mg, 1.2 mmol), 6-methylnaphthalene-1-ol (60 mg, 0.38 mmol; see Intermediate 494), and the mixture was heated at 55° C. for 64 hours. The mixture was diluted with ethyl acetate (10 ml), cooled to room temperature, insoluble materials were removed by filtration, and the filter cake was washed with a small amount of ethyl acetate. The combined filtrate and washes were concentrated under reduced pressure and the residue was dissolved in dichloromethane and purified by normal phase chromatography on silica gel eluting with a gradient of ethyl acetate in hexanes (25-75%) to give the title compound in moderate purity (92 mg) which was used without further manipulation.

LRMS (ESIpos) m/z=566 [M+H]+

Intermediate 491

2-bromo-1-(p-tolyl)ethanone

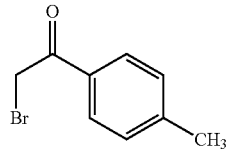

To a solution of 4'-methylacetophenone (6.3 g, 46.9 mmol) in dichloromethane (120 ml) was added glacial acetic acid (5 ml), followed by bromine (2.4 ml, 7.5 g, 47 mmol). After stirring at room temperature for 1 hour, volatiles were removed under reduced pressure to give the title compound in moderate purity (10 g); this material was used without further manipulation.

$^1$H NMR (300 MHz, Chloroform-d) δ 7.92-7.85 (m, 2H), 7.34-7.27 (m, 2H), 4.43 (s, 2H), 2.43 (s, 3H).[1]

$^{13}$C NMR (75 MHz, Chloroform-d) δ 191.11, 145.14, 131.71, 129.71, 129.22, 30.95, 21.89.

Intermediate 492

O-ethyl S-(2-oxo-2-(p-tolyl)ethyl) carbonodithioate

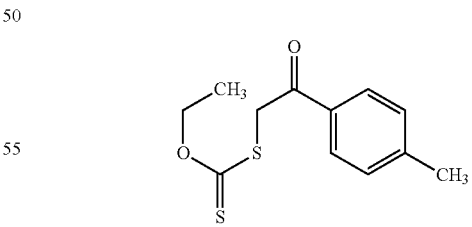

A suspension of crude 2-bromo-1-(p-tolyl)ethanone (10 g, 46.9 mmol; see Intermediate 491) and potassium ethyl xanthate (7.8 g, 28.6 mmol) in acetone (125 ml) was stirred at room temperature for 16 hours. The suspension was filtered to remove precipitated salts, the filter cake was washed three times with acetone (20 ml each), the combined filtrate and washes were concentrated under reduced pressure, and the residue was purified by normal phase chromatography on silica gel eluting with a gradient of ethyl acetate in hexanes (0-10%) to give the crude desired product, which was triturated from hot hexanes mixed with a trace of ethyl acetate (100 ml, 98:2), to give the title compound as a white solid (5.7 g) after filtration.

$^1$H NMR (300 MHz, Chloroform-d) δ 7.96-7.89 (m, 2H), 7.33-7.27 (m, 2H), 4.64 (d, J=7.0 Hz, 4H), 2.44 (s, 3H), 1.40 (t, J=7.1 Hz, 3H).

Intermediate 493

7-methyl-4-oxo-1,2,3,4-tetrahydronaphthalen-1-yl pivalate

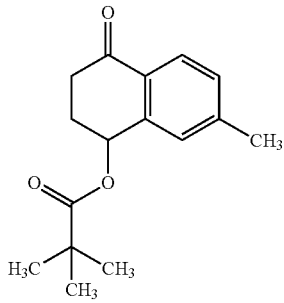

A mixture of O-ethyl S-(2-oxo-2-(4-(methyl)phenyl) ethyl) carbonodithioate (5.3 g, 20.8 mmol; see Intermediate 492) and vinyl pivalate (7 ml, 47.5 mmol) in ethyl acetate (200 ml) was heated to reflux. Lauroyl peroxide was added (2 g), and the mixture was heated for 75 minutes, at which time volatiles were removed under reduced pressure. The residue was dissolved in ethyl acetate (100 ml), the mixture was heated to reflux, and treated with lauroyl peroxide (2 g). After 1 hour, additional lauroyl peroxide (4 g) was added, after additional 1 hour, additional lauroyl peroxide (4 g) was added, and the mixture was then heated for an additional 1 hour, at which time the mixture was cooled to room temperature, volatiles were removed under reduced pressure, and the residue was purified by flash chromography on silica gel (80 g) (loading on a basic alumina pre-column) eluting with a gradient of ethyl acetate in hexanes (0-20%) to give the title compound as an amber gum (600 mg). The material thus obtained was used without further manipulation.

Intermediate 494

6-methylnaphthalen-1-ol

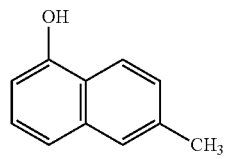

A mixture of 7-methyl-4-oxo-1,2,3,4-tetrahydronaphthalen-1-yl pivalate (600 mg 2.3 mmol see Intermediate 493) and toluene sulfonic acid (50 mg, 0.29 mmol) in toluene (50 ml) was heated to reflux for 3 hours. Additional toluene sulfonic acid (150 mg) was added, and heating continued for an additional 3 hours, after which time the mixture was cooled to room temperature. Volatiles were removed under reduced pressure, and the residue was purified by flash chromatography on silica gel eluting with a gradient of ethyl acetate in hexanes (0-30%) to give the title compound as an off white semi-solid (140 mg).

LRMS (ESIneg) m/z=157 [M−H]$^-$ $^1$H NMR (300 MHz, Chloroform-d) δ 8.12 (d, J=8.6 Hz, 1H), 7.62 (dt, J=1.8, 0.9 Hz, 1H), 7.42-7.33 (m, 2H), 7.30 (dd, J=8.3, 7.3 Hz, 1H), 6.77 (dd, J=7.3, 1.1 Hz, 1H), 2.55 (d, J=0.9 Hz, 3H).

Intermediate 495

(rac)-ethyl 11,12-dimethyl-1-(3-((6-(trifluoromethyl) naphthalen-1-yl)oxy)propyl)-4,5,6,7,9,11-hexahydropyrazolo[4',3':9,10][1,6]oxaazacycloundecino[8, 7,6-hi]indole-2-carboxylate

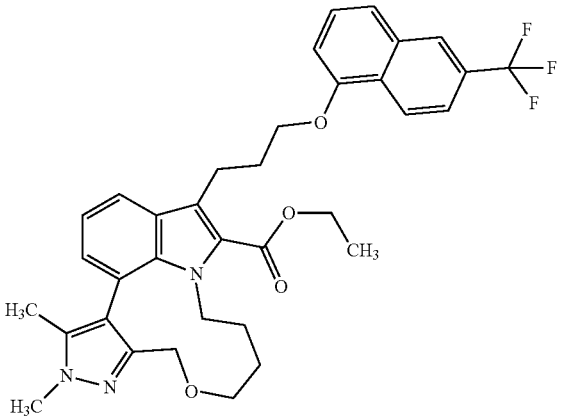 [SMILES: CCOC(=O)c1c(CCCOc2cccc3cc(C(F)(F)F)ccc23)c2cccc3c2n1CCCCOCc1nn(C)c(C)c1-3]

A solution of (rac)-ethyl 1-(3-bromopropyl)-11,12-dimethyl-4,5,6,7,9,11-hexahydropyrazolo[4',3':9,10][1,6] oxaazacycloundecino[8,7,6-hi]indole-2-carboxylate (100 mg, 0.2 mmol; see Intermediate 459) in tetrahydrofuran (10 ml) was treated with caesium carbonate (400 mg, 1.2 mmol), 6-trifluoromethylnaphthalene-1-ol (80 mg, 0.38 mmol; see Intermediate 499), and the mixture was heated to 55° C. for 64 hours. The mixture was then diluted with ethyl acetate (10 ml) and cooled to room temperature. The precipitates were removed by filtration, washed with a small amount of ethyl acetate, and the combined filtrate and washes were concentrated under reduced pressure. The residue was dissolved in dichloromethane and purified by normal phase chromatography on silica gel eluting with a gradient of ethyl acetate in hexanes (25-75%) to give the title compound in modest purity (80 mg), which was carried forward without further manipulation.

LRMS (ESIpos) m/z=620 [M+H]$^+$

Intermediate 496

2-bromo-1-(4-(trifluoromethyl)phenyl)ethanone

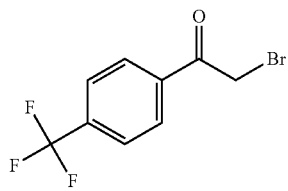 [SMILES: O=C(CBr)c1ccc(C(F)(F)F)cc1]

To a solution of 1-(4-(trifluoromethyl)phenyl)ethanone (5.1 g, 27.1 mmol) in dichloromethane (120 ml) was added glacial acetic acid (5 ml), followed by bromine (1.4 ml, 4.33 g, 27.1 mmol) and the resulting mixture was stirred at room temperature for 30 minutes, after which time volatiles were removed under reduced pressure to give the title compound as a pale orange semi-solid which was used without further manipulation (7.5 g).

Intermediate 497

O-ethyl S-(2-oxo-2-(4-(trifluoromethyl)phenyl)ethyl) carbonodithioate

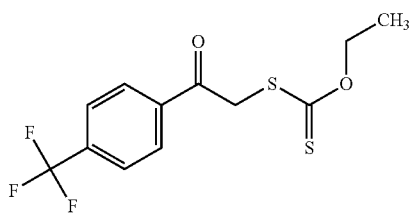 [SMILES: CCOC(=S)SCC(=O)c1ccc(C(F)(F)F)cc1]

A solution of crude 2-bromo-1-(4-(trifluoromethyl)phenyl)ethanone (7.5 g; see Intermediate 496) in acetone (120 ml) was treated with potassium ethyl xanthate (4.49 g, 28.6 mmol) and stirred at room temperature for 14 hours at which time insoluble materials were removed by filtration. The filter cake was washed three times with acetone (20 ml each), and combined filtrate and washes were concentrated under reduced pressure, to give the crude title compound as an pale orange gum (8.8 g). The material thus obtained was used without further manipulation.

Intermediate 498

4-oxo-7-(trifluoromethyl)-1,2,3,4-tetrahydronaphthalen-1-yl pivalate

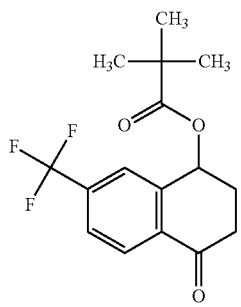 [SMILES: CC(C)(C)C(=O)OC1CCC(=O)c2ccc(C(F)(F)F)cc21]

To a solution of crude O-ethyl S-(2-oxo-2-(4-(trifluoromethyl)phenyl)ethyl) carbonodithioate (8.8 g; see Intermediate 497) in ethyl acetate (200 ml) was treated with vinyl pivalate (8 ml, 54.3 mmol) and heated to reflux. To the refluxing solution was added lauroyl peroxide (2 g), after 1 hour additional lauroyl peroxide (2 g) was added, after 2 hours additional lauroyl peroxide (4 g) was added, after additional 1 hour additional lauroyl peroxide (4 g) was added, and after additional 1 hour additional lauroyl peroxide (4 g) was added. After one further hour, volatiles were removed under reduced pressure, the residue was diluted with hexanes and purified by flash chromatography on silica gel, using a pre-column of basic alumina, eluting with a gradient of ethyl acetate in hexanes (0-20%) to give the title compound in moderate purity (2 g) as a pale yellow gum, which was used without further manipulation.

$^1$H NMR (300 MHz, Chloroform-d) δ 8.17 (d, J=8.1 Hz, 1H), 7.80-7.62 (m, 2H), 6.13 (dd, J=7.3, 3.9 Hz, 1H), 2.95 (ddd, J=17.6, 8.3, 4.8 Hz, 1H), 2.74 (ddd, J=17.6, 8.7, 4.8 Hz, 1H), 2.45 (ddt, J=12.9, 8.5, 4.4 Hz, 1H), 2.39-2.22 (m, 1H), 1.25 (s, 9H).

Intermediate 499

6-(trifluoromethyl)naphthalen-1-ol

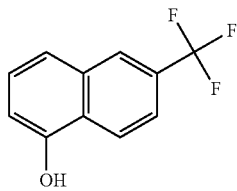 [SMILES: Oc1cccc2cc(C(F)(F)F)ccc12]

A mixture of crude 4-oxo-7-(trifluoromethyl)-1,2,3,4-tetrahydronaphthalen-1-yl pivalate (2 g; see Intermediate 498) and toluene sulfonic acid (1.5 g, 8.71 mmol) in toluene (150 ml) was heated to reflux for 2 hours and then cooled to room temperature. Volatiles were removed, and the residue was purified by flash chromatography on silica gel eluting with a gradient of ethyl acetate in hexanes (0-10%) to give the title compound as a pale yellow solid (504 mg), which was used without further manipulation.

LRMS (ESIneg) m/z=211 [M−H]−

¹H NMR, (400 MHz, Chloroform-d) δ 8.35 (dq, J=8.8, 0.9 Hz, 1H), 8.12 (dt, J=2.0, 1.0 Hz, 1H), 7.65 (dd, J=8.9, 1.9 Hz, 1H), 7.49 (dt, J=8.3, 0.9 Hz, 1H), 7.39 (dd, J=8.3, 7.4 Hz, 1H), 6.96 (dd, J=7.5, 1.0 Hz, 1H), 6.90 (br, 1H).

Intermediate 500

(rac)-ethyl 12-ethyl-10-methyl-1-(3-((6-(trifluoromethyl)naphthalen-1-yl)oxy)propyl)-4,5,6,7,9,10-hexahydropyrazolo[4',3':9,10][1]oxa[6]azacycloundecino[8,7,6-hi]indole-2-carboxylate

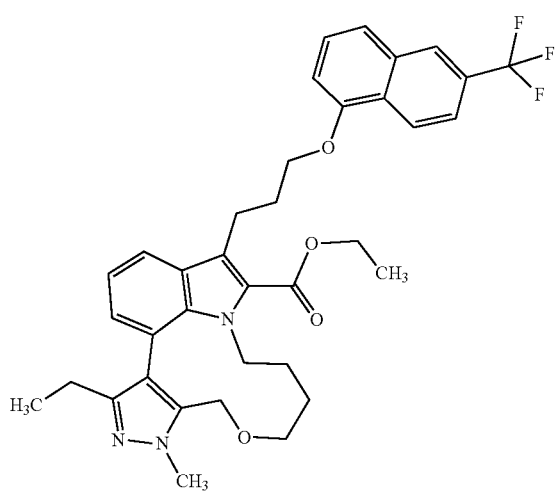 [SMILES: CCOC(=O)c1c(CCCOc2cccc3cc(C(F)(F)F)ccc23)c2cccc3c2n1CCCCOCc1c-3c(CC)nn1C]

A mixture of caesium carbonate (200 mg, 0.61 mmol), 6-(trifluoromethyl)naphthalen-1-ol (70 mg, 0.33 mmol; see Intermediate 499) and (rac)-ethyl 1-(3-bromopropyl)-12-ethyl-10-methyl-4,5,6,7,9,10-hexahydropyrazolo[4',3':9,10][1,6]oxaazacycloundecino[8,7,6-hi]indole-2-carboxylate (107 mg, 0.21 mmol; see Intermediate 455) in tetrahydrofuran (7 ml) was heated to 35° C. for 17 hours, then warmed to 45° C. for 96 hours, cooled to room temperature, then heated to 55° C. for 22 hours. The crude reaction mixture was used in the next step without further manipulation, assuming quantitative yield (208 mg).

LRMS (ESIpos) m/z=634 [M+H]⁺

Intermediate 501

(rac)-ethyl 1-(3-((5-chloronaphthalen-1-yl)oxy)propyl)-10,12-dimethyl-4,5,6,7,9,10-hexahydropyrazolo[4',3':9,10][1]oxa[6]azacycloundecino[8,7,6-h]indole-2-carboxylate

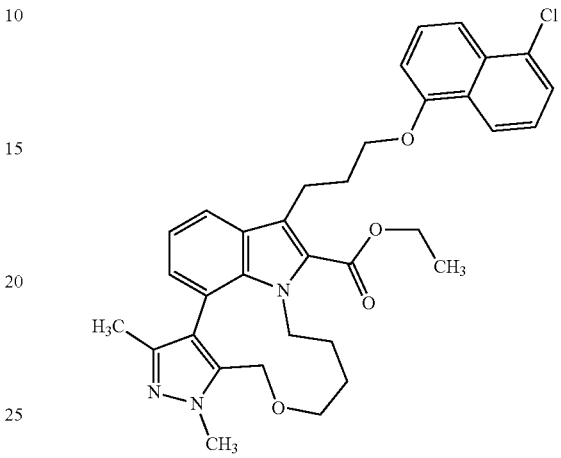

A mixture of (rac)-ethyl 1-(3-bromopropyl)-10,12-dimethyl-4,5,6,7,9,10-hexahydropyrazolo[4',3':9,10][1,6]oxaazacycloundecino[8,7,6-hi]indole-2-carboxylate (100 mg, 0.2 mmol; see Intermediate 503), 5-chloronaphthalen-1-ol (55 mg, 0.3 mmol; see Intermediate 502), and caesium carbonate (360 mg, 1.1 mmol) in tetrahydrofuran (10 ml) was heated to 55° C. for 16 hours. The reaction mixture was diluted with ethyl acetate and the mixture was adsorbed onto celite, subsequent normal phase chromatography eluting with a gradient of methanol in dichloromethane (0-50%) gave the title compound (50 mg) as a gum.

LRMS (ESIpos) m/z=586 [M+H]⁺

Intermediate 502

5-chloronaphthalen-1-ol

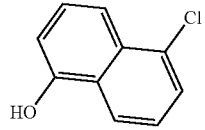

To a stirred solution of 5-aminonaphthalen-1-ol (203 mg, 1.23 mmol) in aqueous hydrochloric acid (1 mL, 1.23 mmol, 37%) and water (1 mL) at 0° C. was added dropwise an aqueous solution of sodium nitrite (135 mg, 1.96 mmol, 0.7 M). A solution of copper (I) chloride (194 mg, 1.96 mmol) in aqueous hydrochloric acid (3 mL, 36%) and acetonitrile (504 µL) was added to the reaction mixture and the mixture was stirred at 65° C. for 20 min, then cooled to room temperature. The reaction mixture was diluted with ethyl acetate, and the organic layer was separated and washed three times with water and then with saturated aqueous sodium chloride solution, dried over sodium sulfate and volatiles were removed under reduced pressure. The residue was purified by flash chromatography on silica gel eluting with a gradient of ethyl acetate in hexanes (0-50%) to give the title compound (110 mg, 50.2% yield).

LRMS (ESIneg): m/z=177.1 [M−H]⁻

1H NMR (300 MHz, Chloroform-d) δ 8.15 (dt, J=8.5, 1.1 Hz, 1H), 7.86 (dt, J=8.6, 0.9 Hz, 1H), 7.59 (dd, J=7.4, 1.2 Hz, 1H), 7.40 (ddd, J=10.1, 8.5, 7.5 Hz, 2H), 6.98-6.83 (m, 1H), 5.34 (s, 1H), 1.26 (s, 0H), 0.87 (d, J=7.7 Hz, 0H).

Intermediate 503

(rac)-ethyl 1-(3-bromopropyl)-10,12-dimethyl-4,5,6,7,9,10-hexahydropyrazolo[4',3':9,10][1,6]oxaazacycloundecino[8,7,6-hi]indole-2-carboxylate

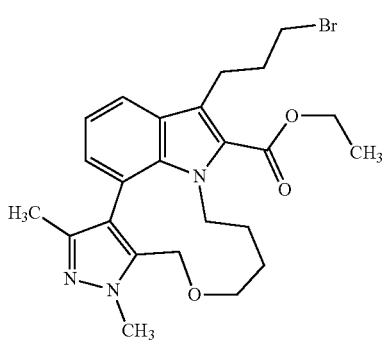 [SMILES: CCOC(=O)c1c(CCCBr)c2cccc3c2n1CCCCOCc1c-3c(C)nn1C]

A solution of (rac)-ethyl 7-(3-hydroxypropyl)-1,3-dimethyl-1,10,11,12,13,15-hexahydropyrazolo[4',3':9,10][1,6]oxazacycloundecino[8,7,6-hi]indole-8-carboxylate (225 mg, 0.53 mmol; see Intermediate 51) and triphenylphosphine (200 mg) in dichloromethane (10 ml) was placed in an ice water bath, and treated with carbon tetrabromide (also referred to herein as tetrabromomethane; 250 mg), after 1 hour of stirring, the volatiles were removed under reduced pressure, and the residue was purified by flash chromatography on silica gel eluting with a gradient of ethyl acetate in hexanes (0-100%), to give the title compound as a tan gum (104 mg).

LRMS (ESIpos) m/z=488 [M+H]⁺

¹H NMR (300 MHz, Chloroform-d) δ 7.72 (dd, J=8.1, 1.3 Hz, 1H), 7.12 (dd, J=8.1, 7.1 Hz, 1H), 6.88 (dd, J=7.1, 1.2 Hz, 1H), 4.72-4.62 (m, 1H), 4.59 (d, J=13.5 Hz, 1H), 4.53-4.31 (m, 3H), 4.22-4.06 (m, 1H), 3.94 (s, 3H), 3.55-3.39 (m, 3H), 3.36-3.11 (m, 2H), 2.86 (ddd, J=11.4, 8.9, 4.2 Hz, 1H), 2.26 (p, J=7.1 Hz, 2H), 2.04 (s, 3H), 1.42 (t, J=7.1 Hz, 3H), 1.35-1.02 (m, 4H).

Intermediate 504 ethyl 11,12,13-trimethyl-1-(4-(naphthalen-1-yloxy)butan-2-yl)-4,5,6,7,9,11-hexahydropyrazolo[4',3':9,10][1]oxa[6]azacycloundecino[8,7,6-hi]indole-2-carboxylate (Mixture of Stereoisomers)

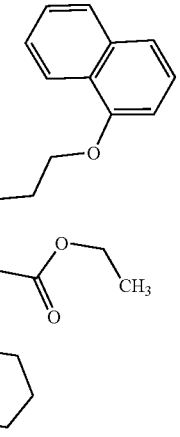

To a solution of triphenylphosphine (780 mg, 3 mmol) in tetrahydrofuran (30 ml) at 0° C. was added diisopropyl azodicarboxylate (0.6 ml, 3 mmol) and the mixture was stirred at that temperature for 15 minutes. A portion of the above white suspension (10 ml, 1 mmol) was added to an ice cold mixture of ethyl 1-(4-hydroxybutan-2-yl)-11,12,13-trimethyl-4,5,6,7,9,11-hexahydropyrazolo[4',3':9,10][1]oxa[6]azacycloundecino[8,7,6-hi]indole-2-carboxylate (mixture of stereoisomers, 230 mg, 0.5 mmol; see Intermediate 464) and 1-naphthol (120 mg, 0.83 mmol) in tetrahydrofuran (10 ml), and the mixture was allowed to warm to room temperature over 20 hours. Volatiles were removed and the residue was purified by flash chromatography on silica gel eluting with a gradient of ethyl acetate in hexanes (25-50%) to give the title compound as a colorless film (70 mg).

LRMS (ESIpos) m/z=580 [M+H]⁺

¹H NMR (400 MHz, Chloroform-d) δ 8.29-8.20 (m, 1H), 7.81-7.71 (m, 2H), 7.49-7.39 (m, 2H), 7.35 (t, J=8.1 Hz, 1H), 7.26 (s, 1H), 7.05 (t, J=8.5 Hz, 1H), 6.62 (dd, J=7.7, 0.9 Hz, 1H), 4.51 (dd, J=22.6, 12.6 Hz, 1H), 4.39 (dd, J=12.5, 4.8 Hz, 1H), 4.31-3.91 (m, 7H), 3.88 (d, J=1.2 Hz, 3H), 3.51-3.32 (m, 1H), 3.32-3.18 (m, 1H), 2.58 (dddd, J=28.0, 22.0, 16.1, 9.4 Hz, 1H), 2.43 (tt, J=13.7, 6.6 Hz, 1H), 2.11-2.02 (m, 3H), 1.84 (d, J=10.7 Hz, 3H), 1.63-1.51 (m, 3H), 1.46-0.99 (m, 7H).

Intermediate 505 ethyl 11,12,13-trimethyl-1-(4-((5,6,7,8-tetrahydronaphthalen-1-yl)oxy)butan-2-yl)-4,5,6,7,9,11-hexahydropyrazolo[4',3':9,10][1]oxa[6]azacycloundecino[8,7,6-hi]indole-2-carboxylate (Mixture of Stereoisomers)

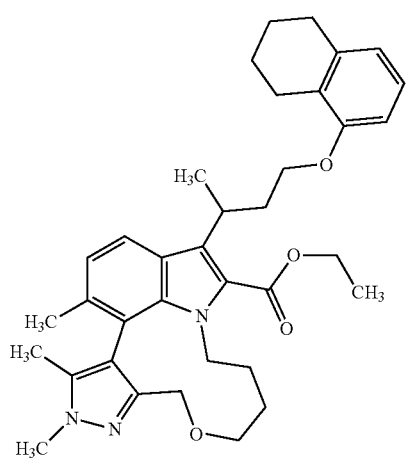 [SMILES: CCOC(=O)c1c(C(C)CCOc2cccc3c2CCCC3)c2ccc(C)c3c2n1CCCCOCc1nn(C)c(C)c1-3]

To a solution of triphenylphosphine (780 mg, 3 mmol) in tetrahydrofuran (30 ml) at 0° C. was added diisopropyl azodicarboxylate (0.6 ml, 3 mmol) and the mixture was stirred at that temperature for 15 minutes. A portion of the above white suspension (10 ml, 1 mmol) was added to an ice cold mixture of ethyl 1-(4-hydroxybutan-2-yl)-11,12,13-trimethyl-4,5,6,7,9,11-hexahydropyrazolo[4',3':9,10][1]oxa[6]azacycloundecino[8,7,6-hi]indole-2-carboxylate (mixture of stereoisomers, 230 mg, 0.5 mmol; see Intermediate 464) and 5,6,7,8-tetrahydronaphthalen-1-ol (120 mg, 0.8 mmol) in tetrahydrofuran (10 ml), and the mixture was allowed to warm to room temperature over 20 hours. Volatiles were removed and the residue was purified by flash chromatography on silica gel eluting with a gradient of ethyl acetate in hexanes (0-100%) to give the title compound as a colorless film (59 mg).
LRMS (ESIpos) m/z=584 [M+H]⁺

Intermediate 506

(rac)-ethyl 10,12-dimethyl-1-(3-((6-(trifluoromethyl)naphthalen-1-yl)oxy)propyl)-4,5,6,7,9,10-hexahydropyrazolo[4',3':9,10][1,6]oxaazacycloundecino[8,7,6-hi]indole-2-carboxylate

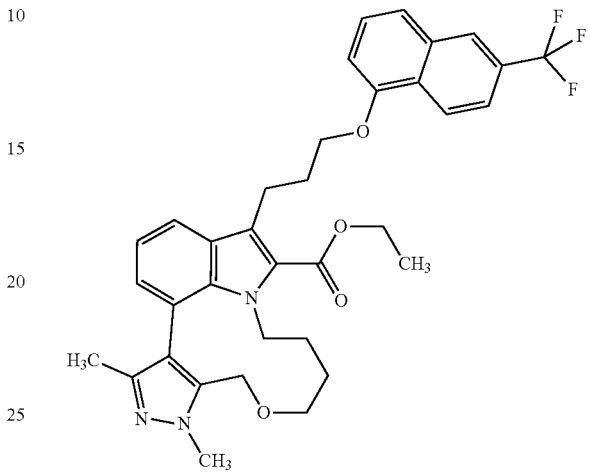

A mixture of (rac)-ethyl 1-(3-hydroxypropyl)-10,12-dimethyl-4,5,6,7,9,10-hexahydropyrazolo[4',3':9,10][1,6]oxaazacycloundecino[8,7,6-hi]indole-2-carboxylate (90 mg, 0.2115 mmol; see Intermediate 51), 6-(trifluoromethyl)naphthalen-1-ol (79 mg, 0.37 mmol; see Intermediate 499), triphenylphosphine (113 mg, 0.43 mmol), and (E)-di-tert-butyl diazene-1,2-dicarboxylate (99 mg, 0.43 mmol), was dissolved in tetrahydrofuran (5 ml) and stirred at room temperature for 17 hours. The volatiles were removed under reduced pressure and the residue was purified by flash chromatography on silica gel eluting with a gradient of ethyl acetate in hexanes (0-100%) to give the title compound along with other materials as a brown gum (81 mg), which was used without further manipulation.
LRMS (ESIpos) m/z=620 [M+H]⁺

Intermediate 507 ethyl 3-ethyl-1-methyl-1H-pyrazole-5-carboxylate

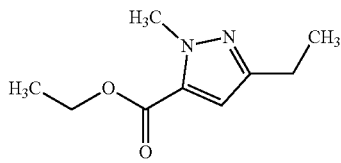

To a solution of diethyl oxalate (7.42 ml, 54.7 mmol) and butan-2-one (5.13 ml, 57.4 mmol) in toluene (200 ml) at 0° C. was added a solution of potassium tert-butoxide (1 M in tetrahydrofuran, 55 ml) over 30 minutes to give an orange solution, this was allowed to warm to room temperature over 16 hours. Volatiles were removed and the residue was dissolved in ethanol (200 ml) and treated with acetic acid (6 ml) and methyl hydrazine (6 ml) and stirred at room temperature for 1 hour, then heated to reflux for 4 hours.

Volatiles were removed and the residue was partitioned between ethyl acetate (100 ml) and water (100 ml). The layers were separated and the organic phase was washed sequentially with a saturated aqueous solution of sodium bicarbonate, and a saturated aqueous solution of sodium chloride, dried over magnesium sulfate, and filtered. Volatiles were removed and the residue was purified by flash chromatography eluting with a gradient of ethyl acetate in hexanes (0-100%) to give the title compound as a pale yellow oil (2.67 g).

LRMS (ESIpos) m/z=183 [M+H]$^+$ $^1$H NMR (300 MHz, Chloroform-d) δ 6.64 (d, J=0.6 Hz, 1H), 4.33 (q, J=7.1 Hz, 2H), 4.12 (s, 3H), 2.72-2.55 (m, 2H), 1.37 (t, J=7.1 Hz, 3H), 1.24 (t, J=7.6 Hz, 3H).

$^{13}$C NMR (101 MHz, Chloroform-d) 6159.98, 153.01, 132.86, 108.89, 60.79, 39.07, 21.18, 14.24, 13.79.

Intermediate 508 ethyl 4-bromo-3-ethyl-1-methyl-1H-pyrazole-5-carboxylate

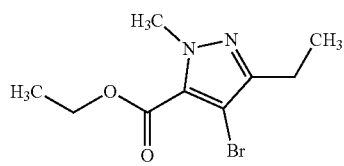

To a 0° C. stirred solution of ethyl 3-ethyl-1-methyl-1H-pyrazole-5-carboxylate (5.39 g, 29.5 mmol; see Intermediate 507) in dichloromethane (98.3 ml) was added a solution of bromine (1.97 ml, 38.3 mmol) in dichloromethane (38.3 ml) dropwise. The resulting mixture was allowed to warm to room temperature over 24 hours with stirring, then the reaction was stopped by the addition of a 10% aqueous solution of sodium thiosulfate (60 ml). The layers were separated and the aqueous phase was extracted twice with dichloromethane (100 ml), the combined organic phases were washed with water, dried over magnesium sulfate, filtered, and volatiles were removed under reduced pressure. The residue was purified by flash chromatography on silica gel eluting with a gradient of ethyl acetate in hexanes (0-30%) to afford the title compound as a colorless oil (6.39 g).

MS (ESIpos) m/z 261=[M+H]$^+$ $^1$H NMR (300 MHz, Chloroform-d) δ 4.39 (qd, J=7.1, 0.5 Hz, 2H), 4.10 (s, 3H), 2.64 (q, J=7.6 Hz, 2H), 1.42 (td, J=7.1, 0.5 Hz, 3H), 1.23 (dd, J=7.8, 7.3 Hz, 3H).

Intermediate 509

(4-bromo-3-ethyl-1-methyl-1H-pyrazol-5-yl)methanol

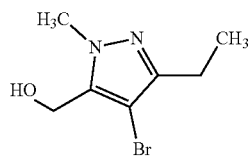

To a 0° C. stirred suspension of lithium aluminum hydride (1.38 g, 36.6 mmol) in tetrahydrofuran (36.6 mL) was added a solution of ethyl 4-bromo-3-ethyl-1-methyl-1H-pyrazole-5-carboxylate (9.57 g, 36.6 mmol; see Intermediate 508) in tetrahydrofuran (36.6 mL) dropwise. Following complete addition, the mixture was warmed to room temperature, stirred for 1 hour and cooled back to 0° C. The mixture was diluted with diethyl ether (50 mL) and then water (1.40 mL) was carefully added. A 15% w/w aqueous sodium hydroxide solution (4.70 mL) was then added to the mixture, followed by water (14.1 mL), and the resulting slurry was warmed to room temperature and stirred for a further 15 minutes. The mixture was dried over magnesium sulfate, filtered, and volatiles were removed under reduced pressure. The residue was purified by flash column chromatography on silica gel eluting with a gradient of ethyl acetate in hexanes (0-100%) to give the title compound as a white solid (6.69 g).

MS (ESIpos) m/z=219 [M+H]$^+$ $^1$H NMR (300 MHz, Chloroform-d) δ 4.65 (d, J=5.8 Hz, 2H), 3.87 (s, 3H), 2.59 (q, J=7.6 Hz, 2H), 2.23-2.14 (m, 1H), 1.21 (t, J=7.6 Hz, 3H).

Experimental Section

EXAMPLES

Example 1-1

(rac)-(E/Z)-3-{[4-(4-acetylpiperazin-1-yl)phenoxy]methyl}-1-methyl-7-[3-(naphthalen-1-yloxy)propyl]-1,10,13,15-tetrahydropyrazolo[4',3':9,10][1,6]oxazacycloundecino[8,7,6-hi]indole-8-carboxylic acid

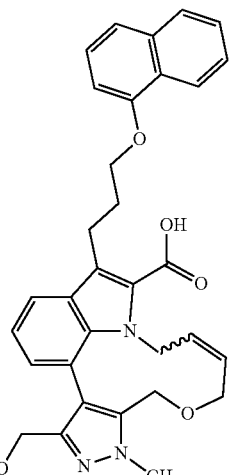
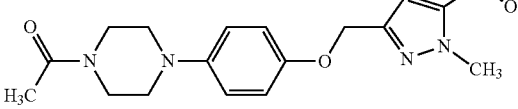

A mixture of (rac)-(E/Z)-ethyl 3-{[4-(4-acetylpiperazin-1-yl)phenoxy]methyl}-1-methyl-7-[3-(naphthalen-1-yloxy)propyl]-1,10,13,15-tetrahydropyrazolo[4',3':9,10][1,6]oxazacycloundecino[8,7,6-hi]indole-8-carboxylate (see Intermediate 1-14; 43.0 mg, 56.0 µmol), THF (2.3 ml), ethanol (1.6 ml) and aqueous lithium hydroxide (1.1 ml, 1.0 M, 1.1 mmol) was stirred for 16 h at room temperature and then for 6 h at 60° C. For work-up, citric acid (235 mg, 1.12 mmol) was added to adjust the pH to 5-6, water was added and the mixture was extracted three times with a mixture of dichloromethane/2-propanol (4:1). The combined organic phases were washed with brine, filtrated through a silicone filter and concentrated. The residue was purified by preparative TLC (silica, ethyl acetate 100%, followed by ethyl acetate/methanol 8:2) to give two products (RF=0.48 and 0.00, respectively)

RF=0.48 (ethyl acetate/methanol 8:2): 11 mg, which was stirred with ethyl acetate to precipitate the title compound (1.9 mg)

LC-MS (Method 2): $R_t$=0.92 min; MS (ESIpos): m/z=740 [M+H]$^+$ $^1$H-NMR (400 MHz, DMSO-d6) δ[ppm]: 1.203 (0.00), 1.637 (5.00), 1.926 (1.00), 1.936 (16.00), 1.958 (1.00), 2.148 (0.00), 2.167 (1.00), 2.179 (0.00), 2.183 (0.00), 2.295 (0.00), 2.300 (2.00), 2.304 (2.00), 2.309 (2.00), 2.313 (0.00), 2.638 (0.00), 2.642 (2.00), 2.646 (2.00), 2.651 (2.00), 2.656 (0.00), 2.736 (1.00), 2.749 (1.00), 2.762 (1.00), 2.774 (1.00), 2.787 (1.00), 2.799 (1.00), 3.121 (0.00), 3.136 (0.00), 3.152 (0.00), 3.170 (0.00), 3.232 (0.00), 3.238 (0.00), 3.251 (0.00), 3.259 (1.00), 3.263 (1.00), 3.275 (1.00), 3.278 (1.00), 3.286 (1.00), 3.293 (1.00), 3.297 (1.00), 3.302 (1.00), 3.311 (2.00), 3.325 (3.00), 3.341 (4.00), 3.491 (5.00), 3.503 (4.00), 3.518 (2.00), 3.535 (2.00), 3.560 (0.00), 3.573 (0.00), 3.579 (0.00), 3.583 (0.00), 3.586 (0.00), 3.751 (0.00), 3.760 (0.00), 3.794 (0.00), 3.886 (0.00), 3.899 (13.00), 4.097 (1.00), 4.116 (1.00), 4.133 (0.00), 4.231 (1.00), 4.265 (1.00), 4.353 (1.00), 4.382 (1.00), 4.469 (2.00), 4.483 (0.00), 4.497 (1.00), 4.507 (0.00), 4.658 (1.00), 4.692 (1.00), 5.126 (0.00), 5.131 (0.00), 5.152 (0.00), 5.156 (0.00), 5.433 (0.00), 5.471 (0.00), 6.523 (4.00), 6.541 (3.00), 6.546 (4.00), 6.646 (3.00), 6.669 (2.00), 6.780 (1.00), 6.797 (2.00), 6.816 (1.00), 6.834 (1.00), 7.290 (0.00), 7.310 (1.00), 7.329 (1.00), 7.384 (2.00), 7.404 (1.00), 7.450 (1.00), 7.453 (1.00), 7.456 (1.00), 7.461 (1.00), 7.464 (2.00), 7.473 (4.00), 7.481 (2.00), 7.488 (1.00), 7.808 (1.00), 7.817 (0.00), 7.826 (0.00), 7.832 (1.00), 8.170 (1.00), 8.176 (0.00), 8.194 (0.00), 8.457 (0.00).

RF=0.00 (ethyl acetate/methanol 8:2): 10 mg corresponds to 1-methyl-7-[3-(naphthalen-1-yloxy)propyl]-3-{[4-(piperazin-1-yl)phenoxy]methyl}-1,10,13,15-tetrahydropyrazolo[4',3':9,10][1,6]oxazacycloundecino[8,7,6-hi]indole-8-carboxylic acid

Example 1-2

(rac)-(E/Z)-1-methyl-7-[3-(naphthalen-1-yloxy)propyl]-3-{[4-(piperazin-1-yl)phenoxy]methyl}-1,10,13,15-tetrahydropyrazolo[4',3':9,10][1,6]oxazacycloundecino[8,7,6-hi]indole-8-carboxylic acid

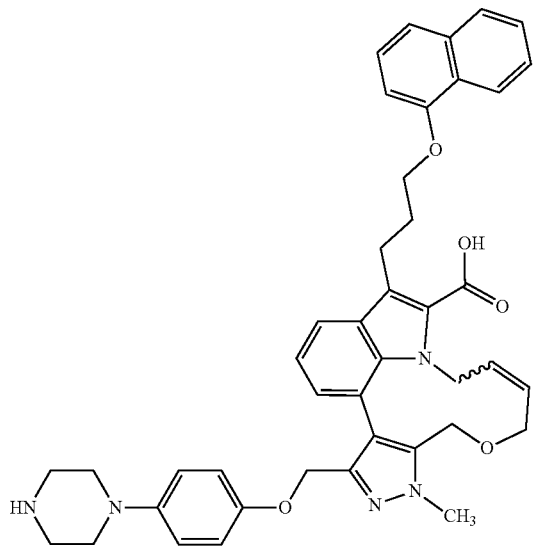 [SMILES: Cn1nc(COc2ccc(N3CCNCC3)cc2)c2c1COCC=CCn1c(C(=O)O)c(CCCOc3cccc4ccccc34)c3cccc-2c31]

The title compound was isolated as side product in the synthesis of (rac)-(E/Z)-3-{[4-(4-acetylpiperazin-1-yl)phenoxy]methyl}-1-methyl-7-[3-(naphthalen-1-yloxy)propyl]-1,10,13,15-tetrahydropyrazolo[4',3':9,10][1,6]oxazacycloundecino[8,7,6-hi]indole-8-carboxylic acid (10 mg).

RF=0.00 (ethyl acetate/methanol 8:2)

LC-MS (Method 2): $R_t$=0.88 min; MS (ESIpos): m/z=698 [M+H]$^+$ $^1$H-NMR (400 MHz, DMSO-d6): δ [ppm]=8.26-8.18 (m, 1H), 7.88-7.80 (m, 1H), 7.54-7.39 (m, 4H), 7.38-7.30 (m, 1H), 6.90-6.77 (m, 2H), 6.70-6.61 (m, 2H), 6.60-6.51 (m, 3H), 5.47 (br d, 1H), 5.21-5.08 (m, 2H), 4.70 (d, 1H), 4.61-4.45 (m, 2H), 4.37 (d, 1H), 4.27 (d, 1H), 4.19-4.07 (m, 2H), 3.93 (s, 3H), 3.83-3.75 (m, 1H), 3.57-3.48 (m, 1H), 3.22-3.13 (m, 1H), 2.85-2.69 (m, 8H), 2.26-2.14 (m, 2H)

Example 1-3

(rac)-3-({4-[4-(diethylsulfamoyl)piperazin-1-yl]
phenoxy}methyl)-1-methyl-7-[3-(naphthalen-1-
yloxy)propyl]-1,10,11,12,13,15-hexahydropyrazolo
[4',3':9,10][1,6]oxazacycloundecino[8,7,6-hi]indole-
8-carboxylic acid

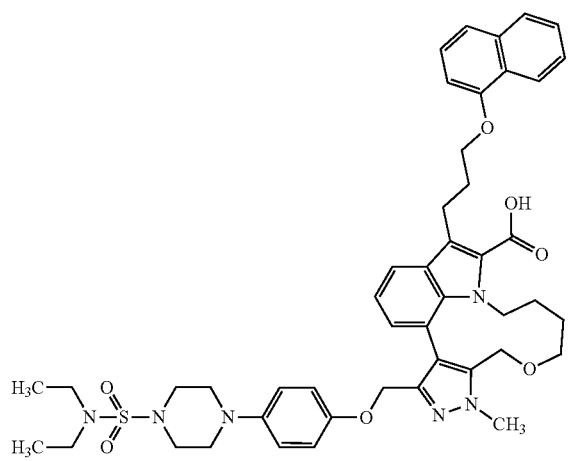 [SMILES: CCN(CC)S(=O)(=O)N1CCN(c2ccc(OCc3nn(C)c4c3-c3cccc5c(CCCOc6cccc7ccccc67)c(C(=O)O)n(c35)CCCCOC4)cc2)CC1]

The title compound was prepared in analogy to the synthesis of (rac)-(E/Z)-3-{[4-(4-acetylpiperazin-1-yl) phenoxy]methyl}-1-methyl-7-[3-(naphthalen-1-yloxy)propyl]-1,10,13,15-tetrahydropyrazolo[4',3':9,10][1,6]oxazacycloundecino[8,7,6-hi]indole-8-carboxylic acid (see Example 1-1) using (rac)-ethyl 3-({4-[4-(diethylsulfamoyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (see Intermediate 1-15; 167 mg, 193 µmol) as starting material. The crude product was purified by flash chromatography (Biotage SNAP cartridge silica 25 g, ethyl acetate/ethanol gradient, 0%→20% ethanol) to give the title compound (84 mg, 50% yield).

LC-MS (Method 2): $R_t$=1.05 min; MS (ESIneg): m/z=833 [M–H]⁻

¹H-NMR (400 MHz, DMSO-d6): d [ppm]=13.14 (br s, 1H), 8.25-8.20 (m, 1H), 7.88-7.83 (m, 1H), 7.68 (br d, 1H), 7.55-7.47 (m, 2H), 7.47-7.42 (m, 1H), 7.38-7.33 (m, 1H), 6.96 (t, 1H), 6.85-6.75 (m, 2H), 6.72-6.60 (m, 2H), 6.55-6.49 (m, 2H), 4.73-4.65 (m, 2H), 4.62-4.51 (m, 1H), 4.46 (d, 1H), 4.28 (d, 1H), 4.16-4.07 (m, 3H), 3.92 (s, 3H), 3.52-3.37 (m, 2H), 3.28-3.21 (m, 2H), 3.16 (q, 4H), 3.07-2.98 (m, 4H), 2.92-2.79 (m, 5H), 2.18 (quin, 2H), 1.39 (br s, 1H), 1.12-1.00 (m, 8H)

The title compound (81 mg) was separated into enantiomers by chiral HPLC [Instrument: Labomatic HD5000, Labocord-5000; Gilson GX-241, Labcol Vario 4000; Column: Chiralpak IA 5µ 250×30 mm; Eluent A: hexane+0.1 Vol-% TFA; Eluent B: ethanol+0.1 Vol-% TFA; isocratic: 50% A+50% B; flow 40.0 ml/min; detection: UV 254 nm] to give enantiomer 1 (9.5 mg) and enantiomer 2 (28.1 mg).

Analytical chiral HPLC method: Instrument: Agilent HPLC 1260; column: Chiralpak IA 3µ 100×4.6 mm; eluent A: hexane+0.1 Vol-% TFA; eluent B: ethanol; isocratic: 50% A+50% B; flow 1.4 ml/min; temperature: 25° C.; detection: DAD 254 nm

Example 1-4

3-({4-[4-(diethylsulfamoyl)piperazin-1-yl]
phenoxy}methyl)-1-methyl-7-[3-(naphthalen-1-
yloxy)propyl]-1,10,11,12,13,15-hexahydropyrazolo
[4',3':9,10][1,6]oxazacycloundecino[8,7,6-hi]indole-
8-carboxylic acid (Enantiomer 1)

The obtained product was re-purified by flash chromatography followed by preparative HPLC [Instrument: Waters Autopurification system; column: Waters XBrigde C18 5µ 100×30 mm; eluent A: water+0.2 Vol-% ammonia (32%), eluent B: acetonitrile; gradient: 0.00-0.50 min 16% B (25→70 ml/min), 0.51-5.50 min 32-52% B (70 ml/min); detection: DAD scan: 210-400 nm] to give the title compound (9.5 mg, 95% purity)

Analytical chiral HPLC (Method see Example 1-3): $R_t$=3.26 min; ee>99.9%

Example 1-5

3-({4-[4-(diethylsulfamoyl)piperazin-1-yl]
phenoxy}methyl)-1-methyl-7-[3-(naphthalen-1-
yloxy)propyl]-1,10,11,12,13,15-hexahydropyrazolo
[4',3':9,10][1,6]oxazacycloundecino[8,7,6-hi]indole-
8-carboxylic acid (Enantiomer 2)

Analytical chiral HPLC (Method see Example 1-3): $R_t$=4.80 min; ee 99.2%

Example 1-6

(rac)-3-({4-[4-(tert-butoxycarbonyl)piperazin-1-yl]
phenoxy}methyl)-1-methyl-7-[3-(naphthalen-1-
yloxy)propyl]-1,10,11,12,13,15-hexahydropyrazolo
[4',3':9,10][1,6]oxazacycloundecino[8,7,6-hi]indole-
8-carboxylic acid

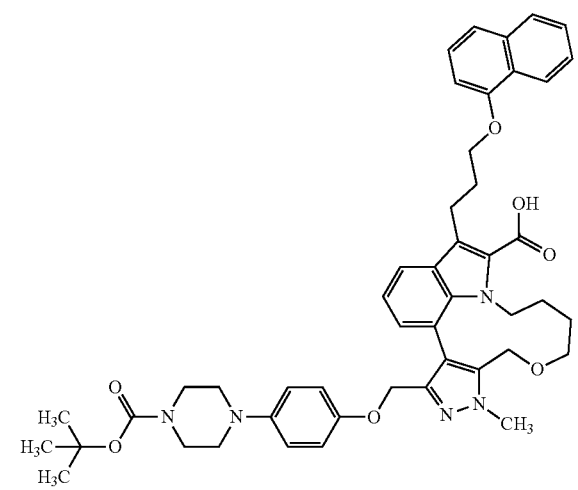 [SMILES: Cn1nc(COc2ccc(N3CCN(C(=O)OC(C)(C)C)CC3)cc2)c2c1COCCCCn1c(C(=O)O)c(CCCOc3cccc4ccccc34)c3cccc-2c31]

A mixture of (rac)-ethyl 3-({4-[4-(tert-butoxycarbonyl) piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (see Intermediate 1-11; 190 mg, 229 µmol), THF (9.3 ml), ethanol (6.7 ml) and aqueous lithium hydroxide (4.6 ml, 1.0 M, 4.6 mmol) was stirred for 32 h at 50-60°

C. For work-up, citric acid (964 mg, 4.59 mmol) was added to adjust the pH to 5-6, water was added and the mixture was extracted three times with a mixture of dichloromethane/2-propanol (4:1). The combined organic phase were washed with brine, filtrated through a silicone filter and concentrated. The residue was purified twice by preparative HPLC (Methode P11 followed by Method P2) to give the title compound (27 mg, 94% purity, 14% yield).

LC-MS (Method 2): $R_t$=1.01 min; MS (ESIpos): m/z=800 [M+H]$^+$ $^1$H-NMR (400 MHz, DMSO-d6): δ [ppm]=13.08 (br s, 1H), 8.26-8.21 (m, 1H), 7.88-7.84 (m, 1H), 7.72 (dd, 1H), 7.55-7.47 (m, 2H), 7.47-7.43 (m, 1H), 7.39-7.34 (m, 1H), 6.98 (t, 1H), 6.87-6.78 (m, 2H), 6.70-6.65 (m, 2H), 6.53-6.48 (m, 2H), 4.75-4.63 (m, 2H), 4.58-4.43 (m, 2H), 4.29 (d, 1H), 4.17-4.04 (m, 3H), 3.92 (s, 3H), 3.52-3.33 (m, 3H), 3.29-3.21 (m, 2H), 3.09-3.00 (m, 4H), 2.96-2.79 (m, 5H), 2.22-213 (m, 2H), 1.41-1.20 (m, 2H), 1.11 (s, 9H)

Example 1-7

(rac)-1-methyl-3-{[4-(4-methylpiperazin-1-yl)phenoxy]methyl}-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid

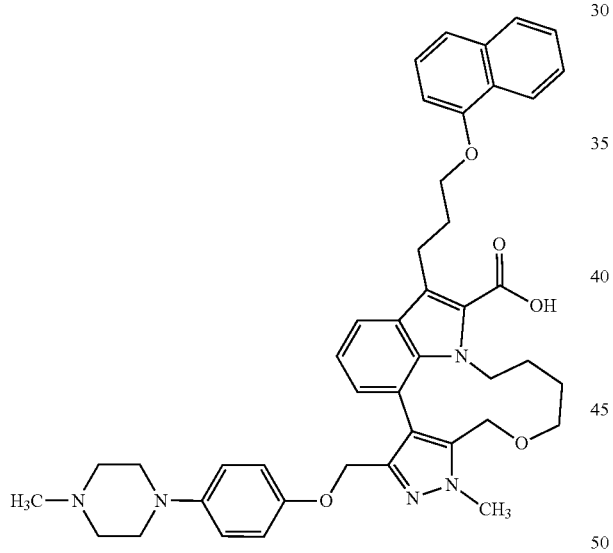

A mixture of (rac)-ethyl 1-methyl-3-{[4-(4-methylpiperazin-1-yl)phenoxy]methyl}-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (see Intermediate 1-16; 75.0 mg, 101 μmol), THF (4.1 ml), ethanol (2.9 ml) and aqueous lithium hydroxide (2.3 ml, 1.0 M, 2.3 mmol) was stirred for 16 h at 50° C. For work-up, citric acid (478 mg, 2.27 mmol) was added to adjust the pH to 5-6, water was added and the mixture was extracted three times with a mixture of dichloromethane/2-propanol (4:1). The combined organic phases were washed with brine, filtrated through a silicone filter and concentrated. The residue was purified by preparative HPLC [Instrument: Waters Autopurification system; column: Phenomenex Kinetex C18 5μ 100×30 mm; eluent A: water+0.1 Vol-% formic acid (99%), eluent B: acetonitrile; gradient: 0.00-0.50 min 16% B (25→70 ml/min), 0.51-5.50 min 33-50% B (70 ml/min), DAD scan: 210-400 nm] to give the title 20.0 mg (93% purity, 26% yield).

LC-MS (Method 3): $R_t$=1.18 min; MS (ESIpos): m/z=714 [M+H]$^+$ $^1$H-NMR (400 MHz, DMSO-d6) δ[ppm]: 0.968 (0.43), 1.048 (0.90), 1.108 (16.00), 1.209 (0.54), 1.233 (1.37), 1.256 (0.86), 1.349 (0.43), 1.362 (0.43), 1.413 (0.54), 2.149 (9.56), 2.173 (1.37), 2.179 (1.47), 2.197 (0.97), 2.309 (2.05), 2.323 (4.35), 2.327 (4.21), 2.332 (3.63), 2.460 (0.72), 2.465 (0.68), 2.518 (7.87), 2.523 (5.72), 2.660 (0.72), 2.665 (1.62), 2.669 (2.23), 2.674 (1.55), 2.679 (0.72), 2.808 (0.58), 2.829 (2.66), 2.841 (3.31), 2.853 (2.41), 3.203 (0.58), 3.221 (0.97), 3.238 (1.04), 3.247 (1.11), 3.255 (1.44), 3.333 (2.37), 3.352 (2.70), 3.366 (2.23), 3.384 (1.91), 3.439 (0.90), 3.457 (1.08), 3.469 (0.86), 3.487 (0.86), 3.505 (0.61), 3.917 (12.30), 3.941 (0.79), 4.069 (0.61), 4.083 (0.68), 4.091 (0.79), 4.107 (1.29), 4.126 (1.15), 4.142 (0.58), 4.151 (0.50), 4.266 (1.26), 4.299 (1.37), 4.425 (1.55), 4.452 (1.80), 4.531 (0.50), 4.566 (0.50), 4.664 (2.16), 4.669 (1.76), 4.693 (1.69), 4.703 (1.40), 6.477 (2.66), 6.500 (3.56), 6.618 (3.63), 6.641 (2.66), 6.793 (1.44), 6.804 (1.29), 6.810 (1.65), 6.819 (1.47), 6.943 (1.33), 6.963 (1.55), 6.981 (1.04), 7.335 (1.08), 7.355 (1.91), 7.374 (1.51), 7.431 (1.98), 7.452 (1.26), 7.488 (0.47), 7.501 (1.22), 7.505 (1.19), 7.509 (1.58), 7.517 (2.70), 7.525 (1.55), 7.528 (1.44), 7.533 (1.40), 7.545 (0.54), 7.685 (1.29), 7.703 (1.19), 7.849 (1.19), 7.858 (0.65), 7.867 (1.04), 7.873 (1.04), 8.224 (1.04), 8.230 (0.93), 8.240 (0.54), 8.248 (1.01).

Example 1-8

(rac)-1-methyl-3-({4-[4-(methylsulfonyl) piperazin-1-yl]phenoxy}methyl)-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid

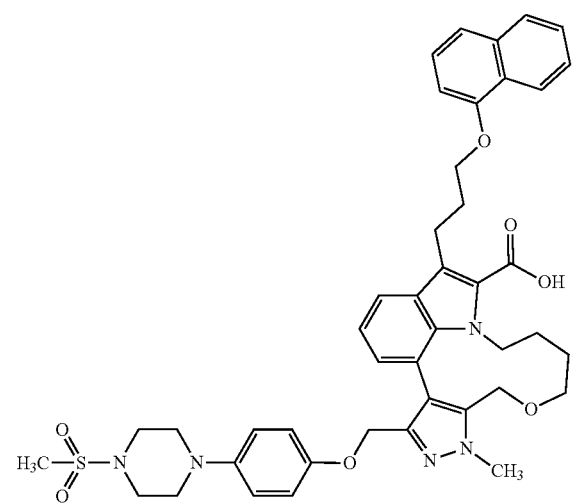 [SMILES: Cn1nc(COc2ccc(N3CCN(S(C)(=O)=O)CC3)cc2)c2c1COCCCCn1c(C(=O)O)c(CCCOc3cccc4ccccc34)c3cccc-2c31]

A mixture of (rac)-ethyl 1-methyl-3-({4-[4-(methylsulfonyl)piperazin-1-yl]phenoxy}methyl)-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (see Intermediate 1-17; 185 mg, 230 μmol), THF (9.3 ml), ethanol (6.7 ml) and aqueous lithium hydroxide (5.2 ml, 1.0 M, 5.2 mmol) was stirred for 16 h at 50° C. For work-up, citric acid (1.09 g, 5.16 mmol) was added to adjust the pH to 5-6, water was added and the mixture was extracted three times with a mixture of dichloromethane/2-propanol (4:1). The combined organic phases were washed with brine, filtrated through a silicone filter and concentrated. The residue was purified by preparative HPLC (Method P1) to give the title compound (61.0 mg, 34% yield).

LC-MS (Method 3): $R_t$=1.42 min; MS (ESIpos): m/z=778 [M+H]$^+$ $^1$H-NMR (400 MHz, DMSO-d6) δ[ppm]: 1.047 (0.82), 2.169 (0.73), 2.186 (1.11), 2.203 (0.77), 2.322 (0.77), 2.326 (1.08), 2.332 (0.77), 2.518 (4.45), 2.522 (3.08), 2.539 (0.82), 2.664 (0.78), 2.668 (1.08), 2.673 (0.77), 2.817 (0.44), 2.857 (16.00), 2.929 (2.00), 2.941 (2.92), 2.954 (2.75), 3.095 (2.84), 3.108 (3.03), 3.119 (2.10), 3.237 (0.40), 3.252 (0.40), 3.270 (0.64), 3.356 (0.75), 3.373 (0.46), 3.389 (0.46), 3.458 (0.51), 3.488 (0.47), 3.920 (10.84), 4.078 (0.55), 4.091 (0.62), 4.099 (0.67), 4.115 (1.42), 4.131 (1.24), 4.147 (0.49), 4.264 (1.13), 4.298 (1.24), 4.446 (1.37), 4.475 (1.68), 4.496 (0.51), 4.532 (0.46), 4.670 (1.37), 4.689 (1.66), 4.704 (1.28), 4.717 (1.42), 6.507 (2.59), 6.530 (3.19), 6.675 (3.35), 6.698 (2.51), 6.793 (1.31), 6.810 (1.42), 6.823 (1.09), 6.826 (1.11), 6.841 (1.29), 6.960 (1.18), 6.981 (1.46), 6.998 (0.97), 7.340 (1.04), 7.360 (1.84), 7.379 (1.37), 7.435 (1.84), 7.456 (1.15), 7.490 (0.40), 7.502 (1.20), 7.508 (1.90), 7.518 (2.50), 7.527 (2.08), 7.532 (1.29), 7.544 (0.44), 7.703 (1.15), 7.705 (1.17), 7.723 (1.09), 7.725 (1.06), 7.850 (1.06), 7.854 (0.80), 7.861 (0.55), 7.868 (0.75), 7.874 (0.91), 8.224 (0.97), 8.231 (0.75), 8.239 (0.46), 8.248 (0.87), 13.175 (0.46).

The title compound (54 mg) was separated into enantiomers by chiral HPLC [Instrument: Labomatic HD5000, Labocord-5000; Gilson GX-241, Labcol Vario 4000, column: Chiralpak IA 5µ 250×20 mm; eluent A: hexane+0.1 vol-% TFA (99%); eluent B: 2-propanol; isocratic: 50% A+50% B; flow 10.0 ml/min; detection: UV 254 nm] to give enantiomer 1 (18.5 mg, see Example 1-9) and enantiomer 2 (21.0 mg, see Example 1-10).

Analytical chiral HPLC method: Instrument: Agilent HPLC 1260; column: Chiralpak IA 3µ 100×4.6 mm; eluent A: hexane+0.1 Vol-% TFA (99%); eluent B: 2-propanol; isocratic: 50% A+50% B; flow 1.4 ml/min; temperature: 25° C.; detection: DAD 254 nm Example 1-9

1-methyl-3-({4-[4-(methylsulfonyl)piperazin-1-yl] phenoxy}methyl)-7-[3-(naphthalen-1-yloxy)propyl]-1,10,11,12,13,15-hexahydropyrazolo[4',3':9,10][1,6] oxazacycloundecino[8,7,6-hi]indole-8-carboxylic acid (Enantiomer 1)

See Example 1-8 for preparation and enantiomer separation.

Analytical chiral HPLC (Method see Example 1-8): $R_t$=3.11 min; ee 96.1%

Example 1-10

1-methyl-3-({4-[4-(methylsulfonyl)piperazin-1-yl] phenoxy}methyl)-7-[3-(naphthalen-1-yloxy)propyl]-1,10,11,12,13,15-hexahydropyrazolo[4',3':9,10][1,6] oxazacycloundecino[8,7,6-hi]indole-8-carboxylic acid (Enantiomer 2)

See Example 1-8 for preparation and enantiomer separation.

Analytical chiral HPLC (Method see Example 1-8): $R_t$=5.11 min; ee 97.4%

Example 1-11

(rac)-3-({4-[4-(cyclopropylsulfonyl)piperazin-1-yl] phenoxy}methyl)-1-methyl-7-[3-(naphthalen-1-yloxy)propyl]-1,10,11,12,13,15-hexahydropyrazolo [4',3':9,10][1,6]oxazacycloundecino[8,7,6-hi]indole-8-carboxylic acid

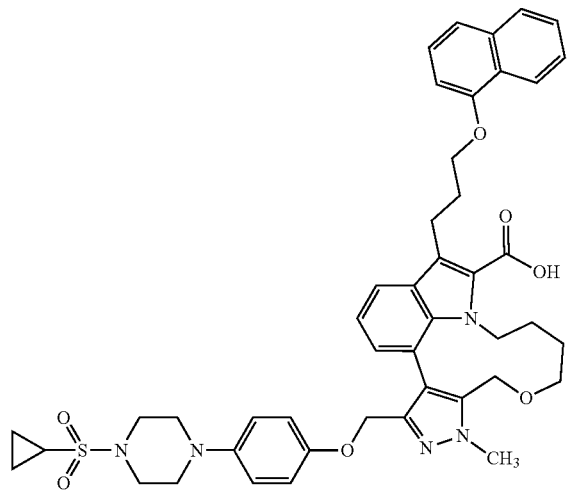 [SMILES: Cn1nc(COc2ccc(N3CCN(S(=O)(=O)C4CC4)CC3)cc2)c2c1COCCCCn1c(C(=O)O)c(CCCOc3cccc4ccccc34)c3cccc-2c31]

A mixture of (rac)-ethyl 3-({4-[4-(cyclopropylsulfonyl) piperazin-1-yl]phenoxy}methyl)-1-methyl-7-[3-(naphthalen-1-yloxy)propyl]-1,10,11,12,13,15-hexahydropyrazolo [4',3':9,10][1,6]oxazacycloundecino[8,7,6-hi]indole-8-carboxylate (see Intermediate 1-18; 205 mg, 246 µmol), THF (10 ml), ethanol (7.2 ml) and aqueous lithium hydroxide (5.5 ml, 1.0 M, 5.5 mmol) was stirred for 16 h at 50° C. For work-up, citric acid (1.16 g, 5.54 mmol) was added to adjust the pH to 5-6, water was added and the mixture was extracted three times with a mixture of dichloromethane/2-propanol (4:1). The combined organic phases were washed with brine, filtrated through a silicone filter and concentrated. The residue was purified by flash chromatography (ethyl acetate/ethanol gradient, 0%→20% ethanol) followed by preparative HPLC (Method P1) to give the title compound (67.0 mg, 33% yield).

LC-MS (Method 3): $R_t$=1.47 min; MS (ESIpos): m/z=804 [M+H]$^+$ $^1$H-NMR (400 MHz, DMSO-d$_6$): δ [ppm]=13.18 (br s, 1H), 8.25-8.21 (m, 1H), 7.88-7.84 (m, 1H), 7.71 (d, 1H), 7.55-7.48 (m, 2H), 7.46-7.43 (m, 1H), 7.36 (t, 1H), 6.98 (t, 1H), 6.85-6.78 (m, 2H), 6.70-6.66 (m, 2H), 6.54-6.49 (m, 2H), 4.73-4.66 (m, 2H), 4.55-4.44 (m, 2H), 4.28 (d, 1H), 4.16-4.04 (m, 3H), 3.92 (s, 3H), 3.51-3.44 (m, 1H), 3.41-3.35 (m, 1H), 3.30-3.22 (m, 1H), 3.22-3.16 (m, 4H), 2.94-2.88 (m, 4H), 2.88-2.80 (m, 1H), 2.59-2.53 (m, 1H), 2.18 (quin, 2H), 1.42-1.32 (m, 1H), 1.29-1.20 (m, 1H), 1.09-1.02 (m, 2H), 1.01-0.87 (m, 4H)

The title compound (60.0 mg) was separated into enantiomers by chiral HPLC [Instrument: Labomatic HD5000, Labocord-5000; Gilson GX-241, Labcol Vario 4000, column: Chiralpak IA 5µ 250×20 mm; eluent A: hexane+0.1 Vol-% TFA (99%); eluent B: 2-propanol; isocratic: 50% A+50% B; flow 15.0 ml/min; detection UV 254 nm] to give enantiomer 1 (21.0 mg, see Example 1-12) and enantiomer 2 (26.0 mg, see Example 1-13).

Analytical chiral HPLC method: Instrument: Agilent HPLC 1260; column: Chiralpak IA 3µ 100×4.6 mm; eluent A: hexane+0.1 Vol-% TFA (99%); eluent B: 2-propanol; isocratic: 50% A+50% B; flow 1.4 ml/min; temperature: 25° C.; detection: DAD 254 nm Example 1-12

3-({4-[4-(cyclopropylsulfonyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (Enantiomer 1)

See Example 1-11 for preparation and enantiomer separation.

Analytical chiral HPLC (Method see Example 1-11): $R_t$=2.98 min; ee 96.6%

Example 1-13

3-({4-[4-(cyclopropylsulfonyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (Enantiomer 2)

See Example 1-11 for preparation and enantiomer separation.

Analytical chiral HPLC (Method see Example 1-11): $R_t$=4.05 min; ee 92.2%

Example 1-14

(rac)-11-({4-[4-(dimethylsulfamoyl)piperazin-1-yl]phenoxy}methyl)-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid

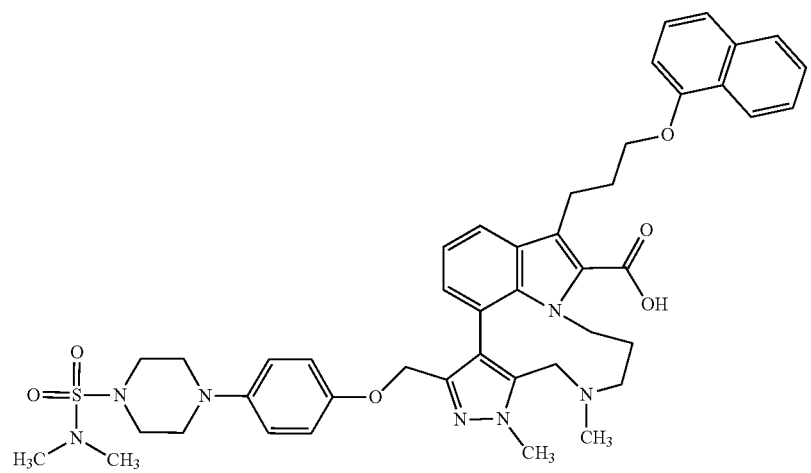 [SMILES: CN1CCCn2c(C(=O)O)c(CCCOc3cccc4ccccc34)c3cccc(c32)-c2c(COc3ccc(N4CCN(S(=O)(=O)N(C)C)CC4)cc3)nn(C)c2C1]

To a solution of (rac)-ethyl 11-({4-[4-(dimethylsulfamoyl)piperazin-1-yl]phenoxy}methyl)-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylate (see Intermediate 1-27; 1.50 g, 1.80 mmol) in THF (73 ml) and methanol (36 ml) was added a solution of lithium hydroxide in water (36 ml, 1.0 M, 36 mmol). The reaction was stirred for 16 hours at 50° C. For work-up, aqueous 1N hydrochloric acid was added until a pH of 5-6 was reached. The mixture was poured into water and was extracted with dichloromethane. The combined organic phases washed with brine and dried over sodium sulfate. After filtration and removal of the solvent, the crude product was purified by flash chromatography (dichloromethane/methanol gradient, 0%→10% methanol) to give the title compound as a racemic mixture (1.2 g).

LC-MS (Method 2): Rt=0.97 min; MS (ESIpos): m/z=806 [M+H]$^+$

The title compound (1.2 g) was separated into enantiomers by chiral HPLC to give enantiomer 1 (see Example 1-15) and enantiomer 2 (see Example 1-16).

Preparative chiral HPLC method: Instrument: Sepiatec: Prep SFC100; column: Chiralpak ID 5 µm 250×30 mm; eluent A: CO2, eluent B: ethanol+0.2 Vol-% diethylamine (99%); isocratic: 43% B; flow 100.0 ml/min temperature: 40° C.; BPR: 150 bar; MWD @ 254 nm Analytical chiral HPLC method: Instrument: Agilent: 1260, Aurora SFC-Module; column: Chiralpak ID 5 µm 100×4.6 mm; eluent A: CO2, eluent B: Ethanol+0.2 Vol-% diethylamine (99%); isocratic: 43% B; low 4.0 ml/min; temperature: 37.5° C.; BPR: 100 bar; MWD @ 254 nm Example 1-15

(+)-11-({4-[4-(dimethylsulfamoyl)piperazin-1-yl]phenoxy}methyl)-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid (Enantiomer 1)

After chiral separation of (rac)-11-({4-[4-(dimethylsulfamoyl)piperazin-1-yl]phenoxy}methyl)-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid (method see Example 1-14) the obtained product was further purified by flash chromatography (dichloromethane/methanol gradient, 2.5%→10% methanol) to give after lyophilisation the title compound (429 mg).

Analytical chiral HPLC (method see Example 1-14): R$_t$=2.90 min.

Specific optical rotation (Method O1): +29.4° (c=1.0 g/100 ml in methanol)

$^1$H-NMR (400 MHz, DMSO-d6) δ[ppm]: 1.231 (1.47), 2.195 (3.44), 2.214 (0.48), 2.523 (0.48), 2.757 (16.00), 2.900 (1.06), 2.913 (1.42), 2.925 (1.26), 3.027 (0.43), 3.178 (1.31), 3.191 (1.47), 3.202 (1.11), 3.357 (0.43), 3.627 (0.52), 3.662 (0.61), 3.881 (4.65), 4.139 (0.44), 4.155 (0.88), 4.170 (0.44), 4.684 (1.05), 4.691 (1.05), 6.492 (1.15), 6.514 (1.43), 6.653 (1.48), 6.676 (1.11), 6.823 (0.61), 6.841 (0.64), 6.920 (0.41), 6.934 (0.77), 6.938 (0.73), 6.955 (0.69), 6.974 (0.74), 7.343 (0.42), 7.363 (0.80), 7.382 (0.60), 7.434 (0.85), 7.455 (0.52), 7.498 (0.48), 7.502 (0.48), 7.507 (0.56), 7.515 (1.05), 7.523 (0.58), 7.526 (0.53), 7.531 (0.53), 7.680 (0.53), 7.683 (0.56), 7.700 (0.50), 7.703 (0.50), 7.849 (0.51), 7.867 (0.45), 7.873 (0.43), 8.216 (0.45), 8.222 (0.42), 8.240 (0.42).

Example 1-16

11-({4-[4-(dimethylsulfamoyl)piperazin-1-yl]phenoxy}methyl)-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid (Enantiomer 2)

After chiral separation of (rac)-11-({4-[4-(dimethylsulfamoyl)piperazin-1-yl]phenoxy}methyl)-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid (method see Example 1-14) the obtained product was further purified by flash chromatography (dichloromethane/methanol gradient, 0%→10% methanol) to give after lyophilisation the title compound (381 mg).

Analytical Chiral HPLC (method see Example 1-14): R$_t$=4.31 min.

$^1$H-NMR (400 MHz, DMSO-d6) δ[ppm]: 1.232 (1.80), 2.195 (4.18), 2.327 (0.43), 2.757 (16.00), 2.901 (1.32), 2.913 (1.82), 2.925 (1.58), 2.991 (0.49), 3.027 (0.53), 3.178 (1.61), 3.191 (1.88), 3.202 (1.38), 3.275 (0.41), 3.358 (0.57), 3.626 (0.64), 3.663 (0.76), 3.881 (5.08), 4.138 (0.55), 4.155 (1.07), 4.170 (0.54), 4.684 (1.28), 4.691 (1.30), 6.492 (1.29), 6.514 (1.59), 6.653 (1.64), 6.676 (1.25), 6.822 (0.72), 6.841 (0.78), 6.920 (0.47), 6.934 (0.91), 6.955 (0.75), 6.974 (0.84), 7.343 (0.45), 7.363 (0.91), 7.382 (0.64), 7.434 (1.00), 7.455 (0.61), 7.498 (0.55), 7.502 (0.59), 7.507 (0.68), 7.514 (1.17), 7.522 (0.72), 7.526 (0.67), 7.531 (0.63), 7.683 (0.66), 7.700 (0.60), 7.849 (0.61), 7.867 (0.54), 7.872 (0.52), 8.215 (0.51), 8.221 (0.51), 8.239 (0.51).

Example 1-17

(rac)-(E/Z)-3-({4-[4-(dimethylsulfamoyl)piperazin-1-yl]phenoxy}methyl)-1-methyl-7-[3-(naphthalen-1-yloxy)propyl]-1,10,13,15-tetrahydropyrazolo[4',3':9,10][1,6]oxazacycloundecino[8,7,6-hi]indole-8-carboxylic acid

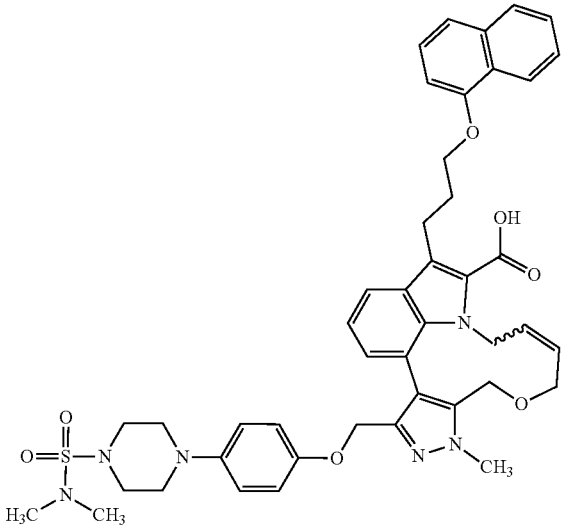 [SMILES: CN(C)S(=O)(=O)N1CCN(c2ccc(OCc3nn(C)c4c3-c3cccc5c(CCCOc6cccc7ccccc67)c(C(=O)O)n(c35)CC=CCOC4)cc2)CC1]

A mixture of (rac)-(E/Z)-ethyl 3-({4-[4-(dimethylsulfamoyl)piperazin-1-yl]phenoxy}methyl)-1-methyl-7-[3-(naphthalen-1-yloxy)propyl]-1,10,13,15-tetrahydropyrazolo

[4',3':9,10][1,6]oxazacycloundecino[8,7,6-hi]indole-8-carboxylate (see Intermediate 1-32; 43.0 mg, 51.6 µmol), THF (2.1 ml), ethanol (1.5 ml) and aqueous lithium hydroxide (1.0 ml, 1.0 M, 1.0 mmol) was stirred for 16 h at room temperature and then for 6 h at 50° C. For work-up, citric acid (217 mg, 1.03 mmol) was added to adjust the pH to 5-6, water was added and the mixture was extracted three times with a mixture of dichloromethane/2-propanol (4:1). The combined organic phases were washed with brine, filtrated through a silicone filter and concentrated. The residue was purified by preparative TLC (silica, ethyl acetate) to give the title compound (20.0 mg, 47% yield).

RF=0.72 (ethyl acetate)

LC-MS (Method 2): $R_t$=0.95 min; MS (ESIneg): m/z=803 [M−H]⁻

¹H-NMR (500 MHz, THF-d₈): δ [ppm]=10.87 (br s, 1H), 8.33-8.28 (m, 1H), 7.77-7.73 (m, 1H), 7.62 (dd, 1H), 7.45-7.39 (m, 2H), 7.35-7.32 (m, 1H), 7.27-7.23 (m, 1H), 6.89 (dd, 1H), 6.71 (d, 1H), 6.69 (dd, 1H), 6.68-6.64 (m, 1H), 6.55-6.51 (m, 2H), 5.53 (br d, 1H), 5.25 (br td, 1H), 5.12 (td, 1H), 4.77 (dd, 1H), 4.65 (d, 1H), 4.60 (d, 1H), 4.47-4.43 (m, 2H), 4.21-4.12 (m, 2H), 3.96 (s, 3H), 3.76-3.71 (m, 1H), 3.67-3.61 (m, 1H), 3.52-3.46 (m, 1H), 3.44-3.37 (m, 1H), 3.20-3.17 (m, 4H), 2.91-2.88 (m, 4H), 2.74 (s, 6H), 2.34 (quin, 2H).

Example 1-18

(rac)-3-({4-[4-(dimethylsulfamoyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid

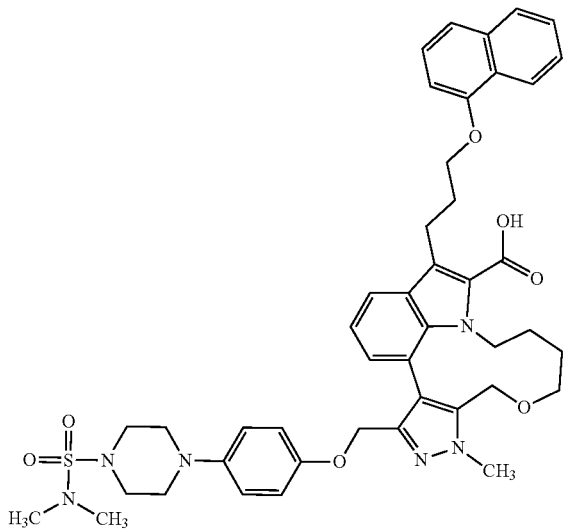 [SMILES: CN(C)S(=O)(=O)N1CCN(c2ccc(OCc3nn(C)c4c3-c3cccc5c(CCCOc6cccc7ccccc67)c(C(=O)O)n(c35)CCCCOC4)cc2)CC1]

A mixture of (rac)-ethyl 3-({4-[4-(dimethylsulfamoyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (see Intermediate 1-33; 153 mg, 183 µmol), THF (7.4 ml), ethanol (5.3 ml) and aqueous lithium hydroxide (3.7 ml, 1.0 M, 3.7 mmol) was stirred for 20 h at 50° C. For work-up, citric acid (770 mg, 3.66 mmol) was added to adjust the pH to 5-6, water was added and the mixture was extracted three times with a mixture of dichloromethane/2-propanol (4:1). The combined organic phases were washed with brine, filtrated through a silicone filter and concentrated. The residue was purified twice by preparative HPLC to give the title compound (28.0 mg, 90% purity, 17% yield).

LC-MS (Method 2): $R_t$=0.94 min; MS (ESIpos): m/z=807 [M+H]⁺

¹H-NMR (400 MHz, DMSO-d6) δ[ppm]: 1.048 (0.48), 1.232 (0.74), 2.164 (0.48), 2.181 (0.72), 2.198 (0.51), 2.323 (0.69), 2.327 (0.93), 2.331 (0.69), 2.518 (5.31), 2.523 (3.35), 2.540 (0.66), 2.665 (0.72), 2.669 (0.96), 2.673 (0.72), 2.741 (16.00), 2.760 (1.92), 2.860 (1.25), 2.872 (1.62), 2.885 (1.41), 3.128 (1.43), 3.141 (1.67), 3.153 (1.23), 3.254 (0.45), 3.388 (0.58), 3.919 (5.08), 3.942 (0.56), 4.096 (0.43), 4.113 (0.69), 4.127 (0.64), 4.265 (0.58), 4.299 (0.63), 4.441 (0.66), 4.469 (0.79), 4.670 (0.72), 4.685 (0.85), 4.704 (0.72), 4.714 (0.72), 6.502 (1.04), 6.525 (1.35), 6.653 (1.59), 6.675 (1.19), 6.792 (0.71), 6.810 (1.07), 6.825 (0.55), 6.952 (0.43), 6.971 (0.64), 7.338 (0.43), 7.358 (0.85), 7.377 (0.63), 7.433 (0.95), 7.453 (0.59), 7.500 (0.59), 7.507 (0.85), 7.516 (1.17), 7.525 (0.88), 7.531 (0.67), 7.691 (0.55), 7.710 (0.48), 7.849 (0.59), 7.866 (0.50), 7.872 (0.50), 8.220 (0.48), 8.227 (0.45), 8.244 (0.48).

The title compound (24.0 mg) was separated into enantiomers by chiral HPLC [Instrument: Sepiatec: Prep SFC100; column: Chiralpak ID 5 µm 250×30 mm; eluent A: carbon dioxide, eluent B: 2-propanol+0.2 vol-% diethylamine (99%); isocratic: 50% B; flow: 100.0 ml/min; temperature: 40° C.; BPR: 150 bar; MWD @ 254 nm] to give enantiomer 1 (10.0 mg, see Example 1-19) and enantiomer 2 (5.0 mg, see Example 1-20).

Analytical chiral HPLC method: Instrument: Agilent: 1260, Aurora SFC-Module; column: Chiralpak ID 5 µm 100×4.6 mm; eluent A: carbon dioxide, eluent B: 2-propanol+0.2 Vol-% diethylamine (99%); isocratic: 50% B; flow 4.0 ml/min; temperature: 37.5° C.; BPR: 100 bar; MWD @ 254 nm Example 1-19

3-({4-[4-(dimethylsulfamoyl) piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (Enantiomer 1)

See Example 1-18 for preparation and enantiomer separation.

Analytical chiral HPLC (Method see Example 1-18): $R_t$=4.31 min; ee 99.5%

Example 1-20

3-({4-[4-(dimethylsulfamoyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (Enantiomer 2)

See Example 1-18 for preparation and enantiomer separation.

Analytical chiral HPLC (Method see Example 1-18): $R_t$=7.30 min; ee 98.3%

Example 1-21

(rac)-3-({4-[4-(cyclopropylcarbonyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid

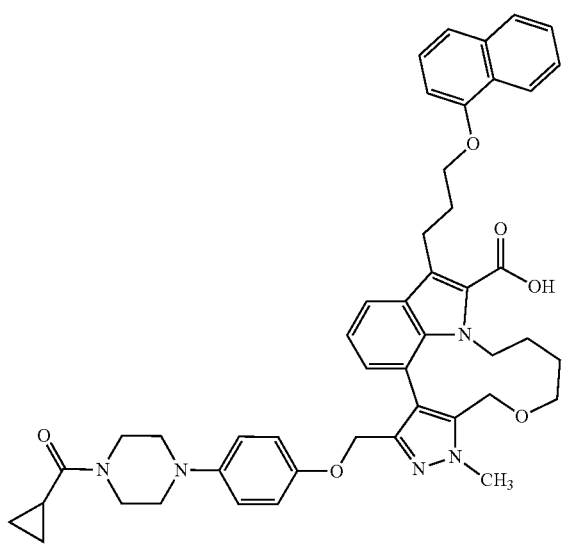 [SMILES: Cn1nc(COc2ccc(N3CCN(C(=O)C4CC4)CC3)cc2)c2c1COCCCCn1c(C(=O)O)c(CCCOc3cccc4ccccc34)c3cccc-2c31]

A mixture of (rac)-ethyl 3-({4-[4-(cyclopropylcarbonyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (see Intermediate 1-34; 188 mg, 236 μmol), THF (9.6 ml), ethanol (6.9 ml) and aqueous lithium hydroxide (5.3 ml, 1.0 M, 5.3 mmol) was stirred for 16 h at 50° C. For work-up, citric acid (1.12 g, 5.31 mmol) was added to adjust the pH to 5-6, water was added and the mixture was extracted three times with a mixture of dichloromethane/2-propanol (4:1). The combined organic phases were washed with brine, filtrated through a silicone filter and concentrated. The residue was purified by flash chromatography (dichloromethane/ethanol gradient, 0%→20% ethanol) to give the title compound (72.0 mg, 39% yield).

LC-MS (Method 1): $R_t$=1.51 min; MS (ESIpos): m/z=768 [M+H]+

$^1$H-NMR (500 MHz, DMSO-$d_6$): d [ppm]=13.18 (br s, 1H), 8.25-8.22 (m, 1H), 7.88-7.84 (m, 1H), 7.71 (d, 1H), 7.54-7.49 (m, 2H), 7.44 (d, 1H), 7.36 (t, 1H), 6.98 (t, 1H), 6.85-6.78 (m, 2H), 6.69-6.65 (m, 2H), 6.53-6.49 (m, 2H), 4.72-4.67 (m, 2H), 4.56-4.49 (m, 1H), 4.46 (d, 1H), 4.29 (d, 1H), 4.16-4.05 (m, 3H), 3.92 (s, 3H), 3.64 (br s, 2H), 3.52-3.43 (m, 3H), 3.38 (br dd, 1H), 3.30-3.22 (m, 1H), 2.88-2.76 (m, 5H), 2.18 (quin, 2H), 1.93-1.88 (m, 1H), 1.41-1.33 (m, 1H), 1.24 (br s, 1H), 1.05 (br s, 2H), 0.73-0.66 (m, 4H)

The title compound (66.0 mg) was separated into enantiomers by chiral HPLC [Instrument: Labomatic HD5000, Labocord-5000; Gilson GX-241, Labcol Vario 4000, column: Chiralpak IB 5μ 250×30 mm; Eluent A: hexane; eluent B: ethanol; gradient: 5-50% B in 20 min+0.1% TFA; flow 40.0 ml/min; detection: UV 254 nm] to give enantiomer 1 (27.8 mg, see Example 1-22) and enantiomer 2 (32.0 mg, see Example 1-23).

Analytical chiral HPLC method: Instrument: Agilent HPLC 1260; column: Chiralpak IB 3μ 100×4.6 mm; eluent A: hexane+0.1 Vol-% TFA; eluent B: ethanol; gradient: 5-50% B in 7 min; flow 1.4 ml/min; temperature: 25° C.; detection: DAD 254 nm

Example 1-22

3-({4-[4-(cyclopropylcarbonyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (Enantiomer 1)

See Example 1-21 for preparation and enantiomer separation.

Analytical chiral HPLC (Method see Example 1-21): $R_t$=6.28 min; ee>99.9%

Example 1-23

3-({4-[4-(cyclopropylcarbonyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (Enantiomer 2)

See Example 1-21 for preparation and enantiomer separation.

Analytical chiral HPLC (Method see Example 1-21): $R_t$=7.01 min; ee 96.9%

Example 1-24

(rac)-3-{[4-(4-acetylpiperazin-1-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid

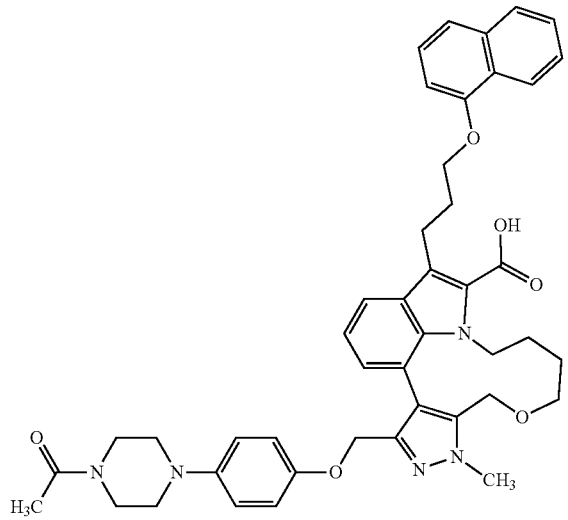 [SMILES: CC(=O)N1CCN(c2ccc(OCc3nn(C)c4c3-c3cccc5c(CCCOc6cccc7ccccc67)c(C(=O)O)n(c35)CCCCOC4)cc2)CC1]

A mixture of (rac)-ethyl 3-{[4-(4-acetylpiperazin-1-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (see Intermediate 1-35; 185 mg, 240 µmol), THF (9.7 ml), ethanol (7.0 ml) and aqueous lithium hydroxide (4.8 ml, 1.0 M, 4.8 mmol) was stirred for 48 h at 50° C. For work-up, citric acid (1.01 g, 4.81 mmol) was added to adjust the pH to 5-6, water was added and the mixture was extracted three times with a mixture of dichloromethane/2-propanol (4:1). The combined organic phases were washed with brine, filtrated through a silicone filter and concentrated. The residue (165 mg) was re-dissolved in dichloromethane (7.5 ml); pyridine (190 µl, 2.4 mmol) and acetic anhydride (89 µl, 940 µmol) were added, and the mixture was stirred for 12 h at room temperature. For work-up, the mixture was diluted with dichloromethane and washed with water, filtrated through a silicon filter and concentrated. The residue was purified twice by preparative HPLC to give the title compound (57.0 mg, 31% yield).

LC-MS (Method 3): $R_t$=1.73 min; MS (ESIpos): m/z=742 $[M+H]^+$ $^1$H-NMR (400 MHz, DMSO-$d_6$): δ [ppm]=13.17 (br s, 1H), 8.25-8.19 (m, 1H), 7.88-7.84 (m, 1H), 7.70 (br d, 1H), 7.55-7.48 (m, 2H), 7.44 (d, 1H), 7.36 (t, 1H), 6.97 (t, 1H), 6.84-6.78 (m, 2H), 6.69-6.64 (m, 2H), 6.54-6.49 (m, 2H), 4.72-4.66 (m, 2H), 4.58-4.50 (m, 1H), 4.46 (d, 1H), 4.28 (d, 1H), 4.16-4.02 (m, 3H), 3.92 (s, 3H), 3.51-3.37 (m, 6H), 3.29-3.21 (m, 1H), 2.86-2.76 (m, 5H), 2.23-2.13 (m, 2H), 1.96 (s, 3H), 1.43-1.33 (m, 1H), 1.28-1.18 (m, 1H), 1.10-1.00 (m, 2H)

The title compound (52.0 mg) was separated into enantiomers by chiral HPLC [Instrument: Labomatic HD5000, Labocord-5000; Gilson GX-241, Labcol Vario 4000, column: Chiralpak AD-H 5µ 250×30 mm; eluent A: hexane+0.1 Vol-% TFA; eluent B: 2-propanol; gradient: 20-50% B in 15 min; flow 40.0 ml/min; UV 254 nm] to give enantiomer 1 (25.0 mg, see Example 1-25) and enantiomer 2 (25.5 mg, see Example 1-26).

Analytical chiral HPLC method: Instrument: Agilent HPLC 1260; column: Chiralpak AD-H 3µ 100×4.6 mm; eluent A: hexane+0.1 Vol-% TFA; eluent B: 2-propanol; gradient: 20-50% B in 7 min; flow 1.4 ml/min; temperature: 25° C.; DAD 254 nm Example 1-25

3-{[4-(4-acetylpiperazin-1-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (Enantiomer 1)

See Example 1-24 for preparation and enantiomer separation.
Analytical chiral HPLC (Method see Example 1-24): $R_t$=3.92 min; ee>99.9%

Example 1-26

3-{[4-(4-acetylpiperazin-1-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (Enantiomer 2)

See Example 1-24 for preparation and enantiomer separation.
Analytical chiral HPLC (Method see Example 1-24): $R_t$=5.22 min; ee>95.8%

Example 1-27

(rac)-3-({4-[4-(methoxyacetyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid

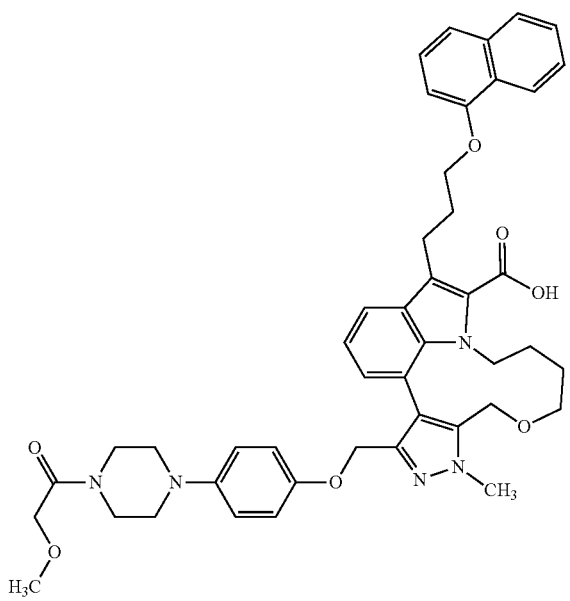 [SMILES: COCC(=O)N1CCN(c2ccc(OCc3nn(C)c4c3-c3cccc5c(CCCOc6cccc7ccccc67)c(C(=O)O)n(c35)CCCCOC4)cc2)CC1]

The title compound was prepared in analogy to the synthesis of (rac)-3-{[4-(4-acetylpiperazin-1-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (see Example 1-24) using (rac)-ethyl 3-({4-[4-(methoxyacetyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (see Intermediate 1-36, 151 mg, 21.4 mmol) as starting material and methoxyacetyl chloride as reagent to give the title compound (35.8 mg, 95% purity, 21% yield).

LC-MS (Method 3): $R_t$=1.40 min; MS (ESIpos): m/z=772 $[M+H]^+$ $^1$H-NMR (400 MHz, DMSO-$d_6$): δ [ppm]=13.20 (br s, 1H), 8.26-8.21 (m, 1H), 7.89-7.84 (m, 1H), 7.70 (br d, 1H), 7.56-7.42 (m, 3H), 7.39-7.33 (m, 1H), 6.97 (t, 1H), 6.86-6.74 (m, 2H), 6.71-6.63 (m, 2H), 6.55-6.48 (m, 2H), 4.73-4.65 (m, 2H), 4.58-4.49 (m, 1H), 4.46 (d, 1H), 4.28 (d, 1H), 4.19-4.00 (m, 5H), 3.92 (s, 3H), 3.52-3.41 (m, 3H), 3.41-3.36 (m, 2H), 3.30-3.22 (m, 4H), 2.88-2.77 (m, 5H), 2.23-2.13 (m, 2H), 1.43-1.17 (m, 3H), 1.09-1.00 (m, 2H)

The title compound (29.0 mg) was separated into enantiomers by chiral HPLC [Instrument: Labomatic HD5000, Labocord-5000; Gilson GX-241, Labcol Vario 4000, Column: Chiralpak ID 5µ 250×30 mm; eluent A: hexane+0.1 Vol-% TFA (99%); Eluent B: ethanol/methanol 1:1; isocratic: 50% A+50% B; flow 40.0 ml/min; UV 254 nm] to give enantiomer 1 (11.0 mg, see Example 1-28) and enantiomer 2 (9.0 mg, see Example 1-29).

Analytical chiral HPLC method: Instrument: Agilent HPLC 1260; column: Chiralpak ID 3µ 100×4.6 mm; eluent A: hexane+0.1 Vol-% TFA (99%); eluent B: ethanol/methanol 1:1; isocratic: 50% A+50% B; flow 1.4 ml/min; temperature: 25° C.; DAD 254 nm Example 1-28

3-({4-[4-(methoxyacetyl)piperazin-1-yl]
phenoxy}methyl)-1-methyl-7-[3-(naphthalen-1-
yloxy)propyl]-1,10,11,12,13,15-hexahydropyrazolo
[4',3':9,10][1,6]oxazacycloundecino[8,7,6-hi]indole-
8-carboxylic acid (Enantiomer 1)

See Example 1-27 for preparation and enantiomer separation.
Analytical chiral HPLC (Method see Example 1-27): $R_t$=3.58 min; ee>95.9%

Example 1-29

3-({4-[4-(methoxyacetyl)piperazin-1-yl]
phenoxy}methyl)-1-methyl-7-[3-(naphthalen-1-
yloxy)propyl]-1,10,11,12,13,15-hexahydropyrazolo
[4',3':9,10][1,6]oxazacycloundecino[8,7,6-hi]indole-
8-carboxylic acid (Enantiomer 2)

See Example 1-27 for preparation and enantiomer separation.
Analytical chiral HPLC (Method see Example 1-27): $R_t$=4.83 min; ee>97.6%

Example 1-30

(rac)-7,9,11-trimethyl-1-[3-(naphthalen-1-yloxy)
propyl]-4,5,6,7,8,9-hexahydropyrazolo[3',4':7,8][1,5]
diazecino[9,10,1-hi]indole-2-carboxylic acid

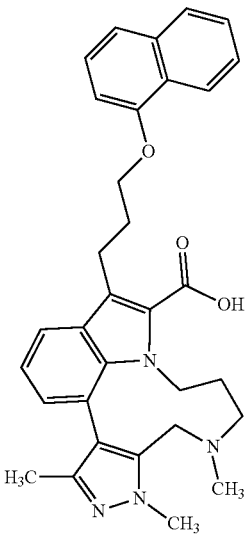 [SMILES: Cc1nn(C)c2c1-c1cccc3c(CCCOc4cccc5ccccc45)c(C(=O)O)n(c13)CCCN(C)C2]

A mixture of (rac)-ethyl 7,9,11-trimethyl-1-[3-(naphthalen-1-yloxy)propyl]-4,5,6,7,8,9-hexahydropyrazolo[3',4':7,8][1,5]diazecino[9,10,1-hi]indole-2-carboxylate (see Intermediate 1-43; 521 mg, 946 µmol), THF (38 ml), ethanol (28 ml) and aqueous lithium hydroxide (19 ml, 1.0 M, 19 mmol) was stirred for 16 h at 50° C. For work-up, citric acid (3.98 g, 18.9 mmol) was added to adjust the pH to 5-6, water was added and the mixture was extracted three times with a mixture of dichloromethane/2-propanol (4:1). The combined organic phases were washed with brine, filtrated through a silicone filter and concentrated. The residue was purified twice by preparative HPLC (Method P12) to give the title compound in two fractions (combined 390 mg, 79% yield), which contained some triphenylphosphine impurities and was used as obtained for separation into enantiomers.

LC-MS (Method 2): $R_t$=0.88 min; MS (ESIpos): m/z=523 [M+H]$^+$ $^1$H-NMR (400 MHz, DMSO-$d_6$): δ [ppm]=8.22 (d, 1H), 7.89-7.84 (m, 1H), 7.71 (dd, 1H), 7.65-7.36 (m, 5H), 7.02 (dd, 1H), 6.92-6.86 (m, 2H), 4.50 (dt, 1H), 4.19 (t, 2H), 3.82-3.74 (m, 4H), 3.59 (br d, 1H), 3.46-3.36 (m, 1H), 3.31-3.22 (m, 1H), 2.96 (br d, 1H), 2.37-2.29 (m, 1H), 2.25-2.13 (m, 5H), 1.92-1.82 (m, 4H), 1.68-1.44 (m, 2H)

The title compound (390 mg) was separated into enantiomers by chiral HPLC [Instrument: Sepiatec: Prep SFC100; column: Chiralpak ID 5 µm 250×30 mm; eluent A: carbon dioxide, eluent B: 2-propanol+0.4 Vol-% diethylamine (99%); isocratic: 25% B; flow 100.0 ml/min temperature: 40° C.; BPR: 150 bar; MWD @ 254 nm] to give enantiomer 1 (125 mg, see Example 1-31) and enantiomer 2 (127 mg, see Example 1-32) as diethyl ammonium salts, also referred to as N-ethylethanamine salts herein.

Analytical chiral HPLC method: Instrument: Agilent: 1260, Aurora SFC-Module; column: Chiralpak ID 5 µm 100×4.6 mm; eluent A: carbon dioxide, eluent B: 2-propanol+0.2 Vol-% diethylamine (99%); isocratic: 25% B; flow 4.0 ml/min; temperature: 37.5° C.; BPR: 100 bar; MWD @ 254 nm Example 1-31

7,9,11-trimethyl-1-[3-(naphthalen-1-yloxy)propyl]-4,
5,6,7,8,9-hexahydropyrazolo[3',4':7,8][1,5]diazecino
[9,10,1-hi]indole-2-carboxylic acid-N-ethyl-
ethanamine salt (Enantiomer 1)

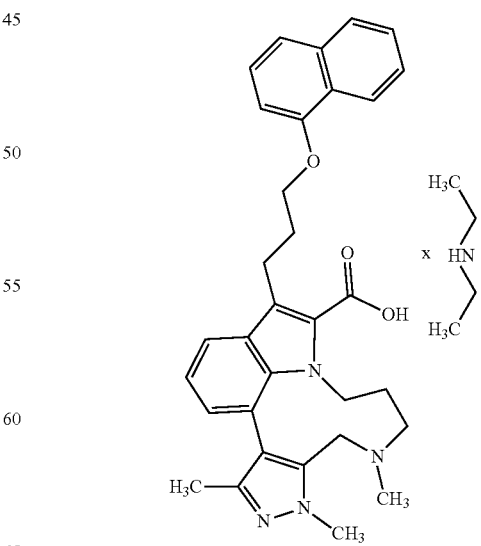

See Example 1-30 for preparation and enantiomer separation.

Analytical chiral HPLC (Method see Example 1-30): $R_t$=3.42 min; ee>95.4%

LC-MS (Method 1): $R_t$=1.17 min; MS (ESIpos): m/z=523 [M+H]$^+$ $^1$H-NMR (400 MHz, DMSO-d6) δ[ppm]: 1.004 (0.58), 1.019 (0.55), 1.085 (1.08), 1.106 (2.80), 1.123 (5.81), 1.141 (2.72), 1.403 (0.53), 1.609 (0.53), 1.789 (0.61), 1.812 (0.66), 1.824 (0.77), 1.865 (16.00), 1.882 (0.48), 2.052 (1.87), 2.141 (1.32), 2.158 (1.93), 2.175 (1.43), 2.212 (11.46), 2.258 (0.69), 2.271 (0.66), 2.300 (1.56), 2.304 (2.03), 2.309 (1.61), 2.496 (6.60), 2.500 (4.36), 2.517 (0.55), 2.642 (1.21), 2.646 (1.61), 2.651 (1.14), 2.808 (1.00), 2.824 (2.35), 2.842 (2.27), 2.859 (0.84), 2.886 (1.77), 2.922 (1.82), 3.125 (0.66), 3.143 (1.06), 3.159 (0.95), 3.178 (0.55), 3.268 (2.46), 3.538 (2.03), 3.573 (2.22), 3.752 (0.77), 3.771 (15.52), 4.132 (1.61), 4.148 (3.17), 4.163 (1.53), 4.557 (0.74), 4.592 (0.69), 6.736 (1.37), 6.753 (1.61), 6.837 (2.01), 6.855 (2.14), 6.902 (1.43), 6.921 (1.98), 6.939 (1.16), 7.326 (1.43), 7.346 (2.75), 7.365 (2.11), 7.408 (2.93), 7.428 (1.64), 7.453 (0.48), 7.457 (0.69), 7.470 (1.72), 7.474 (1.64), 7.480 (1.90), 7.487 (3.62), 7.494 (1.87), 7.500 (1.72), 7.504 (1.82), 7.517 (0.71), 7.521 (0.48), 7.554 (1.48), 7.573 (1.40), 7.823 (1.77), 7.830 (1.00), 7.841 (1.66), 7.846 (1.43), 8.192 (1.53), 8.198 (1.45), 8.217 (1.43).

Example 1-32

7,9,11-trimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid-N-ethylethanamine salt (Enantiomer 2)

See Example 1-30 for preparation and enantiomer separation.

Analytical chiral HPLC (Method see Example 1-30): $R_t$=7.72 min; ee>98.3%

Example 1-33

(rac)-1,3-dimethyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid

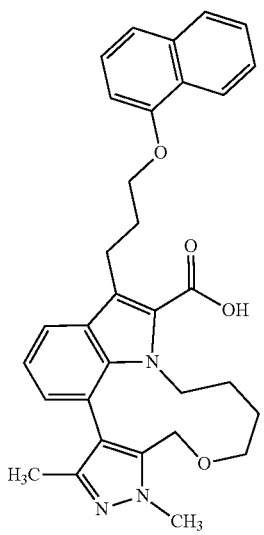 [SMILES: Cc1nn(C)c2c1-c1cccc3c(CCCOc4cccc5ccccc45)c(C(=O)O)n(c13)CCCCOC2]

A mixture of (rac)-ethyl 1,3-dimethyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (see Intermediate 1-46; 450 mg, 816 μmol), THF (33 ml), ethanol (24 ml) and aqueous lithium hydroxide (18 ml, 1.0 M, 18 mmol) was stirred for 16 h at 50° C. For work-up, citric acid (3.86 g, 18.4 mmol) was added to adjust the pH to 5-6, water was added and the mixture was extracted three times with a mixture of dichloromethane/2-propanol (4:1). The combined organic phases were washed with brine, filtrated through a silicone filter and concentrated. The residue was purified twice by flash chromatography (Biotage SNAP cartridge silica 25 g, dichloromethane/ethanol gradient, 0%→20% ethanol and ethyl acetate/ethanol gradient 0%→20% ethanol) to give the title compound (133 mg, 91% purity, 28% yield).

LC-MS (Method 2): $R_t$=0.90 min; MS (ESIpos): m/z=524 [M+H]$^+$ $^1$H-NMR (400 MHz, DMSO-d$_6$): δ [ppm]=13.61-12.51 (m, 1H), 8.22 (d, 1H), 7.84 (d, 1H), 7.69 (br d, 1H), 7.53-7.34 (m, 4H), 7.04-6.96 (m, 1H), 6.87 (d, 1H), 6.77 (br d, 1H), 4.65-4.54 (m, 2H), 4.28-4.11 (m, 3H), 3.99-3.88 (m, 1H), 3.81 (s, 3H), 3.45-3.34 (m, 1H), 3.27-3.13 (m, 1H), 2.74-2.66 (m, 1H), 2.23-2.14 (m, 2H), 2.07-2.06 (m, 1H), 1.79 (s, 3H), 1.39-1.24 (m, 1H), 1.24-1.10 (m, 1H), 1.09-0.83 (m, 2H)

Example 1-34

7,10,11-trimethyl-1-[3-(naphthalen-1-yloxy)propyl]-4,5,6,7,8,10-hexahydropyrazolo[3',4':7,8][1,5]diazecino[9,10,1-hi]indole-2-carboxylic acid-N-ethylethanamine salt (Enantiomer 1)

A mixture of (rac)-ethyl 7,10,11-trimethyl-1-[3-(naphthalen-1-yloxy)propyl]-4,5,6,7,8,10-hexahydropyrazolo[3',4':7,8][1,5]diazecino[9,10,1-hi]indole-2-carboxylate (see Intermediate 1-53; 512 mg, 930 μmol), THF (38 ml), ethanol (27 ml) and aqueous lithium hydroxide (21 ml, 1.0 M, 21 mmol) was stirred for 16 h at 50° C. For work-up, citric acid (4.40 g, 20.9 mmol) was added to adjust the pH to 5-6, water was added and the mixture was extracted three times with a mixture of dichloromethane/2-propanol (4:1). The combined organic phases were washed with brine, filtrated through a silicone filter and concentrated. The residue was purified by preparative HPLC [Instrument: Waters Autopurification system; column: Waters XBrigde C18 5µ 100×30 mm; Eluent A: water+0.2 Vol-% aqueous ammonia (32%), Eluent B: acetonitrile; gradient: 0.00-0.50 min 13% B (25→70 mL/min), 0.51-5.50 min 27-40% B (70 mL/min), DAD scan: 210-400 nm]followed preparative HPLC [Instrument: Waters Autopurification system; column: Phenomenex Kinetex C18 5µ 100×30 mm; eluent A: water+0.1 Vol-% formic acid (99%), eluent B: acetonitrile; gradient: 0.00-0.50 min 14% B (25→70 mL/min), 0.51-5.50 min 29-50% B (70 mL/min), DAD scan: 210-400 nm] to give the title compound as racemic mixture (77.1 mg, 15% yield).

The racemate was separated into enantiomers by chiral HPLC [Instrument: Labomatic HD5000, Labocord-5000; Gilson GX-241, Labcol Vario 4000, column: Chiralpak ID 5µ 250×30 mm; eluent A: hexane+0.1 Vol-% diethylamine (99%); eluent B: ethanol; gradient: 20-50% B in 20 min; flow 40.0 ml/min; UV 254 nm] to give enantiomer 1 (35.5 mg, title compound) and enantiomer 2 (35.5 mg, see Example 1-35).

Analytical chiral HPLC method: Instrument: Agilent HPLC 1260; column: Chiralpak ID 3µ 100×4.6 mm; eluent A: hexane+0.1 Vol-% diethylamine (99%); eluent B: ethanol; gradient: 20-50% B in 7 min; flow 1.4 ml/min; temperature: 25° C.; DAD 254 nm Analytical chiral HPLC: Rt=2.29 min; ee>99%

LC-MS (Method 1): R$_t$=1.26 min; MS (ESIpos): m/z=523 [M+H]$^+$ $^1$H-NMR (400 MHz, DMSO-d6) δ[ppm]: 1.108 (7.28), 1.126 (16.00), 1.137 (1.06), 1.144 (7.45), 1.231 (0.50), 1.531 (1.04), 1.902 (2.48), 1.965 (7.28), 2.008 (12.10), 2.024 (0.71), 2.157 (0.89), 2.175 (1.30), 2.192 (0.92), 2.331 (1.27), 2.336 (0.59), 2.437 (0.77), 2.518 (6.95), 2.522 (4.55), 2.673 (1.27), 2.678 (0.56), 2.789 (1.86), 2.806 (5.62), 2.825 (5.47), 2.843 (1.69), 3.113 (1.27), 3.127 (0.53), 3.146 (1.98), 3.165 (4.64), 3.271 (2.31), 3.286 (1.72), 3.304 (3.90), 3.734 (0.41), 3.770 (12.07), 4.136 (0.68), 4.151 (1.27), 4.162 (1.24), 4.178 (0.56), 4.622 (0.44), 4.657 (0.47), 6.645 (0.95), 6.662 (1.06), 6.846 (1.36), 6.864 (1.77), 6.881 (1.42), 6.899 (0.92), 7.343 (1.06), 7.363 (1.89), 7.382 (1.51), 7.427 (1.95), 7.448 (1.09), 7.485 (0.47), 7.498 (1.36), 7.504 (1.74), 7.513 (2.75), 7.522 (1.98), 7.528 (1.80), 7.540 (0.68), 7.545 (0.50), 7.552 (0.92), 7.845 (1.15), 7.854 (0.59), 7.861 (0.83), 7.868 (0.92), 8.230 (1.04), 8.237 (0.86), 8.246 (0.50), 8.255 (0.92).

Example 1-35

7,10,11-trimethyl-1-[3-(naphthalen-1-yloxy)propyl]-4,5,6,7,8,10-hexahydropyrazolo[3',4':7,8][1,5]diazecino[9,10,1-hi]indole-2-carboxylic acid-N-ethylethanamine salt (Enantiomer 2)

See Example 1-34 for preparation and enantiomer separation.

Analytical chiral HPLC (Method see Example 1-34): R$_t$=3.06 min; ee>99%

Example 1-36

(rac)-2,3-dimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid

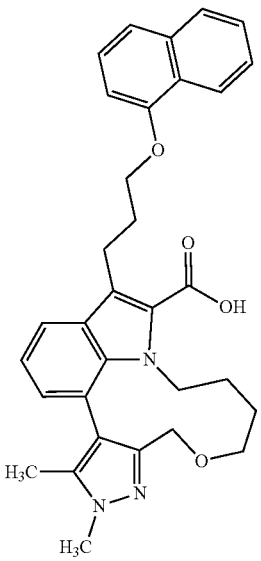 [SMILES: Cc1c2c(nn1C)COCCCCn1c(C(=O)O)c(CCCOc3cccc4ccccc34)c3cccc-2c31]

A mixture of (rac)-ethyl 2,3-dimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylate (see Intermediate 1-56; 758 mg, 1.37 mmol), THF (56 ml), ethanol (40 ml) and aqueous lithium hydroxide (31 ml, 1.0 M, 31 mmol) was stirred for 16 h at 50° C. For work-up, citric acid (6.50 g, 30.9 mmol) was added to adjust the pH to 5-6, water was added and the mixture was extracted three times with a mixture of dichloromethane/2-propanol (4:1). The combined organic phases were washed with brine, filtrated through a silicone filter and concentrated. The residue was purified by flash chromatography (Biotage SNAP cartridge silica, hexanes/ethyl acetate gradient, 50%→100% ethyl acetate) to give the title compound (237 mg, 33% yield, containing 50 mol % ethyl acetate).

LC-MS (Method 2): R$_t$=0.84 min; MS (ESIpos): m/z=524 [M+H]$^+$ $^1$H-NMR (400 MHz, DMSO-d6) δ[ppm]: 1.154 (3.79), 1.172 (7.18), 1.190 (3.54), 1.328 (0.40), 1.816 (14.85), 1.907 (0.55), 1.988 (11.12), 2.191 (0.85), 2.208 (1.25), 2.226 (0.85), 2.332 (2.09), 2.336 (0.90), 2.459 (0.75), 2.518 (10.57), 2.523 (7.43), 2.673 (2.19), 2.678 (1.05), 3.081 (0.65), 3.094 (0.60), 3.107 (0.40), 3.266 (1.10), 3.273 (1.05), 3.285 (1.35), 3.796 (16.00), 3.884 (0.50), 4.000 (0.85), 4.017 (2.59), 4.035 (2.54), 4.053 (0.80), 4.168 (2.29), 4.180 (0.90), 4.199 (3.19), 4.292 (0.45), 4.309 (0.45), 4.494 (1.79), 4.525 (1.55), 5.759 (9.17), 6.879 (1.64), 6.896 (2.09), 6.905 (1.10), 7.021 (0.95), 7.040 (1.35), 7.058 (0.80), 7.362 (1.25), 7.383 (2.19), 7.402 (1.79), 7.445 (2.19), 7.466 (1.30), 7.500 (0.50), 7.512 (1.55), 7.516 (2.59), 7.526 (2.84), 7.535 (2.49), 7.540 (1.74), 7.552 (0.55), 7.693 (1.05), 7.713 (0.95), 7.856 (1.25), 7.860 (0.90), 7.867 (0.70), 7.871 (0.85), 7.874 (0.85), 7.880 (1.10), 8.247 (1.20), 8.255 (0.75), 8.271 (1.05).

The title compound (325 mg) was separated into enantiomers by chiral HPLC [Instrument: Labomatic HD5000, Labocord-5000; Gilson GX-241, Labcol Vario 4000, column: Chiralpak IA 5µ 250×30 mm; eluent A: hexane+0.1 Vol-% TFA; eluent B: ethanol; gradient: 5-40% B in 15 min; flow 40.0 ml/min; UV 254 nm] to give enantiomer 1 (98.2 mg, see Example 1-37) and enantiomer 2 (31.0 mg, see Example 1-38).

Analytical chiral HPLC method: Instrument: Agilent HPLC 1260; column: Chiralpak IA 3µ 100×4.6 mm; eluent A: hexane+0.1 Vol-% TFA; eluent B: ethanol; gradient: 5-50% B in 7 min; flow 1.4 ml/min; temperature: 25° C.; DAD 254 nm

Example 1-37

(+)-2,3-dimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (Enantiomer 1)

See Example 1-36 for preparation and enantiomer separation.

Analytical chiral HPLC (Method see Example 1-36): $R_t$=2.65 min; ee>99.9%

LC-MS (Method 1): $R_t$=1.48 min; MS (ESIpos): m/z=524 [M+H]$^+$

Specific optical rotation (Method O1): +35.6° (c=1.0 g/100 ml in DMSO) (determined from another batch which was prepared analogously)

$^1$H-NMR (400 MHz, DMSO-d$_6$): δ [ppm]=13.10 (br s, 1H), 8.29-8.23 (m, 1H), 7.90-7.84 (m, 1H), 7.72 (dd, 1H), 7.56-7.36 (m, 4H), 7.09-7.02 (m, 1H), 6.94-6.87 (m, 2H), 4.52 (d, 1H), 4.34-4.24 (m, 1H), 4.23-4.15 (m, 3H), 3.97-3.83 (m, 1H), 3.80 (s, 3H), 3.30-3.23 (m, 2H), 3.13-3.03 (m, 1H), 2.26-2.15 (m, 2H), 1.81 (s, 3H), 1.38-1.09 (m, 4H), 1.06-0.92 (m, 1H)

Example 1-38

(−)-2,3-dimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (Enantiomer 2)

See Example 1-36 for preparation and enantiomer separation.

Analytical chiral HPLC (Method see Example 1-36): $R_t$=2.89 min; ee>99.9%

Specific optical rotation (Method O1): −33.1° (c=1.0 g/100 ml in DMSO) (determined from another batch which was prepared analogously)

Example 1-39

(rac)-3-({4-[4-(dimethylsulfamoyl)piperazin-1-yl]phenoxy}methyl)-1-methyl-7-[3-(naphthalen-1-yloxy)propyl]-10,11,12,13,14,15-hexahydro-1H-pyrazolo[4',3':4,5]azacycloundecino[3,2,1-hi]indole-8-carboxylic acid

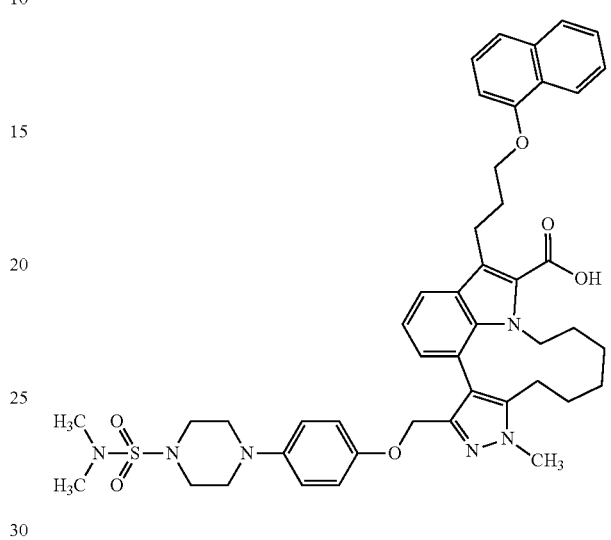

A mixture of (rac)-ethyl 3-({4-[4-(dimethylsulfamoyl)piperazin-1-yl]phenoxy}methyl)-1-methyl-7-[3-(naphthalen-1-yloxy)propyl]-10,11,12,13,14,15-hexahydro-1H-pyrazolo[4',3':4,5]azacycloundecino[3,2,1-hi]indole-8-carboxylate (see Intermediate 1-65; 145 mg, 174 µmol), THF (7.1 ml), ethanol (5.1 ml) and aqueous lithium hydroxide (3.9 ml, 1.0 M, 3.9 mmol) was stirred for 16 h at 50° C. For work-up, citric acid (823 mg, 3.92 mmol) was added to adjust the pH to 5-6, water was added and the mixture was extracted three times with a mixture of dichloromethane/2-propanol (4:1). The combined organic phases were washed with brine, filtrated through a silicone filter and concentrated. The residue was purified by preparative HPLC [Instrument: Waters Autopurification system; column: Phenomenex Kinetex C18 5µ 100×30 mm; eluent A: water+0.1 Vol-% formic acid (99%), eluent B: acetonitrile; gradient: 0.00-0.50 min 34% B (25→70 mL/min), 0.51-5.50 min 68-80% B (70 mL/min), DAD scan: 210-400 nm] to give the title compound (58.0 mg, 40% yield).

LC-MS (Method 3): $R_t$=1.60 min; MS (ESIpos): m/z=805 [M+H]$^+$ $^1$H-NMR (400 MHz, DMSO-d$_6$): δ [ppm]=13.12 (br s, 1H), 8.25-8.21 (m, 1H), 7.90-7.82 (m, 1H), 7.68 (d, 1H), 7.55-7.43 (m, 3H), 7.39-7.34 (m, 1H), 6.97 (t, 1H), 6.82-6.75 (m, 2H), 6.68-6.64 (m, 2H), 6.57-6.52 (m, 2H), 4.77-4.66 (m, 2H), 4.42 (d, 1H), 4.20-4.07 (m, 3H), 3.85 (s, 3H), 3.41-3.35 (m, 1H), 3.28-3.18 (m, 1H), 3.16-3.11 (m, 4H), 2.91-2.84 (m, 4H), 2.80-2.73 (m, 7H), 2.63-2.54 (m, 1H), 2.17 (quin, 2H), 1.95-1.84 (m, 1H), 1.43-1.28 (m, 3H), 1.23-1.12 (m, 1H), 0.90-0.78 (m, 1H), 0.63-0.44 (m, 2H)

The title compound (53 mg) was separated into enantiomers by chiral HPLC to give enantiomer 1 (17.5 mg, see Example 1-40) and enantiomer 2 (17.5 mg, see Example 1-41).

Preparative chiral HPLC method: Instrument: Sepiatec: Prep SFC100; column: Chiralpak IC 5 µm 250×30 mm; eluent A: CO$_2$, eluent B: Ethanol+0.4 Vol-% diethylamine (99%); isocratic: 48% B; flow 100.0 ml/min; temperature: 40° C.; BPR: 150 bar; MWD @ 254 nm Analytical chiral HPLC method: Instrument: Agilent: 1260, Aurora SFC-Modul; column: Chiralpak IC 5 μm 100×4.6 mm; eluent A: $CO_2$, eluent B: ethanol+0.2 Vol-% diethylamine (99%); isocratic: 48% B; flow 4.0 ml/min; temperature: 37.5° C.; BPR: 100 bar; MWD @ 254 nm Example 1-40

3-({4-[4-(dimethylsulfamoyl)piperazin-1-yl] phenoxy}methyl)-1-methyl-7-[3-(naphthalen-1-yloxy)propyl]-10,11,12,13,14,15-hexahydro-1H-pyrazolo[4',3':4,5]azacycloundecino[3,2,1-hi]indole-8-carboxylic acid-N-ethylethanamine salt (Enantiomer 1)

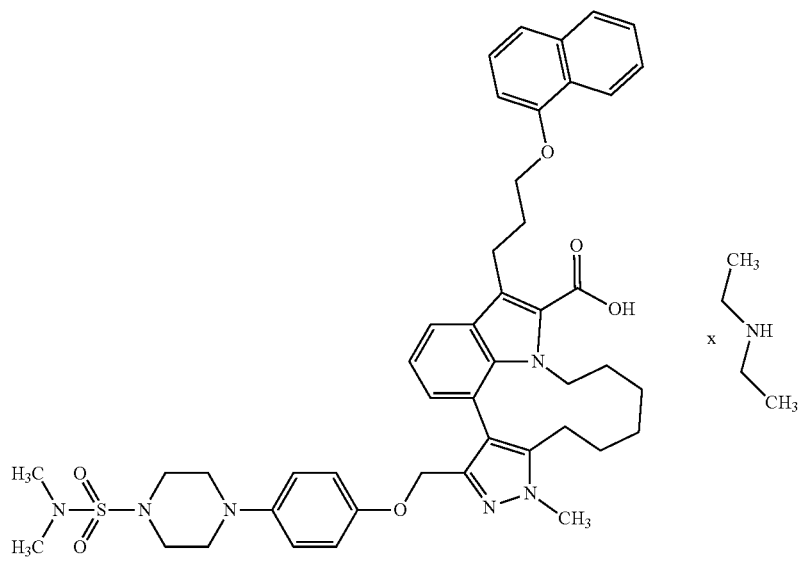

See Example 1-39 for preparation and enantiomer separation.

LC-MS (Method 1): $R_t$=1.62 min; MS (ESIpos): m/z=805 $[M+H]^+$

Analytical chiral HPLC (method see Example 1-39): $R_t$=2.70 min.

$^1$H-NMR (400 MHz, DMSO-d6) δ[ppm]: 1.106 (2.60), 1.127 (2.10), 1.146 (1.09), 1.905 (0.42), 2.156 (0.42), 2.323 (1.76), 2.327 (2.44), 2.331 (1.81), 2.518 (12.18), 2.523 (7.69), 2.665 (1.85), 2.669 (2.52), 2.673 (1.85), 2.739 (16.00), 2.825 (1.93), 2.841 (1.68), 3.095 (1.18), 3.110 (1.51), 3.842 (4.66), 4.123 (0.76), 4.408 (0.63), 4.436 (0.76), 4.641 (0.63), 4.669 (0.55), 6.587 (0.50), 6.610 (1.13), 6.634 (1.93), 6.657 (0.80), 6.818 (0.59), 6.837 (0.63), 7.334 (0.42), 7.355 (0.84), 7.374 (0.59), 7.423 (0.88), 7.444 (0.55), 7.490 (0.55), 7.497 (0.63), 7.505 (1.05), 7.514 (0.67), 7.522 (0.55), 7.840 (0.55), 7.858 (0.46), 7.864 (0.46), 8.206 (0.46), 8.212 (0.42), 8.230 (0.46).

Example 1-41

3-({4-[4-(dimethylsulfamoyl) piperazin-1-yl] phenoxy}methyl)-1-methyl-7-[3-(naphthalen-1-yloxy)propyl]-10,11,12,13,14,15-hexahydro-1H-pyrazolo[4',3':4,5]azacycloundecino[3,2,1-hi]indole-8-carboxylic acid-N-ethylethanamine salt (Enantiomer 2)

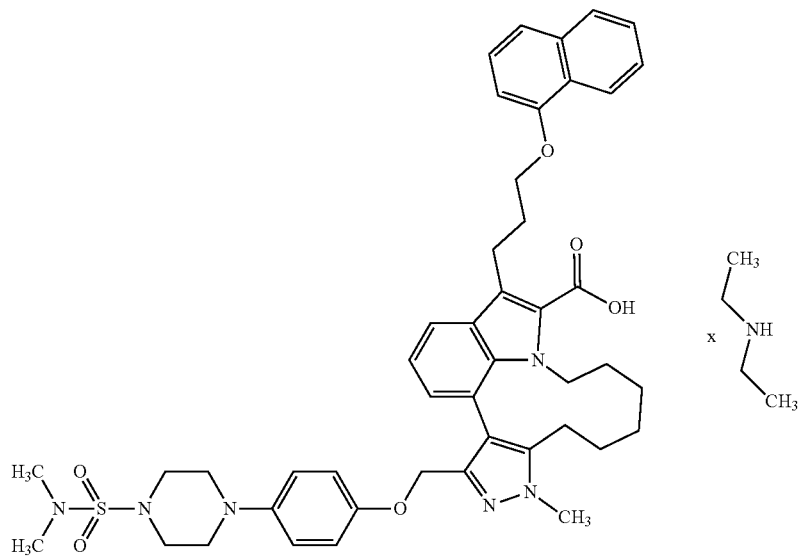

See Example 1-39 for preparation and enantiomer separation.

Analytical chiral HPLC (method see Example 1-39): $R_t$=4.03 min.

LC-MS (Method 1): Rt=1.62 min; MS (ESIpos): m/z=805 [M+H]$^+$

1H-NMR (400 MHz, DMSO-d6): δ [ppm]=8.34-8.12 (m, 1H), 7.92-7.78 (m, 1H), 7.65-7.30 (m, 5H), 7.00-6.76 (m, 2H), 6.72-6.55 (m, 5H), 4.79 (br d, 1H), 4.66 (d, 1H), 4.42 (d, 1H), 4.19-3.99 (m, 3H), 3.84 (s, 3H), 3.20-3.06 (m, 5H), 2.92-2.91 (m, 1H), 2.89-2.71 (m, 13H), 2.70-2.55 (m, 4H), 2.35-2.30 (m, 2H), 2.15 (br d, 2H), 1.91 (br s, 1H), 1.50-1.20 (m, 5H), 1.18-0.40 (m, 12H).

Example 1-42

(rac)-7,9-dimethyl-11-(morpholin-4-ylmethyl)-1-[3-(naphthalen-1-yloxy)propyl]-4,5,6,7,8,9-hexahydropyrazolo[3',4':7,8][1,5]diazecino[9,10,1-hi]indole-2-carboxylic acid

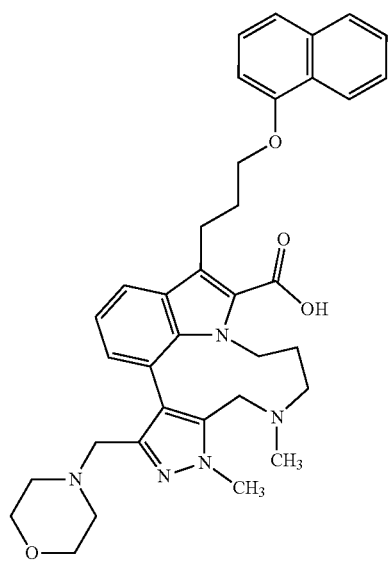 [SMILES: CN1CCCn2c(C(=O)O)c(CCCOc3cccc4ccccc34)c3cccc(c32)-c2c(CN3CCOCC3)nn(C)c2C1]

To a solution of (rac)-ethyl 7,9-dimethyl-11-(morpholin-4-ylmethyl)-1-[3-(naphthalen-1-yloxy)propyl]-4,5,6,7,8,9- hexahydropyrazolo[3',4':7,8][1,5]diazecino[9,10,1-hi]indole-2-carboxylate (see Intermediate 1-72; 430 mg, 676 μmol) in THF (32 ml) and ethanol (16 ml) was added a solution of lithium hydroxide in water (14 ml, 1.0 M, 14 mmol). The reaction mixture was stirred for 20 hours at 50° C., then for 6 hours at 60° C. and finally for 12 days at room temperature. For work-up, the reaction mixture was concentrated under reduced pressure and the residue was purified by flash chromatography (dichloromethane/methanol gradient, 0%→20% methanol) to give after drying under vacuum the title compound (322 mg).

LC-MS (Method 2): Rt=0.86 min; MS (ESIpos): m/z=609 [M+H]$^+$ $^1$H-NMR (400 MHz, DMSO-d6) δ[ppm]: 1.523 (1.37), 1.886 (0.79), 1.907 (0.80), 2.036 (1.71), 2.048 (1.74), 2.157 (2.15), 2.176 (2.83), 2.191 (3.23), 2.209 (2.07), 2.235 (16.00), 2.302 (0.85), 2.318 (0.79), 2.322 (1.40), 2.327 (1.66), 2.332 (1.30), 2.336 (0.92), 2.518 (3.55), 2.523 (2.41), 2.664 (0.70), 2.669 (1.01), 2.673 (0.72), 3.010 (1.81), 3.038 (2.25), 3.046 (2.27), 3.071 (2.60), 3.175 (4.12), 3.208 (4.41), 3.218 (3.02), 3.226 (2.70), 3.234 (2.83), 3.254 (2.03), 3.267 (1.37), 3.287 (1.79), 3.306 (1.30), 3.331 (4.23), 3.356 (1.90), 3.377 (1.20), 3.390 (1.04), 3.611 (2.08), 3.646 (1.91), 3.713 (0.70), 3.724 (1.21), 3.736 (0.70), 3.750 (0.80), 4.136 (2.46), 4.152 (5.12), 4.168 (2.36), 4.487 (1.35), 4.498 (0.79), 4.511 (0.73), 4.523 (1.30), 5.759 (4.13), 6.824 (3.04), 6.827 (3.14), 6.843 (3.42), 6.846 (3.24), 6.905 (2.82), 6.908 (3.07), 6.922 (4.61), 6.925 (4.32), 6.965 (4.20), 6.982 (3.24), 6.984 (4.39), 7.002 (2.65), 7.347 (2.77), 7.367 (4.76), 7.386 (3.81), 7.435 (4.61), 7.456 (2.78), 7.487 (0.61), 7.492 (1.08), 7.504 (3.02), 7.509 (3.06), 7.512 (3.88), 7.520 (6.85), 7.528 (4.06), 7.531 (3.40), 7.535 (3.38), 7.548 (1.20), 7.553 (0.67), 7.682 (3.28), 7.686 (3.42), 7.703 (3.16), 7.706 (3.07), 7.851 (2.70), 7.854 (2.07), 7.860 (1.37), 7.868 (2.03), 7.874 (2.31), 8.228 (2.49), 8.235 (2.13), 8.242 (1.02), 8.244 (1.13), 8.248 (1.37), 8.250 (1.95), 8.253 (2.22).

The title compound (322 mg) was separated into enantiomers by chiral HPLC, followed by flash chromatography to give enantiomer 1 (75 mg, see Example 1-43) and enantiomer 2 (77 mg, see Example 1-44).

Preparative chiral HPLC method: Instrument: Labomatic HD5000, Labocord-5000; Gilson GX-241, Labcol Vario 4000, column: Chiralpak ID 5μ 250×30 mm; Eluent A: hexane+0.1 Vol-% diethylamine (99%); Eluent B: ethanol; isocratic 50% A-50% B; flow: 40.0 ml/min; UV 254 nm Analytical chiral HPLC method: Instrument: Agilent HPLC 1260; column: Chiralpak ID 3μ 100×4.6 mm; Eluent A: hexane+0.1 Vol-% diethylamine (99%); Eluent B: ethanol; gradient: 20-50% B in 7 min; flow 1.4 ml/min; Temperature: 25° C.; DAD 254 nm

Example 1-43

(+)-7,9-dimethyl-11-(morpholin-4-ylmethyl)-1-[3-(naphthalen-1-yloxy)propyl]-4,5,6,7,8,9-hexahydro-pyrazolo[3',4':7,8][1,5]diazecino[9,10,1-hi]indole-2-carboxylic acid (Enantiomer 1)

For the preparation of the racemate see Example 1-42. After separation of enantiomers by preparative chiral HPLC (method see Example 1-42), the obtained product was further purified by flash chromatography (dichloromethane/ethanol gradient, 0%→30% ethanol) to give after lyophilisation the title compound (75 mg).

Analytical chiral HPLC (method see Example 1-42): R$_t$=5.38 min.

Specific optical rotation (Method O1): +81.4 (c=1.0 g/100 ml in DMSO)

Example 1-44

(−)-7,9-dimethyl-11-(morpholin-4-ylmethyl)-1-[3-(naphthalen-1-yloxy)propyl]-4,5,6,7,8,9-hexahydro-pyrazolo[3',4':7,8][1,5]diazecino[9,10,1-hi]indole-2-carboxylic acid (Enantiomer 2)

For the preparation of the racemic title compound see Example 1-42. After separation of enantiomers by preparative chiral HPLC (method see Example 1-42), the obtained product was further purified by flash chromatography (dichloromethane/ethanol gradient, 0%→40% ethanol) to give after lyophilisation the title compound (77 mg).

Analytical chiral HPLC (method see Example 1-42): R$_t$=5.38 min.

Specific optical rotation (Method O1): −83.8° (c=1.0 g/100 ml in DMSO)

Example 1-45

(rac)-7,9-dimethyl-11-({4-[4-(methylsulfonyl)piper-azin-1-yl]phenoxy}methyl)-1-[3-(naphthalen-1-yloxy)propyl]-4,5,6,7,8,9-hexahydropyrazolo[3',4':7, 8][1,5]diazecino[9,10,1-hi]indole-2-carboxylic acid

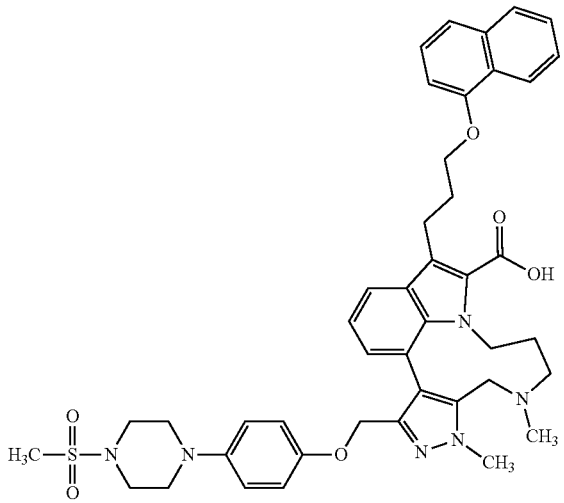 [SMILES: CN1CCCn2c(C(=O)O)c(CCCOc3cccc4ccccc34)c3cccc(c32)-c2c(COc3ccc(N4CCN(S(C)(=O)=O)CC4)cc3)nn(C)c2C1]

To a solution of (rac)-ethyl 7,9-dimethyl-11-({4-[4-(methylsulfonyl)piperazin-1-yl]phenoxy}methyl)-1-[3-(naphthalen-1-yloxy)propyl]-4,5,6,7,8,9-hexahydropyrazolo[3',4':7, 8][1,5]diazecino[9,10,1-hi]indole-2-carboxylate (see Intermediate 1-79; 990 mg, 1.23 mmol) in THF (60 ml) and ethanol (30 ml) was added a solution of lithium hydroxide in water (25 ml, 1.0 M, 25 mmol). The reaction was stirred for 27 hours at 60° C. and for 2 days at room temperature. For work-up, the mixture was concentrated under reduced pressure and the residue was purified twice by flash chromatography (dichloromethane/methanol gradient, 0%→20% methanol, and 0%→10% methanol) to give the title compound (970 mg).

LC-MS (Method 2): Rt=0.91 min; MS (ESIpos): m/z=778 [M+H]$^+$

The title compound (970 mg) was separated into enantiomers by chiral HPLC, followed by flash chromatography, to give enantiomer 1 (260 mg, see Example 1-46) and enantiomer 2 (234 mg, see Example 1-47).

Preparative chiral HPLC method: Instrument: Sepiatec: Prep SFC100; column: Chiralpak ID 5 μm 250×30 mm; eluent A: CO₂, eluent B: ethanol+0.4 Vol-% diethylamine (99%); isocratic: 43% B; flow 100.0 ml/min; temperature: 40° C.; BPR: 150 bar; MWD @ 254 nm.

Analytical chiral HPLC method: Instrument: Agilent: 1260, Aurora SFC-Module; column: Chiralpak ID 5 μm 100×4.6 mm; eluent A: CO₂, eluent B: ethanol+0.2 Vol-% diethylamine (99%); isocratic: 43% B; flow 4.0 ml/min; temperature: 37.5° C.; BPR: 100 bar; MWD @ 254 nm

Example 1-46

(+)-7,9-dimethyl-11-({4-[4-(methylsulfonyl)piperazin-1-yl]phenoxy}methyl)-1-[3-(naphthalen-1-yloxy)propyl]-4,5,6,7,8,9-hexahydropyrazolo[3',4':7,8][1,5]diazecino[9,10,1-hi]indole-2-carboxylic acid (Enantiomer 1)

For the preparation of the racemic title compound see Example 1-45. After separation of enantiomers by preparative chiral HPLC (method see Example 1-45), the obtained product was further purified by flash chromatography (dichloromethane/methanol gradient, 0%→10% methanol) to give after lyophilisation the title compound (260 mg).

Analytical chiral HPLC (method see Example 1-45): $R_t$=2.69 min.

Specific optical rotation (Method O1): +10.5° (c=1.0 g/100 ml in DMSO)

¹H-NMR (400 MHz, DMSO-d6) delta [ppm]: 0.831 (0.50), 0.853 (0.40), 0.858 (0.49), 1.232 (0.43), 1.872 (0.42), 2.194 (7.02), 2.217 (1.00), 2.304 (0.42), 2.323 (0.93), 2.327 (1.12), 2.332 (0.82), 2.518 (3.01), 2.523 (2.09), 2.540 (0.57), 2.665 (0.58), 2.669 (0.82), 2.674 (0.57), 2.875 (16.00), 2.963 (2.33), 2.975 (3.45), 2.988 (3.65), 3.026 (0.90), 3.136 (3.27), 3.150 (3.42), 3.161 (2.37), 3.247 (0.49), 3.261 (0.49), 3.280 (0.73), 3.297 (0.43), 3.358 (0.78), 3.376 (0.50), 3.391 (0.49), 3.626 (1.15), 3.661 (1.14), 3.881 (11.27), 4.142 (1.03), 4.157 (2.08), 4.173 (0.98), 4.302 (0.60), 4.338 (0.57), 4.663 (0.43), 4.693 (2.70), 4.698 (2.65), 4.727 (0.40), 5.759 (0.94), 6.496 (2.91), 6.519 (3.54), 6.673 (3.56), 6.696 (2.72), 6.826 (1.46), 6.845 (1.54), 6.920 (0.82), 6.924 (1.00), 6.937 (1.98), 6.941 (1.83), 6.957 (1.77), 6.976 (1.82), 6.994 (0.82), 7.345 (1.04), 7.365 (1.94), 7.384 (1.48), 7.435 (2.05), 7.456 (1.23), 7.487 (0.46), 7.500 (1.22), 7.504 (1.19), 7.508 (1.47), 7.516 (2.55), 7.524 (1.55), 7.532 (1.29), 7.544 (0.47), 7.683 (1.30), 7.686 (1.34), 7.703 (1.23), 7.706 (1.19), 7.850 (1.19), 7.859 (0.62), 7.868 (1.01), 7.874 (0.98), 8.218 (1.05), 8.224 (0.97), 8.242 (0.98), 13.087 (0.47).

Example 1-47

(−)-7,9-dimethyl-11-({4-[4-(methylsulfonyl)piperazin-1-yl]phenoxy}methyl)-1-[3-(naphthalen-1-yloxy)propyl]-4,5,6,7,8,9-hexahydropyrazolo[3',4':7,8][1,5]diazecino[9,10,1-hi]indole-2-carboxylic acid (Enantiomer 2)

For the preparation of the racemic title compound see Example 1-45. After separation of enantiomers by preparative chiral HPLC (method see Example 1-45), the obtained product was further purified by flash chromatography (dichloromethane/methanol gradient, 0%→10% methanol) to give after lyophilisation the title compound (234 mg).

Analytical chiral HPLC (method see Example 1-45): $R_t$=4.16 min.

Specific optical rotation (Method O1): −13.7° (c=1.0 g/100 ml in DMSO)

¹H-NMR (400 MHz, DMSO-d6) δ[ppm]: 0.808 (0.48), 0.835 (0.42), 1.209 (0.40), 1.850 (0.42), 2.171 (7.16), 2.194 (1.03), 2.282 (0.40), 2.300 (0.80), 2.304 (0.95), 2.309 (0.69), 2.495 (2.62), 2.500 (1.86), 2.517 (0.60), 2.642 (0.47), 2.646 (0.63), 2.651 (0.46), 2.852 (16.00), 2.940 (2.33), 2.952 (3.50), 2.965 (3.71), 3.004 (0.91), 3.114 (3.27), 3.127 (3.48), 3.138 (2.42), 3.224 (0.49), 3.238 (0.49), 3.257 (0.75), 3.276 (0.40), 3.335 (0.82), 3.353 (0.49), 3.368 (0.50), 3.603 (1.15), 3.639 (1.17), 3.859 (11.63), 4.119 (1.04), 4.135 (2.10), 4.150 (1.01), 4.279 (0.62), 4.315 (0.58), 4.641 (0.43), 4.670 (2.73), 4.675 (2.71), 4.705 (0.42), 5.736 (0.75), 6.473 (2.97), 6.496 (3.62), 6.649 (3.58), 6.672 (2.77), 6.803 (1.48), 6.821 (1.57), 6.897 (0.85), 6.901 (1.04), 6.915 (2.03), 6.918 (1.87), 6.934 (1.80), 6.953 (1.89), 6.971 (0.86), 7.321 (1.07), 7.341 (2.00), 7.361 (1.49), 7.412 (2.06), 7.433 (1.27), 7.464 (0.46), 7.477 (1.21), 7.482 (1.20), 7.485 (1.52), 7.493 (2.65), 7.501 (1.57), 7.504 (1.36), 7.509 (1.32), 7.521 (0.47), 7.660 (1.31), 7.663 (1.38), 7.679 (1.26), 7.683 (1.24), 7.827 (1.22), 7.836 (0.63), 7.845 (1.02), 7.851 (1.03), 8.195 (1.07), 8.202 (0.98), 8.211 (0.55), 8.219 (1.03), 13.065 (0.42).

Example 1-48

(rac)-7,9-dimethyl-11-{[4-(methylsulfonyl)phenoxy] methyl}-1-[3-(naphthalen-1-yloxy)propyl]-4,5,6,7,8,9-hexahydropyrazolo[3',4':7,8][1,5]diazecino[9,10,1-hi]indole-2-carboxylic acid

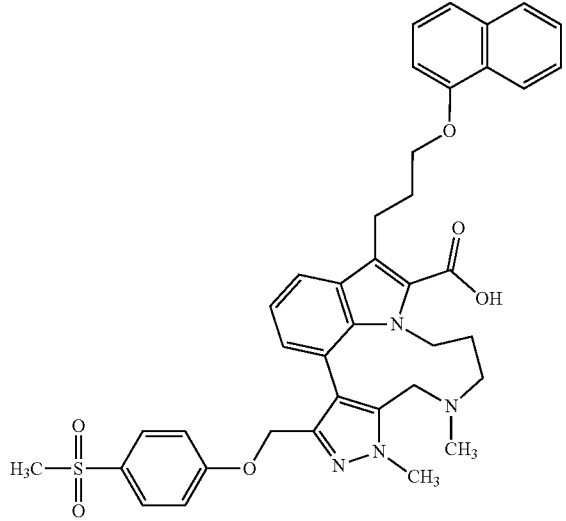 [SMILES: CN1CCCn2c(C(=O)O)c(CCCOc3cccc4ccccc34)c3cccc(c32)-c2c(COc3ccc(S(C)(=O)=O)cc3)nn(C)c2C1]

To a solution of (rac)-ethyl 7,9-dimethyl-11-{[4-(methylsulfonyl)phenoxy]methyl}-1-[3-(naphthalen-1-yloxy)propyl]-4,5,6,7,8,9-hexahydropyrazolo[3',4':7,8][1,5]diazecino[9,10,1-hi]indole-2-carboxylate (see Intermediate 1-86; 350 mg, 486 μmol) in THF (23 ml) and ethanol (11 ml) was added a solution of lithium hydroxide in water (9.7 ml, 1.0 M, 9.7 mmol). The reaction mixture was stirred for 12 days at room temperature. For workup, the reaction mixture was concentrated under reduced pressure and the residue was purified by flash chromatography (dichloromethane/methanol gradient, 0%→20% methanol) to give the title compound (294 mg) as a racemic mixture.

LC-MS (Method 2): Rt=0.92 min; MS (ESIpos): m/z=694 [M+H]$^+$ $^1$H-NMR (400 MHz, DMSO-d6) δ[ppm]: 1.109 (0.61), 1.172 (0.67), 1.232 (0.67), 1.857 (0.41), 1.987 (1.12), 2.165 (0.82), 2.195 (9.34), 2.318 (0.51), 2.322 (0.70), 2.327 (1.00), 2.332 (0.78), 2.518 (2.77), 2.523 (1.84), 2.664 (0.49), 2.669 (0.70), 2.673 (0.51), 3.003 (1.13), 3.039 (1.20), 3.090 (16.00), 3.242 (0.45), 3.256 (0.47), 3.275 (0.71), 3.354 (0.60), 3.372 (0.49), 3.610 (0.55), 3.637 (1.55), 3.674 (1.14), 3.896 (13.12), 4.131 (0.59), 4.146 (1.32), 4.159 (1.29), 4.174 (0.58), 4.278 (0.59), 4.314 (0.54), 4.898 (4.26), 5.759 (8.86), 6.829 (1.48), 6.846 (1.64), 6.855 (0.51), 6.863 (3.97), 6.868 (1.17), 6.880 (1.24), 6.885 (4.25), 6.892 (0.42), 6.927 (0.43), 6.932 (0.79), 6.945 (2.38), 6.950 (4.17), 6.969 (2.20), 6.986 (0.77), 7.341 (1.20), 7.361 (2.14), 7.380 (1.73), 7.431 (2.13), 7.452 (1.29), 7.485 (0.51), 7.497 (1.30), 7.502 (1.19), 7.507 (1.44), 7.514 (3.01), 7.521 (1.42), 7.527 (1.30), 7.531 (1.46), 7.544 (0.55), 7.639 (0.46), 7.647 (4.73), 7.652 (1.25), 7.664 (1.30), 7.669 (4.66), 7.672 (1.73), 7.677 (1.61), 7.691 (1.17), 7.696 (1.18), 7.848 (1.24), 7.856 (0.67), 7.865 (1.17), 7.871 (1.07), 8.221 (1.13), 8.226 (1.04), 8.238 (0.55), 8.243 (0.98), 8.245 (1.05).

The title compound (294 mg) was separated into enantiomers by chiral HPLC, followed by flash chromatography, to give enantiomer 1 (120 mg, see Example 1-49) and enantiomer 2 (125 mg, see Example 1-50).

Preparative chiral HPLC method: Instrument: Labomatic HD5000, Labocord-5000; Gilson GX-241, Labcol Vario 4000, column: Chiralpak IA 5µ 250×30 mm; eluent A: hexane+trifluoro acetic acid; eluent B: ethanol; gradient: 20-50% B in 15 min; flow 40.0 ml/min; UV 254 nm Analytical chiral HPLC method: Instrument: Agilent HPLC 1260; column: Chiralpak IA 3µ 100×4.6 mm; eluent A: hexane+0.1 Vol trifluoroacetic acid; eluent B: ethanol; gradient: 5-50% B in 7 min; flow 1.4 ml/min; temperature: 25° C.; DAD 254 nm Example 1-49

(−)-7,9-dimethyl-11-{[4-(methylsulfonyl)phenoxy]methyl}-1-[3-(naphthalen-1-yloxy)propyl]-4,5,6,7,8,9-hexahydropyrazolo[3',4':7,8][1,5]diazecino[9,10,1-hi]indole-2-carboxylic acid (Enantiomer 1)

For the preparation of the racemic title compound see Example 1-48. After separation of enantiomers by preparative chiral HPLC (method see Example 1-48), the obtained product was further purified by flash chromatography (dichloromethane/methanol gradient, 0%→10% methanol) to give after lyophilisation the title compound (120 mg).

Analytical chiral HPLC (method see Example 1-48): R$_t$=6.62 min.

Specific optical rotation (Method O1): −5.7° (c=1.0 g/100 ml in DMSO)

1H-NMR (400 MHz, DMSO-d6): δ [ppm]=13.35 (br s, 1H), 9.63 (br s, 1H), 8.30-8.13 (m, 1H), 7.96-7.84 (m, 1H), 7.78 (br d, 1H), 7.71-7.62 (m, 2H), 7.58-7.26 (m, 4H), 7.15-6.96 (m, 2H), 6.82 (dd, 3H), 5.03-4.77 (m, 2H), 4.66-4.39 (m, 2H), 4.28-3.99 (m, 7H), 3.70-3.56 (m, 2H), 3.44-3.22 (m, 3H), 3.08 (s, 4H), 2.96 (br s, 2H), 2.62 (br s, 1H), 2.28-2.13 (m, 2H), 1.88 (br s, 2H).

Example 1-50

(+)-7,9-dimethyl-11-{[4-(methylsulfonyl)phenoxy]methyl}-1-[3-(naphthalen-1-yloxy)propyl]-4,5,6,7,8,9-hexahydropyrazolo[3',4':7,8][1,5]diazecino[9,10,1-hi]indole-2-carboxylic acid (Enantiomer 2)

For the preparation of the racemic title compound see Example 1-48. After separation of enantiomers by preparative chiral HPLC (method see Example 1-48), the obtained product was further purified by flash chromatography (dichloromethane/ethanol gradient, 0%→30% ethanol) to give after lyophilisation the title compound (125 mg).

Analytical chiral HPLC (method see Example 1-48): R$_t$=7.62 min.

Specific optical rotation (Method O1): +2.9° (c=1.0 g/100 ml in DMSO)

$^1$H-NMR (400 MHz, DMSO-d6) δ[ppm]: 1.108 (16.00), 1.232 (0.65), 1.883 (0.45), 2.084 (2.13), 2.169 (0.56), 2.186 (0.56), 2.518 (1.54), 2.523 (1.06), 2.669 (0.42), 2.960 (1.12), 3.085 (11.04), 4.040 (2.71), 4.106 (0.56), 4.113 (0.58), 4.129 (0.70), 4.144 (0.45), 4.175 (0.63), 4.189 (0.41), 4.849 (0.63), 4.921 (1.13), 4.951 (0.73), 5.760 (2.23), 6.782 (1.20), 6.804 (1.26), 6.830 (1.10), 6.848 (1.15), 7.010 (0.40), 7.027 (0.76), 7.043 (0.50), 7.062 (0.52), 7.353 (0.78), 7.374 (1.39), 7.393 (1.08), 7.443 (1.47), 7.464 (0.90), 7.512 (0.96), 7.518 (1.30), 7.527 (1.97), 7.536 (1.39), 7.542 (1.02), 7.646 (3.20), 7.652 (0.85), 7.664 (0.89), 7.669 (2.88), 7.769 (0.56), 7.790 (0.50), 7.860 (0.87), 7.870 (0.46), 7.878 (0.65), 7.883 (0.73), 8.242 (0.75), 8.248 (0.63), 8.266 (0.69).

Example 1-51

(rac)-(E/Z)-1-methyl-3-{[4-(methylsulfonyl)phenoxy]methyl}-7-[3-(naphthalen-1-yloxy)propyl]-1,10,13,15-tetrahydropyrazolo[4',3':9,10][1,6]oxazacycloundecino[8,7,6-hi]indole-8-carboxylic acid

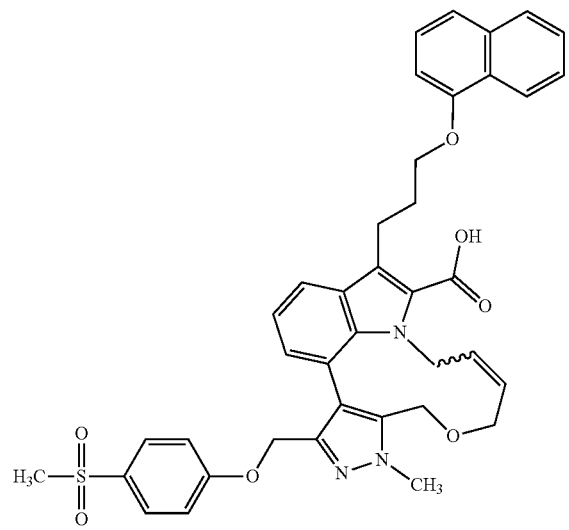 [SMILES: Cn1nc(COc2ccc(S(C)(=O)=O)cc2)c2c1COCC=CCn1c(C(=O)O)c(CCCOc3cccc4ccccc34)c3cccc-2c31]

To a solution of (rac)-(E/Z)-ethyl 1-methyl-3-{[4-(methylsulfonyl)phenoxy]methyl}-7-[3-(naphthalen-1-yloxy)propyl]-1,10,13,15-tetrahydropyrazolo[4',3':9,10][1,6]oxazacycloundecino[8,7,6-hi]indole-8-carboxylate (see Intermediate 1-88; 100 mg, 139 µmol) in THF (6.0 ml) and ethanol (3.0 ml) was added a solution of lithium hydroxide in water (2.8 ml, 1.0 M, 2.8 mmol). The reaction was stirred for 16 hours at 50° C. For work-up, the reaction mixture was concentrated under reduced pressure and the residue was purified by flash chromatography (dichloromethane/ethanol gradient, 0%→10% ethanol) to give the title compound (62 mg) as a racemic mixture.

LC-MS (Method 2): Rt=0.92 min; MS (ESIneg): m/z=691 [M−H]⁻

The title compound (62 mg) was separated into enantiomers by chiral HPLC, followed by trituration with water, to give enantiomer 1 (12 mg, see Example 1-52) and enantiomer 2 (13 mg, see Example 1-53).

Preparative chiral HPLC method: Instrument: Labomatic HD5000, Labocord-5000; Gilson GX-241, Labcol Vario 4000, column: Chiralpak IA 5μ 250×30 mm; eluent A: hexane; eluent B: ethanol; gradient: 20-50% B in 15 min; flow 40.0 ml/min; UV 254 nm Analytical chiral HPLC method: Instrument: Agilent HPLC 1260; column: Chiralpak IA 3μ 100×4.6 mm; eluent A: hexane+0.1 Vol % trifluoroacetic acid; eluent B: ethanol; gradient: 20-50% B in 7 min; flow 1.4 ml/min; temperature: 25° C.; DAD 254 nm Example 1-52

(E/Z)-1-methyl-3-{[4-(methylsulfonyl)phenoxy]methyl}-7-[3-(naphthalen-1-yloxy)propyl]-1,10,13,15-tetrahydropyrazolo[4',3':9,10][1,6]oxazacycloundecino[8,7,6-hi]indole-8-carboxylic acid (Enantiomer 1)

For the preparation of the racemic title compound see Example 1-51. After separation of enantiomers by preparative chiral HPLC (method see Example 1-51), the obtained product was triturated with water to give after lyophilisation the title compound (12 mg).

Analytical chiral HPLC (method see Example 1-51): $R_t$=5.78 min.

¹H-NMR (400 MHz, DMSO-d6) δ[ppm]: 0.852 (0.50), 1.137 (1.45), 1.155 (3.22), 1.173 (1.53), 1.232 (1.95), 2.133 (0.46), 2.153 (0.88), 2.174 (0.88), 2.191 (0.54), 2.318 (0.77), 2.322 (1.65), 2.326 (2.30), 2.331 (1.61), 2.336 (0.73), 2.518 (9.11), 2.522 (6.43), 2.539 (10.95), 2.660 (0.77), 2.664 (1.72), 2.668 (2.33), 2.673 (1.65), 2.678 (0.73), 2.692 (1.42), 2.915 (0.65), 2.933 (0.65), 3.073 (16.00), 3.273 (0.54), 3.283 (0.65), 3.294 (0.88), 3.301 (1.00), 3.478 (0.57), 3.509 (1.00), 3.540 (0.65), 3.786 (0.57), 3.797 (0.73), 3.819 (0.57), 3.829 (0.50), 3.957 (13.93), 4.040 (0.54), 4.047 (0.54), 4.063 (0.73), 4.135 (0.84), 4.149 (0.54), 4.158 (0.57), 4.227 (1.53), 4.261 (1.65), 4.579 (1.61), 4.608 (2.18), 4.638 (0.50), 4.651 (0.54), 4.679 (0.54), 4.741 (1.68), 4.776 (1.57), 4.799 (1.88), 4.829 (1.57), 5.000 (0.38), 5.027 (0.92), 5.050 (1.11), 5.088 (0.46), 5.177 (0.54), 6.791 (1.84), 6.810 (2.26), 6.834 (3.29), 6.856 (3.41), 6.955 (1.15), 6.974 (1.57), 6.993 (0.96), 7.337 (1.19), 7.357 (2.14), 7.376 (1.61), 7.430 (2.22), 7.450 (1.38), 7.483 (0.50), 7.495 (1.26), 7.500 (1.19), 7.506 (1.42), 7.513 (2.91), 7.520 (1.45), 7.526 (1.30), 7.530 (1.45), 7.542 (0.57), 7.628 (0.50), 7.636 (4.71), 7.640 (1.34), 7.653 (1.34), 7.658 (4.52), 7.671 (1.30), 7.691 (1.19), 7.847 (1.34), 7.855 (0.77), 7.865 (1.34), 7.870 (1.15), 8.211 (1.19), 8.217 (1.15), 8.235 (1.19).

Example 1-53

(E/Z)-1-methyl-3-{[4-(methylsulfonyl)phenoxy]methyl}-7-[3-(naphthalen-1-yloxy)propyl]-1,10,13,15-tetrahydropyrazolo[4',3':9,10][1,6]oxazacycloundecino[8,7,6-hi]indole-8-carboxylic acid (Enantiomer 2)

For the preparation of the racemic title compound see Example 1-51. After separation of enantiomers by preparative chiral HPLC (method see Example 1-51), the obtained product was triturated with water to give after lyophilisation the title compound (13 mg).

Analytical chiral HPLC (method see Example 1-51): $R_t$=6.93 min.

¹H-NMR (400 MHz, DMSO-d6) δ[ppm]: 0.852 (0.51), 1.137 (2.73), 1.155 (6.06), 1.173 (2.96), 1.232 (1.99), 2.136 (0.60), 2.155 (0.88), 2.174 (0.92), 2.193 (0.55), 2.318 (0.88), 2.323 (2.03), 2.327 (2.82), 2.332 (1.94), 2.337 (0.83), 2.518 (11.01), 2.523 (7.82), 2.540 (11.84), 2.660 (0.88), 2.665 (2.08), 2.669 (2.87), 2.674 (1.99), 2.679 (0.88), 2.693 (1.76), 2.897 (0.46), 2.916 (1.25), 2.934 (1.20), 3.074 (16.00), 3.283 (0.79), 3.293 (0.88), 3.301 (1.11), 3.479 (0.55), 3.511 (0.97), 3.541 (0.60), 3.786 (0.55), 3.797 (0.69), 3.819 (0.55), 3.831 (0.51), 3.957 (14.15), 4.040 (0.51), 4.048 (0.55), 4.064 (0.69), 4.135 (0.83), 4.150 (0.55), 4.159 (0.55), 4.228 (1.53), 4.262 (1.62), 4.579 (1.62), 4.608 (2.13), 4.639 (0.51), 4.653 (0.51), 4.680 (0.51), 4.742 (1.62), 4.777 (1.53), 4.800 (1.85), 4.829 (1.53), 5.001 (0.42), 5.028 (0.88), 5.051 (1.06), 5.088 (0.42), 5.179 (0.51), 6.791 (1.85), 6.810 (2.22), 6.834 (3.19), 6.857 (3.28), 6.955 (1.11), 6.975 (1.48), 6.993 (0.88), 7.338 (1.20), 7.358 (2.13), 7.377 (1.62), 7.430 (2.22), 7.450 (1.34), 7.483 (0.55), 7.496 (1.34), 7.501 (1.20), 7.507 (1.43), 7.514 (2.91), 7.520 (1.43), 7.526 (1.25), 7.530 (1.39), 7.543 (0.55), 7.636 (4.86), 7.641 (1.34), 7.653 (1.39), 7.658 (4.53), 7.672 (1.20), 7.691 (1.06), 7.848 (1.34), 7.855 (0.69), 7.866 (1.29), 7.871 (1.11), 8.212 (1.25), 8.217 (1.16), 8.236 (1.11).

Example 1-54

(rac)-1-methyl-3-{[4-(methylsulfonyl)phenoxy]methyl}-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid

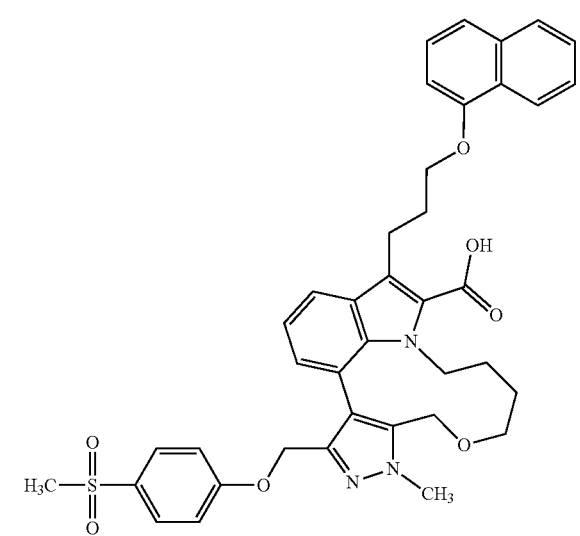 [SMILES: Cn1nc(COc2ccc(S(C)(=O)=O)cc2)c2c1COCCCCn1c(C(=O)O)c(CCCOc3cccc4ccccc34)c3cccc-2c31]

To a solution of (rac)-ethyl 1-methyl-3-{[4-(methylsulfonyl)phenoxy]methyl}-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (see Intermediate 1-89; 240 mg, 332 μmol) in THF (14 ml) and ethanol (7.2 ml) was added a solution of lithium hydroxide in water (6.6 ml, 1.0 M, 6.6 mmol). The reaction was stirred for 2 days at 50° C. For work-up, the reaction mixture was concentrated under reduced pressure and the residue was purified twice by flash chromatography (dichloromethane/methanol isocratic 10% methanol followed by dichloromethane/methanol gradient 0→10% methanol) to give the title compound (216 mg) as a racemic mixture.

The title compound (216 mg) was separated into enantiomers by chiral HPLC to give enantiomer 1 (85 mg, see Example 1-55) and enantiomer 2 (90 mg, see Example 1-56).

Preparative chiral HPLC method: Instrument: Labomatic HD5000, Labocord-5000; Gilson GX-241, Labcol Vario 4000, column: Chiralpak IF 5μ 250×20 mm; eluent A: Hexane+0.1 Vol-% trifluoroacetic acid; eluent B: ethanol; gradient: 20-50% B in 15 min; flow 30.0 ml/min; UV 254 nm Analytical chiral HPLC method: Instrument: Agilent HPLC 1260; column: Chiralpak IF 3μ 100×4.6 mm; eluent A: hexane+0.1 Vol-% trifluoroacetic acid; eluent B: ethanol; gradient: 20-50% B in 7 min; flow 1.4 ml/min; temperature: 25° C.; DAD 254 nm Example 1-55

(−)-1-methyl-3-{[4-(methylsulfonyl)phenoxy]methyl}-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (Enantiomer 1)

See Example 1-54 for preparation and enantiomer separation.
Analytical chiral HPLC (method see Example 1-54): $R_t$=4.51 min.
Specific optical rotation (Method O1): −40.9° (c=1.0 g/100 ml in DMSO)
$^1$H-NMR (400 MHz, DMSO-d6) δ[ppm]: 1.019 (1.14), 1.033 (0.95), 1.114 (1.39), 1.132 (2.88), 1.150 (1.44), 1.210 (0.97), 1.300 (0.49), 1.312 (0.50), 2.052 (2.59), 2.129 (0.88), 2.139 (0.86), 2.300 (0.77), 2.304 (1.10), 2.309 (0.79), 2.642 (0.79), 2.646 (1.12), 2.651 (0.79), 2.806 (0.56), 2.817 (0.45), 2.836 (0.61), 2.894 (0.43), 2.912 (0.41), 3.050 (16.00), 3.211 (0.41), 3.223 (0.54), 3.244 (0.68), 3.261 (0.40), 3.337 (0.47), 3.435 (0.65), 3.450 (0.52), 3.464 (0.61), 3.915 (13.44), 3.989 (0.61), 4.013 (0.41), 4.026 (0.50), 4.043 (0.58), 4.050 (0.58), 4.066 (0.90), 4.081 (0.43), 4.095 (0.45), 4.110 (0.92), 4.124 (0.56), 4.133 (0.56), 4.250 (1.41), 4.284 (1.57), 4.402 (0.65), 4.437 (0.58), 4.651 (1.86), 4.658 (1.87), 4.686 (2.86), 4.851 (2.04), 4.881 (1.68), 6.772 (1.60), 6.790 (1.73), 6.820 (1.46), 6.824 (1.57), 6.839 (5.82), 6.857 (1.37), 6.861 (4.09), 6.930 (1.62), 6.950 (1.91), 6.968 (1.24), 7.313 (1.21), 7.334 (2.18), 7.353 (1.69), 7.407 (2.25), 7.428 (1.41), 7.468 (0.52), 7.480 (1.39), 7.487 (2.00), 7.495 (3.01), 7.504 (2.13), 7.511 (1.57), 7.523 (0.52), 7.611 (0.54), 7.618 (4.85), 7.623 (1.35), 7.636 (1.33), 7.641 (4.27), 7.648 (0.45), 7.667 (1.53), 7.670 (1.60), 7.687 (1.46), 7.690 (1.41), 7.825 (1.33), 7.834 (0.68), 7.843 (0.99), 7.849 (1.14), 8.209 (1.19), 8.216 (1.03), 8.225 (0.56), 8.233 (1.08).

Example 1-56

(+)-1-methyl-3-{[4-(methylsulfonyl)phenoxy]methyl}-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (Enantiomer 2)

See Example 1-54 for preparation and enantiomer separation.
Analytical chiral HPLC (method see Example 1-54): $R_t$=5.55 min.
Specific optical rotation (Method O1): +40.3° (c=1.0 g/100 ml in DMSO)
$^1$H-NMR (400 MHz, DMSO-d6) δ[ppm]: 1.029 (0.74), 1.043 (1.05), 1.055 (0.85), 1.136 (0.82), 1.154 (1.66), 1.172 (0.89), 1.232 (0.88), 1.260 (0.58), 1.321 (0.47), 1.334 (0.50), 2.075 (0.56), 2.139 (0.59), 2.151 (0.77), 2.163 (0.76), 2.323 (0.64), 2.327 (0.91), 2.332 (0.64), 2.518 (3.13), 2.523 (2.32), 2.665 (0.65), 2.669 (0.91), 2.673 (0.62), 2.829 (0.50), 2.858 (0.55), 3.074 (16.00), 3.247 (0.47), 3.268 (0.62), 3.312 (0.50), 3.457 (0.59), 3.471 (0.47), 3.487 (0.56), 3.938 (13.65), 4.013 (0.56), 4.038 (0.42), 4.049 (0.50), 4.066 (0.52), 4.073 (0.52), 4.079 (0.42), 4.089 (0.82), 4.118 (0.40), 4.133 (0.83), 4.148 (0.50), 4.157 (0.49), 4.273 (1.32), 4.307 (1.45), 4.422 (0.62), 4.458 (0.55), 4.674 (1.71), 4.681 (1.74), 4.709 (2.57), 4.875 (1.90), 4.904 (1.60), 6.795 (1.45), 6.813 (1.57), 6.846 (1.51), 6.849 (1.57), 6.853 (0.56), 6.860 (4.39), 6.863 (2.89), 6.866 (2.82), 6.878 (1.25), 6.882 (4.20), 6.890 (0.43), 6.955 (1.74), 6.972 (1.57), 6.974 (1.88), 6.992 (1.25), 7.336 (1.23), 7.357 (2.12), 7.376 (1.63), 7.430 (2.09), 7.451 (1.31), 7.490 (0.46), 7.503 (1.37), 7.509 (1.83), 7.518 (2.82), 7.527 (1.97), 7.533 (1.48), 7.546 (0.50), 7.634 (0.45), 7.641 (4.73), 7.646 (1.20), 7.659 (1.17), 7.664 (4.20), 7.671 (0.40), 7.692 (1.48), 7.694 (1.59), 7.712 (1.45), 7.715 (1.41), 7.848 (1.23), 7.851 (0.91), 7.858 (0.62), 7.866 (0.91), 7.872 (1.07), 8.233 (1.08), 8.239 (0.92), 8.248 (0.50), 8.257 (1.02).

Example 1-57

(rac)-7,9-dimethyl-1-[3-(naphthalen-1-yloxy) propyl]-11-{[4-(tetrahydro-2H-pyran-4-yl)phenoxy]methyl}-4,5,6,7,8,9-hexahydropyrazolo[3',4':7,8][1,5]diazecino[9,10,1-hi]indole-2-carboxylic acid

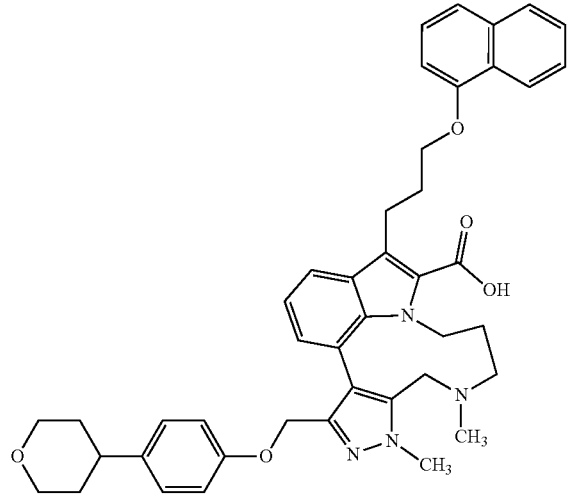 [SMILES: CN1CCCn2c(C(=O)O)c(CCCOc3cccc4ccccc34)c3cccc(c32)-c2c(COc3ccc(C4CCOCC4)cc3)nn(C)c2C1]

To a solution of (rac)-ethyl 7,9-dimethyl-1-[3-(naphthalen-1-yloxy)propyl]-11-{[4-(tetrahydro-2H-pyran-4-yl)phenoxy]methyl}-4,5,6,7,8,9-hexahydropyrazolo[3',4':7,8][1,5]diazecino[9,10,1-hi]indole-2-carboxylate (see Intermediate 1-98; 107 mg, 147 μmol) in THF (7.0 ml) and ethanol (3.5 ml) was added a solution of lithium hydroxide in water (2.9 ml, 1.0 M, 2.9 mmol). The reaction was stirred for 24 hours at 45° C. and then for 9 days at room temperature. For work-up, the reaction mixture was concentrated under reduced pressure and the residue was purified by flash chromatography (dichloromethane/ethanol 1:9) to give the title compound (127 mg) as a racemic mixture.

LC-MS (Method 2): Rt=0.98 min; MS (ESIpos): m/z=700 [M+H]$^+$

The title compound (127 mg) was separated into enantiomers by chiral HPLC, followed by flash chromatography, to give enantiomer 1 (32 mg, see Example 1-58) and enantiomer 2 (19 mg, see Example 1-59).

Preparative chiral HPLC method: Instrument: Sepiatec: Prep SFC100; column: Chiralpak ID 5 μm 250×30 mm; eluent A: $CO_2$, eluent B: ethanol+0.2 Vol-% diethylamine (99%); isocratic: 32% B; flow 100.0 ml/min; temperature: 40° C.; BPR: 150 bar; MWD @ 254 nm Analytical chiral HPLC method: Instrument: Agilent: 1260, Aurora SFC-Module; column: Chiralpak ID 5 μm 100×4.6 mm; eluent A: $CO_2$, eluent B: ethanol+0.2 Vol-% diethylamine (99%); isocratic: 32% B; flow 4.0 ml/min; temperature: 37.5° C.; BPR: 100 bar; MWD @ 254 nm Example 1-58

(+)-7,9-dimethyl-1-[3-(naphthalen-1-yloxy)propyl]-11-{[4-(tetrahydro-2H-pyran-4-yl)phenoxy]methyl}-4,5,6,7,8,9-hexahydropyrazolo[3',4':7,8][1,5]diazecino[9,10,1-hi]indole-2-carboxylic acid (Enantiomer 1)

For the preparation of the racemic title compound see Example 1-57. After separation of enantiomers by preparative chiral HPLC (method see Example 1-57); the obtained product was further purified by flash chromatography (dichloromethane/methanol gradient, 0%→20% methanol) to give after lyophilisation the title compound (32 mg).

Analytical chiral HPLC (method see Example 1-57): $R_t$=2.84 min.

Specific optical rotation (Method O1): +20.0° (c=1.0 g/100 ml in DMSO)

$^1$H-NMR (400 MHz, DMSO-d6) δ[ppm]: 1.232 (1.48), 1.458 (0.68), 1.473 (0.80), 1.487 (1.20), 1.499 (1.84), 1.508 (1.88), 1.520 (1.60), 2.178 (1.01), 2.196 (7.76), 2.323 (0.84), 2.327 (0.97), 2.332 (0.79), 2.518 (3.71), 2.523 (2.33), 2.539 (11.24), 2.665 (0.57), 2.669 (0.79), 2.673 (0.57), 2.993 (0.93), 3.029 (1.00), 3.232 (0.40), 3.247 (0.45), 3.268 (0.84), 3.275 (0.67), 3.283 (1.01), 3.304 (1.51), 3.311 (1.69), 3.330 (16.00), 3.352 (0.99), 3.369 (0.52), 3.386 (0.47), 3.627 (1.20), 3.648 (0.53), 3.663 (1.12), 3.829 (1.28), 3.856 (1.05), 4.130 (0.83), 4.145 (1.67), 4.161 (0.83), 4.312 (0.41), 4.717 (2.25), 4.724 (2.17), 6.519 (2.35), 6.540 (2.57), 6.810 (1.24), 6.829 (1.29), 6.902 (2.73), 6.924 (2.63), 6.930 (1.76), 6.946 (1.33), 6.965 (1.43), 6.983 (0.59), 7.336 (0.84), 7.357 (1.61), 7.376 (1.13), 7.431 (1.68), 7.452 (1.03), 7.495 (0.95), 7.499 (0.91), 7.506 (1.01), 7.513 (1.96), 7.518 (1.05), 7.526 (0.96), 7.530 (1.04), 7.543 (0.40), 7.673 (0.99), 7.689 (0.89), 7.849 (1.01), 7.867 (1.00), 7.872 (0.87), 8.212 (0.88), 8.217 (0.89), 8.236 (0.87).

Example 1-59

(−)-7,9-dimethyl-1-[3-(naphthalen-1-yloxy)propyl]-11-{[4-(tetrahydro-2H-pyran-4-yl)phenoxy]methyl}-4,5,6,7,8,9-hexahydropyrazolo[3',4':7,8][1,5]diazecino[9,10,1-hi]indole-2-carboxylic acid (Enantiomer 2)

For the preparation of the racemic title compound see Example 1-57. After separation of enantiomers by preparative chiral HPLC (method see Example 1-57); the obtained product was further purified by flash chromatography (dichloromethane/methanol gradient, 0%→20% methanol) to give after lyophilisation the title compound (19 mg).

Analytical chiral HPLC (method see Example 1-57): $R_t$=4.64 min.

Specific optical rotation (Method O1): −21.6° (c=1.0 g/100 ml in DMSO)

$^1$H-NMR (400 MHz, DMSO-d6) δ[ppm]: 1.232 (1.23), 1.437 (0.47), 1.458 (0.93), 1.473 (1.12), 1.487 (1.71), 1.499 (2.68), 1.508 (2.66), 1.520 (2.23), 1.547 (0.55), 1.577 (0.43), 1.598 (0.40), 1.839 (0.45), 1.862 (0.47), 1.874 (0.52), 1.896 (0.45), 2.178 (1.33), 2.195 (12.04), 2.211 (1.33), 2.286 (0.47), 2.303 (0.50), 2.318 (0.85), 2.323 (1.35), 2.327 (1.64), 2.332 (1.28), 2.336 (0.83), 2.518 (5.58), 2.523 (4.11), 2.539 (3.54), 2.660 (0.45), 2.665 (1.00), 2.669 (1.40), 2.673 (1.00), 2.678 (0.45), 2.994 (1.42), 3.030 (1.50), 3.234 (0.57), 3.249 (0.64), 3.268 (1.31), 3.275 (0.90), 3.283 (1.40), 3.297 (1.16), 3.304 (2.02), 3.311 (2.16), 3.353 (1.19), 3.372 (0.66), 3.387 (0.66), 3.627 (1.80), 3.650 (0.76), 3.663 (1.71), 3.675 (0.50), 3.829 (1.85), 3.836 (1.35), 3.850 (1.23), 3.856 (1.52), 3.862 (1.28), 3.885 (16.00), 4.130 (1.16), 4.146 (2.40), 4.162 (1.19), 4.308 (0.62), 4.343 (0.59), 4.689 (0.64), 4.718 (3.35), 4.726 (3.28), 4.754 (0.62), 6.518 (3.92), 6.539 (4.20), 6.810 (1.85), 6.828 (1.97), 6.901 (4.37), 6.918 (2.42), 6.923 (4.08), 6.932 (2.54), 6.936 (2.26), 6.948 (2.37), 6.967 (2.35), 6.984 (1.02), 7.337 (1.45), 7.357 (2.61), 7.376 (2.02), 7.431 (2.59), 7.452 (1.61), 7.478 (0.47), 7.482 (0.62), 7.495 (1.59), 7.499 (1.40), 7.507 (1.64), 7.513 (3.23), 7.519 (1.71), 7.526 (1.47), 7.530 (1.71), 7.543 (0.69), 7.547 (0.50), 7.671 (1.47), 7.675 (1.52), 7.691 (1.38), 7.694 (1.38), 7.849 (1.57), 7.856 (0.90), 7.867 (1.66), 7.872 (1.33), 8.212 (1.38), 8.217 (1.33), 8.236 (1.28).

Example 1-60

(rac)-(E/Z)-3-{[4-(4-hydroxytetrahydro-2H-pyran-4-yl)phenoxy]methyl}-1-methyl-7-[3-(naphthalen-1-yloxy)propyl]-1,10,13,15-tetrahydropyrazolo[4',3':9,10][1,6]oxazacycloundecino[8,7,6-hi]indole-8-carboxylic acid

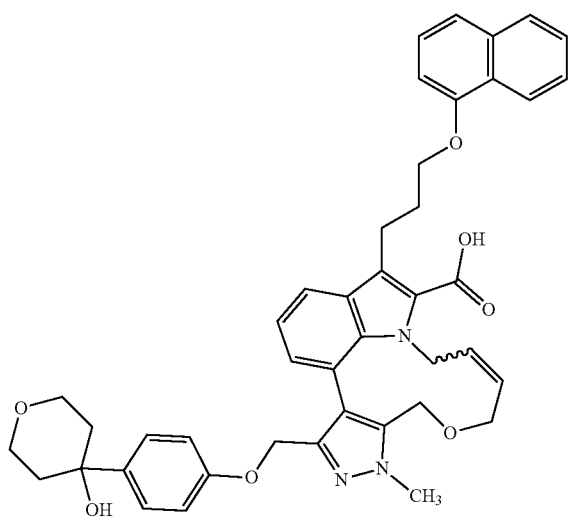 [SMILES: Cn1nc(COc2ccc(C3(O)CCOCC3)cc2)c2c1COCC=CCn1c(C(=O)O)c(CCCOc3cccc4ccccc34)c3cccc-2c31]

To a solution of (rac)-(E/Z)-ethyl 3-{[4-(4-hydroxytetrahydro-2H-pyran-4-yl)phenoxy]methyl}-1-methyl-7-[3-(naphthalen-1-yloxy)propyl]-1,10,13,15-tetrahydropyrazolo[4',3':9,10][1,6]oxazacycloundecino[8,7,6-hi]indole-8-carboxylate (see Intermediate 1-104; 80.0 mg, 108 µmol) in THF (5.2 ml) and ethanol (2.5 ml) was added a solution of lithium hydroxide in water (2.2 ml, 1.0 M, 2.2 mmol). The reaction was stirred for 4 days at room temperature. For work-up, the reaction mixture was concentrated under reduced pressure and the residue was purified by flash chromatography (dichloromethane/methanol gradient, 0%→10% methanol) to give the title compound (35 mg) as a racemic mixture.

LC-MS (Method 2): Rt=0.93 min; MS (ESIneg): m/z=713 [M−H]−

$^1$H-NMR (400 MHz, DMSO-d6) δ[ppm]: 1.071 (3.98), 1.088 (9.23), 1.106 (4.23), 1.232 (1.81), 1.393 (1.91), 1.425 (2.19), 1.770 (0.69), 1.782 (0.66), 1.804 (1.28), 1.834 (0.67), 2.182 (1.15), 2.322 (0.66), 2.327 (0.97), 2.332 (0.67), 2.461 (0.59), 2.518 (3.80), 2.523 (2.53), 2.665 (0.66), 2.669 (0.94), 2.673 (0.64), 2.729 (0.77), 2.888 (0.90), 3.275 (0.53), 3.287 (0.77), 3.308 (1.40), 3.354 (2.24), 3.372 (4.16), 3.389 (4.44), 3.406 (1.41), 3.487 (0.66), 3.518 (1.13), 3.547 (0.76), 3.575 (0.97), 3.587 (1.17), 3.601 (1.84), 3.613 (1.69), 3.660 (1.84), 3.686 (2.32), 3.713 (1.07), 3.788 (0.71), 3.799 (0.86), 3.820 (0.66), 3.831 (0.62), 3.864 (0.54), 3.919 (1.20), 3.946 (16.00), 4.067 (0.66), 4.075 (0.69), 4.091 (1.07), 4.107 (0.54), 4.118 (0.62), 4.133 (1.13), 4.148 (0.72), 4.157 (0.76), 4.171 (0.46), 4.225 (1.79), 4.260 (1.91), 4.417 (1.97), 4.445 (2.34), 4.648 (2.29), 4.675 (2.22), 4.706 (0.69), 4.720 (0.86), 4.734 (2.22), 4.746 (0.92), 4.768 (1.96), 4.800 (1.50), 5.036 (0.61), 5.062 (1.15), 5.085 (1.79), 5.125 (0.74), 5.160 (0.43), 5.169 (0.46), 5.187 (0.62), 5.759 (1.35), 6.549 (4.37), 6.571 (4.59), 6.776 (1.91), 6.793 (3.77), 6.808 (2.22), 6.810 (2.19), 6.955 (1.91), 6.975 (2.27), 6.993 (1.51), 7.168 (0.67), 7.176 (5.02), 7.198 (4.47), 7.332 (1.48), 7.352 (2.70), 7.371 (2.15), 7.428 (2.70), 7.449 (1.74), 7.476 (0.54), 7.480 (0.74), 7.494 (1.64), 7.497 (1.63), 7.505 (1.86), 7.511 (3.49), 7.518 (1.91), 7.525 (1.69), 7.528 (1.81), 7.542 (0.71), 7.546 (0.48), 7.682 (1.83), 7.685 (1.86), 7.702 (1.84), 7.846 (1.74), 7.853 (1.00), 7.865 (1.78), 7.869 (1.50), 8.211 (1.46), 8.216 (1.48), 8.236 (1.38).

Example 1-61

(rac)-3-{[4-(4-hydroxytetrahydro-2H-pyran-4-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid

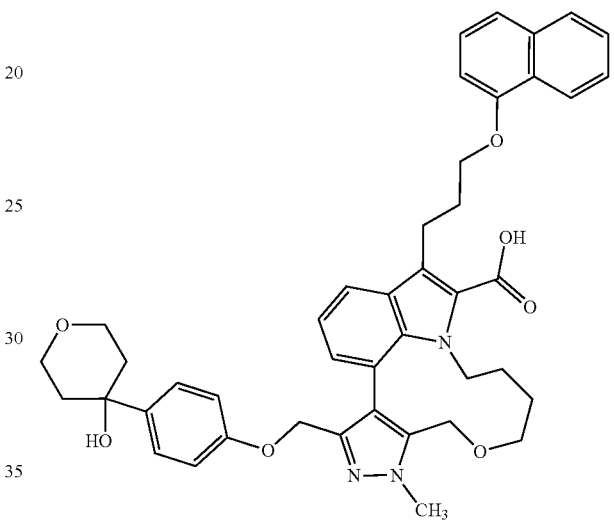

To a solution of (rac)-ethyl 3-{[4-(4-hydroxytetrahydro-2H-pyran-4-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (see Intermediate 1-105; 420 mg, 565 µmol) in THF (27 ml) and ethanol (13 ml) was added a solution of lithium hydroxide in water (11 ml, 1.0 M, 11 mmol). The reaction was stirred for 32 hours at 60° C. For work-up, the reaction mixture was concentrated under reduced pressure and the residue was purified by flash chromatography (dichloromethane/methanol gradient, 0%→10% methanol) to give the title compound (320 mg) as a racemic mixture.

LC-MS (Method 2): Rt=0.91 min; MS (ESIpos): m/z=716 [M+H]+

$^1$H-NMR (400 MHz, DMSO-d6) δ[ppm]: 0.793 (0.56), 1.049 (1.05), 1.231 (0.73), 1.387 (1.91), 1.418 (1.97), 1.762 (0.53), 1.772 (0.63), 1.793 (1.03), 1.805 (1.01), 1.826 (0.58), 1.835 (0.49), 1.908 (0.45), 2.084 (9.83), 2.159 (0.91), 2.175 (1.35), 2.193 (0.95), 2.323 (0.54), 2.327 (0.76), 2.332 (0.51), 2.518 (2.69), 2.523 (1.95), 2.665 (0.55), 2.669 (0.76), 2.673 (0.53), 2.815 (0.55), 2.827 (0.46), 2.844 (0.56), 3.237 (0.54), 3.250 (0.55), 3.270 (0.87), 3.289 (0.51), 3.356 (0.77), 3.374 (0.60), 3.460 (0.65), 3.472 (0.50), 3.490 (0.62), 3.573 (0.76), 3.585 (0.92), 3.600 (1.49), 3.612 (1.32), 3.659 (1.54), 3.687 (1.92), 3.712 (0.91), 3.926 (16.00), 4.075 (0.50), 4.088 (0.91), 4.097 (1.00), 4.113 (1.58), 4.133 (1.32), 4.149 (0.64), 4.157 (0.50), 4.269 (1.50), 4.302 (1.64), 4.502 (1.81), 4.530 (2.47), 4.560 (0.60), 4.674 (1.76), 4.707 (1.65), 4.728 (2.18), 4.756 (1.86), 4.799 (1.67), 5.759 (7.85), 6.591 (4.08), 6.613

(4.27), 6.788 (1.69), 6.805 (1.85), 6.827 (1.67), 6.829 (1.58), 6.845 (1.95), 6.847 (1.86), 6.949 (1.82), 6.969 (1.99), 6.988 (1.35), 7.176 (0.60), 7.183 (4.49), 7.205 (3.94), 7.333 (1.38), 7.353 (2.41), 7.373 (2.01), 7.429 (2.47), 7.450 (1.56), 7.486 (0.59), 7.499 (1.64), 7.503 (1.46), 7.507 (1.85), 7.515 (3.49), 7.523 (1.85), 7.526 (1.55), 7.531 (1.72), 7.544 (0.59), 7.693 (1.60), 7.695 (1.64), 7.713 (1.51), 7.715 (1.47), 7.847 (1.50), 7.855 (0.74), 7.864 (1.31), 7.870 (1.24), 8.228 (1.29), 8.234 (1.15), 8.245 (0.64), 8.252 (1.18).

The title compound (320 mg) was separated into enantiomers by chiral HPLC to give enantiomer 1 and enantiomer 2 of the corresponding elimination product 3-{[4-(3,6-dihydro-2H-pyran-4-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (examples 62 and 63).

Preparative chiral HPLC method: Instrument: Labomatic HD5000, Labocord-5000; Gilson GX-241, Labcol Vario 4000, column: Chiralpak AD 5μ 250×30 mm; eluent A: hexane+0.1 Vol-% trifluoroacetic acid (99%); eluent B: 2-propanol; gradient: 20-50% B in 20 min; flow 40.0 ml/min; UV 254 nm Analytical chiral HPLC method: Instrument: Agilent HPLC 1260; column: Chiralpak AD 3μ 100×4.6 mm; eluent A: hexane+0.1 Vol-% trifluoroacetic acid (99%); eluent B: 2-propanol; Gradient: 20-50% B in 7 min; flow 1.4 ml/min; temperature 25° C.; DAD 254 nm Example 1-62

3-{[4-(3,6-dihydro-2H-pyran-4-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (Enantiomer 1)

Analytical chiral HPLC (method see Example 1-61): $R_t$=3.17 min.

LC-MS (Method 2): Rt=0.92 min; MS (ESIpos): m/z=698 [M+H]$^+$ $^1$H-NMR (400 MHz, DMSO-d6) δ[ppm]: 1.050 (1.54), 1.204 (0.40), 1.231 (3.28), 1.347 (0.58), 2.150 (1.29), 2.168 (1.84), 2.185 (1.29), 2.246 (2.00), 2.322 (0.65), 2.326 (0.89), 2.331 (0.61), 2.518 (3.25), 2.522 (2.16), 2.664 (0.67), 2.669 (0.87), 2.673 (0.61), 2.821 (0.73), 2.834 (0.64), 2.851 (0.74), 3.226 (0.70), 3.242 (0.70), 3.260 (0.99), 3.278 (0.53), 3.348 (1.45), 3.365 (0.85), 3.383 (0.74), 3.445 (0.43), 3.462 (0.86), 3.475 (0.71), 3.492 (0.80), 3.662 (2.24), 3.675 (4.64), 3.689 (2.11), 3.927 (16.00), 4.065 (4.52), 4.072 (4.32), 4.079 (3.22), 4.102 (2.14), 4.274 (1.78), 4.307 (1.99), 4.509 (0.93), 4.525 (2.22), 4.554 (2.68), 4.675 (2.12), 4.709 (1.88), 4.760 (2.39), 4.789 (2.02), 5.758 (3.04), 5.951 (2.00), 6.587 (4.09), 6.609 (4.34), 6.766 (2.00), 6.785 (2.14), 6.832 (1.76), 6.834 (1.85), 6.849 (2.25), 6.954 (1.90), 6.973 (2.30), 6.992 (1.44), 7.127 (4.36), 7.148 (3.90), 7.328 (1.42), 7.348 (2.64), 7.367 (1.90), 7.429 (2.77), 7.450 (1.84), 7.486 (0.70), 7.498 (1.73), 7.503 (1.66), 7.509 (1.87), 7.516 (3.56), 7.523 (1.96), 7.528 (1.76), 7.532 (1.76), 7.545 (0.73), 7.549 (0.49), 7.695 (2.03), 7.712 (1.81), 7.715 (1.81), 7.849 (1.73), 7.857 (0.96), 7.868 (1.62), 7.873 (1.44), 8.218 (1.47), 8.224 (1.45), 8.241 (1.45), 13.170 (0.55).

Example 1-63

3-{[4-(3,6-dihydro-2H-pyran-4-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (Enantiomer 2)

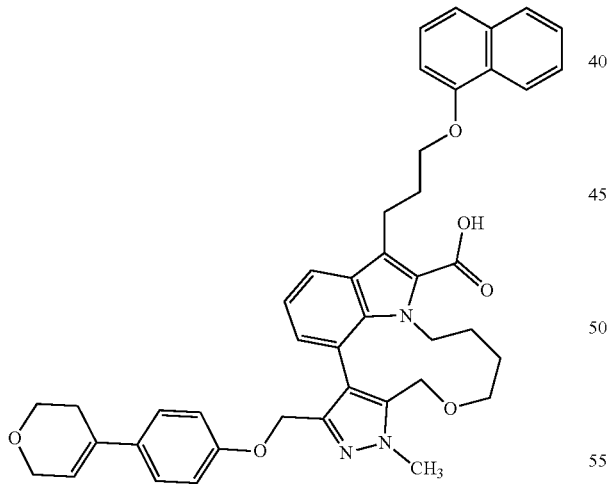

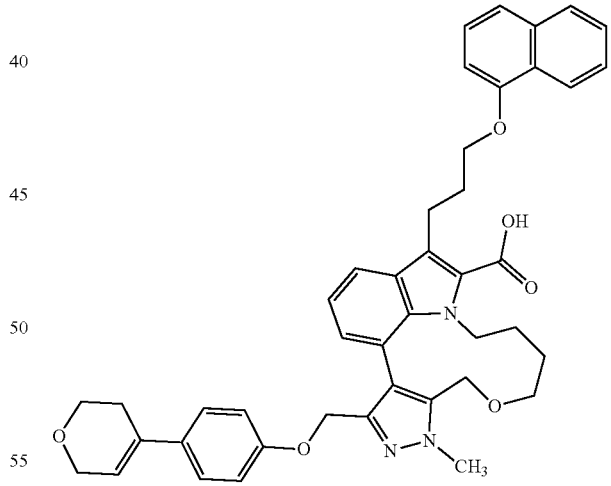

After subjection of (rac)-3-{[4-(4-hydroxytetrahydro-2H-pyran-4-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (320 mg, 447 μmol) to preparative chiral HPLC (method see Example 1-61), the obtained product was further purified by flash chromatography (dichloromethane/methanol gradient, 0%→10% methanol) to give after lyophilisation the title compound (elimination product of Example 1-61) (64 mg).

After subjection of (rac)-3-{[4-(4-hydroxytetrahydro-2H-pyran-4-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (320 mg, 447 μmol) to preparative chiral HPLC (method see Example 1-61), the obtained product was further purified by flash chromatography (dichloromethane/methanol gradient, 0%→10% methanol) to give after lyophilisation the title compound (elimination product of Example 1-61) (81 mg).

Analytical chiral HPLC (method see Example 1-61): R_t=4.43

LC-MS (Method 2): Rt=0.92 min; MS (ESIpos): m/z=698 [M+H]+ min.

¹H-NMR (400 MHz, DMSO-d6) δ[ppm]: 1.050 (1.59), 1.204 (0.41), 1.231 (3.31), 1.347 (0.59), 2.150 (1.31), 2.168 (1.91), 2.184 (1.37), 2.250 (2.07), 2.322 (0.63), 2.326 (0.84), 2.518 (3.52), 2.522 (2.33), 2.664 (0.64), 2.668 (0.82), 2.673 (0.60), 2.822 (0.75), 2.833 (0.66), 2.851 (0.77), 3.226 (0.73), 3.242 (0.74), 3.259 (1.05), 3.278 (0.56), 3.366 (0.87), 3.383 (0.75), 3.445 (0.43), 3.462 (0.89), 3.476 (0.71), 3.492 (0.82), 3.661 (2.29), 3.675 (4.71), 3.689 (2.12), 3.927 (16.00), 4.065 (4.67), 4.072 (4.46), 4.079 (3.34), 4.102 (2.18), 4.274 (1.80), 4.307 (2.03), 4.509 (0.94), 4.524 (2.29), 4.554 (2.70), 4.674 (2.14), 4.708 (1.90), 4.760 (2.43), 4.788 (2.04), 5.758 (3.05), 5.950 (2.04), 6.587 (4.14), 6.608 (4.36), 6.766 (2.07), 6.784 (2.15), 6.834 (1.90), 6.849 (2.32), 6.954 (1.96), 6.973 (2.38), 6.992 (1.43), 7.126 (4.40), 7.148 (3.97), 7.327 (1.44), 7.348 (2.67), 7.367 (1.91), 7.429 (2.86), 7.450 (1.86), 7.481 (0.56), 7.485 (0.71), 7.498 (1.79), 7.503 (1.70), 7.509 (1.91), 7.516 (3.58), 7.523 (1.96), 7.528 (1.77), 7.532 (1.73), 7.545 (0.68), 7.695 (2.05), 7.712 (1.82), 7.849 (1.80), 7.857 (0.99), 7.867 (1.63), 7.872 (1.41), 8.217 (1.57), 8.223 (1.48), 8.241 (1.47), 13.172 (0.54).

Example 1-64

(rac)-(E/Z)-3-{[4-(4-methoxytetrahydro-2H-pyran-4-yl)phenoxy]methyl}-1-methyl-7-[3-(naphthalen-1-yloxy)propyl]-1,10,13,15-tetrahydropyrazolo[4',3':9,10][1,6]oxazacycloundecino[8,7,6-hi]indole-8-carboxylic acid

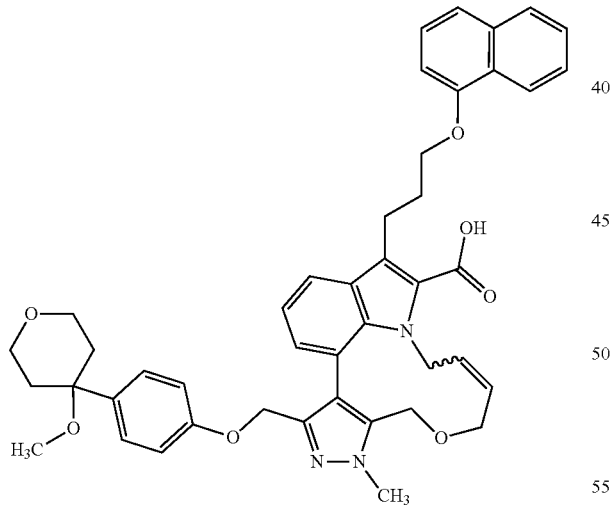

To a solution of (rac)-(E/Z)-ethyl 3-{[4-(4-methoxytetrahydro-2H-pyran-4-yl)phenoxy]methyl}-1-methyl-7-[3-(naphthalen-1-yloxy)propyl]-1,10,13,15-tetrahydropyrazolo[4',3':9,10][1,6]oxazacycloundecino[8,7,6-hi]indole-8-carboxylate (see Intermediate 1-112; 80.0 mg, 106 μmol) in THF (5.2 ml) and ethanol (2.5 ml) was added a solution of lithium hydroxide in water (2.1 ml, 1.0 M, 2.1 mmol). The reaction mixture was stirred for 32 hours at 60° C. For work-up, the reaction mixture was concentrated under reduced pressure and the residue was purified by flash chromatography (dichloromethane/methanol gradient, 0%→10% methanol) to give the title compound (43 mg) as a racemic mixture.

LC-MS (Method 2): Rt=0.97 min; MS (ESIpos): m/z=729 [M+H]+

¹H-NMR (400 MHz, DMSO-d6) δ[ppm]: 1.071 (2.44), 1.088 (4.87), 1.105 (2.35), 1.232 (0.83), 1.720 (1.05), 1.741 (2.28), 1.753 (2.37), 2.160 (0.71), 2.177 (1.05), 2.193 (0.75), 2.322 (0.49), 2.327 (0.69), 2.332 (0.50), 2.518 (2.67), 2.523 (1.80), 2.665 (0.50), 2.669 (0.72), 2.673 (0.51), 2.701 (2.06), 2.710 (16.00), 2.775 (0.69), 3.261 (0.42), 3.274 (0.48), 3.294 (0.75), 3.354 (1.43), 3.371 (2.83), 3.389 (2.51), 3.406 (0.78), 3.481 (0.48), 3.512 (0.87), 3.562 (2.72), 3.572 (2.34), 3.788 (0.49), 3.799 (0.59), 3.821 (0.49), 3.833 (0.42), 3.920 (0.61), 3.931 (0.51), 3.952 (11.73), 4.105 (0.54), 4.121 (1.32), 4.135 (1.35), 4.150 (0.62), 4.159 (0.42), 4.226 (1.36), 4.261 (1.46), 4.456 (1.44), 4.485 (1.76), 4.663 (0.40), 4.688 (2.08), 4.703 (0.60), 4.717 (1.57), 4.737 (1.64), 4.772 (1.41), 5.038 (0.97), 5.061 (0.86), 5.086 (0.78), 5.188 (0.48), 5.198 (0.48), 6.568 (3.01), 6.590 (3.26), 6.790 (1.44), 6.801 (1.53), 6.804 (1.71), 6.808 (1.84), 6.819 (1.73), 6.821 (1.62), 6.973 (1.41), 6.993 (1.65), 7.011 (1.24), 7.058 (3.51), 7.080 (3.15), 7.333 (1.08), 7.354 (1.95), 7.373 (1.55), 7.431 (2.13), 7.452 (1.37), 7.475 (0.42), 7.478 (0.58), 7.492 (1.18), 7.495 (1.22), 7.506 (1.32), 7.511 (2.04), 7.515 (1.41), 7.525 (1.19), 7.529 (1.35), 7.542 (0.58), 7.546 (0.43), 7.693 (1.31), 7.696 (1.41), 7.713 (1.36), 7.715 (1.30), 7.848 (1.33), 7.866 (1.43), 7.871 (1.11), 8.202 (1.05), 8.207 (1.14), 8.226 (1.07).

Example 1-65

(rac)-3-{[4-(4-methoxytetrahydro-2H-pyran-4-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid

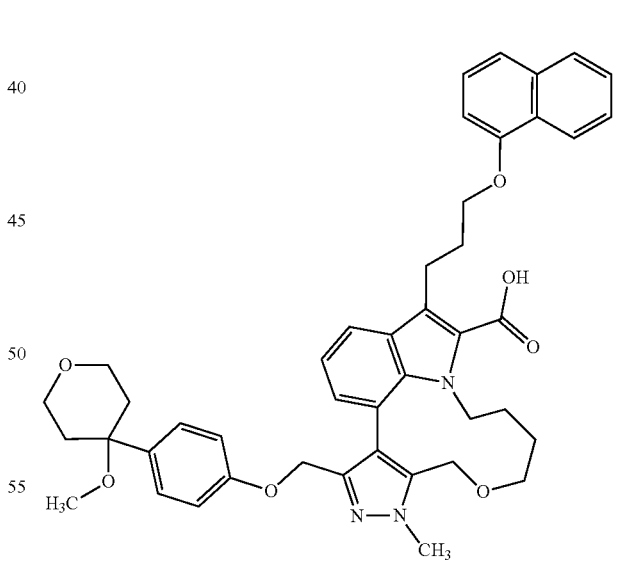

To a solution of (rac)-ethyl 3-{[4-(4-methoxytetrahydro-2H-pyran-4-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (see Intermediate 1-113; 350 mg, 462 μmol) in THF (22 ml) and ethanol (11 ml) was added a solution of lithium hydroxide in water (9.2 ml, 1.0 M, 9.2 mmol). The reaction mixture was stirred for 32 hours at 60° C. For work-up, the reaction mixture was concentrated under reduced pressure and the residue was purified three times by flash chromatography (dichloromethane/methanol gradient, 0%→10% methanol followed by dichloromethane/methanol gradient, 2.5%→10% methanol followed by dichloromethane/ethanol gradient, 0%→10% ethanol) to give the title compound (250 mg) as a racemic mixture.

LC-MS (Method 2): Rt=0.98 min; MS (ESIneg): m/z=729 [M−H]$^-$ $^1$H-NMR (400 MHz, DMSO-d6) δ[ppm]: 1.047 (0.82), 1.231 (0.86), 1.706 (0.56), 1.739 (2.32), 2.150 (0.74), 2.167 (1.14), 2.184 (0.79), 2.327 (0.52), 2.518 (1.89), 2.523 (1.45), 2.669 (0.55), 2.703 (16.00), 2.777 (0.64), 2.817 (0.44), 2.846 (0.47), 3.225 (0.45), 3.240 (0.42), 3.258 (0.66), 3.331 (6.41), 3.350 (1.00), 3.365 (0.53), 3.384 (0.52), 3.461 (0.53), 3.473 (0.42), 3.490 (0.51), 3.550 (2.33), 3.559 (2.27), 3.566 (1.93), 3.575 (1.64), 3.931 (12.20), 4.067 (0.51), 4.107 (0.73), 4.114 (0.72), 4.124 (1.27), 4.130 (1.27), 4.138 (0.70), 4.271 (1.20), 4.305 (1.33), 4.475 (0.50), 4.511 (0.45), 4.542 (1.49), 4.570 (1.75), 4.676 (1.44), 4.710 (1.30), 4.763 (1.73), 4.792 (1.49), 5.759 (8.62), 6.609 (3.06), 6.631 (3.31), 6.790 (1.38), 6.808 (1.49), 6.833 (1.23), 6.836 (1.29), 6.851 (1.56), 6.853 (1.49), 6.961 (1.40), 6.981 (1.64), 6.999 (1.13), 7.064 (3.39), 7.086 (2.95), 7.331 (1.14), 7.351 (1.95), 7.371 (1.54), 7.430 (2.00), 7.450 (1.29), 7.482 (0.50), 7.495 (1.19), 7.499 (1.09), 7.506 (1.30), 7.513 (2.55), 7.519 (1.25), 7.526 (1.16), 7.530 (1.33), 7.543 (0.53), 7.699 (1.29), 7.702 (1.35), 7.719 (1.24), 7.722 (1.18), 7.847 (1.19), 7.854 (0.65), 7.865 (1.24), 7.870 (0.99), 8.216 (1.02), 8.222 (0.98), 8.240 (0.97).

The title compound (250 mg) was separated into enantiomers by chiral HPLC to give enantiomer 1 (32 mg, see Example 1-66) and enantiomer 2 (59 mg, see Example 1-67).

Preparative chiral HPLC method: Instrument: Sepiatec: Prep SFC100; column: Chiralpak IA 5 μm 250×30 mm; eluent A: CO$_2$, eluent B: ethanol+0.4 Vol-% diethylamine (99%); isocratic: 41% B; flow 100.0 ml/min; temperature: 40° C.; BPR: 150 bar; MWD @ 254 nm Analytical chiral HPLC method: Instrument: Agilent: 1260, Aurora SFC-Module; column: Chiralpak IA 5 μm 100×4.6 mm; eluent A: CO$_2$, eluent B: ethanol+0.2 Vol-% diethylamine (99%); isocratic: 41% B; flow 4.0 ml/min; temperature: 37.5° C.; BPR: 100 bar; MWD @ 254 nm.

Example 1-66

3-{[4-(4-methoxytetrahydro-2H-pyran-4-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (Enantiomer 1)

For the preparation of the racemic title compound see Example 1-65. After separation of enantiomers by preparative chiral HPLC (method see Example 1-65); the obtained product was further purified by flash chromatography (dichloromethane/methanol gradient, 0%→10% methanol) to give after lyophilisation the title compound (32 mg).

Analytical chiral HPLC (method see Example 1-65): R$_t$=2.58 min.

LC-MS (Method 2): Rt=0.95 min; MS (ESIneg): m/z=729 [M−H]$^-$ $^1$H-NMR (400 MHz, DMSO-d6) δ[ppm]: 1.045 (1.05), 1.231 (1.99), 1.354 (0.42), 1.705 (0.74), 1.738 (2.89), 2.149 (0.98), 2.166 (1.42), 2.183 (0.98), 2.322 (0.61), 2.326 (0.82), 2.331 (0.59), 2.518 (3.15), 2.522 (2.16), 2.664 (0.66), 2.668 (0.87), 2.673 (0.66), 2.703 (16.00), 2.816 (0.53), 2.829 (0.48), 2.845 (0.56), 3.223 (0.52), 3.238 (0.53), 3.256 (0.78), 3.347 (1.32), 3.364 (0.67), 3.381 (0.63), 3.461 (0.67), 3.473 (0.52), 3.490 (0.61), 3.550 (2.91), 3.558 (2.80), 3.565 (2.38), 3.574 (1.97), 3.930 (12.35), 4.064 (0.60), 4.115 (0.94), 4.124 (1.57), 4.129 (1.53), 4.139 (0.87), 4.271 (1.35), 4.304 (1.50), 4.477 (0.56), 4.513 (0.51), 4.541 (1.61), 4.570 (1.90), 4.676 (1.60), 4.710 (1.45), 4.762 (1.87), 4.791 (1.57), 5.758 (2.55), 6.610 (3.09), 6.632 (3.29), 6.790 (1.60), 6.809 (1.72), 6.832 (1.27), 6.848 (1.53), 6.959 (1.31), 6.979 (1.71), 6.997 (1.04), 7.063 (3.60), 7.086 (3.14), 7.331 (1.12), 7.351 (2.12), 7.370 (1.50), 7.429 (2.17), 7.450 (1.38), 7.482 (0.51), 7.495 (1.26), 7.499 (1.17), 7.506 (1.37), 7.512 (2.61), 7.519 (1.38), 7.526 (1.26), 7.530 (1.32), 7.543 (0.55), 7.698 (1.39), 7.717 (1.30), 7.847 (1.34), 7.854 (0.76), 7.865 (1.30), 7.870 (1.09), 8.215 (1.15), 8.221 (1.13), 8.239 (1.11).

Example 1-67

3-{[4-(4-methoxytetrahydro-2H-pyran-4-yl)phenoxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (Enantiomer 2)

For the preparation of the racemic title compound see Example 1-65. After separation of enantiomers by preparative chiral HPLC (method see Example 1-65); the obtained product was further purified by flash chromatography (dichloromethane/methanol gradient, 0%→10% methanol) to give after lyophilisation the title compound (59 mg).

Analytical chiral HPLC (method see Example 1-65): R$_t$=4.29 min.

LC-MS (Method 2): Rt=0.95 min; MS (ESIneg): m/z=729 [M−H]$^-$ $^1$H-NMR (400 MHz, DMSO-d6) δ[ppm]: 1.047 (1.01), 1.232 (1.93), 1.706 (0.70), 1.739 (2.75), 2.149 (0.94), 2.166 (1.35), 2.183 (0.92), 2.322 (0.65), 2.326 (0.86), 2.331 (0.61), 2.518 (3.25), 2.522 (2.12), 2.664 (0.71), 2.668 (0.94), 2.673 (0.71), 2.703 (16.00), 2.816 (0.52), 2.831 (0.45), 2.846 (0.55), 3.224 (0.49), 3.238 (0.49), 3.257 (0.74), 3.348 (1.05), 3.366 (0.59), 3.382 (0.58), 3.461 (0.64), 3.473 (0.49), 3.491 (0.59), 3.550 (2.79), 3.558 (2.67), 3.565 (2.27), 3.574 (1.89), 3.930 (11.84), 4.065 (0.58), 4.108 (0.86), 4.115 (0.89), 4.124 (1.50), 4.129 (1.46), 4.139 (0.82), 4.271 (1.31), 4.304 (1.44), 4.477 (0.53), 4.511 (0.48), 4.541 (1.57), 4.570 (1.84), 4.676 (1.57), 4.710 (1.40), 4.762 (1.83), 4.791 (1.55), 5.758 (2.50), 6.610 (3.03), 6.631 (3.22), 6.790 (1.56), 6.808 (1.66), 6.834 (1.20), 6.849 (1.46), 6.960 (1.31), 6.980 (1.65), 6.997 (1.03), 7.063 (3.54), 7.086 (3.08), 7.331 (1.10), 7.351 (2.04), 7.370 (1.50), 7.429 (2.11), 7.450 (1.34), 7.482 (0.51), 7.495 (1.26), 7.499 (1.16), 7.506 (1.31), 7.513 (2.58), 7.519 (1.32), 7.526 (1.20), 7.530 (1.31), 7.543 (0.52), 7.700 (1.34), 7.717 (1.23), 7.847 (1.29), 7.854 (0.70), 7.865 (1.26), 7.870 (1.05), 8.215 (1.13), 8.220 (1.10), 8.239 (1.05).

Example 1-68

(rac)-(11Z)-1-methyl-7-[3-(naphthalen-1-yloxy)propyl]-3-[(propan-2-yloxy)methyl]-1,10,13,15-tetrahydropyrazolo[4',3':9,10][1,6]oxazacycloundecino[8,7,6-hi]indole-8-carboxylic acid

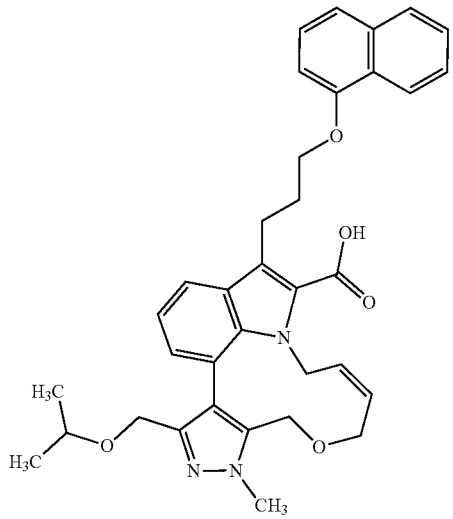 [SMILES: CC(C)OCc1nn(C)c2c1-c1cccc3c(CCCOc4cccc5ccccc45)c(C(=O)O)n(c13)C/C=C\COC2]

To a solution of (rac)-ethyl (11Z)-1-methyl-7-[3-(naphthalen-1-yloxy)propyl]-3-[(propan-2-yloxy)methyl]-1,10,13,15-tetrahydropyrazolo[4',3':9,10][1,6]oxazacycloundecino[8,7,6-hi]indole-8-carboxylate (see Intermediate 1-118; 50.0 mg, 82.3 µmol) in THF (4.0 ml) and ethanol (1.9 ml) was added a solution of lithium hydroxide in water (1.6 ml, 1.0 M, 1.6 mmol). The reaction mixture was stirred for 24 hours at 50° C. For work-up, the reaction mixture was concentrated under reduced pressure and the residue was purified by flash chromatography (dichloromethane/methanol gradient, 0%→10% methanol) to give the title compound (44 mg) as a racemic mixture.

LC-MS (Method 2): Rt=0.92 min; MS (ESIpos): m/z=579 [M+H]+

$^1$H-NMR (400 MHz, DMSO-d6) δ[ppm]: 0.534 (8.86), 0.549 (8.79), 0.686 (8.98), 0.701 (8.94), 0.719 (0.44), 0.736 (0.81), 0.753 (0.63), 1.231 (1.65), 1.903 (1.63), 1.992 (1.42), 2.104 (0.43), 2.118 (0.44), 2.180 (0.54), 2.199 (1.22), 2.216 (1.74), 2.233 (1.21), 2.250 (0.44), 2.323 (0.52), 2.327 (0.76), 2.332 (0.53), 2.518 (2.89), 2.523 (2.09), 2.665 (0.54), 2.669 (0.76), 2.673 (0.53), 3.022 (0.57), 3.037 (1.51), 3.052 (2.04), 3.067 (1.54), 3.083 (0.63), 3.273 (0.42), 3.292 (0.84), 3.379 (0.62), 3.397 (0.92), 3.416 (0.62), 3.430 (0.61), 3.455 (0.45), 3.469 (1.17), 3.501 (1.22), 3.531 (0.79), 3.768 (0.69), 3.780 (0.79), 3.803 (2.67), 3.831 (2.77), 3.872 (1.83), 3.884 (0.64), 3.905 (16.00), 3.912 (2.02), 3.960 (2.80), 3.988 (2.19), 4.164 (1.41), 4.180 (2.86), 4.195 (1.50), 4.230 (1.87), 4.264 (1.94), 4.667 (0.52), 4.694 (0.68), 4.707 (0.82), 4.716 (2.31), 4.733 (0.81), 4.750 (2.03), 5.008 (0.49), 5.035 (0.97), 5.061 (0.62), 5.102 (0.76), 5.144 (0.76), 5.162 (0.47), 5.181 (0.66), 5.191 (0.62), 5.759 (3.16), 6.779 (1.71), 6.781 (1.73), 6.796 (2.06), 6.799 (2.17), 6.822 (0.53), 6.857 (1.87), 6.874 (2.07), 7.012 (1.71), 7.033 (2.08), 7.050 (1.61), 7.290 (0.53), 7.312 (0.47), 7.359 (1.40), 7.380 (2.72), 7.387 (0.43), 7.399 (2.16), 7.442 (2.94), 7.462 (1.66), 7.484 (0.44), 7.489 (0.63), 7.501 (1.71), 7.506 (1.68), 7.510 (1.95), 7.518 (3.80), 7.525 (1.92), 7.530 (1.80), 7.534 (1.99), 7.547 (0.72), 7.551 (0.47), 7.736 (1.78), 7.739 (1.85), 7.756 (1.70), 7.758 (1.65), 7.853 (1.74), 7.861 (0.97), 7.870 (1.70), 7.876 (1.48), 8.218 (1.46), 8.224 (1.32), 8.234 (0.96), 8.242 (1.32).

Example 1-69

(rac)-1-methyl-3-[(propan-2-yloxy)methyl]-7-[3-(5,6,7,8-tetrahydronaphthalen-1-yloxy)propyl]-1,10,11,12,13,15-hexahydropyrazolo[4',3':9,10][1,6]oxazacycloundecino[8,7,6-hi]indole-8-carboxylic acid

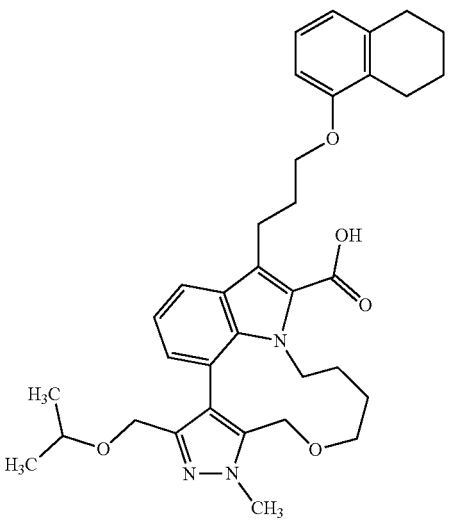 [SMILES: CC(C)OCc1nn(C)c2c1-c1cccc3c(CCCOc4cccc5c4CCCC5)c(C(=O)O)n(c13)CCCCOC2]

To a solution of (rac)-ethyl 1-methyl-3-[(propan-2-yloxy)methyl]-7-[3-(5,6,7,8-tetrahydronaphthalen-1-yloxy)propyl]-1,10,11,12,13,15-hexahydropyrazolo[4',3':9,10][1,6]oxazacycloundecino[8,7,6-hi]indole-8-carboxylate (see Intermediate 1-119; 220 mg, 358 µmol) in THF (17 ml) and ethanol (8.4 ml) was added a solution of lithium hydroxide in water (7.2 ml, 1.0 M, 7.2 mmol). The reaction mixture was stirred for 24 hours at 50° C. For work-up, the reaction mixture was concentrated under reduced pressure and the residue was purified by flash chromatography (dichloromethane/methanol gradient, 0%→10% methanol) to give the title compound (78 mg) as a racemic mixture.

LC-MS (Method 2): Rt=0.98 min; MS (ESIpos): m/z=587 [M+H]+

$^1$H-NMR (400 MHz, DMSO-d6) δ[ppm]: 0.520 (8.11), 0.535 (8.26), 0.749 (8.39), 0.764 (8.45), 1.064 (0.93), 1.071 (1.87), 1.088 (2.97), 1.106 (1.41), 1.232 (1.22), 1.311 (0.44), 1.670 (0.70), 1.677 (1.08), 1.682 (1.07), 1.695 (1.37), 1.709 (1.47), 1.724 (1.38), 1.742 (1.06), 2.019 (0.94), 2.036 (1.46), 2.052 (1.02), 2.327 (0.53), 2.518 (2.11), 2.523 (1.49), 2.612 (1.20), 2.628 (2.34), 2.642 (1.14), 2.665 (1.59), 2.669 (1.44), 2.679 (2.38), 2.694 (1.14), 2.758 (0.46), 2.773 (0.50), 2.788 (0.52), 3.112 (0.55), 3.127 (1.66), 3.142 (2.23), 3.157 (1.80), 3.173 (0.83), 3.178 (0.85), 3.263 (0.40), 3.281 (0.83), 3.299 (0.66), 3.314 (1.11), 3.330 (5.69), 3.354 (0.66), 3.372 (1.24), 3.389 (1.22), 3.406 (0.43), 3.454 (0.66), 3.466 (0.51), 3.472 (0.49), 3.484 (0.58), 3.884 (16.00), 3.893 (1.82), 3.897 (2.44), 3.918 (1.49), 3.924 (3.22), 3.933 (2.73), 3.949 (1.24), 4.002 (0.49), 4.026 (0.62), 4.040 (0.48), 4.059 (2.94), 4.086 (2.13), 4.292 (1.53), 4.325 (1.71), 4.475 (0.70), 4.485 (0.41), 4.511 (0.62), 4.662 (1.87), 4.695 (1.68), 6.580 (1.43), 6.599 (1.68), 6.612 (1.58), 6.631 (1.68), 6.814 (1.58), 6.817 (1.73), 6.832 (1.97), 6.835 (1.89), 6.954 (1.18), 6.974 (1.94), 6.993

(0.94), 7.026 (1.75), 7.044 (1.75), 7.046 (1.91), 7.064 (1.41), 7.686 (1.58), 7.689 (1.72), 7.706 (1.54), 7.709 (1.51).

Example 1-70

(rac)-7,9-dimethyl-1-[3-(naphthalen-1-yloxy) propyl]-11-[(propan-2-yloxy)methyl]-4,5,6,7,8,9-hexahydropyrazolo[3',4':7,8][1,5]diazecino[9,10,1-hi] indole-2-carboxylic acid

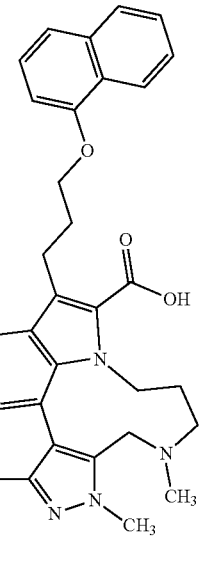

To a solution of (rac)-ethyl 7,9-dimethyl-1-[3-(naphthalen-1-yloxy)propyl]-11-[(propan-2-yloxy)methyl]-4,5,6,7,8,9-hexahydropyrazolo[3',4':7,8][1,5]diazecino[9,10,1-hi]indole-2-carboxylate (see Intermediate 1-123; 200 mg, 329 μmol) in THF (16 ml) and ethanol (7.7 ml) was added a solution of lithium hydroxide in water (6.6 ml, 1.0 M, 6.6 mmol). The reaction mixture was stirred for 2 days at 50° C. For work-up, the reaction mixture was concentrated under reduced pressure and the residue was purified by flash chromatography (dichloromethane/methanol gradient, 3%→10% methanol) to give the title compound (130 mg) as a racemic mixture.

LC-MS (Method 2): Rt=0.92 min; MS (ESIpos): m/z=581 [M+H]+

$^1$H-NMR (400 MHz, DMSO-d6) δ[ppm]: 0.672 (5.82), 0.687 (5.85), 0.767 (5.99), 0.782 (6.04), 1.088 (0.51), 1.230 (0.74), 1.898 (0.51), 1.907 (16.00), 2.171 (0.68), 2.187 (1.10), 2.207 (7.75), 2.322 (0.58), 2.326 (0.68), 2.331 (0.50), 2.518 (1.61), 2.522 (1.09), 2.668 (0.42), 2.992 (0.96), 3.028 (1.01), 3.201 (0.41), 3.216 (1.02), 3.231 (1.43), 3.247 (1.30), 3.262 (0.74), 3.278 (0.70), 3.297 (0.48), 3.332 (3.05), 3.352 (1.12), 3.370 (0.76), 3.388 (0.57), 3.607 (1.07), 3.643 (0.97), 3.745 (0.44), 4.043 (0.61), 4.072 (2.45), 4.081 (2.42), 4.110 (0.61), 4.138 (0.87), 4.154 (1.85), 4.169 (0.86), 4.470 (0.48), 4.506 (0.46), 6.831 (1.13), 6.849 (1.23), 6.900 (0.93), 6.903 (1.01), 6.918 (1.50), 6.921 (1.41), 6.967 (1.30), 6.987 (1.46), 7.005 (0.89), 7.348 (0.89), 7.369 (1.64), 7.388 (1.33), 7.435 (1.68), 7.456 (0.99), 7.502 (1.02), 7.506 (0.98), 7.509 (1.25), 7.518 (2.35), 7.526 (1.28), 7.529 (1.11), 7.533 (1.16), 7.546 (0.44), 7.687 (1.08), 7.691 (1.16), 7.708 (1.07), 7.711 (1.02), 7.849 (0.99), 7.858 (0.52), 7.867 (0.84), 7.873 (0.84), 8.221 (0.86), 8.227 (0.78), 8.238 (0.42), 8.245 (0.81).

The title compound (130 mg) was separated into enantiomers by chiral HPLC, followed by flash chromatography, to give enantiomer 1 (44 mg, see Example 1-71) and enantiomer 2 (46 mg, see Example 1-72).

Preparative chiral HPLC method: Instrument: Labomatic HD5000, Labocord-5000; Gilson GX-241, Labcol Vario 4000, column: Chiralpak IA 5μ 250×30 mm; eluant A: hexane 0.1 Vol % trifluoroacetic acid; eluant B: iso-propanol; gradient: 20-40% B in 15 min; flow 40.0 ml/min; UV 280 nm Analytical chiral HPLC method: Instrument: Agilent HPLC 1260; column: Chiralpak IA 3μ 100×4.6 mm; eluant A: hexan+0.1 Vol % trifluoroacetic acid; eluant B: isopropanol; gradient: 20-50% B in 7 min; flow 1.4 ml/min; temperature: 25° C.; DAD 280 nm Example 1-71

7,9-dimethyl-1-[3-(naphthalen-1-yloxy)propyl]-11-[(propan-2-yloxy)methyl]-4,5,6,7,8,9-hexahydropyrazolo[3',4':7,8][1,5]diazecino[9,10,1-hi]indole-2-carboxylic acid (Enantiomer 1)

For the preparation of the racemic title compound see Example 1-70. After separation of enantiomers by preparative chiral HPLC (method see Example 1-70), the obtained product was further purified by flash chromatography (dichloromethane/methanol gradient, 0%→10% methanol) to give the title compound (44 mg).

Analytical Chiral HPLC (method see Example 1-70): $R_t$=3.01 min.

$^1$H-NMR (400 MHz, CHLOROFORM-d) δ [ppm]: 0.000 (3.72), 0.697 (6.32), 0.711 (6.20), 0.811 (0.47), 0.853 (15.91), 0.868 (16.00), 0.907 (0.41), 0.922 (0.41), 1.124 (1.66), 1.141 (3.18), 1.159 (1.77), 1.184 (1.18), 1.864 (0.59), 1.978 (0.68), 2.058 (0.47), 2.257 (2.29), 2.272 (3.12), 2.289 (2.39), 2.605 (1.84), 3.215 (0.76), 3.230 (1.52), 3.245 (1.91), 3.260 (1.48), 3.275 (0.73), 3.356 (2.86), 3.374 (4.93), 3.387 (2.33), 3.392 (2.73), 3.404 (2.29), 3.422 (2.00), 3.439 (0.97), 3.825 (0.73), 3.943 (0.97), 4.012 (3.93), 4.097 (3.32), 4.113 (3.47), 4.151 (9.58), 4.180 (0.86), 4.529 (0.68), 6.641 (2.30), 6.659 (2.42), 6.928 (0.55), 7.006 (1.43), 7.034 (1.73), 7.053 (2.07), 7.071 (0.98), 7.227 (1.81), 7.246 (1.31), 7.286 (2.19), 7.305 (1.29), 7.356 (1.10), 7.369 (2.62), 7.372 (2.55), 7.389 (4.59), 7.404 (2.85), 7.408 (2.88), 7.420 (1.27), 7.450 (0.51), 7.692 (2.89), 7.711 (2.66), 7.743 (2.19), 7.763 (2.04), 8.193 (1.95), 8.212 (1.84).

Example 1-72

7,9-dimethyl-1-[3-(naphthalen-1-yloxy)propyl]-11-[(propan-2-yloxy)methyl]-4,5,6,7,8,9-hexahydropyrazolo[3',4':7,8][1,5]diazecino[9,10,1-hi]indole-2-carboxylic acid (Enantiomer 2)

For the preparation of the racemic title compound see Example 1-70. After separation of enantiomers by preparative chiral HPLC (method see Example 1-70), the obtained product was further purified by flash chromatography (dichloromethane/methanol gradient, 0%→10% methanol) to give after lyophilization the title compound (46 mg).

Analytical Chiral HPLC (method see Example 1-70): $R_t$=4.08 min.

$^1$H-NMR (400 MHz, CHLOROFORM-d) δ [ppm]: 0.000 (5.90), 0.698 (5.47), 0.712 (5.47), 0.811 (0.64), 0.853 (15.67), 0.868 (16.00), 0.908 (0.55), 0.923 (0.51), 1.124 (6.37), 1.141 (14.09), 1.159 (6.57), 1.184 (1.39), 1.209

(0.68), 1.876 (0.55), 1.978 (0.83), 2.046 (0.48), 2.257 (2.10), 2.274 (2.92), 2.290 (2.33), 2.611 (1.58), 3.216 (0.66), 3.230 (1.38), 3.246 (1.74), 3.261 (1.38), 3.357 (2.64), 3.375 (4.67), 3.386 (3.57), 3.393 (2.72), 3.403 (7.14), 3.421 (6.88), 3.439 (2.41), 3.837 (0.70), 3.945 (0.94), 4.014 (3.32), 4.062 (1.14), 4.100 (3.02), 4.114 (3.26), 4.152 (9.00), 4.526 (0.64), 6.643 (2.09), 6.662 (2.26), 6.928 (0.91), 7.007 (1.30), 7.035 (1.58), 7.053 (1.90), 7.071 (0.88), 7.176 (0.58), 7.205 (1.47), 7.229 (1.66), 7.248 (1.26), 7.288 (2.01), 7.309 (1.19), 7.358 (1.03), 7.372 (2.43), 7.375 (2.37), 7.386 (3.05), 7.391 (4.47), 7.406 (2.80), 7.410 (2.98), 7.423 (1.34), 7.427 (0.99), 7.450 (0.90), 7.695 (2.62), 7.713 (2.49), 7.743 (1.97), 7.763 (1.87), 8.194 (1.70), 8.214 (1.66).

Example 1-73

(rac)-1,14-dimethyl-7-[3-(naphthalen-1-yloxy)propyl]-3-[(propan-2-yloxy)methyl]-10,11,12,13,14,15-hexahydro-1H-pyrazolo[3',4':8,9][1,6]diazacycloundecino[10,11,1-hi]indole-8-carboxylic acid

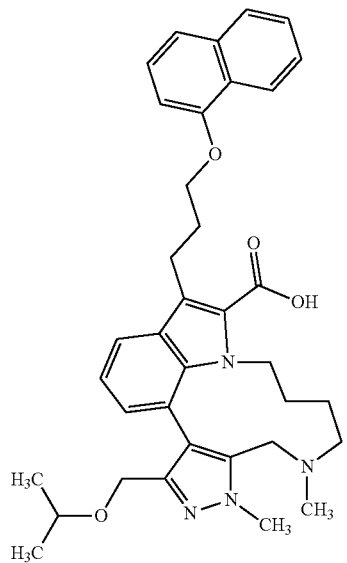 [SMILES: CC(C)OCc1nn(C)c2c1-c1cccc3c(CCCOc4cccc5ccccc45)c(C(=O)O)n(c13)CCCCN(C)C2]

To a solution of (rac)-ethyl 1,14-dimethyl-7-[3-(naphthalen-1-yloxy)propyl]-3-[(propan-2-yloxy)methyl]-10,11,12,13,14,15-hexahydro-1H-pyrazolo[3',4':8,9][1,6]diazacycloundecino[10,11,1-hi]indole-8-carboxylate (see Intermediate 1-127; 420 mg, 674 µmol) in THF (33 ml) and ethanol (16 ml) was added a solution of lithium hydroxide in water (13 ml, 1.0 M, 13 mmol). The reaction was stirred for 3 days at 50° C. For work-up, the reaction mixture was concentrated under reduced pressure and the residue was purified by flash chromatography (dichloromethane/methanol gradient, 3%→10% methanol) to give the title compound (350 mg) as a racemic mixture (contains (rac)-3-(ethoxymethyl)-1,14-dimethyl-7-[3-(1-naphthyloxy)propyl]-10,11,12,13,14,15-hexahydro-1H-pyrazolo[3',4':8,9][1,6]diazacycloundecino[10,11,1-hi]indole-8-carboxylic acid as an impurity). The title compound (350 mg) was further purified by HPLC and then separated into enantiomers by chiral HPLC, followed by flash chromatography, to give enantiomer 1 (14 mg, see Example 1-74) and enantiomer 2 (16 mg, see Example 1-75).

Preparative chiral HPLC method: Instrument: Labomatic HD5000, Labocord-5000; Gilson GX-241, Labcol Vario 4000, column: Chiralpak IA 5µ 250×30 mm; eluant A: hexane 0.1 Vol % trifluoroacetic acid; eluant B: iso-propanol; gradient: 20-50% B in 20 min; flow 40.0 ml/min; UV 254 nm Analytical chiral HPLC method: Instrument: Agilent HPLC 1260; column: Chiralpak IA 3µ 100×4.6 mm; eluant A: hexane+0.1 Vol % trifluoroacetic acid; eluant B: iso-propanol; gradient: 20-50% B in 7 min; flow 1.4 ml/min; temperature: 25° C.; DAD 254 nm Example 1-74

1,14-dimethyl-7-[3-(naphthalen-1-yloxy)propyl]-3-[(propan-2-yloxy)methyl]-10,11,12,13,14,15-hexahydro-1H-pyrazolo[3',4':8,9][1,6]diazacycloundecino[10,11,1-hi]indole-8-carboxylic acid (Enantiomer 1)

For the preparation of the racemic title compound see Example 1-73. After separation of enantiomers by preparative chiral HPLC (method see Example 1-73), the obtained product was further purified by flash chromatography (dichloromethane/methanol gradient, 0%→10% methanol) to give the title compound (14 mg).

LC-MS (Method 1): Rt=1.11 min; MS (ESIpos): m/z=595 [M+H]$^+$

Analytical Chiral HPLC (method see Example 1-73): R$_t$=2.74 min.

$^1$H-NMR (400 MHz, CHLOROFORM-d) δ [ppm]: −0.009 (0.43), 0.000 (11.26), 0.610 (10.88), 0.626 (10.88), 0.766 (0.80), 0.814 (16.00), 0.829 (15.87), 0.854 (0.75), 0.872 (1.08), 0.887 (1.22), 1.125 (2.34), 1.142 (3.93), 1.160 (2.54), 1.184 (2.63), 1.569 (0.70), 1.979 (0.65), 2.242 (1.24), 2.260 (2.82), 2.277 (4.06), 2.293 (2.91), 2.311 (1.34), 2.513 (0.94), 3.160 (0.94), 3.175 (2.06), 3.191 (2.64), 3.206 (1.94), 3.221 (0.81), 3.320 (0.65), 3.339 (1.24), 3.353 (1.26), 3.372 (1.84), 3.388 (1.18), 3.405 (1.75), 3.422 (1.86), 3.433 (1.02), 3.440 (0.96), 3.451 (1.80), 3.469 (1.25), 3.484 (1.23), 3.503 (0.60), 3.988 (2.83), 4.015 (4.46), 4.034 (5.06), 4.070 (1.95), 4.106 (3.03), 4.113 (2.75), 4.122 (3.98), 4.128 (3.93), 4.137 (2.35), 4.142 (2.04), 4.161 (3.64), 4.188 (2.57), 4.717 (0.59), 6.664 (3.63), 6.681 (3.79), 6.784 (2.12), 6.801 (2.41), 6.928 (0.72), 7.001 (1.81), 7.020 (2.74), 7.038 (1.53), 7.177 (0.61), 7.206 (0.54), 7.243 (2.60), 7.282 (3.87), 7.329 (4.95), 7.350 (2.86), 7.391 (1.02), 7.403 (5.01), 7.408 (3.33), 7.414 (4.20), 7.416 (4.19), 7.422 (3.44), 7.427 (4.83), 7.439 (0.95), 7.451 (0.75), 7.716 (3.11), 7.721 (2.31), 7.730 (3.93), 7.733 (3.80), 7.740 (3.29), 7.753 (1.86), 8.268 (1.70), 8.278 (1.66), 8.292 (1.65).

Example 1-75

1,14-dimethyl-7-[3-(naphthalen-1-yloxy)propyl]-3-[(propan-2-yloxy)methyl]-10,11,12,13,14,15-hexahydro-1H-pyrazolo[3',4':8,9][1,6]diazacycloundecino[10,11,1-hi]indole-8-carboxylic acid (Enantiomer 2)

For the preparation of the racemic title compound see Example 1-73. After separation of enantiomers by preparative chiral HPLC (method see Example 1-73) the obtained product was further purified by flash chromatography (dichloromethane/methanol gradient, 0%→10% methanol) to give the title compound (16 mg).

LC-MS (Method 1): Rt=1.11 min; MS (ESIpos): m/z=595 [M+H]+

Analytical Chiral HPLC (method see Example 1-73): R$_t$=3.38 min.

¹H-NMR (400 MHz, CHLOROFORM-d) δ [ppm]: 0.000 (0.54), 0.009 (15.74), 0.018 (0.62), 0.617 (10.07), 0.633 (10.10), 0.773 (0.58), 0.821 (15.91), 0.837 (16.00), 0.848 (2.22), 0.865 (3.10), 0.883 (1.75), 1.134 (3.60), 1.151 (6.40), 1.168 (3.72), 1.193 (3.13), 1.577 (0.74), 1.988 (0.74), 2.251 (1.17), 2.270 (2.66), 2.286 (4.07), 2.302 (3.26), 2.319 (1.70), 2.533 (0.98), 3.114 (0.44), 3.133 (0.43), 3.166 (0.90), 3.182 (1.99), 3.197 (2.59), 3.212 (1.93), 3.227 (1.09), 3.243 (0.57), 3.329 (0.59), 3.348 (1.16), 3.363 (1.20), 3.382 (1.82), 3.397 (1.52), 3.414 (2.79), 3.431 (2.91), 3.449 (1.52), 3.460 (1.93), 3.479 (1.43), 3.494 (1.28), 3.513 (0.65), 3.992 (2.61), 4.020 (4.48), 4.036 (5.46), 4.075 (2.39), 4.116 (2.39), 4.123 (2.37), 4.132 (3.91), 4.137 (4.17), 4.146 (3.10), 4.153 (3.06), 4.168 (3.81), 4.195 (2.45), 4.718 (0.67), 6.674 (3.50), 6.691 (3.81), 6.705 (0.80), 6.792 (2.24), 6.809 (2.55), 6.937 (0.80), 7.009 (1.66), 7.028 (2.56), 7.047 (1.47), 7.215 (0.54), 7.252 (2.67), 7.257 (0.82), 7.272 (4.89), 7.291 (3.87), 7.296 (1.02), 7.339 (5.46), 7.360 (3.21), 7.399 (0.96), 7.413 (5.12), 7.417 (3.55), 7.424 (4.77), 7.431 (3.99), 7.436 (5.27), 7.448 (1.09), 7.460 (0.86), 7.726 (3.40), 7.731 (2.56), 7.739 (4.26), 7.743 (3.71), 7.750 (3.75), 7.761 (1.90), 8.277 (1.86), 8.287 (1.77), 8.301 (1.74).

Example 1-76

(rac)-(E/Z)-1-methyl-7-[3-(naphthalen-1-yloxy)propyl]-3-(phenoxymethyl)-1,10,13,15-tetrahydropyrazolo[4',3':9,10][1,6]oxazacycloundecino[8,7,6-hi]indole-8-carboxylic acid

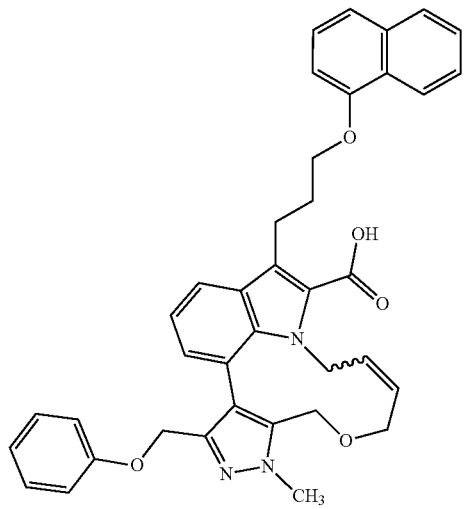 [SMILES: Cn1nc(COc2ccccc2)c2c1COCC=CCn1c(C(=O)O)c(CCCOc3cccc4ccccc34)c3cccc-2c31]

To a solution of (rac)-(E/Z)-ethyl 1-methyl-7-[3-(naphthalen-1-yloxy)propyl]-3-(phenoxymethyl)-1,10,13,15-tetrahydropyrazolo[4',3':9,10][1,6]oxazacycloundecino[8,7,6-hi]indole-8-carboxylate (see Intermediate 1-132; 110 mg, 171 μmol) in THF (7.0 ml) and ethanol (5.0 ml) was added a solution of lithium hydroxide in water (3.4 ml, 1.0 M, 3.4 mmol). The reaction was stirred for 20 hours at 60° C. For work-up, aqueous 1N HCl was added until a pH of 2 was reached. The mixture was poured into water and was extracted with dichloromethane. The combined organic phases washed with brine and dried over sodium sulfate. After filtration and removal of the solvent the crude product was purified by flash chromatography (dichloromethane/methanol gradient, 2%→10% methanol) to give the title compound as a racemic mixture (80 mg).

LC-MS (Method 2): Rt=0.99 min; MS (ESIpos): m/z=614 [M+H]+

The title compound (80 mg) was separated into enantiomers by chiral HPLC, followed by flash chromatography, to give enantiomer 1 (20 mg, see Example 1-77) and enantiomer 2 (18 mg, see Example 1-78).

Preparative chiral HPLC method: Instrument: Sepiatec: Prep SFC100; column: Chiralpak IC 5 μm 250×30 mm; eluent A: CO$_2$, eluent B: 2-propanol+0.4 Vol-% diethylamine (99%); isocratic: 23% B; flow 100.0 ml/min temperature: 40° C.; BPR: 150 bar; MWD @ 254 nm Analytical chiral HPLC method: Instrument: Agilent: 1260, Aurora SFC-Module; column: Chiralpak IC 5 μm 100×4.6 mm; eluent A: CO$_2$, eluent B: 2-propanol+0.2 Vol-% diethylamine (99%); isocratic: 23% B; flow 4.0 ml/min; temperature: 37.5° C.; BPR: 100 bar; MWD @ 254 nm Example 1-77

(E/Z)-1-methyl-7-[3-(naphthalen-1-yloxy)propyl]-3-(phenoxymethyl)-1,10,13,15-tetrahydropyrazolo[4',3':9,10][1,6]oxazacycloundecino[8,7,6-hi]indole-8-carboxylic acid (Enantiomer 1)

For the preparation of the racemic title compound see Example 1-76. After separation of enantiomers by preparative chiral HPLC (method see Example 1-76), the obtained product was further purified by flash chromatography (dichloromethane/methanol gradient, 3%→10% methanol) to give the title compound (20 mg).

Analytical chiral HPLC (method see Example 1-76): R$_t$=3.36 min.

¹H-NMR (400 MHz, DMSO-d6) δ[ppm]: 1.231 (1.32), 2.167 (1.09), 2.178 (1.11), 2.327 (0.53), 2.523 (1.02), 2.669 (0.51), 3.258 (0.52), 3.271 (0.64), 3.290 (0.99), 3.333 (8.63), 3.357 (0.87), 3.373 (0.52), 3.484 (0.68), 3.515 (1.20), 3.545 (0.78), 3.787 (0.69), 3.799 (0.83), 3.820 (0.66), 3.831 (0.64), 3.948 (16.00), 4.052 (0.63), 4.059 (0.69), 4.075 (1.10), 4.098 (0.62), 4.113 (1.14), 4.127 (0.68), 4.137 (0.63), 4.227 (1.86), 4.262 (1.97), 4.426 (2.20), 4.455 (2.64), 4.662 (2.66), 4.680 (0.64), 4.691 (2.32), 4.705 (0.75), 4.718 (0.76), 4.738 (2.35), 4.772 (1.89), 5.028 (0.51), 5.054 (1.07), 5.080 (1.49), 5.126 (0.75), 5.158 (0.45), 5.168 (0.48), 5.186 (0.64), 5.196 (0.67), 5.760 (3.10), 6.589 (3.45), 6.608 (3.68), 6.610 (2.98), 6.721 (1.05), 6.739 (2.26), 6.758 (1.31), 6.782 (2.00), 6.793 (1.97), 6.796 (2.22), 6.800 (2.31), 6.811 (2.21), 6.813 (2.11), 6.957 (1.79), 6.977 (2.23), 6.994 (1.51), 7.038 (2.86), 7.043 (1.06), 7.056 (3.30), 7.060 (3.34), 7.073 (0.81), 7.078 (2.28), 7.339 (1.41), 7.359 (2.61), 7.379 (1.95), 7.432 (2.64), 7.453 (1.63), 7.481 (0.42), 7.485 (0.63), 7.498 (1.59), 7.502 (1.51), 7.507 (1.78), 7.515 (3.46), 7.522 (1.80), 7.527 (1.60), 7.531 (1.76), 7.544 (0.66), 7.549 (0.40), 7.674 (1.80), 7.677 (1.89), 7.694 (1.71), 7.697 (1.69), 7.850 (1.58), 7.858 (0.87), 7.868 (1.47), 7.873 (1.35), 8.210 (1.35), 8.215 (1.34), 8.234 (1.31).

Example 1-78

(E/Z)-1-methyl-7-[3-(naphthalen-1-yloxy)propyl]-3-(phenoxymethyl)-1,10,13,15-tetrahydropyrazolo[4',3':9,10][1,6]oxazacycloundecino[8,7,6-hi]indole-8-carboxylic acid (Enantiomer 2)

For the preparation of the racemic title compound see Example 1-76. After separation of enantiomers by preparative chiral HPLC (method see Example 1-76); the obtained product was further purified by flash chromatography (dichloromethane/methanol gradient, 3%→10% methanol) to give the title compound (18 mg).

Analytical chiral HPLC (method see Example 1-76): $R_t$=4.32 min.

$^1$H-NMR (400 MHz, DMSO-d6) δ[ppm]: 1.071 (2.92), 1.089 (6.43), 1.106 (3.14), 1.232 (1.22), 1.907 (1.10), 2.168 (1.08), 2.179 (1.10), 2.323 (1.22), 2.327 (1.70), 2.331 (1.22), 2.518 (6.20), 2.523 (4.08), 2.665 (1.25), 2.669 (1.73), 2.673 (1.19), 3.252 (0.48), 3.266 (0.62), 3.287 (0.99), 3.354 (2.07), 3.371 (3.40), 3.389 (3.34), 3.407 (0.99), 3.485 (0.68), 3.516 (1.22), 3.547 (0.79), 3.787 (0.68), 3.799 (0.82), 3.820 (0.68), 3.832 (0.59), 3.948 (16.00), 4.054 (0.62), 4.062 (0.65), 4.077 (1.13), 4.099 (0.68), 4.114 (1.16), 4.129 (0.68), 4.138 (0.65), 4.228 (1.84), 4.262 (2.01), 4.428 (2.18), 4.456 (2.61), 4.657 (2.32), 4.671 (0.57), 4.686 (2.04), 4.696 (0.68), 4.711 (0.65), 4.736 (2.63), 4.771 (1.90), 5.028 (0.68), 5.058 (1.02), 5.085 (0.91), 5.138 (0.57), 5.155 (0.54), 5.166 (0.51), 5.184 (0.65), 5.195 (0.68), 6.592 (3.28), 6.611 (3.54), 6.721 (1.08), 6.739 (2.38), 6.758 (1.36), 6.784 (3.00), 6.803 (3.51), 6.952 (1.39), 6.971 (1.90), 6.989 (1.16), 7.039 (3.00), 7.058 (3.40), 7.061 (3.40), 7.074 (0.88), 7.079 (2.35), 7.338 (1.39), 7.359 (2.61), 7.378 (2.04), 7.431 (2.66), 7.452 (1.67), 7.481 (0.42), 7.485 (0.59), 7.497 (1.56), 7.502 (1.50), 7.507 (1.81), 7.514 (3.51), 7.522 (1.76), 7.526 (1.61), 7.531 (1.73), 7.543 (0.68), 7.548 (0.42), 7.667 (1.47), 7.687 (1.36), 7.850 (1.59), 7.858 (0.88), 7.868 (1.53), 7.873 (1.39), 8.209 (1.36), 8.215 (1.33), 8.233 (1.30).

Example 1-79

1-methyl-7-[3-(naphthalen-1-yloxy)propyl]-3-(phenoxymethyl)-1,10,11,12,13,15-hexahydropyrazolo[4',3':9,10][1,6]oxazacycloundecino[8,7,6-hi]indole-8-carboxylic acid (Enantiomer 1)

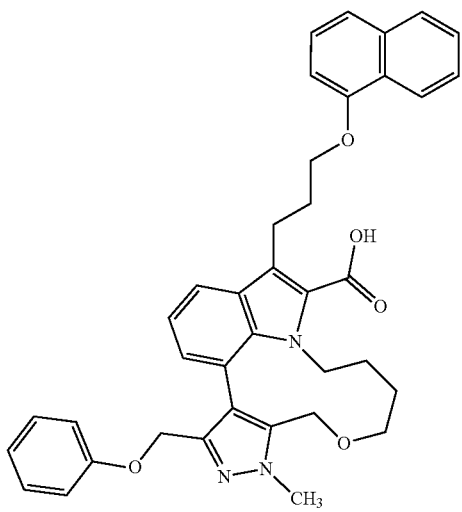 [SMILES: Cn1nc(COc2ccccc2)c2c1COCCCCn1c(C(=O)O)c(CCCOc3cccc4ccccc34)c3cccc-2c31]

To a solution of ethyl 1-methyl-7-[3-(naphthalen-1-yloxy)propyl]-3-(phenoxymethyl)-1,10,11,12,13,15-hexahydropyrazolo[4',3':9,10][1,6]oxazacycloundecino[8,7,6-hi]indole-8-carboxylate (enantiomer 1) (see Intermediate 1-134; 20.4 mg, 31.7 μmol) in THF (1.3 ml) and ethanol (920 μl) was added a solution of lithium hydroxide in water (630 μl, 1.0 M, 630 μmol). The reaction was stirred for 20 days at room temperature. For work-up, aqueous 1 N HCl was added until a pH of 2 was reached. The mixture was poured into water and was extracted with dichloromethane. The combined organic phases were washed with brine and dried over sodium sulfate. After filtration and removal of the solvent the crude product was purified by flash chromatography (dichloromethane/methanol gradient, 2%→10% methanol) to give the title compound (10 mg).

LC-MS (Method 2): Rt=0.96 min; MS (ESIpos): m/z=616 [M+H]$^+$ $^1$H-NMR (400 MHz, CHLOROFORM-d) δ [ppm]: 0.000 (0.61), 0.009 (16.00), 0.018 (0.58), 0.749 (0.56), 0.768 (0.64), 0.775 (0.65), 0.792 (0.73), 0.801 (0.74), 0.820 (1.24), 0.834 (0.65), 1.072 (0.64), 1.092 (0.61), 1.194 (7.94), 1.224 (5.80), 1.263 (0.79), 1.273 (3.56), 1.363 (1.03), 1.367 (0.65), 1.372 (1.31), 1.519 (0.56), 2.231 (0.43), 2.249 (1.12), 2.266 (1.70), 2.282 (1.10), 2.300 (0.56), 2.875 (0.41), 2.896 (0.58), 2.915 (0.41), 3.326 (0.60), 3.341 (0.60), 3.360 (0.98), 3.378 (0.44), 3.411 (0.48), 3.429 (0.99), 3.448 (0.81), 3.463 (0.96), 3.477 (0.61), 3.488 (0.58), 3.970 (15.70), 4.061 (0.89), 4.067 (1.00), 4.076 (1.76), 4.082 (1.74), 4.091 (1.04), 4.097 (0.91), 4.104 (0.68), 4.140 (0.69), 4.169 (0.44), 4.419 (1.42), 4.453 (2.20), 4.526 (0.82), 4.538 (2.63), 4.562 (0.74), 4.572 (1.81), 4.639 (2.02), 4.667 (3.04), 4.765 (3.17), 4.793 (2.19), 6.596 (2.55), 6.598 (3.19), 6.618 (3.73), 6.621 (3.97), 6.641 (1.83), 6.721 (0.95), 6.739 (2.11), 6.757 (1.19), 6.842 (1.53), 6.844 (1.56), 6.859 (2.15), 6.862 (2.04), 6.930 (1.95), 6.936 (0.49), 6.950 (2.24), 6.968 (1.46), 7.026 (2.64), 7.031 (0.96), 7.045 (3.00), 7.048 (3.13), 7.061 (0.81), 7.066 (2.18), 7.230 (1.37), 7.251 (2.42), 7.270 (1.96), 7.323 (2.36), 7.344 (1.44), 7.396 (0.50), 7.405 (3.34), 7.413 (2.41), 7.420 (2.12), 7.429 (3.56), 7.439 (0.52), 7.666 (1.79), 7.669 (1.84), 7.686 (1.69), 7.689 (1.58), 7.716 (1.28), 7.724 (1.32), 7.730 (0.84), 7.733 (0.81), 7.740 (1.10), 8.294 (1.16), 8.303 (0.70), 8.310 (0.96), 8.319 (1.08).

Example 1-80

1-methyl-7-[3-(naphthalen-1-yloxy)propyl]-3-(phenoxymethyl)-1,10,11,12,13,15-hexahydropyrazolo[4',3':9,10][1,6]oxazacycloundecino[8,7,6-hi]indole-8-carboxylic acid (Enantiomer 2)

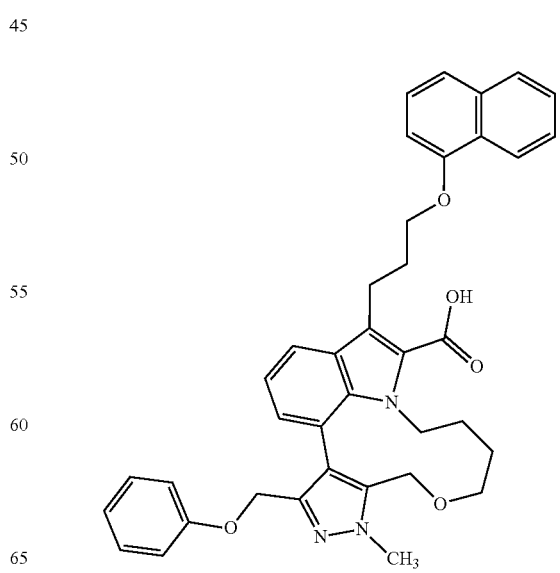

867

To a solution of ethyl 1-methyl-7-[3-(naphthalen-1-yloxy)propyl]-3-(phenoxymethyl)-1,10,11,12,13,15-hexahydropyrazolo[4',3':9,10][1,6]oxazacycloundecino[8,7,6-hi]indole-8-carboxylate (enantiomer 2) (see Intermediate 1-135; 25.8 mg) in THF (1.6 ml) and ethanol (1.2 ml, 20 mmol) was added a solution of lithium hydroxide in water (800 µl, 1.0 M, 800 µmol). The reaction was stirred for 20 days at room temperature. For work-up, aqueous 1 N HCl was added until a pH of 2 was reached. The mixture was poured into water and was extracted with dichloromethane. The combined organic phases were washed with brine and dried over sodium sulfate. After filtration and removal of the solvent the crude product was purified by flash chromatography (dichloromethane/methanol gradient, 2%→10% methanol) to give the title compound (13 mg).

LC-MS (Method 2): Rt=0.95 min; MS (ESIpos): m/z=616 [M+H]$^+$ $^1$H-NMR (400 MHz, CHLOROFORM-d) δ [ppm]: 0.000 (15.55), 0.739 (0.72), 0.764 (0.83), 0.783 (0.90), 0.792 (0.93), 0.810 (1.46), 0.825 (0.79), 1.064 (0.80), 1.082 (0.76), 1.184 (9.55), 1.214 (5.89), 1.253 (1.03), 1.264 (3.74), 1.353 (1.13), 1.362 (1.33), 1.510 (0.70), 2.241 (1.41), 2.256 (2.05), 2.274 (1.36), 2.291 (0.63), 2.866 (0.49), 2.887 (0.74), 2.906 (0.51), 3.317 (0.71), 3.331 (0.74), 3.350 (1.14), 3.369 (0.52), 3.402 (0.58), 3.421 (1.18), 3.439 (1.03), 3.453 (1.18), 3.468 (0.78), 3.961 (16.00), 4.052 (1.09), 4.058 (1.28), 4.066 (2.12), 4.072 (2.10), 4.081 (1.28), 4.087 (1.16), 4.129 (0.83), 4.158 (0.55), 4.410 (1.55), 4.443 (2.46), 4.516 (1.03), 4.529 (2.90), 4.552 (0.92), 4.562 (1.97), 4.630 (2.12), 4.658 (3.17), 4.757 (3.28), 4.785 (2.26), 6.589 (3.46), 6.608 (4.13), 6.611 (4.40), 6.632 (2.18), 6.712 (0.97), 6.730 (2.17), 6.748 (1.25), 6.832 (1.67), 6.835 (1.72), 6.850 (2.36), 6.852 (2.26), 6.921 (1.96), 6.941 (2.36), 6.959 (1.43), 7.017 (2.70), 7.035 (3.38), 7.038 (3.47), 7.057 (2.24), 7.221 (1.40), 7.241 (2.68), 7.260 (2.03), 7.314 (2.72), 7.335 (1.67), 7.387 (0.59), 7.396 (3.32), 7.404 (2.70), 7.412 (2.52), 7.420 (3.63), 7.429 (0.65), 7.657 (1.93), 7.659 (2.03), 7.677 (1.82), 7.680 (1.80), 7.707 (1.48), 7.714 (1.44), 7.721 (1.00), 7.730 (1.30), 8.285 (1.30), 8.293 (0.90), 8.301 (1.16), 8.310 (1.20).

Example 1-81

(rac)-7,9-dimethyl-1-[3-(naphthalen-1-yloxy) propyl]-11-(phenoxymethyl)-4,5,6,7,8,9-hexahydropyrazolo[3',4':7,8][1,5]diazecino[9,10,1-hi]indole-2-carboxylic acid

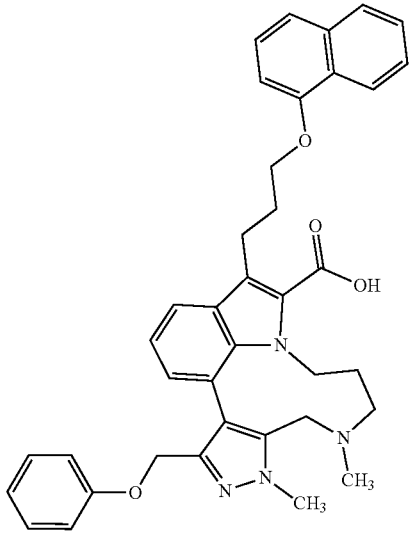 [SMILES: CN1CCCn2c(C(=O)O)c(CCCOc3cccc4ccccc34)c3cccc(c32)-c2c(COc3ccccc3)nn(C)c2C1]

868

To a solution of (rac)-ethyl 7,9-dimethyl-1-[3-(naphthalen-1-yloxy)propyl]-11-(phenoxymethyl)-4,5,6,7,8,9-hexahydropyrazolo[3',4':7,8][1,5]diazecino[9,10,1-hi]indole-2-carboxylate (see Intermediate 1-139; 130 mg, 202 µmol) in THF (8.2 ml) and ethanol (5.9 ml) was added a solution of lithium hydroxide in water (4.0 ml, 1.0 M, 4.0 mmol). The reaction mixture was stirred for 24 hours at 50° C. For work-up, aqueous 1N HCl was added until a pH of 5-6 was reached. The mixture was poured into water and was extracted with dichloromethane. The combined organic phases were washed with brine and dried over sodium sulfate. After filtration and removal of the solvent the crude product was purified by flash chromatography (dichloromethane/methanol gradient, 2%→10% methanol) to give the title compound (81 mg).

LC-MS (Method 2): Rt=1.04 min; MS (ESIpos): m/z=615 [M+H]$^+$

The title compound (81 mg) was separated into enantiomers by chiral HPLC, followed by flash chromatography, to give enantiomer 1 (17 mg, see Example 1-82) and enantiomer 2 (9 mg, see Example 1-83).

Preparative chiral HPLC method: Instrument: Sepiatec: Prep SFC100; column: Chiralpak ID 5 µm 250×30 mm; eluent A: CO$_2$, eluent B: 2-propanol+0.4 Vol-% diethylamine (99%); isocratic: 35% B; flow 100.0 ml/min; temperature: 40° C.; BPR: 150 bar; MWD @ 254 nm Analytical chiral HPLC method: Instrument: Agilent: 1260, Aurora SFC-Module; column: Chiralpak ID 5 µm 100×4.6 mm; eluent A: CO$_2$, eluent B: 2-propanol+0.2 Vol-% diethylamine (99%); isocratic: 35% B; flow 4.0 ml/min; temperature: 37.5° C.; BPR: 100 bar; MWD @ 254 nm Example 1-82

7,9-dimethyl-1-[3-(naphthalen-1-yloxy)propyl]-11-(phenoxymethyl)-4,5,6,7,8,9-hexahydropyrazolo[3',4':7,8][1,5]diazecino[9,10,1-hi]indole-2-carboxylic acid (Enantiomer 1)

For the preparation of the racemic title compound see Example 1-81. After separation of enantiomers by preparative chiral HPLC (method see Example 1-81), the obtained product was further purified by flash chromatography (dichloromethane/methanol gradient, 0.5%→10% methanol) to give the title compound (17 mg).

Analytical chiral HPLC (method see Example 1-81): R$_t$=2.47 min.

$^1$H-NMR (400 MHz, DMSO-d6) δ[ppm]: 0.851 (0.42), 1.232 (2.23), 1.255 (0.59), 1.477 (0.64), 1.590 (0.57), 1.842 (0.57), 1.864 (0.59), 1.876 (0.70), 1.897 (0.61), 1.907 (0.85), 2.166 (1.43), 2.183 (2.53), 2.197 (13.20), 2.295 (0.65), 2.327 (1.43), 2.331 (1.17), 2.344 (0.57), 2.665 (0.67), 2.669 (0.89), 2.673 (0.65), 2.993 (1.67), 3.029 (1.75), 3.233 (0.71), 3.247 (0.76), 3.266 (1.14), 3.285 (0.67), 3.374 (0.91), 3.393 (0.42), 3.633 (1.89), 3.669 (2.11), 3.696 (0.86), 3.722 (0.55), 3.891 (16.00), 4.134 (1.37), 4.150 (2.66), 4.165 (1.38), 4.379 (0.80), 4.403 (0.49), 4.415 (0.74), 4.738 (7.91), 5.760 (5.53), 6.651 (3.72), 6.671 (4.03), 6.757 (1.14), 6.775 (2.44), 6.794 (1.38), 6.823 (2.16), 6.842 (2.29), 6.925 (1.00), 6.938 (3.17), 6.942 (4.94), 6.961 (2.57), 6.979 (0.89), 7.071 (2.93), 7.089 (3.73), 7.092 (3.67), 7.111 (2.29), 7.341 (1.40), 7.361 (2.77), 7.381 (2.02), 7.432 (2.97), 7.452 (1.78), 7.479 (0.49), 7.484 (0.65), 7.497 (1.72), 7.501 (1.65), 7.507 (1.84), 7.514 (3.57), 7.521 (1.95), 7.526 (1.75), 7.530 (1.78), 7.543 (0.68), 7.547 (0.45), 7.661 (1.62), 7.666 (1.64), 7.679 (1.53), 7.684

(1.50), 7.849 (1.80), 7.856 (1.03), 7.866 (1.62), 7.872 (1.49), 8.215 (1.55), 8.220 (1.52), 8.238 (1.47).

Example 1-83

7,9-dimethyl-1-[3-(naphthalen-1-yloxy)propyl]-11-(phenoxymethyl)-4,5,6,7,8,9-hexahydropyrazolo[3',4':7,8][1,5]diazecino[9,10,1-hi]indole-2-carboxylic acid (Enantiomer 2)

For the preparation of the racemic title compound see Example 1-81. After separation of enantiomers by preparative chiral HPLC (method see Example 1-81), the obtained product was further purified by flash chromatography (dichloromethane/methanol gradient, 2.5%→10% methanol) to give the title compound (9 mg).
Analytical chiral HPLC (method see Example 1-81): $R_t$=7.07 min.
$^1$H-NMR (400 MHz, DMSO-d6) δ[ppm]: 0.851 (0.45), 1.232 (2.45), 1.478 (0.74), 1.589 (0.66), 1.842 (0.63), 1.863 (0.69), 1.875 (0.77), 1.897 (0.69), 1.907 (0.80), 2.166 (1.62), 2.197 (13.75), 2.294 (0.74), 2.327 (1.53), 2.344 (0.65), 2.669 (0.92), 2.993 (1.74), 3.029 (1.88), 3.232 (0.76), 3.247 (0.83), 3.266 (1.23), 3.284 (0.72), 3.374 (1.00), 3.393 (0.46), 3.632 (1.94), 3.668 (2.25), 3.696 (0.94), 3.722 (0.62), 3.891 (16.00), 4.135 (1.54), 4.149 (2.94), 4.165 (1.56), 4.378 (0.89), 4.415 (0.83), 4.737 (8.14), 5.759 (4.76), 6.651 (3.88), 6.670 (4.22), 6.757 (1.14), 6.775 (2.48), 6.793 (1.40), 6.823 (2.28), 6.841 (2.44), 6.925 (1.02), 6.943 (5.07), 6.961 (2.57), 6.979 (0.89), 7.071 (2.90), 7.090 (3.98), 7.110 (2.31), 7.341 (1.37), 7.361 (2.77), 7.380 (1.99), 7.431 (3.08), 7.452 (1.90), 7.483 (0.69), 7.497 (1.74), 7.501 (1.77), 7.506 (1.97), 7.513 (3.50), 7.520 (2.08), 7.525 (1.91), 7.530 (1.87), 7.542 (0.71), 7.661 (1.70), 7.666 (1.71), 7.680 (1.65), 7.684 (1.59), 7.849 (1.90), 7.867 (1.71), 7.872 (1.59), 8.214 (1.60), 8.220 (1.62), 8.238 (1.60).

Example 1-84

(rac)-1-[3-(4-chloro-3,5-dimethylphenoxy)propyl]-7,9-dimethyl-11-(phenoxymethyl)-4,5,6,7,8,9-hexahydropyrazolo[3',4':7,8][1,5]diazecino[9,10,1-hi]indole-2-carboxylic acid

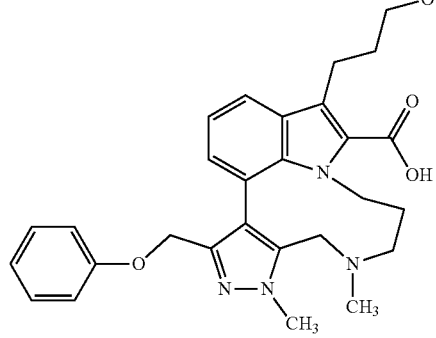

To a solution of (rac)-ethyl 1-[3-(4-chloro-3,5-dimethylphenoxy)propyl]-7,9-dimethyl-11-(phenoxymethyl)-4,5,6,7,8,9-hexahydropyrazolo[3',4':7,8][1,5]diazecino[9,10,1-hi]indole-2-carboxylate (see Intermediate 1-144; 118 mg, 180 µmol) in THF (7.7 ml) and ethanol (3.9 ml) was added a solution of lithium hydroxide in water (3.6 ml, 1.0 M, 3.6 mmol). The reaction mixture was stirred for 18 hours at 40° C. and for 6 hours at 50° C. For work-up, the reaction mixture was concentrated under reduced pressure and the residue was purified by flash chromatography (dichloromethane/methanol gradient, 0%→10% methanol) to give the title compound (83 mg) as a racemic mixture.
LC-MS (Method 2): Rt=1.06 min; MS (ESIpos): m/z=627 [M+H]$^+$
The title compound (83 mg) was separated into enantiomers by chiral HPLC, followed by flash chromatography, to give enantiomer 1 (20 mg, see Example 1-85) and enantiomer 2 (15 mg, see Example 1-86).
Preparative chiral HPLC method: Instrument: Sepiatec: Prep SFC100; column: Chiralpak ID 5 µm 250×30 mm; eluent A: CO$_2$, eluent B: 2-propanol+0.4 Vol-% diethylamine (99%); isocratic: 35% B; flow 100.0 ml/min; temperature: 40° C.; BPR: 150 bar; MWD @ 254 nm
Analytical chiral HPLC method: Instrument: Agilent; 1260, Aurora SFC-Module; column: Chiralpak ID 5 µm 100×4.6 mm; eluent A: CO$_2$, eluent B: 2-propanol+0.2 Vol-% diethylamine (99%); isocratic: 35% B; flow 4.0 ml/min; temperature: 37.5° C.; BPR: 100 bar; MWD @ 254 nm Example 1-85

1-[3-(4-chloro-3,5-dimethylphenoxy)propyl]-7,9-dimethyl-11-(phenoxymethyl)-4,5,6,7,8,9-hexahydropyrazolo[3',4':7,8][1,5]diazecino[9,10,1-hi]indole-2-carboxylic acid (Enantiomer 1)

For the preparation of the racemic title compound see Example 1-84. After separation of enantiomers by preparative chiral HPLC (method see Example 1-84), the obtained product was further purified by flash chromatography (dichloromethane/methanol gradient, 3%→10% methanol) to give after lyophilisation the title compound (20 mg).
Analytical chiral HPLC (method see Example 1-84): $R_t$=1.81 min.
$^1$H-NMR (400 MHz, DMSO-d6) δ[ppm]: 1.232 (1.53), 1.985 (0.78), 2.002 (1.13), 2.019 (0.79), 2.197 (5.59), 2.252 (16.00), 2.323 (0.61), 2.327 (0.61), 2.332 (0.52), 3.006 (0.75), 3.042 (0.81), 3.114 (0.41), 3.131 (0.60), 3.196 (0.58), 3.645 (0.94), 3.681 (1.06), 3.891 (8.63), 3.910 (1.99), 3.926 (0.92), 4.348 (0.44), 4.384 (0.41), 4.748 (4.12), 5.760 (1.42), 6.644 (1.93), 6.664 (2.12), 6.718 (4.66), 6.768 (0.58), 6.787 (1.23), 6.805 (0.69), 6.936 (0.78), 6.951 (1.37), 6.982 (1.09), 7.001 (1.27), 7.019 (0.62), 7.064 (1.47), 7.083 (1.95), 7.104 (1.14), 7.624 (1.01), 7.641 (0.95).

Example 1-86

1-[3-(4-chloro-3,5-dimethylphenoxy)propyl]-7,9-dimethyl-11-(phenoxymethyl)-4,5,6,7,8,9-hexahydropyrazolo[3',4':7,8][1,5]diazecino[9,10,1-hi]indole-2-carboxylic acid (Enantiomer 2)

For the preparation of the racemic title compound see Example 1-84. After separation of enantiomers by preparative chiral HPLC (method see Example 1-84), the obtained product was further purified by flash chromatography (dichloromethane/methanol gradient, 3%→10% methanol) to give after lyophilisation the title compound (15 mg).
Analytical chiral HPLC (method see Example 1-84): $R_t$=3.99 min.
$^1$H-NMR (400 MHz, DMSO-d6) δ[ppm]: 1.167 (0.42), 1.232 (1.91), 1.550 (0.40), 1.985 (0.80), 2.002 (1.16), 2.019

(0.82), 2.197 (5.71), 2.252 (16.00), 2.323 (0.58), 2.327 (0.56), 2.331 (0.49), 3.006 (0.77), 3.043 (0.83), 3.114 (0.41), 3.131 (0.60), 3.196 (0.58), 3.214 (0.40), 3.644 (0.95), 3.680 (1.06), 3.891 (8.47), 3.910 (2.01), 3.926 (0.94), 4.346 (0.47), 4.383 (0.44), 4.748 (4.12), 5.759 (1.04), 6.644 (1.95), 6.663 (2.10), 6.718 (4.68), 6.768 (0.57), 6.786 (1.22), 6.804 (0.69), 6.937 (0.79), 6.951 (1.39), 6.982 (1.07), 7.001 (1.29), 7.019 (0.61), 7.064 (1.47), 7.083 (1.94), 7.104 (1.12), 7.625 (1.04), 7.642 (0.95).

Example 1-87

(rac)-7,9-dimethyl-11-{[4-(morpholin-4-yl)phenoxy]methyl}-1-[3-(naphthalen-1-yloxy)propyl]-4,5,6,7,8,9-hexahydropyrazolo[3',4':7,8][1,5]diazecino[9,10,1-hi]indole-2-carboxylic acid

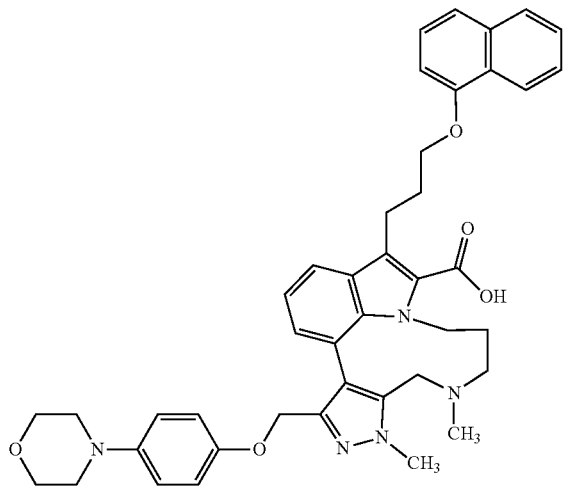 [SMILES: CN1CCCn2c(C(=O)O)c(CCCOc3cccc4ccccc34)c3cccc(c32)-c2c(COc3ccc(N4CCOCC4)cc3)nn(C)c2C1]

To a solution of (rac)-ethyl 7,9-dimethyl-11-{[4-(morpholin-4-yl)phenoxy]methyl}-1-[3-(naphthalen-1-yloxy)propyl]-4,5,6,7,8,9-hexahydropyrazolo[3',4':7,8][1,5]diazecino[9,10,1-hi]indole-2-carboxylate (see Intermediate 1-151; 500 mg, 687 µmol) in THF (12 ml) and ethanol (12 ml) was added a solution of lithium hydroxide in water (12 ml, 1.0 M, 12 mmol). The reaction mixture was stirred for 16 hours at 45° C. For work-up, the reaction mixture was concentrated under reduced pressure and the residue was purified by flash chromatography (dichloromethane/methanol gradient, 0%→10% methanol) to give the title compound (280 mg) as a racemic mixture.

LC-MS (Method 2): Rt=0.91 min; MS (ESIpos): m/z=700 [M+H]$^+$

The title compound (280 mg) was separated into enantiomers by chiral HPLC, followed by flash chromatography, to give enantiomer 1 (72 mg, see Example 1-88) and enantiomer 2 (71 mg, see Example 1-89).

Preparative chiral HPLC method: Instrument: Sepiatec: Prep SFC100; column: Chiralpak ID 5 µm 250×30 mm; eluent A: CO$_2$, eluent B: 2-propanol+0.4 Vol-% diethylamine (99%); isocratic: 52% B; flow 100.0 ml/min: temperature: 40° C.; BPR: 150 bar; MWD @ 254 nm.

Analytical chiral HPLC method: Instrument: Agilent: 1260, Aurora SFC-Module; column: Chiralpak ID 5 µm 100×4.6 mm; eluent A: CO$_2$, eluent B: 2-propanol+0.2 Vol-% diethylamine (99%); isocratic: 52% B; flow 4.0 ml/min; temperature: 37.5° C.; BPR: 100 bar; MWD @ 254 nm.

Example 1-88

(+)-7,9-dimethyl-11-{[4-(morpholin-4-yl)phenoxy]methyl}-1-[3-(naphthalen-1-yloxy) propyl]-4,5,6,7,8,9-hexahydropyrazolo[3',4':7,8][1,5]diazecino[9,10,1-hi]indole-2-carboxylic acid (Enantiomer 1)

For the preparation of the racemic title compound see Example 1-87. After separation of enantiomers by preparative chiral HPLC (method see Example 1-87), the obtained product was further purified by flash chromatography (dichloromethane/ethanol gradient, 0%→30% ethanol) to give after lyophilisation the title compound (72 mg).

Analytical chiral HPLC (method see Example 1-87): R$_t$=1.45 min.

Specific optical rotation (Method O1): +17.1° (c=1.0 g/100 ml in DMSO)

$^1$H-NMR (400 MHz, DMSO-d6) δ[ppm]: 1.232 (0.81), 1.467 (0.52), 1.583 (0.46), 1.840 (0.48), 1.862 (0.50), 1.873 (0.57), 1.897 (0.48), 2.196 (12.56), 2.213 (1.44), 2.289 (0.54), 2.304 (0.55), 2.322 (1.29), 2.326 (1.55), 2.331 (1.09), 2.336 (0.72), 2.518 (5.03), 2.522 (3.31), 2.539 (0.41), 2.659 (0.44), 2.664 (0.87), 2.668 (1.15), 2.673 (0.83), 2.826 (4.12), 2.838 (5.07), 2.850 (4.33), 2.987 (1.52), 3.024 (1.59), 3.236 (0.63), 3.252 (0.67), 3.270 (0.98), 3.289 (0.57), 3.353 (1.39), 3.370 (0.76), 3.386 (0.72), 3.610 (4.66), 3.623 (6.58), 3.634 (4.72), 3.660 (2.00), 3.691 (0.50), 3.880 (16.00), 4.136 (1.35), 4.152 (2.76), 4.168 (1.33), 4.337 (0.74), 4.348 (0.48), 4.362 (0.44), 4.373 (0.68), 4.645 (0.63), 4.674 (3.68), 4.681 (3.53), 4.709 (0.63), 6.488 (3.72), 6.511 (4.90), 6.626 (5.14), 6.644 (1.37), 6.649 (3.66), 6.823 (1.92), 6.841 (2.07), 6.910 (1.07), 6.914 (1.22), 6.928 (2.40), 6.931 (2.18), 6.949 (2.20), 6.968 (2.35), 6.986 (1.13), 7.341 (1.41), 7.362 (2.59), 7.381 (2.03), 7.433 (2.70), 7.453 (1.65), 7.479 (0.48), 7.484 (0.65), 7.497 (1.66), 7.501 (1.48), 7.507 (1.76), 7.514 (3.50), 7.521 (1.79), 7.527 (1.63), 7.531 (1.74), 7.544 (0.72), 7.549 (0.46), 7.673 (1.61), 7.676 (1.65), 7.692 (1.54), 7.695 (1.46), 7.849 (1.63), 7.857 (0.92), 7.868 (1.63), 7.873 (1.39), 8.214 (1.44), 8.220 (1.37), 8.239 (1.31).

Example 1-89

(−)-7,9-dimethyl-11-{[4-(morpholin-4-yl)phenoxy]methyl}-1-[3-(naphthalen-1-yloxy)propyl]-4,5,6,7,8,9-hexahydropyrazolo[3',4':7,8][1,5]diazecino[9,10,1-hi]indole-2-carboxylic acid (Enantiomer 2)

For the preparation of the racemic title compound see Example 1-87. After separation of enantiomers by preparative chiral HPLC (method see Example 1-87), the obtained product was further purified by flash chromatography (dichloromethane/ethanol gradient, 0%→30% ethanol) to give after lyophilisation the title compound (71 mg).

Analytical chiral HPLC (method see Example 1-87): R$_t$=3.58 min.

Specific optical rotation (Method O1): −17.1° (c=1.0 g/100 ml in DMSO)

$^1$H-NMR (400 MHz, DMSO-d6) δ[ppm]: 1.209 (0.57), 1.448 (0.49), 1.559 (0.44), 1.817 (0.46), 1.840 (0.48), 1.852 (0.56), 1.873 (0.46), 2.173 (12.24), 2.192 (1.31), 2.209 (0.43), 2.268 (0.51), 2.282 (0.54), 2.300 (1.20), 2.304 (1.43), 2.310 (0.99), 2.314 (0.64), 2.496 (4.16), 2.500 (2.74), 2.642 (0.79), 2.646 (1.03), 2.651 (0.76), 2.804 (4.04), 2.816 (4.93), 2.827 (4.30), 2.967 (1.45), 3.003 (1.51), 3.218 (0.62), 3.233 (0.62), 3.252 (0.97), 3.270 (0.54), 3.333 (1.15), 3.351 (0.67), 3.367 (0.69), 3.589 (4.62), 3.601 (6.19), 3.612 (4.75), 3.638 (1.89), 3.657 (0.51), 3.673 (0.49), 3.681 (0.44), 3.858 (16.00), 4.115 (1.31), 4.130 (2.68), 4.146 (1.30), 4.310 (0.77), 4.320 (0.48), 4.334 (0.44), 4.346 (0.72), 4.624 (0.69), 4.653 (3.55), 4.660 (3.50), 4.689 (0.69), 6.463 (3.99), 6.468 (1.28), 6.480 (1.54), 6.486 (5.27), 6.495 (0.53), 6.594 (0.57), 6.603 (5.32), 6.609 (1.46), 6.620 (1.33), 6.626 (3.84), 6.801 (1.91), 6.818 (2.05), 6.893 (1.15), 6.896 (1.38), 6.910 (2.64), 6.913 (2.46), 6.930 (2.51), 6.949 (2.55), 6.966 (1.25), 7.319 (1.49), 7.340 (2.68), 7.359 (2.14), 7.411 (2.71), 7.432 (1.66), 7.458 (0.51), 7.462 (0.67), 7.475 (1.74), 7.479 (1.49), 7.486 (1.86), 7.493 (3.63), 7.499 (1.86), 7.505 (1.64), 7.510 (1.82), 7.523 (0.74), 7.527 (0.48), 7.655 (1.74), 7.658 (1.79), 7.674 (1.66), 7.678 (1.61), 7.828 (1.63), 7.835 (0.90), 7.845 (1.64), 7.851 (1.38), 8.192 (1.48), 8.198 (1.38), 8.210 (0.80), 8.215 (1.33), 8.217 (1.35), 13.067 (0.44).

Example 1-90

(rac)-11-({[2-(2-methoxyphenyl)pyrimidin-5-yl]oxy}methyl)-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid

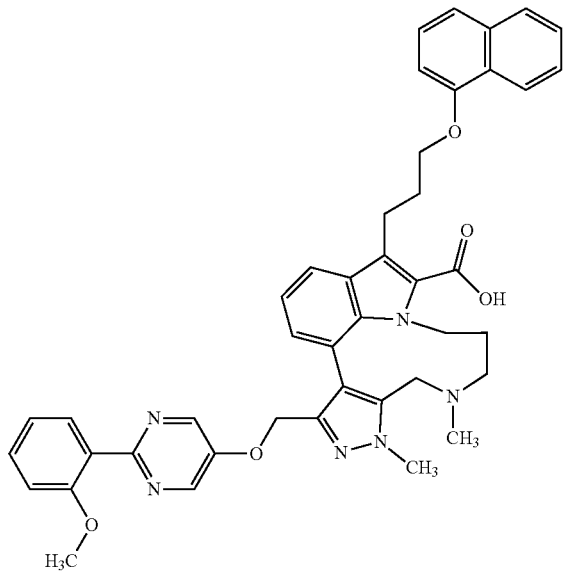 [SMILES: COc1ccccc1-c1ncc(OCc2nn(C)c3c2-c2cccc4c(CCCOc5cccc6ccccc56)c(C(=O)O)n(c24)CCCN(C)C3)cn1]

To a solution of (rac)-ethyl 11-({[2-(2-methoxyphenyl)pyrimidin-5-yl]oxy}methyl)-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylate (see Intermediate 1-159; 47.0 mg, 62.6 μmol) in THF (1.1 ml) and ethanol (1.1 ml) was added a solution of lithium hydroxide in water (1.1 ml, 1.0 M, 1.1 mmol). The reaction mixture was stirred for 18 hours at 45° C. For work-up, the reaction mixture was concentrated under reduced pressure and the residue was purified by flash chromatography (dichloromethane/methanol gradient, 0%→10% methanol) to give the title compound (42 mg) as a racemic mixture.

LC-MS (Method 2): Rt=0.92 min; MS (ESIpos): m/z=723 [M+H]$^+$

The title compound (42 mg) was separated into enantiomers by chiral HPLC to give enantiomer 1 (16 mg, see Example 1-91) and enantiomer 2 (26 mg, see Example 1-92).

Preparative chiral HPLC method: Instrument: Sepiatec: Prep SFC100; column: Chiralpak IA 5 μm 250×30 mm; eluent A: CO$_2$, eluent B: ethanol+0.4 Vol-% diethylamine (99%); isocratic: 40% B; flow 100.0 ml/min; temperature: 40° C.; BPR: 150 bar; MWD @ 254 nm Analytical chiral HPLC method: Instrument: Agilent: 1260, Aurora SFC-Module; column: Chiralpak IA 5 μm 100×4.6 mm; eluent A: CO$_2$, eluent B: ethanol+0.2 Vol-% diethylamine (99%); isocratic: 40% B; flow 4.0 ml/min; temperature: 37.5° C.; BPR: 100 bar; MWD @ 254 nm Example 1-91

11-({[2-(2-methoxyphenyl)pyrimidin-5-yl]oxy}methyl)-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid-N-ethylethanamine salt (Enantiomer 1)

See Example 1-90 for preparation and enantiomer separation.

Analytical chiral HPLC (method see Example 1-90): $R_t$=3.44 min.

¹H-NMR (400 MHz, DMSO-d6) δ[ppm]: 1.122 (2.48), 1.141 (5.13), 1.158 (2.52), 1.232 (1.12), 1.875 (0.41), 2.140 (0.87), 2.157 (1.28), 2.174 (0.87), 2.244 (5.62), 2.292 (0.45), 2.306 (0.45), 2.318 (1.07), 2.322 (2.15), 2.326 (2.85), 2.331 (2.03), 2.336 (1.03), 2.518 (10.01), 2.522 (6.61), 2.539 (0.41), 2.659 (0.87), 2.664 (1.86), 2.668 (2.52), 2.673 (1.78), 2.678 (0.79), 2.835 (0.58), 2.853 (1.70), 2.872 (1.65), 2.889 (0.54), 2.992 (0.99), 3.028 (1.03), 3.193 (0.45), 3.288 (0.95), 3.644 (1.20), 3.680 (1.16), 3.702 (16.00), 3.911 (11.49), 4.110 (1.07), 4.125 (2.11), 4.141 (0.99), 4.924 (0.62), 4.953 (1.41), 4.985 (1.86), 5.014 (0.87), 6.811 (1.36), 6.829 (1.49), 6.876 (0.79), 6.900 (0.79), 6.919 (0.95), 6.937 (0.45), 6.951 (0.91), 6.953 (0.91), 6.970 (1.74), 6.972 (1.70), 6.988 (0.99), 6.991 (0.99), 7.070 (1.49), 7.089 (1.74), 7.310 (1.07), 7.331 (1.86), 7.350 (1.41), 7.357 (1.03), 7.362 (1.12), 7.376 (1.07), 7.378 (1.07), 7.380 (1.20), 7.382 (1.07), 7.396 (0.83), 7.401 (1.03), 7.411 (2.11), 7.414 (2.23), 7.419 (1.57), 7.433 (2.40), 7.438 (1.32), 7.472 (0.50), 7.485 (1.20), 7.490 (1.07), 7.497 (1.24), 7.504 (2.36), 7.509 (1.24), 7.516 (1.12), 7.521 (1.24), 7.533 (0.50), 7.586 (0.62), 7.606 (0.58), 7.837 (1.20), 7.844 (0.66), 7.856 (1.16), 7.860 (0.95), 8.211 (1.03), 8.216 (0.99), 8.234 (0.95), 8.386 (4.42).

Example 1-92

11-({[2-(2-methoxyphenyl)pyrimidin-5-yl]oxy}methyl)-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid-N-ethylethanamine salt (Enantiomer 2)

See Example 1-90 for preparation and enantiomer separation.

Analytical Chiral HPLC (method see Example 1-90): $R_t$=5.35 min.

¹H-NMR (400 MHz, DMSO-d6) δ[ppm]: 1.108 (4.25), 1.131 (1.40), 1.149 (2.91), 1.167 (1.45), 1.232 (1.00), 1.453 (0.40), 1.865 (0.40), 1.876 (0.43), 2.142 (0.86), 2.160 (1.28), 2.177 (0.91), 2.230 (6.27), 2.293 (0.43), 2.305 (0.46), 2.323 (1.60), 2.327 (2.11), 2.331 (1.51), 2.337 (0.83), 2.518 (6.93), 2.523 (4.73), 2.660 (0.57), 2.665 (1.28), 2.669 (1.74), 2.673 (1.23), 2.678 (0.54), 2.873 (1.03), 2.891 (1.00), 2.999 (1.03), 3.036 (1.06), 3.198 (0.43), 3.217 (0.51), 3.593 (0.40), 3.646 (1.23), 3.683 (1.20), 3.701 (16.00), 3.913 (11.66), 4.111 (1.06), 4.126 (2.14), 4.142 (1.03), 4.938 (0.66), 4.967 (1.60), 4.992 (1.97), 5.021 (0.83), 6.813 (1.37), 6.832 (1.48), 6.889 (0.48), 6.905 (1.00), 6.919 (1.06), 6.938 (1.11), 6.951 (1.11), 6.954 (1.28), 6.970 (1.74), 6.972 (1.83), 6.989 (1.00), 6.991 (1.00), 7.070 (1.54), 7.089 (1.80), 7.313 (1.03), 7.334 (1.85), 7.353 (1.43), 7.357 (1.11), 7.362 (1.11), 7.376 (1.00), 7.380 (1.20), 7.382 (1.14), 7.396 (0.77), 7.401 (0.97), 7.414 (3.57), 7.417 (2.14), 7.433 (2.48), 7.436 (2.11), 7.475 (0.46), 7.488 (1.14), 7.492 (1.08), 7.499 (1.23), 7.506 (2.37), 7.512 (1.23), 7.519 (1.14), 7.523 (1.23), 7.536 (0.48), 7.613 (0.71), 7.631 (0.66), 7.840 (1.17), 7.847 (0.66), 7.858 (1.17), 7.863 (0.97), 8.213 (1.03), 8.218 (1.03), 8.236 (0.97), 8.368 (5.56).

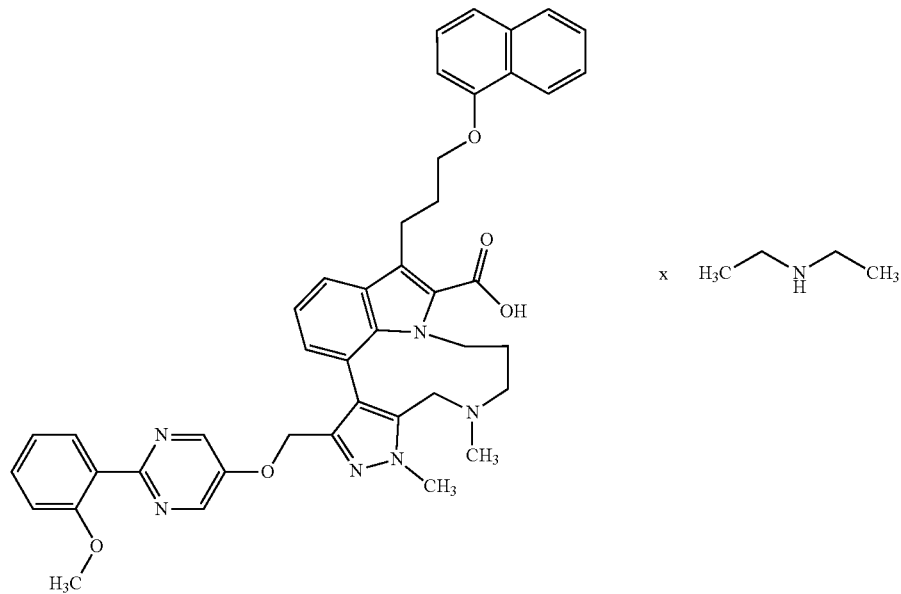

Example 1-93

(rac)-11-[(benzyloxy)methyl]-7,9-dimethyl-1-[3-(naphthalen-1-yloxy)propyl]-4,5,6,7,8,9-hexahydro-pyrazolo[3',4':7,8][1,5]diazecino[9,10,1-hi]indole-2-carboxylic acid

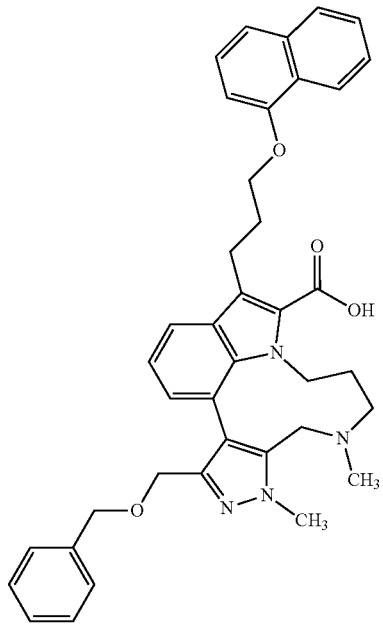 [SMILES: CN1CCCn2c(C(=O)O)c(CCCOc3cccc4ccccc34)c3cccc(c32)-c2c(COCc3ccccc3)nn(C)c2C1]

To a solution of (rac)-ethyl 11-[(benzyloxy)methyl]-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylate (see Intermediate 1-166; 70.0 mg, 107 µmol) in THF (5.2 ml) and ethanol (2.5 ml) was added a solution of lithium hydroxide in water (2.1 ml, 1.0 M, 2.1 mmol). The reaction mixture was stirred for 28 hours at 60° C. For work-up, the reaction mixture was concentrated under reduced pressure and the residue was purified by flash chromatography (dichloromethane/methanol gradient, 0%→10% methanol) to give the title compound (34 mg) as a racemic mixture.

LC-MS (Method 2): Rt=1.00 min; MS (ESIpos): m/z=629 [M+H]$^+$ $^1$H-NMR (400 MHz, DMSO-d6) δ[ppm]: 0.851 (0.63), 1.071 (1.76), 1.088 (4.01), 1.106 (1.84), 1.109 (0.85), 1.232 (3.30), 1.256 (0.60), 1.499 (0.66), 1.548 (0.47), 1.629 (0.58), 1.855 (0.60), 1.877 (0.63), 1.889 (0.71), 1.912 (0.63), 2.184 (1.59), 2.207 (16.00), 2.309 (0.66), 2.322 (1.73), 2.327 (2.20), 2.332 (1.54), 2.337 (0.85), 2.359 (0.52), 2.518 (5.94), 2.523 (4.40), 2.660 (0.49), 2.665 (1.10), 2.669 (1.57), 2.673 (1.10), 2.678 (0.47), 2.997 (1.92), 3.032 (2.06), 3.244 (0.41), 3.263 (0.85), 3.277 (0.96), 3.296 (1.65), 3.331 (12.92), 3.354 (2.17), 3.371 (2.83), 3.389 (2.64), 3.401 (0.85), 3.406 (0.91), 3.625 (2.14), 3.661 (1.95), 3.767 (0.47), 3.793 (0.88), 3.803 (0.58), 3.822 (1.98), 4.152 (3.77), 4.163 (4.15), 4.180 (6.57), 4.213 (4.40), 4.230 (4.21), 4.258 (2.86), 4.264 (4.54), 4.295 (2.17), 4.459 (0.96), 4.470 (0.58), 4.483 (0.55), 4.495 (0.91), 4.554 (1.02), 4.686 (0.63), 5.846 (0.52), 6.835 (2.39), 6.852 (2.67), 6.871 (2.42), 6.876 (2.69), 6.885 (3.30), 6.894 (2.78), 6.913 (1.84), 6.917 (1.92), 6.931 (3.00), 6.934 (2.72), 6.973 (2.78), 6.993 (3.00), 7.010 (1.73), 7.101 (1.04), 7.110 (9.21), 7.117 (7.15), 7.122 (3.27), 7.127 (5.47), 7.331 (1.46), 7.343 (1.15), 7.347 (2.17), 7.367 (3.46), 7.386 (2.75), 7.437 (3.49), 7.458 (2.12), 7.487 (0.49), 7.492 (0.85), 7.504 (2.25), 7.511 (3.24), 7.520 (4.95), 7.528 (3.33), 7.535 (2.61), 7.547 (0.85), 7.552 (0.47), 7.706 (2.20), 7.708 (2.36), 7.725 (2.09), 7.729 (2.17), 7.852 (2.06), 7.855 (1.57), 7.862 (1.13), 7.870 (1.57), 7.875 (1.73), 8.230 (1.81), 8.237 (1.54), 8.246 (0.85), 8.254 (1.65).

Example 1-94

(rac)-(E/Z)-3-[(benzyloxy)methyl]-1-methyl-7-[3-(naphthalen-1-yloxy)propyl]-1,10,13,15-tetrahydro-pyrazolo[4',3':9,10][1,6]oxazacycloundecino[8,7,6-hi]indole-8-carboxylic acid

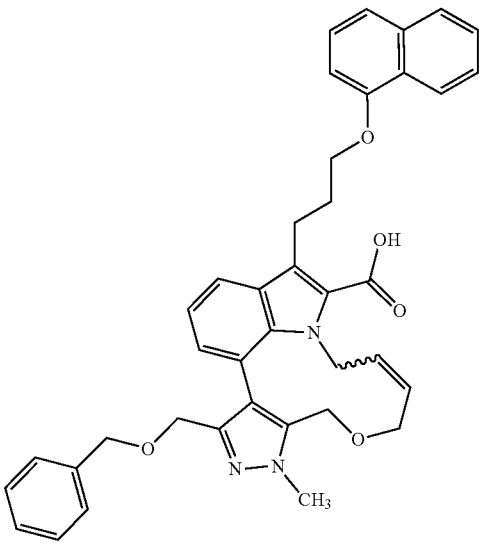 [SMILES: Cn1nc(COCc2ccccc2)c2c1COCC=CCn1c(C(=O)O)c(CCCOc3cccc4ccccc34)c3cccc-2c31]

To a solution of (rac)-(E/Z)-ethyl 3-[(benzyloxy)methyl]-1-methyl-7-[3-(naphthalen-1-yloxy)propyl]-1,10,13,15-tetrahydropyrazolo[4',3':9,10][1,6]oxazacycloundecino[8,7,6-hi]indole-8-carboxylate (see Intermediate 1-168; 70.0 mg, 107 µmol) in THF (5.2 ml) and ethanol (2.5 ml) was added a solution of lithium hydroxide in water (2.1 ml, 1.0 M, 2.1 mmol). The reaction mixture was stirred for 4 days at room temperature. For work-up, the reaction mixture was concentrated under reduced pressure and the residue was purified by flash chromatography (dichloromethane/methanol gradient, 0%→10% methanol) to give the title compound (37 mg) as a racemic mixture.

LC-MS (Method 2): Rt=0.98 min; MS (ESIpos): m/z=628 [M+H]$^+$ $^1$H-NMR (400 MHz, DMSO-d6) δ[ppm]: 0.851 (0.48), 1.232 (3.79), 2.198 (0.47), 2.217 (1.33), 2.233 (2.02), 2.250 (1.40), 2.323 (0.72), 2.327 (0.95), 2.332 (0.70), 2.522 (3.99), 2.664 (0.73), 2.669 (0.98), 2.673 (0.73), 3.357 (2.30), 3.377 (1.92), 3.396 (0.85), 3.410 (0.55), 3.504 (0.77), 3.535 (1.40), 3.566 (0.93), 3.782 (0.85), 3.793 (0.98), 3.815 (0.80), 3.826 (0.72), 3.933 (16.00), 3.970 (1.82), 3.998 (3.47), 4.038 (3.42), 4.067 (1.79), 4.085 (1.87), 4.115 (3.45), 4.176 (4.40), 4.195 (3.20), 4.207 (3.09), 4.225 (2.30), 4.259 (2.22), 4.725 (2.40), 4.740 (0.88), 4.759 (2.37), 4.779 (0.87), 5.039 (0.60), 5.066 (1.27), 5.092 (1.08), 5.105 (0.95), 5.145 (0.87), 5.157 (0.75), 5.169 (0.62), 5.186 (0.82), 5.196 (0.80), 5.759 (0.47), 6.820 (1.95), 6.838 (2.34), 6.851 (2.29), 6.857 (3.00), 6.863 (4.52), 6.874 (2.99), 6.879 (3.04), 7.038 (1.64), 7.057 (2.35), 7.076 (1.48), 7.109 (0.95), 7.118 (6.91), 7.124 (6.19), 7.132 (3.75), 7.135 (3.92), 7.350 (1.42), 7.370 (2.74), 7.389 (1.99), 7.440 (2.95), 7.460 (1.79), 7.482 (0.48), 7.486 (0.67), 7.499 (1.65), 7.503 (1.64), 7.509 (1.87), 7.516 (3.55), 7.523 (1.97), 7.529 (1.77), 7.533 (1.85), 7.546 (0.70), 7.550 (0.50), 7.768 (1.99), 7.787 (1.84), 7.854 (1.79), 7.861 (1.08), 7.872 (1.69), 7.877 (1.52), 8.215 (1.52), 8.221 (1.55), 8.240 (1.53).

Example 1-95

(rac)-3-(hydroxymethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid

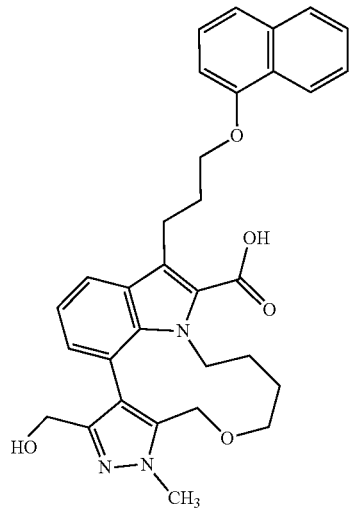 [SMILES: Cn1nc(CO)c2c1COCCCCn1c(C(=O)O)c(CCCOc3cccc4ccccc34)c3cccc-2c31]

To a solution of (rac)-ethyl 3-(hydroxymethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (see Intermediate 1-169; 160 mg, 282 µmol) in THF (14 ml) and ethanol (6.6 ml) was added a solution of lithium hydroxide in water (5.6 ml, 1.0 M, 5.6 mmol). The reaction mixture was stirred for 5 days at room temperature. For work-up, the reaction mixture was concentrated under reduced pressure and the residue was purified by flash chromatography (dichloromethane/methanol gradient, 0%→10% methanol) to give the title compound (110 mg) as a racemic mixture, with small impurities.

LC-MS (Method 1): Rt=1.33 min; MS (ESIpos): m/z=540 [M+H]$^+$ $^1$H-NMR (400 MHz, DMSO-d6) δ[ppm]: 0.833 (0.90), 0.851 (1.81), 1.027 (5.05), 1.036 (6.11), 1.043 (3.35), 1.053 (7.23), 1.071 (3.77), 1.104 (2.18), 1.120 (2.29), 1.138 (1.44), 1.156 (3.61), 1.172 (2.50), 1.213 (4.41), 1.232 (9.73), 1.261 (1.59), 1.366 (1.70), 1.478 (0.53), 1.549 (1.33), 1.628 (0.53), 1.649 (1.49), 1.695 (1.97), 1.712 (2.02), 1.726 (1.86), 1.865 (1.28), 1.907 (2.45), 1.988 (0.90), 2.032 (1.22), 2.052 (1.70), 2.068 (1.28), 2.084 (16.00), 2.192 (2.66), 2.209 (3.83), 2.228 (2.76), 2.323 (2.13), 2.327 (3.14), 2.332 (2.18), 2.518 (10.79), 2.523 (7.81), 2.618 (1.65), 2.635 (3.03), 2.650 (1.54), 2.665 (3.30), 2.669 (4.78), 2.673 (3.46), 2.682 (3.14), 2.699 (1.54), 2.755 (2.34), 2.770 (2.23), 2.784 (2.45), 2.802 (1.28), 3.166 (3.88), 3.246 (1.33), 3.247 (2.39), 3.260 (2.39), 3.278 (3.51), 3.333 (14.46), 3.388 (2.50), 3.412 (3.19), 3.429 (3.14), 3.442 (2.98), 3.504 (1.38), 3.711 (1.01), 3.967 (1.59), 3.984 (3.19), 3.999 (1.75), 4.067 (12.17), 4.076 (11.59), 4.197 (4.04), 4.212 (10.26), 4.224 (4.68), 4.243 (5.69), 4.257 (2.76), 4.376 (0.58), 4.504 (1.81), 4.636 (6.01), 4.644 (3.88), 4.670 (8.66), 4.677 (7.23), 6.620 (2.13), 6.638 (2.60), 6.653 (2.23), 6.803 (4.68), 6.820 (5.37), 6.896 (4.62), 6.914 (5.00), 6.971 (1.59), 6.994 (4.31), 7.012 (5.21), 7.021 (2.18), 7.032 (3.35), 7.040 (2.29), 7.059 (1.44), 7.072 (0.74), 7.095 (0.64), 7.141 (0.53), 7.159 (0.90), 7.176 (0.53), 7.328 (0.48), 7.370 (3.46), 7.390 (6.70), 7.409 (5.48), 7.447 (7.50), 7.468 (4.09), 7.490 (0.96), 7.495 (1.54), 7.508 (4.62), 7.513 (6.91), 7.523 (10.10), 7.532 (7.81), 7.537 (5.32), 7.549 (1.86), 7.555 (1.01), 7.661 (1.70), 7.680 (1.59), 7.710 (3.67), 7.730 (3.46), 7.856 (4.20), 7.866 (2.18), 7.874 (3.08), 7.880 (3.83), 8.240 (3.67), 8.247 (3.08), 8.255 (1.81), 8.264 (3.61).

Example 1-96

(rac)-7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylic acid

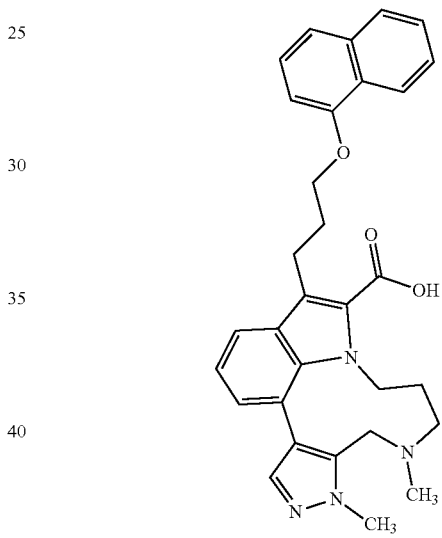

To a solution of (rac)-ethyl 7,9-dimethyl-1-[3-(naphthalen-1-yloxy)propyl]-4,5,6,7,8,9-hexahydropyrazolo[3',4':7,8][1,5]diazecino[9,10,1-hi]indole-2-carboxylate (see Intermediate 1-175; 430 mg, 801 µmol) in THF (39 ml) and ethanol (19 ml) was added a solution of lithium hydroxide in water (16 ml, 1.0 M, 16 mmol). The reaction mixture was stirred for 17 hours at 50° C. For work up, the reaction mixture was concentrated under reduced pressure and the residue was purified by flash chromatography (dichloromethane/methanol gradient, 3%→10% methanol) to give the title compound after trituration with hexane (290 mg) as a racemic mixture.

LC-MS (Method 2): Rt=0.87 min; MS (ESIpos): m/z=509 [M+H]$^+$ $^1$H-NMR (400 MHz, DMSO-d6) δ[ppm]: 1.230 (0.91), 1.548 (0.71), 1.568 (0.77), 1.891 (0.61), 1.912 (0.62), 1.922 (0.70), 1.945 (0.61), 2.150 (0.50), 2.168 (1.51), 2.195 (16.00), 2.318 (0.82), 2.322 (0.85), 2.327 (1.16), 2.347 (0.60), 2.364 (0.59), 2.518 (2.25), 2.523 (1.46), 2.669 (0.51), 3.041 (1.95), 3.077 (2.10), 3.244 (0.86), 3.258 (0.83), 3.277 (1.29), 3.296 (0.72), 3.333 (2.32), 3.363 (1.36), 3.382 (0.88), 3.397 (0.86), 3.638 (2.06), 3.674 (1.86), 3.753 (0.48), 3.763

(0.51), 3.777 (0.57), 3.788 (0.95), 3.799 (0.58), 3.813 (0.66), 3.822 (0.51), 4.150 (1.79), 4.165 (3.78), 4.180 (1.79), 4.461 (0.49), 4.471 (1.10), 4.482 (0.63), 4.496 (0.59), 4.507 (1.03), 4.518 (0.45), 5.759 (6.05), 6.859 (2.37), 6.878 (2.58), 6.909 (1.76), 6.912 (1.95), 6.927 (3.31), 6.930 (3.05), 6.960 (2.80), 6.979 (3.03), 6.997 (1.62), 7.360 (9.39), 7.377 (3.23), 7.397 (2.52), 7.438 (3.45), 7.459 (1.92), 7.482 (0.56), 7.486 (0.77), 7.499 (1.95), 7.503 (1.81), 7.511 (2.02), 7.517 (4.11), 7.523 (2.08), 7.530 (1.90), 7.534 (2.11), 7.547 (0.83), 7.551 (0.56), 7.693 (2.33), 7.696 (2.41), 7.712 (2.23), 7.715 (2.12), 7.851 (2.04), 7.858 (1.14), 7.869 (1.97), 7.874 (1.68), 8.198 (1.78), 8.203 (1.77), 8.222 (1.69), 13.111 (0.40).

Example 1-97

(rac)-9,11-Dimethyl-1-[3-(1-naphthyloxy)propyl]-7-phenyl-4,5,6,7,8,9-hexahydropyrazolo[3',4':7,8][1,5]diazecino[9,10,1-hi]indole-2-carboxylic acid

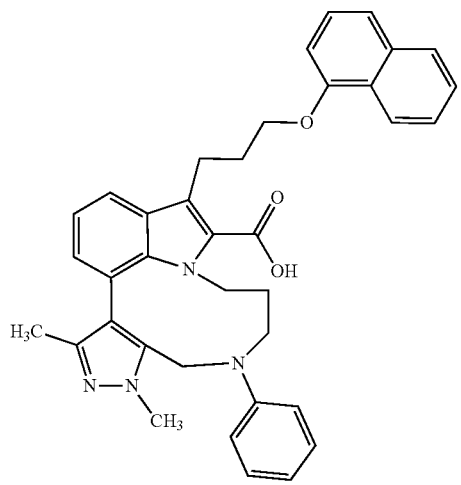 [SMILES: Cc1nn(C)c2c1-c1cccc3c(CCCOc4cccc5ccccc45)c(C(=O)O)n(c13)CCCN(c1ccccc1)C2]

To a solution of (rac)-ethyl 9,11-dimethyl-1-[3-(1-naphthyloxy)propyl]-7-phenyl-4,5,6,7,8,9-hexahydropyrazolo[3',4':7,8][1,5]diazecino[9,10,1-hi]indole-2-carboxylate (see Intermediate 1-179; 34.0 mg, 0.056 mmol, 1.0 eq) in THF (2.0 mL) and methanol (1.0 mL) was added lithium hydroxide (23.3 mg, 0.56 mmol, 10.0 eq) in water (1 mL). The mixture was stirred at 40° C. for 15 hrs. The crude product was purified by preparative HPLC (Instrument: Varian SD-200; Column: Phenomenex Luna 10μ 250×21.6 mm; eluent A: water+0.1% trifluoroacetic acid, Eluent B: acetonitrile+0.1% trifluoroacetic acid; gradient: 0.0 min 95% A→30.0 min 0% A→32.0 min 0% A→35 min 95% A→36.0 min 95% A (stop); flow 20 ml/min; temperature: rt ° C.; detector Varian Variable wavelength UV detector.) to afford the title compound (15.0 mg) as white solid.

MS: m/z=585 [M+H]$^+$.

$^1$H NMR (300 MHz, CDCl$_3$) δ [ppm]=8.33-8.30 (1H), 7.77-7.74 (1H), 7.58-7.55 (1H), 7.46-7.43 (2H), 7.38-7.30 (2H), 7.00-6.92 (4H), 6.72-6.69 (1H), 6.53 (1H), 6.38 (2H), 4.69-4.62 (2H), 4.49 (1H), 4.08-3.91 (4H), 3.82 (3H), 3.35-3.27 (4H), 2.96-2.89 (2H), 2.20-2.13 (2H), 2.00 (3H).

Example 1-98

(rac)-9,11-Dimethyl-7-[4-(morpholin-4-yl)phenyl]-1-[3-(1-naphthyloxy)propyl]-4,5,6,7,8,9-hexahydropyrazolo[3',4':7,8][1,5]diazecino[9,10,1-hi]indole-2-carboxylic acid

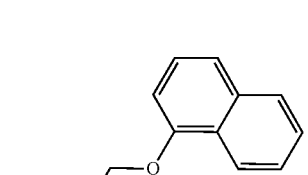

To a solution of (rac)-ethyl 9,11-dimethyl-7-[4-(morpholin-4-yl)phenyl]-1-[3-(1-naphthyloxy)propyl]-4,5,6,7,8,9-hexahydropyrazolo[3',4':7,8][1,5]diazecino[9,10,1-hi]indole-2-carboxylate (see Intermediate 1-183; 40 mg, 0.057 mmol, 1.0 eq) in THF (1.0 mL) and methanol (0.5 mL) was added lithium hydroxide (7.0 mg, 1.1 mmol, 20.0 eq) in water (0.5 mL). The mixture was stirred at 40° C. for 48 hrs. The crude product was purified by preparative HPLC (Instrument: Varian SD-200; Column: Phenomenex Luna 10μ 250×21.6 mm; eluent A: water+0.1% trifluoroacetic acid, Eluent B: acetonitrile+0.1% trifluoroacetic acid; gradient: 0.0 min 95% A→30.0 min 0% A→32.0 min 0% A→35 min 95% A→36.0 min 95% A (stop); flow 20 ml/min; temperature: rt ° C.; detector Varian Variable wavelength UV detector) to afford the title compound (13.9 mg) as white solid.

MS: m/z=670 [M+H]$^+$.

$^1$H NMR (300 MHz, CDCl$_3$) δ [ppm]=8.36-8.32 (1H), 7.79-7.76 (1H), 7.64-7.61 (1H), 7.48-7.45 (2H), 7.40-7.28 (2H), 7.01-6.93 (2H), 6.74 (1H), 6.63 (2H), 6.36 (2H), 4.68-4.60 (1H), 4.42-4.37 (1H), 4.13-4.10 (4H), 3.91-3.86 (1H), 3.83 (3H), 3.75-3.71 (4H), 3.40-3.31 (4H), 2.91-2.88 (6H), 2.24-2.20 (2H), 2.05 (3H).

The title compound (13 mg) was separated into enantiomers by chiral HPLC to give enantiomer 1 (6 mg, see Example 1-99) and enantiomer 2 (6 mg, see Example 1-100).

Preparative chiral HPLC method: Instrument: Berger multigram SFC system; Column: Superchiral S-AD 5μ 250×21.2 mm; eluent A: CO$_2$, Eluent B: isopropyl alcohol, Eluent C: diethyl amine; gradient: isocratic 55% A+45% B+0.05% C (v/v/v); flow 40 ml/min; temperature: 35° C.; detection: 230 nm.

Analytical chiral HPLC method: Column: Superchiral S-AD 5 μm 250×4.6 mm; eluent A: CO$_2$, Eluent B: isopropyl alcohol, Eluent C: diethyl amine; gradient: isocratic 55% A+45% B+0.05% C (v/v/v); flow 2.5 ml/min; temperature: 35° C.; detection: 230 nm.

Example 1-99

9,11-Dimethyl-7-[4-(morpholin-4-yl)phenyl]-1-[3-(1-naphthyloxy)propyl]-4,5,6,7,8,9-hexahydropyrazolo[3',4':7,8][1,5]diazecino[9,10,1-hi]indole-2-carboxylic acid (Enantiomer 1)

See Example 1-98 for preparation and enantiomer separation.
Analytical chiral HPLC (method see Example 1-98): $R_t$=5.1 min.

Example 1-100

9,11-Dimethyl-7-[4-(morpholin-4-yl)phenyl]-1-[3-(1-naphthyloxy)propyl]-4,5,6,7,8,9-hexahydropyrazolo[3',4':7,8][1,5]diazecino[9,10,1-hi]indole-2-carboxylic acid (Enantiomer 2)

See Example 1-98 for preparation and enantiomer separation.
Analytical chiral HPLC (method see Example 1-98): $R_t$=8.48 min.

Example 1-101

(rac)-8,10-Dimethyl-1-[3-(1-naphthyloxy)propyl]-6-phenyl-5,6,7,8-tetrahydro-4H-pyrazolo[3',4':6,7][1,4]diazonino[8,9,1-hi]indole-2-carboxylic acid

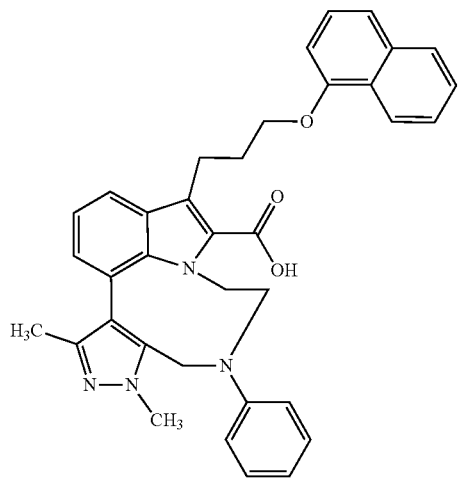 [SMILES: Cc1nn(C)c2c1-c1cccc3c(CCCOc4cccc5ccccc45)c(C(=O)O)n(c13)CCN(c1ccccc1)C2]

To a solution of (rac)-ethyl 8,10-dimethyl-1-[3-(1-naphthyloxy)propyl]-6-phenyl-5,6,7,8-tetrahydro-4H-pyrazolo[3',4':6,7][1,4]diazonino[8,9,1-hi]indole-2-carboxylate (3.5 mg, 0.006 mmol, 1.0 eq; see Intermediate 1-187) in THF (1.0 mL) and methanol (0.5 mL) was added lithium hydroxide (2.5 mg, 0.06 mmol, 10.0 eq) in water (0.5 mL). The mixture was stirred at 50° C. for 15 hrs. The crude product was purified by preparative HPLC (Instrument: Varian SD-200; Column: Phenomenex Luna 10µ 250×21.6 mm; eluent A: water+0.1% trifluoroacetic acid, Eluent B: acetonitrile+0.1% trifluoroacetic acid; gradient: 0.0 min 95% A→30.0 min 0% A→32.0 min 0% A→35 min 95% A→36.0 min 95% A (stop); flow 20 ml/min; temperature: rt ° C.; detector: Varian Variable wavelength UV detector) (to afford the title compound (1.5 mg, 44%) as white solid.
MS: m/z=571 [M+H]⁺.
¹H NMR (300 MHz, CD₃OD₃) δ [ppm]=8.34-8.31 (1H), 7.80-7.77 (1H), 7.50-7.43 (2H), 7.39-7.26 (2H), 7.10-7.04 (1H), 7.00-6.92 (4H), 6.82-6.81 (1H), 6.74-6.67 (3H), 6.27-6.17 (2H), 4.74-4.68 (1H), 4.52-4.41 (2H), 4.32-4.17 (2H), 4.19-3.96 (2H), 3.92 (3H), 3.50-3.23 (2H), 2.35-2.14 (2H), 2.03 (3H).

Example 1-102

(rac)-11-(Methoxymethyl)-7,9-dimethyl-1-[3-(1-naphthyloxy)propyl]-4,5,6,7,8,9-hexahydropyrazolo[3',4':7,8][1,5]diazecino[9,10,1-hi]indole-2-carboxylic acid

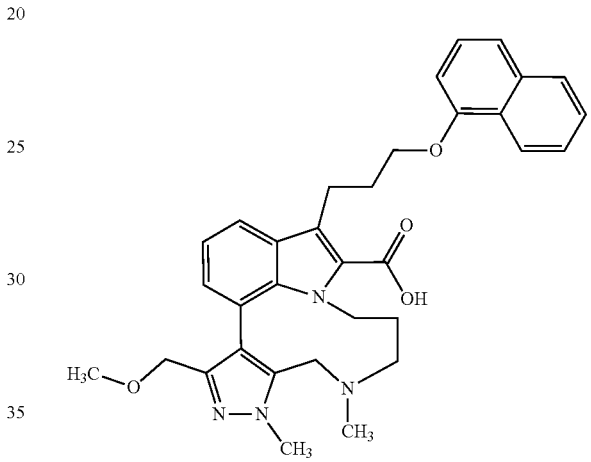

To a solution of (rac)-ethyl 11-(methoxymethyl)-7,9-dimethyl-1-[3-(1-naphthyloxy)propyl]-4,5,6,7,8,9-hexahydropyrazolo[3',4':7,8][1,5]diazecino[9,10,1-hi]indole-2-carboxylate (see Intermediate 1-194; 35.0 mg, 0.06 mmol, 1.0 eq) in THF (1.0 mL) and methanol (0.5 mL) was added lithium hydroxide monohydrate (25.4 mg, 0.60 mmol, 10.0 eq) in water (0.5 mL). The mixture was stirred at 40° C. for 15 hrs. The crude product was purified by flash chromatography (methanol, dichloromethane 1:10) to afford the title compound (13.0 mg, 39.3%) as a white solid.
MS: m/z=553 [M+H]⁺.
¹H NMR (300 MHz, CDCl₃) δ [ppm]=8.36-8.33 (1H), 7.78-7.73 (2H), 7.47-7.44 (2H), 7.40-7.28 (2H), 7.09-7.03 (2H), 6.73-6.71 (1H), 4.58-4.52 (1H), 4.31-4.16 (4H), 3.96 (3H), 3.95-3.86 (1H), 3.54-3.34 (3H), 3.27 (3H), 3.21-3.16 (2H), 2.45-2.31 (2H), 2.23 (3H), 2.11-2.04 (2H), 1.85-1.51 (2H).
The title compound (13 mg) was separated into enantiomers by chiral HPLC to give enantiomer 1 (4 mg, see Example 1-103) and enantiomer 2 (4 mg, see Example 1-104).
Preparative chiral HPLC method Instrument: Berger multigram SFC system; Column: chromegachiral CCA 5µ 250× 21.2 mm; eluent A: CO₂, Eluent B: isopropyl alcohol, Eluent C: diethyl amine; gradient: isocratic 60% A+40% B+0.1% C (v/v/v); flow 40 ml/min; temperature: 35° C.; detection: 220 nm.
Analytical chiral HPLC method: Instrument: Berger analytical SFC system; Column: chromegachiral CCA 5µ 250× 4.6 mm; eluent A: CO₂, Eluent B: isopropyl alcohol, Eluent C: diethyl amine; gradient: isocratic 60% A+40% B+0.1% C (v/v/v); flow 2.5 ml/min; temperature: 35° C.; detection: 220 nm.

Example 1-103

11-(methoxymethyl)-7,9-dimethyl-1-[3-(1-naphthyloxy)propyl]-4,5,6,7,8,9-hexahydropyrazolo[3',4':7,8][1,5]diazecino[9,10,1-hi]indole-2-carboxylic acid (Enantiomer 1)

See Example 1-102 for preparation and enantiomer separation.
Analytical chiral HPLC (method see Example 1-102): $R_t$=2.23 min.

Example 1-104

11-(methoxymethyl)-7,9-dimethyl-1-[3-(1-naphthyloxy)propyl]-4,5,6,7,8,9-hexahydropyrazolo[3',4':7,8][1,5]diazecino[9,10,1-hi]indole-2-carboxylic acid (Enantiomer 2)

See Example 1-102 for preparation and enantiomer separation.
Analytical Chiral HPLC (method see Example 1-102): $R_t$=3.3 min.

Example 1-105

(rac)-7-{4-[4-(Dimethylsulfamoyl)piperazin-1-yl]phenyl}-9,11-dimethyl-1-[3-(1-naphthyloxy)propyl]-4,5,6,7,8,9-hexahydropyrazolo[3',4':7,8][1,5]diazecino[9,10,1-hi]indole-2-carboxylic acid

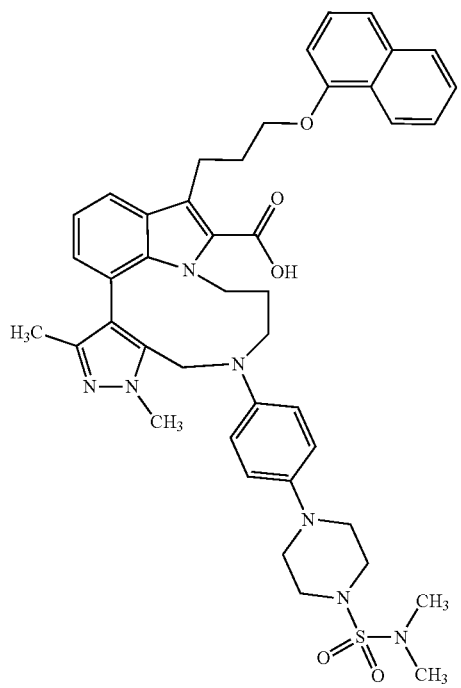 [SMILES: Cc1nn(C)c2c1-c1cccc3c(CCCOc4cccc5ccccc45)c(C(=O)O)n(c13)CCCN(c1ccc(N3CCN(S(=O)(=O)N(C)C)CC3)cc1)C2]

To a solution of (rac)-ethyl 7-{4-[4-(dimethylsulfamoyl)piperazin-1-yl]phenyl}-9,11-dimethyl-1-[3-(1-naphthyloxy)propyl]-4,5,6,7,8,9-hexahydropyrazolo[3',4':7,8][1,5]diazecino[9,10,1-hi]indole-2-carboxylate (see Intermediate 1-200; 41.0 mg, 0.051 mmol, 1.0 eq) in THF (1.0 mL) and methanol (0.5 mL) was added lithium hydroxide (21 mg, 0.51 mmol, 10.0 eq) in water (0.5 mL). The mixture was stirred at 45° C. for 21 hrs. The crude product was purified by preparative. HPLC (Instrument: Varian SD-200; Column: Phenomenex Luna 10μ 250×21.6 mm; eluent A: water+0.1% trifluoroacetic acid, Eluent B: acetonitrile+0.1% trifluoroacetic acid; gradient: 0.0 min 95% A→30.0 min 0% A→32.0 min 0% A→35 min 95% A→36.0 min 95% A (stop); flow 20 ml/min; temperature: rt ° C.; detector Varian Variable wavelength UV detector) to afford the title compound (34 mg, 86%) as a white solid.

MS: m/z=776 [M+H]⁺.

¹H NMR (300 MHz, CDCl₃) δ [ppm]=8.37-8.34 (1H), 7.80-7.77 (1H), 7.67-7.64 (1H), 7.50-7.46 (2H), 7.41-7.30 (2H), 7.06-6.99 (2H), 6.75-6.73 (1H), 6.65-6.62 (2H), 6.36-6.33 (2H), 4.70-4.60 (2H), 4.43-4.38 (1H), 4.17-4.08 (2H), 3.97-3.91 (1H), 3.88 (3H), 3.40-3.35 (4H), 3.30-3.26 (6H), 2.96-2.93 (5H), 2.78 (6H), 2.25-2.19 (2H), 2.10 (3H).

The title compound (30 mg) was separated into enantiomers by chiral HPLC to give enantiomer 1 (12 mg, see Example 1-106) and enantiomer 2 (12 mg, see Example 1-107).

Preparative chiral HPLC method: Instrument: Berger multigram SFC system; Column: Superchiral S-AD 5μ 250×21.2 mm; eluent A: CO₂, Eluent B: isopropyl alcohol, Eluent C: diethyl amine; gradient: isocratic 60% A+40% B+0.1% C (v/v/v); flow 40 ml/min; temperature: 35° C.; detection: 220 nm.

Analytical chiral HPLC method: Berger analytical SFC system; Column: Superchiral S-AD 5μ 250×4.6 mm; eluent A: CO₂, Eluent B: isopropyl alcohol, Eluent C: diethyl amine; gradient: isocratic 60% A+40% B+0.1% C (v/v/v); flow 2.5 ml/min; temperature: 35° C.; detection: 220 nm.

Example 1-106

7-{4-[4-(Dimethylsulfamoyl)piperazin-1-yl]phenyl}-9,11-dimethyl-1-[3-(1-naphthyloxy)propyl]-4,5,6,7,8,9-hexahydropyrazolo[3',4':7,8][1,5]diazecino[9,10,1-hi]indole-2-carboxylic acid (Enantiomer 1)

See Example 1-105 for preparation and enantiomer separation.
Analytical chiral HPLC (method see Example 1-105): $R_t$=6.64 min.

Example 1-107

7-{4-[4-(Dimethylsulfamoyl)piperazin-1-yl]phenyl}-9,11-dimethyl-1-[3-(1-naphthyloxy)propyl]-4,5,6,7,8,9-hexahydropyrazolo[3',4':7,8][1,5]diazecino[9,10,1-hi]indole-2-carboxylic acid (Enantiomer 2)

See Example 1-105 for preparation and enantiomer separation.
Analytical chiral HPLC (method see Example 1-105): $R_t$=6.96 min.

Example 1-108

(rac)-7-{4-[4-(Ethylsulfonyl)piperazin-1-yl]phenyl}-9,11-dimethyl-1-[3-(1-naphthyloxy)propyl]-4,5,6,7,8,9-hexahydropyrazolo[3',4':7,8][1,5]diazecino[9,10,1-hi]indole-2-carboxylic acid

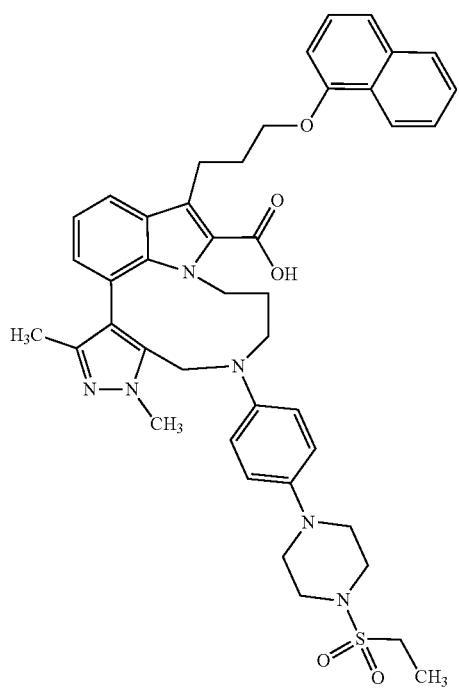 [SMILES: CCS(=O)(=O)N1CCN(c2ccc(N3CCCn4c(C(=O)O)c(CCCOc5cccc6ccccc56)c5cccc(c54)-c4c(C)nn(C)c4C3)cc2)CC1]

To a solution of (rac)-ethyl 7-{4-[4-(ethylsulfonyl)piperazin-1-yl]phenyl}-9,11-dimethyl-1-[3-(1-naphthyloxy)propyl]-4,5,6,7,8,9-hexahydropyrazolo[3',4':7,8][1,5]diazecino[9,10,1-hi]indole-2-carboxylate (see Intermediate 1-201; 35.0 mg, 0.044 mmol, 1.0 eq) in THF (1.0 mL) and methanol (0.5 mL) was added lithium hydroxide (21 mg, 0.51 mmol, 10.0 eq) in water (0.5 mL). The mixture was stirred at 45° C. for 21 hrs. The crude product was purified by preparative HPLC (Instrument: Varian SD-200; Column: Phenomenex Luna 10μ 250×21.6 mm; eluent A: water+0.1% trifluoroacetic acid, Eluent B: acetonitrile+0.1% trifluoroacetic acid; gradient: 0.0 min 95% A→30.0 min 0% A→32.0 min 0% A→35 min 95% A→36.0 min 95% A (stop); flow 20 ml/min; temperature: rt ° C.; detector Varian Variable wavelength UV detector) to afford the title compound (25 mg, 74%) as white solid.

MS: m/z=761 [M+H]$^+$.

$^1$H NMR (300 MHz, CDCl$_3$) δ [ppm]=8.37-8.34 (1H), 7.80-7.77 (1H), 7.67-7.64 (1H), 7.50-7.46 (2H), 7.41-7.30 (2H), 7.06-7.02 (2H), 6.75-6.73 (1H), 6.64-6.61 (2H), 6.34-6.31 (2H), 4.67-4.62 (2H), 4.42-4.37 (1H), 4.18-4.06 (3H), 3.98-3.93 (1H), 3.88 (3H), 3.49-3.37 (2H), 3.32-3.26 (6H), 3.01-2.93 (4H), 2.89-2.82 (2H), 2.30-2.18 (4H), 2.10 (3H), 1.35-1.33 (3H).

The title compound (25 mg) was separated into enantiomers by chiral HPLC to give enantiomer 1 (8 mg, see Example 1-109) and enantiomer 2 (8 mg, see Example 1-110).

Preparative chiral HPLC method: Instrument: Berger multigram SFC system; Column: Superchiral S-AD 5μ 250×21.2 mm; eluent A: CO$_2$, Eluent B: isopropyl alcohol, Eluent C: diethylamine; gradient: isocratic 55% A+45% B+0.05% C (v/v/v); flow 40 ml/min; temperature: 35° C.; detection: 220 nm.

Analytical chiral HPLC method: Instrument: Berger analytical SFC system; Column: Superchiral S-AD 5μ 250×4.6 mm; eluent A: CO$_2$, Eluent B: isopropyl alcohol, Eluent C: diethylamine; gradient: isocratic 60% A+40% B+0.1% C (v/v/v); flow 2.5 ml/min; temperature: 35° C.; detection: 220 nm.

Example 1-109

7-{4-[4-(Ethylsulfonyl)piperazin-1-yl]phenyl}-9,11-dimethyl-1-[3-(1-naphthyloxy)propyl]-4,5,6,7,8,9-hexahydropyrazolo[3',4':7,8][1,5]diazecino[9,10,1-hi]indole-2-carboxylic acid (Enantiomer 1)

See Example 1-108 for preparation and enantiomer separation.

Analytical Chiral HPLC (method see Example 1-108): R$_t$=7.0 min.

Example 1-110

7-{4-[4-(Ethylsulfonyl)piperazin-1-yl]phenyl}-9,11-dimethyl-1-[3-(1-naphthyloxy)propyl]-4,5,6,7,8,9-hexahydropyrazolo[3',4':7,8][1,5]diazecino[9,10,1-hi]indole-2-carboxylic acid (Enantiomer 2)

See Example 1-108 for preparation and enantiomer separation.

Analytical chiral HPLC (method see Example 1-108): R$_t$=7.6 min.

Example 1-111

(rac)-11-({4-[4-(Dimethylsulfamoyl)piperazin-1-yl]phenoxy}methyl)-7,10-dimethyl-1-[3-(1-naphthyloxy) propyl]-4,5,6,7,8,10-hexahydropyrazolo[3',4':7,8][1,5]diazecino[9,10,1-hi]indole-2-carboxylic acid

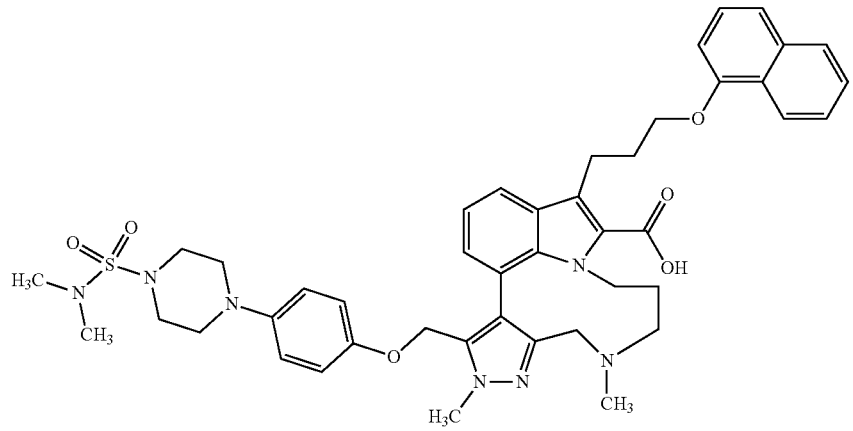 [SMILES: CN1CCCn2c(C(=O)O)c(CCCOc3cccc4ccccc34)c3cccc(c32)-c2c(nn(C)c2COc2ccc(N3CCN(S(=O)(=O)N(C)C)CC3)cc2)C1]

To a solution of ethyl 11-({4-[4-(dimethylsulfamoyl)piperazin-1-yl]phenoxy}methyl)-7,10-dimethyl-1-[3-(1-naphthyloxy)propyl]-4,5,6,7,8,10-hexahydropyrazolo[3',4':7,8][1,5]diazecino[9,10,1-hi]indole-2-carboxylate (see Intermediate 1-210; 60.0 mg, 0.072 mmol, 1.0 eq) in THF (1.0 mL) and methanol (0.5 mL) was added lithium hydroxide monohydrate (30.2 mg, 0.72 mmol, 10.0 eq) in water (0.5 mL). The mixture was stirred at 40° C. for 48 hrs. The crude product was purified by preparative HPLC (Instrument: Varian SD-200; Column: Phenomenex Luna 10μ 250×21.6 mm; eluent A: water+0.1% trifluoroacetic acid, Eluent B: acetonitrile+0.1% trifluoroacetic acid; gradient: 0.0 min 95% A→30.0 min 0% A→32.0 min 0% A→35 min 95% A→36.0 min 95% A (stop); flow 20 ml/min; temperature: rt ° C.; detector Varian Variable wavelength UV detector) to afford the title compound (40.0 mg, 68.9%) as a white solid.

MS: m/z=806 [M+H]$^+$.

$^1$H NMR (300 MHz, CDCl$_3$) δ [ppm]=8.37-8.34 (1H), 7.77-7.69 (2H), 7.48-7.40 (2H), 7.35-7.32 (1H), 7.23-7.19 (2H), 7.02-7.00 (1H), 6.82-6.80 (1H), 6.70-6.62 (5H), 4.90-4.75 (2H), 4.61-4.50 (1H), 4.15-4.08 (2H), 4.02 (3H), 3.47-3.33 (6H), 3.05-3.01 (4H), 2.82 (6H), 2.80-2.40 (6H), 2.35-2.18 (2H), 1.81-1.65 (4H).

The title compound (35 mg) was separated into enantiomers by chiral HPLC to give enantiomer 1 (15 mg, see Example 1-112) and enantiomer 2 (17 mg, see Example 1-113).

Preparative chiral HPLC method: Instrument: Berger multigram SFC system; Column: Superchiral S-AD 5μ 250×21.2 mm; eluent A: CO$_2$, Eluent B: ethanol, Eluent C: diethylamine; gradient: isocratic 75% A+25% B+0.1% C (v/v/v); flow 40 ml/min; temperature: 35° C.; detection: 220 nm.

Analytical chiral HPLC method: Instrument: Berger analytical SFC system; Column: Superchiral S-AD 5μ 250×4.6 mm; eluent A: CO$_2$, Eluent B: ethanol, Eluent C: diethylamine; gradient: isocratic 75% A+25% B+0.1% C (v/v/v); flow 3 ml/min; temperature: 35° C.; detection: 220 nm.

Example 1-112

11-({4-[4-(Dimethylsulfamoyl)piperazin-1-yl]phenoxy}methyl)-7,10-dimethyl-1-[3-(1-naphthyloxy)propyl]-4,5,6,7,8,10-hexahydropyrazolo[3',4':7,8][1,5]diazecino[9,10,1-hi]indole-2-carboxylic acid (Enantiomer 1)

See Example 1-111 for preparation and enantiomer separation.

Analytical chiral HPLC (method see Example 1-111): R$_t$=4.9 min.

Example 1-113

11-({4-[4-(Dimethylsulfamoyl)piperazin-1-yl]phenoxy}methyl)-7,10-dimethyl-1-[3-(1-naphthyloxy)propyl]-4,5,6,7,8,10-hexahydropyrazolo[3',4':7,8][1,5]diazecino[9,10,1-hi]indole-2-carboxylic acid (Enantiomer 2)

See Example 1-111 for preparation and enantiomer separation.

Analytical chiral HPLC (method see Example 1-111): R$_t$=6.0 min.

Example 1-114

(rac)-7,9-Dimethyl-1-[3-(1-naphthyloxy)propyl]-11-{[4-(2-oxopyridin-1(2H)-yl)phenoxy]methyl}-4,5,6,7,8,9-hexahydropyrazolo[3',4':7,8][1,5]diazecino[9,10,1-hi]indole-2-carboxylic acid

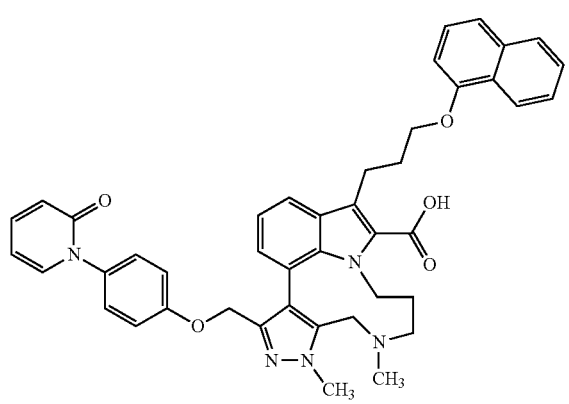 [SMILES: CN1CCCn2c(C(=O)O)c(CCCOc3cccc4ccccc34)c3cccc(c32)-c2c(COc3ccc(-n4ccccc4=O)cc3)nn(C)c2C1]

To a solution of (rac)-ethyl 7,9-dimethyl-1-[3-(1-naphthyloxy)propyl]-11-{[4-(2-oxopyridin-1(2H)-yl)phenoxy]methyl}-4,5,6,7,8,9-hexahydropyrazolo[3',4':7,8][1,5]diazecino[9,10,1-hi]indole-2-carboxylate (see Intermediate 1-221; 40 mg, 0.054 mmol, 1.0 eq) in THF/methanol (2 mL/1 mL) was added lithium hydroxide (23 mg, 0.54 mmol, 10 eq, in 1 mL of water) at room temperature. The reaction mixture was stirred at 40° C. overnight. The mixture was acidified to pH 3 with aqueous 1N HCl and purified by HPLC (Instrument: Varian SD-200; Column: Phenomenex Luna 10µ 250×21.6 mm; eluent A: water+0.1% trifluoroacetic acid, Eluent B: acetonitrile+0.1% trifluoroacetic acid; gradient: 0.0 min 95% A→30.0 min 0% A→32.0 min 0% A→35 min 95% A→36.0 min 95% A (stop); flow 20 ml/min; temperature: rt ° C.; detector Varian Variable wavelength UV detector) to give the title compound (32 mg).

$^1$H NMR (300 MHz, CD$_3$OD) δ [ppm]=8.28-8.23 (1H), 7.77-7.72 (2H), 7.55-7.41 (5H), 7.29-7.27 (1H), 7.04-7.00 (4H), 6.72-6.69 (3H), 6.66-6.63 (1H), 6.36-6.31 (1H), 5.28 (2H), 4.81 (2H), 4.36-4.20 (2H), 4.11-4.03 (2H), 3.88-3.72 (4H), 3.57-3.51 (2H), 2.35-2.23 (2H), 2.05-2.01 (6H).

The title compound (32 mg) was separated into enantiomers by chiral HPLC to give enantiomer 1 (14 mg, see Example 1-115) and enantiomer 2 (12 mg, see Example 1-116).

Preparative chiral HPLC method: Instrument: Berger multigram SFC system; Column: Superchiral S-AD 5µ 250×21.2 mm; eluent A: CO$_2$, Eluent B: isopropyl alcohol, Eluent C: diethyl amine; gradient: isocratic 50% A+50% B+0.05% C (v/v/v); flow 40 ml/min; temperature: 35° C.; detection: 220 nm.

Analytical chiral HPLC method: Instrument: Berger analytical SFC system; Column: Superchiral S-AD 5µ 250×4.6 mm; eluent A: CO$_2$, Eluent B: isopropyl alcohol; gradient: isocratic 50% A+50% B (v/v); flow 2 ml/min; temperature: 35° C.; detection: 220 nm.

Example 1-115

7,9-Dimethyl-1-[3-(1-naphthyloxy)propyl]-11-{[4-(2-oxopyridin-1(2H)-yl)phenoxy]methyl}-4,5,6,7,8,9-hexahydropyrazolo[3',4':7,8][1,5]diazecino[9,10,1-hi]indole-2-carboxylic acid (Enantiomer 1)

See Example 1-114 for preparation and enantiomer separation.

Analytical chiral HPLC (method see Example 1-114): R$_t$=8.09 min.

Example 1-116

7,9-Dimethyl-1-[3-(1-naphthyloxy)propyl]-11-{[4-(2-oxopyridin-1(2H)-yl)phenoxy]methyl}-4,5,6,7,8,9-hexahydropyrazolo[3',4':7,8][1,5]diazecino[9,10,1-hi]indole-2-carboxylic acid (Enantiomer 2)

See Example 1-114 for preparation and enantiomer separation.

Analytical chiral HPLC (method see Example 1-114): R$_t$=12.87 min.

Example 1-117

(rac)-2'-Carboxy-10'-((4-(4-(N,N-dimethylsulfamoyl)piperazin-1-yl) phenoxy)methyl)-8',11'-dimethyl-1'-(3-(naphthalen-1-yloxy)propyl)-4',5',7',8'-tetrahydrospiro[morpholine-4,6'-pyrazolo[3',4':6,7][1,4]diazonino[8,9,1-hi]indol]-4-ium bromide

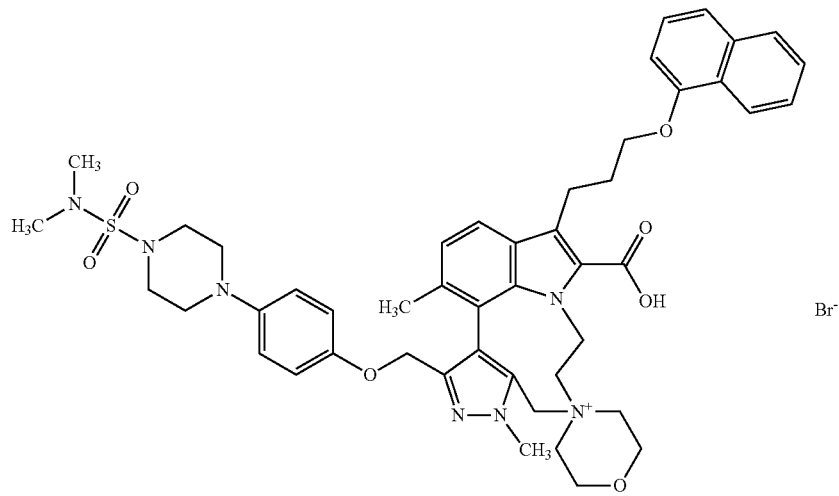 [SMILES: Cc1ccc2c(CCCOc3cccc4ccccc34)c(C(=O)O)n3c2c1-c1c(COc2ccc(N4CCN(S(=O)(=O)N(C)C)CC4)cc2)nn(C)c1C[N+]1(CCOCC1)CC3 ; [Br-]]

A mixture comprising (rac)-2'-ethoxycarbonyl-10'-((4-(4-(N,N-dimethylsulfamoyl)piperazin-1-yl)phenoxy)methyl)-8',11'-dimethyl-1'-(3-(naphthalen-1-yloxy)propyl)-4',5',7',8'-tetrahydrospiro[morpholine-4,6'-pyrazolo[3',4':6,7][1,4]diazonino[8,9,1-hi]indol]-4-ium bromide (see Intermediate 1-232; 4.00 mg, 4.12 μmol), THF (150 μl), methanol (38 μl) and lithium hydroxide (25 μl, 1.0 M in water) was stirred at rt for 2.5 days. The mixture was neutralized by the addition of hydrobromic acid (24 μl, 1.0 M in water) and the crude mixture was purified by preparative TLC (methanol:dichloromethane) to give the title compound (3.20 mg).

LC-MS: m/z=862 [M+H]$^+$.

$^1$H-NMR (400 MHz, METHANOL-d4), δ [ppm]=2.13 (3H), 2.33 (2H), 2.73-2.83 (7H), 2.87-2.95 (4H), 3.14 (1H), 3.19-3.24 (4H), 3.24-3.57 (4H), 3.63-3.77 (2H), 3.83-3.92 (2H), 3.94-4.06 (2H), 4.07-4.20 (3H), 4.17 (3H), 4.44 (1H), 4.50 (1H), 4.64 (1H), 4.71 (1H), 5.11 (1H), 6.37 (2H), 6.64 (2H), 6.73 (1H), 7.04 (1H), 7.27 (1H), 7.35 (1H), 7.39-7.48 (2H), 7.65 (1H), 7.77 (1H), 8.15 (1H).

Example 1-118

(rac)-12-Methoxy-1-[3-(5,6,7,8-tetrahydronaphthalen-1-yloxy)propyl]-4,5,7,8-tetrahydro-10,14-(metheno)[1,4,7]dioxazacyclotetradecino[9,8,7-hi]indole-2-carboxylic acid

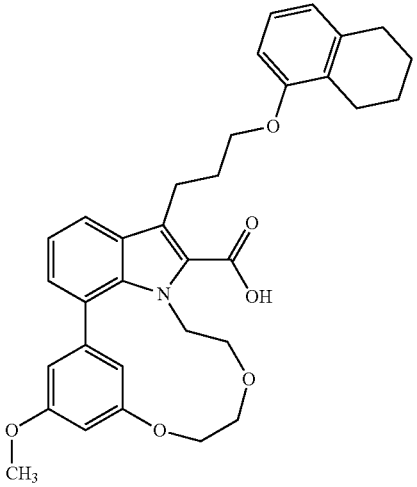 [SMILES: COc1cc2cc(c1)-c1cccc3c(CCCOc4cccc5c4CCCC5)c(C(=O)O)n(c13)CCOCCO2]

A mixture comprising (rac)-ethyl 12-methoxy-1-[3-(5,6,7,8-tetrahydronaphthalen-1-yloxy)propyl]-4,5,7,8-tetrahydro-10,14-(metheno)[1,4,7]dioxazacyclotetradecino[9,8,7-hi]indole-2-carboxylate (see Intermediate 1-235; 19.6 mg, 34.4 μmol), THF (1.0 ml), methanol (300 μl) and lithium hydroxide (210 μl, 1.0 M in water) was stirred at rt overnight. Water was added, the mixture was acidified by the addition of aqueous HCl (pH 3-4) and extracted with dichloromethane. The organic layer was dried over sodium sulfate. After filtration and removal of the solvents, the crude mixture was purified by preparative TLC (EtOH:dichloromethane) to give the title compound (3.8 mg, 19% yield).

MS: m/z=564.2 [M+Na]$^+$.

1H-NMR (400 MHz, DMSO-d6), δ [ppm]=1.64-1.78 (4H), 2.02 (2H), 2.62 (2H), 2.68 (2H), 3.08-3.20 (3H), 3.42 (1H), 3.69 (1H), 3.74-3.87 (2H), 3.76 (3H), 3.94 (2H), 4.00 (1H), 4.48 (1H), 5.01 (1H), 6.48 (1H), 6.50 (1H), 6.63 (2H), 6.96-7.05 (2H), 7.08 (1H), 7.15 (1H), 7.58 (1H).

Example 1-119

(rac)-12-Methoxy-1-[3-(1-naphthyloxy)propyl]-4,5,7,8-tetrahydro-10,14-(metheno)[1,4,7]dioxazacyclotetradecino[9,8,7-hi]indole-2-carboxylic acid

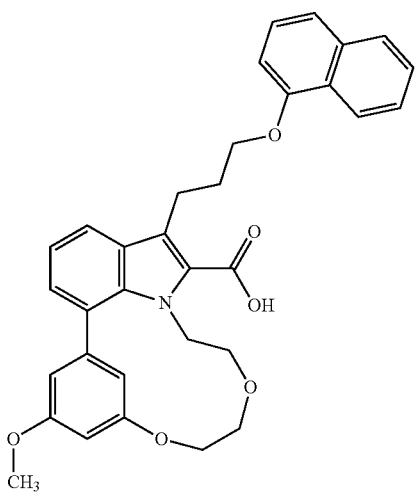

A mixture comprising (rac)-ethyl 12-methoxy-1-[3-(naphthalen-1-yloxy)propyl]-4,5,7,8-tetrahydro-10,14-(metheno)[1,4,7]dioxazacyclotetradecino[9,8,7-hi]indole-2-carboxylate (see Intermediate 1-237; 22.0 mg, 39 μmol), THF (1.0 ml), methanol (350 μl) and lithium hydroxide (233 μl, 1.0 M in water) was stirred at rt overnight. Water was added, the mixture was acidified by the addition of aqueous HCl (pH 3-4) and extracted with dichloromethane. The organic layer was dried over sodium sulfate. After filtration and removal of the solvents, the crude mixture was purified by preparative TLC (EtOH:dichloromethane) to give the title compound (8.3 mg, 38% yield).

MS: m/z=538.2 [M+H]$^+$.

$^1$H-NMR (400 MHz, DMSO-d6), δ [ppm]=2.17 (2H), 3.10-3.46 (4H), 3.68 (1H), 3.74-3.87 (2H), 3.76 (3H), 3.99 (1H), 4.17 (2H), 4.48 (1H), 5.00 (1H), 6.46 (1H), 6.50 (1H), 6.90 (1H), 6.98 (1H), 7.07 (1H), 7.13 (1H), 7.39 (1H), 7.45 (1H), 7.52 (2H), 7.62 (1H), 7.86 (1H), 8.22 (1H).

Example 1-120

(rac)-3-({4-[4-(Carboxymethyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid A mixture comprising (rac)-ethyl 3-({4-[4-(2-methoxy-2-oxoethyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (see Intermediate 1-238; 152 mg, 190 μmol), THF (7.7 mL), ethanol (5.5 mL) and lithium hydroxide (3.8 mL, 1.0 M in water) was stirred at 55° C. for 30 hrs. Water was added, the mixture acidified by the addition of citric acid (pH 5-6) and extracted with dichloromethane. The organic layer was washed with brine and dried. After removal of the solvents the residue was purified by preparative HPLC to give the title compound (62.0 mg, 52% yield).

Preparative HPLC method:

Instrument: Waters Autopurification system; column: Waters XBrigde C18 5μ 100×30 mm; eluent A: water+0.1 Vol-% formic acid (99%), eluent B: acetonitrile; gradient: 0.00-0.50 min 21% B (25→70 mL/min), 0.51-5.50 min 43-63% B (70 mL/min), DAD scan: 210-400 nm MS: m/z=759 [M+H]$^+$ $^1$H-NMR (400 MHz, DMSO-d6), δ [ppm]=1.06 (2H), 1.25 (1H), 1.35 (1H), 2.18 (2H), 2.60 (4H), 2.83 (1H), 2.90 (4H), 3.22-3.52 (5H), 3.92 (3H), 4.03-4.18 (3H), 4.28 (1H), 4.44 (1H), 4.52 (1H), 4.69 (2H), 6.49 (2H), 6.65 (2H), 6.80 (1H), 6.83 (1H), 6.97 (1H), 7.36 (1H), 7.44 (1H), 7.48-7.55 (2H), 7.71 (1H), 7.86 (1H), 8.24 (1H), 12.66-13.69 (1H).

Example 1-121

(rac)-3-({4-[4-(3-hydroxy-3-methylbutyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid ammonium salt

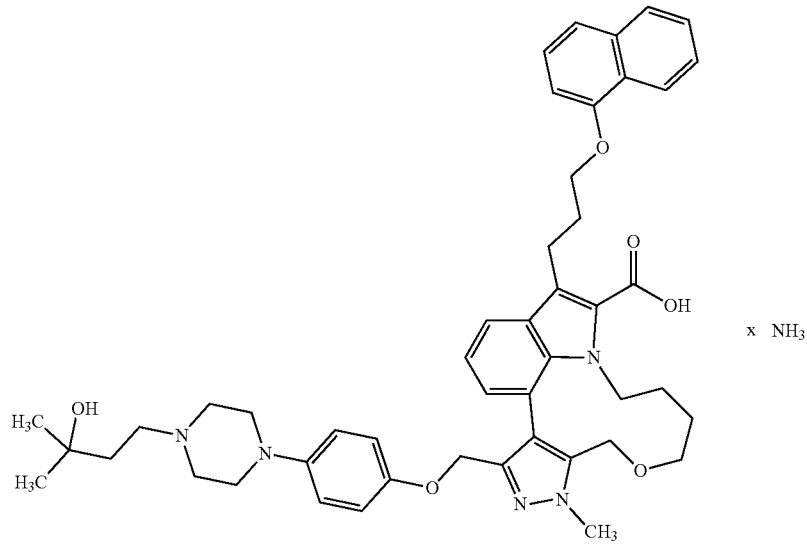

A mixture comprising (rac)-ethyl 3-({4-[4-(3-hydroxy-3-methylbutyl)piperazin-1-yl]phenoxy}methyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (see Intermediate 1-239; 44.0 mg, 54.1 μmol), THF (2.2 mL), ethanol (1.6 mL) and lithium hydroxide (1.2 mL, 1.0 M in water) was stirred at 50° C. for 16 hrs. Water was added, the mixture acidified by the addition of citric acid (pH 5-6) and extracted with dichloromethane. The organic layer was washed with brine and dried. After removal of the solvents the residue was purified by preparative HPLC to give the title compound (7.50 mg).

Preparative HPLC method:

Instrument: Waters Autopurification system; column: YMC Triart C18 5μ 100×30 mm; eluent A: water+0.2 Vol-% aqueous ammonia (32%), eluent B: acetonitrile; gradient: 0.00-0.50 min 14% B (25→70 mL/min), 0.51-5.50 min 28-43% B (70 mL/min), DAD scan: 210-400 nm MS: m/z=786 [M+H]$^+$ $^1$H-NMR (400 MHz, DMSO-d6), δ [ppm]=1.02 (2H), 1.07 (6H), 1.23 (1H), 1.39 (1H), 1.49 (2H), 2.18 (2H), 2.32-2.40 (5H), 2.81 (5H), 3.17-3.52 (4H), 3.92 (3H), 4.02-4.17 (3H), 4.28 (1H), 4.44 (1H), 4.57 (1H), 4.65-4.71 (2H), 6.49 (2H), 6.62 (2H), 6.77-6.83 (2H), 6.95 (1H), 7.36 (1H), 7.44 (1H), 7.48-7.54 (2H), 7.68 (1H), 7.86 (1H), 8.23 (1H).

Example 1-122

(rac)-12-Methoxy-1-[3-(naphthalen-1-yloxy)propyl]-5,6,7,8-tetrahydro-4H-10,14-(metheno)[1,7]oxazacyclotetradecino[9,8,7-hi]indole-2-carboxylic acid

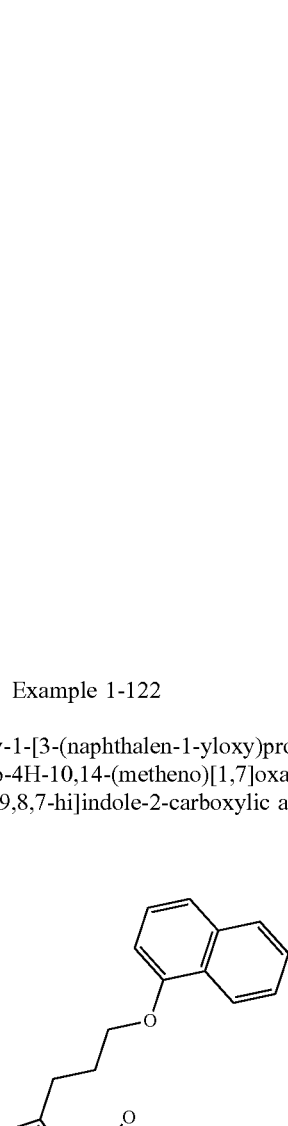

A mixture comprising (rac)-ethyl 12-methoxy-1-[3-(naphthalen-1-yloxy)propyl]-5,6,7,8-tetrahydro-4H-10,14-(metheno)[1,7]oxazacyclotetradecino[9,8,7-hi]indole-2-carboxylate (see Intermediate 1-240; 40.0 mg, 71.0 μmol), THF (2.7 ml), methanol (500 μl) and lithium hydroxide (430 μl, 1.0 M in water) was stirred at 80° C. for 2 hrs and at 50° C. over night. Water was added, the mixture was acidified by the addition of aqueous HCl (pH 3-4) and extracted with dichloromethane. The organic layer was dried over sodium sulfate. After filtration and removal of the solvents the residue was purified by preparative HPLC (method P1) to give the title compound (6.2 mg, 15% yield).

MS: m/z=536.5 [M+H]$^+$ $^1$H-NMR (400 MHz, DMSO-d6) δ[ppm]: 0.60 (1H), 1.43 (2H), 1.73-1.87 (2H), 2.00 (1H), 2.18 (2H), 3.14 (1H), 3.25-3.35 (2H), 3.77 (3H), 3.99 (1H), 4.19 (2H), 4.37 (1H), 4.77 (1H), 6.50 (1H), 6.53 (1H), 6.90 (1H), 7.03 (1H), 7.13 (1H), 7.14 (1H), 7.39 (1H), 7.46 (1H), 7.48-7.56 (2H), 7.74 (1H), 7.87 (1H), 8.22 (1H), 13.16 (1H)

Example 001

(rac)- (E/Z)-8-benzyl-9,11-dimethyl-1-[3-(1-naphthyloxy)propyl]-4,7,8,9-tetrahydropyrazolo[4',3':4,5][1,6]diazecino[3,2,1-hi]indole-2-carboxylic acid

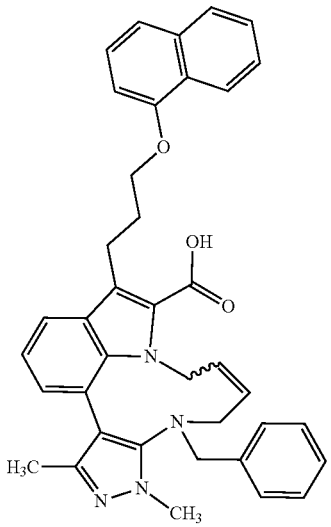 [SMILES: Cc1nn(C)c2c1-c1cccc3c(CCCOc4cccc5ccccc45)c(C(=O)O)n(c13)CC=CCN2Cc1ccccc1]

A mixture of (rac)-ethyl (E/Z)-8-benzyl-9,11-dimethyl-1-[3-(1-naphthyloxy)propyl]-4,7,8,9-tetrahydropyrazolo[4',3':4,5][1,6]diazecino[3,2,1-hi]indole-2-carboxylate (15 mg, 0.024 mmol, see Intermediate 25), lithium hydroxide hydrate (5.04 mg, 0.120 mmol), tetrahydrofuran (0.8 mL), methanol (0.27 mL), and water (1.3 mL) was stirred at 150° C. for 30 min in a microwave. Upon completion, the volatiles were removed and the crude product was purified by reverse phase flash chromatography on C18 silica gel (0-100% acetonitrile/water with 10 mM ammonium formate buffer) to afford, after lyophilization, the title compound (6.8 mg, 0.011 mmol).

$^1$H NMR (500 MHz, MeOD) δ [ppm]: 8.39-8.33 (m, 1H), 7.81-7.76 (m, 1H), 7.64 (d, J=7.8 Hz, 1H), 7.50-7.44 (m, 2H), 7.37 (d, J=8.2 Hz, 1H), 7.31 (t, J=7.9 Hz, 1H), 7.24-7.15 (m, 3H), 7.10 (d, J=6.9 Hz, 2H), 7.01 (t, J=7.5 Hz, 1H), 6.91 (d, J=7.1 Hz, 1H), 6.83 (d, J=7.5 Hz, 1H), 5.68 (dt, J=11.2, 5.6 Hz, 1H), 5.56 (dd, J=18.0, 9.3 Hz, 1H), 5.08 (dd, J=16.6, 5.1 Hz, 1H), 4.55 (dd, J=16.9, 5.2 Hz, 1H), 4.22 (t, J=6.1 Hz, 2H), 3.69 (d, J=13.2 Hz, 1H), 3.61-3.50 (m, 5H), 3.46-3.25 (m, 3H), 2.35 (p, J=6.8 Hz, 2H), 1.95 (s, 3H).

MS: m/z=597.48 [M+H]$^+$

Example 002 and Example 003

(rac)-8-benzyl-9,11-dimethyl-1-[3-(1-naphthyloxy)propyl]-4,5,6,7,8,9-hexahydropyrazolo[4',3':4,5][1,6]diazecino[3,2,1-hi]indole-2-carboxylic acid (Example 002) and (rac)-9,11-dimethyl-1-[3-(1-naphthyloxy)propyl]-4,5,6,7,8,9-hexahydropyrazolo[4',3':4,5][1,6]diazecino[3,2,1-hi]indole-2-carboxylic acid (Example 003)

Example 002

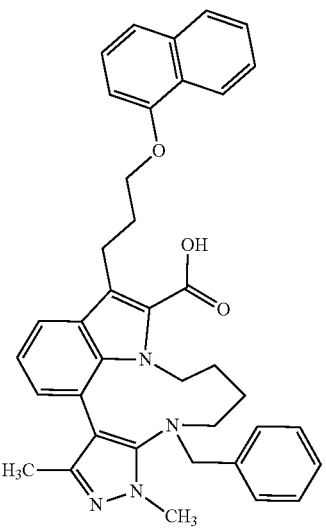

Example 003

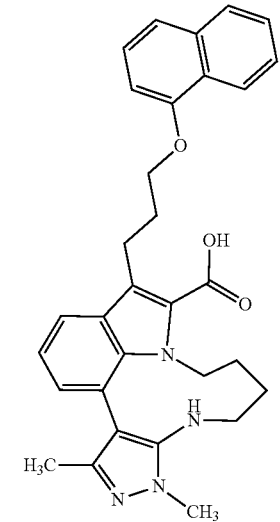

To a solution of (rac)-ethyl (5Z)-8-benzyl-9,11-dimethyl-1-[3-(1-naphthyloxy)propyl]-4,7,8,9-tetrahydropyrazolo[4',3':4,5][1,6]diazecino[3,2,1-hi]indole-2-carboxylate (22 mg, 0.035 mmol, see Intermediate 25) in methanol (704 μl) was added palladium on charcoal (3.75 mg, 3.52 μmol). The mixture was evacuated and purged with hydrogen gas three times and then stirred for 20 h. Upon completion of the reaction, as indicated by LCMS, the mixture was filtered through Celite, rinsed with methanol, and concentrated. The crude residue was treated with lithium hydroxide hydrate (36.8 mg, 0.877 mmol), tetrahydrofuran (1.1 mL), methanol (0.39 mL), and water (2 mL) and the mixture was heated in a microwave at 150° C. for 30 min. Upon completion, the volatiles were removed and the crude product was purified by reverse phase flash chromatography on C18 silica gel (0-100% acetonitrile/water with 0.1% formic acid buffer) to afford, after lyophilization, Example 002 (66.4 mg, 0.108 mmol), and Example 003 (8.8 mg, 0.017 mmol).

Example 002

$^1$H NMR (500 MHz, MeOD) δ [ppm]: 8.37-8.31 (m, 1H), 7.82-7.74 (m, 2H), 7.51-7.46 (m, 2H), 7.38 (d, J=8.3 Hz, 1H), 7.30 (t, J=7.9 Hz, 1H), 7.22-7.13 (m, 3H), 7.02-6.96 (m, 3H), 6.87 (d, J=7.0 Hz, 1H), 6.79 (d, J=7.6 Hz, 1H), 4.66 (dt, J=14.4, 3.9 Hz, 1H), 4.20 (t, J=5.9 Hz, 2H), 4.03-3.95 (m, 1H), 3.76 (d, J=14.2 Hz, 1H), 3.69 (s, 3H), 3.55-3.46 (m, 2H), 3.46-3.38 (m, 1H), 2.92 (dd, J=14.8, 5.4 Hz, 1H), 2.35 (p, J=6.8 Hz, 2H), 1.99-1.89 (m, 4H), 1.48-1.38 (m, 1H), 1.35-1.19 (m, 3H).

MS: m/z=599.50 [M+H]$^+$

Example 003

$^1$H NMR (500 MHz, MeOD) δ [ppm]: 8.24 (d, J=8.0 Hz, 1H), 7.78 (d, J=7.6 Hz, 1H), 7.69 (d, J=7.8 Hz, 1H), 7.50-7.41 (m, 2H), 7.37 (d, J=8.2 Hz, 1H), 7.31 (t, J=7.9 Hz, 1H), 7.00 (t, J=7.5 Hz, 1H), 6.95 (d, J=6.9 Hz, 1H), 6.78 (d, J=7.5 Hz, 1H), 4.64-4.56 (m, 1H), 4.36-4.26 (m, 1H), 4.19 (t, J=6.0 Hz, 2H), 3.64 (s, 3H), 3.49-3.34 (m, 3H), 3.23-3.15 (m, 1H), 2.85 (dt, J=14.9, 4.8 Hz, 1H), 2.37-2.27 (m, 2H), 2.00-1.89 (m, 5H), 1.58 (dd, J=13.5, 11.0 Hz, 1H), 1.52-1.43 (m, 1H), 0.83 (t, J=12.7 Hz, 1H). Amino and carboxylic acid protons do not appear in the spectra.

MS: m/z=509.48 [M+H]$^+$

Example 004

(rac)- (7-benzyl-11-({4-[4-(dimethylsulfamoyl)piperazin-1-yl]phenoxy}methyl)-9-methyl-1-[3-(1-naphthyloxy)propyl]-4,5,6,7,8,9-hexahydropyrazolo[3',4':7,8][1,5]diazecino[9,10,1-hi]indole-2-carboxylic acid

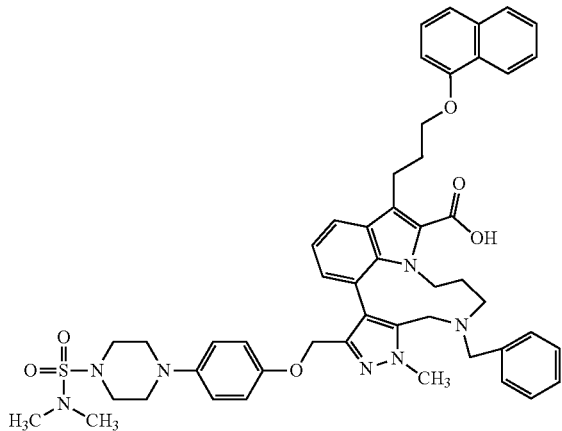 [SMILES: CN(C)S(=O)(=O)N1CCN(c2ccc(OCc3nn(C)c4c3-c3cccc5c(CCCOc6cccc7ccccc67)c(C(=O)O)n(c35)CCCN(Cc3ccccc3)C4)cc2)CC1]

To a solution of (rac)-ethyl 7-benzyl-11-({4-[4-(dimethylsulfamoyl)piperazin-1-yl]phenoxy}methyl)-9-methyl-1-[3-(1-naphthyloxy)propyl]-4,5,6,7,8,9-hexahydropyrazolo[3',4':7,8][1,5]diazecino[9,10,1-hi]indole-2-carboxylate (53.0 mg, 0.056 mmol, see Intermediate 37) in tetrahydrofuran (1 mL) and methanol (0.5 mL) was added lithium hydroxide hydrate (48.0 mg, 1.12 mmol) in water (0.5 mL). The mixture was stirred at 50° C. for 24 h. The crude product was purified by preparative HPLC to afford the title compound (28 mg). m/z=882 [M+H]$^+$ $^1$H NMR (300 MHz, CDCl$_3$) δ [ppm]: 8.39-8.36 (m, 1H), 7.80-7.76 (m, 2H), 7.49-7.45 (m, 2H), 7.41-7.29 (m, 2H), 7.11-6.95 (m, 5H), 6.71-6.59 (m, 7H), 4.82 (s, 2H), 4.49-4.40 (m, 1H), 4.21-4.17 (m, 2H), 3.90-3.83 (m, 4H), 3.58-3.29 (m, 12H), 3.0-2.96 (m, 4H), 2.80 (s, 6H), 2.37-2.25 (m, 4H).

Example 005

(rac)-9,11-dimethyl-1-[3-(5,6,7,8-tetrahydronaphthalen-1-yloxy)propyl]-5,6,8,9-tetrahydro-4H-pyrazolo[4',3':8,9][1,5]oxazecino[7,6,5-hi]indole-2-carboxylic acid

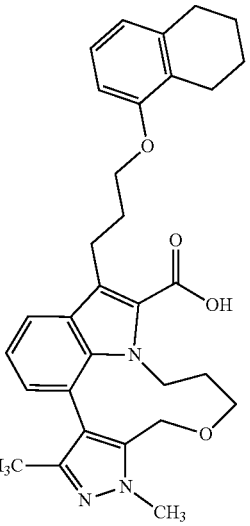

A solution of (rac)-ethyl 9,11-dimethyl-1-[3-(5,6,7,8-tetrahydronaphthalen-1-yloxy)propyl]-5,6,8,9-tetrahydro-4H-pyrazolo[4',3':8,9][1,5]oxazecino[7,6,5-hi]indole-2-carboxylate (35 mg, 0.064 mmol, see Intermediate 44) in methanol (2 ml), tetrahydrofuran (4 ml), and lithium hydroxide (2M in water, 0.5 ml, 1 mmol) was stirred at room temperature for 48 hours, heated to 60° C. for 16 hours, then cooled to room temperature. Volatiles were removed under reduced pressure and the residue was partitioned between ethyl acetate and aqueous hydrochloric acid (3M), the organic layer was washed with saturated aqueous sodium chloride solution and then dried over magnesium sulfate, insoluble material was removed by filtration, volatiles were removed under reduced pressure, and the residue was purified by normal phase chromatography on silica gel (12 g) eluting with a gradient of methanol in dichloromethane (2-4%) to give the title compound (26 mg).

LRMS (ESI) M+H+514, M–H$^-$ 512;

$^1$H NMR (400 MHz, DMSO-d$_6$) δ [ppm]: 13.12 (s, 1H), 7.72 (d, J=8.0 Hz, 1H), 7.15-7.07 (m, 1H), 7.00 (t, J=7.9 Hz, 1H), 6.96 (d, J=6.8 Hz, 1H), 6.68-6.60 (m, 2H), 4.79 (d, J=14.3 Hz, 1H), 4.53 (d, J=14.2 Hz, 1H), 3.99 (t, J=6.1 Hz, 2H), 3.88 (m, 1H), 3.83 (s, 3H), 3.69 (d, J=14.3 Hz, 1H), 3.29 (s, 3H), 2.75-2.59 (m, 4H), 2.36-2.30 (m, 1H), 2.05 (t, J=7.1 Hz, 2H), 1.94 (s, 3H), 1.68 (d, J=29.2 Hz, 6H).

Example 006

(rac)-1,3-dimethyl-7-[3-(5,6,7,8-tetrahydronaphthalen-1-yloxy)propyl]-1,10,11,12,13,15-hexahydropyrazolo[4',3':9,10][1,6]oxazacycloundecino[8,7,6-hi]indole-8-carboxylic acid

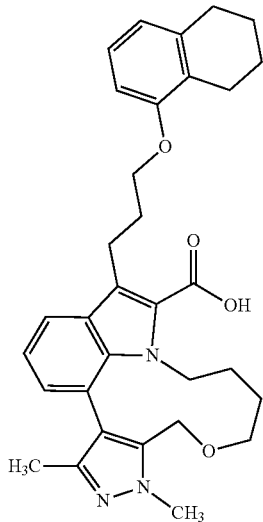 [SMILES: Cc1nn(C)c2c1-c1cccc3c(CCCOc4cccc5c4CCCC5)c(C(=O)O)n(c13)CCCCOC2]

A solution of (rac)-ethyl 1,3-dimethyl-7-[3-(5,6,7,8-tetrahydronaphthalen-1-yloxy)propyl]-1,10,11,12,13,15-hexahydropyrazolo[4',3':9,10][1,6]oxazacycloundecino[8,7,6-hi]indole-8-carboxylate (160 mg 0.28 mmol, see Intermediate 53) in methanol (5 ml), lithium hydroxide (2M in water, 5 ml, 10 mmol), and tetrahydrofuran (5 ml) was heated to 50° C. for 15 hours, then cooled to room temperature. The reaction was diluted with ethyl acetate and aqueous hydrochloric acid (3M), layers were separated and the organic layer was washed with saturated aqueous sodium chloride solution and was then dried over magnesium sulfate, insoluble material was removed by filtration, volatiles were removed under reduced pressure, and the residue was purified by normal phase chromatography on silica gel (12 g) eluting with a gradient of methanol in dichloromethane (0-10%) to give the title compound as a white solid (72 mg).

$^1$H NMR (400 MHz, DMSO-d6) δ[ppm]: 13.09 (s, 1H), 7.71 (dd, J=8.1, 1.3 Hz, 1H), 7.08 (t, J=7.5 Hz, 1H), 6.99 (t, J=7.9 Hz, 1H), 6.85 (dd, J=7.1, 1.2 Hz, 1H), 6.63 (d, J=7.9 Hz, 2H), 4.65 (d, J=13.4 Hz, 1H), 4.54 (dt, J=14.0, 4.5 Hz, 1H), 4.28 (d, J=13.4 Hz, 1H), 3.99 (h, J=5.3, 4.8 Hz, 3H), 3.84 (s, 3H), 3.42 (dt, J=11.6, 6.9 Hz, 1H), 3.29-3.13 (m, 2H), 2.75 (dt, J=11.6, 7.1 Hz, 1H), 2.68 (t, J=5.9 Hz, 2H), 2.63 (t, J=6.2 Hz, 2H), 2.06 (p, J=7.0 Hz, 2H), 1.81 (s, 3H), 1.77-1.63 (m, 4H), 1.37-1.16 (m, 2H), 1.04 (d, J=8.3 Hz, 2H).

LRMS (ESI) M+H+ 528.

The title compound (46 mg) was separated into enantiomers by preparative chiral HPLC to give enantiomer 1 (14 mg, see Example 007) and enantiomer 2 (15 mg, see Example 008).

Preparative chiral HPLC method: Instrument: Sepiatec: Prep SFC100; column: Chiralpak ID 5 μm 250×30 mm; eluent A: $CO_2$, eluent B: 2-propanol+0.4 Vol-% diethylamine (99%); isocratic: 21% B; flow 100.0 ml/min temperature: 40° C.; BPR: 150 bar; MWD @ 254 nm Analytical chiral HPLC method: Instrument: Agilent: 1260, Aurora SFC-Module; column: Chiralpak ID 5 μm 100×4.6 mm; eluent A: $CO_2$, eluent B: 2-propanol+0.2 Vol-% diethylamine (99%); isocratic: 21% B; flow 4.0 ml/min; temperature: 37.5° C.; BPR: 100 bar; MWD @ 254 nm Example 007

1,3-dimethyl-7-[3-(5,6,7,8-tetrahydronaphthalen-1-yloxy)propyl]-1,10,11,12,13,15-hexahydropyrazolo[4',3':9,10][1,6]oxazacycloundecino[8,7,6-hi]indole-8-carboxylic acid-N-ethylethanamine salt (Enantiomer 1)

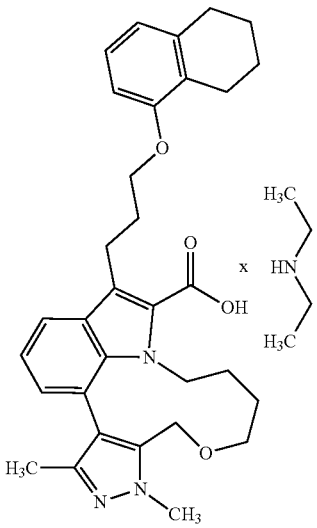

For the preparation of the racemic title compound see Example 006. Separation of enantiomers by preparative chiral HPLC (method see Example 006) gave the title compound (14 mg).

Analytical Chiral HPLC (method see Example 006): $R_t$=2.25 min.

LC-MS (Method 2): $R_t$=0.91 min; MS (ESIpos): m/z=528 [M+H]$^+$ $^1$H-NMR (400 MHz, DMSO-d6) δ[ppm]: 0.968 (0.51), 0.992 (0.43), 1.009 (0.49), 1.023 (0.53), 1.108 (16.00), 1.139 (1.39), 1.144 (0.67), 1.158 (2.52), 1.175 (1.34), 1.233 (0.56), 1.681 (0.72), 1.694 (0.96), 1.708 (1.04), 1.722 (0.92), 1.739 (0.72), 1.816 (8.14), 1.960 (0.45), 2.029 (0.56), 2.047 (0.78), 2.064 (0.57), 2.323 (0.69), 2.327 (0.96), 2.331 (0.69), 2.518 (3.17), 2.523 (2.17), 2.540 (0.45), 2.608 (0.78), 2.624 (1.48), 2.638 (0.73), 2.665 (1.51), 2.669 (1.64), 2.674 (1.45), 2.678 (1.80), 2.695 (0.91), 2.887 (0.70), 2.905 (0.70), 3.224 (0.49), 3.241 (0.41), 3.257 (0.41), 3.404 (0.45), 3.832 (8.80), 3.954 (0.80), 3.970 (1.35), 3.985 (0.65), 4.246 (0.92), 4.279 (1.04), 4.626 (1.39), 4.660 (1.05), 6.614 (1.47), 6.633 (1.42), 6.761 (0.53), 6.778 (0.56), 6.961 (0.72), 6.980 (1.18), 6.999 (0.59), 7.015 (0.54), 7.034 (0.84), 7.052 (0.48), 7.632 (0.61), 7.652 (0.56).

Example 008

1,3-dimethyl-7-[3-(5,6,7,8-tetrahydronaphthalen-1-yloxy)propyl]-1,10,11,12,13,15-hexahydropyrazolo[4',3':9,10][1,6]oxazacycloundecino[8,7,6-hi]indole-8-carboxylic acid-N-ethylethanamine salt (Enantiomer 2)

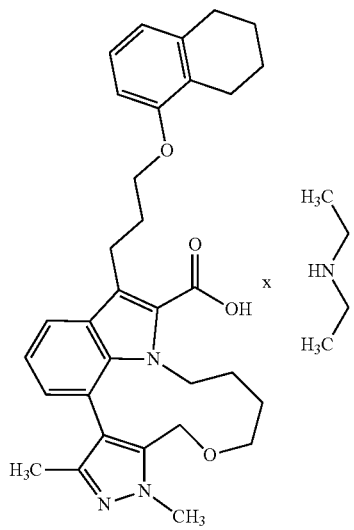

For the preparation of the racemic title compound see Example 006. Separation of enantiomers by preparative chiral HPLC (method see Example 006) gave the title compound (15 mg).

Analytical Chiral HPLC (method see Example 006): $R_t$=4.03 min.

LC-MS (Method 2): $R_t$=0.91 min; MS (ESIpos): m/z=528 [M+H]$^+$ $^1$H-NMR (400 MHz, DMSO-d6) δ[ppm]: 0.968 (0.51), 0.992 (0.65), 1.009 (0.60), 1.089 (0.47), 1.108 (16.00), 1.141 (2.22), 1.159 (4.33), 1.177 (2.19), 1.233 (0.40), 1.679 (0.73), 1.693 (0.96), 1.706 (1.06), 1.720 (0.96), 1.738 (0.72), 1.817 (9.02), 1.960 (0.70), 2.028 (0.57), 2.045 (0.83), 2.062 (0.61), 2.323 (0.56), 2.327 (0.78), 2.331 (0.55), 2.518 (2.69), 2.523 (1.80), 2.606 (0.83), 2.622 (1.55), 2.637 (0.76), 2.665 (1.40), 2.669 (1.42), 2.678 (1.81), 2.694 (0.93), 2.864 (0.48), 2.882 (1.49), 2.900 (1.45), 2.919 (0.46), 3.127 (0.40), 3.220 (0.55), 3.239 (0.47), 3.256 (0.42), 3.402 (0.48), 3.431 (0.40), 3.830 (8.83), 3.952 (0.72), 3.968 (1.37), 3.984 (0.68), 4.243 (1.03), 4.277 (1.13), 4.625 (1.47), 4.658 (1.16), 6.613 (1.46), 6.631 (1.38), 6.635 (1.33), 6.743 (0.57), 6.760 (0.63), 6.958 (0.74), 6.978 (1.21), 6.997 (0.70), 7.003 (0.64), 7.022 (0.90), 7.041 (0.52), 7.616 (0.82), 7.638 (0.72).

Example 009

(rac)-7-[3-(4-chloro-3,5-dimethylphenoxy)propyl]-1,3-dimethyl-1,10,11,12,13,15-hexahydropyrazolo[4',3':9,10][1,6]oxazacycloundecino[8,7,6-hi]indole-8-carboxylic acid

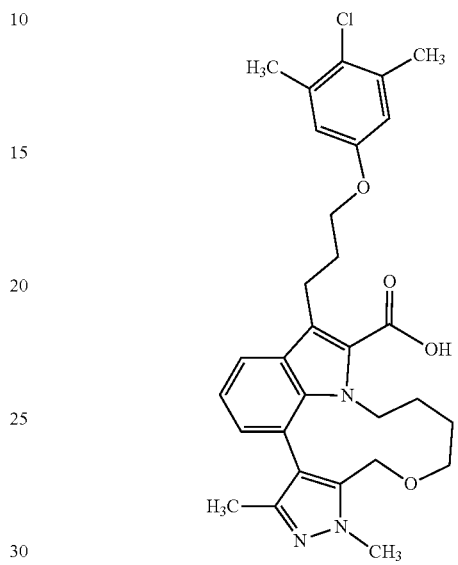

A solution of (rac)-ethyl 7-[3-(4-chloro-3,5-dimethylphenoxy)propyl]-1,3-dimethyl-1,10,11,12,13,15-hexahydropyrazolo[4',3':9,10][1,6]oxazacycloundecino[8,7,6-hi]indole-8-carboxylate (190 mg 0.34 mmol, see Intermediate 54) in methanol (2 ml), tetrahydrofuran (4 ml), and lithium hydroxide (2M in water, 1 ml, 2 mmol), was heated to 60° C. for 48 hours, then cooled to room temperature. The reaction mixture was diluted with ethyl acetate and aqueous hydrochloric acid (3M), layers were separated and the organic layer was washed with saturated aqueous sodium chloride solution, the combined aqueous phases were extracted with ethyl acetate, the combined organic layers were dried over magnesium sulfate, insoluble material was removed by filtration, volatiles were removed under reduced pressure, and the residue was purified by normal phase chromatography on silica gel (4 g) eluting with a gradient of methanol in dichloromethane (0-5%) to give the title compound as a white solid (143 mg).

$^1$H NMR (400 MHz, DMSO-d$_6$) δ [ppm] 13.07 (s, 1H), 7.71 (dd, J=8.0, 1.2 Hz, 1H), 7.09 (t, J=7.5 Hz, 1H), 6.85 (dd, J=7.1, 1.2 Hz, 1H), 6.74 (s, 2H), 4.64 (d, J=13.4 Hz, 1H), 4.59-4.47 (m, 1H), 4.28 (d, J=13.4 Hz, 1H), 3.97 (dd, J=9.3, 4.6 Hz, 3H), 3.84 (s, 3H), 3.42 (dt, J=12.7, 6.9 Hz, 1H), 3.27-3.09 (m, 2H), 2.75 (dt, J=11.7, 7.0 Hz, 1H), 2.27 (s, 6H), 2.10-1.96 (m, 2H), 1.81 (s, 3H), 1.24 (s, 4H).

LRMS (ESI) M+H+537, M−H− 535

The title compound (124 mg) was separated into enantiomers by preparative chiral HPLC to give enantiomer 1 (50 mg, see Example 010) and enantiomer 2 (50 mg, see Example 011).

Preparative chiral HPLC method: Instrument: Sepiatec: Prep SFC100; column: Chiralpak ID 5 μm 250×30 mm; eluent A: $CO_2$, eluent B: 2-propanol+0.4 Vol-% diethylamine (99%); isocratic: 27% B; flow 100.0 ml/min temperature: 40° C.; BPR: 150 bar; MWD @ 254 nm Analytical chiral HPLC method: Instrument: Agilent: 1260, Aurora SFC-Module; column: Chiralpak ID 5 μm 100×4.6 mm; eluent A: $CO_2$, eluent B: 2-propanol+0.2 Vol-% diethylamine (99%); isocratic: 27% B; flow 4.0 ml/min; temperature: 37.5° C.; BPR: 100 bar; MWD @ 254 nm Example 010

7-[3-(4-chloro-3,5-dimethylphenoxy)propyl]-1,3-dimethyl-1,10,11,12,13,15-hexahydropyrazolo[4',3':9,10][1,6]oxazacycloundecino[8,7,6-hi]indole-8-carboxylic acid-N-ethylethanamine salt (Enantiomer 1)

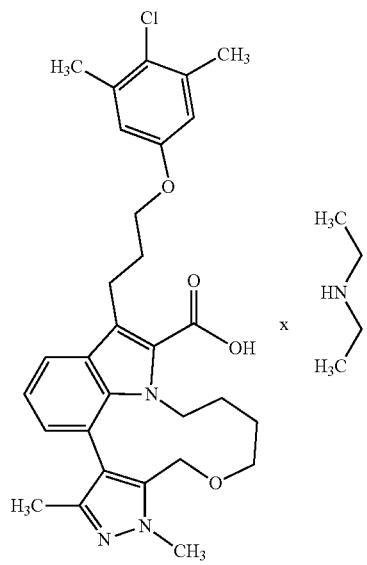

For the preparation of the racemic title compound see Example 009. Separation of enantiomers by preparative chiral HPLC (method see Example 009) gave the title compound (50 mg).

Analytical Chiral HPLC (method see Example 009): $R_t$=1.79 min.

LC-MS (Method 2): $R_t$=0.89 min; MS (ESIpos): m/z=536 [M+H]$^+$

1H-NMR (400 MHz, DMSO-d6): δ [ppm]=7.57 (br d, 1H), 6.98 (t, 1H), 6.75-6.63 (m, 3H), 4.62 (d, 2H), 4.27-4.13 (m, 2H), 4.03-3.73 (m, 6H), 3.23-3.11 (m, 1H), 3.03 (dt, 1H), 2.86 (q, 2H), 2.76-2.67 (m, 1H), 2.23 (s, 6H), 2.08-1.93 (m, 2H), 1.80 (s, 3H), 1.33 (br s, 1H), 1.25-1.05 (m, 1H), 1.05-0.89 (m, 2H)

Example 011

7-[3-(4-chloro-3,5-dimethylphenoxy)propyl]-1,3-dimethyl-1,10,11,12,13,15-hexahydropyrazolo[4',3':9,10][1,6]oxazacycloundecino[8,7,6-hi]indole-8-carboxylic acid-N-ethylethanamine salt (Enantiomer 2)

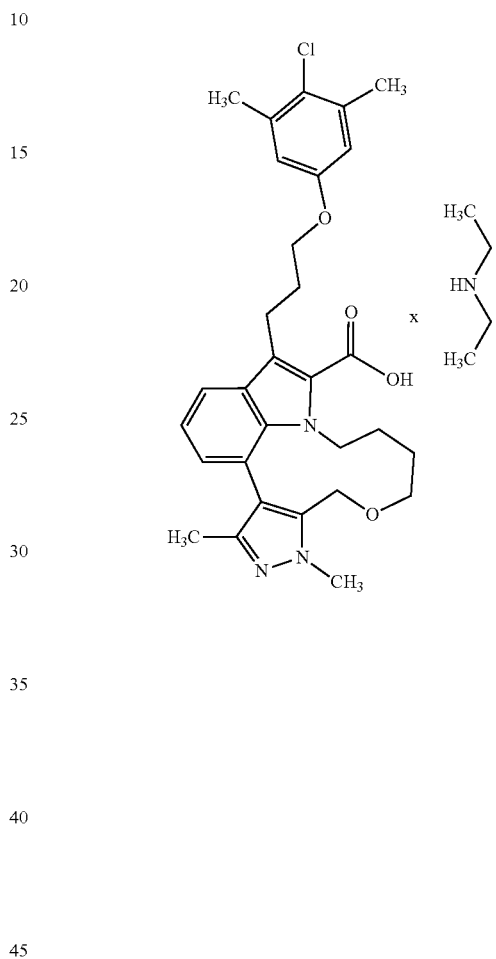

For the preparation of the racemic title compound see Example 009. Separation of enantiomers by preparative chiral HPLC (method see Example 009) gave the title compound (50 mg).

Analytical Chiral HPLC (method see Example 009): $R_t$=3.63 min.

LC-MS (Method 2): $R_t$=0.90 min; MS (ESIpos): m/z=536 [M+H]$^+$ $^1$H-NMR (400 MHz, DMSO-d6) δ[ppm]: 1.026 (0.53), 1.139 (0.96), 1.158 (2.00), 1.176 (1.07), 1.232 (0.62), 1.814 (8.83), 2.007 (0.62), 2.024 (0.87), 2.041 (0.59), 2.262 (16.00), 2.518 (2.74), 2.523 (1.91), 2.540 (6.89), 2.674 (0.56), 2.898 (0.66), 2.916 (0.63), 3.121 (0.43), 3.200 (0.52), 3.404 (0.48), 3.835 (8.51), 3.936 (0.52), 3.944 (0.63), 3.960 (1.15), 3.972 (1.14), 3.988 (0.44), 4.248 (0.97), 4.282 (1.09), 4.626 (1.22), 4.660 (1.09), 6.741 (4.44), 6.791 (0.59), 6.808 (0.67), 7.034 (0.62), 7.053 (0.91), 7.072 (0.56), 7.657 (0.70), 7.676 (0.66).

Example 012

(rac)-1,3-dimethyl-7-{3-[(7-methyl-1-naphthyl)oxy]propyl}-1,10,11,12,13,15-hexahydropyrazolo[4',3':9,10][1,6]oxazacycloundecino[8,7,6-hi]indole-8-carboxylic acid

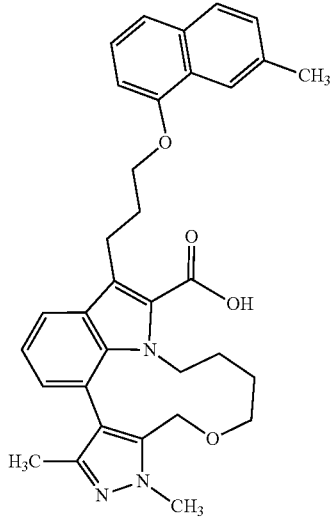 [SMILES: Cc1ccc2cccc(OCCCc3c(C(=O)O)n4c5c(cccc35)-c3c(C)nn(C)c3COCCCC4)c2c1]

A solution of (rac)-ethyl 1,3-dimethyl-7-{3-[(7-methyl-1-naphthyl)oxy]propyl}-1,10,11,12,13,15-hexahydropyrazolo[4',3':9,10][1,6]oxazacycloundecino[8,7,6-hi]indole-8-carboxylate (30 mg 0.05 mmol, see Intermediate 55) in methanol (5 ml), tetrahydrofuran (10 ml), and lithium hydroxide (2M in water, 5 ml, 10 mmol), was heated to 50° C. for 24 hours, then cooled to room temperature. The reaction mixture was diluted with ethyl acetate and aqueous hydrochloric acid (3M), layers were separated and the organic layer was washed with saturated aqueous sodium chloride solution, the combined aqueous phases were extracted with ethyl acetate, the combined organic layers were dried over magnesium sulfate, insoluble material was removed by filtration, volatiles were removed under reduced pressure, and the residue was purified by normal phase chromatography on silica gel (12 g) eluting with a gradient of methanol in dichloromethane (0-5%) to give the title compound as a white solid (26 mg).

$^1$H NMR (400 MHz, Chloroform-d) δ [ppm]: 8.14 (s, 1H), 7.80 (dd, J=8.1, 1.3 Hz, 1H), 7.69 (d, J=8.3 Hz, 1H), 7.36 (d, J=8.2 Hz, 1H), 7.32 (dd, J=8.3, 1.7 Hz, 1H), 7.30-7.21 (m, 1H), 7.09 (dd, J=8.0, 7.1 Hz, 1H), 6.91 (dd, J=7.0, 1.2 Hz, 1H), 6.73 (d, J=7.6 Hz, 1H), 4.67 (dd, J=14.4, 4.3 Hz, 1H), 4.59 (d, J=13.5 Hz, 1H), 4.46 (d, J=13.5 Hz, 1H), 4.20 (q, J=5.9 Hz, 2H), 4.17-4.08 (m, 1H), 3.96 (s, 3H), 3.58-3.34 (m, 3H), 2.86 (ddd, J=13.2, 9.5, 4.2 Hz, 1H), 2.54 (s, 3H), 2.37 (p, J=6.9 Hz, 2H), 1.99 (s, 3H), 1.59-1.45 (m, 1H), 1.36-1.15 (m, 2H), 1.08 (dt, J=14.7, 7.7 Hz, 1H).

LRMS (ESI) M+H+538 M−H− 536.

Example 013

(rac)-1-[3-(4-chloro-3,5-dimethylphenoxy)propyl]-9,11-dimethyl-5,6,8,9-tetrahydro-4H-pyrazolo[4',3':8,9][1,5]oxazecino[7,6,5-hi]indole-2-carboxylic acid

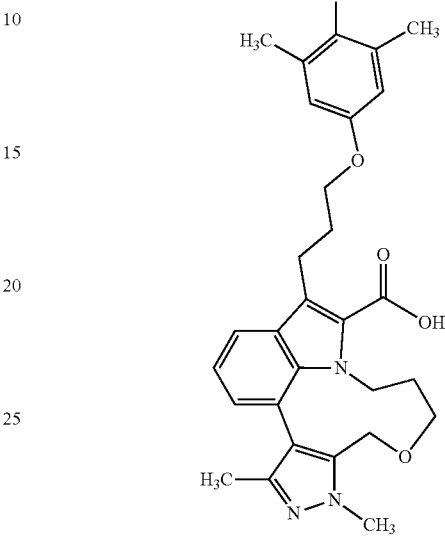

A solution of impure (rac)-ethyl 1-[3-(4-chloro-3,5-dimethylphenoxy)propyl]-9,11-dimethyl-5,6,8,9-tetrahydro-4H-pyrazolo[4',3':8,9][1,5]oxazecino[7,6,5-hi]indole-2-carboxylate (200 mg, see Intermediate 45) in methanol (4 ml), tetrahydrofuran (8 ml) and lithium hydroxide (2M in water, 1 ml, 2 mmol) was heated to 50° C. for 20 hours, then cooled to room temperature, the reaction mixture was diluted with ethyl acetate and aqueous hydrochloric acid (3M), layers were separated, the organic layer was washed with saturated aqueous sodium chloride solution and was then dried over magnesium sulfate, insoluble material was removed by filtration, volatiles were removed under reduced pressure, and the residue was purified by normal phase chromatography on silica gel (4 g) eluting with a gradient of methanol in dichloromethane (0-5%) to give the title compound with other impurities, this was purified by normal phase chromatography on silica gel (12 g) eluting with a gradient of methanol in dichloromethane (2-4%) to yield the title compound as a white solid (40 mg).

LRMS (ESI) M+H+522, M−H− 520;
$^1$H NMR (400 MHz, DMSO-d$_6$) δ [ppm]: 13.11 (s, 1H), 7.72 (dd, J=8.1, 1.3 Hz, 1H), 7.10 (t, J=7.5 Hz, 1H), 6.96 (dd, J=7.1, 1.2 Hz, 1H), 6.76 (s, 2H), 4.78 (d, J=14.3 Hz, 1H), 4.52 (d, J=14.5 Hz, 1H), 4.00-3.93 (m, 2H), 3.90 (d, J=11.7 Hz, 1H), 3.83 (s, 3H), 3.75 (d, J=12.9 Hz, 1H), 3.68 (d, J=14.3 Hz, 1H), 3.28-3.18 (m, 1H), 3.14 (dt, J=13.8, 7.4 Hz, 1H), 2.62 (t, J=11.4 Hz, 1H), 2.28 (s, 6H), 2.03 (q, J=7.1, 6.5 Hz, 2H), 1.94 (s, 3H), 1.62 (m, 2H).

The title compound (28 mg) was separated into enantiomers by preparative chiral HPLC to give enantiomer 1 (6 mg, see Example 014) and enantiomer 2 (5 mg, see Example 015).

Preparative chiral HPLC method: Instrument: Sepiatec: Prep SFC100; column: Chiralpak ID 5 μm 250×30 mm; eluent A: CO$_2$, eluent B: 2-propanol+0.4 Vol-% diethylamine (99%); isocratic: 27% B; flow 100.0 ml/min temperature: 40° C.; BPR: 150 bar; MWD @ 254 nm Analytical chiral HPLC method: Instrument: Agilent: 1260, Aurora SFC-Module; column: Chiralpak ID 5 µm 100×4.6 mm; eluent A: $CO_2$, eluent B: 2-propanol+0.2 Vol-% diethylamine (99%); isocratic: 27% B; flow 4.0 ml/min; temperature: 37.5° C.; BPR: 100 bar; MWD @ 254 nm

Example 014

1-[3-(4-chloro-3,5-dimethylphenoxy)propyl]-9,11-dimethyl-5,6,8,9-tetrahydro-4H-pyrazolo[4',3':8,9][1,5]oxazecino[7,6,5-hi]indole-2-carboxylic acid-N-ethylethanamine salt (Enantiomer 1)

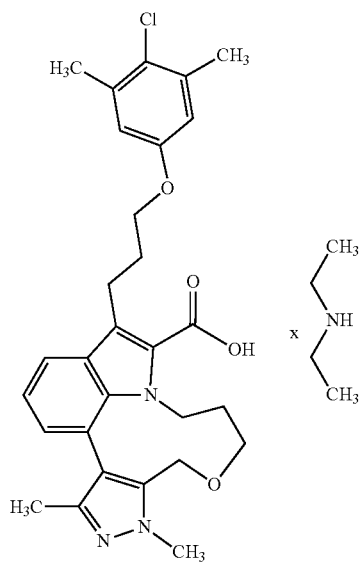

For the preparation of the racemic title compound see Example 013. Separation of enantiomers by preparative chiral HPLC (method see Example 013) gave the title compound (6 mg).

Analytical Chiral HPLC (method see Example 013): $R_t$=1.90 min.

LC-MS (Method 2): $R_t$=0.90 min; MS (ESIpos): m/z=522 [M+H]$^+$ $^1$H-NMR (400 MHz, DMSO-d6) δ[ppm]: 1.108 (3.44), 1.134 (2.63), 1.144 (0.46), 1.152 (6.08), 1.170 (2.79), 1.233 (0.50), 1.933 (9.10), 1.993 (0.69), 2.009 (0.58), 2.259 (16.00), 2.518 (3.90), 2.523 (2.73), 2.580 (0.56), 2.861 (0.71), 2.879 (2.13), 2.897 (2.13), 2.915 (0.67), 3.166 (0.42), 3.609 (0.87), 3.645 (0.87), 3.735 (0.50), 3.756 (0.56), 3.809 (8.69), 3.929 (0.46), 3.937 (0.58), 3.945 (0.96), 3.953 (0.98), 3.961 (0.56), 3.969 (0.46), 4.763 (1.13), 4.798 (1.08), 6.740 (4.38), 6.823 (0.44), 6.840 (0.50), 6.999 (0.46), 7.017 (0.75), 7.036 (0.40), 7.592 (0.48), 7.610 (0.46).

Example 015

1-[3-(4-chloro-3,5-dimethylphenoxy)propyl]-9,11-dimethyl-5,6,8,9-tetrahydro-4H-pyrazolo[4',3':8,9][1,5]oxazecino[7,6,5-hi]indole-2-carboxylic acid-N-ethylethanamine salt (Enantiomer 2)

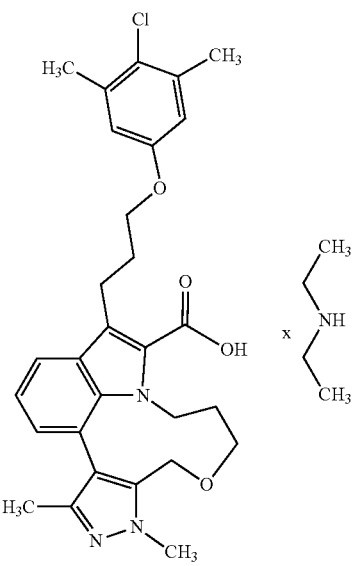

For the preparation of the racemic title compound see Example 013. Separation of enantiomers by preparative chiral HPLC (method see Example 013) gave the title compound (5 mg).

Analytical Chiral HPLC (method see Example 013): $R_t$=3.10 min.

LC-MS (Method 2): $R_t$=0.89 min; MS (ESIpos): m/z=522 [M+H]$^+$ $^1$H-NMR (400 MHz, DMSO-d6) δ[ppm]: 1.108 (10.65), 1.134 (2.64), 1.153 (5.77), 1.170 (2.66), 1.233 (0.50), 1.933 (9.06), 1.993 (0.67), 2.009 (0.57), 2.259 (16.00), 2.518 (3.86), 2.523 (2.71), 2.552 (0.40), 2.581 (0.55), 2.861 (0.69), 2.879 (2.05), 2.897 (2.03), 2.915 (0.63), 3.166 (0.42), 3.609 (0.84), 3.645 (0.86), 3.734 (0.50), 3.757 (0.57), 3.809 (8.70), 3.929 (0.48), 3.937 (0.57), 3.945 (0.96), 3.953 (0.96), 3.961 (0.57), 3.969 (0.46), 4.763 (1.13), 4.798 (1.07), 6.740 (4.32), 6.823 (0.46), 6.840 (0.52), 6.999 (0.48), 7.018 (0.75), 7.036 (0.42), 7.591 (0.52), 7.610 (0.48).

Example 016

(rac)-1,3-dimethyl-7-(3-phenoxypropyl)-1,10,11,12, 13,15-hexahydropyrazolo[4',3':9,10][1,6]oxazacycloundecino[8,7,6-hi]indole-8-carboxylic acid

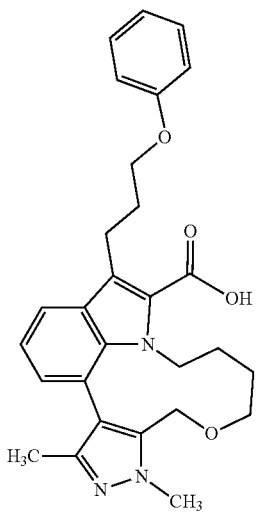 [SMILES: Cc1nn(C)c2c1-c1cccc3c(CCCOc4ccccc4)c(C(=O)O)n(c13)CCCCOC2]

A solution of (rac)-ethyl 1,3-dimethyl-7-(3-phenoxypropyl)-1,10,11,12,13,15-hexah
ydropyrazolo[4',3':9,10][1,6]oxazacycloundecino[8,7,6-hi]indole-8-carboxylate (50 mg, 0.1 mmol, see Intermediate 56) in methanol (4 ml), and lithium hydroxide (2M in water, 2 ml, 4 mmol), was heated to 50° C. for 40 hours, then cooled to room temperature. The reaction mixture was diluted with ethyl acetate and aqueous hydrochloric acid (3M), layers were separated and the organic layer was washed with saturated aqueous sodium chloride, the combined aqueous phases were extracted with ethyl acetate, the combined organic layers were dried over magnesium sulfate, insoluble material was removed by filtration, volatiles were removed under reduced pressure, and the residue was purified by normal phase chromatography on silica gel (4 g) eluting with a gradient of methanol in dichloromethane (0-5%) to give the title compound as a pale yellow foam (25 mg).

$^1$H NMR (400 MHz, DMSO-$d_6$) δ [ppm]: 13.08 (s, 1H), 7.75-7.68 (m, 1H), 7.26 (t, J=7.9 Hz, 2H), 7.08 (t, J=7.6 Hz, 1H), 6.95-6.87 (m, 3H), 6.85 (d, J=7.0 Hz, 1H), 4.64 (d, J=13.4 Hz, 1H), 4.54 (d, J=14.0 Hz, 1H), 4.28 (d, J=13.4 Hz, 1H), 3.99 (t, J=6.8 Hz, 3H), 3.84 (s, 3H), 3.48-3.37 (m, 1H), 3.28-3.09 (m, 2H), 2.84-2.69 (m, 1H), 2.06 (t, J=6.9 Hz, 2H), 1.81 (s, 3H), 1.25 (brs, 4H).

LRMS (ESI) M+H+ 474, M−H− 472;

Example 017

(rac)-1,3-dimethyl-7-[3-(1-naphthyloxy)propyl]-10, 11,12,13,15,16-hexahydro-1H-pyrazolo[4',3':9,10][1, 6]oxazacyclododecino[8,7,6-hi]indole-8-carboxylic acid

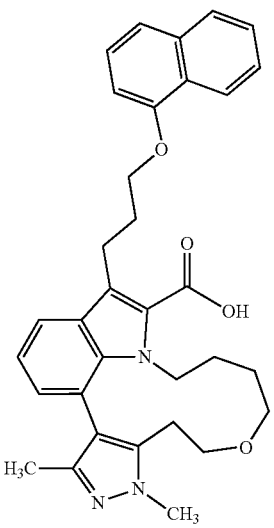 [SMILES: Cc1nn(C)c2c1-c1cccc3c(CCCOc4cccc5ccccc45)c(C(=O)O)n(c13)CCCCOCC2]

To a solution of (rac)-ethyl 1,3-dimethyl-7-[3-(1-naphthyloxy)propyl]-10,11,12,13,15,16-hexahydro-1H-pyrazolo[4',3':9,10][1,6]oxazacyclododecino[8,7,6-hi]indole-8-carboxylate (27 mg, 47.7 µmol, see Intermediate 83) in tetrahydrofuran (1.9 mL) and ethanol (1 mL) was added aqueous lithium hydroxide (2 M, 480 µL, 862 µmol) and the mixture was stirred at 60° C. for 2 d. After cooling to room temperature, aqueous hydrochloric acid (6 N, 400 µL, 2.4 mmol) was added, the resulting mixture was concentrated and purified by flash chromatography on silica gel (0-10% methanol/dichloromethane) to obtain the title compound (21 mg).

MS: m/z=538 [M+H]$^+$

1H NMR (300 MHz, Chloroform-d) δ [ppm]: 8.40 (dd, J=6.5, 3.7 Hz, 1H), 7.76 (ddd, J=24.5, 7.1, 2.3 Hz, 2H), 7.56-7.24 (m, 6H), 7.19-7.05 (m, 1H), 6.98 (dd, J=7.0, 1.3 Hz, 1H), 6.82-6.72 (m, 1H), 4.42 (q, J=8.8, 7.1 Hz, 1H), 4.23 (s, 2H), 3.92 (s, 3H), 3.62 (s, 1H), 3.45 (dt, J=18.1, 8.5 Hz, 3H), 3.28 (dd, J=8.9, 4.9 Hz, 2H), 2.88 (t, J=9.0 Hz, 1H), 2.73 (d, J=15.0 Hz, 1H), 2.38 (t, J=7.1 Hz, 2H), 2.01 (d, J=3.3 Hz, 3H), 1.44 (s, 1H), 1.15 (s, 1H), 0.77 (s, 1H).

Example 018

(rac)-7-{3-[(6-fluoronaphthalen-1-yl)oxy]propyl}-1,3-dimethyl-1,10,11,12,13,15-hexahydropyrazolo[4',3':9,10][1,6]oxazacycloundecino[8,7,6-hi]indole-8-carboxylic acid

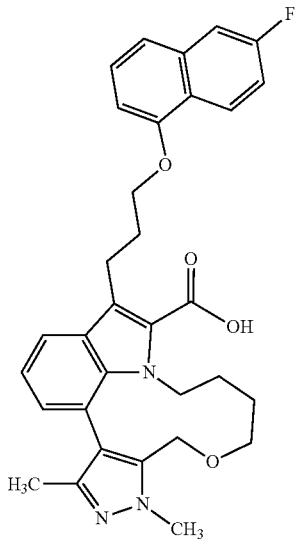 [SMILES: Cc1nn(C)c2c1-c1cccc3c(CCCOc4cccc5cc(F)ccc45)c(C(=O)O)n(c13)CCCCOC2]

A solution of (rac)-ethyl 7-{3-[(6-fluoro-1-naphthyl)oxy]propyl}-1,3-dimethyl-1,10,11,12,13,15-hexahydropyrazolo[4',3':9,10][1,6]oxazacycloundecino[8,7,6-hi]indole-8-carboxylate (50 mg, 0.1 mmol, see Intermediate 57) in methanol (2 ml), tetrahydrofuran (4 ml), and lithium hydroxide (2M in water, 0.5 ml, 1 mmol), was heated to 50° C. for 16 hours, then cooled to room temperature. The reaction mixture was diluted with ethyl acetate and aqueous hydrochloric acid (3M), layers were separated and the organic layer was washed with saturated aqueous sodium chloride solution, the combined aqueous phases were extracted with ethyl acetate, the combined organic layers were dried over magnesium sulfate, insoluble material was removed by filtration, volatiles were removed under reduced pressure, and the residue was purified by normal phase chromatography on silica gel (4 g) eluting with a gradient of methanol in dichloromethane (0-5%) to give the title compound (46 mg).

$^1$H NMR (400 MHz, DMSO-d$_6$) δ 13.15 (s, 1H), 8.27 (dd, J=9.3, 5.9 Hz, 1H), 7.75 (d, J=8.0 Hz, 1H), 7.65 (dd, J=10.5, 2.7 Hz, 1H), 7.44 (s, 1H), 7.43 (d, J=2.5 Hz, 1H), 7.38 (td, J=9.0, 2.9 Hz, 1H), 7.06 (t, J=7.5 Hz, 1H), 6.87 (dd, J=5.5, 3.2 Hz, 1H), 6.85 (d, J=6.8 Hz, 1H), 4.64 (d, J=13.3 Hz, 1H), 4.55 (d, J=14.1 Hz, 1H), 4.26 (d, J=13.4 Hz, 1H), 4.21 (t, J=6.1 Hz, 2H), 4.01 (d, J=10.6 Hz, 1H), 3.84 (s, 3H), 3.48-3.34 (m, 1H), 3.29-3.26 (m, 2H), 2.74 (d, J=11.2 Hz, 1H), 2.21 (t, J=7.0 Hz, 2H), 1.80 (s, 3H), 1.25 (s, 4H). $^{19}$F NMR (376 MHz, DMSO-d$_6$) δ −114.70.

LRMS (ESI) M+H+542 M−H− 540;

The title compound (25 mg) was separated into enantiomers by preparative chiral HPLC to give enantiomer 1 (7.5 mg, see Example 019) and enantiomer 2 (2.7 mg, see Example 020).

Preparative chiral HPLC method: Instrument: Sepiatec Prep SFC100; column: Chiralpak ID 5 μm 250×30 mm; eluent A: CO$_2$, eluent B: 2-propanol+0.4 Vol-% diethylamine (99%); isocratic: 27% B; flow 100.0 ml/min temperature: 40° C.; BPR: 150 bar; MWD @ 254 nm Analytical chiral HPLC method: Instrument: Agilent: 1260, Aurora SFC-Module; column: Chiralpak ID 5 μm 100×4.6 mm; eluent A: CO$_2$, eluent B: 2-propanol+0.2 Vol-% diethylamine (99%); isocratic: 27% B; flow 4.0 ml/min; temperature: 37.5° C.; BPR: 100 bar; MWD @ 254 nm

Example 019

7-{3-[(6-fluoronaphthalen-1-yl)oxy]propyl}-1,3-dimethyl-1,10,11,12,13,15-hexahydropyrazolo[4',3':9,10][1,6]oxazacycloundecino[8,7,6-hi]indole-8-carboxylic acid-N-ethylethanamine salt (Enantiomer 1)

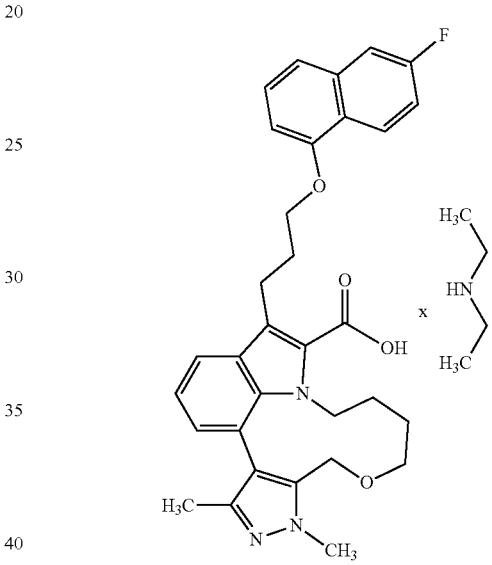

For the preparation of the racemic title compound see Example 018. Separation of enantiomers by preparative chiral HPLC (method see Example 018) gave the title compound (7.5 mg).

Analytical Chiral HPLC (method see Example 018): R$_t$=1.86 min.

LC-MS (Method 2): R$_t$=0.87 min; MS (ESIpos): m/z=542 [M+H]$^+$ $^1$H-NMR (400 MHz, DMSO-d6) δ[ppm]: 0.968 (1.06), 0.992 (0.47), 1.027 (0.57), 1.051 (0.57), 1.082 (0.70), 1.108 (4.26), 1.124 (6.49), 1.142 (13.37), 1.160 (6.39), 1.233 (1.00), 1.389 (0.57), 1.815 (15.87), 2.176 (1.06), 2.194 (1.56), 2.211 (1.16), 2.331 (1.43), 2.518 (8.48), 2.523 (5.56), 2.539 (0.70), 2.673 (1.76), 2.701 (0.67), 2.723 (0.47), 2.828 (1.46), 2.846 (4.26), 2.864 (4.19), 2.883 (1.36), 3.152 (0.53), 3.168 (0.60), 3.185 (0.77), 3.203 (0.43), 3.276 (0.83), 3.295 (1.70), 3.381 (1.13), 3.395 (0.86), 3.412 (0.86), 3.430 (0.43), 3.823 (16.00), 3.847 (0.77), 3.877 (0.43), 4.174 (1.46), 4.189 (3.03), 4.205 (1.53), 4.217 (2.03), 4.250 (2.03), 4.613 (2.26), 4.646 (2.06), 4.673 (0.67), 4.707 (0.63), 6.666 (1.06), 6.683 (1.13), 6.846 (1.30), 6.853 (1.33), 6.861 (1.23), 6.867 (1.40), 6.931 (1.06), 6.950 (1.66), 6.968 (0.96), 7.353 (0.83), 7.360 (0.93), 7.376 (1.43), 7.382 (1.53), 7.393 (0.60), 7.398 (0.96), 7.405 (1.06), 7.414 (2.49), 7.422 (2.86), 7.428 (5.85), 7.443 (0.50), 7.596 (1.26), 7.615 (1.20), 7.633 (1.66), 7.639 (1.66), 7.659 (1.63), 7.665 (1.60), 8.256 (1.36), 8.271 (1.46), 8.279 (1.43), 8.294 (1.33).

Example 020

7-{3-[(6-fluoronaphthalen-1-yl)oxy]propyl}-1,3-dimethyl-1,10,11,12,13,15-hexahydropyrazolo[4',3':9,10][1,6]oxazacycloundecino[8,7,6-hi]indole-8-carboxylic acid-N-ethylethanamine salt (Enantiomer 2)

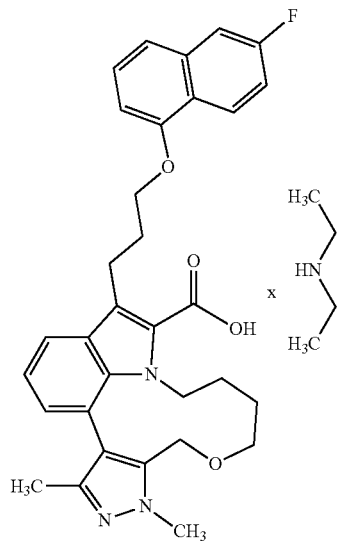

For the preparation of the racemic title compound see Example 018. Separation of enantiomers by preparative chiral HPLC (method see Example 018) gave the title compound (7.5 mg).

Analytical Chiral HPLC (method see Example 018): $R_t$=4.03 min.

LC-MS (Method 2): $R_t$=0.88 min; MS (ESIpos): m/z=542 [M+H]$^+$ $^1$H-NMR (400 MHz, DMSO-d6) δ[ppm]: 0.968 (0.80), 1.003 (0.90), 1.108 (0.72), 1.137 (2.52), 1.144 (0.87), 1.155 (4.88), 1.173 (2.75), 1.232 (1.08), 1.316 (0.51), 1.783 (0.44), 1.807 (16.00), 2.185 (1.08), 2.203 (1.59), 2.220 (1.16), 2.237 (0.41), 2.336 (0.49), 2.518 (5.50), 2.523 (3.70), 2.540 (0.57), 2.678 (0.54), 2.704 (0.51), 2.718 (0.59), 2.733 (0.57), 2.872 (0.54), 2.890 (1.64), 2.908 (1.62), 2.926 (0.51), 3.220 (0.51), 3.235 (0.64), 3.252 (0.87), 3.271 (0.57), 3.371 (0.87), 3.390 (0.95), 3.400 (0.72), 3.419 (0.74), 3.436 (0.41), 3.832 (15.82), 3.934 (0.62), 4.183 (1.46), 4.199 (3.03), 4.214 (1.49), 4.231 (1.90), 4.265 (2.00), 4.588 (0.64), 4.619 (2.67), 4.652 (2.00), 6.770 (1.05), 6.787 (1.21), 6.855 (1.31), 6.863 (1.31), 6.870 (1.18), 6.877 (1.39), 6.996 (1.10), 7.015 (1.67), 7.033 (1.00), 7.354 (0.85), 7.360 (0.95), 7.376 (1.39), 7.383 (1.59), 7.399 (1.03), 7.405 (1.13), 7.422 (2.65), 7.429 (2.83), 7.436 (5.98), 7.450 (0.44), 7.638 (1.62), 7.644 (1.70), 7.664 (1.67), 7.670 (1.72), 7.683 (1.28), 7.703 (1.18), 8.253 (1.36), 8.268 (1.44), 8.276 (1.44), 8.290 (1.34).

Example 021

(rac)-7-{3-[(4-fluoronaphthalen-1-yl)oxy]propyl}-1,3-dimethyl-1,10,11,12,13,15-hexahydropyrazolo[4',3':9,10][1,6]oxazacycloundecino[8,7,6-hi]indole-8-carboxylic acid

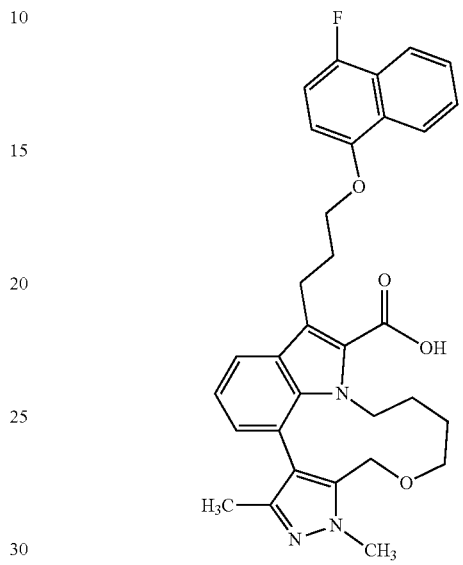

A solution of (rac)-ethyl 7-{3-[(4-fluoro-1-naphthyl)oxy]propyl}-1,3-dimethyl-1,10,11,12,13,15-hexahydropyrazolo[4',3':9,10][1,6]oxazacycloundecino[8,7,6-hi]indole-8-carboxylate (46 mg 0.08 mmol, see Intermediate 59) in methanol (4 ml), and lithium hydroxide (2M in water, 2 ml, 4 mmol), was heated to 50° C. for 40 hours and then cooled to room temperature. Volatiles were removed under reduced pressure and the residue was partitioned between ethyl acetate and aqueous hydrochloric acid (3M), layers were separated and the organic layer was washed with saturated aqueous sodium chloride solution, the combined aqueous phases were extracted with ethyl acetate, the combined organic layers were dried over magnesium sulfate, insoluble material was removed by filtration, volatiles were removed under reduced pressure, and the residue was purified by normal phase chromatography on silica gel (12 g) eluting with a gradient of methanol in dichloromethane (1-5%) to give the title compound as a pale yellow foam (31 mg).

$^1$H NMR (400 MHz, Chloroform-d) δ [ppm]: 8.34 (d, J=7.9 Hz, 1H), 8.04 (d, J=8.8 Hz, 1H), 7.75 (dd, J=8.1, 1.3 Hz, 1H), 7.62-7.47 (m, 2H), 7.08 (dd, J=8.0, 7.1 Hz, 1H), 6.99 (t, J=9.3 Hz, 1H), 6.91 (dd, J=7.1, 1.2 Hz, 1H), 6.62 (dd, J=8.4, 3.8 Hz, 1H), 4.66 (d, J=14.2 Hz, 1H), 4.59 (d, J=13.5 Hz, 1H), 4.46 (d, J=13.4 Hz, 1H), 4.21-4.06 (m, 3H), 3.95 (s, 3H), 3.45 (ddd, J=35.9, 13.7, 7.1 Hz, 3H), 2.86 (t, J=8.9 Hz, 1H), 2.35 (q, J=7.0 Hz, 2H), 1.98 (s, 3H), 1.30-0.99 (m, 4H).

LRMS (ESI) M+H+542, M−H− 540.

The title compound (27 mg) was separated into enantiomers by preparative chiral HPLC to give enantiomer 1 (12.6 mg, see Example 022) and enantiomer 2 (10.3 mg, see Example 023).

Preparative chiral HPLC method: Instrument: Sepiatec: Prep SFC100; column: Chiralpak ID 5 µm 250×30 mm; eluent A: CO$_2$, eluent B: 2-propanol+0.4 Vol-% diethylamine (99%); isocratic: 25% B; flow 100.0 ml/min temperature: 40° C.; BPR: 150 bar; MWD @ 254 nm Analytical chiral HPLC method: Instrument: Agilent: 1260, Aurora SFC-Module; column: Chiralpak ID 5 μm 100×4.6 mm; eluent A: $CO_2$, eluent B: 2-propanol+0.2 Vol-% diethylamine (99%); isocratic: 25% B; flow 4.0 ml/min; temperature: 37.5° C.; BPR: 100 bar; MWD @ 254 nm

Example 022

7-{3-[(4-fluoronaphthalen-1-yl)oxy]propyl}-1,3-dimethyl-1,10,11,12,13,15-hexahydropyrazolo[4',3': 9,10][1,6]oxazacycloundecino[8,7,6-hi]indole-8-carboxylic acid-N-ethylethanamine salt (Enantiomer 1)

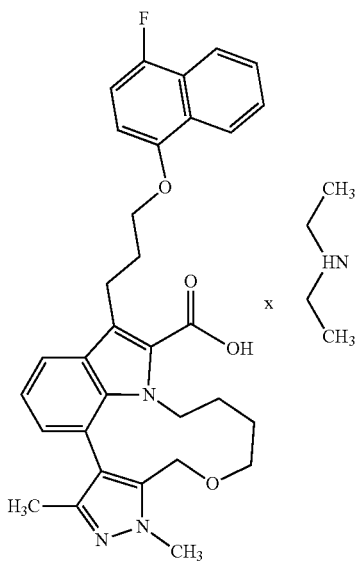

For the preparation of the racemic title compound see Example 021. Separation of enantiomers by preparative chiral HPLC (method see Example 021) gave the title compound (12.6 mg).

Analytical Chiral HPLC (method see Example 021): $R_t$=2.52 min.

LC-MS (Method 2): $R_t$=0.82 min; MS (ESIpos): m/z=542 [M+H]$^+$ $^1$H-NMR (400 MHz, DMSO-d6) δ[ppm]: 0.968 (1.13), 0.980 (0.52), 0.992 (0.50), 1.009 (0.50), 1.030 (0.55), 1.053 (0.52), 1.089 (0.76), 1.108 (4.17), 1.129 (7.03), 1.147 (14.85), 1.165 (7.11), 1.209 (0.39), 1.232 (1.52), 1.389 (0.52), 1.815 (15.19), 1.834 (0.76), 1.888 (0.50), 1.988 (0.66), 2.171 (1.00), 2.188 (1.42), 2.206 (1.05), 2.225 (0.42), 2.232 (0.42), 2.331 (1.10), 2.337 (0.50), 2.518 (5.35), 2.523 (3.65), 2.674 (1.42), 2.678 (0.79), 2.704 (0.60), 2.725 (0.42), 2.835 (1.55), 2.853 (4.75), 2.871 (4.59), 2.889 (1.47), 3.152 (0.50), 3.166 (0.55), 3.183 (0.71), 3.280 (0.76), 3.299 (1.60), 3.382 (0.97), 3.395 (0.73), 3.402 (0.71), 3.412 (0.76), 3.431 (0.42), 3.794 (0.55), 3.823 (16.00), 3.854 (0.66), 4.156 (1.34), 4.172 (2.73), 4.188 (1.36), 4.215 (1.81), 4.249 (1.91), 4.612 (2.15), 4.646 (1.99), 4.669 (0.60), 4.703 (0.58), 6.670 (1.05), 6.687 (1.18), 6.803 (1.02), 6.812 (1.10), 6.823 (1.29), 6.834 (1.23), 6.928 (1.18), 6.947 (1.78), 6.965 (1.02), 7.169 (1.39), 7.190 (1.34), 7.195 (1.47), 7.217 (1.23), 7.599 (1.55), 7.616 (2.44), 7.635 (2.68), 7.640 (2.81), 7.655 (1.36), 7.659 (1.50), 7.672 (0.68), 7.676 (0.55), 7.975 (1.60), 7.993 (1.57), 7.997 (1.31), 8.256 (1.44), 8.275 (1.15).

Example 023

7-{3-[(4-fluoronaphthalen-1-yl)oxy]propyl}-1,3-dimethyl-1,10,11,12,13,15-hexahydropyrazolo[4',3': 9,10][1,6]oxazacycloundecino[8,7,6-hi]indole-8-carboxylic acid-N-ethylethanamine salt (Enantiomer 2)

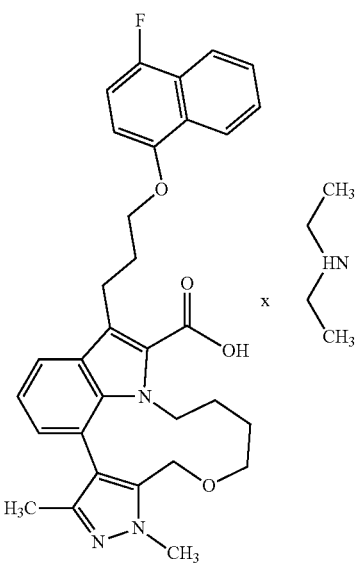

For the preparation of the racemic title compound see Example 021. Separation of enantiomers by preparative chiral HPLC (method see Example 021) gave the title compound (10.3 mg).

Analytical Chiral HPLC (method see Example 021): $R_t$=5.47 min.

LC-MS (Method 2): $R_t$=0.82 min; MS (ESIpos): m/z=542 [M+H]$^+$ $^1$H-NMR (400 MHz, DMSO-d6) δ[ppm]: 0.852 (0.63), 0.968 (1.26), 0.986 (0.58), 1.030 (0.58), 1.089 (0.72), 1.108 (1.08), 1.124 (6.25), 1.142 (12.63), 1.160 (6.16), 1.209 (0.40), 1.232 (2.11), 1.389 (0.54), 1.814 (15.91), 2.171 (0.99), 2.188 (1.44), 2.206 (1.08), 2.337 (0.85), 2.518 (8.90), 2.523 (6.02), 2.674 (2.11), 2.704 (0.58), 2.836 (1.26), 2.853 (3.87), 2.872 (3.82), 2.890 (1.17), 3.174 (0.49), 3.190 (0.63), 3.384 (0.85), 3.397 (0.72), 3.415 (0.72), 3.825 (16.00), 3.864 (0.54), 4.158 (1.30), 4.174 (2.79), 4.189 (1.35), 4.218 (1.80), 4.251 (1.98), 4.613 (2.16), 4.646 (2.34), 4.686 (0.54), 6.683 (0.76), 6.699 (0.85), 6.805 (1.12), 6.815 (1.17), 6.827 (1.39), 6.837 (1.35), 6.936 (0.81), 6.954 (1.35), 6.973 (0.76), 7.171 (1.48), 7.193 (1.48), 7.198 (1.62), 7.219 (1.35), 7.605 (1.48), 7.618 (1.89), 7.621 (1.93), 7.637 (2.97), 7.641 (3.01), 7.657 (1.44), 7.660 (1.62), 7.674 (0.72), 7.976 (1.66), 7.994 (1.62), 7.999 (1.35), 8.256 (1.53), 8.275 (1.26).

Example 024

(rac)-9,11,12-trimethyl-1-[3-(naphthalen-1-yloxy)propyl]-5,6,8,9-tetrahydro-4H-pyrazolo[4',3':8,9][1,5]oxazecino[7,6,5-hi]indole-2-carboxylic acid

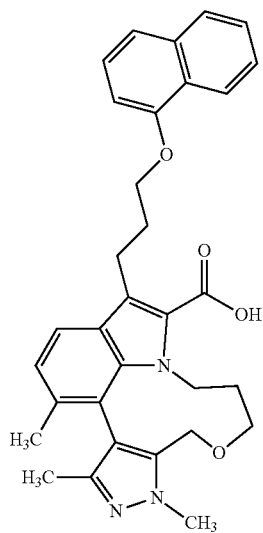 [SMILES: Cc1ccc2c(CCCOc3cccc4ccccc34)c(C(=O)O)n3c2c1-c1c(C)nn(C)c1COCCC3]

A solution of (rac)-ethyl 9,11,12-trimethyl-1-[3-(1-naphthyloxy)propyl]-5,6,8,9-tetrahydro-4H-pyrazolo[4',3':8,9][1,5]oxazecino[7,6,5-hi]indole-2-carboxylate (48 mg 0.089 mmol, see Intermediate 74) in methanol (5 ml), and lithium hydroxide (2M in water, 5 ml, 10 mmol) was heated to 55° C. for 20 hours, then cooled to room temperature. Volatiles were removed under reduced pressure and the residue was partitioned between ethyl acetate and aqueous hydrochloric acid (3M), the organic layer was washed with saturated aqueous sodium chloride solution, the combined aqueous phases were extracted with ethyl acetate, washed with brine, the combined organic phases were dried over magnesium sulfate, insoluble material was removed by filtration, volatiles were removed under reduced pressure, and the residue was purified by normal phase chromatography on silica gel (12 g) eluting with a gradient of methanol in dichloromethane (0-5%) to give the title compound as a white solid (28 mg). (Another batch was prepared accordingly).

$^1$H NMR (400 MHz, Chloroform-d) δ [ppm]: 8.39-8.29 (m, 1H), 7.85-7.70 (m, 2H), 7.50-7.41 (m, 2H), 7.39 (d, J=8.2 Hz, 1H), 7.32 (t, J=7.9 Hz, 1H), 7.11 (dd, J=8.0, 7.0 Hz, 1H), 7.04 (dd, J=7.0, 1.3 Hz, 1H), 6.75 (dd, J=7.6, 1.1 Hz, 1H), 4.72 (d, J=14.3 Hz, 1H), 4.63 (dt, J=14.6, 3.7 Hz, 1H), 4.21 (t, J=6.0 Hz, 2H), 4.02 (ddd, J=14.8, 12.4, 2.6 Hz, 1H), 3.95 (s, 3H), 3.83 (t, J=13.2 Hz, 2H), 3.73 (s, 1H), 3.59-3.34 (m, 2H), 2.71 (t, J=11.8 Hz, 1H), 2.44-2.28 (m, 2H), 2.11 (s, 3H), 1.93-1.78 (m, 1H), 1.74-1.57 (m, 1H).

LRMS (ESI) M+H+510, M−H− 508.

The title compound (197 mg) was separated into enantiomers by preparative chiral HPLC to give enantiomer 1 (72 mg, see Example 025) and enantiomer 2 (74 mg, see Example 026).

Preparative chiral HPLC method: Instrument: Sepiatec: Prep SFC100; column: Chiralpak ID 5 μm 250×30 mm; eluent A: CO$_2$, eluent B: 2-propanol+0.4 Vol-% diethylamine (99%); isocratic: 25% B; flow 100.0 ml/min temperature: 40° C.; BPR: 150 bar; MWD @ 254 nm Analytical chiral HPLC method: Instrument: Agilent: 1260, Aurora SFC-Module; column: Chiralpak ID 5 μm 100×4.6 mm; eluent A: CO$_2$, eluent B: 2-propanol+0.2 Vol-% diethylamine (99%); isocratic: 25% B; flow 4.0 ml/min; temperature: 37.5° C.; BPR: 100 bar; MWD @ 254 nm

Example 025

(+)-9,11,12-trimethyl-1-[3-(naphthalen-1-yloxy)propyl]-5,6,8,9-tetrahydro-4H-pyrazolo[4',3':8,9][1,5]oxazecino[7,6,5-hi]indole-2-carboxylic acid-N-ethylethanamine salt (Enantiomer 1)

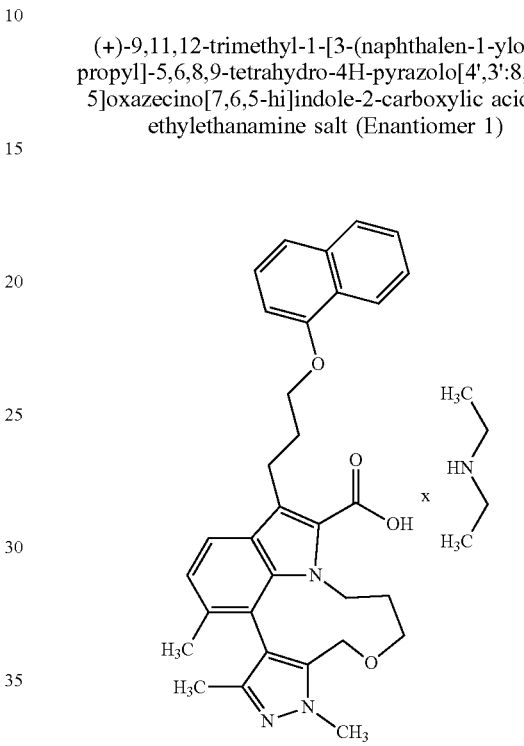

For the preparation of the racemic title compound see Example 024. Separation of enantiomers by preparative chiral HPLC (method see Example 024) gave the title compound (72 mg).

Analytical Chiral HPLC (method see Example 024): R$_t$=2.28 min.

Specific optical rotation (Method O1): +159.5° (c=1.0 g/100 ml in DMSO)

LC-MS (Method 2): Rt=0.88 min; MS (ESIpos): m/z=524 [M+H]$^+$ $^1$H-NMR (400 MHz, DMSO-d6) δ[ppm]: 1.107 (1.01), 1.123 (3.87), 1.141 (8.16), 1.159 (3.97), 1.233 (0.52), 1.406 (0.47), 1.628 (0.49), 1.834 (16.00), 1.987 (12.94), 2.151 (0.91), 2.168 (1.32), 2.185 (0.96), 2.318 (0.47), 2.409 (0.55), 2.439 (0.94), 2.469 (0.99), 2.518 (5.40), 2.523 (3.43), 2.660 (0.47), 2.822 (1.06), 2.840 (3.19), 2.858 (3.12), 2.876 (0.99), 3.116 (0.42), 3.131 (0.47), 3.149 (0.60), 3.249 (0.52), 3.269 (0.99), 3.287 (1.01), 3.483 (0.60), 3.515 (1.95), 3.551 (1.66), 3.650 (0.70), 3.683 (0.60), 3.826 (15.64), 4.150 (1.30), 4.166 (2.78), 4.182 (1.27), 4.613 (0.57), 4.647 (0.55), 4.741 (1.90), 4.776 (1.82), 6.864 (1.69), 6.882 (1.82), 6.923 (1.51), 6.943 (1.61), 7.354 (1.27), 7.374 (2.44), 7.393 (2.00), 7.432 (2.55), 7.453 (1.40), 7.472 (0.49), 7.476 (0.62), 7.489 (1.53), 7.493 (1.38), 7.503 (1.77), 7.509 (2.99), 7.513 (2.83), 7.523 (1.71), 7.527 (2.03), 7.533 (1.19), 7.540 (0.99), 7.544 (0.60), 7.847 (1.51), 7.853 (0.91), 7.866 (1.69), 7.870 (1.30), 8.205 (1.35), 8.209 (1.35), 8.229 (1.25).

Example 026

(−)-9,11,12-trimethyl-1-[3-(naphthalen-1-yloxy)propyl]-5,6,8,9-tetrahydro-4H-pyrazolo[4',3':8,9][1,5]oxazecino[7,6,5-hi]indole-2-carboxylic acid-N-ethylethanamine salt (Enantiomer 2)

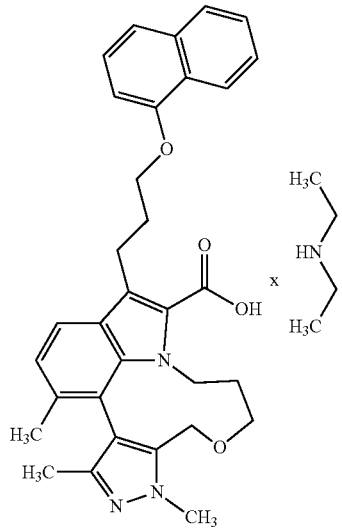

For the preparation of the racemic title compound see Example 024. Separation of enantiomers by preparative chiral HPLC (method see Example 024) gave the title compound (74 mg).

Analytical Chiral HPLC (method see Example 024): $R_t$=5.42 min.

Specific optical rotation (Method O1): −159.7° (c=1.0 g/100 ml in DMSO)

LC-MS (Method 2): Rt=0.86 min; MS (ESIpos): m/z=524 [M+H]+

$^1$H-NMR (400 MHz, DMSO-d6) δ[ppm]: 1.125 (2.42), 1.144 (5.63), 1.162 (2.48), 1.232 (0.71), 1.832 (9.36), 1.991 (7.69), 2.153 (0.54), 2.171 (0.81), 2.187 (0.58), 2.332 (0.79), 2.443 (0.58), 2.518 (4.20), 2.523 (2.70), 2.539 (16.00), 2.673 (0.79), 2.838 (0.58), 2.856 (1.82), 2.874 (1.76), 2.892 (0.56), 3.280 (0.60), 3.523 (1.20), 3.559 (1.05), 3.652 (0.41), 3.829 (9.08), 4.155 (0.79), 4.171 (1.67), 4.187 (0.77), 4.742 (1.11), 4.777 (1.09), 6.869 (1.01), 6.886 (1.07), 6.944 (0.79), 6.965 (0.83), 7.357 (0.79), 7.377 (1.46), 7.396 (1.22), 7.435 (1.52), 7.456 (0.84), 7.491 (0.92), 7.495 (0.84), 7.505 (0.98), 7.511 (1.48), 7.515 (1.01), 7.525 (0.90), 7.529 (1.03), 7.542 (0.99), 7.563 (0.54), 7.849 (0.90), 7.855 (0.54), 7.867 (0.99), 7.872 (0.77), 8.204 (0.81), 8.208 (0.83), 8.226 (0.75), 8.228 (0.75).

Example 027

(rac)-1,3,4-trimethyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid

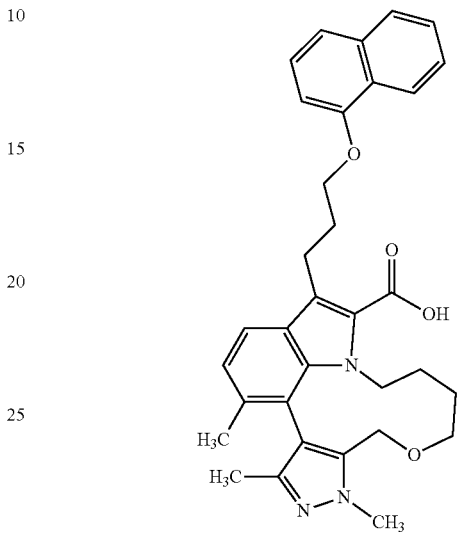

A solution of (rac)-ethyl 1,3,4-trimethyl-7-[3-(1-naphthyloxy)propyl]-1,10,11,12,13,15-hexahydropyrazolo[4',3':9,10][1,6]oxazacycloundecino[8,7,6-hi]indole-8-carboxylate (160 mg, 0.29 mmol, see Intermediate 76) in methanol (10 ml) and tetrahydrofuran (10 ml) was treated with lithium hydroxide (2M in water, 10 ml, 20 mmol), and stirred at 50° C. for 36 hours. The reaction mixture was cooled to room temperature, volatiles were removed and the residue was partitioned between ethyl acetate and aqueous hydrochloric acid (3M), the organic phase was washed with saturated aqueous sodium chloride solution and then dried over magnesium sulfate, solids were removed by filtration, volatiles were removed under reduced pressure, and the residue was purified by normal phase chromatography on silica gel (12 g) eluting with a gradient of methanol in dichloromethane (1-4%) to give the title compound (86 mg).

$^1$H NMR (400 MHz, Chloroform-d) δ [ppm]: 8.43-8.28 (m, 1H), 7.83-7.74 (m, 1H), 7.67 (d, J=8.2 Hz, 1H), 7.50-7.43 (m, 2H), 7.39 (d, J=8.2 Hz, 1H), 7.32 (t, J=7.9 Hz, 1H), 7.04 (d, J=8.3 Hz, 1H), 6.75 (dd, J=7.6, 1.0 Hz, 1H), 4.70-4.53 (m, 2H), 4.33 (d, J=13.4 Hz, 1H), 4.21 (t, J=6.1 Hz, 2H), 4.09 (ddt, J=13.8, 10.3, 4.9 Hz, 1H), 3.98 (s, 3H), 3.58-3.34 (m, 3H), 2.96 (ddd, J=12.2, 8.3, 4.6 Hz, 1H), 2.36 (p, J=6.9 Hz, 2H), 1.98 (s, 3H), 1.93 (s, 3H), 1.52 (td, J=16.1, 12.6, 8.4 Hz, 1H), 1.25 (d, J=10.7 Hz, 2H), 1.15-1.03 (m, 1H).

LRMS (ESI) M+H+538; M−H− 536.

The title compound (65 mg) was separated into enantiomers by preparative chiral HPLC to give enantiomer 1 (20 mg, see Example 028) and enantiomer 2 (18 mg, see Example 029).

Preparative chiral HPLC method: Instrument: Sepiatec: Prep SFC100; column: Chiralpak ID 5 μm 250×30 mm; eluent A: $CO_2$, eluent B: 2-propanol+0.4 Vol-% diethylamine (99%); isocratic: 25% B; flow 100.0 ml/min temperature: 40° C.; BPR: 150 bar; MWD @ 254 nm Analytical chiral HPLC method: Instrument: Agilent: 1260, Aurora SFC-Module; column: Chiralpak ID 5 μm 100×4.6 mm; eluent A: CO₂, eluent B: 2-propanol+0.2 Vol-% diethylamine (99%); isocratic: 25% B; flow 4.0 ml/min; temperature: 37.5° C.; BPR: 100 bar; MWD @ 254 nm Example 028

1,3,4-trimethyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid-N-ethylethanamine salt (Enantiomer 1)

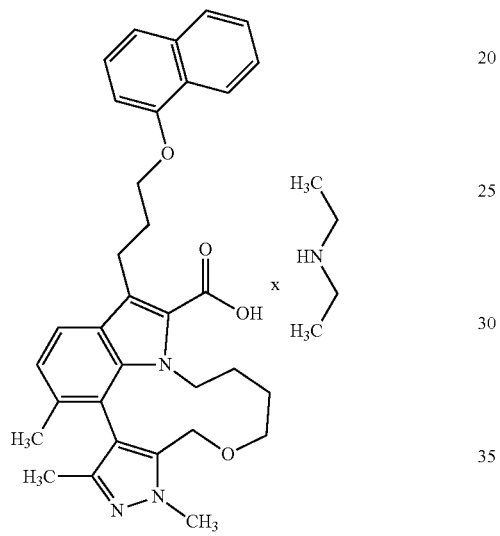

For the preparation of the racemic title compound see Example 027. Separation of enantiomers by preparative chiral HPLC (method see Example 027) gave the title compound (20 mg).

Analytical Chiral HPLC (method see Example 027): R$_t$=2.39 min.

LC-MS (Method 2): R$_t$=0.82 min; MS (ESIpos): m/z=538 [M+H]⁺

¹H-NMR (400 MHz, DMSO-d6) δ[ppm]: 0.968 (1.21), 0.982 (0.59), 0.992 (0.55), 0.995 (0.55), 1.089 (0.62), 1.108 (5.22), 1.131 (5.46), 1.149 (11.42), 1.167 (5.20), 1.209 (0.46), 1.232 (1.19), 1.349 (0.53), 1.743 (16.00), 1.885 (13.04), 2.171 (1.06), 2.189 (1.58), 2.206 (1.14), 2.518 (3.62), 2.523 (2.47), 2.789 (0.44), 2.796 (0.48), 2.808 (0.64), 2.830 (1.45), 2.848 (3.69), 2.866 (3.49), 2.884 (1.12), 3.155 (0.51), 3.171 (0.59), 3.188 (0.82), 3.207 (0.43), 3.259 (0.64), 3.278 (1.24), 3.297 (1.22), 3.312 (1.84), 3.329 (2.54), 3.393 (0.55), 3.407 (0.83), 3.425 (0.73), 3.437 (0.69), 4.097 (1.83), 4.130 (1.99), 4.164 (1.14), 4.181 (2.22), 4.196 (1.14), 4.576 (0.59), 4.611 (0.57), 4.628 (2.24), 4.662 (1.99), 6.868 (1.86), 6.886 (1.99), 6.926 (1.88), 6.947 (2.00), 7.352 (1.37), 7.372 (2.61), 7.391 (2.02), 7.434 (2.73), 7.455 (1.58), 7.480 (0.46), 7.485 (0.64), 7.497 (1.63), 7.502 (1.54), 7.507 (1.83), 7.514 (3.80), 7.521 (3.33), 7.526 (2.29), 7.531 (2.06), 7.543 (2.13), 7.849 (1.60), 7.858 (0.87), 7.867 (1.49), 7.873 (1.37), 8.227 (1.40), 8.232 (1.33), 8.244 (0.73), 8.251 (1.31).

Example 029

1,3,4-trimethyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid-N-ethylethanamine salt (Enantiomer 2)

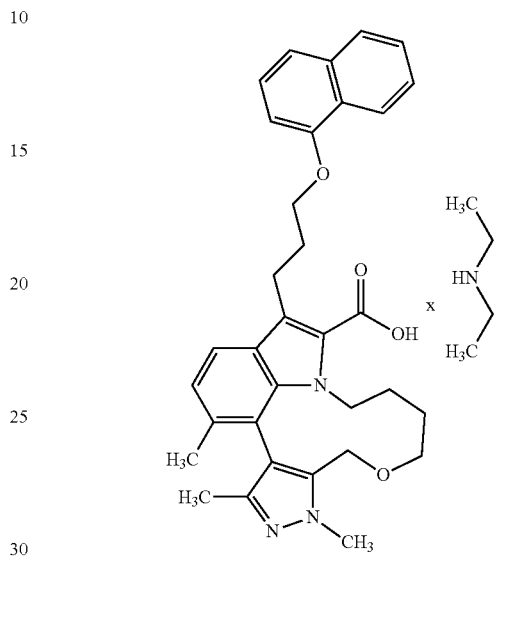

For the preparation of the racemic title compound see Example 027. Separation of enantiomers by preparative chiral HPLC (method see Example 027) gave the title compound (18 mg).

Analytical Chiral HPLC (method see Example 027): R$_t$=6.59 min.

LC-MS (Method 2): R$_t$=0.81 min; MS (ESIpos): m/z=538 [M+H]⁺

¹H-NMR (400 MHz, DMSO-d6) δ[ppm]: 0.852 (0.50), 0.968 (0.89), 0.974 (0.66), 0.992 (0.62), 1.071 (0.54), 1.089 (0.96), 1.108 (13.07), 1.124 (6.77), 1.142 (13.65), 1.160 (6.44), 1.232 (1.48), 1.349 (0.48), 1.745 (16.00), 1.880 (12.84), 1.960 (0.48), 2.170 (1.04), 2.187 (1.56), 2.205 (1.10), 2.518 (4.18), 2.523 (2.87), 2.678 (0.42), 2.784 (0.42), 2.803 (0.66), 2.815 (1.85), 2.833 (4.72), 2.851 (4.32), 2.869 (1.35), 3.141 (0.50), 3.156 (0.56), 3.174 (0.77), 3.253 (0.56), 3.271 (1.12), 3.289 (1.02), 3.305 (1.52), 3.391 (0.54), 3.407 (0.79), 3.424 (0.66), 3.437 (0.66), 3.813 (0.60), 3.846 (15.96), 4.094 (1.79), 4.128 (1.95), 4.164 (1.04), 4.180 (2.04), 4.193 (1.10), 4.594 (0.58), 4.628 (2.62), 4.660 (1.95), 6.867 (1.81), 6.885 (1.95), 6.913 (1.83), 6.934 (1.95), 7.351 (1.33), 7.371 (2.51), 7.391 (1.99), 7.433 (2.66), 7.454 (1.54), 7.479 (0.44), 7.484 (0.66), 7.497 (1.79), 7.501 (2.06), 7.506 (3.18), 7.514 (3.86), 7.521 (2.29), 7.526 (2.99), 7.530 (2.14), 7.543 (0.71), 7.547 (0.44), 7.849 (1.56), 7.857 (0.83), 7.866 (1.48), 7.872 (1.33), 8.227 (1.37), 8.232 (1.29), 8.251 (1.29).

927

Example 038

(rac)- (E/Z)-1,3,4-trimethyl-7-[3-(1-naphthyloxy)propyl]-1,10,13,15-tetrahydropyrazolo[4',3':9,10][1,6]oxazacycloundecino[8,7,6-hi]indole-8-carboxylic acid

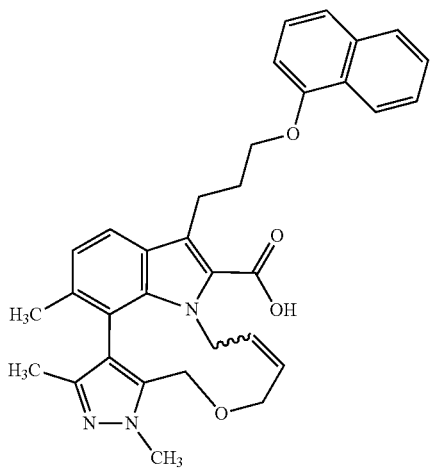 [SMILES: Cc1ccc2c(CCCOc3cccc4ccccc34)c(C(=O)O)n3c2c1-c1c(C)nn(C)c1COCC=CC3]

To a solution of (rac)-ethyl (E/Z)-1,3,4-trimethyl-7-[3-(1-naphthyloxy)propyl]-1,10,13,15-tetrahydropyrazolo[4',3':9,10][1,6]oxazacycloundecino[8,7,6-hi]indole-8-carboxylate (see Intermediate 75, 50 mg, 0.09 mmol) in methanol (4 ml) was treated with lithium hydroxide (2M in water, 2 ml), and heated to 50° C. for 36 hours. Volatiles were removed under reduced pressure and the residue was partitioned between ethyl acetate and aqueous hydrochloric acid (3M), the organic layer was washed with saturated aqueous sodium chloride solution and then dried over magnesium sulfate, solids were removed by filtration, volatiles were removed under reduced pressure, and the residue was purified by normal phase chromatography on silica gel (12 g) eluting with a gradient of methanol in dichloromethane (2-4%) to give the title compound (9 mg).

$^1$H NMR (400 MHz, Chloroform-d) δ 8.39-8.27 (m, 1H), 7.83-7.72 (m, 1H), 7.63 (d, J=8.1 Hz, 1H), 7.52-7.42 (m, 2H), 7.39 (d, J=8.3 Hz, 1H), 7.33 (t, J=7.9 Hz, 1H), 7.05 (d, J=8.2 Hz, 1H), 6.75 (dd, J=7.6, 1.1 Hz, 1H), 5.24-5.10 (m, 2H), 5.08-4.96 (m, 1H), 4.74-4.62 (m, 1H), 4.59 (d, J=13.7 Hz, 1H), 4.39 (d, J=13.7 Hz, 1H), 4.21 (t, J=6.1 Hz, 2H), 4.00 (s, 3H), 3.80 (dd, J=12.7, 4.7 Hz, 1H), 3.66 (t, J=12.2 Hz, 1H), 3.52-3.29 (m, 2H), 2.36 (h, J=6.2 Hz, 2H), 1.93 (s, 3H), 1.84 (s, 3H).

LRMS (ESI) M+H$^+$ 536, M−H$^−$ 534.

928

Example 039

(rac)-1,3,4-trimethyl-7-[3-(5,6,7,8-tetrahydronaphthalen-1-yloxy)propyl]-1,10,11,12,13,15-hexahydropyrazolo[4',3':9,10][1,6]oxazacycloundecino[8,7,6-hi]indole-8-carboxylic acid

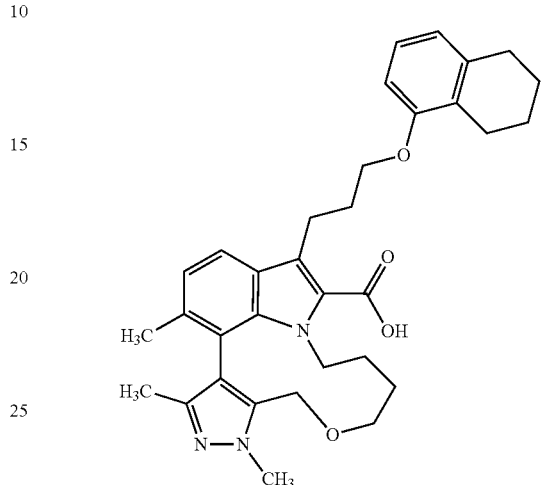

To a solution of (rac)-ethyl 1,3,4-trimethyl-7-[3-(5,6,7,8-tetrahydronaphthalen-1-yloxy)propyl]-1,10,11,12,13,15-hexahydropyrazolo[4',3':9,10][1,6]oxazacycloundecino[8,7,6-hi]indole-8-carboxylate (50 mg, 0.88 mmol, see Intermediate 77) in methanol (4 ml) was added lithium hydroxide (2M in water, 2 ml), and the mixture was heated to 50° C. for 18 hours. Volatiles were removed under reduced pressure and the residue was partitioned between ethyl acetate and aqueous hydrochloric acid (3M), the organic layer was washed with saturated aqueous sodium chloride solution and then dried over magnesium sulfate, solids were removed by filtration, volatiles were removed under reduced pressure, and the residue was purified by normal phase chromatography on silica gel (12 g) eluting with a gradient of methanol in dichloromethane (0-5%) to give the title compound (32 mg).

$^1$H NMR (400 MHz, Chloroform-d) δ [ppm]: 7.64 (d, J=8.2 Hz, 1H), 7.07 (d, J=8.2 Hz, 1H), 7.02 (t, J=7.9 Hz, 1H), 6.72-6.64 (m, 1H), 6.64-6.54 (m, 1H), 4.65 (dt, J=14.3, 3.5 Hz, 1H), 4.61 (d, J=13.5 Hz, 1H), 4.35 (d, J=13.4 Hz, 1H), 4.18-4.08 (m, 1H), 4.04 (t, J=6.2 Hz, 2H), 4.01-3.94 (m, 3H), 3.52 (dt, J=11.6, 6.9 Hz, 1H), 3.45-3.24 (m, 2H), 2.98 (ddd, J=12.1, 8.4, 4.6 Hz, 1H), 2.76 (q, J=5.2 Hz, 4H), 2.21 (p, J=7.0 Hz, 2H), 1.99 (s, 3H), 1.92 (s, 3H), 1.85-1.70 (m, 4H), 1.62-1.44 (m, 1H), 1.36-1.21 (m, 2H), 1.20-1.03 (m, 1H).

LRMS (ESI) M+H$^+$ 542, M−H$^−$ 540.

Example 040

(rac)-7-{3-[(6-chloronaphthalen-1-yl)oxy]propyl}-1,3-dimethyl-1,10,11,12,13,15-hexahydropyrazolo[4',3':9,10][1,6]oxazacycloundecino[8,7,6-hi]indole-8-carboxylic acid

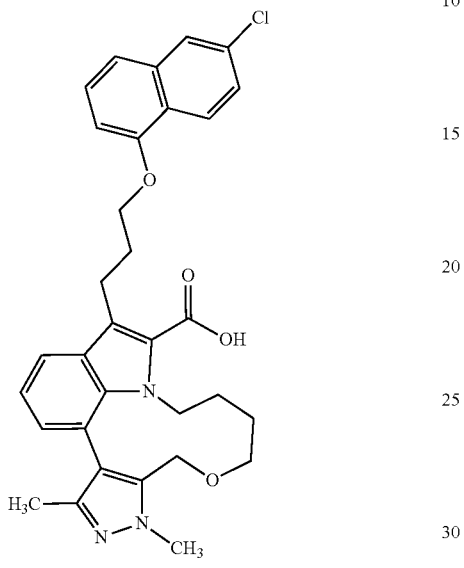

A solution of (rac)-ethyl 7-{3-[(6-chloro-1-naphthyl)oxy]propyl}-1,3-dimethyl-1,10,11,12,13,15-hexahydropyrazolo[4',3':9,10][1,6]oxazacycloundecino[8,7,6-hi]indole-8-carboxylate (82 mg 0.14 mmol, see Intermediate 65) in methanol (5 ml) and lithium hydroxide (2M in water, 5 ml, 10 mmol) was heated to 60° C. for 48 hours and then cooled to room temperature. Volatiles were removed and the residue was diluted with ethyl acetate and aqueous hydrochloric acid (3M), layers were separated and the organic layer was washed with saturated aqueous sodium chloride, combined aqueous phases were extracted with ethyl acetate, the combined organic layers were dried over magnesium sulfate, insoluble material was removed by filtration, volatiles were removed under reduced pressure, and the residue was purified by normal phase chromatography on silica gel (12 g) eluting with a gradient of methanol in dichloromethane (0-5%) to give the title compound as a white solid (47 mg).

LRMS (ESI) M+H+558, M-H- 556;

The title compound (38 mg) was separated into enantiomers by preparative chiral HPLC to give enantiomer 1 (10 mg, see Example 041) and enantiomer 2 (5 mg, see Example 042).

Preparative chiral HPLC method: Instrument: Sepiatec: Prep SFC100; column: Chiralpak IE 5 µm 250×30 mm; eluent A: $CO_2$, eluent B: 2-propanol+0.4 Vol-% diethylamine (99%); isocratic: 33% B; flow 100.0 ml/min temperature: 40° C.; BPR: 150 bar; MWD @ 254 nm Analytical chiral HPLC method: Instrument: Agilent: 1260, Aurora SFC-Module; column: Chiralpak IE 5 µm 100×4.6 mm; eluent A: $CO_2$, eluent B: 2-propanol+0.2 Vol-% diethylamine (99%); isocratic: 22% B; flow 4.0 ml/min; temperature: 37.5° C.; BPR: 100 bar; MWD @ 254 nm

Example 041

7-{3-[(6-chloronaphthalen-1-yl)oxy]propyl}-1,3-dimethyl-1,10,11,12,13,15-hexahydropyrazolo[4',3':9,10][1,6]oxazacycloundecino[8,7,6-hi]indole-8-carboxylic acid-N-ethylethanamine salt (Enantiomer 1)

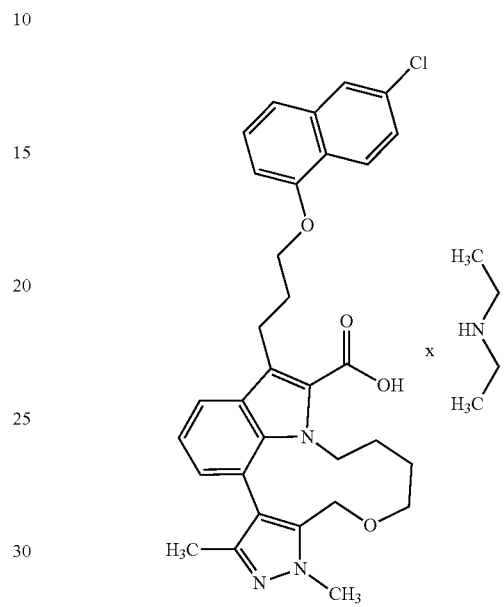

For the preparation of the racemic title compound see Example 040. Separation of enantiomers by preparative chiral HPLC (method see Example 040) gave the title compound (10 mg).

Analytical Chiral HPLC (method see Example 40): $R_t$=2.95 min.

LC-MS (Method 2): Rt=0.92 min; MS (ESIpos): m/z=558 [M+H]$^+$ $^1$H-NMR (400 MHz, DMSO-d6) δ[ppm]: 1.001 (1.28), 1.108 (8.70), 1.136 (2.28), 1.154 (4.59), 1.172 (2.46), 1.232 (1.39), 1.287 (0.70), 1.801 (16.00), 1.880 (0.48), 1.899 (0.62), 1.918 (0.62), 2.155 (0.70), 2.175 (1.28), 2.195 (1.58), 2.208 (1.91), 2.225 (1.36), 2.323 (1.65), 2.327 (2.20), 2.331 (1.61), 2.523 (6.75), 2.540 (1.76), 2.665 (1.61), 2.669 (2.20), 2.673 (1.65), 2.693 (3.96), 2.710 (0.66), 2.724 (0.70), 2.741 (0.70), 2.886 (0.55), 2.905 (1.65), 2.923 (1.61), 2.941 (0.51), 3.242 (0.62), 3.257 (0.81), 3.274 (1.21), 3.283 (1.47), 3.301 (2.09), 3.370 (1.39), 3.388 (1.28), 3.399 (0.84), 3.418 (0.88), 3.434 (0.48), 3.834 (15.67), 3.962 (0.70), 4.189 (1.98), 4.203 (3.27), 4.219 (1.69), 4.232 (2.09), 4.265 (2.13), 4.557 (0.81), 4.592 (0.73), 4.620 (2.35), 4.653 (2.02), 6.804 (1.36), 6.821 (1.54), 6.912 (1.36), 6.922 (2.20), 6.933 (1.43), 7.014 (1.28), 7.033 (1.94), 7.051 (1.14), 7.440 (5.54), 7.452 (4.59), 7.478 (1.98), 7.483 (1.98), 7.500 (2.02), 7.506 (2.06), 7.709 (1.61), 7.729 (1.47), 7.992 (3.60), 7.997 (3.60), 8.196 (3.12), 8.219 (2.83).

Example 042

7-{3-[(6-chloronaphthalen-1-yl)oxy]propyl}-1,3-dimethyl-1,10,11,12,13,15-hexahydropyrazolo[4',3':9,10][1,6]oxazacycloundecino[8,7,6-hi]indole-8-carboxylic acid-N-ethylethanamine salt (Enantiomer 2)

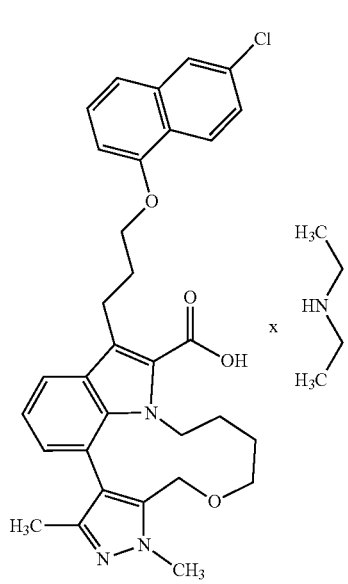

For the preparation of the racemic title compound see Example 040. Separation of enantiomers by preparative chiral HPLC (method see Example 040) gave the title compound (5 mg).

Analytical Chiral HPLC (method see Example 040): $R_t$=4.90 min.

LC-MS (Method 2): Rt=0.90 min; MS (ESIpos): m/z=558 [M+H]$^+$ $^1$H-NMR (400 MHz, DMSO-d6) δ[ppm]: 1.000 (1.48), 1.136 (1.82), 1.154 (3.69), 1.173 (2.05), 1.232 (1.60), 1.799 (16.00), 2.195 (1.33), 2.210 (1.90), 2.227 (1.41), 2.322 (1.60), 2.326 (2.17), 2.331 (1.67), 2.539 (9.58), 2.665 (1.67), 2.669 (2.28), 2.673 (1.82), 2.692 (0.76), 2.715 (0.80), 2.727 (0.76), 2.745 (0.84), 2.895 (0.46), 2.913 (1.41), 2.931 (1.41), 2.949 (0.46), 3.255 (0.61), 3.271 (0.80), 3.290 (1.29), 3.376 (1.10), 3.391 (1.22), 3.420 (0.91), 3.437 (0.46), 3.835 (15.51), 3.979 (0.80), 4.002 (0.57), 4.191 (1.63), 4.205 (3.34), 4.220 (1.79), 4.234 (2.17), 4.268 (2.20), 4.541 (0.87), 4.575 (0.80), 4.621 (2.32), 4.655 (2.01), 6.825 (1.79), 6.842 (2.05), 6.913 (1.37), 6.924 (2.28), 6.935 (1.48), 7.027 (1.52), 7.046 (2.24), 7.065 (1.37), 7.442 (5.55), 7.453 (4.60), 7.479 (1.98), 7.484 (2.01), 7.501 (2.01), 7.506 (2.09), 7.728 (1.90), 7.748 (1.79), 7.993 (3.53), 7.999 (3.61), 8.195 (3.08), 8.217 (2.85).

Example 043

(rac)-9,11-dimethyl-1-[3-(naphthalen-1-yloxy)propyl]-5,6,8,9-tetrahydro-4H-pyrazolo[4',3':8,9][1,5]oxazecino[7,6,5-hi]indole-2-carboxylic acid

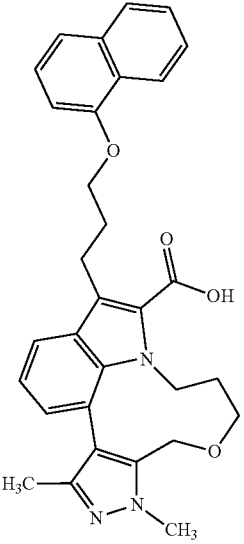 [SMILES: Cc1nn(C)c2c1-c1cccc3c(CCCOc4cccc5ccccc45)c(C(=O)O)n(c13)CCCOC2]

A mixture of (rac)-ethyl 9,11-dimethyl-1-[3-(naphthalen-1-yloxy)propyl]-5,6,8,9-tetrahydro-4H-pyrazolo[4',3':8,9][1,5]oxazecino[7,6,5-hi]indole-2-carboxylate (see Intermediate 134, 230 mg, 428 μmol), ethanol (24 ml) and aqueous lithium hydroxide (8.6 ml, 1.0 M, 8.6 mmol) was stirred for 1 day at 60° C. For work-up, organic solvents were removed under vacuum, citric acid was added to adjust the pH to 5-6, and the mixture was extracted three times with a mixture of dichloromethane/2-propanol (4:1). The combined organic phases were washed with brine, filtered through a silicone filter and concentrated. The residue was purified by flash chromatography (25 g Biotage SNAP cartridge silica, dichloromethane/ethanol gradient, 0%→15% ethanol) followed by preparative HPLC (method P3) to give the title compound 97.8 mg (99% purity, 44% yield).

LC-MS (Method 1): $R_t$=1.48 min; MS (ESIpos): m/z=510 [M+H]$^+$ $^1$H-NMR (400 MHz, DMSO-d6) δ[ppm]: 1.562 (0.55), 1.588 (0.50), 1.628 (0.46), 1.657 (0.53), 1.921 (16.00), 2.074 (4.25), 2.182 (0.99), 2.199 (1.41), 2.216 (1.05), 2.323 (0.71), 2.327 (0.97), 2.331 (0.70), 2.518 (3.40), 2.523 (2.26), 2.555 (0.49), 2.582 (0.84), 2.611 (0.52), 2.665 (0.65), 2.669 (0.90), 2.674 (0.62), 3.254 (0.50), 3.269 (0.62), 3.287 (0.93), 3.307 (0.59), 3.362 (0.97), 3.380 (0.59), 3.396 (0.52), 3.622 (1.84), 3.658 (1.88), 3.701 (0.71), 3.733 (0.65), 3.816 (15.64), 3.853 (0.44), 3.882 (0.87), 3.911 (0.50), 3.918 (0.41), 4.186 (1.47), 4.201 (3.07), 4.215 (1.40), 4.514 (0.82), 4.549 (0.76), 4.746 (2.02), 4.781 (1.93), 6.887 (1.87), 6.905 (2.02), 6.932 (1.78), 6.935 (1.82), 6.949 (2.37), 6.952 (2.14), 7.046 (2.07), 7.065 (2.26), 7.084 (1.52), 7.368 (1.38), 7.388 (2.64), 7.407 (2.20), 7.443 (2.74), 7.464 (1.49), 7.478 (0.52), 7.482 (0.67), 7.495 (1.55), 7.499 (1.37), 7.510 (1.75), 7.514 (2.36), 7.519 (1.72), 7.530 (1.47), 7.533 (1.69), 7.547 (0.71), 7.550 (0.52), 7.750 (1.87), 7.753 (1.93), 7.770 (1.78), 7.773 (1.69), 7.853 (1.64), 7.859 (0.99), 7.872 (1.76), 7.877 (1.37), 8.198 (1.44), 8.201 (1.46), 8.220 (1.37), 13.214 (1.09).

The title compound was separated into enantiomers using chiral preparative HPLC to give enantiomer 1 (45 mg, see example 044) and enantiomer 2 (40 mg, see example 045).

Preparative chiral HPLC method: Instrument: Sepiatec: Prep SFC100; column: Chiralpak I@ 5 μm 250×30 mm; eluent A: carbon dioxide, eluent B: 2-propanol+0.4 vol-% diethylamine (99%); isocratic: 25% B; flow 100.0 ml/min temperature: 40° C.; BPR: 150 bar; MWD @ 254 nm Analytical chiral HPLC method: Instrument: Agilent: 1260, Aurora SFC-Modul; column: Chiralpak ID 5 μm 100×4.6 mm; eluent A: carbon dioxide, eluent B: 2-propanol+0.2 vol-% diethylamine (99%); isocratic: 25% B; flow 4.0 ml/min; temperature: 37.5° C.; BPR: 100 bar; MWD @ 254 nm

Example 044

9,11-dimethyl-1-[3-(naphthalen-1-yloxy)propyl]-5,6,8,9-tetrahydro-4H-pyrazolo[4',3':8,9][1,5]oxazecino[7,6,5-hi]indole-2-carboxylic acid-N-ethyl-ethanamine salt (Enantiomer 1)

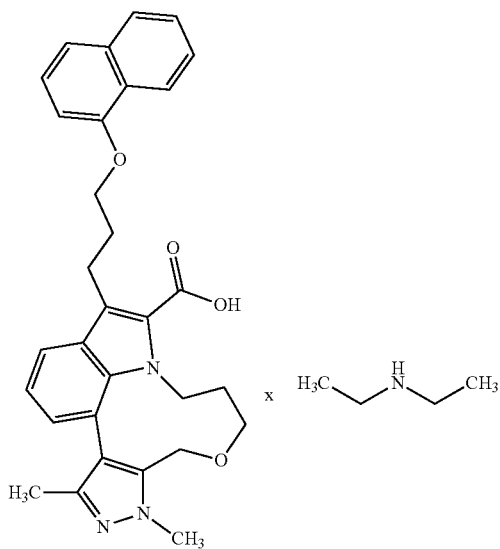

For the preparation of the racemic title compound see Example 043. Separation of enantiomers by preparative chiral HPLC (method see Example 043) gave the title compound (45 mg).

Analytical chiral HPLC (method see Example 043): $R_t$=3.03 min.

LC-MS (Method 1): $R_t$=1.48 min; MS (ESIpos): m/z=510 $[M+H]^+$ $^1$H-NMR (400 MHz, DMSO-d6) δ[ppm]: 0.968 (0.46), 1.108 (16.00), 1.134 (6.05), 1.145 (0.75), 1.153 (13.07), 1.170 (6.23), 1.470 (0.46), 1.734 (0.43), 1.930 (14.79), 2.167 (0.75), 2.182 (1.09), 2.199 (0.80), 2.323 (0.75), 2.327 (1.05), 2.331 (0.77), 2.518 (3.92), 2.523 (2.96), 2.556 (0.95), 2.586 (0.55), 2.665 (0.77), 2.669 (1.07), 2.673 (0.75), 2.845 (1.62), 2.863 (4.98), 2.881 (5.01), 2.900 (1.53), 3.134 (0.41), 3.150 (0.48), 3.167 (0.61), 3.274 (0.66), 3.294 (1.30), 3.571 (1.53), 3.606 (1.55), 3.719 (0.80), 3.728 (0.86), 3.740 (0.82), 3.750 (0.77), 3.804 (14.31), 4.162 (1.32), 4.177 (2.84), 4.193 (1.43), 4.595 (0.61), 4.629 (0.57), 4.747 (1.82), 4.782 (1.73), 6.788 (1.00), 6.805 (1.18), 6.870 (1.66), 6.887 (1.77), 6.952 (1.09), 6.971 (1.59), 6.990 (0.93), 7.353 (1.16), 7.374 (2.30), 7.393 (1.86), 7.432 (2.43), 7.452 (1.32), 7.471 (0.43), 7.476 (0.55), 7.488 (1.37), 7.492 (1.25), 7.502 (1.46), 7.507 (2.64), 7.512 (1.52), 7.521 (1.36), 7.526 (1.50), 7.538 (0.62), 7.543 (0.43), 7.610 (1.09), 7.629 (1.02), 7.847 (1.43), 7.853 (0.84), 7.865 (1.53), 7.870 (1.23), 8.205 (1.25), 8.210 (1.27), 8.229 (1.20).

Example 045

9,11-dimethyl-1-[3-(naphthalen-1-yloxy)propyl]-5,6,8,9-tetrahydro-4H-pyrazolo[4',3':8,9][1,5]oxazecino[7,6,5-hi]indole-2-carboxylic acid-N-ethyl-ethanamine salt (Enantiomer 2)

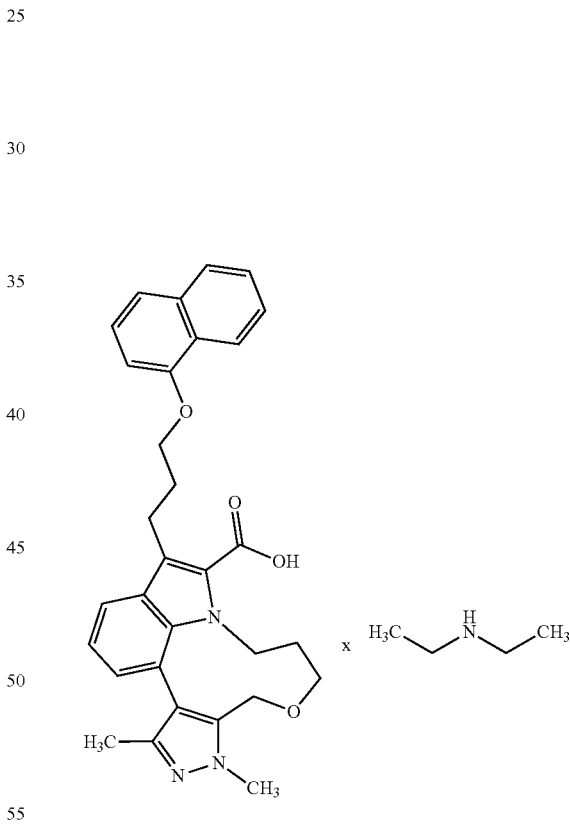

For the preparation of the racemic title compound see Example 043. Separation of enantiomers by preparative chiral HPLC (method see Example 043) gave the title compound (45 mg).

Analytical Chiral HPLC (method see Example 043): $R_t$=6.17 min.

Example 046

(rac)-1-{3-[(6-fluoronaphthalen-1-yl)oxy]propyl}-9,11-dimethyl-5,6,8,9-tetrahydro-4H-pyrazolo[4',3':8,9][1,5]oxazecino[7,6,5-hi]indole-2-carboxylic acid

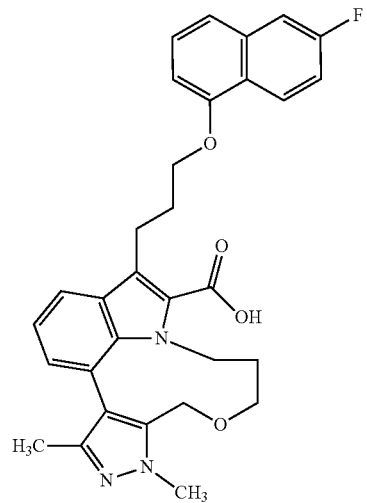 [SMILES: Cc1nn(C)c2c1-c1cccc3c(CCCOc4cccc5cc(F)ccc45)c(C(=O)O)n(c13)CCCOC2]

A solution of (rac)-ethyl 1-{3-[(6-fluoro-1-naphthyl)oxy]propyl}-9,11-dimethyl-5,6,8,9-tetrahydro-4H-pyrazolo[4',3':8,9][1,5]oxazecino[7,6,5-hi]indole-2-carboxylate (see Intermediate 46, 51 mg 0.092 mmol) in methanol (5 ml), and lithium hydroxide (2M in water, 5 ml, 10 mmol) was heated to 55° C. for 20 hours, then cooled to room temperature. Volatiles were removed under reduced pressure and the residue was partitioned between ethyl acetate and aqueous hydrochloric acid (3M), the organic layer was washed with saturated aqueous sodium chloride solution, dried over magnesium sulfate, insoluble material was removed by filtration, volatiles were removed under reduced pressure, and the residue was purified by normal phase chromatography on silica gel (12 g) eluting with a gradient of methanol in dichloromethane (0-5%) to give the title compound as a white solid (42 mg).

LRMS (ESI) M+H$^+$528, M−H$^-$ 526;

$^1$H NMR (400 MHz, DMSO-d$_6$) δ [ppm]: 13.19 (s, 1H), 8.25 (dd, J=9.3, 5.8 Hz, 1H), 7.76 (dd, J=8.0, 1.3 Hz, 1H), 7.66 (dd, J=10.4, 2.7 Hz, 1H), 7.45 (s, 1H), 7.44 (d, J=1.7 Hz, 1H), 7.38 (td, J=8.9, 2.6 Hz, 1H), 7.11-7.03 (m, 1H), 6.95 (dd, J=7.1, 1.2 Hz, 1H), 6.90-6.85 (m, 1H), 4.77 (d, J=14.3 Hz, 1H), 4.54 (d, J=14.6 Hz, 1H), 4.21 (t, J=6.0 Hz, 2H), 3.89 (t, J=15.2 Hz, 1H), 3.83 (s, 3H), 3.72 (d, J=12.6 Hz, 1H), 3.65 (d, J=14.4 Hz, 1H), 3.37-3.22 (m, 2H), 2.59 (t, J=11.4 Hz, 1H), 2.27-2.15 (m, 2H), 1.93 (s, 3H), 1.61 (d, J=32.2 Hz, 2H); $^{19}$F NMR (376 MHz, DMSO-d$_6$) δ −114.70 (ddd, J=10.1, 8.7, 6.0 Hz).

The title compound (37 mg) was separated into enantiomers by chiral HPLC to give enantiomer 1 (15 mg, see Example 047) and enantiomer 2 (15 mg, see Example 048).

Preparative chiral HPLC method: Instrument: Sepiatec: Prep SFC100; column: Chiralpak ID 5 μm 250×30 mm; eluent A: CO$_2$, eluent B: 2-propanol+0.4 Vol-% diethylamine (99%); isocratic: 22% B; flow 100.0 ml/min temperature: 40° C.; BPR: 150 bar; MWD @ 254 nm Analytical chiral HPLC method: Instrument: Agilent: 1260, Aurora SFC-Module; column: Chiralpak ID 5 μm 100×4.6 mm; eluent A: CO$_2$, eluent B: 2-propanol+0.2 Vol-% diethylamine (99%); isocratic: 22% B; flow 4.0 ml/min; temperature: 37.5° C.; BPR: 100 bar; MWD @ 254 nm

Example 047

1-{3-[(6-fluoronaphthalen-1-yl)oxy]propyl}-9,11-dimethyl-5,6,8,9-tetrahydro-4H-pyrazolo[4',3':8,9][1,5]oxazecino[7,6,5-hi]indole-2-carboxylic acid-N-ethylethanamine salt (Enantiomer 1)

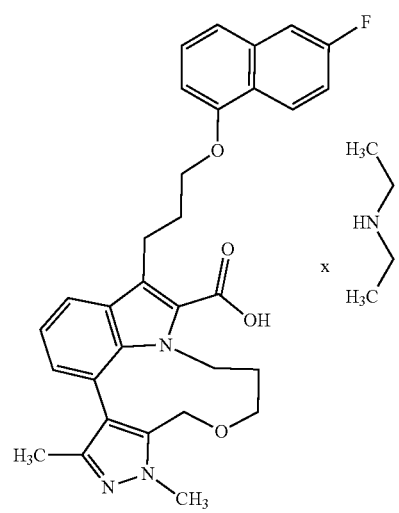

For the preparation of the racemic title compound see Example 046. Separation of enantiomers by preparative chiral HPLC (method see Example 046) gave the title compound (15 mg).

Analytical Chiral HPLC (method see Example 046): R$_t$=3.26 min.

LC-MS (Method 2): Rt=0.84 min; MS (ESIpos): m/z=528 [M+H]$^+$ $^1$H-NMR (400 MHz, DMSO-d6) δ[ppm]: 1.107 (1.58), 1.137 (2.88), 1.154 (6.06), 1.173 (2.91), 1.232 (0.75), 1.518 (0.47), 1.686 (0.47), 1.907 (0.42), 1.920 (16.00), 2.167 (0.87), 2.185 (1.24), 2.201 (0.93), 2.336 (0.42), 2.518 (5.19), 2.522 (3.51), 2.534 (0.82), 2.539 (1.80), 2.562 (0.91), 2.591 (0.53), 2.678 (0.42), 2.873 (0.69), 2.891 (2.15), 2.909 (2.17), 2.928 (0.67), 3.195 (0.44), 3.211 (0.53), 3.228 (0.69), 3.247 (0.49), 3.593 (1.51), 3.629 (1.55), 3.702 (0.69), 3.734 (0.64), 3.810 (16.00), 4.173 (1.31), 4.188 (2.80), 4.204 (1.29), 4.544 (0.67), 4.579 (0.62), 4.746 (1.91), 4.781 (1.84), 6.854 (1.29), 6.862 (1.64), 6.867 (2.04), 6.876 (1.64), 6.885 (1.31), 7.006 (1.13), 7.026 (1.55), 7.043 (0.91), 7.345 (0.82), 7.352 (0.95), 7.367 (1.26), 7.374 (1.38), 7.390 (0.89), 7.397 (0.95), 7.402 (0.42), 7.423 (2.62), 7.428 (2.77), 7.436 (5.64), 7.636 (1.51), 7.643 (1.53), 7.662 (1.55), 7.669 (1.62), 7.681 (1.09), 7.701 (1.00), 8.230 (1.29), 8.245 (1.35), 8.253 (1.33), 8.268 (1.24).

Example 048

1-{3-[(6-fluoronaphthalen-1-yl)oxy]propyl}-9,11-dimethyl-5,6,8,9-tetrahydro-4H-pyrazolo[4',3':8,9][1,5]oxazecino[7,6,5-hi]indole-2-carboxylic acid-N-ethylethanamine salt (Enantiomer 2)

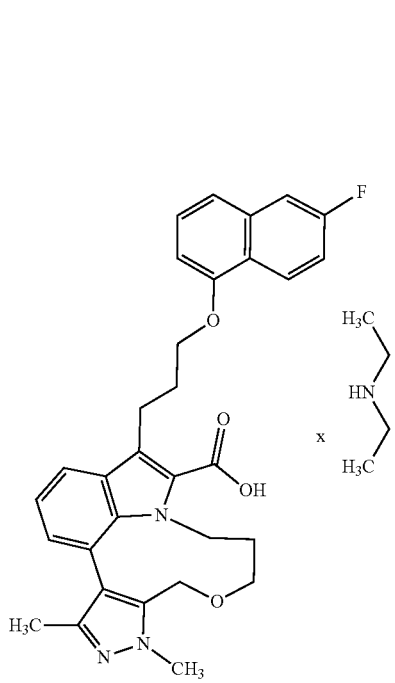

For the preparation of the racemic title compound see Example 046. Separation of enantiomers by preparative chiral HPLC (method see Example 046) gave the title compound (15 mg).

Analytical Chiral HPLC (method see Example 046): $R_t$=6.70 min.

LC-MS (Method 2): Rt=0.84 min; MS (ESIpos): m/z=528 [M+H]$^+$ $^1$H-NMR (400 MHz, DMSO-d6) δ[ppm]: 0.967 (0.39), 1.107 (16.00), 1.134 (2.62), 1.144 (0.49), 1.152 (5.63), 1.170 (2.59), 1.232 (0.86), 1.921 (11.67), 1.959 (0.71), 2.165 (0.71), 2.182 (1.03), 2.198 (0.76), 2.336 (0.46), 2.518 (5.48), 2.522 (3.77), 2.560 (0.73), 2.588 (0.42), 2.673 (1.03), 2.678 (0.44), 2.867 (0.59), 2.886 (1.88), 2.904 (1.81), 2.922 (0.56), 3.212 (0.49), 3.587 (1.10), 3.623 (1.13), 3.704 (0.56), 3.736 (0.54), 3.808 (11.94), 4.171 (1.05), 4.187 (2.30), 4.201 (1.03), 4.551 (0.51), 4.587 (0.49), 4.745 (1.47), 4.781 (1.37), 6.853 (1.49), 6.862 (1.35), 6.866 (1.57), 6.874 (1.25), 6.994 (0.76), 7.013 (1.13), 7.033 (0.64), 7.345 (0.59), 7.352 (0.64), 7.367 (0.95), 7.374 (1.03), 7.390 (0.61), 7.397 (0.69), 7.422 (1.91), 7.426 (2.08), 7.435 (3.79), 7.636 (1.10), 7.642 (1.17), 7.661 (1.71), 7.668 (1.61), 7.684 (0.69), 8.231 (0.93), 8.247 (0.98), 8.255 (0.95), 8.269 (0.91).

Example 049

(rac)-7-{3-[(6-fluoro-7-methylnaphthalen-1-yl)oxy]propyl}-1,3-dimethyl-1,10,11,12,13,15-hexahydro-pyrazolo[4',3':9,10][1,6]oxazacycloundecino[8,7,6-hi]indole-8-carboxylic acid

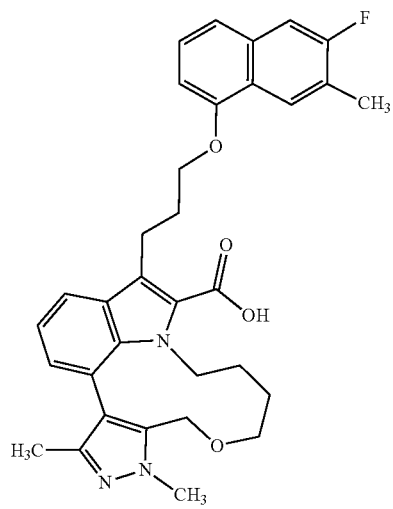 [SMILES: Cc1cc2c(OCCCc3c(C(=O)O)n4c5c(cccc35)-c3c(C)nn(C)c3COCCCC4)cccc2cc1F]

A solution of (rac)-ethyl 7-{3-[(6-fluoro-7-methyl-1-naphthyl)oxy]propyl}-1,3-dimethyl-1,10,11,12,13,15-hexahydropyrazolo[4',3':9,10][1,6]oxazacycloundecino[8,7,6-hi]indole-8-carboxylate (100 mg 0.17 mmol, see Intermediate 70) in methanol (10 ml), tetrahydrofuran (5 ml) and lithium hydroxide (2M in water, 5 ml, 10 mmol), was heated to 50° C. for 7 hours, then cooled to room temperature. Volatiles were removed under reduced pressure and the residue was partitioned between ethyl acetate and aqueous hydrochloric acid (3M), layers were separated and the organic layer was washed with saturated aqueous sodium chloride solution, the combined aqueous phases were extracted with ethyl acetate, the combined organic layers were dried over magnesium sulfate, insoluble material was removed by filtration, volatiles were removed under reduced pressure, and the residue was purified by normal phase chromatography on silica gel (12 g) eluting with a gradient of ethyl acetate in hexanes (50-100%) to give the title compound as a white solid (50 mg).

$^1$H NMR (400 MHz, Chloroform-d) δ [ppm]: 8.18 (d, J=7.9 Hz, 1H), 7.80 (dd, J=8.2, 1.3 Hz, 1H), 7.36 (d, J=10.7 Hz, 1H), 7.30 (s, 1H), 7.29 (s, 2H), 7.12 (dd, J=8.1, 7.1 Hz, 1H), 6.94 (dd, J=7.1, 1.2 Hz, 1H), 6.69 (dd, J=5.2, 3.4 Hz, 1H), 4.69 (dt, J=14.4, 3.9 Hz, 1H), 4.61 (d, J=13.5 Hz, 1H), 4.48 (d, J=13.5 Hz, 1H), 4.19 (dt, J=24.1, 6.7 Hz, 4H), 3.98 (s, 3H), 3.61-3.33 (m, 3H), 2.89 (ddd, J=12.9, 9.1, 4.3 Hz, 1H), 2.48 (t, J=1.4 Hz, 3H), 2.39 (p, J=6.9 Hz, 2H), 2.01 (s, 3H), 1.60-1.50 (m, 1H), 1.36-1.20 (m, 3H), 1.10 (dt, J=15.3, 7.7 Hz, 1H).

LRMS (ESI) M+H+556, M−H− 554.

The title compound (28 mg) was separated into enantiomers by chiral HPLC to give enantiomer 1 (12 mg, see Example 050) and enantiomer 2 (11 mg, see Example 051).

Preparative chiral HPLC method: Instrument: Sepiatec: Prep SFC100; column: Chiralpak IE 5 μm 250×30 mm; eluent A: CO$_2$, eluent B: ethanol+0.4 Vol-% diethylamine (99%); isocratic: 27% B; flow 100.0 ml/min temperature: 40° C.; BPR: 150 bar; MWD @ 254 nm Analytical chiral HPLC method: Instrument: Agilent: 1260, Aurora SFC-Module; column: Chiralpak IE 5 µm 100×4.6 mm; eluent A: $CO_2$, eluent B: ethanol+0.2 Vol-% diethylamine (99%); isocratic: 27% B; flow 4.0 ml/min; temperature: 37.5° C.; BPR: 100 bar; MWD @ 254 nm Example 050

7-{3-[(6-fluoro-7-methylnaphthalen-1-yl)oxy]propyl}-1,3-dimethyl-1,10,11,12,13,15-hexahydropyrazolo[4',3':9,10][1,6]oxazacycloundecino[8,7,6-hi]indole-8-carboxylic acid-N-ethylethanamine salt (Enantiomer 1)

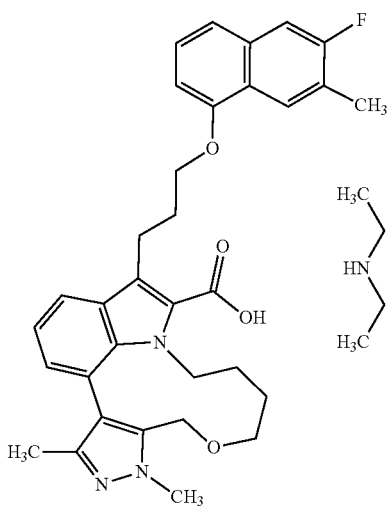

For the preparation of the racemic title compound see Example 049. Separation of enantiomers by preparative chiral HPLC (method see Example 049) gave the title compound (15 mg).

Analytical Chiral HPLC (method see Example 049): $R_t$=2.63 min.

LC-MS (Method 2): Rt=0.87 min; MS (ESIpos): m/z=556 [M+H]$^+$ $^1$H-NMR (400 MHz, DMSO-d6) δ[ppm]: 0.923 (0.47), 0.932 (0.56), 0.950 (0.62), 0.968 (0.64), 0.974 (0.50), 0.992 (0.59), 1.009 (0.59), 1.033 (0.50), 1.068 (0.67), 1.090 (0.70), 1.108 (16.00), 1.124 (4.98), 1.142 (11.02), 1.160 (4.81), 1.232 (0.73), 1.389 (0.41), 1.408 (0.41), 1.808 (11.69), 1.960 (0.44), 2.199 (0.97), 2.212 (0.70), 2.337 (0.62), 2.422 (5.92), 2.518 (6.86), 2.523 (4.84), 2.674 (1.52), 2.678 (0.91), 2.695 (0.53), 2.727 (0.47), 2.830 (1.14), 2.848 (3.40), 2.866 (3.31), 2.884 (1.03), 3.159 (0.44), 3.177 (0.53), 3.288 (1.05), 3.367 (1.11), 3.399 (0.67), 3.821 (12.31), 4.163 (1.08), 4.179 (2.26), 4.194 (1.26), 4.205 (1.55), 4.238 (1.52), 4.609 (1.67), 4.643 (1.55), 4.665 (0.47), 4.700 (0.41), 6.675 (0.73), 6.692 (0.79), 6.801 (1.17), 6.818 (1.23), 6.950 (0.76), 6.969 (1.20), 6.987 (0.67), 7.310 (0.62), 7.330 (1.44), 7.348 (1.38), 7.362 (2.08), 7.382 (0.73), 7.574 (1.90), 7.602 (1.90), 7.621 (0.85), 7.640 (0.76), 8.078 (1.17), 8.099 (1.17).

Example 051

7-{3-[(6-fluoro-7-methylnaphthalen-1-yl)oxy]propyl}-1,3-dimethyl-1,10,11,12,13,15-hexahydropyrazolo[4',3':9,10][1,6]oxazacycloundecino[8,7,6-hi]indole-8-carboxylic acid-N-ethylethanamine salt (Enantiomer 2)

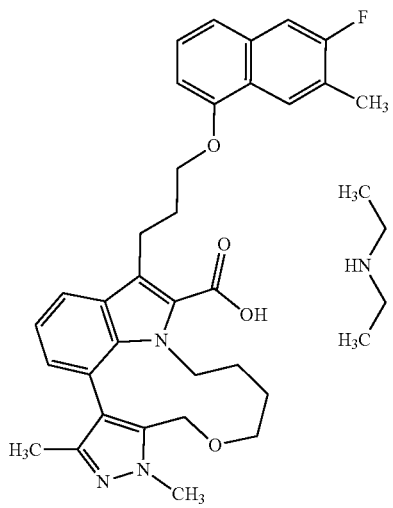

For the preparation of the racemic title compound see Example 049. Separation of enantiomers by preparative chiral HPLC (method see Example 049) gave the title compound (15 mg).

Analytical Chiral HPLC (method see Example 049): $R_t$=3.67 min.

LC-MS (Method 2): Rt=0.87 min; MS (ESIpos): m/z=556 [M+H]$^+$ $^1$H-NMR (400 MHz, DMSO-d6) δ[ppm]: 0.840 (0.42), 0.852 (0.53), 0.860 (0.45), 0.904 (0.53), 0.923 (0.64), 0.937 (0.76), 0.950 (0.72), 0.968 (0.95), 0.974 (0.72), 0.992 (0.80), 1.009 (0.83), 1.032 (0.64), 1.071 (0.64), 1.090 (1.02), 1.108 (5.38), 1.128 (5.50), 1.138 (1.40), 1.146 (11.83), 1.164 (5.19), 1.232 (1.10), 1.389 (0.53), 1.805 (15.55), 1.960 (0.57), 2.184 (0.95), 2.199 (1.33), 2.216 (0.95), 2.337 (0.80), 2.423 (7.92), 2.518 (8.87), 2.523 (6.22), 2.673 (1.90), 2.678 (1.14), 2.699 (0.68), 2.726 (0.57), 2.841 (1.21), 2.859 (3.68), 2.877 (3.56), 2.895 (1.14), 3.158 (0.49), 3.172 (0.57), 3.190 (0.72), 3.210 (0.42), 3.275 (0.87), 3.295 (1.67), 3.369 (1.40), 3.382 (1.02), 3.400 (0.91), 3.419 (0.49), 3.823 (16.00), 3.863 (0.61), 4.165 (1.44), 4.181 (3.00), 4.197 (1.52), 4.207 (1.97), 4.241 (2.01), 4.611 (2.24), 4.644 (2.43), 4.681 (0.53), 6.696 (0.87), 6.713 (0.99), 6.803 (1.55), 6.820 (1.67), 6.963 (0.95), 6.982 (1.52), 7.001 (0.83), 7.312 (0.80), 7.332 (1.93), 7.350 (1.86), 7.364 (2.77), 7.384 (0.99), 7.575 (2.46), 7.602 (2.46), 7.639 (1.06), 7.658 (0.99), 8.077 (1.59), 8.097 (1.59).

Example 052

(rac)-10-(2-methoxyethyl)-7,11-dimethyl-1-[3-(naphthalen-1-yloxy)propyl]-4,5,6,7,8,10-hexahydropyrazolo[3',4':7,8][1,5]diazecino[9,10,1-hi]indole-2-carboxylic acid

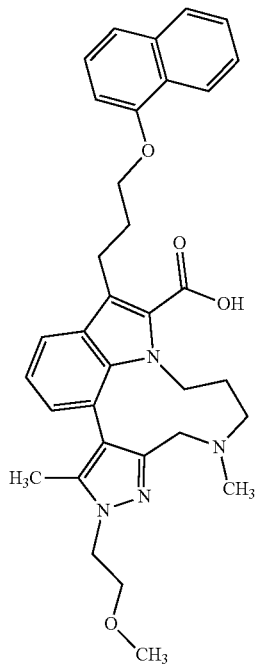 [SMILES: COCCn1nc2c(c1C)-c1cccc3c(CCCOc4cccc5ccccc45)c(C(=O)O)n(c13)CCCN(C)C2]

A mixture of (rac)-ethyl 10-(2-methoxyethyl)-7,11-dimethyl-1-[3-(naphthalen-1-yloxy)propyl]-4,5,6,7,8,10-hexahydropyrazolo[3',4':7,8][1,5]diazecino[9,10,1-hi]indole-2-carboxylate (see Intermediate 139, 77.0 mg, 129 μmol), THF (5.3 ml), ethanol (3.8 ml) and aqueous lithium hydroxide (2.9 ml, 1.0 M, 2.9 mmol) was stirred for 16 h at 50° C. For work-up, citric acid (612 mg, 2.91 mmol) was added to adjust the pH to 5-6, water was added and the mixture was extracted three times with a mixture of dichloromethane/2-propanol (4:1). The combined organic phases were washed with brine, filtered through a silicone filter and concentrated. The residue was purified by flash chromatography (Biotage SNAP cartridge silica, hexanes/ethyl acetate, 50%→100% ethyl acetate) followed by preparative HPLC (method P4) to give the title compound 8.30 mg (90% purity, 10% yield).

LC-MS (Method 1): $R_t$=1.27 min; MS (ESIpos): m/z=567 [M+H]$^+$ $^1$H-NMR (400 MHz, DMSO-d6) δ[ppm]: 0.025 (0.42), 0.893 (0.50), 1.204 (1.28), 1.387 (0.47), 1.395 (0.64), 1.402 (1.39), 1.409 (0.72), 1.418 (0.67), 1.440 (0.53), 1.453 (0.53), 1.461 (0.57), 1.489 (0.74), 1.520 (0.47), 1.544 (0.76), 1.873 (10.48), 1.990 (16.00), 2.032 (0.81), 2.149 (1.33), 2.167 (1.98), 2.183 (4.85), 2.198 (0.66), 2.404 (0.54), 2.431 (0.92), 2.496 (1.59), 2.500 (1.12), 2.518 (10.01), 3.135 (1.44), 3.168 (2.22), 3.197 (0.67), 3.243 (2.85), 3.276 (1.76), 3.310 (1.09), 3.327 (1.63), 3.343 (1.45), 3.357 (1.82), 3.372 (1.22), 3.389 (0.66), 3.633 (0.83), 3.645 (1.16), 3.658 (1.95), 3.671 (1.46), 3.683 (2.00), 3.696 (1.46), 3.703 (3.66), 3.709 (0.94), 3.722 (0.43), 3.756 (0.57), 3.780 (0.60), 3.788 (0.64), 3.813 (0.58), 4.130 (1.49), 4.146 (2.95), 4.161 (1.55), 4.182 (2.05), 4.195 (3.65), 4.209 (1.72), 4.272 (1.23), 4.513 (0.66), 4.523 (0.62), 4.543 (0.56), 4.558 (0.57), 6.749 (1.81), 6.751 (1.81), 6.766 (2.18), 6.769 (2.03), 6.830 (1.88), 6.849 (2.01), 6.915 (1.76), 6.935 (2.16), 6.952 (1.46), 7.330 (1.20), 7.350 (2.39), 7.369 (1.78), 7.413 (2.74), 7.434 (1.59), 7.469 (0.62), 7.482 (1.77), 7.488 (2.63), 7.497 (3.35), 7.506 (2.88), 7.512 (1.80), 7.524 (0.61), 7.627 (1.88), 7.629 (1.89), 7.647 (1.77), 7.827 (1.66), 7.837 (0.88), 7.845 (1.19), 7.850 (1.33), 8.209 (1.43), 8.216 (1.17), 8.225 (0.72), 8.233 (1.30).

Example 053

(rac)-3-methyl-2-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid

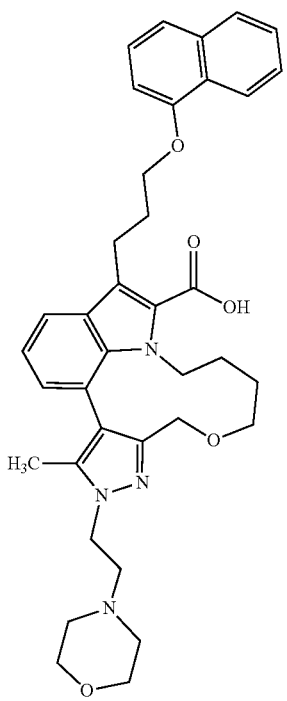 [SMILES: Cc1c2c(nn1CCN1CCOCC1)COCCCCn1c(C(=O)O)c(CCCOc3cccc4ccccc34)c3cccc-2c31]

A mixture of (rac)-ethyl 3-methyl-2-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylate (see Intermediate 142, 757 mg, 1.16 mmol), THF (38 ml), ethanol (27 ml) and aqueous lithium hydroxide (26 ml, 1.0 M, 26 mmol) was stirred for 16 h at 50° C. For work-up, citric acid (5.50 g, 26.2 mmol) was added to adjust the pH to 5-6, water was added and the mixture was extracted three times with a mixture of dichloromethane/2-propanol (4:1). The combined organic phases were washed with brine, filtered through a silicone filter and concentrated. The residue was purified by flash chromatography (25 g Biotage SNAP cartridge silica, dichloromethane/methanol gradient, 0%→20% methanol) to give the title compound (483 mg, 94% purity, 63% yield).

LC-MS (Method 2): $R_t$=0.88 min; MS (ESIpos): m/z=623 [M+H]$^+$ $^1$H-NMR (400 MHz, DMSO-d$_6$): δ [ppm]=13.11 (br s, 1H), 8.28-8.24 (m, 1H), 7.89-7.85 (m, 1H), 7.71 (dd, 1H), 7.56-7.36 (m, 4H), 7.05 (t, 1H), 6.94-6.87 (m, 2H), 4.54 (d, 1H), 4.40-4.09 (m, 6H), 3.93-3.82 (m, 1H), 3.54 (t, 4H), 3.49-3.36 (m, 1H), 3.30-3.22 (m, 2H), 3.13-3.03 (m, 1H), 2.79-2.66 (m, 2H), 2.47-2.35 (m, 4H), 2.28-2.15 (m, 2H), 1.84 (s, 3H), 1.35-1.15 (m, 2H), 1.15-0.95 (m, 2H)

The title compound was separated into enantiomers using chiral preparative HPLC (387 mg) to give enantiomer 1 (174 mg see example 054) and enantiomer 2 (176 mg, see example 055).

Preparative chiral HPLC method: Instrument: Labomatic HD5000, Labocord-5000; Gilson GX-241, Labcol Vario 4000, column: Chiralpak IA 5µ 250×30 mm; eluent A: hexanes+0.1 vol-% diethylamine (99%); eluent B: ethanol; gradient: 20-50% B in 15 min; flow 40.0 ml/min; UV 254 nm Analytical chiral HPLC method: Instrument: Agilent HPLC 1260; column: Chiralpak IA 3µ 100×4.6 mm; eluent A: hexanes+0.1 vol-% diethylamine (99%); eluent B: ethanol; gradient: 20-50% B in 7 min; flow 1.4 ml/min; temperature: 25° C.; DAD 254 nm Example 054

3-methyl-2-[2-(morpholin-4-yl)ethyl]-7-[3-(naphtha-len-1-yloxy)propyl]-2,10,11,12,13,15-hexahydropy-razolo[4',3':9,10][1,6]oxazacycloundecino[8,7,6-hi]indole-8-carboxylic acid-N-ethylethanamine salt
(Enantiomer 1)

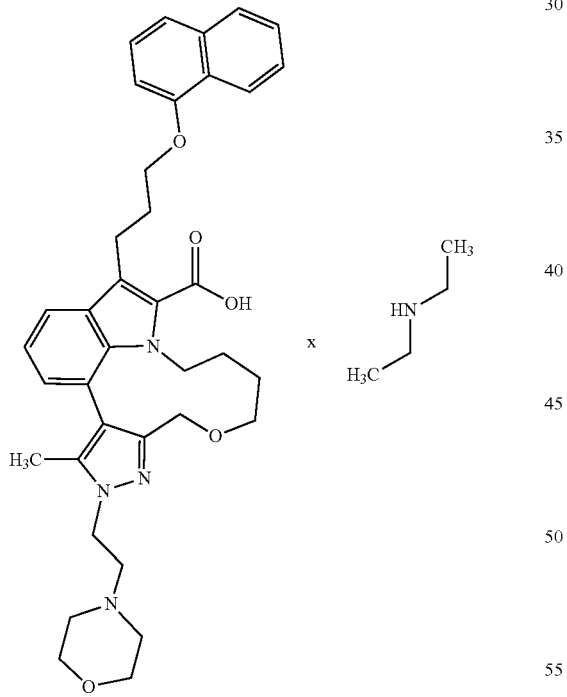

For the preparation of the racemic title compound and separation into enantiomers see Example 053.

Analytical Chiral HPLC (method see Example 053): $R_t$=5.10 min.

LC-MS (Method 2): $R_t$=0.83 min; MS (ESIpos): m/z=623 [M+H]⁺

¹H-NMR (500 MHz, DMSO-d₆): δ [ppm]=8.27-8.24 (m, 1H), 7.88-7.83 (m, 1H), 7.62-7.58 (m, 1H), 7.54-7.49 (m, 2H), 7.44 (d, 1H), 7.37 (t, 1H), 6.97 (t, 1H), 6.89-6.86 (m, 1H), 6.80-6.75 (m, 1H), 4.51-4.41 (m, 2H), 4.28-4.10 (m, 5H), 3.81-3.73 (m, 1H), 3.57-3.51 (m, 4H), 3.24-3.17 (m, 1H), 3.30-3.17 (m, 2H), 3.10-3.04 (m, 1H), 2.83 (q, 3H), 2.78-2.66 (m, 2H), 2.47-2.43 (m, 2H), 2.42-2.38 (m, 2H), 2.23-2.17 (m, 2H), 1.86 (s, 3H), 1.30-1.22 (m, 1H), 1.20-1.05 (m, 8H)

Example 055

3-methyl-2-[2-(morpholin-4-yl)ethyl]-7-[3-(naphtha-len-1-yloxy)propyl]-2,10,11,12,13,15-hexahydropy-razolo[4',3':9,10][1,6]oxazacycloundecino[8,7,6-hi]indole-8-carboxylic acid-N-ethylethanamine salt
(Enantiomer 2)

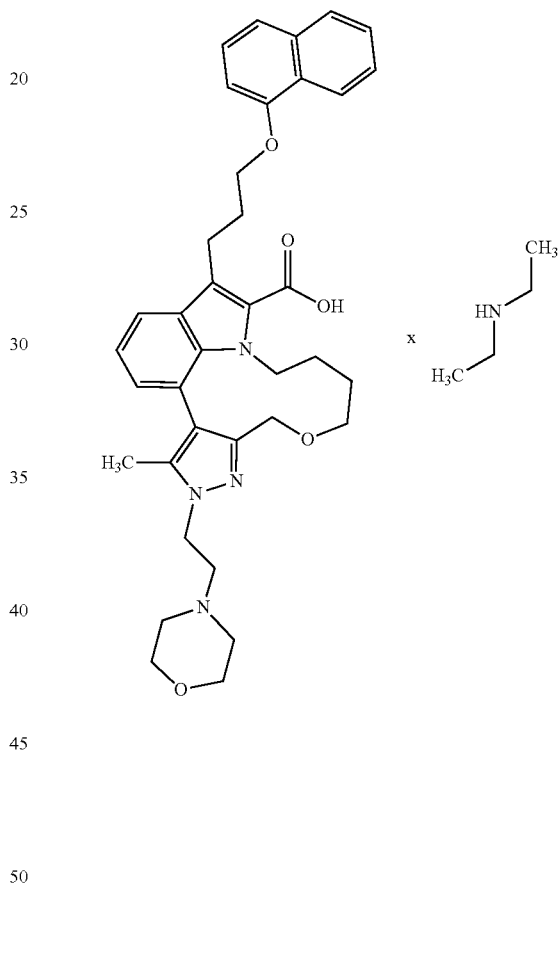

For the preparation of the racemic title compound and separation into enantiomers see Example 053.

Analytical Chiral HPLC (method see Example 053): $R_t$=6.64 min.

Example 056

(rac)-10-(2-methoxyethyl)-7-methyl-11-(morpholin-4-ylmethyl)-1-[3-(naphthalen-1-yloxy)propyl]-4,5,6,7,8,10-hexahydropyrazolo[3',4':7,8][1,5]diazecino[9,10,1-hi]indole-2-carboxylic acid

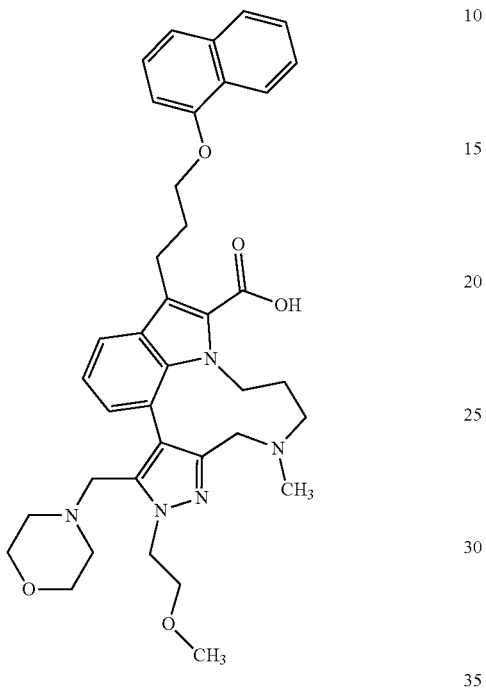

A mixture of (rac)-ethyl 10-(2-methoxyethyl)-7-methyl-11-(morpholin-4-ylmethyl)-1-[3-(naphthalen-1-yloxy)propyl]-4,5,6,7,8,10-hexahydropyrazolo[3',4':7,8][1,5]diazecino[9,10,1-hi]indole-2-carboxylate (see Intermediate 156, 66.0 mg, 97.1 µmol), THF (3.1 ml), ethanol (2.3 ml) and aqueous lithium hydroxide (2.2 ml, 1.0 M, 2.2 mmol) was stirred for 16 h at 50° C. For work-up, citric acid (459 mg, 2.18 mmol) was added to adjust the pH to 5-6, water was added and the mixture was extracted three times with a mixture of dichloromethane/2-propanol (4:1). The combined organic phases were washed with brine, filtered through a silicone filter and concentrated. The residue was purified by flash chromatography (Biotage SNAP cartridge silica, dichloromethane/methanol gradient 0%→20% methanol) to give the title compound 40.0 mg (93% purity, 59% yield).

LC-MS (Method 2): $R_t$=0.91 min; MS (ESIpos): m/z=652 [M+H]$^+$ $^1$H-NMR (400 MHz, DMSO-d$_6$): δ [ppm]=13.31-12.70 (br. s, 1H), 8.30-8.20 (m, 1H), 7.91-7.82 (m, 1H), 7.66 (d, 1H), 7.58-7.31 (m, 4H), 6.95 (t, 1H), 6.85 (d, 1H), 6.77 (d, 1H), 4.63-4.53 (m, 1H), 4.41 (t, 2H), 4.16 (brt, 2H), 3.81-3.68 (m, 3H), 3.54-3.41 (m, 4H), 3.27 (s, 3H), 3.26-3.14 (m, 3H), 2.43-2.36 (m, 1H), 2.28-2.12 (m, 6H), 2.06-1.97 (m, 1H), 1.94-1.82 (m, 3H), 1.64-1.36 (m, 2H).

The title compound was separated into enantiomers using chiral preparative HPLC (33 mg) to give enantiomer 1 (13.5 mg see example 057) and enantiomer 2 (18.5 mg, see example 058).

Preparative chiral HPLC method: Instrument: Labomatic HD5000, Labocord-5000; Gilson GX-241, Labcol Vario 4000, column: Chiralpak AD-H 5µ 250×30 mm; eluent A: hexanes+0.1 vol-% diethylamine (99%); eluent B: ethanol; gradient: 20-50% B in 20 min; flow 40.0 ml/min; UV 254 nm Analytical chiral HPLC method: Instrument: Agilent HPLC 1260; column: Chiralpak AD-H 3µ 100×4.6 mm; eluent A: hexanes+0.1 vol-% diethylamine (99%); eluent B: ethanol; Gradient: 20-50% B in 7 min; flow 1.4 ml/min; temperature: 25° C.; DAD 254 nm

Example 057

10-(2-methoxyethyl)-7-methyl-11-(morpholin-4-ylmethyl)-1-[3-(naphthalen-1-yloxy)propyl]-4,5,6,7,8,10-hexahydropyrazolo[3',4':7,8][1,5]diazecino[9,10,1-hi]indole-2-carboxylic acid (Enantiomer 1)

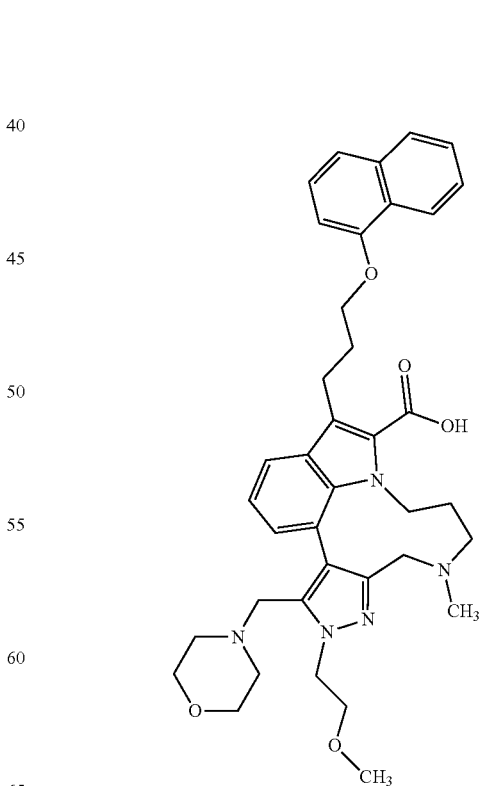

For the preparation of the racemic title compound and separation into enantiomers see Example 056.

Analytical Chiral HPLC (method see Example 056): $R_t$=1.46 min. ee>99%.

LC-MS (Method 1): $R_t$=1.31 min; MS (ESIpos): m/z=652 [M+H]$^+$ $^1$H-NMR (400 MHz, DMSO-d6) δ[ppm]: 1.135 (1.02), 1.144 (0.56), 1.153 (2.03), 1.171 (0.97), 1.229 (0.41), 1.905 (0.41), 2.067 (0.71), 2.197 (0.41), 2.215 (0.61), 2.232 (0.46), 2.323 (2.08), 2.327 (2.95), 2.331 (2.13), 2.518 (16.00), 2.523 (10.72), 2.665 (2.18), 2.669 (2.95), 2.673 (2.18), 2.807 (1.83), 2.913 (0.41), 3.001 (0.61), 3.287 (3.30), 3.298 (1.27), 3.343 (0.46), 3.374 (0.41), 3.795 (0.71), 3.843 (0.30), 3.878 (0.30), 4.230 (0.66), 4.384 (0.41), 4.419 (0.36), 4.619 (0.66), 6.913 (0.51), 6.932 (0.56), 7.170 (1.07), 7.185 (0.56), 7.384 (0.41), 7.405 (0.81), 7.424 (0.66), 7.459 (1.07), 7.479 (0.56), 7.522 (0.81), 7.531 (1.07), 7.541 (0.91), 7.547 (0.61), 7.866 (0.56), 7.889 (0.91), 7.904 (0.46), 8.271 (0.41), 14.788 (2.44).

Example 058

10-(2-methoxyethyl)-7-methyl-11-(morpholin-4-ylmethyl)-1-[3-(naphthalen-1-yloxy)propyl]-4,5,6,7,8,10-hexahydropyrazolo[3',4':7,8][1,5]diazecino[9,10,1-hi]indole-2-carboxylic acid (Enantiomer 2)

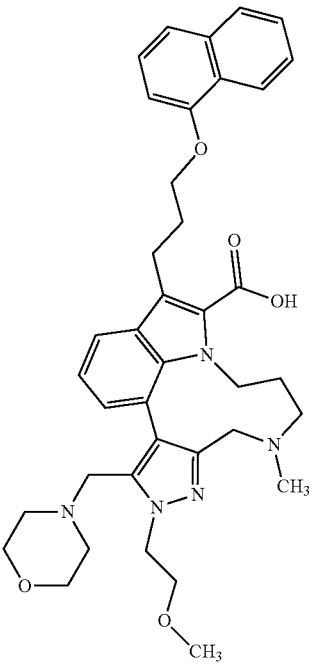 [SMILES: COCCn1nc2c(c1CN1CCOCC1)-c1cccc3c(CCCOc4cccc5ccccc45)c(C(=O)O)n(c13)CCCN(C)C2]

For the preparation of the racemic title compound and separation into enantiomers see Example 056.

Analytical Chiral HPLC (method see Example 056): $R_t$=3.37 min. ee>99%.

Example 059

(rac)-7,11-dimethyl-10-[2-(morpholin-4-yl)ethyl]-1-[3-(naphthalen-1-yloxy)propyl]-4,5,6,7,8,10-hexahydropyrazolo[3',4':7,8][1,5]diazecino[9,10,1-hi]indole-2-carboxylic acid

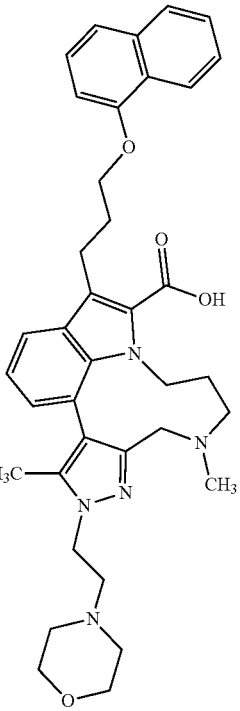

A mixture of (rac)-ethyl 7,11-dimethyl-10-[2-(morpholin-4-yl)ethyl]-1-[3-(naphthalen-1-yloxy)propyl]-4,5,6,7,8,10-hexahydropyrazolo[3',4':7,8][1,5]diazecino[9,10,1-hi]indole-2-carboxylate (see Intermediate 148, 285 mg, 439 µmol), THF (14 ml), ethanol (10 ml) and aqueous lithium hydroxide (9.9 ml, 1.0 M, 9.9 mmol) was stirred for 16 h at 50° C. For work-up, citric acid (2.07 g, 9.87 mmol) was added to adjust the pH to 5-6, water was added and the mixture was extracted three times with a mixture of dichloromethane/2-propanol (4:1). The combined organic phases were washed with brine, filtered through a silicone filter and concentrated. The residue was purified by flash chromatography (Biotage SNAP cartridge silica, dichloromethane/methanol gradient, 0%→20% methanol) to give the title compound 199 mg (90% purity, 66% yield).

LC-MS (Method 2): $R_t$=0.86 min; MS (ESIpos): m/z=622 [M+H]$^+$ $^1$H-NMR (400 MHz, DMSO-d$_6$): δ [ppm]=13.50-12.50 (m, 1H), 8.27-8.22 (m, 1H), 7.90-7.83 (m, 1H), 7.67 (d, 1H), 7.56-7.36 (m, 4H), 6.97 (t, 1H), 6.87 (d, 1H), 6.79 (d, 1H), 4.61-4.50 (m, 1H), 4.25-4.09 (m, 4H), 3.88-3.77 (m, 1H), 3.53 (t, 4H), 3.30-3.18 (m, 2H), 2.79-2.68 (m, 2H), 2.46-2.35 (m, 4H), 2.19 (quin, 2H), 2.12-1.99 (m, 4H), 1.97-1.82 (m, 2H), 1.70-1.46 (m, 2H) The title compound was separated into enantiomers using chiral preparative HPLC (110 mg), followed by additional preparative HPLC, to give enantiomer 1 (15.5 mg see example 060) and enantiomer 2 (16.5 mg, see example 061).

Preparative chiral HPLC method: Instrument: Labomatic HD5000, Labocord-5000; Gilson GX-241, Labcol Vario 4000, column: Chiralpak AD-H 5μ 250×30 mm; eluent A: hexanes+0.1 vol-% diethylamine (99%); eluent B: 2-propanol; gradient: 20-50% B in 15 min; flow 40.0 ml/min; UV 254 nm.

Analytical chiral HPLC method: Instrument: Agilent HPLC 1260; column: Chiralpak AD-H 3μ 100×4.6 mm; eluent A: hexanes+0.1 vol-% diethylamine (99%); eluent B: 2-propanol; gradient: 20-50% B in 7 min; flow 1.4 ml/min; temperature: 25° C.; DAD 254 nm Example 060

7,11-dimethyl-10-[2-(morpholin-4-yl)ethyl]-1-[3-(naphthalen-1-yloxy)propyl]-4,5,6,7,8,10-hexahydropyrazolo[3',4':7,8][1,5]diazecino[9,10,1-hi]indole-2-carboxylic acid (Enantiomer 1)

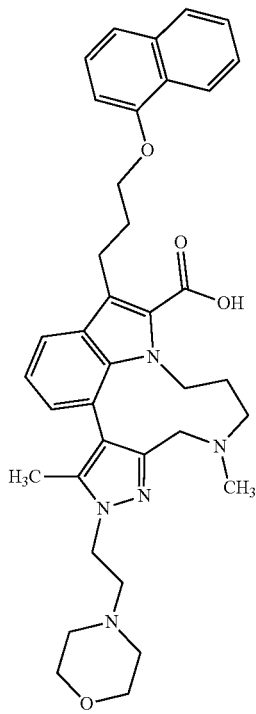 [SMILES: Cc1c2c(nn1CCN1CCOCC1)CN(C)CCCn1c(C(=O)O)c(CCCOc3cccc4ccccc34)c3cccc-2c31]

For the preparation of the racemic title compound and separation into enantiomers see Example 059. The title compound (29 mg) was further purified by preparative HPLC [Instrument: Waters Autopurification system; column: Waters XBrigde C18 5μ 100×30 mm; eluent A: water+ 0.2 vol-% ammonia (32%), eluent B: methanol; gradient: 0.00-0.50 min 23% B (25→70 mL/min), 0.51-5.50 min 47-67% B (70 mL/min), DAD scan: 210-400 nm] to give the title compound (15.5 mg).

Analytical Chiral HPLC (method see Example 059): $R_t$=5.18 min; ee 78.7%

Example 061

7,11-dimethyl-10-[2-(morpholin-4-yl)ethyl]-1-[3-(naphthalen-1-yloxy)propyl]-4,5,6,7,8,10-hexahydropyrazolo[3',4':7,8][1,5]diazecino[9,10,1-hi]indole-2-carboxylic acid (Enantiomer 2)

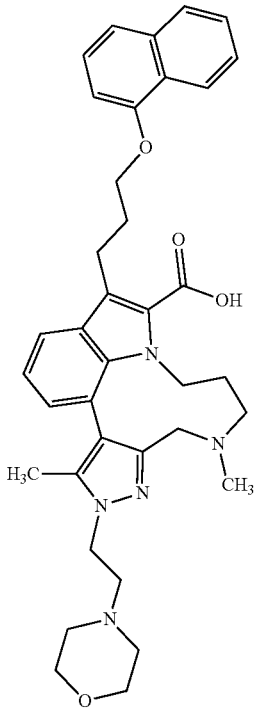 [SMILES: Cc1c2c(nn1CCN1CCOCC1)CN(C)CCCn1c(C(=O)O)c(CCCOc3cccc4ccccc34)c3cccc-2c31]

For the preparation of the racemic title compound and separation into enantiomers see Example 059. The title compound (32 mg) was further purified by preparative HPLC [Instrument: Waters Autopurification system; column: Waters XBrigde C18 5μ 100×30 mm; eluent A: water+ 0.2 vol-% ammonia (32%), eluent B: methanol; gradient: 0.00-0.50 min 25% B (25→70 mL/min), 0.51-5.50 min 49-70% B (70 mL/min), DAD scan: 210-400 nm] to give the title compound (16.5 mg).

Analytical Chiral HPLC (method see Example 059): $R_t$=2.27 min; ee 94.9%

Example 062

(rac)- (11Z)-2,3-dimethyl-7-[3-(naphthalen-1-yloxy)propyl]-2,10,13,15-tetrahydropyrazolo[4',3':9,10][1,6]oxazacycloundecino[8,7,6-hi]indole-8-carboxylic acid

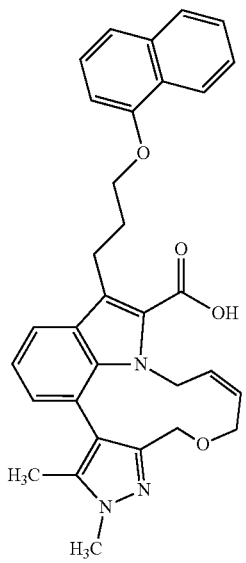 [SMILES: Cc1c2c(nn1C)COC/C=C\Cn1c(C(=O)O)c(CCCOc3cccc4ccccc34)c3cccc-2c31]

A mixture of (rac)-ethyl (11Z)-2,3-dimethyl-7-[3-(naphthalen-1-yloxy)propyl]-2,10,13,15-tetrahydropyrazolo[4',3':9,10][1,6]oxazacycloundecino[8,7,6-hi]indole-8-carboxylate (see Intermediate 158, 30.0 mg, 54.6 μmol), THF (1.8 ml), ethanol (1.3 ml) and aqueous lithium hydroxide (1.2 ml, 1.0 M, 1.2 mmol) was stirred for 16 h at 50° C. For work-up, citric acid (258 mg, 1.23 mmol) was added to adjust the pH to 5-6, water was added and the mixture was extracted three times with a mixture of dichloromethane/2-propanol (4:1). The combined organic phases were washed with brine, filtered through a silicone filter and concentrated. The residue was purified flash chromatography (Biotage SNAP cartridge silica, dichloromethane/methanol gradient, 0%→20% methanol) to give the title compound 19.8 mg (69% yield).

LC-MS (Method 2): $R_t$=0.83 min; MS (ESIpos): m/z=522 [M+H]$^+$ $^1$H-NMR (400 MHz, DMSO-d6) δ[ppm]: 1.145 (0.54), 1.840 (14.43), 2.211 (1.08), 2.228 (1.63), 2.245 (1.19), 2.323 (2.28), 2.327 (3.15), 2.522 (16.00), 2.665 (2.33), 2.669 (3.20), 3.159 (4.56), 3.172 (4.77), 3.573 (0.60), 3.585 (0.76), 3.603 (0.98), 3.616 (0.87), 3.735 (0.87), 3.763 (1.30), 3.792 (0.76), 3.837 (14.37), 4.096 (0.92), 4.108 (0.92), 4.205 (1.52), 4.223 (3.74), 4.236 (1.57), 4.257 (2.60), 4.359 (2.49), 4.391 (1.74), 4.740 (0.60), 4.765 (0.60), 4.988 (0.65), 5.023 (0.54), 5.166 (0.87), 5.187 (0.60), 5.261 (0.71), 5.273 (0.65), 6.816 (1.03), 6.834 (1.19), 6.901 (1.79), 6.919 (1.95), 7.035 (0.98), 7.054 (1.57), 7.074 (0.87), 7.372 (1.14), 7.392 (2.33), 7.411 (1.84), 7.447 (2.66), 7.468 (1.41), 7.490 (0.54), 7.503 (1.41), 7.507 (1.36), 7.512 (1.63), 7.520 (3.04), 7.527 (1.74), 7.532 (1.57), 7.536 (1.63), 7.549 (0.65), 7.716 (1.25), 7.736 (1.14), 7.856 (1.52), 7.874 (1.41), 7.880 (1.36), 8.224 (1.30), 8.229 (1.36), 8.247 (1.36).

Example 063

(rac)-10,11-dimethyl-1-[3-(naphthalen-1-yloxy)propyl]-5,6,8,10-tetrahydro-4H-pyrazolo[4',3':8,9][1,5]oxazecino[7,6,5-hi]indole-2-carboxylic acid

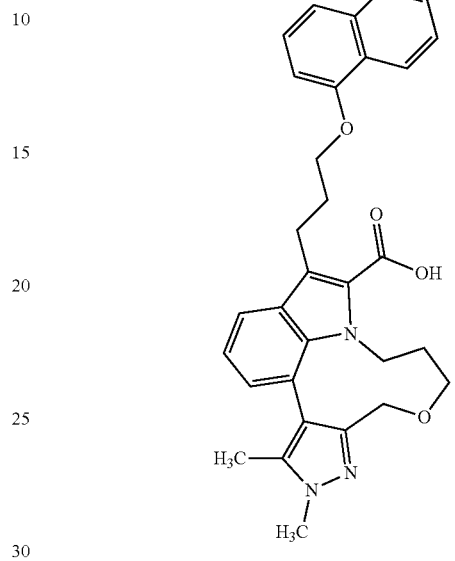

A mixture of (rac)-ethyl 10,11-dimethyl-1-[3-(naphthalen-1-yloxy)propyl]-5,6,8,10-tetrahydro-4H-pyrazolo[4',3':8,9][1,5]oxazecino[7,6,5-hi]indole-2-carboxylate (see Intermediate 157, 120 mg, 223 μmol), THF (9.1 ml), ethanol (6.5 ml) and aqueous lithium hydroxide (4.5 ml, 1.0 M, 4.5 mmol) was stirred for 16 h at 50° C. For work-up, citric acid (1.41 g, 6.70 mmol) was added to adjust the pH to 5-6, water was added and the mixture was extracted three times with a mixture of dichloromethane/2-propanol (4:1). The combined organic phases were washed with brine, filtered through a silicone filter and concentrated. The residue was purified by preparative HPLC (method P7) to give the title compound 48.8 mg (42% yield).

LC-MS (Method 1): $R_t$=1.47 min; MS (ESIpos): m/z=510 [M+H]$^+$ $^1$H-NMR (400 MHz, DMSO-d6) δ[ppm]: 1.580 (0.43), 1.636 (0.52), 2.012 (16.00), 2.178 (0.93), 2.195 (1.36), 2.212 (0.97), 2.332 (0.54), 2.518 (2.83), 2.522 (1.95), 2.539 (1.34), 2.673 (0.55), 3.017 (0.54), 3.036 (0.45), 3.248 (0.48), 3.263 (0.60), 3.282 (0.98), 3.301 (0.80), 3.360 (0.85), 3.379 (0.62), 3.463 (0.51), 3.483 (0.70), 3.492 (0.45), 3.504 (0.41), 3.808 (15.90), 3.908 (1.57), 3.941 (2.17), 3.972 (0.56), 4.000 (0.46), 4.188 (1.35), 4.203 (2.84), 4.218 (1.31), 4.278 (2.13), 4.311 (1.84), 4.565 (0.52), 4.601 (0.47), 6.839 (1.38), 6.841 (1.40), 6.857 (1.67), 6.894 (1.68), 6.912 (1.84), 7.003 (1.62), 7.020 (1.75), 7.022 (1.93), 7.040 (1.33), 7.370 (1.29), 7.391 (2.45), 7.410 (2.03), 7.445 (2.56), 7.466 (1.38), 7.492 (0.57), 7.504 (1.59), 7.509 (1.48), 7.513 (1.81), 7.521 (3.56), 7.528 (1.87), 7.532 (1.61), 7.537 (1.72), 7.549 (0.64), 7.710 (1.48), 7.712 (1.50), 7.729 (1.42), 7.732 (1.36), 7.855 (1.48), 7.863 (0.76), 7.873 (1.29), 7.879 (1.25), 8.223 (1.34), 8.229 (1.20), 8.240 (0.64), 8.245 (1.12), 8.247 (1.24).

The title compound was separated into enantiomers using chiral preparative HPLC (42.6 mg) to give enantiomer 1 (22.0 mg see example 064) and enantiomer 2 (25.3 mg, see example 065).

Preparative chiral HPLC method: Instrument: Labomatic HD5000, Labocord-5000; Gilson GX-241, Labcol Vario 4000, column: Chiralpak AD 5μ 250×30 mm; eluent A: hexanes+0.1 vol-% diethylamine (99%); eluent B: ethanol; gradient: 20-50% B in 20 Min; flow 40.0 ml/min; UV 280 nm Analytical chiral HPLC method: Instrument: Agilent HPLC 1260; column: Chiralpak AD 3μ 100×4.6 mm; eluent A: hexanes+0.1 vol-% diethylamine (99%); eluent B: ethanol; gradient: 20-50% B in 7 Min; flow 1.4 ml/min; temperature: 25° C.; DAD 280 nm Example 064

10,11-dimethyl-1-[3-(naphthalen-1-yloxy)propyl]-5,6,8,10-tetrahydro-4H-pyrazolo[4',3':8,9][1,5]oxazecino[7,6,5-hi]indole-2-carboxylic acid-N-ethylethanamine salt (Enantiomer 1)

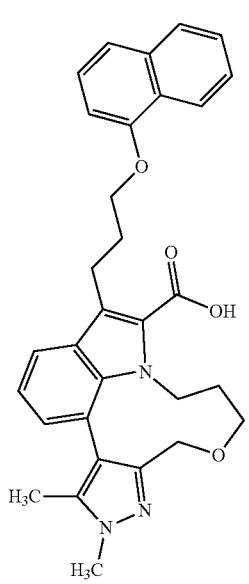 [SMILES: Cc1c2c(nn1C)COCCCn1c(C(=O)O)c(CCCOc3cccc4ccccc34)c3cccc-2c31]

For the preparation of the racemic title compound and separation into enantiomers see Example 063.

Analytical Chiral HPLC (method see Example 063): $R_t$=1.58 min; ee 98.8%

LC-MS (Method 2): $R_t$=0.86 min; MS (ESIpos): m/z=510 [M+H]$^+$ $^1$H-NMR (400 MHz, DMSO-d$_6$): δ [ppm]=8.27-8.21 (m, 1H), 7.89-7.84 (m, 1H), 7.61 (d, 1H), 7.55-7.36 (m, 4H), 6.98-6.87 (m, 2H), 6.73 (d, 1H), 4.67 (br d, 1H), 4.33 (d, 1H), 4.18 (t, 2H), 3.94-3.82 (m, 2H), 3.80 (s, 3H), 3.57-3.47 (m, 1H), 3.25-3.06 (m, 1H), 2.97-2.83 (m, 7H), 2.25-2.11 (m, 2H), 2.01 (s, 3H), 1.82-1.47 (m, 3H), 1.15 (t, 8H)

Example 065

10,11-dimethyl-1-[3-(naphthalen-1-yloxy)propyl]-5,6,8,10-tetrahydro-4H-pyrazolo[4',3':8,9][1,5]oxazecino[7,6,5-hi]indole-2-carboxylic acid-N-ethylethanamine salt (Enantiomer 2)

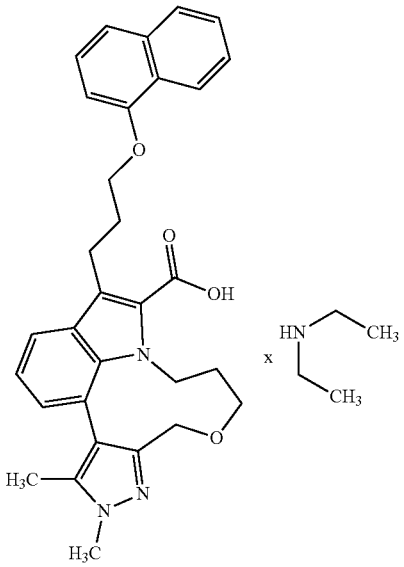

For the preparation of the racemic title compound and separation into enantiomers see Example 063

Analytical Chiral HPLC (method see Example 063): $R_t$=3.93 min; ee 98.5%

Example 066

(rac)-(11Z)-2-Methyl-3-(morpholin-4-ylmethyl)-7-[3-(naphthalen-1-yloxy)propyl]-2,10,13,15-tetrahydropyrazolo[4',3':9,10][1,6]oxazacycloundecino[8,7,6-hi]indole-8-carboxylic acid

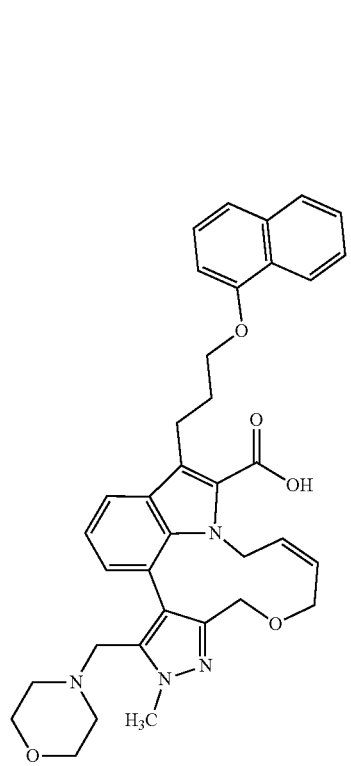 [SMILES: Cn1nc2c(c1CN1CCOCC1)-c1cccc3c(CCCOc4cccc5ccccc45)c(C(=O)O)n(c13)C/C=C\COC2]

A mixture of (rac)-ethyl (11Z)-2-methyl-3-(morpholin-4-ylmethyl)-7-[3-(naphthalen-1-yloxy)propyl]-2,10,13,15-tetrahydropyrazolo[4',3':9,10][1,6]oxazacycloundecino[8,7,6-hi]indole-8-carboxylate (85.0 mg, 134 µmol, see Intermediate 190), THF (4.3 mL), ethanol (3.1 mL) and lithium hydroxide (3.0 mL, 1.0 M in water) was stirred at 50° C. overnight. Water was added, the mixture was acidified by the addition of citric acid (pH 5-6) and extracted with dichloromethane. The organic layer was dried over sodium sulfate. After filtration and removal of the solvents the residue was purified by preparative HPLC (method P1) to give the title compound (40 mg, 49% yield) as mixture of atropisomers.

LC-MS: m/z=607 [M+H]$^+$.

$^1$H-NMR (400 MHz, DMSO-d6), δ [ppm]=2.05 (4H), 2.24 (2H), 2.96 (1H), 3.11 (1H), 3.28-3.45 (6H), 3.62 (1H), 3.79 (1H), 3.95 (3H), 4.20 (2H), 4.24 (1H), 4.41 (1H), 4.70 (1H), 4.97 (1H), 5.15 (1H), 5.27 (1H), 6.83 (1H), 6.88 (1H), 7.04 (1H), 7.38 (1H), 7.46 (1H), 7.52 (2H), 7.75 (1H), 7.87 (1H), 8.24 (1H), 13.29 (1H).

Example 067

(rac)-2,3,14-trimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylic acid

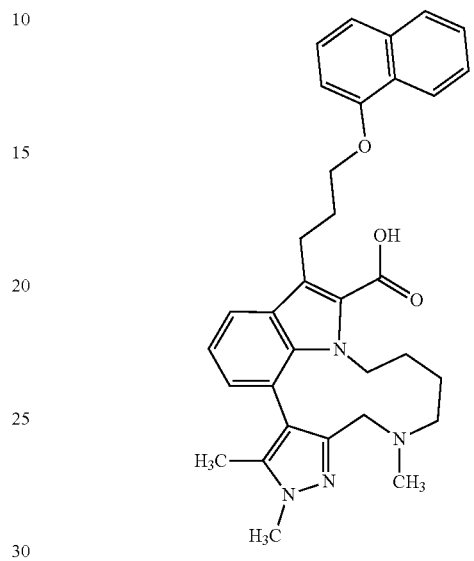

A mixture of (rac)-ethyl 2,3,14-trimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylate (see Intermediate 162, 290 mg, 514 µmol), THF (21 ml), ethanol (15 ml) and aqueous lithium hydroxide (10 ml, 1.0 M, 10 mmol) was stirred for 16 h at 50° C. For work-up, citric acid (2.16 g, 10.3 mmol) was added to adjust the pH to 5-6, water was added and the mixture was extracted three times with a mixture of dichloromethane/2-propanol (4:1). The combined organic phases were washed with brine, filtered through a silicone filter and concentrated. The residue was purified by preparative HPLC (method P4) to give the title compound 74.4 mg (26% yield).

LC-MS (Method 1): R$_t$=1.22 min; MS (ESIneg): m/z=535 [M−H]$^-$ $^1$H-NMR (400 MHz, DMSO-d6) δ[ppm]: 1.045 (1.45), 1.213 (0.59), 1.230 (0.66), 1.801 (16.00), 1.904 (0.76), 1.917 (0.55), 1.939 (0.62), 2.077 (8.13), 2.151 (1.14), 2.168 (0.95), 2.185 (1.26), 2.202 (1.95), 2.220 (1.40), 2.236 (0.74), 2.248 (0.69), 2.261 (0.54), 2.280 (0.55), 2.518 (5.45), 2.522 (3.80), 2.539 (2.47), 3.215 (0.54), 3.234 (0.95), 3.248 (1.00), 3.267 (1.54), 3.287 (1.17), 3.300 (1.83), 3.331 (2.45), 3.341 (2.28), 3.356 (1.67), 3.375 (1.42), 3.393 (0.81), 3.552 (1.93), 3.584 (1.57), 3.880 (0.81), 3.891 (0.69), 3.905 (0.52), 4.183 (1.55), 4.199 (3.30), 4.214 (1.64), 4.366 (0.55), 4.381 (0.54), 4.398 (0.48), 6.822 (1.71), 6.839 (2.04), 6.875 (2.00), 6.894 (2.17), 7.001 (1.80), 7.020 (2.30), 7.039 (1.55), 7.357 (1.40), 7.377 (2.68), 7.397 (2.05), 7.442 (3.04), 7.463 (1.76), 7.496 (0.57), 7.508 (1.86), 7.513 (3.18), 7.523 (3.52), 7.532 (3.31), 7.537 (1.97), 7.549 (0.60), 7.658 (1.90), 7.678 (1.81), 7.854 (1.73), 7.864 (0.86), 7.871 (1.14), 7.877 (1.48), 8.195 (2.43), 8.250 (1.47), 8.258 (1.10), 8.274 (1.35).

The title compound was separated into enantiomers using chiral preparative HPLC (74.4 mg) to give 2 enantiomers. Both enantiomers were repurified by preparative HPLC [column XBridge C18, 100×30 mm, 5 µm; flow 60 mL/min, eluent A: 0,2% aqueous ammonia, eluent B: acetonitrile; gradient 0-5 min: 15% eluent B, 5-17 min: 15-55% eluent B 17.1-20 min: 100% eleuent B] to give enantiomer 1 (28.1 mg see example 068) and enantiomer 2 (21.2 mg, see example 069).

Preparative chiral HPLC method: Instrument: Labomatic HD5000, Labocord-5000; Gilson GX-241, Labcol Vario 4000, column: Chiralpak IE 5μ 250×30 mm; eluent A: hexanes+0.1 vol-% diethylamine (99%); eluent B: ethanol; gradient: 20-50% B in 20 min; flow 40.0 ml/min; UV 254 nm Analytical Chiral HPLC Method:

Instrument: Agilent HPLC 1260; column: Chiralpak IE 3μ 100×4.6 mm; eluent A: hexanes+0.1 vol-% diethylamine (99%); eluent B: ethanol; gradient: 20-50% B in 7 min; flow 1.4 ml/min; temperature: 25° C.; DAD 254 nm Example 068

2,3,14-trimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylic acid (Enantiomer 1)

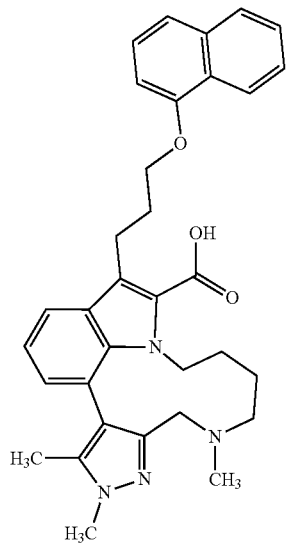 [SMILES: Cc1c2c(nn1C)CN(C)CCCCn1c(C(=O)O)c(CCCOc3cccc4ccccc34)c3cccc-2c31]

For the preparation of the racemic title compound and separation into enantiomers see Example 067:
Analytical Chiral HPLC (method see Example 067): $R_t$=5.92 min. ee>99%

Example 069

2,3,14-trimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylic acid (Enantiomer 2)

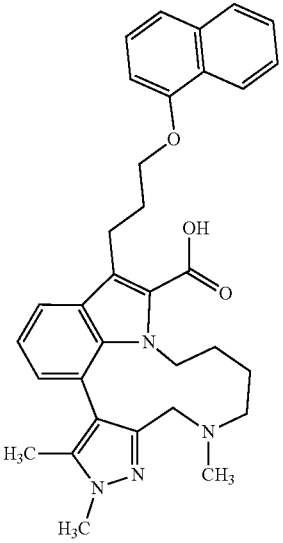 [SMILES: Cc1c2c(nn1C)CN(C)CCCCn1c(C(=O)O)c(CCCOc3cccc4ccccc34)c3cccc-2c31]

For the preparation of the racemic title compound and separation into enantiomers see Example 067.
Analytical Chiral HPLC (method see Example 067): $R_t$=6.58 min. ee>97.6%

Example 070

(rac)-(11Z)-2,3,4-trimethyl-7-[3-(naphthalen-1-yloxy)propyl]-2,10,13,15-tetrahydropyrazolo[4',3':9,10][1,6]oxazacycloundecino[8,7,6-hi]indole-8-carboxylic acid

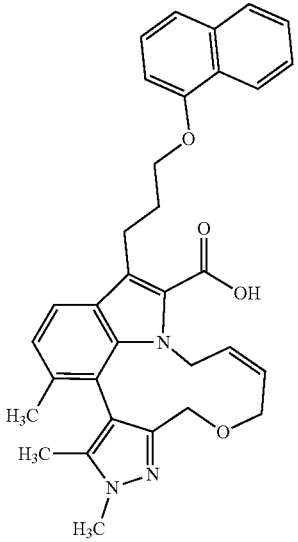 [SMILES: Cc1ccc2c(CCCOc3cccc4ccccc34)c(C(=O)O)n3c2c1-c1c(nn(C)c1C)COC/C=C\C3]

A mixture of (rac)-ethyl (11Z)-2,3,4-trimethyl-7-[3-(naphthalen-1-yloxy)propyl]-2,10,13,15-tetrahydropyrazolo[4',3':9,10][1,6]oxazacycloundecino[8,7,6-hi]indole-8-carboxylate (see Intermediate 164, 75.0 mg, 133 µmol), THF (4.3 ml), ethanol (3.1 ml) and aqueous lithium hydroxide (3.0 ml, 1.0 M, 3.0 mmol) was stirred for 16 h at 50° C. For work-up, citric acid (629 mg, 2.99 mmol) was added to adjust the pH to 5-6, water was added and the mixture was extracted three times with a mixture of dichloromethane/2-propanol (4:1). The combined organic phases were washed with brine, filtered through a silicone filter and concentrated. The residue was purified by flash chromatography (10 g Biotage SNAP cartridge silica, dichloromethane/methanol gradient 0%→10% dichloromethane) to give the title compound 49.6 mg (69% yield).

LC-MS (Method 1): $R_t$=1.48 min; MS (ESIpos): m/z=536 [M+H]$^+$ $^1$H-NMR (400 MHz, DMSO-d$_6$): δ [ppm]=13.18 (br s, 1H), 8.25-8.20 (m, 1H), 7.89-7.84 (m, 1H), 7.63 (d, 1H), 7.55-7.37 (m, 4H), 7.03 (d, 1H), 6.91 (d, 1H), 5.21 (td, 1H), 5.03-4.92 (m, 2H), 4.59 (dd, 1H), 4.41 (d, 1H), 4.24-4.18 (m, 2H), 4.11 (d, 1H), 3.86 (s, 3H), 3.79 (t, 1H), 3.59 (dd, 1H), 3.31-3.23 (m, 2H), 2.67 (dt, 1H), 2.54-2.52 (m, 3H), 2.27-2.17 (m, 2H), 1.89 (s, 3H), 1.76 (s, 3H).

Example 071

(rac)-(11Z)-2-(2-methoxyethyl)-3-methyl-7-[3-(naphthalen-1-yloxy)propyl]-2,10,13,15-tetrahydropyrazolo[4',3':9,10][1,6]oxazacycloundecino[8,7,6-hi]indole-8-carboxylic acid

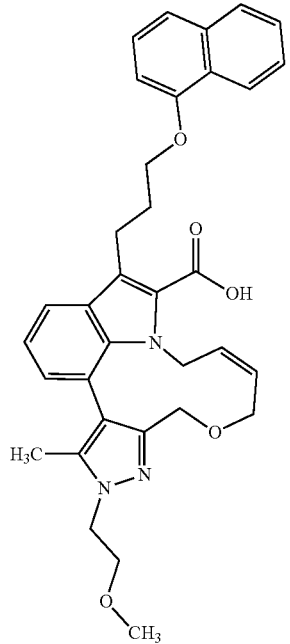 [SMILES: COCCn1nc2c(c1C)-c1cccc3c(CCCOc4cccc5ccccc45)c(C(=O)O)n(c13)C/C=C\COC2]

A mixture of (rac)-ethyl (11Z)-2-(2-methoxyethyl)-3-methyl-7-[3-(naphthalen-1-yloxy)propyl]-2,10,13,15-tetrahydropyrazolo[4',3':9,10][1,6]oxazacycloundecino[8,7,6-hi]indole-8-carboxylate (see Intermediate 143, 75.0 mg, 126 µmol), THF (4.1 ml), ethanol (2.9 ml) and aqueous lithium hydroxide (2.8 ml, 1.0 M, 2.8 mmol) was stirred for 16 h at 50° C. For work-up, citric acid (597 mg, 2.84 mmol) was added to adjust the pH to 5-6, water was added and the mixture was extracted three times with a mixture of dichloromethane/2-propanol (4:1). The combined organic phases were washed with brine, filtered through a silicone filter and concentrated. The residue was purified by flash chromatography (Biotage SNAP cartridge silica, dichloromethane/methanol gradient, 0%→10% methanol) followed by preparative HPLC (method P1) to give the title compound 28.5 mg (39% yield).

LC-MS (Method 2): $R_t$=0.86 min; MS (ESIpos): m/z=566 [M+H]$^+$ $^1$H-NMR (400 MHz, DMSO-d$_6$): δ [ppm]=13.33 (br s, 1H), 8.25-8.21 (m, 1H), 7.89-7.85 (m, 1H), 7.73 (d, 1H), 7.55-7.37 (m, 4H), 7.06 (t, 1H), 6.91 (d, 1H), 6.85 (d, 1H), 5.27 (td, 1H), 5.14 (td, 1H), 4.99 (br d, 1H), 4.67 (dd, 1H), 4.40 (d, 1H), 4.34-4.20 (m, 5H), 3.78-3.68 (m, 3H), 3.62-3.56 (m, 1H), 3.43-3.36 (m, 1H), 3.26 (s, 3H), 2.23 (quin, 2H), 1.84 (s, 3H).

Example 072

(rac)-7,10,11,12-tetramethyl-1-[3-(naphthalen-1-yloxy)propyl]-4,5,6,7,8,10-hexahydropyrazolo[3',4':7,8][1,5]diazecino[9,10,1-hi]indole-2-carboxylic acid

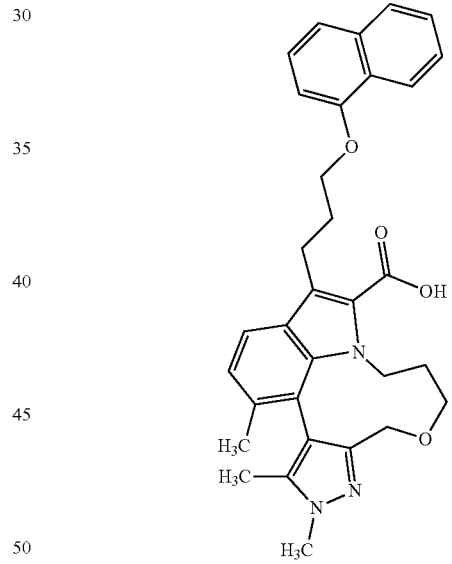

A mixture of (rac)-ethyl 7,10,11,12-tetramethyl-1-[3-(naphthalen-1-yloxy)propyl]-4,5,6,7,8,10-hexahydropyrazolo[3',4':7,8][1,5]diazecino[9,10,1-hi]indole-2-carboxylate formic acid salt (see Intermediate 169, 150 mg, 266 µmol), THF (8.6 ml), ethanol (6.2 ml) and aqueous lithium hydroxide (6.0 ml, 1.0 M, 6.0 mmol) was stirred for 16 h at 50° C. For work-up, citric acid (1.26 g, 5.98 mmol) was added to adjust the pH to 5-6, water was added and the mixture was extracted three times with a mixture of dichloromethane/2-propanol (4:1). The combined organic phases were washed with brine, filtered through a silicone filter and concentrated. The residue was purified by preparative HPLC (method P2) to give the title compound 80.0 mg (52% yield).

LC-MS (Method 2): $R_t$=0.87 min; MS (ESIpos): m/z=537 [M+H]$^+$

¹H-NMR (400 MHz, DMSO-d₆): δ [ppm]=13.67-11.59 (m, 1H), 8.27-8.23 (m, 1H), 7.89-7.84 (m, 1H), 7.57-7.36 (m, 5H), 6.93 (d, 1H), 6.87 (d, 1H), 4.59-4.52 (m, 1H), 4.16 (t, 2H), 3.79 (s, 3H), 3.73 (br dd, 1H), 3.30-3.16 (m, 3H), 3.06 (d, 1H), 2.40 (br t, 1H), 2.22-2.13 (m, 2H), 2.01-1.89 (m, 10H), 1.60-1.48 (m, 1H), 1.42-1.31 (m, 1H).

The title compound was separated into enantiomers using chiral preparative HPLC (78 mg) followed by preparative HPLC for each enantiomer [Instrument: Waters Autopurification system; column: Waters XBrigde C18 5μ 100×30 mm; eluent A: water+0.2 vol-% ammonia (32%), eluent B: acetonitrile; gradient: 0.00-0.50 min 10% B (25→70 mL/min), 0.51-7.50 min 10-35% B (70 mL/min), DAD scan: 210-400 nm] to give enantiomer 1 (17.5 mg see example 073) and enantiomer 2 (15.0 mg, see example 074).

Preparative chiral HPLC method: Instrument: Labomatic HD5000, Labocord-5000; Gilson GX-241, Labcol Vario 4000, column: Chiralpak IE 5μ 250×30 mm; eluent A: hexanes+0.1 vol-% diethylamine (99%); eluent B: ethanol; gradient: 20-50% B in 20 Min; flow 40.0 ml/min; UV 254 nm Analytical chiral HPLC method: Instrument: Agilent HPLC 1260; column: Chiralpak IE 3μ 100×4.6 mm; eluent A: hexanes+0.1 vol-% diethylamine (99%); eluent B: ethanol; gradient: 20-50% B in 7 min; flow 1.4 ml/min; temperature: 25° C.; DAD 254 nm Example 073

7,10,11,12-tetramethyl-1-[3-(naphthalen-1-yloxy)propyl]-4,5,6,7,8,10-hexahydropyrazolo[3',4':7,8][1,5]diazecino[9,10,1-hi]indole-2-carboxylic acid (Enantiomer 1)

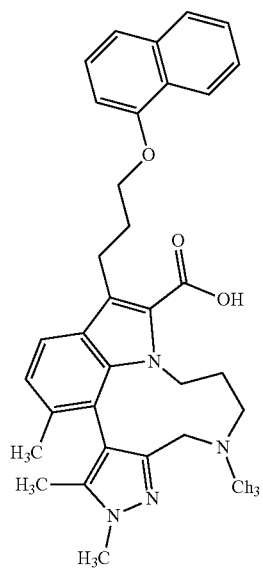

For the preparation of the racemic title compound and separation into enantiomers see Example 072.

Analytical Chiral HPLC (method see Example 072): R$_t$=5.01 min, ee 98.8%.

Example 074

7,10,11,12-tetramethyl-1-[3-(naphthalen-1-yloxy)propyl]-4,5,6,7,8,10-hexahydropyrazolo[3',4':7,8][1,5]diazecino[9,10,1-hi]indole-2-carboxylic acid (Enantiomer 2)

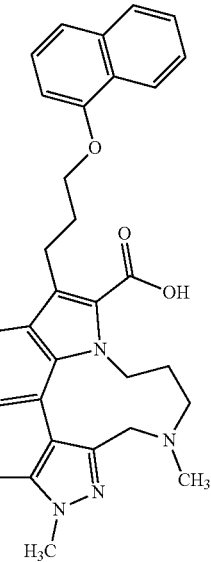

For the preparation of the racemic title compound and separation into enantiomers see Example 072.

Analytical Chiral HPLC (method see Example 072): R$_t$=5.96 min, ee 93.5%.

Example 075

(rac)-2,3,4-trimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid

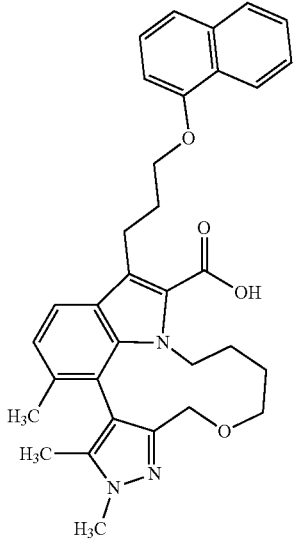 [SMILES: Cc1ccc2c(CCCOc3cccc4ccccc34)c(C(=O)O)n3c2c1-c1c(nn(C)c1C)COCCCC3]

A mixture of (rac)-ethyl 2,3,4-trimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylate (see Intermediate 165, 550 mg, 972 μmol), THF (32 ml), ethanol (23 ml) and aqueous lithium hydroxide (22 ml, 1.0 M, 22 mmol) was stirred for 16 h at 50° C. For work-up, citric acid (4.60 g, 21.9 mmol) was added to adjust the pH to 5-6, water was added and the mixture was extracted three times with a mixture of dichloromethane/2-propanol (4:1). The combined organic phases were washed with brine, filtered through a silicone filter and concentrated. The residue was purified by flash chromatography (Biotage SNAP cartridge silica, dichloromethane/methanol gradient, 0%→10% methanol) followed by preparative HPLC (method P2) to give the title compound 140 mg (24% yield).

LC-MS (Method 2): $R_t$=0.85 min; MS (ESIpos): m/z=538 [M+H]$^+$ $^1$H-NMR (400 MHz, DMSO-d6) δ[ppm]: 0.670 (0.86), 0.688 (0.49), 1.145 (0.49), 1.261 (0.68), 1.277 (0.72), 1.301 (0.56), 1.744 (15.39), 1.907 (0.44), 1.957 (2.10), 1.981 (11.69), 2.010 (1.72), 2.074 (0.82), 2.162 (0.40), 2.181 (1.05), 2.197 (1.47), 2.214 (1.00), 2.318 (0.44), 2.322 (0.98), 2.326 (1.33), 2.332 (1.00), 2.336 (0.47), 2.518 (5.59), 2.522 (3.47), 2.660 (0.42), 2.664 (0.98), 2.669 (1.37), 2.673 (1.00), 2.678 (0.44), 3.143 (0.56), 3.160 (1.72), 3.170 (1.84), 3.224 (0.40), 3.239 (0.65), 3.257 (1.12), 3.276 (1.26), 3.290 (1.65), 3.790 (2.49), 3.818 (16.00), 3.838 (0.47), 4.111 (0.42), 4.152 (0.47), 4.160 (0.75), 4.168 (0.93), 4.176 (1.56), 4.183 (1.77), 4.190 (2.91), 4.199 (1.28), 4.221 (2.72), 4.373 (2.05), 4.404 (1.58), 6.873 (1.61), 6.891 (1.75), 6.988 (2.03), 7.008 (2.17), 7.361 (1.28), 7.381 (2.40), 7.396 (0.51), 7.400 (2.03), 7.446 (2.45), 7.466 (1.42), 7.501 (0.56), 7.513 (1.77), 7.518 (3.21), 7.527 (3.59), 7.537 (3.19), 7.541 (2.05), 7.553 (0.68), 7.584 (2.12), 7.592 (0.40), 7.604 (1.89), 7.858 (1.51), 7.861 (1.09), 7.868 (0.79), 7.872 (0.93), 7.875 (1.02), 7.881 (1.33), 8.248 (1.33), 8.256 (0.89), 8.262 (0.65), 8.267 (0.79), 8.272 (1.16).

The title compound was separated into enantiomers using chiral preparative HPLC (135 mg) to give enantiomer 1 (40 mg see example 076) and enantiomer 2 (20 mg, see example 077).

Preparative chiral HPLC method: Instrument: Sepiatec: Prep SFC100; column: Chiralpak IE 5 μm 250×30 mm; eluent A: carbon dioxide, eluent B: 2-propanol+0.4 vol-% diethylamine (99%); isocratic: 32% B; flow 100.0 ml/min, temperature: 40° C.; BPR: 150 bar; MWD @ 254 nm Analytical chiral HPLC method: Instrument: Agilent: 1260, Aurora SFC-Modul; column: Chiralpak IE 5 μm 100×4.6 mm; eluent A: carbon dixoide, eluent B: 2-propanol+0.2 vol-% diethylamine (99%); isocratic: 32% B; flow 4.0 ml/min; temperature: 37.5° C.; BPR: 100 bar; MWD @ 254 nm Example 076

2,3,4-trimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (Enantiomer 1)

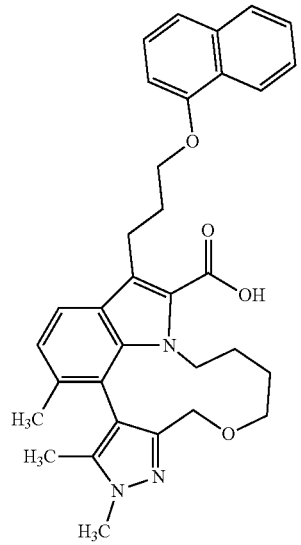 [SMILES: Cc1ccc2c(CCCOc3cccc4ccccc34)c(C(=O)O)n3c2c1-c1c(nn(C)c1C)COCCCC3]

For the preparation of the racemic title compound and separation into enantiomers see Example 075.

Analytical Chiral HPLC (method see Example 075): $R_t$=2.42 min, ee 97.7%.

Example 077

2,3,4-trimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (Enantiomer 2)

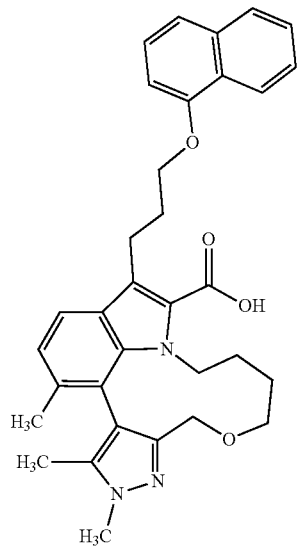 [SMILES: Cc1ccc2c(CCCOc3cccc4ccccc34)c(C(=O)O)n3c2c1-c1c(nn(C)c1C)COCCCC3]

For the preparation of the racemic title compound and separation into enantiomers see Example 075.

Analytical Chiral HPLC (method see Example 075): $R_t$=3.66 min, ee 95.8%.

Example 078

(rac)-2-Methyl-3-(morpholin-4-ylmethyl)-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid

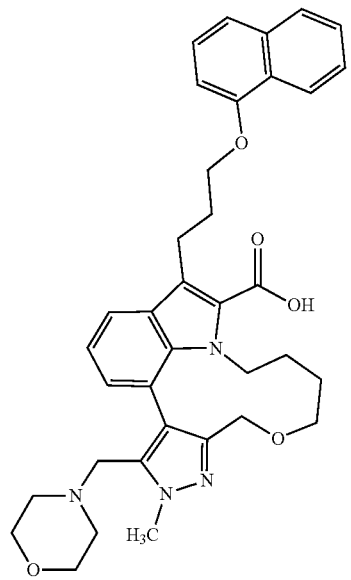

A mixture of (rac)-ethyl 2-methyl-3-(morpholin-4-ylmethyl)-7-[3-(naphthalen-1-yloxy)propyl]-2,10,11,12,13,15-hexahydropyrazolo[4',3':9,10][1,6]oxazacycloundecino[8,7,6-hi]indole-8-carboxylate (295 mg, 463 µmol, see Intermediate 191), THF (15 mL), ethanol (11 mL) and lithium hydroxide (10 mL, 1.0 M in water) was stirred at 50° C. overnight. Water was added, the mixture was acidified by the addition of citric acid (pH 5-6) and extracted with dichloromethane. The organic layer was dried over sodium sulfate. After filtration and removal the title compound was isolated (278 mg, 98% yield).

LC-MS: m/z=609.3 [M+H]⁺.

¹H-NMR (400 MHz, DMSO-d6), δ [ppm]=0.97 (1H), 1.16 (1H), 1.25 (1H), 1.35 (1H), 2.05 (4H), 2.22 (2H), 2.96 (1H), 3.05 (1H), 3.13 (1H), 3.24-3.37 (2H), 3.42 (4H), 3.86 (1H), 3.91 (3H), 4.14-4.28 (5H), 4.52 (1H), 6.85 (1H), 6.89 (1H), 7.02 (1H), 7.37 (1H), 7.45 (1H), 7.53 (2H), 7.71 (1H), 7.85-7.89 (1H), 8.25-8.29 (1H), 13.09 (1H).

The title compound (211 mg) was separated into enantiomers by preparative chiral HPLC to give enantiomer 1 (80 mg, see Example 079) and enantiomer 2 (75 mg, see Example 080).

Preparative chiral HPLC method: Instrument: Sepiatec: Prep SFC100; column: Chiralpak IA 5 µm 250×30 mm; eluent A: carbon dioxide, eluent B: ethanol+0.4 vol-% diethylamine (99%); isocratic: 23% B; flow 100.0 ml/min temperature: 40° C.; BPR: 150 bar; MWD @ 254 nm Analytical chiral HPLC method: Instrument: Agilent: 1260, Aurora SFC-Modul; column: Chiralpak IA 5 µm 100×4.6 mm; eluent A: carbon dioxide, eluent B: ethanol+ 0.2 vol-% diethylamine (99%); isocratic: 23% B; flow 4.0 ml/min; temperature: 37.5° C.; BPR: 100 bar; MWD @ 254 nm

Example 079

2-methyl-3-(morpholin-4-ylmethyl)-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid-N-ethylethanamine salt (Enantiomer 1)

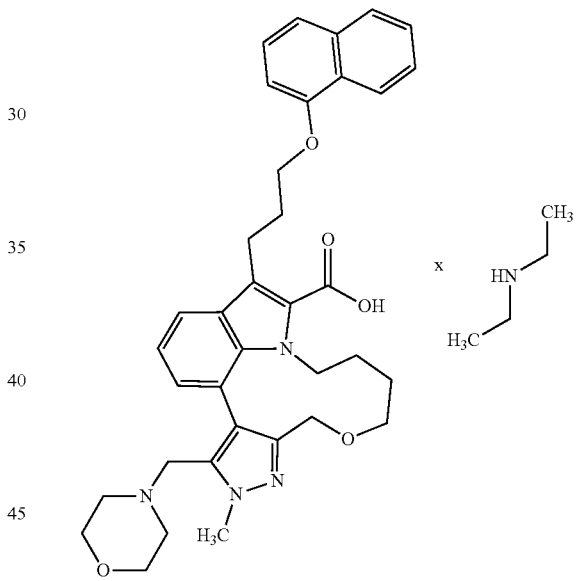

For the preparation of the racemic title compound and separation into enantiomers see Example 078.

Analytical Chiral HPLC (method see Example 078): $R_t$=2.85 min, ee 99.5%.

LC-MS: m/z=609.3 [M+H]⁺.

¹H-NMR (400 MHz, DMSO-d6), δ [ppm]=1.03-1.16 (2H), 1.12 (3.8H), 1.21 (1H), 1.33 (1H), 2.05 (4H), 2.21 (2H), 2.80 (2.6H), 2.92 (1H), 3.11 (2H), 3.18-3.31 (3H), 3.44 (4H), 3.74 (1H), 3.91 (3H), 4.11-4.25 (3H), 4.38 (1H), 4.47 (1H), 6.75 (1H), 6.84 (1H), 6.93 (1H), 7.36 (1H), 7.44 (1H), 7.52 (2H), 7.60 (1H), 7.83-7.89 (1H), 8.24-8.29 (1H).

967

Example 080

2-methyl-3-(morpholin-4-ylmethyl)-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid-N-ethylethanamine salt (Enantiomer 2)

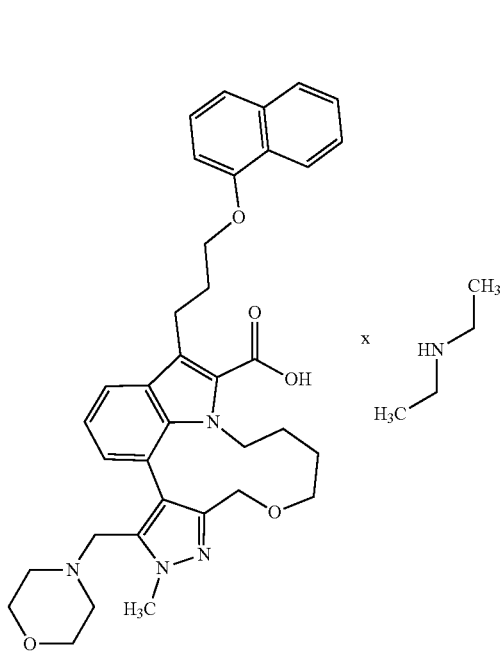

For the preparation of the racemic title compound and separation into enantiomers see Example 078.

Analytical Chiral HPLC (method see Example 078): $R_t$=5.88 min, ee 99.2%.

LC-MS: m/z=609.3 [M+H]$^+$.

$^1$H-NMR (400 MHz, DMSO-d6), δ [ppm]=1.03-1.16 (2H), 1.12 (3.8H), 1.21 (1H), 1.33 (1H), 2.05 (4H), 2.21 (2H), 2.80 (2.6H), 2.92 (1H), 3.11 (2H), 3.18-3.31 (3H), 3.44 (4H), 3.74 (1H), 3.91 (3H), 4.11-4.25 (3H), 4.38 (1H), 4.47 (1H), 6.75 (1H), 6.84 (1H), 6.93 (1H), 7.36 (1H), 7.44 (1H), 7.52 (2H), 7.60 (1H), 7.83-7.89 (1H), 8.24-8.29 (1H).

968

Example 081

(rac)-3-Cyclopropyl-2-ethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid

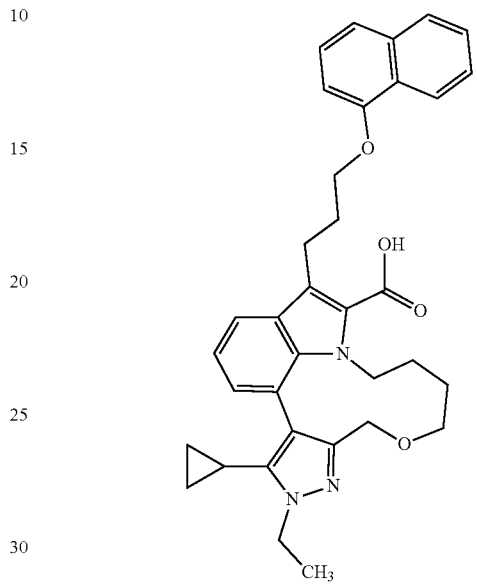

A mixture of (rac)-ethyl 3-cyclopropyl-2-ethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylate (138 mg, 233 µmol, see Intermediate 195), THF (7.6 mL), ethanol (5.4 mL) and lithium hydroxide (5.2 mL, 1.0 M in water) was stirred at 60° C. for 6.75 hrs. Water was added, the mixture was acidified by the addition of citric acid (pH 5-6) and extracted with dichloromethane. The organic layer was dried over sodium sulfate. After filtration and removal of the solvents the residue was purified by preparative HPLC (method P1) to give the title compound (53 mg, 40% yield) as mixture of atropisomers.

LC-MS: m/z=564.3 [M+H]$^+$.

$^1$H-NMR (400 MHz, DMSO-d6), δ [ppm]=0.07 (2H), 0.43 (2H), 1.02 (1H), 1.16 (2H), 1.35 (1H), 1.41 (3H), 1.67 (1H), 2.21 (2H), 3.07 (1H), 3.25-3.37 (3H), 3.85 (1H), 4.13-4.31 (6H), 4.44 (1H), 6.86 (2H), 6.99 (1H), 7.37 (1H), 7.45 (1H), 7.53 (2H), 7.70 (1H), 7.85-7.89 (1H), 8.25-8.30 (1H), 13.12 (1H).

The title compound (49 mg) was separated into enantiomers by preparative chiral HPLC to give enantiomer 1 (16 mg, see Example 082) and enantiomer 2 (17 mg, see Example 083).

Preparative chiral HPLC method: Instrument: Labomatic HD5000, Labocord-5000; Gilson GX-241, Labcol Vario 4000, column: Chiralpak IA 5µ 250×30 mm; eluent A: MTBE+0.1 vol-% diethylamine (99%); eluent B: ethanol; isocratic: 90% A+10% B; flow 50.0 ml/min; UV 280 nm Analytical chiral HPLC method: Instrument: Agilent HPLC 1260; column: Chiralpak IE 3µ 100×4.6 mm; eluent A: hexane+0.1 vol-% diethylamine (99%); eluent B: ethanol; gradient: 20-50% B in 7 min; flow 1.4 ml/min; temperature: 25° C.; DAD 280 nm

Example 082

3-cyclopropyl-2-ethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid-N-ethylethanamine salt (Enantiomer 1)

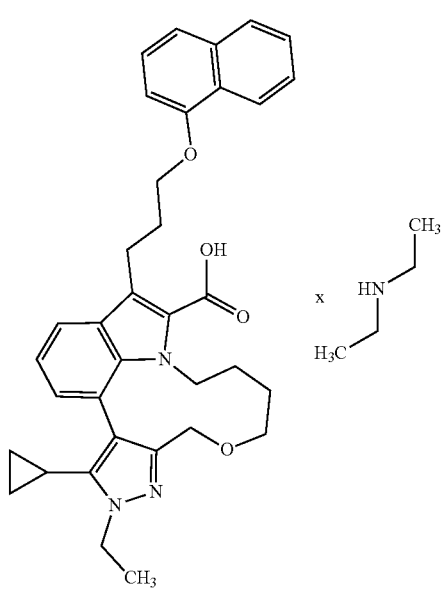

Example 083

3-cyclopropyl-2-ethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid-N-ethylethanamine salt (Enantiomer 2)

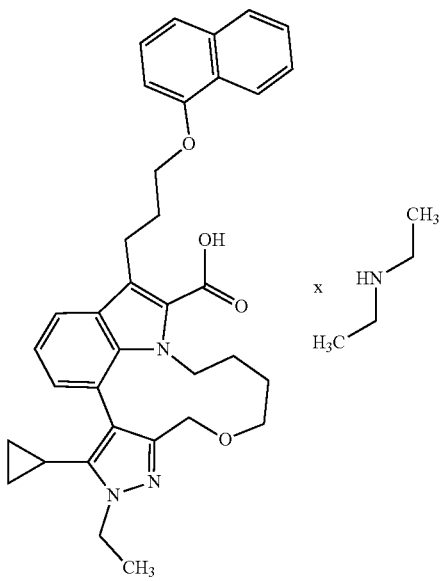

For the preparation of the racemic title compound and separation into enantiomers see Example 081.

Analytical Chiral HPLC (method see Example 081): $R_t$=5.18 min, ee>99%.

LC-MS: m/z=564.3 [M+H]$^+$.

$^1$H-NMR (400 MHz, DMSO-d6), δ [ppm]=0.09 (2H), 0.42 (2H), 1.05-1.18 (3H), 1.15 (1.95H), 1.32 (1H), 1.41 (3H), 1.67 (1H), 2.21 (2H), 2.86 (1.3H), 3.06 (1H), 3.19-3.29 (3H), 3.79 (1H), 4.10-4.20 (3H), 4.25 (2H), 4.36 (1H), 4.41 (1H), 6.78 (1H), 6.84 (1H), 6.94 (1H), 7.36 (1H), 7.44 (1H), 7.52 (2H), 7.62 (1H), 7.83-7.88 (1H), 8.25-8.31 (1H).

For the preparation of the racemic title compound and separation into enantiomers see Example 081.

Analytical Chiral HPLC (method see Example 081): $R_t$=5.67 min, ee 99.4%.

LC-MS: m/z=564.3 [M+H]$^+$.

$^1$H-NMR (400 MHz, DMSO-d6), δ [ppm]=0.09 (2H), 0.42 (2H), 1.05-1.18 (3H), 1.15 (2.0H), 1.32 (1H), 1.41 (3H), 1.67 (1H), 2.21 (2H), 2.86 (1.4H), 3.06 (1H), 3.19-3.29 (3H), 3.79 (1H), 4.10-4.20 (3H), 4.25 (2H), 4.36 (1H), 4.41 (1H), 6.78 (1H), 6.84 (1H), 6.94 (1H), 7.36 (1H), 7.44 (1H), 7.52 (2H), 7.62 (1H), 7.83-7.88 (1H), 8.25-8.31 (1H).

Example 084

(rac)-3-Cyclopropyl-2-(2-methoxyethyl)-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid

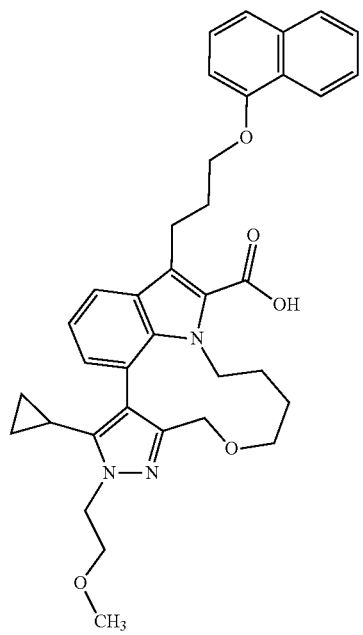 [SMILES: COCCn1nc2c(c1C1CC1)-c1cccc3c(CCCOc4cccc5ccccc45)c(C(=O)O)n(c13)CCCCOC2]

A mixture of (rac)-ethyl 3-cyclopropyl-2-(2-methoxyethyl)-7-[3-(naphthalen-1-yloxy)propyl]-2,10,11,12,13,15-hexahydropyrazolo[4',3':9,10][1,6]oxazacycloundecino[8,7,6-hi]indole-8-carboxylate (250 mg, 402 µmol, see Intermediate 201), THF (16 mL), ethanol (12 mL) and lithium hydroxide (8.0 mL, 1.0 M in water) was stirred at 50° C. for 2 hrs. Water was added, the mixture was acidified by the addition of citric acid (pH 5-6) and extracted with dichloromethane. The organic layer was dried over sodium sulfate. After filtration and removal of the solvents the residue was purified by preparative HPLC (method P5) to give the title compound (108 mg, 36% yield) as mixture of atropisomers.

LC-MS: m/z=594.2 [M+H]$^+$.

$^1$H-NMR (400 MHz, DMSO-d6), δ [ppm]=0.08 (2H), 0.42 (2H), 1.03 (1H), 1.15 (2H), 1.34 (1H), 1.68 (1H), 2.21 (2H), 3.08 (1H), 3.26 (3H), 3.27-3.37 (3H), 3.77 (2H), 3.87 (1H), 4.12-4.20 (3H), 4.27 (1H), 4.37 (2H), 4.45 (1H), 6.85 (1H), 6.88 (1H), 7.00 (1H), 7.37 (1H), 7.45 (1H), 7.53 (2H), 7.70 (1H), 7.84-7.89 (1H), 8.25-8.30 (1H), 13.11 (1H).

The title compound (108 mg) was separated into enantiomers by preparative chiral HPLC to give enantiomer 1 (41.9 mg, see Example 085) and enantiomer 2 (23.5 mg, see Example 086).

Preparative chiral HPLC method: Instrument: Sepiatec: Prep SFC100; column: Chiralpak ID 5 µm 250×30 mm; eluent A carbon dioxide, eluent B: 2-propanol+0.4 vol-% diethylamine (99%); isocratic: 27% B; flow 100.0 ml/min temperature: 40° C.; BPR: 150 bar; MWD 254 nm Analytical chiral HPLC method: Instrument: Agilent: 1260, Aurora SFC-Modul; column: Chiralpak ID 5 µm 100×4.6 mm; eluent A: carbon dioxide, eluent B: 2-propanol+0.2 vol-% diethylamine (99%); isocratic: 27% B; flow 4.0 ml/min; temperature: 37.5° C.; BPR: 100 bar; MWD 254 nm

Example 085

3-Cyclopropyl-2-(2-methoxyethyl)-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid-N-ethylethanamine salt (Enantiomer 1)

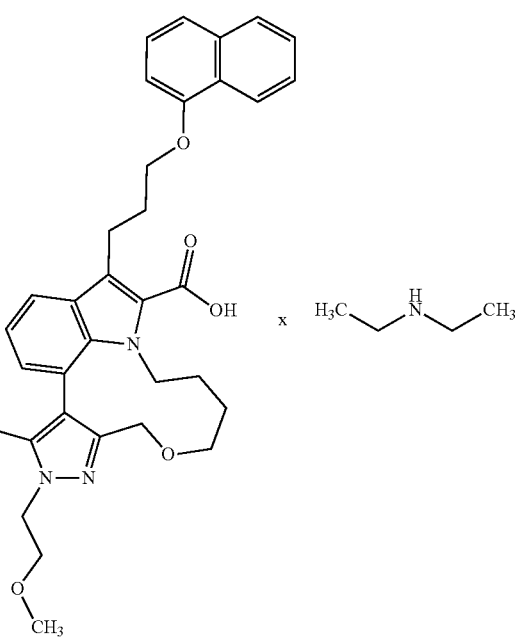

For the preparation of the racemic title compound and separation of enantiomers by preparative chiral HPLC see Example 084.

Analytical Chiral HPLC (method see Example 084): R$_t$=2.85 min, ee 100%.

LC-MS: m/z=594.4 [M+H]$^+$.

$^1$H-NMR (400 MHz, DMSO-d6), δ [ppm]=0.11 (2H), 0.42 (2H), 1.07-1.19 (3H), 1.15 (3.5H), 1.31 (1H), 1.68 (1H), 2.21 (2H), 2.85 (2.3H), 3.07 (1H), 3.19-3.30 (3H), 3.26 (3H), 3.72-3.83 (3H), 4.09-4.21 (3H), 4.31-4.44 (4H), 6.75 (1H), 6.84 (1H), 6.92 (1H), 7.36 (1H), 7.44 (1H), 7.52 (2H), 7.60 (1H), 7.84-7.88 (1H), 8.24-8.29 (1H).

Example 086

3-Cyclopropyl-2-(2-methoxyethyl)-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid-N-ethylethanamine salt (Enantiomer 2)

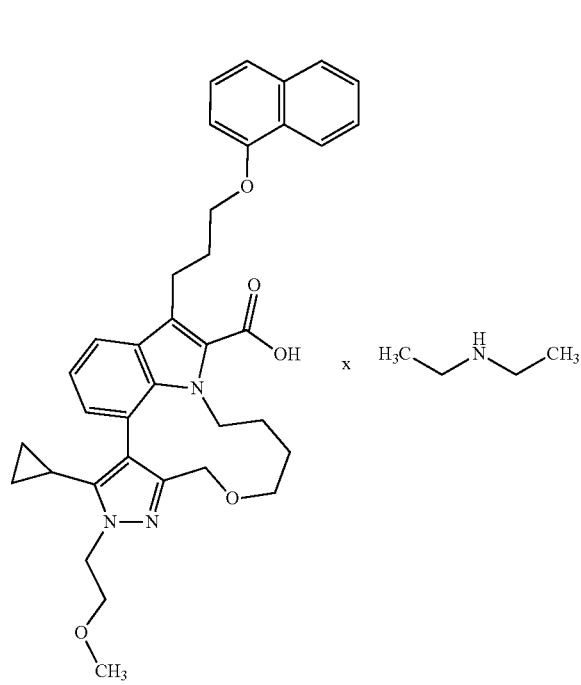

For the preparation of the racemic title compound and separation of enantiomers by preparative chiral HPLC see Example 084.

Analytical Chiral HPLC (method see Example 084): $R_t$=6.78 min, ee 100%

LC-MS: m/z=594.4 [M+H]$^+$.

$^1$H-NMR (400 MHz, DMSO-d6), δ [ppm]=0.11 (2H), 0.42 (2H), 1.07-1.19 (3H), 1.15 (3.5H), 1.31 (1H), 1.68 (1H), 2.21 (2H), 2.85 (2.3H), 3.07 (1H), 3.19-3.30 (3H), 3.26 (3H), 3.72-3.83 (3H), 4.09-4.21 (3H), 4.31-4.44 (4H), 6.75 (1H), 6.84 (1H), 6.92 (1H), 7.36 (1H), 7.44 (1H), 7.52 (2H), 7.60 (1H), 7.84-7.88 (1H), 8.24-8.29 (1H).

Example 087

(rac)-2-Methyl-3-(morpholin-4-ylmethyl)-7-[3-(naphthalen-1-yloxy)propyl]-2,10,11,13,14,16-hexahydropyrazolo[4',3':10,11][1,4,7]dioxazacyclododecino[9,8,7-hi]indole-8-carboxylic acid

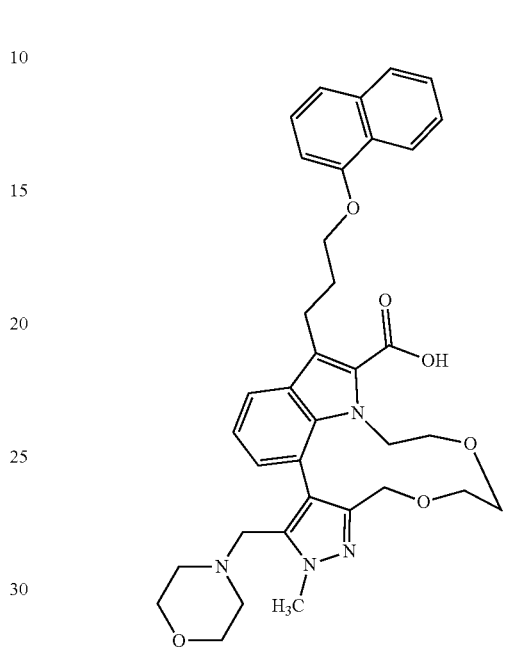

A mixture of (rac)-ethyl 2-methyl-3-(morpholin-4-ylmethyl)-7-[3-(naphthalen-1-yloxy)propyl]-2,10,11,13,14,16-hexahydropyrazolo[4',3':10,11][1,4,7]dioxazacyclododecino[9,8,7-hi]indole-8-carboxylate (30.0 mg, 46.0 μmol, see Intermediate 192), THF (1.5 mL), ethanol (1.1 mL) and lithium hydroxide (1.0 mL, 1.0 M in water) was stirred at 50° C. overnight. Water was added, the mixture was acidified by the addition of citric acid (pH 5-6) and extracted with dichloromethane. The organic layer was dried over sodium sulfate. After filtration and removal of the solvents the residue was purified by preparative HPLC (method P1) to give the title compound (20 mg, 69% yield) as mixture of atropisomers.

LC-MS: m/z=625.3 [M+H]$^+$.

$^1$H-NMR (500 MHz, DMSO-d6), δ [ppm]=1.90-2.11 (4H), 2.22 (2H), 2.85 (1H), 3.18-3.42 (11H), 3.49 (1H), 3.52 (4H), 3.93 (3H), 4.10 (1H), 4.15 (1H), 4.19 (2H), 4.55 (1H), 4.68 (1H), 6.88 (1H), 6.96 (1H), 7.04 (1H), 7.38 (1H), 7.45 (1H), 7.53 (2H), 7.71 (1H), 7.84-7.89 (1H), 8.27-8.31 (1H), 13.16 (1H).

Example 088

(rac)-3-Cyclopropyl-1-ethyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid

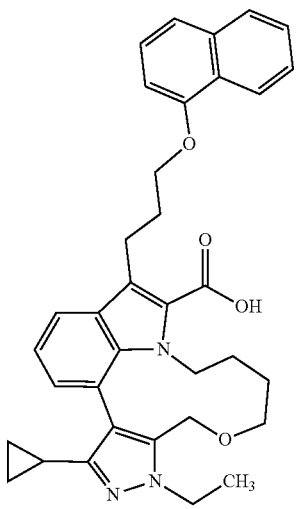 [SMILES: CCn1nc(C2CC2)c2c1COCCCCn1c(C(=O)O)c(CCCOc3cccc4ccccc34)c3cccc-2c31]

A mixture of (rac)-ethyl 3-cyclopropyl-1-ethyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (400 mg, 676 µmol, see Intermediate 198), THF (22 mL), ethanol (16 mL) and lithium hydroxide (15 mL, 1.0 M in water) was stirred at 50° C. overnight. Water was added, the mixture acidified by the addition of citric acid (pH 5-6) and extracted with dichloromethane. The organic layer was dried over sodium sulfate. After filtration and removal of the solvents the residue was purified by preparative HPLC (method P1) to give the title compound (154 mg, 40% yield) as mixture of atropisomers.

LC-MS: m/z=564.3 [M+H]$^+$.

$^1$H-NMR (400 MHz, DMSO-d6), δ [ppm]=0.51-0.63 (4H), 1.00 (2H), 1.16-1.36 (3H), 1.39 (3H), 2.21 (2H), 2.77 (1H), 3.23-3.42 (3H), 4.06-4.17 (3H), 4.17-4.25 (3H), 4.60 (1H), 4.63 (1H), 6.86 (1H), 6.89 (1H), 7.04 (1H), 7.38 (1H), 7.45 (1H), 7.52 (2H), 7.75 (1H), 7.87 (1H), 8.22-8.27 (1H), 13.20 (1H).

The title compound (145 mg) was separated into enantiomers by preparative chiral HPLC to give enantiomer 1 (36.2 mg, see Example 089) and enantiomer 2 (36.8 mg, see Example 090).

Preparative chiral HPLC method: Instrument: Sepiatec: Prep SFC100; column: Chiralpak IE 5 µm 250×30 mm; eluent A carbon dioxide, eluent B: ethanol+0.4 vol-% diethylamine (99%); isocratic: 29% B; flow 100.0 ml/min temperature: 40° C.; BPR: 150 bar; MWD 254 nm Analytical chiral HPLC method: Instrument: Agilent: 1260, Aurora SFC-Modul; column: Chiralpak IE 5 µm 100×4.6 mm; eluent A: carbon dioxide, eluent B: ethanol+0.2 Vol-% Diethylamin (99%); Isokratisch: 29% B; flow 4.0 ml/min; temperature: 37.5° C.; BPR: 100 bar; MWD 254 nm

Example 089

3-cyclopropyl-1-ethyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid-N-ethylethanamine salt (Enantiomer 1)

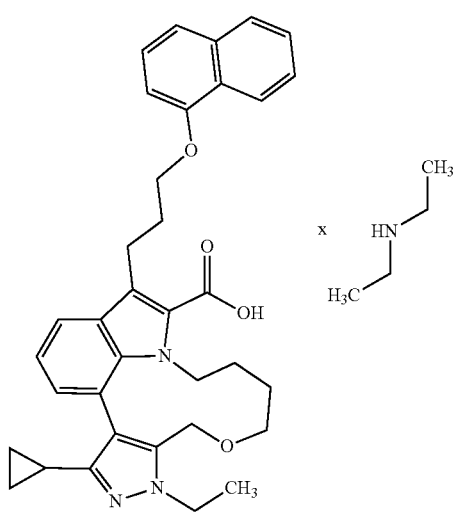

For the preparation of the racemic title compound and separation of enantiomers by preparative chiral HPLC see Example 088.

Analytical Chiral HPLC (method see Example 088): R$_t$=2.30 min, ee 88.7%.

LC-MS: m/z=564.3 [M+H]$^+$.

$^1$H-NMR (400 MHz, DMSO-d6), δ [ppm]=0.52-0.66 (4H), 0.80-1.16 (3H), 1.14 (3.9H), 1.30 (1H), 1.44 (1H), 1.39 (3H), 2.20 (2H), 2.75 (1H), 2.85 (2.6H), 3.17 (1H), 3.26-3.41 (2H), 3.97 (1H), 4.10 (2H), 4.14-4.24 (3H), 4.61 (1H), 4.72 (1H), 6.71 (1H), 6.88 (1H), 6.94 (1H), 7.37 (1H), 7.44 (1H), 7.51 (2H), 7.61 (1H), 7.83-7.88 (1H), 8.21-8.28 (1H).

Example 090

3-cyclopropyl-1-ethyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid-N-ethylethanamine salt (Enantiomer 2)

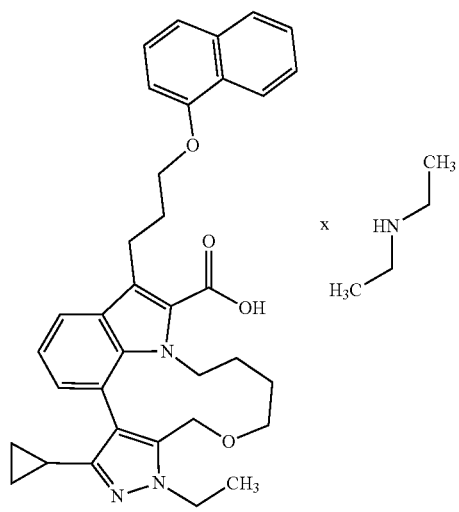

For the preparation of the racemic title compound and separation of enantiomers by preparative chiral HPLC see Example 088.

Analytical Chiral HPLC (method see Example 088): Rt=3.00 min, ee 69.7%

LC-MS: m/z=564.3 [M+H]$^+$.

$^1$H-NMR (400 MHz, DMSO-d6), δ [ppm]=0.52-0.66 (4H), 0.80-1.16 (3H), 1.14 (3.0H), 1.30 (1H), 1.44 (1H), 1.39 (3H), 2.20 (2H), 2.75 (1H), 2.85 (2.0H), 3.17 (1H), 3.26-3.41 (2H), 3.97 (1H), 4.10 (2H), 4.14-4.24 (3H), 4.61 (1H), 4.72 (1H), 6.71 (1H), 6.88 (1H), 6.94 (1H), 7.37 (1H), 7.44 (1H), 7.51 (2H), 7.61 (1H), 7.83-7.88 (1H), 8.21-8.28 (1H).

Example 091

(rac)-(11Z)-3-methyl-7-[3-(naphthalen-1-yloxy)propyl]-2-(2,2,2-trifluoroethyl)-2,10,13,15-tetrahydropyrazolo[4',3':9,10][1,6]oxazacycloundecino[8,7,6-hi]indole-8-carboxylic acid

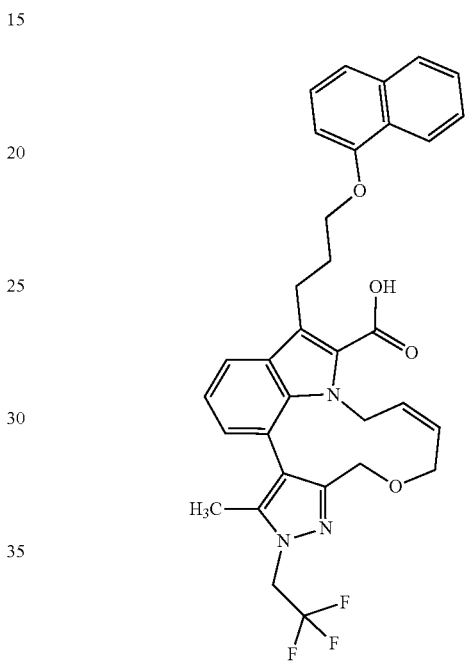

A mixture of (rac)-ethyl (11Z)-3-methyl-7-[3-(naphthalen-1-yloxy)propyl]-2-(2,2,2-trifluoroethyl)-2,10,13,15-tetrahydropyrazolo[4',3':9,10][1,6]oxazacycloundecino[8,7,6-hi]indole-8-carboxylate (see Intermediate 171, 100 mg, 162 µmol), THF (6.6 ml), ethanol (4.7 ml) and aqueous lithium hydroxide (3.2 ml, 1.0 M, 3.2 mmol) was stirred for 16 h at 50° C. For work-up, citric acid (680 mg, 3.24 mmol) was added to adjust the pH to 5-6, water was added and the mixture was extracted three times with a mixture of dichloromethane/2-propanol (4:1). The combined organic phases were filtered through a silicone filter and concentrated. The residue was purified by preparative HPLC (method P8) to give the title compound 2.60 mg (99% purity, 3% yield).

LC-MS (Method 1): R$_t$=1.53 min; MS (ESIpos): m/z=590 [M+H]$^+$ $^1$H-NMR (400 MHz, DMSO-d$_6$): δ [ppm]=13.35 (br s, 1H), 8.25-8.21 (m, 1H), 7.88-7.84 (m, 1H), 7.76 (d, 1H), 7.55-7.44 (m, 3H), 7.42-7.37 (m, 1H), 7.09 (t, 1H), 6.93-6.88 (m, 2H), 5.33-5.14 (m, 4H), 4.99 (br d, 1H), 4.60 (dd, 1H), 4.42 (d, 1H), 4.30 (d, 1H), 4.25-4.19 (m, 2H), 3.76-3.69 (m, 1H), 3.64-3.59 (m, 1H), 3.40-3.34 (m, 1H), 2.27-2.19 (m, 2H), 1.90 (s, 3H).

Example 092

(rac)-2-cyclopropyl-3-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid

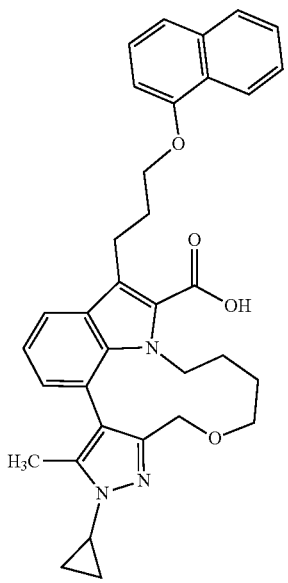 [SMILES: Cc1c2c(nn1C1CC1)COCCCCn1c(C(=O)O)c(CCCOc3cccc4ccccc34)c3cccc-2c31]

A mixture of (rac)-ethyl 2-cyclopropyl-3-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylate (see Intermediate 177, 345 mg, 597 μmol), THF (19 ml), ethanol (14 ml) and aqueous lithium hydroxide (13 ml, 1.0 M, 13 mmol) was stirred for 16 h at 50° C. For work-up, citric acid (2.82 g, 13.4 mmol) was added to adjust the pH to 5-6, water was added and the mixture was extracted three times with a mixture of dichloromethane/2-propanol (4:1). The combined organic phases were washed with brine, filtered through a silicone filter and concentrated. The residue was purified by flash chromatography (Biotage SNAP cartridge silica, hexanes/ethyl acetate gradient, 50%→100% ethyl acetate) followed by preparative HPLC (method P1) to give the title compound (150 mg).

LC-MS (Method 3): Rt=1.49 min; MS (ESIpos): m/z=550 [M+H]$^+$ $^1$H-NMR (400 MHz, DMSO-d$_6$): δ [ppm]=13.12 (br s, 1H), 8.28-8.24 (m, 1H), 7.89-7.85 (m, 1H), 7.71 (dd, 1H), 7.56-7.44 (m, 3H), 7.41-7.36 (m, 1H), 7.08-7.01 (m, 1H), 6.93-6.87 (m, 2H), 4.50 (d, 1H), 4.36-4.24 (m, 1H), 4.23-4.14 (m, 3H), 3.88-3.79 (m, 1H), 3.61-3.55 (m, 1H), 3.43-3.36 (m, 1H), 3.30-3.23 (m, 2H), 3.08-3.00 (m, 1H), 2.21 (quin, 2H), 1.90 (s, 3H), 1.41-0.91 (m, 8H).

The title compound was separated into enantiomers using chiral preparative HPLC to give enantiomer 1 (75 mg, see example 093) and enantiomer 2 (60 mg, see example 094).

Preparative chiral HPLC method: Instrument: Sepiatec: Prep SFC100; column: Chiralpak IA 5 μm 250×30 mm; eluent A: carbon dioxide, eluent B: ethanol+0.4 vol-% diethylamine (99%); isocratic: 23% B; flow 100.0 ml/min temperature: 40° C.; BPR: 150 bar; MWD @ 254 nm Analytical chiral HPLC method: Instrument: Agilent: 1260, Aurora SFC-Modul; column: Chiralpak IA 5 μm 100×4.6 mm; eluent A: carbon dioxide, eluent B: ethanol+0.2 vol-% diethylamine (99%); isocratic: 23% B; flow 4.0 ml/min; temperature: 37.5° C.; BPR: 100 bar; MWD @ 254 nm

Example 093

2-cyclopropyl-3-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid-N-ethylethanamine salt (Enantiomer 1)

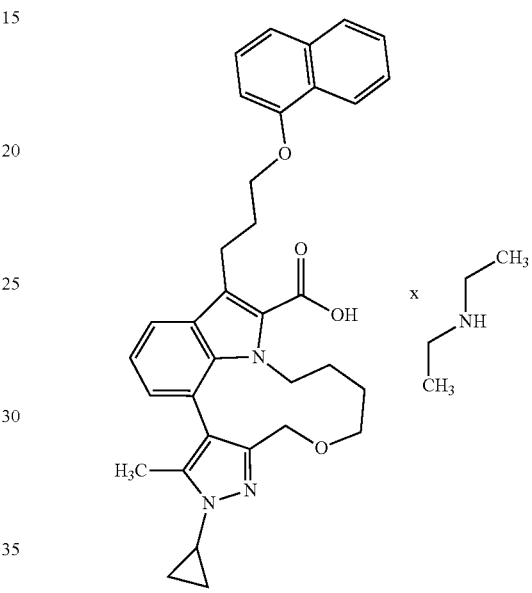

For the preparation of the racemic title compound and separation into enantiomers see Example 092.

Analytical Chiral HPLC (method see Example 092): R$_t$=2.95 min, ee 99.5%.

LC-MS (Method 2): R$_t$=0.92 min; MS (ESIpos): m/z=550 [M+H]$^+$ $^1$H-NMR (400 MHz, DMSO-d6) δ[ppm]: 0.968 (0.52), 0.986 (0.71), 1.002 (1.83), 1.020 (2.83), 1.033 (2.67), 1.042 (1.31), 1.047 (1.42), 1.052 (1.44), 1.058 (1.28), 1.070 (1.17), 1.096 (1.64), 1.108 (16.00), 1.119 (7.55), 1.137 (14.75), 1.155 (7.11), 1.295 (0.63), 1.909 (14.94), 2.183 (1.23), 2.201 (1.85), 2.218 (1.31), 2.323 (1.20), 2.327 (1.66), 2.331 (1.23), 2.518 (8.59), 2.523 (5.34), 2.665 (1.28), 2.669 (1.72), 2.673 (1.25), 2.806 (1.64), 2.824 (4.74), 2.842 (4.72), 2.860 (1.50), 3.027 (0.79), 3.052 (0.57), 3.183 (0.65), 3.198 (0.79), 3.216 (1.14), 3.235 (1.25), 3.284 (2.34), 3.550 (0.49), 3.564 (0.87), 3.577 (1.50), 3.590 (0.84), 3.730 (0.60), 4.155 (2.81), 4.172 (1.96), 4.186 (4.36), 4.201 (0.95), 4.441 (2.62), 4.472 (2.02), 6.755 (1.06), 6.772 (1.23), 6.861 (1.88), 6.880 (2.02), 6.933 (1.12), 6.952 (1.74), 6.971 (0.95), 7.347 (1.25), 7.367 (2.48), 7.387 (1.85), 7.433 (2.64), 7.453 (1.55), 7.490 (0.52), 7.502 (1.69), 7.507 (2.86), 7.517 (3.22), 7.526 (3.03), 7.531 (1.83), 7.543 (0.60), 7.581 (1.34), 7.600 (1.25), 7.849 (1.53), 7.859 (0.82), 7.866 (1.06), 7.872 (1.28), 8.243 (1.36), 8.250 (1.09), 8.266 (1.28).

Example 094

2-cyclopropyl-3-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid-N-ethylethanamine salt (Enantiomer 2)

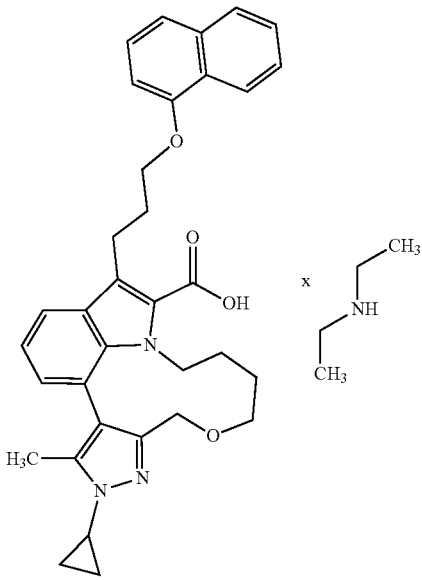

For the preparation of the racemic title compound and separation into enantiomers see Example 092.

Analytical Chiral HPLC (method see Example 092): $R_t$=5.80 min, ee 98.7%.

Example 096

3-methyl-1-[2-(morpholin-4-yl)ethyl]-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid-N-ethylethanamine salt (Enantiomer 1)

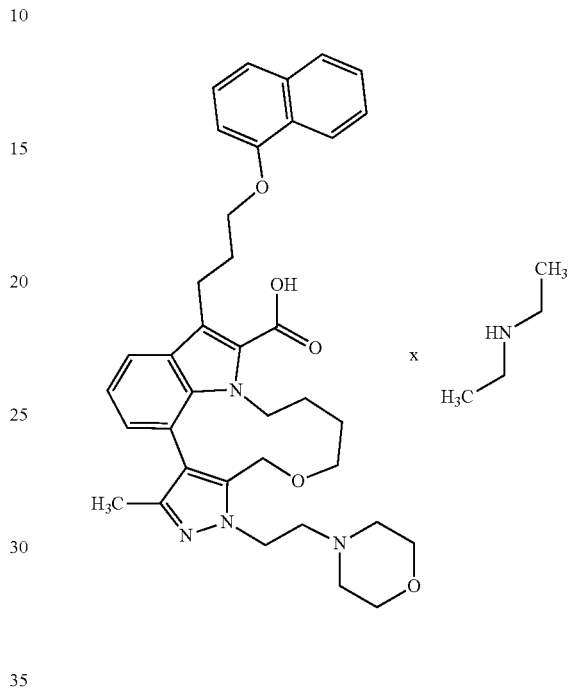

A mixture of (rac)-ethyl 3-methyl-1-[2-(morpholin-4-yl)ethyl]-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (see Intermediate 151, 287 mg, 441 μmol), THF (14 ml), ethanol (10 ml) and aqueous lithium hydroxide (9.9 ml, 1.0 M, 9.9 mmol) was stirred for 16 h at 50° C. For work-up, citric acid (2.09 g, 9.92 mmol) was added to adjust the pH to 5-6, water was added and the mixture was extracted three times with a mixture of dichloromethane/2-propanol (4:1). The combined organic phases were washed with brine, filtered through a silicone filter and concentrated. The residue was purified by preparative HPLC [Instrument: Waters Autopurification system; column: Waters XBrigde C18 5μ 100×30 mm; eluent A: water+0.1 vol-% formic acid (99%), eluent B: methanol; gradient: 0.00-0.50 min 31% B (25→70 mL/min), 0.51-5.50 min 60-87% B (70 mL/min), DAD scan: 210-400 nm] to give the racemate as free acid (78.5 mg) which was directly separated into enantiomers using chiral preparative HPLC to give enantiomer 1 (23.0 mg) and enantiomer 2 (21.0 mg, see example 097), of the corresponding—N-ethylethanamine salts.

Preparative chiral HPLC method: Instrument: Sepiatec: Prep SFC100; column: Chiralpak ID 5 μm 250×30 mm; eluent A carbon dioxide, eluent B: 2-propanol+0.4 vol-% diethylamine (99%); isocratic: 27% B; flow 100.0 ml/min temperature: 40° C.; BPR: 150 bar; MWD 254 nm Analytical chiral HPLC method: Instrument: Agilent: 1260, Aurora SFC-Modul; column: Chiralpak ID 5 μm 100×4.6 mm; eluent A: carbon dioxide, eluent B: 2-propanol+0.2 vol-% diethylamine (99%); isocratic: 27% B; flow 4.0 ml/min; temperature: 37.5° C.; BPR: 100 bar; MWD 254 nm Chiral analytical HPLC: $R_t$=3.34 min; ee>99%

LC-MS (Method 1): $R_t$=1.33 min; MS (ESIpos): m/z=623 [M+H]$^+$ $^1$H-NMR (400 MHz, DMSO-d6) δ[ppm]: 0.967 (1.39), 0.984 (0.62), 1.010 (0.56), 1.042 (0.50), 1.077 (0.50), 1.107 (12.33), 1.127 (7.07), 1.145 (16.00), 1.163 (6.92), 1.231 (0.53), 1.827 (13.75), 1.938 (0.71), 2.180 (0.92), 2.198 (1.36), 2.216 (1.01), 2.318 (0.53), 2.322 (1.18), 2.327 (1.69), 2.332 (1.24), 2.336 (0.56), 2.385 (0.95), 2.401 (1.04), 2.413 (1.57), 2.424 (0.92), 2.518 (7.39), 2.523 (4.85), 2.660 (0.53), 2.665 (1.21), 2.669 (1.74), 2.673 (1.27), 2.678 (0.56), 2.726 (0.53), 2.743 (1.06), 2.757 (1.30), 2.775 (1.15), 2.782 (1.04), 2.801 (1.42), 2.820 (0.80), 2.829 (1.86), 2.847 (4.88), 2.865 (4.73), 2.883 (1.48), 3.155 (0.44), 3.169 (0.50), 3.188 (0.65), 3.368 (1.24), 3.399 (0.77), 3.563 (3.55), 3.575 (6.62), 3.587 (3.58), 3.854 (0.53), 4.172 (1.30), 4.189 (2.87), 4.210 (2.43), 4.226 (2.28), 4.259 (1.57), 4.661 (1.72), 4.694 (1.77), 4.717 (0.50), 6.644 (0.95), 6.661 (1.01), 6.869 (1.57), 6.887 (1.69), 6.929 (0.98), 6.948 (1.51), 6.967 (0.86), 7.350 (1.09), 7.370 (2.13), 7.389 (1.60), 7.432 (2.37), 7.452 (1.33), 7.483 (0.50), 7.495 (1.36), 7.501 (1.39), 7.504 (1.69), 7.512 (2.99), 7.520 (1.72), 7.523 (1.57), 7.528 (1.54), 7.540 (0.56), 7.602 (1.15), 7.622 (1.04), 7.848 (1.42), 7.856 (0.77), 7.865 (1.24), 7.870 (1.21), 8.227 (1.21), 8.234 (1.15), 8.252 (1.15).

Example 097

3-methyl-1-[2-(morpholin-4-yl)ethyl]-7-[3-(naphthalen-1-yloxy)propyl]-1,10,11,12,13,15-hexahydropyrazolo[4',3':9,10][1,6]oxazacycloundecino[8,7-hi]indole-8-carboxylic acid-N-ethylethanamine salt (Enantiomer 2)

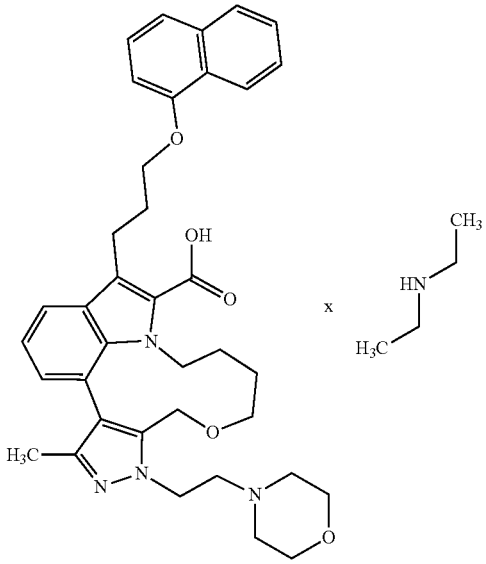

For the preparation of the racemic title compound and separation into enantiomers see Example 096.

Analytical Chiral HPLC (method see Example 096): $R_t$=6.37 min, ee>99%

Example 098

(rac)-(11Z)-3-methyl-7-[3-(naphthalen-1-yloxy)propyl]-1-(2,2,2-trifluoroethyl)-1,10,13,15-tetrahydropyrazolo[4',3':9,10][1,6]oxazacycloundecino[8,7,6-hi]indole-8-carboxylic acid

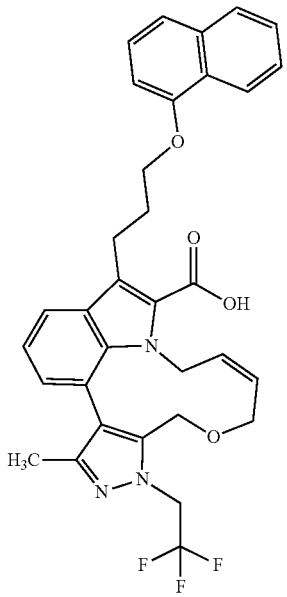 [SMILES: Cc1nn(CC(F)(F)F)c2c1-c1cccc3c(CCCOc4cccc5ccccc45)c(C(=O)O)n(c13)C/C=C\COC2]

A mixture of (rac)-ethyl (11Z)-3-methyl-7-[3-(naphthalen-1-yloxy)propyl]-1-(2,2,2-trifluoroethyl)-1,10,13,15-tetrahydropyrazolo[4',3':9,10][1,6]oxazacycloundecino[8,7,6-hi]indole-8-carboxylate (see Intermediate 173, 100 mg, 162 μmol), THF (5.3 ml), ethanol (3.8 ml) and aqueous lithium hydroxide (3.6 ml, 1.0 M, 3.6 mmol) was stirred for 16 h at 50° C. For work-up, citric acid (765 mg, 3.64 mmol) was added to adjust the pH to 5-6, water was added and the mixture was extracted three times with a mixture of dichloromethane/2-propanol (4:1). The combined organic phases were washed with brine, filtered through a silicone filter and concentrated. The residue was purified by preparative HPLC (method P1) to give the title compound 30.0 mg (31% yield).

LC-MS (Method 3): $R_t$=1.54 min; MS (ESIpos): m/z=590 [M+H]$^+$ $^1$H-NMR (400 MHz, DMSO-d6) δ[ppm]: 1.764 (16.00), 2.231 (0.92), 2.247 (1.39), 2.264 (0.97), 2.518 (2.55), 2.523 (1.74), 3.331 (11.53), 3.348 (1.77), 3.364 (1.37), 3.381 (0.67), 3.512 (0.60), 3.543 (1.10), 3.573 (0.71), 3.761 (0.63), 3.773 (0.74), 3.794 (0.57), 3.805 (0.52), 4.212 (1.31), 4.227 (2.78), 4.242 (1.31), 4.271 (1.62), 4.305 (1.78), 4.556 (0.52), 4.582 (0.60), 4.596 (0.65), 4.623 (0.69), 4.679 (1.75), 4.714 (1.58), 4.933 (0.47), 4.965 (0.96), 4.992 (0.56), 5.027 (0.46), 5.050 (0.50), 5.066 (0.84), 5.088 (0.77), 5.108 (0.97), 5.120 (0.69), 5.143 (1.67), 5.166 (1.24), 5.182 (0.79), 5.189 (0.56), 5.205 (0.44), 6.826 (1.71), 6.829 (1.83), 6.844 (1.96), 6.846 (1.94), 6.899 (1.73), 6.917 (1.86), 7.084 (1.68), 7.104 (2.13), 7.122 (1.50), 7.370 (1.31), 7.391 (2.48), 7.410 (2.08), 7.445 (2.58), 7.466 (1.39), 7.472 (0.58), 7.476 (0.67), 7.490 (1.38), 7.493 (1.32), 7.509 (2.33), 7.513 (2.56), 7.527 (1.37), 7.531 (1.56), 7.544 (0.71), 7.548 (0.53), 7.783 (1.71), 7.785 (1.81), 7.803 (1.67), 7.806 (1.63), 7.853 (1.52), 7.858 (1.02), 7.872 (1.61), 7.876 (1.32), 8.186 (1.36), 8.190 (1.42), 8.210 (1.32).

Example 099

(rac)-3-(methoxymethyl)-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid

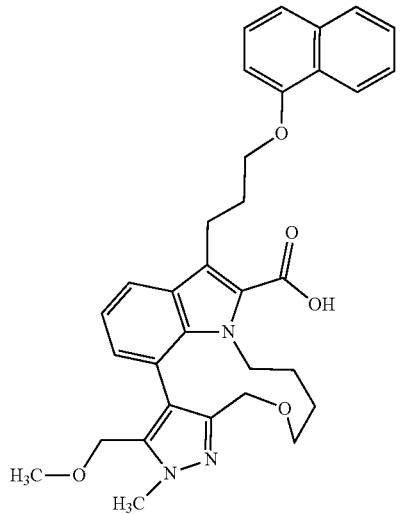 [SMILES: COCc1c2c(nn1C)COCCCCn1c(C(=O)O)c(CCCOc3cccc4ccccc34)c3cccc-2c31]

A mixture of (rac)-ethyl 3-(methoxymethyl)-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylate (370 mg, 636 μmol, intermediate 180), THF (26 ml), ethanol (19 ml) and aqueous lithium hydroxide (13 ml, 1.0 M, 13 mmol) was stirred for 16 h at 50° C. For work-up, the organic solvents were removed under vacuum, and the residue was washed with ethyl acetate. Then, citric acid (2.67 g, 12.7 mmol) was added to the aqueous phase to adjust the pH to 5-6, and the mixture was extracted three times with a mixture of dichloromethane/2-propanol (4:1). The combined organic phases were washed with brine, filtered through a silicone filter and concentrated. The residue was purified by preparative HPLC (method P5) to give the title compound 255 mg (65% yield) and (rac)-3-(methoxymethyl)-2-methyl-7-[3-(5,6,7,8-tetrahydronaphthalen-1-yloxy)propyl]-2,10,11,12,13,15-hexahydropyrazolo[4',3':9,10][1,6]oxazacycloundecino[8,7,6-hi]indole-8-carboxylic acid (40.2 mg, see Example 106)

LC-MS (Method 1): $R_t$=1.47 min; MS (ESIpos): m/z=554 [M+H]$^+$ $^1$H-NMR (400 MHz, DMSO-d$_6$): δ [ppm]=13.14 (br s, 1H), 8.31-8.26 (m, 1H), 7.92-7.87 (m, 1H), 7.76 (dd, 1H), 7.58-7.36 (m, 4H), 7.11-7.04 (m, 1H), 6.98-6.89 (m, 2H), 4.54 (d, 1H), 4.32-4.18 (m, 4H), 4.07-3.99 (m, 1H), 3.97-3.84 (m, 5H), 3.34-3.27 (m, 2H), 3.13 (td, 1H), 3.01 (s, 3H), 2.24 (quin, 2H), 1.44-1.34 (m, 1H), 1.31-1.14 (m, 3H), 1.13-0.98 (m, 1H).

The title compound was separated into enantiomers using chiral preparative HPLC to give enantiomer 1 (115 mg see example 100) and enantiomer 2 (105 mg, see example 101).

Preparative chiral HPLC method: Instrument: Sepiatec: Prep SFC100; column: Chiralpak ID 5 μm 250×30 mm; eluent A: carbon dioxide, eluent B: 2-propanol+0.4 vol-% diethylamine (99%); isocratic: 26% B; flow 100.0 ml/min temperature: 40° C.; BPR: 150 bar; MWD @ 254 nm Analytical chiral HPLC method: Instrument: Agilent: 1260, Aurora SFC-Modul; column: Chiralpak ID 5 μm 100×4.6 mm; eluent A: carbon dioxide, eluent B: 2-propanol+0.2 vol-% diethylamine (99%); isocratic: 26% B; flow 4.0 ml/min; temperature: 37.5° C.; BPR: 100 bar; MWD @ 254 nm Example 100

3-(methoxymethyl)-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid-N-ethylethanamine salt (Enantiomer 1)

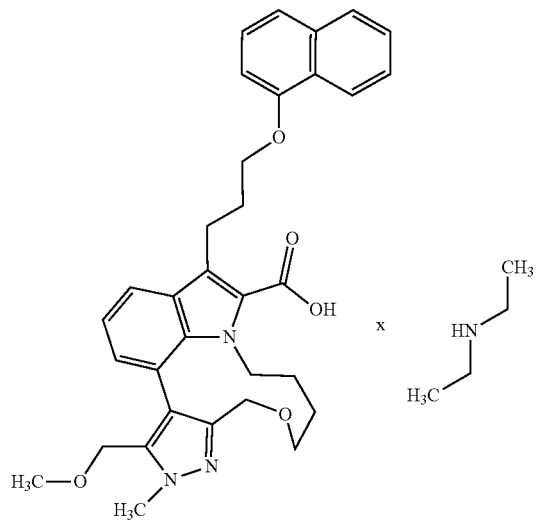

For the preparation of the racemic title compound and separation into enantiomers see Example 099.

Analytical Chiral HPLC (method see Example 099): $R_t$=2.98 min, ee 99.3%.

$^1$H-NMR (400 MHz, DMSO-d6) δ[ppm]: 1.108 (3.92), 1.123 (0.65), 1.143 (3.93), 1.161 (8.40), 1.180 (3.82), 2.194 (0.63), 2.212 (0.97), 2.229 (0.67), 2.518 (1.21), 2.523 (0.86), 2.838 (0.95), 2.856 (3.04), 2.874 (2.96), 2.893 (0.87), 2.998 (16.00), 3.091 (0.42), 3.222 (0.41), 3.240 (0.66), 3.284 (1.08), 3.301 (0.79), 3.315 (0.73), 3.334 (0.41), 3.868 (10.40), 3.875 (1.70), 3.907 (1.65), 4.037 (1.59), 4.069 (1.20), 4.155 (0.44), 4.172 (0.95), 4.182 (0.95), 4.198 (0.44), 4.218 (1.31), 4.249 (1.45), 4.451 (1.30), 4.483 (1.05), 6.777 (0.75), 6.793 (0.90), 6.849 (1.06), 6.867 (1.15), 6.941 (0.89), 6.961 (1.17), 6.979 (0.74), 7.340 (0.85), 7.360 (1.51), 7.380 (1.16), 7.430 (1.52), 7.451 (0.90), 7.500 (1.01), 7.506 (1.62), 7.516 (2.11), 7.525 (1.76), 7.530 (1.11), 7.617 (0.88), 7.634 (0.82), 7.848 (0.88), 7.851 (0.64), 7.858 (0.44), 7.866 (0.59), 7.871 (0.75), 8.241 (0.79), 8.248 (0.62), 8.265 (0.73).

Example 101

3-(methoxymethyl)-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid-N-ethylethanamine salt (Enantiomer 2)

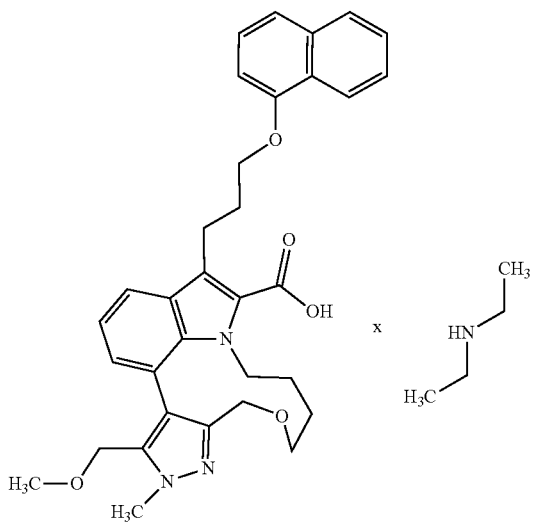

For the preparation of the racemic title compound and separation into enantiomers see Example 099.

Analytical Chiral HPLC (method see Example 099): $R_t$=5.24 min, ee 99.7%.

Example 102

(rac)-3-Cyclopropyl-1-(2-methoxyethyl)-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid

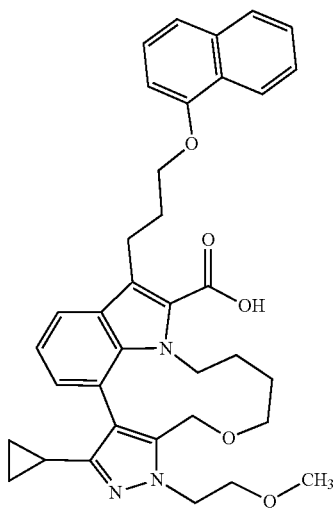

A mixture of (rac)-ethyl 3-cyclopropyl-1-(2-methoxyethyl)-7-[3-(naphthalen-1-yloxy)propyl]-1,10,11,12,13,15-hexahydropyrazolo[4',3':9,10][1,6]oxazacycloundecino[8,7,6-hi]indole-8-carboxylate and (rac)-ethyl 3-cyclopropyl-1-(2-methoxyethyl)-7-[3-(5,6,7,8-tetrahydronaphthalen-1-yloxy)propyl]-1,10,11,12,13,15-hexahydropyrazolo[4',3':9,10][1,6]oxazacycloundecino[8,7,6-hi]indole-8-carboxylate (230 mg, see Intermediate 204), THF (12 mL), ethanol (8.6 mL) and lithium hydroxide (8.3 mL, 1.0 M in water) was stirred at 50° C. overnight. Water was added, the mixture was acidified by the addition of citric acid (pH 5-6) and extracted with dichloromethane. The organic layer was dried over sodium sulfate. After filtration and removal of the solvents the residue was purified by preparative HPLC [Instrument: Waters Autopurification system; column: Waters XBrigde C18 5μ 100×30 mm; eluent A: water+0.1 vol-% formic acid (99%), eluent B: acetonitrile; gradient: 0.00-0.50 min 30% B (25→70 mL/min), 0.51-5.50 min 60-85% B (70 mL/min), DAD scan: 210-400 nm] followed by preparative HPLC [Instrument: Waters Autopurification system; column: Waters XBrigde C18 5μ 100×30 mm; eluent A: water+0.2 Vol-% ammonia (32%), eluent B: acetonitrile; gradient: 0.00-0.50 min 11% B (25→70 mL/min), 0.51-5.50 min 22-36% B (70 mL/min), DAD scan: 210-400 nm] to give the title compound (30.0 mg) as mixture of atropisomers. For the corresponding 5,6,7,8-tetrahydronaphthalen-1-yloxy compound, which was isolated as a second product, see Example 164.

LC-MS: m/z=594.3 [M+H]$^+$.

$^1$H-NMR (400 MHz, DMSO-d6), δ [ppm]=0.52-0.64 (4H), 1.00 (2H), 1.17-1.38 (3H), 2.21 (2H), 2.79 (1H), 3.24-3.44 (3H), 3.27 (3H), 3.72 (2H), 4.07 (1H), 4.16-4.30 (5H), 4.57 (1H), 4.63 (1H), 6.86 (1H), 6.89 (1H), 7.05 (1H), 7.38 (1H), 7.46 (1H), 7.52 (2H), 7.75 (1H), 7.87 (1H), 8.24 (1H), 13.20 (1H).

The title compound (25 mg) was separated into enantiomers by preparative chiral HPLC to give enantiomer 1 (10.5 mg, see Example 103) and enantiomer 2 (12.5 mg, see Example 104).

Preparative chiral HPLC method: Instrument: Sepiatec: Prep SFC100; column: Chiralpak IE 5 μm 250×30 mm; eluent A: carbon dioxide, eluent B: ethanol+0.4 vol-% diethylamine (99%); isocratic: 27% B; flow 100.0 ml/min temperature: 40° C.; BPR: 150 bar; MWD @ 254 nm Analytical chiral HPLC method: Instrument: Agilent: 1260, Aurora SFC-Modul; column: Chiralpak IE 5 μm 100×4.6 mm; eluent A: carbon dioxide, eluent B: ethanol+0.2 vol-% diethylamine (99%); isocratic: 27% B; flow 4.0 ml/min; temperature: 37.5° C.; BPR: 100 bar; MWD @ 254 nm

Example 103

3-cyclopropyl-1-(2-methoxyethyl)-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid-N-ethylethanamine salt (Enantiomer 1)

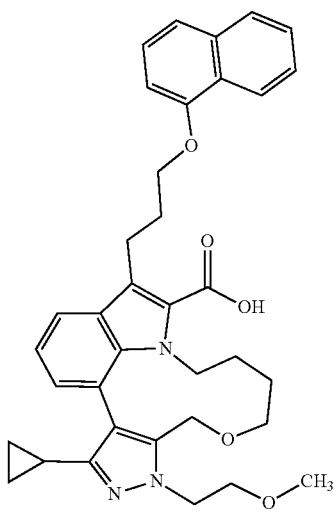 x 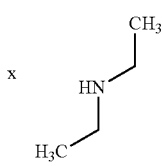

For the preparation of the racemic title compound and separation of enantiomers by preparative chiral HPLC see Example 102.

Analytical Chiral HPLC (method see Example 102): $R_t$=2.79 min, ee 99.3%.

LC-MS: m/z=594.3 [M+H]⁺.

¹H-NMR (400 MHz, DMSO-d6), δ [ppm]=0.52-0.63 (4H), 0.99 (2H), 1.09-1.20 (1H), 1.14 (2.4H), 1.30 (1H), 1.42 (1H), 2.20 (2H), 2.78 (1H), 2.86 (1.6H), 3.20 (1H), 3.27 (3H), 3.25-3.42 (2H), 3.72 (2H), 3.97 (1H), 4.16-4.27 (5H), 4.62 (1H), 4.67 (1H), 6.74 (1H), 6.88 (1H), 6.97 (1H), 7.37 (1H), 7.45 (1H), 7.52 (2H), 7.64 (1H), 7.86 (1H), 8.24 (1H).

Example 104

3-cyclopropyl-1-(2-methoxyethyl)-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid-N-ethylethanamine salt (Enantiomer 2)

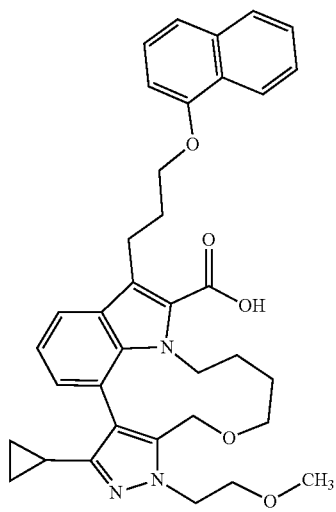 [SMILES: COCCn1nc(C2CC2)c2c1COCCCCn1c(C(=O)O)c(CCCOc3cccc4ccccc34)c3cccc-2c31] x 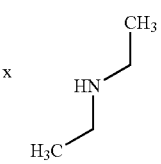

For the preparation of the racemic title compound and separation of enantiomers by preparative chiral HPLC see Example 102.

Analytical Chiral HPLC (method see Example 102): $R_t$=3.99 min, ee 97.0%.

LC-MS: m/z=594.4 [M+H]⁺.

¹H-NMR (400 MHz, DMSO-d6), δ [ppm]=0.52-0.63 (4H), 0.99 (2H), 1.09-1.20 (1H), 1.14 (3.0H), 1.30 (1H), 1.42 (1H), 2.20 (2H), 2.78 (1H), 2.86 (2.0H), 3.20 (1H), 3.27 (3H), 3.25-3.42 (2H), 3.72 (2H), 3.97 (1H), 4.16-4.27 (5H), 4.62 (1H), 4.67 (1H), 6.74 (1H), 6.88 (1H), 6.97 (1H), 7.37 (1H), 7.45 (1H), 7.52 (2H), 7.64 (1H), 7.86 (1H), 8.24 (1H).

Example 105

(rac)-3-(methoxymethyl)-2-methyl-7-[3-(5,6,7,8-tetrahydronaphthalen-1-yloxy)propyl]-2,10,11,12,13,15-hexahydropyrazolo[4',3':9,10][1,6]oxazacycloundecino[8,7,6-hi]indole-8-carboxylic acid

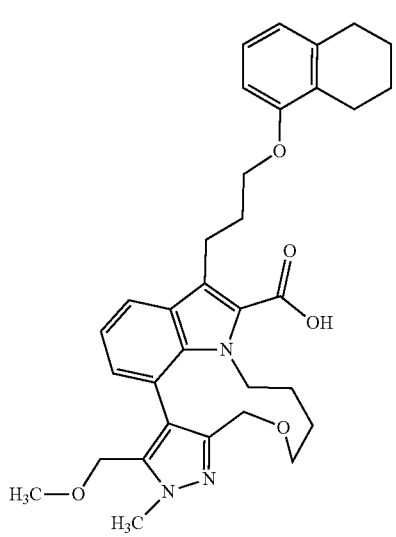 [SMILES: COCc1c2c(nn1C)COCCCCn1c(C(=O)O)c(CCCOc3cccc4c3CCCC4)c3cccc-2c31]

The title compound was isolated in the synthesis of (rac)-3-(methoxymethyl)-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (example 99).

LC-MS (Method 1): Rt=1.57 min; MS (ESIpos): m/z=558 [M+H]$^+$ $^1$H-NMR (500 MHz, DMSO-d$_6$): δ [ppm]=13.03 (br s, 1H), 7.69 (dd, 1H), 7.09 (t, 1H), 7.00-6.91 (m, 2H), 6.64-6.60 (m, 2H), 4.53 (d, 1H), 4.29-4.19 (m, 2H), 4.03-3.84 (m, 8H), 3.31-3.08 (m, 4H), 3.00-2.98 (m, 3H), 2.71-2.61 (m, 4H), 2.12-2.02 (m, 1H), 1.77-1.66 (m, 4H), 1.40-1.30 (m, 1H), 1.29-1.14 (m, 2H), 1.06-0.94 (m, 1H).

Example 107

2-(2-methoxyethyl)-3-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid-N-ethylethanamine salt
(Enantiomer 1)

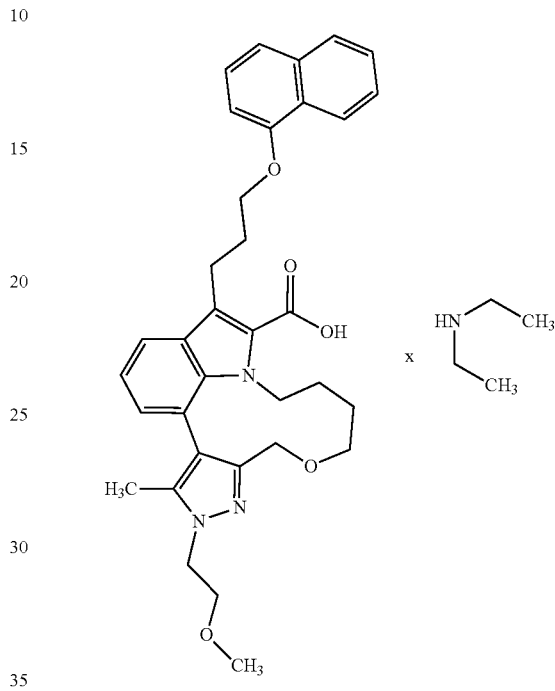

A mixture of (rac)-ethyl 2-(2-methoxyethyl)-3-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylate (400 mg, 671 µmol, intermediate 144), THF (22 ml), ethanol (16 ml) and aqueous lithium hydroxide (15 ml, 1.0 M, 15 mmol) was stirred for 16 h at 50° C. For work-up, citric acid (3.17 g, 15.1 mmol) was added to adjust the pH to 5-6, water was added and the mixture was extracted three times with a mixture of dichloromethane/2-propanol (4:1). The combined organic phases were washed with brine, filtered through a silicone filter and concentrated. The residue was purified by flash chromatography (Biotage SNAP cartridge silica, dichloromethane/methanol gradient, 0%→10% methanol) followed by preparative HPLC [Instrument: Waters Autopurification system; column: Waters XBrigde C18 5µ 100×30 mm; eluent A: water+0.1 vol-% formic acid (99%), eluent B: acetonitrile; gradient: 0.00-0.50 min 28% B (25→70 mL/min), 0.51-5.50 min 55-75% B (70 mL/min), DAD scan: 210-400 nm] to give 132 mg of the title compound as racemic mixture which was directly separated into enantiomers to give enantiomer 1 (60.5 mg) and enantiomer 2 (49.0 mg, see example 108).

Preparative chiral HPLC method: Instrument: Labomatic HD5000, Labocord-5000; Gilson GX-241, Labcol Vario 4000, column: Chiralpak IA 5µ 250×30 mm; eluent A: hexanes+0.1 vol-% diethylamine (99%); eluent B: ethanol; gradient: 20-50% B in 15 min; flow 40.0 ml/min; UV 254 nm Analytical chiral HPLC method: Instrument: Agilent HPLC 1260; column: Chiralpak IA 3µ 100×4.6 mm; eluent A: hexanes+0.1 vol-% diethylamine (99%); eluent B: ethanol; gradient: 20-50% B in 7 min; flow 1.4 ml/min; temperature: 25° C.; DAD 254 nm LC-MS (Method 2): $R_t$=0.87 min; MS (ESIpos): m/z=568 [M+H]$^+$ Chiral analytical HPLC: $R_t$=4.75 min; ee>99%

$^1$H-NMR (400 MHz, DMSO-d6) δ[ppm]: 1.107 (0.60), 1.114 (2.54), 1.133 (5.14), 1.150 (2.54), 1.832 (8.44), 1.905 (0.76), 2.183 (0.51), 2.200 (0.76), 2.217 (0.54), 2.318 (0.54), 2.322 (1.27), 2.326 (1.75), 2.332 (1.24), 2.336 (0.54), 2.518 (6.44), 2.522 (4.23), 2.660 (0.54), 2.664 (1.27), 2.668 (1.75), 2.673 (1.27), 2.678 (0.54), 2.816 (0.42), 2.834 (1.33), 2.852 (1.30), 2.870 (0.42), 3.062 (0.36), 3.240 (16.00), 3.271 (0.64), 3.290 (0.97), 3.678 (0.48), 3.694 (0.82), 3.708 (0.94), 3.722 (0.64), 3.734 (0.33), 4.161 (0.36), 4.176 (0.82), 4.187 (1.88), 4.202 (0.48), 4.218 (1.33), 4.225 (0.60), 4.239 (0.94), 4.250 (0.82), 4.262 (0.42), 4.483 (0.85), 4.515 (0.70), 6.867 (0.88), 6.884 (0.94), 6.959 (0.33), 6.977 (0.48), 7.351 (0.70), 7.372 (1.27), 7.391 (1.03), 7.435 (1.27), 7.456 (0.73), 7.505 (0.91), 7.510 (1.48), 7.520 (1.72), 7.529 (1.45), 7.533 (1.00), 7.607 (0.36), 7.627 (0.33), 7.851 (0.73), 7.854 (0.51), 7.861 (0.39), 7.865 (0.45), 7.868 (0.48), 7.874 (0.64), 8.244 (0.70), 8.252 (0.42), 8.269 (0.60).

Example 108

2-(2-methoxyethyl)-3-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid-N-ethylethanamine salt
(Enantiomer 2)

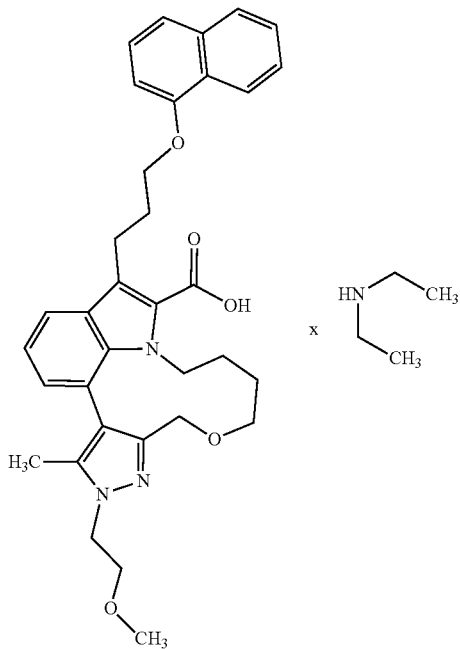

For the preparation of the racemic title compound and separation into enantiomers see Example 107.

Analytical Chiral HPLC (method see Example 107): $R_t$=6.45 min; ee 96.7%

Example 109

(rac)-3-methyl-7-[3-(naphthalen-1-yloxy)propyl]-1-(2,2,2-trifluoroethyl)-1,10,11,12,13,15-hexahydropyrazolo[4',3':9,10][1,6]oxazacycloundecino[8,7,6-hi]indole-8-carboxylic acid

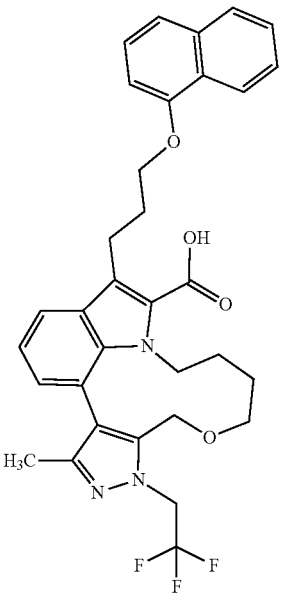 [SMILES: Cc1nn(CC(F)(F)F)c2c1-c1cccc3c(CCCOc4cccc5ccccc45)c(C(=O)O)n(c13)CCCCOC2]

A mixture of (rac)-ethyl 3-methyl-7-[3-(naphthalen-1-yloxy)propyl]-1-(2,2,2-trifluoroethyl)-1,10,11,12,13,15-hexahydropyrazolo[4',3':9,10][1,6]oxazacycloundecino[8,7,6-hi]indole-8-carboxylate (560 mg, 904 μmol, intermediate 174), THF (37 ml), ethanol (26 ml) and aqueous lithium hydroxide (18 ml, 1.0 M, 18 mmol) was stirred for 16 h at 50° C. For work-up, citric acid (3.80 g, 18.1 mmol) was added to adjust the pH to 5-6, water was added and the mixture was extracted three times with a mixture of dichloromethane/2-propanol (4:1). The combined organic phases were washed with brine, filtered through a silicone filter and concentrated. The residue was purified twice by preparative HPLC to give the title compound (213 mg, 39% yield) and (rac)-3-methyl-7-[3-(5,6,7,8-tetrahydronaphthalen-1-yloxy)propyl]-1-(2,2,2-trifluoroethyl)-1,10,11,12,13,15-hexahydropyrazolo[4',3':9,10][1,6]oxazacycloundecino[8,7,6-hi]indole-8-carboxylic acid (93.8 mg, see Example 161).

LC-MS (Method 1): $R_t$=1.60 min; MS (ESIpos): m/z=592 [M+H]$^+$ $^1$H-NMR (400 MHz, DMSO-d$_6$): δ [ppm]=13.22 (br s, 1H), 8.26-8.22 (m, 1H), 7.89-7.84 (m, 1H), 7.78 (dd, 1H), 7.55-7.37 (m, 4H), 7.07 (dd, 1H), 6.91-6.87 (m, 2H), 5.23-5.02 (m, 2H), 4.66 (d, 1H), 4.55 (dt, 1H), 4.35 (d, 1H), 4.24-4.17 (m, 2H), 3.92 (dt, 1H), 3.47-3.35 (m, 2H), 3.31-3.25 (m, 1H), 2.80 (dt, 1H), 2.26-2.17 (m, 2H), 1.84 (s, 3H), 133-1.19 (m, 2H), 1.10-0.94 (m, 2H).

The title compound was separated into enantiomers using chiral preparative HPLC (208 mg) to give enantiomer 1 (90 mg, see example 110) and enantiomer 2 (105 mg, see example 111).

Preparative chiral HPLC method: Instrument: Sepiatec: Prep SFC100; column: Chiralpak IE 5 μm 250×30 mm; eluent A: carbon dioxide, eluent B: ethanol+0.4 vol-% diethylamine (99%); isocratic: 21% B; flow 100.0 ml/min temperature: 40° C.; BPR: 150 bar; MWD @ 254 nm Analytical chiral HPLC method: Instrument: Agilent: 1260, Aurora SFC-Modul; column: Chiralpak IE 5 μm 100×4.6 mm; eluent A: carbon dioxide, eluent B: ethanol+ 0.2 vol-% diethylamine (99%); isocratic: 21% B; flow 4.0 ml/min; temperature: 37.5° C.; BPR: 100 bar; MWD @ 254 nm Example 110

3-methyl-7-[3-(naphthalen-1-yloxy)propyl]-1-(2,2,2-trifluoroethyl)-1,10,11,12,13,15-hexahydropyrazolo[4',3':9,10][1,6]oxazacycloundecino[8,7,6-hi]indole-8-carboxylic acid-N-ethylethanamine salt (Enantiomer 1)

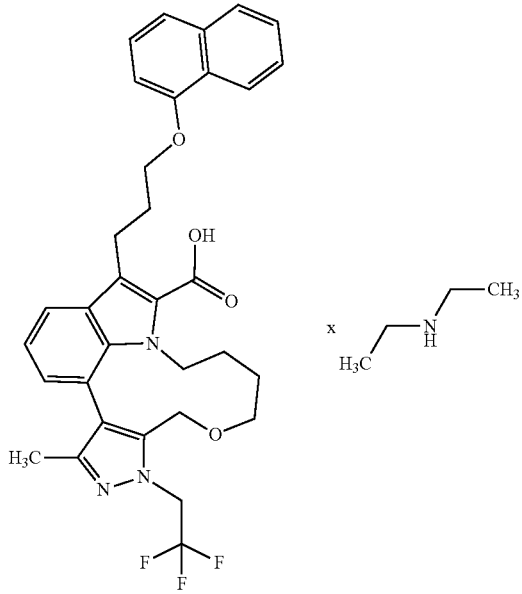

For the preparation of the racemic title compound and separation into enantiomers see Example 109.

Analytical Chiral HPLC (method see Example 109): $R_t$=1.71 min, ee 98.8%.

LC-MS (Method 1): Rt=1.60 min; MS (ESIpos): m/z=592 [M+H]$^+$ $^1$H-NMR (400 MHz, DMSO-d6) δ[ppm]: 0.798 (0.46), 0.815 (0.52), 0.821 (0.56), 0.905 (0.52), 1.009 (0.67), 1.107 (16.00), 1.140 (5.53), 1.158 (12.10), 1.176 (5.32), 1.854 (10.75), 2.185 (0.64), 2.204 (0.94), 2.221 (0.69), 2.327 (0.56), 2.332 (0.41), 2.518 (2.05), 2.523 (1.44), 2.665 (0.40), 2.669 (0.55), 2.839 (1.36), 2.858 (4.26), 2.876 (4.14), 2.894 (1.25), 3.195 (0.54), 3.288 (0.66), 3.308 (1.27), 3.324 (1.53), 3.340 (1.56), 3.385 (0.53), 3.404 (0.65), 3.415 (0.50), 3.433 (0.53), 3.781 (0.42), 4.171 (0.78), 4.187 (1.58), 4.203 (0.79), 4.294 (1.05), 4.328 (1.20), 4.626 (1.21), 4.660 (1.08), 4.697 (0.42), 5.021 (0.51), 5.044 (0.42), 5.135 (0.49), 5.157 (0.51), 6.687 (0.86), 6.704 (0.95), 6.867 (1.17), 6.884 (1.25), 6.940 (0.98), 6.959 (1.30), 6.977 (0.85), 7.348 (0.86), 7.368 (1.64), 7.387 (1.30), 7.430 (1.70), 7.451 (0.97), 7.494 (1.01), 7.498 (0.95), 7.503 (1.18), 7.511 (2.34), 7.518 (1.19), 7.522 (1.04), 7.527 (1.13), 7.539 (0.41), 7.622 (0.99), 7.639 (0.92), 7.846 (1.03), 7.854 (0.53), 7.864 (0.94), 7.870 (0.86), 8.226 (0.89), 8.231 (0.83), 8.250 (0.84).

Example 111

3-methyl-7-[3-(naphthalen-1-yloxy)propyl]-1-(2,2,2-trifluoroethyl)-1,10,11,12,13,15-hexahydropyrazolo[4',3':9,10][1,6]oxazacycloundecino[8,7,6-hi]indole-8-carboxylic acid-N-ethylethanamine salt (Enantiomer 2)

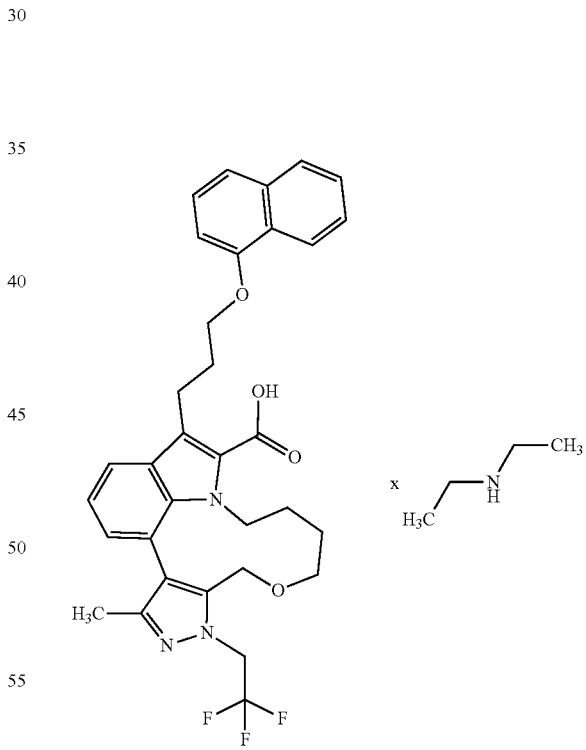

For the preparation of the racemic title compound and separation into enantiomers see Example 109.

Analytical Chiral HPLC (method see Example 109): $R_t$=2.42 min, ee 98.3%.

Example 113

(rac)-7,10-dimethyl-1-[3-(naphthalen-1-yloxy)propyl]-11-(propan-2-yl)-4,5,6,7,8,10-hexahydropyrazolo[3',4':7,8][1,5]diazecino[9,10,1-hi]indole-2-carboxylic acid

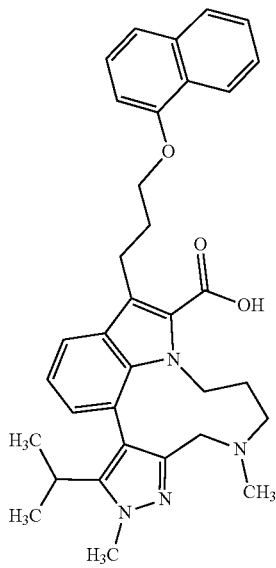 [SMILES: CC(C)c1c2c(nn1C)CN(C)CCCn1c(C(=O)O)c(CCCOc3cccc4ccccc34)c3cccc-2c31]

A mixture of (rac)-ethyl 7,10-dimethyl-1-[3-(naphthalen-1-yloxy)propyl]-11-(propan-2-yl)-4,5,6,7,8,10-hexahydropyrazolo[3',4':7,8][1,5]diazecino[9,10,1-hi]indole-2-carboxylate (140 mg, 242 μmol, intermediate 188), THF (9.8 ml), ethanol (7.0 ml) and aqueous lithium hydroxide (5.4 ml, 1.0 M, 5.4 mmol) was stirred for 1 day at 50° C. For work-up, the organic solvents were removed under vacuum, citric acid (2.90 g, 13.8 mmol) was added and the mixture was stirred for 30 min. The precipitate formed was collected by filtration, and purified by by preparative HPLC (method P4) to give the title compound (82.6 mg, 98% purity, 61% yield).

LC-MS (Method 1): $R_t$=1.30 min; MS (ESIneg): m/z=549 [M−H]⁻

¹H-NMR (400 MHz, DMSO-d6) δ[ppm]: 0.875 (11.20), 0.892 (11.33), 1.037 (11.61), 1.055 (11.84), 1.439 (0.90), 1.462 (0.67), 1.551 (1.08), 1.581 (0.67), 1.791 (16.00), 1.953 (1.26), 1.987 (1.34), 2.159 (1.16), 2.178 (2.21), 2.196 (3.31), 2.213 (2.21), 2.230 (0.74), 2.364 (0.92), 2.393 (1.46), 2.427 (0.87), 2.518 (5.19), 2.522 (3.49), 2.539 (0.98), 2.673 (1.05), 2.993 (0.69), 3.010 (1.75), 3.027 (2.34), 3.045 (1.67), 3.062 (0.64), 3.099 (2.08), 3.131 (3.67), 3.188 (3.29), 3.220 (1.90), 3.236 (0.69), 3.254 (1.23), 3.269 (1.64), 3.287 (2.85), 3.307 (3.62), 3.326 (7.14), 3.358 (2.52), 3.851 (1.28), 3.873 (1.16), 3.903 (0.49), 4.136 (2.29), 4.151 (4.57), 4.167 (2.26), 4.593 (1.05), 4.605 (1.18), 4.626 (1.05), 4.640 (1.00), 6.822 (6.32), 6.839 (7.65), 6.913 (3.60), 6.932 (4.13), 6.950 (2.54), 7.344 (2.39), 7.364 (4.62), 7.384 (3.39), 7.435 (4.93), 7.456 (3.03), 7.500 (1.00), 7.512 (3.54), 7.515 (4.37), 7.526 (5.14), 7.536 (4.29), 7.538 (3.90), 7.550 (1.00), 7.642 (3.31), 7.645 (3.36), 7.662 (3.16), 7.852 (2.85), 7.856 (1.95), 7.865 (2.41), 7.870 (1.85), 7.875 (2.36), 8.158 (1.82), 8.258 (2.47), 8.268 (2.05), 8.282 (2.29).

The title compound was separated into enantiomers using chiral preparative HPLC (method see below). Each enantiomer was then repurified using preparative HPLC [Instrument: Waters Autopurification system; column: Waters XBrigde C18 5μ 100×30 mm; eluent A: water+0.2 vol-% ammonia (32%), eluent B: methanol; gradient: 0.00-0.50 min 25% B (25→70 mL/min), 0.51-5.50 min 51-71% B (70 mL/min), DAD scan: 210-400 nm] to give enantiomer 1 (4.7 mg see example 114) and enantiomer 2 (10.2 mg, see example 115).

Preparative chiral HPLC method: Instrument: Labomatic HD5000, Labocord-5000; Gilson GX-241, Labcol Vario 4000, column: Chiralpak AD-H 5μ 250×30 mm; eluent A: hexanes+0.1 vol-% diethylamine (99%); eluent B: 2-propanol; gradient: 5-50% B in 20 min; flow 40.0 ml/min; UV 254 nm Analytical chiral HPLC method: Instrument: Agilent HPLC 1260; column: Chiralpak AD-H 3μ 100×4.6 mm; eluent A: hexanes+0.1 vol-% diethylamine (99%); eluent B: 2-propanol; gradient: 20-50% B in 7 min; flow 1.4 ml/min; temperature: 25° C.; DAD 254 nm

Example 114

7,10-dimethyl-1-[3-(naphthalen-1-yloxy)propyl]-11-(propan-2-yl)-4,5,6,7,8,10-hexahydropyrazolo[3',4':7,8][1,5]diazecino[9,10,1-hi]indole-2-carboxylic acid (Enantiomer 1)

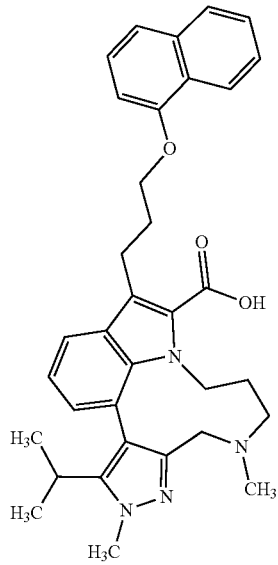 [SMILES: CC(C)c1c2c(nn1C)CN(C)CCCn1c(C(=O)O)c(CCCOc3cccc4ccccc34)c3cccc-2c31]

For the preparation of the racemic title compound and separation into enantiomers see Example 113.

Analytical Chiral HPLC (method see Example 113): $R_t$=1.41 min, ee>99.9%.

Example 115

7,10-dimethyl-1-[3-(naphthalen-1-yloxy)propyl]-11-(propan-2-yl)-4,5,6,7,8,10-hexahydropyrazolo[3',4':7,8][1,5]diazecino[9,10,1-hi]indole-2-carboxylic acid (Enantiomer 2)

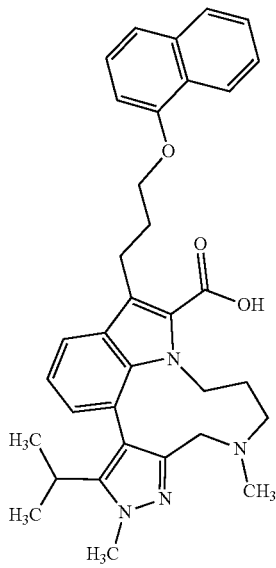 [SMILES: CC(C)c1c2c(nn1C)CN(C)CCCn1c(C(=O)O)c(CCCOc3cccc4ccccc34)c3cccc-2c31]

For the preparation of the racemic title compound and separation into enantiomers see Example 113.
Analytical Chiral HPLC (method see Example 113): $R_t$=2.25 min, ee>99.9%.

Example 116

(rac)-12-Methoxy-1-[3-(5,6,7,8-tetrahydronaphthalen-1-yloxy)propyl]-5,6,7,8-tetrahydro-4H-10,14-(metheno)[1,7]oxazacyclotetradecino[9,8,7-hi]indole-2-carboxylic acid

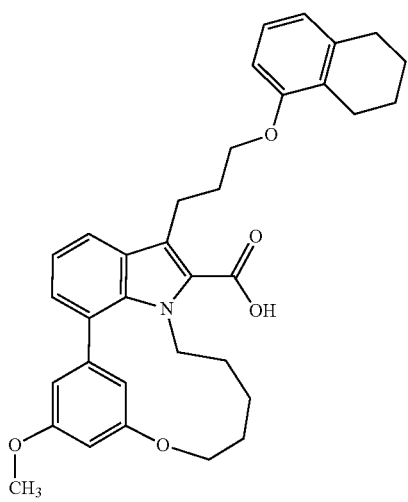 [SMILES: COc1cc2cc(c1)-c1cccc3c(CCCOc4cccc5c4CCCC5)c(C(=O)O)n(c13)CCCCCO2]

A mixture of (rac)-ethyl 12-methoxy-1-[3-(5,6,7,8-tetrahydronaphthalen-1-yloxy)propyl]-5,6,7,8-tetrahydro-4H-10,14-(metheno)[1,7]oxazacyclotetradecino[9,8,7-hi]indole-2-carboxylate (15.2 mg, 26.8 µmol, see Intermediate 207), THF (1.0 mL), methanol (200 µL) and lithium hydroxide (160 µL, 1.0 M in water) was stirred at RT overnight. Water was added, the mixture acidified to pH 3-4 by the addition of aqueous hydrochloric acid and extracted with dichloromethane. The organic layer was dried over sodium sulfate. After filtration and removal of the solvents the residue was purified by preparative TLC (EtOH:dichloromethane) to give the title compound (4.6 mg, 30% yield).

LC-MS: m/z=539.3 [M+H]$^+$.

$^1$H-NMR (400 MHz, DMSO-d6), δ [ppm]=0.64 (1H), 1.32-1.51 (2H), 1.63-1.81 (6H), 1.95-2.09 (3H), 2.62 (2H), 2.68 (2H), 3.04 (1H), 3.11 (2H), 3.77 (3H), 3.94 (2H), 3.99 (1H), 4.53 (1H), 4.74 (1H), 6.47 (1H), 6.51 (1H), 6.63 (2H), 6.95-7.03 (3H), 7.10 (1H), 7.55 (1H).

Example 117

(rac)-13-Methyl-1-[3-(naphthalen-1-yloxy)propyl]-4,5,7,8-tetrahydro-10,14-(metheno)[1,4,7]dioxazacyclotetradecino[9,8,7-hi]indole-2-carboxylic acid

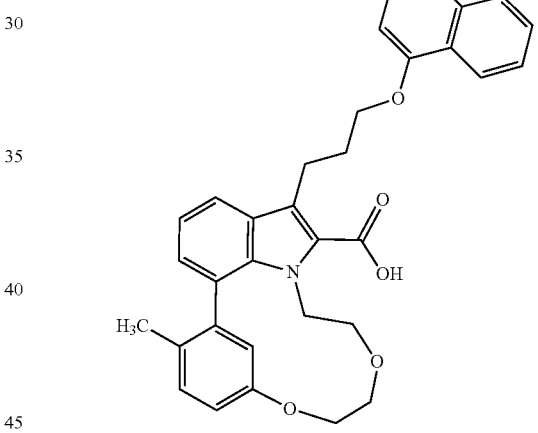

A mixture of (rac)-ethyl 13-methyl-1-[3-(naphthalen-1-yloxy)propyl]-4,5,7,8-tetrahydro-10,14-(metheno)[1,4,7]dioxazacyclotetradecino[9,8,7-hi]indole-2-carboxylate (38.3 mg, 69.7 µmol, see Intermediate 209), THF (2.6 mL), methanol (500 µL) and lithium hydroxide (420 µL, 1.0 M in water) was stirred at 80° C. for 2 hrs. Water was added, the mixture was acidified to pH 3-4 by the addition of aqueous hydrochloric acid and extracted with dichloromethane. The organic layer was dried over sodium sulfate. After filtration and removal of the solvents the residue was purified by preparative HPLC (method P1) and preparative TLC (ethyl acetate:n-hexane) to give the title compound (6.8 mg, 18% yield) as a mixture of atropisomers.

LC-MS: m/z=522.2 [M+H]$^+$.

1H-NMR (400 MHz, DMSO-d6), δ [ppm]=2.00 (3H), 2.18 (2H), 2.77 (1H), 3.17-3.48 (4H), 3.72-3.84 (3H), 4.19 (2H), 4.55 (1H), 4.86 (1H), 6.85 (1H), 6.91 (1H), 6.95-7.04 (2H), 7.15 (1H), 7.34-7.43 (2H), 7.46 (1H), 7.52 (2H), 7.61 (1H), 7.86 (1H), 8.23 (1H).

Example 118

(rac)-(E/Z)-1-methyl-3-{[4-(morpholin-4-yl)phenoxy]methyl}-7-[3-(naphthalen-1-yloxy)propyl]-1,10,13,15-tetrahydropyrazolo[4',3':9,10][1,6]oxazacycloundecino[8,7,6-hi]indole-8-carboxylic acid

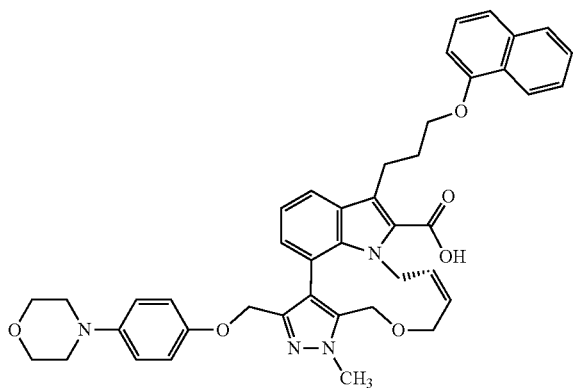

To a solution of (rac)-ethyl (E/Z)-1-methyl-3-{[4-(morpholin-4-yl)phenoxy]methyl}-7-[3-(naphthalen-1-yloxy)propyl]-1,10,13,15-tetrahydropyrazolo[4',3':9,10][1,6]oxazacycloundecino[8,7,6-hi]indole-8-carboxylate (see Intermediate 214, 100 mg, 138 µmol) in THF (2.3 ml) and ethanol (2.3 ml) was added a solution of lithium hydroxide in water (2.3 ml, 1.0 M, 2.3 mmol). The reaction mixture was stirred for 3 days at 45° C. For work-up, the reaction mixture was concentrated under reduced pressure and the residue was purified by flash chromatography (dichloromethane/methanol gradient, 0%→5% methanol) to give the title compound (82 mg) as a racemic mixture.

LC-MS (Method 1): Rt=1.50 min; MS (ESIpos): m/z=699 [M+H]$^+$

The title compound (82 mg) was separated into enantiomers by preparative chiral HPLC, followed by flash chromatography (the product was combined with the product obtained from another batch prepared analogously), to give enantiomer 1 (40 mg, see Example 119) and enantiomer 2 (41 mg, see Example 120).

Preparative chiral HPLC method: Instrument: Labomatic HD5000, Labocord-5000; Gilson GX-241, Labcol Vario 4000, column: Chiralpak IC 5µ 250×30 mm; eluent A: acetonitrile+0.1 Vol-% trifluoroacetic acid; eluent B: ethanol; gradient: 5-50% B 1-21 Min; flow 400.0 ml/min; UV 254 nm.

Analytical chiral HPLC method: Instrument: Agilent HPLC 1260; column: Chiralpak IC 3µ 100×4.6 mm; Eluent A: hexane+0.1 Vol-% trifluoroacetic acid; eluent B: ethanol; gradient: 5-50% B; flow 1.4 ml/min; temperature: 25° C.; DAD 254 nm

Example 119

(+)-(E/Z)-1-methyl-3-{[4-(morpholin-4-yl)phenoxy]methyl}-7-[3-(naphthalen-1-yloxy)propyl]-1,10,13,15-tetrahydropyrazolo[4',3':9,10][1,6]oxazacycloundecino[8,7,6-hi]indole-8-carboxylic acid (Enantiomer 1)

For the preparation of the racemic title compound see Example 118. After separation of enantiomers by preparative preparative chiral HPLC (method see Example 118), the obtained product was further purified by flash chromatography (dichloromethane/methanol gradient, 0%→100% methanol) to give the title compound (40 mg).

Analytical Chiral HPLC (method see Example 118): R$_t$=4.27 min.

Specific optical rotation (Method O1): +22.9° (c=1.0 g/100 ml in DMSO)

$^1$H-NMR (400 MHz, DMSO-d6) δ[ppm]: 0.833 (0.56), 0.851 (1.03), 1.172 (0.56), 1.191 (0.44), 1.232 (7.33), 2.159 (0.74), 2.178 (1.59), 2.196 (1.91), 2.275 (0.44), 2.327 (1.49), 2.331 (1.15), 2.522 (5.00), 2.539 (1.96), 2.669 (1.49), 2.839 (4.51), 3.166 (0.66), 3.253 (0.47), 3.273 (0.83), 3.287 (0.93), 3.306 (1.27), 3.324 (0.78), 3.348 (0.88), 3.365 (1.35), 3.383 (1.18), 3.398 (1.05), 3.417 (0.93), 3.483 (2.65), 3.544 (2.38), 3.589 (5.24), 3.601 (6.20), 3.611 (4.58), 3.789 (1.05), 3.801 (1.18), 3.821 (1.03), 3.834 (0.86), 3.906 (0.51), 3.921 (1.20), 3.942 (16.00), 4.059 (0.42), 4.075 (0.88), 4.083 (0.98), 4.099 (1.47), 4.116 (1.20), 4.134 (1.52), 4.149 (0.96), 4.157 (0.86), 4.174 (0.42), 4.224 (2.21), 4.258 (2.30), 4.357 (2.01), 4.386 (2.38), 4.610 (2.52), 4.638 (2.21), 4.680 (0.66), 4.708 (1.03), 4.722 (1.13), 4.733 (2.55), 4.747 (1.03), 4.767 (2.18), 5.035 (0.76), 5.059 (2.89), 5.091 (1.25), 5.166 (0.64), 5.177 (0.64), 5.194 (0.88), 5.759 (1.42), 6.454 (3.23), 6.476 (3.92), 6.546 (0.91), 6.645 (2.13), 6.668 (1.81), 6.791 (3.60), 6.809 (4.70), 6.971 (1.86), 6.991 (2.65), 7.009 (1.64), 7.341 (1.47), 7.362 (2.99), 7.381 (2.13), 7.436 (3.26), 7.456 (2.06), 7.485 (0.78), 7.498 (1.84), 7.502 (1.86), 7.511 (2.03), 7.517 (3.65), 7.523 (2.08), 7.530 (1.94), 7.534 (1.98), 7.547 (0.76), 7.702 (2.35), 7.721 (2.13), 7.853 (2.08), 7.871 (1.89), 7.876 (1.72), 8.211 (1.67), 8.217 (1.74), 8.235 (1.69).

Example 120

(−)-(E/Z)-1-methyl-3-{[4-(morpholin-4-yl)phenoxy]methyl}-7-[3-(naphthalen-1-yloxy)propyl]-1,10,13,15-tetrahydropyrazolo[4',3':9,10][1,6]oxazacycloundecino[8,7,6-hi]indole-8-carboxylic acid (Enantiomer 2)

For the preparation of the racemic title compound see Example 118. After separation of enantiomers by preparative chiral HPLC (method see Example 118), the obtained product was further purified by flash chromatography (dichloromethane/methanol gradient, 0%→75% methanol) to give the title compound (41 mg).

Analytical Chiral HPLC (method see Example 118): R$_t$=4.97 min.

Specific optical rotation (Method O1): −34.8° (c=1.0 g/100 ml in DMSO)

$^1$H-NMR (400 MHz, DMSO-d6) δ[ppm]: 0.848 (0.50), 1.228 (3.07), 2.193 (1.99), 2.323 (1.64), 2.536 (5.11), 2.665 (1.70), 2.844 (4.93), 3.250 (0.48), 3.269 (0.82), 3.283 (0.98), 3.301 (1.35), 3.320 (0.77), 3.343 (0.82), 3.360 (1.30), 3.378 (1.09), 3.393 (0.85), 3.413 (0.56), 3.478 (1.17), 3.509 (2.04), 3.540 (1.59), 3.589 (5.59), 3.601 (7.13), 3.611 (5.56), 3.786 (1.72), 3.797 (1.77), 3.818 (1.54), 3.829 (1.32), 3.938 (16.00), 4.080 (1.11), 4.096 (1.64), 4.112 (1.35), 4.130 (1.67), 4.145 (1.09), 4.168 (0.53), 4.219 (2.28), 4.253 (2.41), 4.355 (2.12), 4.384 (2.49), 4.608 (2.62), 4.636 (2.23), 4.676 (0.72), 4.704 (1.06), 4.717 (1.30), 4.729 (2.68), 4.742 (1.19), 4.764 (2.28), 5.030 (0.85), 5.055 (3.21), 5.086 (1.48), 5.162 (0.72), 5.173 (0.72), 5.190 (1.01), 6.454 (3.31), 6.476 (4.00), 6.652 (2.17), 6.673 (1.85), 6.787 (3.81), 6.806 (4.85), 6.968 (1.77), 6.987 (2.75), 7.006 (1.54), 7.338 (1.38), 7.358 (2.91), 7.377 (2.01), 7.432 (3.28), 7.453 (2.07), 7.481 (0.79), 7.498 (1.91), 7.507 (2.07), 7.512 (3.55), 7.526 (2.01), 7.530 (1.99), 7.543 (0.79), 7.697 (2.52), 7.717 (2.33), 7.850 (2.12), 7.868 (1.85), 8.212 (1.88), 8.230 (1.80).

Example 121

(rac)-1-methyl-3-{[4-(morpholin-4-yl)phenoxy]methyl}-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid

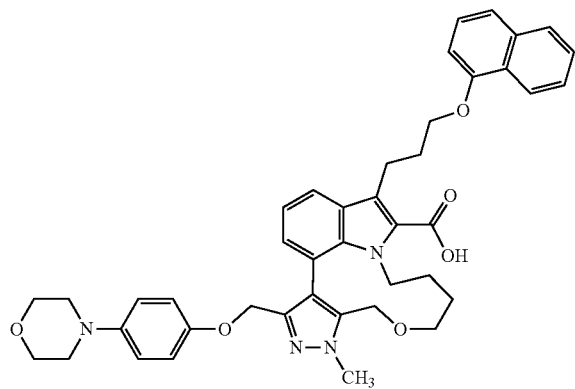

To a solution of (rac)-ethyl 1-methyl-3-{[4-(morpholin-4-yl)phenoxy]methyl}-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (see Intermediate 215, 150 mg, 206 μmol) in THF (3.5 ml) and ethanol (3.5 ml) was added a solution of lithium hydroxide in water (3.5 ml, 1.0 M, 3.5 mmol). The reaction mixture was stirred for 7 days at 45° C. For work-up, the reaction mixture was concentrated under reduced pressure and the residue was purified by flash chromatography (dichloromethane/methanol gradient, 0%→10% methanol) to give the title compound (142 mg) as a racemic mixture.

LC-MS (Method 1): Rt=1.50 min; MS (ESIpos): m/z=701 [M+H]$^+$

The title compound (142 mg) was separated into enantiomers by preparative chiral HPLC, followed by flash chromatography, to give enantiomer 1 (17 mg, see Example 122) and enantiomer 2 (15 mg, see Example 123).

Preparative chiral HPLC method: Instrument: Labomatic HD5000, Labocord-5000; Gilson GX-241, Labcol Vario 4000, column: Chiralpak IA 5μ 250×30 mm; eluent A: hexan eluent B: 2-propanol; gradient: 20-50% B in 15 min+0.1 Vol-% trifluoroacetic acid; flow 40.0 ml/min; UV 254 nm Analytical chiral HPLC method: Instrument: Agilent HPLC 1260; column: Chiralpak IA 3μ 100×4.6 mm; eluent A: hexane+0.1 Vol-% trifluoroacetic acid; eluent B: 2-propanol; gradient: 20-50% B in 7 min; flow 1.4 ml/min; temperature: 25° C.; DAD 254 nm

Example 122

1-methyl-3-{[4-(morpholin-4-yl)phenoxy]methyl}-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (Enantiomer 1)

For the preparation of the racemic title compound see Example 121. After separation of enantiomers by preparative chiral HPLC (method see Example 121), the obtained product was further purified by flash chromatography (dichloromethane/methanol gradient, 3%→7.5% methanol) to give the title compound (17 mg).

Analytical Chiral HPLC (method see Example 121): $R_t$=3.80 min.

$^1$H-NMR (400 MHz, DMSO-d6) δ[ppm]: 0.852 (1.00), 1.051 (1.08), 1.066 (0.95), 1.154 (0.44), 1.172 (0.77), 1.190 (0.51), 1.232 (6.78), 1.361 (0.44), 1.988 (1.59), 2.160 (0.62), 2.167 (1.08), 2.178 (1.23), 2.185 (1.64), 2.202 (1.13), 2.318 (0.46), 2.323 (1.05), 2.327 (1.54), 2.332 (1.08), 2.336 (0.44), 2.518 (4.88), 2.523 (3.67), 2.539 (0.90), 2.660 (0.49), 2.665 (1.10), 2.669 (1.57), 2.673 (1.10), 2.678 (0.49), 2.788 (3.49), 2.800 (4.37), 2.812 (4.52), 2.829 (0.82), 2.841 (0.67), 3.231 (0.54), 3.246 (0.57), 3.264 (0.87), 3.283 (0.46), 3.359 (1.08), 3.376 (0.67), 3.393 (0.67), 3.460 (0.69), 3.471 (0.54), 3.489 (0.67), 3.565 (3.62), 3.578 (4.16), 3.589 (3.78), 3.601 (0.46), 3.920 (16.00), 3.931 (0.80), 3.940 (1.34), 4.035 (0.41), 4.053 (0.44), 4.080 (0.74), 4.089 (0.87), 4.096 (0.92), 4.112 (1.87), 4.129 (1.67), 4.145 (0.72), 4.153 (0.51), 4.268 (1.54), 4.302 (1.70), 4.434 (1.95), 4.462 (2.34), 4.518 (0.51), 4.554 (0.44), 4.672 (2.08), 4.680 (2.47), 4.708 (2.93), 5.759 (2.62), 6.488 (3.26), 6.494 (1.10), 6.511 (4.37), 6.519 (0.46), 6.546 (1.93), 6.615 (0.51), 6.623 (5.11), 6.629 (1.36), 6.641 (1.23), 6.646 (3.62), 6.793 (1.87), 6.813 (2.31), 6.834 (1.52), 6.956 (1.49), 6.976 (1.85), 6.994 (1.23), 7.338 (1.46), 7.359 (2.65), 7.378 (2.03), 7.434 (2.62), 7.455 (1.64), 7.484 (0.46), 7.489 (0.62), 7.501 (1.70), 7.506 (1.44), 7.511 (1.80), 7.518 (3.42), 7.525 (1.82), 7.530 (1.59), 7.535 (1.70), 7.547 (0.67), 7.551 (0.41), 7.700 (1.44), 7.718 (1.31), 7.852 (1.57), 7.860 (0.85), 7.870 (1.54), 7.875 (1.31), 8.221 (1.31), 8.227 (1.28), 8.238 (0.69), 8.246 (1.23).

Example 123

1-methyl-3-{[4-(morpholin-4-yl)phenoxy]methyl}-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (Enantiomer 2)

For the preparation of the racemic title compound see Example 121 After separation of enantiomers by preparative chiral HPLC (method see Example 121), the obtained product was further purified by flash chromatography (dichloromethane/methanol gradient, 3%→7.5% methanol) to give the title compound (15 mg).

Analytical Chiral HPLC (method see Example 121): $R_t$=5.22 min.

$^1$H-NMR (400 MHz, DMSO-d6) δ[ppm]: 0.835 (0.43), 0.852 (1.04), 1.050 (1.11), 1.173 (0.50), 1.190 (0.39), 1.233 (6.71), 1.365 (0.43), 1.988 (0.96), 2.167 (1.07), 2.178 (1.25), 2.185 (1.64), 2.202 (1.11), 2.318 (0.64), 2.323 (1.50), 2.327 (2.14), 2.332 (1.54), 2.336 (0.64), 2.518 (7.21), 2.523 (5.46), 2.539 (0.79), 2.660 (0.68), 2.665 (1.54), 2.669 (2.18), 2.673 (1.54), 2.678 (0.64), 2.786 (3.43), 2.798 (4.32), 2.810 (4.29), 2.841 (0.64), 3.226 (0.50), 3.242 (0.54), 3.259 (0.79), 3.279 (0.46), 3.358 (1.32), 3.375 (0.79), 3.391 (0.75), 3.460 (0.71), 3.472 (0.57), 3.489 (0.64), 3.563 (3.57), 3.578 (4.00), 3.588 (3.50), 3.919 (16.00), 4.074 (0.71), 4.089 (0.75), 4.097 (0.93), 4.113 (1.86), 4.130 (1.68), 4.145 (0.71), 4.153 (0.50), 4.267 (1.57), 4.301 (1.71), 4.434 (1.96), 4.463 (2.32), 4.526 (0.46), 4.562 (0.43), 4.672 (2.18), 4.678 (2.54), 4.706 (3.46), 5.759 (5.46), 6.492 (2.86), 6.514 (3.86), 6.546 (1.18), 6.615 (0.46), 6.623 (4.96), 6.629 (1.32), 6.641 (1.14), 6.646 (3.54), 6.794 (1.82), 6.812 (2.68), 6.827 (1.29), 6.952 (1.21), 6.971 (1.64), 6.989 (1.00), 7.338 (1.43), 7.358 (2.54), 7.377 (1.89), 7.433 (2.54), 7.454 (1.61), 7.483 (0.39), 7.488 (0.61), 7.501 (1.61), 7.505 (1.46), 7.510 (1.79), 7.518 (3.50), 7.525 (1.82), 7.530 (1.57), 7.534 (1.75), 7.547 (0.68), 7.551 (0.43), 7.693 (1.21), 7.712 (1.14), 7.851 (1.54), 7.859 (0.82), 7.869 (1.46), 7.875 (1.29), 8.221 (1.32), 8.226 (1.25), 8.238 (0.71), 8.245 (1.25).

Example 124

(rac)-7,9-dimethyl-11-[2-(morpholin-4-yl)ethyl]-1-[3-(naphthalen-1-yloxy)propyl]-4,5,6,7,8,9-hexahydropyrazolo[3',4':7,8][1,5]diazecino[9,10,1-hi]indole-2-carboxylic acid

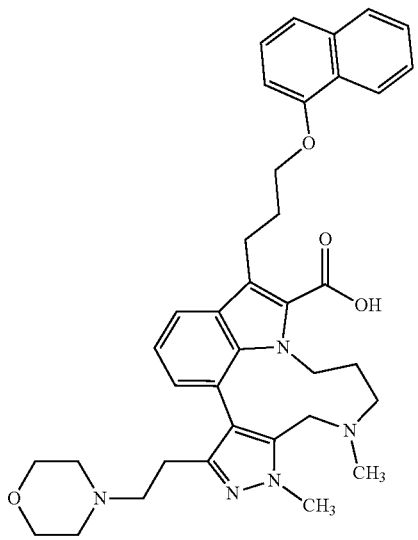 [SMILES: CN1CCCn2c(C(=O)O)c(CCCOc3cccc4ccccc34)c3cccc(c32)-c2c(CCN3CCOCC3)nn(C)c2C1]

To a solution of (rac)-ethyl 7,9-dimethyl-11-[2-(morpholin-4-yl)ethyl]-1-[3-(naphthalen-1-yloxy)propyl]-4,5,6,7,8,9-hexahydropyrazolo[3',4':7,8][1,5]diazecino[9,10,1-hi]indole-2-carboxylate (see Intermediate 226, 91.5 mg, 141 µmol) in THF (6.9 ml, 84 mmol) and ethanol (3.3 ml, 82 mmol) was added a solution of lithium hydroxide in water (2.8 ml, 1.0 M, 2.8 mmol). The reaction mixture was stirred for 24 hours at 50° C. For work-up, the reaction mixture was concentrated under reduced pressure and the residue was purified by flash chromatography (dichloromethane/methanol gradient, 10%→50% methanol) to give the title compound (67 mg) as a racemic mixture.

LC-MS (Method 2): Rt=0.84 min; MS (ESIpos): m/z=622 [M+H]$^+$

The title compound (67 mg) was separated into enantiomers by preparative chiral HPLC, followed by flash chromatography, to give enantiomer 1 (16 mg, see Example 125) and enantiomer 2 (11 mg, see Example 126).

Preparative chiral HPLC method: Instrument: Sepiatec: Prep SFC100; column: Chiralpak ID 5 µm 250×30 mm; eluent A: CO$_2$, eluent B: 2-propanol+0.4 Vol-% diethylamine (99%); isocratic: 30% B; flow 100.0 ml/min temperature: 40° C.; BPR: 150 bar; MWD @ 254 nm Analytical chiral HPLC method: Instrument: Agilent: 1260, Aurora SFC-Module; column: Chiralpak ID 5 µm 100×4.6 mm; eluent A: CO$_2$, eluent B: 2-propanol+0.2 Vol-% diethylamine (99%); isocratic: 30% B; flow 4.0 ml/min; temperature: 37.5° C.; BPR: 100 bar; MWD @ 254 nm Example 125

7,9-dimethyl-11-[2-(morpholin-4-yl)ethyl]-1-[3-(naphthalen-1-yloxy)propyl]-4,5,6,7,8,9-hexahydropyrazolo[3',4':7,8][1,5]diazecino[9,10,1-hi]indole-2-carboxylic acid (Enantiomer 1)

For the preparation of the racemic title compound see Example 124. After separation of enantiomers by preparative chiral HPLC (method see Example 124), the obtained product was further purified by flash chromatography (dichloromethane/methanol gradient, 0%→50% methanol) to give the title compound (16 mg).

LC-MS (Method 2): Rt=0.87 min; MS (ESIpos): m/z=622 [M+H]$^+$

Analytical Chiral HPLC (method see Example 124): R$_t$=3-04 min.

$^1$H-NMR (400 MHz, DMSO-d6) δ[ppm]: 0.832 (0.45), 0.851 (0.74), 1.231 (3.83), 1.477 (0.89), 1.601 (0.80), 1.757 (0.76), 1.814 (0.82), 1.838 (0.87), 1.849 (1.00), 1.873 (0.82), 1.907 (0.67), 1.983 (2.23), 2.060 (1.94), 2.084 (1.54), 2.165 (1.96), 2.182 (3.08), 2.212 (16.00), 2.270 (1.65), 2.288 (4.50), 2.305 (4.06), 2.326 (2.30), 2.406 (2.90), 2.425 (3.74), 2.442 (1.94), 2.539 (2.70), 2.669 (1.45), 2.933 (2.27), 2.969 (2.43), 3.219 (1.98), 3.252 (3.77), 3.288 (3.65), 3.295 (3.79), 3.303 (4.26), 3.322 (4.66), 3.340 (4.32), 3.373 (2.01), 3.573 (2.54), 3.609 (2.50), 3.725 (0.58), 3.751 (0.98), 4.140 (2.27), 4.156 (4.55), 4.171 (2.32), 4.524 (1.11), 4.560 (1.05), 5.759 (2.87), 6.839 (2.92), 6.856 (4.28), 6.870 (2.74), 6.963 (1.87), 6.982 (2.76), 7.000 (1.52), 7.346 (1.60), 7.366 (3.41), 7.386 (2.43), 7.433 (3.86), 7.454 (2.32), 7.486 (0.76), 7.499 (2.09), 7.507 (2.70), 7.516 (4.30), 7.524 (2.94), 7.531 (2.45), 7.544 (0.91), 7.662 (2.27), 7.681 (2.16), 7.849 (2.32), 7.856 (1.34), 7.866 (1.96), 7.871 (1.98), 8.223 (1.96), 8.229 (1.96), 8.246 (2.05).

Example 126

7,9-dimethyl-11-[2-(morpholin-4-yl)ethyl]-1-[3-(naphthalen-1-yloxy)propyl]-4,5,6,7,8,9-hexahydropyrazolo[3',4':7,8][1,5]diazecino[9,10,1-hi]indole-2-carboxylic acid (Enantiomer 2)

For the preparation of the racemic title compound see Example 124. After separation of enantiomers by preparative chiral HPLC (method see Example 124), the obtained product was further purified by flash chromatography (dichloromethane/methanol gradient, 0%→50% methanol) to give the title compound (11 mg).

LC-MS (Method 2): Rt=0.88 min; MS (ESIpos): m/z=622 [M+H]$^+$

Analytical Chiral HPLC (method see Example 124): R$_t$=5.45 min.

$^1$H-NMR (400 MHz, DMSO-d6) δ[ppm]: 1.228 (3.07), 1.486 (1.98), 1.599 (1.86), 1.755 (1.53), 1.846 (2.05), 1.989 (4.88), 2.063 (4.56), 2.202 (16.00), 2.288 (7.45), 2.427 (7.38), 2.665 (1.44), 2.933 (2.38), 2.969 (2.67), 3.253 (7.63), 3.285 (7.58), 3.571 (3.16), 3.604 (3.84), 4.153 (5.62), 4.524 (1.88), 4.554 (1.87), 6.856 (4.49), 6.985 (2.94), 7.362 (2.92), 7.430 (3.51), 7.515 (5.37), 7.688 (2.95), 7.861 (2.88), 8.240 (2.78).

Example 127

(rac)-1,14-dimethyl-7-[3-(naphthalen-1-yloxy)propyl]-10,11,12,13,14,15-hexahydro-1H-pyrazolo[3',4':8,9][1,6]diazacycloundecino[10,11,1-hi]indole-8-carboxylic acid

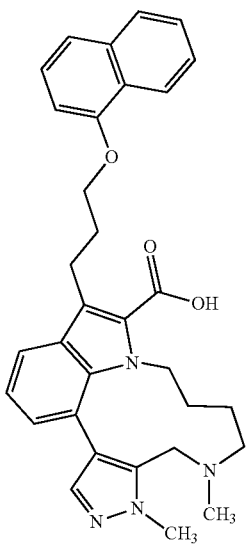 [SMILES: CN1CCCCn2c(C(=O)O)c(CCCOc3cccc4ccccc34)c3cccc(c32)-c2cnn(C)c2C1]

To a solution of (rac)-ethyl 1,14-dimethyl-7-[3-(naphthalen-1-yloxy)propyl]-10,11,12,13,14,15-hexahydro-1H-pyrazolo[3',4':8,9][1,6]diazacycloundecino[10,11,1-hi]indole-8-carboxylate (see Intermediate 240, 280 mg, 508 µmol) in THF (25 ml, 310 mmol) and ethanol (12 ml, 290 mmol) was added a solution of lithium hydroxide in water (10 ml, 1.0 M, 10 mmol). The reaction mixture was stirred for 24 hours at 50° C. For work-up, the reaction mixture was concentrated under reduced pressure and the residue was purified by flash chromatography (dichloromethane/methanol gradient, 1%→10% methanol) to give the title compound (230 mg) as a racemic mixture.

LC-MS (Method 2): $R_t$=0.91 min; MS (ESIpos): m/z=523 [M+H]$^+$ $^1$H-NMR (400 MHz, DMSO-d6) δ[ppm]: 1.231 (0.64), 1.875 (0.41), 1.907 (16.00), 2.163 (5.14), 2.185 (0.81), 2.203 (0.54), 2.436 (0.42), 2.518 (1.12), 2.523 (0.77), 3.262 (0.48), 3.299 (1.04), 3.397 (0.45), 3.684 (0.79), 3.716 (0.69), 3.913 (7.37), 4.174 (0.60), 4.189 (1.16), 4.204 (0.56), 6.830 (0.83), 6.833 (0.80), 6.848 (0.99), 6.850 (0.89), 6.884 (0.87), 6.902 (0.94), 6.992 (0.83), 7.012 (0.97), 7.030 (0.64), 7.366 (0.63), 7.386 (1.21), 7.403 (3.72), 7.445 (1.27), 7.466 (0.70), 7.511 (0.83), 7.516 (1.30), 7.526 (1.55), 7.535 (1.37), 7.540 (0.81), 7.713 (0.86), 7.716 (0.83), 7.733 (0.81), 7.856 (0.75), 7.873 (0.50), 7.879 (0.60), 8.231 (0.65), 8.239 (0.50), 8.255 (0.56).

Example 128

(rac)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid

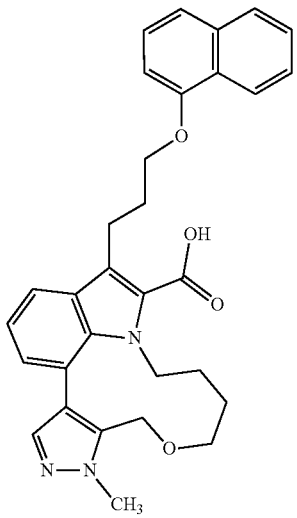 [SMILES: Cn1ncc2c1COCCCCn1c(C(=O)O)c(CCCOc3cccc4ccccc34)c3cccc-2c31]

To a solution of (rac)-ethyl 1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (see Intermediate 243, 120 mg, 223 µmol) in THF (11 ml, 130 mmol) and ethanol (5.2 ml, 130 mmol) was added a solution of lithium hydroxide in water (4.5 ml, 1.0 M, 4.5 mmol). The reaction mixture was stirred for 24 hours at 50° C. For work-up, the reaction mixture was concentrated under reduced pressure and the residue was purified by flash chromatography (dichloromethane/methanol gradient, 0%→100% methanol) to give the title compound (82 mg) as a racemic mixture.

LC-MS (Method 2): $R_t$=0.86 min; MS (ESIpos): m/z=510 [M+H]$^+$ $^1$H-NMR (400 MHz, DMSO-d6) δ[ppm]: 0.851 (0.87), 1.045 (0.71), 1.062 (0.60), 1.167 (0.69), 1.232 (5.21), 1.249 (1.13), 1.268 (1.26), 1.285 (0.84), 1.907 (3.22), 2.104 (0.62), 2.120 (0.89), 2.159 (0.47), 2.178 (1.11), 2.193 (1.46), 2.204 (1.62), 2.221 (1.62), 2.238 (1.02), 2.318 (0.42), 2.323 (0.93), 2.327 (1.33), 2.332 (0.93), 2.337 (0.40), 2.518 (4.79), 2.523 (3.37), 2.660 (0.44), 2.665 (1.04), 2.669 (1.44), 2.673 (1.00), 2.679 (0.58), 2.813 (0.47), 2.843 (0.51), 3.242 (0.49), 3.263 (0.58), 3.276 (0.91), 3.283 (0.89), 3.297 (1.04), 3.375 (0.73), 3.394 (1.18), 3.408 (1.04), 3.427 (1.13), 3.440 (0.78), 3.454 (0.58), 3.474 (0.73), 3.506 (1.09), 3.536 (0.71), 3.770 (0.69), 3.781 (0.67), 3.802 (0.55), 3.814 (0.51), 3.919 (12.27), 3.939 (16.00), 3.968 (1.15), 4.040 (0.49), 4.170 (1.09), 4.185 (2.33), 4.199 (1.80), 4.211 (2.40), 4.226 (1.13), 4.252 (1.66), 4.287 (1.80), 4.297 (1.26), 4.331 (1.33), 4.467 (0.53), 4.502 (0.47), 4.628 (0.51), 4.661 (1.55), 4.694 (1.89), 4.729 (1.89), 4.763 (1.60), 4.958 (0.44), 4.985 (0.87), 5.012 (0.51), 5.064 (0.73), 5.102 (0.62), 5.174 (0.53), 5.184 (0.53), 5.759 (8.90), 6.829 (1.53), 6.831 (1.64), 6.846 (1.82), 6.849 (1.78), 6.867 (1.15), 6.871 (1.29), 6.881 (1.49), 6.885 (1.82), 6.888 (1.62), 6.898 (2.84), 6.917 (1.75), 7.007 (1.40), 7.025 (1.31), 7.027 (1.53), 7.038 (1.82), 7.045 (1.22), 7.056 (1.89), 7.058 (2.06), 7.076 (1.55), 7.365 (1.00), 7.373 (1.38), 7.381 (7.48), 7.386 (2.20), 7.393 (2.73), 7.405 (1.60), 7.412 (2.04), 7.430 (4.99), 7.445 (3.75), 7.466 (1.98), 7.478 (0.55), 7.482 (0.67), 7.491 (0.60), 7.495 (1.49), 7.499 (1.35), 7.504 (1.40), 7.510 (2.17), 7.514 (3.20), 7.521 (3.11), 7.530 (2.11), 7.533 (2.55), 7.537 (1.55), 7.547 (0.78), 7.551 (0.89), 7.739 (1.38), 7.742 (1.62), 7.745 (1.89), 7.747 (1.71), 7.759 (1.29), 7.762 (1.44), 7.765 (1.78), 7.768 (1.58), 7.855 (2.37), 7.873 (2.51), 7.877 (2.11), 8.189 (1.24), 8.193 (1.26), 8.212 (1.86), 8.227 (0.53), 8.234 (0.87).

Example 129

(rac)-7,9-dimethyl-1-[3-(naphthalen-1-yloxy)propyl]-11-{[(2,2,2-trifluoroethyl)amino]methyl}-4,5,6,7,8,9-hexahydropyrazolo[3',4':7,8][1,5]diazecino[9,10,1-hi]indole-2-carboxylic acid (Racemate)

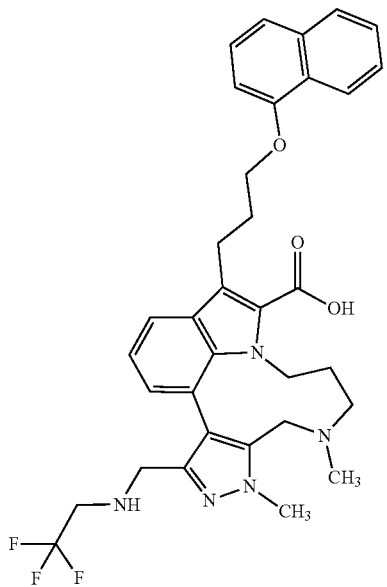 [SMILES: CN1CCCn2c(C(=O)O)c(CCCOc3cccc4ccccc34)c3cccc(c32)-c2c(CNCC(F)(F)F)nn(C)c2C1]

To a solution of (rac)-ethyl 7,9-dimethyl-1-[3-(naphthalen-1-yloxy)propyl]-11-{[(2,2,2-trifluoroethyl)amino]methyl}-4,5,6,7,8,9-hexahydropyrazolo[3',4':7,8][1,5]diazecino[9,10,1-hi]indole-2-carboxylate (see Intermediate 253, 160 mg, 247 μmol) in THF (12 ml) and ethanol (5.8 ml) was added a solution of lithium hydroxide in water (4.9 ml, 1.0 M, 4.9 mmol). The reaction mixture was stirred for 24 hours at 50° C. For work-up, the reaction mixture was concentrated under reduced pressure and the residue was purified by flash chromatography (dichloromethane/methanol gradient, 1%→10% methanol) to give the title compound (104 mg) as a racemic mixture.

LC-MS (Method 2): Rt=1.33 min; MS (ESIpos): m/z=620 [M+H]$^+$

The title compound (104 mg) was separated into enantiomers by preparative chiral HPLC to give enantiomer 1 (35 mg, see Example 130) and enantiomer 2 (31 mg, see Example 131).

Preparative chiral HPLC method: Instrument: Sepiatec: Prep SFC100; column: Chiralpak ID 5 μm 250×30 mm; eluent A: $CO_2$, eluent B: 2-propanol+0.4 Vol-% diethylamine (99%); isocratic: 27% B; flow 100.0 ml/min temperature: 40° C.; BPR: 150 bar; MWD @ 254 nm Analytical chiral HPLC method: Instrument: Agilent: 1260, Aurora SFC-Module; column: Chiralpak ID 5 μm 100×4.6 mm; eluent A: $CO_2$, eluent B: 2-propanol+0.2 Vol-% diethylamine (99%); isocratic: 27% B; flow 4.0 ml/min; temperature: 37.5° C.; BPR: 100 bar; MWD @ 254 nm Example 130

7,9-dimethyl-1-[3-(naphthalen-1-yloxy)propyl]-11-{[(2,2,2-trifluoroethyl)amino]methyl}-4,5,6,7,8,9-hexahydropyrazolo[3',4':7,8][1,5]diazecino[9,10,1-hi]indole-2-carboxylic acid-N-ethylethanamine salt (Enantiomer 1)

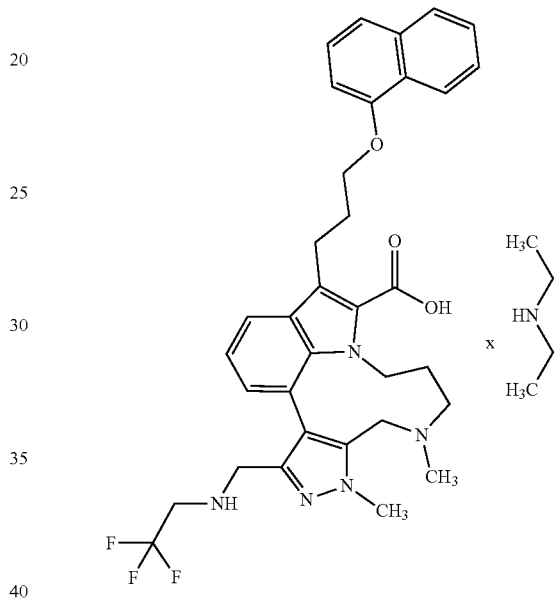

For the preparation of the racemic title compound see Example 129. Separation of enantiomers by preparative chiral HPLC (method see Example 129), gave the title compound (35 mg).

Analytical Chiral HPLC (method see Example 129): R$_t$=2.78 min.

LC-MS (Agilent_pos_100): Rt=1.07 min; MS (ESIpos): m/z=620 [M+H]$^+$ $^1$H-NMR (400 MHz, DMSO-d6) δ[ppm]: 0.852 (0.47), 0.968 (0.61), 1.109 (0.47), 1.132 (2.10), 1.149 (4.57), 1.168 (2.19), 1.209 (0.51), 1.232 (1.87), 1.471 (0.51), 1.620 (0.42), 1.826 (0.47), 1.849 (0.51), 1.862 (0.56), 1.884 (0.51), 2.169 (1.31), 2.187 (2.05), 2.210 (10.59), 2.300 (0.61), 2.331 (2.52), 2.336 (1.40), 2.349 (0.56), 2.518 (10.50), 2.523 (7.28), 2.673 (2.05), 2.866 (0.51), 2.884 (1.59), 2.903 (1.49), 2.921 (0.51), 2.945 (1.54), 2.981 (1.68), 3.072 (0.51), 3.098 (1.49), 3.121 (1.77), 3.146 (1.45), 3.157 (0.47), 3.171 (0.47), 3.182 (0.47), 3.232 (0.61), 3.249 (0.84), 3.269 (0.56), 3.423 (0.75), 3.457 (2.99), 3.471 (2.94), 3.505 (0.70), 3.597 (1.77), 3.633 (1.63), 3.695 (0.47), 3.854 (16.00), 4.156 (1.54), 4.172 (3.13), 4.187 (1.49), 4.508 (0.61), 4.543 (0.56), 6.856 (1.96), 6.874 (2.19), 6.891 (0.93), 6.908 (1.26), 6.961 (1.17), 6.980 (1.63), 6.998 (0.84), 7.353 (1.35), 7.374 (2.71), 7.393 (2.10), 7.437 (2.94), 7.457 (1.68), 7.483 (0.42), 7.488 (0.65), 7.500 (1.68), 7.505 (1.63), 7.509 (2.01), 7.517 (3.64), 7.524 (2.01), 7.528 (1.82), 7.533 (1.87), 7.545 (0.70), 7.660 (1.07), 7.679 (0.98), 7.851 (1.68), 7.859 (0.89), 7.868 (1.49), 7.874 (1.45), 8.222 (1.45), 8.227 (1.35), 8.246 (1.35).

Example 131

7,9-dimethyl-1-[3-(naphthalen-1-yloxy)propyl]-11-{[(2,2,2-trifluoroethyl)amino]methyl}-4,5,6,7,8,9-hexahydropyrazolo[3',4':7,8][1,5]diazecino[9,10,1-hi]indole-2-carboxylic acid-N-ethylethanamine salt (Enantiomer 2)

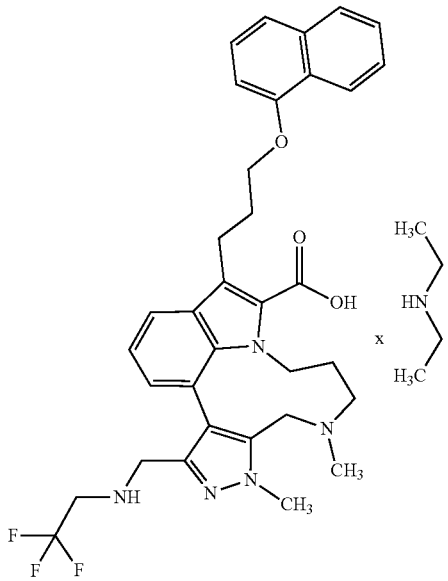

For the preparation of the racemic title compound see Example 129. Separation of enantiomers by preparative chiral HPLC (method see Example 129), gave the title compound (31 mg).

Analytical Chiral HPLC (method see Example 129): R$_t$=3.73 min.

LC-MS (Agilent_pos_100): Rt=1.07 min; MS (ESIpos): m/z=620 [M+H]$^+$ $^1$H-NMR (400 MHz, DMSO-d6) δ[ppm]: 0.968 (0.79), 1.109 (0.69), 1.134 (2.04), 1.144 (0.69), 1.152 (4.44), 1.170 (2.10), 1.209 (0.59), 1.232 (1.31), 1.472 (0.56), 1.621 (0.46), 1.826 (0.53), 1.848 (0.53), 1.861 (0.59), 1.882 (0.53), 2.169 (1.35), 2.187 (2.04), 2.209 (11.10), 2.299 (0.62), 2.318 (1.18), 2.323 (1.74), 2.327 (2.37), 2.331 (1.91), 2.349 (0.53), 2.518 (7.52), 2.523 (5.09), 2.665 (1.48), 2.669 (2.00), 2.673 (1.45), 2.867 (0.53), 2.884 (1.54), 2.903 (1.54), 2.921 (0.56), 2.945 (1.54), 2.981 (1.68), 3.061 (0.43), 3.072 (0.56), 3.098 (1.58), 3.121 (1.84), 3.146 (1.51), 3.157 (0.53), 3.171 (0.49), 3.183 (0.46), 3.217 (0.59), 3.231 (0.66), 3.250 (0.92), 3.269 (0.62), 3.423 (0.79), 3.457 (3.09), 3.471 (3.06), 3.506 (0.72), 3.596 (1.77), 3.632 (1.64), 3.696 (0.49), 3.854 (16.00), 4.156 (1.51), 4.172 (3.09), 4.187 (1.48), 4.509 (0.69), 4.545 (0.62), 6.855 (1.94), 6.874 (2.14), 6.892 (1.05), 6.909 (1.45), 6.961 (1.38), 6.981 (1.77), 6.999 (0.92), 7.353 (1.38), 7.373 (2.66), 7.392 (2.04), 7.436 (2.89), 7.457 (1.68), 7.483 (0.43), 7.487 (0.62), 7.500 (1.64), 7.504 (1.61), 7.509 (1.97), 7.516 (3.58), 7.524 (1.97), 7.528 (1.77), 7.533 (1.87), 7.545 (0.69), 7.550 (0.43), 7.660 (1.25), 7.679 (1.15), 7.851 (1.68), 7.859 (0.92), 7.868 (1.48), 7.874 (1.45), 8.222 (1.41), 8.227 (1.35), 8.246 (1.35).

Example 132

(rac)-(E/Z)-1-methyl-3-(morpholin-4-ylmethyl)-7-[3-(naphthalen-1-yloxy)propyl]-1,10,13,15-tetrahydropyrazolo[4',3':9,10][1,6]oxazacycloundecino[8,7,6-hi]indole-8-carboxylic acid

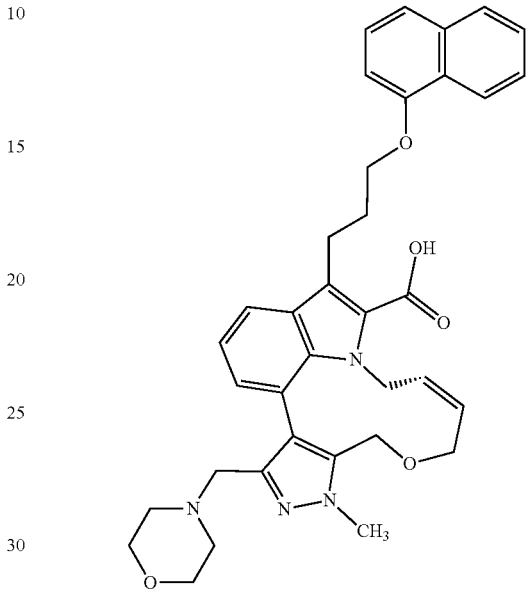

To a solution of (rac)-ethyl (E/Z)-1-methyl-3-(morpholin-4-ylmethyl)-7-[3-(naphthalen-1-yloxy)propyl]-1,10,13,15-tetrahydropyrazolo[4',3':9,10][1,6]oxazacycloundecino[8,7,6-hi]indole-8-carboxylate (see Intermediate 264, 79.0 mg, 124 μmol) in THF (5.0 ml) and ethanol (2.5 ml) was added a solution of lithium hydroxide in water (2.5 ml, 1.0 M, 2.5 mmol). The reaction mixture was stirred for 2 weeks at room temperature. For work-up, the reaction mixture was concentrated under reduced pressure and the residue was purified by flash chromatography (dichloromethane/methanol isocratic 9:1) to give after drying under vacuo the title compound (54 mg) as a racemic mixture.

LC-MS (Method 2): Rt=0.84 min; MS (ESIpos): m/z=607 [M+H]$^+$ $^1$H-NMR (400 MHz, DMSO-d6) δ[ppm]: 1.026 (6.94), 1.041 (7.04), 1.233 (1.02), 1.846 (1.22), 1.862 (1.09), 1.907 (4.42), 2.085 (1.25), 2.098 (1.12), 2.227 (1.28), 2.323 (1.38), 2.327 (1.92), 2.332 (1.34), 2.518 (8.19), 2.523 (5.54), 2.540 (1.06), 2.660 (0.67), 2.665 (1.47), 2.669 (1.98), 2.673 (1.41), 2.896 (0.61), 2.929 (2.94), 2.940 (2.82), 2.973 (0.58), 3.173 (1.09), 3.211 (1.60), 3.219 (1.60), 3.226 (1.66), 3.247 (0.86), 3.301 (1.54), 3.379 (0.70), 3.396 (0.93), 3.415 (0.74), 3.429 (0.58), 3.495 (0.70), 3.526 (1.25), 3.557 (0.86), 3.584 (0.58), 3.599 (0.90), 3.615 (0.54), 3.770 (0.77), 3.781 (0.86), 3.803 (0.77), 3.815 (0.67), 3.866 (1.47), 3.893 (16.00), 4.149 (1.38), 4.164 (2.94), 4.180 (1.50), 4.235 (1.92), 4.270 (2.05), 4.669 (0.58), 4.696 (0.86), 4.706 (2.69), 4.739 (2.37), 5.017 (0.54), 5.048 (1.18), 5.074 (0.70), 5.114 (0.90), 5.155 (1.06), 5.168 (0.58), 5.186 (0.74), 5.196 (0.67), 5.759 (7.46), 6.762 (1.82), 6.765 (1.82), 6.780 (2.08), 6.782 (1.98), 6.839 (1.89), 6.858 (2.18), 6.994 (1.76), 7.013 (2.14), 7.032 (1.54), 7.354 (1.34), 7.374 (2.62), 7.393 (2.08), 7.439 (2.75), 7.459 (1.60), 7.491 (0.61), 7.504 (1.60), 7.508 (1.63), 7.512 (2.02), 7.520 (3.55), 7.528 (2.14), 7.531 (1.86), 7.535 (2.02), 7.548 (0.70), 7.553 (0.45), 7.726 (1.86), 7.729 (1.95), 7.746 (1.79), 7.853 (1.63), 7.861 (0.96), 7.870 (1.44), 7.876 (1.44), 8.221 (1.38), 8.227 (1.31), 8.245 (1.41).

The title compound (52 mg) was separated into enantiomers by preparative chiral HPLC to give enantiomer 1 (25 mg, see Example 133) and enantiomer 2 (20 mg, see Example 134).

Preparative chiral HPLC method: Instrument: Sepiatec: Prep SFC100; column: Chiralpak IE 5 μm 250×30 mm; eluent A: $CO_2$, eluent B: ethanol+0.4 Vol-% diethylamine (99%); isocratic: 37% B; flow 100.0 ml/min temperature: 40° C.; BPR: 150 bar; MWD @ 254 nm Analytical chiral HPLC method: Instrument: Agilent: 1260, Aurora SFC-Module; column: Chiralpak IE 5 μm 100×4.6 mm; eluent A: $CO_2$, eluent B: ethanol+0.2 Vol-% diethylamine (99%); isocratic: 37% B; flow 4.0 ml/min; temperature: 37.5° C.; BPR: 100 bar; MWD @ 254 nm Example 133

(E/Z)-1-methyl-3-(morpholin-4-ylmethyl)-7-[3-(naphthalen-1-yloxy)propyl]-1,10,13,15-tetrahydro-pyrazolo[4',3':9,10][1,6]oxazacycloundecino[8,7,6-hi]indole-8-carboxylic acid-N-ethylethanamine salt (Enantiomer 1)

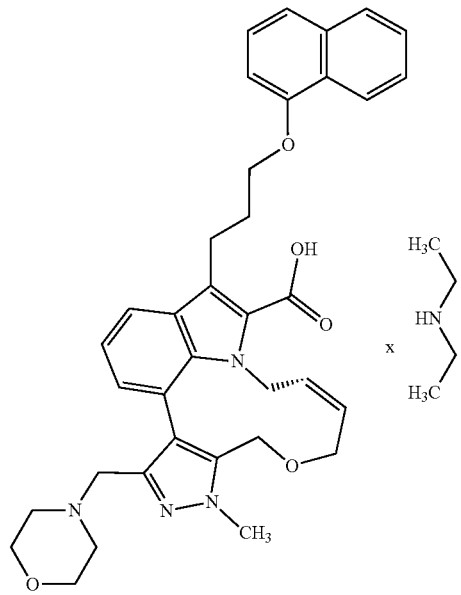

For the preparation of the racemic title compound see Example 132. Separation of enantiomers by preparative chiral HPLC (method see Example 132), gave the title compound (25 mg).

Analytical Chiral HPLC (method see Example 132): $R_t$=2.46 min.

LC-MS (Method 2): $R_t$=0.88 min; MS (ESIpos): m/z=607 [M+H]$^+$ $^1$H-NMR (400 MHz, DMSO-d6) δ[ppm]: 0.852 (0.47), 1.137 (3.11), 1.155 (7.06), 1.173 (3.22), 1.232 (1.19), 1.847 (0.76), 1.860 (1.01), 1.869 (0.90), 1.876 (0.94), 2.088 (0.90), 2.205 (0.87), 2.221 (1.16), 2.239 (0.87), 2.336 (0.72), 2.518 (9.12), 2.523 (5.86), 2.539 (0.90), 2.660 (0.69), 2.877 (0.76), 2.888 (1.09), 2.895 (2.35), 2.914 (2.57), 2.921 (2.79), 2.932 (0.90), 2.943 (2.61), 2.976 (0.94), 3.189 (0.94), 3.214 (1.16), 3.221 (1.45), 3.229 (1.38), 3.237 (1.41), 3.247 (0.80), 3.256 (1.05), 3.278 (0.87), 3.381 (1.01), 3.399 (0.72), 3.415 (0.58), 3.493 (0.58), 3.523 (1.01), 3.554 (0.69), 3.765 (0.62), 3.776 (0.69), 3.798 (0.54), 3.808 (0.54), 3.863 (0.90), 3.891 (16.00), 4.143 (1.12), 4.159 (2.35), 4.175 (1.19), 4.240 (1.67), 4.275 (1.77), 4.660 (0.40), 4.696 (1.99), 4.731 (1.67), 5.035 (0.43), 5.061 (0.76), 5.087 (0.62), 5.152 (0.43), 5.179 (0.90), 6.717 (0.87), 6.735 (0.98), 6.834 (1.56), 6.851 (1.70), 6.964 (0.90), 6.983 (1.38), 7.001 (0.83), 7.348 (1.30), 7.368 (2.32), 7.387 (1.88), 7.433 (2.39), 7.454 (1.41), 7.487 (0.54), 7.499 (1.48), 7.504 (1.38), 7.508 (1.85), 7.516 (3.40), 7.524 (1.85), 7.527 (1.59), 7.532 (1.81), 7.544 (0.65), 7.684 (0.98), 7.704 (0.94), 7.849 (1.38), 7.852 (1.16), 7.857 (0.80), 7.867 (1.27), 7.872 (1.27), 8.219 (1.23), 8.226 (1.16), 8.236 (0.62), 8.243 (1.19).

Example 134

(E/Z)-1-methyl-3-(morpholin-4-ylmethyl)-7-[3-(naphthalen-1-yloxy)propyl]-1,10,13,15-tetrahydro-pyrazolo[4',3':9,10][1,6]oxazacycloundecino[8,7,6-hi]indole-8-carboxylic acid-N-ethylethanamine salt (Enantiomer 2)

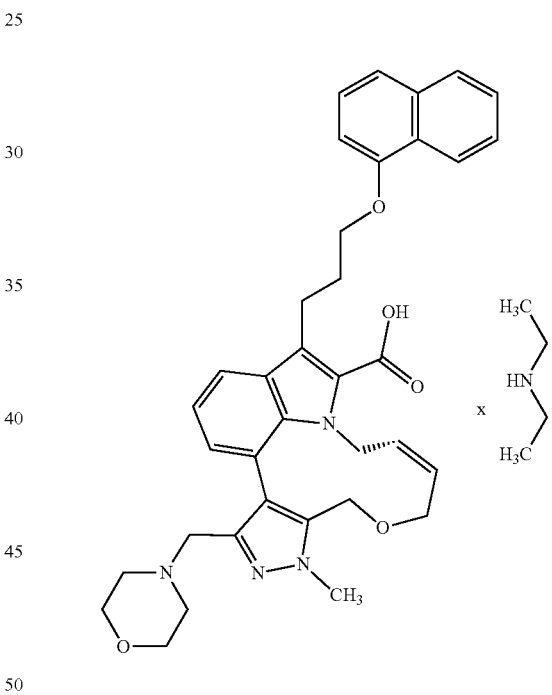

For the preparation of the racemic title compound see Example 132. Separation of enantiomers by preparative chiral HPLC (method see Example 132), gave the title compound (25 mg).

Analytical Chiral HPLC (method see Example 132): $R_t$=3.62 min.

LC-MS (Method 2): $R_t$=0.86 min; MS (ESIpos): m/z=607 [M+H]$^+$ $^1$H-NMR (400 MHz, DMSO-d6) δ[ppm]: 0.852 (0.41), 0.934 (0.44), 1.137 (2.93), 1.156 (6.52), 1.174 (3.00), 1.232 (1.11), 1.845 (0.78), 1.857 (1.07), 1.866 (0.93), 1.874 (1.00), 2.089 (0.93), 2.206 (0.81), 2.221 (1.15), 2.239 (0.85), 2.332 (1.56), 2.336 (0.70), 2.518 (8.74), 2.523 (5.70), 2.539 (1.19), 2.673 (1.56), 2.678 (0.67), 2.880 (0.74), 2.889 (1.07), 2.898 (2.26), 2.917 (2.63), 2.922 (3.07), 2.935 (1.00), 2.942 (2.81), 2.975 (0.96), 3.186 (1.00), 3.212 (1.22), 3.219 (1.48), 3.228 (1.41), 3.235 (1.44), 3.246 (0.81), 3.254 (0.93), 3.262 (0.93), 3.282 (0.96), 3.384 (1.07), 3.403 (0.78), 3.417 (0.59), 3.493 (0.63), 3.524 (1.07), 3.554 (0.74), 3.766 (0.63), 3.777 (0.74), 3.798 (0.56), 3.809 (0.52), 3.891 (16.00), 4.144 (1.15), 4.160 (2.44), 4.176 (1.19), 4.240 (1.70), 4.273 (1.81), 4.668 (0.44), 4.698 (2.19), 4.732 (1.74), 5.059 (0.81), 5.085 (0.59), 5.144 (0.44), 5.156 (0.52), 5.171 (1.04), 5.212 (0.63), 6.725 (1.00), 6.742 (1.15), 6.834 (1.63), 6.852 (1.74), 6.969 (1.04), 6.988 (1.52), 7.007 (0.93), 7.348 (1.30), 7.369 (2.33), 7.388 (1.89), 7.434 (2.44), 7.455 (1.44), 7.487 (0.56), 7.500 (1.56), 7.504 (1.44), 7.509 (1.78), 7.516 (3.52), 7.524 (1.78), 7.528 (1.63), 7.532 (1.70), 7.545 (0.67), 7.691 (1.11), 7.710 (1.04), 7.849 (1.44), 7.858 (0.78), 7.867 (1.26), 7.873 (1.26), 8.219 (1.30), 8.226 (1.19), 8.236 (0.63), 8.244 (1.19).

Example 135

(rac)-1-methyl-3-(morpholin-4-ylmethyl)-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid

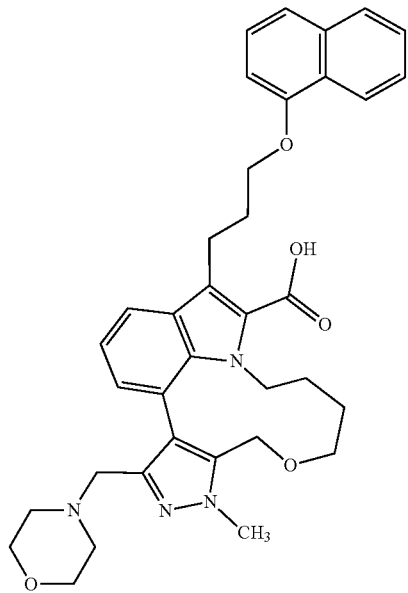 [SMILES: Cn1nc(CN2CCOCC2)c2c1COCCCCn1c(C(=O)O)c(CCCOc3cccc4ccccc34)c3cccc-2c31]

To a solution of (rac)-ethyl 1-methyl-3-(morpholin-4-ylmethyl)-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (see Intermediate 265, 160 mg, 251 μmol) in THF (10 ml) and ethanol (5.0 ml) was added a solution of lithium hydroxide in water (5.0 ml, 1.0 M, 5.0 mmol). The reaction mixture was stirred for 2 days at room temperature. For work-up, the reaction mixture was concentrated under reduced pressure and the residue was purified by flash chromatography (dichloromethane/ethanol gradient, 0%→30% ethanol) to give the title compound (96 mg) as a racemic mixture.

LC-MS (Method 2): Rt=0.81 min; MS (ESIneg): m/z=607 [M−H]⁻

¹H-NMR (400 MHz, DMSO-d6) δ[ppm]: 1.071 (2.04), 1.088 (4.28), 1.106 (2.21), 1.232 (0.54), 1.843 (0.42), 1.862 (0.56), 1.882 (0.66), 1.907 (6.18), 1.915 (0.63), 1.937 (0.42), 2.078 (0.87), 2.095 (1.08), 2.107 (1.53), 2.163 (1.64), 2.179 (1.74), 2.197 (1.86), 2.216 (1.10), 2.332 (1.01), 2.336 (0.42), 2.518 (5.10), 2.523 (3.55), 2.673 (1.01), 2.678 (0.45), 3.066 (1.79), 3.099 (2.33), 3.255 (2.65), 3.291 (6.77), 3.354 (1.79), 3.372 (2.56), 3.389 (2.11), 3.406 (0.78), 3.882 (16.00), 4.057 (0.42), 4.069 (0.61), 4.084 (0.45), 4.092 (0.49), 4.160 (1.36), 4.176 (2.82), 4.192 (1.34), 4.232 (0.73), 4.264 (1.20), 4.345 (1.08), 4.370 (0.94), 4.381 (0.82), 4.396 (0.47), 4.405 (0.42), 4.632 (1.08), 4.637 (1.10), 4.675 (1.20), 4.680 (1.29), 4.745 (1.22), 4.750 (1.15), 4.770 (1.34), 4.776 (1.20), 5.198 (0.66), 5.212 (0.78), 5.229 (0.85), 5.238 (0.42), 5.247 (0.40), 5.255 (0.99), 5.272 (0.96), 5.298 (0.59), 6.865 (1.76), 6.883 (1.95), 6.980 (0.66), 6.995 (1.57), 7.008 (1.64), 7.026 (1.69), 7.045 (0.66), 7.361 (1.32), 7.381 (2.49), 7.400 (2.02), 7.442 (2.58), 7.463 (1.46), 7.500 (0.54), 7.512 (1.83), 7.516 (2.54), 7.526 (3.01), 7.535 (2.42), 7.539 (1.90), 7.551 (0.54), 7.672 (1.06), 7.689 (0.99), 7.855 (1.48), 7.858 (1.03), 7.868 (0.96), 7.872 (0.96), 7.878 (1.25), 8.245 (1.29), 8.257 (0.94), 8.270 (1.20).

The title compound (94 mg) was separated into enantiomers by preparative chiral HPLC, followed by flash chromatography, to give enantiomer 1 (30 mg, see Example 136) and enantiomer 2 (30 mg, see Example 137).

Preparative chiral HPLC method: Instrument: Sepiatec: Prep SFC100; column: Chiralpak IE 5 μm 250×30 mm; eluent A: CO₂, eluent B: 2-propanol+0.4 Vol-% diethylamine (99%); isocratic: 30% B; flow 100.0 ml/min temperature: 40° C.; BPR: 150 bar; MWD @ 254 nm Analytical chiral HPLC method: Instrument: Agilent 1260, Aurora SFC-Module; column: Chiralpak IE 5 μm 100×4.6 mm; eluent A: CO₂, eluent B: 2-propanol+0.2 Vol-% diethylamine (99%); isocratic: 30% B; flow 4.0 ml/min; temperature: 37.5° C.; BPR: 100 bar; MWD @ 254 nm Example 136

1-methyl-3-(morpholin-4-ylmethyl)-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (Enantiomer 1)

For the preparation of the racemic title compound see Example 135. After separation of enantiomers by preparative chiral HPLC (method see Example 135), the obtained product was further purified by flash chromatography (dichloromethane/ethanol gradient, 0%→40% ethanol) to give, after trituration with water, the title compound (30 mg).

Analytical Chiral HPLC (method see Example 135): R$_t$=3.03 min.

LC-MS (Method 2): R$_t$=0.81 min; MS (ESIpos): m/z=609 [M+H]⁺

¹H-NMR (400 MHz, DMSO-d6) δ[ppm]: 0.798 (0.73), 0.815 (0.73), 0.821 (0.76), 0.904 (0.89), 0.922 (0.43), 1.232 (0.73), 1.847 (0.40), 1.866 (0.54), 1.883 (0.65), 1.900 (0.62), 1.918 (0.54), 1.936 (0.40), 2.073 (0.81), 2.090 (0.97), 2.102 (1.38), 2.163 (1.38), 2.182 (1.51), 2.199 (1.70), 2.218 (1.03), 2.332 (1.13), 2.336 (0.51), 2.518 (6.04), 2.522 (4.16), 2.673 (1.19), 2.678 (0.51), 3.068 (1.56), 3.101 (2.08), 3.252 (2.21), 3.275 (2.64), 3.285 (6.07), 3.314 (2.48), 3.883 (16.00), 4.081 (0.62), 4.096 (0.43), 4.104 (0.51), 4.162 (1.27), 4.178 (2.67), 4.193 (1.24), 4.232 (0.67), 4.242 (0.73), 4.263 (1.13), 4.273 (1.05), 4.335 (1.05), 4.349 (1.38), 4.366 (1.08), 4.380 (0.89), 4.399 (0.43), 4.632 (1.03), 4.637 (1.11), 4.675 (1.19), 4.680 (1.27), 4.746 (1.16), 4.751 (1.11), 4.772 (1.32), 4.777 (1.21), 5.191 (0.89), 5.204 (1.38), 5.216 (0.94), 5.229 (0.78), 5.255 (0.97), 5.273 (0.92), 5.298 (0.59), 6.867 (1.70), 6.884 (1.86), 7.001 (0.49), 7.005 (0.81), 7.019 (2.37), 7.025 (3.32), 7.043 (2.35), 7.062 (0.84), 7.363 (1.40), 7.383 (2.48), 7.402 (2.08), 7.444 (2.54), 7.465 (1.43), 7.502 (0.51), 7.514 (1.78), 7.518 (2.51), 7.528 (3.05), 7.537 (2.40), 7.542 (1.97), 7.553

(0.57), 7.694 (1.32), 7.699 (1.38), 7.713 (1.27), 7.717 (1.24), 7.856 (1.43), 7.860 (1.00), 7.870 (0.89), 7.874 (0.94), 7.880 (1.24), 8.246 (1.30), 8.257 (0.89), 8.270 (1.19).

Example 137

1-methyl-3-(morpholin-4-ylmethyl)-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (Enantiomer 2)

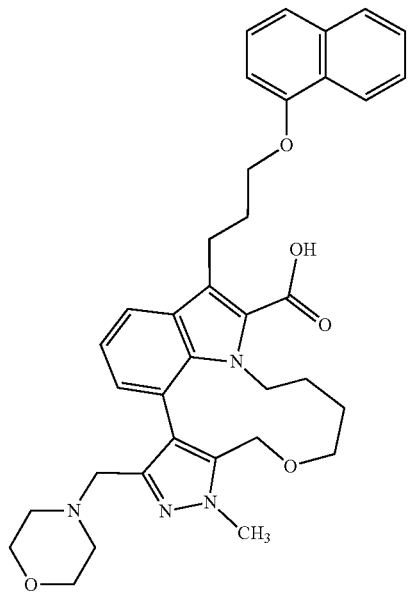 [SMILES: Cn1nc(CN2CCOCC2)c2c1COCCCCn1c(C(=O)O)c(CCCOc3cccc4ccccc34)c3cccc-2c31]

For the preparation of the racemic title compound see Example 135. After separation of enantiomers by preparative chiral HPLC (method see Example 135), the obtained product was further purified by flash chromatography (dichloromethane/ethanol gradient, 0%→40% ethanol) to give, after trituration with water, the title compound (30 mg).

Analytical Chiral HPLC (method see Example 135): $R_t$=5.80 min.

LC-MS (Method 2): $R_t$=0.80 min; MS (ESIpos): m/z=609 [M+H]$^+$ $^1$H-NMR (400 MHz, DMSO-d6) δ[ppm]: 0.798 (0.61), 0.815 (0.61), 0.822 (0.61), 0.905 (0.75), 1.053 (0.75), 1.233 (0.80), 1.865 (0.53), 1.885 (0.61), 1.902 (0.61), 1.907 (0.64), 1.918 (0.55), 2.074 (0.80), 2.091 (0.97), 2.102 (1.38), 2.164 (1.36), 2.182 (1.49), 2.200 (1.66), 2.218 (1.00), 2.337 (0.53), 2.518 (6.17), 2.523 (4.24), 2.674 (1.19), 2.679 (0.53), 3.068 (1.66), 3.101 (2.19), 3.252 (2.33), 3.275 (2.63), 3.286 (6.31), 3.312 (2.41), 3.884 (16.00), 4.081 (0.61), 4.095 (0.44), 4.104 (0.50), 4.162 (1.27), 4.178 (2.63), 4.194 (1.25), 4.232 (0.61), 4.242 (0.64), 4.264 (1.05), 4.273 (1.00), 4.335 (0.97), 4.349 (1.33), 4.367 (1.00), 4.381 (0.86), 4.399 (0.44), 4.632 (1.02), 4.637 (1.08), 4.675 (1.13), 4.681 (1.25), 4.747 (1.13), 4.752 (1.13), 4.772 (1.27), 4.778 (1.16), 5.191 (0.75), 5.204 (1.22), 5.214 (0.91), 5.230 (0.78), 5.255 (0.94), 5.273 (0.94), 5.299 (0.58), 6.867 (1.72), 6.884 (1.85), 7.000 (0.47), 7.003 (0.75), 7.017 (2.13), 7.024 (2.85), 7.043 (2.19), 7.060 (0.80), 7.363 (1.36), 7.384 (2.46), 7.403 (2.02), 7.445 (2.49), 7.465 (1.41), 7.502 (0.50), 7.514 (1.69), 7.518 (2.55), 7.528 (3.02), 7.538 (2.41), 7.542 (1.91), 7.554 (0.55), 7.693 (1.25), 7.697 (1.27), 7.711 (1.13), 7.715 (1.13), 7.857 (1.44), 7.861 (1.00), 7.871 (0.89), 7.875 (0.91), 7.880 (1.22), 8.247 (1.27), 8.257 (0.86), 8.271 (1.19).

Example 138

(rac)-9-methyl-11-(morpholin-4-ylmethyl)-1-[3-(naphthalen-1-yloxy)propyl]-5,6,8,9-tetrahydro-4H-pyrazolo[4',3':8,9][1,5]oxazecino[7,6,5-hi]indole-2-carboxylic acid

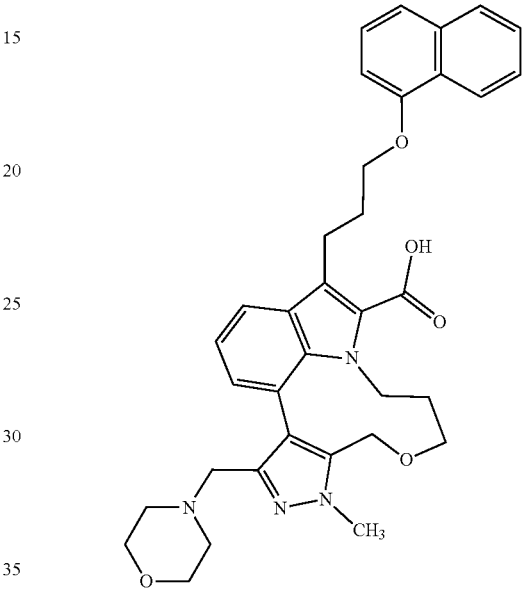

To a solution of (rac)-ethyl 9-methyl-11-(morpholin-4-ylmethyl)-1-[3-(naphthalen-1-yloxy)propyl]-5,6,8,9-tetrahydro-4H-pyrazolo[4',3':8,9][1,5]oxazecino[7,6,5-hi]indole-2-carboxylate (see Intermediate 266, 110 mg, 177 µmol) in THF (7.1 ml) and ethanol (3.5 ml) was added a solution of lithium hydroxide in water (3.5 ml, 1.0 M, 3.5 mmol). The reaction mixture was stirred for 2 weeks at room temperature. For work-up, the reaction mixture was concentrated under reduced pressure and the residue was purified by flash chromatography (dichloromethane/ethanol gradient, 0%→28% ethanol) to give, after crystallization from diethyl ether, the title compound (91 mg) as a racemic mixture.

LC-MS (Method 2): $R_t$=0.78 min; MS (ESIpos): m/z=595 [M+H]$^+$ $^1$H-NMR (400 MHz, DMSO-d6) δ[ppm]: 1.071 (0.66), 1.088 (1.27), 1.106 (0.70), 1.233 (0.45), 1.907 (5.23), 2.080 (0.41), 2.096 (0.52), 2.108 (0.74), 2.119 (0.46), 2.157 (0.64), 2.169 (0.58), 2.188 (0.75), 2.205 (0.73), 2.224 (0.50), 2.518 (2.75), 2.523 (1.97), 3.062 (0.85), 3.095 (1.20), 3.204 (1.20), 3.237 (0.87), 3.303 (2.61), 3.316 (2.54), 3.330 (16.00), 3.354 (0.60), 3.372 (0.82), 3.389 (0.69), 4.112 (0.85), 4.116 (0.66), 4.135 (0.46), 4.143 (0.45), 4.155 (0.67), 4.159 (0.71), 4.168 (0.69), 4.183 (1.36), 4.199 (0.65), 4.704 (0.54), 4.708 (0.53), 4.730 (0.57), 4.734 (0.57), 5.130 (0.48), 6.866 (0.86), 6.884 (0.91), 7.023 (0.91), 7.027 (0.91), 7.032 (1.05), 7.050 (0.94), 7.362 (0.69), 7.382 (1.23), 7.401 (0.99), 7.445 (1.24), 7.465 (0.71), 7.513 (0.86), 7.517 (1.36), 7.527 (1.51), 7.536 (1.30), 7.540 (0.93), 7.703 (0.54), 7.706 (0.56), 7.722 (0.52), 7.856 (0.70), 7.860 (0.50), 7.871 (0.45), 7.874 (0.46), 7.880 (0.61), 8.247 (0.62), 8.255 (0.41), 8.272 (0.60).

The title compound (89 mg) was separated into enantiomers by preparative chiral HPLC, followed by flash chromatography, to give enantiomer 1 (23 mg, see Example 139) and enantiomer 2 (16 mg, see Example 140).

Preparative chiral HPLC method: Instrument: Sepiatec: Prep SFC100; column: Chiralpak IE 5 µm 250×30 mm; eluent A: $CO_2$, eluent B: 2-propanol+0.4 Vol-% diethylamine (99%); isocratic: 33% B; flow 100.0 ml/min temperature: 40° C.; BPR: 150 bar; MWD @ 254 nm Analytical chiral HPLC method: Instrument: Agilent 1260, Aurora SFC-Module; column: Chiralpak IE 5 µm 100×4.6 mm; eluent A: $CO_2$, eluent B: 2-propanol+0.2 Vol-% diethylamine (99%); isocratic: 33% B; flow 4.0 ml/min; temperature: 37.5° C.; BPR: 100 bar; MWD @ 254 nm Example 139

9-methyl-11-(morpholin-4-ylmethyl)-1-[3-(naphthalen-1-yloxy)propyl]-5,6,8,9-tetrahydro-4H-pyrazolo[4',3':8,9][1,5]oxazecino[7,6,5-hi]indole-2-carboxylic acid (Enantiomer 1)

For the preparation of the racemic title compound see Example 138. After separation of enantiomers by preparative chiral HPLC (method see Example 138), the obtained product was further purified by flash chromatography (dichloromethane/ethanol gradient, 0%→30% ethanol) to give, after trituration with water, the title compound (23 mg).

Analytical Chiral HPLC (method see Example 138): $R_t$=2.85 min.

LC-MS (Method 2): $R_t$=0.80 min; MS (ESIpos): m/z=595 [M+H]$^+$ $^1$H-NMR (400 MHz, DMSO-d6) δ[ppm]: 0.851 (0.42), 1.171 (0.40), 1.232 (1.64), 1.256 (1.27), 1.295 (0.47), 1.332 (0.82), 2.078 (0.77), 2.084 (0.65), 2.095 (1.00), 2.107 (1.42), 2.118 (0.87), 2.159 (1.25), 2.171 (1.20), 2.188 (1.55), 2.205 (1.47), 2.224 (0.97), 2.332 (1.07), 2.336 (0.50), 2.518 (5.63), 2.522 (3.86), 2.673 (1.10), 2.678 (0.47), 3.064 (1.55), 3.096 (2.22), 3.203 (2.09), 3.237 (1.50), 3.289 (2.64), 3.301 (4.66), 3.311 (3.59), 3.882 (16.00), 4.104 (0.80), 4.115 (1.92), 4.119 (1.32), 4.136 (1.17), 4.147 (1.10), 4.158 (1.42), 4.162 (1.57), 4.168 (1.50), 4.184 (2.74), 4.200 (1.27), 4.274 (0.97), 4.288 (1.05), 4.306 (0.80), 4.320 (0.75), 4.626 (0.47), 4.638 (0.52), 4.668 (0.67), 4.681 (0.62), 4.709 (1.20), 4.713 (1.17), 4.735 (1.27), 4.739 (1.25), 4.956 (0.57), 4.967 (0.65), 4.998 (0.52), 5.010 (0.50), 5.119 (0.87), 5.133 (1.30), 5.144 (0.82), 5.421 (0.70), 5.434 (0.50), 5.447 (0.75), 5.451 (0.40), 5.464 (0.70), 5.477 (0.47), 5.489 (0.62), 6.867 (1.72), 6.884 (1.94), 7.015 (0.52), 7.019 (0.90), 7.033 (2.57), 7.039 (3.26), 7.057 (2.47), 7.076 (0.90), 7.363 (1.40), 7.383 (2.54), 7.402 (2.12), 7.445 (2.54), 7.466 (1.45), 7.501 (0.50), 7.513 (1.79), 7.518 (2.84), 7.527 (3.14), 7.537 (2.72), 7.541 (1.92), 7.553 (0.57), 7.713 (1.42), 7.717 (1.50), 7.731 (1.35), 7.736 (1.32), 7.857 (1.45), 7.861 (1.02), 7.868 (0.75), 7.872 (0.90), 7.875 (0.95), 7.880 (1.25), 8.247 (1.27), 8.256 (0.80), 8.272 (1.20).

Example 140

9-methyl-11-(morpholin-4-ylmethyl)-1-[3-(naphthalen-1-yloxy)propyl]-5,6,8,9-tetrahydro-4H-pyrazolo[4',3':8,9][1,5]oxazecino[7,6,5-hi]indole-2-carboxylic acid (Enantiomer 2)

For the preparation of the racemic title compound see Example 138. After separation of enantiomers by preparative chiral HPLC (method see Example 138), the obtained product was further purified by flash chromatography (dichloromethane/ethanol gradient, 0%→40% ethanol) to give, after trituration with water, the title compound (16 mg).

Analytical Chiral HPLC (method see Example 138): $R_t$=4.73 min.

LC-MS (Method 2): $R_t$=0.79 min; MS (ESIpos): m/z=595 [M+H]$^+$ $^1$H-NMR (400 MHz, DMSO-d6) δ[ppm]: 0.798 (0.58), 0.815 (0.52), 0.822 (0.52), 0.852 (0.52), 0.905 (0.55), 1.174 (0.67), 1.233 (1.95), 1.257 (1.19), 1.296 (0.43), 1.332 (0.82), 2.078 (0.92), 2.095 (1.19), 2.107 (1.68), 2.158 (1.47), 2.171 (1.44), 2.188 (1.80), 2.207 (1.74), 2.224 (1.19), 2.518 (7.63), 2.523 (5.25), 3.064 (1.71), 3.096 (2.50), 3.204 (2.41), 3.237 (1.71), 3.302 (5.56), 3.312 (4.31), 3.882 (16.00), 3.910 (0.49), 4.105 (0.92), 4.115 (2.11), 4.136 (1.28), 4.147 (1.22), 4.158 (1.59), 4.162 (1.74), 4.169 (1.71), 4.185 (3.11), 4.200 (1.53), 4.275 (1.10), 4.289 (1.19), 4.306 (0.89), 4.320 (0.82), 4.627 (0.55), 4.639 (0.61), 4.669 (0.76), 4.681 (0.73), 4.709 (1.28), 4.713 (1.28), 4.735 (1.37), 4.739 (1.34), 4.968 (0.73), 5.000 (0.58), 5.011 (0.58), 5.120 (0.98), 5.133 (1.53), 5.144 (0.95), 5.421 (0.73), 5.434 (0.55), 5.447 (0.76), 5.464 (0.76), 5.477 (0.52), 5.489 (0.64), 6.867 (1.95), 6.885 (2.17), 7.018 (0.85), 7.032 (2.56), 7.038 (3.27), 7.057 (2.41), 7.075 (0.85), 7.363 (1.40), 7.383 (2.66), 7.403 (2.05), 7.446 (2.81), 7.466 (1.59), 7.502 (0.52), 7.514 (1.83), 7.518 (2.93), 7.528 (3.27), 7.537 (2.90), 7.542 (2.02), 7.554 (0.58), 7.712 (1.47), 7.716 (1.53), 7.731 (1.37), 7.734 (1.34), 7.858 (1.59), 7.861 (1.13), 7.869 (0.92), 7.872 (0.98), 7.875 (1.01), 7.881 (1.34), 8.248 (1.37), 8.256 (0.98), 8.272 (1.28), 13.126 (0.40).

Example 141

(rac)-11-ethyl-7,10-dimethyl-1-[3-(1-naphthyloxy)propyl]-4,5,6,7,8,10-hexahydropyrazolo[3',4':7,8][1,5]diazecino[9,10,1-hi]indole-2-carboxylic acid

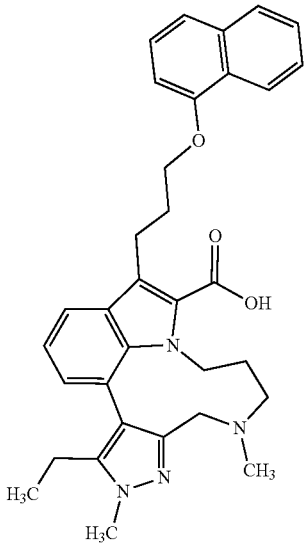 [SMILES: CCc1c2c(nn1C)CN(C)CCCn1c(C(=O)O)c(CCCOc3cccc4ccccc34)c3cccc-2c31]

A mixture of (rac)-ethyl 11-ethyl-7,9,12-trimethyl-1-[3-(naphthalen-1-yloxy)propyl]-4,5,6,7,8,9-hexahydropyrazolo[3',4':7,8][1,5]diazecino[9,10,1-hi]indole-2-carboxylate (160 mg, 283 µmol, see Intermediate 271), THF (14 mL), ethanol (6.7 mL) and lithium hydroxide (5.7 mL, 1.0 M in water) was stirred at 65° C. for 48 hrs. The mixture was concentrated and purified by flash chromatography (Biotage SNAP cartridge silica 120 g, methanol:dichloromethane) to give the title compound (100 mg, 66% yield).

LC-MS: m/z=537.0 [M+H]$^+$.

$^1$H-NMR (400 MHz, DMSO-d6), δ [ppm]=0.93 (3H), 1.43-1.53 (1H), 1.53-1.63 (1H), 1.85-1.92 (3H), 2.01 (1H), 2.19 (2H), 2.36-2.47 (3H), 3.14 (1H), 3.20-3.41 (3H), 3.80 (3H), 3.85 (1H), 4.17 (2H), 4.58 (1H), 6.78 (1H), 6.86 (1H), 6.94 (1H), 7.37 (1H), 7.45 (1H), 7.52 (2H), 7.64 (1H), 7.86 (1H), 8.25 (1H), 12.97 (1H).

The title compound (100 mg) was separated into enantiomers by preparative chiral HPLC to give enantiomer 1 (37 mg, see Example 142) and enantiomer 2 (34 mg, see Example 143).

Preparative chiral HPLC method: Instrument: Labomatic HD5000, Labocord-5000; Gilson GX-241, Labcol Vario 4000, column: Chiralpak IE 5μ 250×30 mm; eluent A: hexane+0.1 Vol-% diethylamine (99%); eluent B: ethanol; gradient: 20-50% B in 20 min; flow 40.0 ml/min; UV 254 nm Analytical chiral HPLC method: Instrument: Agilent HPLC 1260; column: Chiralpak IE 3μ 100×4.6 mm; eluent A: hexan+0.1 Vol-% diethylamine (99%); eluent B: Ethanol; gradient: 20-50% B; flow 1.4 ml/min; temperature: 25° C.; DAD 254 nm

Example 142

11-Ethyl-7,10-dimethyl-1-[3-(1-naphthyloxy)propyl]-4,5,6,7,8,10-hexahydropyrazolo[3',4':7,8][1,5]diazecino[9,10,1-hi]indole-2-carboxylic acid-N-ethylethanamine salt (Enantiomer 1)

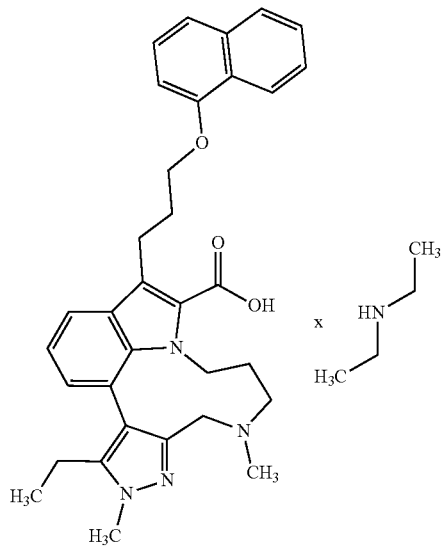

For the preparation of the racemic title compound see Example 141. Separation of enantiomers by preparative preparative chiral HPLC (method see Example 141), gave the title compound (37 mg).

Analytical Chiral HPLC (method see Example 141): R$_t$=4.85 min.

LC-MS: m/z=537.0 [M+H]$^+$.

$^1$H-NMR (400 MHz, DMSO-d6), δ [ppm]=0.93 (3H), 1.16 (2.4H), 1.42-1.62 (2H), 1.90 (3H), 2.00 (1H), 2.19 (2H), 2.36-2.47 (3H), 2.88 (1.5H), 3.14 (1H), 3.18-3.43 (3H), 3.72-3.85 (1H), 3.81 (3H), 4.16 (2H), 4.61 (1H), 6.75 (1H), 6.85 (1H), 6.92 (1H), 7.36 (1H), 7.44 (1H), 7.52 (2H), 7.61 (1H), 7.86 (1H), 8.25 (1H).

Example 143

11-ethyl-7,10-dimethyl-1-[3-(1-naphthyloxy)propyl]-4,5,6,7,8,10-hexahydropyrazolo[3',4':7,8][1,5]diazecino[9,10,1-hi]indole-2-carboxylic acid-N-ethylethanamine salt (Enantiomer 2)

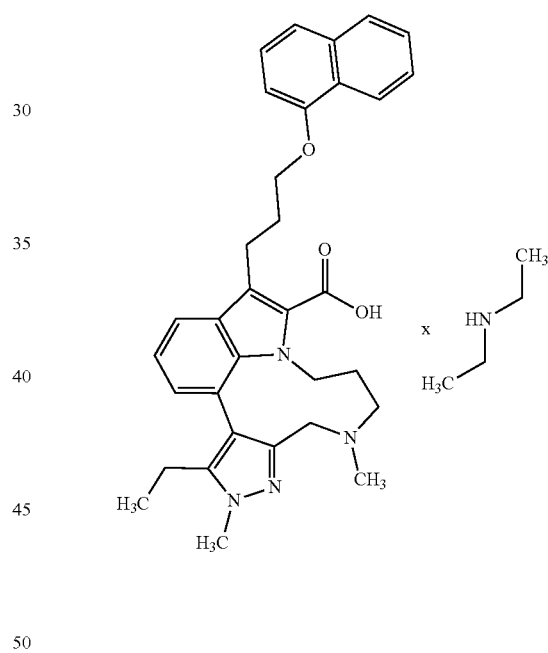

For the preparation of the racemic title compound see Example 141. Separation of enantiomers by preparative preparative chiral HPLC (method see Example 141), gave the title compound (34 mg).

Analytical Chiral HPLC (method see Example 141): R$_t$=5.60 min.

LC-MS: m/z=537.0 [M+H]$^+$.

$^1$H-NMR (400 MHz, DMSO-d6), δ [ppm]=0.93 (3H), 1.16 (2.6H), 1.42-1.62 (2H), 1.90 (3H), 2.00 (1H), 2.19 (2H), 2.36-2.47 (3H), 2.88 (1.7H), 3.14 (1H), 3.18-3.43 (3H), 3.72-3.85 (1H), 3.81 (3H), 4.16 (2H), 4.61 (1H), 6.75 (1H), 6.85 (1H), 6.92 (1H), 7.36 (1H), 7.44 (1H), 7.52 (2H), 7.61 (1H), 7.86 (1H), 8.25 (1H).

Example 144

(rac)-11-ethyl-7,10,12-trimethyl-1-[3-(1-naphth-yloxy)propyl]-4,5,6,7,8,10-hexahydropyrazolo[3',4':7,8][1,5]diazecino[9,10,1-hi]indole-2-carboxylic acid

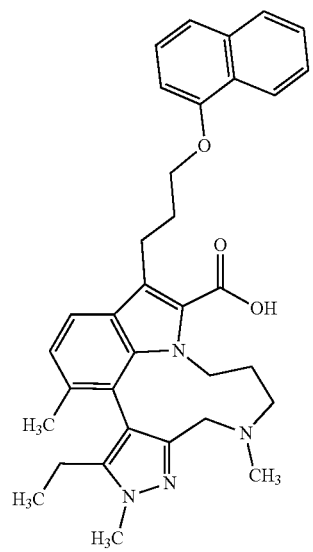 [SMILES: CCc1c2c(nn1C)CN(C)CCCn1c(C(=O)O)c(CCCOc3cccc4ccccc34)c3ccc(C)c-2c31]

A mixture of (rac)- ethyl 11-ethyl-7,10,12-trimethyl-1-[3-(1-naphthyloxy)propyl]-4,5,6,7,8,10-hexahydropyrazolo[3',4':7,8][1,5]diazecino[9,10,1-hi]indole-2-carboxylate (350 mg, 605 µmol, see Intermediate 279), THF (29 mL), ethanol (14 mL) and lithium hydroxide (12 mL, 1.0 M in water) was stirred at 65° C. for 2 days. The mixture was concentrated and the residue purified by flash chromatography (Biotage SNAP cartridge silica 40 g, methanol:dichloromethane) to give the title compound (250 mg, 74% yield) as mixture of atropisomers.

MS: m/z=551.4 [M+H]$^+$.

$^1$H-NMR (400 MHz, DMSO-d6), δ [ppm]=0.88 (3H), 1.40 (2H), 1.87 (1H), 1.92 (3H), 2.06 (3H), 2.16 (2H), 2.23 (1H), 2.29-2.41 (2H), 3.00-3.10 (2H), 3.20 (1H), 3.29-3.43 (2H), 3.82 (3H), 4.15 (2H), 4.77 (1H), 6.79 (1H), 6.84 (1H), 7.35 (2H), 7.43 (1H), 7.51 (2H), 7.85 (1H), 8.24 (1H).

The title compound (250 mg) was separated into enantiomers by preparative chiral HPLC to give enantiomer 1 (58 mg, see Example 145) and enantiomer 2 (66 mg, see Example 146).

Preparative chiral HPLC method: Instrument: Labomatic HD5000, Labocord-5000; Gilson GX-241, Labcol Vario 4000, column: Chiralpak IE 5µ 250×30 mm; eluent A: hexane+0.1 Vol-% diethylamine (99%); eluent B: ethanol; gradient: 20-50% B in 15 min; flow 40.0 ml/min; UV 254 nm Analytical chiral HPLC method: Instrument: Agilent HPLC 1260; column: Chiralpak IE 3µ 100×4.6 mm; eluent A: hexane+0.1 Vol-% diethylamine (99%); eluent B: ethanol; gradient: 20-50% B in 7 min; flow 1.4 ml/min; temperature: 25° C.; DAD 254 nm

Example 145

11-Ethyl-7,10,12-trimethyl-1-[3-(1-naphthyloxy)propyl]-4,5,6,7,8,10-hexahydropyrazolo[3',4':7,8][1,5]diazecino[9,10,1-hi]indole-2-carboxylic acid-N-ethylethanamine salt (Enantiomer 1)

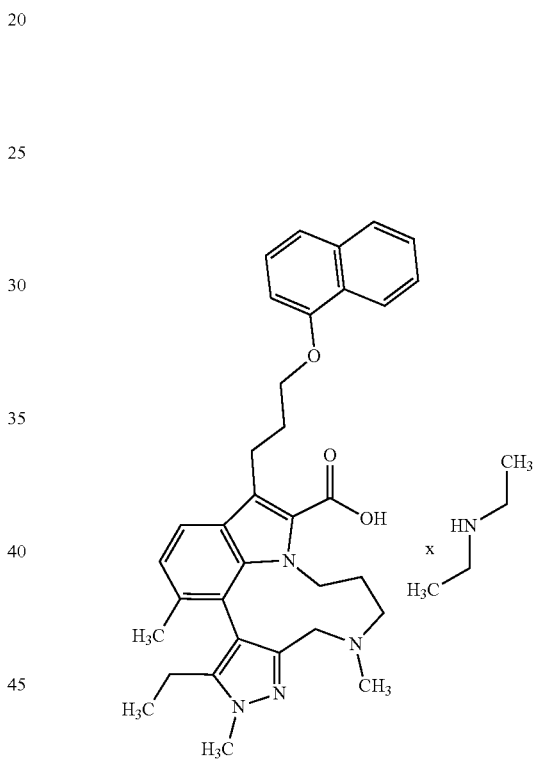

For the preparation of the racemic title compound see Example 144. Separation of enantiomers by preparative preparative chiral HPLC (method see Example 144), gave the title compound (58 mg).

Analytical Chiral HPLC (method see Example 144): R$_t$=4.84 min.

LC-MS: m/z=551.4 [M+H]$^+$.

$^1$H-NMR (400 MHz, DMSO-d6), δ [ppm]=0.87 (3H), 1.35-1.46 (2H), 1.89 (1H), 1.93 (3H), 2.02 (3H), 2.17 (2H), 2.24 (1H), 2.37 (2H), 3.04 (1H), 3.06-3.14 (1H), 3.23 (1H), 3.31 (1H), 3.46 (1H), 3.82 (3H), 4.15 (2H), 4.72 (1H), 6.83 (2H), 7.33-7.46 (3H), 7.51 (2H), 7.85 (1H), 8.24 (1H).

Example 146

11-Ethyl-7,10,12-trimethyl-1-[3-(1-naphthyloxy) propyl]-4,5,6,7,8,10-hexahydropyrazolo[3',4':7,8][1, 5]diazecino[9,10,1-hi]indole-2-carboxylic acid-N-ethylethanamine salt (Enantiomer 2)

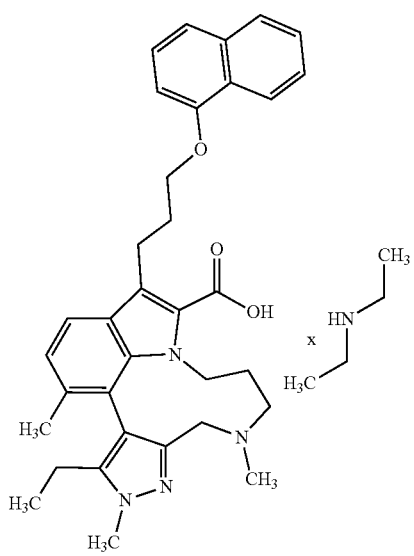

For the preparation of the racemic title compound see Example 144. Separation of enantiomers by preparative preparative chiral HPLC (method see Example 144), gave the title compound (66 mg).

Analytical Chiral HPLC (method see Example 144): $R_t$=5.67 min.

LC-MS: m/z=551.4 [M+H]$^+$.

$^1$H-NMR (400 MHz, DMSO-d6), δ [ppm]=0.87 (3H), 1.35-1.46 (2H), 1.89 (1H), 1.93 (3H), 2.02 (3H), 2.17 (2H), 2.24 (1H), 2.37 (2H), 3.04 (1H), 3.06-3.14 (1H), 3.23 (1H), 3.31 (1H), 3.46 (1H), 3.82 (3H), 4.15 (2H), 4.72 (1H), 6.83 (2H), 7.33-7.46 (3H), 7.51 (2H), 7.85 (1H), 8.24 (1H).

Example 147

(rac)-3-Ethyl-2-methyl-7-[3-(1-naphthyloxy)propyl]-2,10,11,12,13,15-hexahydropyrazolo[4',3':9,10][1,6] oxazacycloundecino[8,7,6-hi]indole-8-carboxylic acid

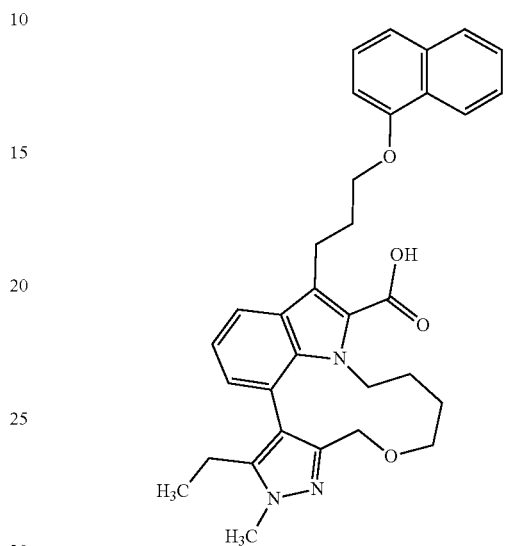

A mixture of (rac)- ethyl 3-ethyl-2-methyl-7-[3-(1-naphthyloxy)propyl]-2,10,11,12,13,15-hexahydropyrazolo[4',3': 9,10][1,6]oxazacycloundecino[8,7,6-hi]indole-8-carboxylate (120 mg, 212 μmol, see Intermediate 274), THF (10 mL), ethanol (5.0 mL) and lithium hydroxide (4.2 mL, 1.0 M in water) was stirred at 65° C. overnight. The mixture was concentrated and the residue was purified by flash chromatography (Biotage, SNAP silica 25 g, methanol:dichloromethane) to give the title compound (95 mg, 83% yield) as mixture of atropisomers.

LC-MS: m/z=538.3 [M+H]$^+$.

$^1$H-NMR (400 MHz, DMSO-d6), δ [ppm]=0.84 (3H), 0.98 (1H), 1.11-1.29 (2H), 1.35 (1H), 1.71 (1H), 2.09-2.29 (3H), 3.11 (1H), 3.24-3.37 (3H), 3.82 (3H), 3.87-4.00 (1H), 4.14-4.32 (4H), 4.51 (1H), 6.88 (1H), 6.91 (1H), 7.05 (1H), 7.38 (1H), 7.46 (1H), 7.53 (2H), 7.71 (1H), 7.87 (1H), 8.27 (1H), 13.09 (1H).

The title compound (95 mg) was separated into enantiomers by preparative chiral HPLC to give enantiomer 1 (23 mg, see Example 148) and enantiomer 2 (25 mg, see Example 149).

Preparative chiral HPLC method: Instrument: Labomatic HD5000, Labocord-5000; Gilson GX-241, Labcol Vario 4000, column: Amylose SA 5μ 250×30 mm; eluent A: hexan+0.1 Vol-% diethylamine (99%); eluent B: ethanol; gradient: 20-63.5% B in 12 min; flow 40.0 ml/min; UV 280 nm Analytical chiral HPLC method: Instrument: Agilent HPLC 1260; column: Amylose SA 3μ 100×4.6 mm; eluent A: hexan+0.1 Vol-% diethylamine (99%); eluent B: ethanol; gradient: 20-50% B in 7 min; flow 1.4 ml/min; temperature: 25° C.; DAD 280 nm

1027

Example 148

3-Ethyl-2-methyl-7-[3-(1-naphthyloxy)propyl]-2,10,11,12,13,15-hexahydropyrazolo[4',3':9,10][1,6]oxazacycloundecino[8,7,6-hi]indole-8-carboxylic acid-N-ethylethanamine salt (Enantiomer 1)

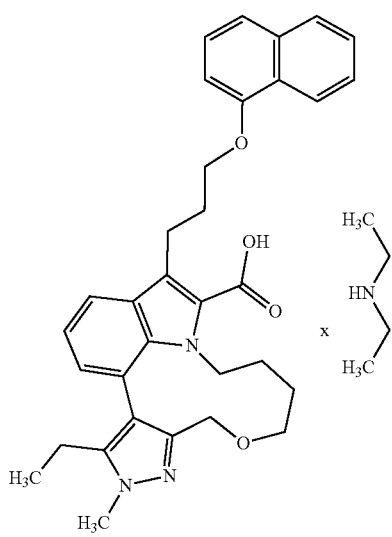

For the preparation of the racemic title compound see Example 147. Separation of enantiomers by preparative preparative chiral HPLC (method see Example 147), gave the title compound (23 mg).

Analytical Chiral HPLC (method see Example 147): $R_t$=1.65 min.

$^1$H-NMR (400 MHz, DMSO-d6), δ [ppm]=0.85 (3H), 1.05-1.25 (3H), 1.15 (3.6H), 1.34 (1H), 2.12-2.29 (4H), 2.85 (2.4H), 3.10 (1H), 3.19-3.31 (3H), 3.82 (4H), 4.12-4.24 (3H), 4.41 (1H), 4.46 (1H), 6.77 (1H), 6.87 (1H), 6.96 (1H), 7.36 (1H), 7.44 (1H), 7.52 (2H), 7.60 (1H), 7.86 (1H), 8.26 (1H), 8.87-10.11 (1H).

1028

Example 149

3-Ethyl-2-methyl-7-[3-(1-naphthyloxy)propyl]-2,10,11,12,13,15-hexahydropyrazolo[4',3':9,10][1,6]oxazacycloundecino[8,7,6-hi]indole-8-carboxylic acid-N-ethylethanamine salt (Enantiomer 2)

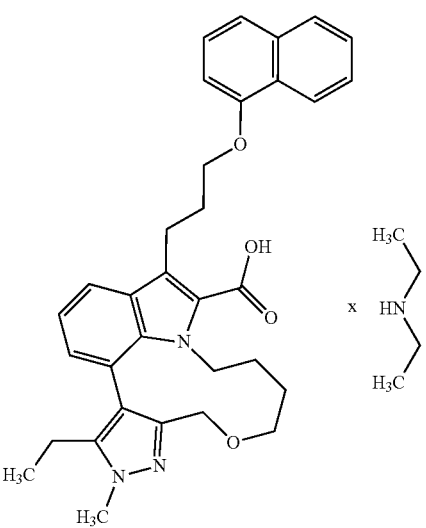

For the preparation of the racemic title compound see Example 147. Separation of enantiomers by preparative preparative chiral HPLC (method see Example 147), gave the title compound (23 mg).

Analytical Chiral HPLC (method see Example 147): $R_t$=2.76 min.

$^1$H-NMR (400 MHz, DMSO-d6), δ [ppm]=0.85 (3H), 1.05-1.25 (3H), 1.15 (3.4H), 1.34 (1H), 2.12-2.29 (4H), 2.86 (2.2H), 3.10 (1H), 3.19-3.31 (3H), 3.82 (4H), 4.12-4.24 (3H), 4.41 (1H), 4.46 (1H), 6.77 (1H), 6.87 (1H), 6.96 (1H), 7.36 (1H), 7.44 (1H), 7.52 (2H), 7.60 (1H), 7.86 (1H), 8.26 (1H).

Example 150

(rac)-1-methyl-3-[2-(morpholin-4-yl)ethyl]-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid

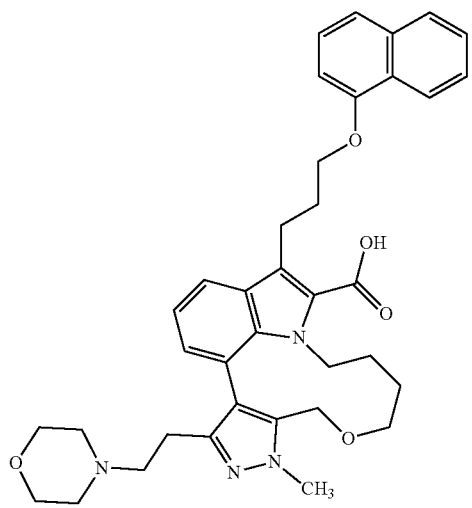 [SMILES: Cn1nc(CCN2CCOCC2)c2c1COCCCCn1c(C(=O)O)c(CCCOc3cccc4ccccc34)c3cccc-2c31]

To a solution of (rac)-ethyl 1-methyl-3-[2-(morpholin-4-yl)ethyl]-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (see Intermediate 234, 160 mg, 246 µmol) in THF (12 ml) and ethanol (5.8 ml) was added a solution of lithium hydroxide in water (4.9 ml, 1.0 M, 4.9 mmol). The reaction mixture was stirred for 48 hours at 65° C. For work-up, the reaction mixture was concentrated under reduced pressure and the residue was purified by flash chromatography (dichloromethane/methanol gradient, 20%→100% methanol) to give the title compound (150 mg) as a racemic mixture.

LC-MS (Method 2): $R_t$=0.87 min; MS (ESIpos): m/z=623 [M+H]$^+$ $^1$H-NMR (400 MHz, DMSO-d6) δ[ppm]: 1.231 (1.02), 1.907 (16.00), 2.209 (0.46), 2.518 (1.24), 2.523 (0.85), 3.309 (0.73), 3.360 (0.68), 3.879 (3.43), 4.204 (0.67), 4.259 (0.50), 4.292 (0.54), 4.642 (0.49), 4.675 (0.44), 5.759 (2.11), 6.882 (0.82), 6.899 (0.82), 7.079 (0.43), 7.390 (0.69), 7.409 (0.55), 7.450 (0.79), 7.471 (0.45), 7.508 (0.47), 7.512 (0.44), 7.517 (0.53), 7.525 (1.07), 7.532 (0.54), 7.537 (0.49), 7.541 (0.53), 7.778 (0.44), 7.796 (0.41), 7.860 (0.46), 7.878 (0.43), 8.231 (0.42).

The title compound (150 mg) was separated into enantiomers by preparative chiral HPLC, followed by flash chromatography, to give enantiomer 1 (26 mg, see Example 151) and enantiomer 2 (34 mg, see Example 152).

Preparative chiral HPLC method: Instrument: Sepiatec: Prep SFC100; column: Chiralpak ID 5 µm 250×30 mm; eluent A: CO$_2$, eluent B: 2-propanol+0.4 Vol-% diethylamine (99%); isocratic: 27% B; flow 100.0 ml/min temperature: 40° C.; BPR: 150 bar; MWD @ 280 nm Analytical chiral HPLC method: Instrument: Agilent: 1260, Aurora SFC-Module; column: Chiralpak ID 5 µm 100×4.6 mm; eluent A: CO$_2$, eluent B: 2-propanol+0.2 Vol-% diethylamine (99%); isocratic: 27% B; flow 4.0 ml/min; temperature: 37.5° C.; BPR: 100 bar; MWD @ 280 nm

Example 151

1-methyl-3-[2-(morpholin-4-yl)ethyl]-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid-N-ethylethanamine salt (Enantiomer 1)

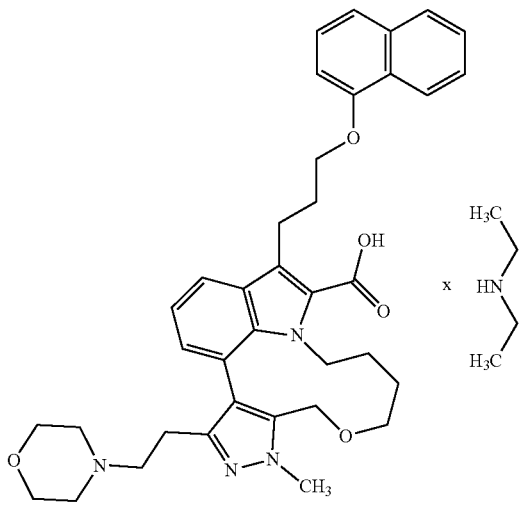

For the preparation of the racemic title compound see Example 150. Separation of enantiomers by preparative chiral HPLC (method see Example 150) gave the title compound (26 mg).

Analytical Chiral HPLC (method see Example 150): $R_t$=2.99 min.

$^1$H-NMR (400 MHz, DMSO-d6) δ[ppm]: 0.967 (0.81), 0.996 (1.11), 1.015 (1.11), 1.028 (3.58), 1.043 (3.91), 1.060 (1.02), 1.108 (6.20), 1.138 (1.53), 1.144 (8.03), 1.163 (16.00), 1.180 (8.00), 1.232 (0.99), 1.349 (0.96), 1.907 (0.63), 2.033 (7.13), 2.084 (5.65), 2.178 (2.23), 2.195 (3.43), 2.212 (2.53), 2.230 (1.59), 2.243 (1.68), 2.259 (2.14), 2.273 (4.39), 2.280 (3.43), 2.299 (4.45), 2.304 (4.12), 2.323 (2.02), 2.327 (2.86), 2.332 (2.41), 2.345 (0.78), 2.518 (7.13), 2.523 (5.02), 2.540 (1.47), 2.665 (1.35), 2.669 (1.77), 2.674 (1.26), 2.739 (0.57), 2.768 (1.05), 2.784 (1.02), 2.804 (0.60), 2.858 (1.77), 2.877 (5.47), 2.895 (5.35), 2.913 (1.68), 3.177 (0.81), 3.195 (1.35), 3.211 (1.44), 3.228 (2.02), 3.247 (1.53), 3.335 (10.74), 3.347 (13.68), 3.358 (10.68), 3.375 (3.94), 3.389 (2.80), 3.405 (2.47), 3.418 (2.08), 3.437 (1.83), 3.453 (1.11), 3.863 (0.81), 3.886 (0.72), 3.912 (1.14), 3.938 (0.75), 4.146 (2.74), 4.161 (5.71), 4.177 (2.77), 4.254 (3.31), 4.288 (3.67), 4.596 (1.17), 4.616 (4.72), 4.650 (3.85), 6.746 (2.11), 6.763 (2.44), 6.841 (3.61), 6.859 (3.91), 6.959 (2.26), 6.978 (3.34), 6.997 (1.98), 7.341 (2.77), 7.361 (5.08), 7.380 (3.85), 7.431 (5.26), 7.452 (3.22), 7.481 (0.75), 7.485 (1.17), 7.498 (3.13), 7.502 (3.07), 7.506 (3.91), 7.514 (7.01), 7.522 (4.06), 7.525 (3.49), 7.530 (3.58), 7.542 (1.35), 7.547 (0.78), 7.660 (2.59), 7.681 (2.38), 7.848 (3.10), 7.856 (1.65), 7.865 (2.62), 7.871 (2.68), 8.228 (2.65), 8.234 (2.44), 8.244 (1.29), 8.252 (2.62).

Example 152

1-methyl-3-[2-(morpholin-4-yl)ethyl]-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid-N-ethylethanamine salt (Enantiomer 2)

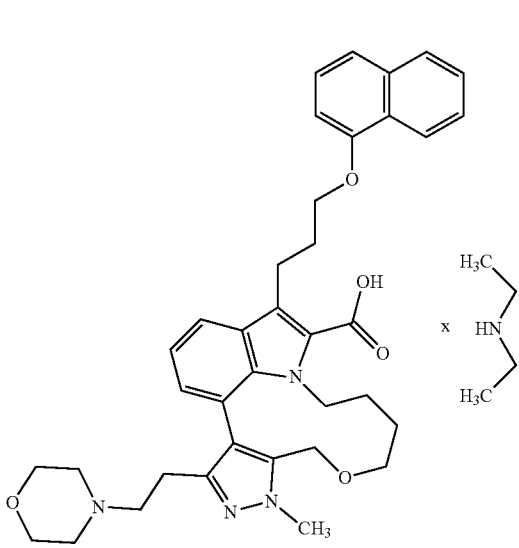

For the preparation of the racemic title compound see Example 150. Separation of enantiomers by preparative chiral HPLC (method see Example 150) gave the title compound (34 mg).

Analytical Chiral HPLC (method see Example 150): $R_t$=6.06 min.

$^1$H-NMR (400 MHz, DMSO-d6) δ[ppm]: 0.967 (1.07), 0.991 (0.72), 1.095 (1.13), 1.107 (4.32), 1.133 (7.39), 1.152 (16.00), 1.169 (7.20), 1.233 (0.66), 1.414 (0.58), 1.903 (1.47), 2.047 (4.64), 2.116 (0.43), 2.172 (1.53), 2.190 (2.39), 2.207 (1.75), 2.239 (0.85), 2.248 (0.72), 2.262 (1.51), 2.268 (1.60), 2.283 (3.56), 2.308 (2.71), 2.312 (2.75), 2.323 (1.90), 2.327 (2.28), 2.332 (2.02), 2.359 (0.83), 2.518 (5.69), 2.523 (4.05), 2.540 (2.28), 2.660 (0.47), 2.665 (0.98), 2.669 (1.34), 2.674 (0.94), 2.679 (0.51), 2.744 (0.83), 2.820 (1.73), 2.839 (5.43), 2.857 (5.18), 2.875 (1.64), 3.120 (0.49), 3.138 (0.87), 3.152 (0.92), 3.171 (1.19), 3.189 (0.72), 3.316 (4.58), 3.336 (9.33), 3.348 (11.31), 3.359 (8.07), 3.399 (2.09), 3.807 (0.60), 3.859 (1.04), 4.139 (1.81), 4.155 (3.71), 4.172 (1.83), 4.245 (2.15), 4.279 (2.39), 4.615 (2.60), 4.648 (2.39), 4.689 (0.81), 4.722 (0.70), 6.654 (1.70), 6.672 (1.92), 6.834 (2.22), 6.852 (2.41), 6.904 (1.77), 6.923 (2.49), 6.941 (1.58), 7.333 (1.60), 7.354 (3.00), 7.373 (2.28), 7.424 (3.39), 7.445 (2.07), 7.476 (0.49), 7.480 (0.75), 7.493 (2.00), 7.497 (2.02), 7.501 (2.56), 7.509 (4.37), 7.517 (2.54), 7.520 (2.26), 7.525 (2.22), 7.538 (0.83), 7.542 (0.51), 7.585 (1.94), 7.603 (1.79), 7.843 (2.05), 7.851 (1.04), 7.861 (1.75), 7.867 (1.73), 8.226 (1.73), 8.232 (1.62), 8.250 (1.60).

Example 153

(rac)-3-Ethyl-2,4-dimethyl-7-[3-(1-naphthyloxy)propyl]-2,10,11,12,13,15-hexahydropyrazolo[4',3':9,10][1,6]oxazacycloundecino[8,7,6-hi]indole-8-carboxylic acid

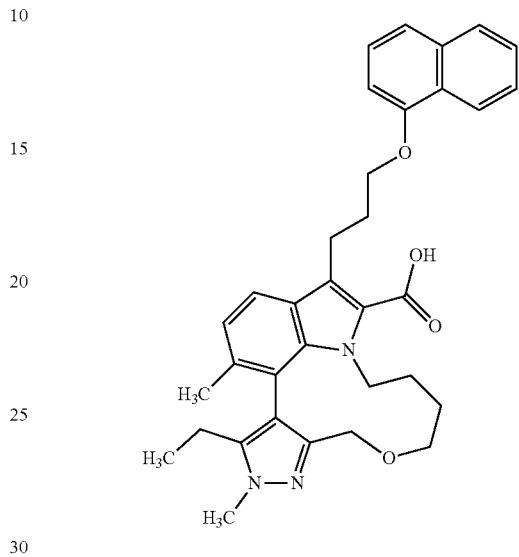

A mixture of (rac)-ethyl 3-ethyl-2,4-dimethyl-7-[3-(1-naphthyloxy)propyl]-2,10,11,12,13,15-hexahydropyrazolo[4',3':9,10][1,6]oxazacycloundecino[8,7,6-hi]indole-8-carboxylate (see Intermediate 282, 260 mg, 448 µmol), THF (22 mL), ethanol (11 mL) and lithium hydroxide (9 mL, 1.0 M in water) was stirred at 65° C. for 2 days. After concentration the residue was purified by flash chromatography (Biotage SNAP cartridge silica 25 g, methanol:dichloromethane) to give the title compound (215 mg, 87% yield).

LC-MS: m/z=552.4 [M+H]$^+$.

$^1$H-NMR (400 MHz, DMSO-d6), δ [ppm]=0.79 (3H), 0.94 (1H), 1.15 (1H), 1.21-1.36 (2H), 1.72 (1H), 2.00 (3H), 2.04-2.25 (4H), 2.54 (3H), 3.15 (1H), 3.23-3.31 (2H), 3.82 (1H), 4.13-4.25 (4H), 4.40 (1H), 6.87 (1H), 7.00 (1H), 7.38 (1H), 7.46 (1H), 7.53 (2H), 7.60 (1H), 7.87 (1H), 8.26 (1H), 12.94 (1H).

The title compound (215 mg) was separated into enantiomers by preparative chiral HPLC, followed by flash chromatography, to give enantiomer 1 (55 mg, see Example 154) and enantiomer 2 (55 mg, see Example 155).

Preparative chiral HPLC method: Instrument: Labomatic HD5000, Labocord-5000; Gilson GX-241, Labcol Vario 4000, column: Amylose SA 5µ 250×30 mm; eluent A: hexan+0.1 Vol-% diethylamine (99%); eluent B: ethanol; gradient: 20-63.5% B in 12 min; flow 40.0 ml/min; UV 280 nm Analytical chiral HPLC method: Instrument: Agilent HPLC 1260; column: Amylose SA 3µ 100×4.6 mm; eluent A: hexane+0.1 Vol-% diethylamine (99%); eluent B: ethanol; gradient: 20-50% B in 7 min; flow 1.4 ml/min; temperature: 25° C.; DAD 280 nm

Example 154

3-Ethyl-2,4-dimethyl-7-[3-(1-naphthyloxy)propyl]-2,10,11,12,13,15-hexahydropyrazolo[4',3':9,10][1,6]oxazacycloundecino[8,7,6-hi]indole-8-carboxylic acid-N-ethylethanamine salt (Enantiomer 1)

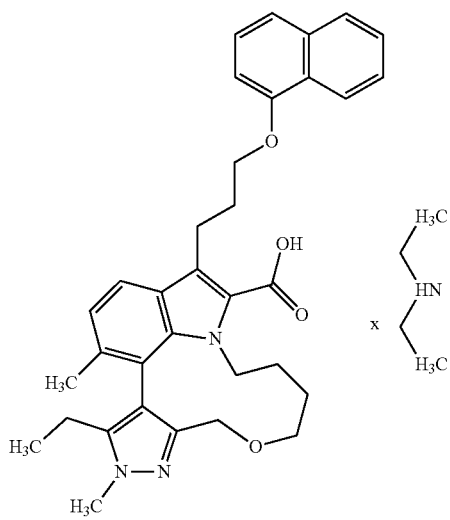

The mixture of atropisomers (rac)-3-Ethyl-2,4-dimethyl-7-[3-(1-naphthyloxy)propyl]-2,10,11,12,13,15-hexahydropyrazolo[4',3':9,10][1,6]oxazacycloundecino[8,7,6-hi]indole-8-carboxylic acid (215 mg, 390 µmol) was separated by preparative HPLC (for preparative chiral HPLC method see Example 153) to give enantiomer 1 with a retention time of 1.47 minutes (for analytical chiral HPLC method see Example 153) of the title compound (55 mg, 26%).

$^1$H-NMR (400 MHz, DMSO-d6), δ [ppm]=0.79 (3H), 1.00 (1H), 1.05-1.09 (1H), 1.06-1.17 (1H), 1.14 (3H), 1.18-1.35 (2H), 1.97 (3H), 2.04-2.12 (1H), 2.12-2.24 (3H), 2.83 (2H), 3.14 (1H), 3.19-3.31 (2H), 3.73 (1H), 3.85 (3H), 4.12-4.24 (3H), 4.27-4.41 (2H), 6.86 (1H), 6.93 (1H), 7.36 (1H), 7.44 (1H), 7.47-7.56 (3H), 7.86 (1H), 8.26 (1H).

Example 155

3-Ethyl-2,4-dimethyl-7-[3-(1-naphthyloxy)propyl]-2,10,11,12,13,15-hexahydropyrazolo[4',3':9,10][1,6]oxazacycloundecino[8,7,6-hi]indole-8-carboxylic acid-N-ethylethanamine salt (Enantiomer 2)

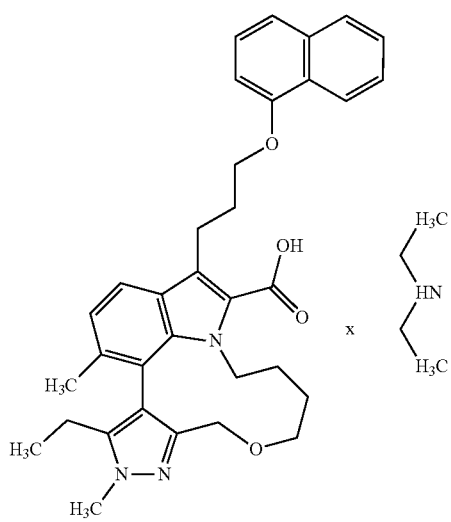

The mixture of atropisomers (rac)-3-Ethyl-2,4-dimethyl-7-[3-(1-naphthyloxy)propyl]-2,10,11,12,13,15-hexahydropyrazolo[4',3':9,10][1,6]oxazacycloundecino[8,7,6-hi]indole-8-carboxylic acid (215 mg, 390 µmol) was separated by preparative chiral HPLC (for method see Example 153) to give enantiomer 2 with a retention time of 2.51 minutes (for analytical chiral HPLC method see Example 153) of the title compound (55 mg, 26%).

$^1$H-NMR (400 MHz, DMSO-d6), δ [ppm]=0.79 (3H), 1.00 (1H), 1.05-1.09 (1H), 1.06-1.17 (1H), 1.14 (3H), 1.18-1.35 (2H), 1.97 (3H), 2.04-2.12 (1H), 2.12-2.24 (3H), 2.83 (2H), 3.14 (1H), 3.19-3.31 (2H), 3.73 (1H), 3.85 (3H), 4.12-4.24 (3H), 4.27-4.41 (2H), 6.86 (1H), 6.93 (1H), 7.36 (1H), 7.44 (1H), 7.47-7.56 (3H), 7.86 (1H), 8.26 (1H).

Example 156

(rac)-3-[(ethylamino)methyl]-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid

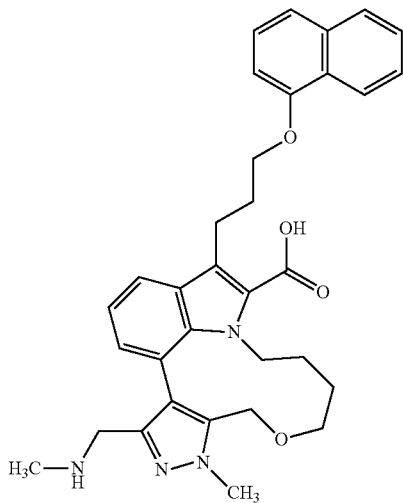

To a solution of (rac)-ethyl 3-[(ethylamino)methyl]-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (see Intermediate 259, 230 mg, 387 µmol) in THF (10 ml) and ethanol (5.0 ml) was added a solution of lithium hydroxide in water (5.0 ml, 1.0 M, 5.0 mmol). The reaction mixture was stirred for 23 hours at 65° C. For work-up, the reaction mixture was concentrated under reduced pressure and the residue was purified by flash chromatography (dichloromethane/methanol gradient, 0%→30% methanol) to give the title compound (162 mg) as a racemic mixture.

LC-MS (Method 2): $R_t$=0.89 min; MS (ESIpos): m/z=567 $[M+H]^+$ $^1$H-NMR (400 MHz, DMSO-d6) δ[ppm]: 0.834 (0.49), 0.852 (1.05), 0.868 (0.49), 0.893 (5.45), 0.911 (11.39), 0.929 (5.94), 0.967 (1.47), 0.984 (1.26), 1.031 (1.54), 1.046 (1.96), 1.108 (0.77), 1.232 (3.91), 1.273 (0.63), 1.368 (1.05), 1.907 (1.61), 1.987 (0.42), 2.160 (1.05), 2.177 (2.59), 2.195 (3.63), 2.211 (2.52), 2.229 (0.91), 2.332 (2.93), 2.336 (1.33), 2.518 (16.00), 2.522 (10.34), 2.546 (1.54), 2.563 (3.42), 2.581 (3.42), 2.598 (1.19), 2.673 (3.14), 2.678 (1.47), 2.794 (1.26), 2.824 (0.70), 3.082 (0.63), 3.165 (1.96), 3.186 (1.54), 3.200 (1.82), 3.219 (2.66), 3.239 (1.82), 3.261 (2.24), 3.279 (3.91), 3.298 (4.19), 3.313 (5.17), 3.330 (5.31), 3.396 (3.07), 3.409 (4.89), 3.425 (2.38), 3.444 (5.31), 3.527 (3.35), 3.563 (1.96), 3.770 (0.56), 3.788 (1.47), 3.829 (1.68), 3.847 (1.47), 3.877 (1.26), 4.165 (3.07), 4.181 (6.36), 4.197 (3.07), 4.230 (3.49), 4.264 (3.84), 4.560 (1.54), 4.594 (1.40), 4.637 (4.26), 4.670 (3.84), 5.759 (1.47), 6.738 (3.28), 6.755 (3.70), 6.861 (4.12), 6.878 (4.40), 6.954 (3.49), 6.974 (4.61), 6.992 (3.07), 7.349 (3.35), 7.369 (5.94), 7.388 (4.96), 7.432 (6.01), 7.453 (3.56), 7.478 (1.19), 7.483 (1.68), 7.495 (4.12), 7.500 (3.70), 7.505 (4.26), 7.512 (8.31), 7.520 (4.40), 7.524 (3.91), 7.528 (4.12), 7.541 (1.68), 7.546 (0.98), 7.650 (3.70), 7.668 (3.28), 7.848 (3.70), 7.856 (2.03), 7.865 (3.35), 7.871 (3.07), 8.226 (4.05), 8.231 (3.07), 8.242 (1.75), 8.250 (3.00).

Example 157

(rac)-7,9-dimethyl-1-[3-(naphthalen-1-yloxy)propyl]-11-[(3-oxomorpholin-4-yl)methyl]-4,5,6,7,8,9-hexahydropyrazolo[3',4':7,8][1,5]diazecino[9,10,1-hi]indole-2-carboxylic acid

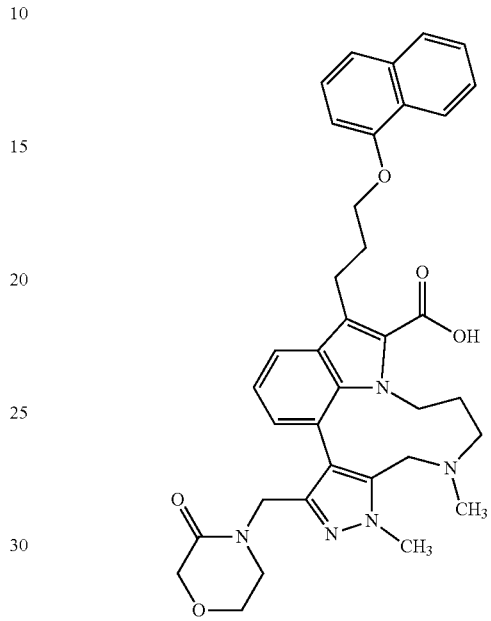

To a solution of (rac)-ethyl 7,9-dimethyl-1-[3-(naphthalen-1-yloxy)propyl]-11-[(3-oxomorpholin-4-yl)methyl]-4,5,6,7,8,9-hexahydropyrazolo[3',4':7,8][1,5]diazecino[9,10,1-hi]indole-2-carboxylate (see Intermediate 254, 120 mg, 185 µmol) in THF (6.0 ml) and ethanol (3.0 ml) was added a solution of lithium hydroxide in water (3.0 ml, 1.0 M, 3.0 mmol). The reaction mixture was stirred for 21 hours at 50° C. For work-up, the reaction mixture was concentrated under reduced pressure and the residue was purified by flash chromatography (dichloromethane/methanol gradient, 0%→100% methanol) to give the title compound (22 mg) as a racemic mixture.

$^1$H-NMR (400 MHz, DMSO-d6) δ[ppm]: 1.031 (0.45), 1.232 (1.50), 1.485 (0.73), 1.786 (0.48), 1.820 (0.57), 1.844 (0.45), 1.907 (1.95), 2.157 (1.12), 2.175 (1.63), 2.193 (1.34), 2.227 (10.51), 2.261 (0.61), 2.272 (0.61), 2.291 (0.48), 2.336 (0.64), 2.518 (7.41), 2.523 (5.11), 2.678 (0.67), 2.886 (0.51), 2.901 (0.67), 2.917 (0.70), 2.928 (0.51), 2.986 (1.50), 3.022 (1.63), 3.037 (0.54), 3.048 (0.86), 3.062 (0.73), 3.081 (0.64), 3.092 (0.45), 3.207 (0.57), 3.223 (0.64), 3.242 (0.89), 3.259 (0.86), 3.274 (1.18), 3.288 (1.66), 3.300 (2.36), 3.382 (0.99), 3.461 (1.72), 3.500 (2.78), 3.601 (3.93), 3.638 (2.91), 3.846 (16.00), 4.141 (1.47), 4.157 (3.03), 4.173 (1.47), 4.220 (1.31), 4.257 (3.19), 4.296 (2.81), 4.333 (1.15), 4.529 (0.64), 4.565 (0.61), 6.855 (2.14), 6.862 (1.15), 6.874 (2.52), 6.941 (1.25), 6.961 (1.66), 6.979 (0.89), 7.354 (1.34), 7.374 (2.55), 7.393 (2.04), 7.436 (2.65), 7.457 (1.50), 7.495 (0.51), 7.507 (1.66), 7.512 (2.97), 7.522 (3.29), 7.531 (3.07), 7.536 (1.92), 7.548 (0.57), 7.650 (1.28), 7.669 (1.09), 7.717 (0.48), 7.852 (1.53), 7.863 (0.80), 7.870 (0.99), 7.875 (1.31), 8.237 (1.34), 8.245 (0.99), 8.262 (1.21).

Example 158

(rac)-3-(methoxymethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid

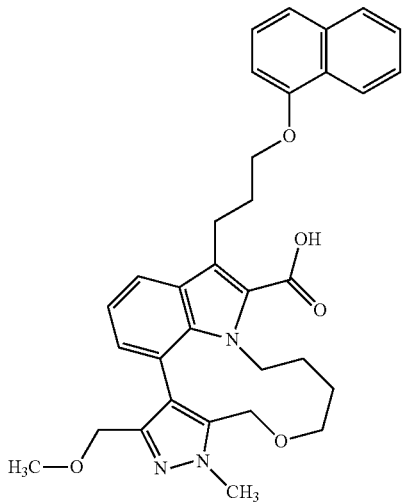 [SMILES: COCc1nn(C)c2c1-c1cccc3c(CCCOc4cccc5ccccc45)c(C(=O)O)n(c13)CCCCOC2]

To a solution of (rac)-ethyl 3-(methoxymethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (see Intermediate 286, 94.0 mg, 162 μmol) in THF (6.5 ml) and ethanol (3.2 ml) was added a solution of lithium hydroxide in water (3.2 ml, 1.0 M, 3.2 mmol). The reaction mixture was stirred for 18 hours at 50° C. For work-up, the reaction mixture was concentrated under reduced pressure and the residue was purified by flash chromatography (dichloromethane/ethanol gradient, 0%→10% ethanol) to give, after crystallization from water, the title compound (70 mg) as a racemic mixture.

LC-MS (Method 2): Rt=0.79 min; MS (ESIpos): m/z=554 [M+H]$^+$ $^1$H-NMR (400 MHz, DMSO-d6) δ[ppm]: 0.835 (2.03), 0.846 (2.10), 1.233 (2.20), 1.869 (0.80), 1.886 (1.03), 1.907 (0.97), 2.206 (1.30), 2.223 (1.03), 2.323 (1.40), 2.327 (2.03), 2.332 (1.67), 2.665 (1.43), 2.669 (2.07), 2.673 (1.70), 3.050 (16.00), 3.287 (1.10), 3.308 (2.10), 3.903 (10.40), 4.037 (1.47), 4.066 (2.10), 4.152 (0.67), 4.165 (2.57), 4.185 (1.37), 4.194 (2.57), 4.200 (2.83), 4.216 (1.83), 4.240 (1.40), 4.250 (1.47), 4.263 (0.73), 4.310 (0.93), 4.324 (1.00), 4.644 (1.00), 4.687 (1.17), 4.753 (1.03), 4.779 (1.17), 5.206 (0.93), 5.219 (1.40), 5.230 (1.07), 5.248 (0.80), 5.265 (0.73), 6.892 (1.37), 6.911 (1.50), 6.998 (0.77), 7.016 (1.50), 7.039 (1.17), 7.059 (1.47), 7.077 (0.67), 7.372 (0.83), 7.393 (1.80), 7.412 (1.40), 7.449 (2.03), 7.469 (1.17), 7.519 (2.07), 7.528 (2.33), 7.538 (2.23), 7.542 (1.80), 7.712 (1.13), 7.731 (1.07), 7.859 (1.13), 7.876 (0.90), 7.882 (1.10), 8.246 (0.97), 8.256 (0.83), 8.270 (1.07).

The title compound (70 mg) was separated into enantiomers by preparative chiral HPLC to give enantiomer 1 (6 mg, see Example 159) and enantiomer 2 (6 mg, see Example 160).

Preparative chiral HPLC method: Instrument: Sepiatec Prep SFC100; column: Chiralpak IC 5 μm 250×30 mm; eluent A: CO$_2$, eluent B: ethanol+0.4 Vol-% diethylamine (99%); isocratic: 15% B; flow 100.0 ml/min temperature: 40° C.; BPR: 150 bar; MWD @ 254 nm Analytical chiral HPLC method: Instrument: Agilent: 1260, Aurora SFC-Module; column: Chiralpak IC 5 μm 100×4.6 mm; eluent A: CO$_2$, eluent B: ethanol+0.2 Vol-% diethylamine (99%); isocratic: 15% B; flow 4.0 ml/min; temperature: 37.5° C.; BPR: 100 bar; MWD @ 254 nm

Example 159

3-(methoxymethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid-N-ethylethanamine salt (Enantiomer 1)

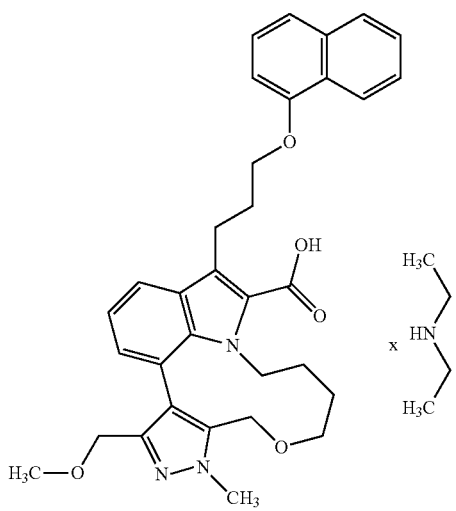

For the preparation of the racemic title compound see Example 158. Separation of enantiomers by preparative chiral HPLC (method see Example 158) gave the title compound (6 mg).

Analytical Chiral HPLC (method see Example 158): R$_t$=2.76 min.

LC-MS (agilent): Rt=1.32 min; MS (ESIpos): m/z=554 [M+H]$^+$ $^1$H-NMR (400 MHz, DMSO-d6) δ[ppm]: 0.852 (0.40), 0.932 (0.52), 1.116 (0.48), 1.123 (0.48), 1.136 (2.25), 1.154 (4.60), 1.173 (2.20), 1.232 (1.18), 1.881 (0.40), 2.004 (2.23), 2.007 (2.20), 2.180 (0.57), 2.198 (0.78), 2.216 (0.57), 2.332 (0.82), 2.518 (4.39), 2.522 (2.81), 2.673 (0.84), 2.859 (0.40), 2.877 (1.16), 2.895 (1.13), 3.053 (16.00), 3.240 (0.61), 3.258 (0.95), 3.276 (0.69), 3.897 (9.72), 4.029 (1.20), 4.058 (1.64), 4.167 (1.83), 4.176 (0.86), 4.192 (1.70), 4.196 (2.12), 4.206 (1.09), 4.236 (0.90), 4.317 (0.55), 4.637 (0.55), 4.643 (0.59), 4.681 (0.65), 4.686 (0.71), 4.742 (0.63), 4.747 (0.63), 4.768 (0.73), 4.773 (0.65), 5.205 (0.52), 5.222 (0.57), 5.248 (0.53), 5.265 (0.52), 6.886 (0.95), 6.903 (1.07), 6.916 (0.48), 6.934 (0.63), 6.984 (0.59), 7.003 (0.80), 7.022 (0.40), 7.364 (0.69), 7.384 (1.32), 7.403 (1.07), 7.440 (1.49), 7.461 (0.80), 7.508 (0.94), 7.513 (1.55), 7.523 (1.72), 7.532 (1.51), 7.536 (1.07), 7.632 (0.52), 7.651 (0.50), 7.853 (0.86), 7.857 (0.59), 7.865 (0.46), 7.868 (0.52), 7.871 (0.55), 7.877 (0.73), 8.245 (0.71), 8.252 (0.50), 8.269 (0.63).

Example 160

3-(methoxymethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid-N-ethylethanamine salt (Enantiomer 2)

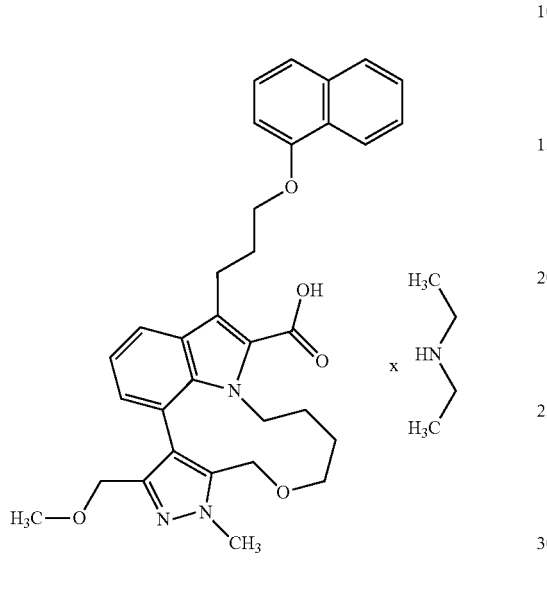

For the preparation of the racemic title compound see Example 158. Separation of enantiomers by preparative chiral HPLC (method see Example 158) gave the title compound (6 mg).

Analytical Chiral HPLC (method see Example 158): $R_t$=3.95 min.

LC-MS (agilent): Rt=1.32 min; MS (ESIpos): m/z=554 [M+H]$^+$ $^1$H-NMR (400 MHz, DMSO-d6) δ[ppm]: 0.833 (0.62), 0.852 (0.77), 0.915 (0.40), 0.932 (0.72), 0.950 (0.45), 1.073 (0.47), 1.089 (0.52), 1.099 (0.50), 1.106 (0.50), 1.116 (0.67), 1.123 (0.62), 1.136 (2.30), 1.154 (4.37), 1.172 (2.17), 1.232 (2.12), 1.256 (0.65), 1.881 (0.55), 2.005 (4.17), 2.008 (4.17), 2.182 (0.77), 2.198 (1.02), 2.218 (0.77), 2.331 (1.07), 2.336 (0.50), 2.518 (5.72), 2.523 (3.87), 2.673 (1.07), 2.864 (0.50), 2.883 (1.40), 2.900 (1.35), 2.919 (0.47), 3.053 (16.00), 3.247 (0.82), 3.266 (1.27), 3.284 (0.97), 3.898 (10.11), 4.030 (1.40), 4.059 (1.95), 4.109 (0.45), 4.132 (0.42), 4.167 (2.15), 4.177 (1.07), 4.196 (2.90), 4.207 (1.42), 4.238 (1.22), 4.262 (0.47), 4.317 (0.70), 4.349 (0.42), 4.643 (0.72), 4.686 (0.85), 4.743 (0.80), 4.769 (0.90), 5.206 (0.65), 5.222 (0.75), 5.248 (0.67), 5.265 (0.65), 5.291 (0.40), 6.887 (1.22), 6.906 (1.35), 6.929 (0.57), 6.946 (0.80), 6.993 (0.70), 7.012 (0.97), 7.030 (0.47), 7.365 (0.75), 7.386 (1.55), 7.405 (1.20), 7.442 (1.77), 7.462 (0.95), 7.510 (1.12), 7.514 (1.75), 7.524 (1.97), 7.533 (1.75), 7.538 (1.22), 7.644 (0.65), 7.664 (0.65), 7.854 (1.02), 7.872 (0.65), 7.878 (0.85), 8.245 (0.85), 8.254 (0.62), 8.270 (0.77).

Example 161

(rac)-3-methyl-7-[3-(5,6,7,8-tetrahydronaphthalen-1-yloxy)propyl]-1-(2,2,2-trifluoroethyl)-1,10,11,12,13,15-hexahydropyrazolo[4',3':9,10][1,6]oxazacycloundecino[8,7,6-hi]indole-8-carboxylic acid

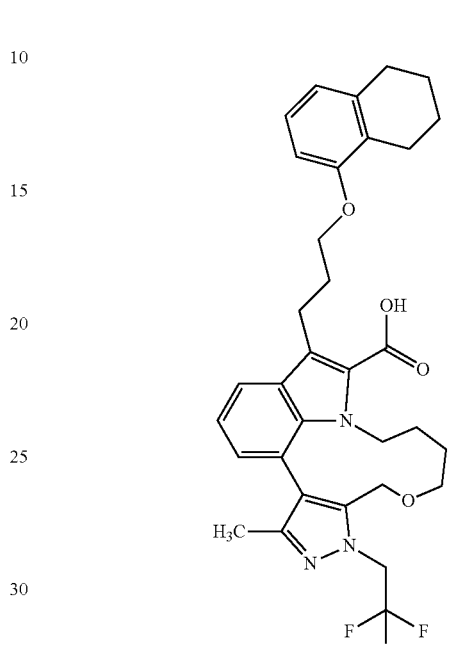

The title compound was isolated as a side product in the synthesis of (rac)-3-methyl-7-[3-(naphthalen-1-yloxy)propyl]-1-(2,2,2-trifluoroethyl)-1,10,11,12,13,15-hexahydropyrazolo[4',3':9,10][1,6]oxazacycloundecino[8,7,6-hi]indole-8-carboxylic acid (Example 109) (93.8 mg).

LC-MS (Method 1): $R_t$=1.68 min; MS (ESIpos): m/z=596.3 [M+H]$^+$ $^1$H-NMR (400 MHz, DMSO-d$_6$): δ [ppm]=13.15 (br s, 1H), 7.73 (dd, 1H), 7.10 (t, 1H), 6.99 (t, 1H), 6.89 (dd, 1H), 6.66-6.61 (m, 2H), 5.23-5.02 (m, 2H), 4.67 (d, 1H), 4.58-4.49 (m, 1H), 4.36 (d, 1H), 4.01-3.87 (m, 3H), 3.49-3.40 (m, 1H), 3.31-3.14 (m, 2H), 2.79 (dt, 1H), 2.71-2.60 (m, 4H), 2.06 (quin, 2H), 1.84 (s, 3H), 1.77-1.65 (m, 4H), 1.33-1.20 (m, 2H), 1.10-0.98 (m, 2H).

The title compound was separated into enantiomers using chiral preparative HPLC (93.8 mg) to give enantiomer 1 (23.8 mg, see example 162) and enantiomer 2 (21.1 mg, see example 163).

Preparative chiral HPLC method: Instrument: Sepiatec: Prep SFC100; column: Chiralpak IE 5 µm 250×30 mm; eluent A carbon dioxide, eluent B: ethanol+0.4 vol-% diethylamine (99%); isocratic: 15% B; flow 100.0 ml/min temperature: 40° C.; BPR: 150 bar; MWD 254 nm Analytical chiral HPLC method: Instrument: Agilent: 1260, Aurora SFC-Modul; column: Chiralpak IE 5 µm 100×4.6 mm; eluent A: carbon dioxide, eluent B: ethanol+0.2 vol-% diethylamine (99%); isocratic: 15% B; flow 4.0 ml/min; temperature: 37.5° C.; BPR: 100 bar; MWD 254 nm

Example 162

3-methyl-7-[3-(5,6,7,8-tetrahydronaphthalen-1-yloxy)propyl]-1-(2,2,2-trifluoroethyl)-1,10,11,12,13,15-hexahydropyrazolo[4',3':9,10][1,6]oxazacycloundecino[8,7,6-hi]indole-8-carboxylic acid-N-ethylethanamine salt (Enantiomer 1)

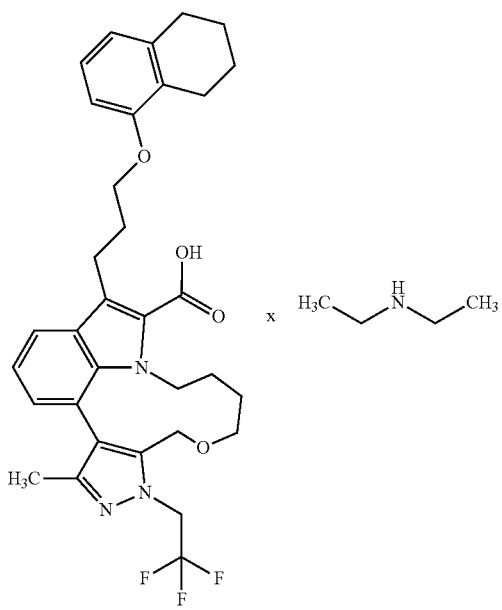

For the preparation of the racemic title compound and separation into enantiomers see Example 161.

Analytical Chiral HPLC (method see Example 161): $R_t$=2.88 min, ee>99%.

$^1$H-NMR (400 MHz, DMSO-d6) δ[ppm]: 0.968 (0.84), 1.018 (0.95), 1.066 (0.46), 1.108 (15.11), 1.133 (7.78), 1.145 (1.75), 1.151 (16.00), 1.169 (7.80), 1.232 (0.80), 1.672 (1.10), 1.678 (1.08), 1.691 (1.48), 1.703 (1.62), 1.717 (1.46), 1.734 (1.10), 1.856 (15.49), 2.024 (0.76), 2.040 (1.08), 2.057 (0.82), 2.323 (0.86), 2.327 (1.20), 2.331 (0.84), 2.518 (4.51), 2.523 (3.18), 2.603 (1.26), 2.619 (2.40), 2.633 (1.14), 2.665 (1.90), 2.669 (2.23), 2.674 (2.97), 2.691 (1.20), 2.744 (0.48), 2.760 (0.51), 2.774 (0.53), 2.831 (1.75), 2.848 (5.29), 2.867 (5.23), 2.885 (1.62), 3.047 (0.44), 3.062 (0.49), 3.080 (0.63), 3.196 (0.74), 3.214 (0.57), 3.230 (0.55), 3.399 (0.44), 3.416 (0.76), 3.428 (0.55), 3.433 (0.55), 3.446 (0.67), 3.761 (0.57), 3.938 (0.74), 3.948 (0.93), 3.955 (1.50), 3.963 (1.50), 3.970 (0.91), 3.979 (0.72), 4.307 (1.46), 4.341 (1.67), 4.634 (1.71), 4.669 (1.67), 4.684 (0.57), 4.719 (0.51), 4.982 (0.44), 5.004 (0.48), 5.021 (0.70), 5.043 (0.59), 5.135 (0.68), 5.158 (0.70), 5.174 (0.53), 5.197 (0.42), 6.607 (2.40), 6.625 (2.19), 6.629 (2.17), 6.682 (1.05), 6.698 (1.14), 6.951 (1.27), 6.962 (1.26), 6.970 (2.07), 6.981 (1.77), 6.990 (1.12), 6.999 (1.03), 7.569 (1.29), 7.587 (1.18).

Example 163

3-methyl-7-[3-(5,6,7,8-tetrahydronaphthalen-1-yloxy)propyl]-1-(2,2,2-trifluoroethyl)-1,10,11,12,13,15-hexahydropyrazolo[4',3':9,10][1,6]oxazacycloundecino[8,7,6-hi]indole-8-carboxylic acid-N-ethylethanamine salt (Enantiomer 2)

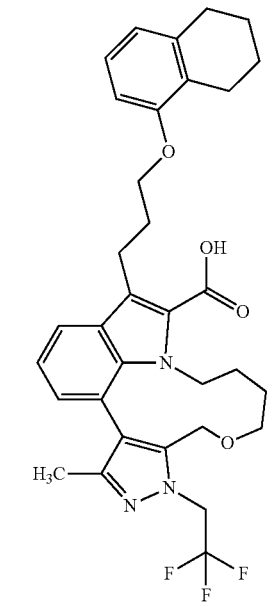 [SMILES: Cc1nn(CC(F)(F)F)c2c1-c1cccc3c(CCCOc4cccc5c4CCCC5)c(C(=O)O)n(c13)CCCCOC2]

For the preparation of the racemic title compound and separation into enantiomers see Example 161.

Analytical Chiral HPLC (method see Example 161): $R_t$=4.26 min, ee>99%.

Example 164

(rac)-3-Cyclopropyl-1-(2-methoxyethyl)-7-[3-(5,6,7,8-tetrahydronaphthalen-1-yloxy)propyl]-1,10,11,12,13,15-hexahydropyrazolo[4',3':9,10][1,6]oxazacycloundecino[8,7,6-hi]indole-8-carboxylic acid

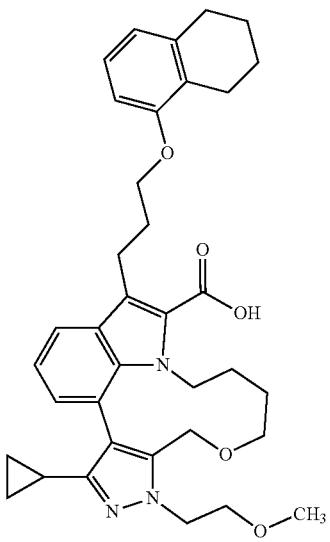 [SMILES: COCCn1nc(C2CC2)c2c1COCCCCn1c(C(=O)O)c(CCCOc3cccc4c3CCCC4)c3cccc-2c31]

A mixture of (rac)-ethyl 3-cyclopropyl-1-(2-methoxyethyl)-7-[3-(naphthalen-1-yloxy)propyl]-1,10,11,12,13,15-hexahydropyrazolo[4',3':9,10][1,6]oxazacycloundecino[8,7,6-hi]indole-8-carboxylate and (rac)-ethyl 3-cyclopropyl-1-(2-methoxyethyl)-7-[3-(5,6,7,8-tetrahydronaphthalen-1-yloxy)propyl]-1,10,11,12,13,15-hexahydropyrazolo[4',3':9,10][1,6]oxazacycloundecino[8,7,6-hi]indole-8-carboxylate (230 mg, see Intermediate 204), THF (12 mL), ethanol (8.6 mL) and lithium hydroxide (8.3 mL, 1.0 M in water) was stirred at 50° C. overnight. Water was added, the mixture was acidified by the addition of citric acid (pH 5-6) and extracted with dichloromethane. The organic layer was dried over sodium sulfate. After filtration and removal of the solvents the residue was purified by preparative HPLC [Instrument: Waters Autopurification system; column: Waters XBrigde C18 5μ 100×30 mm; eluent A: water+0.1 vol-% formic acid (99%), eluent B: acetonitrile; gradient: 0.00-0.50 min 30% B (25→70 mL/min), 0.51-5.50 min 60-85% B (70 mL/min), DAD scan: 210-400 nm] to give the title compound (47.8 mg, 22% yield) as mixture of atropisomers. For the corresponding naphthalen-1-yloxy compound, which was isolated as a second product, see Example 102.

LC-MS: m/z=598.3 [M+H]⁺.

¹H-NMR (500 MHz, DMSO-d6), δ [ppm]=0.53-0.64 (4H), 1.01 (2H), 1.17-1.37 (3H), 1.66-1.77 (4H), 2.06 (2H), 2.63 (2H), 2.69 (2H), 2.80 (1H), 3.13-3.22 (1H), 3.22-3.29 (4H), 3.40 (1H), 3.72 (2H), 3.98 (2H), 4.07 (1H), 4.19-4.31 (3H), 4.56 (1H), 4.64 (1H), 6.63 (2H), 6.88 (1H), 6.99 (1H), 7.09 (1H), 7.71 (1H), 13.11 (1H)

The title compound (32.0 mg) was separated into enantiomers by preparative chiral HPLC to give enantiomer 1 (1.4 mg, see Example 165) and enantiomer 2 (2.7 mg, see Example 166).

Preparative chiral HPLC method: Instrument: Sepiatec: Prep SFC100; column: Chiralpak IE 5 μm 250×30 mm; eluent A carbon dioxide, eluent B: ethanol+0.4 vol-% diethylamine (99%); isocratic: 27% B; flow 100.0 ml/min temperature: 40° C.; BPR: 135 bar; MWD 254 nm Analytical chiral HPLC method: Instrument: Agilent: 1260, Aurora SFC-Modul; column: Chiralpak IE 5 μm 100×4.6 mm; eluent A: carbon dioxide, eluent B: ethanol+ 0.2 vol-% diethylamine (99%); isocratic: 27% B; flow 4.0 ml/min; temperature: 37.5° C.; BPR: 100 bar; MWD 254 nm

Example 165

3-Cyclopropyl-1-(2-methoxyethyl)-7-[3-(5,6,7,8-tetrahydronaphthalen-1-yloxy)propyl]-1,10,11,12,13,15-hexahydropyrazolo[4',3':9,10][1,6]oxazacycloundecino[8,7,6-hi]indole-8-carboxylic acid-N-ethylethanamine salt (Enantiomer 1)

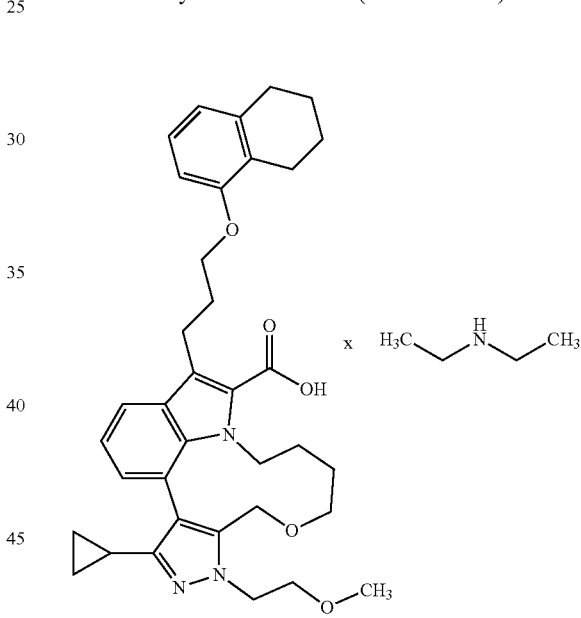

For the preparation of the racemic title compound and separation into enantiomers see Example 164.

Analytical Chiral HPLC (method see Example 164): R$_t$=2.37 min, ee>99%.

LC-MS: m/z=594.4 [M+H]⁺.

¹H-NMR (400 MHz, DMSO-d6), δ [ppm]=0.53-0.62 (4H), 0.94-1.05 (2H), 1.13-1.42 (2H), 1.16 (1.54H), 1.64-1.77 (4H), 2.05 (2H), 2.62 (2H), 2.65-2.71 (3H), 2.78 (1H), 2.90 (0.9H), 3.13 (1H), 3.23 (1H), 3.27 (3H), 3.30-3.46 (1H), 3.72 (2H), 3.97 (2H), 4.01 (1H), 4.19-4.30 (3H), 4.60 (1H), 4.64 (1H), 6.62 (2H), 6.81 (1H), 6.98 (1H), 7.04 (1H), 7.66 (1H)

Example 166

3-Cyclopropyl-1-(2-methoxyethyl)-7-[3-(5,6,7,8-tetrahydronaphthalen-1-yloxy)propyl]-1,10,11,12,13,15-hexahydropyrazolo[4',3':9,10][1,6]oxazacycloundecino[8,7,6-hi]indole-8-carboxylic acid-N-ethylethanamine salt (Enantiomer 2)

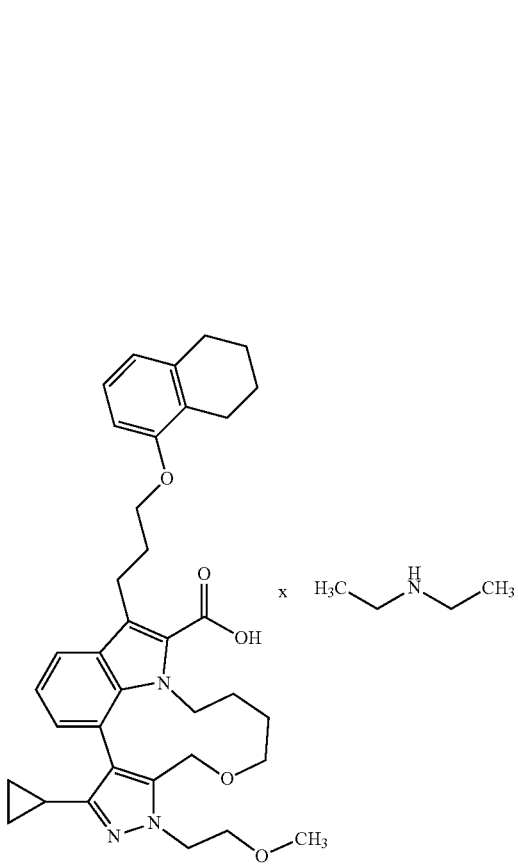

For the preparation of the racemic title compound and separation into enantiomers see Example 164.

Analytical Chiral HPLC (method see Example 164): $R_t$=3.34 min, ee>99%.

LC-MS: m/z=594.4 [M+H]$^+$.

$^1$H-NMR (400 MHz, DMSO-d6), δ [ppm]=0.53-0.62 (4H), 0.94-1.05 (2H), 1.13-1.42 (2H), 1.16 (1.5H), 1.64-1.77 (4H), 2.05 (2H), 2.62 (2H), 2.65-2.71 (3H), 2.78 (1H), 2.90 (1.0H), 3.13 (1H), 3.23 (1H), 3.27 (3H), 3.30-3.46 (1H), 3.72 (2H), 3.97 (2H), 4.01 (1H), 4.19-4.30 (3H), 4.60 (1H), 4.64 (1H), 6.62 (2H), 6.81 (1H), 6.98 (1H), 7.04 (1H), 7.66 (1H)

Example 167

(rac)-3-(ethoxymethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid

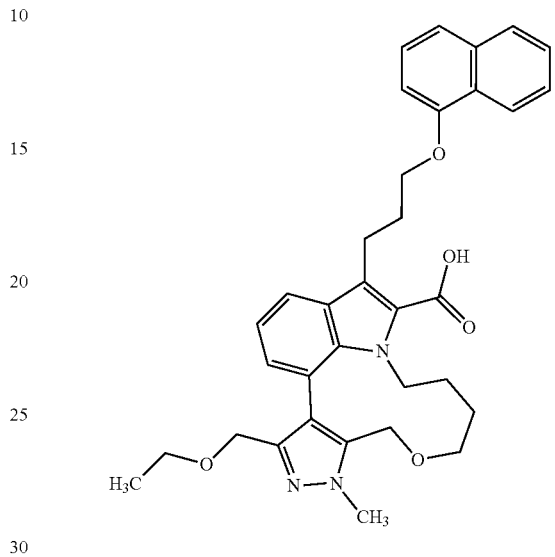

To a solution of a mixture of (rac)-ethyl 3-(ethoxymethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate and (rac)-ethyl 3-(ethoxymethyl)-1-methyl-7-[3-(5,6,7,8-tetrahydronaphthalen-1-yloxy)propyl]-1,10,11,12,13,15-hexahydropyrazolo[4',3':9,10][1,6]oxazacycloundecino[8,7,6-hi]indole-8-carboxylate (280 mg, see Intermediate 293) in THF (23 ml) and ethanol (11 ml) was added a solution of lithium hydroxide in water (9.4 ml, 1.0 M, 9.4 mmol). The reaction mixture was stirred for 24 hours at 50° C. For work-up, the reaction mixture was concentrated under reduced pressure and the residue was purified by HPLC (Instrument: Waters Autopurification system; column: Waters Kinetix C18 5μ 100×30 mm; eluent A: water+0.1 Vol-% formic acid (99%), eluent B: acetonitrile; gradient: 0.00-0.50 min 64% B (25→70 mL/min), 0.51-5.50 min 64-76% B (70 mL/min), DAD scan: 210-400 nm) to give the title compound (17.1 mg) and (rac)-3-(ethoxymethyl)-1-methyl-7-[3-(5,6,7,8-tetrahydronaphthalen-1-yloxy)propyl]-1,10,11,12,13,15-hexahydropyrazolo[4',3':9,10][1,6]oxazacycloundecino[8,7,6-hi]indole-8-carboxylic acid (Example 168, 44 mg) as racemic mixtures, respectively.

The title compound (17 mg) was separated into enantiomers by preparative chiral HPLC, followed by flash chromatography, to give enantiomer 1 (7 mg, see Example 169) and enantiomer 2 (7 mg, see Example 170).

Preparative chiral HPLC method: Instrument: Labomatic HD5000, Labocord-5000; Gilson GX-241, Labcol Vario 4000, column: Chiralpak IF 5μ 250×30 mm; eluent A: hexane+0.1 Vol-% trifluoroacetic acid; Eluent B: 2-propanol; gradient: 20-50% B in 20 min; flow 40.0 ml/min; UV 254 nm Analytical chiral HPLC method: Instrument: Agilent HPLC 1260; Säule: Chiralpak IF 3μ 100×4.6 mm; eluent A:

hexan+0.1 Vol-% trifluoroacetic acid; eluent B: 2-propanol; gradient: 20-50% B in 7 min; flow 1.4 ml/min; temperature: 25° C.; DAD 254 nm

Example 168

(rac)-3-(ethoxymethyl)-1-methyl-7-[3-(5,6,7,8-tetra-hydronaphthalen-1-yloxy)propyl]-1,10,11,12,13,15-hexahydropyrazolo[4',3':9,10][1,6]oxazacycloundecino[8,7,6-hi]indole-8-carboxylic acid

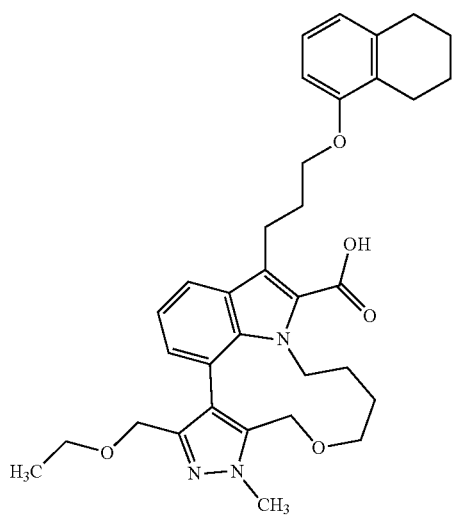

For preparation see Example 167.

The title compound (44 mg) was separated into enantiomers by preparative chiral HPLC, followed by flash chromatography, to give enantiomer 1 (12 mg, see Example 171) and enantiomer 2 (10 mg, see Example 172).

Preparative chiral HPLC method: Instrument: Labomatic HD5000, Labocord-5000; Gilson GX-241, Labcol Vario 4000, column: Chiralpak IF 5μ 250×30 mm; eluent A: hexane+0.1 Vol-% trifluoroacetic acid; Eluent B: 2-propanol; gradient: 20-50% B in 20 min; flow 40.0 ml/min; UV 254 nm Analytical chiral HPLC method: Instrument: Agilent HPLC 1260; Säule: Chiralpak IF 3μ 100×4.6 mm; eluent A: hexane+0.1 Vol-% trifluoroacetic acid; eluent B: 2-propanol; gradient: 20-50% B in 7 min; flow 1.4 ml/min; temperature: 25° C.; DAD 254 nm

Example 169

3-(ethoxymethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (Enantiomer 1)

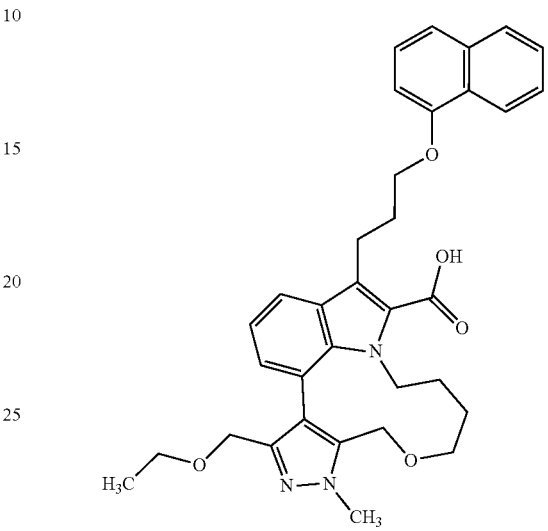

For the preparation of the racemic title compound see Example 167. After separation of enantiomers by preparative chiral HPLC (method see Example 167), the obtained product was further purified by flash chromatography (dichloromethane/methanol gradient, 0%→10% methanol) to give the title compound (7 mg).

Analytical Chiral HPLC (method see Example 167): $R_t$=2.02 min.

$^1$H-NMR (400 MHz, CHLOROFORM-d) δ [ppm]: 0.009 (7.77), 0.820 (0.64), 0.881 (5.06), 0.898 (10.64), 0.916 (5.25), 1.060 (0.58), 1.082 (0.56), 1.134 (0.72), 1.151 (1.30), 1.169 (1.05), 1.193 (3.38), 1.217 (1.24), 1.240 (0.76), 1.476 (0.50), 1.491 (0.46), 1.501 (0.47), 2.261 (0.40), 2.279 (1.11), 2.296 (1.64), 2.313 (1.20), 2.330 (0.44), 2.842 (0.43), 2.853 (0.47), 2.864 (0.64), 2.872 (0.50), 2.883 (0.47), 3.151 (0.92), 3.157 (0.56), 3.169 (1.03), 3.175 (1.50), 3.187 (0.47), 3.192 (1.44), 3.210 (0.49), 3.225 (0.48), 3.243 (1.46), 3.248 (0.46), 3.261 (1.45), 3.266 (1.03), 3.278 (0.53), 3.284 (0.91), 3.348 (0.52), 3.364 (0.69), 3.382 (1.09), 3.402 (0.58), 3.414 (1.14), 3.433 (1.87), 3.452 (1.20), 3.467 (1.05), 3.484 (0.55), 3.948 (16.00), 4.080 (0.43), 4.087 (0.50), 4.112 (0.95), 4.127 (2.10), 4.142 (10.50), 4.157 (1.86), 4.407 (1.42), 4.441 (2.24), 4.523 (2.68), 4.544 (0.53), 4.557 (2.18), 4.579 (0.46), 4.589 (0.73), 6.680 (1.88), 6.697 (1.97), 6.860 (1.77), 6.863 (1.88), 6.878 (2.33), 6.881 (2.16), 6.983 (2.02), 7.001 (1.88), 7.004 (2.31), 7.021 (1.63), 7.253 (1.43), 7.273 (2.64), 7.292 (2.23), 7.335 (2.59), 7.356 (1.48), 7.402 (0.64), 7.411 (3.62), 7.419 (2.86), 7.427 (3.15), 7.435 (3.87), 7.444 (0.73), 7.707 (1.93), 7.710 (2.07), 7.722 (1.65), 7.728 (2.56), 7.730 (2.75), 7.737 (1.41), 7.745 (1.25), 8.292 (1.30), 8.301 (1.10), 8.308 (1.03), 8.316 (1.18).

Example 170

3-(ethoxymethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (Enantiomer 2)

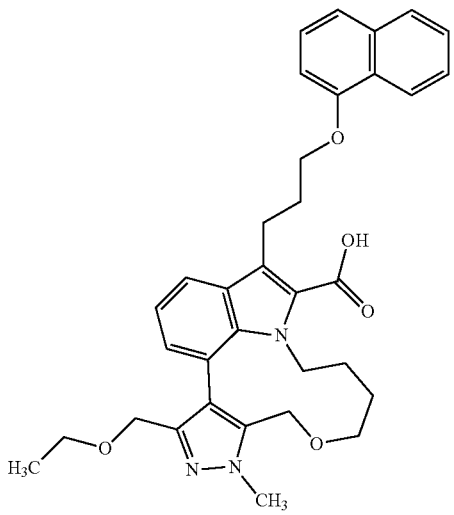 [SMILES: CCOCc1nn(C)c2c1-c1cccc3c(CCCOc4cccc5ccccc45)c(C(=O)O)n(c13)CCCCOC2]

For the preparation of the racemic title compound see Example 167. After separation of enantiomers by preparative chiral HPLC (method see Example 167), the obtained product was further purified by flash chromatography (dichloromethane/methanol gradient, 0%→10% methanol) to give the title compound (7 mg).

Analytical Chiral HPLC (method see Example 167): $R_t$=2.76 min.

$^1$H-NMR (400 MHz, CHLOROFORM-d) δ [ppm]: 0.009 (7.01), 0.820 (0.47), 0.880 (5.25), 0.897 (10.59), 0.914 (5.40), 1.060 (0.64), 1.080 (0.64), 1.134 (1.19), 1.151 (2.08), 1.168 (1.57), 1.193 (3.01), 1.218 (1.15), 1.476 (0.54), 1.492 (0.49), 1.502 (0.50), 2.261 (0.42), 2.278 (1.19), 2.296 (1.77), 2.313 (1.27), 2.329 (0.46), 2.842 (0.45), 2.853 (0.52), 2.863 (0.69), 2.872 (0.54), 2.883 (0.50), 3.151 (0.88), 3.156 (0.53), 3.169 (0.99), 3.174 (1.41), 3.192 (1.34), 3.210 (0.48), 3.225 (0.49), 3.243 (1.40), 3.260 (1.47), 3.265 (1.02), 3.278 (0.56), 3.283 (0.93), 3.348 (0.56), 3.364 (0.73), 3.383 (1.16), 3.397 (0.54), 3.402 (0.63), 3.414 (1.63), 3.432 (2.36), 3.451 (1.35), 3.466 (1.06), 3.483 (0.54), 3.918 (0.40), 3.950 (16.00), 4.077 (0.46), 4.084 (0.49), 4.113 (1.17), 4.126 (2.17), 4.142 (10.35), 4.156 (2.04), 4.173 (0.40), 4.406 (1.43), 4.440 (2.28), 4.522 (2.82), 4.557 (2.39), 4.579 (0.49), 4.590 (0.78), 6.679 (2.00), 6.697 (2.10), 6.859 (1.80), 6.863 (1.86), 6.877 (2.43), 6.880 (2.23), 6.983 (2.10), 7.001 (2.04), 7.003 (2.35), 7.021 (1.62), 7.251 (1.50), 7.272 (2.78), 7.291 (2.27), 7.334 (2.71), 7.354 (1.56), 7.401 (0.64), 7.410 (3.71), 7.418 (2.94), 7.425 (3.27), 7.434 (4.01), 7.443 (0.79), 7.707 (2.02), 7.711 (2.34), 7.721 (1.67), 7.728 (2.93), 7.730 (2.75), 7.736 (1.56), 7.744 (1.31), 8.291 (1.34), 8.300 (1.15), 8.307 (1.09), 8.315 (1.23).

Example 171

3-(ethoxymethyl)-1-methyl-7-[3-(5,6,7,8-tetrahydronaphthalen-1-yloxy)propyl]-1,10,11,12,13,15-hexahydropyrazolo[4',3':9,10][1,6]oxazacycloundecino[8,7,6-hi]indole-8-carboxylic acid (Enantiomer 1)

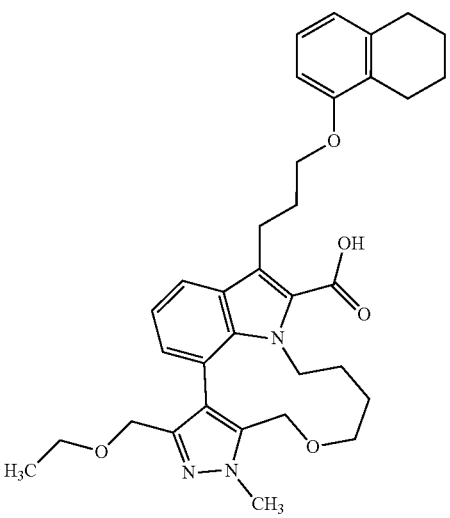 [SMILES: CCOCc1nn(C)c2c1-c1cccc3c(CCCOc4cccc5c4CCCC5)c(C(=O)O)n(c13)CCCCOC2]

For the preparation of the racemic title compound see Example 168. After separation of enantiomers by preparative chiral HPLC (method see Example 168), the obtained product was further purified by flash chromatography (dichloromethane/methanol gradient, 0%→10% methanol) to give the title compound (12 mg).

Analytical Chiral HPLC (method see Example 168): $R_t$=1.78 min.

$^1$H-NMR (400 MHz, CHLOROFORM-d) δ [ppm]: 0.000 (3.44), 0.877 (4.82), 0.895 (10.06), 0.912 (4.85), 1.076 (0.62), 1.096 (0.56), 1.125 (1.08), 1.143 (2.12), 1.160 (1.35), 1.185 (1.71), 1.222 (0.94), 1.475 (0.53), 1.491 (0.49), 1.501 (0.49), 1.688 (1.35), 1.694 (1.40), 1.708 (1.79), 1.720 (1.88), 1.734 (1.72), 1.752 (1.27), 2.122 (1.09), 2.139 (1.55), 2.156 (1.18), 2.173 (0.47), 2.688 (3.49), 2.701 (3.64), 2.714 (1.55), 2.844 (0.48), 2.864 (0.70), 2.884 (0.50), 2.897 (0.40), 3.150 (0.97), 3.156 (0.56), 3.168 (1.07), 3.173 (1.52), 3.191 (1.47), 3.208 (0.50), 3.222 (0.65), 3.239 (1.88), 3.257 (2.05), 3.262 (1.29), 3.274 (1.28), 3.280 (1.17), 3.291 (0.67), 3.301 (0.67), 3.321 (1.11), 3.339 (0.66), 3.355 (0.50), 3.406 (0.84), 3.423 (0.90), 3.441 (0.62), 3.447 (0.74), 3.465 (0.64), 3.476 (0.65), 3.909 (0.48), 3.945 (16.00), 3.954 (2.29), 3.969 (3.63), 3.985 (1.65), 4.077 (0.48), 4.104 (1.04), 4.113 (0.65), 4.134 (7.70), 4.415 (1.47), 4.449 (2.41), 4.525 (2.75), 4.559 (2.57), 4.585 (0.47), 4.595 (0.79), 6.526 (1.74), 6.546 (1.87), 6.608 (1.73), 6.627 (1.92), 6.859 (1.79), 6.861 (1.80), 6.877 (2.23), 6.879 (2.11), 6.938 (1.30), 6.958 (2.21), 6.978 (1.06), 7.013 (1.80), 7.032 (2.13), 7.051 (1.46), 7.676 (1.87), 7.679 (1.89), 7.696 (1.81), 7.699 (1.68).

Example 172

3-(ethoxymethyl)-1-methyl-7-[3-(5,6,7,8-tetrahydronaphthalen-1-yloxy)propyl]-1,10,11,12,13,15-hexahydropyrazolo[4',3':9,10][1,6]oxazacycloundecino[8,7,6-hi]indole-8-carboxylic acid (Enantiomer 2)

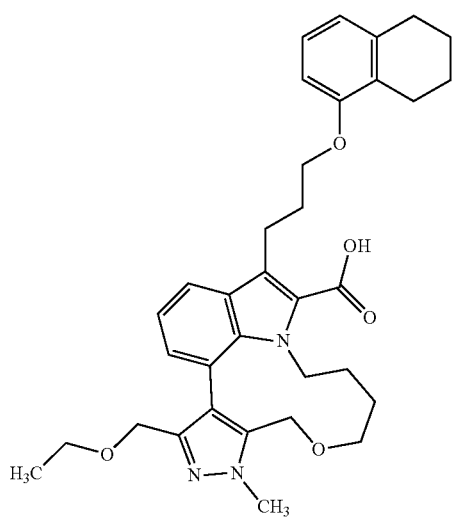 [SMILES: CCOCc1nn(C)c2c1-c1cccc3c(CCCOc4cccc5c4CCCC5)c(C(=O)O)n(c13)CCCCOC2]

For the preparation of the racemic title compound see Example 168. After separation of enantiomers by preparative chiral HPLC (method see Example 168), the obtained product was further purified by flash chromatography (dichloromethane/methanol gradient, 0%→10% methanol) to give the title compound (10 mg).

Analytical Chiral HPLC (method see Example 168): $R_t$=2.39 min.

$^1$H-NMR (400 MHz, CHLOROFORM-d) δ [ppm]: 0.000 (2.65), 0.877 (5.22), 0.895 (11.15), 0.912 (5.22), 1.078 (0.63), 1.097 (0.57), 1.125 (0.69), 1.143 (1.35), 1.160 (1.03), 1.184 (2.19), 1.215 (0.89), 1.224 (0.96), 1.250 (0.50), 1.476 (0.54), 1.491 (0.48), 1.502 (0.49), 1.688 (1.36), 1.693 (1.43), 1.707 (1.83), 1.720 (1.93), 1.734 (1.79), 1.752 (1.31), 2.122 (1.10), 2.139 (1.58), 2.157 (1.20), 2.174 (0.47), 2.676 (1.87), 2.687 (3.86), 2.701 (3.99), 2.714 (1.56), 2.844 (0.49), 2.855 (0.54), 2.864 (0.73), 2.884 (0.50), 2.896 (0.40), 3.150 (0.98), 3.156 (0.58), 3.168 (1.07), 3.173 (1.55), 3.191 (1.51), 3.208 (0.49), 3.222 (0.72), 3.239 (1.92), 3.256 (2.09), 3.262 (1.34), 3.274 (1.46), 3.279 (1.21), 3.292 (0.67), 3.297 (0.63), 3.302 (0.67), 3.322 (1.14), 3.340 (0.70), 3.357 (0.52), 3.407 (0.49), 3.424 (0.54), 3.447 (0.75), 3.465 (0.66), 3.476 (0.68), 3.943 (16.00), 3.954 (2.27), 3.970 (3.91), 3.985 (1.78), 4.078 (0.48), 4.104 (0.99), 4.115 (0.74), 4.134 (8.48), 4.415 (1.52), 4.449 (2.46), 4.525 (2.89), 4.559 (2.60), 4.586 (0.47), 4.596 (0.81), 6.526 (1.85), 6.546 (2.01), 6.607 (1.84), 6.626 (2.06), 6.859 (1.82), 6.862 (1.93), 6.877 (2.31), 6.879 (2.19), 6.938 (1.45), 6.957 (2.42), 6.977 (1.16), 7.013 (1.97), 7.032 (2.30), 7.051 (1.55), 7.676 (1.97), 7.679 (2.06), 7.696 (1.89), 7.699 (1.80).

Example 177

(rac)-3-(methoxymethyl)-1-methyl-7-[3-(naphthalen-1-yloxy)propyl]-1,11,12,13,14,16-hexahydro-10H-pyrazolo[3',4':3,4][1,7]oxazacyclododecino[5,6,7-hi]indole-8-carboxylic acid

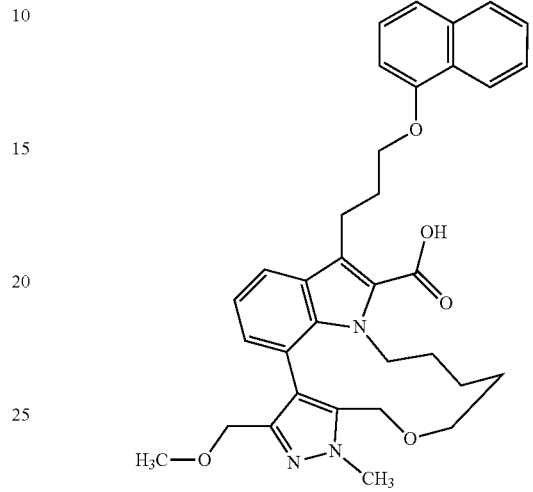

To a solution of (rac)-ethyl 3-(methoxymethyl)-1-methyl-7-[3-(naphthalen-1-yloxy)propyl]-1,11,12,13,14,16-hexahydro-10H-pyrazolo[3',4':3,4][1,7]oxazacyclododecino[5,6,7-hi]indole-8-carboxylate (84.0 mg, 141 µmol; see Intermediate 301) in THF (2.0 ml) and ethanol (1.0 ml) was added a solution of lithium hydroxide in water (1.0 ml, 1.0 M, 1.0 mmol). The reaction mixture was stirred for 12 days at room temperature. For work-up, the reaction mixture was concentrated under reduced pressure and the residue was purified by flash chromatography (dichloromethane/methanol gradient, 0%→10% methanol) to give the title compound (66 mg) as a racemic mixture.

LC-MS (Method 2): Rt=0.81 min; MS (ESIpos): m/z=568 [M+H]$^+$ $^1$H-NMR (400 MHz, DMSO-d6) δ[ppm]: 0.852 (0.46), 1.232 (0.95), 1.463 (0.52), 1.480 (0.65), 1.497 (0.42), 2.185 (0.50), 2.202 (0.65), 2.222 (0.52), 2.518 (3.10), 2.522 (2.06), 3.046 (0.70), 3.053 (16.00), 3.284 (0.63), 3.306 (1.00), 3.917 (8.72), 4.027 (1.28), 4.056 (1.68), 4.162 (1.84), 4.191 (2.24), 4.204 (1.62), 4.219 (1.17), 4.301 (0.44), 4.314 (0.48), 4.801 (1.65), 4.831 (0.93), 4.840 (0.83), 4.845 (0.56), 5.212 (0.57), 5.441 (0.44), 6.892 (0.91), 6.909 (0.98), 6.998 (0.53), 7.012 (0.98), 7.015 (0.94), 7.039 (0.94), 7.058 (1.04), 7.076 (0.50), 7.369 (0.74), 7.390 (1.30), 7.408 (1.09), 7.447 (1.42), 7.468 (0.76), 7.511 (0.94), 7.516 (1.68), 7.526 (1.87), 7.535 (1.71), 7.540 (1.04), 7.710 (0.70), 7.712 (0.71), 7.729 (0.67), 7.857 (0.80), 7.861 (0.57), 7.868 (0.41), 7.872 (0.49), 7.875 (0.53), 7.880 (0.68), 8.240 (0.70), 8.248 (0.50), 8.265 (0.65).

The title compound (63 mg) was separated into enantiomers by preparative chiral HPLC to give enantiomer 1 (16 mg, see Example 178) and enantiomer 2 (15 mg, see Example 179).

Preparative chiral HPLC method: Instrument: Agilent: 1260, Aurora SFC-Modul; column: Chiralpak IC 5 µm 100×4.6 mm; eluent A: CO$_2$, eluent B: 2-propanol+0.2 Vol-% diethylamine (99%); isocratic: 20% B; flow 4.0 ml/min; temperature: 37.5° C.; BPR: 100 bar; MWD @ 254 nm

Example 178

3-(methoxymethyl)-1-methyl-7-[3-(naphthalen-1-yloxy)propyl]-1,11,12,13,14,16-hexahydro-10H-pyrazolo[3',4':3,4][1,7]oxazacyclododecino[5,6,7-hi]indole-8-carboxylic acid-N-ethylethanamine salt
(Enantiomer 1)

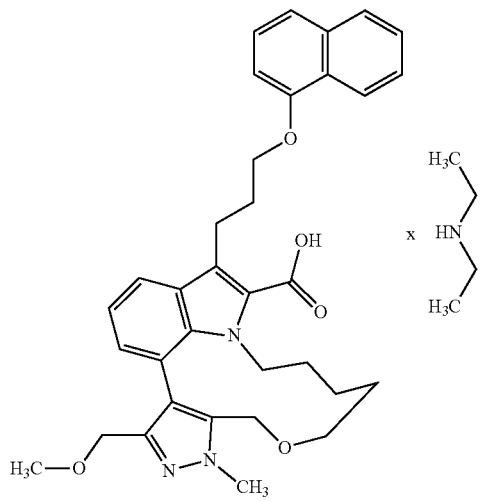

For the preparation of the racemic title compound and separation into its enantiomers see Example 177.

Analytical Chiral HPLC (method see Example 177): $R_t$=2.86 min.

$^1$H-NMR (400 MHz, DMSO-d6) δ[ppm]: 1.138 (0.69), 1.147 (2.48), 1.164 (5.05), 1.183 (2.66), 1.202 (0.53), 1.232 (0.68), 1.435 (0.45), 1.453 (0.81), 1.471 (1.03), 1.489 (0.69), 2.181 (0.83), 2.198 (1.14), 2.216 (0.86), 2.322 (0.46), 2.326 (0.62), 2.331 (0.46), 2.522 (2.36), 2.664 (0.47), 2.668 (0.63), 2.673 (0.46), 2.863 (0.62), 2.881 (1.90), 2.899 (1.83), 2.917 (0.59), 3.057 (16.00), 3.242 (0.99), 3.261 (1.53), 3.279 (1.11), 3.912 (10.56), 4.021 (1.62), 4.050 (2.43), 4.065 (0.44), 4.076 (0.46), 4.164 (2.61), 4.180 (2.33), 4.194 (4.03), 4.211 (2.53), 4.307 (1.15), 4.340 (0.75), 4.794 (2.42), 4.822 (1.18), 4.834 (1.13), 5.439 (0.56), 5.463 (0.43), 5.467 (0.45), 5.480 (0.43), 5.484 (0.42), 5.508 (0.44), 6.882 (1.34), 6.901 (1.47), 6.921 (0.79), 6.939 (1.16), 6.987 (0.94), 7.006 (1.30), 7.024 (0.62), 7.359 (0.83), 7.379 (1.70), 7.398 (1.28), 7.438 (1.94), 7.459 (1.08), 7.505 (1.20), 7.510 (1.97), 7.520 (2.20), 7.529 (2.05), 7.533 (1.31), 7.637 (0.98), 7.656 (0.91), 7.852 (1.11), 7.862 (0.61), 7.869 (0.77), 7.875 (0.92), 8.240 (0.95), 8.247 (0.77), 8.264 (0.90).

Example 179

3-(methoxymethyl)-1-methyl-7-[3-(naphthalen-1-yloxy)propyl]-1,11,12,13,14,16-hexahydro-10H-pyrazolo[3',4':3,4][1,7]oxazacyclododecino[5,6,7-hi]indole-8-carboxylic acid-N-ethylethanamine salt
(Enantiomer 2)

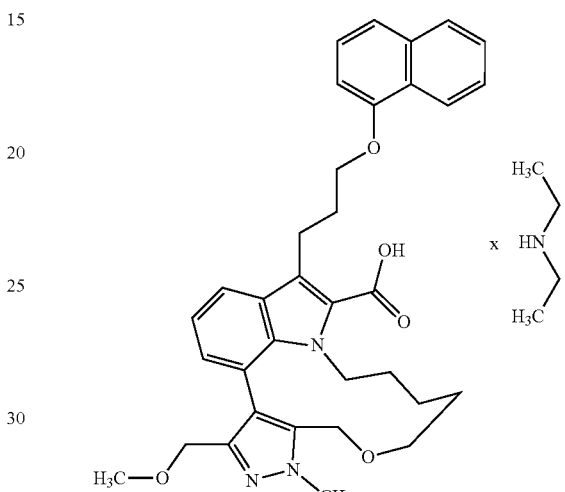

For the preparation of the racemic title compound and separation into its enantiomers see Example 177.

Analytical Chiral HPLC (method see Example 177): $R_t$=5.13 min.

$^1$H-NMR (400 MHz, DMSO-d6) δ[ppm]: 1.138 (0.64), 1.147 (2.20), 1.166 (4.42), 1.183 (2.36), 1.207 (0.50), 1.232 (0.68), 1.436 (0.43), 1.455 (0.79), 1.473 (1.01), 1.491 (0.67), 2.182 (0.82), 2.200 (1.12), 2.218 (0.86), 2.518 (3.05), 2.523 (2.06), 2.869 (0.53), 2.886 (1.59), 2.905 (1.57), 2.923 (0.48), 3.057 (16.00), 3.251 (0.99), 3.270 (1.51), 3.288 (1.17), 3.913 (10.68), 4.022 (1.61), 4.052 (2.34), 4.068 (0.43), 4.079 (0.46), 4.164 (2.52), 4.182 (2.25), 4.194 (3.36), 4.214 (2.43), 4.308 (1.15), 4.340 (0.75), 4.795 (2.31), 4.824 (1.14), 4.835 (1.07), 5.440 (0.52), 5.464 (0.43), 5.468 (0.42), 5.480 (0.41), 5.485 (0.41), 5.508 (0.43), 6.884 (1.28), 6.903 (1.37), 6.937 (0.75), 6.954 (1.16), 6.998 (0.94), 7.017 (1.30), 7.035 (0.61), 7.360 (0.77), 7.381 (1.62), 7.400 (1.20), 7.440 (1.90), 7.461 (1.05), 7.507 (1.15), 7.511 (1.94), 7.521 (2.12), 7.530 (2.02), 7.535 (1.30), 7.652 (0.94), 7.672 (0.90), 7.853 (1.09), 7.863 (0.60), 7.870 (0.77), 7.876 (0.91), 8.241 (0.92), 8.248 (0.75), 8.265 (0.88).

Example 180

(rac)-3-[(3,3-difluoroazetidin-1-yl)methyl]-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid

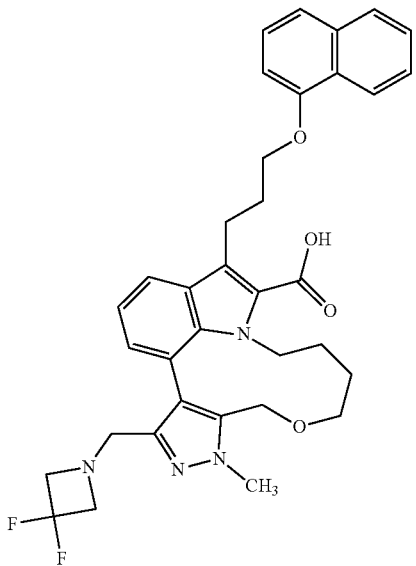 [SMILES: Cn1nc(CN2CC(F)(F)C2)c2c1COCCCCn1c(C(=O)O)c(CCCOc3cccc4ccccc34)c3cccc-2c31]

To a solution of (rac)-ethyl 3-[(3,3-difluoroazetidin-1-yl)methyl]-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (122 mg, 190 µmol; see Intermediate 302) in THF (2.7 ml) and ethanol (1.3 ml) was added a solution of lithium hydroxide in water (1.3 ml, 1.0 M, 1.3 mmol). The reaction mixture was stirred for 4 days at 50° C. For work-up, the reaction mixture was concentrated under reduced pressure and the residue was purified by flash chromatography (dichloromethane/ethanol gradient, 0%→20% ethanol) to give the title compound (113 mg) as a racemic mixture.

LC-MS (Method 2): Rt=0.85 min; MS (ESIpos): m/z=615 [M+H]$^+$ $^1$H-NMR (400 MHz, DMSO-d6) δ[ppm]: 0.902 (0.49), 0.992 (0.89), 1.010 (1.31), 1.024 (0.97), 1.036 (4.89), 1.053 (9.51), 1.071 (5.00), 1.233 (1.49), 1.309 (0.49), 2.066 (0.69), 2.198 (0.97), 2.216 (1.49), 2.233 (1.03), 2.337 (0.51), 2.518 (6.83), 2.523 (4.54), 2.679 (0.57), 2.777 (0.63), 2.789 (0.46), 2.807 (0.66), 3.200 (1.14), 3.233 (1.74), 3.269 (0.49), 3.284 (0.66), 3.302 (1.37), 3.354 (3.86), 3.371 (4.66), 3.385 (1.89), 3.397 (1.54), 3.402 (2.09), 3.418 (1.03), 3.423 (1.74), 3.435 (1.74), 3.440 (1.34), 3.452 (1.34), 3.887 (16.00), 3.906 (0.71), 3.958 (0.60), 3.970 (0.46), 4.180 (1.34), 4.195 (2.86), 4.210 (1.43), 4.227 (1.77), 4.261 (1.86), 4.342 (0.51), 4.355 (0.97), 4.368 (0.49), 4.494 (0.69), 4.505 (0.43), 4.529 (0.63), 4.634 (2.00), 4.668 (1.80), 6.846 (1.40), 6.866 (2.37), 6.885 (1.94), 7.022 (1.60), 7.042 (1.94), 7.060 (1.34), 7.357 (1.43), 7.378 (2.60), 7.397 (2.09), 7.443 (2.63), 7.464 (1.54), 7.493 (0.63), 7.506 (1.63), 7.510 (1.54), 7.514 (1.97), 7.522 (3.51), 7.530 (2.03), 7.533 (1.71), 7.538 (1.77), 7.550 (0.69), 7.749 (1.51), 7.752 (1.57), 7.770 (1.43), 7.855 (1.54), 7.863 (0.80), 7.873 (1.31), 7.879 (1.31), 8.229 (1.37), 8.235 (1.23), 8.245 (0.63), 8.253 (1.23).

The title compound (108 mg) was separated into enantiomers by preparative chiral HPLC to give enantiomer 1 (45 mg, see Example 181) and enantiomer 2 (46 mg, see Example 182).

Preparative chiral HPLC method: Instrument: Sepiatec: Prep SFC100; column: Chiralpak IA 5 µm 250×20 mm; eluent A CO$_2$, eluent B: ethanol+0.4 Vol-% diethylamine (99%); isocratic: 22% B; flow 80.0 ml/min temperature: 40° C.; BPR: 150 bar; MWD @ 254 nm Analytical chiral HPLC method: Instrument: Agilent: 1260, Aurora SFC-Modul; column: Chiralpak IA 5 µm 100×4.6 mm; eluent A: CO$_2$, eluent B: ethanol+0.4 Vol-% diethylamine (99%); isocratic: 22% B; flow 4.0 ml/min; temperature: 37.5° C.; BPR: 100 bar; MWD @ 254 nm

Example 181

3-[(3,3-difluoroazetidin-1-yl)methyl]-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid-N-ethylethanamine salt (Enantiomer 1)

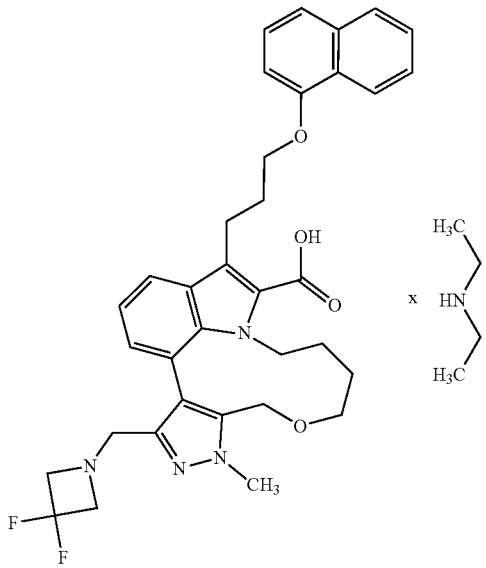

For the preparation of the racemic title compound and separation into its enantiomers see Example 180.

Analytical Chiral HPLC (method see Example 180): R$_t$=2.75 min.

LC-MS (Method 2): R$_t$=0.87 min; MS (ESIpos): m/z=615 [M+H]$^+$ $^1$H-NMR (400 MHz, DMSO-d6) δ[ppm]: 0.964 (0.50), 0.982 (0.55), 1.000 (0.44), 1.025 (0.46), 1.044 (0.42), 1.090 (0.44), 1.125 (7.16), 1.143 (16.00), 1.161 (7.31), 1.232 (0.70), 1.438 (0.39), 2.185 (0.92), 2.202 (1.38), 2.219 (1.01), 2.331 (0.98), 2.337 (0.46), 2.518 (5.60), 2.523 (3.92), 2.674 (1.03), 2.678 (0.50), 2.746 (0.50), 2.759 (0.42), 2.820 (1.69), 2.838 (5.10), 2.856 (5.08), 2.874 (1.60), 3.156 (0.46), 3.172 (0.48), 3.190 (0.72), 3.207 (1.34), 3.240 (1.58), 3.268 (0.57), 3.286 (1.14), 3.331 (5.21), 3.340 (4.95), 3.372 (5.32), 3.378 (4.44), 3.404 (3.41), 3.409 (2.58), 3.422 (0.70), 3.801 (0.53), 4.162 (1.05), 4.178 (2.12), 4.195 (1.09), 4.207 (1.64), 4.241 (1.62), 4.628 (1.84), 4.661 (1.93), 4.684 (0.50), 6.669 (0.98), 6.687 (1.07), 6.851 (1.58), 6.869 (1.71), 6.917 (1.05), 6.936

(1.53), 6.954 (0.94), 7.339 (1.18), 7.360 (2.19), 7.379 (1.66), 7.429 (2.28), 7.450 (1.38), 7.483 (0.50), 7.496 (1.36), 7.500 (1.29), 7.504 (1.64), 7.512 (3.00), 7.520 (1.69), 7.523 (1.44), 7.528 (1.53), 7.540 (0.57), 7.602 (1.14), 7.621 (1.07), 7.847 (1.36), 7.855 (0.72), 7.864 (1.20), 7.870 (1.14), 8.227 (1.16), 8.234 (1.09), 8.244 (0.59), 8.252 (1.12).

Example 182

3-[(3,3-difluoroazetidin-1-yl)methyl]-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid-N-ethylethanamine salt (Enantiomer 2)

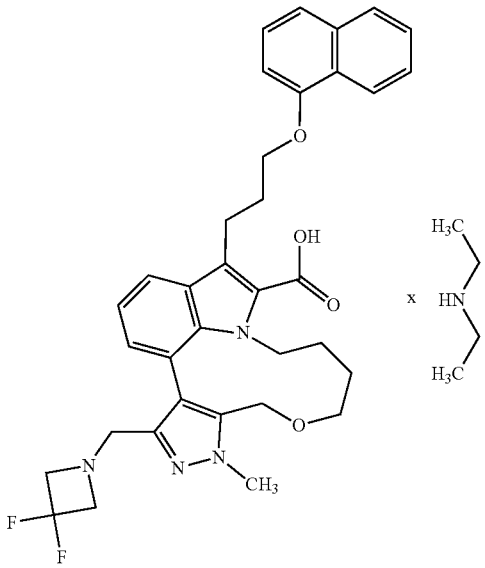

For the preparation of the racemic title compound and separation into its enantiomers see Example 180.
Analytical Chiral HPLC (method see Example 180): $R_t$=4.55 min.
LC-MS (Method 2): $R_t$=0.87 min; MS (ESIpos): m/z=615 [M+H]$^+$
$^1$H-NMR (400 MHz, DMSO-d6) δ[ppm]: 0.815 (0.41), 0.822 (0.46), 0.840 (0.41), 0.905 (0.46), 0.923 (0.41), 0.949 (0.53), 0.962 (0.63), 0.982 (0.69), 1.004 (0.61), 1.018 (0.58), 1.044 (0.51), 1.068 (0.43), 1.099 (0.51), 1.129 (7.47), 1.147 (16.00), 1.165 (7.34), 1.232 (0.89), 1.433 (0.48), 2.168 (0.41), 2.185 (1.14), 2.202 (1.70), 2.220 (1.22), 2.237 (0.43), 2.518 (6.50), 2.523 (4.47), 2.678 (0.58), 2.732 (0.48), 2.748 (0.61), 2.761 (0.53), 2.829 (1.70), 2.846 (5.13), 2.865 (5.03), 2.883 (1.57), 3.164 (0.56), 3.178 (0.63), 3.207 (1.52), 3.240 (1.93), 3.271 (0.76), 3.289 (1.50), 3.331 (5.79), 3.339 (6.40), 3.371 (6.22), 3.378 (5.31), 3.402 (3.96), 3.409 (3.02), 3.423 (0.86), 3.810 (0.63), 3.839 (0.43), 4.163 (1.32), 4.179 (2.64), 4.195 (1.37), 4.208 (1.93), 4.241 (1.96), 4.628 (2.36), 4.640 (0.74), 4.661 (2.23), 4.675 (0.66), 6.679 (1.17), 6.697 (1.30), 6.851 (1.88), 6.870 (2.03), 6.922 (1.24), 6.941 (1.85), 6.960 (1.09), 7.340 (1.35), 7.360 (2.57), 7.379 (1.88), 7.429 (2.72), 7.450 (1.63), 7.479 (0.41), 7.483 (0.61), 7.496 (1.63), 7.500 (1.57), 7.504 (1.93), 7.512 (3.58), 7.520 (1.98), 7.524 (1.75), 7.528 (1.80), 7.541 (0.66), 7.545 (0.41), 7.610 (1.37), 7.629 (1.30), 7.847 (1.60), 7.855 (0.86), 7.864 (1.42), 7.870 (1.37), 8.227 (1.37), 8.234 (1.32), 8.244 (0.71), 8.252 (1.32).

Example 183

(rac)-3-(methoxymethyl)-1,14-dimethyl-7-[3-(naphthalen-1-yloxy)propyl]-10,11,12,13,14,15-hexahydro-1H-pyrazolo[3',4':8,9][1,6]diazacycloundecino[10,11,1-hi]indole-8-carboxylic acid

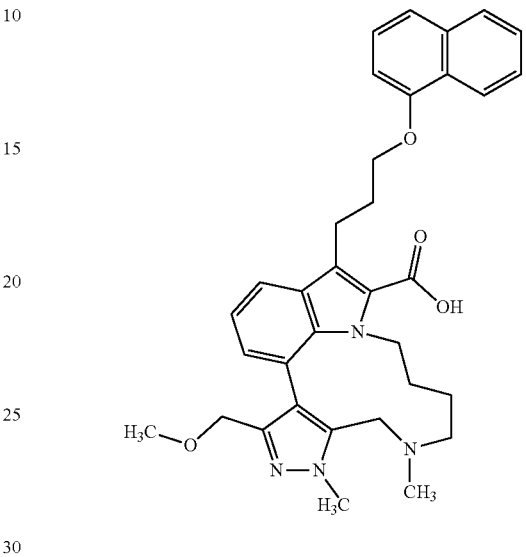

To a solution of (rac)-ethyl 3-(methoxymethyl)-1,14-dimethyl-7-[3-(naphthalen-1-yloxy)propyl]-10,11,12,13,14,15-hexahydro-1H-pyrazolo[3',4':8,9][1,6]diazacycloundecino[10,11,1-hi]indole-8-carboxylate (200 mg, 336 μmol; see Intermediate 306) in THF (4.8 ml) and ethanol (2.4 ml) was added a solution of lithium hydroxide in water (2.4 ml, 1.0 M, 2.4 mmol). The reaction mixture was stirred for 1 day at 50° C. and for 21 hours at 60° C. For work-up, the reaction mixture was concentrated under reduced pressure and the residue was purified by flash chromatography (dichloromethane/ethanol gradient, 0%→10% ethanol) to give the title compound (129 mg) as a racemic mixture.
LC-MS (Method 2): Rt=0.85 min; MS (ESIpos): m/z=567 [M+H]$^+$
$^1$H-NMR (400 MHz, DMSO-d6) δ[ppm]: 1.035 (3.03), 1.053 (5.79), 1.070 (3.14), 1.880 (0.42), 1.907 (1.47), 2.160 (6.08), 2.189 (0.67), 2.206 (0.98), 2.223 (0.66), 2.518 (2.72), 2.523 (1.83), 2.963 (16.00), 3.233 (0.96), 3.245 (0.40), 3.265 (1.24), 3.278 (0.64), 3.298 (0.42), 3.355 (0.84), 3.374 (0.43), 3.389 (0.41), 3.433 (0.53), 3.443 (0.51), 3.449 (0.51), 3.673 (1.01), 3.705 (0.91), 3.898 (9.20), 3.937 (1.04), 3.967 (2.18), 3.995 (2.16), 4.024 (0.90), 4.189 (0.84), 4.205 (1.76), 4.220 (0.82), 6.792 (0.84), 6.810 (0.96), 6.880 (1.11), 6.898 (1.17), 6.992 (0.83), 7.011 (1.14), 7.030 (0.73), 7.363 (0.78), 7.383 (1.51), 7.403 (1.16), 7.446 (1.60), 7.466 (0.90), 7.512 (1.00), 7.517 (1.58), 7.526 (1.81), 7.536 (1.57), 7.540 (1.15), 7.712 (0.90), 7.731 (0.84), 7.857 (0.89), 7.861 (0.62), 7.871 (0.56), 7.874 (0.56), 7.880 (0.77), 8.255 (0.78), 8.266 (0.53), 8.280 (0.73).
The title compound (126 mg) was separated into enantiomers by preparative chiral HPLC to give enantiomer 1 (60 mg, see Example 184) and enantiomer 2 (40 mg, see Example 185).
Preparative chiral HPLC method: Instrument: Sepiatec: Prep SFC100; column: Chiralpak ID 5 μm 250×30 mm; eluent A: $CO_2$, eluent B: 2-propanol+0.4 Vol-% diethylamine (99%); isocratic: 31% B; flow 100.0 ml/min temperature: 40° C.; BPR: 150 bar; MWD @ 254 nm Analytical chiral HPLC method: Instrument: Agilent: 1260, Aurora SFC-Modul; column: Chiralpak ID 5 μm 100×4.6 mm; eluent A: CO₂, eluent B: 2-propanol+0.2 Vol-% diethylamine (99%); isocratic: 31% B; flow 4.0 ml/min; temperature: 37.5° C.; BPR: 100 bar; MWD @ 254 nm

Example 184

3-(methoxymethyl)-1,14-dimethyl-7-[3-(naphthalen-1-yloxy)propyl]-10,11,12,13,14,15-hexahydro-1H-pyrazolo[3',4':8,9][1,6]diazacycloundecino[10,11,1-hi]indole-8-carboxylic acid-N-ethylethanamine salt
(Enantiomer 1)

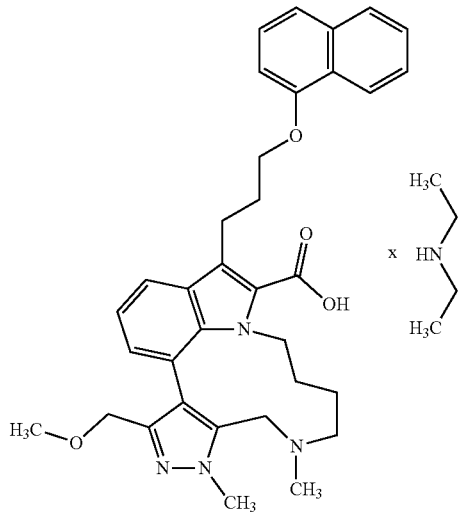

For the preparation of the racemic title compound and separation into its enantiomers see Example 183.

Analytical Chiral HPLC (method see Example 183): $R_t$=3.53 min.

LC-MS (Method 2): $R_t$=0.86 min; MS (ESIpos): m/z=567 [M+H]⁺

¹H-NMR (400 MHz, DMSO-d6) δ[ppm]: 1.027 (6.51), 1.042 (6.37), 1.137 (1.95), 1.154 (3.00), 1.172 (1.39), 2.116 (0.50), 2.159 (5.73), 2.184 (0.66), 2.202 (0.92), 2.219 (0.64), 2.518 (3.67), 2.523 (2.53), 2.540 (0.41), 2.882 (1.06), 2.900 (1.03), 2.967 (16.00), 3.227 (1.11), 3.238 (0.55), 3.259 (1.20), 3.369 (0.72), 3.665 (0.97), 3.697 (0.87), 3.895 (9.12), 3.934 (1.03), 3.963 (2.01), 4.002 (2.00), 4.032 (1.01), 4.183 (0.81), 4.198 (1.67), 4.214 (0.78), 6.739 (0.61), 6.756 (0.69), 6.875 (1.01), 6.893 (1.09), 6.959 (0.62), 6.978 (0.94), 6.996 (0.55), 7.357 (0.73), 7.377 (1.40), 7.396 (1.11), 7.441 (1.48), 7.461 (0.86), 7.509 (0.95), 7.513 (1.59), 7.523 (1.81), 7.532 (1.59), 7.536 (1.09), 7.664 (0.69), 7.683 (0.64), 7.854 (0.86), 7.864 (0.45), 7.868 (0.52), 7.871 (0.55), 7.877 (0.73), 8.253 (0.75), 8.261 (0.52), 8.277 (0.69).

Example 185

3-(methoxymethyl)-1,14-dimethyl-7-[3-(naphthalen-1-yloxy)propyl]-10,11,12,13,14,15-hexahydro-1H-pyrazolo[3',4':8,9][1,6]diazacycloundecino[10,11,1-hi]indole-8-carboxylic acid-N-ethylethanamine salt
(Enantiomer 2)

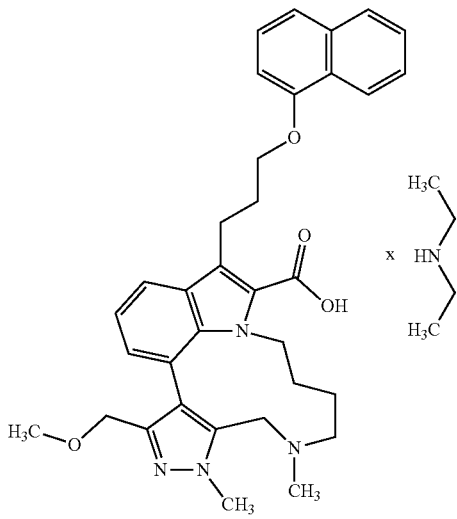

For the preparation of the racemic title compound and separation into its enantiomers see Example 183.

Analytical Chiral HPLC (method see Example 183): $R_t$=10.02 min.

LC-MS (Method 2): $R_t$=0.86 min; MS (ESIpos): m/z=567 [M+H]⁺

¹H-NMR (400 MHz, DMSO-d6) δ[ppm]: 1.027 (5.49), 1.042 (5.41), 1.137 (2.41), 1.156 (3.53), 1.174 (1.66), 1.875 (0.48), 1.907 (0.40), 2.116 (0.42), 2.158 (6.45), 2.183 (0.78), 2.202 (1.07), 2.219 (0.75), 2.518 (3.64), 2.523 (2.48), 2.540 (1.50), 2.862 (0.43), 2.879 (1.28), 2.898 (1.27), 2.916 (0.40), 2.968 (16.00), 3.202 (0.40), 3.226 (1.25), 3.235 (0.71), 3.259 (1.35), 3.386 (0.55), 3.664 (1.11), 3.696 (0.99), 3.857 (0.43), 3.895 (9.91), 3.934 (1.14), 3.963 (2.25), 4.003 (2.22), 4.033 (1.14), 4.182 (0.95), 4.198 (1.92), 4.213 (0.91), 4.593 (0.40), 6.732 (0.75), 6.749 (0.85), 6.873 (1.17), 6.891 (1.25), 6.954 (0.75), 6.973 (1.12), 6.992 (0.66), 7.355 (0.78), 7.376 (1.56), 7.395 (1.20), 7.440 (1.70), 7.460 (0.98), 7.507 (1.08), 7.512 (1.77), 7.522 (1.97), 7.531 (1.81), 7.536 (1.18), 7.658 (0.84), 7.678 (0.78), 7.852 (0.96), 7.864 (0.53), 7.868 (0.60), 7.870 (0.63), 7.876 (0.82), 8.252 (0.84), 8.260 (0.60), 8.276 (0.79).

Example 186

(rac)-2-methyl-7-[3-(naphthalen-1-yloxy)propyl]-3-(trifluoromethyl)-2,10,11,12,13,15-hexahydropyrazolo[4',3':9,10][1,6]oxazacycloundecino[8,7,6-hi]indole-8-carboxylic acid

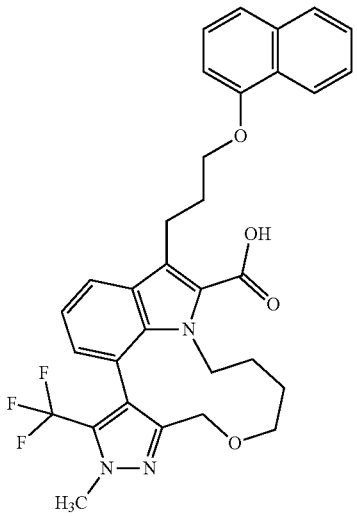 [SMILES: Cn1nc2c(c1C(F)(F)F)-c1cccc3c(CCCOc4cccc5ccccc45)c(C(=O)O)n(c13)CCCCOC2]

To a solution of (rac)-ethyl 2-methyl-7-[3-(naphthalen-1-yloxy)propyl]-3-(trifluoromethyl)-2,10,11,12,13,15-hexahydropyrazolo[4',3':9,10][1,6]oxazacycloundecino[8,7,6-hi]indole-8-carboxylate (130 mg, 215 µmol; see Intermediate 310) in THF (10 ml) and ethanol (5.0 ml) was added a solution of lithium hydroxide in water (4.3 ml, 1.0 M, 4.3 mmol). The reaction mixture was stirred for 2 days at 70° C. For work-up, the reaction mixture was concentrated under reduced pressure and the residue was purified by flash chromatography (dichloromethane/methanol gradient, 3.5%→10% methanol) to give the title compound (105 mg) as a racemic mixture.

LC-MS (Method 1): Rt=1.54 min; MS (ESIpos): m/z=578 [M+H]$^+$ $^1$H-NMR (400 MHz, DMSO-d6) δ[ppm]: 0.851 (0.94), 1.090 (1.09), 1.095 (1.16), 1.109 (3.09), 1.121 (1.24), 1.134 (1.19), 1.145 (1.24), 1.154 (3.97), 1.167 (2.78), 1.172 (7.57), 1.184 (1.04), 1.190 (3.80), 1.211 (1.01), 1.232 (5.22), 1.262 (0.63), 1.268 (0.68), 1.280 (0.71), 1.407 (0.86), 1.907 (2.38), 1.988 (12.51), 2.171 (0.58), 2.188 (1.75), 2.205 (2.71), 2.222 (1.80), 2.239 (0.61), 2.318 (0.46), 2.323 (1.06), 2.327 (1.52), 2.332 (1.06), 2.337 (0.46), 2.518 (5.67), 2.523 (4.13), 2.660 (0.48), 2.665 (1.09), 2.669 (1.52), 2.673 (1.06), 2.679 (0.48), 3.014 (0.51), 3.026 (0.71), 3.039 (1.14), 3.051 (1.24), 3.064 (0.66), 3.076 (0.56), 3.261 (0.73), 3.275 (1.14), 3.294 (2.28), 3.330 (16.00), 3.352 (2.28), 3.368 (1.39), 3.377 (1.16), 3.691 (0.48), 3.704 (0.63), 3.711 (0.63), 3.725 (1.09), 3.739 (0.73), 3.746 (0.78), 3.759 (0.53), 4.000 (0.96), 4.017 (2.84), 4.035 (2.81), 4.053 (1.82), 4.061 (13.70), 4.064 (14.33), 4.167 (1.42), 4.173 (1.62), 4.182 (2.86), 4.188 (2.86), 4.197 (1.65), 4.212 (0.66), 4.266 (3.49), 4.299 (4.05), 4.320 (0.58), 4.335 (0.94), 4.354 (1.11), 4.370 (0.86), 4.388 (0.48), 4.503 (3.70), 4.535 (3.04), 5.759 (0.41), 6.867 (3.01), 6.885 (3.32), 6.976 (2.00), 6.979 (2.13), 6.994 (3.44), 6.996 (3.27), 7.034 (3.37), 7.054 (3.80), 7.072 (2.13), 7.359 (2.38), 7.380 (4.38), 7.399 (3.52), 7.446 (4.33), 7.466 (2.53), 7.495 (0.41), 7.501 (0.89), 7.513 (2.91), 7.517 (5.01), 7.527 (5.57), 7.536 (4.89), 7.540 (3.34), 7.553 (0.99), 7.558 (0.41), 7.749 (2.71), 7.752 (2.86), 7.769 (2.66), 7.772 (2.56), 7.857 (2.46), 7.861 (1.75), 7.868 (1.34), 7.872 (1.52), 7.874 (1.62), 7.880 (2.15), 8.253 (2.20), 8.261 (1.47), 8.267 (1.09), 8.278 (2.08).

The title compound (100 mg) was separated into enantiomers by preparative chiral HPLC to give enantiomer 1 (27 mg, see Example 194) and enantiomer 2 (33 mg, see Example 195).

Preparative chiral HPLC method: Instrument: Labomatic HD5000, Labocord-5000; Gilson GX-241, Labcol Vario 4000, column: Chiralpak AD-H 5µ 250×30 mm; eluent A: hexane+0.1 Vol-% trifluoroacetic acid; eluent B: 2-propanol; gradient: 20-50% B in 20 min; flow 40.0 ml/min; UV 220 nm Analytical chiral HPLC method: Instrument: Agilent HPLC 1260; column: Chiralpak AD-H 3µ 100×4.6 mm; eluent A: hexane+0.1 Vol-% trifluoroacetic acid; eluent B: 2-propanol; gradient: 20-50% B in 7 min; flow 1.4 ml/min; temperature: 25° C.; DAD 220 nm

Example 187

(rac)-1,4-dimethyl-7-[3-(naphthalen-1-yloxy)propyl]-3-propyl-1,10,11,12,13,15-hexahydropyrazolo[4',3':9,10][1,6]oxazacycloundecino[8,7,6-hi]indole-8-carboxylic acid

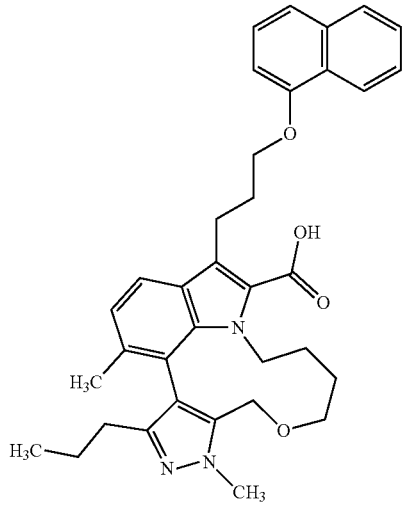 [SMILES: CCCc1nn(C)c2c1-c1c(C)ccc3c(CCCOc4cccc5ccccc45)c(C(=O)O)n(c13)CCCCOC2]

To a solution of (rac)-ethyl 1,4-dimethyl-7-[3-(naphthalen-1-yloxy)propyl]-3-propyl-1,10,11,12,13,15-hexahydropyrazolo[4',3':9,10][1,6]oxazacycloundecino[8,7,6-hi]indole-8-carboxylate (575 mg, 968 µmol; see Intermediate 315) in THF (47 ml) and ethanol (23 ml) was added a solution of lithium hydroxide in water (19 ml, 1.0 M, 19 mmol). The reaction mixture was stirred for 36 hours at 60° C. For work-up, the reaction mixture was concentrated under reduced pressure and the residue was purified by flash chromatography (dichloromethane/acetone gradient, 0%→40% acetone) to give the title compound (430 mg) as a racemic mixture.

LC-MS (Method 2): Rt=0.97 min; MS (ESIpos): m/z=566 [M+H]$^+$ $^1$H-NMR (400 MHz, DMSO-d6) δ[ppm]: 0.673 (3.96), 0.692 (9.23), 0.710 (4.35), 1.047 (0.65), 1.230 (1.46), 1.247 (1.80), 1.265 (2.55), 1.284 (2.29), 1.302 (1.10), 1.918

(11.89), 1.926 (2.03), 2.033 (1.15), 2.044 (1.29), 2.051 (2.14), 2.062 (1.98), 2.069 (1.16), 2.081 (0.99), 2.186 (0.92), 2.204 (1.39), 2.220 (0.96), 2.323 (0.43), 2.327 (0.61), 2.332 (0.42), 2.518 (2.38), 2.523 (1.67), 2.665 (0.56), 2.669 (0.74), 2.674 (0.54), 2.829 (0.67), 2.841 (0.50), 2.858 (0.70), 3.238 (0.40), 3.252 (0.59), 3.271 (1.01), 3.290 (0.72), 3.303 (1.24), 3.428 (0.64), 3.441 (0.67), 3.456 (0.62), 3.873 (16.00), 3.940 (0.53), 3.953 (0.86), 3.974 (0.51), 4.116 (1.61), 4.149 (1.79), 4.165 (1.25), 4.181 (2.23), 4.197 (1.09), 4.431 (0.71), 4.443 (0.43), 4.452 (0.41), 4.466 (0.65), 4.629 (1.85), 4.662 (1.72), 6.862 (1.67), 6.879 (1.78), 6.992 (2.21), 7.012 (2.39), 7.356 (1.30), 7.376 (2.35), 7.395 (1.83), 7.442 (2.40), 7.463 (1.41), 7.492 (0.52), 7.505 (1.41), 7.509 (1.32), 7.513 (1.67), 7.521 (3.22), 7.529 (1.72), 7.533 (1.51), 7.537 (1.64), 7.550 (0.61), 7.619 (2.45), 7.639 (2.20), 7.854 (1.40), 7.862 (0.75), 7.872 (1.25), 7.877 (1.20), 8.233 (1.25), 8.239 (1.15), 8.249 (0.62), 8.257 (1.18).

The title compound (425 mg) was separated into enantiomers by preparative chiral HPLC to give enantiomer 1 (160 mg, see Example 188) and enantiomer 2 (145 mg, see Example 189).

Preparative chiral HPLC method: Instrument: Sepiatec: Prep SFC100; column: Chiralpak ID 5 μm 250×30 mm; eluent A: $CO_2$, eluent B: 2-propanol+0.2 Vol-% diethylamine (99%); isocratic: 23% B; flow 100.0 ml/min temperature: 40° C.; BPR: 150 bar; MWD @ 254 nm Analytical chiral HPLC method: Instrument: Agilent: 1260, Aurora SFC-Modul; column: Chiralpak ID 5 μm 100×4.6 mm; eluent A: $CO_2$, eluent B: 2-propanol+0.2 Vol-% diethylamine (99%); isocratic: 23% B; flow 4.0 ml/min; temperature: 37.5° C.; BPR: 100 bar; MWD @ 254 nm Example 188

1,4-dimethyl-7-[3-(naphthalen-1-yloxy)propyl]-3-propyl-1,10,11,12,13,15-hexahydropyrazolo[4',3':9,10][1,6]oxazacycloundecino[8,7,6-hi]indole-8-carboxylic acid-N-ethylethanamine salt (Enantiomer 1)

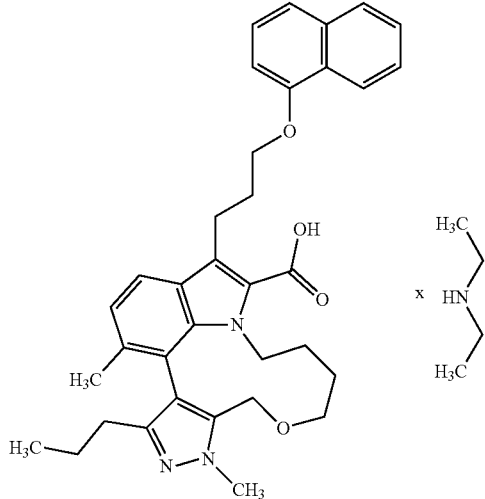

For the preparation of the racemic title compound and separation into its enantiomers see Example 187.
Analytical Chiral HPLC (method see Example 187): $R_t$=2.21 min.

$^1$H-NMR (400 MHz, DMSO-d6) δ[ppm]: 0.682 (5.64), 0.701 (13.01), 0.719 (6.20), 0.967 (1.38), 0.977 (0.67), 0.995 (0.71), 1.063 (0.62), 1.081 (0.64), 1.108 (15.78), 1.138 (7.49), 1.145 (1.58), 1.156 (15.69), 1.174 (7.29), 1.209 (0.45), 1.244 (0.48), 1.262 (1.84), 1.280 (3.47), 1.299 (3.50), 1.318 (1.95), 1.336 (0.85), 1.887 (16.00), 2.026 (0.74), 2.043 (1.53), 2.062 (3.46), 2.081 (2.96), 2.101 (1.22), 2.118 (0.68), 2.162 (0.43), 2.179 (1.30), 2.197 (1.97), 2.215 (1.41), 2.231 (0.48), 2.323 (0.67), 2.327 (0.95), 2.332 (0.65), 2.518 (3.58), 2.523 (2.50), 2.665 (0.70), 2.669 (0.98), 2.674 (0.73), 2.792 (0.56), 2.803 (0.70), 2.820 (0.62), 2.834 (2.12), 2.852 (5.60), 2.871 (5.46), 2.889 (1.63), 3.168 (0.67), 3.183 (0.78), 3.202 (1.19), 3.221 (0.62), 3.244 (0.78), 3.263 (1.49), 3.280 (1.15), 3.295 (1.29), 3.314 (1.22), 3.398 (0.68), 3.415 (1.01), 3.432 (0.91), 3.443 (0.88), 3.461 (0.50), 3.823 (0.47), 4.100 (2.25), 4.133 (2.47), 4.153 (1.16), 4.160 (1.24), 4.169 (2.26), 4.175 (2.26), 4.185 (1.24), 4.562 (0.74), 4.596 (0.68), 4.622 (2.70), 4.656 (2.42), 6.849 (2.29), 6.867 (2.51), 6.916 (2.59), 6.936 (2.82), 7.342 (1.88), 7.362 (3.38), 7.381 (2.70), 7.431 (3.35), 7.452 (2.03), 7.479 (0.56), 7.483 (0.82), 7.495 (2.09), 7.500 (1.97), 7.506 (2.33), 7.513 (5.16), 7.520 (4.20), 7.525 (2.48), 7.529 (2.62), 7.539 (2.42), 7.546 (0.79), 7.848 (1.97), 7.855 (1.07), 7.865 (1.91), 7.871 (1.72), 8.228 (1.78), 8.234 (1.63), 8.245 (0.90), 8.252 (1.61).

Example 189

1,4-dimethyl-7-[3-(naphthalen-1-yloxy)propyl]-3-propyl-1,10,11,12,13,15-hexahydropyrazolo[4',3':9,10][1,6]oxazacycloundecino[8,7,6-hi]indole-8-carboxylic acid-N-ethylethanamine salt (Enantiomer 2)

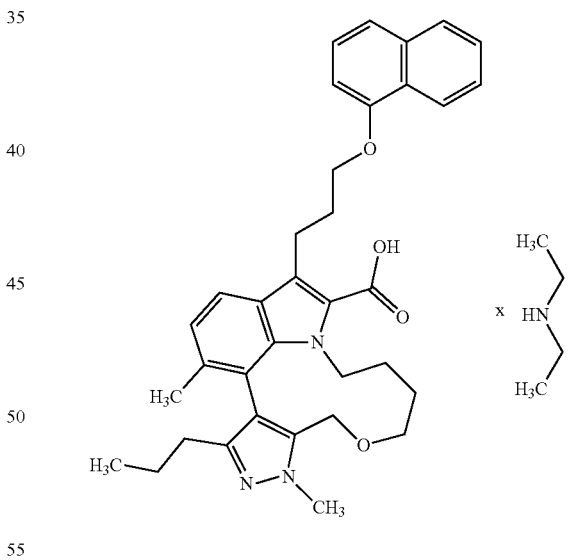

For the preparation of the racemic title compound and separation into its enantiomers see Example 187.
Analytical Chiral HPLC (method see Example 187): $R_t$=5.41 min.

$^1$H-NMR (400 MHz, DMSO-d6) δ[ppm]: 0.682 (5.19), 0.700 (12.23), 0.719 (5.77), 0.967 (1.11), 0.993 (0.69), 1.062 (0.68), 1.080 (0.69), 1.107 (15.72), 1.140 (6.82), 1.158 (14.16), 1.176 (6.30), 1.228 (0.77), 1.243 (0.57), 1.261 (1.89), 1.280 (3.51), 1.298 (3.48), 1.317 (2.03), 1.335 (0.94), 1.887 (16.00), 2.026 (0.73), 2.043 (1.56), 2.061 (3.48), 2.081 (3.07), 2.100 (1.26), 2.117 (0.68), 2.179 (1.44), 2.197 (2.12), 2.214 (1.50), 2.232 (0.51), 2.322 (0.55), 2.326 (0.76), 2.331 (0.55), 2.518 (2.80), 2.522 (1.90), 2.664 (0.58), 2.668 (0.78), 2.673 (0.60), 2.805 (0.77), 2.815 (0.71), 2.837 (2.07), 2.855 (5.18), 2.873 (5.09), 2.891 (1.57), 3.152 (0.41), 3.169 (0.72), 3.185 (0.87), 3.202 (1.30), 3.221 (0.73), 3.245 (0.93), 3.263 (1.61), 3.282 (1.27), 3.296 (1.35), 3.314 (1.16), 3.413 (1.14), 3.431 (1.05), 3.442 (1.00), 3.460 (0.57), 3.824 (0.54), 4.099 (2.25), 4.133 (2.52), 4.159 (1.39), 4.169 (2.44), 4.174 (2.44), 4.184 (1.35), 4.560 (0.82), 4.594 (0.78), 4.622 (2.66), 4.655 (2.38), 6.848 (2.39), 6.866 (2.58), 6.917 (2.71), 6.937 (2.88), 7.341 (1.70), 7.361 (3.24), 7.380 (2.39), 7.430 (3.39), 7.450 (2.02), 7.478 (0.54), 7.482 (0.76), 7.495 (2.03), 7.499 (1.94), 7.504 (2.27), 7.512 (4.55), 7.519 (4.81), 7.528 (2.47), 7.540 (2.98), 7.846 (1.99), 7.855 (1.09), 7.865 (1.86), 7.870 (1.70), 8.227 (1.75), 8.233 (1.68), 8.252 (1.71).

Example 190

(rac)- 2,3-dimethyl-7-[3-(1-naphthyloxy)propyl]-10,11,12,13,14,15-hexahydro-2H-pyrazolo[4',3':4,5]azacycloundecino[3,2,1-hi]indole-8-carboxylic acid

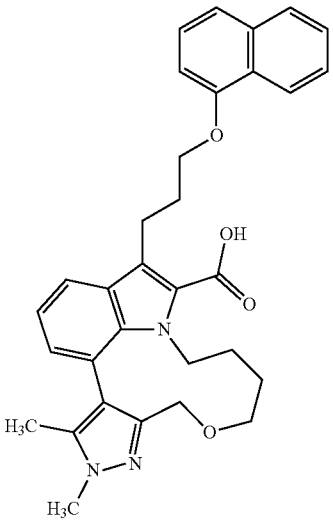 [SMILES: Cc1c2c(nn1C)COCCCCn1c(C(=O)O)c(CCCOc3cccc4ccccc34)c3cccc-2c31]

To a solution of (rac)- ethyl 2,3-dimethyl-7-[3-(1-naphthyloxy)propyl]-10,11,12,13,14,15-hexahydro-2H-pyrazolo[4',3':4,5]azacycloundecino[3,2,1-hi]indole-8-carboxylate (260 mg, 473 μmol; see Intermediate 326) in THF (23 ml) and ethanol (11 ml) was added a solution of lithium hydroxide in water (9.5 ml, 1.0 M, 9.5 mmol). The reaction mixture was stirred for 24 hours at 60° C. For work-up, the reaction mixture was concentrated under reduced pressure and the residue was purified by flash chromatography (dichloromethane/isopropanole gradient, 2%→10% isopropanol) to give the title compound (102 mg) as a racemic mixture.

LC-MS (Method 2): Rt=0.92 min; MS (ESIpos): m/z=522 [M+H]$^+$ $^1$H-NMR (400 MHz, DMSO-d6) δ[ppm]: 0.576 (0.49), 0.605 (0.55), 0.731 (0.50), 0.822 (0.44), 0.836 (0.44), 1.166 (0.95), 1.192 (0.75), 1.230 (0.44), 1.305 (0.93), 1.498 (0.46), 1.732 (0.49), 1.895 (15.84), 1.907 (0.76), 2.189 (1.02), 2.206 (1.57), 2.223 (1.09), 2.323 (0.76), 2.327 (1.02), 2.332 (0.68), 2.337 (0.41), 2.346 (0.56), 2.360 (0.48), 2.377 (0.43), 2.518 (3.11), 2.523 (2.33), 2.543 (0.51), 2.665 (0.55), 2.669 (0.78), 2.673 (0.55), 3.247 (0.58), 3.261 (0.63), 3.280 (1.04), 3.300 (0.64), 3.356 (1.32), 3.371 (0.78), 3.389 (0.75), 3.651 (0.48), 3.779 (16.00), 4.010 (0.41), 4.038 (0.69), 4.067 (0.46), 4.189 (1.40), 4.204 (2.93), 4.219 (1.37), 4.611 (0.65), 4.646 (0.59), 5.759 (11.10), 6.797 (1.67), 6.800 (1.76), 6.815 (1.98), 6.817 (1.92), 6.884 (1.82), 6.901 (1.96), 7.008 (1.78), 7.027 (2.09), 7.046 (1.50), 7.364 (1.40), 7.384 (2.61), 7.403 (2.12), 7.444 (2.68), 7.464 (1.50), 7.490 (0.60), 7.502 (1.62), 7.507 (1.52), 7.511 (1.84), 7.519 (3.67), 7.527 (1.94), 7.530 (1.79), 7.535 (1.82), 7.547 (0.74), 7.552 (0.45), 7.695 (1.73), 7.698 (1.78), 7.715 (1.67), 7.718 (1.61), 7.853 (1.55), 7.861 (0.84), 7.870 (1.39), 7.876 (1.32), 8.225 (1.34), 8.231 (1.24), 8.241 (0.68), 8.249 (1.28).

The title compound (90 mg) was separated into enantiomers by preparative chiral HPLC to give enantiomer 1 (39 mg, see Example 191) and enantiomer 2 (39 mg, see Example 192).

Preparative chiral HPLC method: Instrument: Sepiatec: Prep SFC100; column: Chiralpak IA 5 μm 250×30 mm; eluent A: CO$_2$, eluent B: ethanol+0.4 Vol-% diethylamine (99%); isocratic: 25% B; flow 100.0 ml/min temperature: 40° C.; BPR: 150 bar; MWD @ 254 nm Analytical chiral HPLC method: Instrument: Agilent: 1260, Aurora SFC-Modul; column: Chiralpak IA 5 μm 100×4.6 mm; eluent A: CO$_2$, eluent B: ethanol+0.2 Vol-% diethylamine (99%); isocratic: 25% B; flow 4.0 ml/min; temperature: 37.5° C.; BPR: 100 bar; MWD @ 254 nm Example 191

2,3-dimethyl-7-[3-(1-naphthyloxy)propyl]-10,11,12,13,14,15-hexahydro-2H-pyrazolo[4',3':4,5]azacycloundecino[3,2,1-hi]indole-8-carboxylic acid—N-ethylethanamine salt (Enantiomer 1)

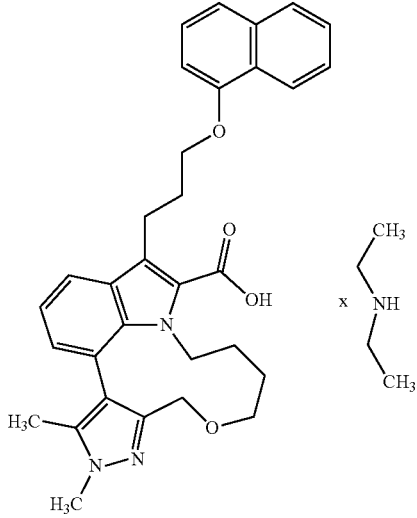

For the preparation of the racemic title compound and separation into its enantiomers see Example 190.

Analytical Chiral HPLC (method see Example 190): R$_t$=2.97 min.

$^1$H-NMR (400 MHz, DMSO-d6) δ[ppm]: 0.596 (0.52), 0.626 (0.59), 0.702 (0.42), 0.734 (0.53), 0.767 (0.51), 0.787 (0.45), 0.798 (0.51), 0.815 (0.51), 0.967 (0.56), 1.108 (1.10), 1.143 (5.00), 1.161 (9.94), 1.179 (4.86), 1.231 (0.42), 1.300 (0.55), 1.349 (0.45), 1.389 (0.53), 1.732 (0.51), 1.895 (16.00), 1.906 (0.64), 2.179 (1.04), 2.197 (1.55), 2.214 (1.13), 2.231 (0.43), 2.323 (0.93), 2.327 (1.13), 2.332 (0.78), 2.337 (0.52), 2.345 (0.62), 2.359 (0.53), 2.377 (0.48), 2.518

(4.10), 2.523 (2.86), 2.665 (0.64), 2.669 (0.88), 2.673 (0.62), 2.850 (1.11), 2.869 (3.56), 2.887 (3.43), 2.905 (1.04), 3.171 (0.58), 3.187 (0.61), 3.205 (0.87), 3.224 (0.53), 3.301 (1.30), 3.320 (2.27), 3.337 (2.17), 3.352 (1.84), 3.938 (0.68), 3.967 (0.42), 4.176 (1.45), 4.192 (3.02), 4.207 (1.39), 4.677 (0.65), 4.712 (0.59), 5.759 (4.44), 6.694 (1.29), 6.711 (1.45), 6.872 (1.85), 6.889 (1.98), 6.939 (1.33), 6.958 (1.84), 6.977 (1.16), 7.351 (1.36), 7.371 (2.53), 7.391 (1.98), 7.433 (2.69), 7.454 (1.52), 7.483 (0.59), 7.496 (1.59), 7.501 (1.55), 7.504 (1.89), 7.513 (3.47), 7.520 (1.95), 7.523 (1.68), 7.528 (1.78), 7.540 (0.62), 7.603 (1.39), 7.621 (1.30), 7.848 (1.53), 7.856 (0.82), 7.865 (1.34), 7.870 (1.30), 8.226 (1.33), 8.232 (1.24), 8.243 (0.68), 8.250 (1.27).

Example 192

2,3-dimethyl-7-[3-(1-naphthyloxy)propyl]-10,11,12,13,14,15-hexahydro-2H-pyrazolo[4',3':4,5]azacycloundecino[3,2,1-hi]indole-8-carboxylic acid—N-ethylethanamine salt (Enantiomer 2)

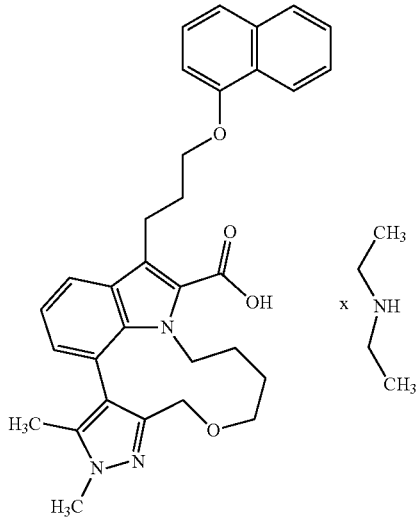

For the preparation of the racemic title compound and separation into its enantiomers see Example 190.

Analytical Chiral HPLC (method see Example 190): $R_t$=5.68 min.

$^1$H-NMR (400 MHz, DMSO-d6) δ[ppm]: 0.599 (0.58), 0.628 (0.66), 0.700 (0.47), 0.732 (0.61), 0.765 (0.61), 0.781 (0.51), 0.797 (0.58), 0.814 (0.56), 0.821 (0.53), 0.967 (0.41), 1.069 (0.51), 1.107 (1.05), 1.144 (5.57), 1.161 (10.86), 1.180 (5.30), 1.230 (0.44), 1.297 (0.63), 1.388 (0.56), 1.732 (0.57), 1.894 (16.00), 2.160 (0.41), 2.178 (1.14), 2.196 (1.68), 2.213 (1.22), 2.230 (0.47), 2.322 (0.93), 2.326 (1.09), 2.331 (0.76), 2.336 (0.56), 2.344 (0.71), 2.358 (0.65), 2.377 (0.58), 2.390 (0.48), 2.518 (3.63), 2.522 (2.58), 2.664 (0.54), 2.668 (0.75), 2.673 (0.53), 2.847 (1.27), 2.865 (3.80), 2.883 (3.76), 2.902 (1.15), 3.163 (0.63), 3.178 (0.69), 3.197 (0.96), 3.216 (0.57), 3.246 (0.41), 3.297 (1.31), 3.316 (2.14), 3.333 (2.02), 3.349 (1.90), 3.366 (1.24), 3.646 (0.43), 3.898 (0.43), 3.926 (0.74), 3.955 (0.47), 4.174 (1.53), 4.189 (3.14), 4.205 (1.45), 4.686 (0.70), 4.721 (0.65), 5.758 (3.30), 6.682 (1.46), 6.699 (1.62), 6.869 (1.93), 6.887 (2.07), 6.931 (1.41), 6.950 (2.01), 6.969 (1.22), 7.348 (1.32), 7.369 (2.60), 7.388 (2.03), 7.431 (2.84), 7.452 (1.62), 7.477 (0.40), 7.482 (0.60), 7.494 (1.63), 7.499 (1.62), 7.503 (1.88), 7.511 (3.56), 7.519 (1.98), 7.522 (1.81), 7.527 (1.74), 7.539 (0.66), 7.592 (1.55), 7.610 (1.44), 7.846 (1.66), 7.854 (0.87), 7.863 (1.44), 7.869 (1.35), 8.226 (1.40), 8.231 (1.31), 8.242 (0.73), 8.250 (1.31).

Example 193

(rac)-7,9,12-trimethyl-1-[3-(naphthalen-1-yloxy)propyl]-11-propyl-4,5,6,7,8,9-hexahydropyrazolo[3',4':7,8][1,5]diazecino[9,10,1-hi]indole-2-carboxylic acid

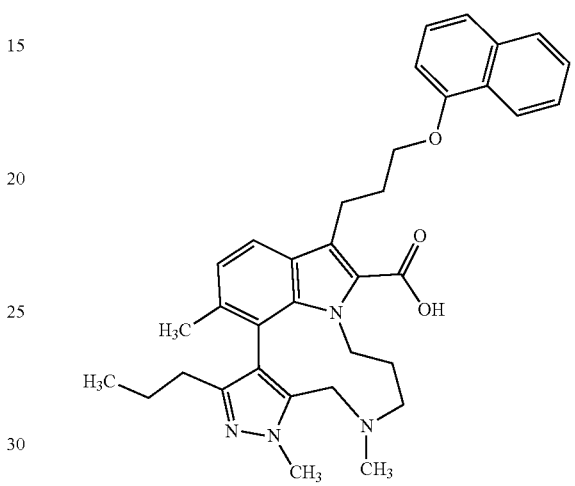

To a solution of (rac)-ethyl 7,9,12-trimethyl-1-[3-(naphthalen-1-yloxy)propyl]-11-propyl-4,5,6,7,8,9-hexahydropyrazolo[3',4':7,8][1,5]diazecino[9,10,1-hi]indole-2-carboxylate (480 mg, 810 µmol; see Intermediate 319) in THF (39 ml) and ethanol (19 ml) was added a solution of lithium hydroxide in water (16 ml, 1.0 M, 16 mmol). The reaction mixture was stirred for 4 days at 40° C. and 6 hours at 70° C. For work-up, the reaction mixture was concentrated under reduced pressure and the residue was purified by flash chromatography (dichloromethane/isopropanol gradient, 2.5%→10% isopropanol) to give the title compound (140 mg) as a racemic mixture.

LC-MS (Method 2): Rt=0.97 min; MS (ESIpos): m/z=565 [M+H]$^+$ $^1$H-NMR (400 MHz, DMSO-d6) δ[ppm]: 0.711 (5.21), 0.729 (11.92), 0.747 (5.77), 1.230 (0.68), 1.275 (0.46), 1.293 (1.84), 1.312 (3.38), 1.330 (3.30), 1.349 (1.99), 1.368 (0.75), 1.406 (0.56), 1.469 (0.45), 1.484 (0.53), 1.619 (0.64), 1.642 (0.62), 1.654 (0.72), 1.678 (0.59), 1.907 (0.52), 2.007 (16.00), 2.045 (0.55), 2.063 (0.85), 2.081 (1.41), 2.099 (2.09), 2.118 (1.18), 2.123 (1.25), 2.142 (2.42), 2.162 (2.26), 2.178 (2.56), 2.198 (2.29), 2.216 (1.20), 2.245 (15.20), 2.323 (0.53), 2.327 (0.75), 2.331 (0.52), 2.518 (2.88), 2.523 (1.98), 2.665 (0.56), 2.669 (0.71), 2.674 (0.50), 2.806 (1.96), 2.841 (2.04), 3.214 (0.64), 3.229 (0.82), 3.248 (1.39), 3.269 (1.16), 3.289 (1.72), 3.307 (1.65), 3.322 (2.20), 3.475 (0.51), 3.502 (0.91), 3.530 (0.55), 3.538 (0.46), 3.585 (2.01), 3.621 (1.88), 4.152 (1.72), 4.167 (3.63), 4.183 (1.71), 4.491 (0.90), 4.502 (0.55), 4.516 (0.53), 4.527 (0.87), 5.759 (5.96), 6.851 (2.28), 6.868 (2.46), 6.966 (2.97), 6.987 (3.18), 7.353 (1.74), 7.374 (3.24), 7.393 (2.58), 7.439 (3.31), 7.459 (1.93), 7.482 (0.56), 7.486 (0.77), 7.499 (1.92), 7.503 (1.77), 7.510 (2.09), 7.516 (4.24), 7.523 (2.10), 7.530 (1.86), 7.533 (2.11), 7.546

(0.84), 7.550 (0.57), 7.583 (3.13), 7.603 (2.80), 7.851 (1.97), 7.859 (1.08), 7.870 (1.93), 7.875 (1.66), 8.220 (1.69), 8.226 (1.66), 8.244 (1.60).

The title compound (130 mg) was separated into enantiomers by preparative chiral HPLC to give enantiomer 1 (48 mg, see Example 196) and enantiomer 2 (41 mg, see Example 197).

Preparative chiral HPLC method: Instrument: Sepiatec: Prep SFC100; column: Chiralpak ID 5 μm 250×30 mm; eluent A: $CO_2$, eluent B: 2-propanol+0.4 Vol-% diethylamine (99%); isocratic: 25% B; flow 100.0 ml/min temperature: 40° C.; BPR: 150 bar; MWD @ 254 nm Analytical chiral HPLC method: Instrument: Agilent: 1260, Aurora SFC-Modul; column: Chiralpak ID 5 μm 100×4.6 mm; eluent A: $CO_2$, eluent B: 2-propanol+0.2 Vol-% diethylamine (99%); isocratic: 25% B; flow 4.0 ml/min; temperature: 37.5° C.; BPR: 100 bar; MWD @ 254 nm Example 194

2-methyl-7-[3-(naphthalen-1-yloxy) propyl]-3-(trifluoromethyl)-2,10,11,12,13,15-hexahydropyrazolo[4',3':9,10][1,6]oxazacycloundecino[8,7,6-hi]indole-8-carboxylic acid (Enantiomer 1)

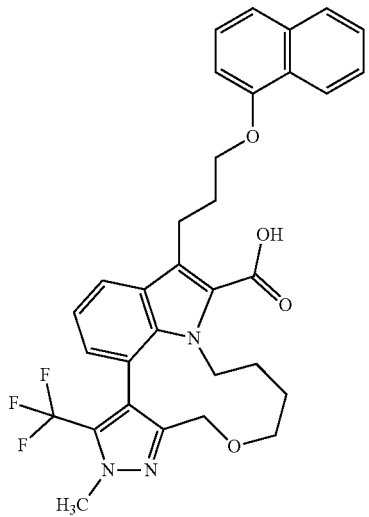 [SMILES: Cn1nc2c(c1C(F)(F)F)-c1cccc3c(CCCOc4cccc5ccccc45)c(C(=O)O)n(c13)CCCCOC2]

For the preparation of the racemic title compound and separation into its enantiomers see Example 186.
Analytical Chiral HPLC (method see Example 186): $R_t$=1.67 min.
$^1$H-NMR (400 MHz, DMSO-d6) δ[ppm]: 0.851 (0.74), 0.886 (0.41), 0.967 (0.81), 1.089 (1.58), 1.108 (10.67), 1.136 (1.58), 1.145 (1.50), 1.154 (1.43), 1.173 (1.27), 1.185 (1.41), 1.232 (4.59), 1.262 (0.91), 1.280 (1.15), 1.297 (0.62), 1.405 (0.96), 1.907 (0.43), 2.189 (2.08), 2.205 (3.15), 2.222 (2.17), 2.323 (1.03), 2.327 (1.41), 2.332 (1.03), 2.523 (5.92), 2.665 (1.07), 2.669 (1.41), 2.673 (1.05), 3.015 (0.64), 3.027 (0.84), 3.040 (1.39), 3.052 (1.48), 3.065 (0.84), 3.077 (0.72), 3.245 (0.43), 3.264 (0.86), 3.278 (1.29), 3.297 (2.51), 3.321 (2.51), 3.341 (1.67), 3.354 (2.17), 3.371 (1.70), 3.378 (1.50), 3.546 (2.17), 3.695 (0.81), 3.708 (1.00), 3.715 (1.00), 3.729 (1.46), 3.750 (1.10), 3.764 (0.79), 4.064 (16.00), 4.174 (1.98), 4.183 (3.41), 4.188 (3.41), 4.198 (2.15), 4.229 (0.53), 4.267 (3.53), 4.299 (4.23), 4.311 (0.86), 4.330 (1.27), 4.347 (1.39), 4.364 (1.07), 4.382 (0.60), 4.506 (4.01), 4.539 (3.22), 6.868 (3.22), 6.886 (3.61), 6.984 (2.39), 6.987 (2.70), 7.001 (4.27), 7.005 (4.13), 7.039 (3.61), 7.059 (4.18), 7.077 (2.24), 7.360 (2.17), 7.381 (4.25), 7.400 (3.30), 7.447 (4.59), 7.468 (2.70), 7.496 (0.48), 7.501 (0.88), 7.513 (3.03), 7.518 (4.97), 7.527 (5.42), 7.537 (5.04), 7.541 (3.51), 7.553 (1.05), 7.755 (3.15), 7.758 (3.30), 7.775 (3.03), 7.778 (3.06), 7.858 (2.60), 7.868 (1.55), 7.872 (1.74), 7.875 (1.84), 7.880 (2.29), 8.253 (2.34), 8.261 (1.74), 8.278 (2.17), 13.188 (0.48).

Example 195

2-methyl-7-[3-(naphthalen-1-yloxy)propyl]-3-(trifluoromethyl)-2,10,11,12,13,15-hexahydropyrazolo[4',3':9,10][1,6]oxazacycloundecino[8,7,6-hi]indole-8-carboxylic acid (Enantiomer 2)

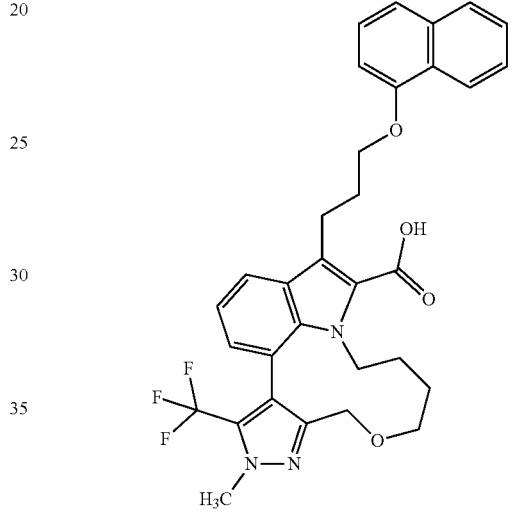

For the preparation of the racemic title compound and separation into its enantiomers see Example 186.
Analytical Chiral HPLC (method see Example 186): $R_t$=2.51 min.
$^1$H-NMR (400 MHz, DMSO-d6) δ[ppm]: 0.851 (0.52), 0.967 (2.12), 1.071 (1.15), 1.088 (2.01), 1.108 (10.84), 1.123 (1.28), 1.136 (1.46), 1.144 (2.01), 1.154 (1.44), 1.173 (1.17), 1.185 (0.99), 1.214 (1.08), 1.232 (2.07), 1.388 (0.97), 1.404 (0.86), 1.907 (0.56), 2.171 (0.63), 2.188 (1.92), 2.205 (3.04), 2.222 (2.01), 2.239 (0.68), 2.323 (0.92), 2.327 (1.33), 2.332 (0.92), 2.337 (0.41), 2.518 (5.77), 2.523 (3.97), 2.665 (0.92), 2.669 (1.33), 2.673 (0.92), 2.679 (0.41), 3.015 (0.59), 3.027 (0.79), 3.040 (1.31), 3.052 (1.37), 3.065 (0.77), 3.077 (0.65), 3.264 (0.83), 3.278 (1.22), 3.297 (2.48), 3.321 (2.43), 3.340 (1.51), 3.354 (2.10), 3.371 (1.71), 3.378 (1.33), 3.389 (1.22), 3.573 (1.49), 3.695 (0.86), 3.708 (0.99), 3.715 (0.97), 3.729 (1.44), 3.743 (0.99), 3.750 (1.06), 3.764 (0.77), 4.061 (15.41), 4.064 (16.00), 4.168 (1.67), 4.173 (1.83), 4.183 (3.29), 4.188 (3.29), 4.199 (1.87), 4.204 (1.71), 4.267 (3.92), 4.299 (4.62), 4.313 (0.68), 4.329 (1.15), 4.347 (1.37), 4.363 (1.01), 4.381 (0.56), 4.506 (4.37), 4.538 (3.56), 6.869 (3.36), 6.885 (3.72), 6.984 (2.88), 6.987 (3.25), 7.001 (5.14), 7.005 (4.75), 7.039 (4.64), 7.059 (4.89), 7.077 (2.79), 7.360 (2.77), 7.381 (4.85), 7.400 (3.99), 7.447 (4.91), 7.468 (2.88), 7.496 (0.50), 7.501 (1.04), 7.513 (3.34), 7.518 (5.70), 7.527 (6.33), 7.537 (5.54), 7.541 (3.83), 7.553 (1.19), 7.558 (0.50), 7.755 (3.61), 7.758 (3.83), 7.775 (3.45), 7.778 (3.36), 7.851 (0.45), 7.857 (2.79), 7.861 (1.98), 7.868 (1.49), 7.872 (1.74), 7.875 (1.87), 7.880 (2.41), 8.253 (2.48), 8.262 (1.62), 8.268 (1.17), 8.278 (2.37), 13.185 (0.43).

Example 196

7,9,12-trimethyl-1-[3-(naphthalen-1-yloxy)propyl]-11-propyl-4,5,6,7,8,9-hexahydropyrazolo[3',4':7,8][1,5]diazecino[9,10,1-hi]indole-2-carboxylic acid-N-ethylethanamine salt (Enantiomer 1)

Example 197

7,9,12-trimethyl-1-[3-(naphthalen-1-yloxy)propyl]-11-propyl-4,5,6,7,8,9-hexahydropyrazolo[3',4':7,8][1,5]diazecino[9,10,1-hi]indole-2-carboxylic acid-N-ethylethanamine salt (Enantiomer 2)

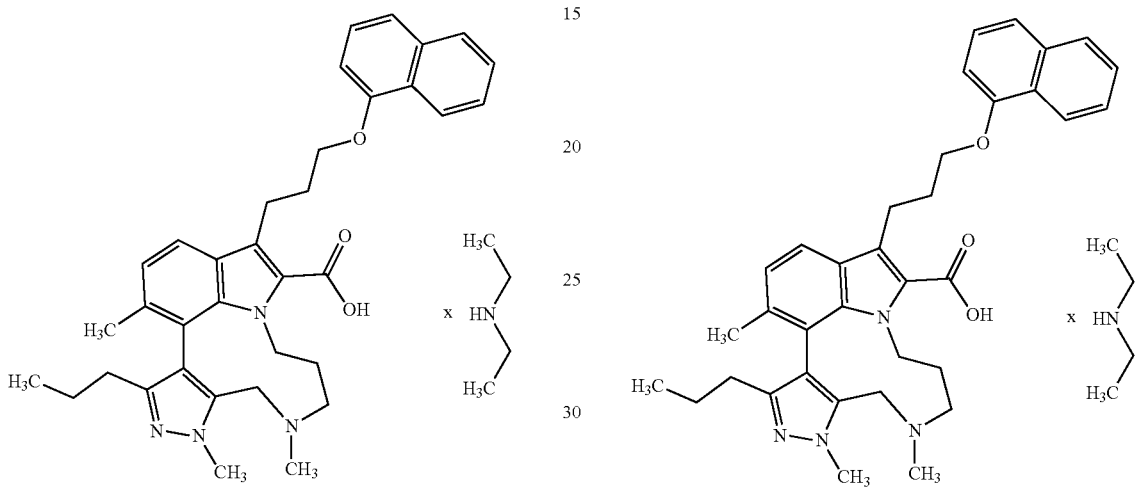

For the preparation of the racemic title compound and separation into its enantiomers see Example 193.

Analytical Chiral HPLC (method see Example 193): $R_t$=2.06 min.

¹H-NMR (400 MHz, DMSO-d6) δ[ppm]: 0.713 (5.08), 0.731 (12.21), 0.750 (5.69), 0.967 (0.67), 1.108 (9.06), 1.137 (3.69), 1.144 (0.84), 1.156 (7.48), 1.173 (3.61), 1.280 (0.50), 1.299 (1.92), 1.317 (3.90), 1.336 (3.78), 1.354 (2.27), 1.373 (0.81), 1.520 (0.54), 1.613 (0.65), 1.636 (0.64), 1.650 (0.75), 1.674 (0.61), 2.001 (16.00), 2.046 (0.51), 2.064 (0.87), 2.082 (1.42), 2.100 (2.24), 2.118 (2.17), 2.138 (2.39), 2.157 (2.06), 2.174 (2.14), 2.178 (2.30), 2.193 (2.21), 2.227 (0.77), 2.253 (14.84), 2.323 (0.61), 2.327 (0.88), 2.331 (0.64), 2.518 (3.71), 2.523 (2.47), 2.665 (0.58), 2.669 (0.82), 2.673 (0.61), 2.796 (1.93), 2.831 (2.04), 2.844 (1.01), 2.863 (2.94), 2.881 (2.85), 2.899 (0.88), 3.179 (0.67), 3.194 (0.80), 3.212 (1.25), 3.231 (0.71), 3.249 (0.82), 3.268 (1.52), 3.286 (1.19), 3.300 (1.33), 3.318 (1.24), 3.398 (0.71), 3.434 (0.95), 3.462 (0.57), 3.578 (2.02), 3.613 (1.89), 4.146 (1.60), 4.162 (3.38), 4.177 (1.65), 4.537 (0.81), 4.573 (0.80), 6.843 (2.30), 6.861 (2.43), 6.931 (2.64), 6.952 (2.83), 7.346 (1.70), 7.366 (3.21), 7.385 (2.50), 7.433 (3.25), 7.453 (1.99), 7.478 (0.51), 7.481 (0.77), 7.494 (1.85), 7.498 (1.76), 7.505 (2.03), 7.512 (4.09), 7.518 (2.09), 7.525 (2.06), 7.530 (2.58), 7.534 (2.75), 7.542 (1.14), 7.547 (0.85), 7.555 (2.30), 7.848 (1.93), 7.855 (1.11), 7.866 (1.94), 7.871 (1.68), 8.218 (1.68), 8.224 (1.68), 8.243 (1.65).

For the preparation of the racemic title compound and separation into its enantiomers see Example 193.

Analytical Chiral HPLC (method see Example 193): $R_t$=4.09 min.

¹H-NMR (400 MHz, DMSO-d6) δ[ppm]: 0.712 (5.15), 0.731 (12.51), 0.749 (5.80), 0.967 (0.72), 1.108 (14.50), 1.139 (3.09), 1.144 (0.82), 1.157 (6.38), 1.175 (2.93), 1.279 (0.42), 1.297 (1.84), 1.316 (3.70), 1.334 (3.68), 1.353 (2.24), 1.372 (0.76), 1.388 (0.59), 1.514 (0.52), 1.614 (0.64), 1.639 (0.63), 1.651 (0.73), 1.674 (0.61), 2.002 (16.00), 2.046 (0.51), 2.064 (0.86), 2.081 (1.45), 2.100 (2.20), 2.119 (1.97), 2.139 (2.43), 2.159 (2.11), 2.175 (2.27), 2.179 (2.20), 2.194 (2.30), 2.230 (0.80), 2.250 (15.04), 2.323 (0.56), 2.327 (0.78), 2.331 (0.55), 2.518 (3.19), 2.523 (2.23), 2.665 (0.57), 2.669 (0.80), 2.673 (0.55), 2.798 (1.93), 2.834 (2.05), 2.851 (0.82), 2.870 (2.48), 2.888 (2.39), 2.906 (0.74), 3.189 (0.65), 3.204 (0.80), 3.222 (1.26), 3.241 (0.74), 3.254 (0.81), 3.273 (1.55), 3.292 (1.19), 3.306 (1.33), 3.325 (1.17), 3.424 (0.60), 3.452 (0.90), 3.480 (0.53), 3.580 (2.01), 3.615 (1.86), 4.147 (1.64), 4.163 (3.47), 4.178 (1.64), 4.525 (0.82), 4.549 (0.51), 4.560 (0.81), 6.845 (2.27), 6.863 (2.46), 6.941 (2.73), 6.961 (2.91), 7.348 (1.71), 7.368 (3.22), 7.387 (2.56), 7.434 (3.29), 7.455 (1.93), 7.478 (0.55), 7.483 (0.77), 7.495 (1.97), 7.500 (1.72), 7.507 (2.03), 7.513 (4.28), 7.519 (2.11), 7.526 (1.85), 7.530 (2.15), 7.547 (3.21), 7.568 (2.39), 7.849 (1.94), 7.856 (1.10), 7.867 (1.96), 7.872 (1.66), 8.219 (1.70), 8.224 (1.66), 8.243 (1.62).

Example 198

(rac)-3-ethyl-1-[2-(morpholin-4-yl)ethyl]-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid

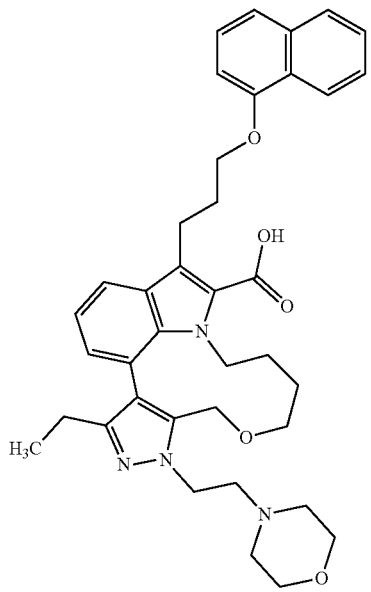 [SMILES: CCc1nn(CCN2CCOCC2)c2c1-c1cccc3c(CCCOc4cccc5ccccc45)c(C(=O)O)n(c13)CCCCOC2]

To a solution of (rac)-ethyl 3-ethyl-1-[2-(morpholin-4-yl)ethyl]-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (540 mg, 812 μmol; see Intermediate 333) in a mixture of THF (40 ml) and ethanol (27 ml) was added an aqueous solution of lithium hydroxide (16 ml, 1.0 M, 16 mmol). The resulting mixture was stirred at 60° C. for 48 hours. After removal of all volatiles the residue was subjected to flash chromatography (Biotage SNAP cartridge silica, dichloromethane/methanol gradient, 0%→100% methanol) to give the title compound (400 mg).

LC-MS (Method 2): Rt=0.85 min; MS (ESIpos): m/z=638 [M+H]$^+$ $^1$H-NMR (400 MHz, DMSO-d6) δ[ppm]: 0.873 (6.74), 0.892 (16.00), 0.911 (7.18), 0.990 (1.37), 1.008 (1.74), 1.071 (4.88), 1.088 (9.37), 1.105 (4.72), 1.230 (1.33), 1.292 (0.59), 1.303 (0.67), 1.314 (0.59), 2.144 (1.53), 2.163 (4.96), 2.182 (5.21), 2.201 (2.62), 2.216 (1.98), 2.233 (1.39), 2.250 (0.52), 2.332 (0.59), 2.370 (0.69), 2.380 (1.44), 2.397 (1.52), 2.409 (2.21), 2.420 (1.22), 2.518 (4.91), 2.523 (3.72), 2.674 (0.62), 2.731 (0.61), 2.748 (1.13), 2.763 (1.46), 2.780 (1.43), 2.798 (1.80), 2.815 (1.33), 2.829 (1.08), 2.834 (1.01), 2.846 (1.01), 2.864 (0.91), 2.880 (0.41), 3.247 (0.42), 3.266 (0.78), 3.281 (1.12), 3.299 (2.02), 3.330 (4.04), 3.349 (3.06), 3.353 (3.41), 3.371 (5.75), 3.382 (1.44), 3.388 (4.79), 3.397 (1.37), 3.406 (2.19), 3.427 (1.03), 3.443 (0.45), 3.559 (4.81), 3.571 (8.92), 3.582 (4.98), 3.998 (0.40), 4.008 (0.47), 4.021 (0.52), 4.032 (0.91), 4.043 (0.57), 4.056 (0.58), 4.067 (0.48), 4.187 (1.90), 4.202 (4.19), 4.218 (3.03), 4.235 (2.56), 4.247 (3.30), 4.259 (1.44), 4.281 (2.51), 4.508 (1.02), 4.519 (0.61), 4.531 (0.55), 4.543 (0.95), 4.659 (2.39), 4.693 (2.18), 6.815 (2.42), 6.819 (2.53), 6.833 (2.86), 6.836 (2.70), 6.878 (2.42), 6.894 (2.69), 7.026 (2.61), 7.043 (2.69), 7.045 (3.04), 7.063 (2.19), 7.361 (2.05), 7.381 (3.61), 7.400 (2.97), 7.444 (3.77), 7.464 (2.12), 7.487 (0.57), 7.491 (0.88), 7.504 (2.19), 7.508 (2.08), 7.512 (2.66), 7.520 (5.11), 7.528 (2.68), 7.532 (2.42), 7.536 (2.59), 7.549 (0.98), 7.553 (0.59), 7.737 (2.41), 7.739 (2.59), 7.756 (2.35), 7.759 (2.29), 7.854 (2.18), 7.862 (1.15), 7.872 (1.98), 7.877 (1.90), 8.230 (1.95), 8.236 (1.78), 8.247 (0.92), 8.252 (1.66), 8.255 (1.81).

The title compound (400 mg) was separated into enantiomers by preparative chiral HPLC to give enantiomer 1 (124.5 mg, see Example 199) and enantiomer 2 (121.4 mg, see Example 200).

Preparative chiral SFC method: Instrument: Sepiatec: Prep SFC100; column: Chiralpak IA 5 μm 250×30 mm; Eluent A: $CO_2$, Eluent B: ethanol+0.2 Vol-% aqueous ammonia (32%); isocratic: 22% B; flow 100.0 ml/min; temperature: 40° C.; BPR: 150 bar; MWD @ 220 nm Analytical chiral SFC method: Instrument: Agilent: 1260, Aurora SFC-Modul; column: Chiralpak IA 5 μm 100×4.6 mm; eluent A: $CO_2$, eluent B: ethanol+0.2 Vol-% aqueous ammonia (32%); 22% B; flow 4.0 ml/min; temperature: 37.5° C.; BPR: 100 bar; MWD @ 220 nm

Example 199

3-ethyl-1-[2-(morpholin-4-yl)ethyl]-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (Enantiomer 1)

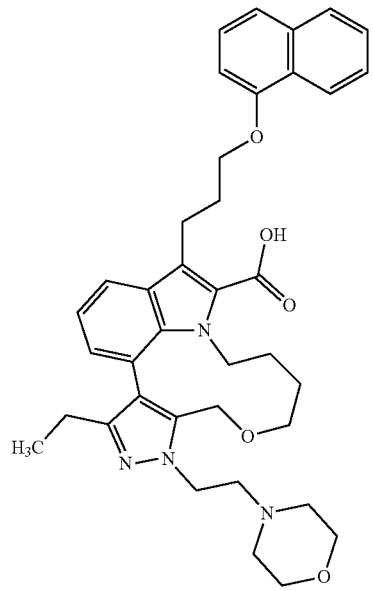 [SMILES: CCc1nn(CCN2CCOCC2)c2c1-c1cccc3c(CCCOc4cccc5ccccc45)c(C(=O)O)n(c13)CCCCOC2]

For the preparation of the racemic title compound see Example 198. Separation of enantiomers by preparative chiral SFC (method see Example 198) gave the title compound (124.5 mg).

Analytical Chiral SFC (method see Example 198): $R_t$=2.91 min.

LC-MS (Method 2): Rt=0.90 min; MS (ESIneg): m/z=636 [M−H]$^-$ $^1$H-NMR (400 MHz, DMSO-d6) δ[ppm]: 0.708 (1.23), 0.727 (2.79), 0.745 (1.49), 0.776 (0.69), 0.798 (2.00), 0.814 (2.38), 0.821 (2.72), 0.835 (3.36), 0.840 (3.15), 0.847 (4.44), 0.854 (6.13), 0.864 (11.46), 0.875 (10.15), 0.880 (8.23), 0.894 (16.00), 0.904 (3.36), 0.913 (7.90), 0.922 (1.77), 0.931 (1.13), 0.991 (2.62), 1.004 (2.92), 1.018 (2.62), 1.043 (5.44), 1.062 (1.49), 1.108 (1.56), 1.135 (3.82), 1.140 (5.31), 1.150 (4.31), 1.155 (5.08), 1.176 (1.92), 1.231 (3.28), 1.262 (1.87), 1.335 (1.23), 1.428 (0.82), 1.447 (1.97), 1.466 (1.87), 1.485 (0.72), 2.012 (1.49), 2.026 (0.74), 2.043 (1.97), 2.067 (0.67), 2.106 (1.10), 2.132 (1.36), 2.137 (1.67), 2.146 (2.33), 2.165 (6.10), 2.184 (6.54), 2.203 (3.90), 2.212 (3.59), 2.230 (2.62), 2.279 (0.97), 2.326 (1.97), 2.380 (2.77), 2.396 (3.05), 2.408 (4.03), 2.669 (1.77), 2.714 (0.87), 2.730 (1.10), 2.746 (1.74), 2.762 (2.23), 2.779 (2.31), 2.798 (2.62), 2.816 (2.18), 2.829 (2.18), 2.854 (1.54), 3.250 (1.51), 3.264 (1.90), 3.281 (2.69), 3.301 (2.33), 3.320 (2.82), 3.339 (3.67), 3.356 (2.87), 3.372 (2.67), 3.392 (2.67), 3.423 (1.92), 3.559 (7.33), 3.570 (12.87), 3.582 (7.36), 3.981 (0.77), 4.007 (1.36), 4.032 (0.90), 4.183 (2.97), 4.198 (5.82), 4.214 (4.59), 4.242 (5.38), 4.277 (3.49), 4.532 (1.41), 4.567 (1.28), 4.658 (3.15), 4.691 (2.85), 6.788 (3.03), 6.805 (3.41), 6.872 (3.28), 6.891 (3.51), 7.008 (2.44), 7.026 (3.67), 7.045 (2.26), 7.357 (2.00), 7.377 (4.13), 7.397 (3.00), 7.440 (4.87), 7.461 (2.82), 7.488 (1.08), 7.501 (2.72), 7.505 (2.97), 7.509 (3.38), 7.517 (5.28), 7.525 (3.41), 7.533 (2.85), 7.546 (1.05), 7.713 (3.15), 7.734 (2.90), 7.852 (3.00), 7.870 (2.56), 7.875 (2.41), 8.229 (2.51), 8.234 (2.36), 8.252 (2.38).

Example 200

3-ethyl-1-[2-(morpholin-4-yl)ethyl]-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (Enantiomer 2)

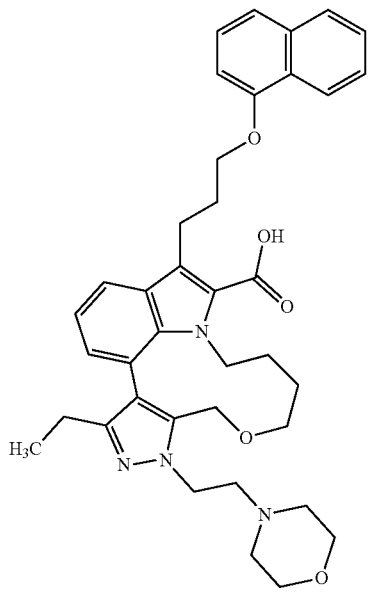 [SMILES: CCc1nn(CCN2CCOCC2)c2c1-c1cccc3c(CCCOc4cccc5ccccc45)c(C(=O)O)n(c13)CCCCOC2]

For the preparation of the racemic title compound see Example 198. Separation of enantiomers by preparative chiral SFC (method see Example 198) gave the title compound (121.4 mg).
Analytical Chiral SFC (method see Example 198): $R_t$=3.72 min.
LC-MS (Method 2): Rt=0.90 min; MS (ESIneg): m/z=636 [M−H]⁻
¹H-NMR (400 MHz, DMSO-d6) δ[ppm]: 0.708 (1.66), 0.727 (3.84), 0.745 (1.99), 0.769 (0.51), 0.776 (0.84), 0.785 (0.86), 0.797 (2.60), 0.802 (2.05), 0.814 (3.02), 0.821 (3.38), 0.835 (3.84), 0.840 (3.58), 0.847 (5.23), 0.854 (7.57), 0.863 (13.48), 0.875 (9.95), 0.880 (9.42), 0.886 (3.46), 0.894 (16.00), 0.904 (3.69), 0.913 (7.86), 0.922 (1.88), 0.964 (1.32), 0.984 (2.45), 1.002 (2.58), 1.018 (2.32), 1.044 (6.66), 1.062 (1.90), 1.067 (1.43), 1.083 (0.90), 1.088 (0.75), 1.100 (0.77), 1.107 (0.99), 1.118 (0.66), 1.135 (4.55), 1.140 (6.38), 1.150 (4.90), 1.156 (6.27), 1.170 (1.41), 1.179 (1.24), 1.211 (1.50), 1.220 (1.61), 1.236 (1.52), 1.254 (0.93), 1.263 (1.39), 1.337 (1.06), 1.350 (0.95), 1.428 (0.93), 1.447 (2.47), 1.466 (2.32), 1.485 (0.82), 1.988 (0.44), 2.012 (1.99), 2.027 (0.86), 2.043 (2.54), 2.068 (0.66), 2.083 (0.49), 2.106 (1.24), 2.117 (0.57), 2.130 (1.17), 2.137 (1.92), 2.147 (2.10), 2.166 (5.94), 2.185 (6.20), 2.203 (3.44), 2.211 (3.27), 2.229 (2.38), 2.281 (1.06), 2.323 (1.74), 2.326 (1.85), 2.337 (0.90), 2.358 (1.02), 2.380 (2.36), 2.393 (2.63), 2.408 (3.60), 2.669 (1.52), 2.673 (1.50), 2.688 (0.66), 2.698 (0.60), 2.714 (0.90), 2.729 (1.04), 2.746 (1.57), 2.761 (2.01), 2.779 (2.10), 2.798 (2.49), 2.817 (1.88), 2.829 (1.81), 2.853 (1.41), 2.871 (0.66), 3.245 (1.30), 3.260 (1.59), 3.278 (2.23), 3.298 (1.70), 3.318 (1.96), 3.337 (2.76), 3.354 (2.18), 3.371 (2.12), 3.392 (2.34), 3.405 (1.74), 3.422 (1.77), 3.559 (6.62), 3.570 (12.05), 3.582 (6.80), 3.977 (0.64), 4.003 (1.21), 4.028 (0.79), 4.181 (2.58), 4.197 (5.14), 4.213 (3.97), 4.242 (4.99), 4.276 (3.29), 4.537 (1.19), 4.571 (1.10), 4.657 (3.00), 4.691 (2.74), 6.784 (2.80), 6.800 (3.18), 6.872 (3.00), 6.890 (3.27), 7.005 (2.45), 7.024 (3.44), 7.042 (2.21), 7.356 (1.88), 7.376 (3.88), 7.395 (2.91), 7.439 (4.57), 7.460 (2.63), 7.487 (0.93), 7.500 (2.41), 7.504 (2.56), 7.509 (3.07), 7.516 (5.12), 7.524 (3.11), 7.528 (2.94), 7.533 (2.80), 7.546 (1.06), 7.710 (2.94), 7.729 (2.74), 7.851 (2.78), 7.859 (1.52), 7.869 (2.38), 7.874 (2.32), 8.229 (2.21), 8.234 (2.18), 8.252 (2.21).

Example 201

(rac)-3-ethyl-2-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid

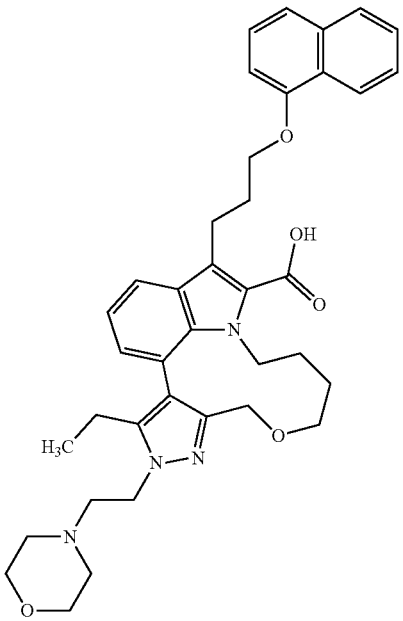 [SMILES: CCc1c2c(nn1CCN1CCOCC1)COCCCCn1c(C(=O)O)c(CCCOc3cccc4ccccc34)c3cccc-2c31]

To a solution of (rac)-ethyl 3-ethyl-2-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylate (1.28 g, 1.93 mmol; see Intermediate 338) in a mixture of THF (94 ml) and ethanol (65 ml) was added an aqueous solution of lithium hydroxide (39 ml, 1.0 M, 39 mmol). The resulting mixture was stirred at 60° C. for 48 hours. After removal of all volatiles the residue was subjected to flash chromatography (Biotage SNAP cartridge silica, dichloromethane/methanol gradient, 0%→100% methanol) to give the title compound (1.1 g).

LC-MS (Method 2): Rt=0.86 min; MS (ESIpos): m/z=638 [M+H]$^+$ $^1$H-NMR (400 MHz, DMSO-d6) δ[ppm]: 0.792 (6.66), 0.811 (15.14), 0.829 (6.83), 0.975 (0.88), 0.994 (1.02), 1.110 (0.59), 1.144 (1.31), 1.172 (0.76), 1.229 (1.38), 1.250 (1.07), 1.343 (0.95), 1.756 (0.59), 1.908 (0.62), 2.084 (5.93), 2.183 (1.33), 2.201 (3.43), 2.220 (5.67), 2.233 (4.84), 2.251 (3.38), 2.270 (1.41), 2.288 (0.60), 2.297 (1.48), 2.401 (1.22), 2.418 (3.14), 2.429 (6.21), 2.442 (6.38), 2.454 (3.33), 2.518 (3.76), 2.523 (2.62), 2.697 (0.55), 2.713 (1.19), 2.729 (1.97), 2.745 (2.48), 2.761 (1.31), 2.771 (1.28), 2.788 (2.83), 2.804 (1.86), 2.820 (1.34), 2.837 (0.59), 3.072 (0.69), 3.084 (0.83), 3.097 (1.52), 3.110 (1.47), 3.123 (1.02), 3.135 (0.78), 3.249 (0.62), 3.269 (2.07), 3.281 (3.21), 3.299 (5.03), 3.318 (5.93), 3.335 (5.29), 3.531 (7.34), 3.542 (12.97), 3.554 (7.24), 3.582 (0.45), 3.599 (0.55), 3.873 (0.66), 3.882 (0.81), 3.906 (1.53), 3.916 (0.91), 3.930 (0.98), 3.939 (0.74), 4.106 (0.62), 4.122 (1.22), 4.141 (1.57), 4.158 (2.59), 4.172 (6.91), 4.196 (5.24), 4.203 (7.34), 4.210 (5.03), 4.227 (2.16), 4.245 (1.86), 4.252 (1.50), 4.269 (1.34), 4.286 (1.03), 4.307 (0.62), 4.508 (4.71), 4.539 (4.16), 5.759 (16.00), 6.872 (4.10), 6.890 (4.41), 6.913 (3.60), 6.915 (3.74), 6.931 (4.69), 6.933 (4.55), 7.030 (4.07), 7.050 (4.93), 7.068 (3.05), 7.359 (3.02), 7.367 (0.41), 7.379 (5.81), 7.398 (4.47), 7.445 (5.95), 7.466 (3.47), 7.496 (0.48), 7.501 (1.12), 7.513 (3.81), 7.517 (5.57), 7.527 (6.66), 7.536 (5.48), 7.540 (4.34), 7.552 (1.21), 7.557 (0.47), 7.701 (3.98), 7.704 (4.12), 7.721 (3.78), 7.724 (3.69), 7.857 (3.34), 7.861 (2.31), 7.871 (2.17), 7.874 (2.09), 7.880 (2.86), 7.889 (0.45), 8.255 (2.95), 8.265 (2.14), 8.278 (2.74).

The title compound (1.1 g) was separated into enantiomers by preparative chiral HPLC to give enantiomer 1 (502 mg, see Example 202) and enantiomer 2 (500 mg, see Example 203).

Preparative chiral HPLC method: Instrument: Labomatic HD5000, Labocord-5000; Gilson GX-241, Labcol Vario 4000, column: Chiralpak AD-H 5µ 250×30 mm; Eluent A: hexane+0.1 Vol-% trifluoroacetic acid (99%); Eluent B: isopropanol; Gradient: 24-46% B; flow 50.0 ml/min, 19 min; UV 254 nm Analytical chiral HPLC method Instrument: Agilent HPLC 1260; column: Chiralpak AD-H 3µ 100×4.6 mm; Eluent A: hexane+0.1 Vol-% trifluoroacetic acid (99%); Eluent B: isopropanol; Gradient: 5-50% B in 7 min; Flow 1.4 ml/min; Temperature: 25° C.; DAD 254 nm Example 202

3-ethyl-2-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (Enantiomer 1)

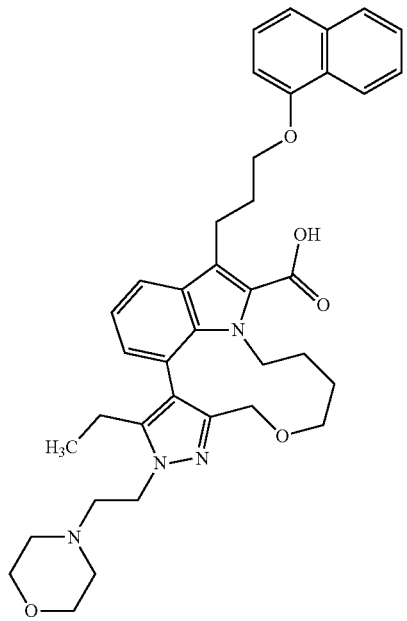 [SMILES: CCc1c2c(nn1CCN1CCOCC1)COCCCCn1c(C(=O)O)c(CCCOc3cccc4ccccc34)c3cccc-2c31]

For the preparation of the racemic title compound see Example 201. Separation of enantiomers by preparative chiral HPLC (method see Example 201) gave the title compound (502 mg).

Analytical Chiral HPLC (method see Example 201): R$_t$=2.57 min.

LC-MS (Method 2): Rt=0.89 min; MS (ESIpos): m/z=638 [M+H]$^+$ $^1$H-NMR (400 MHz, DMSO-d6) δ[ppm]: 0.776 (0.55), 0.794 (1.32), 0.813 (0.86), 0.830 (5.75), 0.849 (12.54), 0.868 (6.20), 1.006 (2.06), 1.019 (0.96), 1.034 (0.90), 1.084 (1.61), 1.108 (16.00), 1.144 (0.86), 1.172 (1.10), 1.208 (1.22), 1.233 (1.26), 1.245 (1.08), 1.259 (2.04), 1.358 (0.96), 1.422 (0.47), 2.171 (1.00), 2.190 (2.04), 2.209 (3.40), 2.220 (3.10), 2.281 (1.45), 2.299 (1.71), 2.318 (1.79), 2.322 (1.28), 2.327 (1.43), 2.331 (1.12), 2.337 (1.26), 2.518 (6.77), 2.523 (4.44), 2.665 (0.86), 2.669 (1.20), 2.673 (0.88), 3.062 (0.67), 3.074 (0.79), 3.087 (1.45), 3.100 (1.41), 3.112 (1.02), 3.125 (0.84), 3.257 (1.04), 3.275 (1.22), 3.309 (3.93), 3.321 (4.08), 3.634 (2.06), 3.835 (1.04), 3.846 (1.18), 3.869 (1.81), 3.880 (1.39), 3.892 (1.32), 3.931 (0.69), 4.011 (0.92), 4.177 (1.90), 4.193 (3.85), 4.200 (7.01), 4.232 (4.32), 4.258 (0.88), 4.276 (1.28), 4.293 (1.35), 4.314 (1.10), 4.331 (0.73), 4.456 (0.67), 4.474 (1.14), 4.492 (1.79), 4.517 (1.96), 4.533 (4.91), 4.564 (3.75), 5.758 (5.50), 6.874 (3.61), 6.892 (3.87), 6.922 (3.36), 6.925 (3.65), 6.940 (4.26), 6.942 (4.22), 7.049 (3.55), 7.068 (4.40), 7.086 (2.75), 7.362 (2.69), 7.382 (5.05), 7.401 (3.91), 7.449 (5.16), 7.469 (3.08), 7.497 (0.55), 7.501 (1.12), 7.513 (3.14), 7.519 (5.54), 7.528 (6.62), 7.538 (5.93), 7.543 (3.69), 7.555 (1.20), 7.560 (0.59), 7.730 (3.55), 7.733 (3.73), 7.750 (3.34), 7.753 (3.34), 7.860 (2.98), 7.870 (1.53), 7.878 (2.08), 7.883 (2.57), 8.243 (0.41), 8.251 (2.55), 8.258 (2.10), 8.266 (1.22), 8.275 (2.47).

Example 203

3-ethyl-2-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (Enantiomer 2)

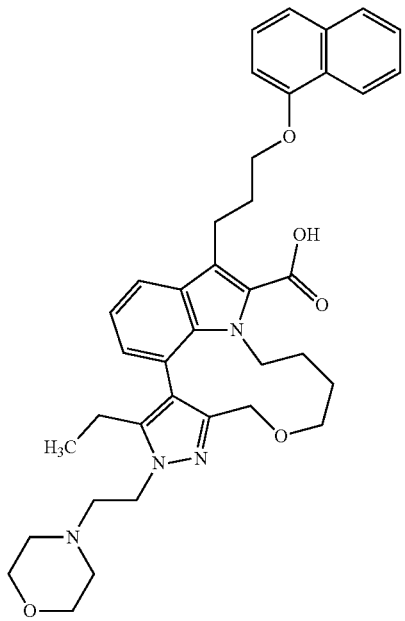 [SMILES: CCc1c2c(nn1CCN1CCOCC1)COCCCCn1c(C(=O)O)c(CCCOc3cccc4ccccc34)c3cccc-2c31]

For the preparation of the racemic title compound see Example 201. Separation of enantiomers by preparative chiral HPLC (method see Example 201) gave the title compound (500 mg).

Analytical Chiral HPLC (method see Example 201): $R_t$=4.38 min.

LC-MS (Method 2): Rt=0.87 min; MS (ESIpos): m/z=638 [M+H]$^+$ $^1$H-NMR (400 MHz, DMSO-d6) δ[ppm]: 0.775 (0.73), 0.782 (0.48), 0.794 (1.69), 0.813 (1.08), 0.830 (6.05), 0.849 (12.98), 0.868 (6.53), 1.006 (2.43), 1.019 (1.19), 1.034 (1.02), 1.083 (2.21), 1.107 (16.00), 1.144 (0.94), 1.172 (1.19), 1.200 (1.37), 1.231 (1.46), 1.259 (2.37), 1.272 (0.81), 1.284 (0.71), 1.333 (0.87), 1.359 (1.08), 1.405 (0.69), 1.422 (0.67), 1.440 (0.54), 2.045 (0.44), 2.057 (0.46), 2.171 (1.06), 2.190 (2.14), 2.208 (3.64), 2.227 (3.33), 2.280 (1.50), 2.299 (1.83), 2.318 (1.85), 2.327 (1.39), 2.331 (1.16), 2.337 (1.33), 2.522 (5.14), 2.665 (0.83), 2.669 (1.16), 2.673 (0.87), 3.062 (0.71), 3.074 (0.85), 3.088 (1.52), 3.100 (1.50), 3.113 (1.10), 3.126 (0.87), 3.257 (1.12), 3.274 (1.33), 3.309 (4.27), 3.321 (4.45), 3.639 (2.46), 3.846 (1.25), 3.868 (1.93), 3.880 (1.58), 3.892 (1.44), 3.930 (0.83), 4.008 (1.00), 4.177 (2.02), 4.193 (4.12), 4.200 (7.32), 4.232 (4.49), 4.260 (0.98), 4.277 (1.42), 4.295 (1.52), 4.314 (1.23), 4.331 (0.85), 4.458 (0.81), 4.475 (1.33), 4.493 (2.08), 4.520 (2.29), 4.533 (5.03), 4.564 (3.89), 5.758 (2.87), 6.874 (3.79), 6.892 (4.06), 6.922 (3.41), 6.925 (3.74), 6.940 (4.37), 6.942 (4.37), 7.049 (3.41), 7.068 (4.43), 7.086 (2.77), 7.361 (2.60), 7.382 (5.04), 7.401 (3.91), 7.448 (5.33), 7.469 (3.22), 7.496 (0.58), 7.501 (1.04), 7.513 (3.18), 7.519 (5.41), 7.528 (6.58), 7.537 (5.97), 7.543 (3.75), 7.555 (1.21), 7.560 (0.65), 7.730 (3.58), 7.733 (3.93), 7.750 (3.45), 7.753 (3.52), 7.860 (3.04), 7.870 (1.64), 7.878 (2.19), 7.883 (2.68), 8.251 (2.62), 8.258 (2.19), 8.266 (1.33), 8.275 (2.62).

Example 204

(rac)-3-ethyl-4-methyl-2-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid

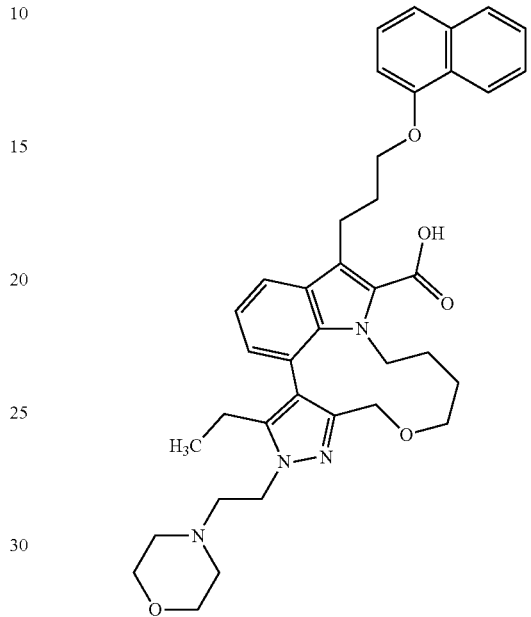

To a solution of (rac)-ethyl 3-ethyl-4-methyl-2-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylate (700 mg, 1.03 mmol; see Intermediate 341) in a mixture of THF (50 ml) and ethanol (35 ml) was added an aqueous solution of lithium hydroxide (21 ml, 1.0 M, 21 mmol). The resulting mixture was stirred at 70° C. for three days. After removal of all volatiles the residue was subjected to flash chromatography (Biotage SNAP cartridge silica, dichloromethane/methanol gradient, 0%→100% methanol) to give the title compound (560 mg).

LC-MS (Method 2): Rt=0.87 min; MS (ESIpos): m/z=652 [M+H]$^+$ $^1$H-NMR (400 MHz, DMSO-d6) δ[ppm]: 0.739 (3.93), 0.758 (8.87), 0.777 (4.11), 0.940 (0.52), 0.961 (0.55), 1.132 (0.66), 1.232 (1.07), 1.296 (1.06), 1.310 (0.87), 1.907 (0.54), 1.994 (16.00), 2.113 (0.46), 2.131 (0.84), 2.149 (1.53), 2.168 (1.69), 2.176 (1.66), 2.194 (2.19), 2.205 (1.94), 2.212 (1.70), 2.222 (1.36), 2.231 (0.85), 2.427 (4.54), 2.438 (3.42), 2.454 (0.47), 2.458 (0.44), 2.463 (0.41), 2.518 (3.86), 2.523 (2.70), 2.714 (0.65), 2.730 (1.10), 2.746 (1.72), 2.761 (1.09), 2.774 (1.72), 2.789 (1.12), 2.805 (0.65), 3.131 (0.43), 3.146 (0.73), 3.157 (0.77), 3.171 (0.52), 3.183 (0.43), 3.247 (0.93), 3.264 (1.70), 3.279 (2.32), 3.297 (1.95), 3.520 (4.05), 3.531 (5.80), 3.542 (4.08), 3.834 (0.76), 3.860 (0.50), 4.155 (1.50), 4.173 (2.82), 4.183 (2.70), 4.190 (3.04), 4.197 (4.10), 4.206 (2.33), 4.227 (3.83), 4.240 (1.40), 4.258 (0.87), 4.382 (2.76), 4.414 (2.21), 6.864 (2.30), 6.881 (2.52), 6.988 (3.01), 7.008 (3.25), 7.357 (1.99), 7.377 (3.45), 7.396 (2.76), 7.445 (3.39), 7.466 (2.03), 7.501 (0.71), 7.513 (2.36), 7.518 (3.77), 7.528 (4.26), 7.537 (3.53), 7.541 (2.55), 7.553 (0.79), 7.585 (3.31), 7.605

(2.96), 7.858 (1.95), 7.861 (1.37), 7.869 (1.02), 7.872 (1.20), 7.875 (1.29), 7.881 (1.67), 8.253 (1.77), 8.261 (1.09), 8.267 (0.82), 8.278 (1.59).

The title compound (560 mg) was separated into enantiomers by preparative chiral HPLC to give enantiomer 1 (10.6 mg, see Example 205) and enantiomer 2 (40.4 mg, see Example 206).

Preparative chiral HPLC method: Instrument: Labomatic HD5000, Labocord-5000; Gilson GX-241, Labcol Vario 4000, column: XBrigde C18 5µ 150×30 mm; Eluent B: water+0.2 Vol-% aqueous ammonia (32%); Eluent C: acetonitrile; Gradient: 2.5-9.5 min 28-52% C, 9.5-11.5 min 100% C; Flow 50.0 ml/min; UV 254 nm Analytical chiral HPLC method: Instrument: Waters Alliance 2695; column: Chiralpak AD-H 3µ 100×4.6 mm; Eluent A: hexane+0.1 Vol-% trifluoroacetic acid (99%); Eluent B: isopropanol; Gradient: 20-50% B in 7 min; Flow 1.4 ml/min; Temperature: 25° C.; DAD 254 nm Example 205

3-ethyl-4-methyl-2-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (Enantiomer 1)

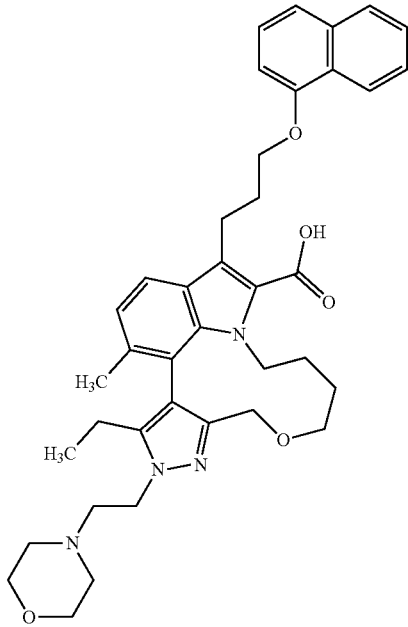 [SMILES: CCc1c2c(nn1CCN1CCOCC1)COCCCCn1c(C(=O)O)c(CCCOc3cccc4ccccc34)c3ccc(C)c-2c31]

For the preparation of the racemic title compound see Example 204. Separation of enantiomers by preparative chiral HPLC (method see Example 204) gave the title compound (10.6 mg).

Analytical Chiral HPLC (method see Example 204): $R_t$=2.98 min.

$^1$H-NMR (400 MHz, DMSO-d6) δ[ppm]: 0.740 (3.88), 0.759 (8.57), 0.778 (3.98), 0.936 (0.62), 0.958 (0.64), 1.136 (2.14), 1.154 (3.45), 1.173 (1.89), 1.231 (1.44), 1.297 (1.28), 1.312 (1.04), 1.353 (0.44), 1.907 (0.42), 1.996 (16.00), 2.111 (0.50), 2.130 (0.90), 2.148 (1.57), 2.167 (1.75), 2.176 (1.80), 2.195 (2.36), 2.204 (2.15), 2.213 (1.86), 2.439 (2.52), 2.518 (3.81), 2.523 (2.62), 2.777 (0.80), 2.921 (0.43), 3.145 (0.83), 3.157 (0.86), 3.172 (0.58), 3.235 (0.43), 3.250 (1.03), 3.268 (1.86), 3.281 (2.50), 3.299 (2.04), 3.538 (4.52), 3.815 (0.47), 3.839 (0.86), 3.864 (0.58), 4.158 (1.32), 4.174 (2.81), 4.183 (3.09), 4.197 (4.88), 4.214 (1.94), 4.228 (4.21), 4.248 (1.12), 4.267 (0.50), 4.385 (2.77), 4.417 (2.19), 5.759 (3.01), 6.865 (2.45), 6.883 (2.63), 6.992 (3.15), 7.013 (3.42), 7.358 (1.72), 7.378 (3.31), 7.398 (2.55), 7.447 (3.48), 7.467 (2.05), 7.502 (0.69), 7.514 (2.23), 7.519 (3.63), 7.528 (3.99), 7.538 (3.62), 7.542 (2.47), 7.554 (0.75), 7.592 (3.56), 7.612 (3.18), 7.859 (2.00), 7.873 (1.22), 7.876 (1.26), 7.882 (1.68), 8.254 (1.72), 8.262 (1.21), 8.278 (1.61).

Example 206

3-ethyl-4-methyl-2-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (Enantiomer 2)

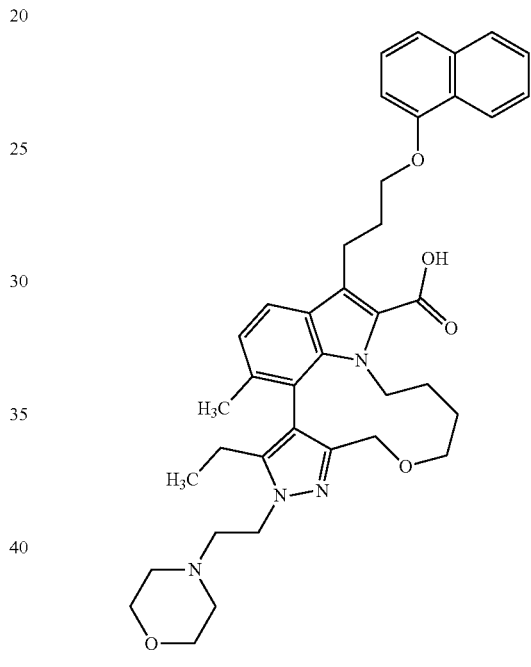

For the preparation of the racemic title compound see Example 204. Separation of enantiomers by preparative chiral HPLC (method see Example 204) gave the title compound (40.4 mg).

Analytical Chiral HPLC (method see Example 204): $R_t$=5.63 min.

$^1$H-NMR (400 MHz, DMSO-d6) δ[ppm]: 0.739 (3.93), 0.758 (8.78), 0.777 (4.06), 0.938 (0.57), 0.959 (0.62), 1.137 (1.34), 1.155 (1.65), 1.173 (0.90), 1.231 (0.58), 1.296 (1.17), 1.311 (0.96), 1.907 (0.47), 1.995 (16.00), 2.112 (0.47), 2.130 (0.87), 2.149 (1.56), 2.168 (1.74), 2.175 (1.74), 2.194 (2.33), 2.204 (2.11), 2.212 (1.86), 2.221 (1.50), 2.427 (4.94), 2.437 (3.80), 2.518 (3.94), 2.523 (2.62), 2.540 (1.08), 2.714 (0.67), 2.730 (1.12), 2.746 (1.77), 2.761 (1.23), 2.774 (1.79), 2.789 (1.16), 2.805 (0.67), 2.910 (0.47), 2.928 (0.46), 3.146 (0.82), 3.157 (0.83), 3.172 (0.57), 3.183 (0.47), 3.233 (0.41), 3.249 (0.99), 3.266 (1.83), 3.280 (2.50), 3.297 (2.03), 3.331 (4.24), 3.519 (4.24), 3.531 (6.21), 3.542 (4.35), 3.812 (0.45), 3.837 (0.86), 3.862 (0.55), 4.155 (1.57), 4.173 (3.06), 4.182 (2.87), 4.190 (3.29), 4.196 (4.43), 4.206 (2.44), 4.227 (4.06), 4.239 (1.44), 4.258 (0.80), 4.383 (2.82), 4.414 (2.21), 5.759 (8.32), 6.863 (2.43), 6.882 (2.62), 6.989 (3.16), 7.010 (3.36), 7.357

(1.75), 7.377 (3.32), 7.396 (2.52), 7.445 (3.48), 7.466 (2.07), 7.502 (0.67), 7.514 (2.21), 7.518 (3.62), 7.528 (3.97), 7.537 (3.55), 7.542 (2.46), 7.554 (0.74), 7.587 (3.47), 7.607 (3.08), 7.858 (1.98), 7.872 (1.21), 7.876 (1.25), 7.882 (1.69), 8.254 (1.71), 8.262 (1.19), 8.278 (1.59).

Example 207

(rac)-3-methoxy-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylate

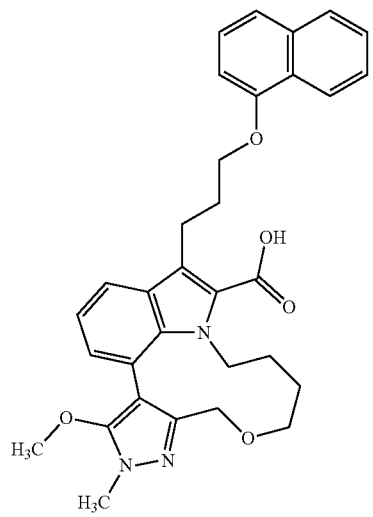 [SMILES: COc1c2c(nn1C)COCCCCn1c(C(=O)O)c(CCCOc3cccc4ccccc34)c3cccc-2c31]

To a solution of (rac)-ethyl 3-methoxy-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylate (455 mg, 801 μmol; see Intermediate 347) in a mixture of THF (11 ml) and ethanol (5.7 ml) was added an aqueous solution of lithium hydroxide (5.7 ml, 1.0 M, 5.7 mmol). The resulting mixture was stirred at 50° C. for two days, followed by stirring at 70° C. for 5 hours. Finally stirring was continued for three days at room temperature. After removal of all volatiles the residue was subjected to flash chromatography (Biotage SNAP cartridge silica, dichloromethane/methanol gradient, 0%→10% methanol) to give crude product, which was subjected to a second chromatography (Biotage SNAP cartridge silica, dichloromethane/acetonitril gradient, 0%→40% acetonitril). This resulted in the isolation of the title compound (227 mg).

LC-MS (Method 2): Rt=0.83 min; MS (ESIpos): m/z=540 [M+H]$^+$ $^1$H-NMR (400 MHz, DMSO-d6) δ[ppm]: 1.209 (0.53), 1.232 (0.61), 1.907 (0.42), 2.189 (0.50), 2.206 (0.80), 2.223 (0.51), 2.518 (2.19), 2.523 (1.38), 3.274 (0.54), 3.293 (1.05), 3.318 (16.00), 3.329 (6.26), 4.044 (1.11), 4.075 (1.17), 4.156 (0.74), 4.173 (1.34), 4.188 (0.62), 4.461 (1.07), 4.492 (0.97), 5.759 (1.58), 6.857 (0.88), 6.874 (0.96), 7.011 (1.45), 7.015 (2.12), 7.032 (1.27), 7.050 (0.41), 7.354 (0.72), 7.374 (1.30), 7.393 (1.07), 7.442 (1.26), 7.463 (0.74), 7.513 (0.92), 7.516 (1.16), 7.527 (1.42), 7.535 (1.01), 7.537 (1.12), 7.540 (1.06), 7.710 (0.74), 7.715 (0.75), 7.728 (0.68), 7.733 (0.68), 7.855 (0.72), 7.859 (0.50), 7.868 (0.53), 7.872 (0.46), 7.879 (0.63), 8.250 (0.66), 8.261 (0.51), 8.275 (0.61).

The title compound (220 mg) was separated into enantiomers by preparative chiral HPLC to give enantiomer 1 (46 mg, see Example 208) and enantiomer 2 (31 mg, see Example 209).

Preparative chiral HPLC method: Instrument: Labomatic HD5000, Labocord-5000; Gilson GX-241, Labcol Vario 4000, column: Chiralpak AD 5μ 250×30 mm; Eluent A: hexane+0.1 Vol-% trifluoroacetic acid; Eluent B: isopropanol; isocratic: 80-20% runtime 20 min; Flow 50 ml/min; UV 254 nm Analytical chiral HPLC method: Instrument: Agilent HPLC 1260; column: Chiralpak AD 3μ 100×4.6 mm; Eluent A: hexane+0.1 Vol-% trifluoroacetic acid; Eluent B: isopropanol; Gradient: 20-50% B in 7 min; Flow 1.4 ml/min; temperature: 25° C.; DAD 254 nm Example 208

3-methoxy-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylate (Enantiomer 1)

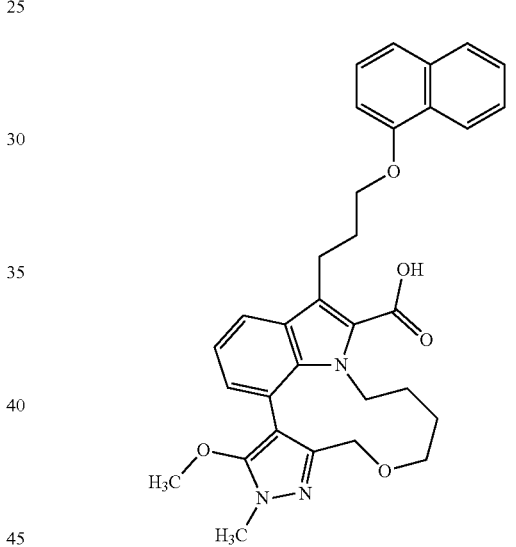

For the preparation of the racemic title compound see Example 207. Separation of enantiomers by preparative chiral HPLC (method see Example 207) gave the title compound (134 mg), which was then subjected to nonchiral flash chromatography (Biotage SNAP cartridge silica, dichloromethane/acetonitrile gradient, 0%→85% acetonitrile) to give the title compound (46 mg).

Analytical Chiral HPLC (method see Example 207): R$_t$=2.30 min.

$^1$H-NMR (400 MHz, DMSO-d6) δ[ppm]: 1.234 (0.58), 2.075 (0.42), 2.190 (0.47), 2.207 (0.75), 2.223 (0.49), 2.518 (1.75), 2.523 (1.25), 3.278 (0.54), 3.285 (0.60), 3.297 (1.12), 3.318 (16.00), 3.327 (0.63), 3.330 (1.28), 3.335 (0.50), 3.340 (1.14), 3.351 (0.48), 3.652 (9.40), 4.044 (1.14), 4.076 (1.24), 4.158 (0.74), 4.174 (1.30), 4.189 (0.60), 4.464 (1.16), 4.495 (1.04), 6.859 (0.84), 6.876 (0.91), 7.007 (0.46), 7.019 (2.07), 7.025 (1.50), 7.038 (1.55), 7.056 (0.50), 7.355 (0.71), 7.376 (1.24), 7.395 (1.01), 7.443 (1.20), 7.464 (0.72), 7.514 (0.87), 7.518 (1.11), 7.528 (1.35), 7.536 (0.96), 7.538 (1.08), 7.541 (0.97), 7.718 (0.89), 7.724 (0.90), 7.735 (0.73), 7.741

(0.73), 7.856 (0.68), 7.860 (0.47), 7.869 (0.50), 7.874 (0.44), 7.880 (0.58), 8.251 (0.62), 8.262 (0.48), 8.276 (0.58).

Example 209

3-methoxy-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylate (Enantiomer 2)

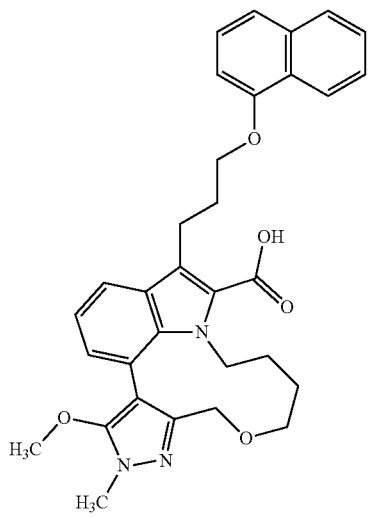 [SMILES: COc1c2c(nn1C)COCCCCn1c(C(=O)O)c(CCCOc3cccc4ccccc34)c3cccc-2c31]

For the preparation of the racemic title compound see Example 207. Separation of enantiomers by preparative chiral HPLC (method see Example 207) gave the title compound (81 mg), which was then subjected to nonchiral flash chromatography (Biotage SNAP cartridge silica, dichloromethane/acetonitrile gradient, 0%→75% acetonitrile) to give the title compound (31 mg).

Analytical Chiral HPLC (method see Example 207): $R_t$=3.09 min.

$^1$H-NMR (400 MHz, DMSO-d6) δ[ppm]: 1.215 (0.59), 1.233 (0.61), 2.075 (0.43), 2.190 (0.53), 2.207 (0.83), 2.223 (0.55), 2.327 (0.41), 2.518 (1.48), 2.523 (1.03), 2.669 (0.43), 3.276 (0.59), 3.286 (0.63), 3.295 (1.20), 3.318 (16.00), 3.330 (7.36), 4.045 (1.10), 4.076 (1.20), 4.158 (0.86), 4.173 (1.43), 4.188 (0.66), 4.463 (1.14), 4.494 (1.00), 6.858 (0.93), 6.876 (0.99), 7.003 (0.46), 7.015 (1.82), 7.018 (2.17), 7.020 (1.63), 7.036 (1.43), 7.053 (0.45), 7.355 (0.74), 7.375 (1.33), 7.394 (1.06), 7.442 (1.32), 7.463 (0.79), 7.514 (0.97), 7.517 (1.19), 7.528 (1.46), 7.538 (1.16), 7.541 (1.06), 7.715 (0.83), 7.720 (0.83), 7.732 (0.74), 7.738 (0.75), 7.856 (0.75), 7.860 (0.51), 7.869 (0.56), 7.873 (0.48), 7.879 (0.64), 8.251 (0.69), 8.262 (0.54), 8.276 (0.61).

Example 210

(rac)-1-methyl-7-[3-(naphthalen-1-yloxy)propyl]-3-[(pyrimidin-5-yloxy)methyl]-1,10,11,12,13,15-hexahydropyrazolo[4',3':9,10][1,6]oxazacycloundecino[8,7,6-hi]indole-8-carboxylic acid

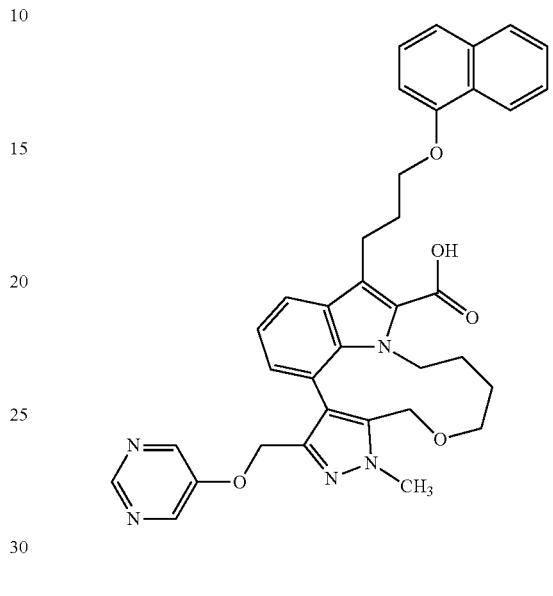

(rac)-ethyl 1-methyl-7-[3-(naphthalen-1-yloxy)propyl]-3-[(pyrimidin-5-yloxy)methyl]-1,10,11,12,13,15-hexahydropyrazolo[4',3':9,10][1,6]oxazacycloundecino[8,7,6-hi]indole-8-carboxylate (see Intermediate 348; 150 mg, 232 μmol) was stirred in a mixture of THF (3.3 ml), ethanol (1.6 ml) and an aqueous lithium hydroxide solution (1.6 ml, 1.0 M, 1.6 mmol) for 5 days at room temperature and another day at 50° C. After concentration to dryness the residue was purified by flash chromatography (Biotage SNAP cartridge silica 25 g, dichloromethane/methanol gradient, 0%-10% methanol) to give the title compound (127 mg).

LC-MS (Method 2): Rt=0.86 min; MS (ESIpos): m/z=619 [M+H]$^+$ $^1$H-NMR (400 MHz, DMSO-d6) δ[ppm]: 1.047 (1.03), 1.145 (0.44), 1.232 (1.29), 2.085 (0.85), 2.140 (1.07), 2.337 (0.66), 2.518 (8.57), 2.523 (5.92), 2.674 (1.54), 2.679 (0.74), 2.812 (0.55), 2.825 (0.40), 2.842 (0.59), 3.197 (0.44), 3.211 (0.48), 3.231 (0.63), 3.463 (0.66), 3.476 (0.59), 3.492 (0.63), 3.942 (16.00), 3.960 (2.35), 3.989 (0.55), 4.061 (0.59), 4.069 (0.66), 4.085 (1.03), 4.101 (0.85), 4.116 (1.10), 4.131 (0.63), 4.140 (0.55), 4.293 (1.51), 4.326 (1.62), 4.497 (0.48), 4.533 (0.40), 4.678 (1.84), 4.712 (1.62), 4.734 (2.06), 4.763 (2.46), 4.952 (2.43), 4.982 (2.13), 5.759 (5.37), 6.807 (1.84), 6.826 (2.72), 6.843 (1.18), 6.948 (1.18), 6.967 (1.58), 6.986 (0.96), 7.341 (1.29), 7.362 (2.35), 7.381 (2.02), 7.386 (0.51), 7.433 (2.57), 7.454 (1.58), 7.494 (0.55), 7.506 (1.73), 7.511 (2.94), 7.516 (0.85), 7.521 (3.24), 7.530 (3.09), 7.535 (1.84), 7.547 (0.59), 7.668 (1.25), 7.686 (1.07), 7.851 (1.51), 7.854 (1.07), 7.861 (0.70), 7.868 (1.07), 7.874 (1.32), 8.152 (0.44), 8.188 (1.21), 8.216 (10.85), 8.231 (1.43), 8.239 (0.92), 8.244 (0.59), 8.246 (0.55), 8.256 (1.14), 8.623 (1.58), 8.628 (11.55), 8.633 (0.48).

Example 211

1-methyl-7-[3-(naphthalen-1-yloxy)propyl]-3-[(pyrimidin-5-yloxy)methyl]-1,10,11,12,13,15-hexahydropyrazolo[4',3':9,10][1,6]oxazacycloundecino[8,7,6-hi]indole-8-carboxylic acid (Enantiomer 1)

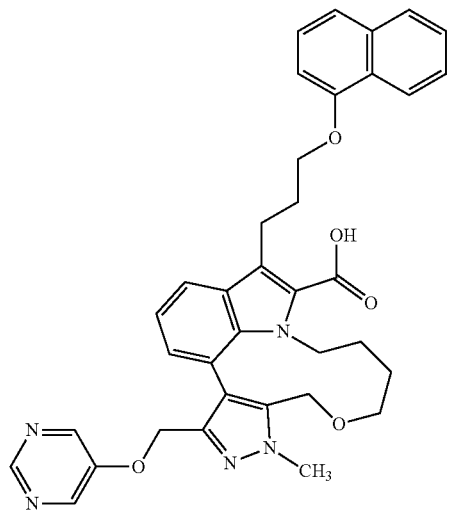 [SMILES: Cn1nc(COc2cncnc2)c2c1COCCCCn1c(C(=O)O)c(CCCOc3cccc4ccccc34)c3cccc-2c31]

(rac)-1-methyl-7-[3-(naphthalen-1-yloxy)propyl]-3-[(pyrimidin-5-yloxy)methyl]-1,10,11,12,13,15-hexahydropyrazolo[4',3':9,10][1,6]oxazacycloundecino[8,7,6-hi]indole-8-carboxylic acid (see Example 210; 125 mg, 202 μmol) was separated into the enantiomers by chiral HPLC.

Preparative chiral HPLC method: Instrument: Labomatic HD5000, Labocord-5000; Gilson GX-241, Labcol Vario 4000, column: Chiralpak AD 5μ 250×30 mm; Eluent A: hexane+0.1 Vol-% trifluoroacetic acid; Eluent B: isopropanol; isocratic: 60-40% runtime 20 min; Flow 50 ml/min; UV 254 nm Analytical chiral HPLC method: Instrument: Agilent HPLC 1260; Säule: Chiralpak AD 3μ 100×4.6 mm; Eluent A: hexane+0.1 Vol-% trifluoroacetic acid; Eluent B: isopropanol; Gradient: 20-50% B in 7 min; Flow 1.4 ml/min; Temperature: 25° C.; DAD 254 nm The preparative chiral HPLC yielded the title compound (46 mg).

Analytical Chiral HPLC: $R_t$=5.32 min.

LC-MS (Method 2): Rt=0.83 min; MS (ESIpos): m/z=619 [M+H]⁺

$^1$H-NMR (400 MHz, DMSO-d6) δ[ppm]: 1.049 (1.15), 1.062 (0.92), 1.107 (0.54), 1.136 (3.04), 1.154 (6.81), 1.173 (3.15), 1.233 (1.23), 1.262 (0.88), 2.140 (0.96), 2.337 (0.69), 2.518 (9.00), 2.523 (6.12), 2.674 (1.58), 2.679 (0.77), 2.816 (0.54), 2.828 (0.42), 2.846 (0.58), 2.903 (0.73), 2.921 (0.92), 2.933 (0.92), 2.952 (0.69), 3.207 (0.42), 3.220 (0.46), 3.240 (0.69), 3.464 (0.69), 3.478 (0.54), 3.494 (0.62), 3.926 (0.62), 3.944 (14.69), 3.962 (0.88), 4.000 (0.58), 4.024 (0.42), 4.062 (0.50), 4.070 (0.54), 4.086 (0.92), 4.102 (0.73), 4.118 (1.00), 4.133 (0.58), 4.142 (0.54), 4.295 (1.42), 4.329 (1.54), 4.480 (0.69), 4.491 (0.42), 4.515 (0.62), 4.679 (1.73), 4.713 (1.54), 4.735 (1.88), 4.765 (2.27), 4.955 (2.31), 4.984 (2.00), 6.808 (1.50), 6.826 (1.62), 6.841 (1.69), 6.845 (1.73), 6.859 (2.23), 6.862 (2.04), 6.958 (1.77), 6.975 (1.58), 6.978 (1.92), 6.996 (1.38), 7.343 (1.19), 7.364 (2.15), 7.383 (1.77), 7.435 (2.27), 7.456 (1.42), 7.495 (0.50), 7.508 (1.54), 7.513 (2.69), 7.523 (3.04), 7.532 (2.81), 7.537 (1.77), 7.549 (0.58), 7.678 (1.58), 7.681 (1.65), 7.698 (1.50), 7.701 (1.38), 7.852 (1.35), 7.856 (1.00), 7.863 (0.73), 7.867 (0.85), 7.870 (0.96), 7.875 (1.19), 8.175 (0.73), 8.207 (16.00), 8.216 (0.65), 8.233 (1.27), 8.240 (0.88), 8.245 (0.65), 8.257 (1.12), 8.623 (0.50), 8.628 (9.50), 8.633 (0.46), 13.183 (0.85).

Example 212

1-methyl-7-[3-(naphthalen-1-yloxy)propyl]-3-[(pyrimidin-5-yloxy)methyl]-1,10,11,12,13,15-hexahydropyrazolo[4',3':9,10][1,6]oxazacycloundecino[8,7,6-hi]indole-8-carboxylic acid (Enantiomer 2)

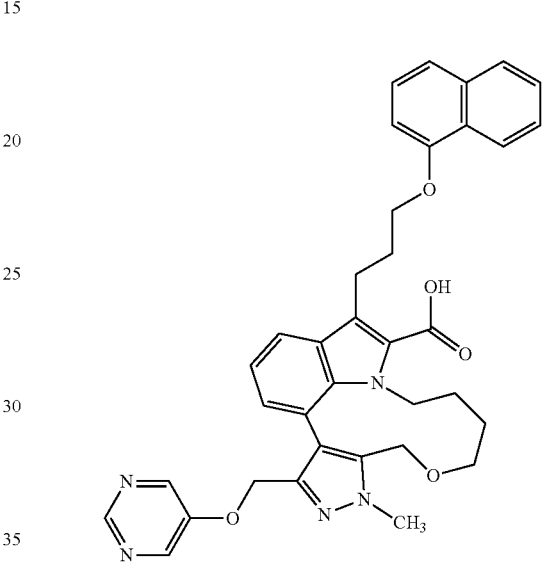

The preparative chiral HPLC of the racemic material (rac)-1-methyl-7-[3-(naphthalen-1-yloxy)propyl]-3-[(pyrimidin-5-yloxy)methyl]-1,10,11,12,13,15-hexahydropyrazolo[4',3':9,10][1,6]oxazacycloundecino[8,7,6-hi]indole-8-carboxylic acid (see Example 210; 125 mg, 202 μmol) is described in example 211 and yielded 21 mg of the title compound.

Analytical Chiral HPLC (method see Example 210): $R_t$=7.43 min.

LC-MS (Method 2): Rt=0.82 min; MS (ESIpos): m/z=619 [M+H]⁺

$^1$H-NMR (400 MHz, DMSO-d6) δ[ppm]: 0.852 (0.57), 1.048 (1.50), 1.085 (0.81), 1.136 (2.84), 1.154 (6.21), 1.173 (3.05), 1.233 (1.87), 1.268 (1.18), 1.976 (0.45), 1.993 (0.69), 2.063 (0.49), 2.140 (1.62), 2.336 (0.73), 2.518 (9.66), 2.523 (6.58), 2.679 (0.77), 2.817 (0.65), 2.829 (0.53), 2.846 (0.69), 2.903 (0.49), 2.921 (0.73), 2.933 (0.73), 2.951 (0.49), 3.207 (0.49), 3.221 (0.57), 3.240 (0.77), 3.257 (0.45), 3.448 (0.49), 3.464 (0.85), 3.478 (0.69), 3.494 (0.73), 3.926 (1.79), 3.944 (15.59), 3.962 (0.53), 3.991 (0.53), 4.000 (0.73), 4.014 (0.53), 4.023 (0.53), 4.036 (0.45), 4.062 (0.61), 4.070 (0.65), 4.086 (1.02), 4.102 (0.81), 4.117 (1.26), 4.133 (0.65), 4.142 (0.57), 4.295 (1.62), 4.329 (1.75), 4.480 (0.85), 4.490 (0.57), 4.504 (0.49), 4.515 (0.73), 4.679 (1.91), 4.713 (1.71), 4.735 (1.99), 4.765 (2.40), 4.955 (2.44), 4.984 (2.07), 6.808 (1.54), 6.826 (1.71), 6.841 (1.87), 6.845 (1.83), 6.859 (2.40), 6.862 (2.19), 6.958 (1.83), 6.978 (1.91), 6.996 (1.38), 7.343 (1.30), 7.364 (2.27), 7.383 (1.91), 7.435 (2.31), 7.456 (1.54), 7.495 (0.61), 7.508 (1.71), 7.513 (2.92), 7.522 (3.29), 7.532 (3.09), 7.537 (2.03), 7.549 (0.65), 7.678 (1.71), 7.681 (1.75), 7.698

(1.58), 7.701 (1.50), 7.852 (1.38), 7.855 (1.06), 7.862 (0.97), 7.867 (1.02), 7.870 (1.02), 7.875 (1.22), 7.885 (0.41), 8.207 (16.00), 8.216 (0.97), 8.233 (1.34), 8.240 (1.02), 8.257 (1.14), 8.628 (9.26), 13.184 (0.69).

Example 213

(rac)-3-[(cyclopropyloxy)methyl]-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid

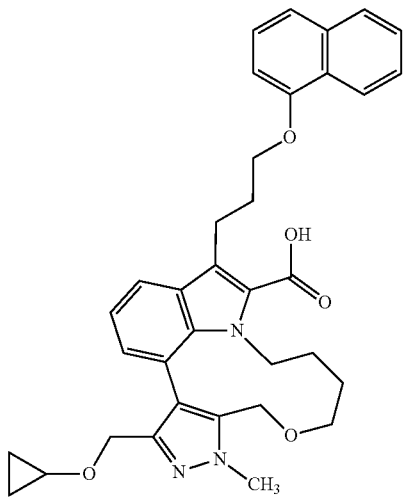 [SMILES: Cn1nc(COC2CC2)c2c1COCCCCn1c(C(=O)O)c(CCCOc3cccc4ccccc34)c3cccc-2c31]

To a solution of (rac)-ethyl 3-[(cyclopropyloxy)methyl]-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (see Intermediate 349; 110 mg, 181 µmol) in a mixture of THF (2.6 ml) and ethanol (1.3 ml) was added an aqueous solution of lithium hydroxide (1.3 ml, 1.0 M, 1.3 mmol). The resulting mixture was stirred at 50° C. for two days, followed by stirring at 70° C. for 5 hours. After removal of all volatiles the residue was subjected to flash chromatography (Biotage SNAP cartridge silica, dichloromethane/methanol gradient, 0%→10% methanol) to give the title compound (34 mg).

LC-MS (Method 2): Rt=0.86 min; MS (ESIpos): m/z=580 [M+H]$^+$ $^1$H-NMR (400 MHz, DMSO-d6) δ[ppm]: −0.547 (0.59), −0.539 (0.62), −0.514 (0.45), −0.072 (0.57), −0.063 (0.78), −0.054 (1.24), −0.040 (1.55), −0.031 (0.74), −0.027 (0.81), −0.016 (0.59), 0.085 (0.52), 0.090 (0.40), 0.101 (0.71), 0.108 (0.45), 0.114 (0.62), 0.796 (0.74), 0.880 (0.74), 1.071 (0.97), 1.228 (0.59), 1.252 (1.21), 1.260 (4.90), 1.283 (0.69), 1.300 (0.97), 1.318 (0.71), 1.785 (0.40), 2.206 (0.64), 2.223 (1.00), 2.238 (1.43), 2.255 (1.02), 2.326 (0.50), 2.364 (0.43), 2.546 (5.23), 2.551 (3.49), 2.706 (0.50), 2.769 (0.45), 2.783 (0.48), 2.800 (0.50), 3.026 (0.64), 3.034 (0.86), 3.041 (1.24), 3.049 (0.93), 3.056 (0.67), 3.282 (0.57), 3.296 (0.57), 3.315 (0.86), 3.416 (0.45), 3.434 (0.76), 3.450 (0.83), 3.467 (1.16), 3.485 (0.71), 3.498 (0.64), 3.914 (16.00), 3.941 (0.48), 3.952 (2.14), 3.979 (2.64), 3.999 (0.50), 4.151 (2.52), 4.178 (2.09), 4.194 (1.31), 4.210 (2.71), 4.225 (1.36), 4.306 (1.59), 4.340 (1.76), 4.474 (0.55), 4.509 (0.52), 4.680 (2.00), 4.714 (1.74), 6.823 (1.16), 6.840 (1.38), 6.883 (1.69), 6.900 (1.74), 7.011 (1.26), 7.031 (1.62), 7.049 (1.16), 7.384 (1.33), 7.395 (0.95), 7.399 (0.67), 7.405 (2.57), 7.410 (1.24), 7.414 (1.16), 7.418 (0.74), 7.424 (2.09), 7.429 (1.19), 7.467 (2.42), 7.488 (1.40), 7.527 (0.50), 7.539 (1.76), 7.543 (2.59), 7.553 (2.95), 7.562 (2.47), 7.567 (1.93), 7.578 (0.57), 7.767 (1.31), 7.784 (1.21), 7.794 (0.62), 7.798 (0.40), 7.813 (0.83), 7.881 (1.45), 7.885 (1.05), 7.893 (0.78), 7.895 (0.86), 7.899 (1.00), 7.905 (1.28), 8.273 (1.24), 8.281 (0.86), 8.297 (1.07), 8.593 (0.55), 8.597 (0.76), 8.602 (0.43), 8.607 (0.76), 8.612 (0.55).

Example 214

3-[(cyclopropyloxy)methyl]-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (Enantiomer 1)

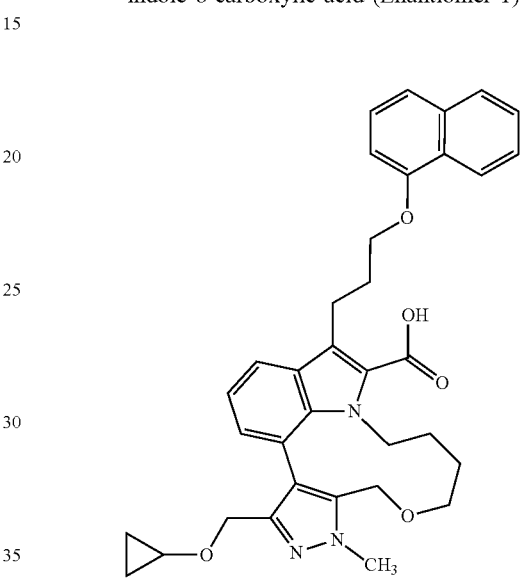

(rac)-3-[(cyclopropyloxy)methyl]-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (see Example 213, 30.0 mg, 51.8 µmol) was separated into the enantiomers by chiral HPLC.

Preparative chiral HPLC method: Instrument: Labomatic HD5000, Labocord-5000; Gilson GX-241, Labcol Vario 4000, column: Chiralpak ID 5µ 250×30 mm; Eluent A: hexane+0.1 Vol-% trifluoroacetic acid (99%); Eluent B: 2-propanol; Gradient: 30→50% B in 10 min; Flow 40.0 ml/min; UV 220 nm Analytical chiral HPLC method: Instrument: Waters Alliance 2695Agilent HPLC 1260; column: Chiralpak ID 3µ 100×4.6 mm; Eluent A: hexane+0.1 Vol-% trifluoroacetic acid (99%); Eluent B: 2-propanol; Isocratic: 50% A+50% B; Flow 1.4 ml/min; Temperature: 25° C.; DAD 220 nm The preparative chiral HPLC yielded the title compound (11 mg).

Analytical Chiral HPLC: R$_t$=2.95 min.

LC-MS (Method 2): Rt=0.87 min; MS (ESIpos): m/z=581 [M+H]$^+$ $^1$H-NMR (400 MHz, DMSO-d6) δ[ppm]: −0.553 (0.83), −0.545 (0.75), −0.538 (0.72), −0.529 (0.48), −0.520 (0.59), −0.075 (0.64), −0.066 (0.91), −0.056 (1.28), −0.048 (1.10), −0.041 (1.92), −0.031 (0.85), −0.027 (0.88), −0.016 (0.69), 0.087 (0.59), 0.092 (0.51), 0.103 (0.83), 0.111 (0.67), 0.116 (0.72), 0.132 (0.51), 0.778 (0.61), 0.795 (1.04), 0.812 (0.75), 0.881 (0.53), 1.074 (1.39), 1.183 (1.15), 1.202 (1.60), 1.234 (1.20), 1.261 (2.48), 1.285 (1.31), 1.325 (1.10), 1.361 (0.67), 2.223 (1.15), 2.239 (1.68), 2.257 (1.20), 2.547 (6.86), 2.552

(4.54), 2.568 (0.56), 2.771 (0.59), 2.785 (0.61), 2.802 (0.69), 3.020 (0.43), 3.027 (0.77), 3.035 (1.12), 3.042 (1.42), 3.049 (1.07), 3.057 (0.77), 3.288 (0.69), 3.303 (0.69), 3.321 (1.02), 3.419 (0.53), 3.437 (0.91), 3.454 (0.99), 3.470 (1.42), 3.488 (0.85), 3.499 (0.77), 3.916 (16.00), 3.951 (2.62), 3.978 (3.31), 4.005 (0.51), 4.015 (0.45), 4.154 (2.83), 4.180 (2.40), 4.196 (1.60), 4.211 (3.21), 4.227 (1.55), 4.308 (1.79), 4.342 (1.98), 4.467 (0.77), 4.503 (0.75), 4.682 (2.22), 4.715 (1.95), 6.832 (1.63), 6.849 (1.98), 6.885 (1.92), 6.903 (2.06), 7.017 (1.55), 7.036 (2.08), 7.054 (1.36), 7.386 (1.34), 7.406 (2.62), 7.426 (2.00), 7.469 (2.83), 7.489 (1.63), 7.529 (0.53), 7.541 (1.87), 7.545 (2.78), 7.555 (3.15), 7.564 (2.80), 7.569 (2.00), 7.580 (0.59), 7.774 (1.74), 7.792 (1.63), 7.883 (1.66), 7.897 (1.04), 7.900 (1.10), 7.907 (1.42), 8.275 (1.39), 8.283 (1.02), 8.299 (1.26).

Example 215

3-[(cyclopropyloxy)methyl]-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (Enantiomer 2)

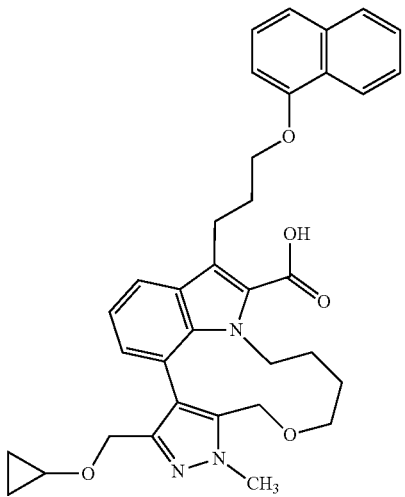 [SMILES: Cn1nc(COC2CC2)c2c1COCCCCn1c(C(=O)O)c(CCCOc3cccc4ccccc34)c3cccc-2c31]

The preparative chiral HPLC of the racemic material (rac)-3-[(cyclopropyloxy)methyl]-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (see Example 213, 30.0 mg, 51.8 μmol) is described in example 214 and yielded 10 mg of the title compound.

Analytical Chiral HPLC (method see Example 214): $R_t$=5.70 min.

LC-MS (Method 2): Rt=0.87 min; MS (ESIpos): m/z=581 [M+H]$^+$ $^1$H-NMR (400 MHz, DMSO-d6) δ[ppm]: −0.533 (0.73), −0.525 (0.73), −0.501 (0.53), −0.057 (0.63), −0.048 (0.89), −0.039 (1.39), −0.025 (1.92), −0.011 (0.89), 0.000 (0.69), 0.102 (0.60), 0.118 (0.83), 0.125 (0.63), 0.131 (0.69), 0.146 (0.46), 0.826 (0.50), 0.896 (0.56), 1.088 (1.29), 1.199 (1.26), 1.217 (1.92), 1.276 (2.31), 1.301 (0.99), 1.340 (0.99), 2.238 (1.06), 2.254 (1.59), 2.271 (1.12), 2.563 (7.34), 2.567 (5.02), 2.584 (0.53), 2.787 (0.56), 2.799 (0.56), 2.816 (0.63), 3.043 (0.73), 3.050 (1.02), 3.057 (1.29), 3.065 (1.02), 3.072 (0.69), 3.300 (0.63), 3.314 (0.63), 3.332 (0.89), 3.433 (0.50), 3.451 (0.86), 3.467 (0.99), 3.484 (1.36), 3.502 (0.86), 3.514 (0.73), 3.931 (16.00), 3.967 (2.51), 3.994 (3.11), 4.016 (0.46), 4.168 (2.74), 4.194 (2.31), 4.211 (1.49), 4.226 (2.98), 4.241 (1.42), 4.323 (1.75), 4.356 (1.95), 4.487 (0.69), 4.522 (0.63), 4.696 (2.15), 4.731 (1.88), 6.842 (1.42), 6.858 (1.62), 6.899 (1.85), 6.918 (2.02), 7.029 (1.36), 7.048 (1.88), 7.066 (1.16), 7.401 (1.22), 7.421 (2.41), 7.441 (1.88), 7.484 (2.68), 7.504 (1.52), 7.544 (0.46), 7.556 (1.65), 7.560 (2.64), 7.570 (3.01), 7.579 (2.68), 7.583 (1.92), 7.595 (0.53), 7.784 (1.55), 7.803 (1.45), 7.898 (1.52), 7.912 (0.96), 7.916 (0.99), 7.921 (1.29), 8.290 (1.29), 8.298 (0.93), 8.314 (1.26).

Example 216

(rac)-1-methyl-7-[3-(naphthalen-1-yloxy)propyl]-3-(trifluoromethyl)-1,10,11,12,13,15-hexahydropyrazolo[4',3':9,10][1,6]oxazacycloundecino[8,7,6-hi]indole-8-carboxylic acid

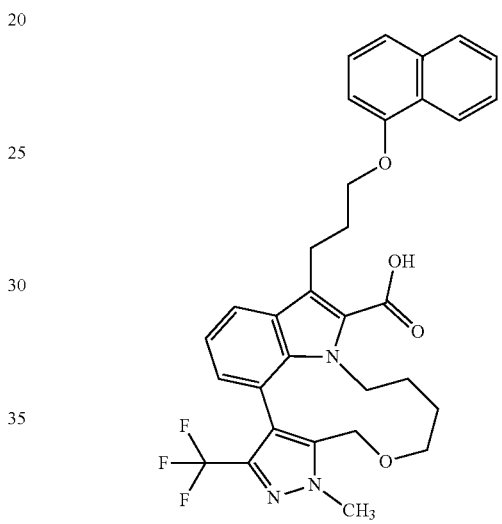

To a solution of (rac)-ethyl 1-methyl-7-[3-(naphthalen-1-yloxy)propyl]-3-(trifluoromethyl)-1,10,11,12,13,15-hexahydropyrazolo[4',3':9,10][1,6]oxazacycloundecino[8,7,6-hi]indole-8-carboxylate (see Intermediate 353; 890 mg, 1.47 mmol) in a mixture of THF (72 ml) and ethanol (50 ml) was added an aqueous solution of lithium hydroxide (29 ml, 1.0 M, 29 mmol). The resulting mixture was stirred at 60° C. for 32 hours. After removal of all volatiles the residue was subjected to flash chromatography (Biotage SNAP cartridge silica, dichloromethane/methanol gradient, 0%→100% methanol) to give the title compound (620 mg).

LC-MS (Method 1): Rt=1.51 min; MS (ESIpos): m/z=579 [M+H]$^+$ $^1$H-NMR (400 MHz, DMSO-d6) δ[ppm]: 0.979 (0.75), 0.996 (0.75), 1.027 (1.42), 1.043 (1.51), 1.059 (0.62), 1.231 (1.47), 1.285 (0.78), 1.353 (0.75), 1.907 (0.40), 2.179 (0.58), 2.196 (1.48), 2.214 (2.14), 2.231 (1.58), 2.518 (7.57), 2.523 (5.53), 2.812 (0.46), 2.831 (0.92), 2.842 (0.78), 2.860 (0.96), 2.877 (0.49), 3.270 (0.68), 3.285 (0.99), 3.304 (1.77), 3.331 (8.58), 3.363 (1.17), 3.378 (0.82), 3.450 (0.50), 3.464 (0.94), 3.480 (0.96), 3.494 (0.88), 3.511 (0.49), 3.817 (0.47), 3.827 (0.52), 3.840 (0.65), 3.852 (1.01), 3.862 (0.63), 3.876 (0.63), 3.887 (0.52), 3.949 (0.46), 4.017 (16.00), 4.187 (1.94), 4.203 (4.12), 4.218 (2.07), 4.256 (2.53), 4.290 (2.73), 4.516 (1.18), 4.541 (0.63), 4.552 (1.06), 4.701 (2.95), 4.735 (2.68), 6.879 (2.63), 6.896 (2.91), 6.916 (2.49), 6.918 (2.62), 6.934 (3.15), 6.936 (3.04), 7.046 (2.79), 7.066 (3.22), 7.084 (2.16), 7.364 (1.97), 7.384 (3.71), 7.403 (3.06), 7.445 (3.83), 7.466 (2.23), 7.486 (0.68), 7.490 (0.95), 7.503 (2.29), 7.507 (2.19), 7.513 (2.65), 7.520 (4.99), 7.527 (2.66), 7.532 (2.35), 7.537 (2.58), 7.549 (1.04), 7.554 (0.65), 7.799 (2.59), 7.802 (2.68), 7.819 (2.55), 7.822 (2.42), 7.855 (2.23), 7.863 (1.28), 7.873 (2.19), 7.878 (1.96), 8.229 (1.97), 8.234 (1.86), 8.246 (1.09), 8.253 (1.86), 13.267 (0.56).

The title compound (620 mg) was separated into enantiomers by preparative chiral HPLC to give enantiomer 1 (215 mg, see Example 217) and enantiomer 2 (210 mg, see Example 218).

Preparative chiral HPLC method: Instrument: Labomatic HD5000, Labocord-5000; Gilson GX-241, Labcol Vario 4000, column: Chiralpak ID 5µ 250×30 mm; Eluent A: hexane+0.1 Vol-% trifluoroacetic acid (99%); Eluent B: 2-propanol; Gradient: 20→50% B in 20 min; Flow 40.0 ml/min; UV 254 nm Analytical chiral HPLC method: Instrument: Waters Alliance 2695Agilent HPLC 1260; column: Chiralpak ID 3µ 100×4.6 mm; Eluent A: hexane+0.1 Vol-% trifluoroacetic acid (99%); Eluent B: 2-propanol; Gradient: 20-50% B in 7 min; Flow 1.4 ml/min; Temperature: 25° C.; DAD 254 nm Example 217

1-methyl-7-[3-(naphthalen-1-yloxy)propyl]-3-(trifluoromethyl)-1,10,11,12,13,15-hexahydropyrazolo [4',3':9,10][1,6]oxazacycloundecino[8,7,6-hi]indole-8-carboxylic acid (Enantiomer 1)

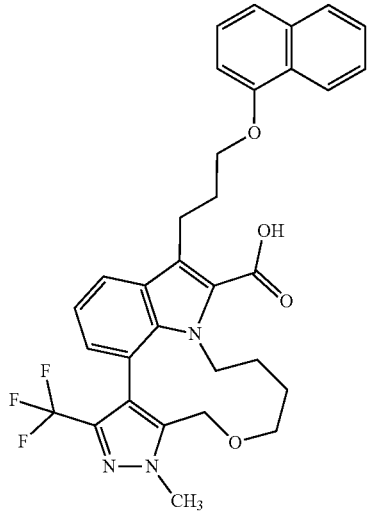 [SMILES: Cn1nc(C(F)(F)F)c2c1COCCCCn1c(C(=O)O)c(CCCOc3cccc4ccccc34)c3cccc-2c31]

For the preparation of the racemic title compound see Example 216. Separation of enantiomers by preparative chiral HPLC (method see Example 216) gave the title compound (215 mg).

Analytical Chiral HPLC (method see Example 216): $R_t$=1.73 min.

$^1$H-NMR (400 MHz, DMSO-d6) δ[ppm]: 0.967 (0.46), 0.979 (0.45), 0.997 (0.44), 1.027 (0.45), 1.043 (0.49), 1.108 (16.00), 1.260 (0.42), 1.278 (0.56), 1.296 (0.57), 1.355 (0.43), 2.197 (0.89), 2.214 (1.31), 2.232 (0.96), 2.518 (1.98), 2.523 (1.27), 2.831 (0.57), 2.843 (0.48), 2.861 (0.60), 3.288 (0.56), 3.307 (0.90), 3.327 (0.80), 3.346 (0.93), 3.365 (0.54), 3.380 (0.41), 3.466 (0.58), 3.481 (0.60), 3.495 (0.54), 3.845 (0.40), 3.855 (0.66), 3.880 (0.41), 4.018 (9.99), 4.188 (1.28), 4.203 (2.62), 4.219 (1.38), 4.257 (1.61), 4.291 (1.76), 4.513 (0.76), 4.524 (0.45), 4.536 (0.41), 4.548 (0.71), 4.701 (1.82), 4.735 (1.64), 5.759 (1.53), 6.879 (1.61), 6.897 (1.78), 6.921 (1.47), 6.924 (1.53), 6.939 (1.90), 6.941 (1.84), 7.049 (1.52), 7.069 (1.93), 7.087 (1.22), 7.364 (1.09), 7.384 (2.15), 7.403 (1.65), 7.446 (2.34), 7.466 (1.31), 7.490 (0.50), 7.504 (1.26), 7.507 (1.25), 7.513 (1.46), 7.520 (2.70), 7.528 (1.49), 7.532 (1.33), 7.537 (1.38), 7.550 (0.53), 7.803 (1.58), 7.806 (1.64), 7.823 (1.54), 7.826 (1.51), 7.856 (1.35), 7.863 (0.76), 7.873 (1.25), 7.878 (1.16), 8.229 (1.13), 8.235 (1.12), 8.253 (1.11).

Example 218

1-methyl-7-[3-(naphthalen-1-yloxy)propyl]-3-(trifluoromethyl)-1,10,11,12,13,15-hexahydropyrazolo [4',3':9,10][1,6]oxazacycloundecino[8,7,6-hi]indole-8-carboxylic acid (Enantiomer 2)

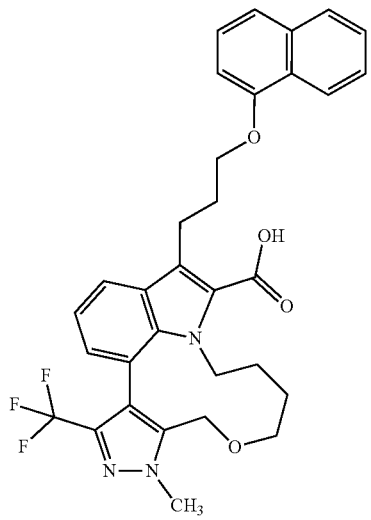 [SMILES: Cn1nc(C(F)(F)F)c2c1COCCCCn1c(C(=O)O)c(CCCOc3cccc4ccccc34)c3cccc-2c31]

For the preparation of the racemic title compound see Example 216. Separation of enantiomers by preparative chiral HPLC (method see Example 216) gave the title compound (210 mg).

Analytical Chiral HPLC (method see Example 216): $R_t$=2.89 min.

$^1$H-NMR (400 MHz, DMSO-d6) δ[ppm]: 1.172 (16.00), 2.262 (0.66), 2.279 (0.98), 2.296 (0.71), 2.587 (1.05), 2.896 (0.42), 2.925 (0.44), 3.352 (0.40), 3.371 (0.66), 3.391 (0.59), 3.411 (0.67), 3.531 (0.44), 3.545 (0.44), 3.561 (0.40), 3.920 (0.49), 4.082 (7.13), 4.253 (0.93), 4.268 (1.87), 4.283 (0.93), 4.321 (1.16), 4.355 (1.26), 4.577 (0.60), 4.612 (0.57), 4.765 (1.32), 4.800 (1.18), 5.823 (0.59), 6.943 (1.18), 6.961 (1.28), 6.985 (1.08), 6.987 (1.12), 7.003 (1.40), 7.005 (1.36), 7.114 (1.07), 7.134 (1.38), 7.151 (0.86), 7.429 (0.77), 7.449 (1.54), 7.468 (1.17), 7.510 (1.67), 7.531 (0.94), 7.568 (0.91), 7.572 (0.89), 7.578 (1.02), 7.584 (1.93), 7.592 (1.07), 7.597 (0.96), 7.602 (0.98), 7.867 (1.15), 7.870 (1.20), 7.888 (1.11), 7.920 (0.98), 7.928 (0.54), 7.938 (0.89), 7.943 (0.83), 8.293 (0.83), 8.299 (0.82), 8.318 (0.82).

Example 219

(rac)-1-methyl-7-[3-(naphthalen-1-yloxy)propyl]-3-(2,2,2-trifluoroethyl)-1,10,11,12,13,15-hexahydropyrazolo[4',3':9,10][1,6]oxazacycloundecino[8,7,6-hi]indole-8-carboxylic acid

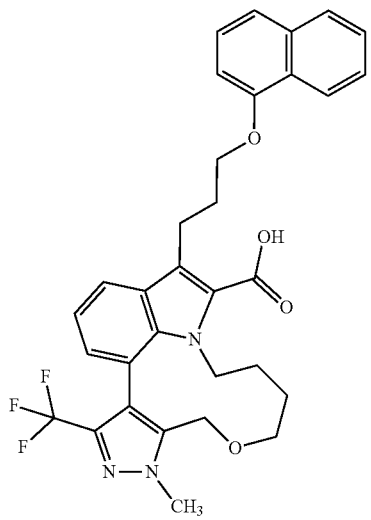 [SMILES: Cn1nc(C(F)(F)F)c2c1COCCCCn1c(C(=O)O)c(CCCOc3cccc4ccccc34)c3cccc-2c31]

To a solution of (rac)-ethyl 1-methyl-7-[3-(naphthalen-1-yloxy)propyl]-3-(2,2,2-trifluoroethyl)-1,10,11,12,13,15-hexahydropyrazolo[4',3':9,10][1,6]oxazacycloundecino[8,7,6-hi]indole-8-carboxylate (see Intermediate 359; 700 mg, 1.13 mmol) in a mixture of THF (55 ml) and ethanol (38 ml) was added an aqueous solution of lithium hydroxide (23 ml, 1.0 M, 23 mmol). The resulting mixture was stirred at 60° C. for 17 hours. After removal of all volatiles the residue was subjected to flash chromatography (Biotage SNAP cartridge silica, dichloromethane/2-propanol gradient, 0%→100% 2-propanol) to give the title compound (410 mg).

LC-MS (Method 1): Rt=1.51 min; MS (ESIpos): m/z=579 [M+H]$^+$ $^1$H-NMR (400 MHz, DMSO-d6) δ[ppm]: 0.979 (0.75), 0.996 (0.75), 1.027 (1.42), 1.043 (1.51), 1.059 (0.62), 1.231 (1.47), 1.285 (0.78), 1.353 (0.75), 1.907 (0.40), 2.179 (0.58), 2.196 (1.48), 2.214 (2.14), 2.231 (1.58), 2.518 (7.57), 2.523 (5.53), 2.812 (0.46), 2.831 (0.92), 2.842 (0.78), 2.860 (0.96), 2.877 (0.49), 3.270 (0.68), 3.285 (0.99), 3.304 (1.77), 3.331 (8.58), 3.363 (1.17), 3.378 (0.82), 3.450 (0.50), 3.464 (0.94), 3.480 (0.96), 3.494 (0.88), 3.511 (0.49), 3.817 (0.47), 3.827 (0.52), 3.840 (0.65), 3.852 (1.01), 3.862 (0.63), 3.876 (0.63), 3.887 (0.52), 3.949 (0.46), 4.017 (16.00), 4.187 (1.94), 4.203 (4.12), 4.218 (2.07), 4.256 (2.53), 4.290 (2.73), 4.516 (1.18), 4.541 (0.63), 4.552 (1.06), 4.701 (2.95), 4.735 (2.68), 6.879 (2.63), 6.896 (2.91), 6.916 (2.49), 6.918 (2.62), 6.934 (3.15), 6.936 (3.04), 7.046 (2.79), 7.066 (3.22), 7.084 (2.16), 7.364 (1.97), 7.384 (3.71), 7.403 (3.06), 7.445 (3.83), 7.466 (2.23), 7.486 (0.68), 7.490 (0.95), 7.503 (2.29), 7.507 (2.19), 7.513 (2.65), 7.520 (4.99), 7.527 (2.66), 7.532 (2.35), 7.537 (2.58), 7.549 (1.04), 7.554 (0.65), 7.799 (2.59), 7.802 (2.68), 7.819 (2.55), 7.822 (2.42), 7.855 (2.23), 7.863 (1.28), 7.873 (2.19), 7.878 (1.96), 8.229 (1.97), 8.234 (1.86), 8.246 (1.09), 8.253 (1.86), 13.267 (0.56).

The title compound (400 mg) was separated into enantiomers by preparative chiral HPLC to give enantiomer 1 (114 mg, see Example 220) and enantiomer 2 (101 mg, see Example 221).

Preparative chiral HPLC method: Instrument: Labomatic HD5000, Labocord-5000; Gilson GX-241, Labcol Vario 4000, column: YMC Amylose SA 5μ 250×30 mm; Eluent A: hexane+0.1 Vol-% N-ethylethanamine (99%); Eluent B: ethanol; Gradient: 20→50% B in 20 min; Flow 40.0 ml/min; UV 254 nm Analytical chiral HPLC method: Instrument: Agilent HPLC 1260; column: YMC Amylose SA 3μ 100×4.6 mm; Eluent A: hexane+0.1 Vol-% N-ethylethanamine (99%); Eluent B: ethanol; Gradient: 20-50% B in 7 min; Flow 1.4 ml/min; Temperature: 25° C.; DAD 254 nm

Example 220

1-methyl-7-[3-(naphthalen-1-yloxy)propyl]-3-(2,2,2-trifluoroethyl)-1,10,11,12,13,15-hexahydropyrazolo[4',3':9,10][1,6]oxazacycloundecino[8,7,6-hi]indole-8-carboxylic acid-N-ethylethanamine salt (Enantiomer 1)

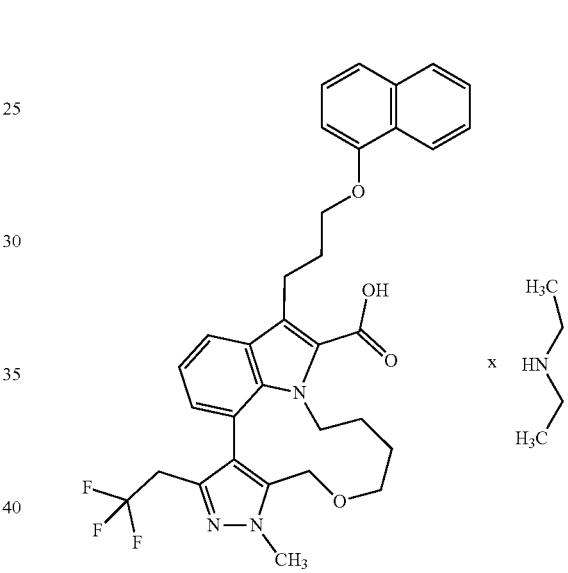

For the preparation of the racemic title compound see Example 219. Separation of enantiomers by preparative chiral HPLC (method see Example 219) gave the title compound (114 mg).

Analytical Chiral HPLC (method see Example 219): R$_t$=1.56 min.

$^1$H-NMR (400 MHz, DMSO-d6) δ[ppm]: 0.967 (0.87), 0.982 (0.48), 0.994 (0.58), 1.006 (0.67), 1.035 (0.52), 1.084 (0.43), 1.107 (2.08), 1.135 (6.95), 1.144 (1.33), 1.154 (16.00), 1.171 (7.00), 2.190 (0.71), 2.209 (1.03), 2.224 (0.75), 2.518 (2.69), 2.523 (1.71), 2.799 (0.40), 2.827 (2.21), 2.845 (5.77), 2.864 (5.61), 2.882 (1.69), 3.038 (0.50), 3.066 (0.49), 3.076 (0.71), 3.105 (0.63), 3.160 (0.42), 3.175 (0.49), 3.193 (0.74), 3.225 (0.74), 3.254 (0.85), 3.263 (0.95), 3.280 (1.13), 3.292 (1.19), 3.313 (1.15), 3.330 (1.17), 3.410 (0.42), 3.426 (0.64), 3.438 (0.53), 3.456 (0.57), 3.783 (0.53), 3.908 (13.37), 4.174 (0.79), 4.185 (1.51), 4.190 (1.53), 4.204 (2.10), 4.238 (1.54), 4.641 (2.01), 4.675 (1.86), 5.759 (0.79), 6.655 (1.11), 6.672 (1.22), 6.852 (1.43), 6.870 (1.57), 6.927 (1.22), 6.946 (1.63), 6.965 (1.09), 7.338 (1.10), 7.358 (1.99), 7.378 (1.57), 7.426 (2.11), 7.447 (1.28), 7.476 (0.49), 7.489 (1.30), 7.493 (1.13), 7.501 (1.37), 7.507 (2.76), 7.513 (1.39), 7.520 (1.22), 7.524 (1.36), 7.537 (0.54), 7.620 (1.25), 7.637

(1.15), 7.844 (1.26), 7.851 (0.72), 7.862 (1.30), 7.868 (1.06), 8.221 (1.09), 8.226 (1.07), 8.245 (1.05).

Example 221

1-methyl-7-[3-(naphthalen-1-yloxy)propyl]-3-(2,2,2-trifluoroethyl)-1,10,11,12,13,15-hexahydropyrazolo[4',3':9,10][1,6]oxazacycloundecino[8,7,6-hi]indole-8-carboxylic acid-N-ethylethanamine salt (Enantiomer 2)

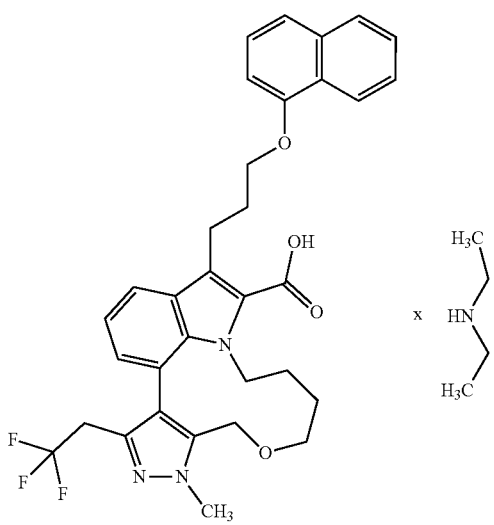

For the preparation of the racemic title compound see Example 219. Separation of enantiomers by preparative chiral HPLC (method see Example 219) gave the title compound (101 mg).

Analytical Chiral HPLC (method see Example 219): $R_t$=5.10 min.

$^1$H-NMR (400 MHz, DMSO-d6) δ[ppm]: 0.795 (0.47), 0.967 (0.79), 0.982 (0.54), 1.006 (0.93), 1.035 (0.66), 1.084 (0.68), 1.107 (2.06), 1.138 (6.95), 1.156 (16.00), 1.175 (7.22), 1.259 (0.76), 2.191 (0.76), 2.209 (1.13), 2.224 (0.82), 2.518 (2.80), 2.523 (1.83), 2.801 (0.45), 2.820 (0.51), 2.833 (2.32), 2.852 (6.07), 2.869 (5.68), 2.888 (1.76), 3.039 (0.52), 3.067 (0.54), 3.077 (0.78), 3.106 (0.68), 3.164 (0.45), 3.180 (0.53), 3.197 (0.92), 3.223 (0.86), 3.252 (0.87), 3.262 (1.10), 3.282 (1.22), 3.290 (1.07), 3.299 (1.02), 3.316 (1.26), 3.332 (1.13), 3.408 (0.45), 3.426 (0.70), 3.439 (0.58), 3.456 (0.60), 3.789 (0.57), 3.908 (14.22), 4.174 (0.87), 4.186 (1.69), 4.190 (1.70), 4.205 (2.30), 4.238 (1.64), 4.641 (2.13), 4.665 (0.63), 4.675 (1.89), 5.759 (0.58), 6.662 (1.19), 6.679 (1.33), 6.853 (1.59), 6.871 (1.71), 6.931 (1.27), 6.951 (1.77), 6.969 (1.13), 7.338 (1.20), 7.359 (2.23), 7.378 (1.70), 7.426 (2.30), 7.447 (1.37), 7.476 (0.54), 7.489 (1.38), 7.494 (1.23), 7.501 (1.46), 7.507 (2.90), 7.513 (1.48), 7.520 (1.35), 7.525 (1.50), 7.537 (0.60), 7.625 (1.36), 7.643 (1.26), 7.844 (1.35), 7.851 (0.78), 7.863 (1.38), 7.868 (1.17), 8.221 (1.22), 8.226 (1.18), 8.245 (1.14).

Example 222

(rac)-1,14-dimethyl-7-[3-(naphthalen-1-yloxy)propyl]-3-(2,2,2-trifluoroethyl)-10,11,12,13,14,15-hexahydro-1H-pyrazolo[3',4':8,9][1,6]diazacycloundecino[10,11,1-hi]indole-8-carboxylic acid

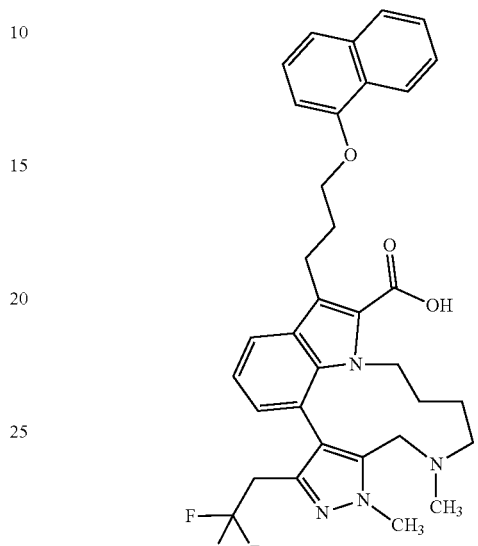

To a solution of (rac)-ethyl 1,14-dimethyl-7-[3-(naphthalen-1-yloxy)propyl]-3-(2,2,2-trifluoroethyl)-10,11,12,13,14,15-hexahydro-1H-pyrazolo[3',4':8,9][1,6]diazacycloundecino[10,11,1-hi]indole-8-carboxylate (see Intermediate 363; 210 mg, 332 μmol) in a mixture of THF (16 ml) and ethanol (11 ml) was added an aqueous solution of lithium hydroxide (6.6 ml, 1.0 M, 6.6 mmol). The resulting mixture was stirred at 40° C. for 4 days. After removal of all volatiles the residue was subjected to flash chromatography (Biotage SNAP cartridge silica, dichloromethane/2-propanol gradient, 0%→100% 2-propanol) to give the title compound (170 mg).

LC-MS (Method 2): Rt=0.95 min; MS (ESIpos): m/z=606 [M+H]$^+$ $^1$H-NMR (400 MHz, DMSO-d6) δ[ppm]: 0.723 (0.45), 0.751 (0.51), 0.984 (0.44), 1.094 (0.53), 1.230 (2.49), 1.348 (0.40), 1.907 (0.88), 1.933 (0.42), 2.154 (10.00), 2.178 (0.60), 2.195 (1.03), 2.212 (1.45), 2.229 (1.03), 2.428 (0.46), 2.452 (0.47), 2.470 (0.51), 2.518 (2.19), 2.523 (1.50), 3.017 (0.57), 3.045 (0.60), 3.055 (0.85), 3.084 (0.74), 3.222 (0.85), 3.232 (0.45), 3.243 (1.83), 3.250 (1.16), 3.260 (1.26), 3.276 (2.36), 3.294 (1.35), 3.333 (2.64), 3.352 (1.62), 3.371 (0.78), 3.386 (0.64), 3.681 (1.64), 3.714 (1.46), 3.844 (0.67), 3.872 (0.44), 3.920 (16.00), 4.196 (1.37), 4.212 (2.86), 4.227 (1.33), 4.563 (0.63), 4.598 (0.58), 5.759 (5.34), 6.815 (1.60), 6.817 (1.63), 6.832 (1.88), 6.880 (1.80), 6.898 (1.96), 7.029 (1.79), 7.048 (2.11), 7.066 (1.47), 7.361 (1.42), 7.381 (2.57), 7.400 (2.05), 7.446 (2.62), 7.466 (1.52), 7.498 (0.50), 7.511 (1.66), 7.515 (3.01), 7.525 (3.28), 7.534 (3.09), 7.539 (1.93), 7.551 (0.59), 7.752 (1.72), 7.754 (1.80), 7.771 (1.64), 7.774 (1.58), 7.856 (1.50), 7.859 (1.07), 7.866 (0.77), 7.871 (0.92), 7.873 (0.98), 7.879 (1.29), 8.253 (1.30), 8.260 (0.93), 8.276 (1.24).

The title compound (160 mg) was separated into enantiomers by preparative chiral HPLC to give enantiomer 1 (62 mg, see Example 223) and enantiomer 2 (74 mg, see Example 224).

Preparative chiral HPLC method: Instrument: Sepiatec: Prep SFC100; column: Chiralpak IA 5 μm 250×30 mm; Eluent A: CO$_2$, Eluent B: ethanol+0.2 Vol-% aqueous ammonia (32%); Isocratic: 20% B; Flow 100.0 ml/min Temperature: 40° C.; BPR: 150 bar; MWD @ 220 nm Analytical chiral HPLC method: Instrument: Agilent: 1260, Aurora SFC-Modul; Column: Chiralpak IA 5 μm 100×4.6 mm; Eluent A: CO$_2$, Eluent B: ethanol+0.2 Vol-% aqueous ammonia (32%); Isocratic: 20% B; Flow 4.0 ml/min; Temperature: 37.5° C.; BPR: 100 bar; MWD @ 220 nm Example 223

1,14-dimethyl-7-[3-(naphthalen-1-yloxy)propyl]-3-(2,2,2-trifluoroethyl)-10,11,12,13,14,15-hexahydro-1H-pyrazolo[3',4':8,9][1,6]diazacycloundecino[10,11,1-hi]indole-8-carboxylic acid (Enantiomer 1)

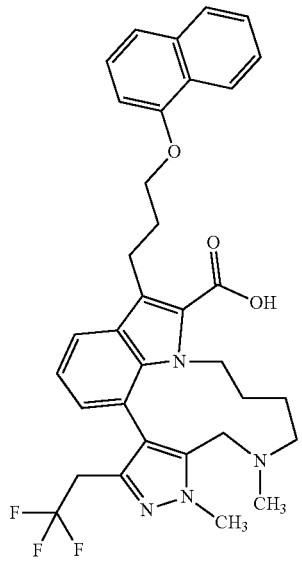 [SMILES: CN1CCCCn2c(C(=O)O)c(CCCOc3cccc4ccccc34)c3cccc(c32)-c2c(CC(F)(F)F)nn(C)c2C1]

For the preparation of the racemic title compound see Example 222. Separation of enantiomers by preparative chiral HPLC (method see Example 222) gave the title compound (62 mg).

Analytical Chiral HPLC (method see Example 222): R$_t$=2.23 min.

$^1$H-NMR (400 MHz, DMSO-d6) δ[ppm]: 0.707 (1.21), 0.725 (2.57), 0.743 (1.72), 0.777 (1.36), 0.798 (2.13), 0.802 (2.17), 0.814 (2.22), 0.821 (2.43), 0.833 (2.30), 0.841 (3.07), 0.845 (3.20), 0.852 (4.25), 0.861 (8.35), 0.878 (4.58), 0.895 (1.67), 0.903 (1.78), 0.912 (1.38), 0.922 (1.13), 0.962 (1.72), 0.984 (1.84), 1.038 (3.12), 1.061 (2.72), 1.067 (2.22), 1.081 (1.44), 1.088 (1.95), 1.105 (1.09), 1.130 (2.18), 1.134 (2.80), 1.149 (3.31), 1.159 (0.90), 1.199 (1.11), 1.205 (1.11), 1.232 (1.30), 1.248 (0.75), 1.292 (1.23), 1.354 (1.76), 1.361 (1.28), 1.387 (1.09), 1.420 (1.11), 1.439 (1.55), 1.458 (1.26), 1.478 (0.54), 1.869 (0.67), 1.907 (1.53), 1.919 (1.40), 2.005 (0.92), 2.036 (1.25), 2.100 (0.61), 2.132 (1.07), 2.152 (11.40), 2.210 (2.59), 2.268 (0.54), 2.284 (0.44), 2.326 (1.25), 2.411 (0.80), 2.432 (1.00), 2.668 (1.38), 2.763 (0.42), 3.007 (0.71), 3.034 (0.77), 3.045 (1.02), 3.073 (0.92), 3.237 (2.89), 3.269 (3.28), 3.292 (1.95), 3.332 (2.74), 3.370 (1.90), 3.388 (1.34), 3.675 (2.01), 3.708 (1.82), 3.769 (0.54), 3.798 (0.90), 3.828 (0.59), 3.917 (16.00), 4.206 (3.03), 4.598 (0.77), 4.631 (0.71), 6.769 (1.92), 6.787 (2.18), 6.873 (1.95), 6.892 (2.11), 7.000 (1.55), 7.019 (2.40), 7.037 (1.38), 7.354 (1.17), 7.374 (2.55), 7.393 (1.74), 7.440 (3.20), 7.461 (1.92), 7.494 (0.56), 7.511 (2.91), 7.520 (3.20), 7.530 (3.12), 7.546 (0.71), 7.710 (1.84), 7.731 (1.78), 7.852 (1.92), 7.870 (1.40), 7.875 (1.63), 8.250 (1.36), 8.272 (1.38).

Example 224

1,14-dimethyl-7-[3-(naphthalen-1-yloxy)propyl]-3-(2,2,2-trifluoroethyl)-10,11,12,13,14,15-hexahydro-1H-pyrazolo[3',4':8,9][1,6]diazacycloundecino[10,11,1-hi]indole-8-carboxylic acid (Enantiomer 2)

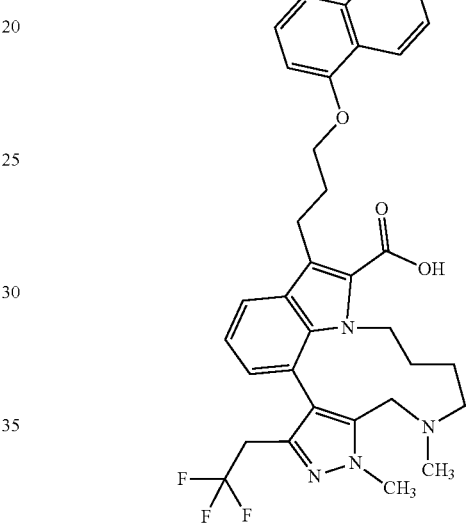

For the preparation of the racemic title compound see Example 222. Separation of enantiomers by preparative chiral HPLC (method see Example 222) gave the title compound (74 mg).

Analytical Chiral HPLC (method see Example 222): R$_t$=4.73 min.

$^1$H-NMR (400 MHz, DMSO-d6) δ[ppm]: 0.706 (1.28), 0.724 (3.02), 0.743 (1.80), 0.769 (0.67), 0.777 (1.55), 0.784 (1.02), 0.789 (0.88), 0.795 (1.60), 0.799 (1.68), 0.803 (1.88), 0.807 (1.60), 0.816 (1.72), 0.821 (1.57), 0.826 (1.38), 0.833 (2.63), 0.841 (2.93), 0.844 (3.85), 0.852 (5.56), 0.860 (9.41), 0.870 (2.82), 0.877 (5.46), 0.888 (1.00), 0.895 (1.58), 0.898 (1.55), 0.901 (1.24), 0.907 (1.63), 0.913 (0.95), 0.917 (0.91), 0.924 (0.97), 0.962 (1.82), 0.984 (1.78), 1.036 (4.18), 1.047 (0.95), 1.061 (2.76), 1.067 (1.83), 1.081 (2.07), 1.100 (0.45), 1.109 (0.42), 1.128 (2.66), 1.132 (4.10), 1.144 (3.15), 1.147 (3.99), 1.162 (0.67), 1.181 (0.49), 1.199 (1.47), 1.213 (0.72), 1.230 (3.74), 1.247 (0.88), 1.265 (0.81), 1.292 (1.50), 1.355 (1.83), 1.361 (1.24), 1.371 (0.59), 1.388 (0.92), 1.418 (1.32), 1.437 (2.02), 1.456 (1.66), 1.475 (0.64), 1.869 (0.52), 1.895 (0.77), 1.907 (1.71), 1.919 (2.08), 1.988 (0.69), 2.003 (1.17), 2.034 (1.52), 2.099 (0.72), 2.120 (0.41), 2.130 (1.10), 2.152 (9.68), 2.171 (1.05), 2.197 (2.07), 2.202 (2.04), 2.223 (1.05), 2.250 (0.42), 2.264 (0.58), 2.285 (0.45), 2.298 (0.47), 2.317 (0.55), 2.322 (0.77), 2.326 (0.99), 2.332 (0.80), 2.336 (0.56), 2.432 (0.66), 2.447 (0.75), 2.465 (1.13), 2.518 (4.57), 2.522 (3.08), 2.668 (1.11), 2.673 (0.81), 2.760 (0.49), 3.002 (0.58), 3.031 (0.61), 3.041 (0.85), 3.069 (0.74), 3.200 (0.55), 3.235 (2.24), 3.256 (1.47), 3.267 (2.72), 3.295 (1.24), 3.325 (1.49), 3.673 (1.72), 3.705 (1.53), 3.778 (0.64), 3.808 (0.41), 3.915 (16.00), 4.188 (1.21), 4.203 (2.32), 4.218 (1.16), 4.618 (0.52), 4.651 (0.50), 6.748 (1.50), 6.765 (1.69), 6.869 (1.58), 6.888 (1.69), 6.986 (1.50), 7.005 (2.05), 7.024 (1.32), 7.350 (1.11), 7.370 (2.21), 7.390 (1.64), 7.438 (2.66), 7.458 (1.58), 7.491 (0.47), 7.503 (1.46), 7.508 (2.52), 7.518 (2.91), 7.527 (2.68), 7.532 (1.75), 7.544 (0.56), 7.691 (1.50), 7.711 (1.39), 7.850 (1.60), 7.861 (0.78), 7.868 (1.06), 7.874 (1.32), 8.247 (1.11), 8.254 (0.97), 8.271 (1.06).

Example 225

(rac)-3-[(E)-2-fluoroethenyl]-1,14-dimethyl-7-[3-(naphthalen-1-yloxy)propyl]-10,11,12,13,14,15-hexahydro-1H-pyrazolo[3',4':8,9][1,6]diazacycloundecino[10,11,1-hi]indole-8-carboxylic acid

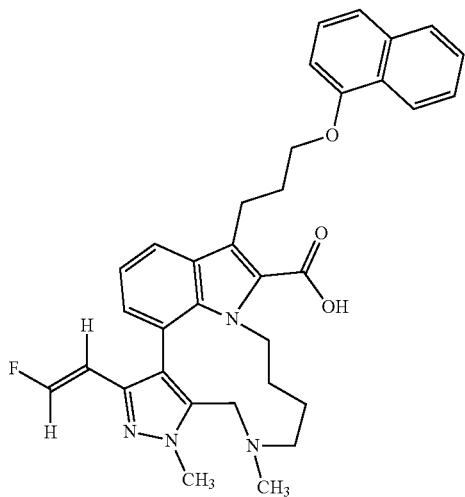 [SMILES: CN1CCCCn2c(C(=O)O)c(CCCOc3cccc4ccccc34)c3cccc(c32)-c2c(/C=C/F)nn(C)c2C1]

To a solution of (rac)-ethyl 3-[(E)-2-fluoroethenyl]-1,14-dimethyl-7-[3-(naphthalen-1-yloxy)propyl]-10,11,12,13,14,15-hexahydro-1H-pyrazolo[3',4':8,9][1,6]diazacycloundecino[10,11,1-hi]indole-8-carboxylate (see Intermediate 371; 100 mg, 168 μmol) in a mixture of THF (8.2 ml) and ethanol (5.7 ml) was added an aqueous solution of lithium hydroxide (3.4 ml, 1.0 M, 3.4 mmol). The resulting mixture was stirred at 40° C. for 3 days. After removal of all volatiles, the residue was subjected to flash chromatography (Biotage SNAP cartridge silica, dichloromethane/2-propanol gradient, 0%→100% 2-propanol) to give the title compound (70 mg).

LC-MS (Method 2): Rt=0.92 min; MS (ESIpos): m/z=568 [M+H]$^+$ $^1$H-NMR (400 MHz, DMSO-d6) δ[ppm]: 0.706 (0.50), 0.734 (0.58), 0.850 (0.47), 0.977 (0.48), 1.027 (12.90), 1.042 (13.27), 1.089 (0.58), 1.230 (2.73), 1.255 (0.42), 1.348 (0.61), 1.853 (0.41), 1.882 (0.71), 1.907 (0.69), 2.155 (10.30), 2.178 (0.54), 2.198 (1.09), 2.215 (1.53), 2.233 (1.08), 2.406 (0.48), 2.429 (0.50), 2.447 (0.47), 2.518 (3.86), 2.523 (2.46), 3.248 (1.67), 3.271 (0.86), 3.282 (2.14), 3.304 (1.40), 3.366 (1.12), 3.386 (0.71), 3.400 (0.64), 3.676 (1.70), 3.709 (1.50), 3.836 (0.42), 3.865 (0.76), 3.896 (16.00), 4.178 (1.06), 4.193 (2.18), 4.208 (1.15), 4.599 (0.69), 4.634 (0.62), 5.758 (4.94), 5.888 (1.56), 5.916 (1.92), 5.939 (1.66), 5.967 (1.73), 6.498 (1.71), 6.526 (1.70), 6.710 (1.61), 6.738 (1.63), 6.843 (1.68), 6.846 (1.74), 6.864 (3.49), 6.884 (1.98), 7.029 (1.73), 7.047 (1.94), 7.049 (2.15), 7.067 (1.50), 7.356 (1.39), 7.376 (2.57), 7.395 (2.04), 7.444 (2.69), 7.464 (1.60), 7.500 (0.54), 7.512 (1.84), 7.516 (2.96), 7.527 (3.27), 7.535 (2.90), 7.540 (2.05), 7.552 (0.62), 7.767 (1.77), 7.770 (1.84), 7.787 (1.63), 7.790 (1.58), 7.856 (1.54), 7.860 (1.10), 7.867 (0.85), 7.870 (0.96), 7.873 (1.02), 7.879 (1.33), 8.250 (1.36), 8.259 (0.93), 8.275 (1.29).

The title compound (60 mg) was separated into enantiomers by preparative chiral HPLC to give enantiomer 1 (9.5 mg, see Example 226) and enantiomer 2 (9.7 mg, see Example 227).

Preparative chiral HPLC method: Instrument: Sepiatec: Prep SFC100; column: Chiralpak IG 5 μm 250×30 mm; Eluent A: CO$_2$, Eluent B: ethanol+0.2 Vol-% aqueous ammonia (32%); Isocratic: 25% B; Flow 100.0 ml/min Temperature: 40° C.; BPR: 150 bar; MWD @ 220 nm Analytical chiral HPLC method: Instrument: Agilent: 1260, Aurora SFC-Modul; column: Chiralpak IG 5 μm 100×4.6 mm; Eluent A: CO$_2$, eluent B: Ethanol+0.2 Vol-% aqueous ammonia (32%); Isocratic: 25% B; Flow 4.0 ml/min; Temperature: 37.5° C.; BPR: 100 bar; MWD @ 220 nm Example 226

3-[(E)-2-fluoroethenyl]-1,14-dimethyl-7-[3-(naphthalen-1-yloxy)propyl]-10,11,12,13,14,15-hexahydro-1H-pyrazolo[3',4':8,9][1,6]diazacycloundecino[10,11,1-hi]indole-8-carboxylic acid (Enantiomer 1)

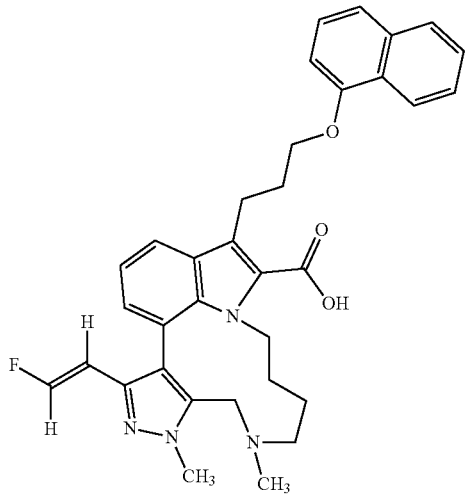

For the preparation of the racemic title compound see Example 225. Separation of enantiomers by preparative chiral HPLC (method see Example 225) gave the title compound (9.5 mg).

Analytical Chiral HPLC (method see Example 225): R$_t$=1.35 min.

$^1$H-NMR (400 MHz, DMSO-d6) δ[ppm]: 0.729 (3.22), 0.877 (4.40), 0.922 (3.97), 1.067 (3.82), 1.095 (3.24), 1.214 (3.72), 1.360 (3.11), 1.542 (1.01), 1.876 (2.90), 2.144 (16.00), 2.213 (6.78), 2.332 (1.42), 2.666 (0.73), 3.245 (4.29), 3.275 (5.58), 3.363 (2.90), 3.667 (3.23), 3.698 (2.98), 4.184 (6.65), 4.628 (2.37), 4.656 (2.23), 5.758 (1.36), 5.891 (1.61), 5.919 (2.00), 5.941 (1.90), 5.969 (1.69), 6.495 (1.64), 6.522 (1.56), 6.706 (1.73), 6.733 (1.72), 6.834 (4.83), 6.852 (4.56), 7.028 (3.57), 7.365 (3.67), 7.435 (4.42), 7.520 (7.09), 7.746 (3.57), 7.760 (3.51), 7.859 (3.68), 8.259 (3.52).

Example 227

3-[(E)-2-fluoroethenyl]-1,14-dimethyl-7-[3-(naphthalen-1-yloxy)propyl]-10,11,12,13,14,15-hexahydro-1H-pyrazolo[3',4':8,9][1,6]diazacycloundecino[10,11,1-hi]indole-8-carboxylic acid (Enantiomer 2)

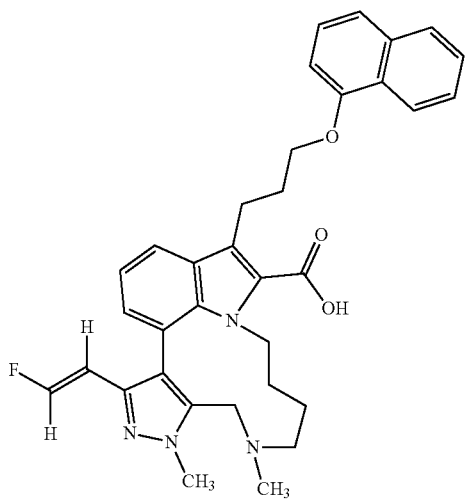 [SMILES: CN1CCCCn2c(C(=O)O)c(CCCOc3cccc4ccccc34)c3cccc(c32)-c2c(/C=C/F)nn(C)c2C1]

For the preparation of the racemic title compound see Example 225. Separation of enantiomers by preparative chiral HPLC (method see Example 225) gave the title compound (9.7 mg).

Analytical Chiral HPLC (method see Example 225): $R_t$=3.62 min.

$^1$H-NMR (400 MHz, DMSO-d6) δ[ppm]: 0.733 (2.81), 0.814 (3.36), 0.858 (4.43), 0.877 (4.80), 0.920 (4.28), 1.067 (3.47), 1.098 (3.14), 1.140 (1.60), 1.197 (3.06), 1.362 (2.54), 1.543 (0.96), 1.876 (2.53), 1.905 (1.98), 2.142 (16.00), 2.214 (5.74), 2.324 (1.04), 2.416 (3.34), 2.665 (0.85), 2.803 (0.58), 3.243 (3.79), 3.274 (5.02), 3.365 (2.38), 3.665 (3.09), 3.698 (2.86), 3.841 (2.82), 4.184 (5.91), 4.633 (1.90), 4.659 (1.85), 5.757 (1.08), 5.889 (1.55), 5.919 (1.90), 5.940 (1.80), 5.969 (1.70), 6.493 (1.60), 6.521 (1.53), 6.705 (1.62), 6.732 (1.62), 6.814 (3.56), 6.829 (4.27), 6.852 (3.76), 6.869 (3.60), 7.026 (3.46), 7.363 (3.39), 7.381 (2.60), 7.434 (4.26), 7.453 (3.19), 7.518 (6.40), 7.740 (3.31), 7.757 (3.22), 7.861 (3.34), 8.257 (3.11).

Example 228

3-(2,2-difluoroethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid

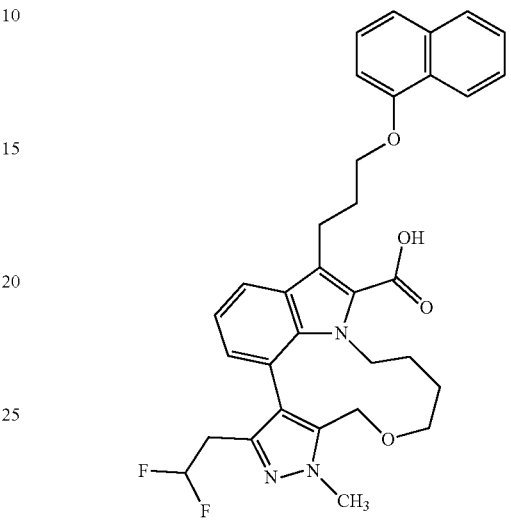

To a solution of (rac)-ethyl 3-(2,2-difluoroethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (see Intermediate 375; 250 mg, 415 μmol) in a mixture of THF (20 ml) and ethanol (14 ml) was added an aqueous solution of lithium hydroxide (8.3 ml, 1.0 M, 8.3 mmol). The resulting mixture was stirred at 40° C. for 24 hours. After removal of all volatiles the residue was subjected to flash chromatography (Biotage SNAP cartridge silica, dichloromethane/2-propanol gradient, 0%-100% 2-propanol) to give the title compound (81 mg).

LC-MS (Method 2): Rt=0.89 min; MS (ESIpos): m/z=575 [M+H]$^+$ $^1$H-NMR (400 MHz, DMSO-d6) δ[ppm]: 1.027 (1.43), 1.042 (1.18), 1.230 (2.08), 1.250 (0.61), 1.319 (0.45), 2.200 (0.91), 2.218 (1.34), 2.235 (0.95), 2.322 (0.50), 2.327 (0.69), 2.332 (0.50), 2.518 (2.79), 2.523 (1.85), 2.665 (0.53), 2.669 (0.86), 2.673 (0.89), 2.678 (0.55), 2.684 (0.52), 2.709 (0.44), 2.717 (0.74), 2.729 (0.69), 2.751 (0.70), 2.763 (0.83), 2.796 (0.72), 2.807 (0.56), 2.814 (0.73), 2.826 (0.51), 2.833 (0.55), 2.844 (0.79), 3.267 (0.45), 3.282 (0.64), 3.301 (1.13), 3.330 (5.05), 3.364 (0.73), 3.380 (0.53), 3.428 (0.77), 3.442 (0.62), 3.457 (0.70), 3.900 (16.00), 3.932 (0.41), 3.944 (0.40), 3.956 (0.63), 3.968 (0.41), 3.979 (0.43), 4.188 (1.30), 4.203 (2.72), 4.218 (1.26), 4.241 (1.70), 4.275 (1.81), 4.482 (0.67), 4.517 (0.60), 4.639 (2.00), 4.673 (1.80), 5.759 (6.11), 5.847 (0.67), 5.976 (0.61), 5.988 (1.38), 5.999 (0.62), 6.129 (0.57), 6.845 (1.49), 6.848 (1.56), 6.863 (1.81), 6.865 (1.79), 6.878 (1.79), 6.894 (1.85), 7.036 (1.77), 7.055 (1.83), 7.057 (2.05), 7.074 (1.51), 7.360 (1.36), 7.381 (2.50), 7.400 (2.08), 7.443 (2.53), 7.464 (1.42), 7.490 (0.58), 7.502 (1.56), 7.507 (1.45), 7.512 (1.76), 7.520 (3.62), 7.527 (1.75), 7.531 (1.60), 7.535 (1.71), 7.548 (0.68), 7.763 (1.60), 7.766 (1.63), 7.784 (1.57), 7.786 (1.51), 7.854 (1.49), 7.862 (0.79), 7.872 (1.37), 7.877 (1.28), 8.227 (1.32), 8.233 (1.21), 8.244 (0.64), 8.250 (1.14), 8.252 (1.24).

The title compound (70 mg) was separated into enantiomers by preparative chiral HPLC to give enantiomer 1 (14 mg, see Example 229) and enantiomer 2 (15 mg, see Example 230).

Preparative chiral SFC method: Instrument: Sepiatec: Prep SFC100; column: Chiralpak IG 5 μm 250×30 mm; Eluent A: $CO_2$, Eluent B: ethanol+0.2 Vol-% aqueous ammonia (32%); 20% B; Flow 100.0 ml/min Temperature: 40° C.; BPR: 150 bar; MWD @ 220 nm Analytical chiral SFC method: Instrument: Agilent: 1260, Aurora SFC-Modul; column: Chiralpak IG 5 μm 100×4.6 mm; Eluent A: $CO_2$, Eluent B: ethanol+0.2 Vol-% aqueous ammonia (32%); 20% B; Flow 4.0 ml/min; Temperature: 37.5° C.; BPR: 100 bar; MWD @ 220 nm Example 229

3-(2,2-difluoroethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (Enantiomer 1)

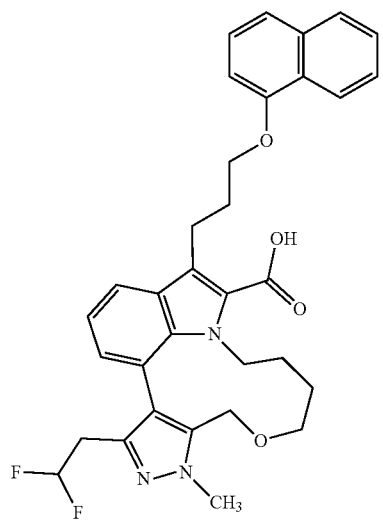 [SMILES: Cn1nc(CC(F)F)c2c1COCCCCn1c(C(=O)O)c(CCCOc3cccc4ccccc34)c3cccc-2c31]

For the preparation of the racemic title compound see Example 228. Separation of enantiomers by preparative chiral HPLC (method see Example 228) gave the title compound (14 mg).

Analytical Chiral HPLC (method see Example 228): $R_t$=1.48 min.

$^1$H-NMR (400 MHz, DMSO-d6) δ[ppm]: 0.816 (2.31), 0.860 (2.08), 0.879 (2.22), 1.022 (4.75), 1.068 (2.70), 1.087 (2.77), 1.140 (1.39), 1.228 (3.25), 1.325 (2.25), 2.116 (0.62), 2.219 (4.84), 2.325 (0.81), 2.682 (1.87), 2.723 (2.82), 2.763 (2.90), 2.809 (3.23), 3.297 (2.85), 3.347 (3.19), 3.365 (3.15), 3.424 (2.65), 3.899 (16.00), 4.200 (6.22), 4.239 (3.31), 4.273 (3.04), 4.494 (2.00), 4.525 (1.83), 4.637 (2.89), 4.670 (2.54), 5.846 (0.93), 5.988 (1.86), 6.128 (0.92), 6.840 (3.35), 6.855 (4.21), 6.871 (3.94), 6.889 (3.50), 7.050 (3.21), 7.376 (3.25), 7.394 (2.50), 7.439 (4.05), 7.459 (2.92), 7.516 (5.67), 7.758 (3.17), 7.777 (3.08), 7.853 (3.12), 7.869 (3.00), 8.233 (2.98), 8.248 (2.83).

Example 230

3-(2,2-difluoroethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (Enantiomer 2)

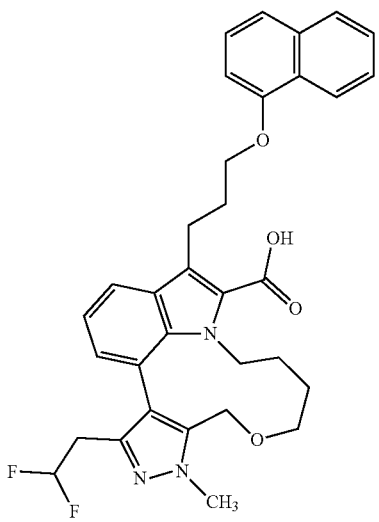 [SMILES: Cn1nc(CC(F)F)c2c1COCCCCn1c(C(=O)O)c(CCCOc3cccc4ccccc34)c3cccc-2c31]

For the preparation of the racemic title compound see Example 228. Separation of enantiomers by preparative chiral HPLC (method see Example 228) gave the title compound (15 mg).

Analytical Chiral HPLC (method see Example 228): $R_t$=2.76 min.

Example 231

(rac)-1-methyl-3-{[(1-methyl-1H-imidazol-2-yl)methoxy]methyl}-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid

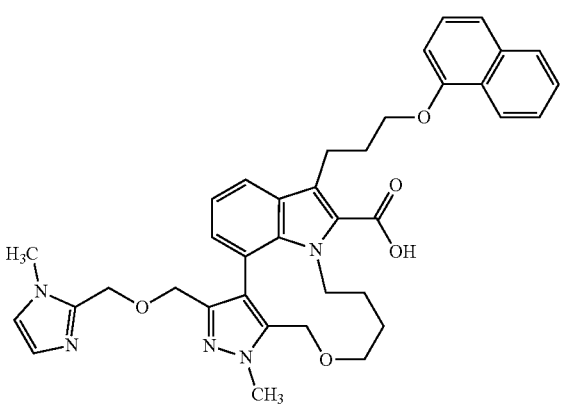 [SMILES: Cn1ccnc1COCc1nn(C)c2c1-c1cccc3c(CCCOc4cccc5ccccc45)c(C(=O)O)n(c13)CCCCOC2]

(rac)-Ethyl 3-(bromomethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (see Intermediate 258; 150 mg, 238 μmol) and (1-methyl-1H-imidazol-2-yl)methanol (40.0 mg, 357 μmol) were provided in DMF under an argon atmosphere and cooling and sodium hydride (47.6 mg, 60% purity, 1.19 mmol) was added. The reaction mixture was stirred over night at room temperature, was diluted with water and extracted with ethyl acetate. The combined organic phases were filtered through a silicone filter and concentrated. Purification by HPLC (method P2) yielded 77.7 mg (98% purity, 51% yield) of the title compound.

LC-MS (Method 2): $R_t$=0.92 min; MS (ESIpos): m/z=634 [M+H]$^+$ $^1$H-NMR (400 MHz, DMSO-d6) δ[ppm]: 0.981 (0.42), 0.999 (0.42), 1.134 (0.44), 1.752 (0.83), 1.907 (0.50), 2.183 (0.77), 2.202 (1.14), 2.220 (0.84), 2.518 (3.63), 2.523 (2.45), 2.674 (0.70), 2.777 (0.47), 3.157 (0.55), 3.173 (0.63), 3.204 (16.00), 3.223 (1.03), 3.282 (2.08), 3.408 (1.80), 3.421 (1.41), 3.439 (1.16), 3.455 (0.75), 3.893 (11.94), 3.921 (0.50), 4.016 (1.14), 4.044 (2.37), 4.077 (2.31), 4.104 (1.16), 4.168 (1.09), 4.184 (2.50), 4.201 (1.12), 4.219 (1.34), 4.243 (6.75), 4.253 (1.62), 4.567 (0.41), 4.639 (1.48), 4.672 (1.33), 6.648 (3.48), 6.650 (3.69), 6.681 (0.70), 6.698 (0.80), 6.874 (1.41), 6.892 (1.61), 6.903 (3.92), 6.905 (3.73), 6.922 (1.17), 6.941 (0.67), 7.342 (1.03), 7.362 (1.95), 7.381 (1.50), 7.426 (2.03), 7.447 (1.19), 7.486 (0.42), 7.498 (1.28), 7.504 (2.09), 7.513 (2.56), 7.523 (2.27), 7.528 (1.41), 7.540 (0.45), 7.613 (0.83), 7.632 (0.77), 7.845 (1.19), 7.855 (0.59), 7.863 (0.81), 7.868 (0.98), 8.237 (1.05), 8.245 (0.81), 8.252 (0.50), 8.262 (0.94).

The title compound was separated into enantiomers by preparative chiral HPLC to give enantiomer 1 (18.8 mg, see Example 232) and enantiomer 2 (18.9 mg, see Example 233).

Preparative chiral HPLC method: Instrument: Labomatic HD5000, Labocord-5000; Gilson GX-241, Labcol Vario 4000, column: Amylose SA 5μ 250×30 mm; eluent A: hexane+0.1 Vol-% diethylamine (99%); eluent B: ethanol; gradient: 20-50% B in 20 min; flow 40.0 ml/min; UV 254 nm.

Analytical chiral HPLC method: Instrument: Agilent HPLC 1260; column: Amylose SA 3μ 100×4.6 mm; eluent A: hexane+0.1 Vol-% diethylamine (99%); eluent B: ethanol; gradient: 20-50% B in 7 min; flow 1.4 ml/min; temperature: 25° C.; DAD 254 nm.

Example 232

(+)-1-methyl-3-{[(1-methyl-1H-imidazol-2-yl)methoxy]methyl}-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (Enantiomer 1)

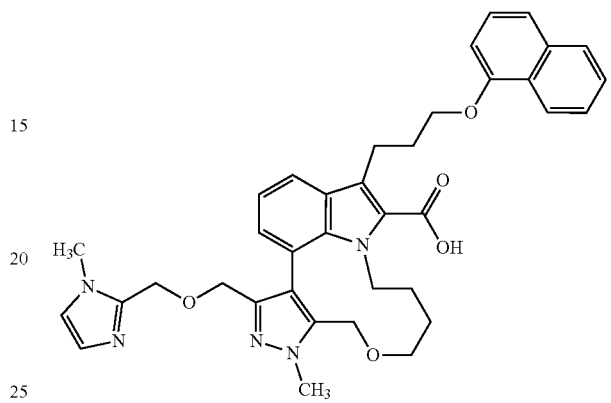

For the preparation of the racemic title compound and separation into its enantiomers see Example 231.

Analytical Chiral HPLC (method see Example 231): $R_t$=3.18 min.

Specific optical rotation (Method O1): +42.5° (c=1.0000 g/100 ml in CHCl$_3$)

LC-MS (Method 1): $R_t$=1.15 min; MS (ESIpos): m/z=634 [M+H]$^+$

Example 233

(−)-1-methyl-3-{[(1-methyl-1H-imidazol-2-yl)methoxy]methyl}-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (Enantiomer 2)

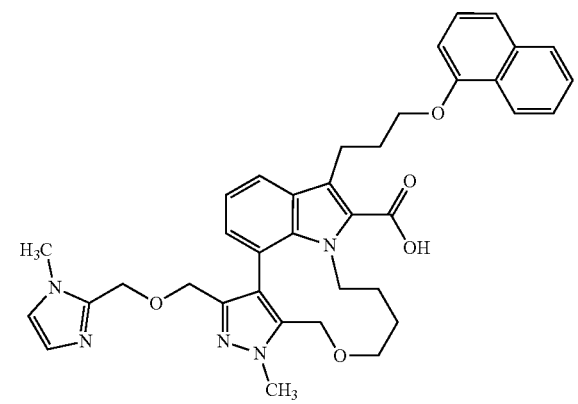 [SMILES: Cn1ccnc1COCc1nn(C)c2c1-c1cccc3c(CCCOc4cccc5ccccc45)c(C(=O)O)n(c13)CCCCOC2]

For the preparation of the racemic title compound and separation into its enantiomers see Example 231.

Analytical Chiral HPLC (method see Example 231): $R_t$=4.73 min.

Specific optical rotation (Method O1): −40.6° (c=1.0000 g/100 ml in CHCl$_3$)

LC-MS (Method 1): R$_t$=1.16 min; MS (ESIpos): m/z=634 [M+H]$^+$

Example 234

(rac)-3-(difluoromethoxy)-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid

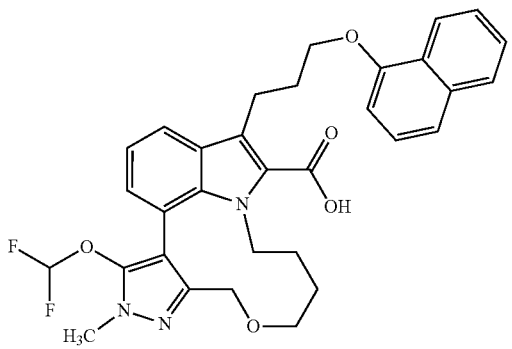 [SMILES: Cn1nc2c(c1OC(F)F)-c1cccc3c(CCCOc4cccc5ccccc45)c(C(=O)O)n(c13)CCCCOC2]

A mixture of (rac)-ethyl 3-(difluoromethoxy)-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylate (see Intermediate 397; 425 mg, 704 µmol) in THF (7.0 ml), ethanol (2.0 ml) and aqueous lithium hydroxide (3.5 ml, 1.0 M, 3.5 mmol) was stirred for 72 h at room temperature and for 3 h at 55° C. Aqueous solution of lithium hydroxide (3.5 ml, 1.0 M, 3.5 mmol) was added and the reaction mixture was stirred for 22 h at 55° C. and for 58 h at 65° C. Aqueous solution of lithium hydroxide (3.5 ml, 1.0 M, 3.5 mmol) was added and the reaction mixture was stirred for 48 h at 65° C. and for 24 h at 80° C. Further aqueous solution of lithium hydroxide (2.1 ml, 1.0 M, 2.1 mmol) was added and the reaction mixture was stirred for 72 h at 80° C. 1,4-Dioxane (4.0 ml) and ethanol (3 ml) were added and the reaction mixture was stirred for 3 h at 100° C. An aqueous citric acid solution (10%) was added to adjust the pH to 3-4 and the mixture was extracted with ethyl acetate. The combined organic phases were washed with brine, filtered through a silicone filter and concentrated. Purification by by flash chromatography on silica gel (dichloromethane/methanol) yielded 221 mg (99% purity, 54% yield) of the title compound.

LC-MS (Method 1): R$_t$=1.51 min; MS (ESIneg): m/z=574 [M−H]$^−$ $^1$H-NMR (400 MHz, DMSO-d6) δ[ppm]: 1.103 (16.00), 1.212 (0.52), 1.232 (0.82), 2.185 (0.48), 2.202 (0.75), 2.219 (0.51), 2.518 (1.32), 2.523 (0.88), 3.073 (5.32), 3.288 (0.65), 3.297 (0.51), 3.772 (7.07), 4.131 (1.06), 4.162 (1.46), 4.176 (0.83), 4.182 (0.81), 4.191 (0.48), 4.197 (0.41), 4.497 (1.07), 4.529 (0.93), 6.604 (0.81), 6.784 (1.59), 6.864 (0.87), 6.881 (0.94), 6.963 (0.69), 6.979 (0.52), 6.982 (0.60), 6.996 (1.13), 7.000 (1.04), 7.021 (1.12), 7.040 (1.21), 7.058 (0.58), 7.357 (0.70), 7.378 (1.24), 7.397 (1.01), 7.445 (1.26), 7.466 (0.75), 7.514 (0.90), 7.517 (1.14), 7.528 (1.38), 7.535 (0.99), 7.537 (1.10), 7.541 (1.01), 7.728 (0.80), 7.731 (0.86), 7.747 (0.76), 7.751 (0.75), 7.856 (0.72), 7.860 (0.49), 7.870 (0.52), 7.874 (0.45), 7.880 (0.62), 8.253 (0.65), 8.264 (0.51), 8.278 (0.59).

The title compound was separated into enantiomers by preparative chiral HPLC to give enantiomer 1 (89.1 mg, see Example 235) and enantiomer 2 (87.6 mg, see Example 236).

Preparative chiral HPLC method: Instrument: Labomatic HD5000, Labocord-5000; Gilson GX-241, Labcol Vario 4000, column: YMC Cellulose SB 5µ 250×30 mm; eluent A: hexane+0.1 Vol-% TFA (99%); eluent B: 2-propanol; gradient: 10-30% B in 20 min; flow 40.0 ml/min; UV 254 nm.

Analytical chiral HPLC method: Instrument: Waters Alliance 2695 Agilent HPLC 1260; column: YMC Cellulose SB 3µ 100×4.6 mm; eluent A: hexane+0.1 Vol-% TFA (99%); eluent B: 2-propanol; gradient: 5-50% B in 7 min; flow 1.4 ml/min; temperature: 25° C.; DAD 254 nm.

Example 235

(−)-3-(difluoromethoxy)-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (Enantiomer 1)

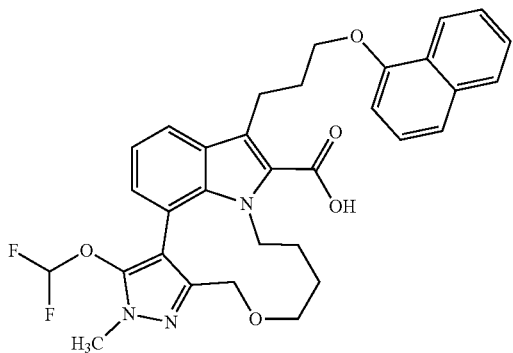 [SMILES: Cn1nc2c(c1OC(F)F)-c1cccc3c(CCCOc4cccc5ccccc45)c(C(=O)O)n(c13)CCCCOC2]

For the preparation of the racemic title compound and separation into its enantiomers see Example 234.

Analytical Chiral HPLC (method see Example 234): R$_t$=1.73 min.

Specific optical rotation (Method O1): −40.5° (c=1.0000 g/100 ml in DMSO)

LC-MS (Method 1): R$_t$=1.50 min; MS (ESIpos): m/z=576 [M+H]$^+$ $^1$H-NMR (400 MHz, DMSO-d6) δ[ppm]: 1.107 (16.00), 1.215 (0.46), 1.225 (0.47), 2.185 (0.42), 2.202 (0.64), 2.219 (0.43), 2.518 (1.07), 2.522 (0.68), 3.290 (0.55), 3.318 (0.73), 3.332 (0.72), 3.341 (0.66), 3.771 (6.02), 4.131 (0.89), 4.162 (1.28), 4.176 (0.73), 4.182 (0.70), 4.191 (0.40), 4.499 (0.92), 4.530 (0.81), 6.606 (0.73), 6.786 (1.41), 6.865 (0.75), 6.882 (0.81), 6.965 (0.60), 6.984 (0.47), 6.988 (0.58), 7.002 (1.08), 7.005 (1.01), 7.024 (1.10), 7.044 (1.10), 7.062 (0.56), 7.359 (0.59), 7.379 (1.09), 7.398 (0.88), 7.445 (1.08), 7.466 (0.64), 7.514 (0.76), 7.518 (0.97), 7.528 (1.19), 7.536 (0.85), 7.538 (0.96), 7.541 (0.86), 7.732 (0.78), 7.736 (0.80), 7.752 (0.74), 7.755 (0.70), 7.857 (0.60), 7.861 (0.42), 7.870 (0.44), 7.880 (0.52), 8.253 (0.56), 8.264 (0.43), 8.278 (0.50).

Example 236

(+)-3-(difluoromethoxy)-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (Enantiomer 2)

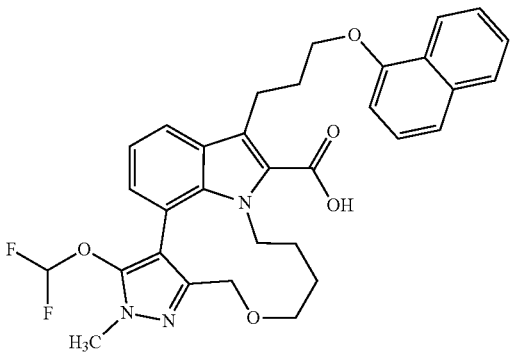 [SMILES: Cn1nc2c(c1OC(F)F)-c1cccc3c(CCCOc4cccc5ccccc45)c(C(=O)O)n(c13)CCCCOC2]

For the preparation of the racemic title compound and separation into its enantiomers see Example 234.

Analytical Chiral HPLC (method see Example 234): $R_t$=2.19 min.

Specific optical rotation (Method O1): +42.7° (c=1.0000 g/100 ml in DMSO)

LC-MS (Method 1): $R_t$=1.50 min; MS (ESIpos): m/z=576 [M+H]$^+$

Example 237

(rac)-1,3,15-Trimethyl-7-[3-(naphthalen-1-yloxy)propyl]-1,10,11,12,13,14,15,16-octahydropyrazolo[4',3':4,5][1,7]diazacyclododecino[3,2,1-hi]indole-8-carboxylic acid

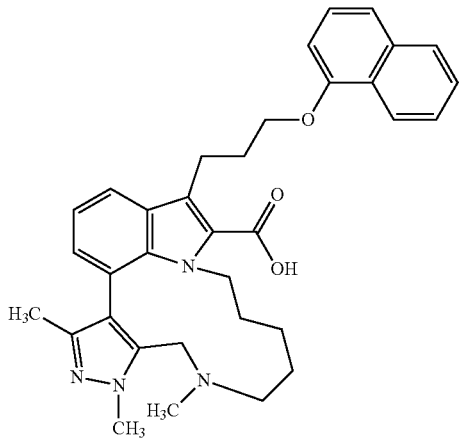 [SMILES: Cc1nn(C)c2c1-c1cccc3c(CCCOc4cccc5ccccc45)c(C(=O)O)n(c13)CCCCCN(C)C2]

A mixture of (rac)-ethyl 1,3,15-trimethyl-7-[3-(naphthalen-1-yloxy)propyl]-1,10,11,12,13,14,15,16-octahydropyrazolo[4',3':4,5][1,7]diazacyclododecino[3,2,1-hi]indole-8-carboxylate (610 mg, 94% purity, 991 μmol; see Intermediate 409), THF (45 mL), ethanol (22 mL) and an aqueous solution of lithium hydroxide (20 mL, 1.0 M) was stirred at 70° C. overnight and at 80° C. for 7 hours. The mixture was neutralized by the addition of HCl (1.0 M in water) and was adjusted to pH 6 by the addition of buffer. The mixture was extracted with dichloromethane/methanol (9:1) and the organic layer was dried over sodium sulfate. After filtration and concentration, the residue was purified by chromatography by Biotage (SNAP silica 100 g, MeOH:dichloromethane) to give the title compound (411 mg, 72% yield).

LC-MS: m/z=551.4 [M+H]$^+$.

$^1$H-NMR (400 MHz, DMSO-d6), δ [ppm]=0.55 (1H), 0.73 (1H), 0.89-1.17 (3H), 1.34 (1H), 1.84 (3H), 1.90 (1H), 2.15-2.27 (6H), 3.18-3.45 (3H), 3.66 (1H), 3.84 (3H), 4.07 (1H), 4.20 (2H), 4.50 (1H), 6.89 (2H), 7.06 (1H), 7.38 (1H), 7.45 (1H), 7.52 (2H), 7.70 (1H), 7.87 (1H), 8.24 (1H), 12.81-13.58 (1H).

Example 238

(+)-1,3,15-trimethyl-7-[3-(naphthalen-1-yloxy)propyl]-1,10,11,12,13,14,15,16-octahydropyrazolo[4',3':4,5][1,7]diazacyclododecino[3,2,1-hi]indole-8-carboxylic acid (Enantiomer 1)

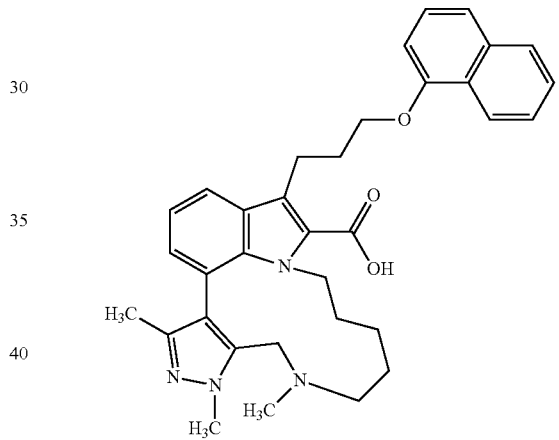

A racemic mixture of 1,3,15-trimethyl-7-[3-(naphthalen-1-yloxy)propyl]-1,10,11,12,13,14,15,16-octahydropyrazolo[4',3':4,5][1,7]diazacyclododecino[3,2,1-hi]indole-8-carboxylic acid (200 mg, 363 μmol; see Example 237) was separated by preparative chiral HPLC (instrument: Labomatic HD5000, Labocord-5000; Gilson GX-241, Labcol Vario 4000; column: Chiralpak IE 5p 250×30 mm; eluent A: hexane+0.1 Vol-% diethylamine (99%); eluent B: 2-propanol; isocratic: 50% A+50% B; flow 40 mL/min; UV 254 nm) to give 73.8 mg (35% yield) of the title compound. Analytic chiral HPLC: ee=99.9%; retention time: 2.57 minutes (instrument: Agilent 1260; column: Chiralpak IE 3 μm 100×4.6 mm; eluent A: hexane+0.1 Vol-% diethylamine (99%), eluent B: 2-propanol; isocratic: 50% A+50% B; flow 1.4 mL/min; temperature: 25° C.; DAD @ 254 nm); $[\alpha]_D^{20}$=+71.0° (c=1.0, CHCl$_3$).

$^1$H-NMR (400 MHz, DMSO-d6), δ [ppm]=0.56 (1H), 0.74 (1H), 0.89-1.19 (3H), 1.33 (1H), 1.84 (3H), 1.90 (1H), 2.15-2.27 (6H), 3.21-3.45 (3H), 3.66 (1H), 3.84 (3H), 4.05 (1H), 4.20 (2H), 4.53 (1H), 6.88 (2H), 7.05 (1H), 7.38 (1H), 7.45 (1H), 7.52 (2H), 7.68 (1H), 7.86 (1H), 8.24 (1H), 13.15 (1H).

Example 239

(−)-1,3,15-trimethyl-7-[3-(naphthalen-1-yloxy)propyl]-1,10,11,12,13,14,15,16-octahydropyrazolo[4',3':4,5][1,7]diazacyclododecino[3,2,1-hi]indole-8-carboxylic acid (Enantiomer 2)

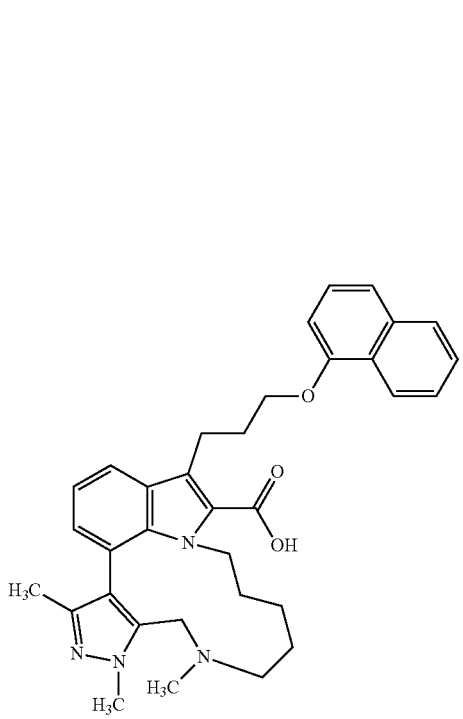 [SMILES: Cc1nn(C)c2c1-c1cccc3c(CCCOc4cccc5ccccc45)c(C(=O)O)n(c13)CCCCCN(C)C2]

A racemic mixture of 1,3,15-trimethyl-7-[3-(naphthalen-1-yloxy)propyl]-1,10,11,12,13,14,15,16-octahydropyrazolo[4',3':4,5][1,7]diazacyclododecino[3,2,1-hi]indole-8-carboxylic acid (200 mg, 363 μmol; see Example 237) was separated by preparative chiral HPLC (instrument: Labomatic HD5000, Labocord-5000; Gilson GX-241, Labcol Vario 4000; column: Chiralpak IE 5μ 250×30 mm; eluent A: hexane+0.1 Vol-% diethylamine (99%); eluent B: 2-propanol; isocratic: 50% A+50% B; flow 40 mL/min; UV 254 nm) to give 57.7 mg (27% yield) of the title compound.

Analytic chiral HPLC: ee=99.0%; retention time: 4.88 minutes (instrument: Agilent 1260; column: Chiralpak IE 3 μm 100×4.6 mm; eluent A: hexane+0.1 Vol-% diethylamine (99%), eluent B: 2-propanol; isocratic: 50% A+50% B; flow 1.4 mL/min; temperature: 25° C.; DAD @ 254 nm); $[\alpha]_D^{20}$=−66.0° (c=1.0, CHCl$_3$)

$^1$H-NMR (400 MHz, DMSO-d6), δ [ppm]=0.56 (1H), 0.74 (1H), 0.90-1.18 (3H), 1.34 (1H), 1.84 (3H), 1.89 (1H), 2.16-2.28 (6H), 3.21-3.46 (3H), 3.66 (1H), 3.84 (3H), 4.06 (1H), 4.20 (2H), 4.52 (1H), 6.88 (2H), 7.06 (1H), 7.38 (1H), 7.45 (1H), 7.52 (2H), 7.69 (1H), 7.86 (1H), 8.24 (1H), 13.16 (1H).

Example 240

(rac)-1,3,15-Trimethyl-7-[3-(5,6,7,8-tetrahydronaphthalen-1-yloxy)propyl]-1,10,11,12,13,14,15,16-octahydropyrazolo[4',3':4,5][1,7]diazacyclododecino[3,2,1-hi]indole-8-carboxylic acid To a solution of 1,3,15-trimethyl-7-[3-(naphthalen-1-yloxy)propyl]-1,10,11,12,13,14,15,16-octahydropyrazolo[4',3':4,5][1,7]diazacyclododecino[3,2,1-hi]indole-8-carboxylic acid (50.0 mg, 90.8 μmol; see Example 237) in ethanol (2 mL) and THF (2 mL) were added palladium (30 mg, 10% on charcoal) and the mixture was reacted with an atmosphere of hydrogen at 50° C. and 11 bar for 20 hours. After filtration and concentration the residue was purified by preparative TLC (MeOH:dichloromethane) to give the title compound (12.8 mg, 25% yield).

LC-MS: m/z=555.5 [M+H]$^+$.

$^1$H-NMR (400 MHz, DMSO-d6), δ [ppm]=0.56 (1H), 0.74 (1H), 0.92 (1H), 1.05 (1H), 1.16 (1H), 1.30 (1H), 1.70 (4H), 1.83 (3H), 1.91 (1H), 2.04 (2H), 2.22 (1H), 2.24 (3H), 2.62 (2H), 2.67 (2H), 3.10 (1H), 3.21 (1H), 3.41 (1H), 3.65 (1H), 3.83 (3H), 3.90-4.01 (3H), 4.58 (1H), 6.61 (2H), 6.77 (1H), 6.96 (1H), 7.01 (1H), 7.55 (1H).

Example 241

3-methyl-7-[3-(naphthalen-1-yloxy)propyl]-2-(2,2,2-trifluoroethyl)-2,10,11,12,13,15-hexahydropyrazolo[4',3':9,10][1,6]oxazacycloundecino[8,7,6-hi]indole-8-carboxylic acid (Enantiomer 1)

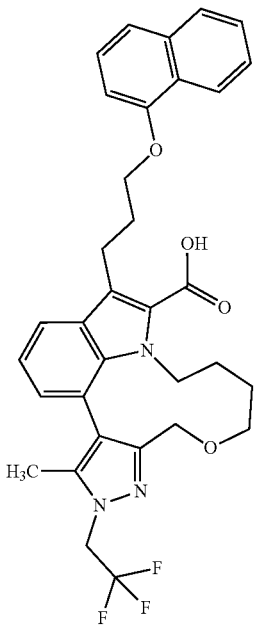 [SMILES: Cc1c2c(nn1CC(F)(F)F)COCCCCn1c(C(=O)O)c(CCCOc3cccc4ccccc34)c3cccc-2c31]

A mixture of (rac)-ethyl 3-methyl-7-[3-(naphthalen-1-yloxy)propyl]-2-(2,2,2-trifluoroethyl)-2,10,11,12,13,15-hexahydropyrazolo[4',3':9,10][1,6]oxazacycloundecino[8,7,6-hi]indole-8-carboxylate (410 mg, 662 μmol; see Intermediate 421), THF (27 ml), ethanol (19 ml) and aqueous solution of lithium hydroxide (13 ml, 1.0 M, 13 mmol) was stirred for 4 h at 50° C. For work-up, organic solvents were removed under vacuum, citric acid (2.78 g, 13.2 mmol) was added and the mixture was stirred for 10 min. The precipitate was collected by filtration, washed with water and then purified by preparative HPLC (Method P5) to give the title compound (180 mg, 46% yield) as a racemic mixture. The racemate was separated into enantiomers by preparative chiral HPLC followed by preparative HPLC (Method P5) and flash chromatography (10 g Biotage SNAP cartridge silica, dichloromethane/ethanol gradient 0%→6% ethanol) to give enantiomer 1 (7.8 mg) and enantiomer 2 (1.6 mg, see Example 242).

Preparative chiral HPLC method: Instrument: Sepiatec: Prep SFC100; column: Chiralpak ID 5 μm 250×30 mm; eluent A carbon dioxide, eluent B: ethanol+0.4 vol-% diethylamine (99%); isocratic: 13% B; flow 100.0 ml/min temperature: 40° C.; BPR: 150 bar; MWD 254 nm Analytical chiral HPLC method: Instrument: Agilent: 1260, Aurora SFC-Modul; column: Chiralpak ID 5 μm 100×4.6 mm; eluent A: carbon dioxide, eluent B: ethanol+0.2 vol-% diethylamine (99%); isocratic: 13% B; flow 4.0 ml/min; temperature: 37.5° C.; BPR: 100 bar; MWD 254 nm Analytical Chiral HPLC (method see Example 241): $R_t$=2.99 min. ee 95.4%

LC-MS (Method 1): $R_t$=1.56 min; MS (ESIpos): m/z=592 [M+H]$^+$ $^1$H-NMR (400 MHz, DMSO-d6) δ[ppm]: 0.974 (0.41), 0.988 (0.44), 0.999 (0.44), 1.147 (0.64), 1.161 (0.59), 1.179 (0.73), 1.191 (0.86), 1.205 (0.63), 1.215 (0.56), 1.230 (0.73), 1.296 (0.41), 1.328 (0.48), 1.871 (12.72), 2.195 (0.98), 2.213 (1.45), 2.230 (1.05), 2.323 (0.69), 2.327 (0.97), 2.331 (0.69), 2.518 (3.70), 2.523 (2.59), 2.665 (0.70), 2.669 (0.97), 2.674 (0.67), 2.728 (1.09), 2.888 (1.36), 3.056 (0.75), 3.069 (0.69), 3.081 (0.47), 3.264 (0.44), 3.279 (0.70), 3.297 (1.62), 3.315 (1.83), 3.330 (16.00), 3.352 (0.77), 3.367 (0.52), 3.772 (0.69), 3.783 (0.41), 3.796 (0.44), 4.183 (1.03), 4.198 (3.92), 4.208 (1.09), 4.229 (2.36), 4.287 (0.55), 4.306 (0.58), 4.325 (0.47), 4.559 (2.19), 4.590 (1.95), 5.140 (0.42), 5.148 (0.45), 5.162 (1.12), 5.171 (1.14), 5.185 (1.08), 5.194 (1.09), 5.210 (0.45), 6.880 (1.86), 6.898 (1.98), 6.956 (1.56), 6.959 (1.70), 6.974 (2.17), 6.977 (2.09), 7.053 (1.97), 7.073 (2.34), 7.091 (1.48), 7.363 (1.42), 7.384 (2.69), 7.403 (2.19), 7.447 (2.73), 7.467 (1.56), 7.500 (0.53), 7.512 (1.75), 7.517 (3.11), 7.526 (3.45), 7.536 (3.08), 7.540 (2.00), 7.552 (0.63), 7.728 (1.78), 7.731 (1.86), 7.749 (1.69), 7.751 (1.66), 7.858 (1.53), 7.861 (1.08), 7.868 (0.80), 7.872 (0.94), 7.875 (1.00), 7.881 (1.33), 8.247 (1.37), 8.255 (0.92), 8.271 (1.25), 13.152 (0.58).

Example 242

3-methyl-7-[3-(naphthalen-1-yloxy)propyl]-2-(2,2,2-trifluoroethyl)-2,10,11,12,13,15-hexahydropyrazolo[4',3':9,10][1,6]oxazacycloundecino[8,7,6-hi]indole-8-carboxylic acid (Enantiomer 2)

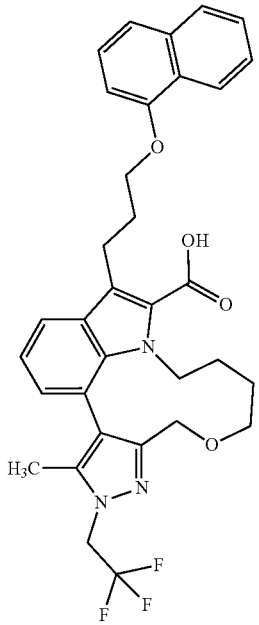 [SMILES: Cc1c2c(nn1CC(F)(F)F)COCCCCn1c(C(=O)O)c(CCCOc3cccc4ccccc34)c3cccc-2c31]

For the preparation of the racemic title compound and separation into its enantiomers see Example 241.

Analytical Chiral HPLC (method see Example 241): $R_t$=4.29 min, ee 95.9%

$^1$H-NMR (400 MHz, METHANOL-d4) δ [ppm]: 0.088 (0.32), 0.098 (0.51), 0.100 (0.65), 0.874 (0.23), 0.883 (0.29), 0.901 (0.46), 0.917 (0.19), 1.141 (0.16), 1.150 (0.19), 1.176 (0.37), 1.194 (0.23), 1.211 (0.28), 1.229 (0.21), 1.234 (0.20), 1.239 (0.19), 1.269 (0.19), 1.289 (1.96), 1.307 (1.09), 1.332 (0.42), 1.339 (0.72), 1.380 (0.20), 1.389 (0.22), 1.400 (0.68), 1.409 (0.22), 1.426 (0.25), 1.433 (0.19), 1.440 (0.23), 1.450 (0.19), 1.931 (5.67), 2.275 (0.19), 2.294 (0.20), 2.307 (0.43), 2.325 (0.60), 2.341 (0.46), 2.659 (16.00), 3.011 (0.30), 3.185 (0.16), 3.199 (0.30), 3.211 (0.32), 3.226 (0.19), 3.373 (0.25), 3.381 (0.25), 3.388 (0.51), 3.395 (0.35), 3.406 (0.67), 3.425 (0.37), 3.449 (0.23), 3.468 (0.49), 3.482 (0.26), 3.486 (0.30), 3.502 (0.25), 3.866 (0.19), 3.878 (0.16), 3.889 (0.28), 3.900 (0.18), 3.912 (0.21), 4.179 (0.71), 4.194 (1.54), 4.209 (0.69), 4.315 (1.08), 4.347 (1.19), 4.374 (0.25), 4.394 (0.26), 4.409 (0.21), 4.668 (1.13), 4.700 (0.98), 4.931 (0.51), 4.953 (0.97), 4.974 (0.89), 4.996 (0.29), 6.785 (0.69), 6.787 (0.70), 6.804 (0.77), 6.806 (0.74), 6.970 (0.64), 6.974 (0.71), 6.988 (1.16), 6.991 (1.03), 7.029 (1.04), 7.048 (1.04), 7.067 (0.61), 7.302 (0.62), 7.322 (1.06), 7.341 (0.95), 7.381 (0.99), 7.402 (0.55), 7.456 (0.19), 7.466 (1.46), 7.473 (0.74), 7.476 (0.77), 7.482 (0.84), 7.483 (0.88), 7.491 (1.55), 7.501 (0.21), 7.724 (0.78), 7.727 (0.85), 7.743 (0.81), 7.746 (0.76), 7.783 (0.55), 7.789 (0.33), 7.793 (0.35), 7.798 (0.56), 7.806 (0.47), 8.311 (0.50), 8.318 (0.41), 8.320 (0.40), 8.325 (0.27), 8.328 (0.26), 8.330 (0.25), 8.335 (0.47).

Example 243

(rac)-2-[2-(dimethylamino)ethyl]-3-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid trifluoroacetic acid salt

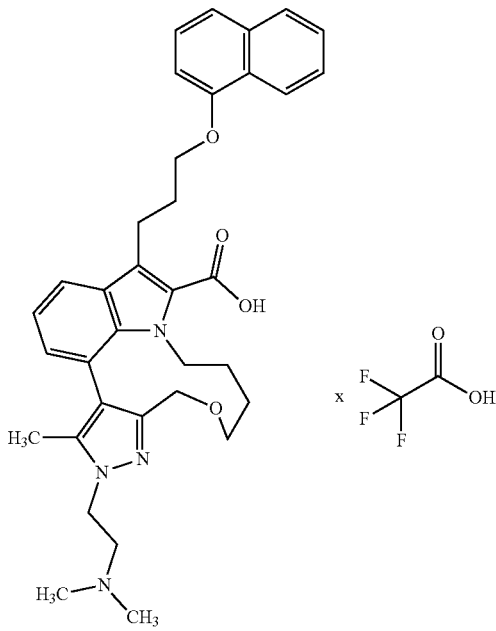 [SMILES: Cc1c2c(nn1CCN(C)C)COCCCCn1c(C(=O)O)c(CCCOc3cccc4ccccc34)c3cccc-2c31 ; O=C(O)C(F)(F)F]

A mixture of (rac)-ethyl 2-[2-(dimethylamino)ethyl]-3-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylate (90.0 mg, 148 µmol; see Intermediate 424), THF (6.0 ml), ethanol (4.3 ml) and aqueous solution of lithium hydroxide (3.0 ml, 1.0 M, 3.0 mmol) was stirred for 20 h at 60° C. For work-up, organic solvents were removed under vacuum, citric acid (2.78 g, 13.2 mmol) was added and the mixture was extracted several times with a mixture of dichloromethane and 2-propanol (4:1). The combined organic phases were filter through a silicone filter and concentrated. The residue was purified twice by preparative HPLC [Instrument: Waters Autopurification system; column: Waters XBrigde C18 5µ 100×30 mm; eluent A: water+0.2 vol-% aqueous ammonia (32%), eluent B: acetonitrile; gradient: 0.00-0.50 min 11% B (25→70 mL/min), 0.51-5.50 min 22-32% B (70 mL/min), DAD scan: 210-400 nm; second purification: eluent A: water+0.1 vol-% trifluoroacetic acid (99%), eluent B: acetonitrile; gradient: 0.00-0.50 min 19% B (25→70 mL/min), 0.51-5.50 min 38-52% B (70 mL/min)] to give the title compound 12.3 mg (92% purity, 11% yield).

LC-MS (Method 1): $R_t$=1.28 min; MS (ESIpos): m/z=581 [M+H]$^+$ $^1$H-NMR (400 MHz, DMSO-d6) δ[ppm]: 0.860 (0.22), 0.899 (0.18), 0.967 (0.97), 0.995 (0.43), 1.010 (0.50), 1.107 (6.36), 1.144 (1.26), 1.179 (0.68), 1.209 (0.72), 1.231 (0.90), 1.348 (0.50), 1.388 (0.18), 1.879 (16.00), 1.907 (0.14), 2.081 (0.22), 2.192 (1.15), 2.214 (1.40), 2.230 (1.04), 2.249 (0.36), 2.318 (0.68), 2.322 (1.55), 2.326 (2.16), 2.331 (1.47), 2.336 (0.68), 2.518 (8.56), 2.522 (5.75), 2.539 (0.32), 2.544 (0.18), 2.549 (0.22), 2.660 (0.72), 2.664 (1.62), 2.668 (2.19), 2.673 (1.55), 2.678 (0.68), 2.769 (0.25), 2.850 (4.49), 3.042 (0.32), 3.055 (0.36), 3.067 (0.72), 3.081 (0.65), 3.093 (0.47), 3.105 (0.32), 3.252 (0.25), 3.269 (0.50), 3.290 (1.04), 3.303 (2.01), 3.370 (0.83), 3.552 (0.83), 3.818 (0.29), 3.829 (0.36), 3.852 (0.68), 3.863 (0.40), 3.874 (0.43), 3.885 (0.32), 4.186 (1.08), 4.195 (1.91), 4.200 (1.91), 4.211 (3.02), 4.242 (2.23), 4.283 (0.40), 4.299 (0.58), 4.317 (0.65), 4.333 (0.47), 4.354 (0.29), 4.454 (0.65), 4.470 (1.29), 4.483 (1.29), 4.501 (0.58), 4.520 (0.25), 4.538 (2.16), 4.570 (1.87), 6.880 (1.83), 6.897 (2.05), 6.914 (2.05), 6.917 (2.12), 6.932 (2.48), 6.935 (2.27), 6.958 (0.22), 7.052 (2.16), 7.069 (2.05), 7.071 (2.34), 7.090 (1.76), 7.097 (0.29), 7.214 (0.22), 7.364 (1.58), 7.385 (2.70), 7.404 (2.19), 7.449 (2.80), 7.470 (1.62), 7.495 (0.36), 7.500 (0.65), 7.513 (1.73), 7.519 (2.44), 7.528 (3.85), 7.537 (2.77), 7.542 (1.91), 7.555 (0.68), 7.559 (0.32), 7.732 (1.98), 7.736 (2.01), 7.752 (1.83), 7.755 (1.76), 7.860 (1.62), 7.863 (1.22), 7.870 (0.79), 7.878 (1.19), 7.884 (1.37), 7.893 (0.18), 8.245 (1.40), 8.252 (1.15), 8.260 (0.68), 8.269 (1.29), 9.540 (0.32), 13.140 (0.40).

Example 244

(rac)-1-[2-(dimethylamino)ethyl]-3-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid trifluoroacetic acid salt

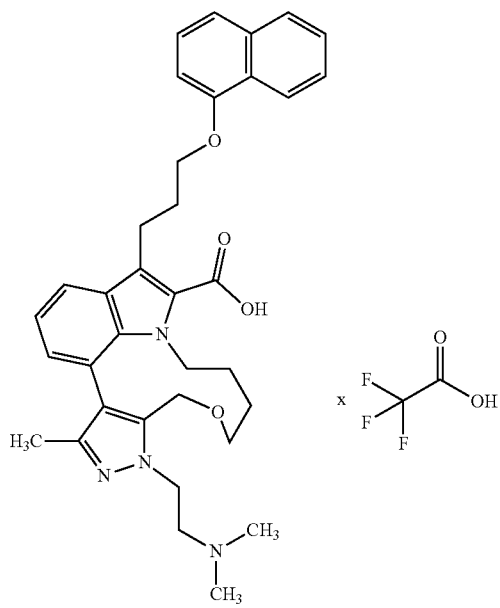 [SMILES: Cc1nn(CCN(C)C)c2c1-c1cccc3c(CCCOc4cccc5ccccc45)c(C(=O)O)n(c13)CCCCOC2 ; O=C(O)C(F)(F)F]

The title compound (27.6 mg; 91% purity, 20% yield) was prepared in analogy to the synthesis of Example 243 using (rac)-ethyl 1-[2-(dimethylamino)ethyl]-3-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (110 mg, 181 µmol; see Intermediate 427) as starting material.

LC-MS (Method 1): R$_t$=1.28 min; MS (ESIpos): m/z=581 [M+H]$^+$ $^1$H-NMR (400 MHz, DMSO-d$_6$): δ [ppm]=13.23 (br s, 1H), 9.46 (br s, 1H), 8.27-8.19 (m, 1H), 7.91-7.83 (m, 1H), 7.79 (dd, 1H), 7.56-7.37 (m, 4H), 7.12-7.04 (m, 1H), 6.90 (d, 1H), 6.84 (d, 1H), 4.73 (d, 1H), 4.61-4.45 (m, 3H), 4.29-4.14 (m, 3H), 4.01-3.95 (m, 1H), 2.91 (br s, 6H), 2.88-2.77 (m, 1H), 2.27-2.16 (m, 2H), 1.86 (s, 3H), 1.49-1.18 (m, 2H), 1.08-0.95 (m, 2H).

Example 247

(rac)-1-[3-(naphthalen-1-yloxy)propyl]-4,5,6,7,13,14-hexahydro-9H,12H-[1,3]oxazino[3",2":1',5']pyrazolo[4',3':9,10][1,6]oxazacycloundecino[8,7,6-hi]indole-2-carboxylic acid

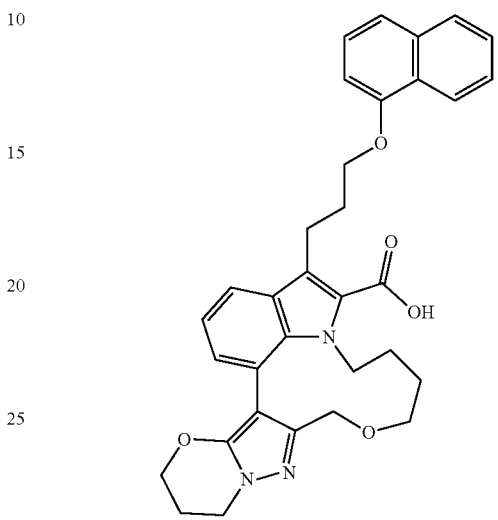

A mixture of (rac)-ethyl 1-[3-(naphthalen-1-yloxy)propyl]-4,5,6,7,13,14-hexahydro-9H,12H-[1,3]oxazino[3",2":1',5']pyrazolo[4',3':9,10][1,6]oxazacycloundecino[8,7,6-hi]indole-2-carboxylate (220 mg, 380 µmol; see Intermediate 430), ethanol (13 ml), THF (18 ml) and aqueous solution of lithium hydroxide (7.6 ml, 1.0 M, 7.6 mmol) was stirred for 16 h at 60° C. Aqueous solution of lithium hydroxide (5.0 ml, 1.0 M, 5.0 mmol) was added and the mixture was stirred for another 4 h at 60° C. For work-up, organic solvents were removed under vacuum, citric acid was added and the mixture was extracted several times with a mixture of dichloromethane and 2-propanol (4:1). The combined organic phases were filtered through a silicone filter and concentrated. The residue was purified by preparative HPLC (Method P9) to give the title compound 118 mg (55% yield).

LC-MS (Method 1): R$_t$=1.45 min; MS (ESIpos): m/z=552 [M+H]$^+$ $^1$H-NMR (400 MHz, DMSO-d6) δ[ppm]: 1.011 (2.05), 1.022 (1.99), 1.145 (1.49), 1.192 (4.54), 1.205 (4.54), 1.217 (4.36), 1.229 (3.67), 1.353 (2.12), 1.407 (1.31), 1.907 (1.18), 2.074 (2.37), 2.150 (4.61), 2.166 (8.65), 2.183 (10.58), 2.200 (7.72), 2.218 (3.30), 2.322 (2.80), 2.326 (3.86), 2.331 (2.68), 2.336 (1.31), 2.518 (12.20), 2.522 (8.78), 2.539 (1.62), 2.664 (2.74), 2.668 (3.74), 2.673 (2.55), 2.678 (1.12), 3.140 (1.43), 3.166 (3.49), 3.179 (3.05), 3.189 (2.61), 3.205 (2.05), 3.229 (2.80), 3.244 (2.86), 3.263 (5.04), 3.282 (5.54), 3.292 (4.17), 3.307 (4.36), 3.355 (5.73), 3.374 (3.05), 3.389 (3.18), 3.407 (1.43), 4.069 (11.33), 4.082 (2.80), 4.100 (13.26), 4.111 (6.54), 4.120 (4.42), 4.129 (4.79), 4.139 (6.47), 4.158 (6.16), 4.167 (10.77), 4.183 (16.00), 4.200 (14.07), 4.215 (7.28), 4.229 (5.17), 4.244 (2.80), 4.322 (1.68), 4.339 (2.74), 4.357 (2.86), 4.377 (2.18), 4.394 (1.43), 4.506 (10.71), 4.537 (9.59), 6.886 (8.84), 6.903 (9.65), 6.927 (6.97), 6.929 (7.66), 6.944 (11.08), 6.947 (10.40), 6.996 (10.46), 7.016 (11.39), 7.034 (6.85), 7.367 (6.72), 7.388 (12.64), 7.407 (10.46), 7.448 (13.07), 7.469 (7.28), 7.499 (1.00), 7.505 (2.68), 7.516 (10.21), 7.519 (11.27), 7.522 (8.65), 7.530 (11.95), 7.537 (9.34), 7.540 (11.27), 7.543 (10.83), 7.554 (2.55), 7.560 (0.81), 7.675 (8.78), 7.678 (8.96), 7.695 (8.09), 7.698 (7.78), 7.858 (7.41), 7.863 (4.86), 7.871 (6.72), 7.875 (4.67), 7.882 (6.35), 7.890 (0.93), 8.253 (6.54), 8.263 (5.35), 8.277 (5.91), 13.116 (1.74).

The title compound (118 mg) was separated into its enantiomers by preparative chiral HPLC to give enantiomer 1 (45.4 mg, see Example 248) and enantiomer 2 (49.8 mg, see Example 249).

Preparative chiral HPLC method: Instrument: Labomatic HD5000, Labocord-5000; Gilson GX-241, Labcol Vario 4000, column: Chiralpak AD-H 5μ 250×30 mm; eluent A: hexane+0.1 vol-% trifluoroacetic acid; eluent B: 2-propanol; gradient: 20-50% B in 20 min; flow 40.0 ml/min; UV 254 nm Analytical chiral HPLC method: Instrument: Agilent HPLC 1260; column: Chiralpak AD-H 3μ 100×4.6 mm; eluent A: hexane+0.1 vol-% trifluoroacetic acid; eluent B: 2-propanol; gradient: 20-50% B in 7 min; flow 1.4 ml/min; temperature: 25° C.; DAD 254 nm Example 248

1-[3-(naphthalen-1-yloxy)propyl]-4,5,6,7,13,14-hexahydro-9H,12H-[1,3]oxazino[3",2":1',5']pyrazolo[4',3':9,10][1,6]oxazacycloundecino[8,7,6-hi]indole-2-carboxylic acid (Enantiomer 1)

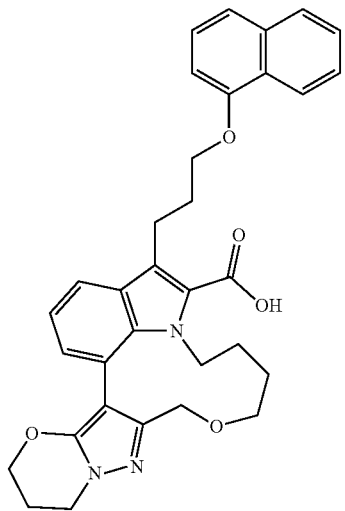 [SMILES: O=C(O)c1c(CCCOc2cccc3ccccc23)c2cccc3c2n1CCCCOCc1nn2c(c1-3)OCCC2]

For the preparation of the racemic title compound and separation into its enantiomers see Example 247.

Analytical Chiral HPLC (method see Example 247): R$_t$=3.00 min, e.e. 98.4%.

$^1$H-NMR (400 MHz, DMSO-d6) δ[ppm]: 1.002 (0.86), 1.024 (0.86), 1.108 (1.29), 1.145 (1.22), 1.154 (0.86), 1.192 (1.87), 1.205 (1.94), 1.217 (1.87), 1.230 (1.87), 1.353 (1.00), 1.907 (1.87), 2.151 (1.79), 2.166 (3.52), 2.183 (4.38), 2.201 (3.16), 2.318 (1.36), 2.323 (3.09), 2.327 (4.38), 2.331 (3.09), 2.337 (1.43), 2.518 (16.00), 2.523 (10.98), 2.540 (3.16), 2.660 (1.36), 2.665 (3.09), 2.669 (4.30), 2.674 (3.01), 2.678 (1.36), 3.165 (1.43), 3.180 (1.29), 3.205 (1.00), 3.226 (1.15), 3.242 (1.15), 3.260 (1.79), 3.279 (2.15), 3.292 (1.79), 3.354 (2.44), 3.372 (1.36), 3.388 (1.29), 4.069 (4.59), 4.082 (1.22), 4.100 (5.52), 4.113 (2.73), 4.130 (2.22), 4.139 (3.16), 4.148 (2.08), 4.167 (4.09), 4.183 (6.17), 4.200 (5.52), 4.216 (2.94), 4.230 (2.08), 4.245 (1.15), 4.325 (0.65), 4.341 (1.08), 4.360 (1.15), 4.379 (0.93), 4.505 (4.23), 4.536 (3.73), 5.759 (4.81), 6.886 (3.59), 6.904 (3.87), 6.925 (2.30), 6.941 (3.37), 6.994 (3.23), 7.013 (3.87), 7.031 (2.15), 7.367 (2.73), 7.388 (5.02), 7.407 (4.02), 7.448 (5.17), 7.469 (2.94), 7.505 (1.00), 7.517 (3.80), 7.519 (4.30), 7.522 (3.52), 7.530 (4.88), 7.538 (3.59), 7.541 (4.30), 7.543 (4.30), 7.554 (1.08), 7.674 (2.87), 7.692 (2.65), 7.859 (2.87), 7.863 (1.94), 7.871 (2.65), 7.876 (1.87), 7.882 (2.51), 8.253 (2.65), 8.263 (2.15), 8.276 (2.37).

Example 249

1-[3-(naphthalen-1-yloxy)propyl]-4,5,6,7,13,14-hexahydro-9H,12H-[1,3]oxazino[3",2":1',5']pyrazolo[4',3':9,10][1,6]oxazacycloundecino[8,7,6-hi]indole-2-carboxylic acid (Enantiomer 2)

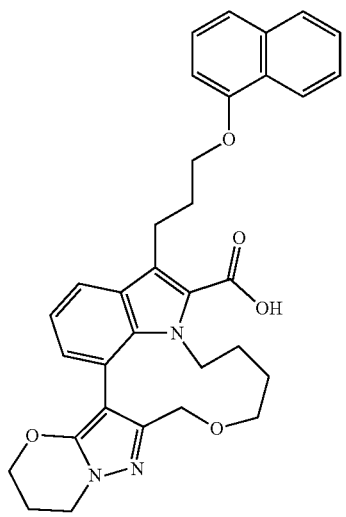

For the preparation of the racemic title compound and separation into its enantiomers see Example 247.

Analytical Chiral HPLC (method see Example 247): R$_t$=4.88 min, e.e. 93.4%.

$^1$H-NMR (400 MHz, DMSO-d6) δ[ppm]: 0.984 (1.11), 0.998 (1.18), 1.009 (1.18), 1.021 (1.18), 1.108 (2.08), 1.145 (1.25), 1.194 (2.70), 1.206 (2.77), 1.218 (2.63), 1.231 (2.63), 1.353 (1.32), 1.907 (1.73), 2.151 (2.56), 2.167 (5.06), 2.184 (6.23), 2.201 (4.57), 2.218 (1.94), 2.318 (1.39), 2.323 (3.05), 2.327 (4.23), 2.331 (2.98), 2.337 (1.32), 2.518 (16.00), 2.523 (11.15), 2.540 (1.18), 2.660 (1.39), 2.665 (3.12), 2.669 (4.23), 2.673 (2.98), 2.678 (1.32), 3.142 (0.83), 3.159 (1.87), 3.166 (2.08), 3.172 (1.80), 3.181 (1.80), 3.189 (1.45), 3.205 (1.18), 3.231 (1.59), 3.246 (1.66), 3.265 (3.12), 3.284 (3.19), 3.292 (2.42), 3.307 (2.22), 3.357 (2.98), 3.375 (1.66), 3.390 (1.80), 3.409 (0.76), 3.962 (0.69), 4.069 (6.58), 4.082 (1.73), 4.100 (7.83), 4.113 (4.02), 4.122 (2.56), 4.129 (2.70), 4.140 (3.67), 4.147 (3.74), 4.159 (3.88), 4.168 (6.10), 4.184 (9.70), 4.200 (8.38), 4.216 (4.23), 4.230 (3.05), 4.245 (1.66), 4.319 (0.97), 4.336 (1.66), 4.355 (1.66), 4.374 (1.32), 4.391 (0.90), 4.507 (6.10), 4.538 (5.54), 5.759 (15.58), 6.887 (5.13), 6.905 (5.54), 6.930 (4.16), 6.933 (4.50), 6.947 (6.65), 6.951 (6.23), 6.999 (6.03), 7.018 (6.72), 7.036 (3.88), 7.368 (3.81), 7.389 (7.20), 7.408 (5.89), 7.450 (7.48), 7.470 (4.16), 7.505 (1.45), 7.517 (5.61), 7.520 (6.16), 7.523 (5.06), 7.531 (7.00), 7.538 (5.19), 7.542 (6.23), 7.543 (6.16), 7.555 (1.52), 7.678 (5.06), 7.681 (5.26), 7.698 (4.78), 7.701 (4.57), 7.859 (4.16), 7.863 (2.77), 7.872 (3.88), 7.877 (2.63), 7.883 (3.53), 8.246 (0.62), 8.253 (3.81), 8.264 (3.05), 8.277 (3.39), 13.103 (1.87).

Example 250

(rac)-1-[3-(naphthalen-1-yloxy)propyl]-4,5,6,7,12,13-hexahydro-9H,15H-[1,4]oxazino[4'',3'':1',5']pyrazolo[4',3':9,10][1,6]oxazacycloundecino[8,7,6-hi]indole-2-carboxylic acid

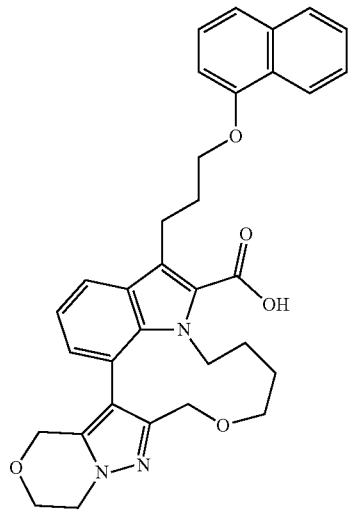 [SMILES: O=C(O)c1c(CCCOc2cccc3ccccc23)c2cccc3c2n1CCCCOCc1nn2c(c1-3)COCC2]

A mixture of (rac)-ethyl 1-[3-(naphthalen-1-yloxy)propyl]-4,5,6,7,12,13-hexahydro-9H,15H-[1,4]oxazino[4'',3'':1',5']pyrazolo[4',3':9,10][1,6]oxazacycloundecino[8,7,6-hi]indole-2-carboxylate (310 mg, 535 µmol; see Intermediate 433), ethanol (18 ml), THF (25 ml) and aqueous solution of lithium hydroxide (11 ml, 1.0 M, 11 mmol) was stirred for 16 h at 60° C. For work-up, organic solvents were removed under vacuum, citric acid was added and the mixture was extracted several times with a mixture of dichloromethane and 2-propanol (4:1). The combined organic phases were filtered through a silicone filter and concentrated. The residue was purified by preparative HPLC (Method P9) to give the title compound 146 mg (94% purity, 46% yield).

LC-MS (Method 1): $R_t$=1.45 min; MS (ESIpos): m/z=552 [M+H]$^+$ $^1$H-NMR (400 MHz, DMSO-d6) δ[ppm]: 1.012 (1.82), 1.022 (1.95), 1.033 (1.95), 1.145 (1.88), 1.173 (4.08), 1.187 (4.14), 1.198 (3.83), 1.210 (2.51), 1.231 (1.69), 1.349 (1.95), 1.407 (1.00), 1.907 (1.25), 2.074 (2.20), 2.188 (3.95), 2.205 (5.77), 2.222 (4.52), 2.240 (1.76), 2.318 (1.25), 2.323 (2.76), 2.327 (3.89), 2.331 (2.76), 2.337 (1.19), 2.518 (14.37), 2.523 (9.98), 2.540 (0.69), 2.660 (1.25), 2.665 (2.82), 2.669 (3.95), 2.674 (2.76), 2.678 (1.32), 3.069 (1.38), 3.083 (1.63), 3.094 (3.26), 3.108 (2.89), 3.118 (2.20), 3.133 (1.51), 3.235 (1.00), 3.252 (1.82), 3.268 (3.07), 3.286 (6.53), 3.299 (7.09), 3.307 (7.09), 3.369 (1.44), 3.859 (1.32), 3.871 (1.69), 3.883 (1.69), 3.893 (3.07), 3.905 (1.82), 3.917 (2.01), 3.929 (1.51), 4.058 (4.58), 4.071 (11.61), 4.082 (8.09), 4.097 (2.89), 4.103 (2.95), 4.109 (2.70), 4.130 (3.51), 4.144 (5.15), 4.157 (2.07), 4.182 (4.77), 4.192 (8.60), 4.196 (8.60), 4.207 (5.21), 4.212 (5.21), 4.224 (12.99), 4.229 (5.96), 4.236 (6.15), 4.243 (3.26), 4.255 (12.11), 4.274 (14.93), 4.290 (13.80), 4.303 (1.76), 4.310 (1.76), 4.317 (1.88), 4.327 (4.77), 4.352 (2.89), 4.368 (2.20), 4.388 (1.32), 4.407 (0.94), 4.440 (0.63), 4.551 (10.04), 4.582 (8.72), 6.882 (8.47), 6.899 (9.47), 6.921 (0.69), 6.954 (6.71), 6.956 (7.28), 6.971 (10.04), 6.974 (9.66), 7.034 (9.47), 7.043 (1.13), 7.053 (10.67), 7.061 (1.32), 7.072 (6.53), 7.080 (0.63), 7.363 (6.53), 7.372 (0.94), 7.384 (11.98), 7.393 (1.44), 7.403 (9.85), 7.412 (0.94), 7.445 (12.67), 7.466 (7.22), 7.492 (1.38), 7.497 (2.76), 7.509 (8.22), 7.514 (13.99), 7.524 (16.00), 7.533 (15.06), 7.538 (8.60), 7.550 (2.89), 7.555 (1.19), 7.706 (8.09), 7.709 (8.41), 7.726 (8.22), 7.729 (7.84), 7.746 (0.56), 7.856 (7.28), 7.859 (5.08), 7.866 (3.45), 7.871 (4.39), 7.873 (5.02), 7.879 (6.15), 7.888 (0.82), 8.213 (0.50), 8.218 (0.50), 8.231 (1.07), 8.239 (6.46), 8.246 (4.52), 8.251 (2.76), 8.253 (2.70), 8.263 (5.58), 13.162 (1.38).

The title compound (145 mg) was separated into its enantiomers by preparative chiral HPLC to give enantiomer 1 (60.0 mg, see Example 251) and enantiomer 2 (45.0 mg, see Example 252).

Preparative chiral HPLC method: Instrument: Sepiatec: Prep SFC100; column: Chiralpak ID 5 µm 250×30 mm; eluent A: carbon dioxide, eluent B: 2-propanol+0.4 vol-% diethylamine (99%); isocratic: 35% B; flow 100.0 ml/min temperature: 40° C.; BPR: 150 bar; MWD @ 220 nm Analytical chiral HPLC method: Instrument: Agilent: 1260, Aurora SFC-Modul; column: Chiralpak ID 5 µm 100×4.6 mm; eluent A: carbon dioxide, eluent B: 2-propanol+0.2 vol-% diethylamine (99%); isocratic: 35% B; flow 4.0 ml/min; temperature: 37.5° C.; BPR: 100 bar; MWD @ 220 nm Example 251

1-[3-(naphthalen-1-yloxy)propyl]-4,5,6,7,12,13-hexahydro-9H,15H-[1,4]oxazino[4'',3'':1',5']pyrazolo[4',3':9,10][1,6]oxazacycloundecino[8,7,6-hi]indole-2-carboxylic acid-N-ethylethanamine salt
(Enantiomer 1)

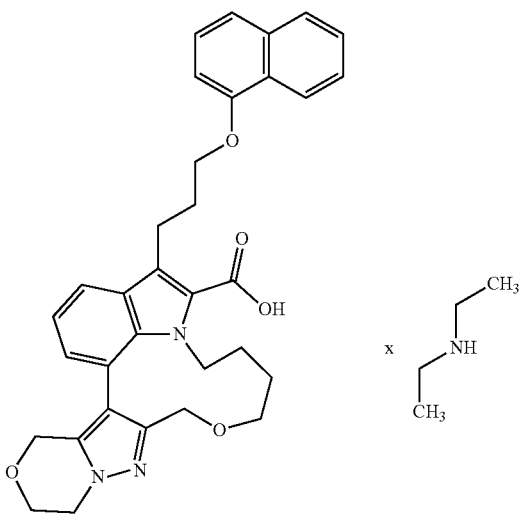

For the preparation of the racemic title compound and separation into its enantiomer see Example 250.

Analytical Chiral HPLC (method see Example 250): $R_t$=2.29 min, e.e. 99.1%.

$^1$H-NMR (400 MHz, DMSO-d6) δ[ppm]: 0.968 (0.71), 1.108 (16.00), 1.138 (4.33), 1.144 (1.29), 1.156 (8.20), 1.174 (3.94), 1.209 (0.66), 1.277 (0.49), 1.293 (0.59), 1.301 (0.41), 1.331 (0.42), 1.930 (1.71), 2.181 (0.83), 2.198 (1.20), 2.216 (0.88), 2.323 (0.73), 2.327 (1.00), 2.331 (0.73), 2.518 (3.42), 2.523 (2.37), 2.665 (0.74), 2.669 (1.01), 2.674 (0.71), 2.850 (0.88), 2.867 (2.66), 2.886 (2.66), 2.904 (0.81), 3.088 (0.63), 3.101 (0.51), 3.114 (0.44), 3.204 (0.41), 3.219 (0.54), 3.238 (0.81), 3.257 (0.58), 3.287 (1.73), 3.759 (0.51), 3.824 (0.46), 4.054 (0.91), 4.068 (2.32), 4.079 (1.59), 4.094 (0.56), 4.106 (0.47), 4.127 (0.68), 4.140 (1.00), 4.155 (0.66), 4.163 (0.73), 4.179 (1.49), 4.188 (1.57), 4.204 (0.79), 4.214 (0.71), 4.226 (2.77), 4.244 (1.07), 4.257 (2.55), 4.281 (2.66), 4.294 (2.71), 4.331 (0.54), 4.417 (0.42), 4.435 (0.42), 4.521 (1.79), 4.552 (1.54), 6.856 (0.83), 6.870 (2.25), 6.887 (1.81), 6.973 (1.07), 6.992 (1.49), 7.011 (0.78), 7.352 (1.23), 7.372 (2.27), 7.391 (1.79), 7.436 (2.32), 7.457 (1.34), 7.490 (0.56), 7.502 (1.45), 7.507 (2.30), 7.517 (3.04), 7.526 (2.62), 7.532 (1.71), 7.544 (0.54), 7.627 (1.07), 7.646 (0.98), 7.850 (1.34), 7.853 (0.98), 7.860 (0.66), 7.868 (0.91), 7.873 (1.12), 8.236 (1.18), 8.243 (0.93), 8.251 (0.52), 8.260 (1.10).

Example 252

1-[3-(naphthalen-1-yloxy)propyl]-4,5,6,7,12,13-hexahydro-9H,15H-[1,4]oxazino[4",3":1',5']pyrazolo[4',3':9,10][1,6]oxazacycloundecino[8,7,6-hi]indole-2-carboxylic acid-N-ethylethanamine salt
(Enantiomer 2)

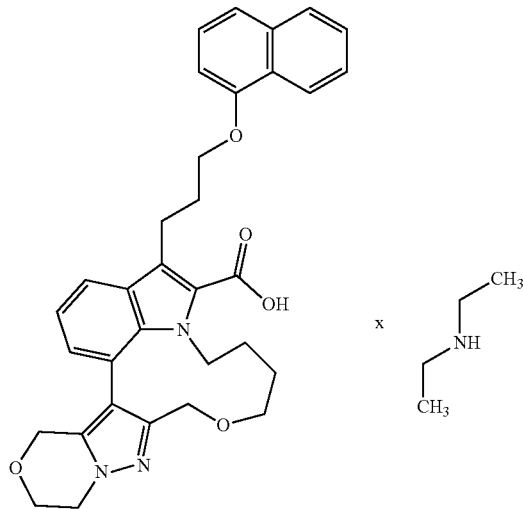

For the preparation of the racemic title compound and separation into its enantiomer see Example 250.

Analytical Chiral HPLC (method see Example 250): $R_t$=5.55 min, e.e. 99.0%.

$^1$H-NMR (400 MHz, DMSO-d6) δ[ppm]: 0.968 (0.85), 1.108 (16.00), 1.138 (1.46), 1.144 (5.23), 1.163 (9.66), 1.181 (4.73), 1.208 (0.59), 1.231 (0.42), 1.334 (0.59), 1.348 (0.58), 2.182 (1.16), 2.199 (1.70), 2.217 (1.24), 2.234 (0.45), 2.323 (0.61), 2.327 (0.83), 2.331 (0.61), 2.518 (3.00), 2.523 (1.97), 2.665 (0.61), 2.669 (0.85), 2.673 (0.61), 2.855 (1.08), 2.874 (3.35), 2.892 (3.27), 2.910 (1.00), 3.076 (0.45), 3.088 (0.89), 3.100 (0.74), 3.113 (0.62), 3.209 (0.61), 3.224 (0.85), 3.242 (1.23), 3.261 (0.91), 3.275 (1.33), 3.291 (2.57), 3.310 (2.38), 3.323 (2.59), 3.806 (0.42), 3.828 (0.71), 3.850 (0.50), 4.054 (1.30), 4.067 (3.25), 4.079 (2.26), 4.094 (0.76), 4.106 (0.64), 4.127 (0.95), 4.140 (1.40), 4.155 (0.91), 4.163 (1.05), 4.179 (2.05), 4.188 (2.09), 4.203 (1.09), 4.213 (0.98), 4.226 (3.62), 4.243 (1.43), 4.257 (3.41), 4.281 (3.64), 4.293 (3.72), 4.330 (0.74), 4.415 (0.64), 4.434 (0.65), 4.448 (0.58), 4.522 (2.50), 4.554 (2.12), 6.868 (2.66), 6.879 (1.95), 6.886 (2.72), 6.977 (1.56), 6.996 (2.19), 7.015 (1.20), 7.351 (1.50), 7.371 (2.93), 7.391 (2.28), 7.436 (3.14), 7.456 (1.82), 7.489 (0.61), 7.502 (1.87), 7.507 (3.00), 7.517 (3.79), 7.526 (3.37), 7.531 (2.07), 7.543 (0.68), 7.632 (1.67), 7.652 (1.56), 7.849 (1.80), 7.859 (0.92), 7.867 (1.27), 7.873 (1.53), 8.236 (1.56), 8.243 (1.27), 8.250 (0.74), 8.260 (1.47).

Example 253

(rac)-1-[3-(naphthalen-1-yloxy)propyl]-4,5,6,7,12,13,14,15-octahydro-9H-pyrido[1",2":1',5']pyrazolo[4',3':9,10][1,6]oxazacycloundecino[8,7,6-hi]indole-2-carboxylic acid

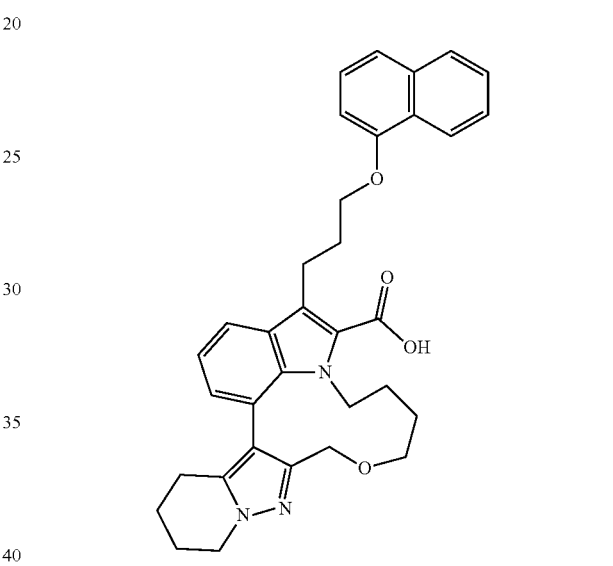

The title compound 72.5 mg (27% yield) was prepared in analogy to the synthesis of Example 247 using (rac)-ethyl 1-[3-(naphthalen-1-yloxy)propyl]-4,5,6,7,12,13,14,15-octahydro-9H-pyrido[1",2":1',5']pyrazolo[4',3':9,10][1,6]oxazacycloundecino[8,7,6-hi]indole-2-carboxylate (280 mg, 485 µmol; see Intermediate 436) as starting material.

LC-MS (Method 1): $R_t$=1.52 min; MS (ESIpos): m/z=550 [M+H]$^+$ $^1$H-NMR (400 MHz, DMSO-d6) δ[ppm]: 1.007 (0.45), 1.017 (0.45), 1.036 (9.48), 1.053 (16.00), 1.071 (9.77), 1.176 (0.93), 1.231 (0.41), 1.326 (0.45), 1.353 (1.92), 1.635 (0.56), 1.651 (0.58), 1.669 (0.41), 1.698 (0.41), 1.712 (0.65), 1.726 (0.60), 1.945 (1.21), 1.959 (1.68), 1.974 (1.13), 2.139 (0.68), 2.155 (1.35), 2.181 (1.47), 2.195 (1.26), 2.204 (1.58), 2.222 (1.21), 2.238 (0.48), 2.518 (2.72), 2.523 (1.84), 3.074 (0.73), 3.088 (0.65), 3.098 (0.48), 3.256 (0.77), 3.270 (1.25), 3.285 (1.40), 3.365 (0.77), 3.425 (1.13), 3.434 (1.19), 3.442 (1.17), 3.450 (1.13), 3.904 (0.68), 3.915 (0.41), 3.927 (0.44), 4.021 (0.66), 4.036 (0.77), 4.052 (0.90), 4.069 (0.41), 4.185 (3.47), 4.193 (2.60), 4.216 (3.02), 4.320 (0.60), 4.340 (0.95), 4.355 (1.22), 4.539 (2.24), 4.570 (1.96), 6.879 (1.79), 6.896 (2.00), 6.921 (1.64), 6.924 (1.68), 6.939 (2.19), 6.941 (2.08), 7.026 (2.08), 7.046 (2.34), 7.064 (1.54), 7.362 (1.44), 7.383 (2.65), 7.402 (2.16), 7.445 (2.68), 7.466 (1.52), 7.497 (0.60), 7.509 (1.80), 7.514 (3.02), 7.525 (3.55), 7.533 (3.30), 7.539 (1.89), 7.551 (0.62), 7.689 (1.83), 7.691 (1.87), 7.708 (1.74), 7.712 (1.70), 7.855 (1.54), 7.859 (1.11), 7.865 (0.78), 7.870 (0.94), 7.873 (1.02), 7.879 (1.31), 8.242 (1.38), 8.249 (1.01), 8.257 (0.62), 8.266 (1.27).

The title compound (72 mg) was separated into its enantiomers by preparative chiral HPLC to give enantiomer 1 (10.3 mg, see Example 254) and enantiomer 2 (8.1 mg, see Example 255).

Preparative chiral HPLC method: Instrument: Labomatic HD5000, Labocord-5000; Gilson GX-241, Labcol Vario 4000, column: Chiralpak AD 5μ 250×30 mm; eluent A: hexane+0.1 vol-% trifluoroacetic acid (99%); eluent B: 2-propanol; gradient: 20→50% B in 20 min; flow 40.0 ml/min; UV 254 nm Analytical chiral HPLC method: Instrument: Waters Alliance 2695Agilent HPLC 1260; column: Chiralpak AD 3μ 100×4.6 mm; eluent A: hexane+0.1 vol-% trifluoroacetic acid (99%); eluent B: 2-propanol; gradient: 20-50% B in 7 min; flow 1.4 ml/min; temperature: 25° C.; DAD 254 nm Example 254

1-[3-(naphthalen-1-yloxy)propyl]-4,5,6,7,12,13,14,15-octahydro-9H-pyrido[1'',2'':1',5']pyrazolo[4',3':9,10][1,6]oxazacycloundecino[8,7,6-hi]indole-2-carboxylic acid (Enantiomer 1)

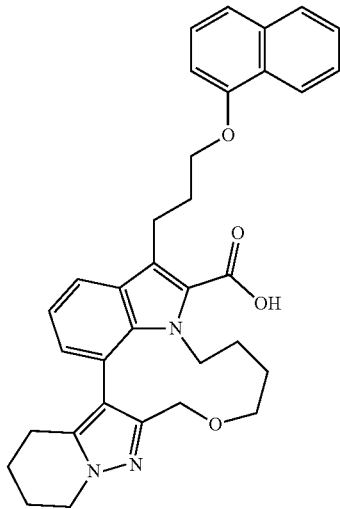 [SMILES: O=C(O)c1c(CCCOc2cccc3ccccc23)c2cccc3c2n1CCCCOCc1nn2c(c1-3)CCCC2]

For the preparation of the racemic title compound and separation into its enantiomer see Example 253.

Analytical Chiral HPLC (method see Example 253): $R_t$=2.60 min, e.e. >99%.

$^1$H-NMR (400 MHz, DMSO-d6) δ[ppm]: 0.787 (0.46), 0.851 (0.42), 0.860 (0.38), 0.968 (1.42), 1.010 (0.84), 1.019 (0.80), 1.108 (16.00), 1.144 (2.14), 1.175 (2.60), 1.209 (1.34), 1.232 (2.22), 1.256 (1.03), 1.296 (0.84), 1.332 (1.19), 1.349 (0.92), 1.620 (0.65), 1.636 (0.84), 1.652 (0.84), 1.669 (0.61), 1.700 (0.57), 1.713 (0.92), 1.727 (0.84), 1.746 (0.54), 1.907 (0.65), 1.946 (1.68), 1.960 (2.37), 1.975 (1.65), 2.114 (0.54), 2.140 (0.96), 2.156 (1.88), 2.169 (1.49), 2.183 (1.99), 2.204 (2.26), 2.222 (1.68), 2.239 (0.69), 2.323 (1.65), 2.327 (2.30), 2.331 (1.65), 2.337 (0.77), 2.518 (8.38), 2.523 (5.74), 2.537 (0.54), 2.660 (0.77), 2.665 (1.65), 2.669 (2.26), 2.673 (1.61), 2.678 (0.73), 3.048 (0.42), 3.063 (0.50), 3.074 (1.00), 3.088 (0.88), 3.098 (0.69), 3.113 (0.50), 3.265 (1.65), 3.282 (2.11), 3.304 (1.61), 3.362 (0.92), 3.379 (0.42), 3.867 (0.42), 3.877 (0.50), 3.900 (0.88), 3.911 (0.57), 3.923 (0.57), 4.005 (0.46), 4.021 (0.92), 4.037 (1.07), 4.053 (1.22), 4.068 (0.57), 4.186 (4.94), 4.189 (4.36), 4.217 (4.06), 4.306 (0.42), 4.323 (0.73), 4.342 (0.80), 4.360 (0.65), 4.377 (0.42), 4.538 (2.91), 4.569 (2.56), 6.878 (2.45), 6.896 (2.68), 6.919 (1.80), 6.935 (2.33), 7.023 (2.11), 7.043 (2.68), 7.061 (1.61), 7.362 (1.76), 7.382 (3.33), 7.402 (2.60), 7.445 (3.52), 7.466 (2.03), 7.498 (0.69), 7.510 (2.18), 7.515 (3.71), 7.524 (4.29), 7.534 (4.02), 7.539 (2.37), 7.551 (0.77), 7.688 (2.11), 7.705 (1.99), 7.856 (1.99), 7.866 (1.00), 7.873 (1.34), 7.879 (1.72), 8.242 (1.76), 8.249 (1.34), 8.255 (0.80), 8.266 (1.65), 13.114 (0.46).

Example 255

1-[3-(naphthalen-1-yloxy)propyl]-4,5,6,7,12,13,14,15-octahydro-9H-pyrido[1'',2'':1',5']pyrazolo[4',3':9,10][1,6]oxazacycloundecino[8,7,6-hi]indole-2-carboxylic acid (Enantiomer 2)

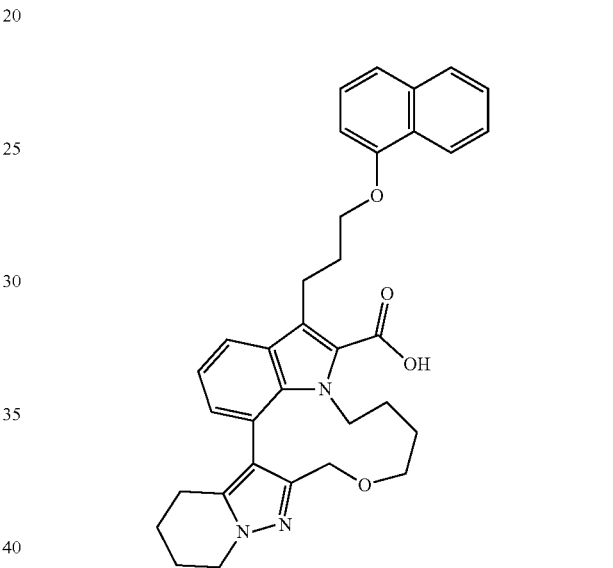

For the preparation of the racemic title compound and separation into its enantiomer see Example 253.

Analytical Chiral HPLC (method see Example 253): $R_t$=3.45 min, e.e. 93.6%.

$^1$H-NMR (400 MHz, DMSO-d6) δ[ppm]: 0.787 (0.64), 0.851 (0.64), 0.860 (0.52), 0.968 (1.57), 1.010 (1.05), 1.019 (1.05), 1.108 (16.00), 1.144 (2.79), 1.174 (3.43), 1.209 (1.75), 1.232 (3.37), 1.256 (1.75), 1.296 (1.22), 1.332 (1.63), 1.349 (1.28), 1.621 (0.81), 1.636 (1.05), 1.652 (1.05), 1.669 (0.76), 1.700 (0.76), 1.713 (1.11), 1.727 (0.99), 1.746 (0.70), 1.907 (0.70), 1.946 (2.04), 1.961 (2.79), 1.975 (1.98), 2.114 (0.58), 2.140 (1.11), 2.156 (2.21), 2.183 (2.39), 2.204 (2.68), 2.223 (2.04), 2.239 (0.81), 2.323 (2.56), 2.327 (3.43), 2.331 (2.44), 2.337 (1.16), 2.518 (13.27), 2.523 (8.96), 2.660 (1.16), 2.665 (2.56), 2.669 (3.49), 2.673 (2.44), 3.048 (0.52), 3.073 (1.16), 3.088 (1.05), 3.098 (0.81), 3.113 (0.58), 3.231 (0.41), 3.265 (1.98), 3.282 (2.44), 3.361 (1.11), 3.879 (0.58), 3.901 (0.99), 3.924 (0.70), 4.004 (0.52), 4.021 (1.05), 4.037 (1.22), 4.053 (1.40), 4.069 (0.70), 4.186 (5.76), 4.189 (5.24), 4.217 (4.77), 4.306 (0.52), 4.324 (0.87), 4.341 (0.99), 4.359 (0.76), 4.377 (0.47), 4.538 (3.37), 4.569 (2.91), 6.879 (2.91), 6.897 (3.14), 6.919 (2.04), 6.936 (2.62), 7.023 (2.21), 7.043 (3.03), 7.061 (1.75), 7.363 (2.04), 7.383 (3.84), 7.402 (3.03), 7.445 (4.13), 7.466 (2.33), 7.498 (0.81), 7.510 (2.50), 7.515 (4.25), 7.525 (5.00), 7.534 (4.60), 7.539 (2.68), 7.551 (0.87), 7.556 (0.41), 7.688 (2.39), 7.706 (2.27), 7.856 (2.39), 7.866 (1.16), 7.873 (1.57), 7.880 (1.98), 8.242 (2.09), 8.249 (1.57), 8.266 (1.92), 13.115 (0.64).

Example 256

1,3,4-trimethyl-7-[4-(naphthalen-1-yloxy)butan-2-yl]-1,10,11,12,13,15-hexahydropyrazolo[4',3':9,10][1,6]oxazacycloundecino[8,7,6-hi]indole-8-carboxylic acid (Mixture of Stereoisomers)

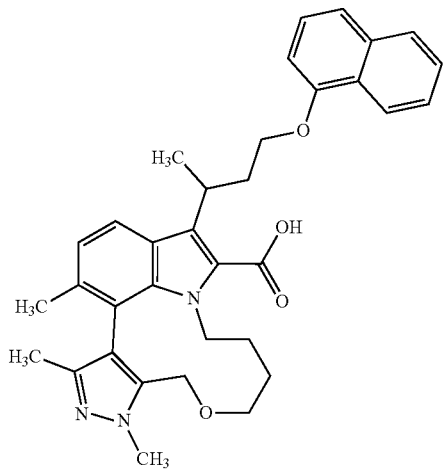 [SMILES: Cc1ccc2c(C(C)CCOc3cccc4ccccc34)c(C(=O)O)n3c2c1-c1c(C)nn(C)c1COCCCC3]

A mixture of ethyl 10,12,13-trimethyl-1-(4-(naphthalen-1-yloxy)butan-2-yl)-4,5,6,7,9,10-hexahydropyrazolo[4',3':9,10][1]oxa[6]azacycloundecino[8,7,6-hi]indole-2-carboxylate (mixture of stereoisomers; 108 mg; see Intermediate 447), methanol (25 ml), and aqueous solution of lithium hydroxide (2M, 4 ml) was heated to 55° C. for 74 hours, at which time additional aqueous solution of lithium hydroxide (2M, 2 ml) was added and the mixture was heated for an additional 24 hours. The mixture was diluted with ethyl acetate and aqueous hydrochloric acid (3M), the layers were separated, the organic phase was washed with saturated aqueous sodium chloride solution, and the combined aqueous phases were back extracted with ethyl acetate. The combined organic phases were dried over magnesium sulfate, insoluble materials were removed by filtration, and the filtrate was concentrated under reduced pressure. The residue was purified by flash chromatography on silica gel eluting with a gradient of ethyl acetate in hexanes (0-100%) to give the title compound as a colorless gum (56 mg) as a mixture of diastereomers.

LRMS (ESIneg) m/z=550 [M–H]⁻

$^1$H NMR (400 MHz, Chloroform-d) δ 8.34-8.01 (m, 1H), 7.86 (dd, J=18.0, 8.3 Hz, 1H), 7.76-7.66 (m, 1H), 7.38 (dddt, J=12.5, 7.0, 3.6, 1.8 Hz, 2H), 7.35-7.28 (m, 1H), 7.25-7.19 (m, 1H), 7.07 (dd, J=18.5, 8.3 Hz, 1H), 6.62 (dd, J=11.7, 7.5 Hz, 1H), 4.54 (dd, J=35.5, 13.3 Hz, 1H), 4.46-4.25 (m, 2H), 4.19-3.97 (m, 3H), 3.97-3.89 (m, 4H), 3.38 (ddt, J=95.1, 12.3, 6.1 Hz, 1H), 3.04-2.78 (m, 1H), 2.75-2.37 (m, 2H), 2.00 (d, J=7.0 Hz, 3H), 1.93 (d, J=8.1 Hz, 3H), 1.63 (dd, J=18.1, 7.1 Hz, 3H), 1.27 (tdd, J=16.9, 8.6, 3.7 Hz, 2H), 1.15-1.02 (m, 1H), 1.01-0.69 (m, 1H).

$^{13}$C NMR (101 MHz, CDCl3) δ 122.15, 122.19, 122.40, 127.45, 126.35, 124.94, 119.94, 77.16, 125.95, 122.40, 104.37, 58.40, 58.33, 42.63, 58.31, 28.65, 67.07, 58.33, 66.91, 42.60, 36.72, 66.28, 66.27, 36.25, 36.22, 20.87, 11.94, 21.32, 27.71, 27.64, 21.04, 20.96

The title compound was separated into single stereoisomers by preparative chiral HPLC (Method 1 first followed by method 2) to give isomer 1 (7.0 mg, see Example 257), isomer 2 (3.4 mg, see Example 258), isomer 3 (4.9 mg, see Example 259) and isomer 4 (1.3 mg, see Example 260).

Preparative chiral HPLC Method 1: Instrument: Labomatic HD5000, Labocord-5000; Gilson GX-241, Labcol Vario 4000, column: Chiralpak IF 5µ 250×30 mm; eluent A: hexane+0.1 Vol-% TFA (99%); eluent B: 2-propanol; Gradient: 20-50% B in 20 min; flow 40.0 ml/min; UV 254 nm.

Preparative chiral HPLC method 2: Instrument: Labomatic HD5000, Labocord-5000; Gilson GX-241, Labcol Vario 4000, column: Chiralpak AD-H 5µ 250×30 mm; eluent A: hexane+0.1 Vol-% TFA (99%); eluent B: 2-propanol; Gradient: 20-50% B in 20 min; flow 40.0 ml/min; UV 254 nm.

Analytical chiral HPLC method: Agilent HPLC 1260; column: Chiralpak IF 3µ 100×4.6 mm; eluent A: hexane+0.1 Vol-% TFA (99%); eluent B: 2-propanol; gradient: 20-50% B in 7 min; flow 1.4 ml/min; temperature: 25° C.; DAD 254 nm.

Example 257

1,3,4-trimethyl-7-[4-(naphthalen-1-yloxy)butan-2-yl]-1,10,11,12,13,15-hexahydropyrazolo[4',3':9,10][1,6]oxazacycloundecino[8,7,6-hi]indole-8-carboxylic acid (Stereoisomer 1)

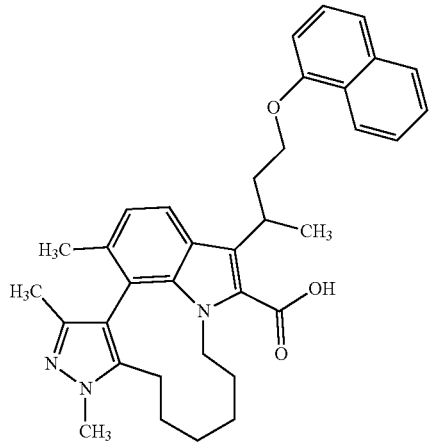 [SMILES: Cc1ccc2c(C(C)CCOc3cccc4ccccc34)c(C(=O)O)n3c2c1-c1c(C)nn(C)c1CCCCCC3]

For the preparation of the mixture of stereoisomers and the separation of the isomers see Example 256.

Analytical Chiral HPLC (method see Example 256): $R_t$=1.88 min.

LC-MS (Method 1): $R_t$=1.54 min; MS (ESIpos): m/z=553 [M+H]⁺

$^1$H-NMR (400 MHz, DMSO-d6) δ[ppm]: 0.629 (0.46), 0.748 (0.40), 0.767 (0.50), 0.783 (0.46), 0.967 (0.56), 1.067 (0.85), 1.076 (0.87), 1.107 (2.20), 1.136 (1.33), 1.144 (0.65), 1.154 (2.74), 1.173 (1.35), 1.232 (1.15), 1.349 (0.69), 1.484 (5.77), 1.501 (5.87), 1.741 (16.00), 1.759 (0.59), 1.919 (0.50), 1.939 (12.33), 2.399 (0.54), 2.416 (0.77), 2.433 (0.67), 2.518 (5.33), 2.523 (3.53), 2.749 (0.69), 2.760 (0.50), 2.766 (0.46), 2.778 (0.75), 2.912 (0.52), 2.931 (0.52), 3.136 (0.61), 3.148 (0.75), 3.165 (0.56), 3.821 (15.64), 3.850 (0.99), 3.857 (0.93), 3.880 (2.06), 3.914 (2.02), 4.017 (0.69), 4.025 (0.61), 4.033 (0.54), 4.041 (0.97), 4.057 (0.54), 4.073 (0.44), 4.097 (0.97), 4.114 (1.59), 4.130 (0.99), 4.138 (0.85), 4.190 (0.42), 4.202 (0.73), 4.214 (0.44), 4.237 (0.65), 4.520 (2.02), 4.553 (1.92), 6.684 (1.76), 6.702 (1.84), 7.074 (2.10), 7.095 (2.20), 7.266 (1.35), 7.287 (2.46), 7.306 (1.92), 7.336 (0.85), 7.339 (0.89), 7.357 (4.06), 7.377 (2.60), 7.447 (1.15), 7.450 (1.21), 7.464 (1.01), 7.467 (1.90), 7.470 (1.39), 7.484 (0.99), 7.487 (0.97), 7.781 (1.96), 7.801 (1.72), 7.846 (1.94), 7.867 (1.80), 7.880 (1.76), 7.901 (1.57).

Example 258

1,3,4-trimethyl-7-[4-(naphthalen-1-yloxy)butan-2-yl]-1,10,11,12,13,15-hexahydropyrazolo[4',3':9,10][1,6]oxazacycloundecino[8,7,6-hi]indole-8-carboxylic acid (Stereoisomer 2)

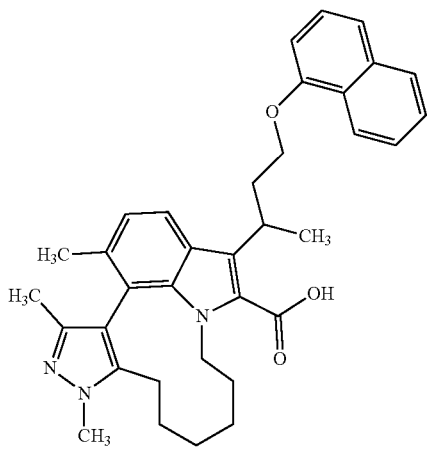 [SMILES: Cc1ccc2c(C(C)CCOc3cccc4ccccc34)c(C(=O)O)n3c2c1-c1c(C)nn(C)c1CCCCCC3]

For the preparation of the mixture of stereoisomers and the separation of the isomers see Example 256.

Analytical Chiral HPLC (method see Example 256): $R_t$=1.95 min.

LC-MS (Method 1): $R_t$=1.54 min; MS (ESIpos): m/z=553 [M+H]$^+$ $^1$H-NMR (400 MHz, CHLOROFORM-d) δ [ppm]: 0.000 (2.93), 0.792 (0.90), 0.809 (1.31), 0.825 (0.87), 0.962 (0.67), 1.042 (1.64), 1.139 (3.03), 1.149 (3.02), 1.184 (8.80), 1.205 (2.44), 1.214 (2.29), 1.263 (1.44), 1.357 (5.87), 1.400 (1.86), 1.483 (1.82), 1.500 (1.76), 1.537 (1.23), 1.564 (11.52), 1.581 (11.25), 1.785 (0.89), 1.835 (1.77), 1.872 (12.31), 1.913 (16.00), 2.013 (0.72), 2.030 (1.01), 2.068 (0.63), 2.105 (0.51), 2.362 (1.26), 2.380 (1.75), 2.396 (2.12), 2.414 (1.77), 2.430 (1.12), 2.448 (1.17), 2.462 (1.71), 2.484 (1.91), 2.497 (1.62), 2.519 (1.39), 2.943 (1.86), 3.420 (1.55), 3.562 (1.19), 3.904 (2.24), 3.922 (3.42), 3.945 (11.13), 3.971 (3.56), 3.995 (1.80), 4.010 (1.00), 4.215 (0.99), 4.232 (1.56), 4.254 (2.66), 4.272 (1.49), 4.286 (1.99), 4.365 (1.12), 4.401 (0.93), 4.501 (2.30), 4.535 (1.90), 6.555 (3.28), 6.574 (3.44), 6.921 (0.47), 6.928 (0.76), 6.977 (4.26), 6.998 (4.25), 7.168 (2.33), 7.207 (3.49), 7.239 (0.48), 7.260 (4.51), 7.281 (2.84), 7.311 (0.99), 7.323 (2.50), 7.330 (3.45), 7.339 (5.58), 7.347 (3.35), 7.355 (2.71), 7.368 (1.11), 7.396 (0.55), 7.408 (0.57), 7.451 (0.85), 7.647 (2.66), 7.653 (2.25), 7.662 (1.45), 7.671 (2.31), 7.685 (0.62), 7.705 (0.64), 7.774 (4.18), 7.795 (3.68), 8.176 (2.34), 8.194 (2.04), 8.200 (2.14).

Example 259

1,3,4-trimethyl-7-[4-(naphthalen-1-yloxy)butan-2-yl]-1,10,11,12,13,15-hexahydropyrazolo[4',3':9,10][1,6]oxazacycloundecino[8,7,6-hi]indole-8-carboxylic acid (Stereoisomer 3)

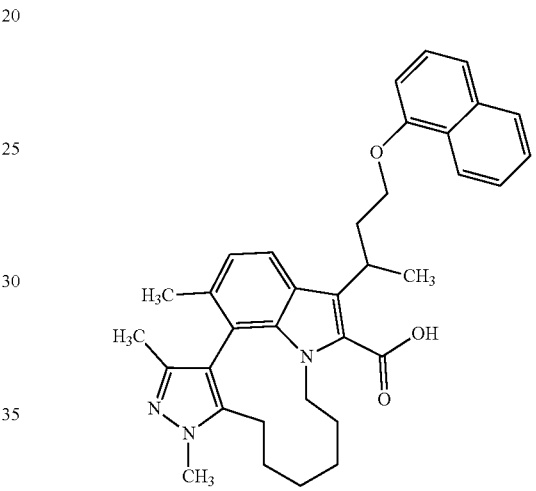

For the preparation of the mixture of stereoisomers and the separation of the isomers see Example 256.

Analytical Chiral HPLC (method see Example 256): $R_t$=2.91 min.

LC-MS (Method 1): $R_t$=1.54 min; MS (ESIpos): m/z=553 [M+H]$^+$ $^1$H-NMR (400 MHz, DMSO-d6) δ[ppm]: 0.631 (0.50), 0.769 (0.53), 1.068 (0.79), 1.107 (0.67), 1.136 (5.01), 1.154 (11.08), 1.173 (5.30), 1.230 (1.73), 1.256 (0.53), 1.349 (1.32), 1.482 (6.07), 1.500 (6.10), 1.741 (16.00), 1.762 (0.85), 1.884 (0.44), 1.907 (0.50), 1.937 (12.69), 2.332 (1.23), 2.336 (0.56), 2.397 (0.56), 2.413 (0.79), 2.430 (0.67), 2.455 (0.44), 2.518 (7.30), 2.523 (4.89), 2.678 (0.56), 2.748 (0.73), 2.760 (0.53), 2.777 (0.79), 2.893 (1.14), 2.911 (3.43), 2.929 (3.40), 2.948 (1.05), 3.138 (0.64), 3.152 (0.76), 3.167 (0.59), 3.821 (15.97), 3.847 (1.20), 3.857 (0.94), 3.868 (0.82), 3.882 (2.26), 3.915 (1.99), 4.015 (0.73), 4.024 (0.64), 4.040 (1.03), 4.054 (0.59), 4.069 (0.47), 4.092 (0.76), 4.104 (1.00), 4.118 (1.20), 4.126 (1.03), 4.142 (0.82), 4.209 (0.70), 4.220 (0.47), 4.231 (0.41), 4.244 (0.62), 4.521 (2.08), 4.554 (1.96), 6.682 (1.82), 6.701 (1.90), 7.069 (1.99), 7.090 (2.08), 7.266 (1.35), 7.286 (2.49), 7.305 (1.96), 7.336 (0.91), 7.340 (0.94), 7.357 (4.37), 7.378 (2.78), 7.447 (1.17), 7.450 (1.20), 7.468 (1.88), 7.470 (1.38), 7.485 (1.00), 7.487 (0.94), 7.782 (2.02), 7.802 (1.82), 7.839 (1.76), 7.860 (1.64), 7.883 (1.79), 7.904 (1.61).

Example 260

1,3,4-trimethyl-7-[4-(naphthalen-1-yloxy)butan-2-yl]-1,10,11,12,13,15-hexahydropyrazolo[4',3':9,10][1,6]oxazacycloundecino[8,7,6-hi]indole-8-carboxylic acid (Stereoisomer 4)

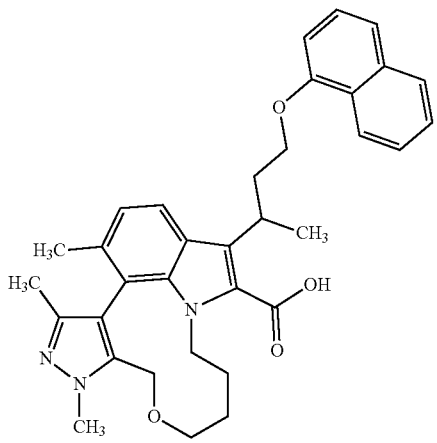 [SMILES: Cc1ccc2c(C(C)CCOc3cccc4ccccc34)c(C(=O)O)n3c2c1-c1c(C)nn(C)c1COCCCC3]

For the preparation of the mixture of stereoisomers and the separation of the isomers see Example 256.

Analytical Chiral HPLC (method see Example 256): $R_t$=3.97 min.

LC-MS (Method 1): $R_t$=1.54 min; MS (ESIpos): m/z=553 [M+H]$^+$ $^1$H-NMR (400 MHz, CHLOROFORM-d) δ [ppm]: 0.000 (7.54), 0.792 (1.30), 0.810 (2.17), 0.827 (1.06), 1.059 (1.16), 1.184 (14.55), 1.206 (3.47), 1.215 (4.29), 1.263 (2.48), 1.358 (12.60), 1.412 (1.35), 1.485 (1.35), 1.513 (1.45), 1.531 (1.45), 1.563 (7.06), 1.581 (7.06), 1.829 (1.69), 1.846 (1.78), 1.909 (16.00), 2.024 (2.14), 2.061 (2.46), 2.106 (2.00), 2.359 (1.06), 2.378 (1.28), 2.393 (1.37), 2.412 (1.20), 2.478 (1.13), 2.491 (0.96), 2.797 (0.41), 2.969 (0.99), 3.422 (0.96), 3.905 (2.17), 3.973 (1.59), 4.013 (5.11), 4.200 (0.72), 4.217 (0.80), 4.251 (1.23), 4.283 (1.30), 4.362 (0.65), 4.508 (1.20), 4.542 (1.08), 6.557 (1.71), 6.576 (1.73), 6.922 (1.04), 6.929 (1.42), 6.981 (2.34), 7.002 (2.43), 7.178 (1.76), 7.217 (1.71), 7.236 (0.43), 7.271 (2.41), 7.291 (1.49), 7.332 (0.65), 7.347 (2.19), 7.357 (2.75), 7.366 (2.27), 7.382 (0.58), 7.451 (1.66), 7.661 (1.47), 7.667 (1.04), 7.685 (1.18), 7.788 (2.46), 7.809 (2.10), 8.167 (1.13), 8.192 (1.20).

Example 261

3-ethyl-7-{4-[(6-fluoronaphthalen-1-yl)oxy]butan-2-yl}-1,4-dimethyl-1,10,11,12,13,15-hexahydropyrazolo[4',3':9,10][1,6]oxazacycloundecino[8,7,6-hi]indole-8-carboxylic acid (Mixture of Stereoisomers)

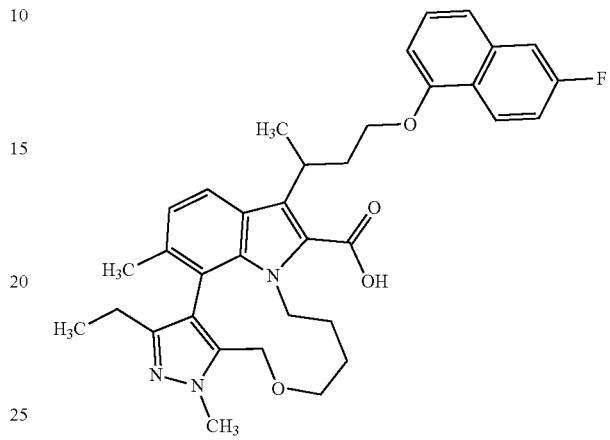

A mixture of ethyl 12-ethyl-1-(4-((6-fluoronaphthalen-1-yl)oxy)butan-2-yl)-10,13-dimethyl-4,5,6,7,9,10-hexahydropyrazolo[4',3':9,10][1]oxa[6]azacycloundecino[8,7,6-hi]indole-2-carboxylate (mixture of stereoisomers; 158 mg; see Intermediate 451), ethanol (5 ml), and aqueous solution of lithium hydroxide (2M, 5 ml) was heated to 80° C. for 17 hours; volatiles were removed, and the residue was partitioned between ethyl acetate and aqueous hydrochloric acid (3M). The layers were separated and the aqueous phase was extracted with ethyl acetate, the combined organic layers were washed with saturated aqueous sodium chloride solution and dried over magnesium sulfate. Insoluble materials were removed by filtration, and the residue was adsorbed onto celite. The residue was purified by flash chromatography on silica gel eluting with a gradient ethyl acetate in hexanes (50-100%) to give the title compound as an off white solid as a mixture of diasteromers (102 mg) as an off white solid.

LRMS (ESIneg) m/z=582 [M–H]$^−$

Less polar pair of diasteromers $^1$H NMR (400 MHz, Chloroform-d) δ 8.07 (dd, J=9.2, 5.8 Hz, 1H), 7.89 (d, J=8.3 Hz, 1H), 7.34 (dd, J=10.0, 2.6 Hz, 1H), 7.31-7.21 (m, 3H), 7.17-6.99 (m, 2H), 6.62-6.50 (m, 1H), 4.53 (d, J=13.3 Hz, 1H), 4.47-4.25 (m, 2H), 4.23-4.02 (m, 4H), 3.97 (s, 3H), 3.41-3.25 (m, 1H), 2.92 (dt, J=11.7, 7.0 Hz, 1H), 2.66 (ddt, J=11.6, 9.8, 5.8 Hz, 1H), 2.51 (dq, J=13.1, 6.3 Hz, 1H), 2.31 (q, J=7.6 Hz, 2H), 2.07 (s, 1H), 2.04 (s, 3H), 1.63 (d, J=7.1 Hz, 3H), 1.28 (t, J=7.1 Hz, 1H), 1.24 (d, J=2.9 Hz, 0H), 1.17-1.06 (m, 0H), 1.01 (t, J=7.6 Hz, 3H), 0.97-0.88 (m, 0H), 0.77 (dt, J=14.4, 7.2 Hz, 1H);

$^{13}$C NMR (101 MHz, CDCl3) δ 125.03, 122.14, 110.33, 77.16, 127.24, 118.92, 122.23, 114.77, 103.46, 57.99, 42.56, 28.52, 58.00, 66.84, 42.58, 36.56, 65.82, 65.85, 36.01, 35.98, 20.18, 20.76, 21.12, 27.52, 27.49, 13.11, 20.75, 20.73;

More polar pair of diasteromers $^1$H NMR (400 MHz, Chloroform-d) δ 8.27 (dd, J=9.3, 5.8 Hz, 1H), 7.85 (d, J=8.3 Hz, 1H), 7.33 (dt, J=10.0, 2.2 Hz, 1H), 7.31-7.22 (m, 2H), 7.20-7.12 (m, 1H), 7.08 (t, J=8.3 Hz, 1H), 6.57 (dt, J=6.5, 3.3 Hz, 1H), 4.57 (dd, J=28.3, 13.4

Hz, 1H), 4.50-4.40 (m, 1H), 4.40-4.26 (m, 2H), 4.20-4.01 (m, 2H), 3.99 (s, 4H), 3.53 (dt, J=12.3, 6.5 Hz, 1H), 3.08-2.95 (m, 1H), 2.70-2.53 (m, 1H), 2.47 (dq, J=13.6, 6.9 Hz, 1H), 2.30 (p, J=7.9 Hz, 2H), 2.03 (d, J=7.0 Hz, 3H), 1.66 (d, J=7.1 Hz, 3H), 1.53-1.38 (m, 1H), 1.30-1.19 (m, 2H), 1.14 (dd, J=14.2, 7.8 Hz, 1H), 0.99 (dt, J=11.9, 7.6 Hz, 3H);

$^{13}$C NMR (101 MHz, CDCl3) δ 124.93, 121.97, 110.32, 77.16, 127.30, 119.06, 114.91, 122.31, 103.73, 58.19, 42.58, 58.13, 28.18, 42.57, 66.76, 66.74, 36.63, 65.67, 65.72, 35.92, 35.97, 20.26, 20.79, 21.03, 27.61, 21.07, 27.58, 20.99, 13.03.

The title compound was separated into single stereoisomers by preparative chiral HPLC (Method 1 first followed by method 2) to give isomer 1 (12.7 mg, see Example 262), isomer 2 (20.2 mg, see Example 263), isomer 3 (11.5 mg, see Example 264) and isomer 4 (16.5 mg, see Example 265).

Preparative chiral HPLC Method 1: Instrument: Labomatic HD5000, Labocord-5000; Gilson GX-241, Labcol Vario 4000, column: Chiralpak IF 5μ 250×30 mm; eluent A: hexane+0.1 Vol-% TFA (99%); eluent B: 2-propanol; Gradient: 10-30% B in 20 min; flow 40.0 ml/min; UV 254 nm.

Preparative chiral HPLC method 2: Instrument: Labomatic HD5000, Labocord-5000; Gilson GX-241, Labcol Vario 4000, column: Chiralpak AD-H 5μ 250×30 mm; eluent A: hexane+0.1 Vol-% TFA (99%); eluent B: 2-propanol; Gradient: 5-30% B in 20 min; flow 40.0 ml/min; UV 254 nm.

Analytical chiral HPLC method: Agilent HPLC 1260; column: Chiralpak IF 3μ 100×4.6 mm; eluent A: hexane+0.1 Vol-% TFA (99%); eluent B: 2-propanol; gradient: 10-30% B in 7 min; flow 1.4 ml/min; temperature: 25° C.; DAD 254 nm.

Example 262

3-ethyl-7-{4-[(6-fluoronaphthalen-1-yl)oxy]butan-2-yl}-1,4-dimethyl-1,10,11,12,13,15-hexahydropyrazolo[4',3':9,10][1,6]oxazacycloundecino[8,7,6-hi]indole-8-carboxylic acid (Stereoisomer 1)

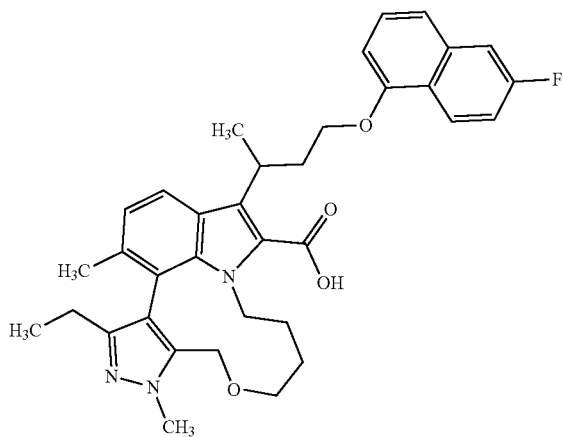 [SMILES: CCc1nn(C)c2c1-c1c(C)ccc3c(C(C)CCOc4cccc5cc(F)ccc45)c(C(=O)O)n(c13)CCCCOC2]

For the preparation of the mixture of stereoisomers and the separation of the isomers see Example 261.

Analytical Chiral HPLC (method see Example 261): $R_t$=2.35 min.

LC-MS (Method 1): $R_t$=1.58 min; MS (ESIpos): m/z=584 [M+H]$^+$ $^1$H-NMR (400 MHz, DMSO-d6) δ[ppm]: 0.850 (3.72), 0.869 (8.40), 0.888 (3.80), 1.013 (1.03), 1.107 (16.00), 1.136 (2.05), 1.154 (4.20), 1.172 (2.12), 1.232 (0.76), 1.482 (4.53), 1.499 (4.65), 1.946 (9.87), 2.055 (0.96), 2.062 (0.42), 2.074 (2.79), 2.093 (2.69), 2.112 (0.81), 2.396 (0.40), 2.413 (0.61), 2.429 (0.50), 2.518 (3.92), 2.523 (2.74), 2.727 (0.53), 2.756 (0.56), 2.902 (0.51), 2.920 (0.67), 2.933 (0.65), 2.951 (0.50), 3.171 (0.45), 3.183 (0.58), 3.199 (0.45), 3.834 (12.26), 3.867 (0.72), 3.882 (0.59), 3.895 (1.49), 3.928 (1.45), 4.042 (0.53), 4.058 (0.84), 4.071 (0.72), 4.084 (1.15), 4.100 (0.92), 4.107 (0.84), 4.124 (0.68), 4.169 (0.65), 4.204 (0.54), 4.530 (1.54), 4.564 (1.45), 6.654 (1.00), 6.660 (1.03), 6.671 (0.96), 6.676 (1.04), 7.078 (1.87), 7.099 (1.98), 7.174 (0.61), 7.181 (0.72), 7.197 (0.96), 7.204 (1.04), 7.219 (0.64), 7.225 (0.72), 7.308 (0.42), 7.329 (1.54), 7.346 (3.19), 7.363 (0.44), 7.562 (1.09), 7.568 (1.17), 7.588 (1.12), 7.594 (1.14), 7.849 (1.99), 7.870 (1.76), 7.885 (1.00), 7.900 (1.03), 7.908 (0.98), 7.923 (0.93).

Example 263

3-ethyl-7-{4-[(6-fluoronaphthalen-1-yl)oxy]butan-2-yl}-1,4-dimethyl-1,10,11,12,13,15-hexahydropyrazolo[4',3':9,10][1,6]oxazacycloundecino[8,7,6-hi]indole-8-carboxylic acid (Stereoisomer 2)

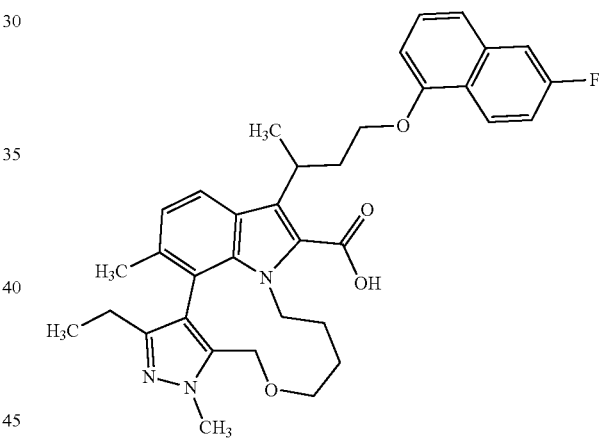

For the preparation of the mixture of stereoisomers and the separation of the isomers see Example 261.

Analytical Chiral HPLC (method see Example 261): $R_t$=2.48 min.

LC-MS (Method 1): $R_t$=1.58 min; MS (ESIpos): m/z=584 [M+H]$^+$ $^1$H-NMR (400 MHz, DMSO-d6) δ[ppm]: 0.797 (2.33), 0.816 (5.49), 0.835 (2.54), 1.055 (0.55), 1.071 (0.58), 1.084 (0.52), 1.107 (16.00), 1.136 (2.51), 1.154 (5.53), 1.173 (2.91), 1.194 (0.70), 1.232 (0.59), 1.504 (2.98), 1.522 (2.97), 1.925 (6.37), 2.016 (0.44), 2.033 (1.09), 2.036 (1.14), 2.052 (1.08), 2.055 (1.07), 2.062 (0.43), 2.323 (0.50), 2.327 (0.76), 2.332 (0.58), 2.381 (0.41), 2.397 (0.42), 2.518 (2.84), 2.523 (1.97), 2.665 (0.47), 2.669 (0.65), 2.673 (0.47), 2.902 (0.69), 2.918 (0.74), 2.921 (0.87), 2.933 (0.85), 2.951 (0.67), 3.363 (0.45), 3.867 (7.93), 3.925 (0.67), 3.943 (0.73), 4.006 (0.53), 4.087 (0.42), 4.138 (0.88), 4.172 (0.96), 4.223 (0.42), 4.624 (1.03), 4.658 (0.94), 6.710 (0.80), 6.726 (0.85), 7.010 (1.18), 7.032 (1.25), 7.313 (0.41), 7.319 (0.47), 7.335 (0.98), 7.342 (0.77), 7.354 (1.05), 7.364 (0.52), 7.373 (0.88), 7.391 (1.34), 7.411 (0.53), 7.608 (0.71), 7.615 (0.74), 7.634 (0.72), 7.641 (0.71), 7.772 (1.27), 7.792 (1.12), 8.129 (0.65), 8.143 (0.70), 8.152 (0.69), 8.166 (0.67).

Example 264

3-ethyl-7-{4-[(6-fluoronaphthalen-1-yl)oxy]butan-2-yl}-1,4-dimethyl-1,10,11,12,13,15-hexahydropyrazolo[4',3':9,10][1,6]oxazacycloundecino[8,7,6-hi]indole-8-carboxylic acid (Stereoisomer 3)

Example 265

3-ethyl-7-{4-[(6-fluoronaphthalen-1-yl)oxy]butan-2-yl}-1,4-dimethyl-1,10,11,12,13,15-hexahydropyrazolo[4',3':9,10][1,6]oxazacycloundecino[8,7,6-hi]indole-8-carboxylic acid (Stereoisomer 4)

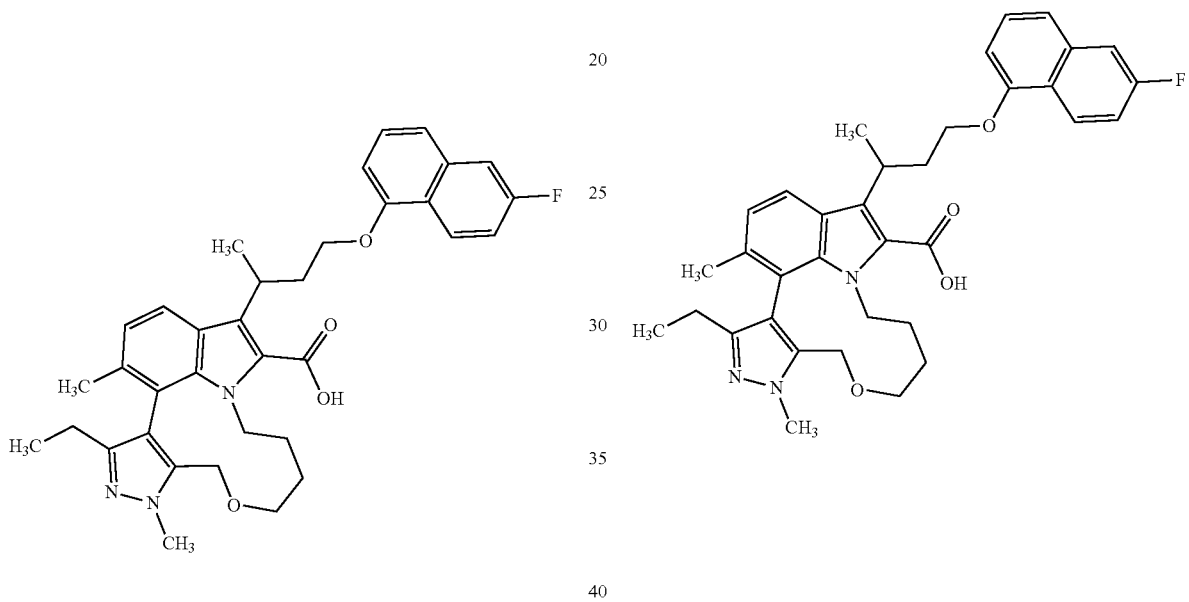

For the preparation of the mixture of stereoisomers and the separation of the isomers see Example 261.

Analytical Chiral HPLC (method see Example 261): $R_t$=3.23 min.

LC-MS (Method 1): $R_t$=1.58 min; MS (ESIpos): m/z=584 [M+H]$^+$ $^1$H-NMR (400 MHz, DMSO-d6) δ[ppm]: 0.850 (1.62), 0.860 (0.43), 0.869 (3.54), 0.888 (1.64), 0.967 (1.02), 1.013 (0.49), 1.020 (0.47), 1.026 (0.42), 1.085 (0.53), 1.107 (16.00), 1.136 (0.97), 1.144 (0.73), 1.154 (1.92), 1.173 (0.95), 1.232 (0.47), 1.482 (1.90), 1.499 (1.85), 1.947 (4.00), 2.055 (0.47), 2.062 (0.64), 2.069 (0.62), 2.075 (1.17), 2.094 (1.16), 2.518 (2.26), 2.523 (1.52), 3.658 (1.53), 3.864 (0.42), 3.873 (0.50), 3.896 (0.70), 3.929 (0.67), 4.084 (0.50), 4.100 (0.41), 4.531 (0.61), 4.565 (0.56), 6.677 (0.41), 7.078 (0.74), 7.099 (0.80), 7.204 (0.44), 7.329 (0.58), 7.347 (1.26), 7.562 (0.42), 7.568 (0.45), 7.588 (0.43), 7.594 (0.44), 7.849 (0.77), 7.870 (0.71).

For the preparation of the mixture of stereoisomers and the separation of the isomers see Example 261.

Analytical Chiral HPLC (method see Example 261): $R_t$=4.76 min.

LC-MS (Method 1): $R_t$=1.58 min; MS (ESIpos): m/z=584 [M+H]$^+$ $^1$H-NMR (400 MHz, DMSO-d6) δ[ppm]: 0.783 (0.76), 0.797 (1.92), 0.802 (0.65), 0.816 (4.36), 0.835 (2.09), 0.851 (0.52), 0.859 (0.49), 0.862 (0.48), 0.869 (0.54), 0.967 (0.79), 1.021 (0.70), 1.050 (0.52), 1.054 (0.52), 1.071 (0.54), 1.085 (1.35), 1.107 (16.00), 1.136 (1.14), 1.144 (0.90), 1.154 (2.22), 1.160 (0.55), 1.172 (1.29), 1.194 (0.63), 1.201 (0.65), 1.214 (0.43), 1.232 (0.49), 1.268 (0.47), 1.285 (0.75), 1.297 (0.43), 1.504 (2.59), 1.522 (2.52), 1.532 (0.43), 1.925 (5.21), 2.033 (0.87), 2.036 (0.91), 2.046 (0.55), 2.052 (0.90), 2.055 (1.03), 2.058 (1.17), 2.062 (0.91), 2.069 (0.44), 2.396 (0.41), 2.518 (3.70), 2.523 (2.36), 3.363 (0.47), 3.378 (0.45), 3.867 (6.41), 3.880 (0.60), 3.925 (0.73), 3.931 (0.48), 3.943 (0.61), 4.005 (0.43), 4.086 (0.44), 4.138 (0.74), 4.172 (0.81), 4.624 (0.84), 4.658 (0.75), 6.710 (0.63), 6.726 (0.66), 7.011 (0.95), 7.032 (1.02), 7.335 (0.76), 7.341 (0.63), 7.354 (0.84), 7.364 (0.43), 7.373 (0.70), 7.391 (0.48), 7.411 (0.42), 7.608 (0.57), 7.615 (0.58), 7.634 (0.57), 7.641 (0.57), 7.772 (1.02), 7.792 (0.91), 8.128 (0.50), 8.143 (0.52), 8.152 (0.52), 8.166 (0.49).

Example 266

(rac)-3-ethyl-7-{3-[(6-fluoronaphthalen-1-yl)oxy]propyl}-1,4-dimethyl-1,10,11,12,13,15-hexahydropyrazolo[4',3':9,10][1,6]oxazacycloundecino[8,7,6-hi]indole-8-carboxylic acid

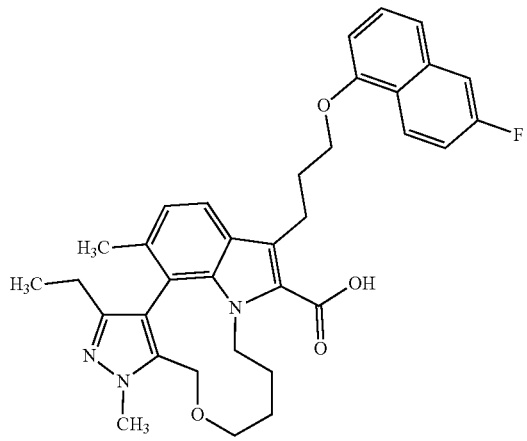 [SMILES: CCc1nn(C)c2c1-c1c(C)ccc3c(CCCOc4cccc5cc(F)ccc45)c(C(=O)O)n(c13)CCCCOC2]

A mixture of (rac)-ethyl 12-ethyl-1-(3-((6-fluoronaphthalen-1-yl)oxy)propyl)-10,13-dimethyl-4,5,6,7,9,10-hexahydropyrazolo[4',3':9,10][1]oxa[6]azacycloundecino[8,7,6-hi]indole-2-carboxylate (150 mg, 250 µmol; see Intermediate 471) and aqueous solution of lithium hydroxide (2 M, 5 ml, 10.0 mmol) in ethanol (5 mL) was heated at 70° C. for 23 hours. The reaction mixture was cooled to room temperature and volatiles were removed under reduced pressure. The residue was diluted with water, acidified to pH 2 with aqueous hydrochloric acid (1 M) and extracted three times with ethyl acetate. The combined organic extracts were dried over magnesium sulfate, solids were removed by filtration and volatiles were removed under reduced pressure. The residue was purified by flash chromatography on silica gel eluting with a gradient of ethyl acetate in hexanes (25-100%) to give the title compound (130 mg).

MS (ESIpos): m/z=570.4 [M+H]$^+$ $^1$H NMR (400 MHz, Chloroform-d) δ 8.35 (dd, J=9.2, 5.8 Hz, 1H), 7.65 (d, J=8.2 Hz, 1H), 7.41-7.26 (m, 3H), 7.21 (td, J=8.8, 2.6 Hz, 1H), 7.03 (d, J=8.2 Hz, 1H), 6.68 (dd, J=6.9, 1.8 Hz, 1H), 4.60 (dd, J=13.3, 7.3 Hz, 2H), 4.34 (d, J=13.4 Hz, 1H), 4.23-4.05 (m, 4H), 4.00 (s, 3H), 3.46 (dddd, J=25.7, 20.8, 13.4, 7.2 Hz, 3H), 2.98 (ddd, J=12.5, 8.5, 4.8 Hz, 1H), 2.42-2.23 (m, 4H), 2.05 (s, 1H), 1.99 (s, 3H), 1.26 (dq, J=12.3, 5.6, 5.1 Hz, 5H), 1.09 (dq, J=14.9, 8.2 Hz, 1H), 0.98 (t, J=7.6 Hz, 3H).

$^{13}$C NMR (101 MHz, CDCl$_3$) δ 171.34, 166.96, 162.50, 160.06, 155.11, 152.02, 139.91, 137.82, 136.63, 135.69, 135.60, 129.05, 127.46, 126.58, 125.07, 124.98, 124.21, 123.02, 122.83, 120.57, 119.40, 119.35, 117.44, 115.82, 115.29, 115.04, 110.73, 110.53, 103.98, 103.96, 77.48, 77.36, 77.16, 76.84, 67.82, 65.81, 60.55, 58.09, 42.88, 36.76, 30.66, 29.83, 27.96, 22.28, 21.16, 21.05, 20.89, 20.32, 14.32, 13.23.

The title compound was separated into enantiomers by preparative chiral HPLC to give enantiomer 1 (25.3 mg, see Example 267) and enantiomer 2 (26.1 mg, see Example 268).

Preparative chiral HPLC method: Instrument: Labomatic HD5000, Labocord-5000; Gilson GX-241, Labcol Vario 4000, column: Chiralpak ID 5µ 250×30 mm; eluent A: hexane+0.1 Vol-% TFA (99%); eluent B: 2-propanol; Gradient: 20-50% B in 20 min; flow 40.0 ml/min; UV 280 nm.

Analytical chiral HPLC method: Agilent HPLC 1260; column: Chiralpak ID 3µ 100×4.6 mm; eluent A: hexane+ 0.1 Vol-% TFA (99%); eluent B: 2-propanol; gradient: 20-50% B in 7 min; flow 1.4 ml/min; temperature: 25° C.; DAD 280 nm.

Example 267

(+)-3-ethyl-7-{3-[(6-fluoronaphthalen-1-yl)oxy]propyl}-1,4-dimethyl-1,10,11,12,13,15-hexahydropyrazolo[4',3':9,10][1,6]oxazacycloundecino[8,7,6-hi]indole-8-carboxylic acid (Enantiomer 1)

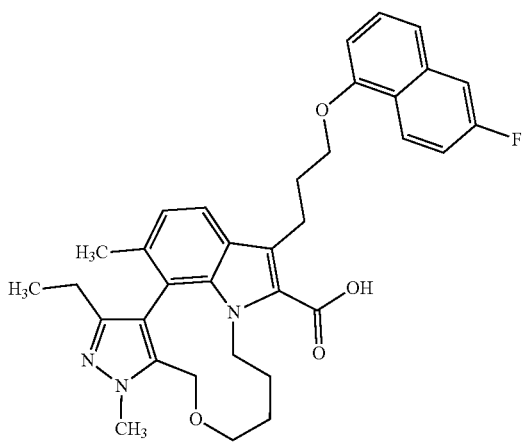 [SMILES: CCc1nn(C)c2c1-c1c(C)ccc3c(CCCOc4cccc5cc(F)ccc45)c(C(=O)O)n(c13)CCCCOC2]

For the preparation of the racemic title compound and separation into its enantiomers see Example 266.

Analytical Chiral HPLC (method see Example 266): R$_t$=1.93 min.

Specific optical rotation (Method O1): +61.0° (c=1.0000 g/100 ml in DMSO)

LC-MS (Method 1): R$_t$=1.59 min; MS (ESIpos): m/z=571 [M+H]$^+$ $^1$H-NMR (400 MHz, DMSO-d6) δ[ppm]: 0.835 (1.77), 0.854 (4.07), 0.872 (1.84), 0.967 (0.62), 1.107 (16.00), 1.144 (0.43), 1.230 (0.60), 1.922 (4.94), 2.054 (0.45), 2.073 (1.39), 2.092 (1.35), 2.111 (0.42), 2.180 (0.40), 2.198 (0.59), 2.214 (0.43), 2.518 (2.21), 2.522 (1.41), 3.267 (0.43), 3.300 (0.44), 3.768 (1.06), 4.119 (0.71), 4.153 (0.79), 4.175 (0.54), 4.190 (1.08), 4.205 (0.53), 4.630 (0.79), 4.664 (0.71), 6.849 (0.50), 6.856 (0.51), 6.864 (0.46), 6.871 (0.53), 7.005 (0.96), 7.025 (1.02), 7.378 (0.52), 7.385 (0.56), 7.407 (0.44), 7.426 (0.91), 7.434 (1.06), 7.440 (2.24), 7.620 (1.09), 7.641 (1.18), 7.649 (0.65), 7.668 (0.59), 7.675 (0.59), 8.253 (0.50), 8.269 (0.54), 8.277 (0.53), 8.291 (0.50).

Example 268

(−)-3-ethyl-7-{3-[(6-fluoronaphthalen-1-yl)oxy]propyl}-1,4-dimethyl-1,10,11,12,13,15-hexahydropyrazolo[4',3':9,10][1,6]oxazacycloundecino[8,7,6-hi]indole-8-carboxylic acid (Enantiomer 2)

For the preparation of the racemic title compound and separation into its enantiomers see Example 266.

Analytical Chiral HPLC (method see Example 266): $R_t$=4.96 min.

Specific optical rotation (Method O1): −56.0° (c=1.0000 g/100 ml in DMSO)

LC-MS (Method 1): $R_t$=1.59 min; MS (ESIpos): m/z=571 [M+H]$^+$ $^1$H-NMR (400 MHz, DMSO-d6) δ[ppm]: 0.835 (1.86), 0.854 (4.16), 0.872 (1.91), 0.967 (0.71), 1.107 (16.00), 1.144 (0.49), 1.230 (0.69), 1.922 (5.28), 2.054 (0.50), 2.073 (1.48), 2.092 (1.44), 2.111 (0.45), 2.180 (0.47), 2.197 (0.68), 2.214 (0.48), 2.522 (1.19), 3.267 (0.49), 3.300 (0.49), 3.871 (6.38), 4.119 (0.77), 4.153 (0.86), 4.175 (0.62), 4.190 (1.20), 4.205 (0.59), 4.630 (0.85), 4.663 (0.77), 6.849 (0.54), 6.855 (0.56), 6.864 (0.51), 6.871 (0.56), 7.005 (1.02), 7.025 (1.09), 7.378 (0.56), 7.385 (0.61), 7.407 (0.46), 7.425 (1.00), 7.434 (1.19), 7.440 (2.34), 7.620 (1.15), 7.641 (1.34), 7.649 (0.70), 7.668 (0.65), 7.675 (0.62), 8.253 (0.54), 8.269 (0.58), 8.277 (0.57), 8.291 (0.53).

Example 269

(rac)-1-(3-(4-chloro-3,5-dimethylphenoxy)propyl)-12-ethyl-10,13-dimethyl-4,5,6,7,9,10-hexahydropyrazolo[4',3':9,10][1]oxa[6]azacycloundecino[8,7,6-hi]indole-2-carboxylic acid

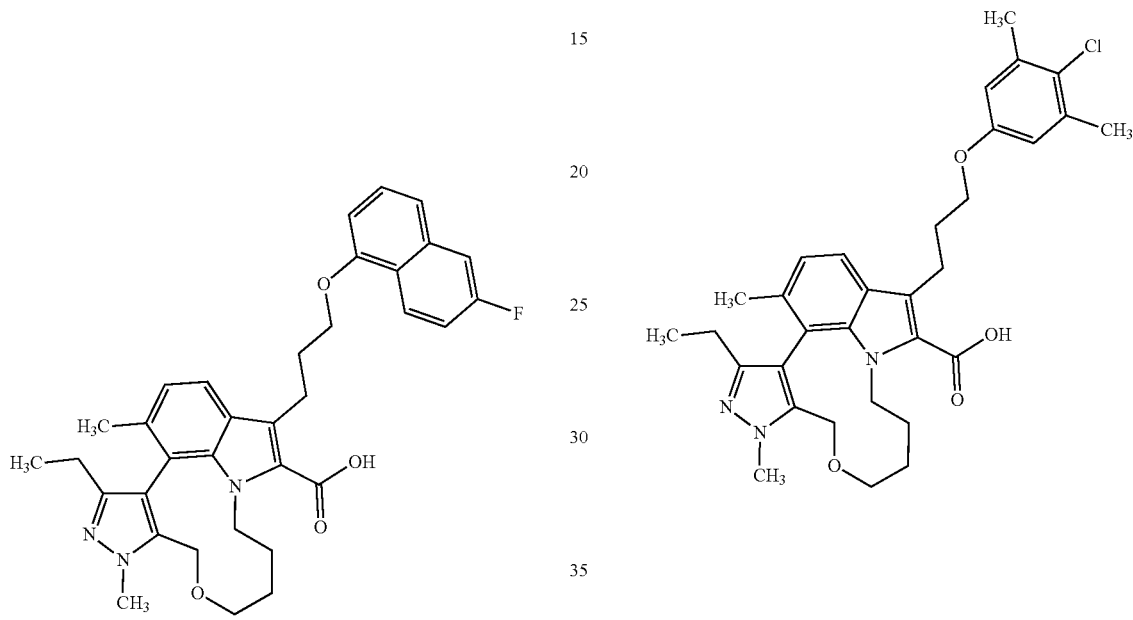

A mixture of (rac)-ethyl 1-(3-(4-chloro-3,5-dimethylphenoxy)propyl)-12-ethyl-10,13-dimethyl-4,5,6,7,9,10-hexahydropyrazolo[4',3':9,10][1]oxa[6]azacycloundecino[8,7,6-hi]indole-2-carboxylate (260 mg, 439 μmol, see Intermediate 473) and aqueous solution of lithium hydroxide (2 M, 8.75 mL, 17.5 mmol) in ethanol (9 mL) was heated at 70° C. for 48 hours. The reaction mixture was cooled to room temperature and volatiles were removed under reduced pressure. The mixture was diluted with water, acidified to pH 2 with aqueous hydrochloric acid (1 M) and extracted three times with ethyl acetate. The combined organic extracts were dried over magnesium sulfate, solids were removed by filtration and volatiles were removed under reduced pressure. The residue was purified by flash chromatography on silica gel eluting with a gradient of ethyl acetate in hexanes (25-100%) to give the title compound (159 mg, 282 μmol).

LRMS (ESIpos): m/z=564.5 [M+H]$^+$ $^1$H NMR (400 MHz, Chloroform-d) δ 9.61 (s, 1H), 7.59 (d, J=8.2 Hz, 1H), 7.01 (d, J=8.2 Hz, 1H), 6.58 (s, 2H), 4.59 (dd, J=16.0, 13.6 Hz, 2H), 4.32 (d, J=13.4 Hz, 1H), 4.08 (q, J=7.2 Hz, 10H), 3.97 (s, 4H), 3.56-3.44 (m, 1H), 3.29 (ddp, J=20.7, 13.6, 7.3 Hz, 2H), 2.96 (ddd, J=11.7, 7.8, 4.6 Hz, 1H), 2.33-2.21 (m, 2H), 2.22-2.10 (m, 2H), 2.02 (d, J=2.7 Hz, 0H), 2.00 (s, 13H), 1.96 (s, 3H), 1.50 (s, 2H), 1.32-1.15 (m, 22H), 1.09 (dd, J=4.9, 2.4 Hz, 0H), 0.99-0.89 (m, 3H), 0.83 (dtd, J=12.2, 6.4, 1.8 Hz, 6H).

Example 270

(rac)-12-ethyl-10,13-dimethyl-1-(3-((5,6,7,8-tetrahydronaphthalen-1-yl)oxy)propyl)-4,5,6,7,9,10-hexahydropyrazolo[4',3':9,10][1]oxa[6]azacycloundecino[8,7,6-hi]indole-2-carboxylic acid

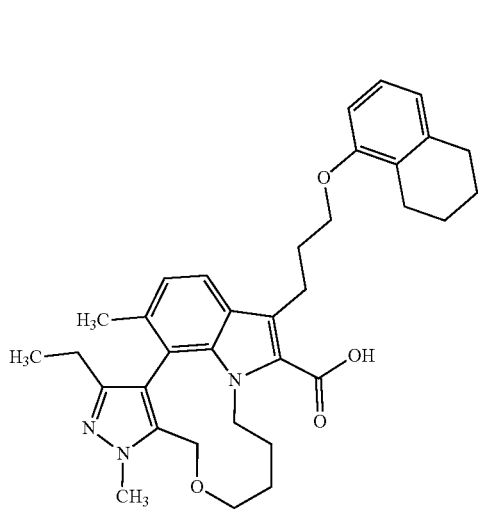 [SMILES: CCc1nn(C)c2c1-c1c(C)ccc3c(CCCOc4cccc5c4CCCC5)c(C(=O)O)n(c13)CCCCOC2]

A mixture of (rac)-ethyl 12-ethyl-10,13-dimethyl-1-(3-((5,6,7,8-tetrahydronaphthalen-1-yl)oxy)propyl)-4,5,6,7,9,10-hexahydropyrazolo[4',3':9,10][1]oxa[6]azacycloundecino[8,7,6-hi]indole-2-carboxylate (200 mg, 342 µmol; see Intermediate 472) and aqueous solution of lithium hydroxide (2 M, 6.80 mL) in ethanol (7 mL) was heated at 70° C. for 45 hours. The reaction mixture was cooled to room temperature and volatiles were removed under reduced pressure. The residue was diluted with water, acidified to pH 2 with aqueous hydrochloric acid (1 M) and extracted three times with ethyl acetate. The combined organic extracts were dried over magnesium sulfate, solids were removed by filtration and the volatiles were removed under reduced pressure. The residue was purified by flash chromatography on silica gel eluting with a gradient of ethyl acetate in hexanes (25-100%) to give the title compound (150 mg, 269 µmol).

LRMS (ESIpos): m/z=556.5 [M+H]$^+$ $^1$H NMR (400 MHz, Chloroform-d) δ 7.65 (d, J=8.2 Hz, 1H), 7.07 (d, J=8.2 Hz, 1H), 7.02 (t, J=7.9 Hz, 1H), 6.68 (d, J=7.7 Hz, 1H), 6.61 (d, J=8.0 Hz, 1H), 4.63 (dd, J=18.0, 13.7 Hz, 2H), 4.36 (d, J=13.4 Hz, 1H), 4.13 (q, J=7.2 Hz, 1H), 4.05 (t, J=6.2 Hz, 2H), 4.01 (s, 3H), 3.55 (dt, J=13.2, 6.7 Hz, 1H), 3.46-3.27 (m, 2H), 3.05-2.94 (m, 1H), 2.76 (q, J=5.9 Hz, 4H), 2.31 (q, J=7.6 Hz, 2H), 2.29-2.16 (m, 2H), 2.05 (s, 2H), 2.00 (s, 3H), 1.86-1.70 (m, 4H), 1.63-1.46 (m, 1H), 1.27 (t, J=7.1 Hz, 2H), 1.20-1.06 (m, 1H), 0.99 (t, J=7.6 Hz, 3H).

Example 271

3-ethyl-1,4-dimethyl-7-[4-(naphthalen-1-yloxy)butan-2-yl]-1,10,11,12,13,15-hexahydropyrazolo[4',3':9,10][1,6]oxazacycloundecino[8,7,6-hi]indole-8-carboxylic acid (Mixture of Stereoisomers)

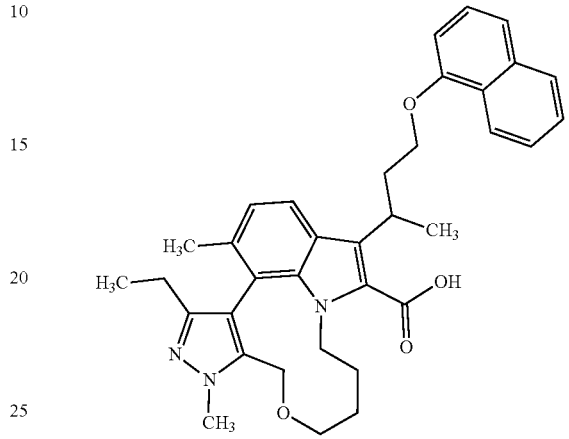

A mixture of ethyl 12-ethyl-10,13-dimethyl-1-(4-(naphthalen-1-yloxy)butan-2-yl)-4,5,6,7,9,10-hexahydropyrazolo[4',3':9,10][1,6]oxaazacycloundecino[8,7,6-hi]indole-2-carboxylate (mixture of stereoisomers, 85 mg; see Intermediate 461), ethanol (8 ml), and aqueous solution of lithium hydroxide (2M, 5 ml) was heated to 80° C. for 21 hours, volatiles were removed, and the residue partitioned between ethyl acetate and aqueous hydrochloric acid (3M), the layers were separated and the aqueous phase were extracted with ethyl acetate, the combined organic layers were washed with saturated aqueous sodium chloride solution, dried over magnesium sulfate, insoluble materials were removed by filtration, and the residue was concentrated under reduced pressure. The residue was purified by flash chromatography on silica gel eluting with a gradient of ethyl acetate in hexanes (0-100%) to give the title compound as an off white solid (64 mg).

LRMS (ESI)neg m/z=564 [M−H]$^-$ $^1$H NMR (400 MHz, Chloroform-d) δ 8.31-8.03 (m, 1H), 7.85 (dd, J=17.3, 8.3 Hz, 1H), 7.76-7.69 (m, 1H), 7.39 (tdd, J=9.0, 5.3, 1.4 Hz, 1H), 7.35-7.28 (m, 2H), 7.25-7.17 (m, 1H), 7.06 (dd, J=17.4, 8.3 Hz, 1H), 6.60 (t, J=6.8 Hz, 1H), 4.54 (dd, J=34.1, 13.4 Hz, 1H), 4.46-4.24 (m, 2H), 4.16-4.08 (m, 2H), 4.03 (ddd, J=19.2, 9.3, 4.2 Hz, 2H), 3.96 (d, J=9.9 Hz, 3H), 3.59-3.21 (m, 1H), 3.08-2.81 (m, 1H), 2.74-2.57 (m, 1H), 2.49 (dp, J=14.1, 6.8 Hz, 1H), 2.35-2.21 (m, 2H), 2.00 (d, J=6.8 Hz, 3H), 1.63 (dd, J=16.2, 7.1 Hz, 3H), 1.25 (dd, J=15.7, 8.5 Hz, 1H), 1.10 (dd, J=22.5, 13.4 Hz, 2H), 0.97 (dt, J=12.7, 7.6 Hz, 3H), 0.92-0.69 (m, 1H).

The title compound was separated into single stereoisomers by preparative chiral HPLC to give isomer 1 (11.5 mg, see Example 272), isomer 2 (3.0 mg, see Example 273), isomer 3 (14 mg, see Example 274) and isomer 4 (2.0 mg, see Example 275).

Preparative chiral HPLC method: Instrument: Labomatic HD5000, Labocord-5000; Gilson GX-241, Labcol Vario 4000, column: Chiralpak IG 5µ 250×30 mm; eluent A: hexane+0.1 Vol-% TFA (99%); eluent B: 2-propanol; Gradient: 10-40% B in 20 min; flow 50.0 ml/min; UV 220 nm.

Analytical chiral HPLC method: Agilent HPLC 1260; column: Chiralpak IG 3µ 100×4.6 mm; eluent A: hexane+ 0.1 Vol-% TFA (99%); eluent B: 2-propanol; gradient: 10-40% B in 7 min; flow 1.4 ml/min; temperature: 25° C.; DAD 220 nm.

Example 272

3-ethyl-1,4-dimethyl-7-[4-(naphthalen-1-yloxy)butan-2-yl]-1,10,11,12,13,15-hexahydropyrazolo[4',3': 9,10][1,6]oxazacycloundecino[8,7,6-hi]indole-8-carboxylic acid (Stereoisomer 1)

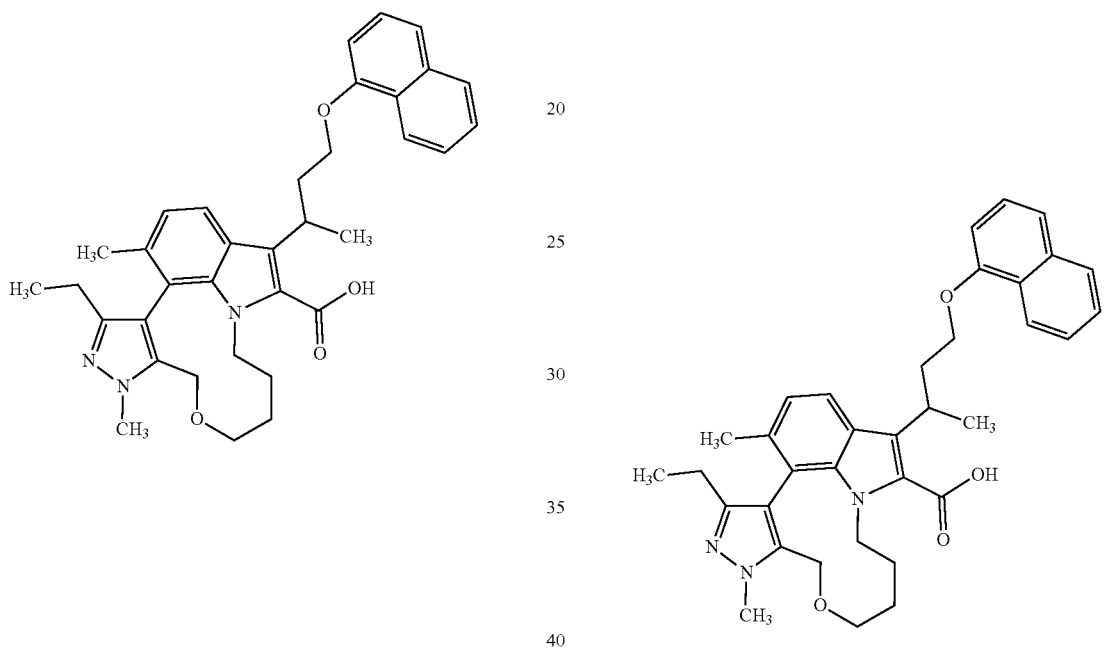

For the preparation of the mixture of stereoisomers and the separation of the isomers see Example 271.

Analytical Chiral HPLC (method see Example 271): $R_t$=2.13 min.

LC-MS (Method 1): $R_t$=1.57 min; MS (ESIpos): m/z=566 [M+H]$^+$ $^1$H-NMR (400 MHz, CHLOROFORM-d) δ [ppm]: 0.628 (0.57), 0.645 (0.82), 0.662 (0.94), 0.679 (0.76), 0.792 (1.02), 0.809 (1.25), 0.829 (0.96), 0.845 (0.74), 0.896 (4.58), 0.915 (9.16), 0.934 (4.47), 0.959 (0.84), 0.977 (0.63), 1.012 (0.97), 1.118 (0.48), 1.154 (3.02), 1.172 (5.35), 1.189 (4.14), 1.203 (1.65), 1.222 (1.27), 1.261 (1.45), 1.520 (7.83), 1.538 (7.77), 1.935 (16.00), 2.103 (1.49), 2.204 (1.40), 2.223 (3.71), 2.242 (3.56), 2.261 (1.26), 2.397 (0.69), 2.414 (0.98), 2.431 (1.15), 2.447 (0.96), 2.544 (0.78), 2.568 (0.92), 2.579 (0.76), 2.603 (0.51), 2.794 (0.55), 2.810 (1.09), 2.823 (0.95), 2.840 (1.23), 2.858 (0.64), 2.916 (0.72), 3.157 (0.63), 3.173 (1.10), 3.188 (1.13), 3.202 (0.95), 3.218 (0.52), 3.418 (0.42), 3.628 (0.69), 3.645 (1.60), 3.663 (1.57), 3.680 (0.65), 3.895 (15.08), 3.923 (1.74), 3.950 (1.11), 3.959 (1.02), 3.974 (0.86), 4.007 (3.75), 4.040 (4.26), 4.052 (1.70), 4.196 (1.01), 4.213 (1.36), 4.236 (1.34), 4.255 (1.42), 4.267 (1.60), 4.292 (0.92), 4.303 (1.26), 4.399 (2.91), 4.432 (2.52), 6.513 (2.58), 6.532 (2.71), 7.010 (3.05), 7.031 (3.21), 7.137 (1.45), 7.158 (3.04), 7.177 (2.24), 7.233 (3.45), 7.253 (2.96), 7.269 (2.28), 7.287 (1.70), 7.321 (1.58), 7.339 (2.32), 7.356 (1.17), 7.637 (2.71), 7.657 (2.40), 7.806 (3.00), 7.826 (2.82), 7.967 (2.44), 7.988 (2.32).

Example 273

3-ethyl-1,4-dimethyl-7-[4-(naphthalen-1-yloxy)butan-2-yl]-1,10,11,12,13,15-hexahydropyrazolo[4',3': 9,10][1,6]oxazacycloundecino[8,7,6-hi]indole-8-carboxylic acid (Stereoisomer 2)

For the preparation of the mixture of stereoisomers and the separation of the isomers see Example 271.

Analytical Chiral HPLC (method see Example 271): $R_t$=2.55 min.

LC-MS (Method 1): $R_t$=1.56 min; MS (ESIpos): m/z=566 [M+H]$^+$ $^1$H-NMR (400 MHz, CHLOROFORM-d) δ [ppm]: 0.000 (2.45), 0.810 (2.79), 0.859 (4.84), 0.877 (8.32), 0.895 (5.12), 1.060 (2.56), 1.185 (14.47), 1.356 (2.85), 1.565 (8.39), 1.583 (8.50), 1.917 (15.29), 2.107 (1.32), 2.226 (3.55), 2.398 (2.61), 2.611 (10.80), 2.941 (2.15), 3.443 (1.88), 3.669 (0.69), 3.883 (2.24), 3.951 (16.00), 4.253 (3.01), 4.286 (2.83), 4.336 (1.85), 4.368 (1.58), 4.497 (2.81), 4.530 (2.36), 6.531 (2.55), 6.550 (2.72), 6.975 (2.79), 6.995 (2.91), 7.267 (3.68), 7.287 (2.70), 7.351 (4.43), 7.669 (2.41), 7.775 (2.87), 7.795 (2.62), 8.201 (2.16).

Example 274

3-ethyl-1,4-dimethyl-7-[4-(naphthalen-1-yloxy)bu-tan-2-yl]-1,10,11,12,13,15-hexahydropyrazolo[4',3':9,10][1,6]oxazacycloundecino[8,7,6-hi]indole-8-carboxylic acid (Stereoisomer 3)

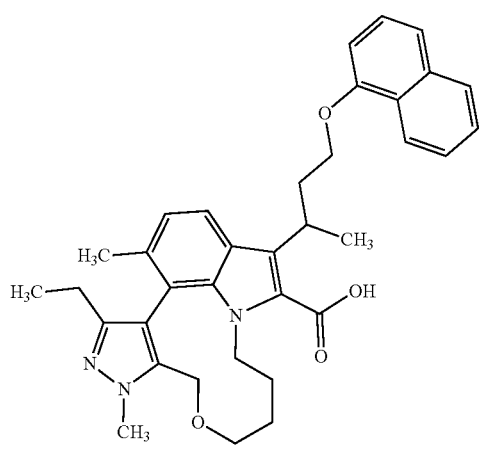 [SMILES: CCc1nn(C)c2c1-c1c(C)ccc3c(C(C)CCOc4cccc5ccccc45)c(C(=O)O)n(c13)CCCCOC2]

For the preparation of the mixture of stereoisomers and the separation of the isomers see Example 271.

Analytical Chiral HPLC (method see Example 271): $R_t$=3.73 min.

LC-MS (Method 1): $R_t$=1.57 min; MS (ESIpos): m/z=566 [M+H]$^+$ $^1$H-NMR (400 MHz, CHLOROFORM-d) δ [ppm]: 0.000 (6.51), 0.652 (1.42), 0.786 (2.62), 0.804 (2.67), 0.809 (2.92), 0.823 (2.19), 0.846 (1.28), 0.861 (0.78), 0.928 (8.24), 0.961 (4.41), 1.016 (1.57), 1.067 (1.16), 1.095 (0.78), 1.142 (1.60), 1.157 (3.40), 1.175 (6.61), 1.185 (7.91), 1.206 (3.82), 1.223 (3.47), 1.263 (0.68), 1.282 (0.54), 1.293 (0.48), 1.312 (0.72), 1.330 (1.12), 1.347 (0.73), 1.356 (0.90), 1.404 (0.41), 1.423 (0.43), 1.457 (0.94), 1.521 (15.95), 1.539 (16.00), 1.675 (0.53), 1.818 (0.64), 1.945 (7.25), 2.104 (1.39), 2.242 (3.76), 2.398 (1.33), 2.414 (1.87), 2.431 (2.17), 2.448 (1.80), 2.546 (1.44), 2.570 (1.81), 2.581 (1.52), 2.604 (1.00), 2.837 (1.33), 3.174 (1.66), 3.350 (0.58), 3.422 (1.48), 3.631 (0.73), 3.648 (1.65), 3.666 (1.64), 3.684 (0.68), 3.908 (5.35), 3.921 (5.62), 4.001 (4.44), 4.016 (5.59), 4.038 (4.60), 4.056 (2.62), 4.079 (1.06), 4.216 (2.25), 4.239 (2.31), 4.256 (1.80), 4.285 (1.76), 4.339 (1.20), 4.357 (1.04), 4.406 (1.64), 4.527 (1.08), 6.514 (4.78), 6.533 (5.01), 6.856 (1.38), 6.876 (1.45), 7.014 (5.03), 7.035 (5.22), 7.139 (2.50), 7.159 (5.26), 7.179 (3.88), 7.233 (7.00), 7.253 (5.55), 7.266 (3.45), 7.285 (2.51), 7.322 (2.30), 7.341 (3.38), 7.357 (1.80), 7.458 (1.86), 7.477 (1.68), 7.638 (5.12), 7.658 (4.59), 7.814 (5.70), 7.835 (5.32), 7.953 (4.15), 7.974 (3.92).

Example 275

3-ethyl-1,4-dimethyl-7-[4-(naphthalen-1-yloxy)bu-tan-2-yl]-1,10,11,12,13,15-hexahydropyrazolo[4',3':9,10][1,6]oxazacycloundecino[8,7,6-hi]indole-8-carboxylic acid (Stereoisomer 4)

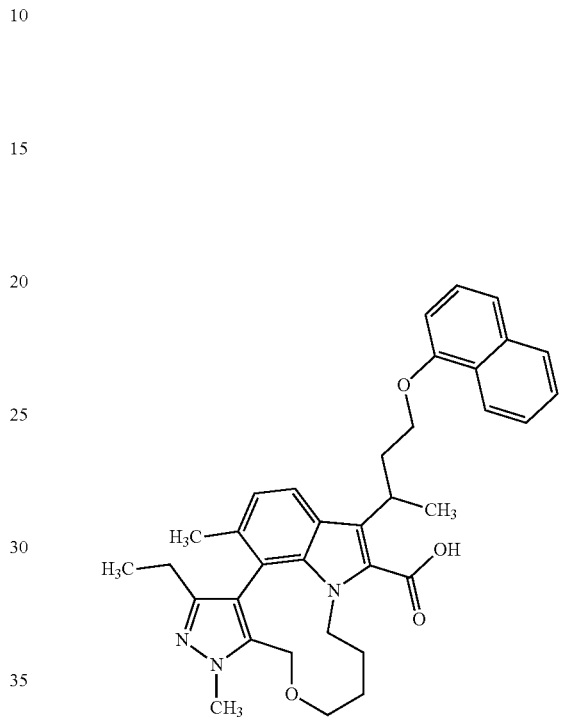

For the preparation of the mixture of stereoisomers and the separation of the isomers see Example 271.

Analytical Chiral HPLC (method see Example 271): $R_t$=4.53 min.

LC-MS (Method 1): $R_t$=1.56 min; MS (ESIpos): m/z=566 [M+H]$^+$ $^1$H-NMR (400 MHz, CHLOROFORM-d) δ [ppm]: 0.000 (4.77), 0.773 (1.91), 0.783 (2.08), 0.810 (2.98), 0.826 (1.81), 0.938 (3.06), 1.140 (3.72), 1.160 (4.24), 1.184 (16.00), 1.215 (3.66), 1.263 (2.16), 1.332 (1.09), 1.357 (2.43), 1.396 (1.40), 1.494 (1.23), 1.567 (8.62), 1.584 (8.47), 1.960 (2.10), 2.017 (2.06), 2.107 (1.48), 2.272 (3.43), 2.402 (5.06), 2.453 (4.75), 2.980 (0.64), 3.336 (0.78), 3.353 (0.86), 3.405 (0.99), 3.424 (1.30), 3.485 (0.99), 3.633 (0.58), 3.650 (1.07), 3.668 (1.01), 3.888 (2.30), 3.956 (2.78), 4.243 (1.85), 4.549 (0.74), 6.537 (2.24), 6.555 (2.30), 6.880 (0.41), 6.929 (1.36), 6.979 (1.87), 6.997 (1.85), 7.269 (3.58), 7.289 (2.65), 7.343 (3.76), 7.353 (4.07), 7.364 (3.83), 7.451 (1.48), 7.481 (0.62), 7.662 (2.22), 7.682 (2.06), 7.783 (2.41), 7.802 (2.22), 8.185 (2.08), 8.205 (2.04).

Example 276

7-{4-[(6-fluoronaphthalen-1-yl)oxy]butan-2-yl}-2,3,4-trimethyl-2,10,11,12,13,15-hexahydropyrazolo[4',3':9,10][1,6]oxazacycloundecino[8,7,6-hi]indole-8-carboxylic acid (Mixture of Stereoisomers)

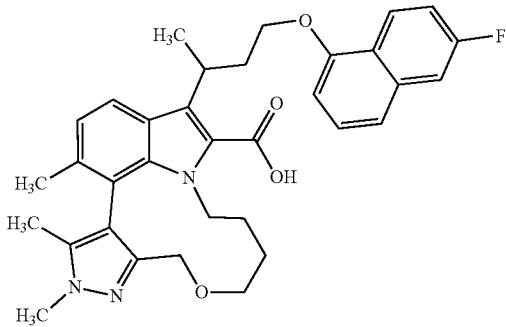 [SMILES: Cc1ccc2c(C(C)CCOc3cccc4cc(F)ccc34)c(C(=O)O)n3c2c1-c1c(nn(C)c1C)COCCCC3]

A mixture of ethyl 1-(4-((6-fluoronaphthalen-1-yl)oxy)butan-2-yl)-11,12,13-trimethyl-4,5,6,7,9,11-hexahydropyrazolo[4',3':9,10][1,6]oxaazacycloundecino[8,7,6-hi]indole-2-carboxylate (mixture of stereoisomers; 100 mg, 0.18 mmol; see Intermediate 465), ethanol (15 ml), and aqueous solution of lithium hydroxide (2 M, 2 ml) was heated to 70° C. for 48 hours. Volatiles were removed, and the residue was partitioned between ethyl acetate and aqueous hydrochloric acid (3M), the layers were separated and the aqueous phase was extracted with ethyl acetate. The combined organic layers were washed with saturated aqueous sodium chloride solution and dried over sodium sulfate. Insoluble materials were removed by filtration, and the residue was concentrated under reduced pressure. The residue was purified by flash chromatography on silica gel eluting with a gradient of ethyl acetate in hexanes (0-100%) to give the title compound as a white solid (60 mg).

LRMS (ESIneg) m/z=568 [M−H]⁻

$^1$H NMR (400 MHz, DMSO-d$_6$) δ 12.99 (s, 1H), 8.19-8.06 (m, 1H), 7.78 (dd, J=17.3, 8.2 Hz, 1H), 7.61 (ddd, J=12.8, 10.3, 2.6 Hz, 1H), 7.36 (td, J=9.8, 8.8, 3.8 Hz, 2H), 7.28 (td, J=8.9, 2.7 Hz, 1H), 7.05 (dd, J=13.5, 8.2 Hz, 1H), 6.77-6.65 (m, 1H), 4.35 (dd, J=28.0, 12.5 Hz, 1H), 4.19 (dd, J=12.5, 9.7 Hz, 1H), 4.10 (d, J=6.9 Hz, 1H), 4.06-3.90 (m, 2H), 3.81 (d, J=2.5 Hz, 3H), 3.79-3.70 (m, 2H), 3.24-2.99 (m, 2H), 2.46-2.35 (m, 2H), 2.00 (d, J=4.1 Hz, 3H), 1.74 (d, J=20.8 Hz, 3H), 1.49 (dd, J=12.2, 7.1 Hz, 3H), 1.34-0.75 (m, 4H).

The title compound was separated into single stereoisomers by preparative chiral HPLC (Method 1 first followed by method 2) to give isomer 1 (7.4 mg, see Example 277), isomer 2 (10.7 mg, see Example 278), isomer 3 (4.7 mg, see Example 279) and isomer 4 (5.7 mg, see Example 280).

Preparative chiral HPLC Method 1: Instrument: Sepiatec: Prep SFC100; column: Chiralpak IG 5 μm 250×30 mm; eluent A CO$_2$, eluent B: 2-propanol+0.4 Vol-% diethylamine (99%); isocratic: 18% B; flow 100.0 ml/min temperature: 40° C.; BPR: 150 bar; MWD @ 220 nm.

Preparative chiral HPLC method 2: Instrument: Labomatic HD5000, Labocord-5000; Gilson GX-241, Labcol Vario 4000, column: Amylose SA 5μ 250×30 mm; eluent A: hexane+0.1 Vol-% diethylamine (99%); eluent B: 2-propanol; gradient: 20-50% B in 20 min; flow 40.0 ml/min; UV 254 nm.

Analytical chiral HPLC method: Instrument: Agilent: 1260, Aurora SFC-Modul; column: Chiralpak IG 5 μm 100×4.6 mm; eluent A: CO$_2$, eluent B: 2-propanol+0.2 Vol-% diethylamine (99%); isocratic: 18% B; flow 4.0 ml/min; temperature: 37.5° C.; BPR: 100 bar; MWD @ 220 nm.

Example 277

7-{4-[(6-fluoronaphthalen-1-yl)oxy]butan-2-yl}-2,3,4-trimethyl-2,10,11,12,13,15-hexahydropyrazolo[4',3':9,10][1,6]oxazacycloundecino[8,7,6-hi]indole-8-carboxylic acid (Stereoisomer 1)

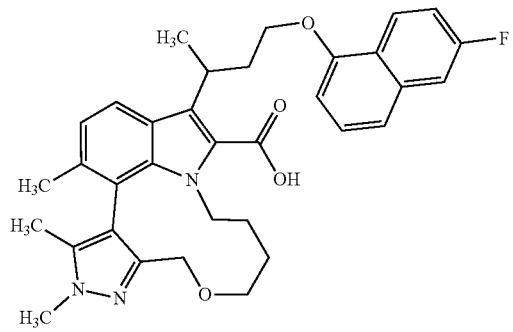 [SMILES: Cc1ccc2c(C(C)CCOc3cccc4cc(F)ccc34)c(C(=O)O)n3c2c1-c1c(nn(C)c1C)COCCCC3]

For the preparation of the mixture of stereoisomers and the separation of the isomers see Example 276.

Analytical Chiral HPLC (method see Example 276): R$_t$=2.85 min.

LC-MS (Method 1): R$_t$=1.54 min; MS (ESIpos): m/z=570 [M+H]⁺

$^1$H-NMR (400 MHz, DMSO-d6) δ[ppm]: 0.981 (0.56), 0.991 (0.58), 1.026 (1.24), 1.041 (1.16), 1.087 (0.48), 1.118 (2.53), 1.137 (6.26), 1.154 (2.35), 1.237 (1.48), 1.254 (1.12), 1.478 (5.67), 1.496 (5.75), 1.710 (15.50), 1.905 (0.94), 1.966 (11.95), 2.083 (0.44), 2.115 (0.78), 2.288 (0.40), 2.306 (0.66), 2.322 (1.62), 2.326 (1.62), 2.332 (1.16), 2.336 (0.86), 2.417 (0.56), 2.439 (0.74), 2.453 (0.74), 2.518 (5.17), 2.522 (3.39), 2.665 (0.88), 2.669 (1.20), 2.673 (0.88), 2.840 (0.60), 2.858 (1.74), 2.876 (1.68), 2.895 (0.58), 3.098 (0.52), 3.110 (0.60), 3.124 (0.98), 3.135 (0.96), 3.150 (0.78), 3.162 (0.72), 3.717 (0.44), 3.739 (0.70), 3.762 (0.54), 3.799 (16.00), 3.947 (0.72), 3.964 (1.10), 3.979 (1.02), 3.993 (1.24), 4.008 (0.82), 4.017 (0.72), 4.030 (0.76), 4.047 (1.02), 4.066 (1.10), 4.181 (2.03), 4.212 (2.51), 4.354 (2.31), 4.385 (1.72), 6.718 (1.76), 6.736 (1.84), 6.962 (1.56), 6.982 (1.62), 7.315 (0.86), 7.322 (1.06), 7.326 (1.06), 7.338 (1.60), 7.345 (2.95), 7.360 (1.12), 7.366 (2.69), 7.385 (2.93), 7.405 (1.16), 7.603 (1.56), 7.609 (1.56), 7.629 (1.56), 7.635 (1.50), 7.680 (1.34), 7.700 (1.22), 8.140 (1.24), 8.155 (1.32), 8.163 (1.24), 8.177 (1.14).

Example 278

7-{4-[(6-fluoronaphthalen-1-yl)oxy]butan-2-yl}-2,3,4-trimethyl-2,10,11,12,13,15-hexahydropyrazolo[4',3':9,10][1,6]oxazacycloundecino[8,7,6-hi]indole-8-carboxylic acid (Stereoisomer 2)

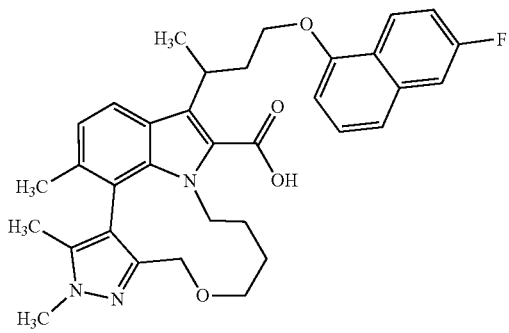 [SMILES: Cc1ccc2c(C(C)CCOc3cccc4cc(F)ccc34)c(C(=O)O)n3c2c1-c1c(nn(C)c1C)COCCCC3]

For the preparation of the mixture of stereoisomers and the separation of the isomers see Example 276.

Analytical Chiral HPLC (method see Example 276): $R_t$=3.77 min.

LC-MS (Method 1): $R_t$=1.52 min; MS (ESIpos): m/z=570 [M+H]$^+$ $^1$H-NMR (400 MHz, DMSO-d6) δ[ppm]: 0.875 (0.47), 0.990 (0.68), 1.008 (0.49), 1.026 (1.41), 1.041 (1.49), 1.069 (0.68), 1.087 (0.90), 1.105 (0.90), 1.119 (0.79), 1.131 (2.54), 1.137 (2.01), 1.150 (4.59), 1.168 (2.09), 1.451 (5.75), 1.469 (5.81), 1.764 (15.47), 1.905 (0.68), 1.959 (0.45), 1.980 (12.22), 2.114 (0.58), 2.336 (0.56), 2.358 (0.64), 2.375 (0.86), 2.392 (0.71), 2.406 (0.55), 2.423 (0.68), 2.446 (0.86), 2.462 (0.90), 2.518 (5.23), 2.522 (3.38), 2.855 (0.56), 2.872 (1.64), 2.891 (1.62), 2.909 (0.53), 3.048 (0.53), 3.062 (0.85), 3.074 (0.92), 3.088 (0.68), 3.100 (0.62), 3.191 (1.26), 3.210 (1.18), 3.691 (0.49), 3.713 (0.79), 3.737 (0.60), 3.807 (16.00), 3.978 (0.83), 4.002 (0.96), 4.018 (0.53), 4.044 (0.58), 4.062 (0.64), 4.085 (0.53), 4.104 (0.66), 4.121 (1.11), 4.137 (1.43), 4.155 (2.71), 4.186 (2.75), 4.281 (2.37), 4.312 (1.60), 6.662 (1.56), 6.678 (1.62), 7.005 (1.79), 7.025 (1.90), 7.257 (0.75), 7.263 (0.86), 7.279 (1.37), 7.285 (1.50), 7.301 (0.88), 7.308 (1.58), 7.329 (1.94), 7.347 (2.18), 7.356 (2.97), 7.374 (0.88), 7.573 (1.49), 7.579 (1.54), 7.599 (1.52), 7.605 (1.52), 7.734 (1.58), 7.754 (1.49), 8.085 (1.26), 8.100 (1.35), 8.108 (1.32), 8.123 (1.22).

Example 279

7-{4-[(6-fluoronaphthalen-1-yl)oxy]butan-2-yl}-2,3,4-trimethyl-2,10,11,12,13,15-hexahydropyrazolo[4',3':9,10][1,6]oxazacycloundecino[8,7,6-hi]indole-8-carboxylic acid (Stereoisomer 3)

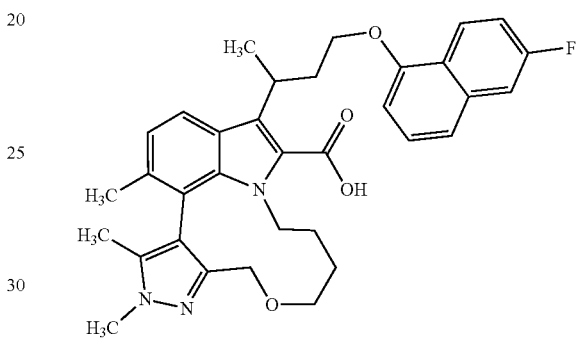

For the preparation of the mixture of stereoisomers and the separation of the isomers see Example 276.

Analytical Chiral HPLC (method see Example 276): $R_t$=6.06 min.

LC-MS (Method 1): $R_t$=1.52 min; MS (ESIpos): m/z=570 [M+H]$^+$ $^1$H-NMR (400 MHz, DMSO-d6) δ[ppm]: 0.850 (0.48), 0.966 (1.09), 1.001 (0.44), 1.107 (1.73), 1.121 (2.29), 1.140 (4.08), 1.158 (2.13), 1.230 (3.16), 1.254 (1.66), 1.347 (0.72), 1.482 (6.06), 1.500 (6.13), 1.709 (15.39), 1.905 (0.55), 1.972 (12.51), 2.297 (0.44), 2.322 (1.37), 2.327 (1.75), 2.331 (1.77), 2.348 (0.72), 2.415 (0.65), 2.435 (0.91), 2.449 (0.91), 2.522 (4.65), 2.664 (0.95), 2.668 (1.28), 2.673 (0.95), 2.853 (0.51), 2.871 (1.43), 2.889 (1.41), 2.907 (0.48), 3.099 (0.53), 3.124 (1.01), 3.136 (0.99), 3.150 (0.82), 3.729 (0.48), 3.753 (0.78), 3.799 (16.00), 3.940 (0.80), 3.957 (1.12), 3.973 (0.72), 3.985 (0.69), 4.000 (1.26), 4.014 (0.95), 4.023 (1.16), 4.040 (1.26), 4.059 (1.45), 4.078 (1.22), 4.095 (0.74), 4.180 (2.06), 4.211 (2.57), 4.359 (2.36), 4.390 (1.81), 6.722 (1.89), 6.739 (1.96), 6.977 (1.75), 6.998 (1.83), 7.316 (0.88), 7.322 (1.05), 7.329 (1.09), 7.338 (1.66), 7.345 (2.11), 7.349 (2.46), 7.360 (1.16), 7.367 (2.48), 7.386 (3.12), 7.407 (1.22), 7.604 (1.60), 7.610 (1.62), 7.630 (1.60), 7.636 (1.56), 7.700 (1.54), 7.720 (1.39), 8.135 (1.28), 8.150 (1.37), 8.159 (1.33), 8.173 (1.22).

Example 280

7-{4-[(6-fluoronaphthalen-1-yl)oxy]butan-2-yl}-2,3,4-trimethyl-2,10,11,12,13,15-hexahydropyrazolo[4',3':9,10][1,6]oxazacycloundecino[8,7,6-hi]indole-8-carboxylic acid (Stereoisomer 4)

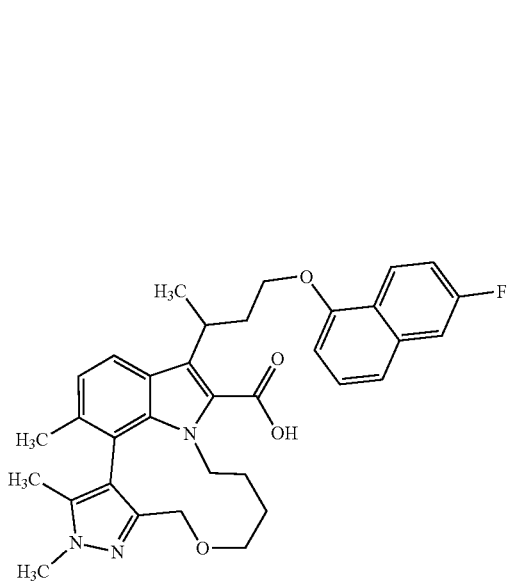 [SMILES: Cc1ccc2c(C(C)CCOc3cccc4cc(F)ccc34)c(C(=O)O)n3c2c1-c1c(nn(C)c1C)COCCCC3]

For the preparation of the mixture of stereoisomers and the separation of the isomers see Example 276.

Analytical Chiral HPLC (method see Example 276): $R_t$=6.83 min.

LC-MS (Method 1): $R_t$=1.55 min; MS (ESIpos): m/z=570 [M+H]$^+$ $^1$H-NMR (400 MHz, DMSO-d6) δ[ppm]: 0.850 (0.93), 0.950 (0.47), 0.966 (0.80), 0.982 (0.82), 1.107 (2.82), 1.131 (2.55), 1.149 (4.51), 1.168 (2.35), 1.230 (2.57), 1.254 (0.68), 1.347 (0.70), 1.451 (6.12), 1.470 (6.26), 1.499 (0.62), 1.710 (1.07), 1.764 (15.36), 1.905 (0.89), 1.981 (12.77), 2.322 (1.05), 2.326 (1.42), 2.331 (1.11), 2.359 (0.74), 2.377 (0.97), 2.393 (0.84), 2.408 (0.66), 2.423 (0.89), 2.446 (1.07), 2.522 (4.24), 2.665 (0.95), 2.668 (1.21), 2.673 (0.93), 2.856 (0.60), 2.874 (1.69), 2.892 (1.65), 2.910 (0.58), 3.048 (0.66), 3.062 (1.01), 3.074 (1.07), 3.088 (0.82), 3.100 (0.76), 3.189 (1.52), 3.715 (0.86), 3.739 (0.66), 3.807 (16.00), 3.963 (0.49), 3.979 (0.99), 4.002 (1.09), 4.021 (0.74), 4.041 (0.70), 4.060 (0.80), 4.076 (0.62), 4.105 (0.70), 4.133 (1.46), 4.155 (2.86), 4.186 (2.80), 4.282 (2.45), 4.313 (1.67), 6.662 (1.71), 6.679 (1.75), 7.007 (1.89), 7.027 (1.96), 7.256 (0.86), 7.263 (0.93), 7.279 (1.50), 7.285 (1.59), 7.301 (0.99), 7.308 (1.63), 7.329 (2.16), 7.347 (2.55), 7.356 (3.17), 7.375 (0.95), 7.573 (1.59), 7.579 (1.59), 7.599 (1.61), 7.605 (1.61), 7.736 (1.67), 7.757 (1.52), 8.085 (1.34), 8.099 (1.44), 8.107 (1.36), 8.123 (1.24).

Example 281

(rac)-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid

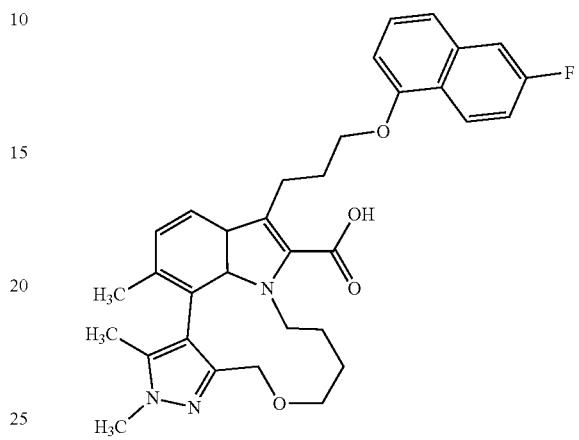

A mixture of (rac)-ethyl 12-ethyl-1-(3-((6-fluoronaphthalen-1-yl)oxy)propyl)-11-methyl-4,5,6,7,9,11-hexahydropyrazolo[4',3':9,10][1]oxa[6]azacycloundecino[8,7,6-hi]indole-2-carboxylate (160 mg, 274 µmol; see Intermediate 477) and aqueous solution of lithium hydroxide (2 M, 5.45 mL, 10.9 mmol) in ethanol (6 mL) was heated to 70° C. for 24 hours. The reaction mixture was cooled to room temperature and volatiles were removed under reduced pressure. The mixture was diluted with water, acidified to pH 2 with aqueous hydrochloric acid (1 M) and extracted three times with ethyl acetate. The combined organic extracts were dried over magnesium sulfate, solids were removed by filtration and volatiles were removed under reduced pressure. The residue was purified by flash chromatography on silica gel eluting with a gradient of ethyl acetate in hexanes (0-70%) to give the title compound (120 mg, 215 µmol).

LRMS (ESIpos): m/z=556.4 [M+H]$^+$ $^1$H NMR (300 MHz, Chloroform-d) δ 8.37 (dd, J=9.2, 5.8 Hz, 1H), 7.72 (dd, J=8.0, 1.3 Hz, 1H), 7.43-7.15 (m, 4H), 7.16-6.97 (m, 2H), 6.70 (dd, J=6.8, 1.8 Hz, 1H), 4.70 (d, J=12.6 Hz, 1H), 4.48-4.31 (m, 2H), 4.25-3.99 (m, 4H), 3.91 (s, 3H), 3.46 (dd, J=8.8, 5.9 Hz, 3H), 3.28 (dt, J=11.7, 6.0 Hz, 1H), 2.45-2.18 (m, 4H), 2.05 (s, 1H), 1.53 (s, 1H), 1.48-1.32 (m, 0H), 1.26 (t, J=7.1 Hz, 2H), 0.93 (t, J=7.6 Hz, 3H).

The title compound was separated into enantiomers by preparative chiral HPLC to give enantiomer 1 (34.0 mg, see Example 282) and enantiomer 2 (33.1 mg, see Example 283).

Preparative chiral HPLC method: Instrument: Labomatic HD5000, Labocord-5000; Gilson GX-241, Labcol Vario 4000, column: Chiralpak IG 5µ 250×30 mm; eluent A: hexane+0.1 Vol-% diethylamine (99%); eluent B: ethanol; Gradient: 20-50% B in 20 min; flow 40.0 ml/min; UV 254 nm.

Analytical chiral HPLC method: Agilent HPLC 1260; column: Chiralpak IG 3µ 100×4.6 mm; eluent A: hexane+0.1 Vol-% diethylamine (99%); eluent B: ethanol; Gradient: 20-50% B in 7 min; flow 1.4 ml/min; temperature: 25° C.; DAD 254 nm.

Example 282

(+)-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid-N-ethylethanamine salt
(Enantiomer 1)

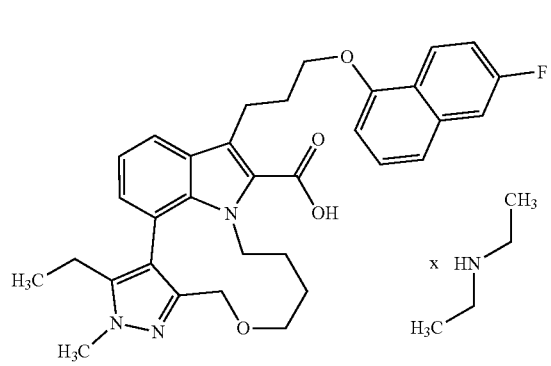

For the preparation of the racemic title compound and separation into its enantiomers see Example 281.

Analytical Chiral HPLC (method see Example 281): $R_t$=2.12 min.

Specific optical rotation (Method O1): +34.4° (c=1.0000 g/100 ml in DMSO)

LC-MS (Method 1): $R_t$=1.51 min; MS (ESIpos): m/z=556 [M+H]$^+$ $^1$H-NMR (400 MHz, DMSO-d6) δ[ppm]: 0.826 (3.32), 0.844 (7.20), 0.863 (3.53), 1.121 (8.51), 1.140 (16.00), 1.157 (8.28), 1.230 (0.48), 1.315 (0.80), 1.899 (0.49), 2.140 (0.46), 2.159 (0.91), 2.177 (1.82), 2.195 (2.40), 2.207 (3.48), 2.225 (2.68), 2.243 (1.20), 2.263 (0.52), 2.326 (0.85), 2.669 (0.93), 2.796 (2.16), 2.815 (6.11), 2.833 (6.04), 2.851 (2.07), 3.090 (1.19), 3.112 (1.00), 3.190 (1.13), 3.205 (1.64), 3.223 (2.81), 3.245 (3.85), 3.263 (3.85), 3.772 (0.67), 3.796 (1.07), 3.821 (15.87), 4.166 (3.11), 4.173 (2.62), 4.190 (2.65), 4.197 (3.45), 4.434 (2.94), 4.464 (2.46), 6.726 (1.78), 6.743 (2.06), 6.825 (1.55), 6.829 (1.61), 6.842 (1.61), 6.846 (1.64), 6.916 (1.49), 6.935 (2.33), 6.953 (1.29), 7.358 (0.83), 7.364 (0.96), 7.380 (2.11), 7.386 (1.82), 7.402 (3.04), 7.409 (1.75), 7.418 (5.23), 7.437 (0.74), 7.546 (1.97), 7.565 (1.84), 7.630 (1.58), 7.637 (1.64), 7.656 (1.64), 7.663 (1.58), 8.267 (1.36), 8.282 (1.51), 8.290 (1.46), 8.305 (1.33).

Example 283

(−)-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid-N-ethylethanamine salt
(Enantiomer 2)

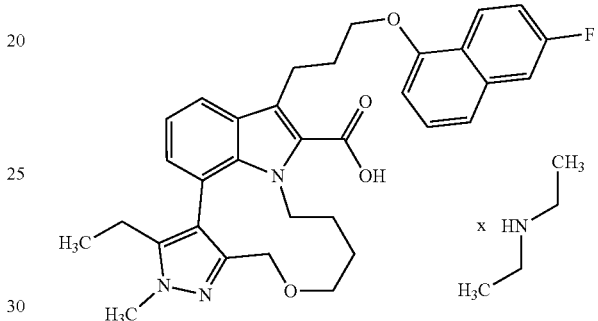

For the preparation of the racemic title compound and separation into its enantiomers see Example 281.

Analytical Chiral HPLC (method see Example 281): $R_t$=3.94 min.

Specific optical rotation (Method O1): −33.6° (c=1.0000 g/100 ml in DMSO)

LC-MS (Method 1): $R_t$=1.51 min; MS (ESIpos): m/z=556 [M+H]$^+$ $^1$H-NMR (400 MHz, DMSO-d6) δ[ppm]: 0.824 (3.32), 0.843 (7.24), 0.862 (3.53), 1.126 (7.07), 1.145 (13.52), 1.163 (6.95), 1.229 (0.68), 1.329 (0.72), 1.900 (0.55), 2.139 (0.48), 2.157 (0.90), 2.175 (1.81), 2.193 (2.51), 2.207 (3.43), 2.226 (2.63), 2.244 (1.19), 2.263 (0.51), 2.326 (0.80), 2.669 (0.85), 2.807 (1.81), 2.826 (5.06), 2.843 (5.00), 2.861 (1.70), 3.089 (1.16), 3.115 (0.94), 3.195 (1.14), 3.209 (1.67), 3.228 (2.91), 3.248 (4.00), 3.266 (3.84), 3.779 (0.66), 3.821 (16.00), 4.166 (3.05), 4.173 (2.48), 4.190 (2.63), 4.196 (3.47), 4.417 (0.76), 4.437 (2.99), 4.468 (2.30), 6.736 (1.74), 6.753 (2.00), 6.826 (1.53), 6.830 (1.57), 6.843 (1.60), 6.847 (1.60), 6.922 (1.49), 6.941 (2.32), 6.959 (1.27), 7.358 (0.84), 7.364 (0.95), 7.381 (2.07), 7.386 (1.82), 7.402 (3.11), 7.409 (1.65), 7.419 (5.17), 7.437 (0.70), 7.554 (1.93), 7.573 (1.81), 7.630 (1.61), 7.637 (1.65), 7.656 (1.64), 7.663 (1.57), 8.267 (1.38), 8.282 (1.49), 8.290 (1.45), 8.305 (1.31).

Example 284

(rac)-7-{3-[(6-fluoronaphthalen-1-yl)oxy]propyl}-3-methyl-2-[2-(morpholin-4-yl)ethyl]-2,10,11,12,13,15-hexahydropyrazolo[4',3':9,10][1,6]oxazacycloundecino[8,7,6-hi]indole-8-carboxylic acid

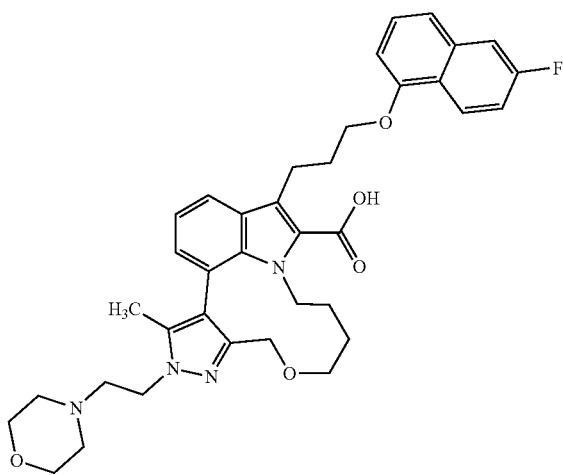 [SMILES: Cc1c2c(nn1CCN1CCOCC1)COCCCCn1c(C(=O)O)c(CCCOc3cccc4cc(F)ccc34)c3cccc-2c31]

A mixture of (rac)-ethyl 1-(3-((6-fluoronaphthalen-1-yl)oxy)propyl)-12-methyl-11-(2-morpholinoethyl)-4,5,6,7,9,11-hexahydropyrazolo[4',3':9,10][1]oxa[6]azacycloundecino[8,7,6-hi]indole-2-carboxylate (300 mg, 448 µmol; see Intermediate 481) and aqueous solution of lithium hydroxide (2 M, 9 mL) in ethanol (10 mL) was heated at 70° C. for 18 hours. The reaction mixture was cooled to room temperature, volatiles were removed under reduced pressure, the residue was diluted with water, acidified to pH 2 with aqueous hydrochloric acid and extracted three times with ethyl acetate. The combined organic extracts were dried over magnesium sulfate, solids were removed by filtration and volatiles were removed under reduced pressure. The residue was purified by flash chromatography on silica gel eluting with a gradient of methanol in dichloromethane (0-15%) to give the title compound (287 mg, 447 µmol).

LRMS (ESIpos): m/z=641 [M+H]$^+$ $^1$H NMR (400 MHz, Chloroform-d) δ 8.35 (dd, J=9.3, 5.7 Hz, 1H), 7.69 (dd, J=8.2, 1.0 Hz, 1H), 7.39 (dd, J=10.0, 2.7 Hz, 1H), 7.36-7.31 (m, 2H), 7.22 (dd, J=9.1, 2.7 Hz, 1H), 7.13-7.05 (m, 1H), 7.00 (dd, J=7.1, 1.3 Hz, 1H), 6.70 (dd, J=6.5, 2.1 Hz, 1H), 4.71 (d, J=12.5 Hz, 1H), 4.46-4.29 (m, 2H), 4.21 (dt, J=13.5, 6.5 Hz, 4H), 4.03-3.88 (m, 1H), 3.70 (t, J=4.6 Hz, 4H), 3.50-3.35 (m, 3H), 3.27-3.10 (m, 1H), 2.92-2.79 (m, 2H), 2.61-2.46 (m, 4H), 2.41-2.23 (m, 2H), 1.89 (s, 3H), 1.62-1.08 (m, 4H).

The title compound was separated into enantiomers by preparative chiral HPLC to give enantiomer 1 (78.0 mg, see Example 285) and enantiomer 2 (93.0 mg, see Example 286).

Preparative chiral HPLC method: Instrument: Labomatic HD5000, Labocord-5000; Gilson GX-241, Labcol Vario 4000, column: Chiralpak IG 5µ 250×30 mm; eluent A: hexane+0.1 Vol-% diethylamine (99%); eluent B: ethanol; Gradient: 20-50% B in 20 min; flow 40.0 ml/min; UV 254 nm.

Analytical chiral HPLC method: Agilent HPLC 1260; column: Chiralpak IG 3µ 100×4.6 mm; eluent A: hexane+0.1 Vol-% diethylamine (99%); eluent B: ethanol; Gradient: 20-50% B in 7 min; flow 1.4 ml/min; temperature: 25° C.; DAD 254 nm.

Example 285

(+)-7-{3-[(6-fluoronaphthalen-1-yl)oxy]propyl}-3-methyl-2-[2-(morpholin-4-yl)ethyl]-2,10,11,12,13,15-hexahydropyrazolo[4',3':9,10][1,6]oxazacycloundecino[8,7,6-hi]indole-8-carboxylic acid-N-ethylethanamine salt (Enantiomer 1)

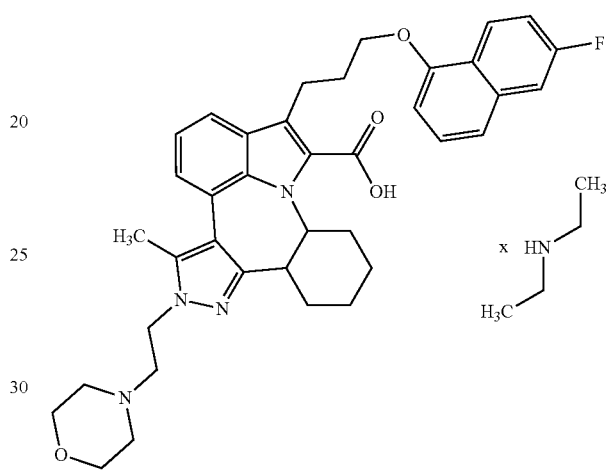

For the preparation of the racemic title compound and separation into its enantiomers see Example 284.

Analytical Chiral HPLC (method see Example 284): R$_t$=3.35 min.

Specific optical rotation (Method O1): +39.5° (c=1.0000 g/100 ml in DMSO)

LC-MS (Method 1): R$_t$=1.41 min; MS (ESIpos): m/z=642 [M+H]$^+$ $^1$H-NMR (400 MHz, DMSO-d6) δ[ppm]: 1.076 (1.01), 1.127 (7.35), 1.145 (16.00), 1.163 (7.74), 1.231 (0.58), 1.258 (0.64), 1.854 (15.79), 1.902 (0.71), 2.179 (1.19), 2.197 (1.82), 2.214 (1.27), 2.231 (0.43), 2.322 (0.71), 2.327 (0.96), 2.332 (0.73), 2.372 (0.88), 2.388 (1.21), 2.400 (1.78), 2.411 (1.09), 2.444 (1.77), 2.456 (1.37), 2.518 (4.26), 2.522 (2.76), 2.660 (0.46), 2.665 (0.86), 2.669 (1.60), 2.673 (0.96), 2.685 (0.91), 2.701 (1.35), 2.717 (0.73), 2.722 (0.73), 2.739 (1.27), 2.755 (0.96), 2.772 (0.58), 2.813 (1.80), 2.831 (5.37), 2.849 (5.27), 2.867 (1.67), 3.058 (0.86), 3.069 (0.79), 3.082 (0.76), 3.095 (0.54), 3.153 (0.66), 3.172 (1.06), 3.186 (1.17), 3.205 (1.67), 3.278 (4.16), 3.525 (3.85), 3.536 (6.34), 3.547 (3.73), 3.758 (0.73), 3.778 (0.53), 4.117 (0.73), 4.137 (0.81), 4.153 (1.62), 4.174 (1.96), 4.185 (3.88), 4.201 (1.30), 4.216 (3.65), 4.232 (0.86), 4.251 (0.63), 4.461 (2.76), 4.477 (0.66), 4.492 (2.38), 6.737 (1.37), 6.755 (1.57), 6.834 (1.34), 6.840 (1.39), 6.851 (1.30), 6.857 (1.42), 6.929 (1.44), 6.949 (2.05), 6.967 (1.21), 7.360 (0.86), 7.366 (1.01), 7.382 (1.45), 7.388 (1.88), 7.407 (2.54), 7.419 (2.92), 7.424 (5.42), 7.440 (0.54), 7.560 (1.59), 7.578 (1.47), 7.632 (1.60), 7.638 (1.67), 7.658 (1.60), 7.664 (1.62), 8.267 (1.39), 8.282 (1.42), 8.291 (1.42), 8.305 (1.34).

Example 286

(−)-7-{3-[(6-fluoronaphthalen-1-yl)oxy]propyl}-3-methyl-2-[2-(morpholin-4-yl)ethyl]-2,10,11,12,13,15-hexahydropyrazolo[4',3':9,10][1,6]oxazacycloundecino[8,7,6-hi]indole-8-carboxylic acid-N-ethylethanamine salt (Enantiomer 2)

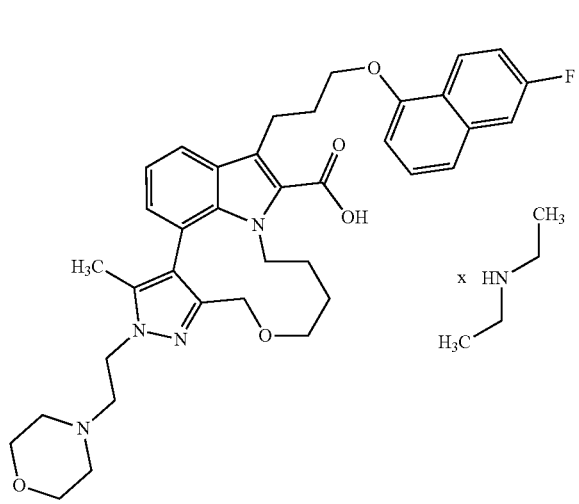

For the preparation of the racemic title compound and separation into its enantiomers see Example 284.

Analytical Chiral HPLC (method see Example 284): $R_t$=5.73 min.

Specific optical rotation (Method O1): −29.8° (c=1.0000 g/100 ml in DMSO)

LC-MS (Method 1): $R_t$=1.41 min; MS (ESIpos): m/z=642 [M+H]$^+$ $^1$H-NMR (400 MHz, DMSO-d6) δ[ppm]: 0.797 (0.48), 0.814 (0.55), 0.821 (0.56), 0.904 (0.49), 1.083 (1.22), 1.125 (7.53), 1.144 (15.89), 1.162 (7.81), 1.204 (0.72), 1.233 (0.92), 1.259 (0.95), 1.418 (0.79), 1.469 (0.81), 1.855 (16.00), 1.901 (0.67), 2.181 (1.36), 2.198 (2.05), 2.214 (1.46), 2.231 (0.55), 2.322 (0.79), 2.327 (1.06), 2.332 (0.83), 2.372 (1.16), 2.388 (1.57), 2.401 (2.21), 2.411 (1.48), 2.445 (2.21), 2.456 (1.82), 2.522 (3.56), 2.669 (1.73), 2.685 (1.06), 2.701 (1.55), 2.717 (0.86), 2.723 (0.85), 2.740 (1.45), 2.756 (1.09), 2.772 (0.69), 2.788 (0.42), 2.809 (1.76), 2.827 (5.05), 2.845 (4.92), 2.863 (1.66), 3.058 (0.99), 3.069 (0.92), 3.082 (0.85), 3.154 (0.67), 3.171 (1.06), 3.187 (1.23), 3.204 (1.69), 3.278 (4.11), 3.525 (4.34), 3.536 (7.21), 3.547 (4.22), 3.757 (0.81), 3.777 (0.60), 4.102 (0.41), 4.117 (0.85), 4.137 (0.97), 4.153 (1.92), 4.174 (2.21), 4.186 (4.15), 4.200 (1.64), 4.216 (3.97), 4.232 (1.04), 4.251 (0.72), 4.460 (2.80), 4.491 (2.36), 6.735 (1.53), 6.752 (1.71), 6.834 (1.38), 6.839 (1.43), 6.850 (1.41), 6.856 (1.48), 6.928 (1.41), 6.947 (2.10), 6.965 (1.22), 7.360 (0.85), 7.366 (0.97), 7.382 (1.53), 7.388 (1.94), 7.407 (2.70), 7.424 (5.38), 7.440 (0.62), 7.558 (1.73), 7.577 (1.57), 7.632 (1.59), 7.638 (1.59), 7.658 (1.59), 7.665 (1.55), 8.268 (1.34), 8.283 (1.48), 8.291 (1.43), 8.306 (1.36).

Example 287

(rac)-3-ethyl-7-{3-[(6-fluoronaphthalen-1-yl)oxy]propyl}-1-methyl-1,10,11,12,13,15-hexahydropyrazolo[4',3':9,10][1,6]oxazacycloundecino[8,7,6-hi]indole-8-carboxylic acid

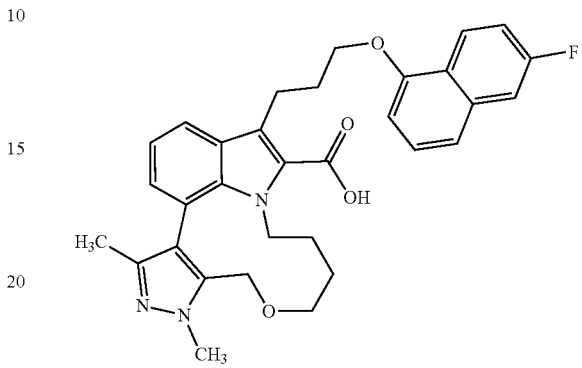

A solution of (rac)-ethyl 12-ethyl-1-(3-((6-fluoronaphthalen-1-yl)oxy)propyl)-10-methyl-4,5,6,7,9,10-hexahydropyrazolo[4',3':9,10][1]oxa[6]azacycloundecino[8,7,6-hi]indole-2-carboxylate (390 mg, 668 μmol; see Intermediate 482) in ethanol (74 mL) was treated with aqueous solution of lithium hydroxide (13.3 mL, 26.7 mmol, 2 M) and heated at 70° C. for 29 hours. The mixture was cooled to room temperature, volatiles were removed under reduced pressure, the residue was diluted with water, acidified to pH 2 aqueous hydrochloric acid and extracted three times with ethyl acetate. The combined organic extracts were dried over magnesium sulfate, solids were removed by filtration and volatiles were removed under reduced pressure. The residue was purified by flash chromatography on silica gel eluting with a gradient of ethyl acetate in hexanes (0-70%) to give the title compound (260 mg, 467 μmol).

LRMS (ESIpos): m/z=556.4 [M+H]$^+$ $^1$H NMR (400 MHz, Chloroform-d) δ 8.34 (dd, J=9.3, 5.8 Hz, 1H), 7.75 (dd, J=8.0, 1.3 Hz, 1H), 7.43-7.29 (m, 3H), 7.28-7.18 (m, 1H), 7.12-7.03 (m, 1H), 6.93 (dd, J=7.0, 1.2 Hz, 1H), 6.74-6.67 (m, 1H), 4.61 (dd, J=17.3, 13.7 Hz, 2H), 4.46 (d, J=13.4 Hz, 1H), 4.25-4.09 (m, 3H), 3.96 (s, 3H), 3.56-3.36 (m, 2H), 2.90 (s, 1H), 2.36 (s, 2H), 2.43-2.27 (m, 2H), 1.32-1.17 (m, 3H), 1.12 (d, J=8.4 Hz, 1H), 1.01 (t, J=7.6 Hz, 3H).

The title compound was separated into enantiomers by preparative chiral HPLC to give enantiomer 1 (80.0 mg, see Example 288) and enantiomer 2 (80.0 mg, see Example 289).

Preparative chiral HPLC method: Instrument: Sepiatec: Prep SFC100; column: Chiralpak IG 5 μm 250×30 mm; eluent A CO$_2$, eluent B: ethanol+0.2 Vol-% aqueous ammonia (32%); isocratic: 20% B; flow 100.0 ml/min temperature: 40° C.; BPR: 150 bar; MWD @ 220 nm.

Analytical chiral HPLC method: Instrument: Agilent: 1260, Aurora SFC-Modul; column: Chiralpak IG 5 μm 100×4.6 mm; eluent A: CO$_2$, eluent B: 2-propanol+0.2 Vol-% aqueous ammonia (32%); isocratic: 20% B; flow 4.0 ml/min; temperature: 37.5° C.; BPR: 100 bar; MWD @ 220 nm.

Example 288

(+)-3-ethyl-7-{3-[(6-fluoronaphthalen-1-yl)oxy]propyl}-1-methyl-1,10,11,12,13,15-hexahydropyrazolo[4',3':9,10][1,6]oxazacycloundecino[8,7,6-hi]indole-8-carboxylic acid (Enantiomer 1)

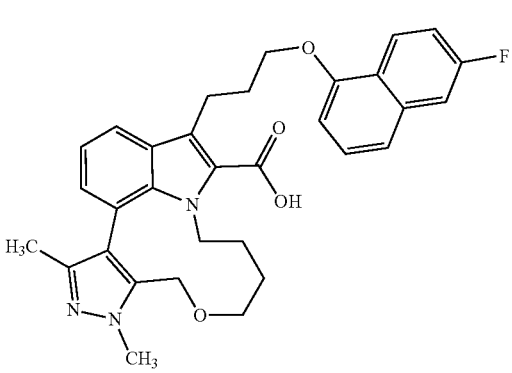 [SMILES: Cc1nn(C)c2c1-c1cccc3c(CCCOc4cccc5cc(F)ccc45)c(C(=O)O)n(c13)CCCCOC2]

For the preparation of the racemic title compound and separation into its enantiomers see Example 287.

Analytical Chiral HPLC (method see Example 287): $R_t$=1.68 min.

Specific optical rotation (Method O1): +67.7° (c=1.0000 g/100 ml in DMSO)

LC-MS (Method 1): $R_t$=1.53 min; MS (ESIpos): m/z=556 [M+H]+

1H-NMR (400 MHz, DMSO-d6) δ[ppm]: 0.729 (0.64), 0.797 (1.09), 0.802 (0.87), 0.807 (0.51), 0.813 (1.16), 0.820 (1.32), 0.839 (0.98), 0.849 (0.98), 0.854 (1.41), 0.865 (1.68), 0.881 (8.05), 0.900 (16.00), 0.919 (7.33), 0.964 (0.50), 0.985 (1.21), 1.009 (1.76), 1.052 (1.31), 1.062 (0.90), 1.068 (0.69), 1.083 (0.50), 1.142 (1.01), 1.149 (1.00), 1.157 (0.83), 1.164 (1.08), 1.178 (0.74), 1.214 (1.09), 1.227 (0.87), 1.265 (0.74), 1.292 (1.01), 1.354 (0.51), 1.459 (0.42), 1.907 (0.74), 1.919 (0.42), 2.074 (1.26), 2.083 (1.64), 2.113 (0.54), 2.131 (1.34), 2.137 (1.07), 2.149 (2.90), 2.156 (2.93), 2.167 (3.17), 2.175 (3.18), 2.187 (2.09), 2.193 (2.45), 2.209 (2.43), 2.224 (1.81), 2.242 (0.64), 2.518 (3.22), 2.523 (2.08), 2.725 (0.53), 2.743 (0.94), 2.755 (0.85), 2.773 (1.05), 2.791 (0.51), 3.250 (1.70), 3.264 (2.25), 3.283 (3.31), 3.332 (6.54), 3.347 (6.07), 3.405 (2.98), 3.416 (2.32), 3.435 (2.09), 3.450 (1.26), 3.970 (0.57), 3.993 (1.01), 4.018 (0.76), 4.027 (0.57), 4.183 (2.08), 4.199 (4.16), 4.214 (2.04), 4.235 (2.72), 4.268 (2.94), 4.520 (1.07), 4.544 (0.62), 4.555 (1.00), 4.611 (3.17), 4.644 (2.79), 6.817 (2.49), 6.820 (2.56), 6.835 (3.15), 6.850 (1.91), 6.857 (1.89), 6.865 (1.75), 6.871 (1.94), 7.015 (2.54), 7.035 (3.16), 7.053 (2.20), 7.352 (1.10), 7.358 (1.31), 7.374 (1.94), 7.380 (2.07), 7.396 (1.34), 7.402 (1.48), 7.421 (3.44), 7.429 (4.12), 7.435 (8.51), 7.450 (0.69), 7.637 (2.32), 7.644 (2.40), 7.663 (2.35), 7.670 (2.34), 7.713 (2.52), 7.715 (2.58), 7.733 (2.43), 8.250 (1.80), 8.266 (1.93), 8.274 (1.87), 8.288 (1.77).

Example 289

(−)-3-ethyl-7-{3-[(6-fluoronaphthalen-1-yl)oxy]propyl}-1-methyl-1,10,11,12,13,15-hexahydropyrazolo[4',3':9,10][1,6]oxazacycloundecino[8,7,6-hi]indole-8-carboxylic acid (Enantiomer 2)

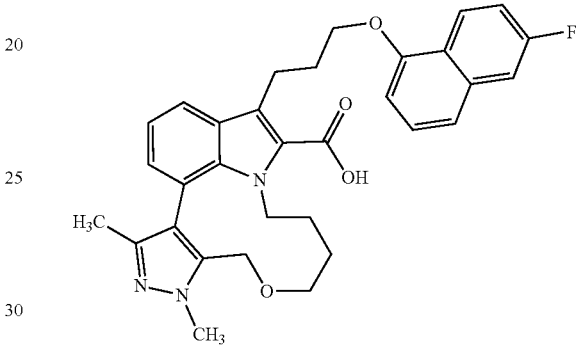

For the preparation of the racemic title compound and separation into its enantiomers see Example 287.

Analytical Chiral HPLC (method see Example 287): $R_t$=3.90 min.

Specific optical rotation (Method O1): −75.4° (c=1.0000 g/100 ml in DMSO)

LC-MS (Method 1): $R_t$=1.53 min; MS (ESIpos): m/z=556 [M+H]+

1H-NMR (400 MHz, DMSO-d6) δ[ppm]: 0.727 (0.51), 0.797 (1.02), 0.802 (0.79), 0.814 (1.11), 0.821 (1.26), 0.840 (0.91), 0.848 (0.79), 0.854 (1.16), 0.864 (1.48), 0.872 (1.53), 0.881 (5.46), 0.900 (10.08), 0.919 (4.86), 0.964 (0.43), 0.984 (0.91), 1.010 (1.29), 1.047 (1.13), 1.062 (0.78), 1.067 (0.55), 1.083 (0.44), 1.137 (0.83), 1.143 (0.81), 1.152 (0.65), 1.159 (0.91), 1.174 (0.48), 1.211 (0.78), 1.292 (0.70), 1.907 (0.54), 2.131 (0.85), 2.137 (0.78), 2.149 (1.96), 2.156 (2.00), 2.167 (2.18), 2.175 (2.19), 2.194 (1.74), 2.209 (1.76), 2.224 (1.27), 2.518 (3.17), 2.523 (2.03), 2.744 (0.67), 2.756 (0.60), 2.772 (0.78), 3.405 (2.13), 3.435 (1.42), 3.847 (16.00), 3.970 (0.41), 3.994 (0.67), 4.018 (0.52), 4.185 (1.39), 4.199 (2.70), 4.214 (1.37), 4.235 (1.89), 4.268 (2.02), 4.520 (0.68), 4.555 (0.62), 4.611 (2.22), 4.645 (1.96), 6.819 (1.71), 6.836 (2.10), 6.851 (1.23), 6.857 (1.23), 6.865 (1.21), 6.872 (1.23), 7.015 (1.60), 7.034 (2.17), 7.053 (1.39), 7.352 (0.69), 7.359 (0.75), 7.375 (1.24), 7.381 (1.34), 7.403 (0.95), 7.421 (2.33), 7.430 (2.90), 7.436 (5.55), 7.450 (0.49), 7.638 (1.57), 7.644 (1.63), 7.664 (1.59), 7.670 (1.58), 7.714 (1.66), 7.733 (1.57), 8.251 (1.07), 8.266 (1.16), 8.274 (1.15), 8.289 (1.05).

Example 290

(rac)-12-ethyl-11-methyl-1-(3-((5,6,7,8-tetrahydronaphthalen-1-yl)oxy)propyl)-4,5,6,7,9,11-hexahydropyrazolo[4',3':9,10][1]oxa[6]azacycloundecino[8,7,6-hi]indole-2-carboxylic acid

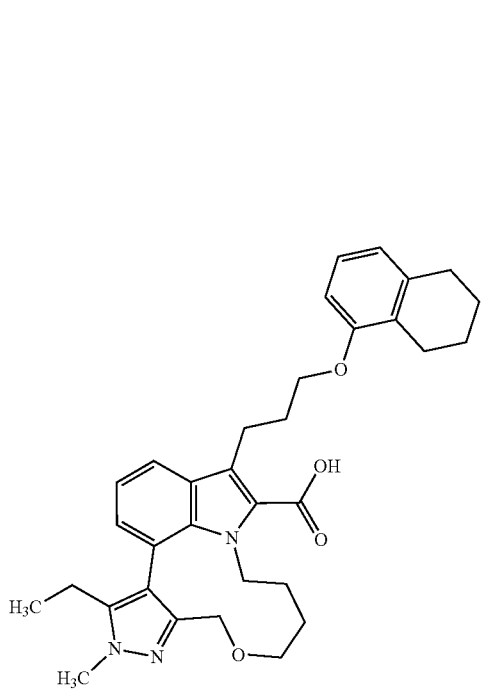 [SMILES: CCc1c2c(nn1C)COCCCCn1c(C(=O)O)c(CCCOc3cccc4c3CCCC4)c3cccc-2c31]

A solution of (rac)-ethyl 12-ethyl-11-methyl-1-(3-((5,6,7,8-tetrahydronaphthalen-1-yl)oxy)propyl)-4,5,6,7,9,11-hexahydropyrazolo[4',3':9,10][1]oxa[6]azacycloundecino[8,7,6-hi]indole-2-carboxylate (170 mg, 298 μmol; see Intermediate 484) in ethanol (6.5 mL) was treated with aqueous solution of lithium hydroxide (2M, 6 ml) and heated to 70° C. for 24 hours. The reaction mixture was cooled to room temperature, volatiles were removed under reduced pressure, the residue was diluted with water, acidified to pH 2 with aqueous hydrochloric acid (1 M) and extracted with ethyl acetate. The combined organic extracts were dried over magnesium sulfate, solids were removed by filtration and volatiles were removed under reduced pressure. The residue was purified by flash chromatography on silica gel eluting with a gradient of ethyl acetate in hexanes (0-85%) to give the title compound (142 mg, 263 μmol).

LRMS (ESIpos): m/z=542.4 [M+H]$^+$ $^1$H NMR (300 MHz, Chloroform-d) δ 10.38 (s, 2H), 7.74 (d, J=8.0 Hz, 1H), 7.24-6.98 (m, 3H), 6.66 (dd, J=18.8, 7.9 Hz, 2H), 4.73 (d, J=12.6 Hz, 1H), 4.51-4.38 (m, 2H), 4.10 (dt, J=21.0, 6.7 Hz, 3H), 3.94 (s, 3H), 3.54-3.23 (m, 3H), 2.78 (q, J=5.8 Hz, 4H), 2.41-2.17 (m, 4H), 2.07 (s, 1H), 1.90-1.70 (m, 4H), 1.67-1.51 (m, 1H), 1.43 (tt, J=6.7, 2.5 Hz, 1H), 1.26 (q, J=7.3 Hz, 3H), 0.96 (t, J=7.5 Hz, 3H).

Example 291

(rac)-12-ethyl-10-methyl-1-(3-((5,6,7,8-tetrahydronaphthalen-1-yl)oxy)propyl)-4,5,6,7,9,10-hexahydropyrazolo[4',3':9,10][1]oxa[6]azacycloundecino[8,7,6-hi]indole-2-carboxylic acid

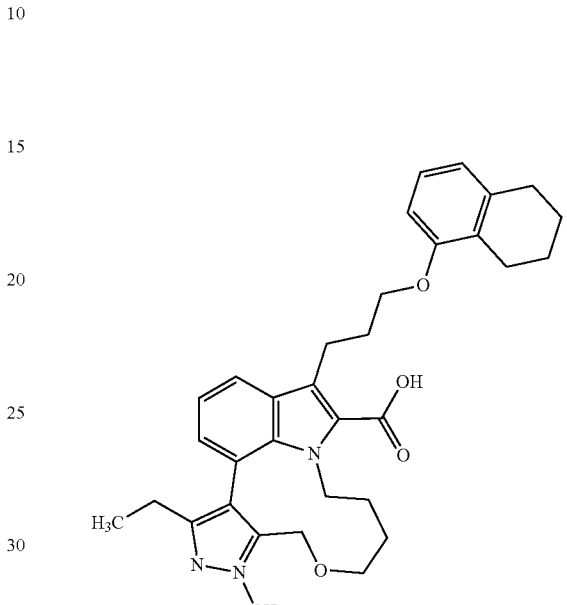

A solution of (rac)-ethyl 12-ethyl-10-methyl-1-(3-((5,6,7,8-tetrahydronaphthalen-1-yl)oxy)propyl)-4,5,6,7,9,10-hexahydropyrazolo[4',3':9,10][1]oxa[6]azacycloundecino[8,7,6-hi]indole-2-carboxylate (350 mg, 614 μmol; see Intermediate 483) in ethanol (13 mL) was treated with aqueous solution of lithium hydroxide (2M, 12.2 mL, 24.5 mmol) and heated at 70° C. for 24 hours. The reaction mixture was cooled to room temperature, volatiles were removed under reduced pressure, the residue was diluted with water, acidified to pH 2 with aqueous hydrochloric acid and extracted three times with ethyl acetate. The combined organic extracts were dried over magnesium sulfate, solids were removed by filtration and volatiles were removed under reduced pressure. The residue was purified by flash chromatography on silica gel eluting with a gradient of ethyl acetate in hexanes (0-70%) to give the title compound (190 mg, 333 μmol).

MS (ESIpos): m/z=542.4 [M+H]$^+$ $^1$H NMR (300 MHz, Chloroform-d) δ 7.75 (dd, J=8.0, 1.3 Hz, 1H), 7.17-6.88 (m, 3H), 6.65 (dd, J=22.9, 7.8 Hz, 2H), 4.66 (d, J=14.2 Hz, 1H), 4.60 (d, J=13.5 Hz, 1H), 4.48 (d, J=13.4 Hz, 1H), 4.25-4.11 (m, 1H), 4.05 (t, J=6.1 Hz, 2H), 3.99 (s, 3H), 3.63-3.45 (m, 1H), 3.45-3.27 (m, 2H), 2.92 (s, 1H), 2.75 (d, J=5.8 Hz, 4H), 2.37 (qd, J=7.5, 2.6 Hz, 2H), 2.28-2.16 (m, 2H), 1.78 (s, 6H), 1.23 (q, J=14.6, 13.4 Hz, 5H), 1.02 (t, J=7.6 Hz, 3H).

Example 292

(rac)-7-{3-[(6-fluoronaphthalen-1-yl)oxy]propyl}-3,4-dimethyl-2-[2-(morpholin-4-yl)ethyl]-2,10,11,12,13,15-hexahydropyrazolo[4',3':9,10][1,6]oxazacycloundecino[8,7,6-hi]indole-8-carboxylic acid

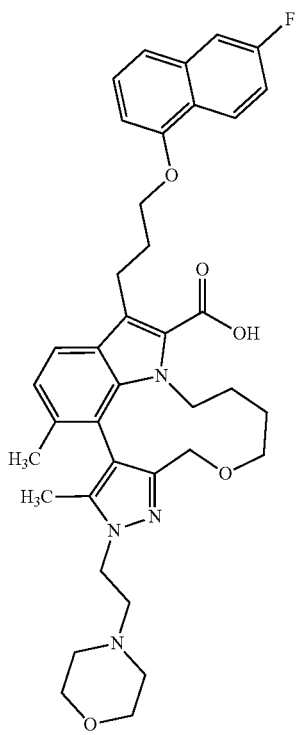 [SMILES: Cc1ccc2c(CCCOc3cccc4cc(F)ccc34)c(C(=O)O)n3c2c1-c1c(nn(CCN2CCOCC2)c1C)COCCCC3]

A solution of (rac)-ethyl 1-(3-((6-fluoronaphthalen-1-yl)oxy)propyl)-12,13-dimethyl-11-(2-morpholinoethyl)-4,5,6,7,9,11-hexahydropyrazolo[4',3':9,10][1]oxa[6]azacycloundecino[8,7,6-hi]indole-2-carboxylate (200 mg, 292 µmol; see Intermediate 488) in ethanol (6 mL) was treated with aqueous solution of lithium hydroxide (2 M, 5.80 mL, 11.6 mmol) and heated at 70° C. for 21 hours. The reaction mixture was cooled to room temperature, volatiles were removed under reduced pressure, the residue was diluted with water, acidified to pH 2 with aqueous hydrochloric acid and extracted three times with ethyl acetate. The combined organic extracts were dried over magnesium sulfate, solids were removed by filtration and volatiles were removed under reduced pressure. The residue was purified by flash chromatography on silica gel eluting with a gradient of methanol in dichloromethane (0-5%) to give the title compound (95 mg, 145 µmol).

MS (ESIpos): m/z=655.3 [M+H]$^+$ $^1$H NMR (300 MHz, Chloroform-d) δ 11.93 (s, 1H), 8.36 (dd, J=9.2, 5.8 Hz, 1H), 7.60 (d, J=8.2 Hz, 1H), 7.44-7.29 (m, 3H), 7.22 (td, J=8.8, 2.6 Hz, 1H), 7.04 (d, J=8.2 Hz, 1H), 6.69 (dd, J=6.7, 2.0 Hz, 1H), 4.58 (d, J=12.6 Hz, 1H), 4.44 (d, J=12.5 Hz, 1H), 4.39-4.33 (m, 1H), 4.30 (t, J=6.8 Hz, 2H), 4.15 (dt, J=17.7, 6.7 Hz, 2H), 3.91 (t, J=10.9 Hz, 1H), 3.70 (t, J=4.6 Hz, 4H), 3.43 (q, J=8.1, 6.9 Hz, 3H), 3.33-3.18 (m, 1H), 2.88 (t, J=6.7 Hz, 2H), 2.56 (h, J=7.0 Hz, 4H), 2.33 (h, J=6.1, 5.5 Hz, 2H), 2.07 (s, 3H), 1.85 (s, 3H), 1.55-1.06 (m, 4H).

The title compound was separated into enantiomers by preparative chiral HPLC to give enantiomer 1 (27.8 mg, see Example 293) and enantiomer 2 (24.2 mg, see Example 294).

Preparative chiral HPLC method: Instrument: Labomatic HD5000, Labocord-5000; Gilson GX-241, Labcol Vario 4000, column: YMC Amylose SA 5µ 250×50 mm; eluent A: hexane+0.1 Vol-% diethylamine (99%); eluent B: 2-propanol; gradient: 20-50% B in 15 min; flow 40.0 ml/min; UV 254 nm.

Analytical chiral HPLC method: Instrument: Agilent HPLC 1260; column: YMC Amylose SA 3µ 100×4.6 mm; eluent A: hexane+0.1 Vol-% diethylamine (99%); eluent B: 2-propanol; gradient: 20-50% B in 7 min; flow 1.4 ml/min; temperature: 25° C.; DAD 254 nm.

Example 293

(+)-7-{3-[(6-fluoronaphthalen-1-yl)oxy]propyl}-3,4-dimethyl-2-[2-(morpholin-4-yl)ethyl]-2,10,11,12,13,15-hexahydropyrazolo[4',3':9,10][1,6]oxazacycloundecino[8,7,6-hi]indole-8-carboxylic acid-N-ethylethanamine salt (Enantiomer 1)

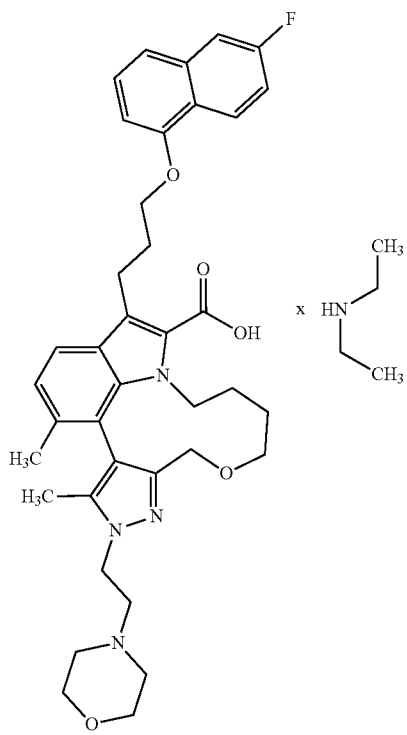

For the preparation of the racemic title compound and separation into its enantiomers see Example 292.

Analytical Chiral HPLC (method see Example 292): R$_t$=2.98 min.

Specific optical rotation (Method O1): +22.0° (c=1.0000 g/100 ml in DMSO)

LC-MS (Method 1): R$_t$=1.26 min; MS (ESIpos): m/z=656 [M+H]$^+$ $^1$H-NMR (400 MHz, DMSO-d6) δ[ppm]: 0.697 (0.42), 0.840 (1.11), 0.858 (1.11), 1.051 (2.00), 1.085 (1.70), 1.123 (7.74), 1.141 (14.50), 1.160 (7.40), 1.237 (3.18), 1.525 (0.47), 1.779 (16.00), 1.902 (1.21), 1.952 (14.87), 2.173

(2.74), 2.189 (3.67), 2.206 (2.86), 2.327 (3.13), 2.408 (7.84), 2.420 (8.31), 2.670 (2.37), 2.687 (1.75), 2.704 (2.84), 2.722 (2.74), 2.739 (1.63), 2.755 (0.94), 2.811 (2.51), 2.829 (6.41), 2.847 (6.19), 2.865 (2.29), 3.148 (2.10), 3.171 (2.24), 3.186 (2.05), 3.203 (2.54), 3.525 (8.78), 3.738 (1.23), 3.917 (0.47), 3.932 (0.47), 4.165 (3.40), 4.178 (3.85), 4.190 (3.38), 4.203 (4.24), 4.234 (3.92), 4.260 (0.99), 4.346 (3.70), 4.377 (2.79), 6.839 (1.90), 6.855 (2.00), 6.919 (2.49), 6.939 (2.71), 7.368 (1.11), 7.391 (2.69), 7.412 (3.82), 7.428 (6.73), 7.484 (2.64), 7.504 (2.42), 7.637 (1.87), 7.643 (2.05), 7.663 (1.92), 7.669 (2.00), 8.266 (1.58), 8.281 (1.73), 8.289 (1.80), 8.304 (1.58).

Example 294

(−)-7-{3-[(6-fluoronaphthalen-1-yl)oxy]propyl}-3,4-dimethyl-2-[2-(morpholin-4-yl)ethyl]-2,10,11,12,13,15-hexahydropyrazolo[4',3':9,10][1,6]oxazacycloundecino[8,7,6-hi]indole-8-carboxylic acid-N-ethylethanamine salt (Enantiomer 2)

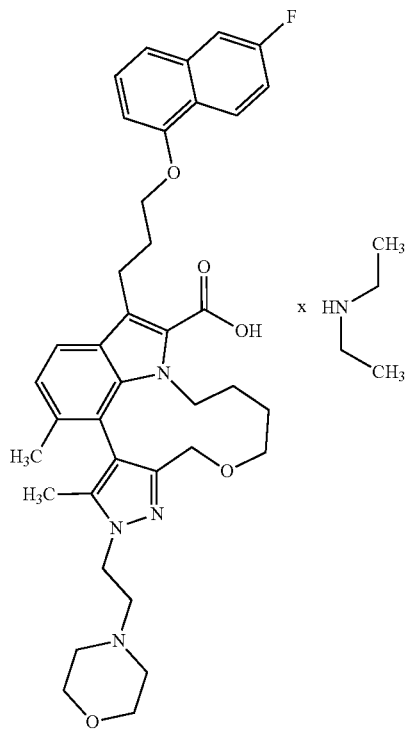

For the preparation of the racemic title compound and separation into its enantiomers see Example 292.

Analytical Chiral HPLC (method see Example 292): $R_t$=4.64 min.

Specific optical rotation (Method O1): −22.3° (c=1.0000 g/100 ml in DMSO)

LC-MS (Method 1): $R_t$=1.26 min; MS (ESIpos): m/z=656 [M+H]$^+$ $^1$H-NMR (400 MHz, DMSO-d6) δ[ppm]: 0.697 (0.48), 0.821 (0.65), 0.840 (1.27), 0.858 (1.24), 1.006 (1.08), 1.027 (1.21), 1.049 (1.40), 1.088 (1.48), 1.121 (5.17), 1.139 (9.67), 1.157 (4.88), 1.236 (2.88), 1.292 (1.29), 1.526 (0.51), 1.778 (16.00), 1.904 (1.08), 1.956 (14.03), 2.171 (2.40), 2.188 (3.23), 2.206 (2.56), 2.327 (3.21), 2.409 (7.11), 2.421 (7.54), 2.669 (2.26), 2.689 (1.59), 2.705 (2.53), 2.723 (2.45), 2.739 (1.45), 2.756 (0.84), 2.810 (1.56), 2.827 (3.88), 2.846 (3.77), 2.864 (1.43), 3.148 (1.72), 3.174 (1.86), 3.190 (1.72), 3.207 (2.21), 3.255 (3.31), 3.515 (4.90), 3.526 (7.54), 3.537 (4.85), 3.745 (1.02), 3.917 (0.51), 3.932 (0.51), 4.167 (2.96), 4.179 (3.34), 4.192 (2.99), 4.203 (3.80), 4.234 (3.58), 4.260 (0.86), 4.349 (3.29), 4.381 (2.15), 6.838 (1.62), 6.843 (1.78), 6.854 (1.70), 6.859 (1.83), 6.927 (2.18), 6.947 (2.40), 7.363 (1.00), 7.369 (1.13), 7.385 (1.80), 7.392 (2.45), 7.414 (3.72), 7.430 (6.33), 7.445 (0.94), 7.494 (2.21), 7.514 (1.99), 7.638 (1.80), 7.644 (1.91), 7.664 (1.83), 7.670 (1.86), 8.266 (1.51), 8.282 (1.67), 8.290 (1.70), 8.305 (1.51).

Example 295

(rac)-7-{3-[(6-chloronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid

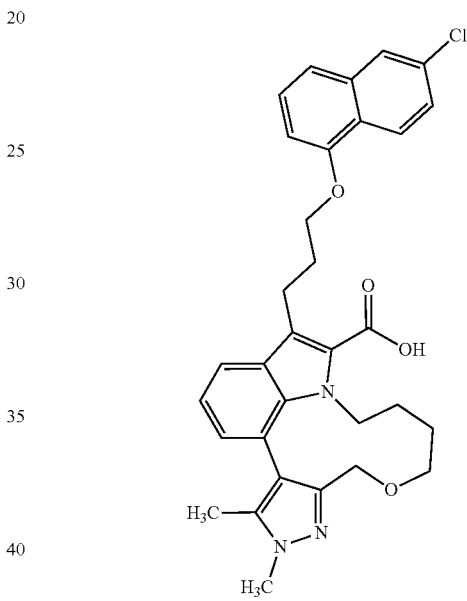

Crude (rac)-ethyl 1-(3-((6-chloronaphthalen-1-yl)oxy)propyl)-11,12-dimethyl-4,5,6,7,9,11-hexahydropyrazolo[4',3':9,10][1,6]oxaazacycloundecino[8,7,6-hi]indole-2-carboxylate (125 mg; see Intermediate 466) was dissolved in ethanol (15 ml), treated with aqueous solution of lithium hydroxide (2 M, 2 ml), and heated to 75° C. for 18 hours. The mixture was then cooled to room temperature, volatiles were removed under reduced pressure, and the residue was partitioned between ethyl acetate (50 ml) and aqueous hydrogen chloride (3 N, 50 ml). The layers were separated and the organic phase was washed with aqueous saturated sodium chloride solution, the combined aqueous washes were back extracted with ethyl acetate, and the combined organic phases were dried over sodium sulfate. Insoluble materials were removed by filtration, and the volatiles were removed under reduced pressure. The resulting residue was purified by normal phase flash chromatography on silica gel eluting with a gradient of ethyl acetate in hexanes (50-100%) to give the title compound as an off white solid (89 mg).

LRMS (ESIneg) m/z=556 [M−H]$^-$ $^1$H NMR (300 MHz, Chloroform-d) δ 8.34-8.24 (m, 1H), 7.74 (d, J=2.1 Hz, 1H), 7.70 (dd, J=8.0, 1.3 Hz, 1H), 7.38 (dd, J=8.9, 2.0 Hz, 1H), 7.34 (d, J=0.9 Hz, 1H), 7.27 (t, J=8.3

Hz, 1H), 7.10 (dd, J=7.9, 7.1 Hz, 1H), 7.01 (dd, J=7.1, 1.3 Hz, 1H), 6.72 (dd, J=7.5, 1.2 Hz, 1H), 4.71 (d, J=12.6 Hz, 1H), 4.42 (d, J=12.5 Hz, 2H), 4.18 (t, J=6.4 Hz, 2H), 4.08-3.96 (m, 1H), 3.88 (s, 3H), 3.57-3.34 (m, J=7.3, 6.8 Hz, 3H), 3.26 (dt, J=11.8, 6.0 Hz, 1H), 2.44-2.27 (m, 2H), 1.90 (s, 3H), 1.60-1.29 (m, 2H), 1.23-1.11 (m, 2H).

The title compound was separated into enantiomers by preparative chiral HPLC to give enantiomer 1 (24.1 mg, see Example 296) and enantiomer 2 (23.2 mg, see Example 297).

Preparative chiral HPLC method: Instrument: Labomatic HD5000, Labocord-5000; Gilson GX-241, Labcol Vario 4000, column: Chiralpak IG 5μ 250×30 mm; eluent A: hexane+0.1 Vol-% diethylamine (99%); eluent B: 2-propanol; isocratic 80:20; flow 40.0 ml/min; UV 254 nm.

Analytical chiral HPLC method: Agilent HPLC 1260; column: Chiralpak IG 3μ 100×4.6 mm; eluent A: hexane+0.1 Vol-% diethylamine (99%); eluent B: 2-propanol; isocratic 80:20; flow 1.4 ml/min; temperature: 25° C.; DAD 254 nm.

Example 296

(+)-7-{3-[(6-chloronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid-N-ethylethanamine salt (Enantiomer 1)

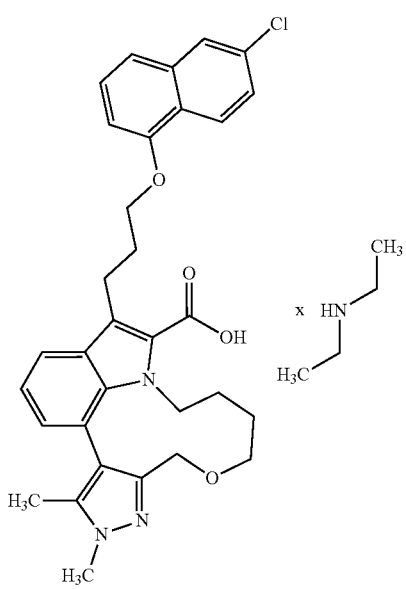

For the preparation of the racemic title compound and separation into its enantiomers see Example 295.

Analytical Chiral HPLC (method see Example 295): $R_t$=2.62 min.

Specific optical rotation (Method O1): +44.2° (c=1.0000 g/100 ml in DMSO)

LC-MS (Method 1): $R_t$=1.57 min; MS (ESIpos): m/z=558 [M+H]$^+$ $^1$H-NMR (400 MHz, DMSO-d6) δ[ppm]: 1.070 (0.62), 1.088 (0.98), 1.097 (1.03), 1.123 (7.38), 1.141 (16.00), 1.159 (7.35), 1.235 (0.85), 1.298 (0.55), 1.820 (14.90), 2.180 (1.02), 2.197 (1.55), 2.214 (1.07), 2.331 (0.70), 2.518 (3.82), 2.523 (2.50), 2.673 (0.72), 2.808 (1.83), 2.826 (5.55), 2.844 (5.53), 2.862 (1.72), 3.067 (0.72), 3.092 (0.58), 3.155 (0.40), 3.174 (0.70), 3.188 (0.80), 3.207 (1.20), 3.252 (1.67), 3.269 (2.40), 3.790 (15.58), 4.149 (0.43), 4.157 (0.68), 4.173 (3.50), 4.186 (1.55), 4.203 (2.75), 4.438 (2.28), 4.469 (1.92), 6.728 (1.13), 6.746 (1.33), 6.884 (1.17), 6.893 (1.18), 6.898 (1.13), 6.906 (1.32), 6.920 (1.42), 6.939 (1.75), 6.957 (1.10), 7.422 (2.95), 7.427 (2.55), 7.435 (5.58), 7.483 (1.93), 7.489 (2.07), 7.506 (2.07), 7.512 (2.02), 7.554 (1.32), 7.571 (1.25), 7.983 (3.12), 7.989 (3.17), 8.218 (2.85), 8.241 (2.62).

Example 297

(−)-7-{3-[(6-chloronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid-N-ethylethanamine salt (Enantiomer 2)

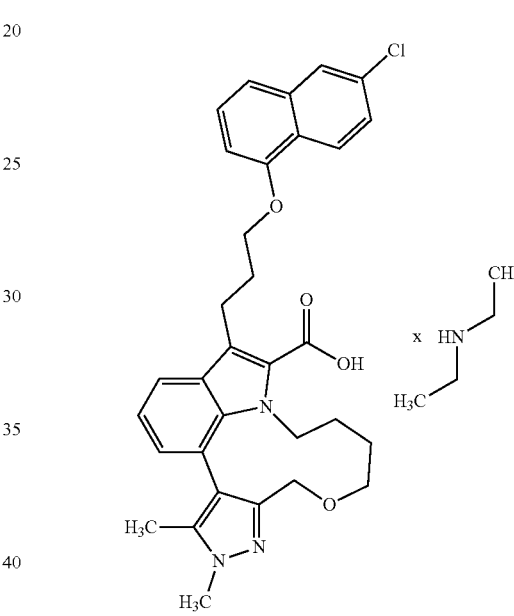

For the preparation of the racemic title compound and separation into its enantiomers see Example 295.

Analytical Chiral HPLC (method see Example 295): $R_t$=4.64 min.

Specific optical rotation (Method O1): −41.7° (c=1.0000 g/100 ml in DMSO)

LC-MS (Method 1): $R_t$=1.57 min; MS (ESIpos): m/z=558 [M+H]$^+$ $^1$H-NMR (400 MHz, DMSO-d6) δ[ppm]: 1.026 (1.39), 1.042 (1.42), 1.070 (0.48), 1.083 (0.73), 1.087 (0.91), 1.094 (0.87), 1.105 (0.88), 1.120 (7.70), 1.138 (16.00), 1.156 (7.87), 1.235 (0.65), 1.258 (0.41), 1.276 (0.42), 1.295 (0.47), 1.822 (13.56), 1.898 (0.53), 1.959 (0.58), 2.180 (0.92), 2.198 (1.43), 2.215 (0.97), 2.331 (0.49), 2.518 (2.81), 2.523 (1.79), 2.673 (0.50), 2.794 (1.88), 2.812 (5.88), 2.830 (5.67), 2.848 (1.78), 3.066 (0.65), 3.078 (0.53), 3.091 (0.53), 3.166 (0.64), 3.180 (0.69), 3.198 (1.05), 3.217 (0.70), 3.246 (1.40), 3.255 (1.42), 3.266 (1.91), 3.281 (1.71), 3.299 (2.12), 3.764 (0.60), 3.790 (13.65), 4.147 (0.41), 4.155 (0.61), 4.174 (2.64), 4.185 (1.47), 4.205 (2.37), 4.431 (1.96), 4.462 (1.84), 4.486 (0.42), 6.708 (1.20), 6.723 (1.40), 6.880 (1.10), 6.889 (1.06), 6.894 (1.06), 6.903 (1.30), 6.907 (1.47), 6.926 (1.75), 6.944 (1.15), 7.419 (2.64), 7.425 (2.28), 7.433 (5.08), 7.483 (1.80), 7.488 (1.86), 7.505 (1.85), 7.511 (1.87), 7.535 (1.32), 7.536 (1.35), 7.554 (1.27), 7.557 (1.23), 7.983 (2.87), 7.988 (2.84), 8.218 (2.55), 8.241 (2.39).

Example 298

(rac)-3-ethyl-7-{3-[(5-fluoronaphthalen-1-yl)oxy]propyl}-1-methyl-1,10,11,12,13,15-hexahydropyrazolo[4',3':9,10][1,6]oxazacycloundecino[8,7,6-hi]indole-8-carboxylic acid

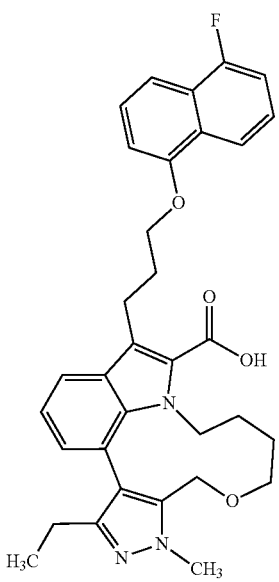 [SMILES: CCc1nn(C)c2c1-c1cccc3c(CCCOc4cccc5c(F)cccc45)c(C(=O)O)n(c13)CCCCOC2]

Step A

A mixture of caesium carbonate (200 mg, 0.61 mmol), 5-fluoronaphthalen-1-ol (60 mg, 0.37 mmol) and (rac)-ethyl 1-(3-bromopropyl)-12-ethyl-10-methyl-4,5,6,7,9,10-hexahydropyrazolo[4',3':9,10][1,6]oxaazacycloundecino[8,7,6-hi]indole-2-carboxylate (107 mg, 0.21 mmol; see Intermediate 455) in tetrahydrofuran (7 ml) was heated to 35° C. for 17 hours, then warmed to 45° C. for 96 hours, cooled to room temperature, then heated to 55° C. for 22 hours. The crude reaction mixture was used in the next step without further manipulation.

LRMS (ESIpos) m/z 584 [M+H]$^+$

Step B

To the crude product mixture of (rac)-ethyl-3-ethyl-7-{3-[(5-fluoronaphthalen-1-yl)oxy]propyl}-1-methyl-1,10,11,12,13,15-hexahydropyrazolo[4',3':9,10][1,6]oxazacycloundecino[8,7,6-hi]indole-8-carboxylate (116 mg theory) (Example 298, step A) in tetrahydrofuran (7 ml) was added ethanol (2 ml) and aqueous solution of lithium hydroxide (2 M, 2.5 ml), and the resulting suspension was heated to 70° C. for 24 hours. The reaction was cooled to room temperature, volatiles were removed under reduced pressure, and the residue was partitioned between ethyl acetate (50 ml) and aqueous hydrochloric acid (3N, 50 ml). The organic phase was washed with saturated aqueous sodium chloride solution, the combined aqueous phases were back extracted with ethyl acetate, and combined organic layers were then dried over sodium sulfate. Insoluble materials were removed by filtration, and volatiles were removed under reduced pressure. The residue was purified by flash chromatography on silica gel eluting with a gradient of methanol in dichloromethane (0-10%) to give the title compound as an off white foam (40 mg).

LRMS (ESIneg) m/z 554 [M−H]$^−$ $^1$H NMR (300 MHz, Chloroform-d) δ 8.13 (dt, J=8.5, 1.0 Hz, 1H), 7.76 (dd, J=8.1, 1.3 Hz, 1H), 7.63 (d, J=8.4 Hz, 1H), 7.43-7.31 (m, 2H), 7.14 (ddd, J=10.7, 7.7, 1.0 Hz, 1H), 7.07 (dd, J=8.1, 7.1 Hz, 1H), 6.92 (dd, J=7.1, 1.2 Hz, 1H), 6.79 (dd, J=7.8, 0.9 Hz, 1H), 4.73-4.62 (m, 1H), 4.59 (d, J=13.5 Hz, 1H), 4.46 (d, J=13.4 Hz, 1H), 4.20 (t, J=6.1 Hz, 3H), 3.98 (s, 3H), 3.59-3.37 (m, 3H), 2.97-2.82 (m, 1H), 2.37 (dtd, J=10.3, 7.4, 4.2 Hz, 4H), 1.63-1.45 (m, 1H), 1.34-1.07 (m, 3H), 1.02 (t, J=7.6 Hz, 3H).

The title compound was separated into enantiomers by preparative chiral HPLC to give enantiomer 1 (6.6 mg, see Example 300) and enantiomer 2 (7.7 mg, see Example 299).

Preparative chiral HPLC method: Instrument: Sepiatec: Prep SFC100; column: Chiralpak IG 5 μm 250×30 mm; eluent A CO$_2$, eluent B: ethanol; isocratic: 33% B; flow 100.0 ml/min temperature: 40° C.; BPR: 150 bar; MWD @ 220 nm.

Analytical chiral HPLC method: Instrument: Agilent 1260, Aurora SFC-Modul; column: Chiralpak IG 5 μm 100×4.6 mm; eluent A: CO$_2$, eluent B: ethanol; isocratic: 33% B; flow 4.0 ml/min; temperature: 37.5° C.; BPR: 100 bar; MWD @ 220 nm.

Example 299

3-ethyl-7-{3-[(5-fluoronaphthalen-1-yl)oxy]propyl}-1-methyl-1,10,11,12,13,15-hexahydropyrazolo[4',3':9,10][1,6]oxazacycloundecino[8,7,6-hi]indole-8-carboxylic acid (Enantiomer 2)

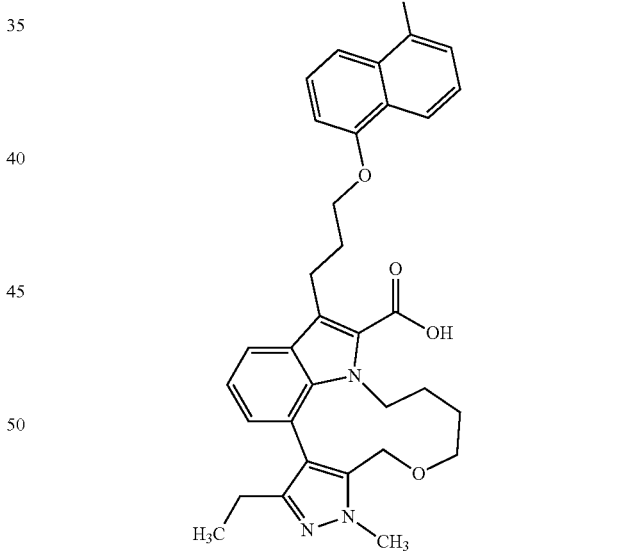

For the preparation of the racemic title compound and separation into its enantiomers see Example 298.

Analytical Chiral HPLC (method see Example 298): R$_t$=1.33 min.

LC-MS (Method 1): R$_t$=1.57 min; MS (ESIpos): m/z=557 [M+H]$^+$ $^1$H-NMR (400 MHz, DMSO-d6) δ[ppm]: 0.797 (0.73), 0.814 (0.74), 0.821 (0.78), 0.839 (0.43), 0.881 (4.73), 0.900 (10.88), 0.919 (4.86), 1.011 (1.12), 1.156 (0.61), 1.173 (0.43), 1.205 (1.23), 1.221 (0.58), 1.235 (0.67), 1.288 (0.48), 2.129 (0.80), 2.136 (0.67), 2.147 (1.92), 2.155 (1.93), 2.166

(1.93), 2.174 (1.95), 2.185 (0.89), 2.193 (1.36), 2.202 (1.25), 2.211 (1.47), 2.230 (1.13), 2.518 (4.47), 2.523 (2.88), 2.746 (0.61), 2.758 (0.52), 2.775 (0.67), 3.235 (0.47), 3.254 (0.78), 3.269 (1.08), 3.287 (1.88), 3.388 (1.54), 3.407 (1.30), 3.418 (0.95), 3.436 (0.95), 3.452 (0.50), 3.847 (16.00), 3.999 (0.63), 4.011 (0.41), 4.023 (0.43), 4.205 (1.38), 4.221 (2.88), 4.232 (2.66), 4.266 (1.95), 4.513 (0.73), 4.524 (0.43), 4.548 (0.65), 4.611 (2.10), 4.645 (1.84), 6.822 (1.45), 6.840 (1.71), 6.989 (1.80), 7.007 (1.99), 7.014 (1.69), 7.034 (1.93), 7.052 (1.32), 7.337 (0.86), 7.339 (0.87), 7.356 (1.23), 7.364 (0.91), 7.384 (1.17), 7.464 (0.89), 7.475 (1.45), 7.484 (1.27), 7.496 (2.88), 7.504 (0.93), 7.515 (1.90), 7.564 (2.57), 7.585 (1.49), 7.719 (1.56), 7.721 (1.54), 7.739 (1.47), 8.049 (2.18), 8.070 (1.93).

Example 300

3-ethyl-7-{3-[(5-fluoronaphthalen-1-yl)oxy]propyl}-1-methyl-1,10,11,12,13,15-hexahydropyrazolo[4',3':9,10][1,6]oxazacycloundecino[8,7,6-hi]indole-8-carboxylic acid (Enantiomer 1)

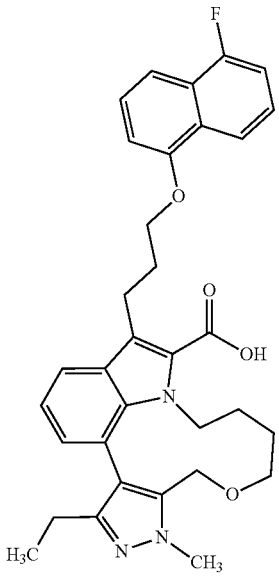 [SMILES: CCc1nn(C)c2c1-c1cccc3c(CCCOc4cccc5c(F)cccc45)c(C(=O)O)n(c13)CCCCOC2]

For the preparation of the racemic title compound and separation into its enantiomers see Example 298.

Analytical Chiral HPLC (method see Example 298): $R_t$=0.81 min.

LC-MS (Method 1): $R_t$=1.57 min; MS (ESIpos): m/z=557 [M+H]$^+$ $^1$H-NMR (400 MHz, DMSO-d6) δ[ppm]: 0.797 (0.70), 0.814 (0.75), 0.821 (0.77), 0.839 (0.43), 0.881 (4.70), 0.900 (10.81), 0.919 (5.01), 1.011 (1.18), 1.103 (0.43), 1.138 (0.50), 1.156 (1.08), 1.174 (0.68), 1.205 (0.91), 1.222 (0.58), 1.231 (0.62), 1.288 (0.50), 2.130 (0.81), 2.136 (0.70), 2.147 (1.97), 2.155 (1.97), 2.166 (2.01), 2.174 (1.99), 2.185 (0.93), 2.194 (1.45), 2.202 (1.16), 2.211 (1.57), 2.230 (1.20), 2.518 (4.68), 2.523 (3.08), 2.746 (0.64), 2.758 (0.54), 2.775 (0.68), 3.254 (0.68), 3.269 (0.95), 3.287 (1.64), 3.388 (1.10), 3.407 (1.08), 3.418 (0.81), 3.436 (0.87), 3.452 (0.43), 3.847 (16.00), 3.999 (0.66), 4.010 (0.43), 4.023 (0.44), 4.205 (1.43), 4.221 (3.02), 4.232 (2.73), 4.266 (2.01), 4.513 (0.75), 4.524 (0.44), 4.537 (0.41), 4.548 (0.70), 4.611 (2.15), 4.645 (1.92), 6.825 (1.49), 6.840 (1.76), 6.989 (1.86), 7.008 (2.09), 7.015 (1.74), 7.034 (1.99), 7.052 (1.32), 7.339 (0.89), 7.356 (1.24), 7.365 (0.93), 7.384 (1.20), 7.464 (0.97), 7.475 (1.53), 7.485 (1.32), 7.496 (2.96), 7.504 (0.97), 7.515 (1.97), 7.564 (2.63), 7.585 (1.53), 7.721 (1.63), 7.739 (1.53), 8.049 (2.24), 8.070 (2.05).

Example 301

(rac)-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid

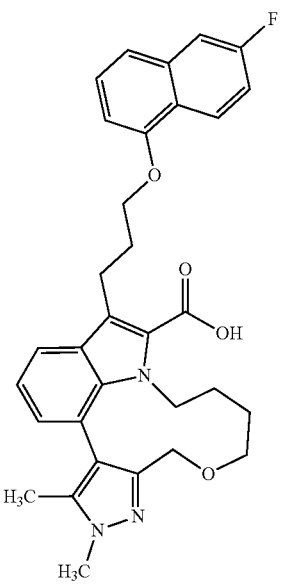 [SMILES: Cc1c2c(nn1C)COCCCCn1c(C(=O)O)c(CCCOc3cccc4cc(F)ccc34)c3cccc-2c31]

Crude (rac)-ethyl 1-(3-((6-fluoronaphthalen-1-yl)oxy)propyl)-11,12-dimethyl-4,5,6,7,9,11-hexahydropyrazolo[4',3':9,10][1,6]oxaazacycloundecino[8,7,6-hi]indole-2-carboxylate (130 mg; see Intermediate 460) was dissolved in ethanol (15 ml), treated with aqueous solution of lithium hydroxide (2 M, 2 ml), and heated to 75° C. for 18 hours. The mixture was cooled to room temperature, volatiles were removed under reduced pressure, and the residue was partitioned between ethyl acetate (50 ml) and aqueous hydrochloric acid (3M, 50 ml). The organic layers were washed with saturated aqueous sodium chloride solution, the combined aqueous phases were back extracted with ethyl acetate, and the combined organic layers were dried over sodium sulfate. Insoluble materials were removed by filtration, and the filtrate was concentrated under reduced pressure. The resulting residue was purified by normal phase chromatography on silica gel eluting with a gradient of ethyl acetate in hexanes (50-100%) to give the title compound as an off white solid (99 mg).

LRMS (ESIneg) m/z=540 [M−H]$^-$ $^1$H NMR (300 MHz, Chloroform-d) δ 8.36 (dd, J=9.3, 5.8 Hz, 1H), 7.71 (dd, J=8.0, 1.3 Hz, 1H), 7.42-7.28 (m, 3H), 7.26-7.18 (m, 1H), 7.10 (dd, J=7.9, 7.1 Hz, 1H), 7.02 (dd, J=7.1, 1.3 Hz, 1H), 6.70 (dd, J=6.9, 1.7 Hz, 1H), 4.71 (d, J=12.6 Hz, 1H), 4.39 (dd, J=13.3, 5.2 Hz, 2H), 4.19 (t, J=6.1 Hz, 2H), 4.02 (t, J=11.9 Hz, 1H), 3.88 (s, 3H), 3.44 (td, J=8.7, 8.3, 5.8 Hz, 3H), 3.23 (t, J=9.2 Hz, 1H), 2.36 (q, J=6.8 Hz, 2H), 1.90 (s, 3H), 1.57-1.09 (m, 4H).

The title compound was separated into enantiomers by preparative chiral HPLC to give enantiomer 1 (19.2 mg, see Example 303) and enantiomer 2 (15.7 mg, see Example 302).

Preparative chiral HPLC method: Instrument: Labomatic HD5000, Labocord-5000; Gilson GX-241, Labcol Vario 4000, column: Chiralpak IC 5μ 250×30 mm; Eluent A: hexane+0.1 Vol-% trifluoroacetic acid (99%); Eluent B: 2-propanol; isocratic 80% A+20% B; Flow 40.0 ml/min; UV 220 nm.

Analytical chiral HPLC method: Instrument: Agilent HPLC 1260; column: Chiralpak IC 3μ 100×4.6 mm; Eluent A: hexane+0.1 Vol-% trifluoroacetic acid (99%); Eluent B: 2-propanol; isocratic 80% A+20% B; Flow 1.4 ml/min; Temperature: 25° C.; DAD 220 nm.

Example 302

(+)-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid (Enantiomer 2)

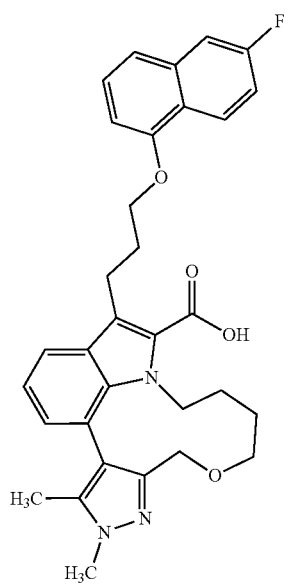 [SMILES: Cc1c2c(nn1C)COCCCCn1c(C(=O)O)c(CCCOc3cccc4cc(F)ccc34)c3cccc-2c31]

For the preparation of the racemic title compound and separation into its enantiomers see Example 301.

Analytical Chiral HPLC (method see Example 301): $R_t$=2.82 min.

Specific optical rotation (Method O1): +35.9° (c=1.0000 g/100 ml in DMSO)

LC-MS (Method 1): $R_t$=1.48 min; MS (ESIpos): m/z=542 [M+H]$^+$ $^1$H-NMR (400 MHz, DMSO-d6) δ[ppm]: 1.000 (0.42), 1.136 (0.61), 1.154 (1.10), 1.172 (0.94), 1.185 (0.66), 1.199 (0.57), 1.209 (0.49), 1.232 (0.63), 1.314 (0.75), 1.330 (0.79), 1.812 (14.82), 2.190 (0.93), 2.206 (1.46), 2.223 (1.02), 2.518 (8.14), 2.522 (5.49), 3.081 (0.72), 3.094 (0.68), 3.106 (0.50), 3.259 (0.94), 3.266 (0.86), 3.274 (1.26), 3.292 (1.51), 3.311 (0.74), 3.323 (1.12), 3.341 (0.63), 3.356 (0.52), 3.796 (16.00), 3.860 (0.79), 3.871 (0.80), 3.884 (0.74), 3.894 (1.01), 3.904 (0.72), 3.917 (0.69), 3.928 (0.57), 4.168 (2.17), 4.181 (1.13), 4.199 (3.85), 4.209 (1.24), 4.276 (0.57), 4.295 (0.60), 4.314 (0.49), 4.499 (2.03), 4.530 (1.76), 6.856 (1.13), 6.863 (1.23), 6.871 (1.08), 6.878 (1.27), 6.903 (1.70), 6.906 (1.81), 6.921 (2.20), 6.924 (2.09), 7.032 (1.76), 7.050 (1.84), 7.052 (2.14), 7.070 (1.48), 7.366 (0.72), 7.373 (0.91), 7.388 (1.18), 7.395 (1.34), 7.406 (0.52), 7.411 (0.90), 7.417 (0.96), 7.427 (2.14), 7.435 (2.44), 7.442 (5.42), 7.456 (0.49), 7.642 (1.34), 7.649 (1.45), 7.668 (1.38), 7.675 (1.43), 7.698 (1.76), 7.701 (1.84), 7.718 (1.68), 7.720 (1.67), 8.262 (1.21), 8.277 (1.27), 8.286 (1.26), 8.300 (1.21).

Example 303

(−)-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid (Enantiomer 1)

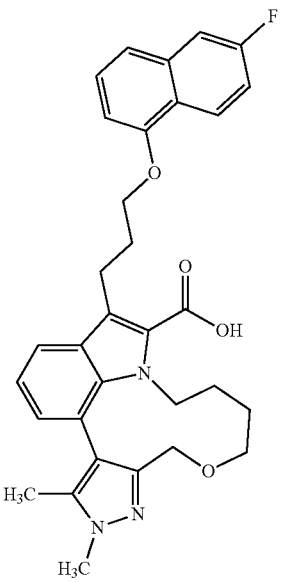

For the preparation of the racemic title compound and separation into its enantiomers see Example 301.

Analytical Chiral HPLC (method see Example 301): $R_t$=2.00 min.

Specific optical rotation (Method O1): −32.2° (c=1.0000 g/100 ml in DMSO)

LC-MS (Method 1): $R_t$=1.48 min; MS (ESIpos): m/z=542 [M+H]$^+$ $^1$H-NMR (400 MHz, DMSO-d6) δ[ppm]: 0.990 (0.47), 1.111 (0.63), 1.129 (0.50), 1.136 (1.03), 1.154 (1.97), 1.172 (1.42), 1.198 (0.62), 1.209 (0.55), 1.232 (0.68), 1.314 (1.22), 1.330 (1.17), 1.812 (14.62), 2.189 (1.02), 2.206 (1.62), 2.223 (1.13), 2.240 (0.42), 2.322 (0.65), 2.326 (0.92), 2.332 (0.68), 2.522 (6.03), 2.664 (0.65), 2.669 (0.92), 2.673 (0.70), 3.068 (0.45), 3.080 (0.82), 3.093 (0.77), 3.105 (0.57), 3.119 (0.43), 3.259 (1.10), 3.265 (1.00), 3.274 (1.43), 3.292 (1.70), 3.311 (0.87), 3.323 (1.27), 3.341 (0.80), 3.356 (0.67), 3.361 (0.53), 3.378 (0.45), 3.796 (16.00), 3.860 (0.48), 3.871 (0.53), 3.884 (0.55), 3.894 (0.87), 3.905 (0.58), 3.917 (0.58), 3.929 (0.47), 4.168 (2.33), 4.181 (1.23), 4.198 (4.12), 4.210 (1.35), 4.275 (0.62), 4.294 (0.65), 4.314 (0.52), 4.499 (2.18), 4.530 (1.90), 6.856 (1.22), 6.862 (1.28), 6.871 (1.17), 6.878 (1.35), 6.903 (1.73), 6.906 (1.85), 6.921 (2.27), 6.924 (2.22), 7.032 (1.82), 7.052 (2.23), 7.070 (1.43), 7.366 (0.78), 7.373 (0.87), 7.388 (1.30), 7.395 (1.45), 7.406 (0.58), 7.410 (0.92), 7.417 (1.00), 7.426 (2.30), 7.435 (2.62), 7.442 (5.62), 7.456

(0.53), 7.642 (1.45), 7.649 (1.53), 7.668 (1.50), 7.675 (1.52), 7.698 (1.82), 7.700 (1.95), 7.717 (1.77), 7.720 (1.70), 8.262 (1.28), 8.277 (1.35), 8.285 (1.35), 8.300 (1.25).

Example 304

(rac)-11-(3-((6-chloronaphthalen-1-yl)oxy)propyl)-12-ethyl-10-methyl-4,5,6,7,9,10-hexahydropyrazolo[4',3':9,10][1,6]oxaazacycloundecino[8,7,6-hi]indole-2-carboxylic acid

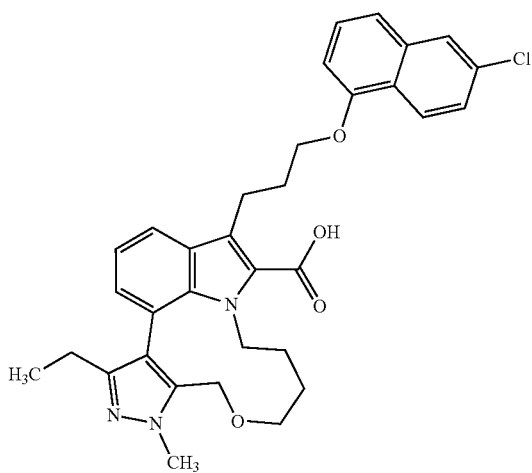 [SMILES: CCc1nn(C)c2c1-c1cccc3c(CCCOc4cccc5cc(Cl)ccc45)c(C(=O)O)n(c13)CCCCOC2]

To crude (rac)-ethyl 12-ethyl-10-methyl-1-(3-((6-chloronaphthalen-1-yl)oxy)propyl)-4,5,6,7,9,10-hexahydropyrazolo[4',3':9,10][1,6]oxaazacycloundecino[8,7,6-hi]indole-2-carboxylate (120 mg, see Intermediate 489) in tetrahydrofuran (7 ml) was added ethanol (2 ml) and aqueous solution of lithium hydroxide (2 M, 2.5 ml), and the resulting suspension was heated to 70° C. for 24 hours. The reaction was cooled to room temperature, volatiles were removed under reduced pressure, and the residue was partitioned between ethyl acetate (50 ml) and aqueous hydrochloric acid (3N, 50 ml). The organic phase was washed with saturated aqueous sodium chloride solution, the combined aqueous phases were back extracted with ethyl acetate, and the combined organic layers were then dried over sodium sulfate. Insoluble materials were removed by filtration, and volatiles were removed under reduced pressure. The residue was purified by flash chromatography on silica gel eluting with a gradient of methanol in dichloromethane (0-10%) to give the title compound as a tan foam (65 mg).

LRMS (ESIneg) m/z=570 [M−H]⁻

¹H NMR (300 MHz, Chloroform-d) δ 11.51 (s, 1H), 8.27 (d, J=9.0 Hz, 1H), 7.75 (dd, J=8.1, 1.6 Hz, 2H), 7.39-7.27 (m, 3H), 7.08 (dd, J=8.1, 7.1 Hz, 1H), 6.92 (dd, J=7.1, 1.2 Hz, 1H), 6.71 (dd, J=7.4, 1.3 Hz, 1H), 4.65 (d, J=14.4 Hz, 1H), 4.59 (d, J=13.5 Hz, 1H), 4.46 (d, J=13.4 Hz, 1H), 4.19 (t, J=6.1 Hz, 3H), 3.97 (s, 3H), 3.59-3.35 (m, 3H), 3.03-2.80 (m, 1H), 2.36 (dtd, J=12.8, 7.3, 6.3, 2.7 Hz, 4H), 1.56 (t, J=12.5 Hz, 1H), 1.37-1.06 (m, 3H), 1.01 (t, J=7.6 Hz, 3H).

The title compound was separated into enantiomers by preparative chiral HPLC to give enantiomer 1 (9.4 mg, see Example 305) and enantiomer 2 (7.1 mg, see Example 306).

Preparative chiral HPLC method: Instrument: Sepiatec: Prep SFC100; column: Chiralpak IG 5 μm 250×30 mm; eluent A CO₂, eluent B: ethanol; isocratic: 35% B; flow 100.0 ml/min temperature: 40° C.; BPR: 150 bar; MWD @ 220 nm.

Analytical chiral HPLC method: Instrument: Agilent: 1260, Aurora SFC-Modul; column: Chiralpak IG 5 μm 100×4.6 mm; eluent A: CO₂, eluent B: ethanol; isocratic: 35% B; flow 4.0 ml/min; temperature: 37.5° C.; BPR: 100 bar; MWD @ 220 nm.

Example 305

7-{3-[(6-chloronaphthalen-1-yl)oxy]propyl}-3-ethyl-1-methyl-1,10,11,12,13,15-hexahydropyrazolo[4',3':9,10][1,6]oxazacycloundecino[8,7,6-hi]indole-8-carboxylic acid (Enantiomer 1)

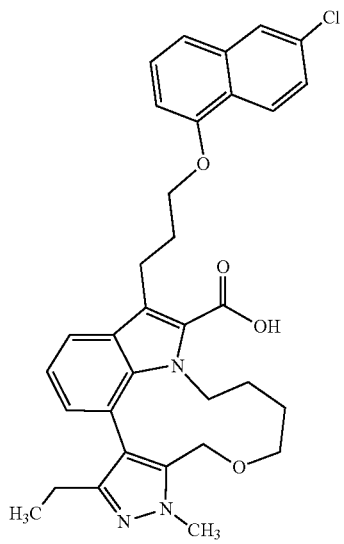 [SMILES: CCc1nn(C)c2c1-c1cccc3c(CCCOc4cccc5cc(Cl)ccc45)c(C(=O)O)n(c13)CCCCOC2]

For the preparation of the racemic title compound and separation into its enantiomers see Example 304.

Analytical Chiral HPLC (method see Example 304): R$_t$=0.96 min.

LC-MS (Method 1): R$_t$=1.63 min; MS (ESIpos): m/z=572 [M+H]⁺

¹H-NMR (400 MHz, DMSO-d6) δ[ppm]: 0.878 (4.79), 0.897 (10.61), 0.916 (4.96), 1.004 (1.51), 1.137 (1.04), 1.235 (1.01), 2.083 (6.42), 2.115 (0.54), 2.125 (0.87), 2.131 (0.81), 2.144 (2.13), 2.150 (2.16), 2.163 (2.16), 2.169 (2.12), 2.182 (1.13), 2.189 (1.33), 2.195 (1.34), 2.213 (1.85), 2.229 (1.30), 2.247 (0.48), 2.322 (0.64), 2.326 (0.87), 2.331 (0.64), 2.522 (3.21), 2.664 (0.66), 2.668 (0.88), 2.673 (0.66), 2.749 (0.78), 2.761 (0.64), 2.779 (0.84), 3.264 (0.66), 3.279 (0.96), 3.297 (1.70), 3.369 (1.21), 3.388 (0.93), 3.405 (1.12), 3.416 (0.85), 3.434 (0.96), 3.451 (0.45), 3.849 (16.00), 3.990 (0.43), 4.001 (0.52), 4.013 (0.85), 4.025 (0.55), 4.035 (0.57), 4.047 (0.43), 4.187 (1.64), 4.203 (3.30), 4.217 (1.66), 4.234 (2.04), 4.267 (2.16), 4.495 (0.96), 4.506 (0.57), 4.518 (0.52), 4.530 (0.88), 4.612 (2.28), 4.645 (2.01), 6.841 (2.00), 6.844 (2.04), 6.859 (2.37), 6.861 (2.31), 6.906 (1.40), 6.917 (2.31), 6.928 (1.51), 7.027 (1.85), 7.046 (2.42), 7.064 (1.54), 7.440 (5.22), 7.451 (5.25), 7.477 (2.13), 7.483 (2.06), 7.500 (2.09), 7.505 (2.22), 7.731 (2.09), 7.733 (2.15), 7.750 (2.00), 7.993 (3.66), 7.998 (3.69), 8.194 (3.25), 8.216 (2.97).

Example 306

7-{3-[(6-chloronaphthalen-1-yl)oxy]propyl}-3-ethyl-1-methyl-1,10,11,12,13,15-hexahydropyrazolo[4',3':9,10][1,6]oxazacycloundecino[8,7,6-hi]indole-8-carboxylic acid (Enantiomer 2)

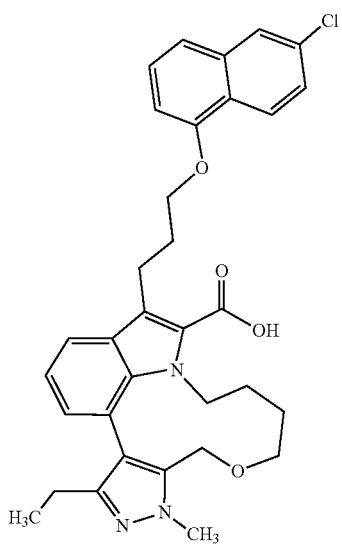 [SMILES: CCc1nn(C)c2c1-c1cccc3c(CCCOc4cccc5cc(Cl)ccc45)c(C(=O)O)n(c13)CCCCOC2]

For the preparation of the racemic title compound and separation into its enantiomers see Example 304.

Analytical Chiral HPLC (method see Example 304): $R_t$=1.88 min.

LC-MS (Method 1): $R_t$=1.63 min; MS (ESIpos): m/z=572 [M+H]$^+$ $^1$H-NMR (400 MHz, DMSO-d6) δ[ppm]: 0.878 (4.66), 0.897 (10.76), 0.916 (5.00), 1.004 (1.24), 1.018 (1.03), 1.035 (0.61), 1.052 (0.42), 1.137 (1.04), 1.233 (0.80), 2.083 (7.57), 2.115 (0.53), 2.126 (0.79), 2.132 (0.69), 2.144 (1.96), 2.151 (1.98), 2.163 (2.01), 2.170 (1.96), 2.182 (0.96), 2.189 (1.11), 2.195 (1.09), 2.213 (1.53), 2.230 (1.08), 2.331 (0.66), 2.518 (4.29), 2.522 (2.67), 2.673 (0.69), 2.749 (0.67), 2.760 (0.55), 2.778 (0.72), 3.263 (0.51), 3.278 (0.71), 3.297 (1.27), 3.370 (0.74), 3.388 (0.66), 3.405 (0.92), 3.421 (0.67), 3.434 (0.82), 3.849 (16.00), 4.001 (0.43), 4.013 (0.72), 4.024 (0.47), 4.035 (0.48), 4.187 (1.38), 4.203 (2.88), 4.218 (1.41), 4.234 (1.86), 4.267 (1.99), 4.495 (0.82), 4.507 (0.48), 4.519 (0.45), 4.531 (0.76), 4.612 (2.12), 4.646 (1.88), 6.841 (1.88), 6.843 (1.90), 6.858 (2.23), 6.861 (2.12), 6.906 (1.33), 6.917 (2.18), 6.928 (1.43), 7.027 (1.88), 7.046 (2.27), 7.064 (1.57), 7.440 (4.84), 7.452 (5.00), 7.477 (2.06), 7.483 (2.20), 7.500 (2.22), 7.505 (2.17), 7.730 (1.88), 7.733 (1.93), 7.750 (1.80), 7.753 (1.73), 7.993 (3.49), 7.998 (3.44), 8.194 (3.10), 8.217 (2.88).

Example 307

(rac)-11,12-dimethyl-1-(3-((6-methylnaphthalen-1-yl)oxy)propyl)-4,5,6,7,9,11-hexahydropyrazolo[4',3':9,10][1,6]oxaazacycloundecino[8,7,6-hi]indole-2-carboxylic acid (rac)-Ethyl 11,12-dimethyl-1-(3-((6-methylnaphthalen-1-yl)oxy)propyl)-4,5,6,7,9,11-hexahydropyrazolo[4',3':9,10][1,6]oxaazacycloundecino[8,7,6-hi]indole-2-carboxylate (92 mg; see Intermediate 490) was dissolved in ethanol (15 ml) treated with aqueous solution of lithium hydroxide (2 M, 2 ml), and the mixture was heated to 75° C. for 42 hours. The mixture was cooled to room temperature, volatiles were removed under reduced pressure, and the residue was partitioned between ethyl acetate (50 ml) and aqueous hydrochloric acid (3 M, 50 ml). The layers were separated, and the organic layer was washed with saturated aqueous sodium chloride solution. The combined aqueous phases were back extracted with ethyl acetate (50 ml), the combined organic layers were dried over sodium sulfate, insoluble materials were removed by filtration, the filtrate was concentrated under reduced pressure, and the residue was purified by normal phase chromatography eluting with a gradient of ethyl acetate in hexanes (50-100%), to give the title compound as an off white solid (75 ml).

LRMS (ESIneg) m/z=1536 [M−H]$^-$ $^1$H NMR (300 MHz, Chloroform-d) δ 8.27 (d, J=8.6 Hz, 1H), 7.73 (dd, J=8.0, 1.3 Hz, 1H), 7.56 (p, J=0.9 Hz, 1H), 7.35-7.27 (m, 3H), 7.10 (dd, J=7.9, 7.1 Hz, 1H), 7.01 (dd, J=7.1, 1.3 Hz, 1H), 6.68 (dd, J=6.2, 2.4 Hz, 1H), 4.71 (d, J=12.5 Hz, 1H), 4.49-4.32 (m, 2H), 4.19 (t, J=6.1 Hz, 2H), 4.11-3.94 (m, 1H), 3.87 (s, 3H), 3.56-3.34 (m, J=7.2 Hz, 3H), 3.32-3.15 (m, 1H), 2.49 (d, J=0.9 Hz, 3H), 2.36 (q, J=7.0 Hz, 2H), 1.90 (s, 3H), 1.60-1.08 (m, 4H).

The title compound was separated into enantiomers by preparative chiral HPLC to give enantiomer 1 (16.7 mg, see Example 308) and enantiomer 2 (17.4 mg, see Example 309).

Preparative chiral HPLC method: Instrument: Sepiatec: Prep SFC100; column: Chiralpak IG 5 μm 250×30 mm; eluent A CO$_2$, eluent B: ethanol; isocratic: 35% B; flow 100.0 ml/min temperature: 40° C.; BPR: 150 bar; MWD @ 220 nm.

Analytical chiral HPLC method: Instrument: Agilent: 1260, Aurora SFC-Modul; column: Chiralpak IG 5 μm 100×4.6 mm; eluent A: $CO_2$, eluent B: ethanol; isocratic: 35% B; flow 4.0 ml/min; temperature: 37.5° C.; BPR: 100 bar; MWD @ 220 nm.

Example 308

2,3-dimethyl-7-{3-[(6-methylnaphthalen-1-yl)oxy]propyl}-2,10,11,12,13,15-hexahydropyrazolo[4',3':9,10][1,6]oxazacycloundecino[8,7,6-hi]indole-8-carboxylic acid (Enantiomer 1)

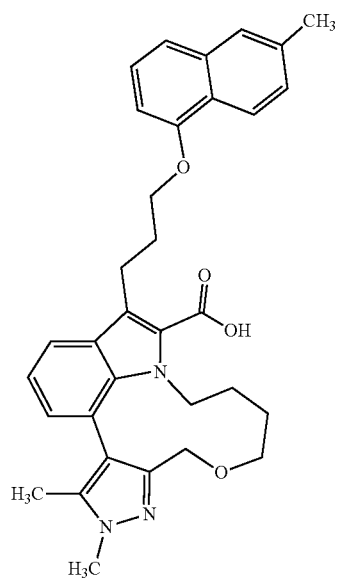 [SMILES: Cc1ccc2c(OCCCc3c(C(=O)O)n4c5c(cccc35)-c3c(nn(C)c3C)COCCCC4)cccc2c1]

For the preparation of the racemic title compound and separation into its enantiomers see Example 307.

Analytical Chiral HPLC (method see Example 307): $R_t$=1.14 min.

LC-MS (Method 1): $R_t$=1.53 min; MS (ESIpos): m/z=538 $[M+H]^+$ $^1$H-NMR (400 MHz, DMSO-d6) δ[ppm]: 0.814 (0.44), 0.821 (0.44), 0.904 (0.47), 0.999 (0.47), 1.035 (0.61), 1.052 (0.98), 1.070 (0.52), 1.137 (0.82), 1.156 (0.64), 1.174 (0.76), 1.184 (0.66), 1.198 (0.57), 1.205 (0.69), 1.222 (0.41), 1.236 (0.40), 1.327 (0.48), 1.814 (15.05), 2.074 (0.92), 2.083 (1.36), 2.182 (1.06), 2.199 (1.63), 2.216 (1.13), 2.231 (0.41), 2.468 (11.42), 2.518 (3.70), 2.522 (2.28), 2.629 (0.52), 3.067 (0.41), 3.079 (0.81), 3.092 (0.75), 3.105 (0.54), 3.259 (1.47), 3.264 (1.50), 3.277 (1.99), 3.298 (2.29), 3.796 (16.00), 3.865 (0.40), 3.877 (0.42), 3.888 (0.73), 3.899 (0.45), 3.911 (0.47), 4.167 (4.00), 4.182 (1.17), 4.198 (2.59), 4.284 (0.58), 4.301 (0.62), 4.321 (0.49), 4.495 (2.22), 4.526 (1.92), 6.788 (1.33), 6.792 (1.33), 6.805 (1.37), 6.810 (1.37), 6.894 (1.64), 6.896 (1.68), 6.912 (2.11), 7.022 (1.72), 7.042 (2.16), 7.060 (1.36), 7.305 (0.73), 7.326 (2.47), 7.343 (6.28), 7.361 (1.99), 7.363 (1.95), 7.632 (2.73), 7.690 (1.75), 7.692 (1.80), 7.710 (1.65), 7.712 (1.60), 8.136 (2.42), 8.158 (2.29).

Example 309

2,3-dimethyl-7-{3-[(6-methylnaphthalen-1-yl)oxy]propyl}-2,10,11,12,13,15-hexahydropyrazolo[4',3':9,10][1,6]oxazacycloundecino[8,7,6-hi]indole-8-carboxylic acid (Enantiomer 2)

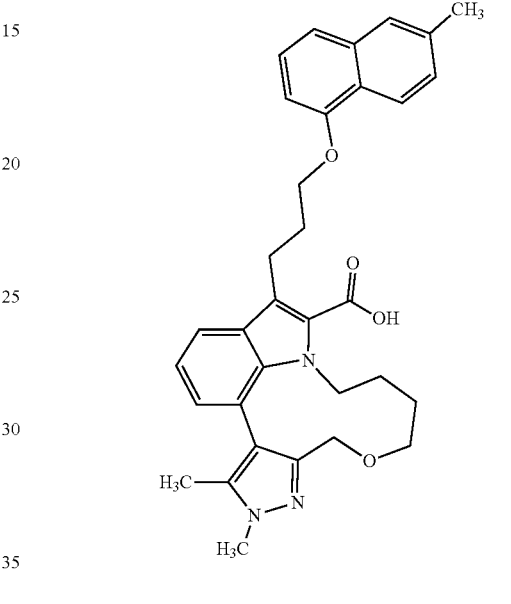

For the preparation of the racemic title compound and separation into its enantiomers see Example 307.

Analytical Chiral HPLC (method see Example 307): $R_t$=1.46 min.

LC-MS (Method 1): $R_t$=1.53 min; MS (ESIpos): m/z=538 $[M+H]^+$ $^1$H-NMR (400 MHz, DMSO-d6) δ[ppm]: 0.999 (0.53), 1.137 (0.80), 1.173 (0.84), 1.185 (0.74), 1.199 (0.66), 1.205 (0.84), 1.221 (0.44), 1.327 (0.54), 1.814 (15.69), 2.074 (2.45), 2.084 (0.93), 2.182 (1.18), 2.199 (1.81), 2.216 (1.25), 2.322 (0.61), 2.327 (0.81), 2.331 (0.60), 2.468 (12.38), 2.522 (2.81), 2.629 (0.61), 2.665 (0.63), 2.669 (0.84), 2.673 (0.63), 3.067 (0.44), 3.080 (0.88), 3.093 (0.83), 3.105 (0.58), 3.118 (0.43), 3.264 (1.60), 3.277 (2.10), 3.299 (2.28), 3.796 (16.00), 3.866 (0.46), 3.888 (0.81), 3.900 (0.51), 3.911 (0.54), 3.922 (0.41), 4.167 (4.34), 4.182 (1.35), 4.198 (2.77), 4.284 (0.66), 4.302 (0.71), 4.319 (0.57), 4.495 (2.35), 4.526 (2.02), 6.788 (1.43), 6.792 (1.43), 6.805 (1.51), 6.810 (1.48), 6.896 (1.81), 6.912 (2.25), 7.022 (1.75), 7.042 (2.28), 7.060 (1.37), 7.305 (0.76), 7.326 (2.52), 7.343 (6.65), 7.361 (2.18), 7.363 (2.15), 7.632 (3.01), 7.692 (1.93), 7.710 (1.80), 8.136 (2.54), 8.158 (2.42).

Example 310

(rac)-12-ethyl-10-methyl-1-(3-((6-(trifluoromethyl) naphthalen-1-yl)oxy)propyl)-4,5,6,7,9,10-hexahydropyrazolo[4',3':9,10][1]oxa[6]azacycloundecino[8,7,6-h]indole-2-carboxylic acid

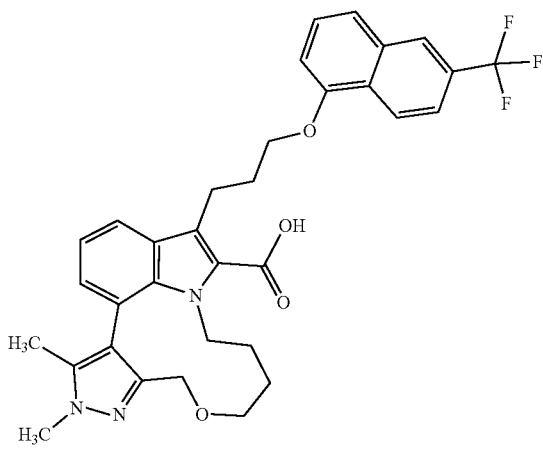 [SMILES: Cc1c2c(nn1C)COCCCCn1c(C(=O)O)c(CCCOc3cccc4cc(C(F)(F)F)ccc34)c3cccc-2c31]

Crude (rac)-ethyl 11,12-dimethyl-1-(3-((6-(trifluoromethyl)naphthalen-1-yl)oxy)propyl)-4,5,6,7,9,11-hexahydropyrazolo[4',3':9,10][1,6]oxaazacycloundecino[8,7,6-hi]indole-2-carboxylate (80 mg; see Intermediate 495) was dissolved in ethanol (15 ml) and treated with aqueous solution of lithium hydroxide (2 M, 2 ml) and the mixture was heated to 75° C. for 18 hours. The reaction mixture was cooled to room temperature, volatiles were removed under reduced pressure, and the residue was partitioned between ethyl acetate (50 ml) and aqueous hydrogen chloride (3 N, 50 ml). The layers were separated, and the organic phase was washed with saturated sodium chloride solution, the combined aqueous washes were extracted with ethyl acetate (50 ml), and the combined organic layers were dried over sodium sulfate and filtered. Volatiles were removed under reduced pressure, and the residue was purified by normal phase chromatography on silica gel, eluting with a gradient of ethyl acetate in hexanes (50-100%) to give the title compound as an off white solid (60 mg).

LRMS (ESIneg) m/z=590 [M–H]$^-$ $^1$H NMR (300 MHz, Chloroform-d) δ 8.47 (dd, J=8.8, 1.2 Hz, 1H), 8.12-8.03 (m, 1H), 7.70 (dd, J=7.9, 1.3 Hz, 1H), 7.62 (dd, J=8.9, 1.8 Hz, 1H), 7.50-7.37 (m, 2H), 7.09 (dd, J=7.9, 7.1 Hz, 1H), 7.00 (dd, J=7.1, 1.3 Hz, 1H), 6.84 (dd, J=7.1, 1.6 Hz, 1H), 4.70 (d, J=12.6 Hz, 1H), 4.50-4.34 (m, 2H), 4.21 (t, J=6.1 Hz, 2H), 4.10-3.99 (m, 1H), 3.88 (s, 3H), 3.45 (dt, J=15.8, 8.0 Hz, 3H), 3.24 (dt, J=12.6, 6.5 Hz, 1H), 2.37 (p, J=7.1 Hz, 2H), 1.89 (s, 3H), 1.61-1.31 (m, 2H), 1.30-1.09 (m, 2H).

The title compound was separated into enantiomers by preparative chiral HPLC to give enantiomer 1 (14.9 mg, see Example 311) and enantiomer 2 (20.0 mg, see Example 312).

Preparative chiral HPLC method: Instrument: Labomatic HD5000, Labocord-5000; Gilson GX-241, Labcol Vario 4000, column: Chiralpak IC 5μ 250×30 mm; Eluent A: hexane+0.1 Vol-% trifluoroacetic acid (99%); Eluent B: 2-propanol; isocratic 80% A+20% B; Flow 40.0 ml/min; UV 220 nm.

Analytical chiral HPLC method: Instrument: Agilent HPLC 1260; column: Chiralpak IC 3μ 100×4.6 mm; Eluent A: hexane+0.1 Vol-% trifluoroacetic acid (99%); Eluent B: 2-propanol; isocratic 80% A+20% B; Flow 1.4 ml/min; Temperature: 25° C.; DAD 220 nm.

Example 311

2,3-dimethyl-7-(3-{[6-(trifluoromethyl)naphthalen-1-yl]oxy}propyl)-2,10,11,12,13,15-hexahydropyrazolo[4',3':9,10][1,6]oxazacycloundecino[8,7,6-hi]indole-8-carboxylic acid (Enantiomer 1)

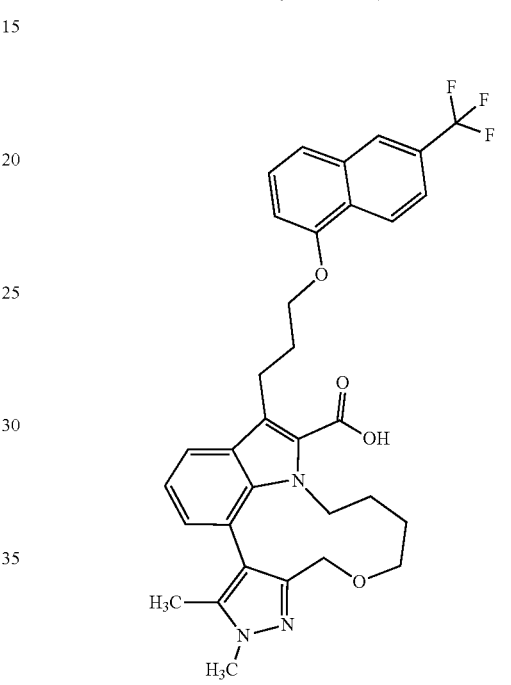

For the preparation of the racemic title compound and separation into its enantiomers see Example 310.

Analytical Chiral HPLC (method see Example 310): $R_t$=1.50 min.

LC-MS (Method 1): $R_t$=1.57 min; MS (ESIpos): m/z=592 [M+H]$^+$ $^1$H-NMR (400 MHz, DMSO-d6) δ[ppm]: 0.851 (0.58), 0.988 (0.42), 1.026 (0.55), 1.042 (0.44), 1.135 (0.67), 1.154 (0.78), 1.172 (0.75), 1.192 (0.58), 1.204 (0.53), 1.217 (0.47), 1.235 (1.29), 1.315 (0.84), 1.330 (0.80), 1.805 (15.16), 2.212 (0.98), 2.228 (1.49), 2.245 (1.02), 2.331 (0.91), 2.336 (0.40), 2.518 (4.93), 2.523 (3.20), 2.673 (0.91), 2.678 (0.42), 3.078 (0.75), 3.091 (0.69), 3.103 (0.49), 3.260 (0.84), 3.268 (0.82), 3.277 (0.84), 3.292 (1.02), 3.310 (1.44), 3.331 (1.42), 3.350 (0.69), 3.365 (0.51), 3.794 (16.00), 3.858 (0.44), 3.870 (0.49), 3.882 (0.49), 3.892 (0.80), 3.903 (0.53), 3.916 (0.53), 3.927 (0.42), 4.165 (2.09), 4.196 (2.33), 4.219 (1.02), 4.234 (1.98), 4.248 (1.07), 4.275 (0.64), 4.295 (0.60), 4.313 (0.49), 4.493 (2.15), 4.524 (1.86), 6.900 (1.82), 6.903 (1.80), 6.918 (2.33), 6.920 (2.15), 7.025 (1.98), 7.044 (2.22), 7.063 (1.98), 7.067 (1.93), 7.086 (1.98), 7.530 (1.40), 7.550 (2.53), 7.569 (1.62), 7.671 (2.26), 7.691 (1.75), 7.698 (1.95), 7.701 (1.93), 7.718 (1.78), 7.721 (1.69), 7.733 (1.42), 7.738 (1.38), 7.755 (1.44), 7.760 (1.44), 8.371 (2.40), 8.399 (1.69), 8.422 (1.53).

Example 312

2,3-dimethyl-7-(3-{[6-(trifluoromethyl)naphthalen-1-yl]oxy}propyl)-2,10,11,12,13,15-hexahydropyrazolo[4',3':9,10][1,6]oxazacycloundecino[8,7,6-hi]indole-8-carboxylic acid (Enantiomer 2)

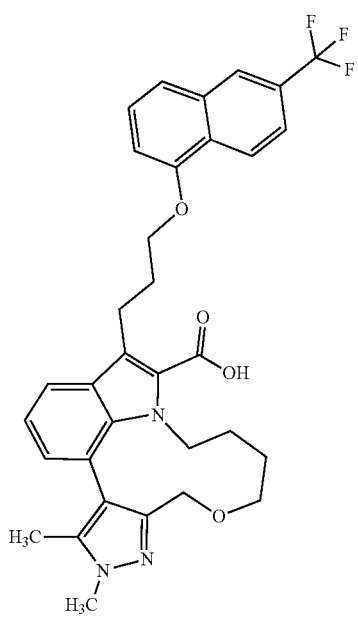 [SMILES: Cc1c2c(nn1C)COCCCCn1c(C(=O)O)c(CCCOc3cccc4cc(C(F)(F)F)ccc34)c3cccc-2c31]

For the preparation of the racemic title compound and separation into its enantiomers see Example 310.

Analytical Chiral HPLC (method see Example 310): $R_t$=2.04 min.

LC-MS (Method 3): $R_t$=1.52 min; MS (ESIpos): m/z=592 [M+H]$^+$ $^1$H-NMR (400 MHz, DMSO-d6) δ[ppm]: 0.991 (0.48), 1.143 (0.57), 1.167 (0.75), 1.178 (0.70), 1.191 (0.59), 1.203 (0.50), 1.322 (0.49), 1.805 (16.00), 2.211 (1.10), 2.228 (1.69), 2.244 (1.15), 2.331 (0.57), 2.518 (3.44), 2.523 (2.16), 2.539 (0.49), 3.065 (0.41), 3.077 (0.82), 3.091 (0.76), 3.103 (0.53), 3.259 (0.97), 3.273 (1.06), 3.288 (1.42), 3.794 (15.85), 3.865 (0.41), 3.878 (0.44), 3.888 (0.76), 3.899 (0.46), 3.911 (0.49), 4.165 (2.20), 4.196 (2.51), 4.219 (1.15), 4.232 (2.18), 4.246 (1.15), 4.264 (0.48), 4.281 (0.64), 4.300 (0.65), 4.315 (0.52), 4.491 (2.29), 4.522 (1.96), 6.894 (1.77), 6.896 (1.76), 6.912 (2.29), 6.914 (2.11), 7.021 (1.88), 7.041 (2.29), 7.058 (1.66), 7.065 (2.05), 7.084 (2.14), 7.528 (1.45), 7.548 (2.66), 7.568 (1.65), 7.669 (2.48), 7.693 (2.62), 7.714 (1.83), 7.733 (1.51), 7.736 (1.47), 7.755 (1.58), 7.759 (1.54), 8.369 (2.69), 8.399 (1.88), 8.422 (1.69).

Example 313

(rac)-12-ethyl-10-methyl-1-(3-((6-(trifluoromethyl)naphthalen-1-yl)oxy)propyl)-4,5,6,7,9,10-hexahydropyrazolo[4',3':9,10][1,6]oxaazacycloundecino[8,7,6-hi]indole-2-carboxylic acid

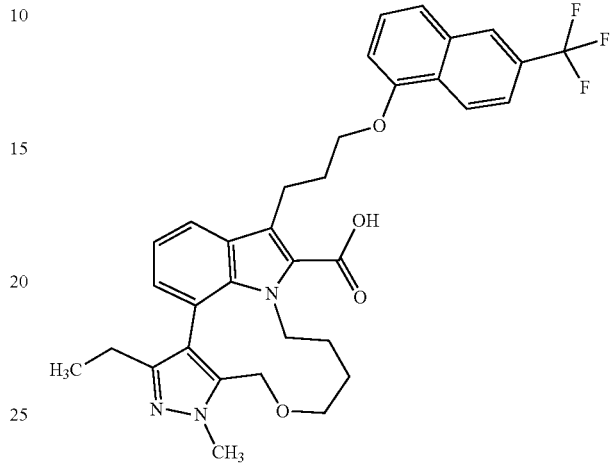

To crude (rac)-ethyl 12-ethyl-10-methyl-1-(3-((6-(trifluoromethyl)naphthalen-1-yl)oxy)propyl)-4,5,6,7,9,10-hexahydropyrazolo[4',3':9,10][1]oxa[6]azacycloundecino[8,7,6-hi]indole-2-carboxylate (126 mg, see Intermediate 500) in tetrahydrofuran (7 ml) was added ethanol (2 ml) and aqueous solution of lithium hydroxide (2 M, 2.5 ml), and the resulting suspension was heated to 70° C. for 24 hours. The reaction mixture was cooled to room temperature, volatiles were removed under reduced pressure, and the residue was partitioned between ethyl acetate (50 ml) and aqueous hydrochloric acid (3 N, 50 ml). The organic phase was washed with saturated aqueous sodium chloride solution, the combined aqueous phases were back extracted with ethyl acetate, and the combined organic layers were then dried over sodium sulfate. Insoluble materials were removed by filtration, and volatiles were removed under reduced pressure. The residue was purified by flash chromatography on silica gel eluting with a gradient of methanol in dichloromethane (0-10%) to give the title compound as an off white foam (83 mg).

LRMS (ESIneg) m/z=604 [M–H]$^-$ $^1$H NMR (300 MHz, Chloroform-d) δ 8.49-8.38 (m, 1H), 8.07 (dd, J=1.8, 1.0 Hz, 1H), 7.75 (dd, J=8.1, 1.3 Hz, 1H), 7.61 (dd, J=8.9, 1.8 Hz, 1H), 7.49-7.36 (m, 2H), 7.07 (dd, J=8.0, 7.1 Hz, 1H), 6.92 (dd, J=7.1, 1.2 Hz, 1H), 6.84 (dd, J=7.2, 1.5 Hz, 1H), 4.74-4.61 (m, 1H), 4.58 (d, J=13.5 Hz, 1H), 4.45 (d, J=13.4 Hz, 1H), 4.20 (q, J=5.2, 4.4 Hz, 3H), 3.98 (s, 3H), 3.46 (dp, J=13.5, 7.3, 6.7 Hz, 3H), 2.91 (td, J=9.3, 8.9, 5.2 Hz, 1H), 2.35 (dt, J=9.3, 7.4 Hz, 4H), 1.51 (t, J=13.0 Hz, 1H), 1.34-1.03 (m, 3H), 0.99 (t, J=7.6 Hz, 3H).

The title compound was separated into enantiomers by preparative chiral HPLC to give enantiomer 1 (14.3 mg, see Example 314) and enantiomer 2 (15.0 mg, see Example 315).

Preparative chiral HPLC method: Instrument: Sepiatec: Prep SFC100; column: Chiralpak IG 5 μm 250×30 mm; eluent A CO$_2$, eluent B: ethanol; isocratic: 26% B; flow 100.0 ml/min temperature: 40° C.; BPR: 150 bar; MWD @ 220 nm.

Analytical chiral HPLC method: Instrument: Agilent: 1260, Aurora SFC-Modul; column: Chiralpak IG 5 μm 100×4.6 mm; eluent A: CO₂, eluent B: ethanol; isocratic: 26% B; flow 4.0 ml/min; temperature: 37.5° C.; BPR: 100 bar; MWD @ 220 nm.

Example 314

3-ethyl-1-methyl-7-(3-{[6-(trifluoromethyl)naphthalen-1-yl]oxy}propyl)-1,10,11,12,13,15-hexahydropyrazolo[4',3':9,10][1,6]oxazacycloundecino[8,7,6-hi]indole-8-carboxylic acid (Enantiomer 1)

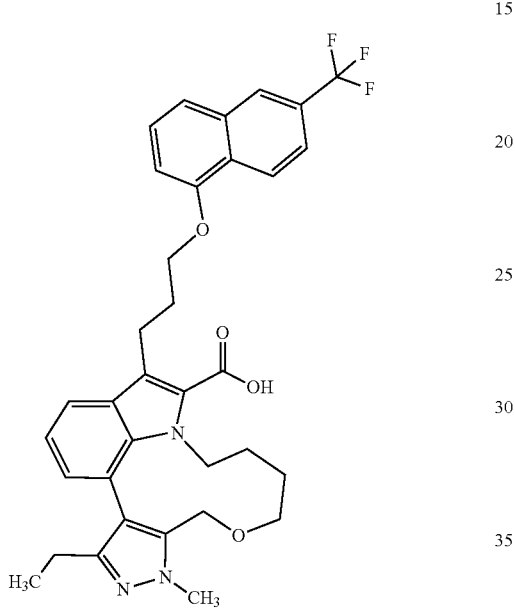

For the preparation of the racemic title compound and separation into its enantiomers see Example 313.

Analytical Chiral HPLC (method see Example 313): $R_t$=0.80 min.

LC-MS Method 1): $R_t$=1.63 min; MS (ESIpos): m/z=606 [M+H]⁺

¹H-NMR (400 MHz, DMSO-d6) δ[ppm]: 0.797 (0.44), 0.813 (0.47), 0.820 (0.47), 0.875 (4.66), 0.894 (10.59), 0.904 (0.86), 0.913 (4.99), 0.999 (1.16), 1.205 (0.66), 1.235 (0.76), 1.244 (0.69), 1.255 (0.64), 2.124 (0.76), 2.130 (0.71), 2.142 (1.98), 2.149 (1.97), 2.161 (1.95), 2.168 (1.91), 2.180 (0.71), 2.187 (0.75), 2.202 (0.55), 2.205 (0.55), 2.216 (1.00), 2.233 (1.46), 2.251 (1.02), 2.331 (0.75), 2.518 (4.17), 2.523 (2.71), 2.745 (0.64), 2.757 (0.53), 2.775 (0.69), 3.281 (0.67), 3.383 (1.13), 3.400 (1.13), 3.412 (0.73), 3.429 (0.78), 3.847 (16.00), 3.997 (0.42), 4.009 (0.69), 4.020 (0.47), 4.032 (0.46), 4.228 (2.73), 4.240 (2.88), 4.255 (1.60), 4.262 (2.28), 4.500 (0.80), 4.511 (0.47), 4.524 (0.42), 4.535 (0.73), 4.607 (2.11), 4.640 (1.87), 6.837 (1.78), 6.841 (1.75), 6.855 (2.13), 6.858 (1.91), 7.023 (1.73), 7.042 (2.06), 7.044 (2.15), 7.062 (2.73), 7.083 (2.04), 7.528 (1.37), 7.548 (2.55), 7.568 (1.60), 7.667 (2.38), 7.688 (1.75), 7.718 (1.47), 7.723 (1.46), 7.735 (2.04), 7.738 (2.64), 7.745 (1.69), 7.755 (1.77), 7.758 (1.64), 8.368 (2.60), 8.380 (1.86), 8.403 (1.60).

Example 315

3-ethyl-1-methyl-7-(3-{[6-(trifluoromethyl)naphthalen-1-yl]oxy}propyl)-1,10,11,12,13,15-hexahydropyrazolo[4',3':9,10][1,6]oxazacycloundecino[8,7,6-hi]indole-8-carboxylic acid (Enantiomer 2)

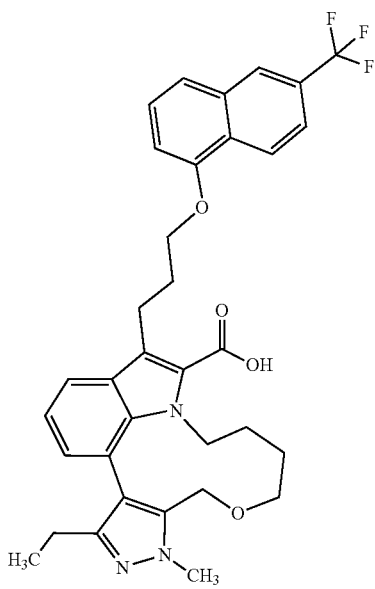 [SMILES: CCc1nn(C)c2c1-c1cccc3c(CCCOc4cccc5cc(C(F)(F)F)ccc45)c(C(=O)O)n(c13)CCCCOC2]

For the preparation of the racemic title compound and separation into its enantiomers see Example 313.

Analytical Chiral HPLC (method see Example 313): $R_t$=1.33 min.

LC-MS Method 1): $R_t$=1.63 min; MS (ESIpos): m/z=606 [M+H]⁺

¹H-NMR (400 MHz, DMSO-d6) δ[ppm]: 0.797 (0.62), 0.813 (0.64), 0.820 (0.65), 0.875 (4.85), 0.885 (0.70), 0.894 (11.20), 0.904 (1.07), 0.913 (5.05), 0.922 (0.49), 0.999 (1.14), 1.205 (0.70), 1.232 (0.67), 1.255 (0.55), 2.124 (0.75), 2.131 (0.70), 2.142 (1.94), 2.150 (1.96), 2.161 (1.96), 2.169 (1.92), 2.180 (0.69), 2.188 (0.75), 2.202 (0.55), 2.206 (0.55), 2.216 (1.00), 2.233 (1.47), 2.250 (1.04), 2.518 (3.75), 2.523 (2.49), 2.743 (0.62), 2.756 (0.54), 2.773 (0.69), 3.278 (0.70), 3.381 (1.17), 3.399 (1.17), 3.410 (0.75), 3.428 (0.80), 3.847 (16.00), 3.992 (0.42), 4.004 (0.67), 4.016 (0.44), 4.027 (0.44), 4.227 (2.73), 4.239 (2.90), 4.255 (1.61), 4.261 (2.28), 4.504 (0.77), 4.515 (0.47), 4.528 (0.42), 4.539 (0.70), 4.606 (2.09), 4.639 (1.87), 6.833 (1.66), 6.851 (1.94), 7.020 (1.61), 7.040 (2.04), 7.058 (1.72), 7.063 (2.01), 7.082 (2.04), 7.527 (1.42), 7.547 (2.56), 7.567 (1.64), 7.666 (2.39), 7.687 (1.74), 7.717 (1.49), 7.722 (1.51), 7.731 (1.82), 7.733 (1.82), 7.740 (1.74), 7.744 (1.72), 7.751 (1.72), 8.368 (2.59), 8.380 (1.84), 8.403 (1.62).

Example 316

(rac)-1-(3-((5-chloronaphthalen-1-yl)oxy)propyl)-10,12-dimethyl-4,5,6,7,9,10-hexahydropyrazolo[4',3':9,10][1,6]oxaazacycloundecino[8,7,6-hi]indole-2-carboxylic acid

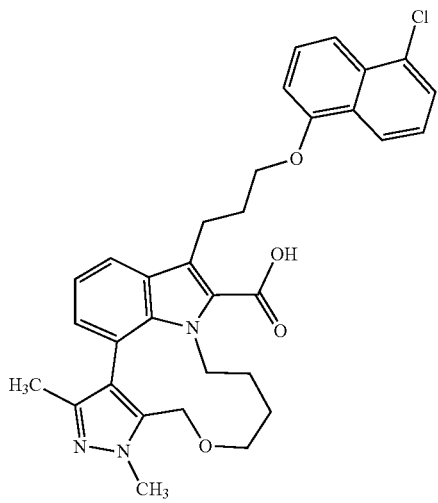 [SMILES: Cc1nn(C)c2c1-c1cccc3c(CCCOc4cccc5c(Cl)cccc45)c(C(=O)O)n(c13)CCCCOC2]

To a solution of (rac)-ethyl 1-(3-((5-chloronaphthalen-1-yl)oxy)propyl)-10,12-dimethyl-4,5,6,7,9,10-hexahydropyrazolo[4',3':9,10][1]oxa[6]azacycloundecino[8,7,6-hi]indole-2-carboxylate (50 mg; see Intermediate 501) in ethanol (5 ml) was added an aqueous solution of lithium hydroxide (2 ml, 2 N), the mixture was heated to 80° C. for 66 hours and then cooled to room temperature. Volatiles were removed under reduced pressure and the residue was suspended in a mixture of ethyl acetate (100 ml) and aqueous HCl (3 N, 100 ml). The layers were separated and the organic layer was washed with saturated aqueous sodium chloride solution, dried over sodium sulfate and filtered. Volatiles were removed under reduced pressure and the residue was purified by normal phase flash chromatography on silica gel (8 g) eluting with a gradient of methanol in dichloromethane (0-5%) to give the title compound as a tacky off white solid (23 mg).

LRMS (ESIneg) m/z=556 [M−H]$^-$ $^1$H NMR (300 MHz, Chloroform-d) δ 8.30 (dt, J=8.4, 1.0 Hz, 1H), 7.80 (d, J=8.6 Hz, 1H), 7.75 (dd, J=8.1, 1.3 Hz, 1H), 7.56 (dd, J=7.4, 1.1 Hz, 1H), 7.48-7.39 (m, 1H), 7.35 (dd, J=8.5, 7.4 Hz, 1H), 7.08 (dd, J=8.1, 7.1 Hz, 1H), 6.91 (dd, J=7.1, 1.2 Hz, 1H), 6.80 (d, J=7.7 Hz, 1H), 4.67 (d, J=14.2 Hz, 1H), 4.59 (d, J=13.4 Hz, 1H), 4.46 (d, J=13.4 Hz, 1H), 4.20 (t, J=6.0 Hz, 2H), 4.16-4.06 (m, 1H), 3.96 (s, 3H), 3.46 (tq, J=13.6, 7.3, 6.6 Hz, 3H), 2.94-2.78 (m, 1H), 2.36 (p, J=6.9 Hz, 2H), 2.00 (s, 3H), 1.64-1.44 (m, 1H), 1.31-1.01 (m, 3H).

Example 317

(+)-1,3-dimethyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (Enantiomer 1)

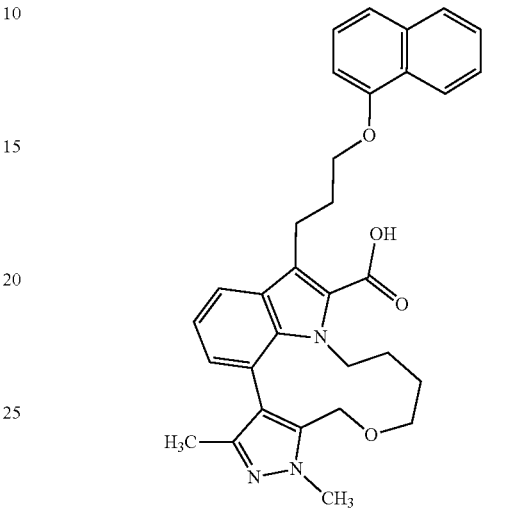

For the preparation of the racemic title compound see Example 1-33

Preparative chiral HPLC method: Instrument: Sepiatec: Prep SFC100; column: Chiralpak ID 5 μm 250×30 mm; eluent A: CO$_2$, eluent B: 2-propanol+0.4 Vol-% diethylamine (99%); isocratic: 25% B; flow 100.0 ml/min temperature: 40° C.; BPR: 150 bar; MWD @ 254 nm Analytical chiral HPLC method: Instrument: Agilent: 1260, Aurora SFC-Modul; column: Chiralpak ID 5 μm 100×4.6 mm; eluent A: CO$_2$, eluent B: 2-propanol+0.2 Vol-% diethylamine (99%); isocratic: 25% B; flow 4.0 ml/min; temperature: 37.5° C.; BPR: 100 bar; MWD @ 254 nm Analytical Chiral HPLC: R$_t$=1.85 min.

Specific optical rotation (Method O1): +26.2° (c=1.0 g/100 ml in DMSO)

$^1$H-NMR (400 MHz, DMSO-d6) δ[ppm]: 1.138 (1.88), 1.143 (4.47), 1.161 (9.96), 1.180 (4.41), 1.232 (0.52), 1.835 (0.43), 1.852 (0.87), 1.870 (1.10), 1.888 (1.03), 1.911 (15.67), 2.116 (0.75), 2.181 (1.08), 2.198 (1.45), 2.217 (1.12), 2.518 (4.51), 2.523 (3.08), 2.673 (0.85), 2.858 (1.16), 2.877 (3.62), 2.895 (3.48), 2.913 (1.08), 3.237 (1.24), 3.256 (1.95), 3.274 (1.37), 3.833 (16.00), 4.024 (0.54), 4.037 (0.62), 4.051 (0.50), 4.059 (0.58), 4.176 (1.47), 4.192 (3.15), 4.207 (1.92), 4.235 (1.68), 4.312 (1.26), 4.343 (0.75), 4.371 (0.41), 4.387 (0.58), 4.395 (0.48), 4.407 (0.62), 4.421 (0.54), 4.428 (0.43), 4.639 (1.12), 4.644 (1.18), 4.682 (1.26), 4.687 (1.39), 4.742 (1.26), 4.747 (1.22), 4.767 (1.45), 4.772 (1.28), 5.162 (0.50), 5.200 (0.46), 5.217 (0.87), 5.226 (0.41), 5.234 (0.43), 5.243 (1.12), 5.260 (1.08), 5.285 (0.68), 6.888 (2.84), 6.905 (3.29), 6.985 (1.20), 7.004 (1.70), 7.022 (0.91), 7.363 (1.39), 7.383 (2.61), 7.402 (2.15), 7.439 (2.77), 7.460 (1.49), 7.494 (0.54), 7.506 (1.76), 7.511 (3.04), 7.520 (3.56), 7.530 (3.17), 7.534 (1.92), 7.546 (0.62), 7.618 (1.18), 7.637 (1.12), 7.852 (1.57), 7.856 (1.14), 7.863 (0.83), 7.867 (0.97), 7.870 (1.06), 7.875 (1.35), 8.240 (1.39), 8.248 (1.01), 8.252 (0.66), 8.264 (1.30).

Example 318

(−)-1,3-dimethyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (Enantiomer 2)

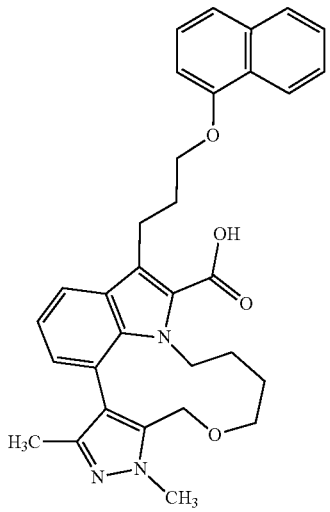 [SMILES: Cc1nn(C)c2c1-c1cccc3c(CCCOc4cccc5ccccc45)c(C(=O)O)n(c13)CCCCOC2]

For the preparation of the racemic title compound see Example 1-33

Preparative chiral HPLC method: Instrument: Sepiatec: Prep SFC100; column: Chiralpak ID 5 μm 250×30 mm; eluent A: $CO_2$, eluent B: 2-propanol+0.4 Vol-% diethylamine (99%); isocratic: 25% B; flow 100.0 ml/min temperature: 40° C.; BPR: 150 bar; MWD @ 254 nm Analytical chiral HPLC method: Instrument: Agilent: 1260, Aurora SFC-Modul; column: Chiralpak ID 5 μm 100×4.6 mm; eluent A: $CO_2$, eluent B: 2-propanol+0.2 Vol-% diethylamine (99%); isocratic: 25% B; flow 4.0 ml/min; temperature: 37.5° C.; BPR: 100 bar; MWD @ 254 nm Analytical Chiral HPLC: $R_t$=5.33 min.

Specific optical rotation (Method O1): −23.9° (c=1.0 g/100 ml in DMSO)

$^1$H-NMR (400 MHz, DMSO-d6) δ[ppm]: 1.140 (4.70), 1.158 (10.36), 1.176 (4.68), 1.233 (0.73), 1.832 (0.40), 1.851 (0.83), 1.868 (1.06), 1.888 (1.03), 1.911 (16.00), 1.960 (0.68), 2.116 (0.60), 2.179 (1.03), 2.197 (1.38), 2.216 (1.08), 2.318 (0.43), 2.322 (0.98), 2.327 (1.43), 2.332 (1.06), 2.336 (0.45), 2.518 (5.03), 2.523 (3.50), 2.660 (0.45), 2.665 (1.01), 2.669 (1.43), 2.673 (1.03), 2.678 (0.43), 2.854 (1.16), 2.872 (3.62), 2.890 (3.47), 2.909 (1.08), 3.231 (1.13), 3.251 (1.79), 3.269 (1.21), 3.833 (15.90), 4.021 (0.48), 4.033 (0.58), 4.048 (0.45), 4.056 (0.55), 4.176 (1.41), 4.192 (3.04), 4.207 (1.81), 4.234 (1.46), 4.312 (1.06), 4.343 (0.63), 4.371 (0.40), 4.387 (0.55), 4.395 (0.45), 4.406 (0.60), 4.421 (0.50), 4.428 (0.43), 4.639 (1.08), 4.644 (1.16), 4.682 (1.21), 4.687 (1.33), 4.742 (1.23), 4.747 (1.21), 4.767 (1.43), 4.772 (1.26), 5.157 (0.55), 5.200 (0.43), 5.217 (0.83), 5.226 (0.40), 5.235 (0.40), 5.243 (1.11), 5.260 (1.06), 5.286 (0.65), 6.888 (2.21), 6.898 (1.33), 6.905 (2.29), 6.980 (1.08), 6.999 (1.56), 7.017 (0.81), 7.363 (1.38), 7.383 (2.62), 7.402 (2.19), 7.439 (2.72), 7.459 (1.43), 7.493 (0.53), 7.505 (1.69), 7.510 (3.09), 7.520 (3.45), 7.529 (3.25), 7.534 (1.96), 7.546 (0.63), 7.611 (1.06), 7.630 (1.01), 7.852 (1.53), 7.855 (1.11), 7.863 (0.78), 7.867 (0.93), 7.870 (1.03), 7.875 (1.33), 8.240 (1.36), 8.248 (0.98), 8.252 (0.65), 8.264 (1.28).

Example 319

(rac)-3-[(4-methoxyphenoxy)methyl]-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid

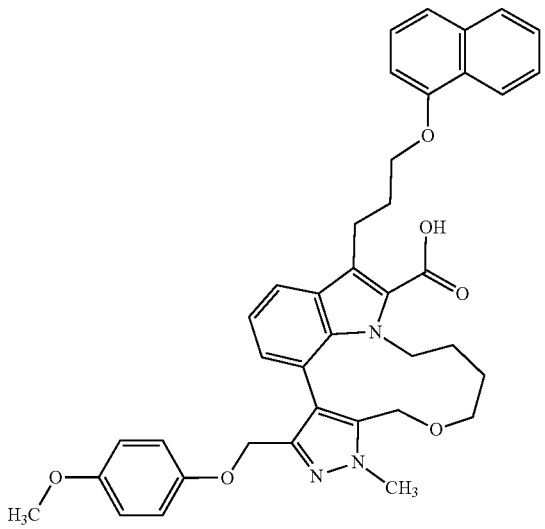 [SMILES: COc1ccc(OCc2nn(C)c3c2-c2cccc4c(CCCOc5cccc6ccccc56)c(C(=O)O)n(c24)CCCCOC3)cc1]

The title compound was prepared in analogy to the synthetic procedures described before. Yield: 122 mg (94% purity)

LC-MS (Method 2): Rt=0.89 min; MS (ESIpos): m/z=646 [M+H]$^+$ $^1$H-NMR (400 MHz, DMSO-d6) δ[ppm]: 1.036 (0.48), 1.049 (0.61), 1.053 (0.63), 1.233 (0.52), 2.085 (13.93), 2.159 (0.53), 2.176 (0.80), 2.193 (0.56), 2.323 (0.46), 2.327 (0.64), 2.332 (0.45), 2.518 (2.52), 2.523 (1.75), 2.665 (0.49), 2.669 (0.66), 2.674 (0.48), 3.266 (0.48), 3.349 (0.60), 3.558 (16.00), 3.563 (1.07), 3.582 (0.43), 3.922 (9.60), 3.942 (0.46), 4.100 (0.56), 4.108 (0.44), 4.117 (0.97), 4.133 (0.94), 4.270 (0.92), 4.303 (1.02), 4.451 (1.21), 4.480 (1.51), 4.672 (1.20), 4.678 (1.61), 4.706 (2.00), 6.529 (2.15), 6.535 (0.68), 6.546 (0.89), 6.552 (3.45), 6.611 (0.52), 6.620 (3.77), 6.626 (0.93), 6.637 (0.74), 6.643 (2.28), 6.801 (1.04), 6.818 (1.20), 6.820 (1.20), 6.822 (1.09), 6.826 (0.96), 6.841 (1.09), 6.843 (1.04), 6.958 (1.07), 6.978 (1.17), 6.996 (0.83), 7.339 (0.84), 7.360 (1.44), 7.379 (1.16), 7.433 (1.46), 7.454 (0.91), 7.501 (0.94), 7.506 (0.84), 7.509 (1.08), 7.518 (2.10), 7.525 (1.09), 7.529 (0.93), 7.533 (1.04), 7.697 (0.91), 7.700 (0.96), 7.717 (0.88), 7.720 (0.86), 7.850 (0.86), 7.858 (0.46), 7.868 (0.76), 7.874 (0.75), 8.229 (0.77), 8.236 (0.73), 8.252 (0.63), 8.253 (0.69).

The title compound (118 mg) was separated into enantiomers by preparative chiral HPLC to give enantiomer 1 (44 mg, see Example 320) and enantiomer 2 (51 mg, see Example 321).

Preparative chiral HPLC method: Instrument: Sepiatec: Prep SFC100; column: Chiralpak IA 5 μm 250×20 mm; eluent A $CO_2$, eluent B: Ethanol+0.4 Vol-% diethylamine (99%); isocratic: 35% B; flow 100.0 ml/min temperature: 40° C.; BPR: 150 bar; MWD @ 254 nm Analytical chiral HPLC method: Instrument: Agilent: 1260, Aurora SFC-Modul; column: Chiralpak IA 5 μm 100×4.6 mm; eluent A: $CO_2$, eluent B: ethanol+0.4 Vol-% diethylamine (99%); isocratic: 35% B; Flow 4.0 ml/min; temperature: 37.5° C.; BPR: 100 bar; MWD @ 254 nm Example 320

3-[(4-methoxyphenoxy)methyl]-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid-N-ethylethanamine salt (Enantiomer 1)

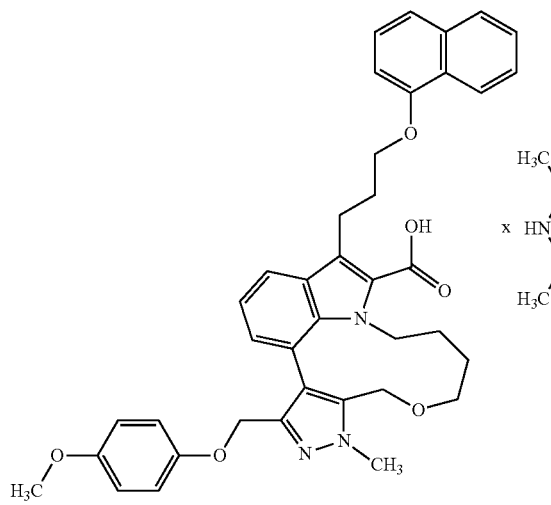

For the preparation of the racemic title compound and separation into its enantiomers see Example 319.

Analytical Chiral HPLC (method see Example 319): $R_t$=2.84 min.

LC-MS (Method 2): $R_t$=0.90 min; MS (ESIpos): m/z=646 [M+H]$^+$ $^1$H-NMR (400 MHz, DMSO-d6) δ[ppm]: 1.130 (3.58), 1.147 (7.43), 1.166 (3.78), 1.233 (0.66), 2.154 (0.66), 2.171 (1.03), 2.188 (0.72), 2.337 (0.46), 2.518 (5.31), 2.523 (3.72), 2.678 (0.44), 2.833 (0.94), 2.851 (2.27), 2.869 (2.21), 2.888 (0.70), 3.449 (0.42), 3.542 (16.00), 3.910 (9.73), 4.106 (0.50), 4.115 (0.57), 4.123 (1.01), 4.129 (1.01), 4.139 (0.59), 4.146 (0.50), 4.251 (0.98), 4.285 (1.07), 4.464 (1.27), 4.492 (1.60), 4.650 (1.81), 4.662 (1.46), 4.678 (1.46), 4.695 (1.25), 6.594 (0.61), 6.617 (3.41), 6.628 (5.07), 6.635 (0.66), 6.644 (0.48), 6.650 (0.77), 6.688 (0.50), 6.706 (0.57), 6.802 (1.11), 6.820 (1.20), 6.879 (0.57), 6.898 (0.90), 6.917 (0.50), 7.324 (0.85), 7.344 (1.55), 7.364 (1.16), 7.419 (1.55), 7.440 (0.96), 7.490 (0.94), 7.494 (0.83), 7.500 (1.03), 7.507 (2.14), 7.514 (1.05), 7.519 (0.92), 7.523 (1.03), 7.536 (0.42), 7.587 (0.61), 7.605 (0.57), 7.841 (0.94), 7.849 (0.52), 7.859 (0.92), 7.864 (0.81), 8.220 (0.81), 8.225 (0.79), 8.244 (0.77).

Example 321

3-[(4-methoxyphenoxy)methyl]-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid-N-ethylethanamine salt (Enantiomer 2)

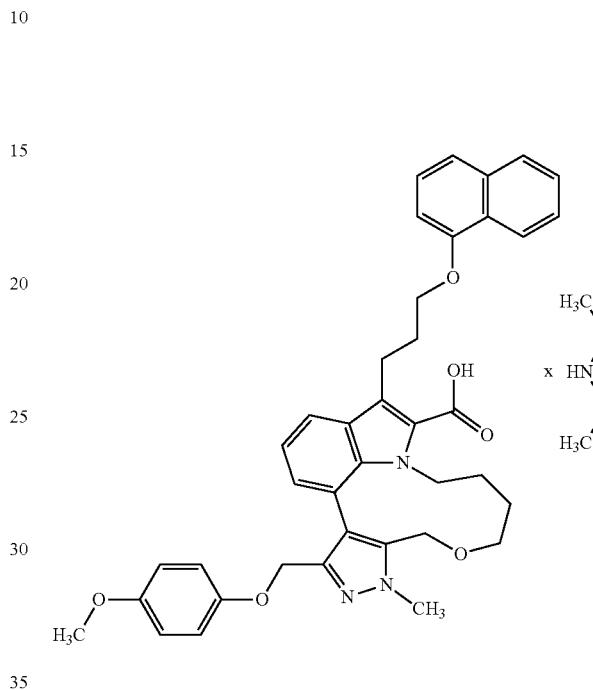

For the preparation of the racemic title compound and separation into its enantiomers see Example 319.

Analytical Chiral HPLC (method see Example 319): $R_t$=3.76 min.

LC-MS (Method 2): $R_t$=0.90 min; MS (ESIpos): m/z=646 [M+H]$^+$ $^1$H-NMR (400 MHz, DMSO-d6) δ[ppm]: 1.044 (1.01), 1.142 (2.40), 1.161 (4.50), 1.179 (2.51), 1.232 (1.19), 1.425 (0.51), 2.157 (1.09), 2.174 (1.64), 2.191 (1.15), 2.327 (1.19), 2.539 (3.70), 2.669 (1.25), 2.801 (0.53), 2.815 (0.60), 2.831 (0.58), 2.865 (0.62), 2.883 (1.62), 2.901 (1.56), 2.919 (0.55), 3.183 (0.53), 3.199 (0.57), 3.216 (0.72), 3.234 (0.41), 3.433 (0.43), 3.451 (0.76), 3.462 (0.64), 3.480 (0.68), 3.548 (16.00), 3.915 (11.34), 4.014 (0.60), 4.103 (0.76), 4.119 (1.60), 4.131 (1.58), 4.146 (0.76), 4.258 (1.38), 4.292 (1.54), 4.458 (1.64), 4.486 (2.05), 4.586 (0.55), 4.620 (0.49), 4.663 (3.12), 4.690 (1.85), 4.698 (1.68), 6.566 (1.77), 6.589 (3.88), 6.623 (5.09), 6.640 (1.07), 6.646 (2.22), 6.748 (0.92), 6.765 (1.07), 6.800 (1.68), 6.818 (1.75), 6.914 (0.92), 6.932 (1.42), 6.951 (0.78), 7.329 (0.97), 7.350 (1.99), 7.369 (1.38), 7.424 (2.20), 7.445 (1.38), 7.481 (0.49), 7.494 (1.27), 7.498 (1.33), 7.503 (1.50), 7.511 (2.55), 7.518 (1.56), 7.522 (1.44), 7.527 (1.36), 7.540 (0.53), 7.635 (1.09), 7.655 (1.05), 7.845 (1.38), 7.862 (1.21), 7.868 (1.15), 8.224 (1.15), 8.229 (1.15), 8.247 (1.19).

Example 322

1-methyl-3-({4-[(methylsulfonyl)amino]phenoxy}methyl)-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid-N-ethylethanamine salt (Enantiomer 1)

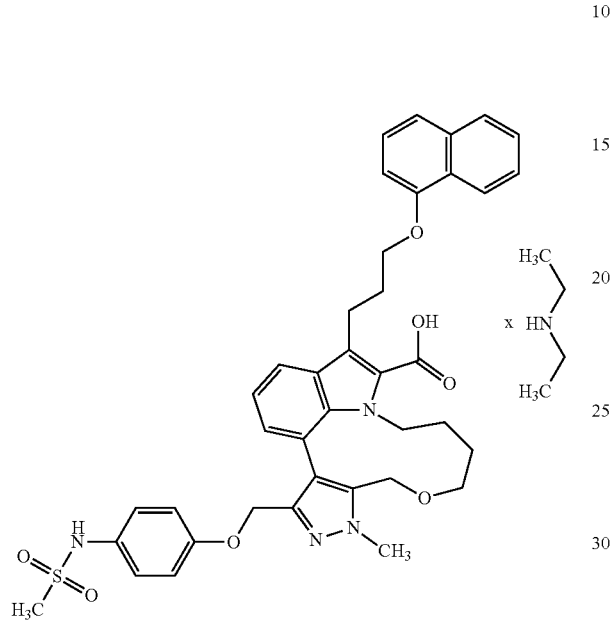

The title compound was prepared in analogy to the synthetic procedures described before.

Yield: 15 mg (95% purity)

LC-MS (Method 2): $R_t$=0.80 min; MS (ESIpos): m/z=709 [M+H]$^+$ $^1$H-NMR (400 MHz, DMSO-d6) δ[ppm]: 0.960 (0.68), 0.975 (0.72), 0.992 (0.64), 1.009 (0.47), 1.027 (0.42), 1.133 (4.67), 1.137 (3.99), 1.151 (9.89), 1.169 (4.97), 1.232 (0.98), 1.430 (0.38), 2.116 (1.49), 2.181 (1.15), 2.198 (1.70), 2.215 (1.19), 2.337 (0.81), 2.518 (9.51), 2.523 (6.71), 2.540 (2.29), 2.639 (15.07), 2.678 (0.85), 2.811 (0.68), 2.823 (0.55), 2.840 (0.68), 2.857 (1.36), 2.875 (3.31), 2.893 (3.18), 2.911 (1.02), 3.184 (0.47), 3.198 (0.55), 3.218 (0.72), 3.235 (0.42), 3.374 (1.10), 3.390 (0.81), 3.785 (0.55), 3.835 (16.00), 4.113 (1.49), 4.146 (1.70), 4.165 (1.15), 4.181 (2.08), 4.196 (1.06), 4.220 (1.78), 4.257 (2.04), 4.415 (0.72), 4.450 (0.68), 4.507 (2.16), 4.544 (1.91), 4.556 (1.95), 4.589 (1.70), 6.404 (1.02), 6.420 (1.06), 6.554 (4.03), 6.576 (4.58), 6.796 (5.05), 6.818 (4.16), 6.851 (1.15), 6.872 (2.93), 6.891 (2.33), 7.349 (1.19), 7.369 (2.33), 7.389 (1.78), 7.433 (2.59), 7.453 (1.49), 7.489 (0.51), 7.502 (1.53), 7.508 (2.16), 7.517 (3.23), 7.526 (2.33), 7.532 (1.70), 7.544 (0.59), 7.622 (1.23), 7.641 (1.15), 7.850 (1.53), 7.859 (0.81), 7.867 (1.19), 7.873 (1.32), 8.234 (1.36), 8.241 (1.32), 8.249 (0.68), 8.258 (1.27).

Example 323

1-methyl-3-({4-[(methylsulfonyl)amino]phenoxy}methyl)-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid-N-ethylethanamine salt (Enantiomer 2)

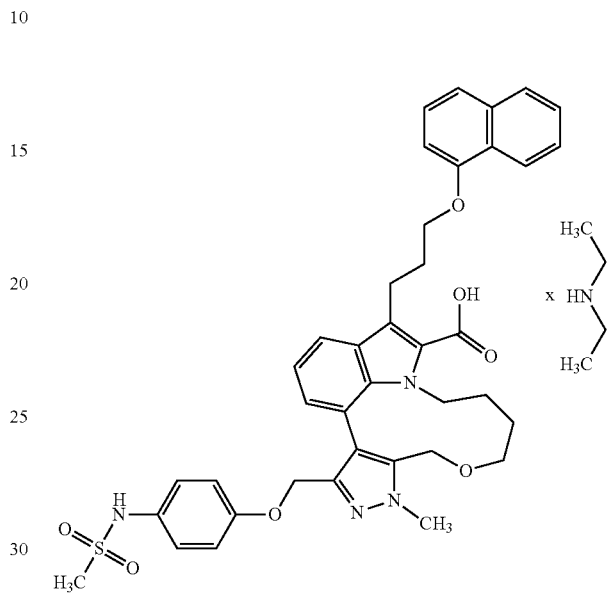

The title compound was prepared in analogy to the synthetic procedures described before.

Yield: 15 mg (94% purity)

LC-MS (Method 2): $R_t$=0.79 min; MS (ESIpos): m/z=709 [M+H]$^+$ $^1$H-NMR (400 MHz, DMSO-d6) δ[ppm]: 0.975 (0.78), 0.992 (0.82), 1.009 (0.55), 1.027 (1.01), 1.042 (0.87), 1.133 (4.39), 1.137 (6.13), 1.151 (9.10), 1.170 (4.34), 1.234 (0.96), 1.415 (0.46), 2.116 (2.42), 2.181 (1.19), 2.198 (1.74), 2.216 (1.19), 2.337 (0.87), 2.518 (10.65), 2.523 (7.36), 2.639 (15.04), 2.678 (1.01), 2.794 (0.87), 2.810 (0.69), 2.823 (0.59), 2.839 (0.69), 2.858 (1.23), 2.876 (2.97), 2.894 (2.88), 2.912 (0.91), 3.187 (0.50), 3.200 (0.59), 3.219 (0.78), 3.240 (0.46), 3.375 (1.19), 3.391 (0.87), 3.788 (0.59), 3.835 (16.00), 3.919 (0.41), 4.113 (1.51), 4.147 (1.74), 4.166 (1.19), 4.181 (2.10), 4.197 (1.10), 4.220 (1.74), 4.257 (2.06), 4.415 (0.73), 4.450 (0.64), 4.507 (2.19), 4.544 (1.92), 4.556 (2.01), 4.589 (1.65), 6.405 (1.05), 6.423 (1.10), 6.554 (3.93), 6.577 (4.66), 6.797 (5.03), 6.818 (4.21), 6.852 (1.14), 6.872 (3.25), 6.891 (2.61), 7.349 (1.23), 7.369 (2.33), 7.389 (1.74), 7.433 (2.56), 7.453 (1.46), 7.489 (0.55), 7.502 (1.60), 7.508 (2.19), 7.517 (3.15), 7.526 (2.38), 7.532 (1.65), 7.545 (0.55), 7.623 (1.28), 7.643 (1.14), 7.850 (1.55), 7.859 (0.82), 7.867 (1.19), 7.873 (1.28), 8.234 (1.42), 8.241 (1.28), 8.250 (0.69), 8.258 (1.28).

Example 324

(rac)-7,10-dimethyl-1-[3-(naphthalen-1-yloxy)propyl]-11-(trifluoromethyl)-4,5,6,7,8,10-hexahydropyrazolo[3',4':7,8][1,5]diazecino[9,10,1-hi]indole-2-carboxylic acid

Example 325

(rac)-1-methyl-7-[3-(naphthalen-1-yloxy)propyl]-3-[(2-oxopiperidin-1-yl)methyl]-1,10,11,12,13,15-hexahydropyrazolo[4',3':9,10][1,6]oxazacycloundecino[8,7,6-hi]indole-8-carboxylic acid

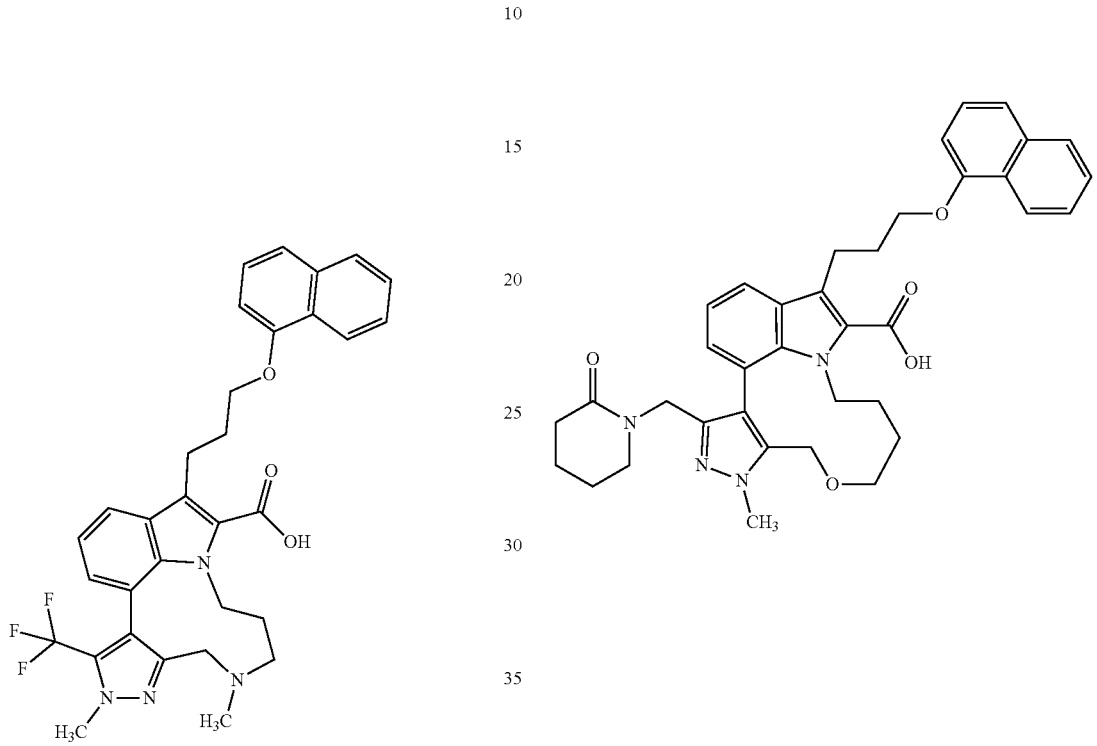

The title compound was prepared in analogy to the synthetic procedures described before.

Yield: 180 mg (98% purity)

LC-MS (Method 2): Rt=0.97 min; MS (ESIpos): m/z=577 [M+H]$^+$ $^1$H-NMR (400 MHz, DMSO-d6) δ[ppm]: 1.779 (7.70), 1.907 (16.00), 2.036 (0.46), 2.071 (0.54), 2.178 (0.73), 2.195 (1.10), 2.212 (0.76), 2.327 (0.59), 2.332 (0.56), 2.337 (0.43), 2.365 (0.49), 2.518 (1.61), 2.523 (1.18), 2.669 (0.42), 3.181 (1.00), 3.214 (1.37), 3.274 (0.48), 3.292 (0.80), 3.333 (3.76), 3.345 (1.45), 3.366 (1.40), 3.379 (0.51), 3.600 (0.42), 4.032 (5.94), 4.034 (6.11), 4.148 (0.69), 4.159 (1.35), 4.163 (1.34), 4.175 (0.70), 4.666 (0.41), 6.841 (1.34), 6.849 (1.32), 6.852 (1.45), 6.859 (1.52), 6.867 (1.80), 6.870 (1.68), 6.946 (1.56), 6.964 (1.37), 6.967 (1.64), 6.984 (1.09), 7.351 (1.08), 7.371 (1.88), 7.391 (1.49), 7.438 (1.89), 7.459 (1.13), 7.509 (1.24), 7.514 (2.28), 7.524 (2.50), 7.533 (2.31), 7.539 (1.42), 7.550 (0.46), 7.713 (1.32), 7.716 (1.37), 7.733 (1.25), 7.736 (1.24), 7.853 (1.08), 7.856 (0.77), 7.863 (0.55), 7.868 (0.65), 7.870 (0.72), 7.876 (0.95), 8.246 (0.97), 8.253 (0.67), 8.270 (0.91).

The title compound was prepared in analogy to the synthetic procedures described before.

Yield: 57.1 mg (97% purity)

LC-MS (Method 1): R$_t$=1.41 min; MS (ESIpos): m/z=621 [M+H]$^+$ $^1$H-NMR (400 MHz, DMSO-d6) δ[ppm]: 1.014 (1.24), 1.029 (1.00), 1.174 (0.57), 1.189 (0.69), 1.204 (0.72), 1.220 (0.79), 1.237 (0.93), 1.256 (0.79), 1.284 (1.00), 1.301 (1.24), 1.318 (1.36), 1.334 (1.12), 1.671 (0.76), 1.686 (1.67), 1.702 (1.48), 1.717 (0.55), 2.164 (0.93), 2.181 (1.41), 2.198 (1.03), 2.318 (0.43), 2.322 (1.00), 2.326 (1.38), 2.332 (0.95), 2.336 (0.43), 2.518 (5.17), 2.522 (3.43), 2.540 (0.43), 2.631 (0.57), 2.642 (0.74), 2.660 (1.14), 2.664 (1.36), 2.668 (1.65), 2.673 (1.38), 2.729 (0.41), 2.850 (0.69), 2.867 (0.86), 2.879 (1.36), 2.888 (1.03), 2.896 (1.00), 2.909 (0.57), 3.226 (0.62), 3.241 (0.57), 3.259 (0.86), 3.278 (0.52), 3.385 (0.55), 3.403 (0.86), 3.418 (0.83), 3.431 (1.03), 3.444 (0.83), 3.459 (0.81), 3.869 (16.00), 3.896 (0.64), 3.988 (0.64), 4.159 (1.76), 4.175 (2.86), 4.197 (4.44), 4.205 (5.56), 4.238 (1.91), 4.478 (0.69), 4.489 (0.43), 4.514 (0.62), 4.614 (1.93), 4.648 (1.76), 5.758 (15.12), 6.815 (1.48), 6.831 (1.72), 6.875 (1.74), 6.892 (1.86), 6.984 (1.62), 7.003 (1.98), 7.021 (1.41), 7.357 (1.34), 7.378 (2.46), 7.397 (2.00), 7.438 (2.62), 7.459 (1.45), 7.496 (0.55), 7.508 (1.81), 7.513 (2.89), 7.523 (3.22), 7.532 (2.79), 7.537 (1.93), 7.548 (0.60), 7.710 (1.57), 7.712 (1.65), 7.730 (1.50), 7.852 (1.50), 7.856 (1.10), 7.863 (0.81), 7.867 (0.93), 7.870 (1.03), 7.875 (1.29), 8.149 (0.67), 8.239 (1.31), 8.247 (0.91), 8.263 (1.22).

Example 326

1-methyl-7-[3-(naphthalen-1-yloxy)propyl]-3-[(2-oxopiperidin-1-yl)methyl]-1,10,11,12,13,15-hexahydropyrazolo[4',3':9,10][1,6]oxazacycloundecino[8,7,6-hi]indole-8-carboxylic acid (Enantiomer 1)

Example 327

1-methyl-7-[3-(naphthalen-1-yloxy)propyl]-3-[(2-oxopiperidin-1-yl)methyl]-1,10,11,12,13,15-hexahydropyrazolo[4',3':9,10][1,6]oxazacycloundecino[8,7,6-hi]indole-8-carboxylic acid (Enantiomer 2)

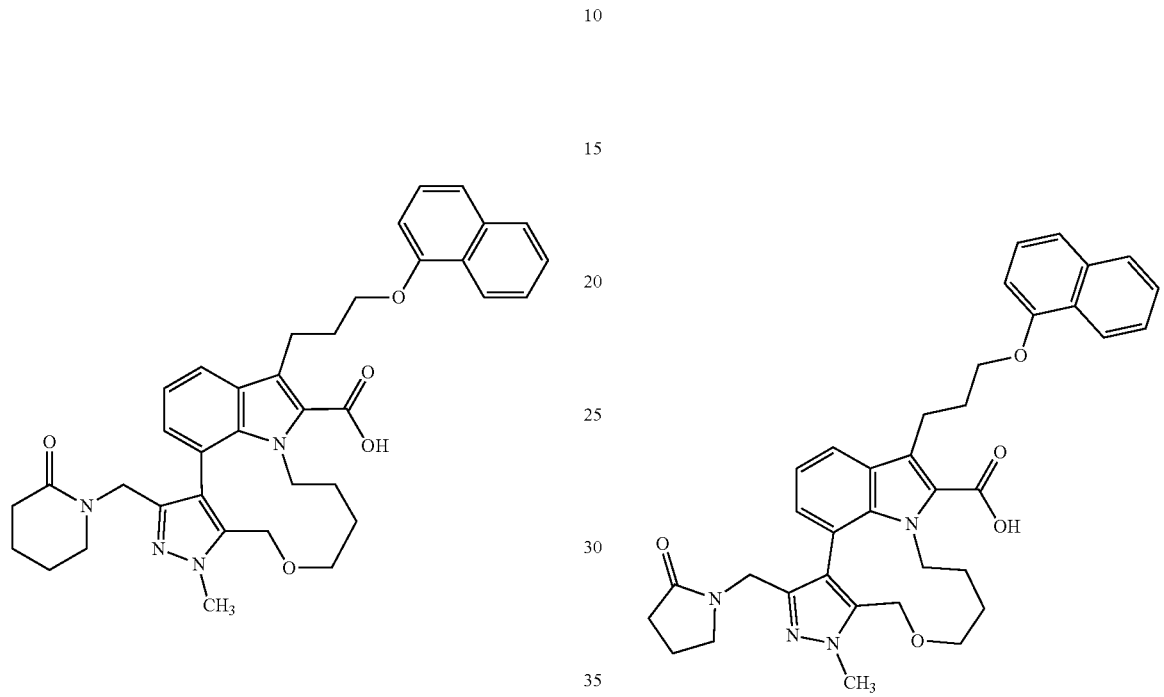

The title compound was prepared in analogy to the synthetic procedures described before.

Yield: 10.7 mg (96% purity)

LC-MS (Method 1): $R_t$=1.41 min; MS (ESIpos): m/z=621 [M+H]$^+$ $^1$H-NMR (400 MHz, DMSO-d6) δ[ppm]: 0.966 (0.56), 1.006 (1.24), 1.026 (2.00), 1.040 (1.55), 1.106 (5.10), 1.138 (4.09), 1.156 (8.25), 1.175 (4.22), 1.235 (1.35), 1.254 (1.10), 1.273 (0.99), 1.289 (1.17), 1.303 (0.94), 1.399 (0.52), 1.686 (0.52), 1.714 (0.65), 1.730 (0.97), 1.745 (0.49), 1.796 (0.72), 2.138 (0.40), 2.156 (1.24), 2.173 (1.89), 2.190 (1.30), 2.518 (5.12), 2.522 (3.30), 2.564 (0.43), 2.579 (0.65), 2.592 (0.81), 2.609 (0.79), 2.673 (1.03), 2.811 (0.43), 2.831 (0.99), 2.844 (1.37), 2.855 (2.09), 2.874 (3.66), 2.891 (3.15), 2.910 (0.97), 3.160 (1.03), 3.176 (1.10), 3.194 (1.39), 3.212 (1.19), 3.438 (3.35), 3.455 (2.40), 3.472 (1.78), 3.502 (3.19), 3.858 (16.00), 3.886 (0.97), 3.903 (0.67), 3.927 (0.45), 4.145 (1.55), 4.162 (3.24), 4.181 (8.90), 4.194 (2.18), 4.227 (2.00), 4.556 (0.65), 4.605 (2.31), 4.638 (1.87), 6.723 (1.17), 6.739 (1.33), 6.864 (1.89), 6.882 (2.09), 6.931 (1.26), 6.950 (1.87), 6.969 (1.12), 7.346 (1.30), 7.367 (2.58), 7.386 (1.93), 7.428 (2.90), 7.449 (1.64), 7.487 (0.58), 7.500 (1.80), 7.504 (2.97), 7.514 (3.33), 7.523 (3.15), 7.528 (1.91), 7.540 (0.58), 7.638 (1.39), 7.657 (1.30), 7.845 (1.66), 7.855 (0.88), 7.863 (1.12), 7.868 (1.42), 8.229 (1.42), 8.236 (1.08), 8.253 (1.28).

The title compound was prepared in analogy to the synthetic procedures described before.

Yield: 6.30 mg (93% purity)

LC-MS (Method 1): $R_t$=1.41 min; MS (ESIpos): m/z=621 [M+H]$^+$ $^1$H-NMR (400 MHz, DMSO-d6) δ[ppm]: 0.967 (0.51), 1.009 (1.38), 1.026 (2.50), 1.042 (2.00), 1.107 (9.22), 1.135 (2.94), 1.153 (5.41), 1.171 (3.01), 1.232 (1.45), 1.255 (1.09), 1.295 (1.20), 1.310 (0.98), 1.347 (0.65), 1.388 (0.54), 1.674 (0.44), 1.701 (0.65), 1.718 (0.98), 1.768 (0.62), 2.158 (1.20), 2.175 (1.81), 2.192 (1.31), 2.518 (8.38), 2.522 (5.51), 2.596 (0.58), 2.610 (0.73), 2.626 (0.73), 2.673 (1.56), 2.835 (0.80), 2.862 (1.67), 2.879 (2.25), 2.897 (1.89), 2.915 (0.58), 3.181 (0.58), 3.199 (0.62), 3.214 (0.80), 3.390 (1.63), 3.407 (1.52), 3.424 (1.60), 3.442 (1.45), 3.459 (1.12), 3.474 (0.87), 3.503 (3.70), 3.863 (16.00), 3.890 (0.54), 3.932 (0.58), 4.150 (1.56), 4.167 (3.12), 4.187 (7.69), 4.198 (2.29), 4.232 (2.00), 4.532 (0.58), 4.564 (0.54), 4.609 (2.10), 4.642 (1.89), 6.752 (0.87), 6.769 (0.98), 6.869 (1.89), 6.887 (2.03), 6.948 (0.98), 6.966 (1.56), 6.985 (0.91), 7.351 (1.27), 7.371 (2.50), 7.391 (1.92), 7.432 (2.79), 7.453 (1.60), 7.491 (0.51), 7.503 (1.71), 7.508 (2.98), 7.517 (3.34), 7.527 (3.05), 7.531 (1.96), 7.543 (0.62), 7.662 (1.12), 7.681 (1.05), 7.848 (1.60), 7.859 (0.87), 7.866 (1.12), 7.871 (1.41), 8.234 (1.38), 8.241 (1.05), 8.258 (1.31).

Example 328

(rac)-1-methyl-7-[3-(naphthalen-1-yloxy)propyl]-3-[(2-oxopyrrolidin-1-yl)methyl]-1,10,11,12,13,15-hexahydropyrazolo[4',3':9,10][1,6]oxazacycloundecino[8,7,6-hi]indole-8-carboxylic acid

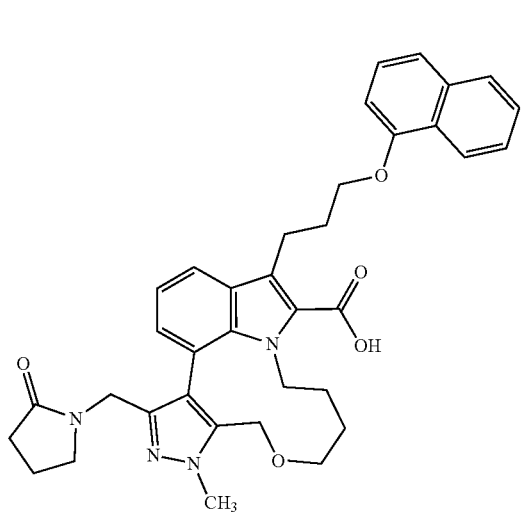 [SMILES: Cn1nc(CN2CCCC2=O)c2c1COCCCCn1c(C(=O)O)c(CCCOc3cccc4ccccc34)c3cccc-2c31]

The title compound was prepared in analogy to the synthetic procedures described before.

Yield: 49.1 mg (100% purity)

LC-MS (Method 1): $R_t$=1.37 min; MS (ESIpos): m/z=607 [M+H]$^+$ $^1$H-NMR (400 MHz, DMSO-d6) δ[ppm]: 1.024 (1.23), 1.275 (0.91), 1.430 (0.50), 1.439 (0.54), 1.453 (0.57), 1.565 (0.54), 1.579 (0.60), 1.703 (1.10), 1.724 (1.64), 1.742 (1.32), 1.765 (0.82), 2.173 (0.94), 2.190 (1.39), 2.208 (1.04), 2.518 (12.54), 2.523 (7.72), 2.543 (0.60), 2.756 (0.47), 2.769 (0.54), 2.778 (1.07), 2.791 (1.07), 2.801 (0.66), 2.814 (0.54), 2.853 (0.72), 2.865 (0.57), 2.882 (0.79), 2.969 (0.54), 2.983 (0.63), 2.991 (1.07), 3.005 (1.04), 3.013 (0.63), 3.027 (0.47), 3.237 (0.63), 3.251 (0.63), 3.269 (0.91), 3.289 (0.57), 3.365 (0.69), 3.382 (0.91), 3.399 (0.76), 3.416 (0.98), 3.432 (1.01), 3.443 (0.82), 3.460 (0.76), 3.882 (16.00), 3.905 (0.82), 3.932 (1.98), 3.969 (2.99), 4.080 (2.87), 4.117 (1.92), 4.155 (1.42), 4.171 (2.87), 4.187 (1.45), 4.233 (1.73), 4.266 (1.92), 4.478 (0.76), 4.513 (0.69), 4.625 (2.08), 4.658 (1.83), 5.759 (10.68), 6.826 (1.51), 6.844 (1.76), 6.874 (1.89), 6.891 (2.02), 6.982 (1.61), 7.002 (2.08), 7.020 (1.39), 7.352 (1.32), 7.373 (2.58), 7.392 (2.08), 7.436 (2.77), 7.457 (1.61), 7.497 (0.54), 7.509 (1.83), 7.513 (2.93), 7.523 (3.28), 7.532 (2.93), 7.537 (2.14), 7.549 (0.63), 7.712 (1.67), 7.730 (1.57), 7.852 (1.57), 7.863 (0.91), 7.867 (1.01), 7.870 (1.10), 7.875 (1.42), 8.240 (1.35), 8.248 (1.01), 8.264 (1.29).

Example 329

1-methyl-7-[3-(naphthalen-1-yloxy)propyl]-3-[(2-oxopyrrolidin-1-yl)methyl]-1,10,11,12,13,15-hexahydropyrazolo[4',3':9,10][1,6]oxazacycloundecino[8,7,6-hi]indole-8-carboxylic acid (Enantiomer 2)

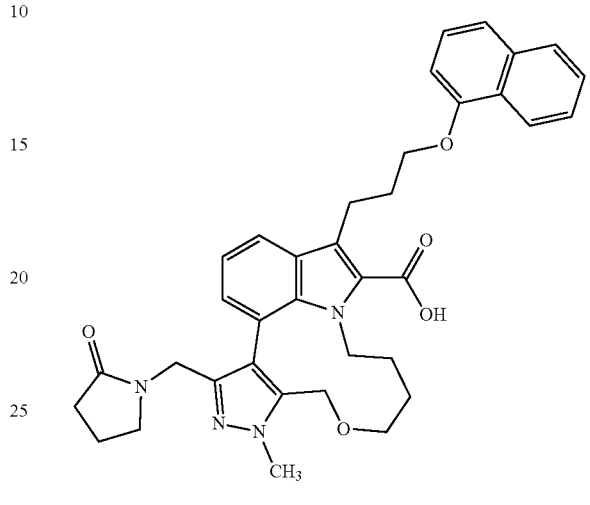

The title compound was prepared in analogy to the synthetic procedures described before.

Yield: 15.3 mg (100% purity)

$^1$H-NMR (400 MHz, DMSO-d6) δ[ppm]: 0.798 (2.21), 0.803 (1.21), 0.814 (2.46), 0.821 (2.50), 0.840 (1.51), 0.851 (1.25), 0.886 (1.21), 0.904 (2.24), 0.922 (1.18), 1.021 (1.51), 1.049 (1.43), 1.084 (0.55), 1.135 (1.03), 1.142 (0.59), 1.154 (1.88), 1.172 (0.99), 1.234 (2.94), 1.274 (1.77), 1.289 (1.58), 1.454 (0.74), 1.505 (0.44), 1.524 (0.44), 1.564 (0.66), 1.578 (0.74), 1.633 (0.44), 1.657 (0.51), 1.675 (0.48), 1.700 (1.29), 1.717 (2.17), 1.741 (1.66), 1.758 (0.96), 1.848 (0.74), 2.045 (0.92), 2.069 (2.57), 2.083 (3.90), 2.095 (1.36), 2.154 (0.59), 2.171 (1.21), 2.189 (1.73), 2.209 (1.40), 2.230 (0.70), 2.322 (1.54), 2.326 (2.13), 2.331 (1.54), 2.373 (0.48), 2.388 (0.51), 2.394 (0.59), 2.406 (0.66), 2.412 (0.81), 2.664 (1.58), 2.668 (2.13), 2.673 (1.58), 2.759 (0.51), 2.772 (0.63), 2.781 (1.18), 2.794 (1.21), 2.803 (0.77), 2.817 (0.63), 2.838 (0.44), 2.854 (0.88), 2.865 (0.66), 2.883 (0.96), 2.902 (0.63), 2.971 (0.66), 2.993 (1.21), 3.007 (1.18), 3.015 (0.70), 3.029 (0.51), 3.242 (0.74), 3.255 (0.74), 3.275 (0.96), 3.293 (0.48), 3.367 (0.55), 3.384 (0.92), 3.404 (0.88), 3.417 (1.07), 3.430 (1.14), 3.443 (1.03), 3.460 (0.92), 3.882 (16.00), 3.932 (2.69), 3.969 (4.23), 4.004 (1.32), 4.080 (4.49), 4.117 (4.08), 4.156 (4.38), 4.172 (6.14), 4.188 (4.78), 4.233 (5.30), 4.267 (5.00), 4.345 (2.06), 4.361 (2.24), 4.377 (1.73), 4.471 (1.58), 4.494 (1.10), 4.505 (1.40), 4.625 (2.43), 4.658 (2.13), 6.831 (1.95), 6.834 (1.99), 6.849 (2.39), 6.872 (2.02), 6.891 (2.13), 6.986 (1.80), 7.006 (2.28), 7.024 (1.43), 7.352 (1.32), 7.373 (2.57), 7.392 (1.95), 7.436 (2.76), 7.457 (1.58), 7.497 (0.59), 7.509 (1.91), 7.513 (2.91), 7.523 (3.24), 7.532 (2.91), 7.537 (2.02), 7.549 (0.63), 7.718 (2.02), 7.736 (1.88), 7.851 (1.62), 7.869 (1.07), 7.875 (1.36), 8.240 (1.40), 8.247 (1.07), 8.264 (1.29).

Example 330

1-methyl-7-[3-(naphthalen-1-yloxy)propyl]-3-[(2-oxopyrrolidin-1-yl)methyl]-1,10,11,12,13,15-hexa-hydropyrazolo[4',3':9,10][1,6]oxazacycloundecino[8,7,6-hi]indole-8-carboxylic acid (Enantiomer 1)

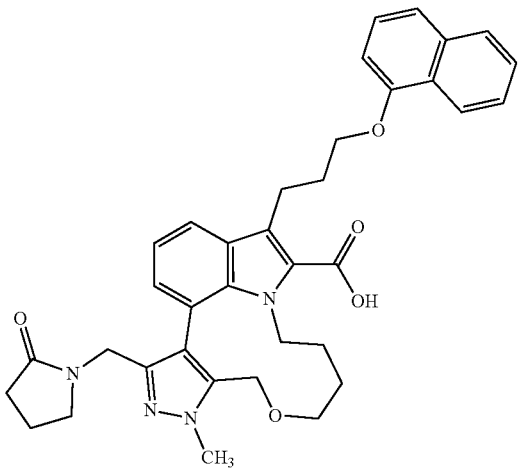 [SMILES: Cn1nc(CN2CCCC2=O)c2c1COCCCCn1c(C(=O)O)c(CCCOc3cccc4ccccc34)c3cccc-2c31]

The title compound was prepared in analogy to the synthetic procedures described before.

Yield: 9.90 mg (100% purity)

$^1$H-NMR (400 MHz, DMSO-d6) δ[ppm]: 0.797 (7.21), 0.802 (3.32), 0.814 (7.51), 0.821 (7.51), 0.831 (1.28), 0.840 (3.94), 0.850 (1.64), 0.867 (0.92), 0.886 (3.94), 0.904 (7.67), 0.922 (4.09), 0.972 (0.72), 1.029 (3.12), 1.049 (2.91), 1.090 (0.66), 1.108 (0.72), 1.123 (0.92), 1.135 (2.71), 1.142 (1.38), 1.154 (5.37), 1.160 (0.97), 1.172 (2.71), 1.233 (3.68), 1.255 (2.56), 1.263 (2.71), 1.274 (3.58), 1.287 (4.50), 1.305 (4.65), 1.314 (1.74), 1.323 (2.25), 1.330 (0.97), 1.430 (1.33), 1.439 (1.48), 1.445 (1.43), 1.454 (1.53), 1.470 (1.18), 1.486 (0.97), 1.504 (1.07), 1.524 (1.12), 1.542 (1.07), 1.563 (1.38), 1.579 (1.58), 1.600 (1.12), 1.610 (0.87), 1.617 (0.97), 1.633 (1.12), 1.656 (1.23), 1.674 (1.18), 1.700 (2.91), 1.717 (4.96), 1.741 (3.63), 1.758 (2.25), 1.783 (0.92), 1.799 (0.82), 1.815 (0.56), 1.844 (1.43), 1.848 (1.43), 1.907 (0.72), 2.031 (0.51), 2.042 (1.48), 2.045 (1.53), 2.068 (8.74), 2.083 (16.00), 2.095 (2.86), 2.139 (0.77), 2.154 (1.69), 2.169 (2.81), 2.189 (4.04), 2.209 (3.58), 2.229 (1.84), 2.358 (1.02), 2.373 (1.48), 2.387 (1.53), 2.393 (1.64), 2.398 (0.87), 2.406 (1.58), 2.411 (2.04), 2.424 (0.56), 2.430 (0.51), 2.518 (12.58), 2.522 (8.13), 2.541 (1.23), 2.758 (1.18), 2.772 (1.38), 2.781 (2.71), 2.794 (2.76), 2.803 (1.69), 2.817 (1.38), 2.837 (0.92), 2.854 (1.89), 2.866 (1.43), 2.883 (2.15), 2.902 (1.48), 2.919 (0.92), 2.932 (0.87), 2.950 (0.66), 2.971 (1.43), 2.985 (1.64), 2.993 (2.76), 3.007 (2.61), 3.015 (1.43), 3.029 (1.07), 3.222 (0.77), 3.242 (1.53), 3.256 (1.53), 3.275 (2.15), 3.293 (1.02), 3.368 (1.07), 3.385 (1.94), 3.403 (1.74), 3.417 (2.20), 3.430 (2.35), 3.444 (2.10), 3.459 (1.89), 3.474 (0.87), 3.905 (1.02), 3.932 (5.11), 3.950 (1.69), 3.969 (8.38), 4.003 (1.02), 4.080 (7.11), 4.117 (4.96), 4.156 (3.63), 4.171 (7.16), 4.187 (3.58), 4.233 (4.50), 4.267 (4.96), 4.345 (1.48), 4.361 (2.76), 4.377 (1.58), 4.393 (0.66), 4.411 (1.33), 4.428 (1.33), 4.446 (0.87), 4.471 (2.45), 4.483 (1.69), 4.494 (1.58), 4.506 (2.35), 4.624 (5.67), 4.658 (5.27), 4.986 (2.15), 5.202 (1.58), 6.831 (4.65), 6.834 (4.81), 6.849 (5.67), 6.852 (5.42), 6.873 (4.60), 6.891 (4.81), 6.986 (4.40), 7.006 (5.42), 7.024 (3.73), 7.352 (3.27), 7.373 (6.19), 7.392 (4.75), 7.436 (6.49), 7.456 (3.68), 7.496 (1.28), 7.508 (4.40), 7.513 (6.85), 7.523 (7.72), 7.532 (6.85), 7.536 (4.70), 7.548 (1.48), 7.715 (4.70), 7.718 (4.81), 7.735 (4.40), 7.738 (4.19), 7.851 (3.73), 7.855 (2.66), 7.863 (2.10), 7.866 (2.30), 7.869 (2.40), 7.875 (3.12), 8.133 (0.56), 8.240 (3.27), 8.248 (2.35), 8.264 (2.96).

Example 331

(rac)-3-[(dimethylamino)methyl]-1-methyl-7-[3-(naphthalen-1-yloxy)propyl]-1,10,11,12,13,15-hexa-hydropyrazolo[4',3':9,10][1,6]oxazacycloundecino[8,7,6-hi]indole-8-carboxylic acid

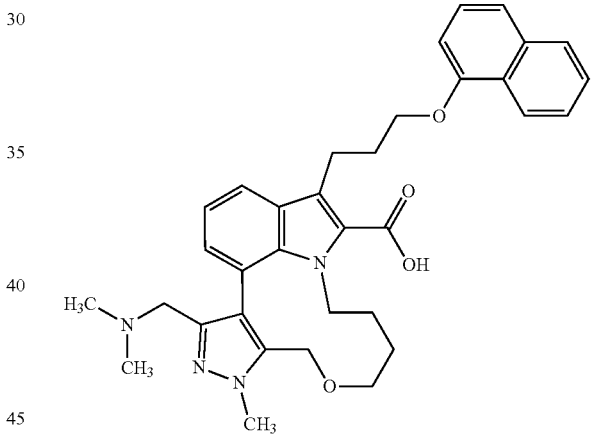

The title compound was prepared in analogy to the synthetic procedures described before.

Yield: 70.4 mg (90% purity)

LC-MS (Method 1): $R_t$=1.13 min; MS (ESIpos): m/z=567 [M+H]$^+$ $^1$H-NMR (400 MHz, DMSO-d6) δ[ppm]: 1.006 (0.88), 1.220 (0.41), 1.890 (0.47), 1.907 (1.04), 1.924 (16.00), 2.195 (0.91), 2.213 (1.33), 2.230 (0.95), 2.326 (0.79), 2.669 (0.78), 2.780 (0.53), 2.793 (0.46), 2.809 (0.53), 2.922 (1.26), 2.934 (0.63), 2.955 (1.94), 3.117 (1.69), 3.150 (1.45), 3.886 (8.77), 3.934 (0.47), 3.972 (0.59), 4.001 (0.95), 4.163 (1.10), 4.179 (2.14), 4.194 (1.12), 4.224 (1.14), 4.258 (1.24), 4.488 (0.56), 4.523 (0.53), 4.630 (1.28), 4.664 (1.12), 5.758 (5.15), 6.792 (1.12), 6.810 (1.28), 6.850 (1.29), 6.868 (1.41), 6.981 (0.94), 7.000 (1.35), 7.019 (0.81), 7.348 (0.81), 7.368 (1.59), 7.387 (1.10), 7.435 (1.92), 7.456 (1.13), 7.488 (0.42), 7.501 (1.10), 7.509 (1.33), 7.517 (2.05), 7.525 (1.38), 7.533 (1.08), 7.705 (1.17), 7.725 (1.10), 7.850 (1.17), 7.867 (0.91), 7.873 (0.90), 8.229 (0.91), 8.235 (0.87), 8.252 (0.85).

Example 332

(rac)-1-methyl-7-[3-(naphthalen-1-yloxy)propyl]-3-(piperidin-1-ylmethyl)-1,10,11,12,13,15-hexahydropyrazolo[4',3':9,10][1,6]oxazacycloundecino[8,7,6-hi]indole-8-carboxylic acid

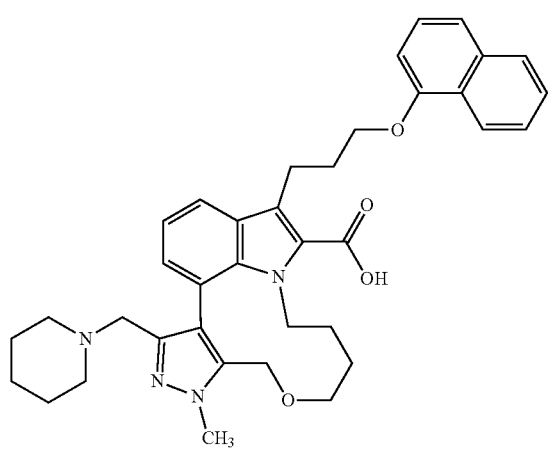 [SMILES: Cn1nc(CN2CCCCC2)c2c1COCCCCn1c(C(=O)O)c(CCCOc3cccc4ccccc34)c3cccc-2c31]

The title compound was prepared in analogy to the synthetic procedures described before.

Yield: 98.9 mg (94% purity)

LC-MS (Method 1): $R_t$=1.22 min; MS (ESIpos): m/z=607 [M+H]$^+$ $^1$H-NMR (400 MHz, DMSO-d6) δ[ppm]: 0.952 (0.66), 1.076 (1.28), 1.099 (0.98), 1.172 (1.67), 1.221 (3.20), 1.233 (3.61), 1.458 (0.52), 1.902 (14.72), 2.005 (1.44), 2.070 (1.39), 2.173 (1.39), 2.191 (2.10), 2.208 (1.48), 2.226 (0.52), 2.322 (1.03), 2.327 (1.35), 2.331 (1.00), 2.665 (0.98), 2.669 (1.37), 2.673 (0.98), 2.735 (0.46), 2.755 (0.75), 2.775 (0.48), 2.910 (2.05), 2.943 (2.67), 3.106 (2.65), 3.122 (0.89), 3.140 (2.53), 3.165 (10.25), 3.286 (2.97), 3.788 (0.46), 3.814 (0.73), 3.861 (16.00), 3.886 (0.68), 4.134 (1.69), 4.150 (3.17), 4.168 (1.57), 4.228 (1.80), 4.261 (1.96), 4.620 (2.19), 4.653 (2.24), 4.699 (0.68), 6.601 (1.23), 6.618 (1.35), 6.821 (2.12), 6.840 (2.33), 6.864 (1.23), 6.883 (1.94), 6.901 (1.10), 7.325 (1.39), 7.345 (2.69), 7.365 (1.92), 7.417 (2.90), 7.438 (1.78), 7.479 (0.59), 7.492 (1.83), 7.498 (2.51), 7.507 (3.49), 7.516 (2.90), 7.522 (1.94), 7.534 (0.87), 7.547 (1.48), 7.566 (1.30), 7.839 (1.71), 7.848 (0.91), 7.856 (1.30), 7.862 (1.44), 8.226 (1.48), 8.233 (1.28), 8.240 (0.78), 8.250 (1.37).

Example 333

1-methyl-7-[3-(naphthalen-1-yloxy)propyl]-3-(piperidin-1-ylmethyl)-1,10,11,12,13,15-hexahydropyrazolo[4',3':9,10][1,6]oxazacycloundecino[8,7,6-hi]indole-8-carboxylic acid (Enantiomer 1)

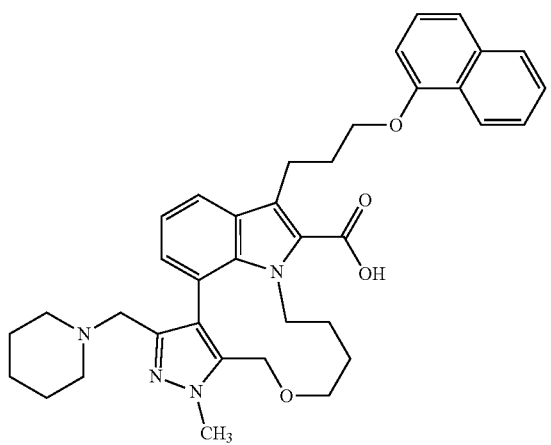

The title compound was prepared in analogy to the synthetic procedures described before.

Yield: 29.0 mg (100% purity)

LC-MS (Method 1): $R_t$=1.19 min; MS (ESIpos): m/z=607 [M+H]$^+$ $^1$H-NMR (400 MHz, DMSO-d6) δ[ppm]: 0.967 (0.43), 1.107 (16.00), 1.127 (3.12), 1.145 (6.85), 1.163 (3.74), 1.204 (1.49), 1.904 (0.46), 1.976 (0.58), 2.073 (0.58), 2.180 (0.65), 2.197 (0.99), 2.214 (0.68), 2.518 (2.85), 2.522 (1.95), 2.673 (0.57), 2.823 (0.81), 2.841 (2.09), 2.859 (2.07), 2.877 (0.64), 2.913 (1.05), 2.946 (1.39), 3.079 (1.20), 3.113 (0.91), 3.205 (0.51), 3.404 (0.64), 3.418 (0.53), 3.434 (0.46), 3.865 (8.99), 3.886 (0.53), 4.135 (0.80), 4.150 (1.66), 4.167 (0.78), 4.240 (0.93), 4.273 (1.01), 4.625 (1.43), 4.658 (1.30), 6.668 (0.64), 6.685 (0.70), 6.819 (1.05), 6.838 (1.12), 6.903 (0.69), 6.923 (1.00), 6.941 (0.61), 7.329 (0.77), 7.350 (1.43), 7.369 (1.11), 7.423 (1.50), 7.444 (0.92), 7.495 (0.93), 7.499 (0.92), 7.502 (1.14), 7.511 (1.99), 7.519 (1.24), 7.526 (0.96), 7.607 (0.74), 7.626 (0.68), 7.842 (0.88), 7.851 (0.46), 7.860 (0.72), 7.866 (0.73), 8.226 (0.77), 8.233 (0.68), 8.250 (0.70).

Example 334

1-methyl-7-[3-(naphthalen-1-yloxy)propyl]-3-(piperidin-1-ylmethyl)-1,10,11,12,13,15-hexahydropyrazolo[4',3':9,10][1,6]oxazacycloundecino[8,7,6-hi]indole-8-carboxylic acid (Enantiomer 2)

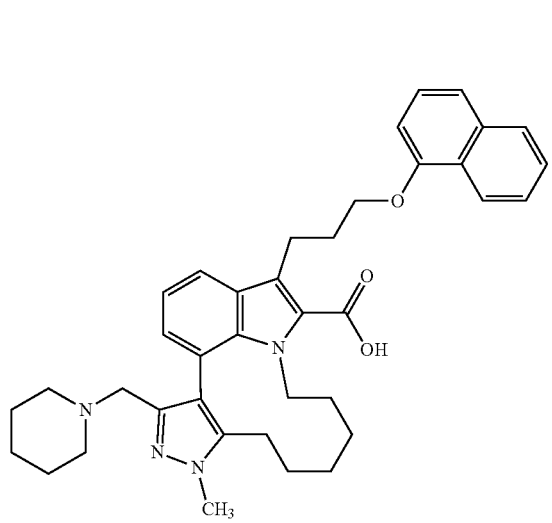 [SMILES: Cn1nc(CN2CCCCC2)c2c1CCCCCCn1c(C(=O)O)c(CCCOc3cccc4ccccc34)c3cccc-2c31]

The title compound was prepared in analogy to the synthetic procedures described before.

Yield: 16.1 mg (97% purity)

LC-MS (Method 1): $R_t$=1.20 min; MS (ESIpos): m/z=607 [M+H]$^+$ $^1$H-NMR (400 MHz, DMSO-d6) δ[ppm]: 0.852 (0.46), 0.967 (0.90), 0.974 (0.46), 0.995 (0.63), 1.010 (0.61), 1.050 (0.53), 1.071 (0.58), 1.084 (0.56), 1.107 (10.25), 1.135 (3.61), 1.145 (2.30), 1.154 (7.78), 1.171 (5.28), 1.232 (1.79), 1.349 (0.53), 1.377 (0.51), 1.388 (0.53), 1.944 (1.02), 1.960 (1.12), 2.078 (1.02), 2.182 (1.16), 2.199 (1.72), 2.217 (1.19), 2.332 (0.99), 2.337 (0.46), 2.518 (5.48), 2.523 (3.66), 2.674 (1.07), 2.792 (0.48), 2.805 (0.51), 2.822 (0.53), 2.852 (0.68), 2.870 (1.99), 2.888 (1.89), 2.906 (0.68), 2.916 (1.82), 2.949 (2.50), 3.064 (2.16), 3.096 (1.53), 3.208 (0.68), 3.223 (0.75), 3.241 (1.04), 3.261 (0.75), 3.377 (1.60), 3.395 (1.09), 3.413 (0.97), 3.425 (0.85), 3.443 (0.75), 3.459 (0.44), 3.869 (16.00), 3.888 (0.46), 3.953 (0.73), 4.136 (1.41), 4.152 (2.96), 4.169 (1.38), 4.250 (1.65), 4.283 (1.79), 4.572 (0.63), 4.607 (0.61), 4.629 (2.06), 4.662 (1.82), 6.722 (1.14), 6.739 (1.31), 6.823 (1.87), 6.841 (1.99), 6.934 (1.28), 6.954 (1.79), 6.972 (1.09), 7.336 (1.43), 7.356 (2.59), 7.375 (1.96), 7.428 (2.67), 7.449 (1.65), 7.486 (0.56), 7.499 (1.70), 7.504 (1.72), 7.506 (2.21), 7.514 (3.61), 7.523 (2.28), 7.530 (1.82), 7.542 (0.61), 7.652 (1.31), 7.672 (1.19), 7.846 (1.58), 7.855 (0.80), 7.863 (1.21), 7.869 (1.31), 8.229 (1.36), 8.236 (1.24), 8.245 (0.65), 8.253 (1.33).

Example 335

(rac)-1-methyl-7-[3-(naphthalen-1-yloxy)propyl]-3-(pyrrolidin-1-ylmethyl)-1,10,11,12,13,15-hexahydropyrazolo[4',3':9,10][1,6]oxazacycloundecino[8,7,6-hi]indole-8-carboxylic acid

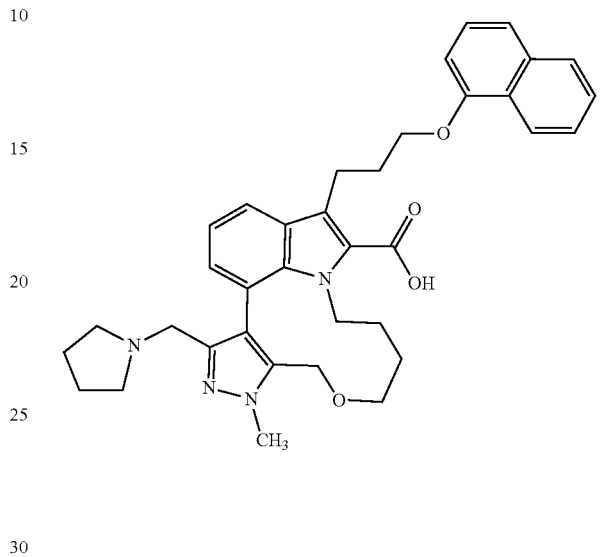

The title compound was prepared in analogy to the synthetic procedures described before.

Yield: 53.3 mg (95% purity)

LC-MS (Method 1): $R_t$=1.16 min; MS (ESIpos): m/z=593 [M+H]$^+$ $^1$H-NMR (400 MHz, DMSO-d6) δ[ppm]: 1.021 (1.74), 1.227 (0.96), 1.252 (0.81), 1.270 (1.05), 1.288 (0.81), 1.317 (0.78), 1.478 (3.64), 1.493 (6.29), 1.509 (3.43), 1.527 (0.72), 2.191 (2.20), 2.208 (3.76), 2.225 (3.70), 2.241 (3.25), 2.317 (2.83), 2.322 (2.89), 2.326 (3.55), 2.331 (2.86), 2.518 (6.32), 2.522 (4.39), 2.539 (0.45), 2.660 (0.69), 2.664 (1.44), 2.668 (1.92), 2.673 (1.41), 2.678 (0.75), 2.765 (0.63), 2.782 (1.11), 2.795 (1.02), 2.812 (1.20), 2.830 (0.66), 3.069 (0.54), 3.101 (0.81), 3.134 (3.46), 3.167 (4.06), 3.230 (1.56), 3.249 (2.38), 3.263 (2.38), 3.282 (3.31), 3.301 (2.38), 3.323 (2.68), 3.341 (3.52), 3.365 (5.62), 3.374 (3.22), 3.398 (4.93), 3.413 (3.01), 3.428 (2.68), 3.442 (2.62), 3.457 (1.95), 3.708 (0.48), 3.905 (1.77), 3.936 (0.75), 3.945 (0.90), 3.960 (0.93), 3.969 (1.29), 3.981 (0.84), 3.994 (0.84), 4.003 (0.90), 4.155 (2.47), 4.170 (5.05), 4.186 (2.53), 4.245 (3.01), 4.278 (3.22), 4.495 (1.29), 4.506 (0.78), 4.519 (0.72), 4.530 (1.20), 4.636 (3.64), 4.670 (3.22), 5.758 (2.95), 6.804 (2.98), 6.807 (3.07), 6.822 (3.61), 6.824 (3.43), 6.844 (3.04), 6.862 (3.28), 6.874 (0.51), 6.986 (3.28), 7.006 (3.73), 7.024 (2.59), 7.347 (2.32), 7.367 (4.30), 7.386 (3.25), 7.435 (4.63), 7.456 (2.80), 7.485 (0.63), 7.489 (0.99), 7.501 (2.71), 7.506 (2.74), 7.509 (3.61), 7.518 (6.26), 7.526 (3.76), 7.528 (3.19), 7.533 (3.22), 7.546 (1.17), 7.551 (0.63), 7.712 (3.04), 7.714 (3.22), 7.731 (2.89), 7.734 (2.83), 7.849 (2.74), 7.858 (1.47), 7.867 (2.32), 7.873 (2.35), 8.176 (16.00), 8.229 (2.44), 8.236 (2.17), 8.245 (1.17), 8.253 (2.14).

Example 336

1-methyl-7-[3-(naphthalen-1-yloxy)propyl]-3-(pyrrolidin-1-ylmethyl)-1,10,11,12,13,15-hexahydropyrazolo[4',3':9,10][1,6]oxazacycloundecino[8,7,6-hi]indole-8-carboxylic acid (Enantiomer 1)

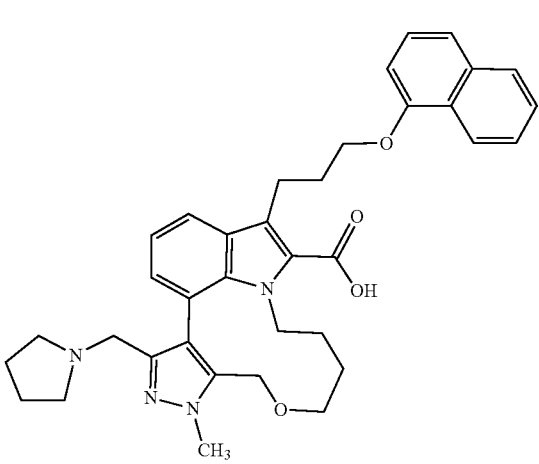 [SMILES: Cn1nc(CN2CCCC2)c2c1COCCCCn1c(C(=O)O)c(CCCOc3cccc4ccccc34)c3cccc-2c31]

The title compound was prepared in analogy to the synthetic procedures described before.

Yield: 18.6 mg (90% purity)

LC-MS (Method 1): $R_t$=1.14 min; MS (ESIpos): m/z=593 [M+H]$^+$ $^1$H-NMR (400 MHz, DMSO-d6) δ[ppm]: 1.018 (1.21), 1.111 (1.73), 1.126 (1.73), 1.141 (2.91), 1.159 (6.39), 1.178 (3.06), 1.232 (1.48), 1.256 (0.82), 1.295 (0.97), 1.332 (0.82), 1.756 (1.15), 1.770 (1.79), 1.787 (2.36), 1.826 (0.73), 1.907 (0.70), 2.205 (0.94), 2.222 (1.36), 2.240 (1.00), 2.256 (0.39), 2.336 (0.55), 2.471 (1.18), 2.518 (6.45), 2.522 (4.09), 2.543 (0.52), 2.546 (0.48), 2.678 (0.58), 2.803 (0.55), 2.822 (0.48), 2.878 (0.85), 2.894 (1.36), 2.909 (1.82), 2.924 (1.73), 2.943 (1.12), 3.285 (0.58), 3.302 (0.91), 3.321 (1.79), 3.343 (2.12), 3.362 (1.64), 3.378 (1.48), 3.817 (0.82), 3.831 (0.85), 3.853 (1.15), 3.867 (1.21), 3.880 (0.52), 3.894 (0.73), 3.915 (0.52), 3.984 (16.00), 4.003 (0.70), 4.062 (1.00), 4.074 (1.00), 4.097 (0.82), 4.111 (0.79), 4.195 (1.33), 4.211 (2.79), 4.226 (1.33), 4.251 (1.73), 4.284 (1.79), 4.485 (0.76), 4.496 (0.45), 4.508 (0.45), 4.520 (0.70), 4.688 (1.88), 4.721 (1.76), 6.888 (1.85), 6.905 (2.00), 6.937 (1.88), 6.940 (1.97), 6.955 (2.27), 6.958 (2.21), 7.083 (2.00), 7.101 (1.94), 7.103 (2.21), 7.121 (1.61), 7.371 (1.36), 7.392 (2.58), 7.411 (2.15), 7.450 (2.70), 7.471 (1.52), 7.488 (0.48), 7.492 (0.67), 7.505 (1.61), 7.509 (1.36), 7.517 (1.79), 7.523 (3.24), 7.529 (1.70), 7.537 (1.55), 7.541 (1.67), 7.554 (0.70), 7.558 (0.45), 7.818 (1.88), 7.821 (1.94), 7.838 (1.79), 7.841 (1.67), 7.861 (1.58), 7.867 (0.88), 7.879 (1.73), 7.884 (1.33), 8.221 (1.42), 8.226 (1.33), 8.245 (1.30), 10.103 (0.52).

Example 337

1-methyl-7-[3-(naphthalen-1-yloxy)propyl]-3-(pyrrolidin-1-ylmethyl)-1,10,11,12,13,15-hexahydropyrazolo[4',3':9,10][1,6]oxazacycloundecino[8,7,6-hi]indole-8-carboxylic acid (Enantiomer 2)

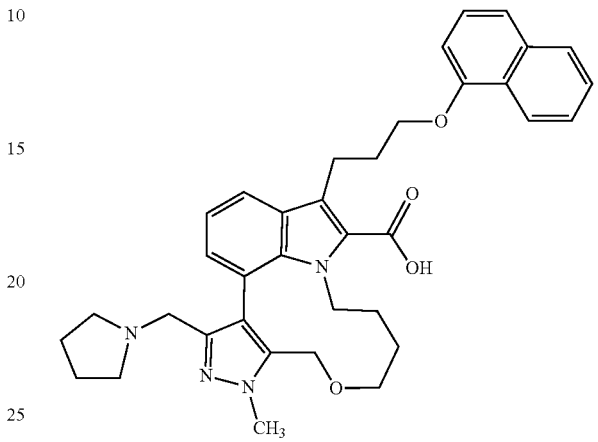

The title compound was prepared in analogy to the synthetic procedures described before.

Yield: 21.0 mg (90% purity)

LC-MS (Method 1): $R_t$=1.14 min; MS (ESIpos): m/z=593 [M+H]$^+$ $^1$H-NMR (400 MHz, CHLOROFORM-d) δ [ppm]: 0.000 (0.50), 1.142 (1.71), 1.158 (1.72), 1.299 (0.70), 1.315 (0.61), 3.400 (0.40), 3.935 (1.74), 4.125 (0.63), 4.360 (0.44), 4.507 (1.33), 4.539 (0.85), 5.230 (16.00), 7.260 (0.44), 7.316 (0.79), 7.337 (0.45), 7.390 (0.70), 7.401 (0.75), 7.413 (0.76), 7.707 (0.47), 7.730 (0.47), 7.740 (0.57), 7.760 (0.49).

Example 338

(rac)-3-(aminomethyl)-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid

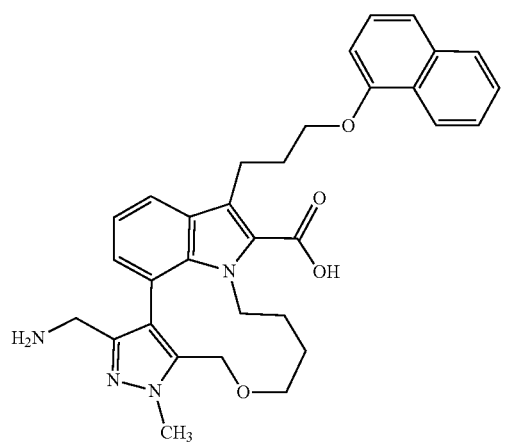 [SMILES: Cn1nc(CN)c2c1COCCCCn1c(C(=O)O)c(CCCOc3cccc4ccccc34)c3cccc-2c31]

The title compound was prepared in analogy to the synthetic procedures described before.

Yield: 28.0 mg (91% purity)

LC-MS (Method 1): $R_t$=1.10 min; MS (ESIpos): m/z=539 [M+H]$^+$ $^1$H-NMR (400 MHz, DMSO-d6) δ[ppm]: 0.938 (0.42), 0.958 (0.51), 0.991 (0.59), 1.352 (16.00), 1.741 (1.33), 1.748 (1.22), 1.751 (1.37), 1.757 (3.83), 1.762 (0.76), 1.766 (1.12), 1.774 (1.18), 2.181 (2.53), 2.191 (1.03), 2.209 (0.74), 2.518 (3.94), 2.523 (2.78), 2.729 (0.48), 2.752 (0.40), 3.079 (0.51), 3.158 (0.93), 3.192 (1.39), 3.248 (2.19), 3.379 (5.31), 3.443 (3.49), 3.582 (2.86), 3.584 (2.00), 3.589 (1.62), 3.592 (1.77), 3.599 (3.89), 3.605 (1.66), 3.609 (1.35), 3.613 (1.58), 3.615 (2.15), 3.753 (0.48), 3.783 (0.59), 3.812 (0.44), 3.884 (0.95), 3.908 (6.93), 4.174 (0.91), 4.190 (1.68), 4.206 (1.03), 4.214 (1.10), 4.247 (0.97), 4.612 (0.44), 4.641 (1.26), 4.675 (0.93), 6.695 (0.91), 6.713 (0.99), 6.869 (1.81), 6.891 (1.09), 6.930 (0.90), 6.950 (1.26), 6.969 (0.80), 7.353 (0.59), 7.373 (1.20), 7.392 (0.88), 7.433 (1.81), 7.454 (1.03), 7.496 (0.99), 7.501 (1.05), 7.504 (1.33), 7.513 (2.23), 7.521 (1.28), 7.524 (1.26), 7.528 (1.16), 7.541 (0.46), 7.617 (0.99), 7.634 (0.93), 7.849 (1.14), 7.857 (0.59), 7.867 (0.95), 7.872 (0.90), 8.227 (0.88), 8.233 (0.86), 8.251 (1.05), 8.256 (1.28).

Example 339

(rac)-3-[(acetylamino)methyl]-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid

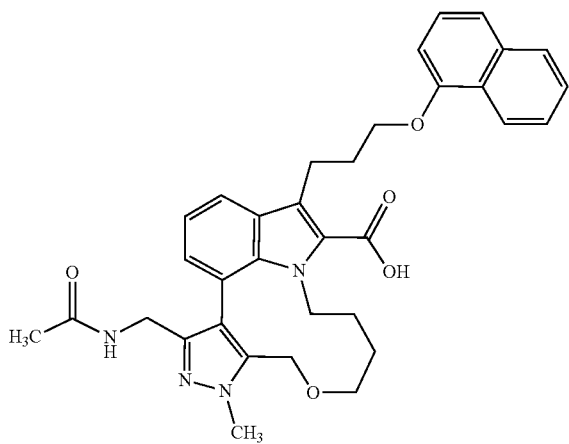 [SMILES: CC(=O)NCc1nn(C)c2c1-c1cccc3c(CCCOc4cccc5ccccc45)c(C(=O)O)n(c13)CCCCOC2]

The title compound was prepared in analogy to the synthetic procedures described before.

Yield: 6.20 mg (98% purity)

LC-MS (Method 1): $R_t$=1.29 min; MS (ESIpos): m/z=581 [M+H]$^+$ $^1$H-NMR (400 MHz, DMSO-d6) δ[ppm]: 1.021 (1.17), 1.232 (0.74), 1.353 (16.00), 1.542 (9.59), 1.907 (0.42), 2.181 (3.28), 2.198 (1.80), 2.216 (1.27), 2.327 (3.07), 2.332 (2.28), 2.518 (12.66), 2.523 (8.05), 2.669 (3.13), 2.673 (2.23), 2.772 (0.53), 2.785 (0.53), 2.801 (0.64), 3.263 (0.85), 3.380 (0.90), 3.413 (0.48), 3.430 (0.79), 3.442 (0.64), 3.460 (0.69), 3.760 (0.95), 3.772 (0.90), 3.798 (1.32), 3.809 (1.38), 3.880 (1.47), 3.904 (0.74), 3.934 (1.43), 3.950 (1.43), 3.972 (1.11), 3.987 (1.06), 4.171 (1.43), 4.187 (2.81), 4.202 (1.43), 4.230 (1.70), 4.263 (1.80), 4.553 (0.53), 4.589 (0.48), 4.635 (1.96), 4.668 (1.70), 5.759 (6.25), 6.653 (0.74), 6.793 (0.79), 6.809 (0.90), 6.869 (1.43), 6.882 (1.80), 6.901 (1.96), 6.975 (0.79), 6.994 (1.32), 7.012 (0.74), 7.358 (1.17), 7.378 (2.33), 7.397 (1.80), 7.438 (2.65), 7.459 (1.48), 7.494 (0.53), 7.506 (1.64), 7.511 (2.65), 7.521 (3.02), 7.530 (2.81), 7.535 (1.75), 7.547 (0.53), 7.694 (0.95), 7.713 (0.90), 7.763 (0.74), 7.777 (1.22), 7.789 (0.69), 7.853 (1.59), 7.863 (0.85), 7.869 (1.06), 7.876 (1.27), 8.239 (1.38), 8.247 (1.06), 8.263 (1.17).

Example 340

3-[(acetylamino)methyl]-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (Enantiomer 1)

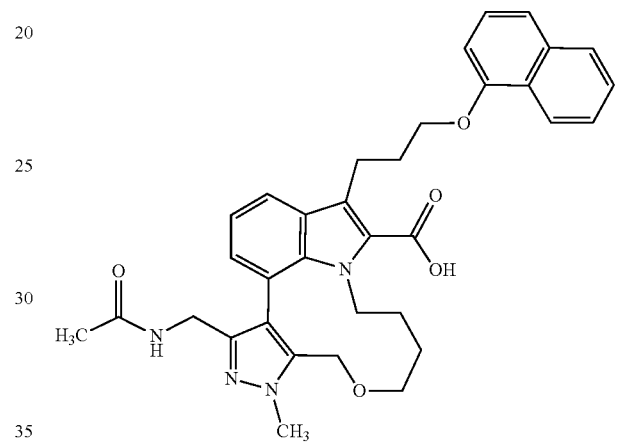

The title compound was prepared in analogy to the synthetic procedures described before.

Yield: 48.8 mg (99% purity)

LC-MS (Method 1): $R_t$=1.32 min; MS (ESIpos): m/z=581 [M+H]$^+$ $^1$H-NMR (400 MHz, DMSO-d6) δ[ppm]: 0.776 (0.55), 0.795 (1.30), 0.814 (0.70), 0.862 (0.43), 0.968 (0.96), 0.990 (0.64), 1.006 (1.87), 1.027 (0.77), 1.035 (1.00), 1.042 (0.74), 1.061 (0.49), 1.084 (1.53), 1.108 (6.78), 1.132 (7.08), 1.150 (14.47), 1.168 (7.12), 1.260 (2.30), 1.406 (0.47), 1.425 (0.76), 1.441 (0.72), 1.444 (0.72), 1.598 (13.94), 2.178 (1.17), 2.196 (1.78), 2.213 (1.25), 2.230 (0.42), 2.518 (4.61), 2.523 (3.06), 2.751 (0.47), 2.768 (0.60), 2.780 (0.53), 2.832 (1.78), 2.850 (5.57), 2.868 (5.42), 2.886 (1.66), 3.165 (0.60), 3.180 (0.62), 3.198 (0.87), 3.216 (0.47), 3.404 (0.68), 3.421 (0.93), 3.432 (0.74), 3.450 (0.76), 3.468 (0.42), 3.770 (0.98), 3.782 (0.94), 3.808 (1.53), 3.820 (1.57), 3.839 (0.42), 3.873 (16.00), 3.901 (0.94), 3.908 (1.61), 3.923 (1.44), 3.946 (0.89), 3.960 (0.93), 4.162 (1.21), 4.178 (2.44), 4.194 (1.32), 4.219 (1.85), 4.253 (1.93), 4.628 (2.12), 4.662 (2.30), 4.689 (0.59), 6.694 (1.19), 6.711 (1.36), 6.870 (1.89), 6.888 (2.08), 6.917 (1.25), 6.936 (1.87), 6.954 (1.11), 7.346 (1.34), 7.367 (2.63), 7.386 (2.08), 7.429 (2.85), 7.450 (1.61), 7.485 (0.57), 7.498 (1.64), 7.504 (2.29), 7.513 (3.53), 7.522 (2.55), 7.528 (1.83), 7.541 (0.64), 7.609 (1.38), 7.629 (1.30), 7.742 (0.74), 7.755 (1.32), 7.768 (0.74), 7.847 (1.62), 7.856 (0.83), 7.864 (1.25), 7.870 (1.40), 8.234 (1.42), 8.241 (1.23), 8.249 (0.64), 8.258 (1.32).

Example 341

3-[(acetylamino)methyl]-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (Enantiomer 2)

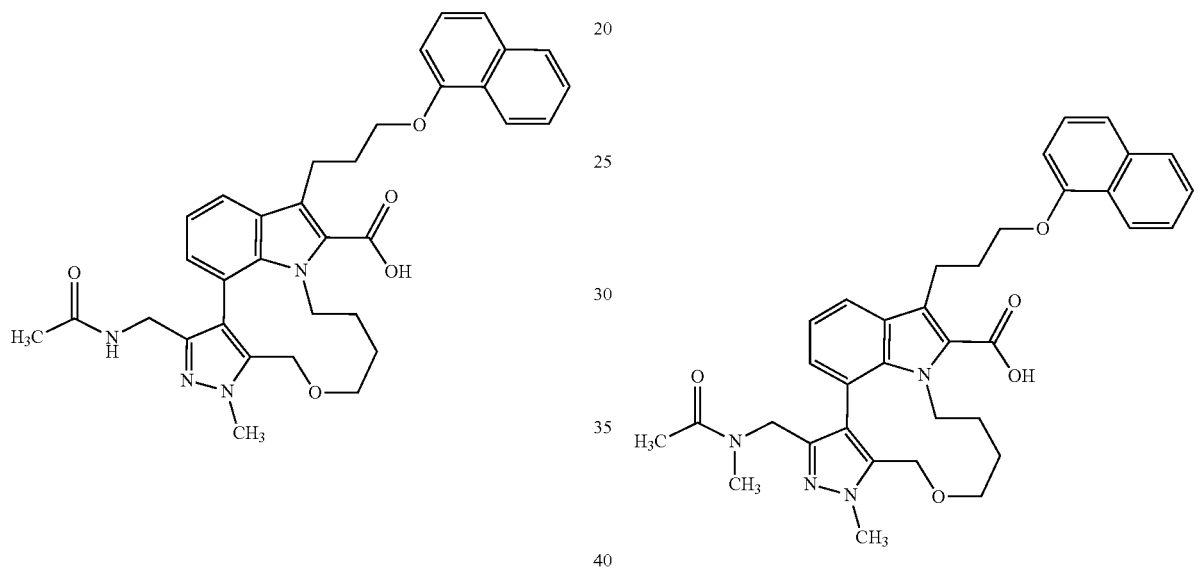

The title compound was prepared in analogy to the synthetic procedures described before.

Yield: 42.3 mg (98% purity)

LC-MS (Method 1): $R_t$=1.32 min; MS (ESIpos): m/z=581 [M+H]$^+$ $^1$H-NMR (400 MHz, DMSO-d6) δ[ppm]: 0.776 (0.47), 0.795 (1.11), 0.814 (0.61), 0.862 (0.41), 0.968 (1.27), 0.989 (0.68), 1.006 (1.76), 1.022 (0.68), 1.035 (0.94), 1.061 (0.55), 1.084 (1.33), 1.108 (5.27), 1.132 (6.43), 1.150 (13.01), 1.168 (6.39), 1.209 (0.45), 1.232 (0.41), 1.260 (1.80), 1.406 (0.47), 1.425 (0.76), 1.444 (0.70), 1.597 (13.91), 2.178 (1.21), 2.196 (1.86), 2.213 (1.29), 2.230 (0.43), 2.518 (4.88), 2.523 (3.13), 2.673 (0.86), 2.751 (0.51), 2.768 (0.64), 2.780 (0.55), 2.831 (1.62), 2.849 (4.92), 2.867 (4.81), 2.885 (1.50), 3.166 (0.63), 3.181 (0.64), 3.198 (0.90), 3.216 (0.49), 3.403 (0.72), 3.421 (0.96), 3.431 (0.76), 3.450 (0.80), 3.468 (0.43), 3.770 (0.96), 3.782 (0.94), 3.808 (1.54), 3.820 (1.60), 3.840 (0.43), 3.873 (16.00), 3.908 (1.62), 3.923 (1.45), 3.946 (0.92), 3.960 (0.94), 4.162 (1.27), 4.177 (2.52), 4.194 (1.33), 4.220 (1.86), 4.253 (1.95), 4.628 (2.19), 4.662 (2.36), 4.688 (0.63), 4.694 (1.23), 6.712 (1.39), 6.870 (1.99), 6.888 (2.13), 6.917 (1.27), 6.936 (1.91), 6.954 (1.11), 7.347 (1.35), 7.367 (2.66), 7.386 (2.07), 7.429 (1.87), 7.450 (1.60), 7.485 (0.55), 7.498 (1.64), 7.504 (2.36), 7.513 (3.44), 7.523 (2.62), 7.528 (1.84), 7.540 (0.61), 7.609 (1.41), 7.629 (1.33), 7.743 (0.76), 7.755 (1.39), 7.768 (0.76), 7.847 (1.62), 7.856 (0.84), 7.864 (1.25), 7.870 (1.41), 8.234 (1.41), 8.241 (1.23), 8.249 (0.68), 8.258 (1.35).

Example 342

(rac)-3-{[acetyl(methyl)amino]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid The title compound was prepared in analogy to the synthetic procedures described before.

Yield: 26.8 mg (94% purity)

LC-MS (Method 1): $R_t$=1.34 min; MS (ESIpos): m/z=595 [M+H]$^+$ $^1$H-NMR (400 MHz, DMSO-d6) δ[ppm]: 1.042 (0.58), 1.297 (0.49), 1.343 (4.49), 1.353 (16.00), 1.481 (3.30), 2.181 (2.69), 2.475 (10.42), 2.518 (10.49), 2.540 (6.29), 3.413 (0.56), 3.432 (0.53), 3.445 (0.51), 3.461 (0.44), 3.877 (3.40), 3.905 (4.39), 3.972 (0.56), 4.011 (0.97), 4.044 (0.63), 4.089 (0.85), 4.128 (0.53), 4.165 (1.19), 4.172 (1.09), 4.237 (0.46), 4.268 (1.02), 4.277 (0.66), 4.305 (0.66), 4.310 (0.63), 4.622 (0.49), 4.649 (0.66), 4.656 (0.53), 4.683 (0.53), 5.759 (2.96), 6.652 (0.70), 6.826 (0.44), 6.843 (0.44), 6.860 (1.09), 6.869 (2.02), 6.877 (0.78), 6.887 (0.56), 6.989 (0.46), 7.000 (0.44), 7.020 (0.56), 7.352 (0.68), 7.373 (1.31), 7.392 (0.97), 7.437 (1.48), 7.457 (0.87), 7.510 (0.97), 7.514 (1.51), 7.524 (1.65), 7.533 (1.51), 7.538 (1.07), 7.746 (0.46), 7.852 (0.85), 7.869 (0.58), 7.875 (0.70), 8.236 (0.51), 8.244 (0.66), 8.260 (0.51).

Example 343

1-methyl-7-[3-(naphthalen-1-yloxy)propyl]-3-({[(2,2,2-trifluoroethyl)carbamoyl]oxy}methyl)-1,10,11,12,13,15-hexahydropyrazolo[4',3':9,10][1,6]oxazacycloundecino[8,7,6-hi]indole-8-carboxylic acid (Enantiomer 1)

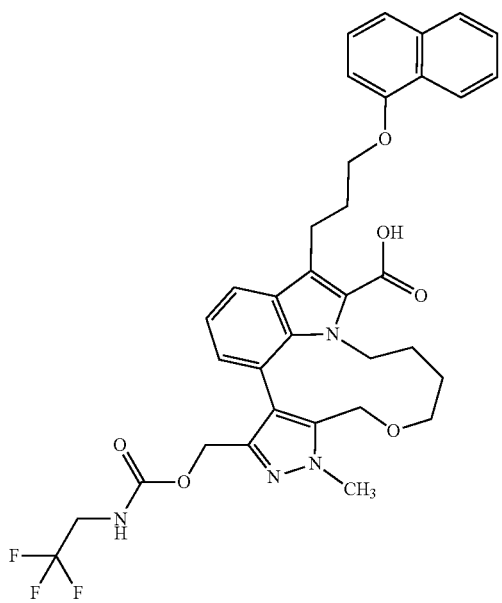 [SMILES: Cn1nc(COC(=O)NCC(F)(F)F)c2c1COCCCCn1c(C(=O)O)c(CCCOc3cccc4ccccc34)c3cccc-2c31]

The title compound was prepared in analogy to the synthetic procedures described before.

Analytical chiral HPLC method: Instrument: Agilent HPLC 1260; column: Chiralpak AD 3µ 100×4.6 mm; Eluent A: Hexane+0.1 Vol-% trifluoroacetic acid; Eluent B: 2-propanol; Gradient: 20-50% B in 7 min; Flow 1.4 ml/min; Temperature: 25° C.; DAD 254 nm Analytical Chiral HPLC: $R_t$=3.08 min.

LC-MS (Method 2): Rt=0.89 min; MS (ESIpos): m/z=664 [M+H]$^+$ $^1$H-NMR (400 MHz, DMSO-d6) δ[ppm]: 0.852 (0.60), 1.033 (1.08), 1.050 (1.20), 1.138 (0.47), 1.154 (0.52), 1.233 (1.89), 1.316 (0.82), 1.331 (0.77), 2.193 (0.82), 2.210 (1.20), 2.227 (0.86), 2.337 (0.77), 2.518 (10.15), 2.523 (6.92), 2.540 (0.52), 2.679 (0.82), 2.812 (0.43), 2.888 (0.47), 3.263 (0.47), 3.277 (0.56), 3.296 (0.95), 3.352 (1.03), 3.369 (0.60), 3.385 (0.52), 3.434 (0.65), 3.449 (0.52), 3.463 (0.60), 3.588 (0.69), 3.608 (0.82), 3.630 (0.65), 3.914 (16.00), 3.934 (0.77), 3.964 (0.47), 4.186 (1.12), 4.201 (2.41), 4.217 (1.16), 4.247 (1.51), 4.281 (1.63), 4.502 (0.56), 4.537 (0.47), 4.572 (0.86), 4.603 (1.25), 4.658 (1.63), 4.693 (2.15), 4.727 (0.90), 6.846 (1.08), 6.864 (1.33), 6.885 (1.68), 6.903 (1.76), 7.014 (1.68), 7.032 (1.72), 7.034 (1.89), 7.052 (1.33), 7.363 (1.25), 7.383 (2.28), 7.402 (1.85), 7.444 (2.49), 7.465 (1.38), 7.491 (0.52), 7.504 (1.38), 7.508 (1.29), 7.513 (1.63), 7.520 (3.14), 7.528 (1.59), 7.532 (1.51), 7.537 (1.59), 7.549 (0.65), 7.690 (0.47), 7.706 (0.90), 7.722 (0.47), 7.756 (1.68), 7.758 (1.76), 7.775 (1.59), 7.778 (1.55), 7.855 (1.38), 7.863 (0.73), 7.873 (1.33), 7.879 (1.20), 8.232 (1.12), 8.238 (1.03), 8.256 (1.03), 13.178 (0.82).

Example 344

1-methyl-7-[3-(naphthalen-1-yloxy)propyl]-3-(2-oxa-6-azaspiro[3.3]hept-6-ylmethyl)-1,10,11,12,13,15-hexahydropyrazolo[4',3':9,10][1,6]oxazacycloundecino[8,7,6-hi]indole-8-carboxylic acid-N-ethylethanamine salt (Enantiomer 1)

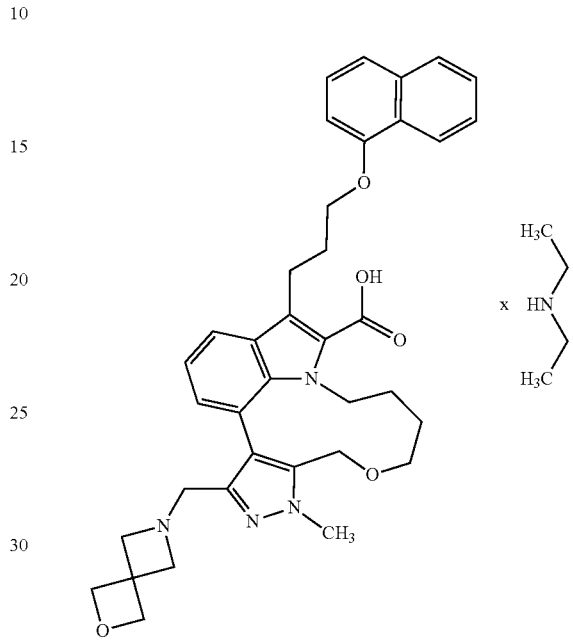

The title compound was prepared in analogy to the synthetic procedures described before.

Analytical chiral SFC method: Instrument: Agilent: 1260, Aurora SFC-Modul; column: Chiralpak IC 5 µm 100×4.6 mm; Eluent A: $CO_2$, Eluent B: 2-Propanol+0.2 Vol-% N-ethylethanamine (99%); 37% B; Flow 4.0 ml/min; Temperature: 37.5° C.; BPR: 100 bar; MWD @ 220 nm Analytical Chiral SFC: $R_t$=2.52 min.

LC-MS (Method 2): Rt=0.81 min; MS (ESIpos): m/z=622 [M+H]$^+$ $^1$H-NMR (400 MHz, DMSO-d6) δ[ppm]: 0.990 (1.23), 0.999 (0.27), 1.109 (16.00), 1.204 (1.31), 1.223 (2.79), 1.242 (0.35), 1.798 (0.29), 1.820 (0.61), 1.906 (0.18), 2.122 (1.99), 2.174 (4.82), 2.186 (0.23), 2.204 (0.25), 2.220 (0.17), 2.518 (1.74), 2.523 (1.22), 2.750 (0.67), 2.980 (0.35), 2.990 (0.42), 3.007 (0.85), 3.012 (0.63), 3.045 (0.79), 3.062 (0.40), 3.115 (0.43), 3.147 (0.31), 3.389 (0.23), 3.401 (0.18), 3.853 (2.70), 4.163 (0.20), 4.179 (0.40), 4.195 (0.22), 4.204 (0.30), 4.237 (0.29), 4.404 (0.28), 4.421 (1.45), 4.426 (1.45), 4.443 (0.25), 4.612 (0.39), 4.645 (0.28), 6.693 (0.19), 6.710 (0.21), 6.853 (0.28), 6.871 (0.30), 6.938 (0.21), 6.957 (0.28), 6.975 (0.17), 7.345 (0.22), 7.366 (0.39), 7.385 (0.31), 7.433 (0.43), 7.454 (0.25), 7.499 (0.25), 7.503 (0.25), 7.507 (0.30), 7.514 (0.55), 7.523 (0.31), 7.526 (0.27), 7.530 (0.27), 7.636 (0.21), 7.656 (0.19), 7.849 (0.25), 7.867 (0.21), 7.872 (0.21), 8.226 (0.21), 8.233 (0.20), 8.250 (0.19).

Example 345

1-methyl-7-[3-(naphthalen-1-yloxy)propyl]-3-(2-oxa-6-azaspiro[3.3]hept-6-ylmethyl)-1,10,11,12,13,15-hexahydropyrazolo[4',3':9,10][1,6]oxazacycloundecino[8,7,6-hi]indole-8-carboxylic acid-N-ethylethanamine salt (Enantiomer 2)

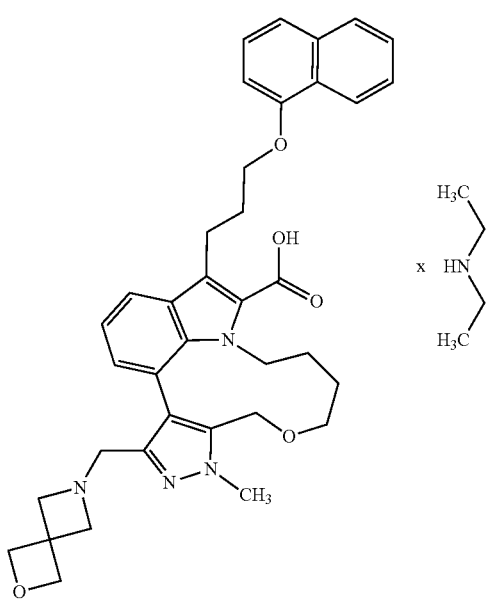

The title compound was prepared in analogy to the synthetic procedures described before.

Analytical chiral SFC method: Instrument: Agilent: 1260, Aurora SFC-Modul; column: Chiralpak IC 5 μm 100×4.6 mm; Eluent A: $CO_2$, Eluent B: 2-Propanol+0.2 Vol-% N-ethylethanamine (99%); 37% B; Flow 4.0 ml/min; Temperature: 37.5° C.; BPR: 100 bar; MWD @ 220 nm Analytical Chiral SFC: $R_t$=3.56 min.

LC-MS (Method 2): Rt=0.81 min; MS (ESIpos): m/z=622 [M+H]$^+$ $^1$H-NMR (400 MHz, DMSO-d6) δ[ppm]: 0.888 (1.21), 0.934 (0.59), 0.961 (0.56), 0.991 (7.34), 1.017 (1.92), 1.042 (0.76), 1.066 (0.68), 1.073 (0.65), 1.088 (0.59), 1.105 (1.04), 1.111 (3.10), 1.121 (0.76), 1.145 (0.99), 1.153 (0.90), 1.179 (1.16), 1.195 (1.27), 1.207 (8.01), 1.226 (16.00), 1.261 (0.62), 1.267 (0.87), 1.286 (0.54), 1.402 (0.40), 1.786 (1.02), 1.790 (1.02), 1.800 (1.81), 1.821 (3.81), 1.906 (0.73), 2.113 (11.77), 2.175 (1.13), 2.185 (0.87), 2.204 (1.33), 2.219 (1.02), 2.332 (1.16), 2.336 (0.51), 2.518 (5.73), 2.523 (4.15), 2.673 (1.21), 2.678 (0.56), 2.756 (3.84), 2.962 (0.68), 2.981 (2.06), 2.993 (2.29), 3.012 (5.90), 3.046 (4.40), 3.064 (2.23), 3.119 (2.37), 3.151 (1.86), 3.172 (0.51), 3.188 (0.59), 3.205 (0.73), 3.224 (0.54), 3.333 (2.88), 3.385 (1.35), 3.397 (1.10), 3.415 (0.93), 3.812 (0.42), 3.876 (2.37), 4.161 (1.02), 4.176 (2.12), 4.192 (1.35), 4.200 (2.14), 4.234 (1.86), 4.402 (1.30), 4.406 (1.75), 4.423 (8.16), 4.427 (8.30), 4.444 (1.33), 4.610 (2.09), 4.644 (1.81), 6.673 (1.19), 6.690 (1.30), 6.849 (1.58), 6.868 (1.66), 6.926 (1.27), 6.946 (1.81), 6.963 (1.19), 7.341 (1.13), 7.362 (2.20), 7.381 (1.66), 7.430 (2.51), 7.451 (1.52), 7.483 (0.54), 7.496 (1.38), 7.501 (1.47), 7.504 (1.81), 7.513 (3.13), 7.520 (1.78), 7.524 (1.69), 7.528 (1.55), 7.541 (0.65), 7.617 (1.38), 7.637 (1.19), 7.847 (1.55), 7.855 (0.76), 7.865 (1.30), 7.870 (1.27), 8.225 (1.16), 8.231 (1.16), 8.249 (1.04).

Example 346

(rac)-3-{[(4-carbamoylbenzyl)oxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid

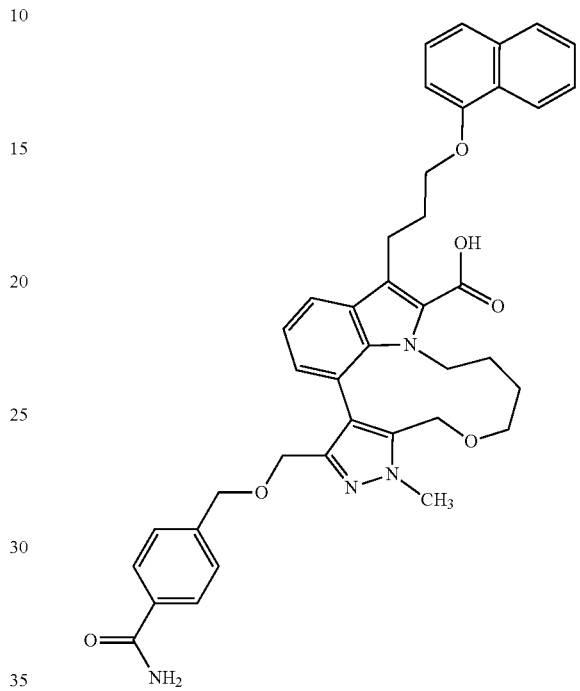

The title compound was prepared in analogy to the synthetic procedures described before.

LC-MS (Method 2): Rt=0.91 min; MS (ESIpos): m/z=674 [M+H]$^+$ $^1$H-NMR (400 MHz, DMSO-d6) δ[ppm]: 0.852 (0.50), 1.046 (0.92), 1.233 (2.18), 1.353 (0.54), 1.907 (1.03), 2.198 (0.96), 2.216 (1.42), 2.232 (1.07), 2.337 (0.69), 2.518 (9.34), 2.523 (6.28), 2.679 (0.73), 2.818 (0.54), 2.831 (0.46), 2.848 (0.54), 3.275 (0.46), 3.309 (1.19), 3.375 (0.92), 3.393 (0.57), 3.408 (0.54), 3.437 (0.65), 3.451 (0.57), 3.467 (0.61), 3.879 (0.54), 3.914 (16.00), 3.936 (1.42), 4.029 (0.54), 4.055 (0.77), 4.090 (1.19), 4.119 (3.14), 4.131 (3.10), 4.159 (1.38), 4.164 (1.38), 4.180 (2.68), 4.195 (1.38), 4.203 (1.49), 4.235 (2.53), 4.263 (1.68), 4.277 (2.56), 4.297 (1.72), 4.309 (1.22), 4.487 (0.61), 4.523 (0.54), 4.663 (1.84), 4.696 (1.65), 5.760 (2.79), 6.850 (2.68), 6.867 (3.06), 6.978 (3.60), 6.999 (3.60), 7.009 (1.34), 7.029 (1.68), 7.047 (1.11), 7.287 (1.22), 7.342 (1.45), 7.363 (2.53), 7.382 (2.26), 7.433 (2.60), 7.454 (1.57), 7.493 (0.54), 7.505 (1.76), 7.510 (2.99), 7.520 (3.37), 7.529 (3.18), 7.534 (1.95), 7.546 (0.61), 7.670 (4.36), 7.690 (4.06), 7.754 (1.30), 7.773 (1.22), 7.849 (1.65), 7.853 (1.30), 7.861 (1.34), 7.867 (2.14), 7.873 (2.14), 8.153 (0.46), 8.237 (1.30), 8.245 (0.96), 8.250 (0.61), 8.262 (1.19).

Example 347

3-{[(4-cyanobenzyl)oxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid-N-ethylethanamine salt (Enantiomer 1)

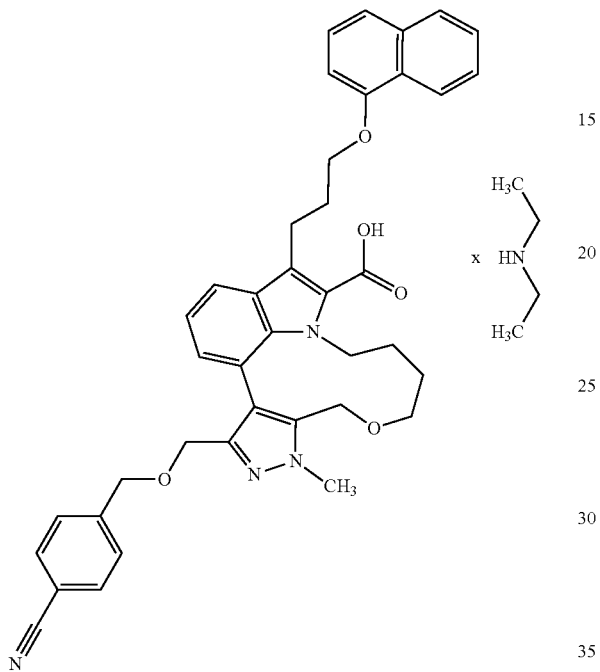

The title compound was prepared in analogy to the synthetic procedures described before.

Analytical chiral HPLC method: Instrument: Agilent HPLC 1260; column: YMC Cellulose SC 3μ 100×4.6 mm; Eluent A: hexane+0.1 Vol-% N-ethylethanamine (99%); Eluent B: ethanol; Gradient: 20-50% B in 7 min; flow 1.4 ml/min; Temperature: 25° C.; DAD 254 nm Analytical Chiral HPLC: $R_t$=3.30 min.

$^1$H-NMR (400 MHz, DMSO-d6) δ[ppm]: 0.851 (0.51), 0.967 (1.21), 0.994 (0.51), 1.009 (0.70), 1.028 (0.62), 1.045 (0.58), 1.069 (0.55), 1.083 (0.47), 1.109 (0.93), 1.134 (5.53), 1.144 (1.48), 1.152 (12.54), 1.170 (6.11), 1.208 (0.93), 1.231 (1.91), 1.256 (0.55), 1.348 (0.78), 1.440 (0.43), 1.906 (0.47), 2.181 (1.17), 2.198 (1.83), 2.216 (1.32), 2.336 (0.74), 2.518 (8.76), 2.522 (5.96), 2.673 (1.67), 2.678 (0.78), 2.806 (0.47), 2.821 (0.58), 2.836 (0.55), 2.851 (1.60), 2.869 (4.32), 2.888 (4.17), 2.905 (1.28), 3.200 (0.47), 3.215 (0.55), 3.233 (0.70), 3.254 (0.47), 3.379 (1.01), 3.398 (0.47), 3.418 (0.47), 3.436 (0.74), 3.449 (0.62), 3.464 (0.66), 3.902 (16.00), 3.927 (1.87), 3.960 (0.55), 3.991 (0.51), 4.099 (1.60), 4.127 (3.50), 4.141 (1.64), 4.154 (5.26), 4.173 (1.56), 4.182 (1.91), 4.234 (1.48), 4.250 (1.79), 4.268 (2.73), 4.283 (2.18), 4.337 (2.73), 4.371 (1.48), 4.557 (0.43), 4.592 (0.43), 4.653 (2.10), 4.687 (1.91), 6.737 (0.70), 6.754 (0.78), 6.821 (1.87), 6.839 (2.02), 6.945 (0.86), 6.964 (1.36), 6.982 (0.74), 7.058 (3.54), 7.079 (3.78), 7.326 (1.40), 7.346 (2.57), 7.365 (1.95), 7.422 (2.69), 7.443 (1.67), 7.477 (0.43), 7.481 (0.62), 7.494 (1.67), 7.498 (1.64), 7.503 (1.99), 7.511 (3.74), 7.518 (2.02), 7.523 (1.79), 7.527 (1.79), 7.540 (0.74), 7.544 (0.47), 7.558 (4.91), 7.578 (4.59), 7.595 (0.43), 7.666 (0.93), 7.685 (0.86), 7.843 (1.71), 7.851 (0.86), 7.861 (1.52), 7.866 (1.36), 8.227 (1.52), 8.234 (1.32), 8.251 (1.32).

Example 348

3-{[(4-cyanobenzyl)oxy]methyl}-1-methyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid-N-ethylethanamine salt (Enantiomer 2)

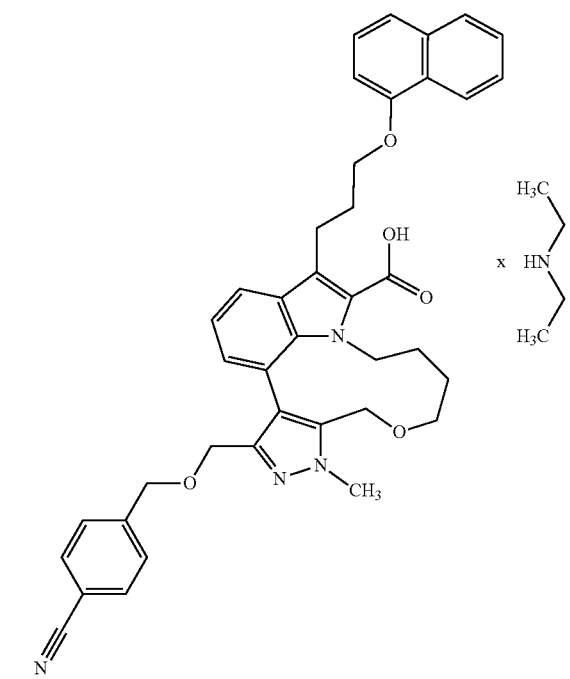

The title compound was prepared in analogy to the synthetic procedures described before.

Analytical chiral HPLC method: Instrument: Agilent HPLC 1260; column: YMC Cellulose SC 3μ 100×4.6 mm; Eluent A: hexane+0.1 Vol-% N-ethylethanamine (99%); Eluent B: ethanol; Gradient: 20-50% B in 7 min; flow 1.4 ml/min; Temperature: 25° C.; DAD 254 nm Analytical Chiral HPLC: $R_t$=3.96 min.

$^1$H-NMR (400 MHz, DMSO-d6) δ[ppm]: 0.852 (0.55), 0.968 (0.73), 0.987 (0.49), 1.006 (0.73), 1.018 (0.55), 1.034 (0.49), 1.084 (0.70), 1.108 (6.39), 1.130 (7.39), 1.148 (16.00), 1.167 (7.67), 1.232 (1.86), 1.259 (0.94), 1.349 (0.79), 1.469 (0.43), 2.182 (1.10), 2.199 (1.67), 2.216 (1.22), 2.232 (0.43), 2.337 (0.61), 2.518 (6.75), 2.523 (4.62), 2.678 (0.61), 2.822 (0.58), 2.835 (2.22), 2.853 (5.93), 2.871 (5.57), 2.889 (1.70), 3.178 (0.49), 3.193 (0.49), 3.211 (0.67), 3.374 (1.06), 3.392 (0.49), 3.435 (0.64), 3.452 (0.58), 3.466 (0.61), 3.899 (14.69), 3.927 (1.76), 4.098 (1.52), 4.126 (3.16), 4.136 (1.52), 4.153 (5.87), 4.168 (1.43), 4.181 (1.52), 4.241 (1.52), 4.246 (1.79), 4.275 (2.77), 4.280 (2.37), 4.338 (2.46), 4.372 (1.28), 4.606 (0.46), 4.653 (2.07), 4.686 (1.67), 6.699 (0.76), 6.716 (0.88), 6.814 (1.67), 6.832 (1.79), 6.922 (0.88), 6.941 (1.40), 6.959 (0.79), 7.067 (3.16), 7.087 (3.47), 7.320 (1.28), 7.341 (2.34), 7.360 (1.73), 7.419 (2.46), 7.440 (1.61), 7.479 (0.55), 7.491 (1.46), 7.496 (1.37), 7.502 (1.64), 7.509 (3.32), 7.516 (1.67), 7.521 (1.58), 7.525 (1.58), 7.538 (0.67), 7.564 (4.41), 7.585 (4.14), 7.600 (0.49), 7.634 (1.00), 7.653 (0.91), 7.841 (1.52), 7.849 (0.79), 7.859 (1.43), 7.864 (1.25), 8.227 (1.34), 8.232 (1.25), 8.251 (1.19).

Example 349

(rac)-4-methoxy-2,3-dimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid

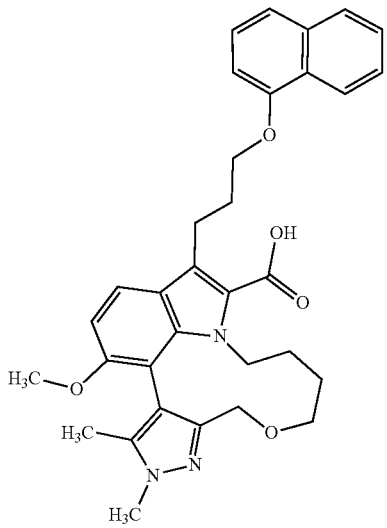 [SMILES: COc1ccc2c(CCCOc3cccc4ccccc34)c(C(=O)O)n3c2c1-c1c(nn(C)c1C)COCCCC3]

The title compound was prepared in analogy to the synthetic procedures described before.

LC-MS (Method 2): Rt=0.80 min; MS (ESIpos): m/z=555 [M+H]$^+$ $^1$H-NMR (400 MHz, DMSO-d6) δ[ppm]: 0.925 (0.42), 1.100 (0.50), 1.137 (0.63), 1.232 (2.47), 1.268 (0.60), 1.774 (15.92), 2.179 (0.95), 2.197 (1.44), 2.214 (0.95), 2.318 (0.47), 2.518 (5.99), 2.523 (4.15), 3.092 (0.60), 3.103 (0.58), 3.117 (0.42), 3.165 (1.10), 3.219 (0.45), 3.235 (0.97), 3.252 (1.44), 3.270 (1.18), 3.287 (1.10), 3.664 (14.79), 3.675 (0.92), 3.681 (1.18), 3.709 (0.53), 3.793 (16.00), 4.138 (2.02), 4.169 (3.18), 4.185 (2.08), 4.200 (1.23), 4.238 (0.45), 4.395 (2.10), 4.425 (1.81), 5.759 (2.44), 6.876 (1.60), 6.892 (1.73), 6.927 (1.76), 6.949 (1.87), 7.362 (1.31), 7.383 (2.34), 7.402 (1.89), 7.445 (2.31), 7.466 (1.34), 7.502 (0.47), 7.514 (1.60), 7.518 (2.29), 7.528 (2.81), 7.537 (2.23), 7.541 (1.94), 7.553 (0.53), 7.655 (1.58), 7.677 (1.44), 7.857 (1.34), 7.861 (0.92), 7.871 (0.87), 7.874 (0.87), 7.880 (1.16), 8.241 (1.21), 8.253 (0.89), 8.266 (1.13).

Example 350

4-methoxy-2,3-dimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid-N-ethylethanamine salt (Enantiomer 1)

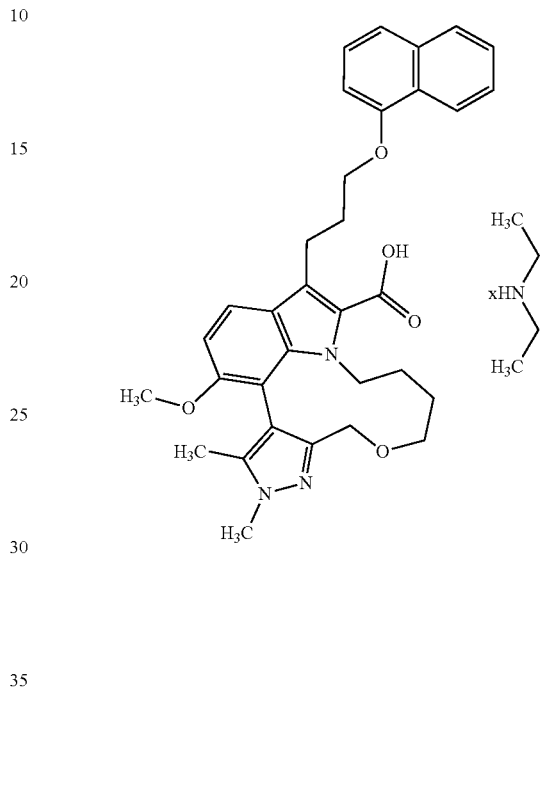

The title compound was prepared in analogy to the synthetic procedures described before.

Analytical chiral HPLC method: Instrument: Agilent HPLC 1260; column: YMC Amylose SA 3μ 100×4.6 mm; Eluent A: hexane+0.1 Vol-% N-ethylethanamine (99%); Eluent B: ethanol; Gradient: 20-50% B in 7 min; Flow 1.4 ml/min; Temperature: 25° C.; DAD 254 nm Analytical Chiral HPLC: $R_t$=2.00 min.

LC-MS (Method 2): Rt=0.80 min; MS (ESIpos): m/z=555 [M+H]$^+$ $^1$H-NMR (400 MHz, DMSO-d6) δ[ppm]: 1.084 (0.56), 1.128 (7.60), 1.147 (16.00), 1.165 (7.95), 1.231 (0.88), 1.250 (0.48), 1.260 (0.52), 1.776 (11.64), 2.181 (0.79), 2.198 (1.21), 2.215 (0.82), 2.518 (2.29), 2.523 (1.57), 2.844 (2.18), 2.863 (6.91), 2.881 (6.59), 2.899 (2.06), 3.091 (0.50), 3.103 (0.50), 3.201 (0.43), 3.216 (0.54), 3.234 (1.24), 3.252 (0.91), 3.259 (0.96), 3.278 (1.11), 3.296 (0.94), 3.310 (1.23), 3.329 (1.41), 3.664 (0.49), 3.675 (0.76), 3.791 (11.61), 4.140 (1.57), 4.170 (2.33), 4.175 (1.48), 4.182 (1.27), 4.191 (0.72), 4.198 (0.63), 4.382 (1.61), 4.413 (1.34), 6.866 (1.30), 6.887 (2.13), 6.910 (1.79), 7.355 (0.99), 7.376 (1.83), 7.395 (1.43), 7.441 (1.86), 7.461 (1.09), 7.509 (1.21), 7.514 (2.07), 7.524 (2.41), 7.533 (2.13), 7.538 (1.38), 7.550 (0.42), 7.605 (1.62), 7.627 (1.47), 7.854 (1.05), 7.858 (0.76), 7.865 (0.59), 7.869 (0.66), 7.872 (0.70), 7.878 (0.94), 8.240 (0.95), 8.248 (0.66), 8.264 (0.89).

Example 351

4-methoxy-2,3-dimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid-N-ethylethanamine salt (Enantiomer 2)

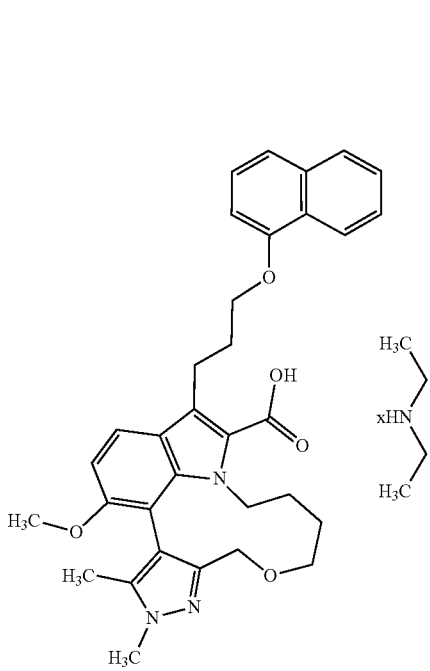

The title compound was prepared in analogy to the synthetic procedures described before.

Analytical chiral HPLC method: Instrument: Agilent HPLC 1260; column: YMC Amylose SA 3μ 100×4.6 mm; Eluent A: hexane+0.1 Vol-% N-ethylethanamine (99%); Eluent B: ethanol; Gradient: 20-50% B in 7 min; Flow 1.4 ml/min; Temperature: 25° C.; DAD 254 nm Analytical Chiral HPLC: $R_t$=3.63 min.

LC-MS (Method 2): Rt=0.79 min; MS (ESIpos): m/z=555 [M+H]$^+$ $^1$H-NMR (400 MHz, DMSO-d6) δ[ppm]: 1.084 (0.47), 1.118 (6.96), 1.137 (16.00), 1.155 (7.35), 1.232 (0.86), 1.260 (0.47), 1.776 (9.51), 2.179 (0.65), 2.197 (1.01), 2.214 (0.68), 2.518 (3.36), 2.523 (2.29), 2.826 (1.91), 2.844 (6.12), 2.862 (5.91), 2.880 (1.79), 3.090 (0.40), 3.102 (0.40), 3.211 (0.42), 3.230 (0.93), 3.249 (0.76), 3.274 (0.98), 3.293 (0.82), 3.331 (3.07), 3.669 (0.45), 3.791 (9.84), 4.140 (1.32), 4.170 (1.98), 4.182 (1.04), 4.191 (0.61), 4.198 (0.50), 4.381 (1.35), 4.411 (1.11), 6.866 (1.09), 6.883 (2.44), 6.905 (1.40), 7.355 (0.84), 7.376 (1.54), 7.395 (1.20), 7.440 (1.57), 7.461 (0.92), 7.509 (1.03), 7.514 (1.74), 7.524 (2.04), 7.533 (1.79), 7.538 (1.18), 7.599 (1.21), 7.621 (1.11), 7.854 (0.89), 7.858 (0.64), 7.865 (0.48), 7.869 (0.56), 7.872 (0.61), 7.878 (0.78), 8.239 (0.79), 8.247 (0.56), 8.264 (0.75).

Example 352

4-methoxy-1,3-dimethyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid ammonium salt (Enantiomer 1)

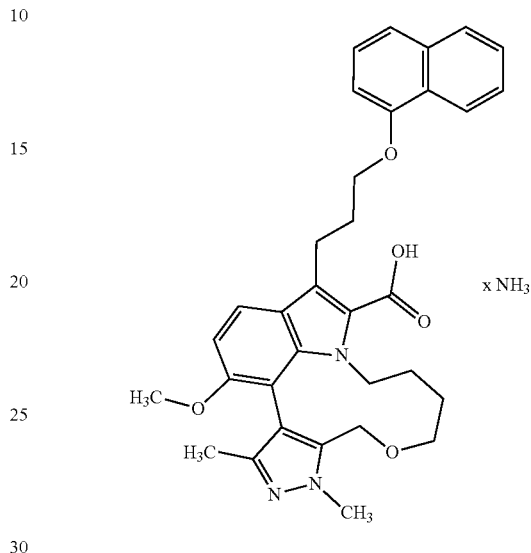

The title compound was prepared in analogy to the synthetic procedures described before.

Analytical chiral SFC method: Instrument: Agilent: 1260, Aurora SFC-Modul; column: Chiralpak IA 5 μm 100×4.6 mm; Eluent A: $CO_2$, Eluent B: ethanol+0.2 Vol-% aqueous ammonia (32%); 23% B; Flow 4.0 ml/min; Temperature: 37.5° C.; BPR: 100 bar; MWD @ 220 nm Analytical Chiral SFC: $R_t$=2.13 min.

LC-MS (Method 2): Rt=0.80 min; MS (ESIpos): m/z=555 [M+H]$^+$ $^1$H-NMR (400 MHz, DMSO-d6) δ[ppm]: 0.704 (0.51), 0.723 (1.25), 0.742 (0.65), 0.798 (1.45), 0.803 (0.89), 0.814 (1.58), 0.821 (1.72), 0.833 (1.36), 0.840 (1.67), 0.844 (2.01), 0.852 (4.91), 0.859 (3.59), 0.871 (1.43), 0.876 (2.37), 0.886 (0.91), 0.896 (0.47), 0.904 (1.63), 0.923 (0.85), 0.961 (0.58), 0.984 (0.83), 0.991 (0.67), 1.007 (0.58), 1.030 (2.16), 1.061 (0.65), 1.067 (0.71), 1.071 (0.74), 1.087 (0.74), 1.109 (0.85), 1.115 (0.98), 1.126 (2.79), 1.141 (2.88), 1.160 (0.87), 1.189 (0.71), 1.207 (0.62), 1.232 (2.97), 1.255 (0.87), 1.428 (0.78), 1.447 (0.76), 1.750 (14.04), 1.998 (0.69), 2.029 (0.74), 2.126 (0.56), 2.180 (1.16), 2.199 (1.58), 2.210 (1.18), 2.230 (0.60), 2.252 (0.42), 2.331 (1.23), 2.413 (0.47), 2.518 (5.58), 2.523 (3.55), 2.673 (1.03), 2.678 (0.65), 2.770 (0.54), 2.785 (0.58), 2.797 (0.60), 3.219 (0.49), 3.234 (0.60), 3.252 (0.85), 3.271 (0.60), 3.388 (0.89), 3.404 (0.85), 3.418 (0.74), 3.434 (0.40), 3.639 (16.00), 3.651 (0.89), 3.832 (15.11), 3.868 (0.62), 4.152 (1.72), 4.186 (2.79), 4.194 (2.63), 4.210 (1.25), 4.461 (0.58), 4.496 (0.51), 4.574 (2.03), 4.608 (1.83), 6.882 (1.63), 6.900 (1.74), 6.934 (2.28), 6.956 (2.39), 7.365 (1.09), 7.385 (2.23), 7.404 (1.72), 7.444 (2.68), 7.465 (1.50), 7.493 (0.49), 7.505 (1.32), 7.514 (1.81), 7.522 (2.97), 7.530 (1.81), 7.538 (1.61), 7.550 (0.56), 7.692 (1.87), 7.714 (1.72), 7.855 (1.56), 7.863 (0.80), 7.872 (1.27), 7.878 (1.32), 8.225 (1.16), 8.231 (1.12), 8.249 (1.14).

Example 353

4-methoxy-1,3-dimethyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid ammonium salt (Enantiomer 2)

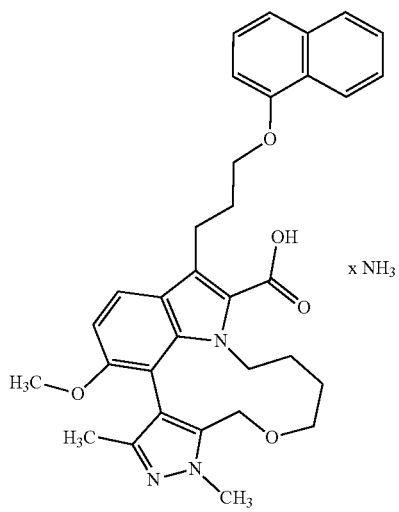 [SMILES: COc1ccc2c(CCCOc3cccc4ccccc34)c(C(=O)O)n3c2c1-c1c(C)nn(C)c1COCCCC3]

The title compound was prepared in analogy to the synthetic procedures described before.

Analytical chiral SFC method: Instrument: Agilent: 1260, Aurora SFC-Modul; column: Chiralpak IA 5 μm 100×4.6 mm; Eluent A: $CO_2$, Eluent B: ethanol+0.2 Vol-% aqueous ammonia (32%); 23% B; Flow 4.0 ml/min; Temperature: 37.5° C.; BPR: 100 bar; MWD @ 220 nm Analytical Chiral SFC: $R_t$=2.80 min.

LC-MS (Method 2): Rt=0.80 min; MS (ESIpos): m/z=555 [M+H]$^+$ $^1$H-NMR (400 MHz, DMSO-d6) δ[ppm]: 0.704 (0.51), 0.723 (1.33), 0.741 (0.64), 0.795 (0.46), 0.799 (0.54), 0.804 (0.49), 0.807 (0.44), 0.815 (0.67), 0.822 (0.77), 0.833 (1.28), 0.843 (1.90), 0.851 (4.90), 0.859 (3.54), 0.870 (1.44), 0.875 (2.36), 0.896 (0.54), 0.899 (0.46), 0.904 (0.59), 0.962 (0.59), 0.984 (0.85), 1.028 (2.15), 1.061 (0.69), 1.067 (0.67), 1.085 (0.62), 1.092 (0.64), 1.123 (2.79), 1.139 (2.77), 1.155 (0.79), 1.232 (1.77), 1.425 (0.82), 1.444 (0.79), 1.751 (13.82), 1.907 (0.44), 1.995 (0.69), 2.026 (0.82), 2.124 (0.56), 2.180 (0.97), 2.197 (1.62), 2.214 (1.00), 2.337 (0.64), 2.518 (5.97), 2.523 (4.18), 2.678 (0.54), 2.765 (0.51), 2.780 (0.59), 2.794 (0.54), 3.210 (0.44), 3.226 (0.56), 3.243 (0.74), 3.264 (0.51), 3.388 (0.90), 3.404 (0.79), 3.416 (0.69), 3.636 (16.00), 3.831 (15.08), 3.856 (0.62), 4.151 (1.72), 4.184 (2.72), 4.193 (2.46), 4.209 (1.18), 4.472 (0.51), 4.507 (0.46), 4.574 (2.05), 4.607 (1.82), 6.880 (1.56), 6.899 (1.67), 6.925 (2.00), 6.947 (2.05), 7.363 (1.10), 7.384 (2.18), 7.403 (1.69), 7.443 (2.64), 7.464 (1.49), 7.492 (0.46), 7.505 (1.31), 7.513 (1.79), 7.521 (2.95), 7.530 (1.74), 7.532 (1.67), 7.537 (1.56), 7.549 (0.56), 7.681 (1.49), 7.702 (1.36), 7.854 (1.56), 7.863 (0.77), 7.871 (1.28), 7.877 (1.33), 8.225 (1.10), 8.231 (1.03), 8.248 (1.08).

Example 354

(rac)-2,3-dimethyl-7-[2-(naphthalen-1-yl)ethyl]-2,10,11,12,13,15-hexahydropyrazolo[4',3':9,10][1,6]oxazacycloundecino[8,7,6-hi]indole-8-carboxylic acid

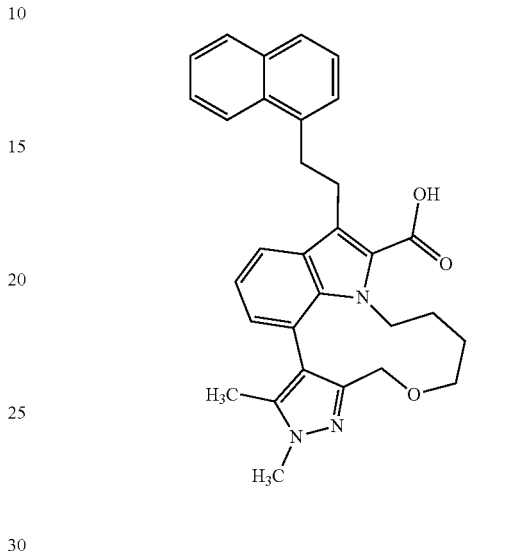

To a solution of (rac)-2,3-dimethyl-7-(naphthalen-1-ylethynyl)-2,10,11,12,13,15-hexahydropyrazolo[4',3':9,10][1,6]oxazacycloundecino[8,7,6-hi]indole-8-carboxylic acid (see Intermediate 382; 20.0 mg, 40.9 μmol) in THF (10 ml), Pd/C (10%, 20 mg) was added, and the mixture was reacted with an atmosphere of hydrogen at normal pressure for 5 h. Then the reaction mixture was filtered, and the filtrate was combined with a batch from an identical reaction on 20 mg scale. After evaporation, the crude product was subjected to flash chromatography (Biotage SNAP cartridge silica, dichloromethane/ethanol gradient, 0%-20% ethanol) to give the title compound (44 mg).

LC-MS (Method 2): Rt=0.77 min; MS (ESIpos): m/z=494 [M+H]$^+$ $^1$H-NMR (400 MHz, DMSO-d6) δ[ppm]: 0.798 (0.47), 0.814 (0.51), 0.821 (0.51), 0.904 (0.59), 1.035 (2.73), 1.041 (0.61), 1.052 (4.70), 1.066 (0.45), 1.070 (2.73), 1.177 (0.57), 1.203 (0.72), 1.232 (2.12), 1.325 (0.47), 1.374 (2.03), 1.402 (0.53), 1.731 (0.61), 1.829 (16.00), 2.518 (4.30), 2.522 (3.03), 2.673 (0.87), 3.096 (0.74), 3.109 (0.68), 3.122 (0.47), 3.284 (0.93), 3.295 (1.12), 3.353 (1.61), 3.364 (1.21), 3.377 (1.27), 3.388 (2.06), 3.423 (0.61), 3.434 (0.53), 3.440 (0.51), 3.452 (0.40), 3.769 (0.70), 3.807 (15.77), 3.903 (0.66), 3.926 (0.42), 4.185 (2.10), 4.216 (2.29), 4.312 (0.49), 4.330 (0.55), 4.343 (0.57), 4.511 (2.14), 4.542 (1.84), 5.759 (9.03), 6.916 (1.46), 6.918 (1.53), 6.934 (1.78), 7.093 (1.63), 7.114 (2.10), 7.131 (1.57), 7.404 (0.49), 7.421 (2.69), 7.428 (2.37), 7.437 (6.29), 7.445 (0.59), 7.499 (0.61), 7.502 (0.68), 7.516 (1.38), 7.518 (1.55), 7.535 (1.48), 7.539 (1.61), 7.546 (1.40), 7.558 (0.72), 7.562 (1.40), 7.565 (1.31), 7.578 (0.66), 7.582 (0.59), 7.639 (1.70), 7.641 (1.86), 7.658 (1.67), 7.661 (1.59), 7.771 (1.21), 7.780 (1.14), 7.785 (0.93), 7.795 (1.04), 7.911 (1.50), 7.915 (1.65), 7.934 (1.40), 8.316 (1.21), 8.336 (1.17).

Example 355

(rac)-2,3-dimethyl-7-{2-[4-(trifluoromethyl)phenyl]ethyl}-2,10,11,12,13,15-hexahydropyrazolo[4',3':9,10][1,6]oxazacycloundecino[8,7,6-hi]indole-8-carboxylic acid

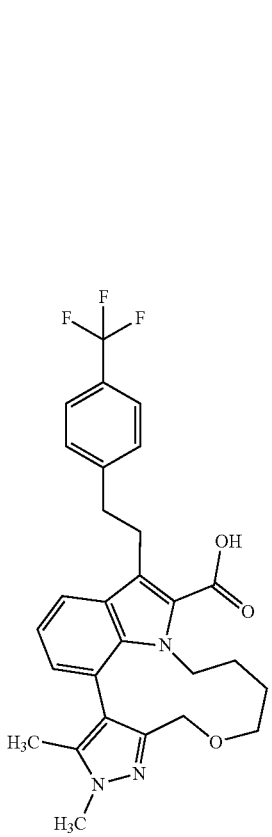 [SMILES: Cc1c2c(nn1C)COCCCCn1c(C(=O)O)c(CCc3ccc(C(F)(F)F)cc3)c3cccc-2c31]

A solution of (rac)-ethyl 2,3-dimethyl-7-{2-[4-(trifluoromethyl)phenyl]ethyl}-2,10,11,12,13,15-hexahydropyrazolo[4',3':9,10][1,6]oxazacycloundecino[8,7,6-hi]indole-8-carboxylate (see Intermediate 384; 50.0 mg, 92.7 μmol) in a mixture of THF (1 ml), ethanol (910 μl) and an aqueous lithium hydroxide solution (910 μl, 1.0 M, 910 μmol) was stirred for 3 days at room temperature, followed by 1 day at 45° C. and finally 8 hours at 55° C. After evaporation the residue was dissolved in a small amount of DMSO and subjected to preparative HPLC according method P8 to give the title compound (9 mg)

LC-MS (Method 2): Rt=0.74 min; MS (ESIpos): m/z=513 [M+H]$^+$ $^1$H-NMR (400 MHz, DMSO-d6) δ[ppm]: 1.235 (5.83), 1.817 (15.43), 2.327 (8.11), 2.668 (7.77), 2.970 (3.20), 3.089 (1.71), 3.799 (16.00), 4.180 (2.40), 4.210 (2.86), 4.494 (2.51), 4.524 (2.17), 6.878 (1.71), 7.072 (2.06), 7.426 (4.00), 7.447 (5.03), 7.590 (5.60), 7.609 (4.91), 7.641 (2.06).

Example 356

(rac)-2,3-dimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylic acid

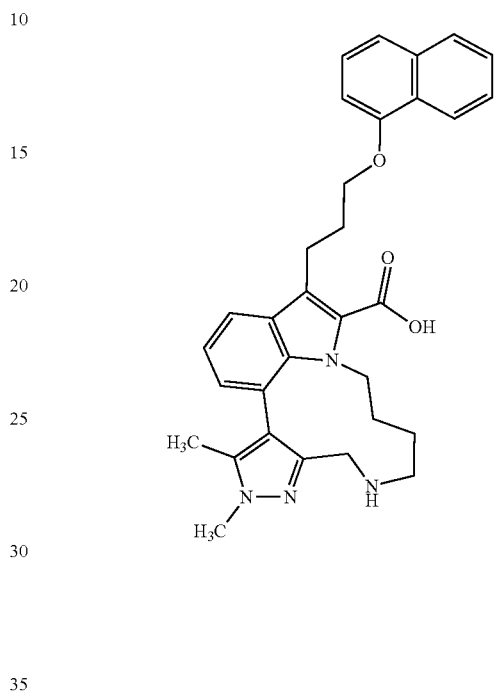

To a solution of (rac)-ethyl 2,3-dimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylate (see Intermediate 391; 200 mg, 363 μmol) in a mixture of THF (18 ml) and ethanol (12 ml) was added an aqueous lithium hydroxide solution (7.3 ml, 1.0 M, 7.3 mmol). The mixture then was stirred for 3 days at 40° C. After evaporation, the residue was dissolved in a small amount of DMSO and subjected to preparative HPLC according method P8 to give the title compound (51.2 mg).

LC-MS (Method 2): Rt=0.71 min; MS (ESIpos): m/z=524 [M+H]$^+$ $^1$H-NMR (400 MHz, DMSO-d6) δ[ppm]: 0.780 (0.50), 0.806 (0.62), 0.832 (0.46), 0.920 (0.46), 0.937 (0.59), 1.064 (0.66), 1.230 (1.42), 1.335 (0.53), 1.902 (16.00), 1.983 (0.67), 2.003 (0.51), 2.028 (0.76), 2.052 (0.50), 2.140 (1.17), 2.157 (1.70), 2.175 (1.35), 2.323 (0.85), 2.327 (1.10), 2.331 (0.83), 2.539 (7.62), 2.561 (0.69), 2.665 (0.83), 2.669 (1.05), 2.673 (0.80), 3.068 (0.57), 3.085 (0.85), 3.100 (0.96), 3.118 (1.15), 3.138 (0.87), 3.165 (1.40), 3.505 (1.31), 3.577 (1.51), 3.612 (1.63), 3.724 (0.64), 3.751 (0.94), 3.768 (1.05), 3.820 (12.77), 3.855 (0.85), 4.137 (1.47), 4.153 (2.59), 4.170 (1.40), 4.671 (0.66), 4.705 (0.64), 6.622 (1.51), 6.640 (1.65), 6.854 (1.78), 6.873 (1.92), 6.887 (1.35), 6.906 (1.97), 6.925 (1.10), 7.340 (1.10), 7.360 (2.15), 7.379 (1.58), 7.423 (2.56), 7.443 (1.47), 7.480 (0.64), 7.493 (1.72), 7.498 (2.29), 7.508 (3.00), 7.517 (2.49), 7.523 (1.79), 7.541 (1.94), 7.561 (1.53), 7.841 (1.58), 7.850 (0.92), 7.858 (1.23), 7.864 (1.28), 8.236 (1.35), 8.242 (1.21), 8.259 (1.26).

Example 357

(rac)-2,3-dimethyl-7-[2-(naphthalen-2-yloxy)ethyl]-2,10,11,12,13,15-hexahydropyrazolo[4',3':9,10][1,6]oxazacycloundecino[8,7,6-hi]indole-8-carboxylic acid

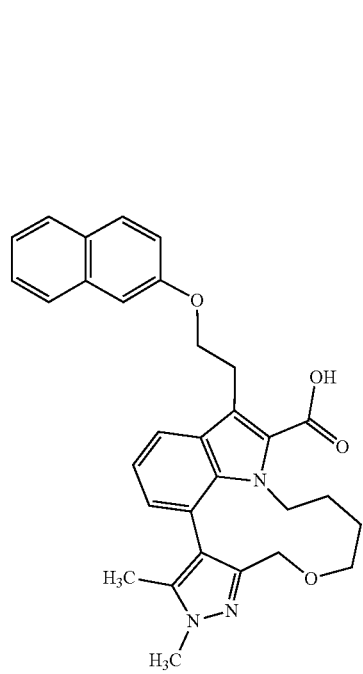 [SMILES: Cc1c2c(nn1C)COCCCCn1c(C(=O)O)c(CCOc3ccc4ccccc4c3)c3cccc-2c31]

To a solution of (rac)-ethyl 2,3-dimethyl-7-[2-(naphthalen-2-yloxy)ethyl]-2,10,11,12,13,15-hexahydropyrazolo[4',3':9,10][1,6]oxazacycloundecino[8,7,6-hi]indole-8-carboxylate (see Intermediate 387; 115 mg, 50% purity, 107 µmol) in a mixture of THF (5 ml) and ethanol (2.5 ml) was added an aqueous lithium hydroxide solution (2.5 ml, 1.0 M, 2.5 mmol). The mixture then was stirred 19 hours at 45° C. After evaporation, the residue was dissolved in a small amount of DMSO and subjected to preparative HPLC according method P8 to give the title compound (51.2 mg).

LC-MS (Method 2): Rt=0.80 min; MS (ESIpos): m/z=511 [M+H]$^+$ $^1$H-NMR (400 MHz, DMSO-d6) δ[ppm]: 1.058 (0.73), 1.184 (1.19), 1.233 (1.83), 1.355 (0.82), 1.832 (15.85), 3.063 (0.46), 3.088 (1.10), 3.101 (1.06), 3.111 (0.79), 3.125 (0.55), 3.288 (1.55), 3.536 (0.88), 3.553 (1.03), 3.572 (0.82), 3.602 (1.13), 3.619 (0.88), 3.804 (16.00), 3.904 (0.91), 4.181 (2.37), 4.212 (2.74), 4.259 (1.16), 4.275 (2.16), 4.296 (2.19), 4.312 (1.37), 4.335 (1.00), 4.352 (0.85), 4.369 (0.70), 4.495 (2.62), 4.526 (2.19), 6.911 (1.58), 6.929 (1.83), 7.124 (1.31), 7.143 (3.80), 7.163 (2.62), 7.170 (2.22), 7.303 (1.19), 7.321 (2.31), 7.340 (1.76), 7.378 (3.10), 7.406 (1.55), 7.426 (2.22), 7.444 (1.22), 7.777 (3.59), 7.798 (8.30), 7.820 (5.14).

Example 358

(rac)-(11Z)-2-methyl-3-[(4-methylpiperazin-1-yl)methyl]-7-[3-(naphthalen-1-yloxy)propyl]-2,10,13,15-tetrahydropyrazolo[4',3':9,10][1,6]oxazacycloundecino[8,7,6-hi]indole-8-carboxylic acid

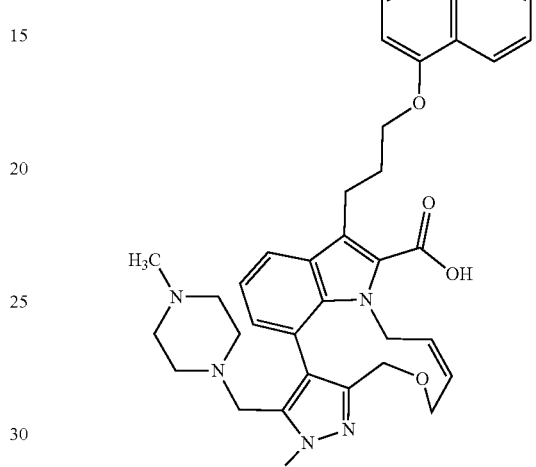

The title compound was prepared in analogy to the synthetic procedures described before.

Yield: 3.40 mg

LC-MS (Method 1): R$_t$=1.17 min; MS (ESIpos): m/z=620 [M+H]$^+$ $^1$H-NMR (400 MHz, DMSO-d6) δ[ppm]: 1.137 (0.67), 1.145 (0.87), 1.232 (1.00), 2.203 (1.47), 2.220 (2.13), 2.237 (1.47), 2.318 (1.27), 2.323 (2.87), 2.327 (4.07), 2.331 (2.87), 2.337 (1.33), 2.518 (15.80), 2.523 (11.07), 2.660 (2.20), 2.665 (3.87), 2.669 (5.00), 2.674 (3.67), 2.678 (2.07), 3.409 (4.53), 3.453 (0.53), 3.471 (0.60), 3.507 (2.13), 3.920 (16.00), 3.936 (1.13), 4.191 (2.53), 4.860 (1.00), 5.475 (1.60), 5.500 (1.67), 5.568 (1.33), 5.611 (1.47), 6.394 (0.73), 6.419 (1.40), 6.437 (0.67), 6.445 (0.80), 6.462 (1.33), 6.488 (0.67), 6.592 (0.40), 6.625 (0.47), 6.872 (2.20), 6.888 (2.40), 6.915 (1.87), 6.925 (1.53), 6.934 (3.20), 6.953 (3.40), 6.960 (1.27), 6.987 (0.93), 7.021 (2.73), 7.023 (3.00), 7.039 (2.00), 7.041 (1.93), 7.362 (1.60), 7.382 (3.13), 7.402 (2.80), 7.429 (3.40), 7.450 (1.67), 7.468 (0.67), 7.472 (0.87), 7.485 (2.07), 7.489 (1.80), 7.500 (4.40), 7.504 (3.93), 7.509 (2.40), 7.519 (4.00), 7.536 (0.93), 7.540 (0.67), 7.845 (2.00), 7.852 (1.20), 7.864 (2.13), 7.869 (1.67), 8.211 (1.73), 8.215 (1.73), 8.235 (1.60), 10.645 (1.13).

Example 359

(rac)-2-methyl-3-[(4-methylpiperazin-1-yl)methyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid

Example 360

(rac)-7-methyl-1-[3-(naphthalen-1-yloxy)propyl]-5,6,7,8,12,13-hexahydro-4H,11H-[1,3]oxazino[3'',2'':1',5']pyrazolo[3',4':7,8][1,5]diazecino[9,10,1-hi]indole-2-carboxylic acid

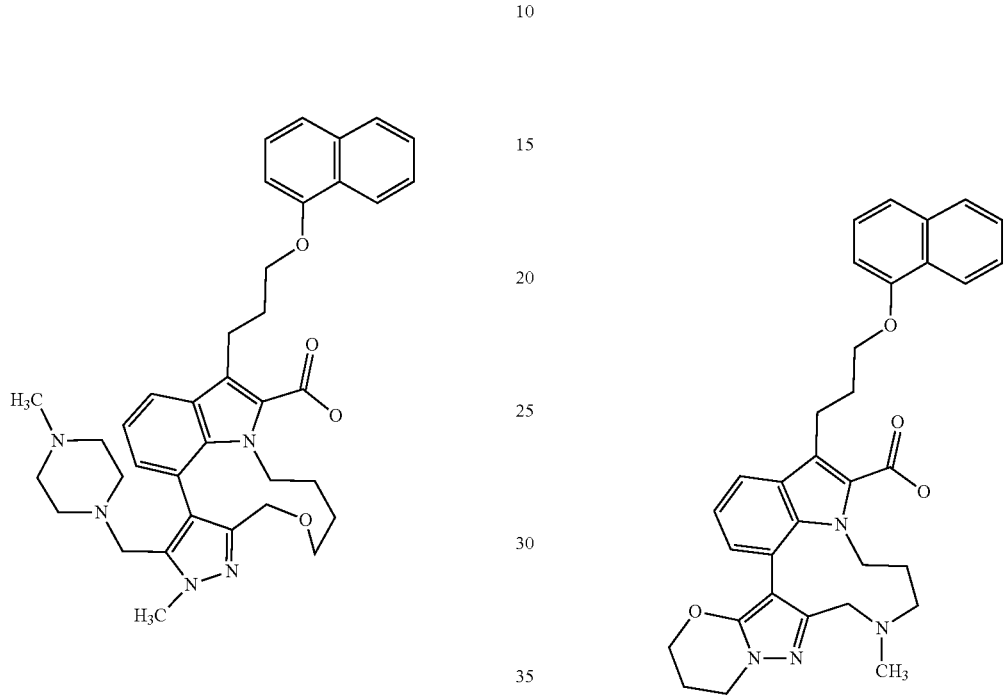

The title compound was prepared in analogy to the synthetic procedures described before.

Yield: 4.10 mg (90% purity)

LC-MS (Method 1): $R_t$=1.09 min; MS (ESIpos): m/z=622 [M+H]$^+$ $^1$H-NMR (400 MHz, METHANOL-d4) δ [ppm]: 0.010 (1.75), 0.723 (3.72), 0.741 (8.39), 0.760 (4.11), 1.188 (2.01), 1.206 (6.99), 1.215 (4.07), 1.224 (3.15), 1.233 (3.23), 1.312 (1.66), 1.743 (1.31), 1.759 (1.31), 2.194 (2.23), 2.211 (2.67), 2.227 (1.97), 2.547 (13.90), 2.553 (9.09), 2.571 (8.79), 2.840 (1.57), 2.939 (1.84), 2.956 (1.75), 3.051 (1.88), 3.087 (2.97), 3.123 (2.27), 3.142 (2.10), 3.456 (2.01), 3.491 (1.75), 3.834 (16.00), 3.853 (9.31), 4.095 (3.10), 4.106 (4.07), 4.121 (1.79), 4.234 (1.97), 4.264 (2.75), 4.274 (1.79), 4.346 (1.66), 4.378 (3.19), 4.409 (1.79), 4.762 (3.63), 6.304 (1.36), 6.339 (1.27), 6.736 (1.31), 6.754 (2.97), 6.771 (1.79), 6.907 (3.28), 6.919 (7.21), 6.927 (2.97), 6.935 (2.62), 7.230 (1.40), 7.250 (3.10), 7.269 (2.45), 7.294 (4.68), 7.315 (2.23), 7.368 (4.72), 7.372 (3.02), 7.379 (3.72), 7.386 (3.32), 7.391 (4.94), 7.512 (1.44), 7.519 (1.44), 7.534 (1.36), 7.692 (2.67), 7.705 (2.23), 7.716 (2.23), 8.232 (1.79), 8.240 (1.84), 8.252 (1.70).

The title compound was prepared in analogy to the synthetic procedures described before.

Yield: 81.2 mg (98% purity)

LC-MS (Method 1): $R_t$=1.20 min; MS (ESIneg): m/z=549 [M–H]$^-$ $^1$H-NMR (400 MHz, DMSO-d$_6$): δ [ppm]=13.09-12.81 (m, 1H), 8.26-8.22 (m, 1H), 7.89-7.84 (m, 1H), 7.64 (dd, 1H), 7.56-7.35 (m, 4H), 6.93-6.83 (m, 3H), 4.63-4.55 (m, 1H), 4.27-4.04 (m, 7H), 3.46-3.36 (m, 2H), 3.29-3.14 (m, 3H), 2.24-2.11 (m, 4H), 2.11-2.03 (m, 1H), 1.89 (br. s, 3H), 1.72-1.61 (m, 1H), 1.56-1.44 (m, 1H)

Example 361

(rac)-7-methyl-1-[3-(naphthalen-1-yloxy)propyl]-5,6,7,8,11,12,13,14-octahydro-4H-pyrido[1",2":1',5']pyrazolo[3',4':7,8][1,5]diazecino[9,10,1-hi]indole-2-carboxylic acid

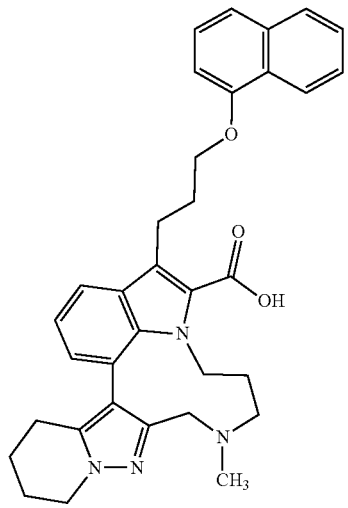 [SMILES: CN1CCCn2c(C(=O)O)c(CCCOc3cccc4ccccc34)c3cccc(c32)-c2c(nn3c2CCCC3)C1]

The title compound was prepared in analogy to the synthetic procedures described before.

Yield: 51.1 mg (98% purity)

LC-MS (Method 1): $R_t$=1.30 min; MS (ESIneg): m/z=547 [M−H]⁻

¹H-NMR (400 MHz, DMSO-d6) δ[ppm]: 1.173 (1.16), 1.231 (1.39), 1.388 (2.32), 1.396 (0.89), 1.528 (0.85), 1.611 (1.03), 1.741 (2.23), 1.778 (1.16), 1.908 (12.92), 1.964 (2.23), 1.979 (2.64), 1.993 (1.92), 2.034 (0.94), 2.068 (1.03), 2.151 (0.63), 2.169 (1.92), 2.186 (2.99), 2.202 (2.06), 2.219 (0.72), 2.287 (0.58), 2.302 (1.07), 2.318 (1.43), 2.323 (2.37), 2.327 (3.58), 2.332 (2.37), 2.337 (1.21), 2.344 (1.56), 2.360 (0.67), 2.435 (0.85), 2.462 (1.56), 2.518 (11.58), 2.523 (7.46), 2.533 (1.43), 2.540 (16.00), 2.559 (1.21), 2.574 (0.45), 2.660 (0.80), 2.665 (1.92), 2.669 (2.68), 2.673 (1.83), 2.679 (0.80), 3.171 (1.88), 3.204 (3.13), 3.236 (1.25), 3.250 (1.39), 3.270 (4.07), 3.288 (1.79), 3.331 (14.26), 3.365 (2.10), 3.384 (1.65), 3.403 (0.76), 3.877 (0.80), 3.899 (0.94), 3.908 (0.98), 3.932 (0.89), 4.014 (0.54), 4.029 (1.07), 4.045 (1.43), 4.061 (1.88), 4.076 (0.85), 4.107 (0.89), 4.122 (2.06), 4.137 (1.52), 4.153 (3.49), 4.168 (5.50), 4.183 (2.41), 4.540 (0.89), 4.549 (0.98), 4.570 (0.85), 4.585 (0.89), 6.805 (2.91), 6.808 (3.04), 6.822 (3.75), 6.826 (3.66), 6.855 (3.17), 6.873 (3.40), 6.924 (3.49), 6.943 (3.40), 6.944 (4.02), 6.962 (2.82), 7.355 (2.37), 7.376 (4.42), 7.395 (3.58), 7.438 (4.69), 7.458 (2.68), 7.488 (0.72), 7.492 (1.12), 7.505 (3.08), 7.512 (4.07), 7.521 (6.53), 7.529 (4.20), 7.536 (3.31), 7.548 (1.16), 7.553 (0.63), 7.640 (3.08), 7.643 (3.22), 7.660 (2.99), 7.663 (2.77), 7.851 (2.77), 7.860 (1.43), 7.869 (2.10), 7.875 (2.37), 8.151 (3.44), 8.227 (2.50), 8.234 (2.10), 8.243 (1.21), 8.252 (2.23).

Example 362

11,12,13-trimethyl-1-(4-(naphthalen-1-yloxy)butan-2-yl)-4,5,6,7,9,11-hexahydropyrazolo[4',3':9,10][1,6]oxaazacycloundecino[8,7,6-hi]indole-2-carboxylic acid (Mixture of Stereoisomers)

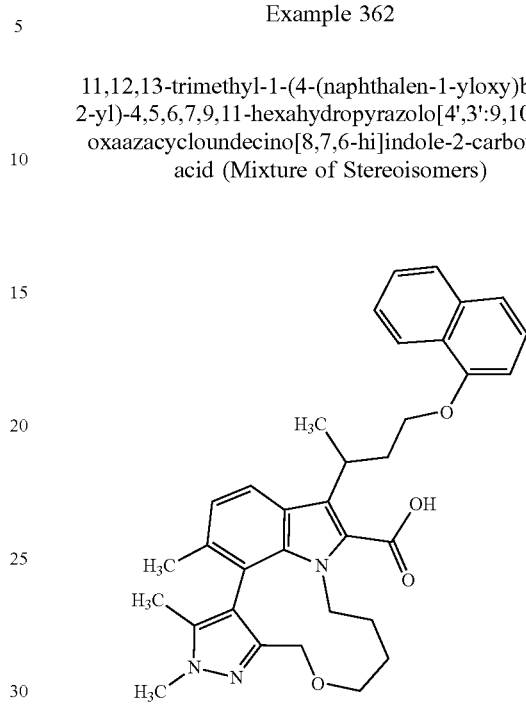

A mixture of ethyl 1-(4-((naphthalen-1-yl)oxy)butan-2-yl)-11,12,13-trimethyl-4,5,6,7,9,11-hexahydropyrazolo[4',3':9,10][1,6]oxaazacycloundecino[8,7,6-hi]indole-2-carboxylate (70 mg, 0.12 mmol; see Intermediate 504), ethanol (15 ml), and an aqueous solution of lithium hydroxide (2 M, 2 ml) was heated to 70° C. for 48 hours. Volatiles were removed, and the residue was partitioned between ethyl acetate and aqueous hydrochloric acid (3M). The layers were separated and the aqueous phase was extracted with ethyl acetate, the combined organic layers were washed with saturated aqueous sodium chloride solution and dried over sodium sulfate. Insoluble materials were removed by filtration, volatiles were removed under reduced pressure, and the residue was purified by flash chromatography on silica gel eluting with a gradient ethyl acetate in hexanes (0-100%) to give the title compound as a white solid (30 mg).

LRMS (ESIneg) m/z 550 [M−H]⁻

¹H NMR (400 MHz, DMSO-d₆) δ 13.02 (s, 1H), 8.12 (d, J=8.2 Hz, 1H), 7.87-7.74 (m, 2H), 7.55-7.42 (m, 2H), 7.40 (d, J=8.1 Hz, 1H), 7.32 (td, J=7.9, 4.4 Hz, 1H), 7.05 (dd, J=11.9, 8.3 Hz, 1H), 6.74 (dd, J=17.8, 7.6 Hz, 1H), 4.36 (dd, J=27.6, 12.5 Hz, 1H), 4.20 (dd, J=12.5, 8.7 Hz, 1H), 4.16-4.09 (m, 1H), 4.09-3.93 (m, 2H), 3.82 (d, J=3.8 Hz, 3H), 3.81-3.75 (m, 2H), 3.26-3.03 (m, 2H), 2.45-2.35 (m, 2H), 2.00 (d, J=2.1 Hz, 3H), 1.75 (d, J=22.3 Hz, 3H), 1.51 (dd, J=11.1, 7.1 Hz, 3H), 1.36-0.82 (m, 4H).

Example 363

11,12,13-trimethyl-1-(4-((5,6,7,8-tetrahydronaphthalen-1-yl)oxy)butan-2-yl)-4,5,6,7,9,11-hexahydropyrazolo[4',3':9,10][1,6]oxaazacycloundecino[8,7,6-hi]indole-2-carboxylic acid (Mixture of Stereoisomers)

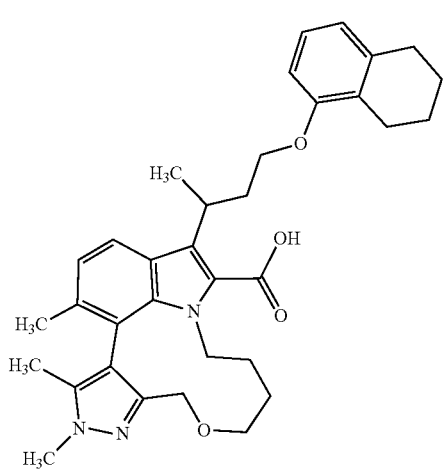 [SMILES: Cc1ccc2c(C(C)CCOc3cccc4c3CCCC4)c(C(=O)O)n3c2c1-c1c(nn(C)c1C)COCCCC3]

A mixture of ethyl 11,12,13-trimethyl-1-(4-((5,6,7,8-tetrahydronaphthalen-1-yl)oxy)butan-2-yl)-4,5,6,7,9,11-hexahydropyrazolo[4',3':9,10][1]oxa[6]azacycloundecino[8,7,6-hi]indole-2-carboxylate (59 mg, 0.1 mmol; see Intermediate 505), ethanol (15 ml), and an aqueous solution of lithium hydroxide (2 M, 2 ml) was heated to 70° C. for 48 hours. Volatiles were removed, and the residue were partitioned between ethyl acetate and aqueous hydrochloric acid (3M). The layers were separated and the aqueous phase was extracted with ethyl acetate, the combined organic layers were washed with saturated aqueous sodium chloride and dried over sodium sulfate. Insoluble materials were removed by filtration, volatiles removed under reduced pressure and the residue was purified by flash chromatography on silica gel eluting with a gradient ethyl acetate in hexanes (0-100%) to give the title compound as a orange film (28 mg).

LRMS (ESIneg) m/z=554 [M−H]−

$^1$H NMR (400 MHz, Chloroform-d) δ 7.83-7.72 (m, 1H), 7.10-7.02 (m, 1H), 6.93 (td, J=7.9, 5.1 Hz, 1H), 6.62 (dd, J=7.6, 4.8 Hz, 1H), 6.47 (dq, J=8.0, 3.9, 3.3 Hz, 1H), 4.66-4.53 (m, 1H), 4.46-4.26 (m, 1H), 4.26-4.03 (m, 2H), 4.01-3.77 (m, 6H), 3.59-2.92 (m, 2H), 2.79-2.56 (m, 4H), 2.54-2.22 (m, 2H), 2.15-2.02 (m, 3H), 1.99 (d, J=1.9 Hz, 1H), 1.93 (d, J=6.4 Hz, 1H), 1.84 (d, J=9.2 Hz, 2H), 1.72 (dp, J=18.7, 6.0 Hz, 4H), 1.56 (dt, J=12.6, 7.4 Hz, 3H), 1.47-1.00 (m, 4H).

Example 364

(rac)-10,12-dimethyl-1-(3-((6-(trifluoromethyl)naphthalen-1-yl)oxy)propyl)-4,5,6,7,9,10-hexahydropyrazolo[4',3':9,10][1,6]oxaazacycloundecino[8,7,6-hi]indole-2-carboxylic acid

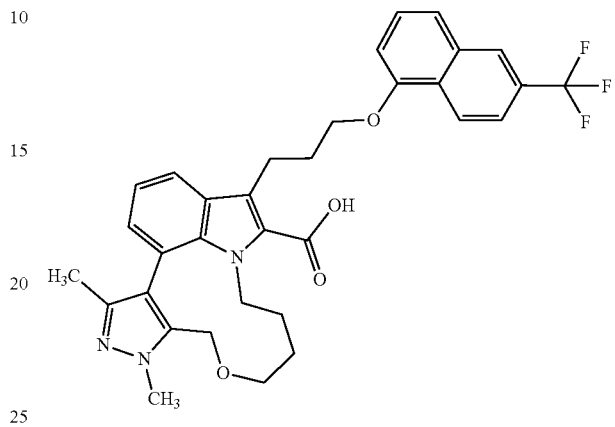

A solution of (rac)-ethyl 10,12-dimethyl-1-(3-((6-(trifluoromethyl)naphthalen-1-yl)oxy)propyl)-4,5,6,7,9,10-hexahydropyrazolo[4',3':9,10][1,6]oxaazacycloundecino[8,7,6-hi]indole-2-carboxylate (81 mg; see Intermediate 506) in ethanol (10 ml) was treated with an aqueous solution of lithium hydroxide (2 N, 3 ml) and the mixture was heated to reflux for 3 hours. The mixture was cooled to room temperature, volatiles were removed under reduced pressure, and the residue was partitioned between ethyl acetate and aqueous hydrochloric acid (3M). The organic layer was washed with saturated aqueous sodium chloride solution, the combined aqueous washes were back extracted with ethyl acetate, and the combined organic phases were dried over magnesium sulfate. Insoluble materials were removed by filtration, and the filtrate was concentrated under reduced pressure. The residue was purified by flash chromatography on silica gel eluting with a gradient of methanol in dichloromethane (0-5%) to give the title compound as a white foam (27 mg).

LRMS (ESIneg) m/z 590 [M−H]−

$^1$H NMR (400 MHz, DMSO-d$_6$) δ 13.15 (s, 1H), 8.39 (d, J=8.8 Hz, 1H), 8.36 (s, 1H), 7.74 (td, J=9.0, 8.4, 1.6 Hz, 2H), 7.68 (d, J=8.2 Hz, 1H), 7.55 (t, J=8.0 Hz, 1H), 7.11-7.01 (m, 2H), 6.84 (dd, J=7.1, 1.2 Hz, 1H), 4.63 (d, J=13.4 Hz, 1H), 4.55 (dt, J=14.1, 4.6 Hz, 1H), 4.31-4.20 (m, 3H), 4.00 (ddt, J=13.8, 9.1, 4.8 Hz, 1H), 3.84 (s, 3H), 3.39 (dq, J=16.3, 7.8, 7.4 Hz, 2H), 3.31 (s, 1H), 2.74 (dt, J=12.5, 7.0 Hz, 1H), 2.24 (q, J=6.9 Hz, 2H), 1.80 (s, 3H), 1.35-1.13 (m, 2H), 1.00 (s, 2H);

$^{19}$F NMR (376 MHz, DMSO-d$_6$) δ −60.73.

Experimental Section

BIOLOGICAL ASSAYS

Examples were tested in selected biological assays one or more times. When tested more than once, data are reported as either average values or as median values, wherein
the average value, also referred to as the arithmetic mean value, represents the sum of the values obtained divided by the number of times tested, and the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

An empty field in any of the following tables means that the respective compound has not been tested in that Assay.

The in vitro activity of the compounds of the present invention can be demonstrated in the following assays.

Protein-Protein Interaction Assay: MCL-1/Noxa BH3 Peptide (MCL-1 Assay)

The dose-dependent inhibition by the compounds described in this invention of the interaction between MCL-1 and the BH3 domain of Noxa (both human) was determined using a steady state binding competition assay with time-resolved fluorescence energy transfer (TR-FRET) readout. For that purpose MCL-1 (amino acids 173-329, N-terminal fused to Maltose Binding Protein (MBP)) and a synthetic Noxa BH3-derived peptide of sequence Biotin-PEG2-PEG2-PAELEVE-Nva-ATQLRRFGDKLN-FRQKLL-amide (SEQ ID NO: 1) served as protein receptor and tracer ligand respectively. The MBP-MCL-1 was purchased from Beryllium (Bedford, Mass., USA). The expression and purification of this protein construct has been described elsewhere (DOI:10.1371/journal.pone.0125010). The Noxa BH3-derived peptide can be obtained from e.g. Biosyntan (Berlin, Germany).

In the assay 11 different concentrations of each compound (0.1 nM, 0.33 nM, 1.1 nM, 3.8 nM, 13 nM, 44 nM, 0.15 µM, 0.51 µM, 1.7 µM, 5.9 µM and 20 µM) were typically measured as duplicates in the same microtiter plate. For that, 100-fold concentrated DMSO solutions were prepared by serial dilutions (1:3.4) of a 2 mM stock solution in a clear, 384-well microtiter plate (Greiner Bio-One, Frickenhausen, Germany). From there, 50 nl were transferred in a dark test plate (Greiner Bio-One, Frickenhausen, Germany). The assay was initiated by addition of 2 µl of a 2,5-fold concentrated MBP-MCL-1 solution (usually for a 1 nM end concentration in 5 µl reaction volume) in aqueous assay buffer [50 mM Tris/HCl pH 7, 100 mM sodium chloride (NaCl), 50 mM potassium fluoride (KF), 0.005% Tween-20, 2 mM DTT, 0.1% bovine gamma globulin (BGG)] to the compounds in the assay plate. This was followed by a 10-minute incubation step at 22° C. for pre-equilibration of the putative complex between MBP-MCL-1 and the compounds. After that, 3 µl of a 1.67-fold concentrated solution (in assay buffer) consisting of Noxa BH3-derived peptide (1 nM end concentration) and TR-FRET detection reagents [1.67 nM anti-MBP-Eu cryptate and 1.67 nM streptavidin-XL665 (both from Cisbio Bioassays, Codolet, France)], were added.

The mixture was incubated in the dark for one hour at 22° C. and then overnight at 4° C. The formation of MCL-1/Noxa complexes was determined by measuring the resonance energy transfer of the anti-MBP-Eu-cryptate antibody to the streptavidin-XL665 present in the reaction. For that purpose, the fluorescence emission at 620 nm and 665 nm after excitation at 330-350 nm was measured in a TR-FRET measuring instrument, for instance a Rubystar or a Pherastar (both from BMG Lab Technologies, Offenburg, Germany) or a Viewlux (Perkin-Elmer). The ratio of the emission at 665 nm and at 622 nm was used as indicator of the amount of MCL-1/NOXA complexes present.

The resulting data (ratio) were normalized, taking 0% inhibition as the mean value of control measurements (usually 32 data points) where all reagents were included. In this case 50 nl DMSO were used instead of compounds. A 100% inhibition corresponded to the mean value of control measurements (usually 32 data points) where all reagents except MCL-1 were included. $IC_{50}$ values were determined by regression analysis based on a 4 parameter equation (minimum, maximum, $IC_{50}$, Hill; $Y=Max+(Min-Max)/(1+(X/IC_{50})^{Hill})$ using the Screener Software (Genedata).

Protein-Protein Interaction Assay: BCL-XL/Bad BH3 Peptide (BCL-XL Assay)

The dose-dependent inhibition by the compounds described in this invention of the interaction between BCL-XL and the BH3 domain of Bad (both human) was determined using a steady state binding competition assay with time-resolved fluorescence energy transfer (TR-FRET) readout. For that purpose BCL-XL (amino acids 1-212, C-terminal fused to a hexahistidine (6×His) tag (SEQ ID NO: 3) and a synthetic Bad BH3-derived peptide of sequence Biotin-PEG2-PEG2-NLWAAQRYGRELRR-Nle-SDEFVDSFKK-amide (SEQ ID NO: 2) served as protein receptor and tracer ligand respectively. The recombinant BCL-XL protein (expressed in *E. coli*) was purchased from BPS Bioscience (San Diego, Calif., USA). The Bad BH3-derived peptide can be obtained from e.g. Biosyntan (Berlin, Germany).

In the assay 11 different concentrations of each compound (0.1 nM, 0.33 nM, 1.1 nM, 3.8 nM, 13 nM, 44 nM, 0.15 µM, 0.51 µM, 1.7 µM, 5.9 µM and 20 µM) were typically measured as duplicates in the same microtiter plate. For that, 100-fold concentrated DMSO solutions were prepared by serial dilutions (1:3.4) of a 2 mM stock solution in a clear, 384-well microtiter plate (Greiner Bio-One, Frickenhausen, Germany). From there, 50 nl were transferred in a dark test plate (Greiner Bio-One, Frickenhausen, Germany). The assay was initiated by addition of 2 µl of a 2,5-fold concentrated His-BCL-XL solution (usually for a 1 nM end concentration in 5 µl reaction volume) in aqueous assay buffer [50 mM Tris/HCl pH 7, 100 mM sodium chloride (NaCl), 50 mM potassium fluoride (KF), 0.005% Tween-20, 2 mM DTT, 0.1% bovine gamma globulin (BGG)] to the compounds in the assay plate. This was followed by a 10-minute incubation step at 22° C. for pre-equilibration of the putative complex between His-BCL-XL and the compounds. After that, 3 µl of a 1.67-fold concentrated solution (in assay buffer) consisting of Bad BH3-derived peptide (1 nM end concentration) and TR-FRET detection reagents [1.67 nM anti-His-Eu cryptate and 1.67 nM streptavidin-XL665 (both from Cisbio Bioassays, Codolet, France)], were added.

The mixture was incubated in the dark for one hour at 22° C. and then overnight at 4° C. The formation of BCL-XL/Bad complexes was determined by measuring the resonance energy transfer of the anti-His- Eu-cryptate antibody to the streptavidin-XL665 present in the reaction. For that purpose, the fluorescence emission at 620 nm and 665 nm after excitation at 330-350 nm was measured in a TR-FRET measuring instrument, for instance a Rubystar or a Pherastar (both from BMG Lab Technologies, Offenburg, Germany) or a Viewlux (Perkin-Elmer). The ratio of the emission at 665 nm and at 622 nm was used as indicator of the amount of BCL-XL/Bad complexes present.

The resulting data (ratio) were normalized, taking 0% inhibition as the mean value of control measurements (usually 32 data points) where all reagents were included. In this case 50 nl DMSO were used instead of compounds. A 100% inhibition corresponded to the mean value of control measurements (usually 32 data points) where all reagents except BCL-XL were included. $IC_{50}$ values were determined by regression analysis based on a 4 parameter equation (minimum, maximum, $IC_{50}$, Hill; Y=Max+(Min−Max)/(1+(X/$IC_{50}$)^Hill) using the Screener Software (Genedata).

Protein-Protein Interaction Assay: BCL-2/Bad BH3 Peptide (BCL-2 Assay)

The dose-dependent inhibition by the compounds described in this invention of the interaction between BCL-2 and the BH3 domain of Bad (both human) was determined using a steady state binding competition assay with time-resolved fluorescence energy transfer (TR-FRET) readout. For that purpose BCL-2 (amino acids 1-211, C-terminal fused to a hexahistidine (6×His) tag (SEQ ID NO: 3) and a synthetic Bad BH3-derived peptide of sequence Biotin-PEG2-PEG2-NLWAAQRYGRELRR-Nle-SDEFVDSFKK-amide (SEQ ID NO: 2) served as protein receptor and tracer ligand respectively. The recombinant BCL-2 protein (expressed in *E. coli*) was purchased from BPS Bioscience (San Diego, Calif., USA). The Bad BH3-derived peptide can be obtained from e.g. Biosyntan (Berlin, Germany).

In the assay 11 different concentrations of each compound (0.1 nM, 0.33 nM, 1.1 nM, 3.8 nM, 13 nM, 44 nM, 0.15 μM, 0.51 μM, 1.7 μM, 5.9 μM and 20 μM) were typically measured as duplicates in the same microtiter plate. For that, 100-fold concentrated DMSO solutions were prepared by serial dilutions (1:3.4) of a 2 mM stock solution in a clear, 384-well microtiter plate (Greiner Bio-One, Frickenhausen, Germany). From there, 50 nl were transferred in a dark test plate (Greiner Bio-One, Frickenhausen, Germany). The assay was initiated by addition of 2 μl of a 2,5-fold concentrated His-BCL-2 solution (usually for a 1 nM end concentration in 5 μl reaction volume) in aqueous assay buffer [50 mM Tris/HCl pH 7, 100 mM sodium chloride (NaCl), 50 mM potassium fluoride (KF), 0.005% Tween-20, 2 mM DTT, 0.1% bovine gamma globulin (BGG)] to the compounds in the assay plate. This was followed by a 10-minute incubation step at 22° C. for pre-equilibration of the putative complex between His-BCL-2 and the compounds. After that, 3 μl of a 1.67-fold concentrated solution (in assay buffer) consisting of Bad BH3-derived peptide (1 nM end concentration) and TR-FRET detection reagents [1.67 nM anti-His-Eu cryptate and 1.67 nM streptavidin-XL665 (both from Cisbio Bioassays, Codolet, France)], were added.

The mixture was incubated in the dark for one hour at 22° C. and then overnight at 4° C. The formation of BCL-2/Bad complexes was determined by measuring the resonance energy transfer of the anti-His-Eu-cryptate antibody to the streptavidin-XL665 present in the reaction. For that purpose, the fluorescence emission at 620 nm and 665 nm after excitation at 330-350 nm was measured in a TR-FRET measuring instrument, for instance a Rubystar or a Pherastar (both from BMG Lab Technologies, Offenburg, Germany) or a Viewlux (Perkin-Elmer). The ratio of the emission at 665 nm and at 622 nm was used as indicator of the amount of BCL-2/Bad complexes present.

The resulting data (ratio) were normalized, taking 0% inhibition as the mean value of control measurements (usually 32 data points) where all reagents were included. In this case 50 nl DMSO were used instead of compounds. A 100% inhibition corresponded to the mean value of control measurements (usually 32 data points) where all reagents except BCL-2 were included. $IC_{50}$ values were determined by regression analysis based on a 4 parameter equation (minimum, maximum, $IC_{50}$, Hill; Y=Max+(Min−Max)/(1+(X/$IC_{50}$)^Hill) using the Screener Software (Genedata).

TABLE 1

$IC_{50}$ values of selected examples in biochemical MCL-1 assay and biochemical BCL-2, BCL-XL Assay

| Example | MCL-1 Assay [M] (median) | BCL-2 Assay [M] (median) | BCL-XL Assay [M] (median) |
| --- | --- | --- | --- |
| 1-1 | | | |
| 1-2 | 7.06E−8 | | |
| 1-3 | 3.78E−9 | | |
| 1-4 | 3.04E−7 | | |
| 1-5 | 1.51E−9 | | |
| 1-6 | 1.87E−8 | | |
| 1-7 | 1.58E−8 | | |
| 1-8 | 1.87E−9 | | |
| 1-9 | 2.42E−8 | | |
| 1-10 | 9.30E−10 | >2.00E−5 | >2.00E−5 |
| 1-11 | 1.75E−8 | | |
| 1-12 | 6.88E−8 | | |
| 1-13 | 7.96E−10 | >2.00E−5 | >2.00E−5 |
| 1-15 | 3.03E−9 | >2.00E−5 | |
| 1-16 | 8.48E−8 | | |
| 1-17 | 1.27E−8 | | |
| 1-18 | | | |
| 1-19 | 5.27E−8 | | |
| 1-20 | 2.85E−9 | | |
| 1-21 | 1.06E−9 | | |
| 1-22 | 7.87E−10 | >2.00E−5 | >2.00E−5 |
| 1-23 | 3.23E−8 | | |
| 1-24 | 2.31E−9 | | |
| 1-25 | 1.31E−7 | | |
| 1-26 | 1.63E−9 | | |
| 1-27 | 2.08E−9 | | |
| 1-28 | 7.09E−8 | | |
| 1-29 | 1.19E−9 | | |
| 1-30 | 6.52E−9 | | |
| 1-31 | 4.62E−9 | >2.00E−5 | >2.00E−5 |
| 1-32 | 4.92E−8 | | |
| 1-33 | 9.00E−9 | | |
| 1-34 | 6.71E−9 | | |
| 1-35 | 1.10E−7 | | |
| 1-36 | 3.28E−9 | >2.00E−5 | >2.00E−5 |
| 1-37 | 1.72E−9 | >2.00E−5 | >2.00E−5 |
| 1-38 | 7.51E−8 | | |
| 1-39 | 2.51E−9 | | |
| 1-40 | 3.68E−8 | | |
| 1-41 | 1.06E−9 | | |
| 1-42 | 2.02E−8 | | |
| 1-43 | 7.99E−9 | >2.00E−5 | >2.00E−5 |
| 1-44 | 1.77E−8 | | |
| 1-46 | 1.43E−9 | 2.34E−6 | >2.00E−5 |
| 1-47 | 1.93E−8 | | |
| 1-49 | 5.42E−8 | | |
| 1-50 | 1.67E−8 | | |
| 1-52 | 2.81E−7 | | |
| 1-53 | 1.62E−8 | | |
| 1-55 | 1.67E−7 | | |
| 1-56 | 6.84E−9 | | |
| 1-58 | 1.89E−8 | | |
| 1-59 | 9.38E−8 | | |
| 1-60 | 1.71E−8 | | |
| 1-61 | 2.93E−9 | | |
| 1-62 | 6.70E−7 | | |
| 1-63 | 8.64E−9 | | |
| 1-64 | 9.88E−8 | | |
| 1-65 | 3.10E−8 | | |
| 1-66 | 9.43E−9 | | |
| 1-67 | 3.40E−7 | | |
| 1-68 | 2.69E−8 | | |
| 1-69 | 1.18E−8 | | |
| 1-70 | 2.00E−8 | | |
| 1-71 | 2.83E−9 | | |
| 1-72 | 1.26E−8 | | |
| 1-73 | 7.13E−9 | | |
| 1-74 | 4.79E−9 | >2.00E−5 | >2.00E−5 |
| 1-75 | 5.93E−9 | | |
| 1-76 | | | |

TABLE 1-continued

IC$_{50}$ values of selected examples in biochemical MCL-1 assay and biochemical BCL-2, BCL-XL Assay

| Example | MCL-1 Assay [M] (median) | BCL-2 Assay [M] (median) | BCL-XL Assay [M] (median) |
|---|---|---|---|
| 1-77 | 1.88E−7 | | |
| 1-78 | 9.05E−7 | | |
| 1-79 | 6.56E−7 | | |
| 1-80 | 5.01E−8 | | |
| 1-81 | 9.94E−8 | | |
| 1-82 | 1.13E−7 | | |
| 1-83 | 2.40E−7 | | |
| 1-84 | 1.10E−7 | | |
| 1-85 | 2.62E−7 | | |
| 1-86 | 2.78E−7 | | |
| 1-88 | 7.89E−9 | | |
| 1-89 | 5.41E−8 | | |
| 1-91 | 1.02E−8 | | |
| 1-92 | 6.80E−9 | | |
| 1-93 | 7.49E−8 | | |
| 1-94 | 1.41E−7 | | |
| 1-95 | 3.90E−9 | | |
| 1-96 | 1.73E−8 | | |
| 1-97 | 1.75E−7 | | |
| 1-99 | 2.03E−8 | | |
| 1-100 | 3.59E−8 | | |
| 1-101 | 3.19E−7 | | |
| 1-103 | 7.35E−9 | | |
| 1-104 | 3.55E−9 | >2.00E−5 | >2.00E−5 |
| 1-106 | 1.63E−8 | | |
| 1-107 | 8.97E−8 | | |
| 1-109 | 1.85E−8 | | |
| 1-110 | 5.81E−8 | | |
| 1-112 | 1.20E−8 | | |
| 1-113 | 2.77E−8 | | |
| 1-115 | 4.79E−8 | | |
| 1-116 | 1.37E−8 | | |
| 1-118 | 2.18E−6 | | |
| 1-119 | 2.31E−6 | | |
| 1-120 | 4.66E−9 | | |
| 1-121 | 4.36E−9 | | |
| 1-122 | 6.88E−6 | | |
| 001 | 1.01E−6 | | |
| 002 | 3.53E−7 | | |
| 003 | 4.33E−8 | | |
| 004 | 1.17E−7 | | |
| 005 | 6.60E−8 | | |
| 006 | 8.31E−9 | | |
| 007 | 9.87E−10 | | |
| 008 | 1.26E−7 | | |
| 009 | 6.32E−9 | | |
| 010 | 4.96E−9 | | |
| 011 | 1.62E−7 | | |
| 012 | 2.74E−8 | | |
| 013 | 3.45E−8 | | |
| 014 | 9.95E−9 | | |
| 015 | 9.58E−9 | | |
| 016 | 4.95E−7 | | |
| 017 | 8.96E−9 | >2.00E−5 | >2.00E−5 |
| 018 | 4.53E−9 | | |
| 019 | 8.62E−10 | >2.00E−5 | >2.00E−5 |
| 020 | 6.46E−8 | | |
| 021 | 1.10E−8 | | |
| 022 | 1.63E−9 | | |
| 023 | 1.69E−9 | >2.00E−5 | >2.00E−5 |
| 024 | 1.51E−8 | | |
| 025 | 1.84E−9 | | |
| 026 | 2.34E−8 | | |
| 027 | 5.27E−9 | | |
| 028 | 2.34E−7 | | |
| 029 | 2.20E−7 | | |
| 038 | 9.65E−9 | | |
| 039 | 5.01E−9 | >2.00E−5 | >2.00E−5 |
| 040 | 1.44E−8 | | |
| 041 | 4.44E−9 | >2.00E−5 | >2.00E−5 |
| 042 | 5.66E−8 | | |
| 043 | 1.27E−8 | | |
| 044 | 3.57E−9 | | |
| 045 | 2.59E−8 | | |
| 046 | 1.08E−8 | | |
| 047 | 2.86E−9 | >2.00E−5 | >2.00E−5 |
| 048 | 1.36E−8 | | |
| 049 | 3.18E−9 | | |
| 050 | 8.82E−9 | | |
| 051 | 7.37E−8 | | |
| 052 | 2.80E−8 | | |
| 053 | 3.41E−9 | | |
| 054 | 1.56E−9 | | |
| 055 | 4.10E−8 | | |
| 056 | 4.90E−8 | | |
| 057 | 4.53E−8 | >2.00E−5 | >2.00E−5 |
| 058 | 1.16E−7 | | |
| 059 | 2.39E−8 | | |
| 060 | 5.44E−9 | >2.00E−5 | >2.00E−5 |
| 061 | 3.22E−8 | >2.00E−5 | >2.00E−5 |
| 062 | 1.31E−8 | | |
| 063 | 1.06E−8 | | |
| 064 | 1.15E−8 | | |
| 065 | 3.93E−8 | | |
| 066 | 2.85E−8 | | |
| 067 | 2.21E−8 | | |
| 068 | 4.42E−9 | | |
| 069 | 1.62E−7 | | |
| 070 | 6.52E−9 | | |
| 071 | 4.12E−9 | | |
| 072 | 3.40E−9 | | |
| 073 | 2.06E−9 | >2.00E−5 | >2.00E−5 |
| 074 | 2.69E−8 | >2.00E−5 | >2.00E−5 |
| 075 | 1.71E−9 | | |
| 076 | 1.45E−9 | | |
| 077 | 3.42E−8 | | |
| 078 | 1.31E−8 | | |
| 079 | 3.25E−9 | | |
| 080 | 3.12E−8 | | |
| 081 | 1.50E−8 | | |
| 082 | 4.37E−9 | >2.00E−5 | >2.00E−5 |
| 083 | 1.72E−7 | | |
| 084 | 3.09E−9 | | |
| 085 | 4.51E−9 | >2.00E−5 | >2.00E−5 |
| 086 | 7.28E−8 | | |
| 087 | 9.70E−8 | | |
| 088 | 6.94E−9 | | |
| 089 | 3.84E−9 | | |
| 090 | 1.03E−8 | | |
| 091 | 2.02E−8 | | |
| 092 | 7.08E−9 | | |
| 093 | 1.19E−9 | >2.00E−5 | >2.00E−5 |
| 094 | 1.20E−7 | | |
| 096 | 1.36E−9 | | |
| 097 | 5.89E−8 | | |
| 098 | 8.27E−8 | | |
| 099 | 4.30E−9 | | |
| 100 | 4.24E−8 | | |
| 101 | 1.85E−9 | | |
| 102 | 6.82E−9 | | |
| 103 | 2.98E−9 | | |
| 104 | 1.06E−7 | | |
| 105 | 2.68E−9 | | |
| 107 | 1.71E−9 | >2.00E−5 | >2.00E−5 |
| 108 | 5.43E−8 | | |
| 109 | 1.11E−8 | | |
| 110 | 1.24E−8 | | |
| 111 | 3.27E−7 | | |
| 113 | 1.97E−8 | >2.00E−5 | >2.00E−5 |
| 114 | 3.03E−9 | | |
| 115 | 8.29E−8 | | |
| 116 | 8.28E−6 | | |
| 117 | 6.33E−7 | | |
| 119 | 2.13E−8 | | |
| 120 | 2.72E−8 | | |
| 122 | 5.77E−8 | | |
| 123 | 3.14E−9 | | |

TABLE 1-continued

IC$_{50}$ values of selected examples in biochemical MCL-1 assay and biochemical BCL-2, BCL-XL Assay

| Example | MCL-1 Assay [M] (median) | BCL-2 Assay [M] (median) | BCL-XL Assay [M] (median) |
|---|---|---|---|
| 124 | 1.87E−8 | | |
| 125 | 1.08E−8 | | |
| 126 | 8.45E−8 | | |
| 127 | 1.44E−8 | | |
| 128 | 4.03E−8 | | |
| 129 | 2.22E−8 | | |
| 130 | 3.31E−8 | | |
| 131 | 1.91E−8 | | |
| 132 | 3.35E−8 | | |
| 133 | 1.86E−8 | | |
| 134 | 3.22E−7 | | |
| 135 | 1.47E−8 | | |
| 136 | 2.28E−8 | | |
| 137 | 1.07E−8 | | |
| 138 | 1.35E−8 | | |
| 139 | 4.22E−8 | | |
| 140 | 1.14E−8 | | |
| 141 | 7.27E−9 | >2.00E−5 | >2.00E−5 |
| 142 | 5.23E−9 | | |
| 143 | 3.08E−8 | | |
| 144 | 3.34E−9 | >2.00E−5 | >2.00E−5 |
| 145 | 1.17E−9 | >2.00E−5 | >2.00E−5 |
| 146 | 9.01E−9 | | |
| 147 | 3.77E−9 | | |
| 148 | 9.19E−10 | >2.00E−5 | >2.00E−5 |
| 149 | 6.66E−8 | | |
| 150 | 7.61E−9 | | |
| 151 | 1.33E−8 | | |
| 152 | 3.79E−7 | | |
| 153 | 4.80E−9 | >2.00E−5 | >2.00E−5 |
| 154 | 1.28E−9 | >2.00E−5 | >2.00E−5 |
| 155 | 4.80E−8 | | |
| 156 | 1.52E−7 | | |
| 157 | 2.89E−7 | | |
| 159 | 2.38E−8 | | |
| 160 | 2.08E−8 | | |
| 161 | 5.21E−8 | | |
| 162 | 7.61E−9 | | |
| 163 | 6.37E−7 | | |
| 164 | 1.07E−8 | | |
| 165 | 2.89E−9 | | |
| 166 | 4.10E−8 | | |
| 169 | 1.84E−8 | | |
| 170 | 2.97E−9 | | |
| 171 | 2.68E−9 | | |
| 172 | 1.44E−7 | | |
| 177 | 1.07E−8 | | |
| 178 | 1.81E−8 | | |
| 179 | 9.43E−9 | | |
| 180 | 1.77E−8 | | |
| 181 | 7.77E−9 | | |
| 182 | 1.22E−7 | | |
| 183 | 2.25E−9 | | |
| 184 | 1.60E−9 | | |
| 185 | 2.11E−7 | | |
| 186 | 1.57E−8 | | |
| 187 | 2.61E−9 | | |
| 188 | 1.46E−9 | | |
| 189 | 1.42E−7 | | |
| 190 | 5.46E−9 | | |
| 191 | 2.73E−9 | | |
| 192 | 1.23E−7 | | |
| 193 | 2.33E−9 | | |
| 194 | 7.35E−9 | | |
| 195 | 5.32E−8 | | |
| 196 | 1.61E−9 | | |
| 197 | 1.04E−7 | | |
| 198 | 2.80E−9 | | |
| 199 | 1.26E−9 | | |
| 200 | 2.48E−8 | | |
| 201 | 4.27E−9 | | |
| 202 | 4.62E−8 | | |
| 203 | 2.10E−9 | | |
| 204 | 3.75E−9 | | |
| 205 | 1.65E−9 | | |
| 206 | 1.55E−8 | | |
| 207 | 6.81E−9 | | |
| 208 | 3.73E−9 | | |
| 209 | 2.50E−8 | | |
| 211 | 1.74E−7 | | |
| 212 | 6.37E−9 | | |
| 213 | 1.34E−8 | | |
| 214 | 5.24E−9 | | |
| 215 | 1.82E−7 | | |
| 216 | 5.80E−9 | | |
| 217 | 2.51E−9 | | |
| 218 | 5.59E−7 | | |
| 219 | 1.40E−8 | | |
| 220 | 3.23E−9 | | |
| 221 | 3.53E−7 | | |
| 222 | 5.97E−9 | | |
| 223 | 4.24E−9 | | |
| 224 | 3.95E−7 | | |
| 225 | 3.20E−9 | | |
| 226 | 3.02E−9 | | |
| 227 | 9.09E−8 | | |
| 228 | 4.26E−9 | | |
| 229 | 5.59E−9 | | |
| 230 | 1.85E−7 | | |
| 231 | 2.62E−8 | | |
| 232 | 9.74E−9 | | |
| 233 | 2.42E−7 | | |
| 234 | 1.39E−8 | | |
| 235 | 7.79E−8 | | |
| 236 | 6.78E−9 | | |
| 237 | 4.99E−9 | | |
| 238 | 3.26E−9 | | |
| 239 | 9.27E−8 | | |
| 240 | 8.85E−9 | | |
| 241 | 7.51E−9 | | |
| 242 | 2.58E−7 | | |
| 243 | 7.78E−9 | | |
| 244 | 6.64E−9 | | |
| 247 | 6.15E−9 | | |
| 248 | 4.74E−9 | | |
| 249 | 4.27E−8 | | |
| 250 | 7.88E−9 | | |
| 251 | 4.84E−8 | | |
| 252 | 3.70E−9 | | |
| 253 | 8.67E−9 | | |
| 254 | 2.14E−9 | | |
| 255 | 6.70E−8 | | |
| 256 | 4.25E−8 | | |
| 257 | 6.69E−7 | | |
| 258 | 1.20E−5 | | |
| 259 | 5.77E−7 | | |
| 260 | 8.75E−9 | | |
| 261 | 3.73E−9 | | |
| 262 | 3.88E−8 | | |
| 263 | 9.26E−7 | | |
| 264 | 1.32E−7 | | |
| 265 | 5.85E−9 | | |
| 266 | 2.59E−9 | | |
| 267 | 3.70E−10 | | |
| 268 | 4.07E−8 | | |
| 269 | 7.74E−9 | | |
| 270 | 5.78E−9 | | |
| 271 | 3.06E−8 | | |
| 272 | 9.83E−7 | | |
| 273 | 5.89E−9 | | |
| 274 | 1.56E−6 | | |
| 275 | 3.97E−6 | | |
| 276 | 7.56E−9 | | |
| 277 | 1.30E−9 | | |
| 278 | 1.42E−7 | | |
| 279 | 1.60E−6 | | |
| 280 | 1.94E−7 | | |
| 281 | 1.63E−9 | | |

TABLE 1-continued

IC$_{50}$ values of selected examples in biochemical MCL-1 assay and biochemical BCL-2, BCL-XL Assay

| Example | MCL-1 Assay [M] (median) | BCL-2 Assay [M] (median) | BCL-XL Assay [M] (median) |
|---|---|---|---|
| 282 | 1.09E−9 | | |
| 283 | 4.44E−8 | | |
| 284 | 2.21E−9 | | |
| 285 | 7.82E−10 | | |
| 286 | 2.72E−8 | | |
| 287 | 2.06E−9 | | |
| 288 | 1.49E−9 | | |
| 289 | 1.06E−7 | | |
| 290 | 2.80E−9 | | |
| 291 | 2.38E−9 | | |
| 292 | 1.84E−9 | | |
| 293 | 6.76E−10 | | |
| 294 | 5.79E−9 | | |
| 295 | 5.28E−9 | | |
| 296 | 3.31E−9 | | |
| 297 | 1.26E−7 | | |
| 298 | 1.70E−9 | | |
| 299 | 1.66E−7 | | |
| 300 | 1.27E−9 | | |
| 301 | 1.43E−9 | | |
| 302 | 1.26E−9 | | |
| 303 | 2.68E−8 | | |
| 304 | 1.05E−8 | | |
| 305 | 5.36E−9 | | |
| 306 | 2.86E−7 | | |
| 307 | 1.29E−8 | | |
| 308 | 5.07E−9 | | |
| 309 | 1.33E−7 | | |
| 310 | 3.31E−8 | | |
| 311 | 5.43E−7 | | |
| 312 | 2.20E−8 | | |
| 313 | 9.99E−8 | | |
| 314 | 3.35E−8 | | |
| 315 | 9.19E−7 | | |
| 316 | 3.08E−9 | | |
| 317 | 1.15E−8 | | |
| 318 | 1.31E−8 | | |
| 319 | 3.71E−8 | | |
| 320 | 2.26E−8 | | |
| 321 | 6.39E−7 | | |
| 322 | 1.08E−6 | | |
| 323 | 3.20E−7 | | |
| 324 | 2.70E−8 | | |
| 325 | 8.02E−8 | | |
| 326 | 5.15E−7 | | |
| 327 | 1.03E−7 | | |
| 328 | 4.67E−8 | | |
| 329 | 3.00E−6 | | |
| 330 | 1.53E−7 | | |
| 331 | 1.85E−7 | | |
| 332 | 2.03E−7 | | |
| 333 | 1.04E−6 | | |
| 334 | 9.17E−8 | | |
| 335 | 1.80E−7 | | |
| 336 | 1.32E−7 | | |
| 337 | 9.77E−7 | | |
| 338 | 4.80E−8 | | |
| 339 | 3.20E−8 | | |
| 340 | 2.19E−8 | | |
| 341 | 6.51E−7 | | |
| 342 | 4.51E−8 | | |
| 343 | 3.25E−7 | | |
| 344 | 4.33E−7 | | |
| 345 | 2.60E−8 | | |
| 346 | 1.42E−8 | | |
| 347 | 3.43E−7 | | |
| 348 | 1.96E−8 | | |
| 349 | 8.19E−8 | | |
| 350 | 5.63E−8 | | |
| 351 | 2.03E−6 | | |
| 352 | 4.54E−8 | | |
| 353 | 1.28E−6 | | |
| 354 | 2.96E−7 | | |
| 355 | 1.51E−6 | | |
| 356 | 9.43E−9 | | |
| 357 | 4.09E−8 | | |
| 358 | 1.73E−8 | | |
| 359 | 7.50E−8 | | |
| 360 | 1.98E−8 | | |
| 361 | 2.48E−8 | | |
| 362 | 1.87E−8 | | |
| 363 | 4.20E−8 | | |
| 364 | 6.33E−8 | | |

An aspect of the invention are compounds of formula (I) which have an IC$_{50}$ of less or equal to 5 E-8, particularly less or equal to 1 E-8 and more particularly less or equal to 5 E-9.

Cellular Assays

Induction of Caspase-3/7 Activity Upon Treatment of Cells with Selected Compounds The BH3-domain of MCL-1 sequesters pro-apoptotic proteins, thereby inhibiting apoptosis. In contrast, MCL-1 inhibitors are expected to antagonize this effect leading to an increase in apoptosis, which can be determined by measuring the activity of caspase-3/7.

The activity of caspase-3/7 was determined in DLBCL (Diffuse large B-cell lymphoma) cell lines (SUDHL5 and SUDHL10) upon treatment with different compounds, using the Caspase-Glo® 3/7 reagent from Promega (G8092).

The different cell lines were plated in culture medium (RPMI 1640 [GIBCO #22400-089]supplemented with 10% Fetal Bovine Serum) at a density of 3,300 cells in 30 µl/well in a sterile, solid black, flat bottom, polystyrene, TC-treated 384-well microplate (Corning #3571) using Multidrop Combi Reagent Dispenser. As a control, medium without cells was also added to the plate. Cells were incubated in a humidified incubator at 37° C. overnight.

On the next day, the cells were treated with compounds (stock solution, 10 mM in DMSO) using the HP D300 Digital Dispenser in a concentration range of 3.3×10e-5 M (33 µM) to 5×10e-9 M (5 nM) in a single-dot curve with at least 16 dilutions and a DMSO concentration of 0.33%. Rim wells were excluded. The cells were incubated for 3 h hours in a humidified incubator at 37° C. After this incubation, 30 µl of Caspase-Glo® 3/7 reagent (Promega G8092) was added to each well using the Multidrop Combi Reagent Dispenser, followed by 1 h incubation at 37° C. Finally, luminescence was read at 0.1 ms, with a gain of 3000 using the PHERAstar FS microplate reader (BMG Labtech).

For the evaluation of the results, the background measured with "medium-only" was subtracted from all other values. Then, the values were normalized to DMSO-only treated cells (every value was divided by the mean of the DMSO control). The Bella DRC Master Sheet was used to calculate EC50s, with fixed C0=1 and CI=plateau/max induction for the reference compound.

TABLE 3

EC$_{50}$ values of selected examples in cellular caspase induction assay

| Example | Caspase SUDHL5 [M] (median) | Caspase SUDHL10 [M] (median) |
|---|---|---|
| 1-1 | 1.48E−5 | 2.25E−5 |
| 1-2 | >3.30E−5 | >3.30E−5 |
| 1-3 | 2.00E−6 | 2.36E−6 |
| 1-4 | 1.52E−5 | 5.18E−6 |
| 1-5 | 2.52E−6 | 2.62E−6 |
| 1-6 | 7.67E−6 | 1.19E−5 |
| 1-7 | >3.30E−5 | >3.30E−5 |
| 1-8 | 5.79E−7 | 9.53E−7 |
| 1-9 | 1.25E−5 | 1.47E−5 |
| 1-10 | 4.86E−7 | 7.55E−7 |
| 1-11 | 4.05E−7 | 6.52E−7 |
| 1-12 | 1.83E−5 | 2.04E−5 |
| 1-13 | 3.24E−7 | 6.14E−7 |
| 1-15 | 1.17E−6 | 1.82E−6 |
| 1-16 | >3.30E−5 | >3.30E−5 |
| 1-17 | 3.73E−6 | 4.39E−6 |
| 1-18 | 1.22E−6 | 1.94E−6 |
| 1-19 | 1.72E−5 | 2.06E−5 |
| 1-20 | 1.63E−6 | 1.95E−6 |
| 1-21 | 2.34E−6 | 2.82E−6 |
| 1-22 | 1.56E−6 | 2.21E−6 |
| 1-23 | 2.13E−5 | 2.30E−5 |
| 1-24 | 4.28E−6 | 6.61E−6 |
| 1-25 | 1.61E−6 | 3.89E−6 |
| 1-26 | >3.30E−5 | >3.30E−5 |
| 1-27 | 4.42E−6 | 7.50E−6 |
| 1-28 | >3.30E−5 | >3.30E−5 |
| 1-29 | 2.64E−6 | 5.26E−6 |
| 1-30 | 1.56E−5 | 3.01E−5 |
| 1-31 | 4.33E−6 | 7.27E−6 |
| 1-32 | >3.30E−5 | 2.29E−5 |
|  |  | 2.04E−5 |
|  |  | >3.30E−5 |
|  |  | >3.30E−5 |
| 1-33 | 5.78E−6 | 1.37E−5 |
| 1-34 | 4.50E−6 | 6.15E−6 |
| 1-35 | 2.69E−5 | >3.30E−5 |
| 1-36 | 3.94E−6 | 7.51E−6 |
| 1-37 | 2.44E−6 | 3.84E−6 |
| 1-38 | >3.30E−5 | >3.30E−5 |
| 1-39 | 3.47E−6 | 2.45E−6 |
| 1-40 | 2.16E−5 | >3.30E−5 |
| 1-41 | 7.23E−7 | 8.97E−7 |
| 1-42 | 1.09E−5 | 1.49E−5 |
| 1-43 | 6.57E−6 | 1.11E−5 |
| 1-44 | 1.24E−5 | 9.76E−6 |
| 1-46 | 7.76E−7 | 1.74E−6 |
| 1-47 | 9.12E−6 | 9.54E−6 |
| 1-49 | 2.04E−5 | 1.88E−5 |
| 1-50 | 6.14E−6 | 6.71E−6 |
| 1-52 | 3.10E−5 | >3.30E−5 |
| 1-53 | 1.02E−5 | 7.50E−6 |
| 1-55 | >3.30E−5 | >3.30E−5 |
| 1-56 | 5.70E−6 | 7.13E−6 |
| 1-58 | 1.22E−5 | 1.73E−5 |
| 1-59 | 1.79E−5 | 1.51E−5 |
| 1-60 | 1.95E−5 | 2.59E−5 |
| 1-61 | 6.16E−6 | 1.07E−5 |
| 1-62 | 1.45E−5 | 1.31E−5 |
| 1-63 | 7.66E−6 | 7.32E−6 |
| 1-64 | 1.99E−5 | 2.94E−5 |
| 1-65 | 1.63E−6 | 1.75E−5 |
| 1-66 | 6.15E−6 | 8.47E−6 |
| 1-67 | 1.61E−5 | 1.78E−5 |
| 1-68 | >3.30E−5 | >3.30E−5 |
| 1-69 | >3.30E−5 | >3.30E−5 |
| 1-70 | >3.30E−5 | >3.30E−5 |
| 1-71 | >3.30E−5 | >3.30E−5 |
| 1-72 | >3.30E−5 | >3.30E−5 |
| 1-73 | 6.83E−6 | 1.19E−5 |
| 1-74 | 8.87E−6 | 2.03E−5 |
| 1-75 | 3.05E−5 | >3.30E−5 |
|  | >3.30E−5 |  |
| 1-76 | >3.30E−5 | >3.30E−5 |
| 1-77 | >3.30E−5 | >3.30E−5 |
| 1-78 | >3.30E−5 | >3.30E−5 |
| 1-79 | >3.30E−5 | 2.07E−5 |
| 1-80 | >3.30E−5 | >3.30E−5 |
| 1-81 | >3.30E−5 | >3.30E−5 |
| 1-82 | >3.30E−5 | >3.30E−5 |
| 1-83 | >3.30E−5 | >3.30E−5 |
| 1-84 | >3.30E−5 | >3.30E−5 |
| 1-85 | >3.30E−5 | >3.30E−5 |
| 1-86 | >3.30E−5 | >3.30E−5 |
| 1-88 | 6.03E−6 | 6.35E−6 |
| 1-89 | 1.17E−5 | 2.75E−5 |
| 1-91 | 6.34E−6 | 7.32E−6 |
| 1-92 | 3.88E−6 | 4.47E−6 |
| 1-93 | >3.30E−5 | 3.18E−5 |
| 1-94 | >3.30E−5 | >3.30E−5 |
| 1-95 | 1.08E−5 | 2.27E−5 |
| 1-96 | 2.39E−5 | >3.30E−5 |
| 1-97 | >3.00E−5 | >3.00E−5 |
| 1-99 | 9.00E−6 | 1.35E−5 |
| 1-100 | 2.84E−5 | >3.30E−5 |
|  |  | 3.06E−5 |
| 1-101 | >3.30E−5 | >3.30E−5 |
| 1-103 | 2.83E−6 | 7.79E−6 |
| 1-104 | 4.96E−6 | 8.64E−6 |
| 1-106 | 1.15E−5 | 9.37E−6 |
| 1-107 | 1.94E−5 | 1.28E−5 |
|  | >3.30E−5 | >3.30E−5 |
| 1-109 | 7.09E−6 | 8.86E−6 |
| 1-110 | 1.53E−5 | 1.53E−5 |
| 1-112 | 2.32E−6 | 3.34E−6 |
| 1-113 | 1.05E−5 | 9.08E−6 |
| 1-115 | >3.30E−5 | 3.29E−5 |
| 1-116 | 1.69E−5 | 1.99E−5 |
| 1-118 | >3.30E−5 | >3.30E−5 |
| 1-119 | >3.30E−5 | >3.30E−5 |
| 1-120 | >3.30E−5 | >3.30E−5 |
| 1-121 | 2.66E−6 | 8.04E−6 |
| 1-122 | >3.30E−5 | >3.30E−5 |
| 001 | >3.30E−5 | 2.91E−5 |
| 002 | >3.30E−5 | 2.24E−5 |
| 003 | >3.30E−5 | 2.91E−5 |
| 004 | 1.25E−5 | 2.58E−5 |
| 005 | >3.30E−5 | >3.30E−5 |
| 006 | 6.95E−6 | 1.64E−5 |
|  |  | >3.30E−5 |
| 007 | 2.85E−6 | 1.20E−5 |
| 008 | >3.30E−5 | >3.30E−5 |
| 009 | 9.89E−6 | 1.78E−5 |
| 010 | 6.62E−6 | 1.86E−5 |
| 011 | >3.30E−5 | >3.30E−5 |
| 012 | >3.30E−5 | >3.30E−5 |
| 013 | >3.30E−5 | >3.30E−5 |
| 014 | 2.66E−5 | >3.30E−5 |
| 015 | 2.57E−5 | 2.92E−5 |
| 016 | >3.30E−5 | >3.30E−5 |
| 017 | 1.47E−5 | >3.30E−5 |
|  |  | 3.19E−5 |
| 018 | 4.43E−6 | 9.64E−6 |
| 019 | 1.52E−6 | 5.16E−6 |
| 020 | >3.30E−5 | >3.30E−5 |
| 021 | 1.34E−5 | >3.30E−5 |
| 022 | 4.19E−6 | 1.76E−5 |
| 023 | 2.15E−6 | 7.46E−6 |
| 024 | 1.26E−5 | 2.51E−5 |
| 025 | 3.04E−6 | 1.11E−5 |
| 026 | 2.38E−5 | 2.02E−5 |
| 027 | 6.70E−6 | 2.04E−5 |
| 028 | >3.30E−5 | >3.30E−5 |
| 029 | >3.30E−5 | >3.30E−5 |
| 038 | 1.39E−5 | >3.30E−5 |
| 039 | 7.47E−6 | 2.48E−5 |
| 040 | 2.10E−5 | >3.30E−5 |

TABLE 3-continued

EC$_{50}$ values of selected examples in cellular caspase induction assay

| Example | Caspase SUDHL5 [M] (median) | Caspase SUDHL10 [M] (median) |
|---|---|---|
| 041 | 1.31E−5 | 1.82E−5 |
| 042 | >3.30E−5 | >3.30E−5 |
| 043 | 1.87E−5 | >3.30E−5 |
| 044 | 6.63E−6 | 2.53E−5 |
| 045 | >3.30E−5 | 3.27E−5 |
| 046 | 5.70E−6 | 1.70E−5 |
| 047 | 2.96E−6 | 6.66E−6 |
| 048 | 1.32E−5 | 1.78E−5 |
| 049 | 1.42E−5 | >3.30E−5 |
| 050 | 6.30E−6 | 1.88E−5 |
| 051 | >3.30E−5 | >3.30E−5 |
| 052 | 2.99E−5 | >3.30E−5 |
| 053 | 2.51E−6 | 5.67E−6 |
| 054 | 1.47E−6 | 6.64E−6 |
| 055 | >3.30E−5 | >3.30E−5 |
| 056 | >3.30E−5 | >3.30E−5 |
| 057 | 2.79E−5 | 2.47E−5 |
| 058 | >3.30E−5 | >3.30E−5 |
| 059 | 1.59E−5 | 2.77E−5 |
| 060 | 5.13E−6 | 8.54E−6 |
| 061 | 2.19E−5 | 1.86E−5 |
| 062 | 5.90E−6 | 1.81E−5 |
| 063 | 7.71E−6 | 1.65E−5 |
| 064 | 4.98E−6 | 1.75E−5 |
| 065 | >3.30E−5 | >3.30E−5 |
| 066 | >3.30E−5 | 2.90E−5 |
| 067 | >3.30E−5 | >3.30E−5 |
| 068 | 1.63E−6 | 1.19E−5 |
| 069 | >3.30E−5 | >3.30E−5 |
| 070 | 5.40E−6 | 8.62E−6 |
| 071 | 5.04E−6 | 1.11E−5 |
| 072 | 4.54E−6 | 4.91E−6 |
| 073 | 2.12E−6 | 2.94E−6 |
| 074 | >3.30E−5 | >3.30E−5 |
| 075 | 3.25E−6 | 6.36E−6 |
| 076 | 1.32E−6 | 3.54E−6 |
| 077 | >3.30E−5 | >3.30E−5 |
| 078 | 1.41E−5 | >3.30E−5 |
| 079 | 3.85E−6 | 9.85E−6 |
| 080 | >3.30E−5 | >3.30E−5 |
| 081 | 7.21E−6 | 1.90E−5 |
| 082 | 8.69E−6 | 3.05E−5 |
| 083 | >3.30E−5 | >3.30E−5 |
| 084 | 7.55E−6 | 1.49E−5 |
| 085 | 3.59E−6 | 1.55E−5 |
| 086 | >3.30E−5 | >3.30E−5 |
| 087 | >3.30E−5 | >3.30E−5 |
| 088 | 1.35E−5 | >3.30E−5 |
| 089 | 6.76E−6 | 2.41E−5 |
| 090 | >3.30E−5 | >3.30E−5 |
| 091 | 2.35E−5 | 3.18E−5 |
| 092 | 6.16E−6 | 2.02E−5 |
| 093 | 2.83E−6 | 6.64E−6 |
| 094 | >3.30E−5 | >3.30E−5 |
| 096 | 1.34E−6 | 3.97E−6 |
| 097 | >3.30E−5 | >3.30E−5 |
| 098 | >3.30E−5 | >3.30E−5 |
| 099 | 5.20E−6 | 1.28E−5 |
| 100 | >3.30E−5 | >3.30E−5 |
| 101 | 1.74E−6 | 3.43E−6 |
| 102 | 8.26E−6 | >3.30E−5 |
| 103 | 2.66E−6 | 8.71E−6 |
| 104 | >3.30E−5 | >3.30E−5 |
| 105 | 8.27E−6 | 2.39E−5 |
| 107 | 1.47E−6 | 4.91E−6 |
| 108 | >3.30E−5 | >3.30E−5 |
| 109 | >3.30E−5 | >3.30E−5 |
| 110 | 8.06E−6 | 2.60E−5 |
| 111 | >3.30E−5 | >3.30E−5 |
| 113 | | |
| 114 | 8.86E−6 | 1.77E−5 |
| 115 | >3.30E−5 | 3.05E−5 |
| 116 | >3.30E−5 | >3.30E−5 |
| 117 | >3.30E−5 | >3.30E−5 |
| 119 | 1.95E−5 | 2.25E−5 |
| 120 | 3.14E−5 | 1.84E−5 |
| 122 | 2.75E−5 | 2.18E−5 |
| 123 | 4.11E−6 | 7.36E−6 |
| 124 | 1.12E−5 | 1.34E−5 |
| 125 | 6.20E−6 | 1.40E−5 |
| 126 | 2.79E−5 | >3.30E−5 |
| 127 | >3.30E−5 | >3.30E−5 |
| 128 | >3.30E−5 | >3.30E−5 |
| 129 | >3.30E−5 | >3.30E−5 |
| 130 | 1.89E−5 | 2.44E−5 |
| | | >3.30E−5 |
| 131 | 2.59E−5 | 3.09E−5 |
| 132 | 2.54E−5 | >3.30E−5 |
| 133 | 1.76E−5 | 3.28E−5 |
| 134 | >3.30E−5 | >3.30E−5 |
| 135 | 1.21E−5 | >3.30E−5 |
| 136 | >3.30E−5 | >3.30E−5 |
| 137 | 1.29E−5 | 2.21E−5 |
| 138 | 1.11E−5 | >3.30E−5 |
| 139 | >3.30E−5 | >3.30E−5 |
| 140 | 1.49E−5 | 2.03E−5 |
| | | >3.30E−5 |
| 141 | 4.08E−6 | 7.30E−6 |
| 142 | 4.73E−6 | 1.25E−5 |
| 143 | 2.50E−5 | >3.30E−5 |
| 144 | 2.85E−6 | 3.91E−6 |
| 145 | 8.89E−7 | 2.57E−6 |
| 146 | >3.30E−5 | >3.30E−5 |
| 147 | 2.26E−6 | 7.48E−6 |
| 148 | 8.81E−7 | 3.48E−6 |
| 149 | >3.30E−5 | >3.30E−5 |
| 150 | >3.30E−5 | 2.80E−5 |
| 151 | 2.75E−5 | >3.30E−5 |
| 152 | >3.30E−5 | >3.30E−5 |
| 153 | 1.70E−6 | 5.12E−6 |
| 154 | 6.61E−7 | 1.70E−6 |
| 155 | >3.30E−5 | >3.30E−5 |
| 156 | >3.30E−5 | >3.30E−5 |
| 157 | >3.30E−5 | >3.30E−5 |
| 159 | 1.38E−5 | 2.86E−5 |
| | | >3.30E−5 |
| 160 | 1.79E−5 | >3.30E−5 |
| 161 | 1.50E−5 | >3.30E−5 |
| 162 | 5.35E−6 | 2.32E−5 |
| 163 | >3.30E−5 | >3.30E−5 |
| 164 | 1.20E−5 | >3.30E−5 |
| 165 | 5.25E−6 | 1.91E−5 |
| 166 | 3.07E−5 | >3.30E−5 |
| 169 | >3.30E−5 | >3.30E−5 |
| 170 | 5.36E−6 | 1.56E−5 |
| 171 | 6.48E−6 | 1.34E−5 |
| 172 | >3.30E−5 | >3.30E−5 |
| 177 | 2.33E−5 | >3.30E−5 |
| 178 | 1.28E−5 | >3.30E−5 |
| | | 3.00E−5 |
| 179 | 1.19E−5 | 2.69E−5 |
| 180 | 1.45E−5 | 2.82E−5 |
| 181 | 5.11E−6 | 1.61E−5 |
| 182 | >3.30E−5 | >3.30E−5 |
| 183 | 1.46E−5 | 5.89E−6 |
| 184 | 8.03E−7 | 2.90E−6 |
| 185 | >3.30E−5 | >3.30E−5 |
| 186 | 9.85E−6 | 1.86E−5 |
| 187 | 3.71E−6 | 1.33E−5 |
| 188 | 2.82E−6 | 7.76E−6 |
| 189 | >3.30E−5 | >3.30E−5 |
| 190 | 3.13E−6 | 7.26E−6 |
| 191 | 2.09E−6 | 7.16E−6 |
| 192 | >3.30E−5 | >3.30E−5 |
| 193 | 2.47E−6 | 8.35E−6 |
| 194 | 5.09E−6 | 1.51E−5 |
| 195 | >3.30E−5 | >3.30E−5 |
| 196 | 1.39E−6 | 2.85E−6 |

TABLE 3-continued

EC$_{50}$ values of selected examples in cellular caspase induction assay

| Example | Caspase SUDHL5 [M] (median) | Caspase SUDHL10 [M] (median) |
|---|---|---|
| 197 | 2.87E−5 | >3.30E−5 |
| 198 | 1.72E−6 | 6.94E−6 |
| 199 | 8.99E−7 | 3.46E−6 |
| 200 | >3.30E−5 | 1.88E−5 |
| 201 | 2.53E−6 | 8.57E−6 |
| 202 | 3.02E−5 | >3.30E−5 |
| 203 | 1.61E−6 | 7.45E−6 |
| 204 | 1.73E−6 | 6.09E−6 |
| 205 | 1.33E−6 | 2.49E−6 |
| 206 | 1.31E−5 | 1.75E−5 |
| 207 | 4.85E−6 | 1.14E−5 |
| 208 | 2.99E−6 | 1.40E−5 |
| 209 | >3.30E−5 | >3.30E−5 |
| 211 | >3.30E−5 | >3.30E−5 |
| 212 | 7.34E−6 | 1.99E−5 |
| 213 | >3.30E−5 | >3.30E−5 |
| 214 | 1.49E−5 | 2.07E−5 |
|  |  | >3.30E−5 |
| 215 | >3.30E−5 | >3.30E−5 |
| 216 | 1.00E−5 | 2.87E−5 |
| 217 | 3.50E−6 | 1.34E−5 |
| 218 | >3.30E−5 | >3.30E−5 |
| 219 | 1.28E−5 | >3.30E−5 |
| 220 | 1.01E−5 | 2.24E−5 |
|  |  | >3.30E−5 |
| 221 | >3.30E−5 | >3.30E−5 |
| 222 | 1.44E−5 | 1.82E−5 |
| 223 | 6.96E−6 | 2.62E−5 |
| 224 | >3.30E−5 | >3.30E−5 |
| 225 | 1.65E−5 | 1.96E−5 |
|  |  | >3.30E−5 |
| 226 | 3.15E−6 | 1.42E−5 |
| 227 | >3.30E−5 | >3.30E−5 |
| 228 | 1.39E−5 | 3.15E−5 |
| 229 | 5.55E−6 | 3.08E−5 |
| 230 | >3.30E−5 | >3.30E−5 |
| 231 | 1.73E−5 | 1.61E−5 |
| 232 | 9.57E−6 | 1.31E−5 |
| 233 | 2.53E−5 | >3.30E−5 |
| 234 | 3.01E−5 | 3.16E−5 |
| 235 | >3.30E−5 | >3.30E−5 |
| 236 | 1.12E−5 | 2.51E−5 |
| 237 | 5.55E−6 | 1.57E−5 |
| 238 | 4.88E−6 | 2.26E−5 |
| 239 | >3.30E−5 | >3.30E−5 |
| 240 | 1.16E−5 | >3.30E−5 |
| 241 | 3.75E−6 | 1.71E−5 |
| 242 | >3.30E−5 | >3.30E−5 |
| 243 | 7.09E−6 | 1.65E−5 |
| 244 | 2.69E−6 | 6.42E−6 |
| 247 | 5.21E−6 | 1.73E−5 |
| 248 | 3.17E−6 | 1.29E−5 |
| 249 | >3.30E−5 | >3.30E−5 |
| 250 | 1.09E−5 | 2.20E−5 |
| 251 | >3.30E−5 | >3.30E−5 |
| 252 | 4.79E−6 | 1.72E−5 |
| 253 | 6.70E−6 | 1.86E−5 |
| 254 | 3.01E−6 | 7.24E−6 |
| 255 | >3.30E−5 | >3.30E−5 |
| 256 | >3.30E−5 | >3.30E−5 |
| 257 | >3.30E−5 | >3.30E−5 |
| 258 | >3.30E−5 | >3.30E−5 |
| 259 | 3.13E−5 | >3.30E−5 |
| 260 | 1.02E−5 | 1.13E−5 |
| 261 | 1.77E−6 | 3.52E−6 |
| 262 | 2.26E−5 | >3.30E−5 |
| 263 | >3.30E−5 | >3.30E−5 |
| 264 | >3.30E−5 | >3.30E−5 |
| 265 | 2.71E−6 | 1.01E−5 |
| 266 | 1.79E−6 | 4.47E−6 |
| 267 | 1.14E−6 | 4.60E−6 |
| 268 | >3.30E−5 | >3.30E−5 |
| 269 | 4.83E−6 | 1.32E−5 |
| 270 | 6.18E−6 | 1.93E−5 |
| 271 | >3.30E−5 | >3.30E−5 |
| 272 | >3.30E−5 | 2.38E−5 |
| 273 | 5.37E−6 | 1.59E−5 |
| 274 | >3.30E−5 | 3.17E−5 |
| 275 | >3.30E−5 | 2.16E−5 |
| 276 | 4.07E−6 | 1.03E−5 |
| 277 | 1.40E−6 | 1.80E−6 |
| 278 | 2.63E−5 | >3.30E−5 |
| 279 | 2.55E−5 | 2.66E−5 |
| 280 | >3.30E−5 | 3.24E−5 |
| 281 | 1.45E−6 | 2.78E−6 |
| 282 | 3.85E−7 | 9.06E−7 |
| 283 | 3.07E−5 | >3.30E−5 |
|  | >3.30E−5 |  |
| 284 | 1.84E−6 | 3.73E−6 |
| 285 | 6.46E−7 | 1.41E−6 |
| 286 | 1.18E−5 | >3.30E−5 |
| 287 | 5.14E−6 | 1.30E−5 |
| 288 | 1.57E−6 | 5.85E−6 |
| 289 | >3.30E−5 | >3.30E−5 |
| 290 | 3.38E−6 | 1.36E−5 |
| 291 | 8.51E−6 | 3.20E−5 |
|  |  | >3.30E−5 |
| 292 | 6.71E−7 | 1.21E−6 |
| 293 | 3.09E−7 | 9.47E−7 |
| 294 | 6.95E−6 | 1.08E−5 |
| 295 | 1.70E−6 | 1.90E−5 |
| 296 | 3.23E−6 | 1.87E−5 |
| 297 | >3.30E−5 | >3.30E−5 |
| 298 | 8.78E−6 | 2.05E−5 |
| 299 | >3.30E−5 | >3.30E−5 |
| 300 | 3.93E−6 | 2.07E−5 |
| 301 | 1.19E−6 | 3.29E−6 |
| 302 | 6.74E−7 | 4.20E−6 |
| 303 | >3.30E−5 | >3.30E−5 |
| 304 | >3.30E−5 | >3.30E−5 |
| 305 |  |  |
| 306 |  |  |
| 307 | >3.30E−5 | >3.30E−5 |
| 308 | 7.18E−6 | >3.30E−5 |
| 309 | >3.30E−5 | >3.30E−5 |
| 310 | 2.74E−5 | 2.13E−5 |
| 311 | >3.30E−5 | >3.30E−5 |
| 312 |  |  |
| 313 | >3.30E−5 | >3.30E−5 |
| 314 | >3.30E−5 | >3.30E−5 |
| 315 | >3.30E−5 | 2.01E−5 |
| 316 | 1.77E−5 | >3.30E−5 |
| 317 | 2.45E−5 | >3.30E−5 |
| 318 | 2.64E−5 | >3.30E−5 |
| 319 | 1.84E−5 | 3.07E−5 |
| 320 | 1.38E−5 | 1.57E−5 |
|  |  | >3.30E−5 |
| 321 | 3.03E−5 | >3.30E−5 |
| 322 | >3.30E−5 | >3.30E−5 |
| 323 | >3.30E−5 | >3.30E−5 |
| 324 | >3.30E−5 | 3.21E−5 |
|  |  | >3.30E−5 |
| 325 | >3.30E−5 | >3.30E−5 |
| 326 | >3.30E−5 | >3.30E−5 |
| 327 | >3.30E−5 | >3.30E−5 |
| 328 | >3.30E−5 | >3.30E−5 |
| 329 | >3.30E−5 | >3.30E−5 |
| 330 | >3.30E−5 | >3.30E−5 |
| 331 | >3.30E−5 | >3.30E−5 |
| 332 | 1.89E−5 | >3.30E−5 |
| 333 | 1.73E−5 | >3.30E−5 |
| 334 | 1.69E−5 | 2.57E−5 |
| 335 | 2.72E−5 | >3.30E−5 |
| 336 | >3.30E−5 | >3.30E−5 |
| 337 | >3.30E−5 | >3.30E−5 |
| 338 | >3.30E−5 | >3.30E−5 |
| 339 | >3.30E−5 | >3.30E−5 |
| 340 | 2.11E−5 | >3.30E−5 |

TABLE 3-continued $EC_{50}$ values of selected examples in cellular caspase induction assay

| Example | Caspase SUDHL5 [M] (median) | Caspase SUDHL10 [M] (median) |
|---|---|---|
| 341 | >3.30E-5 | >3.30E-5 |
| 342 | 2.50E-5 | >3.30E-5 |
| 343 | 2.97E-5 | >3.30E-5 |
| 344 | >3.30E-5 | >3.30E-5 |
| 345 | 7.02E-6 | 1.28E-5 |
| 346 | 2.51E-5 | 3.24E-5 |
| 347 | >3.30E-5 | >3.30E-5 |
| 348 | 1.46E-5 | 1.68E-5 |
| 349 | 3.10E-5 | >3.30E-5 |
| 350 | 2.43E-5 | >3.30E-5 |
|  | >3.30E-5 |  |
| 351 | >3.30E-5 | >3.30E-5 |
| 352 | >3.30E-5 | >3.30E-5 |
| 353 | >3.30E-5 | >3.30E-5 |
| 354 | >3.30E-5 | >3.30E-5 |
| 355 | >3.30E-5 | >3.30E-5 |
| 356 | 2.78E-5 | >3.30E-5 |
|  | >3.30E-5 |  |
| 357 | >3.30E-5 | >3.30E-5 |
| 358 | >3.30E-5 | >3.30E-5 |
| 359 | >3.30E-5 | >3.30E-5 |
| 360 | 3.26E-5 | >3.30E-5 |
| 361 | 1.01E-5 | >3.30E-5 |
| 362 | 2.62E-5 | >3.30E-5 |
| 363 | 2.02E-5 | 2.31E-5 |
| 364 | 2.42E-5 | >3.30E-5 |

Induction of Cytotoxicity Upon Treatment of Cells with Selected Compounds

In principle, compounds that induce apoptosis will concomitantly induce cell cytotoxicity. Therefore, cytotoxicity assays were run in parallel in SUDHL5 and SUDHL10 cells.

The different cell lines were plated in culture medium (RPMI 1640 [GIBCO #22400-089]supplemented with 10% Fetal Bovine Serum) at a density of 3,300 cells in 30 μl/well in a sterile, solid black, flat bottom, polystyrene, TC-treated 384-well microplate (Corning #3571) using Multidrop Combi Reagent Dispenser. As a control, medium without cells was also added to the plate. Cells were incubated in a humidified incubator at 37° C. overnight. On the next day, the cells were treated with compounds (stock solution, 10 mM in DMSO) using the HP D300 Digital Dispenser in a concentration range of 3.3×10e-5 M (33 μM) to 5×10e-9 M (5 nM) in a single-dot curve with at least 16 dilutions and a DMSO concentration of 0.33%. Rim wells were excluded. The cells were incubated for 5 h hours in a humidified incubator at 37° C. After this incubation, 30 μl of CellTiter-Glo® Luminescent Cell Viability reagent (Promega, G7573) was added to each well using the Multidrop Combi Reagent Dispenser, followed by 15 min incubation on a shaker at room temperature. Finally, luminescence was read at 0.1 ms, with a gain of 3000 using the PHERAstar FS microplate reader (BMG Labtech).

For the evaluation of the results, each value was normalized to DMSO-only treated cells (every value was divided by the mean of the DMSO control). The Bella DRC Master Sheet was used to calculate IC50s, with fixed CI=0 and C0=1.

Assessment of the Anti-Proliferative Effect of Compounds in Different Cell Lines The impact of compounds on the proliferation of different cell lines was assessed using the CellTiter-Glo® Luminescent Cell Viability reagent from Promega (G7573). Of note, SUDHL10 and SUDHL5 (DLBCL), NCI-H929 (Multiple Myeloma), A2780 (ovarian carcinoma) as well as MV-4-11 (AML) cells are sensitive to MCL-1 inhibition.

The different cell lines were plated in culture medium (RPMI 1640 [Biochrom; #FG 1215]supplemented with 10% Fetal Calf Serum [Biochrom; #S 0415]) at a density of 3,300 cells (for suspension cells) or 800 cells (for adherent cells) in 30 μl/well in a sterile, solid black, flat bottom, polystyrene, TC-treated 384-well microplate (Corning #3571) using Multidrop Combi Reagent Dispenser. In parallel, cells were plated in a reference (day 0) plate for time zero determination. Cells were incubated in a humidified incubator at 37° C. overnight.

On the next day, cells were treated with compounds (stock solution, 10 mM in DMSO) using the HP D300 Digital Dispenser in a concentration range of 3.3×10e-5 M (33 μM) to 5×10e-9 M (5 nM) in a single-dot curve with at least 16 dilutions and a DMSO concentration of 0.33%. Rim wells were excluded. The cells were incubated for 72 h hours in a humidified incubator at 37° C. The day 0 plate was measured by adding 30 μL/well of CTG solution (CellTiter-Glo® Luminescent Cell Viability reagent, Promega G7573) to time zero wells in the reference plate followed by a 10 minutes incubation and luminescence reading at 0.1 ms. using the PHERAstar FS microplate reader (BMG Labtech).

After 72 h incubation, the treated plates were measured in the same way as the day 0 plate mentioned above. The Bella DRC Master Sheet was used to calculate IC50s, with CI=day 0 values and C0=DMSO control values.

Table 2 shows the results of the proliferation assays.

TABLE 2

$IC_{50}$ values of selected examples in cellular cytotoxicity induction assay and antiproliferation assay

| Example | Cytotox SUDHL5 [M] (median) | Cytotox SUDHL10 [M] (median) | Antiproli SUDHL5 [M] (median) | Antiproli SUDHL10 [M] (median) |
|---|---|---|---|---|
| 1-1 | >3.30E-5 | >3.30E-5 |  |  |
| 1-2 | >3.30E-5 | >3.30E-5 |  |  |
| 1-3 | 2.68E-6 | 2.64E-6 | 1.27E-6 | 1.90E-6 |
| 1-4 | 1.83E-5 | 7.42E-6 | 2.43E-6 | 1.73E-6 |
| 1-5 | 3.20E-6 | 4.77E-6 | 7.67E-7 | 1.02E-6 |
| 1-6 | 1.15E-5 | >3.30E-5 | 1.37E-6 |  |
| 1-7 | >3.30E-5 | 8.17E-6 | 1.63E-6 | >3.30E-5 |
| 1-8 | 8.33E-7 | 1.07E-6 | 9.83E-7 | 1.44E-6 |
| 1-9 | 9.46E-6 | 9.08E-6 | 3.37E-6 | 1.17E-5 |
| 1-10 | 4.33E-7 | 4.74E-7 | 1.26E-6 | 1.35E-6 |
| 1-11 | 8.89E-7 | 1.03E-6 | 7.61E-7 | 9.28E-7 |
| 1-12 | 1.73E-5 | 1.43E-5 | 5.72E-6 | 8.96E-6 |
| 1-13 | 4.10E-7 | 4.36E-7 | 7.58E-7 | 1.38E-6 |
| 1-15 | 1.38E-6 | 1.94E-6 | 1.36E-6 | 1.56E-6 |
| 1-16 | >3.30E-5 | >3.30E-5 | 8.21E-6 | 5.63E-6 |
| 1-17 | 4.36E-6 | 6.88E-6 | 2.99E-6 | 4.25E-6 |
| 1-18 | 1.75E-6 | 2.29E-6 | 9.33E-7 | 1.33E-6 |
| 1-19 | 2.70E-5 | 2.52E-5 | 5.87E-6 |  |
| 1-20 | 2.11E-6 | 3.06E-6 | 1.25E-6 | 2.19E-6 |
| 1-21 | 2.31E-6 | 3.26E-6 | 2.41E-6 | 2.49E-6 |
| 1-22 | 1.37E-6 | 2.70E-6 | 1.58E-6 | 2.19E-6 |
| 1-23 | 2.45E-5 | >3.30E-5 | 1.15E-5 | 5.59E-6 |
| 1-24 | 2.23E-6 | 4.33E-6 | 4.70E-6 | 6.52E-6 |
| 1-25 | 2.68E-6 | 4.02E-6 | 2.86E-5 |  |
| 1-26 | >3.30E-5 | >3.30E-5 |  |  |
| 1-27 | 3.53E-6 | 8.44E-6 | 2.95E-6 | 6.30E-6 |
| 1-28 | >3.30E-5 | >3.30E-5 |  |  |
| 1-29 | 3.29E-6 | 6.87E-6 | 3.26E-6 |  |
| 1-30 | >3.30E-5 | >3.30E-5 | 1.04E-5 | 1.36E-5 |
| 1-31 | 4.60E-6 | 1.61E-5 | 3.12E-6 | 4.55E-6 |
| 1-32 | >3.30E-5 | 3.23E-5 | 1.63E-5 | 1.18E-5 |
| 1-33 | 7.47E-6 | 2.19E-5 | 9.78E-6 | 1.83E-5 |
| 1-34 | 3.36E-6 | 4.53E-6 | 1.31E-5 | >3.30E-5 |

TABLE 2-continued

IC$_{50}$ values of selected examples in cellular cytotoxicity induction assay and antiproliferation assay

| Example | Cytotox SUDHL5 [M] (median) | Cytotox SUDHL10 [M] (median) | Antiproli SUDHL5 [M] (median) | Antiproli SUDHL10 [M] (median) |
|---|---|---|---|---|
| 1-35 | 2.02E−5 | 1.18E−5 | 2.56E−5 | 3.25E−5 |
| 1-36 | 3.69E−6 | 1.40E−5 | 2.63E−6 | 6.09E−6 |
| 1-37 | 1.92E−6 | 8.41E−6 | 2.54E−6 | 3.00E−6 |
| 1-38 | >3.30E−5 | >3.30E−5 | 2.30E−5 | 1.49E−5 |
| 1-39 | 2.05E−6 | 1.82E−6 | 5.77E−6 | 2.14E−5 |
| 1-40 | 1.69E−5 | 2.30E−5 | 5.80E−6 | 1.93E−6 |
| 1-41 | 7.69E−7 | 1.52E−6 |  | 1.10E−5 |
| 1-42 | 1.19E−5 | >3.30E−5 | 7.08E−6 | 1.64E−5 |
| 1-43 | 6.90E−6 | 1.48E−5 | 9.58E−6 | 8.34E−6 |
| 1-44 | 1.26E−5 | >3.30E−5 | 6.96E−6 | 7.73E−6 |
|  |  | 1.03E−5 |  |  |
| 1-46 | 1.53E−6 | 2.29E−6 | 9.89E−7 | 8.61E−7 |
| 1-47 | 1.08E−5 | 1.32E−5 | 3.91E−6 | 3.99E−6 |
| 1-49 | 3.30E−5 | 2.50E−5 | 1.22E−5 | 9.58E−6 |
| 1-50 | 5.74E−6 | 1.26E−5 | 5.52E−6 | 9.59E−6 |
| 1-52 | 3.15E−5 | 2.71E−5 | 1.25E−5 | 7.55E−6 |
| 1-53 | 6.49E−6 | 7.89E−6 | 1.36E−5 | 7.20E−6 |
| 1-55 | >3.30E−5 | 1.73E−5 | 1.34E−5 | 9.09E−6 |
| 1-56 | 5.72E−6 | 2.95E−5 | >3.30E−5 | >3.30E−5 |
| 1-58 | 1.20E−5 | 2.14E−5 | 1.17E−5 | 7.32E−6 |
| 1-59 | 1.24E−5 | 2.01E−5 | 1.06E−5 | 6.64E−6 |
| 1-60 | 2.10E−5 | 3.27E−5 | 1.30E−5 | 9.02E−6 |
| 1-61 | 1.33E−5 | 2.11E−5 | 5.41E−6 |  |
| 1-62 | 1.20E−5 | 1.96E−5 | 1.02E−5 | 3.36E−6 |
| 1-63 | 6.23E−6 | 7.04E−6 | 3.37E−6 | 7.77E−6 |
| 1-64 | 2.65E−5 | >3.30E−5 | 1.20E−5 | 7.40E−6 |
|  | >3.30E−5 |  |  |  |
|  | >3.30E−5 |  |  |  |
|  | 3.12E−6 |  |  |  |
|  | 2.47E−5 |  |  |  |
| 1-65 | >3.30E−5 | 3.13E−5 |  | 3.71E−6 |
| 1-66 | 5.49E−6 | 1.45E−5 | 3.95E−6 | 9.23E−6 |
| 1-67 | 1.22E−5 | 2.29E−5 | 9.80E−6 | 2.95E−6 |
| 1-68 | >3.30E−5 | >3.30E−5 | 1.39E−5 | 1.76E−5 |
| 1-69 | 2.71E−5 | >3.30E−5 | >3.30E−5 | >3.30E−5 |
| 1-70 | >3.30E−5 | 2.78E−5 |  | 1.31E−5 |
| 1-71 | 1.98E−6 | >3.30E−5 |  | 2.13E−5 |
|  | >3.30E−5 |  |  |  |
| 1-72 | 8.53E−6 | 1.98E−5 | 2.38E−5 | 1.37E−5 |
| 1-73 | 7.00E−6 | 1.53E−5 | 3.68E−6 | 9.04E−6 |
| 1-74 | 9.82E−6 | 1.42E−5 | 9.62E−6 | 1.17E−6 |
| 1-75 | 7.17E−6 | 1.90E−5 | 1.56E−5 | 1.12E−5 |
|  | >3.30E−5 | >3.30E−5 |  |  |
| 1-76 | >3.30E−5 | >3.30E−5 | 2.10E−5 | 1.13E−5 |
| 1-77 | >3.30E−5 | >3.30E−5 | 2.96E−5 | 1.52E−5 |
| 1-78 | >3.30E−5 | >3.30E−5 | 1.79E−5 | 1.08E−5 |
| 1-79 | >3.30E−5 | 3.09E−5 |  |  |
| 1-80 | >3.30E−5 | >3.30E−5 |  |  |
| 1-81 | >3.30E−5 | >3.30E−5 | >3.30E−5 | 2.78E−5 |
| 1-82 | >3.30E−5 | >3.30E−5 | 2.77E−5 | 1.42E−5 |
| 1-83 | >3.30E−5 | >3.30E−5 | 2.06E−5 | 1.12E−5 |
| 1-84 | >3.30E−5 | >3.30E−5 | 1.18E−5 | 8.37E−6 |
| 1-85 | >3.30E−5 | >3.30E−5 | 2.50E−5 | 1.03E−5 |
| 1-86 | >3.30E−5 | >3.30E−5 | 1.96E−5 | 9.45E−6 |
| 1-88 | 5.90E−6 | 6.19E−6 | >3.30E−5 | >3.30E−5 |
| 1-89 | 1.39E−5 | 1.14E−5 | >3.30E−5 | 2.02E−5 |
| 1-91 | 5.99E−6 | 9.23E−6 | 2.48E−6 | 4.30E−6 |
| 1-92 | 2.90E−6 | 5.77E−6 | 3.21E−6 | 3.83E−6 |
| 1-93 | >3.30E−5 | >3.30E−5 |  |  |
| 1-94 | >3.30E−5 | >3.30E−5 |  |  |
| 1-95 | 1.98E−5 | >3.30E−5 | 4.80E−6 |  |
| 1-96 | 1.84E−5 | 2.95E−5 | >3.30E−5 | 1.44E−5 |
| 1-97 | >3.00E−5 | >3.00E−5 | 1.18E−5 | 7.07E−6 |
| 1-99 | 1.30E−5 | 1.93E−5 | 8.76E−6 | 4.63E−6 |
| 1-100 | >3.30E−5 | >3.30E−5 | 9.42E−6 | 6.21E−6 |
|  |  | 3.29E−5 |  |  |
| 1-101 | >3.30E−5 | >3.30E−5 |  | 1.05E−5 |
| 1-103 | 3.97E−6 | 1.27E−5 | 3.92E−6 | 1.02E−5 |
| 1-104 | 7.21E−6 | 1.78E−5 | 3.62E−6 |  |
| 1-106 | 1.49E−5 | 1.89E−5 | 4.15E−6 |  |
| 1-107 | 1.61E−5 | 2.89E−5 |  |  |
|  | >3.30E−5 | >3.30E−5 |  |  |
| 1-109 | 8.44E−6 | 1.48E−5 | 4.55E−6 | 4.08E−6 |
| 1-110 | 1.53E−5 | 1.69E−5 | 4.04E−6 | 2.58E−6 |
| 1-112 | 3.30E−5 | 5.46E−6 | 2.72E−6 |  |
| 1-113 | 1.31E−5 | 2.06E−5 | 1.05E−5 |  |
| 1-115 | >3.30E−5 | >3.30E−5 | 2.13E−5 | 1.24E−5 |
| 1-116 | 1.32E−5 | >3.30E−5 | 3.25E−6 | 1.18E−5 |
| 1-118 | >3.30E−5 | >3.30E−5 |  | 2.20E−5 |
| 1-119 | >3.30E−5 | >3.30E−5 |  | >3.30E−5 |
| 1-120 | >3.30E−5 | >3.30E−5 |  | >3.30E−5 |
| 1-121 | 3.07E−6 | 6.21E−6 | 5.79E−6 | 5.07E−6 |
| 1-122 | >3.30E−5 | >3.30E−5 |  | >3.30E−5 |
| 001 | 2.61E−5 | >3.30E−5 | >3.30E−5 | 9.57E−6 |
| 002 | 2.12E−5 | 3.18E−5 | 1.42E−5 | 6.26E−6 |
| 003 | >3.30E−5 | >3.30E−5 | >3.30E−5 | 1.54E−5 |
| 004 | 1.47E−5 | 2.57E−5 | 9.77E−6 | 2.04E−6 |
| 005 | >3.30E−5 | >3.30E−5 |  | >3.30E−5 |
| 006 | 7.28E−6 | 1.99E−5 | 3.22E−6 | 4.99E−6 |
|  |  | >3.30E−5 |  |  |
| 007 | 3.54E−6 | 6.00E−6 | 5.16E−6 | 3.10E−6 |
| 008 | >3.30E−5 | >3.30E−5 | 2.59E−5 | 1.55E−5 |
| 009 | 1.11E−5 | 2.04E−5 | 3.62E−6 | 8.05E−6 |
| 010 | 7.40E−6 | 2.27E−5 | 1.27E−5 | 3.91E−6 |
| 011 | >3.30E−5 | >3.30E−5 | 2.02E−5 | 1.18E−5 |
| 012 | 3.14E−5 | >3.30E−5 |  | 7.15E−6 |
| 013 | >3.30E−5 | >3.30E−5 |  | 4.83E−6 |
| 014 | 2.27E−5 | >3.30E−5 | 2.23E−5 | 7.24E−6 |
| 015 | 2.10E−5 | 2.87E−5 | 1.13E−5 | 8.48E−6 |
| 016 | >3.30E−5 | >3.30E−5 |  | >3.30E−5 |
| 017 | 1.36E−5 | >3.30E−5 | 6.09E−6 | 2.17E−5 |
| 018 | 3.77E−6 | 9.04E−6 | 2.32E−6 | 7.88E−6 |
| 019 | 1.68E−6 | 3.76E−6 | 3.65E−6 | 4.45E−6 |
| 020 | 2.31E−5 | >3.30E−5 | 1.72E−5 | 6.75E−6 |
| 021 | 1.82E−5 | >3.30E−5 | 2.40E−5 | 5.25E−6 |
| 022 | 4.08E−6 | 2.02E−5 | 7.53E−6 | 6.52E−6 |
| 023 | 1.84E−6 | 5.85E−6 | 4.32E−6 | 9.57E−6 |
| 024 | 1.32E−5 | 3.23E−5 | 1.27E−5 | 5.57E−6 |
|  |  | >3.30E−5 |  |  |
| 025 | 2.98E−6 | 8.77E−6 | 6.44E−6 | 4.29E−6 |
| 026 | 2.41E−5 | 2.58E−5 | 8.59E−6 |  |
| 027 | 8.54E−6 | 2.59E−5 | 9.27E−6 | 7.34E−6 |
| 028 | >3.30E−5 | >3.30E−5 | 2.97E−5 | 1.81E−5 |
| 029 | >3.30E−5 | >3.30E−5 | 1.82E−5 | 1.38E−5 |
| 038 | 1.46E−5 | >3.30E−5 | 1.64E−5 | 1.46E−5 |
| 039 | 8.59E−6 | 2.97E−5 | 1.11E−5 | 1.30E−5 |
| 040 | 1.66E−5 | >3.30E−5 | 1.33E−5 | 3.25E−6 |
| 041 | 1.02E−5 | 1.46E−5 | 9.88E−6 |  |
| 042 | >3.30E−5 | 3.00E−5 | 4.97E−6 |  |
| 043 | 1.79E−5 | >3.30E−5 | 1.05E−5 | 4.93E−6 |
| 044 | 6.01E−6 | 2.34E−5 | 7.61E−6 | 1.10E−5 |
| 045 | 2.59E−5 | 2.89E−5 | 5.73E−6 |  |
| 046 | 6.09E−6 | 2.33E−5 | 6.27E−6 | 3.94E−6 |
| 047 | 3.22E−6 | 6.49E−6 | 4.41E−6 | 3.61E−6 |
| 048 | 1.19E−5 | 1.71E−5 | 4.84E−6 |  |
| 049 | 1.13E−5 | 3.14E−5 | 1.10E−5 | 6.98E−6 |
| 050 | 4.45E−6 | 9.61E−6 | 1.41E−5 | 7.75E−6 |
| 051 | 3.00E−5 | 2.02E−5 | 8.91E−6 | 4.39E−6 |
| 052 | 2.68E−6 | 2.97E−5 | 2.15E−6 | 1.30E−5 |
| 053 | 3.00E−6 | 7.75E−6 | 1.47E−6 | 7.88E−6 |
| 054 | 1.61E−6 | 4.68E−6 | 8.08E−7 | 2.44E−6 |
| 055 | >3.30E−5 | >3.30E−5 |  | 1.17E−5 |
| 056 | >3.30E−5 | >3.30E−5 |  | 2.00E−5 |
| 057 | 2.50E−5 | 2.39E−5 | 1.04E−5 | 1.21E−5 |
| 058 | >3.30E−5 | >3.30E−5 |  | 2.05E−5 |
| 059 | 2.54E−6 | 1.90E−5 | 6.96E−6 | 1.99E−5 |
| 060 | 4.30E−6 | 7.87E−6 | 1.79E−6 | 1.16E−5 |
| 061 | 1.63E−5 | 1.75E−5 | 8.04E−6 | 8.37E−6 |
| 062 | 6.67E−6 | 2.43E−5 | 4.17E−6 | 4.49E−6 |
| 063 | 7.73E−6 | 1.16E−5 | 3.98E−6 | 5.35E−6 |
| 064 | 7.53E−6 | 2.59E−5 | 1.12E−5 |  |

TABLE 2-continued

IC$_{50}$ values of selected examples in cellular cytotoxicity induction assay and antiproliferation assay

| Example | Cytotox SUDHL5 [M] (median) | Cytotox SUDHL10 [M] (median) | Antiproli SUDHL5 [M] (median) | Antiproli SUDHL10 [M] (median) |
|---|---|---|---|---|
| 065 | >3.30E-5 | >3.30E-5 | 2.61E-5 | |
| 066 | >3.30E-5 | >3.30E-5 | | 6.96E-6 |
| 067 | >3.30E-5 | >3.30E-5 | | 5.38E-6 |
| 068 | 2.25E-6 | 5.02E-6 | 2.53E-6 | 1.87E-6 |
| 069 | >3.30E-5 | >3.30E-5 | >3.30E-5 | 2.11E-5 |
| 070 | 4.28E-6 | 9.59E-6 | 2.00E-6 | 8.58E-6 |
| 071 | 7.45E-6 | 1.76E-5 | 6.23E-6 | 2.59E-6 |
| 072 | 3.43E-6 | 6.12E-6 | 1.11E-6 | 5.65E-6 |
| 073 | 1.79E-6 | 3.67E-6 | 3.23E-6 | 6.86E-6 |
| 074 | 1.20E-5 | 1.17E-5 | 1.14E-5 | 1.26E-5 |
| 075 | 3.66E-6 | 8.23E-6 | 3.21E-6 | 2.63E-6 |
| 076 | 1.63E-6 | 3.63E-6 | 2.53E-6 | 4.49E-6 |
| 077 | >3.30E-5 | >3.30E-5 | 2.73E-5 | 1.17E-5 |
| 078 | 9.93E-6 | >3.30E-5 | 7.96E-6 | 1.44E-5 |
| 079 | 4.24E-6 | 8.83E-6 | 6.70E-6 | |
| 080 | >3.30E-5 | >3.30E-5 | 1.56E-5 | |
| 081 | 7.06E-6 | 2.26E-5 | 9.61E-6 | 9.62E-6 |
| 082 | 8.19E-6 | >3.30E-5 | 1.81E-5 | 7.79E-6 |
| 083 | >3.30E-5 | >3.30E-5 | 2.68E-6 | 1.47E-5 |
| 084 | 6.60E-6 | 2.06E-5 | 7.19E-6 | 3.87E-6 |
| 085 | 3.91E-6 | 1.97E-5 | 6.22E-6 | 3.08E-6 |
| 086 | 3.15E-5 | >3.30E-5 | 1.72E-5 | 7.00E-6 |
| 087 | >3.30E-5 | >3.30E-5 | >3.30E-5 | 1.41E-5 |
| 088 | 1.10E-5 | >3.30E-5 | 1.76E-5 | 2.67E-5 |
| 089 | 7.00E-6 | 3.00E-5 | 1.71E-5 | |
| 090 | >3.30E-5 | >3.30E-5 | 1.50E-5 | |
| 091 | 1.48E-5 | 1.89E-5 | 6.92E-6 | |
| 092 | 6.75E-6 | 2.23E-5 | 8.25E-6 | 2.06E-6 |
| 093 | 2.10E-6 | 7.20E-6 | 3.38E-6 | 1.03E-5 |
| 094 | >3.30E-5 | >3.30E-5 | 3.11E-5 | 1.64E-5 |
| 096 | 1.09E-6 | 3.70E-6 | 2.32E-6 | 7.13E-6 |
| 097 | 3.05E-5 | >3.30E-5 | 2.25E-5 | 1.21E-5 |
| 098 | 2.94E-5 | >3.30E-5 | 2.74E-5 | 1.15E-5 |
| 099 | 3.86E-6 | 1.75E-5 | 8.47E-6 | 1.08E-5 |
| 100 | >3.30E-5 | >3.30E-5 | 1.61E-5 | 1.71E-5 |
| 101 | 2.03E-6 | 4.00E-6 | 1.32E-6 | 4.47E-6 |
| 102 | 6.12E-6 | >3.30E-5 | 1.32E-5 | |
| 103 | 3.55E-6 | 8.83E-6 | 4.28E-6 | 7.52E-6 |
| 104 | >3.30E-5 | >3.30E-5 | 2.00E-5 | 1.02E-5 |
| 105 | 7.19E-6 | 1.92E-5 | 1.01E-5 | 9.89E-6 |
| 107 | 1.73E-6 | 4.65E-6 | 3.82E-6 | 5.32E-6 |
| 108 | >3.30E-5 | >3.30E-5 | 1.51E-5 | 1.17E-5 |
| 109 | >3.30E-5 | >3.30E-5 | 1.56E-5 | |
| 110 | 6.54E-6 | 2.37E-5 | 1.24E-5 | 1.72E-5 |
| 111 | >3.30E-5 | >3.30E-5 | >3.30E-5 | 5.45E-6 |
| 113 | 6.84E-6 | 7.90E-6 | | 6.99E-6 |
| 114 | 6.61E-6 | 8.59E-6 | 3.28E-6 | 5.31E-6 |
| 115 | 1.13E-5 | 1.49E-5 | | 4.86E-6 |
| 116 | >3.30E-5 | >3.30E-5 | | >3.30E-5 |
| 117 | >3.30E-5 | >3.30E-5 | | >3.30E-5 |
| 119 | 2.85E-5 | >3.30E-5 | 1.35E-5 | 2.00E-5 |
| 120 | 3.21E-5 | >3.30E-5 | 1.08E-5 | 1.40E-5 |
| 122 | 2.92E-5 | >3.30E-5 | 1.03E-5 | 1.17E-5 |
| 123 | 3.13E-6 | 2.10E-5 | 2.28E-6 | 1.01E-5 |
| 124 | 1.71E-5 | 1.61E-5 | 6.64E-6 | 3.05E-6 |
| 125 | 6.30E-6 | 1.39E-5 | 2.53E-6 | 7.66E-6 |
| 126 | 2.73E-5 | >3.30E-5 | 1.68E-5 | 1.51E-5 |
| 127 | >3.30E-5 | >3.30E-5 | | 9.32E-6 |
| 128 | >3.30E-5 | >3.30E-5 | | 1.29E-5 |
| 129 | >3.30E-5 | >3.30E-5 | | 6.99E-6 |
| 130 | 1.53E-5 | 1.71E-5 | 1.17E-5 | 6.42E-6 |
| | | >3.30E-5 | | |
| 131 | 1.46E-5 | 2.88E-5 | 1.17E-5 | 1.16E-5 |
| 132 | 2.81E-5 | 1.69E-5 | 1.78E-5 | 6.00E-6 |
| 133 | 1.84E-5 | 2.95E-5 | 1.62E-6 | 4.25E-6 |
| 134 | >3.30E-5 | >3.30E-5 | 2.14E-6 | 1.63E-6 |
| 135 | 1.06E-5 | >3.30E-5 | 7.26E-6 | 1.01E-5 |
| 136 | >3.30E-5 | >3.30E-5 | | 8.90E-6 |
| 137 | 8.98E-6 | 3.06E-5 | 2.67E-6 | 5.90E-6 |
| 138 | 1.13E-5 | >3.30E-5 | | 1.16E-5 |
| 139 | >3.30E-5 | >3.30E-5 | | 2.67E-5 |
| 140 | 1.67E-5 | 2.30E-5 | 1.17E-5 | 1.79E-5 |
| 141 | | >3.30E-5 | | |
| 141 | 3.66E-6 | 7.87E-6 | 1.39E-6 | 1.00E-5 |
| 142 | 6.07E-6 | 1.34E-5 | 8.25E-6 | 1.89E-5 |
| 143 | 1.36E-5 | 2.69E-5 | 1.44E-5 | 2.02E-5 |
| 144 | 2.55E-6 | 5.02E-6 | 1.33E-6 | 5.89E-6 |
| 145 | 1.40E-6 | 2.40E-6 | 1.85E-6 | 4.25E-6 |
| 146 | 1.66E-6 | 2.67E-6 | 1.93E-6 | 1.05E-5 |
| 147 | 2.80E-6 | 9.53E-6 | 3.06E-6 | 3.93E-6 |
| 148 | 9.08E-7 | 2.40E-6 | 2.56E-6 | 5.87E-6 |
| 149 | >3.30E-5 | >3.30E-5 | 1.26E-5 | |
| 150 | 2.69E-5 | >3.30E-5 | 2.11E-5 | |
| 151 | 1.91E-5 | >3.30E-5 | >3.30E-5 | 2.01E-5 |
| 152 | >3.30E-5 | >3.30E-5 | >3.30E-5 | 1.76E-5 |
| 153 | 1.65E-6 | 5.10E-6 | 7.96E-7 | 4.09E-6 |
| 154 | 1.08E-6 | 2.03E-6 | 2.26E-6 | 4.11E-6 |
| 155 | >3.30E-5 | >3.30E-5 | | 8.34E-6 |
| 156 | >3.30E-5 | >3.30E-5 | >3.30E-5 | 2.23E-5 |
| 157 | >3.30E-5 | >3.30E-5 | >3.30E-5 | >3.30E-5 |
| 159 | 1.76E-5 | 3.05E-5 | 1.75E-5 | 2.98E-5 |
| | | >3.30E-5 | | >3.30E-5 |
| 160 | 2.05E-5 | >3.30E-5 | 1.14E-5 | 1.49E-5 |
| | | | >3.30E-5 | |
| 161 | 1.06E-5 | >3.30E-5 | 1.36E-6 | 1.26E-5 |
| 162 | 8.92E-6 | 2.30E-5 | 6.96E-6 | |
| 163 | 2.93E-5 | >3.30E-5 | 1.17E-5 | 6.35E-6 |
| 164 | 9.23E-6 | 3.07E-5 | 1.60E-5 | 1.69E-5 |
| 165 | 5.71E-6 | 2.37E-5 | 1.13E-5 | |
| 166 | 2.81E-6 | >3.30E-5 | 1.26E-5 | |
| 169 | 1.74E-5 | 2.01E-5 | 2.68E-5 | 2.02E-5 |
| | >3.30E-5 | >3.30E-5 | | |
| 170 | 6.94E-6 | 2.00E-5 | 1.01E-5 | 4.36E-6 |
| 171 | 5.08E-6 | 1.39E-5 | 2.24E-6 | 6.45E-6 |
| 172 | >3.30E-5 | >3.30E-5 | | 1.53E-5 |
| 177 | 2.14E-5 | >3.30E-5 | >3.30E-5 | |
| 178 | 1.30E-5 | >3.30E-5 | 9.37E-6 | >3.30E-5 |
| | | | | 2.21E-5 |
| 179 | 1.22E-5 | >3.30E-5 | 1.48E-5 | >3.30E-5 |
| | | 3.15E-5 | | 1.37E-5 |
| 180 | 1.10E-5 | 3.11E-5 | 7.77E-6 | 8.97E-6 |
| 181 | 6.68E-6 | 1.67E-5 | 6.23E-6 | 8.23E-6 |
| 182 | >3.30E-5 | >3.30E-5 | 1.91E-5 | 6.02E-6 |
| 183 | 1.88E-6 | 5.55E-6 | 2.43E-6 | 4.14E-6 |
| 184 | 8.82E-7 | 2.94E-6 | 1.34E-6 | 1.20E-6 |
| 185 | 2.75E-5 | >3.30E-5 | 1.98E-5 | 8.53E-6 |
| 186 | 1.14E-5 | 2.61E-5 | 8.69E-6 | 1.40E-5 |
| 187 | 3.85E-6 | 1.07E-5 | 7.27E-6 | 1.41E-5 |
| 188 | 2.95E-6 | 6.61E-6 | 3.39E-6 | 9.83E-6 |
| 189 | 2.86E-5 | >3.30E-5 | 1.09E-5 | 2.01E-5 |
| 190 | 3.85E-6 | 9.19E-6 | 2.35E-6 | 5.34E-6 |
| 191 | 1.87E-6 | 5.01E-6 | 3.23E-6 | 4.64E-6 |
| 192 | >3.30E-5 | >3.30E-5 | 2.03E-5 | 9.22E-6 |
| 193 | 2.30E-6 | 7.65E-6 | 4.45E-6 | 7.14E-6 |
| 194 | 5.46E-6 | 1.63E-5 | 7.95E-6 | 6.28E-6 |
| 195 | >3.30E-5 | >3.30E-5 | 5.84E-6 | 1.32E-5 |
| 196 | 1.36E-6 | 2.92E-6 | 1.45E-6 | 2.19E-6 |
| 197 | 1.93E-5 | 1.55E-5 | 1.78E-5 | 8.15E-6 |
| 198 | 2.05E-6 | 6.77E-6 | 3.35E-6 | 7.48E-6 |
| 199 | 9.25E-7 | 2.92E-6 | 1.65E-6 | 1.13E-6 |
| 200 | 2.41E-5 | 1.99E-5 | 1.87E-5 | 1.12E-5 |
| 201 | 2.57E-6 | 7.98E-6 | 4.30E-6 | 7.54E-6 |
| 202 | >3.30E-5 | 2.87E-5 | 2.52E-5 | 1.74E-5 |
| 203 | 1.32E-6 | 4.31E-6 | 2.19E-6 | 1.78E-6 |
| 204 | 1.90E-6 | 5.63E-6 | 4.17E-6 | 5.15E-6 |
| 205 | 1.38E-6 | 2.92E-6 | 2.00E-6 | |
| 206 | 1.40E-6 | 1.60E-6 | 1.03E-5 | |
| 207 | 4.45E-6 | 1.08E-5 | 5.28E-6 | 7.76E-6 |
| 208 | 2.63E-6 | 9.98E-6 | 3.12E-6 | |
| 209 | >3.30E-5 | >3.30E-5 | 1.58E-5 | |
| 211 | >3.30E-5 | >3.30E-5 | 2.44E-6 | 4.44E-6 |
| 212 | 6.68E-6 | 2.02E-5 | 5.11E-6 | 3.63E-6 |

TABLE 2-continued

IC$_{50}$ values of selected examples in cellular cytotoxicity induction assay and antiproliferation assay

| Example | Cytotox SUDHL5 [M] (median) | Cytotox SUDHL10 [M] (median) | Antiproli SUDHL5 [M] (median) | Antiproli SUDHL10 [M] (median) |
|---|---|---|---|---|
| 213 | >3.30E−5 | >3.30E−5 | 2.49E−6 | 5.12E−6 |
| 214 | 1.14E−5 | 1.55E−5 >3.30E−5 | 9.08E−6 | |
| 215 | >3.30E−5 | >3.30E−5 | 1.48E−5 | |
| 216 | 1.04E−5 | 3.11E−5 | 1.27E−5 | |
| 217 | 3.92E−6 | 1.58E−5 | 5.58E−6 | |
| 218 | 2.76E−5 | >3.30E−5 | 1.71E−5 | |
| 219 | 9.71E−6 | 2.47E−5 | 9.95E−6 | 1.36E−5 |
| 220 | 9.69E−6 | >3.30E−5 | 1.05E−5 | |
| 221 | >3.30E−5 | >3.30E−5 | 9.75E−6 | |
| 222 | 1.15E−5 | 2.01E−5 | 9.85E−6 | |
| 223 | 8.33E−6 | 2.88E−5 >3.30E−5 | 9.92E−6 | |
| 224 | >3.30E−5 | 3.20E−5 | 6.03E−6 | |
| 225 | 1.32E−5 | 3.27E−5 >3.30E−5 | 7.21E−6 | |
| 226 | 3.41E−6 | 3.04E−5 | 3.15E−6 | |
| 227 | >3.30E−5 | >3.30E−5 | 8.96E−6 | |
| 228 | 1.14E−5 | >3.30E−5 | 9.88E−6 | |
| 229 | 4.93E−6 | >3.30E−5 | 5.31E−6 | |
| 230 | 3.09E−5 | >3.30E−5 | 1.54E−5 | |
| 231 | 1.33E−5 | 1.60E−5 | 8.10E−6 | 1.14E−5 |
| 232 | 7.50E−6 | 1.32E−5 | 2.94E−6 | 1.97E−5 |
| 233 | 2.15E−5 | >3.30E−5 | 9.23E−6 | 1.85E−5 |
| 234 | 2.71E−5 | >3.30E−5 | 3.15E−5 | 1.98E−5 |
| 235 | >3.30E−5 | >3.30E−5 | 1.22E−5 | |
| 236 | 1.06E−5 | 2.52E−5 | 9.48E−6 | |
| 237 | 6.60E−6 | 1.18E−5 | 5.65E−6 | |
| 238 | 4.16E−6 | 7.83E−6 | | |
| 239 | >3.30E−5 | 3.03E−5 | | |
| 240 | 1.26E−5 | >3.30E−5 | 1.19E−5 | |
| 241 | 4.64E−6 | 1.92E−5 | 9.89E−6 | |
| 242 | >3.30E−5 | >3.30E−5 | 1.52E−5 | 2.74E−6 |
| 243 | 6.44E−6 | 1.46E−5 | 1.11E−5 | |
| 244 | 3.20E−6 | 6.60E−6 | 5.23E−6 | 5.00E−6 |
| 247 | 6.79E−6 | 1.90E−5 | 5.26E−6 | 9.30E−6 |
| 248 | 3.38E−6 | 1.29E−5 | 6.51E−6 | 8.78E−6 |
| 249 | >3.30E−5 | >3.30E−5 | 1.79E−5 | 7.58E−6 |
| 250 | 1.33E−5 | 2.18E−5 | 9.30E−6 | 9.70E−6 |
| 251 | >3.30E−5 | >3.30E−5 | 6.23E−6 | 5.15E−6 |
| 252 | 5.17E−6 | 2.09E−5 | 8.78E−6 | 6.31E−6 |
| 253 | 6.70E−6 | 1.96E−5 | 5.74E−6 | 1.17E−5 |
| 254 | 3.21E−6 | 8.11E−6 | 2.32E−6 | |
| 255 | >3.30E−5 | 3.28E−5 | 1.39E−5 | |
| 256 | 2.29E−5 | >3.30E−5 | 1.50E−5 | 9.20E−6 |
| 257 | >3.30E−5 | >3.30E−5 | 2.00E−5 | 8.12E−6 |
| 258 | >3.30E−5 | >3.30E−5 | 1.92E−5 | 1.18E−5 |
| 259 | >3.30E−5 | >3.30E−5 | >3.30E−5 | 2.96E−5 |
| 260 | 6.30E−6 | 1.18E−5 | 3.61E−6 | |
| 261 | 2.02E−5 | 3.80E−6 | 1.17E−6 | 4.66E−6 |
| 262 | 1.67E−5 | 2.15E−5 | 4.20E−6 | |
| 263 | >3.30E−5 | 2.79E−5 | 4.61E−6 | |
| 264 | >3.30E−5 | >3.30E−5 | 1.67E−5 | |
| 265 | 2.09E−6 | 7.35E−6 | 2.58E−6 | |
| 266 | 1.76E−6 | 4.99E−6 | 9.96E−7 | 2.83E−6 |
| 267 | 1.11E−6 | 3.66E−6 | 1.89E−6 | |
| 268 | >3.30E−5 | >3.30E−5 | 7.41E−6 | |
| 269 | 4.98E−6 | 1.47E−5 | 2.26E−6 | 7.27E−6 |
| 270 | 5.39E−6 | 2.19E−5 | 5.37E−6 | 1.20E−5 |
| 271 | 3.28E−5 | >3.30E−5 | 1.27E−5 | |
| 272 | >3.30E−5 | 2.50E−5 | 2.76E−6 | |
| 273 | 4.58E−6 | 1.62E−5 | 3.74E−6 | |
| 274 | >3.30E−5 | >3.30E−5 | 3.93E−6 | |
| 275 | >3.30E−5 | 2.83E−5 | 3.33E−6 | |
| 276 | 5.23E−6 | 1.03E−5 | 5.85E−6 | 7.32E−6 |
| 277 | 2.10E−6 | 2.28E−6 | 2.05E−6 | |
| 278 | 2.48E−5 | >3.30E−5 | 1.19E−5 | |
| 279 | 2.05E−5 | 2.94E−5 | 7.56E−6 | |
| 280 | >3.30E−5 | 3.07E−5 | 1.18E−5 | |
| 281 | 1.85E−6 | 2.58E−6 | 2.48E−6 | 6.99E−6 |
| 282 | 6.16E−7 | 7.80E−7 | 5.78E−7 | |
| 283 | 2.17E−5 | 3.05E−5 | 8.33E−6 | |
| 284 | 2.46E−6 | 4.25E−6 | 2.82E−6 | 7.01E−6 |
| 285 | 7.50E−7 | 2.81E−6 | 9.39E−7 | |
| 286 | 1.20E−5 | >3.30E−5 | 5.11E−6 | |
| 287 | 5.19E−6 | 1.58E−5 | 7.20E−6 | 8.10E−6 |
| 288 | 1.68E−6 | 6.54E−6 | 1.54E−6 | |
| 289 | 2.90E−5 >3.30E−5 | >3.30E−5 | 1.05E−5 | |
| 290 | 3.61E−5 | 1.19E−5 | 5.06E−6 | |
| 291 | 8.60E−6 | >3.30E−5 | 8.71E−6 | |
| 292 | 1.13E−6 | 1.52E−6 | 1.59E−6 | |
| 293 | 4.23E−7 | 9.88E−7 | 6.43E−7 | |
| 294 | 5.95E−6 | 1.08E−5 | 5.96E−6 | |
| 295 | 1.61E−5 | 1.80E−5 | 9.86E−6 | |
| 296 | 5.31E−6 | 1.43E−5 | 5.20E−6 | |
| 297 | 2.83E−5 | 2.77E−5 | 5.16E−6 | |
| 298 | 9.10E−6 | 2.27E−5 | 1.09E−5 | |
| 299 | >3.30E−5 | >3.30E−5 | 7.39E−6 | |
| 300 | 5.80E−6 | 2.25E−5 | 5.13E−6 | |
| 301 | 1.60E−6 | 3.50E−6 | 2.00E−6 | |
| 302 | 1.05E−6 | 3.49E−6 | 1.99E−6 | |
| 303 | >3.30E−5 | >3.30E−5 | 6.97E−6 | |
| 304 | >3.30E−5 | >3.30E−5 | 9.84E−6 | |
| 305 | | | | |
| 306 | | | | |
| 307 | >3.30E−5 | >3.30E−5 | 1.19E−5 | |
| 308 | 5.61E−6 | >3.30E−5 | | |
| 309 | >3.30E−5 | >3.30E−5 | | |
| 310 | 2.36E−5 | 1.75E−5 | 5.42E−6 | |
| 311 | 2.12E−5 | 1.49E−5 | | |
| 312 | | | | |
| 313 | 3.09E−5 | 2.71E−5 | 7.48E−6 | |
| 314 | 1.56E−5 | 2.09E−5 | | |
| 315 | 1.48E−5 | 1.58E−5 | | |
| 316 | 1.94E−5 | >3.30E−5 | 1.43E−5 | |
| 317 | 1.55E−5 | >3.30E−5 | 2.71E−5 | >3.30E−5 |
| 318 | 1.62E−5 | >3.30E−5 | 1.84E−5 | 2.72E−5 |
| 319 | 2.11E−5 | 2.83E−5 | 1.21E−5 | 5.93E−6 |
| 320 | 1.10E−5 | 2.29E−5 | 5.43E−6 | 9.36E−6 |
| 321 | 2.97E−5 | 2.56E−5 | 1.22E−5 | 4.61E−6 |
| 322 | >3.30E−5 | >3.30E−5 | 2.46E−5 | 1.90E−5 |
| 323 | >3.30E−5 | >3.30E−5 | 1.32E−5 | 1.36E−5 |
| 324 | 2.92E−5 | 2.68E−5 >3.30E−5 | 1.59E−5 | 1.62E−5 |
| 325 | >3.30E−5 | >3.30E−5 | 2.13E−5 | 1.45E−5 |
| 326 | >3.30E−5 | >3.30E−5 | 3.18E−5 | 1.14E−5 |
| 327 | >3.30E−5 | >3.30E−5 | 2.48E−5 | 1.30E−5 |
| 328 | >3.30E−5 | >3.30E−5 | 1.87E−5 | 1.90E−5 |
| 329 | >3.30E−5 | >3.30E−5 | >3.30E−5 | >3.30E−5 |
| 330 | >3.30E−5 | >3.30E−5 | >3.30E−5 | 2.49E−5 |
| 331 | >3.30E−5 | >3.30E−5 | >3.30E−5 | >3.30E−5 |
| 332 | 1.94E−5 | >3.30E−5 | 9.13E−6 | 2.02E−5 |
| 333 | 2.89E−5 | >3.30E−5 | 8.44E−6 | 8.22E−6 |
| 334 | 1.85E−5 | 2.67E−5 | 1.68E−5 | 1.54E−5 |
| 335 | 2.57E−5 | 2.77E−5 | 1.93E−5 | 2.24E−5 |
| 336 | >3.30E−5 | >3.30E−5 | >3.30E−5 | >3.30E−5 |
| 337 | >3.30E−5 | >3.30E−5 | 1.97E−5 | >3.30E−5 |
| 338 | >3.30E−5 | >3.30E−5 | >3.30E−5 | >3.30E−5 |
| 339 | >3.30E−5 | >3.30E−5 | >3.30E−5 | >3.30E−5 |
| 340 | 1.56E−5 | >3.30E−5 | 4.71E−6 | >3.30E−5 |
| 341 | 2.64E−5 | >3.30E−5 | 6.48E−6 | >3.30E−5 |
| 342 | >3.30E−5 | >3.30E−5 | 3.15E−5 | 1.90E−5 |
| 343 | >3.30E−5 | >3.30E−5 | 1.92E−6 | 1.11E−6 |
| 344 | >3.30E−5 | >3.30E−5 | 2.08E−5 | 1.44E−5 |
| 345 | 8.32E−6 | 1.32E−5 | 7.32E−6 | 5.68E−6 |
| 346 | 2.02E−6 | >3.30E−5 | 9.09E−6 | 3.54E−6 |
| 347 | >3.30E−5 | >3.30E−5 | 4.20E−6 | |
| 348 | 1.38E−5 | 2.81E−5 | 5.12E−6 | |
| 349 | 2.43E−5 | >3.30E−5 | 1.86E−5 | 1.67E−5 |
| 350 | 2.07E−5 | 3.11E−5 >3.30E−5 | 1.38E−5 | |

TABLE 2-continued

IC$_{50}$ values of selected examples in cellular cytotoxicity induction assay and antiproliferation assay

| Example | Cytotox SUDHL5 [M] (median) | Cytotox SUDHL10 [M] (median) | Antiproli SUDHL5 [M] (median) | Antiproli SUDHL10 [M] (median) |
|---|---|---|---|---|
| 351 | >3.30E−5 | >3.30E−5 | 2.07E−5 | |
| 352 | >3.30E−5 | >3.30E−5 | 1.19E−5 | |
| 353 | >3.30E−5 | >3.30E−5 | 8.32E−6 | |
| 354 | >3.30E−5 | >3.30E−5 | >3.30E−5 | |
| 355 | >3.30E−5 | >3.30E−5 | 3.20E−5 | |
| 356 | >3.30E−5 | >3.30E−5 | 2.53E−5 | |
|     |          |          | >3.30E−5 | |
| 357 | >3.30E−5 | >3.30E−5 | 3.27E−5 | |
| 358 | >3.30E−5 | >3.30E−5 | 2.06E−5 | |
| 359 | >3.30E−5 | >3.30E−5 | >3.30E−5 | >3.30E−5 |
| 360 | >3.30E−5 | >3.30E−5 | 2.12E−5 | 1.44E−5 |
| 361 | 1.09E−5 | 1.84E−5 | 3.66E−6 | 7.70E−6 |
| 362 | 2.72E−5 | >3.30E−5 | 1.27E−5 | |
| 363 | 1.68E−5 | 2.97E−5 | 1.14E−5 | 1.13E−5 |
| 364 | 1.92E−5 | >3.30E−5 | 9.54E−6 | |
|     |          | 2.04E−5  |          | |

An aspect of the invention are compounds of formula (I) having an IC$_{50}$ of cytotoxic or antiproliferative effect of less or equal to 5 E-6, particularly 1 E-6, more particularly less or equal to 5-R-7. Table 4 shows the results of the OPM2, A2780, MV4-11, SK-MEL-2 NCI-H929 proliferation assays.

TABLE 4

IC$_{50}$ values of selected examples in antiproliferation assay

| Example | OPM2 [M] (median) | A2780 [M] (median) | MV-4-11 [M] (median) | SK-MEL-2 [M] (median) | NCI-H1703 [M] (median) |
|---|---|---|---|---|---|
| 1-1 | | | | | |
| 1-2 | | | | | |
| 1-3 | 2.11E−6 | 4.86E−6 | | | |
| 1-4 | 3.36E−6 | 2.47E−6 | | | |
| 1-5 | 1.13E−6 | 6.24E−6 | 7.20E−7 | | |
| 1-6 | | | | | |
| 1-7 | >3.30E−5 | >3.30E−5 | | | |
| 1-8 | 1.24E−6 | 6.31E−6 | 3.57E−6 | | |
| 1-9 | >3.30E−5 | >3.30E−5 | 8.59E−6 | | |
| 1-10 | 2.81E−6 | 1.19E−5 | 2.29E−6 | 1.12E−5 | 5.52E−6 |
| 1-11 | 1.51E−6 | 4.31E−6 | 2.44E−6 | | |
| 1-12 | >3.30E−5 | >3.30E−5 | 6.78E−6 | | |
| 1-13 | 6.34E−7 | 7.74E−6 | 1.35E−6 | 4.96E−6 | 2.67E−6 |
| 1-15 | 1.91E−6 | 7.24E−6 | 3.52E−6 | >3.30E−5 | 1.10E−5 |
| 1-16 | 1.15E−5 | | | | |
| 1-17 | 4.37E−6 | 8.94E−6 | | | |
| 1-18 | 1.57E−6 | 8.79E−6 | | | |
| 1-19 | | | | | |
| 1-20 | 2.32E−6 | 1.38E−5 | | | |
| 1-21 | 3.61E−6 | 1.29E−5 | | | |
| 1-22 | 2.56E−6 | 1.83E−5 | | | |
| 1-23 | 1.70E−5 | 1.43E−5 | | | |
| 1-24 | 2.97E−5 | >3.30E−5 | | | |
| 1-25 | 1.08E−5 | 1.70E−5 | | | |
| 1-26 | 2.00E−6 | 2.48E−5 | | | |
| 1-27 | 8.75E−6 | 2.23E−5 | | | |
| 1-28 | 1.98E−5 | 3.12E−5 | | | |
| 1-29 | 4.53E−6 | 2.38E−5 | 2.58E−6 | | |
| 1-30 | 2.28E−5 | | | | |
| 1-31 | 1.05E−5 | >3.30E−5 | 2.61E−6 | | |
| 1-32 | 2.76E−5 | 1.82E−5 | | | |
| 1-33 | 2.23E−5 | >3.30E−5 | | | |
| 1-34 | 2.69E−5 | >3.30E−5 | 8.89E−6 | | |
| 1-35 | >3.30E−5 | >3.30E−5 | 1.96E−5 | | |
| 1-36 | 1.01E−5 | >3.30E−5 | | | |
| 1-37 | 6.53E−6 | 3.02E−5 | 4.02E−6 | | |
| 1-38 | 3.22E−5 | >3.30E−5 | | | |
| 1-39 | >3.30E−5 | >3.30E−5 | | | |
| 1-40 | 5.38E−6 | 3.95E−6 | 4.94E−6 | | |
| 1-41 | 2.17E−6 | 5.32E−6 | | | |
| 1-42 | 3.29E−5 | >3.30E−5 | | | |
| 1-43 | 1.81E−5 | 2.48E−5 | 6.59E−6 | | |
| 1-44 | 1.13E−5 | 1.95E−5 | | | |
| 1-46 | 1.52E−6 | 7.08E−6 | 7.20E−7 | | |
| 1-47 | 8.35E−6 | 6.40E−6 | | | |
| 1-49 | >3.30E−5 | 2.31E−5 | 1.21E−5 | | |
| 1-50 | 1.21E−5 | 1.83E−5 | 1.05E−5 | | |
| 1-52 | 3.20E−5 | 2.26E−5 | 7.75E−6 | | |
| 1-53 | >3.30E−5 | 2.48E−5 | | | |

TABLE 4-continued

IC$_{50}$ values of selected examples in antiproliferation assay

| Example | OPM2 [M] (median) | A2780 [M] (median) | MV-4-11 [M] (median) | SK-MEL-2 [M] (median) | NCI-H1703 [M] (median) |
|---|---|---|---|---|---|
| 1-55 | >3.30E−5 | 2.59E−5 | | | |
| 1-56 | >3.30E−5 | >3.30E−5 | | | |
| 1-58 | 2.01E−5 | 1.31E−5 | | | |
| 1-59 | 1.26E−5 | 1.16E−5 | | | |
| 1-60 | >3.30E−5 | 2.88E−5 | | | |
| 1-61 | | | | | |
| 1-62 | 7.60E−6 | 5.49E−6 | | | |
| 1-63 | 1.18E−5 | 1.11E−5 | | | |
| 1-64 | 2.15E−5 | 1.21E−5 | | | |
| 1-65 | | | | | |
| 1-66 | 1.18E−5 | 1.22E−5 | | | |
| 1-67 | 1.19E−5 | 6.25E−6 | | | |
| 1-68 | >3.30E−5 | 2.87E−5 | | | |
| 1-69 | >3.30E−5 | >3.30E−5 | | | |
| 1-70 | 1.22E−5 | 1.82E−5 | | | |
| 1-71 | 2.57E−5 | 2.55E−5 | | | |
| 1-72 | 1.53E−5 | 1.85E−5 | | | |
| 1-73 | 1.17E−5 | 1.82E−5 | | | |
| 1-74 | 1.60E−5 | 1.91E−5 | | | |
| 1-75 | 9.37E−6 | 1.39E−5 | | | |
| 1-76 | >3.30E−5 | | | | |
| 1-77 | >3.30E−5 | | | | |
| 1-78 | 3.06E−5 | | | | |
| 1-79 | | | | | |
| 1-80 | | | | | |
| 1-81 | >3.30E−5 | | | | |
| 1-82 | >3.30E−5 | | | | |
| 1-83 | >3.30E−5 | | | | |
| 1-84 | >3.30E−5 | | | | |
| 1-85 | >3.30E−5 | | | | |
| 1-86 | 2.43E−5 | | | | |
| 1-88 | >3.30E−5 | >3.30E−5 | | | |
| 1-89 | >3.30E−5 | >3.30E−5 | | | |
| 1-91 | 8.37E−6 | 7.55E−6 | 2.62E−6 | | |
| 1-92 | 9.60E−6 | 6.23E−6 | 1.57E−6 | | |
| 1-93 | | | | | |
| 1-94 | | | | | |
| 1-95 | | | | | |
| 1-96 | >3.30E−5 | 2.05E−5 | | | |
| 1-97 | 1.43E−5 | | | | |
| 1-99 | 1.98E−5 | 1.12E−5 | 7.19E−6 | | |
| 1-100 | 1.94E−5 | 1.38E−5 | | | |
| 1-101 | >3.30E−5 | 1.97E−5 | | | |
| 1-103 | 1.58E−5 | >3.30E−5 | | | |
| 1-104 | | | 4.44E−6 | | |
| 1-106 | | 8.83E−6 | | | |
| 1-107 | | | | | |
| 1-109 | 8.14E−6 | 8.70E−6 | 6.94E−6 | | |
| 1-110 | 8.62E−6 | 7.54E−6 | | | |
| 1-112 | | | 2.69E−6 | | |
| 1-113 | | | 1.20E−5 | | |
| 1-115 | >3.30E−5 | | | | |
| 1-116 | 2.96E−5 | >3.30E−5 | | | |
| 1-118 | >3.30E−5 | 3.25E−5 | | | |
| 1-119 | >3.30E−5 | >3.30E−5 | | | |
| 1-120 | >3.30E−5 | >3.30E−5 | | | |
| 1-121 | 8.33E−6 | 9.61E−6 | | | |
| 1-122 | 2.77E−5 | 2.80E−5 | | | |
| 001 | >3.30E−5 | | | | |
| 002 | >3.30E−5 | | | | |
| 003 | >3.30E−5 | | | | |
| 004 | 1.09E−5 | 7.13E−6 | | | |
| 005 | >3.30E−5 | >3.30E−5 | | | |
| 006 | 1.90E−5 | >3.30E−5 | | | |
| | >3.30E−5 | 2.49E−5 | | | |
| 007 | | >3.30E−5 | 8.03E−6 | | |
| | | 3.25E−5 | | | |
| 008 | | 2.46E−5 | | | |
| 009 | 2.10E−5 | 2.25E−5 | | | |
| 010 | | 2.06E−5 | | | |
| 011 | | 1.58E−5 | | | |
| 012 | 2.17E−5 | 3.13E−5 | | | |
| 013 | >3.30E−5 | 3.27E−5 | | | |
| 014 | | >3.30E−5 | | | |

TABLE 4-continued

IC$_{50}$ values of selected examples in antiproliferation assay

| Example | OPM2 [M] (median) | A2780 [M] (median) | MV-4-11 [M] (median) | SK-MEL-2 [M] (median) | NCI-H1703 [M] (median) |
|---|---|---|---|---|---|
| 015 | | 1.23E−5 | 1.33E−5 | | |
| 016 | >3.30E−5 | >3.30E−5 | | | |
| 017 | 2.78E−5 | >3.30E−5 | | | |
| | >3.30E−5 | | | | |
| 018 | 9.67E−6 | >3.30E−5 | | | |
| 019 | | >3.30E−5 | | | |
| 020 | | 1.37E−5 | | | |
| 021 | >3.30E−5 | >3.30E−5 | | | |
| | | 2.52E−5 | | | |
| 022 | | 2.59E−5 | | | |
| 023 | 6.79E−6 | 2.00E−5 | 2.29E−6 | | |
| | | >3.30E−5 | | | |
| 024 | >3.30E−5 | >3.30E−5 | | | |
| | | 2.21E−5 | | | |
| 025 | | 3.04E−5 | | | |
| | | >3.30E−5 | | | |
| 026 | | 1.97E−5 | 1.14E−5 | | |
| 027 | >3.30E−5 | 2.54E−5 | 2.98E−5 | | |
| 028 | | 1.94E−5 | | | |
| 029 | | 2.01E−5 | | | |
| 038 | | >3.30E−5 | | | |
| 039 | | 2.14E−5 | | | |
| 040 | | 1.90E−5 | | | |
| 041 | | 1.81E−5 | | | |
| 042 | | 1.02E−5 | | | |
| 043 | | >3.30E−5 | | | |
| | | 2.60E−5 | | | |
| 044 | | >3.30E−5 | 4.10E−6 | | |
| 045 | | 2.78E−5 | | | |
| 046 | | 2.65E−5 | | | |
| 047 | | 2.69E−5 | 5.38E−6 | | |
| 048 | | 1.01E−5 | | | |
| 049 | | 1.57E−5 | | | |
| 050 | | 3.01E−5 | | | |
| 051 | | 1.53E−5 | | | |
| 052 | 3.07E−5 | 7.41E−6 | | | |
| 053 | 1.11E−5 | >3.30E−5 | | | |
| 054 | 7.46E−6 | 2.48E−5 | | | |
| 055 | >3.30E−5 | >3.30E−5 | | | |
| 056 | >3.30E−5 | >3.30E−5 | | | |
| 057 | >3.30E−5 | 3.01E−5 | | | |
| 058 | >3.30E−5 | >3.30E−5 | | | |
| 059 | 2.52E−5 | 2.91E−5 | | | |
| 060 | 1.27E−5 | 2.21E−5 | | | |
| 061 | 2.51E−5 | 1.14E−5 | 8.02E−6 | | |
| 062 | 1.67E−5 | 2.26E−5 | | | |
| 063 | 1.36E−5 | 2.02E−5 | | | |
| 064 | | 3.14E−5 | | | |
| 065 | | >3.30E−5 | | | |
| 066 | >3.30E−5 | 2.80E−5 | | | |
| 067 | 1.48E−5 | 2.72E−6 | | | |
| 068 | 9.82E−6 | 1.85E−5 | 1.69E−5 | | |
| 069 | | >3.30E−5 | | | |
| 070 | 1.34E−5 | 1.87E−5 | | | |
| 071 | 1.30E−5 | 1.89E−5 | | | |
| 072 | 8.23E−6 | 9.51E−6 | | | |
| 073 | | 1.40E−5 | | | |
| 074 | | 1.30E−5 | 7.04E−6 | | |
| 075 | 1.10E−5 | 1.97E−5 | | | |
| 076 | | 2.28E−5 | | | |
| 077 | | 2.06E−5 | | | |
| 078 | | 1.96E−5 | | | |
| 079 | | 1.66E−5 | 2.37E−6 | | |
| 080 | | 2.41E−5 | 1.21E−5 | | |
| 081 | 1.44E−5 | 1.74E−5 | | | |
| 082 | | 1.68E−5 | | | |
| 083 | | 1.38E−5 | | | |
| 084 | 2.67E−5 | 1.77E−5 | | | |
| 085 | | 2.15E−5 | | | |
| 086 | | 1.36E−5 | | | |
| 087 | | >3.30E−5 | | | |
| 088 | | 2.35E−5 | | | |
| 089 | | >3.30E−5 | | | |
| 090 | | 1.98E−5 | | | |
| 091 | | 7.10E−6 | | | |

TABLE 4-continued

IC$_{50}$ values of selected examples in antiproliferation assay

| Example | OPM2 [M] (median) | A2780 [M] (median) | MV-4-11 [M] (median) | SK-MEL-2 [M] (median) | NCI-H1703 [M] (median) |
|---|---|---|---|---|---|
| 092 |  | 2.48E−5 |  |  |  |
| 093 |  | 2.71E−5 |  |  |  |
| 094 |  | 2.58E−5 |  |  |  |
| 096 |  | 2.79E−5 | 1.45E−6 |  |  |
| 097 |  | 2.84E−5 |  |  |  |
| 098 |  | 2.09E−5 |  |  |  |
| 099 |  | 2.11E−5 |  |  |  |
| 100 |  | >3.30E−5 |  |  |  |
| 101 | 4.37E−6 | 2.71E−5 | 1.85E−6 |  |  |
| 102 |  | >3.30E−5 |  |  |  |
| 103 |  | >3.30E−5 |  |  |  |
|  |  | 2.72E−5 |  |  |  |
| 104 |  | 2.21E−5 |  |  |  |
| 105 |  | 1.49E−5 |  |  |  |
| 107 |  | >3.30E−5 |  |  |  |
|  |  | 2.08E−5 |  |  |  |
| 108 |  | 1.52E−5 |  |  |  |
| 109 |  | 1.90E−5 |  |  |  |
| 110 |  | >3.30E−5 | 1.33E−5 |  |  |
| 111 |  | 2.61E−5 |  |  |  |
| 113 | 1.42E−5 | 8.81E−6 |  |  |  |
| 114 | 1.10E−5 | 7.06E−6 | 4.54E−6 |  |  |
| 115 | 1.90E−5 | 1.19E−5 |  |  |  |
| 116 | 1.79E−5 | 2.21E−5 |  |  |  |
| 117 | >3.30E−5 | >3.30E−5 |  |  |  |
| 119 | 6.62E−6 | 1.21E−5 | 8.87E−6 |  |  |
| 120 | 4.36E−6 | 1.11E−5 | 1.13E−5 |  |  |
| 122 | 2.79E−6 | 7.40E−6 |  |  |  |
| 123 | 4.32E−6 | 1.14E−5 |  |  |  |
| 124 | 1.48E−5 | 1.10E−5 |  |  |  |
| 125 | 1.15E−5 | 8.42E−6 | 2.02E−6 |  |  |
| 126 | >3.30E−5 | 3.19E−5 |  |  |  |
| 127 | >3.30E−5 | 2.44E−5 |  |  |  |
| 128 | >3.30E−5 | 3.04E−5 |  |  |  |
| 129 | >3.30E−5 | 1.70E−5 |  |  |  |
| 130 | 6.00E−6 | 1.11E−5 |  |  |  |
| 131 | 1.71E−5 | 1.48E−5 | 6.24E−6 |  |  |
| 132 | 1.17E−5 | 1.34E−5 |  |  |  |
| 133 |  | 1.51E−5 | 6.84E−6 |  |  |
| 134 |  | 2.07E−5 |  |  |  |
| 135 | >3.30E−5 | >3.30E−5 |  |  |  |
| 136 | >3.30E−5 | >3.30E−5 |  |  |  |
| 137 | >3.30E−5 | >3.30E−5 | 6.78E−6 |  |  |
| 138 | >3.30E−5 | >3.30E−5 |  |  |  |
| 139 | >3.30E−5 | >3.30E−5 |  |  |  |
| 140 | >3.30E−5 | >3.30E−5 | 2.27E−5 |  |  |
| 141 | 9.12E−6 | 1.48E−5 |  |  |  |
| 142 |  | 2.25E−5 |  |  |  |
| 143 |  | 1.21E−5 | 1.20E−5 |  |  |
| 144 | 5.52E−6 | 1.17E−5 |  |  |  |
| 145 | 3.22E−6 | 1.36E−5 | 4.30E−6 | 1.17E−5 | 6.53E−6 |
| 146 |  | 1.37E−5 |  |  |  |
| 147 | 1.05E−5 | 2.44E−5 | 1.37E−5 |  |  |
| 148 | 2.74E−6 | 2.00E−5 | 9.73E−7 | 2.67E−5 | 9.36E−6 |
| 149 |  | 2.84E−5 |  |  |  |
| 150 |  | >3.30E−5 |  |  |  |
| 151 |  | >3.30E−5 |  |  |  |
| 152 |  | >3.30E−5 |  |  |  |
| 153 | 8.40E−6 | 1.52E−5 |  |  |  |
| 154 | 2.00E−6 | 1.72E−5 | 1.36E−6 | 1.84E−5 | 6.84E−6 |
| 155 |  | 2.25E−5 |  |  |  |
| 156 |  | >3.30E−5 |  |  |  |
| 157 |  | >3.30E−5 |  |  |  |
| 159 | >3.30E−5 | >3.30E−5 |  |  |  |
| 160 | >3.30E−5 | >3.30E−5 |  |  |  |
| 161 |  | 1.62E−5 |  |  |  |
| 162 |  | 2.55E−5 |  |  |  |
| 163 |  | 2.75E−5 |  |  |  |
| 164 |  | 2.03E−5 |  |  |  |
| 165 |  | 2.15E−5 | 8.15E−6 |  |  |
| 166 |  | 2.82E−5 | 1.88E−5 |  |  |
| 169 | 2.04E−5 | 2.02E−5 |  |  |  |
| 170 | 1.34E−5 | 2.67E−5 |  |  |  |
| 171 | 1.23E−5 | >3.30E−5 |  |  |  |
| 172 | >3.30E−5 | >3.30E−5 |  |  |  |

TABLE 4-continued

IC$_{50}$ values of selected examples in antiproliferation assay

| Example | OPM2 [M] (median) | A2780 [M] (median) | MV-4-11 [M] (median) | SK-MEL-2 [M] (median) | NCI-H1703 [M] (median) |
|---|---|---|---|---|---|
| 177 | | >3.30E−5 | | | |
| 178 | | >3.30E−5 | | | |
| 179 | | >3.30E−5 | 9.83E−6 | | |
| 180 | | 2.36E−5 | | | |
| 181 | | 2.46E−5 | 1.80E−5 | | |
| 182 | | 1.75E−5 | | | |
| 183 | | >3.30E−5 | | | |
| | | 2.39E−5 | | | |
| 184 | | >3.30E−5 | 1.52E−6 | | |
| 185 | | 1.88E−5 | | | |
| 186 | | >3.30E−5 | | | |
| | | 2.28E−5 | | | |
| 187 | | 2.17E−5 | | | |
| | | >3.30E−5 | | | |
| 188 | | 2.42E−5 | | | |
| 189 | | 1.78E−5 | | | |
| 190 | | 2.02E−5 | | | |
| 191 | | 2.55E−5 | 2.58E−6 | | |
| 192 | | 1.80E−5 | | | |
| 193 | | 1.90E−5 | | | |
| 194 | | 1.82E−5 | | | |
| 195 | | 1.27E−5 | | | |
| 196 | | 1.53E−5 | 4.83E−6 | | |
| 197 | | 1.49E−5 | | | |
| 198 | | 2.25E−5 | | | |
| 199 | | 1.57E−5 | 7.51E−6 | 2.90E−5 | 1.46E−5 |
| 200 | | 2.57E−5 | | | |
| 201 | | 1.63E−5 | | | |
| | | >3.30E−5 | | | |
| 202 | | 3.17E−5 | | | |
| 203 | | 2.21E−5 | 2.80E−6 | | |
| 204 | | 1.78E−5 | | | |
| 205 | | 1.03E−5 | 2.83E−6 | | |
| 206 | | 2.28E−5 | 1.92E−5 | | |
| 207 | | 2.47E−5 | | | |
| 208 | | 2.03E−5 | 2.68E−6 | | |
| 209 | | 1.58E−5 | | | |
| 211 | | >3.30E−5 | | | |
| 212 | | 2.15E−5 | 5.00E−6 | | |
| | | >3.30E−5 | | | |
| 213 | | 2.91E−5 | | | |
| 214 | 2.90E−5 | 7.00E−5 | | | |
| | | >3.30E−5 | >3.30E−5 | | |
| 215 | >3.30E−5 | 2.33E−5 | | | |
| 216 | 2.02E−5 | | | | |
| 217 | | >3.30E−5 | 1.52E−5 | | |
| | | 2.92E−5 | | | |
| 218 | | 2.52E−5 | 3.05E−5 | | |
| 219 | | >3.30E−5 | | | |
| 220 | | >3.30E−5 | 2.27E−5 | | |
| 221 | | 3.28E−5 | >3.30E−5 | | |
| 222 | | 2.46E−5 | 7.87E−6 | | |
| 223 | | >3.30E−5 | 1.79E−5 | | |
| 224 | | 1.45E−5 | 1.22E−5 | | |
| 225 | | 2.33E−5 | 1.85E−5 | | |
| 226 | | >3.30E−5 | 2.09E−5 | | |
| 227 | | 1.65E−5 | 1.66E−5 | | |
| 228 | | >3.30E−5 | >3.30E−5 | | |
| 229 | | >3.30E−5 | >3.30E−5 | | |
| | | 2.95E−5 | | | |
| 230 | | 2.95E−5 | 2.46E−5 | | |
| | | >3.30E−5 | | | |
| 231 | | >3.30E−5 | | | |
| 232 | | >3.30E−5 | | | |
| 233 | | >3.30E−5 | | | |
| 234 | | 3.04E−5 | | | |
| 235 | | 1.80E−5 | 2.07E−5 | | |
| 236 | | 2.60E−5 | 2.19E−5 | | |
| 237 | | 1.90E−5 | 1.35E−5 | | |
| 238 | | >3.30E−5 | 1.46E−5 | | |
| | | 2.47E−5 | | | |
| 239 | | 2.27E−5 | 1.07E−5 | | |
| 240 | | >3.30E−5 | 2.56E−5 | | |
| 241 | | 2.89E−5 | | | |
| 242 | | 2.59E−6 | | | |

TABLE 4-continued

IC$_{50}$ values of selected examples in antiproliferation assay

| Example | OPM2 [M] (median) | A2780 [M] (median) | MV-4-11 [M] (median) | SK-MEL-2 [M] (median) | NCI-H1703 [M] (median) |
|---|---|---|---|---|---|
| 243 |  | 1.43E−5 |  |  |  |
| 244 |  | 1.84E−5 |  |  |  |
| 247 |  | 3.04E−5 |  |  |  |
|  |  | >3.30E−5 |  |  |  |
| 248 |  | 2.34E−5 |  |  |  |
|  |  | >3.30E−5 |  |  |  |
| 249 |  | 1.82E−5 |  |  |  |
| 250 |  | 2.29E−5 |  |  |  |
|  |  | >3.30E−5 |  |  |  |
| 251 |  | 2.84E−5 |  |  |  |
| 252 |  | 3.16E−5 | 1.04E−5 |  |  |
|  |  | >3.30E−5 |  |  |  |
| 253 |  | 2.83E−5 | 7.59E−6 |  |  |
| 254 |  | >3.30E−5 | 8.59E−6 |  |  |
|  |  | 2.25E−5 |  |  |  |
| 255 |  | 2.48E−5 | 1.31E−5 |  |  |
| 256 |  | 2.03E−5 |  |  |  |
| 257 |  | 1.90E−5 |  |  |  |
| 258 |  | 2.30E−5 |  |  |  |
| 259 |  | 2.21E−5 |  |  |  |
| 260 |  | 2.20E−5 | 4.35E−6 |  |  |
| 261 |  | 1.85E−5 |  |  |  |
| 262 |  | 7.54E−6 |  |  |  |
| 263 |  | 1.01E−5 |  |  |  |
| 264 |  | 1.92E−5 |  |  |  |
| 265 |  | >3.30E−5 | 2.75E−6 |  |  |
|  |  | 1.21E−5 |  |  |  |
| 266 |  | 2.83E−5 |  |  |  |
| 267 |  | 2.15E−5 | 7.02E−6 | 2.00E−5 | 1.36E−5 |
| 268 |  | 2.29E−5 | 7.46E−6 |  |  |
| 269 |  | 2.93E−5 |  |  |  |
| 270 |  | >3.30E−5 |  |  |  |
| 271 |  | 1.83E−5 |  |  |  |
| 272 |  | 7.15E−6 | 4.89E−6 |  |  |
| 273 |  | 4.18E−6 | 4.53E−6 |  |  |
| 274 |  | 1.17E−5 | 8.02E−6 |  |  |
| 275 |  | 7.02E−6 | 4.52E−6 |  |  |
| 276 |  | 1.22E−5 | 1.20E−5 |  |  |
| 277 |  | 1.50E−5 | 8.78E−6 |  |  |
| 278 |  | 1.26E−5 | 1.49E−5 |  |  |
| 279 |  | 7.50E−6 | 1.57E−5 |  |  |
| 280 |  | 8.02E−6 | 1.11E−5 |  |  |
| 281 |  | 1.39E−5 | 4.74E−6 |  |  |
| 282 |  | 8.66E−6 | 3.69E−6 | 1.25E−5 | 4.85E−6 |
| 283 |  | 1.50E−5 | 1.46E−5 |  |  |
| 284 |  | 1.52E−5 | 8.62E−6 |  |  |
| 285 |  | 1.22E−5 | 3.61E−6 | 1.09E−5 | 6.98E−6 |
| 286 |  | 1.26E−5 | 1.73E−5 |  |  |
| 287 |  | 3.05E−5 | 1.49E−5 |  |  |
| 288 |  | >3.30E−5 | 9.86E−6 | >3.30E−5 | 1.76E−5 |
| 289 |  | 2.23E−5 | 1.89E−5 |  |  |
| 290 |  | >3.30E−5 | 9.57E−6 |  |  |
|  |  | 2.62E−5 |  |  |  |
| 291 |  | >3.30E−5 | 1.82E−5 |  |  |
| 292 |  | 1.58E−5 | 8.52E−6 |  |  |
| 293 |  | 1.08E−5 | 2.08E−6 |  |  |
| 294 |  | 1.88E−5 | 1.53E−5 |  |  |
| 295 |  | 1.72E−5 | 1.58E−5 |  |  |
| 296 |  | 2.07E−5 | 1.52E−5 |  |  |
| 297 |  | 1.33E−5 | 1.90E−5 |  |  |
| 298 |  | 2.66E−5 | 9.40E−6 |  |  |
| 299 |  | 2.32E−5 | 2.63E−5 |  |  |
| 300 |  | >3.30E−5 | 2.15E−5 |  |  |
| 301 |  | 1.56E−5 | 5.99E−6 |  |  |
| 302 |  | 2.25E−5 | 4.78E−6 |  |  |
| 303 |  | 2.40E−5 | 2.61E−5 |  |  |
| 304 |  | 1.34E−5 | 3.13E−5 |  |  |
| 305 |  | >3.30E−5 | 1.36E−5 |  |  |
| 306 |  | 1.02E−5 | 1.50E−5 |  |  |
| 307 |  | 1.76E−5 | 1.84E−5 |  |  |
| 308 |  | >3.30E−5 | >3.30E−5 |  |  |
| 309 |  | >3.30E−5 | >3.30E−5 |  |  |
| 310 |  | 6.58E−6 | 1.31E−5 |  |  |
| 311 |  | 1.11E−5 | 1.16E−5 |  |  |
| 312 |  | 1.05E−5 | 1.28E−5 |  |  |

TABLE 4-continued

IC$_{50}$ values of selected examples in antiproliferation assay

| Example | OPM2 [M] (median) | A2780 [M] (median) | MV-4-11 [M] (median) | SK-MEL-2 [M] (median) | NCI-H1703 [M] (median) |
|---|---|---|---|---|---|
| 313 | | 1.05E−5 | 2.00E−5 | | |
| 314 | | 1.56E−5 | 1.35E−5 | | |
| 315 | | 8.63E−6 | 1.16E−5 | | |
| 316 | | >3.30E−5 | >3.30E−5 | | |
| 317 | | >3.30E−5 | 2.34E−5 | | |
| 318 | | >3.30E−5 | 3.28E−5 | | |
| 319 | | 1.26E−5 | | | |
| 320 | | 1.41E−5 | | | |
| 321 | | 1.00E−5 | | | |
| 322 | | >3.30E−5 | | | |
| 323 | | 2.18E−5 | | | |
| 324 | | 2.46E−5 | | | |
| 325 | | >3.30E−5 | | | |
| 326 | | >3.30E−5 | | | |
| 327 | | 3.12E−5 | | | |
| 328 | | >3.30E−5 | | | |
| 329 | | >3.30E−5 | | | |
| 330 | | >3.30E−5 | | | |
| 331 | | >3.30E−5 | | | |
| 332 | | >3.30E−5 | | | |
| 333 | | 1.67E−5 | | | |
| 334 | | 2.87E−5 | 1.47E−5 | | |
| 335 | | 2.35E−5 | | | |
| 336 | | >3.30E−5 | | | |
| 337 | | >3.30E−5 | | | |
| 338 | | >3.30E−5 | | | |
| 339 | | >3.30E−5 | | | |
| 340 | | >3.30E−5 | | | |
| 341 | | >3.30E−5 | | | |
| 342 | | >3.30E−5 | | | |
| 343 | | 1.90E−5 | | | |
| 344 | | >3.30E−5 | | | |
| 345 | | 1.59E−5 | 7.47E−6 | | |
| 346 | | 2.32E−5 | | | |
| 347 | | 9.45E−6 | 1.20E−5 | | |
| 348 | | 1.46E−5 | 4.15E−6 | | |
| 349 | | >3.30E−5 | | | |
| 350 | | >3.30E−5 | 1.53E−5 | | |
| 351 | | >3.30E−5 | >3.30E−5 | | |
| 352 | | >3.30E−5 | 1.05E−5 | | |
| 353 | | 2.17E−5 | 3.11E−5 | | |
| 354 | | 2.73E−5 | >3.30E−5 | | |
| 355 | | >3.30E−5 | >3.30E−5 | | |
| 356 | | >3.30E−5 | >3.30E−5 | | |
| 357 | | >3.30E−5 | 3.19E−5 | | |
| 358 | | 1.20E−5 | | | |
| 359 | | >3.30E−5 | | | |
| 360 | | >3.30E−5 | | | |
| 361 | | >3.30E−5 | | | |
| 362 | | 1.41E−5 | | | |
| 363 | | 1.54E−5 | | | |
| 364 | | 1.69E−5 | 2.42E−5 | | |

An aspect of the invention are compounds of formula (I) having an IC$_{50}$ in the antiproliferation assay disclosed above of less or equal to 1 E-5, particularly less or equal to 5-E-6, more particularly less or equal to 1 E-6.

The cell lines used for the proliferation assays are examples of tumor indications and listed in the following table 5:

TABLE 5

| Cell line | origin | Indication |
|---|---|---|
| SUDHL5 | DSMZ | B-cell lymphoma (GC-DLBCL) |
| SUDHL10 | DSMZ | B-cell lymphoma (GC-DLBCL) |
| OPM2 | DSMZ | Multiple Myeloma |
| A2780 | ECACC | Ovarian carcinoma |
| MV-4-11 | ATCC | Acute monocytic leukemia |
| SK-MEL-2 | ATCC | Melanoma |
| NCI-H1703 | ATCC | Lung Cancer |
| Hs578T | ATCC | Breast Cancer |
| Rec1 | ATCC | Mantle cell lymphoma |
| HBL-1 | | B-cell lymphoma (ABC-DLBCL) |
| BxPC3 | ATCC | Pancreas cancer |

Caco-2 Permeation Assay

Caco-2 cells (purchased from DSMZ Braunschweig, Germany) were seeded at a density of 4.5×10$^4$ cell per well on 24 well insert plates, 0.4 µm pore size, and grown for 15 days in DMEM medium supplemented with 10% fetal bovine serum, 1% GlutaMAX (100×, GIBCO), 100 U/ml penicillin, 100 µg/ml streptomycin (GIBCO) and 1% non essential amino acids (100×). Cells were maintained at 37° C. in a humified 5% $CO_2$ atmosphere. Medium was changed every 2-3 day. Before running the permeation assay, the culture medium was replaced by an FCS-free hepes-carbonate transport puffer (pH 7.2). For assessment of monolayer integrity the transepithelial electrical resistance (TEER) was measured. Test compounds were predissolved in DMSO and added either to the apical or basolateral compartment in final concentration of 2 µM. Before and after 2 h incubation at 37° C. samples were taken from both compartments. Analysis of compound content was done after precipitation with methanol by LC/MS/MS analysis. Permeability (Papp) was calculated in the apical to basolateral (A→B) and basolateral to apical (B→A) directions. The apparent permeability was calculated using following equation:

$$P_{app}=(V_r/P_o)(1/S)(P_2/t)$$

Where $V_r$ is the volume of medium in the receiver chamber, $P_o$ is the measured peak area of the test drug in the donor chamber at t=o, S the surface area of the monolayer, $P_2$ is the measured peak area of the test drug in the acceptor chamber after 2 h of incubation, and t is the incubation time. The efflux ratio basolateral (B) to apical (A) was calculated by dividing the $P_{app}$ B–A by the $P_{app}$ A–B. In addition the compound recovery was calculated. As assay control reference compounds were analyzed in parallel.

Investigation of In Vitro Metabolic Stability in Rat Hepatocytes

Hepatocytes from Han Wistar rats were isolated via a 2-step perfusion method. After perfusion, the liver was carefully removed from the rat: the liver capsule was opened and the hepatocytes were gently shaken out into a Petri dish with ice-cold WME. The resulting cell suspension was filtered through sterile gaze in 50 ml falcon tubes and centrifuged at 50×g for 3 min at room temperature. The cell pellet was resuspended in 30 ml WME and centrifuged through a Percoll® gradient for 2 times at 100×g. The hepatocytes were washed again with Williams' medium E (WME) and resuspended in medium containing 5% FCS. Cell viability was determined by trypan blue exclusion.

For the metabolic stability assay liver cells were distributed in WME containing 5% FCS to glass vials at a density of $1.0 \times 10^6$ vital cells/ml. The test compound was added to a final concentration of 1 µM. During incubation, the hepatocyte suspensions were continuously shaken and aliquots were taken at 2, 8, 16, 30, 45 and 90 min, to which equal volumes of cold methanol were immediately added. Samples were frozen at −20° C. over night, after subsequently centrifuged for 15 minutes at 3000 rpm and the supernatant was analyzed with an Agilent 1200 HPLC-system with LCMS/MS detection.

The half-life of a test compound was determined from the concentration-time plot. From the half-life the intrinsic clearances were calculated. Together with the additional parameters liver blood flow, amount of liver cells in vivo and in vitro. The hepatic in vivo blood clearance (CL) and the maximal oral bioavailability ($F_{max}$) was calculated. The following parameter values were used: Liver blood flow—4.2 L/h/kg rat; specific liver weight—32 g/kg rat body weight; liver cells in vivo-$1.1 \times 10^8$ cells/g liver, liver cells in vitro—$0.5 \times 10^6$/ml.

In Vivo Pharmacokinetics in Rats

For in vivo pharmacokinetic experiments test compounds are administered to male Wistar rats intravenously at doses of 0.3 to 1 mg/kg and intragastral at doses of 0.5 to 10 mg/kg formulated as solutions using solubilizers such as PEG400 in well-tolerated amounts.

For pharmacokinetics after intravenous administration test compounds are given as i.v. bolus and blood samples are taken at 2 min, 8 min, 15 min, 30 min, 45 min, 1 h, 2 h, 4 h, 6 h, 8 h and 24 h after dosing. Depending on the expected half-life additional samples are taken at later time points (e.g., 48 h, 72 h). For pharmacokinetics after intragastral administration test compounds are given intragastral to fasted rats and blood samples are taken at 5 min, 15 min, 30 min, 45 min, 1 h, 2 h, 4 h, 6 h, 8 h and 24 h after dosing. Depending on the expected half-life additional samples are taken at later time points (e.g., 48 h, 72 h). Blood is collected into Lithium-Heparintubes (Monovetten®, Sarstedt) and centrifuged for 15 min at 3000 rpm. An aliquot of 100 µL from the supernatant (plasma) is taken and precipitated by addition of 400 µL cold acetonitril and frozen at −20° C. over night. Samples are subsequently thawed and centrifuged at 3000 rpm, 4° C. for 20 minutes. Aliquots of the supernatants are taken for analytical testing using an Agilent 1200 HPLC-system with LCMS/MS detection. PK parameters are calculated by non-compartmental analysis using a PK calculation software.

PK parameters derived from concentration-time profiles after i.v.: CLplasma: Total plasma clearance of test compound (in L/kg/h); CLblood: Total blood clearance of test compound: CLplasma*Cp/Cb (in L/kg/h) with Cp/Cb being the ratio of concentrations in plasma and blood. PK parameters calculated from concentration time profiles after i.g.: Cmax: Maximal plasma concentration (in mg/L); Cmaxnorm: Cmax divided by the administered dose (in kg/L); Tmax: Time point at which Cmax was observed (in h). Parameters calculated from both, i.v. and i.g. concentration-time profiles: AUCnorm: Area under the concentration-time curve from t=0 h to infinity (extrapolated) divided by the administered dose (in kg*h/L); AUC(0-tlast)norm: Area under the concentration-time curve from t=0 h to the last time point for which plasma concentrations could be measured divided by the administered dose (in kg*h/L); t½: terminal half-life (in h); F: oral bioavailability: AUCnorm after intragastral administration divided by AUCnorm after intravenous administration (in %).

The suitability of the compounds of the present invention for the treatment of hyperproliferative disorders can be demonstrated in animal models of the following cancer types: Lymphoma, Non-Hodgkin-Lymphoma type, Diffuse Large B-cell Lymphoma subtype, ovarian cancer, multiple myeloma, acute leukemia, acute myeloid leucemia type. For this purpose, human tumor cells of the respective cancer type are injected subcutaneously into immunocompromised mice. Once the primary tumor growth is established the animals will be then randomized to receive treatment with either compound at maximum tolerated dose or vehicle control for a certain period of time. The difference between those groups in terms of the tumor growth will be used to access the treatment efficacy. The principles of such xenograft studies are summarized in Richmond, A.; Su, Y. (2008). "Mouse xenograft models vs GEM models for human cancer therapeutics". Disease Models and Mechanisms 1 (2-3): 78-82. doi:10.1242/dmm.000976.

The invention claimed is:
1. A compound of general formula (I):

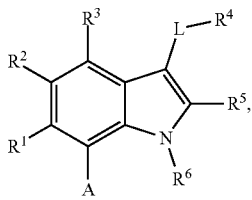

in which
A is

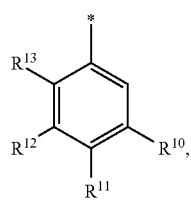

whereby optionally one or two of the groups selected from $CR^{11}$, $CR^{12}$ and $CR^{13}$ may be replaced by a nitrogen atom,
wherein $R^6$ and $R^{10}$, together with three carbon atoms of the phenyl ring, two carbon atoms of the indole moiety and the nitrogen atom to which $R^6$ is attached, form a 9- to 16-membered ring and * is the point of attachment of these moieties to the indole carbon atom bearing the A substituent;
$R^1$ and $R^2$ are each independently selected from a hydrogen atom, a halogen atom, a cyano group, a $C_1$-$C_3$-alkyl group, and a $C_1$-$C_3$-alkoxy group;
$R^3$ is selected from a hydrogen atom, a halogen atom, a cyano group, a $C_1$-$C_3$-alkyl group, a $C_1$-$C_3$-haloalkyl group, a $C_1$-$C_3$-alkoxy group, a $C_1$-$C_3$-alkylthio group, a —S(O)—($C_1$-$C_3$-alkyl) group, a —S(O)$_2$—($C_1$-$C_3$-alkyl) group, a $C_1$-$C_3$-haloalkoxy group, a $C_1$-$C_3$-haloalkylthio group, and a $C_3$-$C_5$-cycloalkyl group;
$R^4$ is selected from an aryl group and a heteroaryl group, each of which is optionally substituted with one, two, three, four or five substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, a ($C_1$-$C_3$)-haloalkyl-S-group, and a $C_3$-$C_5$-cycloalkyl group;
L is a group —(CH$_2$)$_m$-E- wherein any CH$_2$ group is optionally substituted with one or two substituents and each substituent is independently selected from a halogen atom, a cyano group, a hydroxyl group, a $C_1$-$C_3$-alkyl group, and a $C_1$-$C_3$-alkoxy group, or two substituents are optionally taken together with their intervening atoms to form a saturated or partially unsaturated 3-6-membered cycloalkyl ring, or a 3-8 membered saturated or partially unsaturated heterocyclic ring having 1-2 heteroatoms independently selected from an oxygen atom, a sulfur atom, a —S(O)— group, a —S(O)$_2$— group, and a —NR$^{14}$— group;

E is a bond, an oxygen atom, a sulfur atom, a —S(O)— group, a —S(O)$_2$— group or a —NR$^{14}$— group and constitutes the connecting element to $R^4$;
where $R^{14}$ is a hydrogen atom or a $C_1$-$C_3$-alkyl group;
m is 2, 3, or 4;
$R^5$ is selected from a COOH group, a

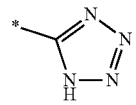

group, a —C(O)—NHS(O)$_2$($C_1$-$C_6$-alkyl) group, a —C(O)—NHS(O)$_2$($C_3$-$C_6$-cycloalkyl) group, a —C(O)—NHS(O)$_2$(aryl) group, a —C(O)—NHS(O)$_2$(CH$_2$)$_s$NHCO ($C_1$-$C_6$-alkyl) group, a —C(O)—NHS(O)$_2$(CH$_2$)$_s$NHCO ($C_3$-$C_6$-cycloalkyl) group, and a —C(O)—NHS(O)$_2$ (CH$_2$)$_s$NHCO(aryl) group;
s is 0, 1, 2, or 3;
—$R^6$-$R^{10}$— is selected from $^\#$—(CH$_2$)$_n$—(B)$_t$—(CH$_2$)$_p$—$^{\#\#}$, $^\#$—(C$_2$-C$_6$-alkenylene)-(B)$_t$—(CH$_2$)$_p$—$^{\#\#}$, $^\#$—(CH$_2$)$_n$—(B)$_t$—(C$_2$-C$_6$-alkenylene)-$^{\#\#}$, and $^\#$—(CH$_2$)$_q$—(B)—(CH$_2$)$_r$—(B)—(CH$_2$)$_v$—$^{\#\#}$,
where one or more CH$_2$ groups are optionally substituted with one or more substituents selected from a halogen atom, a hydroxyl group, a NR$^{17}$R$^{18}$ group, a $C_1$-$C_3$-alkyl group, a $C_1$-$C_3$-haloalkyl group, a $C_1$-$C_3$-alkoxy group, and a $C_1$-$C_3$-haloalkoxy group, wherein $^\#$ is the point of attachment with the indole nitrogen atom and $^{\#\#}$ is the point of attachment with the carbon atom of the phenyl moiety bearing the $R^{10}$ substituent;
n is 2, 3, 4, 5, 6, 7, 8, 9, or 10;
t is 0 or 1;
p is 0, 1, 2, 3, 4, 5, or 6;
q is 2, 3, 4, 5, or 6;
r is 2, 3, 4, 5, or 6;
v is 0, 1, or 2;
where the integers selected for variables n, t, p, q, r, and v result in forming a 9- to 16-membered ring;
B is independently selected from a —C(O)NR$^{15}$— group, a —NR$^{15}$C(O)— group, a —N(R$^{15}$)— group, a —N(R$^{15}$)—C(=O)—N(R$^{15}$)— group, a —O—C (=O)—N(R$^{15}$)— group, a —N(R$^{15}$)—C(=O)—O— group, —O—, —S—, —S(O)—, —S(O)$_2$—, a —S(O) NR$^{15}$— group, a —NR$^{15}$S(O)— group, a —S(O)$_2$NR$^{15}$— group, a —NR$^{15}$S(O)$_2$— group, a

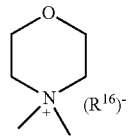

group and —[N$^+$(R$^{21}$R$^{22}$)—(R$^{16}$)$^-$] group;
$R^{15}$ is independently selected from a hydrogen atom, a $C_1$-$C_6$-alkyl group
which is optionally substituted with one or more substituents selected from a halogen atom, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a heterocycloalkyl group, an aryl group, a (R$^{19}$)-(heterocycloalkylene)-(arylene)-O— group, a (heterocycloalkyl)-(arylene)-O— group, an aryl-O— group, an aryl-(C$_1$-C$_3$-alkylene)-O— group, a (R$^{20}$)—S(O)$_2$-arylene-O— group, a (R$^{20}$)S(O)$_2$-(heterocycloalkylene)-(arylene)-O— group, an (aryl)-(heteroarylene)-O— group, and an (aryl)-(heteroarylene)-O—(C$_1$-C$_3$-alkylene)- group;

a phenyl group, a group

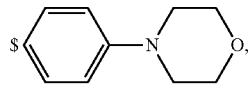

a group

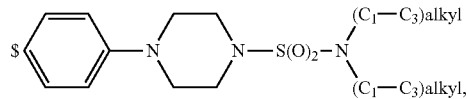

and a group

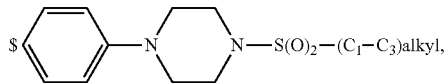

where $ is the point of attachment to the nitrogen atom, to which R$^{15}$ is attached, where R$^{16}$ is a pharmaceutically acceptable anion;

where R$^{17}$ and R$^{18}$ are each independently selected from a hydrogen atom, a C$_1$-C$_6$-alkyl group, a C$_1$-C$_6$-haloalkyl group, a C$_3$-C$_5$-cycloalkyl group, a C$_1$-C$_3$-alkyl-C(O)— group, a C$_1$-C$_3$-alkylS(O)$_2$— group, and a C$_1$-C$_3$-alkyl-O—C(=O)— group;

where R$^{19}$ is selected from a hydrogen atom, a hydroxyl group, a cyano group, a C$_1$-C$_3$-alkyl group, a C$_1$-C$_6$-hydroxyalkyl group, a C$_1$-C$_3$-alkoxy group, a C(O)OR$^{21}$—(C$_1$-C$_3$-alkylene)- group, a —C(O)OR$^{21}$ group, a —C(O)NR$^{21}$R$^{22}$ group, a (C$_1$-C$_3$-alkyl)-O—(C$_1$-C$_3$-alkylene)-C(O)— group, a (C$_1$-C$_6$-alkyl)-C(O)-group, and a C$_3$-C$_6$-cycloalkyl-C(O)— group;

where R$^{20}$ is selected from a C$_1$-C$_3$-alkyl group, a C$_3$-C$_6$-cycloalkyl group, and a NR$^{21}$R$^{22}$ group;

where R$^{21}$ and R$^{22}$ are independently selected from a hydrogen atom and a C$_1$-C$_6$-alkyl group;

R$^{11}$ and R$^{13}$ are each independently selected from a hydrogen atom, a halogen atom, a C$_1$-C$_3$-alkyl group, and a C$_1$-C$_3$-alkoxy group; and R$^{12}$ is selected from a hydrogen atom, a C$_1$-C$_3$-alkoxy group, a C$_1$-C$_3$-alkyl group, a C$_1$-C$_3$-haloalkyl group, a C$_1$-C$_3$-haloalkoxy group, and a NR$^{17}$R$^{18}$ group;

or a tautomer, an N-oxide, or a salt thereof or a salt of a tautomer or a N-oxide or a mixture of same.

2. The compound of general formula (I) according to claim 1:

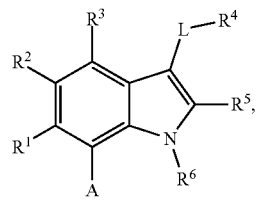

in which

A is

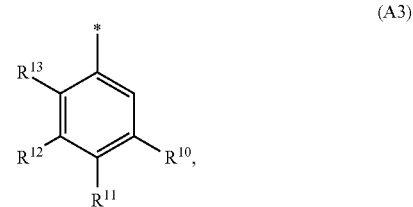

wherein R$^6$ and R$^{10}$, together with three carbon atoms of the phenyl ring, two carbon atoms of the indole moiety and the nitrogen atom to which R$^6$ is attached, form a 9- to 16-membered ring and * is the point of attachment of these moieties to the indole carbon atom bearing the A substituent;

R$^1$ and R$^2$ are each independently selected from a hydrogen atom, a halogen atom, a cyano group, a C$_1$-C$_3$-alkyl group and a C$_1$-C$_3$-alkoxy group;

R$^3$ is selected from a hydrogen atom, a halogen atom, a cyano group, a C$_1$-C$_3$-alkyl group, a C$_1$-C$_3$-haloalkyl group, a C$_1$-C$_3$-alkoxy group, a C$_1$-C$_3$-alkylthio group, a —S(O)—(C$_1$-C$_3$-alkyl) group, a —S(O)$_2$—(C$_1$-C$_3$-alkyl) group, a C$_1$-C$_3$-haloalkoxy group, a C$_1$-C$_3$-haloalkylthio group and a C$_3$-C$_5$-cycloalkyl group;

R$^4$ is selected from an aryl group and a heteroaryl group, each of which is optionally substituted with one, two, three, four or five substituents and each substituent is independently selected from a halogen atom, a cyano group, a C$_1$-C$_3$-alkyl group, a C$_1$-C$_3$-haloalkyl group, a C$_1$-C$_3$-alkoxy group, a C$_1$-C$_3$-thioalkyl group, a C$_1$-C$_3$-haloalkoxy group, a (C$_1$-C$_3$)-haloalkyl-S— group, and a C$_3$-C$_5$-cycloalkyl group;

L is a group —(CH$_2$)$_m$-E- wherein any CH$_2$ group is optionally substituted with one or two substituents and each substituent is independently selected from a halogen atom, a cyano group, a hydroxyl group, a C$_1$-C$_3$-alkyl group and a C$_1$-C$_3$-alkoxy group, or two substituents are optionally taken together with their intervening atoms to form a saturated or partially unsaturated 3-6-membered cycloalkyl ring, or a 3-8 membered saturated or partially unsaturated heterocyclic ring having 1-2 heteroatoms independently selected from an oxygen atom, a sulfur atom, a —S(O)— group, a —S(O)$_2$— group, and a —NR$^{14}$— group;

E is a bond, an oxygen atom, a sulfur atom, a —S(O)— group, a —S(O)$_2$— group or a —NR$^{14}$— group and constitutes the connecting element to R$^4$, where $R^{14}$ is a hydrogen atom or a $C_1$-$C_3$-alkyl group;
m is 2, 3, or 4;
$R^5$ is selected from a COOH group, a

*[tetrazole structure]* group, a —C(O)—NHS(O)$_2$($C_1$-$C_6$-alkyl) group, a —C(O)—NHS(O)$_2$($C_3$-$C_6$-cycloalkyl) group, a —C(O)—NHS(O)$_2$(aryl) group, a —C(O)—NHS(O)$_2$(CH$_2$)$_s$NHCO($C_1$-$C_6$-alkyl) group, a —C(O)—NHS(O)$_2$(CH$_2$)$_s$NHCO($C_3$-$C_6$-cycloalkyl) group, and a —C(O)—NHS(O)$_2$(CH$_2$)$_s$NHCO(aryl) group;
s is 0, 1, 2, or 3;
—$R^6$-$R^{10}$— is selected from $^\#$—(CH$_2$)$_n$—(B)$_t$—(CH$_2$)$_p$—$^{190\ \#\#}$, $^\#$—(C$_2$-C$_6$-alkenylene)-(B)$_t$—(CH$_2$)$_p$—$^{\#\#}$, $^\#$—(CH$_2$)$_n$—(B)$_t$—(C$_2$-C$_6$-alkenylene)-$^{\#\#}$, and $^\#$—(CH$_2$)$_q$—(B)—(CH$_2$)$_r$—(B)—(CH$_2$)$_v$—$^{\#\#}$,
where one or more CH$_2$ groups are optionally substituted with one or more substituents selected from a halogen atom, a hydroxyl group, a $NR^{17}R^{18}$ group, a $C_1$-$C_3$-alkyl group, a $C_1$-$C_3$-haloalkyl group, a $C_1$-$C_3$-alkoxy group, and a $C_1$-$C_3$-haloalkoxy group, wherein $^\#$ is the point of attachment with the indole nitrogen atom and $^{\#\#}$ is the point of attachment with the carbon atom of the phenyl moiety bearing the $R^{10}$ substituent;
n is 2, 3, 4, 5, 6, 7, 8, 9, or 10;
t is 0 or 1;
p is 0, 1, 2, 3, 4, 5, or 6;
q is 2, 3, 4, 5, or 6;
r is 2, 3, 4, 5, or 6;
v is 0, 1, or 2;
where the integers selected for variables n, t, p, q, r, and v result in forming a 9- to 16-membered ring;
B is independently selected from a —C(O)NR$^{15}$— group, a —NR$^{15}$C(O)— group, a —N(R$^5$)— group, a —N(R$^{15}$)—C(=O)—N(R$^{15}$)— group, a —O—C(=O)—N(R$^{15}$)— group, a —N(R$^5$)—C(=O)—O— group, —O—, —S—, —S(O)—, —S(O)$_2$—, a —S(O)NR$^{15}$— group, a —NR$^{15}$S(O)— group, a —S(O)$_2$NR$^{15}$— group, a —NR$^{15}$S(O)$_2$— group, and a

*[morpholinium structure with (R$^{16}$)$^-$]* group;
$R^{15}$ is independently selected from a hydrogen atom, a $C_1$-$C_6$-alkyl group
which is optionally substituted with one or more substituents selected from a halogen atom, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a heterocycloalkyl group, an aryl group, a (R$^{19}$)-(heterocycloalkylene)-(arylene)-O— group, an aryl-O— group, an aryl-(C$_1$-C$_3$-alkylene)-O— group, a (R$^{20}$)—S(O)$_2$-arylene-O— group, a (R$^{20}$)S(O)$_2$-heterocycloalkylene-arylene-O— group and an aryl-heteroarylene-O— group;
a phenyl group, a group

*[phenyl-morpholine structure]*, a group

*[phenyl-piperazine-S(O)$_2$-N((C$_1$-C$_3$)alkyl)$_2$ structure]* and
a group

*[phenyl-piperazine-S(O)$_2$-(C$_1$-C$_3$)alkyl structure]*, where $ is the point of attachment to the nitrogen atom, to which $R^{15}$ is attached,
where $R^{16}$ is a pharmaceutically acceptable anion;
where $R^{17}$ and $R^{18}$ are each independently selected from a hydrogen atom, a $C_1$-$C_6$-alkyl group, a $C_1$-$C_6$-haloalkyl group, a $C_3$-$C_5$-cycloalkyl group, a $C_1$-$C_3$-alkyl-C(O)— group, a $C_1$-$C_3$-alkylS(O)$_2$— group, and a $C_1$-$C_3$-alkyl-O—C(=O)— group;
where $R^{19}$ is selected from a hydrogen atom, a hydroxyl group, a cyano group, a $C_1$-$C_3$-alkyl group, a $C_1$-$C_6$-hydroxyalkyl group, a $C_1$-$C_3$-alkoxy group, a C(O)OR$^{21}$—(C$_1$-C$_3$-alkylene)- group, a —C(O)OR$^{21}$ group, a —C(O)NR$^{21}$R$^{22}$ group, a (C$_1$-C$_3$-alkyl)-O—(C$_1$-C$_3$-alkylene)-C(O)— group, a (C$_1$-C$_6$-alkyl)-C(O)-group, and a $C_3$-$C_6$-cycloalkyl-C(O)— group;
where $R^{20}$ is selected from a $C_1$-$C_3$-alkyl group, a $C_3$-$C_6$-cycloalkyl group, and a NR$^{21}$R$^{22}$ group;
where $R^{21}$ and $R^{22}$ are independently selected from a hydrogen atom and a $C_1$-$C_6$-alkyl group;
$R^{11}$ and $R^{13}$ are each independently selected from a hydrogen atom, a halogen atom, a $C_1$-$C_3$-alkyl group, and a $C_1$-$C_3$-alkoxy group; and
$R^{12}$ is selected from a hydrogen atom, a $C_1$-$C_3$-alkoxy group, a $C_1$-$C_3$-alkyl group, a $C_1$-$C_3$-haloalkyl group, a $C_1$-$C_3$-haloalkoxy group, and a NR$^{17}$R$^{18}$ group;
or a tautomer, an N-oxide, or a salt thereof or a salt of a tautomer or a N-oxide or a mixture of same.

3. The compound of general formula (I) according to claim 1 in which
A is (A3)

*[phenyl structure with R$^{13}$, R$^{12}$, R$^{11}$, R$^{10}$ substituents]*, wherein R⁶ and R¹⁰, together with three carbon atoms of the phenyl ring, two carbon atoms of the indole moiety and the nitrogen atom to which R⁶ is attached, form a 9- to 13-membered ring and * is the point of attachment of these moieties to the indole carbon atom bearing the A substituent;

R¹ and R² are each independently selected from a hydrogen atom, a $C_1$-$C_3$-alkyl group, and a $C_1$-$C_3$-alkoxy group;

R³ is selected from a hydrogen atom, a halogen atom, a $C_1$-$C_3$-alkyl group, and a $C_1$-$C_3$-alkoxy group;

R⁴ is an aryl group, which is optionally substituted with one, two, or three substituents and each substituent is independently selected from a halogen atom, a $C_1$-$C_3$-alkyl group, and a $C_1$-$C_3$-haloalkyl group;

L is a group —(CH₂)$_m$-E- wherein any CH₂ group is optionally substituted with an $C_1$-$C_3$-alkyl group;

E is an oxygen atom;

m is 2, or 3;

R⁵ is a COOH group;

—R⁶-R¹⁰— is $^\#$—(CH₂)$_q$—(B)—(CH₂)$_r$—(B)—(CH₂)$_v$—$^{\#\#}$, wherein $^\#$ is the point of attachment with the indole nitrogen atom and $^{\#\#}$ is the point of attachment with the carbon atom of the phenyl moiety bearing the R¹⁰ substituent;

n is 2, 3, 4, 5, or 6;

t is 0 or 1;

p is 0 or 1;

q is 2;

r is 2;

v is 0 or 1;

where the integers selected for variables n, t, p, q, r, and v result in forming a 9- to 13-membered ring;

B is independently selected from a —N(R¹⁵)— group, —O—, and a

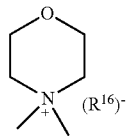

group;

R¹⁵ is independently selected from a hydrogen atom, a $C_1$-$C_3$-alkyl group which is optionally substituted with a phenyl group, a phenyl group, a group

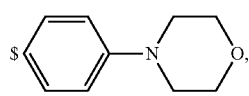

a group

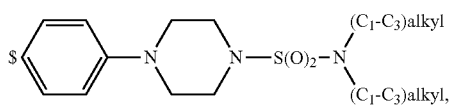

and a group

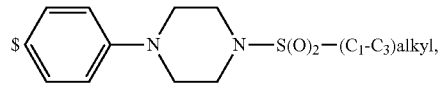

where $ is the point of attachment to the nitrogen atom, to which R¹⁵ is attached;

where R¹⁶ is a pharmaceutically acceptable anion;

where R¹⁹ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a C(O)OR²¹—($C_1$-$C_3$-alkylene)- group, a —C(O)OR²¹ group, a —C(O)NR²¹R²² group, a ($C_1$-$C_3$-alkyl)-O—($C_1$-$C_3$-alkylene)-C(O)— group, a ($C_1$-$C_3$-alkyl)-C(O)-group, and a $C_3$-$C_6$-cycloalkyl-C(O)— group;

where R²⁰ is selected from a $C_1$-$C_3$-alkyl group, a $C_3$-$C_6$-cycloalkyl group, and a NR²¹R²² group;

where R²¹ and R²² are independently selected from a hydrogen atom and a $C_1$-$C_3$-alkyl group;

R¹¹ and R¹³ are independently selected from a hydrogen atom, and a $C_1$-$C_3$-alkyl group; and R¹² is selected from a hydrogen atom and a $C_1$-$C_3$-alkoxy group;

or a tautomer, an N-oxide, or a salt thereof or a salt of a tautomer or a N-oxide or a mixture of same.

4. The compound according to claim 1, wherein A is

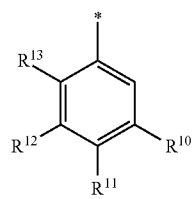

(A3)

where R⁶ and R¹⁰, together with three carbon atoms of the phenyl ring, two carbon atoms of the indole moiety and the nitrogen atom to which R⁶ is attached, form a 12-membered ring and * is the point of attachment of these moieties to indole carbon atom bearing the A substituent;

R¹, R², and R³ are each independently hydrogen, a methyl group or a methoxy group;

R⁴ is selected from a 1-naphthyl group,
  which is optionally substituted with one or two substituents and each substituent is independently selected from a fluorine atom, a chlorine atom, a methyl group and a trifluoromethyl group;
a 4-chloro-3,5-dimethyl-phenyl-1-yl group, and
a 5,6,7,8-tetrahydronaphthalen-1-yl group;

L is —(CH₂)₃-E- and E is —O—;

R⁵ is —COOH;

—R⁶-R¹⁰— is selected from $^\#$—(CH₂)₂—O—(CH₂)₂—O—$^{\#\#}$ and $^\#$(CH₂)₅—O—$^{\#\#}$, wherein $^\#$ is the point of attachment with the indole nitrogen atom and $^{\#\#}$ is the point of attachment with the carbon atom of the phenyl moiety bearing the R¹⁰ substituent;

$R^{15}$ is selected from a hydrogen atom, a methyl group, a phenyl group, a benzyl group, a group

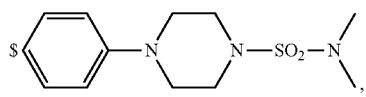

a group

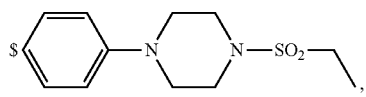

and a group

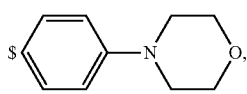

where $ is the point of attachment to the nitrogen atom, to which $R^{15}$ is attached;

$R^{11}$ is a hydrogen atom;

$R^{12}$ is a hydrogen atom or a methoxy group; and $R^{13}$ is a hydrogen atom or a methyl group;

or a tautomer, an N-oxide, or a salt thereof or a salt of a tautomer or a N-oxide or a mixture of same.

5. The compound according to claim 1, wherein A is

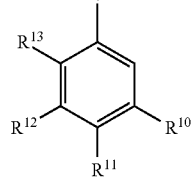

(A3)

where $R^6$ and $R^{10}$, together with three carbon atoms of the phenyl ring, two carbon atoms of the indole moiety and the nitrogen atom to which $R^6$ is attached, form a 12-membered ring and * is the point of attachment of these moieties to the indole carbon atom bearing the A substituent;

$R^1$, $R^2$, and $R^3$ are each a hydrogen atom or a methyl group;

$R^4$ is selected from a 1-naphthyl group, a 4-chloro-3,5-dimethyl-phenyl-1-yl group, and a 5,6,7,8-tetrahydronaphthalen-1-yl group;

L is —$(CH_2)_3$-E- and E is —O—;

$R^5$ is —COOH;

—$R^6$-$R^{10}$— is selected from $^{\#}$—$(CH_2)_2$—O—$(CH_2)_2$—O—$^{\#\#}$ and $^{\#}(CH_2)_5$—O—$^{\#\#}$, wherein $^{\#}$ is the point of attachment with the indole nitrogen atom and $^{\#\#}$ is the point of attachment with the carbon atom of the phenyl moiety bearing the $R^{10}$ substituent;

$R^{15}$ is selected from a methyl group, a phenyl group, a group,

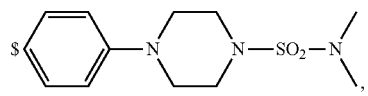

a group

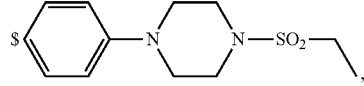

and a group

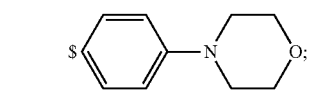

where $ is the point of attachment to the nitrogen atom, to which $R^{15}$ is attached;

$R^{12}$ is a methoxy group; and $R^{11}$ and $R^{13}$ are each a hydrogen atom;

or a tautomer, an N-oxide, or a salt thereof or a salt of a tautomer or a N-oxide or a mixture of same.

6. A method of preparing a compound of general formula (I) according to claim 1, said method comprising the step of reacting an intermediate compound of general formula (II):

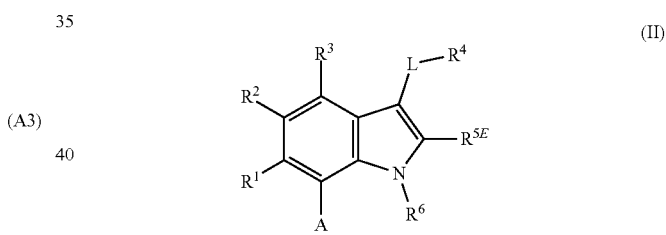

(II)

in which $R^1$, $R^2$, $R^3$, $R^4$, $R^6$, A and L are as defined for the compound of general formula (I) according to claim 1, and $R^{5E}$ represents a carboxylic ester group or a benzyl ester group, with an alkali hydroxide in a mixture of water with THF and/or an aliphatic alcohol of formula $C_1$-$C_3$-alkyl-OH, at a temperature between 0° C. and 100° C. including 0° C. and 100° C., to transform the group $R^{5E}$ into a group $R^5$ as defined for the compounds of general formula (I), and subsequently optionally converting the free acid group $R^5$ into a pharmaceutically acceptable salt thereof to obtain a compound of general formula (I)

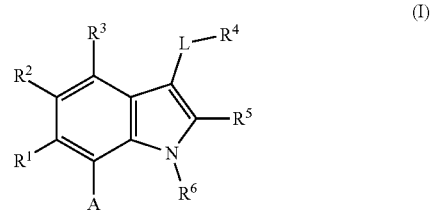

(I)

in which $R^1$, $R^2$, $R^3$, $R^4$, $R^5$, $R^6$, A and L are as defined for the compound of general formula (I) according to claim 1 or a stereoisomer, a tautomer, an N-oxide, a hydrate, a solvate, or a salt thereof, or a mixture of same and optionally separating enantiomers by means of preparative HPLC on a chiral stationary phase.

7. A method of inhibiting proliferation of a cell and/or inducing apoptosis in a cell, comprising contacting the cell with a compound of formula (I) according to claim 1.

8. A method of treating a disease, comprising administering a compound of general formula (I) according to claim 1 to a subject, wherein the disease is a hyperproliferative disease.

9. The method of claim 8, wherein the hyperproliferative disease is cancer.

10. The method according to claim 9, wherein the cancer is selected from breast cancer; lung cancer; lymphoma; acute leukemia; melanoma; multiple myeloma; ovarian cancer; and pancreas cancer.

11. A pharmaceutical composition comprising a compound of general formula (I) according to claim 1 and one or more pharmaceutically acceptable excipients.

12. A method of treating cancer, comprising administering a pharmaceutical composition according to claim 11 to a subject.

13. A method of inhibiting proliferation of a cell and/or inducing apoptosis in a cell, comprising contacting the cell with the pharmaceutical composition according to claim 11.

14. A pharmaceutical combination comprising:
one or more compounds of general formula (I) according to claim 1, and
one or more further anti-cancer agents.

15. An intermediate compound of general formula (II):

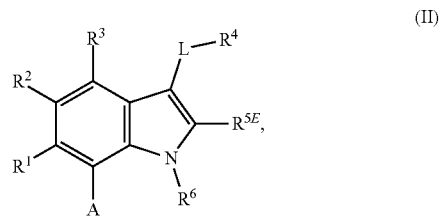

in which $R^1$, $R^2$, $R^3$, $R^4$, $R^6$, A and L are as defined for the compound of general formula (I) according to claim 1, and $R^{5E}$ represents a carboxylic ester group.

16. The method according to claim 10, wherein the lymphoma is selected from non-Hodgkin-lymphoma type, diffuse large B-cell lymphoma (DLBCL), and mantle cell lymphoma.

17. The method according to claim 16, wherein the DLBCL is germinal B-cell-DLBCL or acute B-cell DLBCL.

18. The method according to claim 10, wherein the acute leukemia is acute myeloid leukemia or acute monocytic leukemia.

\* \* \* \* \*